(12) United States Patent
Wang et al.

(10) Patent No.: US 11,964,989 B2
(45) Date of Patent: *Apr. 23, 2024

(54) KRAS G12D INHIBITORS

(71) Applicants: Mirati Therapeutics, Inc., San Diego, CA (US); Array BioPharma Inc., Boulder, CO (US)

(72) Inventors: Xiaolun Wang, San Diego, CA (US); Aaron Craig Burns, San Diego, CA (US); James Gail Christensen, San Diego, CA (US); John Michael Ketcham, San Diego, CA (US); John David Lawson, Carlsbad, CA (US); Matthew Arnold Marx, San Diego, CA (US); Christopher Ronald Smith, San Diego, CA (US); Shelley Allen, Boulder, CO (US); James F. Blake, Longmont, CO (US); Mark Joseph Chicarelli, Boulder, CO (US); Joshua Ryan Dahlke, Longmont, CO (US); Donghua Dai, Superior, CO (US); Jay Bradford Fell, Longmont, CO (US); John Peter Fischer, Longmont, CO (US); Macedonio J. Mejia, Denver, CO (US); Brad Newhouse, Boulder, CO (US); Phong Nguyen, Boulder, CO (US); Jacob Matthew O'Leary, Denver, CO (US); Spencer Pajk, Boulder, CO (US); Martha E. Rodriguez, Boulder, CO (US); Pavel Savechenkov, Boulder, CO (US); Tony P. Tang, Boulder, CO (US); Guy P.A. Vigers, Boulder, CO (US); Qian Zhao, Boulder, CO (US); Dean Russell Kahn, Boulder, CO (US); John Gaudino, Boulder, CO (US); Michael Christopher Hilton, Boulder, CO (US)

(73) Assignees: Mirati Therapeutics, Inc., San Diego, CA (US); Array BioPharma Inc., Boulder, CO (US)

(*) Notice: Subject to any disclaimer, the term of this patent is extended or adjusted under 35 U.S.C. 154(b) by 0 days.

This patent is subject to a terminal disclaimer.

(21) Appl. No.: 17/869,575

(22) Filed: Jul. 20, 2022

(65) Prior Publication Data

US 2023/0077225 A1  Mar. 9, 2023

Related U.S. Application Data

(63) Continuation of application No. 17/005,004, filed on Aug. 27, 2020, now Pat. No. 11,453,683.

(60) Provisional application No. 63/058,188, filed on Jul. 29, 2020, provisional application No. 63/052,840, filed on Jul. 16, 2020, provisional application No. 62/893,604, filed on Aug. 29, 2019.

(51) Int. Cl.
C07D 519/00 (2006.01)

(52) U.S. Cl.
CPC .................. C07D 519/00 (2013.01)

(58) Field of Classification Search
CPC ...................................... C07D 519/00
USPC ........................................ 514/249
See application file for complete search history.

(56) References Cited

U.S. PATENT DOCUMENTS

| | | | |
|---|---|---|---|
| 8,163,763 B2 | 4/2012 | Bergeron et al. | |
| 8,426,401 B2 | 4/2013 | Bian et al. | |
| 9,562,019 B2 | 2/2017 | Djaballah et al. | |
| 9,840,516 B2 | 12/2017 | Li et al. | |
| 10,125,134 B2 | 11/2018 | Blake et al. | |
| 11,453,683 B1 * | 9/2022 | Wang | A61P 35/00 |

(Continued)

FOREIGN PATENT DOCUMENTS

| | | |
|---|---|---|
| WO | 02/053558 A1 | 7/2002 |
| WO | 02/087513 A2 | 11/2002 |

(Continued)

OTHER PUBLICATIONS

Figueras, A. et al., "The impact of KRAS mutations on VEGF-A production and tumour vascular network", BMC Cancer 2013, 13:125.

(Continued)

Primary Examiner — Kahsay Habte
(74) Attorney, Agent, or Firm — Wood, Phillips, Katz, Clark & Mortimer

(57) ABSTRACT

Compounds that inhibit KRas G12D. In particular, compounds that inhibit the activity of KRas G12D, pharmaceutical compositions comprising the compounds and methods of use therefor, and in particular, methods of treating cancer. The compounds have a general structure represented by Formula (I):

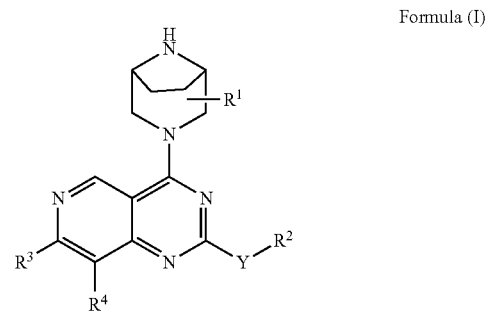

Formula (I)

or a pharmaceutically acceptable salt thereof.

19 Claims, No Drawings

(56) References Cited

U.S. PATENT DOCUMENTS

| | | |
|---|---|---|
| 2003/0191143 A1 | 10/2003 | Pitts et al. |
| 2010/0081654 A1 | 4/2010 | Stockwell et al. |
| 2011/0269244 A1 | 11/2011 | Petter et al. |
| 2013/0029978 A1 | 1/2013 | Kamino et al. |
| 2014/0288045 A1 | 9/2014 | Ren et al. |
| 2015/0175558 A1 | 6/2015 | Stockwell et al. |
| 2015/0239900 A1 | 8/2015 | Li et al. |
| 2016/0031898 A1 | 2/2016 | Ren et al. |
| 2016/0108019 A1 | 4/2016 | Li et al. |
| 2016/0166571 A1 | 6/2016 | Janes et al. |
| 2016/0229836 A1 | 8/2016 | Stockwell et al. |
| 2016/0264627 A1 | 9/2016 | Henning et al. |
| 2016/0297774 A1 | 10/2016 | Li et al. |
| 2017/0022184 A1 | 1/2017 | Li et al. |
| 2017/0115303 A1 | 4/2017 | Cravatt et al. |
| 2017/0190672 A1 | 7/2017 | Mani et al. |
| 2017/0197945 A1 | 7/2017 | Li et al. |
| 2018/0015087 A1 | 1/2018 | Liu et al. |
| 2018/0118757 A1 | 5/2018 | Li et al. |
| 2018/0118761 A1 | 5/2018 | Sebti et al. |
| 2018/0127396 A1 | 5/2018 | Li et al. |
| 2018/0141927 A1 | 5/2018 | Li et al. |
| 2018/0155348 A1 | 6/2018 | Li et al. |
| 2018/0162812 A1 | 6/2018 | Ren et al. |
| 2018/0177767 A1 | 6/2018 | Lanman et al. |
| 2018/0194748 A1 | 7/2018 | Li et al. |
| 2018/0201610 A1 | 7/2018 | Tao et al. |
| 2018/0273515 A1 | 9/2018 | Li et al. |
| 2018/0273523 A1 | 9/2018 | Li et al. |
| 2018/0273577 A1 | 9/2018 | Revenko et al. |
| 2018/0282307 A1 | 10/2018 | Li et al. |
| 2018/0282308 A1 | 10/2018 | Li et al. |
| 2018/0289683 A1 | 10/2018 | McCormick et al. |
| 2020/0399297 A1 | 12/2020 | Campbell et al. |

FOREIGN PATENT DOCUMENTS

| | | |
|---|---|---|
| WO | 2007/146122 A2 | 12/2007 |
| WO | 2008/009078 A2 | 1/2008 |
| WO | 2009/047255 A1 | 4/2009 |
| WO | 2010/014939 A1 | 2/2010 |
| WO | 2010/120996 A1 | 10/2010 |
| WO | 2013/155223 A1 | 10/2013 |
| WO | 2014/143659 A1 | 9/2014 |
| WO | 2014/152588 A1 | 9/2014 |
| WO | 2016/049568 A1 | 3/2015 |
| WO | 2015/054572 A1 | 4/2015 |
| WO | 2016/025650 A1 | 2/2016 |
| WO | 2016/044772 A1 | 3/2016 |
| WO | 2016/049565 A1 | 3/2016 |
| WO | 2016/164675 A1 | 10/2016 |
| WO | 2016/168540 A1 | 10/2016 |
| WO | 2017/058728 A1 | 4/2017 |
| WO | 2017/058768 A1 | 4/2017 |
| WO | 2017/058792 A1 | 4/2017 |
| WO | 2017/058805 A1 | 4/2017 |
| WO | 2017/058807 A1 | 4/2017 |
| WO | 2017/058902 A1 | 4/2017 |
| WO | 2017/058915 A1 | 4/2017 |
| WO | 2017/070256 A2 | 4/2017 |
| WO | 2017/079864 A1 | 5/2017 |
| WO | 2017/080980 A1 | 5/2017 |
| WO | 2017/087528 A1 | 5/2017 |
| WO | 2017/100546 A1 | 6/2017 |
| WO | 2018/064510 A1 | 4/2018 |
| WO | 2018/068017 A1 | 4/2018 |
| WO | 2018/102452 A2 | 6/2018 |
| WO | 2018/102453 A1 | 6/2018 |
| WO | 2018/112420 A1 | 6/2018 |
| WO | 2018/115380 A1 | 6/2018 |
| WO | 2018/119183 A2 | 6/2018 |
| WO | 2018/140512 A1 | 8/2018 |
| WO | 2018/140513 A1 | 8/2018 |
| WO | 2018/140514 A1 | 8/2018 |
| WO | 2018/140598 A1 | 8/2018 |
| WO | 2018/140599 A1 | 8/2018 |
| WO | 2018/140600 A1 | 8/2018 |
| WO | 2018/143315 A1 | 8/2018 |
| WO | 2018/195439 A2 | 10/2018 |
| WO | 2019/051291 A1 | 3/2019 |
| WO | 202063594 | 4/2020 |
| WO | 202098488 | 5/2020 |
| WO | 202027202 | 8/2020 |
| WO | 2020163598 | 8/2020 |
| WO | 2020165670 | 8/2020 |
| WO | 2020169838 | 8/2020 |
| WO | 2020171499 | 8/2020 |
| WO | 2020172332 | 8/2020 |
| WO | 2020176693 | 9/2020 |
| WO | 2020176963 | 9/2020 |
| WO | 2020177629 | 9/2020 |
| WO | 2020178282 | 9/2020 |
| WO | 2020181142 | 9/2020 |
| WO | 2020198125 | 10/2020 |
| WO | 2020204359 | 10/2020 |
| WO | 2020205473 | 10/2020 |
| WO | 2020205486 | 10/2020 |
| WO | 2020212895 | 10/2020 |
| WO | 2020214537 | 10/2020 |
| WO | 2020221239 | 11/2020 |
| WO | 2020230028 | 11/2020 |
| WO | 2020230091 | 11/2020 |
| WO | 2020231806 | 11/2020 |
| WO | 2020231808 | 11/2020 |
| WO | 2020232130 | 11/2020 |
| WO | 2020233592 | 11/2020 |
| WO | 2020234103 | 11/2020 |
| WO | 2020236940 | 11/2020 |
| WO | 2020236947 | 11/2020 |
| WO | 2020236948 | 11/2020 |
| WO | 2020247914 | 12/2020 |
| WO | 2020252336 | 12/2020 |
| WO | 2020252353 | 12/2020 |
| WO | 2021000885 | 1/2021 |
| WO | 2021023154 | 2/2021 |
| WO | 2021023247 | 2/2021 |
| WO | 2021027911 | 2/2021 |
| WO | 2021027943 | 2/2021 |
| WO | 2021031952 | 2/2021 |
| WO | 2021034992 | 2/2021 |
| WO | 2021037018 | 3/2021 |
| WO | 2021041671 | 3/2021 |
| WO | 2021043322 | 3/2021 |
| WO | 2021045279 | 3/2021 |
| WO | 2021050732 | 3/2021 |
| WO | 2021051034 | 3/2021 |
| WO | 2021052499 | 3/2021 |
| WO | 2021055728 | 3/2021 |
| WO | 2021057832 | 4/2021 |
| WO | 2021058018 | 4/2021 |
| WO | 2021061515 | 4/2021 |
| WO | 2021061749 | 4/2021 |
| WO | 2021063346 | 4/2021 |
| WO | 2021068898 | 4/2021 |
| WO | 2021075147 | 4/2021 |
| WO | 2021076655 | 4/2021 |
| WO | 2021078285 | 4/2021 |
| WO | 2021078312 | 4/2021 |
| WO | 2021080359 | 4/2021 |
| WO | 2021081212 | 4/2021 |
| WO | 2021083167 | 5/2021 |
| WO | 2021084765 | 5/2021 |
| WO | 2021085653 | 5/2021 |
| WO | 2021086833 | 5/2021 |
| WO | 2021088458 | 5/2021 |
| WO | 2021088938 | 5/2021 |
| WO | 2021091956 | 5/2021 |
| WO | 2021091967 | 5/2021 |
| WO | 2021091982 | 5/2021 |
| WO | 2021093758 A1 | 5/2021 |
| WO | 2021104431 A1 | 6/2021 |
| WO | 2021106230 A1 | 6/2021 |
| WO | 2021106231 A1 | 6/2021 |
| WO | 2021107160 A1 | 6/2021 |

(56) References Cited

FOREIGN PATENT DOCUMENTS

| | | |
|---|---|---|
| WO | 2021108683 A1 | 6/2021 |
| WO | 2021109737 A1 | 6/2021 |
| WO | 2021113595 A1 | 6/2021 |
| WO | 2021120045 A1 | 6/2021 |
| WO | 2021121330 A1 | 6/2021 |
| WO | 2021121367 A1 | 6/2021 |
| WO | 2021121371 A1 | 6/2021 |
| WO | 2021121397 A1 | 6/2021 |
| WO | 2021126120 A1 | 6/2021 |
| WO | 2021126799 A1 | 6/2021 |
| WO | 2021127404 A1 | 6/2021 |
| WO | 2021129820 A1 | 7/2021 |
| WO | 2021129824 A1 | 7/2021 |
| WO | 2021139678 A1 | 7/2021 |
| WO | 2021139748 A1 | 7/2021 |
| WO | 2021141628 A1 | 7/2021 |
| WO | 2021142252 A1 | 7/2021 |
| WO | 2021143693 A1 | 7/2021 |
| WO | 2021145520 A1 | 7/2021 |
| WO | 2021145521 A1 | 7/2021 |
| WO | 2021147965 A1 | 7/2021 |
| WO | 2021147967 A1 | 7/2021 |
| WO | 2021150613 A1 | 7/2021 |
| WO | 2021152149 A1 | 8/2021 |
| WO | 2021168193 A1 | 8/2021 |
| WO | 2021169963 A1 | 9/2021 |
| WO | 2021169990 A1 | 9/2021 |
| WO | 2021173923 A1 | 9/2021 |
| WO | 2021175199 A1 | 9/2021 |
| WO | 2021177721 A1 | 9/2021 |
| WO | 2021178740 A2 | 9/2021 |
| WO | 2021178741 A1 | 9/2021 |
| WO | 2021180181 A1 | 9/2021 |
| WO | 2021185233 A1 | 9/2021 |
| WO | 2021190467 A2 | 9/2021 |
| WO | 2021197499 A1 | 10/2021 |
| WO | 2021203768 A1 | 10/2021 |
| WO | 2021207172 A1 | 10/2021 |
| WO | 2021211864 A1 | 10/2021 |
| WO | 2021215544 A1 | 10/2021 |
| WO | 2021216770 A1 | 10/2021 |
| WO | 2021217019 A1 | 10/2021 |
| WO | 2021090855 A1 | 11/2021 |
| WO | 2021218110 A1 | 11/2021 |
| WO | 2021219072 A1 | 11/2021 |
| WO | 2021219090 A2 | 11/2021 |
| WO | 2021219091 A1 | 11/2021 |
| WO | 2021228161 A1 | 11/2021 |
| WO | 2021231526 A1 | 11/2021 |
| WO | 2021236475 A1 | 11/2021 |
| WO | 2021239058 A1 | 12/2021 |
| WO | 2021243280 A1 | 12/2021 |
| WO | 2021244603 A1 | 12/2021 |
| WO | 2021245051 A1 | 12/2021 |
| WO | 2021245055 A1 | 12/2021 |
| WO | 2021245499 A1 | 12/2021 |
| WO | 2021248079 A1 | 12/2021 |
| WO | 2021248082 A1 | 12/2021 |
| WO | 2021248083 A1 | 12/2021 |
| WO | 2021248090 A1 | 12/2021 |
| WO | 2021248095 A1 | 12/2021 |
| WO | 2021249563 A1 | 12/2021 |
| WO | 2021252339 A1 | 12/2021 |
| WO | 2021257828 A1 | 12/2021 |
| WO | 2021259331 A1 | 12/2021 |
| WO | 2022002102 A1 | 1/2022 |
| WO | 2022015375 A1 | 1/2022 |
| WO | 2022017339 A1 | 1/2022 |
| WO | 2022028346 A1 | 2/2022 |
| WO | 2022028492 A1 | 2/2022 |
| WO | 2022031678 A1 | 2/2022 |
| WO | 2022036176 A1 | 2/2022 |

OTHER PUBLICATIONS

Ambrogio, C. et al., "KRAS Dimerization Impacts MEK Inhibitor Sensitivity and Oncogenic Activity of Mutant KRAS", Cell 172, 1-12, Feb. 8, 2018, Elsevier Inc.

Burgess, M. et al., "KRAS Allelic Imbalance Enhances Fitness and Modulates MAP Kinase Dependence in Cancer", Cell 168, 817-829, Feb. 23, 2017, Elsevier Inc.

Serafimova et al., "Reversible targeting of noncatalytic cysteines with chemically tuned electrophiles", Nat Chem Biol.; 8(5):471-476. doi:10.1038/nchembio.925.

\* cited by examiner

KRAS G12D INHIBITORS

FIELD OF THE INVENTION

The present invention relates to compounds that inhibit KRas G12D. In particular, the present invention relates to compounds that inhibit the activity of KRas G12D, pharmaceutical compositions comprising the compounds and methods of use therefor.

BACKGROUND OF THE INVENTION

Kirsten Rat Sarcoma 2 Viral Oncogene Homolog ("KRas") is a small GTPase and a member of the Ras family of oncogenes. KRas serves as a molecular switch cycling between inactive (GDP-bound) and active (GTP-bound) states to transduce upstream cellular signals received from multiple tyrosine kinases to downstream effectors to regulate a wide variety of processes, including cellular proliferation (e.g., see Alamgeer et al., (2013) Current Opin Pharmcol. 13:394-401).

The role of activated KRas in malignancy was observed over thirty years ago (e.g., see Santos et al., (1984) Science 223:661-664). Aberrant expression of KRas accounts for up to 20% of all cancers and oncogenic KRas mutations that stabilize GTP binding and lead to constitutive activation of KRas and downstream signaling have been reported in 25-30% of lung adenocarcinomas. (e.g., see Samatar and Poulikakos (2014) Nat Rev Drug Disc 13(12): 928-942 doi: 10.1038/nrd428). Single nucleotide substitutions that result in missense mutations at codons 12 and 13 of the KRas primary amino acid sequence comprise approximately 40% of these KRas driver mutations in lung adenocarcinoma. KRAS G12D mutation is present in 25.0% of all pancreatic ductal adenocarcinoma patients, 13.3% of all colorectal carcinoma patients, 10.1% of all rectal carcinoma patients, 4.1% of all non-small cell lung carcinoma patients and 1.7% of all small cell lung carcinoma patients (e.g., see The AACR Project GENIE Consortium, (2017) Cancer Discovery; 7(8):818-831. Dataset Version 4).

The well-known role of KRas in malignancy and the discovery of these frequent mutations in KRas in various tumor types made KRas a highly attractive target of the pharmaceutical industry for cancer therapy. Notwithstanding thirty years of large-scale discovery efforts to develop inhibitors of KRas for treating cancer, no KRas inhibitor has yet demonstrated sufficient safety and/or efficacy to obtain regulatory approval (e.g., see McCormick (2015) Clin Cancer Res. 21 (8):1797-1801).

Compounds that inhibit KRas activity are still highly desirable and under investigation, including those that disrupt effectors such as guanine nucleotide exchange factors (e.g., see Sun et al., (2012) Agnew Chem Int Ed Engl. 51(25):6140-6143 doi: 10.1002/anie201201358) as well recent advances in the covalent targeting of an allosteric pocket of KRas G12C (e.g., see Ostrem et al., (2013) Nature 503:548-551 and Fell et al., (2018) ACS Med. Chem. Lett. 9:1230-1234).

Clearly there remains a continued interest and effort to develop inhibitors of KRas, particularly inhibitors of activating KRas mutants, especially KRas G12D.

Thus, there is a need to develop new KRas G12D inhibitors that demonstrate sufficient efficacy for treating KRas G12D-mediated cancer.

SUMMARY OF THE INVENTION

In one aspect of the invention, compounds are provided that inhibit KRas G12D activity.

In certain embodiments, the compounds are represented by Formula (I):

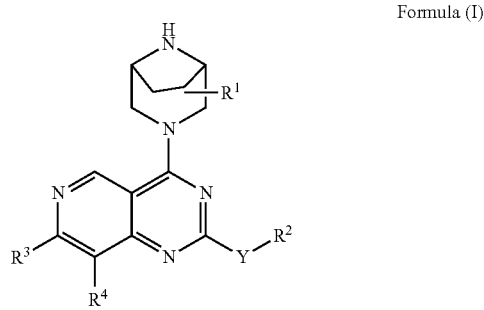

Formula (I)

or a pharmaceutically acceptable salt thereof:
wherein:
$R^1$ is hydrogen, hydroxy, halogen, C1-C3 alkyl, C1-C3 cyanoalkyl, C1-C3 hydroxyalkyl, HC(=O)—, —CO$_2$R$^5$, —CO$_2$N(R$^5$)$_2$ or a 5-6 membered heteroaryl;

Y is a bond, O or NR$^5$;

$R^2$ is hydrogen, —N(R$^5$)$_2$, heterocyclyl, C1-C6 alkyl, -L-heterocyclyl, -L-aryl, -L-heteroaryl, -L-cycloalkyl, -L-N(R$^5$)$_2$, -L-NHC(=NH)NH$_2$, -L-C(O)N(R$^5$)$_2$, -L-C1-C6 haloalkyl, -L-OR$^5$, -L-(CH$_2$OR$^5$)(CH$_2$)$_n$OR$^5$, -L-NR$^5$C(O)-aryl, -L-COOH, or -LC(=O)OC1-C6 alkyl, wherein the heterocyclyl and the aryl portion of -L-NR$^5$C(O)-aryl and the heterocyclyl portion of -L-heterocyclyl and the cycloalkyl portion of the -L-cycloalkyl may be optionally substituted with one or more R$^6$, and wherein the aryl or heteroaryl of the -L-aryl and the -L-heteroaryl may be optionally substituted with one or more R$^7$;

each L is independently a C1-C4 alkylene optionally substituted with hydroxy, C1-C4 hydroxyalkyl or heteroaryl;

$R^3$ is aryl or heteroaryl, wherein the aryl or the heteroaryl is optionally substituted with one or more R$^8$;

$R^4$ is hydrogen, halogen or C1-C3 alkyl;

each R$^5$ is independently hydrogen or C1-C3 alkyl;

each R$^6$ is independently halogen, hydroxy, C1-C3 hydroxyalkyl, C1-C3 alkyl, C1-C3 haloalkyl, C1-C3 alkoxy, cyano, -Q-phenyl, -Q-phenylSO$_2$F, —NHC(O)phenyl, —NHC(O)phenylSO$_2$F, C1-C3 alkyl substituted pyrazolyl, araC1-C3 alkyl-, tert-butyldimethylsilyloxyCH$_2$—, —N(R$^5$)$_2$, (C1-C3 alkoxy) C1-C3 alkyl-, (C1-C3 alkyl)C(=O), oxo, (C1-C3 haloalkyl)C(=O)—, —SO$_2$F, (C1-C3 alkoxy)C1-C3 alkoxy, —CH$_2$OC(O)N(R$^5$)$_2$, —CH$_2$NHC(O)OC1-C6 alkyl, —CH$_2$NHC(O)N(R$^5$)$_2$, —CH$_2$NHC(O)C1-C6 alkyl, —CH$_2$(pyrazolyl), —CH$_2$NHSO$_2$C1-C6 alkyl, —CH$_2$OC(O)heterocyclyl, —OC(O)N(R$^5$)$_2$, —OC(O)NH(C1-C3 alkyl)O(C1-C3 alkyl), —OC(O)NH(C1-C3 alkyl)O(C1-C3 alkyl)phenyl(C1-C3 alkyl)N(CH$_3$)$_2$, —OC(O)NH(C1-C3 alkyl)O(C1-C3 alkyl)phenyl or —OC(O)heterocyclyl, —CH$_2$heterocyclyl, wherein the phenyl of —NHC(O)phenyl or —OC(O)NH(C1-C3 alkyl)O(C1-C3 alkyl)phenyl is optionally substituted with —C(O)H or OH and wherein the heterocyclyl of —CH$_2$heterocyclyl is optionally substituted with oxo;

Q is a bond or O;

each $R^7$ is independently halogen, hydroxy, HC(=O)—, C1-C4 alkyl, C1-C4 alkoxy, C1-C4 haloalkyl, C1-C4 hydroxyalkyl, or —N($R^5$)$_2$; and each $R^8$ is independently halogen, cyano, hydroxy, C1-C4 alkyl, —S—C1-C3 alkyl, C2-C4 alkenyl, C2-C4 alkynyl, C2-C4 hydroxyalkynyl, C1-C3 cyanoalkyl, triazolyl, C1-C3 haloalkyl, —O— C1-C3 haloalkyl, —S— C1-C3 haloalkyl, C1-C3 alkoxy, hydroxyC1-C3 alkyl, —CH$_2$C(=O)N($R^5$)$_2$, —C3-C4 alkynyl(N$R^5$)$_2$, —N($R^5$)$_2$, deuteroC2-C4 alkynyl, (C1-C3 alkoxy)haloC1-C3 alkyl-, or C3-C6 cycloalkyl wherein said C3-C6 cycloalkyl is optionally substituted with halogen or C1-C3 alkyl.

In another aspect of the invention, pharmaceutical compositions are provided comprising a therapeutically effective amount of a compound of the present invention or a pharmaceutically acceptable salt thereof and a pharmaceutically acceptable excipient.

In yet another aspect of the invention, methods for inhibiting KRas G12D activity in a in a cell, comprising contacting the cell with a compound of Formula (I), or a pharmaceutically acceptable salt thereof, or a pharmaceutical composition thereof as defined herein. In one embodiment, the contacting is in vitro. In one embodiment, the contacting is in vivo.

Also provided herein is a method of inhibiting cell proliferation, in vitro or in vivo, the method comprising contacting a cell with an effective amount of a compound of Formula (I), or a pharmaceutically acceptable salt thereof, or a pharmaceutical composition thereof as defined herein.

Also provided are methods for treating cancer in a patient comprising administering a therapeutically effective amount of a compound or pharmaceutical composition of the present invention or a pharmaceutically acceptable salt thereof to a patient in need thereof.

Also provided herein is a method of treating a KRas G12D-associated disease or disorder in a patient in need of such treatment, the method comprising administering to the patient a therapeutically effective amount of a compound of Formula (I), or a pharmaceutically acceptable salt thereof, or a pharmaceutical composition thereof as defined herein.

Also provided herein is a compound of Formula (I), or a pharmaceutically acceptable salt thereof, or a pharmaceutical composition thereof as defined herein for use in therapy.

Also provided herein is a compound of Formula (I), or a pharmaceutically acceptable salt thereof or a pharmaceutical composition thereof as defined herein for use in the treatment of cancer.

Also provided herein is a compound of Formula (I), or a pharmaceutically acceptable salt thereof for use in the inhibition of KRas G12D.

Also provided herein is a compound of Formula (I), or a pharmaceutically acceptable salt thereof or a pharmaceutical composition thereof as defined herein, for use in the treatment of a KRas G12D-associated disease or disorder.

Also provided herein is the use of a compound of Formula (I), or a pharmaceutically acceptable salt thereof, as defined herein in the manufacture of a medicament for the treatment of cancer.

Also provided herein is a use of a compound of Formula (I), or a pharmaceutically acceptable salt thereof, as defined herein in the manufacture of a medicament for the inhibition of activity of KRas G12D.

Also provided herein is the use of a compound of Formula (I), or a pharmaceutically acceptable salt thereof, as defined herein, in the manufacture of a medicament for the treatment of a KRas G12D-associated disease or disorder.

Also provided herein is a method for treating cancer in a patient in need thereof, the method comprising (a) determining that the cancer is associated with a KRas G12D mutation (i.e., a KRas G12D-associated cancer); and (b) administering to the patient a therapeutically effective amount of a compound of Formula (I), or a pharmaceutically acceptable salt thereof, or a pharmaceutical composition thereof.

Also provided herein is a process for preparing a compound of Formula (I), or a pharmaceutically acceptable salt thereof.

Also provided herein is a compound of Formula (I), or a pharmaceutically acceptable salt thereof obtained by a process of preparing the compound as defined herein.

DETAILED DESCRIPTION OF THE INVENTION

The present invention relates to inhibitors of KRas G12D. In particular, the present invention relates to compounds that inhibit the activity of KRas G12D, pharmaceutical compositions comprising a therapeutically effective amount of the compounds and methods of use therefor.

Definitions

Unless defined otherwise, all technical and scientific terms used herein have the same meaning as is commonly understood by one of skill in the art to which this invention belongs. All patents, patent applications, and publications referred to herein are incorporated by reference.

As used herein, "KRas G12D" refers to a mutant form of a mammalian KRas protein that contains an amino acid substitution of an aspartic acid for a glycine at amino acid position 12. The assignment of amino acid codon and residue positions for human KRas is based on the amino acid sequence identified by UniProtKB/Swiss-Prot P01116: Variantp.Gly12Asp.

As used herein, a "KRas G12D inhibitor" refers to compounds of the present invention that are represented by Formula (I), as described herein. These compounds are capable of negatively modulating or inhibiting all or a portion of the enzymatic activity of KRas G12D.

A "KRas G12D-associated disease or disorder" as used herein refers to diseases or disorders associated with or mediated by or having a KRas G12D mutation. A non-limiting example of a KRas G12D-associated disease or disorder is a KRas G12D-associated cancer.

As used herein, the term "subject," "individual," or "patient," used interchangeably, refers to any animal, including mammals such as mice, rats, other rodents, rabbits, dogs, cats, swine, cattle, sheep, horses, primates, and humans. In some embodiments, the patient is a human. In some embodiments, the subject has experienced and/or exhibited at least one symptom of the disease or disorder to be treated and/or prevented. In some embodiments, the subject has been identified or diagnosed as having a cancer having a KRas G12D mutation (e.g., as determined using a regulatory agency-approved, e.g., FDA-approved, assay or kit). In some embodiments, the subject has a tumor that is positive for a KRas G12D mutation (e.g., as determined using a regulatory agency-approved assay or kit). The subject can be a subject with a tumor(s) that is positive for a KRas G12D mutation (e.g., identified as positive using a regulatory agency-approved, e.g., FDA-approved, assay or kit). The subject can be a subject whose tumors have a KRas G12D mutation (e.g., where the tumor is identified as such using a regulatory agency-approved, e.g., FDA-approved, kit or assay). In some embodiments, the subject is suspected of having a KRas G12D gene-associated cancer. In some embodiments, the subject has a clinical record indicating that the subject has a tumor that has a KRas G12D mutation (and optionally the clinical record indicates that the subject should be treated with any of the compositions provided herein).

In some embodiments of any of the methods or uses described herein, an assay is used to determine whether the patient has KRas G12D mutation using a sample (e.g., a biological sample or a biopsy sample (e.g., a paraffin-embedded biopsy sample) from a patient (e.g., a patient suspected of having a KRas G12D-associated cancer, a patient having one or more symptoms of a KRas G12D-associated cancer, and/or a patient that has an increased risk of developing a KRas G12D-associated cancer) can include, for example, next generation sequencing, immunohistochemistry, fluorescence microscopy, break apart FISH analysis, Southern blotting, Western blotting, FACS analysis, Northern blotting, and PCR-based amplification (e.g., RT-PCR and quantitative real-time RT-PCR). As is well-known in the art, the assays are typically performed, e.g., with at least one labelled nucleic acid probe or at least one labelled antibody or antigen-binding fragment thereof.

The term "regulatory agency" is a country's agency for the approval of the medical use of pharmaceutical agents with the country. For example, a non-limiting example of a regulatory agency is the U.S. Food and Drug Administration (FDA).

The term "acyl" refers to —C(O)CH$_3$.

The terms "C1-C6 alkyl", "C1-C4 alkyl" and "C1-C3 alkyl" as employed herein refers to straight and branched chain aliphatic groups having from 1-6 carbon atoms, or 1-4 carbon atoms, or 1-3 carbon atoms, respectively. Examples of alkyl groups include, without limitation, methyl, ethyl, propyl, isopropyl, butyl, isobutyl, sec-butyl, tert-butyl, pentyl, and hexyl.

The terms "C1-C3 haloalkyl" and "C1-C4 haloalkyl" refer to a C1-C3 alkyl chain or C1-C4 alkyl chain, respectively, as defined herein in which one or more hydrogen has been replaced by a halogen. Examples include trifluoromethyl, difluoromethyl and fluoromethyl.

An "C1-C4 alkylene," group is a C1-C4 alkyl group, as defined hereinabove, that is positioned between and serves to connect two other chemical groups. Exemplary alkylene groups include, without limitation, methylene, ethylene, propylene, and butylene.

The terms "C1-C3 alkoxy" and "C1-C4 alkoxy" refer to —OC1-C3 alkyl and —OC1-C4 alkyl, respectively, wherein the alkyl portion is as defined herein above.

The term "cycloalkyl" as employed herein includes saturated and partially unsaturated cyclic hydrocarbon groups having 3 to 12 carbons, for example 3 to 8 carbons, and as a further example 3 to 6 carbons, wherein the cycloalkyl group additionally is optionally substituted with one or more R$^6$ groups as defined herein. Examples of cycloalkyl groups include, without limitation, cyclopropyl, cyclobutyl, cyclopentyl, cyclopentenyl, cyclohexyl, cyclohexenyl, cyclohep-tyl, and cyclooctyl. The term "cycloalkyl" also includes bridged cycloalkyls, such as bicyclo[1.1.1]pentanyl.

As used herein, the terms "C1-C3 hydroxyalkyl" and "C1-C4 hydroxyalkyl" refer to —C1-C3 alkylene-OH and —C1-C4 alkylene-OH, respectively.

As used herein, the term "C2-C4 hydroxyalkynyl" refers to —C2-C4 alkynylene-OH.

An "aryl" group is a C$_6$-C$_{14}$ aromatic moiety comprising one to three aromatic rings, which is optionally substituted with one or more R$^6$ or with one or more R$^7$ as defined herein. As one embodiment, the aryl group is a C$_6$-C$_{10}$ aryl group. Examples of aryl groups include, without limitation, phenyl, naphthyl, anthracenyl, fluorenyl, and dihydrobenzofuranyl. "Aryl" also refers to bicyclic or tricyclic ring systems in which one or two rings, respectively, of said aryl ring system may be saturated or partially saturated, and wherein if said ring system includes two saturated rings, said saturated rings may be fused or spirocyclic. An example of an aryl ring system comprising two saturated rings wherein the rings are spirocyclic includes the following ring system:

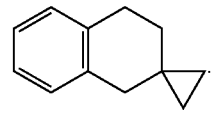 [SMILES: c1ccc2c(c1)CCC1(CC1)C2]

An "araC1-C6 alkyl" or "arylalkyl" group comprises an aryl group covalently linked to an alkyl group, either of which may independently be optionally substituted or unsubstituted. An example of an aralkyl group is (C$_6$-C$_{10}$)aryl(C$_1$-C$_6$)alkyl-, including, without limitation, benzyl, phenethyl, and naphthylmethyl. An example of a substituted araC1-C6 alkyl is wherein the alkyl group is substituted with hydroxyalkyl.

A "heterocyclyl" or "heterocyclic" group is a ring structure having from 3 to 12 atoms, for example 4 to 8 atoms, wherein one or more atoms are selected from the group consisting of N, O, and S wherein the ring N atom may be oxidized to N—O, and the ring S atom may be oxidized to SO or SO$_2$, the remainder of the ring atoms being carbon. The heterocyclyl may be a monocyclic, a bicyclic, a spirocyclic or a bridged ring system. The heterocyclic group is optionally substituted with one or more R$^6$ on ring carbon or ring nitrogen at one or more positions, wherein R$^6$ is as defined for Formula I. The heterocyclic group is also independently optionally substituted on a ring nitrogen atom with alkyl, aralkyl, alkylcarbonyl, or on sulfur with lower alkyl. Examples of heterocyclic groups include, without limitation, epoxy, azetidinyl, aziridinyl, tetrahydrofuranyl, tetrahydropyranyl, pyrrolidinyl, pyrrolidinonyl, piperidinyl, piperazinyl, imidazolidinyl, imidazopyridinyl, thiazolidinyl, dithianyl, trithianyl, dioxolanyl, oxazolidinyl, oxazolidinonyl, decahydroquinolinyl, piperidonyl, 4-piperidinonyl, quinuclidinyl, thiomorpholinyl, thiomorpholinyl 1,1 dioxide, morpholinyl, azepanyl, oxazepanyl, azabicyclohexanyls, azabicycloheptanyl, azabicyclooctanyls, azabicyclononanyls (e.g., octahydroindolizinyl), azaspiroheptanyls, dihydro-1H,3H,5H-oxazolo[3,4-c]oxazolyl, tetrahydro-1'H, 3'H-spiro[cyclopropane-1,2'-pyrrolizine], hexahydro-1H-pyrrolizinyl, hexahydro-1H-pyrrolo[2,1-c][1,4]oxazinyl, octahydroindolizinyl, oxaazaspirononanyls, oxaazaspirooctanyls, diazaspirononanyls, oxaazabiocycloheptanyls, hexahydropyrrolizinyl 4 (1H)-oxide, tetrahydro-2H-thiopyranyl 1-oxide and tetrahydro-2H-thiopyranyl 1,1-dioxide. Specifically excluded from the scope of this term are compounds having adjacent annular O and/or S atoms.

As used herein, the term "heteroaryl" refers to groups having 5 to 14 ring atoms, preferably 5, 6, 9, or 10 ring atoms; having 6, 10, or 14 π electrons shared in a cyclic array; and having, in addition to carbon atoms, from one to three heteroatoms per ring selected from the group consisting of N, O, and S. Examples of heteroaryl groups include acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, 6,7-dihydro-5H-pyrrolo[1,2-a]imidazole, furanyl, furazanyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolinyl, 2H-pyrrolyl, pyrrolyl, quinazolinyl, quinolinyl, 4H-quinolizinyl, quinoxalinyl, quinuclidinyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. "Heteroaryl" also refers to bicyclic ring systems having, in addition to carbon atoms, from one to three heteroatoms per ring selected from the group consisting of N, O, and S in which one ring system may be saturated or partially saturated.

As used herein, "an effective amount" of a compound is an amount that is sufficient to negatively modulate or inhibit the activity of KRas G12D. Such amount may be administered as a single dosage or may be administered according to a regimen, whereby it is effective.

As used herein, a "therapeutically effective amount" of a compound is an amount that is sufficient to ameliorate, or in some manner reduce a symptom or stop or reverse progression of a condition, or negatively modulate or inhibit the activity of KRas G12D. Such amount may be administered as a single dosage or may be administered according to a regimen, whereby it is effective.

As used herein, treatment means any manner in which the symptoms or pathology of a condition, disorder or disease are ameliorated or otherwise beneficially altered. Treatment also encompasses any pharmaceutical use of the compositions herein.

As used herein, amelioration of the symptoms of a particular disorder by administration of a particular pharmaceutical composition refers to any lessening, whether permanent or temporary, lasting or transient that can be attributed to or associated with administration of the composition.

Compounds

In one aspect of the invention, compounds are provided represented by Formula (I):

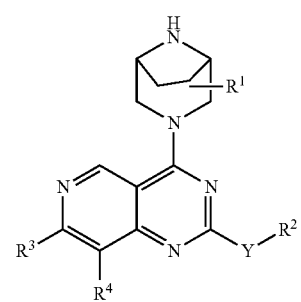

Formula (I)

or a pharmaceutically acceptable salt thereof:
wherein:
$R^1$ is hydrogen, hydroxy, halogen, C1-C3 alkyl, C1-C3 cyanoalkyl, C1-C3 hydroxyalkyl, HC(=O)—, —CO$_2$R$^5$, —CO$_2$N(R$^5$)$_2$ or a 5-6 membered heteroaryl;

Y is a bond, O or NR$^5$;

$R^2$ is hydrogen, —N(R$^5$)$_2$, heterocyclyl, C1-C6 alkyl, -L-heterocyclyl, -L-aryl, -L-heteroaryl, -L-cycloalkyl, -L-N(R$^5$)$_2$, -L-NHC(=NH)NH$_2$, -L-C(O)N(R$^5$)$_2$, -L-C1-C6 haloalkyl, -L-OR$^5$, -L-(CH$_2$OR$^5$)(CH$_2$)$_n$OR$^5$, -L-NR$^5$C(O)-aryl, -L-COOH, or -LC(=O)OC1-C6 alkyl, wherein the heterocyclyl and the aryl portion of -L-NR$^5$C(O)-aryl and the heterocyclyl portion of -L-heterocyclyl and the cycloalkyl portion of the -L-cycloalkyl may be optionally substituted with one or more R$^6$, and wherein the aryl or heteroaryl of the -L-aryl and the -L-heteroaryl may be optionally substituted with one or more R$^7$;

each L is independently a C1-C4 alkylene optionally substituted with hydroxy, C1-C4 hydroxyalkyl or heteroaryl;

$R^3$ is aryl or heteroaryl, wherein the aryl or the heteroaryl is optionally substituted with one or more R$^8$;

$R^4$ is hydrogen, halogen or C1-C3 alkyl;

each R$^5$ is independently hydrogen or C1-C3 alkyl;

each R$^6$ is independently halogen, hydroxy, C1-C3 hydroxyalkyl, C1-C3 alkyl, C1-C3 haloalkyl, C1-C3 alkoxy, cyano, -Q-phenyl, -Q-phenylSO$_2$F, —NHC(O)phenyl, —NHC(O)phenylSO$_2$F, C1-C3 alkyl substituted pyrazolyl, araC1-C3 alkyl-, tert-butyldimethylsilyloxyCH$_2$-, —N(R$^5$)$_2$, (C1-C3 alkoxy)C1-C3 alkyl-, (C1-C3 alkyl)C(=O), oxo, (C1-C3 haloalkyl)C(=O)—, —SO$_2$F, (C1-C3 alkoxy)C1-C3 alkoxy, —CH$_2$OC(O)N(R$^5$)$_2$, —CH$_2$NHC(O)OC1-C6 alkyl, —CH$_2$NHC(O)N(R$^5$)$_2$, —CH$_2$NHC(O)C1-C6 alkyl, —CH$_2$(pyrazolyl), —CH$_2$NHSO$_2$C1-C6 alkyl, —CH$_2$OC(O)heterocyclyl, —OC(O)N(R$^5$)$_2$, —OC(O)NH(C1-C3 alkyl)O(C1-C3 alkyl), —OC(O)NH(C1-C3 alkyl)O(C1-C3 alkyl)phenyl(C1-C3 alkyl)N(CH$_3$)$_2$, —OC(O)NH(C1-C3 alkyl)O(C1-C3 alkyl)phenyl or —OC(O)heterocyclyl, —CH$_2$heterocyclyl, wherein the phenyl of —NHC(O)phenyl or —OC(O)NH(C1-C3 alkyl)O(C1-C3 alkyl)phenyl is optionally substituted with —C(O)H or OH and wherein the heterocyclyl of —CH$_2$heterocyclyl is optionally substituted with oxo;
Q is a bond or O;
each R$^7$ is independently halogen, hydroxy, HC(=O)—, C1-C4 alkyl, C1-C4 alkoxy, C1-C4 haloalkyl, C1-C4 hydroxyalkyl, or —N(R$^5$)$_2$; and
each R$^8$ is independently halogen, cyano, hydroxy, C1-C4 alkyl, —S—C1-C3 alkyl, C2-C4 alkenyl, C2-C4 alkynyl, C2-C4 hydroxyalkynyl, C1-C3 cyanoalkyl, triazolyl, C1-C3 haloalkyl, —O— C1-C3 haloalkyl, —S— C1-C3 haloalkyl, C1-C3 alkoxy, hydroxyC1-C3 alkyl, —CH$_2$C(=O)N(R$^5$)$_2$, —C3-C4 alkynyl(NR$^5$)$_2$, —N(R$^5$)$_2$, deuteroC2-C4 alkynyl, (C1-C3 alkoxy)haloC1-C3 alkyl-, or C3-C6 cycloalkyl wherein said C3-C6 cycloalkyl is optionally substituted with halogen or C1-C3 alkyl.

In one embodiment of the compounds of Formula (I), R$^1$ is halogen, hydroxy, C1-C3 alkyl, C1-C3 cyanoalkyl, C1-C3 hydroxyalkyl, HC(=O)—, —CO$_2$R$^5$, or —CO$_2$N(R$^5$)$_2$.

In certain embodiments, R$^1$ is hydrogen.

In certain embodiments, R$^1$ is hydroxy.

In other embodiments, R$^1$ is —CO$_2$R$^5$. In certain embodiments, R$^5$ is hydrogen. In other embodiments, R$^5$ is C1-C3 alkyl.

In another embodiment, R$^1$ is —C(O)$_2$N(R$^5$)$_2$. In certain embodiments, each R$^5$ is hydrogen, each R$^5$ is an independently selected C1-C3 alkyl, or one R$^5$ is hydrogen and the second R$^5$ is C1-C3 alkyl.

In one embodiment, Y is a bond.

In one embodiment of the compounds of Formula (I), Y is a bond and R$^2$ is hydrogen, —N(R$^5$)$_2$, or heterocyclyl optionally substituted with one or more R$^6$.

In certain embodiments, R$^2$ is —N(R$^5$)$_2$. In one embodiment, each R$^5$ is hydrogen. In one embodiment, each R$^5$ is an independently selected C1-C3 alkyl. In one embodiment, one R$^5$ is hydrogen and the second R$^5$ is C1-C3 alkyl. In certain embodiments, Y is a bond and R$^2$ is —N(R$^5$)$_2$.

In other embodiments, R$^2$ is heterocyclyl. In one embodiment R$^2$ is heterocyclyl and the heterocyclyl is azetidinyl, pyrrolidinyl, tetrahydro-2H-thiopyran 1,1-dioxide or 1,6λk$^2$-diazaspiro[3.3]heptanyl. In certain embodiments, Y is a bond and R$^2$ is heterocyclyl.

In certain embodiments, the heterocyclyl is azetidinyl substituted with one R$^6$. In certain embodiments, the heterocyclyl is azetidinyl substituted with one R$^6$, wherein R$^6$ is hydroxy, hydroxyalkyl, or —N(R$^5$)$_2$. In certain embodiments, the heterocyclyl is azetidinyl substituted with two R$^6$ groups independently selected from —N(R$^5$)$_2$ and C1-C3 alkyl. In certain embodiments, Y is a bond and the heterocyclyl is azetidinyl substituted with one R$^6$, wherein R$^6$ is hydroxy, hydroxyalkyl, or —N(R$^5$)$_2$. In certain embodiments, Y is a bond and the heterocyclyl is azetidinyl substituted with two R$^6$ groups independently selected from —N(R$^5$)$_2$ and C1-C3 alkyl.

In one embodiment, Y is O.

In one embodiment, Y is O and R$^2$ is C1-C6 alkyl, -L-heterocyclyl optionally substituted with one or more R$^6$, -L-heteroaryl, wherein the heteroaryl portion is optionally substituted with one or more R$^7$, -L-aryl, wherein the aryl portion is optionally substituted with one or more R$^7$, -L-cycloalkyl, wherein the cycloalkyl portion is optionally substituted with one or more R$^6$, -L-N(R$^5$)$_2$, -L-NC(=NH)—NH$_2$, -L-C(O)N(R$^5$)$_2$, -L-C1-C6 haloalkyl, -L-COR$^5$, -L-(CH$_2$OR$^5$)(CH$_2$)$_n$OR$^5$, -L-NR$^5$C(O)-aryl.

In one embodiment of the compounds of Formula (I), Y is O and R$^2$ is C1-C6 alkyl. In certain embodiments, the C1-C6 alkyl is methyl, ethyl, isopropyl or isobutyl.

In one embodiment of the compounds of Formula (I), Y is O and R$^2$ is -L-heterocyclyl optionally substituted with one or more R$^6$.

In one embodiment, Y is O and R$^2$ is heterocyclyl wherein the heterocyclyl is tetrahydropyranyl optionally substituted with two halogens. In certain embodiment, the two halogens are both fluoro.

In another embodiment, Y is O and R$^2$ is -L-heterocyclyl wherein L is methylene and the heterocyclyl is hexahydro-1H-pyrrolizinyl, hexahydro-3H-pyrrolizin-3-one, hexahydro-1H-pyrrolo[2,1-c][1,4]oxazinyl, octahydroindolizinyl, hexahydropyrrolizine 4 (1H)-oxide, azetidinyl, pyrrolidinyl, pyrrolidin-2-one, oxetanyl, piperidinyl, 1-azabicyclo[2.2.1]heptanyl, morpholinyl, oxa-5-azabicyclo[2.2.1]heptan-5-yl, thiopyranyl, 6-oxa-2x$^2$-azaspiro[3.4]octanyl, 7-oxa-2x$^2$-azaspiro[3.5]nonanyl, 2',3'-dihydrospiro[cyclopropane-1,1'-indenyl], (2S)-1-azabicyclo[2.2.1]heptan-2-yl or tetrahydrofuranyl.

In certain embodiments, Y is O and R$^2$ is -L-heterocyclyl wherein L is methylene and the heterocyclyl is hexahydro-1H-pyrrolizinyl.

In certain embodiments, Y is O and R$^2$ is -L-heterocyclyl wherein L is methylene and the heterocyclyl is hexahydro-1H-pyrrolizinyl is optionally substituted with one R$^6$, wherein R$^6$ is halogen, hydroxy, hydroxyalkyl, C1-C3 haloalkyl, C1-C3 alkyl, C1-C3 alkoxy, phenyl, tert-butyldimethylsilyloxyCH$_2$— or pyrazolyl, wherein the pyrazolyl is optionally substituted with C1-C3 alkyl. In one embodiment, the C1-C3 haloalkyl is chloromethyl. In another embodiment, the pyrazolyl is substituted with C1-C3 alkyl. In other embodiments, the hexahydro-1H-pyrrolizinyl is substituted with two R$^6$ groups, wherein each R$^6$ is an independently selected C1-C3 alkyl. In certain embodiments, the heterocyclyl is hexahydro-1H-pyrrolizinyl which is unsubstituted.

In certain embodiments, Y is O and R$^2$ is -L-heterocyclyl wherein L is methylene and the heterocyclyl is azetidinyl substituted with one R$^6$, wherein R$^6$ is C1-C3 alkyl.

In certain embodiments, Y is O and R$^2$ is -L-heterocyclyl wherein L is methylene and the heterocyclyl is pyrrolidinyl substituted with one R$^6$, wherein R$^6$ is C1-C3 hydroxyalkyl, C1-C3 haloalkyl, C1-C3 alkyl, C1-C3 alkoxy, C1-C3 aralkyl, or -Q-phenyl, wherein Q is O, and —NHC(O)phenyl. In one embodiment, the phenyl group of the -Q-phenyl is substituted with SO$_2$F.

In another embodiment, the phenyl group of the —NHC(O)phenyl is substituted with SO$_2$F. In one embodiment, the C1-C3 aralkyl is benzyl.

In other embodiments, Y is O and R$^2$ is -L-heterocyclyl wherein L is methylene and the pyrrolidinyl is substituted with two R$^6$ groups, wherein one R$^6$ is C1-C3 alkyl and the other R$^6$ is C1-C3 alkoxy or halogen.

In certain embodiments, Y is O and R$^2$ is -L-heterocyclyl wherein L is methylene and the heterocyclyl is pyrrolidin-2-one substituted with one R$^6$, wherein R$^6$ is C1-C3 alkyl.

In certain embodiments, Y is O and R$^2$ is -L-heterocyclyl wherein L is methylene and the heterocyclyl is piperidinyl substituted with one R$^6$, wherein R$^6$ is acetyl, (C1-C3 alkoxy)C1-C3 alkoxy, or —C(O)CH$_2$Cl.

In certain embodiments, Y is O and R$^2$ is -L-heterocyclyl wherein L is methylene and the heterocyclyl is (2S)-1-azabicyclo[2.2.1]heptan-2-yl.

In one embodiment of the compounds of Formula (I), Y is O, R$^2$ is -L-heterocyclyl wherein L is ethylene or propylene and the heterocyclyl is morpholinyl or oxa-5-azabicyclo[2.2.1]heptan-5-yl.

In one embodiment of the compounds of Formula (I), Y is O and $R^2$ is -L-heteroaryl, wherein the heteroaryl portion is optionally substituted with one or more $R^7$. In certain embodiments, L is ethylene and the heteroaryl is benzimidazolyl, optionally substituted with one or more $R^7$. In one embodiment, $R^7$ is C1-C4 alkyl.

In certain embodiments, Y is O and $R^2$ is -L-heteroaryl.

In certain embodiments, Y is O and $R^2$ is -L-heteroaryl, wherein L is methylene or ethylene.

In certain embodiments, Y is O and $R^2$ is -L-heteroaryl, wherein L is methylene or ethylene and the heteroaryl is pyridyl, pyrazolyl, imidazolyl, triazolyl, 4,5,6,7-tetrahydro-1H-indazolyl, benzimidazolyl, imidazo[1,2-a]pyridinyl, or pyrimidinyl.

In certain embodiments, Y is O and $R^2$ is -L-heteroaryl, wherein the heteroaryl is pyridyl substituted with one $R^7$. In certain embodiments, Y is O and $R^2$ is -L-heteroaryl, wherein the heteroaryl is pyridyl substituted with one $R^7$ wherein $R^7$ is halogen, C1-C4 haloalkyl, C1-C4 hydroxyalkyl, C1-C4 alkyl, —N($R^5$)$_2$, or C1-C4 alkoxy.

In certain embodiments, Y is O and $R^2$ is -L-heteroaryl, wherein L is methylene or ethylene and the heteroaryl is pyrazolyl substituted with one $R^7$. In certain embodiments, Y is O and $R^2$ is -L-heteroaryl, wherein L is methylene or ethylene and the heteroaryl is pyrazolyl substituted with one $R^7$ wherein $R^7$ is halogen, C1-C4 haloalkyl, C1-C4 hydroxyalkyl, C1-C4 alkyl, alkoxy or —N($R^5$)$_2$.

In certain embodiments, Y is O and $R^2$ is -L-heteroaryl, wherein L is methylene or ethylene and the heteroaryl is imidazolyl substituted with one $R^7$. In certain embodiments, Y is O and $R^2$ is -L-heteroaryl, wherein L is methylene or ethylene and the heteroaryl is imidazolyl substituted with one $R^7$ wherein $R^7$ is C1-C4 alkyl, C1-C4 haloalkyl, or C1-C4 hydroxyalkyl.

In certain embodiments, Y is O and $R^2$ is -L-heteroaryl, wherein L is methylene or ethylene and the heteroaryl is triazolyl substituted with one $R^7$. In certain embodiments, Y is O and $R^2$ is -L-heteroaryl, wherein L is methylene or ethylene and the heteroaryl is triazolyl substituted with one $R^7$, wherein $R^7$ is C1-C4 alkyl.

In one embodiment of the compounds of Formula (I), Y is O and $R^2$ is -L-aryl, wherein the aryl portion is optionally substituted with one or more $R^7$. In certain embodiments, L is ethylene and the aryl is phenyl. In one embodiment, the phenyl is substituted with one $R^7$. In one embodiment, the phenyl is substituted with one $R^7$, wherein $R^7$ is halogen. In one embodiment, the phenyl is substituted with two $R^7$ groups. In one embodiment, the phenyl is substituted with two $R^7$ groups. In one embodiment, the phenyl is substituted with two $R^7$ groups wherein one $R^7$ is hydroxy and one $R^7$ is HC(=O)—.

In one embodiment of the compounds of Formula (I), Y is O and $R^2$ is -L-cycloalkyl, wherein the cycloalkyl portion is optionally substituted with one or more $R^6$. In one embodiment, L is methylene. In one embodiment, the cycloalkyl is cyclopropyl, cyclobutyl, cyclopentyl or cyclohexyl. In certain embodiments, the cyclopropyl and cyclopentyl are each substituted with one $R^6$. In certain embodiments, the cyclopropyl and cyclopentyl are each substituted with one $R^6$, wherein $R^6$ is haloalkyl. In certain embodiments, the cyclobutyl and cyclohexyl are each substituted with two $R^6$ groups. In certain embodiments, the cyclobutyl and cyclohexyl are each substituted with two $R^6$ groups, wherein each $R^6$ group is halogen.

In one embodiment of the compounds of Formula (I), Y is O, and $R^2$ is -L-N($R^5$)$_2$. In certain embodiments, L is ethylene. In certain embodiments, $R^5$ is C1-C3 alkyl.

In one embodiment of the compounds of Formula (I), Y is O, and $R^2$ is -L-NC(=NH)—NH$_2$. In certain embodiments, L is ethylene or propylene.

In one embodiment of the compounds of Formula (I), Y is O, and $R^2$ is -L-C(O)N($R^5$)$_2$. In certain embodiments, L is ethylene and each $R^5$ is C1-C3 alkyl.

In one embodiment of the compounds of Formula (I), Y is O, and $R^2$ is -L-C1-C6 haloalkyl. In certain embodiments, L is methylene. In certain embodiments, the haloalkyl is 1,1,3,3-tetrafluoropropanyl or trifluoromethyl. In other embodiments, L is ethylene or propylene and the haloalkyl is trifluoromethyl.

In one embodiment of the compounds of Formula (I), Y is O, and $R^2$ is -L-COR$^5$. In certain embodiments, L is propylene and $R^5$ is hydrogen or C1-C3 alkyl. In certain embodiments, L is propylene that is substituted with hydroxy, hydroxyalkyl or heteroaryl and $R^5$ is hydrogen or C1-C3 alkyl. In one embodiment, the heteroaryl is pyridyl.

In one embodiment of the compounds of Formula (I), Y is O, and $R^2$ is -L-(CH$_2$OR$^5$)(CH$_2$)$_n$OR$^5$. In certain embodiments, L is methylene, each $R^5$ is independently hydrogen or C1-C3 alkyl, and n is one or two.

In one embodiment of the compounds of Formula (I), Y is O, and $R^2$ is -L-NR$^5$C(O)-aryl. In certain embodiments, L is methylene, $R^5$ is hydrogen. In one embodiment the aryl is phenyl. In one embodiment, the phenyl is substituted with one $R^6$, wherein $R^6$ is —SO$_2$F.

In one embodiment of the compounds of Formula (I), $R^3$ is aryl optionally substituted with one or more $R^8$. In certain embodiments, the aryl is selected from the group consisting of phenyl, naphthyl, 1,2,3,4-tetrahydronaphthalenyl and 2,3-dihydro-1H-indenyl, wherein each is optionally substituted with one or more $R^8$.

In one embodiment, the aryl is phenyl substituted with one or more $R^8$ groups. In one embodiment, the aryl is phenyl substituted with one or more $R^8$ groups independently selected from halogen, C1-C3 haloalkyl and —O—C1-C3 haloalkyl. In certain embodiments the phenyl is substituted with two $R^8$ groups. In certain embodiments the phenyl is substituted with two $R^8$ groups, wherein the two $R^8$ groups are two independently selected C1-C3 haloalkyl groups, or —O—C1-C3 haloalkyl and halogen.

In one embodiment, the aryl is 2,3-dihydro-1H-indenyl optionally substituted with one or more $R^8$. In one embodiment, the aryl is 2,3-dihydro-1H-indenyl optionally substituted with one $R^8$. In one embodiment, $R^8$ is C1-C alkyl.

In one embodiment, the aryl is naphthyl substituted with one or more $R^8$ groups. In one embodiment, the aryl is naphthyl substituted with one or more $R^8$ groups independently selected from halogen, cyano, hydroxy, C1-C3 alkyl, —S-C1-C3 alkyl, C2-C4 alkenyl, C2-C4 alkynyl, C2-C4 hydroxyalkynyl, C1-C3 cyanoalkyl, triazolyl, C1-C3 haloalkyl and —O—C1-C3 haloalkyl.

In one embodiment, the aryl is naphthyl substituted with hydroxy. In one embodiment, the aryl is naphthyl substituted with halogen. In certain embodiments, the halogen is chlorine, fluorine or bromine. In other embodiments, the halogen is chlorine.

In one embodiment, the aryl is naphthyl substituted with C1-C3 alkyl, wherein the C1-C3 alkyl is methyl or ethyl.

In one embodiment, the aryl is naphthyl substituted with C2-C4 alkenyl. In certain embodiments, the C2-C4 alkenyl is prop-2-enyl.

In one embodiment, the aryl is naphthyl substituted with C2-C4 alkynyl. In certain embodiments, the C2-C4 alkynyl is ethyne or prop-2-ynyl.

In one embodiment, the aryl is naphthyl substituted with one or two $R^8$, wherein each $R^8$ is halogen, cyano, hydroxy, C1-C3 alkyl, —S—C1-C3 alkyl, C2-C4 alkenyl, C2-C4 alkynyl, C2-C4 hydroxyalkynyl, C1-C3 cyanoalkyl, or triazolyl. In one embodiment, the aryl is naphthyl substituted with two $R^8$ groups independently selected from halogen, hydroxy, C1-C3 alkyl and C2-C4 alkynyl.

In one embodiment of the compounds of Formula (I), $R^3$ is heteroaryl optionally substituted with one or more $R^8$. In one embodiment, the heteroaryl is isoquinolinyl, indazolyl, or benzo[d][1,3]dioxolyl optionally substituted with one or more $R^8$. In one embodiment, the heteroaryl is indazolyl optionally substituted with one or more $R^8$. In one embodiment, the heteroaryl is indazolyl optionally substituted with C1-C3 alkyl. In other embodiments, the heteroaryl is isoquinolinyl optionally substituted with one or more $R^8$. In other embodiments, the heteroaryl is isoquinolinyl optionally substituted with halogen or C2-C4 alkynyl. In certain embodiments, the heteroaryl is benzo[d][1,3]dioxolyl optionally substituted with two $R^8$ groups. In certain embodiments, the heteroaryl is benzo[d][1,3]dioxolyl optionally substituted with two $R^8$ groups, wherein each $R^8$ group is an independently selected halogen. In one embodiment, the two halogens are gem-difluoro substitutions.

In one embodiment of the compounds of Formula (I), $R^4$ is hydrogen.

In one embodiment of the compounds of Formula (I), $R^4$ is halogen. In one embodiment, $R^4$ is fluorine. In one embodiment, $R^4$ is chlorine.

In one embodiment of the compounds of Formula (I), $R^4$ is C1-C3 alkyl. In one embodiment, $R^4$ is methyl.

Nonlimiting examples of compounds of Formula (I) are selected from the group consisting of:

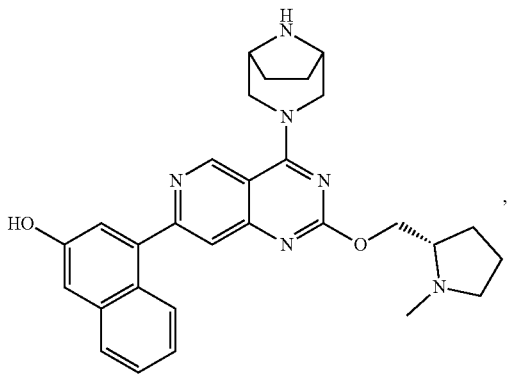

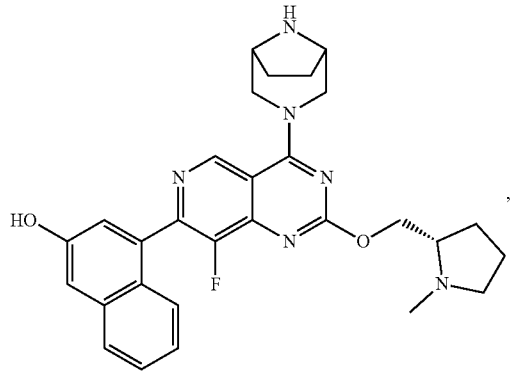

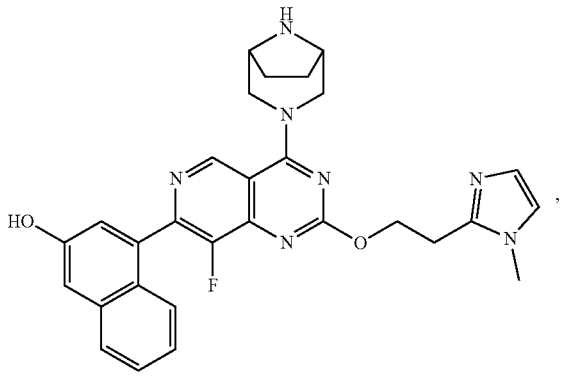

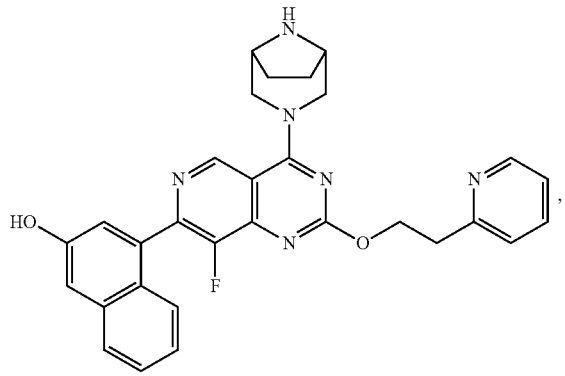

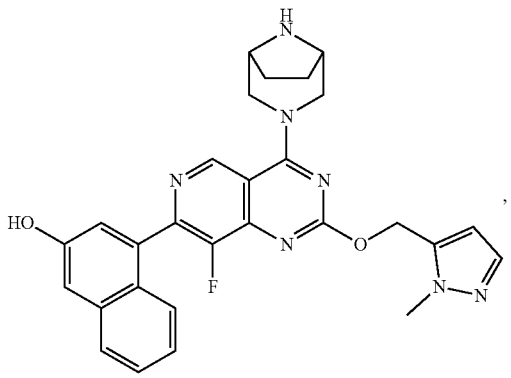

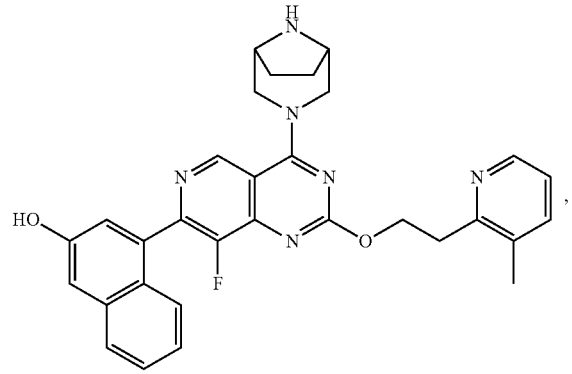

15
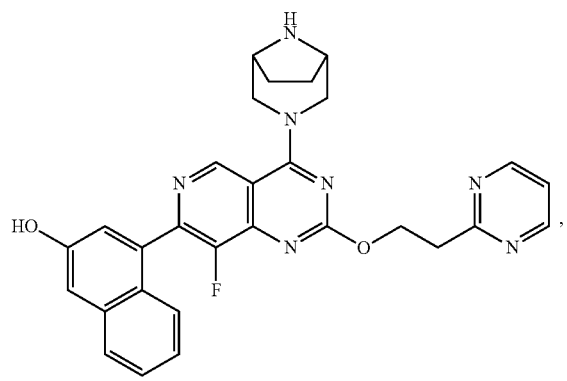
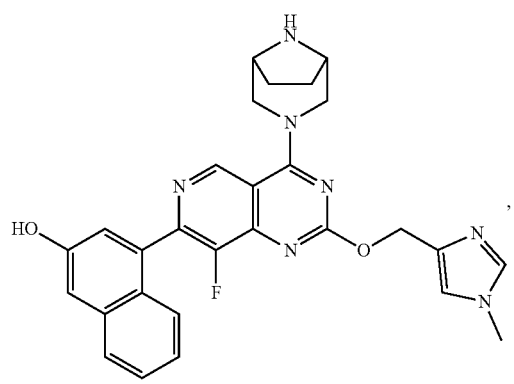
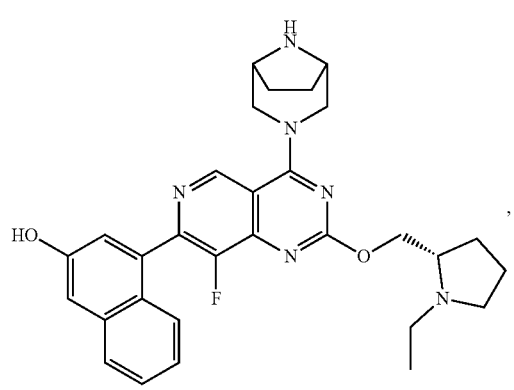
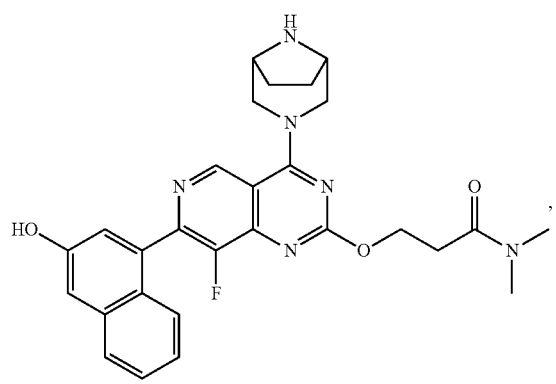
16
-continued
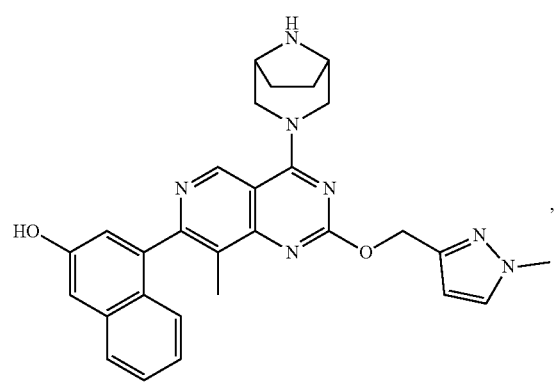
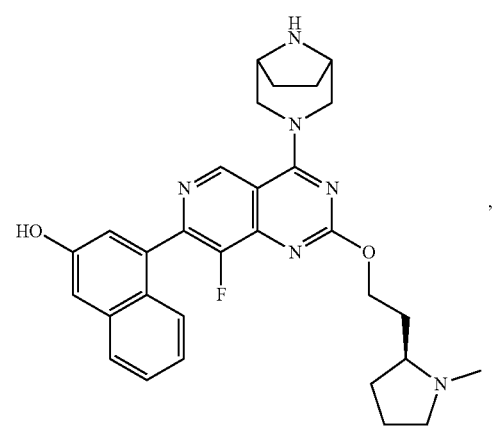
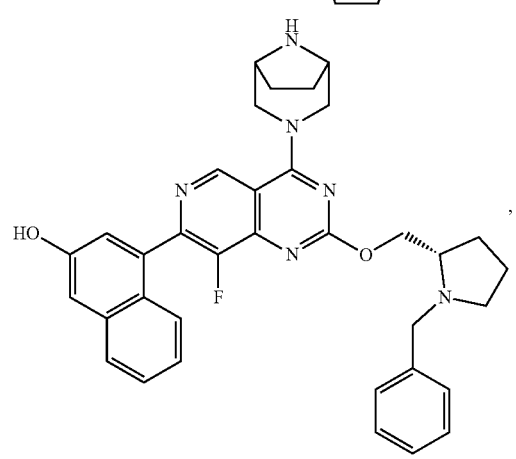
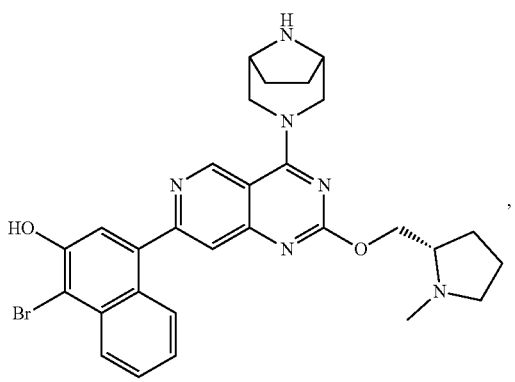

-continued
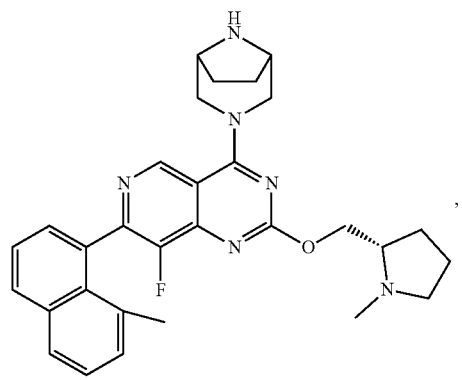
,
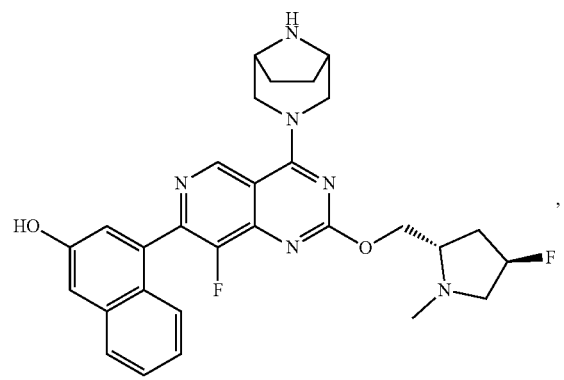
,
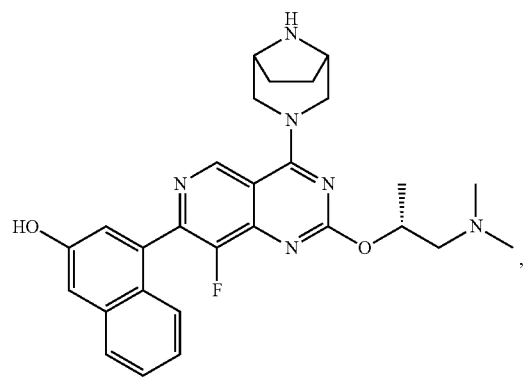
,
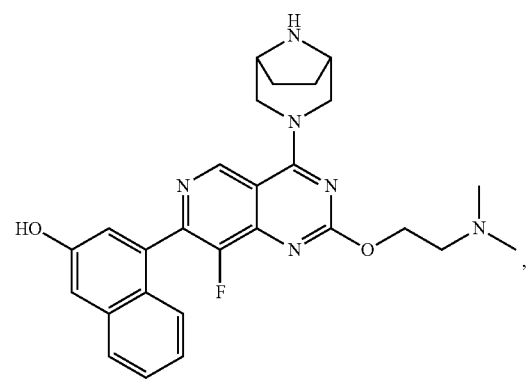
,
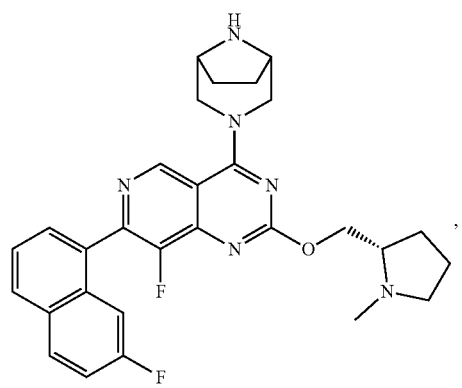
,
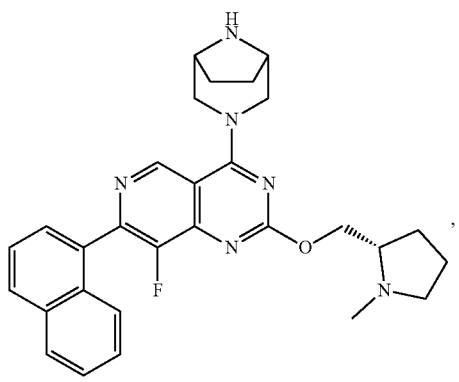
,
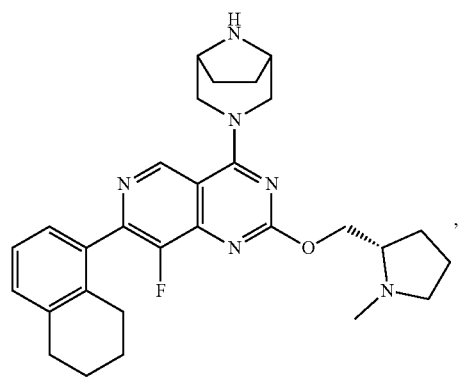
,
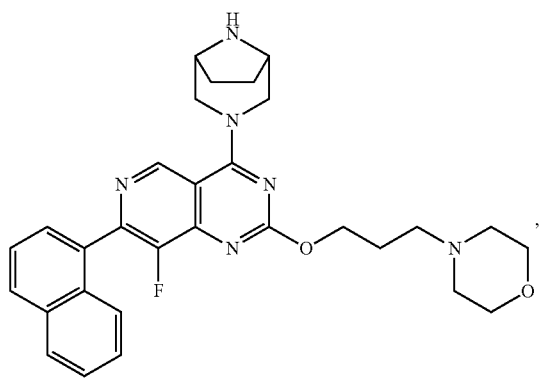
, -continued
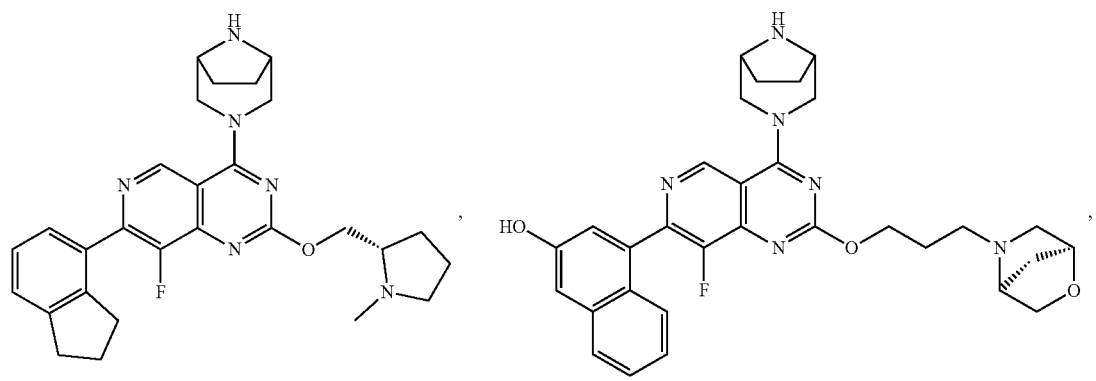
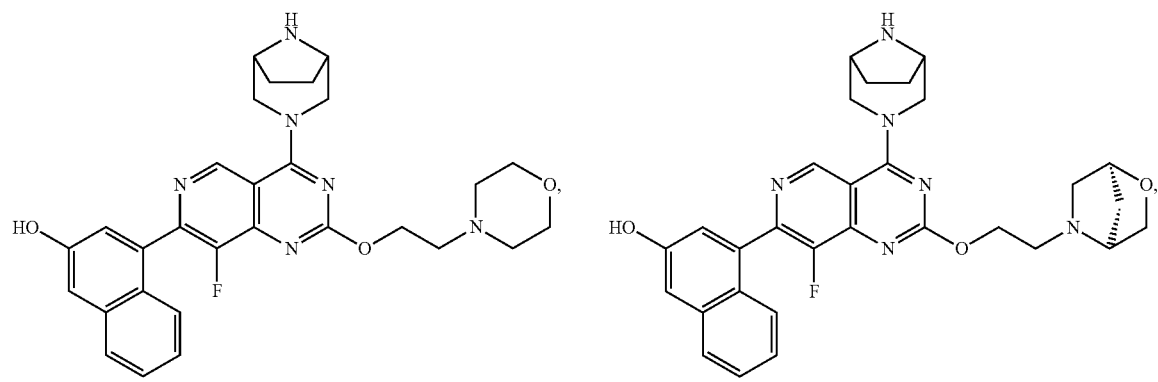
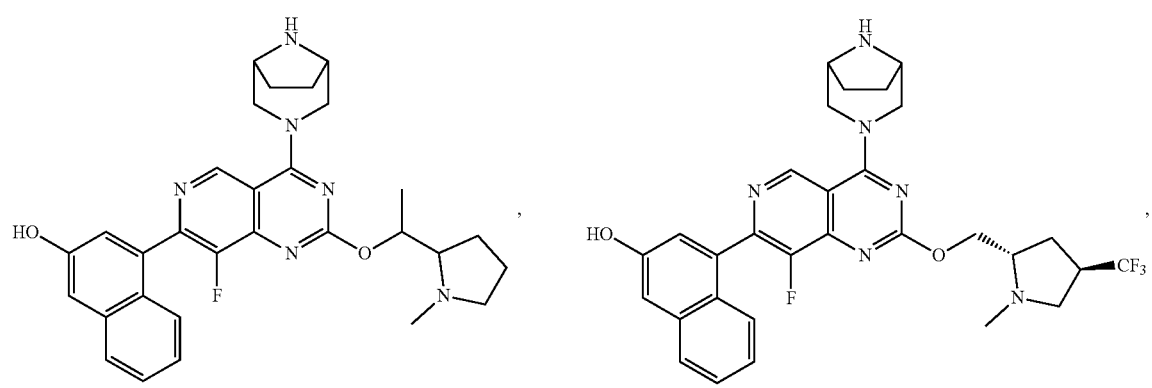
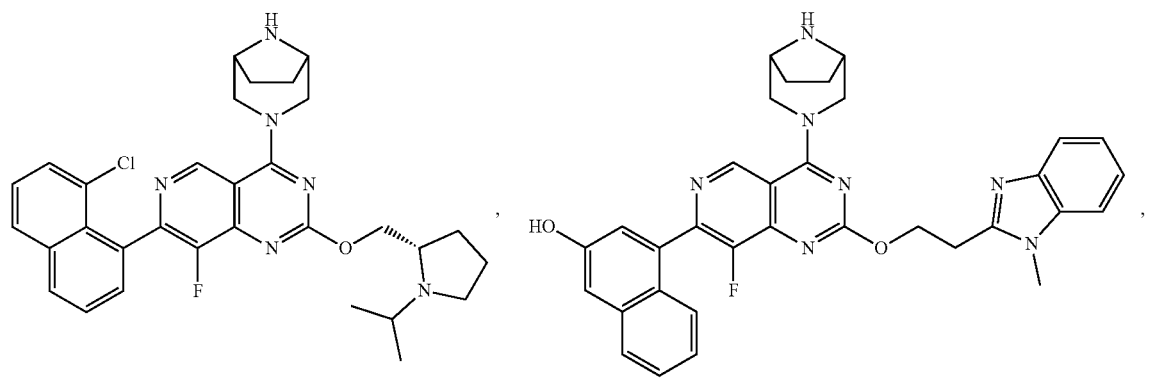

-continued
21
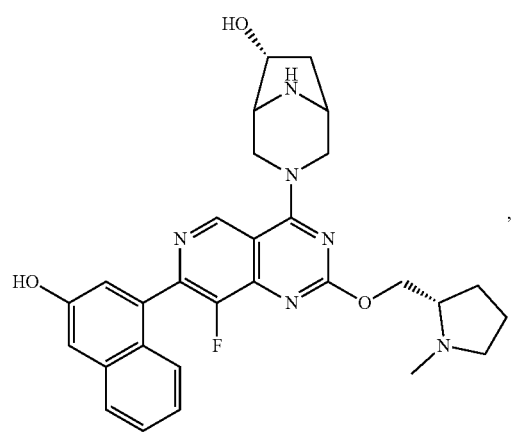
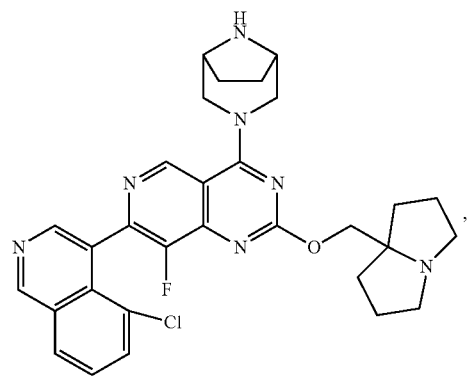
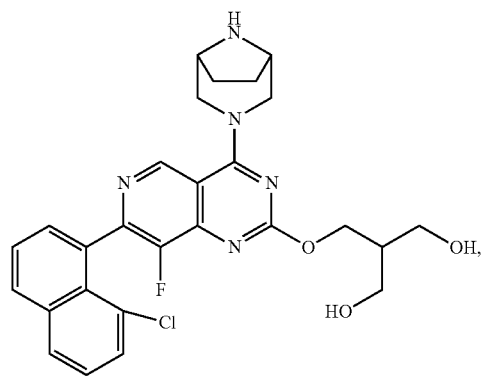
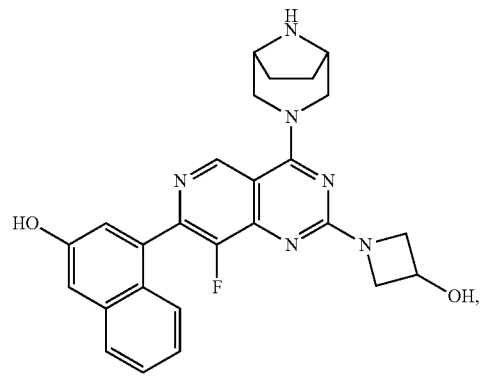
22
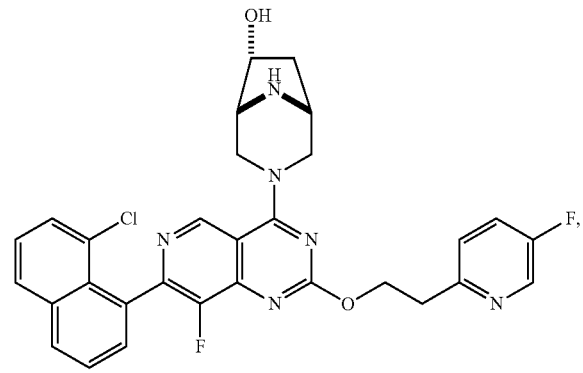
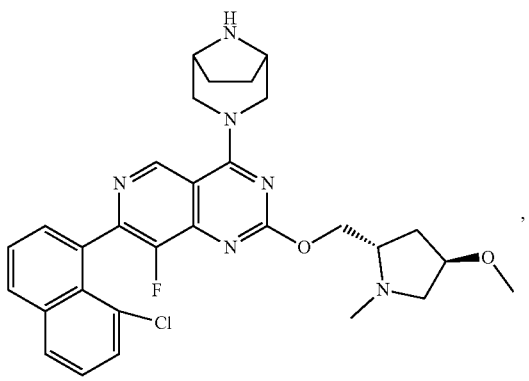
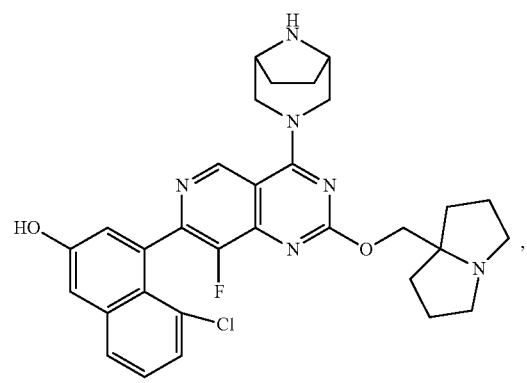
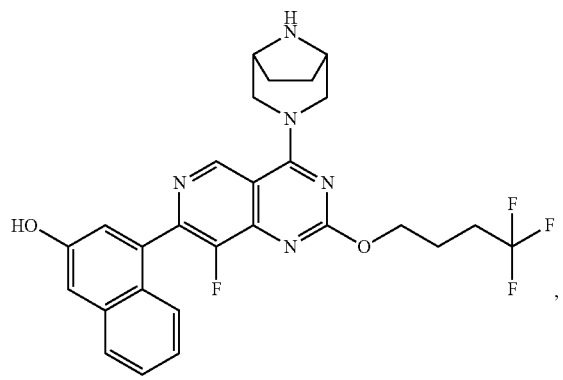

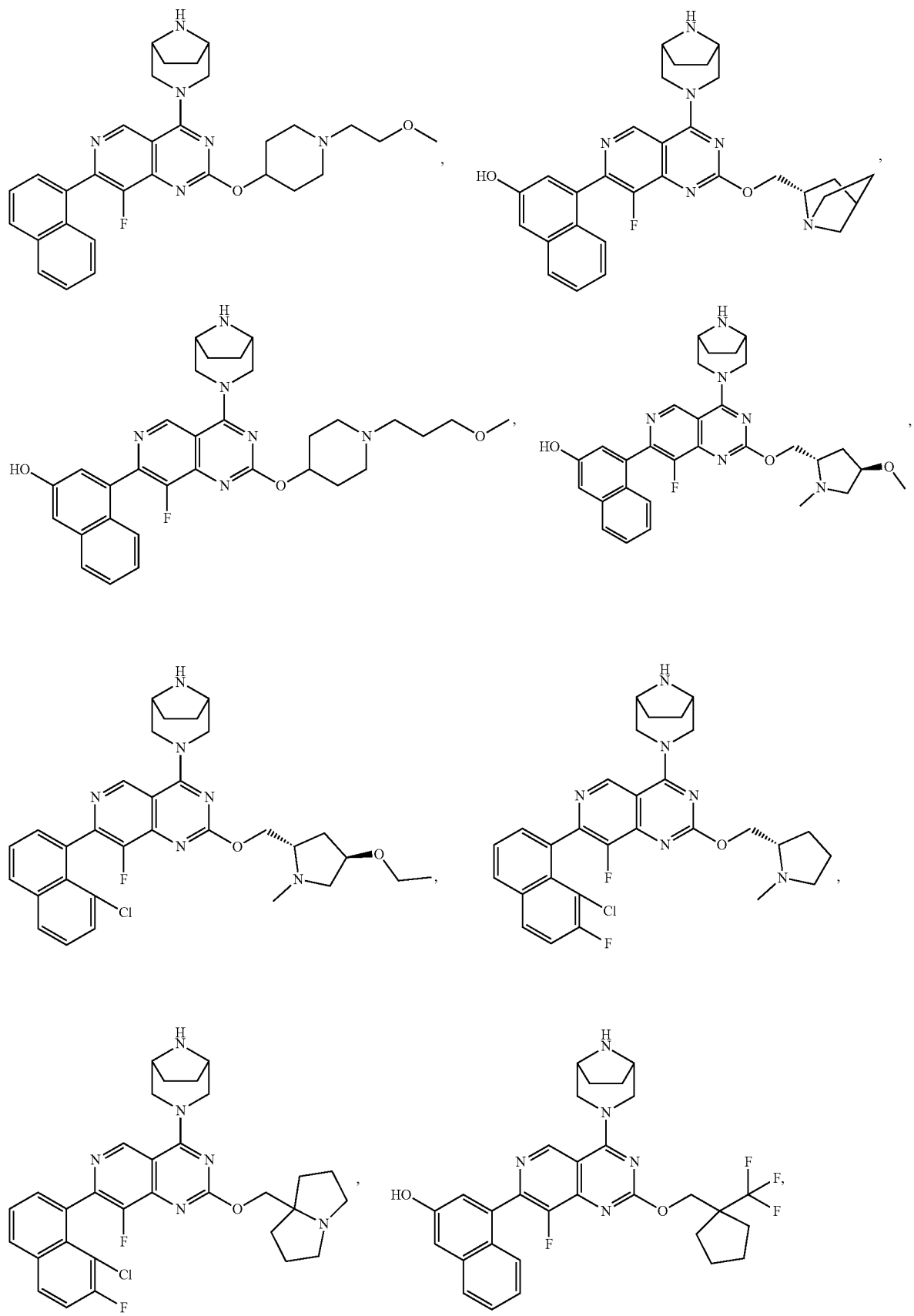

-continued
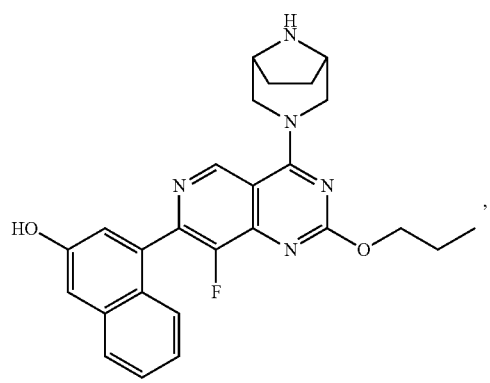
,
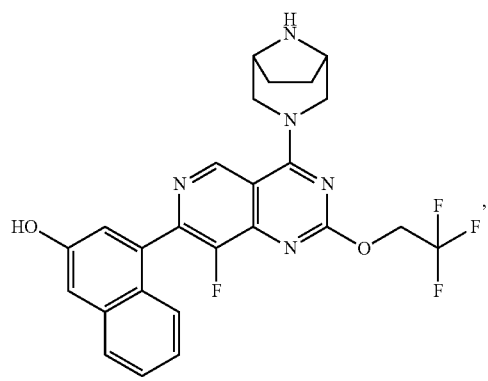
,
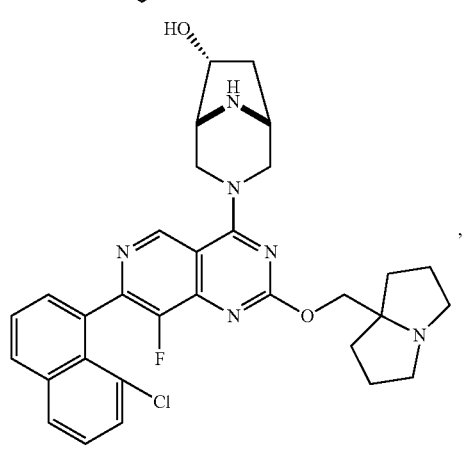
,
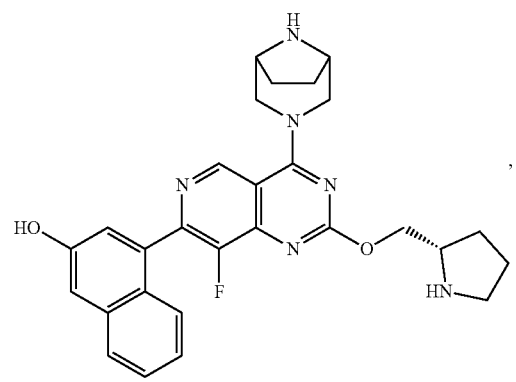
,
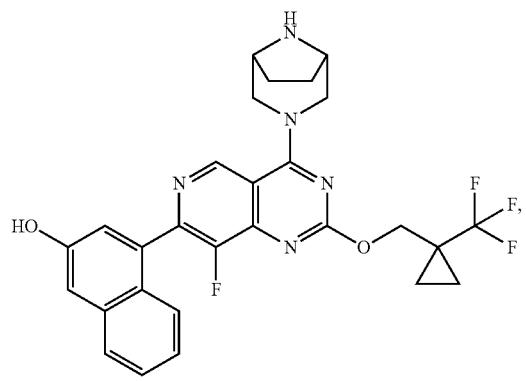
,
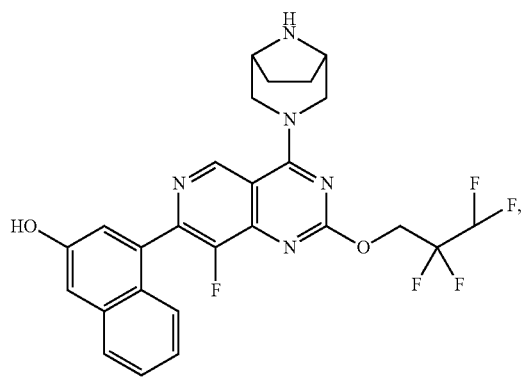
,
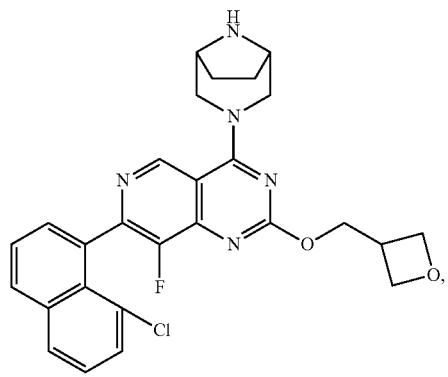
,
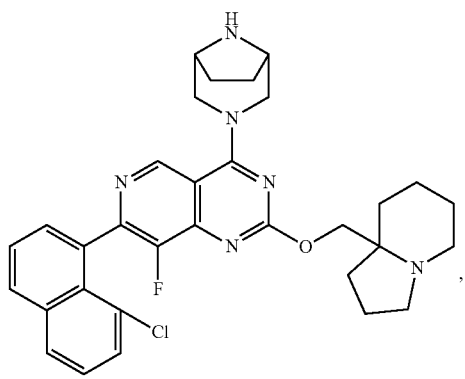
, -continued
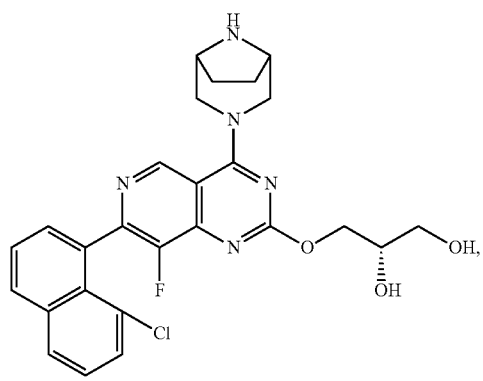
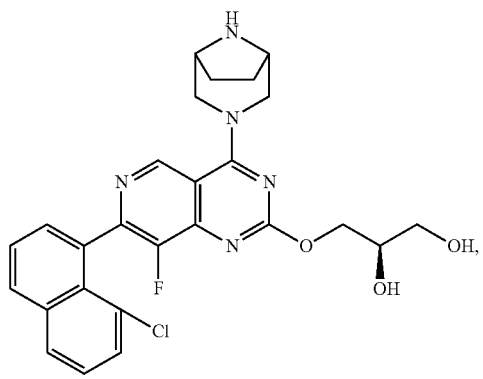
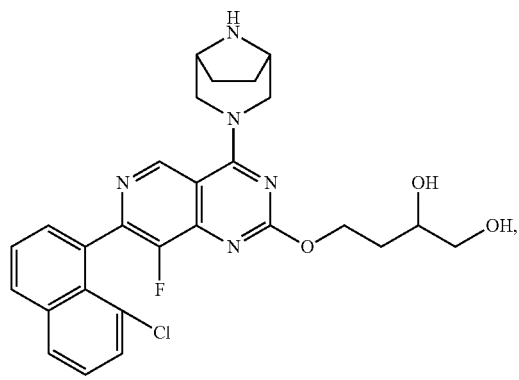
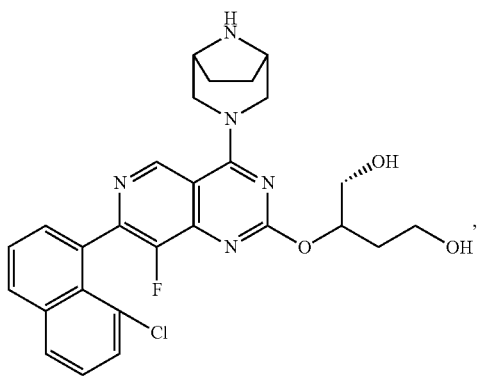
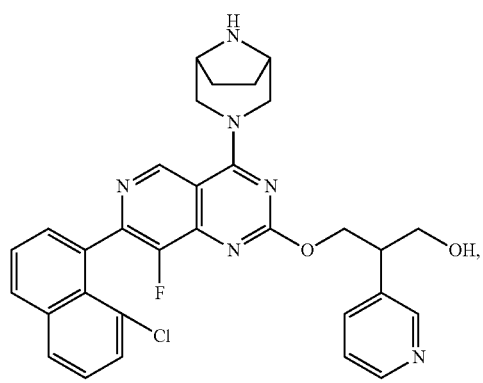
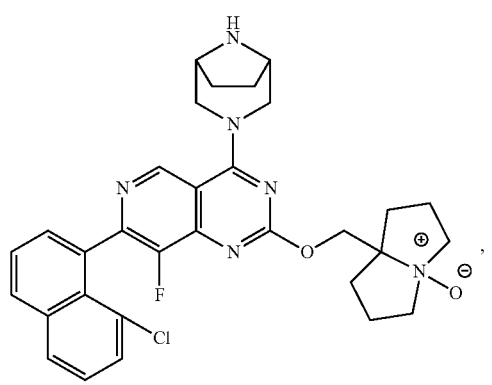
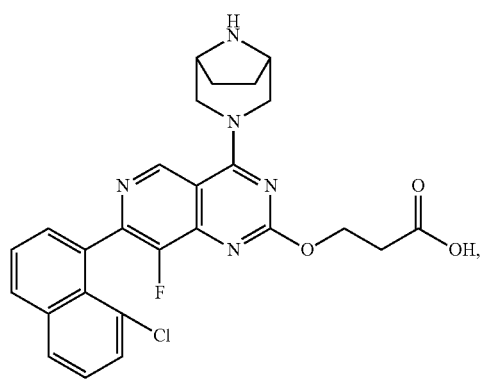
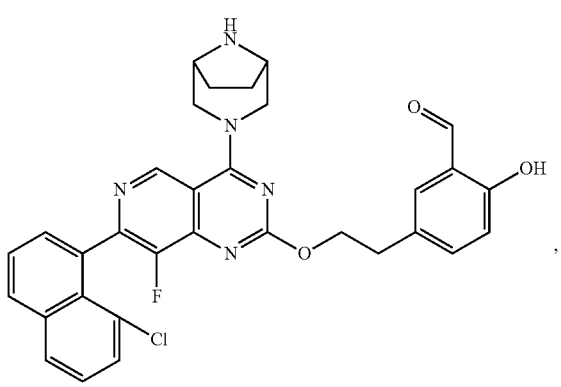

-continued
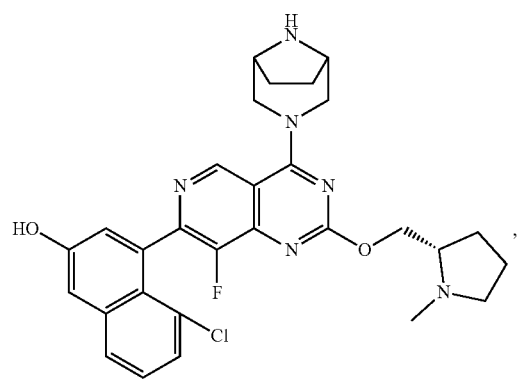
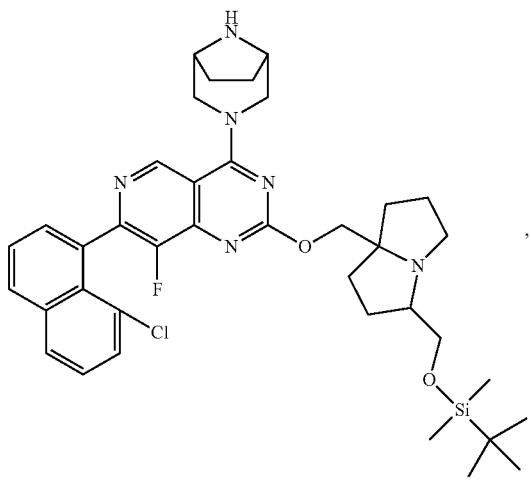
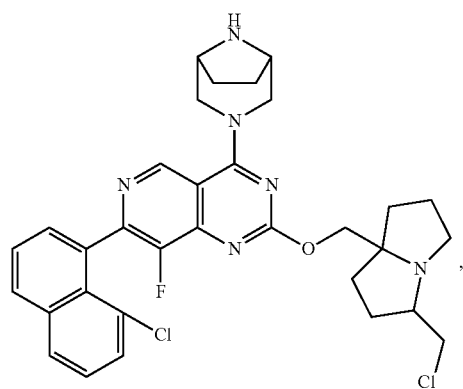
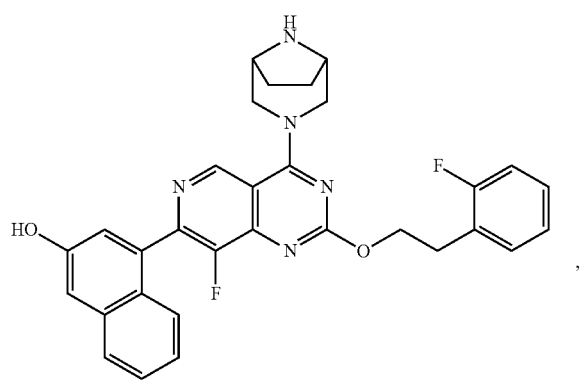
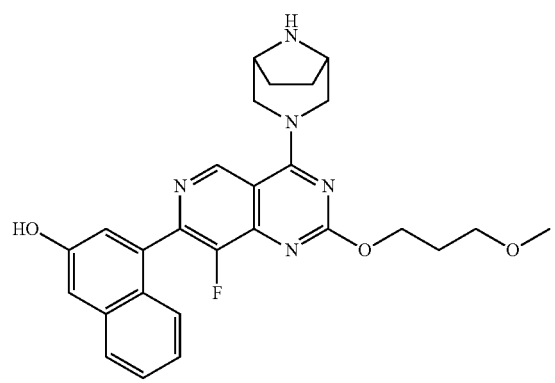
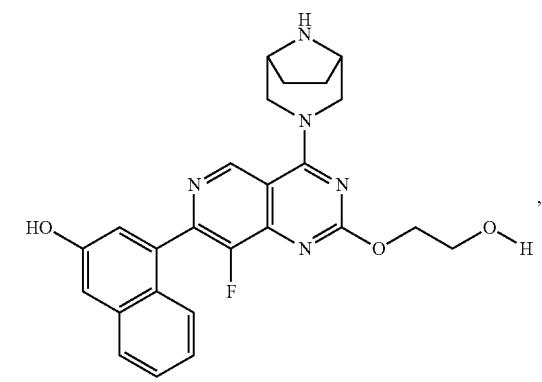
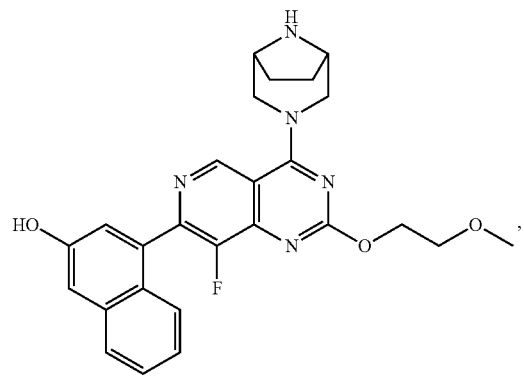
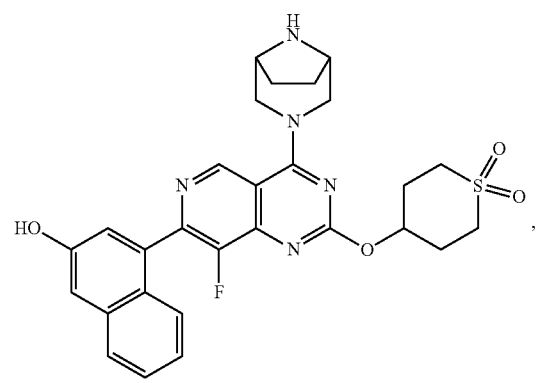

31
-continued
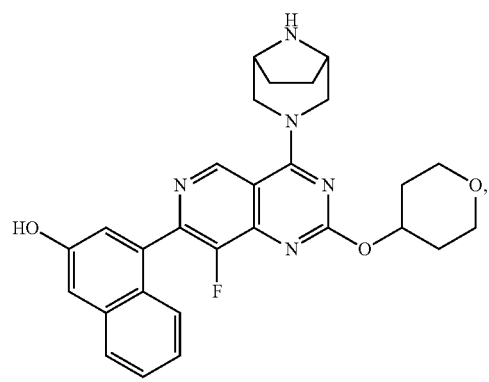
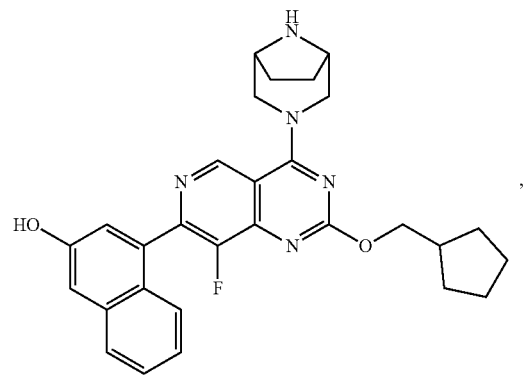
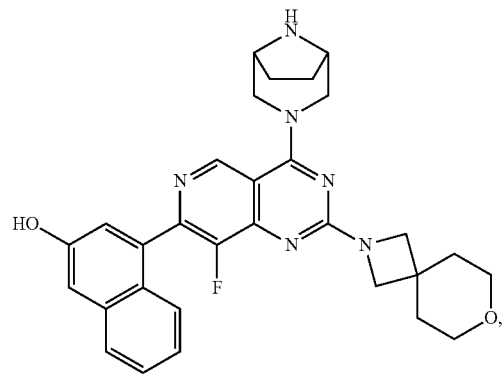
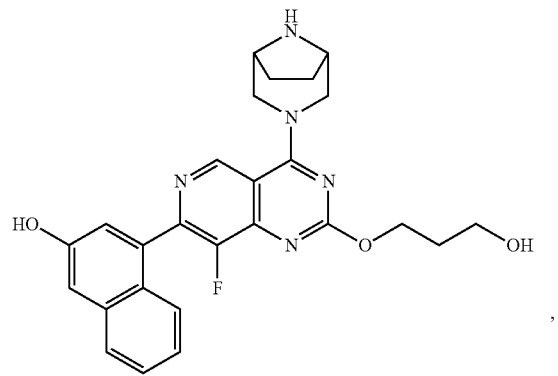
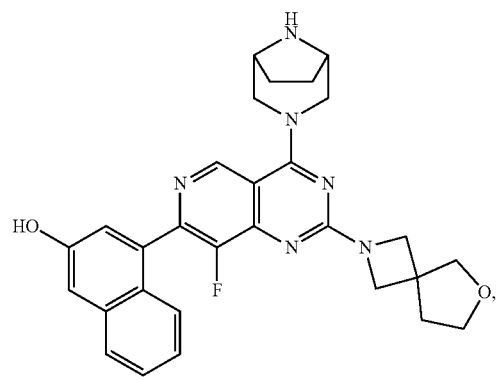
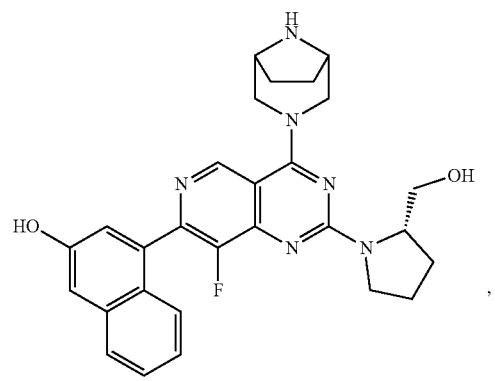
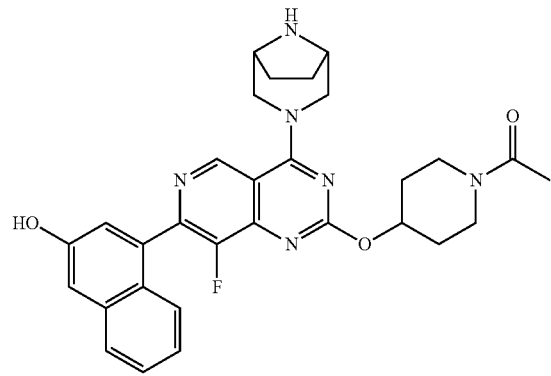
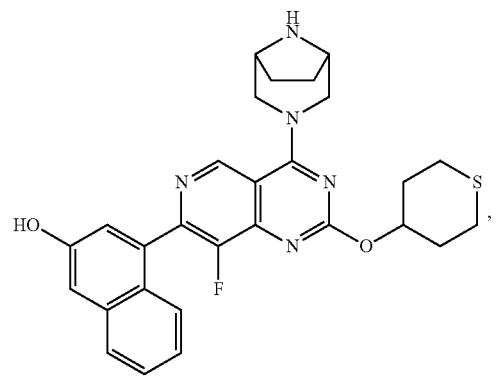
32

33
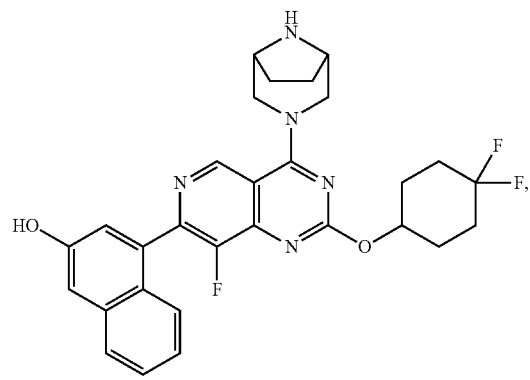
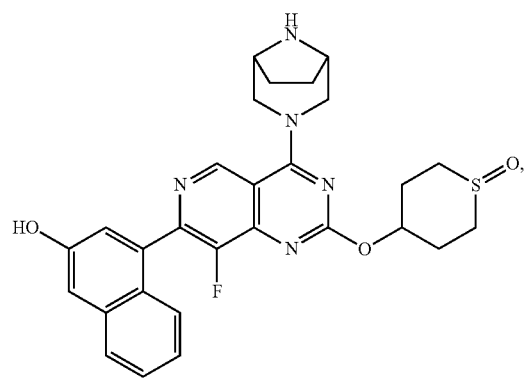
34
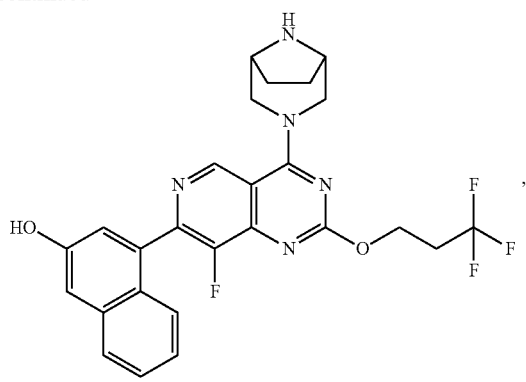
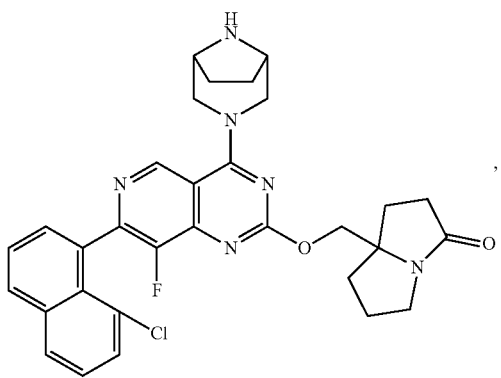
-continued
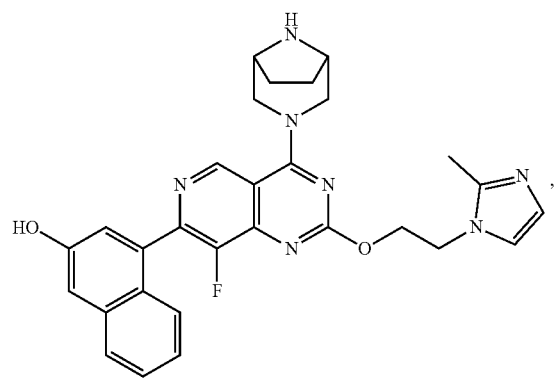
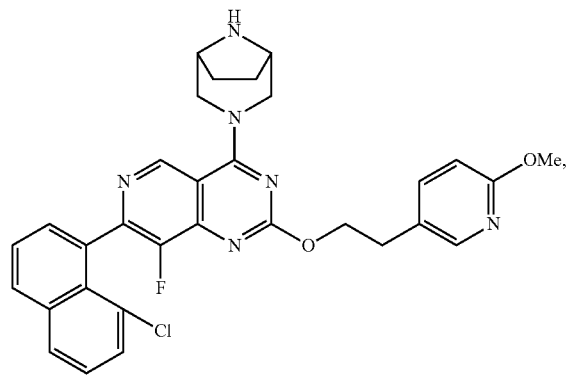
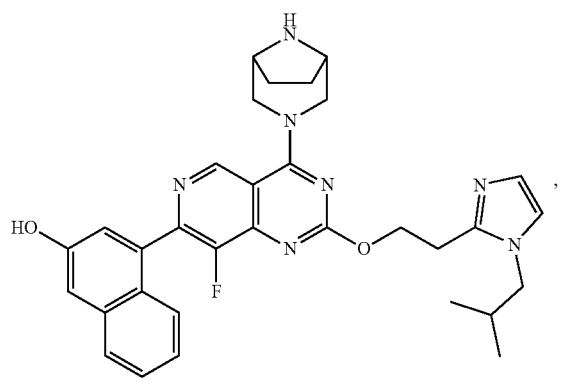
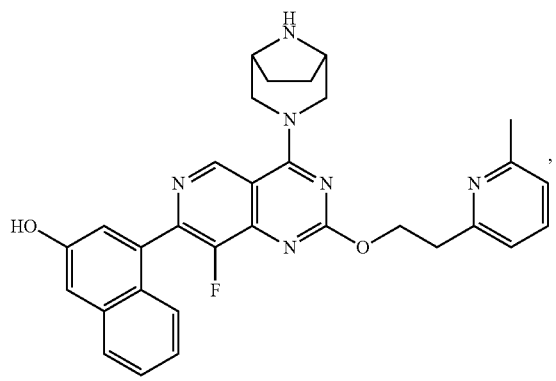

35
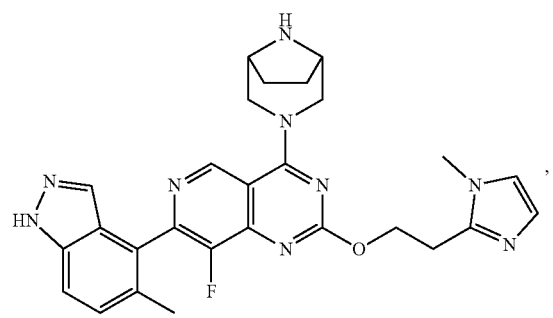
36
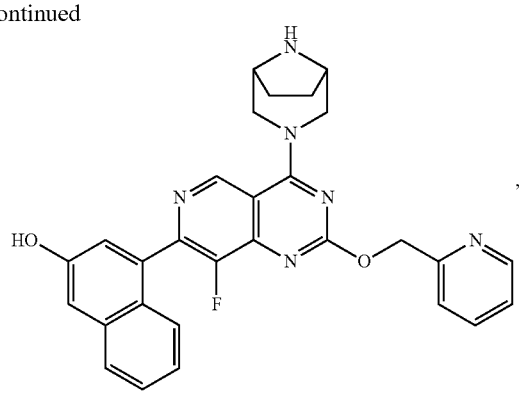
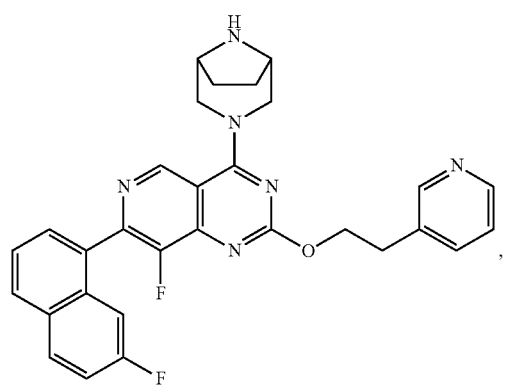
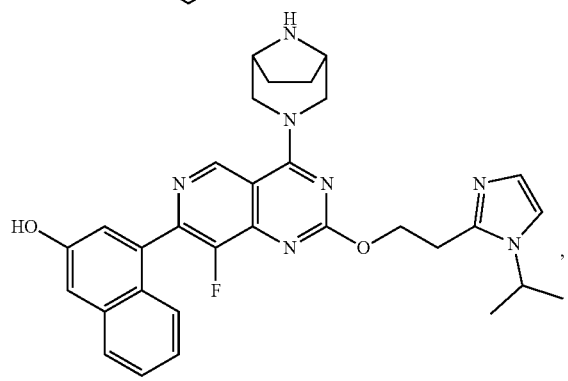
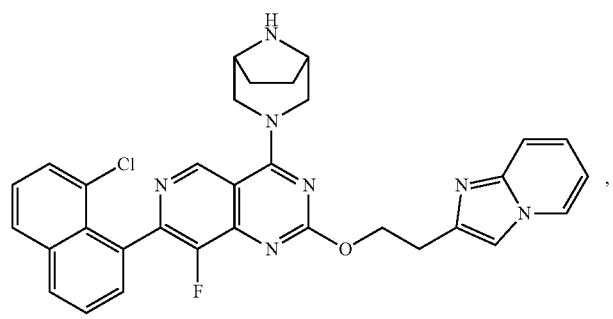
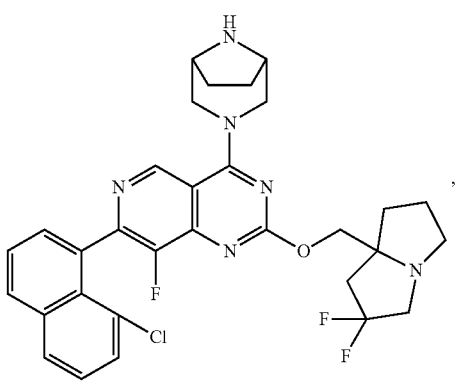
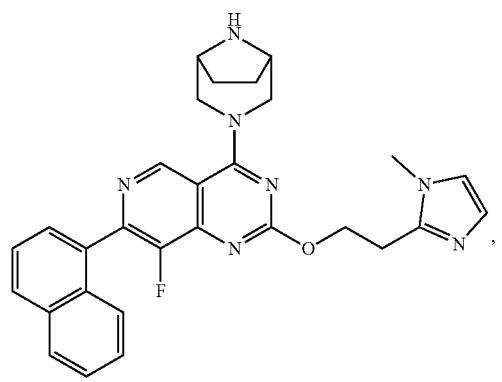
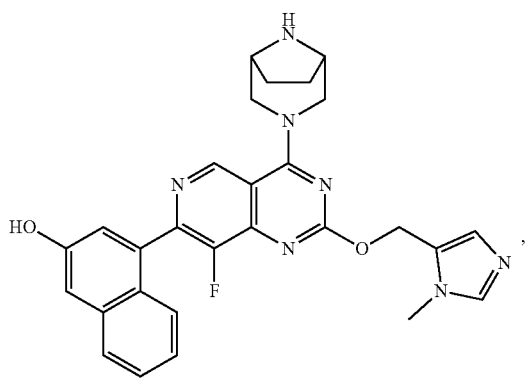

37
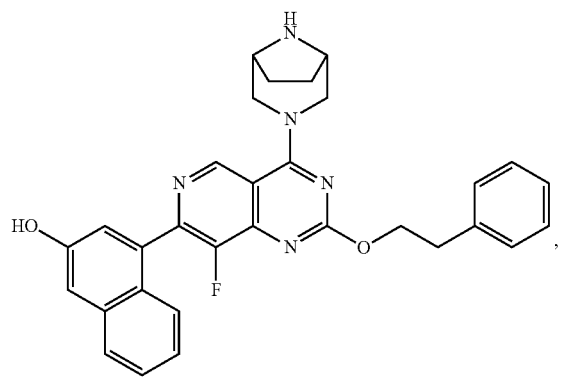
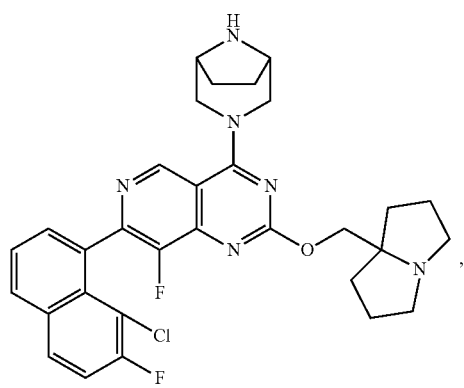
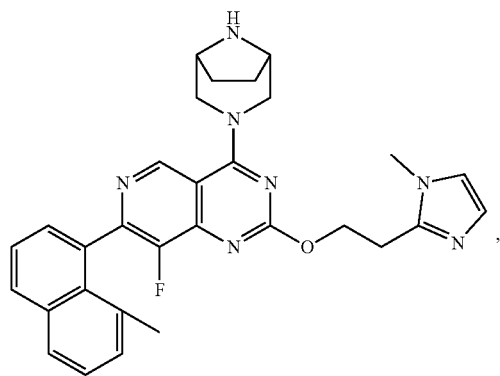
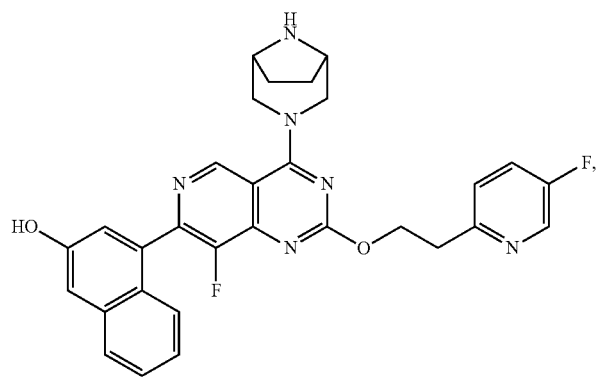
38
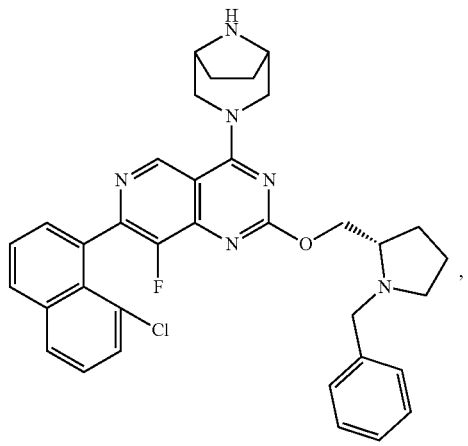
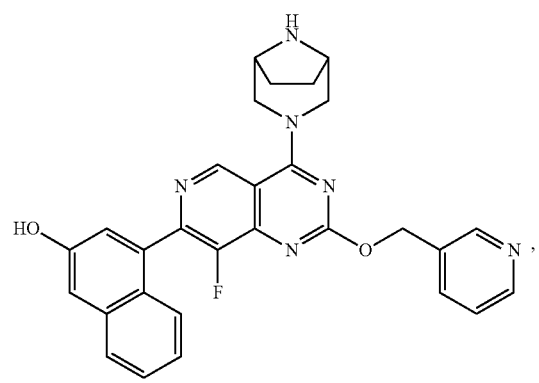
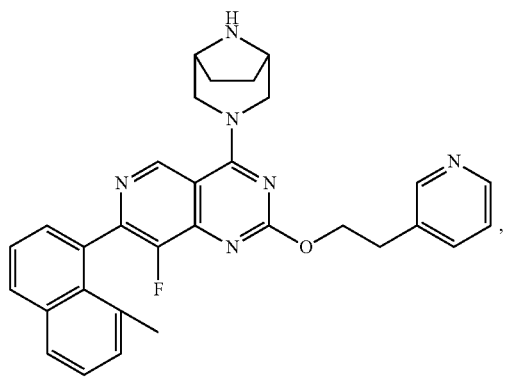
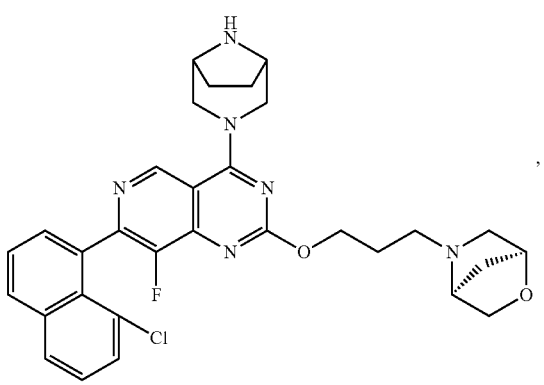

-continued
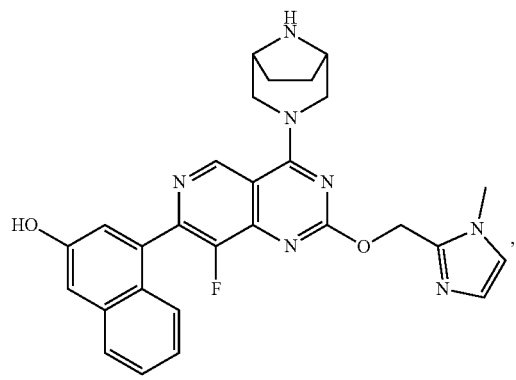
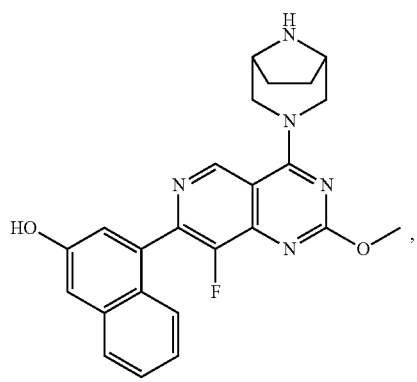
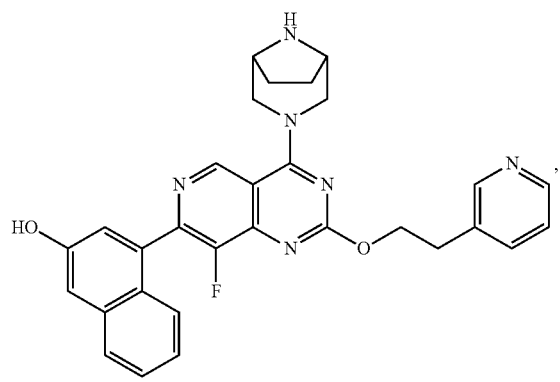
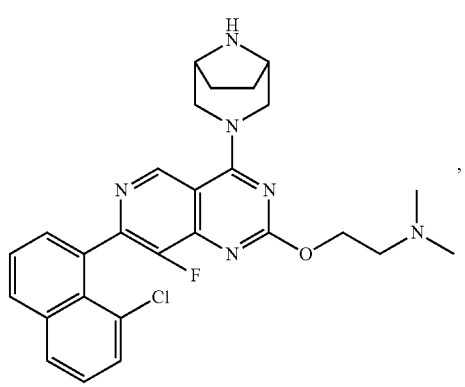
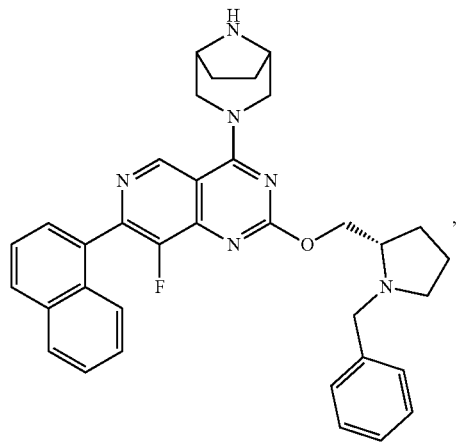
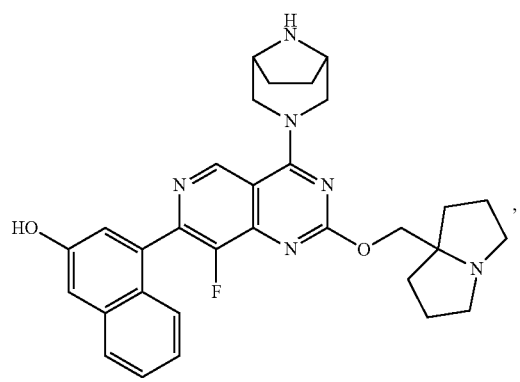
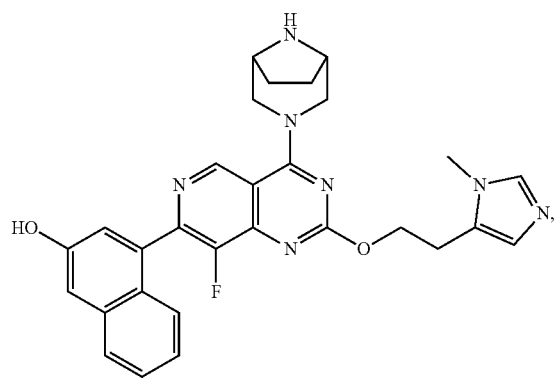
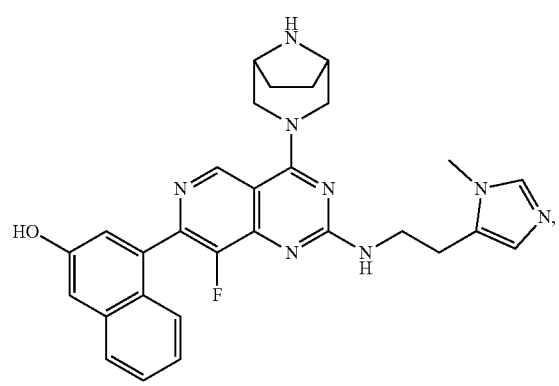

41 42
-continued
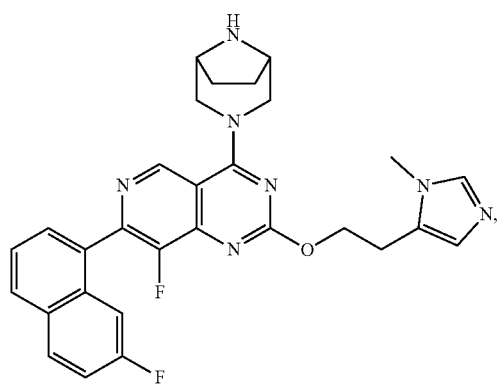,
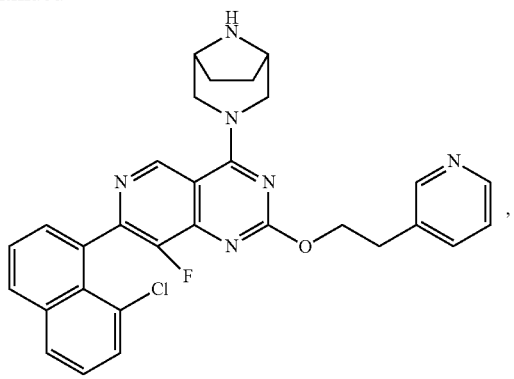,
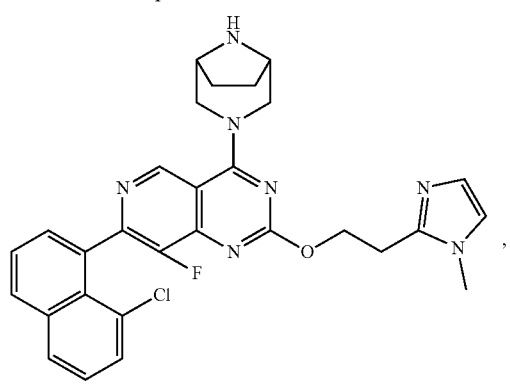,
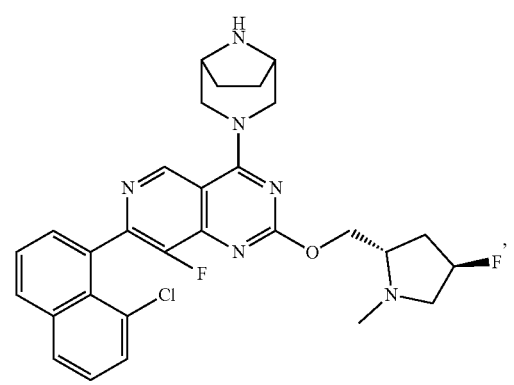,
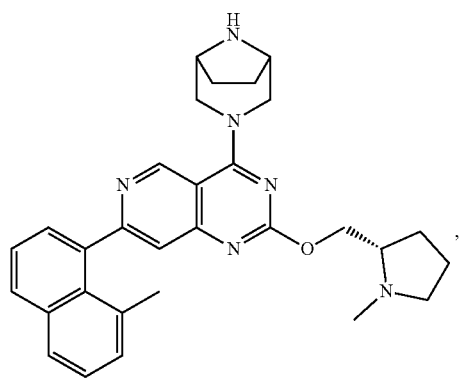,
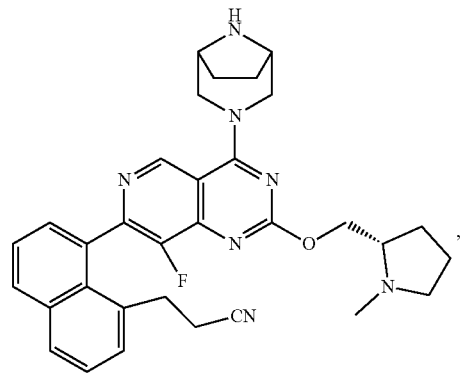,
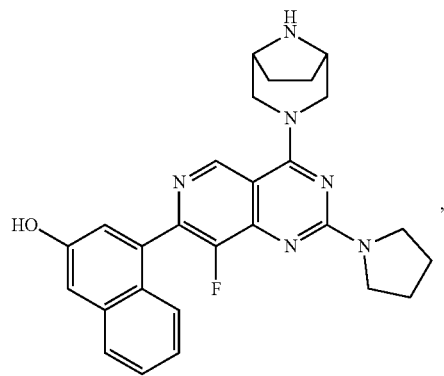,
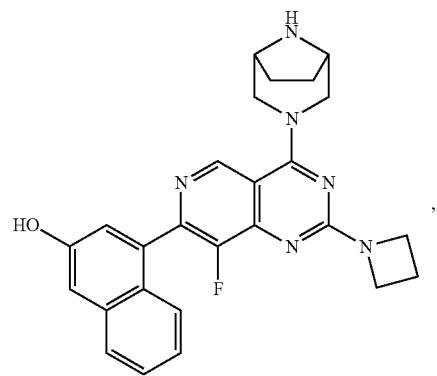, -continued
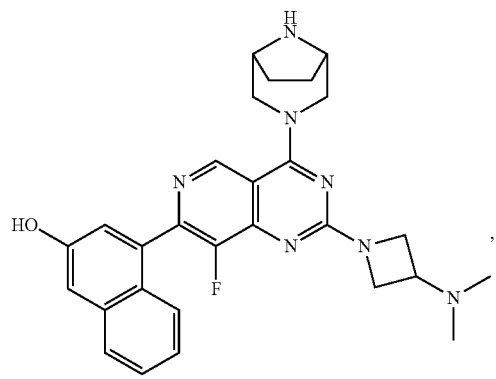
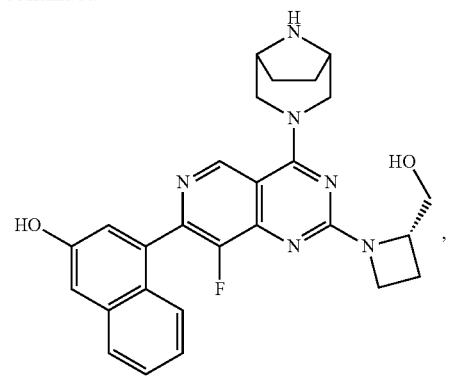
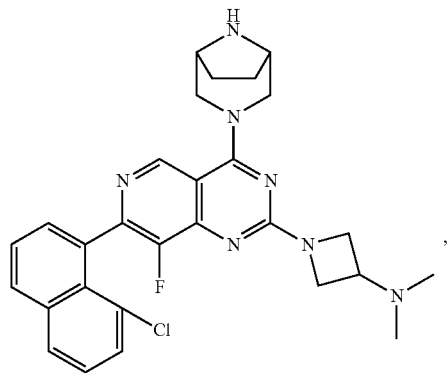
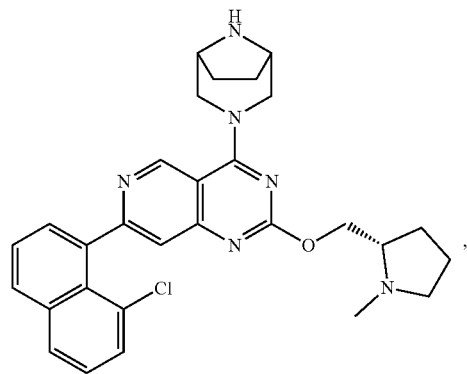
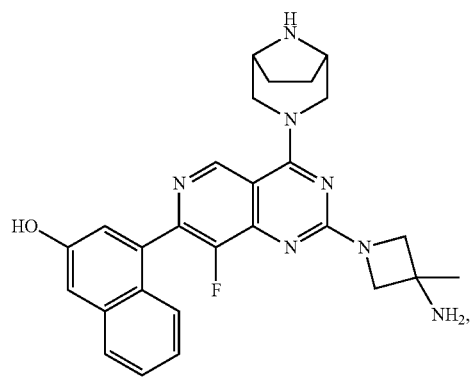
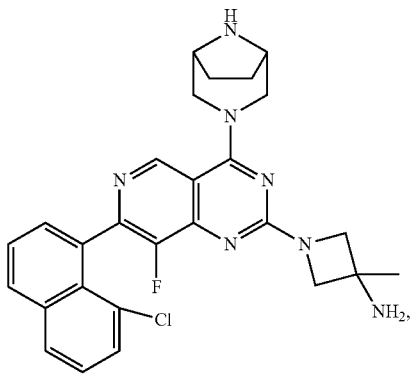
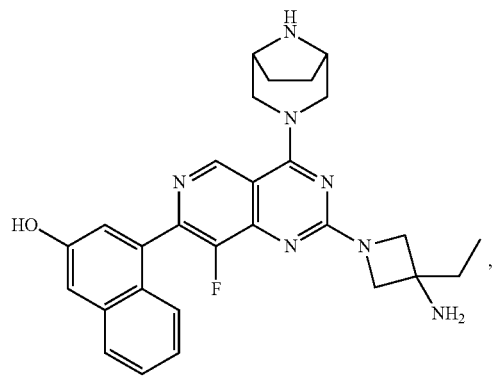
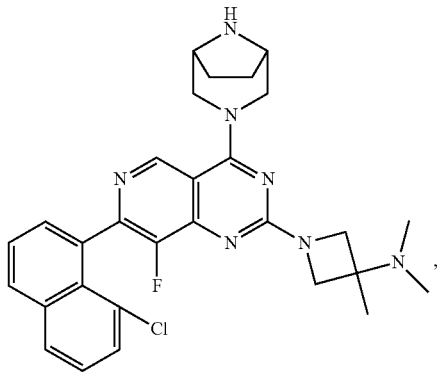

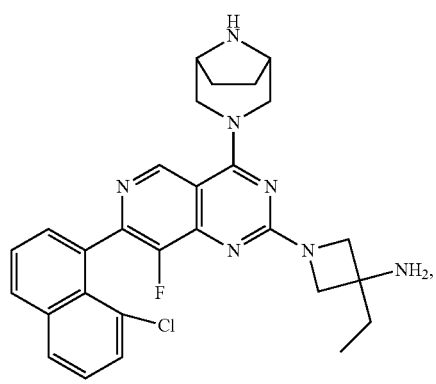
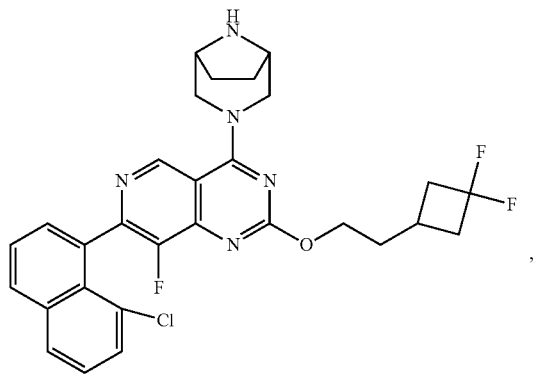
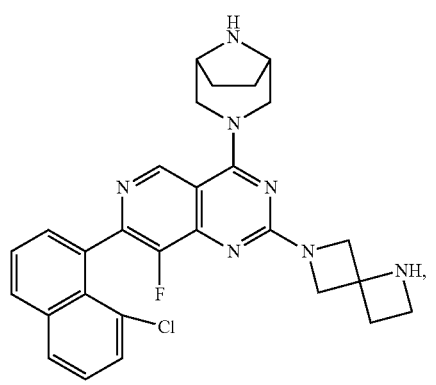
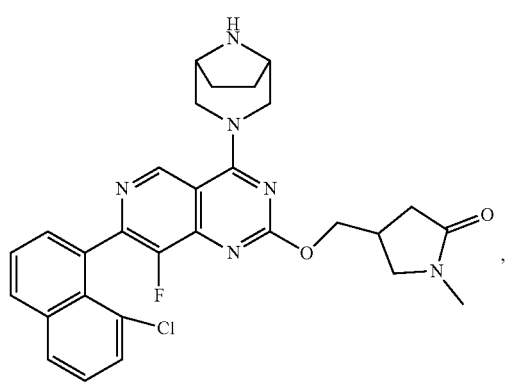
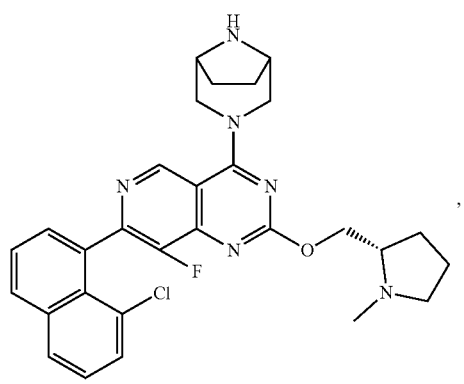
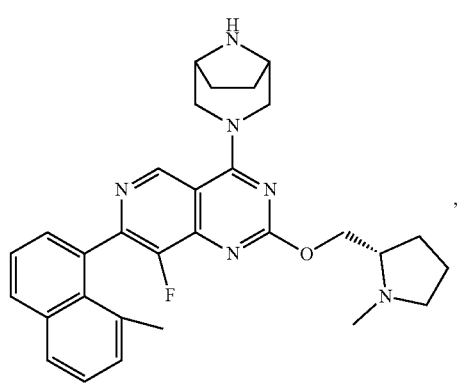
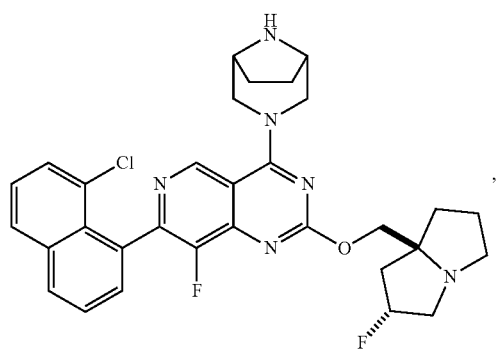
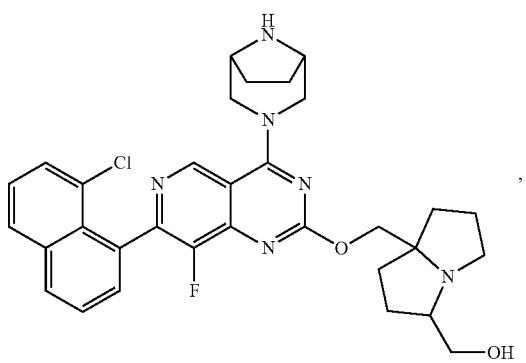

47
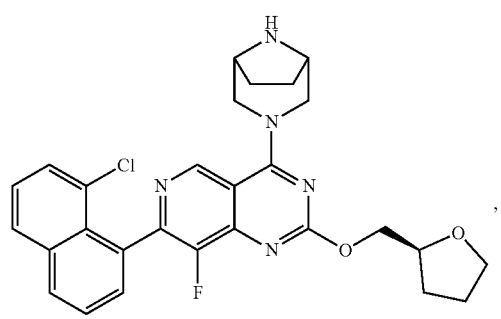
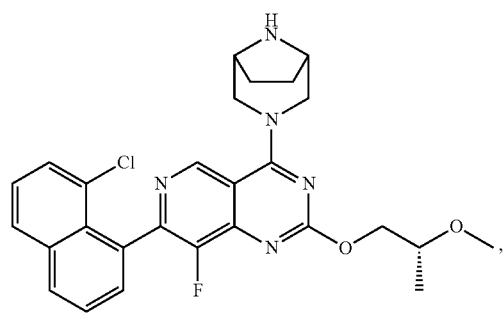
48
-continued
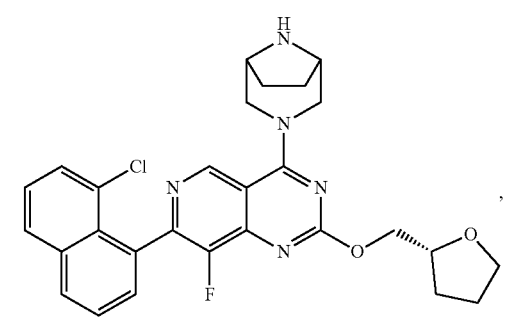
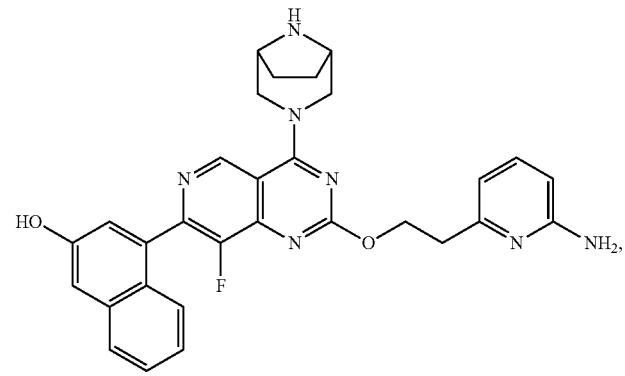
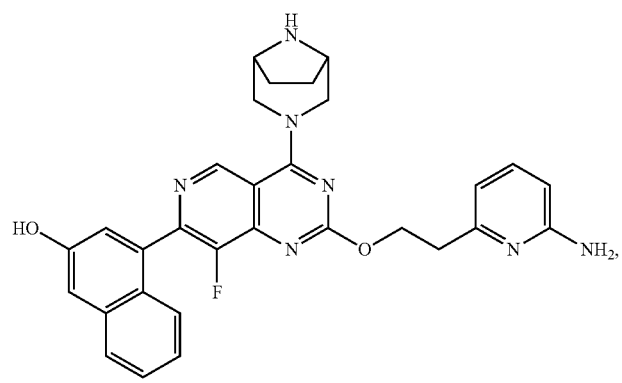
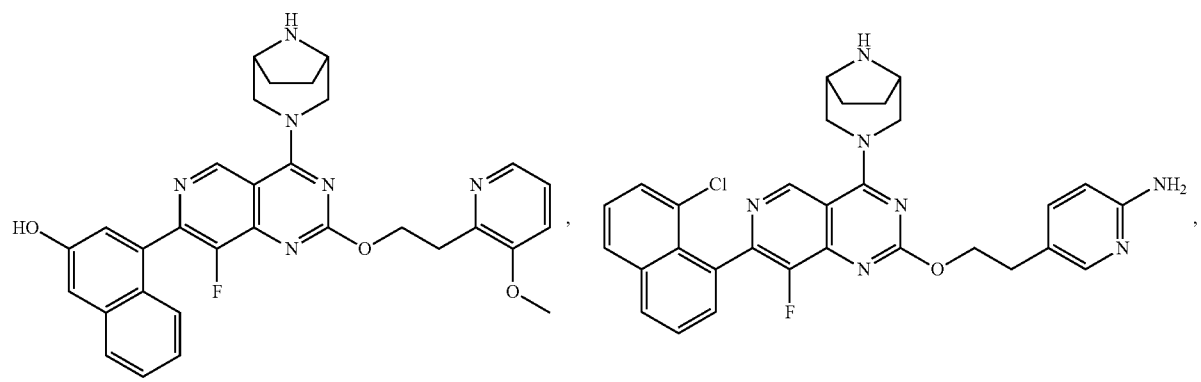

-continued
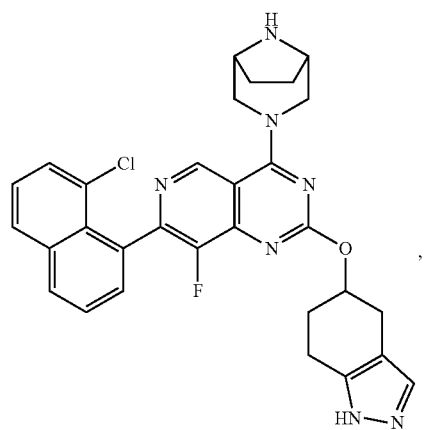
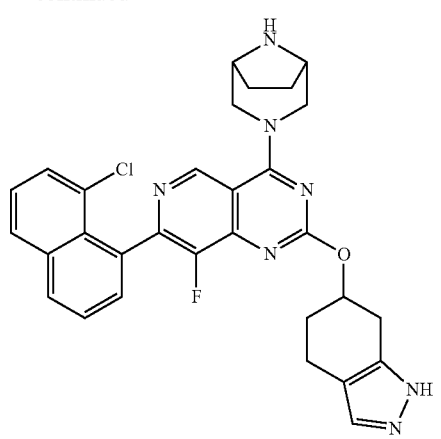
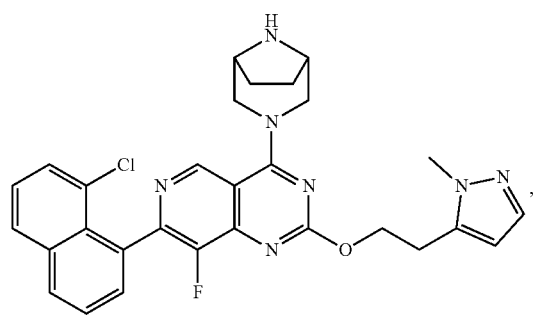
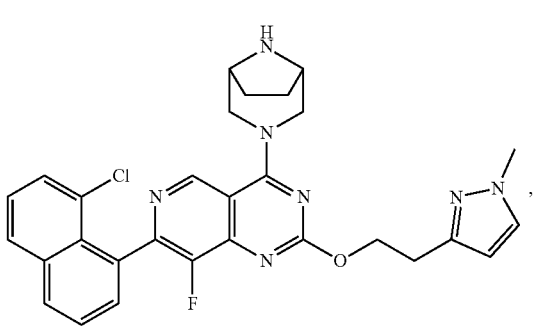
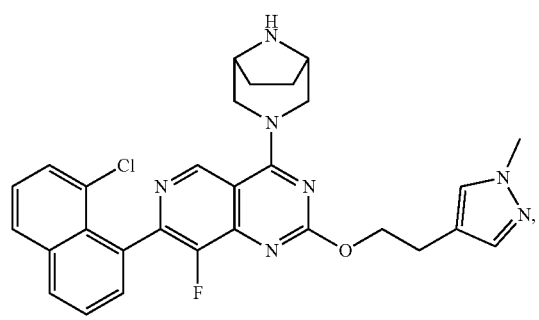
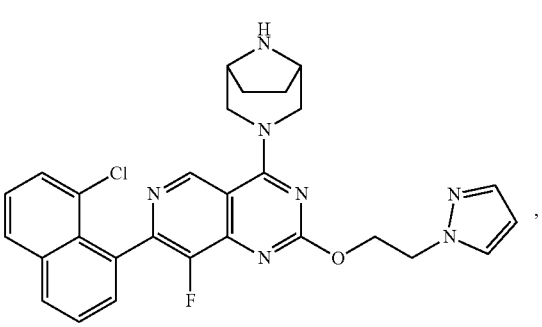
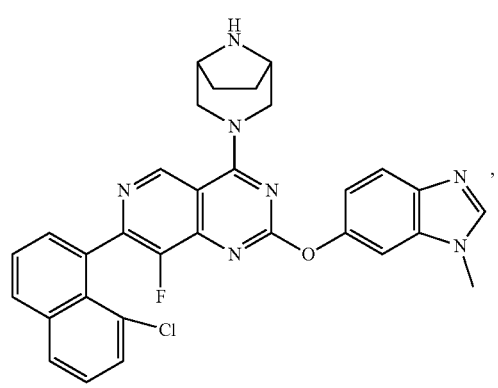
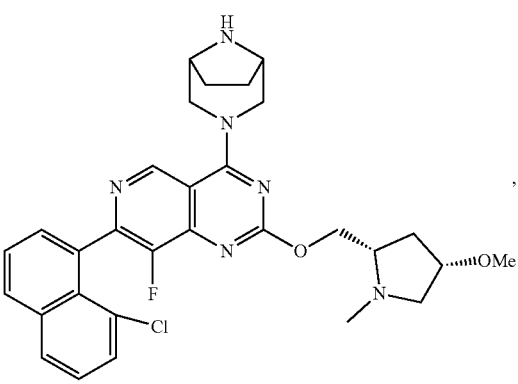

-continued
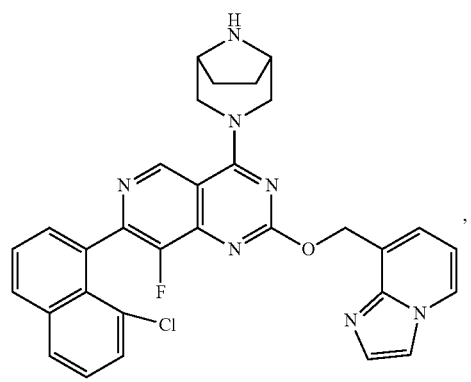
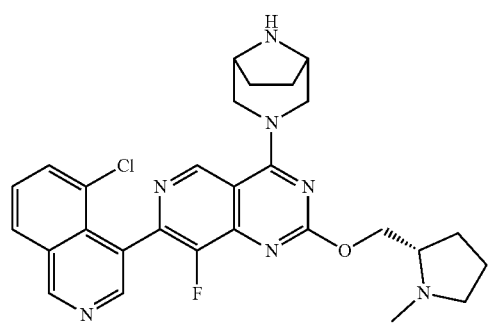
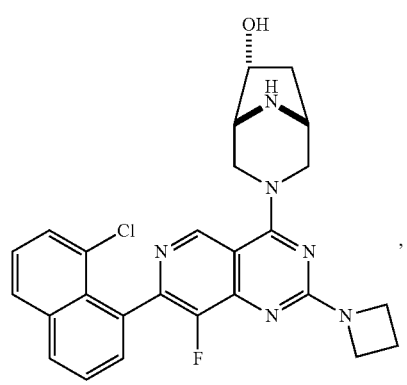
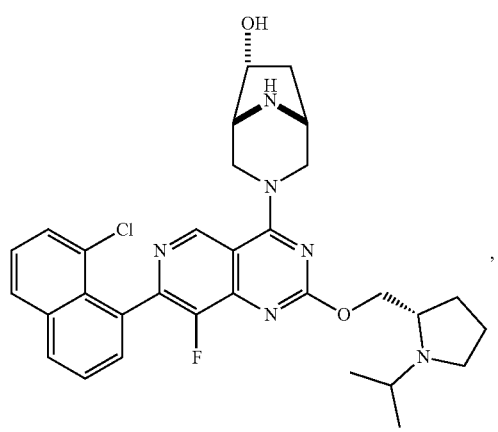
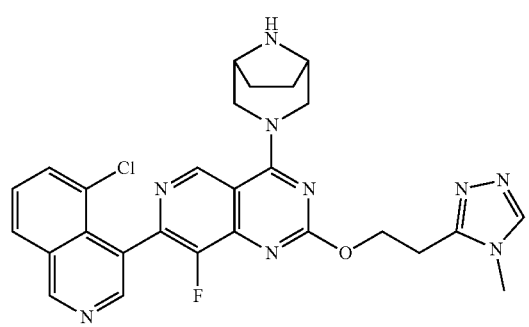
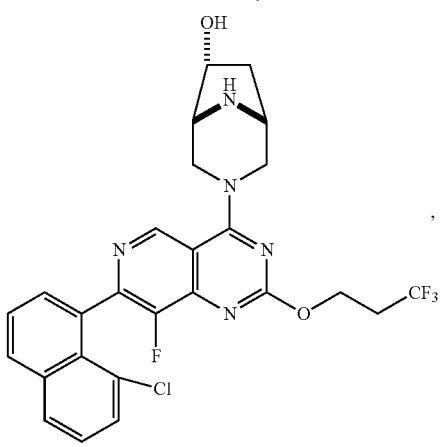
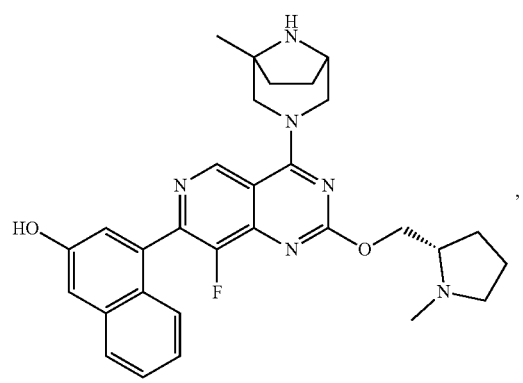
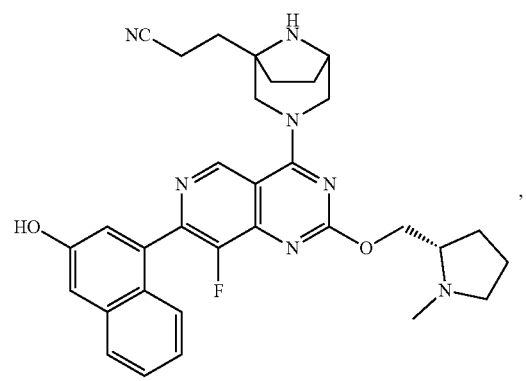

53
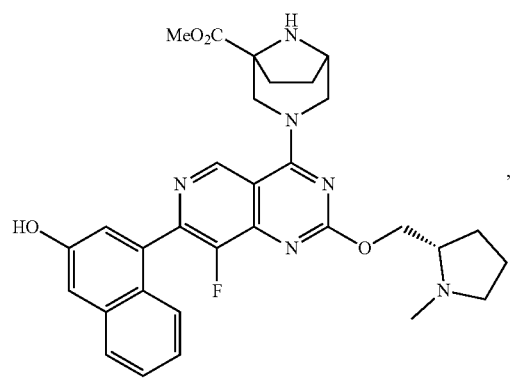
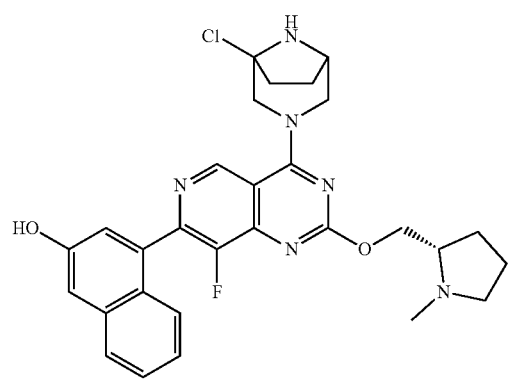
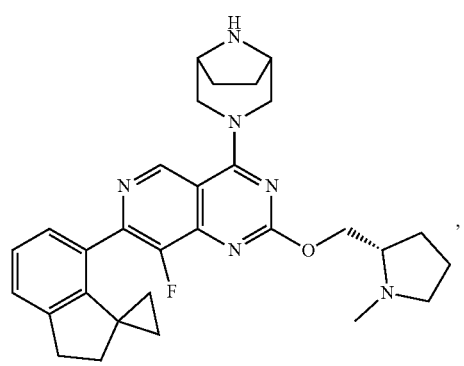
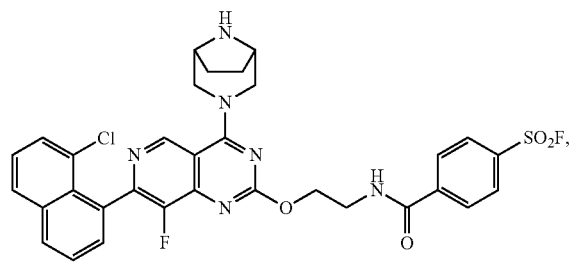
54
-continued
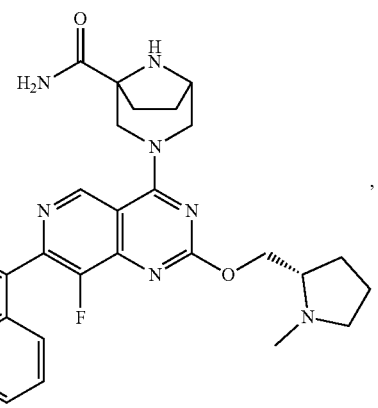
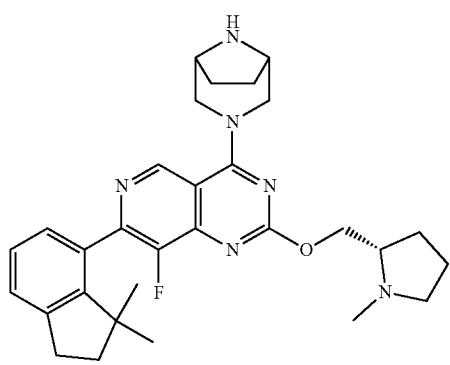
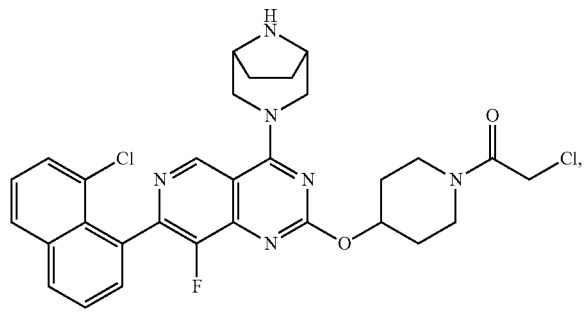
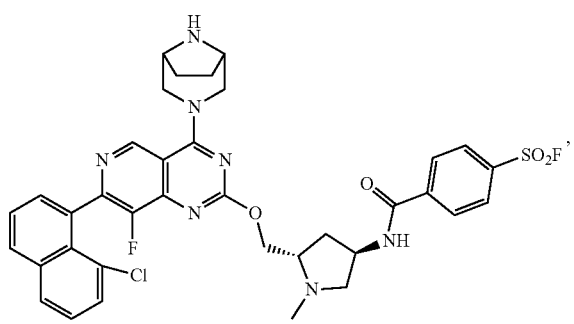

55
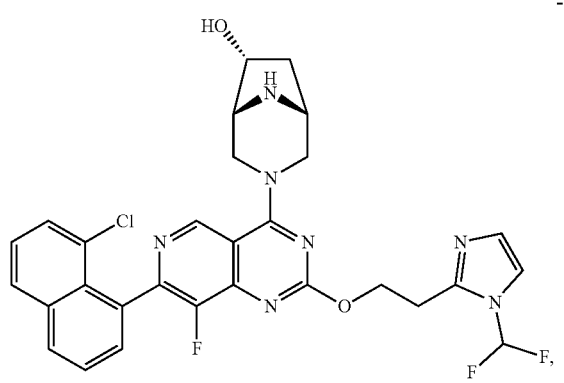
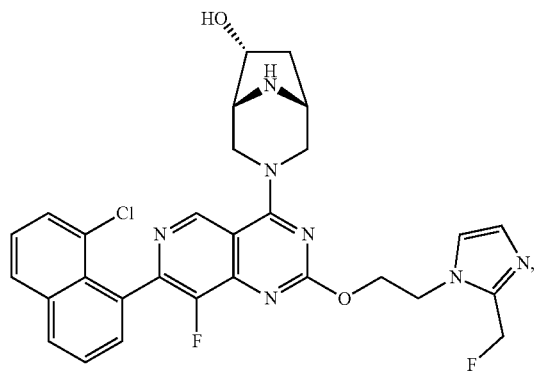
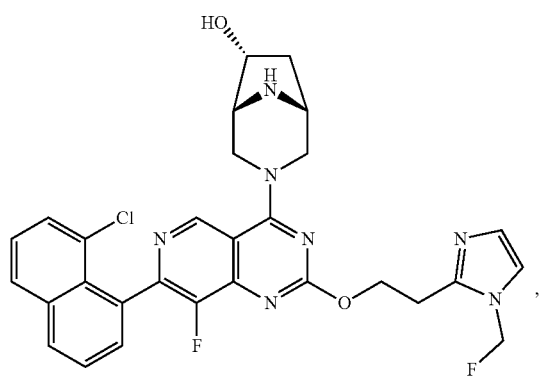
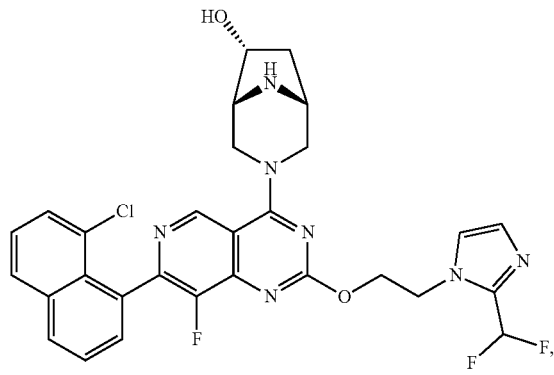
56
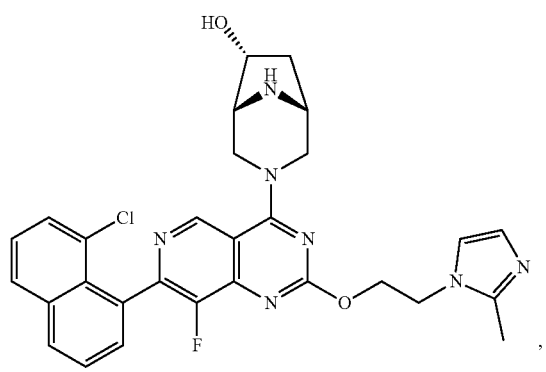
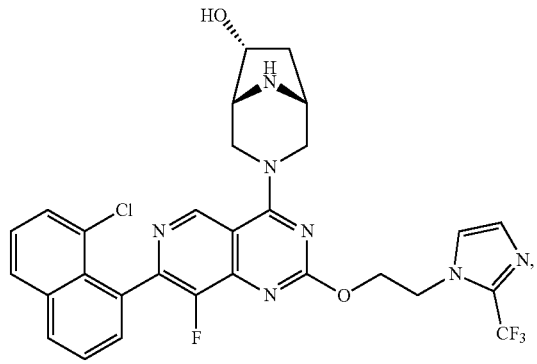
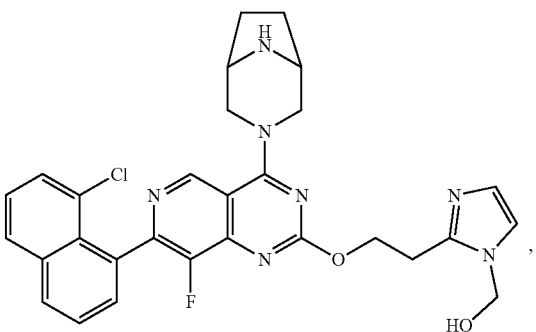
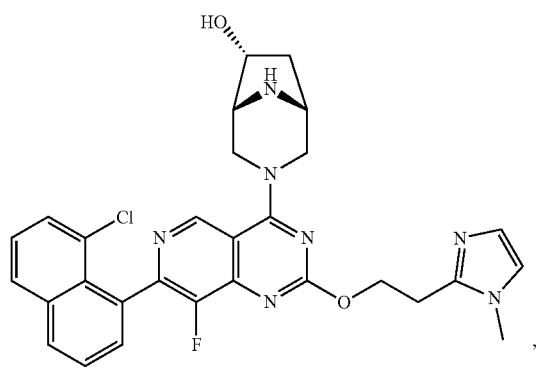

-continued
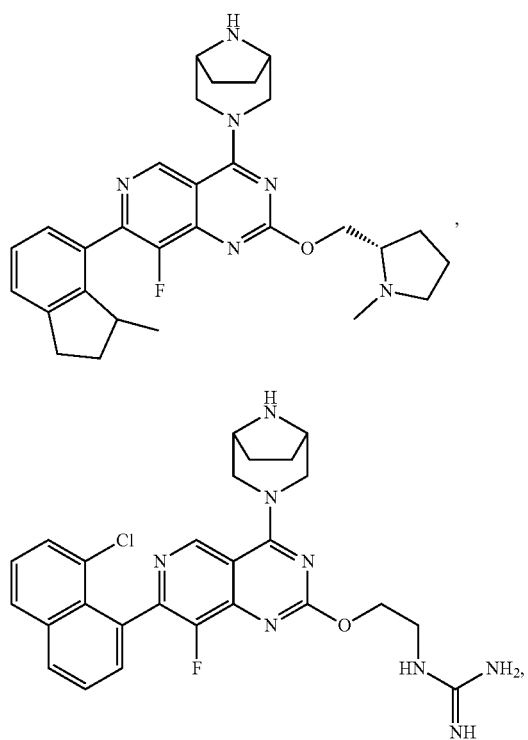
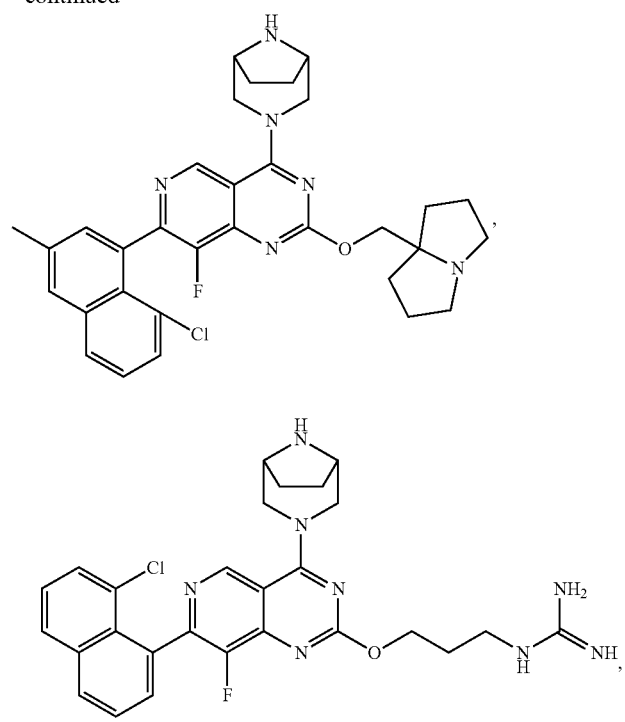
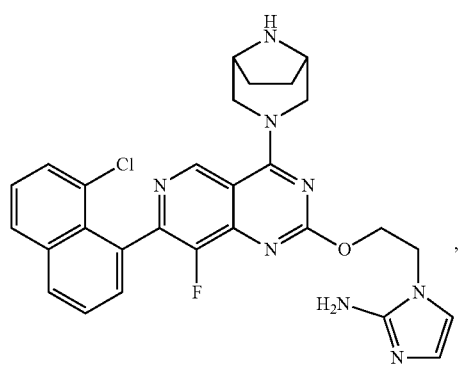
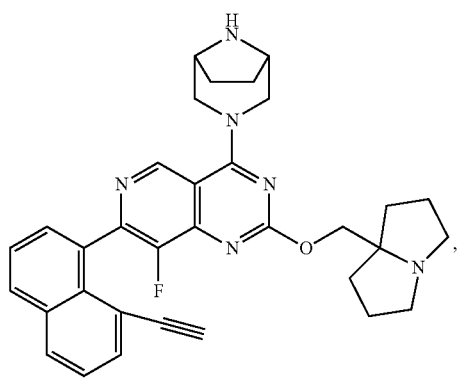
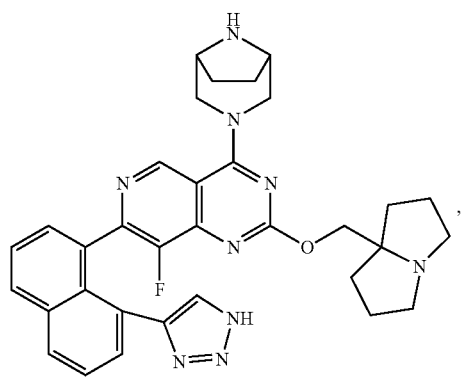
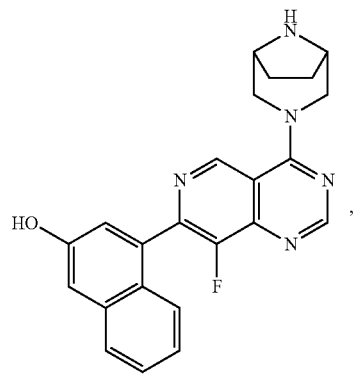

-continued
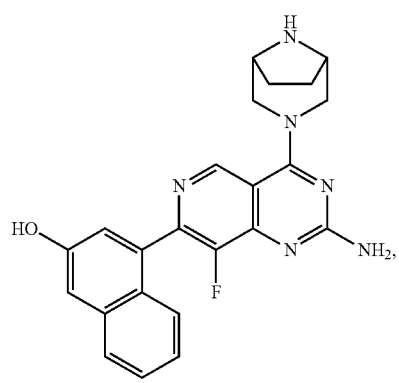
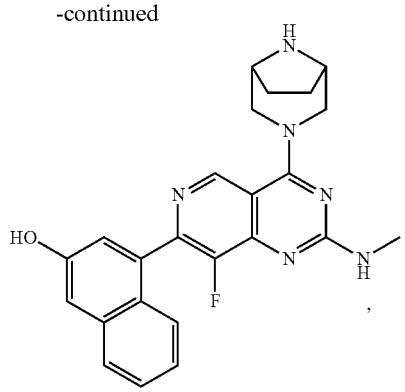
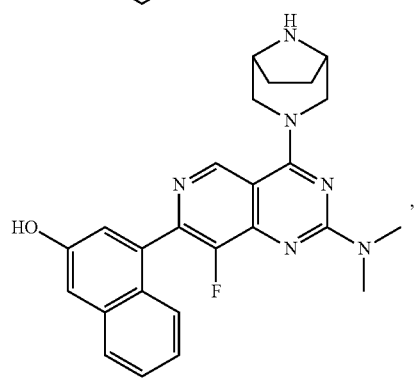
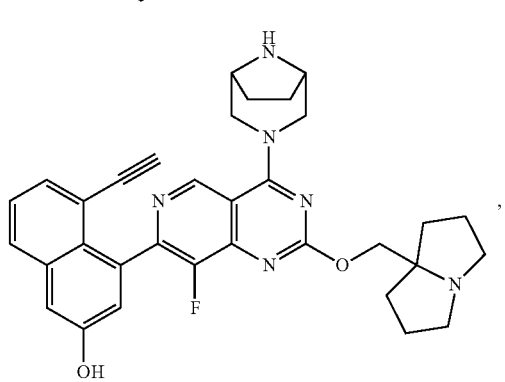
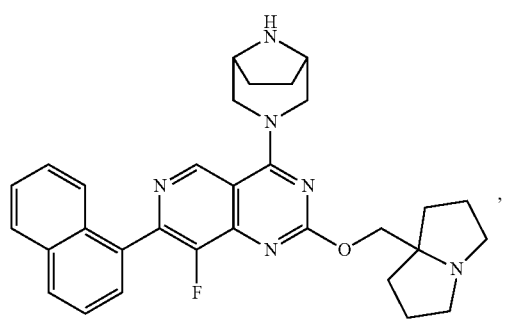
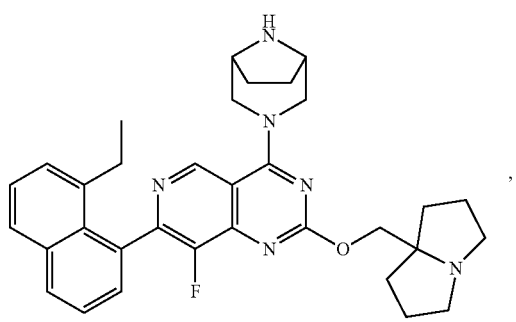
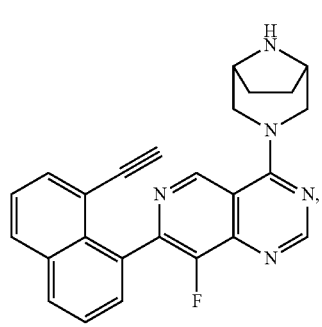
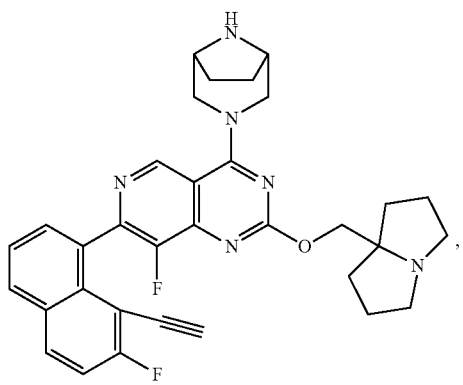

61
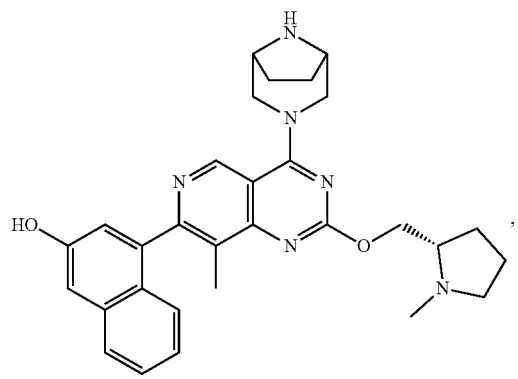
62
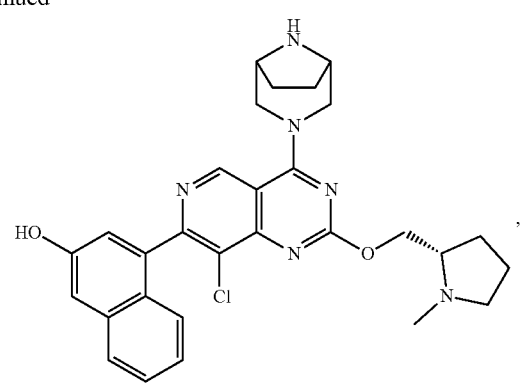
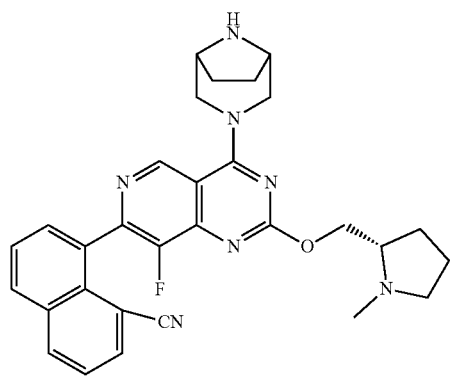
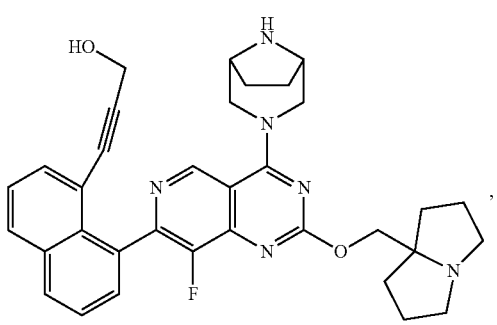
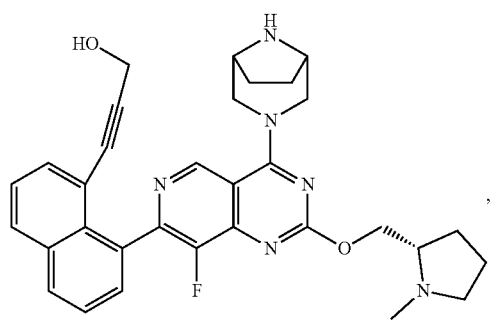
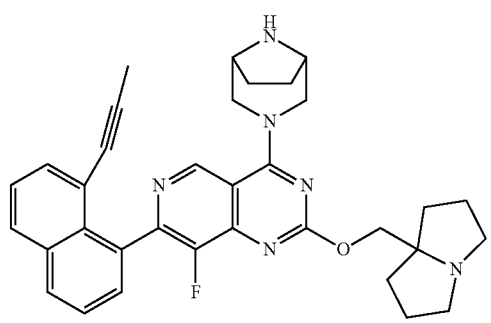
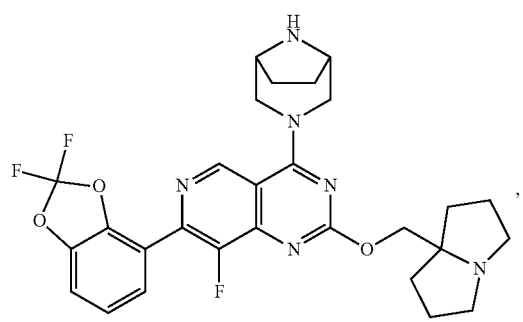
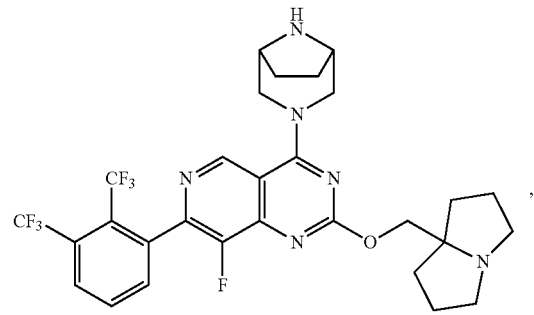

-continued
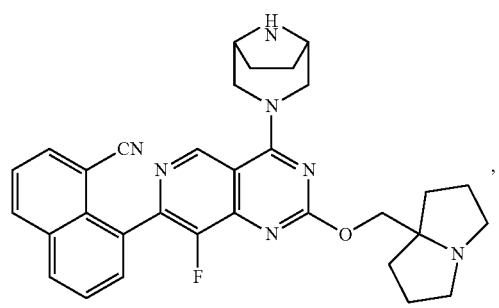
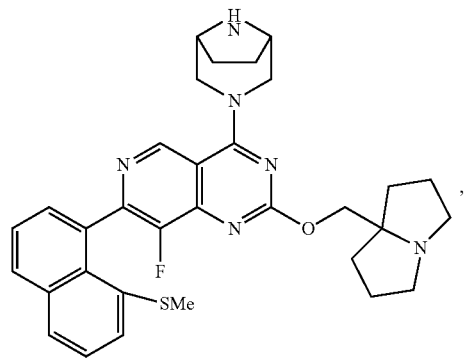
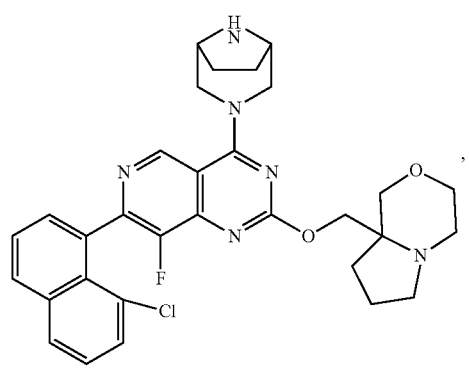
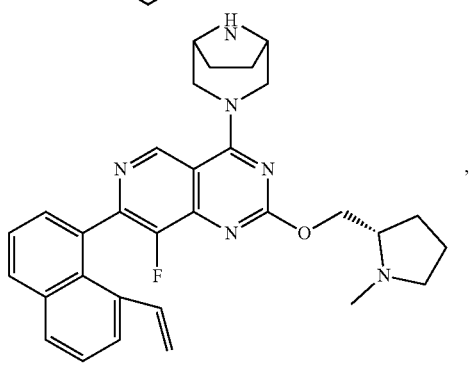
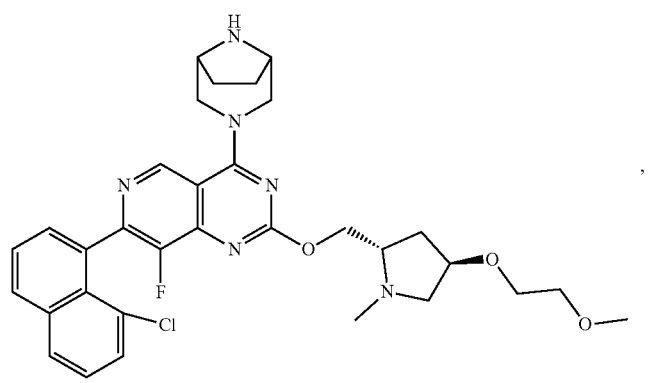
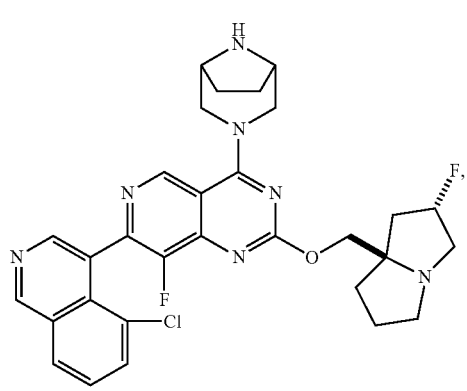
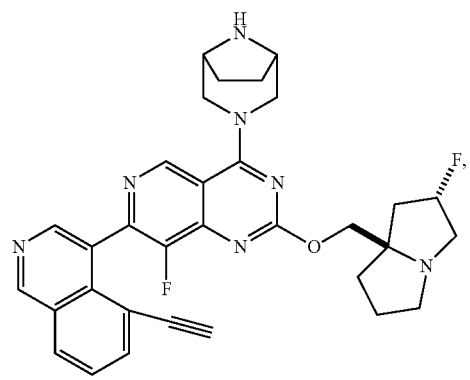
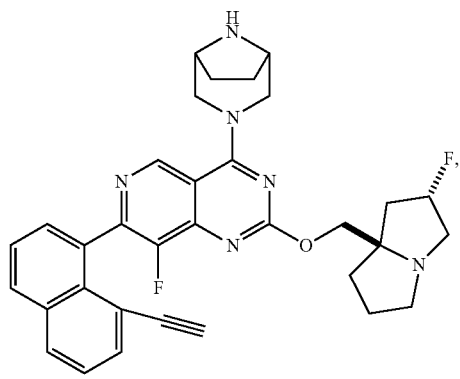

65
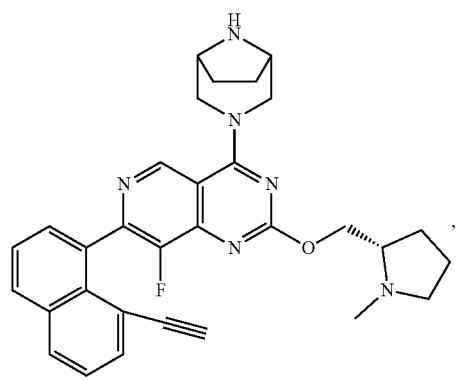
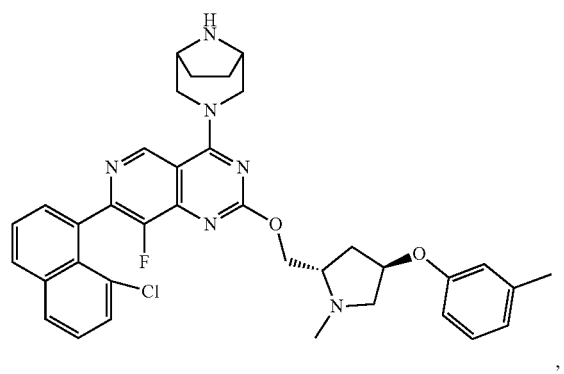
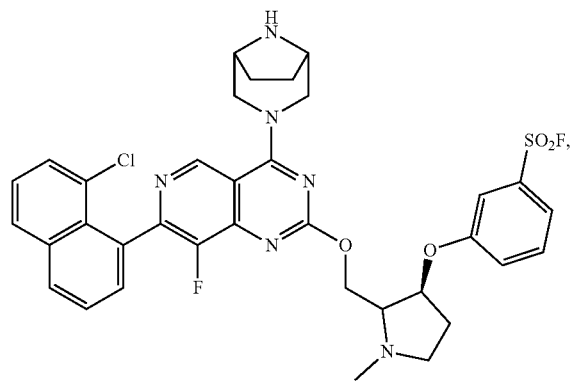
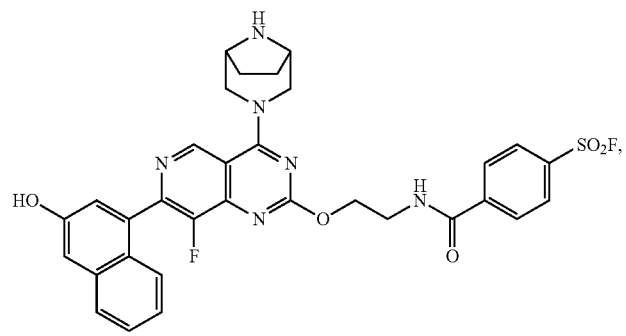
66
-continued
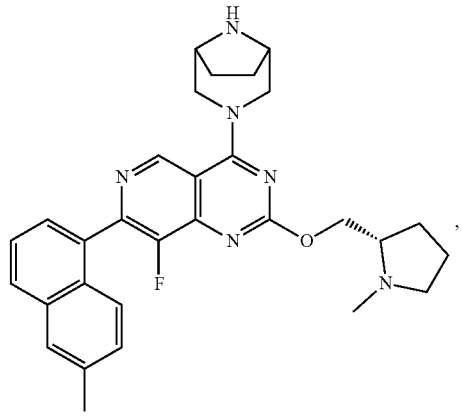
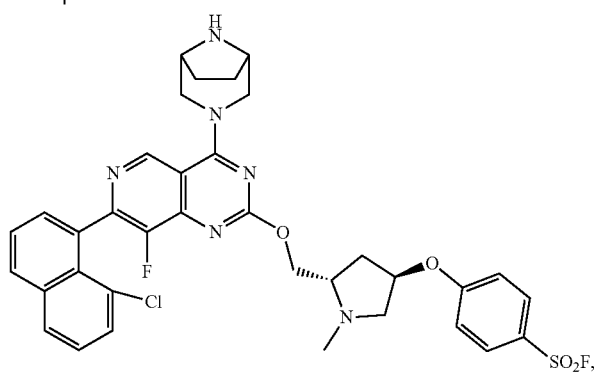
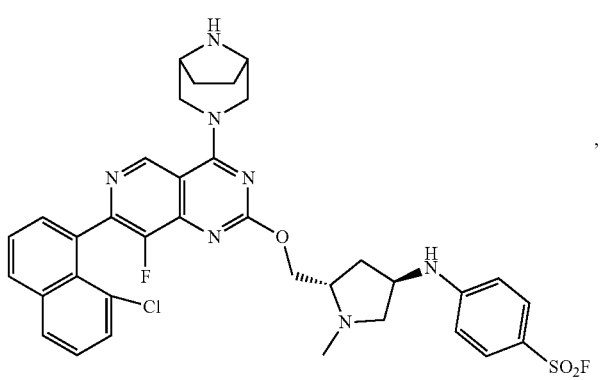
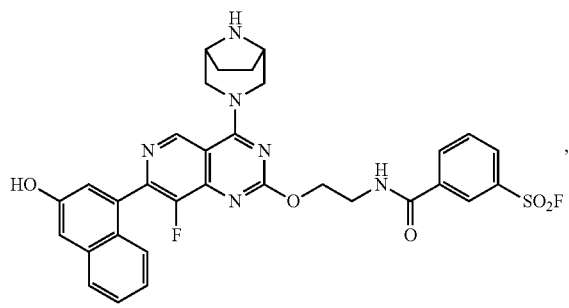

-continued
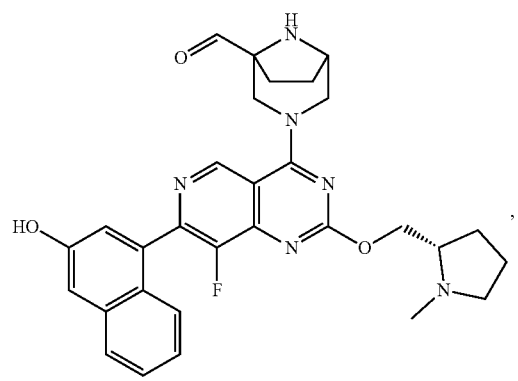
,
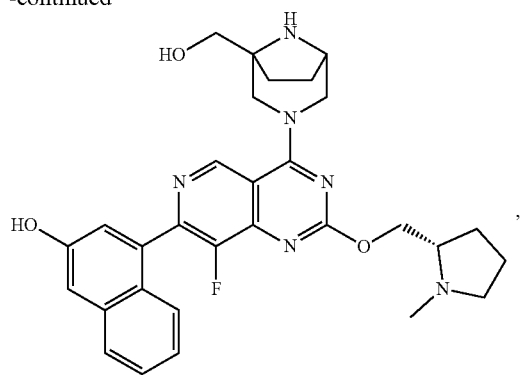
,
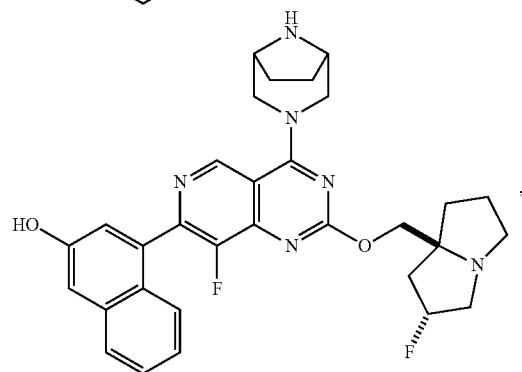
,
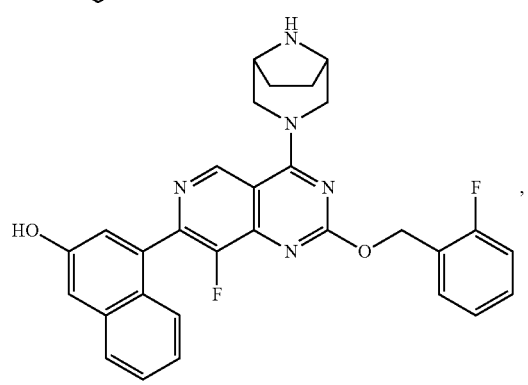
,
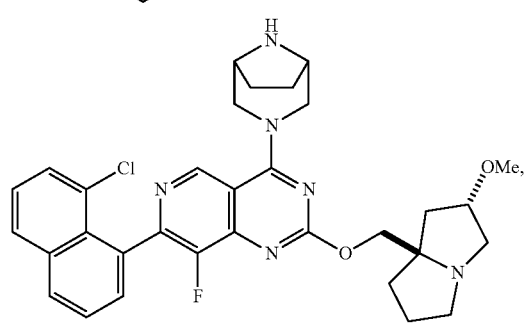
,
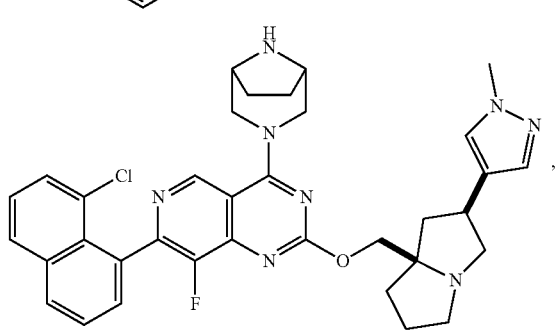
,
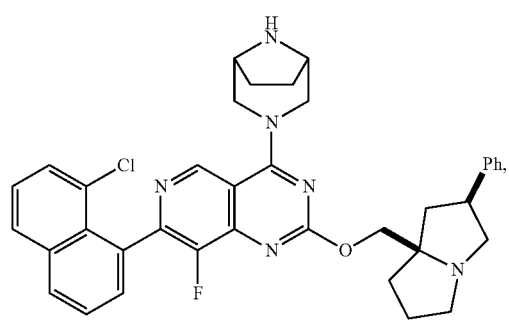
,
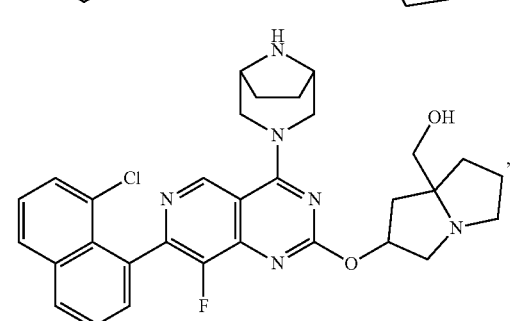
,
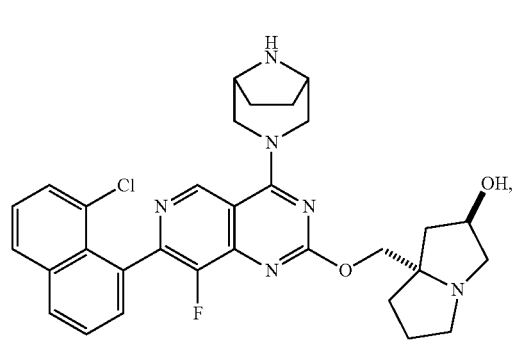
,
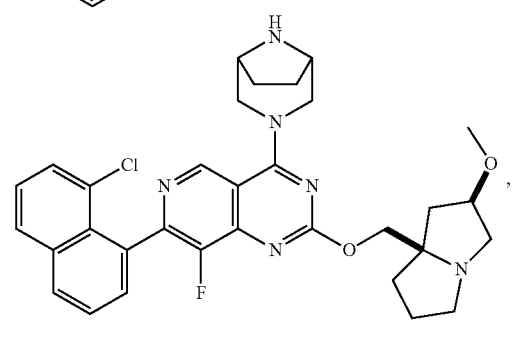
,

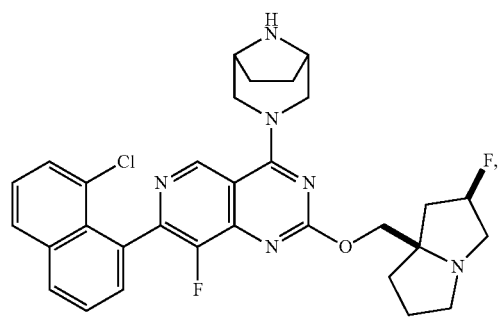
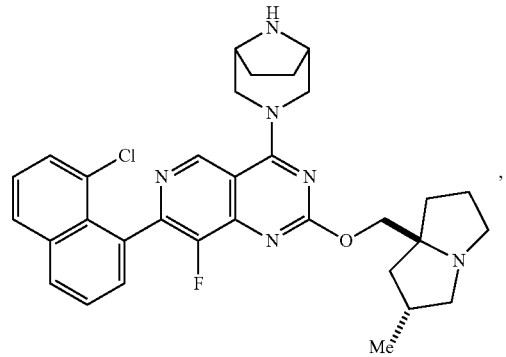
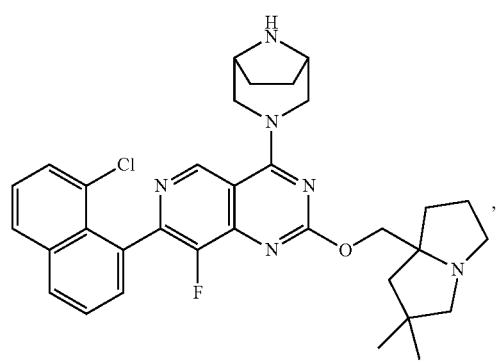
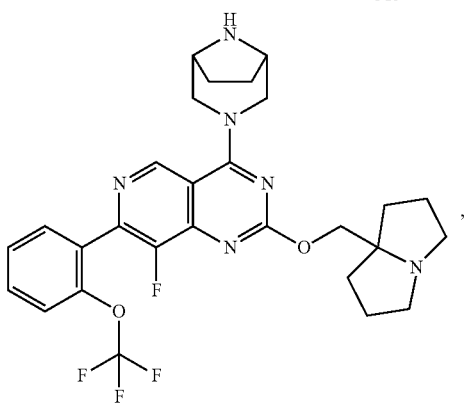
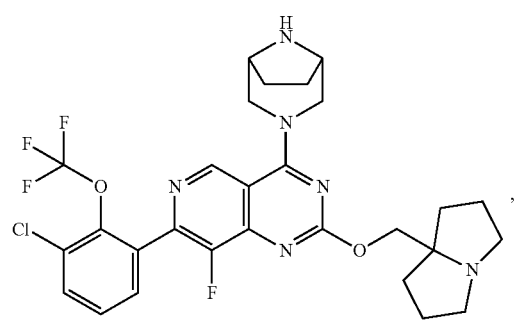
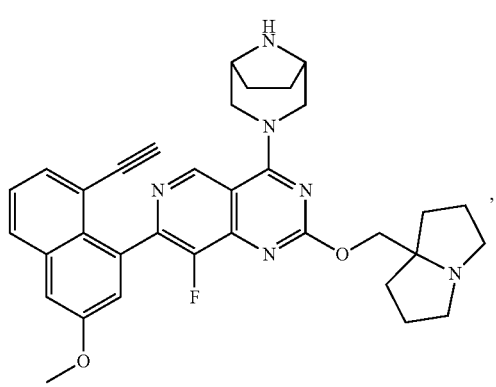
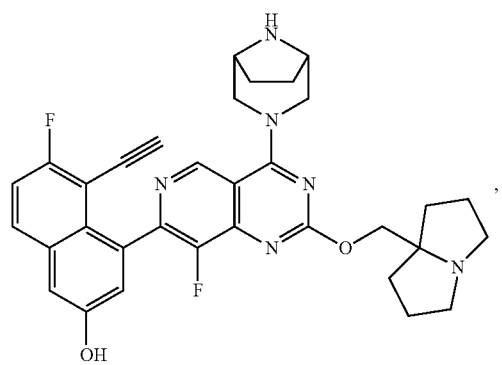
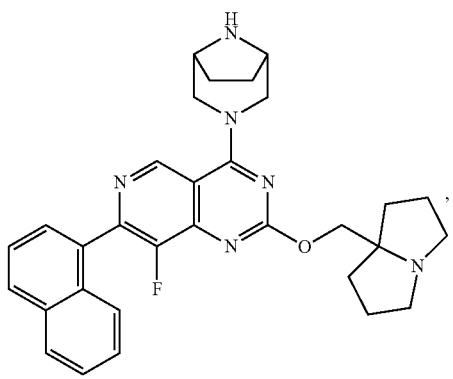

71
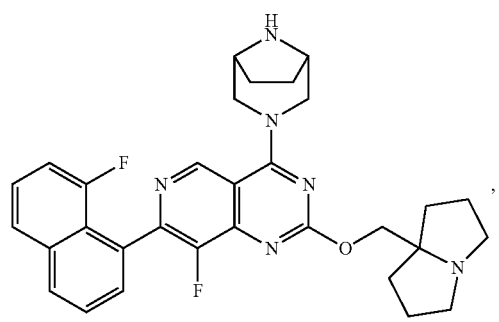
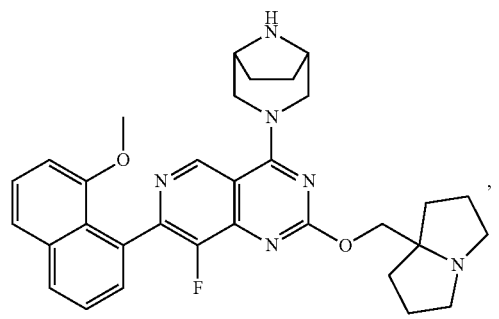
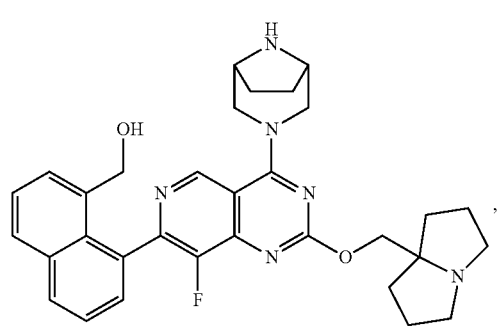
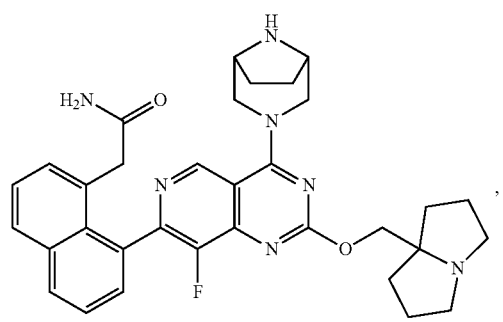
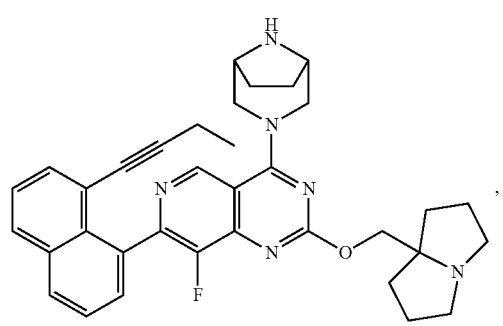
72
-continued
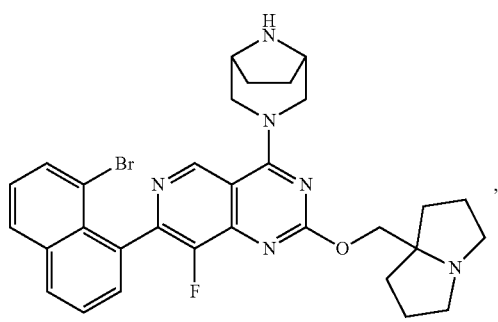
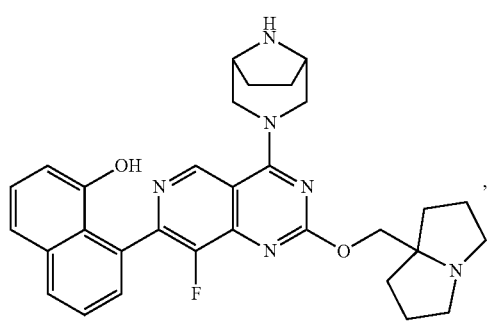
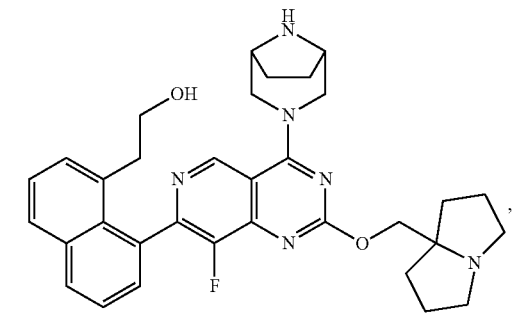
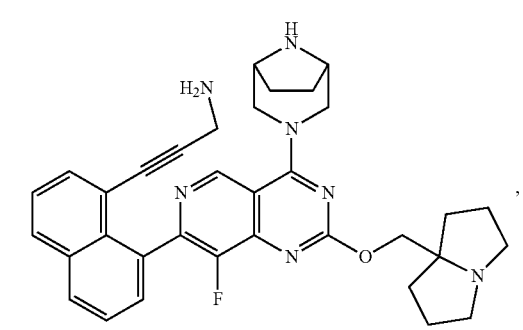
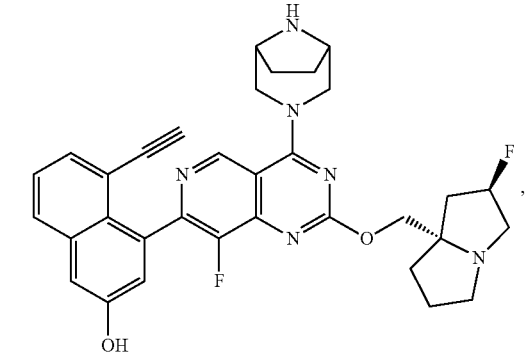

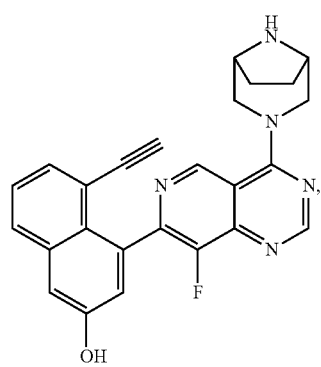
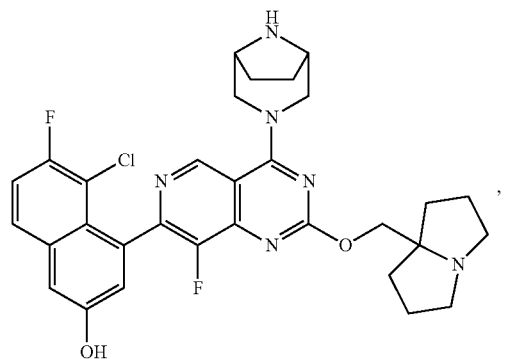
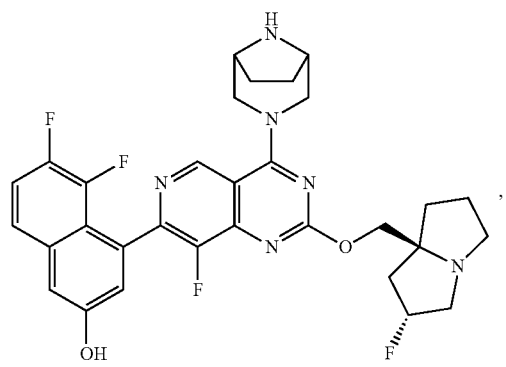
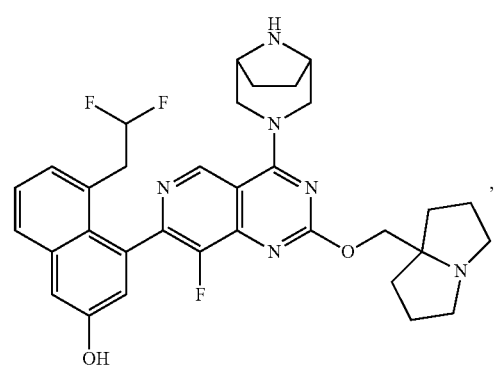
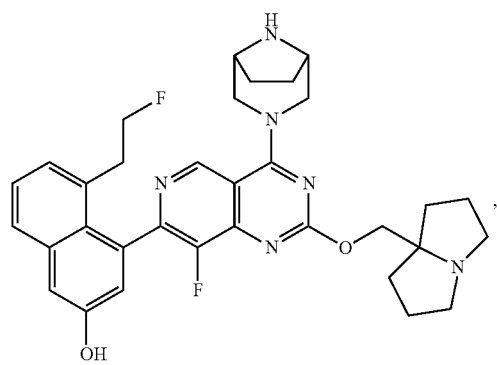
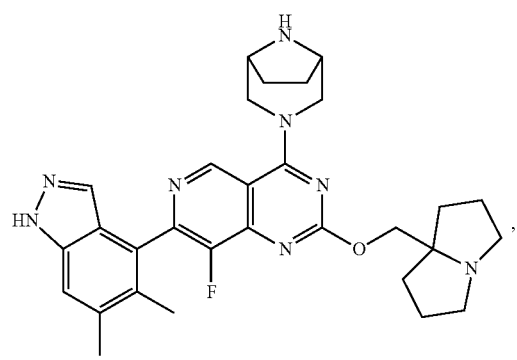
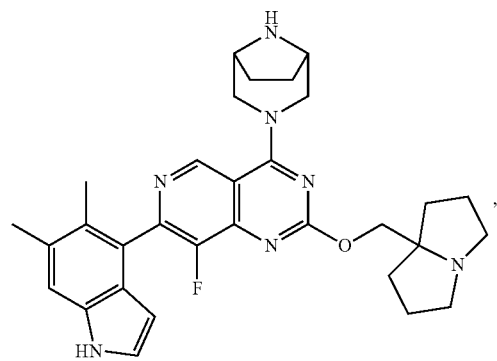
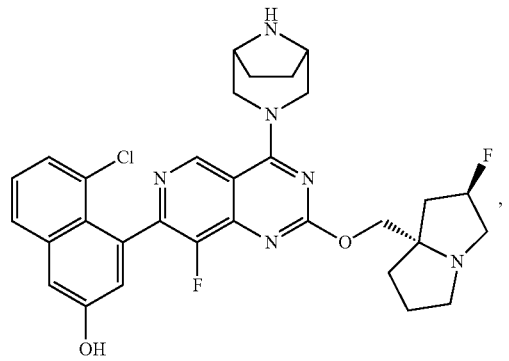

75
76
-continued
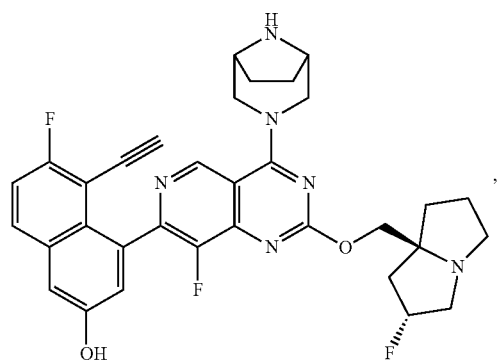
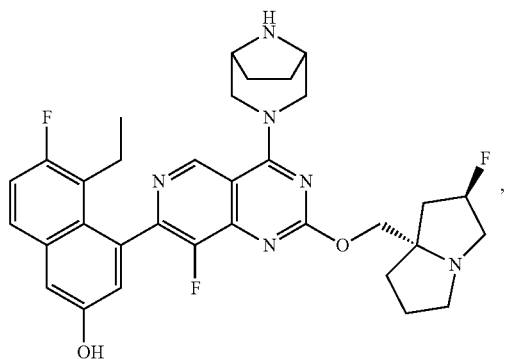
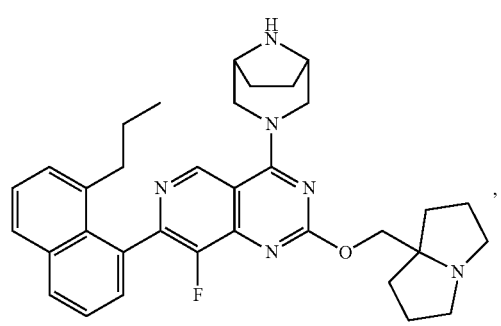
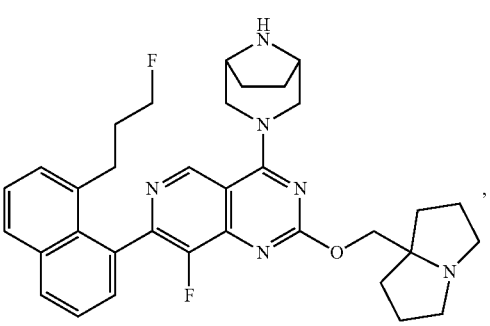
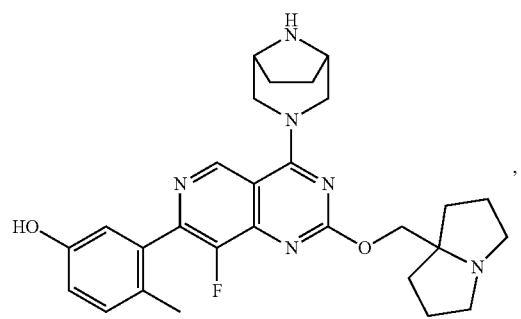
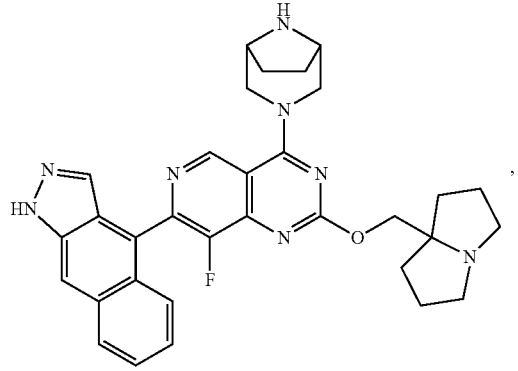
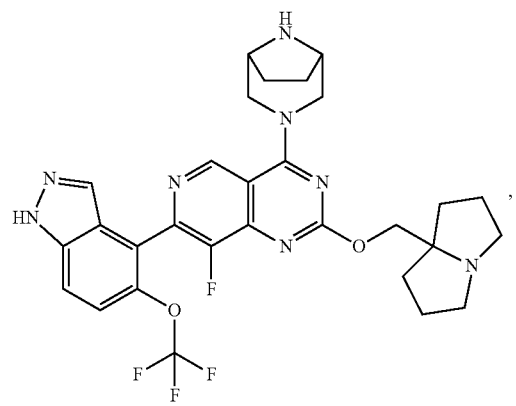
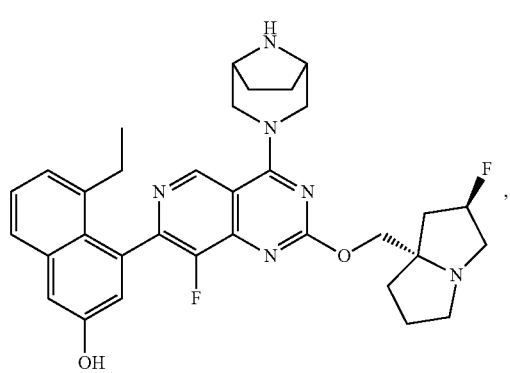

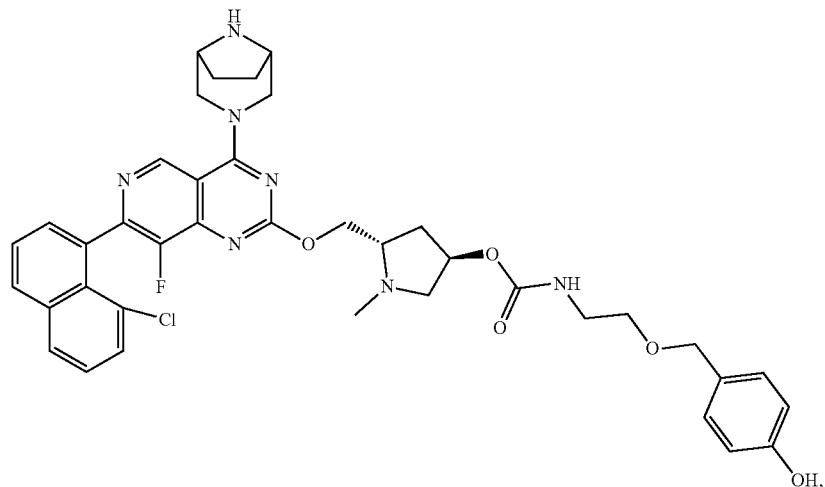
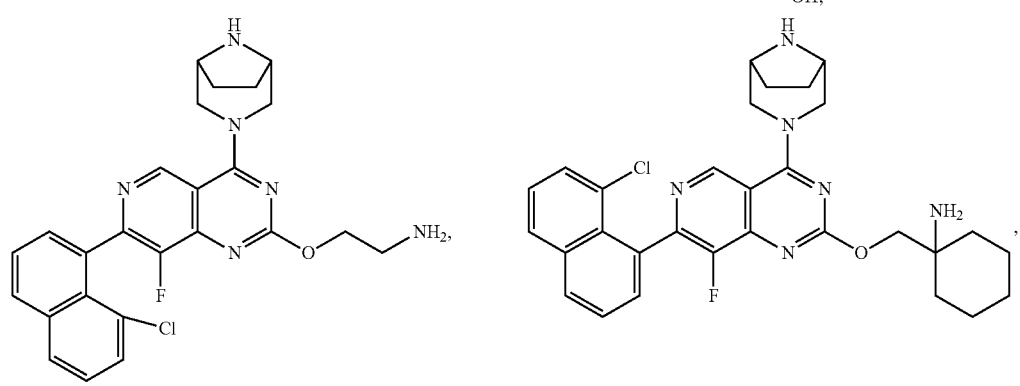
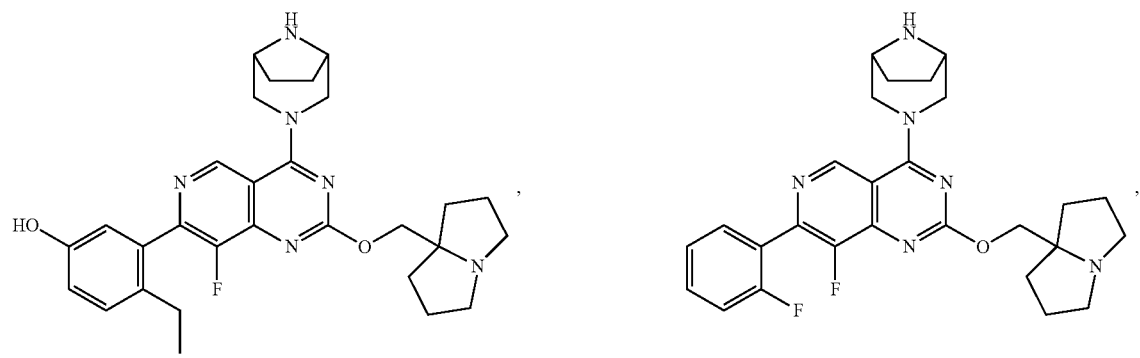
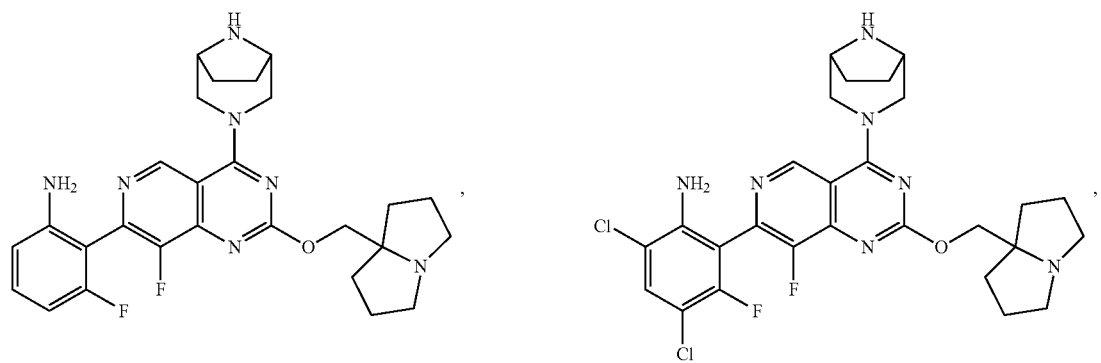

-continued
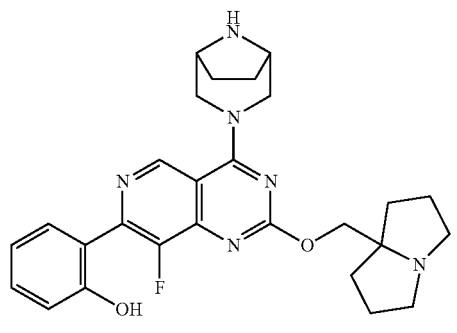
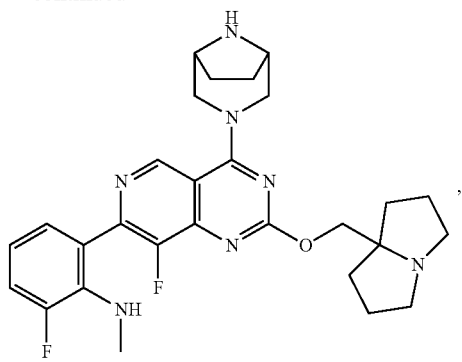
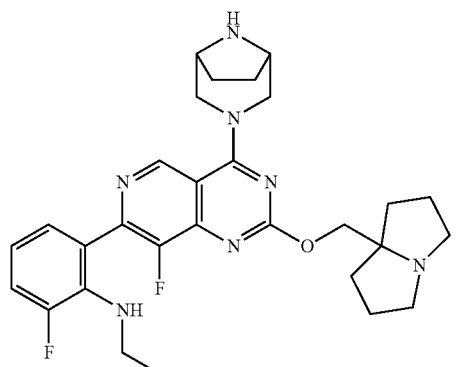
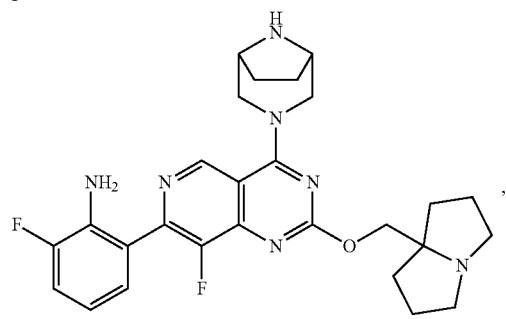
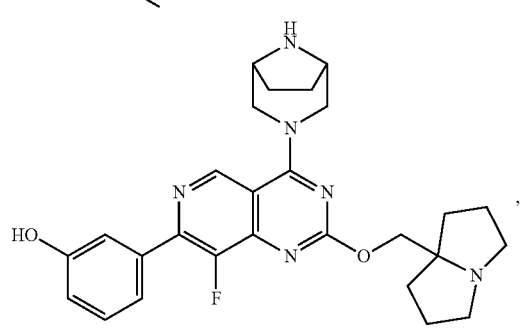
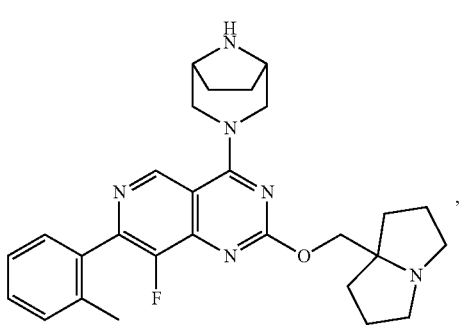
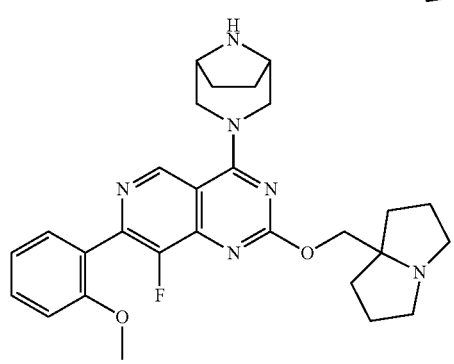
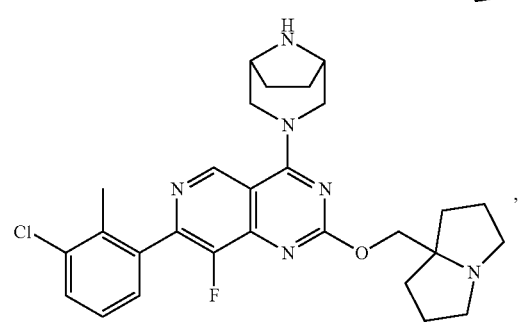
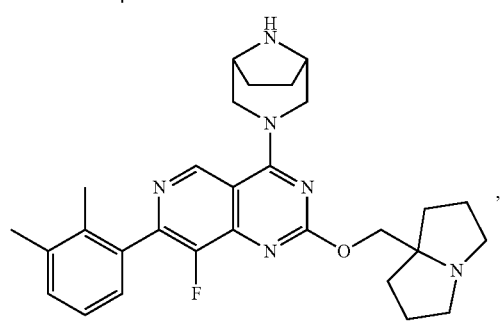
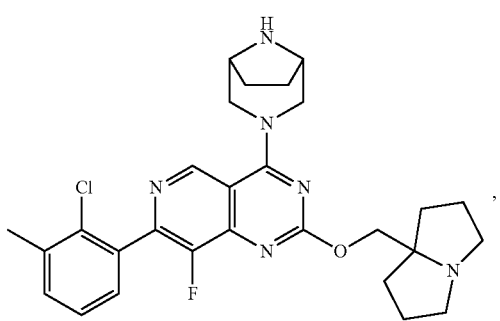

-continued
81
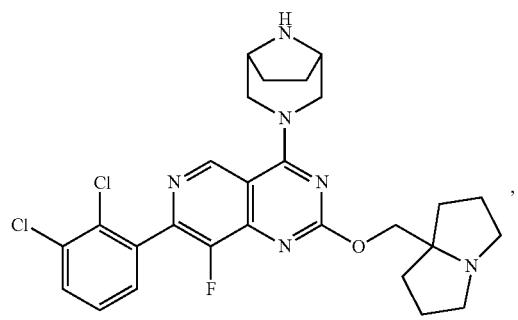
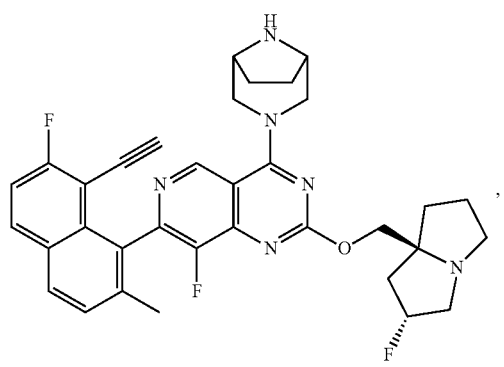
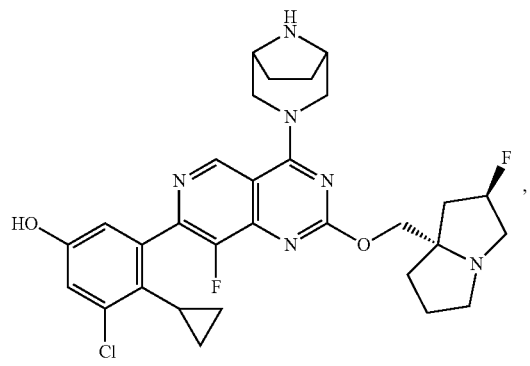
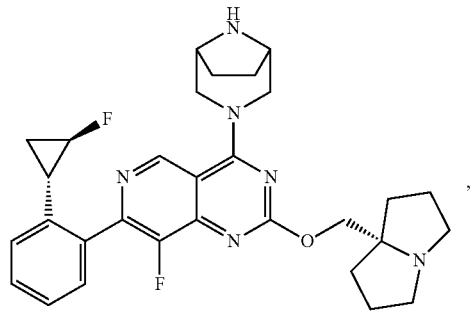
82
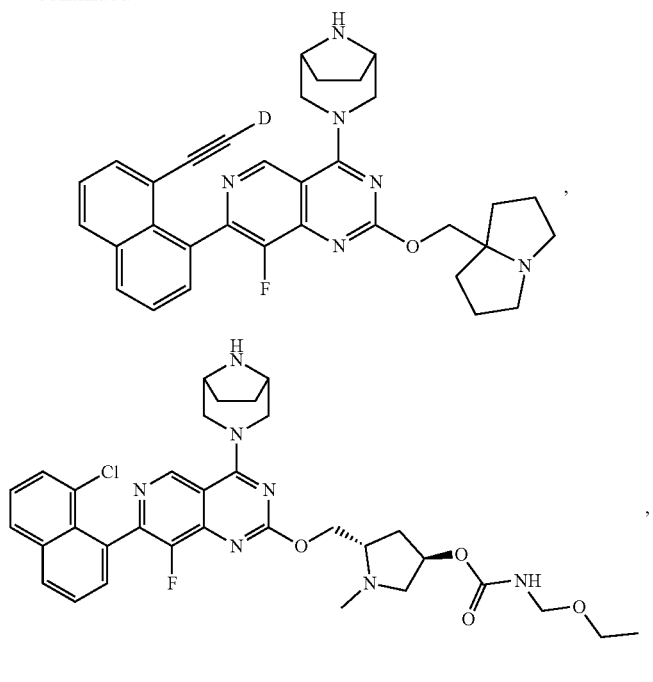
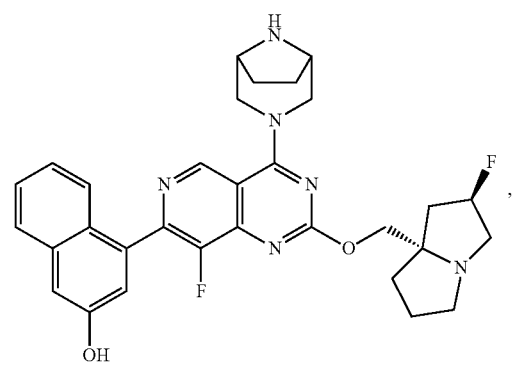
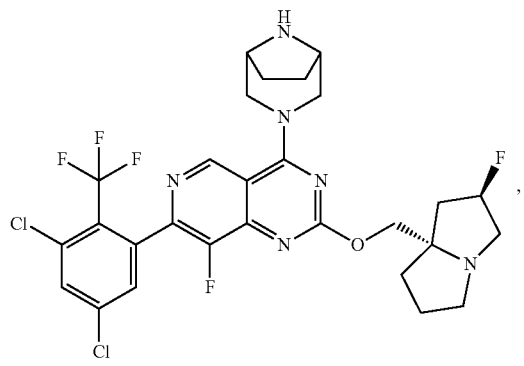
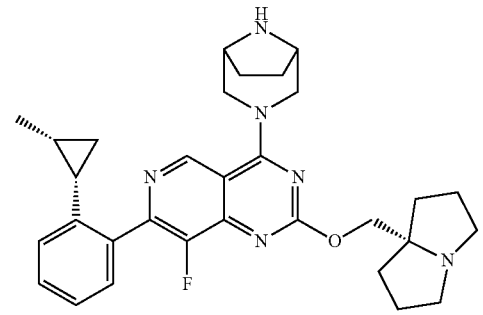

-continued
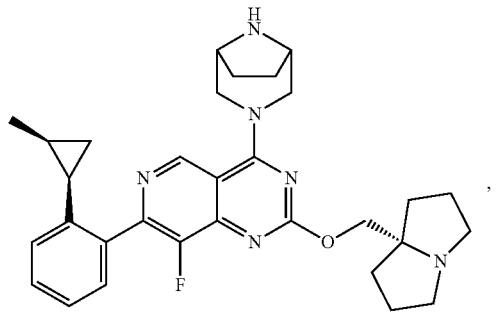,
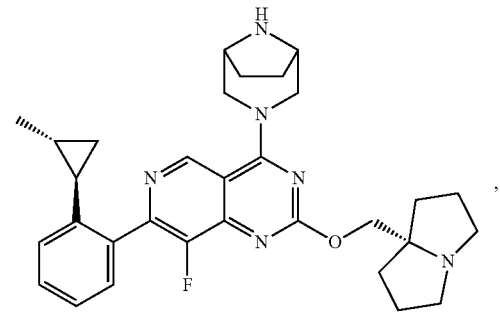,
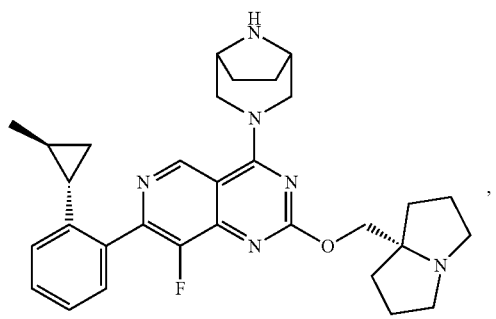,
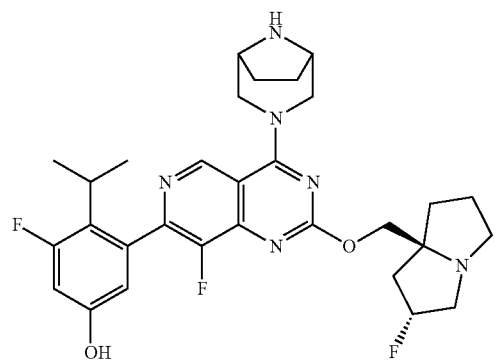,
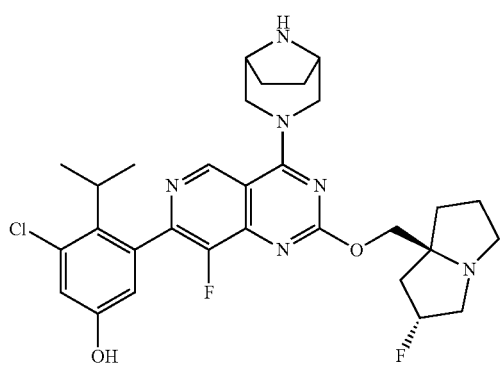,
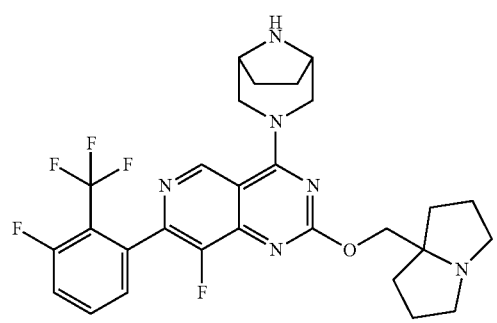,
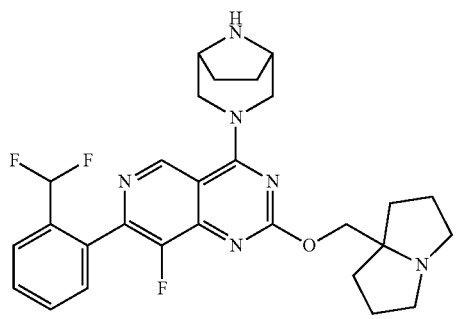,
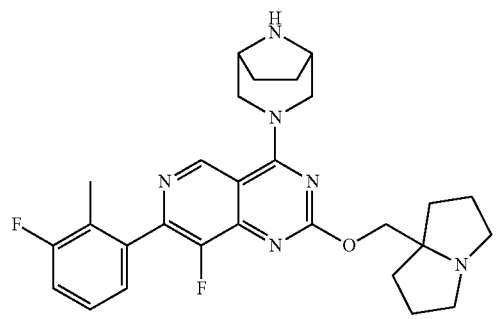,
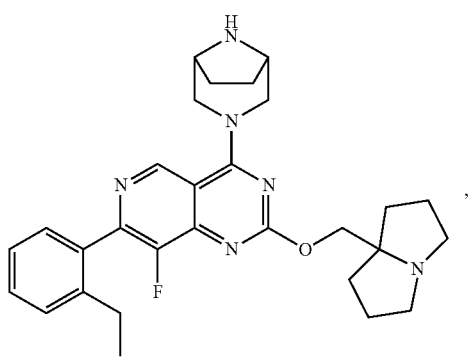,
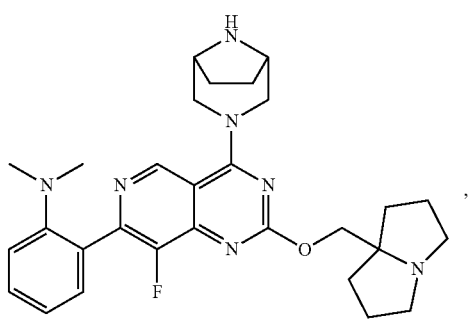,

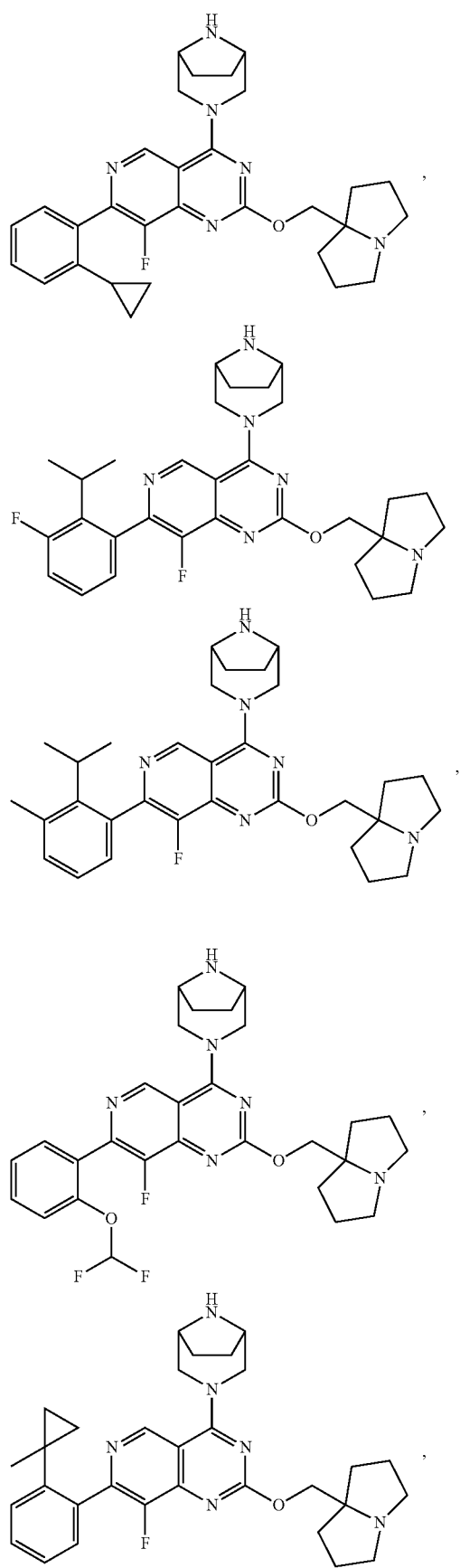
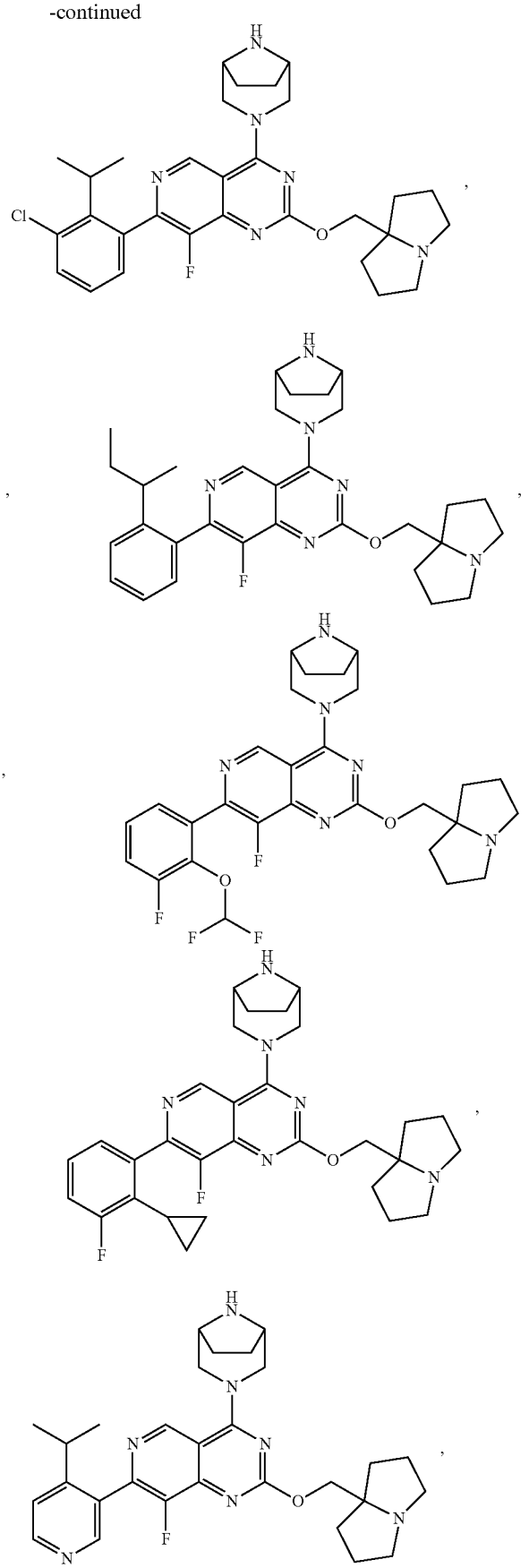

-continued
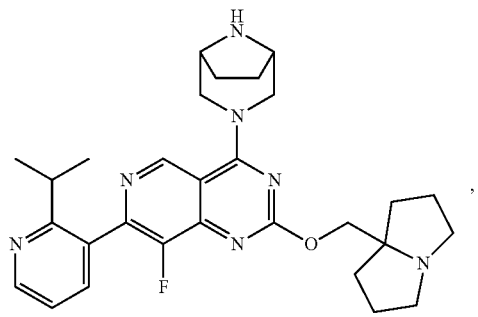
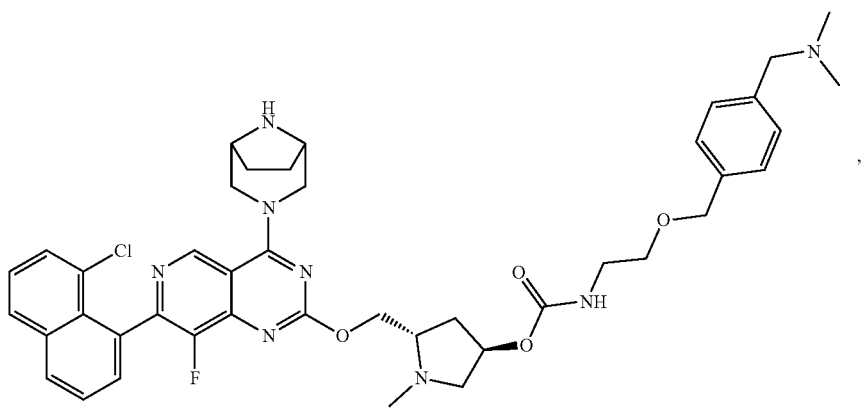
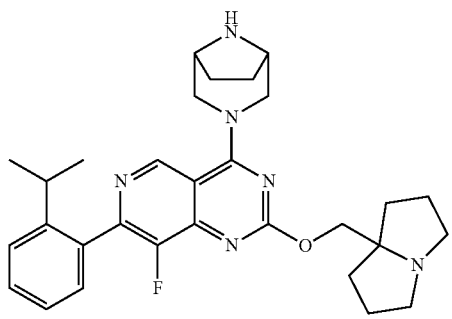, 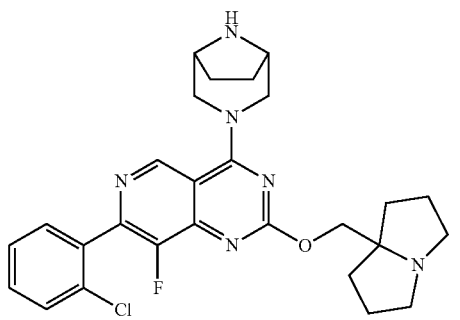,
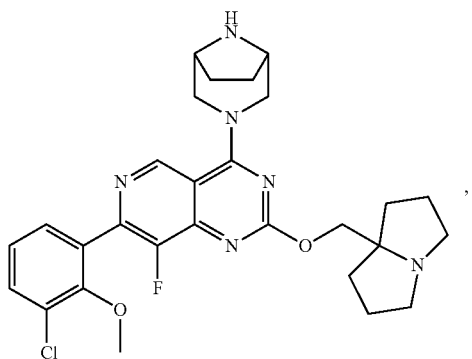, 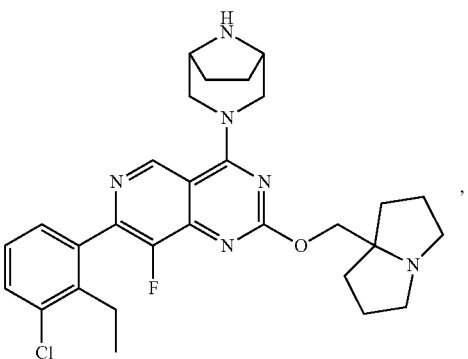, 89
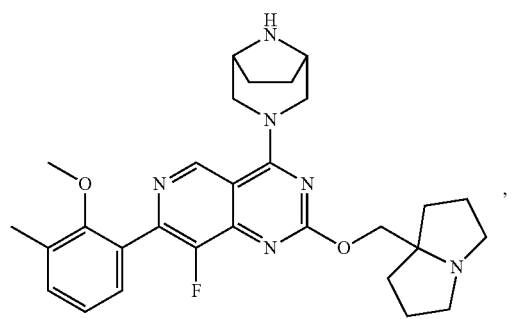,
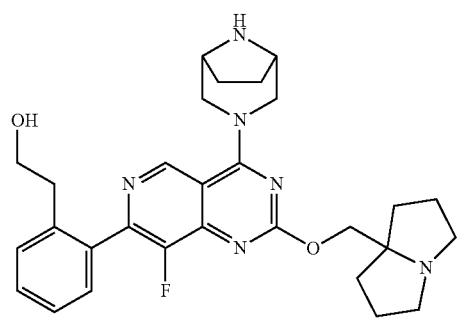,
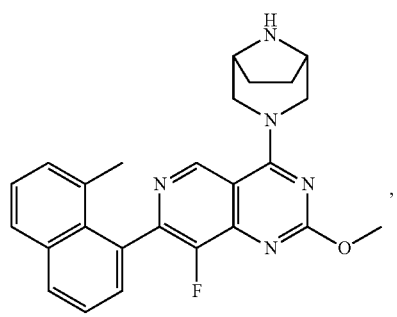,
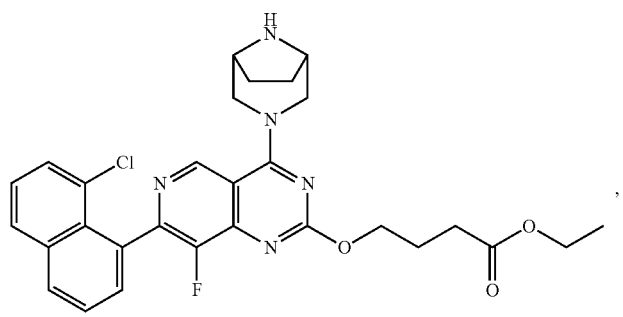,
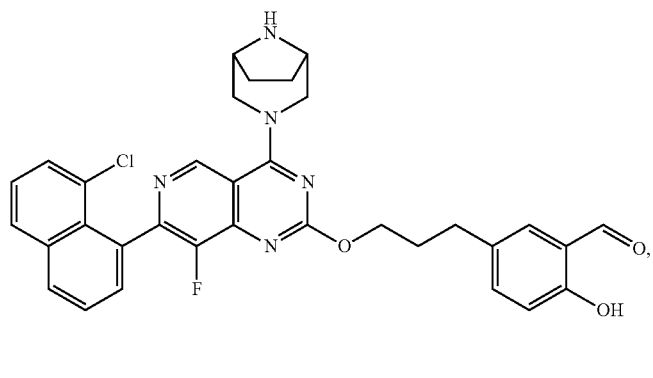,
90
-continued
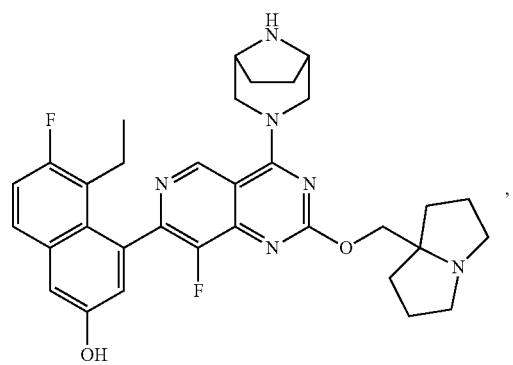,
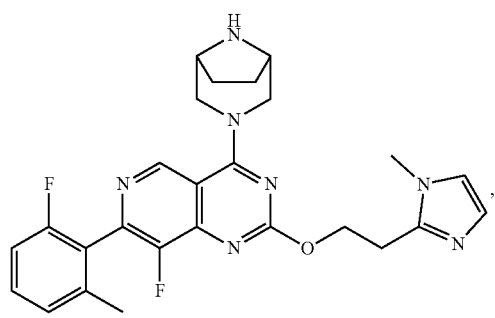,
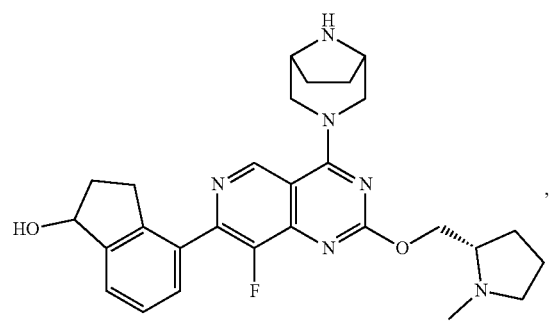,
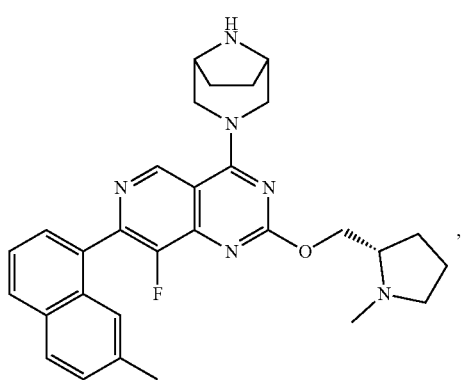, 91
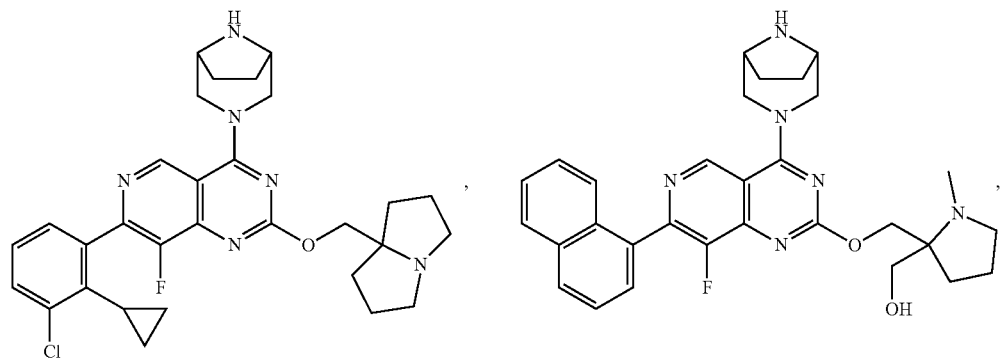
92
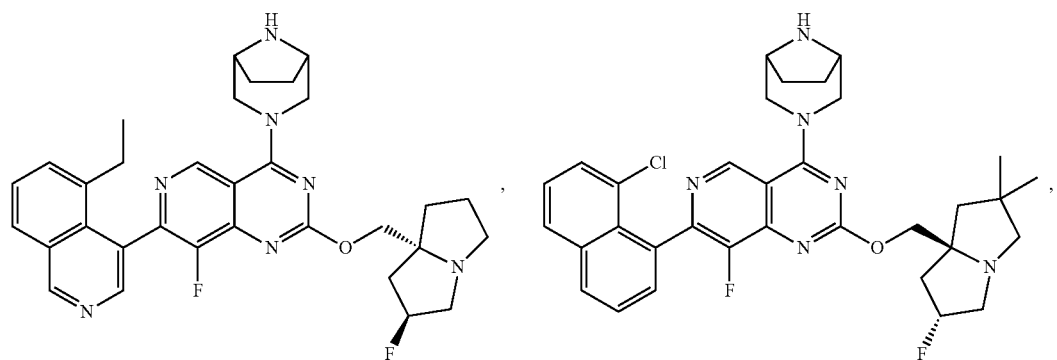
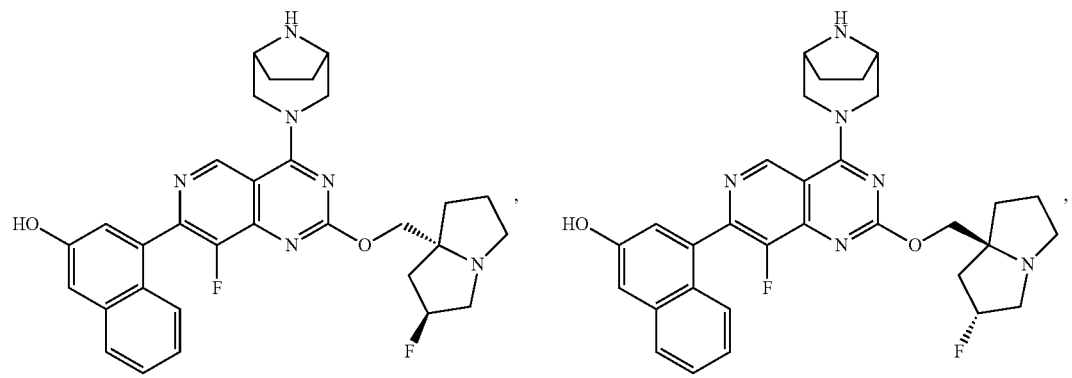
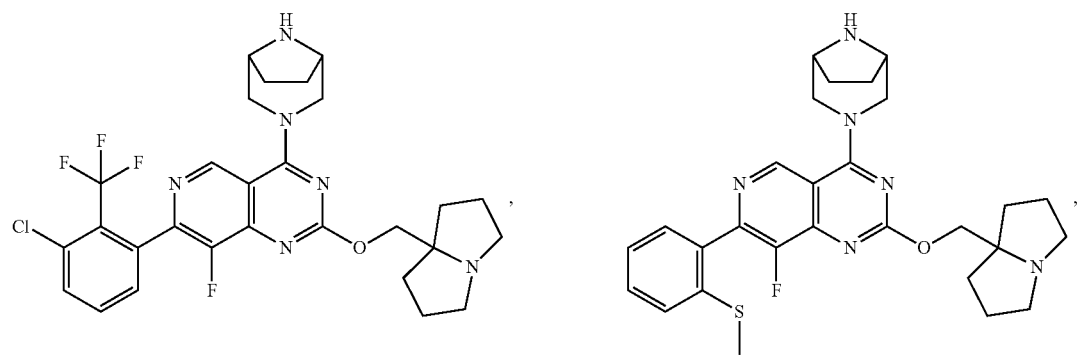

93
94
-continued
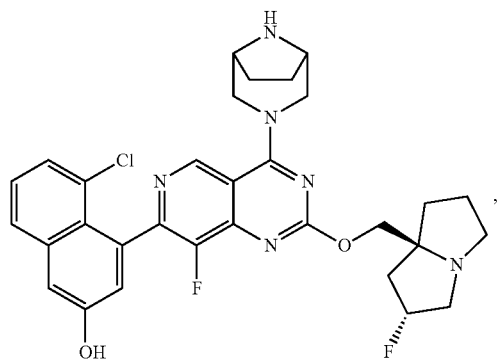
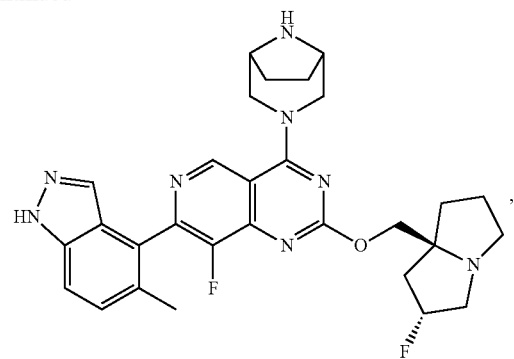
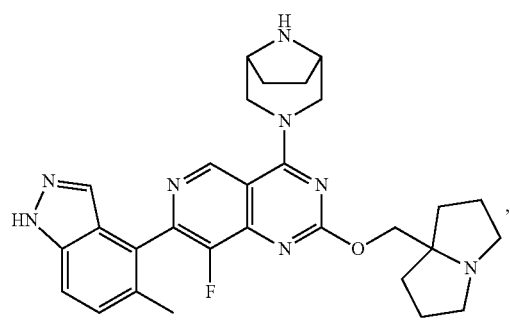
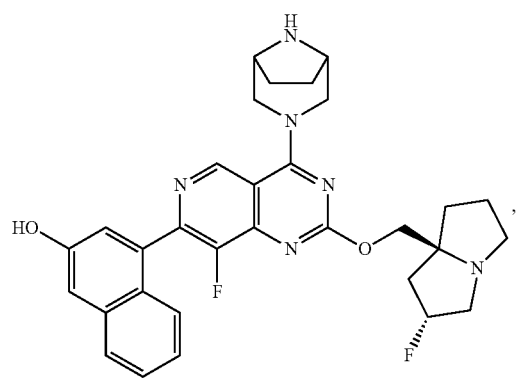
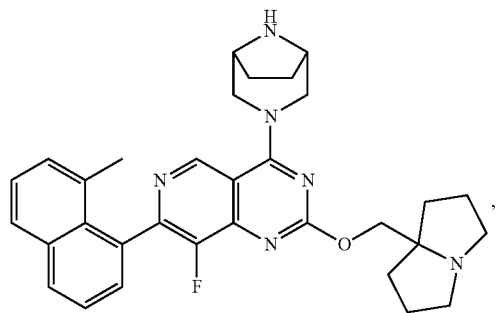
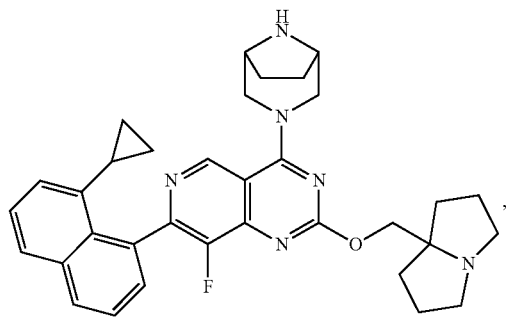
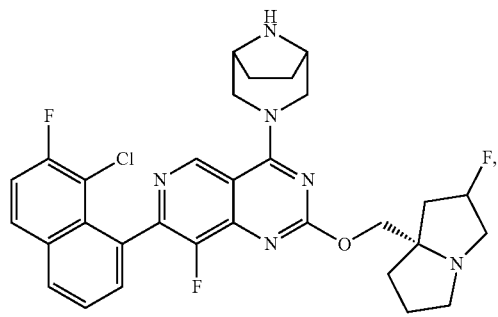
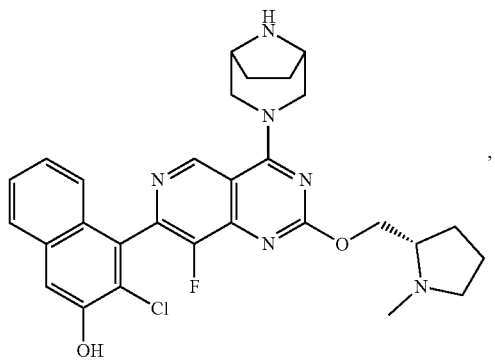

-continued
95
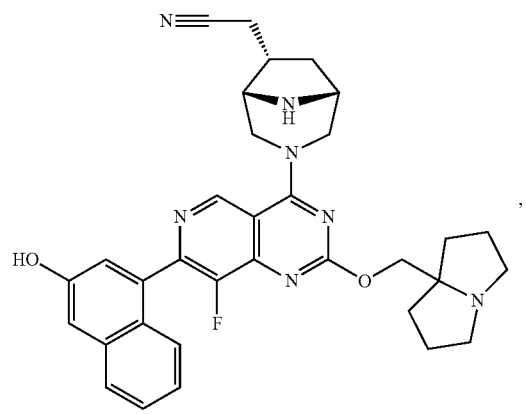
96
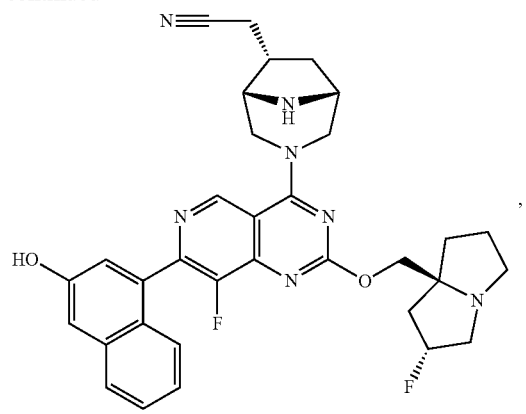
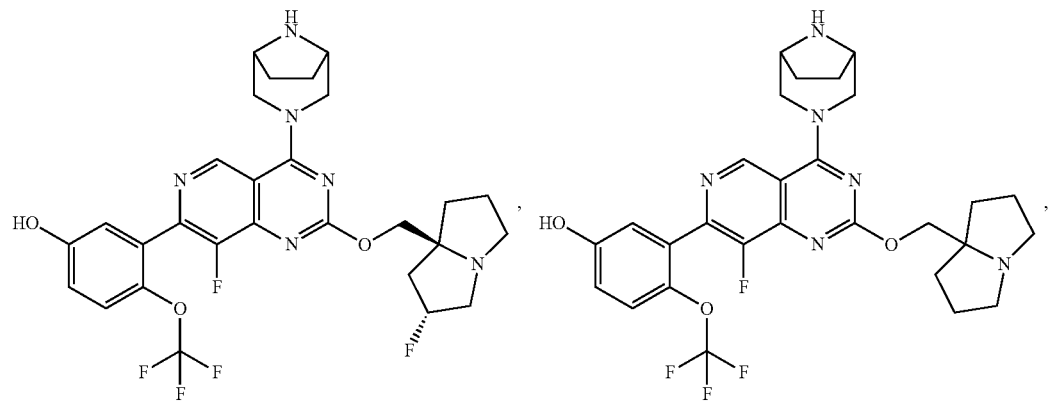
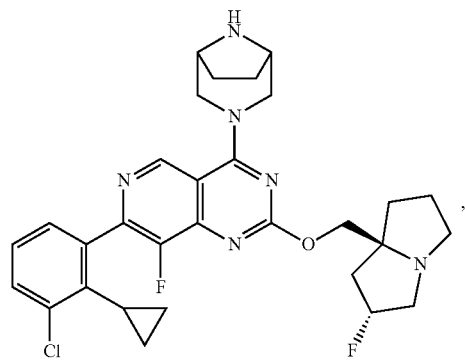
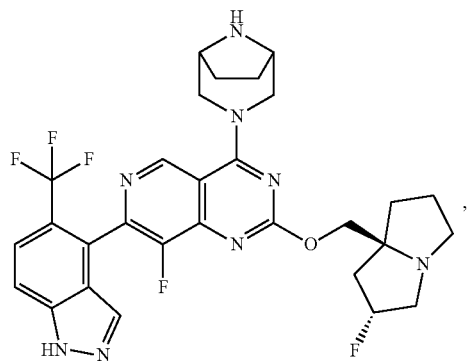
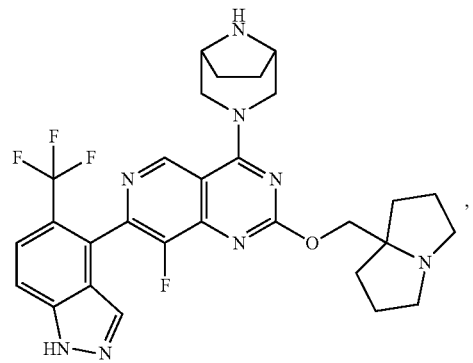
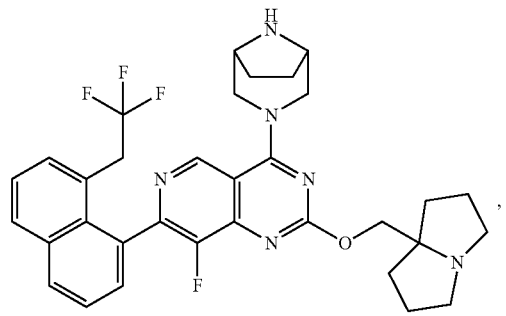

-continued
97
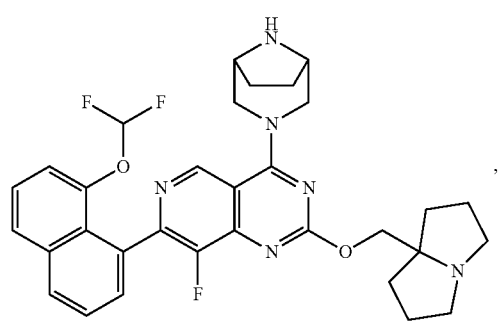,
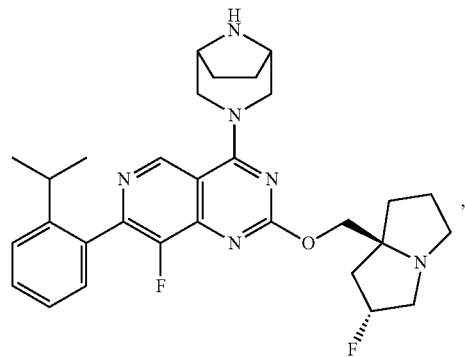,
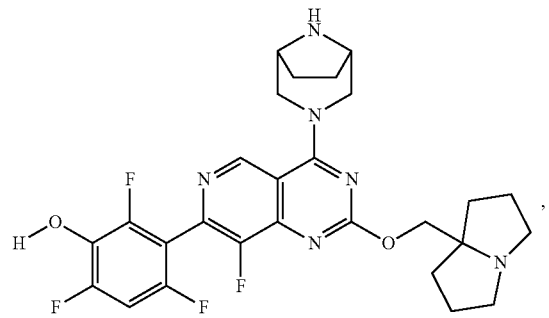,
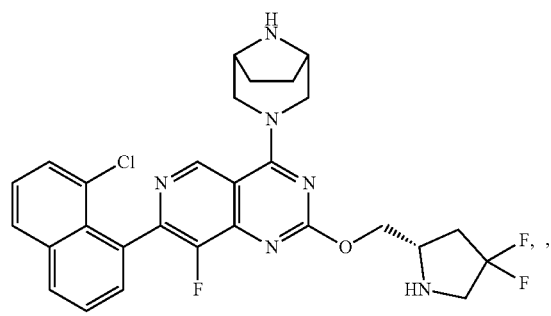,
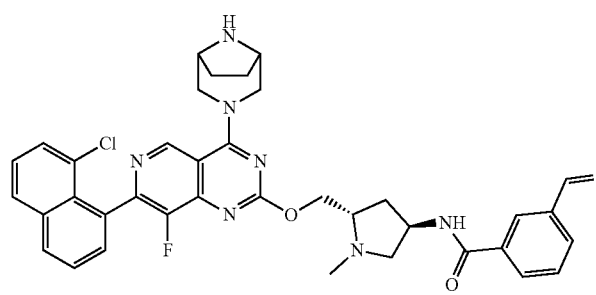,
98
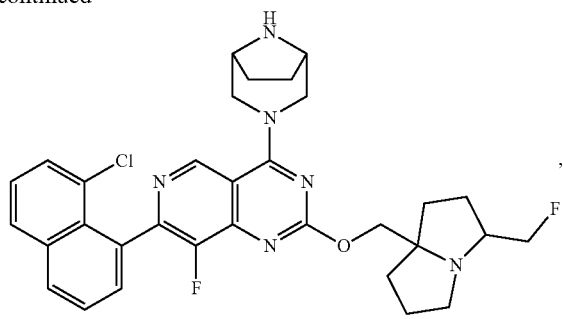,
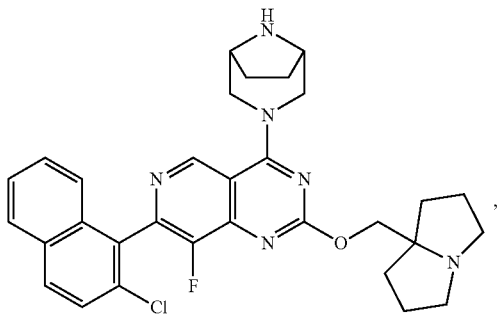,
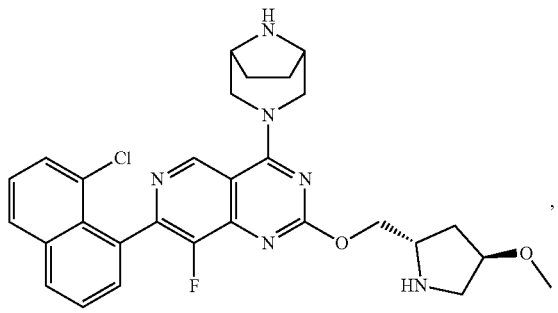,
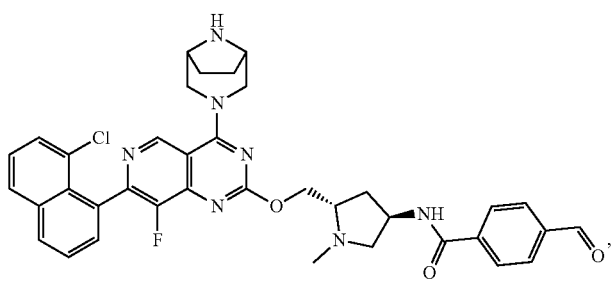,
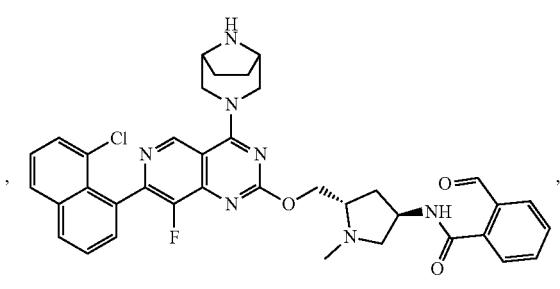, -continued
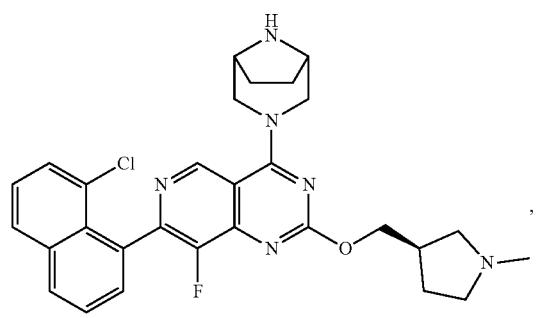 99
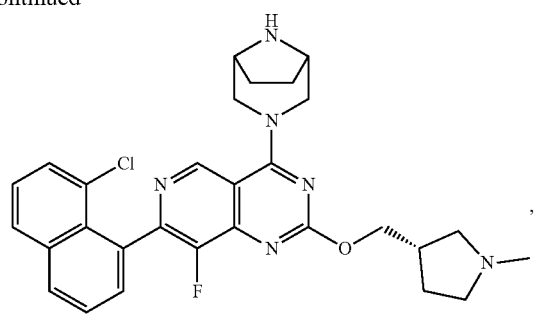 100
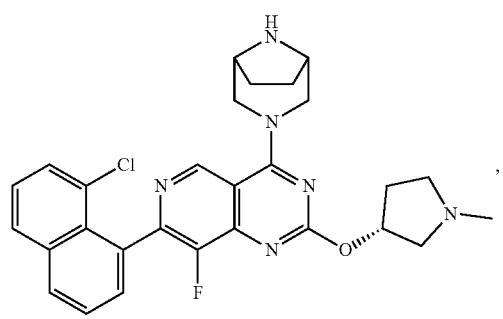
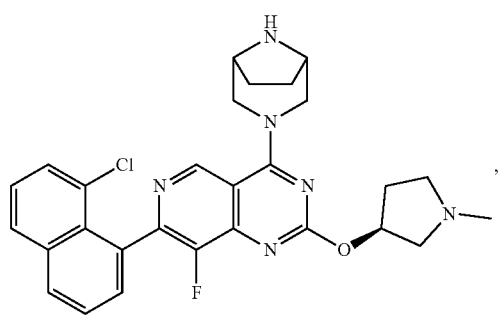
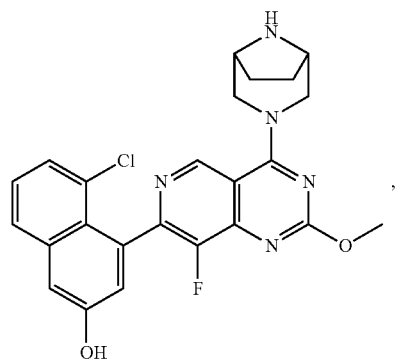
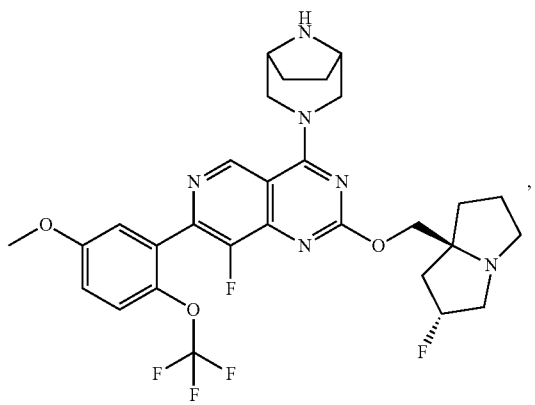
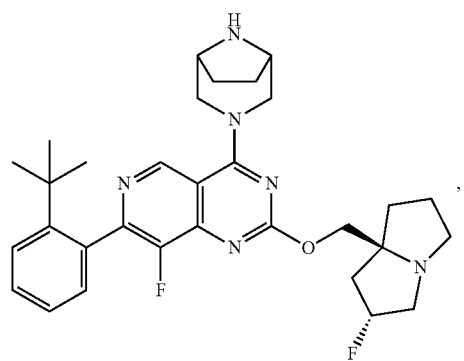
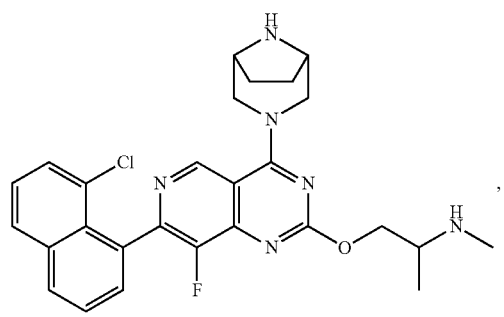

-continued
101
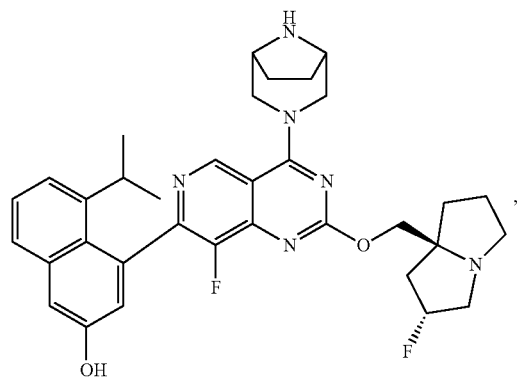
102
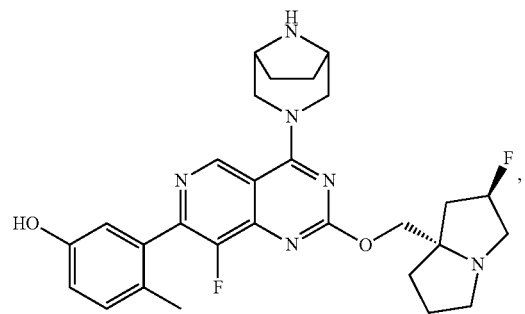
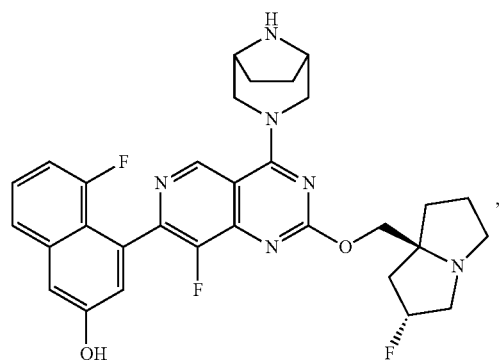
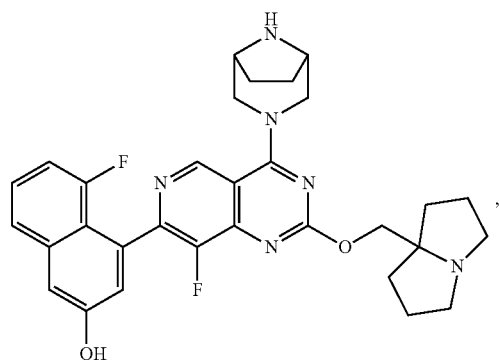
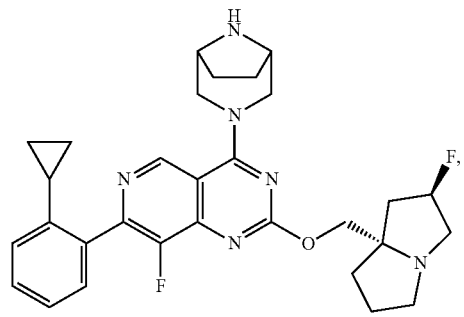
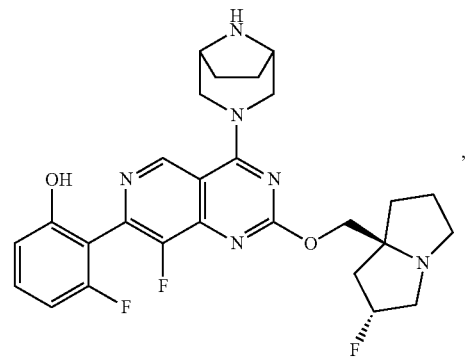
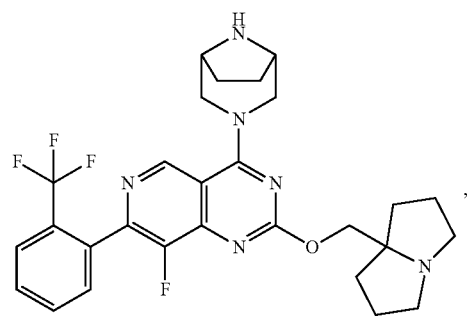
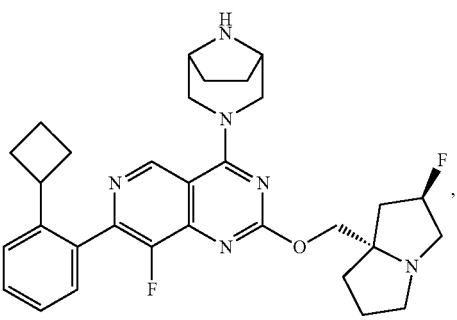

103
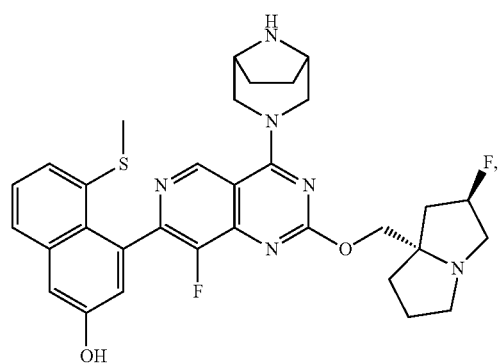
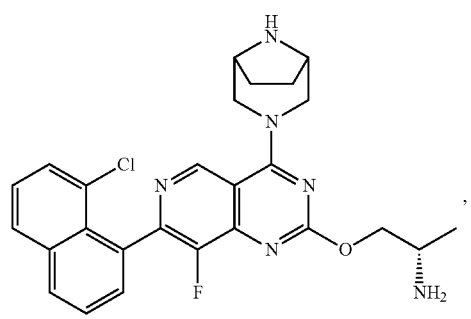
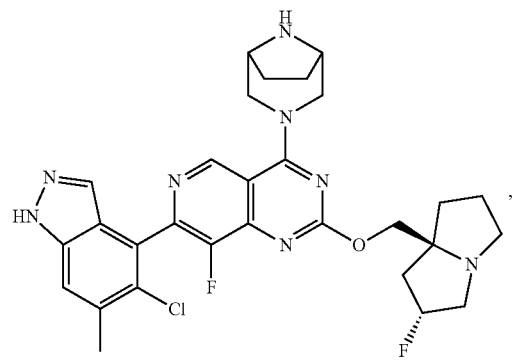
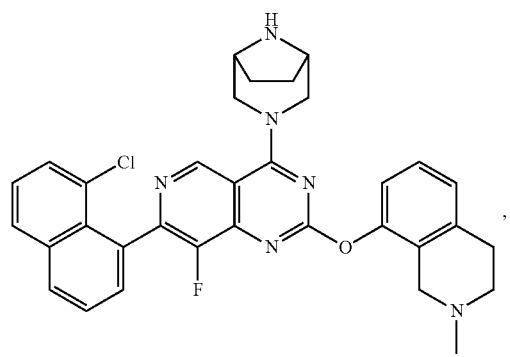
104
-continued
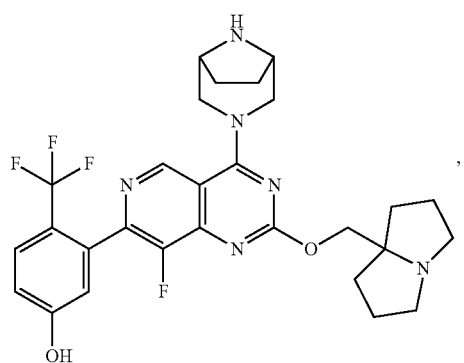
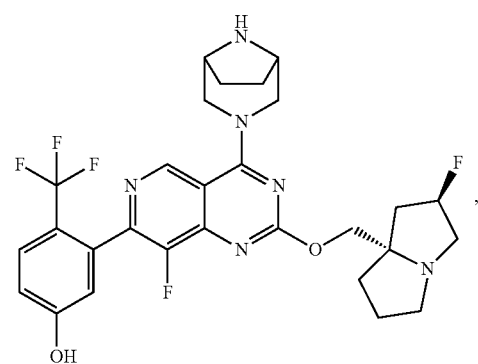
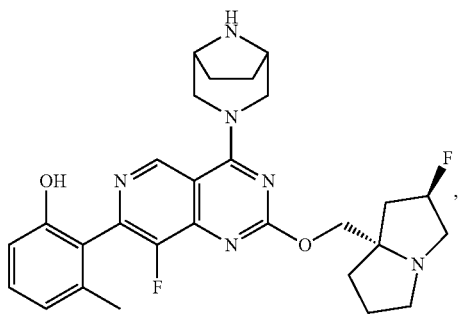
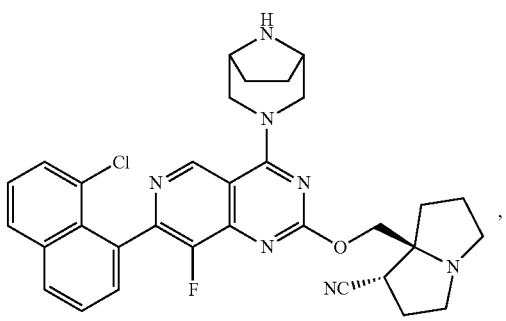

105
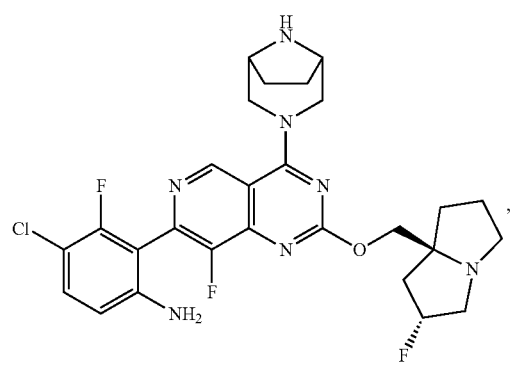
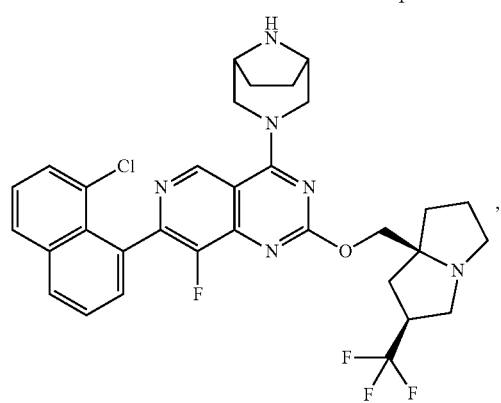
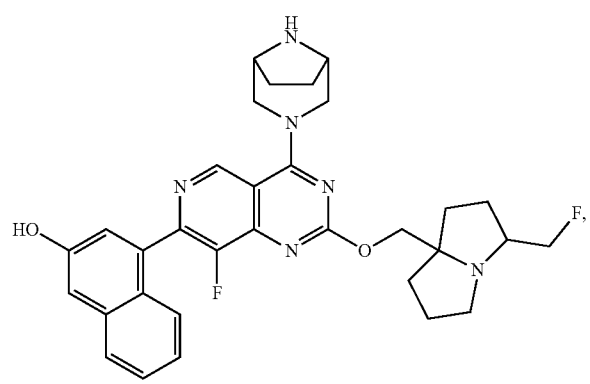
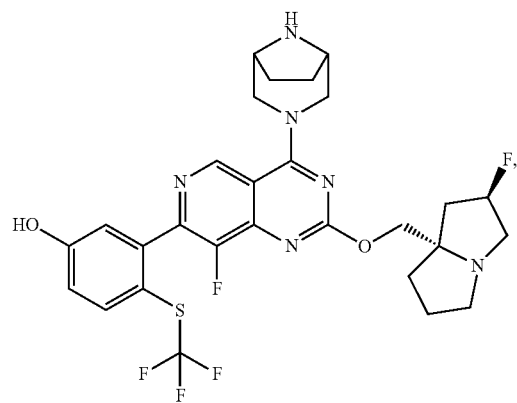
106
-continued
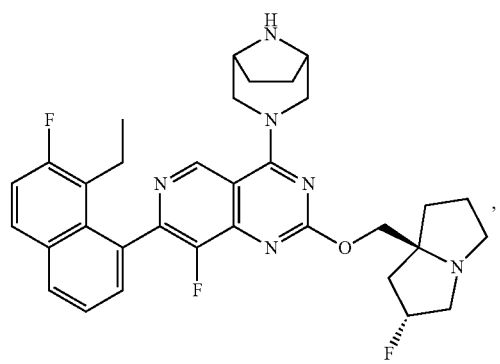
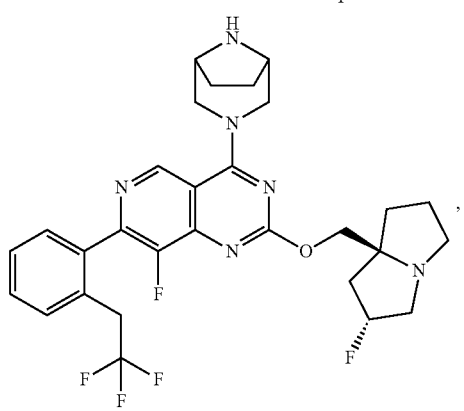
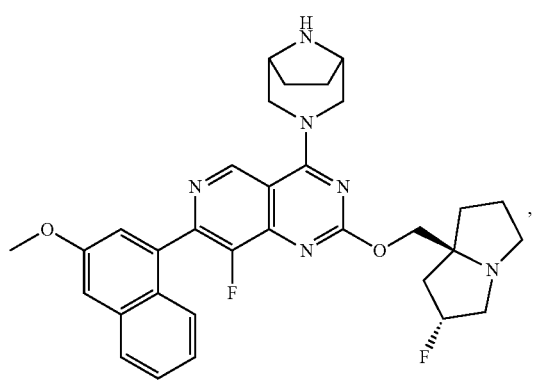
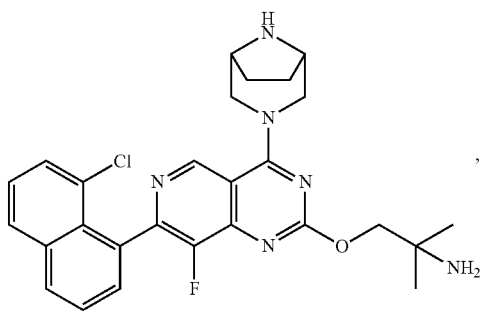

-continued
107
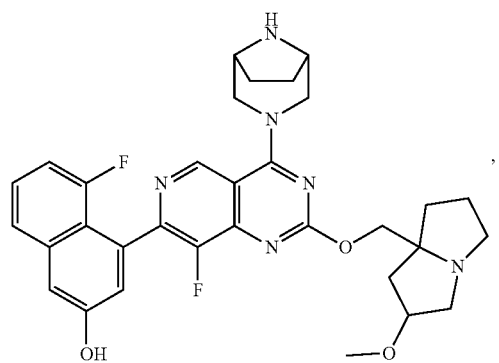
,
108
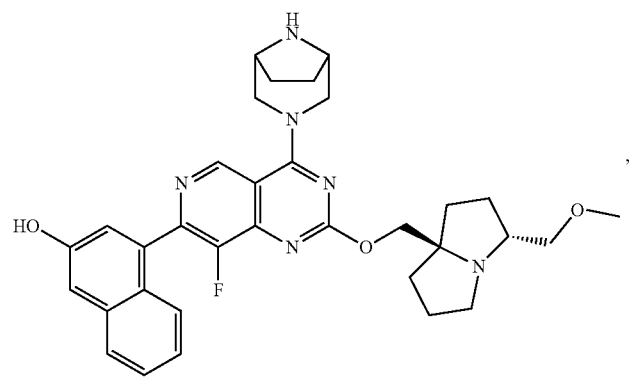
,
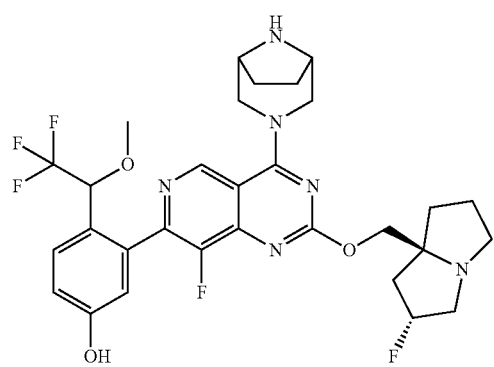
,
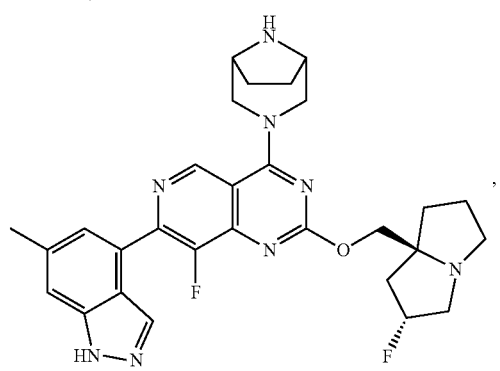
,
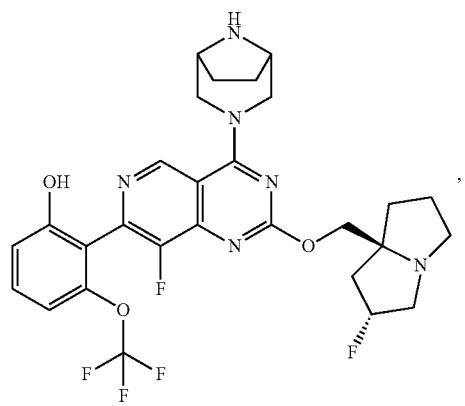
,
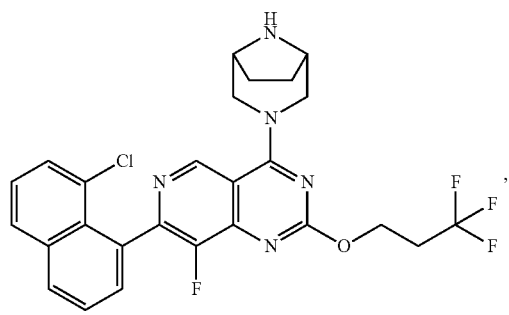
,
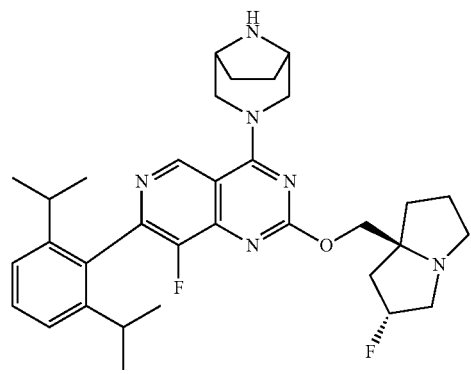
,
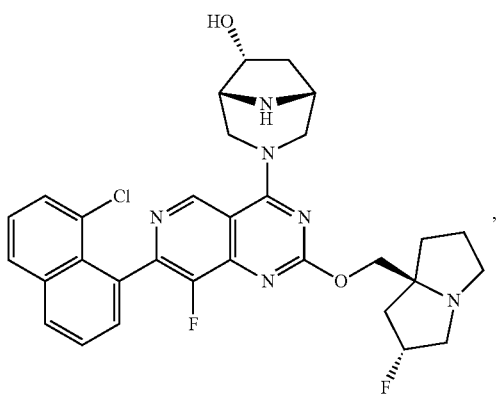
, 109
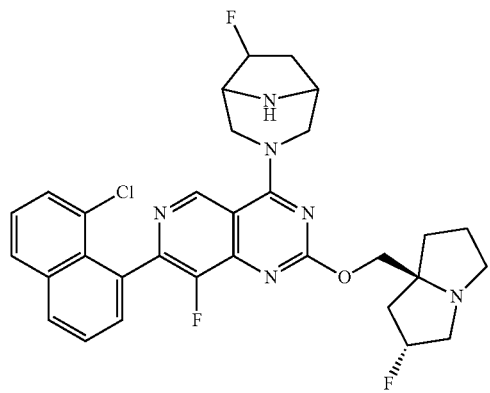
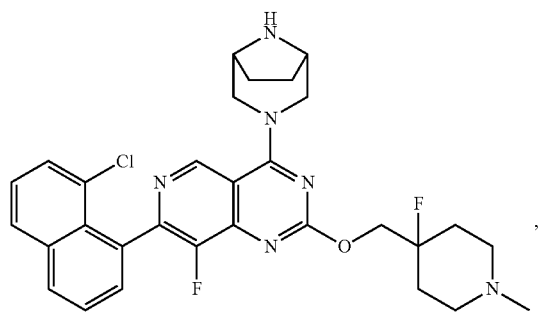
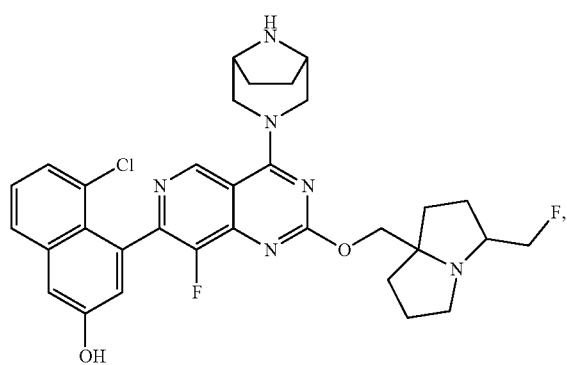
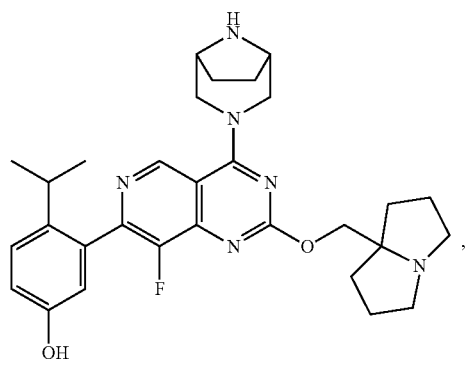
110
-continued
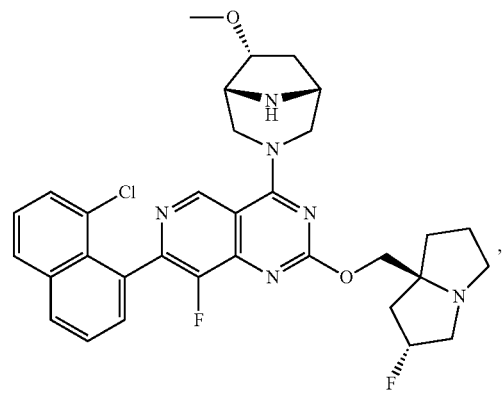
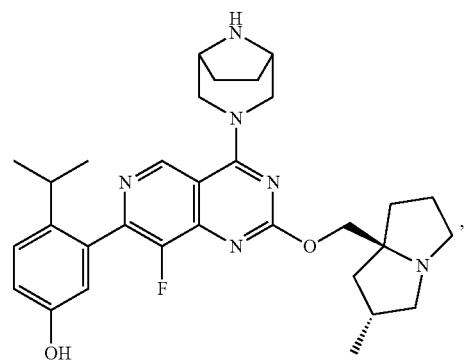
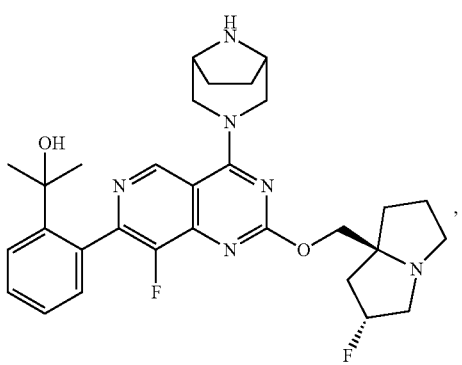
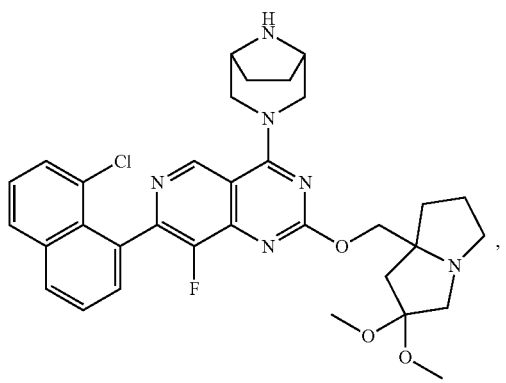

-continued
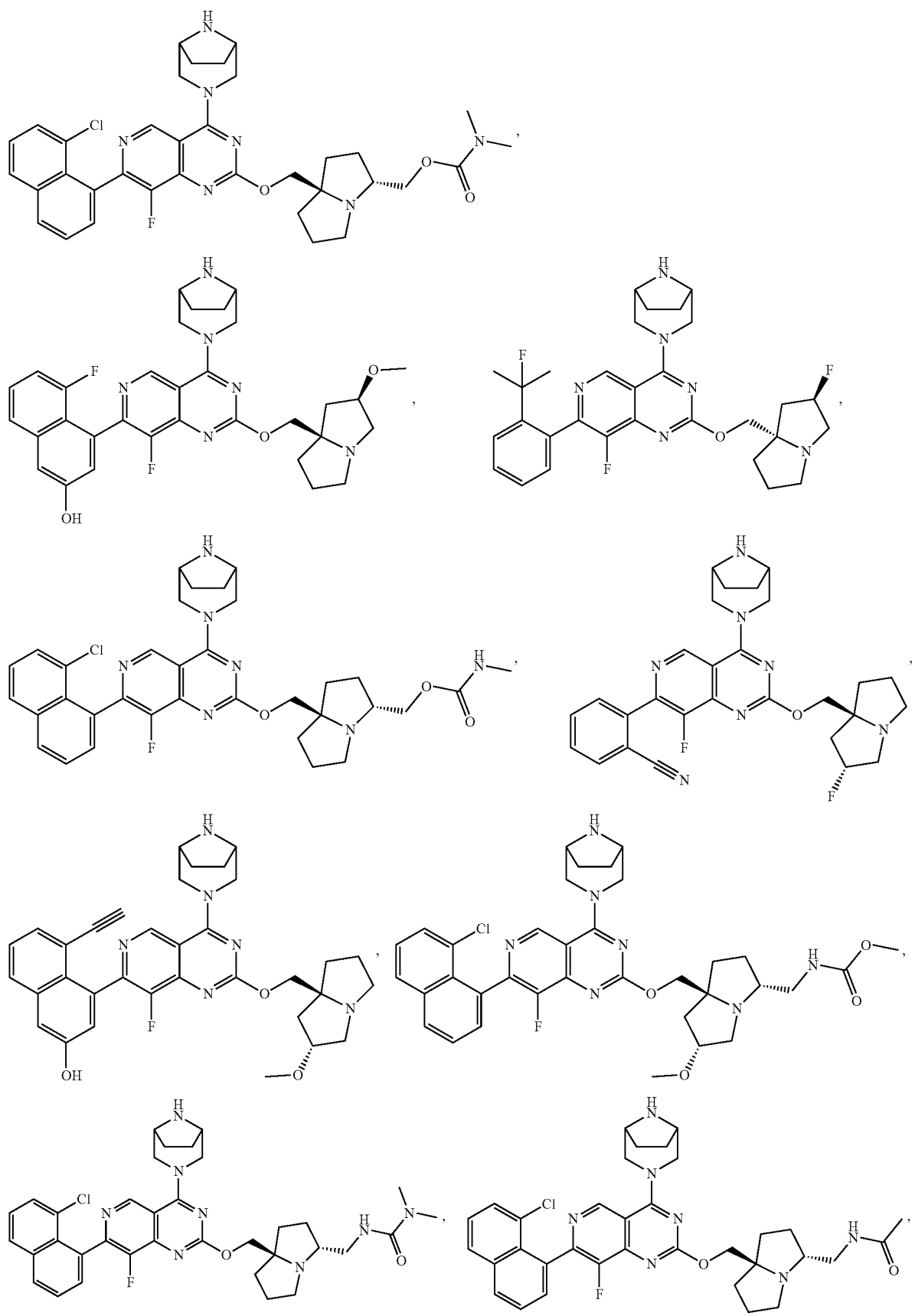

113 114
-continued
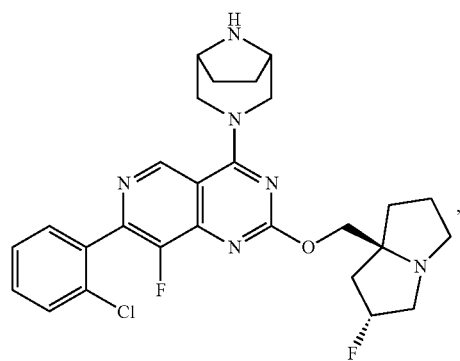, 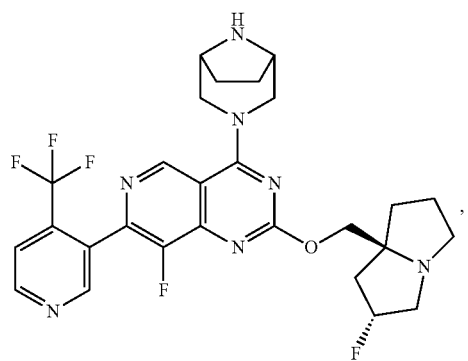,
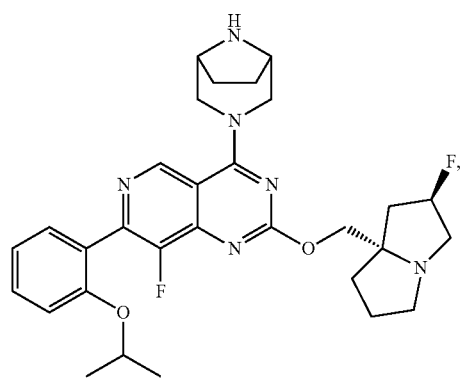, 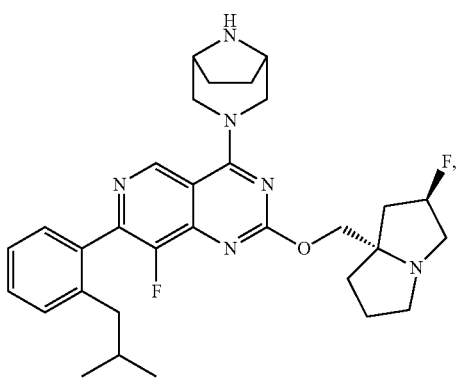,
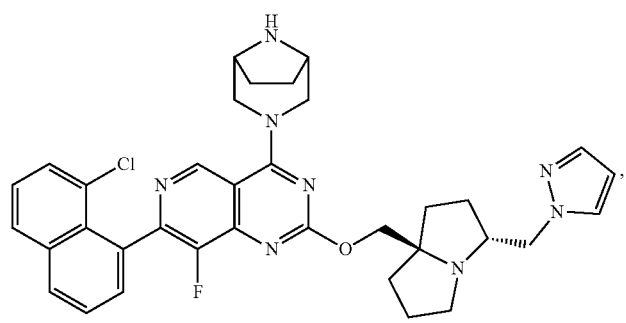, 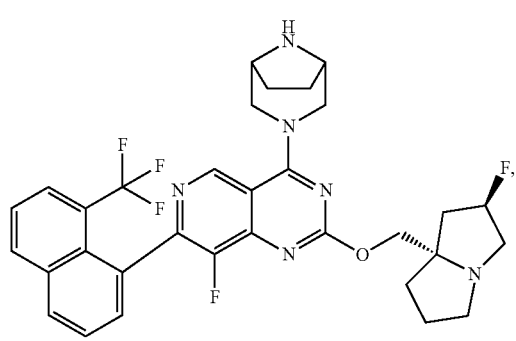,
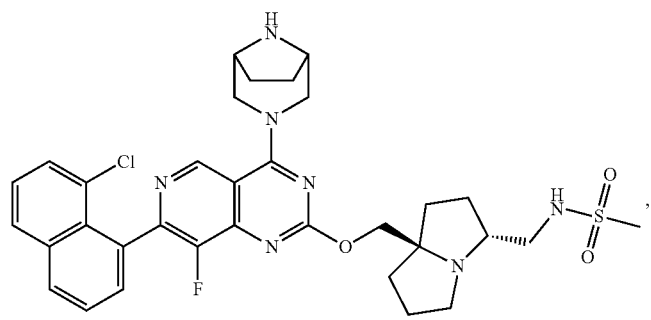, 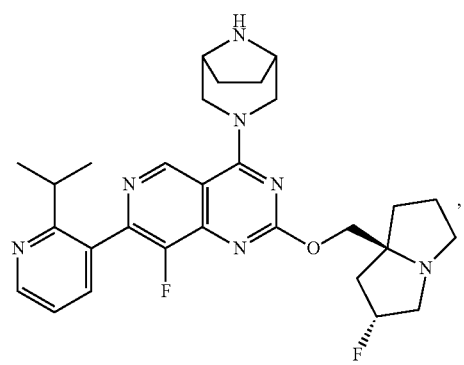, 115 116
-continued
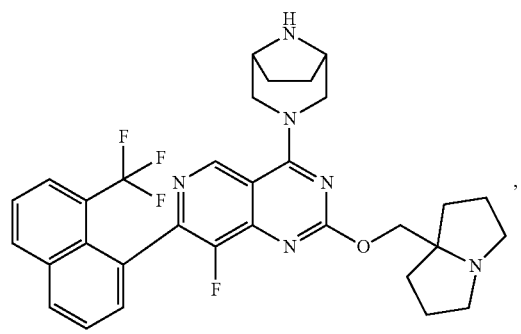
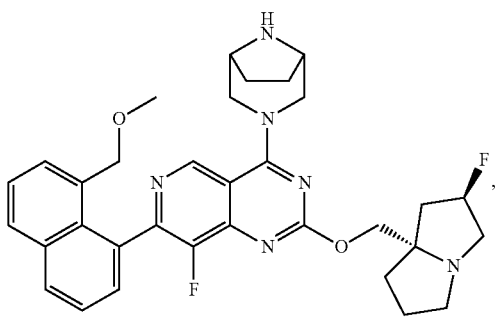
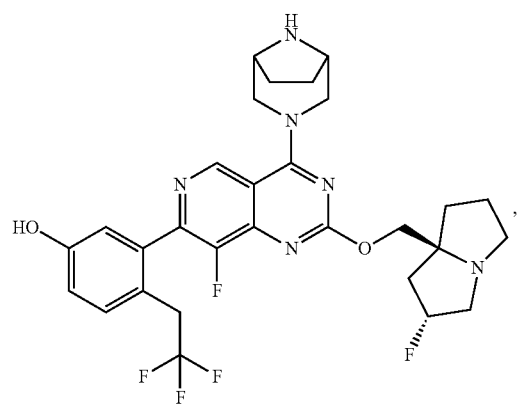
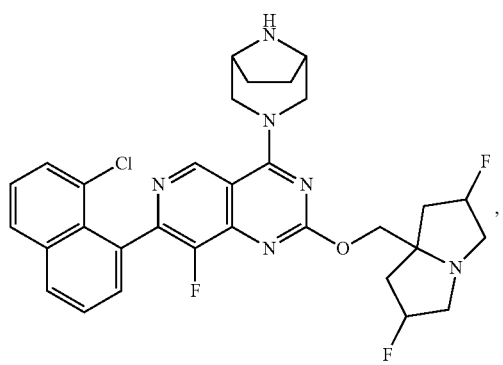
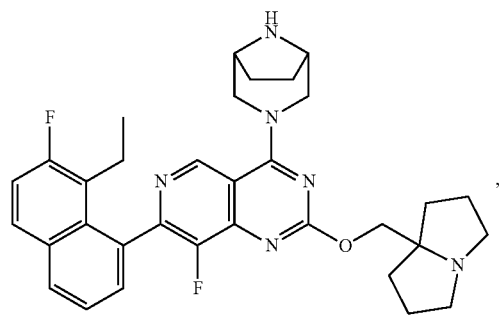
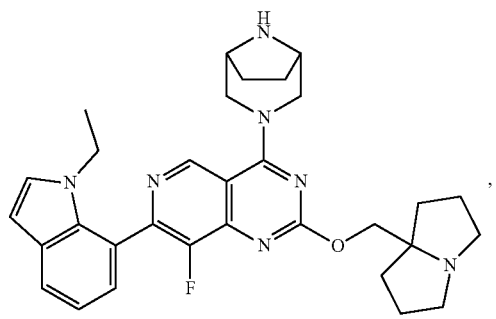
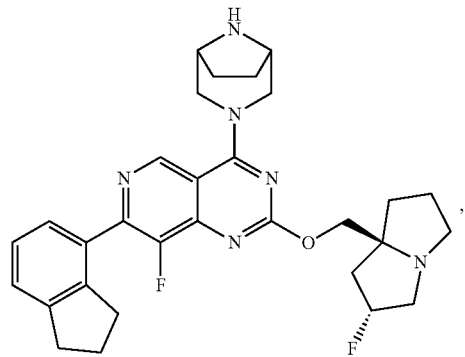
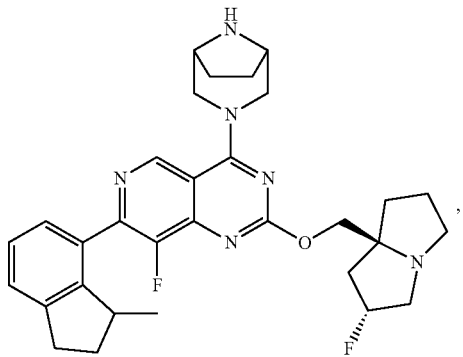

117
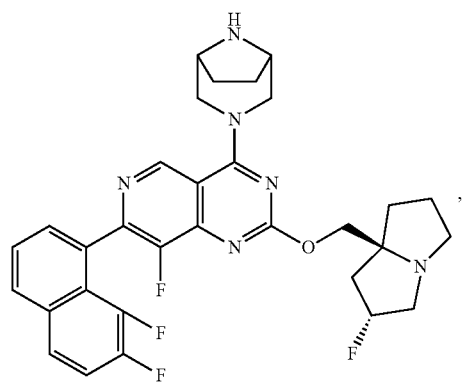
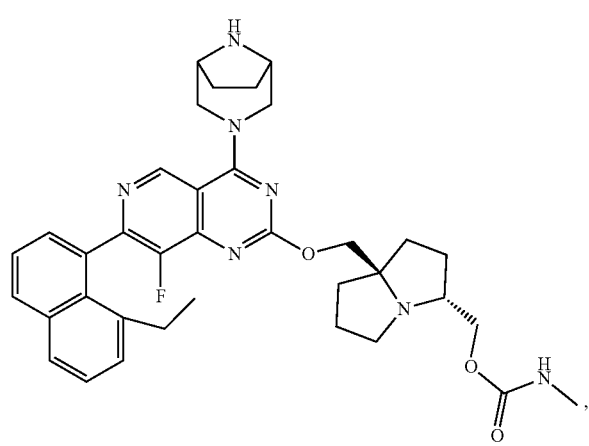
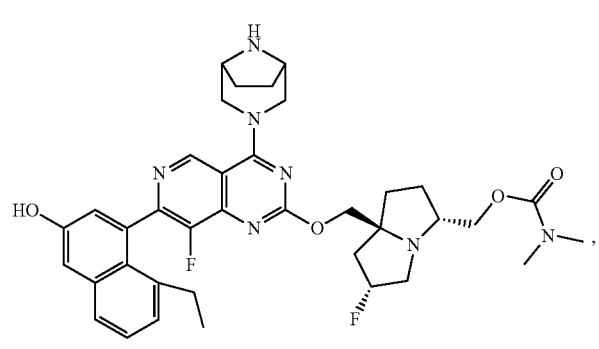
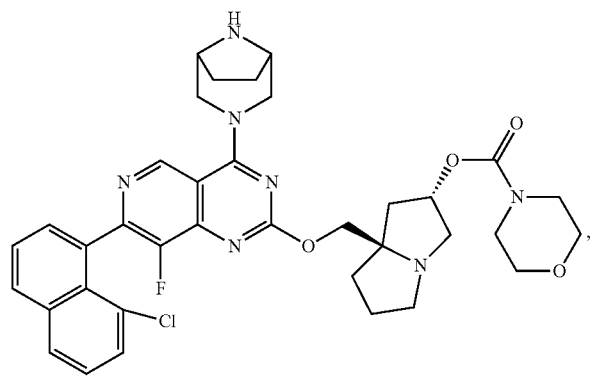
118
-continued
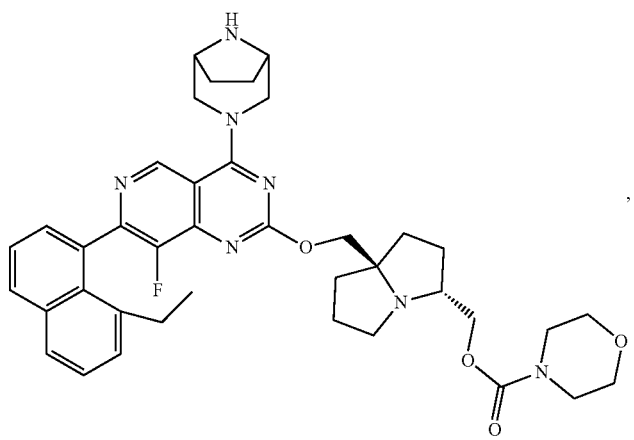
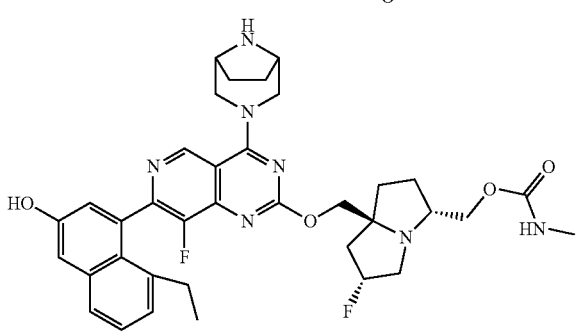
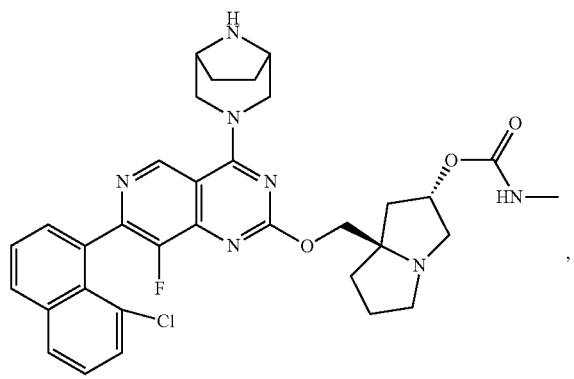
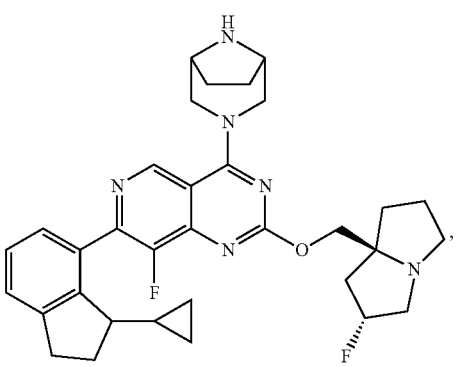

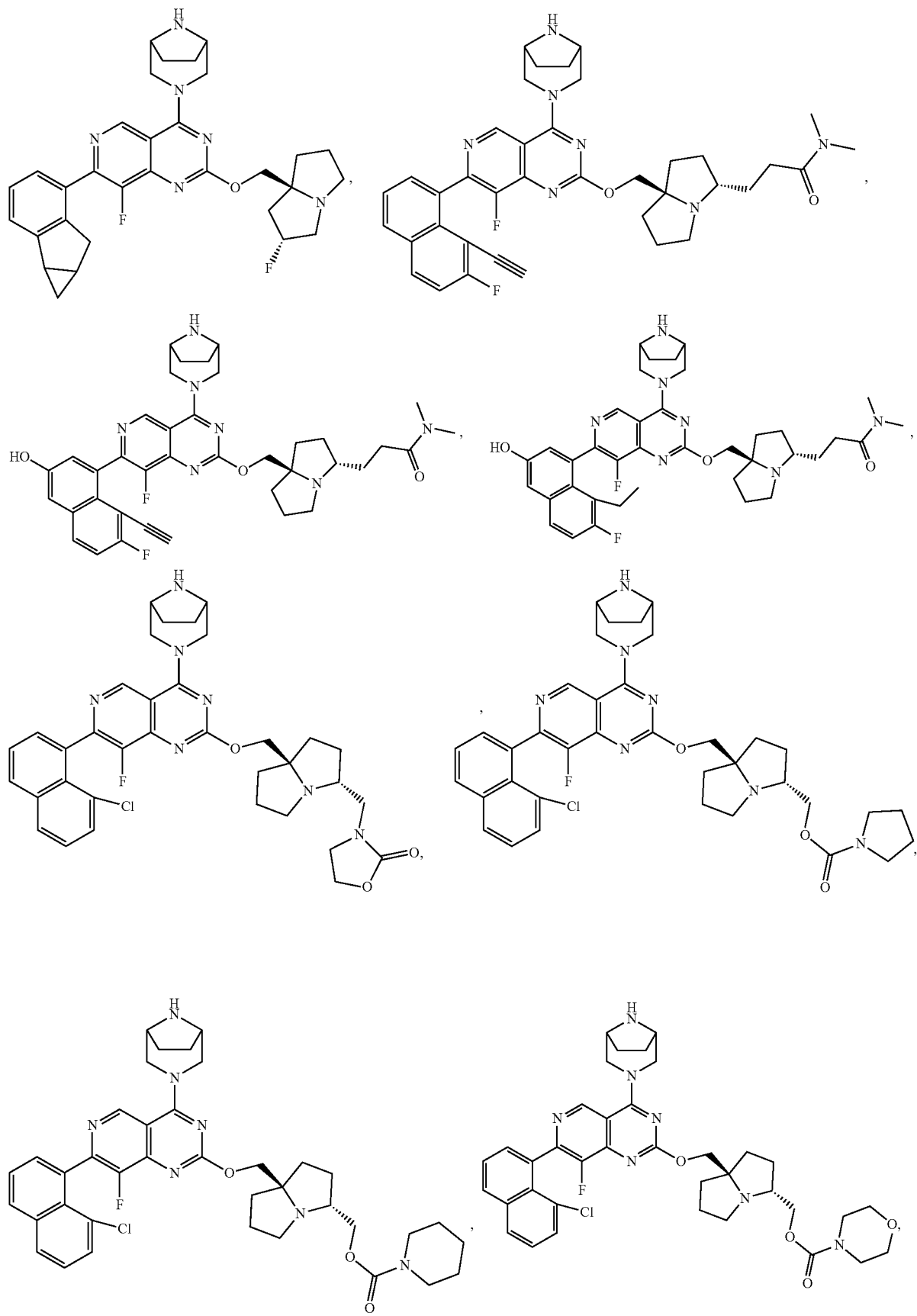

-continued
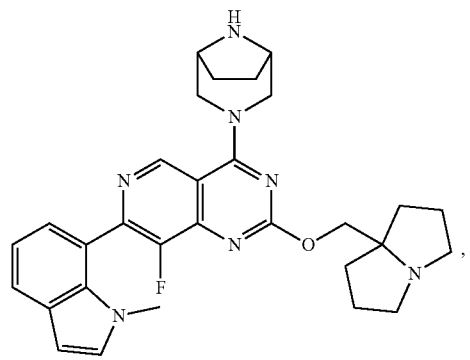
121
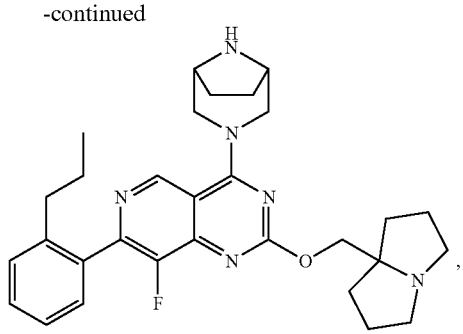
122
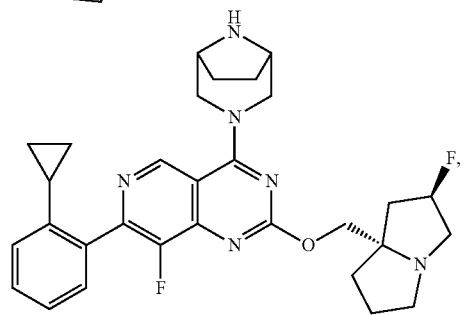
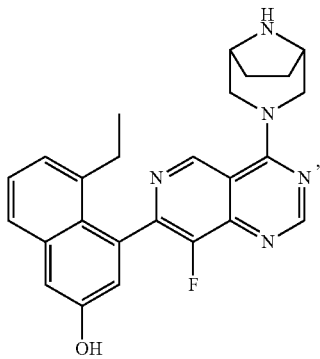
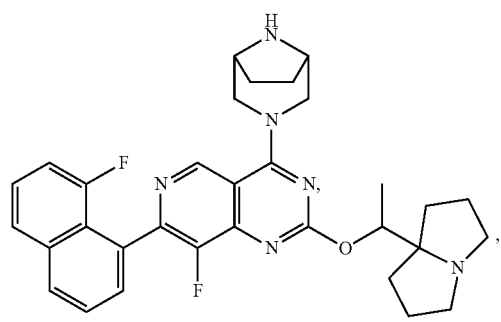
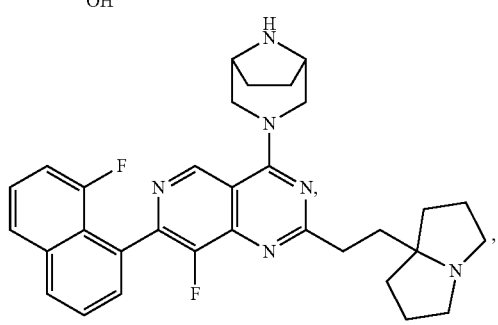
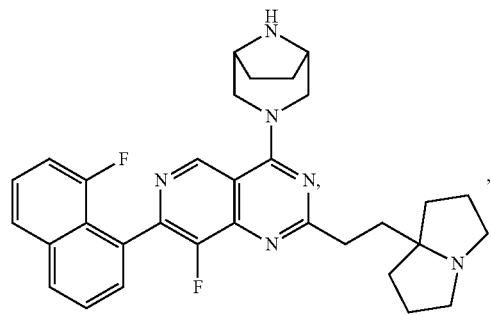
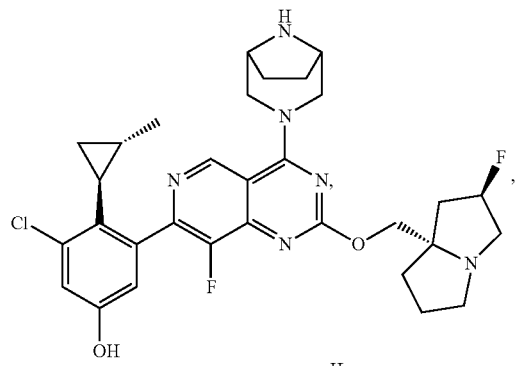
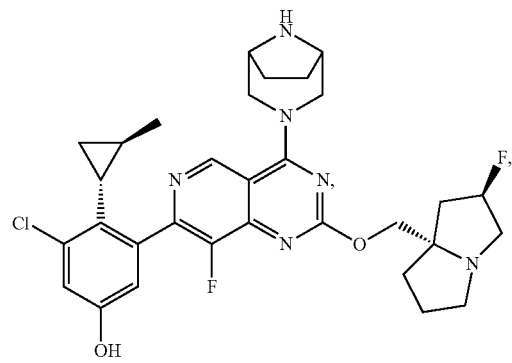
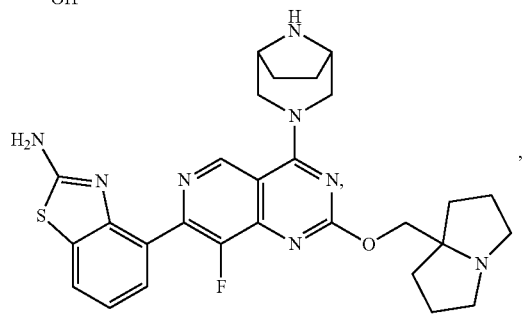

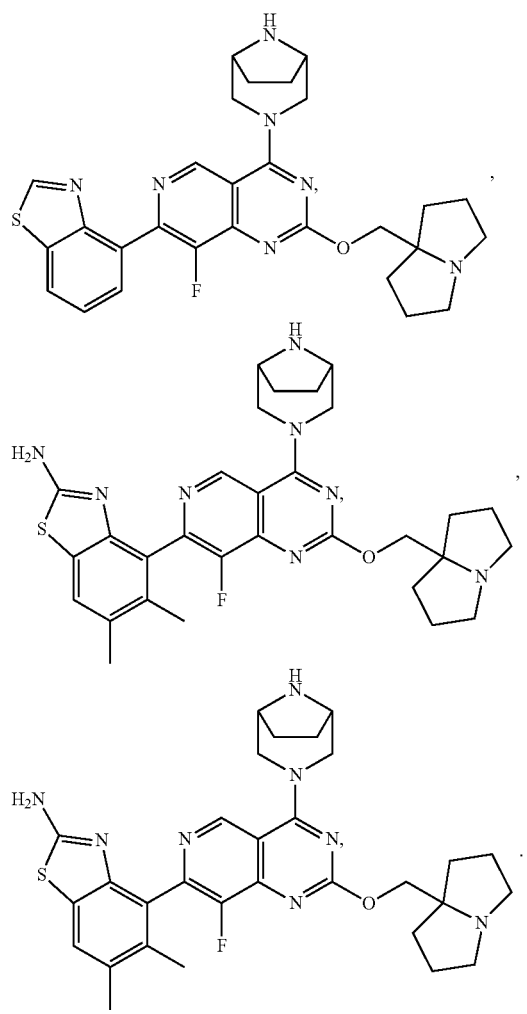

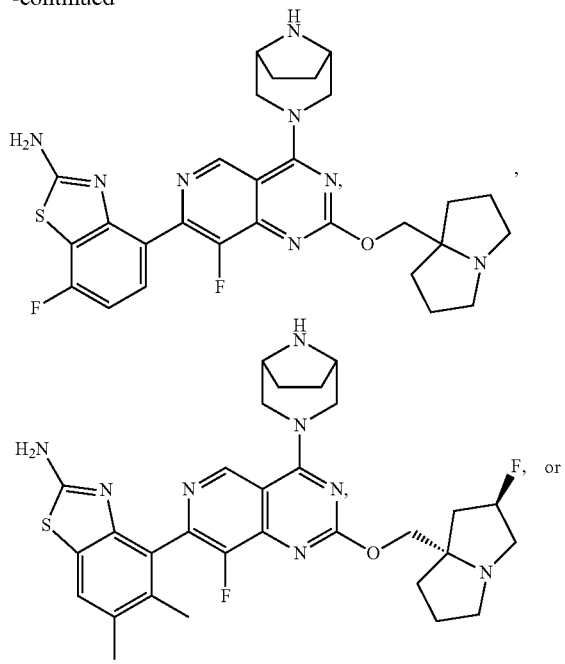

and pharmaceutically acceptable salts thereof. In one embodiment, the compounds of Formula (I) include bis-hydrochloride, tris-hydrochloride, trifluoroacetic acid, bis-trifluoroacetic acid, and tris-trifluoroacetic acid salts of the above compounds. The compounds of Formula (I) or pharmaceutically acceptable salt thereof may be formulated into pharmaceutical compositions.

Pharmaceutical Compositions

In another aspect, the invention provides pharmaceutical compositions comprising a KRas G12D inhibitor according to the invention and a pharmaceutically acceptable carrier, excipient, or diluent. Compounds of the invention may be formulated by any method well known in the art and may be prepared for administration by any route, including, without limitation, parenteral, intraperitoneal, intradermal, intracardiac, intraventricular, intracranial, intracerebrospinal, intrasynovial, intrathecal administration, intramuscular injection, intravitreous injection, intravenous injection, intra-arterial injection, oral, buccal, sublingual, transdermal, topical, intranasal, intratracheal, intrarectal, subcutaneous, and topical administration. In certain embodiments, compounds of the invention are administered intravenously in a hospital setting. In one embodiment, administration may be by the oral route. In some embodiments, the provided pharmaceutical compositions may be administered to a subject in need of treatment by injection systemically, such as by intravenous injection; or by injection or application to the relevant site, such as by direct injection via syringe, or direct application to the site when the site is exposed in surgery; or by topical administration.

Parenteral administration can be by bolus injection or continuous infusion. Pharmaceutical compositions for injection may be presented in unit dosage form, e.g., in ampoules or in multi-dose containers, with an added preservative.

The provided pharmaceutical compositions can also be formulated as a depot preparation. Such long acting formulations may be administered by implantation (for example subcutaneously or intramuscularly) or by intramuscular injection. Thus, for example, the formulations may be modified with suitable polymeric or hydrophobic materials (for example as an emulsion in an acceptable oil) or ion exchange resins, or as sparingly soluble derivatives, for example, as a sparingly soluble salt.

The pharmaceutical compositions may, if desired, be presented in a vial, pack or a medical device, including but not limited to a dispenser device which may contain one or more unit dosage forms containing the active ingredient. In one embodiment the dispenser device can comprise a syringe having a single dose of the liquid formulation ready for injection. The syringe can be accompanied by instructions for administration.

The characteristics of the carrier will depend on the route of administration. As used herein, the term "pharmaceutically acceptable" means a non-toxic material that is compatible with a biological system such as a cell, cell culture, tissue, or organism, and that does not interfere with the effectiveness of the biological activity of the active ingredient(s). Thus, compositions according to the invention may contain, in addition to the inhibitor, diluents, fillers, salts, buffers, stabilizers, solubilizers, and other materials well known in the art. The preparation of pharmaceutically acceptable formulations is described in, e.g., Remington's Pharmaceutical Sciences, 18th Edition, ed. A. Gennaro, Mack Publishing Co., Easton, Pa., 1990.

As used herein, the term pharmaceutically acceptable salt refers to salts that retain the desired biological activity of the above-identified compounds and exhibit minimal or no undesired toxicological effects. Examples of such salts include, but are not limited to acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalacturonic acid. The compounds can also be administered as pharmaceutically acceptable quaternary salts known by those skilled in the art, which specifically include the quaternary ammonium salt of the formula —NR+Z—, wherein R is hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

The active compound is included in the pharmaceutically acceptable carrier or diluent in an amount sufficient to deliver to a patient a therapeutically effective amount without causing serious toxic effects in the patient treated. In one embodiment, a dose of the active compound for all of the above-mentioned conditions is in the range from about 0.01 to 300 mg/kg, for example 0.1 to 100 mg/kg per day, and as a further example 0.5 to about 25 mg per kilogram body weight of the recipient per day. A typical topical dosage will range from 0.01-3% wt/wt in a suitable carrier. The effective dosage range of the pharmaceutically acceptable derivatives can be calculated based on the weight of the parent compound to be delivered. If the derivative exhibits activity in itself, the effective dosage can be estimated as above using the weight of the derivative, or by other means known to those skilled in the art.

The pharmaceutical compositions comprising compounds of the present invention may be used in the methods of use described herein.

Methods of Use

In yet another aspect, the invention provides for methods for inhibiting KRas G12D activity in a cell, comprising contacting the cell in which inhibition of KRas G12D activity is desired with an effective amount of a compound of Formula (I), pharmaceutically acceptable salts thereof, or pharmaceutical compositions containing the compound or pharmaceutically acceptable salt thereof. In one embodiment, the contacting is in vitro. In one embodiment, the contacting is in vivo.

As used herein, the term "contacting" refers to the bringing together of indicated moieties in an in vitro system or an in vivo system. For example, "contacting" a KRas G12D with a compound provided herein includes the administration of a compound provided herein to an individual or patient, such as a human, having KRas G12D, as well as, for example, introducing a compound provided herein into a sample containing a cellular or purified preparation containing the KRas G12D.

In one embodiment, a cell in which inhibition of KRas G12D activity is desired is contacted with an effective amount of a compound of Formula (I) or pharmaceutically acceptable salt thereof to negatively modulate the activity of KRas G12D.

By negatively modulating the activity of KRas G12D, the methods described herein are designed to inhibit undesired cellular proliferation resulting from enhanced KRas G12D activity within the cell. The cells may be contacted in a single dose or multiple doses in accordance with a particular treatment regimen to effect the desired negative modulation of KRas G12D. The ability of compounds to bind KRas G12D may be monitored in vitro using well known methods, including those described in Examples A and B below. In addition, the inhibitory activity of exemplary compounds in cells may be monitored, for example, by measuring the inhibition of KRas G12D activity of the amount of phosphorylated ERK, for example using the method described in Example C below.

In another aspect, methods of treating cancer in a patient in need thereof, comprising administering to said patient a therapeutically effective amount of a compound of Formula (I) or a pharmaceutically acceptable salt thereof, or a pharmaceutical composition comprising the compound or pharmaceutically acceptable salt thereof are provided.

The compositions and methods provided herein may be used for the treatment of a KRas G12D-associated cancer in a patient in need thereof, comprising administering to said patient a therapeutically effective amount of a compound of Formula (I), a pharmaceutically acceptable salt thereof, or a pharmaceutical composition comprising the compound or pharmaceutically acceptable salt thereof are provided. In one embodiment, the KRas G12D-associated cancer is lung cancer.

The compositions and methods provided herein may be used for the treatment of a wide variety of cancers including tumors such as lung, prostate, breast, brain, skin, cervical carcinomas, testicular carcinomas, etc. More particularly, cancers that may be treated by the compositions and methods of the invention include, but are not limited to tumor types such as astrocytic, breast, cervical, colorectal, endometrial, esophageal, gastric, head and neck, hepatocellular, laryngeal, lung, oral, ovarian, prostate and thyroid carcinomas and sarcomas. More specifically, these compounds can be used to treat: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Biliary tract: gall bladder carcinoma, ampullary carcinoma, cholangiocarcinoma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma); Skin: malignant melanoma, basal cell carcinoma, squamous cell carcinoma, Kaposi's sarcoma, moles dysplastic nevi, lipoma, angioma, dermatofibroma, keloids, psoriasis; and Adrenal glands: neuroblastoma. In certain embodiments, the cancer is non-small cell lung cancer, small cell lung cancer, colorectal cancer, rectal cancer or pancreatic cancer. In certain embodiments, the cancer is non-small cell lung cancer.

The concentration and route of administration to the patient will vary depending on the cancer to be treated. The compounds, pharmaceutically acceptable salts thereof and pharmaceutical compositions comprising such compounds and salts also may be co-administered with other antineoplastic compounds, e.g., chemotherapy, or used in combination with other treatments, such as radiation or surgical intervention, either as an adjuvant prior to surgery or post-operatively.

Also provided herein is a compound of Formula (I) or a pharmaceutically acceptable salt thereof, or a pharmaceutical composition thereof as defined herein for use in therapy.

Also provided herein is a compound of Formula (I) or a pharmaceutically acceptable salt thereof, or a pharmaceutical composition thereof as defined herein for use in the treatment of cancer.

Also provided herein is a compound of Formula (I) or a pharmaceutically acceptable salt thereof, or a pharmaceutical composition thereof for use in the inhibition of KRas G12D.

Also provided herein is a compound of Formula (I) or a pharmaceutically acceptable salt thereof, or a pharmaceutical composition thereof as defined herein, for use in the treatment of a KRas G12D-associated disease or disorder.

Also provided herein is the use of a compound of Formula (I) or a pharmaceutically acceptable salt thereof, as defined herein in the manufacture of a medicament for the treatment of cancer.

Also provided herein is a use of a compound of Formula (I) or a pharmaceutically acceptable salt thereof, as defined herein in the manufacture of a medicament for the inhibition of activity of KRas G12D.

Also provided herein is the use of a compound of Formula (I) or a pharmaceutically acceptable salt thereof, as defined herein, in the manufacture of a medicament for the treatment of a KRas G12D-associated disease or disorder.

Also provided herein is a method for treating cancer in a patient in need thereof, the method comprising (a) determining that cancer is associated with a KRas G12D mutation (e.g., a KRas G12D-associated cancer) (e.g., as determined using a regulatory agency-approved, e.g., FDA-approved, assay or kit); and (b) administering to the patient a therapeutically effective amount of a compound of Formula (I), or a pharmaceutically acceptable salt thereof, or a pharmaceutical composition thereof.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trials including first-in-human, dose ranging and efficacy trials, in healthy patients and/or those suffering from a given disorder, may be completed according to methods well known in the clinical and medical arts.

REACTION SCHEMES AND EXAMPLES

The compounds of the present invention may be prepared from commercially available reagents using the synthetic methods and reaction schemes described herein, or using other reagents and conventional methods well known to those skilled in the art.

For instance, compounds of the present invention may be prepared according to the General Reaction Schemes I-V.

General Reaction Schemes

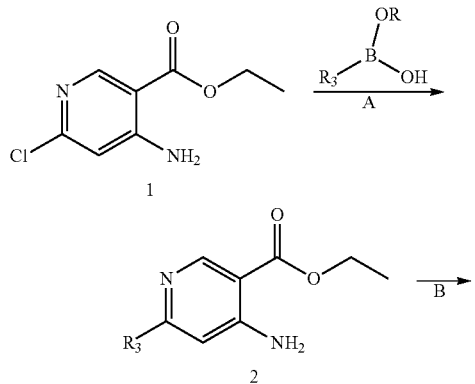

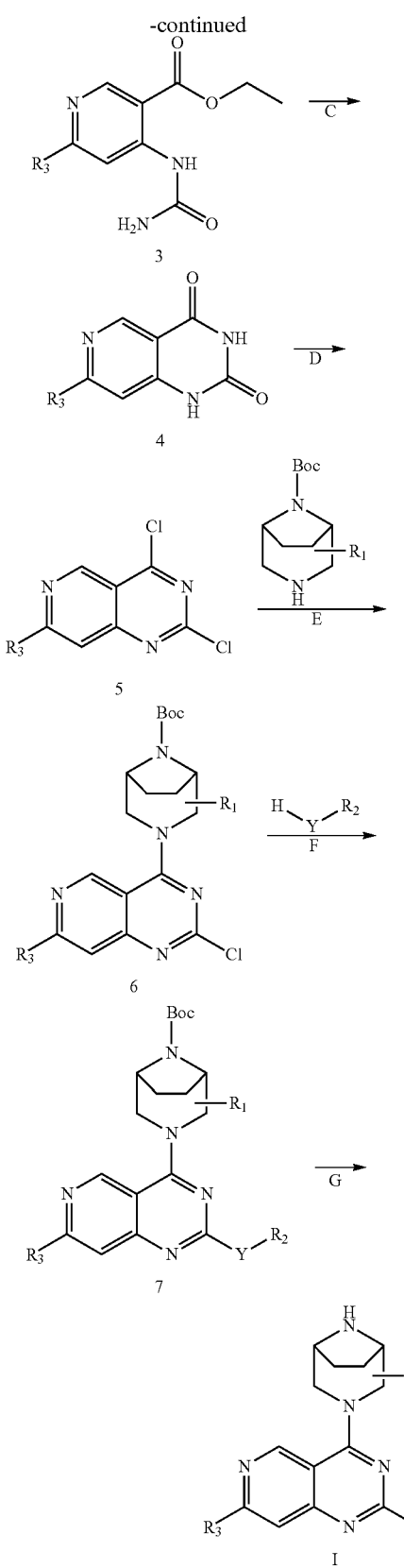

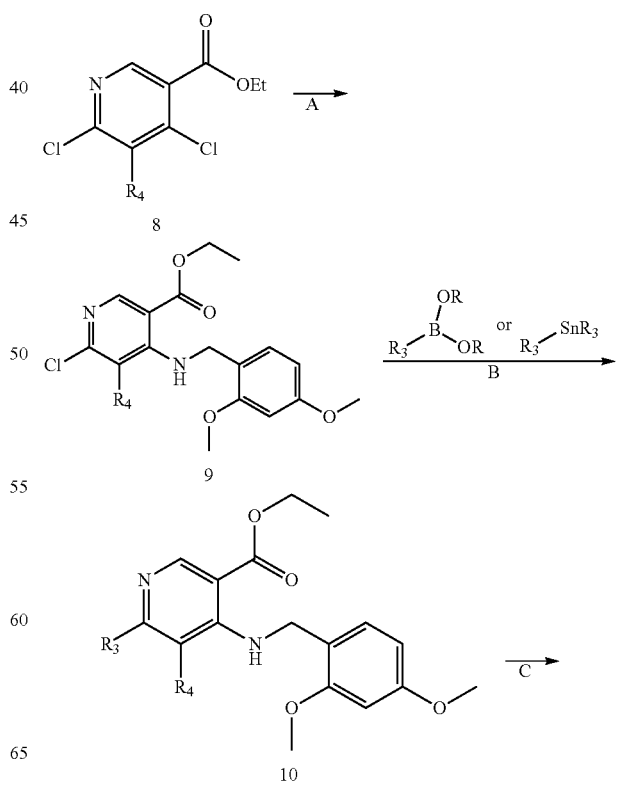

to Scheme I. In step A, ethyl 4-amino-6-chloronicotinate (1) is coupled to an aryl boronic acid (ester) to provide compound (2). This Suzuki coupling proceeds in a solvent such as dioxane and in the presence of a base such as potassium carbonate and a catalyst such as Xphos/Pd$_2$(dba)$_3$. In step B, compound (2) is subjected to phosgene and then reacts with ammonia in a solvent such as dichloromethane and in the presence of a base such as N-ethyl-N-isopropylpropan-2-amine to form urea (3). In step C, the cyclization of compound (3) in the presence of a base such as cesium carbonate in a solvent such as toluene and at elevated temperature gives compound (4). In step D, dichloroazaquinazoline (5) is prepared from compound (4) with phosphoryl trichloride and N-ethyl-N-isopropylpropan-2-amine. In step E, compound (5) undergoes a S$_N$Ar reaction with optionally substituted mono-Boc protected diazabicyclo[3.2.1]octane in a solvent such as dimethylformamide and in the presence of a base such as N-ethyl-N-isopropylpropan-2-amine to give compound (6). In step F, the substituent —Y—R$^2$ is introduced by substitution of the chlorine with a nucleophile having the formula H—Y—R$^2$ in a polar solvent such as dioxane in the presence of a base such as cesium carbonate to provide compound (7). In step G, the Boc group of compound (7) is removed using conditions known in the art, for example with cold 4 N HCl in a solvent such as dioxane, to provide compound (I). In some cases, the species R$^2$ and/or R$^3$ will also contain protecting group(s), which can be removed before or after step G in the synthetic sequence.

Compounds (1), (2), (3), (4), (5) (6) and (7) as shown and described above for Scheme I are useful as intermediates for preparing compounds of Formula (I) and are provided as further aspects of the invention.

SCHEME II

Compounds of Formula (I) wherein all of the substituents are as defined for Formula I, with the exception that —Y—R$^2$ is other than hydrogen, can be prepared according

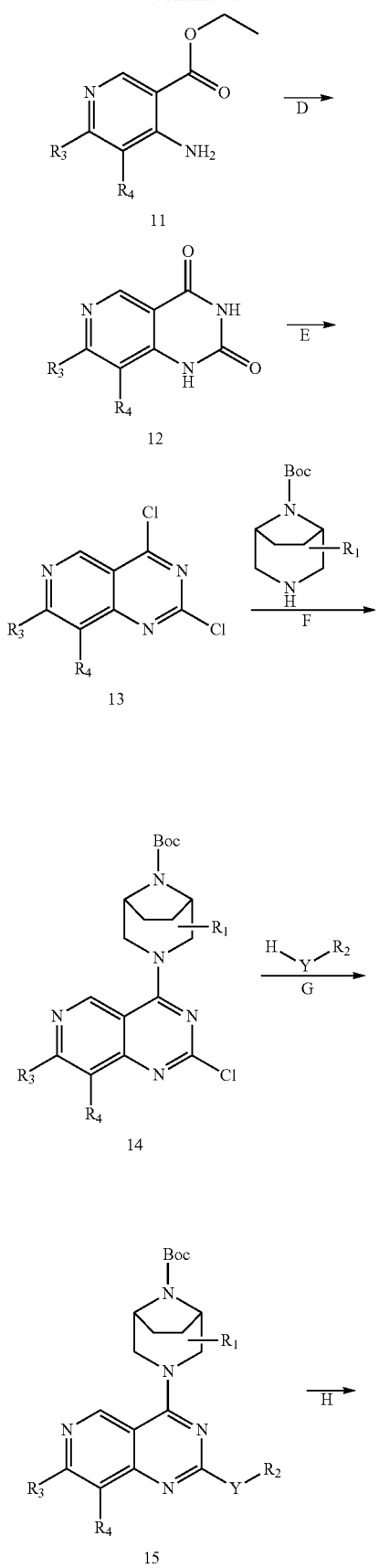

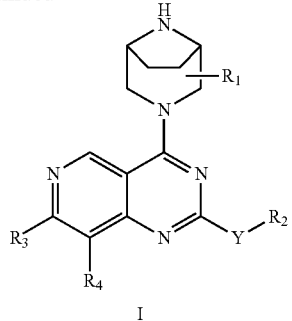

I

Compounds of Formula (I) wherein all of the substituents are as defined for Formula I, with the exception that —Y—R² is other than hydrogen, can be prepared according to Scheme II. In step A, the 4-chlorine of nicotinate derivative (8) is substituted with 2,4-dimethoxybenzylamine in a polar solvent such as dioxane and in the presence of a base such as N-ethyl-N-isopropylpropan-2-amine to give compound (9). In step B, compound (9) is coupled with an aryl boronic acid ester or aryl stannane under the Suzuki or Stille reaction conditions to give compound (10). In step C, the 2,4-dimethoxybenzyl group of compound (10) is removed with trifluoroacetic acid and in a solvent such as dichloromethane to give compound (11). In step D, compound (11) is treated with trichloroacetyl isocyanate in THF and then ammonia in methanol, and the cyclization is facilitated with heat to give pyridopyrimidinedione (12). In step E, dichloroazaquinazoline (13) is prepared from compound (12) with phosphoryl trichloride and N-ethyl-N-isopropylpropan-2-amine. In step F, compound (13) undergoes a $S_N Ar$ reaction with optionally substituted mono-Boc protected diazabicyclo[3.2.1]octane in a solvent such as N,N-dimethylacetamide and in the presence of a base such as N-ethyl-N-isopropylpropan-2-amine to give compound (14). In step G, the substituent —Y—R² is introduced by substitution of the chlorine with a nucleophile having the formula H—Y—R² in a polar solvent such as dioxane in the presence of a base such as cesium carbonate to provide compound (15). In step H, the Boc group of compound (15) is removed using conditions known in the art, for example with trifluoroacetic acid in a solvent such as dichloromethane, to provide compound (I). In some cases, the species R² and/or R³ will also contain protecting group(s), which can be removed before or after step H in the synthetic sequence.

Compounds (8), (9), (10), (11), (12), (13), (14) and (15) as shown and described above for Scheme II are useful as intermediates for preparing compounds of Formula (I) and are provided as further aspects of the invention.

SCHEME III

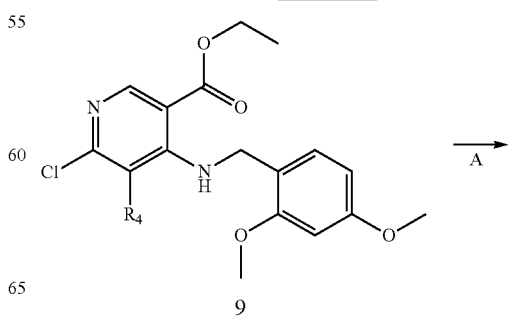

9

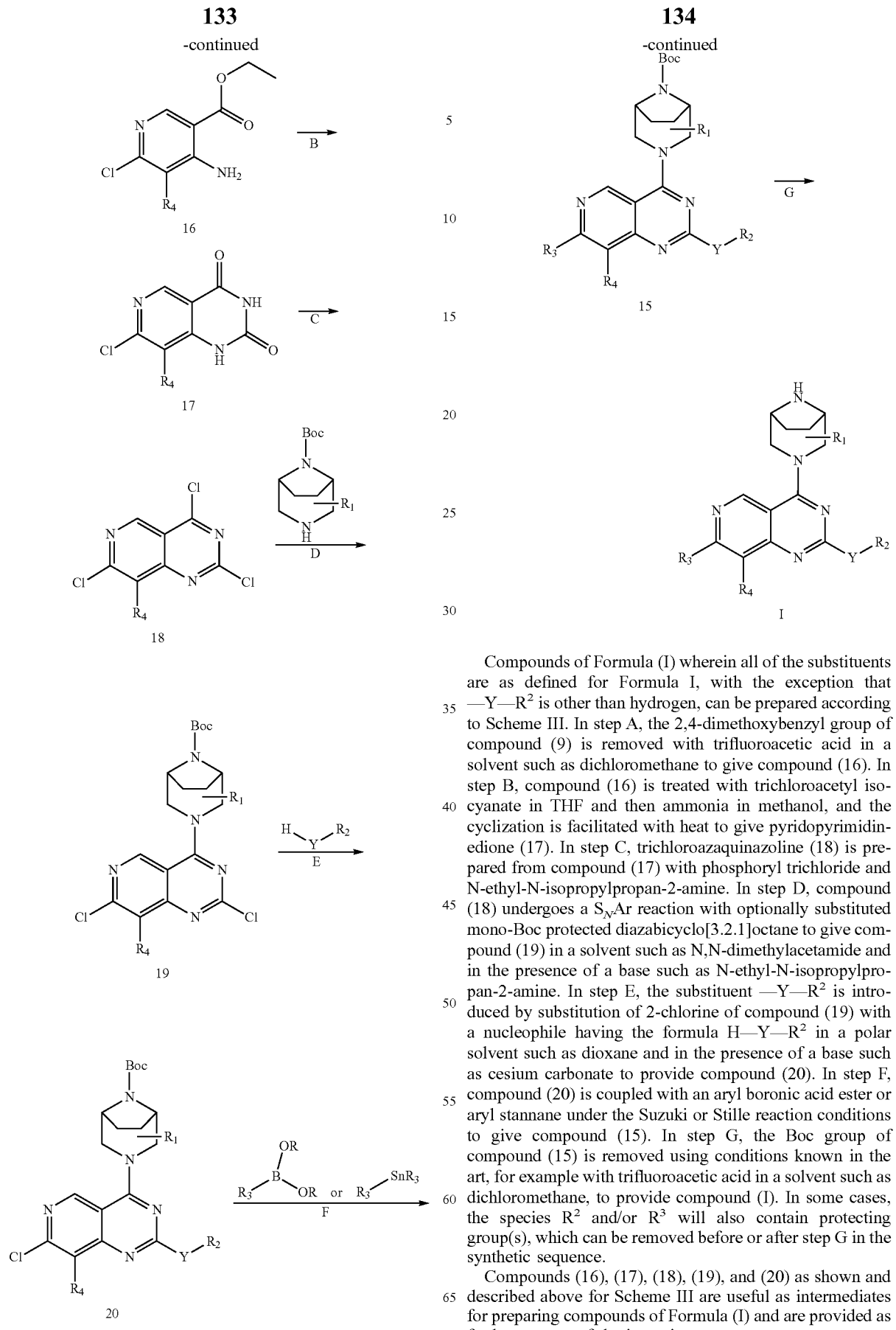

Compounds of Formula (I) wherein all of the substituents are as defined for Formula I, with the exception that —Y—R² is other than hydrogen, can be prepared according to Scheme III. In step A, the 2,4-dimethoxybenzyl group of compound (9) is removed with trifluoroacetic acid in a solvent such as dichloromethane to give compound (16). In step B, compound (16) is treated with trichloroacetyl isocyanate in THF and then ammonia in methanol, and the cyclization is facilitated with heat to give pyridopyrimidinedione (17). In step C, trichloroazaquinazoline (18) is prepared from compound (17) with phosphoryl trichloride and N-ethyl-N-isopropylpropan-2-amine. In step D, compound (18) undergoes a S$_N$Ar reaction with optionally substituted mono-Boc protected diazabicyclo[3.2.1]octane to give compound (19) in a solvent such as N,N-dimethylacetamide and in the presence of a base such as N-ethyl-N-isopropylpropan-2-amine. In step E, the substituent —Y—R² is introduced by substitution of 2-chlorine of compound (19) with a nucleophile having the formula H—Y—R² in a polar solvent such as dioxane and in the presence of a base such as cesium carbonate to provide compound (20). In step F, compound (20) is coupled with an aryl boronic acid ester or aryl stannane under the Suzuki or Stille reaction conditions to give compound (15). In step G, the Boc group of compound (15) is removed using conditions known in the art, for example with trifluoroacetic acid in a solvent such as dichloromethane, to provide compound (I). In some cases, the species R² and/or R³ will also contain protecting group(s), which can be removed before or after step G in the synthetic sequence.

Compounds (16), (17), (18), (19), and (20) as shown and described above for Scheme III are useful as intermediates for preparing compounds of Formula (I) and are provided as further aspects of the invention.

SCHEME IV

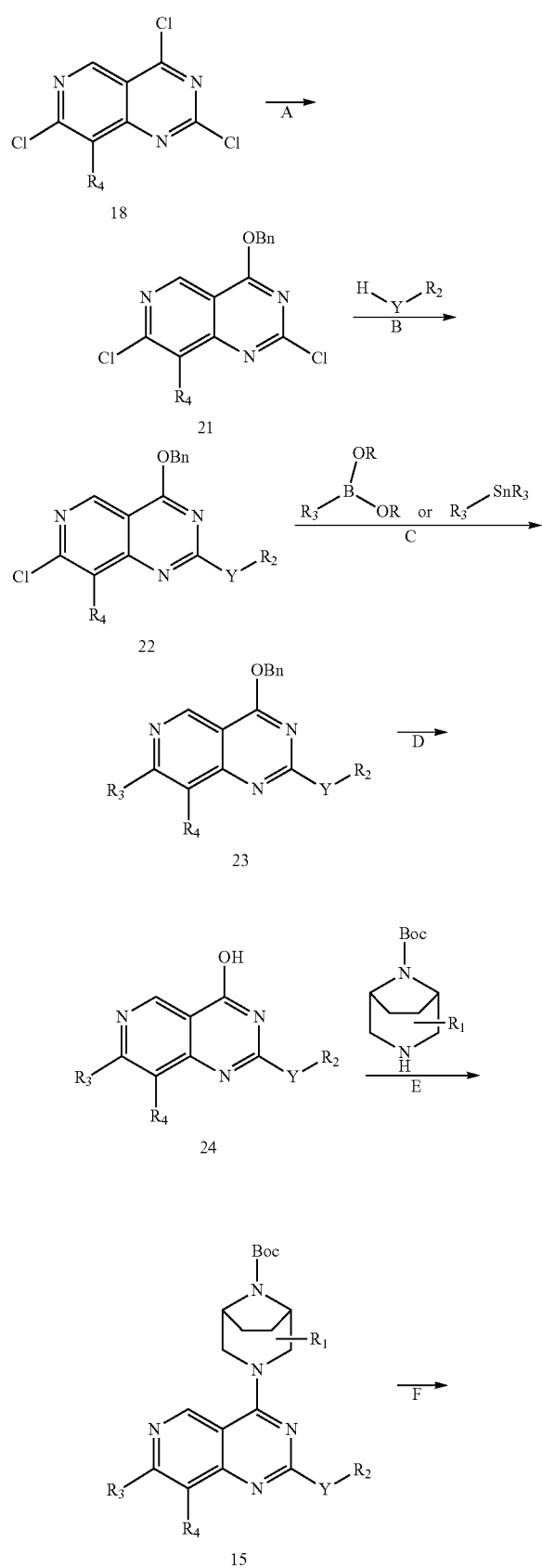

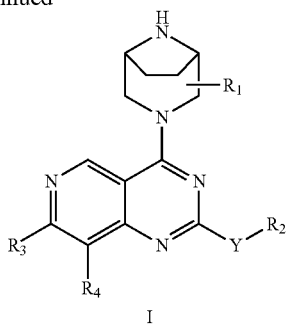

Compounds of Formula (I) wherein all of the substituents are as defined for Formula I, with the exception that —Y—R² is other than hydrogen, can be prepared according to Scheme IV. In step A, 4-chlorine of trichloroazaquinazoline (18) is substituted with a benzyl alcohol in a polar solvent such as dioxane and in the presence of a base such as N-ethyl-N-isopropylpropan-2-amine to provide compound (21). In step B, the substituent —Y—R² is introduced by substitution of 2-chlorine of compound (21) with a nucleophile having the formula H—Y—R² in a polar solvent such as dioxane and in the presence of a base such as cesium carbonate to provide compound (20). In step C, compound (22) is coupled with an aryl boronic acid ester or aryl stannane under the Suzuki or Stille reaction conditions to give compound (23). In step D, the benzyl group of compound (23) is removed under the palladium-catalyzed hydrogenation condition in a solvent such as ethyl acetate to give compound (24). In step E, compound (24) is coupled with optionally substituted mono-Boc protected diazabicyclo[3.2.1]octane to provide compound (15). This reaction proceeds with an activating reagent such as 2-(3H-[1,2,3]triazolo[4,5-b]pyridin-3-yl)-1,1,3,3-tetramethylisouronium hexafluorophosphate(V) in a polar solvent such as N,N-dimethylacetamide. In step F, the Boc group of compound (15) is removed using conditions known in the art, for example with trifluoroacetic acid in a solvent such as dichloromethane, to provide compound (I). In some cases, the species R² and/or R³ will also contain protecting group(s), which can be removed before or after step G in the synthetic sequence.

Compounds (21), (22), (23), and (24) as shown and described above for Scheme IV are useful as intermediates for preparing compounds of Formula (I) and are provided as further aspects of the invention.

SCHEME V

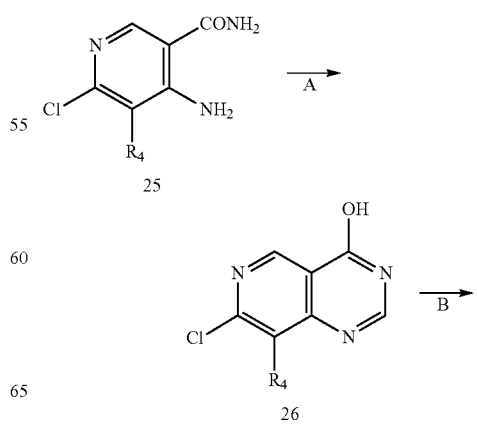

SCHEME VI

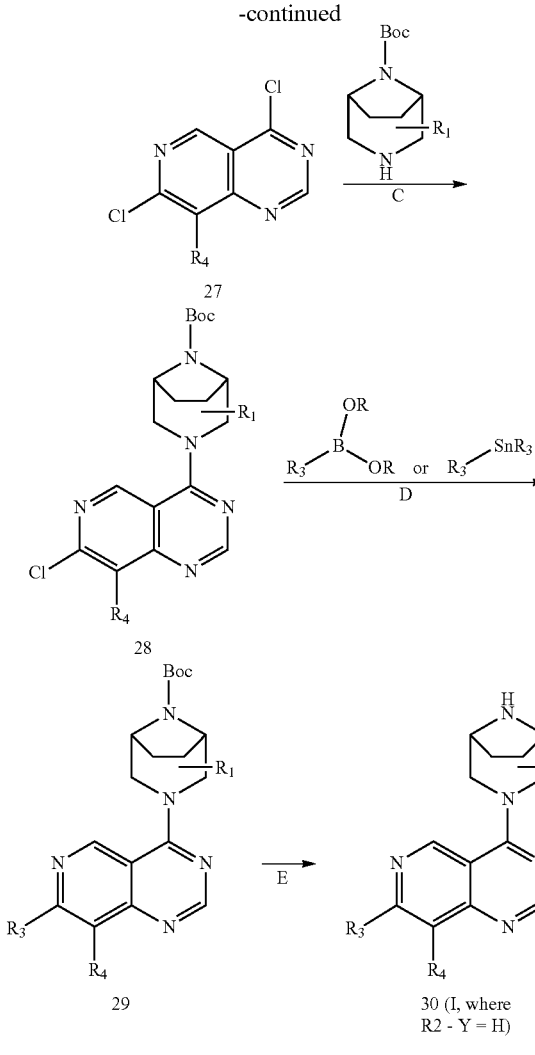

Compounds of Formula (I) wherein Y is a bond, R² is hydrogen, and R¹, R³ and R⁴ are as defined for Formula I can be prepared according to Scheme V. In step A, nicotinamide derivative (25) reacts with trimethoxymethane in acetic acid to give azaquinazoline compound (26). In step B, the chlorination of compound 26 with phosphoryl trichloride and N-ethyl-N-isopropylpropan-2-amine provides dichloro-azaquinazoline (27). In step C, compound (27) undergoes a S$_N$Ar reaction with optionally substituted mono-Boc protected diazabicyclo[3.2.1]octane in a solvent such as N,N-dimethylacetamide and in the presence of a base such as N-ethyl-N-isopropylpropan-2-amine to give compound (28). In step D, compound (28) is coupled with an aryl boronic acid ester or aryl stannane under the Suzuki or Stille reaction conditions to give compound (29). In step E, the Boc group of compound (29) is removed using conditions known in the art, for example with cold 4N HCl and in a solvent such as dioxane, to provide compound (30). In some cases, the species R³ will also contain a protecting group, which can be removed before or after step G in the synthetic sequence.

Compounds (25), (26), (27), (28), and (29) as shown and described above for Scheme V are useful as intermediates for preparing compounds of Formula (I) and are provided as further aspects of the invention.

Compounds of Formula (I) wherein all substituents are as defined for Formula I, with the exception that —Y—R² is other than hydrogen, can be prepared according to Scheme VI. In step A, compound (14) undergoes a Sonogashira coupling reaction in a polar solvent such as acetonitrile to provide compound (15). In step B, the Boc group of compound (15) is removed using conditions known in the art, for example with trifluoroacetic acid in a solvent such as dichloromethane, to provide compound (I). In some cases, the species R² and/or R³ will also contain protecting/masking group(s), which can be removed before or after step B in the synthetic sequence.

The compounds of the present invention may have one or more chiral center and may be synthesized as stereoisomeric mixtures, isomers of identical constitution that differ in the arrangement of their atoms in space. The compounds may be used as mixtures or the individual components/isomers may be separated using commercially available reagents and conventional methods for isolation of stereoisomers and enantiomers well-known to those skilled in the art, e.g., using CHIRALPAK® (Sigma-Aldrich) or CHIRALCEL® (Diacel Corp) chiral chromatographic HPLC columns according to the manufacturer's instructions. Alternatively, compounds of the present invention may be synthesized using optically pure, chiral reagents and intermediates to prepare individual isomers or enantiomers. Unless otherwise indicated, all chiral (enantiomeric and diastereomeric) and racemic forms are within the scope of the invention. Unless otherwise indicated, whenever the specification, including the claims, refers to compounds of the invention, the term "compound" is to be understood to encompass all chiral (enantiomeric and diastereomeric) and racemic forms.

The compounds of the present invention may be in anhydrous, solvated or hydrated forms, and all such forms are included within the scope of the invention.

The following Intermediates are intended to illustrate further certain embodiments of the invention and are not intended to limit the scope of the invention.

Intermediate 1

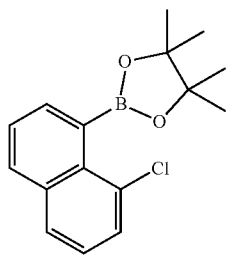 [SMILES: CC1(C)OB(c2cccc3cccc(Cl)c23)OC1(C)C]

2-(8-chloronaphthalen-1-yl)-4,4,5,5-tetramethyl-1,3,2-dioxaborolane

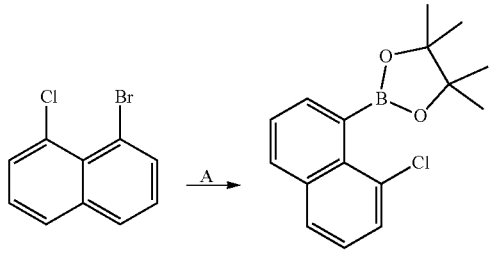

Step A. To a solution of 1-bromo-8-chloronaphthalene (20.0 g, 82.81 mmol) in dioxane (414 ml, 82.8 mmol) was added KOAc (24.38 g, 248.4 mmol) and 4,4,4',4',5,5,5',5'-octamethyl-2,2'-bi(1,3,2-dioxaborolane) (63.09 g, 248.4 mmol) and the reaction was degassed with Ar for 15 minutes followed by the addition of PdCl$_2$(dppf) (6.059 g, 8.281 mmol). The reaction was heated to 95° C. for 18 hrs. The dark mixture was filtered, and the filtrate was partitioned between water (400 mL) and EtOAc (400 mL). The aqueous layer was extracted with EtOAc (2×200 mL) and the combined organic phases were washed with brine (200 mL), dried over Na$_2$SO$_4$, filtered and concentrated to afford a black solid. The solid was filtered through a silica gel plug in a 2 L fritted funnel eluting with hexanes to 10% EtOAc/hexanes to afford partially purified product as a bright yellow solid. This was further purified by dividing in half and purifying on a 330 g Redisep cartridge (Isolera) eluting with 0-8% EtOAc/hexanes. Clean fractions from both lots were combined and concentrated to afford the product as a pale yellow solid. (14.8 g, 62%). $^1$H NMR (400 MHz, (CDCl$_3$) δ 7.86 (dd, J=8.0, 1.2 Hz, 1H), 7.75 (dd, J=7.7, 1.2 Hz, 1H), 7.66 (dd, J=7.0, 1.2 Hz, 1H), 7.57 (dd, J=7.5, 1.1 Hz, 1H), 7.50 (dd, J=7.1, 6.9 Hz, 1H), 7.36 (dd, J=8.2, 7.4 Hz, 1H), 1.44 (s, 12H).

Intermediate 2

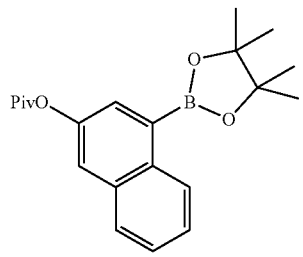

4-(4,4,5,5-tetramethyl-1,3,2-dioxaborolan-2-yl)naphthalen-2-yl pivalate

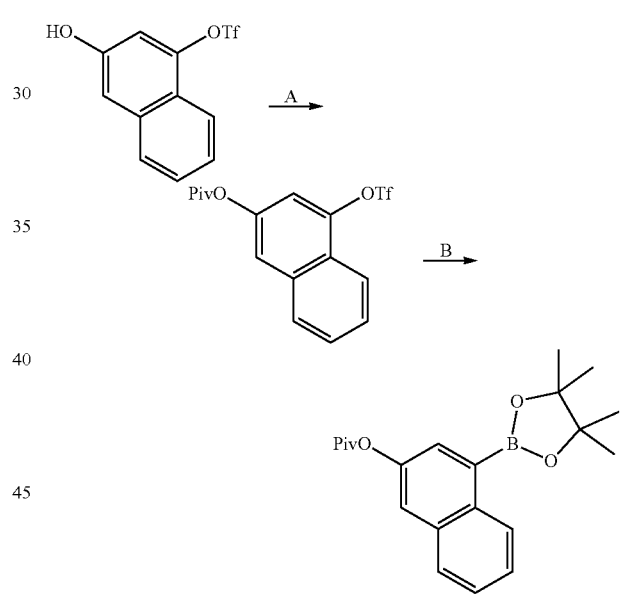

Step A: 4-(((trifluoromethyl)sulfonyl)oxy)naphthalen-2-yl pivalate. A solution of 3-hydroxynaphthalen-1-yl trifluoromethanesulfonate (1.00 g, 3.42 mmol) in DCM (17 mL) was cooled to 0° C. Triethylamine (0.52 mL, 3.8 mmol) was added followed by pivaloyl chloride (0.46 mL, 3.8 mmol) and reaction mixture stirred at 0° C. for 1 hour. The reaction was warmed to r.t. and poured into hexane (100 mL). The organics washed with sat. NaHCO$_3$, water and brine (10 mL each), dried over Na$_2$SO$_4$ and evaporated in vacuo. The residue was chromatographed on silica gel eluting with 2 to 10% EtOAc/hexanes to yield 4-(((trifluoromethyl)sulfonyl)oxy)naphthalen-2-yl pivalate (1.229 g, 95%). $^1$H NMR (400 MHz, CDCl$_3$): 8.07-8.02 (m, 1H), 7.87-7.82 (m, 1H), 7.64-7.56 (m, 3H), 7.26 (d, J=2.1 Hz, 1H), 1.39 (s, 9H).

Step B: 4-(4,4,5,5-tetramethyl-1,3,2-dioxaborolan-2-yl) naphthalen-2-yl pivalate. A mixture of 4-(((trifluoromethyl) sulfonyl)oxy)naphthalen-2-yl pivalate (1.220 g, 3.24 mmol), potassium acetate (0.95 g, 9.7 mmol, 3 eq.), 1,1'-bis(diphenylphosphino)ferrocene (90 mg, 0.16 mmol), dichloro[1,1'-bis(diphenylphosphino)ferrocene]palladium dichloromethane adduct (132 mg, 0.16 mmol, 0.05 eq.), 4,4,4',4',5,5,5',5'-octamethyl-2,2'-bi(1,3,2-dioxaborolane) (1.207 g, 4.76 mmol) and dioxane (15 mL) under $N_2$ atmosphere was stirred for 5 hours at 100° C. The reaction was cooled to r.t and partitioned between a mixture of EtOAc and hexanes (20 mL/100 mL) and water (50 mL). The layers were separated. The organic layer was washed with water and brine (20 mL each), dried over $Na_2SO_4$ and concentrated in vacuo. The residue was chromatographed on silica gel eluting with 20 to 50% dichloromethane/hexanes to yield 4-(4,4,5,5-tetramethyl-1,3,2-dioxaborolan-2-yl)naphthalen-2-yl pivalate (0.778 g, 68%). $^1$H NMR (400 MHz, $CDCl_3$): 8.75 (dm, J~8.3 Hz, 1H), 7.79-7.71 (m, 2H), 7.60 (d, J=2.4 Hz, 1H), 7.51-7.43 (m, 2H), 1.40 (s, 12H), 1.39 (s, 9H).

Intermediate 3

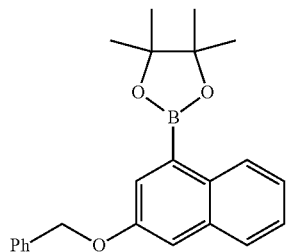 [SMILES: CC1(C)OB(c2cc(OCc3ccccc3)cc3ccccc23)OC1(C)C]

2-(3-(benzyloxy)naphthalen-1-yl)-4,4,5,5-tetramethyl-1,3,2-dioxaborolane

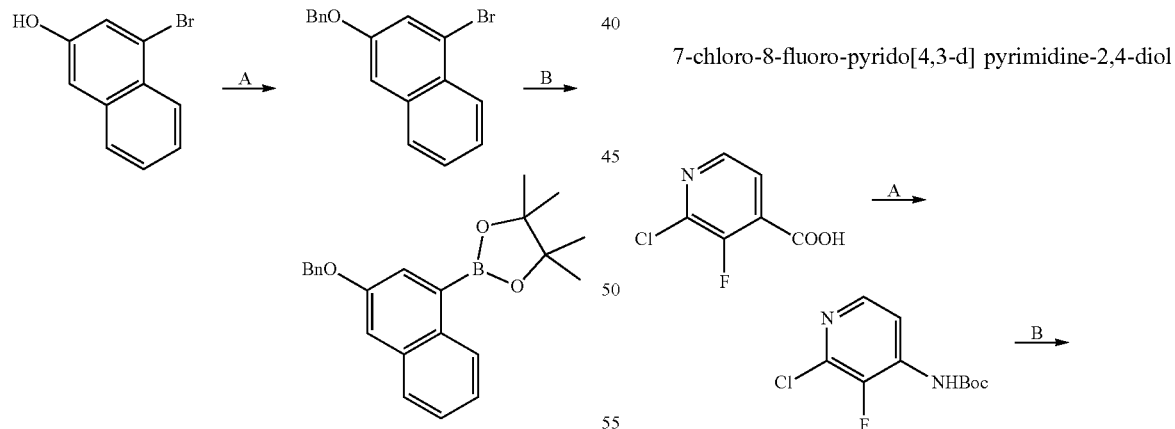

Step A. 3-(benzyloxy)-1-bromonaphthalene. A solution of 4-bromonaphthalen-2-ol (5.0 g, 22.41 mmol) in DMF (50 mL) was treated with sodium hydride (986 mg, 60%, 24.66 mmol) and heated to 50° C. for 1 hr under $N_2$. After cooling to room temperature, benzyl bromide (3.47 mL, 29.1 mmol) was added, followed by tetrabutylammonium iodide (828 mg, 2.24 mmol). The mixture was stirred for 16 h and then partitioned between water (200 mL) and EtOAc (200 mL). The aqueous layer was extracted with EtOAc (2×100 mL) and the combined organic phases were washed with water (4×100 mL) and brine (50 mL) then dried over $Na_2SO_4$, filtered and concentrated. The residue was purified by flash column chromatography eluting with 0-15% EtOAc/hexanes, then for a second time eluting with 0-5% EtOAc/hexanes to afford 3-(benzyloxy)-1-bromonaphthalene (6.16 g, 19.7 mmol, 88%).

Step B. 2-(3-(benzyloxy)naphthalen-1-yl)-4,4,5,5-tetramethyl-1,3,2-dioxaborolane. 3-(Benzyloxy)-1-bromonaphthalene (1.23 g, 3.93 mmol), 4,4,4',4',5,5,5',5'-octamethyl-2,2'-bi(1,3,2-dioxaborolane) (2.99 g, 11.8 mmol) and potassium acetate (1.16 g, 11.8 mmol) were combined in dioxanes (20 mL) and purged with Ar for 5 min. $PdCl_2$(dppf) (0.287 g, 0.393 mmol) was added and the reaction heated to 95° C. for 6 h and then stirred at room temperature for 16 h. The mixture was partitioned between water (100 mL) and EtOAc (50 mL) and the aqueous layer was extracted with EtOAc (2×30 mL). The combined organic phases were washed with brine (30 mL), dried over $Na_2SO_4$, filtered and concentrated in vacuo. The residue was purified by flash column chromatography, eluting with 0-15% EtOAc/hexanes to afford 2-(3-(benzyloxy)naphthalen-1-yl)-4,4,5,5-tetramethyl-1,3,2-dioxaborolane (1.25 g, 3.47 mmol, 88%) H NMR (400 MHz, $(CDCl_3)$ δ 8.66 (d, J=8.3 Hz, 1H), 7.85 (d, J=2.3 Hz, 1H), 7.49 (d, J=8.2 Hz, 2H), 7.35 (m, 7H), 5.19 (s, 2H), 1.41 (s, 12H).

Intermediate 4

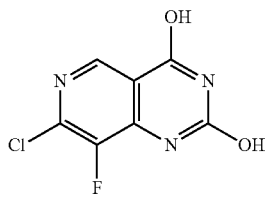 [SMILES: Oc1nc(O)c2cnc(Cl)c(F)c2n1]

7-chloro-8-fluoro-pyrido[4,3-d] pyrimidine-2,4-diol

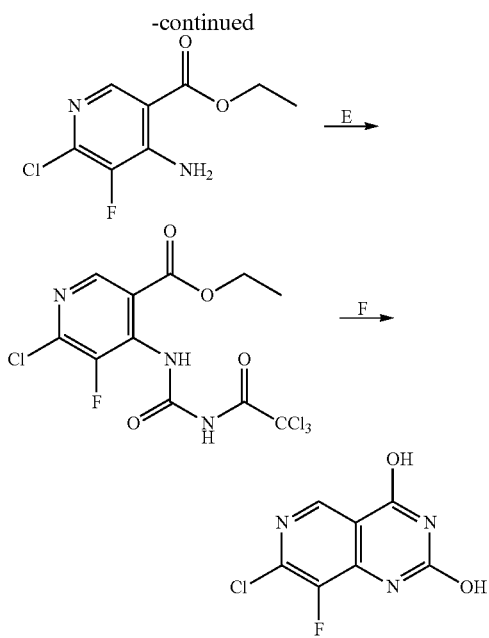

Step A. tert-butyl N-(2-chloro-3-fluoro-4-pyridyl)carbamate. A mixture of 2-chloro-3-fluoro-pyridine-4-carboxylic acid (180 g, 1.03 mol, 1.0 eq), 4 Å molecular sieve (300 g) and Et$_3$N (311 g, 3.08 mol, 428 mL, 3.0 eq) in toluene (1.3 L) and t-BuOH (1.01 kg, 13.6 mol, 1.3 L, 13.3 eq) was stirred at 110° C. for 0.5 hour under nitrogen. The mixture was cooled to 25° C. and diphenylphosphoryl azide (423 g, 1.54 mol, 333 mL, 1.5 eq) was added. The mixture was stirred at 110° C. for 5 hours. Upon completion, the mixture was diluted with water (2000 mL) and extracted with ethyl acetate (2×2000 mL). The combined organic layers were washed with brine (1×2000 mL), dried over sodium sulfate, filtered and concentrated under vacuum. The residue was purified by column chromatography (SiO$_2$, Petroleum ether/Ethyl acetate=100/1 to 5/1). tert-butyl N-(2-chloro-3-fluoro-4-pyridyl)carbamate (197 g, 799 mmol, 78% yield, 100% purity) was obtained as a white solid. LCMS [ESI, M+1]: 247; LCMS [ESI, M−55]: 191. $^1$H NMR (400 MHz, methanol-d$_4$) δ=8.11 (t, J=5.6 Hz, 1H), 7.99 (d, J=5.6 Hz, 1H), 1.52 (s, 9H).

Step B. 2-chloro-3-fluoro-pyridin-4-amine. To a solution of tert-butyl N-(2-chloro-3-fluoro-4-pyridyl)carbamate (199 g, 807 mmol, 1.0 eq) in MeCN (250 mL) was added HCl/dioxane (4 M, 796 mL, 3.95 eq). The mixture was stirred at 25° C. for 2 hours. Upon completion, the mixture was filtered, and the filter cake was diluted with saturated NaHCO$_3$ solution (2000 mL) and extracted with ethyl acetate (2×2000 mL). The combined organic layers were dried over sodium sulfate, filtered and concentrated under vacuum. 2-chloro-3-fluoro-pyridin-4-amine (107 g, 731 mmol, 91% yield, 99.9% purity) was obtained as a yellow solid and used in the next step without further purification. LCMS [ESI, M+1]: 147. $^1$H NMR (400 MHz, methanol-d$_4$) δ=7.61 (d, J=5.6 Hz, 1H), 6.67 (t, J=6.0 Hz, 1H).

Step C. 2-chloro-3-fluoro-5-iodo-pyridin-4-amine. To a solution of 2-chloro-3-fluoro-pyridin-4-amine (107 g, 730 mmol, 1.0 eq) and NIS (197 g, 876 mmol, 1.2 eq) in MeCN (550 mL) was added p-toluene sulfonic acid monohydrate (6.94 g, 36.5 mmol, 0.05 eq). The mixture was stirred at 70° C. for 16 hours. Upon completion, the mixture was diluted with water (300 mL) and ethyl acetate (2000 mL). The organic layer was washed with saturated Na$_2$CO$_3$ solution (2×1500 mL), saturated Na$_2$SO$_3$ (1×2000 mL) solution and brine (1×1500 mL), dried over Na$_2$SO$_4$, filtered and concentrated under vacuum. 2-chloro-3-fluoro-5-iodo-pyridin-4-amine (190 g, 676 mmol, 93% yield, 97.2% purity) was obtained as a yellow solid and used for next steps without further purification. LCMS [ESI, M+1]: 273. $^1$H NMR (400 MHz, methanol-d$_4$) δ=8.06 (s, 1H).

Step D. 4-amino-6-chloro-5-fluoro-pyridine-3-carboxylate. To a solution of 2-chloro-3-fluoro-5-iodo-pyridin-4-amine (78.4 g, 288 mmol, 1.0 eq) in EtOH (1500 mL) was added Pd(PPh$_3$)$_2$Cl$_2$ (20.2 g, 28.8 mmol, 0.1 eq) and Et$_3$N (105 g, 1.04 mol, 144 mL, 3.61 eq) under nitrogen. The suspension was degassed under vacuum and purged with nitrogen several times. The mixture was stirred under CO$_2$ (15.0 psi) at 80° C. for 15 hours. Upon completion, the mixture was filtered, and the filtrate was concentrated under vacuum to remove 70% of MeOH and the residue was filtered. The combined filter cakes were concentrated under vacuum. ethyl 4-amino-6-chloro-5-fluoro-pyridine-3-carboxylate (142 g, crude) was obtained as a yellow solid. LCMS [ESI, M+1]: 219. $^1$H NMR (400 MHz, dmso-d$_6$) δ=8.36 (s, 1H), 7.49-7.42 (m, 2H), 4.31 (q, J=7.2 Hz, 2H), 1.31 (t, J=7.2 Hz, 3H).

Step E. ethyl-6-chloro-5-fluoro-4-[(2,2,2-trichloroacetyl)carbamoylamino]pyridine-3-carboxylate. To a solution of ethyl 4-amino-6-chloro-5-fluoro-pyridine-3-carboxylate (20.3 g, 73.2 mmol, 1.0 eq) in THF (60 mL) was added 2,2,2-trichloroacetyl isocyanate (20.7 g, 110 mmol, 13.0 mL, 1.5 eq) at 25° C. The mixture was stirred at 25° C. for 10 min. Upon completion, the mixture was concentrated under vacuum. The crude product was triturated with MTBE (200 mL) at 25° C. for 5 min. Ethyl 6-chloro-5-fluoro-4-[(2,2,2-trichloroacetyl)carbamoylamino]pyridine-3-carboxylate (29.3 g, 67.74 mmol, 92% yield, 94.1% purity) was obtained as a gray solid. LCMS [ESI, M+1]: 408.

Step F. 7-chloro-8-fluoro-pyrido[4,3-d] pyrimidine-2,4-diol. To a solution of ethyl 6-chloro-5-fluoro-4-[(2,2,2-trichloroacetyl)carbamoylamino]pyridine-3-carboxylate (29.3 g, 63.1 mmol, 1.0 eq) in MeOH (290 mL) was added NH$_3$·MeOH (29 mL, 20% purity) at 25° C. The mixture was stirred at 25° C. for 1 h. Upon completion, the mixture was concentrated under vacuum. The crude product was triturated with MTBE (200 mL) at 25° C. for 10 min. 7-Chloro-8-fluoro-pyrido[4,3-d] pyrimidine-2,4-diol (18 g, crude) was obtained as a brown solid. LCMS [ESI, M+1]: 216. $^1$H NMR (400 MHz, dmso-d$_6$) δ=8.35 (br s, 1H).

Intermediate 5

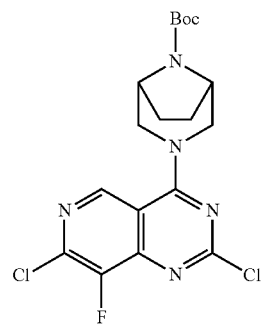 [SMILES: CC(C)(C)OC(=O)N1C2CCC1CN(c1nc(Cl)nc3c(F)c(Cl)ncc13)C2]

145 tert-butyl3-(2,7-dichloro-8-fluoro-pyrido[4,3-d]pyrimidin-4-yl)-3,8-diazabicyclo[3.2.1]octane-8-carboxylate

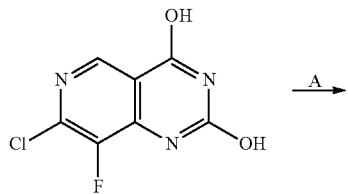

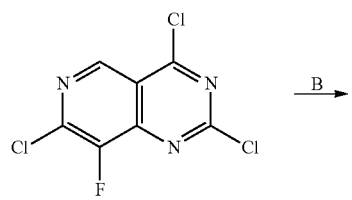

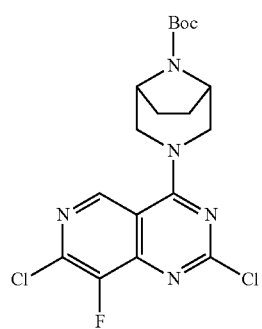

Step A. 2,4,7-trichloro-8-fluoro-pyrido[4,3-d]pyrimidine. A mixture of 7-chloro-8-fluoro-pyrido[4,3-d]pyrimidine-2,4-diol (5 g, 23.2 mmol, 1.0 eq) and N-ethyl-N-isopropyl-propan-2-amine (15 g, 116 mmol, 20.2 mL, 5.0 eq) in POCl$_3$ (82.5 g, 538 mmol, 50 mL, 23.2 eq) was stirred at 100° C. for 1 hour. After completion, the mixture was concentrated under vacuum to give 2,4,7-trichloro-8-fluoro-pyrido[4,3-d]pyrimidine (6.5 g, crude) and used in next step without further purification. Yellow oil.

Step B. tert-butyl-3-(2,7-dichloro-8-fluoro-pyrido[4,3-d]pyrimidin-4-yl)-3,8-diazabicyclo[3.2.1]octane-8-carboxylate. To a solution of 2,4,7-trichloro-8-fluoro-pyrido[4,3-d]pyrimidine (6.5 g, crude) and N-ethyl-N-isopropylpropan-2-amine (20 g, 155 mmol, 26.9 mL,) in dichloromethane (20 mL) was added tert-butyl 3,8-diazabicyclo[3.2.1]octane-8-carboxylate (4.92 g, 23.2 mmol) at −40° C. After stirring at −40° C. for 0.5 h, the mixture was diluted with water (20 mL), extracted with dichloromethane (2×20 mL). The combined organic layers were washed with brine (30 mL), dried over Na$_2$SO$_4$, filtered and concentrated under vacuum, affording tert-butyl-3-(2,7-dichloro-8-fluoro-pyrido[4,3-d]pyrimidin-4-yl)-3,8-diazabicyclo[3.2.1]octane-8-carboxylate (4 g, two steps 42% yield). Yellow solid. LCMS [ESI, M+1]: 428.

146

Intermediate 6

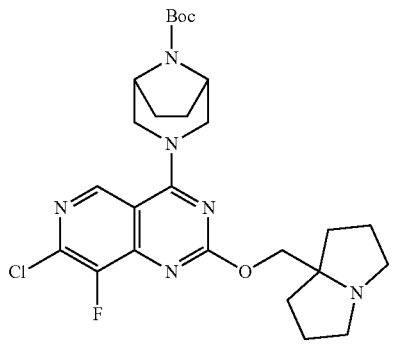 [SMILES: CC(C)(C)OC(=O)N1C2CCC1CN(c1nc(OCC34CCCN3CCC4)nc3c(F)c(Cl)ncc13)C2]

tert-butyl (1R,5S)-3-(7-chloro-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate

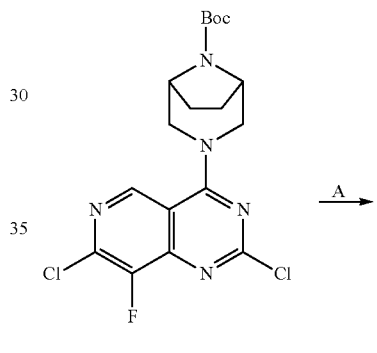

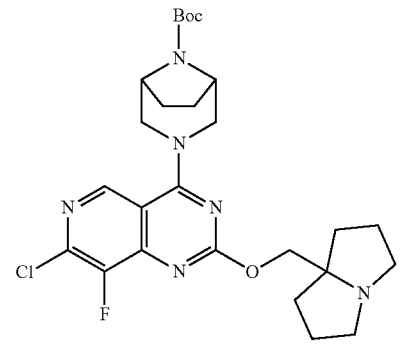

Step A. tert-butyl (1R,5S)-3-(7-chloro-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate. A mixture of tert-butyl-3-(2,7-dichloro-8-fluoro-pyrido[4,3-d]pyrimidin-4-yl)-3,8-diazabicyclo[3.2.1]octane-8-carboxylate (2 g, 4.67 mmol, 1.0 eq), (tetrahydro-1H-pyrrolizin-7a(5H)-yl)methanol (1.32 g, 9.34 mmol, 2.0 eq) and DIEA (1.81 g, 14.0 mmol, 2.44 mL, 3.0 eq) in dioxane (30 mL) was stirred at 80° C. for 6 hours. After completion, the mixture was diluted with water (30 mL), extracted with ethyl acetate (2×40 mL). The combined organic layers were washed with brine (30 mL), dried over Na$_2$SO$_4$, filtered and concentrated under vacuum. The residue was purified by reversed phase flash chromatography [water (formic acid, 0.1%)/acetonitrile] to give the title compound (1.83 g, 73% yield). Yellow solid. LCMS (ESI, M+1): 533.

Intermediate 7

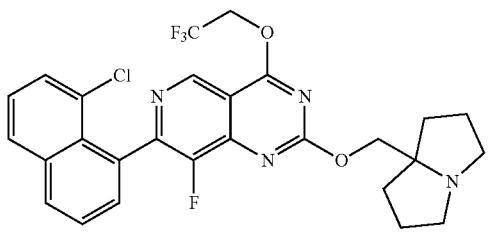

7-(8-chloronaphthalen-1-yl)-8-fluoro-2-((tetrahydro-1H-pyrrolizin-7a(5H)-yl)methoxy)-4-(2,2,2-trifluoroethoxy)pyrido[4,3-d]pyrimidine

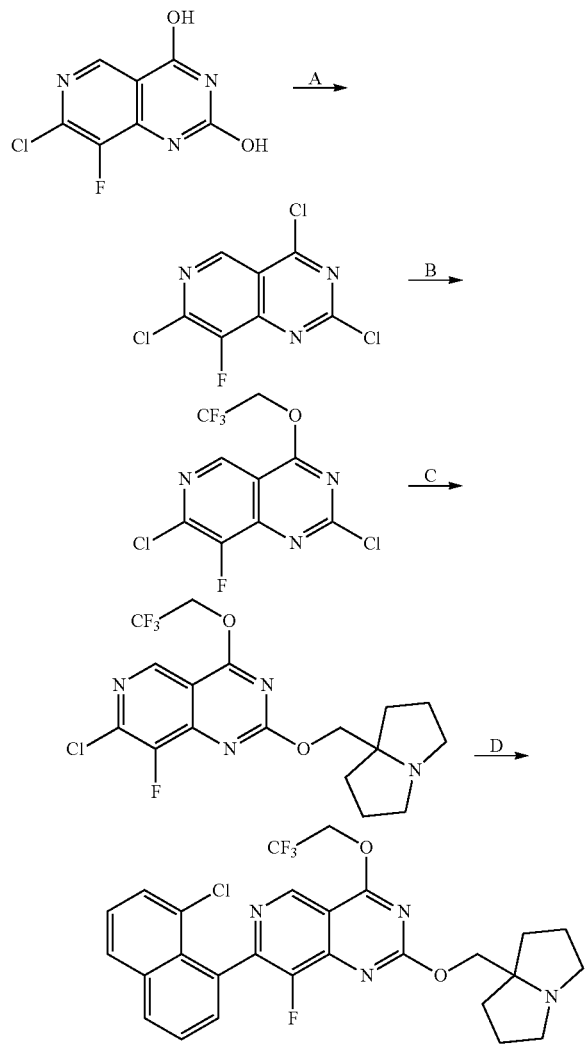

Step A. 2,4,7-trichloro-8-fluoro-pyrido[4,3-d]pyrimidine. To a mixture of -chloro-8-fluoro-pyrido[4,3-d]pyrimidine-2,4-diol (20 g, 92.8 mmol, 1.00 eq) in toluene (100 mL) was added $POCl_3$ (42.7 g, 278 mmol, 25.9 mL, 3.00 eq) and N-ethyl-N-isopropylpropan-2-amine (36.0 g, 278 mmol, 48.5 mL, 3.00 eq) at 0° C. The mixture was stirred at 110° C. for 3 hours. After completion, the mixture was concentrate under reduced pressure at 40° C. to dryness affording 2,4,7-trichloro-8-fluoro-pyrido[4,3-d]pyrimidine (23.4 g, crude) as a black oil.

Step B. 2,7-dichloro-8-fluoro-4-(2,2,2-trifluoroethoxy) pyrido[4,3-d]pyrimidine. To a solution of 2,2,2-trifluoroethanol (11.1 g, 111 mmol, 8.01 mL, 1.20 eq) in toluene (200 mL) was added t-BuONa (26.7 g, 278 mmol, 3.00 eq) at 0° C. The mixture was first stirred at 10° C. for 0.5 hour. Then the above mixture was added to 2,4,7-trichloro-8-fluoro-pyrido[4,3-d]pyrimidine (23.4 g, 92.7 mmol, 1.00 eq) in toluene (200 mL) at −10° C. After addition, the mixture was stirred at −10° C.~25° C. for 16 hours. After monitored, a mixture of t-BuONa (1.78 g, 18.5 mmol, 0.2 eq) and 2,2,2-trifluoroethanol (1.85 g, 18.5 mmol, 1.33 mL, 0.20 eq) in toluene (20.0 mL) was added thereto at 0° C. The mixture was continued to stir at 25° C. for 30 hours. After completion, the mixture was poured onto $SiO_2$ column, purified by column chromatography ($SiO_2$, petroleum ether/ethyl acetate=30/1 to 10/1), and then further purified by reversed-phase flash (0.1% formic acid condition) affording 2,7-dichloro-8-fluoro-4-(2,2,2-trifluoroethoxy)pyrido[4,3-d]pyrimidine (16.3 g, 55.6% yield); Yellow solid; LCMS [ESI, M+1]: 316.

Step C. 7-chloro-8-fluoro-2-((tetrahydro-1H-pyrrolizin-7a(5H)-yl)methoxy)-4-(2,2,2-trifluoroethoxy)pyrido[4,3-d] pyrimidine. To a mixture of (tetrahydro-1H-pyrrolizin-7a (5H)-yl)methanol (17.9 g, 126 mmol, 2.00 eq), 4 Å MS (15.0 g) and N-ethyl-N-isopropylpropan-2-amine (16.4 g, 126 mmol, 22.0 mL, 2.00 eq) in 2-methyltetrahydrofuran (200 mL) was added 2,7-dichloro-8-fluoro-4-(2,2,2-trifluoroethoxy)pyrido[4,3-d]pyrimidine (20.0 g, 63.3 mmol, 1.00 eq) in 2-methyltetrahydrofuran (200 mL) at 0~ 5° C. The mixture was stirred at 0-25° C. for 2 hours. After completion, the mixture was filtered and washed with ethyl acetate (100 mL). The filtrate was quenched by saturated $NH_4Cl$ aqueous solution (300 mL), and the organic layer was separated and dried over anhydrous $Na_2SO_4$. The mixture was filtered, and the filtrate was concentrated under reduced pressure at 40° C. to dryness. The crude product was triturated with $CH_3CN$ (20 mL) at 25° C. for 15 minutes and filtered, the filter cake was dried in vacuum at 40° C. affording the title compound (18.2 g, 64.6% yield). Light yellow solid. $^1$H NMR (400 MHz, $CDCl_3$) δ 8.99 (s, 1H), 5.03 (q, J=8.4 Hz, 2H), 4.32 (s, 2H), 3.23-3.05 (m, 2H), 2.67 (td, J=6.8, 10.4 Hz, 2H), 2.11-1.96 (m, 2H), 1.96-1.85 (m, 4H), 1.74-1.69 (m, 2H); LCMS [ESI, M+1]: 421.

Step D. 7-(8-chloronaphthalen-1-yl)-8-fluoro-2-((tetrahydro-1H-pyrrolizin-7a(5H)-yl)methoxy)-4-(2,2,2-trifluoroethoxy)pyrido[4,3-d]pyrimidine. To a mixture of 7-chloro-8-fluoro-2-((tetrahydro-1H-pyrrolizin-7a(5H)-yl) methoxy)-4-(2,2,2-trifluoroethoxy)pyrido[4,3-d]pyrimidine (5.00 g, 11.9 mmol, 1.00 eq), (8-chloronaphthalen-1-yl) trimethylstannane (7.73 g, 23.8 mmol, 2.00 eq) in toluene (150 mL) was added 4 Å MS (5.00 g) at 25° C. The mixture was stirred at 25° C. for 1 hour. Then CuI (792 mg, 4.16 mmol, 0.35 eq), Pd(dppf)Cl$_2$ (1.30 g, 1.78 mmol, 0.15 eq) and BINAP (1.85 g, 2.97 mmol, 0.25 eq) were added thereto at 25° C. The mixture was degassed under vacuum and purged with N2 several times over 30 minutes. Then the mixture was heated to 90° C. and stirred for 2 hours. The mixture was cooled to 25° C., and then (8-chloronaphthalen-1-yl)trimethylstannane (1.93 g, 5.94 mmol, 0.50 eq) was added thereto at 25° C. The mixture was heated to 90° C. and stirred for 1 hour. After completion, the mixture was filtered, and the filtrate was concentrated under reduced pressure at 40° C. to dryness. The crude product was purified by reversed-phase flash (0.1% formic acid condition) affording the title compound (2.3 g, 33.9% yield); Yellow solid. $^1$H NMR (400 MHz, CDCl$_3$) δ 9.25 (s, 1H), 8.02 (dd, J=1.2, 8.0 Hz, 1H), 7.89 (dd, J=0.8, 8.0 Hz, 1H), 7.65-7.60 (m, 1H), 7.59-7.53 (m, 2H), 7.46-7.41 (m, 1H), 5.08 (q, J=8.0 Hz, 2H), 4.46 (s, 2H), 3.32 (br d, J=3.8 Hz, 2H), 2.83-2.70 (m, 2H), 2.20-2.09 (m, 2H), 2.03-1.90 (m, 4H), 1.82-1.72 (m, 2H); LCMS [ESI, M+1]: 547.

Intermediate 8

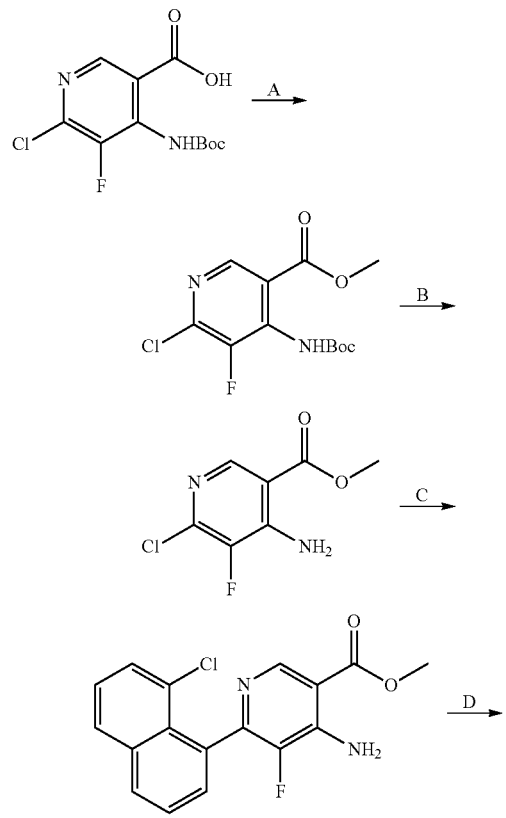

2,4-dichloro-7-(8-chloro-1-naphthyl)-8-fluoro-pyrido[4,3-d]pyrimidine

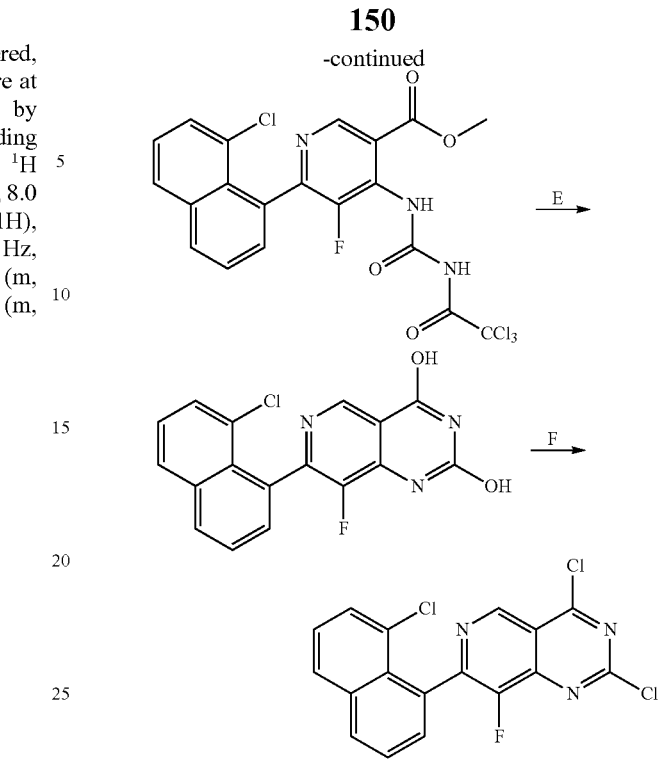

Step A. methyl 4-(tert-butoxycarbonylamino)-6-chloro-5-fluoro-pyridine-3-carboxylate. To a solution of 4-((tert-butoxycarbonyl)amino)-6-chloro-5-fluoronicotinic acid (14.3 g, 49.2 mmol, 1 eq) in MeOH (70 mL) and toluene (210 mL) was added TMSCHN$_2$ (2 M in hexane, 44.3 mL, 1.8 eq) slowly. After stirring at 15° C. for 2 hours, the mixture was quenched with 2N HCl (100 mL) and layers were separated. The organic phase was washed with saturated aqueous NaHCO$_3$ (150 mL), followed by brine (150 mL). The organic layer was dried over Na$_2$SO$_4$, filtered and concentrated under vacuum. The residue was purified by silica gel chromatography (petroleum ether/ethyl acetate 10/1 to 1/1) to give methyl 4-(tert-butoxycarbonylamino)-6-chloro-5-fluoro-pyridine-3-carboxylate (15 g, 91%). Colorless oil; Rf=0.50 (3:1 petroleum ether/ethyl acetate); $^1$H NMR (400 MHz, CDCl$_3$): δ 8.85 (br s, 1H), 8.68 (s, 1H), 3.98 (s, 3H), 1.57-1.49 (m, 9H); LCMS [ESI, M+1]: 305.

Step B. methyl 4-amino-6-chloro-5-fluoro-pyridine-3-carboxylate. To a solution of methyl 4-(tert-butoxycarbonylamino)-6-chloro-5-fluoro-pyridine-3-carboxylate (15 g, 49.2 mmol, 1.0 eq) in MeCN (150 mL) was added HCl·dioxane (4 M, 290 mL, 23.6 eq) at 0° C. The mixture was stirred at 15° C. for 0.5 hour, and the solvent was removed under reduced pressure. The residue was diluted with saturated Na$_2$CO$_3$ solution (100 mL) and extracted with ethyl acetate (3×200 mL). The organic layers were dried over Na$_2$SO$_4$ and concentrated under vacuum to give methyl 4-amino-6-chloro-5-fluoro-pyridine-3-carboxylate (9.07 g, 89%) which was used directly in the next step without further purification. Orange solid; LCMS [ESI, M+1]: 205.

Step C. methyl 4-amino-6-(8-chloro-1-naphthyl)-5-fluoro-pyridine-3-carboxylate. A mixture of methyl 4-amino-6-chloro-5-fluoro-pyridine-3-carboxylate (6 g, 29.3 mmol, 1.0 eq), (8-chloronaphthalen-1-yl)trimethylstannane (21.0 g, 64.5 mmol, 2.2 eq), CuI (1.68 g, 8.80 mmol, 0.3 eq), Pd(dppf)Cl$_2$ (2.15 g, 2.93 mmol, 0.1 eq), and BINAP (3.65 g, 5.87 mmol, 0.2 eq) in toluene (120 mL) was degassed and then heated to 100° C. for 11 hours under N$_2$.

The mixture was filtered and the filtrate was concentrated under vacuum. The residue was diluted with water (50 mL) and extracted with ethyl acetate (2×60 mL). The organic layers were dried over Na₂SO₄ and concentrated under vacuum. The residue was purified by chromatography (Al₂O₃, petroleum ether/ethyl acetate 30/1 to 1/1). The product was triturated with a mixed solution (DMAc/methanol 1/2, 30 mL) at 15° C. for 10 minutes to give methyl 4-amino-6-(8-chloro-1-naphthyl)-5-fluoro-pyridine-3-carboxylate (5.33 g, 54%). Yellow solid; Rf=0.20 (3:1 petroleum ether/ethyl acetate); LCMS [ESI, M+1]: 331.

Step D. methyl 6-(8-chloro-1-naphthyl)-5-fluoro-4-[(2,2,2-trichloroacetyl)carbamoylamino] pyridine-3-carboxylate. To a solution of methyl 4-amino-6-(8-chloro-1-naphthyl)-5-fluoro-pyridine-3-carboxylate (5.5 g, 16.6 mmol, 1.0 eq) in THF (82 mL) was added 2,2,2-trichloroacetyl isocyanate (3.45 g, 18.3 mmol, 2.17 mL, 1.1 eq) dropwise. The mixture was stirred at 15° C. for 10 minutes, and the mixture was concentrated under vacuum. The residue was triturated with MTBE (20 mL) at 15° C. for 15 minutes to give methyl 6-(8-chloro-1-naphthyl)-5-fluoro-4-[(2,2,2-trichloroacetyl)carbamoylamino] pyridine-3-carboxylate (8 g, crude). Yellow solid; LCMS [ESI, M+1]: 520.

Step E. 7-(8-chloro-1-naphthyl)-8-fluoro-pyrido[4,3-d]pyrimidine-2,4-diol. A suspension of methyl 6-(8-chloro-1-naphthyl)-5-fluoro-4-[(2,2,2-trichloroacetyl)carbamoylamino] pyridine-3-carboxylate (8 g, 15.4 mmol, 1.0 eq) in NH₃·MeOH (20 mL, 20% purity) was stirred at 15° C. for 0.5 hour, the mixture was concentrated under vacuum. The residue was triturated with MTBE (30 mL) at 15° C. for 15 minutes to give 7-(8-chloro-1-naphthyl)-8-fluoro-pyrido[4,3-d]pyrimidine-2,4-diol (5.3 g, two steps 93%). Yellow solid; ¹H NMR (400 MHz, DMSO): δ 9.59-8.27 (m, 1H), 8.24-8.13 (m, 1H), 8.11-8.03 (m, 1H), 7.74-7.61 (m, 2H), 7.60-7.52 (m, 2H), 3.59-3.31 (m, 2H); LCMS [ESI, M+1]: 342.

Step F. 2,4-dichloro-7-(8-chloro-1-naphthyl)-8-fluoro-pyrido[4,3-d]pyrimidine. A solution of POCl₃ (1.62 g, 10.6 mmol, 985 μL, 36.2 eq) and N-ethyl-N-isopropylpropan-2-amine (189 mg, 1.46 mmol, 255 μL, 5.0 eq) was stirred at 0° C., followed by the addition of 7-(8-chloro-1-naphthyl)-8-fluoro-pyrido[4,3-d]pyrimidine-2,4-diol (0.1 g, 293 μmol, 1.0 eq). The suspension was stirred at 110° C. for 1 hour, the mixture was concentrated under vacuum to give 2,4-dichloro-7-(8-chloro-1-naphthyl)-8-fluoro-pyrido[4,3-d]pyrimidine (0.11 g, crude) which was used directly in the next step without further purification. Black oil.

Intermediate 9

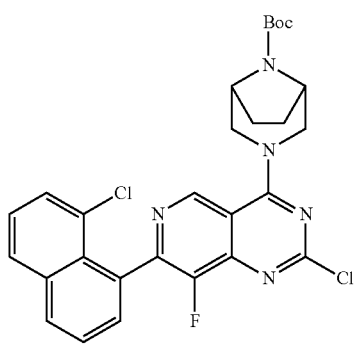 [SMILES: CC(C)(C)OC(=O)N1C2CCC1CN(c1nc(Cl)nc3c(F)c(-c4cccc5cccc(Cl)c45)ncc13)C2]

tert-butyl 3-[2-chloro-7-(8-chloro-1-naphthyl)-8-fluoro-pyrido[4,3-d]pyrimidin-4-yl]-3,8-diazabicyclo[3.2.1]octane-8-carboxylate

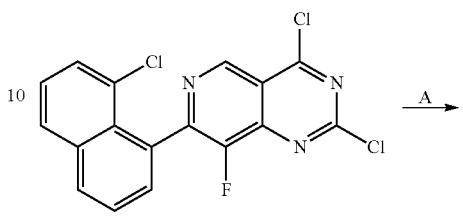

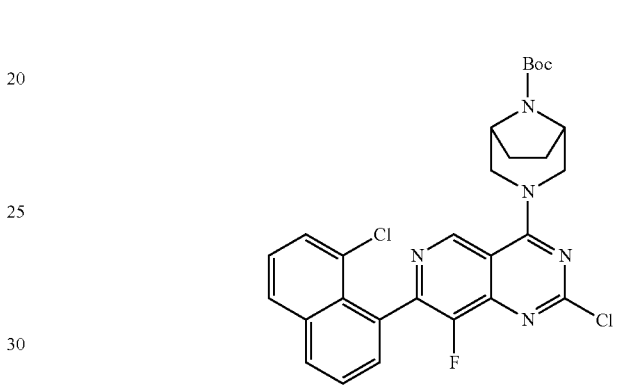

Step A. tert-butyl 3-[2-chloro-7-(8-chloro-1-naphthyl)-8-fluoro-pyrido[4,3-d]pyrimidin-4-yl]-3,8-diazabicyclo[3.2.1]octane-8-carboxylate. To a solution of 2,4-dichloro-7-(8-chloronaphthalen-1-yl)-8-fluoropyrido[4,3-d]pyrimidine (2.11 g, 5.57 mmol, 1.0 eq) in DCM (40 mL) was added N-ethyl-N-isopropylpropan-2-amine (3.60 g, 27.9 mmol, 4.85 mL, 5.0 eq) at −40° C. until the pH of the resulting mixture was adjusted to 8 followed by the addition of tert-butyl 3,8-diazabicyclo[3.2.1]octane-8-carboxylate (1.06 g, 5.02 mmol, 0.9 eq). Then mixture was stirred at −40° C. for 0.5 hour, the mixture was added to water (50 mL) and layers were separated. The aqueous phase was extracted with ethyl acetate (50 mL). Combined organic layers were dried over Na₂SO₄, filtered and concentrated under vacuum. The residue was purified by chromatography (Al₂O₃, petroleum ether/ethyl acetate 10/1 to 1/1) to give tert-butyl 3-[2-chloro-7-(8-chloro-1-naphthyl)-8-fluoro-pyrido[4,3-d]pyrimidin-4-yl]-3,8-diazabicyclo[3.2.1]octane-8-carboxylate (2 g, 63%). Yellow solid; Rf=0.30 (petroleum ether/ethyl acetate 3/1); LCMS [ESI, M+1]: 554.

Intermediate 10

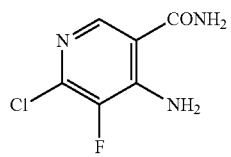 [SMILES: NC(=O)c1cnc(Cl)c(F)c1N]

4-amino-6-chloro-5-fluoro-pyridine-3-carboxamide

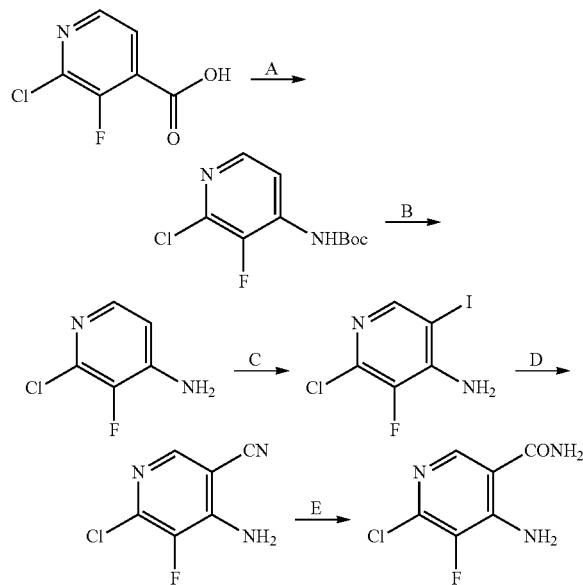

Step A. tert-butyl N-(2-chloro-3-fluoro-4-pyridyl)carbamate. A mixture of 2-chloro-3-fluoro-pyridine-4-carboxylic acid (180 g, 1.03 mol, 1.0 eq), 4 A molecular sieve (300 g) and Et₃N (311 g, 3.08 mol, 428 mL, 3.0 eq) in toluene (1.3 L) and t-BuOH (1.01 kg, 13.6 mol, 1.3 L, 13.3 eq) was stirred at 110° C. for 0.5 hour under nitrogen. The mixture was cooled to 25° C. and diphenylphosphoryl azide (423 g, 1.54 mol, 333 mL, 1.5 eq) was added. The mixture was stirred at 110° C. for 5 hours. Upon completion, the mixture was diluted with water (2000 mL) and extracted with ethyl acetate (2×2000 mL). The combined organic layers were washed with brine (1×2000 mL), dried over sodium sulfate, filtered and concentrated under vacuum. The residue was purified by column chromatography (SiO₂, Petroleum ether/Ethyl acetate=100/1 to 5/1). tert-butyl N-(2-chloro-3-fluoro-4-pyridyl)carbamate (197 g, 799 mmol, 78% yield, 100% purity) was obtained as a white solid. LCMS [ESI, M+1]: 247; LCMS [ESI, M−55]: 191. ¹H NMR (400 MHz, methanol-d₄) δ=8.11 (t, J=5.6 Hz, 1H), 7.99 (d, J=5.6 Hz, 1H), 1.52 (s, 9H).

Step B. 2-chloro-3-fluoropyridin-4-amine. To a solution of tert-butyl N-(2-chloro-3-fluoro-4-pyridyl)carbamate (199 g, 807 mmol, 1.0 eq) in MeCN (250 mL) was added HCl/dioxane (4 M, 796 mL, 3.95 eq). The mixture was stirred at 25° C. for 2 hours. Upon completion, the mixture was filtered, and the filter cake was diluted with saturated NaHCO₃ solution (2000 mL) and extracted with ethyl acetate (2×2000 mL). The combined organic layers were dried over sodium sulfate, filtered and concentrated under vacuum. 2-chloro-3-fluoropyridin-4-amine (107 g, 91% yield) was obtained as a yellow solid. LCMS [ESI, M+1]: 147. ¹H NMR (400 MHz, methanol-d₄) δ=7.61 (d, J=5.6 Hz, 1H), 6.67 (t, J=6.0 Hz, 1H).

Step C. 2-chloro-3-fluoro-5-iodopyridin-4-amine. To a solution of 2-chloro-3-fluoropyridin-4-amine (107 g, 730 mmol, 1.0 eq) and NIS (197 g, 876 mmol, 1.2 eq) in MeCN (550 mL) was added p-toluene sulfonic acid monohydrate (6.94 g, 36.5 mmol, 0.05 eq). The mixture was stirred at 70° C. for 16 hours. Upon completion, the mixture was diluted with water (300 mL) and ethyl acetate (2000 mL), The organic layer was washed with saturated Na₂CO₃ solution (2×1500 mL), saturated Na₂SO₃ (2000 mL) solution and brine (1500 mL), dried over Na₂SO₄, filtered and concentrated under vacuum. 2-chloro-3-fluoro-5-iodopyridin-4-amine (190 g, 93% yield) was obtained as a yellow solid. LCMS [ESI, M+1]: 273. ¹H NMR (400 MHz, methanol-d₄) δ=8.06 (s, 1H).

Step D. 4-amino-6-chloro-5-fluoro-pyridine-3-carbonitrile. To a mixture of 2-chloro-3-fluoro-5-iodopyridin-4-amine (440 g, 1.61 mol, 1.0 eq) and 4 A MS (150 g) in DMF (3.5 L) was added Pd(PPh₃)₄ (93.31 g, 80.75 mmol, 0.05 eq) and Zn(CN)₂ (246.54 g, 2.10 mol, 133.27 mL, 1.3 eq) in one portion at 25° C. under N₂. Then the mixture was heated to 100° C. and stirred for 2 hours. The mixture was cooled to 20° C., then poured into brine (2000 mL) and stirred for 5 min. The aqueous phase was extracted with ethyl acetate (2000 mL×6). The combined organic phase was washed with brine (2000 mL*3), dried with anhydrous Na₂SO₄, filtered and concentrated in vacuum. The crude product (1100 g) was triturated with ethyl acetate (100 mL) at 25° C. for 30 min, filtered and concentrated in vacuum. 4-amino-6-chloro-5-fluoro-pyridine-3-carbonitrile (230 g, 83% yield) was obtained as a yellow solid. ¹H NMR (400 MHz, DMSO-d6) δ=8.20 (s, 1H), 7.65 (br s, 2H).

Step E. 4-amino-6-chloro-5-fluoro-pyridine-3-carboxamide. To the H2SO₄ (146 g, 1.46 mol, 79.3 mL, 98% purity, 5.0 eq) was added 4-amino-6-chloro-5-fluoro-pyridine-3-carbonitrile (50 g, 291 mmol, 1.0 eq) at 10° C. The reaction mixture was heated to 60° C. for 1 h. Upon completion, the reaction mixture was poured into ice water (1 L) with stirring. A yellow solid was precipitated. The mixture was filtered. The filter cake was triturated with saturated NaHCO₃ (50 mL) and filtered. The combined filtrate was basified by solid Na₂CO₃ to pH=7. A yellow solid was precipitated. The mixture was filtered. The filter cake was washed with water (2×10 mL). The combined filter cakes were dried in vacuum to provide 4-amino-6-chloro-5-fluoro-pyridine-3-carboxamide (44 g, 80% yield). Yellow solid. LCMS [ESI, M+1]: 190; ¹H ¹H NMR (400 MHz, CD₃SOCD₃) δ 8.31 (s, 1H), 8.10 (br s, 1H), 7.77-7.47 (m, 3H).

Intermediate 11

(1R,5S)-tert-butyl-3-(7-chloro-8-fluoropyrido[4,3-d]pyrimidin-4-yl)-3,8-diazabicyclo [3.2.1]octane-8-carboxylate

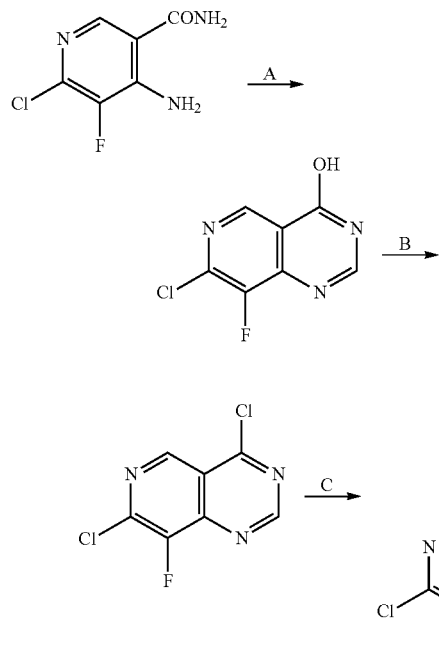

Step A. 7-chloro-8-fluoropyrido[4,3-d]pyrimidin-4-ol. To a solution of 4-amino-6-chloro-5-fluoronicotinamide (4 g, 21.1 mmol, 1.0 eq) in acetic acid (40 mL) was added trimethoxymethane (49.3 g, 464 mmol, 50.9 mL, 22 eq) dropwise. The mixture was stirred at 135° C. for 2 hours. The mixture was diluted with water (150 mL) and extracted with ethyl acetate (2×100 mL). The combined organic layers were washed with brine (60 mL), dried over $Na_2SO_4$, filtered and concentrated in vacuum. The residue was triturated with acetonitrile (10 mL) to give 7-chloro-8-fluoropyrido[4,3-d]pyrimidin-4-ol (2.2 g, 52% yield). Yellow solid. $^1$H NMR (400 MHz, DMSO-$d_6$) δ=12.99 (br s, 1H), 8.94 (s, 1H), 8.40 (s, 1H). LCMS [ESI, M+1]: 200.

Step B. 4,7-dichloro-8-fluoropyrido[4,3-d]pyrimidine. To a solution of 7-chloro-8-fluoropyrido[4,3-d]pyrimidin-4-ol (2.2 g, 11.0 mmol, 1.0 eq) in N-ethyl-N-isopropylpropan-2-amine (2.85 g, 22.0 mmol, 3.84 mL, 2 eq) was added $POCl_3$ (82.5 g, 538 mmol, 50 mL, 48.8 eq). The mixture was stirred at 110° C. for 3 h. The mixture was concentrated in vacuum to give 4,7-dichloro-8-fluoropyrido[4,3-d]pyrimidine (8.3 g, crude). Yellow oil.

Step C. (1R,5S)-tert-butyl 3-(7-chloro-8-fluoropyrido[4,3-d]pyrimidin-4-yl)-3,8-diazabicyclo [3.2.1]octane-8-carboxylate. To a solution of 4,7-dichloro-8-fluoropyrido[4,3-d]pyrimidine (7.8 g, crude) and (1R,5S)-tert-butyl 3,8-diazabicyclo[3.2.1]octane-8-carboxylate (9.11 g, 42.9 mmol) in dichloromethane (80 mL) was added N-ethyl-N-isopropylpropan-2-amine (23.1 g, 179 mmol, 31.2 mL). The mixture was stirred at 15° C. for 1 h. After completion, the mixture was diluted with water (150 mL) and extracted with ethyl acetate (2×80 mL). The combined organic layers were washed with brine (60 mL), dried over $Na_2SO_4$, filtered and concentrated in vacuum. The residue was triturated with ethyl acetate (8 mL) and filtered. The filter cake was dried in vacuum to give (1R,5S)-tert-butyl-3-(7-chloro-8-fluoropyrido[4,3-d]pyrimidin-4-yl)-3,8-diazabicyclo[3.2.1]octane-8-carboxylate (2 g, two steps 46%). Yellow solid. $^1$H NMR (400 MHz, CDCl$_3$) δ=8.86 (s, 1H), 8.75 (s, 1H), 4.56 (br d, J=11.2 Hz, 2H), 4.38 (br s, 2H), 3.71 (s, 2H), 1.98-1.92 (m, 2H), 1.67 (br d, J=7.6 Hz, 2H), 1.53 (s, 9H). LCMS [ESI, M+1]: 394.

Intermediate 12

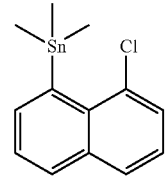

(8-chloro-1-naphthyl)-trimethyl-stannane

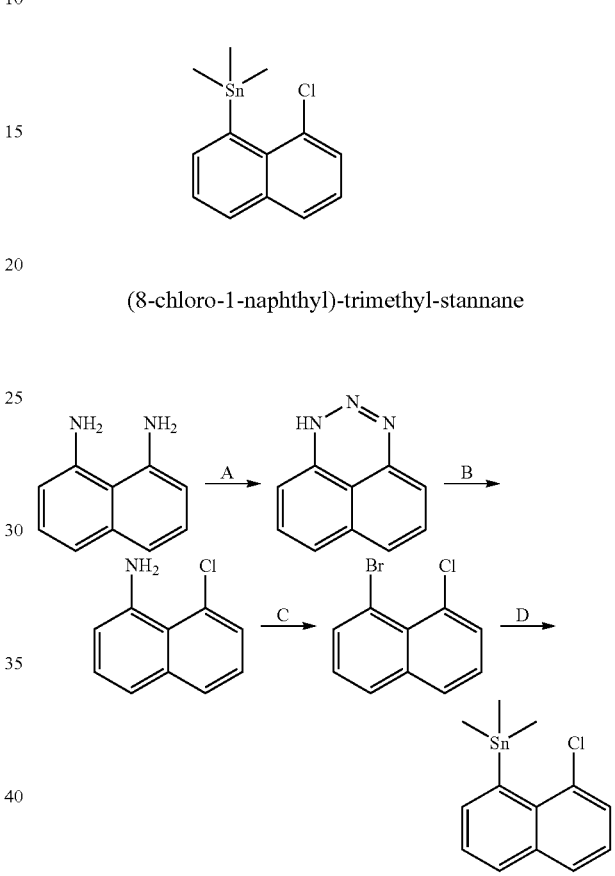

Step A. 1H-naphtho[1,8-de][1,2,3]triazine. To a solution of naphthalene-1,8-diamine (100 g, 632 mmol, 1 eq) in AcOH (200 mL) and EtOH (1000 mL) was added isoamyl nitrite (72.6 g, 619 mmol, 83.4 mL, 0.98 eq) dropwise over a period of 2 hours with temperature controlled between 18 and 21° C. under a cold-water bath. After the addition, the resulting red suspension was stirred at 25° C. for 16 hours. The solid was collected by filtration, washed with ethanol (2×500 mL) and dried under vacuum to give 1H-naphtho[1,8-de][1,2,3]triazine (84 g, 496 mmol, 79% yield). Red crystalline solid; LCMS [ESI, M+1]: 170.

Step B. 8-chloronaphthalen-1-amine. To a solution of 1H-naphtho[1,8-de][1,2,3]triazine (84 g, 496 mmol, 1 eq) in HCl (1.5 L) was added Cu (2.10 g, 33.1 mmol, 234 μL, 0.07 eq). The mixture was stirred at 25° C. for 12 hours. The resulting mixture was diluted with water (500 mL) and heated at 85° C. for 30 mins. The resulting almost clear aqueous solution was filtered, cooled, basified with aqueous ammonia (until blue to litmus paper) and the solution was extracted with ether acetate (2×1000 mL). The combined extracts were dried over $Na_2SO_4$, filtered and concentrated under vacuum. The residue was purified by column chromatography (SiO$_2$, Petroleum ether/Ethyl acetate=200/1 to 5/1) to give 8-chloronaphthalen-1-amine (57 g, 259 mmol, 52% yield, 81% purity). Red solid; LCMS [ESI, M+1]: 178.

Step C. 1-bromo-8-chloronaphthalene. To a solution of 8-chloronaphthalen-1-amine (57 g, 320 mmol, 1 eq) and TsOH·H$_2$O (219 g, 1.16 mol, 3.6 eq) in MeCN (1000 mL) was added a solution of NaNO$_2$ (39.8 g, 577 mmol, 1.8 eq) and CuBr (138 g, 963 mmol, 29.3 mL, 3 eq) in H$_2$O (120 mL) at −5° C., then the reaction mixture was stirred at 25° C. for 12 hours. The reaction mixture was added saturated Na$_2$SO$_3$ solution (100 mL), stirred for 15 mins, and then extracted with ethyl acetate (3×1000 mL). The combined organic layers were washed with brine (500 mL), dried over Na$_2$SO$_4$, filtered and concentrated under reduced pressure to give a residue. The residue was purified by column chromatography (SiO$_2$, Petroleum ether) to give 1-bromo-8-chloronaphthalene (56 g, 229 mmol, 72% yield, 99% purity). White solid; $^1$H NMR (400 MHz, CDCl$_3$) δ 7.93 (dd, J=1.2, 7.6 Hz, 1H), 7.82 (dd, J=1.2, 8.4, 1H), 7.79 (dd, J=1.2, 8.4, 1H), 7.67 (dd, J=1.2, 7.6 Hz, 1H), 7.37 (t, J=8.0 Hz, 1H), 7.28 (t, J=8.0 Hz, 1H).

Step D. (8-chloronaphthalen-1-yl)trimethylstannane. To a mixture of 1-bromo-8-chloronaphthalene (37 g, 153 mmol, 1.0 eq) and trimethyl(trimethylstannyl) stannane (151 g, 460 mmol, 95.3 mL, 3 eq) in toluene (750 mL) was added Pd(PPh$_3$)$_4$ (17.7 g, 15.3 mmol, 0.1 eq) in one portion at 100° C. under N$_2$. The mixture was stirred at 100° C. for 12 hours. The reaction mixture was diluted with H$_2$O (500 mL) and extracted with ethyl acetate (2×1 L). The combined organic layers were washed with saturated brine (3×500 mL), dried over Na$_2$SO$_4$, filtered and concentrated under vacuum. The residue was purification by column chromatography (SiO$_2$, petroleum ether:ethyl acetate=1:0), and then further purified by reversed phase flash chromatography [water (0.10% FA/acetonitrile)] to give (8-chloronaphthalen-1-yl)trimethylstannane (47 g, 144 mmol, 94% yield). Yellow oil. $^1$H NMR (400 MHz, CDCl$_3$) δ 7.88-7.82 (m, 2H), 7.82-7.76 (m, 1H), 7.64-7.59 (m, 1H), 7.52-7.44 (m, 1H), 7.41-7.34 (m, 1H), 0.52-0.34 (m, 9H).

Intermediate 13

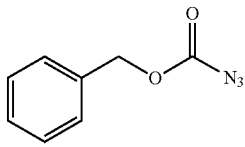 [SMILES: [N-]=[N+]=NC(=O)OCc1ccccc1]

Benzyl Carbonazidate

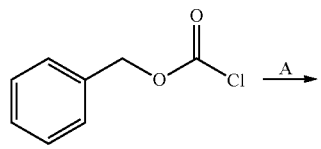

Step A. Benzyl carbonazidate. Benzyl carbonochloridate (100 mg, 586 μmol, 83.3 μL, 1.0 equivalent) was added to a well-stirred suspension of NaN$_3$ (45.7 mg, 703 μmol, 1.2 equivalent) in acetone (10 mL) at 10° C. The mixture was stirred at 10° C. for 1 hour. The mixture was then poured into a Celite pad. The filtrate was collected and concentrated by rotary evaporation to give benzyl N-diazocarbamate (100 mg, crude) as colorless oil and used to next step without purification.

Intermediate 14

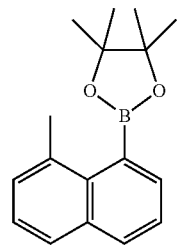 [SMILES: Cc1cccc2cccc(B3OC(C)(C)C(C)(C)O3)c12]

4,4,5,5-tetramethyl-2-(8-methylnaphthalen-1-yl)-1,3,2-dioxaborolane

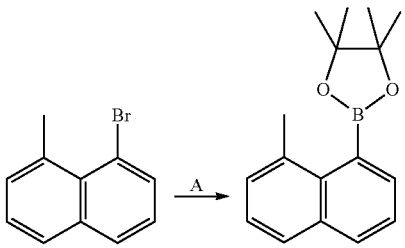

Step A. 4,4,5,5-tetramethyl-2-(8-methylnaphthalen-1-yl)-1,3,2-dioxaborolane. To a solution of 1-bromo-8-methylnaphthalene (0.700 g, 3.17 mmol) in dioxane (15.8 ml) was added potassium acetate (0.932 g, 9.50 mmol) and 4,4,4',4',5,5,5',5'-octamethyl-2,2'-bi(1,3,2-dioxaborolane) (2.41 g, 9.50 mmol) and the reaction sparged with N2 for 15 minutes, followed by the addition of PdCl$_2$(dppf) (0.232 g, 0.317 mmol). The reaction was heated to 95° C. for 18 hrs. The reaction was concentrated in vacuo and taken up in DCM. The slurry was filtered through GF/F filter paper and the organics was concentrated in vacuo. The material was chromatographed twice using 10→100% Ethyl acetate/hexane as eluent to give 4,4,5,5-tetramethyl-2-(8-methylnaphthalen-1-yl)-1,3,2-dioxaborolane (576 mg, 2.15 mmol, 68% yield). HPLC (5-95% ACN/H$_2$O+0.1% TFA) 3.701 min.

Intermediate 15

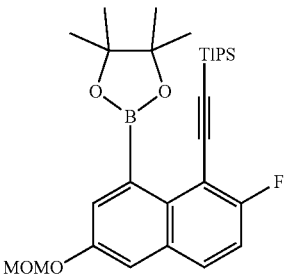

((2-fluoro-6-(methoxymethoxy)-8-(4,4,5,5-tetramethyl-1,3,2-dioxaborolan-2-yl)naphthalen-1-yl)ethynyl)triisopropylsilane

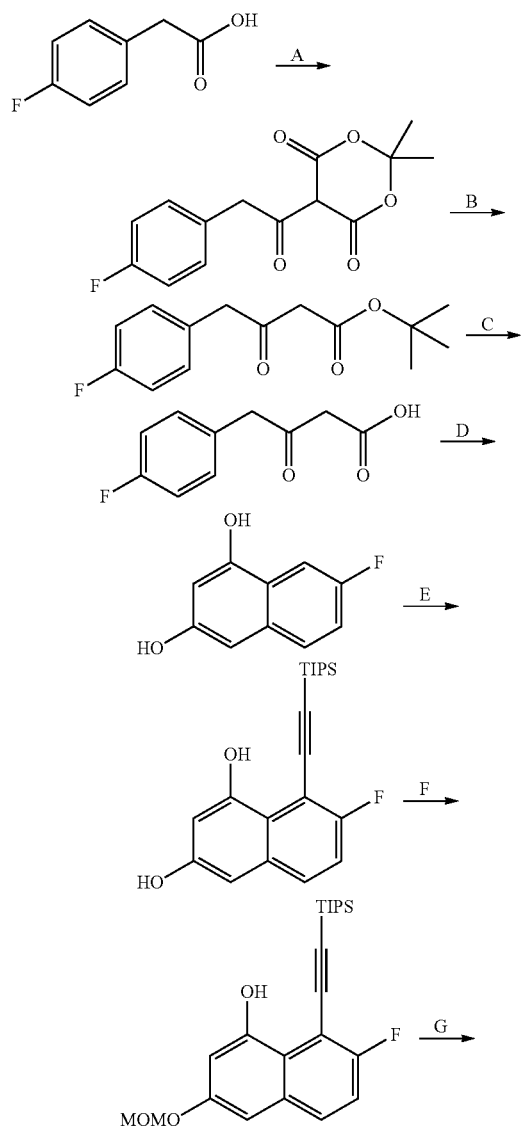

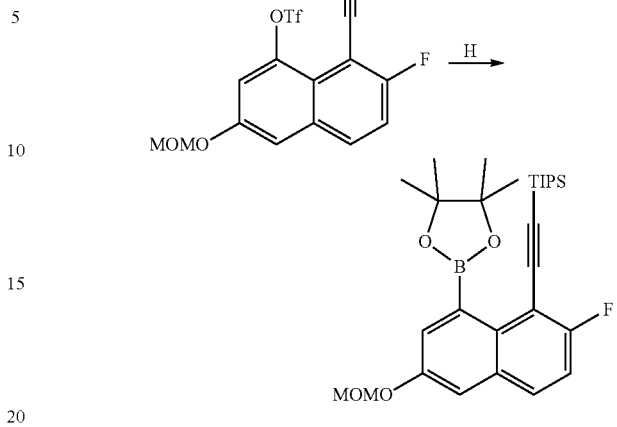

Step A. 5-(2-(4-fluorophenyl)acetyl)-2,2-dimethyl-1,3-dioxane-4,6-dione. To a solution of 2-(4-fluorophenyl)acetic acid (500 g, 3.24 mol, 1 eq), Meldrum's acid (514 g, 3.57 mol, 1.1 eq), DMAP (33.7 g, 275 mmol, 0.085 eq) in $CH_3CN$ (1500 mL) was added DIPEA (901 g, 6.97 mol, 1.21 L, 2.15 eq) while maintaining the temperature below 45° C., and then pivaloyl chloride (430 g, 3.57 mol, 439 mL, 1.1 eq) was slowly added over 3 hours while maintaining the temperature below 45° C. The resulted solution was stirred at 45° C. for 3 hours. The mixture solution was cooled to 0° C., then 1N HCl (5 L) was slowly added, and the resulted solution was stirred at 0° C. for 2 hours. Lot of solid was generated, and the mixture was filtered to give the crude yellow solid. The crude was washed with $CH_3CN/H_2O$ (3 L/12 L) to give 5-(2-(4-fluorophenyl)acetyl)-2,2-dimethyl-1,3-dioxane-4,6-dione (800 g, 88% yield). White Solid; $^1H$ NMR (400 MHz, DMSO-d6) δ=15.35 (s, 1H), 7.40-7.38 (m, 2H), 7.05-7.01 (m, 2H), 4.40 (s, 2H), 1.72 (s, 6H).

Step B. tert-butyl 4-(4-fluorophenyl)-3-oxobutanoate. A solution of 5-(2-(4-fluorophenyl)acetyl)-2,2-dimethyl-1,3-dioxane-4,6-dione (1 kg) in t-BuOH (3 L) was stirred at 90° C. for 2 hours, then the mixture solution was concentrated to give the crude solid, and the crude solid was washed with petroleum ether (350 mL) to give tert-butyl 4-(4-fluorophenyl)-3-oxobutanoate (850 g, 94% yield). Light-yellow Solid; $^1H$ NMR (400 MHz, DMSO-d6) δ=7.27-7.18 (m, 2H), 7.18-7.08 (m, 2H), 3.86 (s, 2H), 3.55 (s, 2H), 1.40 (s, 9H).

Step C. 4-(4-fluorophenyl)-3-oxobutanoic acid. A solution of tert-butyl 4-(4-fluorophenyl)-3-oxobutanoate (800 g, 3.17 mol, 1 eq) and TFA (2.46 kg, 21.6 mol, 1.6 L, 6.81 eq) in DCM (1.6 L) was stirred at 20° C. for 1 hour. The mixture was concentrated to dryness. The residue was washed with petroleum ether (500 mL) to give 4-(4-fluorophenyl)-3-oxobutanoic acid (516 g, 83% yield). White Solid; $^1H$ NMR (400 MHz, $CDCl_3$-d) δ=10.01 (s, 1H), 7.20-7.17 (m, 2H), 7.07-7.03 (m, 2H), 3.84 (s, 2H), 3.54-3.52 (m, 2H).

Step D. 7-fluoronaphthalene-1,3-diol. A solution of 4-(4-fluorophenyl)-3-oxobutanoic acid (450 g, 2.29 mol, 1 eq) in $CF_3SO_3H$ (8.5 kg, 56 mol, 5 L, 25 eq) was stirred at 25° C. for 24 hours, the reaction was cooled to 0° C., and slowly added to ice-water (15 L). Precipitates were formed, and the mixture was filtered to give the crude product. Then crude was slurred with petroleum ether (1 L), and filtered to give the 7-fluoronaphthalene-1,3-diol (325 g, 79% yield). Light-yellow Solid.

Step E. 7-fluoro-8-((triisopropylsilyl)ethynyl)naphthalene-1,3-diol. To the mixture of 7-fluoronaphthalene-1,3-diol (120 g, 673 mmol, 1 eq), 2-bromoethynyl(triisopropyl)silane (184 g, 707 mmol, 1.05 eq), AcOK (132 g, 1.34 mol, 2 eq) in dioxane (800 mL) was added dichlororuthenium; 1-isopropyl-4-methyl-benzene dimer (41.3 g, 67.4 mmol, 0.1 eq)under $N_2$. The mixture was stirred at 110° C. for 2 hours. The mixture was filtered and concentrated to give a residue. Then the residue was purified by column chromatography ($SiO_2$, Petroleum ether/Ethyl acetate=1/0 to 5/1) to give 7-fluoro-8-((triisopropylsilyl)ethynyl)naphthalene-1,3-diol (213 g, 88% yield) was obtained. Black Oil; LCMS [ESI, M+1]: 359.2

Step F. 7-fluoro-3-(methoxymethoxy)-8-((triisopropylsilyl)ethynyl)naphthalen-1-ol. To the mixture of 7-fluoro-8-((triisopropylsilyl)ethynyl)naphthalene-1,3-diol (170 g, 474 mmol, 1 eq), DIEA (184 g, 1.42 mol, 3 eq) and DCM (1700 mL) was added MOMCl (49.8 g, 618 mmol, 1.3 eq) at 0° C. The mixture was warmed to 15° C. and stirred for 0.5 hour. The reaction mixture was diluted with ice-water (1000 mL) and extracted with ethyl acetate (500 mL×2). The combined organic phase was washed with brine (1000 mL), dried over anhydrous sodium sulfate, filtered and concentrated to give a residue. The residue was purified by column chromatography ($SiO_2$, Petroleum ether/Ethyl acetate=1/0 to 50/1) to give 7-fluoro-3-(methoxymethoxy)-8-((triisopropylsilyl)ethynyl)naphthalen-1-ol (96 g, 50% yield). Yellow Solid; $^1$H NMR (400 MHz, $CDCl_3$-d) δ=9.13 (s, 1H), 7.68-7.64 (m, 1H), 7.21-7.16 (m, 1H), 6.97-6.96 (m, 1H), 6.81-6.80 (m, 1H), 5.26 (s, 2H), 3.51 (s, 3H), 1.24-1.17 (m, 21H). LCMS [ESI, M+1]: 403.2.

Step G: 7-fluoro-3-(methoxymethoxy)-8-((triisopropylsilyl)ethynyl)naphthalen-1-yl trifluoromethanesulfonate. To the solution of 7-fluoro-3-(methoxymethoxy)-8-((triisopropylsilyl)ethynyl)naphthalen-1-ol (80 g, 198 mmol, 1 eq), DIEA (77.0 g, 596 mmol, 104 mL, 3 eq) in DCM (1200 mL) was added $Tf_2O$ (84.1 g, 298 mmol, 49.2 mL, 1.5 eq) at −40° C., and the mixture was stirred at −40° C. for 0.5 hour. The reaction mixture was diluted with ice-water (500 mL), and then extracted with DCM (300 mL). The combined organic phase was dried over $Na_2SO_4$ and concentrated to dryness. The residue was purified by column chromatography ($SiO_2$, Petroleum ether/Ethyl acetate=1/0 to 60/1) to afford 7-fluoro-3-(methoxymethoxy)-8-((triisopropylsilyl)ethynyl)naphthalen-1-yl trifluoromethanesulfonate (100 g, 94% yield). Yellow oil;

Step H. ((2-fluoro-6-(methoxymethoxy)-8-(4,4,5,5-tetramethyl-1,3,2-dioxaborolan-2-yl)naphthalen-1-yl)ethynyl)triisopropylsilane. To the mixture of 7-fluoro-3-(methoxymethoxy)-8-((triisopropylsilyl)ethynyl)naphthalen-1-yl trifluoromethanesulfonate (105 g, 196 mmol, 1 eq), 4,4,5,5-tetramethyl-2-(4,4,5,5-tetramethyl-1,3,2-dioxaborolan-2-yl)-1,3,2-dioxaborolane (100 g, 393 mmol, 2 eq), AcOK (57.8 g, 589 mmol, 3 eq) in toluene (1100 mL) was added Pd(dppf)$Cl_2$ (14.4 g, 20 mmol, 0.1 eq). The mixture was degassed and stirred at 130° C. for 3 hours. The reaction mixture was filtered and concentrated to give a residue. To the residue was added EtOAc (1000 mL) and water (800 mL). The organic phase was washed with brine (500 mL), dried over anhydrous sodium sulfate, filtered and concentrated to give a residue. The residue was purified by column chromatography ($SiO_2$, Petroleum ether/Ethyl acetate=100/1 to 3/1) and triturated with MeCN (40 mL) to give ((2-fluoro-6-(methoxymethoxy)-8-(4,4,5,5-tetramethyl-1,3,2-dioxaborolan-2-yl)naphthalen-1-yl)ethynyl)triisopropylsilane (41 g, 43% yield). Yellow Solid; $^1$H NMR (400 MHz, $CDCl_3$-d) δ=7.69-7.65 (m, 1H), 7.51 (d, J=2.4 Hz, 1H), 7.38 (d, J=2.4 Hz, 1H), 7.25 (t, J=8.8 Hz, 1H), 5.28 (s, 2H), 3.50 (s, 3H), 1.44 (s, 12H), 1.18-1.16 (m, 21H); LCMS [ESI, M+1]: 513.4.

Intermediate 16

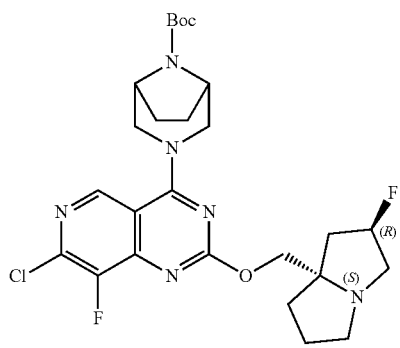

tert-butyl (1R,5S)-3-(7-chloro-8-fluoro-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate

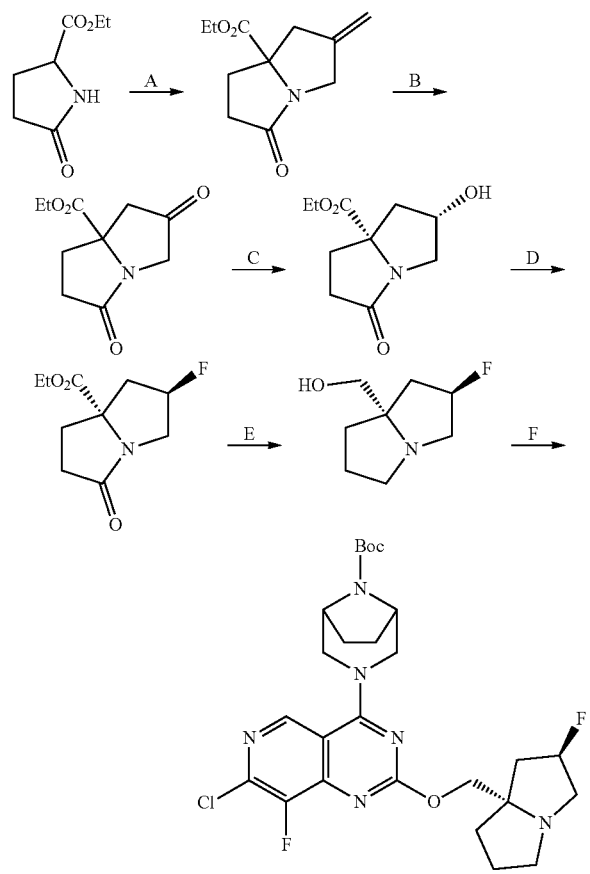

Step A. Ethyl 2-methylene-5-oxotetrahydro-1H-pyrrolizine-7a(5H)-carboxylate. To a mixture of ethyl 5-oxopyrrolidine-2-carboxylate (1.50 kg, 9.54 mol, 1.00 eq) and 3-chloro-2-(chloromethyl)prop-1-ene (1.91 kg, 15.3 mol, 1.77 L, 1.60 eq) in THF (7.50 L) was added LiHMDS (1 M, 19.1 L, 2.00 eq) drop-wise at −40° C. under N$_2$. The mixture was stirred at 25° C. for 20 hrs. The reaction mixture was poured into HCl (1 M, 2.50 L) and pH was adjusted to 7 with HCl (2 M) at 0° C. The mixture was extracted with EtOAc (4.50 L×3). The combined organic layers were washed with brine (4.50 L), dried over Na$_2$SO$_4$, filtered and concentrated under reduced pressure to give a residue. The residue was purified by column chromatography (SiO$_2$, Petroleum ether/Ethyl acetate=10/1 to 1/1, Rf=0.40) to afford the title compound (898 g, 3.88 mol, 40.6% yield, 82% purity) as a yellow oil. LCMS: Rt=0.716 min, m/z=210.1 (M+H). $^1$H NMR: 400 MHz CDCl$_3$δ: 5.02-5.07 (m, 2H), 4.28 (m, 1H), 4.16-4.22 (m, 2H), 3.71 (dd, J=15.6, 1.6 Hz, 1H), 3.04 (m, 1H), 2.73-2.80 (m, 1H), 2.57-2.64 (m, 1H), 2.41-2.49 (m, 2H), 2.03-2.17 (m, 2H), 1.24-1.30 (m, 3H).

Step B. ethyl 2,5-dioxotetrahydro-1H-pyrrolizine-7a(5H)-carboxylate. To a mixture of ethyl 2-methylene-5-oxotetrahydro-1H-pyrrolizine-7a(5H)-carboxylate (165 g, 646 mmol, 1.00 eq) in DCM (1650 mL) and MeOH (165 mL) was added O3 (15 psi) at −70° C. under N$_2$. The solution became pale blue, and then the mixture was purged by N2 for 30 min. Me$_2$S (80.4 g, 1.29 mol, 95.0 mL, 2.00 eq) was added to the mixture at −70° C. The mixture was stirred at 25° C. for 16 hours. The reaction mixture was concentrated under reduced pressure to give a residue. The residue was purified by column chromatography (SiO$_2$, Petroleum ether/Ethyl acetate=10/1 to 1/1, Rf=0.50) to afford the title compound (821 g, 3.62 mol, 93.3% yield, 93.1% purity) as a yellow oil. LCMS: Rt=0.543 min, m/z=212.1 (M+H). $^1$H NMR: 400 MHz CDCl$_3$δ: 4.23 (m, 2H), 4.12 (m, 1H), 3.56 (m, 1H), 2.96-3.01 (m, 2H), 2.77-2.86 (m, 1H), 2.43-2.50 (m, 2H), 2.14-2.22 (m, 1H), 1.28 (m, 1H).

Step C. ethyl 2-hydroxy-5-oxotetrahydro-1H-pyrrolizine-7a(5H)-carboxylate. To a solution of ethyl 2,5-dioxotetrahydro-1H-pyrrolizine-7a(5H)-carboxylate (257 g, 1.22 mol, 1.00 eq) in EtOH (1300 mL) was slowly added NaBH$_4$ (13.8 g, 365 mmol, 0.30 eq) at 0° C. under N$_2$. The mixture was stirred at 0° C. for 10 min. The reaction was quenched with saturated NH$_4$Cl (65.0 mL) at 5° C. and stirred at 5° C. for 0.5 hr, then the mixture was concentrated under reduced pressure to give a residue. The residue was purified by column chromatography (SiO$_2$, Petroleum ether/Ethyl acetate=10/1 to 1/1) to afford the title compound (56.8% yield) as a yellow oil. $^1$H NMR: 400 MHz CDCl$_3$δ: 4.65 (s, 1H), 4.14 (q, J=7.2 Hz, 2H), 3.95 (dd, J=12.8, 6.0 Hz, 1H), 3.10 (d, J=12.8 Hz, 1H), 2.75-2.84 (m, 2H), 2.49-2.49 (m, 2H), 2.39-2.45 (m, 1H), 2.02-2.10 (m, 1H), 1.84 (dd, J=13.6, 6.0 Hz, 1H), 1.30 (t, J=7.2 Hz, 1H).

Step D. ethyl (2S,7aR)-2-fluoro-5-oxotetrahydro-1H-pyrrolizine-7a(5H)-carboxylate. To a solution of ethyl 2-hydroxy-5-oxotetrahydro-1H-pyrrolizine-7a(5H)-carboxylate (150 g, 642 mmol, 1.00 eq) in DCM (750 mL) was added a solution of DAST (131 g, 813 mmol, 107 mL, 1.50 eq) drop-wise at −70° C. under N$_2$. The reaction mixture was warmed to 25° C. stirred at 25° C. for 16 hours. The reaction mixture was quenched with MeOH (40.0 mL) at 10° C., then diluted with water (750 mL) and extracted with DCM (750 mL×3). The combined organic layers were washed with brine (750 mL), dried over Na$_2$SO$_4$, filtered and concentrated under reduced pressure to give a residue. The residue was purified by column chromatography (SiO$_2$, Petroleum ether/Ethyl acetate=1/0 to 0/1, Rf=0.30) to afford ethyl 2-fluoro-5-oxotetrahydro-1H-pyrrolizine-7a(5H)-carboxylate (50.6% yield, 74.7% purity) as a yellow oil. This compound (61 g, 283.43 mmol, 1.00 eq) was further purified by HPLC (column: Welch ultimate XB-NH$_2$250*50*10 um; mobile phase: [Heptane-EtOH (0.1% NH$_3$·H$_2$O)]; B %: 10%-10%, 10 min) to give a yellow oil (49.0 g, 226.08 mmol, 99.3% purity). $^1$H NMR: 400 MHz CDCl$_3$δ: 5.30 (m, 1H), 4.10-4.23 (m, 3H), 3.11-3.14 (m, 1H), 2.67-2.76 (m, 3H), 2.41-2.45 (m, 1H), 2.03-2.12 (m, 2H), 1.23-1.29 (m, 3H). SFC separation (column: DAICEL CHIRALPAK IC (250 mm*50 mm, 10 um); mobile phase: [0.1% NH$_3$·H$_2$O IPA]; B %: 40%-40%, 4.7 min; 200 min, desired product: Peak 2, Rt=1.959 min) of the racemic material (280 g, 1.22 mol, 1 eq) gave the title compound (114 g, 96.0% purity).

Step E. ((2R,7aS)-2-fluorotetrahydro-1H-pyrrolizin-7a(5H)-yl)methanol. To a suspension of LiAlH$_4$ (33.1 g, 871 mmol, 1.50 eq) in THF (625 mL) was added a solution of ethyl (2S,7aR)-2-fluoro-5-oxotetrahydro-1H-pyrrolizine-7a(5H)-carboxylate (125 g, 581 mmol, 1.00 eq) in THF (375 mL) drop-wise at 0° C. under N$_2$. The reaction mixture was warmed to 70° C. and stirred at 70° C. for 3 hours. The mixture was cooled to 0° C. Then to the mixture was added water (33.0 mL), NaOH (15%, 99.0 mL) and water (99 mL) dropwise in sequence 0° C. After addition, the mixture was stirred at 0° C. stirred for 5 min. The mixture was filtered, and the filtered cake was washed with EtOAc (1000 mL×2). The filtrate was dried with MgSO$_4$, filtered, and concentrated under reduced pressure to give a residue. The residue was purified by column chromatography (SiO$_2$, DCM:MeOH=100/1 to 10/1) to afford the title compound (180 g, 1.10 mol, 94.7% yield, 97.3% purity) as a yellow oil. $^1$H NMR: 400 MHz CDCl$_3$δ: 5.12-5.27 (m, 1H), 3.25 (s, 2H), 3.14-3.18 (m, 2H), 3.12-3.13 (m, 1H), 3.02-3.09 (m, 1H), 2.01-2.11 (m, 2H), 1.75-1.86 (m, 4H).

Step F. tert-butyl (1R,5S)-3-(7-chloro-8-fluoro-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate. To the mixture of tert-butyl (1R,5S)-3-(2,7-dichloro-8-fluoropyrido[4,3-d]pyrimidin-4-yl)-3,8-diazabicyclo[3.2.1]octane-8-carboxylate (538 mg, 1.26 mmol, 1.0 eq), ((2R,7aS)-2-fluorotetrahydro-1H-pyrrolizin-7a(5H)-yl)methanol (200 mg, 1.26 mmol, 1.0 eq), DIEA (487 mg, 3.77 mmol, 3.0 eq) in dioxane (6 mL) was added 4 A MS (150 mg). The mixture was stirred at 90° C. for 24 hours. After completion, the reaction mixture was diluted with ethyl acetate (20 mL) and water (15 mL), and then extracted with ethyl acetate (20 mL×2). The combined organic phases were washed with saturated brine 20 mL, dried over Na$_2$SO$_4$ and concentrated. The residue was purified by reversed phase flash chromatography [water (FA 0.1%)/acetonitrile] to give the title compound (260 mg, 37% yield). Yellow solid. LCMS [ESI, M+1]:551.2.

Intermediate 17

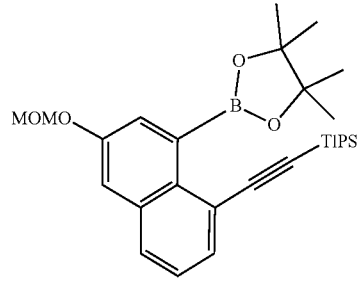

triisopropyl-[2-[6-(methoxymethoxy)-8-(4,4,5,5-tetramethyl-1,3,2-dioxaborolan-2-yl)-1-naphthyl]ethynyl]silane

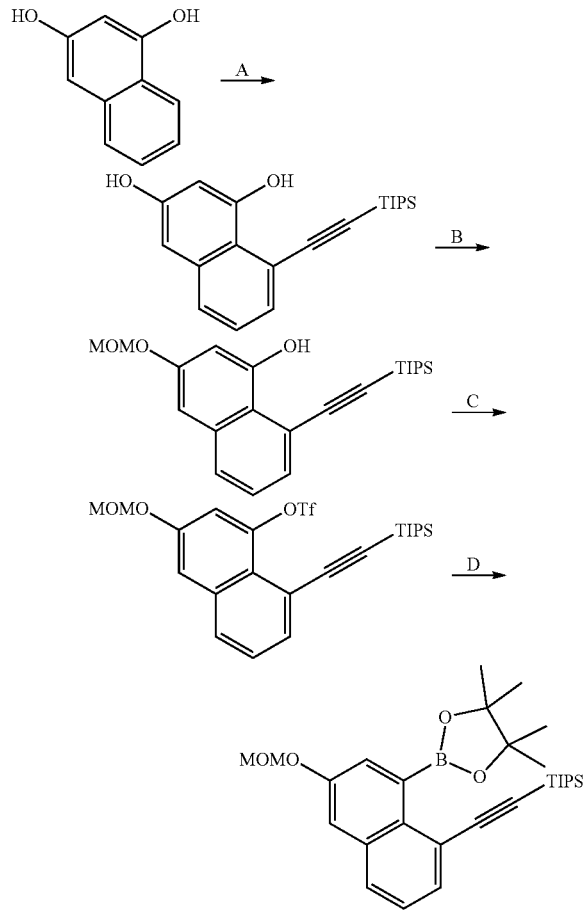

Step A. 8-(2-triisopropylsilylethynyl)naphthalene-1,3-diol. A mixture of naphthalene-1,3-diol (50 g, 312 mmol, 1 eq), 2-bromoethynyl(triisopropyl)silane (97.9 g, 375 mmol, 1.2 eq), dichlororuthenium; 1-isopropyl-4-methyl-benzene (19.1 g, 31.2 mmol, 0.1 eq), AcOK (61.3 g, 624 mmol, 2 eq) in dioxane (600 mL) was stirred at 110° C. for 12 hours. After completion, the mixture was filtered, diluted with water (1 L), and extracted with ethyl acetate (2×1 L). The combined organic layer was washed with brine (1 L), dried over $Na_2SO_4$, filtered and concentrated under vacuum. The residue was purified by column chromatography ($SiO_2$, petroleum ether/ethyl acetate=3/1, Rf=0.68) to give the title compound (100 g, 89% yield). Yellow oil. Rf=0.68 (petroleum ether/ethyl acetate=3/1). LCMS [ESI, M+1]: 341.3.

Step B. 3-(methoxymethoxy)-8-(2-triisopropylsilylethynyl)naphthalen-1-ol. To a mixture of 8-(2-triisopropylsilylethynyl)naphthalene-1,3-diol (180 g, 529 mmol, 1 eq) and DIEA (205 g, 1.59 mol, 276 mL, 3 eq) in dichloromethane (1500 mL) was added MOMCl (63.8 g, 793 mmol, 60.2 mL, 1.5 eq) at 0° C. After stirred at 0° C. for 0.5 hour, the mixture was diluted with water (1 L) and separated. The water phase was extracted with dichloromethane (500 mL). The combined organic layer was washed with brine (1 L) dried over $Na_2SO_4$, filtered and concentrated under vacuum. The residue was purified by column chromatography ($SiO_2$, petroleum ether/ethyl acetate=3/1, Rf=0.6) to give the title compound (126 g, 60% yield). Black solid. LCMS [ESI, M+1]: 285.3. $^1$H NMR (400 MHz, chloroform-d) δ=9.25 (s, 1H), 7.69 (dd, J=0.8, 8.0 Hz, 1H), 7.50 (dd, J=1.2, 7.2 Hz, 1H), 7.31 (dd, J=7.2, 8.4 Hz, 1H), 6.98 (d, J=2.4 Hz, 1H), 6.78 (d, J=2.4 Hz, 1H), 5.27 (s, 2H), 3.51 (s, 3H), 1.20-1.16 (m, 21H).

Step C. [3-(methoxymethoxy)-8-(2-triisopropylsilylethynyl)-1-naphthyl]trifluoromethanesulfonate. To a mixture of 3-(methoxymethoxy)-8-(2-triisopropylsilylethynyl)naphthalen-1-ol (200 g, 520.04 mmol, 1 eq) and DIEA (202 g, 1.56 mol, 272 mL, 3 eq) in dichloromethane (2000 mL) was added $Tf_2O$ (220 g, 780 mmol, 129 mL, 1.5 eq) at −40° C. After stirred at −40° C. for 0.5 hour, the mixture was quenched with water (2 L) and separated. The water phase was extracted with dichloromethane (500 mL). The combined organic layer was washed with brine (1 L), dried over $Na_2SO_4$, filtered and concentrated under vacuum. The residue was purified by column chromatography ($SiO_2$, petroleum ether/ethyl acetate=5/1, Rf=0.24), to give the title compound (250 g, 92% yield). Yellow oil.

Step D. triisopropyl-[2-[6-(methoxymethoxy)-8-(4,4,5,5-tetramethyl-1,3,2-dioxaborolan-2-yl)-1-naphthyl]ethynyl]silane. A mixture of [3-(methoxymethoxy)-8-(2-triisopropylsilylethynyl)-1-naphthyl]trifluoromethanesulfonate (230 g, 445 mmol, 1 eq), 4,4,5,5-tetramethyl-2-(4,4,5,5-tetramethyl-1,3,2-dioxaborolan-2-yl)-1,3,2-dioxaborolane (226 g, 890 mmol, 2 eq), $Pd(dppf)Cl_2$ (32.6 g, 44.5 mmol, 0.1 eq) and KOAc (152.92 g, 1.56 mol, 3.5 eq) in toluene (2 L) was stirred at 110° C. for 3 hours under $N_2$. After completion, the mixture was filtered and concentrated under vacuum. The residue was diluted with water (1 L) and extracted with ethyl acetate (1 L×2). The combined organic layer was washed with brine (1 L), dried over $Na_2SO_4$, filtered and concentrated under vacuum. The residue was purified by column chromatography ($SiO_2$, petroleum ether/ethyl acetate=20/1, Rf=0.39). The compound was triturated with acetonitrile (500 mL) to give 98 g pure product. The filtrate was purified by reversed phase flash chromatography [water (FA, 0.1%)/acetonitrile] to further give 27 g product. Total of the title compound is 125 g (57% yield). Yellow solid. $^1$H NMR (400 MHz, chloroform-d) δ=7.72-7.67 (m, 2H), 7.48 (d, J=2.4 Hz, 1H), 7.40-7.32 (m, 2H), 5.29 (s, 2H), 3.51 (s, 3H), 1.44 (s, 12H), 1.19-1.15 (m, 21H).

Intermediate 18

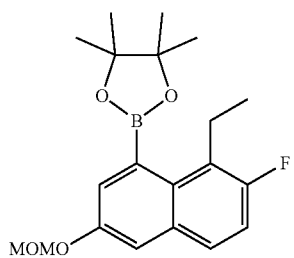

2-(8-ethyl-7-fluoro-3-(methoxymethoxy)naphthalen-1-yl)-4,4,5,5-tetramethyl-1,3,2-dioxaborolane

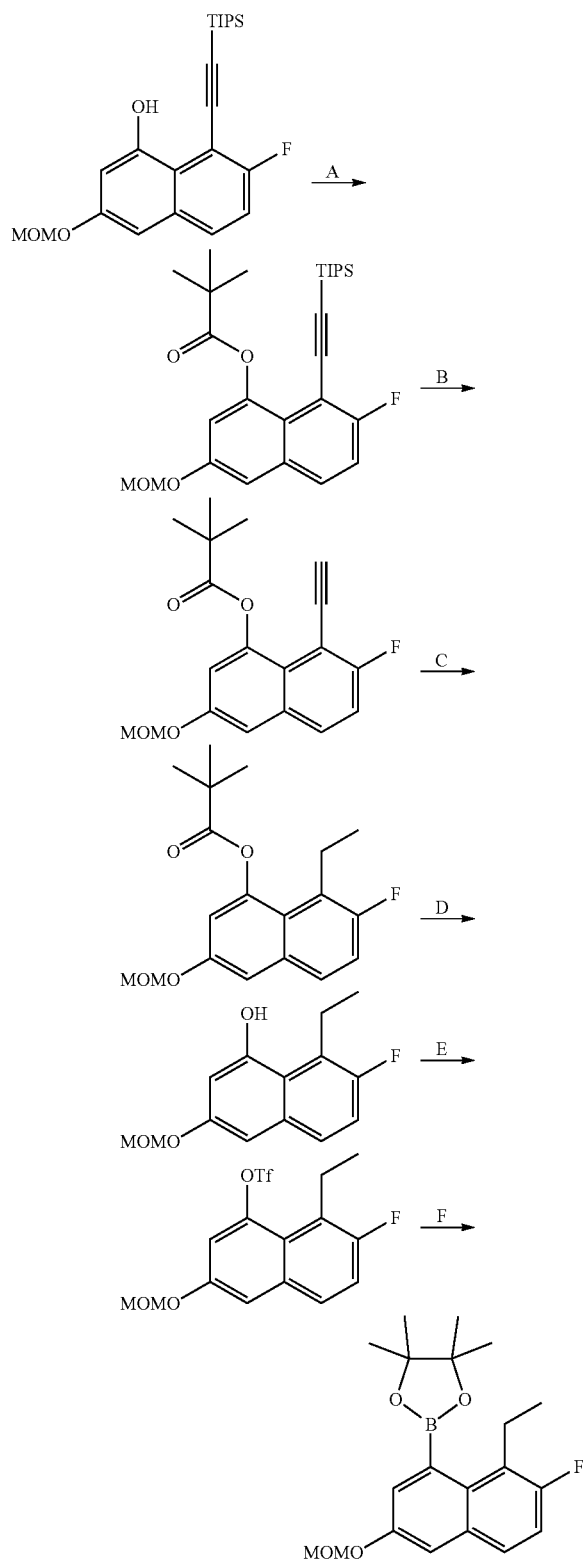

Step A. 7-fluoro-3-(methoxymethoxy)-8-((triisopropylsilyl)ethynyl)naphthalen-1-yl pivalate. To the solution of 7-fluoro-3-(methoxymethoxy)-8-((triisopropylsilyl)ethynyl)naphthalen-1-ol (2.00 g, 4.97 mmol, 1.0 eq), DMAP (122 mg, 999 μmol, 0.2 eq), TEA (1.51 g, 14.9 mmol, 3.0 eq) in DCM (20 mL) was added 2,2-dimethylpropanoyl chloride (1.80 g, 14.9 mmol, 3.0 eq) dropwise at 0° C., and then the mixture was stirred at 20° C. for 1 hour. After completion, the reaction mixture was diluted with DCM (15 mL) and water (15 mL), and then the aqueous layer was extracted with DCM (10 mL), The combined organic phase was dried over $Na_2SO_4$ and concentrated. The residue was purified by column chromatography ($SiO_2$, Petroleum ether/Ethyl acetate=1/0 to 15/1) to give the title compound (3.00 g, crude). Yellow oil. LCMS [ESI, M+1]:487.2.

Step B. 8-ethynyl-7-fluoro-3-(methoxymethoxy)naphthalen-1-yl pivalate. To the solution of 7-fluoro-3-(methoxymethoxy)-8-((triisopropylsilyl)ethynyl)naphthalen-1-yl pivalate (3.00 g, 6.16 mmol, 1.0 eq) in DMF (50 mL) was added CsF (9.36 g, 61.6 mmol, 10 eq), and the mixture was stirred at 20° C. for 0.25 hour. After completion, to the reaction mixture was added water (250 mL), and then the mixture was extracted with ethyl acetate (2×120 mL). The combined organic phase was washed with brine 100 mL, dried over $Na_2SO_4$ and concentrated to give the title compound (2.20 g, crude). Yellow oil. LCMS [ESI, M+1]: 331.1.

Step C. 8-ethyl-7-fluoro-3-(methoxymethoxy)naphthalen-1-yl pivalate. To the solution of 8-ethynyl-7-fluoro-3-(methoxymethoxy)naphthalen-1-yl pivalate (2.00 g, 6.05 mmol, 1.0 eq) in MeOH (20 mL) was added Pd/C (200 mg, 10% purity) under $N_2$. The suspension was degassed under vacuum and purged with H2 several times. The mixture was stirred under $H_2$ (15 psi) at 20° C. for 20 minutes. After completion, the mixture was filtered and concentrated to give the title compound (1.06 g, crude). LCMS [ESI, M+1]: 335.1.

Step D. 8-ethyl-7-fluoro-3-(methoxymethoxy)naphthalen-1-ol. To the solution of 8-ethyl-7-fluoro-3-(methoxymethoxy)naphthalen-1-yl pivalate (1.00 g, 2.99 mmol, 1.0 eq) in MeOH (15 mL) was added KOH (504 mg, 8.98 mmol, 3.0 eq), and the mixture was stirred at 20° C. for 0.5 hour. After completion, the reaction solution was adjusted to pH=4 with 0.5 M HCl at 0° C. and extracted with ethyl acetate (80 mL×2), the combined organic phase was washed with brine 50 mL, dried over anhydrous sodium sulfate, filtered and concentrated. The residue was purified by column chromatography ($SiO_2$, Petroleum ether/Ethyl acetate=50/1 to 10/1) to give the title compound (570 mg, four steps 51% yield). Yellow solid. $^1$H NMR (400 MHz, $CDCl_3$) δ=7.55-7.43 (m, 1H), 7.18 (t, J=9.2 Hz, 1H), 6.98 (d, J=2.4 Hz, 1H), 6.57 (d, J=2.0 Hz, 1H), 5.32 (s, 1H), 5.25 (s, 2H), 3.52 (s, 3H), 3.40-3.25 (m, 2H), 1.30 (t, J=7.6 Hz, 3H).

Step E. 8-ethyl-7-fluoro-3-(methoxymethoxy)naphthalen-1-yl trifluoromethane sulfonate. To the solution of 8-ethyl-7-fluoro-3-(methoxymethoxy)naphthalen-1-ol (520 mg, 2.08 mmol, 1.0 eq), DIEA (806 mg, 6.24 mmol, 3.0 eq) in DCM (10 mL), trifluoromethylsulfonyl trifluoromethanesulfonate (879 mg, 3.12 mmol, 1.5 eq) was added dropwise at −40° C., and then the mixture was stirred at −40° C. for 0.5 hr. After completion, the reaction mixture was quenched with ice-water (15 mL), and then extracted with DCM (2×15 mL). The combined organic phase was dried over $Na_2SO_4$ and concentrated. The residue was purified by column chromatography ($SiO_2$, Petroleum ether/Ethyl acetate=100/1 to 30/1) to give the title compound (620 mg, 78% yield). Yellow oil. $^1$H NMR (400 MHz, $CDCl_3$) δ=7.67-7.59 (m, 1H), 7.43 (d, J=2.4 Hz, 1H), 7.37 (d, J=2.4

Hz, 1H), 7.33-7.27 (m, 1H), 5.29 (s, 2H), 3.53 (s, 3H), 3.33-3.14 (m, 2H), 1.25 (t, J=7.6 Hz, 3H).

Step F. 2-(8-ethyl-7-fluoro-3-(methoxymethoxy)naphthalen-1-yl)-4,4,5,5-tetramethyl-1,3,2-dioxaborolane. To the mixture of 8-ethyl-7-fluoro-3-(methoxymethoxy)naphthalen-1-yl trifluoromethane sulfonate (500 mg, 1.31 mmol, 1.0 eq), 4,4,5,5-tetramethyl-2-(4,4,5,5-tetramethyl-1,3,2-dioxaborolan-2-yl)-1,3,2-dioxaborolane (665 mg, 2.62 mmol, 2.0 eq), AcOK (385 mg, 3.92 mmol, 3.0 eq) in dioxane (6 mL) was added Pd(dppf)Cl$_2$ (96.0 mg, 131 μmol, 0.1 eq) under N$_2$. The mixture was degassed and stirred at 100° C. for 1 hour. After completion, the mixture was diluted with ethyl acetate (20 mL) and water (10 mL), and extracted with ethyl acetate (10 mL). The combined organic phases were washed with saturated brine (10 mL), dried over anhydrous sodium sulfate, filtered and concentrated. The residue was purified by column chromatography (SiO$_2$, Petroleum ether/Ethyl acetate=100/1 to 25/1) to give the title compound (143 mg, 30% yield). Yellow oil. $^1$H NMR (400 MHz, CDCl$_3$) δ=7.62-7.53 (m, 1H), 7.44-7.34 (m, 2H), 7.21 (t, J=9.2 Hz, 1H), 5.28 (s, 2H), 3.51 (s, 3H), 3.20-3.06 (m, 2H), 1.45 (s, 12H), 1.30-1.25 (m, 3H).

Intermediate 19

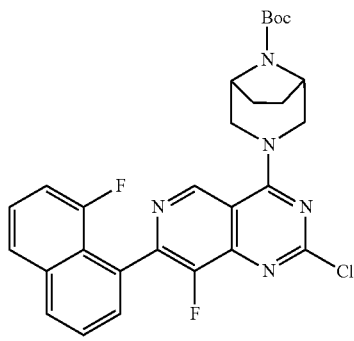 [SMILES: CC(C)(C)OC(=O)N1C2CCC1CN(c1nc(Cl)nc3c(F)c(-c4cccc5cccc(F)c45)ncc13)C2]

tert-butyl (1R,5S)-3-(2-chloro-8-fluoro-7-(8-fluoronaphthalen-1-yl)pyrido[4,3-d]pyrimidin-4-yl)-3,8-diazabicyclo[3.2.1]octane-8-carboxylate

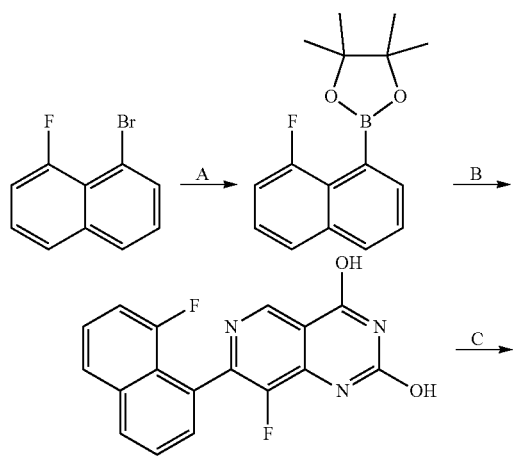

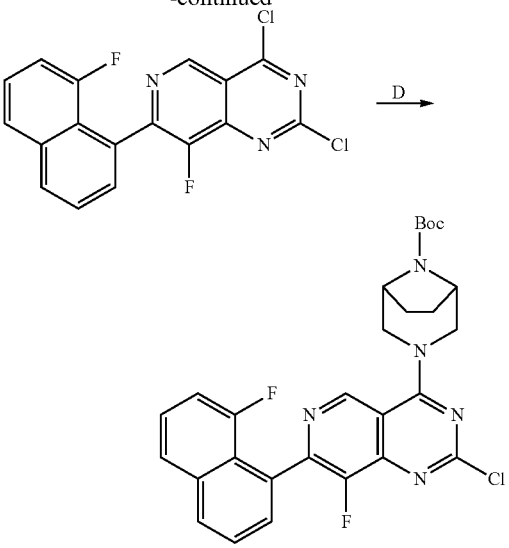

Step A. 2-(8-fluoronaphthalen-1-yl)-4,4,5,5-tetramethyl-1,3,2-dioxaborolane. A solution of 1-bromo-8-fluoronaphthalene (55.0 g, 244 mmol, 1.00 eq) in THF (850 mL) was degassed and purged with N2 for 3 times, and then n-BuLi (2.5 M, 117 mL, 1.20 eq) was added drop-wise at −70° C. The mixture was stirred at −70° C. for 1 hr under N$_2$ atmosphere. Then added a solution of 2-isopropoxy-4,4,5,5-tetramethyl-1,3,2-dioxaborolane (63.6 g, 342 mmol, 69.8 mL, 1.40 eq) in THF (150 mL) at −70° C. The resulting mixture was stirred at −70° C. for 1 hr. LCMS showed 1-bromo-8-fluoronaphthalene was consumed completely and one main peak with desired mass (RT=1.073 min) was detected. The reaction mixture was quenched by NH$_4$Cl solution (500 mL) at 10° C., then diluted with H$_2$O (300 mL) and extracted with PE (500 mL×3). The combined organic layers were washed with brine (500 mL×2), dried over Na$_2$SO$_4$, filtered and concentrated under reduced pressure to give a residue. The residue was purified by flash silica gel chromatography (ISCO®; 100 g SepaFlash® Silica Flash Column, Eluent of 0~4% Ethyl acetate/Petroleum ether, TLC: Petroleum ether/Ethyl acetate=10/1, Rf=0.67) to give compound the title compound (30.0 g, 110 mmol, 45.1% yield, 100% purity) as a light yellow solid. LCMS: M+1, 273.

Step B. 8-fluoro-7-(8-fluoronaphthalen-1-yl)pyrido[4,3-d]pyrimidine-2,4-diol. To a solution of 2-(8-fluoronaphthalen-1-yl)-4,4,5,5-tetramethyl-1,3,2-dioxaborolane (947 mg, 3.48 mmol, 1.50 eq) and 7-chloro-8-fluoropyrido[4,3-d]pyrimidine-2,4-diol (0.50 g, 2.32 mmol, 1.0 eq) in EtOH (15 mL) were added K$_3$PO$_4$ (1.50 M, 4.64 mL, 3.0 eq) and Ad2nBuP Pd G3 (cataCXium® A Pd G3) (253 mg, 348 μmol, 0.15 eq) under N$_2$. The mixture was stirred at 80° C. for 2 hours. The reaction mixture was diluted with water (100 mL) and extracted with ethyl acetate (3×200 mL). The combined organic layers were dried over Na$_2$SO$_4$, filtered and concentrated under reduced pressure to give a residue. The residue was purified by reversed phase flash chromatography (C18, 0.1% FA in water, 0-40% ACN) to give the title compound (800 mg, 50% yield); White solid. $^1$H NMR (400 MHz, chloroform-d) δ 11.24-9.47 (m, 2H), 9.04 (s, 1H), 8.01-7.85 (m, 1H), 7.66 (d, J=8.4 Hz, 1H), 7.57-7.32 (m, 3H), 7.09-6.96 (m, 1H). LCMS [ESI, M+1]: 326.1.

Step C. 2,4-dichloro-8-fluoro-7-(8-fluoronaphthalen-1-yl)pyrido[4,3-d]pyrimidine. To a solution of 8-fluoro-7-(8- fluoronaphthalen-1-yl)pyrido[4,3-d]pyrimidine-2,4-diol (800 mg, 2.46 mmol, 1.0 eq) in POCl₃ (10 mL) was added DIEA (954 mg, 7.38 mmol, 1.29 mL, 3.0 eq) under N2. The mixture was stirred at 110° C. for 1 hour. The mixture was concentrated under vacuum to give the title compound (900 mg, crude). Black oil.

Step D. (1R,5S)-tert-butyl 3-(2-chloro-8-fluoro-7-(8-fluoronaphthalen-1-yl)pyrido[4,3-d]pyrimidin-4-yl)-3,8-diazabicyclo[3.2.1]octane-8-carboxylate. To a solution of 2,4-dichloro-8-fluoro-7-(8-fluoronaphthalen-1-yl)pyrido[4,3-d]pyrimidine (390 mg, 872 μmol, 81% purity, 1.0 eq) in DMAc (10 mL) were added DIEA (338 mg, 2.62 mmol, 456 μL, 3.0 eq) and tert-butyl 3,8-diazabicyclo[3.2.1]octane-8-carboxylate (194 mg, 916 μmol, 1.05 eq). The mixture was stirred at 20° C. for 1 hour. The reaction mixture was diluted with water (30 mL) and extracted with ethyl acetate (3×10 mL). The combined organic layers were dried over Na₂SO₄, filtered and concentrated under reduced pressure to give a residue. The residue was purified by reversed phase flash chromatography (C18, 0.1% FA in water, 0-90% ACN) affording the title compound (420 mg, two steps yield: 32%). Yellow solid. ¹H NMR (400 MHz, chloroform-d) δ 9.13 (s, 1H), 8.05-7.98 (m, 1H), 7.75 (d, J=8.0 Hz, 1H), 7.68-7.55 (m, 2H), 7.51-7.42 (m, 1H), 7.18-7.08 (m, 1H), 4.80-4.51 (m, 2H), 4.50-4.27 (m, 2H), 3.95-3.56 (m, 2H), 2.04-1.93 (m, 2H), 1.85-1.72 (m, 2H), 1.53 (s, 9H). LCMS [ESI, M+1]: 538.2.

Intermediate 20

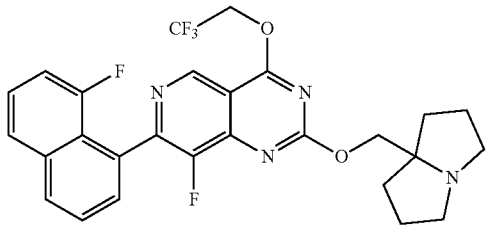 [SMILES: Fc1c(-c2cccc3cccc(F)c23)ncc2c(OCC(F)(F)F)nc(OCC34CCCN3CCC4)nc12]

8-fluoro-7-(8-fluoronaphthalen-1-yl)-2-((tetrahydro-1H-pyrrolizin-7a(5H)-yl)methoxy)-4-(2,2,2-trifluoroethoxy)pyrido[4,3-d]pyrimidine

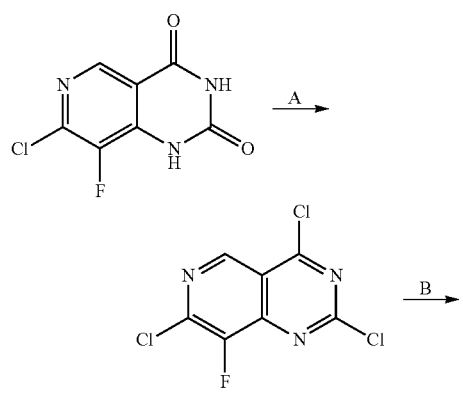

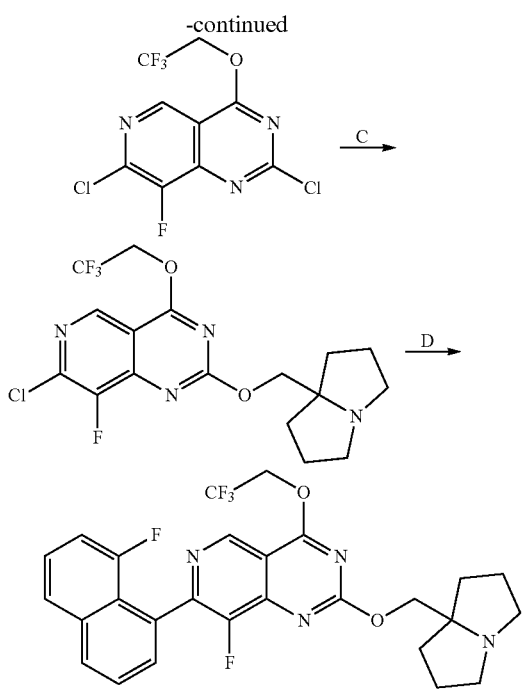

Step A. 2,4,7-trichloro-8-fluoropyrido[4,3-d]pyrimidine. To a solution of 7-chloro-8-fluoropyrido[4,3-d]pyrimidine-2,4 (1H,3H)-dione (100 g, 463 mmol, 1.00 eq) in toluene (500 mL) were added POCl₃ (213 g, 1.39 mol, 129 mL, 3.00 eq) and DIEA (179 g, 1.39 mol, 242 mL, 3.00 eq) at 0° C. The mixture was stirred at 110° C. for 5 h. The reaction was distilled in vacuum (80° C., water pump) to give 2,4,7-trichloro-8-fluoropyrido[4,3-d]pyrimidine (100 g, 396.10 mmol, 85.39% yield) as brown oil.

Step B. 2,7-dichloro-8-fluoro-4-(2,2,2-trifluoroethoxy)pyrido[4,3-d]pyrimidine. To a solution of 2,4,7-trichloro-8-fluoropyrido[4,3-d]pyrimidine (100 g, 396 mmol, 1.00 eq) and 2, 2, 2-trifluoroethanol (59.4 g, 594 mmol, 42.7 mL, 1.50 eq) in toluene (2 L) was added t-BuONa (152 g, 1.58 mol, 4.00 eq) at 25° C. The mixture was stirred at 25° C. for 2 hr. The reaction mixture was filtered through a pad of Celite, washed with brine (3 L×2) and concentrated under reduced pressure to give a residue, which was purified by reversed-phase HPLC (0.1% FA condition) to give 2,7-dichloro-8-fluoro-4-(2,2,2-trifluoroethoxy)pyrido[4,3-d]pyrimidine (45.0 g, 140 mmol, 35.5% yield, 99.0% purity) as a brown solid. LCMS: M+1, 316.

Step C. 7-chloro-8-fluoro-2-((tetrahydro-1H-pyrrolizin-7a(5H)-yl)methoxy)-4-(2,2,2-trifluoroethoxy)pyrido[4,3-d]pyrimidine. A mixture of (tetrahydro-1H-pyrrolizin-7a(5H)-yl)methanol (35.7 g, 253 mmol, 2.00 eq), DIEA (32.7 g, 253 mmol, 44.0 mL, 2.00 eq) and 4 A MS (40.0 g) in 2-methyltetrahydrofuran (400 mL) was stirred at 25° C. for 1 hr. Then a solution of 2,7-dichloro-8-fluoro-4-(2,2,2-trifluoroethoxy)pyrido[4,3-d]pyrimidine (40.0 g, 126 mmol, 1.00 eq) in 2-methyltetrahydrofuran (400 mL) was added and the resulting mixture was stirred at 25° C. for 2 hrs. The reaction mixture was filtered. The filtrate was washed with sat. aq. NH₄Cl solution (1 L×2), dried over Na₂SO₄, filtered and concentrated under reduced pressure to give a residue. The residue was triturated with acetonitrile (300 mL) at 25° C. for 30 min to give 7-chloro-8-fluoro-2-((tetrahydro-1H-pyrrolizin-7a(5H)-yl)methoxy)-4-(2,2,2-trifluoroethoxy)

pyrido[4,3-d]pyrimidine (26.0 g, 61.1 mmol, 48.3% yield, 99.0% purity) as a light yellow solid. LCMS: M+1, 421.

Step D. 8-fluoro-7-(8-fluoronaphthalen-1-yl)-2-((tetrahydro-1H-pyrrolizin-7a(5H)-yl)methoxy)-4-(2,2,2-trifluoroethoxy)pyrido[4,3-d]pyrimidine. A mixture of 7-chloro-8-fluoro-2-((tetrahydro-1H-pyrrolizin-7a(5H)-yl)methoxy)-4-(2,2,2-trifluoroethoxy)pyrido[4,3-d]pyrimidine (17.0 g, 40.4 mmol, 1.00 eq), 2-(8-fluoronaphthalen-1-yl)-4,4,5,5-tetramethyl-1,3,2-dioxaborolane (16.4 g, 60.6 mmol, 1.50 eq), BrettPhos Pd G3 (4.25 g, 4.69 mmol, 1.16e-1 eq), K$_3$PO$_4$ (1.5 M, 80.8 mL, 3.00 eq) in toluene (170 mL) was degassed and purged with N2 for 3 times, and then the mixture was stirred at 65° C. for 4 hrs under N$_2$ atmosphere. The reaction mixture was filtered. The filtrate was extracted with toluene (170 mL×3). The combined organic layers were dried over Na$_2$SO$_4$, filtered and concentrated under reduced pressure to give a residue. The residue was purified by reversed-phase HPLC (0.1% FA condition) to give 8-fluoro-7-(8-fluoronaphthalen-1-yl)-2-((tetrahydro-1H-pyrrolizin-7a(5H)-yl)methoxy)-4-(2,2,2-trifluoroethoxy)pyrido[4,3-d]pyrimidine (10.85 g, 16.6 mmol, 41.2% yield, 95.8% purity) as a yellow solid. NMR: δ 9.28 (s, 1H), 8.23 (d, J=8.1 Hz, 1H), 7.97 (d, J=8.1 Hz, 1H), 7.81-7.76 (m, 1H), 7.68 (dd, J=0.9, 7.2 Hz, 1H), 7.61 (dt, J=5.1, 7.9 Hz, 1H), 7.34 (dd, J=7.1, 13.3 Hz, 1H), 5.47-5.37 (m, 2H), 4.77-4.67 (m, 2H), 3.56-3.49 (m, 2H), 3.22 (td, J=6.0, 11.7 Hz, 2H), 2.27-2.00 (m, 8H); LCMS: M+1, 531.

Intermediate 21

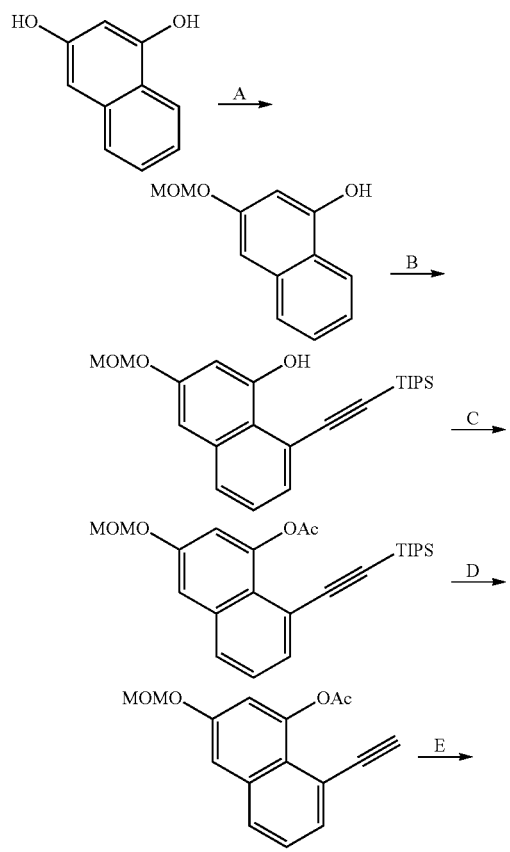

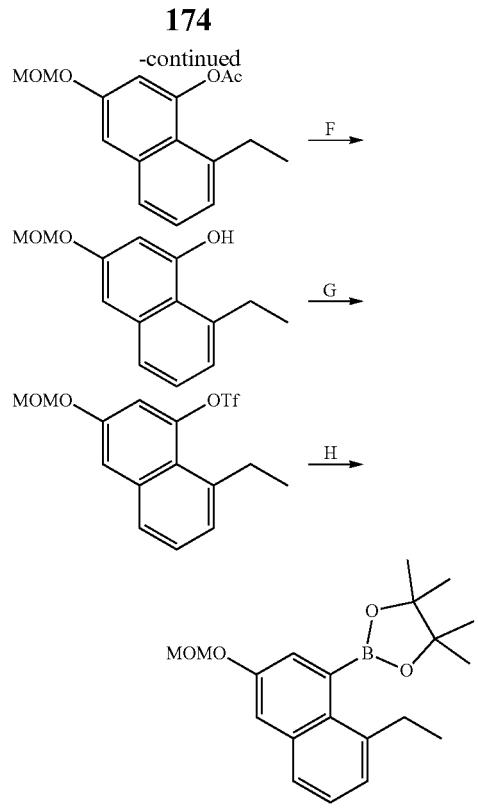

2-[8-ethyl-3-(methoxymethoxy)-1-naphthyl]-4,4,5,5-tetramethyl-1,3,2-dioxaborolane

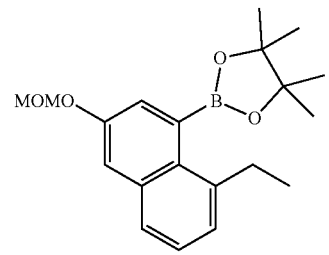

Step A. 3-(methoxymethoxy)naphthalen-1-ol. To a solution of naphthalene-1,3-diol (50 g, 312 mmol, 1.0 eq) and DIEA (120 g, 935 mmol, 163 mL, 3.0 eq) in dichloromethane (400 mL) was added chloro(methoxy)methane (27.5 g, 342 mmol, 1.1 eq) dropwise at 0-5° C. over 30 minutes. The mixture was stirred at 25° C. for 16 hours. The reaction mixture was quenched with saturated NaHCO$_3$ aqueous solution (100 mL) below 5° C. and diluted with H$_2$O (300 mL). The organic layer was separated and H$_2$O (100 mL) was added. The pH of the mixture was adjusted to 3-4 with 2N HCl below 10° C. The organic layer was separated, dried over Na$_2$SO$_4$, filtered and concentrated under reduced pressure to give a residue. The residue was purified by silica gel column chromatography (petroleum ether/ethyl acetate=10/1, 8/1) to give the title compound (31.3 g, 49% yield). Red brown liquid. $^1$H NMR (400 MHz, chloroform-d) δ=8.17-8.08 (m, 1H), 7.71-7.61 (m, 1H), 7.45-7.30 (m, 2H), 7.02-6.63 (m, 2H), 5.38-5.28 (m, 2H), 3.56-3.53 (m, 3H).

Step B. 3-(methoxymethoxy)-8-(2-triisopropylsilylethynyl)naphthalen-1-ol. A mixture of 3-(methoxymethoxy)

naphthalen-1-ol (20 g, 97.9 mmol, 1.0 eq), (bromoethynyl)triisopropylsilane (32 g, crude), K₂CO₃ (13.6 g, 98.4 mmol, 1.0 eq), sodium acetate (2 g, 24.4 mmol, 0.25 eq) and dichlororuthenium; 1-isopropyl-4-methyl-benzene dimer (9.00 g, 14.7 mmol, 0.15 eq) in DCE (200 mL) was degassed and purged with N2 for 3 times. The mixture was stirred at 40° C. for 13 hours under N₂ atmosphere. The reaction mixture was filtered through a pad of Celite. The filtrate was concentrated under reduced pressure to give a residue. The residue was purified by silica gel column chromatography (SiO₂, petroleum ether/ethyl acetate=1/0 to 50/1) to give the title compound (10.6 g, 28% yield). Yellow liquid. $^1$H NMR (400 MHz, chloroform-d) δ=9.26 (s, 1H), 7.69 (dd, J=0.8, 8.4 Hz, 1H), 7.50 (dd, J=1.2, 7.2 Hz, 1H), 7.33-7.29 (m, 1H), 6.97 (d, J=2.4 Hz, 1H), 6.77 (d, J=2.4 Hz, 1H), 5.27 (s, 2H), 3.52 (s, 3H), 1.29-1.14 (m, 21H).

Step C. 3-(methoxymethoxy)-8-(2-triisopropylsilylethynyl)-1-naphthyl acetate. To a mixture of 3-(methoxymethoxy)-8-(2-triisopropylsilylethynyl)naphthalen-1-ol (10 g, 26.0 mmol, 1.0 eq) and DIEA (8.40 g, 65.0 mmol, 11.3 mL, 2.5 eq) in dichloromethane (100 mL) was added acetyl chloride (3.06 g, 39.0 mmol, 2.78 mL, 1.5 eq) at 0° C. The mixture was stirred at 0° C. for 0.5 hour. After completion, the mixture was diluted with water (100 mL) and separated. The water phase was extracted with dichloromethane (50 mL). The combined organic layer was washed with brine (70 mL), dried over Na₂SO₄, filtered and concentrated under vacuum. The residue was purified by column chromatography (SiO₂, petroleum ether/ethyl acetate=3/1) to give the title compound (9 g, 80% yield). Yellow oil. Rf=0.28 (petroleum ether/ethyl acetate=3/1). $^1$H NMR (400 MHz, chloroform-d) δ=7.72 (dd, J=0.8, 8.4 Hz, 1H), 7.67 (dd, J=1.2, 7.2 Hz, 1H), 7.36 (dd, J=7.2, 8.4 Hz, 1H), 7.32 (d, J=2.4 Hz, 1H), 6.96 (d, J=2.4 Hz, 1H), 5.28 (s, 2H), 3.52 (s, 3H), 2.44 (s, 3H), 1.19 (s, 21H).

Step D. 8-ethynyl-3-(methoxymethoxy)naphthalen-1-yl acetate. A mixture of 3-(methoxymethoxy)-8-(2-triisopropylsilylethynyl)-1-naphthyl acetate (9.3 g, 21.8 mmol, 1 eq) and CsF (23.2 g, 153 mmol, 5.63 mL, 7 eq) in DMF (90 mL) was stirred at 25° C. for 1 hour. After completion, the mixture was diluted with ethyl acetate (150 mL), washed with brine (3×100 mL), dried over Na₂SO₄, filtered and concentrated under vacuum. The residue was purified by column chromatography (SiO₂, petroleum ether/ethyl acetate=3/1) to give the title compound (2.5 g, 42% yield). Yellow oil. Rf=0.21 (petroleum ether/ethyl acetate=3/1). [ESI, M+1]: 271.2 Step E. [8-ethyl-3-(methoxymethoxy)-1-naphthyl] acetate. A mixture of [8-ethynyl-3-(methoxymethoxy)-1-naphthyl] acetate (2.5 g, 9.25 mmol, 1 eq) and Pd/C (60 mg, 10% purity) in methanol (10 mL) was stirred at 25° C. for 10 minutes under H₂ at 15 psi. After completion, the mixture was filtered and concentrated under vacuum to give the title compound (2.1 g, 83% yield) and used in the next step without further purification. Yellow oil. [ESI, M−41]: 233.3.

Step F. 8-ethyl-3-(methoxymethoxy)naphthalen-1-ol. A mixture of [8-ethyl-3-(methoxymethoxy)-1-naphthyl] acetate (2 g, 7.29 mmol, 1 eq) and LiOH (873 mg, 36.5 mmol, 5 eq) in THF (20 mL) and H₂O (6 mL) was stirred at 25° C. for 1 hour. After completion, the mixture was diluted with water (50 mL), and extracted with ethyl acetate (2×50 mL). The combined organic layer was washed with brine. The residue was purified by column chromatography (SiO₂, petroleum ether/ethyl acetate=5/1,) to give the title compound (1.42 g, 66% yield). Yellow oil. Rf=0.26 (petroleum ether/ethyl acetate=5/1). $^1$H NMR (400 MHz, chloroform-d) δ=7.53 (d, J=8.0 Hz, 1H), 7.3 (t, J=3.6 Hz, 1H), 7.11 (d, J=7.2 Hz, 1H), 7.00 (d, J=2.4 Hz, 1H), 6.55 (d, J=2.4 Hz, 1H), 5.27 (s, 2H), 3.53 (s, 3H), 3.30 (q, J=7.4 Hz, 2H), 1.33 (t, J=7.2 Hz, 3H).

Step G. [8-ethyl-3-(methoxymethoxy)-1-naphthyl] trifluoromethanesulfonate. To a mixture of 8-ethyl-3-(methoxymethoxy)naphthalen-1-ol (1.4 g, 6.03 mmol, 1 eq) and DIEA (3.12 g, 24.1 mmol, 4.20 mL, 4 eq) in dichloromethane (20 mL) was added Tf₂O (2.55 g, 9.04 mmol, 1.49 mL, 1.5 eq) at −40° C. The mixture was stirred at −40° C. for 0.5 hour. After completion, the mixture was diluted with water (20 mL) and separated. The water phase was extracted with dichloromethane (10 mL), and the combined organic layer was washed with brine (20 mL), dried over Na₂SO₄, filtered and concentrated under vacuum. The residue was purified by column chromatography (SiO₂, petroleum ether/ethyl acetate=5/1, Rf=0.67) to give the title compound (1.87 g, 83% yield). Yellow oil. Rf=0.67 (petroleum ether/ethyl acetate=5/1).

Step H. 2-[8-ethyl-3-(methoxymethoxy)-1-naphthyl]-4,4,5,5-tetramethyl-1,3,2-dioxaborolane. A mixture of [8-ethyl-3-(methoxymethoxy)-1-naphthyl] trifluoromethanesulfonate (1.8 g, 4.94 mmol, 1 eq), 4,4,5,5-tetramethyl-2-(4,4,5,5-tetramethyl-1,3,2-dioxaborolan-2-yl)-1,3,2-dioxaborolane (3.14 g, 12.4 mmol, 2.5 eq), KOAc (1.21 g, 12.4 mmol, 2.5 eq) and Pd(dppf)Cl₂ (362 mg, 494 μmol, 0.1 eq) in dioxane (20 mL) was stirred at 110° C. for 2 hours. After completion, the mixture was diluted with water (20 mL) and extracted with ethyl acetate (2×20 mL). The combined organic layer was washed with brine (20 mL), dried over Na₂SO₄, filtered and concentrated under vacuum. The residue was purified by column chromatography (SiO₂, petroleum ether/ethyl acetate=30/1) to give the title compound (810 mg, 46% yield). Yellow oil. Rf=0.7 (petroleum ether/ethyl acetate=10/1). $^1$H NMR (400 MHz, chloroform-d) δ=7.60 (dd, J=0.8, 8.0 Hz, 1H), 7.42 (d, J=2.8 Hz, 1H), 7.40-7.33 (m, 2H), 7.27-7.24 (m, 1H), 5.30 (s, 2H), 3.52 (s, 3H), 3.19 (q, J=7.2 Hz, 2H), 1.45 (s, 12H), 1.36 (t, J=7.2 Hz, 3H).

Intermediate 22

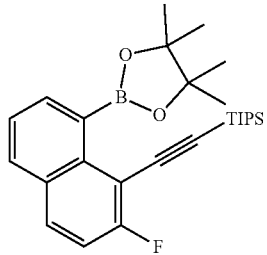

((2-fluoro-8-(4,4,5,5-tetramethyl-1,3,2-dioxaborolan-2-yl)naphthalen-1-yl)ethynyl)triisopropylsilane

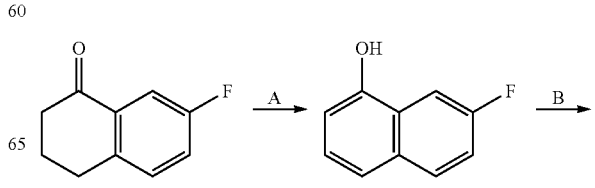

-continued

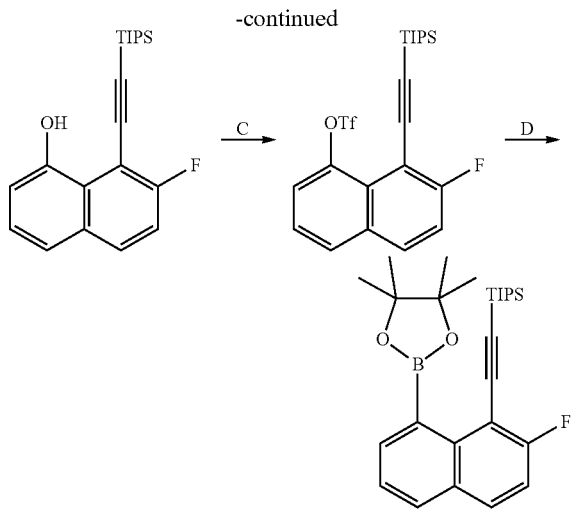

Step A. 7-fluoronaphthalen-1-ol. To a solution of 7-fluoro-3,4-dihydronaphthalen-1 (2H)-one (75.0 g, 457 mmol, 1.00 eq) in acetic acid (1.50 L) and hydrogen bromide in AcOH (33%, 7.50 mL) was added bromine (80.3 g, 503 mmol, 25.9 mL, 1.1 eq) in acetic acid (50 mL) at 0° C., and the mixture was stirred at 25° C. for 3 hours. The mixture was diluted with DCM (1.5 L), washed with water (3×500 mL). The organic layer was dried over anhydrous sodium sulfate, filtered and concentrated to afford a brown oil, which was dissolved in DMF (750 mL). Lithium bromide (67.4 g, 777 mmol, 19.5 mL, 1.70 eq), lithium carbonate (57.4 g, 777 mmol, 1.70 eq) were added. The reaction mixture was stirred at 160° C. for 3.5 hours. The reaction was diluted with ethyl acetate (1.00 L), washed with brine (2×500 mL), dried with anhydrous sodium sulfate, filtered and concentrated in vacuum to give a residue. The residue was purified by silica gel chromatography (petroleum ether/ethyl acetate=1/0 to 5/1) affording the title compound (61.0 g, 82% yield). Brown solid; $^1$H NMR (400 MHz, CDCl$_3$) δ=7.84-7.77 (m, 2H), 7.44 (d, J=8.0 Hz, 1H), 7.31-7.24 (m, 2H), 6.84 (d, J=7.6 Hz, 1H), 5.39 (s, 1H).

Step B. 7-fluoro-8-(2-triisopropylsilylethynyl)naphthalen-1-ol. To a solution of (bromoethynyl)triisopropylsilane (72.0 g, 275 mmol, 1.20 eq) and 7-fluoronaphthalen-1-ol (37.2 g, 230 mmol, 1.0 eq) in DCE (500 mL) were added dichlororuthenium; 1-isopropyl-4-methyl-benzene (21.1 g, 34.4 mmol, 0.15 eq), K$_2$CO$_3$ (31.7 g, 230 mmol, 1.0 eq) and NaOAc (3.77 g, 45.9 mmol, 0.20 eq). The mixture was stirred at 40° C. for 12 hours. The reaction mixture was filtered and concentrated under reduced pressure to give a residue. The residue was purified by column chromatography (SiO$_2$, petroleum ether/ethyl acetate=1/0 to 50/1) affording the title compound (73.0 g, 93% yield). Yellow oil; $^1$H NMR (400 MHz, CDCl$_3$) δ 9.10 (s, 1H), 7.79 (dd, J=5.6, 8.8 Hz, 1H), 7.41-7.33 (m, 2H), 7.23 (t, J=8.8 Hz, 1H), 7.08-7.00 (m, 1H), 1.24-1.14 (m, 21H); LCMS [ESI, M+1, 2M+1]: 343.1, 685.3.

Step C. [7-fluoro-8-(2-triisopropylsilylethynyl)-1-naphthyl] trifluoromethanesulfonate. To a solution of 7-fluoro-8-(2-triisopropylsilylethynyl)naphthalen-1-ol (73.0 g, 213 mmol, 1.00 eq) in DCM (600 mL) were added DIEA (55.1 g, 426 mmol, 74.2 mL, 2.00 eq) and Tf$_2$O (90.2 g, 320 mmol, 52.7 mL, 1.50 eq) at −40° C. The mixture was stirred at −40° C. for 0.5 hour. The combined reaction mixture was filtered and concentrated under reduced pressure to give a residue. The mixture was purified by column chromatography (SiO$_2$, petroleum ether/ethyl acetate=1/0 to 50/1) affording the title compound (78.0 g, 77% yield). Yellow solid; $^1$H NMR (400 MHz, CDCl$_3$) δ 7.88-7.79 (m, 2H), 7.59-7.52 (m, 1H), 7.46 (t, J=8.0 Hz, 1H), 7.37 (t, J=8.8 Hz, 1H), 1.32-1.16 (m, 21H).

Step D. ((2-fluoro-8-(4,4,5,5-tetramethyl-1,3,2-dioxaborolan-2-yl)naphthalen-1-yl)ethynyl)triisopropylsilane. To a solution of [7-fluoro-8-(2-triisopropylsilylethynyl)-1-naphthyl]trifluoromethanesulfonate (20.0 g, 42.1 mmol, 1.00 eq) and bis(pinacolato)diboron (16.0 g, 63.2 mmol, 1.50 eq) in dioxane (6.00 mL) were added KOAc (8.27 g, 84.3 mmol, 2.0 eq) and Pd(dppf)Cl$_2$ (3.08 g, 4.21 mmol, 0.10 eq). The mixture was stirred at 110° C. for 12 hours. The mixture was filtered and concentrated under reduced pressure to give a residue. The residue was purified by column chromatography (SiO$_2$, petroleum ether/ethyl acetate=1/0 to 10/1) affording the title compound (9.0 g, 47% yield). Yellow solid; $^1$H NMR (400 MHz, CDCl$_3$) δ 7.85-7.75 (m, 3H), 7.43 (dd, J=7.2, 8.0 Hz, 1H), 7.30-7.24 (m, 1H), 1.45 (s, 12H), 1.21-1.14 (m, 21H); LCMS [ESI, M+1]: 453.2.

Intermediate 23

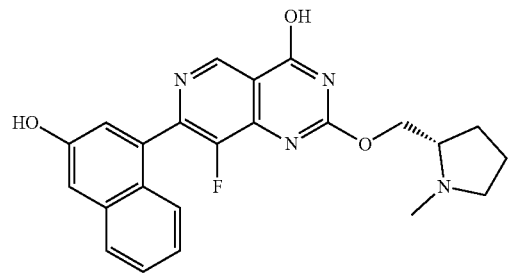 [SMILES: CN1CCC[C@H]1COc1nc(O)c2cnc(-c3cc(O)cc4ccccc34)c(F)c2n1]

(S)-8-fluoro-7-(3-hydroxynaphthalen-1-yl)-2-((1-methylpyrrolidin-2-yl)methoxy)pyrido[4,3-d]pyrimidin-4-ol

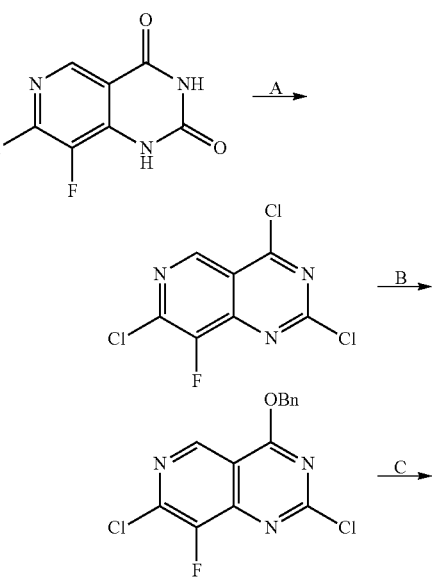

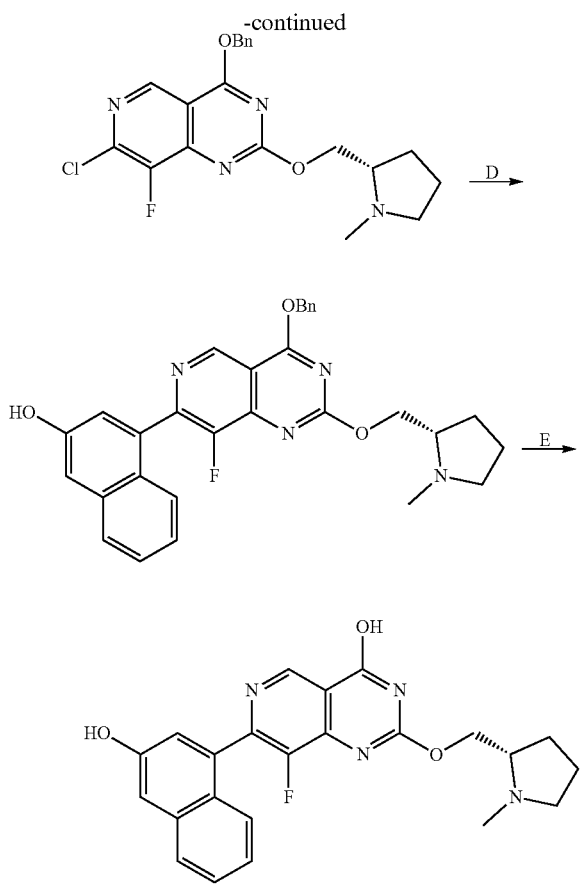

Step A. 2,4,7-trichloro-8-fluoropyrido[4,3-d]pyrimidine. To a flask containing 7-chloro-8-fluoropyrido[4,3-d] pyrimidine-2,4 (1H,3H)-dione (0.93 g, 4.3 mmol) was added POCl₃ (8 mL, 86 mmol). The mixture was cooled with an ice bath and DIPEA (2 mL, 13 mmol) was added. The ice bath was removed and the mixture was stirred at 100° C. for 20 hours. The solution was cooled and concentrated to give a brown oil. The oil was dissolved in DCM and the solution was quenched with a mixture of K₃PO₄ (37%, 10 mL) and ice (20 g). The mixture was stirred for 10 minutes. The two layers were separated, and the organic layer was further washed with brine, dried over Na₂SO₄, and concentrated to give crude 2,4,7-trichloro-8-fluoropyrido[4,3-d]pyrimidine which was used immediately without purification assuming 100% yield Step B. 4-(benzyloxy)-2,7-dichloro-8-fluoropyrido[4,3-d]pyrimidine. To a flask containing crude 2,4,7-trichloro-8-fluoropyrido[4,3-d]pyrimidine (1.5 g, 4.3 mmol) were added molecular sieves (3 Å, 0.4 g), 1,4-dioxane (22 mL), benzyl alcohol (0.50 mL, 4.7 mmol) and DIPEA (2.0 mL, 13 mmol). The mixture was stirred at 60° C. under N₂ for 7 hours. The mixture was concentrated to dryness and diluted with EtOAc. The mixture was filtered through a pad of Celite, and the filtrate was concentrated in vacuo. The residue was purified by flash chromatography eluting with 0-25% ethyl acetate/hexanes to afford 4-(benzyloxy)-2,7-dichloro-8-fluoropyrido[4,3-d]pyrimidine (0.68 g, 49%). LCMS (MM-ES+APCI, Pos): m/z 324.1 (M+H).

Step C. (S)-4-(benzyloxy)-7-chloro-8-fluoro-2-((1-methylpyrrolidin-2-yl)methoxy)pyrido[4,3-d]pyrimidine. To a solution of 4-(benzyloxy)-2,7-dichloro-8-fluoropyrido[4,3-d]pyrimidine (1.3 g, 4.0 mmol) in 1,4-dioxane (40 mL) was added (S)-(1-methylpyrrolidin-2-yl)methanol (0.67 mL, 5.6 mmol) followed by Cs₂CO₃ (3.27 g, 10 mmol). The mixture was heated at 80° C. under N₂ for 3 hours followed by stirring at room temperature for 15 hours. The mixture was diluted with ethyl acetate and filtered through a pad of Celite. The filtrate was concentrated, and the residue was purified by preparative C18 HPLC (Gilson, 0-95% CH₃CN/H₂O with 0.1% TFA as modifier). The desired fractions were combined, basified with Na₂CO₃ (2 M), and extracted with EtOAc. The combined organic extract was washed with brine, dried over Na₂SO₄ and concentrated to afford (S)-4-(benzyloxy)-7-chloro-8-fluoro-2-((1-methylpyrrolidin-2-yl)methoxy)pyrido[4,3-d]pyrimidine (0.91 g, 56%). LCMS (MM-ES+APCI, Pos): m/z 403.1 (M+H).

Step D. (S)-4-(4-(benzyloxy)-8-fluoro-2-((1-methylpyrrolidin-2-yl)methoxy)pyrido[4,3-d]pyrimidin-7-yl)naphthalen-2-ol. A flask containing a solution of 4-(4,4,5,5-tetramethyl-1,3,2-dioxaborolan-2-yl)naphthalen-2-ol (0.58 g, 2.1 mmol), (S)-4-(benzyloxy)-7-chloro-8-fluoro-2-((1-methylpyrrolidin-2-yl)methoxy)pyrido[4,3-d]pyrimidine (0.66 g, 1.6 mmol), Na₂CO₃ (2 mL, 4 mmol), Pd(PPh₃)₄ (0.19 g, 0.16 mmol) in dioxane (16 mL) was sparged with N2. The mixture was heated under N₂ at 80° C. for 7 hours and cooled to room temperature. The resulting mixture was quenched with water and extracted with EtOAc. The combined EtOAc extract was dried over Na₂SO₄, concentrated, and purified by preparative C18 HPLC (Gilson, 5-95% CH₃CN/H₂O with 0.1% TFA). The desired fractions were combined, basified with NaHCO₃(Sat.) and extracted with DCM. The combined DCM extract was dried over Na₂SO₄, filtered and concentrated to afford (S)-4-(4-(benzyloxy)-8-fluoro-2-((1-methylpyrrolidin-2-yl)methoxy)pyrido[4,3-d]pyrimidin-7-yl)naphthalen-2-ol (0.39 g, 46% yield). LCMS (MM-ES+APCI, Pos): m/z 511.2 (M+H).

Step E. (S)-8-fluoro-7-(3-hydroxynaphthalen-1-yl)-2-((1-methylpyrrolidin-2-yl)methoxy)pyrido[4,3-d]pyrimidin-4-ol. To a flask with a stir bar was added Pd/C (160 mg, 0.15 mmol). A solution of (S)-4-(4-(benzyloxy)-8-fluoro-2-((1-methylpyrrolidin-2-yl)methoxy)pyrido[4,3-d]pyrimidin-7-yl)naphthalen-2-ol (0.39 g, 0.75 mmol) in EtOAc (15 mL) was added. The flask was closed with a septum and stirred under a balloon of H2 at room temperature for 15 hours. The mixture was filtered through Celite and the Celite was further washed with DCM/MeOH (2:1, 200 mL). The combined organics were concentrated and dried to afford (S)-8-fluoro-7-(3-hydroxynaphthalen-1-yl)-2-((1-methylpyrrolidin-2-yl)methoxy)pyrido[4,3-d]pyrimidin-4-ol (0.29 g, 92% yield). LCMS (MM-ES+APCI, Pos): m/z 421.2 (M+H).

Intermediate 24

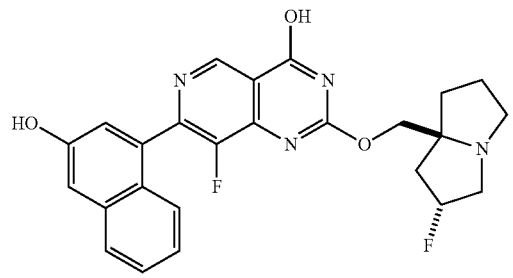

181

8-fluoro-2-(((2R,7aS)-2-fluorotetrahydro-1H-pyr-rolizin-7a(5H)-yl)methoxy)-7-(3-hydroxynaphtha-len-1-yl)pyrido[4,3-d]pyrimidin-4-ol (racemic, trans)

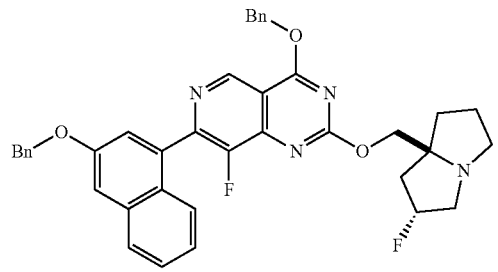

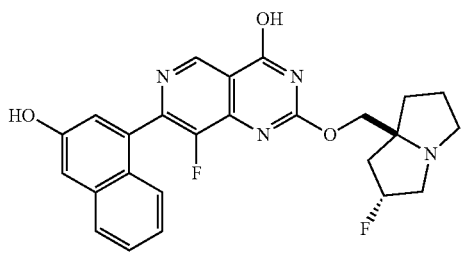

4-(benzyloxy)-7-(3-(benzyloxy)naphthalen-1-yl)-8-fluoro-2-(((2R,7aS)-2-fluorotetrahydro-1H-pyrrolizin-7a(5H)-yl)methoxy)pyrido[4,3-d]pyrimidine. Synthesized according to intermediate 23 substituting racemic ((2R,7aS)-2-fluorotetrahydro-1H-pyrrolizin-7a(5H)-yl)methanol for (S)-(1-methylpyrrolidin-2-yl)methanol in step C and 2-(3-(benzyloxy)naphthalen-1-yl)-4,4,5,5-tetramethyl-1,3,2-dioxaborolane for 4-(4,4,5,5-tetramethyl-1,3,2-dioxaborolan-2-yl)naphthalen-2-ol in step D. LCMS (MM-ES+APCI, Pos): m/z 645.3 (M+H).

Step A. 8-fluoro-2-(((2R,7aS)-2-fluorotetrahydro-1H-pyrrolizin-7a(5H)-yl)methoxy)-7-(3-hydroxynaphthalen-1-yl)pyrido[4,3-d]pyrimidin-4-ol. To 4-(benzyloxy)-7-(3-(benzyloxy)naphthalen-1-yl)-8-fluoro-2-(((2R,7aS)-2-fluorotetrahydro-1H-pyrrolizin-7a(5H)-yl)methoxy)pyrido[4,3-d]pyrimidine (1.0 g, 1.6 mmol) in DCM (200 mL) at −70° C. were added 1,2,3,4,5-pentamethylbenzene (1.2 g, 7.8 mmol) and dropwise trichloroborane (8.0 mL, 7.7 mmol). The reaction was stirred at −70° C. for 30 minutes and warmed to 0° C. The reaction was stirred at 0° C. for two hours and quenched with sat. NaHCO₃ (150 mL). The aqueous layer was extracted with IPA/DCM (20%, 3×). The combined organic phases were then dried over Na₂SO₄, filtered, and concentrated. The material was triturated with ether and the solids filtered to give 8-fluoro-2-(((2R,7aS)-2-fluorotetrahydro-1H-pyrrolizin-7a(5H)-yl)methoxy)-7-(3-hydroxynaphthalen-1-yl)pyrido[4,3-d]pyrimidin-4-ol (0.59 g, 82% yield). LCMS (MM-ES+APCI, Pos): m/z 465.1 (M+H).

182

Intermediate 25

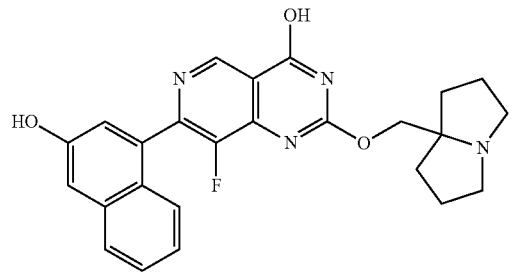 [SMILES: Oc1cc(-c2ncc3c(O)nc(OCC45CCCN4CCC5)nc3c2F)c2ccccc2c1]

8-fluoro-7-(3-hydroxynaphthalen-1-yl)-2-((tetra-hydro-1H-pyrrolizin-7a(5H)-yl)methoxy)pyrido[4,3-d]pyrimidin-4-ol

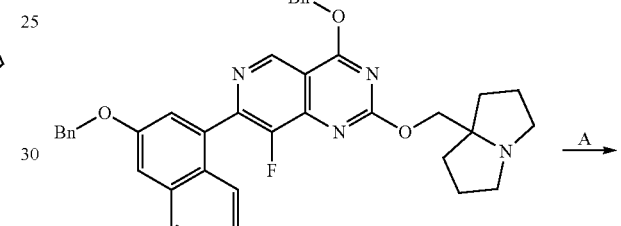

4-(benzyloxy)-7-(3-(benzyloxy)naphthalen-1-yl)-8-fluoro-2-((tetrahydro-1H-pyrrolizin-7a(5H)-yl)methoxy)pyrido[4,3-d]pyrimidine. Synthesized according to intermediate 23 substituting tetrahydro-1H-pyrrolizin-7a(5H)-yl)methanol for (S)-(1-methylpyrrolidin-2-yl)methanol in step C and 2-(3-(benzyloxy)naphthalen-1-yl)-4,4,5,5-tetramethyl-1,3,2-dioxaborolane for 4-(4,4,5,5-tetramethyl-1,3,2-dioxaborolan-2-yl)naphthalen-2-ol in step D. LCMS (MM-ES+APCI, Pos): m/z 627.3 (M+H).

Step A. 8-fluoro-7-(3-hydroxynaphthalen-1-yl)-2-((tetra-hydro-1H-pyrrolizin-7a(5H)-yl)methoxy)pyrido[4,3-d]pyrimidin-4-ol. To 4-(benzyloxy)-7-(3-(benzyloxy)naphthalen-1-yl)-8-fluoro-2-((tetrahydro-1H-pyrrolizin-7a(5H)-yl)methoxy)pyrido[4,3-d]pyrimidine (5.3 g, 8.38 mmol) in THF/MeOH (10 mL/6 mL) was added Pd(OH)₂/C (4.7 g, 3.4 mmol). The mixture was flushed with N2 and H2, and then stirred at 45 psi H2 for 16 hours. The reaction was filtered through Celite and the Celite was washed with 20% MeOH/DCM. The filtrate was concentrated to afford 8-fluoro-7-(3-hydroxynaphthalen-1-yl)-2-((tetrahydro-1H-pyrrolizin-7a(5H)-yl)methoxy)pyrido[4,3-d]pyrimidin-4-ol (2.1 g, 56% yield). LCMS (MM-ES+APCI, Pos): m/z 447.3 (M+H).

183
Intermediate 26

184
Example 1

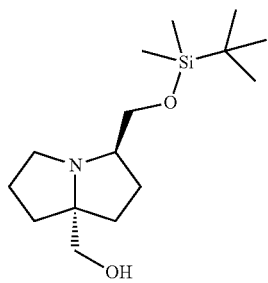 [SMILES: CC(C)(C)[Si](C)(C)OC[C@H]1CC[C@@]2(CO)CCCN12]

((3R,7aR)-3-(((tert-butyldimethylsilyl)oxy)methyl)
tetrahydro-1H-pyrrolizin-7a(5H)-yl)methanol

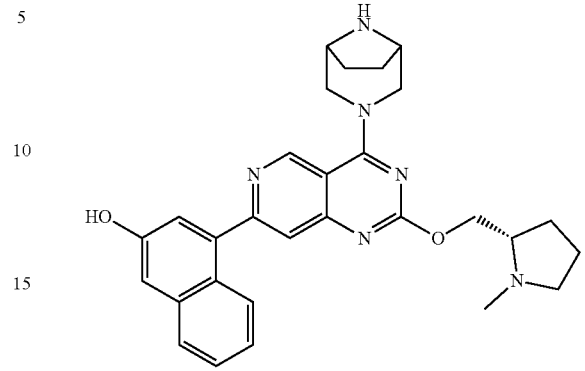

4-(4-((1R,5S)-3,8-diazabicyclo[3.2.1]octan-3-yl)-2-
(((S)-1-methylpyrrolidin-2-yl)methoxy)pyrido[4,3-d]
pyrimidin-7-yl)naphthalen-2-ol tris-hydrochloride
salt

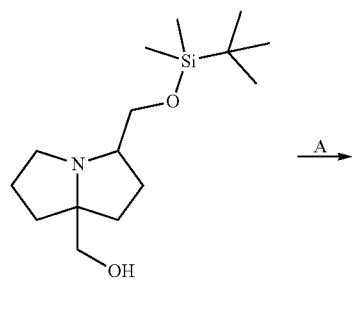

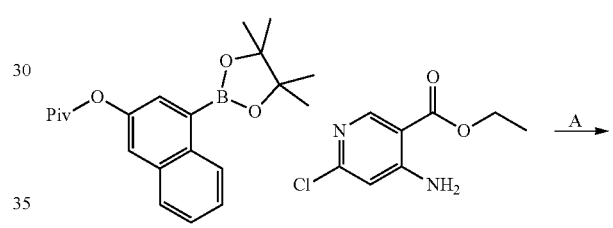

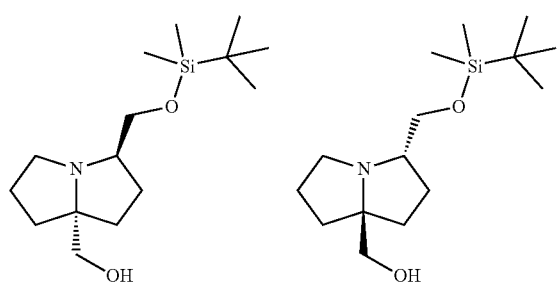

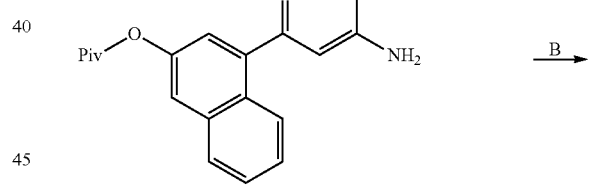

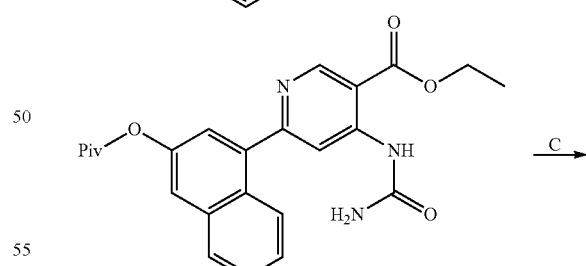

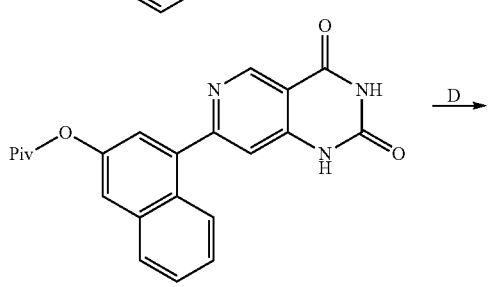

A mixture of (3-(((tert-butyldimethylsilyl)oxy)methyl)tetrahydro-1H-pyrrolizin-7a(5H)-yl)methanol was separated by Lotus Separations using chiral SFC using an AD-H (3×25 cm) column injecting with 1 mL of a 20 mg/mL solution of compound in methanol eluting with 20% methanol/C02 at 100 bar of pressure with 70 mL/min. flow rate and monitoring 220 nM. The following Examples are intended to illustrate further certain embodiments of the invention and are not intended to limit the scope of the invention.

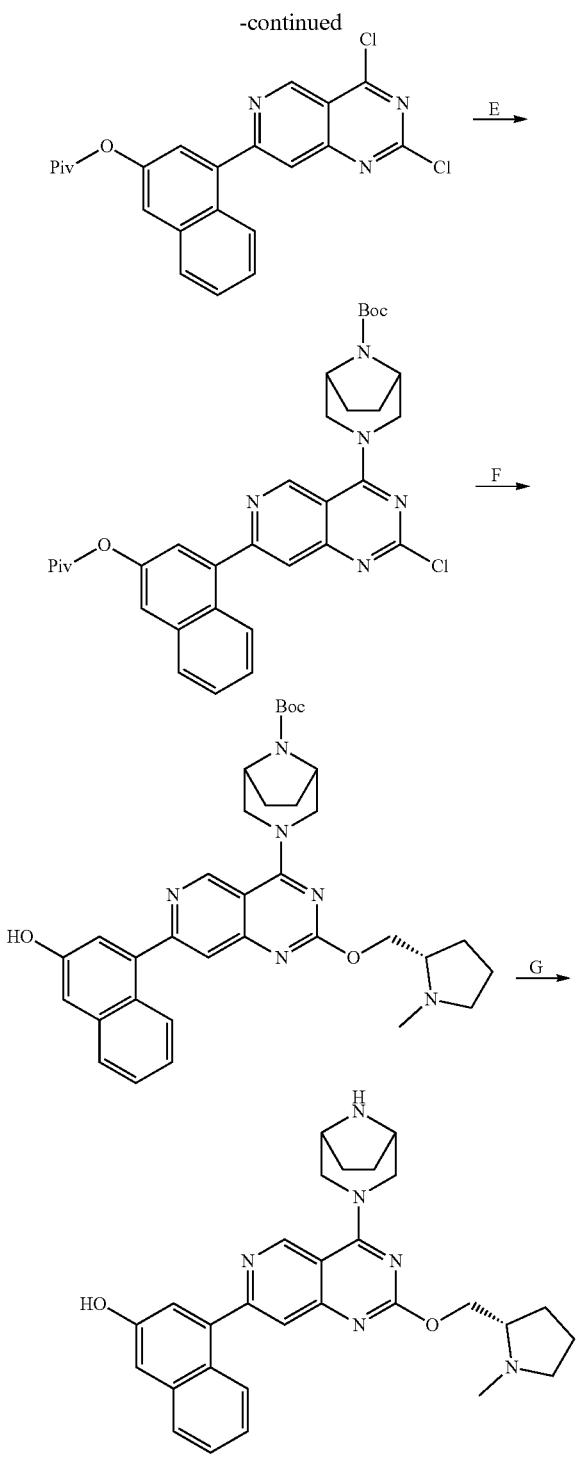

Step A. Ethyl 4-amino-6-(3-(pivaloyloxy)naphthalen-1-yl)nicotinate. To a solution of ethyl 4-amino-6-chloronicotinate (0.850 g, 4.24 mmol) in dioxane was added potassium carbonate (2.00 M solution, 10.6 ml, 21.2 mmol) and 4-(4,4,5,5-tetramethyl-1,3,2-dioxaborolan-2-yl)naphthalen-2-yl pivalate (2.25 g, 6.36 mmol) and the reaction was sparged with nitrogen for 15 min. To the mixture were added Xphos (0.150 g, 0.318 mmol) and Pd₂(dba)₃ (0.150 g, 0.159 mmol) and the reaction was heated for 24 h at 80° C. The reaction was diluted with EtOAc and washed with water and brine, dried over MgSO₄ and concentrated in vacuo. The residue was purified by flash chromatography eluting with 0-100% EtOAc/CH₂Cl₂ as eluent to give ethyl 4-amino-6-(3-(pivaloyloxy)naphthalen-1-yl)nicotinate (1.23 g, 3.13 mmol, 74.0% yield). LCMS (MM-ES+APCI, Pos): m/z 393.2 (M+H).

Step B. Ethyl 6-(3-(pivaloyloxy)naphthalen-1-yl)-4-ureidonicotinate. To a solution of 20% phosgene (813 mg, 1.64 mmol) in CH₂Cl₂ (5.48 ml, 0.20 M) cooled to 0° C. was added a solution of ethyl 4-amino-6-(3-(pivaloyloxy)naphthalen-1-yl)nicotinate (430 mg, 1.10 mmol) and N-ethyl-N-isopropylpropan-2-amine (393 μL, 2.19 mmol) in CH₂Cl₂ (5.48 ml). The reaction was stirred for 1 hr while warming to ambient temperature. To the reaction mixture was added ammonia in dioxane (4.40 ml, 2.19 mmol) and the resulting mixture was stirred an additional 1 h. The reaction was concentrated in vacuo and the residue was diluted with MeOH and filtered to collect solid, washing with MeOH (2×). The solid was dried in vacuo for 24 h to give ethyl 6-(3-(pivaloyloxy)naphthalen-1-yl)-4-ureidonicotinate (337 mg, 0.774 mmol, 70.6%). LCMS (MM-ES+APCI, Pos): m/z 436.3 (M+H).

Step C. 4-(2,4-Dioxo-1,2,3,4-tetrahydropyrido[4,3-d]pyrimidin-7-yl)naphthalen-2-yl pivalate. A solution of ethyl 6-(3-(pivaloyloxy)naphthalen-1-yl)-4-ureidonicotinate (130 mg, 0.269 mmol) and Cs₂CO₃ (500 mg, 1.53 mmol) in toluene (10.0 ml, 0.269 mmol) was heated at reflux for 1 h. The reaction mixture was transferred to a separatory funnel washing with EtOAc and acidified to pH 5 with HCl (6N). The organic layer was separated and washed with brine, dried over Na₂SO₄ and concentrated to afford 4-(2,4-dioxo-1,2,3,4-tetrahydropyrido[4,3-d]pyrimidin-7-yl)naphthalen-2-yl pivalate (118 mg, 0.273 mmol, 90% pure, 100% yield). LCMS (MM-ES+APCI, Pos): m/z 393.2 (M+H).

Step D. 4-(2,4-Dichloropyrido[4,3-d]pyrimidin-7-yl)naphthalen-2-yl pivalate. A mixture of 4-(2,4-dioxo-1,2,3,4-tetrahydropyrido[4,3-d]pyrimidin-7-yl)naphthalen-2-yl pivalate (104 mg, 0.240 mmol), phosphoryl trichloride (0.500 ml, 5.37 mmol) and N-ethyl-N-isopropylpropan-2-amine (0.209 ml, 1.20 mmol) was heated at 100° C. The reaction mixture was cooled to ambient temperature and concentrated in vacuo. The residue was partitioned between water (3 mL) and EtOAc (20 mL). The organic layer was dried over MgSO₄, filtered, and evaporated in vacuo. The residue was used without further purification. 4-(2,4-dichloropyrido[4,3-d]pyrimidin-7-yl)naphthalen-2-yl pivalate (70.0 mg, 0.168 mmol, 70%). LCMS (MM-ES+APCI, Pos): m/z 426.1 (100%)/428.1 (60%) (M, M+2).

Step E. tert-Butyl 3-(2-chloro-7-(3-(pivaloyloxy)naphthalen-1-yl)pyrido[4,3-d]pyrimidin-4-yl)-3,8-diazabicyclo[3.2.1]octane-8-carboxylate. A solution of 4-(2,4-dichloropyrido[4,3-d]pyrimidin-7-yl)naphthalen-2-yl pivalate (70.0 mg, 0.164 mmol), N-ethyl-N-isopropylpropan-2-amine (42.4 mg, 0.328 mmol) and tert-butyl 3,8-diazabicyclo[3.2.1]octane-8-carboxylate (52.3 mg, 0.246 mmol) in N,N-dimethylacetamide (1.00 ml) was stirred at ambient temperature for 2 h. The solvent was removed in vacuo and the residue was partitioned between EtOAc and 10% NaHCO₃. The organic layer was washed with brine, dried and concentrated. The residue was purified by flash chromatography eluting with 20-50% EtOAc/hexanes to give tert-butyl 3-(2-chloro-7-(3-(pivaloyloxy)naphthalen-1-yl)pyrido[4,3-d]pyrimidin-4-yl)-3,8-diazabicyclo[3.2.1]octane-8-carboxylate (22.0 mg, 0.037 mmol, 22.3%). LCMS (MM-ES+APCI, Pos): m/z 602.3 (100%)/604.3 (30%) (M, M+2).

Step F. tert-Butyl (1R,5S)-3-(7-(3-hydroxynaphthalen-1-yl)-2-(((S)-1-methylpyrrolidin-2-yl)methoxy)pyrido[4,3-d]pyrimidin-4-yl)-3,8-diazabicyclo[3.2.1]octane-8-carboxylate. A mixture of tert-butyl 3-(2-chloro-7-(3-(pivaloyloxy) naphthalen-1-yl)pyrido[4,3-d]pyrimidin-4-yl)-3,8-diazabicyclo[3.2.1]octane-8-carboxylate (22.0 mg, 0.037 mmol), (S)-(1-methylpyrrolidin-2-yl)methanol (13.0 mg, 0.110 mmol), Cs$_2$CO$_3$ (36.0 mg, 0.11 mmol) in dioxane (0.500 mL) was sparged with argon and heated at 80° C. for 5 h. The reaction mixture was cooled to ambient temperature and partitioned between EtOAc and water. The organic phase was washed with water, brine, dried over Na$_2$SO$_4$ and concentrated in vacuo. The residue was purified by flash chromatography eluting with 5% MeOH+0.5% NH$_4$OH/CH$_2$Cl$_2$ to afford the desired product (11.0 mg 0.018 mmol, 50.0%). LCMS (MM-ES+APCI, Pos): m/z 597.4 (M+H).

Step G. 4-(4-((1R,5S)-3,8-Diazabicyclo[3.2.1]octan-3-yl)-2-(((S)-1-methylpyrrolidin-2-yl)methoxy)pyrido[4,3-d]pyrimidin-7-yl)naphthalen-2-ol tris-hydrochloride salt. To a stirred solution of tert-butyl 3-(7-(3-hydroxynaphthalen-1-yl)-2-(((S)-1-methylpyrrolidin-2-yl)methoxy)pyrido[4,3-d]pyrimidin-4-yl)-3,8-diazabicyclo[3.2.1]octane-8-carboxylate (11.0 mg, 0.018 mmol) in CH$_2$Cl$_2$ (0.500 mL), was added cold 4N HCl in dioxane (922 µL, 3.69 mmol) and the reaction mixture was stirred at ambient temperature for 2 h, and then concentrated in vacuo to afford 4-(4-((1R,5S)-3,8-diazabicyclo[3.2.1]octan-3-yl)-2-(((S)-1-methylpyrrolidin-2-yl)methoxy)pyrido[4,3-d]pyrimidin-7-yl)naphthalen-2-ol tris-hydrochloride salt (11.0 mg, 0.018 mmol, 100%). LCMS (MM-ES+APCI, Pos): m/z 497.3 (M+H).

Example 2

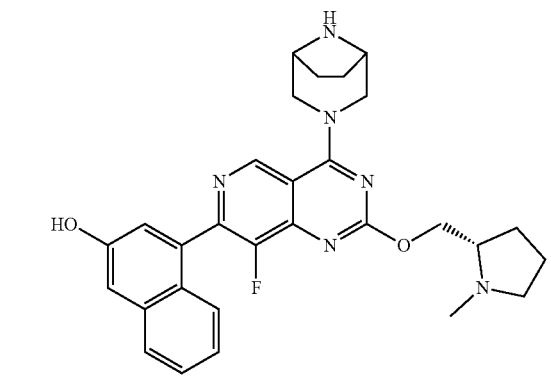 [SMILES: CN1CCC[C@H]1COc1nc(N2CC3CCC(C2)N3)c2cnc(-c3cc(O)cc4ccccc34)c(F)c2n1]

4-(4-((1R,5S)-3,8-diazabicyclo[3.2.1]octan-3-yl)-8-fluoro-2-(((S)-1-methylpyrrolidin-2-yl)methoxy) pyrido[4,3-d]pyrimidin-7-yl)naphthalen-2-ol bis(2,2,2-trifluoroacetate)

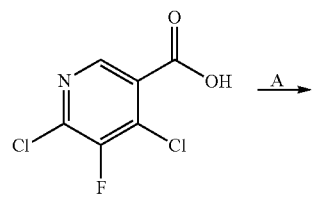

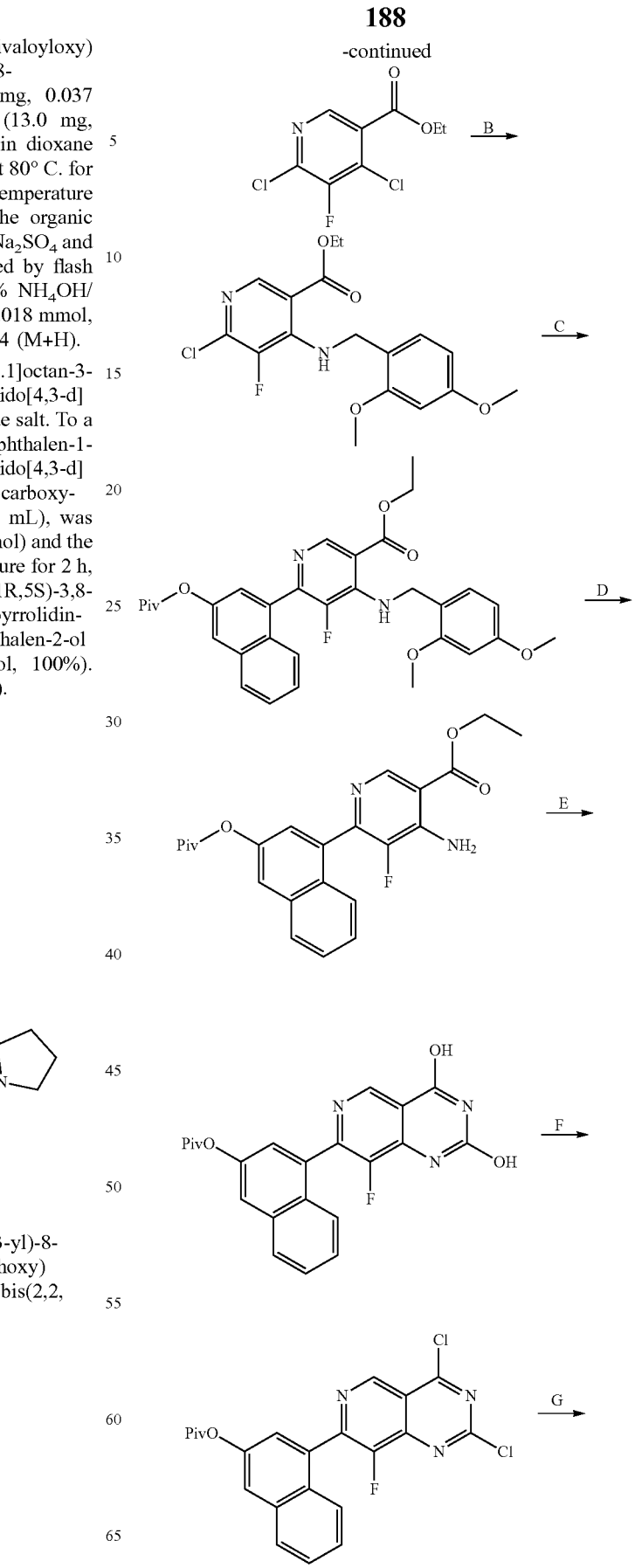

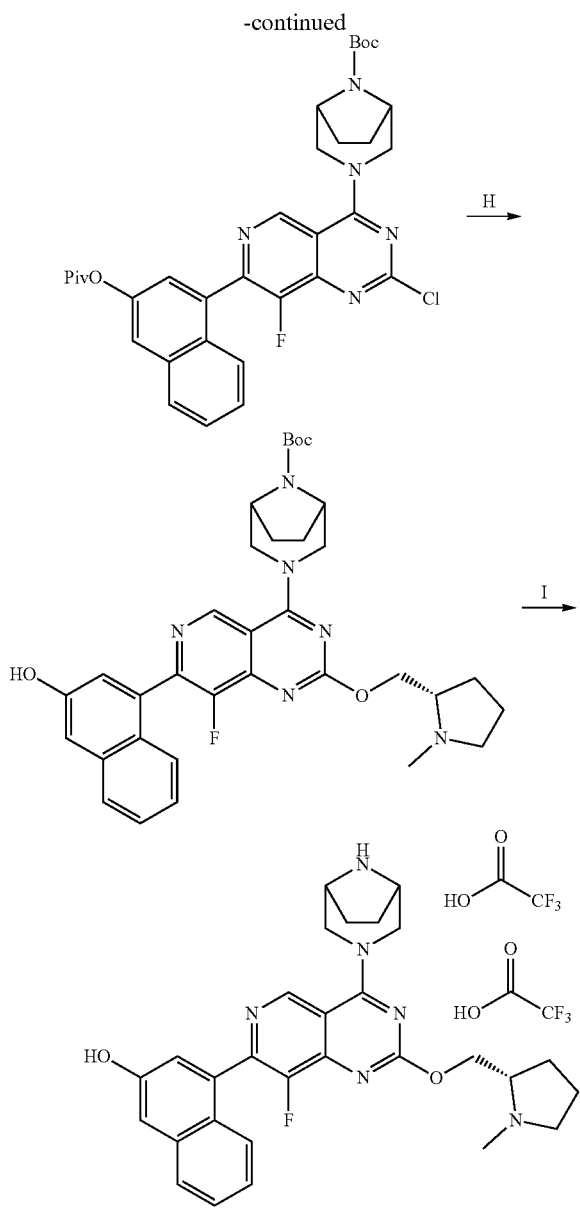

Step A. Ethyl 4,6-dichloro-5-fluoronicotinate. A solution of 4,6-dichloro-5-fluoro-3-pyridinecarboxylic acid (10.0 g, 47.6 mmol) in ethanol (238 ml, 47.6 mmol) was heated at 80° C. and thionyl chloride (6.95 ml, 95.2 mmol) was added dropwise through the condenser. The mixture was stirred at 65° C. overnight. The reaction was concentrated in vacuo and the residue was partitioned between EtOAc/water. The organic layer was washed with NaHCO$_3$, dried and concentrated to give a residue that was purified by flash chromatography eluting with a 0-100 ethyl acetate/hexanes gradient. The product fractions were collected and concentrated to give the desired product (9.61 g, 40.4 mmol, 85%). LCMS (MM-ES+APCI, Pos): m/z 237.9 (100%), 240.1 (50%) (M, M+2).

Step B. Ethyl 6-chloro-4-((2,4-dimethoxybenzyl)amino)-5-fluoronicotinate. To a mixture of ethyl 4,6-dichloro-5-fluoronicotinate (750 mg, 3.15 mmol) and N-ethyl-N-isopropylpropan-2-amine (1.38 ml, 7.88 mmol) in dioxane (15.8 ml, 3.15 mmol) was added 2,4-dimethoxybenzylamine (521 µL, 3.47 mmol) and the mixture heated at 40° C. for 18 h. The mixture was diluted with EtOAc and water and the layers were separated. The aqueous layer was extracted with EtOAc (3×). The combined organic layers were dried over Na$_2$SO$_4$, filtered, and concentrated. The residue was purified by flash chromatography eluting with 0-25% EtOAc/hexanes to give ethyl 6-chloro-4-((2,4-dimethoxybenzyl)amino)-5-fluoronicotinate (862 mg, 2.34 mmol, 74% yield). LCMS (MM-ES+APCI, Pos): m/z 369.1 (M+H).

Step C. Ethyl 4-((2,4-dimethoxybenzyl)amino)-5-fluoro-6-(3-(pivaloyloxy)naphthalen-1-yl)nicotinate. To a solution of ethyl 6-chloro-4-((2,4-dimethoxybenzyl)amino)-5-fluoronicotinate (0.862 g, 2.34 mmol) in dioxane (11.7 ml) were added potassium carbonate (2.0 M, 5.84 ml, 11.7 mmol) and 4-(4,4,5,5-tetramethyl-1,3,2-dioxaborolan-2-yl)naphthalen-2-yl pivalate (1.04 g, 2.92 mmol), and the reaction mixture was sparged with argon followed by addition of Pd$_2$dba$_3$ (0.080 g, 0.088 mmol) and 2-(dicyclohexylphosphino)-2',4',6'-tri-1-propyl-1,1'-biphenyl (0.084 g, 0.175 mmol) (XPhos). The mixture was heated at 80° C. for 5 h. The reaction was filtered through Celite, diluted with EtOAc and the organic layer was washed with water, brine, dried over Na$_2$SO$_4$ and concentrated in vacuo. The residue was purified by flash chromatography eluting with 0-25% EtOAc/hexanes as eluent to give ethyl 4-((2,4-dimethoxybenzyl)amino)-5-fluoro-6-(3-(pivaloyloxy)naphthalen-1-yl)nicotinate (835 mg, 1.49 mmol, 64% yield). LCMS (MM-ES+APCI, Pos): m/z 561.2 (M+H).

Step D. Ethyl 4-amino-5-fluoro-6-(3-(pivaloyloxy)naphthalen-1-yl)nicotinate. A mixture of ethyl 4-((2,4-dimethoxybenzyl)amino)-5-fluoro-6-(3-(pivaloyloxy)naphthalen-1-yl)nicotinate (810 mg, 1.44 mmol) in CH$_2$Cl$_2$ (14.4 ml) was treated with TFA (1.11 ml, 14.4 mmol) at 0° C. After stirring at RT for 1 h, the reaction mixture was diluted with a solution of saturated NaHCO$_3$, extracted with EtOAc. The organic layer was dried over Mg$_2$SO$_4$, filtered, and concentrated in vacuo to give ethyl 4-amino-5-fluoro-6-(3-(pivaloyloxy)naphthalen-1-yl)nicotinate (528 mg, 1.29 mmol, 89% yield). LCMS (MM-ES+APCI, Pos): m/z 411.2 (M+H).

Step E. 4-(8-fluoro-2,4-dioxo-1,2,3,4-tetrahydropyrido[4,3-d]pyrimidin-7-yl)naphthalen-2-yl pivalate. To a solution of ethyl 4-amino-5-fluoro-6-(3-(pivaloyloxy)naphthalen-1-yl)nicotinate (1.33 g, 3.24 mmol) in THF (6.48 ml, 3.24 mmol) at 0° C. was added trichloroacetyl isocyanate (0.461 ml, 3.89 mmol). The mixture was stirred at rt for 2 h. The solvent was removed in vacuo and MeOH (16.2 ml, 3.24 mmol) and ammonia (16.2 ml, 3.24 mmol) (7M in MeOH) were added to the residue. The mixture was heated at 70° C. for 2 h. The solvent was removed in vacuo (no heat). The residue was diluted with CH$_2$Cl$_2$ and solids was removed by filtration to afford the first crop of product (941 mg). The filtrate was purified by flash chromatography eluting with 0-100% EtOAc/hexanes to give 202 mg more product. 4-(8-fluoro-2,4-dioxo-1,2,3,4-tetrahydropyrido[4,3-d]pyrimidin-7-yl)naphthalen-2-yl pivalate (total 1.14 g, 1.96 mmol, 60.4% yield). LCMS (MM-ES+APCI, Pos): m/z 408.1 (M+H).

Step F. 4-(2,4-dichloro-8-fluoropyrido[4,3-d]pyrimidin-7-yl)naphthalen-2-yl pivalate. A mixture of 4-(8-fluoro-2,4-dihydroxypyrido[4,3-d]pyrimidin-7-yl)naphthalen-2-yl pivalate (162 mg, 0.278 mmol) in phosphorous oxychloride (1.39 ml, 0.278 mmol) was treated with N-ethyl-N-isopropylpropan-2-amine (139 µL, 0.278 mmol). The mixture was stirred at 110° C. for 18 h. The mixture was evaporated in vacuo. The residue was dissolved with CH$_2$Cl$_2$ and washed with NaHCO$_3$ (sat. aq.), and the layers were separated. The organics were filtered and concentrated in vacuo to give 4-(2,4-dichloro-8-fluoropyrido[4,3-d]pyrimidin-7-yl)naphthalen-2-yl pivalate (149 mg, 0.168 mmol, 60.2% yield, used crude). LCMS (MM-ES+APCI, Pos): m/z 444.1 (100%), 446 (70%) (M, M+2).

Step G. tert-butyl (1R,5S)-3-(2-chloro-8-fluoro-7-(3-(pivaloyloxy)naphthalen-1-yl)pyrido[4,3-d]pyrimidin-4-yl)-3,8-diazabicyclo[3.2.1]octane-8-carboxylate. A mixture of 4-(2, 4-dichloro-8-fluoropyrido[4,3-d]pyrimidin-7-yl) naphthalen-2-yl pivalate (149 mg, 0.302 mmol) and 8-boc-3,8-diazabicyclo[3.2.1]octane (51.3 mg, 0.241 mmol) in DMA (1.51 mL) was treated with N-ethyl-N-isopropylpropan-2-amine (264 µL, 1.51 mmol) at RT. The mixture was stirred at RT for 18 h. The mixture was diluted with water and the aqueous layer extracted with EtOAc (3×). The combined organic layers were filtered and concentrated in vacuo. The residue was purified by flash chromatography eluting with 0-20% EtOAc/hexanes to give tert-butyl (1R, 5S)-3-(2-chloro-8-fluoro-7-(3-(pivaloyloxy)naphthalen-1-yl)pyrido[4,3-d]pyrimidin-4-yl)-3,8-diazabicyclo[3.2.1]octane-8-carboxylate (77.0 mg, 0.124 mmol, 41% yield). LCMS (MM-ES+APCI, Pos): m/z 620.2 (100%), 621.3 (40%) (M, M+2).

Step H. tert-butyl (1R,5S)-3-(8-fluoro-7-(3-hydroxynaphthalen-1-yl)-2-(((S)-1-methylpyrrolidin-2-yl)methoxy)pyrido[4,3-d]pyrimidin-4-yl)-3,8-diazabicyclo[3.2.1]octane-8-carboxylate. A mixture of tert-butyl (1R,5S)-3-(2-chloro-8-fluoro-7-(3-(pivaloyloxy)naphthalen-1-yl)pyrido [4,3-d]pyrimidin-4-yl)-3,8-diazabicyclo[3.2.1]octane-8-carboxylate (77 mg, 0.12 mmol) and dioxane (1.24 ml) was treated with (S)-(1-methylpyrrolidin-2-yl)methanol (21.0 mg, 0.18 mmol) and Cs$_2$CO$_3$ (81.0 mg, 0.250 mmol) at RT. The mixture was stirred at 70° C. for 18 h. The mixture was diluted with NaHCO$_3$ (sat. aq.) and then extracted with EtOAc. The organic layer was filtered and concentrated in vacuo. The residue was purified by flash chromatography eluting with 0-20% MeOH/CH$_2$Cl$_2$+0.25% NH$_4$OH to give tert-butyl (1R,5S)-3-(8-fluoro-7-(3-hydroxynaphthalen-1-yl)-2-(((S)-1-methylpyrrolidin-2-yl)methoxy)pyrido[4,3-d] pyrimidin-4-yl)-3,8-diazabicyclo[3.2.1]octane-8-carboxylate (17.0 mg, 0.022 mmol, 18% yield). LCMS (MM-ES+APCI, Pos): m/z 615.3 (100%) (M+H).

Step I. 4-(4-((1R,5S)-3,8-diazabicyclo[3.2.1]octan-3-yl)-8-fluoro-2-(((S)-1-methylpyrrolidin-2-yl)methoxy)pyrido [4,3-d]pyrimidin-7-yl)naphthalen-2-ol bis(2,2,2-trifluoroacetate). To a solution of tert-butyl (1R,5S)-3-(8-fluoro-7-(3-hydroxynaphthalen-1-yl)-2-(((S)-1-methylpyrrolidin-2-yl) methoxy)pyrido[4,3-d]pyrimidin-4-yl)-3,8-diazabicyclo [3.2.1]octane-8-carboxylate (10.0 mg, 0.016 mmol) in CH$_2$Cl$_2$ (163 µL) was added TFA (13.0 µL, 0.160 mmol) at 0° C. The mixture was stirred at r.t. for 2 h. The reaction mixture was concentrated in vacuo and the residue was purified by preparative C18 HPLC (Gilson, 5-95% CH$_3$CN/ H$_2$O with 0.1% TFA) to afford 4-(4-((1R,5S)-3,8-diazabicyclo[3.2.1]octan-3-yl)-8-fluoro-2-(((S)-1-methylpyrrolidin-2-yl)methoxy)pyrido[4,3-d]pyrimidin-7-yl)naphthalen-2-ol bis(2,2,2-trifluoroacetate) (9.00 mg, 0.012 mmol, 74% yield). LCMS (MM-ES+APCI, Pos): m/z 515.2 (100%) (M+H).

Example 3

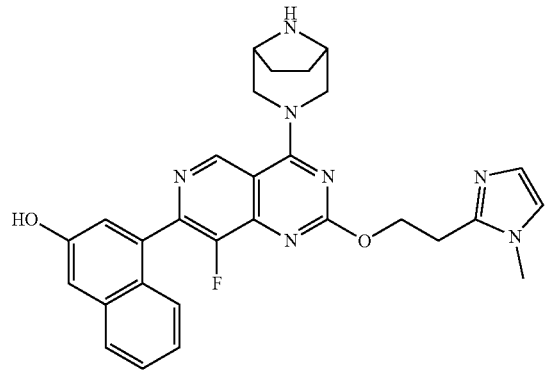 [SMILES: Cn1ccnc1CCOc1nc(N2CC3CCC(C2)N3)c2cnc(-c3cc(O)cc4ccccc34)c(F)c2n1]

4-(4-((1R,5S)-3,8-diazabicyclo[3.2.1]octan-3-yl)-8-fluoro-2-(2-(1-methyl-1H-imidazol-2-yl)ethoxy) pyrido[4,3-d]pyrimidin-7-yl)naphthalen-2-ol

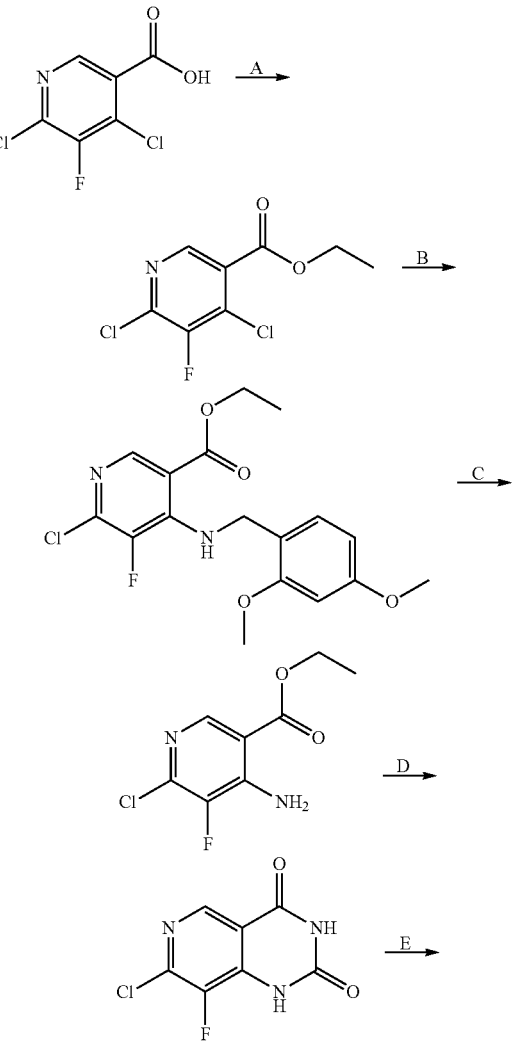

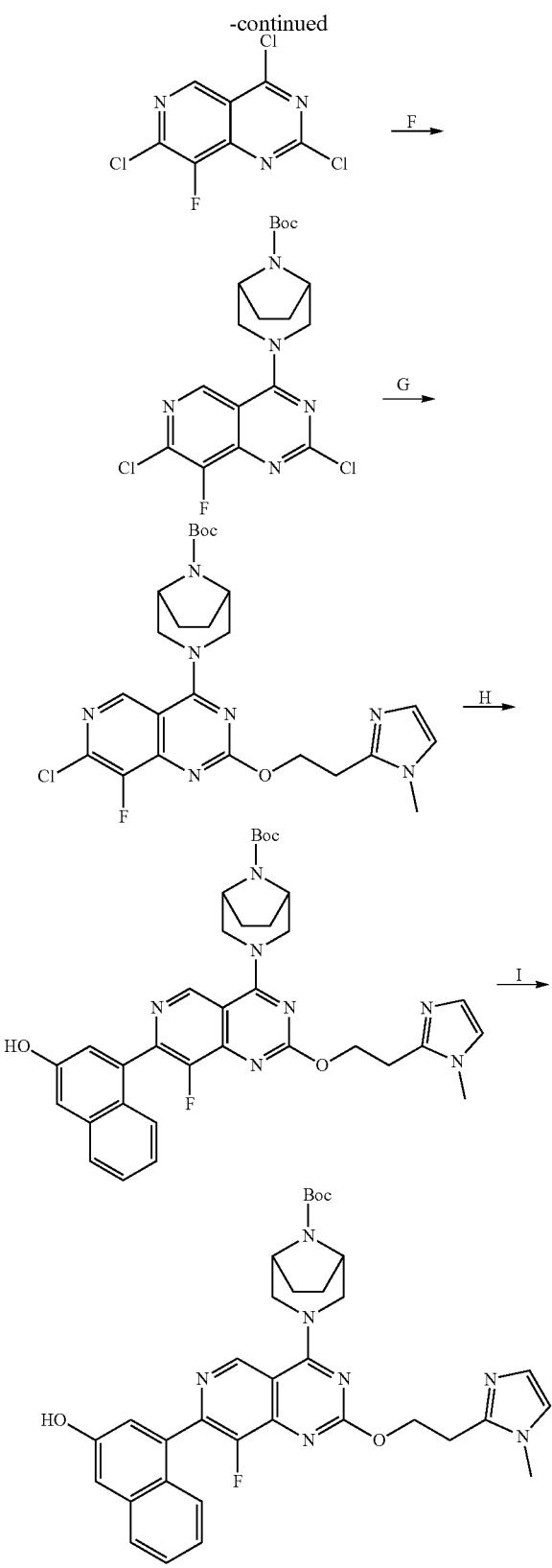

Step A. Ethyl 4,6-dichloro-5-fluoronicotinate: A solution of 4,6-dichloro-5-fluoro-3-pyridinecarboxylic acid, (50 g, 238 mmol) in ethanol (1191 mL) was heated at 80° C. and thionyl chloride (34.8 mL, 476 mmol) was added dropwise. The mixture was stirred at 65° C. then cooled and concentrated in vacuo. The residue was partitioned between EtOAc and water and the organic phase was washed with sat. NaHCO₃, dried over Na₂SO₄, filtered and concentrated to afford ethyl 4,6-dichloro-5-fluoronicotinate (50.4 g, 890% yield). LCMS (MM-ES+APC, Pos): m/z 248.1 (M+H).

Step B. Ethyl 6-chloro-4-((2,4-dimethoxybenzyl)amino)-5-fluoronicotinate: To a mixture of ethyl 4,6-dichloro-5-fluoronicotinate (50.4 g, 212 mmol) and N-ethyl-N-isopropylpropan-2-amine (92.4 mL, 529 mmol) in dioxane (605 mL) was added 2,4-dimethoxybenzylamine (35.0 mL, 233 mmol) and the mixture stirred at 50° C. for 18 h. The mixture was partitioned between EtOAc and water and the aqueous layer extracted with EtOAc (2×). The combined organic phases were filtered, dry loaded onto silica gel and purified by flash column chromatography eluting with 0-50%0 EtOAc/hexanes to afford ethyl 6-chloro-4-((2,4-dimethoxybenzyl)amino)-5-fluoronicotinate (55.0 g, 700% yield). LCMS (MM-ES+APCI, Pos): m/z 369.1 (M+H).

Step C. Ethyl 4-amino-6-chloro-5-fluoronicotinate: A solution of ethyl 6-chloro-4-((2,4-dimethoxybenzyl)amino)-5-fluoronicotinate (1.06 g, 2.87 mmol) in CH₂Cl₂ (19.2 mL) at 0° C. was treated dropwise with TFA (4.43 mL, 57.5 mmol). The mixture was stirred for 45 min, then diluted with CH₂Cl₂ (30.0 mL), and treated with 1M K₃PO₄ (30.0 mL). The mixture was filtered through GF paper and the filtrate layers were separated. The aqueous layer was extracted with CH₂Cl₂ (2×20 mL) and the combined organic phases were washed with brine (20 mL), dried over Na₂SO₄, filtered and concentrated to afford ethyl 4-amino-6-chloro-5-fluoronicotinate (657 mg, 105% yield) as a white solid. LCMS (MM-ES+APCI, Pos): m/z 219.0 (M+H).

Step D. 7-Chloro-8-fluoropyrido[4,3-d]pyrimidine-2,4(1H,3H)-dione: To a suspension of ethyl 4-amino-6-chloro-5-fluoronicotinate (628 mg, 2.87 mmol) in THF (6 mL) cooled to 0° C. was added trichloroacetyl isocyanate (0.410 mL, 3.45 mmol). The mixture was stirred at rt for 30 min then concentrated in vacuo. The residue was suspended in MeOH (14.4 mL), cooled to 0° C. and treated with ammonia (7M in MeOH, 14.4 mL, 101 mmol). The mixture was stirred at rt for 16 h. The solids were filtered, washed with methanol and dried in vacuo to afford 7-chloro-8-fluoropyrido[4,3-d]pyrimidine-2,4 (1H,3H)-dione (656 mg, 106% yield) as a white solid.

Step E. 2,4,7-Trichloro-8-fluoropyrido[4,3-d]pyrimidine: A mixture of 7-chloro-8-fluoropyrido[4,3-d]pyrimidine-2,4-diol (663 mg, 3.08 mmol) in phosphorous oxychloride (15.4 mL, 3.08 mmol) was treated with N-ethyl-N-isopropylpropan-2-amine (1.54 mL, 3.08 mmol). The mixture was heated to 110° C. where it stirred for 18 h. The cooled mixture was concentrated in vacuo. The residue was dissolved in CH₂Cl₂ and washed with water (3×) and sat. NaHCO₃. The organic layer was filtered and concentrated in vacuo to afford 2,4,7-trichloro-8-fluoropyrido[4,3-d]pyrimidine (656 mg, 2.60 mmol, 85% yield). LCMS (MM-ES+APCI, Pos): m/z 219.0 (M+H).

Step F. tert-Butyl (1R,5S)-3-(2,7-dichloro-8-fluoropyrido[4,3-d]pyrimidin-4-yl)-3,8-diazabicyclo[3.2.1]octane-8-carboxylate: A solution of 2,4,7-trichloro-8-fluoropyrido[4,3-d]pyrimidine (254 mg, 0.500 mmol) in DMA (2.5 mL) at 0° C. was treated with 8-Boc-3,8-diazabicyclo[3.2.1]octane (85.4 mg, 0.400 mmol) and N-ethyl-N-isopropylpropan-2-amine (439 µL, 2.52 mmol). The mixture was stirred at rt for 1 h, and then partitioned between EtOAc and water. The aqueous layer was extracted with EtOAc (2×) and the combined organic phases were filtered and concentrated in vacuo. The residue was purified by flash column chromatography eluting with 0-50% EtOAc/hexanes to afford tert-butyl (1R,5S)-3-(2,7-dichloro-8-fluoropyrido[4,3-d]pyrimidin-4-yl)-3,8-diazabicyclo[3.2.1]octane-8-carboxylate (110 mg, 51% yield). LCMS (MM-ES+APCI, Pos): m/z 429.1 (M+H).

Step G. tert-butyl (1R,5S)-3-(7-chloro-8-fluoro-2-(2-(1-methyl-1H-imidazol-2-yl)ethoxy)pyrido[4,3-d]pyrimidin-4-yl)-3,8-diazabicyclo[3.2.1]octane-8-carboxylate: A mixture of tert-butyl (1R,5S)-3-(2,7-dichloro-8-fluoropyrido[4,3-d]pyrimidin-4-yl)-3,8-diazabicyclo[3.2.1]octane-8-carboxylate (50.0 mg, 0.117 mmol) in dioxane (11.7 mL) was treated with 2-(1-methyl-1H-imidazol-2-yl)ethan-1-ol (29.5 mg, 0.233 mmol) and Cs$_2$CO$_3$ (114 mg, 0.350 mmol) and stirred at 70° C. for 18 h. The mixture was diluted with brine (40 mL) and extracted with EtOAc (3×20 mL). The combined organic layers were dried over Na$_2$SO$_4$, filtered, and concentrated in vacuo. The residue was purified by flash column chromatography eluting with 0-5% MeOH/CH$_2$Cl$_2$ to afford tert-butyl (1R,5S)-3-(7-chloro-8-fluoro-2-(2-(1-methyl-1H-imidazol-2-yl)ethoxy)pyrido[4,3-d]pyrimidin-4-yl)-3,8-diazabicyclo[3.2.1]octane-8-carboxylate (34.3 mg, 57% yield) as a yellow solid. LCMS (MM-ES+APCI, Pos): m/z 518.2 (M+H).

Step H. tert-Butyl (1R,5S)-3-(7-chloro-8-fluoro-2-(2-(1-methyl-1H-imidazol-2-yl)ethoxy)pyrido[4,3-d]pyrimidin-4-yl)-3,8-diazabicyclo[3.2.1]octane-8-carboxylate: A mixture of 4-(4,4,5,5-tetramethyl-1,3,2-dioxaborolan-2-yl)naphthalen-2-ol (26.8 mg, 0.099 mmol), tert-butyl (1R,5S)-3-(7-chloro-8-fluoro-2-(2-(1-methyl-1H-imidazol-2-yl)ethoxy)pyrido[4,3-d]pyrimidin-4-yl)-3,8-diazabicyclo[3.2.1]octane-8-carboxylate (34.3 mg, 0.066 mmol), K$_2$CO$_3$ (0.099 mL, 2.00 M, 0.200 mmol) and Pd(PPh$_3$)$_4$ (7.65 mg, 0.007 mmol) in dioxane (662 µL) was sparged with argon and heated at 85° C. for 18 hr then stirred at rt for 48 h. The mixture was diluted with water (30 mL) and extracted with EtOAc (3×15 mL). The combined organic layers were washed with brine (20 mL), dried over Na$_2$SO$_4$, filtered and concentrated in vacuo. The residue was purified by flash column chromatography eluting with 15-100% EtOAc/hexanes then again eluting with 0-10% MeOH/CH$_2$Cl$_2$ to afford tert-butyl (1R,5S)-3-(7-chloro-8-fluoro-2-(2-(1-methyl-1H-imidazol-2-yl)ethoxy)pyrido[4,3-d]pyrimidin-4-yl)-3,8-diazabicyclo[3.2.1]octane-8-carboxylate (23.7 mg, 57% yield). LCMS (MM-ES+APCI, Pos): m/z 626.3 (M+H).

Step I. 4-(4-((1R,5S)-3,8-diazabicyclo[3.2.1]octan-3-yl)-8-fluoro-2-(2-(1-methyl-1H-imidazol-2-yl)ethoxy)pyrido[4,3-d]pyrimidin-7-yl)naphthalen-2-ol: To a solution of tert-butyl (1R,5S)-3-(8-fluoro-7-(3-hydroxynaphthalen-1-yl)-2-(2-(1-methyl-1H-imidazol-2-yl)ethoxy)pyrido[4,3-d]pyrimidin-4-yl)-3,8-diazabicyclo[3.2.1]octane-8-carboxylate (23.7 mg, 0.038 mmol) in CH$_2$Cl$_2$ (0.760 mL) at 0° C. was added TFA (58.4 µL, 0.758 mmol). The mixture was stirred at rt for 2 h, and then TFA (58.4 µL, 0.758 mmol) was added. After stirring for a further 2 h the solution was poured into a mixture of sat. NaHCO$_3$ (20 mL) and EtOAc (15 mL). The aqueous layer was extracted with EtOAc (2×15 mL) and the combined organic layers were washed with brine (15 mL), dried over Na$_2$SO$_4$, filtered and concentrated in vacuo. The residue was purified by flash column chromatography eluting with a 0-20% MeOH/CH$_2$Cl, 2% NH$_4$OH then by Gilson prep HPLC (0-95% ACN/water/0.1% TFA over 20 min). Pure fractions were added to a mixture of sat. NaHCO$_3$ (20 mL) and EtOAc (15 mL). The aqueous layer was extracted with EtOAc (2×15 mL) and the combined organic layers were washed with brine (15 mL), dried over Na$_2$SO$_4$, filtered and concentrated in vacuo to afford 4-(4-((1R,5S)-3,8-diazabicyclo[3.2.1]octan-3-yl)-8-fluoro-2-(2-(1-methyl-1H-imidazol-2-yl)ethoxy)pyrido[4,3-d]pyrimidin-7-yl)naphthalen-2-ol (9 mg, 43% yield) as a beige film. LCMS (MM-ES+APCI, Pos): m/z 526.2 (M+H).

Example 4

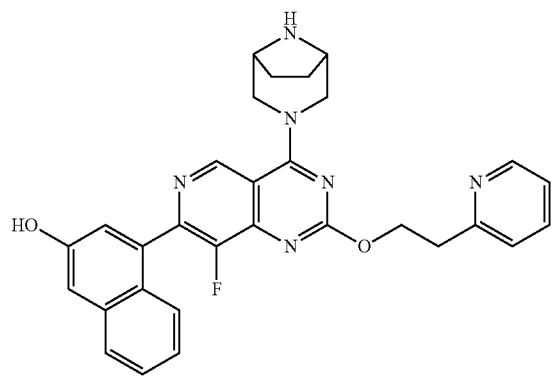 [SMILES: Oc1cc(-c2ncc3c(N4CC5CCC(C4)N5)nc(OCCc4ccccn4)nc3c2F)c2ccccc2c1]

4-(4-((1R,5S)-3,8-diazabicyclo[3.2.1]octan-3-yl)-8-fluoro-2-(2-(pyridin-2-yl)ethoxy)pyrido[4,3-d]pyrimidin-7-yl)naphthalen-2-ol Synthesized according to Example 3, Steps G-I substituting 2-(pyridin-2-yl)ethan-1-ol in place of 2-(1-methyl-1H-imidazol-2-yl)ethan-1-ol (28.1 mg, 64%). LCMS (MM-ES+APCI, Pos): m/z 523.2 (M+H).

Example 5

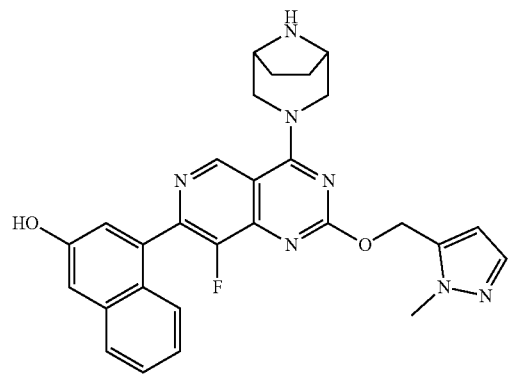 [SMILES: Cn1nccc1COc1nc(N2CC3CCC(C2)N3)c2cnc(-c3cc(O)cc4ccccc34)c(F)c2n1]

4-(4-((1R,5S)-3,8-diazabicyclo[3.2.1]octan-3-yl)-8-fluoro-2-((1-methyl-1H-pyrazol-5-yl)methoxy)pyrido[4,3-d]pyrimidin-7-yl)naphthalen-2-ol Synthesized according to Example 3, Steps G-I substituting (1-methyl-1H-pyrazol-5-yl)methanol in place of 2-(1-methyl-1H-imidazol-2-yl)ethan-1-ol (23.7 mg, 63%). LCMS (MM-ES+APCI, Pos): m/z 512.2 (M+H).

Example 6

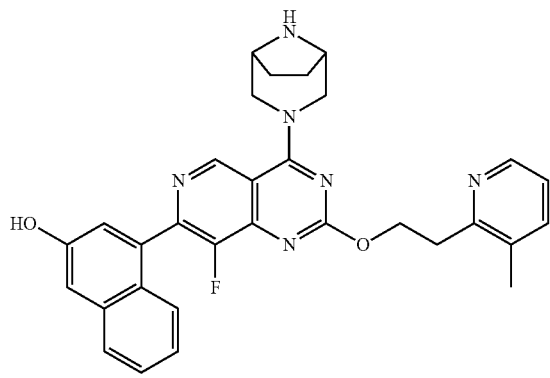 [SMILES: Cc1cccnc1CCOc1nc(N2CC3CCC(C2)N3)c2cnc(-c3cc(O)cc4ccccc34)c(F)c2n1]

4-(4-((1R,5S)-3,8-diazabicyclo[3.2.1]octan-3-yl)-8-fluoro-2-(2-(3-methylpyridin-2-yl)ethoxy)pyrido[4,3-d]pyrimidin-7-yl)naphthalen-2-ol Synthesized according to Example 3, Steps G-I substituting 2-(3-methylpyridin-2-yl)ethan-1-ol in place of 2-(1-methyl-1H-imidazol-2-yl)ethan-1-ol (14.9 mg, 30%). LCMS (MM-ES+APCI, Pos): m/z 537.2 (M+H).

Example 8

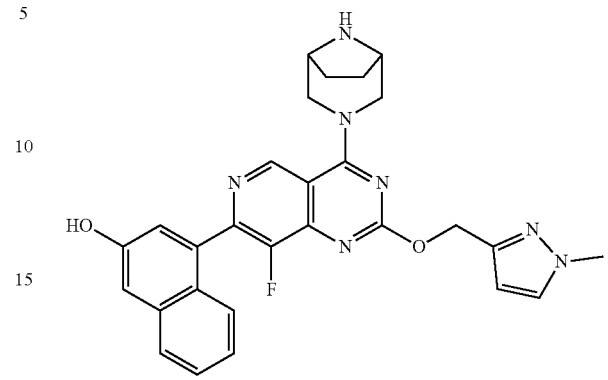

4-(4-((1R,5S)-3,8-diazabicyclo[3.2.1]octan-3-yl)-8-fluoro-2-((1-methyl-1H-pyrazol-3-yl)methoxy)pyrido[4,3-d]pyrimidin-7-yl)naphthalen-2-ol Synthesized according to Example 3, Steps G-I substituting (1-methyl-1H-pyrazol-3-yl)methanol in place of 2-(1-methyl-1H-imidazol-2-yl)ethan-1-ol (9.2 mg, 11%). LCMS (MM-ES+APCI, Pos): m/z 512.2 (M+H).

Example 7

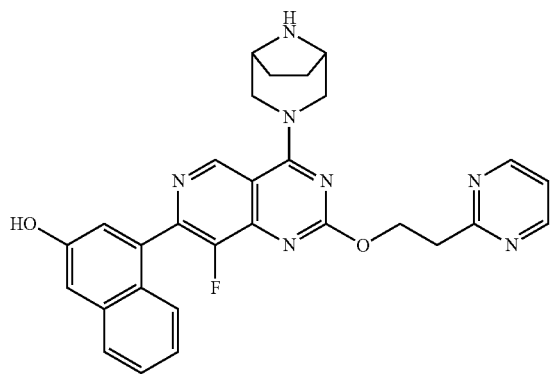 [SMILES: Oc1cc(-c2ncc3c(N4CC5CCC(C4)N5)nc(OCCc4ncccn4)nc3c2F)c2ccccc2c1]

4-(4-((1R,5S)-3,8-diazabicyclo[3.2.1]octan-3-yl)-8-fluoro-2-(2-(pyrimidin-2-yl)ethoxy)pyrido[4,3-d]pyrimidin-7-yl)naphthalen-2-ol Synthesized according to Example 3, Steps G-I substituting 2-(pyrimidin-2-yl)ethan-1-ol in place of 2-(1-methyl-1H-imidazol-2-yl)ethan-1-ol (7.1 mg, x mmol, 17%). LCMS (MM-ES+APCI, Pos): m/z 524.2 (M+H).

Example 9

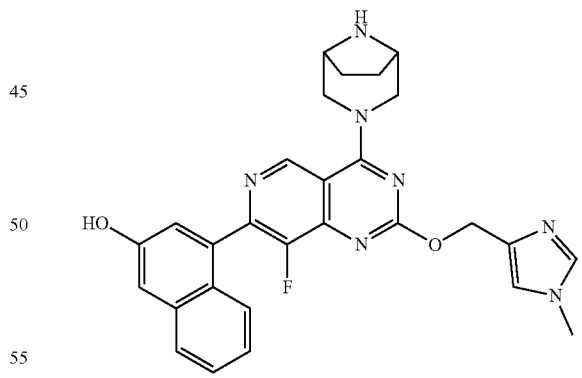

4-(4-((1R,5S)-3,8-diazabicyclo[3.2.1]octan-3-yl)-8-fluoro-2-((1-methyl-1H-imidazol-4-yl)methoxy)pyrido[4,3-d]pyrimidin-7-yl)naphthalen-2-ol Synthesized according to Example 3, Steps G-I substituting (1-methyl-1H-imidazol-4-yl)methanol in place of 2-(1-methyl-1H-imidazol-2-yl)ethan-1-ol (8.6 mg, 36%). LCMS (MM-ES+APCI, Pos): m/z 512.2 (M+H).

Example 10

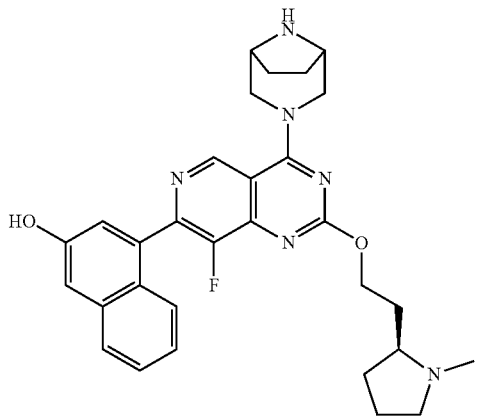 [SMILES: CN1CCC[C@H]1CCOc1nc(N2CC3CCC(C2)N3)c2cnc(-c3cc(O)cc4ccccc34)c(F)c2n1]

4-(4-((1R,5S)-3,8-diazabicyclo[3.2.1]octan-3-yl)-8-fluoro-2-(2-((S)-1-methylpyrrolidin-2-yl)ethoxy)pyrido[4,3-d]pyrimidin-7-yl)naphthalen-2-ol Synthesized similarly to Example 3, Steps G-I substituting (S)-2-(1-methylpyrrolidin-2-yl)ethanol in place of 2-(1-methyl-1H-imidazol-2-yl)ethan-1-ol (1.03 mg, 0.00195 mmol, 3.5%). LCMS (MMN-ES+APCI, Pos): m/z 529.3 (M+H).

Example 11

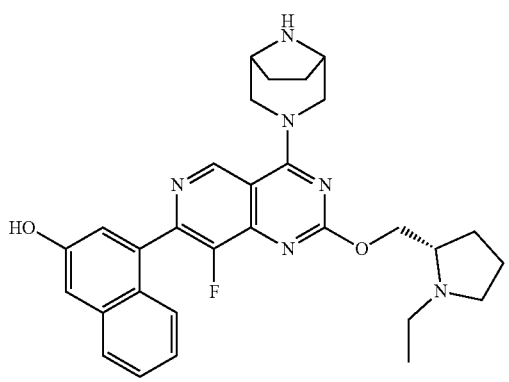 [SMILES: CCN1CCC[C@H]1COc1nc(N2CC3CCC(C2)N3)c2cnc(-c3cc(O)cc4ccccc34)c(F)c2n1]

4-(4-((1R,5S)-3,8-diazabicyclo[3.2.1]octan-3-yl)-2-(((S)-1-ethylpyrrolidin-2-yl)methoxy)-8-fluoro-pyrido[4,3-d]pyrimidin-7-yl)naphthalen-2-ol Synthesized similarly to Example 3, Steps G-I substituting [(2S)-1-Ethyl-2-pyrrolidinyl]methanol in place of 2-(1-methyl-1H-imidazol-2-yl)ethan-1-ol (1.38 mg, 0.00262 mmol, 2.4%). LCMS (MM-ES+APCI, Pos): m/z 529.3 (M+H).

Example 12

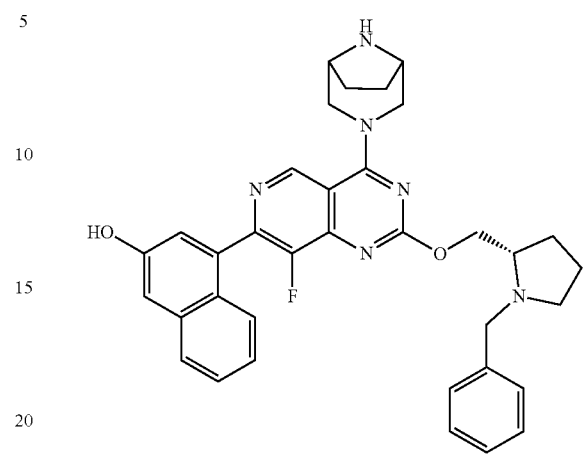

4-(2-(((S)-1-benzylpyrrolidin-2-yl)methoxy)-4-((1R,5S)-3,8-diazabicyclo[3.2.1]octan-3-yl)-8-fluoro-pyrido[4,3-d]pyrimidin-7-yl)naphthalen-2-ol Synthesized similarly to Example 3, Steps G-I substituting (S)-(−)-1-benzyl-2-pyrrolidinemethanol in place of 2-(1-methyl-1H-imidazol-2-yl)ethan-1-ol (2.67 mg, 0.00452 mmol, 10.4%). LCMS (MM-ES+APCI, Pos): m/z 591.2 (M+H).

Example 13

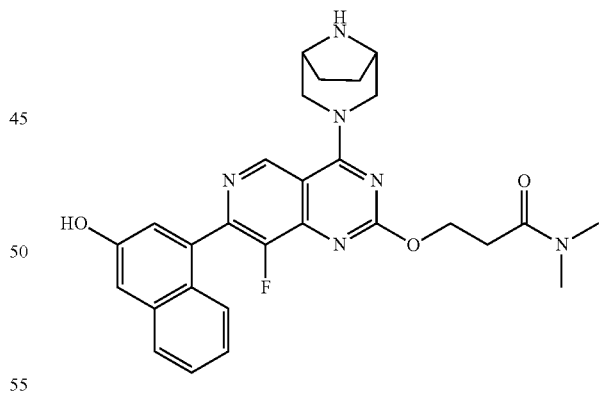

3-((4-((1R,5S)-3,8-diazabicyclo[3.2.1]octan-3-yl)-8-fluoro-7-(3-hydroxynaphthalen-1-yl)pyrido[4,3-d]pyrimidin-2-yl)oxy)-N,N-dimethylpropanamide Synthesized similarly to Example 3, Steps G-I substituting 3-hydroxy-N,N-dimethylpropanamide in place of 2-(1-methyl-1H-imidazol-2-yl)ethan-1-ol (0.885 mg, 0.00171 mmol, 3.52%). LCMS (MM-ES+APCI, Pos): m/z 517.2 (M+H).

201

Example 14

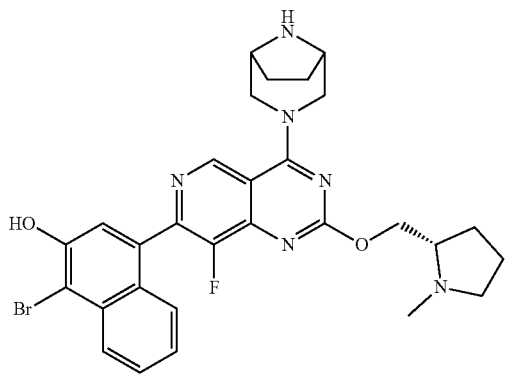 [SMILES: CN1CCC[C@H]1COc1nc(N2CC3CCC(C2)N3)c2cnc(-c3cc(O)c(Br)c4ccccc34)c(F)c2n1]

4-(4-(((1R,5S)-3,8-diazabicyclo[3.2.1]octan-3-yl)-8-fluoro-2-(((S)-1-methylpyrrolidin-2-yl)methoxy)pyrido[4,3-d]pyrimidin-7-yl)-1-bromonaphthalen-2-ol

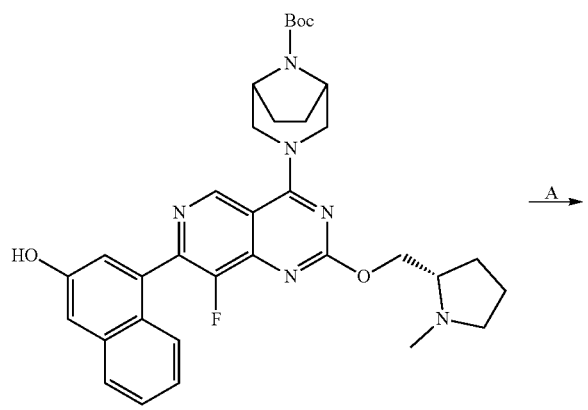

→ A

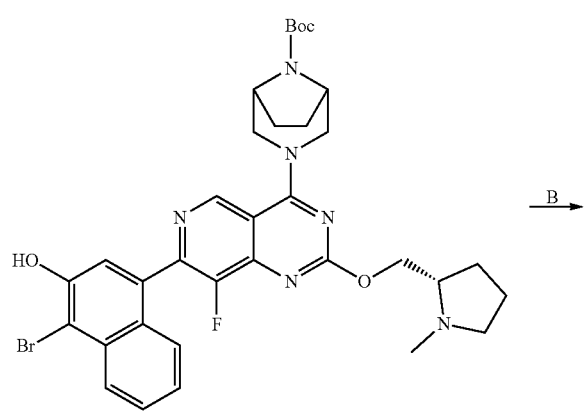

→ B

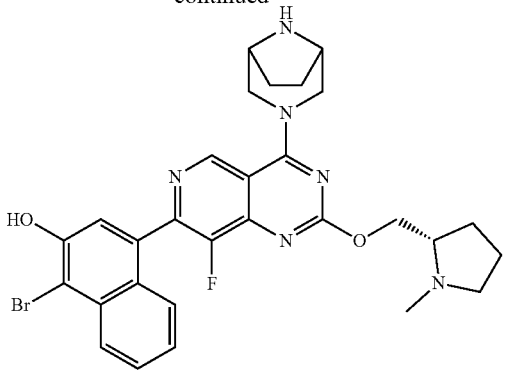

Step A. Tert-butyl (1R,5S)-3-(7-(4-bromo-3-hydroxynaphthalen-1-yl)-8-fluoro-2-(((S)-1-methylpyrrolidin-2-yl)methoxy)pyrido[4,3-d]pyrimidin-4-yl)-3,8-diazabicyclo[3.2.1]octane-8-carboxylate. To a solution of tert-butyl (1R,5S)-3-(8-fluoro-7-(3-hydroxynaphthalen-1-yl)-2-(((S)-1-methylpyrrolidin-2-yl)methoxy)pyrido[4,3-d]pyrimidin-4-yl)-3,8-diazabicyclo[3.2.1]octane-8-carboxylate (79.0 mg, 0.130 mmol, synthesis in Example 2) in DMF was added N-bromosuccinimide (27.0 mg, 0.150 mmol). The solution was stirred at rt for 5 hours. Water was added to the reaction and the mixture was extracted two times with ethyl acetate. Pooled organic layers were washed three times with water, dried over magnesium sulfate, filtered, and concentrated. Crude product was purified by silica gel column (24 g, 0 to 20% MeOH/DCM) to give the desired product (36.0 mg, 0.052 mmol, 40%). LCMS (MM-ES+APCI, Pos): m/z 693.2 (M+H).

Step B. 4-(4-((1R,5S)-3,8-diazabicyclo[3.2.1]octan-3-yl)-8-fluoro-2-(((S)-1-methylpyrrolidin-2-yl)methoxy)pyrido[4,3-d]pyrimidin-7-yl)-1-bromonaphthalen-2-ol. To a 0° C. solution of tert-butyl (1R,5S)-3-(7-(4-bromo-3-hydroxynaphthalen-1-yl)-8-fluoro-2-(((S)-1-methylpyrrolidin-2-yl)methoxy)pyrido[4,3-d]pyrimidin-4-yl)-3,8-diazabicyclo[3.2.1]octane-8-carboxylate (36 mg, 0.052 mmol) in DCM (1.04 ml) was added TFA (160 μL, 2.08 mmol) and the reaction was stirred at 0° C. for 15 min. The reaction was warmed to rt and stirred for several hours. The reaction mixture was concentrated in vacuo. The residue was purified by silica gel column eluting with 10 to 70% MeOH/DCM to give the product as a trifluoroacetic acid salt. The product was partitioned between 1 M Na₂CO₃ (aq.) and chloroform/isopropanol (3:1). The organic layer was separated, and concentrated. Chloroform was added to the residue. The mixture was filtered and concentrated to give the title compound as a yellow solid (5.16 mg, 8.70 mmol, 17%). LCMS (MM-ES+APCI, Pos): m/z 593.2 (M+H).

Example 15

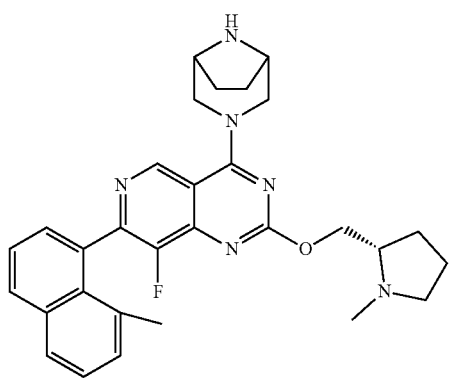 [SMILES: Cc1cccc2cccc(-c3ncc4c(N5CC6CCC(C5)N6)nc(OC[C@@H]5CCCN5C)nc4c3F)c12]

4-((1R,5S)-3,8-diazabicyclo[3.2.1]octan-3-yl)-8-fluoro-7-(8-methylnaphthalen-1-yl)-2-(((S)-1-methylpyrrolidin-2-yl)methoxy)pyrido[4,3-d]pyrimidine

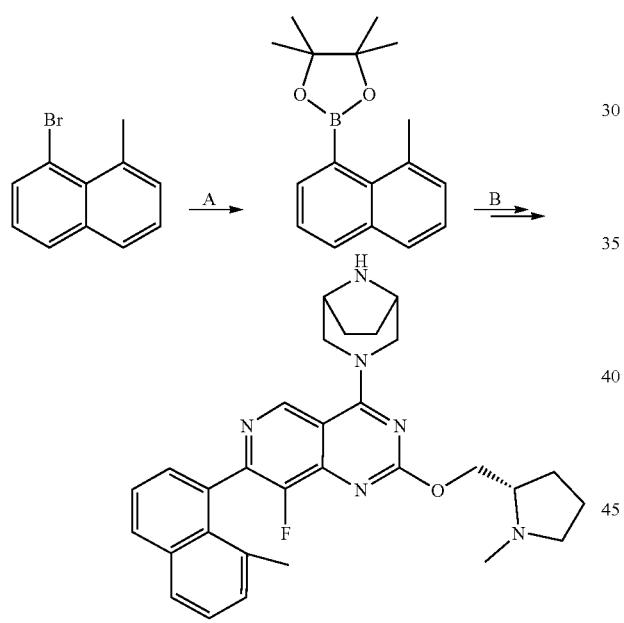

Step A. 4,4,5,5-tetramethyl-2-(8-methylnaphthalen-1-yl)-1,3,2-dioxaborolane. To a solution of 1-bromo-8-methylnaphthalene (0.700 g, 3.17 mmol) in dioxane (15.8 ml) were added potassium acetate (0.932 g, 9.50 mmol) and 4,4,4',4',5,5,5',5'-octamethyl-2,2'-bi(1,3,2-dioxaborolane) (2.41 g, 9.50 mmol) and the reaction sparged with N2 for 15 minutes, followed by addition of PdCl$_2$(dppf) (0.232 g, 0.317 mmol). The reaction was heated to 95° C. for 18 hrs. The reaction was concentrated in vacuo and taken up in DCM. The slurry was filtered through GF/F paper and the organics concentrated in vacuo. The material was chromatographed twice using 10→100% ethyl acetate/hexane as eluent to give 4,4,5,5-tetramethyl-2-(8-methylnaphthalen-1-yl)-1,3,2-dioxaborolane (576 mg, 2.15 mmol, 68% yield). HPLC (5-95% ACN/H$_2$O+0.1% TFA) 3.701 min.

Step B. The title compound was synthesized according to Example 2, Steps C-I substituting 4,4,5,5-tetramethyl-2-(8-methylnaphthalen-1-yl)-1,3,2-dioxaborolane in place of 4-(4,4,5,5-tetramethyl-1,3,2-dioxaborolan-2-yl)naphthalen-2-yl pivalate (17.0 mg, 78%). LCMS (MM-ES+APCI, Pos): m/z 513.3 [M+H].

Example 16

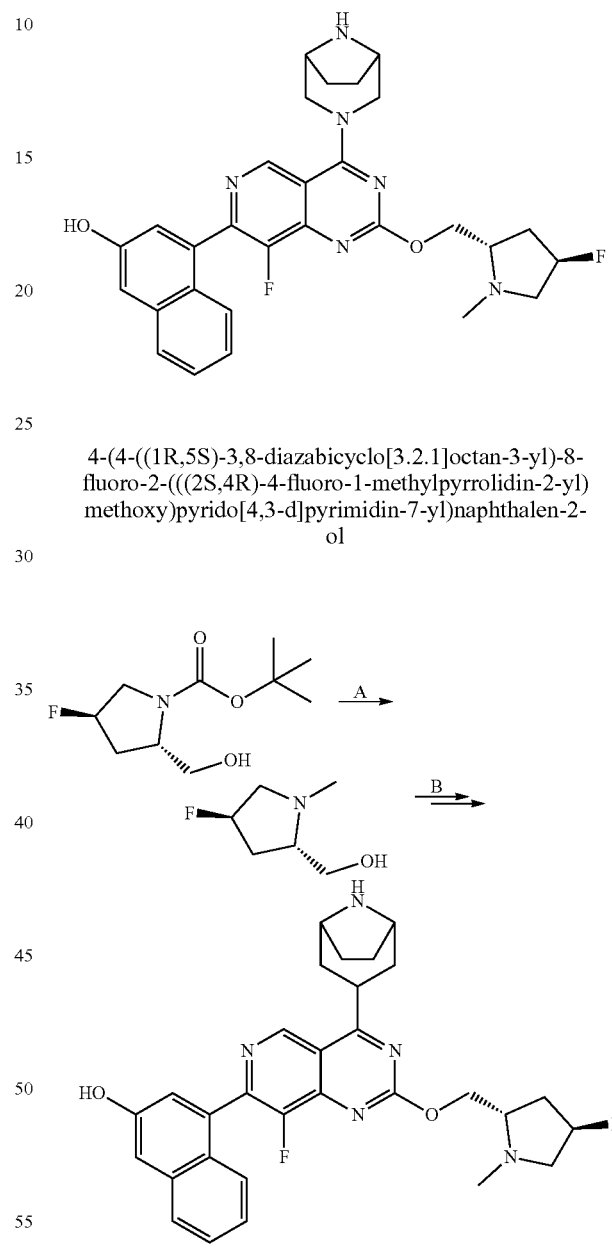

4-(4-((1R,5S)-3,8-diazabicyclo[3.2.1]octan-3-yl)-8-fluoro-2-(((2S,4R)-4-fluoro-1-methylpyrrolidin-2-yl)methoxy)pyrido[4,3-d]pyrimidin-7-yl)naphthalen-2-ol Step A. ((2S,4R)-4-fluoro-1-methylpyrrolidin-2-yl)methanol. (2S,4R)-1-(tert-Butoxycarbonyl)-4-fluoro-2-hydroxymethylpyrrolidine (1.70 g, 7.75 mmol) which was dissolved in Formic acid (14.6 ml) then formaldehyde (11.7 ml, 155 mmol) (37% aqueous) was added. The mixture was heated to 65° C. where it stirred for 4 h. The mixture was evaporated in vacuo and further dried under high vacuum for 3 h to give ((2S,4R)-4-fluoro-1-methylpyrrolidin-2-yl)methanol (1.00 g, 5.26 mmol, 67.8% yield) which was used crude in the next reaction.

Step B. The title compound was synthesized according to Example 3, Steps G-I substituting ((2S,4R)-4-fluoro-1-methylpyrrolidin-2-yl)methanol in place of 2-(1-methyl-1H-imidazol-2-yl)ethan-1-ol (8.00 mg, 65%). LCMS (MM-ES+APCI, Pos): m/z 533.2 [M+H].

Example 17

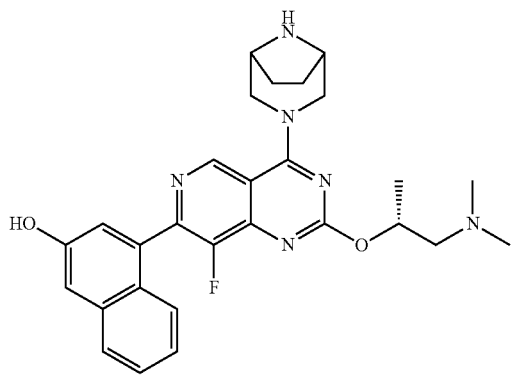 [SMILES: C[C@H](CN(C)C)Oc1nc(N2CC3CCC(C2)N3)c2cnc(-c3cc(O)cc4ccccc34)c(F)c2n1]

4-(4-((1R,5S)-3,8-diazabicyclo[3.2.1]octan-3-yl)-2-(((R)-1-(dimethylamino)propan-2-yl)oxy)-8-fluoro-pyrido[4,3-d]pyrimidin-7-yl)naphthalen-2-ol Synthesized according to Example 2, Steps D-I substituting (R)-1-(dimethylamino)propan-2-ol in place of (S)-(1-methylpyrrolidin-2-yl)methanol (4.00 mg, 33%). LCMS (MM-ES+APCI, Pos): m/z 503.2 [M+H].

Example 18

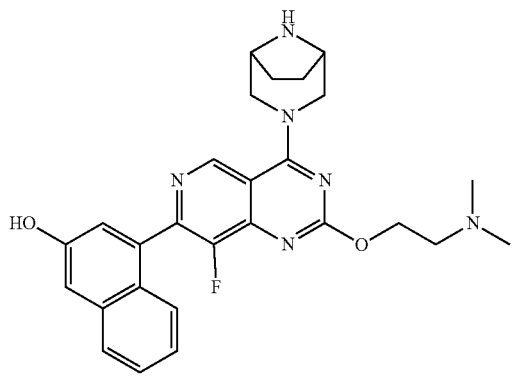 [SMILES: CN(C)CCOc1nc(N2CC3CCC(C2)N3)c2cnc(-c3cc(O)cc4ccccc34)c(F)c2n1]

4-(4-((1R,5S)-3,8-diazabicyclo[3.2.1]octan-3-yl)-2-(2-(dimethylamino)ethoxy)-8-fluoropyrido[4,3-d]pyrimidin-7-yl)naphthalen-2-ol Synthesized according to Example 2, Steps D-I substituting N,N-dimethylethanolamine in place of (S)-(1-methylpyrrolidin-2-yl)methanol (7.00 mg, 58%). LCMS (MM-ES+APCI, Pos): m/z 489.2 [M+H].

Example 19

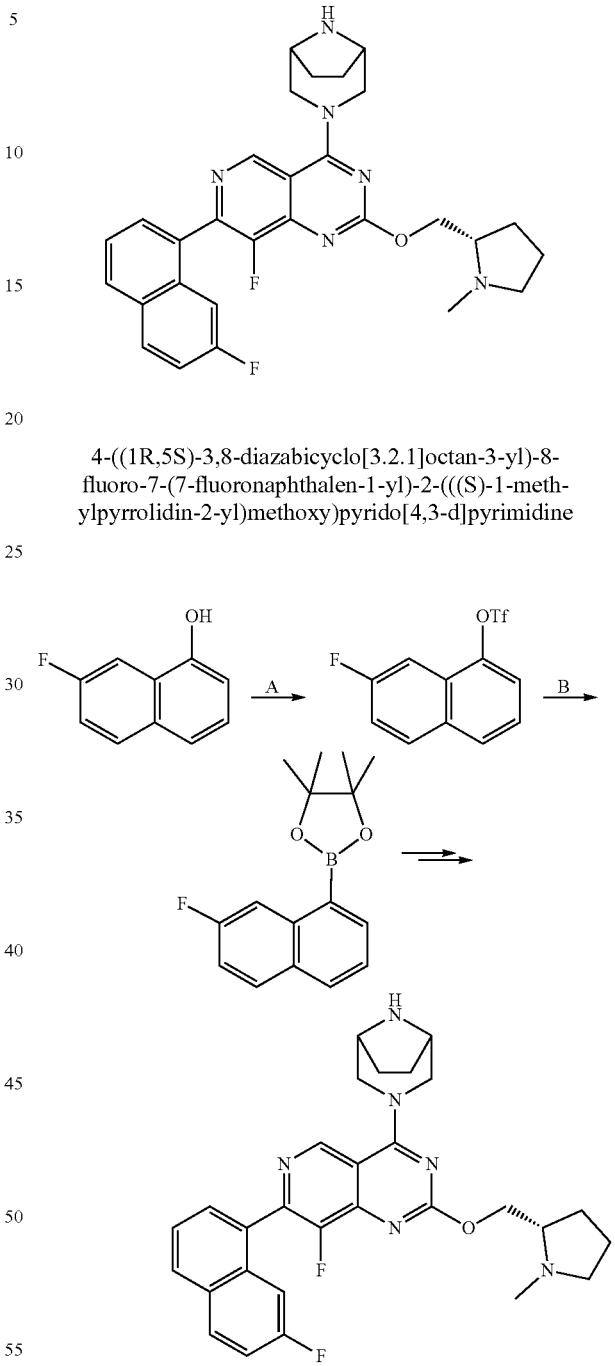

4-((1R,5S)-3,8-diazabicyclo[3.2.1]octan-3-yl)-8-fluoro-7-(7-fluoronaphthalen-1-yl)-2-(((S)-1-methylpyrrolidin-2-yl)methoxy)pyrido[4,3-d]pyrimidine Step A. 7-fluoronaphthalen-1-yl trifluoromethanesulfonate. To a solution of 7-fluoronaphthalen-1-ol (500 mg, 3.08 mmol) in DMA (15.4 ml) were added N-ethyl-N-isopropylpropan-2-amine (0.539 ml, 3.08 mmol) and then N-phenyl-bis(trifluoromethanesulfonimide) (1.65 g, 4.62 mmol) at rt. The resulting mixture was stirred at rt for 18 h. The reaction mixture was diluted with aq. sat. NaHCO₃, extracted with EtOAc, and the organic layer was filtered. The filtrate was evaporated in vacuo and purified by chromatography eluting with 0-50% EtOAc/hexane to give 7-fluoronaphthalen-1-yl trifluoromethanesulfonate (905 mg, 3.08 mmol, 99% yield). LCMS 3.577 min.

Step B. 2-(7-fluoronaphthalen-1-yl)-4,4,5,5-tetramethyl-1,3,2-dioxaborolane. To a solution of 7-fluoronaphthalen-1-yl trifluoromethanesulfonate (0.500 g, 1.69 mmol) in dioxane (8.49 ml) were added potassium acetate (467 mg, 5.07 mmol) and 4,4,4',4',5,5,5',5'-octamethyl-2,2'-bi(1,3,2-dioxaborolane) (1.29 g, 5.07 mmol). The reaction was sparged with N2 for 15 minutes, followed by addition of PdCl$_2$(dppf) (124 mg, 0.169 mmol) and the reaction mixture was heated to 95° C. for 18 hrs. The reaction was concentrated in vacuo and taken up in DCM. The slurry was filtered through GF/F paper and the filtrate was concentrated in vacuo. The residue was purified by flash chromatography using 10→100% DCM/hexane as eluent to give 2-(7-fluoronaphthalen-1-yl)-4,4,5,5-tetramethyl-1,3,2-dioxaborolane (180 mg, 0.661 mmol, 39%). HPLC 3.86 min.

The title compound was synthesized according to Example 3, Steps G-I substituting (S)-(1-methylpyrrolidin-2-yl)methanol in place of 2-(1-methyl-1H-imidazol-2-yl)ethan-1-ol and 2-(7-fluoronaphthalen-1-yl)-4,4,5,5-tetramethyl-1,3,2-dioxaborolane in place of 4-(4,4,5,5-tetramethyl-1,3,2-dioxaborolan-2-yl)naphthalen-2-ol (6 mg, 50%). LCMS (MM-ES+APCI, Pos): m/z 517.3 (M+H).

Example 20

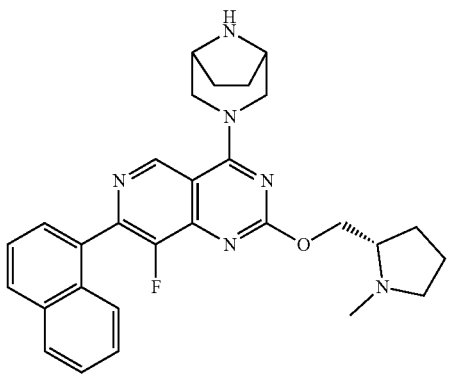 [SMILES: CN1CCC[C@H]1COc1nc(N2CC3CCC(C2)N3)c2cnc(-c3cccc4ccccc34)c(F)c2n1]

4-((1R,5S)-3,8-diazabicyclo[3.2.1]octan-3-yl)-8-fluoro-2-(((S)-1-methylpyrrolidin-2-yl)methoxy)-7-(naphthalen-1-yl)pyrido[4,3-d]pyrimidine Synthesized according Example 3, Steps G-I substituting (S)-(1-methylpyrrolidin-2-yl)methanol in place of 2-(1-methyl-1H-imidazol-2-yl)ethan-1-ol and naphthalen-1-yl-boronic acid in place of 4-(4,4,5,5-tetramethyl-1,3,2-dioxaborolan-2-yl)naphthalen-2-ol (2.00 mg, 8%). LCMS (MM-ES+APCI, Pos): m/z 499.2 (M+H).

Example 21

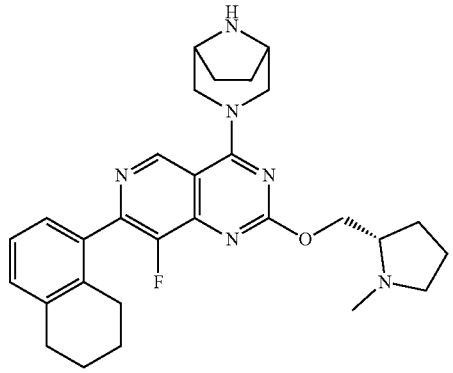 [SMILES: CN1CCC[C@H]1COc1nc(N2CC3CCC(C2)N3)c2cnc(-c3cccc4c3CCCC4)c(F)c2n1]

4-((1R,5S)-3,8-diazabicyclo[3.2.1]octan-3-yl)-8-fluoro-2-(((S)-1-methylpyrrolidin-2-yl)methoxy)-7-(5,6,7,8-tetrahydronaphthalen-1-yl)pyrido[4,3-d]pyrimidine

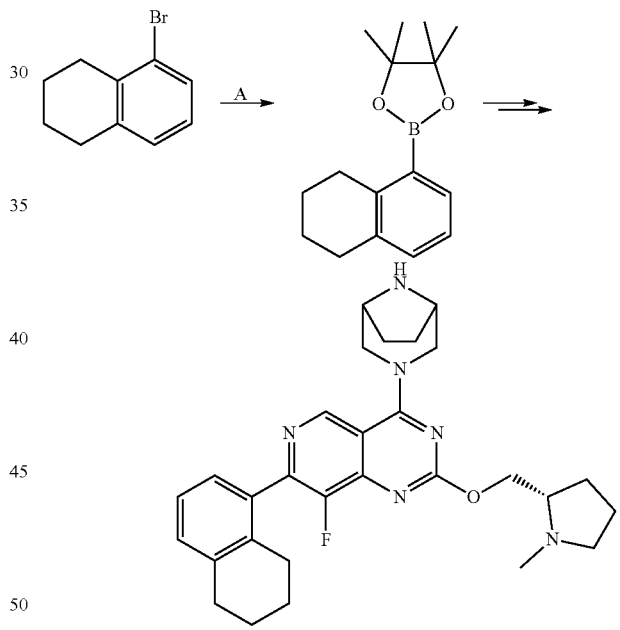

Step A. 4,4,5,5-tetramethyl-2-(5,6,7,8-tetrahydronaphthalen-1-yl)-1,3,2-dioxaborolane. To a solution of 5-bromo-1,2,3,4-tetrahydronaphthalene (700 mg, 3.32 mmol) in dioxane (16.6 ml) were added potassium acetate (976 mg, 9.95 mmol) and 4,4,4',4',5,5,5',5'-octamethyl-2,2'-bi(1,3,2-dioxaborolane) (2.53 g, 9.95 mmol) and the reaction was sparged with N2 for 15 minutes followed by addition of PdCl$_2$(dppf) (243 mg, 0.332 mmol). The reaction was heated at 95° C. for 18 hrs. The reaction was concentrated in vacuo and taken up in DCM. The slurry was filtered through GF/F paper and the organics was concentrated in vacuo. The material was chromatographed using 0-30% ethyl acetate/hexane as eluent to give 4,4,5,5-tetramethyl-2-(5,6,7,8-tetrahydronaphthalen-1-yl)-1,3,2-dioxaborolane (1.27 g, 3.94 mmol, 119% yield). LC 4.02 min.

The title compound was synthesized according to Example 3, Steps G-I substituting (S)-(1-methylpyrrolidin-2-yl)methanol in place of 2-(1-methyl-1H-imidazol-2-yl)ethan-1-ol and 4,4,5,5-tetramethyl-2-(5,6,7,8-tetrahydronaphthalen-1-yl)-1,3,2-dioxaborolane in place of 4-(4,4,5,5-tetramethyl-1,3,2-dioxaborolan-2-yl)naphthalen-2-ol (23.0 mg, 100%). LCMS (MM-ES+APCI, Pos): m/z 503.3 (M+H).

Example 22

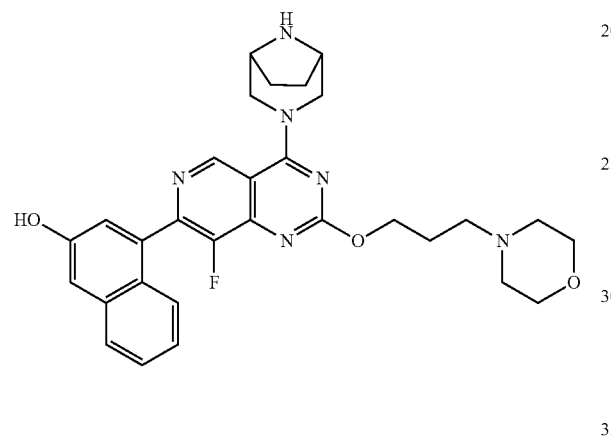

4-(4-((1R,5S)-3,8-diazabicyclo[3.2.1]octan-3-yl)-8-fluoro-2-(3-morpholinopropoxy)pyrido[4,3-d]pyrimidin-7-yl)naphthalen-2-ol Synthesized according Example 3, Steps G-I substituting N-3-morpholinopropan-1-ol in place of 2-(1-methyl-1H-imidazol-2-yl)ethan-1-ol (6.00 mg, 100%). LCMS (MM-ES+APCI, Pos): m/z 545.3 (M+H).

Example 23

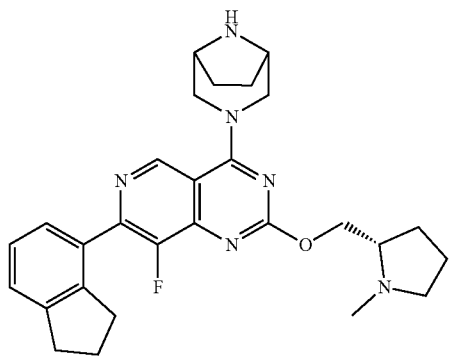 [SMILES: CN1CCC[C@H]1COc1nc(N2CC3CCC(C2)N3)c2cnc(-c3cccc4c3CCC4)c(F)c2n1]

4-((1R,5S)-3,8-diazabicyclo[3.2.1]octan-3-yl)-7-(2,3-dihydro-1H-inden-4-yl)-8-fluoro-2-(((S)-1-methylpyrrolidin-2-yl)methoxy)pyrido[4,3-d]pyrimidine

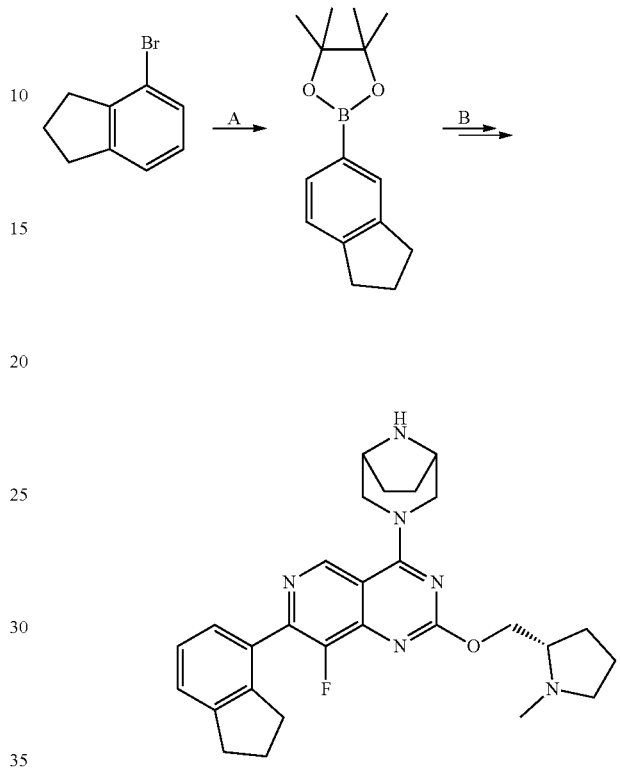

Step A. 2-(2,3-dihydro-1H-inden-4-yl)-4,4,5,5-tetramethyl-1,3,2-dioxaborolane. To a solution of 4-bromo-2,3-dihydro-1H-indene (500 mg, 2.54 mmol) in dioxane (12.7 ml) were added potassium acetate (747 mg, 7.61 mmol) and 4,4,4',4',5,5,5',5'-octamethyl-2,2'-bi(1,3,2-dioxaborolane) (1.93 g, 7.61 mmol). The reaction was sparged with N2 for 15 minutes, followed by addition of PdCl$_2$(dppf) (186 mg, 0.254 mmol) and the reaction was heated to 95° C. for 18 hrs. The reaction was concentrated in vacuo and taken up in DCM. The slurry was filtered through GF/F paper and the organics concentrated in vacuo. The material was chromatographed using 0→30% ethyl acetate/hexane as eluent to give 2-(2,3-dihydro-1H-inden-4-yl)-4,4,5,5-tetramethyl-1,3,2-dioxaborolane (340 mg, 1.39 mmol, 55% yield). HPLC 3.916 min.

Step B. The title compound was synthesized according Example 3, Steps G-I substituting (S)-(1-methylpyrrolidin-2-yl)methanol in place of 2-(1-methyl-1H-imidazol-2-yl)ethan-1-ol and substituting 2-(2,3-dihydro-1H-inden-4-yl)-4,4,5,5-tetramethyl-1,3,2-dioxaborolane in place of 4-(4,4,5,5-tetramethyl-1,3,2-dioxaborolan-2-yl)naphthalen-2-ol (2.00 mg, 21%). LCMS (MM-ES+APCI, Pos): m/z 489.2 (M+H).

Example 24

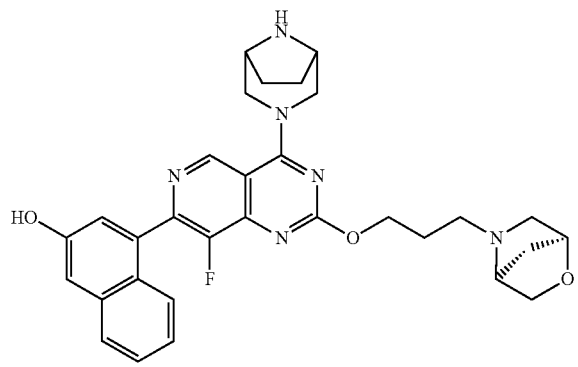

4-(2-(3-((1S,4S)-2-oxa-5-azabicyclo[2.2.1]heptan-5-yl)propoxy)-4-((1R,5S)-3,8-diazabicyclo[3.2.1]octan-3-yl)-8-fluoropyrido[4,3-d]pyrimidin-7-yl)naphthalen-2-ol Synthesized according Example 3, Steps G-I substituting 3-((1S,4S)-2-oxa-5-azabicyclo[2.2.1]heptan-5-yl)propan-1-ol in place of 2-(1-methyl-1H-imidazol-2-yl)ethan-1-ol (4.00 mg, 100%). LCMS (MM-ES+APCI, Pos): m/z 557.3 (M+H).

Example 25

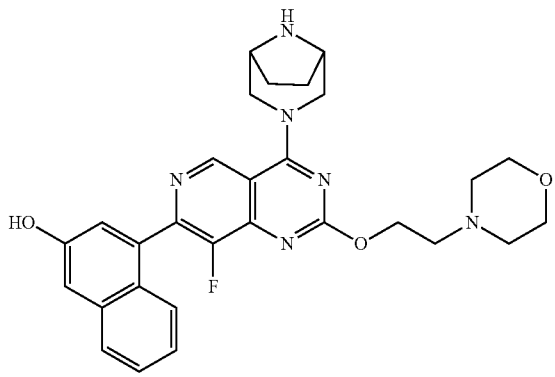 [SMILES: Oc1cc(-c2ncc3c(N4CC5CCC(C4)N5)nc(OCCN4CCOCC4)nc3c2F)c2ccccc2c1]

4-(4-((1R,5S)-3,8-diazabicyclo[3.2.1]octan-3-yl)-8-fluoro-2-(2-morpholinoethoxy)pyrido[4,3-d]pyrimidin-7-yl)naphthalen-2-ol Synthesized according to Example 3, Steps G-I substituting N-hydroxyethylmorpholine in place of 2-(1-methyl-1H-imidazol-2-yl)ethan-1-ol (15.0 mg, 100%). LCMS (MM-ES+APCI, Pos): m/z 531.2 (M+H).

Example 26

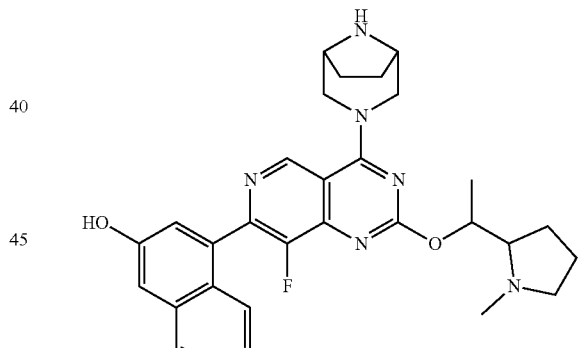

4-(2-(2-((1S,4S)-2-oxa-5-azabicyclo[2.2.1]heptan-5-yl)ethoxy)-4-((1R,5S)-3,8-diazabicyclo[3.2.1]octan-3-yl)-8-fluoropyrido[4,3-d]pyrimidin-7-yl)naphthalen-2-ol The title compound was synthesized according to Example 3, Steps G-I substituting 2-((1S,4S)-2-oxa-5-azabicyclo[2.2.1]heptan-5-yl)ethan-1-ol in place of 2-(1-methyl-1H-imidazol-2-yl)ethan-1-ol (4 mg, 0.005 mmol, 56%). LCMS (MM-ES+APCI, Pos): m/z 543.2 (M+H).

Example 27

4-(4-((1R,5S)-3,8-diazabicyclo[3.2.1]octan-3-yl)-8-fluoro-2-(1-(1-methylpyrrolidin-2-yl)ethoxy)pyrido[4,3-d]pyrimidin-7-yl)naphthalen-2-ol

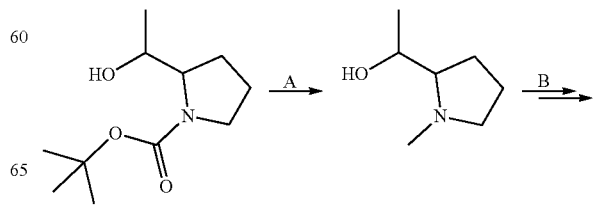

213

-continued

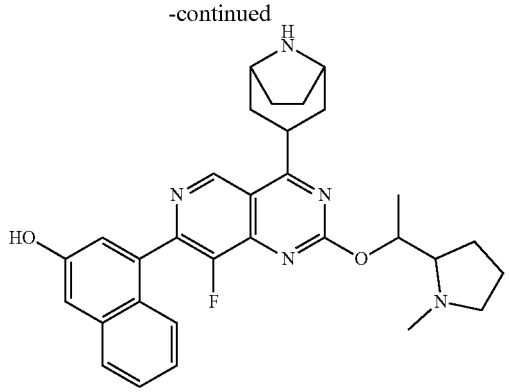

214

-continued

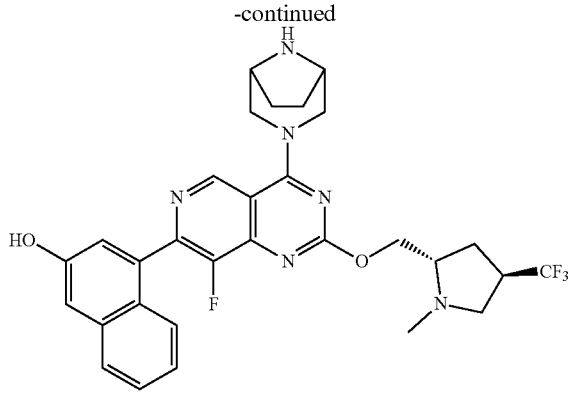

Step A: 1-(1-methylpyrrolidin-2-yl)ethan-1-ol. A mixture of tert-butyl 2-(1-hydroxyethyl)pyrrolidine-1-carboxylate (0.500 g, 2.32 mmol) in formic acid (4.38 ml) was added formaldehyde (3.49 ml, 46.4 mmol) (37% aqueous) and the mixture heated to 65° C. and stirred for 4 h. The mixture was evaporated in vacuo and further dried under high vacuum for 3 h to give 1-(1-methylpyrrolidin-2-yl)ethan-1-ol (462 mg, 2.15 mmol, 92% yield).

Step B: The title compound was synthesized according to Example 3, Steps G-I substituting 1-(1-methylpyrrolidin-2-yl)ethan-1-ol in place of 2-(1-methyl-1H-imidazol-2-yl)ethan-1-ol (4.00 mg, 83%). LCMS (MM-ES+APCI, Pos): m/z 529.3 (M+H).

Step A. ((2S,4R)-1-methyl-4-(trifluoromethyl)pyrrolidin-2-yl)methanol. A mixture of tert-butyl (2S,4R)-2-(hydroxymethyl)-4-(trifluoromethyl)pyrrolidine-1-carboxylate (0.500 g, 1.86 mmol) in formic acid (3.50 ml) was added formaldehyde (2.79 ml, 37.1 mmol) (37% aqueous) and the mixture heated to 65° C. and stirred for 4 h. The mixture was evaporated in vacuo and further dried under high vacuum for 18 h to give ((2S,4R)-1-methyl-4-(trifluoromethyl)pyrrolidin-2-yl)methanol (769 mg, 2.52 mmol, 136% yield).

Step B. The title compound was synthesized according to Example 3, Steps G-I substituting ((2S,4R)-1-methyl-4-(trifluoromethyl)pyrrolidin-2-yl)methanol in place of 2-(1-methyl-1H-imidazol-2-yl)ethan-1-ol (3.00 mg, 42%). LCMS (MM-ES+APCI, Pos): m/z 583.2 (M+H).

Example 28

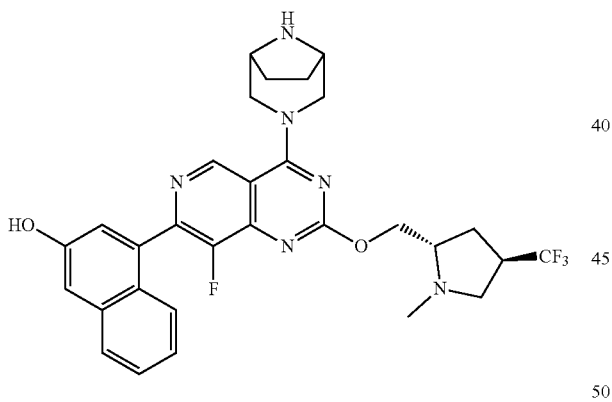

4-(4-((1R,5S)-3,8-diazabicyclo[3.2.1]octan-3-yl)-8-fluoro-2-(((2S,4R)-1-methyl-4-(trifluoromethyl)pyrrolidin-2-yl)methoxy)pyrido[4,3-d]pyrimidin-7-yl)naphthalen-2-ol Example 29

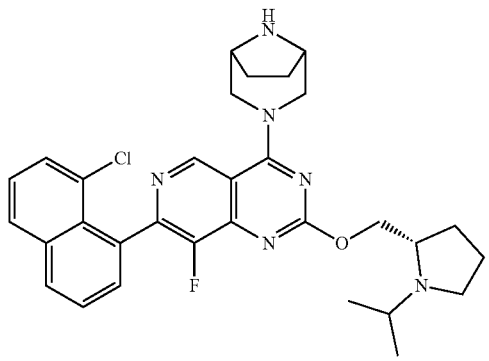 [SMILES: CC(C)N1CCC[C@H]1COc1nc(N2CC3CCC(C2)N3)c2cnc(-c3cccc4cccc(Cl)c34)c(F)c2n1]

4-((1R,5S)-3,8-diazabicyclo[3.2.1]octan-3-yl)-7-(8-chloronaphthalen-1-yl)-8-fluoro-2-(((S)-1-isopropylpyrrolidin-2-yl)methoxy)pyrido[4,3-d]pyrimidine

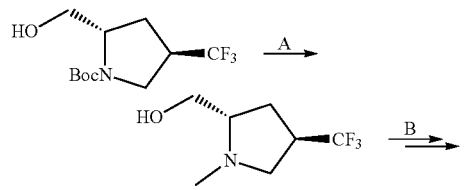

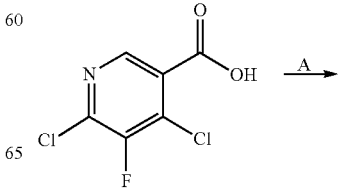

215
-continued

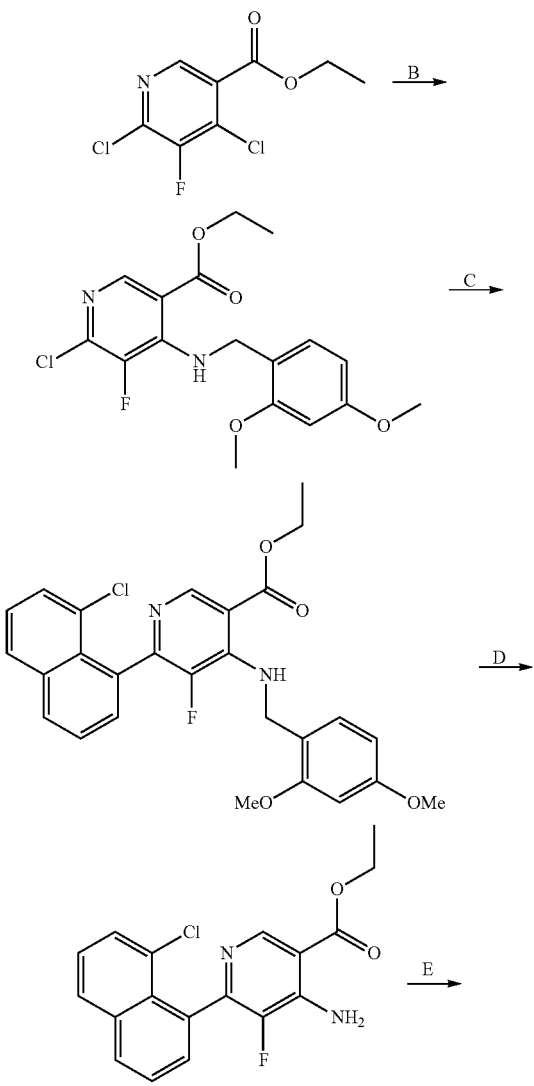

216
-continued

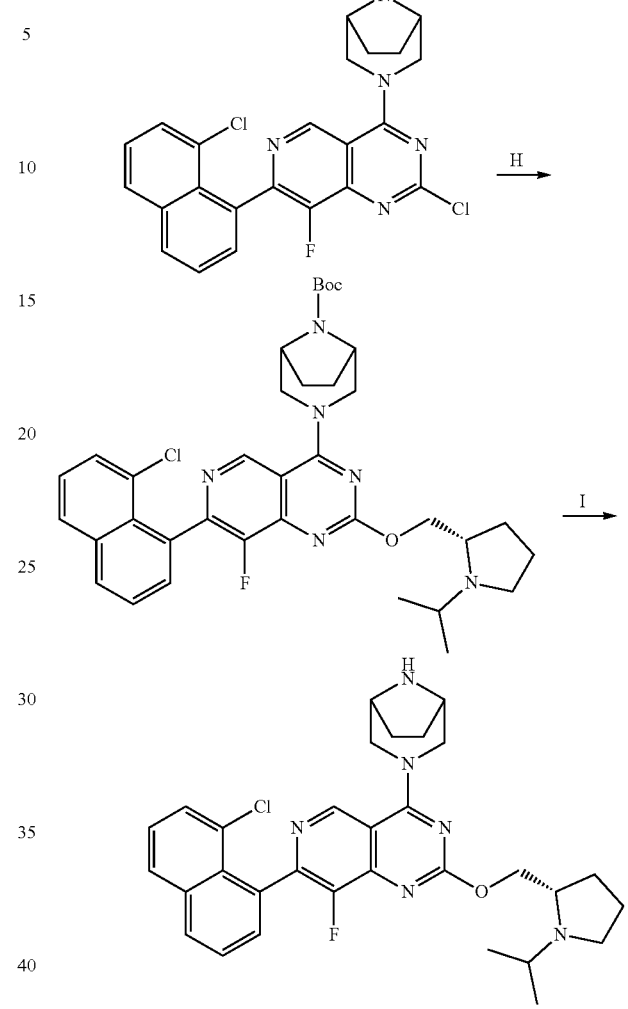

Step A. Ethyl 4,6-dichloro-5-fluoronicotinate. A solution of 4,6-dichloro-5-fluoro-3-pyridinecarboxylic acid (10.0 g, 47.6 mmol) in ethanol (238 ml, 47.6 mmol) was heated at 80° C. and thionyl chloride (6.95 ml, 95.2 mmol) was added dropwise through the condenser. The resulting mixture was stirred at 65° C. overnight. The reaction mixture was concentrated, and the residue was partitioned between EtOAc/water. The organic layer was washed with NaHCO$_3$, dried and concentrated to give a residue that was purified by flash chromatography eluting with a 0-100 EtOAc/hexanes gradient. The product fractions were collected and concentrated to give the desired product (9.61 g, 40.4 mmol, 85%). LCMS (MM-ES+APCI, Pos): m/z 237.9 (100%), 240.1 (50%) (M, M+2).

Step B. Ethyl 6-chloro-4-((2,4-dimethoxybenzyl)amino)-5-fluoronicotinate. To a mixture of ethyl 4,6-dichloro-5-fluoronicotinate (750 mg, 3.15 mmol) and N-ethyl-N-isopropylpropan-2-amine (1.38 ml, 7.88 mmol) in dioxane (15.8 ml, 3.15 mmol) was added 2,4-dimethoxybenzylamine (520 µL, 3.47 mmol) and the resulting mixture was heated at 40° C. for 18 h. The mixture was diluted with EtOAc and water. The aqueous layer was extracted with EtOAc (3×), and the combined organic layers were dried over Na$_2$SO$_4$, filtered, and concentrated. The residue was purified by flash chromatography eluting with 0-25% EtOAc/hexanes to give ethyl 6-chloro-4-((2,4-dimethoxybenzyl)amino)-5-fluoronicotinate (862 mg, 2.34 mmol, 74% yield). LCMS (MM-ES+APCI, Pos): m/z 369.1 (M+H).

Step C. Ethyl 6-(8-chloronaphthalen-1-yl)-4-((2,4-dimethoxybenzyl)amino)-5-fluoronicotinate. Ethyl 6-chloro-4-((2,4-dimethoxybenzyl)amino)-5-fluoronicotinate (4.48 g, 12.1 mmol), 2-(8-chloronaphthalen-1-yl)-4,4,5,5-tetramethyl-1,3,2-dioxaborolane (10.5 g, 36.4 mmol), $K_2CO_3$ (8.39 g, 60.7 mmol) and Pd(PPh$_3$)$_4$ (1.40 g, 1.21 mmol) were combined in toluene (100 mL), EtOH (50 mL) and water (25 mL) in a sealed vessel and stirred at 100° C. for 2 hours. The cooled mixture was partitioned between water (300 mL) and EtOAc (300 mL) and the aqueous phase was extracted with EtOAc (2×200 mL). The combined organic phases were washed with brine (200 mL), dried over $Na_2SO_4$, filtered and concentrated. The residue was purified by flash column chromatography eluting with 0 to 40 to 50% EtOAc/hexanes to give ethyl 6-(8-chloronaphthalen-1-yl)-4-((2,4-dimethoxybenzyl)amino)-5-fluoronicotinate (2.51 g, 5.07 mmol, 42% yield). LCMS (MM-ES+APCI, Pos): m/z 495.1 (M+).

Step D. Ethyl 4-amino-6-(8-chloronaphthalen-1-yl)-5-fluoronicotinate. To a solution of ethyl 6-(8-chloronaphthalen-1-yl)-4-((2,4-dimethoxybenzyl)amino)-5-fluoronicotinate (2.51 g, 5.07 mmol) in DCM (35 mL) was added TFA (7.81 mL, 101 mmol). The mixture was stirred for 1.5 hours and then carefully basified with 1M $K_3PO_4$. After filtration through GF paper, the filtrate was extracted with DCM (3×30 mL) and the combined organic phases were washed with brine (30 mL), dried over $Na_2SO_4$, filtered and concentrated to give ethyl 4-amino-6-(8-chloronaphthalen-1-yl)-5-fluoronicotinate (1.74 g, 5.05 mmol, 99% yield). LCMS (MM-ES+APCI, Pos): m/z 345.0 (M+).

Step E. 7-(8-chloronaphthalen-1-yl)-8-fluoropyrido[4,3-d]pyrimidine-2,4 (1H,3H)-dione. To a suspension of ethyl 4-amino-6-(8-chloronaphthalen-1-yl)-5-fluoronicotinate (1.74 g, 5.05 mmol) in THF (10 mL) cooled to 0° C. was added trichloroacetyl isocyanate (718 μL, 6.06 mmol). The mixture was stirred for 30 min, then concentrated, suspended in MeOH (25.2 mL), cooled to 0° C. and treated with ammonia (7M in MeOH, 14.4 mL, 101 mmol). The mixture was warmed to room temperature over 16 hours, filtered, washed with minimal methanol and dried in vacuo to give 7-(8-chloronaphthalen-1-yl)-8-fluoropyrido[4,3-d]pyrimidine-2,4 (1H,3H)-dione (1.38 g, 4.04 mmol, 80% yield). LCMS (MM-ES+APCI, Pos): m/z 342.0 (M+H).

Step F. 2,4-dichloro-7-(8-chloronaphthalen-1-yl)-8-fluoropyrido[4,3-d]pyrimidine. To a suspension of 7-(8-chloronaphthalen-1-yl)-8-fluoropyrido[4,3-d]pyrimidine-2,4 (1H,3H)-dione (0.96 g, 2.82 mmol) in POCl$_3$ (14.1 mL) was added N-ethyl-N-isopropylpropan-2-amine (1.41 mL). The mixture was warmed to 110° C. and stirred for 1.5 hours. The cooled mixture was concentrated and dried in vacuo. The residue was partitioned between EtOAc (50 mL) and water (50 mL), and then NaHCO$_3$ was added until basic. The aqueous layer was extracted with EtOAc (2×30 mL). The combined organic phases were washed with NaHCO$_3$ (20 mL) and brine (20 mL), then dried over $Na_2SO_4$, filtered and concentrated to give 2,4-dichloro-7-(8-chloronaphthalen-1-yl)-8-fluoropyrido[4,3-d]pyrimidine which was used without purification, assuming 100% yield. LCMS (MM-ES+APCI, Pos): m/z 378.0 (M+).

Step G. tert-butyl (1R,5S)-3-(2-chloro-7-(8-chloronaphthalen-1-yl)-8-fluoropyrido[4,3-d]pyrimidin-4-yl)-3,8-diazabicyclo[3.2.1]octane-8-carboxylate. To a solution of 2,4-dichloro-7-(8-chloronaphthalen-1-yl)-8-fluoropyrido[4,3-d]pyrimidine (1.07 g, 2.83 mmol) in DCM (30 mL) was added tert-butyl (1R,5S)-3,8-diazabicyclo[3.2.1]octane-8-carboxylate (540 mg, 2.54 mmol) followed by Et$_3$N (1.18 mL, 8.48 mmol). After stirred at room temperature for 2 hours, the mixture was partitioned between sat. NaHCO$_3$ (50 mL) and DCM (50 mL). The aqueous layer was extracted with DCM (2×30 mL) and the combined organic phases were washed with brine (20 mL), dried over $Na_2SO_4$, filtered and concentrated. The residue was purified by flash chromatography eluting with 5-40% EtOAc/hexanes to give tert-butyl (1R,5S)-3-(2-chloro-7-(8-chloronaphthalen-1-yl)-8-fluoropyrido[4,3-d]pyrimidin-4-yl)-3,8-diazabicyclo[3.2.1]octane-8-carboxylate (1.29 g, 2.33 mmol, 82% yield). LCMS (MM-ES+APCI, Pos): m/z 554.2 (M+).

Step H. tert-butyl (1R,5S)-3-(7-(8-chloronaphthalen-1-yl)-8-fluoro-2-(((S)-1-isopropylpyrrolidin-2-yl)methoxy)pyrido[4,3-d]pyrimidin-4-yl)-3,8-diazabicyclo[3.2.1]octane-8-carboxylate. A mixture of tert-butyl (1R,5S)-3-(2-chloro-7-(8-chloronaphthalen-1-yl)-8-fluoropyrido[4,3-d]pyrimidin-4-yl)-3,8-diazabicyclo[3.2.1]octane-8-carboxylate (50 mg, 0.09 mmol) and (S)-(1-isopropylpyrrolidin-2-yl)methanol (65 mg, 0.45 mmol) in dioxane (0.9 mL) was treated with Cs$_2$CO$_3$ (88 mg, 0.27 mmol) and stirred in a sealed tube at 70° C. for 16 hours. The cooled mixture was partitioned between water (10 mL) and EtOAc (10 mL) and the aqueous layer was extracted with EtOAc (2×10 mL). The combined organic phases were washed with brine (10 mL), dried over $Na_2SO_4$, filtered and concentrated. The residue was purified by flash chromatography eluting with a gradient of 0 to 20 to 50 to 100% (20% MeOH/DCM)/DCM to give tert-butyl (1R,5S)-3-(7-(8-chloronaphthalen-1-yl)-8-fluoro-2-(((S)-1-isopropylpyrrolidin-2-yl)methoxy)pyrido[4,3-d]pyrimidin-4-yl)-3,8-diazabicyclo[3.2.1]octane-8-carboxylate (19 mg, 0.029 mmol, 32% yield). LCMS (MM-ES+APCI, Pos): m/z 661.3 (M+).

Step I. 4-((1R,5S)-3,8-diazabicyclo[3.2.1]octan-3-yl)-7-(8-chloronaphthalen-1-yl)-8-fluoro-2-(((S)-1-isopropylpyrrolidin-2-yl)methoxy)pyrido[4,3-d]pyrimidine. To a solution of tert-butyl (1R,5S)-3-(7-(8-chloronaphthalen-1-yl)-8-fluoro-2-(((S)-1-isopropylpyrrolidin-2-yl)methoxy)pyrido[4,3-d]pyrimidin-4-yl)-3,8-diazabicyclo[3.2.1]octane-8-carboxylate (19 mg, 0.029 mmol) in DCM (1 mL) was added TFA (200 ul). The mixture was stirred at room temperature for 1.5 hours, and then concentrated in vacuo. The residue was purified by reverse phase preparative HPLC (5-95% ACN/water/0.1% TFA over 20 min). Clean fractions containing the desired product were combined, basified with sat. NaHCO$_3$ and extracted with DCM (3×10 mL). Combined organic phases were dried over $Na_2SO_4$, filtered and concentrated to give 4-((1R,5S)-3,8-diazabicyclo[3.2.1]octan-3-yl)-7-(8-chloronaphthalen-1-yl)-8-fluoro-2-(((S)-1-isopropylpyrrolidin-2-yl)methoxy)pyrido[4,3-d]pyrimidine (11 mg, 0.02 mmol, 68% yield). LCMS (MM-ES+APCI, Pos): m/z 561.2 (M+).

Example 30
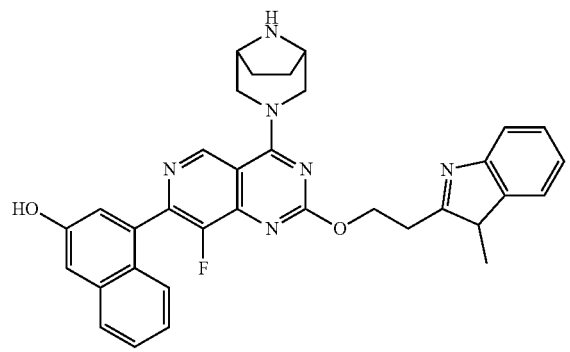 [SMILES: CC1C(CCOc2nc(N3CC4CCC(C3)N4)c3cnc(-c4cc(O)cc5ccccc45)c(F)c3n2)=Nc2ccccc21]
4-(4-(((1R,5S)-3,8-diazabicyclo[3.2.1]octan-3-yl)-8-fluoro-2-(2-(1-methyl-1H-benzo[d]imidazol-2-yl)ethoxy)pyrido[4,3-d]pyrimidin-7-yl)naphthalen-2-ol
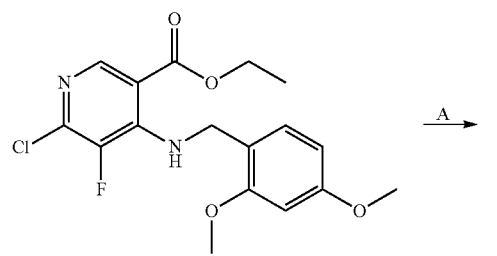
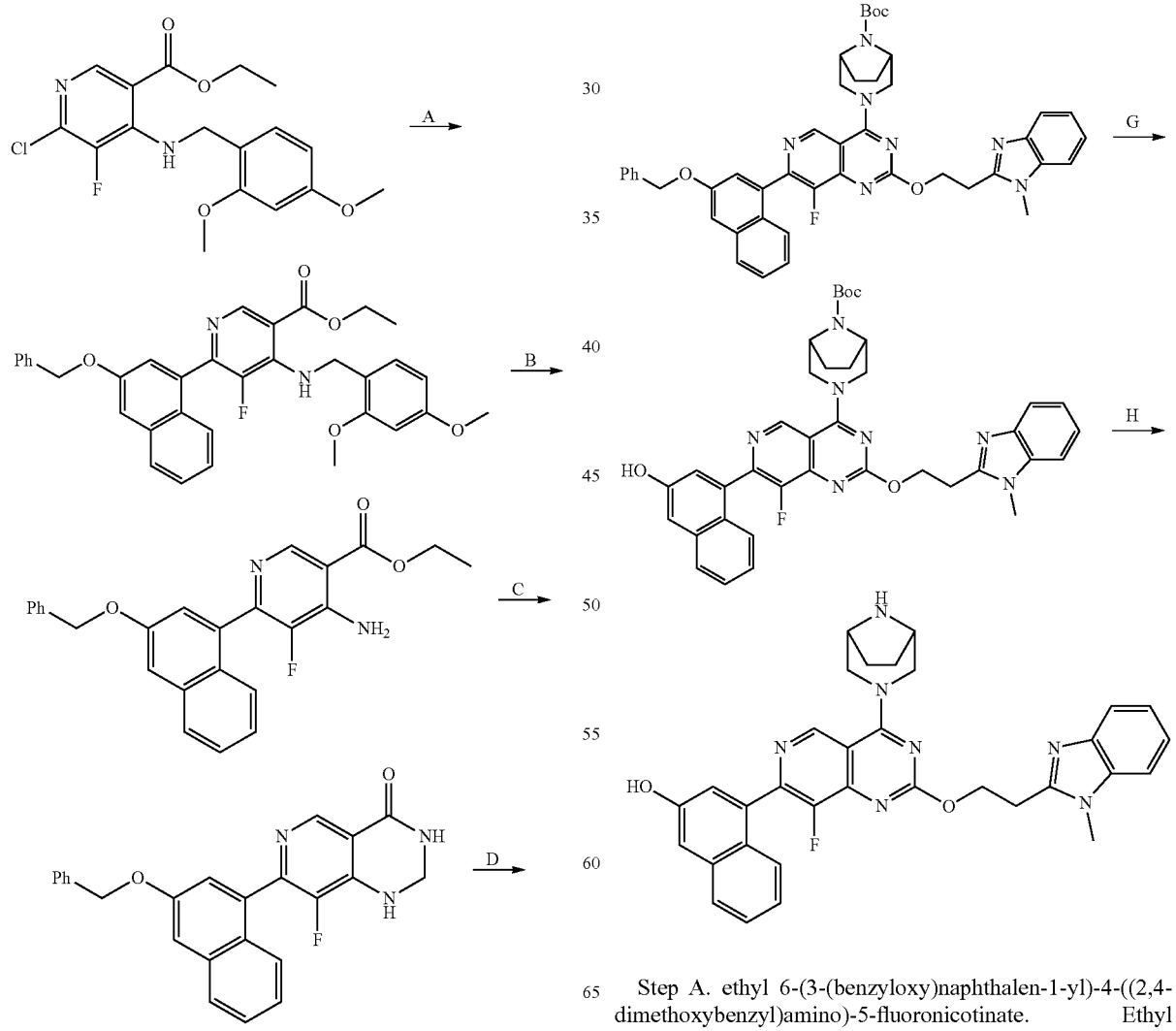
Step A. ethyl 6-(3-(benzyloxy)naphthalen-1-yl)-4-((2,4-dimethoxybenzyl)amino)-5-fluoronicotinate. Ethyl 6-chloro-4-((2,4-dimethoxybenzyl)amino)-5-fluoronicotinate (1.0 g, 2.71 mmol), 2-(3-(benzyloxy)naphthalen-1-yl)-4,4,5,5-tetramethyl-1,3,2-dioxaborolane (1.75 g, 3.25 mmol) and Pd(PPh$_3$)$_4$ (313 mg, 0.271 mmol) were combined in dioxanes (14 mL) and treated with K$_2$CO$_3$ (4.07 mL, 2M, 8.13 mmol). The mixture was stirred in a sealed vessel at 85° C. for 16 h, then cooled, and partitioned between water (50 mL) and EtOAc (50 mL). The aqueous layer was extracted with EtOAc (2×30 mL) and the combined organic phases were washed with brine (30 mL), dried over Na$_2$SO$_4$, filtered and concentrated. The residue was purified by flash chromatography eluting with 5-40% EtOAc/hexanes to afford ethyl 6-(3-(benzyloxy)naphthalen-1-yl)-4-((2,4-dimethoxybenzyl)amino)-5-fluoronicotinate (1.21 g, 2.14 mmol, 790%). L CMS (MM-ES+APCI, Pos): m/z 567.2 (M+H).

Step B. ethyl 4-amino-6-(3-(benzyloxy)naphthalen-1-yl)-5-fluoronicotinate. To a solution of ethyl 6-(3-(benzyloxy)naphthalen-1-yl)-4-((2,4-dimethoxybenzyl)amino)-5-fluoronicotinate (1.21 g, 2.14 mmol) in dry DCM (14.2 mL) was added TFA (3.29 mL, 42.7 mmol). The mixture was stirred for 1 h, then carefully basified with 1M K$_3$PO$_4$, and filtered through GF paper. The filtrate was extracted with DCM (3×30 mL) and the combined organic phases were washed with brine (30 mL), dried over Na$_2$SO$_4$, filtered and concentrated to afford ethyl 4-amino-6-(3-(benzyloxy)naphthalen-1-yl)-5-fluoronicotinate (0.884 g, 2.12 mmol, 99%). LCMS (MM-ES+APCI, Pos): m/z 417.1 (M+H).

Step C. 7-(3-(benzyloxy)naphthalen-1-yl)-8-fluoropyrido[4,3-d]pyrimidine-2,4 (1H,3H)-dione. To a suspension of ethyl 4-amino-6-(3-(benzyloxy)naphthalen-1-yl)-5-fluoronicotinate (884 mg, 2.12 mmol) in THF (5 mL) cooled to 0° C. was added trichloroacetyl isocyanate (302 µL, 2.55 mmol). The mixture was stirred for 30 min then concentrated. The residue was suspended in MeOH (10 mL), cooled to 0° C. and treated with ammonia (7M in MeOH, 6 mL, 42.5 mmol). The mixture was warmed to room temperature over 16 h, the solids were filtered, washed with minimal methanol and dried in vacuo to afford 7-(3-(benzyloxy)naphthalen-1-yl)-8-fluoropyrido[4,3-d]pyrimidine-2,4 (1H,3H)-dione (720 mg, 1.74 mmol, 82%) as a white solid. LCMS (MM-ES+APCI, Pos): m/z 414.1 (M+H).

Step D. 7-(3-(benzyloxy)naphthalen-1-yl)-2,4-dichloro-8-fluoropyrido[4,3-d]pyrimidine. To a suspension of 7-(3-(benzyloxy)naphthalen-1-yl)-8-fluoropyrido[4,3-d]pyrimidine-2,4 (1H,3H)-dione (200 mg, 0.484 mmol) in POCl$_3$ (2.42 mL) was added N-ethyl-N-isopropylpropan-2-amine (242 ul). The mixture was warmed to 110° C., stirred for 2 h, cooled, and concentrated. The residue was partitioned between EtOAc (20 mL) and NaHCO$_3$ (20 mL). The aqueous layer was extracted with EtOAc (2×10 mL) and the combined organic phases were washed with brine (10 mL), dried over Na$_2$SO$_4$, filtered and concentrated to afford 7-(3-(benzyloxy)naphthalen-1-yl)-2,4-dichloro-8-fluoropyrido[4,3-d]pyrimidine (247 mg, 0.55 mmol, 113%) which was used as crude, assuming 100% yield. LCMS (MM-ES+APCI, Pos): m/z 450.0 (M+).

Step E. tert-butyl (1R,5S)-3-(7-(3-(benzyloxy)naphthalen-1-yl)-2-chloro-8-fluoropyrido[4,3-d]pyrimidin-4-yl)-3,8-diazabicyclo[3.2.1]octane-8-carboxylate. To a suspension of 7-(3-(benzyloxy)naphthalen-1-yl)-2,4-dichloro-8-fluoropyrido[4,3-d]pyrimidine (218 mg, 0.48 mmol) in DCE (5 mL) was added tert-butyl (1R,5S)-3,8-diazabicyclo[3.2.1]octane-8-carboxylate (82 mg, 0.39 mmol) followed by Et$_3$N (202 µL, 1.45 mmol). The mixture was stirred at room temperature for 3 h, and then partitioned between water (20 mL) and DCM (20 mL). The aqueous layer was extracted with DCM (2×10 mL) and the combined organic phases were washed brine (10 mL), dried over Na$_2$SO$_4$, filtered and concentrated. The residue was purified by flash chromatography eluting with 0-40% EtOAc/hexanes to afford tert-butyl (1R,5S)-3-(7-(3-(benzyloxy)naphthalen-1-yl)-2-chloro-8-fluoropyrido[4,3-d]pyrimidin-4-yl)-3,8-diazabicyclo[3.2.1]octane-8-carboxylate (201 mg, 0.32 mmol, 66%) as a foam. LCMS (MM-ES+APCI, Pos): m/z 626.2 (M+).

Step F. tert-butyl (1R,5S)-3-(7-(3-(benzyloxy)naphthalen-1-yl)-8-fluoro-2-(2-(1-methyl-1H-benzo[d]imidazol-2-yl)ethoxy)pyrido[4,3-d]pyrimidin-4-yl)-3,8-diazabicyclo[3.2.1]octane-8-carboxylate. To a solution of tert-butyl (1R,5S)-3-(7-(3-(benzyloxy)naphthalen-1-yl)-2-chloro-8-fluoropyrido[4,3-d]pyrimidin-4-yl)-3,8-diazabicyclo[3.2.1]octane-8-carboxylate (50 mg, 0.08 mmol) and 2-(1-methyl-1H-benzo[d]imidazol-2-yl)ethan-1-ol dihydrate (25 mg, 0.12 mmol) in dioxane (1 mL) was added Cs$_2$CO$_3$ (78 mg, 0.24 mmol). The mixture was stirred in a sealed tube at 70° C. for 16 h then cooled and partitioned between water (20 mL) and EtOAc (20 mL). The aqueous layer was extracted with EtOAc (2×10 mL) and the combined organic phases were washed with brine (10 mL), dried over Na$_2$SO$_4$, filtered and concentrated. The residue was purified by flash chromatography eluting with 0-20% (MeOH/DCM)/DCM to afford tert-butyl (1R,5S)-3-(7-(3-(benzyloxy)naphthalen-1-yl)-8-fluoro-2-(2-(1-methyl-1H-benzo[d]imidazol-2-yl)ethoxy)pyrido[4,3-d]pyrimidin-4-yl)-3,8-diazabicyclo[3.2.1]octane-8-carboxylate (28 mg, 0.037 mmol, 46%) as a white solid.

Step G. tert-butyl (1R,5S)-3-(8-fluoro-7-(3-hydroxynaphthalen-1-yl)-2-(2-(1-methyl-1H-benzo[d]imidazol-2-yl)ethoxy)pyrido[4,3-d]pyrimidin-4-yl)-3,8-diazabicyclo[3.2.1]octane-8-carboxylate. To a suspension of tert-butyl (1R,5S)-3-(7-(3-(benzyloxy)naphthalen-1-yl)-8-fluoro-2-(2-(1-methyl-1H-benzo[d]imidazol-2-yl)ethoxy)pyrido[4,3-d]pyrimidin-4-yl)-3,8-diazabicyclo[3.2.1]octane-8-carboxylate (28 mg, 0.037 mmol) in MeOH (2 mL) was added 10% Pd/C (wet, Degussa type, 10 mg). The mixture was hydrogenated under a double-walled balloon for 16 h, and then filtered through GF paper. The filtrate was concentrated to afford tert-butyl (1R,5S)-3-(8-fluoro-7-(3-hydroxynaphthalen-1-yl)-2-(2-(1-methyl-1H-benzo[d]imidazol-2-yl)ethoxy)pyrido[4,3-d]pyrimidin-4-yl)-3,8-diazabicyclo[3.2.1]octane-8-carboxylate (22 mg, 0.033 mmol, 89%) as a solid. LCMS (MM-ES+APCI, Pos): m/z 676.3 (M+H).

Step H. 4-(4-((1R,5S)-3,8-diazabicyclo[3.2.1]octan-3-yl)-8-fluoro-2-(2-(1-methyl-1H-benzo[d]imidazol-2-yl)ethoxy)pyrido[4,3-d]pyrimidin-7-yl)naphthalen-2-ol. To a solution of tert-butyl(1R,5S)-3-(8-fluoro-7-(3-hydroxynaphthalen-1-yl)-2-(2-(1-methyl-1H-benzo[d]imidazol-2-yl)ethoxy)pyrido[4,3-d]pyrimidin-4-yl)-3,8-diazabicyclo[3.2.1]octane-8-carboxylate (22 mg, 0.033 mmol) in DCM (0.65 mL) was added TFA (50 µL, 0.65 mmol). The mixture was stirred at room temperature for 3 h and then partitioned between sat. NaHCO$_3$ (20 mL) and DCM (20 mL). The aqueous layer was extracted with DCM (2×5 mL) and the combined organic phases were washed with brine (5 mL), dried over Na$_2$SO$_4$, filtered and concentrated. The residue was purified by flash chromatography eluting with 0-40-100% (20% MeOH/DCM)/DCM to afford 4-(4-((1R,5S)-3,8-diazabicyclo[3.2.1]octan-3-yl)-8-fluoro-2-(2-(1-methyl-1H-benzo[d]imidazol-2-yl)ethoxy)pyrido[4,3-d]pyrimidin-7-yl)naphthalen-2-ol (6.3 mg. 0.011 mmol, 34%) as a white solid. LCMS (MM-ES+APCI, Pos): m/z 576.2 (M+H).

Example 31

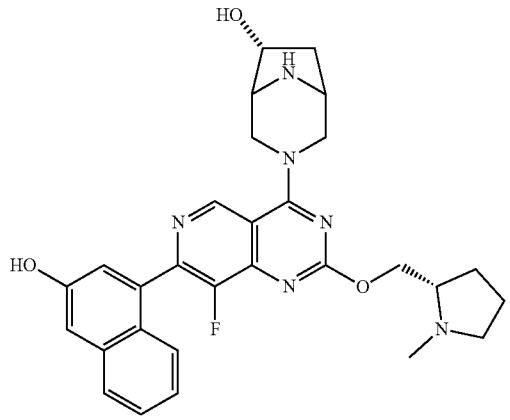 [SMILES: CN1CCC[C@H]1COc1nc(N2CC3C[C@@H](O)C(C2)N3)c2cnc(-c3cc(O)cc4ccccc34)c(F)c2n1]

3-(8-fluoro-7-(3-hydroxynaphthalen-1-yl)-2-(((S)-1-methylpyrrolidin-2-yl)methoxy)pyrido[4,3-d]pyrimidin-4-yl)-3,8-diazabicyclo[3.2.1]octan-6-ol

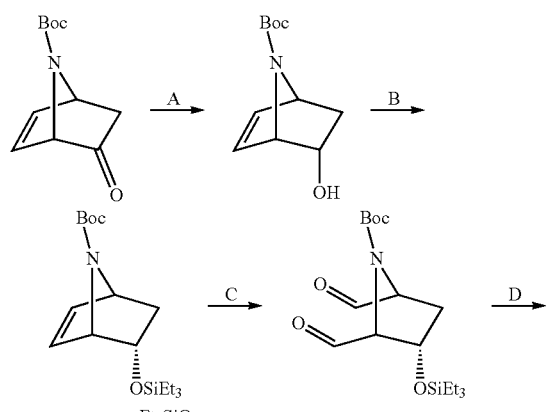

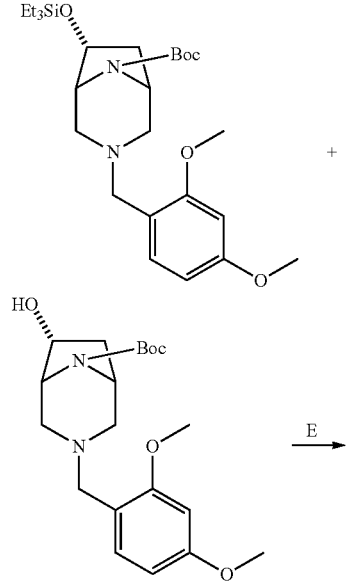

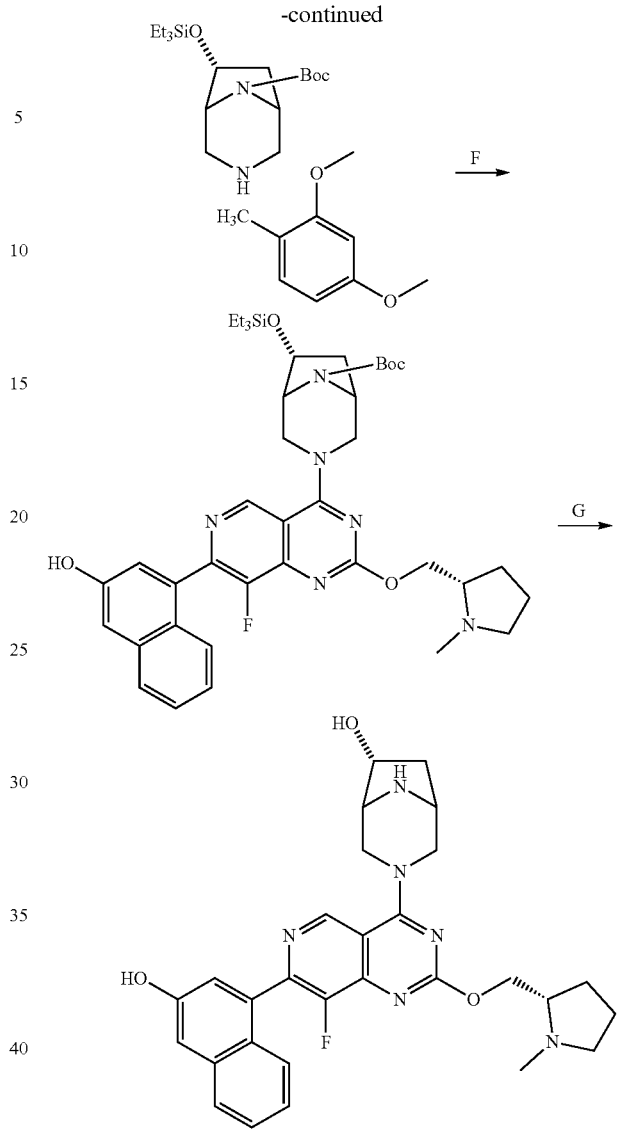

Step A. Tert-butyl (1S,4S,5S)-5-hydroxy-7-azabicyclo[2.2.1]hept-2-ene-7-carboxylate. To a stirred solution of tert-butyl-5-oxo-7-azabicyclo[2.2.1]hept-2-ene-7-carboxylate (500 mg, 2.39 mmol) in ethanol (5 mL) was added solid sodium borohydride (45 mg, 1.19 mmol) in several portions. The suspension was stirred at rt for 1 h. The reaction was partitioned between water (20 mL) and EtOAc (30 mL), and the layers were separated. The organic layer was washed with brine (5 mL), dried over $Na_2SO_4$ and concentrated in vacuo. The colorless solid was dried on air and washed with 20% EtOAc/hexane (3×0.5 mL). The combined aqueous phases were extracted with EtOAc, dried over $Na_2SO_4$, concentrated in vacuo, combined with washings from the main material and chromatographed on silica gel eluting with 20 to 50% EtOAc/hex. The fractions containing product were combined with the initially obtained solid to give tert-butyl 5-hydroxy-7-azabicyclo[2.2.1]hept-2-ene-7-carboxylate (500 mg, 99%). $^1$H NMR (400 MHz, CDCl$_3$): 6.59 (s, 1H), 6.32 (s, 1H), 4.71 (s, 1H), 4.68 (s, 1H), 4.55-4.45 (m, 1H), 2.35 (ddd, J=11.9, 8.0, 5.4 Hz, 1H), 1.49 (br. s., 1H), 1.40 (s, 9H), 1.40 (m, 1H).

Step B tert-butyl 5-((triethylsilyl)oxy)-7-azabicyclo[2.2.1]hept-2-ene-7-carboxylate. To a stirred solution tert-butyl 5-hydroxy-7-azabicyclo[2.2.1]hept-2-ene-7-carboxylate (500 mg, 2.37 mmol) and triethylamine (660 µL, 4.73 mmol) in dichloromethane (4.7 mL) was added chlorotriethylsilane (0.60 mL, 3.6 mmol) dropwise. The reaction mixture was stirred at rt overnight. The reaction was partitioned between water (10 mL) and MTBE (15 mL), and the organic layer was separated and washed with brine (5 mL), dried over $Na_2SO_4$ and concentrated in vacuo. The residue was chromatographed on silica gel using 10 to 40% EtOAc/hexane as eluent to give tert-butyl 5-((triethylsilyl)oxy)-7-azabicyclo[2.2.1]hept-2-ene-7-carboxylate (718 mg, 93%) as a colorless liquid. LCMS (MM-ES+APCI, Pos): m/z 226.3 (M-Boc+H). $^1$H NMR (400 MHz, $CDCl_3$): 6.47 (s, 1H), 6.23 (s, 1H), 4.57 (br.s., 2H), 4.45-4.39 (m, 1H), 2.22 (ddd, J=11.5, 7.8, 4.5 Hz, 1H), 1.40 (s, 9H), 0.92 (t, J=7.8 Hz, 9H), 0.87 (dd, J=11.5, 2.3 Hz, 1H), 0.57 (q, J=7.9 Hz, 6H).

Step C. Tert-butyl (2R,3S,5S)-2,5-diformyl-3-((triethylsilyl)oxy)pyrrolidine-1-carboxylate. A stirred solution of tert-butyl 5-((triethylsilyl)oxy)-7-azabicyclo[2.2.1]hept-2-ene-7-carboxylate (718 mg, 2.21 mmol) in dichloromethane (11 mL) was cooled in a dry ice—ethanol bath and ozone (~1% in O2) flow was introduced. After the reaction mixture attained a blue color (~45 min), it was flushed with N2 and a solution of triphenylphosphine (1446 mg, 5.51 mmol) in DCM (5 mL) was added dropwise. The resulting solution of crude tert-butyl 2,5-diformyl-3-((triethylsilyl)oxy)pyrrolidine-1-carboxylate was warmed to r.t. over 1 hour and was used immediately in the next reaction.

Step D. Tert-butyl 3-(2,4-dimethoxybenzyl)-6-((triethylsilyl)oxy)-3,8-diazabicyclo[3.2.1]octane-8-carboxylate and tert-butyl 3-(2,4-dimethoxybenzyl)-6-hydroxy-3,8-diazabicyclo[3.2.1]octane-8-carboxylate. To a stirred solution of crude tert-butyl-2,5-diformyl-3-((triethylsilyl)oxy)pyrrolidine-1-carboxylate (789 mg, 2.21 mmol) in dichloromethane (45 mL) was added solid sodium triacetoxyborohydride (1169 mg, 5.52 mmol) in one portion followed by a solution of (2,4-dimethoxyphenyl)methanamine (369 mg, 2.21 mmol) in DCM (1 ml) portion wise at a rate of -0.1 mL/min. After completion of addition the reaction was stirred 90 min at rt, and then 2M $Na_2CO_3$ (10 mL) was added. The reaction stirred one more hour and the layers were separated. The organic phase was washed with water and brine (10 mL each), dried over $Na_2SO_4$ and evaporated in vacuo. The residue was chromatographed on silica gel using 10 to 20 to 40% EtOAc/hexane as eluent to yield tert-butyl 3-(2,4-dimethoxybenzyl)-6-((triethylsilyl)oxy)-3,8-diazabicyclo[3.2.1]octane-8-carboxylate (251 mg, 23%) and tert-butyl 3-(2,4-dimethoxybenzyl)-6-hydroxy-3,8-diazabicyclo[3.2.1]octane-8-carboxylate (155 mg, 19%) as colorless crystalline solid. LCMS (MM-ES+APCI, Pos): m/z 493.3 (M+H).

Step E. Tert-butyl 3-(2,4-dimethoxybenzyl)-6-((triethylsilyl)oxy)-3,8-diazabicyclo[3.2.1]octane-8-carboxylate: To a stirred solution of tert-butyl 3-(2,4-dimethoxybenzyl)-6-((triethylsilyl)oxy)-3,8-diazabicyclo[3.2.1]octane-8-carboxylate (251 mg, 0.509 mmol) in MeOH (4 mL) was added 20% palladium hydroxide on carbon (200 mg) and the reaction mixture was degassed. A hydrogen atmosphere (rubber balloon) was introduced and the reaction was stirred for 1 h. The slurry was filtered through Celite and the Celite washed with MeOH (3×2 mL). The combined organic layers were evaporated in vacuo. The residue was dissolved in MTBE (1 mL), filtered through a cotton plug and concentrated under $N_2$ flow to yield tert-butyl-3-(2,4-dimethoxybenzyl)-6-((triethylsilyl)oxy)-3,8-diazabicyclo[3.2.1]octane-8-carboxylate as a 1:1 mixture with 2,4-dimethoxytoluene. The material was used in the next step without further purification. LCMS (MM-ES+APCI, Pos): m/z 343.3 (M+H).

Step F. Tert-butyl 3-(8-fluoro-7-(3-hydroxynaphthalen-1-yl)-2-(((S)-1-methylpyrrolidin-2-yl)methoxy)pyrido[4,3-d]pyrimidin-4-yl)-6-((triethylsilyl)oxy)-3,8-diazabicyclo[3.2.1]octane-8-carboxylate. To a stirred solution of (S)-8-fluoro-7-(3-hydroxynaphthalen-1-yl)-2-((1-methylpyrrolidin-2-yl)methoxy)pyrido[4,3-d]pyrimidin-4-ol (50 mg, 0.119 mmol) in N,N-dimethylacetamide (0.6 mL) under $N_2$ was added N-ethyl-N-isopropylpropan-2-amine (0.1 mL, 0.6 mmol) and the solution was stirred for 15 min at rt. Solid 2-(3H-[1,2,3]triazolo[4,5-b]pyridin-3-yl)-1,1,3,3-tetramethylisouronium (HATU reagent, 181 mg, 0.476 mmol) was added. The reaction was stirred 10 min and then cooled on an ice bath. A solution of tert-butyl 6-((triethylsilyl)oxy)-3,8-diazabicyclo[3.2.1]octane-8-carboxylate and 2,4-dimethoxy-1-methylbenzene (1:1) (59 mg, 0.12 mmol) in DMA (0.1 mL) was added. The reaction mixture was warmed to rt and stirred for 1 hr. Triethylamine (0.1 mL) and water (0.2 mL) were added and the reaction mixture stirred overnight. The reaction was evaporated under vacuum and the residue was chromatographed on silica gel with 4 to 10% [10% $NH_4OH$/methanol]/dichloromethane as eluent to yield tert-butyl 3-(8-fluoro-7-(3-hydroxynaphthalen-1-yl)-2-(((S)-1-methylpyrrolidin-2-yl)methoxy)pyrido[4,3-d]pyrimidin-4-yl)-6-((triethylsilyl)oxy)-3,8-diazabicyclo[3.2.1]octane-8-carboxylate as colorless solid (37 mg, 42%). LCMS (MM-ES+APCI, Pos): m/z 745.3 (M+H).

Step G. 3-(8-fluoro-7-(3-hydroxynaphthalen-1-yl)-2-(((S)-1-methylpyrrolidin-2-yl)methoxy)pyrido[4,3-d]pyrimidin-4-yl)-3,8-diazabicyclo[3.2.1]octan-6-ol. Synthesized according to Example 2, Step I using tert-butyl 3-(8-fluoro-7-(3-hydroxynaphthalen-1-yl)-2-(((S)-1-methylpyrrolidin-2-yl)methoxy)pyrido[4,3-d]pyrimidin-4-yl)-6-((triethylsilyl)oxy)-3,8-diazabicyclo[3.2.1]octane-8-carboxylate in place of tert-butyl (1R,5S)-3-(8-fluoro-7-(3-hydroxynaphthalen-1-yl)-2-(((S)-1-methylpyrrolidin-2-yl)methoxy)pyrido[4,3-d]pyrimidin-4-yl)-3,8-diazabicyclo[3.2.1]octane-8-carboxylate. Colorless solid, yield 30%. LCMS (MM-ES+APCI, Pos): m/z 531.2 (M+H).

Example 32

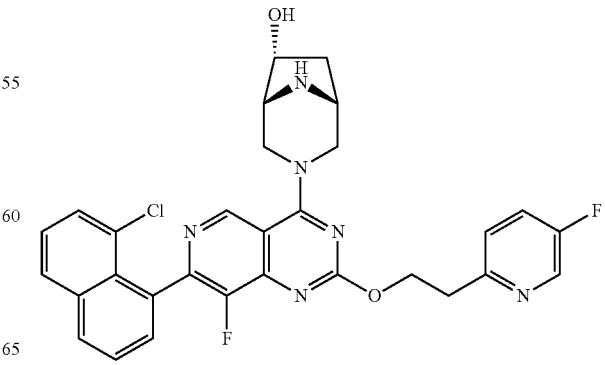

(1R,5R,6R)-3-(7-(8-chloronaphthalen-1-yl)-8-fluoro-2-(2-(5-fluoropyridin-2-yl)ethoxy)pyrido[4,3-d]pyrimidin-4-yl)-3,8-diazabicyclo[3.2.1]octan-6-ol

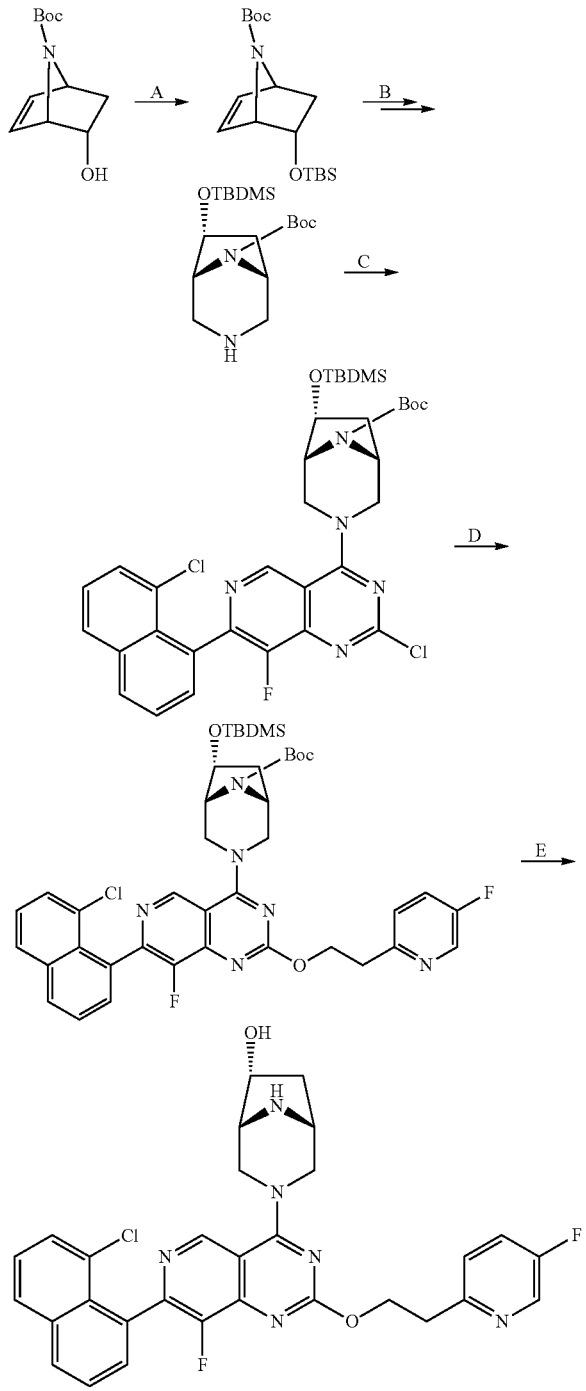

Step A. tert-butyl (1S,4S,5S)-5-((tert-butyldimethylsilyl)oxy)-7-azabicyclo[2.2.1]hept-2-ene-7-carboxylate. A mixture of tert-butyl (1S,4S,5S)-5-hydroxy-7-azabicyclo[2.2.1]hept-2-ene-7-carboxylate (4.1 g, 19 mmol), imidazole (2.0 g, 29 mmol), and tert-butylchlorodimethylsilane (3.5 g, 23 mmol) in N,N-dimethylformamide (8 mL) was stirred at 30° C. for 1 hour and then at r.t. overnight. The reaction mixture was quenched with MeOH (2 mL), stirred for 1 h at r.t., and partitioned between water (50 mL) and MTBE (100 mL). The organic layer was washed with brine (5 mL), dried over Na$_2$SO$_4$, evaporated in vacuo, and chromatographed on silica gel eluting with 10 to 40% EtOAc/hexane to yield the title compound as a colorless oil (5.6 g, 89%).

Step B. tert-butyl (6R)-6-((tert-butyldimethylsilyl)oxy)-3,8-diazabicyclo[3.2.1]octane-8-carboxylate. Synthesized according to Example 31, steps C-E substituting tert-butyl (1S,4S,5S)-5-((tert-butyldimethylsilyl)oxy)-7-azabicyclo[2.2.1]hept-2-ene-7-carboxylate for tert-butyl (1S,4S,5S)-5-((triethylsilyl)oxy)-7-azabicyclo[2.2.1]hept-2-ene-7-carboxylate in Step C. LCMS (MM-ES+APCI, Pos): m/z 343.2 (M+H).

Step C. tert-butyl (1R,5R,6R)-6-((tert-butyldimethylsilyl)oxy)-3-(2-chloro-7-(8-chloronaphthalen-1-yl)-8-fluoropyrido[4,3-d]pyrimidin-4-yl)-3,8-diazabicyclo[3.2.1]octane-8-carboxylate. To a suspension of 2,4-dichloro-7-(8-chloronaphthalen-1-yl)-8-fluoropyrido[4,3-d]pyrimidine (0.90 g, 2.4 mmol) in DCE (24 mL) was added tert-butyl (1R,5R,6R)-6-((tert-butyldimethylsilyl)oxy)-3,8-diazabicyclo[3.2.1]octane-8-carboxylate (810 mg, 2.4 mmol) followed by Et$_3$N (0.99 mL, 7.1 mmol). The mixture was stirred at room temperature for 2 h and then partitioned between sat. NaHCO$_3$ (50 mL) and DCM (50 mL). The aqueous layer was extracted with DCM (2×30 mL) and the combined organic phases were washed with brine (20 mL), dried over Na$_2$SO$_4$, filtered and concentrated. The residue was purified by flash chromatography eluting with 5-35% EtOAc/hexanes to give tert-butyl (1R,5R,6R)-6-((tert-butyldimethylsilyl)oxy)-3-(2-chloro-7-(8-chloronaphthalen-1-yl)-8-fluoropyrido[4,3-d]pyrimidin-4-yl)-3,8-diazabicyclo[3.2.1]octane-8-carboxylate (1.08 g, 1.58 mmol, 66% yield). LCMS (MM-ES+APCI, Pos): m/z 684.2 (M+H).

Step D. tert-butyl (1R,5R,6R)-6-((tert-butyldimethylsilyl)oxy)-3-(7-(8-chloronaphthalen-1-yl)-8-fluoro-2-(2-(5-fluoropyridin-2-yl)ethoxy)pyrido[4,3-d]pyrimidin-4-yl)-3,8-diazabicyclo[3.2.1]octane-8-carboxylate. A mixture of tert-butyl (1R,5R,6R)-6-((tert-butyldimethylsilyl)oxy)-3-(2-chloro-7-(8-chloronaphthalen-1-yl)-8-fluoropyrido[4,3-d]pyrimidin-4-yl)-3,8-diazabicyclo[3.2.1]octane-8-carboxylate (75 mg, 0.11 mmol) and 2-(5-fluoropyridin-2-yl)ethan-1-ol (62, 0.44 mmol) in dioxane (1 mL) was treated with Cs$_2$CO$_3$ (110 mg, 0.33 mmol) and stirred in a sealed tube at 70° C. for 16 h. The cooled mixture was partitioned between water (10 mL) and EtOAc (10 mL) and the aqueous layer was extracted with EtOAc (2×10 mL). The combined organic phases were washed with brine (10 mL), dried over Na$_2$SO$_4$, filtered and concentrated. The residue was purified by flash chromatography eluting with 0-50% EtOAc/hexanes to afford tert-butyl (1R,5R,6R)-6-((tert-butyldimethylsilyl)oxy)-3-(7-(8-chloronaphthalen-1-yl)-8-fluoro-2-(2-(5-fluoropyridin-2-yl)ethoxy)pyrido[4,3-d]pyrimidin-4-yl)-3,8-diazabicyclo[3.2.1]octane-8-carboxylate (22 mg, 0.028 mmol, 25% yield). LCMS (MM-ES+APCI, Pos): m/z 789.3 (M+H).

Step E. (1R,5R,6R)-3-(7-(8-chloronaphthalen-1-yl)-8-fluoro-2-(2-(5-fluoropyridin-2-yl)ethoxy)pyrido[4,3-d]pyrimidin-4-yl)-3,8-diazabicyclo[3.2.1]octan-6-ol. A solution of tert-butyl (1R,5R,6R)-6-((tert-butyldimethylsilyl)oxy)-3-(7-(8-chloronaphthalen-1-yl)-8-fluoro-2-(2-(5-fluoropyridin-2-yl)ethoxy)pyrido[4,3-d]pyrimidin-4-yl)-3,8-diazabicyclo[3.2.1]octane-8-carboxylate (22 mg, 0.03 mmol) in THF (2 mL) was treated with TBAF (42 µL, 0.04 mmol) and stirred at room temperature for 2 h. The mixture was partitioned between water (10 mL) and EtOAc (10 mL) and the aqueous layer was extracted with EtOAc (2×10 mL). The combined organic phases were washed with brine (10 mL), dried over Na₂SO₄, filtered and concentrated. The residue was dissolved in DCM (1 mL) and treated with TFA (100 ul). After stirring for 2 h, a further 300 μL of TFA was added and stirring continued for 2 h. The mixture was concentrated in vacuo and then purified on Gilson prep HPLC (0-95% ACN/water/0.1% TFA over 20 min). The fractions were worked up with sat. NaHCO₃ and DCM to afford (1R,5R,6R)-3-(7-(8-chloronaphthalen-1-yl)-8-fluoro-2-(2-(5-fluoropyridin-2-yl)ethoxy)pyrido[4,3-d]pyrimidin-4-yl)-3,8-diazabicyclo[3.2.1]octan-6-ol (5 mg, 0.0087 mmol, 31% yield). LCMS (MM-ES+APCI, Pos): m/z 575.2 (M+H).

Example 33

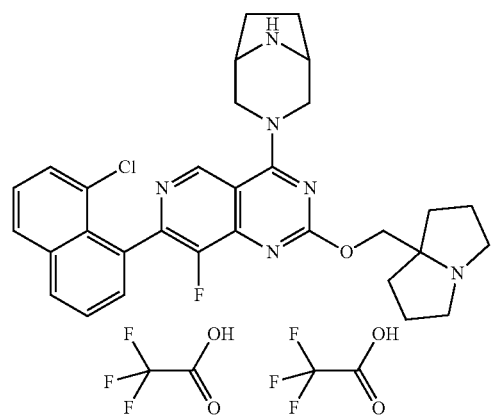

4-((1R,5S)-3,8-diazabicyclo[3.2.1]octan-3-yl)-7-(5-chloroisoquinolin-4-yl)-8-fluoro-2-((tetrahydro-1H-pyrrolizin-7a(5H)-yl)methoxy)pyrido[4,3-d]pyrimidine bis(2,2,2-trifluoroacetate)

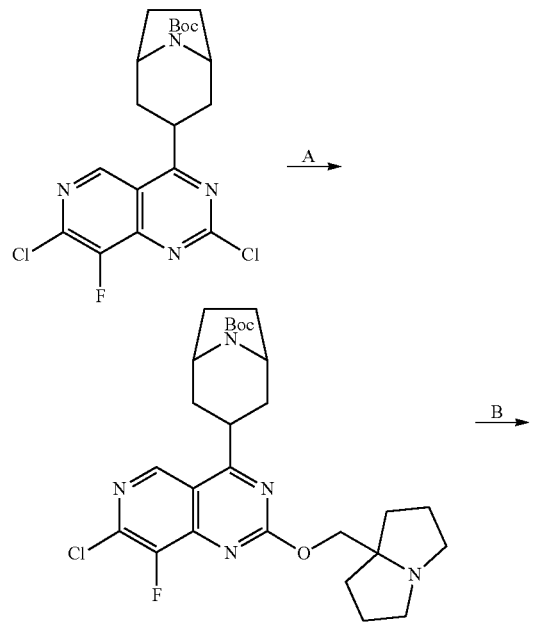

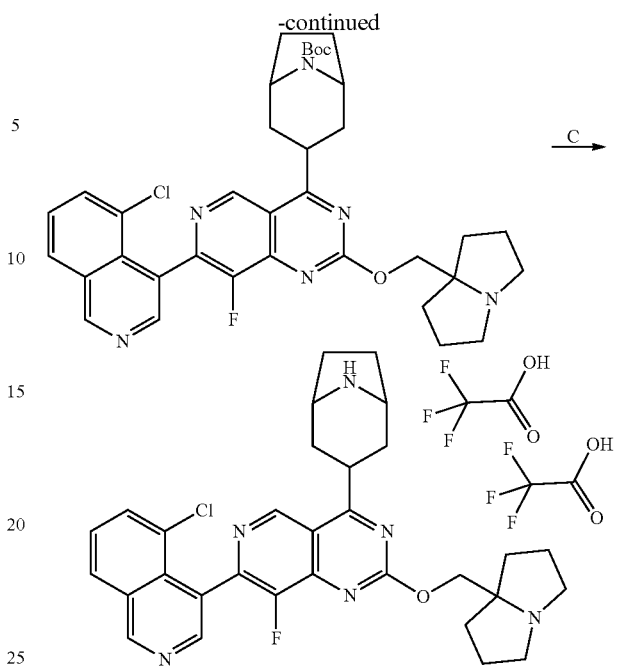

Step A. Tert-butyl (1R,5S)-3-(7-chloro-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate Synthesized according to Example 3, Step G substituting (tetrahydro-1H-pyrrolizin-7a(5H)-yl)methanol in place of 2-(1-methyl-1H-imidazol-2-yl)ethan-1-ol to afford tert-butyl (1R,5S)-3-(7-chloro-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (155 mg, 0.291 mmol, 42%). LCMS (MM-ES+APCI, Pos): m/z 533.2 (M+H).

Step B. tert-butyl (1R,5S)-3-(7-(5-chloroisoquinolin-4-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate: A mixture of tert-butyl (1R,5S)-3-(7-chloro-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (50 mg, 0.094 mmol), 5-chloro-4-(trimethylstannyl)isoquinoline (91.9 mg, 0.281 mmol), BINAP (11.7 mg, 0.019 mmol) and copper(I) iodide (5.4 mg, 0.028 mmol) in toluene (3.13 mL) was degassed with argon for 5 minutes. PdCl₂(dppf) (6.9 mg, 0.009 mmol) was added and the mixture was stirred in a sealed tube at 90° C. for 16 hours. The cooled mixture was partitioned between EtOAc (15 mL) and water (20 mL), and then filtered through GF paper. The aqueous layer was extracted with EtOAc (2×10 mL) and the combined organic phases were washed with brine (20 mL), dried over Na₂SO₄, filtered and concentrated in vacuo. The residue was purified by flash column chromatography eluting with 0-100% (20% MeOH/CH₂Cl₂)/CH₂Cl₂, then 100% (20% MeOH/CH₂Cl₂, 2% NH₄OH)/CH₂Cl₂ to afford tert-butyl (1R,5S)-3-(7-(5-chloroisoquinolin-4-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (10.3 mg, 0.016 mmol, 17%). LCMS (MM-ES+APCI, Pos): m/z 660.3 (M+H).

Step C. 4-((1R,5S)-3,8-diazabicyclo[3.2.1]octan-3-yl)-7-(5-chloroisoquinolin-4-yl)-8-fluoro-2-((tetrahydro-1H-pyrrolizin-7a(5H)-yl)methoxy)pyrido[4,3-d]pyrimidine bis(2,2, 2-trifluoroacetate): To solution of tert-butyl (1R,5S)-3-(7-(5-chloroisoquinolin-4-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (10.3 mg, 0.016 mmol) in CH$_2$Cl$_2$ (0.312 mL) was added TFA (0.024 mL, 0.312 mmol). The mixture was stirred at room temperature for 2 hours. The reaction was concentrated in vacuo. The residue was purified on Gilson prep HPLC (5-95% ACN/H$_2$O over 20 minutes) and then lyophilized to afford 4-((1R,5S)-3,8-diazabicyclo[3.2.1]octan-3-yl)-7-(5-chloroisoquinolin-4-yl)-8-fluoro-2-((tetrahydro-1H-pyrrolizin-7a(5H)-yl)methoxy)pyrido[4,3-d]pyrimidine bis(2,2,2-trifluoroacetate) (6.4 mg, 0.008 mmol, 52%). LCMS (MM-ES+APCI, Pos): m/z 560.2 (M+H).

Example 34

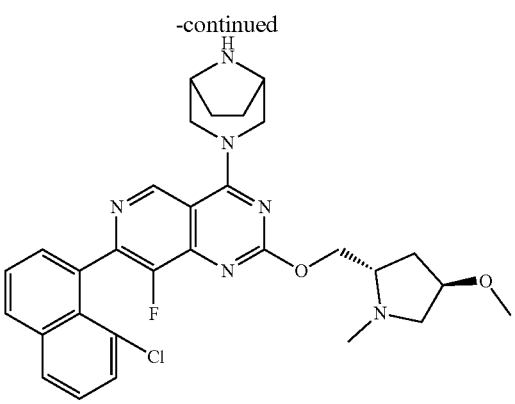

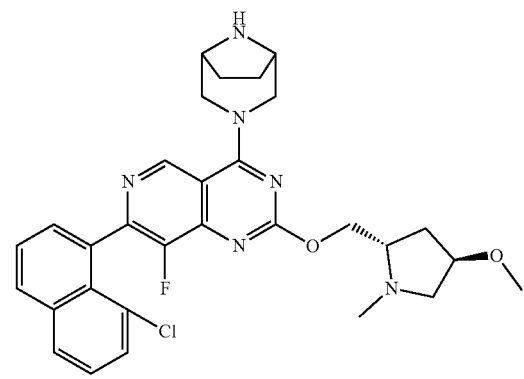 [SMILES: CO[C@@H]1C[C@@H](COc2nc(N3CC4CCC(C3)N4)c3cnc(-c4cccc5cccc(Cl)c45)c(F)c3n2)N(C)C1]

4-((1R,5S)-3,8-diazabicyclo[3.2.1]octan-3-yl)-7-(8-chloronaphthalen-1-yl)-8-fluoro-2-(((2S,4R)-4-methoxy-1-methylpyrrolidin-2-yl)methoxy)pyrido[4,3-d]pyrimidine

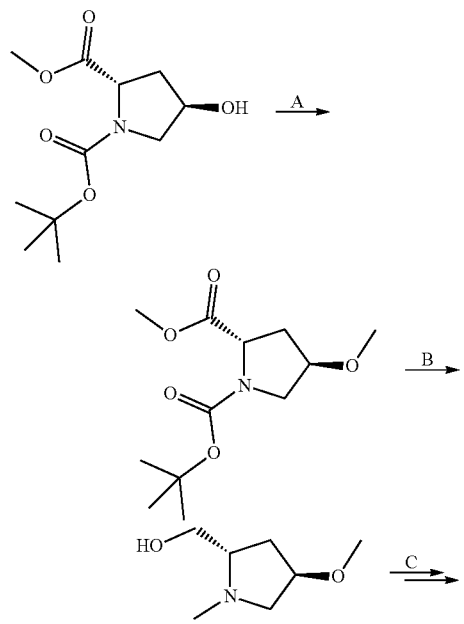

Step A. 1-(tert-butyl) 2-methyl (2S,4R)-4-methoxypyrrolidine-1,2-dicarboxylate: A mixture of 1-(tert-butyl) 2-methyl (2S,4R)-4-hydroxypyrrolidine-1,2-dicarboxylate (500 mg, 2.04 mol), iodomethane (0.330 ml, 5.30 mmol) and silver oxide (520 mg, 2.24 mmol) in acetonitrile (2.1 ml) was stirred at room temperature overnight. Additional silver oxide (520 mg, 2.24 mmol) and iodomethane (0.330 ml, 5.30 mmol) were added and the reaction was stirred at room temperature overnight. Water was added to the reaction mixture and the mixture was extracted twice with ethyl acetate. Pooled organic layers were dried over magnesium sulfate, filtered, and concentrated. The crude mixture was purified by silica gel column to give 1-(tert-butyl) 2-methyl (2S,4R)-4-methoxypyrrolidine-1,2-dicarboxylate as an oil. $^1$H NMR (400 MHz, (CDCl$_3$) δ 4.31 (t, 1H, J=8.0 Hz), 3.73 (s, 3H), 3.72 (s, 3H), 3.65-3.54 (m, 3H), 2.38-2.27 (m, 2H), 1.40 (s, 9H).

Step B. ((2S,4R)-4-methoxy-1-methylpyrrolidin-2-yl) methanol: 1-(tert-butyl) 2-methyl (2S,4R)-4-methoxypyrrolidine-1,2-dicarboxylate (422 mg, 163 mmol) in oxolane (54 ml) in an ice bath was added dropwise to lithium aluminum hydride (4.88 ml, 4.88 mmol). The reaction stirred for 30 minutes followed by heating to 66° C. for 3 hours and stirred at rt overnight. The reaction was quenched by dropwise addition of 1.5 ml of sat. sodium sulfate (aq.) at 0° C. and the reaction was stirred for 1 hour. The mixture was filtered through a bed of Celite. The filtrate was concentrated. The residue was taken up in chloroform and filtered to give ((2S,4R)-4-methoxy-1-methylpyrrolidin-2-yl)methanol as an oil. $^1$H NMR (400 MHz, (CDCl$_3$) δ 3.89-3.83 (m, 1H), 3.69-3.64 (m, 1H), 3.41-3.37 (m, 2H), 3.28 (s, 3H), 2.63-2.59 (m, 1H), 2.33 (s, 3H), 2.10-2.02 (m, 1H), 1.87-1.81 (m, 2H).

Step C. 4-((1R,5S)-3,8-Diazabicyclo[3.2.1]octan-3-yl)-7-(8-chloronaphthalen-1-yl)-8-fluoro-2-(((2S,4R)-4-methoxy-1-methylpyrrolidin-2-yl)methoxy)pyrido[4,3-d]pyrimidine was synthesized according to Example 29, Step H substituting ((2S,4R)-4-methoxy-1-methylpyrrolidin-2-yl)methanol in place of (S)-(1-isopropylpyrrolidin-2-yl)methanol followed by deprotection using Example 2, Step I (13.10 mg, 0.023 mmol, 26% yield). LCMS (MM-ES+APCI, Pos): m/z 563.2 [M+H].

Example 35

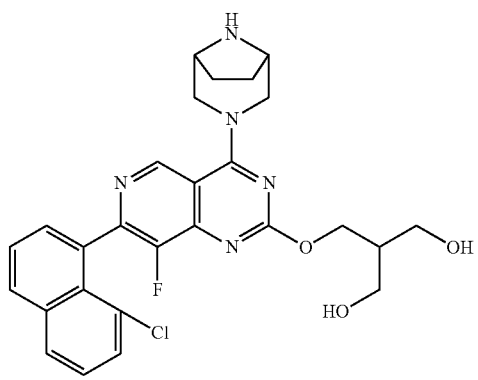 [SMILES: OCC(CO)COc1nc(N2CC3CCC(C2)N3)c2cnc(-c3cccc4cccc(Cl)c34)c(F)c2n1]

2-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)propane-1,3-diol

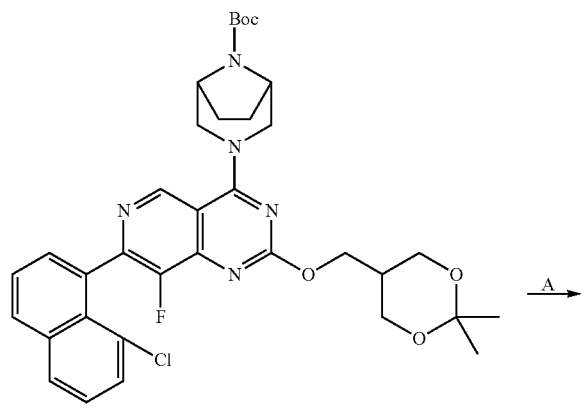

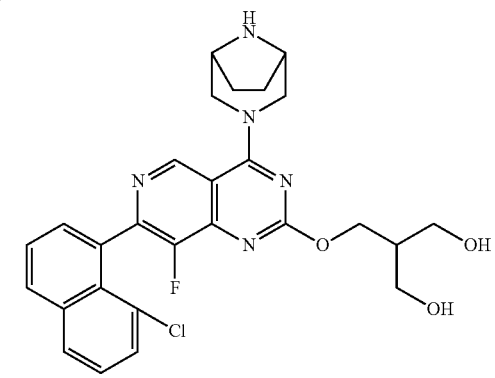

Tert-butyl (1R,5S)-3-(7-(8-chloronaphthalen-1-yl)-2-((2,2-dimethyl-1,3-dioxan-5-yl)methoxy)-8-fluoropyrido[4,3-d]pyrimidin-4-yl)-3,8-diazabicyclo[3.2.1]octane-8-carboxylate: Synthesized according to Example 29, Step H substituting (2,2-dimethyl-1,3-dioxan-5-yl)methanol in place of (S)-(1-isopropylpyrrolidin-2-yl)methanol.

Step A. 2-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)propane-1,3-diol: To a crude mixture of tert-butyl (1R,5S)-3-(7-(8-chloronaphthalen-1-yl)-2-((2,2-dimethyl-1,3-dioxan-5-yl)methoxy)-8-fluoropyrido[4,3-d]pyrimidin-4-yl)-3,8-diazabicyclo[3.2.1]octane-8-carboxylate (60 mg, 0.09034 mmol) were added DCM (0.5 ml), TFA (0.25 ml), and water (0.25 ml), and the mixture was stirred at rt for 3 hours. The solvent was removed and the residue was purified by preparative HPLC (5 to 95% $CH_3CN:H_2O$ with 0.1% TFA, 15 minutes) to give impure product which was further purified by preparative HPLC (5 to 95% $CH_3CN:H_2O$ with 0.1% TFA, 20 minutes) to give desired product (TFA salt). The fraction containing product was added to sat. $NaHCO_3$, and extracted 2× with ethyl acetate. Pooled organic layers were dried over magnesium sulfate, filtered, and concentrated to give desired product (free base) as a white solid (4.31 mg, 0.00823 mmol, 9.1% yield). LCMS (MM-ES+APCI, Pos): m/z 524.2 [M+H].

Example 36

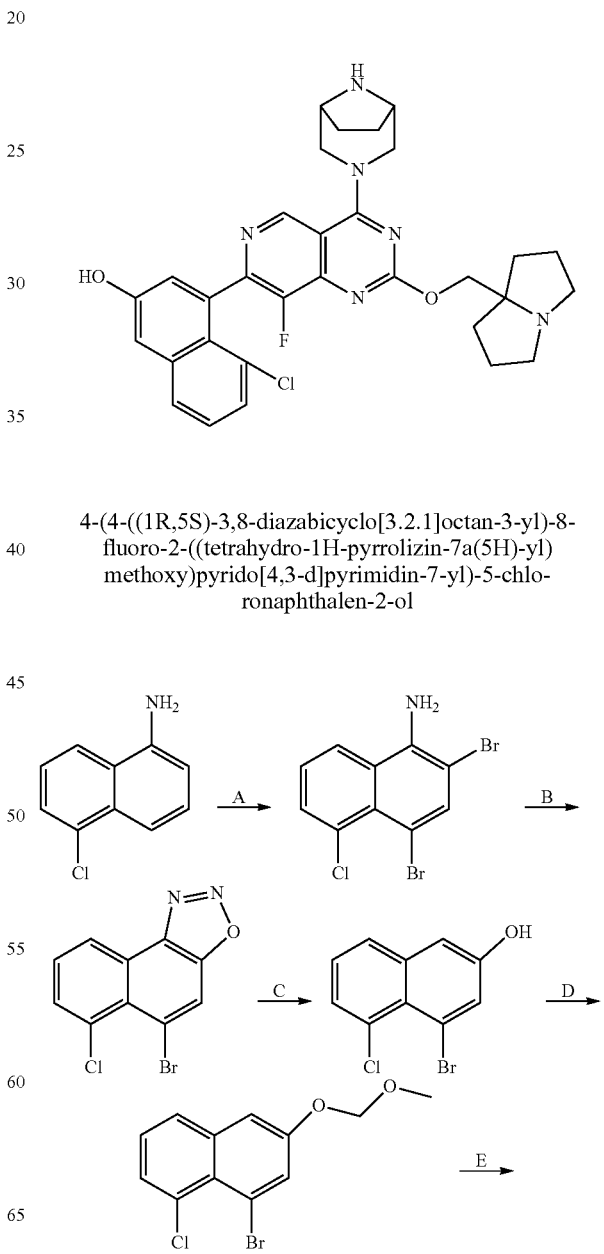

4-(4-((1R,5S)-3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)-5-chloronaphthalen-2-ol

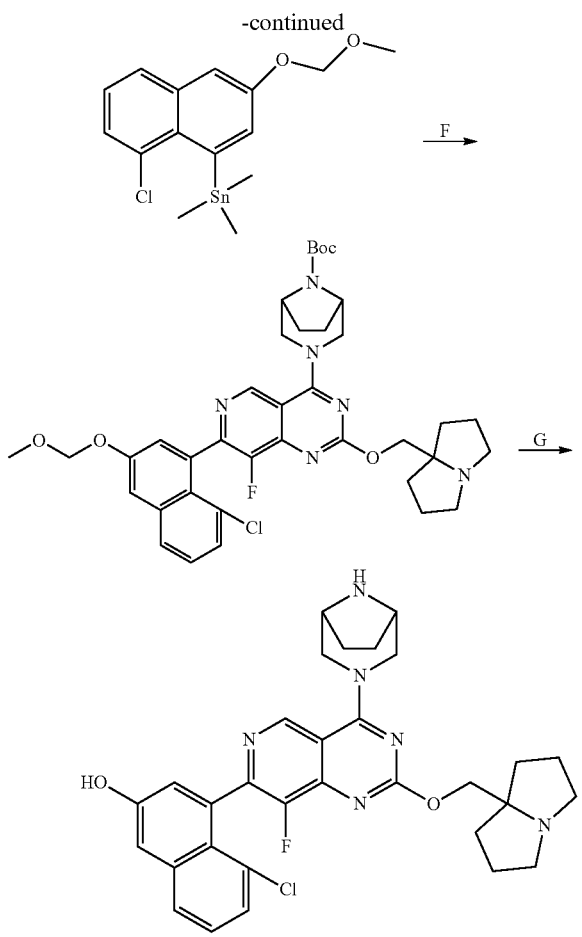

Step A. 2,4-dibromo-5-chloronaphthalen-1-amine: To a solution of 5-Chloronaphthalen-1-amine (1000 mg, 5.63 mmol) in chloroform (30 ml) was added bromine (0.58 ml, 11.3 mmol) in chloroform (30 ml) dropwise. The mixture was heated at 50° C. overnight. Additional bromine (0.58 ml, 11.3 mmol) in 30 ml of chloroform was added dropwise at room temperature and the mixture was warmed to 50° C. for 4 more hours. The reaction was cooled to rt and concentrated in vacuo. Water was added to the residue and the aqueous layer was extracted three times with ethyl acetate. Pooled organic layers were dried over magnesium sulfate, filtered, and concentrated. The residue was purified by silica gel column to give 2,4-dibromo-5-chloronaphthalen-1-amine as a brown solid. $^1$H NMR 400 MHz, (CDCl$_3$) δ 7.94 (s, 1H), 7.76 (d, 1H, J=8.0 Hz), 7.64 (d, 1H, J=8.0 Hz), 7.36 (t, 1H, J=8.0 Hz), 4.46 (bs, 2H).

Step B. 5-bromo-6-chloronaphtho[1,2-d][1,2,3]oxadiazole: 2,4-dibromo-5-chloronaphthalen-1-amine (900 mg, 2.68 mmol) was dissolved in acetic acid (22 ml) and propionic acid (2.2 ml) and cooled in an ice bath followed by addition of sodium nitrite (278 mg, 4.02 mmol) and the reaction was stirred at 0° C. for one hour and rt for one hour. Water was added to the reaction and the aqueous layer was extracted three times with ethyl acetate. The pooled organic layers were dried over magnesium sulfate, filtered, and concentrated. Crude product was purified by silica gel column to give 5-bromo-6-chloronaphtho[1,2-d][1,2,3]oxadiazole as a brown/yellow solid. $^1$H NMR 400 MHz, (CDCl$_3$) δ 7.45-7.38 (m, 2H), 7.31 (s, 1H), 7.22 (dd, 1H, J=8.0, 4.0 Hz).

Step C. 4-bromo-5-chloronaphthalen-2-ol: 5-bromo-6-chloronaphtho[1,2-d][1,2,3]oxadiazole (282 mg, 0.995 mmol) was dissolved in ethanol (15 ml) and THF (15 ml) at 0° C. Sodium borohydride (86.5 mg, 2.29 mmol) was added and warmed up to rt over 2 hours. The solvent was removed, and water was added to the residue. The mixture was acidified with 2 M HCl (aq.) and extracted two times with ethyl acetate. Pooled organic layers were dried over magnesium sulfate, filtered, and concentrated. Crude product was purified by silica gel column to give 4-bromo-5-chloronaphthalen-2-ol as a yellow solid. $^1$H NMR 500 MHz, (CDCl$_3$) δ 7.61-7.58 (m, 2H), 7.48 (d, 1H, J=10.0 Hz), 7.30 (d, 1H, J=10.0 Hz), 7.15 (s, 1H), 5.02 (s, 1H).

Step D. 1-bromo-8-chloro-3-(methoxymethoxy)naphthalene: To a solution of 4-bromo-5-chloronaphthalen-2-ol (203 mg, 0.788 mmol) in THF (3900 μL) at 0° C. was added sodium hydride (47.3 mg, 1.18 mmol). The mixture was stirred at 0° C. for 30 minutes followed by addition of chloromethyl methyl ether (77.8 μL, 1.02 mmol) and the mixture was warmed to room temperature over 2 hours. The reaction was concentrated in vacuo. The residue was partitioned between EtOAc and water and the layers were separated. The aqueous layer was extracted with additional ethyl acetate. Pooled organic layers were dried over magnesium sulfate, filtered, and concentrated. The crude material was purified by silica gel column to give 1-bromo-8-chloro-3-(methoxymethoxy)naphthalene as solid. $^1$H NMR 500 MHz, (CDCl$_3$) δ 7.68 (s, 1H), 7.65 (d, 1H, J=10.0 Hz), 7.49 (d, 1H, J=10.0 Hz), 7.36 (s, 1H), 7.29 (t, 1H, J=10.0 Hz), 5.26 (s, 2H), 3.51 (s, 3H).

Step E. (8-chloro-3-(methoxymethoxy)naphthalen-1-yl)trimethylstannane: A mixture of 1-bromo-8-chloro-3-(methoxymethoxy)naphthalene (200 mg, 0.663 mmol), 1,1,1,2,2,2-hexamethyldistannane (0.69 ml, 3.32 mmol) and toluene (4.1 ml) was sparged with argon for 5 minutes. Tetrakis(triphenylphosphine) Pd(0) (76.6 mg, 0.0663 mmol) was added and the reaction sparged with argon for a few more minutes. The mixture was heated at 110° C. overnight. The reaction was diluted with water and the aqueous layer extracted 2× with hexane. The pooled organic layers were washed with brine, dried over magnesium sulfate, filtered, and concentrated. Crude product was purified by silica gel column to give (8-chloro-3-(methoxymethoxy)naphthalen-1-yl)trimethylstannane as an oil. $^1$H NMR 500 MHz, (CDCl$_3$) δ 7.67 (d, 1H, J=10.0 Hz), 7.56 (s, 1H), 7.46 (d, 1H, J=10.0 Hz), 7.37 (s, 1H), 7.31 (t, 1H, J=10.0 Hz), 5.30 (s, 2H), 3.53 (s, 3H), 0.42 (s, 9H).

Step F. tert-butyl (1R,5S)-3-(7-(8-chloro-3-(methoxymethoxy)naphthalen-1-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate: A mixture of tert-butyl (1R,5S)-3-(7-chloro-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (192 mg, 0.36 mmol), (8-chloro-3-(methoxymethoxy)naphthalen-1-yl)trimethylstannane (208 mg, 0.54 mmol), Copper(I) iodide (20.6 mg, 0.108 mmol), and BINAP (44.9 mg, 0.072 mmol) in toluene (4.0 ml) was sparged with argon for five minutes. Dichloro[1,1'-bis(diphenylphosphino)ferrocene]palladium (II) dichloromethane adduct (29.4 mg, 0.036 mmol) was added and the mixture was sparged with argon for 5 more minutes. The mixture was heated at 90° C. overnight. The reaction was diluted with water and the aqueous layer extracted two times with ethyl acetate. Pooled organic layers were dried over magnesium sulfate, filtered, and concentrated. Crude material was purified by silica gel column to give tert-butyl (1R,5S)-3-(7-(8-chloro-3-

(methoxymethoxy)naphthalen-1-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate. LCMS (MM-ES+APCI, Pos): m/z 719.3 [M+H].

Step G. 4-(4-((1R,5S)-3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)-5-chloronaphthalen-2-ol: To a solution of tert-butyl (1R,5S)-3-(7-(8-chloro-3-(methoxymethoxy)naphthalen-1-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (80 mg, 0.11 mmol) in MeOH (1.1 ml) was added hydrochloric acid solution (4.0 M in 1,4-dioxane, 139 μL, 0.556 mmol). The mixture was stirred at room temperature for 4 hours. Additional hydrochloric acid solution (139 μL, 0.556 mmol) was added and the reaction stirred at rt for 1.5 hours. The reaction was concentrated in vacuo and the residue purified by preparative HPLC C18 (Gilson, 5-50% ACN/H$_2$O with 0.1% TFA) to afford 4-(4-((1R,5S)-3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)-5-chloronaphthalen-2-ol (7.86 mg, 0.00978 mmol, 8.8% yield.) LCMS (MM-ES+APCI, Pos): m/z 575.1 [M+H].

Example 37

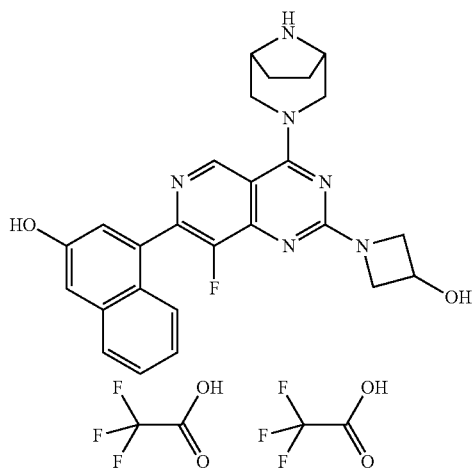

1-(4-((1R,5S)-3,8-diazabicyclo[3.2.1]octan-3-yl)-8-fluoro-7-(3-hydroxynaphthalen-1-yl)pyrido[4,3-d]pyrimidin-2-yl)azetidin-3-ol bis(2,2,2-trifluoroacetate)

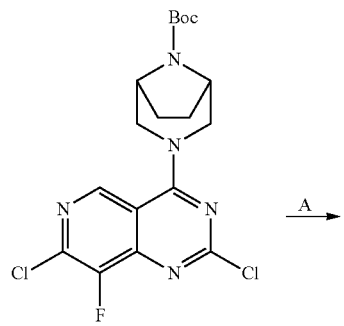

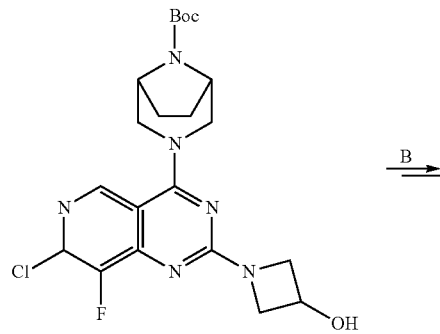

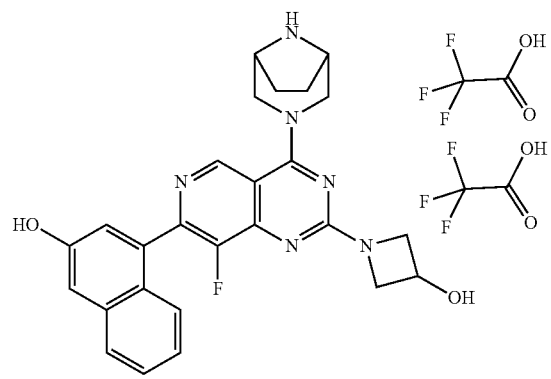

Step A. tert-butyl (1R,5S)-3-(7-chloro-8-fluoro-2-(3-hydroxyazetidin-1-yl)pyrido[4,3-d]pyrimidin-4-yl)-3,8-diazabicyclo[3.2.1]octane-8-carboxylate: To a mixture of tert-butyl (1R,5S)-3-(2,7-dichloro-8-fluoropyrido[4,3-d]pyrimidin-4-yl)-3,8-diazabicyclo[3.2.1]octane-8-carboxylate (100 mg, 0.233 mmol) in dioxane (4 ml) were added azetidin-3-ol (HCl salt, 95%; 27 mg, 0.234 mmol), and Cs$_2$CO$_3$ (228 mg, 0.700 mmol) at rt. The mixture was stirred at 80° C. for 18 hours. Additional azetidin-3-ol (HCl salt, 27 mg, 0.234 mmol) and Cs$_2$CO$_3$ (228 mg, 0.700 mmol) were added and the mixture was heated at 80° C. for 3.5 hours. The mixture was diluted with water and extracted two times with ethyl acetate. Pooled organic layers were dried over magnesium sulfate, filtered, and concentrated. Crude material was purified by silica gel column (24 g, 20 to 50% EtOAc/Hex) to give tert-butyl (1R,5S)-3-(7-chloro-8-fluoro-2-(3-hydroxyazetidin-1-yl)pyrido[4,3-d]pyrimidin-4-yl)-3,8-diazabicyclo[3.2.1]octane-8-carboxylate (19 mg, 0.0409 mmol, 17% yield). LCMS (MM-ES+APCI, Pos): m/z 465.2 (M+H).

Step B: The title compound was synthesized according to Example 3, Step H substituting tert-butyl (1R,5S)-3-(7-chloro-8-fluoro-2-(3-hydroxyazetidin-1-yl)pyrido[4,3-d]pyrimidin-4-yl)-3,8-diazabicyclo[3.2.1]octane-8-carboxylate in place of tert-butyl (1R,5S)-3-(7-chloro-8-fluoro-2-(2-(1-methyl-1H-imidazol-2-yl)ethoxy)pyrido[4,3-d]pyrimidin-4-yl)-3,8-diazabicyclo[3.2.1]octane-8-carboxylate followed by Example 2, step I (1.16 mg, 0.0024 mmol, 70%). LCMS (MM-ES+APCI, Pos): m/z 473.2 (M+H).

Example 38

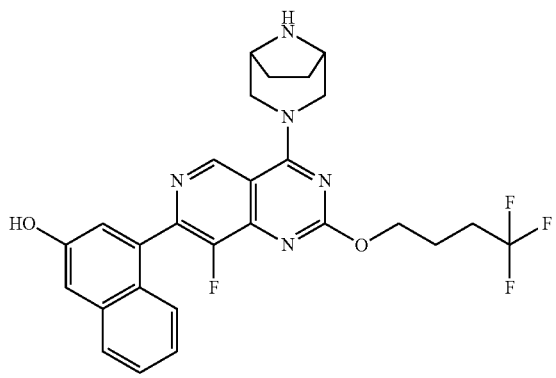 [SMILES: Oc1cc(-c2ncc3c(N4CC5CCC(C4)N5)nc(OCCCC(F)(F)F)nc3c2F)c2ccccc2c1]

4-(4-((1R,5S)-3,8-diazabicyclo[3.2.1]octan-3-yl)-8-fluoro-2-(4,4,4-trifluorobutoxy)pyrido[4,3-d]pyrimidin-7-yl)naphthalen-2-ol Synthesized according to Example 3, Step G and H substituting 4,4,4-trifluorobutan-1-ol in place of 2-(1-methyl-1H-imidazol-2-yl)ethan-1-ol followed by deprotection using Example 2, Step I (45.0 mg, 0.085 mmol, 80%). LCMS (MM-ES+APCI, Pos): m/z 528.2 [M+H].

Example 39

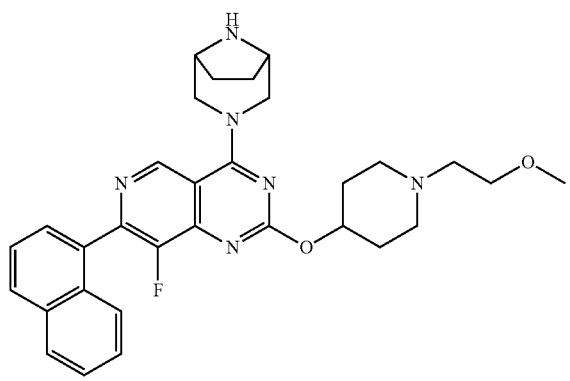 [SMILES: COCCN1CCC(Oc2nc(N3CC4CCC(C3)N4)c3cnc(-c4cccc5ccccc45)c(F)c3n2)CC1]

4-((1R,5S)-3,8-diazabicyclo[3.2.1]octan-3-yl)-8-fluoro-2-((1-(2-methoxyethyl)piperidin-4-yl)oxy)-7-(naphthalen-1-yl)pyrido[4,3-d]pyrimidine Synthesized according to Example 3, Step G substituting 1-(2-methoxyethyl)piperidin-4-ol in place of 2-(1-methyl-1H-imidazol-2-yl)ethan-1-ol and Example 3, Step H substituting naphthalen-1-ylboronic acid in place of 4-(4,4,5,5-tetramethyl-1,3,2-dioxaborolan-2-yl)naphthalen-2-ol followed by deprotection according to the method of Example 2, Step I (7.26 mg, 0.012 mmol, 91% yield). LCMS (MM-ES+APCI, Pos): m/z 543.2 [M+H].

Example 40

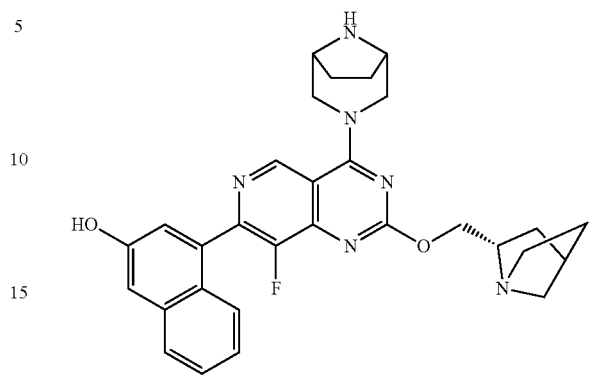

4-(2-(((2 S)-1-azabicyclo[2.2.1]heptan-2-yl)methoxy)-4-((1R,S)-3,8-diazabicyclo[3.2.1]octan-3-yl)-8-fluoropyrido[4,3-d]pyrimidin-7-yl)naphthalen-2-ol

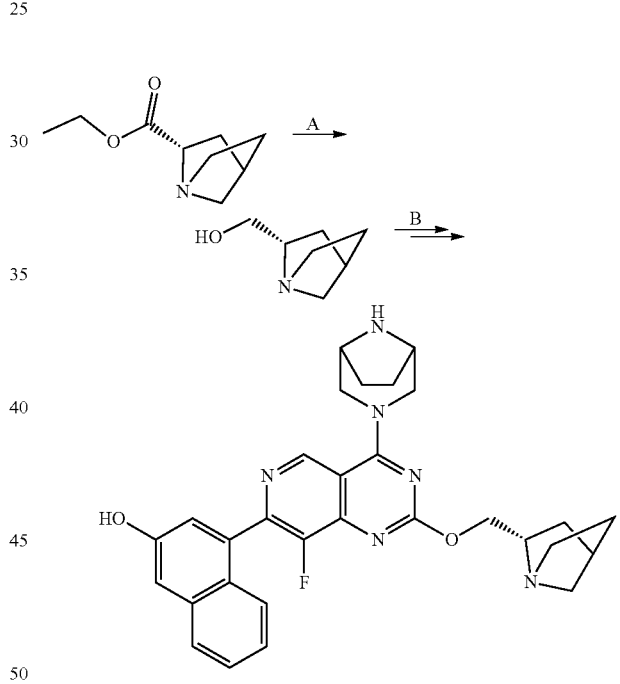

Step A. (1R,2S,4R)-1-azabicyclo[2.2.1]heptan-2-yl)methanol: Lithium aluminum hydride (1M in THF, 2.56 ml, 2.56 mmol) was stirred and cooled in an ice bath. (1R,2S,4R)-ethyl 1-azabicyclo[2.2.1]heptane-2-carboxylate (0.255 g, 1.51 mmol) in THF (2 ml) was added dropwise. The reaction was warmed to room temperature and stirred overnight. The reaction was quenched by dropwise addition of 0.8 ml of sat. sodium sulfate (aq.) at 0° C. and the reaction was stirred for 1 hour. The mixture was filtered through a bed of Celite. The filtrate was concentrated. The residue was taken up in chloroform and filtered to give a crude ((1R,2S,4R)-1-azabicyclo[2.2.1]heptan-2-yl)methanol. $^1$H NMR (400 MHz, (CDCl$_3$) δ 3.32-3.21 (m, 2H), 2.84-2.77 (m, 1H), 2.73-2.66 (m, 1H), 2.53-2.47 (m, 2H), 2.41 (d, 1H, J=10.0 Hz), 2.17 (d, 1H, J=10.0 Hz), 1.63-1.54 (m, 1H), 1.29-1.23 (m, 2H), 1.15-1.08 (m, 1H), 1.01-0.95 (m, 1H).

Step B: The title compound was synthesized according to Example 3, Step G and H substituting (1R,2S,4R)-1-azabicyclo[2.2.1]heptan-2-yl)methanol in place of 2-(1-methyl-1H-imidazol-2-yl)ethan-1-ol followed by deprotection using Example 2, Step I (15.59 mg, 0.030 mmol, 22% yield). LCMS (MM-ES+APCI, Pos): m/z 527.3 [M+H].

Example 41

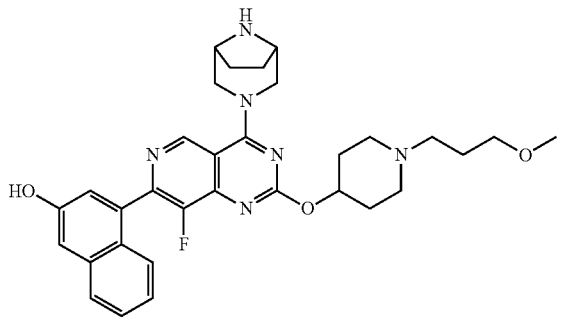 [SMILES: COCCCN1CCC(Oc2nc(N3CC4CCC(C3)N4)c3cnc(-c4cc(O)cc5ccccc45)c(F)c3n2)CC1]

4-(4-((1R,5S)-3,8-diazabicyclo[3.2.1]octan-3-yl)-8-fluoro-2-((1-(3-methoxypropyl)piperidin-4-yl)oxy)pyrido[4,3-d]pyrimidin-7-yl)naphthalen-2-ol Synthesized according to Example 3, Step G and H substituting 1-(3-methoxypropyl)-4-piperidinol in place of 2-(1-methyl-1H-imidazol-2-yl)ethan-1-ol followed by deprotection using Example 2, Step I (11.6 mg, 0.020 mmol, 34% yield). LCMS (MM-ES+APCI, Pos): m/z 573.3 [M+H].

Example 42

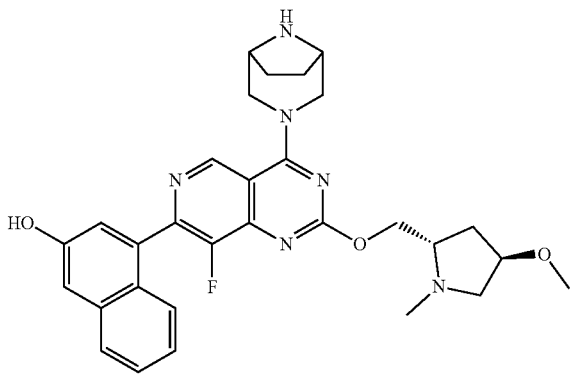 [SMILES: CO[C@@H]1C[C@@H](COc2nc(N3CC4CCC(C3)N4)c3cnc(-c4cc(O)cc5ccccc45)c(F)c3n2)N(C)C1]

4-(4-((1R,5S)-3,8-diazabicyclo[3.2.1]octan-3-yl)-8-fluoro-2-(((2S,4R)-4-methoxy-1-methylpyrrolidin-2-yl)methoxy)pyrido[4,3-d]pyrimidin-7-yl)naphthalen-2-ol Synthesized according to Example 3, Step G and H substituting ((2S,4R)-4-methoxy-1-methylpyrrolidin-2-yl)methanol in place of 2-(1-methyl-1H-imidazol-2-yl)ethan-1-ol followed by deprotection using Example 2, Step I (8.32 mg, 0.015 mmol, 35% yield). LCMS (MM-ES+APCI, Pos): m/z 545.3 [M+H].

Example 43

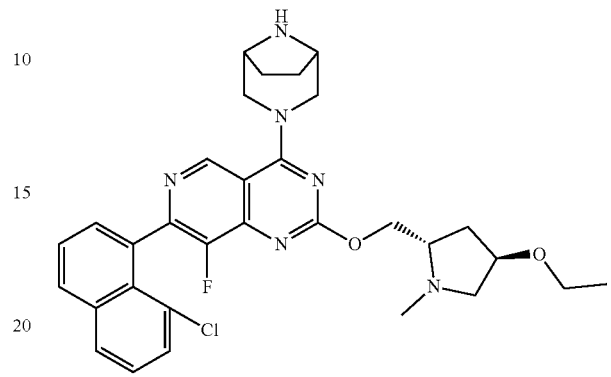

4-((1R,5S)-3,8-diazabicyclo[3.2.1]octan-3-yl)-7-(8-chloronaphthalen-1-yl)-2-(((2S,4R)-4-ethoxy-1-methylpyrrolidin-2-yl)methoxy)-8-fluoropyrido[4,3-d]pyrimidine Synthesized according to Example 34 substituting ethyl iodide for methyl iodide in Step A (6.95 mg, 0.00897 mmol, 87% yield). LCMS (MM-ES+APCI, Pos): m/z 577.2 [M+H].

Example 44

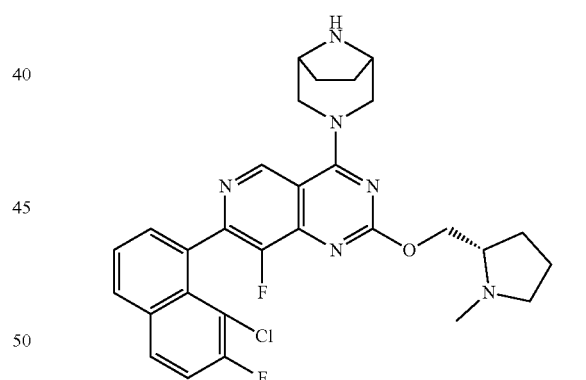

4-((1R,5S)-3,8-diazabicyclo[3.2.1]octan-3-yl)-7-(8-chloro-7-fluoronaphthalen-1-yl)-8-fluoro-2-(((S)-1-methylpyrrolidin-2-yl)methoxy)pyrido[4,3-d]pyrimidine

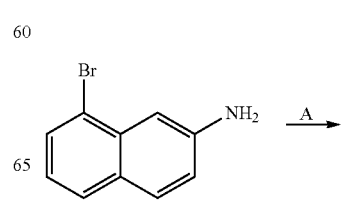

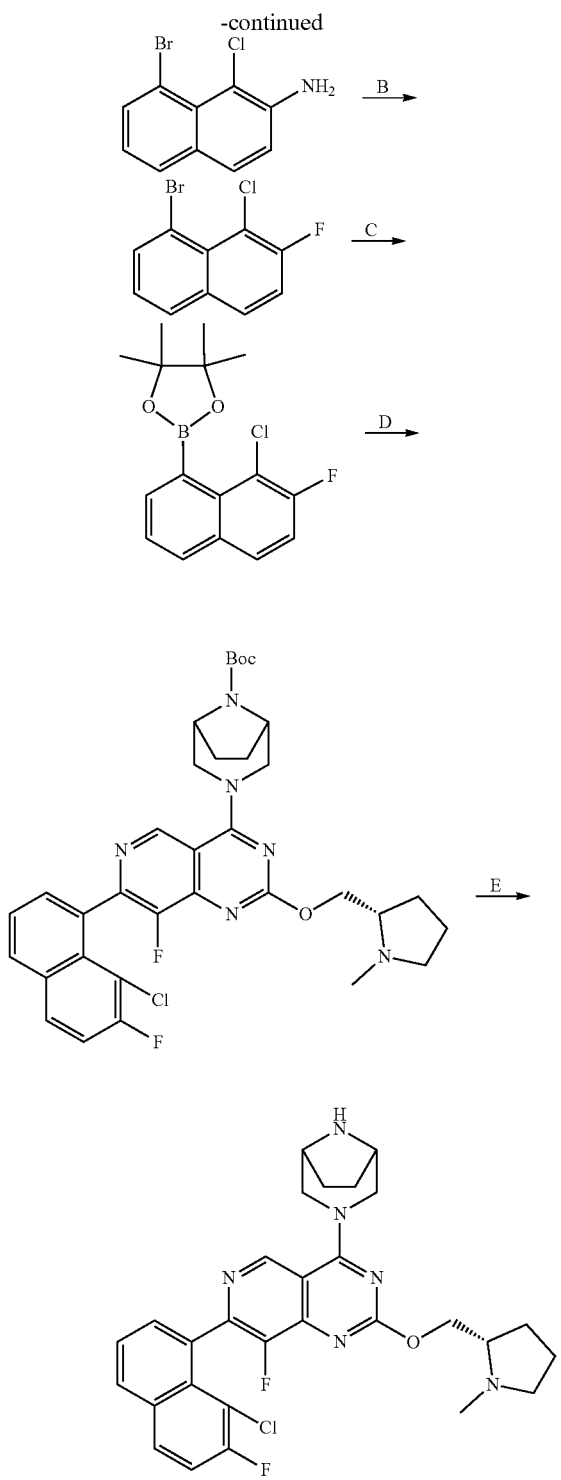

Step A. 8-bromo-1-chloronaphthalen-2-amine: To a mixture of 8-bromonaphthalen-2-amine (2.3 g, 10 mmol) in CCl$_4$ (104 ml, 10 mmol) was added NCS (1.4 g, 10 mmol) and the resulting mixture was heated at 50° C. for 2 h. The mixture was cooled to rt and stirred overnight. The slurry was filtered to isolate solid product. The solid was purified by column chromatography eluting with 0-20% hex/EtOAc to give product (1.9 g, 72%). LCMS (MM-ES+APCI, Pos): m/z 256.1, 258.1 [M+H]

Step B. 8-bromo-1-chloro-2-fluoronaphthalene: A slurry of nitrosonium tetrafluoroborate (378 mg, 3.23 mmol) in DCM (2.5 ml) was cooled in an ice bath. 8-bromo-1-chloronaphthalen-2-amine (680 mg, 2.65 mmol) was added. The mixture was stirred for 1 hour and the solvent was removed. 1,2-dichlorobenzene (10 ml) was added and the reaction mixture was heated at 160 to 180° C. for one hour. The solvent was removed, and the residue was purified by silica gel column (80 g, 100% hexane) to give 8-bromo-1-chloro-2-fluoronaphthalene as a white solid. $^1$H NMR 400 MHz, (CDCl$_3$) δ 7.95-7.93 (m, 1H), 7.80 (d, 1H, J=8.0 Hz), 7.76 (dd, 1H, J=8.0, 4.0 Hz), 7.36 (t, 1H, J=8.0 Hz), 7.26 (t, 1H, J=8.0 Hz).

Step C. 2-(8-chloro-7-fluoronaphthalen-1-yl)-4,4,5,5-tetramethyl-1,3,2-dioxaborolane: To a solution of 8-bromo-1-chloro-2-fluoronaphthalene (223 mg, 0.859 mmol) in dioxane (4.3 ml) were added potassium acetate (253 mg, 2.58 mmol) and 4,4,4',4',5,5,5',5'-octamethyl-2,2'-bi(1,3,2-dioxaborolane) (436 mg, 1.72 mmol). The reaction mixture was sparged with argon for 5 minutes. PdCl$_2$(dppf) (31.4 mg, 0.0430 mmol) was added, and the reaction mixture was heated to 95° C. for 6 hours. The reaction was cooled to rt and water was added. The aqueous layer was extracted 2× with ethyl acetate/hexane (1:1). The pooled organic layers were dried over magnesium sulfate, filtered, and concentrated. The crude material was purified by silica gel column (24 g, 0 to 10% EtOAc/Hexane) to give 2-(8-chloro-7-fluoronaphthalen-1-yl)-4,4,5,5-tetramethyl-1,3,2-dioxaborolane as a white solid. $^1$H NMR 400 MHz, (CDCl$_3$) δ 7.84 (d, 1H, J=8.0 Hz), 7.75 (dd, 1H, J=8.0, 4.0 Hz), 7.70 (d, 1H, J=8.0 Hz), 7.49-7.45 (m, 1H), 7.32 (t, 1H, J=8.0 Hz), 1.45 (s, 12H).

Step D. tert-butyl (1R,5S)-3-(7-(8-chloro-7-fluoronaphthalen-1-yl)-8-fluoro-2-(((S)-1-methylpyrrolidin-2-yl)methoxy)pyrido[4,3-d]pyrimidin-4-yl)-3,8-diazabicyclo[3.2.1]octane-8-carboxylate: A mixture of 2-(8-chloro-7-fluoronaphthalen-1-yl)-4,4,5,5-tetramethyl-1,3,2-dioxaborolane (157 mg, 0.514 mmol), tert-butyl (1R,5S)-3-(7-chloro-8-fluoro-2-(((S)-1-methylpyrrolidin-2-yl)methoxy)pyrido[4,3-d]pyrimidin-4-yl)-3,8-diazabicyclo[3.2.1]octane-8-carboxylate (synthesized according to Example 3, Step A-G substituting (S)-(1-methylpyrrolidin-2-yl)methanol in place of 2-(1-methyl-1H-imidazol-2-yl)ethan-1-ol) (124 mg, 0.245 mmol), K$_2$CO$_3$ (169 mg, 1.22 mmol) and Pd(Ph$_3$P)$_4$ (28.3 mg, 0.0245 mmol) in toluene (2.4 ml), EtOH (0.64 mL), and water (0.32 mL) was sparged with argon for 5 minutes, heated at 85° C. overnight. The mixture was cooled to room temperature water was added and the mixture extracted 2× with ethyl acetate. The pooled organics were dried over magnesium sulfate, filtered, and concentrated. Crude was purified by silica gel column (24 g, 0 to 10% MeOH/DCM) to give a crude product. LCMS (MM-ES+APCI, Pos): m/z 651.1 [M+H].

Step E: 4-((1R,5S)-3,8-diazabicyclo[3.2.1]octan-3-yl)-7-(8-chloro-7-fluoronaphthalen-1-yl)-8-fluoro-2-(((S)-1-methylpyrrolidin-2-yl)methoxy)pyrido[4,3-d]pyrimidine The title compound was synthesized according to the method of Example 2, step I (6.93 mg, 0.093 mmol, 86% yield). LCMS (MM-ES+APCI, Pos): m/z 551.2 [M+H].

Example 45

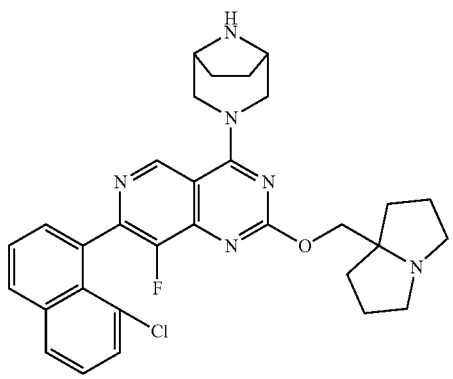 [SMILES: Fc1c(-c2cccc3cccc(Cl)c23)ncc2c(N3CC4CCC(C3)N4)nc(OCC34CCCN3CCC4)nc12]

4-((1R,5S)-3,8-diazabicyclo[3.2.1]octan-3-yl)-7-(8-chloronaphthalen-1-yl)-8-fluoro-2-((tetrahydro-1H-pyrrolizin-7a(5H)-yl)methoxy)pyrido[4,3-d]pyrimidine Synthesized according to Example 29, Step H substituting tetrahydro-1H-pyrrolizine-7a(5H)-methanol in place of (S)-(1-isopropylpyrrolidin-2-yl)methanol followed by deprotection using Example 2, Step I (5.93 mg, 0.00786 mmol, 18% yield). LCMS (MM-ES+APCI, Pos): m/z 559.2 [M+H].

Example 46

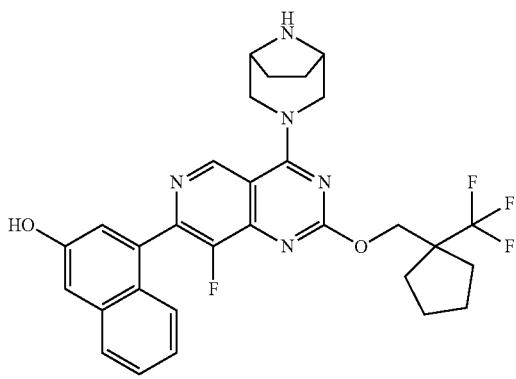 [SMILES: Oc1cc(-c2ncc3c(N4CC5CCC(C4)N5)nc(OCC4(C(F)(F)F)CCCC4)nc3c2F)c2ccccc2c1]

4-(4-((1R,5S)-3,8-diazabicyclo[3.2.1]octan-3-yl)-8-fluoro-2-((1-(trifluoromethyl)cyclopentyl)methoxy)pyrido[4,3-d]pyrimidin-7-yl)naphthalen-2-ol Synthesized according to Example 3, Step G and H substituting [1-(trifluoromethyl)cyclopentyl]methanol in place of 2-(1-methyl-1H-imidazol-2-yl)ethan-1-ol followed by deprotection according to the method of Example 2, Step I (10.29 mg, 0.013 mmol, 9% yield). LCMS (MM-ES+APCI, Pos): m/z 568.2 [M+H].

Example 47

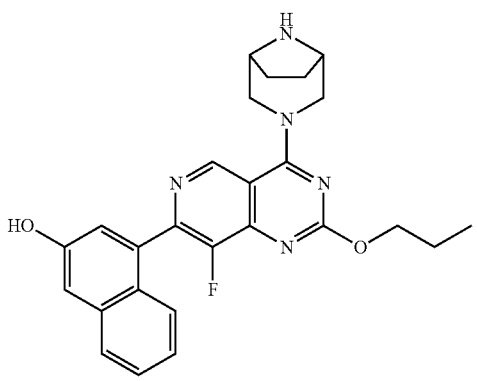 [SMILES: CCCOc1nc(N2CC3CCC(C2)N3)c2cnc(-c3cc(O)cc4ccccc34)c(F)c2n1]

4-(4-((1R,5S)-3,8-diazabicyclo[3.2.1]octan-3-yl)-8-fluoro-2-propoxypyrido[4,3-d]pyrimidin-7-yl)naphthalen-2-ol Synthesized according to Example 3, Step G and H substituting 1-Propanol in place of 2-(1-methyl-1H-imidazol-2-yl)ethan-1-ol followed by deprotection according to the method of Example 2, Step I (37.91 mg, 0.0578 mmol, 32% yield). LCMS (MM-ES+APCI, Pos): m/z 460.2 [M+H].

Example 48

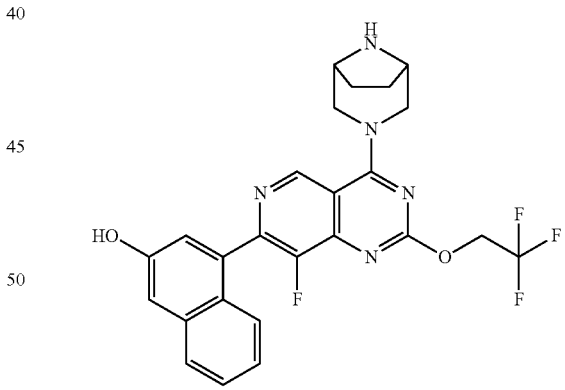

4-(4-((1R,5S)-3,8-diazabicyclo[3.2.1]octan-3-yl)-8-fluoro-2-(2,2,2-trifluoroethoxy)pyrido[4,3-d]pyrimidin-7-yl)naphthalen-2-ol Synthesized according to Example 3, Step G and H substituting 2,2,2-Trifluoroethanol in place of 2-(1-methyl-1H-imidazol-2-yl)ethan-1-ol followed by deprotection according to the method of Example 2, Step I (42.15 mg, 0.0606 mmol, 33% yield). LCMS (MM-ES+APCI, Pos): m/z 500.2 [M+H].

Example 49

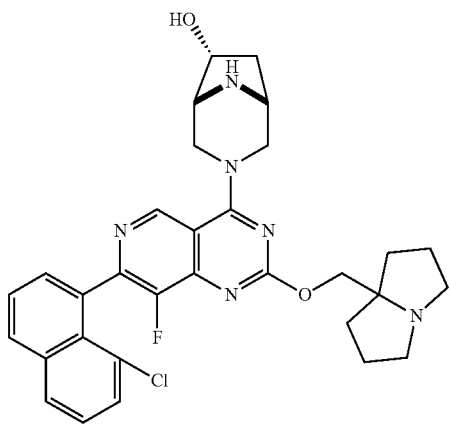

(1R,5R,6R)-3-(7-(8-chloronaphthalen-1-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octan-6-ol

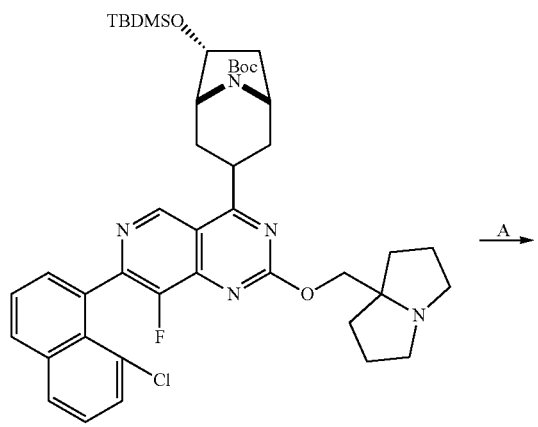

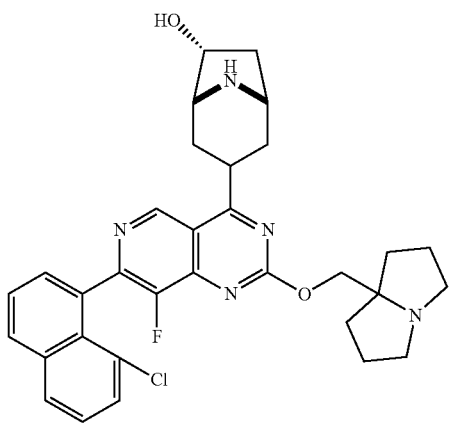

Tert-butyl 6-((tert-butyldimethylsilyl)oxy)-3-(7-(8-chloronaphthalen-1-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate: Synthesized according to Example 2, Step H substituting tert-butyl 6-((tert-butyldimethylsilyl)oxy)-3-(2-chloro-7-(8-chloronaphthalen-1-yl)-8-fluoropyrido[4,3-d]pyrimidin-4-yl)-3,8-diazabicyclo[3.2.1]octane-8-carboxylate and hexahydro-1H-pyrrolizin-7a-ylmethanol in place of tert-butyl (1R,5S)-3-(2-chloro-8-fluoro-7-(3-(pivaloyloxy)naphthalen-1-yl)pyrido[4,3-d]pyrimidin-4-yl)-3,8-diazabicyclo[3.2.1]octane-8-carboxylate and (S)-(1-methylpyrrolidin-2-yl)methanol.

Step A: 3-(7-(8-chloronaphthalen-1-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octan-6-ol: A mixture tert-butyl 6-((tert-butyldimethylsilyl)oxy)-3-(7-(8-chloronaphthalen-1-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (27 mg, 0.034200 mmol) was placed in 7:3 DCM:TFA (1 mL) and stirred at RT for 3 hour. Solvents were removed and 2.5 M HCl in ethanol (3 ml) was added to the residue. The mixture was stirred at rt for 3 hours. The reaction was concentrated and the residue was purified by preparative HPLC (5 to 95% CH$_3$CN:H$_2$O with 0.1% TFA) to give 3-(7-(8-chloronaphthalen-1-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octan-6-ol (10.29, 0.0128 mmol, 38% yield). LCMS (MM-ES+APCI, Pos): m/z 575.2 [M+H].

Example 50

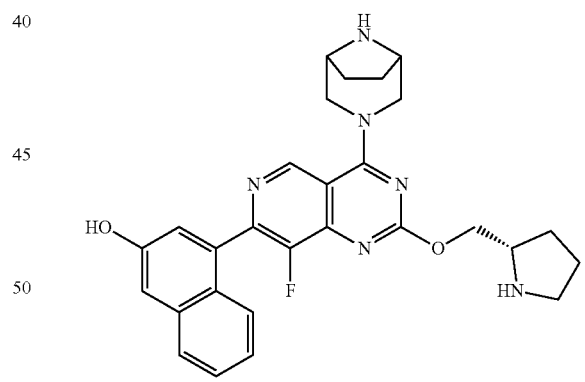

4-(4-((1R,5S)-3,8-diazabicyclo[3.2.1]octan-3-yl)-8-fluoro-2-(((S)-pyrrolidin-2-yl)methoxy)pyrido[4,3-d]pyrimidin-7-yl)naphthalen-2-ol Synthesized according to Example 3, Step G and H substituting tert-butyl (S)-2-(hydroxymethyl)pyrrolidine-1-carboxylate in place of 2-(1-methyl-1H-imidazol-2-yl)ethan-1-ol followed by deprotection according to the method of Example 2, Step I (53.03 mg, 0.0761 mmol, 97% yield). LCMS (MM-ES+APCI, Pos): m/z 501.2 [M+H].

Example 51

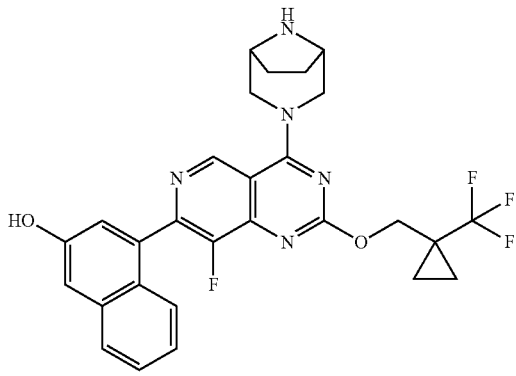 [SMILES: Oc1cc(-c2ncc3c(N4CC5CCC(C4)N5)nc(OCC4(C(F)(F)F)CC4)nc3c2F)c2ccccc2c1]

4-(4-((1R,5S)-3,8-diazabicyclo[3.2.1]octan-3-yl)-8-fluoro-2-((1-(trifluoromethyl)cyclopropyl)methoxy)pyrido[4,3-d]pyrimidin-7-yl)naphthalen-2-ol Synthesized according to Example 3, Step G and H substituting [1-(Trifluoromethyl)cyclopropyl]methanol in place of 2-(1-methyl-1H-imidazol-2-yl)ethan-1-ol followed by deprotection according to the method of Example 2, Step I (18.0 mg, 0.0245 mmol, 15.7% yield). LCMS (MM-ES+APCI, Pos): m/z 540.2 [M+H].

Example 52

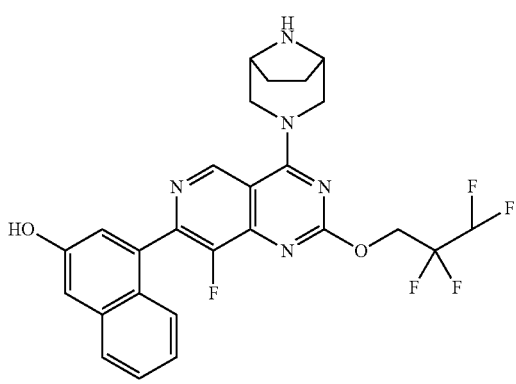 [SMILES: Oc1cc(-c2ncc3c(N4CC5CCC(C4)N5)nc(OCC(F)(F)C(F)F)nc3c2F)c2ccccc2c1]

4-(4-((1R,5S)-3,8-diazabicyclo[3.2.1]octan-3-yl)-8-fluoro-2-(2,2,3,3-tetrafluoropropoxy)pyrido[4,3-d]pyrimidin-7-yl)naphthalen-2-ol Synthesized according to Example 3, Step G and H substituting 2,2,3,3-Tetrafluoropropan-1-ol in place of 2-(1-methyl-1H-imidazol-2-yl)ethan-1-ol and deprotection according to the method of Example 2, Step I (31.7 mg, 0.0435 mmol, 33.5% yield). LCMS (MM-ES+APCI, Pos): m/z 532.2 [M+H].

Example 53

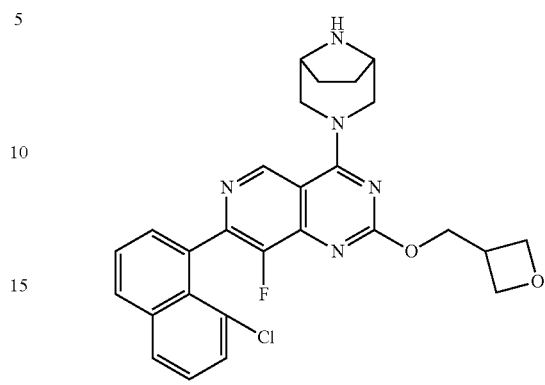

4-((1R,5S)-3,8-diazabicyclo[3.2.1]octan-3-yl)-7-(8-chloronaphthalen-1-yl)-8-fluoro-2-(oxetan-3-yl-methoxy)pyrido[4,3-d]pyrimidine Synthesized according to Example 29, Step H substituting oxetan-3-ylmethanol in place of (S)-(1-isopropylpyrrolidin-2-yl)methanol followed by deprotection using Example 2, Step I (10.4 mg, 0.0206 mmol, 34% yield). LCMS (MM-ES+APCI, Pos): m/z 506.2 [M+H].

Example 54

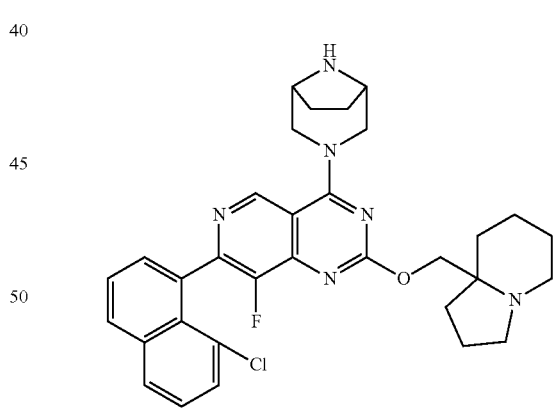

4-((1R,5S)-3,8-diazabicyclo[3.2.1]octan-3-yl)-7-(8-chloronaphthalen-1-yl)-8-fluoro-2-((hexahydroin-dolizin-8a(1H)-yl)methoxy)pyrido[4,3-d]pyrimidine Synthesized according to Example 29, Step H substituting (hexahydroindolizin-8a(1H)-yl)methanol in place of (S)-(1-isopropylpyrrolidin-2-yl)methanol followed by deprotection using Example 2, Step I (6.20 mg, 0.00806 mmol, 42% yield). LCMS (MM-ES+APCI, Pos): m/z 573.3 [M+H].

Example 55

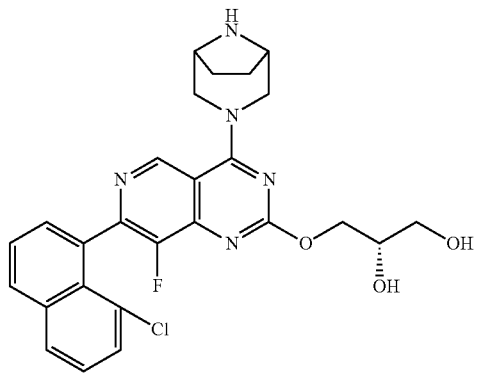 [SMILES: OC[C@H](O)COc1nc(N2CC3CCC(C2)N3)c2cnc(-c3cccc4cccc(Cl)c34)c(F)c2n1]

(S)-3-((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)propane-1,2-diol Synthesized according to Example 29, Step H substituting (R)-(−)-2,2-Dimethyl-1,3-dioxolane-4-methanol in place of (S)-(1-isopropylpyrrolidin-2-yl)methanol followed by deprotection using Example 35, Step A (15.1, 0.025 mmol, 23% yield). LCMS (MM-ES+APCI, Pos): m/z 510.2 [M+H].

Example 56

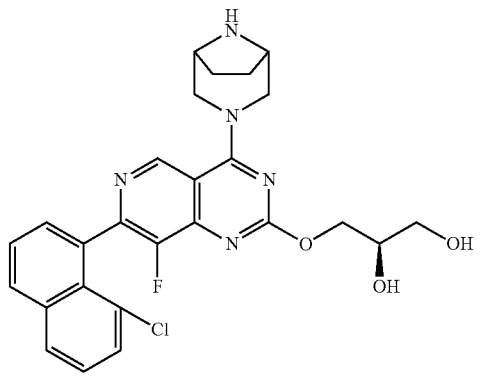 [SMILES: OC[C@@H](O)COc1nc(N2CC3CCC(C2)N3)c2cnc(-c3cccc4cccc(Cl)c34)c(F)c2n1]

(R)-3-((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)propane-1,2-diol Synthesized according to Example 29, Step H substituting (s)-(+)-2,2-dimethyl-1,3-dioxolane-4-methanol in place of (S)-(1-isopropylpyrrolidin-2-yl)methanol followed by deprotection using Example 35, Step A (16.6 mg, 0.0324 mmol, 30% yield). LCMS (MM-ES+APCI, Pos): m/z 510.2 [M+H].

Example 57

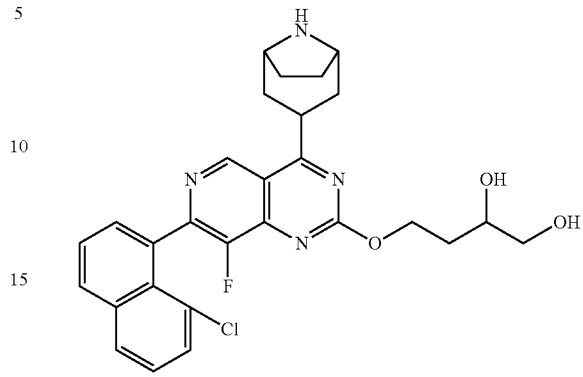

4-((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)butane-1,2-diol Synthesized according to Example 29, Step H substituting 2-(2,2-Dimethyl-1,3-dioxolan-4-yl)ethanol in place of (S)-(1-isopropylpyrrolidin-2-yl)methanol followed by deprotection using Example 35, Step A (12.1 mg, 0.0194 mmol, 31% yield). LCMS (MM-ES+APCI, Pos): m/z 524.2 [M+H].

Example 58

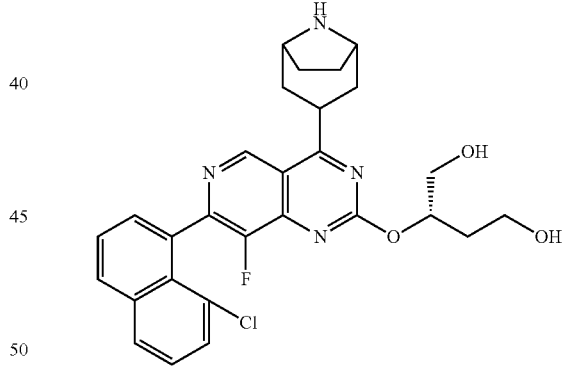

(S)-2-((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)butane-1,4-diol

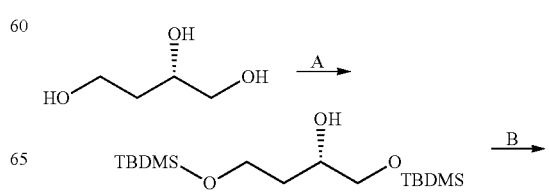

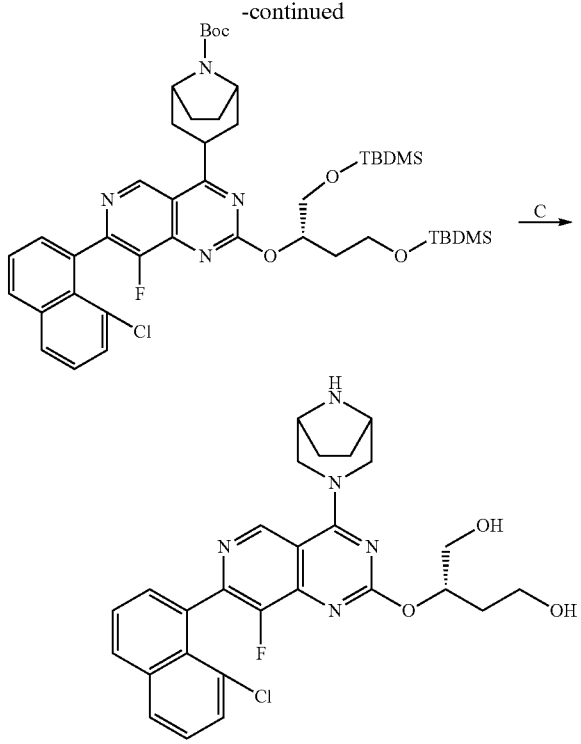

Step A. (S)-2,2,3,3,10,10,11,11-octamethyl-4,9-dioxa-3,10-disiladodecan-6-ol: To a mixture of (S)-(−)-1,2,4-butanetriol (776 mg, 7.3 mmol), tert-butyldimethylsilyl chloride (2425 mg, 16.1 mmol), and 4-(dimethylamino)pyridine (89.3 mg, 0.73 mmol) in dichloromethane (15.6 ml) was added triethylamine (1.77 g, 17.55 mmol). The reaction mixture was stirred at room temperature overnight. Chloroform was added to the mixture and the organics were washed with saturated sodium bicarbonate, dried over magnesium sulfate, filtered, and concentrated. Crude product was purified by silica gel column to give (S)-2,2,3,3,10,10,11,11-octamethyl-4,9-dioxa-3,10-disiladodecan-6-ol. LCMS (MM-ES+APCI, Pos): m/z 335.3 [M+H].

Step B. tert-butyl (1R,5S)-3-(7-(8-chloronaphthalen-1-yl)-8-fluoro-2-(((S)-2,2,3,3,10,10,11,11-octamethyl-4,9-dioxa-3,10-disiladodecan-6-yl)oxy)pyrido[4,3-d]pyrimidin-4-yl)-3,8-diazabicyclo[3.2.1]octane-8-carboxylate: To a solution of (S)-2,2,3,3,10,10,11,11-octamethyl-4,9-dioxa-3,10-disiladodecan-6-ol (30 mg, 0.090 mmol) in dimethyl formamide (0.5 ml) cooled in an ice bath was added sodium hydride (5.6 mg, 0.23 mmol). After 5 minutes, the reaction was warmed to rt and stirred at rt for 50 minutes. The reaction was cooled in an ice bath and tert-butyl (1R,5S)-3-(2-chloro-7-(8-chloronaphthalen-1-yl)-8-fluoropyrido[4,3-d]pyrimidin-4-yl)-3,8-diazabicyclo[3.2.1]octane-8-carboxylate (50 mg, 0.090 mmol) was added. The reaction was warmed to rt over 3 hours. The reaction was quenched with water and the aqueous layer extracted twice with ethyl acetate. Pooled organic layers were dried over magnesium sulfate, filtered, and concentrated. Crude material was purified by silica gel column to give tert-butyl (1R,5S)-3-(7-(8-chloronaphthalen-1-yl)-8-fluoro-2-(((S)-2,2,3,3,10,10,11,11-octamethyl-4,9-dioxa-3,10-disiladodecan-6-yl)oxy)pyrido[4,3-d]pyrimidin-4-yl)-3,8-diazabicyclo[3.2.1]octane-8-carboxylate.

Step C. (S)-2-((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)butane-1,4-diol: tert-butyl (1R,5S)-3-(7-(8-chloronaphthalen-1-yl)-8-fluoro-2-(((S)-2,2,3,3,10,10,11,11-octamethyl-4,9-dioxa-3,10-disiladodecan-6-yl)oxy)pyrido[4,3-d]pyrimidin-4-yl)-3,8-diazabicyclo[3.2.1]octane-8-carboxylate (11 mg, 0.013 mmol) was added to HCl (2 ml, 2.5 M in ethanol) at 0° C. and the mixture was stirred for 2 hours. The reaction was concentrated in vacuo. To the residue were added DCM (0.75 ml) and TFA (0.25 ml) and the reaction was stirred at rt for 1 hour. The reaction was concentrated in vacuo and the residue was purified by preparative HPLC (5 to 95% CH$_3$CN:H$_2$O with 0.1% TFA, 20 minutes) to give (S)-2-((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)butane-1,4-diol (3.52 mg, 0.00566 mmol, 44% yield). LCMS (MM-ES+APCI, Pos): m/z 524.2 [M+H].

Example 59

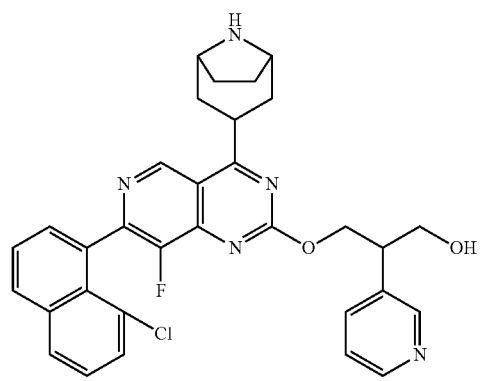 [SMILES: OCC(COc1nc(C2CC3CCC(C2)N3)c2cnc(-c3cccc4cccc(Cl)c34)c(F)c2n1)c1cccnc1]

3-((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)-2-(pyridin-3-yl)propan-1-ol Synthesized according to Example 29, Step H substituting 2-(pyridin-3-yl)propane-1,3-diol in place of (S)-(1-isopropylpyrrolidin-2-yl)methanol followed by deprotection using Example 2, Step I (25.23 mg, 0.0377 mmol, 87% yield). LCMS (MM-ES+APCI, Pos): m/z 571.3 [M+H].

Example 60

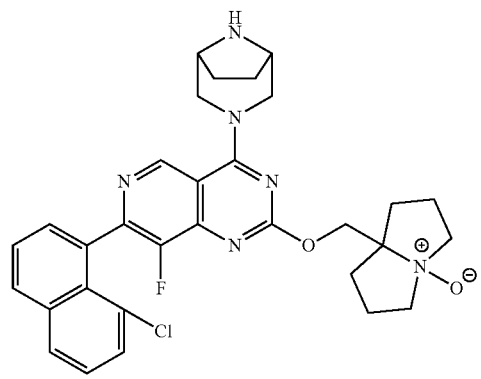 [SMILES: [O-][N+]12CCCC1(COc1nc(N3CC4CCC(C3)N4)c3cnc(-c4cccc5cccc(Cl)c45)c(F)c3n1)CCC2]

7a-(((4-(((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)hexahydropyrrolizine 4(1H)-oxide

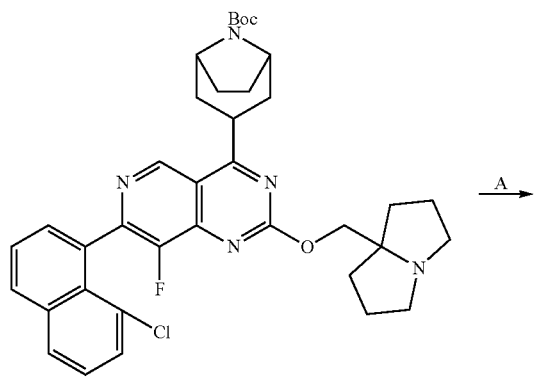

Step A. 7a-(((4-(((1R,5S)-8-(tert-butoxycarbonyl)-3,8-diazabicyclo[3.2.1]octan-3-yl)-7-(8-chloronaphthalen-1-yl)-8-fluoropyrido[4,3-d]pyrimidin-2-yl)oxy)methyl)hexahydropyrrolizine 4(1H)-oxide: To a solution of tert-butyl (1R,5S)-3-(7-(8-chloronaphthalen-1-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (26 mg, 0.039 mmol) in dichloromethane (0.4 ml) was added 3-chloroperoxybenzoic acid (12 mg, 0.051 mmol) at RT. The solution was stirred for 1 hour. Additional 3-Chloroperoxybenzoic acid (12 mg, 0.051 mmol) was added and the reaction was stirred at rt for one more hour. To the reaction was added sat. NaHCO₃ and the aqueous layer extracted twice with ethyl acetate. Pooled organic layers were dried over magnesium sulfate, filtered, and concentrated. Crude product was purified by silica gel column to give 7a-(((4-(((1R,5S)-8-(tert-butoxycarbonyl)-3,8-diazabicyclo[3.2.1]octan-3-yl)-7-(8-chloronaphthalen-1-yl)-8-fluoropyrido[4,3-d]pyrimidin-2-yl)oxy)methyl)hexahydropyrrolizine 4(1H)-oxide. ¹H NMR 400 MHz, (CDCl₃) δ 9.01 (s, 1H), 8.00-7.98 (m, 1H), 7.87 (d, 1H, J=8.0 Hz), 7.61-7.52 (m, 3H), 7.41 (t, 1H, J=8.0), 4.85 (s, 2H), 4.7-4.3 (m, 4H), 3.71-3.68 (m, 6H), 2.50-2.31 (m, 4H), 2.04-1.94 (m, 6H), 1.80 (bs, 2H), 1.51 (s, 9H).

Step B: 7a-(((4-(((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)hexahydropyrrolizine 4(1H)-oxide. 7a-(((4-(((1R,5S)-8-(tert-butoxycarbonyl)-3,8-diazabicyclo[3.2.1]octan-3-yl)-7-(8-chloronaphthalen-1-yl)-8-fluoropyrido[4,3-d]pyrimidin-2-yl)oxy)methyl)hexahydropyrrolizine 4(1H)-oxide was deprotected according to the method of Example 2, Step I (5.55 mg, 0.00825 mmol, 37% yield). LCMS (MM-ES+APCI, Pos): m/z 575.3 [M+H].

Example 61

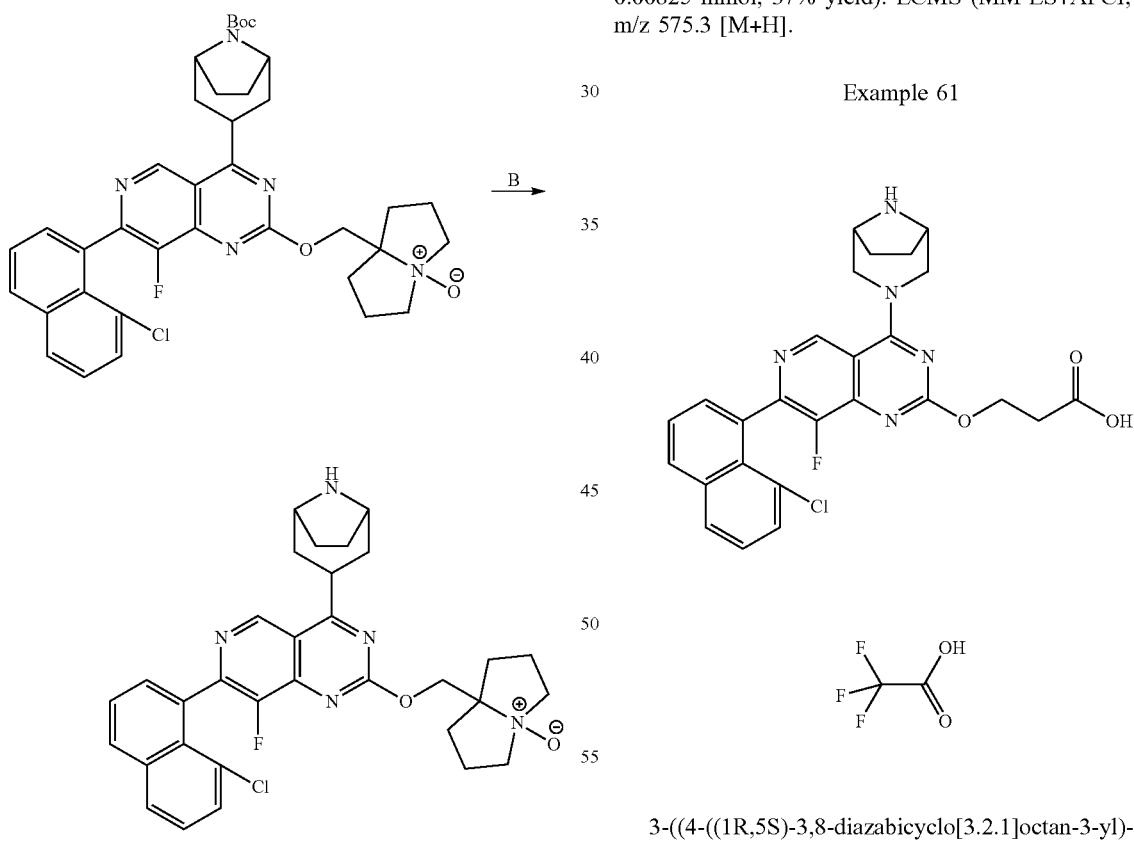

3-((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)propanoic acid Compound with 2,2,2-trifluoroacetaldehyde Synthesized according to Example 29, Step H substituting ethyl 3-hydroxypropanoate in place of (S)-(1-isopropylpyrrolidin-2-yl)methanol followed by deprotection using Example 2, Step I (1.66 mg, 0.00275 mmol, 16% yield). LCMS (MM-ES+APCI, Pos): m/z 530.3 [M+Na].

Example 62

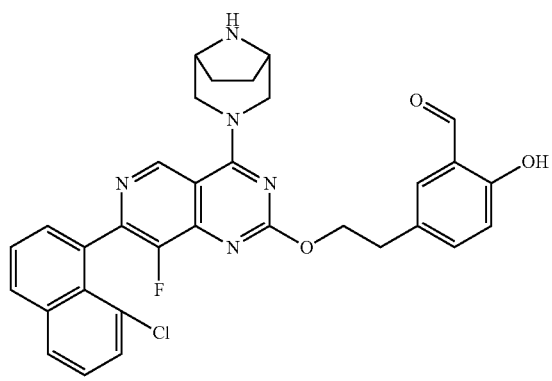 [SMILES: O=Cc1cc(CCOc2nc(N3CC4CCC(C3)N4)c3cnc(-c4cccc5cccc(Cl)c45)c(F)c3n2)ccc1O]

5-(2-((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)ethyl)-2-hydroxybenzaldehyde

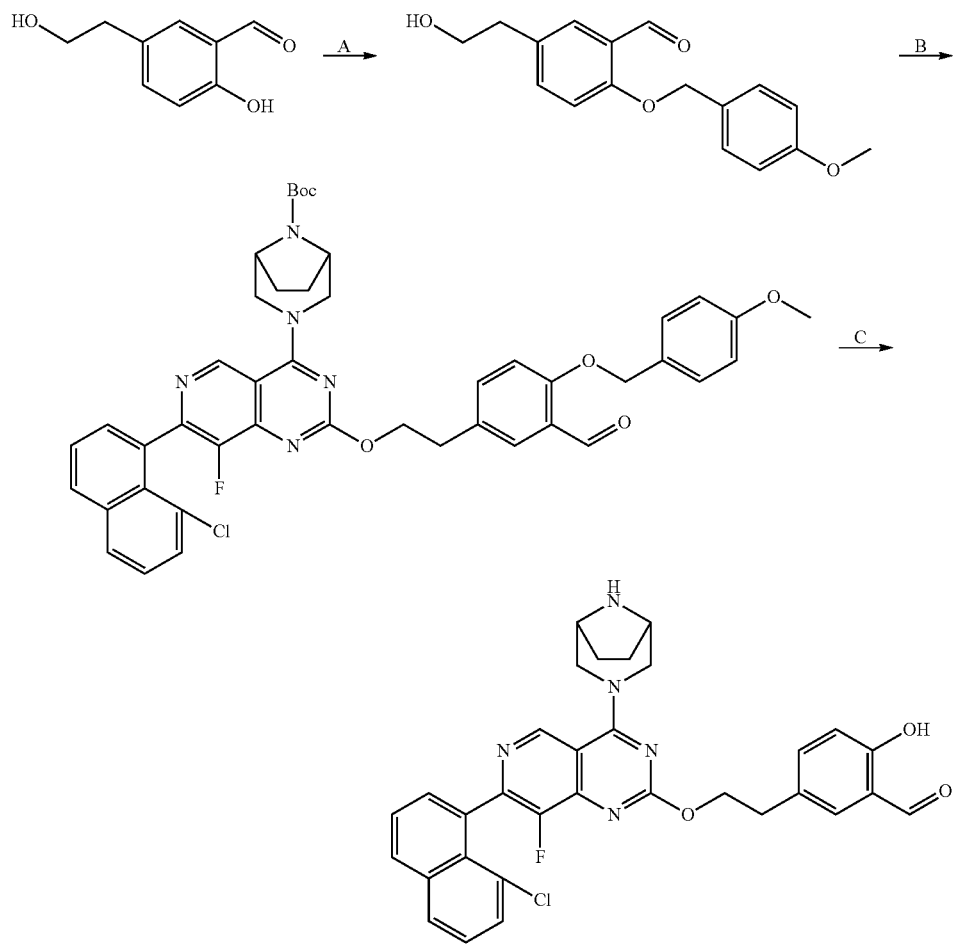

Step A. 5-(2-hydroxyethyl)-2-((4-methoxybenzyl)oxy)benzaldehyde: A mixture of 2-hydroxy-5-(2-hydroxyethyl)-benzaldehyde (220 mg, 1.32 mmol), 4-methoxybenzyl chloride (248 mg, 1.58 mmol), and potassium carbonate (366 mg, 2.64 mmol) in DMF (1.86 ml) was heated at 60° C. for 2 hours. The reaction was cooled to room temperature and water was added. The aqueous mixture was extracted two times with ethyl acetate. The pooled organic layers were washed two times with water, dried over magnesium sulfate, filtered and concentrated in vacuo. The crude mixture was purified by silica gel column to give 5-(2-hydroxyethyl)-2-((4-methoxybenzyl)oxy)benzaldehyde. $^1$H NMR 400 MHz, (CDCl$_3$) δ 10.48 (s, 1H), 7.68 (d, 1H, J=4.0 Hz), 7.41-7.39 (m, 1H), 7.35-7.32 (m, 2H), 7.00 (d, 1H, J=8.0 Hz), 6.93-6.90 (m, 2H), 5.09 (s, 2H), 3.84-3.81 (m, 5H), 2.82 (t, 2H, J=8.0 Hz).

Step B. tert-butyl (1R,5S)-3-(7-(8-chloronaphthalen-1-yl)-8-fluoro-2-(3-formyl-4-((4-methoxybenzyl)oxy)phenethoxy)pyrido[4,3-d]pyrimidin-4-yl)-3,8-diazabicyclo[3.2.1]octane-8-carboxylate: To a stirred solution of tert-butyl (1R,5S)-3-(2-chloro-7-(8-chloronaphthalen-1-yl)-8-fluoropyrido[4,3-d]pyrimidin-4-yl)-3,8-diazabicyclo[3.2.1]octane-8-carboxylate (50 mg, 0.090 mmol), 5-(2-hydroxyethyl)-2-((4-methoxybenzyl)oxy)benzaldehyde (189 mg, 0.66 mmol), and BINAP (11.2 mg, 0.018 mmol) in toluene (0.45 ml) was added Cs$_2$CO$_3$ (88.1 mg, 0.27 mmol) neat as a solid at room temperature under nitrogen. The reaction was sparged with argon for 5 minutes and then palladium (II) acetate (2.02 mg, 0.009 mmol) was added. The reaction was heated at 110° C. for 3 hours. The reaction was cooled to rt, water was added, and the aqueous layer was extracted 2× with ethyl acetate. The pooled organic layers were dried over magnesium sulfate, filtered, and concentrated. The crude material was purified by silica gel column (24 g, 0 to 15% ethyl acetate/DCM as eluent) to give tert-butyl (1R,5S)-3-(7-(8-chloronaphthalen-1-yl)-8-fluoro-2-(3-formyl-4-((4-methoxybenzyl)oxy)phenethoxy)pyrido[4,3-d]pyrimidin-4-yl)-3,8-diazabicyclo[3.2.1]octane-8-carboxylate. LCMS (MM-ES+APCI, Pos): m/z 804.2 [M+H].

Step C. 5-(2-((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)ethyl)-2-hydroxybenzaldehyde: To a solution of tert-butyl(1R,5S)-3-(7-(8-chloronaphthalen-1-yl)-8-fluoro-2-(3-formyl-4-((4-methoxybenzyl)oxy)phenethoxy)pyrido[4,3-d]pyrimidin-4-yl)-3,8-diazabicyclo[3.2.1]octane-8-carboxylate (27 mg, 0.033 mmol) in DCM (0.75 ml) was added TFA (0.25 ml) and the reaction was stirred at rt for 1 hour. The reaction solution was partitioned between sat. NaHCO₃ and ethyl acetate and the layers were separated. The aqueous layer was extracted with additional ethyl acetate. The pooled organic layers were dried over magnesium sulfate, filtered, and concentrated. The crude material was purified by silica gel column to give 5-(2-((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)ethyl)-2-hydroxybenzaldehyde (8.83 mg, 0.015 mmol, 45% yield). LCMS (MM-ES+APCI, Pos): m/z 584.2 [M+H].

Example 63

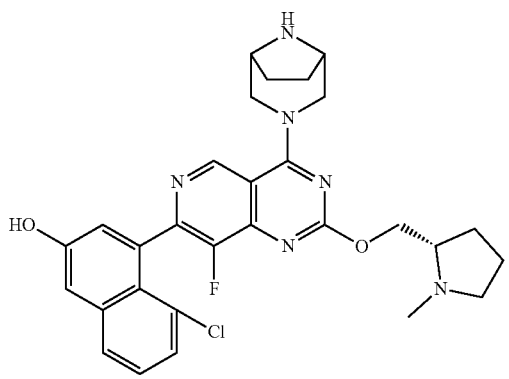 [SMILES: CN1CCC[C@H]1COc1nc(N2CC3CCC(C2)N3)c2cnc(-c3cc(O)cc4cccc(Cl)c34)c(F)c2n1]

4-(4-((1R,5S)-3,8-diazabicyclo[3.2.1]octan-3-yl)-8-fluoro-2-(((S)-1-methylpyrrolidin-2-yl)methoxy)pyrido[4,3-d]pyrimidin-7-yl)-5-chloronaphthalen-2-ol Synthesized according to Example 36, Step A to G substituting tert-butyl (1R,5S)-3-(7-chloro-8-fluoro-2-(((S)-1-methylpyrrolidin-2-yl)methoxy)pyrido[4,3-d]pyrimidin-4-yl)-3,8-diazabicyclo[3.2.1]octane-8-carboxylate (synthesized according to Example 3, Step A-G substituting (S)-(1-methylpyrrolidin-2-yl)methanol in place of 2-(1-methyl-1H-imidazol-2-yl)ethan-1-ol) in place of tert-butyl (1R,5S)-3-(7-chloro-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate in step F (6.08 mg, 0.00816 mmol, 7.2% yield). LCMS (MM-ES+APCI, Pos): m/z 549.3 [M+H].

Example 64

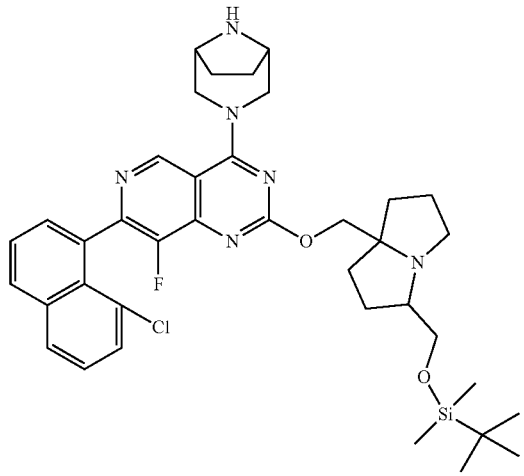 [SMILES: CC(C)(C)[Si](C)(C)OCC1CCC2(COc3nc(N4CC5CCC(C4)N5)c4cnc(-c5cccc6cccc(Cl)c56)c(F)c4n3)CCCN12]

4-((1R,5S)-3,8-diazabicyclo[3.2.1]octan-3-yl)-2-((3-((tert-butyldimethylsilyl)oxy)methyl)tetrahydro-1H-pyrrolizin-7a(5H)-yl)methoxy)-7-(8-chloronaphthalen-1-yl)-8-fluoropyrido[4,3-d]pyrimidine Synthesized according to Example 2, Step H using tert-butyl (1R,5S)-3-(2-chloro-7-(8-chloronaphthalen-1-yl)-8-fluoropyrido[4,3-d]pyrimidin-4-yl)-3,8-diazabicyclo[3.2.1]octane-8-carboxylate and (3-(((tert-butyldimethylsilyl)oxy)methyl)tetrahydro-1H-pyrrolizin-7a(5H)-yl)methanol as starting materials and deprotection according to the method of Example 2, Step I (5.72 mg, 0.00614 mmol, 21% yield). LCMS (MM-ES+APCI, Pos): m/z 703.3 [M+H].

Examples 65 & 66

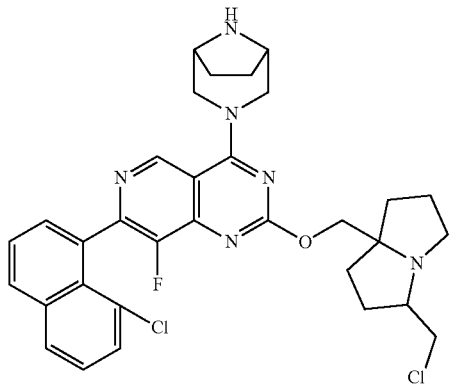

first eluting peak

261

-continued

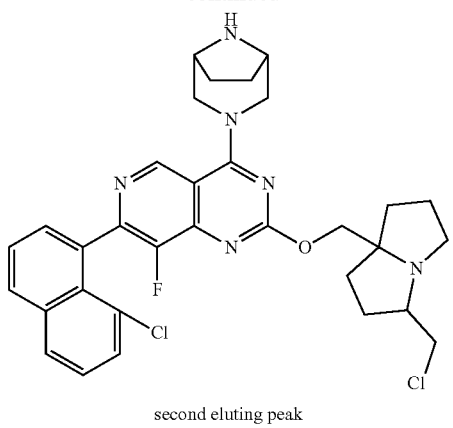 [SMILES: Fc1c(-c2cccc3cccc(Cl)c23)ncc2c(N3CC4CCC(C3)N4)nc(OCC34CCCN3C(CCl)CC4)nc12]

second eluting peak 4-((1R,5S)-3,8-diazabicyclo[3.2.1]octan-3-yl)-2-((3-(chloromethyl)tetrahydro-H-pyrrolizin-7a(5H)-yl)methoxy)-7-(8-chloronaphthalen-1-yl)-8-fluoro-pyrido[4,3-d]pyrimidine isomer 1 and 4-((1R,5S)-3,8-diazabicyclo[3.2.1]octan-3-yl)-2-((3-(chloromethyl)tetrahydro-1H-pyrrolizin-7a(5H)-yl)methoxy)-7-(8-chloronaphthalen-1-yl)-8-fluoropyrido[4,3-d]pyrimidine isomer 2

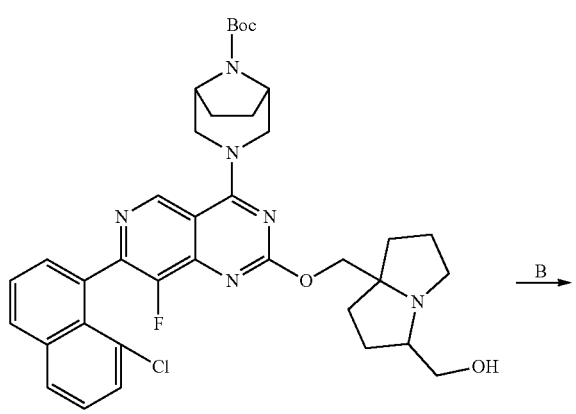

262

-continued

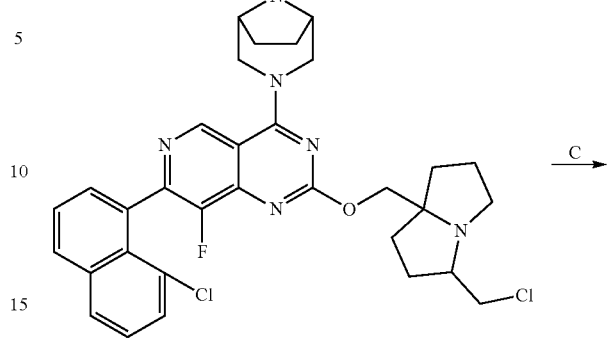

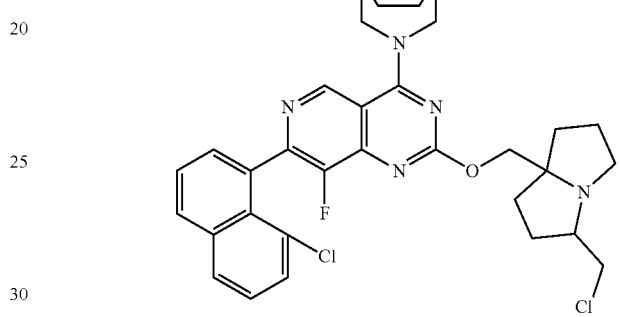

first eluting peak

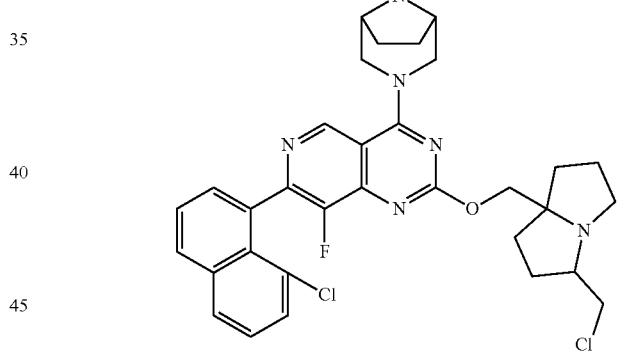

second eluting peak

Step A. tert-butyl (1R,5S)-3-(7-(8-chloronaphthalen-1-yl)-8-fluoro-2-((3-(hydroxymethyl)tetrahydro-1H-pyrrolizin-7a(5H)-yl)methoxy)pyrido[4,3-d]pyrimidin-4-yl)-3,8-diazabicyclo[3.2.1]octane-8-carboxylate: To a stirring solution of tert-butyl (1R,5S)-3-(2-((3-(((tert-butyldimethyl-silyl)oxy)methyl)tetrahydro-1H-pyrrolizin-7a(5H)-yl)methoxy)-7-(8-chloronaphthalen-1-yl)-8-fluoropyrido[4,3-d]pyrimidin-4-yl)-3,8-diazabicyclo[3.2.1]octane-8-carboxylate (90 mg, 0.11 mmol) in tetrahydrofuran (1.1 ml) was added tetrabutylammonium fluoride (123 µL, 0.12 mmol). The mixture was stirred at room temperature for 2 hours. Additional tetrabutylammonium fluoride (123 µL, 0.12 mmol) was added and the reaction was stirred at room temperature overnight. The mixture was concentrated and the residue purified by silica gel column to give a crude tert-butyl (1R,5S)-3-(7-(8-chloronaphthalen-1-yl)-8-fluoro-2-((3-(hydroxymethyl)tetrahydro-1H-pyrrolizin-7a(5H)-yl)

methoxy)pyrido[4,3-d]pyrimidin-4-yl)-3,8-diazabicyclo[3.2.1]octane-8-carboxylate. LCMS (MM-ES+APCI, Pos): m/z 689.3 [M+H].

Step B. tert-butyl (1R,5S)-3-(2-((3-(chloromethyl)tetrahydro-1H-pyrrolizin-7a(5H)-yl)methoxy)-7-(8-chloronaphthalen-1-yl)-8-fluoropyrido[4,3-d]pyrimidin-4-yl)-3,8-diazabicyclo[3.2.1]octane-8-carboxylate: A solution of tert-butyl (1R,5S)-3-(7-(8-chloronaphthalen-1-yl)-8-fluoro-2-((3-(hydroxymethyl)tetrahydro-1H-pyrrolizin-7a(5H)-yl)methoxy)pyrido[4,3-d]pyrimidin-4-yl)-3,8-diazabicyclo[3.2.1]octane-8-carboxylate (55 mg, 0.080 mmol) and pyridine (19 µL, 0.24 mmol) in dichloromethane (0.8 ml) was cooled to 0° C. and thionyl chloride was added (17 µL, 0.239 mmol). The reaction was stirred at 0° C. for 30 minutes and at rt for one hour. Additional pyridine (19 µL, 0.24 mmol) and thionyl chloride (17.4 µL, 0.239 mmol) were added and the reaction was stirred at rt for one hour. The reaction was concentrated in vacuo and the material used in the next step. LCMS (MM-ES+APCI, Pos): m/z 707.3 [M+H].

Step C: 4-((1R,5S)-3,8-diazabicyclo[3.2.1]octan-3-yl)-2-(((3R,7aS)-3-(chloromethyl)tetrahydro-1H-pyrrolizin-7a(5H)-yl)methoxy)-7-(8-chloronaphthalen-1-yl)-8-fluoropyrido[4,3-d]pyrimidine and 4-((1R,5S)-3,8-diazabicyclo[3.2.1]octan-3-yl)-2-(((3S,7aS)-3-(chloromethyl)tetrahydro-1H-pyrrolizin-7a(5H)-yl)methoxy)-7-(8-chloronaphthalen-1-yl)-8-fluoropyrido[4,3-d]pyrimidine: Synthesized according to Example 2, Step I to yield two isomeric products. (9.45 mg, 0.0113 mmol). LCMS (MM-ES+APCI, Pos): m/z 607.2 [M+H]. (3.57 mg, 0.00428 mmol). LCMS (MM-ES+APCI, Pos): m/z 607.2 [M+H].

Example 67

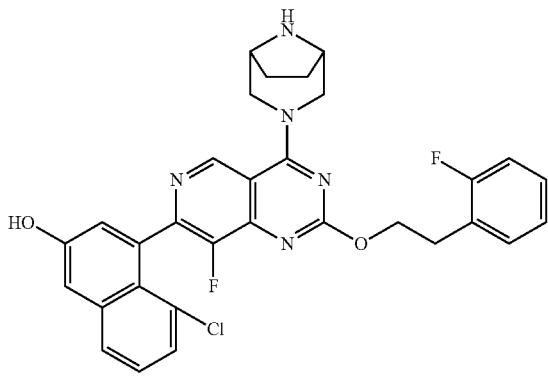 [SMILES: Oc1cc(-c2ncc3c(N4CC5CCC(C4)N5)nc(OCCc4ccccc4F)nc3c2F)c2c(Cl)cccc2c1]

4-(4-((1R,5S)-3,8-diazabicyclo[3.2.1]octan-3-yl)-8-fluoro-2-(2-fluorophenethoxy)pyrido[4,3-d]pyrimidin-7-yl)naphthalen-2-ol Synthesized similarly to Example 3 Steps G-H substituting 2-fluorophenethyl alcohol in place of 2-(1-methyl-1H-imidazol-2-yl)ethan-1-ol and deprotected according to the method of Example 2, Step I (67.5 mg, 0.125 mmol, 53%). LCMS (MM-ES+APCI, Pos): m/z 540.2 (M+H).

Example 68

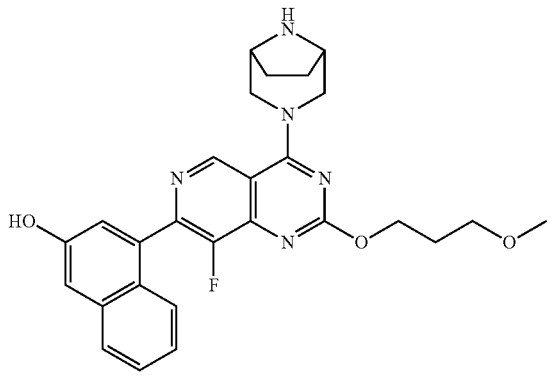 [SMILES: COCCCOc1nc(N2CC3CCC(C2)N3)c2cnc(-c3cc(O)cc4ccccc34)c(F)c2n1]

4-(4-((1R,5S)-3,8-diazabicyclo[3.2.1]octan-3-yl)-8-fluoro-2-(3-methoxypropoxy)pyrido[4,3-d]pyrimidin-7-yl)naphthalen-2-ol Synthesized similarly to Example 3 Steps G-H substituting 3-methoxypropan-1-ol in place of 2-(1-methyl-1H-imidazol-2-yl)ethan-1-ol and deprotected according to the method of Example 2, Step I (86.5 mg, 0.177 mmol, 95%). LCMS (MM-ES+APCI, Pos): m/z 490.2 (M+H).

Example 69

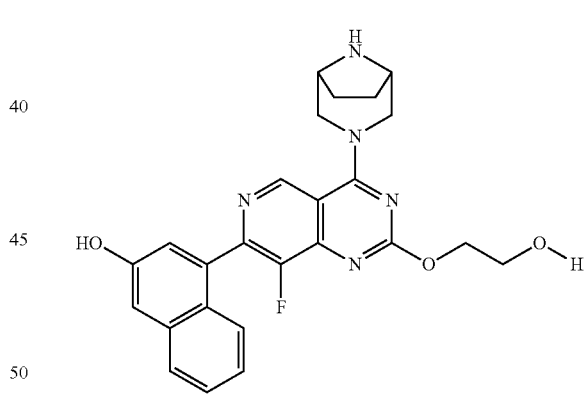

4-(4-((1R,5S)-3,8-diazabicyclo[3.2.1]octan-3-yl)-8-fluoro-2-(2-hydroxyethoxy)pyrido[4,3-d]pyrimidin-7-yl)naphthalen-2-ol Synthesized similarly to Example 3 Steps G-H substituting ethylene glycol (40 equivalents) in place of 2-(1-methyl-1H-imidazol-2-yl)ethan-1-ol and deprotected according to the method of Example 2, Step I (86.0 mg, 0.186 mmol, 95%). LCMS (MM-ES+APCI, Pos): m/z 462.2 (M+H).

Example 70

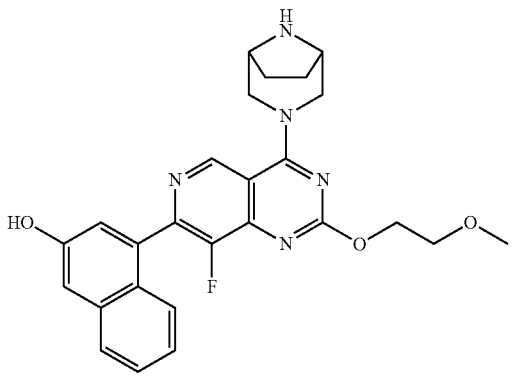 [SMILES: COCCOc1nc(N2CC3CCC(C2)N3)c2cnc(-c3cc(O)cc4ccccc34)c(F)c2n1]

4-(4-((1R,5S)-3,8-diazabicyclo[3.2.1]octan-3-yl)-8-fluoro-2-(2-methoxyethoxy)pyrido[4,3-d]pyrimidin-7-yl)naphthalen-2-ol Synthesized similarly to Example 3 Steps G-H substituting 2-methoxyethanol in place of 2-(1-methyl-1H-imidazol-2-yl)ethan-1-ol and deprotected according to the method of Example 2, Step I (28.0 mg, 0.0588 mmol, 68%). LCMS (MM-ES+APCI, Pos): m/z 476.2 (M+H).

Example 71

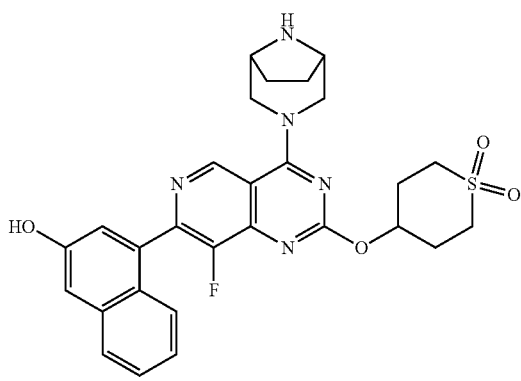 [SMILES: O=S1(=O)CCC(Oc2nc(N3CC4CCC(C3)N4)c3cnc(-c4cc(O)cc5ccccc45)c(F)c3n2)CC1]

4-((4-((1R,5S)-3,8-diazabicyclo[3.2.1]octan-3-yl)-8-fluoro-7-(3-hydroxynaphthalen-1-yl)pyrido[4,3-d]pyrimidin-2-yl)oxy)tetrahydro-2H-thiopyran 1,1-dioxide Synthesized similarly to Example 3 Steps G-H substituting 1,1-dioxo-hexahydro-2H-thiopyran-4-ol in place of 2-(1-methyl-1H-imidazol-2-yl)ethan-1-ol and deprotected according to the method of Example 2, Step I (10.6 mg, 0.0192 mmol, 42%). LCMS (MM-ES+APCI, Pos): m/z 550.2 (M+H).

Example 72

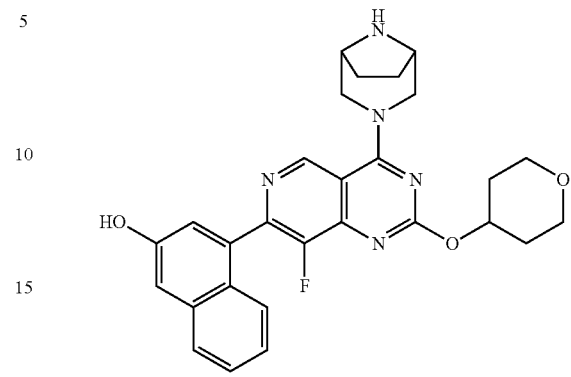

4-(4-((1R,5S)-3,8-diazabicyclo[3.2.1]octan-3-yl)-8-fluoro-2-((tetrahydro-2H-pyran-4-yl)oxy)pyrido[4,3-d]pyrimidin-7-yl)naphthalen-2-ol Synthesized similarly to Example 3 Steps G-H substituting tetrahydro-2H-pyran-4-ol in place of 2-(1-methyl-1H-imidazol-2-yl)ethan-1-ol and deprotected according to the method of Example 2, Step I (75.9 mg, 0.151 mmol, 91%). LCMS (MM-ES+APCI, Pos): m/z 502.3 (M+H).

Example 73

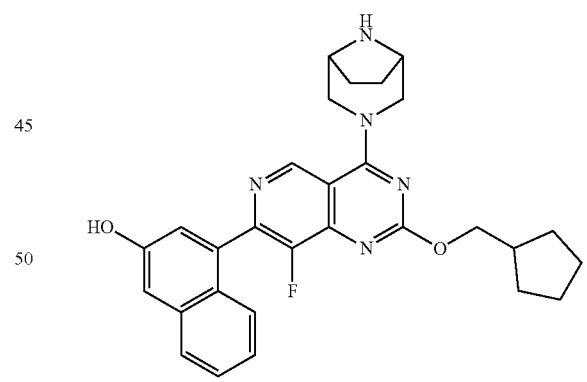

4-(4-((1R,5S)-3,8-diazabicyclo[3.2.1]octan-3-yl)-2-(cyclopentylmethoxy)-8-fluoropyrido[4,3-d]pyrimidin-7-yl)naphthalen-2-ol Synthesized similarly to Example 3 Steps G-H substituting cyclopentanemethanol in place of 2-(1-methyl-1H-imidazol-2-yl)ethan-1-ol and deprotected according to the method of Example 2, Step I (28.0 mg, 0.056 mmol, 26%). LCMS (MM-ES+APCI, Pos): m/z 500.3 (M+H).

Example 74

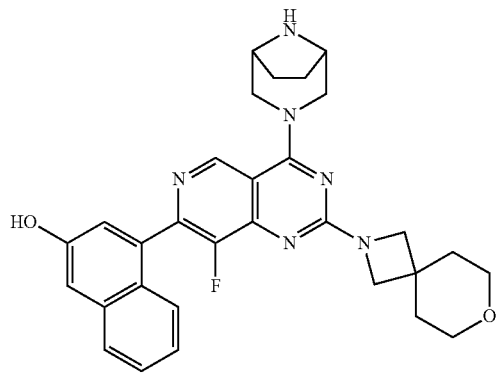 [SMILES: Oc1cc(-c2ncc3c(N4CC5CCC(C4)N5)nc(N4CC5(CCOCC5)C4)nc3c2F)c2ccccc2c1]

4-(4-((1R,5S)-3,8-diazabicyclo[3.2.1]octan-3-yl)-8-fluoro-2-(7-oxa-2-azaspiro[3.5]nonan-2-yl)pyrido[4,3-d]pyrimidin-7-yl)naphthalen-2-ol Synthesized similarly to Example 3 Steps G-H substituting 7-oxa-2-azaspiro[3.5]nonane HCl in place of 2-(1-methyl-1H-imidazol-2-yl)ethan-1-ol and deprotected according to the method of Example 2, Step I (94.1 mg, 0.179 mmol, 64%). LCMS (MM-ES+APCI, Pos): m/z 527.2 (M+H).

Example 76

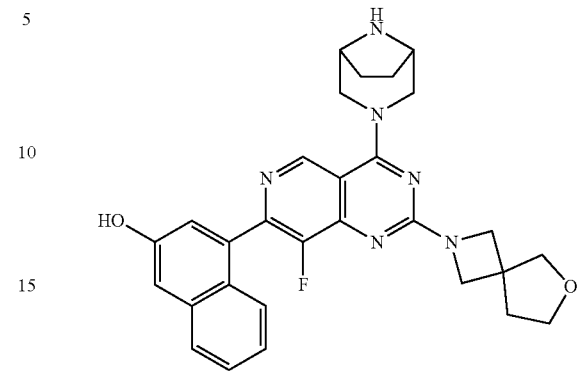

4-(4-((1R,5S)-3,8-diazabicyclo[3.2.1]octan-3-yl)-8-fluoro-2-(6-oxa-2-azaspiro[3.4]octan-2-yl)pyrido[4,3-d]pyrimidin-7-yl)naphthalen-2-ol Synthesized similarly to Example 3 Steps G-H substituting 6-oxa-2-azaspiro[3.4]octane in place of 2-(1-methyl-1H-imidazol-2-yl)ethan-1-ol and deprotected according to the method of Example 2, Step I (52.0 mg, 0.101 mmol, 79%). LCMS (MM-ES+APCI, Pos): m/z 513.3 (M+H).

Example 75

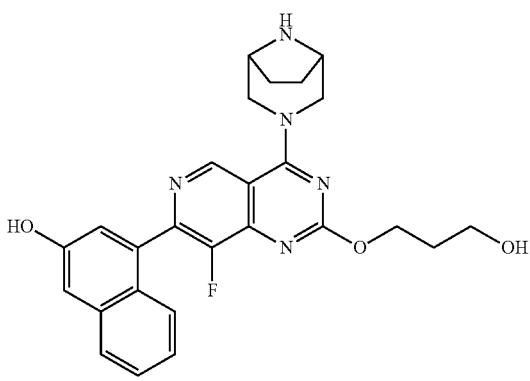 [SMILES: OCCCOc1nc(N2CC3CCC(C2)N3)c2cnc(-c3cc(O)cc4ccccc34)c(F)c2n1]

4-(4-((1R,5S)-3,8-diazabicyclo[3.2.1]octan-3-yl)-8-fluoro-2-(3-hydroxypropoxy)pyrido[4,3-d]pyrimidin-7-yl)naphthalen-2-ol Synthesized similarly to Example 3 Steps G-H substituting 1,3-propanediol (40 equivalence) in place of 2-(1-methyl-1H-imidazol-2-yl)ethan-1-ol and deprotected according to the method of Example 2, Step I (11.4 mg, 0.0239 mmol, 20%). LCMS (MM-ES+APCI, Pos): m/z 476.2 (M+H).

Example 77

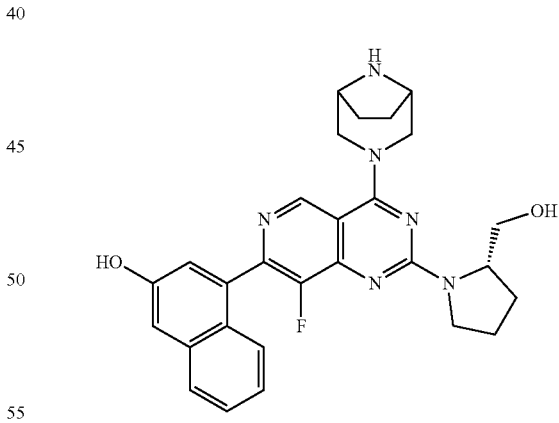

4-(4-((1R,5S)-3,8-diazabicyclo[3.2.1]octan-3-yl)-8-fluoro-2-((S)-2-(hydroxymethyl)pyrrolidin-1-yl)pyrido[4,3-d]pyrimidin-7-yl)naphthalen-2-ol Synthesized similarly to Example 3 Steps G-H substituting (S)-pyrrolidin-2-ylmethanol in place of 2-(1-methyl-1H-imidazol-2-yl)ethan-1-ol and deprotected according to the method of Example 2, Step I (50.0 mg, 0.100 mmol, 17%). LCMS (MM-ES+APCI, Pos): m/z 501.2 (M+H).

Example 78

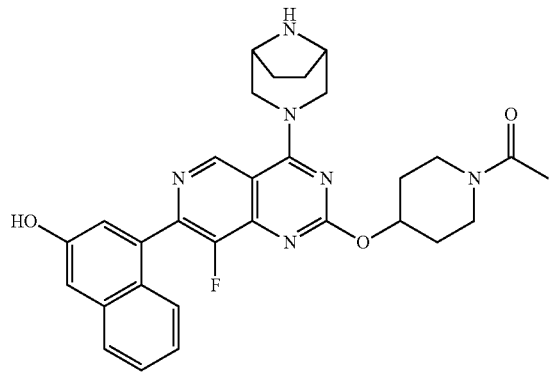 [SMILES: CC(=O)N1CCC(Oc2nc(N3CC4CCC(C3)N4)c3cnc(-c4cc(O)cc5ccccc45)c(F)c3n2)CC1]

1-(4-((4-(((1R,5S)-3,8-diazabicyclo[3.2.1]octan-3-yl)-8-fluoro-7-(3-hydroxynaphthalen-1-yl)pyrido[4,3-d]pyrimidin-2-yl)oxy)piperidin-1-yl)ethan-1-one Synthesized similarly to Example 3 Steps G-H substituting 1-(4-hydroxypiperidin-1-yl)ethan-1-one in place of 2-(1-methyl-1H-imidazol-2-yl)ethan-1-ol and deprotected according to the method of Example 2, Step I (6.50 mg, 0.0120 mmol, 38%). LCMS (MM-ES+APCI, Pos): m/z 543.3 (M+H).

Example 80

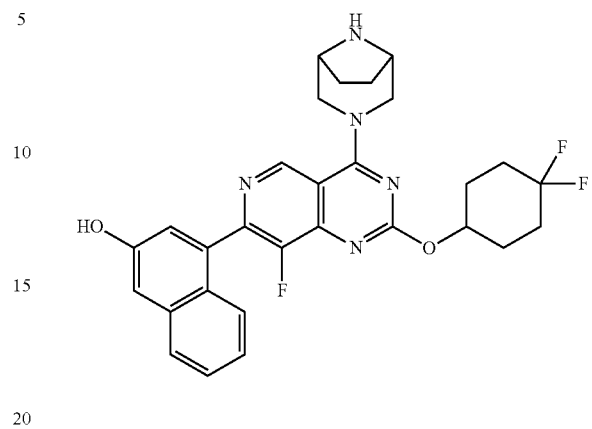

4-(4-((1R,5S)-3,8-diazabicyclo[3.2.1]octan-3-yl)-2-((4,4-difluorocyclohexyl)oxy)-8-fluoropyrido[4,3-d]pyrimidin-7-yl)naphthalen-2-ol Synthesized similarly to Example 3 Steps G-H substituting 4,4-difluorocyclohexanol in place of 2-(1-methyl-1H-imidazol-2-yl)ethan-1-ol and deprotected according to the method of Example 2, Step I (14.3 mg, 0.0268 mmol, 24%). LCMS (MM-ES+APCI, Pos): m/z 536.2 (M+H).

Example 79

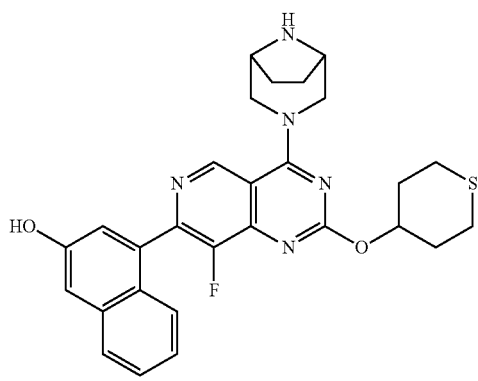

4-(4-((1R,5S)-3,8-diazabicyclo[3.2.1]octan-3-yl)-8-fluoro-2-((tetrahydro-2H-thiopyran-4-yl)oxy)pyrido[4,3-d]pyrimidin-7-yl)naphthalen-2-ol Synthesized similarly to Example 3 Steps G-H substituting tetrahydro-2H-thiopyran-4-ol in place of 2-(1-methyl-1H-imidazol-2-yl)ethan-1-ol and deprotected according to the method of Example 2, Step I (53.9 mg, 0.104 mmol, 82%). LCMS (MM-ES+APCI, Pos): m/z 518.2 (M+H).

Example 81

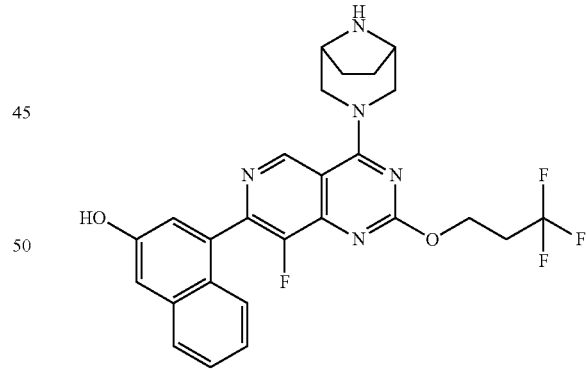

4-(4-((1R,5S)-3,8-diazabicyclo[3.2.1]octan-3-yl)-8-fluoro-2-(3,3,3-trifluoropropoxy)pyrido[4,3-d]pyrimidin-7-yl)naphthalen-2-ol Synthesized similarly to Example 3 Steps G-H substituting 3,3,3-trifluoropropan-1-ol in place of 2-(1-methyl-1H-imidazol-2-yl)ethan-1-ol and deprotected according to the method of Example 2, Step I (77.2 mg, 0.150 mmol, 62%). LCMS (MM-ES+APCI, Pos): m/z 514.2 (M+H).

Example 82

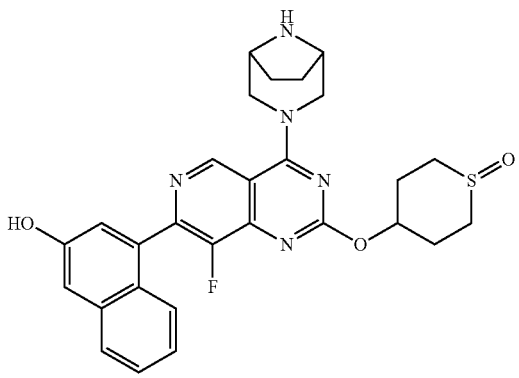 [SMILES: O=S1CCC(Oc2nc(N3CC4CCC(C3)N4)c3cnc(-c4cc(O)cc5ccccc45)c(F)c3n2)CC1]

4-((4-((1R,5S)-3,8-diazabicyclo[3.2.1]octan-3-yl)-8-fluoro-7-(3-hydroxynaphthalen-1-yl)pyrido[4,3-d]pyrimidin-2-yl)oxy)tetrahydro-2H-thiopyran 1-oxide

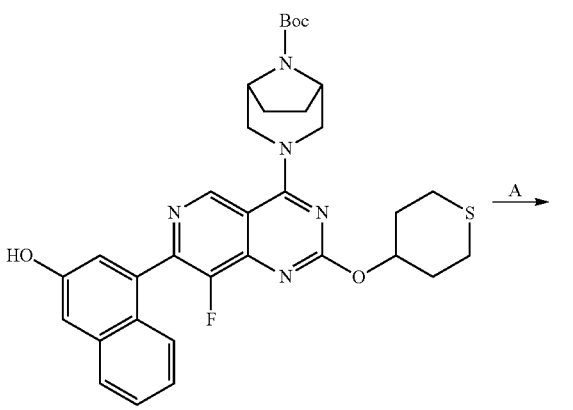

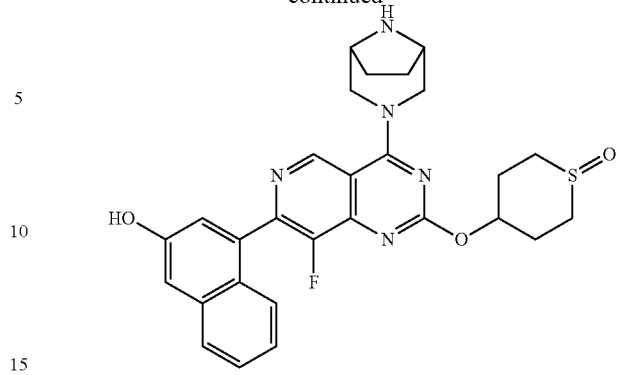

Step A. tert-butyl (1R,5S)-3-(8-fluoro-7-(3-hydroxynaphthalen-1-yl)-2-((1-oxidotetrahydro-2H-thiopyran-4-yl)oxy)pyrido[4,3-d]pyrimidin-4-yl)-3,8-diazabicyclo[3.2.1]octane-8-carboxylate: A solution of tert-butyl (1R,5S)-3-(8-fluoro-7-(3-hydroxynaphthalen-1-yl)-2-((tetrahydro-2H-thiopyran-4-yl)oxy)pyrido[4,3-d]pyrimidin-4-yl)-3,8-diazabicyclo[3.2.1]octane-8-carboxylate (93 mg, 0.15 mmol) in THF (3.0 ml) was added 3-chloroperoxybenzoic acid (35 mg, 0.15 mmol) and the reaction stirred at rt for 2 hours. The reaction was diluted with water and the aqueous layer was extracted twice with ethyl acetate. The pooled organic layers were dried over magnesium sulfate, filtered, and concentrated. Crude product was purified by silica gel column to give tert-butyl (1R,5S)-3-(8-fluoro-7-(3-hydroxynaphthalen-1-yl)-2-((1-oxidotetrahydro-2H-thiopyran-4-yl)oxy)pyrido[4,3-d]pyrimidin-4-yl)-3,8-diazabicyclo[3.2.1]octane-8-carboxylate as a solid. LCMS (MM-ES+APCI, Pos): m/z 634.2 [M+H].

Step B: 4-((4-((1R,5S)-3,8-diazabicyclo[3.2.1]octan-3-yl)-8-fluoro-7-(3-hydroxynaphthalen-1-yl)pyrido[4,3-d]pyrimidin-2-yl)oxy)tetrahydro-2H-thiopyran 1-oxide: tert-butyl (1R,5S)-3-(8-fluoro-7-(3-hydroxynaphthalen-1-yl)-2-((1-oxidotetrahydro-2H-thiopyran-4-yl)oxy)pyrido[4,3-d]pyrimidin-4-yl)-3,8-diazabicyclo[3.2.1]octane-8-carboxylate was deprotected according to the method of Example 2, Step I (37.9 mg, 0.0498 mmol, 85%). LCMS (MM-ES+APCI, Pos): m/z 534.1 (M+H).

Example 83

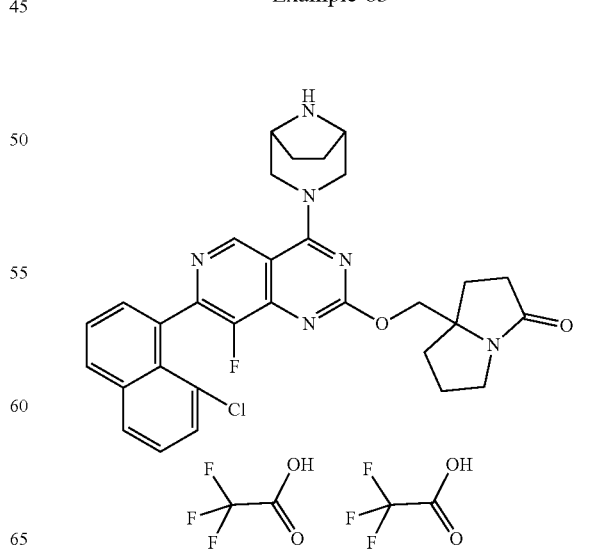

273

7a-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)hexahydro-3H-pyrrolizin-3-one bis(2,2,2-trifluoroacetate)

Synthesized according to Example 29 substituting 7a-(hydroxymethyl)hexahydro-3H-pyrrolizin-3-one in place of (S)-(1-methylpyrrolidin-2-yl)methanol in Step G (39.6 mg, 0.25 mmol, 68%). The final product was prepared as the TFA salt. LCMS (MM-ES+APCI, Pos): m/z 573.2 [M+H].

Example 84

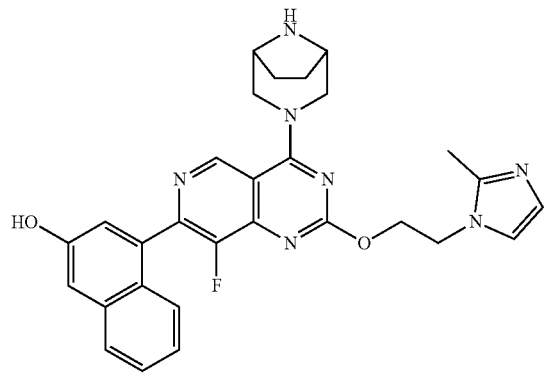 [SMILES: Cc1nccn1CCOc1nc(N2CC3CCC(C2)N3)c2cnc(-c3cc(O)cc4ccccc34)c(F)c2n1]

4-(4-((1R,5S)-3,8-diazabicyclo[3.2.1]octan-3-yl)-8-fluoro-2-(2-(2-methyl-1H-imidazol-1-yl)ethoxy)pyrido[4,3-d]pyrimidin-7-yl)naphthalen-2-ol Synthesized according to Example 3, Steps G-I substituting 2-(2-methyl-1H-imidazol-1-yl)ethan-1-ol in place of 2-(1-methyl-1H-imidazol-2-yl)ethan-1-ol to afford 4-(4-((1R,5S)-3,8-diazabicyclo[3.2.1]octan-3-yl)-8-fluoro-2-(2-(2-methyl-1H-imidazol-1-yl)ethoxy)pyrido[4,3-d]pyrimidin-7-yl)naphthalen-2-ol (13.1 mg, 0.24 mmol, 40%). LCMS (MM-ES+APCI, Pos): m/z 526.2 (M+H).

Example 85

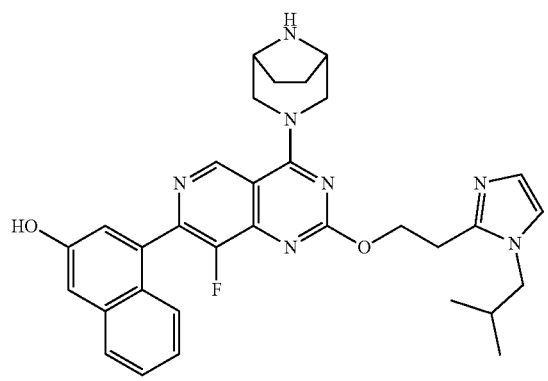 [SMILES: CC(C)Cn1ccnc1CCOc1nc(N2CC3CCC(C2)N3)c2cnc(-c3cc(O)cc4ccccc34)c(F)c2n1]

4-(4-((1R,5S)-3,8-diazabicyclo[3.2.1]octan-3-yl)-8-fluoro-2-(2-(1-isobutyl-1H-imidazol-2-yl)ethoxy)pyrido[4,3-d]pyrimidin-7-yl)naphthalen-2-ol Synthesized according to Example 3, Steps G-I substituting 2-(1-isobutyl-1H-imidazol-2-yl)ethan-1-ol in place of 2-(1-methyl-1H-imidazol-2-yl)ethan-1-ol to afford 4-(4-((1R,5S)-3,8-diazabicyclo[3.2.1]octan-3-yl)-8-fluoro-2-(2-(1-isobutyl-1H-imidazol-2-yl)ethoxy)pyrido[4,3-d]pyrimidin-7-yl)naphthalen-2-ol (42.4 mg, 0.71 mmol, 55%). LCMS (MM-ES+APCI, Pos): m/z 568.2 (M+H).

Example 86

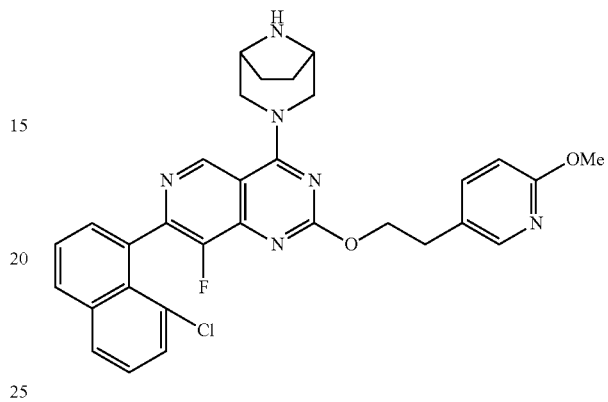

4-((1R,5S)-3,8-diazabicyclo[3.2.1]octan-3-yl)-7-(8-chloronaphthalen-1-yl)-8-fluoro-2-(2-(6-methoxypyridin-3-yl)ethoxy)pyrido[4,3-d]pyrimidine Synthesized according to Example 29, Steps H-I substituting 2-(6-methoxypyridin-3-yl)ethan-1-ol in place of (S)-(1-isopropylpyrrolidin-2-yl)methanol to afford 4-((1R,5S)-3,8-diazabicyclo[3.2.1]octan-3-yl)-7-(8-chloronaphthalen-1-yl)-8-fluoro-2-(2-(6-methoxypyridin-3-yl)ethoxy)pyrido[4,3-d]pyrimidine (36.6 mg, 0.027 mmol, 42%). LCMS (MM-ES+APCI, Pos): m/z 571.2 (M+H).

Example 87

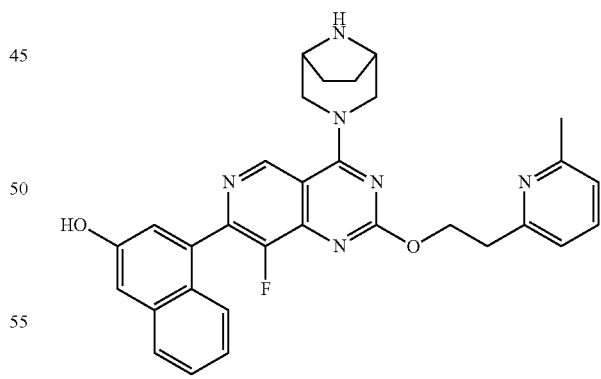

4-(4-((1R,5S)-3,8-diazabicyclo[3.2.1]octan-3-yl)-8-fluoro-2-(2-(6-methylpyridin-2-yl)ethoxy)pyrido[4,3-d]pyrimidin-7-yl)naphthalen-2-ol Synthesized according to Example 3, Steps G-I substituting 2-(6-methylpyridin-2-yl)ethan-1-ol in place of 2-(1-methyl-1H-imidazol-2-yl)ethan-1-ol to afford 4-(4-((1R, 5S)-3,8-diazabicyclo[3.2.1]octan-3-yl)-8-fluoro-2-(2-(6- methylpyridin-2-yl)ethoxy)pyrido[4,3-d]pyrimidin-7-yl)naphthalen-2-ol (33.8 mg, 0.061 mmol, 56%). LCMS (MM-ES+APCI, Pos): m/z 537.2 (M+H).

Example 88

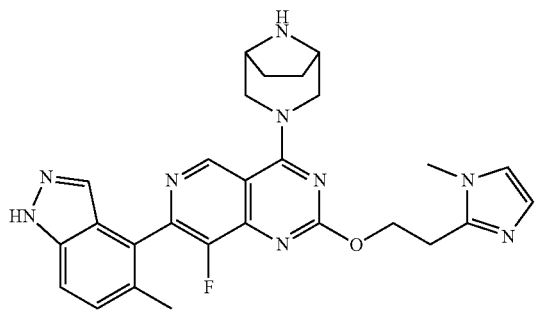 [SMILES: Cc1ccc2[nH]ncc2c1-c1ncc2c(N3CC4CCC(C3)N4)nc(OCCc3nccn3C)nc2c1F]

4-((1R,5S)-3,8-diazabicyclo[3.2.1]octan-3-yl)-8-fluoro-2-(2-(1-methyl-1H-imidazol-2-yl)ethoxy)-7-(5-methyl-1H-indazol-4-yl)pyrido[4,3-d]pyrimidine Synthesized according to Example 3, Steps H-I substituting (5-methyl-1H-indazol-4-yl)boronic acid in place of 4-(4,4,5,5-tetramethyl-1,3,2-dioxaborolan-2-yl)naphthalen-2-ol to afford 4-((1R,5S)-3,8-diazabicyclo[3.2.1]octan-3-yl)-8-fluoro-2-(2-(1-methyl-1H-imidazol-2-yl)ethoxy)-7-(5-methyl-1H-indazol-4-yl)pyrido[4,3-d]pyrimidine (7.1 mg, 0.013 mmol, 48%). LCMS (MM-ES+APCI, Pos): m/z 514.2 (M+H).

Example 89

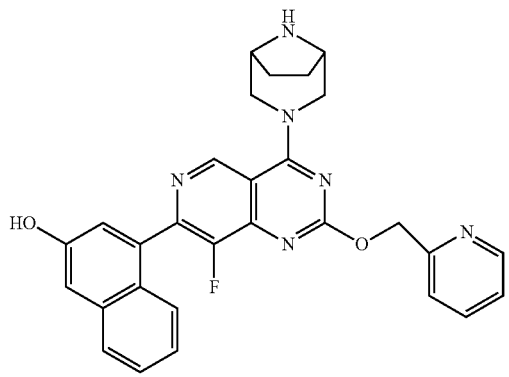 [SMILES: Oc1cc(-c2ncc3c(N4CC5CCC(C4)N5)nc(OCc4ccccn4)nc3c2F)c2ccccc2c1]

4-(4-((1R,5S)-3,8-diazabicyclo[3.2.1]octan-3-yl)-8-fluoro-2-(pyridin-2-ylmethoxy)pyrido[4,3-d]pyrimidin-7-yl)naphthalen-2-ol Synthesized according to Example 3, Steps G-I substituting pyridin-2-ylmethanol in place of 2-(1-methyl-1H-imidazol-2-yl)ethan-1-ol to afford 4-(4-((1R,5S)-3,8-diazabicyclo[3.2.1]octan-3-yl)-8-fluoro-2-(pyridin-2-ylmethoxy)pyrido[4,3-d]pyrimidin-7-yl)naphthalen-2-ol (2.8 mg, 0.053 mmol, 56%). LCMS (MM-ES+APCI, Pos): m/z 509.2 (M+H).

Example 90

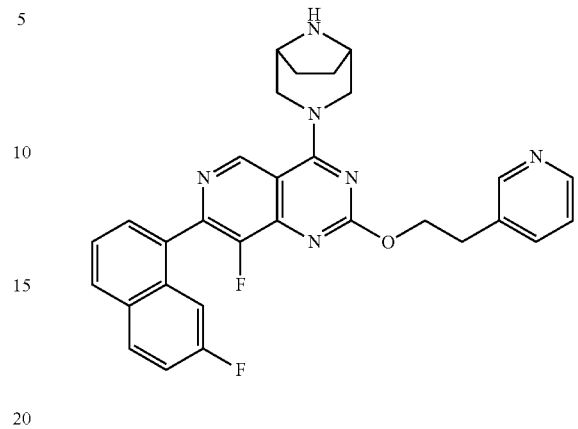

4-((1R,5S)-3,8-diazabicyclo[3.2.1]octan-3-yl)-8-fluoro-7-(7-fluoronaphthalen-1-yl)-2-(2-(pyridin-3-yl)ethoxy)pyrido[4,3-d]pyrimidine Synthesized according to Example 3, Steps G-I substituting 2-(pyridin-3-yl)ethan-1-ol in place of 2-(1-methyl-1H-imidazol-2-yl)ethan-1-ol in Step G and 2-(7-fluoronaphthalen-1-yl)-4,4,5,5-tetramethyl-1,3,2-dioxaborolane in place of 4-(4,4,5,5-tetramethyl-1,3,2-dioxaborolan-2-yl)naphthalen-2-ol in Step H to afford 4-((1R,5S)-3,8-diazabicyclo[3.2.1]octan-3-yl)-8-fluoro-7-(7-fluoronaphthalen-1-yl)-2-(2-(pyridin-3-yl)ethoxy)pyrido[4,3-d]pyrimidine (16.9 mg, 0.032 mmol, 54%). LCMS (MM-ES+APCI, Pos): m/z 525.2 (M+H).

Example 91

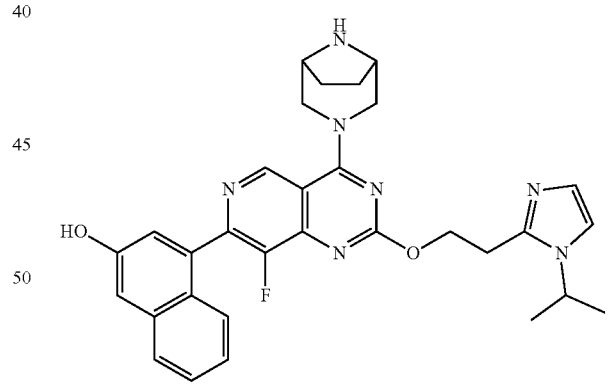

4-(4-((1R,5S)-3,8-diazabicyclo[3.2.1]octan-3-yl)-8-fluoro-2-(2-(1-isopropyl-1H-imidazol-2-yl)ethoxy)pyrido[4,3-d]pyrimidin-7-yl)naphthalen-2-ol Synthesized according to Example 3, Steps G-I substituting 2-(1-isopropyl-1H-imidazol-2-yl)ethan-1-ol in place of 2-(1-methyl-1H-imidazol-2-yl)ethan-1-ol to afford 4-(4-((1R,5S)-3,8-diazabicyclo[3.2.1]octan-3-yl)-8-fluoro-2-(2-(1-isopropyl-1H-imidazol-2-yl)ethoxy)pyrido[4,3-d]pyrimidin-7-yl)naphthalen-2-ol (30.9 mg, 0.053 mmol, 64%). LCMS (MM-ES+APCI, Pos): m/z 554.3 (M+H).

Example 92

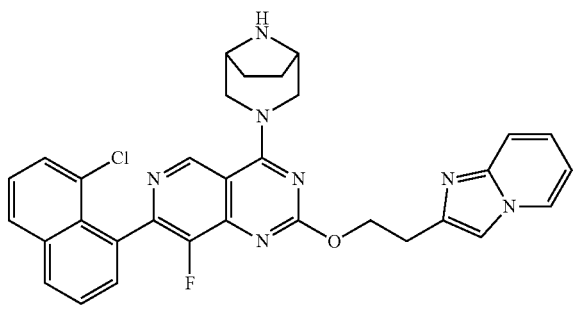 [SMILES: Fc1c(-c2cccc3cccc(Cl)c23)ncc2c(N3CC4CCC(C3)N4)nc(OCCc3cn4ccccc4n3)nc12]

4-((1R,5S)-3,8-diazabicyclo[3.2.1]octan-3-yl)-7-(8-chloronaphthalen-1-yl)-8-fluoro-2-(2-(imidazo[1,2-a]pyridin-2-yl)ethoxy)pyrido[4,3-d]pyrimidine Synthesized according to Example 30, Steps A-F, H substituting 2-(8-chloronaphthalen-1-yl)-4,4,5,5-tetramethyl-1,3,2-dioxaborolane in place of 2-(3-(benzyloxy)naphthalen-1-yl)-4,4,5,5-tetramethyl-1,3,2-dioxaborolane in Step A and 2-(imidazo[1,2-a]pyridin-2-yl)ethan-1-ol in place of 2-(1-methyl-1H-benzo[d]imidazol-2-yl)ethan-1-ol dihydrate in Step F to afford 4-((1R,5S)-3,8-diazabicyclo[3.2.1]octan-3-yl)-7-(8-chloronaphthalen-1-yl)-8-fluoro-2-(2-(imidazo[1,2-a]pyridin-2-yl)ethoxy)pyrido[4,3-d]pyrimidine (5.2 mg, 0.009 mmol, 55%). LCMS (MM-ES+APCI, Pos): m/z 580.2 (M+H).

Example 93

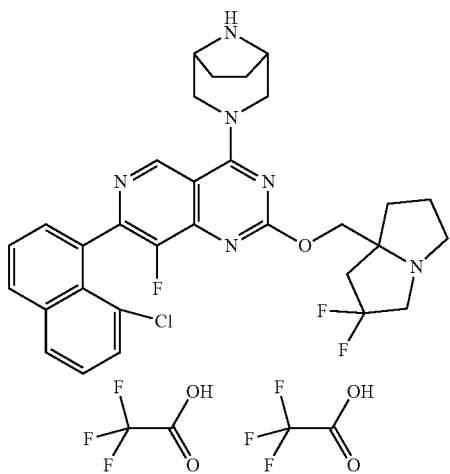

4-((1R,5S)-3,8-diazabicyclo[3.2.1]octan-3-yl)-7-(8-chloronaphthalen-1-yl)-2-((2,2-difluorotetrahydro-1H-pyrrolizin-7a(5H)-yl)methoxy)-8-fluoropyrido[4,3-d]pyrimidine bis(2,2,2-trifluoroacetate)

Synthesized according to Example 29, Steps H-I substituting (2,2-difluorotetrahydro-1H-pyrrolizin-7a(5H)-yl)methanol in place of (S)-(1-isopropylpyrrolidin-2-yl)methanol to afford 4-((1R,5S)-3,8-diazabicyclo[3.2.1]octan-3-yl)-7-(8-chloronaphthalen-1-yl)-2-((2,2-difluorotetrahydro-1H-pyrrolizin-7a(5H)-yl)methoxy)-8-fluoropyrido[4,3-d]pyrimidine bis(2,2,2-trifluoroacetate) (9.4 mg, 0.011 mmol, 25%). LCMS (MM-ES+APCI, Pos): m/z 595.2 (M+H).

Example 94

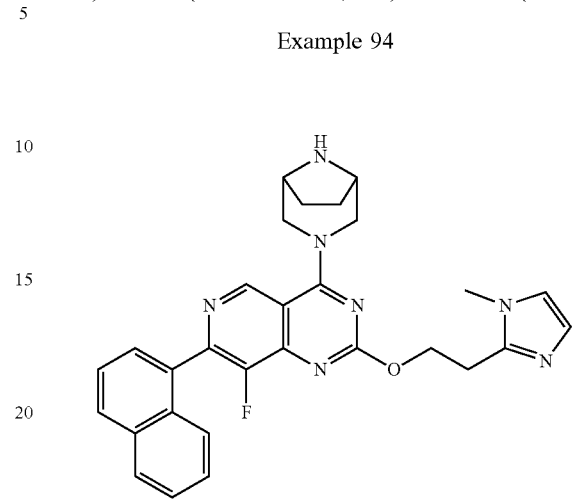

4-((1R,5S)-3,8-diazabicyclo[3.2.1]octan-3-yl)-8-fluoro-2-(2-(1-methyl-1H-imidazol-2-yl)ethoxy)-7-(naphthalen-1-yl)pyrido[4,3-d]pyrimidine Synthesized according to Example 3, Steps H-I substituting 4,4,5,5-tetramethyl-2-(naphthalen-1-yl)-1,3,2-dioxaborolane in place of 4-(4,4,5,5-tetramethyl-1,3,2-dioxaborolan-2-yl)naphthalen-2-ol to afford 4-((1R,5S)-3,8-diazabicyclo[3.2.1]octan-3-yl)-8-fluoro-2-(2-(1-methyl-1H-imidazol-2-yl)ethoxy)-7-(naphthalen-1-yl)pyrido[4,3-d]pyrimidine (8.1 mg, 0.015 mmol, 49%). LCMS (MM-ES+APCI, Pos): m/z 510.2 (M+H).

Example 95

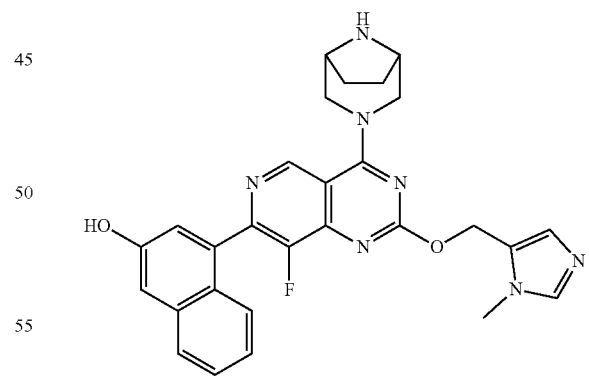

4-(4-((1R,5S)-3,8-diazabicyclo[3.2.1]octan-3-yl)-8-fluoro-2-((1-methyl-1H-imidazol-5-yl)methoxy)pyrido[4,3-d]pyrimidin-7-yl)naphthalen-2-ol Synthesized according to Example 3, Steps G-I substituting (1-methyl-1H-imidazol-5-yl)methanol in place of 2-(1-methyl-1H-imidazol-2-yl)ethan-1-ol to afford 4-(4-((1R,5S)-3,8-diazabicyclo[3.2.1]octan-3-yl)-8-fluoro-2-((1- methyl-1H-imidazol-5-yl)methoxy)pyrido[4,3-d]pyrimidin-7-yl)naphthalen-2-ol (10.6 mg, 0.019 mmol, 45%). LCMS (MM-ES+APCI, Pos): m/z 512.3 (M+H).

Example 96

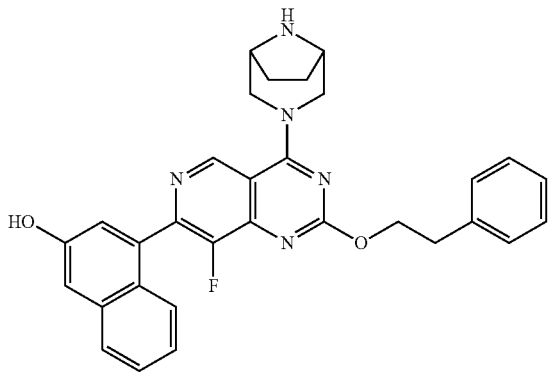 [SMILES: Oc1cc(-c2ncc3c(N4CC5CCC(C4)N5)nc(OCCc4ccccc4)nc3c2F)c2ccccc2c1]

4-(4-((1R,5S)-3,8-diazabicyclo[3.2.1]octan-3-yl)-8-fluoro-2-phenethoxypyrido[4,3-d]pyrimidin-7-yl)naphthalen-2-ol Synthesized according to Example 3, Steps G-I substituting 2-phenylethan-1-ol in place of 2-(1-methyl-1H-imidazol-2-yl)ethan-1-ol to afford 4-(4-((1R,5S)-3,8-diazabicyclo[3.2.1]octan-3-yl)-8-fluoro-2-phenethoxypyrido[4,3-d]pyrimidin-7-yl)naphthalen-2-ol (29.8 mg, 0.055 mmol, 75%). LCMS (MM-ES+APCI, Pos): m/z 522.2 (M+H).

Example 97

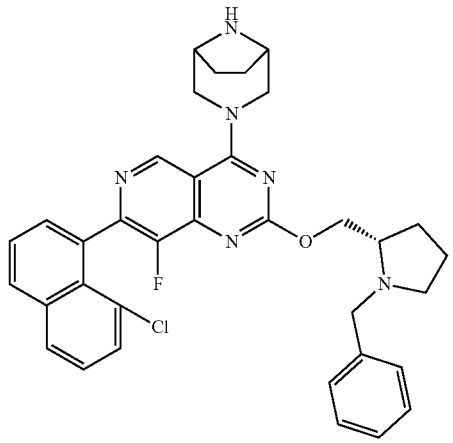 [SMILES: Fc1c(-c2cccc3cccc(Cl)c23)ncc2c(N3CC4CCC(C3)N4)nc(OC[C@@H]3CCCN3Cc3ccccc3)nc12]

2-(((S)-1-benzylpyrrolidin-2-yl)methoxy)-4-((1R,5S)-3,8-diazabicyclo[3.2.1]octan-3-yl)-7-(8-chloronaphthalen-1-yl)-8-fluoropyrido[4,3-d]pyrimidine Synthesized according to Example 30, Steps A-F,H substituting 2-(8-chloronaphthalen-1-yl)-4,4,5,5-tetramethyl-1,3,2-dioxaborolane in place of 2-(3-(benzyloxy)naphthalen-1-yl)-4,4,5,5-tetramethyl-1,3,2-dioxaborolane in Step A and (S)-(1-benzylpyrrolidin-2-yl)methanol in place of 2-(1-methyl-1H-benzo[d]imidazol-2-yl)ethan-1-ol dihydrate in Step F to afford 2-(((S)-1-benzylpyrrolidin-2-yl)methoxy)-4-((1R,5S)-3,8-diazabicyclo[3.2.1]octan-3-yl)-7-(8-chloronaphthalen-1-yl)-8-fluoropyrido[4,3-d]pyrimidine (1.4 mg, 0.002 mmol, 4%). LCMS (MM-ES+APCI, Pos): m/z 609.3 (M+H).

Example 98

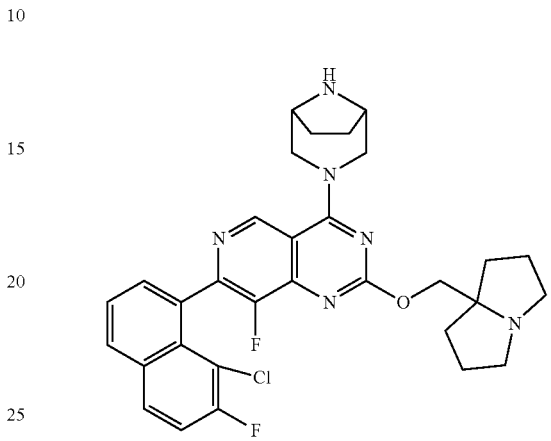

4-((1R,5S)-3,8-diazabicyclo[3.2.1]octan-3-yl)-7-(8-chloro-7-fluoronaphthalen-1-yl)-8-fluoro-2-((tetrahydro-1H-pyrrolizin-7a(5H)-yl)methoxy)pyrido[4,3-d]pyrimidine bis(2,2,2-trifluoroacetate)

Synthesized according to Example 29, Steps C-I substituting 2-(8-chloro-7-fluoronaphthalen-1-yl)-4,4,5,5-tetramethyl-1,3,2-dioxaborolane (Synthesized according to Example 44, step A-C) in place of 2-(8-chloronaphthalen-1-yl)-4,4,5,5-tetramethyl-1,3,2-dioxaborolane in Step C and (tetrahydro-1H-pyrrolizin-7a(5H)-yl)methanol in place of (S)-(1-isopropylpyrrolidin-2-yl)methanol in Step H to afford 4-((1R,5S)-3,8-diazabicyclo[3.2.1]octan-3-yl)-7-(8-chloro-7-fluoronaphthalen-1-yl)-8-fluoro-2-((tetrahydro-1H-pyrrolizin-7a(5H)-yl)methoxy)pyrido[4,3-d]pyrimidine bis(2,2,2-trifluoroacetate) (10.4 mg, 0.013 mmol, 22%). LCMS (MM-ES+APCI, Pos): m/z 577.2 (M+H).

Example 99

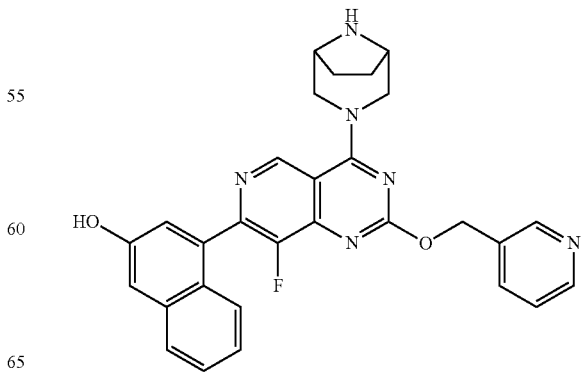

281

4-(4-((1R,5S)-3,8-diazabicyclo[3.2.1]octan-3-yl)-8-fluoro-2-(pyridin-3-ylmethoxy)pyrido[4,3-d]pyrimidin-7-yl)naphthalen-2-ol Synthesized according to Example 3, Steps G-I substituting pyridin-3-ylmethanol in place of 2-(1-methyl-1H-imidazol-2-yl)ethan-1-ol to afford 4-(4-((1R,5S)-3,8-diazabicyclo[3.2.1]octan-3-yl)-8-fluoro-2-(pyridin-3-ylmethoxy)pyrido[4,3-d]pyrimidin-7-yl)naphthalen-2-ol (22.1 mg, 0.042 mmol, 47%). LCMS (MM-ES+APCI, Pos): m/z 509.2 (M+H).

Example 100

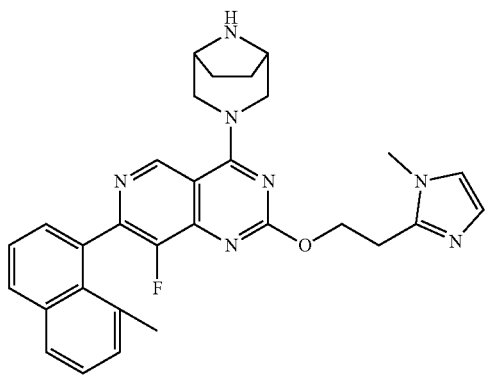 [SMILES: Cc1cccc2cccc(-c3ncc4c(N5CC6CCC(C5)N6)nc(OCCc5nccn5C)nc4c3F)c12]

4-((1R,5S)-3,8-diazabicyclo[3.2.1]octan-3-yl)-8-fluoro-2-(2-(1-methyl-1H-imidazol-2-yl)ethoxy)-7-(8-methylnaphthalen-1-yl)pyrido[4,3-d]pyrimidine Synthesized according to Example 3, Steps H-I substituting 4,4,5,5-tetramethyl-2-(8-methylnaphthalen-1-yl)-1,3,2-dioxaborolane in place of 4-(4,4,5,5-tetramethyl-1,3,2-dioxaborolan-2-yl)naphthalen-2-ol to afford 4-((1R,5S)-3,8-diazabicyclo[3.2.1]octan-3-yl)-8-fluoro-2-(2-(1-methyl-1H-imidazol-2-yl)ethoxy)-7-(8-methylnaphthalen-1-yl)pyrido[4,3-d]pyrimidine (4.1 mg, 0.007 mmol, 30%). LCMS (MM-ES+APCI, Pos): m/z 524.2 (M+H).

Example 101

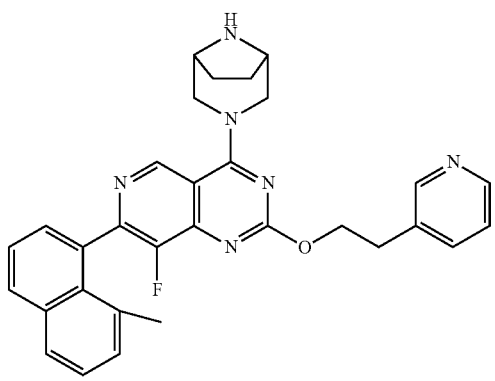 [SMILES: Cc1cccc2cccc(-c3ncc4c(N5CC6CCC(C5)N6)nc(OCCc5cccnc5)nc4c3F)c12]

282

(1S,4S)-5-(3-((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)propyl)-2-oxa-5-azabicyclo[2.2.1]heptane Synthesized according to Example 3, Steps G-I substituting 2-(pyridin-3-yl)ethan-1-ol in place of 2-(1-methyl-1H-imidazol-2-yl)ethan-1-ol in Step G and 4,4,5,5-tetramethyl-2-(8-methylnaphthalen-1-yl)-1,3,2-dioxaborolane in place of 4-(4,4,5,5-tetramethyl-1,3,2-dioxaborolan-2-yl)naphthalen-2-ol in Step H to afford 4-((1R,5S)-3,8-diazabicyclo[3.2.1]octan-3-yl)-8-fluoro-7-(8-methylnaphthalen-1-yl)-2-(2-(pyridin-3-yl)ethoxy)pyrido[4,3-d]pyrimidine (13.0 mg, 0.024 mmol, 36%). LCMS (MM-ES+APCI, Pos): m/z 521.2 (M+H).

Example 102

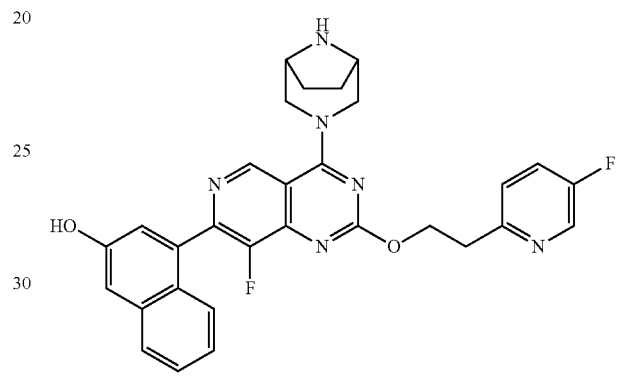

4-(4-((1R,5S)-3,8-diazabicyclo[3.2.1]octan-3-yl)-8-fluoro-2-(2-(5-fluoropyridin-2-yl)ethoxy)pyrido[4,3-d]pyrimidin-7-yl)naphthalen-2-ol Synthesized according to Example 3, Steps G-I substituting 2-(5-fluoropyridin-2-yl)ethan-1-ol in place of 2-(1-methyl-1H-imidazol-2-yl)ethan-1-ol to afford 4-(4-((1R,5S)-3,8-diazabicyclo[3.2.1]octan-3-yl)-8-fluoro-2-(2-(5-fluoropyridin-2-yl)ethoxy)pyrido[4,3-d]pyrimidin-7-yl)naphthalen-2-ol (79.2 mg, 0.145 mmol, 76%). LCMS (MM-ES+APCI, Pos): m/z 541.2 (M+H).

Example 103

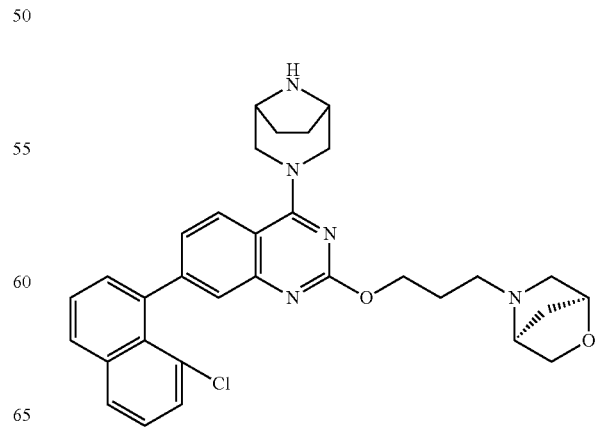

283

(1S,4S)-5-(3-((4-((1R,5S)-3,8-diazabicyclo[3.2.1]
octan-3-yl)-7-(8-chloronaphthalen-1-yl)-8-fluoro-
pyrido[4,3-d]pyrimidin-2-yl)oxy)propyl)-2-oxa-5-
azabicyclo[2.2.1]heptane Synthesized according to Example 3, Steps G-I substituting 3-((1S,4S)-2-oxa-5-azabicyclo[2.2.1]heptan-5-yl)propan-1-ol in place of 2-(1-methyl-1H-imidazol-2-yl)ethan-1-ol in Step G and 2-(8-chloronaphthalen-1-yl)-4,4,5,5-tetramethyl-1,3,2-dioxaborolane in place of 4-(4,4,5,5-tetramethyl-1,3,2-dioxaborolan-2-yl)naphthalen-2-ol in Step H to afford (1S,4S)-5-(3-((4-((1R,5S)-3,8-diazabicyclo[3.2.1]octan-3-yl)-7-(8-chloronaphthalen-1-yl)-8-fluoro-pyrido[4,3-d]pyrimidin-2-yl)oxy)propyl)-2-oxa-5-azabicyclo[2.2.1]heptane (5.1 mg, 0.009 mmol, 29%). LCMS (MM-ES+APCI, Pos): m/z 575.2 (M+H).

Example 104

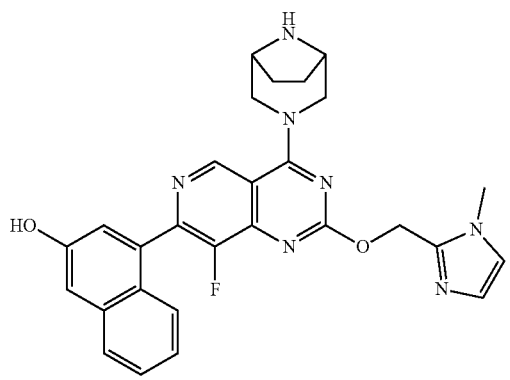 [SMILES: Cn1ccnc1COc1nc(N2CC3CCC(C2)N3)c2cnc(-c3cc(O)cc4ccccc34)c(F)c2n1]

4-(4-((1R,5S)-3,8-diazabicyclo[3.2.1]octan-3-yl)-8-
fluoro-2-((1-methyl-1H-imidazol-2-yl)methoxy)
pyrido[4,3-d]pyrimidin-7-yl)naphthalen-2-ol Synthesized according to Example 3, Steps G-I substituting (1-methyl-1H-imidazol-2-yl)methanol in place of 2-(1-methyl-1H-imidazol-2-yl)ethan-1-ol to afford 4-(4-((1R,5S)-3,8-diazabicyclo[3.2.1]octan-3-yl)-8-fluoro-2-((1-methyl-1H-imidazol-2-yl)methoxy)pyrido[4,3-d]pyrimidin-7-yl)naphthalen-2-ol (12.8 mg, 0.025 mmol, 42%). LCMS (MM-ES+APCI, Pos): m/z 512.2 (M+H).

Example 105

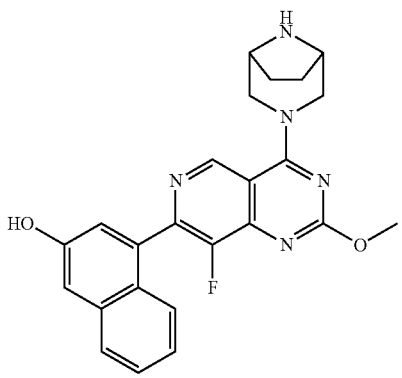 [SMILES: COc1nc(N2CC3CCC(C2)N3)c2cnc(-c3cc(O)cc4ccccc34)c(F)c2n1]

284

4-(4-((1R,5S)-3,8-diazabicyclo[3.2.1]octan-3-yl)-8-
fluoro-2-methoxypyrido[4,3-d]pyrimidin-7-yl)naph-
thalen-2-ol

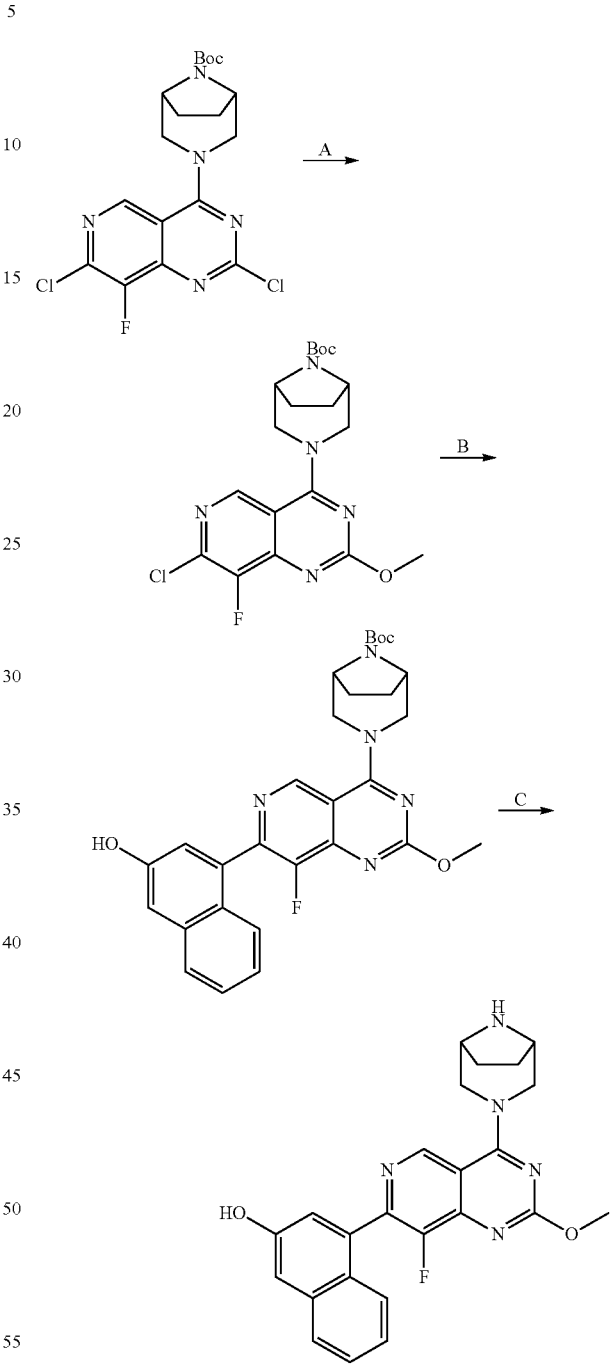

Step A. tert-butyl (1R,5S)-3-(7-chloro-8-fluoro-2-methoxypyrido[4,3-d]pyrimidin-4-yl)-3,8-diazabicyclo[3.2.1]octane-8-carboxylate: To a solution of tert-butyl (1R,5S)-3-(2,7-dichloro-8-fluoropyrido[4,3-d]pyrimidin-4-yl)-3,8-diazabicyclo[3.2.1]octane-8-carboxylate (200 mg, 0.467 mmol) in anhydrous THF (20 mL) at room temperature was added NaOMe (0.117 mL, 0.514 mmol). The mixture was stirred for 16 hours. The mixture was partitioned between sat. NH₄Cl (75 mL) and EtOAc (30 mL), and the aqueous layer was extracted with EtOAc (2×30 mL). The combined organic phases were washed with brine (40 mL), dried over Na$_2$SO$_4$, filtered and concentrated in vacuo. The residue was purified by flash column chromatography eluting with 5-60% EtOAc/hexanes to afford tert-butyl (1R,5S)-3-(7-chloro-8-fluoro-2-methoxypyrido[4,3-d]pyrimidin-4-yl)-3,8-diazabicyclo[3.2.1]octane-8-carboxylate (97.2 mg, 0.229 mmol, 49%). LCMS (MM-ES+APCI, Pos): m/z 424.1 (M+H).

Step B. tert-butyl (1R,5S)-3-(8-fluoro-7-(3-hydroxynaphthalen-1-yl)-2-methoxypyrido[4,3-d]pyrimidin-4-yl)-3,8-diazabicyclo[3.2.1]octane-8-carboxylate: A mixture of 4-(4,4,5,5-tetramethyl-1,3,2-dioxaborolan-2-yl)naphthalen-2-ol (93 mg, 0.344 mmol), tert-butyl (1R,5S)-3-(7-chloro-8-fluoro-2-methoxypyrido[4,3-d]pyrimidin-4-yl)-3,8-diazabicyclo[3.2.1]octane-8-carboxylate (97 mg, 0.229 mmol), K$_2$CO$_3$ (0.344 mL, 0.688 mmol), Pd(PPh$_3$)$_4$ (26.5 mg, 0.023 mmol) in dioxane (2.3 mL, 0.229 mmol) was sparged with argon and heated at 85° C. for 16 hours. The mixture was diluted with water (60 mL) and extracted with EtOAc (3×30 mL). The combined organic layers were washed with brine (50 mL), dried over Na$_2$SO$_4$, filtered and concentrated in vacuo. The residue was purified by flash column chromatography eluting with 0-50% EtOAc/hexanes to afford tert-butyl (1R,5S)-3-(8-fluoro-7-(3-hydroxynaphthalen-1-yl)-2-methoxypyrido[4,3-d]pyrimidin-4-yl)-3,8-diazabicyclo[3.2.1]octane-8-carboxylate (106.4 mg, 0.200 mmol, 87%). LCMS (MM-ES+APCI, Pos): m/z 532.2 (M+H).

Step C. 4-(4-((1R,5S)-3,8-diazabicyclo[3.2.1]octan-3-yl)-8-fluoro-2-methoxypyrido[4,3-d]pyrimidin-7-yl)naphthalen-2-ol: To a solution of tert-butyl (1R,5S)-3-(8-fluoro-7-(3-hydroxynaphthalen-1-yl)-2-methoxypyrido[4,3-d]pyrimidin-4-yl)-3,8-diazabicyclo[3.2.1]octane-8-carboxylate (106 mg, 0.2002 mmol) in CH$_2$Cl$_2$ (4 ml, 0.2002 mmol) was added TFA (0.308 mL, 4.003 mmol) at 0° C. The mixture was stirred at room temperature for 4 hours. The solution was poured into a mixture of saturated bicarbonate (20 mL) and EtOAc (15 mL). The aqueous layer was washed with EtOAc (2×15 mL). The combined organic layers were washed with saturated bicarbonate (15 mL), brine (15 mL), dried over Na$_2$SO$_4$, and concentrated in vacuo. The residue was purified by flash column chromatography eluting with 0-100% (20% MeOH/CH$_2$Cl$_2$)/CH$_2$Cl$_2$ gradient to afford 4-(4-((1R,5S)-3,8-diazabicyclo[3.2.1]octan-3-yl)-8-fluoro-2-methoxypyrido[4,3-d]pyrimidin-7-yl)naphthalen-2-ol (71.9 mg, 0.167 mmol, 83%). LCMS (MM-ES+APCI, Pos): m/z 432.1 (M+H).

Example 106

4-(4-((1R,5S)-3,8-diazabicyclo[3.2.1]octan-3-yl)-8-fluoro-2-(2-(pyridin-3-yl)ethoxy)pyrido[4,3-d]pyrimidin-7-yl)naphthalen-2-ol Synthesized according to Example 3, Steps G-I substituting 2-(pyridin-3-yl)ethan-1-ol in place of 2-(1-methyl-1H-imidazol-2-yl)ethan-1-ol to afford 4-(4-((1R,5S)-3,8-diazabicyclo[3.2.1]octan-3-yl)-8-fluoro-2-(2-(pyridin-3-yl)ethoxy)pyrido[4,3-d]pyrimidin-7-yl)naphthalen-2-ol (16.5 mg, 0.031 mmol, 38%). LCMS (MM-ES+APCI, Pos): m/z 523.2 (M+H).

Example 107

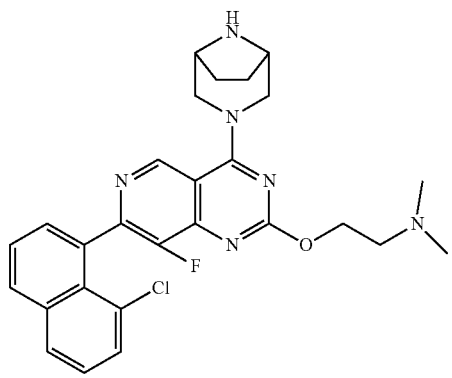

2-((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)-N,N-dimethylethan-1-amine Synthesized according to Example 3, Steps G-I substituting 2-(dimethylamino)ethan-1-ol in place of 2-(1-methyl-1H-imidazol-2-yl)ethan-1-ol in Step G and 2-(8-chloronaphthalen-1-yl)-4,4,5,5-tetramethyl-1,3,2-dioxaborolane in place of 4-(4,4,5,5-tetramethyl-1,3,2-dioxaborolan-2-yl)naphthalen-2-ol in Step H to afford 2-((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)-N,N-dimethylethan-1-amine (5.1 mg, 0.010 mmol, 9%). LCMS (MM-ES+APCI, Pos): m/z 507.2 (M+H).

Example 108

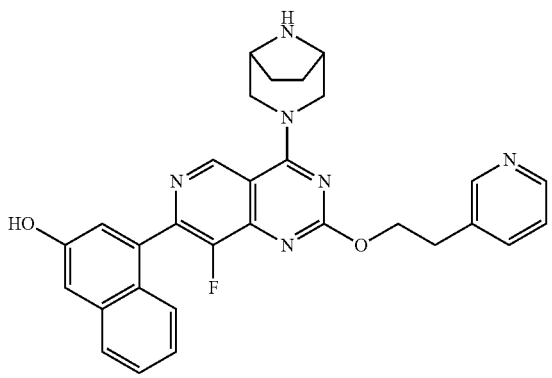 [SMILES: Oc1cc(-c2ncc3c(N4CC5CCC(C4)N5)nc(OCCc4cccnc4)nc3c2F)c2ccccc2c1]

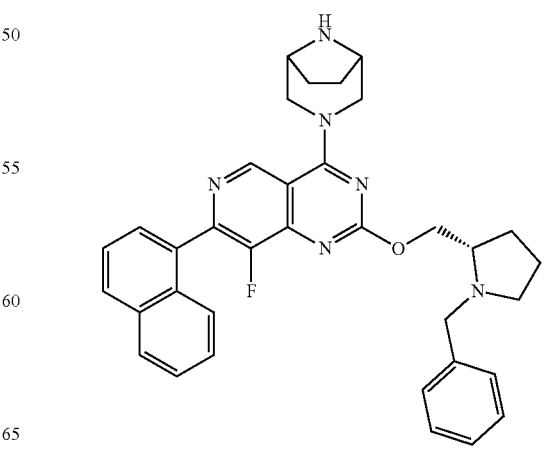

287

2-(((S)-1-benzylpyrrolidin-2-yl)methoxy)-4-((1R,5S)-3,8-diazabicyclo[3.2.1]octan-3-yl)-8-fluoro-7-(naphthalen-1-yl)pyrido[4,3-d]pyrimidine Synthesized according to Example 3, Steps G-I substituting (S)-(1-benzylpyrrolidin-2-yl)methanol in place of 2-(1-methyl-1H-imidazol-2-yl)ethan-1-ol in Step G and 4,4,5,5-tetramethyl-2-(naphthalen-1-yl)-1,3,2-dioxaborolane in place of 4-(4,4,5,5-tetramethyl-1,3,2-dioxaborolan-2-yl)naphthalen-2-ol in Step H to afford 2-(((S)-1-benzylpyrrolidin-2-yl)methoxy)-4-((1R,5S)-3,8-diazabicyclo[3.2.1]octan-3-yl)-8-fluoro-7-(naphthalen-1-yl)pyrido[4,3-d]pyrimidine (23 mg, 0.039 mmol, 56%). LCMS (MM-ES+APCI, Pos): m/z 575.3 (M+H).

Example 109

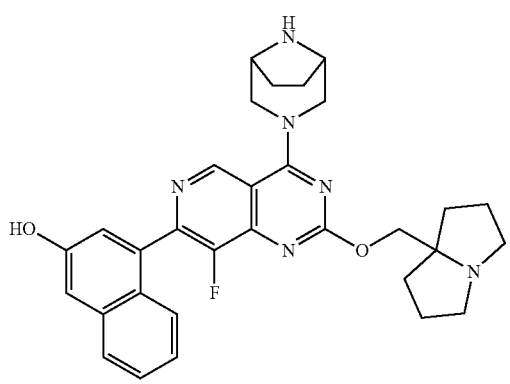 [SMILES: Oc1cc(-c2ncc3c(N4CC5CCC(C4)N5)nc(OCC45CCCN4CCC5)nc3c2F)c2ccccc2c1]

4-(4-((1R,5S)-3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)naphthalen-2-ol bis(2,2,2-trifluoroacetate)

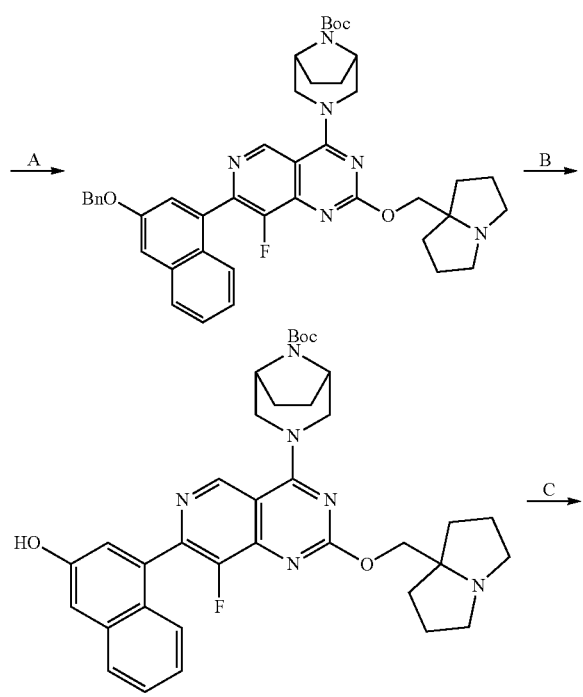

288

-continued

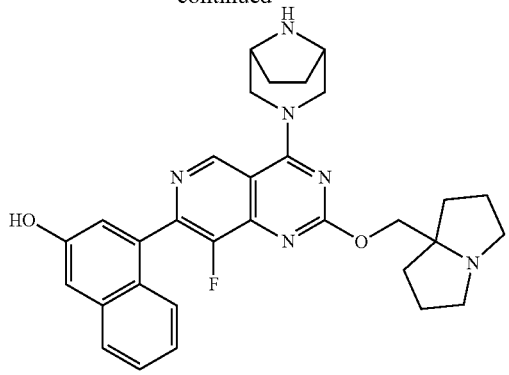

Step A: Synthesized according to Example 3, Steps G-H substituting (tetrahydro-1H-pyrrolizin-7a(5H)-yl)methanol in place of 2-(1-methyl-1H-imidazol-2-yl)ethan-1-ol in Step G and 2-(3-(benzyloxy)naphthalen-1-yl)-4,4,5,5-tetramethyl-1,3,2-dioxaborolane in place of 4-(4,4,5,5-tetramethyl-1,3,2-dioxaborolan-2-yl)naphthalen-2-ol in Step H to afford tert-butyl (1R,5S)-3-(7-(3-(benzyloxy)naphthalen-1-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (28.6 mg, 0.039 mmol, 42%). LCMS (MM-ES+APCI, Pos): m/z 731.4 (M+H).

Step B. tert-butyl (1R,5S)-3-(8-fluoro-7-(3-hydroxynaphthalen-1-yl)-2-((tetrahydro-1H-pyrrolizin-7a(5H)-yl)methoxy)pyrido[4,3-d]pyrimidin-4-yl)-3,8-diazabicyclo[3.2.1]octane-8-carboxylate: A stirred mixture of tert-butyl (1R,5S)-3-(7-(3-(benzyloxy)naphthalen-1-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (28.6 mg, 0.039 mmol), and Pd/C (5% Degussa type, 15 mg, 0.141 mmol) in MeOH (0.196 mL, 0.039 mmol) was degassed and left stirred under $H_2$ atmosphere for 2 hours. The Pd/C was filtered off and washed with MeOH. The filtrate was concentrated in vacuo to afford tert-butyl (1R,5S)-3-(8-fluoro-7-(3-hydroxynaphthalen-1-yl)-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (20.3 mg, 0.032 mmol, 81%). LCMS (MM-ES+APCI, Pos): m/z 641.3 (M+H).

Step C. 4-(4-((1R,5S)-3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)naphthalen-2-ol bis(2,2,2-trifluoroacetate): To a solution of tert-butyl (1R,5S)-3-(8-fluoro-7-(3-hydroxynaphthalen-1-yl)-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (20.3 mg, 0.032 mmol) in $CH_2Cl_2$ (0.634 mL, 0.032 mmol) was added TFA (0.049 mL, 0.634 mmol). The mixture was stirred at room temperature for 2 hours. The reaction was concentrated in vacuo. The residue was purified by Gilson prep HPLC (5-95% ACN/$H_2O$ over 20 minutes), and then lyophilized to afford 4-(4-((1R,5S)-3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)naphthalen-2-ol bis(2,2,2-trifluoroacetate) (7.5 mg, 0.010 mmol, 30%). LCMS (MM-ES+APCI, Pos): m/z 541.3 (M+H).

Example 110

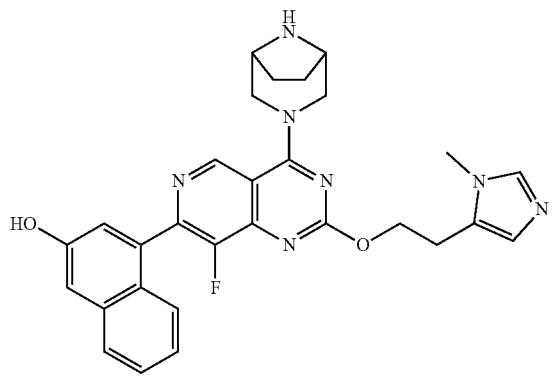 [SMILES: Cn1cncc1CCOc1nc(N2CC3CCC(C2)N3)c2cnc(-c3cc(O)cc4ccccc34)c(F)c2n1]

4-(4-((1R,5S)-3,8-diazabicyclo[3.2.1]octan-3-yl)-8-fluoro-2-(2-(1-methyl-1H-imidazol-5-yl)ethoxy)pyrido[4,3-d]pyrimidin-7-yl)naphthalen-2-ol Synthesized according to Example 3, Steps G-I substituting 2-(1-methyl-1H-imidazol-5-yl)ethan-1-ol in place of 2-(1-methyl-1H-imidazol-2-yl)ethan-1-ol to afford 4-(4-((1R,5S)-3,8-diazabicyclo[3.2.1]octan-3-yl)-8-fluoro-2-(2-(1-methyl-1H-imidazol-5-yl)ethoxy)pyrido[4,3-d]pyrimidin-7-yl)naphthalen-2-ol (14.6 mg, 0.027 mmol, 57%). LCMS (MM-ES+APCI, Pos): m/z 526.2 (M+H).

Example 111

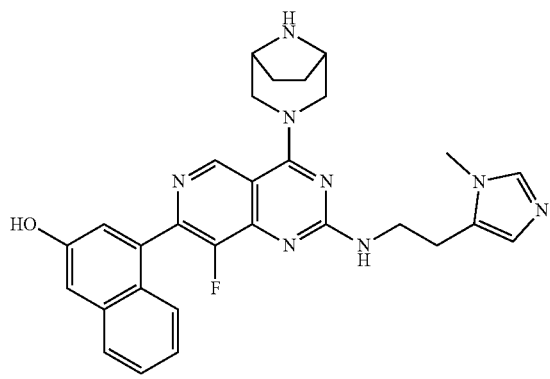 [SMILES: Cn1cncc1CCNc1nc(N2CC3CCC(C2)N3)c2cnc(-c3cc(O)cc4ccccc34)c(F)c2n1]

4-(4-((1R,5S)-3,8-diazabicyclo[3.2.1]octan-3-yl)-8-fluoro-2-((2-(1-methyl-1H-imidazol-2-yl)ethyl)amino)pyrido[4,3-d]pyrimidin-7-yl)naphthalen-2-ol Synthesized according to Example 3, Steps G-I substituting 2-(1-methyl-1H-imidazol-2-yl)ethan-1-amine dihydrochloride in place of 2-(1-methyl-1H-imidazol-2-yl)ethan-1-ol to afford 4-(4-((1R,5S)-3,8-diazabicyclo[3.2.1]octan-3-yl)-8-fluoro-2-((2-(1-methyl-1H-imidazol-2-yl)ethyl)amino)pyrido[4,3-d]pyrimidin-7-yl)naphthalen-2-ol (16.9 mg, 0.032 mmol, 39%). LCMS (MM-ES+APCI, Pos): m/z 525.2 (M+H).

Example 112

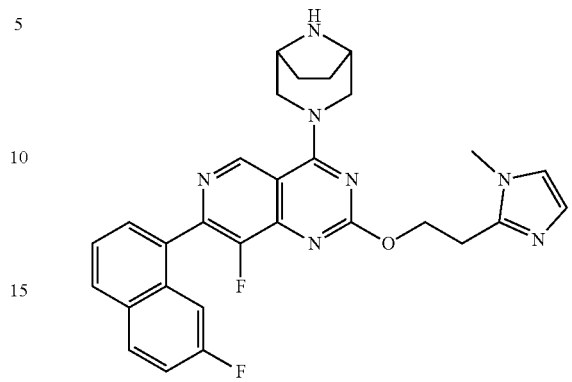

4-((1R,5S)-3,8-diazabicyclo[3.2.1]octan-3-yl)-8-fluoro-7-(7-fluoronaphthalen-1-yl)-2-(2-(1-methyl-1H-imidazol-2-yl)ethoxy)pyrido[4,3-d]pyrimidine Synthesized according to Example 3, Steps G-I substituting 2-(7-fluoronaphthalen-1-yl)-4,4,5,5-tetramethyl-1,3,2-dioxaborolane in place of 4-(4,4,5,5-tetramethyl-1,3,2-dioxaborolan-2-yl)naphthalen-2-ol to afford 4-((1R,5S)-3,8-diazabicyclo[3.2.1]octan-3-yl)-8-fluoro-7-(7-fluoronaphthalen-1-yl)-2-(2-(1-methyl-1H-imidazol-2-yl)ethoxy)pyrido[4,3-d]pyrimidine (12.5 mg, 0.024 mmol, 65%). LCMS (MM-ES+APCI, Pos): m/z 528.2 (M+H).

Example 113

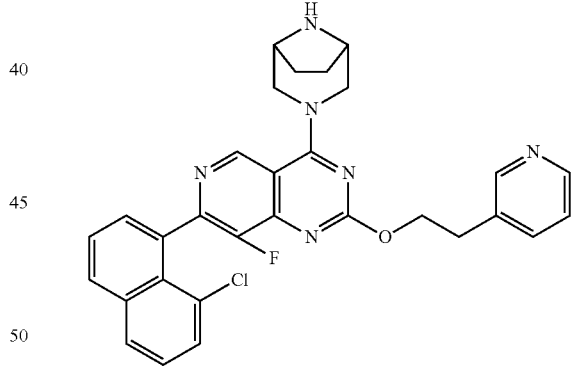

4-((1R,5S)-3,8-diazabicyclo[3.2.1]octan-3-yl)-7-(8-chloronaphthalen-1-yl)-8-fluoro-2-(2-(pyridin-3-yl)ethoxy)pyrido[4,3-d]pyrimidine Synthesized according to Example 3, Steps G-I substituting 2-(pyridin-3-yl)ethan-1-ol in place of 2-(1-methyl-1H-imidazol-2-yl)ethan-1-ol in Step G and 2-(8-chloronaphthalen-1-yl)-4,4,5,5-tetramethyl-1,3,2-dioxaborolane in place of 4-(4,4,5,5-tetramethyl-1,3,2-dioxaborolan-2-yl)naphthalen-2-ol in Step H to afford 4-((1R,5S)-3,8-diazabicyclo[3.2.1]octan-3-yl)-7-(8-chloronaphthalen-1-yl)-8-fluoro-2-(2-(pyridin-3-yl)ethoxy)pyrido[4,3-d]pyrimidine (9.0 mg, 0.016 mmol, 28%). LCMS (MM-ES+APCI, Pos): m/z 541.2 (M+H).

Example 114

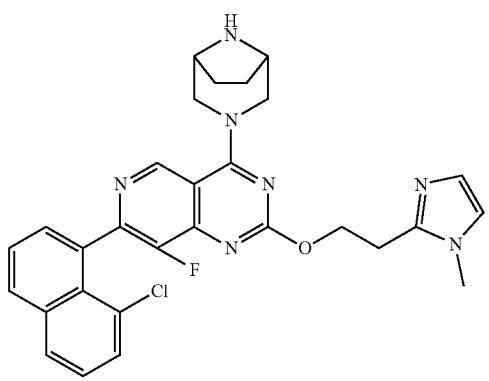 [SMILES: Cn1ccnc1CCOc1nc(N2CC3CCC(C2)N3)c2cnc(-c3cccc4cccc(Cl)c34)c(F)c2n1]

4-((1R,5S)-3,8-diazabicyclo[3.2.1]octan-3-yl)-7-(8-chloronaphthalen-1-yl)-8-fluoro-2-(2-(1-methyl-1H-imidazol-2-yl)ethoxy)pyrido[4,3-d]pyrimidine Synthesized according to Example 3, Steps G-I substituting 2-(8-chloronaphthalen-1-yl)-4,4,5,5-tetramethyl-1,3,2-dioxaborolane in place of 4-(4,4,5,5-tetramethyl-1,3,2-dioxaborolan-2-yl)naphthalen-2-ol to afford 4-((1R,5S)-3,8-diazabicyclo[3.2.1]octan-3-yl)-7-(8-chloronaphthalen-1-yl)-8-fluoro-2-(2-(1-methyl-1H-imidazol-2-yl)ethoxy)pyrido[4,3-d]pyrimidine (3.7 mg, 0.007 mmol, 20%). LCMS (MM-ES+APCI, Pos): m/z 544.2 (M+H).

Example 115

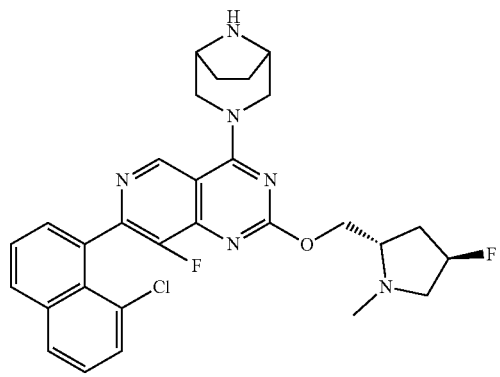 [SMILES: CN1C[C@H](F)C[C@H]1COc1nc(N2CC3CCC(C2)N3)c2cnc(-c3cccc4cccc(Cl)c34)c(F)c2n1]

4-((1R,5S)-3,8-diazabicyclo[3.2.1]octan-3-yl)-7-(8-chloronaphthalen-1-yl)-8-fluoro-2-(((2S,4R)-4-fluoro-1-methylpyrrolidin-2-yl)methoxy)pyrido[4,3-d]pyrimidine Synthesized according to Example 3, Steps G-I substituting ((2S,4R)-4-fluoro-1-methylpyrrolidin-2-yl)methanol in place of 2-(1-methyl-1H-imidazol-2-yl)ethan-1-ol in Step G and 2-(8-chloronaphthalen-1-yl)-4,4,5,5-tetramethyl-1,3,2-dioxaborolane in place of 4-(4,4,5,5-tetramethyl-1,3,2-dioxaborolan-2-yl)naphthalen-2-ol in Step H to afford 4-((1R,5S)-3,8-diazabicyclo[3.2.1]octan-3-yl)-7-(8-chloronaphthalen-1-yl)-8-fluoro-2-(((2S,4R)-4-fluoro-1-methylpyrrolidin-2-yl)methoxy)pyrido[4,3-d]pyrimidine (6.5 mg, 0.012 mmol, 19%). LCMS (MM-ES+APCI, Pos): m/z 551.2 (M+H).

Example 116

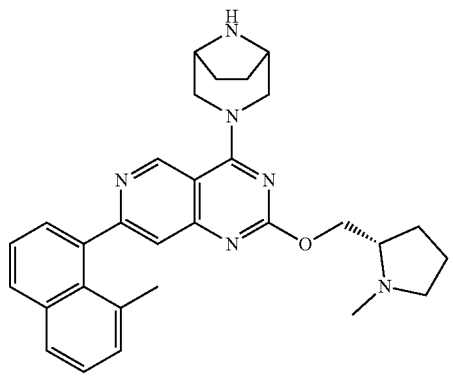 [SMILES: Cc1cccc2cccc(-c3cc4nc(OC[C@@H]5CCCN5C)nc(N5CC6CCC(C5)N6)c4cn3)c12]

4-((1R,5S)-3,8-diazabicyclo[3.2.1]octan-3-yl)-7-(8-methylnaphthalen-1-yl)-2-(((S)-1-methylpyrrolidin-2-yl)methoxy)pyrido[4,3-d]pyrimidine Step A. 4,4,5,5-tetramethyl-2-(8-methylnaphthalen-1-yl)-1,3,2-dioxaborolane. To a solution of 1-bromo-8-methylnaphthalene (1 g, 4.5 mmol) in dioxane (23 mL) were added potassium acetate (1.3 g, 14 mmol) and 4,4,4',4',5,5,5',5'-octamethyl-2,2'-bi(1,3,2-dioxaborolane) (3.4 g, 14 mmol) and the reaction was sparged with N2 for 15 minutes, followed by addition of PdCl₂(dppf) (330 mg, 0.45 mmol). The reaction was heated to 95° C. for 18 hrs. The reaction was concentrated in vacuo and taken up in DCM. The slurry was filtered through GF/F paper and the organics concentrated in vacuo. The crude material was chromatographed using 0→30% ethyl acetate/hexane as eluent to give 4,4,5, 5-tetramethyl-2-(8-methylnaphthalen-1-yl)-1,3,2-dioxa-borolane (1.5 g, 4.5 mmol, 99% yield). HPLC (5-95% ACN/H₂O+0.1% TFA) 4.67 min.

Step B: 4-((1R,5S)-3,8-diazabicyclo[3.2.1]octan-3-yl)-7-(8-methylnaphthalen-1-yl)-2-(((S)-1-methylpyrrolidin-2-yl)methoxy)pyrido[4,3-d]pyrimidine. Synthesized according to Example 3, Steps G-I substituting (S)-(1-methylpyrrolidin-2-yl)methanol in place of 2-(1-methyl-1H-imidazol-2-yl)ethan-1-ol and 4,4,5,5-tetramethyl-2-(8-methylnaphthalen-1-yl)-1,3,2-dioxaborolane in place of 4-(4,4,5,5-tetramethyl-1,3,2-dioxaborolan-2-yl)naphthalen-2-ol (8.0 mg, 0.015 mmol, 25%). LCMS (MM-ES+APCI, Pos): m/z 495.2 (M+H).

Example 117

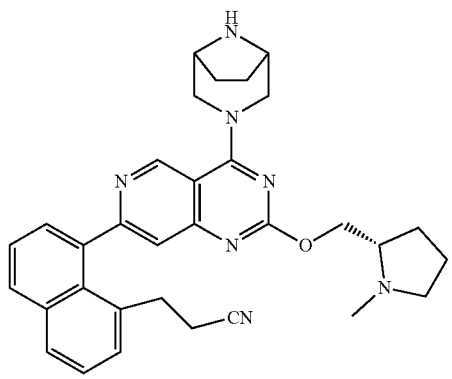 [SMILES: CN1CCC[C@H]1COc1nc(N2CC3CCC(C2)N3)c2cnc(-c3cccc4cccc(CCC#N)c34)cc2n1]

3-(8-(4-((1R,5S)-3,8-diazabicyclo[3.2.1]octan-3-yl)-8-fluoro-2-(((S)-1-methylpyrrolidin-2-yl)methoxy)pyrido[4,3-d]pyrimidin-7-yl)naphthalen-1-yl)propanenitrile bis(2,2,2-trifluoroacetate)

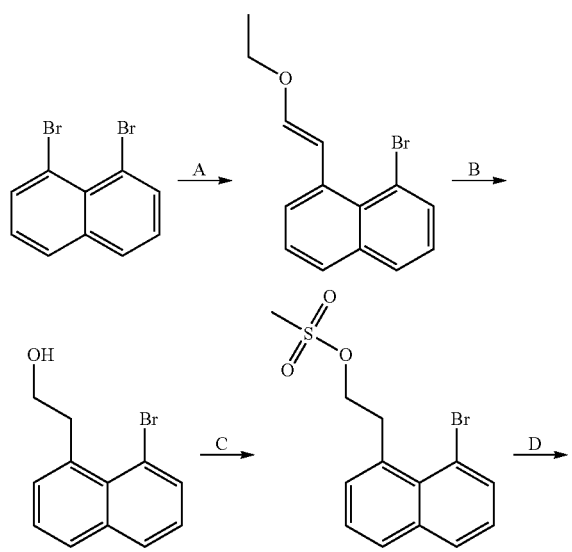

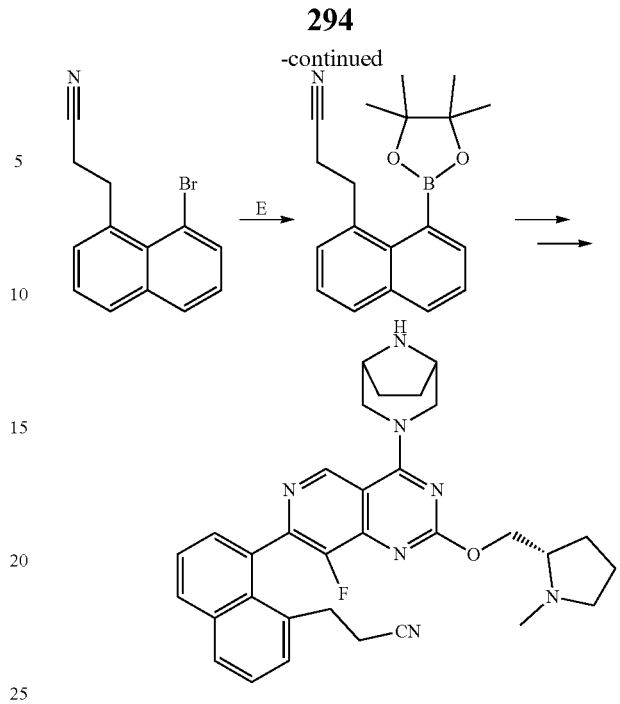

Step A. (E)-1-bromo-8-(2-ethoxyvinyl)naphthalene. A mixture of 1,8-dibromonaphthalene (1.00 g, 3.50 mmol), Pd(PPh₃)₄ (0.404 g, 0.350 mmol), 2M Na₂CO₃ (5.25 ml, 10.5 mmol) and 1,4-dioxane (20 ml) was degassed and neat (E)-2-(2-ethoxyvinyl)-4,4,5,5-tetramethyl-1,3,2-dioxaborolane (0.83 g, 4.2 mmol) was added via syringe. The reaction mixture was stirred at 95° C. for two and one-half days. The mixture was cooled and partitioned between EtOAc (30 mL) and water (100 mL). The layers were separated. The organic layer was washed with brine, decanted, dried over Na₂SO₄ and concentrated in vacuo and the residue was chromatographed on silica gel eluting with 2% EtOAc/Hexanes to give (E)-1-bromo-8-(2-ethoxyvinyl)naphthalene as yellow oil, crystallizing at −20° C. ¹H NMR (400 MHz, CDCl₃): 7.82 (dd, J=7.5, 1.3 Hz, 1H), 7.77 (dd, J=8.3, 1.3 Hz, 1H), 7.76-7.69 (m, 1H), 7.41-7.35 (m, 2H), 7.22 (dd, J=8.0, 7.4 Hz, 1H), 7.11 (d, J=12.5 Hz, 1H), 6.55 (d, J=12.5 Hz, 1H), 4.02 (q, J=7.0 Hz, 2H), 1.40 (t, J=7.0 Hz, 3H).

Step B. 2-(8-bromonaphthalen-1-yl)ethan-1-ol. To a stirred solution of (E)-1-bromo-8-(2-ethoxyvinyl)naphthalene (200 mg, 0.72 mmol) in tetrahydrofuran (2.5 ml) was added conc. aq. hydrogen chloride (0.5 ml, 3.00 mmol) at once and the reaction mixture was stirred for 1 h. The mixture was partitioned between EtOAc (20 mL) and water (10 mL) and the layers were separated. The organic layer was washed with 0.5M NaHCO₃ and poured into a flask. Sodium borohydride (273 mg, 7.2 mmol) was added with vigorous stirring. After 1 h, the organic layer was decanted, washed with sat. NaHCO₃ and brine (5 mL each), dried over Na₂SO₄ and evaporated in vacuo to yield 2-(8-bromonaphthalen-1-yl)ethan-1-ol as pale yellow crystalline solid, yield was nearly quantitative.

Step C. 2-(8-bromonaphthalen-1-yl)ethyl methanesulfonate. A stirred solution of crude 2-(8-bromonaphthalen-1-yl)ethan-1-ol (181 mg, 0.721 mmol) and N-ethyl-N-isopropylpropan-2-amine (0.19 ml, 1.1 mmol) in dichloromethane (5 ml) was cooled in an ice-salt bath and methanesulfonyl chloride (67 µL, 0.87 mmol) was added dropwise. The reaction mixture was warmed to rt during 2 h, and then partitioned between hexane-EtOAc (1:1, 15 mL) and 0.5M NaHCO₃ (5 mL). The layers were separated. The organic phase was washed with brine, dried over Na₂SO₄, and evaporated in vacuo. The residue was dissolved in MTBE (2 mL), filtered and evaporated under N₂ to yield crude 2-(8-bromonaphthalen-1-yl)ethyl methanesulfonate as a colorless oil.

Step D. 3-(8-bromonaphthalen-1-yl)propanenitrile. A mixture of crude 2-(8-bromonaphthalen-1-yl)ethyl methanesulfonate (393 mg, 1.19 mmol), sodium cyanide (88 mg, 1.8 mmol) and N,N-dimethylacetamide (2.4 mL) was stirred at r.t. for 3 days, then heated to 50° C. for 4 h. The mixture was cooled and partitioned between EtOAc (15 mL) and water (10 mL). The layers were separated. The organic phase was washed with brine, dried over Na₂SO₄ and evaporated in vacuo. The residue was chromatographed on silica gel eluting with 10% EtOAc/hexane to yield 3-(8-bromonaphthalen-1-yl)propanenitrile as colorless heavy oil (290 mg, 93%).

Step E. 3-(8-(4,4,5,5-tetramethyl-1,3,2-dioxaborolan-2-yl)naphthalen-1-yl)propanenitrile. To a solution of 3-(8-bromonaphthalen-1-yl)propanenitrile (74 mg, 0.28 mmol) in dioxane (1.42 mL) were added potassium acetate (1.3 g, 0.85 mmol) and 4,4,4',4',5,5,5',5'-octamethyl-2,2'-bi(1,3,2-dioxaborolane) (217 mg, 0.85 mmol) and the reaction was sparged with N2 for 15 minutes followed by addition of PdCl₂(dppf) (21 mg, 0.028 mmol). The reaction was heated to 95° C. for 18 hrs. The reaction was concentrated in vacuo and taken up in DCM. The slurry was filtered through GF/F paper and the organics was concentrated in vacuo. The material was chromatographed using 0→30% ethyl acetate/hexane as eluent to give 3-(8-(4,4,5,5-tetramethyl-1,3,2-dioxaborolan-2-yl)naphthalen-1-yl)propanenitrile (48 mg, 0.08 mmol, 27% yield). 1H-NMR (400 MHz, CDCl₃) δ 7.89-7.93 (m, 2H), 7.72-7.8 (m, 2H), 7.38-7.55 (m, 2H), 3.45 (t, 2H), 2.77 (t, 2H), 1.26 (s, 12H).

Step F: 3-(8-(4-((1R,5S)-3,8-diazabicyclo[3.2.1]octan-3-yl)-8-fluoro-2-(((S)-1-methylpyrrolidin-2-yl)methoxy)pyrido[4,3-d]pyrimidin-7-yl)naphthalen-1-yl)propanenitrile bis(2,2,2-trifluoroacetate). Synthesized according to Example 3, Steps G-I substituting (S)-(1-methylpyrrolidin-2-yl)methanol in place of 2-(1-methyl-1H-imidazol-2-yl)ethan-1-ol and 3-(8-(4,4,5,5-tetramethyl-1,3,2-dioxaborolan-2-yl)naphthalen-1-yl)propanenitrile (32.5 mg, 0.074 mmol) in place of 4-(4,4,5,5-tetramethyl-1,3,2-dioxaborolan-2-yl)naphthalen-2-ol (5.0 mg, 0.006 mmol, 60%). LCMS (MM-ES+APCI, Pos): m/z 552.3 (M+H).

Example 118

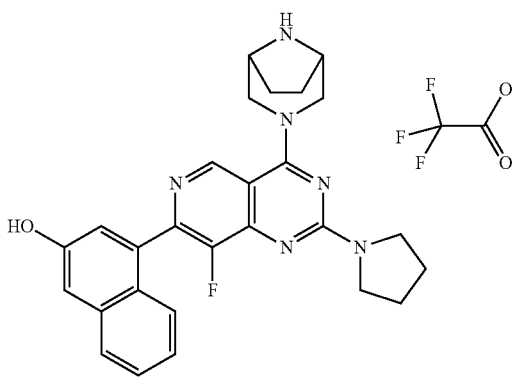

4-(4-((1R,5S)-3,8-diazabicyclo[3.2.1]octan-3-yl)-8-fluoro-2-(pyrrolidin-1-yl)pyrido[4,3-d]pyrimidin-7-yl)naphthalen-2-ol 2,2,2-trifluoroacetate Synthesized according to Example 3, Steps G-I substituting pyrrolidine in place of 2-(1-methyl-1H-imidazol-2-yl)ethan-1-ol (49 mg, 0.084 mmol, 68%). LCMS (MM-ES+APCI, Pos): m/z 471.2 (M+H).

Example 119

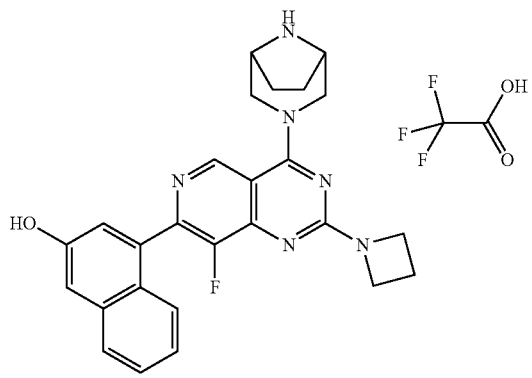 [SMILES: Oc1cc(-c2ncc3c(N4CC5CCC(C4)N5)nc(N4CCC4)nc3c2F)c2ccccc2c1 ; O=C(O)C(F)(F)F]

4-(2-(azetidin-1-yl)-4-((1R,5S)-3,8-diazabicyclo[3.2.1]octan-3-yl)-8-fluoropyrido[4,3-d]pyrimidin-7-yl)naphthalen-2-ol 2,2,2-trifluoroacetate Synthesized according to Example 3, Steps G-I substituting azetidine in place of 2-(1-methyl-1H-imidazol-2-yl)ethan-1-ol (34 mg, 0.06 mmol, 88%). LCMS (MM-ES+APCI, Pos): m/z 457.2 (M+H).

Example 120

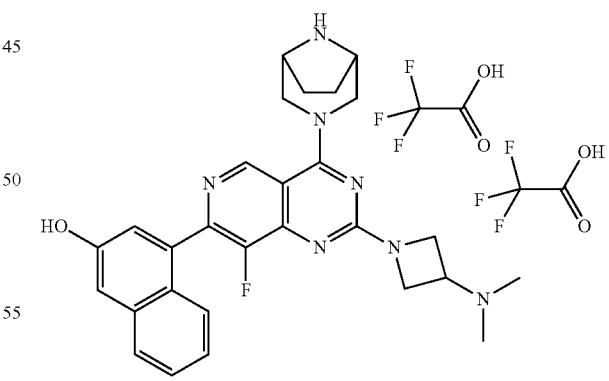

4-(4-((1R,5S)-3,8-diazabicyclo[3.2.1]octan-3-yl)-2-(3-(dimethylamino)azetidin-1-yl)-8-fluoropyrido[4,3-d]pyrimidin-7-yl)naphthalen-2-ol bis(2,2,2-trifluoroacetate)

Synthesized according to Example 3, Steps G-I substituting N, N-dimethylazetidin-3-amine hydrochloride in place of 2-(1-methyl-1H-imidazol-2-yl)ethan-1-ol (30 mg, 0.041 mmol, 88%). LCMS (MM-ES+APCI, Pos): m/z 500.3 (M+H).

Example 121

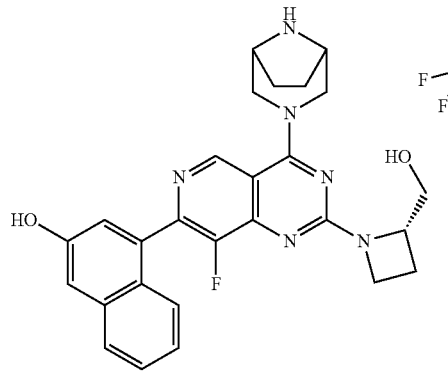

4-(4-((1R,5S)-3,8-diazabicyclo[3.2.1]octan-3-yl)-8-fluoro-2-((S)-2-(hydroxymethyl)azetidin-1-yl)pyrido[4,3-d]pyrimidin-7-yl)naphthalen-2-ol 2,2,2-trifluoroacetate Synthesized according to Example 3, Steps G-I substituting (S)-2-azetidinemethanol in place of 2-(1-methyl-1H-imidazol-2-yl)ethan-1-ol (20.9 mg, 0.035 mmol, 100%). LCMS (MM-ES+APCI, Pos): m/z 487.2 (M+H).

Example 122

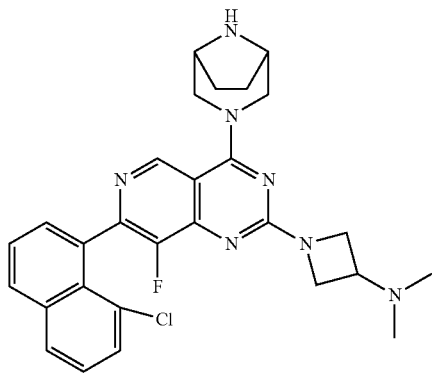 [SMILES: CN(C)C1CN(c2nc(N3CC4CCC(C3)N4)c3cnc(-c4cccc5cccc(Cl)c45)c(F)c3n2)C1]

1-(4-((1R,5S)-3,8-diazabicyclo[3.2.1]octan-3-yl)-7-(8-chloronaphthalen-1-yl)-8-fluoropyrido[4,3-d]pyrimidin-2-yl)-N,N-dimethylazetidin-3-amine Synthesized according to Example 3, Steps G-I substituting N,N-dimethylazetidin-3-amine hydrochloride in place of 2-(1-methyl-1H-imidazol-2-yl)ethan-1-ol and 2-(8-chloronaphthalen-1-yl)-4,4,5,5-tetramethyl-1,3,2-dioxaborolane in place of 4-(4,4,5,5-tetramethyl-1,3,2-dioxaborolan-2-yl)naphthalen-2-ol (5 mg, 0.01 mmol, 37%). LCMS (MM-ES+APCI, Pos): m/z 518.2 (M+H).

Example 123

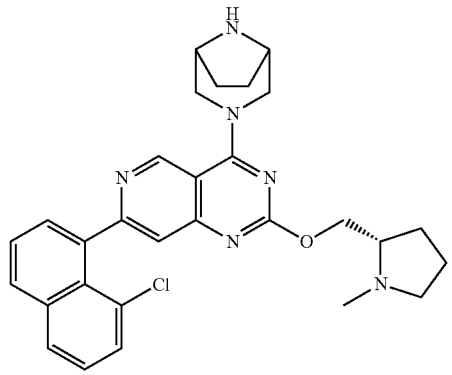 [SMILES: CN1CCC[C@H]1COc1nc(N2CC3CCC(C2)N3)c2cnc(-c3cccc4cccc(Cl)c34)cc2n1]

4-((1R,5S)-3,8-diazabicyclo[3.2.1]octan-3-yl)-7-(8-chloronaphthalen-1-yl)-2-(((S)-1-methylpyrrolidin-2-yl)methoxy)pyrido[4,3-d]pyrimidine Synthesized according to Example 3 steps D-I, substituting ethyl 4-amino-6-chloronicotinate for ethyl 4-amino-6-chloro-5-fluoronicotinate in step D while substituting (S)-(1-methylpyrrolidin-2-yl)methanol in place of 2-(1-methyl-1H-imidazol-2-yl)ethan-1-ol in step G and 2-(8-chloronaphthalen-1-yl)-4,4,5,5-tetramethyl-1,3,2-dioxaborolane in place of 4-(4,4,5,5-tetramethyl-1,3,2-dioxaborolan-2-yl)naphthalen-2-ol in step H (6 mg, 0.012 mmol, 21%). LCMS (MM-ES+APCI, Pos): m/z 515.2 (M+H).

Example 124

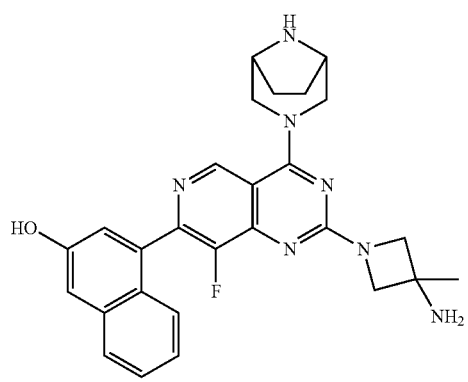 [SMILES: CC1(N)CN(c2nc(N3CC4CCC(C3)N4)c3cnc(-c4cc(O)cc5ccccc45)c(F)c3n2)C1]

4-(2-(3-amino-3-methylazetidin-1-yl)-4-((1R,5S)-3,8-diazabicyclo[3.2.1]octan-3-yl)-8-fluoropyrido[4,3-d]pyrimidin-7-yl)naphthalen-2-ol Synthesized according to Example 3, Steps G-I substituting 3-(Boc-amino)-3-methylazetidine hydrochloride in place of 2-(1-methyl-1H-imidazol-2-yl)ethan-1-ol (24 mg, 0.05 mmol, 42%). LCMS (MM-ES+APCI, Pos): m/z 486.2 (M+H).

Example 125

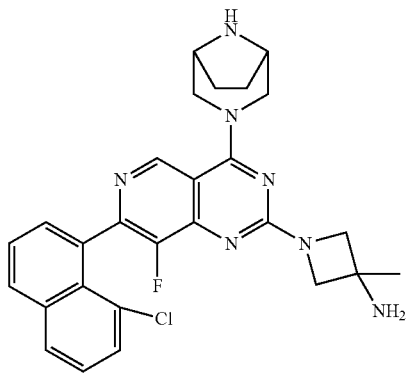 [SMILES: CC1(N)CN(c2nc(N3CC4CCC(C3)N4)c3cnc(-c4cccc5cccc(Cl)c45)c(F)c3n2)C1]

1-(4-((1R,5S)-3,8-diazabicyclo[3.2.1]octan-3-yl)-7-(8-chloronaphthalen-1-yl)-8-fluoropyrido[4,3-d]pyrimidin-2-yl)-3-methylazetidin-3-amine Synthesized according to Example 3, Steps G-I substituting 3-(Boc-amino)-3-methylazetidine hydrochloride in place of 2-(1-methyl-1H-imidazol-2-yl)ethan-1-ol and 2-(8-chloronaphthalen-1-yl)-4,4,5,5-tetramethyl-1,3,2-dioxaborolane in place of 4-(4,4,5,5-tetramethyl-1,3,2-dioxaborolan-2-yl)naphthalen-2-ol (54 mg, 0.11 mmol, 51%). LCMS (MM-ES+APCI, Pos): m/z 504.2 (M+H).

Example 126

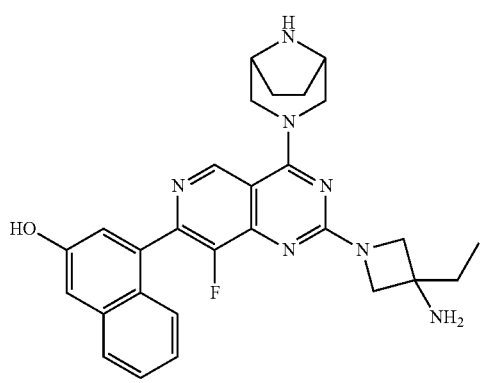 [SMILES: CCC1(N)CN(c2nc(N3CC4CCC(C3)N4)c3cnc(-c4cc(O)cc5ccccc45)c(F)c3n2)C1]

4-(2-(3-amino-3-ethylazetidin-1-yl)-4-((1R,5S)-3,8-diazabicyclo[3.2.1]octan-3-yl)-8-fluoropyrido[4,3-d]pyrimidin-7-yl)naphthalen-2-ol Synthesized according to Example 3, Steps G-I substituting 3-(Boc-amino)-3-ethylazetidine hydrochloride in place of 2-(1-methyl-1H-imidazol-2-yl)ethan-1-ol (34 mg, 0.068 mmol, 41%). LCMS (MM-ES+APCI, Pos): m/z 500.2 (M+H).

Example 127

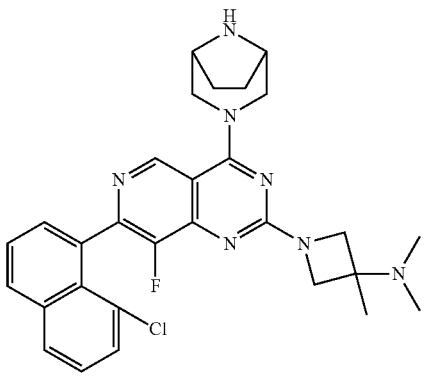 [SMILES: CN(C)C1(C)CN(c2nc(N3CC4CCC(C3)N4)c3cnc(-c4cccc5cccc(Cl)c45)c(F)c3n2)C1]

1-(4-((1R,5S)-3,8-diazabicyclo[3.2.1]octan-3-yl)-7-(8-chloronaphthalen-1-yl)-8-fluoropyrido[4,3-d]pyrimidin-2-yl)-N,N,3-trimethylazetidin-3-amine Synthesized according to Example 29, Steps H-I substituting N,N,3-trimethylazetidin-3-amine hydrochloride in place of (S)-(1-isopropylpyrrolidin-2-yl)methanol (21 mg, 0.039 mmol, 100%). LCMS (MM-ES+APCI, Pos): m/z 532.2 (M+H).

Example 128

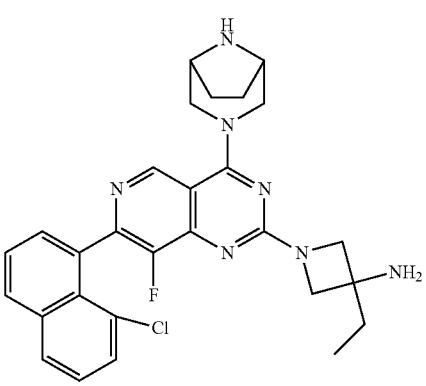 [SMILES: CCC1(N)CN(c2nc(N3CC4CCC(C3)N4)c3cnc(-c4cccc5cccc(Cl)c45)c(F)c3n2)C1]

1-(4-((1R,5S)-3,8-diazabicyclo[3.2.1]octan-3-yl)-7-(8-chloronaphthalen-1-yl)-8-fluoropyrido[4,3-d]pyrimidin-2-yl)-3-ethylazetidin-3-amine Synthesized according to Example 29, Steps H-I substituting 3-(Boc-amino)-3-ethylazetidine hydrochloride in place of (S)-(1-isopropylpyrrolidin-2-yl)methanol (7 mg, 0.013 mmol, 88%). LCMS (MM-ES+APCI, Pos): m/z 518.2 (M+H).

Example 129

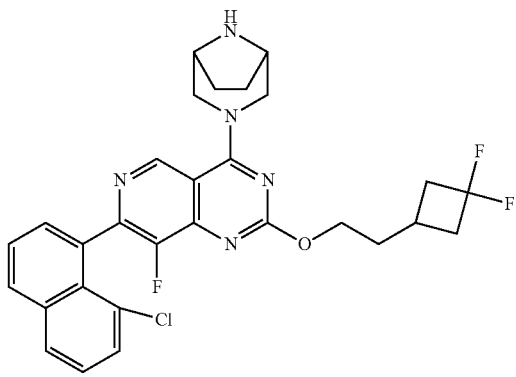 [SMILES: Fc1c(-c2cccc3cccc(Cl)c23)ncc2c(N3CC4CCC(C3)N4)nc(OCCC3CC(F)(F)C3)nc12]

4-((1R,5S)-3,8-diazabicyclo[3.2.1]octan-3-yl)-7-(8-chloronaphthalen-1-yl)-2-(2-(3,3-difluorocyclobutyl)ethoxy)-8-fluoropyrido[4,3-d]pyrimidine Synthesized according to Example 29, Steps H-I substituting (3,3-Difluorocyclobutyl)ethanol in place of (S)-(1-isopropylpyrrolidin-2-yl)methanol (15 mg, 0.027 mmol, 59%). LCMS (MM-ES+APCI, Pos): m/z 554.2 (M+H).

Example 130

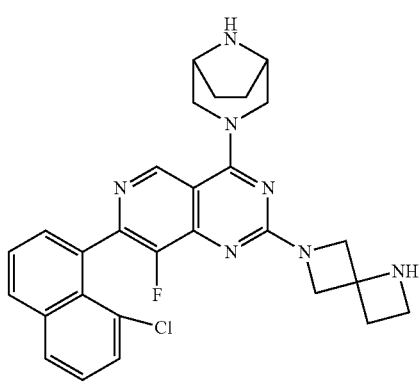 [SMILES: Fc1c(-c2cccc3cccc(Cl)c23)ncc2c(N3CC4CCC(C3)N4)nc(N3CC4(CCN4)C3)nc12]

4-((1R,5S)-3,8-diazabicyclo[3.2.1]octan-3-yl)-7-(8-chloronaphthalen-1-yl)-8-fluoro-2-(1,6-diazaspiro[3.3]heptan-6-yl)pyrido[4,3-d]pyrimidine Synthesized according to Example 29, Steps H-I substituting 3,6-Diazaspiro[3.3]heptane-3-carboxylic acid tert-butyl ester in place of (S)-(1-isopropylpyrrolidin-2-yl)methanol (7 mg, 0.014 mmol, 18%). LCMS (MM-ES+APCI, Pos): m/z 516.2 (M+H).

Example 131

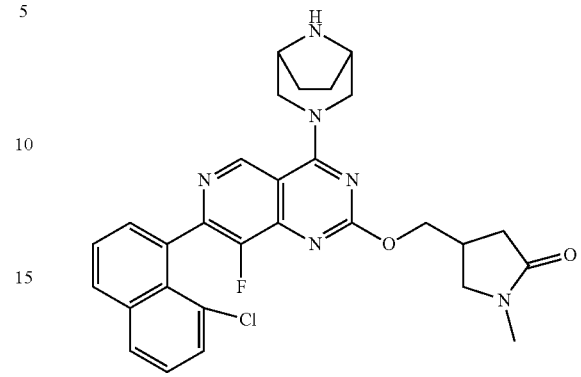

4-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)-1-methylpyrrolidin-2-one Synthesized according to Example 29, Steps H-I substituting 4-(Hydroxymethyl)-1-methylpyrrolidin-2-one in place of (S)-(1-isopropylpyrrolidin-2-yl)methanol (25 mg, 0.046 mmol, 67%). LCMS (MM-ES+APCI, Pos): m/z 547.2 (M+H).

Example 132

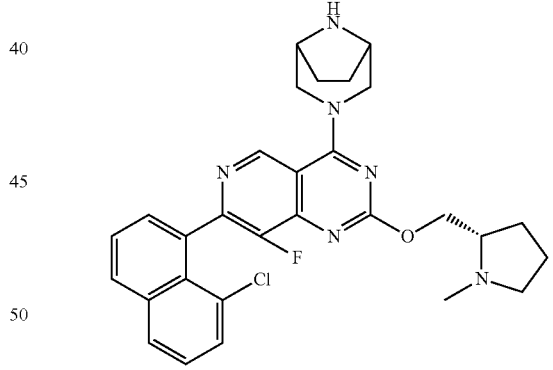

4-((1R,5S)-3,8-diazabicyclo[3.2.1]octan-3-yl)-7-(8-chloronaphthalen-1-yl)-8-fluoro-2-(((S)-1-methylpyrrolidin-2-yl)methoxy)pyrido[4,3-d]pyrimidine Synthesized according to Example 3, Steps G-I substituting (S)-(1-methylpyrrolidin-2-yl)methanol in place of 2-(1-methyl-1H-imidazol-2-yl)ethan-1-ol and 2-(8-chloronaphthalen-1-yl)-4,4,5,5-tetramethyl-1,3,2-dioxaborolane in place of 4-(4,4,5,5-tetramethyl-1,3,2-dioxaborolan-2-yl)naphthalen-2-ol (7 mg, 0.013 mmol, 72%). LCMS (MM-ES+APCI, Pos): m/z 533.2 (M+H).

Example 133

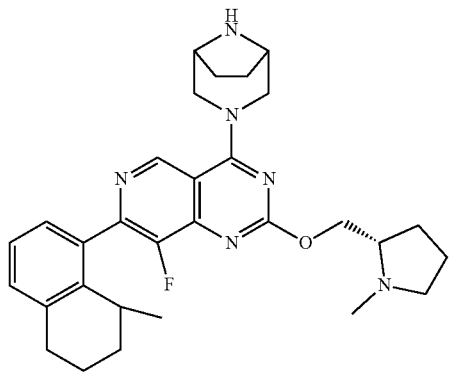 [SMILES: CC1CCCc2cccc(-c3ncc4c(N5CC6CCC(C5)N6)nc(OC[C@@H]5CCCN5C)nc4c3F)c21]

4-((1R,5S)-3,8-diazabicyclo[3.2.1]octan-3-yl)-8-fluoro-7-(8-methyl-5,6,7,8-tetrahydronaphthalen-1-yl)-2-(((S)-1-methylpyrrolidin-2-yl)methoxy)pyrido[4,3-d]pyrimidine

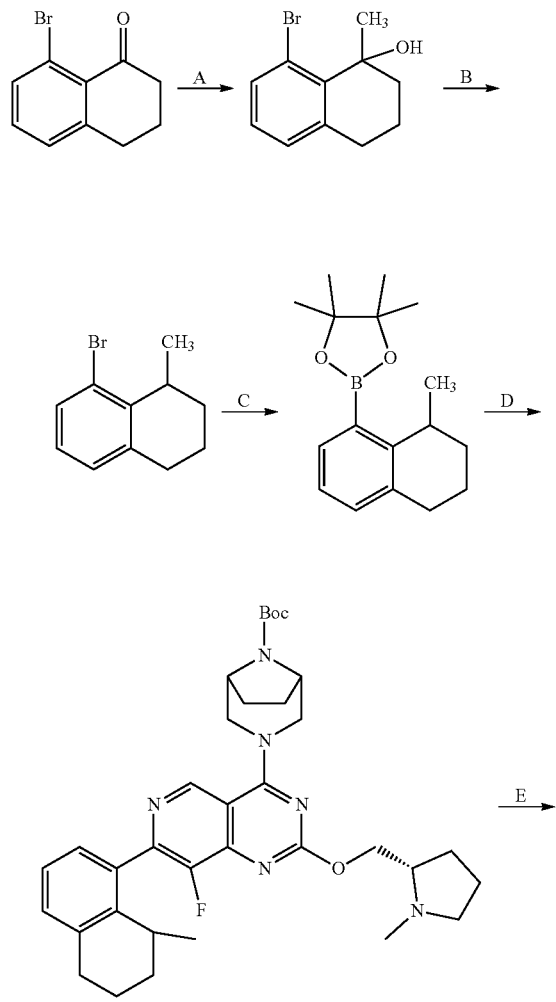

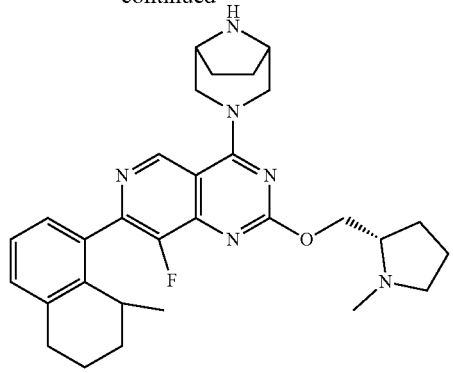

Step A. 8-bromo-1-methyl-1,2,3,4-tetrahydronaphthalen-1-ol. A stirred solution of 8-bromo-3,4-dihydro-2H-naphthalen-1-one (1500 mg, 6.66 mmol) in tetrahydrofuran (22 mL) was cooled on ice-acetone bath and methylmagnesium bromide (2.67 mL, 8.00 mmol) in diethyl ether was added dropwise. The reaction mixture was stirred at −30° C. for 1 h and warmed to rt. The mixture was cooled in an ice bath and added dropwise to a stirred mixture of ice (50 g) and acetic acid (10 mL). The suspension was extracted with MTBE (100 mL). The organic layers were separated and washed with water, 2M $Na_2CO_3$ and brine (20 mL each) and the combined water phases were reextracted with MTBE. The combined organic extracts were evaporated in vacuo, re-dissolved in methanol (10 mL) and 35% hydrazine (2 mL) was added. The reaction mixture was heated to reflux for 1 h. The reaction was cooled, partitioned between hexane and water (50 mL each) and the layers were separated. The organic phase was washed with water and brine (20 mL each), dried over $Na_2SO_4$ and concentrated in vacuo. The combined aqueous phases were reextracted with hexane (30 ml), concentrated in vacuo and combined with the previous extracts. The material was chromatographed on silica gel using 10% EtOAc/hexane as eluent to give 8-bromo-1-methyl-1,2,3,4-tetrahydronaphthalen-1-ol (937 mg, 58%) as colorless smelly solid. LCMS (MM-ES+APCI, Pos): m/z 223.1 (M-OH).

Step B. 8-Bromo-1-methyl-1,2,3,4-tetrahydronaphthalene. A stirred solution of 8-bromo-1-methyl-1,2,3,4-tetrahydronaphthalen-1-ol (500 mg, 2.07 mmol) in dichloromethane (10 mL) was cooled in a dry ice-acetone bath and triethylsilane (1.66 mL, 10.4 mmol) was added followed by addition of 2,2,2-trifluoroacetic acid (0.48 mL, 6.2 mmol) dropwise. The reaction mixture was warmed to −30° C. over 20 min, then to −20° C. over 1 h, and to rt overnight. The mixture was partitioned between water (10 mL) and hexane (30 mL) and the organic layer was separated. The organic phase was washed with sat. $NaHCO_3$, dried over $Na_2SO_4$, evaporated carefully under reduced pressure and chromatographed on silica gel with pentane as eluent to yield 8-bromo-1-methyl-1,2,3,4-tetrahydronaphthalene (310 mg, 66%) as colorless oil.

Step C. 4,4,5,5-tetramethyl-2-(8-methyl-5,6,7,8-tetrahydronaphthalen-1-yl)-1,3,2-dioxaborolane. A stirred solution of 8-bromo-1-methyl-1,2,3,4-tetrahydronaphthalene (300 mg, 1.33 mmol) in tetrahydrofuran (7 mL) under $N_2$ was cooled in a C02-acetone bath and butyllithium (0.59 mL, 1.47 mmol) was added dropwise over 5 min. The solution was stirred for 5 min at −78° C. and 2-isopropoxy-4,4,5,5-tetramethyl-1,3,2-dioxaborolane (0.33 mL, 1.60 mmol) was added dropwise. The reaction mixture was warmed to rt over 2 h and partitioned between hexane (30 mL) and sat. NH₄Cl (10 mL). The organic layer was separated. The organic layer was washed with water and brine (10 mL each), dried over Na₂SO₄ and concentrated in vacuo. The residue was chromatographed on silica gel using 2 to 10% ethyl acetate/hexane as eluent to give 4,4,5,5-tetramethyl-2-(8-methyl-5,6,7,8-tetrahydronaphthalen-1-yl)-1,3,2-dioxaborolane (289 mg, 80%) as colorless viscous oil. ¹H NMR (400 MHz, CDCl₃): 7.58 (dm, J=7.1 Hz, 2H), 7.11 (dm, J=7.5 Hz, 2H), 7.06 (t, J=7.2 Hz, 2H), 3.72-3.63 (m, 1H), 2.84-2.69 (m, 2H), 1.93-1.83 (m, 2H), 1.76-1.66 (m, 2H), 1.35 (s, 6H), 1.34 (s, 6H), 1.20 (d, J=7.0 Hz, 3H).

Step D. Tert-butyl (1R,5S)-3-(8-fluoro-7-(8-methyl-5,6,7,8-tetrahydronaphthalen-1-yl)-2-(((S)-1-methylpyrrolidin-2-yl)methoxy)pyrido[4,3-d]pyrimidin-4-yl)-3,8-diazabicyclo[3.2.1]octane-8-carboxylate. Synthesized according to Example 3 step G-H, substituting (S)-(1-methylpyrrolidin-2-yl)methanol in place of 2-(1-methyl-1H-imidazol-2-yl)ethan-1-ol in step G and substituting 4,4,5,5-tetramethyl-2-(8-methyl-5,6,7,8-tetrahydronaphthalen-1-yl)-1,3,2-dioxaborolane in place of 4-(4,4,5,5-tetramethyl-1,3,2-dioxaborolan-2-yl)naphthalen-2-ol to afford the title compound as colorless solid (26%). LCMS (MM-ES+APCI, Pos): m/z 617.3 (M+H).

Step E. 4-((1R,5S)-3,8-diazabicyclo[3.2.1]octan-3-yl)-8-fluoro-7-(8-methyl-5,6,7,8-tetrahydronaphthalen-1-yl)-2-(((S)-1-methylpyrrolidin-2-yl)methoxy)pyrido[4,3-d]pyrimidine. Synthesized similarly to Example 3 Step I, using tert-butyl (1R,5S)-3-(8-fluoro-7-(8-methyl-5,6,7,8-tetrahydronaphthalen-1-yl)-2-(((S)-1-methylpyrrolidin-2-yl)methoxy)pyrido[4,3-d]pyrimidin-4-yl)-3,8-diazabicyclo[3.2.1]octane-8-carboxylate in place of tert-butyl (1R,5S)-3-(8-fluoro-7-(3-hydroxynaphthalen-1-yl)-2-(2-(1-methyl-1H-imidazol-2-yl)ethoxy)pyrido[4,3-d]pyrimidin-4-yl)-3,8-diazabicyclo[3.2.1]octane-8-carboxylate. Submitted as the freebase LCMS (MM-ES+APCI, Pos): m/z 517.3 (M+H).

Example 134

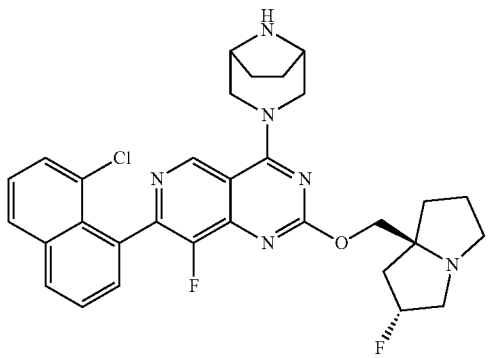 [SMILES: Fc1c(-c2cccc3cccc(Cl)c23)ncc2c(N3CC4CCC(C3)N4)nc(OC[C@@]34CCCN3C[C@H](F)C4)nc12]

4-((1R,5S)-3,8-diazabicyclo[3.2.1]octan-3-yl)-7-(8-chloronaphthalen-1-yl)-8-fluoro-2-((2-fluorotetrahydro-1H-pyrrolizin-7a(5H)-yl)methoxy)pyrido[4,3-d]pyrimidine

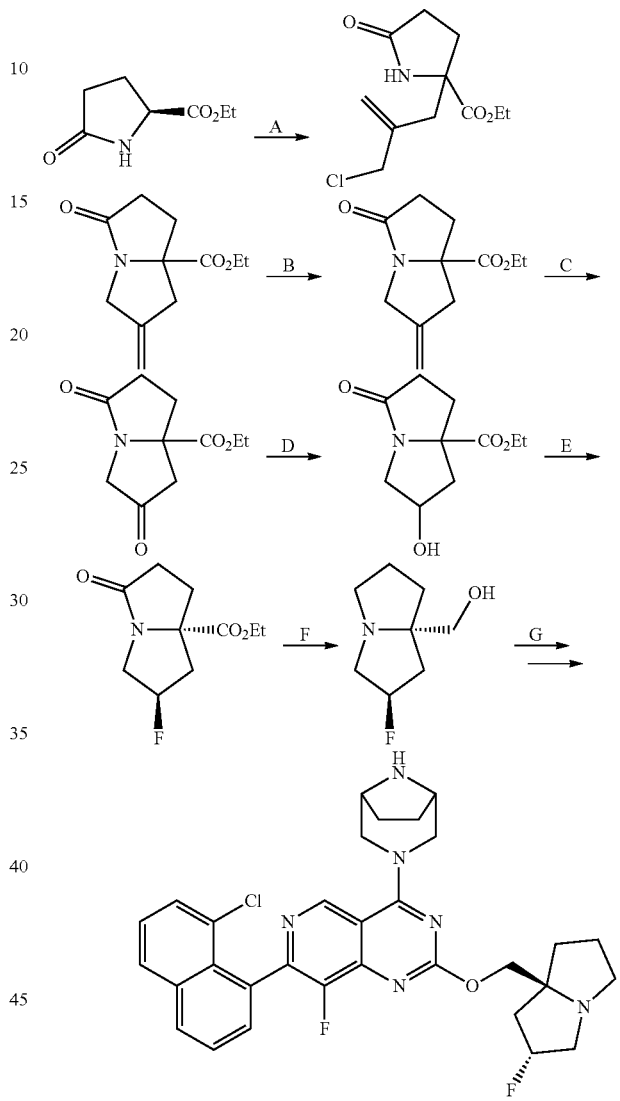

Step A. Ethyl 2-(2-(chloromethyl)allyl)-5-oxopyrrolidine-2-carboxylate. To a stirred solution of ethyl (S)-5-oxopyrrolidine-2-carboxylate (5.7 g, 36.3 mmol) and 3-chloro-2-(chloromethyl)prop-1-ene (16.8 ml, 145 mmol) in 36 mL of THF at −40° C. under nitrogen was added LiHMDS (76.2 ml, 76.2 mmol) (1M in THF) by slow cannulation. After 15 minutes, the cooling bath was removed. The reaction was warmed to room temperature and stirred for 2 hours. The reaction was quenched with saturated ammonium chloride solution (20 mL) and then partially concentrated to about 60 mL. The residual material was partitioned between ethyl acetate (100 mL) and water (100 mL) and the layers were separated. The organics were washed 1×100 mL with brine, dried over MgSO₄, filtered and concentrated. The crude product was purified by flash chromatography eluting with an ethyl acetate/hexanes gradient (20% to 80% ethyl acetate). The crude product (5.55 g total) contained a mixture (approximately 2.7:1) of ethyl 2-(2-(chloromethyl)allyl)-5-oxopyrrolidine-2-carboxylate and ethyl 2-methylene-5-oxotetrahydro-1H-pyrrolizine-7a(5H)-carboxylate (product of the step B) and was carried on crude without further purification.

Step B. Ethyl 2-methylene-5-oxotetrahydro-1H-pyrrolizine-7a(5H)-carboxylate. To a stirred suspension of NaH (139 mg, 3.47 mmol) in 40 mL of THF at 0° C. under nitrogen was added a 2.7:1 mixture of ethyl 2-(2-(chloromethyl)allyl)-5-oxopyrrolidine-2-carboxylate and ethyl 2-methylene-5-oxotetrahydro-1H-pyrrolizine-7a(5H)-carboxylate (710 mg, 2.89 mmol) as a solution in 20 mL of THF by syringe. After the addition was complete, the mixture was heated to reflux overnight. The reaction was cooled to room temperature and quenched with water (20 mL). The majority of the THF was removed by rotary evaporation and the residual solution was partitioned between ethyl acetate (50 mL) and water (50 mL). The organics were dried over MgSO$_4$, filtered and concentrated to yield ethyl 2-methylene-5-oxotetrahydro-1H-pyrrolizine-7a(5H)-carboxylate an orange oil which was carried on crude without further purification.

Step C. Ethyl 2,5-dioxotetrahydro-1H-pyrrolizine-7a(5H)-carboxylate. To a stirred solution of crude ethyl 2-methylene-5-oxotetrahydro-1H-pyrrolizine-7a(5H)-carboxylate (1.1 g, 5.26 mmol) in 14 mL of dichloromethane at −78° C. was added ozone gas via a pipet inserted into the solution. Ozone was continuously passed through the solution until a light blue color appeared (about 15 minutes). The ozone generator was turned off and oxygen was then passed through the reaction for about 5 minutes. The ozone generator was disconnected and nitrogen gas was passed through the solution for another 5 minutes. Polymer-bound triphenylphosphine (3.50 g, 10.5 mmol) was added neat as a solid at −78° C. The reaction was warmed to rt and slowly stirred overnight. The reaction mixture was filtered and concentrated to yield 1 g of a light yellow oil which was carried on crude without further purification.

Step D. Ethyl 2-hydroxy-5-oxotetrahydro-1H-pyrrolizine-7a(5H)-carboxylate. Ethyl 2,5-dioxotetrahydro-1H-pyrrolizine-7a(5H)-carboxylate (1.08 g, 5.113 mmol) was charged to a 50 mL round bottom flask equipped with a stir bar and nitrogen inlet with methanol (17 ml, 5.1 mmol). To the stirring solution was added sodium borohydride neat (0.14 g, 3.8 mmol). After 5 minutes the mixture was quenched slowly with 10% aqueous K$_2$CO$_3$ and the aqueous layer was extracted with 5 portions of 25% IPA/DCM. The combined organics were dried over Na$_2$SO$_4$ and concentrated in vacuo to yield 969 mg of a white solid which was carried on crude without further purification.

Step E. Ethyl 2-fluoro-5-oxotetrahydro-1H-pyrrolizine-7a(5H)-carboxylate. To a stirred solution of crude ethyl 2-hydroxy-5-oxotetrahydro-1H-pyrrolizine-7a(5H)-carboxylate (4.8:1 cis:trans isomers) (1 g, 4.69 mmol) in dichloromethane (14.2 ml, 4.69 mmol) at −78° C. was added Deoxo-Fluor (0.86 ml, 4.7 mmol) neat by syringe. The reaction was stirred overnight and warmed to rt. The mixture was then partitioned between 25% IPA/DCM and water and the layers were separated. The aqueous layer was washed 3× with 25% IPA/DCM and the organics were combined and dried over Na$_2$SO$_4$. The crude product was concentrated purified by flash chromatography eluting with an ethyl acetate/hexanes gradient (0% to 60% ethyl acetate) to yield ethyl 2-fluoro-5-oxotetrahydro-1H-pyrrolizine-7a(5H)-carboxylate as a clear oil containing a single racemic trans diastereomer (210 mg, 0.98 mmol, 21%). $^1$H NMR (400 MHz, CDCl$_3$) δ 5.30, (m, 1H), 4.21 (m, 2H), 3.16 (m, 1H), 2.73 (m, 4H), 2.45 (m, 1H), 2.19 (m, 2H), 1.28 (m, 3H).

Step F. (2-fluorotetrahydro-1H-pyrrolizin-7a(5H)-yl)methanol. Ethyl 2-fluoro-5-oxotetrahydro-1H-pyrrolizine-7a(5H)-carboxylate (0.21 g, 0.990 mmol) and dry THF (2 ml) were charged to a 25 mL pear shaped flask equipped with a stir bar. The mixture was cooled to 0° C. and LAH (1M in THF) (2.97 ml, 2.97 mmol) was added dropwise. The vessel was equipped with a cold-water condenser and heated to 70° C. for 4 hours. The mixture was diluted with ethyl ether, cooled to 0° C. and quenched with 110 µL DI water. 110 µL of 15% aqueous NaOH was added to the mixture, followed by 330 µL of DI water. The vessel was warmed to room temperature and stirred for 15 minutes. To the mixture was added anhydrous magnesium sulfate. The mixture stirred for 15 minutes before being filtered and concentrated in vacuo. LCMS (MM-ES+APCI, Pos): m/z 160.2 (M+H).

Step G. 4-((1R,5S)-3,8-diazabicyclo[3.2.1]octan-3-yl)-7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidine was synthesized according to Example 29, Steps H-I substituting ((2R,7aS)-2-fluorotetrahydro-1H-pyrrolizin-7a(5H)-yl)methanol in place of (S)-(1-isopropylpyrrolidin-2-yl)methanol (34 mg, 0.058 mmol, 62%). Submitted as a TFA salt. LCMS (MM-ES+APCI, Pos): m/z 577.2 (M+H).

Example 135

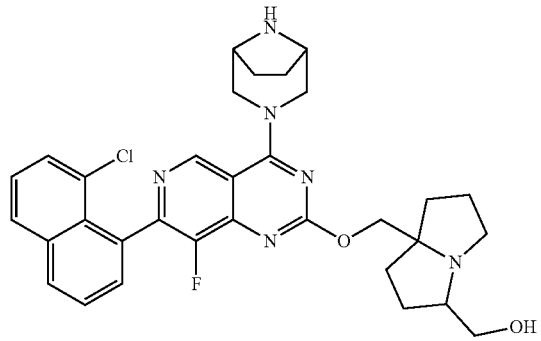 [SMILES: OCC1CCC2(COc3nc(N4CC5CCC(C4)N5)c4cnc(-c5cccc6cccc(Cl)c56)c(F)c4n3)CCCN12]

(7a-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)hexahydro-1H-pyrrolizin-3-yl)methanol

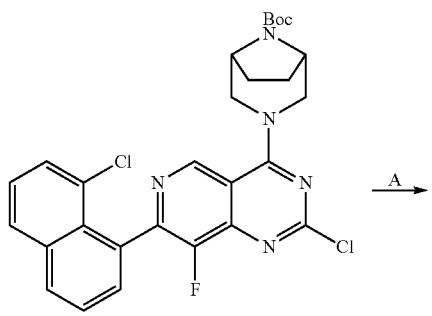

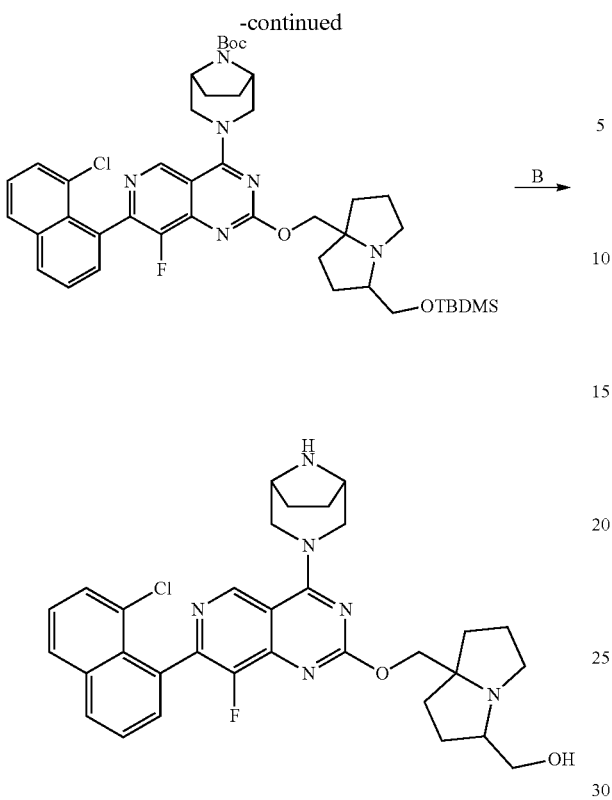

phase preparative HPLC (5-95% ACN/water/0.1% TFA over 20 min). Fractions containing the product were frozen and lyophilized overnight to provide the desired product as a white solid. LCMS (MM-ES+APCI, Pos): m/z 589.3 (M+H).

Example 136

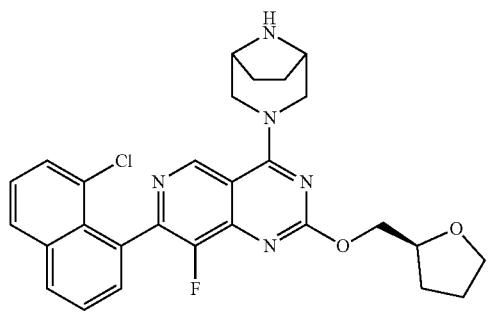 [SMILES: Fc1c(-c2cccc3cccc(Cl)c23)ncc2c(N3CC4CCC(C3)N4)nc(OC[C@@H]3CCCO3)nc12]

4-((1R,5S)-3,8-diazabicyclo[3.2.1]octan-3-yl)-7-(8-chloronaphthalen-1-yl)-8-fluoro-2-(((S)-tetrahydrofuran-2-yl)methoxy)pyrido[4,3-d]pyrimidine Synthesized according to Example 29, Steps H-I substituting (S)-(tetrahydrofuran-2-yl)methanol in place of (S)-(1-isopropylpyrrolidin-2-yl)methanol (21 mg, 0.033 mmol, 49%). Submitted as a TFA salt. LCMS (MM-ES+APCI, Pos): m/z 520.2 (M+H).

Example 137

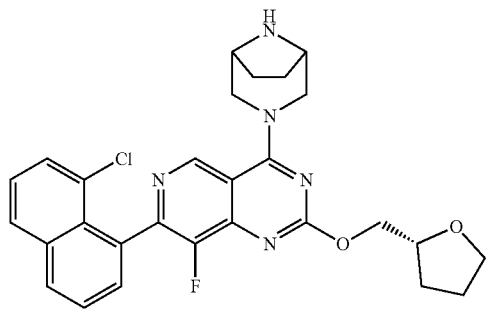 [SMILES: Fc1c(-c2cccc3cccc(Cl)c23)ncc2c(N3CC4CCC(C3)N4)nc(OC[C@H]3CCCO3)nc12]

4-((1R,5S)-3,8-diazabicyclo[3.2.1]octan-3-yl)-7-(8-chloronaphthalen-1-yl)-8-fluoro-2-(((R)-tetrahydrofuran-2-yl)methoxy)pyrido[4,3-d]pyrimidine Synthesized according to Example 29, Steps H-I substituting (R)-(tetrahydrofuran-2-yl)methanol in place of (S)-(1-isopropylpyrrolidin-2-yl)methanol (21 mg, 0.033 mmol, 49%). Submitted as a TFA salt. LCMS (MM-ES+APCI, Pos): m/z 520.2 (M+H).

Step A. tert-butyl (1R,5S)-3-(2-((3-(((tert-butyldimethylsilyl)oxy)methyl)tetrahydro-1H-pyrrolizin-7a(5H)-yl)methoxy)-7-(8-chloronaphthalen-1-yl)-8-fluoropyrido[4,3-d]pyrimidin-4-yl)-3,8-diazabicyclo[3.2.1]octane-8-carboxylate: To a mixture of (3-(((tert-butyldimethylsilyl)oxy)methyl)tetrahydro-1H-pyrrolizin-7a(5H)-yl)methanol (0.046 g, 0.16 mmol), tert-butyl (1R,5S)-3-(2-chloro-7-(8-chloronaphthalen-1-yl)-8-fluoropyrido[4,3-d]pyrimidin-4-yl)-3,8-diazabicyclo[3.2.1]octane-8-carboxylate (0.03 g, 0.054 mmol), potassium carbonate (0.022 g, 0.16 mmol) and BINAP (0.0067 g, 0.011 mmol) in 0.27 mL of toluene was added Palladium(II) acetate (0.0012 g, 0.0054 mmol) in a 10 mL glass pressure vessel equipped with a stir bar. The mixture was sparged with argon for 5 minutes, then sealed and heated to 110° C. for 8 hours. The vessel was cooled to room temperature and the mixture was filtered, concentrated in vacuo, and purified by column chromatography (Redisep 4 g, 0 to 20% MeOH/DCM with 1% NH$_4$OH). (15 mg, 0.019 mmol, 35%). LCMS (MM-ES+APCI, Pos): m/z 803.3 (M+H).

Step B. (7a-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)hexahydro-1H-pyrrolizin-3-yl)methanol: Tert-butyl (1R,5S)-3-(2-((3-(((tert-butyldimethylsilyl)oxy)methyl)tetrahydro-1H-pyrrolizin-7a(5H)-yl)methoxy)-7-(8-chloronaphthalen-1-yl)-8-fluoropyrido[4,3-d]pyrimidin-4-yl)-3,8-diazabicyclo[3.2.1]octane-8-carboxylate (0.015 g, 0.0187 mmol) was constituted in dichloromethane (0.5 ml, 0.0187 mmol) and stirred at room temperature. 2,2,2-trifluoroacetic acid (0.5 ml, 0.0187 mmol) was added dropwise to the vessel and the mixture was stirred at room temperature for 2.25 hours. The mixture was concentrated in vacuo and purified by reverse

Example 138

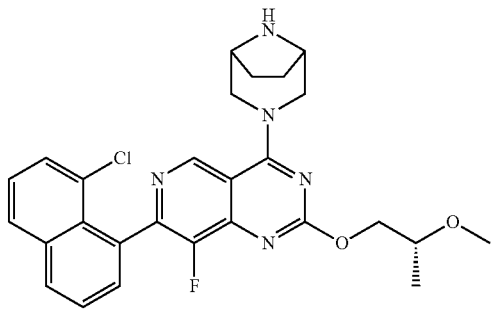 [SMILES: CO[C@H](C)COc1nc(N2CC3CCC(C2)N3)c2cnc(-c3cccc4cccc(Cl)c34)c(F)c2n1]

4-((1R,5S)-3,8-diazabicyclo[3.2.1]octan-3-yl)-7-(8-chloronaphthalen-1-yl)-8-fluoro-2-((R)-2-methoxypropoxy)pyrido[4,3-d]pyrimidine Synthesized according to Example 29, Steps H-I substituting (R)-2-methoxypropan-1-ol in place of (S)-(1-isopropylpyrrolidin-2-yl)methanol (1 mg, 0.0014 mmol, 4%). LCMS (MM-ES+APCI, Pos): m/z 508.2 (M+H).

Example 139

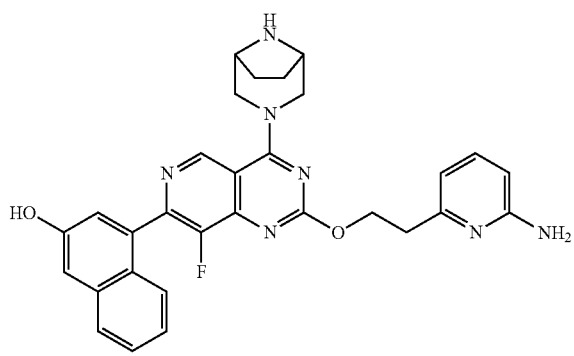 [SMILES: Nc1cccc(CCOc2nc(N3CC4CCC(C3)N4)c3cnc(-c4cc(O)cc5ccccc45)c(F)c3n2)n1]

4-(2-(2-(6-aminopyridin-2-yl)ethoxy)-4-((1R,5S)-3,8-diazabicyclo[3.2.1]octan-3-yl)-8-fluoropyrido[4,3-d]pyrimidin-7-yl)naphthalen-2-ol Synthesized according to Example 30 substituting 2-(6-aminopyridin-2-yl)ethan-1-ol in place of 2-(1-methyl-1H-benzo[d]imidazol-2-yl)ethan-1-ol dihydrate in Step F (9.7 mg, 0.018 mmol, 46%). LCMS (MM-ES+APCI, Pos): m/z 538.2 (M+H).

Example 140

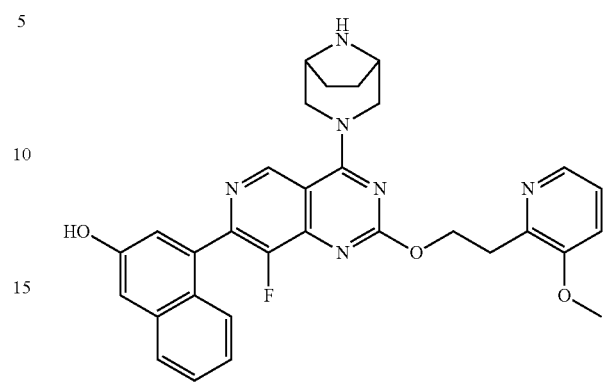

4-(4-((1R,5S)-3,8-diazabicyclo[3.2.1]octan-3-yl)-8-fluoro-2-(2-(3-methoxypyridin-2-yl)ethoxy)pyrido[4,3-d]pyrimidin-7-yl)naphthalen-2-ol Synthesized according to Example 30 substituting 2-(3-methoxypyridin-2-yl)ethan-1-ol in place of 2-(1-methyl-1H-benzo[d]imidazol-2-yl)ethan-1-ol dihydrate in Step F (12.7 mg, 0.023 mmol, 68%). LCMS (MM-ES+APCI, Pos): m/z 553.2 (M+H).

Example 141

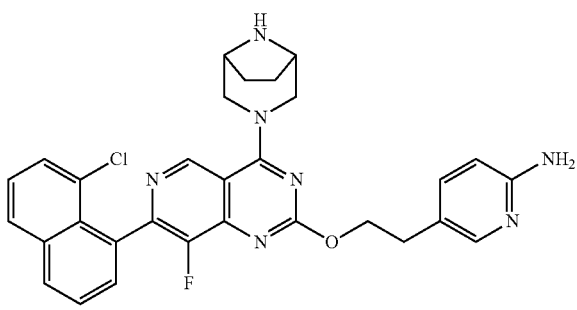 [SMILES: Nc1ccc(CCOc2nc(N3CC4CCC(C3)N4)c3cnc(-c4cccc5cccc(Cl)c45)c(F)c3n2)cn1]

5-(2-((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)ethyl)pyridin-2-amine Synthesized according to Example 29 substituting 2-(6-aminopyridin-3-yl)ethan-1-ol in place of (S)-(1-isopropylpyrrolidin-2-yl)methanol in Step H (21 mg, 0.038 mmol, 69%). LCMS (MM-ES+APCI, Pos): m/z 556.2 (M+H).

Example 142

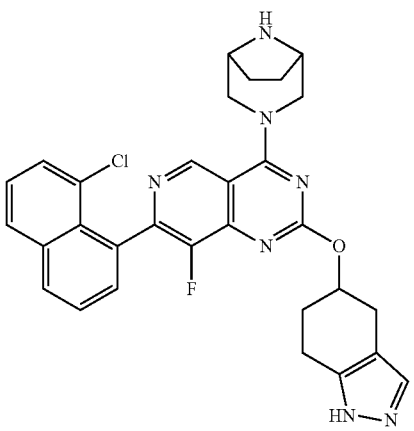 [SMILES: Fc1c(-c2cccc3cccc(Cl)c23)ncc2c(N3CC4CCC(C3)N4)nc(OC3CCc4[nH]ncc4C3)nc12]

4-((1R,5S)-3,8-diazabicyclo[3.2.1]octan-3-yl)-7-(8-chloronaphthalen-1-yl)-8-fluoro-2-((4,5,6,7-tetrahydro-1H-indazol-5-yl)oxy)pyrido[4,3-d]pyrimidine Synthesized according to Example 29 substituting 4,5,6,7-tetrahydro-1H-indazol-5-ol in place of (S)-(1-isopropylpyrrolidin-2-yl)methanol in Step H (8.6 mg, 0.015 mmol, 41%). LCMS (MM-ES+APCI, Pos): m/z 556.2 (M+H).

Example 143

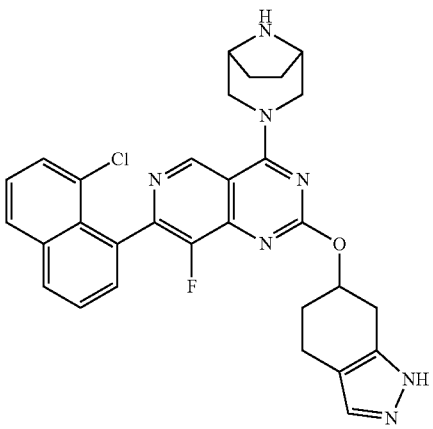

4-((1R,5S)-3,8-diazabicyclo[3.2.1]octan-3-yl)-7-(8-chloronaphthalen-1-yl)-8-fluoro-2-((4,5,6,7-tetrahydro-1H-indazol-6-yl)oxy)pyrido[4,3-d]pyrimidine Synthesized according to Example 29 substituting 4,5,6,7-tetrahydro-1H-indazol-6-ol in place of (S)-(1-isopropylpyrrolidin-2-yl)methanol in Step H (16 mg, 0.029 mmol, 56%). LCMS (MM-ES+APCI, Pos): m/z 556.2 (M+H).

Example 144

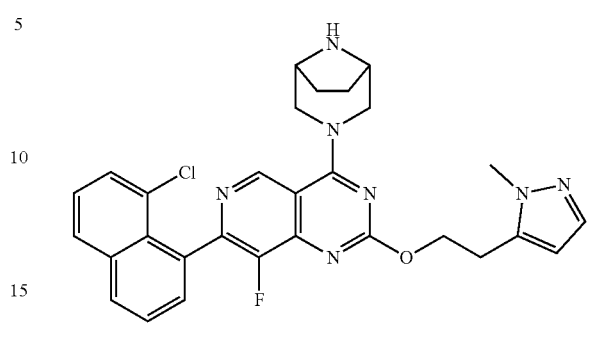

4-((1R,5S)-3,8-diazabicyclo[3.2.1]octan-3-yl)-7-(8-chloronaphthalen-1-yl)-8-fluoro-2-(2-(1-methyl-1H-pyrazol-5-yl)ethoxy)pyrido[4,3-d]pyrimidine Synthesized according to Example 29 substituting 2-(1-methyl-1H-pyrazol-5-yl)ethan-1-ol in place of (S)-(1-isopropylpyrrolidin-2-yl)methanol in Step H (11 mg, 0.020 mmol, 52%). LCMS (MM-ES+APCI, Pos): m/z 544.2 (M+H).

Example 145

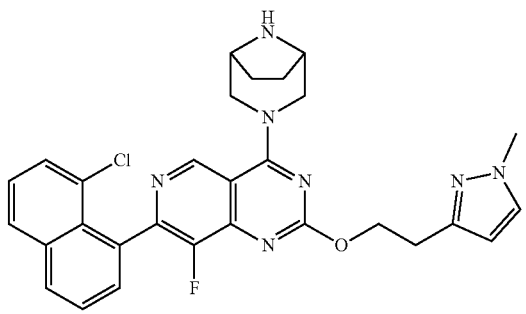 [SMILES: Cn1ccc(CCOc2nc(N3CC4CCC(C3)N4)c3cnc(-c4cccc5cccc(Cl)c45)c(F)c3n2)n1]

4-((1R,5S)-3,8-diazabicyclo[3.2.1]octan-3-yl)-7-(8-chloronaphthalen-1-yl)-8-fluoro-2-(2-(1-methyl-1H-pyrazol-3-yl)ethoxy)pyrido[4,3-d]pyrimidine Synthesized according to Example 29 substituting 2-(1-methyl-1H-pyrazol-3-yl)ethan-1-ol in place of (S)-(1-isopropylpyrrolidin-2-yl)methanol in Step H (10 mg, 0.018 mmol, 39%). LCMS (MM-ES+APCI, Pos): m/z 544.2 (M+H).

Example 146

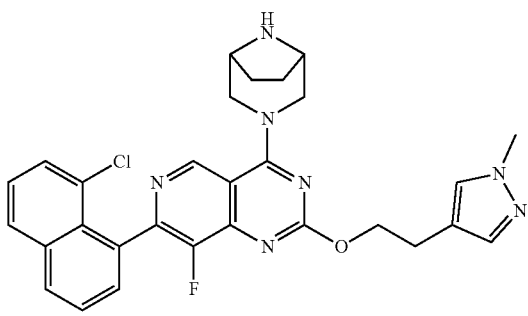 [SMILES: Cn1cc(CCOc2nc(N3CC4CCC(C3)N4)c3cnc(-c4cccc5cccc(Cl)c45)c(F)c3n2)cn1]

4-((1R,5S)-3,8-diazabicyclo[3.2.1]octan-3-yl)-7-(8-chloronaphthalen-1-yl)-8-fluoro-2-(2-(1-methyl-1H-pyrazol-4-yl)ethoxy)pyrido[4,3-d]pyrimidine Synthesized according to Example 29 substituting 2-(1-methyl-1H-pyrazol-4-yl)ethan-1-ol in place of (S)-(1-isopropylpyrrolidin-2-yl)methanol in Step H (19 mg, 0.035 mmol, 70%). LCMS (MM-ES+APCI, Pos): m/z 544.2 (M+H).

Example 148

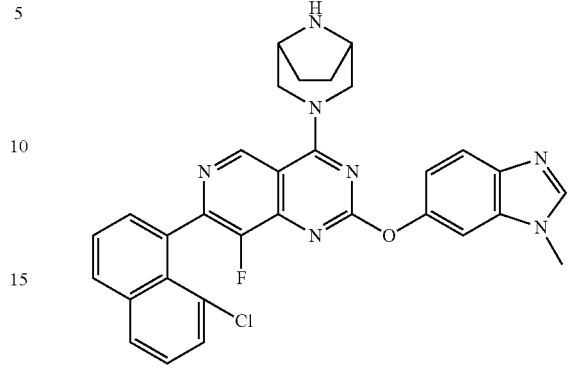

4-((1R,5S)-3,8-diazabicyclo[3.2.1]octan-3-yl)-7-(8-chloronaphthalen-1-yl)-8-fluoro-2-((1-methyl-1H-benzo[d]imidazol-6-yl)oxy)pyrido[4,3-d]pyrimidine Synthesized according to Example 29 substituting 1-methyl-1H-benzo[d]imidazol-6-ol in place of (S)-(1-isopropylpyrrolidin-2-yl)methanol in Step H (20 mg, 0.035 mmol, 57%). LCMS (MM-ES+APCI, Pos): m/z 566.2 (M+H).

Example 147

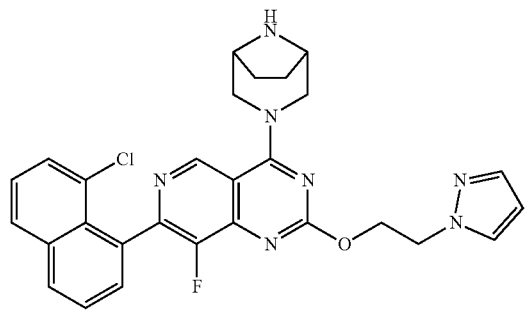 [SMILES: Fc1c(-c2cccc3cccc(Cl)c23)ncc2c(N3CC4CCC(C3)N4)nc(OCCn3cccn3)nc12]

2-(2-(1H-pyrazol-1-yl)ethoxy)-4-((1R,5S)-3,8-diazabicyclo[3.2.1]octan-3-yl)-7-(8-chloronaphthalen-1-yl)-8-fluoropyrido[4,3-d]pyrimidine Synthesized according to Example 29 substituting 2-(1H-pyrazol-1-yl)ethan-1-ol in place of (S)-(1-isopropylpyrrolidin-2-yl)methanol in Step H (12 mg, 0.023 mmol, 22%). LCMS (MM-ES+APCI, Pos): m/z 530.2 (M+H).

Example 149

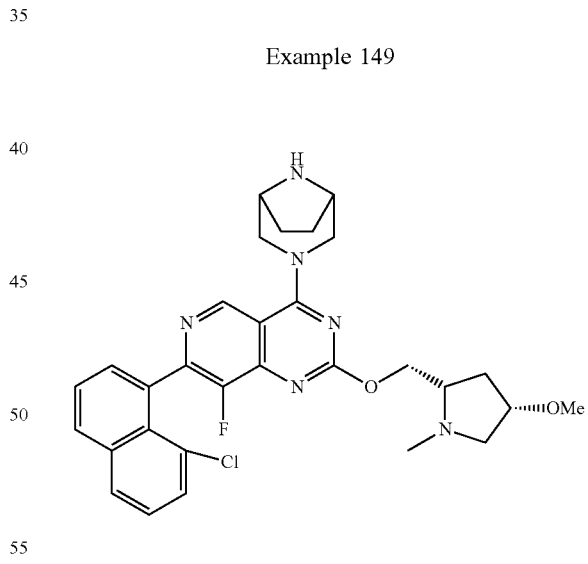

4-((1R,5S)-3,8-diazabicyclo[3.2.1]octan-3-yl)-7-(8-chloronaphthalen-1-yl)-8-fluoro-2-(((2S,4S)-4-methoxy-1-methylpyrrolidin-2-yl)methoxy)pyrido[4,3-d]pyrimidine Synthesized according to Example 29 substituting ((2S,4S)-4-methoxy-1-methylpyrrolidin-2-yl)methanol in place of (S)-(1-isopropylpyrrolidin-2-yl)methanol in Step H (16 mg, 0.028 mmol, 67%). LCMS (MM-ES+APCI, Pos): m/z 563.3 (M+H).

Example 150

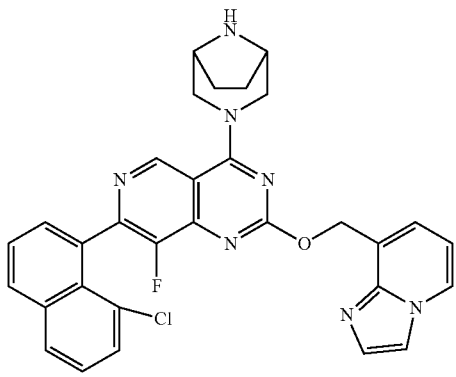 [SMILES: Fc1c(-c2cccc3cccc(Cl)c23)ncc2c(N3CC4CCC(C3)N4)nc(OCc3cccn4ccnc34)nc12]

4-((1R,5S)-3,8-diazabicyclo[3.2.1]octan-3-yl)-7-(8-chloronaphthalen-1-yl)-8-fluoro-2-(imidazo[1,2-a]pyridin-8-ylmethoxy)pyrido[4,3-d]pyrimidine Synthesized according to Example 29 substituting imidazo[1,2-a]pyridin-8-ylmethanol in place of (S)-(1-isopropylpyrrolidin-2-yl)methanol in Step H (17 mg, 0.030 mmol, 43%). LCMS (MM-ES+APCI, Pos): m/z 566.2 (M+H).

Example 151

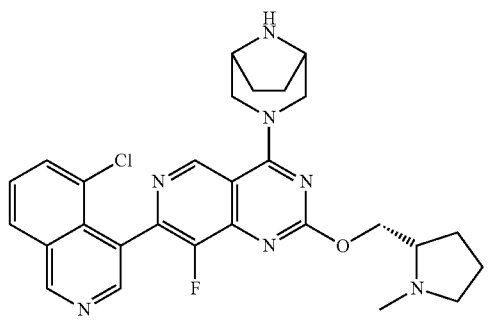

4-((1R,5S)-3,8-diazabicyclo[3.2.1]octan-3-yl)-7-(5-chloroisoquinolin-4-yl)-8-fluoro-2-(((S)-1-methylpyrrolidin-2-yl)methoxy)pyrido[4,3-d]pyrimidine Synthesized according to Example 33 substituting (S)-(1-methylpyrrolidin-2-yl)methanol in place of (tetrahydro-1H-pyrrolizin-7a(5H)-yl)methanol in Step G (14 mg, 0.026 mmol, 44%). LCMS (MM-ES+APCI, Pos): m/z 534.2 (M+H).

Example 152

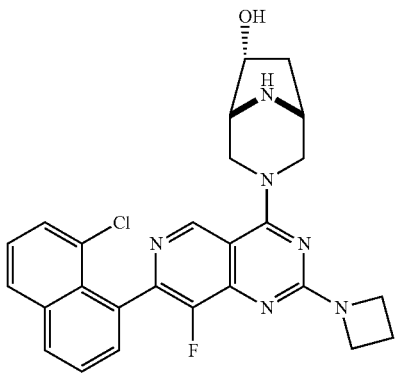

(1R,5R,6R)-3-(2-(azetidin-1-yl)-7-(8-chloronaphthalen-1-yl)-8-fluoropyrido[4,3-d]pyrimidin-4-yl)-3,8-diazabicyclo[3.2.1]octan-6-ol Synthesized according to Example 32 substituting azetidine in place of 2-(5-fluoropyridin-2-yl)ethan-1-ol in Step B (26 mg, 0.053 mmol, 52% yield). LCMS (MM-ES+APCI, Pos): m/z 491.2 (M+H).

Example 153

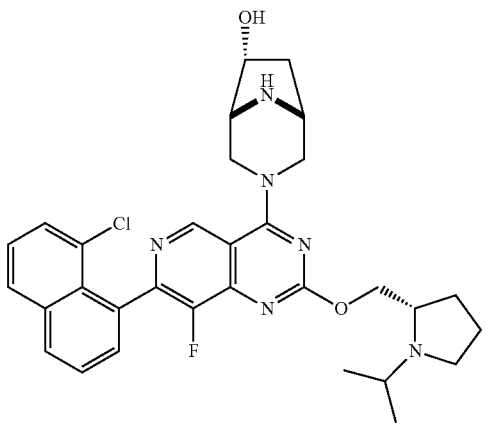

(1R,5R,6R)-3-(7-(8-chloronaphthalen-1-yl)-8-fluoro-2-(((S)-1-isopropylpyrrolidin-2-yl)methoxy)pyrido[4,3-d]pyrimidin-4-yl)-3,8-diazabicyclo[3.2.1]octan-6-ol Synthesized according to Example 32 substituting (S)-(1-isopropylpyrrolidin-2-yl)methanol in place of 2-(5-fluoropyridin-2-yl)ethan-1-ol in Step B (5 mg, 0.0087 mmol, 62% yield). LCMS (MM-ES+APCI, Pos): m/z 577.3 (M+H).

Example 154

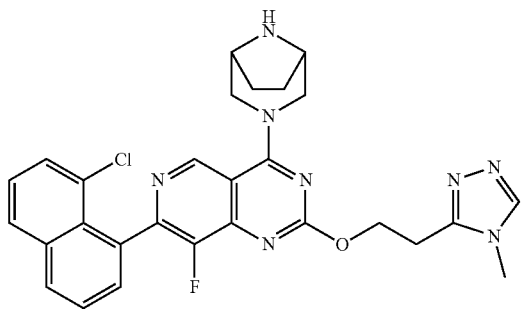 [SMILES: Cn1cnnc1CCOc1nc(N2CC3CCC(C2)N3)c2cnc(-c3cccc4cccc(Cl)c34)c(F)c2n1]

4-((1R,5S)-3,8-diazabicyclo[3.2.1]octan-3-yl)-7-(8-chloronaphthalen-1-yl)-8-fluoro-2-(2-(4-methyl-4H-1,2,4-triazol-3-yl)ethoxy)pyrido[4,3-d]pyrimidine Synthesized according to Example 29 substituting 2-(4-methyl-4H-1,2,4-triazol-3-yl)ethan-1-ol in place of (S)-(1-isopropylpyrrolidin-2-yl)methanol in Step H (19 mg, 0.035 mmol, 53% yield). LCMS (MM-ES+APCI, Pos): m/z 545.2 (M+H).

Example 156

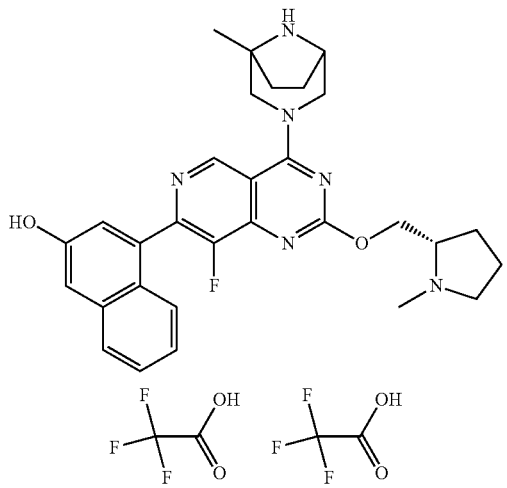

4-(8-fluoro-4-(1-methyl-3,8-diazabicyclo[3.2.1]octan-3-yl)-2-(((S)-1-methylpyrrolidin-2-yl)methoxy)pyrido[4,3-d]pyrimidin-7-yl)naphthalen-2-ol bis(2,2,2-trifluoroacetate)

Example 155

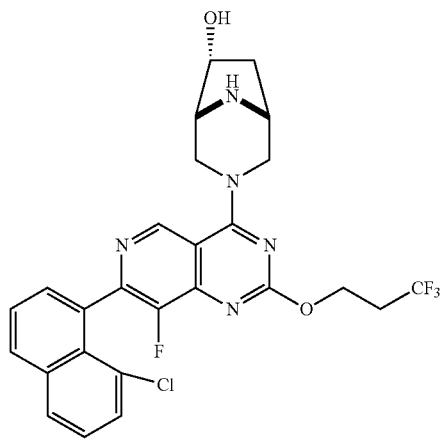

(1R,5R,6R)-3-(7-(8-chloronaphthalen-1-yl)-8-fluoro-2-(3,3,3-trifluoropropoxy)pyrido[4,3-d]pyrimidin-4-yl)-3,8-diazabicyclo[3.2.1]octan-6-ol Synthesized according to Example 32 substituting 3,3,3-trifluoropropan-1-ol in place of 2-(5-fluoropyridin-2-yl)ethan-1-ol in Step B (12 mg, 0.022 mmol, 24% yield). LCMS (MM-ES+APCI, Pos): m/z 548.2 (M+H).

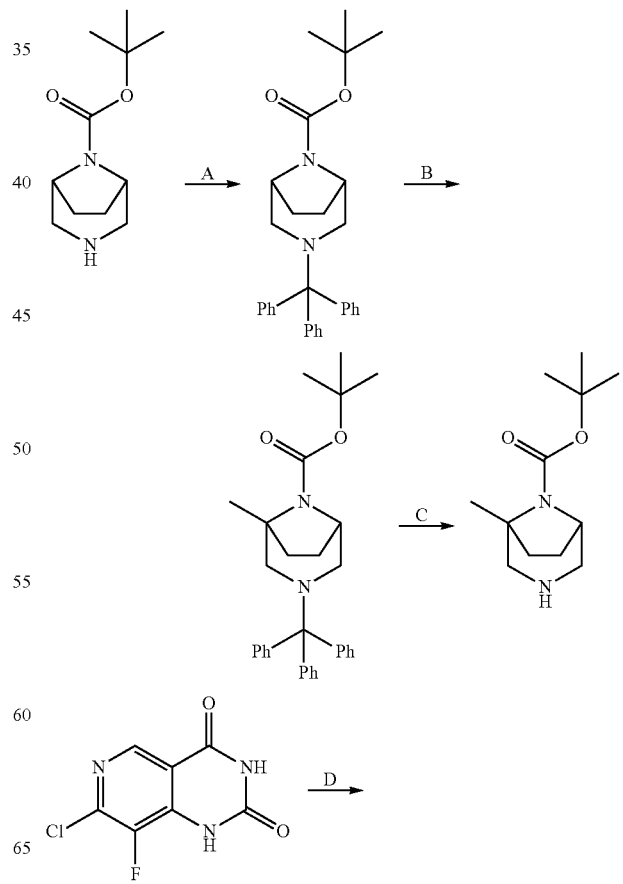

321
-continued

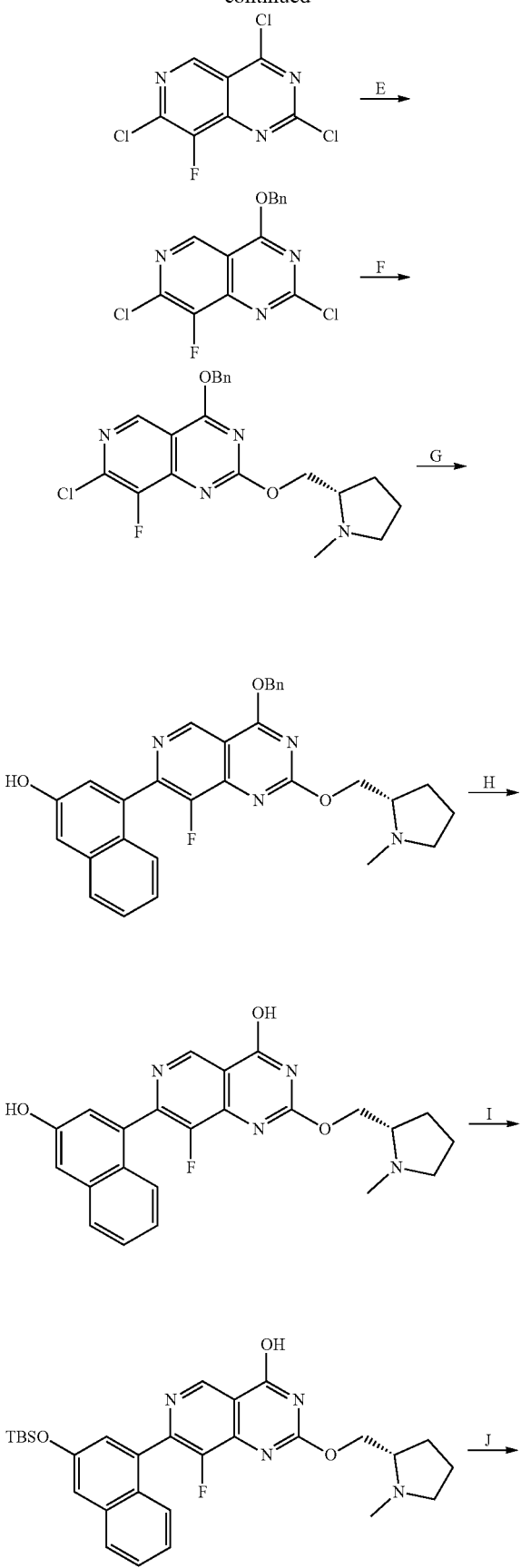

322
-continued

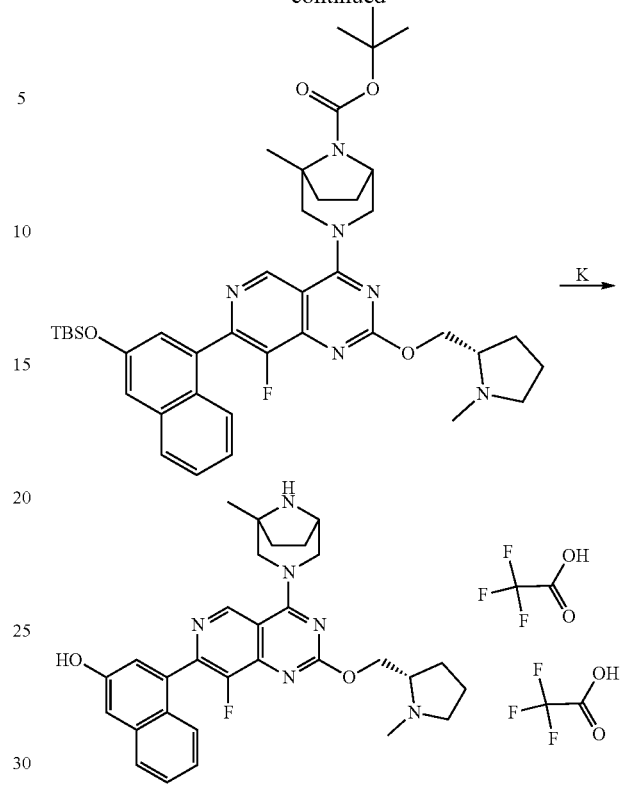

Step A. tert-butyl (1R,5S)-3-trityl-3,8-diazabicyclo[3.2.1]octane-8-carboxylate. To a solution of tert-butyl (1R,5S)-3,8-diazabicyclo[3.2.1]octane-8-carboxylate (1.0 g, 4.7 mmol) and triethyl amine (0.79 ml, 5.6 mmol) in DCM (23 mL) was added Trityl-Cl (1.4 g, 5.0 mmol) and the reaction was stirred at rt for 1 day. Additional tert-butyl (1R,5S)-3,8-diazabicyclo[3.2.1]octane-8-carboxylate (0.40 g) was added and the reaction was stirred for 8 h. The reaction was diluted with DCM and washed with water and brine. The organics were concentrated to a residue and purified by flash chromatography eluting with 0→50% EtOAc/Hex to give the title compound (2.0 g, 93%).

Step B. tert-butyl 1-methyl-3-trityl-3,8-diazabicyclo[3.2.1]octane-8-carboxylate. To a suspension of tert-butyl (1R,5S)-3-trityl-3,8-diazabicyclo[3.2.1]octane-8-carboxylate (0.30 g, 0.66 mmol) and N,N,N',N'-tetramethylethylenediamine (0.23 ml, 1.5 mmol) in diethyl ether (4.4 ml) at −30° C. under $N_2$ was added sBuli (1.4 M in cyclohexane, 1.1 ml, 1.5 mmol). After addition, the mixture was slowly warmed to 0° C. to give a yellow suspension. The mixture was stirred at 0° C. for 30 min followed by addition of iodomethane (0.041 ml, 0.66 mmol). After addition, the resulting mixture was stirred at 0° C. for 15 min and quenched with $NH_4Cl$ (Sat.). The mixture was then extracted with DCM and the DCM extract was dried over $Na_2SO_4$ and concentrated to give the crude desired product (0.29 g, 0.62 mmol, 94%) as a white solid. LCMS (MM-ES+APCI, Pos): m/z 227.3 (M+H-Ph$_3$C).

Step C. tert-butyl 1-methyl-3,8-diazabicyclo[3.2.1]octane-8-carboxylate. To a solution of tert-butyl 1-methyl-3-trityl-3,8-diazabicyclo[3.2.1]octane-8-carboxylate (0.28 g, 0.60 mmol) in 1,4-dioxane (6.0 ml) at rt was added HCl (1.0 N, 1.8 ml, 1.8 mmol). The solution was stirred at rt for 1 h and was then treated with solid NaHCO$_3$ (0.15 g, 1.8 mmol). The mixture was stirred at rt for 10 min. The resulting mixture was concentrated to dryness to give a white solid. The solid was extracted with DCM (10 ml) and the resulting suspension was passed through a short pad of celite. The filtrate was concentrated to give the crude desired product (0.31 g) as a white semi-solid.

Step D. 2,4,7-trichloro-8-fluoropyrido[4,3-d]pyrimidine. To a flask containing 7-chloro-8-fluoropyrido[4,3-d]pyrimidine-2,4 (1H,3H)-dione (0.93 g, 4.3 mmol) was added POCl$_3$ (8.0 ml, 86 mmol). The mixture was cooled with an ice bath and DIPEA (2.2 ml, 13 mmol) was added. The ice bath was removed, and mixture was heated between 100-110° C. until a clear solution was obtained (~20 h). The resulting solution was cooled and concentrated to give a brown oil. The oil was dissolved in DCM and the solution was quenched with a mixture of K$_3$PO$_4$ (37%, 10 ml) and ice (20 g). The resulting mixture was vigorously stirred for 10 min. The resulting two layers were separated and the organic layer was further washed with brine, dried over Na$_2$SO$_4$ and concentrated to give the crude desired product (1.5 g) as a brown solid.

Step E. 4-(benzyloxy)-2,7-dichloro-8-fluoropyrido[4,3-d] pyrimidine. To a flask containing crude 2,4,7-trichloro-8-fluoropyrido[4,3-d]pyrimidine (1.5 g, ~4.3 mmol) were added MS (3 A, 0.40 g), 1,4-dioxane (22 ml), benzyl alcohol (0.49 ml, 4.7 mmol) and DIPEA (2.3 ml, 13 mmol). The mixture was stirred at 60° C. under N$_2$ for 7 h. The mixture was concentrated to dryness and diluted with EtOAc. The resulting mixture was filtered through a short pad of Celite. The filtrate was concentrated, and the residue was purified by flash chromatography eluting with 0-25% Ethyl Acetate/hexanes to give the desired product (0.68 g, 2.1 mmol, 49%) as a white solid. LCMS (MM-ES+APCI, Pos): m/z 324.1 (M+H).

Step F. (S)-4-(benzyloxy)-7-chloro-8-fluoro-2-((1-methylpyrrolidin-2-yl)methoxy)pyrido[4,3-d]pyrimidine. To a solution of 4-(benzyloxy)-2,7-dichloro-8-fluoropyrido[4,3-d]pyrimidine (1.30 g, 4.01 mmol) in 1,4-dioxane (40 ml) was added (S)-(1-methylpyrrolidin-2-yl)methanol (0.667 ml, 5.61 mmol) followed by Cs$_2$CO$_3$ (3.27 g, 10.0 mmol). The mixture was heated at 80° C. under N$_2$ for 3 h and left stirring at rt for 15 h. The resulting mixture was diluted with ethyl acetate and filtered through a short pad of Celite. The filtrate was concentrated, and the residue was purified by preparative C18 HPLC (Gilson, 0-95% CH$_3$CN/H$_2$O with 0.1% TFA). The desired fractions were combined, basified with Na$_2$CO$_3$ (2 M) and extracted with EtOAc. The combined organic extract was washed with brine, dried over Na$_2$SO$_4$ and concentrated to give the desired product (0.91 g, 2.26 mmol, 56%) as an off-white solid. LCMS (MM-ES+APCI, Pos): m/z 403.1 (100%), 405.1 (50%) (M+H, M+3H.

Step G. (S)-4-(4-(benzyloxy)-8-fluoro-2-((1-methylpyrrolidin-2-yl)methoxy)pyrido[4,3-d]pyrimidin-7-yl)naphthalen-2-ol. A flask containing a mixture of (S)-4-(benzyloxy)-7-chloro-8-fluoro-2-((1-methylpyrrolidin-2-yl)methoxy) pyrido[4,3-d]pyrimidine (1.63 mmol), 4-(4,4,5,5-tetramethyl-1,3,2-dioxaborolan-2-yl)naphthalen-2-ol (0.575 g, 2.13 mmol), Na$_2$CO$_3$ (2.05 ml, 4.10 mmol), Pd(PPh$_3$)$_4$ (0.19 g, 0.16 mmol) in dioxane (16.4 ml) was sparged with N2. The mixture was heated under N$_2$ at 80° C. for 7 h and cooled to rt. The resulting mixture was quenched with water and extracted with EtOAc. The combined EtOAc extract was dried over Na$_2$SO$_4$ concentrated and purified by preparative C18 HPLC (Gilson, 5-95% CH$_3$CN/H$_2$O with 0.1% TFA). The desired fractions were combined, basified with NaHCO$_3$(Sat.) and extracted with DCM. The combined DCM extract was dried (Na$_2$SO$_4$) and concentrated to give the desired product (385 mg, 0.75 mmol, 46%) as an off-white solid. LCMS (MM-ES+APCI, Pos): m/z 511.2 (M+H).

Step H. (S)-8-fluoro-7-(3-hydroxynaphthalen-1-yl)-2-((1-methylpyrrolidin-2-yl)methoxy)pyrido[4,3-d]pyrimidin-4-ol. To a flask with a stir bar was added Pd/C (160 mg, 0.151 mmol). Then a solution of (S)-4-(4-(benzyloxy)-8-fluoro-2-((1-methylpyrrolidin-2-yl)methoxy)pyrido[4,3-d]pyrimidin-7-yl)naphthalen-2-ol (385 mg, 0.75 mmol) in EtOAc (15 ml) was added. The flask was closed with a septum and stirred under a balloon of H2 at rt for 15 h. The mixture was filtered through Celite and the Celite was further washed with DCM/MeOH (2:1, 200 ml). The combined organics were concentrated and dried to give the desired product (290 mg, 0.69 mmol, 92%) as an off-white solid. LCMS (MM-ES+APCI, Pos): m/z 421.2 (M+H).

Step I. (S)-7-(3-((tert-butyldimethylsilyl)oxy)naphthalen-1-yl)-8-fluoro-2-((1-methylpyrrolidin-2-yl)methoxy)pyrido [4,3-d]pyrimidin-4-ol. To a solution of (S)-8-fluoro-7-(3-hydroxynaphthalen-1-yl)-2-((1-methylpyrrolidin-2-yl) methoxy)pyrido[4,3-d]pyrimidin-4-ol (250 mg, 0.60 mmol) and imidazole (202 mg, 2.97 mmol) in DMF (5.9 ml) was added TBS-Cl (448 mg, 2.97 mmol). The mixture was stirred at rt for 3 h and diluted with EtOAc. The organics were washed with water (50 ml×2), dried over Na$_2$SO$_4$ and concentrated. The residue was purified by flash chromatography eluting with MeOH/EtOAc (0-30% with 2% Et$_3$N) to give the desired product (230 mg, 0.43 mmol, 72%) as an off-white solid. LCMS (MM-ES+APCI, Pos): m/z 535.2 (M+H).

Step J. tert-butyl 3-(7-(3-((tert-butyldimethylsilyl)oxy) naphthalen-1-yl)-8-fluoro-2-(((S)-1-methylpyrrolidin-2-yl) methoxy)pyrido[4,3-d]pyrimidin-4-yl)-1-methyl-3,8-diazabicyclo[3.2.1]octane-8-carboxylate. To a mixture of tert-butyl 1-methyl-3,8-diazabicyclo[3.2.1]octane-8-carboxylate (23 mg, 0.10 mmol), (S)-7-(3-((tert-butyldimethylsilyl)oxy) naphthalen-1-yl)-8-fluoro-2-((1-methylpyrrolidin-2-yl) methoxy)pyrido[4,3-d]pyrimidin-4-ol (27 mg, 0.050 mmol), 2-(3H-[1,2,3]triazolo[4,5-b]pyridin-3-yl)-1,1,3,3-tetramethylisouronium hexafluorophosphate(V) (38 mg, 0.10 mmol) in N,N-dimethylacetamide (0.50 ml) was added N-ethyl-N-isopropylpropan-2-amine (26 μL, 0.15 mmol). The solution was stirred at rt for 15 h and quenched with EtOAc. The resulting solution was washed with water, dried over Na$_2$SO$_4$ and concentrated to give the crude desired product as a brown oil (17.0 mg, 0.023 mmol, 45%). LCMS (MM-ES+APCI, Pos): m/z 743.3 (M+H).

Step K. 4-(8-fluoro-4-(1-methyl-3,8-diazabicyclo[3.2.1] octan-3-yl)-2-(((S)-1-methylpyrrolidin-2-yl)methoxy) pyrido[4,3-d]pyrimidin-7-yl)naphthalen-2-ol bis(2,2,2-trifluoroacetate). To a solution of the crude tert-butyl 3-(7-(3-((tert-butyldimethylsilyl)oxy)naphthalen-1-yl)-8-fluoro-2-(((S)-1-methylpyrrolidin-2-yl)methoxy)pyrido[4,3-d] pyrimidin-4-yl)-1-methyl-3,8-diazabicyclo[3.2.1]octane-8-carboxylate (17 mg, 0.023 mmol) in DCM (1.0 ml) was added TFA (0.3 ml). The solution was stirred at rt for 3 h. To the mixture was then added TBAF (0.1 ml, 1 M, 0.1 mmol). The resulting mixture was stirred at rt for 10 min and concentrated to dryness. The residue was purified by preparative C18 HPLC (Gilson, 5-95% CH$_3$CN/H$_2$O with 0.1% TFA). The desired fractions were combined and concentrated to give the title compound (6 mg, 0.008 mmol, 35% over 2 steps) as a yellow solid. LCMS (MM-ES+APCI, Pos): m/z 529.3 (M+H).

325
Example 157
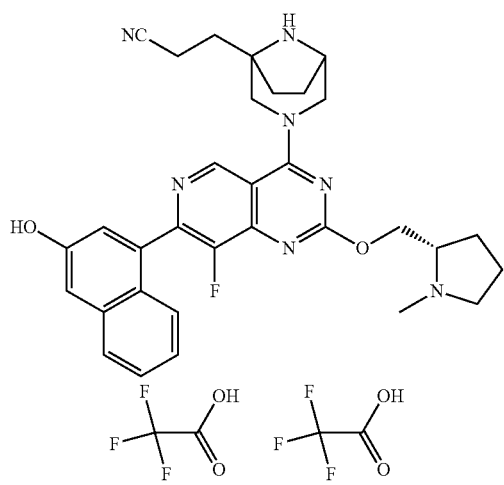
3-(3-(8-fluoro-7-(3-hydroxynaphthalen-1-yl)-2-(((S)-1-methylpyrrolidin-2-yl)methoxy)pyrido[4,3-d]pyrimidin-4-yl)-3,8-diazabicyclo[3.2.1]octan-1-yl)propanenitrile bis(2,2,2-trifluoroacetate)
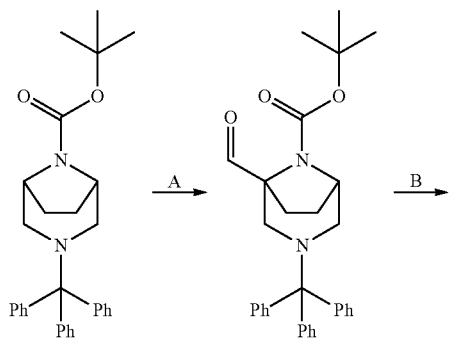
326
-continued
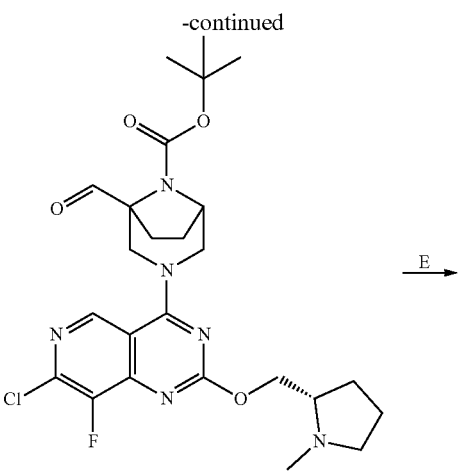
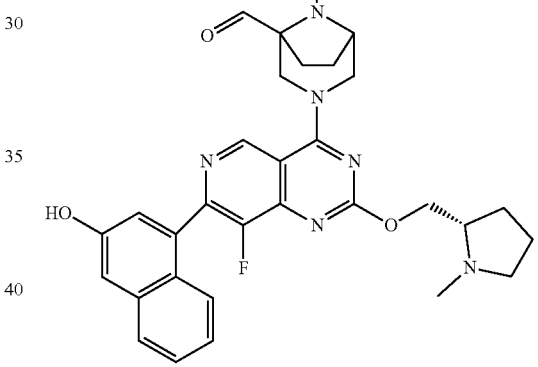
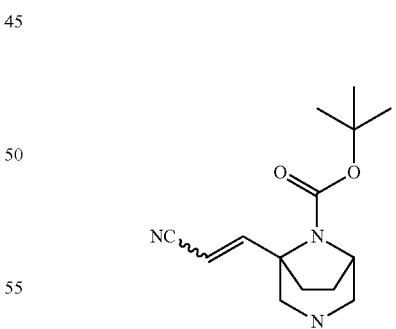
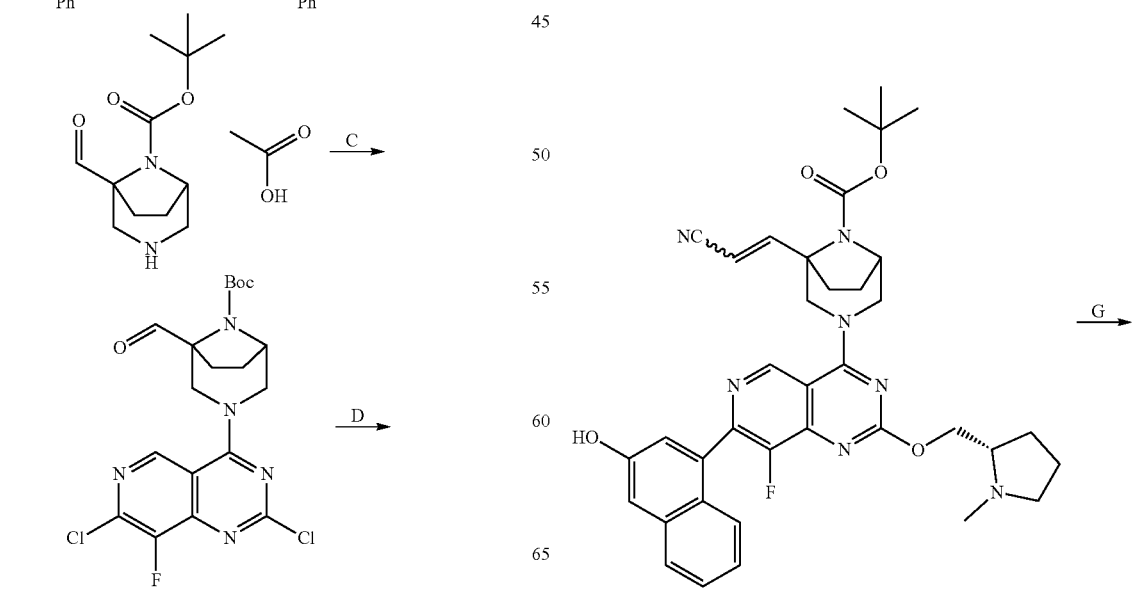

-continued

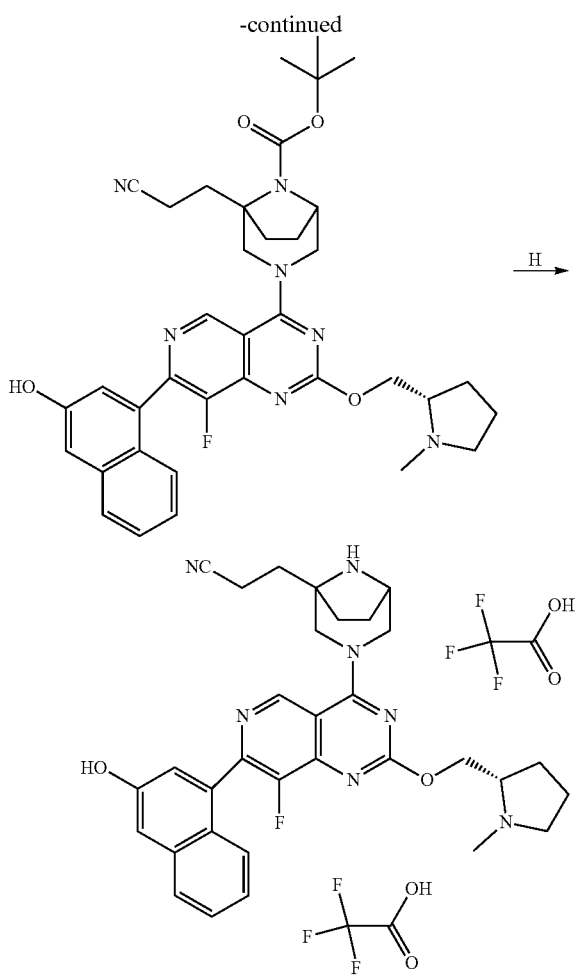

Step A. tert-butyl 1-formyl-3-trityl-3,8-diazabicyclo[3.2.1]octane-8-carboxylate. To a suspension of tert-butyl (1R,5S)-3-trityl-3,8-diazabicyclo[3.2.1]octane-8-carboxylate (1.36 g, 2.99 mmol) and N,N,N',N'-tetramethylethylenediamine (0.77 ml, 5.1 mmol) in diethyl ether (19.9 ml) at 0° C. was added sBuli (3.6 ml, 5.1 mmol). The mixture was stirred at 0° C. for 1.5 h to give an orange suspension. Ethyl formate (0.73 ml, 8.97 mmol) was added and the mixture was continued to stir at 0° C. for 15 min before quenching with NH₄Cl (Sat.). The mixture was diluted with EtOAc and washed with water. The organic layer was dried over Na₂SO₄, filtered, concentrated and purified by flash chromatography eluting with 0-20% ethyl acetate/hexanes to give the desired product (689 mg, 1.43 mmol, 48%) as a white solid. LCMS (MM-ES+APCI, Pos): m/z 185.2 (M+H-Ph₃C-isobutene).

Step B. tert-butyl 1-formyl-3,8-diazabicyclo[3.2.1]octane-8-carboxylate acetate. To a solution of tert-butyl 1-formyl-3-trityl-3,8-diazabicyclo[3.2.1]octane-8-carboxylate (600 mg, 1.24 mmol) in DCM (2.5 ml) was added acetic acid (2.5 ml). The mixture was stirred at 50° C. for 1 h and was then concentrated to dryness. The residue was co-evaporated with heptane (5 ml×3) to give the crude desired product as a solid.

Step C. tert-butyl (1R,5S)-3-(2,7-dichloro-8-fluoropyrido[4,3-d]pyrimidin-4-yl)-1-formyl-3,8-diazabicyclo[3.2.1]octane-8-carboxylate. To a solution of tert-butyl 1-formyl-3,8-diazabicyclo[3.2.1]octane-8-carboxylate acetate (0.42 g, 1.4 mmol) in DCM (7.0 ml) was added N-ethyl-N-isopropylpropan-2-amine (0.98 ml, 5.60 mmol), followed by 2,4,7-trichloro-8-fluoropyrido[4,3-d]pyrimidine (0.50 g, 1.96 mmol). The mixture was stirred at rt for 1 h, concentrated, and purified by flash chromatography eluting with 0-50% EtOAc/hexanes to give the desired product (0.24 g, 0.53 mmol, 38%) as an off-white solid. LCMS (MM-ES+APCI, Pos): m/z 456.1 (100%), 458.1 (50%) (M+H, M+3).

Step D. tert-butyl 3-(7-chloro-8-fluoro-2-(((S)-1-methylpyrrolidin-2-yl)methoxy)pyrido[4,3-d]pyrimidin-4-yl)-1-formyl-3,8-diazabicyclo[3.2.1]octane-8-carboxylate. To a solution of tert-butyl (1R,5S)-3-(2,7-dichloro-8-fluoropyrido[4,3-d]pyrimidin-4-yl)-1-formyl-3,8-diazabicyclo[3.2.1]octane-8-carboxylate (0.23 g, 0.504 mmol) in 1,4-dioxane (2.5 ml) was added (S)-(1-methylpyrrolidin-2-yl)methanol (0.078 ml, 0.66 mmol) followed by Cs₂CO₃ (0.25 g, 0.76 mmol). The mixture was heated at 70° C. for 1.5 h and then cooled to rt. The resulting mixture was diluted with EtOAc (30 ml), washed with water (30 ml) and NH₄Cl (sat., 20 ml). The solution was then dried over Na₂SO₄ and concentrated to dryness to give an oil. The oil was purified by flash chromatography eluting with 0-10% MeOH/EtOAc to give the desired product (186 mg, 0.35 mmol, 69%) as a white solid. LCMS (MM-ES+APCI, Pos): m/z 567.2 (100%), 569.3 (50%) (M+H, M+3).

Step E. tert-butyl 3-(8-fluoro-7-(3-hydroxynaphthalen-1-yl)-2-(((S)-1-methylpyrrolidin-2-yl)methoxy)pyrido[4,3-d]pyrimidin-4-yl)-1-formyl-3,8-diazabicyclo[3.2.1]octane-8-carboxylate. A mixture of tert-butyl 3-(7-chloro-8-fluoro-2-(((S)-1-methylpyrrolidin-2-yl)methoxy)pyrido[4,3-d]pyrimidin-4-yl)-1-formyl-3,8-diazabicyclo[3.2.1]octane-8-carboxylate (140 mg, 0.26 mmol), 4-(4,4,5,5-tetramethyl-1,3,2-dioxaborolan-2-yl)naphthalen-2-ol (106 mg, 0.39 mmol), Na₂CO₃ (0.39 ml, 0.79 mmol), and Pd(PPh₃)₄ (30.2 mg, 0.026 mmol) in dioxane (3.7 ml) was sparged with N2 and heated in a sealed tube at 85° C. for 15 h. The mixture was cooled to rt and quenched with EtOAc (30 ml), water (20 ml) and NH₄Cl (sat.). The resulting two layers were separated. The organic layer was dried over Na₂SO₄, filtered, concentrated, and the residue was purified by flash chromatography eluting with 0-15% MeOH/EtOAc to give the desired product (136 mg, 0.21 mmol, 81%) as a light yellow solid. LCMS (MM-ES+APCI, Pos): m/z 643.3 (M+H).

Step F. tert-butyl 1-(2-cyanovinyl)-3-(8-fluoro-7-(3-hydroxynaphthalen-1-yl)-2-(((S)-1-methylpyrrolidin-2-yl)methoxy)pyrido[4,3-d]pyrimidin-4-yl)-3,8-diazabicyclo[3.2.1]octane-8-carboxylate. To a solution of tert-butyl 3-(8-fluoro-7-(3-hydroxynaphthalen-1-yl)-2-(((S)-1-methylpyrrolidin-2-yl)methoxy)pyrido[4,3-d]pyrimidin-4-yl)-1-formyl-3,8-diazabicyclo[3.2.1]octane-8-carboxylate (33 mg, 0.051 mmol) in THF (1.0 ml) at 0° C. was added diethyl cyanomethylphosphonate (25 μL, 0.15 mmol) followed by NaH (6.2 mg, 0.15 mmol). The solution was stirred at 0° C. for 0.5 h. The mixture was then concentrated to dryness to give a yellow solid. The solid was partitioned between NaHCO₃(Sat.) and DCM/IPA (5:1). The two layers were separated, and the organic layer was dried and concentrated to give the crude desired product (40 mg, 0.060 mmol, 117.0%) as a light brown solid. LCMS (MM-ES+APCI, Pos): m/z 666.3 (M+H).

Step G. tert-butyl 1-(2-cyanoethyl)-3-(8-fluoro-7-(3-hydroxynaphthalen-1-yl)-2-(((S)-1-methylpyrrolidin-2-yl)methoxy)pyrido[4,3-d]pyrimidin-4-yl)-3,8-diazabicyclo[3.2.1]octane-8-carboxylate. A mixture of tert-butyl 1-((E)-2-cyanovinyl)-3-(8-fluoro-7-(3-hydroxynaphthalen-1-yl)-2-(((S)-1-methylpyrrolidin-2-yl)methoxy)pyrido[4,3-d]pyrimidin-4-yl)-3,8-diazabicyclo[3.2.1]octane-8- carboxylate (25 mg, 0.038 mmol), Pd/C (40.0 mg, 0.038 mmol) and MeOH (2 ml) was stirred under a balloon of H2 at rt for 3 h. The mixture was filtered through a short pad of Celite. The Celite was rinsed with MeOH and the combined filtrate was concentrated to give the crude desired product (24 mg, 0.036 mmol, 95%) as a light yellow material. LCMS (MM-ES+APCI, Pos): m/z 668.2 (M+H).

Step H. 3-(3-(8-fluoro-7-(3-hydroxynaphthalen-1-yl)-2-(((S)-1-methylpyrrolidin-2-yl)methoxy)pyrido[4,3-d]pyrimidin-4-yl)-3,8-diazabicyclo[3.2.1]octan-1-yl)propanenitrile bis(2,2,2-trifluoroacetate). To a solution of tert-butyl 1-(2-cyanoethyl)-3-(8-fluoro-7-(3-hydroxynaphthalen-1-yl)-2-(((S)-1-methylpyrrolidin-2-yl)methoxy)pyrido[4,3-d]pyrimidin-4-yl)-3,8-diazabicyclo[3.2.1]octane-8-carboxylate (24 mg, 0.036 mmol) in DCM (1.0 ml) was added TFA (0.3 ml). The mixture was stirred at rt for 2 h and concentrated. The residue was purified by preparative C18 HPLC (Gilson, 0-95% CH₃CN/H₂O with 0.1% TFA). The desired fractions were combined and concentrated to give the title compound (13 mg, 0.016 mmol, 45%) as a yellow solid. LCMS (MM-ES+APCI, Pos): m/z 568.2 (M+H).

Example 158

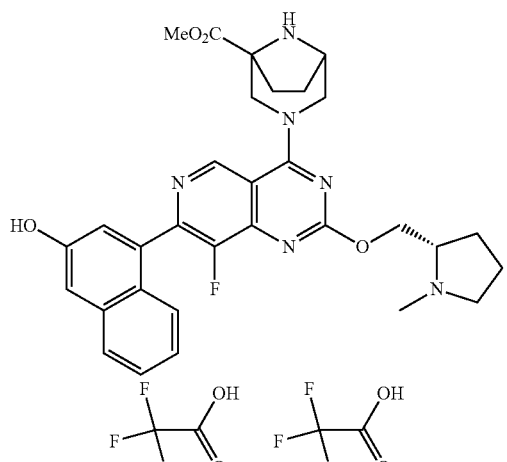

methyl 3-(8-fluoro-7-(3-hydroxynaphthalen-1-yl)-2-(((S)-1-methylpyrrolidin-2-yl)methoxy)pyrido[4,3-d]pyrimidin-4-yl)-3,8-diazabicyclo[3.2.1]octane-1-carboxylate bis(2,2,2-trifluoroacetate)

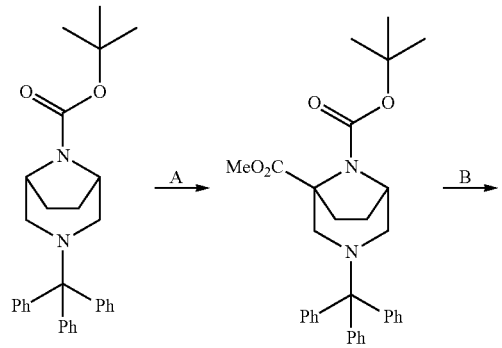

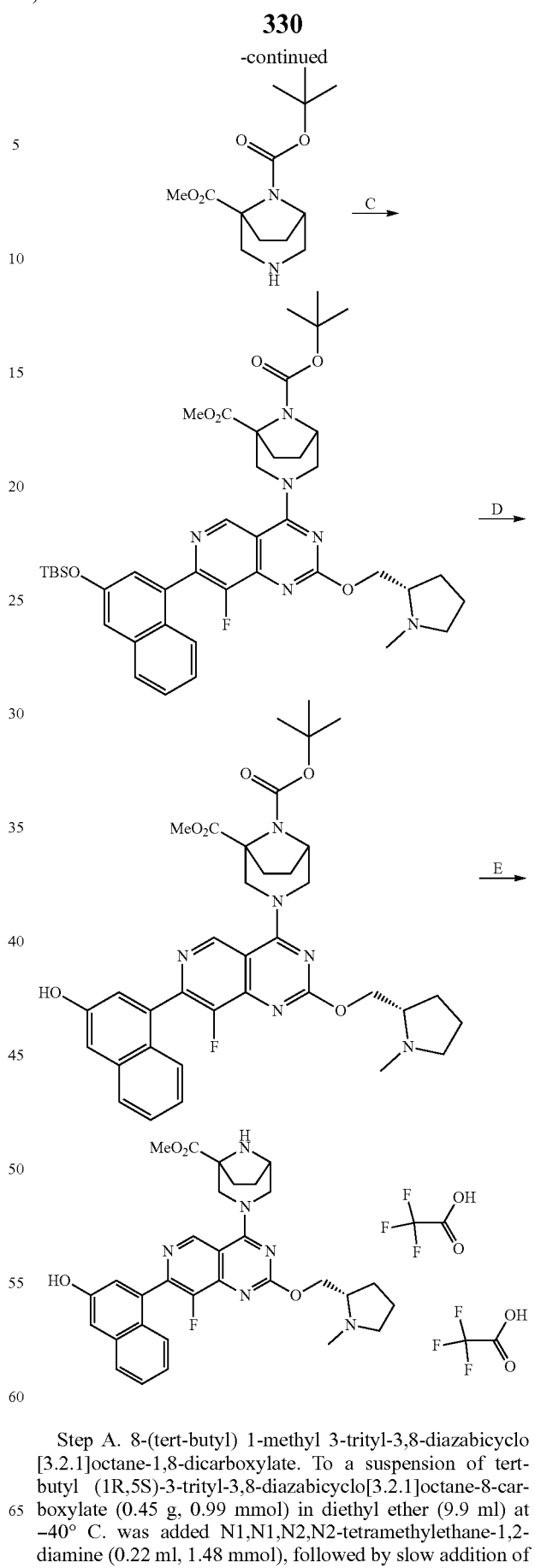

Step A. 8-(tert-butyl) 1-methyl 3-trityl-3,8-diazabicyclo[3.2.1]octane-1,8-dicarboxylate. To a suspension of tert-butyl (1R,5S)-3-trityl-3,8-diazabicyclo[3.2.1]octane-8-carboxylate (0.45 g, 0.99 mmol) in diethyl ether (9.9 ml) at −40° C. was added N1,N1,N2,N2-tetramethylethane-1,2-diamine (0.22 ml, 1.48 mmol), followed by slow addition of sec-butyllithium (1.06 ml, 1.48 mmol). The mixture was warmed to 0° C. and maintained at that temperature for 30 min before cooling to −70° C. Then, methyl chloroformate (0.15 ml, 1.98 mmol) was added slowly. The mixture was warmed to rt and quenched with NH₄Cl (sat.). The mixture was extracted with EtOAc and the extract was dried over Na₂SO₄, concentrated and purified by flash chromatography eluting with 0-40% ethyl acetate/hexanes to give the desired product (505 mg, 0.99 mmol, 100%) as a white solid. LCMS (MM-ES+APCI, Pos): m/z 271.2 (M+H-Ph3C).

Step B. tert-butyl 1-formyl-3,8-diazabicyclo[3.2.1]octane-8-carboxylate acetate. To a solution of 8-(tert-butyl) 1-methyl 3-trityl-3,8-diazabicyclo[3.2.1]octane-1,8-dicarboxylate (157 mg, 0.31 mmol) in 1,4-dioxane (3.1 ml) at rt was added HCl (1.0 N, 0.77 ml, 0.77 mmol). The solution was stirred at rt for 1 h and was then treated with NaHCO₃ (77.2 mg, 0.92 mmol). The mixture was stirred at rt for 30 min and concentrated to dryness to give a white solid. The solid was extracted with DCM (10 ml) and passed through a filter plug. The filtrate was concentrated to give the crude desired product as a white solid.

Step C. 8-(tert-butyl) 1-methyl 3-(7-(3-((tert-butyldimethylsilyl)oxy)naphthalen-1-yl)-8-fluoro-2-(((S)-1-methylpyrrolidin-2-yl)methoxy)pyrido[4,3-d]pyrimidin-4-yl)-3,8-diazabicyclo[3.2.1]octane-1,8-dicarboxylate. To a mixture of 8-(tert-butyl) 1-methyl 3,8-diazabicyclo[3.2.1]octane-1,8-dicarboxylate (71 mg, 0.26 mmol), (S)-7-(3-((tert-butyldimethylsilyl)oxy)naphthalen-1-yl)-8-fluoro-2-((1-methylpyrrolidin-2-yl)methoxy)pyrido[4,3-d]pyrimidin-4-ol (Synthesized according to Example 156) (70 mg, 0.13 mmol), 2-(3H-[1,2,3]triazolo[4,5-b]pyridin-3-yl)-1,1,3,3-tetramethylisouronium hexafluorophosphate(V) (100 mg, 0.26 mmol) in N,N-dimethylacetamide (1.3 ml) was added N-ethyl-N-isopropylpropan-2-amine (69 μL, 0.39 mmol). The solution was stirred at rt for 1.5 h, and then quenched with EtOAc. The resulting mixture was washed with water, dried over Na₂SO₄ and concentrated. The residue was purified by flash chromatography eluting with 0-100% ethyl acetate/hexanes (with 2% Et₃N) to give the desired product (87 mg, 0.11 mmol, 84%) as a white solid. LCMS (MM-ES+APCI, Pos): m/z 787.3 (M+H).

Step D. 8-(tert-butyl) 1-methyl 3-(8-fluoro-7-(3-hydroxynaphthalen-1-yl)-2-(((S)-1-methylpyrrolidin-2-yl)methoxy)pyrido[4,3-d]pyrimidin-4-yl)-3,8-diazabicyclo[3.2.1]octane-1,8-dicarboxylate. To a solution of 8-(tert-butyl) 1-methyl 3-(7-(3-((tert-butyldimethylsilyl)oxy)naphthalen-1-yl)-8-fluoro-2-(((S)-1-methylpyrrolidin-2-yl)methoxy)pyrido[4,3-d]pyrimidin-4-yl)-3,8-diazabicyclo[3.2.1]octane-1,8-dicarboxylate (80 mg, 0.10 mmol) in THF (1.0 ml) and methanol (0.50 ml, 0.10 mmol) was added lithium hydroxide (0.30 ml, 0.61 mmol). The mixture was stirred at rt for 4 h and then quenched with NH₄Cl (sat.). The mixture was extracted with EtOAc and the extract was dried over Na₂SO₄, filtered and concentrated. The residue was purified by flash chromatography eluting with 0-100% MeOH/EtOAc (with 2% Et₃N) to give the desired product (8.0 mg, 0.012 mmol, 12%) as a white solid. LCMS (MM-ES+APCI, Pos): m/z 673.2 (M+H).

Step E. methyl 3-(8-fluoro-7-(3-hydroxynaphthalen-1-yl)-2-(((S)-1-methylpyrrolidin-2-yl)methoxy)pyrido[4,3-d]pyrimidin-4-yl)-3,8-diazabicyclo[3.2.1]octane-1-carboxylate bis(2,2,2-trifluoroacetate). To a solution of 8-(tert-butyl) 1-methyl 3-(8-fluoro-7-(3-hydroxynaphthalen-1-yl)-2-(((S)-1-methylpyrrolidin-2-yl)methoxy)pyrido[4,3-d]pyrimidin-4-yl)-3,8-diazabicyclo[3.2.1]octane-1,8-dicarboxylate (8.0 mg, 0.012 mmol) in DCM (1.0 ml) was added TFA (0.3 ml). The mixture was stirred at rt and concentrated. The residue was purified by preparative C18 HPLC (Gilson, 0-95% CH₃CN/H₂O with 0.1% TFA). The desired fractions were combined and concentrated to give the desired product (8.0 mg, 0.010 mmol, 84%) as a yellow solid. LCMS (MM-ES+APCI, Pos): m/z 573.2 (M+H).

Example 159

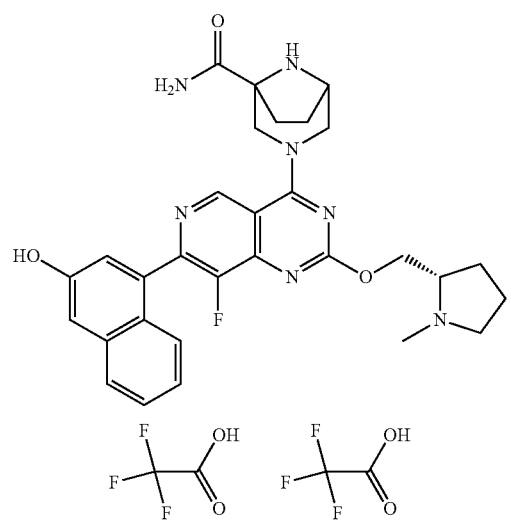

3-(8-fluoro-7-(3-hydroxynaphthalen-1-yl)-2-(((S)-1-methylpyrrolidin-2-yl)methoxy)pyrido[4,3-d]pyrimidin-4-yl)-3,8-diazabicyclo[3.2.1]octane-1-carboxamide bis(2,2,2-trifluoroacetate)

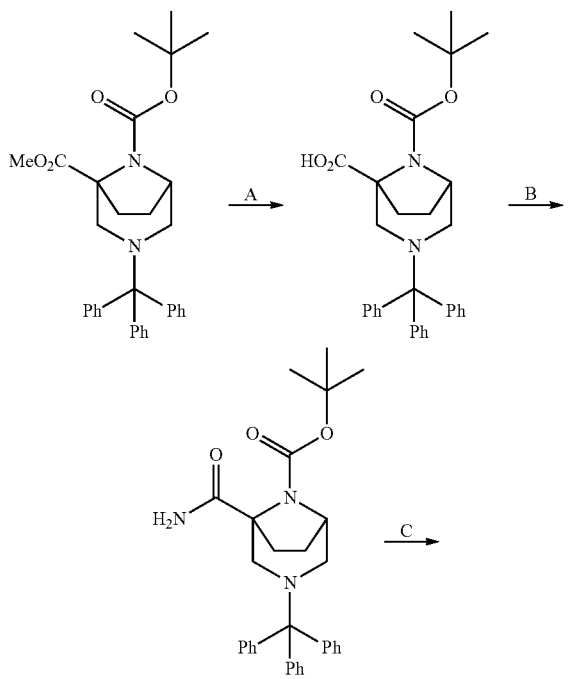

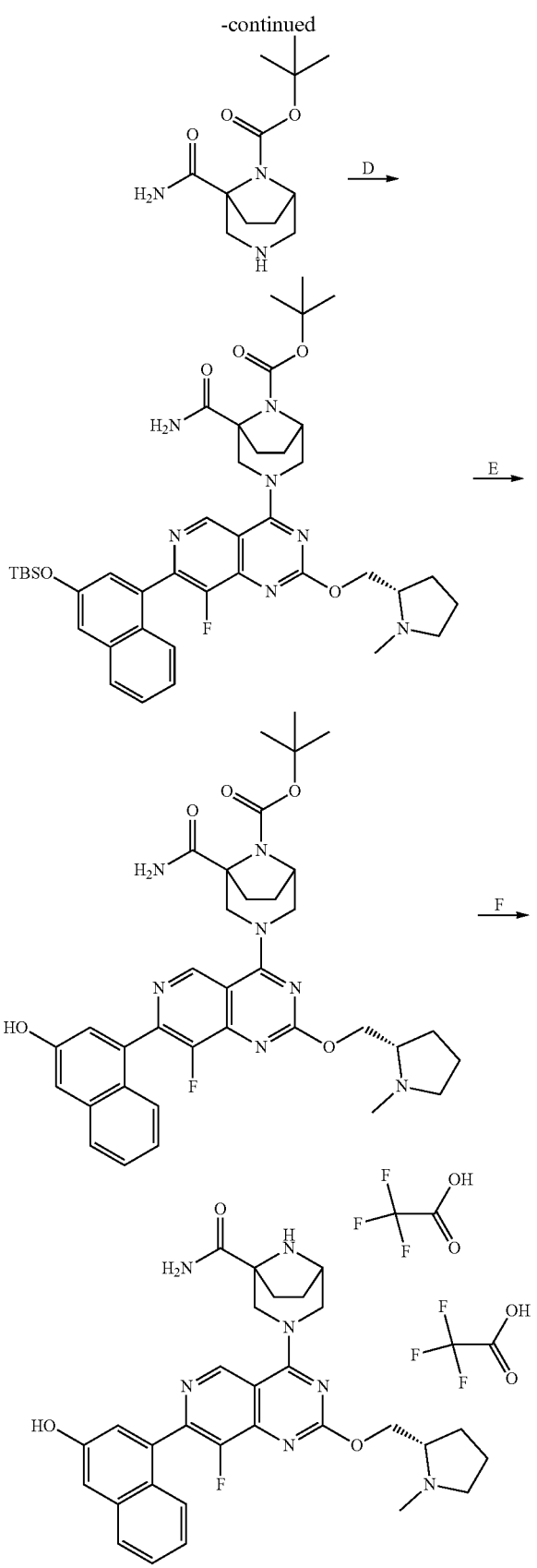

Step A. 8-(tert-butoxycarbonyl)-3-trityl-3,8-diazabicyclo[3.2.1]octane-1-carboxylic acid. To a solution of 8-(tert-butyl) 1-methyl 3-trityl-3,8-diazabicyclo[3.2.1]octane-1,8-dicarboxylate (131 mg, 0.26 mmol) in dioxane (5.0 ml) was added NaOH (2 M, 2.2 ml, 4.4 mmol). The mixture was heated at 80° C. for 20 h. The mixture was cooled to rt, acidified with citric acid (10%, 10 ml) and extracted with EtOAc. The organics were dried over Na$_2$SO$_4$, concentrated and purified by flash chromatography eluting with EtOAc in hexanes (0-100%) to give the desired product (96 mg, 0.19 mmol, 75%) as a white foam. LCMS (MM-ES+APCI, Pos): m/z 201.0 (M+H-Ph$_3$C-isobutene).

Step B. tert-butyl 1-carbamoyl-3-trityl-3,8-diazabicyclo[3.2.1]octane-8-carboxylate. To a solution of 8-(tert-butoxycarbonyl)-3-trityl-3,8-diazabicyclo[3.2.1]octane-1-carboxylic acid (96 mg, 0.19 mmol) and HOBT (59 mg, 0.39 mmol) in DMF (1.9 ml) was added EDC (74 mg, 0.39 mmol). The mixture was stirred at rt for 1 h, and NH$_4$OH (0.2 ml, 0.19 mmol) was added. The resulting mixture was stirred at rt for 0.5 h. The mixture was quenched with EtOAc, washed with citric acid (10%, 20 ml), NaHCO$_3$ (Sat.), dried over Na$_2$SO$_4$ and concentrated and purified with silica column using EtOAc in hexanes (0-100%) as eluent to give the desired product (49 mg, 0.098 mmol, 51%) as a white solid. LCMS (MM-ES+APCI, Pos): m/z 256.3 (M+H-Ph$_3$C).

Step C. tert-butyl 1-carbamoyl-3,8-diazabicyclo[3.2.1]octane-8-carboxylate. To a solution of tert-butyl 1-carbamoyl-3-trityl-3,8-diazabicyclo[3.2.1]octane-8-carboxylate (49 mg, 0.098 mmol) in 1,4-dioxane (0.99 ml) at rt was added HCl (0.20 ml, 0.20 mmol). The solution was stirred at rt for 1 h. The mixture was treated with solid NaHCO$_3$ (17 mg, 0.20 mmol) and stirred at rt for 30 min. The resulting mixture was concentrated to dryness to give a white solid. The solid was triturated with DCM (10 ml) and passed through a filter plug. The filtrate was concentrated to give the crude desired product as a white solid.

Step D. tert-butyl 3-(7-(3-((tert-butyldimethylsilyl)oxy)naphthalen-1-yl)-8-fluoro-2-(((S)-1-methylpyrrolidin-2-yl)methoxy)pyrido[4,3-d]pyrimidin-4-yl)-1-carbamoyl-3,8-diazabicyclo[3.2.1]octane-8-carboxylate. To a mixture of tert-butyl 1-carbamoyl-3,8-diazabicyclo[3.2.1]octane-8-carboxylate (24 mg, 0.095 mmol), (S)-7-(3-((tert-butyldimethylsilyl)oxy)naphthalen-1-yl)-8-fluoro-2-((1-methylpyrrolidin-2-yl)methoxy)pyrido[4,3-d]pyrimidin-4-ol (synthesized according to Example 156) (30 mg, 0.056 mmol), 2-(3H-[1,2,3]triazolo[4,5-b]pyridin-3-yl)-1,1,3,3-tetramethylisouronium hexafluorophosphate(V) (43 mg, 0.11 mmol) in N,N-dimethylacetamide (0.56 ml) was added N-ethyl-N-isopropylpropan-2-amine (29 µL, 0.17 mmol). The solution was stirred at rt for 1 h. The mixture was purified by preparative C18 HPLC (Gilson, 0-95% CH$_3$CN/H$_2$O with 0.1% TFA). The desired reactions were combined, basified with NaHCO$_3$(Sat.) and extracted with EtOAc. The EtOAc extract was dried over Na$_2$SO$_4$ and concentrated to give the impure desired product (50 mg, 0.039 mmol, 115%) as a yellow solid. LCMS (MM-ES+APCI, Pos): m/z 772.2 (M+H).

Step E. tert-butyl 1-carbamoyl-3-(8-fluoro-7-(3-hydroxynaphthalen-1-yl)-2-(((S)-1-methylpyrrolidin-2-yl)methoxy)pyrido[4,3-d]pyrimidin-4-yl)-3,8-diazabicyclo[3.2.1]octane-8-carboxylate. To a solution of tert-butyl 3-(7-(3-((tert-butyldimethylsilyl)oxy)naphthalen-1-yl)-8-fluoro-2-(((S)-1-methylpyrrolidin-2-yl)methoxy)pyrido[4,3-d]pyrimidin-4-yl)-1-carbamoyl-3,8-diazabicyclo[3.2.1]octane-8-carboxylate (50 mg, 0.065 mmol) in THF (0.90 ml) at 0° C. was added TBAF (0.18 ml, 0.18 mmol). The solution was stirred at rt for 1 h and was purified by preparative C18 HPLC (Gilson, 0-95% CH$_3$CN/H$_2$O with 0.1% TFA). The desired fractions were combined, basified with NaHCO$_3$(Sat.) and extracted with EtOAc. The EtOAc extract was dried over Na$_2$SO$_4$ and concentrated to give the desired product (31 mg, 0.047 mmol, 72%) as a white solid. LCMS (MM-ES+APCI, Pos): m/z 658.3 (M+H).

Step F. 3-(8-fluoro-7-(3-hydroxynaphthalen-1-yl)-2-(((S)-1-methylpyrrolidin-2-yl)methoxy)pyrido[4,3-d]pyrimidin-4-yl)-3,8-diazabicyclo[3.2.1]octane-1-carboxamide bis(2,2,2-trifluoroacetate). To a solution of tert-butyl 1-carbamoyl-3-(8-fluoro-7-(3-hydroxynaphthalen-1-yl)-2-(((S)-1-methylpyrrolidin-2-yl)methoxy)pyrido[4,3-d]pyrimidin-4-yl)-3,8-diazabicyclo[3.2.1]octane-8-carboxylate (25 mg, 0.038 mmol) in dichloromethane (1.0 ml) was added 2,2,2-trifluoroacetic acid (0.3.0 ml). The mixture was concentrated, and the residue was purified by preparative C18 HPLC (Gilson, 0-95% CH$_3$CN/H$_2$O with 0.1% TFA). The desired fractions were combined and lyophilized to give the title compound (5 mg, 0.0064 mmol, 17%) as a hygroscopic yellow solid. LCMS (MM-ES+APCI, Pos): m/z 558.2 (M+H).

Example 160

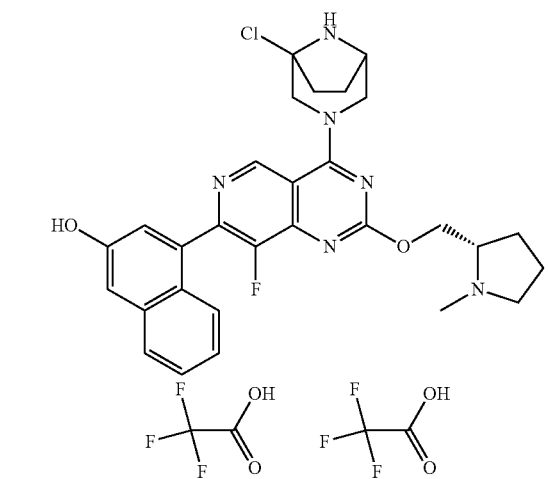

4-(4-(1-chloro-3,8-diazabicyclo[3.2.1]octan-3-yl)-8-fluoro-2-(((S)-1-methylpyrrolidin-2-yl)methoxy)pyrido[4,3-d]pyrimidin-7-yl)naphthalen-2-ol bis(2,2,2-trifluoroacetate)

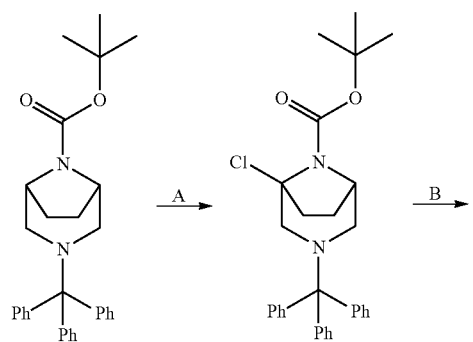

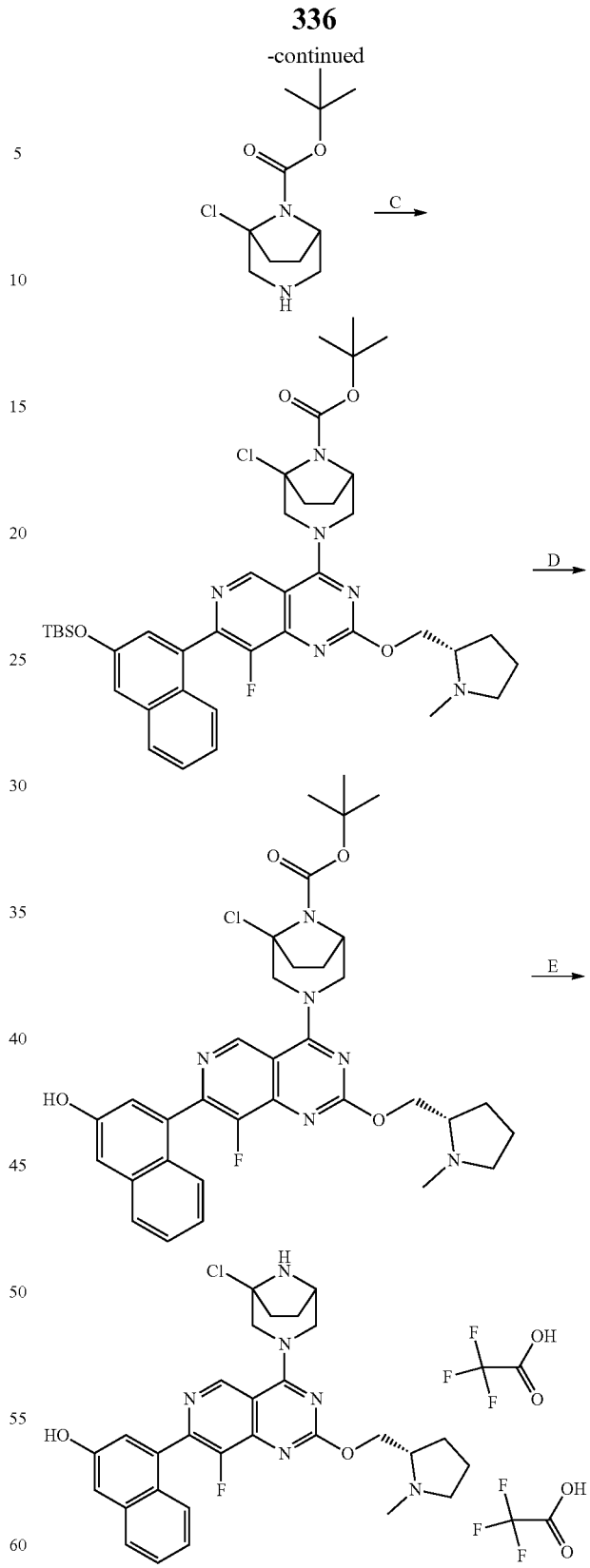

Step A. tert-butyl 1-chloro-3-trityl-3,8-diazabicyclo[3.2.1]octane-8-carboxylate. To a suspension of tert-butyl (1R,5S)-3-trityl-3,8-diazabicyclo[3.2.1]octane-8-carboxylate (136 mg, 0.30 mmol) in ethoxyethane (3.0 ml, 0.30 mmol) at −40° C. was added N1,N1,N2,N2-tetramethylethane-1,2-diamine (68 μL, 0.45 mmol), followed by slow addition of sec-butyllithium (0.32 ml, 0.45 mmol). The mixture was warmed to 0° C. and maintained at that temperature for 20 min before cooling to −70° C. Then, Hexachloroethane (142 mg, 0.60 mmol) was added. The mixture was warmed to rt and quenched with NH₄Cl (sat.). The mixture was extracted with EtOAc, and the EtOAc extract was dried over Na₂SO₄, concentrated and purified by flash chromatography eluting with EtOAc in hexanes (0-20%) to give the desired product (123 mg, 0.25 mmol, 84%) as a white foam. LCMS (MM-ES+APCI, Pos): m/z 191.2 (100%), 193.1 (40%) (M+H-Ph3C-isobutene, M+3-Ph3C-isobutene).

Step B. tert-butyl 1-chloro-3,8-diazabicyclo[3.2.1]octane-8-carboxylate. To a solution of tert-butyl 1-chloro-3-trityl-3,8-diazabicyclo[3.2.1]octane-8-carboxylate (123 mg, 0.25 mmol) in 1,4-dioxane (2.5 ml, 0.25 mmol) at rt was added HCl (0.63 ml, 0.63 mmol). The solution was stirred at rt for 1 h. The mixture was treated with solid NaHCO₃ (63 mg, 0.76 mmol) and stirred at rt for 30 min. The resulting mixture was concentrated to dryness to give a white solid. The solid was triturated with DCM (10 ml) and passed through a filter plug. The filtrate was concentrated to give the crude desired product as a white solid.

Step C. tert-butyl 3-(7-(3-((tert-butyldimethylsilyl)oxy) naphthalen-1-yl)-8-fluoro-2-(((S)-1-methylpyrrolidin-2-yl) methoxy)pyrido[4,3-d]pyrimidin-4-yl)-1-chloro-3,8-diazabicyclo[3.2.1]octane-8-carboxylate. To a mixture of tert-butyl 1-chloro-3,8-diazabicyclo[3.2.1]octane-8-carboxylate (28 mg, 0.11 mmol), (S)-7-(3-((tert-butyldimethylsilyl)oxy) naphthalen-1-yl)-8-fluoro-2-((1-methylpyrrolidin-2-yl) methoxy)pyrido[4,3-d]pyrimidin-4-ol (30 mg, 0.056 mmol), 2-(3H-[1,2,3]triazolo[4,5-b]pyridin-3-yl)-1,1,3,3-tetramethylisouronium hexafluorophosphate(V) (43 mg, 0.11 mmol) in N,N-dimethylacetamide (0.56 ml) was added N-ethyl-N-isopropylpropan-2-amine (29 μL, 0.17 mmol). The solution was stirred at rt for 1.5 h. The mixture was purified by preparative C18 HPLC (Gilson, 0-95% CH₃CN/H₂O with 0.1% TFA). The desired fractions were combined, basified with NaHCO₃(Sat.) and extracted with EtOAc. The EtOAc extract was dried over Na₂SO₄ and concentrated to give the desired product (30 mg, 0.039 mmol, 70%) as a white solid. LCMS (MM-ES+APCI, Pos): m/z 763.3 (100%), 765.2 (50%) (M+H, M+3).

Step D. tert-butyl 1-chloro-3-(8-fluoro-7-(3-hydroxynaphthalen-1-yl)-2-(((S)-1-methylpyrrolidin-2-yl) methoxy)pyrido[4,3-d]pyrimidin-4-yl)-3,8-diazabicyclo [3.2.1]octane-8-carboxylate. To a solution of tert-butyl 3-(7-(3-((tert-butyldimethylsilyl)oxy)naphthalen-1-yl)-8-fluoro-2-(((S)-1-methylpyrrolidin-2-yl)methoxy)pyrido[4,3-d] pyrimidin-4-yl)-1-chloro-3,8-diazabicyclo[3.2.1]octane-8-carboxylate (30 mg, 0.039 mmol) in THF (1.0 ml) at 0° C. was added TBAF (0.20 ml, 1.0 M, 0.20 mmol). The mixture was stirred at 0° C. for 30 min. The mixture was diluted with EtOAc and washed with water. The organic solution was dried over Na₂SO₄ and concentrated to give the crude desired product as a white solid.

Step E. 4-(4-(1-chloro-3,8-diazabicyclo[3.2.1]octan-3-yl)-8-fluoro-2-(((S)-1-methylpyrrolidin-2-yl)methoxy) pyrido[4,3-d]pyrimidin-7-yl)naphthalen-2-ol bis(2,2,2-trifluoroacetate). To a solution of tert-butyl 1-chloro-3-(8-fluoro-7-(3-hydroxynaphthalen-1-yl)-2-(((S)-1-methylpyrrolidin-2-yl)methoxy)pyrido[4,3-d]pyrimidin-4-yl)-3,8-diazabicyclo[3.2.1]octane-8-carboxylate (26 mg, 0.04 mmol, 0.040 mmol) in DCM (2.0 ml, 0.040 mmol) was added TFA (0.40 ml, 0.040 mmol). The solution was stirred at rt for 1 h and concentrated to dryness. The residue was purified by preparative C18 HPLC (Gilson, 0-95% CH₃CN/H₂O with 0.1% TFA). The desired fractions were combined and concentrated to the title compound (16 mg, 0.020 mmol, 50%) as a yellow solid. LCMS (MM-ES+APCI, Pos): m/z 549.2 (M+H).

Example 161

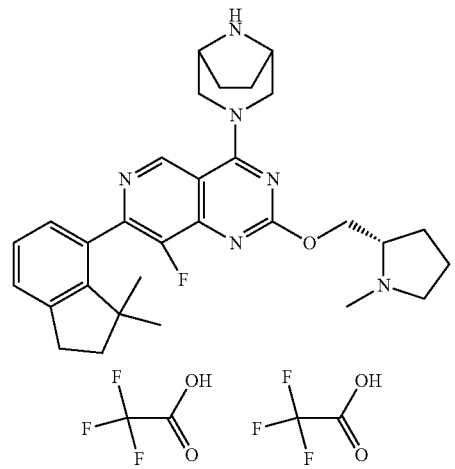

4-((1R,5S)-3,8-diazabicyclo[3.2.1]octan-3-yl)-7-(3, 3-dimethyl-2,3-dihydro-1H-inden-4-yl)-8-fluoro-2-(((S)-1-methylpyrrolidin-2-yl)methoxy)pyrido[4,3-d] pyrimidine bis(2,2,2-trifluoroacetate)

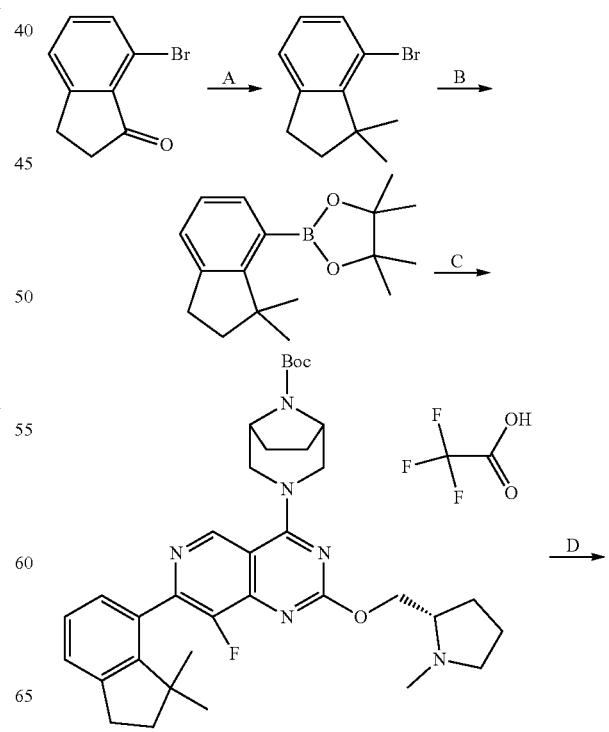

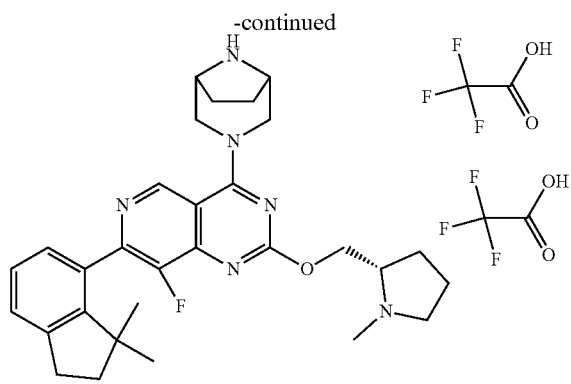

Step A. 7-bromo-1,1-dimethyl-2,3-dihydro-1H-indene. To a suspension of TiCl₄ (0.49 ml, 4.40 mmol) in DCM (5.0 ml) at −40° C. was added dropwise dimethylzine (2 M, 2.2 ml, 4.40 mmol). After addition, the resulting mixture was stirred at −40 and −30° C. for 20 min. Then, a solution of 7-bromo-2,3-dihydro-1H-inden-1-one (422 mg, 2.00 mmol) in DCM (2.0 ml) was added dropwise. After addition, the mixture was warmed to rt and left stirring at rt for 15 h. The mixture was quenched with NH₄Cl (Sat.) and extracted with DCM. The DCM extract was dried over Na₂SO₄ and filtered through a short pad of Celite. The filtrate was concentrated to dryness to give a yellow oil. The oil was dissolved in DCM (5 ml) and cooled to 0° C. mCPBA (70%, 492 mg, 2.0 mmol) was added. The resulting mixture was stirred at 0° C. for 1 h and then quenched with Na₂S₂O₃ (10%, 5 ml) and NaHCO₃ (sat., 5 ml) and the layers were separated. The organics were dried over Na₂SO₄, concentrated and purified by flash chromatography eluting with hexanes to give the desired product (297 mg, 1.32 mmol, 66%) as a colorless oil. ¹H NMR (400 MHz, (CDCl₃) δ 7.30 (d, J=7.6 Hz, 1H), 7.11 (d, J=7.6 Hz, 1H), 6.97 (t, J=7.6 Hz, 1H), 2.87 (t, J=7.4 Hz, 2H), 1.94 (d, J=7.4 Hz, 2H), 1.42 (s, 6H).

Step B. 2-(3,3-dimethyl-2,3-dihydro-1H-inden-4-yl)-4,4,5,5-tetramethyl-1,3,2-dioxaborolane. To a solution of 7-bromo-1,1-dimethyl-2,3-dihydro-1H-indene (280 mg, 1.24 mmol) in THF (20 ml) at −70° C. was added butyllithium (0.75 ml, 1.87 mmol). The reaction was stirred at −70° C. for 1 h. 2-isopropoxy-4,4,5,5-tetramethyl-1,3,2-dioxaborolane (0.38 ml, 1.87 mmol) was then added to the mixture. The cold bath was removed, and the reaction was warmed to rt and stirred at rt for additional 2 h. The reaction was quenched with NH₄Cl (sat.) and extracted with EtOAc. The organic solution was dried over Na₂SO₄, concentrated and purified by flash chromatography eluting with 0-100% EtOAc/hexanes to give the desired product (380 mg, 1.40 mmol, 112%) as a colorless oil. ¹H NMR (400 MHz, (CDCl₃) δ 7.55 (d, J=7.2 Hz, 1H), 7.23 (d, J=7.2 Hz, 1H), 7.11 (t, J=7.2 Hz, 1H), 2.85 (t, J=7.6 Hz, 2H), 1.88 (d, J=7.6 Hz, 2H), 1.40 (s, 6H), 1.35 (s, 12H).

Step C. tert-butyl (1R,5S)-3-(7-(3,3-dimethyl-2,3-dihydro-1H-inden-4-yl)-8-fluoro-2-(((S)-1-methylpyrrolidin-2-yl)methoxy)pyrido[4,3-d]pyrimidin-4-yl)-3,8-diazabicyclo[3.2.1]octane-8-carboxylate 2,2,2-trifluoroacetate. To a vial containing a mixture of tert-butyl (1R,5S)-3-(7-chloro-8-fluoro-2-(((S)-1-methylpyrrolidin-2-yl)methoxy)pyrido[4,3-d]pyrimidin-4-yl)-3,8-diazabicyclo[3.2.1]octane-8-carboxylate (synthesized according to Example 3, Step A-G substituting (S)-(1-methyl-1H-imidazol-2-yl)ethan-1-ol in place of 2-(1-methyl-1H-imidazol-2-yl)ethan-1-ol) (50 mg, 0.098 mmol), K₃PO₄ (42 mg, 0.20 mmol), Pd₂(dba)₃ (14 mg, 0.015 mmol) and S-Phos (12 mg, 0.030 mmol) was added a solution of 2-(3,3-dimethyl-2,3-dihydro-1H-inden-4-yl)-4,4,5,5-tetramethyl-1,3,2-dioxaborolane (54 mg, 0.20 mmol) in 2-methylbutan-2-ol (1.0 ml). The vial was purged with N2, sealed with a cap and heated at 90° C. for 15 h. The mixture was cooled to rt and was purified by preparative C18 HPLC (Gilson, 0-95% CH₃CN/H₂O with 0.1% TFA). The desired fractions were combined and concentrated to give the desired product (11 mg, 0.015 mmol, 15%) as a yellow solid. LCMS (MM-ES+APCI, Pos): m/z 617.4 (M+H).

Step D. 4-((1R,5S)-3,8-diazabicyclo[3.2.1]octan-3-yl)-7-(3,3-dimethyl-2,3-dihydro-1H-inden-4-yl)-8-fluoro-2-(((S)-1-methylpyrrolidin-2-yl)methoxy)pyrido[4,3-d]pyrimidine bis(2,2,2-trifluoroacetate). To a solution of tert-butyl (1R,5S)-3-(7-(3,3-dimethyl-2,3-dihydro-1H-inden-4-yl)-8-fluoro-2-(((S)-1-methylpyrrolidin-2-yl)methoxy)pyrido[4,3-d]pyrimidin-4-yl)-3,8-diazabicyclo[3.2.1]octane-8-carboxylate (11 mg, 0.018 mmol) in DCM (1.0 ml) was added TFA (0.30 ml). The solution was stirred at rt for 1 h and was concentrated to dryness. The residue was purified by preparative C18 HPLC (Gilson, 0-95% CH₃CN/H₂O with 0.1% TFA). The desired fractions were combined and concentrated to give the title compound (8 mg, 0.015 mmol, 87%) as a yellow material. LCMS (MM-ES+APCI, Pos): m/z 517.3 (M+H).

Example 162

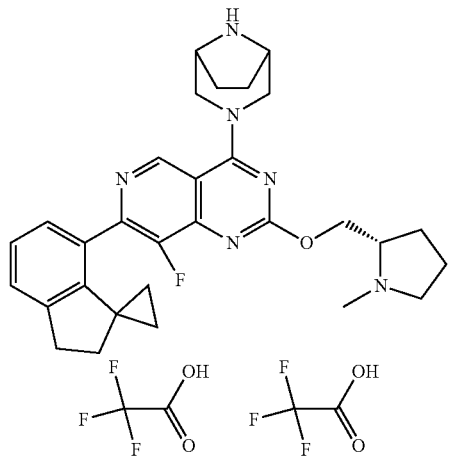

4-((1R,5S)-3,8-diazabicyclo[3.2.1]octan-3-yl)-7-(2',3'-dihydrospiro[cyclopropane-1,1'-inden]-7'-yl)-8-fluoro-2-(((S)-1-methylpyrrolidin-2-yl)methoxy)pyrido[4,3-d]pyrimidine bis(2,2,2-trifluoroacetate)

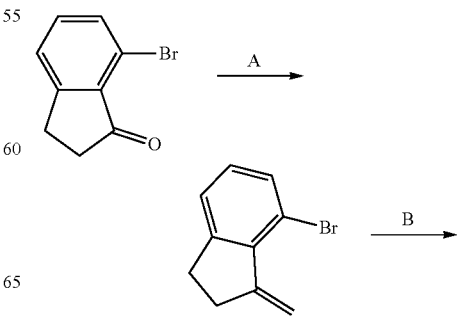

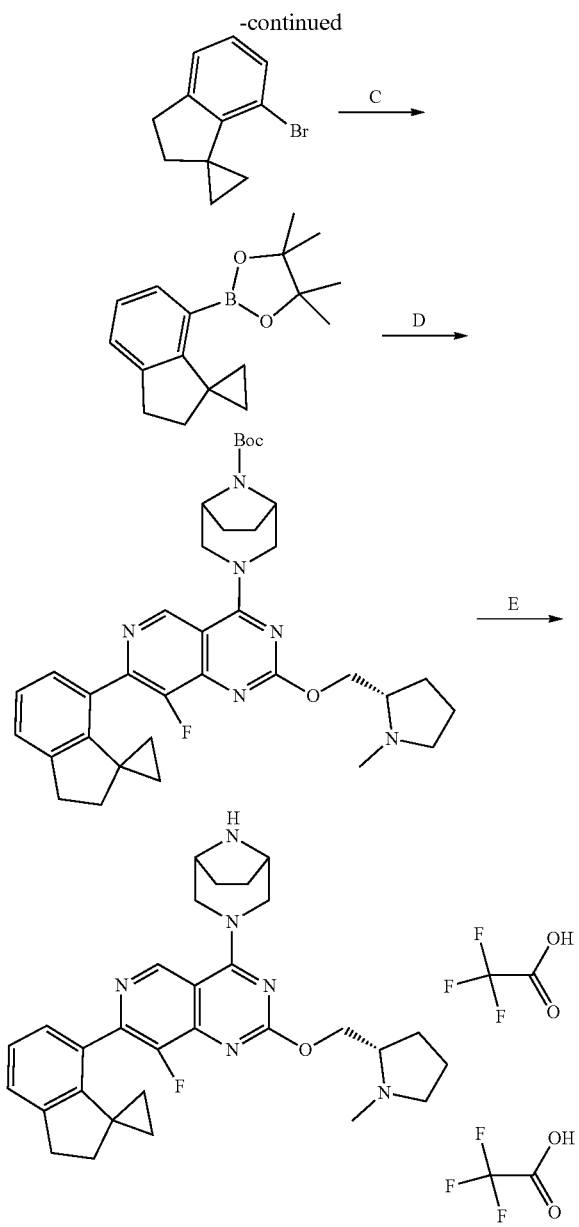

Step A. 7-bromo-1-methylene-2,3-dihydro-1H-indene. To a suspension of Methyltriphenylphosphonium bromide (1.32 g, 3.70 mmol) in tetrahydrofuran (28.4 ml) was added potassium 2-methylpropan-2-olate (3.70 ml, 3.70 mmol) and the reaction was stirred for 1 h to give a yellow suspension. 7-Bromo-2,3-dihydro-1H-inden-1-one (0.60 g, 2.84 mmol) was added to the mixture and it was stirred at rt for 2 h to give a grey suspension. The mixture was quenched with NH$_4$Cl (sat.) and extracted with hexanes. The extract was dried over Na$_2$SO$_4$, concentrated and purified by flash chromatography eluting with 0-10% EtOAc/hexanes to give the desired product (528 mg, 2.53 mmol, 89%) as a light yellow oil. $^1$H NMR (400 MHz, (CDCl$_3$) δ 7.39 (d, J=7.2 Hz, 1H), 7.20 (d, J=7.2 Hz, 1H), 7.02 (t, J=7.2 Hz, 1H), 6.24 (m, 1H), 5.22 (m, 1H), 2.95 (m, 2H), 2.83 (m, 2H).

Step B. 7'-bromo-2',3'-dihydrospiro[cyclopropane-1,1'-indene. To a solution of DCM (6.2 ml) at 0° C. under N$_2$ was added a solution of diethylzinc (5.0 ml, 4.97 mmol) in hexanes. The solution was stirred at 0° C. for 5 min and a solution of TFA (0.38 ml, 4.97 mmol) in DCM (2.5 ml) was added dropwise. After addition, the solution was continued to stir at 0° C. for 20 min before introducing a solution of diiodomethane (0.40 ml, 4.97 mmol) in DCM (2.5 ml). The resulting mixture was stirred at 0° C. for 20 min then a solution of 7-bromo-1-methylene-2,3-dihydro-1H-indene (520 mg, 2.49 mmol) in DCM (2.5 ml) was added. The mixture was warmed to rt and continued to stir at rt for 1 h. The mixture was then quenched with HCl (1.0 M, 5 ml, 5.0 mmol) and water (5 ml). The mixture was stirred at rt for 3 min and the two layers were separated. The organic layer was dried over Na$_2$SO$_4$, concentrated and purified by flash chromatography eluting with hexanes to give the desired product (485 mg, 2.17 mmol, 87%) as a colorless oil. 1H NMR (400 MHz, (CDCl$_3$) δ 7.22 (m, 1H), 7.11 (m, 1H), 6.92 (m, 1H), 2.98 (t, J=7.6 Hz, 2H), 2.07 (t, J=7.6 Hz, 1H), 1.78 (dd, J=4.4 Hz, 6.4 Hz, 2H), 0.74 (dd, J=4.4 Hz, 6.4 Hz, 2H).

Step C. 2-(2',3'-dihydrospiro[cyclopropane-1,1'-inden]-7'-yl)-4,4,5,5-tetramethyl-1,3,2-dioxaborolane. To a solution of 7'-bromo-2',3'-dihydrospiro[cyclopropane-1,1'-indene] (485 mg, 2.17 mmol) in dioxane (11 ml) were added potassium acetate (640 mg, 6.52 mmol), 4,4,4',4',5,5,5',5'-octamethyl-2,2'-bi(1,3,2-dioxaborolane) (1.66 g, 6.52 mmol) and PdCl$_2$(dppf) (159 mg, 0.22 mmol). The mixture was flushed with N2 for 1 minute, closed with a cap and heated at 100° C. for 7 h. The mixture was cooled to rt, diluted with EtOAc and washed with NaHSO$_4$ (10%, 10 ml). The organic solution was dried over Na$_2$SO$_4$ and purified by flash chromatography eluting with 0-100% EtOAc/hexanes to the desired product (160 mg, 0.59 mol, 27%) a light-yellow oil. $^1$H NMR (400 MHz, (CDCl$_3$) δ 7.46 (m, 1H), 7.23 (m, 1H), 7.07 (m, 1H), 2.97 (t, J=7.6 Hz, 2H), 2.03 (t, J=7.6 Hz, 1H), 1.46 (dd, J=4.4 Hz, 6.4 Hz, 2H), 0.81 (dd, J=4.4 Hz, 6.4 Hz, 2H).

Step D. tert-butyl (1R,5S)-3-(7-(2',3'-dihydrospiro[cyclopropane-1,1'-inden]-7'-yl)-8-fluoro-2-(((S)-1-methylpyrrolidin-2-yl)methoxy)pyrido[4,3-d]pyrimidin-4-yl)-3,8-diazabicyclo[3.2.1]octane-8-carboxylate. To a mixture of tert-butyl (1R,5S)-3-(7-chloro-8-fluoro-2-(((S)-1-methylpyrrolidin-2-yl)methoxy)pyrido[4,3-d]pyrimidin-4-yl)-3,8-diazabicyclo[3.2.1]octane-8-carboxylate (synthesized according to Example 3, Step A-G substituting (S)-(1-methylpyrrolidin-2-yl)methanol in place of 2-(1-methyl-1H-imidazol-2-yl)ethan-1-ol) (50 mg, 0.099 mmol), K$_3$PO$_4$ (42 mg, 0.20 mmol), Pd$_2$(dba)$_3$ (14 mg, 0.015 mmol) and S-Phos (12 mg, 0.030 mmol) was added a solution of 2-(2',3'-dihydrospiro[cyclopropane-1,1'-inden]-7'-yl)-4,4,5,5-tetramethyl-1,3,2-dioxaborolane (53 mg, 0.20 mmol) in 2-methylbutan-2-ol (0.99 ml). The vial was purged with N2, sealed with a vial and heated at 100° C. for 20 h. The mixture was cooled to rt and was purified by preparative C18 HPLC (Gilson, 0-95% CH$_3$CN/H$_2$O with 0.1% TFA). The desired fractions were combined and concentrated. The remaining solution was quenched with NaHCO$_3$(Sat.) and extracted with DCM. The DCM extract was dried over Na$_2$SO$_4$ and concentrated to give the desired product (12 mg, 0.020 mmol, 20%) as a light-yellow solid. LCMS (MM-ES+APCI, Pos): m/z 615.3 (M+H).

Step E. 4-((1R,5S)-3,8-diazabicyclo[3.2.1]octan-3-yl)-7-(2',3'-dihydrospiro[cyclopropane-1,1'-inden]-7'-yl)-8-fluoro-2-(((S)-1-methylpyrrolidin-2-yl)methoxy)pyrido[4,3-d]pyrimidine bis(2,2,2-trifluoroacetate). To a solution of tert-butyl (1R,5S)-3-(7-(2',3'-dihydrospiro[cyclopropane-1,1'-inden]-7'-yl)-8-fluoro-2-(((S)-1-methylpyrrolidin-2-yl)methoxy)pyrido[4,3-d]pyrimidin-4-yl)-3,8-diazabicyclo[3.2.1]octane-8-carboxylate (12 mg, 0.020 mmol) in DCM (1.2 ml) was added TFA (0.3 ml). The mixture was stirred at rt for 1.5 h and concentrated to dryness. The residue was purified by preparative C18 HPLC (Gilson, 0-95% CH₃CN/H₂O with 0.1% TFA). The desired fractions were combined and concentrated to give the title compound (10 mg, 0.013 mmol, 69%) as an off-white solid. LCMS (MM-ES+APCI, Pos): m/z 515.3 (M+H).

Example 163

-continued

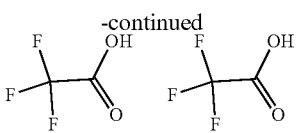

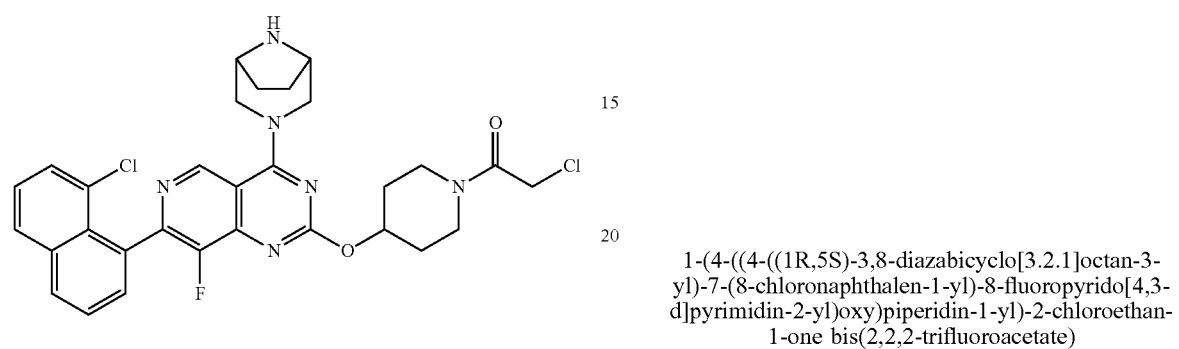

1-(4-((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)piperidin-1-yl)-2-chloroethan-1-one bis(2,2,2-trifluoroacetate)

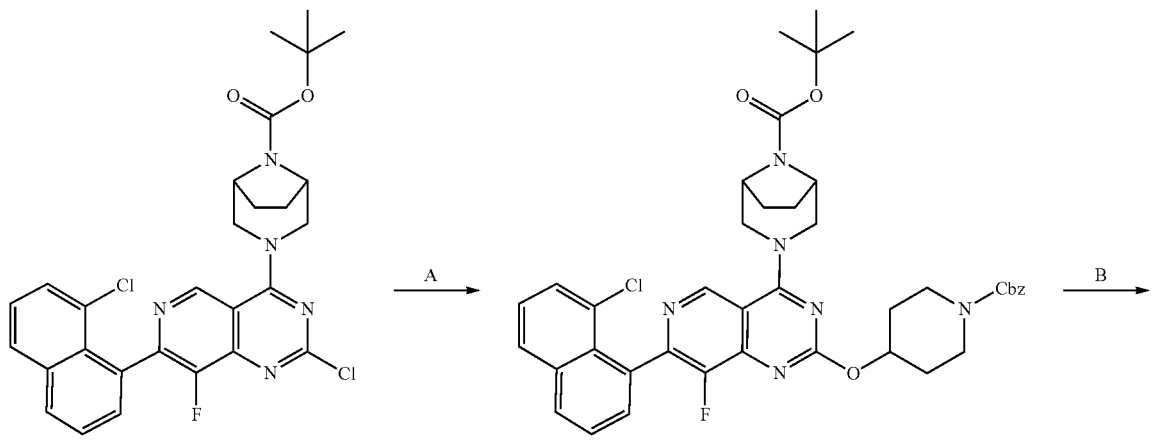

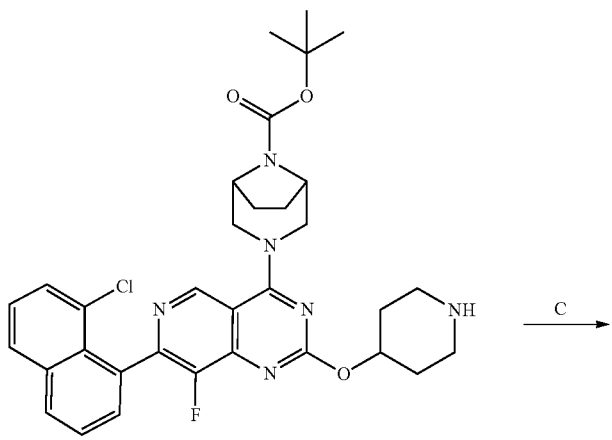

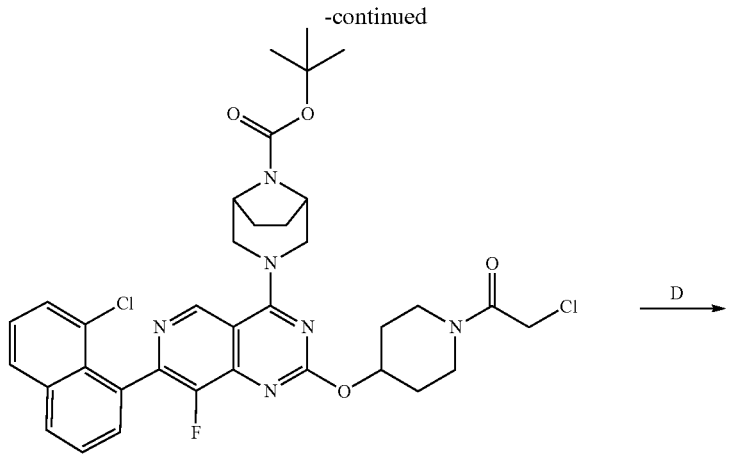

Step A. tert-butyl (1R,5S)-3-(2-((1-((benzyloxy)carbonyl)piperidin-4-yl)oxy)-7-(8-chloronaphthalen-1-yl)-8-fluoropyrido[4,3-d]pyrimidin-4-yl)-3,8-diazabicyclo[3.2.1]octane-8-carboxylate. To a solution of tert-butyl (1R,5S)-3-(2-chloro-7-(8-chloronaphthalen-1-yl)-8-fluoropyrido[4,3-d]pyrimidin-4-yl)-3,8-diazabicyclo[3.2.1]octane-8-carboxylate (100 mg, 0.18 mmol) and benzyl 4-hydroxypiperidine-1-carboxylate (84.9 mg, 0.36 mmol) in 1,4-dioxane (3.6 ml) was added $Cs_2CO_3$ (118 mg, 0.36 mmol). The mixture was stirred at 80° C. for 16 h and then at 100° C. for 24 h. The mixture was cooled and partitioned between brine and EtOAc. The EtOAc layer was dried over $Na_2SO_4$, and concentrated. The residue purified by flash chromatography eluting with a 0-100 EtOAc/hexanes gradient. The desired fractions were combined and concentrated to give the title product (114 mg, 0.15 mmol, 84%) as a colorless oil. LCMS (MM-ES+APCI, Pos): m/z 754.3 (M+H).

Step B. tert-butyl (1R,5S)-3-(7-(8-chloronaphthalen-1-yl)-8-fluoro-2-(piperidin-4-yloxy)pyrido[4,3-d]pyrimidin-4-yl)-3,8-diazabicyclo[3.2.1]octane-8-carboxylate. A mixture of tert-butyl (1R,5S)-3-(2-((1-((benzyloxy)carbonyl)piperidin-4-yl)oxy)-7-(8-chloronaphthalen-1-yl)-8-fluoropyrido[4,3-d]pyrimidin-4-yl)-3,8-diazabicyclo[3.2.1]octane-8-carboxylate (110 mg, 0.15 mmol), Pd—C (7.8 mg, 0.0073 mmol) and EtOH (2.9 ml) was stirred under a balloon of H2 at rt for 6 h and Celite was added to the mixture. The mixture was filtered through a short pad of Celite and extracted with MeOH (5 ml). The filtrate was concentrated to give the crude desired product (70 mg, 0.11 mmol, 77%) as a white foam. LCMS (MM-ES+APCI, Pos): m/z 619.3 (100%), 621.3 (50%) (M+H, M+3).

Step C. tert-butyl (1R,5S)-3-(2-((1-(2-chloroacetyl)piperidin-4-yl)oxy)-7-(8-chloronaphthalen-1-yl)-8-fluoropyrido[4,3-d]pyrimidin-4-yl)-3,8-diazabicyclo[3.2.1]octane-8-carboxylate. To a solution of tert-butyl (1R,5S)-3-(7-(8-chloronaphthalen-1-yl)-8-fluoro-2-(piperidin-4-yloxy)pyrido[4,3-d]pyrimidin-4-yl)-3,8-diazabicyclo[3.2.1]octane-8-carboxylate (31 mg, 0.0501 mmol) in DCM (1.0 ml) at 0° C. was added $Et_3N$ (21 µL, 0.15 mmol), followed by chloroacetyl chloride (12 µL, 0.15 mmol). The mixture was stirred at 0° C. for 20 min and quenched with $NaHCO_3$ (Sat. solution). The mixture was extracted with DCM. The extract was dried over $Na_2SO_4$, concentrated and purified by flash chromatography eluting with a 0-100 EtOAc/hexanes gradient. The desired fractions were combined and concentrated to give the title product (13 mg, 0.019 mmol, 37%) as a white solid. LCMS (MM-ES+APCI, Pos): m/z 695.2 (100%), 697.3 (50%) (M+H, M+3).

Step D. 1-(4-((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)piperidin-1-yl)-2-chloroethan-1-one bis(2,2,2-trifluoroacetate). To a solution of tert-butyl (1R,5S)-3-(2-((1-(2-chloroacetyl)piperidin-4-yl)oxy)-7-(8-chloronaphthalen-1-yl)-8-fluoropyrido[4,3-d]pyrimidin-4-yl)-3,8-diazabicyclo[3.2.1]octane-8-carboxylate (13 mg, 0.019 mmol) in DCM (1.0 ml) was added TFA (1.0 ml). The mixture was stirred at rt for 1 h and concentrated to dryness. The residue was dissolved in DCM (1 ml), followed by addition of hexanes (1 ml). The resulting suspension was concentrated and dried to give the title compound (15 mg, 0.018 mmol, 97%) as a light-yellow solid. Note: the crude product contained about 2:1 ratio of the desired product and the Des-Cl product. LCMS (MM-ES+APCI, Pos): m/z 595.2 (100%), 597.2 (50%) (M+H, M+3).

347
Example 164
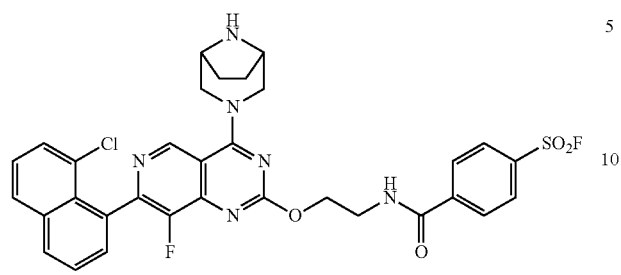
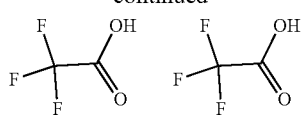
4-((2-((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)ethyl)carbamoyl)benzene-sulfonyl fluoride bis(2,2,2-trifluoroacetate)
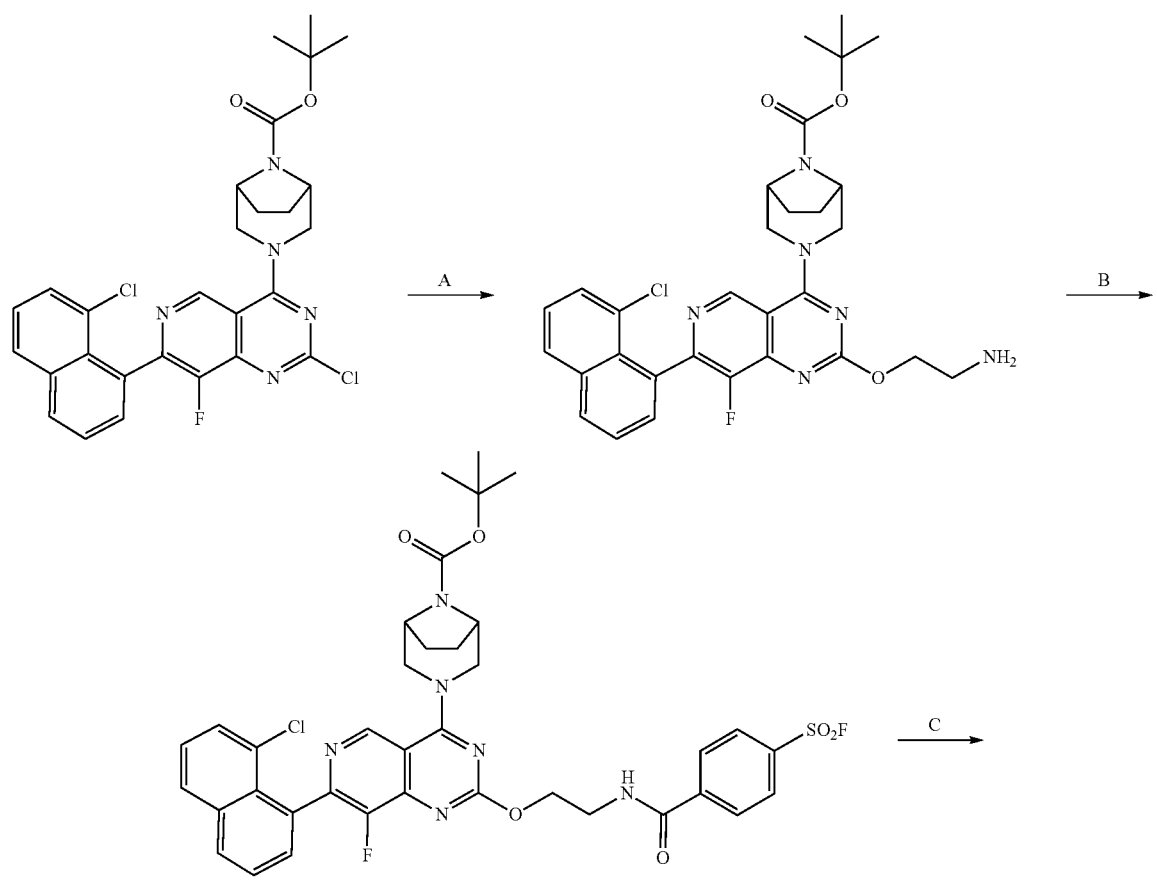
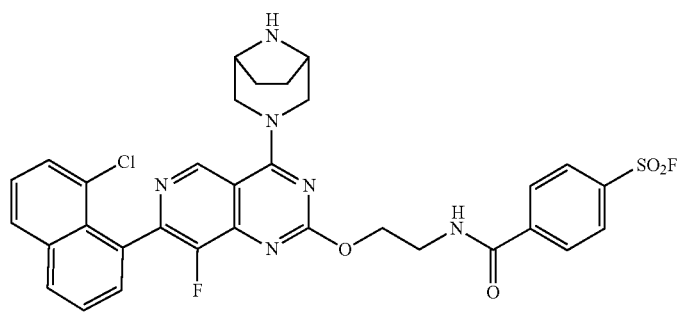
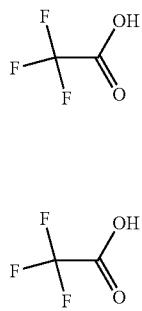

Step A. tert-butyl (1R,5S)-3-(2-(2-aminoethoxy)-7-(8-chloronaphthalen-1-yl)-8-fluoropyrido[4,3-d]pyrimidin-4-yl)-3,8-diazabicyclo[3.2.1]octane-8-carboxylate. To a suspension of NaH (40 mg, 1.0 mmol) in THF (2.0 ml) at 0° C. was added 2-aminoethan-1-ol (60 µL, 1.0 mmol). The mixture was stirred at 0° C. for 10 min and cooled to −10° C. Then, tert-butyl (1R,5S)-3-(2-chloro-7-(8-chloronaphthalen-1-yl)-8-fluoropyrido[4,3-d]pyrimidin-4-yl)-3,8-diazabicyclo[3.2.1]octane-8-carboxylate (111 mg, 0.20 mmol) was added. The resulting mixture was stirred between −10° C. and −5° C. for 1 h and quenched with NH$_4$Cl (sat.). The mixture was concentrated and was purified by preparative C18 HPLC (Gilson, 0-95% CH$_3$CN/H$_2$O with 0.1% TFA). The desired fractions were combined and concentrated. The residue was dissolved in DCM and hexanes and concentrated to give the title product (68 mg, 0.12 mmol, 59%) as a white solid. LCMS (MM-ES+APCI, Pos): m/z 579.3 (100%), 581.2 (50%) (M+H, M+3).

Step B. tert-butyl (1R,5S)-3-(7-(8-chloronaphthalen-1-yl)-8-fluoro-2-(2-(4-(fluorosulfonyl)-benzamido)ethoxy)pyrido[4,3-d]pyrimidin-4-yl)-3,8-diazabicyclo[3.2.1]octane-8-carboxylate. To a suspension of 4-(fluorosulfonyl)benzoyl chloride (15 mg, 0.059 mmol) in DCM (0.98 ml) at 0° C. was added tert-butyl (1R,5S)-3-(2-(2-aminoethoxy)-7-(8-chloronaphthalen-1-yl)-8-fluoropyrido[4,3-d]pyrimidin-4-yl)-3,8-diazabicyclo[3.2.1]octane-8-carboxylate (17 mg, 0.029 mmol), followed by Et$_3$N (8 µL, 0.059 mmol). The solution was stirred at 0° C. for 30 min and quenched with NaHCO$_3$ (sat. solution). The organic layer was collected, concentrated and purified by flash chromatography eluting with a 0-100 EtOAc/hexanes gradient. The desired fractions were combined and concentrated to give the title product (13 mg, 0.017 mmol, 58%) as a white solid. LCMS (MM-ES+APCI, Pos): m/z 765.2 (100%), 767.2 (50%) (M+H, M+3).

Step C. 4-((2-((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)ethyl)carbamoyl)benzenesulfonyl fluoride bis(2,2,2-trifluoroacetate). To a solution of tert-butyl (1R,5S)-3-(7-(8-chloronaphthalen-1-yl)-8-fluoro-2-(2-(4-(fluorosulfonyl)benzamido)ethoxy)pyrido[4,3-d]pyrimidin-4-yl)-3,8-diazabicyclo[3.2.1]octane-8-carboxylate (13 mg, 0.017 mmol) in DCM (1.0 ml) was added TFA (1.0 ml). The solution was stirred at rt for 1 h and concentrated to dryness. The residue was dissolved in DCM and transferred into a vial containing hexanes. The suspension was concentrated to dryness to give the crude title compound (16 mg, 0.018 mmol, 105%) as a white solid. LCMS (MM-ES+APCI, Pos): m/z 665.2 (100%), 667.1 (50%) (M+H, M+3).

Example 165

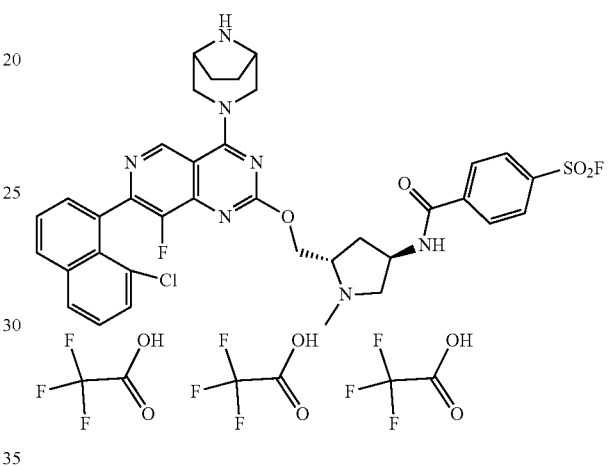

4-(((3R,5S)-5-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)-1-methylpyrrolidin-3-yl)carbamoyl)benzenesulfonyl fluoride tris(2,2,2-trifluoroacetate)

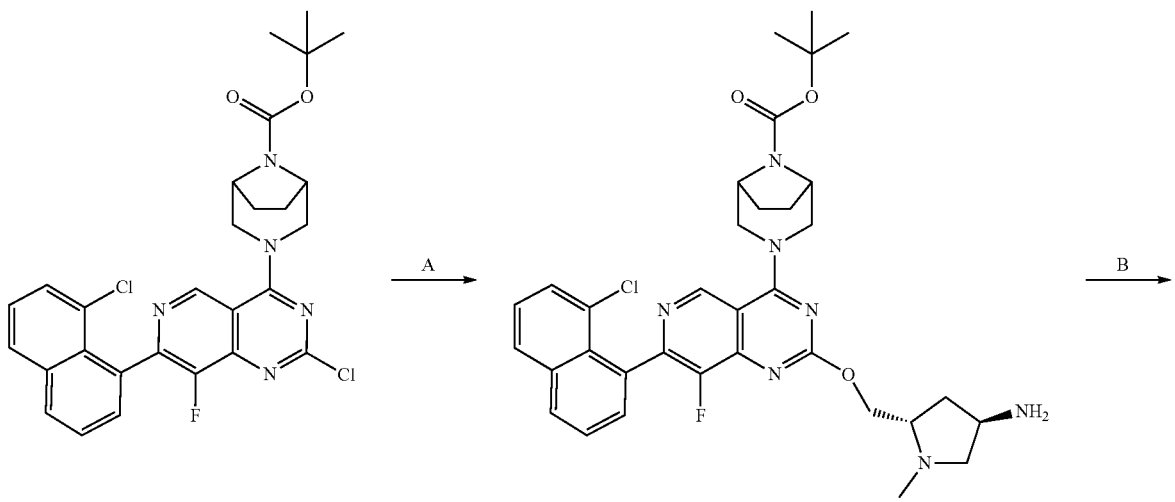

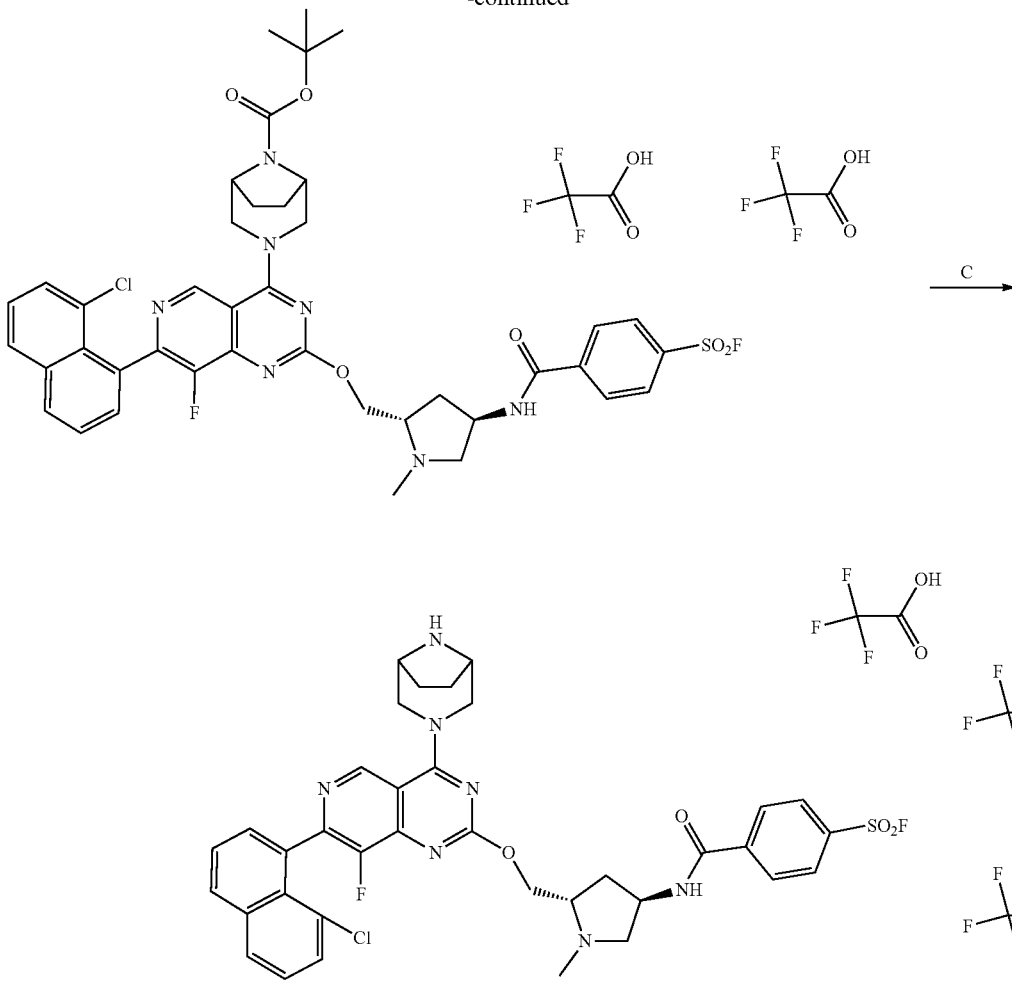

Step A. tert-butyl (1R,5S)-3-(2-(((2S,4R)-4-amino-1-methylpyrrolidin-2-yl)methoxy)-7-(8-chloronaphthalen-1-yl)-8-fluoropyrido[4,3-d]pyrimidin-4-yl)-3,8-diazabicyclo[3.2.1]octane-8-carboxylate. To a solution of tert-butyl (1R,5S)-3-(2-chloro-7-(8-chloronaphthalen-1-yl)-8-fluoropyrido[4,3-d]pyrimidin-4-yl)-3,8-diazabicyclo[3.2.1]octane-8-carboxylate (248 mg, 0.45 mmol) in DMF (4.5 ml) at −10° C. was added NaH (48 mg, 1.2 mmol), followed by addition of ((2S,4R)-4-amino-1-methylpyrrolidin-2-yl)methanol (64.1 mg, 0.492 mmol). The mixture was stirred at 0° C. for 15 h. The mixture was purified by preparative C18 HPLC (Gilson, 0-95% CH$_3$CN/H$_2$O with 0.1% TFA). The desired fractions were combined, basified with NaHCO$_3$ (Sat.) and extracted with DCM/IPA (10.1). The combined extracts were dried over Na$_2$SO$_4$ and concentrated to give the title product (72 mg, 0.11 mmol, 25%) as an off-white solid. LCMS (MM-ES+APCI, Pos): m/z 648.3 (100%), 650.3 (50%) (M+H, M+3).

Step B. tert-butyl (1R,5S)-3-(7-(8-chloronaphthalen-1-yl)-8-fluoro-2-(((2S,4R)-4-(4-(fluorosulfonyl)benzamido)-1-methylpyrrolidin-2-yl)methoxy)pyrido[4,3-d]pyrimidin-4-yl)-3,8-diazabicyclo[3.2.1]octane-8-carboxylate bis(2,2,2-trifluoroacetate). To a solution of tert-butyl (1R,5S)-3-(2-(((2S,4R)-4-amino-1-methylpyrrolidin-2-yl)methoxy)-7-(8-chloronaphthalen-1-yl)-8-fluoropyrido[4,3-d]pyrimidin-4-yl)-3,8-diazabicyclo[3.2.1]octane-8-carboxylate (22 mg, 0.034 mmol) in DCM (1.1 ml) at 0° C. was added Et$_3$N (9.5 µL, 0.068 mmol), followed by 4-(fluorosulfonyl)benzoyl chloride (17 mg, 0.068 mmol). The mixture was stirred at 0° C. for 0.5 h and was concentrated to dryness. The residue was purified by preparative C18 HPLC (Gilson, 0-95% CH$_3$CN/H$_2$O with 0.1% TFA). The desired fractions were combined and lyophilized to give the desired product (30 mg, 0.028 mmol, 83% yield) as a white solid.

Step C. 4-(((3R,5S)-5-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)-1-methylpyrrolidin-3-yl)carbamoyl)benzenesulfonyl fluoride tris(2,2,2-trifluoroacetate). To a solution of tert-butyl (1R,5S)-3-(7-(8-chloronaphthalen-1-yl)-8-fluoro-2-(((2S,4R)-4-(4-(fluorosulfonyl)benzamido)-1-methylpyrrolidin-2-yl)methoxy)pyrido[4,3-d]pyrimidin-4-yl)-3,8-diazabicyclo[3.2.1]octane-8-carboxylate (25 mg, 0.02354 mmol) in dichloromethane (0.95 ml, 0.024 mmol) was added 2,2,2-trifluoroacetic acid (0.47 ml). The solution was stirred at rt for 0.5 h and concentrated to dryness to give the title compound (26 mg, 0.024 mmol, 103% yield) as a white solid. LCMS (MM-ES+APCI, Pos): m/z 734.2 (100%), 736.2 (50%) (M+H, M+3).

Example 166

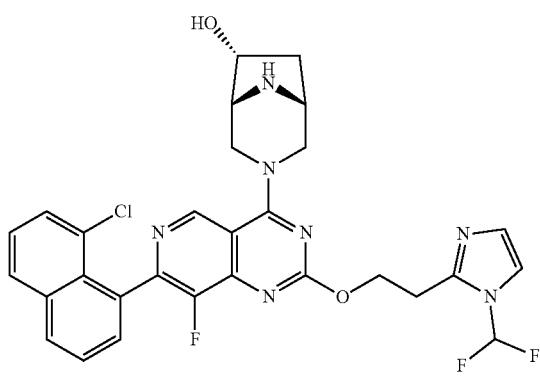 [SMILES: O[C@@H]1C[C@@H]2CN(c3nc(OCCc4nccn4C(F)F)nc4c(F)c(-c5cccc6cccc(Cl)c56)ncc34)C[C@H]1N2]

(1R,5R,6R)-3-(7-(8-chloronaphthalen-1-yl)-2-(2-(1-(difluoromethyl)-1H-imidazol-2-yl)ethoxy)-8-fluoro-pyrido[4,3-d]pyrimidin-4-yl)-3,8-diazabicyclo[3.2.1]octan-6-ol

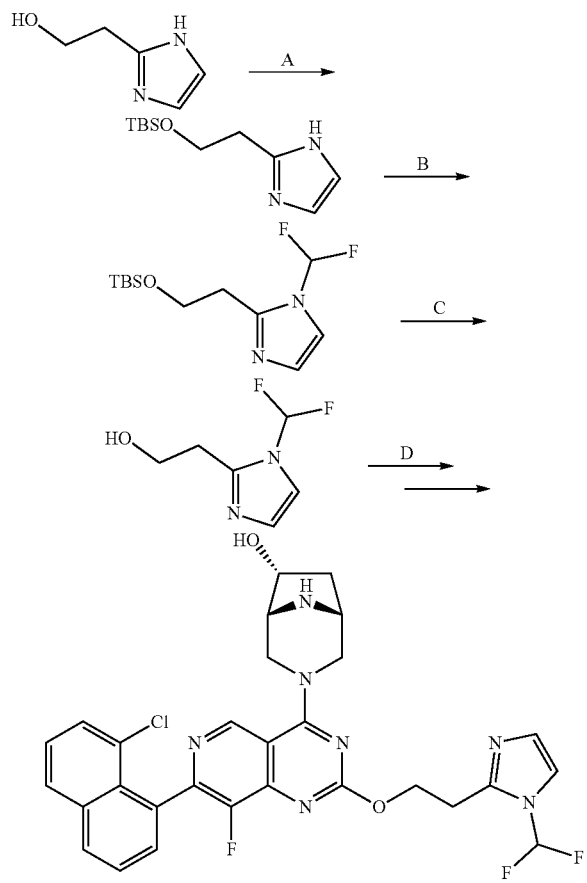

Step A: 2-(2-((tert-butyldimethylsilyl)oxy)ethyl)-1H-imidazole. To 2-(1H-imidazol-2-yl)ethan-1-ol (1.00 g, 8.92 mmol) in DMF (10 mL) was added 1H-imidazole (3.04 g, 44.6 mmol) and tert-butylchlorodimethylsilane (1.48 g, 9.81 mmol). The reaction was stirred at rt for 18 hours. The mixture was diluted with EtOAc (50 mL) and washed with water and brine. The mixture was dried over $Na_2SO_4$, concentrated and purified by flash chromatography using 0-100% EtOAc in hexanes as eluent to provide product (1.81 g, 7.97 mmol, 89%). LCMS (MM-ES+APCI, Pos): m/z 227.1 (M+H).

Step B: 2-(2-((tert-butyldimethylsilyl)oxy)ethyl)-1-(difluoromethyl)-1H-imidazole. To 2-(2-((tert-butyldimethylsilyl)oxy)ethyl)-1H-imidazole (1.00 g, 4.42 mmol) in DMF (20 mL) was added sodium hydride (0.265 g, 6.63 mmol). The mixture was stirred for 30 minutes. Chlorodifluoromethane (0.420 g, 4.86 mmol) was then bubbled through the reaction mixture for 5 minutes. The reaction was then sealed and stirred at 50° C. for 3 hours. The mixture was diluted with EtOAc (50 mL), washed with water, brine, dried over $Na_2SO_4$ and concentrated. The material was purified by flash chromatography using 0 to 100% EtOAc in hexanes as eluent to provide product (380 mg, 1.37 mmol, 32%). LCMS (MM-ES+APCI, Pos): m/z 277.1 (M+H)

Step C: 2-(1-(difluoromethyl)-1H-imidazol-2-yl)ethan-1-ol. To 2-(2-((tert-butyldimethylsilyl)oxy)ethyl)-1-(difluoromethyl)-1H-imidazole (380 mg, 1.37 mmol) in THF (15 mL) at 0° C. was added TBAF (2 ml, 2.06 mmol). The cold bath was removed, and the reaction was stirred at rt for 2 hours. The mix was diluted with EtOAc (50 mL) and washed with water, brine, dried over $Na_2SO_4$ and concentrated. The material was purified by flash chromatography using 0 to 100% EtOAc in hexanes as eluent to provide product (180 mg, 1.1 mmol, 81%). LCMS (MM-ES+APCI, Pos): m/z 163.2 (M+H).

Step D: (1R,5R,6R)-3-(7-(8-chloronaphthalen-1-yl)-2-(2-(1-(difluoromethyl)-1H-imidazol-2-yl)ethoxy)-8-fluoro-pyrido[4,3-d]pyrimidin-4-yl)-3,8-diazabicyclo[3.2.1]octan-6-ol. Synthesized according to Example 32 substituting 2-(1-(difluoromethyl)-1H-imidazol-2-yl)ethan-1-ol in place of 2-(5-fluoropyridin-2-yl)ethan-1-ol in Step B (15 mg, 0.024 mmol, 65% yield). LCMS (MM-ES+APCI, Pos): m/z 596.2 (M+H).

Example 167

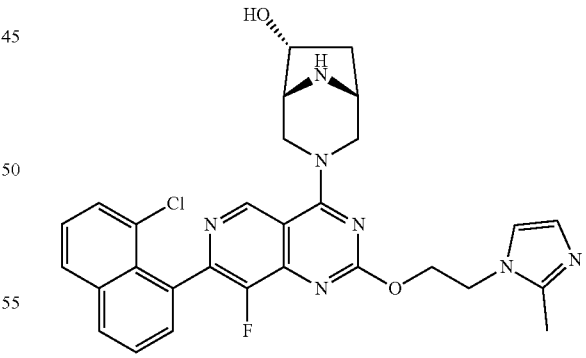

(1R,5R,6R)-3-(7-(8-chloronaphthalen-1-yl)-8-fluoro-2-(2-(2-methyl-1H-imidazol-1-yl)ethoxy)pyrido[4,3-d]pyrimidin-4-yl)-3,8-diazabicyclo[3.2.1]octan-6-ol Synthesized according to Example 32 substituting 2-(1-methyl-1H-imidazol-2-yl)ethan-1-ol in place of 2-(5-fluoropyridin-2-yl)ethan-1-ol in Step B (10 mg, 0.017 mmol, 53% yield). LCMS (MM-ES+APCI, Pos): m/z 560.1 (M+).

Example 168

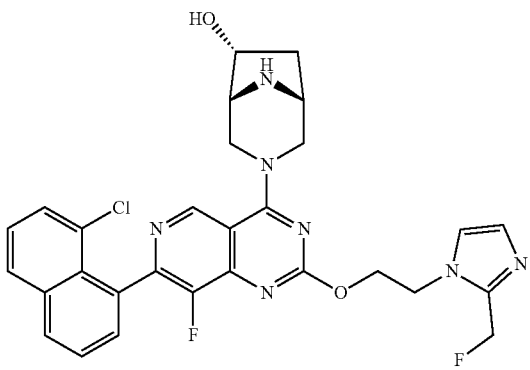 [SMILES: O[C@@H]1C[C@@H]2CN(c3nc(OCCn4ccnc4CF)nc4c(F)c(-c5cccc6cccc(Cl)c56)ncc34)C[C@H]1N2]

(1R,5R,6R)-3-(7-(8-chloronaphthalen-1-yl)-8-fluoro-2-(2-(2-(fluoromethyl)-1H-imidazol-1-yl)ethoxy)pyrido[4,3-d]pyrimidin-4-yl)-3,8-diazabicyclo[3.2.1]octan-6-ol

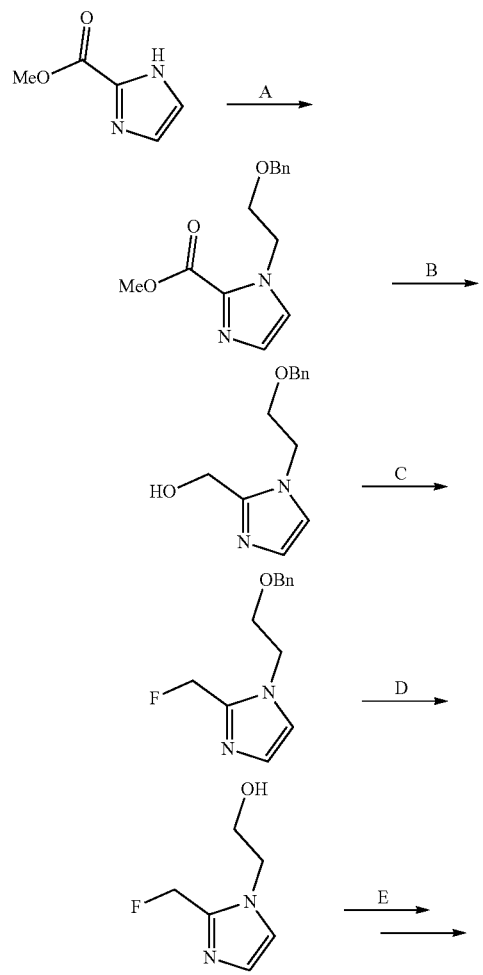

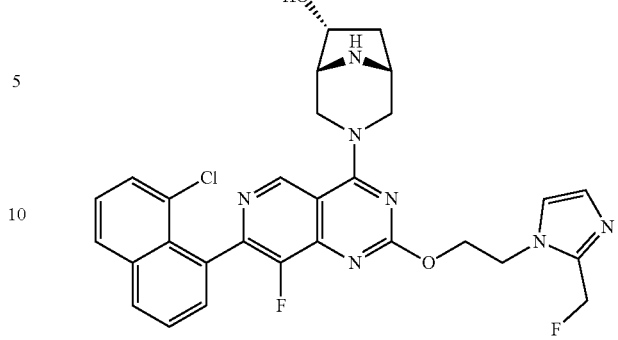

Step A: methyl 1-(2-(benzyloxy)ethyl)-1H-imidazole-2-carboxylate. To methyl 1H-imidazole-2-carboxylate (2.87 g, 22.8 mmol) in DMF (30 mL) were added $K_2CO_3$ (4.72 g, 34.1 mmol) and ((2-bromoethoxy)methyl)benzene (3.96 ml, 25.0 mmol). The reaction was heated at 80° C. for 3 hours. The mixture was diluted with EtOAc (200 mL), washed with water and brine, dried over $Na_2SO_4$ and concentrated. The residue was purified by flash chromatography using 0 to 100% EtOAc in hexanes as eluent to give product (3.91 g, 15.0 mmol, 66%). LCMS (MM-ES+APCI, Pos): m/z 261.1 (M+H).

Step B: (1-(2-(benzyloxy)ethyl)-1H-imidazol-2-yl)methanol. To methyl 1-(2-(benzyloxy)ethyl)-1H-imidazole-2-carboxylate (3.8 g, 15 mmol) in THF (30 mL) was added $LiBH_4$ (3.6 ml, 7.3 mmol). The reaction was stirred at rt for overnight. The mix was diluted with EtOAc (200 mL), washed with water and brine, dried over $Na_2SO_4$ and concentrated. The residue was purified by flash chromatography with 0 to 100% using EtOAc in hexanes as eluent to give product (2.51 g, 10.77 mmol, 80%). LCMS (MM-ES+APCI, Pos): m/z 233.1 (M+H).

Step C: 1-(2-(benzyloxy)ethyl)-2-(fluoromethyl)-1H-imidazole. Triethylamine (1.07 ml, 7.75 mmol), 1,1,2,2,3,3,4,4,4-nonafluorobutane-1-sulfonyl fluoride (0.464 ml, 2.58 mmol) and triethylamine trihydrofluoride (0.429 ml, 2.58 mmol) were added sequentially to a solution of (1-(2-(benzyloxy)ethyl)-1H-imidazol-2-yl)methanol (0.200 g, 0.861 mmol) in MeCN (10 mL) at 0° C. The cold bath was removed after 15 minutes and the mixture stirred for 2 hours. The reaction mixture was then diluted with water (20 mL) and extracted with EtOAc (3×20 mL). The combined organic layers were washed with brine (70 mL), dried over $Na_2SO_4$, filtered and concentrated in vacuo. The residue was purified by silica gel chromatography using 0 to 100% EtOAc/heptane as eluent to give product (101 mg, 0.43 mmol, 50%). LCMS (MM-ES+APCI, Pos): m/z 235.1 (M+H).

Step D: 2-(2-(fluoromethyl)-1H-imidazol-1-yl)ethan-1-ol. To 1-(2-(benzyloxy)ethyl)-2-(fluoromethyl)-1H-imidazole (100 mg, 0.427 mmol) in MeOH (10 mL) was added $Pd(OH)_2$/C (65.1 mg, 0.0854 mmol). The reaction mixture was flushed with N2 and then H2 and stirred under a H2 balloon for 16 hours. The mixture was filtered through Celite and washed with MeOH. The filtrate was then concentrated to give crude product which was used in the next step reaction without further purification (60 mg, 0.41 mmol, 99%). LCMS (MM-ES+APCI, Pos): m/z 145.1 (M+H).

Step E: (1R,5R,6R)-3-(7-(8-chloronaphthalen-1-yl)-8-fluoro-2-(2-(2-(fluoromethyl)-1H-imidazol-1-yl)ethoxy)pyrido[4,3-d]pyrimidin-4-yl)-3,8-diazabicyclo[3.2.1]octan-6-ol. Synthesized according to Example 32 substituting 2-(2-(fluoromethyl)-1H-imidazol-1-yl)ethan-1-ol in place of 2-(5-fluoropyridin-2-yl)ethan-1-ol in Step B (10 mg, 0.016 mmol, 37% yield). LCMS (MM-ES+APCI, Pos): m/z 578.2 (M+H).

Example 169

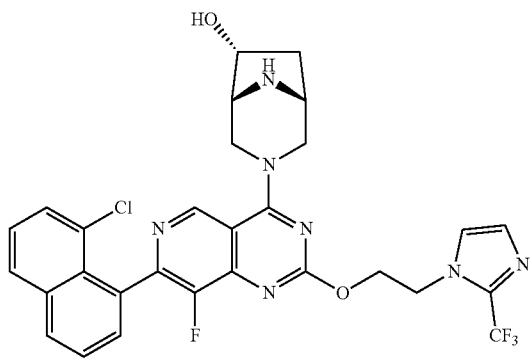 [SMILES: O[C@@H]1C[C@@H]2CN(c3nc(OCCn4ccnc4C(F)(F)F)nc4c(F)c(-c5cccc6cccc(Cl)c56)ncc34)C[C@H]1N2]

(1R,5R,6R)-3-(7-(8-chloronaphthalen-1-yl)-8-fluoro-2-(2-(2-(trifluoromethyl)-1H-imidazol-1-yl)ethoxy)pyrido[4,3-d]pyrimidin-4-yl)-3,8-diazabicyclo[3.2.1]octan-6-ol

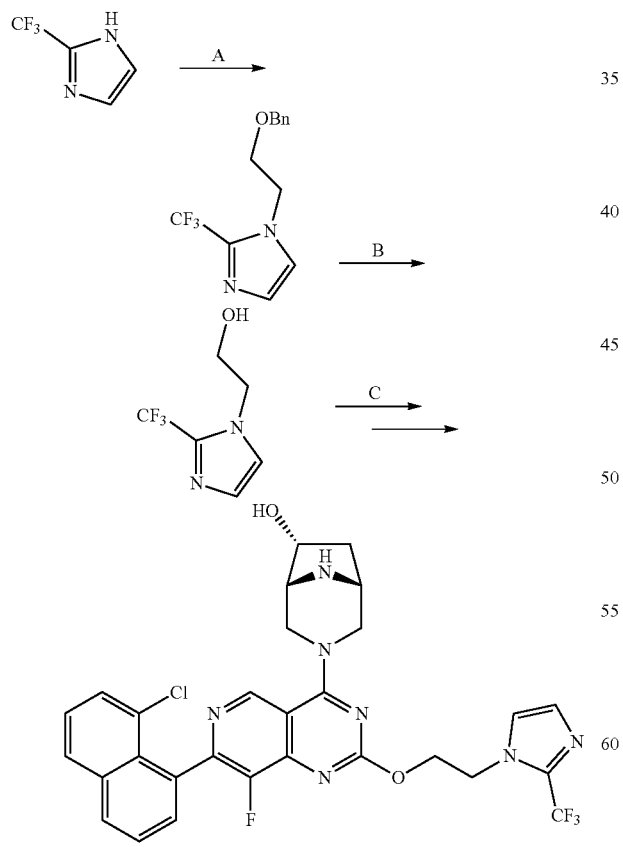

Step A: 1-(2-(benzyloxy)ethyl)-2-(trifluoromethyl)-1H-imidazole. To a solution of 2-(trifluoromethyl)-1H-imidazole (2 g, 14.7 mmol) in DMF (30 mL) were added $K_2CO_3$ (3.05 g, 22.0 mmol) and ((2-bromoethoxy)methyl)benzene (2.56 ml, 16.2 mmol). The reaction was heated at 80° C. for 3 hours. The mixture was diluted with EtOAc (200 mL), washed with water and brine, dried over $Na_2SO_4$ and concentrated. The residue was purified by flash chromatography with 0 to 100% EtOAc/hexanes as eluent to give product (3.51 g, 12.95 mmol, 88%). LCMS (MM-ES+APCI, Pos): m/z 271.1 (M+).

Step B: 2-(2-(trifluoromethyl)-1H-imidazol-1-yl)ethan-1-ol. To a solution of 1-(2-(benzyloxy)ethyl)-2-(trifluoromethyl)-1H-imidazole (450 mg, 1.67 mmol) in MeOH (20 mL) was added $Pd(OH)_2/C$ (127 mg, 0.167 mmol). The reaction mixture was flushed with N2 and H2 and then stirred under a H2 balloon for 16 hours. The mixture was filtered through Celite and washed with MeOH. The filtrate was then concentrated to give crude product which was used in next step reaction without further purification (280 mg, 1.55 mmol, 93%). LCMS (MM-ES+APCI, Pos): m/z 181.2 (M+H).

Step C: (1R,5R,6R)-3-(7-(8-chloronaphthalen-1-yl)-8-fluoro-2-(2-(2-(trifluoromethyl)-1H-imidazol-1-yl)ethoxy)pyrido[4,3-d]pyrimidin-4-yl)-3,8-diazabicyclo[3.2.1]octan-6-ol. Synthesized according to Example 32 substituting 2-(2-(trifluoromethyl)-1H-imidazol-1-yl)ethan-1-ol in place of 2-(5-fluoropyridin-2-yl)ethan-1-ol in Step B (15 mg, 0.023 mmol, 77% yield). LCMS (MM-ES+APCI, Pos): m/z 614.2 (M+H).

Example 170

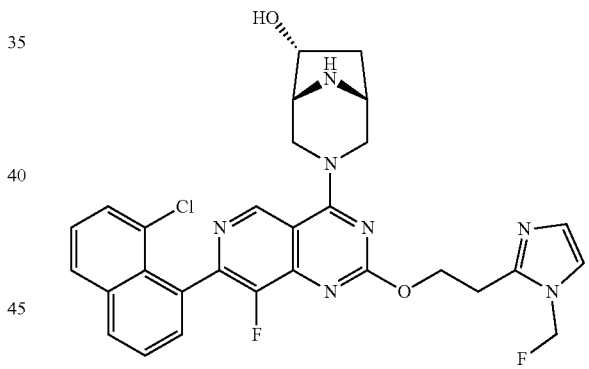

(1R,5R,6R)-3-(7-(8-chloronaphthalen-1-yl)-8-fluoro-2-(2-(1-(fluoromethyl)-1H-imidazol-2-yl)ethoxy)pyrido[4,3-d]pyrimidin-4-yl)-3,8-diazabicyclo[3.2.1]octan-6-ol

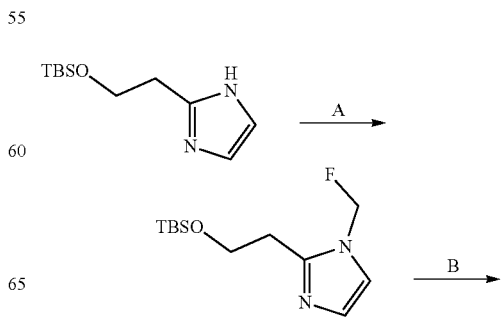

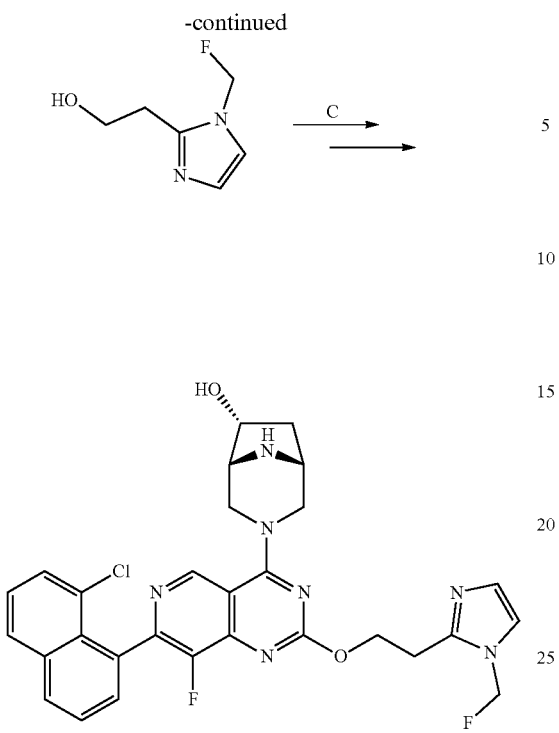

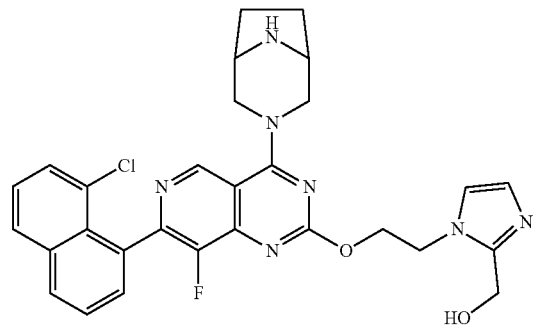 [SMILES: OCc1nccn1CCOc1nc(N2CC3CCC(C2)N3)c2cnc(-c3cccc4cccc(Cl)c34)c(F)c2n1]

Example 171

(1-(2-((4-(3,8-diazabicyclo[3.2.1]octan-3-yl)-7-(8-chloronaphthalen-1-yl)-8-fluoropyrido[4,3-d]pyrimidin-2-yl)oxy)ethyl)-1H-imidazol-2-yl)methanol Step A: 2-(2-((tert-butyldimethylsilyloxy)ethyl)-1-(fluoromethyl)-1H-imidazole. To a solution of 2-(2-((tert-butyldimethylsilyl)oxy)ethyl)-1H-imidazole (1.00 g, 4.42 mmol) in DMF (20 mL) was added sodium hydride (0.265 g, 6.63 mmol). The mixture was stirred for 30 minutes. Chlorofluoromethane (0.333 g, 4.86 mmol) was then bubbled through the reaction mixture for 5 minutes. The reaction was then sealed and stirred at 70° C. for 18 hours. The mixture was diluted with EtOAc (50 mL), washed with water and brine, dried over $Na_2SO_4$ and concentrated. The material was purified by flash chromatography with 0 to 100% using EtOAc in hexanes as eluent (0-100%) to give product (650 mg, 2.51 mmol, 57%). LCMS (MM-ES+APCI, Pos): m/z 259.2 (M+H).

Step B: 2-(1-(fluoromethyl)-1H-imidazol-2-yl)ethan-1-ol. To a solution of 2-(2-((tert-butyldimethylsilyl)oxy)ethyl)-1-(fluoromethyl)-1H-imidazole (500 mg, 1.93 mmol) in THF (20 mL) at 0° C. was added TBAF (1935 µL, 1.93 mmol). The reaction was stirred at rt for 2 hours. The mixture was diluted with EtOAc (50 mL), washed with water and brine, dried over $Na_2SO_4$ and concentrated. The material was purified by flash chromatography with 0 to 100% EtOAc in hexanes as eluent to give product (150 mg, 1.03 mmol, 54%). LCMS (MM-ES+APCI, Pos): m/z 145.2 (M+H).

Step C: (1R,5R,6R)-3-(7-(8-chloronaphthalen-1-yl)-8-fluoro-2-(2-(1-(fluoromethyl)-1H-imidazol-2-yl)ethoxy)pyrido[4,3-d]pyrimidin-4-yl)-3,8-diazabicyclo[3.2.1]octan-6-ol. Synthesized according to Example 32 substituting 2-(1-(fluoromethyl)-1H-imidazol-2-yl)ethan-1-ol in place of 2-(5-fluoropyridin-2-yl)ethan-1-ol in Step B (6 mg, 0.01 mmol, 33% yield). LCMS (MM-ES+APCI, Pos): m/z 578.2 (M+H).

Step A: 1-(2-(benzyloxy)ethyl)-2-(((tert-butyldimethylsilyl)oxy)methyl)-1H-imidazole. To a solution of (1-(2-(benzyloxy)ethyl)-1H-imidazol-2-yl)methanol (400 mg, 1.72 mmol) in DMF (3 mL) were added 1H-imidazole (586 mg, 8.61 mmol) and tert-butylchlorodimethylsilane (519 mg, 3.44 mmol). The reaction was stirred at rt for overnight. The mixture was diluted with EtOAc (20 mL), washed with water and brine, dried over Na₂SO₄ and concentrated. The material was purified by flash chromatography with 0 to 100% using EtOAc in hexanes as eluent to give product (500 mg, 1.44 mmol, 84%). LCMS (MM-ES+APCI, Pos): m/z 347.2 (M+H).

Step B: 2-(2-((((tert-butyldimethylsilyl)oxy)methyl)-1H-imidazol-1-yl)ethan-1-ol. To a solution of 1-(2-(benzyloxy)ethyl)-2-((((tert-butyldimethylsilyl)oxy)methyl)-1H-imidazole (500 mg, 1.44 mmol) in MeOH (15 mL) was added Pd(OH)₂/C (500 mg, 0.712 mmol). The reaction was purged with N2 and H2 and stirred at rt under H₂ balloon for overnight. The mixture was filtered through Celite and the Celite washed with MeOH. The solution was concentrated to give crude product (350 mg, 1.36 mmol, 95%). LCMS (MM-ES+APCI, Pos): m/z 257.2 (M+H).

Step C: (1-(2-((4-(3,8-diazabicyclo[3.2.1]octan-3-yl)-7-(8-chloronaphthalen-1-yl)-8-fluoropyrido[4,3-d]pyrimidin-2-yl)oxy)ethyl)-1H-imidazol-2-yl)methanol. Synthesized according to Example 32 substituting tert-butyl (1R,5S)-3,8-diazabicyclo[3.2.1]octane-8-carboxylate in place of 6-((tert-butyldimethylsilyl)oxy)-3,8-diazabicyclo[3.2.1]octane-8-carboxylate in step A and 2-(2-((((tert-butyldimethylsilyl)oxy)methyl)-1H-imidazol-1-yl)ethan-1-ol in place of 2-(5-fluoropyridin-2-yl)ethan-1-ol in Step B (22 mg, 0.037 mmol, 58% yield). LCMS (MM-ES+APCI, Pos): m/z 560.2 (M+H).

Example 172

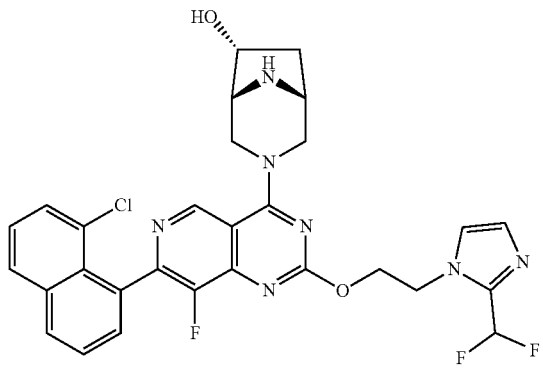 [SMILES: O[C@@H]1C[C@@H]2CN(c3nc(OCCn4ccnc4C(F)F)nc4c(F)c(-c5cccc6cccc(Cl)c56)ncc34)C[C@H]1N2]

(1R,5R,6R)-3-(7-(8-chloronaphthalen-1-yl)-2-(2-(2-(difluoromethyl)-1H-imidazol-1-yl)ethoxy)-8-fluoropyrido[4,3-d]pyrimidin-4-yl)-3,8-diazabicyclo[3.2.1]octan-6-ol

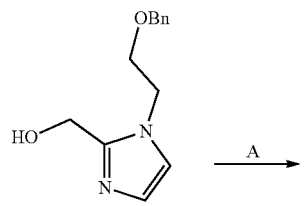

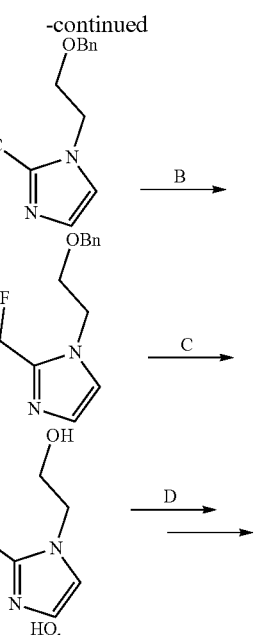

Step A: 1-(2-(benzyloxy)ethyl)-1H-imidazole-2-carbaldehyde. To (1-(2-(benzyloxy)ethyl)-1H-imidazol-2-yl)methanol (2.4 g, 10.3 mmol) in DCM (50 mL) at 0° C. was added Dess-Martin (6.57 g, 15.5 mmol) portion wise. The reaction was stirred at 0° C. for 3 hours. The mixture was diluted with water (50 mL) and extracted with DCM (50 mL). The organic layer was washed with water and brine, dried over Na₂SO₄ and concentrated. The residue was purified by flash chromatography with 0 to 100% EtOAc in hexanes as eluent to give product (1.61 g, 6.97 mmol, 68%). LCMS (MM-ES+APCI, Pos): m/z 231.1 (M+H).

Step B: 1-(2-(benzyloxy)ethyl)-2-(difluoromethyl)-1H-imidazole. 1-(2-(benzyloxy)ethyl)-1H-imidazole-2-carbaldehyde (620 mg, 2.69 mmol) was added to a pre-dried flask under nitrogen. Anhydrous DCM (15 ml) was added followed by deoxofluor (993 µL, 5.39 mmol) and finally EtOH (2 drops). The mixture was stirred at rt for 4 hours and then partitioned between sat. NaHCO₃ (aq.) and DCM. The organic layer was separated, washed with brine, dried over MgSO₄ and concentrated. The residue was purified by silica gel chromatography with 0 to 100% EtOAc/heptane as eluent to give product (320 mg, 1.26 mmol, 47%). LCMS (MM-ES+APCI, Pos): m/z 253.1 (M+H).

Step C: 2-(2-(difluoromethyl)-1H-imidazol-1-yl)ethan-1-ol. To 1-(2-(benzyloxy)ethyl)-2-(difluoromethyl)-1H-imidazole (310 mg, 1.23 mmol) in MeOH (15 mL) was added Pd(OH)₂/C (187 mg, 0.246 mmol). The reaction mixture was flashed with N2 and H2, and stirred under H₂ at 50 psi for 16 hours. The mixture was filtered through Celite and washed with MeOH. The filtrate was then concentrated to give crude product which was used in the next step reaction without further purification (160 mg, 0.98 mmol, 80%). LCMS (MM-ES+APCI, Pos): m/z 163.1 (M+H).

Step D: (1R,5R,6R)-3-(7-(8-chloronaphthalen-1-yl)-2-(2-(2-(difluoromethyl)-1H-imidazol-1-yl)ethoxy)-8-fluoropyrido[4,3-d]pyrimidin-4-yl)-3,8-diazabicyclo[3.2.1]octan-6-ol. Synthesized according to Example 32 substituting 2-(2-(difluoromethyl)-1H-imidazol-1-yl)ethan-1-ol in place of 2-(5-fluoropyridin-2-yl)ethan-1-ol in Step B (15 mg, 0.024 mmol, 64% yield). LCMS (MM-ES+APCI, Pos): m/z 596.2 (M+H).

Example 173

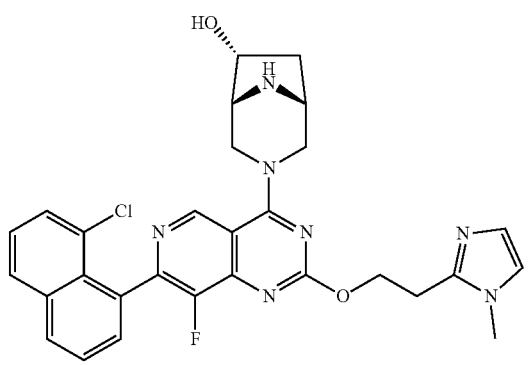 [SMILES: Cn1ccnc1CCOc1nc(N2C[C@H]3C[C@@H](O)[C@@H](C2)N3)c2cnc(-c3cccc4cccc(Cl)c34)c(F)c2n1]

(1R,5R,6R)-3-(7-(8-chloronaphthalen-1-yl)-8-fluoro-2-(2-(1-methyl-1H-imidazol-2-yl)ethoxy)pyrido[4,3-d]pyrimidin-4-yl)-3,8-diazabicyclo[3.2.1]octan-6-ol Synthesized according to Example 32 substituting 2-(1-methyl-1H-imidazol-2-yl)ethan-1-ol in place of 2-(5-fluoropyridin-2-yl)ethan-1-ol in Step B (15 mg, 0.024 mmol, 64% yield). LCMS (MM-ES+APCI, Pos): m/z 560.1 (M+H).

Example 174

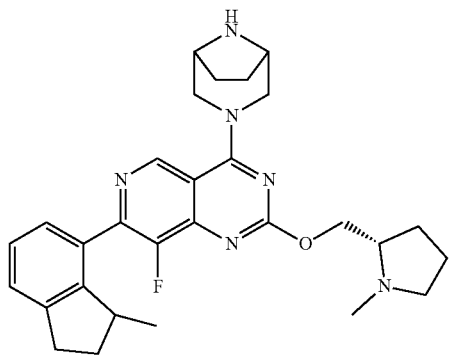 [SMILES: CC1CCc2cccc(-c3ncc4c(N5CC6CCC(C5)N6)nc(OC[C@@H]5CCCN5C)nc4c3F)c21]

4-((1R,5S)-3,8-diazabicyclo[3.2.1]octan-3-yl)-8-fluoro-7-(3-methyl-2,3-dihydro-1H-inden-4-yl)-2-(((S)-1-methylpyrrolidin-2-yl)methoxy)pyrido[4,3-d]pyrimidine

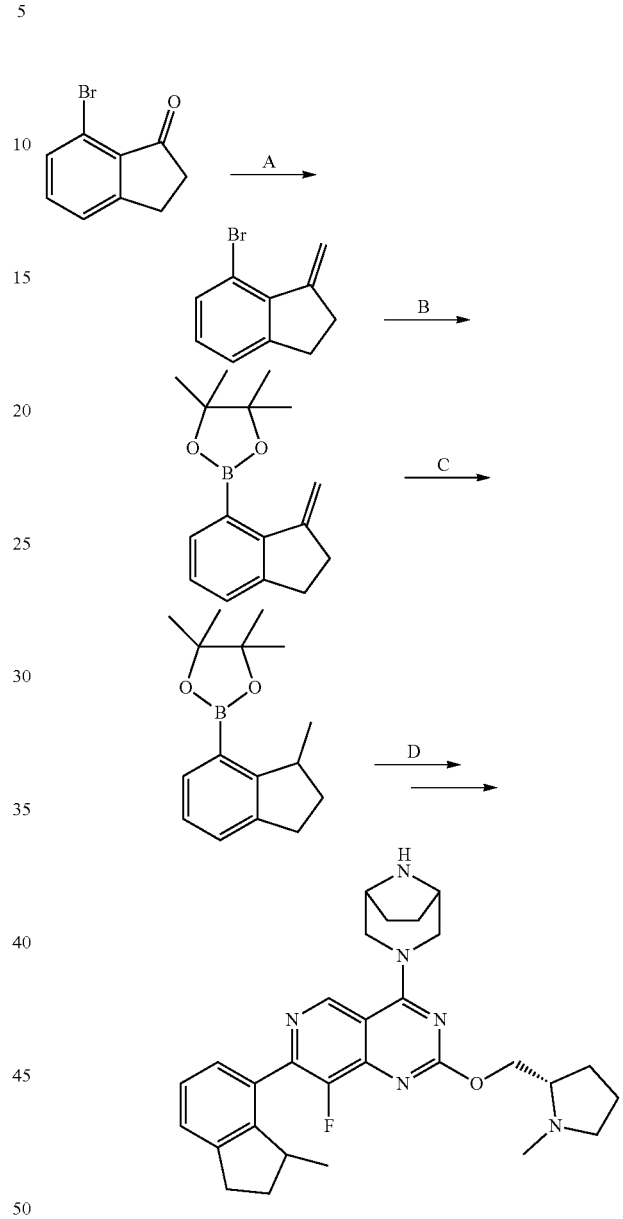

Step A. 7-bromo-1-methylene-2,3-dihydro-1H-indene. To methyl triphenyl phosphonium bromide (1320 mg, 3.70 mmol) in THF (30 mL) was added potassium 2-methylpropan-2-olate (3600 µL, 3.70 mmol) and the reaction stirred for one hour. 7-Bromo-2,3-dihydro-1H-inden-1-one (600 mg, 2.84 mmol) in THF (10 mL) was then added to the mixture and the reaction stirred for 3 hours. The reaction was quenched with NH$_4$Cl sat. solution and extracted with Et$_2$O (2×). The combined organics were dried (Na$_2$SO$_4$), concentrated and purified by flash chromatography eluting with 0-30% EtOAc/hexane to give 7-bromo-1-methylene-2,3-dihydro-1H-indene (490 mg, 2.34 mmol, 82%).

Step B. 4,4,5,5-tetramethyl-2-(3-methylene-2,3-dihydro-1H-inden-4-yl)-1,3,2-dioxaborolane. To 7-bromo-1-methylene-2,3-dihydro-1H-indene (500 mg, 2.39 mmol) in THF (20 mL) at −70° C. was added butyllithium (1148 µL, 2.87 mmol). The reaction was stirred at −70° C. for one hour. 2-isopropoxy-4,4,5,5-tetramethyl-1,3,2-dioxaborolane (634 µL, 3.11 mmol) was then added to the mixture and the cold bath was removed. The reaction was warmed to rt and stirred for two hours. The reaction was quenched with NH₄Cl sat. solution and extracted with Et₂O (2×). The combined organic was dried (Na₂SO₄), concentrated and purified by flash chromatography eluting with 0-30% EtOAc/hexane to give 4,4,5,5-tetramethyl-2-(3-methylene-2,3-dihydro-1H-inden-4-yl)-1,3,2-dioxaborolane (280 mg, 1.09 mmol, 46%).

Step C. 4,4,5,5-tetramethyl-2-(3-methyl-2,3-dihydro-1H-inden-4-yl)-1,3,2-dioxaborolane. To 4,4,5,5-tetramethyl-2-(3-methylene-2,3-dihydro-1H-inden-4-yl)-1,3,2-dioxaborolane (280 mg, 1.09 mmol) in MeOH (10 mL) was added Pd—C (50 mg, 0.0470 mmol). The reaction was purged with N2 and H2 (3×) and then stirred under H₂ balloon for one hour. The reaction was then purged with N2 and filtered through Celite. The Celite was washed with MeOH. The filtrate was concentrated to give crude 4,4,5,5-tetramethyl-2-(3-methyl-2,3-dihydro-1H-inden-4-yl)-1,3,2-dioxaborolane (252 mg, 0.98 mmol, 89%). ¹HNMR (400 MHz, CDCl₃) δ (ppm) 7.81 (1H, d, J=7.5 Hz), 7.28 (1H, t, J=7.5 Hz), 7.16 (1H, d, J=7.5 Hz), 3.62 (1H, m), 3.01 (1H, m), 2.78 (1H, m), 2.21 (1H, m), 1.79 (1H, m), 1.19 (3H, d, J=7.8 Hz).

Synthesized according to Example 2, Steps C-I substituting 4,4,5,5-tetramethyl-2-(3-methyl-2,3-dihydro-1H-inden-4-yl)-1,3,2-dioxaborolane in place of 4-(4,4,5,5-tetramethyl-1,3,2-dioxaborolan-2-yl)naphthalen-2-yl pivalate. LCMS (MM-ES+APCI, Pos): m/z 503.3 (M+H).

Example 175

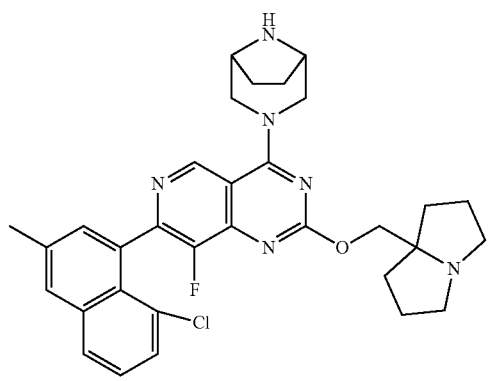 [SMILES: Cc1cc(-c2ncc3c(N4CC5CCC(C4)N5)nc(OCC45CCCN4CCC5)nc3c2F)c2c(Cl)cccc2c1]

4-((1R,5S)-3,8-diazabicyclo[3.2.1]octan-3-yl)-7-(8-chloro-3-methylnaphthalen-1-yl)-8-fluoro-2-((hexahydro-1H-pyrrolizin-7a-yl)methoxy)pyrido[4,3-d]pyrimidine

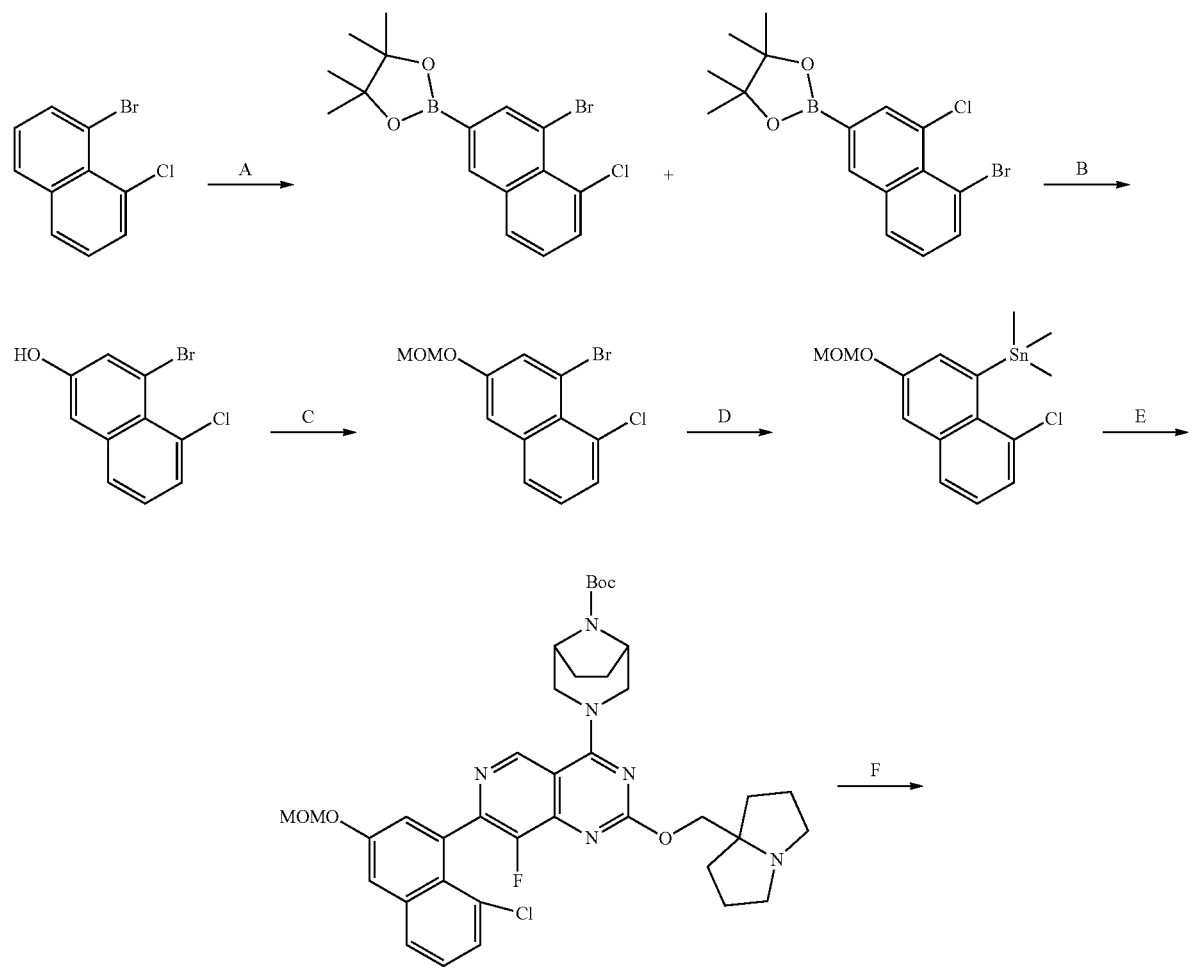

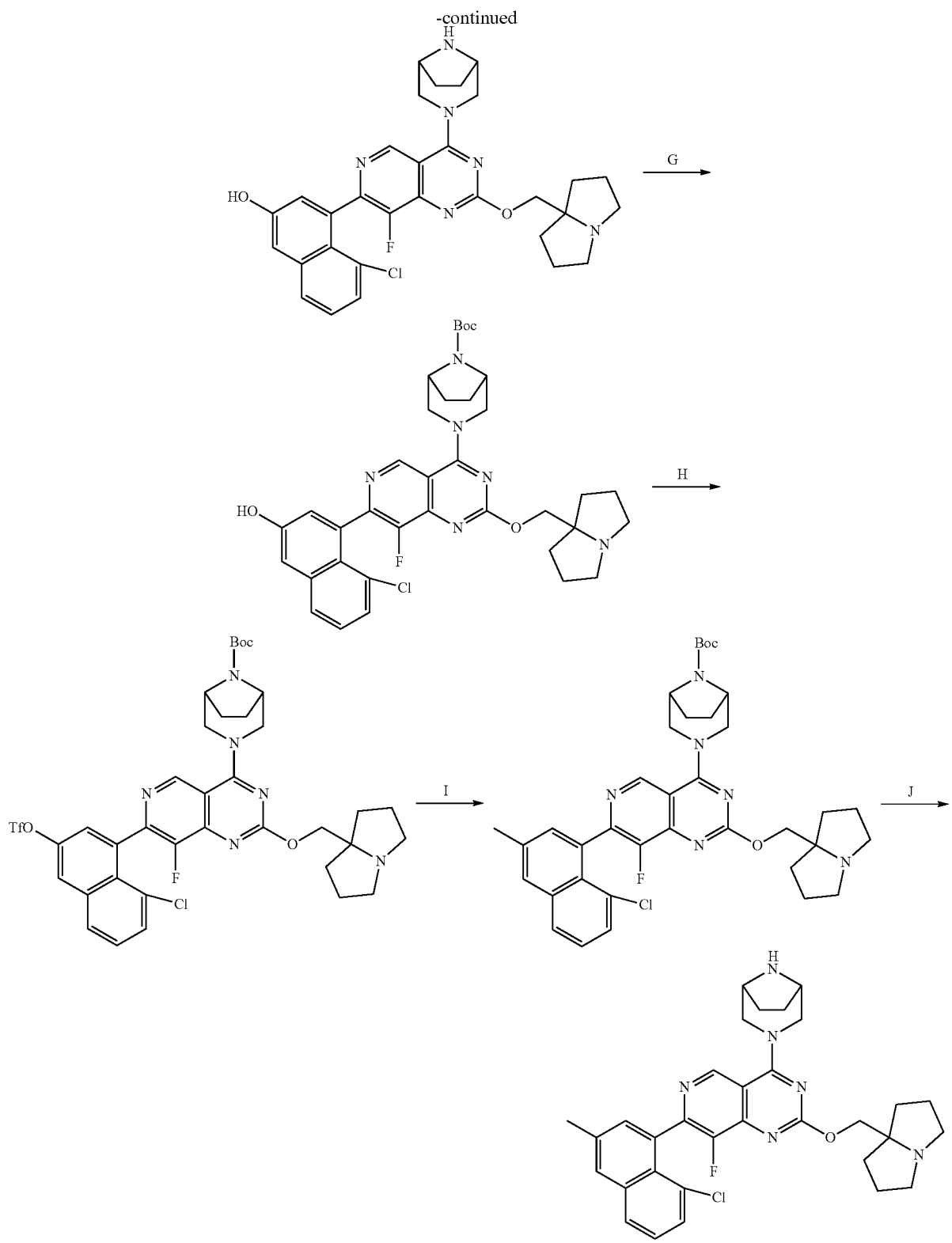

Step A. 2-(4-bromo-5-chloronaphthalen-2-yl)-4,4,5,5-tetramethyl-1,3,2-dioxaborolane and 2-(5-bromo-4-chloronaphthalen-2-yl)-4,4,5,5-tetramethyl-1,3,2-dioxaborolane. A mixture of 1-bromo-8-chloro-naphthalene (1.5 g, 6.21 mmol, 1.0 eq), 4,4,5,5-tetramethyl-1,3,2-dioxaborolane (2.38 g, 18.6 mmol, 2.70 mL, 3.0 eq), (1,5-cyclooctadiene) (methoxy)iridium(I) dimer (205 mg, 310 μmol, 0.05 eq), and 4-tert-butyl-2-(4-tert-butyl-2-pyridyl)pyridine (100 mg, 372 μmol, 0.06 eq) in THF (20 mL) was degassed and purged with N2 for 3 times. The mixture was stirred at 60° C. for 10 hours under N₂ atmosphere. The reaction mixture was concentrated under vacuum. The residue was purified by reversed phase flash chromatography [water (0.1% formic acid)/acetonitrile)] to give 2-(4-bromo-5-chloronaphthalen-2-yl)-4,4,5,5-tetramethyl-1,3,2-dioxaborolane and 2-(5-bromo-4-chloronaphthalen-2-yl)-4,4,5,5-tetramethyl-1,3,2-dioxaborolane (total 4.5 g) as brown oil.

Step B. 4-bromo-5-chloronaphthalen-2-ol. To a solution of 2-(4-bromo-5-chloronaphthalen-2-yl)-4,4,5,5-tetramethyl-1,3,2-dioxaborolane and 2-(5-bromo-4-chloronaphthalen-2-yl)-4,4,5,5-tetramethyl-1,3,2-dioxaborolane (3.5 g, 9.52 mmol, 1.0 eq) in $H_2O$ (35 mL) and THF (10 mL) were added AcOH (36.7 g, 611 mmol, 35.0 mL, 64.2 eq) and $H_2O_2$ (20.6 g, 182 mmol, 17.5 mL, 30% purity, 19.1 eq). The mixture was stirred at 10° C. for 1 hour. The reaction mixture was quenched with saturated $NaHSO_3$ solution (30 mL) and extracted with ethyl acetate (3×50 mL). The combined organic layers were washed with brine (30 mL), dried over $Na_2SO_4$, filtered and concentrated under reduced pressure to give the residue. The residue was purified by column chromatography ($SiO_2$, petroleum ether/ethyl acetate=10/1 to 3/1) and further purified twice by SFC (column: DAICEL CHIRALPAK AD-H (250 mm*30 mm, 5 μm); mobile phase: [0.1% $NH_3H_2O$ MEOH]; B %: 30%-30%, 3.4 min; 950 min) and (column: DAICEL CHIRALPAK AD-H (250 mm*30 mm, 5 μm); mobile phase: [0.1% $NH_3 \cdot H_2O$ MEOH]; B %: 35%-35%, 2.4 min, 680 min) to give 4-bromo-5-chloronaphthalen-2-ol (1.5 g, 61% yield). Yellow solid. LCMS [ESI, M–1]: 257.

Step C. 1-bromo-8-chloro-3-(methoxymethoxy)naphthalene. To a solution of 4-bromo-5-chloronaphthalen-2-ol (700 mg, 2.72 mmol, 1.0 eq) in dichloromethane (15 mL) were added MOMCl (1.7 g, 21.1 mmol, 1.60 mL, 7.77 eq) and DIEA (702 mg, 5.44 mmol, 946 μL, 2.0 eq) at 0° C. The mixture was stirred at 10° C. for 1 hour. The reaction mixture was diluted with water (10 mL) and extracted with dichloromethane (3×20 mL). The combined organic layers were washed with brine (20 mL), dried over $Na_2SO_4$, filtered and concentrated under reduced pressure to give a residue. The residue was purified by column chromatography ($SiO_2$, petroleum ether/ethyl acetate=50/1 to 3/1) to give 1-bromo-8-chloro-3-(methoxymethoxy)naphthalene (700 mg, 85% yield). White solid. $^1$H NMR (400 MHz, chloroform-d) δ=7.71-7.63 (m, 2H), 7.51 (dd, J=1.2, 7.6 Hz, 1H), 7.38 (d, J=2.4 Hz, 1H), 7.31 (t, J=8.0 Hz, 1H), 5.28 (s, 2H), 3.52 (s, 3H).

Step D. (8-chloro-3-(methoxymethoxy)naphthalen-1-yl)trimethylstannane. A mixture of 1-bromo-8-chloro-3-(methoxymethoxy)naphthalen (2.3 g, 7.63 mmol, 1.0 eq), trimethyl(trimethylstannyl) stannane (7.50 g, 22.9 mmol, 4.74 mL, 3.0 eq), and Pd(PPh$_3$)$_4$ (881 mg, 762 μmol, 0.1 eq) in toluene (50 mL) was degassed and purged with N2 for 3 times, and then the mixture was stirred at 110° C. for 12 hours under $N_2$ atmosphere. The reaction mixture was diluted with water (30 mL) and extracted with ethyl acetate (3×50 mL). The combined organic layers were washed with brine (30 mL), dried over $Na_2SO_4$, filtered and concentrated under reduced pressure to give a residue. The residue was purified by column chromatography ($SiO_2$, petroleum ether/ethyl acetate=20/1 to 5/1) to give (8-chloro-3-(methoxymethoxy)naphthalen-1-yl)trimethylstannane (1.5 g, 51% yield). Colorless oil. $^1$H NMR (400 MHz, chloroform-d) δ=7.72-7.66 (m, 1H), 7.57 (d, J=2.8 Hz, 1H), 7.50-7.45 (m, 1H), 7.38 (d, J=2.8 Hz, 1H), 7.36-7.30 (m, 1H), 5.32 (s, 2H), 3.54 (s, 3H), 0.45 (s, 9H).

Step E. (1R,5S)-tert-butyl 3-(7-(8-chloro-3-(methoxymethoxy)naphthalen-1-yl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate. A mixture of (8-chloro-3-(methoxymethoxy)naphthalen-1-yl)trimethylstannane (867 mg, 2.25 mmol, 3.0 eq), tert-butyl (1R,5S)-3-(7-chloro-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (400 mg, 750 μmol, 1.0 eq), CuI (42.9 mg, 225 μmol, 0.3 eq), BINAP (93.4 mg, 150 μmol, 0.2 eq) and Pd(dppf)Cl$_2$ (54.9 mg, 75.1 μmol, 0.1 eq) in toluene (10 mL) was degassed and purged with N2 for 3 times, and then the mixture was stirred at 100° C. for 8 hours under $N_2$ atmosphere. The mixture was diluted with water (20 mL) and extracted with ethyl acetate (3×30 mL). The combined organic layers were washed with brine (20 mL), dried over $Na_2SO_4$, filtered and concentrated under reduced pressure to give a residue. The residue was purified by reversed phase flash chromatography [water (0.1% formic acid)/acetonitrile)] to give (1R,5S)-tert-butyl 3-(7-(8-chloro-3-(methoxymethoxy)naphthalen-1-yl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (300 mg, 52% yield). Yellow solid. LCMS [ESI, M+1]: 719.

Step F. 4-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)-5-chloronaphthalen-2-ol. A solution of (1R,5S)-tert-butyl 3-(7-(8-chloro-3-(methoxymethoxy)naphthalen-1-yl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (300 mg, 417 μmol, 1.0 eq) in HCl·MeOH (4 M, 3 mL, 28.8 eq) was stirred at 10° C. for 30 minutes. The reaction mixture was concentrated under vacuum to give 4-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)-5-chloronaphthalen-2-ol (270 mg, crude, 2HCl). Yellow solid. The solid was used to next step directly without further purification. LCMS [ESI, M+1]: 575.

Step G. (1R,5S)-tert-butyl 3-(7-(8-chloro-3-hydroxynaphthalen-1-yl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate. To a solution of 4-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)-5-chloronaphthalen-2-ol (270 mg, 416 μmol, 1.0 eq, 2HCl) in DCM (5 mL) were added DIEA (269 mg, 2.08 mmol, 362 μL, 5.0 eq) and Boc$_2$O (90.9 mg, 416 μmol, 95. μL, 1.0 eq). The mixture was stirred at 20° C. for 1 hour. The reaction mixture was diluted with water (5 mL) and extracted with DCM (3×5 mL). The combined organic layers were washed with brine (5 mL), dried over $Na_2SO_4$, filtered and concentrated under reduced pressure to give a residue. The residue was purified by reversed phase flash chromatography [water (0.1% formic acid)/acetonitrile)] to give (1R,5S)-tert-butyl 3-(7-(8-chloro-3-hydroxynaphthalen-1-yl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (210 mg, 65% yield). Yellow solid. LCMS [ESI, M+1]: 675.

Step H. (1R,5S)-tert-butyl 3-(7-(8-chloro-3-(((trifluoromethyl)sulfonyl)oxy)naphthalen-1-yl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate. To a solution of (1R,5S)-tert-butyl 3-(7-(8-chloro-3-hydroxynaphthalen-1-yl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate 70 mg, 103 μmol, 1.0 eq) in DCM (3 mL) was added Tf$_2$O (58.5 mg, 207 μmol, 34.4 μL, 2.0 eq) and DIEA (53.6 mg, 414 μmol, 72.2 μL, 4.0 eq). The mixture was stirred at 0° C. for 1 hour. The reaction mixture was diluted with water (5 mL) and extracted with DCM (3×10 mL). The combined organic layers were washed with brine (10 mL), dried over $Na_2SO_4$, filtered and concentrated under reduced pressure to give a residue. The residue was purified by preparative TLC (SiO$_2$, DCM:MeOH=10:1) to give (1R,5S)-tert-butyl 3-(7-(8-chloro-3-(((trifluoromethyl)sulfonyl)oxy)naphthalen-1-yl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (60 mg, 72% yield). Yellow solid. LCMS [ESI, M+1]: 807.

Step I. (1R,5S)-tert-butyl 3-(7-(8-chloro-3-methylnaphthalen-1-yl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate. A mixture of (1R,5S)-tert-butyl 3-(7-(8-chloro-3-(((trifluoromethyl)sulfonyl)oxy)naphthalen-1-yl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (40 mg, 49.5 μmol, 1.0 eq), methylboronic acid (29.7 mg, 495 μmol, 10.0 eq), $Na_2CO_3$ (15.7 mg, 148 μmol, 3.0 eq), Pd(PPh$_3$)$_4$ (5.73 mg, 4.96 μmol, 0.1 eq) in THF (1 mL) and $H_2O$ (0.3 mL) was degassed and purged with N2 for 3 times, and then the mixture was stirred at 60° C. for 1 hour under $N_2$ atmosphere. The reaction mixture was diluted with water (5 mL) and extracted with ethyl acetate (3×5 mL). The combined organic layers were washed with brine (5 mL), dried over $Na_2SO_4$, filtered and concentrated under reduced pressure. The residue was purified by preparative TLC (SiO$_2$, DCM:MeOH=5:1) to give (1R,5S)-tert-butyl 3-(7-(8-chloro-3-methylnaphthalen-1-yl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (20 mg, 57% yield). Yellow solid. LCMS [ESI, M+1]: 673.

Step J. 4-((1R,5S)-3,8-diazabicyclo[3.2.1]octan-3-yl)-7-(8-chloro-3-methylnaphthalen-1-yl)-8-fluoro-2-((hexahydro-1H-pyrrolizin-7a-yl)methoxy)pyrido[4,3-d]pyrimidine. To a solution of (1R,5S)-tert-butyl 3-(7-(8-chloro-3-methylnaphthalen-1-yl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (20 mg, 29.7 μmol, 1.0 eq) in MeCN (150 ul) was added HCl·dioxane (4 M, 148 μL, 1.0 eq). The mixture was stirred at 20° C. for 30 minutes. The reaction mixture was concentrated under vacuum and diluted with water (1 mL). The mixture was adjusted to pH~8 with saturated NaHCO$_3$ aqueous solution and extracted with ethyl acetate (3×5 mL). The combined organic layers were washed with brine (5 mL), dried over $Na_2SO_4$, filtered and concentrated under reduced pressure to give the residue. The residue was purified with preparative HPLC (column: Waters Xbridge 150*25 mm*5 μm; mobile phase: [water (10 mM NH$_4$HCO$_3$)-ACN]; B %: 28%-58%, 10 min) to give 4-((1R,5S)-3,8-diazabicyclo[3.2.1]octan-3-yl)-7-(8-chloro-3-methylnaphthalen-1-yl)-8-fluoro-2-((hexahydro-1H-pyrrolizin-7a-yl)methoxy)pyrido[4,3-d]pyrimidine (4 mg, 23% yield). White solid. $^1$H NMR (400 MHz, chloroform-d) δ=9.00 (s, 1H), 7.81-7.73 (m, 2H), 7.49-7.33 (m, 3H), 4.64 (d, J=12.4 Hz, 1H), 4.56 (d, J=11.2 Hz, 1H), 4.29 (br s, 2H), 3.72-3.57 (m, 4H), 3.25 (br s, 2H), 2.77-2.64 (m, 2H), 2.54 (s, 3H), 2.23-2.12 (m, 2H), 2.02-1.87 (m, 7H), 1.78-1.67 (m, 3H). LCMS [ESI, M+1]: 573.

Example 176

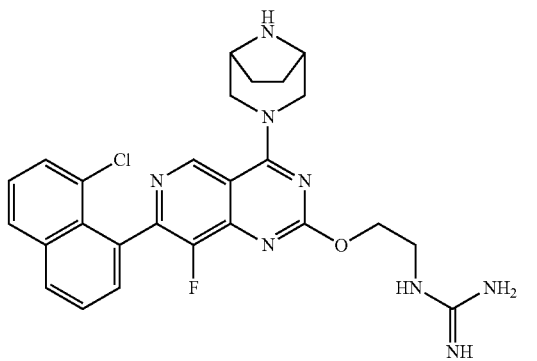 [SMILES: N=C(N)NCCOc1nc(N2CC3CCC(C2)N3)c2cnc(-c3cccc4cccc(Cl)c34)c(F)c2n1]

1-[2-[7-(8-chloro-1-naphthyl)-4-(3,8-diazabicyclo[3.2.1]octan-3-yl)-8-fluoro-pyrido[4,3-d]pyrimidin-2-yl]oxyethyl]guanidine

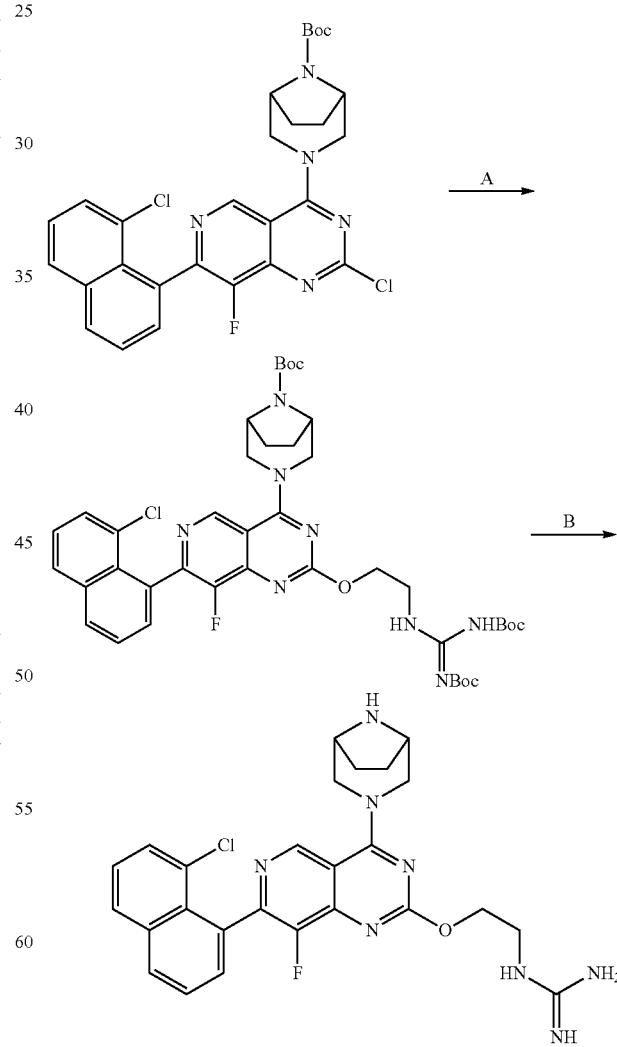

Step A. tert-butyl 3-[2-[2-[[(Z)—N,N'-bis(tert-butoxycarbonyl)carbamimidoyl]amino]ethoxy]-7-(8-chloro-1-naph-

373 thyl)-8-fluoro-pyrido[4,3-d]pyrimidin-4-yl]-3,8-diazabicyclo[3.2.1]octane-8-carboxylate. To a mixture of tert-butyl N-[(tert-butoxycarbonylamino)-(2-hydroxyethylamino)methylene]carbamate (123 mg, 406 mol, 1.5 eq) in THF (3 mL) was added NaH (21.6 mg, 541 µmol, 60% purity, 2.0 eq) at 0° C. After the mixture was stirred at 0° C. for 0.5 hour, tert-butyl (1R,5S)-3-(2-chloro-7-(8-chloronaphthalen-1-yl)-8-fluoropyrido[4,3-d]pyrimidin-4-yl)-3,8-diazabicyclo[3.2.1]octane-8-carboxylate (150 mg, 271 µmol, 1.0 eq) was added. The mixture was stirred at 0° C. for 0.5 hour under N₂. After completion, the mixture was quenched by H₂O (3 mL) at 0° C. Then the mixture was diluted with ethyl acetate (6 mL) and water (5 mL) then separated. The aqueous phase was extracted with ethyl acetate (2×5 mL). Then the combined organic layers were washed with saturated brine (8 mL), dried over Na₂SO₄, filtered and concentrated under vacuum. The residue was purified by reversed phase flash chromatography [water (formic acid 0.1%)/acetonitrile] to give the title compound (169 mg, 51% yield) as a yellow solid; $^1$H NMR (400 MHz, CDCl₃-d) δ=11.48 (s, 1H), 9.02 (s, 1H), 8.69 (br t, J=5.2 Hz, 1H), 8.00 (dd, J=1.6, 7.6 Hz, 1H), 7.88 (dd, J 0.8, 8.0 Hz, 1H), 7.63-7.54 (m, 3H), 7.45-7.40 (m, 1H), 4.69-4.58 (m, 3H), 4.52 (br d, J=12.4 Hz, 1H), 4.41 (br d, J=2.0 Hz, 2H), 3.96-3.86 (m, 2H), 3.81-3.57 (m, 2H), 2.02-1.96 (m, 2H), 1.88-1.77 (m, 2H), 1.53 (s, 9H), 1.50 (s, 9H), 1.46 (s, 9H); LCMS [ESI, M+1]: 821.

Step B. 1-[2-[7-(8-chloro-1-naphthyl)-4-(3,8-diazabicyclo[3.2.1]octan-3-yl)-8-fluoro-pyrido[4,3-d]pyrimidin-2-yl]oxyethyl]guanidine. A mixture of tert-butyl 3-[2-[2-[[(Z)—N,N'-bis(tert-butoxycarbonyl)carbamimidoyl]amino]ethoxy]-7-(8-chloro-1-naphthyl)-8-fluoro-pyrido[4,3-d]pyrimidin-4-yl]-3,8-diazabicyclo[3.2.1]octane-8-carboxylate (50.0 mg, 60.9 µmol, 1.0 eq) and TFA (1 mL) was stirred at 20° C. for 0.5 hour. After completion, the mixture was concentrated under vacuum. Then the pH value was adjusted to 9 with saturated Na₂CO₃ solution and methanol (24 mL) was added. The precipitated solid was filtered and the filtrate was concentrated under vacuum. The residue was purified by preparative HPLC (column: Phenomenex Synergi C18 150*30 mm*4 µm; mobile phase: [water (0.225% formic acid)-ACN]; B %: 0%-30%, 10 min) to give 1-[2-[7-(8-chloro-1-naphthyl)-4-(3,8-diazabicyclo[3.2.1]octan-3-yl)-8-fluoro-pyrido[4,3-d]pyrimidin-2-yl]oxyethyl]guanidine (8.72 mg, 25% yield, formic acid) as a white solid; $^1$H NMR (400 MHz, methanol-d₄) δ=9.10 (s, 1H), 8.49 (br s, 1H), 8.17-8.12 (m, 1H), 8.04-8.00 (m, 1H), 7.72-7.67 (m, 1H), 7.63-7.57 (m, 2H), 7.55-7.49 (m, 1H), 4.78 (br d, J=13.6 Hz, 2H), 4.62 (t, J=5.2 Hz, 2H), 4.15 (br s, 2H), 3.93 (br d, J=13.2 Hz, 2H), 3.66 (t, J=5.2 Hz, 2H), 2.13-2.00 (m, 4H); LCMS (ESI, M/2+1, M+1): 261, 521.

Example 177

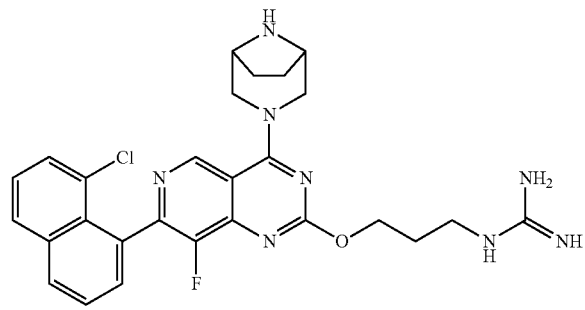 [SMILES: N=C(N)NCCCOc1nc(N2CC3CCC(C2)N3)c2cnc(-c3cccc4cccc(Cl)c34)c(F)c2n1]

374

1-[3-[7-(8-chloro-1-naphthyl)-4-(3,8-diazabicyclo[3.2.1]octan-3-yl)-8-fluoro-pyrido[4,3-d]pyrimidin-2-yl]oxypropyl]guanidine

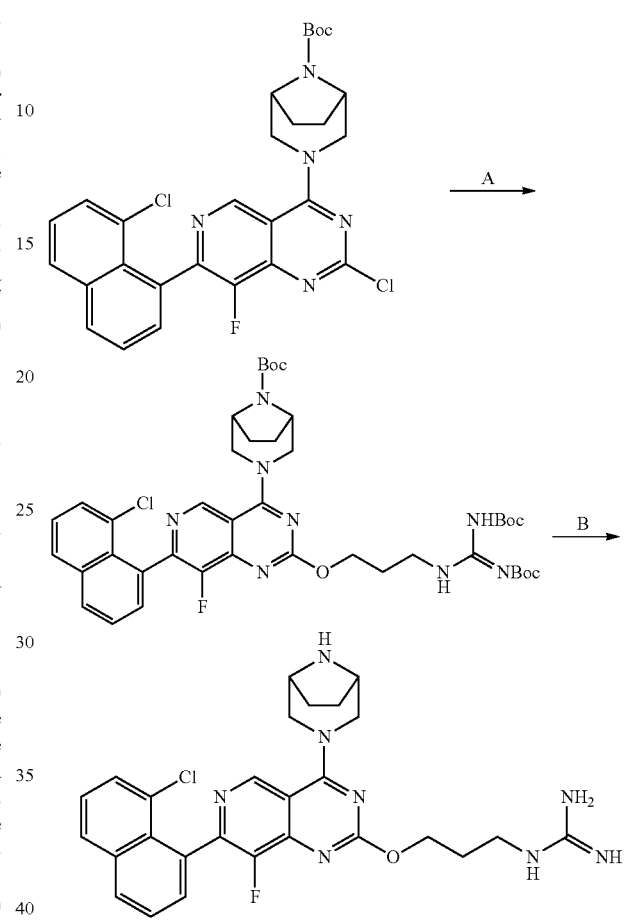

Step A. tert-butyl 3-[2-[3-[[(Z)—N,N-bis(tert-butoxycarbonyl)carbamimidoyl]amino]propoxy]-7-(8-chloro-1-naphthyl)-8-fluoro-pyrido[4,3-d]pyrimidin-4-yl]-3,8-diazabicyclo[3.2.1]octane-8-carboxylate. To a solution of tert-butyl N-[(tert-butoxycarbonylamino)-(3-hydroxypropylamino)methylene]carbamate (85.9 mg, 270 µmol, 1.5 eq) in THF (2 mL) was added NaH (14.4 mg, 361 µmol, 60% purity, 2.0 eq) at 0° C. After the mixture was stirred at 0° C. for 0.5 hour, tert-butyl (1R,5S)-3-(2-chloro-7-(8-chloronaphthalen-1-yl)-8-fluoropyrido[4,3-d]pyrimidin-4-yl)-3,8-diazabicyclo[3.2.1]octane-8-carboxylate (100 mg, 180 µmol, 1.0 eq) was added. The mixture was stirred at 0° C. for 0.5 hour, quenched with water (2 mL) and extracted with ethyl acetate (2×5 mL). The organic layers were dried over Na₂SO₄ and concentrated under vacuum. The residue was purified by reversed phase flash chromatography [water (0.1% formic acid)/acetonitrile]. The desired fractions were collected, neutralized with solid NaHCO₃, concentrated under vacuum to remove MeCN to give tert-butyl 3-[2-[3-[[(Z)—N,N-bis(tert-butoxycarbonyl)carbamimidoyl]amino]propoxy]-7-(8-chloro-1-naphthyl)-8-fluoro-pyrido[4,3-d]pyrimidin-4-yl]-3,8-diazabicyclo[3.2.1]octane-8-carboxylate (140 mg, 92%) as a pink solid; $^1$H NMR (400 MHz, CDCl₃): δ 11.53-11.45 (m, 1H), 9.02 (s, 1H), 8.47 (br t, J=5.2 Hz, 1H), 8.03-7.97 (m, 1H), 7.89 (dd, J=1.2, 8.4 Hz, 1H), 7.65-7.52 (m, 3H), 7.46-7.39 (m, 1H), 4.66-4.49 (m, 4H), 4.48-4.29 (m, 2H), 3.79-3.57 (m, 4H), 2.21-2.11 (m, 2H), 2.03-1.96 (m, 2H), 1.91-1.76 (m, 2H), 1.53 (s, 9H), 1.50 (s, 9H), 1.46 (s, 9H).

Step B. 1-[3-[7-(8-chloro-1-naphthyl)-4-(3,8-diazabicyclo[3.2.1]octan-3-yl)-8-fluoro-pyrido[4,3-d]pyrimidin-2-yl]oxypropyl]guanidine. A mixture of tert-butyl 3-[2-[3-[[(Z)—N,N-bis(tert-butoxycarbonyl)carbamimidoyl]amino]propoxy]-7-(8-chloro-1-naphthyl)-8-fluoro-pyrido[4,3-d]pyrimidin-4-yl]-3,8-diazabicyclo[3.2.1]octane-8-carboxylate (70 mg, 83.8 μmol, 1.0 eq) and TFA (191 mg, 1.68 mmol, 124 μL, 20 eq) was stirred at 15° C. for 1 hour. The solvent was removed under reduced pressure. The residue was diluted with MeOH (0.5 mL) and neutralized with saturated Na$_2$CO$_3$ solution (0.3 mL). The mixture was filtered, and the filtrate was purified with preparative HPLC (column: Phenomenex Synergi C18 150*25*10 μm; mobile phase: [water (0.225% formic acid)-ACN]; B %: 4%-34%, 10 min). The desired fractions were collected and lyophilized to give 1-[3-[7-(8-chloro-1-naphthyl)-4-(3,8-diazabicyclo[3.2.1]octan-3-yl)-8-fluoro-pyrido[4,3-d]pyrimidin-2-yl]oxypropyl]guanidine (23.2 mg, 47% yield, formic acid) as a yellow solid; $^1$H NMR (400 MHz, CD$_3$OD): δ 9.09 (s, 1H), 8.15 (dd, J=0.8, 8.0 Hz, 1H), 8.02 (dd, J=12, 8.4 Hz, 1H), 7.73-7.66 (m, 1H), 7.64-7.57 (m, 2H), 7.55-7.49 (m, 1H), 4.80 (br d, J=14.0 Hz, 2H), 4.58 (t, J=6.0 Hz, 2H), 4.18-4.10 (m, 2H), 3.97-3.86 (m, 2H), 3.43 (t, J=6.8 Hz, 2H), 2.15 (br s, 6H); LCMS [ESI, M+1]: 535.

Example 178

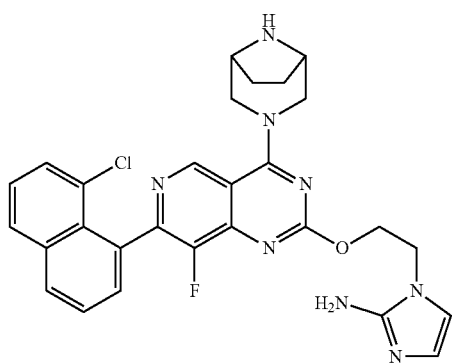 [SMILES: Nc1nccn1CCOc1nc(N2CC3CCC(C2)N3)c2cnc(-c3cccc4cccc(Cl)c34)c(F)c2n1]

1-[2-[7-(8-chloro-1-naphthyl)-4-(3,8-diazabicyclo[3.2.1]octan-3-yl)-8-fluoro-pyrido[4,3-d]pyrimidin-2-yl]oxyethyl]imidazol-2-amine

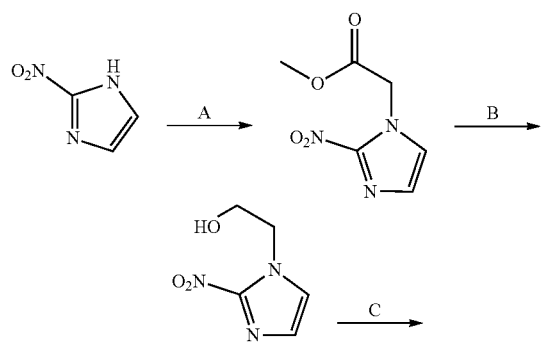

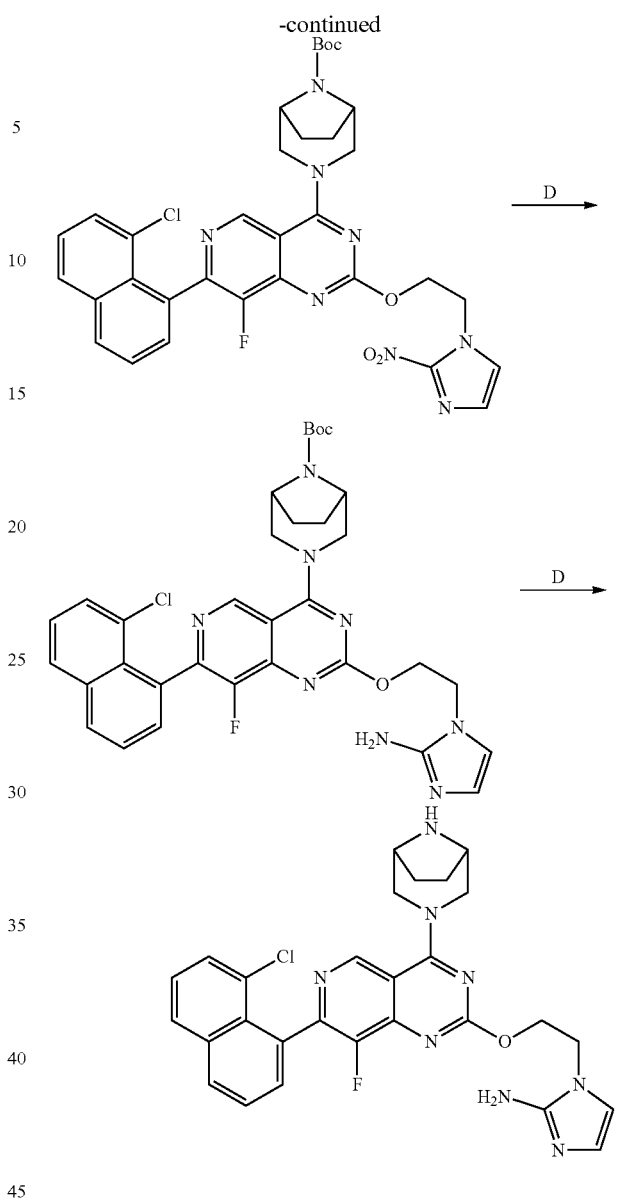

Step A. methyl 2-(2-nitro-1H-imidazol-1-yl)acetate. To a solution of 2-nitro-1H-imidazole (5 g, 44.2 mmol, 1.0 eq), CH$_3$ONa (3.58 g, 66.3 mmol, 1.5 eq) in DMF (50 mL) was added methyl 2-chloroacetate (4.80 g, 44.2 mmol, 3.90 mL, 1.0 eq) dropwise at 90° C. The mixture was stirred at 110° C. for 1 h. After completion, the mixture was diluted with water (100 mL) and extracted with ethyl acetate (2×80 mL). The combined organic layers were washed with brine (60 mL), dried over Na$_2$SO$_4$, filtered and concentrated in vacuum to give methyl 2-(2-nitro-1H-imidazol-1-yl)acetate (6.7 g, crude) as a yellow solid. LCMS [ESI, M+1]: 186.

Step B. 2-(2-nitro-1H-imidazol-1-yl)ethanol. To a solution of methyl 2-(2-nitro-1H-imidazol-1-yl)acetate (6.7 g, crude) in ethanol (60 mL) was added NaBH$_4$ (6.85 g, 181 mmol) in portions at 0° C. The mixture was stirred at 15° C. for 1.5 h. After completion, the mixture was concentrated in vacuum. The residue was purified by reverse phase chromatography (0.1% formic acid) and lyophilized to give 2-(2-nitro-1H-imidazol-1-yl)ethanol (1.4 g, two steps 20% yield) as a yellow solid. $^1$H NMR (400 MHz, MeOD) δ=8.54 (s, 1H), 7.47 (d, J=1.2 Hz, 1H), 7.13 (s, 1H), 4.59-4.57 (m, 2H), 3.90-3.87 (m, 2H).

Step C. tert-butyl 3-[7-(8-chloro-1-naphthyl)-8-fluoro-2-[2-(2-nitroimidazol-1-yl) ethoxy]pyrido[4,3-d]pyrimidin-4-yl]-3,8-diazabicyclo[3.2.1]octane-8-carboxylate. A mixture of tert-butyl 3-[2-chloro-7-(8-chloro-1-naphthyl)-8-fluoro-pyrido[4,3-d]pyrimidin-4-yl]-3,8-diazabicyclo[3.2.1]octane-8-carboxylate (0.2 g, 361 μmol, 1.0 eq), 2-(2-nitro-1H-imidazol-1-yl)ethanol (113 mg, 721 μmol, 2.0 eq), BINAP (44.9 mg, 72.1 μmol, 0.2 eq), Cs$_2$CO$_3$ (353 mg, 1.08 mmol, 3.0 eq) and Pd(OAc)$_2$ (8.10 mg, 36.1 μmol, 0.1 eq) in toluene (10 mL) was stirred at 100° C. for 5 hours under N$_2$. After completion, the mixture was diluted with water (10 mL), extracted with ethyl acetate (2×20 mL). The combined organic layers were washed with brine (10 mL), dried over Na$_2$SO$_4$, filtered and concentrated under vacuum. The residue was purified by reversed phase chromatography [water (formic acid, 0.1%)/acetonitrile] to give tert-butyl 3-[7-(8-chloro-1-naphthyl)-8-fluoro-2-[2-(2-nitroimidazol-1-yl)ethoxy]pyrido[4,3-d]pyrimidin-4-yl]-3,8-diazabicyclo[3.2.1]octane-8-carboxylate (40 mg, 16% yield). Yellow solid. LCMS [ESI, M+1]: 675.

Step D. tert-butyl 3-[2-[2-(2-aminoimidazol-1-yl)ethoxy]-7-(8-chloro-1-naphthyl)-8-fluoro-pyrido[4,3-d]pyrimidin-4-yl]-3,8-diazabicyclo[3.2.1]octane-8-carboxylate. A mixture of tert-butyl 3-[7-(8-chloro-1-naphthyl)-8-fluoro-2-[2-(2-nitroimidazol-1-yl) ethoxy]pyrido[4,3-d]pyrimidin-4-yl]-3,8-diazabicyclo[3.2.1]octane-8-carboxylate (40 mg, 59.3 μmol, 1.0 eq) Fe (33.1 mg, 593 μmol, 10 eq), and NH$_4$Cl (6.34 mg, 119 μmol, 2.0 eq) in EtOH (2.0 mL) was stirred at 60° C. for 1 hour. After completion, the mixture was filtered, diluted with water (6.0 mL), and extracted with ethyl acetate (2×10 mL). The combined organic layers were washed with brine (5.0 mL), dried over Na$_2$SO$_4$, filtered and concentrated under vacuum. The residue was purified by reversed phase chromatography [water (formic acid, 0.1%)/acetonitrile] to give tert-butyl 3-[2-[2-(2-aminoimidazol-1-yl)ethoxy]-7-(8-chloro-1-naphthyl)-8-fluoro-pyrido[4,3-d]pyrimidin-4-yl]-3,8-diazabicyclo[3.2.1]octane-8-carboxylate (40 mg, crude) as a yellow oil. LCMS [ESI, M+1]: 645.

Step E. 1-[2-[7-(8-chloro-1-naphthyl)-4-(3,8-diazabicyclo[3.2.1]octan-3-yl)-8-fluoro-pyrido[4,3-d]pyrimidin-2-yl]oxyethyl]imidazol-2-amine. To a solution of tert-butyl 3-[2-[2-(2-aminoimidazol-1-yl)ethoxy]-7-(8-chloro-1-naphthyl)-8-fluoro-pyrido[4,3-d]pyrimidin-4-yl]-3,8-diazabicyclo[3.2.1]octane-8-carboxylate (35 mg, crude) in dichloromethane (2.0 mL) was added 2,6-LUTIDINE (69.8 mg, 651 μmol, 75.8 ul) at −40° C., the mixture was stirred at −40° C. for 10 mins, and trimethylsilyl trifluoromethanesulfonate (72.4 mg, 326 μmol, 58.8 ul) was added. The mixture was stirred at 0° C. for 10 minutes. After completion, the mixture was concentrated under vacuum. The residue was purified using preparative HPLC (column: Waters Xbridge 150*25 mm*5 μm; mobile phase: [water (10 mM NH$_4$HCO$_3$)-ACN]; B %: 20%-50%, 10 min) to give 1-[2-[7-(8-chloro-1-naphthyl)-4-(3,8-diazabicyclo[3.2.1]octan-3-yl)-8-fluoro-pyrido[4,3-d]pyrimidin-2-yl]oxyethyl]imidazol-2-amine (6.63 mg, two steps 20% yield) as a white solid; $^1$H NMR (400 MHz, chloroform-d) δ=9.06 (s, 1H), 8.02 (dd, J=1.2, 7.6 Hz, 1H), 7.90 (dd, J=1.2, 8.4 Hz, 1H), 7.65-7.55 (m, 3H), 7.41 (t, J=8.0 Hz, 1H), 6.59 (dd, J=1.6, 18.4 Hz, 2H), 4.73-4.64 (m, 2H), 4.62-4.47 (m, 4H), 4.17 (t, J=6.4 Hz, 2H), 3.70 (br s, 2H), 3.68-3.59 (m, 2H), 1.83 (br s, 4H). LCMS [ESI, M+1]: 545.

Example 179

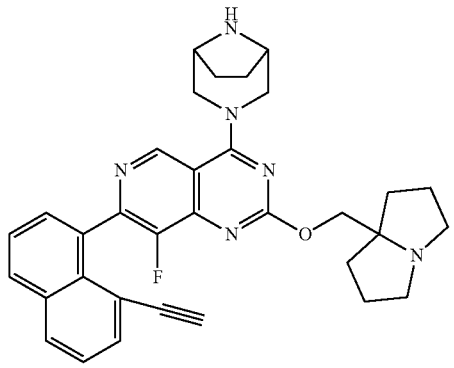 [SMILES: C#Cc1cccc2cccc(-c3ncc4c(N5CC6CCC(C5)N6)nc(OCC56CCCN5CCC6)nc4c3F)c12]

4-((1R,5S)-3,8-diazabicyclo[3.2.1]octan-3-yl)-7-(8-ethynylnaphthalen-1-yl)-8-fluoro-2-((hexahydro-1H-pyrrolizin-7a-yl)methoxy)pyrido[4,3-d]pyrimidine

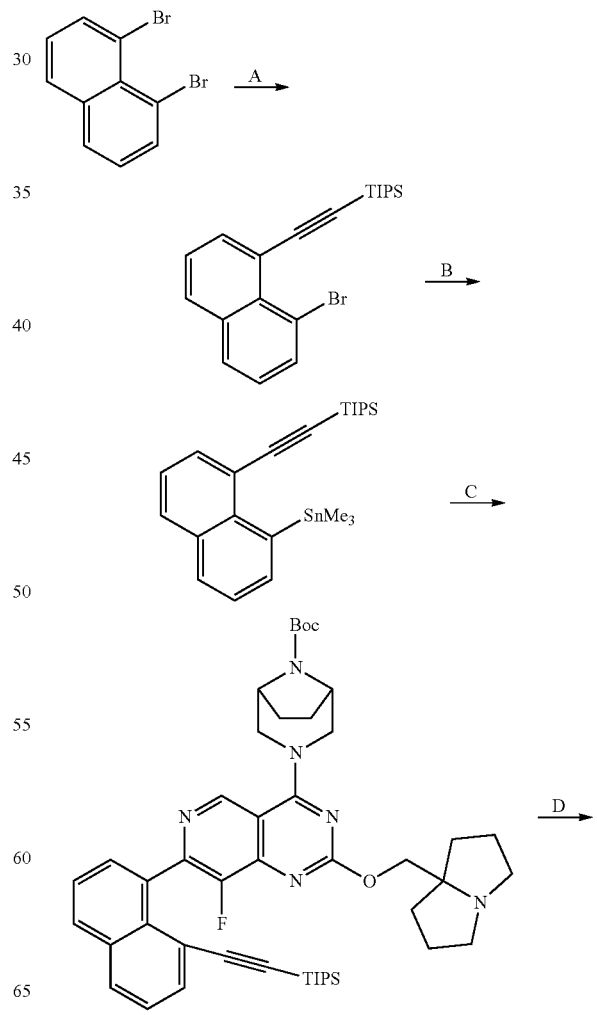

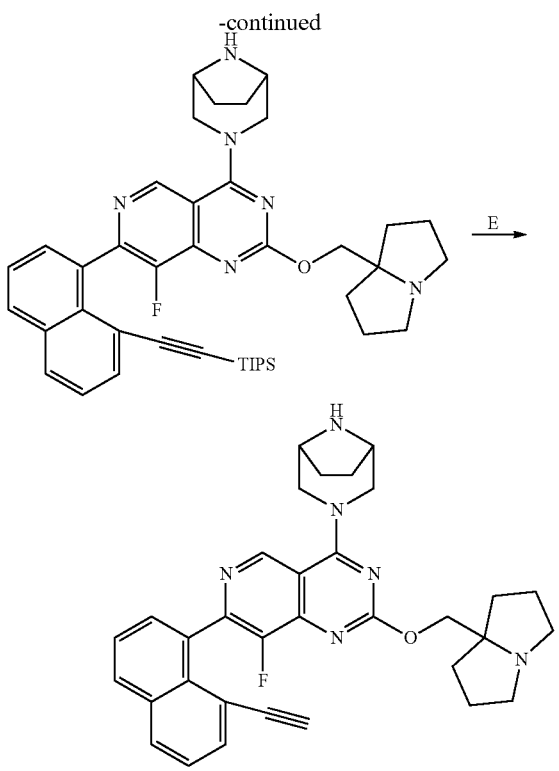

Step A. ((8-bromonaphthalen-1-yl)ethynyl)triisopropylsilane. A mixture of 1,8-dibromonaphthalene (7 g, 24.5 mmol, 1.0 eq), ethynyl(triisopropyl)silane (4.91 g, 26.9 mmol, 6.04 mL, 1.1 eq), CuI (466 mg, 2.45 mmol, 0.1 eq), PPh$_3$ (642 mg, 2.45 mmol, 0.1 eq) and Pd(PPh$_3$)$_2$Cl$_2$ (859 mg, 1.22 mmol, 0.05 eq) in TEA (100 mL) was stirred at 80° C. for 3 hours under N$_2$. After completion, the mixture was diluted with water (50 mL), extracted with ethyl acetate (2×50 mL). The combined organic layers were washed with brine (50 mL), dried over Na$_2$SO$_4$, filtered and concentrated under vacuum. The residue was purified by column chromatography (SiO$_2$, petroleum ether/ethyl acetate=1/0) to give 2-(8-bromo-1-naphthyl)ethynyl-triisopropyl-silane (7 g, 74% yield) as a yellow solid. $^1$H NMR (400 MHz, chloroform-d) δ=7.87 (dd, J=1.2, 7.2 Hz, 1H), 7.82-7.73 (m, 3H), 7.41-7.34 (m, 1H), 7.25 (t, J=7.6 Hz, 1H), 1.19-1.16 (m, 21H).

Step B. triisopropyl-[2-(8-trimethylstannyl-1-naphthyl)ethynyl]silane. A mixture of 2-(8-bromo-1-naphthyl)ethynyl-triisopropyl-silane (6.5 g, 16.8 mmol, 1.0 eq), trimethyl(trimethylstannyl)stannane (27.5 g, 83.9 mmol, 17.4 mL, 5.0 eq) and Pd(PPh$_3$)$_4$ (1.94 g, 1.68 mmol, 0.1 eq) in toluene (100 mL) was stirred at 110° C. for 48 hours under N$_2$. After completion, the mixture was diluted with water (100 mL). The mixture was extracted with ethyl acetate (2×100 mL). The combined organic layers were washed with brine (100 mL), dried over Na$_2$SO$_4$, filtered and concentrated under vacuum. The residue was purified by column chromatography (SiO$_2$, ethyl acetate/petroleum ether=0/1) and then re-purified with reversed phase chromatography [water (formic acid, 0.1%)/acetonitrile] to give triisopropyl-[2-(8-trimethylstannyl-1-naphthyl)ethynyl]silane (0.65 g, 8% yield) as a colorless oil. $^1$H NMR (400 MHz, chloroform-d) δ=7.90 (dd, J=1.2, 7.2 Hz, 1H), 7.86-7.79 (m, 3H), 7.47-7.39 (m, 2H), 1.25-1.18 (m, 21H), 0.54-0.44 (m, 9H).

Step C. (1R,5S)-tert-butyl-3-(8-fluoro-2-((hexahydro-1H-pyrrolizin-7a-yl)methoxy)-7-(8-((triisopropylsilyl)ethynyl)naphthalen-1-yl)pyrido[4,3-d]pyrimidin-4-yl)-3,8-diazabicyclo[3.2.1]octane-8-carboxylate. A mixture of tert-butyl (1R,5S)-3-(7-chloro-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (250 mg, 469 μmol, 1.0 eq), triisopropyl-[2-(8-trimethylstannyl-1-naphthyl)ethynyl]silane (331 mg, 703 μmol, 1.5 eq), CuI (26.8 mg, 140 μmol, 0.3 eq), BINAP (58.4 mg, 93.8 μmol, 0.2 eq) and Pd(dppf)Cl$_2$ (34.3 mg, 46.9 μmol, 0.1 eq) in toluene (5 mL) was degassed and purged with N2 for 3 times. The mixture was stirred at 90° C. for 8 hours under N$_2$ atmosphere. The reaction mixture was diluted with water (20 mL) and extracted with ethyl acetate (3×30 mL). The combined organic layers were washed with brine (20 mL), dried over Na$_2$SO$_4$, filtered and concentrated under reduced pressure to give a residue. The residue was purified by column chromatography (SiO$_2$, ethyl acetate/methanol=100/1 to 10/1) and further purified by reversed phase flash chromatography [water (0.1% formic acid)/acetonitrile)] to give (1R,5S)-tert-butyl-3-(8-fluoro-2-((hexahydro-1H-pyrrolizin-7a-yl)methoxy)-7-(8-(((triisopropylsilyl)ethynyl)naphthalen-1-yl)pyrido[4,3-d]pyrimidin-4-yl)-3,8-diazabicyclo[3.2.1]octane-8-carboxylate (100 mg, 25% yield) as a yellow solid. LCMS [ESI, M+1]: 805.

Step D. 4-((1R,5S)-3,8-diazabicyclo[3.2.1]octan-3-yl)-8-fluoro-2-((hexahydro-1H-pyrrolizin-7a-yl)methoxy)-7-(8-((triisopropylsilyl)ethynyl)naphthalen-1-yl)pyrido[4,3-d]pyrimidine. To a solution of (1R,5S)-tert-butyl-3-(8-fluoro-2-((hexahydro-1H-pyrrolizin-7a-yl)methoxy)-7-(8-((triisopropylsilyl)ethynyl)naphthalen-1-yl)pyrido[4,3-d]pyrimidin-4-yl)-3,8-diazabicyclo[3.2.1]octane-8-carboxylate (60 mg, 74.5 μmol, 1 eq) in ACN (500 ul) was added HCl·dioxane (4 M, 372 ul). The mixture was stirred at 0° C. for 30 minutes. The reaction mixture was concentrated under vacuum. The residue was diluted with water (2 mL) and the pH was adjusted to ~8 with saturated NaHCO$_3$ aqueous solution. The mixture was extracted with ethyl acetate (3×10 mL). The combined organic layers were washed with brine (10 mL), dried over Na$_2$SO$_4$, filtered and concentrated under reduced pressure to give 4-((1R,5S)-3,8-diazabicyclo[3.2.1]octan-3-yl)-8-fluoro-2-((hexahydro-1H-pyrrolizin-7a-yl)methoxy)-7-(8-((triisopropylsilyl)ethynyl)naphthalen-1-yl)pyrido[4,3-d]pyrimidine (50 mg, 95% yield) as a yellow solid. LCMS [ESI, M+1]: 705.

Step E. 4-((1R,5S)-3,8-diazabicyclo[3.2.1]octan-3-yl)-7-(8-ethynylnaphthalene-1-yl)-8-fluoro-2-((hexahydro-1H-pyrrolizin-7a-yl)methoxy)pyrido[4,3-d]pyrimidine. A mixture of 4-((1R,5S)-3,8-diazabicyclo[3.2.1]octan-3-yl)-8-fluoro-2-((hexahydro-1H-pyrrolizin-7a-yl)methoxy)-7-(8-((triisopropylsilyl)ethynyl)naphthalen-1-yl)pyrido[4,3-d]pyrimidine (45 mg, 63.8 μmol, 1 eq) and CsF (96.9 mg, 638 μmol, 23.5 μL, 10 eq) in DMF (1 mL) was stirred at 15° C. for 3 hours. The reaction mixture was diluted with ethyl acetate (10 mL) and washed with water (3×5 mL). The combined organic layers were washed with brine (5 mL), dried over Na$_2$SO$_4$, filtered and concentrated under reduced pressure to give a residue. The residue was purified with preparative HPLC (column: Waters Xbridge 150*25 mm*5 μm; mobile phase: [water (10 mM NH$_4$HCO$_3$)-ACN]; B %: 28%-58%, 10 min). The desired fraction was collected and lyophilized to give 4-((1R,5S)-3,8-diazabicyclo[3.2.1]octan-3-yl)-7-(8-ethynylnaphthalen-1-yl)-8-fluoro-2-((hexahydro-1H-pyrrolizin-7a-yl)methoxy)pyrido[4,3-d]pyrimidine (6.17 mg, 17% yield) as a yellow solid. $^1$H NMR (400 MHz, chloroform-d) δ=8.99 (s, 1H), 8.03-7.92 (m, 2H), 7.75 (dd, J=1.2, 7.2 Hz, 1H), 7.64-7.56 (m, 2H), 7.46 (dd, J=7.2, 8.0 Hz, 1H), 4.73-4.50 (m, 2H), 4.32-4.15 (m, 2H), 3.72-

3.53 (m, 4H), 3.24-3.07 (m, 2H), 2.72-2.60 (m, 2H), 2.56 (s, 1H), 2.21-2.07 (m, 2H), 1.94-1.75 (m, 10H); LCMS [ESI, M+1]: 549.

Example 180

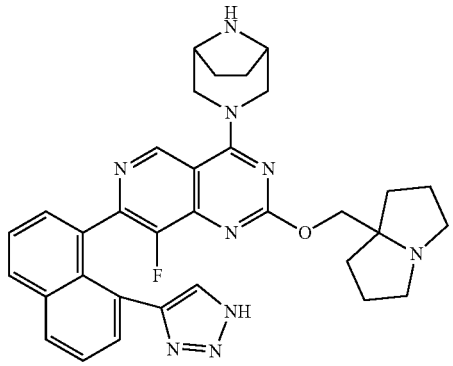 [SMILES: Fc1c(-c2cccc3cccc(-c4c[nH]nn4)c23)ncc2c(N3CC4CCC(C3)N4)nc(OCC34CCCN3CCC4)nc12]

7-(8-(1H-1,2,3-triazol-4-yl)naphthalen-1-yl)-4-((1R, 5S)-3,8-diazabicyclo[3.2.1]octan-3-yl)-8-fluoro-2-((hexahydro-1H-pyrrolizin-7a-yl)methoxy)pyrido[4, 3-d]pyrimidine

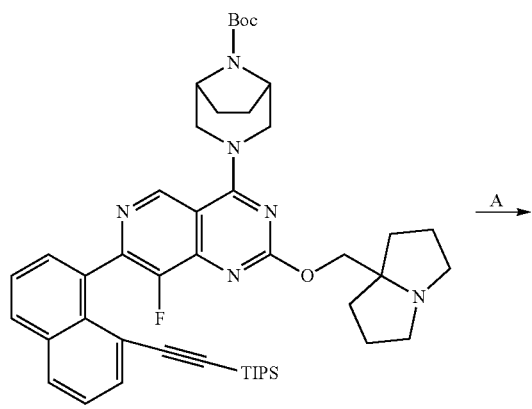

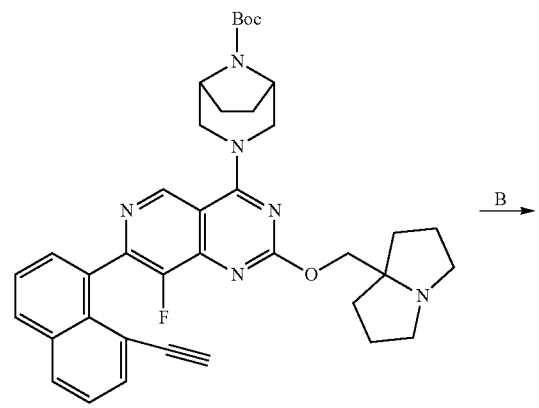

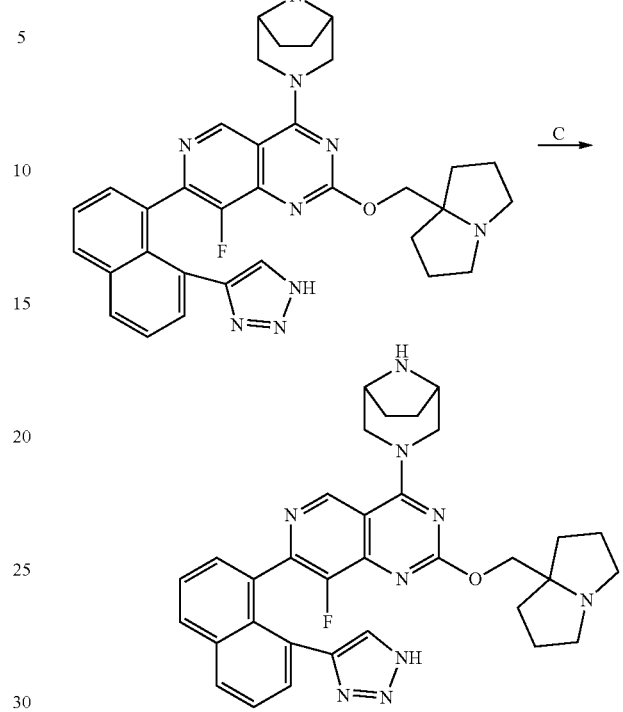

Step A. (1R,5S)-tert-butyl 3-(7-(8-ethynylnaphthalen-1-yl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate. tert-butyl (1R,5S)-3-(8-fluoro-2-((tetrahydro-1H-pyrrolizin-7a(5H)-yl)methoxy)-7-(8-((triisopropylsilyl)ethynyl)naphthalen-1-yl)pyrido[4,3-d]pyrimidin-4-yl)-3,8-diazabicyclo[3.2.1]octane-8-carboxylate (30 mg, 37.3 μmol, 1.0 eq) and CsF (28.3 mg, 186 μmol, 5.0 eq) in DMF (1 mL) was stirred at 15° C. for 3 hours. The reaction mixture was diluted with ethyl acetate (10 mL) and washed with water (3×5 mL). The organic layer was washed with brine (5 mL), dried over Na$_2$SO$_4$, filtered and concentrated under reduced pressure to give (1R,5S)-tert-butyl 3-(7-(8-ethynylnaphthalen-1-yl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (24 mg, 99% yield) as yellow oil and used to next step without purification. LCMS [ESI, M+1]: 649.

Step B. (1R,5S)-tert-butyl 3-(7-(8-(1H-1,2,3-triazol-4-yl)naphthalen-1-yl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate. To a solution of (1R,5S)-tert-butyl 3-(7-(8-ethynylnaphthalen-1-yl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (50 mg, 77.1 μmol, 1.0 eq) in CHCl$_3$ (1 mL) was added tetrakis(acetonitrile)copper(I) hexafluorophosphate (2.87 mg, 7.71 μmol, 0.1 eq) and benzyl N-diazocarbamate (27.3 mg, 154 μmol, 2.0 eq). The mixture was stirred at 50° C. for 2 hours. The reaction mixture was concentrated under vacuum. The residue was purified by preparative HPLC (column: Phenomenex luna C18 150*25 mm*10 μm; mobile phase: [water (0.1% TFA)-ACN]; B %: 22%-52%, 10 min) to give (1R,5S)-tert-butyl 3-(7-(8-(1H-1,2,3-triazol-4-yl)naphthalen-1-yl)-8-fluoro-2-((hexahydro-1H-pyrrolizin-7a- yl)methoxy)pyrido[4,3-d]pyrimidin-4-yl)-3,8-diazabicyclo [3.2.1]octane-8-carboxylate (10 mg, 15% yield, TFA) as a yellow solid. ¹H NMR (400 MHz, chloroform-d) δ=8.97 (s, 1H), 8.10 (dd, J=1.6, 7.8 Hz, 1H), 8.05 (dd, J=1.2, 8.0 Hz, 1H), 7.76-7.64 (m, 2H), 7.63-7.50 (m, 2H), 7.13 (s, 1H), 4.85 (d, J=12.0 Hz, 1H), 4.71-4.22 (m, 5H), 3.89 (br s, 2H), 3.83-3.74 (m, 1H), 3.67-3.54 (m, 1H), 3.19-3.01 (m, 2H), 2.61-2.46 (m, 1H), 2.41-2.23 (m, 3H), 2.22-2.08 (m, 2H), 2.06-1.74 (m, 6H), 1.53 (s, 9H). LCMS [ESI, M+1]: 692.

Step C. 7-(8-(1H-1,2,3-triazol-4-yl)naphthalen-1-yl)-4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidine. To a solution of (1R,5S)-tert-butyl 3-(7-(8-(1H-1,2,3-triazol-4-yl)naphthalen-1-yl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (10 mg, 12.4 μmol, 1.0 eq, TFA) in acetonitrile (100 ul) was added HCl·dioxane (4 M, 100 ul). The mixture was stirred at 10° C. for 30 minutes. The reaction mixture was concentrated under vacuum and the residue was diluted with acetonitrile (2.0 mL). The mixture was adjusted to pH~7 with saturated NaHCO₃ aqueous solution. The residue was purified with preparative HPLC (column: Phenomenex Synergi C18 150*25*10 μm; mobile phase: [water (0.225% FA)-ACN]; B %: 12%-42%, 9 min) to give 7-(8-(1H-1,2,3-triazol-4-yl)naphthalen-1-yl)-4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidine (2.73 mg, 36% yield,) as off-white solid. ¹H NMR (400 MHz, methanol-d₄) δ=8.87 (s, 1H), 8.2 (t, J=7.6 Hz, 2H), 7.80-7.63 (m, 3H), 7.53 (d, J=6.4 Hz, 1H), 7.36 (s, 1H), 4.95 (br s, 1H), 4.72-4.50 (m, 3H), 4.14-3.97 (m, 3H), 3.81-3.62 (m, 3H), 3.31-3.23 (m, 2H), 2.39-2.02 (m, 12H). LCMS [ESI, M+1]: 592. SFC analysis: Column: Chiralcel OD-3 50×4.6 mm I.D., 3 μm; Mobile phase: Phase A for C02, and Phase B for MeOH (0.05% DEA); Gradient elution: 40% MeOH (0.05% DEA) in C02; Flow rate: 3 mL/min; Wavelength: 220 nm; Column Temp: 35 C; Back Pressure: 100 Bar.

Example 181

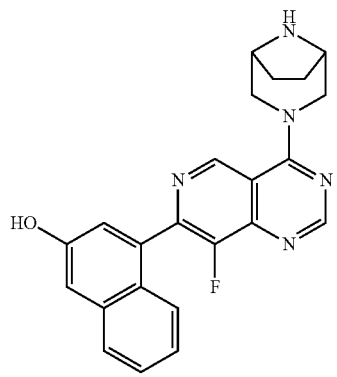 [SMILES: Oc1cc(-c2ncc3c(N4CC5CCC(C4)N5)ncnc3c2F)c2ccccc2c1]

4-(4-((1R,5S)-3,8-diazabicyclo[3.2.1]octan-3-yl)-8-fluoropyrido[4,3-d]pyrimidin-7-yl)naphthalen-2-ol

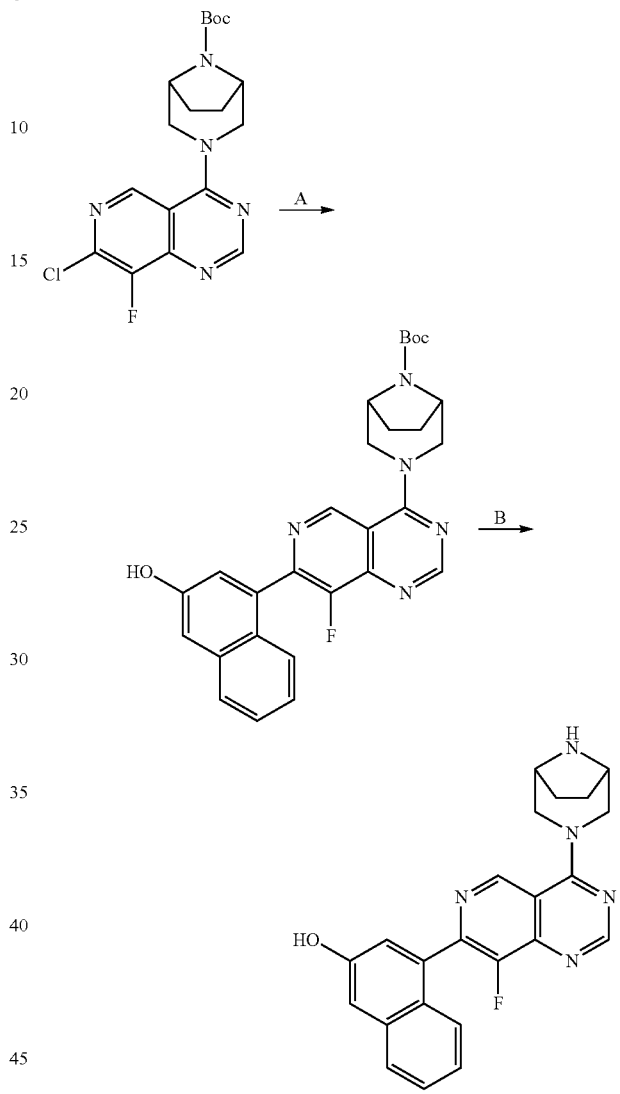

Step A. (1R,5S)-tert-butyl 3-(8-fluoro-7-(3-hydroxynaphthalen-1-yl)pyrido[4,3-d]pyrimidin-4-yl)-3,8-diazabicyclo[3.2.1]octane-8-carboxylate. To a mixture of (1R,5S)-tert-butyl 3-(7-chloro-8-fluoropyrido[4,3-d]pyrimidin-4-yl)-3,8-diazabicyclo[3.2.1]octane-8-carboxylate (200 mg, 508 μmol, 1.0 eq), 4-(4,4,5,5-tetramethyl-1,3,2-dioxaborolan-2-yl)naphthalen-2-ol (206 mg, 762 μmol, 1.5 eq) and Cs₂CO₃ (414 mg, 1.27 mmol, 2.5 eq) in dioxane (5 mL) and water (0.5 mL) was added Pd(PPh₃)₄ (58.7 mg, 50.8 μmol, 0.1 eq). The mixture was stirred at 100° C. for 3 hours. After completion, the mixture was diluted with water (50 mL) and extracted with ethyl acetate (2×80 mL). The combined organic layers were washed with brine (40 mL), dried over Na₂SO₄, filtered and concentrated in vacuum. The residue was purified with reverse phase chromatography (0.1% formic acid) to give (1R,5S)-tert-butyl 3-(8-fluoro-7-(3-hydroxynaphthalen-1-yl)pyrido[4,3-d]pyrimidin-4-yl)-3,8-diazabicyclo[3.2.1]octane-8-carboxylate (180 mg, 71% yield) as a yellow solid. ¹H NMR (400 MHz, DMSO-d₆)

δ=10.10 (br s, 1H), 9.33 (s, 1H), 8.74 (s, 1H), 7.80 (d, J=8.0 Hz, 1H), 7.56 (br d, J=8.4 Hz, 1H), 7.44 (dt, J=0.9, 7.5 Hz, 1H), 7.30 (dd, J=2.4, 13.3 Hz, 2H), 7.24 (ddd, J 1.2, 6.8, 8.4 Hz, 1H), 4.63 (br d, J=12.4 Hz, 2H), 4.28 (br s, 2H), 3.70 (br d, J=12.4 Hz, 2H), 1.90-1.76 (m, 2H), 1.66 (br d, J=7.6 Hz, 2H), 1.47 (s, 9H). LCMS [ESI, M+1]: 502.

Step B. 4-(4-((1R,5S)-3,8-diazabicyclo[3.2.1]octan-3-yl)-8-fluoropyrido[4,3-d]pyrimidin-7-yl)naphthalen-2-ol. To a solution of (1R,5S)-tert-butyl 3-(8-fluoro-7-(3-hydroxynaphthalen-1-yl)pyrido[4,3-d]pyrimidin-4-yl)-3,8-diazabicyclo[3.2.1]octane-8-carboxylate (160 mg, 319 μmol, 1.0 eq) in acetonitrile (2 mL) was added HCl/dioxane (4 M, 1 mL, 12.5 eq) dropwise. The mixture was stirred at 15° C. for 1 h. The mixture was concentrated in vacuum. The residue was purified by preparative HPLC (column: Shim-pack C18 150*25*10 μm; mobile phase: [water (0.225% formic acid)-ACN]; B %: 5%-35%, 10 min) and lyophilized to give 4-(4-((1R,5S)-3,8-diazabicyclo[3.2.1]octan-3-yl)-8-fluoropyrido[4,3-d]pyrimidin-7-yl)naphthalen-2-ol (51.7 mg, 39% yield) as an off-white solid. $^1$H NMR (400 MHz, MeOD) δ=9.39-9.18 (m, 1H), 8.93-8.69 (m, 1H), 7.77 (d, J=8.0 Hz, 1H), 7.55 (br d, J=8.4 Hz, 1H), 7.49-7.40 (m, 1H), 7.31 (d, J=2.0 Hz, 1H), 7.29-7.21 (m, 2H), 4.89 (br s, 2H), 4.06 (br s, 2H), 3.90 (br dd, J=4.0, 13.6 Hz, 2H), 2.11-1.88 (m, 4H). LCMS [ESI, M+1]: 402.

Example 182

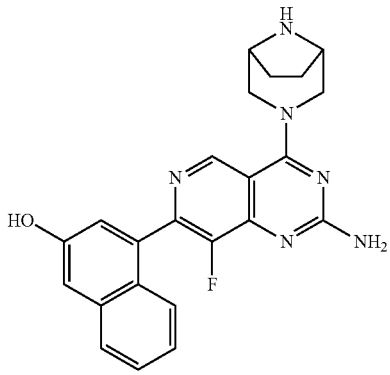 [SMILES: Nc1nc(N2CC3CCC(C2)N3)c2cnc(-c3cc(O)cc4ccccc34)c(F)c2n1]

4-[2-amino-4-(3,8-diazabicyclo[3.2.1]octan-3-yl)-8-fluoro-pyrido[4,3-d]pyrimidin-7-yl]naphthalen-2-ol

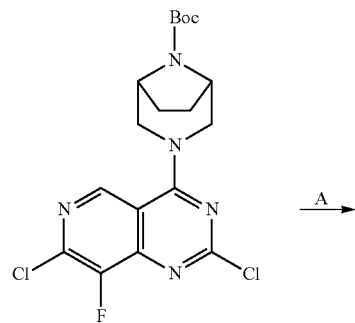

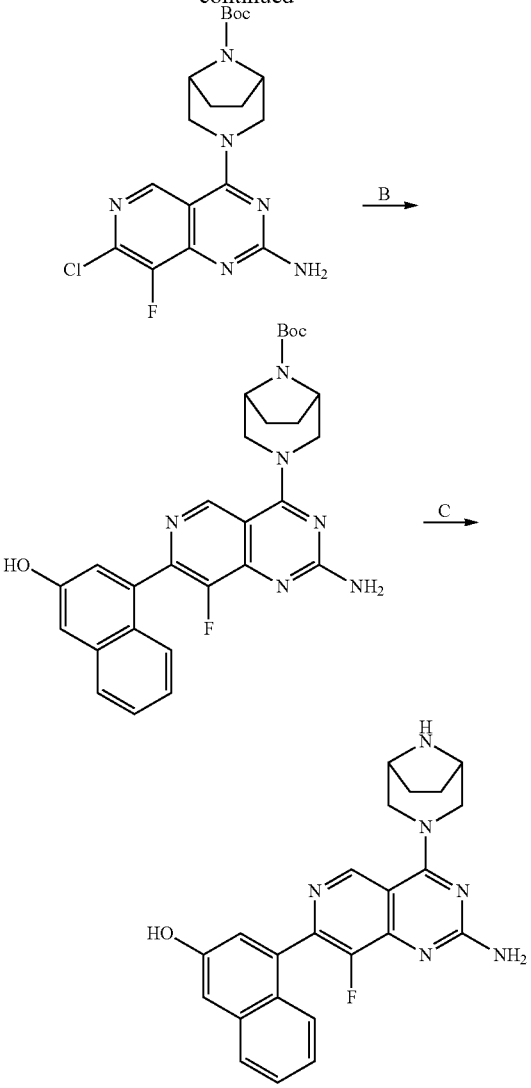

Step A. tert-butyl 3-(2-amino-7-chloro-8-fluoro-pyrido[4,3-d]pyrimidin-4-yl)-3,8-diazabicyclo [3.2.1]octane-8-carboxylate. To a suspension of tert-butyl (1R,5S)-3-(2,7-dichloro-8-fluoropyrido[4,3-d]pyrimidin-4-yl)-3,8-diazabicyclo[3.2.1]octane-8-carboxylate (0.3 g, 700 μmol, 1.0 eq) in i-PrOH (1.5 mL) was added NH$_3$·H$_2$O (1.96 g, 14.0 mmol, 2.16 mL, 20 eq) dropwise. The resulting mixture was heated to 70° C. and stirred for 6 hours at 70° C. in a sealed tube. The solvent was removed under reduced pressure. The residue was purified by reversed phase chromatography [water (0.1% formic acid)/acetonitrile]. The desired fractions were collected, neutralized with solid NaHCO$_3$, concentrated under vacuum to remove MeCN and extracted with ethyl acetate (2×20 mL). The organic layers were dried over Na$_2$SO$_4$ and concentrated under vacuum to give tert-butyl-3-(2-amino-7-chloro-8-fluoro-pyrido[4,3-d]pyrimidin-4-yl)-3,8-diazabicyclo[3.2.1]octane-8-carboxylate (100 mg, 34% yield) as a yellow solid; $^1$H NMR (400 MHz, DMSO-d6): δ 8.62 (s, 1H), 7.48-6.92 (m, 2H), 4.47-4.27 (m, 2H), 4.24-4.13 (m, 2H), 3.57-3.40 (m, 2H), 1.85-1.73 (m, 2H), 1.72-1.62 (m, 2H), 1.45 (s, 9H).

Step B. tert-butyl 3-[2-amino-8-fluoro-7-(3-hydroxy-1-naphthyl)pyrido[4,3-d]pyrimidin-4-yl]-3,8-diazabicyclo

[3.2.1]octane-8-carboxylate. A mixture of tert-butyl-3-(2-amino-7-chloro-8-fluoro-pyrido[4,3-d]pyrimidin-4-yl)-3,8-diazabicyclo[3.2.1]octane-8-carboxylate (0.09 g, 220 µmol, 1.0 eq), 4-(4,4,5,5-tetramethyl-1,3,2-dioxaborolan-2-yl)naphthalen-2-ol (101 mg, 374 µmol, 1.7 eq), Pd(PPh$_3$)$_4$ (25.4 mg, 22.0 µmol, 0.1 eq) and Cs$_2$CO$_3$ (143 mg, 440 µmol, 2.0 eq) in dioxane (2 mL) and H$_2$O (0.4 mL) was degassed and then heated to 100° C. for 7 hours under N2. The mixture was filtered, and the filtrate was diluted with water (3 mL) and extracted with ethyl acetate (2×5 mL). The organic layers were dried over Na$_2$SO$_4$ and concentrated under vacuum. The residue was purified by reversed phase chromatography [water (0.1% formic acid)/acetonitrile]. The desired fractions were collected, neutralized with solid NaHCO$_3$, concentrated under vacuum to remove MeCN and extracted with ethyl acetate (2×10 mL). The organic layers were dried over Na$_2$SO$_4$ and concentrated under vacuum to give tert-butyl 3-[2-amino-8-fluoro-7-(3-hydroxy-1-naphthyl)pyrido[4,3-d]pyrimidin-4-yl]-3,8-diazabicyclo[3.2.1]octane-8-carboxylate (102 mg, 77% yield) as a yellow solid; $^1$H NMR (400 MHz, DMSO-d6): δ 9.93 (s, 1H), 8.93 (s, 1H), 7.78 (d, J=8.4 Hz, 1H), 7.66-7.62 (m, 1H), 7.55-7.53 (m, 1H), 7.45-7.40 (m, 1H), 7.24-7.20 (m, 1H), 7.19-7.17 (m, 1H), 4.51-4.34 (m, 2H), 4.29-4.19 (m, 2H), 3.58-3.46 (m, 2H), 3.39-3.34 (m, 2H), 1.88-1.73 (m, 4H), 1.46 (s, 9H).

Step C. 4-[2-amino-4-(3,8-diazabicyclo[3.2.1]octan-3-yl)-8-fluoro-pyrido[4,3-d]pyrimidin-7-yl]naphthalen-2-ol. To a solution of tert-butyl 3-[2-amino-8-fluoro-7-(3-hydroxy-1-naphthyl)pyrido[4,3-d]pyrimidin-4-yl]-3,8-diazabicyclo[3.2.1]octane-8-carboxylate (97 mg, 161 µmol, 1.0 eq) in DCM (90 ul) was added TFA (276 mg, 2.42 mmol, 179 µL, 15 eq). The mixture was stirred at 20° C. for 0.5 hour, and the solvent was removed under reduced pressure. The residue was neutralized with saturated aqueous Na$_2$CO$_3$ (3 mL) and extracted with ethyl acetate (3×5 mL). The organic layers were dried over Na$_2$SO$_4$ and concentrated under vacuum. The residue was purified by preparative HPLC (column: Phenomenex Synergi C18 150*25*10 µm; mobile phase: [water (0.225% formic acid)-ACN]; B %: 1%-26%, 10 min). The desired fractions were collected and lyophilized to give 4-[2-amino-4-(3,8-diazabicyclo[3.2.1]octan-3-yl)-8-fluoro-pyrido[4,3-d]pyrimidin-7-yl]naphthalen-2-ol (43.7 mg, 58% yield, formic acid). Yellow solid; $^1$H NMR (400 MHz, D$_2$O): δ 8.47 (s, 1H), 7.77-7.72 (m, 1H), 7.45-7.39 (m, 1H), 7.36-7.31 (m, 1H), 7.29 (d, J=2.4 Hz, 1H), 7.22-7.16 (m, 1H), 7.07 (d, J=2.4 Hz, 1H), 4.45-4.37 (m, 2H), 4.12-4.05 (m, 2H), 3.67 (br d, J=14.0 Hz, 2H), 1.98-1.87 (m, 2H), 1.86-1.72 (m, 2H); LCMS [ESI, M+1]: 417.

Example 183

4-[4-(3,8-diazabicyclo[3.2.1]octan-3-yl)-8-fluoro-2-(methylamino)pyrido[4,3-d]pyrimidin-7-yl]naphthalen-2-ol

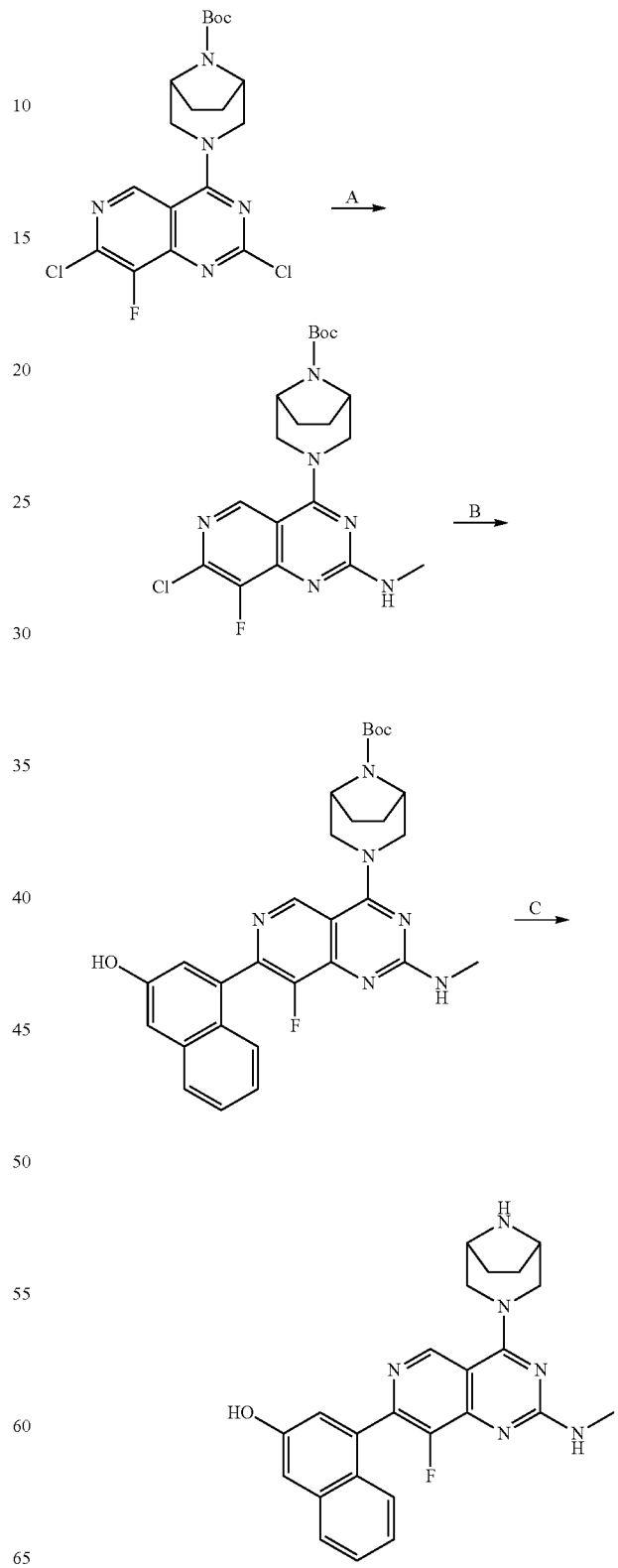

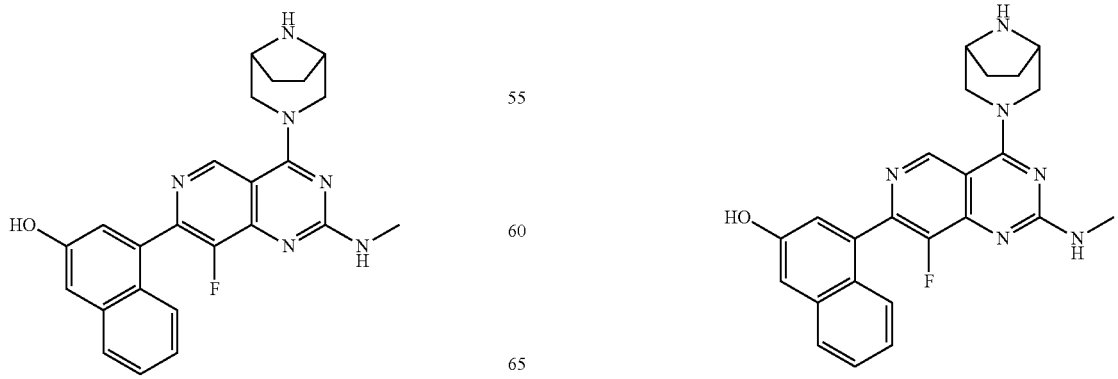

Step A. tert-butyl-3-[7-chloro-8-fluoro-2-(methylamino)pyrido[4,3-d]pyrimidin-4-yl]-3,8-diazabicyclo[3.2.1]octane-8-carboxylate. To a solution of tert-butyl (1R,5S)-3-(2,7-dichloro-8-fluoropyrido[4,3-d]pyrimidin-4-yl)-3,8-diazabicyclo[3.2.1]octane-8-carboxylate (0.1 g, 233 μmol, 1.0 eq) in dioxane (1.0 mL) was added methanamine (2 M in THF, 1.17 mL, 10 eq). The mixture was stirred 15° C. for 2 hours in a sealed tube, and the solvent was removed under reduced pressure to give tert-butyl-3-[7-chloro-8-fluoro-2-(methylamino)pyrido[4,3-d]pyrimidin-4-yl]-3,8-diazabicyclo[3.2.1]octane-8-carboxylate (102 mg, 98% yield) which was used directly in the next step without further purification as a yellow solid; LCMS [ESI, M+1]: 423.

Step B. tert-butyl 3-[8-fluoro-7-(3-hydroxy-1-naphthyl)-2-(methylamino)pyrido[4,3-d]pyrimidin-4-yl]-3,8-diazabicyclo[3.2.1]octane-8-carboxylate. A mixture of tert-butyl-3-[7-chloro-8-fluoro-2-(methylamino)pyrido[4,3-d]pyrimidin-4-yl]-3,8-diazabicyclo[3.2.1]octane-8-carboxylate (75.0 mg, 177 μmol, 1.0 eq), 4-(4,4,5,5-tetramethyl-1,3,2-dioxaborolan-2-yl)naphthalen-2-ol (71.9 mg, 266 μmol, 1.5 eq), $Cs_2CO_3$ (144 mg, 443 μmol, 2.5 eq) and $Pd(PPh_3)_4$ (20.5 mg, 17.8 μmol, 0.1 eq) in dioxane (1.4 mL) and $H_2O$ (0.14 mL) was degassed and then heated to 90° C. for 3 hours under $N_2$. After completion, the reaction mixture was poured into 1 mL of water and extracted with ethyl acetate (1 mL×2). The combined organic phase dried with anhydrous $Na_2SO_4$, filtered and concentrated in vacuum. The crude product was purified by preparative TLC (petroleum ether/ethyl acetate=1:1) to give tert-butyl 3-[8-fluoro-7-(3-hydroxy-1-naphthyl)-2-(methylamino)pyrido[4,3-d]pyrimidin-4-yl]-3,8-diazabicyclo[3.2.1]octane-8-carboxylate (40 mg, 31% yield) as a yellow solid; Rf=0.67 (1/1 petroleum ether/ethyl acetate); LCMS [ESI, M+1]: 531.

Step C. 4-[4-(3,8-diazabicyclo[3.2.1]octan-3-yl)-8-fluoro-2-(methylamino)pyrido[4,3-d]pyrimidin-7-yl]naphthalen-2-ol. To a mixture of tert-butyl 3-[8-fluoro-7-(3-hydroxy-1-naphthyl)-2-(methylamino)pyrido[4,3-d]pyrimidin-4-yl]-3,8-diazabicyclo[3.2.1]octane-8-carboxylate (40 mg, 75.4 μmol, 1.0 eq) in ACN (0.2 mL) was added HCl·dioxane (4.0 M, 0.4 mL, 21 eq). The mixture was stirred at 15° C. for 0.5 hour. After completion, the mixture was concentrated in vacuum. The pH was adjusted to 8 with saturated $Na_2CO_3$ solution. The aqueous layer was extracted with a mixed mixture (ethyl acetate/methanol=10/1, 1.5 mL×2). The combined organic phase was dried over anhydrous $Na_2SO_4$ and concentrated in vacuo. The crude product was purified by preparative HPLC (column: Waters Xbridge 150*25 mm*5 μm; mobile phase: [water (10 mM $NH_4HCO_3$)-ACN]; B %: 15%-45%, 10 min). The desired fractions was collected and lyophilized to give 4-[4-(3,8-diazabicyclo[3.2.1]octan-3-yl)-8-fluoro-2-(methylamino)pyrido[4,3-d]pyrimidin-7-yl]naphthalen-2-ol (12.7 mg, 38% yield) as a yellow solid; $^1$H NMR (400 MHz, $CDCl_3$): δ 8.90 (s, 1H), 7.79-7.72 (m, 1H), 7.70 (br d, J=8.4 Hz, 1H), 7.50-7.42 (m, 1H), 7.41-7.35 (m, 1H), 7.27-7.20 (m, 2H), 5.96-5.75 (m, 1H), 4.62-4.26 (m, 2H), 3.69-3.46 (m, 4H), 3.02 (br s, 3H), 1.84-1.76 (m, 4H); LCMS [ESI, M+1]: 431.

Example 184

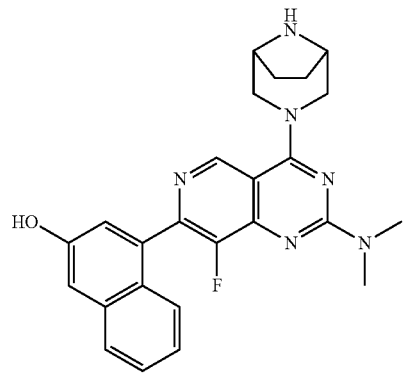

4-[4-(3,8-diazabicyclo[3.2.1]octan-3-yl)-2-(dimethylamino)-8-fluoro-pyrido[4,3-d]pyrimidin-7-yl]naphthalen-2-ol Synthesized according to Example 183 substituting dimethylamine in place of methylamine (15.0 mg, 24% yield) as a white solid; $^1$H NMR (400 MHz, $CDCl_3$): δ 8.87 (s, 1H), 7.67 (br d, J=8.4 Hz, 1H), 7.63 (d, J=8.0 Hz, 1H), 7.40-7.35 (m, 1H), 7.33-7.31 (m, 1H), 7.26-7.21 (m, 1H), 7.14-7.11 (m, 1H), 4.45-4.36 (m, 2H), 3.67-3.58 (m, 2H), 3.57-3.48 (m, 2H), 3.29 (s, 6H), 1.87-1.78 (m, 4H); LCMS [ESI, M+1]: 445.

Example 185

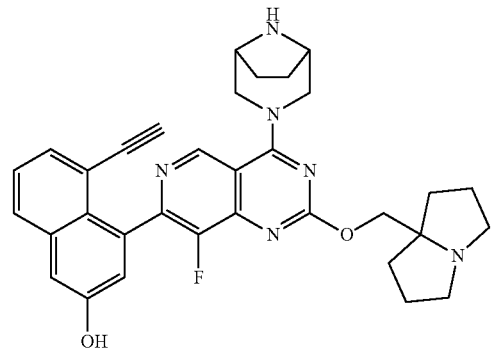 [SMILES: C#Cc1cccc2cc(O)cc(-c3ncc4c(N5CC6CCC(C5)N6)nc(OCC56CCCN5CCC6)nc4c3F)c12]

4-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)-5-ethynylnaphthalen-2-ol

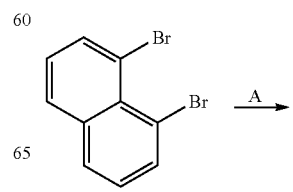

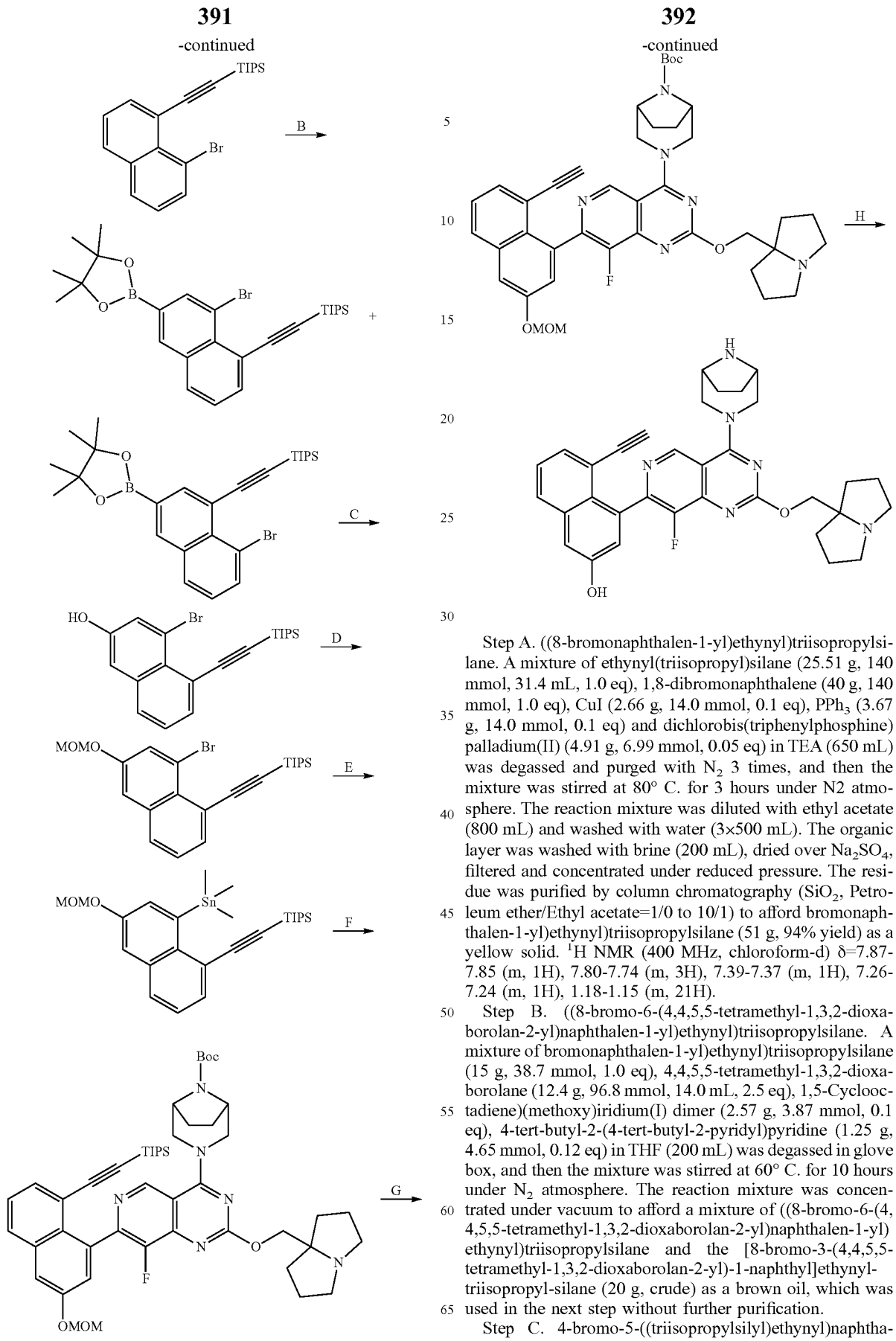

Step A. ((8-bromonaphthalen-1-yl)ethynyl)triisopropylsilane. A mixture of ethynyl(triisopropyl)silane (25.51 g, 140 mmol, 31.4 mL, 1.0 eq), 1,8-dibromonaphthalene (40 g, 140 mmol, 1.0 eq), CuI (2.66 g, 14.0 mmol, 0.1 eq), PPh$_3$ (3.67 g, 14.0 mmol, 0.1 eq) and dichlorobis(triphenylphosphine)palladium(II) (4.91 g, 6.99 mmol, 0.05 eq) in TEA (650 mL) was degassed and purged with N$_2$ 3 times, and then the mixture was stirred at 80° C. for 3 hours under N2 atmosphere. The reaction mixture was diluted with ethyl acetate (800 mL) and washed with water (3×500 mL). The organic layer was washed with brine (200 mL), dried over Na$_2$SO$_4$, filtered and concentrated under reduced pressure. The residue was purified by column chromatography (SiO$_2$, Petroleum ether/Ethyl acetate=1/0 to 10/1) to afford bromonaphthalen-1-yl)ethynyl)triisopropylsilane (51 g, 94% yield) as a yellow solid. $^1$H NMR (400 MHz, chloroform-d) δ=7.87-7.85 (m, 1H), 7.80-7.74 (m, 3H), 7.39-7.37 (m, 1H), 7.26-7.24 (m, 1H), 1.18-1.15 (m, 21H).

Step B. ((8-bromo-6-(4,4,5,5-tetramethyl-1,3,2-dioxaborolan-2-yl)naphthalen-1-yl)ethynyl)triisopropylsilane. A mixture of bromonaphthalen-1-yl)ethynyl)triisopropylsilane (15 g, 38.7 mmol, 1.0 eq), 4,4,5,5-tetramethyl-1,3,2-dioxaborolane (12.4 g, 96.8 mmol, 14.0 mL, 2.5 eq), 1,5-Cyclooctadiene)(methoxy)iridium(I) dimer (2.57 g, 3.87 mmol, 0.1 eq), 4-tert-butyl-2-(4-tert-butyl-2-pyridyl)pyridine (1.25 g, 4.65 mmol, 0.12 eq) in THF (200 mL) was degassed in glove box, and then the mixture was stirred at 60° C. for 10 hours under N$_2$ atmosphere. The reaction mixture was concentrated under vacuum to afford a mixture of ((8-bromo-6-(4,4,5,5-tetramethyl-1,3,2-dioxaborolan-2-yl)naphthalen-1-yl)ethynyl)triisopropylsilane and the [8-bromo-3-(4,4,5,5-tetramethyl-1,3,2-dioxaborolan-2-yl)-1-naphthyl]ethynyl-triisopropyl-silane (20 g, crude) as a brown oil, which was used in the next step without further purification.

Step C. 4-bromo-5-((triisopropylsilyl)ethynyl)naphthalen-2-ol. To a solution of [8-bromo-6-(4,4,5,5-tetramethyl- 1,3,2-dioxaborolan-2-yl)-1-naphthyl]ethynyl-triisopropylsilane and [8-bromo-3-(4,4,5,5-tetramethyl-1,3,2-dioxaborolan-2-yl)-1-naphthyl]ethynyl-triisopropyl-silane (20 g, 39.0 mmol, 1.0 eq) in H₂O (150 mL) and THF (300 mL) were added H₂O₂ (36.3 g, 320 mmol, 30.8 mL, 30% purity, 8.2 eq) and AcOH (161 g, 2.69 mol, 154 mL, 69 eq). The mixture was stirred at 10° C. for 1 hour. Upon completion, the reaction mixture was quenched with saturated NaHSO₃ solution (100 mL) and extracted with ethyl acetate (3×200 mL). The combined organic layers were washed with brine (200 mL), dried over Na₂SO₄, filtered and concentrated under reduced pressure. The residue was purified by column chromatography (SiO₂, Petroleum ether/Ethyl acetate=100/1 to 3/1) and further purified by reversed phase flash chromatography [water (0.1% formic acid)/acetonitrile]. SFC chromatography showed the ratio of Peak 1 (Ret.time: 1.223 min)/Peak 2 (Ret.time: 1.429 min)=66/33. The residue was separated by SFC (column: DAICEL CHIRALPAK IG (250 mm*50 mm, 10 μm); mobile phase: [0.1% NH₃H₂O IPA]; B %: 25%-25%, 2.7 min; 135 min) to afford 4-bromo-5-((triisopropylsilyl)ethynyl)naphthalen-2-ol (Peak 1, 1.5 g, 9.54% yield) as a yellow solid. $^1$H NMR (400 MHz, chloroform-d) δ=7.73-7.72 (m, 1H), 7.62 (m, 1H), 7.49 (d, J=2.8 Hz, 1H), 7.33 (m, 1H), 7.12 (d, J=2.8 Hz, 1H), 1.20-1.16 (m, 21H).

Step D. ((8-bromo-6-(methoxymethoxy)naphthalen-1-yl)ethynyl)triisopropylsilane. To a solution of 4-bromo-5-(2-triisopropylsilylethynyl)naphthalen-2-ol (1 g, 2.48 mmol, 1.0 eq) in DCM (20 mL) were added DIEA (961 mg, 7.44 mmol, 1.30 mL, 3.0 eq) and methoxymethyl chloride (299 mg, 3.72 mmol, 282 μL, 1.5 eq). The mixture was stirred at 0° C. for 30 minutes. Upon completion, the reaction mixture was diluted with water (20 mL) and extracted with DCM (3×30 mL). The combined organic layers were washed with brine (20 mL), dried over Na₂SO₄, filtered and concentrated under reduced pressure. The residue was purified by column chromatography (SiO₂, Petroleum ether/Ethyl acetate=100/1 to 5/1) to afford ((8-bromo-6-(methoxymethoxy)naphthalen-1-yl)ethynyl)triisopropylsilane (900 mg, 81% yield) as a white solid. $^1$H NMR (400 MHz, chloroform-d) δ=7.76-7.74 (m, 2H), 7.60 (d, J=2.8 Hz, 1H), 7.37-7.35 (m, 2H), 5.27 (s, 2H), 3.53 (s, 3H), 1.20-1.16 (m, 21H).

Step E. triisopropyl((6-(methoxymethoxy)-8-(trimethylstannyl)naphthalen-1-yl)ethynyl)silane. A mixture of 2-[8-bromo-6-(methoxymethoxy)-1-naphthyl]ethynyl-triisopropyl-silane (1.10 g, 2.46 mmol, 1.0 eq), trimethyl(trimethylstannyl)stannane (4.03 g, 12.29 mmol, 2.55 mL, 5 eq.), Pd(PPh₃)₄ (284 mg, 246 μmol, 0.1 eq) in toluene (20 mL) was degassed and purged with N2 for 3 times, and then the mixture was stirred at 110° C. for 12 hours under N₂ atmosphere. Upon completion, the reaction mixture was diluted with water (20 mL) and extracted with ethyl acetate (3×20 mL). The combined organic layers were washed with and brine (20 mL), dried over Na₂SO₄, filtered and concentrated under reduced pressure. The residue was purified by reversed phase flash chromatography [water (0.1% formic acid)/acetonitrile)] to afford triisopropyl((6-(methoxymethoxy)-8-(trimethylstannyl)naphthalen-1-yl)ethynyl)silane (300 mg, 23% yield) as a yellow oil. $^1$H NMR (400 MHz, chloroform-d) δ=7.76-7.72 (m, 2H), 7.51 (s, 1H), 7.38-7.34 (m, 2H), 5.30 (s, 2H), 3.54 (s, 3H), 1.20-1.18 (m, 21H), 0.49 (s, 9H).

Step F. (1R,5S)-tert-butyl-3-(8-fluoro-2-((hexahydro-1H-pyrrolizin-7a-yl)methoxy)-7-(3-(methoxymethoxy)-8-((triisopropylsilyl)ethynyl)naphthalen-1-yl)pyrido[4,3-d]pyrimidin-4-yl)-3,8-diazabicyclo[3.2.1]octane-8-carboxylate. A mixture of tert-butyl (1R,5S)-3-(7-chloro-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (150 mg, 281.4 μmol, 1.0 eq), triisopropyl((6-(methoxymethoxy)-8-(trimethylstannyl)naphthalen-1-yl)ethynyl)silane (299 mg, 563 μmol, 2.0 eq), CuI (16.1 mg, 84.4 μmol, 0.3 eq), BINAP (35.0 mg, 56.3 μmol, 0.2 eq) and Pd(dppf)Cl₂ (20.6 mg, 28.1 μmol, 0.1 eq) in toluene (3 mL) was degassed and purged with N₂ for 3 times, and then the mixture was stirred at 100° C. for 12 hours under N₂ atmosphere. Upon completion, the reaction mixture was diluted with water (20 mL) and extracted with ethyl acetate (3×30 mL). The combined organic layers were washed with brine (20 mL), dried over Na₂SO₄, filtered and concentrated under reduced pressure. The residue was purified by reversed phase flash chromatography [water (0.1% formic acid)/acetonitrile)] to obtain (1R,5S)-tert-butyl-3-(8-fluoro-2-((hexahydro-1H-pyrrolizin-7a-yl)methoxy)-7-(3-(methoxymethoxy)-8-((triisopropylsilyl)ethynyl)naphthalen-1-yl)pyrido[4,3-d]pyrimidin-4-yl)-3,8-diazabicyclo[3.2.1]octane-8-carboxylate (60 mg, 18.24% yield) as a yellow solid. LCMS [ESI, M+1]: 865.

Step G. (1R,5S)-tert-butyl-3-(7-(8-ethynyl-3-(methoxymethoxy)naphthalen-1-yl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate. To a solution of (1R,5S)-tert-butyl-3-(8-fluoro-2-((hexahydro-1H-pyrrolizin-7a-yl)methoxy)-7-(3-(methoxymethoxy)-8-((triisopropylsilyl)ethynyl)naphthalen-1-yl)pyrido[4,3-d]pyrimidin-4-yl)-3,8-diazabicyclo[3.2.1]octane-8-carboxylate (50.0 mg, 57.8 μmol, 1.0 eq) in DMF (1 mL) was added CsF (87.8 mg, 578 μmol, 21.3 μL, 10 eq). The mixture was stirred at 20° C. for 2 hours. After completion, the reaction mixture was diluted with ethyl acetate (10 mL) and washed with water (3×5 mL). The combined organic layers were washed with saturated brine (10 mL), dried over Na₂SO₄, filtered and concentrated under reduced pressure. The residue was purified by reversed phase flash chromatography [water (0.1% formic acid)/acetonitrile)] to afford (1R,5S)-tert-butyl-3-(8-fluoro-2-((hexahydro-1H-pyrrolizin-7a-yl)methoxy)-7-(3-(methoxymethoxy)-8-((triisopropylsilyl)ethynyl)naphthalen-1-yl)pyrido[4,3-d]pyrimidin-4-yl)-3,8-diazabicyclo[3.2.1]octane-8-carboxylate (30 mg, 72.50% yield) as a brown solid. LCMS [ESI, M+1]: 709.

Step H. 4-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)-5-ethynylnaphthalen-2-ol. A mixture of (1R,5S)-tert-butyl-3-(8-fluoro-2-((hexahydro-1H-pyrrolizin-7a-yl)methoxy)-7-(3-(methoxymethoxy)-8-((triisopropylsilyl)ethynyl)naphthalen-1-yl)pyrido[4,3-d]pyrimidin-4-yl)-3,8-diazabicyclo[3.2.1]octane-8-carboxylate (25.0 mg, 35.3 μmol, 1.0 eq) and HCl/MeOH (4 M, 300 μL, 34 eq) was stirred at 10° C. for 20 minutes. The reaction mixture was concentrated under vacuum. The residue was purified by preparative HPLC (column: Phenomenex Synergi C18 150*25*10 μm; mobile phase: [water (0.225% formic acid-ACN]; B %: 2%-32%, 10 min). The desired fraction was collected and lyophilized to give 4-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)-5-ethynylnaphthalen-2-ol (2.12 mg, 8.8% yield, 2FA) as a brown solid. $^1$H NMR (400 MHz, CD₃OD) δ=9.09 (s, 1H), 8.49 (br s, 2H), 7.83 (d, J=7.4 Hz, 1H), 7.51 (d, J=6.0 Hz, 1H), 7.42-7.34 (m, 2H), 7.16 (d, J=2.8 Hz, 1H), 4.72-4.61 (m, 4H), 4.04 (s, 2H), 3.90 (m, 2H), 3.72-3.68 (m, 2H), 3.26 (m, 2H), 3.04 (s, 1H), 2.33-1.98 (m, 12H). LCMS [ESI, M+1]: 565.

Example 186

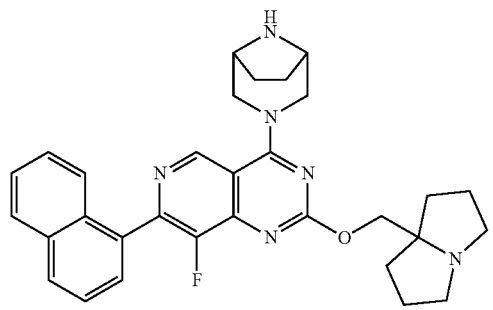 [SMILES: Fc1c(-c2cccc3ccccc23)ncc2c(N3CC4CCC(C3)N4)nc(OCC34CCCN3CCC4)nc12]

4-((1R,5S)-3,8-diazabicyclo[3.2.1]octan-3-yl)-8-fluoro-7-(naphthalen-1-yl)-2-((tetrahydro-1H-pyrrolizin-7a(5H)-yl)methoxy)pyrido[4,3-d]pyrimidine

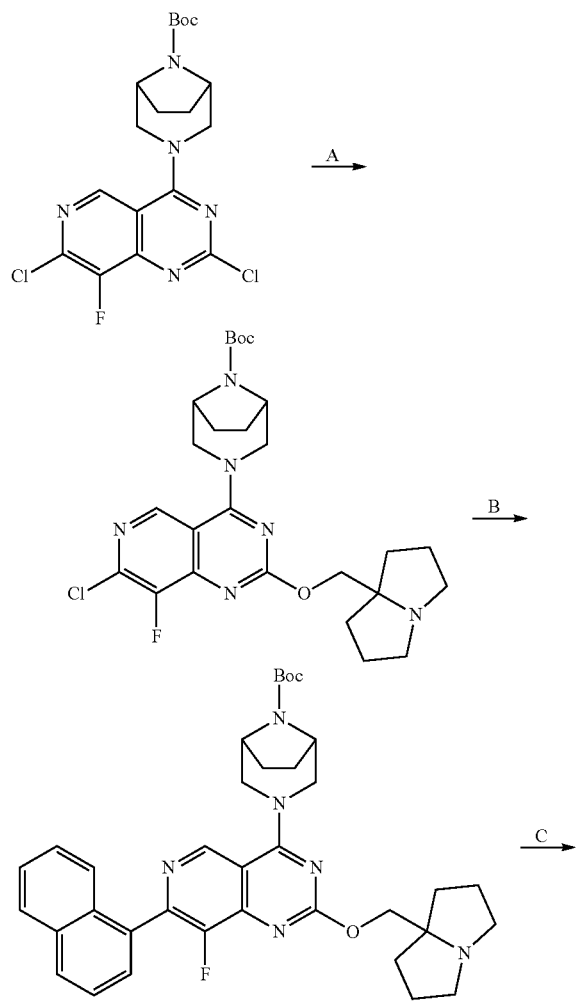

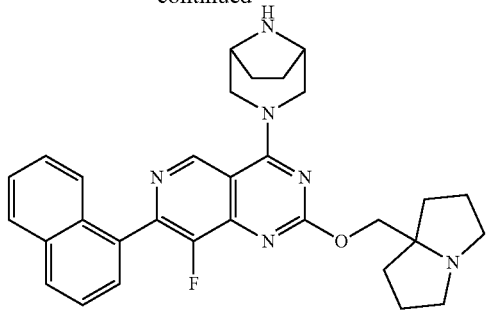

Step A. tert-butyl (1R,5S)-3-(7-chloro-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate. To a mixture of tert-butyl (1R,5S)-3-(2,7-dichloro-8-fluoropyrido[4,3-d]pyrimidin-4-yl)-3,8-diazabicyclo[3.2.1]octane-8-carboxylate (300 mg, 700 μmol, 1.0 eq) and (tetrahydro-1H-pyrrolizin-7a(5H)-yl)methanol (247 mg, 1.75 mmol, 2.5 eq) in dioxane (6 mL) was added DIEA (272 mg, 2.10 mmol, 366 μL, 3.0 eq). The mixture was stirred at 80° C. for 12 hours. After completion, the mixture was diluted with ethyl acetate (6 mL) and water (6 mL), and then separated. The aqueous phase was extracted with ethyl acetate (2×5 mL), and the combined organic layers were washed with saturated brine (7 mL), dried over $Na_2SO_4$, filtered and concentrated under vacuum. The residue was purified by reversed phase flash chromatography [water (formic acid, 0.1%)/acetonitrile] to give the title compound (245 mg, 65% yield) as a yellow solid; LCMS [ESI, M+1]: 533.

Step B. tert-butyl (1R,5S)-3-(8-fluoro-7-(naphthalen-1-yl)-2-((tetrahydro-1H-pyrrolizin-7a(5H)-yl)methoxy)pyrido[4,3-d]pyrimidin-4-yl)-3,8-diazabicyclo[3.2.1]octane-8-carboxylate. To a mixture of tert-butyl (1R,5S)-3-(7-chloro-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (215 mg, 403 μmol, 1.0 eq), 1-naphthylboronic acid (208 mg, 1.21 mmol, 3.0 eq) and $Cs_2CO_3$ (394 mg, 1.21 mmol, 3.0 eq) in dioxane (3 mL) and $H_2O$ (1 mL) was added $Pd(PPh_3)_4$ (46.6 mg, 40.3 μmol, 0.10 eq) under $N_2$. The mixture was stirred at 90° C. for 1 hour. After completion, the mixture was diluted with ethyl acetate (6 mL) and water (7 mL). The aqueous phase was extracted with ethyl acetate (2×5 mL), the combined organic layers were washed with saturated brine (8 mL), dried over $Na_2SO_4$, filtered and concentrated under vacuum. The residue was purified by reversed phase flash chromatography [water (formic acid, 0.1%)/acetonitrile] to give the title compound (281 mg, 82% yield) as a yellow solid; LCMS [ESI, M+1]: 625.

Step C. 4-((1R,5S)-3,8-diazabicyclo[3.2.1]octan-3-yl)-8-fluoro-7-(naphthalen-1-yl)-2-((tetrahydro-1H-pyrrolizin-7a(5H)-yl)methoxy)pyrido[4,3-d]pyrimidine. To a mixture of tert-butyl (1R,5S)-3-(8-fluoro-7-(naphthalen-1-yl)-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (150 mg, 175 μmol, 1.0 eq) in acetonitrile (1.5 mL) was added HCl·dioxane (4 M, 3 mL, 68 eq) at 0° C. The mixture was stirred at 0° C. for 0.5 hour. After completion, the mixture was concentrated under vacuum. Then the pH value was adjusted to 9 with saturated $Na_2CO_3$ solution and the mixture was washed with methanol (2×6 mL), filtered and concentrated under vacuum. The residue was purified with preparative HPLC (column: Waters Xbridge 150*25 mm*5 µm; mobile phase: [water (10 mM NH₄HCO₃)-ACN]; B %: 30%-60%, 10 min) twice the title compound (22.5 mg, 24% yield) as a white solid; ¹H NMR (400 MHz, CDCl₃-d) δ=9.10 (s, 1H), 7.95 (dd, J=7.6, 18.0 Hz, 2H), 7.85-7.80 (m, 1H), 7.68 (d, J=7.2 Hz, 1H), 7.63-7.57 (m, 1H), 7.55-7.42 (m, 2H), 4.61 (br d, J=11.2 Hz, 2H), 4.21 (s, 2H), 3.72-3.60 (m, 4H), 3.18-3.07 (m, 2H), 2.71-2.60 (m, 2H), 2.17-2.07 (m, 2H), 1.92-1.81 (m, 8H), 1.73-1.64 (m, 2H); LCMS [ESI, M/2+1, M+1]:263, 525.

Example 187

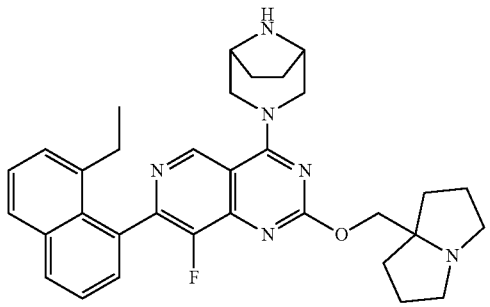 [SMILES: CCc1cccc2cccc(-c3ncc4c(N5CC6CCC(C5)N6)nc(OCC56CCCN5CCC6)nc4c3F)c12]

4-((1R,5S)-3,8-diazabicyclo[3.2.1]octan-3-yl)-7-(8-ethylnaphthalen-1-yl)-8-fluoro-2-((tetrahydro-1H-pyrrolizin-7a(5H)-yl)methoxy)pyrido[4,3-d]pyrimidine

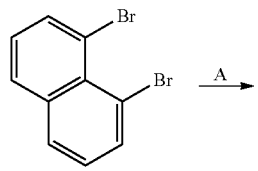

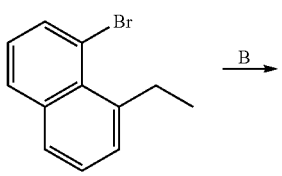

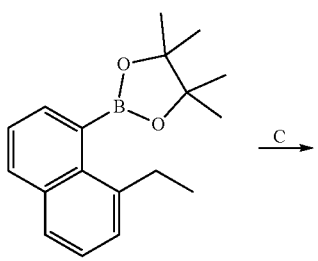

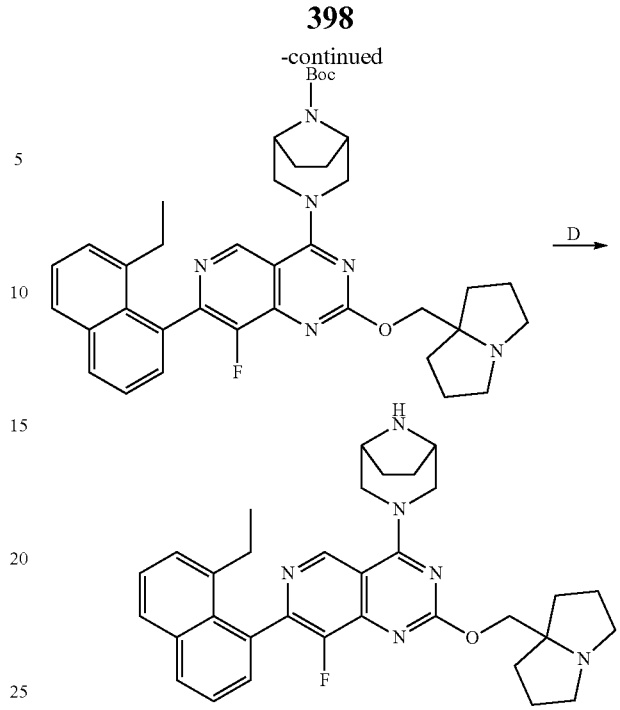

Step A. 1-bromo-8-ethyl-naphthalene. To a mixture of 1,8-dibromonaphthalene (10 g, 34.9 mmol, 1.0 eq) and Pd(dppf)Cl₂ (1.79 g, 2.45 mmol, 0.07 eq) in THF (75 mL) was added ZnEt₂ (1 M, 17.5 mL, 0.5 eq) at −78° C., and the mixture was stirred at 20° C. for 12 hours. The reaction mixture was concentrated under reduced pressure to dryness. The residue was diluted with water (50 mL) and extracted with ethyl acetate (3×50 mL). The combined organic layers were washed with brine (2×30 mL), dried over anhydrous sodium sulfate and filtered. The filtrate was concentrated under reduced pressure to dryness. The crude product was triturated with petroleum ether (50 mL) at 25° C. for 20 minutes, then filtered and washed with petroleum ether (20 mL). The filtrate was concentrated under reduced pressure to dryness. The crude product was purified by reversed phase chromatography (0.1% formic acid condition) to give 1-bromo-8-ethyl-naphthalene (3.3 g, 38% yield). Yellow oil; ¹H NMR (400 MHz, CDCl₃-d) δ=7.70 (dd, J=2.0, 7.6 Hz, 1H), 7.65 (dd, J=1.2, 8.0 Hz, 1H), 7.58 (dd, J=2.4, 7.2 Hz, 1H), 7.30-7.23 (m, 2H), 7.12-7.04 (m, 1H), 3.44 (q, J=7.2 Hz, 2H), 1.23 (t, J=7.6 Hz, 3H).

Step B. 2-(8-ethyl-1-naphthyl)-4,4,5,5-tetramethyl-1,3,2-dioxaborolane. A mixture of 1-bromo-8-ethyl-naphthalene (600 mg, 2.55 mmol, 1.0 eq), bis(pinacolato)diboron (1.62 g, 6.38 mmol, 2.5 eq), KOAc (1.50 g, 15.3 mmol, 6.0 eq), Pd(dppf)Cl₂ (187 mg, 255 µmol, 0.1 eq) in DMF (12 mL) was stirred at 80° C. for 12 hours under N₂. The mixture was diluted with ethyl acetate (20 mL) water (20 mL) and separated. The organic layer was washed with water (3×15 mL) and brine (15 mL), dried over Na₂SO₄, filtered and concentrated under vacuum. The residue was purified by column chromatography (SiO₂, petroleum ether/ethyl acetate=1/0) to give 2-(8-ethyl-1-naphthyl)-4,4,5,5-tetramethyl-1,3,2-dioxaborolane (450 mg, 60% yield) as a white solid; ¹H NMR (400 MHz, CDCl₃-d) δ=7.88 (dd, J=1.2, 8.4 Hz, 1H), 7.76-7.61 (m, 2H), 7.48-7.37 (m, 3H), 3.24 (q, J=7.2 Hz, 2H), 1.46 (s, 12H), 1.39 (t, J=7.2 Hz, 3H).

Step C. tert-butyl (1R,5S)-3-(7-(8-ethylnaphthalen-1-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate. A mixture of tert-butyl (1R,5S)-3-(7-chloro-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (200 mg, 375 μmol, 1.0 eq), 2-(8-ethyl-1-naphthyl)-4,4,5,5-tetramethyl-1,3,2-dioxaborolane (265 mg, 938 μmol, 2.5 eq), Pd(PPh₃)₄ (43.4 mg, 37.5 μmol, 0.1 eq), Cs₂CO₃ (367 mg, 1.13 mmol, 3.0 eq) in dioxane (5.0 mL) and H₂O (1.0 mL) was degassed and purged with N₂ 3 times and then the mixture was stirred at 90° C. for 10 hours under N₂ atmosphere. The reaction mixture was diluted with water (10 mL) and extracted with ethyl acetate (3×15 mL). The combined organic layers were washed with brine (15 mL), dried over Na₂SO₄, filtered and concentrated under reduced pressure. The residue was purified by column chromatography (SiO₂, petroleum ether/ethyl acetate=1/0 to 0/1) and further purified by reversed phase flash chromatography [water (0.1% formic acid)/acetonitrile)] to give the title compound (40 mg, 15% yield). Yellow solid; LCMS [ESI, M+1]: 653.

Step D. 4-((1R,5S)-3,8-diazabicyclo[3.2.1]octan-3-yl)-7-(8-ethylnaphthalen-1-yl)-8-fluoro-2-((tetrahydro-1H-pyrrolizin-7a(5H)-yl)methoxy)pyrido[4,3-d]pyrimidine. To a solution of tert-butyl (1R,5S)-3-(7-(8-ethylnaphthalen-1-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (45 mg, 68.9 μmol, 1 eq) in acetonitrile (0.5 mL) was added HCl·dioxane (4 M, 1.0 mL) at 0° C., the mixture was stirred at 0° C. for 30 minutes. The mixture was concentrated and was diluted with water (1.0 mL). The pH of the mixture was adjusted to ~8 with saturated NaHCO₃ aqueous solution and extracted with dichloromethane (3×5 mL). The combined organic layers were dried over Na₂SO₄, filtered and concentrated. The residue was purified with preparative HPLC (column: Waters X bridge 150*25 mm*5 μm; mobile phase: [water (10 mM NH₄HCO₃)-ACN]; B %: 28%-58%, 10 min). The desired fraction was collected and concentrated under vacuum to remove acetonitrile. The mixture was lyophilized to the title compound (15.2 mg, 39% yield) as a white solid; ¹H NMR (400 MHz, CDCl₃-d) δ=8.99 (s, 1H), 7.96 (d, J=8.0 Hz, 1H), 7.80 (d, J 8.0 Hz, 1H), 7.54-7.41 (m, 3H), 7.36 (d, J=6.8 Hz, 1H), 4.65 (br d, J=12.0 Hz, 1H), 4.52 (br d, J=11.6 Hz, 1H), 4.23-4.16 (m, 2H), 3.72-3.56 (m, 4H), 3.15-3.06 (m, 2H), 2.69-2.60 (m, 2H), 2.49-2.33 (m, 2H), 2.14-2.08 (m, 2H), 1.94-1.81 (m, 8H), 1.72-1.63 (m, 2H), 0.96 (t, J=7.6 Hz, 3H); LCMS [ESI, M+1]: 553.

Example 188

4-(3,8-diazabicyclo[3.2.1]octan-3-yl)-7-(8-ethynyl-1-naphthyl)-8-fluoro-pyrido[4,3-d]pyrimidine

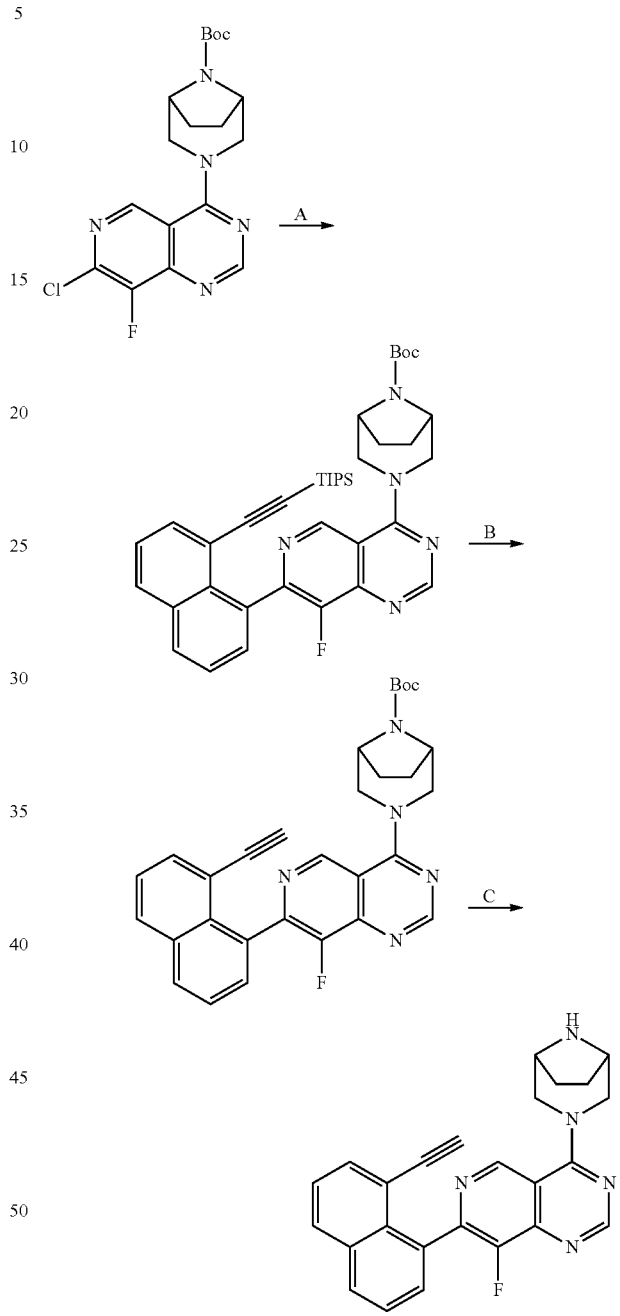

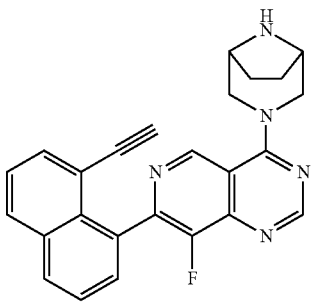 [SMILES: C#Cc1cccc2cccc(-c3ncc4c(N5CC6CCC(C5)N6)ncnc4c3F)c12]

Step A. tert-butyl 3-[8-fluoro-7-[8-(2-triisopropylsilyl-ethynyl)-1-naphthyl]pyrido[4,3-d]pyrimidin-4-yl]-3,8-diazabicyclo[3.2.1]octane-8-carboxylate. To a mixture of tert-butyl (1R,5S)-3-(7-chloro-8-fluoropyrido[4,3-d]pyrimidin-4-yl)-3,8-diazabicyclo[3.2.1]octane-8-carboxylate (200 mg, 508 μmol, 1.0 eq), triisopropyl((8-(trimethylstannyl)naphthalen-1-yl)ethynyl)silane (359 mg, 762 μmol, 1.5 eq), CuI (29.0 mg, 152 μmol, 0.30 eq) and BINAP (63.2 mg, 102 μmol, 0.20 eq) in toluene (4 mL) was added Pd(dppf)Cl₂ (37.2 mg, 50.8 μmol, 0.10 eq) under N₂. The mixture was stirred at 95° C. for 14 hours. After completion, the mixture was filtered. Then the mixture was diluted with ethyl acetate (8 mL) and water (10 mL) and then separated. The aqueous phase was extracted with ethyl acetate (1×8 mL), and the organic layer was washed with saturated brine (10 mL), dried over Na$_2$SO$_4$, filtered and concentrated under vacuum. The residue was purified by column chromatography (Al$_2$O$_3$, petroleum ether: ethyl acetate=3/1-0/1) and reversed phase chromatography [water (formic acid, 0.1%)/acetonitrile] to give tert-butyl 3-[8-fluoro-7-[8-(2-triisopropylsilylethynyl)-1-naphthyl]pyrido[4,3-d]pyrimidin-4-yl]-3,8-diazabicyclo[3.2.1]octane-8-carboxylate (167 mg, 49% yield) as a yellow solid; LCMS [ESI, M+1]: 666.

Step B. tert-butyl 3-[7-(8-ethynyl-1-naphthyl)-8-fluoro-pyrido[4,3-d]pyrimidin-4-yl]-3,8-diazabicyclo[3.2.1]octane-8-carboxylate. To a mixture of tert-butyl 3-[8-fluoro-7-[8-(2-triisopropylsilylethynyl)-1-naphthyl]pyrido[4,3-d]pyrimidin-4-yl]-3,8-diazabicyclo[3.2.1]octane-8-carboxylate (130 mg, 195 μmol, 1.0 eq) in DMF (2 mL) was added CsF (297 mg, 1.95 mmol, 72.0 μL, 10 eq). The mixture was stirred at 25° C. for 0.5 hour. After completion, the residue was purified directly with reversed phase chromatography [water (formic acid, 0.1%)/acetonitrile] to give tert-butyl 3-[7-(8-ethynyl-1-naphthyl)-8-fluoro-pyrido[4,3-d]pyrimidin-4-yl]-3,8-diazabicyclo[3.2.1]octane-8-carboxylate (70 mg, 69% yield) as a brown solid; LCMS [ESI, M+1]: 510.

Step C. 4-(3,8-diazabicyclo[3.2.1]octan-3-yl)-7-(8-ethynyl-1-naphthyl)-8-fluoro-pyrido[4,3-d]pyrimidine. To a solution of tert-butyl 3-[7-(8-ethynyl-1-naphthyl)-8-fluoro-pyrido[4,3-d]pyrimidin-4-yl]-3,8-diazabicyclo[3.2.1]octane-8-carboxylate (70 mg, 137 μmol, 1.0 eq) in acetonitrile (1 mL) was added HCl·dioxane (4 M, 2 mL, 58 eq) at 0° C. The mixture was stirred at 0° C. for 0.5 hour. After completion, the mixture was concentrated under vacuum. The pH was adjusted to 9 with saturated Na$_2$CO$_3$ solution and the mixture was extracted with ethyl acetate (10 mL). The organic layer was concentrated under vacuum. The residue was purified by preparative HPLC (column: Waters Xbridge 150*25 mm*5 μm; mobile phase: [water (10 mM NH$_4$HCO$_3$)-ACN]; B %: 18%-48%, 10 min) to give 4-(3,8-diazabicyclo[3.2.1]octan-3-yl)-7-(8-ethynyl-1-naphthyl)-8-fluoro-pyrido[4,3-d]pyrimidine (35.7 mg, 63% yield) as a yellow solid; $^1$H NMR (400 MHz, CDCl$_3$-d) δ=9.12 (s, 1H), 8.81-8.77 (m, 1H), 8.04-7.95 (m, 2H), 7.77 (dd, J=1.2, 7.2 Hz, 1H), 7.64-7.60 (m, 2H), 7.48 (dd, J=7.2, 8.0 Hz, 1H), 4.69-4.56 (m, 2H), 3.73-3.63 (m, 4H), 2.49 (s, 1H), 1.86-1.72 (m, 4H); LCMS [ESI, M+1]: 410.

Example 189

4-((1R,5S)-3,8-diazabicyclo[3.2.1]octan-3-yl)-7-(8-ethynyl-7-fluoronaphthalen-1-yl)-8-fluoro-2-((tetrahydro-1H-pyrrolizin-7a(5H)-yl)methoxy)pyrido[4,3-d]pyrimidine

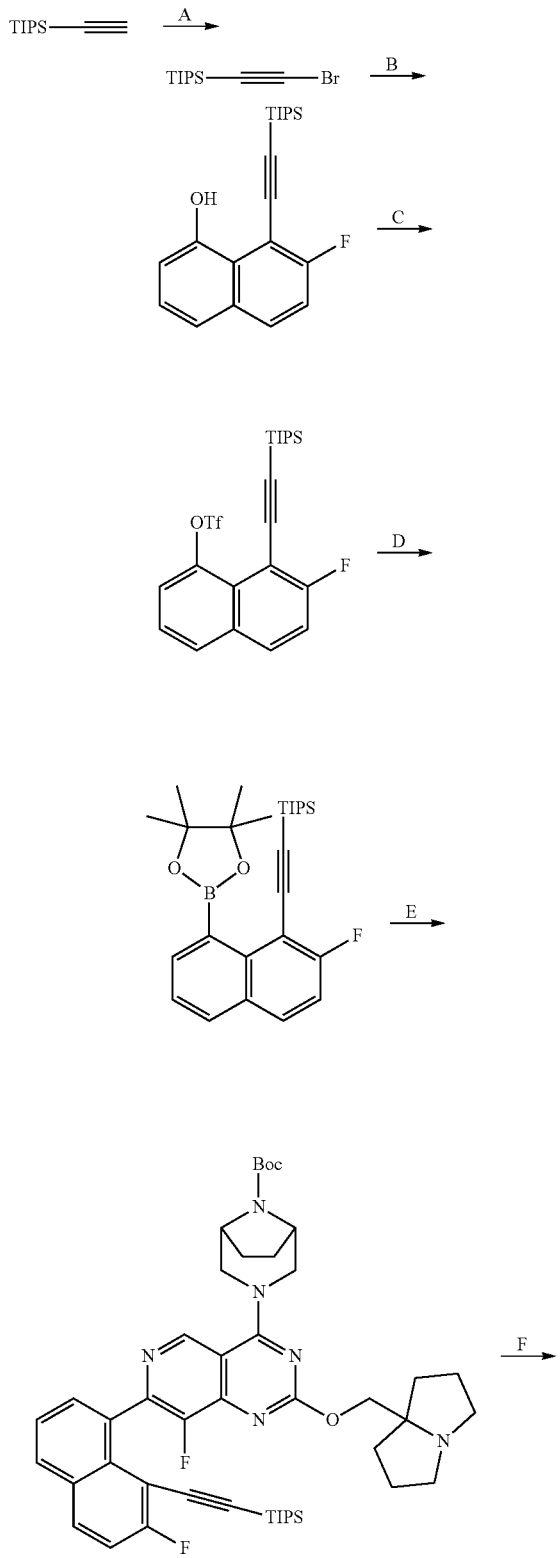

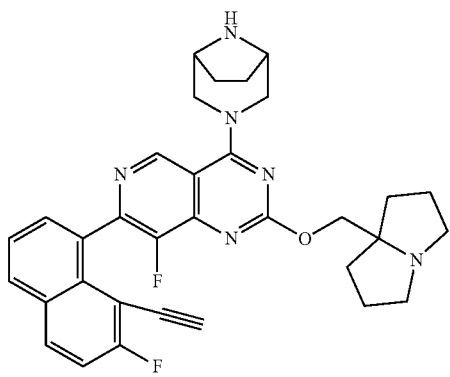 [SMILES: C#Cc1c(F)ccc2cccc(-c3ncc4c(N5CC6CCC(C5)N6)nc(OCC56CCCN5CCC6)nc4c3F)c12]

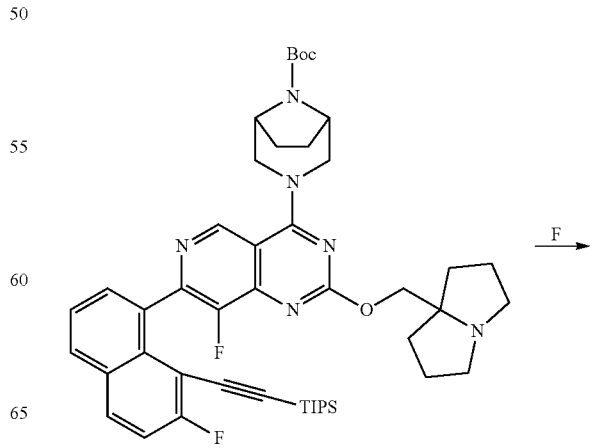

-continued

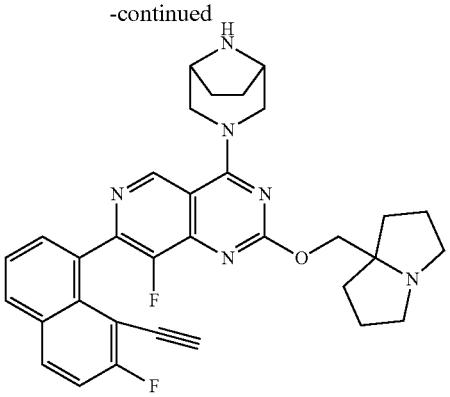

Step A. (bromoethynyl)triisopropylsilane. To a solution of ethynyltriisopropylsilane (1.00 g, 5.48 mmol, 1.23 mL, 1.00 eq) in acetone (30.0 mL) was added NBS (1.13 g, 6.36 mmol, 1.16 eq) followed by silver nitrate (93.1 mg, 548 μmol, 0.10 eq), and the reaction was stirred at 25° C. for 12 hours. Then the mixture was poured into ice. After ice being allowed to melt, the aqueous layer was extracted with petroleum ether (3×30 mL). The combined organic layers were dried over sodium sulfate, filtered and concentrated in vacuum affording (bromoethynyl)triisopropylsilane (1.20 g, 84% yield) as a brown oil; $^1$H NMR (400 MHz, CDCl$_3$) δ 1.25-0.83 (m, 21H).

Step B. 7-fluoro-8-(2-triisopropylsilylethynyl)naphthalen-1-ol. To a solution of (bromoethynyl)triisopropylsilane (445 mg, 1.70 mmol, 1.20 eq) and 7-fluoronaphthalen-1-ol (230 mg, 1.42 mmol, 1.00 eq) in DCE (4.00 mL) was added potassium carbonate (196 mg, 1.42 mmol, 1.00 eq), sodium acetate (23.3 mg, 284 μmol, 0.20 eq) and Dichloro(p-cymene)ruthenium(II) dimer (217 mg, 355 μmol, 0.25 eq). The mixture was stirred at 40° C. for 12 hours. The reaction was cooled to 25° C. and filtered, and the filtrate was concentrated in vacuum to give a residue. The residue was purified by preparative TLC (petroleum ether/ethyl acetate=10/1) affording 7-fluoro-8-(2-triisopropylsilylethynyl)naphthalen-1-ol (450 mg, 93% yield) as a brown solid; LCMS [ESI, 2M+1]: 685.1.

Step C. [7-fluoro-8-(2-triisopropylsilylethynyl)-1-naphthyl] trifluoromethanesulfonate. To a solution of 7-fluoro-8-(2-triisopropylsilylethynyl)naphthalen-1-ol (450 mg, 1.31 mmol, 1.00 eq) in DCM (5.00 mL) were added DIEA (509 mg, 3.94 mmol, 687 μL, 3.00 eq) and trifluoromethanesulfonic anhydride (556 mg, 1.97 mmol, 325 μL, 1.50 eq.) at −40° C. The mixture was stirred at 25° C. for 0.5 hour. The mixture was purified by column chromatography (SiO$_2$, petroleum ether/ethyl acetate=1/0 to 100/1) affording [7-fluoro-8-(2-triisopropylsilylethynyl)-1-naphthyl] trifluoromethanesulfonate (560 mg, 90% yield). Yellow oil; $^1$H NMR (400 MHz, DMSO-d6) δ 8.25 (dd, J=5.6, 9.2 Hz, 1H), 8.19 (dd, J=0.8, 8.0 Hz, 1H), 7.80-7.75 (m, 1H), 7.74-7.70 (m, 1H), 7.69-7.66 (m, 1H), 1.22-1.10 (m, 21H).

Step D. 2-[2-fluoro-8-(4,4,5,5-tetramethyl-1,3,2-dioxaborolan-2-yl)-1-naphthyl]ethynyl-triisopropyl-silane. To a solution of [7-fluoro-8-(2-triisopropylsilylethynyl)-1-naphthyl]trifluoromethanesulfonate (250 mg, 527 μmol, 1.00 eq) and 4,4,5,5-tetramethyl-2-(4,4,5,5-tetramethyl-1,3,2-dioxaborolan-2-yl)-1,3,2-dioxaborolane (200 mg, 790 μmol, 1.50 eq) in dioxane (6.00 mL) were added Pd(dppf)Cl$_2$ (38.5 mg, 52.7 μmol, 0.10 eq) and dry potassium acetate (103 mg, 1.05 mmol, 2.00 eq) under nitrogen atmosphere. The mixture was stirred at 110° C. for 12 hours under nitrogen atmosphere. The mixture was concentrated in vacuum to give a residue. The residue was purified by column chromatography by preparative TLC (SiO$_2$, petroleum ether/ethyl acetate=100/1) affording 2-[2-fluoro-8-(4,4,5,5-tetramethyl-1,3,2-dioxaborolan-2-yl)-1-naphthyl]ethynyl-triisopropyl-silane (80.0 mg, crude) as a red solid; $^1$H NMR (400 MHz, DMSO-d6) δ 8.07 (dd, J=6.0, 9.2 Hz, 1H), 8.04 (dd, J=1.2, 8.2 Hz, 1H), 7.73 (d, J=6.4 Hz, 1H), 7.57-7.53 (m, 1H), 7.52 (dd, J=1.6, 6.8 Hz, 1H), 1.34 (s, 12H), 1.24-1.21 (m, 2H), 1.14-1.09 (m, 19H).

Step E. tert-butyl (1R,5S)-3-(8-fluoro-7-(7-fluoro-8-((triisopropylsilyl)ethynyl)naphthalen-1-yl)-2-((tetrahydro-1H-pyrrolizin-7a(5H)-yl)methoxy)pyrido[4,3-d]pyrimidin-4-yl)-3,8-diazabicyclo[3.2.1]octane-8-carboxylate. To a solution of tert-butyl (1R,5S)-3-(7-chloro-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (94.2 mg, 177 μmol, 1.00 eq) and 2-[2-fluoro-8-(4,4,5,5-tetramethyl-1,3,2-dioxaborolan-2-yl)-1-naphthyl]ethynyl-triisopropyl-silane (80.0 mg, 177 μmol, 1.00 eq) in dioxane (0.80 mL) and water (0.10 mL) were added Pd(PPh$_3$)$_4$ (20.4 mg, 17.7 μmol, 0.10 eq), potassium bifluoride (13.8 mg, 177 μmol, 5.83 μL, 1.00 eq) and cesium carbonate (173 mg, 530 μmol, 3.00 eq) under nitrogen atmosphere. The mixture was stirred at 100° C. for 6 hours. The mixture was concentrated in vacuum to give a residue. The residue was purified by preparative TLC (SiO$_2$, dichloromethane/methanol=10/1) to afford the title compound (25.0 mg, 17% yield) as a red solid; LCMS [ESI, M+1]: 823.3.

Step F. 4-((1R,5S)-3,8-diazabicyclo[3.2.1]octan-3-yl)-7-(8-ethynyl-7-fluoronaphthalen-1-yl)-8-fluoro-2-((tetrahydro-1H-pyrrolizin-7a(5H)-yl)methoxy)pyrido[4,3-d]pyrimidine. To a solution of tert-butyl (1R,5S)-3-(8-fluoro-7-(7-fluoro-8-((triisopropylsilyl)ethynyl)naphthalen-1-yl)-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (25.0 mg, 30.3 μmol, 1.00 eq) in DMF (0.50 mL) was added cesium fluoride (36.9 mg, 243 μmol, 8.96 μL, 8.00 eq). The mixture was stirred at 25° C. for 2 hours. The residue was poured into water (1.00 mL) and stirred for 5 minutes. The aqueous phase was extracted with ethyl acetate (2×3 mL). The combined organic phase was washed with brine (2×3 mL), dried with anhydrous sodium sulfate, filtered and concentrated in vacuum to give a residue. Then the residue was dissolved in acetonitrile (0.50 mL) and HCl·dioxane (0.50 mL) was added. The mixture was stirred at 25° C. for 0.5 hour. The mixture was concentrated in vacuum to give a residue. The resulting mixture was adjusted to pH~8 with ammonium hydroxide (1.00 mL) and dissolved in DMF (1.00 mL). The mixture was purified with preparative HPLC (neutral condition column: Waters Xbridge 150*25 mm*5 μm; mobile phase: [water (10 mM NH$_4$HCO$_3$)-ACN]; B %: 28%-58%, 10 min) affording the title compound (6.00 mg, 34% yield) as a yellow solid; $^1$H NMR (400 MHz, CDCl$_3$) δ 8.98 (s, 1H), 7.99-7.92 (m, 2H), 7.64-7.56 (m, 2H), 7.34 (t, J=8.8 Hz, 1H), 4.70-4.51 (m, 2H), 4.28-4.16 (m, 2H), 3.68 (br d, J=4.4 Hz, 3H), 3.61 (br d, J=12.8 Hz, 1H), 3.20-3.07 (m, 2H), 2.84 (s, 1H), 2.72-2.58 (m, 2H), 2.20-2.07 (m, 2H), 1.93-1.80 (m, 8H), 1.68-1.64 (m, 2H); LCMS [ESI, M+1]: 567.2.

Example 190

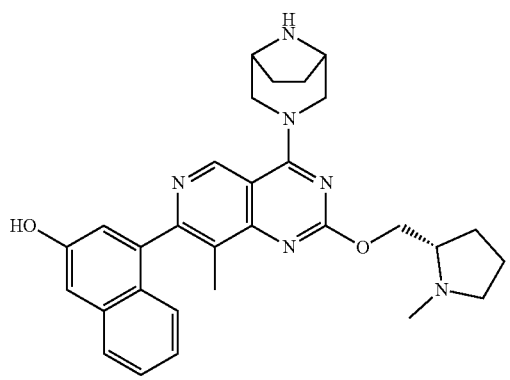 [SMILES: Cc1c(-c2cc(O)cc3ccccc23)ncc2c(N3CC4CCC(C3)N4)nc(OC[C@@H]3CCCN3C)nc12]

4-(4-((1R,5S)-3,8-diazabicyclo[3.2.1]octan-3-yl)-8-methyl-2-(((S)-1-methylpyrrolidin-2-yl)methoxy)pyrido[4,3-d]pyrimidin-7-yl)naphthalen-2-ol

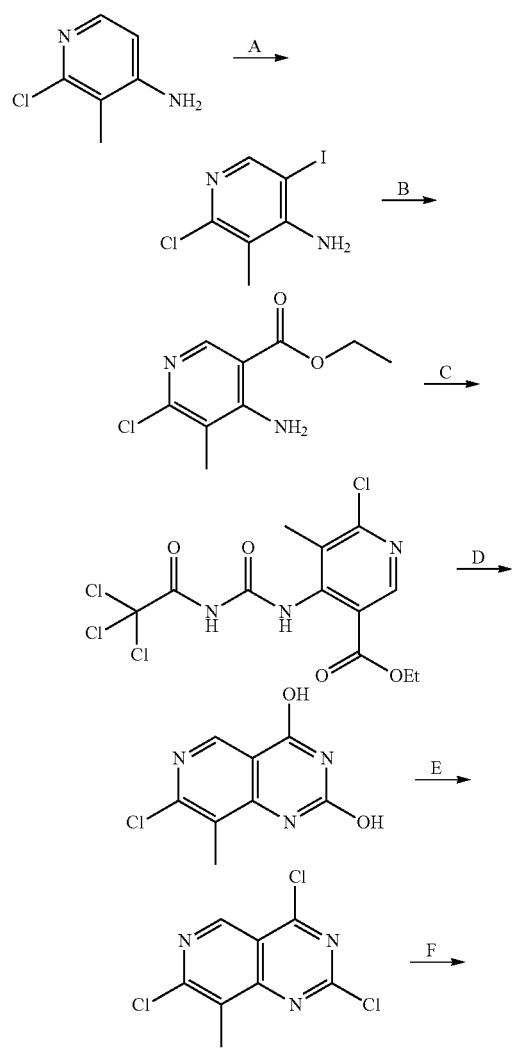

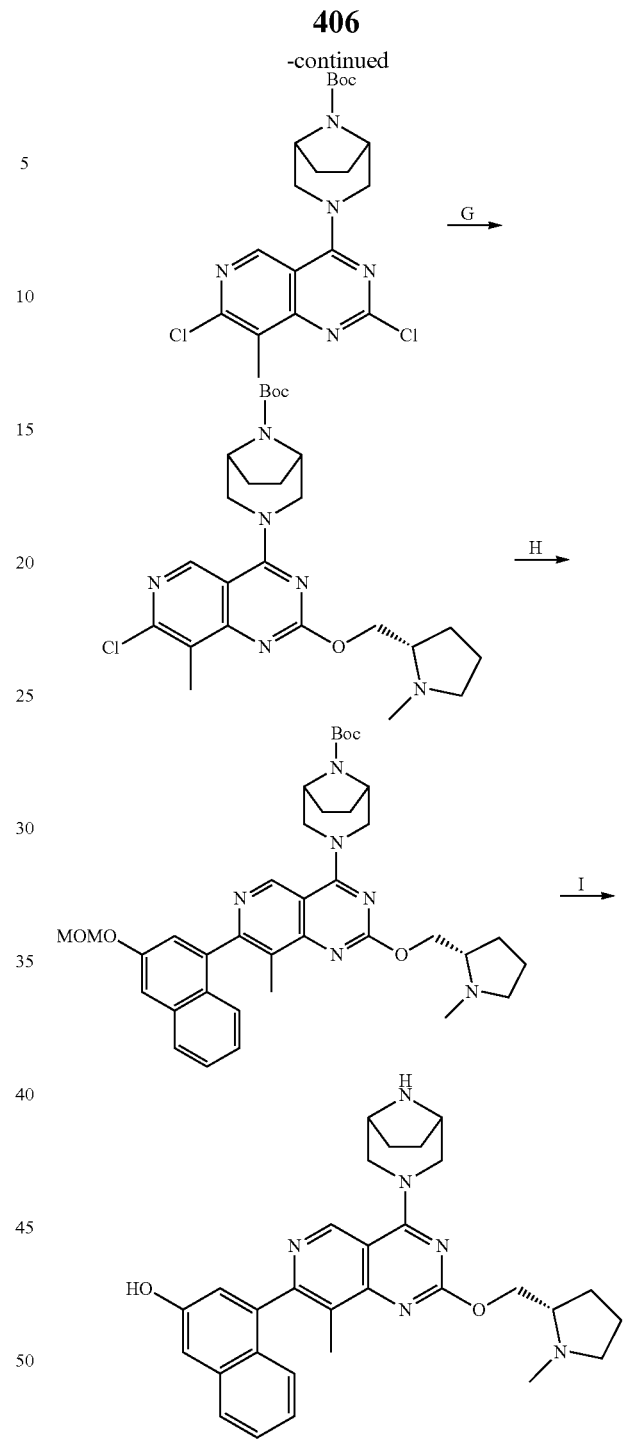

Step A. 2-chloro-5-iodo-3-methylpyridin-4-amine. To a solution of 2-chloro-3-methylpyridin-4-amine (1.00 g, 7.01 mmol, 1.00 eq) in acetonitrile (25.0 mL) was added N-Iodosuccinimide (1.89 g, 8.42 mmol, 1.20 eq). The mixture was stirred at 70° C. for 12 hours. The reaction mixture was concentrated under reduced pressure to give a residue. The residue was purified by column chromatography (SiO$_2$, Petroleum ether:Ethyl acetate=1:0 to 1:1) to afford 2-chloro-5-iodo-3-methylpyridin-4-amine (760 mg, 2.83 mmol, 40% yield). Brown solid; $^1$H NMR (400 MHz, DMSO-d6) δ 8.17 (s, 1H), 6.25 (br s, 2H), 2.56 (s, 3H).

Step B. ethyl-4-amino-6-chloro-5-methylnicotinate. To a solution of 2-chloro-5-iodo-3-methylpyridin-4-amine (710 mg, 2.64 mmol, 1.00 eq) in ethyl alcohol (25.0 mL) were added triethylamine (5.16 g, 51.0 mmol, 7.10 mL, 19.3 eq) and Pd(PPh$_3$)$_2$Cl$_2$ (186 mg, 264 µmol, 0.10 eq) under nitrogen. The suspension was degassed under vacuum and purged with carbon monoxide several times. The mixture was stirred under carbon monoxide (15.0 psi) at 80° C. for 15 hours. The reaction mixture was filtered and concentrated under reduced pressure to give a residue. The residue was purified by column chromatography (SiO$_2$, Petroleum ether:Ethyl acetate=5:1 to 2:1) to afford ethyl-4-amino-6-chloro-5-methylnicotinate (453 mg, 2.11 mmol, 80% yield) as a yellow solid; $^1$H NMR (400 MHz, DMSO-d6) δ 8.44 (s, 1H), 4.31 (q, J=7.2 Hz, 2H), 2.17 (s, 3H), 1.32 (t, J=7.2 Hz, 3H).

Step C. ethyl 6-chloro-5-methyl-4-(3-(2,2,2-trichloroacetyl)ureido)nicotinate. To a solution of ethyl-4-amino-6-chloro-5-methylnicotinate (450 mg, 2.10 mmol, 1.00 eq) in THF (5.00 mL) was added 2,2,2-trichloroacetyl isocyanate (474 mg, 2.52 mmol, 298 µL, 1.20 eq). The mixture was stirred at 20° C. for 2 hours. The reaction mixture was concentrated under reduced pressure to give a residue. The residue was triturated with methyl tert-butyl ether (10.0 mL) to afford ethyl 6-chloro-5-methyl-4-(3-(2,2,2-trichloroacetyl)ureido)nicotinate (1.00 g, crude) as a white solid; LCMS [ESI, M+1]: 403.9.

Step D. 7-chloro-8-methylpyrido[4,3-d]pyrimidine-2,4-diol. To a solution of ethyl 6-chloro-5-methyl-4-(3-(2,2,2-trichloroacetyl)ureido)nicotinate (1.00 g, 2.48 mmol, 1.00 eq) in methyl alcohol (20.0 mL) was added ammonia (3.1 M, 800 µL, 1.00 eq). The mixture was stirred at 20° C. for 2 hours. The reaction mixture was concentrated under reduced pressure affording 7-chloro-8-methylpyrido[4,3-d]pyrimidine-2,4-diol (1.05 g, crude) as a yellow solid.

Step E. 2,4,7-trichloro-8-methylpyrido[4,3-d]pyrimidine. To a solution of 7-chloro-8-methylpyrido[4,3-d]pyrimidine-2,4-diol (900 mg, 4.25 mmol, 1.00 eq) in phosphorus oxychloride (16.5 g, 108 mmol, 10.0 mL, 25.3 eq) was added diisopropylethylamine (1.10 g, 8.51 mmol, 1.48 mL, 2.00 eq). The mixture was stirred at 120° C. for 2 hours. The reaction mixture was concentrated under reduced pressure to give a residue. The residue was purified by column chromatography (SiO$_2$, Petroleum ether:Ethyl acetate=10:1 to 1:1) to give 2,4,7-trichloro-8-methylpyrido[4,3-d]pyrimidine (400 mg, 1.60 mmol, 38% yield, 99% purity) as a yellow solid; $^1$H NMR (400 MHz, CDCl$_3$) δ 9.35 (s, 1H), 2.79 (s, 3H); LCMS [ESI, M+1]: 247.8.

Step F. (1R,5S)-tert-butyl 3-(2,7-dichloro-8-methylpyrido[4,3-d]pyrimidin-4-yl)-3,8-diazabicyclo[3.2.1]octane-8-carboxylate. To a solution of 2,4,7-trichloro-8-methylpyrido[4,3-d]pyrimidine (300 mg, 1.21 mmol, 1.00 eq) in dichloromethane (10.0 mL) were added N-ethyl-N-isopropylpropan-2-amine (312 mg, 2.41 mmol, 420 µL, 2.00 eq), tert-butyl 3,8-diazabicyclo[3.2.1]octane-8-carboxylate (256 mg, 1.21 mmol, 1.00 eq) and 4 A MS (300 mg). The mixture was stirred at −78° C. for 0.5 hour. The reaction mixture was concentrated under reduced pressure to give a residue. The residue was purified by column chromatography (SiO$_2$, Petroleum ether:Ethyl acetate=5:1 to 2:1) to afford (1R,5S)-tert-butyl 3-(2,7-dichloro-8-methylpyrido[4,3-d]pyrimidin-4-yl)-3,8-diazabicyclo[3.2.1]octane-8-carboxylate (448 mg, 1.06 mmol, 87% yield) as a yellow solid; $^1$H NMR (400 MHz, CDCl$_3$) δ 8.80 (s, 1H), 4.44 (br d, J=11.6 Hz, 2H), 4.37-4.22 (m, 2H), 3.70-3.52 (m, 2H), 2.58 (s, 3H), 1.92-1.81 (m, 2H), 1.60 (br d, J=7.2 Hz, 2H), 1.45 (s, 9H).

Step G. (1R,5S)-tert-butyl 3-(7-chloro-8-methyl-2-(((S)-1-methylpyrrolidin-2-yl)methoxy)pyrido[4,3-d]pyrimidin-4-yl)-3,8-diazabicyclo[3.2.1]octane-8-carboxylate. To a solution of (1R,5S)-tert-butyl-3-(2,7-dichloro-8-methylpyrido[4,3-d]pyrimidin-4-yl)-3,8-diazabicyclo[3.2.1]octane-8-carboxylate (290 mg, 683 µmol, 1.00 eq) in dioxane (5.00 mL) was added N-ethyl-N-isopropylpropan-2-amine (442 mg, 3.42 mmol, 595 µL, 5.00 eq) and [(2S)-1-methylpyrrolidin-2-yl]methanol (394 mg, 3.42 mmol, 406 µL, 5.00 eq). The mixture was stirred at 100° C. for 12 hours. The reaction mixture was concentrated under reduced pressure to give a residue. The residue was purified by preparative TLC (SiO$_2$, Petroleum ether:Ethyl acetate=0:1) to afford (1R,5S)-tert-butyl-3-(7-chloro-8-methyl-2-(((S)-1-methylpyrrolidin-2-yl)methoxy)pyrido[4,3-d]pyrimidin-4-yl)-3,8-diazabicyclo[3.2.1]octane-8-carboxylate (130 mg, 249 µmol, 36% yield, 96% purity) as a yellow solid; LCMS [ESI, M+1]: 503.0.

Step H. (1R,5S)-tert-butyl-3-(7-(3-hydroxynaphthalen-1-yl)-8-methyl-2-(((S)-1-methylpyrrolidin-2-yl)methoxy)pyrido[4,3-d]pyrimidin-4-yl)-3,8-diazabicyclo[3.2.1]octane-8-carboxylate. A mixture of (1R,5S)-tert-butyl 3-(7-chloro-8-methyl-2-(((S)-1-methylpyrrolidin-2-yl)methoxy)pyrido[4,3-d]pyrimidin-4-yl)-3,8-diazabicyclo[3.2.1]octane-8-carboxylate (110 mg, 219 µmol, 1.00 eq.), 2-[3-(methoxymethoxy)-1-naphthyl]-4,4,5,5-tetramethyl-1,3,2-dioxaborolane (229 mg, 437 µmol, 2.00 eq), potassium carbonate (60.4 mg, 437 µmol, 2.00 eq), Bis(di-tert-butylphosphino)ferrocene]dichloropalladium(II) (14.3 mg, 21.9 µmol, 0.10 eq) in dimethyl formamide (2.00 mL) was degassed and purged with nitrogen for 3 times. The mixture was stirred at 120° C. for 12 hours under nitrogen atmosphere. The reaction mixture was diluted with water (10.0 mL) and extracted with ethyl acetate (3×10.0 mL). The combined organic layers were washed with brine (10.0 mL), dried, filtered and concentrated under reduced pressure to give a residue. The residue was purified by preparative TLC (SiO$_2$, Petroleum ether:Ethyl acetate=0:1) to afford 1R,5S)-tert-butyl 3-(7-(3-hydroxynaphthalen-1-yl)-8-methyl-2-(((S)-1-methylpyrrolidin-2-yl)methoxy)pyrido[4,3-d]pyrimidin-4-yl)-3,8-diazabicyclo[3.2.1]octane-8-carboxylate (35.0 mg, 48.8 µmol, 22% yield, 91% purity) as a brown oil; LCMS [ESI, M+1]: 655.2.

Step I. 4-(4-((1R,5S)-3,8-diazabicyclo[3.2.1]octan-3-yl)-8-methyl-2-(((S)-1-methylpyrrolidin-2-yl)methoxy)pyrido[4,3-d]pyrimidin-7-yl)naphthalen-2-ol. To a solution of (1R,5S)-tert-butyl-3-(7-(3-hydroxynaphthalen-1-yl)-8-methyl-2-(((S)-1-methylpyrrolidin-2-yl)methoxy)pyrido[4,3-d]pyrimidin-4-yl)-3,8-diazabicyclo[3.2.1]octane-8-carboxylate (15.0 mg, 20.9 µmol, 1.00 eq) in acetonitrile (0.50 mL) was added HCl·dioxane (4.00 M, 0.50 mL, 95.6 eq). The mixture was stirred at 25° C. for 1 hour. The reaction mixture was concentrated under reduced pressure to give a residue. The residue was purified with preparative HPLC (HCl condition and TFA condition) to afford 4-(4-((1R,5S)-3,8-diazabicyclo[3.2.1]octan-3-yl)-8-methyl-2-(((S)-1-methylpyrrolidin-2-yl)methoxy)pyrido[4,3-d]pyrimidin-7-yl)naphthalen-2-ol (5.29 mg, 8.17 µmol, 39% yield, 96% purity, TFA) as a yellow gum; $^1$H NMR (400 MHz, DMSO-d6) δ 10.11 (br s, 1H), 9.51-9.46 (m, 1H), 9.27 (s, 2H), 7.81 (d, J=8.4 Hz, 1H), 7.47-7.40 (m, 1H), 7.27 (d, J=2.4 Hz, 1H), 7.24-7.17 (m, 2H), 7.06 (d, J=2.0 Hz, 1H), 4.81-4.75 (m, 1H), 4.74-4.63 (m, 3H), 4.21 (br s, 2H), 3.92-3.84 (m, 3H), 3.17-3.12 (m, 1H), 2.97 (br s, 3H), 2.91-2.75 (m, 1H), 2.37-2.25 (m, 1H), 2.21 (s, 3H), 2.15-1.88 (m, 8H); LCMS [ESI, M+1]: 511.1.

Example 191

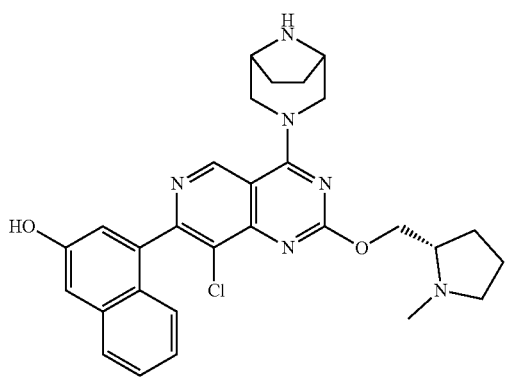

4-(4-((1R,5S)-3,8-diazabicyclo[3.2.1]octan-3-yl)-8-chloro-2-(((S)-1-methylpyrrolidin-2-yl)methoxy)pyrido[4,3-d]pyrimidin-7-yl)naphthalen-2-ol

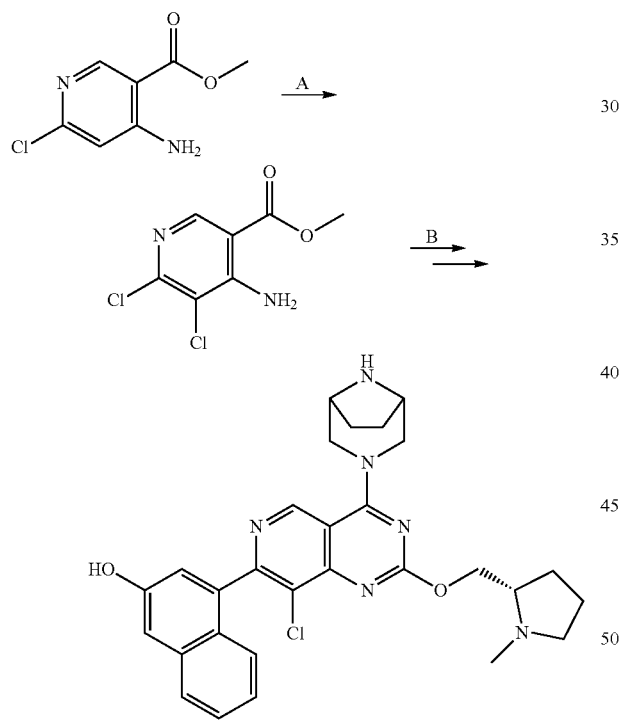

Step A. Methyl 4-amino-5,6-dichloronicotinate. To a solution of methyl 4-amino-6-chloro-pyridine-3-carboxylate (100 mg, 536 μmol, 1.00 eq) in acetonitrile (1.00 mL) was added N-chlorosuccinimide (286 mg, 2.14 mmol, 4.00 eq). The mixture was stirred at 50° C. for 2 hours. The reaction mixture was concentrated under reduced pressure to give a residue. The residue was purified by column chromatography (SiO₂, petroleum ether/ethyl acetate=20:1) to afford the title compound (70.0 mg, 317 μmol, 59% yield). White solid; 1H NMR (400 MHz, CDCl₃-d) δ 8.64 (s, 1H), 3.94 (s, 3H).

Step B. 4-(4-((1R,5S)-3,8-diazabicyclo[3.2.1]octan-3-yl)-8-chloro-2-(((S)-1-methylpyrrolidin-2-yl)methoxy)pyrido[4,3-d]pyrimidin-7-yl)naphthalen-2-ol. Synthesized according to Example 190 step B-I, substituting methyl 4-amino-5,6-dichloronicotinate in place of ethyl-4-amino-6-chloro-5-methylnicotinate to afford the title compound (16.1 mg, 24.5 μmol, 33% yield, 98.4% purity, TFA) as a yellow solid. ¹H NMR (400 MHz, DMSO-d₆) δ 9.30 (s, 1H), 7.79 (d, J=8.0 Hz, 1H), 7.46-7.37 (m, 1H), 7.29-7.23 (m, 2H), 7.22-7.15 (m, 1H), 7.09 (d, J=2.8 Hz, 1H), 4.84-4.76 (m, 1H), 4.73-4.65 (m, 3H), 4.22-4.18 (m, 2H), 3.91 (br d, J=13.6 Hz, 2H), 3.89-3.84 (m, 1H), 3.70-3.62 (m, 1H), 3.18-3.12 (m, 1H), 2.96 (br s, 3H), 2.30-2.23 (m, 1H), 2.10-2.02 (m, 1H), 1.99-1.82 (m, 6H); LCMS [ESI, M+1]: 531.3.

Example 192

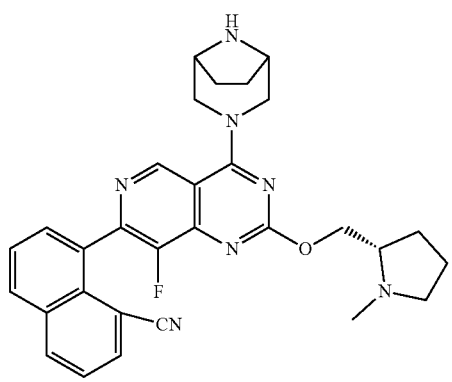 [SMILES: CN1CCC[C@H]1COc1nc(N2CC3CCC(C2)N3)c2cnc(-c3cccc4cccc(C#N)c34)c(F)c2n1]

4-(4-((1R,5S)-3,8-diazabicyclo[3.2.1]octan-3-yl)-8-fluoro-2-(2-(2-methyl-1H-imidazol-1-yl)ethoxy)pyrido[4,3-d]pyrimidin-7-yl)naphthalen-2-ol Synthesized according to Example 3, Steps G-I substituting S-prolinol for 2-(1-methyl-1H-imidazol-2-yl)ethan-1-ol in Step G and substituting 8-(4,4,5,5-tetramethyl-1,3,2-dioxaborolan-2-yl)-1-naphthonitrile for 4-(4,4,5,5-tetramethyl-1,3,2-dioxaborolan-2-yl)naphthalen-2-ol in Step H to afford 4-(4-((1R,5S)-3,8-diazabicyclo[3.2.1]octan-3-yl)-8-fluoro-2-(2-(2-methyl-1H-imidazol-1-yl)ethoxy)pyrido[4,3-d]pyrimidin-7-yl)naphthalen-2-ol (15 mg, 36%). LCMS (MM-ES+APCI, Pos): m/z 524.3 (M+H).

Example 193

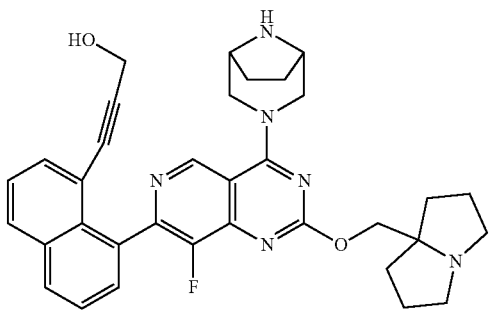 [SMILES: OCC#Cc1cccc2cccc(-c3ncc4c(N5CC6CCC(C5)N6)nc(OCC56CCCN5CCC6)nc4c3F)c12]

3-(8-(4-((1R,5S)-3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)naphthalen-1-yl)prop-2-yn-1-ol

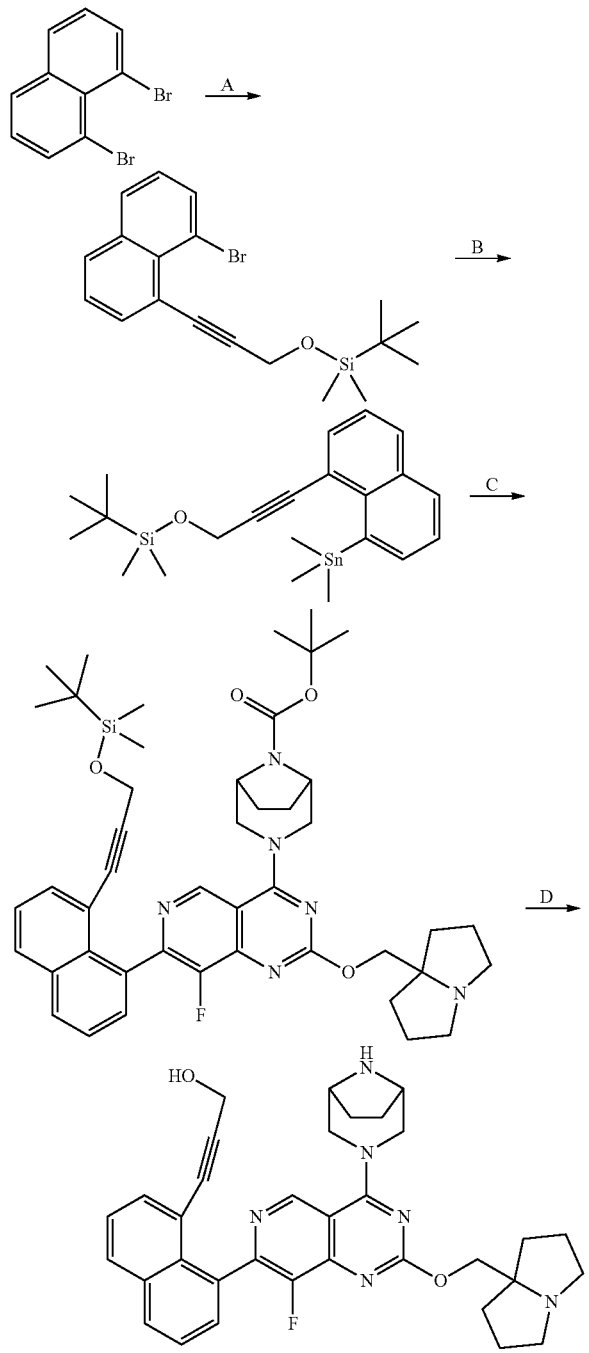

Step A. ((3-(8-bromonaphthalen-1-yl)prop-2-yl-1-yl)oxy)(tert-butyl)dimethylsilane. To a mixture of 1,8-dibromonaphthalene (7.5 g, 26 mmol), copper(I) iodide (0.50 g, 2.6 mmol), triphenylphosphine (0.69 g, 2.6 mmol) and tert-butyldimethyl(2-propynyloxy)silane (5.4 g, 31 mmol) was added triethylamine (50 mL) and the reaction was sparged with Ar for 10 minutes followed by addition of trans-dichlorobis(triphenylphosphine)palladium (II) (0.92 g, 1.3 mmol) and copper(I) iodide (0.50 g, 2.6 mmol). The reaction was heated to 80 C for 3 hours. Additional tert-butyldimethyl(2-propynyloxy)silane (3 g) was added and the reaction stirred for 3 additional hours. The reaction was poured into water and extracted with MTBE. The layers were separated. The organics were washed with water, brine, dried over MgSO$_4$ and concentrated in vacuo. The residue was chromatographed using hexanes as eluent to give impure product. The residue was purified by reverse preparative HPLC using 50→100% ACN/water with 0.1% formic acid as modifier to give ((3-(8-bromonaphthalen-1-yl)prop-2-yn-1-yl)oxy)(tert-butyl)dimethylsilane (1.0 g, 2.7 mmol, 10% yield). $^1$H NMR (400 MHz, CDCl$_3$). δ 7.80 (m, 4H), 7.40 (m, 1H), 7.26 (t, J=7.8 Hz, 1H), 4.64 (s, 2H), 0.96 (s, 9H), 0.20 (s, 6H) ppm.

Step B. tert-butyldimethyl((3-(8-trimethylstannyl)naphthalen-1-yl)prop-2-yn-1-yl)oxy)silane. To a solution of ((3-(8-bromonaphthalen-1-yl)prop-2-yn-1-yl)oxy)(tert-butyl)dimethylsilane (1.0 g, 2.7 mmol) in THF (30 mL) cooled to −78° C. under an atmosphere of Ar was added butyl lithium (1.2 mL, 2.9 mmol) and the reaction was held at −78° C. for 30 minutes followed by addition of chlorotrimethylstannane (0.58 g, 2.9 mmol). The reaction was warmed to rt and stirred for 4 hours. The reaction was poured into water and extracted with MTBE. The layers were separated. The organics were washed with brine, dried over MgSO$_4$ and concentrated in vacuo. The residue was purified by reverse preparative HPLC with 80 to 100% ACN/water with 0.2% formic acid as eluent to give the desired product (0.74 g, 60%). $^1$H NMR (400 MHz, CDCl$_3$): δ 7.81 (m, 4H), 7.42 (m, 2H), 4.62 (s, 2H), 0.96 (s, 9H), 0.44 (s, 9H), 0.20 (s, 6H) ppm.

Step C. tert-butyl 3-(7-(8-(3-((tert-butyldimethylsilyl)oxy)prop-1-yn-1-yl)naphthalen-1-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate. To the mixture of copper(I) iodide (0.011 g, 0.056 mmol), BINAP (0.023 g, 0.038 mmol), PdCl$_2$(dppf)-CH$_2$Cl$_2$ adduct (0.015 g, 0.019 mmol), tert-butyl 3-(7-chloro-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (0.10 g, 0.19 mmol) and tert-butyldimethyl((3-(8-(trimethylstannyl)naphthalen-1-yl)prop-2-yn-1-yl)oxy) silane (0.22 g, 0.49 mmol) in a microwave vial was added toluene (2 mL) and the slurry was sparged with Ar for 10 minutes. The reaction was capped and heated to 100° C. overnight. The reaction was loaded directly on a column and eluted with 1:1 DCM/EtOAc followed by 0 to 10% MeOH/DCM with 0.2% NH$_4$OH as modifier to give 3-(7-(8-(3-((tert-butyldimethylsilyl)oxy)prop-1-yn-1-yl)naphthalen-1-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (70% purity; 0.050 g, 0.063 mmol, 34% yield).

Step D. 3-(8-(4-(3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)naphthalen-1-yl)prop-2-yn-1-ol. To a solution of tert-butyl 3-(7-(8-(3-((tert-butyldimethylsilyl)oxy)prop-1-yn-1-yl)naphthalen-1-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (0.050 g, 0.063 mmol) in DCM (1 mL) was added TFA (0.5 mL) and the reaction was stirred at rt for 1 hr. The reaction was concentrated in vacuo and the material purified by Gilson eluting with 0 to 95% ACN/water with 0.1% TFA as modifier. Fractions containing product were combined and partitioned between EtOAc and

413 sat. bicarb. The layers were separated. The organics were washed with brine, dried over MgSO₄ and concentrated in vacuo to give 3-(8-(4-(3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)naphthalen-1-yl)prop-2-yn-1-ol (0.004 g, 0.0069 mmol, 11% yield). LCMS (MM-ES+APCI, Pos): m/z 579.3 (M+H).

Example 194

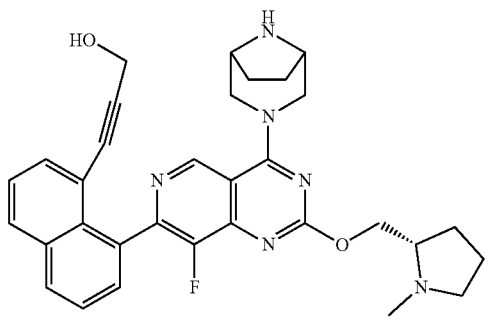 [SMILES: CN1CCC[C@H]1COc1nc(N2CC3CCC(C2)N3)c2cnc(-c3cccc4cccc(C#CCO)c34)c(F)c2n1]

3-(8-(4-((1R,5S)-3,8-diazabicyclo[3.2.1]octan-3-yl)-8-fluoro-2-(((S)-1-methylpyrrolidin-2-yl)methoxy)pyrido[4,3-d]pyrimidin-7-yl)naphthalen-1-yl)prop-2-yn-1-ol Synthesized according to Example 193, substituting tert-butyl 3-(7-chloro-8-fluoro-2-(((S)-1-methylpyrrolidin-2-yl)methoxy)pyrido[4,3-d]pyrimidin-4-yl)-3,8-diazabicyclo[3.2.1]octane-8-carboxylate in place of tert-butyl 3-(7-chloro-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate to afford the title compound (11.4 mg, 31%). LCMS (MM-ES+APCI, Pos): m/z 553.3 (M+H).

Example 195

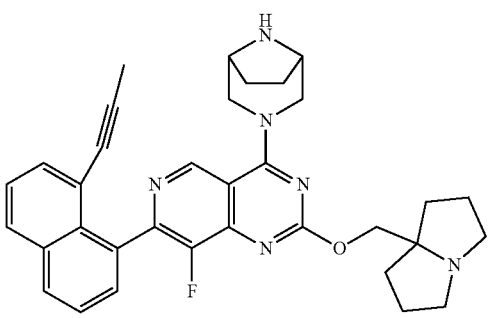 [SMILES: CC#Cc1cccc2cccc(-c3ncc4c(N5CC6CCC(C5)N6)nc(OCC56CCCN5CCC6)nc4c3F)c12]

414

4-((1R,5S)-3,8-diazabicyclo[3.2.1]octan-3-yl)-8-fluoro-7-(8-(prop-1-yn-1-yl)naphthalen-1-yl)-2-((tetrahydro-1H-pyrrolizin-7a(5H)-yl)methoxy)pyrido[4,3-d]pyrimidine

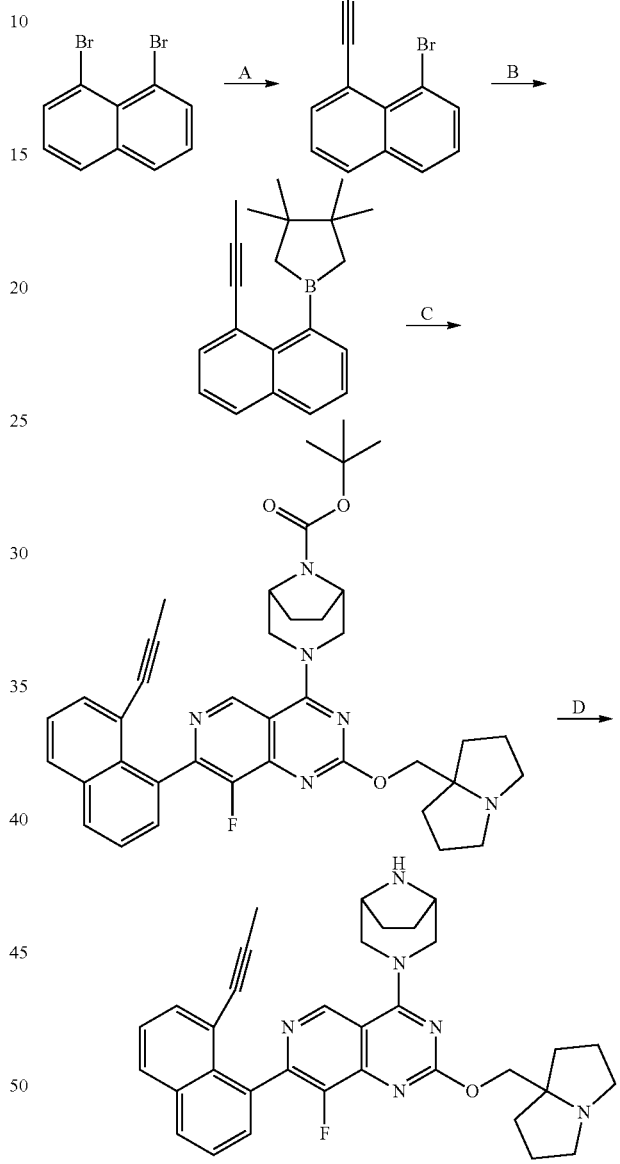

Step A. 1-bromo-8-(prop-1-yn-1-yl)naphthalene. To a solution of 1,8-dibromonaphthalene (2.0 g, 7.0 mmol) in DMSO (40 mL) were added but-2-ynoic acid (0.71 g, 8.4 mmol), 1,4-bis(diphenylphosphanyl)butane, (0.30 g, 0.70 mmol), 2,3,4,6,7,8,9,10-octahydropyrimido[1,2-a]azepine (3.2 g, 21 mmol), and trans-Dichlorobis(triphenylphosphine)palladium (II) (0.25 g, 0.35 mmol) and the reaction was sparged with Ar for 10 minutes and heated to 100° C. for 1 hr. The reaction was cooled and partitioned between MTBE and water and the layers were separated. The organics were washed with water, brine, dried over MgSO₄ and concentrated in vacuo. The residue was chromatographed using 0 to 50% DCM/Hexane as eluent to give 1-bromo-8-

(prop-1-yn-1-yl)naphthalene (0.40 g, 1.6 mmol, 23% yield). ¹H NMR (400 MHz, CDCl₃): δ 7.83 (dd, J 7.6, 1.1 Hz, 1H), 7.75 (m, 3H), 7.38 (dd, J=8.2, 7.4 Hz, 1H), 7.23 (t, J=7.43 Hz, 1H), 2.15 (s, 3H) ppm.

Step B: 4,4,5,5-tetramethyl-2-(8-(prop-1-yn-1-yl)naphthalen-1-yl)-1,3,2-dioxaborolane. To a solution of 1-bromo-8-(prop-1-yn-1-yl)naphthalene (0.39 g, 1.6 mmol) in THF (15 mL) cooled to −78° C. was added butyl lithium (0.70 mL, 1.8 mmol) and the reaction mixture was stirred at −78° C. for 20 minutes followed by addition of 2-isopropoxy-4,4,5,5-tetramethyl-1,3,2-dioxaborolane (0.30 g, 1.6 mmol). The reaction was warmed to rt for 1 hr. The reaction mixture was partitioned between water and MTBE and the layers were separated. The organics were washed with brine, dried over MgSO₄ and concentrated in vacuo. The material was purified by chromatography using 0 to 50% DCM/Hex as eluent to give 4,4,5,5-tetramethyl-2-(8-(prop-1-yn-1-yl)naphthalen-1-yl)-1,3,2-dioxaborolane (0.30 g, 1.0 mmol, 65% yield). ¹H NMR (400 MHz, CDCl₃): δ 7.82 (dd, J=7.8, 1.2 Hz, 1H), 7.72 (m, 3H), 7.43 (m, 1H), 7.36 (m, 1H), 2.2 (s, 3H), 1.44 (s, 12H) ppm.

Step C. tert-butyl (1R,5S)-3-(8-fluoro-7-(8-(prop-1-yn-1-yl)naphthalen-1-yl)-2-((tetrahydro-1H-pyrrolizin-7a(5H)-yl)methoxy)pyrido[4,3-d]pyrimidin-4-yl)-3,8-diazabicyclo[3.2.1]octane-8-carboxylate. To a slurry of tert-butyl (1R,5S)-3-(7-chloro-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (0.070 g, 0.13 mmol) and 4,4,5,5-tetramethyl-2-(8-(prop-1-yn-1-yl)naphthalen-1-yl)-1,3,2-dioxaborolane (0.12 g, 0.39 mmol) in dioxanes (2 mL) was added K₂CO₃ (2M, 0.26 mL, 0.53 mmol) and the reaction was sparged with Ar for 10 minutes followed by addition RuPhos Pd G3 (40 mg). The reaction was heated to 90° C. for 2 hrs. The reaction mixture was directly purified by column chromatography eluting with 1:1 DCM/EtOAc followed by 0 to 10% MeOH/DCM with 0.2% NH₄OH as modifier to give tert-butyl (1R,5S)-3-(8-fluoro-7-(8-(prop-1-yn-1-yl)naphthalen-1-yl)-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (0.10 g, 0.15 mmol, 115% yield).

Step D. 4-((1R,5S)-3,8-diazabicyclo[3.2.1]octan-3-yl)-8-fluoro-7-(8-(prop-1-yn-1-yl)naphthalen-1-yl)-2-((tetrahydro-1H-pyrrolizin-7a(5H)-yl)methoxy)pyrido[4,3-d]pyrimidine. To a solution of tert-butyl (1R,5S)-3-(8-fluoro-7-(8-(prop-1-yn-1-yl)naphthalen-1-yl)-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (0.050 g, 0.0754 mmol) in DCM (1 mL) was added TFA (0.5 mL) and the reaction was stirred at rt for 1 hr. The reaction was concentrated in vacuo and the material was purified by Gilson reverse preparative HPLC eluting with 5 to 95% ACN/water with 0.2% TFA as modifier. Fractions containing the desired product were pooled and partitioned between EtOAc and sat. NaHCO₃. The layers were separated. The organics were washed with brine, dried over MgSO₄ and concentrated in vacuo to give 4-((1R,5S)-3,8-diazabicyclo[3.2.1]octan-3-yl)-8-fluoro-7-(8-(prop-1-yn-1-yl)naphthalen-1-yl)-2-((tetrahydro-1H-pyrrolizin-7a(5H)-yl)methoxy)pyrido[4,3-d]pyrimidine (0.0113 g, 0.0201 mmol, 26.6% yield). LCMS (MM-ES+APCI, Pos): m/z 563.3 (M+H).

Example 196

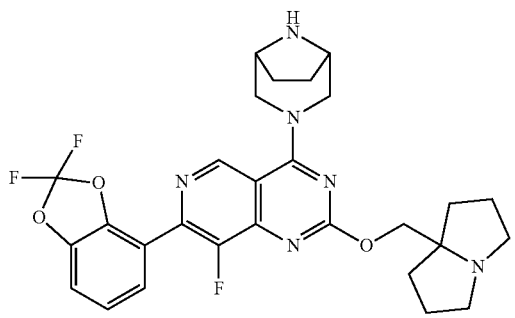 [SMILES: Fc1c(-c2cccc3c2OC(F)(F)O3)ncc2c(N3CC4CCC(C3)N4)nc(OCC34CCCN3CCC4)nc12]

4-((1R,5S)-3,8-diazabicyclo[3.2.1]octan-3-yl)-7-(2,2-difluorobenzo[d][1,3]dioxol-4-yl)-8-fluoro-2-((tetrahydro-1H-pyrrolizin-7a(5H)-yl)methoxy)pyrido[4,3-d]pyrimidine

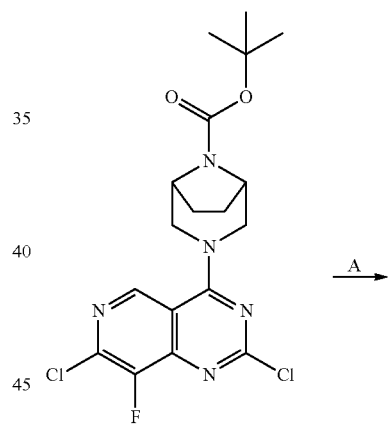

A →

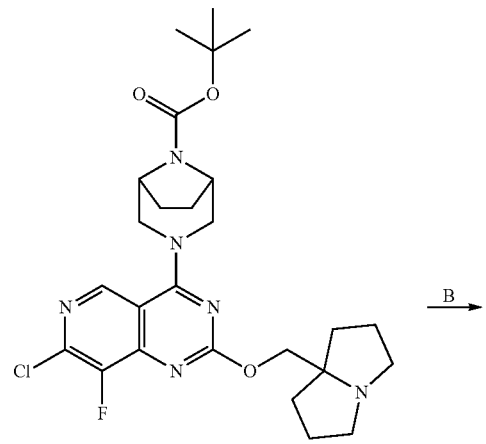

B →

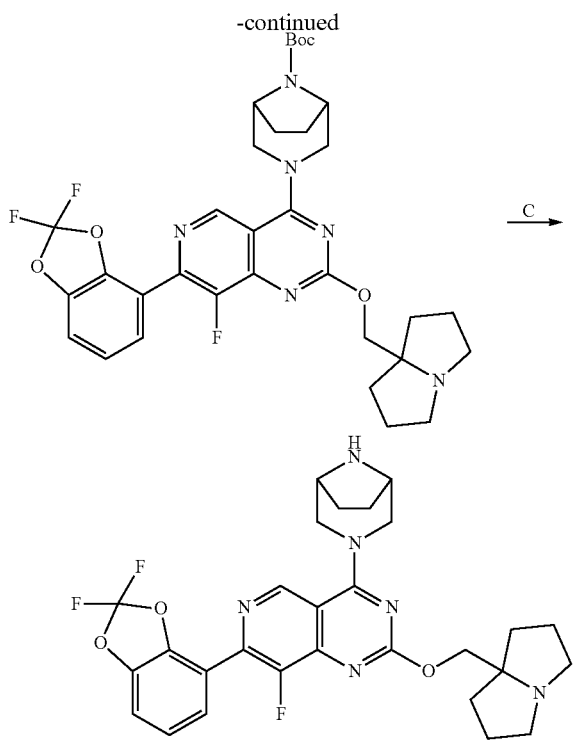

Step A: tert-butyl (1R,5S)-3-(7-chloro-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate. A mixture of tert-butyl (1R,5S)-3-(2,7-dichloro-8-fluoropyrido[4,3-d]pyrimidin-4-yl)-3,8-diazabicyclo[3.2.1]octane-8-carboxylate (1 g, 2.33 mmol) and 1,4-dioxane (23.3 mL) was treated with (tetrahydro-1H-pyrrolizin-7a(5H)-yl)methanol (0.5 g, 3.5 mmol) and cesium carbonate (2.28 g, 7 mmol) at room temperature. The mixture was stirred at 95° C. overnight. The mixture was diluted with water and extracted with EtOAc. The combined organic layers were washed with brine, dried over Na₂SO₄, filtered, and concentrated in vacuo. The concentrate was purified by chromatography eluting with 0%-10% DCM:MeOH (2% NH₄OH modifier) to afford tert-butyl (1R,5S)-3-(7-chloro-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (0.592 g, 1.11 mmol, 47.6% yield). LCMS (MM-ES+APCI, Pos): m/z 533.3 (M+H).

Step B: tert-butyl (1R,5S)-3-(7-(2,2-difluorobenzo[d][1,3]dioxol-4-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate. 2,2-Difluorobenzo[1,3]dioxole-4-boronic acid (114 mg, 0.563 mmol), tert-butyl (1R,5S)-3-(7-chloro-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (100 mg, 0.188 mmol) and potassium carbonate (2M aqueous) (0.281 mL, 0.563 mmol) in dioxane (1.9 mL) were mixed in a pressure vessel equipped with a stir bar. The mixture was sparged with Argon for 15 minutes and RuPhos Palladacycle Gen. 3 (62.8 mg, 0.075 mmol) was added. The reaction was immediately capped and stirred at 90° C. overnight. The reaction was cooled to room temperature and the mixture was diluted with water and EtOAc. The layers were separated. The aqueous layer was extracted 3× with EtOAc and the combined organics were dried over Na₂SO₄, concentrated in vacuo and purified by column chromatography (0% to 15% MeOH/DCM with 2% NH₄OH) to afford tert-butyl (1R,5S)-3-(7-(2,2-difluorobenzo[d][1,3]dioxol-4-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (85 mg, 0.13 mmol, 69.2% yield). LCMS (MM-ES+APCI, Pos): m/z 655.3 (M+H).

Step C: 4-((1R,5S)-3,8-diazabicyclo[3.2.1]octan-3-yl)-7-(2,2-difluorobenzo[d][1,3]dioxol-4-yl)-8-fluoro-2-((tetrahydro-1H-pyrrolizin-7a(5H)-yl)methoxy)pyrido[4,3-d]pyrimidine. Tert-butyl (1R,5S)-3-(7-(2,2-difluorobenzo[d][1,3]dioxol-4-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (85 mg, 0.13 mmol) was dissolved in DCM (1.3 mL) and treated with TFA (0.05 mL, 0.65 mmol). The reaction was stirred at room temperature for 1 hour. The reaction was concentrated in vacuo and purified by prep HPLC (Gilson, 5 to 95% ACN with 0.1% TFA as modifier). Fractions containing the desired product were combined and partitioned between DCM and 1M NaOH and the layers were separated. The combined organics were washed with brine, dried over Na₂SO₄ and concentrated in vacuo to give 4-((1R,5S)-3,8-diazabicyclo[3.2.1]octan-3-yl)-7-(2,2-difluorobenzo[d][1,3]dioxol-4-yl)-8-fluoro-2-((tetrahydro-1H-pyrrolizin-7a(5H)-yl)methoxy)pyrido[4,3-d]pyrimidine (55.2 mg, 0.1 mmol, 76.7% yield). LCMS (MM-ES+APCI, Pos): m/z 555.3 (M+H).

Example 197

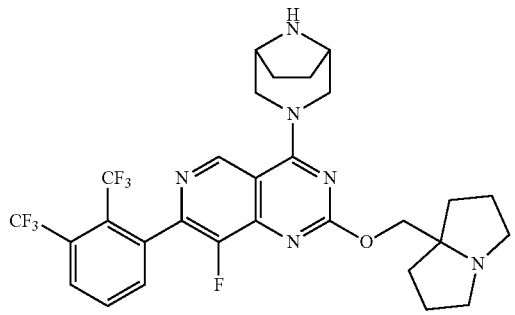 [SMILES: Fc1c(-c2cccc(C(F)(F)F)c2C(F)(F)F)ncc2c(N3CC4CCC(C3)N4)nc(OCC34CCCN3CCC4)nc12]

4-((1R,5S)-3,8-diazabicyclo[3.2.1]octan-3-yl)-7-(2,3-bis(trifluoromethyl)phenyl)-8-fluoro-2-((tetrahydro-1H-pyrrolizin-7a(5H)-yl)methoxy)pyrido[4,3-d]pyrimidine Synthesized according to Example 196 substituting (2,3-bis(trifluoromethyl)phenyl)boronic acid in place of 2,2-difluorobenzo[1,3]dioxole-4-boronic acid in step B to afford tert-butyl (1R,5S)-3-(7-(2,3-bis(trifluoromethyl)phenyl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (39.3 mg, 0.06 mmol, 29.5% yield). LCMS (MM-ES+APCI, Pos): m/z 611.2 (M+H).

Example 198

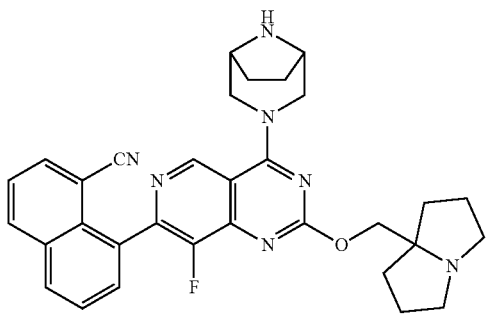 [SMILES: N#Cc1cccc2cccc(-c3ncc4c(N5CC6CCC(C5)N6)nc(OCC56CCCN5CCC6)nc4c3F)c12]

8-(4-((1R,5S)-3,8-diazabicyclo[3.2.1]octan-3-yl)-8-
fluoro-2-((tetrahydro-1H-pyrrolizin-7a(5H)-yl)
methoxy)pyrido[4,3-d]pyrimidin-7-yl)-1-naphthoni-
trile Synthesized according to Example 196 substituting 8-(4,4,5,5-tetramethyl-1,3,2-dioxaborolan-2-yl)-1-naphthonitrile in place of 2,2-difluorobenzo[1,3]dioxole-4-boronic acid and methanesulfonato(2-dicyclohexylphosphino-2',4',6'-tri-1-propyl-1,1'-biphenyl)(2'-amino-1,1'-biphenyl-2-yl)palladium(II) in place of RuPhos Palladacycle Gen. 3 in step B to afford 8-(4-((1R,5S)-3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)-1-naphthonitrile (10.8 mg, 0.02 mmol, 42.6% yield). LCMS (MM-ES+APCI, Pos): m/z 550.3 (M+H).

Example 199

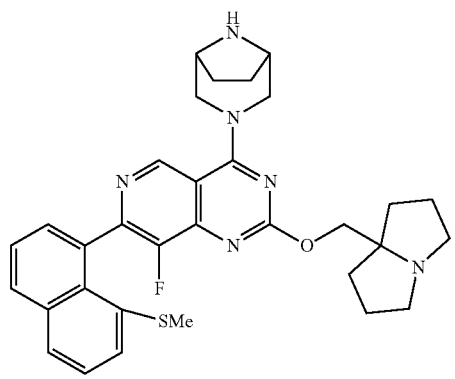 [SMILES: CSc1cccc2cccc(-c3ncc4c(N5CC6CCC(C5)N6)nc(OCC56CCCN5CCC6)nc4c3F)c12]

4-((1R,5S)-3,8-diazabicyclo[3.2.1]octan-3-yl)-8-
fluoro-7-(8-(methylthio)naphthalen-1-yl)-2-((tetra-
hydro-1H-pyrrolizin-7a(5H)-yl)methoxy)pyrido[4,3-
d]pyrimidine

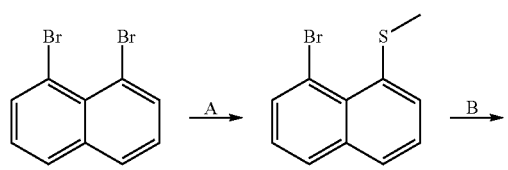

-continued

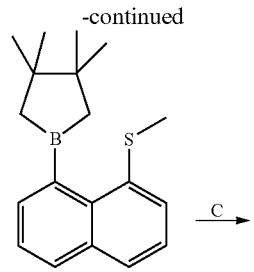

Step A. (8-bromonaphthalen-1-yl)(methyl)sulfane. To a stirred solution of 1,8-dibromonaphthalene (500 mg, 1.75 mmol) in tetrahydrofuran (25 mL) under $N_2$ cooled to −78° C. was added butyl lithium (0.77 mL, 1.9 mmol) dropwise and the solution was stirred at −78° C. for 30 min. Dimethyl disulfide (0.17 mL, 1.9 mmol) was added dropwise and the reaction mixture was stirred while warming to 0° C. To the reaction was added a solution of tetrakis(acetonitrile)copper (I)hexafluorophosphate (749 mg, 2.01 mmol) in water-THF 1:1 (10 mL) at once and the reaction stirred for 1 h at rt. The reaction was filtered through Celite and the Celite was washed with MTBE (2*5 mL). The filtrate was concentrated under $N_2$ to ~5 mL and partitioned between water (5 mL) and hexane (20 mL). The layers were separated. The organic phase was washed with water and sat. $NaHCO_3$ (5 mL each), dried over $Na_2SO_4$ and evaporated in vacuo. The residue was chromatographed on silica gel using hexane as eluent to yield (8-bromonaphthalen-1-yl)(methyl)sulfane (328 mg, 74%). ¹H NMR (400 MHz, CDCl₃): δ 7.82 (dd, J 7.4, 1.2 Hz, 1H), 7.77 (dd, J=8.2, 1.1 Hz, 1H), 7.61 (dd, J=6.6, 2.8 Hz, 1H), 7.42-7.35 (m, 2H), 7.24 (t, J=7.9 Hz, 1H), 2.55 (s, 3H) ppm.

Step B. 4,4,5,5-tetramethyl-2-(8-(methylthio)naphthalen-1-yl)-1,3,2-dioxaborolane. To a stirred solution of (8-bromonaphthalen-1-yl)(methyl)sulfane (200 mg, 0.79 mmol) in tetrahydrofuran (8 mL) under N₂ cooled to −78° C. was added butyl lithium (0.35 mL, 0.87 mmol) dropwise and the solution was stirred at −78° C. for 30 min. 2-isopropoxy-4,4,5,5-tetramethyl-1,3,2-dioxaborolane (176 mg, 0.95 mmol) was added dropwise and the reaction mixture stirred while warming to 0° C. The reaction was quenched with 0.5M NaHCO₃ (5 mL) and the mixture extracted with MTBE (20 mL). The layers were separated. The organic phase was washed with brine, dried over Na₂SO₄ and evaporated in vacuo. The residue was chromatographed on silica gel using 5 to 10% EtOAc/hexane as eluent to yield 4,4,5,5-tetramethyl-2-(8-(methylthio)naphthalen-1-yl)-1,3,2-dioxaborolane (188 mg, 79%). ¹H NMR (400 MHz, CDCl₃): δ 7.83 (dd, J=8.1, 1.2 Hz, 1H), 7.80 (d, J=7.6 Hz, 2H), 7.62 (dd, J=6.8, 1.2 Hz, 1H), 7.48 (dd, J=8.1, 6.9 Hz, 1H), 7.41 (t, J=7.6 Hz, 1H), 2.41 (s, 3H), 1.45 (s, 12H) ppm.

Step C. tert-butyl (1R,5S)-3-(8-fluoro-7-(8-(methylthio)naphthalen-1-yl)-2-((tetrahydro-1H-pyrrolizin-7a(5H)-yl)methoxy)pyrido[4,3-d]pyrimidin-4-yl)-3,8-diazabicyclo[3.2.1]octane-8-carboxylate. A mixture of tert-butyl (1R,5S)-3-(7-chloro-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (50 mg, 0.094 mmol), 4,4,5,5-tetramethyl-2-(8-(methylthio)naphthalen-1-yl)-1,3,2-dioxaborolane (42 mg, 0.14 mmol), Pd(PPh₃)₄ (11 mg, 0.0094 mmol) in 1,4-dioxane (1 mL) was added 2M Na₂CO₃ (0.14 mL, 0.28 mmol) and the mixture was degassed. The mixture was capped and stirred at 60° C. overnight and then at 90° C. for 4 h. The mixture was cooled, and partitioned between water (5 mL) and EtOAc (10 mL). The layers were separated. The organic phase was washed with brine, dried over Na₂SO₄ and evaporated in vacuo. The residue was slurried in MeOH—H₂O 1:1 with ~1% TFA (2 mL) and separated and the residual oil was extracted with MeOH—H₂O 1:1 with ~1% TFA (1 mL). The combined aqueous phase was filtered and chromatographed by reverse preparative HPLC using 5-95% MeCN/water with 0.1% TFA as modifier. The purest fraction was freebased and extracted with DCM (2×10 mL). The organic phase was dried over Na₂CO₃, filtered and evaporated in vacuo to yield tert-butyl (1R,5S)-3-(8-fluoro-7-(8-(methylthio)naphthalen-1-yl)-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (4.0 mg, 6.3%). LCMS (MM-ES+APCI, Pos): m/z 671.3 [M+H].

Step D. 4-((1R,5S)-3,8-diazabicyclo[3.2.1]octan-3-yl)-8-fluoro-7-(8-(methylthio)naphthalen-1-yl)-2-((tetrahydro-1H-pyrrolizin-7a(5H)-yl)methoxy)pyrido[4,3-d]pyrimidine. Synthesized according to Example 1, Step G deprotection using tert-butyl (1R,5S)-3-(8-fluoro-7-(8-(methylthio)naphthalen-1-yl)-2-((tetrahydro-1H-pyrrolizin-7a(5H)-yl)methoxy)pyrido[4,3-d]pyrimidin-4-yl)-3,8-diazabicyclo[3.2.1]octane-8-carboxylate to yield 4-((1R,5S)-3,8-diazabicyclo[3.2.1]octan-3-yl)-8-fluoro-7-(8-(methylthio)

naphthalen-1-yl)-2-((tetrahydro-1H-pyrrolizin-7a(5H)-yl)methoxy)pyrido[4,3-d]pyrimidine (3.28 mg, 96%). LCMS (MM-ES+APCI, Pos): m/z 571.3 [M+H].

Example 200

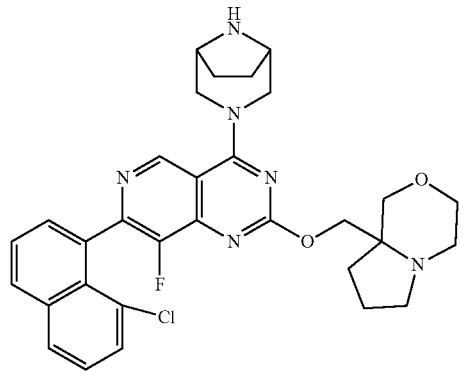 [SMILES: Fc1c(-c2cccc3cccc(Cl)c23)ncc2c(N3CC4CCC(C3)N4)nc(OCC34CCCN3CCOC4)nc12]

8a-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)hexahydro-1H-pyrrolo[2,1-c][1,4]oxazine

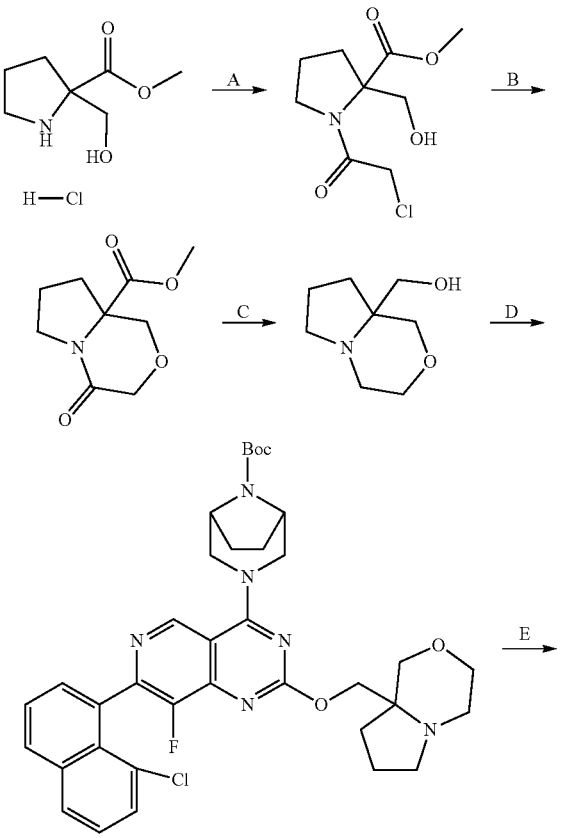

423

-continued

[chemical structure]

Step A. Methyl 1-(2-chloroacetyl)-2-(hydroxymethyl) pyrrolidine-2-carboxylate. A mixture of methyl 2-(hydroxymethyl)pyrrolidine-2-carboxylate hydrochloride (978 mg, 5.00 mmol) and dichloromethane (50 mL) was added triethylamine (1.74 mL, 12.5 mmol) and the reaction was stirred until dissolution of the crystals. The mixture was cooled to 0° C. and 2-chloroacetyl chloride (0.44 mL, 5.5 mmol) was added dropwise. The mixture was warmed to rt, stirred for 2 h, and then refluxed for 1 h. The mixture was evaporated in vacuo and the residue was chromatographed on silica gel with 4 to 20% MeOH/DCM as eluent to yield methyl 1-(2-chloroacetyl)-2-(hydroxymethyl)pyrrolidine-2-carboxylate. LCMS (MM-ES+APCI, Pos): m/z 236.1 [M+H].

Step B. Methyl 4-oxotetrahydro-1H-pyrrolo[2,1-c][1,4]oxazine-8a(6H)-carboxylate. To a stirred solution of methyl 1-(2-chloroacetyl)-2-(hydroxymethyl)pyrrolidine-2-carboxylate (830 mg, 3.52 mmol) in 2-methylpropan-2-ol (18 mL) was added potassium 2-methylpropan-2-olate (0.44 g, 3.9 mmol) in several portions and the reaction mixture was stirred at rt for 3 h. Water and EtOAc were added (5 mL each). The organics were concentrated in vacuo and the aqueous layer was filtered. The filtrate was evaporated under $N_2$, acidified with $H_3PO_4$ to pH 2, saturated with NaCl and was extracted with 10% MeOH/DCM (3*20 mL). The combined organic phases were dried over $Na_2SO_4$, evaporated in vacuo and chromatographed on silica gel using 60 to 100% EtOAc/hexane as eluent to yield methyl 4-oxotetrahydro-1H-pyrrolo[2,1-c][1,4]oxazine-8a(6H)-carboxylate (528 mg, 75%). LCMS (MM-ES+APCI, Pos): m/z 200.2 [M+H].

Step C. (Tetrahydro-1H-pyrrolo[2,1-c][1,4]oxazin-8a (6H)-yl)methanol. A solution of methyl 4-oxotetrahydro-1H-pyrrolo[2,1-c][1,4]oxazine-8a(6H)-carboxylate (528 mg, 2.65 mmol) in diethyl ether was added dropwise to a stirred and refluxed mixture of $LiAlH_4$ (402 mg, 10.6 mmol) and diethyl ether (53 mL) under $N_2$ atmosphere. The reaction was stirred at reflux for 2 h followed by stirring overnight at rt. The reaction was quenched with $H_2O$ and NaOH, and the slurry was filtered. The aqueous layer was saturated with KOH and layers were separated. The ether layer was dried over KOH, filtered and concentrated under $N_2$. The crude material was dissolved in methanol (5 mL) and dihydroxypalladium on carbon (20%, 372 mg) was added. The reaction mixture was degassed and stirred under hydrogen atmosphere for 3 h. The slurry was filtered through Celite, concentrated in vacuo. The residue was chromatographed on silica gel with 4 to 8% MeOH/DCM with 10% $NH_4OH$ as additive to yield (tetrahydro-1H-pyrrolo[2,1-c][1,4]oxazin-8a(6H)-yl)methanol (0.15 g, 36%). LCMS (MM-ES+APCI, Pos): m/z 158.2 [M+H].

Step D. tert-butyl (1R,5S)-3-(7-(8-chloronaphthalen-1-yl)-8-fluoro-2-((tetrahydro-1H-pyrrolo[2,1-c][1,4]oxazin-8a(6H)-yl)methoxy)pyrido[4,3-d]pyrimidin-4-yl)-3,8-diazabicyclo[3.2.1]octane-8-carboxylate. Synthesized according to Example 29, Step H using (tetrahydro-1H-pyrrolo[2,1-c][1,4]oxazin-8a(6H)-yl)methanol in place of (S)-(1-isopropylpyrrolidin-2-yl)methanol to yield tert-butyl (1R,5S)-3-(7-(8-chloronaphthalen-1-yl)-8-fluoro-2-((tetrahydro-1H-pyrrolo[2,1-c][1,4]oxazin-8a(6H)-yl)methoxy)pyrido[4,3-d]pyrimidin-4-yl)-3,8-diazabicyclo[3.2.1]octane-8-carboxylate (37 mg, 61%). LCMS (MM-ES+APCI, Pos): m/z 675.3 [M+H].

Step E. 8a-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)hexahydro-1H-pyrrolo[2,1-c][1,4]oxazine. Synthesized according to Example 29, Step I deprotection using tert-butyl (1R,5S)-3-(7-(8-chloronaphthalen-1-yl)-8-fluoro-2-((tetrahydro-1H-pyrrolo[2,1-c][1,4]oxazin-8a(6H)-yl)methoxy)pyrido[4,3-d]pyrimidin-4-yl)-3,8-diazabicyclo[3.2.1]octane-8-carboxylate to yield 8a-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)hexahydro-1H-pyrrolo[2,1-c][1,4]oxazine (22 mg, 71%). LCMS (MM-ES+APCI, Pos): m/z 575.2 [M+H].

Example 201

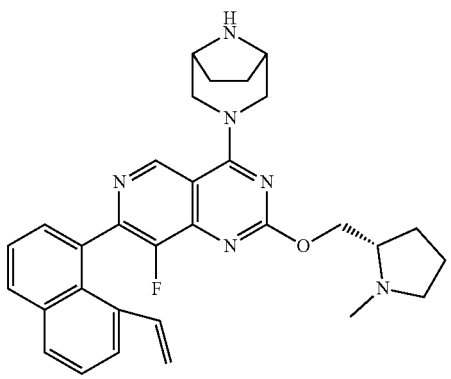 [SMILES: C=Cc1cccc2cccc(-c3ncc4c(N5CC6CCC(C5)N6)nc(OC[C@@H]5CCCN5C)nc4c3F)c12]

4-((1R,5S)-3,8-diazabicyclo[3.2.1]octan-3-yl)-8-fluoro-2-(((S)-1-methylpyrrolidin-2-yl)methoxy)-7-(8-vinylnaphthalen-1-yl)pyrido[4,3-d]pyrimidine

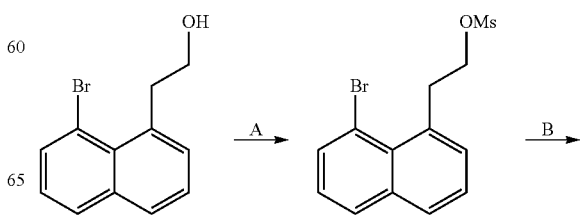

-continued

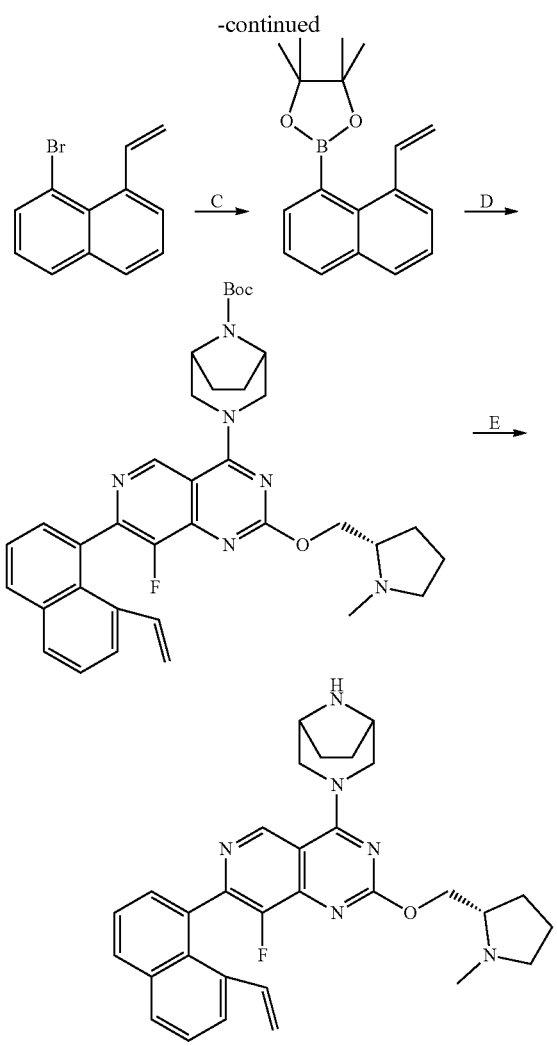

Step A. 2-(8-bromonaphthalen-1-yl)ethyl methanesulfonate. A stirred solution of crude 2-(8-bromonaphthalen-1-yl)ethan-1-ol (0.18 g, 0.72 mmol) and N-ethyl-N-isopropylpropan-2-amine (0.19 mL, 1.1 mmol) in dichloromethane (5 mL) was cooled to 0° C. and methanesulfonyl chloride (0.067 mL, 0.87 mmol) was added dropwise. The reaction mixture was warmed to r.t. over 2 hours and partitioned between hexane/EtOAc (1:1, 15 mL) and 0.5M NaHCO$_3$ (5 mL). The organic phase was washed with brine, dried over Na$_2$SO$_4$, and evaporated in vacuo. The material was dissolved in MTBE (2 mL), filtered, and evaporated under N$_2$ to give the crude product (0.22 g, 93%).

Step B. 1-Bromo-8-vinylnaphthalene. A solution of 2-(8-bromonaphthalen-1-yl)ethyl methanesulfonate (1.19 mmol) in tetrahydrofuran (12 mL) under N$_2$ cooled to −10° C. was added potassium 2-methylpropan-2-olate (0.34 g, 3 mmol) in several portions. The solution was warmed to rt and stirred at rt for 1 h. The reaction mixture was partitioned between water (20 mL) and hexane (30 mL) and the layers were separated. The organic layer was washed with water, sat. NaHCO$_3$ and brine (5 mL each), dried over Na$_2$CO$_3$, evaporated in vacuo and chromatographed on silica gel using hexane as eluent to yield 1-bromo-8-vinylnaphthalene as colorless oil (0.25 g, 90%).

Step C. 4,4,5,5-tetramethyl-2-(8-vinylnaphthalen-1-yl)-1,3,2-dioxaborolane. Synthesized according to intermediate 1 using 1-bromo-8-vinylnaphthalene in place of 1-bromo-8-chloronaphthalene to yield 4,4,5,5-tetramethyl-2-(8-vinylnaphthalen-1-yl)-1,3,2-dioxaborolane (108 mg, 90%). $^1$H NMR (400 MHz, CDCl$_3$): δ 7.85 (dd, J=8.2, 1.4 Hz, 1H), 7.76 (dd, J=8.2, 1.4 Hz, 1H), 7.67 (dd, J=6.6, 1.4 Hz, 1H), 7.56 (ddd, J=7.0, 1.3, 0.7 Hz, 1H), 7.50-7.40 (m, 3H), 5.77 (dd, J=17.2, 1.4 Hz, 1H), 5.38 (dd, J=10.3, 1.5 Hz, 1H), 1.43 (s, 12H) ppm.

Step D. tert-butyl (1R,5S)-3-(8-fluoro-2-(((S)-1-methylpyrrolidin-2-yl)methoxy)-7-(8-vinylnaphthalen-1-yl)pyrido[4,3-d]pyrimidin-4-yl)-3,8-diazabicyclo[3.2.1]octane-8-carboxylate. Synthesized according to Example 1, Step A using tert-butyl (1R,5S)-3-(7-chloro-8-fluoro-2-(((S)-1-methylpyrrolidin-2-yl)methoxy)pyrido[4,3-d]pyrimidin-4-yl)-3,8-diazabicyclo[3.2.1]octane-8-carboxylate (synthesized according to Example 3, Step A-G substituting (S)-(1-methylpyrrolidin-2-yl)methanol in place of 2-(1-methyl-1H-imidazol-2-yl)ethan-1-ol) and 4,4,5,5-tetramethyl-2-(8-vinylnaphthalen-1-yl)-1,3,2-dioxaborolane as coupling partners to yield tert-butyl (1R,5S)-3-(8-fluoro-2-(((S)-1-methylpyrrolidin-2-yl)methoxy)-7-(8-vinylnaphthalen-1-yl)pyrido[4,3-d]pyrimidin-4-yl)-3,8-diazabicyclo[3.2.1]octane-8-carboxylate (7 mg, 11%). LCMS (MM-ES+APCI, Pos): m/z 625.3 [M+H].

Step E. 4-((1R,5S)-3,8-diazabicyclo[3.2.1]octan-3-yl)-8-fluoro-2-(((S)-1-methylpyrrolidin-2-yl)methoxy)-7-(8-vinylnaphthalen-1-yl)pyrido[4,3-d]pyrimidine. Synthesized according to Example 1, Step G using tert-butyl (1R,5S)-3-(8-fluoro-2-(((S)-1-methylpyrrolidin-2-yl)methoxy)-7-(8-vinylnaphthalen-1-yl)pyrido[4,3-d]pyrimidin-4-yl)-3,8-diazabicyclo[3.2.1]octane-8-carboxylate in place of tert-butyl 3-(7-(3-hydroxynaphthalen-1-yl)-2-(((S)-1-methylpyrrolidin-2-yl)methoxy)pyrido[4,3-d]pyrimidin-4-yl)-3,8-diazabicyclo[3.2.1]octane-8-carboxylate to yield the title compound (1.8 mg, 30%). LCMS (MM-ES+APCI, Pos): m/z 525.3 [M+H].

Example 202

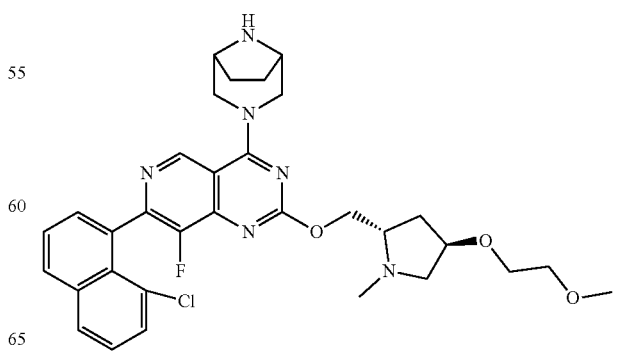

4-((1R,5S)-3,8-diazabicyclo[3.2.1]octan-3-yl)-7-(8-chloronaphthalen-1-yl)-8-fluoro-2-(((2S,4R)-4-(2-methoxyethoxy)-1-methylpyrrolidin-2-yl)methoxy)pyrido[4,3-d]pyrimidine

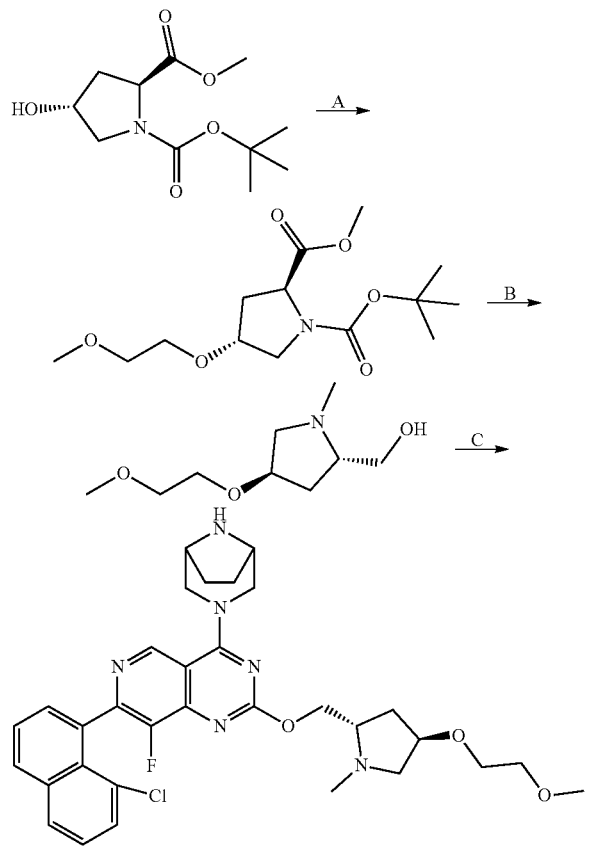

Step A. 1-(tert-butyl) 2-methyl (2S,4R)-4-(2-methoxyethoxy)pyrrolidine-1,2-dicarboxylate. To a solution of 1-(tert-butyl) 2-methyl (2S,4R)-4-hydroxypyrrolidine-1,2-dicarboxylate (1.0 g, 4.1 mmol) in DMF (20 mL) under $N_2$ at rt was added sodium hydride (196 mg, 60%, 4.89 mmol) portion wise. After bubbling was ceased (30 min), 1-bromo-2-methoxyethane (575 µL, 6.12 mmol) was added and the mixture stirred for 2 hrs. A further 300 µL of 1-bromo-2-methoxyethane was added and stirring was continued for 16 hrs. The mixture was partitioned between water (100 mL) and EtOAc (50 mL) and the aqueous layer was extracted with EtOAc (2×30 mL). The combined organic phases were washed with water (6×30 mL) and brine (30 mL), then dried over $Na_2SO_4$, filtered and concentrated. The residue was purified by flash column chromatography eluting with 0-25% (20% MeOH/DCM)/DCM to afford 1-(tert-butyl) 2-methyl (2S,4R)-4-(2-methoxyethoxy)pyrrolidine-1,2-dicarboxylate (0.29 g, 0.97 mmol, 24.0% yield). LCMS (MM-ES+APCI, Pos): m/z 304.1 (M+H).

Step B. ((2S,4R)-4-(2-methoxyethoxy)-1-methylpyrrolidin-2-yl)methanol. To a solution of 1-(tert-butyl) 2-methyl (2S,4R)-4-(2-methoxyethoxy)pyrrolidine-1,2-dicarboxylate (295 mg, 0.97 mmol) in THF (10 mL) under $N_2$ at 0° C. was added lithium aluminum hydride solution (2.92 mL, 1M, 2.92 mmol) dropwise over 10 min. The mixture was stirred for 30 minutes, heated to reflux for 3 hours, then cooled to 0° C., and quenched by dropwise addition of 0.5 mL of saturated sodium sulfate. After stirring for 1 hour, the mixture was filtered through a bed of Celite. The filtrate was dried over $Na_2SO_4$, filtered and concentrated to afford ((2S,4R)-4-(2-methoxyethoxy)-1-methylpyrrolidin-2-yl)methanol (0.15 g, 0.80 mmol, 83% yield). LCMS (MM-ES+APCI, Pos): m/z 190.1 (M+H).

Step C. 4-((1R,5S)-3,8-diazabicyclo[3.2.1]octan-3-yl)-7-(8-chloronaphthalen-1-yl)-8-fluoro-2-(((2S,4R)-4-(2-methoxyethoxy)-1-methylpyrrolidin-2-yl)methoxy)pyrido[4,3-d]pyrimidine. Synthesized according to Example 29, substituting ((2S,4R)-4-(2-methoxyethoxy)-1-methylpyrrolidin-2-yl)methanol in place of (S)-(1-isopropylpyrrolidin-2-yl)methanol in Step H to afford 4-((1R,5S)-3,8-diazabicyclo[3.2.1]octan-3-yl)-7-(8-chloronaphthalen-1-yl)-8-fluoro-2-(((2S,4R)-4-(2-methoxyethoxy)-1-methylpyrrolidin-2-yl)methoxy)pyrido[4,3-d]pyrimidine (12.7 mg, 0.02 mmol, 74% yield). LCMS (MM-ES+APCI, Pos): m/z 607.3 (M+H).

Example 203

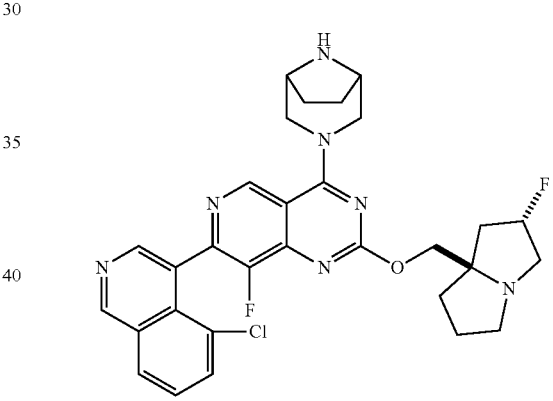

4-((1R,5S)-3,8-diazabicyclo[3.2.1]octan-3-yl)-7-(5-chloroisoquinolin-4-yl)-8-fluoro-2-(((2S,7aR)-2-fluorotetrahydro-1H-pyrrolizin-7a(5H)-yl)methoxy)pyrido[4,3-d]pyrimidine

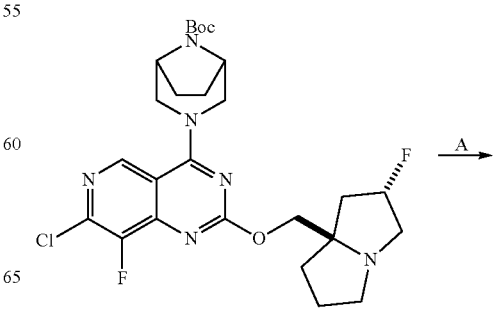

429 -continued

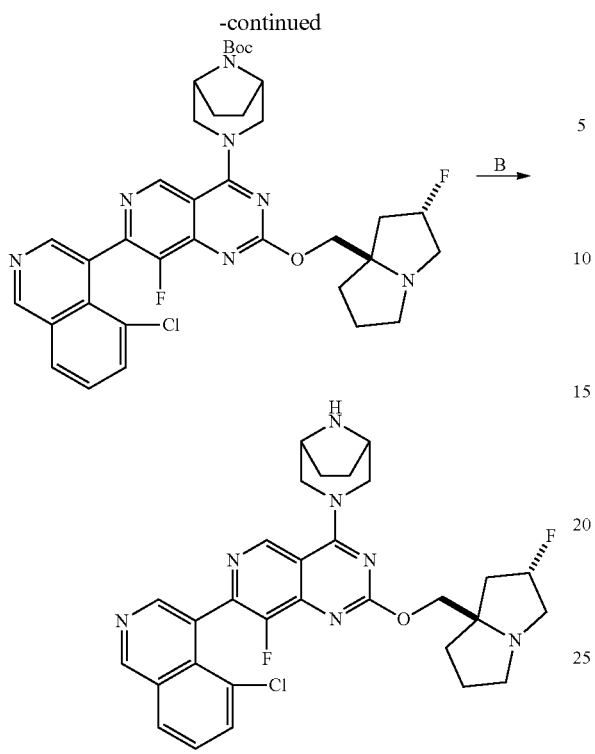

430 Example 204

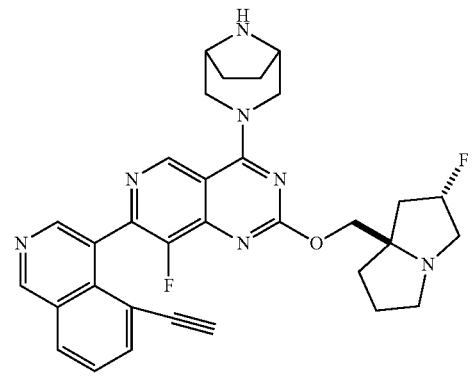

4-((1R,5S)-3,8-diazabicyclo[3.2.1]octan-3-yl)-7-(5-ethynylisoquinolin-4-yl)-8-fluoro-2-(((2S,7aR)-2-fluorotetrahydro-1H-pyrrolizin-7a(5H)-yl)methoxy)pyrido[4,3-d]pyrimidine Step A. Tert-butyl (1R,5S)-3-(7-(5-chloroisoquinolin-4-yl)-8-fluoro-2-(((2S,7aR)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate. Synthesized according to Example 33, Step B substituting tert-butyl (1R,5S)-3-(7-chloro-8-fluoro-2-(((2S,7aR)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate in place of tert-butyl (1R,5S)-3-(7-chloro-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate to afford tert-butyl (1R,5S)-3-(7-(5-chloroisoquinolin-4-yl)-8-fluoro-2-(((2S,7aR)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (100 mg, 0.133 mmol, 73%). LCMS (MM-ES+APCI, Pos): m/z 679.2 (M+H).

Step B. 4-((1R,5S)-3,8-diazabicyclo[3.2.1]octan-3-yl)-7-(5-chloroisoquinolin-4-yl)-8-fluoro-2-(((2S,7aR)-2-fluorotetrahydro-1H-pyrrolizin-7a(5H)-yl)methoxy)pyrido[4,3-d]pyrimidine. To a solution of tert-butyl (1R,5S)-3-(7-chloro-8-fluoro-2-(((2S,7aR)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (33 mg, 0.049 mmol) in CH$_2$Cl$_2$ (1 mL) was added HCl (1 mL, 4 N in dioxane). The mixture was stirred for 30 minutes at room temperature. The product was collected by vacuum filtration and dried in vacuo affording 4-((1R,5S)-3,8-diazabicyclo[3.2.1]octan-3-yl)-7-(5-chloroisoquinolin-4-yl)-8-fluoro-2-(((2S,7aR)-2-fluorotetrahydro-1H-pyrrolizin-7a(5H)-yl)methoxy)pyrido[4,3-d]pyrimidine as the dihydrochloride salt (16 mg, 0.025 mmol, 51%). LCMS (MM-ES+APCI, Pos): m/z 578.2 (M+H).

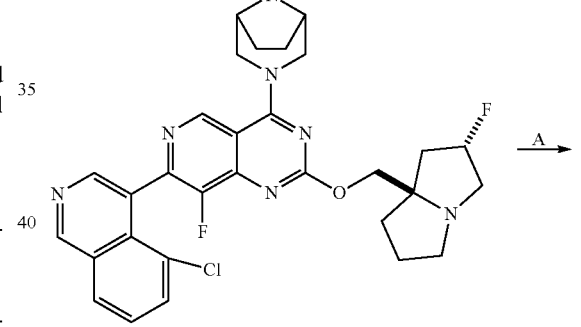

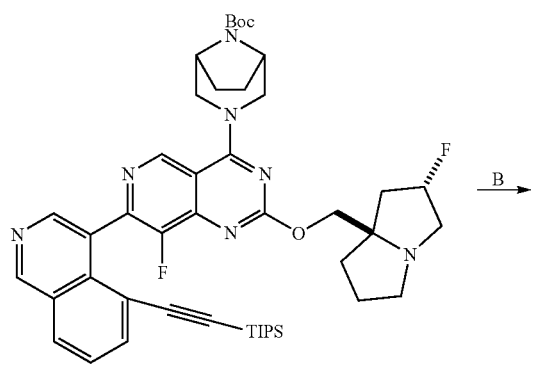

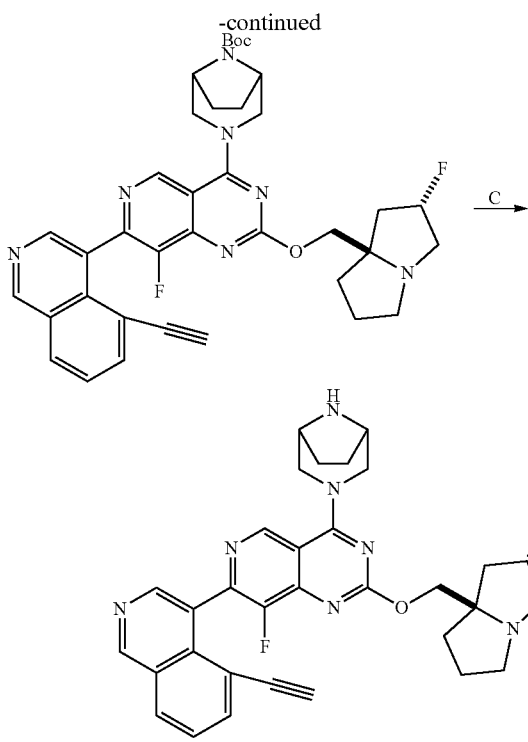

Step A: Tert-butyl (1R,5S)-3-(8-fluoro-2-(((2S,7aR)-2-fluorotetrahydro-1H-pyrrolizin-7a(5H)-yl)methoxy)-7-(5-((triisopropylsilyl)ethynyl)isoquinolin-4-yl)pyrido[4,3-d]pyrimidin-4-yl)-3,8-diazabicyclo[3.2.1]octane-8-carboxylate. To a solution of tert-butyl (1R,5S)-3-(7-(5-chloroisoquinolin-4-yl)-8-fluoro-2-(((2S,7aR)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (49 mg, 0.072 mmol) in CH₃CN (1.5 mL) were added dicyclohexyl(2',4',6'-triisopropyl-[1,1'-biphenyl]-2-yl)phosphane (21 mg, 0.044 mmol), cesium carbonate (47 mg, 0.145 mmol), bis(acetonitrile)palladium(II) dichloride (4 mg, 0.015 mmol) and triisopropylsilylacetylene (81 µL, 0.361 mmol). After purging with argon, the vial was heated to 85° C. for 2.5 hours. The cooled mixture was diluted with EtOAc, filtered through Celite, and concentrated in vacuo. The residue was purified by flash chromatography eluting with 0-50% (20% MeOH/CH₂Cl₂)/CH₂Cl₂, to afford tert-butyl (1R,5S)-3-(8-fluoro-2-(((2S,7aR)-2-fluorotetrahydro-1H-pyrrolizin-7a(5H)-yl)methoxy)-7-(5-((triisopropylsilyl)ethynyl)isoquinolin-4-yl)pyrido[4,3-d]pyrimidin-4-yl)-3,8-diazabicyclo[3.2.1]octane-8-carboxylate (28 mg, 0.034 mmol, 47%). LCMS (MM-ES+APCI, Pos): m/z 825.2 (M+H).

Step B. Tert-butyl (1R,5S)-3-(7-(5-ethynylisoquinolin-4-yl)-8-fluoro-2-(((2S,7aR)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate. To a solution of tert-butyl (1R,5S)-3-(8-fluoro-2-(((2S,7aR)-2-fluorotetrahydro-1H-pyrrolizin-7a(5H)-yl)methoxy)-7-(5-((triisopropylsilyl)ethynyl)isoquinolin-4-yl)pyrido[4,3-d]pyrimidin-4-yl)-3,8-diazabicyclo[3.2.1]octane-8-carboxylate (28 mg, 0.034 mmol) in THF (0.7 mL) was added tetrabutylammonium fluoride (0.175 mL, 0.175 mmol, 1 M in THF). The mixture was stirred at room temperature for 30 minutes and then suspended between EtOAc and water and the layers were separated. The aqueous phase was extracted twice with EtOAc. The combined organics were dried over MgSO₄, filtered, and concentrated in vacuo to furnish tert-butyl (1R,5S)-3-(7-(5-ethynylisoquinolin-4-yl)-8-fluoro-2-(((2S,7aR)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (23 mg, 0.034 mmol, >99%). LCMS (MM-ES+APCI, Pos): m/z 668.3 (M+H).

Step C. 4-((1R,5S)-3,8-diazabicyclo[3.2.1]octan-3-yl)-7-(5-ethynylisoquinolin-4-yl)-8-fluoro-2-(((2S,7aR)-2-fluorotetrahydro-1H-pyrrolizin-7a(5H)-yl)methoxy)pyrido[4,3-d]pyrimidine. Synthesized according to Example 203, Step B substituting tert-butyl (1R,5S)-3-(7-(5-ethynylisoquinolin-4-yl)-8-fluoro-2-(((2S,7aR)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate in place of tert-butyl (1R,5S)-3-(7-(5-chloroisoquinolin-4-yl)-8-fluoro-2-(((2S,7aR)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate to afford 4-((1R,5S)-3,8-diazabicyclo[3.2.1]octan-3-yl)-7-(5-ethynylisoquinolin-4-yl)-8-fluoro-2-(((2S,7aR)-2-fluorotetrahydro-1H-pyrrolizin-7a(5H)-yl)methoxy)pyrido[4,3-d]pyrimidine as the dihydrochloride salt (1.8 mg, 0.003 mmol, 8%). LCMS (MM-ES+APCI, Pos): m/z 568.2 (M+H).

Example 205

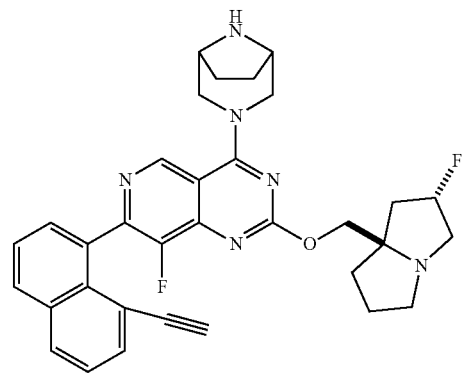

4-((1R,5S)-3,8-diazabicyclo[3.2.1]octan-3-yl)-7-(8-ethynylnaphthalen-1-yl)-8-fluoro-2-(((2S,7aR)-2-fluorotetrahydro-1H-pyrrolizin-7a(5H)-yl)methoxy)pyrido[4,3-d]pyrimidine

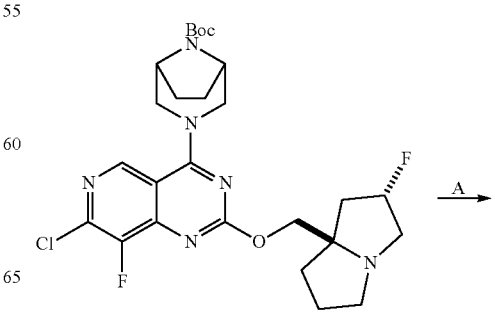

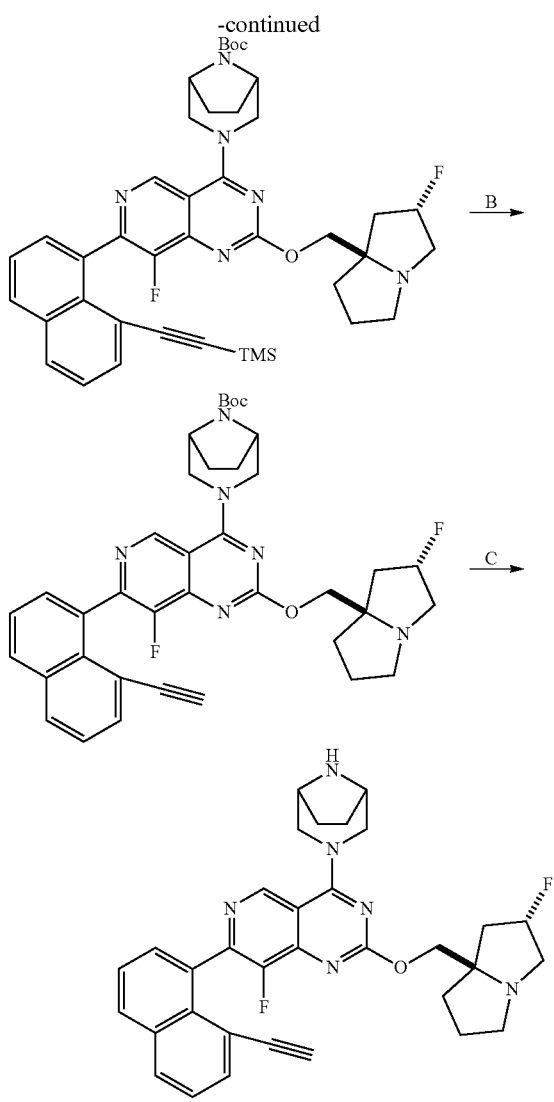

Step A. Tert-butyl (1R,5S)-3-(8-fluoro-2-(((2S,7aR)-2-fluorotetrahydro-1H-pyrrolizin-7a(5H)-yl)methoxy)-7-(8-((trimethylsilyl)ethynyl)naphthalen-1-yl)pyrido[4,3-d]pyrimidin-4-yl)-3,8-diazabicyclo[3.2.1]octane-8-carboxylate. A vial containing tert-butyl (1R,5S)-3-(7-chloro-8-fluoro-2-(((2S,7aR)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (75 mg, 0.14 mmol) and trimethyl((8-(trimethylstannyl)naphthalen-1-yl)ethynyl)silane (79 mg, 0.2 mmol) in toluene (500 ul) was purged with argon. Copper(I) iodide (8 mg, 0.04 mmol) and palladium tetrakis(triphenylphosphine) (31 mg, 0.027 mmol) were added and the suspension was sparged with argon for 5 minutes. The vial was sealed and heated to 100° C. for 16 hours. To the reaction mixture was added additional trimethyl((8-(trimethylstannyl)naphthalen-1-yl)ethynyl)silane (79 mg, 0.20 mmol), copper(I) iodide (8 mg, 0.041 mmol) and palladium tetrakis(triphenylphosphine) (31 mg, 0.027 mmol). After stirred for 3.5 hours at 100° C. the reaction mixture was cooled and diluted with ethyl acetate (5 mL). The organics were washed with water, dried over MgSO$_4$, and concentrated in vacuo. The residue was purified by flash chromatography eluting with 0-50% (20% MeOH/CH$_2$Cl$_2$)/CH$_2$Cl$_2$, to afford tert-butyl (1R,5S)-3-(8-fluoro-2-(((2S,7aR)-2-fluorotetrahydro-1H-pyrrolizin-7a(5H)-yl)methoxy)-7-(8-((trimethylsilyl)ethynyl)naphthalen-1-yl)pyrido[4,3-d]pyrimidin-4-yl)-3,8-diazabicyclo[3.2.1]octane-8-carboxylate (27 mg, 0.037 mmol, 27%). LCMS (MM-ES+APCI, Pos): m/z 740.3 (M+H).

Step B. Tert-butyl (1R,5S)-3-(7-(8-ethynylnaphthalen-1-yl)-8-fluoro-2-(((2S,7aR)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate. Synthesized according to Example 204, Step B substituting tert-butyl (1R,5S)-3-(8-fluoro-2-(((2S,7aR)-2-fluorotetrahydro-1H-pyrrolizin-7a(5H)-yl)methoxy)-7-(8-((trimethylsilyl)ethynyl)naphthalen-1-yl)pyrido[4,3-d]pyrimidin-4-yl)-3,8-diazabicyclo[3.2.1]octane-8-carboxylate in place of tert-butyl (1R,5S)-3-(8-fluoro-2-(((2S,7aR)-2-fluorotetrahydro-1H-pyrrolizin-7a(5H)-yl)methoxy)-7-(5-((triisopropylsilyl)ethynyl)isoquinolin-4-yl)pyrido[4,3-d]pyrimidin-4-yl)-3,8-diazabicyclo[3.2.1]octane-8-carboxylate to afford tert-butyl (1R,5S)-3-(7-(8-ethynylnaphthalen-1-yl)-8-fluoro-2-(((2S,7aR)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (26 mg, 0.039 mmol, >99%). LCMS (MM-ES+APCI, Pos): m/z 667.3 (M+H).

Step C. 4-((1R,5S)-3,8-diazabicyclo[3.2.1]octan-3-yl)-7-(8-ethynylnaphthalen-1-yl)-8-fluoro-2-(((2S,7aR)-2-fluorotetrahydro-1H-pyrrolizin-7a(5H)-yl)methoxy)pyrido[4,3-d]pyrimidine. Synthesized according to Example 204, Step C substituting tert-butyl (1R,5S)-3-(7-(8-ethynylnaphthalen-1-yl)-8-fluoro-2-(((2S,7aR)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate in place of tert-butyl (1R,5S)-3-(7-(5-chloroisoquinolin-4-yl)-8-fluoro-2-(((2S,7aR)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate to afford 4-((1R,5S)-3,8-diazabicyclo[3.2.1]octan-3-yl)-7-(8-ethynylnaphthalen-1-yl)-8-fluoro-2-(((2S,7aR)-2-fluorotetrahydro-1H-pyrrolizin-7a(5H)-yl)methoxy)pyrido[4,3-d]pyrimidine as the dihydrochloride salt (3.9 mg, 0.006 mmol, 45%). LCMS (MM-ES+APCI, Pos): m/z 567.3 (M+H).

Example 206

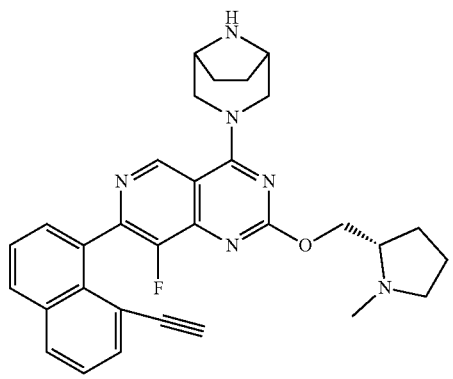 [SMILES: C#Cc1cccc2cccc(-c3ncc4c(N5CC6CCC(C5)N6)nc(OC[C@@H]5CCCN5C)nc4c3F)c12]

435

4-((1R,5S)-3,8-diazabicyclo[3.2.1]octan-3-yl)-7-(8-ethynylnaphthalen-1-yl)-8-fluoro-2-(((S)-1-methylpyrrolidin-2-yl)methoxy)pyrido[4,3-d]pyrimidine

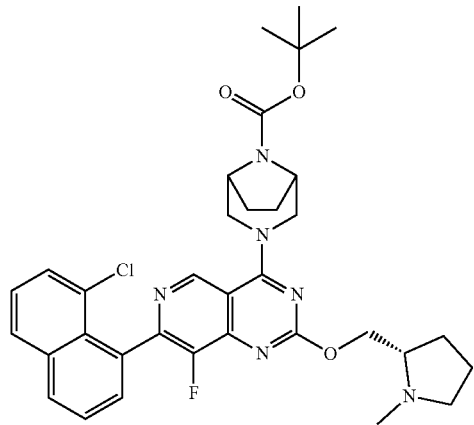

↓ A

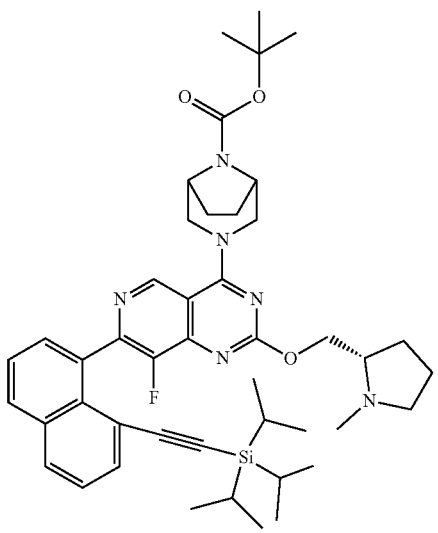

↓ B

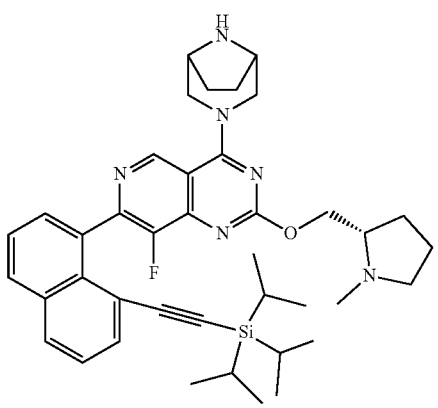

↓ C

436

-continued

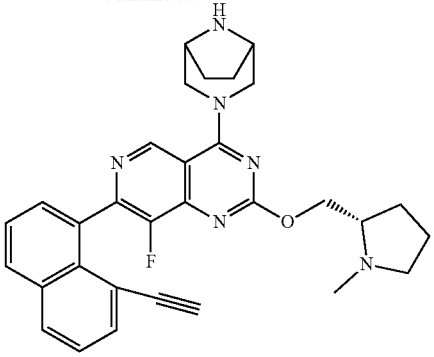 [SMILES: C#Cc1cccc2cccc(-c3ncc4c(N5CC6CCC(C5)N6)nc(OC[C@@H]5CCCN5C)nc4c3F)c12]

Step A. tert-butyl (1R,5S)-3-(8-fluoro-2-(((S)-1-methylpyrrolidin-2-yl)methoxy)-7-(8-((triisopropylsilyl)ethynyl)naphthalen-1-yl)pyrido[4,3-d]pyrimidin-4-yl)-3,8-diazabicyclo[3.2.1]octane-8-carboxylate. To a vial containing tert-butyl (1R,5S)-3-(7-(8-chloronaphthalen-1-yl)-8-fluoro-2-(((S)-1-methylpyrrolidin-2-yl)methoxy)pyrido[4,3-d]pyrimidin-4-yl)-3,8-diazabicyclo[3.2.1]octane-8-carboxylate (synthesized according to Example 132, 33 mg, 0.042 mmol, 80% purity), dichlorobis(acetonitrile)palladium(II) (2.2 mg, 0.0083 mmol), 2-(Dicyclohexylphosphino)-2,4,6-Triisopropylbiphenyl (11.9 mg, 0.025 mmol) and cesium carbonate (27 mg, 0.083 mmol) under $N_2$ was added acetonitrile (0.80 mL), followed by triisopropylsilylacetylene (47 µL, 0.21 mmol). The vial was closed and heated at 85° C. for 2.5 h. Then it was cooled to rt and was purified by preparative C18 HPLC (Gilson, 0-95% $CH_3CN/H_2O$ with 0.1% TFA). The desired fractions were combined and basified with $NaHCO_3$ (Sat.) and extracted with EtOAc. The EtOAc extract was washed with water, brine and dried ($Na_2SO_4$). The resulting solution was concentrated to the desired product (23 mg, 0.030 mmol, 71% yield) as a brown solid. LCMS (MM-ES+APCI, Pos): m/z 779.5 (M+H).

Step B. 4-((1R,5S)-3,8-diazabicyclo[3.2.1]octan-3-yl)-8-fluoro-2-(((S)-1-methylpyrrolidin-2-yl)methoxy)-7-(8-((triisopropylsilyl)ethynyl)naphthalen-1-yl)pyrido[4,3-d]pyrimidine. To a solution of tert-butyl (1R,5S)-3-(8-fluoro-2-(((S)-1-methylpyrrolidin-2-yl)methoxy)-7-(8-((triisopropylsilyl)ethynyl)naphthalen-1-yl)pyrido[4,3-d]pyrimidin-4-yl)-3,8-diazabicyclo[3.2.1]octane-8-carboxylate (22 mg, 0.028 mmol) in DCM (0.9 mL) at 0° C. was added $BCl_3$ (1.0 M in DCM, 0.10 mL, 0.10 mmol). The mixture was stirred at 0° C. for 20 min, and quenched with $NaHCO_3$ (sat.). The mixture extracted with DCM. The extract was dried over $Na_2SO_4$ and concentrated to give the crude desired product as a brown solid. LCMS (MM-ES+APCI, Pos): m/z 679.4 (M+H).

Step C. 4-((1R,5S)-3,8-diazabicyclo[3.2.1]octan-3-yl)-7-(8-ethynylnaphthalen-1-yl)-8-fluoro-2-(((S)-1-methylpyrrolidin-2-yl)methoxy)pyrido[4,3-d]pyrimidine. To a solution of the 4-((1R,5S)-3,8-diazabicyclo[3.2.1]octan-3-yl)-8-fluoro-2-(((S)-1-methylpyrrolidin-2-yl)methoxy)-7-(8-((triisopropylsilyl)ethynyl)naphthalen-1-yl)pyrido[4,3-d]pyrimidine in THF (0.6 mL) was added TBAF (1.0 M, 0.050 mL, 0.050 mmol). The mixture was stirred at 0° C. for 0.5 h and was purified by preparative C18 HPLC (Gilson, 0-95% $CH_3CN/H_2O$ with 0.1% $NH_4OAc$). The desired fractions were combined and neutralized with $NaHCO_3$ (sat.). The mixture was extracted with DCM/IPA (5:1). The extract was dried over $Na_2SO_4$ and concentrated to give the title compound (12 mg, 0.023 mmol, 82% yield over 2 steps) as a brown solid. LCMS (MM-ES+APCI, Pos): m/z 523.3 (M+H).

Example 207

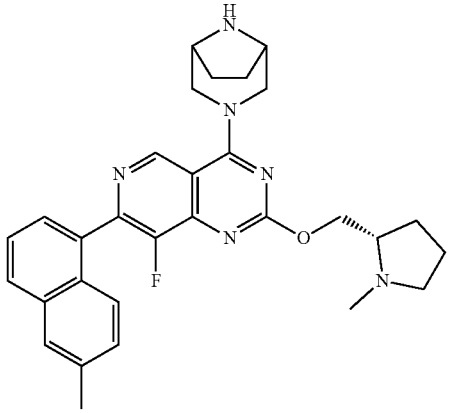 [SMILES: Cc1ccc2c(-c3ncc4c(N5CC6CCC(C5)N6)nc(OC[C@@H]5CCCN5C)nc4c3F)cccc2c1]

4-((1R,5S)-3,8-diazabicyclo[3.2.1]octan-3-yl)-8-fluoro-7-(6-methylnaphthalen-1-yl)-2-(((S)-1-methylpyrrolidin-2-yl)methoxy)pyrido[4,3-d]pyrimidine

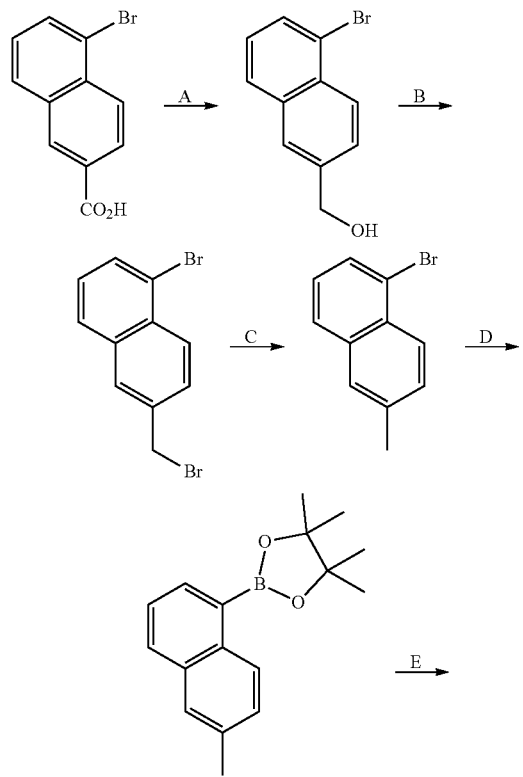

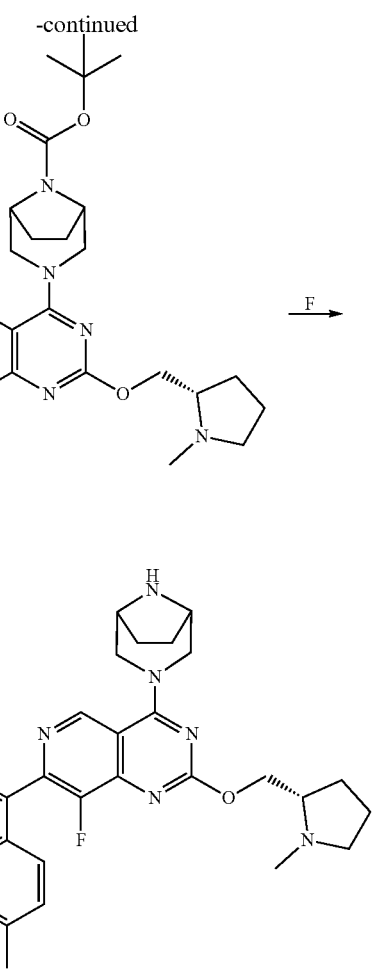

Step A. (5-bromonaphthalen-2-yl)methanol. To a suspension of 5-bromo-2-naphthoic acid (0.51 g, 2.0 mmol) in THF (10 mL, 2.0 mmol) at 0° C. was added borane-methyl sulfide complex (0.48 mL, 5.1 mmol) slowly. After addition, the ice bath was removed, and the mixture was stirred at rt for 18 h. The mixture was heated at 45° C. for 2 h to give a clear solution. The solution was cooled to 0° C. and quenched with MeOH (2 mL). The solution was stirred at 0° C. for 10 min followed by addition of ice (2 g) and water (10 mL). The resulting mixture was stirred at rt for 1 h. The solution was then extracted with EtOAc (40 mL). The organics was washed with water (40 mL), brine (20 mL), dried over $Na_2SO_4$ and concentrated to give crude desired product (0.47 g, 2.0 mmol, 98% yield) as a white solid. $^1$H NMR (400 MHz, (CDCl$_3$) δ 8.22 (d, J=8.8 Hz, 1H), 7.78 (m, 3H), 7.57 (d, J=8.8 Hz, 1H), 7.32 (m, 1H), 4.89 (s, 2H) ppm.

Step B. 1-bromo-6-(bromomethyl)naphthalene. To a solution of (5-bromonaphthalen-2-yl)methanol (120 mg, 0.51 mmol) in DCM (3.4 mL) was added phosphorus tribromide (72 μL, 0.76 mmol). The mixture was stirred at rt for 6 h and then diluted with DCM. The layers were separated, and the organics were washed with water, NaHCO$_3$ (sat.) and brine. The organics were dried over $Na_2SO_4$ and concentrated to give the crude desired product (88 mg, 0.29 mmol, 58% yield) as a white solid. $^1$H NMR (400 MHz, (CDCl$_3$) δ 8.22 (d, J=8.8 Hz, 1H), 7.83 (d, J=1.6 Hz, 1H), 7.78 (d, J=7.8 Hz, 2H), 7.62 (dd, J=1.6, 8.8 Hz, 1H), 7.34 (t, J=7.8 Hz, 1H), 4.67 (s, 2H) ppm.

Step C. 1-bromo-6-methylnaphthalene. To a solution of 1-bromo-6-(bromomethyl)naphthalene (84 mg, 0.28 mmol) in DMSO (2.8 mL) was added NaBH$_4$ (85 mg, 2.2 mmol). The mixture was stirred at rt for 1 h. The mixture was quenched with water and extracted with EtOAc/hexanes (1:1). The extract was washed with water, brine, dried over Na$_2$SO$_4$ and concentrated to give the crude desired product (24 mg, 0.11 mmol, 39% yield) as light purple oil.

Step D. 4,4,5,5-tetramethyl-2-(6-methylnaphthalen-1-yl)-1,3,2-dioxaborolane. To a vial containing 1-bromo-6-methylnaphthalene (24 mg, 0.11 mmol), potassium acetate (32 mg, 0.33 mmol), 4,4,4',4',5,5,5',5'-octamethyl-2,2'-bi(1,3,2-dioxaborolane) (84 mg, 0.33 mmol) and PdCl$_2$(dppf) (8.0 mg, 0.011 mmol) was added dioxane (1.1 mL). The mixture was flushed with N$_2$ for 1 minute, closed with a cap and heated to 90° C. for 15 hrs. The mixture was cooled to rt, quenched with EtOAc and hexanes. The mixture was filtered through a filter plug and the filtrate was concentrated and purified by flash chromatography eluting with 0-25% EtOAc/hexanes (0-15%) to give the desired product (27 mg, 0.10 mmol, 92% yield) as a colorless oil. $^1$H NMR (400 MHz, (CDCl$_3$) δ 8.64 (d, J=8.6 Hz, 1H), 7.99 (d, J=8.0 Hz, 1H), 7.84 (dd, J=1.4, 8.0 Hz, 1H), 7.59 (s, 1H), 7.42 (t, J=7.6 Hz, 1H), 7.36 (dd, J=1.4, 8.6 Hz, 1H), 2.50 (S, 3H), 1.42 (s, 12H) ppm.

Step E. tert-butyl (1R,5S)-3-(8-fluoro-7-(6-methylnaphthalen-1-yl)-2-(((S)-1-methylpyrrolidin-2-yl)methoxy)pyrido[4,3-d]pyrimidin-4-yl)-3,8-diazabicyclo[3.2.1]octane-8-carboxylate. To a vial containing a mixture of tert-butyl (1R,5S)-3-(7-chloro-8-fluoro-2-(((S)-1-methylpyrrolidin-2-yl)methoxy)pyrido[4,3-d]pyrimidin-4-yl)-3,8-diazabicyclo[3.2.1]octane-8-carboxylate (synthesized according to Example 3, Step A-G substituting (S)-(1-methylpyrrolidin-2-yl)methanol in place of 2-(1-methyl-1H-imidazol-2-yl)ethan-1-ol) (38 mg, 0.075 mmol), 4,4,5,5-tetramethyl-2-(6-methylnaphthalen-1-yl)-1,3,2-dioxaborolane (28 mg, 0.11 mmol) and Pd(PPh$_3$)$_4$ (8.7 mg, 0.0075 mmol) were added dioxane (0.75 mL) and NaOH (2.0 M, 75 µL, 0.15 mmol). The mixture was sparged with N$_2$ and the vial was closed. The mixture was heated at 85° C. for 20 h. The mixture was cooled to rt and purified by preparative C18 HPLC (Gilson, 0-95% CH$_3$CN/H$_2$O with 0.1% TFA). The desired fractions were combined and neutralized with NaHCO$_3$ (sat.). The mixture was extracted with DCM and the layers were separated. The combined extract was dried over Na$_2$SO$_4$ and concentrated to give the desired product (46 mg, 0.075 mmol, 100%) as a white solid. LCMS (MM-ES+APCI, Pos): m/z 613.3 (M+H).

Step F. 4-((1R,5S)-3,8-diazabicyclo[3.2.1]octan-3-yl)-8-fluoro-7-(6-methylnaphthalen-1-yl)-2-(((S)-1-methylpyrrolidin-2-yl)methoxy)pyrido[4,3-d]pyrimidine. To a solution of tert-butyl (1R,5S)-3-(8-fluoro-7-(6-methylnaphthalen-1-yl)-2-(((S)-1-methylpyrrolidin-2-yl)methoxy)pyrido[4,3-d]pyrimidin-4-yl)-3,8-diazabicyclo[3.2.1]octane-8-carboxylate (40 mg, 0.065 mmol) in DCM (1.0 mL, 0.065 mmol) was added TFA (0.50 mL, 0.065 mmol). The solution was stirred at rt for 1 h and concentrated to dryness. The residue was purified by preparative C18 HPLC (Gilson, 0-95% CH$_3$CN/H$_2$O with 0.1% TFA). The desired fractions were combined and neutralized with NaHCO$_3$ (sat.). The mixture was extracted with DCM. The combined extract was dried over Na$_2$SO$_4$ and concentrated to give the desired product (20 mg, 0.039 mmol, 60% yield) as a white solid. LCMS (MM-ES+APCI, Pos): m/z 513.3 (M+H).

Example 208

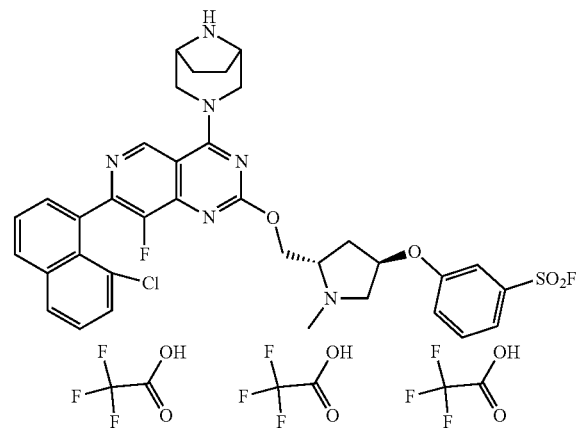

3-(((3R,5S)-5-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)-1-methylpyrrolidin-3-yl)oxy)benzenesulfonyl fluoride tris (2,2,2-trifluoroacetate)

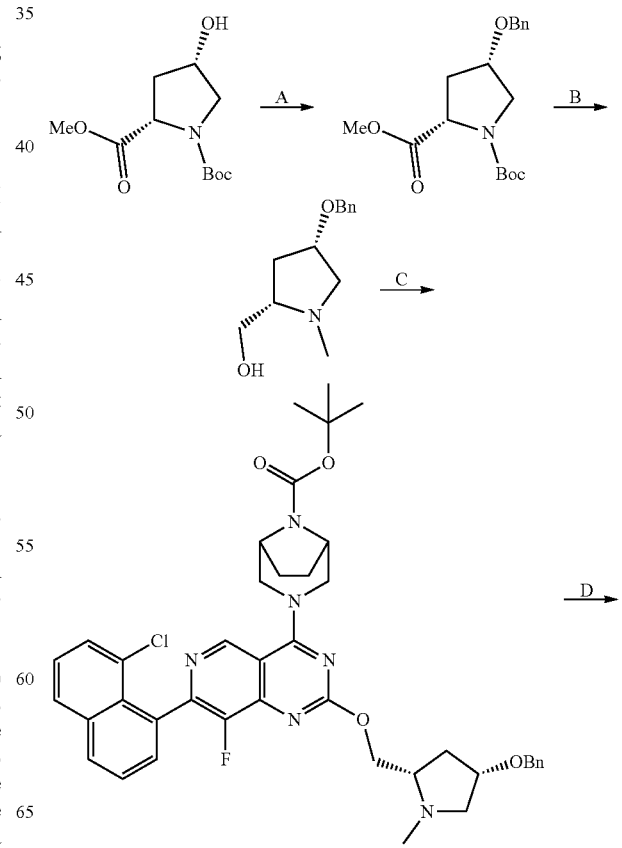

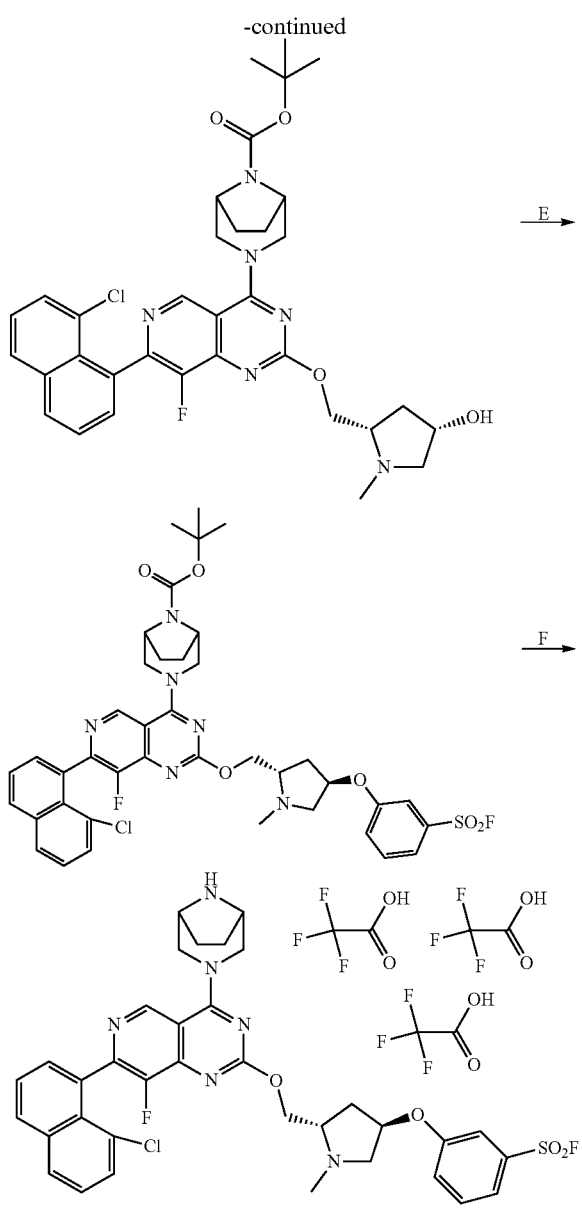

Step A. 1-(tert-butyl) 2-methyl (2 S,4 S)-4-(benzyloxy) pyrrolidine-1,2-dicarboxylate. To a mixture of 1-(tert-butyl) 2-methyl (2S,4S)-4-hydroxypyrrolidine-1,2-dicarboxylate (0.49 g, 2.00 mmol) and TBAI (0.15 g, 0.40 mmol) in tetrahydrofuran (13 mL) at 0° C. was added BnBr (0.31 mL, 2.60 mmol) followed by NaH (96 mg, 60%, 2.40 mmol). The mixture was stirred at 0° C. for 10 min, warmed to rt and stirred at rt for 15 h. The mixture was quenched with NH₄Cl (sat.) and extracted with EtOAc. The combined EtOAc extract was dried over Na₂SO₄, concentrated and purified by flash chromatography eluting with 0-15% EtOAc/hexanes to give the desired product (458 mg, 1.37 mmol, 68% yield) as a yellow oil. LCMS (MM-ES+APCI, Pos): m/z 236.2 (M+H-Boc).

Step B. ((2S,4S)-4-(benzyloxy)-1-methylpyrrolidin-2-yl)methanol. To a solution of 1-(tert-butyl) 2-methyl (2S,4S)-4-(benzyloxy)pyrrolidine-1,2-dicarboxylate (450 mg, 1.34 mmol) in THF (13 mL) at 0° C. under N₂ was added LAH (powder) (102 mg, 2.68 mmol) in three portions over 5 min. The mixture was stirred at 0° C. for 20 min until bubbling stopped and then heated at 60° C. for 2.5 h. The mixture was cooled to 0° C. and brine (1.5 mL) was added slowly. After addition, the mixture was stirred at 0° C. for additional 30 min and filtered through a short pad of Celite. The Celite was washed with THF. The combined filtrate was washed with brine. The brine solution was further extracted with DCM. The combined organic extracts were dried over Na₂SO₄ and concentrated to give the crude desired product (0.28 g, 1.27 mmol, 94.3% yield) as yellow oil. LCMS (MM-ES+APCI, Pos): m/z 222.3 (M+H).

Step C. tert-butyl (1R,5S)-3-(2-(((2S,4S)-4-(benzyloxy)-1-methylpyrrolidin-2-yl)methoxy)-7-(8-chloronaphthalen-1-yl)-8-fluoropyrido[4,3-d]pyrimidin-4-yl)-3,8-diazabicyclo[3.2.1]octane-8-carboxylate. To a solution of tert-butyl (1R,5S)-3-(2-chloro-7-(8-chloronaphthalen-1-yl)-8-fluoropyrido[4,3-d]pyrimidin-4-yl)-3,8-diazabicyclo[3.2.1]octane-8-carboxylate (0.33 g, 0.60 mmol) and ((2S,4S)-4-(benzyloxy)-1-methylpyrrolidin-2-yl)methanol (0.17 g, 0.77 mmol) in THF (6.0 mL) at 0° C. was added NaH (31 mg, 60%, 0.77 mmol). The mixture was stirred at 0° C. for 0.5 h, warmed to rt and stirred at rt for 1 h. The mixture was quenched with NH₄Cl (Sat., 0.5 mL). The mixture was concentrated to dryness. The residue was purified with preparative C18 HPLC (Gilson, 0-95% CH₃CN/H₂O with 0.1% TFA). The desired fractions were combined and concentrated to remove CH₃CN. The remaining solution was basified and extracted with DCM. The combined extract was dried over Na₂SO₄ and concentrated to give the desired product (298 mg, 0.40 mmol, 68% yield) as a white solid. LCMS (MM-ES+APCI, Pos): m/z 739.3 (100%), 741.3 (50%) (M+H, M+3).

Step D. tert-butyl (1R,5S)-3-(7-(8-chloronaphthalen-1-yl)-8-fluoro-2-(((2S,4S)-4-hydroxy-1-methylpyrrolidin-2-yl)methoxy)pyrido[4,3-d]pyrimidin-4-yl)-3,8-diazabicyclo [3.2.1]octane-8-carboxylate. To a solution of tert-butyl (1R, 5S)-3-(2-(((2S,4S)-4-(benzyloxy)-1-methylpyrrolidin-2-yl)methoxy)-7-(8-chloronaphthalen-1-yl)-8-fluoropyrido[4,3-d]pyrimidin-4-yl)-3,8-diazabicyclo[3.2.1]octane-8-carboxylate (290 mg, 0.39 mmol) in DCM (4.0 mL) at 0° C. was added BCl₃ (1.6 mL, 1.0 M, 1.6 mmol). After addition, the solution was slowly warmed to rt and stirred at rt for 1 h. The mixture was quenched with ice and NaHCO₃ (sat.) and extracted with DCM/IPA (5:1). The combined extract was dried Na₂SO₄ and concentrated to give an off-white solid. The solid was purified by preparative C18 HPLC (Gilson, 0-95% CH₃CN/H₂O with 0.1% TFA). The desired fractions were combined and neutralized with NaHCO₃ (sat.). The aqueous layer was extracted with DCM. The combined DCM extract was dried over Na₂SO₄ and concentrated to give a white solid. The solid was dissolved in DCM (4 mL) and treated with Boc-Anhydride (86 mg, 0.39 mmol). The mixture was stirred at rt for 1 h. The mixture was concentrated and the residue was purified by preparative C18 HPLC (Gilson, 0-95% CH₃CN/H₂O with 0.1% TFA). The desired fractions were combined and neutralized with NaHCO₃ (sat.). The aqueous layer was extracted with DCM. The combined DCM extract was dried over Na₂SO₄ and concentrated to give the desired product (42 mg, 0.065 mmol, 17% yield) as a white solid. LCMS (MM-ES+APCI, Pos): m/z 649.3 (100%), 651.3 (50%) (M+H, M+3).

Step E. tert-butyl (1R,5S)-3-(7-(8-chloronaphthalen-1-yl)-8-fluoro-2-(((2S,4R)-4-(3-(fluorosulfonyl)phenoxy)-1-methylpyrrolidin-2-yl)methoxy)pyrido[4,3-d]pyrimidin-4-yl)-3,8-diazabicyclo[3.2.1]octane-8-carboxylate. To a mixture of tert-butyl (1R,5S)-3-(7-(8-chloronaphthalen-1-yl)-8-fluoro-2-(((2S,4S)-4-hydroxy-1-methylpyrrolidin-2-yl)methoxy)pyrido[4,3-d]pyrimidin-4-yl)-3,8-diazabicyclo [3.2.1]octane-8-carboxylate (20 mg, 0.031 mmol), 3-hydroxybenzenesulfonyl fluoride (11 mg, 0.062 mmol) and triphenylphosphine (16 mg, 0.062 mmol) in a vial under $N_2$ was added THF (616 μL,) followed by DIAD (12 μL, 0.062 mmol). The solution was stirred at 45° C. for 1 h. The mixture was cooled to rt and purified by preparative C18 HPLC (Gilson, 0-95% $CH_3CN/H_2O$ with 0.1% TFA). The desired fractions were combined and neutralized with $NaHCO_3$(Sat.). The aqueous layer was extracted with DCM. The combined DCM extract was dried over $Na_2SO_4$ and concentrated to give the desired product (20 mg, 0.025 mmol, 80% yield) as an off-white solid. LCMS (MM-ES+APCI, Pos): m/z 807.3 (100%), 809.3 (50%) (M+H, M+3).

Step F. 3-(((3R,5S)-5-(((4-((1R,5S)-3,8-diazabicyclo[3.2.1]octan-3-yl)-7-(8-chloronaphthalen-1-yl)-8-fluoro-pyrido[4,3-d]pyrimidin-2-yl)oxy)methyl)-1-methylpyrrolidin-3-yl)oxy)benzenesulfonyl fluoride tris(2,2,2-trifluoroacetate). To a solution of tert-butyl (1R,5S)-3-(7-(8-chloronaphthalen-1-yl)-8-fluoro-2-(((2S,4R)-4-(3-(fluorosulfonyl)phenoxy)-1-methylpyrrolidin-2-yl)methoxy)pyrido[4,3-d]pyrimidin-4-yl)-3,8-diazabicyclo[3.2.1]octane-8-carboxylate (20 mg, 0.025 mmol) in DCM (1.0 mL) at rt was added TFA (0.5 mL). The solution was stirred at rt for 1 h and concentrated to dryness. The residue was purified by preparative C18 HPLC (Gilson, 0-95% $CH_3CN/H_2O$ with 0.1% TFA). The desired fractions were combined and concentrated to give the title compound (22 mg, 0.021 mmol, 85% yield) as a white solid. LCMS (MM-ES+APCI, Pos): m/z 707.2 (100%), 709.2 (50%) (M+H, M+3).

Example 209

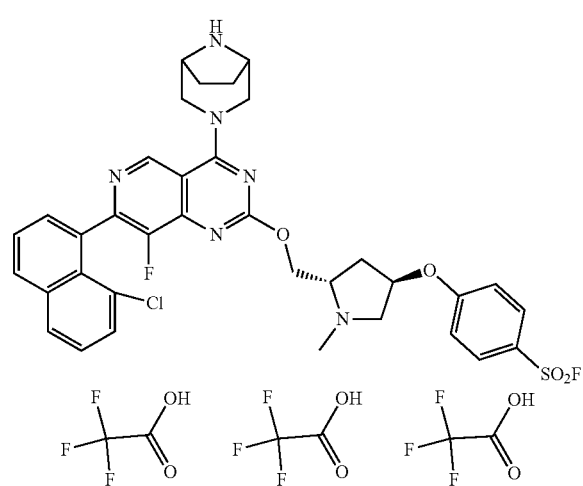

4-(((3R,5S)-5-(((4-((1R,5S)-3,8-diazabicyclo[3.2.1]octan-3-yl)-7-(8-chloronaphthalen-1-yl)-8-fluoro-pyrido[4,3-d]pyrimidin-2-yl)oxy)methyl)-1-methylpyrrolidin-3-yl)oxy)benzenesulfonyl fluoride tris (2,2,2-trifluoroacetate)

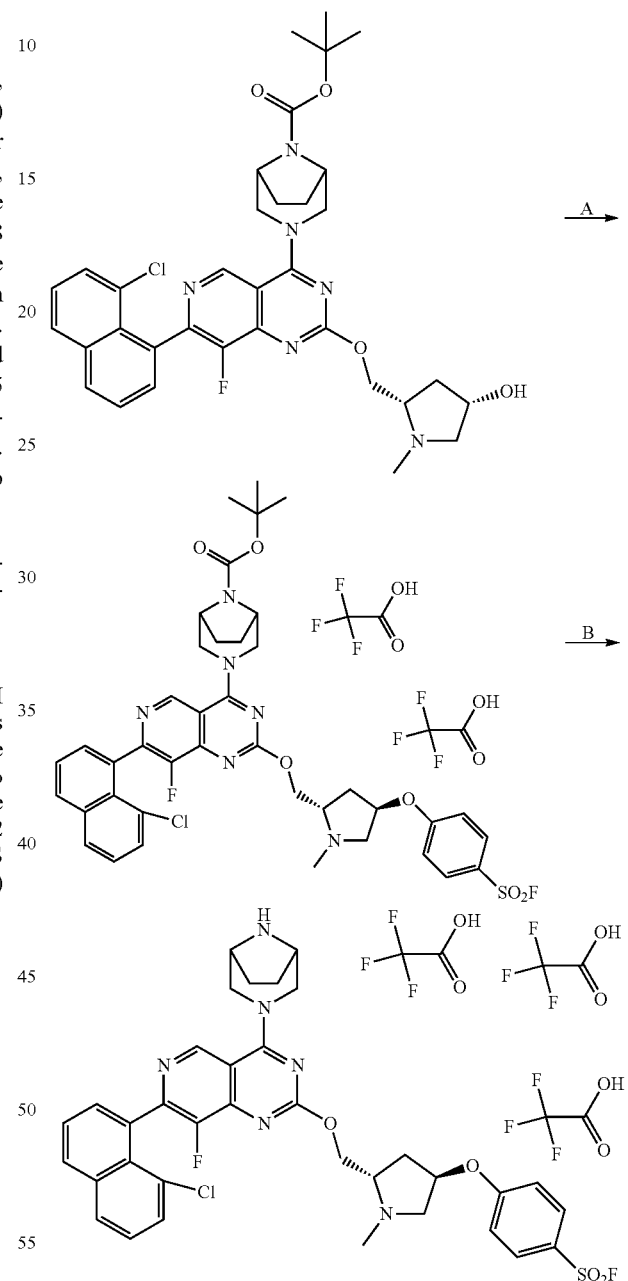

Step A. tert-butyl (1R,5S)-3-(7-(8-chloronaphthalen-1-yl)-8-fluoro-2-(((2S,4R)-4-(4-(fluorosulfonyl)phenoxy)-1-methylpyrrolidin-2-yl)methoxy)pyrido[4,3-d]pyrimidin-4-yl)-3,8-diazabicyclo[3.2.1]octane-8-carboxylate bis(2,2,2-trifluoroacetate). To a mixture of tert-butyl (1R,5S)-3-(7-(8-chloronaphthalen-1-yl)-8-fluoro-2-(((2S,4S)-4-hydroxy-1-methylpyrrolidin-2-yl)methoxy)pyrido[4,3-d]pyrimidin-4-yl)-3,8-diazabicyclo[3.2.1]octane-8-carboxylate (15 mg, 0.023 mmol), 4-hydroxybenzenesulfonyl fluoride (8.1 mg, 0.046 mmol) and triphenylphosphine (12 mg, 0.046 mmol) in a vial under N₂ was added THF (0.46 mL) followed by DIAD (9.0 µL, 0.046 mmol). The solution was stirred at rt for 15 h and was purified by preparative C18 HPLC (Gilson, 0-95% CH₃CN/H₂O with 0.1% TFA). The desired fractions were combined and lyophilized to give the desired product (9 mg, 0.0087 mmol, 38% yield) as an off-white solid. LCMS (MM-ES+APCI, Pos): m/z 807.3 (100%), 809.3 (50%) (M+H, M+3).

Step B. 4-(((3R,5S)-5-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)-1-methylpyrrolidin-3-yl)oxy)benzenesulfonyl fluoride tris(2,2,2-trifluoroacetate). To a solution of tert-butyl (1R,5S)-3-(7-(8-chloronaphthalen-1-yl)-8-fluoro-2-(((2S,4R)-4-(4-(fluorosulfonyl)phenoxy)-1-methylpyrrolidin-2-yl)methoxy)pyrido[4,3-d]pyrimidin-4-yl)-3,8-diazabicyclo[3.2.1]octane-8-carboxylate bis(2,2,2-trifluoroacetate) (9 mg, 0.009 mmol) in DCM (1.0 mL) at rt was added TFA (0.5 mL). The solution was stirred at rt for 1 h. The solution was concentrated to dryness to give the title compound (9 mg, 0.009 mmol, 99% yield) as a white solid. LCMS (MM-ES+APCI, Pos): m/z 707.2 (100%), 709.2 (50%) (M+H, M+3).

Example 210

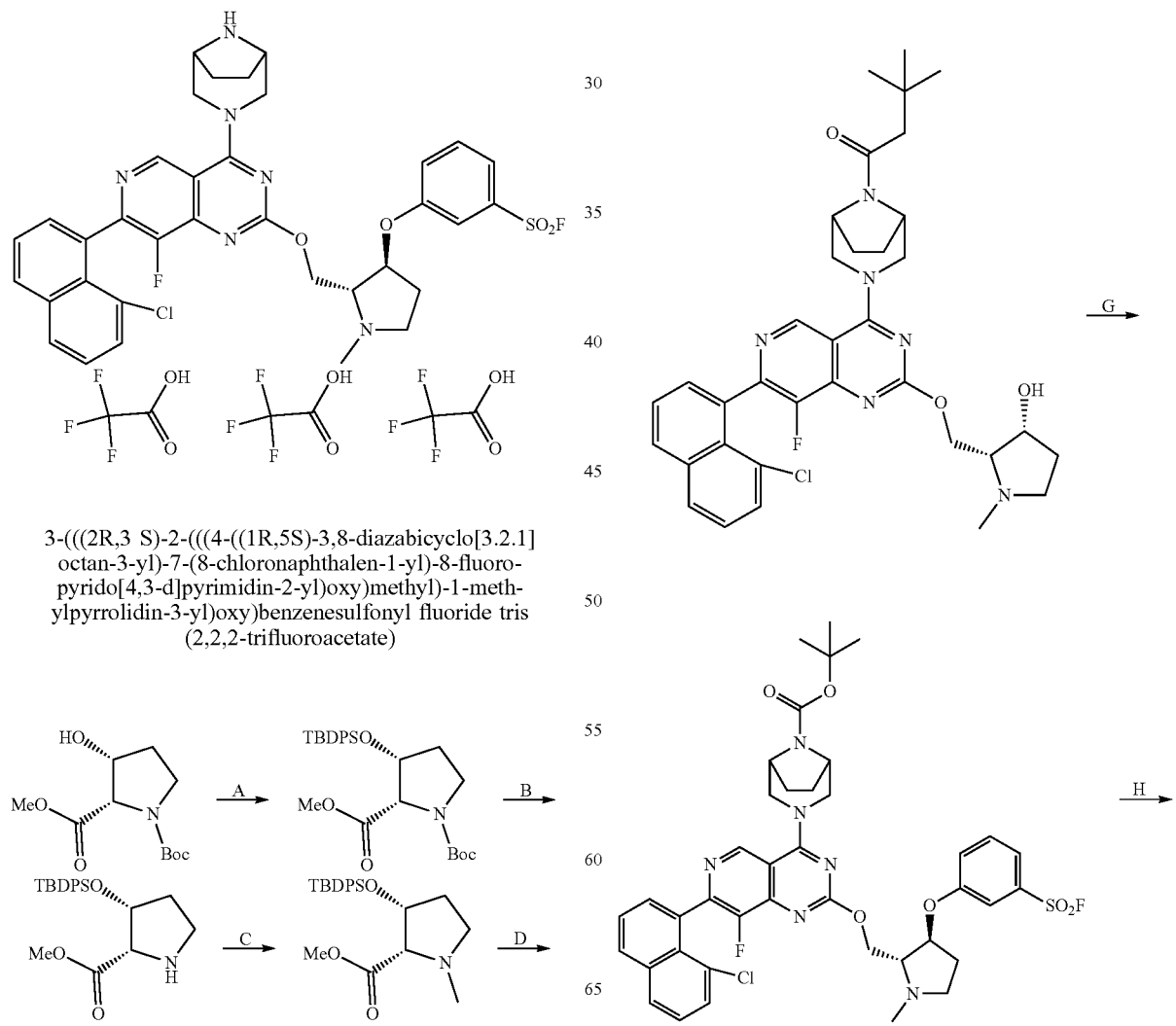

3-(((2R,3S)-2-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)-1-methylpyrrolidin-3-yl)oxy)benzenesulfonyl fluoride tris(2,2,2-trifluoroacetate)

-continued

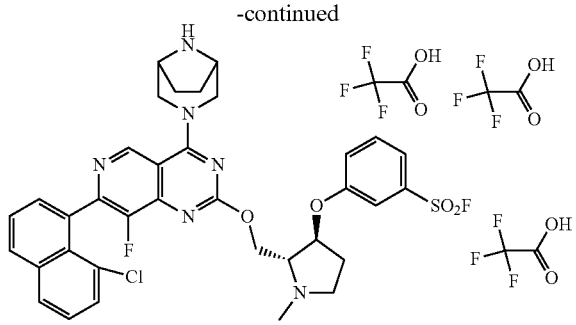

Step A. 1-(tert-butyl) 2-methyl (2S,3R)-3-((tert-butyldiphenylsilyl)oxy)pyrrolidine-1,2-dicarboxylate. To a solution of 1-(tert-butyl) 2-methyl (2S,3R)-3-hydroxypyrrolidine-1,2-dicarboxylate (222 mg, 0.91 mmol), imidazole (185 mg, 2.72 mmol) in DMF (4.5 mL) was added tert-butylchlorodiphenylsilane (0.47 mL, 1.81 mmol). The mixture was stirred at rt for 22 h. Additional tert-butylchlorodiphenylsilane (1 eq) was added. The mixture was heated at 50° C. for 3 h and then cooled to rt. The reaction was diluted with EtOAc/hexanes (1:1, 50 mL) and washed with water (50 mL×2). The organic solution was dried over $Na_2SO_4$, concentrated and purified by flash chromatography eluting with 0-20% EtOAc/hexanes to give the desired product (385 mg, 0.80 mmol, 88% yield) as a colorless gel. LCMS (MM-ES+APCI, Pos): m/z 384.3 (M+H-Boc).

Step B. methyl (2S,3R)-3-((tert-butyldiphenylsilyl)oxy)pyrrolidine-2-carboxylate. To a solution of 1-(tert-butyl) 2-methyl (2S,3R)-3-((tert-butyldiphenylsilyl)oxy)pyrrolidine-1,2-dicarboxylate (350 mg, 0.72 mmol) in DCM (3.6 mL) was added TFA (0.9 mL). The solution was stirred at rt for 0.5 h and basified to pH 9 with $NaHCO_3$ (sat.). The mixture was extracted with DCM. The DCM extract was dried over $Na_2SO_4$ and concentrated to give the crude desired product (280 mg, 0.72 mmol, 100%) as a colorless oil. LCMS (MM-ES+APCI, Pos): m/z 384.2 (M+H).

Step C. methyl (2S,3R)-3-((tert-butyldiphenylsilyl)oxy)-1-methylpyrrolidine-2-carboxylate. To a solution of methyl (2S,3R)-3-((tert-butyldiphenylsilyl)oxy)pyrrolidine-2-carboxylate (276 mg, 0.72 mmol) in MeOH (3.6 mL) were added paraformaldehyde (0.27 mL, 37%, 3.60 mmol) and acetic acid (41 µL, 0.72 mmol) followed by $NaBH_3CN$ (181 mg, 2.88 mmol). The mixture was stirred at rt for 1 h and was then quenched with $NaHCO_3$. The mixture was extracted with MTBE. The organics were dried over $Na_2SO_4$ and concentrated to give the crude desired product (290 mg, 0.73 mmol, 101%) as a pale yellow oil. LCMS (MM-ES+APCI, Pos): m/z 398.2 (M+H).

Step D. ((2R,3R)-3-((tert-butyldiphenylsilyl)oxy)-1-methylpyrrolidin-2-yl)methanol. A mixture of methyl (2S,3R)-3-((tert-butyldiphenylsilyl)oxy)-1-methylpyrrolidine-2-carboxylate (129 mg, 0.32 mmol), potassium borohydride (105 mg, 1.95 mmol), zinc chloride (133 mg, 0.97 mmol) and dioxane (6.5 mL) was heated at 100° C. for 2 h. The mixture was cooled to rt and the slurry was filtered. The filter cake was further washed with EtOAc. The filtrate was treated with HCl (1 M, 5 mL) and then the mixture was basified with $NaHCO_3$ (sat.). The organics were separated. The organic layer was dried over $Na_2SO_4$ and concentrated to dryness. The residue was purified by preparative C18 HPLC (Gilson, 0-95% $CH_3CN/H_2O$ with 0.1% TFA). The desired fractions were combined and neutralized with $NaHCO_3$(Sat.). The aqueous layer extracted with DCM. The organics were dried over $Na_2SO_4$ and concentrated to give the desired product (65 mg, 0.18 mmol, 54% yield) as a white solid. LCMS (MM-ES+APCI, Pos): m/z 370.3 (M+H).

Step E. tert-butyl (1R,5S)-3-(2-(((2R,3R)-3-((tert-butyldiphenylsilyl)oxy)-1-methylpyrrolidin-2-yl)methoxy)-7-(8-chloronaphthalen-1-yl)-8-fluoropyrido[4,3-d]pyrimidin-4-yl)-3,8-diazabicyclo[3.2.1]octane-8-carboxylate. To a solution of tert-butyl (1R,5S)-3-(2-chloro-7-(8-chloronaphthalen-1-yl)-8-fluoropyrido[4,3-d]pyrimidin-4-yl)-3,8-diazabicyclo[3.2.1]octane-8-carboxylate (117 mg, 0.21 mmol) and ((2R,3R)-3-((tert-butyldiphenylsilyl)oxy)-1-methylpyrrolidin-2-yl)methanol (65 mg, 0.18 mmol) in THF (1.8 mL) at −10° C. was added NaH (16 mg, 60%, 0.40 mmol). The mixture was warmed to rt and stirred at rt for 18 h. The mixture was then quenched with $NH_4Cl$ (sat.) and extracted with EtOAc. The organics were dried over $Na_2SO_4$, concentrated and purified by flash chromatography eluting with 0-10% MeOH/DCM to give the desired product (150 mg, 96%) as a yellow solid. LCMS (MM-ES+APCI, Pos): m/z 787.2 (100%), 789.2 (50%) (M+H-Boc, M+3-Boc).

Step F. tert-butyl (1R,5S)-3-(7-(8-chloronaphthalen-1-yl)-8-fluoro-2-(((2R,3R)-3-hydroxy-1-methylpyrrolidin-2-yl)methoxy)pyrido[4,3-d]pyrimidin-4-yl)-3,8-diazabicyclo[3.2.1]octane-8-carboxylate. To a solution of tert-butyl (1R,5S)-3-(2-(((2R,3R)-3-((tert-butyldiphenylsilyl)oxy)-1-methylpyrrolidin-2-yl)methoxy)-7-(8-chloronaphthalen-1-yl)-8-fluoropyrido[4,3-d]pyrimidin-4-yl)-3,8-diazabicyclo[3.2.1]octane-8-carboxylate (145 mg, 0.16 mmol) in THF (0.80 mL) was added TBAF (0.82 mL, 1.0 M, 0.82 mmol). The solution was stirred at rt for 16 h. The mixture was quenched with water and extracted with EtOAc. The organics were washed with brine and concentrated to dryness. The residue was purified by flash chromatography eluting with 0-10% MeOH/DCM to give the desired product (56 mg, 0.086 mmol, 53% yield) as a white solid. LCMS (MM-ES+APCI, Pos): m/z 649.3 (100%), 651.3 (50%) (M+H, M+3).

Step G. tert-butyl (1R,5S)-3-(7-(8-chloronaphthalen-1-yl)-8-fluoro-2-(((2R,3S)-3-(3-(fluorosulfonyl)phenoxy)-1-methylpyrrolidin-2-yl)methoxy)pyrido[4,3-d]pyrimidin-4-yl)-3,8-diazabicyclo[3.2.1]octane-8-carboxylate. To a mixture of tert-butyl (1R,5S)-3-(7-(8-chloronaphthalen-1-yl)-8-fluoro-2-(((2R,3R)-3-hydroxy-1-methylpyrrolidin-2-yl)methoxy)pyrido[4,3-d]pyrimidin-4-yl)-3,8-diazabicyclo[3.2.1]octane-8-carboxylate (20 mg, 0.031 mmol), 3-hydroxybenzenesulfonyl fluoride (11 mg, 0.062 mmol) and triphenylphosphine (16 mg, 0.062 mmol) in a vial under $N_2$ was added THF (0.6 mL) followed by DIAD (12 µL, 0.062 mmol). The solution was stirred at 45° C. for 1 h. The mixture was cooled to rt and purified by preparative C18 HPLC (Gilson, 0-95% $CH_3CN/H_2O$ with 0.1% TFA). The desired fractions were combined and neutralized with $NaHCO_3$ (sat.). The aqueous layer was extracted with EtOAc. The organics were dried over $Na_2SO_4$ and concentrated to give the desired product (11 mg, 0.014 mmol, 44% yield) as an off-white solid. LCMS (MM-ES+APCI, Pos): m/z 807.3 (100%), 809.3 (50%) (M+H, M+3).

Step H. 3-(((2R,3S)-2-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)-1-methylpyrrolidin-3-yl)oxy)benzenesulfonyl fluoride tris(2,2,2-trifluoroacetate). To a solution of tert-butyl (1R,5S)-3-(7-(8-chloronaphthalen-1-yl)-8-fluoro-2-(((2R,3S)-3-(3-(fluorosulfonyl)phenoxy)-1-methylpyrrolidin-2-yl)methoxy)pyrido[4,3-d]pyrimidin-4-yl)-3,8-diazabicyclo[3.2.1]octane-8-carboxylate (11 mg, 0.014 mmol) in DCM (1.0 mL) at rt was added TFA (0.5 mL). The solution was stirred at rt for 1 h and concentrated to dryness. The residue was purified by preparative C18 HPLC (Gilson, 0-95% CH₃CN/H₂O with 0.1% TFA). The desired fractions were combined and lyophilized to give the title compound (11 mg, 0.011 mmol, 77% yield) as a white solid. LCMS (MM-ES+APCI, Pos): m/z 707.2 (100%), 709.2 (50%) (M+H, M+3).

Example 211

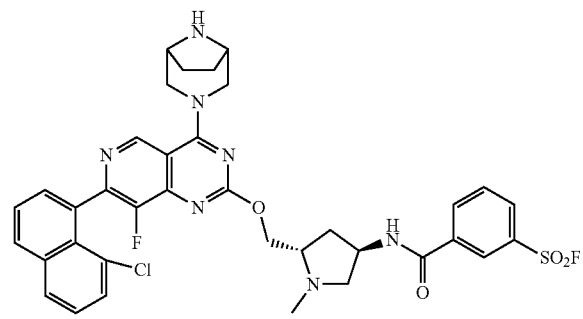

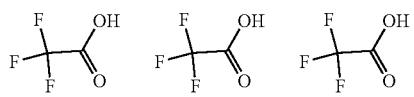

3-(((3R,5S)-5-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)-1-methylpyrrolidin-3-yl)carbamoyl)benzenesulfonyl fluoride tris(2,2,2-trifluoroacetate)

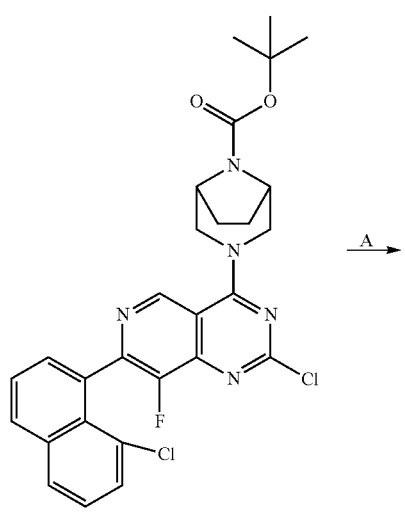

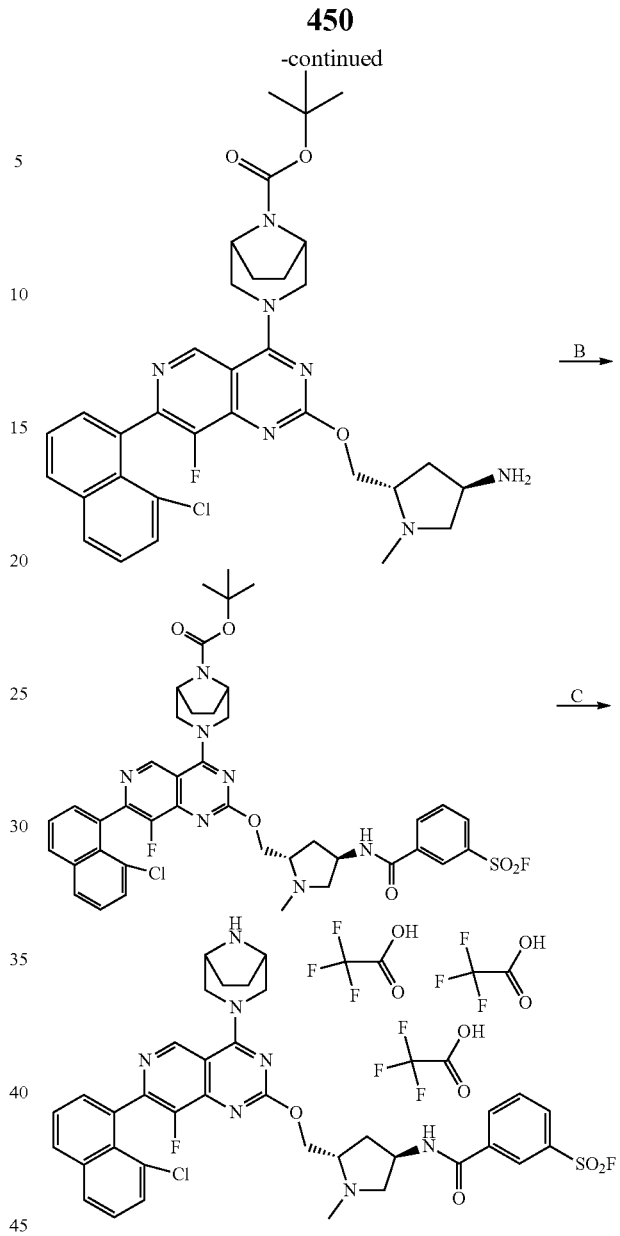

Step A. tert-butyl (1R,5S)-3-(2-(((2S,4R)-4-amino-1-methylpyrrolidin-2-yl)methoxy)-7-(8-chloronaphthalen-1-yl)-8-fluoropyrido[4,3-d]pyrimidin-4-yl)-3,8-diazabicyclo[3.2.1]octane-8-carboxylate. To a solution of ((2S,4R)-4-amino-1-methylpyrrolidin-2-yl)methanol (64.1 mg, 0.49 mmol) in DMF (4.5 mL) at −10° C. was added NaH (47.3 mg, 60%, 1.18 mmol). The mixture was stirred at −10° C. for 5 min. followed by addition of tert-butyl (1R,5S)-3-(2-chloro-7-(8-chloronaphthalen-1-yl)-8-fluoropyrido[4,3-d]pyrimidin-4-yl)-3,8-diazabicyclo[3.2.1]octane-8-carboxylate (248 mg, 0.45 mmol). The mixture was warmed to 0° C. and stirred at 0° C. for 15 h. The mixture was purified by preparative C18 HPLC (Gilson, 0-95% CH₃CN/H₂O with 0.1% TFA). The desired fractions were combined and basified with NaHCO₃ (sat.) and the aqueous layer was extracted with DCM/IPA (10:1). The organics were dried over Na₂SO₄ and concentrated to give the desired product (72 mg, 0.11 mmol, 25% yield) as an off-white solid. LCMS (MM-ES+APCI, Pos): m/z 648.3 (100%), 650.3 (50%) (M+H, M+3).

Step B. tert-butyl (1R,5S)-3-(7-(8-chloronaphthalen-1-yl)-8-fluoro-2-(((2S,4R)-4-(3-(fluorosulfonyl)benzamido)-1-methylpyrrolidin-2-yl)methoxy)pyrido[4,3-d]pyrimidin-4-yl)-3,8-diazabicyclo[3.2.1]octane-8-carboxylate bis(2,2,2-trifluoroacetate). A mixture of tert-butyl (1R,5S)-3-(2-(((2S,4R)-4-amino-1-methylpyrrolidin-2-yl)methoxy)-7-(8-chloronaphthalen-1-yl)-8-fluoropyrido[4,3-d]pyrimidin-4-yl)-3,8-diazabicyclo[3.2.1]octane-8-carboxylate (22 mg, 0.034 mmol), 3-(fluorosulfonyl)benzoic acid (20.8 mg, 0.10 mmol), 3-(((ethylimino)methylene)amino)-N,N-dimethylpropan-1-amine hydrochloride (19.5 mg, 0.10 mmol) and triethylamine (24 µL, 0.17 mmol) in DCM (1.1 mL) was stirred at rt for 2 h and was quenched with water (2 drops) and $CH_3CN$. The mixture was concentrated to dryness and the residue was purified by preparative C18 HPLC (Gilson, 0-95% $CH_3CN/H_2O$ with 0.1% TFA). The desired fractions were combined and lyophilized to give the desired product (26 mg, 0.025 mmol, 72% yield) as a white solid. LCMS (MM-ES+APCI, Pos): m/z 834.3 (100%), 836.3 (50%) (M+H, M+3).

Step C. 3-(((3R,5S)-5-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)-1-methylpyrrolidin-3-yl)carbamoyl)benzenesulfonyl fluoride tris(2,2,2-trifluoroacetate). To a solution of tert-butyl (1R,5S)-3-(7-(8-chloronaphthalen-1-yl)-8-fluoro-2-(((2S,4R)-4-(3-(fluorosulfonyl)benzamido)-1-methylpyrrolidin-2-yl)methoxy)pyrido[4,3-d]pyrimidin-4-yl)-3,8-diazabicyclo[3.2.1]octane-8-carboxylate bis(2,2,2-trifluoroacetate) (20 mg, 0.019 mmol) in DCM (1.0 mL) was added 2,2,2-trifluoroacetic acid (0.50 mL). The solution was stirred at rt for 1 h and concentrated to dryness to give the title compound (21 mg, 0.020 mmol, 104% yield) as an off-white solid. LCMS (MM-ES+APCI, Pos): m/z 734.2 (100%), 736.2 (50%) (M+H, M+3).

Example 212

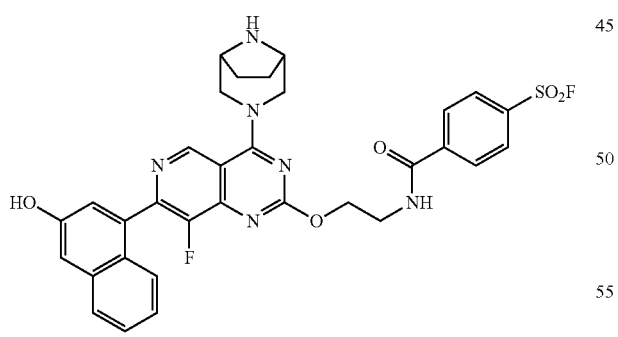

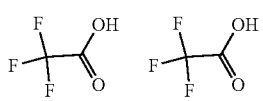

4-((2-((4-((1R,5S)-3,8-diazabicyclo[3.2.1]octan-3-yl)-8-fluoro-7-(3-hydroxynaphthalen-1-yl)pyrido[4,3-d]pyrimidin-2-yl)oxy)ethyl)carbamoyl)benzenesulfonyl fluoride bis(2,2,2-trifluoroacetate)

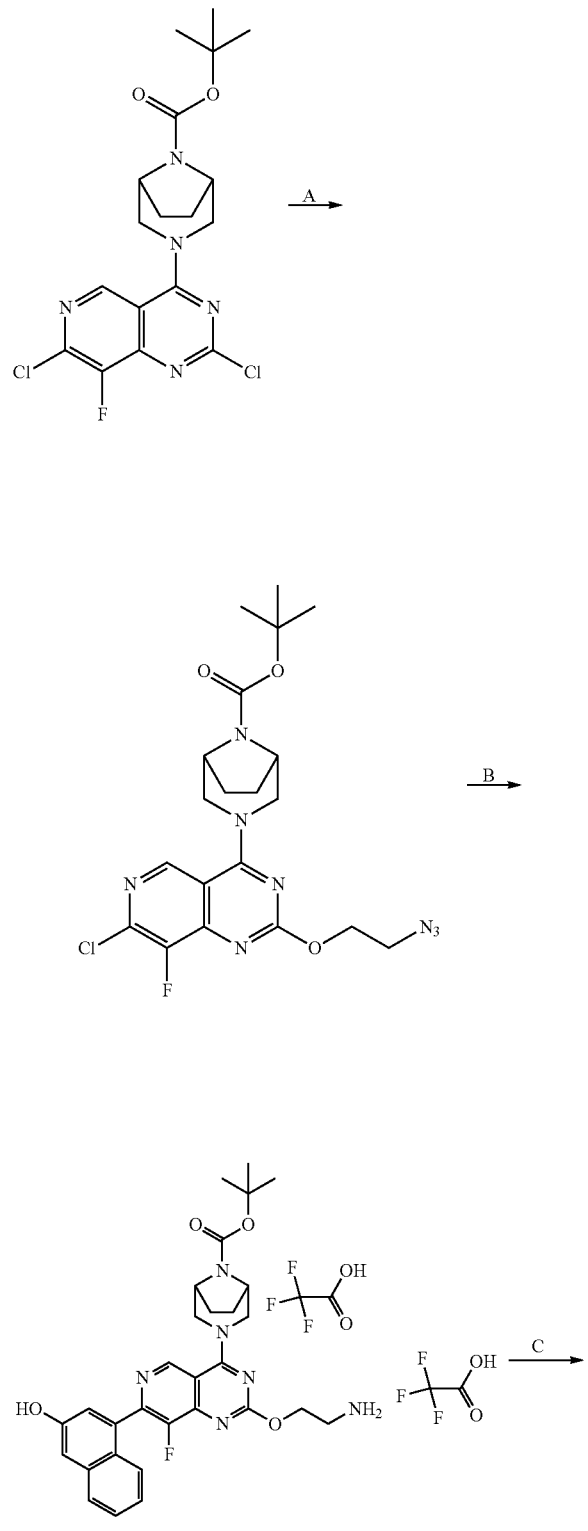

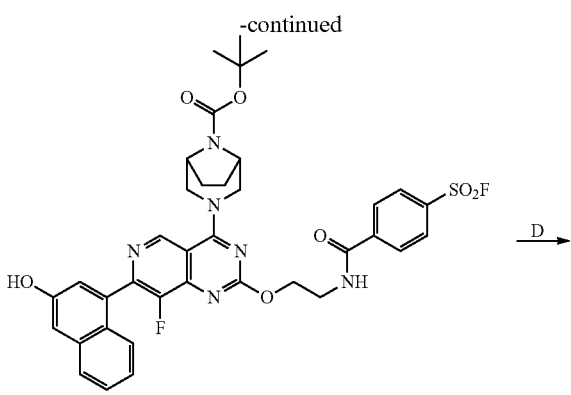

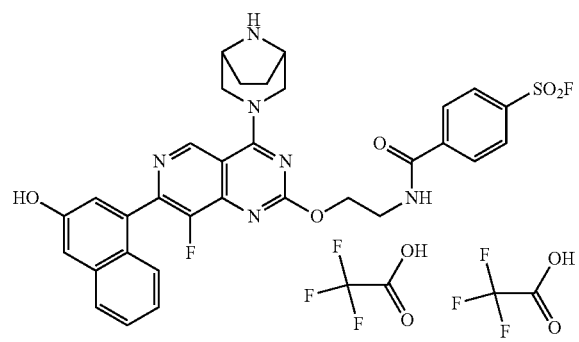

Step A. tert-butyl (1R,5S)-3-(2-(2-azidoethoxy)-7-chloro-8-fluoropyrido[4,3-d]pyrimidin-4-yl)-3,8-diazabicyclo[3.2.1]octane-8-carboxylate. To a solution of 2-azidoethan-1-ol (43.5 mg, 0.50 mmol) in THF (5.0 mL) at 0° C. was added NaH (26.0 mg, 60%, 0.65 mmol). The mixture was stirred at 0° C. for 10 min and tert-butyl (1R,5S)-3-(2,7-dichloro-8-fluoropyrido[4,3-d]pyrimidin-4-yl)-3,8-diazabicyclo[3.2.1]octane-8-carboxylate (214 mg, 0.50 mmol) was added. The mixture was stirred at 0° C. for 1 h. The mixture was quenched with NH₄Cl (sat.) and extracted with EtOAc. The organics were dried over Na₂SO₄, concentrated and purified by flash chromatography eluting with 0-70% EtOAc/hexanes to give the desired product (207 mg, 0.43 mmol, 87% yield) as a white solid. LCMS (MM-ES+APCI, Pos): m/z 479.2 (100%), 481.2 (50%) (M+H, M+3).

Step B. tert-butyl (1R,5S)-3-(2-(2-aminoethoxy)-8-fluoro-7-(3-hydroxynaphthalen-1-yl)pyrido[4,3-d]pyrimidin-4-yl)-3,8-diazabicyclo[3.2.1]octane-8-carboxylate bis (2,2,2-trifluoroacetate). To a vial containing a mixture of 4-(4,4,5,5-tetramethyl-1,3,2-dioxaborolan-2-yl)naphthalen-2-ol (135 mg, 0.50 mmol), tert-butyl (1R,5S)-3-(2-(2-azidoethoxy)-7-chloro-8-fluoropyrido[4,3-d]pyrimidin-4-yl)-3,8-diazabicyclo[3.2.1]octane-8-carboxylate (200 mg, 0.42 mmol) and Pd(PPh₃)₄ (48.3 mg, 0.042 mmol) under Ar were added K₂CO₃ (0.63 mL, 2.0 M, 1.26 mmol) and dioxane. The vial was closed and heated at 80° C. for 18 h. The mixture was cooled, concentrated and purified by preparative C18 HPLC (Gilson, 0-95% CH₃CN/H₂O with 0.1% TFA). The fractions containing product were combined and lyophilized to give the desired product (37 mg, 0.047 mmol, 11% yield) as a yellow solid. LCMS (MM-ES+APCI, Pos): m/z 561.3 (M+H)

Step C. tert-butyl (1R,5S)-3-(8-fluoro-2-(2-(4-(fluorosulfonyl)benzamido)ethoxy)-7-(3-hydroxynaphthalen-1-yl)pyrido[4,3-d]pyrimidin-4-yl)-3,8-diazabicyclo[3.2.1]octane-8-carboxylate 2,2,2-trifluoroacetate. To a solution of tert-butyl (1R,5S)-3-(2-(2-aminoethoxy)-8-fluoro-7-(3-hydroxynaphthalen-1-yl)pyrido[4,3-d]pyrimidin-4-yl)-3,8-diazabicyclo[3.2.1]octane-8-carboxylate bis(2,2,2-trifluoroacetate) (16 mg, 0.020 mmol) in DCM (0.80 mL) at 0° C. was added Et₃N (9.0 μL, 0.065 mmol) followed by 4-(fluorosulfonyl)benzoyl chloride (7.5 mg, 0.030 mmol). The mixture was stirred at 0° C. for 1 h and quenched with water (2 drops) and CH₃CN. The mixture was concentrated to dryness and the residue purified by preparative C18 HPLC (Gilson, 0-95% CH₃CN/H₂O with 0.1% TFA). The desired fractions were combined and lyophilized to the desired product (11 mg, 0.013 mmol, 63% yield) as a white solid. LCMS (MM-ES+APCI, Pos): m/z 747.1 (M+H).

Step D. 4-((2-((4-((1R,5S)-3,8-diazabicyclo[3.2.1]octan-3-yl)-8-fluoro-7-(3-hydroxynaphthalen-1-yl)pyrido[4,3-d]pyrimidin-2-yl)oxy)ethyl)carbamoyl)benzenesulfonyl fluoride bis(2,2,2-trifluoroacetate). To a solution of tert-butyl (1R,5S)-3-(8-fluoro-2-(2-(4-(fluorosulfonyl)benzamido)ethoxy)-7-(3-hydroxynaphthalen-1-yl)pyrido[4,3-d]pyrimidin-4-yl)-3,8-diazabicyclo[3.2.1]octane-8-carboxylate 2,2,2-trifluoroacetate (11 mg, 0.013 mmol) in DCM (1.0 mL) was added 2,2,2-trifluoroacetic acid (0.50 mL). The solution was stirred at rt for 1 h and concentrated to dryness to give the title compound (5 mg, 0.0058 mmol, 45% yield) as an off-white solid. LCMS (MM-ES+APCI, Pos): m/z 647.1 (M+H).

Example 213

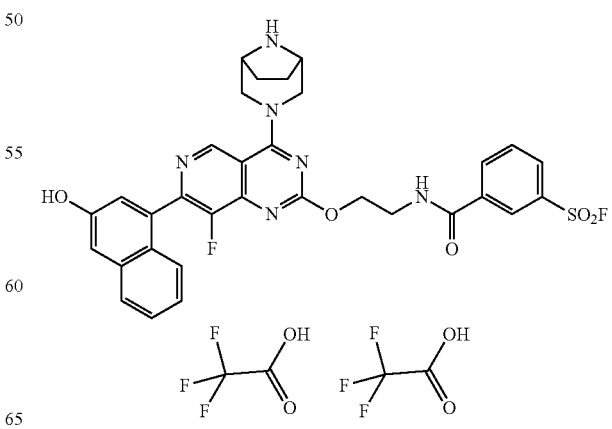

3-((2-((4-((1R,5S)-3,8-diazabicyclo[3.2.1]octan-3-yl)-8-fluoro-7-(3-hydroxynaphthalen-1-yl)pyrido[4,3-d]pyrimidin-2-yl)oxy)ethyl)carbamoyl)benzene-sulfonyl fluoride bis(2,2,2-trifluoroacetate)
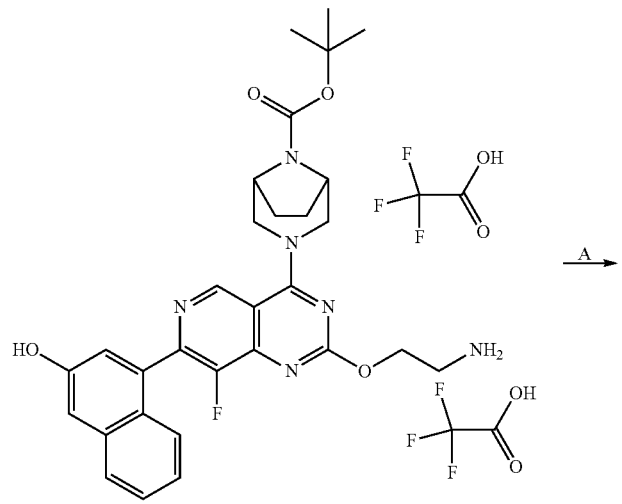
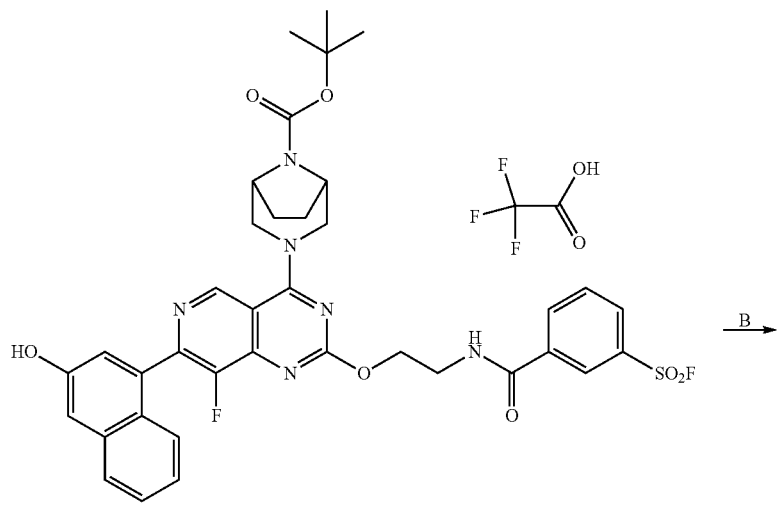
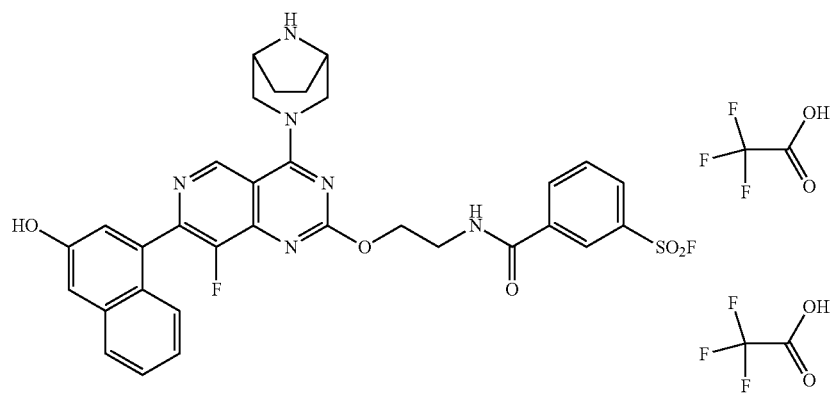

Step A. tert-butyl (1R,5S)-3-(8-fluoro-2-(2-(3-(fluorosulfonyl)benzamido)ethoxy)-7-(3-hydroxynaphthalen-1-yl)pyrido[4,3-d]pyrimidin-4-yl)-3,8-diazabicyclo[3.2.1]octane-8-carboxylate 2,2,2-trifluoroacetate. To a stirred solution of tert-butyl (1R,5S)-3-(2-(2-aminoethoxy)-8-fluoro-7-(3-hydroxynaphthalen-1-yl)pyrido[4,3-d]pyrimidin-4-yl)-3,8-diazabicyclo[3.2.1]octane-8-carboxylate bis(2,2,2-trifluoroacetate (15 mg, 0.019 mmol) in DCM (1.0 mL) was added HCl (4.0 M in dioxane) (19 µL, 0.076 mmol) dropwise to give a yellow suspension. The suspension was concentrated to dryness. The residue was suspended in DCM (0.76 mL) followed by addition of 3-(fluorosulfonyl)benzoic acid (7.8 mg, 0.038 mmol), 3-(((ethylimino)methylene)amino)-N,N-dimethylpropan-1-amine hydrochloride (7.3 mg, 0.038 mmol) and triethylamine (19 µL, 0.13 mmol). The mixture was stirred at rt for 2 h. Additional 3-(fluorosulfonyl)benzoic acid (7.8 mg, 0.038 mmol), 3-(((ethylimino)methylene)amino)-N,N-dimethylpropan-1-amine hydrochloride (7.3 mg, 0.038 mmol) and Et₃N (8 µL, 0.057 mmol) were added and the reaction stirred at rt for 1 h. The reaction was quenched with water (2 drops) and CH₃CN. The mixture was concentrated to dryness and the residue purified by preparative C18 HPLC (Gilson, 0-95% CH₃CN/H₂O with 0.1% TFA). The desired fractions were combined and lyophilized to give the desired product (11 mg, 0.013 mmol, 67% yield) as a white solid. LCMS (MM-ES+APCI, Pos): m/z 747.1 (M+H).

Step B. 3-((2-((4-((1R,5S)-3,8-diazabicyclo[3.2.1]octan-3-yl)-8-fluoro-7-(3-hydroxynaphthalen-1-yl)pyrido[4,3-d]pyrimidin-2-yl)oxy)ethyl)carbamoyl)benzenesulfonyl fluoride bis(2,2,2-trifluoroacetate). To a solution of tert-butyl (1R,5S)-3-(8-fluoro-2-(2-(3-(fluorosulfonyl)benzamido)ethoxy)-7-(3-hydroxynaphthalen-1-yl)pyrido[4,3-d]pyrimidin-4-yl)-3,8-diazabicyclo[3.2.1]octane-8-carboxylate 2,2,2-trifluoroacetate (11 mg, 0.013 mmol) in DCM (1.0 mL, 0.013 mmol) was added 2,2,2-trifluoroacetic acid (0.50 mL). The solution was stirred at rt for 1 h and concentrated to dryness to give the title compound (12 mg, 0.014 mmol, 107% yield) as an off-white solid. LCMS (MM-ES+APCI, Pos): m/z 647.1 (M+H).

Example 214

3-(8-fluoro-7-(3-hydroxynaphthalen-1-yl)-2-(((S)-1-methylpyrrolidin-2-yl)methoxy)pyrido[4,3-d]pyrimidin-4-yl)-3,8-diazabicyclo[3.2.1]octane-1-carbaldehyde

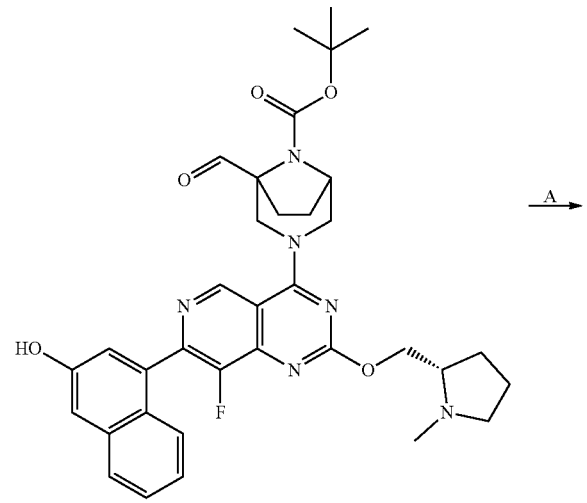

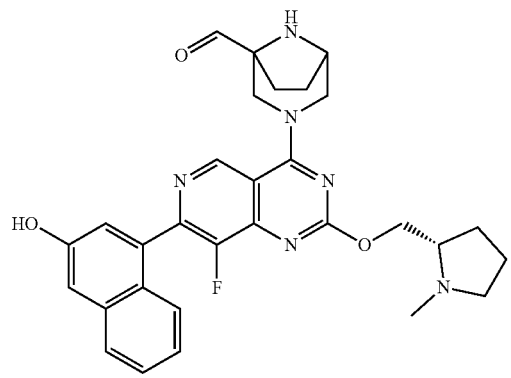

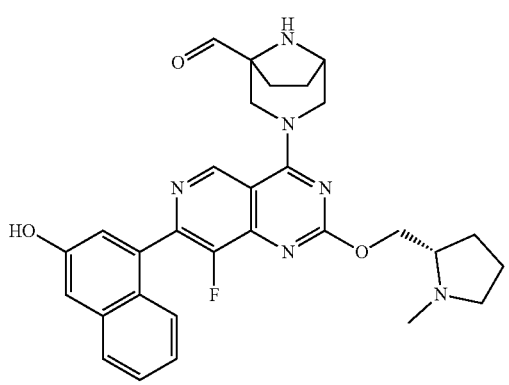 [SMILES: CN1CCC[C@H]1COc1nc(N2CC3CCC(C=O)(C2)N3)c2cnc(-c3cc(O)cc4ccccc34)c(F)c2n1]

Step A. 3-(8-fluoro-7-(3-hydroxynaphthalen-1-yl)-2-(((S)-1-methylpyrrolidin-2-yl)methoxy)pyrido[4,3-d]pyrimidin-4-yl)-3,8-diazabicyclo[3.2.1]octane-1-carbaldehyde. To a solution of tert-butyl 3-(8-fluoro-7-(3-hydroxynaphthalen-1-yl)-2-(((S)-1-methylpyrrolidin-2-yl)methoxy)pyrido[4,3-d]pyrimidin-4-yl)-1-formyl-3,8-diazabicyclo[3.2.1]octane-8-carboxylate (synthesized in Example 157) (50.0 mg, 0.078 mmol) in DCM (0.78 mL) was added TFA (0.26 mL, 0.078 mmol). The solution was stirred at rt for 0.5 h and concentrated to dryness to give a yellow solid. The solid was partitioned between NaHCO₃ (Sat.) and DCM/IPA (5:1). The two layers were separated, and the organic layer was dried over Na₂SO₄ and concentrated to give the title compound (36 mg, 85%) as a light brown solid. LCMS (MM-ES+APCI, Pos): m/z 543.2 (M+H).

Example 215

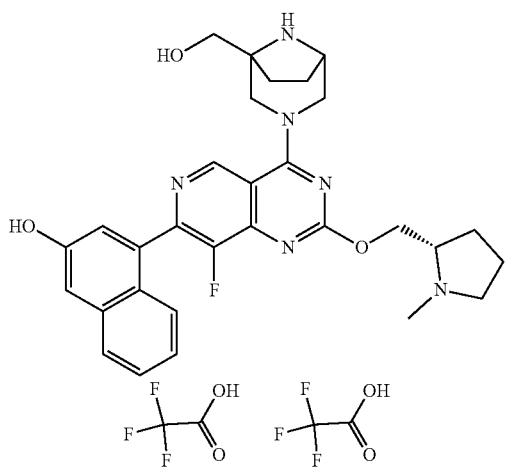

4-(8-fluoro-4-(1-(hydroxymethyl)-3,8-diazabicyclo[3.2.1]octan-3-yl)-2-(((S)-1-methylpyrrolidin-2-yl)methoxy)pyrido[4,3-d]pyrimidin-7-yl)naphthalen-2-ol bis(2,2,2-trifluoroacetate)

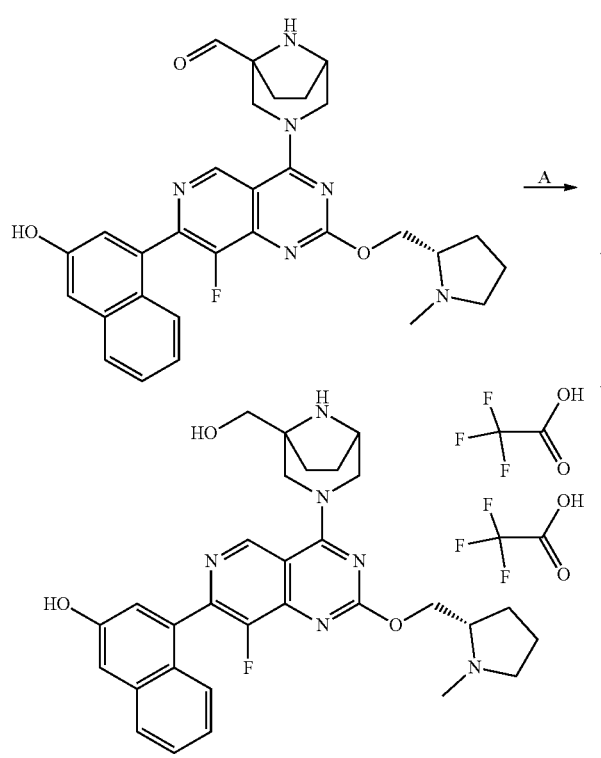

Step A. 4-(8-fluoro-4-(1-(hydroxymethyl)-3,8-diazabicyclo[3.2.1]octan-3-yl)-2-(((S)-1-methylpyrrolidin-2-yl)methoxy)pyrido[4,3-d]pyrimidin-7-yl)naphthalen-2-ol bis (2,2,2-trifluoroacetate). To a solution of 3-(8-fluoro-7-(3-hydroxynaphthalen-1-yl)-2-(((S)-1-methylpyrrolidin-2-yl)methoxy)pyrido[4,3-d]pyrimidin-4-yl)-3,8-diazabicyclo[3.2.1]octane-1-carbaldehyde (Example 158) (18 mg, 0.033 mmol) in methanol (1.0 mL) was added sodium borohydride (2.5 mg, 0.066 mmol). The solution was stirred at rt for 15 min and concentrated to dryness. The residue was purified by preparative C18 HPLC (Gilson, 0-95% CH$_3$CN/H$_2$O with 0.1% TFA). The desired fractions were combined and concentrated to give the title compound (15 mg, 59%) as a yellow solid. LCMS (MM-ES+APCI, Pos): m/z 545.2 (M+H).

Example 216

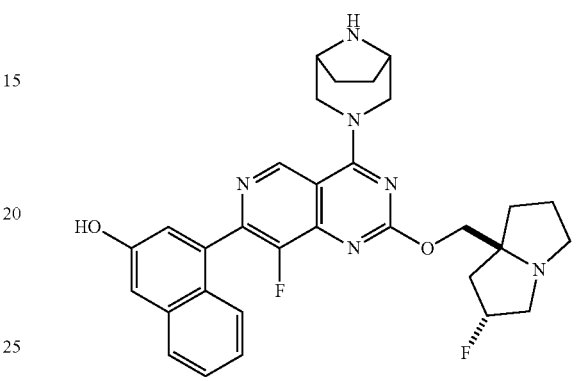

4-(4-((1R,5S)-3,8-diazabicyclo[3.2.1]octan-3-yl)-8-fluoro-2-(((2R)-2-fluorotetrahydro-1H-pyrrolizin-7a(5H)-yl)methoxy)pyrido[4,3-d]pyrimidin-7-yl)naphthalen-2-ol (racemic, trans)

Synthesized according to Example 3, Steps G-I substituting ((2R,7aS)-2-fluorotetrahydro-1H-pyrrolizin-7a(5H)-yl)methanol in place of 2-(1-methyl-1H-imidazol-2-yl)ethan-1-ol in Step G to afford 4-(4-((1R,5S)-3,8-diazabicyclo[3.2.1]octan-3-yl)-8-fluoro-2-(((2R)-2-fluorotetrahydro-1H-pyrrolizin-7a(5H)-yl)methoxy)pyrido[4,3-d]pyrimidin-7-yl)naphthalen-2-ol (1.5 mg, 0.002 mmol, 2%). LCMS (MM-ES+APCI, Pos): m/z 559.2 (M+H).

Example 217

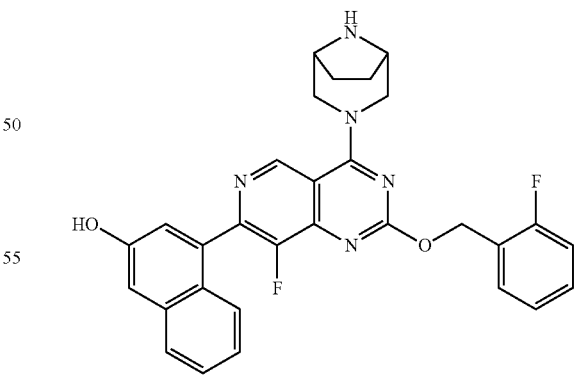

4-(4-((1R,5S)-3,8-diazabicyclo[3.2.1]octan-3-yl)-8-fluoro-2-((2-fluorobenzyl)oxy)pyrido[4,3-d]pyrimidin-7-yl)naphthalen-2-ol Synthesized according to Example 3, Steps G and H substituting 2-fluorobenzyl alcohol in place of 2-(1-methyl- 1H-imidazol-2-yl)ethan-1-ol followed by deprotection according to the method of Example 2, Step I (4.17 mg, 0.00794 mmol, 16%). LCMS (MM-ES+APCI, Pos): m/z 526.2 [M+H].

Example 218

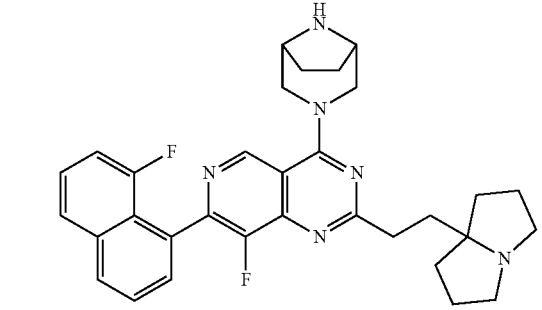

4-((1R,5S)-3,8-diazabicyclo[3.2.1]octan-3-yl)-8-fluoro-7-(8-fluoronaphthalen-1-yl)-2-(2-(tetrahydro-1H-pyrrolizin-7a(5H)-yl)ethyl)pyrido[4,3-d]pyrimidine

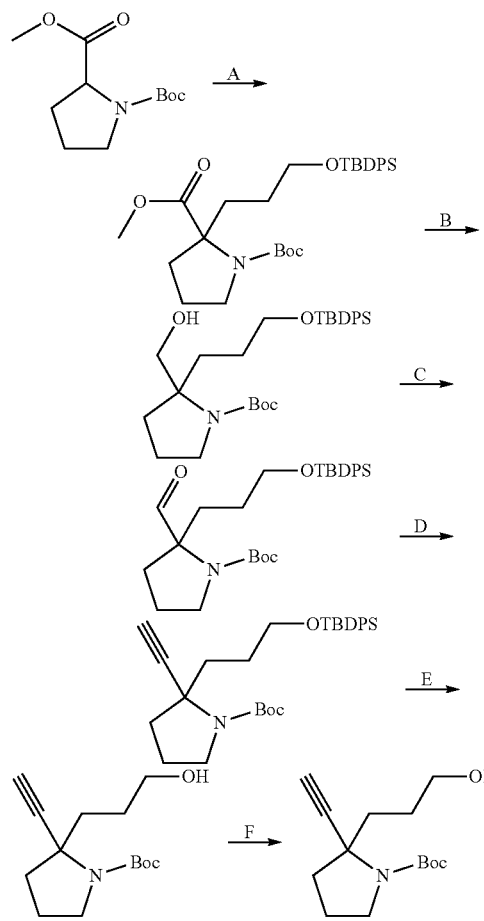

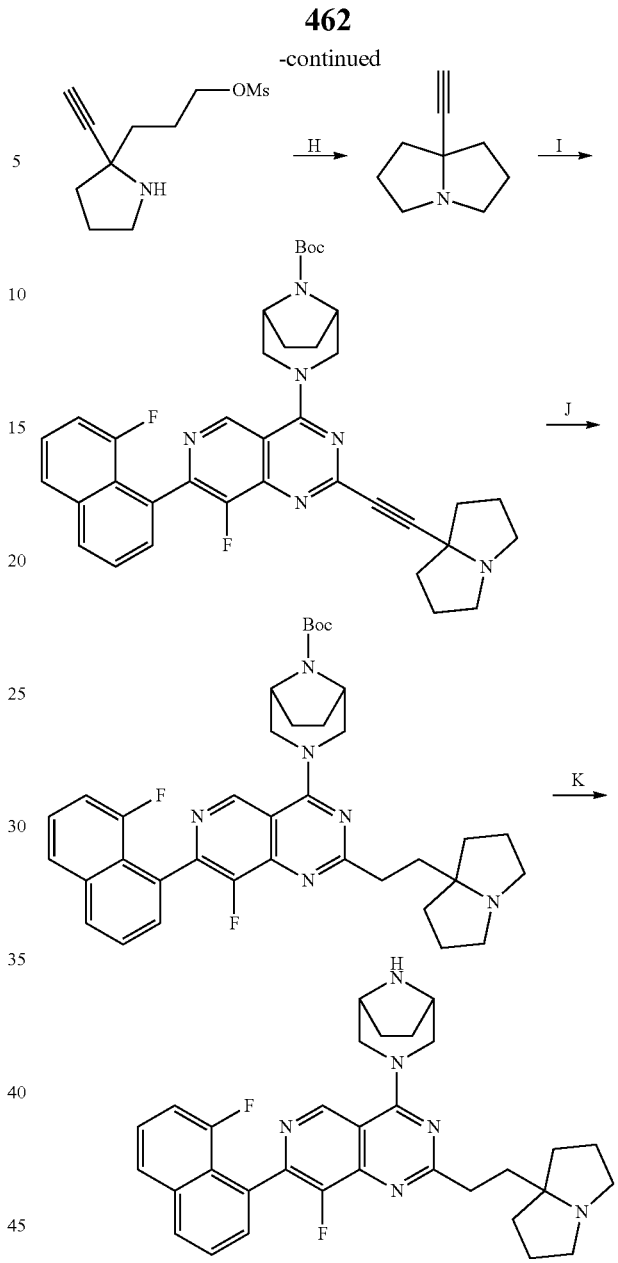

Step A. 1-tert-butyl 2-methyl 2-(3-((tert-butyldiphenylsilyl)oxy)propyl)pyrrolidine-1,2-dicarboxylate. To a solution of 1-(tert-butyl) 2-methyl pyrrolidine-1,2-dicarboxylate (10.0 g, 43.6 mmol, 1.0 eq) in THF (200 mL) was added LDA (2.0 M, 26.2 mL, 1.20 eq). The mixture was stirred at −70° C. for 1 hour. To the reaction mixture was added (3-bromopropoxy)(tert-butyl)diphenylsilane (16.5 g, 43.6 mmol, 1.0 eq) at −70° C. The mixture was stirred at 20° C. for 12 hours. The reaction mixture was diluted with $H_2O$ (200 mL) and extracted with ethyl acetate (3×200 mL). The combined organic layers were dried over $Na_2SO_4$, filtered and concentrated under reduced pressure to give a residue. The residue was purified by column chromatography ($SiO_2$, Petroleum ether/Ethyl acetate 1/0 to 1/1) affording the title compound (9.50 g, 41% yield). Yellow oil; $^1H$ NMR (400 MHz, chloroform-d) δ 7.71-7.62 (m, 4H), 7.48-7.33 (m, 6H), 3.78-3.57 (m, 6H), 3.44-3.31 (m, 1H), 2.34-2.05 (m, 2H), 2.03-1.69 (m, 4H), 1.64-1.48 (m, 2H), 1.47-1.33 (m, 9H), 1.11-1.02 (m, 9H). LCMS [ESI, M−99]: 426.1.

Step B. tert-butyl 2-(3-((tert-butyldiphenylsilyl)oxy)propyl)-2-(hydroxymethyl)pyrrolidine-1-carboxylate. To a solution of 1-tert-butyl 2-methyl 2-(3-((tert-butyldiphenylsilyl)oxy)propyl)pyrrolidine-1,2-dicarboxylate (5.0 g, 9.51 mmol, 1.0 eq) in THF (100 mL) was added LiAlH$_4$ (1.08 g, 28.5 mmol, 3.0 eq) in portions during a period of 30 minutes at −40° C. under N$_2$ atmosphere and the mixture was stirred at −40° C. for 1 hour. After completion, the reaction mixture was quenched by saturated Na$_2$SO$_4$ aqueous (10 mL) at 0° C. The mixture was dried over Na$_2$SO$_4$, filtered and concentrated under reduced pressure to give the title compound (4.2 g, 88% yield). White solid. $^1$H NMR (400 MHz, DMSO-d6) δ=7.65-7.55 (m, 4H), 7.49-7.38 (m, 6H), 4.78-4.63 (m, 1H), 3.71-3.47 (m, 4H), 3.41-3.34 (m, 1H), 3.25-3.12 (m, 1H), 2.08-1.99 (m, 1H), 1.94-1.42 (m, 7H), 1.34 (d, J=7.6 Hz, 9H), 0.98 (d, J=3.2 Hz, 9H). LCMS [ESI, M−99, M+1]: 398.4, 498.3.

Step C. tert-butyl 2-(3-((tert-butyldiphenylsilyl)oxy)propyl)-2-formylpyrrolidine-1-carboxylate. To a solution of tert-butyl 2-(3-((tert-butyldiphenylsilyl)oxy)propyl)-2-(hydroxymethyl)pyrrolidine-1-carboxylate (1.0 g, 2.01 mmol, 1.0 eq) in DCM (20 mL) was added (1,1-diacetoxy-3-oxo-1,2-benziodoxol-1-yl) acetate (1.28 g, 3.01 mmol, 1.5 eq) at 0° C. The mixture was stirred at 0° C. for 1 hour. After completion, the reaction mixture was concentrated under reduced pressure and purified by column chromatography (SiO$_2$, petroleum ether: ethyl acetate=20/1 to 8/1) to give the title compound (0.85 g, 85% yield). Colorless oil; $^1$H NMR (400 MHz, DMSO-d6) δ=9.34 (d, J=6.0 Hz, 1H), 7.61 (br d, J=7.2 Hz, 4H), 7.48-7.39 (m, 6H), 3.69-3.60 (m, 2H), 3.55-3.43 (m, 1H), 1.88-1.78 (m, 2H), 1.86-1.41 (m, 7H), 1.39-1.27 (m, 9H), 0.99 (d, J=4.8 Hz, 9H). LCMS [ESI, M−99]: 396.1.

Step D. tert-butyl 2-(3-((tert-butyldiphenylsilyl)oxy)propyl)-2-ethynylpyrrolidine-1-carboxylate. To a solution of tert-butyl 2-(3-((tert-butyldiphenylsilyl)oxy)propyl)-2-formylpyrrolidine-1-carboxylate (5.50 g, 11.1 mmol, 1.0 eq) in MeOH (60 mL) was added K$_2$CO$_3$ (4.60 g, 33.3 mmol, 3.0 eq) and 1-diazo-1-dimethoxyphosphoryl-propan-2-one (3.20 g, 16.6 mmol, 1.50 eq). The mixture was stirred at 15° C. for 1 hour. The reaction mixture was filtered and the filtrate was concentrated under reduced pressure to give a residue. The residue was purified by column chromatography (SiO$_2$, Petroleum ether/Ethyl acetate=100/1 to 5/1) affording the title compound (5.50 g, 95% yield). Yellow oil; $^1$H NMR (400 MHz, chloroform-d) δ 7.72-7.64 (m, 4H), 7.46-7.35 (m, 6H), 3.78-3.52 (m, 3H), 3.37-3.21 (m, 1H), 2.42-2.13 (m, 3H), 2.04-1.88 (m, 2H), 1.87-1.68 (m, 3H), 1.60-1.51 (m, 1H), 1.47 (s, 9H), 1.06 (s, 9H). LCMS [ESI, M−99]: 392.3.

Step E. tert-butyl 2-ethynyl-2-(3-hydroxypropyl)pyrrolidine-1-carboxylate. To a solution of tert-butyl 2-(3-((tert-butyldiphenylsilyl)oxy)propyl)-2-ethynylpyrrolidine-1-carboxylate (2.0 g, 4.07 mmol, 1.0 eq) in MeOH (20 mL) was added KF (2.36 g, 40.7 mmol, 953 µL, 10.0 eq). The mixture was stirred at 60° C. for 48 hours. The reaction mixture was filtered and concentrated under reduced pressure to give a residue. The residue was purified by column chromatography (SiO$_2$, Petroleum ether/Ethyl acetate=10/1 to 1/1) affording the title compound (900 mg, 87% yield). Yellow oil. $^1$H NMR (400 MHz, chloroform-d) δ 3.74-3.50 (m, 3H), 3.35-3.24 (m, 1H), 2.46-2.12 (m, 3H), 2.03-1.87 (m, 2H), 1.85-1.73 (m, 3H), 1.61-1.52 (m, 1H), 1.47 (s, 9H).

Step F. tert-butyl 2-ethynyl-2-(3-((methylsulfonyl)oxy)propyl)pyrrolidine-1-carboxylate. To a solution of tert-butyl 2-ethynyl-2-(3-hydroxypropyl)pyrrolidine-1-carboxylate (800 mg, 3.16 mmol, 1.0 eq) in DCM (10 mL) were added TEA (959 mg, 9.47 mmol, 1.32 mL, 3.0 eq) and MsCl (543 mg, 4.74 mmol, 367 µL, 1.50 eq). The mixture was stirred at 0° C. for 1 hour. After completion, the reaction mixture was diluted with H$_2$O (10 mL) and extracted with DCM (3×10 mL). The combined organic layers were dried over Na$_2$SO$_4$, filtered and concentrated under reduced pressure to give a residue. The residue was purified by column chromatography (SiO$_2$, Petroleum ether/Ethyl acetate=50/1 to 3/1) affording the title compound (1.0 g, 95% yield). Yellow oil. $^1$H NMR (400 MHz, chloroform-d) δ 4.35-4.19 (m, 2H), 3.74-3.47 (m, 1H), 3.37-3.25 (m, 1H), 3.13 (s, 1H), 3.01 (s, 3H), 2.55-2.14 (m, 3H), 2.01-1.88 (m, 3H), 1.87-1.77 (m, 2H), 1.47 (s, 9H).

Step G. 3-(2-ethynylpyrrolidin-2-yl)propyl methanesulfonate. To a solution of tert-butyl 2-ethynyl-2-(3-((methylsulfonyl)oxy)propyl)pyrrolidine-1-carboxylate (1.0 g, 3.02 mmol, 1.0 eq) in ACN (5.0 mL) was added HCl·dioxane (4.0 M, 5.0 mL, 6.63 eq). The mixture was stirred at 0° C. for 0.5 hour. Then the mixture was warmed to 15° C. and stirred for 12 hours. After completion, the reaction mixture was concentrated under reduced pressure to give the title compound (1.0 g, crude); White solid.

Step H. 7a-ethynylhexahydro-1H-pyrrolizine. To a solution of 3-(2-ethynylpyrrolidin-2-yl)propyl methanesulfonate (1.0 g, 4.32 mmol, 1.0 eq) in ACN (20 mL) was added K$_2$CO$_3$ (5.97 g, 43.2 mmol, 10.0 eq). The mixture was stirred at 15° C. for 2 hours. The reaction mixture was filtered and the filtrate was concentrated under reduced pressure to give the title compound (270 mg, two steps yield: 66%); Yellow oil. $^1$H NMR (400 MHz, methanol-d4) δ 3.87-3.53 (m, 2H), 3.19-3.10 (m, 1H), 2.78 (s, 1H), 2.75-2.63 (m, 2H), 2.57-2.42 (m, 1H), 2.31-2.21 (m, 1H), 2.21-2.11 (m, 1H), 2.01-1.84 (m, 4H).

Step I. (1R,5S)-tert-butyl 3-(8-fluoro-7-(8-fluoronaphthalen-1-yl)-2-((hexahydro-1H-pyrrolizin-7a-yl)ethynyl)pyrido[4,3-d]pyrimidin-4-yl)-3,8-diazabicyclo[3.2.1]octane-8-carboxylate. To a solution of tert-butyl (1R,5S)-3-(2-chloro-8-fluoro-7-(8-fluoronaphthalen-1-yl)pyrido[4,3-d]pyrimidin-4-yl)-3,8-diazabicyclo[3.2.1]octane-8-carboxylate (100 mg, 186 µmol, 1.0 eq) and 7a-ethynylhexahydro-1H-pyrrolizine (126 mg, 929 µmol, 5.0 eq) in TEA (1.0 mL) and ACN (1.0 mL) were added Pd(PPh$_3$)$_2$Cl$_2$ (26.1 mg, 37.2 µmol, 0.2 eq), CuI (35.4 mg, 186 µmol, 1.0 eq). The mixture was stirred at 80° C. for 2 hours. The reaction mixture was concentrated under reduced pressure to remove solvent. The residue was diluted with H$_2$O (10 mL) and extracted with ethyl acetate (3×10 mL). The combined organic layers were dried over Na$_2$SO$_4$, filtered and concentrated under reduced pressure to give a residue. The residue was purified by prep-TLC (SiO$_2$, DCM: MeOH=10:1) affording the title compound (80 mg, 67% yield); Yellow solid. LCMS [ESI, M+1]: 637.2.

Step J. (1R,5S)-tert-butyl 3-(8-fluoro-7-(8-fluoronaphthalen-1-yl)-2-(2-(hexahydro-1H-pyrrolizin-7a-yl)ethynyl)pyrido[4,3-d]pyrimidin-4-yl)-3,8-diazabicyclo[3.2.1]octane-8-carboxylate. To a solution of (1R,5S)-tert-butyl 3-(8-fluoro-7-(8-fluoronaphthalen-1-yl)-2-((hexahydro-1H-pyrrolizin-7a-yl)ethynyl)pyrido[4,3-d]pyrimidin-4-yl)-3,8-diazabicyclo[3.2.1]octane-8-carboxylate (80 mg, 126 µmol, 1.0 eq) in MeOH (3 mL) was added Pd/C (20 mg, 10% purity). The suspension was degassed under vacuum and purged with H2 several times. The mixture was stirred under H$_2$ (15 psi) at 20° C. for 1 hour. The reaction mixture was filtered and concentrated under reduced pressure to give the title compound (80 mg, crude). Yellow solid. LCMS [ESI, M+1]: 641.3.

Step K. 4-((1R,5S)-3,8-diazabicyclo[3.2.1]octan-3-yl)-8-fluoro-7-(8-fluoronaphthalen-1-yl)-2-(2-(hexahydro-1H-pyrrolizin-7a-yl)ethyl)pyrido[4,3-d]pyrimidine. To a solution of (1R,5S)-tert-butyl 3-(8-fluoro-7-(8-fluoronaphthalen-1-yl)-2-(2-(hexahydro-1H-pyrrolizin-7a-yl)ethyl)pyrido[4,3-d]pyrimidin-4-yl)-3,8-diazabicyclo[3.2.1]octane-8-carboxylate (80 mg, 125 μmol, 1.0 eq) in ACN (1.0 mL) was added HCl·dioxane (4.0 M, 1.14 mL, 36.6 eq). The mixture was stirred at 0° C. for 0.5 hour. After completion, the reaction mixture was concentrated under reduced pressure to give residue. The residue was purified by prep-HPLC (column: Phenomenex luna C18 150*25 mm*10 um; mobile phase: [water (0.225% FA)-ACN]; B %: 7%-37%, 11 min) and lyophilized to give the title compound (15.7 mg, 1.6 FA, two steps yield: 20%); Yellow solid. $^1$H NMR (400 MHz, methanol-d4) δ 9.24 (s, 1H), 8.15 (br d, J=8.0 Hz, 1H), 7.88 (d, J=7.6 Hz, 1H), 7.77-7.69 (m, 1H), 7.68-7.62 (m, 1H), 7.60-7.52 (m, 1H), 7.26-7.14 (m, 1H), 4.95-4.90 (m, 2H), 4.13-3.98 (m, 2H), 3.97-3.83 (m, 2H), 3.67-3.55 (m, 2H), 3.28-3.13 (m, 4H), 2.44-2.34 (m, 2H), 2.27-1.88 (m, 12H). LCMS [ESI, M+1]: 541.3.

Example 219

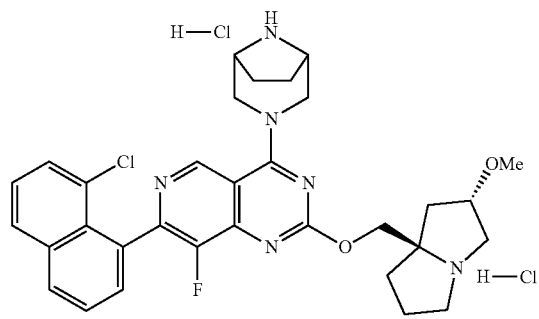

4-((1R,5S)-3,8-diazabicyclo[3.2.1]octan-3-yl)-7-(8-chloronaphthalen-1-yl)-8-fluoro-2-((2-methoxytetrahydro-1H-pyrrolizin-7a(5H)-yl)methoxy)pyrido[4,3-d]pyrimidine bis-hydrochloride

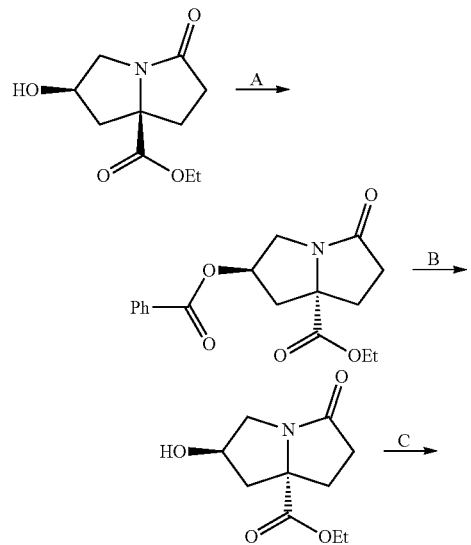

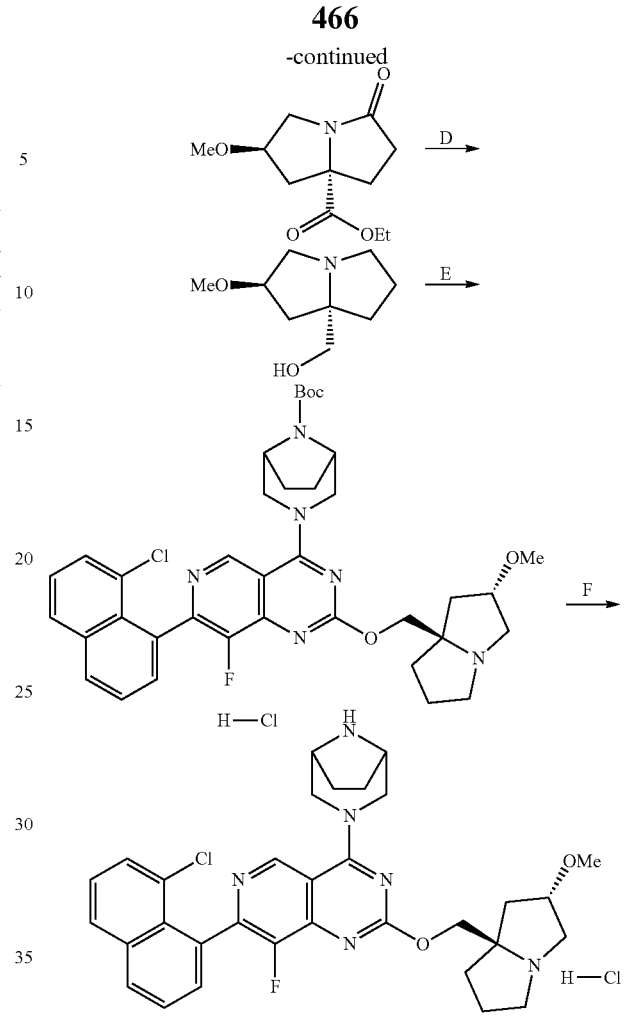

Step A. Ethyl 2-(benzoyloxy)-5-oxotetrahydro-1H-pyrrolizine-7a(5H)-carboxylate. A mixture of ethyl 2-hydroxy-5-oxotetrahydro-1H-pyrrolizine-7a(5H)-carboxylate (2.7:1 cis:trans) (0.25 g, 1.17 mmol), THF (5.86 mL), triphenylphosphine (0.461 g, 1.76 mmol) and benzoic acid (0.214 g, 1.76 mmol) was cooled to 0° C. Diisopropyl (E)-diazene-1,2-dicarboxylate (0.34 mL, 1.76 mmol) was added dropwise and the mixture was warmed to room temperature. After 1.5 hours, the mixture was diluted with ethyl acetate and washed once with 10% K$_2$CO$_3$. The organics were dried over Na$_2$SO$_4$ and concentrated in vacuo. The crude material was purified by column chromatography using 10 to 70% EtOAc/hexanes as eluent to give ethyl 2-(benzoyloxy)-5-oxotetrahydro-1H-pyrrolizine-7a(5H)-carboxylate as a clear oil (126 mg, 0.397 mmol, 34%) which was determined to be only trans diastereomer (racemic) based on NMR analysis. $^1$H NMR (400 MHz, CDCl$_3$) δ 7.95, (d, J=7.2 Hz, 2H), 7.58 (t, J=7.2 Hz, 1H), 7.45 (t, J=7.6 Hz, 2H), 5.62 (s, 1H), 4.24 (q, J=6.8 Hz, 2H), 4.13 (d, J=12.8 Hz, 1H), 3.40-3.47 (m, 1H), 2.72-2.90 (m, 3H), 2.42-2.53 (m, 1H), 2.11-2.20 (m, 2H), 1.32 (t, 6.8 Hz, 3H) ppm.

Step B. Methyl 2-hydroxy-5-oxotetrahydro-1H-pyrrolizine-7a(5H)-carboxylate. Ethyl 2-(benzoyloxy)-5-oxotetrahydro-1H-pyrrolizine-7a(5H)-carboxylate (0.233 g, 0.734 mmol), MeOH (1.47 mL, 0.734 mmol), and potassium carbonate (0.0203 g, 0.147 mmol) were stirred at rt for 1 hour. The mixture was diluted with a small amount of water and EtOAc and the aqueous layer was extracted 3× with EtOAc. The combined organics were dried over Na₂SO₄ and concentrated in vacuo. The crude material was purified by column chromatography using ethyl acetate as eluent to yield methyl 2-hydroxy-5-oxotetrahydro-1H-pyrrolizine-7a(5H)-carboxylate (trans racemate) as a white powder (99.0 mg, 0.497 mmol, 68%). ¹H NMR (400 MHz, CDCl₃) δ 4.62 (s, 1H), 3.85 (d, J=12.8 Hz, 1H), 3.76 (s, 3H), 3.17-3.25 (m, 1H), 2.64-2.84 (m, 2H), 2.51-2.59 (m, 1H), 2.39-2.48 (m, 1H), 2.21 (q, J=10.8 Hz, 1H), 1.96 (d, J=15.6 Hz, 1H), 1.68 (s, 1H) ppm.

Step C. Methyl 2-methoxy-5-oxotetrahydro-1H-pyrrolizine-7a(5H)-carboxylate. To a mixture of methyl 2-hydroxy-5-oxotetrahydro-1H-pyrrolizine-7a(5H)-carboxylate (trans racemate) (0.04 g, 0.201 mmol), silver(I) oxide (0.186 g, 0.803 mmol) and acetonitrile (1.00 mL) was added iodomethane (0.100 mL, 1.61 mmol) dropwise. The mixture was stirred at room temperature for 48 hours, then diluted with ethyl acetate, filtered, concentrated in vacuo and used without further purification.

Step D. (2-methoxytetrahydro-1H-pyrrolizin-7a(5H)-yl) methanol. Methyl 2-methoxy-5-oxotetrahydro-1H-pyrrolizine-7a(5H)-carboxylate (0.0395 g, 0.185 mmol) in THF (0.37 mL) was cooled to 0° C. and lithium aluminum hydride (1M THF solution) (0.55 mL, 0.55 mmol) was added dropwise. The mixture was heated to 70° C. for 4 hours. The mixture was diluted with ethyl ether, cooled to 0° C. and quenched with 21 µL of water followed by addition of 21 µL of 15% aqueous NaOH and 63 µL of water. The vessel was warmed to room temperature and stirred for 15 minutes. To the mixture was added anhydrous magnesium sulfate. The mixture was stirred for 15 minutes before being filtered and concentrated. The material was used crude in the next reaction.

Step E. Tert-butyl (1R,5S)-3-(7-(8-chloronaphthalen-1-yl)-8-fluoro-2-((2-methoxytetrahydro-1H-pyrrolizin-7a(5H)-yl)methoxy)pyrido[4,3-d]pyrimidin-4-yl)-3,8-diazabicyclo[3.2.1]octane-8-carboxylate. Dioxane (0.21 mL), (2-methoxytetrahydro-1H-pyrrolizin-7a(5H)-yl)methanol (trans racemate) (17.5 mg, 0.0254 mmol), tert-butyl (1R,5S)-3-(2-chloro-7-(8-chloronaphthalen-1-yl)-8-fluoro-pyrido[4,3-d]pyrimidin-4-yl)-3,8-diazabicyclo[3.2.1]octane-8-carboxylate (0.030 g, 0.054 mmol), RuPhos Palladacycle G3 (1.77 mg, 0.00212 mmol) and cesium carbonate (0.0414 g, 0.127 mmol) were charged to a 10 mL glass pressure vessel equipped with a stir bar. The mixture was sparged with argon for 5 minutes and then sealed and heated to 90° C. for 8 hours. The mixture was cooled to room temperature, filtered, concentrated in vacuo and purified by column chromatography eluting with 5 to 15% MeOH/DCM with 1% NH₄OH as modifier to furnish tert-butyl (1R,5S)-3-(7-(8-chloronaphthalen-1-yl)-8-fluoro-2-((2-methoxytetrahydro-1H-pyrrolizin-7a(5H)-yl)methoxy)pyrido[4,3-d]pyrimidin-4-yl)-3,8-diazabicyclo[3.2.1]octane-8-carboxylate (17.5 mg, 0.0254 mmol, 60%). LCMS (MM-ES+APCI, Pos): m/z 689.3 (M+H).

Step F. 4-((1R,5S)-3,8-diazabicyclo[3.2.1]octan-3-yl)-7-(8-chloronaphthalen-1-yl)-8-fluoro-2-((2-methoxytetrahydro-1H-pyrrolizin-7a(5H)-yl)methoxy)pyrido[4,3-d]pyrimidine bis-hydrochloride. Tert-butyl (1R,5S)-3-(7-(8-chloronaphthalen-1-yl)-8-fluoro-2-((2-methoxytetrahydro-1H-pyrrolizin-7a(5H)-yl)methoxy)pyrido[4,3-d]pyrimidin-4-yl)-3,8-diazabicyclo[3.2.1]octane-8-carboxylate (0.0175 g, 0.025 mmol) was diluted with dichloromethane (1 mL). To the stirred mixture was added HCl (4M in dioxane) (1 mL, 0.025 mmol). After 25 minutes, the volatiles were removed in vacuo to yield 4-((1R,5S)-3,8-diazabicyclo[3.2.1]octan-3-yl)-7-(8-chloronaphthalen-1-yl)-8-fluoro-2-((2-methoxytetrahydro-1H-pyrrolizin-7a(5H)-yl)methoxy)pyrido[4,3-d]pyrimidine bis-hydrochloride as a yellow solid (13.1 mg, 0.0198 mmol, 78%). LCMS (MM-ES+APCI, Pos): m/z 589.3 (M+H).

Example 220

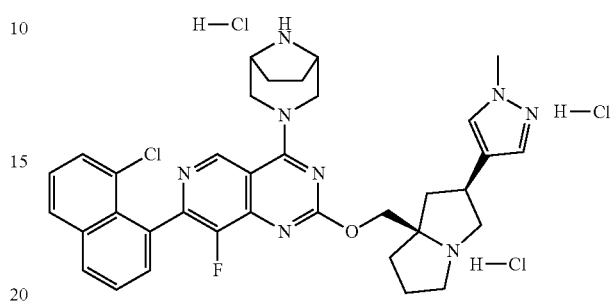

4-((1R,5S)-3,8-diazabicyclo[3.2.1]octan-3-yl)-7-(8-chloronaphthalen-1-yl)-8-fluoro-2-((2-(1-methyl-1H-pyrazol-4-yl)tetrahydro-1H-pyrrolizin-7a(5H)-yl) methoxy)pyrido[4,3-d]pyrimidine tris-hydrochloride salt Synthesized according to Example 219, steps E-F substituting (2-(1-methyl-1H-pyrazol-4-yl)tetrahydro-1H-pyrrolizin-7a(5H)-yl)methanol hydrochloride (cis racemate) for (2-methoxytetrahydro-1H-pyrrolizin-7a(5H)-yl)methanol to yield 4-((1R,5S)-3,8-diazabicyclo[3.2.1]octan-3-yl)-7-(8-chloronaphthalen-1-yl)-8-fluoro-2-((2-(1-methyl-1H-pyrazol-4-yl)tetrahydro-1H-pyrrolizin-7a(5H)-yl)methoxy) pyrido[4,3-d]pyrimidine bis-hydrochloride as a cis racemate (0.033 g, 0.044 mmol, 98% yield). LCMS (MM-ES+APCI, Pos): m/z 639.3 (M+H).

Example 221

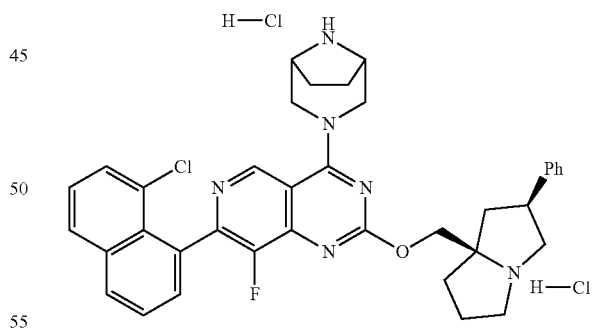

4-((1R,5S)-3,8-diazabicyclo[3.2.1]octan-3-yl)-7-(8-chloronaphthalen-1-yl)-8-fluoro-2-((2-phenyltetrahydro-1H-pyrrolizin-7a(5H)-yl)methoxy)pyrido[4,3-d]pyrimidine bis-hydrochloride salt Synthesized according to Example 219, steps E-F substituting (2-phenyltetrahydro-1H-pyrrolizin-7a(5H)-yl)methanol (cis racemate) for (2-methoxytetrahydro-1H-pyrrolizin-7a(5H)-yl)methanol. (14.2 mg, 0.0200 mmol, 95%). LCMS (MM-ES+APCI, Pos): m/z 635.3 (M+H).

Example 222

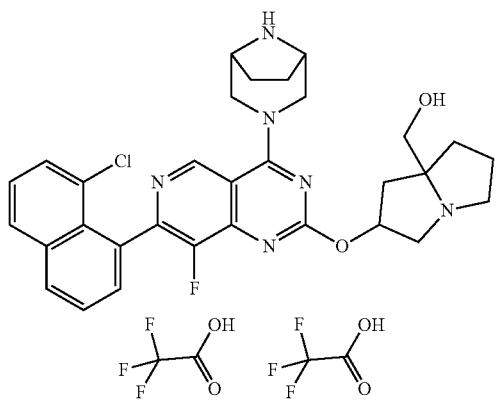

(2-((4-((1R,5S)-3,8-diazabicyclo[3.2.1]octan-3-yl)-
7-(8-chloronaphthalen-1-yl)-8-fluoropyrido[4,3-d]
pyrimidin-2-yl)oxy)tetrahydro-1H-pyrrolizin-7a
(5H)-yl)methanol bis-TFA salt

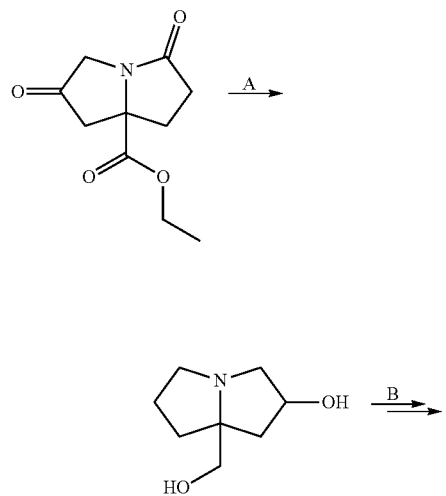

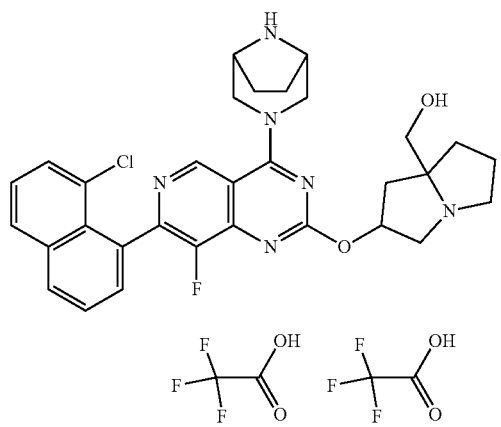

Step A. 7a-(hydroxymethyl)hexahydro-1H-pyrrolizin-2-ol. Ethyl 2,5-dioxotetrahydro-1H-pyrrolizine-7a(5H)-carboxylate (1 g, 4.7 mmol) in THF (9.5 mL, 4.7 mmol) was cooled to 0° C. and Lithium Aluminum Hydride (1.0 M in THF) (14 mL, 14 mmol) was added dropwise. After stirred for 10 minutes, the mixture was heated to 70° C. for 2 hours. The mixture was diluted with ethyl ether, cooled to 0° C. and quenched with addition of 539 µL water, 539 µL of 15% aqueous NaOH and 1617 µL of water. The vessel was warmed to room temperature and stirred for 15 minutes. To the mixture was added anhydrous magnesium sulfate. The mixture was stirred for 15 minutes before being filtered. The solution was concentrated in vacuo and used crude in the next reaction.

Step B: The title compound was synthesized according to Example 219, steps E-F substituting 7a-(hydroxymethyl)hexahydro-1H-pyrrolizin-2-ol for (2-methoxytetrahydro-1H-pyrrolizin-7a(5H)-yl)methanol. The crude residue was purified by preparative C18 HPLC (Gilson, 5-50% CH$_3$CN/H$_2$O with 0.1% TFA). Fractions containing the desired product were pooled and lyophilized to yield (2-((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)tetrahydro-1H-pyrrolizin-7a(5H)-yl)methanol as the bis TFA salt (5.00 mg, 0.00623 mmol, 16.2%). LCMS (MM-ES+APCI, Pos): m/z 575.3 (M+H).

Example 223

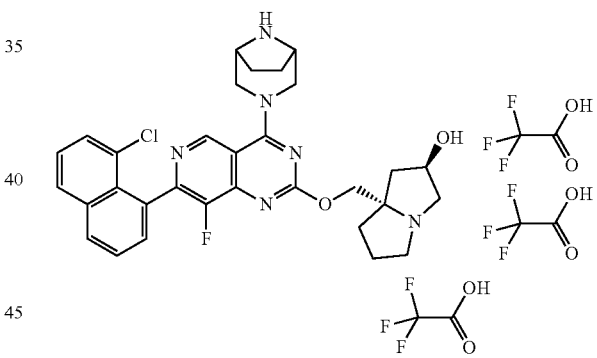

7a-(((4-((1R,5S)-3,8-diazabicyclo[3.2.1]octan-3-yl)-
7-(8-chloronaphthalen-1-yl)-8-fluoropyrido[4,3-d]
pyrimidin-2-yl)oxy)methyl)hexahydro-1H-pyrrolizin-2-ol bis-2,2,2-trifluoroacetate Synthesized according to Example 219, steps E-F substituting 7a-(hydroxymethyl)hexahydro-1H-pyrrolizin-2-ol for ((2-methoxytetrahydro-1H-pyrrolizin-7a(5H)-yl)methanol. The crude residue was purified by preparative C18 HPLC (Gilson, 5-50% CH$_3$CN/H$_2$O with 0.1% TFA). Fractions containing the desired product were pooled and lyophilized overnight to yield 7a-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)hexahydro-1H-pyrrolizin-2-ol bis-2,2,2-trifluoroacetate (5.00 mg, 0.00623 mmol, 16.2%). LCMS (MM-ES+APCI, Pos): m/z 575.3 (M+H).

Example 224

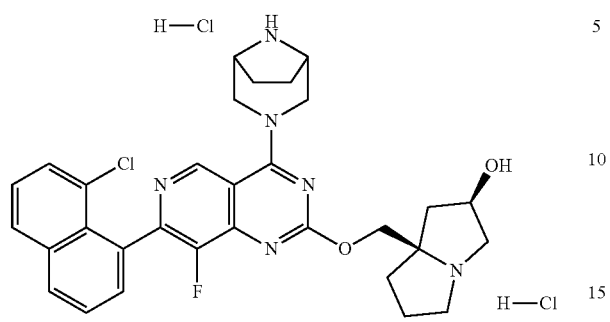

7a-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)hexahydro-1H-pyrrolizin-2-ol bis-hydrochloride Synthesized according to Example 219, steps E-F substituting 7a-(hydroxymethyl)hexahydro-1H-pyrrolizin-2-ol for (2-methoxytetrahydro-1H-pyrrolizin-7a(5H)-yl)methanol to yield (2-((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)tetrahydro-1H-pyrrolizin-7a(5H)-yl)methanol bis-hydrochloride as a colorless solid, cis racemate (6.07 mg, 0.0099 mmol, 100%). LCMS (MM-ES+APCI, Pos): m/z 575.3 (M+H).

Example 225

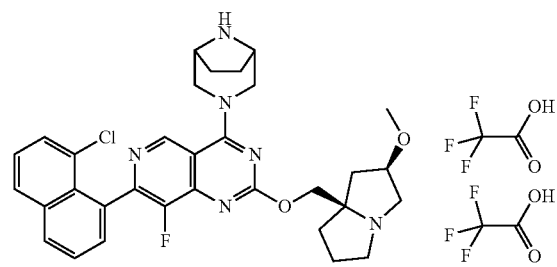

4-((1R,5S)-3,8-diazabicyclo[3.2.1]octan-3-yl)-7-(8-chloronaphthalen-1-yl)-8-fluoro-2-((2-methoxytetrahydro-1H-pyrrolizin-7a(5H)-yl)methoxy)pyrido[4,3-d]pyrimidine bis-2,2,2-trifluoroacetate

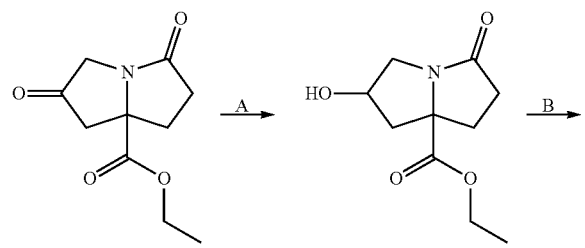

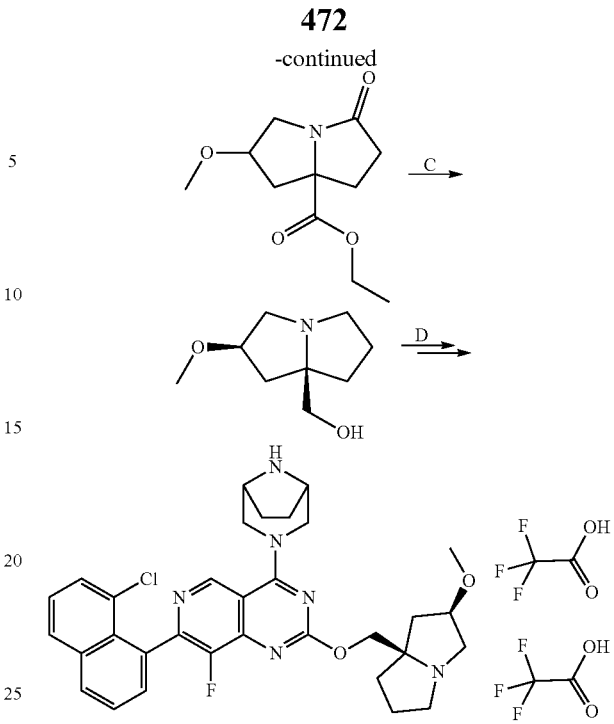

Step A. Ethyl 2-hydroxy-5-oxotetrahydro-1H-pyrrolizine-7a(5H)-carboxylate. To a stirred solution of ethyl 2,5-dioxotetrahydro-1H-pyrrolizine-7a(5H)-carboxylate (2.25 g, 10.7 mmol) in MeOH (35.5 mL) at 0° C. was added NaBH$_4$ (0.101 g, 2.66 mmol) neat as a solid. After 15 minutes the reaction was quenched slowly with 10% aqueous potassium carbonate and the layers were separated. The aqueous layer was extracted 3× with 25% isopropyl alcohol/dichloromethane. The organics were combined, dried over Na$_2$SO$_4$ and concentrated in vacuo to give ethyl 2-hydroxy-5-oxotetrahydro-1H-pyrrolizine-7a(5H)-carboxylate as a tan solid (1.85 g, 8.68 mmol, 81.4%).

Step B. Ethyl 2-methoxy-5-oxotetrahydro-1H-pyrrolizine-7a(5H)-carboxylate. Ethyl 2-hydroxy-5-oxotetrahydro-1H-pyrrolizine-7a(5H)-carboxylate (0.235 g, 1.10 mmol) and DMF (2.20 mL, 1.10 mmol) were charged to a 10 mL pear shaped flask and cooled to 0° C. Sodium hydride (0.0529 g, 1.32 mmol) was added and the mixture was stirred for 5 minutes. Iodomethane (0.0823 mL, 1.32 mmol) was added dropwise and the mixture was warmed to room temperature. After 16 hours the mixture was quenched with water and diluted with ethyl acetate. The layers were separated. The organic layer was washed 5× with brine and concentrated in vacuo to yield product which was used crude in the next reaction.

Step C. 2-methoxytetrahydro-1H-pyrrolizin-7a(5H)-yl)methanol. Crude ethyl 2-methoxy-5-oxotetrahydro-1H-pyrrolizine-7a(5H)-carboxylate (0.063 g, 0.28 mmol) in THF (0.55 mL, 0.28 mmol) was cooled to 0° C. and lithium aluminum hydride (1M in THF) (0.83 mL, 0.83 mmol) was added dropwise. After stirred for 10 minutes, the mixture was heated to 70° C. for 2 hours. The mixture was diluted with ethyl ether, cooled to 0° C. and quenched by of 32 µL water, 32 µL of 15% aqueous NaOH followed by 96 µL of water. The vessel was warmed to room temperature and stirred for 15 minutes. To the mixture was added anhydrous magnesium sulfate. The mixture was stirred for 15 minutes before being filtered. The solution was concentrated in vacuo and used crude in the next reaction.

Step D. The title compound was synthesized according to Example 219, steps E-F. The crude residue was purified with preparative HPLC eluting with 5 to 95% CH₃CN/H₂O with 0.1% TFA as modifier. Fractions containing product were pooled and lyophilized overnight to yield 4-((1R,5S)-3,8-diazabicyclo[3.2.1]octan-3-yl)-7-(8-chloronaphthalen-1-yl)-8-fluoro-2-((2-methoxytetrahydro-1H-pyrrolizin-7a(5H)-yl)methoxy)pyrido[4,3-d]pyrimidine bis-2,2,2-trifluoroacetate as the cis racemate (3.63 mg, 0.00616 mmol, 76%). LCMS (MM-ES+APCI, Pos): m/z 589.2 (M+H).

Example 226

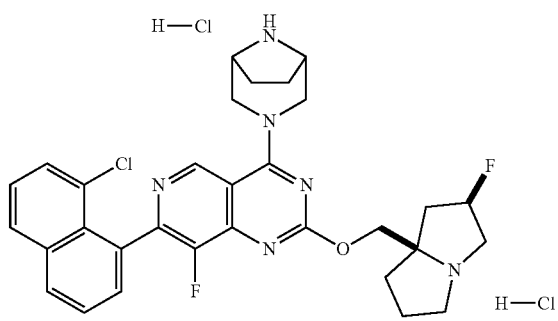

4-((1R,5S)-3,8-diazabicyclo[3.2.1]octan-3-yl)-7-(8-chloronaphthalen-1-yl)-8-fluoro-2-((2-fluorotetrahydro-1H-pyrrolizin-7a(5H)-yl)methoxy)pyrido[4,3-d]pyrimidine bis-hydrochloride

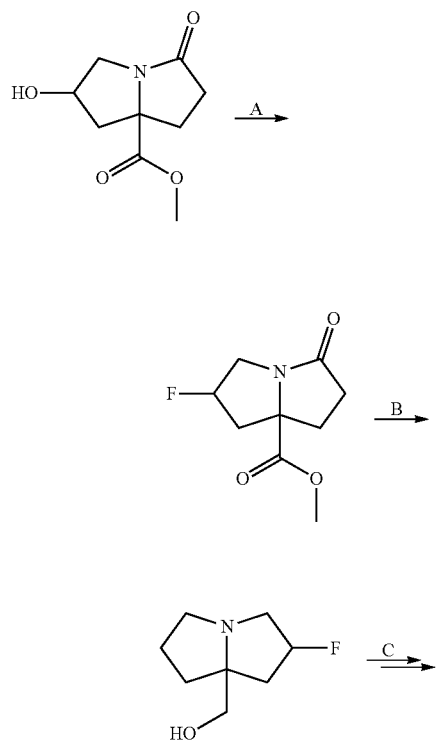

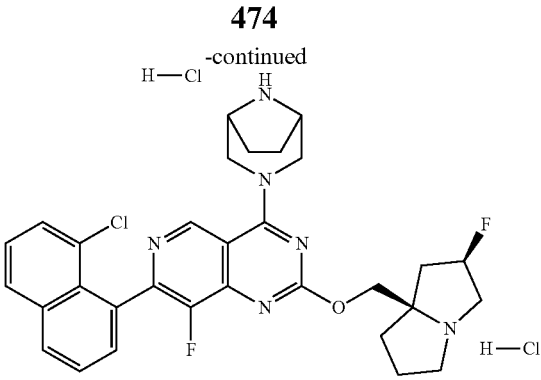

Step A. Methyl 2-fluoro-5-oxotetrahydro-1H-pyrrolizine-7a(5H)-carboxylate. To a stirred solution of methyl 2-hydroxy-5-oxotetrahydro-1H-pyrrolizine-7a(5H)-carboxylate (0.0490 g, 0.250 mmol) in dichloromethane (0.67 mL, 0.22 mmol) at −78° C. was added Deoxofluor (0.044 mL, 0.25 mmol) neat by syringe. The reaction was slowly warmed to rt and stirred overnight. The mixture was heated to 40° C. for 4 hours, cooled to rt, quenched with methanol, and stirred for 5 minutes. The crude material was concentrated in vacuo and purified by column chromatography eluting with 0 to 100% EtOAc/hexanes. The fractions containing the desired product were pooled and concentrated to yield methyl 2-fluoro-5-oxotetrahydro-1H-pyrrolizine-7a(5H)-carboxylate as a clear oil (7.00 mg, 0.033 mmol, 13%). ¹H NMR (400 MHz, CDCl₃) δ 5.30-5.49 (m, 1H), 3.91-4.08 (m, 1H), 3.79 (s, 3H), 3.32-3.47 (m, 1H), 2.77-3.01 (m, 2H), 2.39-2.54 (m, 2H), 2.09-2.22 (m, 1H), 1.73-1.92 (m, 1H) ppm.

Step B. (2-fluorotetrahydro-1H-pyrrolizin-7a(5H)-yl)methanol. Methyl 2-fluoro-5-oxotetrahydro-1H-pyrrolizine-7a(5H)-carboxylate (0.015 g, 0.0697 mmol) in THF (0.139 mL, 0.0697 mmol) was cooled to 0° C. and lithium aluminum hydride (1M in THF) (0.209 mL, 0.209 mmol) was added dropwise. The mixture was heated to 70° C. for 4 hours. The mixture was diluted with ethyl ether, cooled to 0° C. and quenched with by addition of 8 µL water, 8 µL of 15% aqueous NaOH followed by 24 µL of water. The vessel was warmed to room temperature and stirred for 15 minutes. To the mixture was added anhydrous magnesium sulfate. The mixture was stirred for 15 minutes before being filtered. Volatiles were removed in vacuo to yield (2-fluorotetrahydro-1H-pyrrolizin-7a(5H)-yl)methanol as a yellow oil which was used in the next step without further purification.

Step C. 4-((1R,5S)-3,8-diazabicyclo[3.2.1]octan-3-yl)-7-(8-chloronaphthalen-1-yl)-8-fluoro-2-((2-fluorotetrahydro-1H-pyrrolizin-7a(5H)-yl)methoxy)pyrido[4,3-d]pyrimidine bis-hydrochloride was synthesized according to Example 219, steps E-F substituting (2-fluorotetrahydro-1H-pyrrolizin-7a(5H)-yl)methanol for (2-methoxytetrahydro-1H-pyrrolizin-7a(5H)-yl)methanol to yield 4-((1R,5S)-3,8-diazabicyclo[3.2.1]octan-3-yl)-7-(8-chloronaphthalen-1-yl)-8-fluoro-2-((2-fluorotetrahydro-1H-pyrrolizin-7a(5H)-yl)methoxy)pyrido[4,3-d]pyrimidine bis-hydrochloride as the cis racemate (3.84 mg, 0.00591 mmol, 80%). LCMS (MM-ES+APCI, Pos): m/z 577.2 (M+H).

Example 227

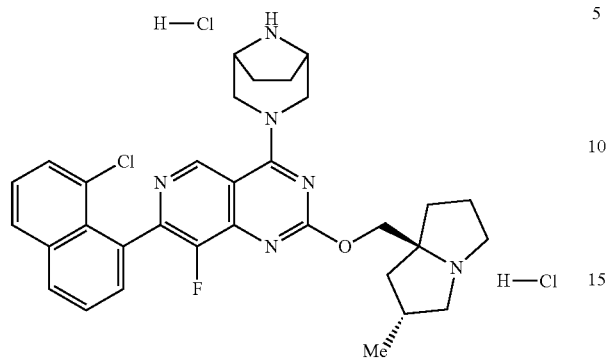

4-((1R,5S)-3,8-diazabicyclo[3.2.1]octan-3-yl)-7-(8-chloronaphthalen-1-yl)-8-fluoro-2-((2-methyltetrahydro-1H-pyrrolizin-7a(5H)-yl)methoxy)pyrido[4,3-d]pyrimidine bis-hydrochloride

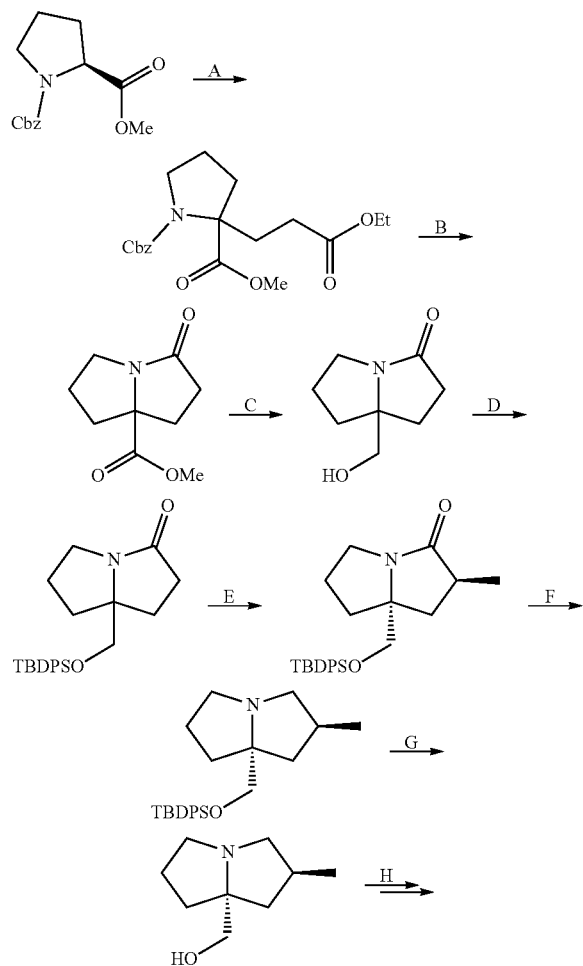

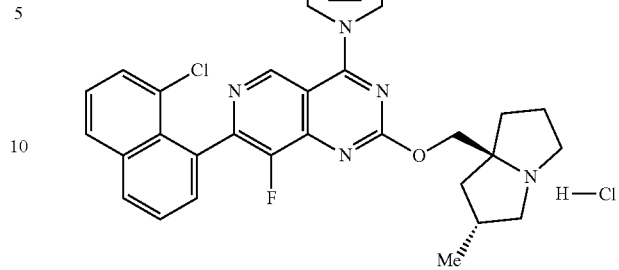

Step A. 1-benzyl 2-methyl 2-(3-ethoxy-3-oxopropyl)pyrrolidine-1,2-dicarboxylate. 1-Benzyl 2-methyl (S)-pyrrolidine-1,2-dicarboxylate (3.40 mL, 15.2 mmol) in tetrahydrofuran (76 mL) was chilled to −78° C. and lithium diisopropylamide (2M THF solution) (9.11 mL, 18.2 mmol) was then added by syringe over a 5 minute period. The mixture was stirred at −78° C. for 1 hr. Ethyl 3-bromopropanoate (5.827 mL, 45.58 mmol) was added neat. Once the addition was complete, the cooling bath was removed. The mixture was stirred for 3 hours, quenched with sat. ammonium chloride solution and water, and extracted with EtOAc. The extracts were dried over sodium sulfate and concentrated under reduced pressure. The crude material was purified by column chromatography eluting with 20% to 70% EtOAc/hexanes. The material was used crude in the next reaction.

Step B. Methyl 3-oxotetrahydro-1H-pyrrolizine-7a(5H)-carboxylate. 1-benzyl 2-methyl 2-(3-ethoxy-3-oxopropyl)pyrrolidine-1,2-dicarboxylate (2.97 g, 8.17 mmol), methanol (81.7 mL), and dihydroxypalladium (1.15 g, 1.63 mmol) were placed in a sealed flask and stirred at room temperature under nitrogen. The mixture was purged with H2 via a double-walled balloon. The mixture was stirred at room temperature for 1 hour. The vessel was purged with N$_2$ for 5 minutes and then filtered through GF/F paper. Volatiles were removed in vacuo and the mixture was constituted in toluene (81.7 mL, 8.17 mmol). The mixture was heated at 110° C. overnight, concentrated and purified by column chromatography eluting with 0 to 10% MeOH/DCM with 1% NH$_4$OH as additive to afford methyl 3-oxotetrahydro-1H-pyrrolizine-7a(5H)-carboxylate (860 mg, 4.69 mmol, 57%) as an orange oil. $^1$H NMR (400 MHz, CDCl$_3$) δ 3.76 (s, 3H), 3.63-3.71 (m, 1H), 3.11-3.19 (m, 1H), 2.75-2.86 (m, 1H), 2.52-2.58 (m, 1H), 2.38-2.47 (m, 2H), 2.02-2.12 (m, 3H), 1.63-1.17 (m, 1H) ppm.

Step C. 7a-(hydroxymethyl)hexahydro-3H-pyrrolizin-3-one. Methyl 3-oxotetrahydro-1H-pyrrolizine-7a(5H)-carboxylate (0.86 g, 4.7 mmol) and methanol (9.4 mL) were cooled to 0° C. and sodium borohydride (0.71 g, 19 mmol) was added slowly. The mixture was warmed to room temperature, whereupon significant exotherm was observed. The vessel was placed in ice bath for 10 minutes to stir. The ice bath was removed and the mixture was stirred for overnight at rt. The mixture was quenched with sat. aq. NH$_4$Cl, stirred for 5 minutes and diluted with water and ethyl acetate. The layers were separated. The aqueous layer was washed 3× with 25% IPA/DCM. The combined organics were dried over Na$_2$SO$_4$ and concentrated in vacuo to product which was used crude in the next reaction.

Step D. 7a-(((tert-butyldiphenylsilyl)oxy)methyl)hexahydro-3H-pyrrolizin-3-one. 7a-(hydroxymethyl)hexahydro- 3H-pyrrolizin-3-one (0.59 g, 3.8 mmol), dichloromethane (7.6 mL), 1H-imidazole (0.39 g, 5.8 mmol), and tert-butylchlorodiphenylsilane (1 mL, 4 mmol) were combined and stirred for 72 h at room temperature. The mixture was diluted with DCM and the organics was washed 2× with water. The organics were dried over Na₂SO₄, concentrated in vacuo, and purified by column chromatography with 0 to 100% EtOAc/hexanes as eluent to yield 7a-(((tert-butyldiphenylsilyl)oxy)methyl)hexahydro-3H-pyrrolizin-3-one as a white powder (760 mg, 1.93 mmol, 51%). ¹H NMR (400 MHz, CDCl₃) δ 7.62-7.66 (m, 4H), 7.36-7.47 (m, 6H), 3.63-3.72 (m, 1H), 3.45-3.54 (m, 2H), 2.76-2.95 (m, 2H), 2.26-2.43 (m, 2H), 1.78-2.02 (m, 4H), 1.45-1.57 (m, 1H). 1.06 (s, 9H) ppm.

Step E. 7a-(((tert-butyldiphenylsilyl)oxy)methyl)-2-methylhexahydro-3H-pyrrolizin-3-one. 7a-(((tert-butyldiphenylsilyl)oxy)methyl)hexahydro-3H-pyrrolizin-3-one (0.76 g, 1.93 mmol) and tetrahydrofuran (5.52 mL, 1.93 mmol) were placed under N₂ and cooled to −78° C. Lithium diisopropylamide (2M THF solution) (1.26 mL, 2.51 mmol) was added dropwise to the stirring solution via syringe and the mixture was stirred for 30 minutes. Iodomethane (0.15 mL, 2.5 mmol) was added dropwise via syringe and the reaction stirred for 3 hours. The mixture was quenched with sat. aq. NH₄Cl. The solution was extracted with EtOAc 3×. The combined organic layers were dried over Na₂SO₄, and concentrated in vacuo. The mixture was purified by column chromatography with 10 to 90% ethyl acetate/hexanes as eluent to yield 7a-(((tert-butyldiphenylsilyl)oxy)methyl)-2-methylhexahydro-3H-pyrrolizin-3-one as a yellow oil (384 mg, 0.942 mmol, 49%), trans racemate isolated. ¹H NMR (400 MHz, CDCl₃) δ 7.64 (d, J=7.2 Hz, 4H), 7.36-7.47 (m, 6H), 3.62-3.72 (m 1H), 3.44-3.55 (m, 2H), 2.86-2.98 (m, 2H), 2.47-2.55 (m, 1H), 1.88-2.00 (m, 3H), 1.38-1.52 (m, 2H), 1.13 (d, J=7.2 Hz, 3H), 1.05 (s, 9H) ppm.

Step F. 7a-(((tert-butyldiphenylsilyl)oxy)methyl)-2-methylhexahydro-1H-pyrrolizine. (2R,7aS)-7a-(((tert-butyldiphenylsilyl)oxy)methyl)-2-methylhexahydro-3H-pyrrolizin-3-one (0.192 g, 0.471 mmol) in THF (1.9 mL) was cooled to 0° C. and lithium aluminum hydride (THF 1M solution) (1.41 mL, 1.41 mmol) was added dropwise. The mixture was heated to 70° C. for 4 hours. The mixture was cooled to room temperature, diluted with ethyl ether, cooled to 0° C. and quenched with 54 μL water, 54 μL of 15% aqueous NaOH followed by 162 μL of water. The vessel was warmed to room temperature and stirred for 15 minutes. To the mixture was added anhydrous magnesium sulfate. The mixture was stirred for 15 minutes before being filtered. The filter cake was washed with ethyl ether and the combined organics were concentrated in vacuo and the product used crude in the next reaction.

Step G. (2-methyltetrahydro-1H-pyrrolizin-7a(5H)-yl)methanol. 7a-(((tert-butyldiphenylsilyl)oxy)methyl)-2-methylhexahydro-1H-pyrrolizine (141 mg, 0.358 mmol) and THF (1.1 mL) were treated with HF Pyridine solution (70% HF, 0.46 mmol, 120 μL) dropwise, via syringe and the mixture was stirred at room temperature for 16 hours. The mixture was quenched with 10% aq K₂CO₃ and diluted with ethyl acetate. The layers were separated. The aqueous layer was extracted with dichloromethane 3×. The aqueous layer was then diluted with brine and extracted with 25% IPA/DCM×4. The combined organic extracts were dried over Na₂SO₄ and concentrated in vacuo to yield a yellow oil which was used in the next step without further purification.

Step H. The title compound was synthesized according to Example 219, steps E-F substituting (2-methyltetrahydro-1H-pyrrolizin-7a(5H)-yl)methanol for (2-methoxytetrahydro-1H-pyrrolizin-7a(5H)-yl)methanol to yield 4-((1R,5S)-3,8-diazabicyclo[3.2.1]octan-3-yl)-7-(8-chloronaphthalen-1-yl)-8-fluoro-2-((2-methyltetrahydro-1H-pyrrolizin-7a(5H)-yl)methoxy)pyrido[4,3-d]pyrimidine bis-hydrochloride, trans racemate (10.0 mg, 0.0155 mmol, 99%). LCMS (MM-ES+APCI, Pos): m/z 573.3 (M+H).

Example 228

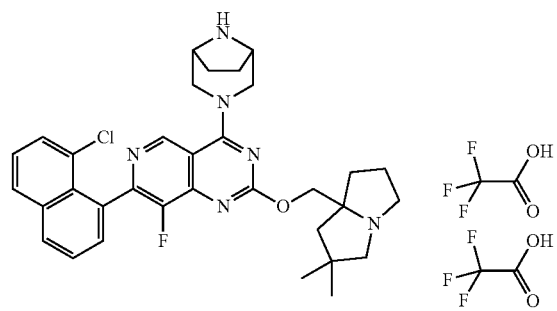

4-((1R,5S)-3,8-diazabicyclo[3.2.1]octan-3-yl)-7-(8-chloronaphthalen-1-yl)-2-((2,2-dimethyltetrahydro-1H-pyrrolizin-7a(5H)-yl)methoxy)-8-fluoropyrido[4,3-d]pyrimidine bis-2,2,2-trifluoroacetate

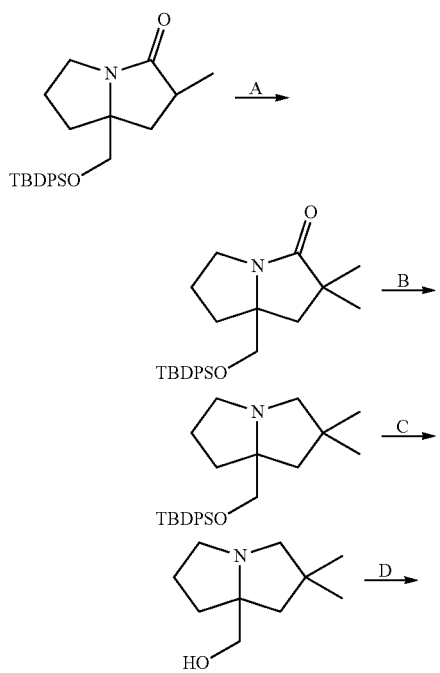

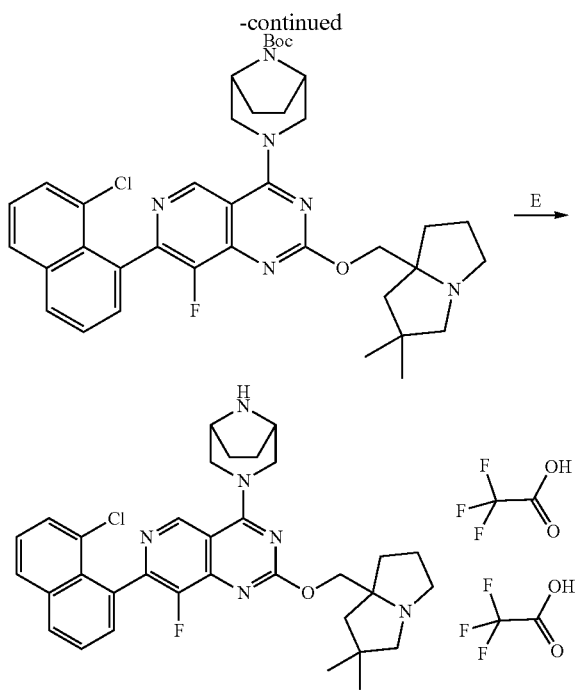

Step A. 7a-(((tert-butyldiphenvlsilyl)oxy)methyl)-2,2-dimethylhexahydro-3H-pyrrolizin-3-one. 7a-(((tert-butyldiphenylsilyl)oxy)methyl)-2-methylhexahydro-3H-pyrrolizin-3-one (0.07 g, 0.17 mmol) and tetrahydrofuran (0.49 mL) were placed under $N_2$ and cooled to −78° C. Lithium diisopropylamide (2M THF solution) (0.17 mL, 0.34 mmol) was added dropwise to the stirring solution via syringe and the mixture was stirred for 45 minutes. Iodomethane (0.0160 mL, 0.258 mmol) was added dropwise via syringe and stirred for 3 hours. The mixture was quenched with saturated aqueous $NH_4Cl$. The solution was extracted with EtOAc 3×, the combined organics dried over $Na_2SO_4$ and concentrated in vacuo. The mixture was purified by column chromatography with 0 to 80% EtOAc/Hex to yield 7a-(((tert-butyldiphenylsilyl)oxy)methyl)-2,2-dimethylhexahydro-3H-pyrrolizin-3-one as a yellow oil (60 mg, 0.142 mmol, 83%). $^1$H NMR (400 MHz, $CDCl_3$) δ 7.63-7.67 (m, 4H), 7.36-7.47 (m, 6H), 3.68-3.77 (m, 1H), 3.55 (d, J=10.0 Hz, 1H), 3.46 (d, J=10.0 Hz, 1H), 2.96-3.04 (m, 1H), 2.10-2.19 (m, 2H), 1.91-2.00 (m, 2H), 1.75 (d, J=13.2 Hz, 1H), 1.34-1.43 (m, 1H), 1.15 (s, 6H), 1.06 (s, 9H) ppm.

Step B. 7a-(((tert-butyldiphenylsilyl)oxy)methyl)-2,2-dimethylhexahydro-1H-pyrrolizine. 7a-(((tert-butyldiphenylsilyl)oxy)methyl)-2,2-dimethylhexahydro-3H-pyrrolizin-3-one (0.06 g, 0.14 mmol) in dry THF (0.57 mL, 0.14 mmol) was cooled to 0° C. and lithium aluminum hydride (1M in THF) (0.43 mL, 0.43 mmol) was added dropwise. The mixture was heated to 70° C. for 4 hours. The mixture was cooled to room temperature, diluted with ethyl ether, cooled to 0° C. and quenched with 16 μL water. 16 μL of 15% aqueous NaOH was added to the mixture, followed by 48 μL of water. The vessel was warmed to room temperature and stirred for 15 minutes. To the mixture was added anhydrous magnesium sulfate. The mixture was stirred for 15 minutes before being filtered. Filtrate was washed with ethyl ether and combined organics were concentrated in vacuo. Product was used without further purification, colorless oil.

Step C. (2,2-dimethyltetrahydro-1H-pyrrolizin-7a(5H)-yl)methanol. 7a-(((tert-butyldiphenylsilyl)oxy)methyl)-2,2-dimethylhexahydro-1H-pyrrolizine (0.051 g, 0.13 mmol) was combined with 4M HCl in dioxane (1.6 mL, 6.3 mmol). The mixture was stirred at room temperature for 16 hours. Volatiles were removed in vacuo and the crude mixture was constituted in 5 mL of ACN and washed 4× with 2 mL of hexanes. The acetonitrile layer was concentrated in vacuo to yield a tan oil and the product used without further purification.

Step D. Tert-butyl (1R,5S)-3-(7-(8-chloronaphthalen-1-yl)-2-((2,2-dimethyltetrahydro-1H-pyrrolizin-7a(5H)-yl)methoxy)-8-fluoropyrido[4,3-d]pyrimidin-4-yl)-3,8-diazabicyclo[3.2.1]octane-8-carboxylate. Toluene (0.30 mL), ((2,2-dimethyltetrahydro-1H-pyrrolizin-7a(5H)-yl)methanol (0.020 g, 0.12 mmol), tert-butyl (1R,5S)-3-(2-chloro-7-(8-chloronaphthalen-1-yl)-8-fluoropyrido[4,3-d]pyrimidin-4-yl)-3,8-diazabicyclo[3.2.1]octane-8-carboxylate (0.033 g, 0.06 mmol), potassium carbonate (0.025 g, 0.18 mmol), BINAP (0.0075 g, 0.012 mmol) and diacetoxypalladium (0.0013 g, 0.0060 mmol) were charged to a 10 mL glass pressure vessel equipped with a stir bar. The mixture was sparged with argon for 5 minutes, then sealed, and heated to 110° C. for 12 hours. The vessel was cooled to room temperature and the mixture was filtered, concentrated in vacuo, and purified by column chromatography eluting with 0 to 20% MeOH/DCM with 1% $NH_4OH$ as additive to yield tert-butyl (1R,5S)-3-(7-(8-chloronaphthalen-1-yl)-2-((2,2-dimethyltetrahydro-1H-pyrrolizin-7a(5H)-yl)methoxy)-8-fluoropyrido[4,3-d]pyrimidin-4-yl)-3,8-diazabicyclo[3.2.1]octane-8-carboxylate (15 mg, 0.022 mmol, 36%). LCMS (MM-ES+APCI, Pos): m/z 687.3 (M+H).

Step E. 4-((1R,5S)-3,8-diazabicyclo[3.2.1]octan-3-yl)-7-(8-chloronaphthalen-1-yl)-2-((2,2-dimethyltetrahydro-1H-pyrrolizin-7a(5H)-yl)methoxy)-8-fluoropyrido[4,3-d]pyrimidine bis-2,2,2-trifluoroacetate. Tert-butyl (1R,5S)-3-(7-(8-chloronaphthalen-1-yl)-2-((2,2-dimethyltetrahydro-1H-pyrrolizin-7a(5H)-yl)methoxy)-8-fluoropyrido[4,3-d]pyrimidin-4-yl)-3,8-diazabicyclo[3.2.1]octane-8-carboxylate (0.015 g, 0.022 mmol), and 2,2,2-trifluoroacetic acid (1 mL) were stirred at room temperature for 15 minutes. Volatiles were removed in vacuo and the crude residue was purified by preparative C18 HPLC Gilson eluting with 5 to 95% $CH_3CN/H_2O$ with 0.1% TFA as modifier to yield 4-((1R,5S)-3,8-diazabicyclo[3.2.1]octan-3-yl)-7-(8-chloronaphthalen-1-yl)-2-((2,2-dimethyltetrahydro-1H-pyrrolizin-7a(5H)-yl)methoxy)-8-fluoropyrido[4,3-d]pyrimidine bis-2,2,2-trifluoroacetate as the racemate (3.60 mg, 0.0044 mmol, 20%). LCMS (MM-ES+APCI, Pos): m/z 587.2 (M+H).

Example 229

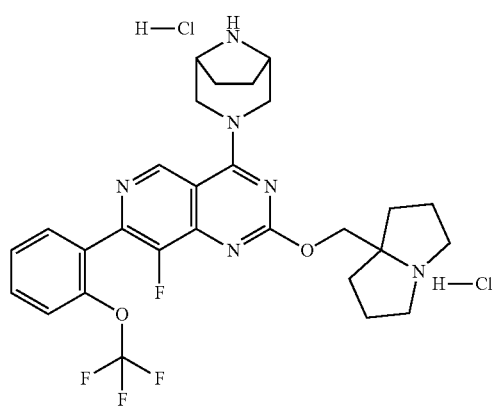

4-((1R,5S)-3,8-diazabicyclo[3.2.1]octan-3-yl)-8-fluoro-2-((tetrahydro-1H-pyrrolizin-7a(5H)-yl)methoxy)-7-(2-(trifluoromethoxy)phenyl)pyrido[4,3-d]pyrimidine bis-hydrochloride

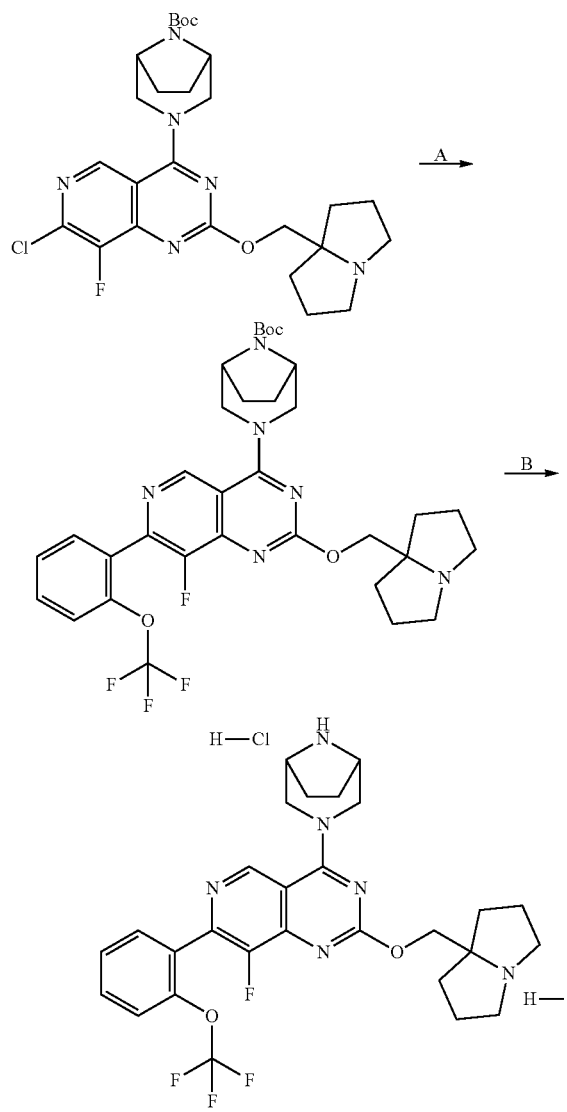

Step A. Tert-butyl (1R,5S)-3-(8-fluoro-2-((tetrahydro-1H-pyrrolizin-7a(5H)-yl)methoxy)-7-(2-(trifluoromethoxy)phenyl)pyrido[4,3-d]pyrimidin-4-yl)-3,8-diazabicyclo[3.2.1]octane-8-carboxylate. Dioxane (0.625 mL), (2-(trifluoromethoxy)phenyl)boronic acid (0.0193 g, 0.0937 mmol), tert-butyl (1R,5S)-3-(7-chloro-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (0.0333 g, 0.0625 mmol), RuPhos Palladacycle Gen. 3 (0.0026 g, 0.0031 mmol) and potassium carbonate (2M aqueous) (0.093 mL, 0.19 mmol) were charged to a 10 mL glass pressure vessel equipped with a stir bar. The mixture was sparged with argon for 5 minutes, then sealed and heated to 90° C. for 8 hours. The mixture was cooled to rt and diluted with water and EtOAc. The aqueous layer was extracted 3× with EtOAc. The combined organics were dried over Na₂SO₄, concentrated in vacuo and purified by column chromatography eluting with 0 to 20% MeOH/DCM with 1% NH₄OH as additive to give tert-butyl (1R,5S)-3-(8-fluoro-2-((tetrahydro-1H-pyrrolizin-7a(5H)-yl)methoxy)-7-(2-(trifluoromethoxy)phenyl)pyrido[4,3-d]pyrimidin-4-yl)-3,8-diazabicyclo[3.2.1]octane-8-carboxylate (246 mg, 0.0373 mmol, 60%). LCMS (MM-ES+APCI, Pos): m/z 659.3 (M+H).

Step B. 4-((1R,5S)-3,8-diazabicyclo[3.2.1]octan-3-yl)-8-fluoro-2-((tetrahydro-1H-pyrrolizin-7a(5H)-yl)methoxy)-7-(2-(trifluoromethoxy)phenyl)pyrido[4,3-d]pyrimidine bis-hydrochloride. Tert-butyl (1R,5S)-3-(8-fluoro-2-((tetrahydro-1H-pyrrolizin-7a(5H)-yl)methoxy)-7-(2-(trifluoromethoxy)phenyl)pyrido[4,3-d]pyrimidin-4-yl)-3,8-diazabicyclo[3.2.1]octane-8-carboxylate (0.03 g, 0.046 mmol), dichloromethane (0.5 mL, 0.046 mmol), and 4M HCl in Dioxane (1.14 mL, 4.55 mmol) were charged to a 25 mL pear shaped flask. The mixture was stirred at room temperature for 15 min and then volatiles were removed in vacuo to furnish 4-((1R,5S)-3,8-diazabicyclo[3.2.1]octan-3-yl)-8-fluoro-2-((tetrahydro-1H-pyrrolizin-7a(5H)-yl)methoxy)-7-(2-(trifluoromethoxy)phenyl)pyrido[4,3-d]pyrimidine bis-hydrochloride (25.0 mg, 0.0396 mmol, 87%). LCMS (MM-ES+APCI, Pos): m/z 559.2 (M+H).

Example 230

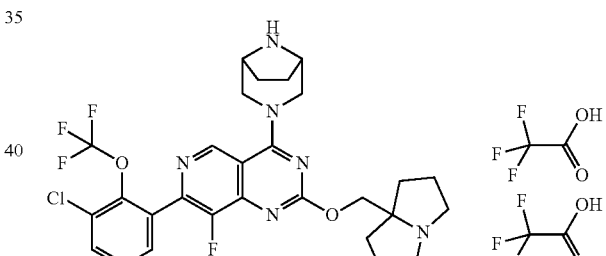

4-((1R,5S)-3,8-diazabicyclo[3.2.1]octan-3-yl)-7-(3-chloro-2-(trifluoromethoxy)phenyl)-8-fluoro-2-((tetrahydro-1H-pyrrolizin-7a(5H)-yl)methoxy)pyrido[4,3-d]pyrimidine bis(2,2,2-trifluoroacetate

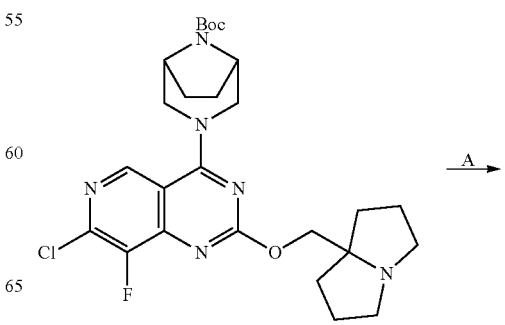

483

-continued

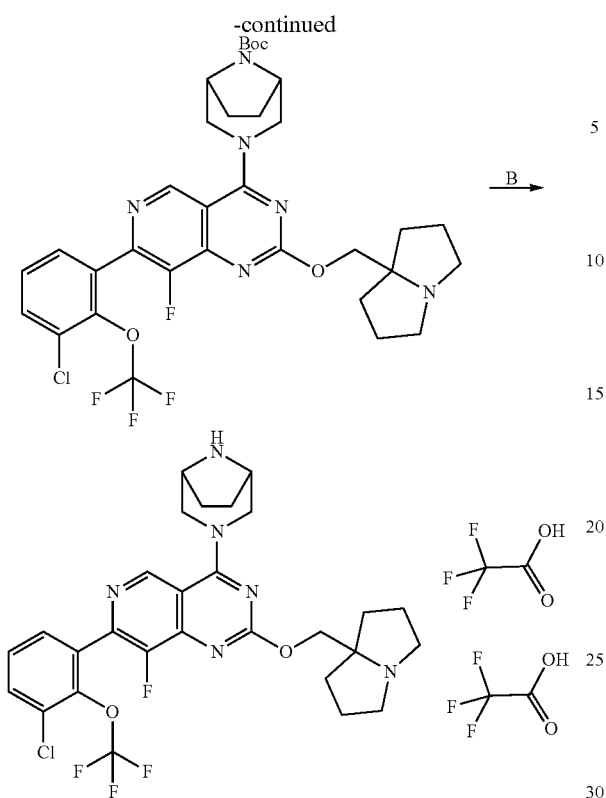

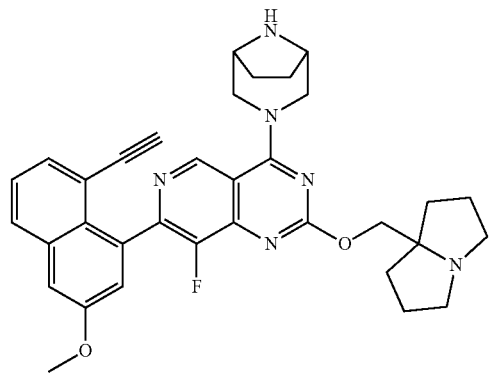 [SMILES: C#Cc1cccc2cc(OC)cc(-c3ncc4c(N5CC6CCC(C5)N6)nc(OCC56CCCN5CCC6)nc4c3F)c12]

Step A. Tert-butyl (1R,5S)-3-(7-(3-chloro-2-(trifluoromethoxy)phenyl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate. Tert-butyl (1R,5S)-3-(7-chloro-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (0.044 g, 0.083 mmol), (3-chloro-2-(trifluoromethoxy)phenyl)boronic acid (0.01 g, 0.042 mmol), 2M aqueous $K_2CO_3$ (0.062 mL, 0.12 mmol), dioxane (0.42 mL), and RuPhos Palladacyle G3 (0.0017 g, 0.0021 mmol) were charged to a 10 mL glass pressure vessel equipped with a stir bar. The mixture was sparged with argon for 5 minutes, then sealed and heated to 90° C. for 8 hours. The mixture was cooled to rt and diluted with ethyl acetate and water. The layers were separated. The aqueous layer was extracted 3× with ethyl acetate. The combined organics were dried over $Na_2SO_4$, concentrated in vacuo and purified by column chromatography eluting with 0 to 20% MeOH/DCM with 1% $NH_4OH$ as additive to give impure product which was carried crude to the next reaction.

Step B. 4-((1R,5S)-3,8-diazabicyclo[3.2.1]octan-3-yl)-7-(3-chloro-2-(trifluoromethoxy)phenyl)-8-fluoro-2-((tetrahydro-1H-pyrrolizin-7a(5H)-yl)methoxy)pyrido[4,3-d]pyrimidine bis-2,2,2-trifluoroacetate. Tert-butyl (1R,5S)-3-(7-(3-chloro-2-(trifluoromethoxy)phenyl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (0.02 g, 0.0072 mmol) was charged to a 25 mL pear shaped flask and diluted with dichloromethane (0.5 mL) and hydrogen chloride (4M in dioxane) (0.5 mL, 0.0072 mmol). The mixture was stirred for 15 minutes at room temperature and then concentrated in vacuo. The crude residue was purified by preparative C18 HPLC eluting with 5-95% $CH_3CN/H_2O$ with 0.1% TFA as additive. Fractions containing the desired product were pooled and lyophilized overnight to yield 4-((1R,5S)-3,8-diazabicyclo[3.2.1]octan-3-yl)-7-(3-chloro-2-(trifluoromethoxy)phenyl)-8-fluoro-2-((tetrahydro-1H-pyrrolizin-7a(5H)-yl)methoxy)pyrido[4,3-d]pyrimidine bis(2,2,2-trifluoroacetate) (0.001 g, 0.0012 mmol, 17% yield). LCMS (MM-ES+APCI, Pos): m/z 593.2 (M+H).

Example 231

4-((1R,5S)-3,8-diazabicyclo[3.2.1]octan-3-yl)-7-(8-ethynyl-3-methoxynaphthalen-1-yl)-8-fluoro-2-((hexahydro-1H-pyrrolizin-7a-yl)methoxy)pyrido[4,3-d]pyrimidine

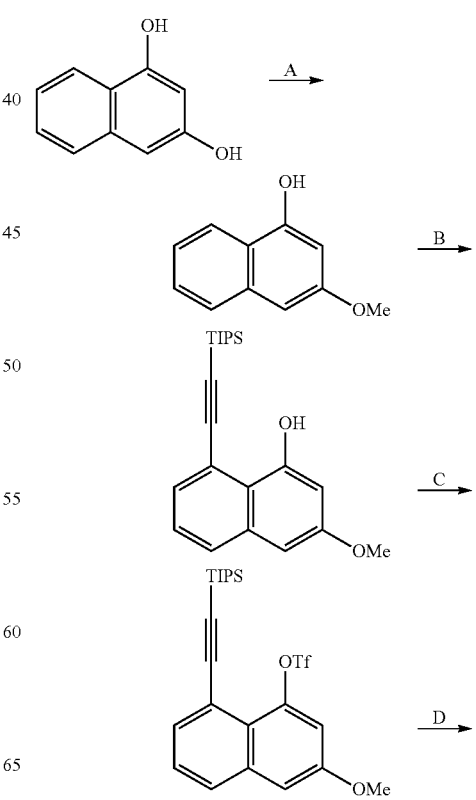

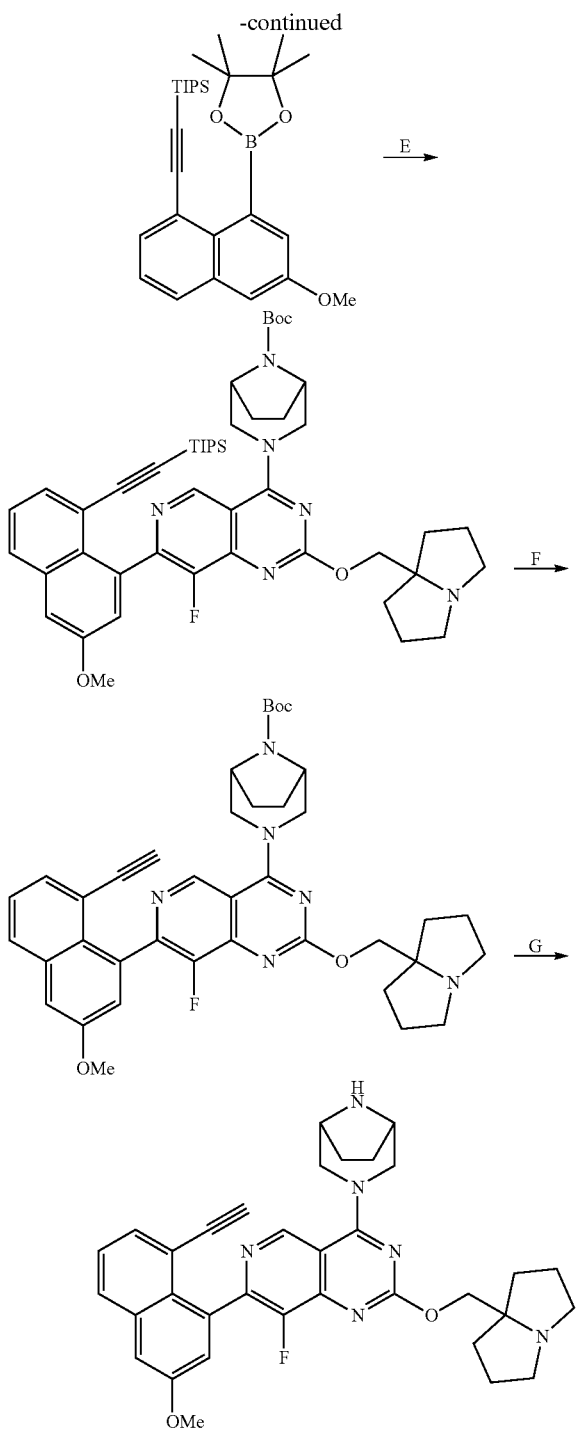

Step A. 3-methoxynaphthalen-1-ol. HCl gas was bubbled for 10 min at 0° C. into a solution of naphthalene-1,3-diol (15 g, 93.6 mmol, 1.0 eq) in MeOH (10 mL), the mixture was stirred at 20° C. for 2 hours. The mixture was concentrated to dryness. The residue was purified by reversed phase HPLC (0.1% FA condition) to give the title compound (10.7 g, 56.9 mmol, 61% yield). Brown solid. 1H NMR (400 MHz, CDCl$_3$-d) δ=8.10 (d, J=8.3 Hz, 1H), 7.72 (d, J=8.2 Hz, 1H), 7.47 (m, 1H), 7.36 (t, J=7.3 Hz, 1H), 6.80 (d, J=2.2 Hz, 1H), 6.55 (d, J=2.3 Hz, 1H), 5.76 (s, 1H), 3.91 (s, 3H), 1.99 (s, 1H). LCMS (ESI, M+1): 175.

Step B. 3-methoxy-8-((triisopropylsilyl)ethynyl)naphthalen-1-ol. A mixture of 3-methoxynaphthalen-1-ol (5 g, 28.7 mmol, 1.0 equiv), (bromoethynyl)triisopropylsilane (9 g, 34.4 mmol, 1.2 eq), K$_2$CO$_3$ (3.97 g, 28.7 mmol, 1.0 eq), dichlororuthenium; 1-isopropyl-4-methyl-benzene (2.64 g, 4.31 mmol, 0.15 eq) and NaOAc (470.93 mg, 5.74 mmol, 0.2 eq) in DCE (3 mL) was stirred at 40° C. for 16 hours. After completion, the mixture was diluted with water (100 mL), extracted with ethyl acetate (100 mL). The organic layer was washed with saturated brine (100 mL), dried over Na$_2$SO$_4$, filtered and concentrated to dryness. The residue was purified by reversed-phase HPLC (0.1% FA condition) to give the title compound (10.5 g, 28.13 mmol, 98% yield). Brown oil. $^1$H NMR (400 MHz, CDCl$_3$-d) δ=9.23 (s, 1H), 7.70~7.68 (d, J=8.0, 1H), 7.49~7.47 (d, J=8.0 Hz, 1H), 7.33~7.29 (m, 1H), 6.76~6.75 (m, 1H), 6.70~6.69 (m, 1H), 3.89 (s, 3H), 1.29~1.09 (m, 21H). LCMS (ESI, M+1): 355.

Step C. [3-methoxy-8-(2-triisopropylsilylethynyl)-1-naphthyl] trifluoromethanesulfonate. To a mixture of 3-methoxy-8-((triisopropylsilyl)ethynyl)naphthalen-1-ol (3.0 g, 8.46 mmol, 1.0 eq) in dichloromethane (30 mL) were added DIEA (2.19 g, 16.9 mmol, 2.95 mL, 2.0 eq) and Tf$_2$O (3.58 g, 12.7 mmol, 2.09 mL, 1.5 eq) at −30° C. The mixture was stirred at −40° C. for 0.5 hour. After completion, the mixture was diluted with water (20 mL) and then separated. The organic layer was washed with saturated brine (15 mL). The aqueous phase was extracted with ethyl acetate (2×15 mL), and the combined organic layer was washed with saturated brine (6 mL). The combined organic layer was dried over Na$_2$SO$_4$, filtered and concentrated under vacuum. The residue was purified by column chromatography (SiO$_2$, petroleum ether/ethyl acetate=1/0) to give the title compound (3.76 g, 91% yield). Yellow oil. Rf=0.5 (10:1, petroleum ether/ethyl acetate). $^1$H NMR (400 MHz, CDCl$_3$-d) δ=7.74-7.70 (m, 2H), 7.43 (dd, J=7.2, 8.4 Hz, 1H), 7.23 (d, J=2.4 Hz, 1H), 7.15 (d, J=2.4 Hz, 1H), 3.93 (s, 3H), 1.20-1.14 (m, 19H). LCMS (ESI, M+1): 487.

Step D. Triisopropyl-[2-[6-methoxy-8-(4,4,5,5-tetramethyl-1,3,2-dioxaborolan-2-yl)-1-naphthyl]ethynyl]silane. To a mixture of [3-methoxy-8-(2-triisopropylsilylethynyl)-1-naphthyl]trifluoromethanesulfonate (1.28 g, 2.63 mmol, 1.0 eq) and 4,4,5,5-tetramethyl-2-(4,4,5,5-tetramethyl-1,3,2-dioxaborolan-2-yl)-1,3,2-dioxaborolane (1.34 g, 5.26 mmol, 2.0 eq) in dioxane (20 mL) was added KOAc (774 mg, 7.89 mmol, 3.0 eq). The mixture was degassed and then Pd(dppf)Cl$_2$ (192 mg, 263 μmol, 0.10 eq) was added into the above mixture under N$_2$. The mixture was stirred at 110° C. for 1 hour under N$_2$. After completion, the mixture was diluted with ethyl acetate (20 mL) and water (25 mL), and then separated. The aqueous phase was extracted with ethyl acetate (20 mL), and the combined organic layer was washed with saturated brine (25 mL), dried over Na$_2$SO$_4$, filtered and concentrated under vacuum. The residue was purified by column chromatography (SiO$_2$, petroleum ether/ethyl acetate=50/1) twice. The residue was purified by reversed phase flash chromatography [water (FA, 0.1%)/acetonitrile] to give the title compound (555 mg, 23% yield). Red oil. Rf=0.6 (10:1, petroleum ether/ethyl acetate). $^1$H NMR (400 MHz, CDCl$_3$-d) δ=7.70-7.66 (m, 2H), 7.42 (d, J=2.8 Hz, 1H), 7.35 (t, J=7.6 Hz, 1H), 7.12 (d, J=2.8 Hz, 1H), 3.91 (s, 3H), 1.43 (s, 12H), 1.16 (s, 21H). LCMS (ESI, M+1): 465.

Step E. tert-butyl (1R,5S)-3-(8-fluoro-7-(3-methoxy-8-((triisopropylsilyl)ethynyl)naphthalen-1-yl)-2-((tetrahydro-1H-pyrrolizin-7a(5H)-yl)methoxy)pyrido[4,3-d]pyrimidin-4-yl)-3,8-diazabicyclo[3.2.1]octane-8-carboxylate. A mixture of tert-butyl (1R,5S)-3-(7-chloro-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (55 mg, 103 μmol, 1.0 eq), triisopropyl-[2-[6-methoxy-8-(4,4,5,5-tetramethyl-1,3,2-dioxaborolan-2-yl)-1-naphthyl]ethynyl]silane (62.3 mg, 134 μmol, 1.30 eq) and Cs₂CO₃ (101 mg, 310 μmol, 3.0 eq) in dioxane (1.5 mL) and H₂O (0.5 mL) was degassed. Then Pd(dppf)Cl₂ (7.55 mg, 10.3 μmol, 0.10 eq) was added into the above mixture and the mixture was stirred at 100° C. for 2.5 hours under N₂. After completion, the mixture was diluted with ethyl acetate (10 mL) and water (15 mL), and then separated. The aqueous phase was extracted with ethyl acetate (2×10 mL). The combined organic layer was washed with saturated brine (15 mL), dried over Na₂SO₄, filtered, and concentrated under vacuum. The residue was purified by column chromatography (SiO₂, ethyl acetate/methanol=10/1) and reversed phase flash [water (FA, 0.1%)/acetonitrile] to give the title compound (21 mg, 8.8% yield). Brown solid. Rf=0.25 (10:1, dichloromethane: methanol). LCMS (ESI, M+1): 835.

Step F. tert-butyl (1R,5S)-3-(7-(8-ethynyl-3-methoxynaphthalen-1-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate. To a mixture of tert-butyl (1R,5S)-3-(8-fluoro-7-(3-methoxy-8-((triisopropylsilyl)ethynyl)naphthalen-1-yl)-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (77.0 mg, 33.2 μmol, 1.0 eq, 36% purity) in DMF (2 mL) was added CsF (25.2 mg, 166 μmol, 6.12 μL, 5.0 eq). The mixture was stirred at 25° C. for 1 hour. After completion, the mixture was purified directly without work up. The residue was purified by reversed phase flash chromatography [water (FA, 0.10%)/acetonitrile] to give the title compound (33 mg, crude).

Step G. 4-((1R,5S)-3,8-diazabicyclo[3.2.1]octan-3-yl)-7-(8-ethynyl-3-methoxynaphthalen-1-yl)-8-fluoro-2-((tetrahydro-1H-pyrrolizin-7a(5H)-yl)methoxy)pyrido[4,3-d]pyrimidine. To a mixture of tert-butyl (1R,5S)-3-(7-(8-ethynyl-3-methoxynaphthalen-1-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (33.0 mg, 33.5 μmol, 1.0 eq) in acetonitrile (0.5 mL) was added HCl·dioxane (4 M, 1 mL, 119 eq) at 0° C. The mixture was stirred at 0° C. for 0.5 hour. After completion, the mixture was concentrated under vacuum and the pH value was adjusted to 9 with concentrate NaHCO₃ (3 mL). Then the mixture was diluted with ethyl acetate (4 mL) and water (2 mL) then separated. The aqueous phase was extracted with ethyl acetate (2×4 mL), the combined organic layer was washed with saturated brine (6 mL), dried over Na₂SO₄, filtered and concentrated under vacuum. The residue was purified by prep-HPLC (column: Shim-pack C18 150*25*10 um; mobile phase: [water (0.225% FA)-ACN]; B %: 7%-37%, 10 min) to give the title compound (8.92 mg, two steps 44% yield). Yellow solid. ¹H NMR (400 MHz, METHANOL-d4) δ=9.09 (s, 1H), 8.49 (s, 2H), 7.97 (dd, J=1.0, 8.3 Hz, 1H), 7.57 (dd, J=1.2, 7.2 Hz, 1H), 7.51 (d, J=2.6 Hz, 1H), 7.49-7.44 (m, 1H), 7.23 (d, J=2.7 Hz, 1H), 4.77 (m, 2H), 4.66 (d, J=2.2 Hz, 2H), 4.02 (br s, 2H), 3.99 (s, 3H), 3.90 (br t, J=12.8 Hz, 2H), 3.73-3.64 (m, 2H), 3.29-3.23 (m, 2H), 3.07 (s, 1H), 2.38-2.29 (m, 2H), 2.25-2.02 (m, 8H), 2.00-1.92 (m, 2H). LCMS (ESI, M/2+1, M+1): 290, 579.

Example 232

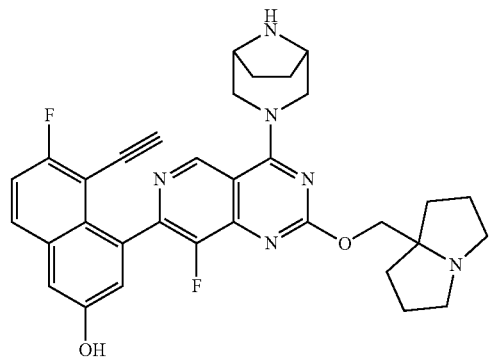 [SMILES: C#Cc1c(F)ccc2cc(O)cc(-c3ncc4c(N5CC6CCC(C5)N6)nc(OCC56CCCN5CCC6)nc4c3F)c12]

4-(4-((1R,5S)-3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)-5-ethynyl-6-fluoronaphthalen-2-ol

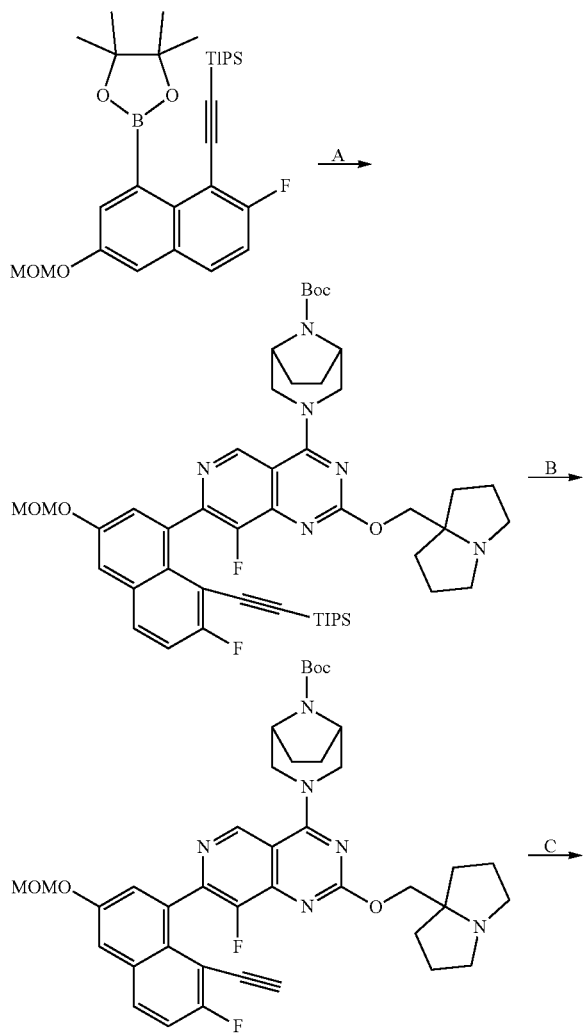

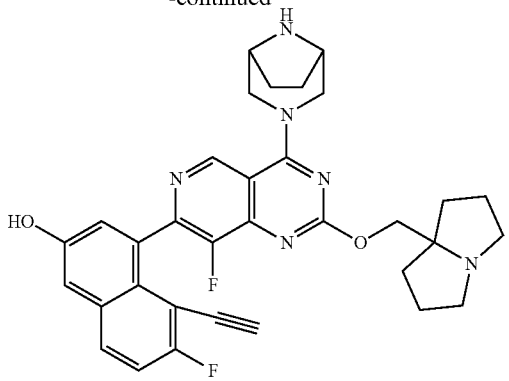

Step A. tert-butyl (1R,5S)-3-(8-fluoro-7-(7-fluoro-3-(methoxymethoxy)-8-((triisopropylsilyl)ethynyl)naphthalen-1-yl)-2-((tetrahydro-1H-pyrrolizin-7a(5H)-yl)methoxy)pyrido[4,3-d]pyrimidin-4-yl)-3,8-diazabicyclo[3.2.1]octane-8-carboxylate. A mixture of tert-butyl (1R,5S)-3-(7-chloro-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (100 mg, 188 μmol, 1.00 eq), cesium carbonate (122 mg, 375 μmol, 2.00 eq) in dioxane (3.00 mL) and water (1.00 mL) was degassed under vacuum and purged with nitrogen several times. Then Pd(dppf)Cl₂ (13.7 mg, 18.8 μmol, 0.1 eq) and ((2-fluoro-6-(methoxymethoxy)-8-(4,4,5,5-tetramethyl-1,3,2-dioxaborolan-2-yl)naphthalen-1-yl)ethynyl)triisopropylsilane (144 mg, 281 μmol, 1.50 eq) were added and purged with nitrogen several times. The reaction was stirred at 100° C. for 1 hour under nitrogen atmosphere. The reaction was filtered and concentrated in vacuum to give a residue. The residue was purified by silica gel chromatography (petroleum ether/ethyl acetate=10/1 to dichloromethane/methanol=10/1) affording the title compound (40.0 mg, 24% yield). Brown solid; LCMS [ESI, M+1]: 883.5.

Step B. tert-butyl (1R,5S)-3-(7-(8-ethynyl-7-fluoro-3-(methoxymethoxy)naphthalen-1-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate. To a solution of tert-butyl (1R,5S)-3-(8-fluoro-7-(7-fluoro-3-(methoxymethoxy)-8-((triisopropylsilyl)ethynyl)naphthalen-1-yl)-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (40.0 mg, 45.3 μmol, 1.00 eq) in DMF (0.50 mL) was added cesium fluoride (34.4 mg, 226 μmol, 8.35 μL, 5.00 eq), and the reaction was stirred at 25° C. for 1 hour. The reaction was diluted with ethyl acetate (10.0 mL), washed with brine (2×10.0 mL), dried with anhydrous sodium sulfate, filtered and concentrated in vacuum affording the title compound (20.0 mg, 61% yield). Brown oil; LCMS [ESI, M+1]: 727.3.

Step C. 4-(4-((1R,5S)-3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)-5-ethynyl-6-fluoronaphthalen-2-ol. A solution of tert-butyl (1R,5S)-3-(7-(8-ethynyl-7-fluoro-3-(methoxymethoxy)naphthalen-1-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (20.0 mg, 27.5 μmol, 1.00 eq) in acetonitrile (0.50 mL) and HCl·dioxane (0.50 mL) was stirred at 25° C. for 0.5 hour. The reaction was concentrated in vacuum at 25° C. to give a residue. Then the residue was adjusted to pH~7 with saturated sodium bicarbonate aqueous solution (0.50 mL), and the aqueous phase was extracted with DCM (2×10.0 mL). The combined organic phase was washed with brine (2×10.0 mL), dried with anhydrous sodium sulfate, filtered and concentrated in vacuum to give a residue. The residue was purified by prep-HPLC (column: Waters Xbridge C18 150*50 mm*10 um; mobile phase: [water (10 mM NH₄HCO₃)-ACN]; B %: 22%-52%, 10 min) affording the title compound (6.42 mg, 39% yield). Yellow solid; ¹H NMR (400 MHz, CDCl₃) δ=8.90 (s, 1H), 7.64 (dd, J=6.0, 9.2 Hz, 1H), 7.22-7.14 (m, 3H), 4.61 (br d, J=11.6 Hz, 1H), 4.45 (br d, J=12.0 Hz, 1H), 4.22 (s, 2H), 3.71-3.45 (m, 4H), 3.20-3.10 (m, 2H), 2.77 (s, 1H), 2.70-2.62 (m, 2H), 2.15-2.05 (m, 2H), 1.92-1.84 (m, 4H), 1.76-1.63 (m, 6H); LCMS [ESI, M+1]: 583.2.

Example 233

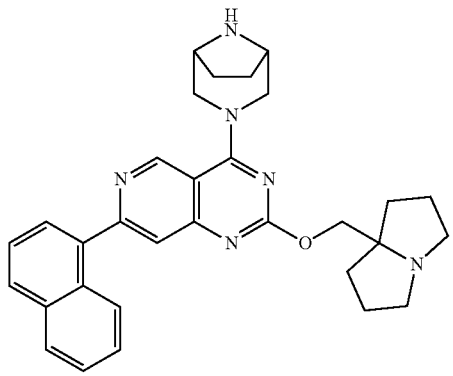 [SMILES: c1ccc2c(-c3cc4nc(OCC56CCCN5CCC6)nc(N5CC6CCC(C5)N6)c4cn3)cccc2c1]

4-((1R,5S)-3,8-diazabicyclo[3.2.1]octan-3-yl)-7-(naphthalen-1-yl)-2-((tetrahydro-1H-pyrrolizin-7a(5H)-yl)methoxy)pyrido[4,3-d]pyrimidine

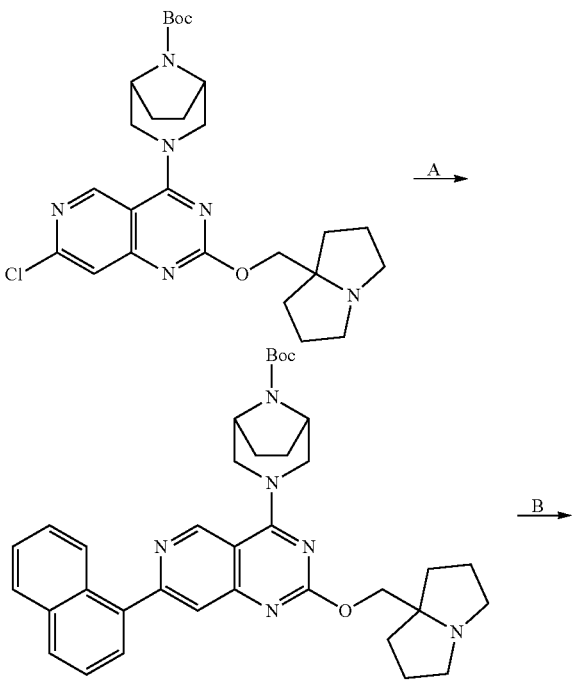

491
-continued

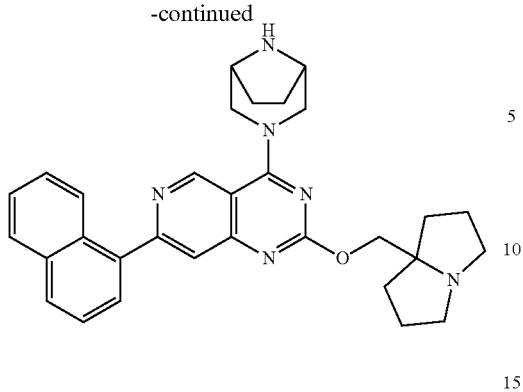

Step A. 4-((1R,5S)-3,8-diazabicyclo[3.2.1]octan-3-yl)-7-(naphthalen-1-yl)-2-((tetrahydro-1H-pyrrolizin-7a(5H)-yl)methoxy)pyrido[4,3-d]pyrimidine. To a mixture of tert-butyl (1R,5S)-3-(7-chloro-2-((tetrahydro-1H-pyrrolizin-7a(5H)-yl)methoxy)pyrido[4,3-d]pyrimidin-4-yl)-3,8-diazabicyclo [3.2.1]octane-8-carboxylate (300 mg, 524 μmol, 1.0 eq), 1-naphthylboronic acid (180 mg, 1.05 mmol, 2.0 eq) in dioxane (6 mL) and H$_2$O (2 mL) were added Cs$_2$CO$_3$ (512 mg, 1.57 mmol, 3.0 eq), Pd(PPh$_3$)$_4$ (60.6 mg, 52.4 μmol, 0.1 eq) in one portion under N$_2$. The mixture was stirred at 90° C. for 2 hours. The reaction mixture was quenched by of water (10 mL), then diluted with water (10 mL), and extracted with EtOAc (20 mL). The combined organic layers were washed with saturated sodium chloride solution (20 mL), dried over anhydrous sodium sulfate, filtered and concentrated under reduced pressure to give a residue. The residue was purified by column chromatography (SiO$_2$, DCM:MeOH=50:1-10:1) to give (1R,5S)-tert-butyl 3-(2-((hexahydro-1H-pyrrolizin-7a-yl)methoxy)-7-(naphthalen-1-yl)pyrido[4,3-d]pyrimidin-4-yl)-3,8-diazabicyclo[3.2.1] octane-8-carboxylate (0.31 g, 77% yield). Yellow solid; LCMS (ESI, M+1): 607.

Step B. 4-((1R,5S)-3,8-diazabicyclo[3.2.1]octan-3-yl)-7-(naphthalen-1-yl)-2-((tetrahydro-1H-pyrrolizin-7a(5H)-yl)methoxy)pyrido[4,3-d]pyrimidine. To a mixture of tert-butyl (1R,5S)-3-(7-(naphthalen-1-yl)-2-((tetrahydro-1H-pyrrolizin-7a(5H)-yl)methoxy)pyrido[4,3-d]pyrimidin-4-yl)-3, 8-diazabicyclo[3.2.1]octane-8-carboxylate (300 mg, 494 μmol, 1 eq) and MeCN (2 mL) was added HCl/dioxane (4 M, 1 mL, 8.09 eq) in one portion. The mixture was stirred at 25° C. for 1 hour. The residue was concentrated under reduced pressure to give a residue. The residue was purified by prep-HPLC (column: Phenomenex Synergi C18 150*25*10 um; mobile phase: [water (0.225% FA)-ACN]; B %: 15%-45%, 9 min) to give 4-((1R,5S)-3,8-diazabicyclo [3.2.1]octan-3-yl)-2-((hexahydro-1H-pyrrolizin-7a-yl)methoxy)-7-(naphthalen-1-yl)pyrido[4,3-d]pyrimidine (8.97 mg, 3.5% yield). Off-white solid; $^1$H NMR (400 MHz, DMSO-d6) δ=9.35 (s, 1H), 8.31 (s, 1H), 8.10 (s, 1H), 8.05-8.01 (m, 1H), 7.69-7.68 (m, 1H), 7.66-7.64 (m, 1H), 7.61-7.64 (m, 3H), 4.54 (d, J=12.4 Hz, 2H), 4.41 (s, 2H), 3.71-3.68 (m, 4H), 3.38-3.34 (m, 2H), 3.06-3.01 (m, 2H), 2.09-2.01 (m, 4H), 1.96-1.87 (m, 4H), 1.80-1.78 (m, 2H), 1.76-1.69 (m, 2H). LCMS (ESI, M+1): 507.

492
Example 234

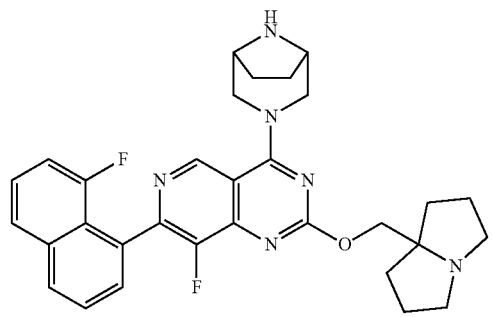 [SMILES: Fc1c(-c2cccc3cccc(F)c23)ncc2c(N3CC4CCC(C3)N4)nc(OCC34CCCN3CCC4)nc12]

4-((1R,5S)-3,8-diazabicyclo[3.2.1]octan-3-yl)-8-fluoro-7-(8-fluoronaphthalen-1-yl)-2-((tetrahydro-1H-pyrrolizin-7a(5H)-yl)methoxy)pyrido[4,3-d]pyrimidine

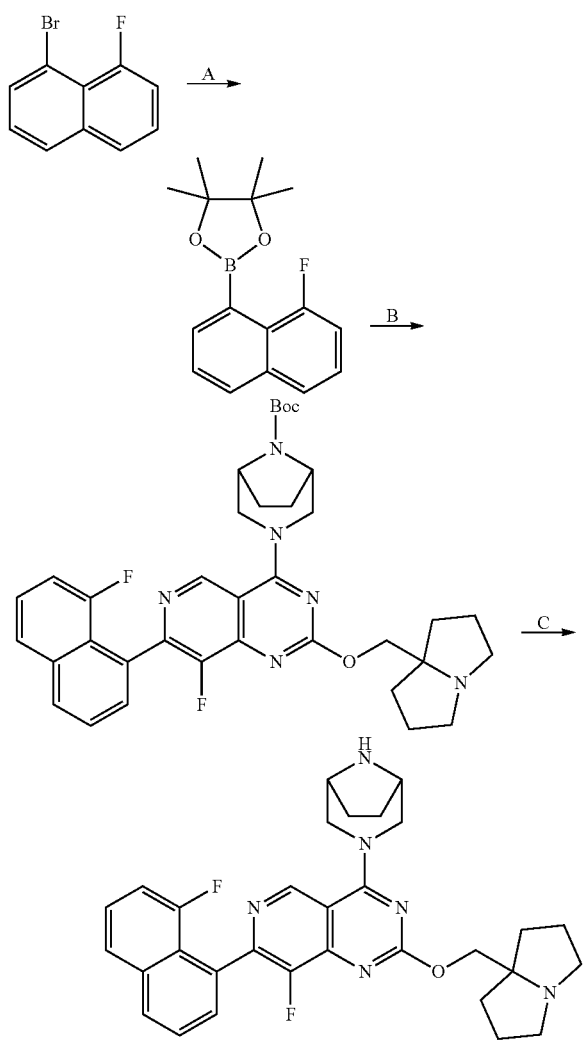

Step A. 2-(8-fluoro-1-naphthyl)-4,4,5,5-tetramethyl-1,3,2-dioxaborolane. To a mixture of 1-bromo-8-fluoronaphthalene (300 mg, 1.33 mmol, 1.0 eq), 4,4,5,5-tetramethyl-2-(4,4,5,5-tetramethyl-1,3,2-dioxaborolan-2-yl)-1,3,2-dioxaborolane (1.02 g, 4.00 mmol, 3.0 eq) and KOAc (457.88 mg, 4.67 mmol, 3.5 eq) in DMSO (6 mL) was added Pd(dppf)Cl$_2$ (48.8 mg, 66.7 μmol, 0.05 eq) under N$_2$. The mixture was stirred at 80° C. for 3 hours under N$_2$. After completion, the mixture was diluted with ethyl acetate (8 mL), washed with water (15 mL), and then separated. The aqueous phase was extracted with ethyl acetate (10 mL). The combined organic layers were washed with saturated brine (3×10 mL), dried over Na$_2$SO$_4$, filtered and concentrated under vacuum. The residue was purified by column chromatography (SiO$_2$, petroleum ether/ethyl acetate=0/1-10/1) to give 2-(8-fluoro-1-naphthyl)-4,4,5,5-tetramethyl-1,3,2-dioxaborolane (220 mg, 61% yield). Yellow solid. Rf=0.7 (5:1, petroleum ether/ethyl acetate). $^1$H NMR (400 MHz, CDCl$_3$-d) δ=7.90-7.86 (m, 1H), 7.69-7.61 (m, 2H), 7.50 (dd, J=6.8, 8.0 Hz, 1H), 7.43-7.35 (m, 1H), 7.16 (ddd, J=0.8, 7.6, 11.2 Hz, 1H), 1.46 (s, 12H).

Step B. tert-butyl (1R,5S)-3-(8-fluoro-7-(8-fluoronaphthalen-1-yl)-2-((tetrahydro-1H-pyrrolizin-7a(5H)-yl)methoxy)pyrido[4,3-d]pyrimidin-4-yl)-3,8-diazabicyclo[3.2.1]octane-8-carboxylate. To a mixture of tert-butyl (1R,5S)-3-(7-chloro-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (120 mg, 225 μmol, 1.0 eq), 2-(8-fluoro-1-naphthyl)-4,4,5,5-tetramethyl-1,3,2-dioxaborolane (79.6 mg, 293 μmol, 1.3 eq) and Cs$_2$CO$_3$ (220 mg, 675 μmol, 3.0 eq) in dioxane (3 mL) and H$_2$O (1 mL) was added Pd(dppf)Cl$_2$ (16.47 mg, 22.51 μmol, 0.10 eq) under N$_2$. The mixture was stirred at 90° C. for 5 hours. After completion, the mixture was diluted with ethyl acetate (8 mL) and water (8 mL), and then separated. The aqueous phase was extracted with ethyl acetate (2×8 mL), the combined organic layer was washed with saturated brine (10 mL), dried over Na$_2$SO$_4$, filtered and concentrated under vacuum. The residue was purified by reversed phase flash chromatography [water (FA, 0.1%)/acetonitrile] to give tert-butyl tert-butyl (1R,5S)-3-(8-fluoro-7-(8-fluoronaphthalen-1-yl)-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (33 mg, 22% yield). Yellow solid. $^1$H NMR (400 MHz, CDCl$_3$-d) δ=9.02 (s, 1H), 8.02-7.97 (m, 1H), 7.74 (d, J=8.0 Hz, 1H), 7.65-7.57 (m, 2H), 7.49-7.41 (m, 1H), 7.15-7.08 (m, 1H), 4.70-4.52 (m, 2H), 4.39 (br s, 2H), 4.22 (s, 2H), 3.78-3.58 (m, 2H), 3.19-3.10 (m, 2H), 2.65 (td, J=6.8, 10.0 Hz, 2H), 2.14-2.07 (m, 2H), 2.0-1.94 (m, 2H), 1.91-1.86 (m, 4H), 1.82-1.76 (m, 2H), 1.72-1.66 (m, 2H), 1.53 (s, 9H). LCMS [ESI, M+1]: 643.

Step C. 4-((1R,5S)-3,8-diazabicyclo[3.2.1]octan-3-yl)-8-fluoro-7-(8-fluoronaphthalen-1-yl)-2-((tetrahydro-1H-pyrrolizin-7a(5H)-yl)methoxy)pyrido[4,3-d]pyrimidine. To a mixture of tert-butyl (1R,5S)-3-(8-fluoro-7-(8-fluoronaphthalen-1-yl)-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (45 mg, 70.0 μmol, 1.0 eq) in acetonitrile (0.5 mL) was added HCl·dioxane (4 M, 1 mL, 57 eq) at 0° C. The mixture was stirred at 0° C. for 0.5 hour. After completion, the mixture was concentrated under vacuum. Then the pH value was adjusted to 9 with saturated Na$_2$CO$_3$ solution and the mixture was extracted with EtOAc (2×8 mL). The organic layers were dried and concentrated under vacuum. The residue was purified by prep-HPLC (column: Waters Xbridge 150*25 mm*Sum; mobile phase: [water (10 mM NH$_4$HCO$_3$)-ACN]; B %: 18%-48%, 10 min) to give 4-((1R,5S)-3,8-diazabicyclo[3.2.1]octan-3-yl)-8-fluoro-7-(8-fluoronaphthalen-1-yl)-2-((tetrahydro-1H-pyr-rolizin-7a(5H)-yl)methoxy)pyrido[4,3-d]pyrimidine (18.69 mg, 49% yield). White solid. $^1$H NMR (400 MHz, CDCl$_3$-d) δ=9.02 (s, 1H), 7.98 (td, J=1.6, 7.6 Hz, 1H), 7.76-7.71 (m, 1H), 7.64-7.56 (m, 2H), 7.48-7.41 (m, 1H), 7.11 (ddd, J=0.8, 7.6, 12.4 Hz, 1H), 4.65 (br d, J=12.4 Hz, 1H), 4.54 (br d, J=11.6 Hz, 1H), 4.19 (s, 2H), 3.67 (br s, 3H), 3.59 (br d, J=12.4 Hz, 1H), 3.15-3.07 (m, 2H), 2.64 (td, J=6.8, 10.0 Hz, 2H), 2.14-2.06 (m, 2H), 1.92-1.82 (m, 8H), 1.70-1.64 (m, 2H). LCMS [ESI, M+1, M/2+1]: 543, 272.

Example 235

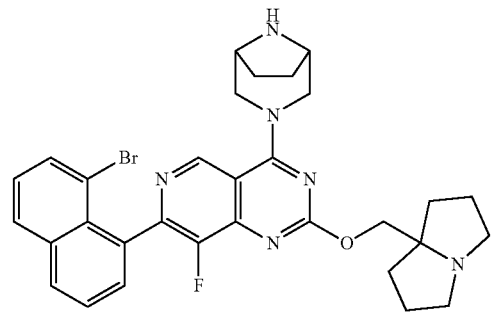 [SMILES: Fc1c(-c2cccc3cccc(Br)c23)ncc2c(N3CC4CCC(C3)N4)nc(OCC34CCCN3CCC4)nc12]

4-((1R,5S)-3,8-diazabicyclo[3.2.1]octan-3-yl)-7-(8-bromonaphthalen-1-yl)-8-fluoro-2-((tetrahydro-1H-pyrrolizin-7a(5H)-yl)methoxy)pyrido[4,3-d]pyrimidine

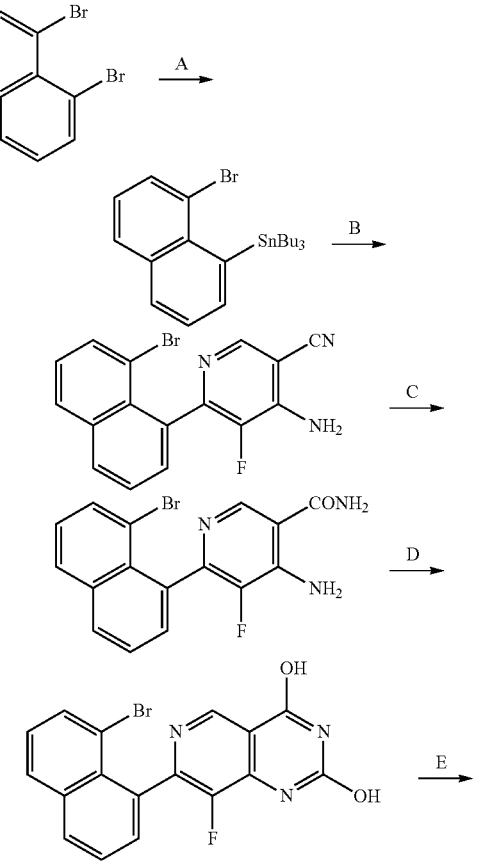

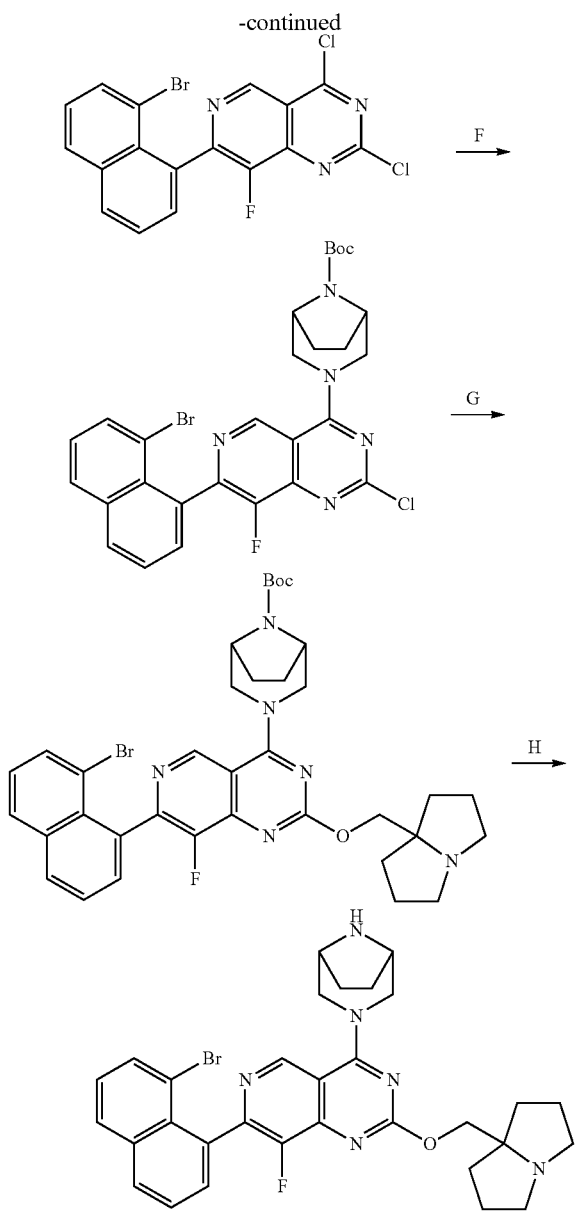

Step A. (8-bromonaphthalen-1-yl)tributylstannane. A solution of 1,8-dibromonaphthalene (12 g, 41.9 mmol, 1.0 eq) in THF (550 mL) was added n-Buli (2.5 M, 16.8 mL, 1.0 eq) dropwise at −70° C. for 40 minutes and then tributyl (chloro)stannane (13.7 g, 41.9 mmol, 11.3 mL, 1.0 eq) was added to the mixture. The mixture was stirred at −50° C. for 1 hour and warmed up to 20° C. for 12 hours. The reaction mixture was diluted with water (500 mL) and extracted with ethyl acetate (3×500 mL). The combined organic layers were washed with brine (500 mL), dried over Na$_2$SO$_4$, filtered and concentrated under reduced pressure to give a residue. The residue was purified by reversed phase flash chromatography [water (0.1% formic acid)/acetonitrile)] to give (8-bromonaphthalen-1-yl)tributylstannane (14 g, 67% yield) as yellow oil. $^1$H NMR (400 MHz, chloroform-d) δ=7.89-7.78 (m, 4H), 7.49-7.42 (m, 1H), 7.29 (t, J=7.6 Hz, 1H), 1.64-1.50 (m, 6H), 1.42-1.19 (m, 12H), 0.89 (t, J=7.2 Hz, 9H).

Step B. 4-amino-6-(8-bromonaphthalen-1-yl)-5-fluoronicotinonitrile. A mixture of (8-bromonaphthalen-1-yl)tributylstannane (2.0 g, 4.03 mmol, 1.0 eq), 4-amino-6-chloro-5-fluoronicotinonitrile (synthesized according to Intermediate 10, 1.18 g, 6.85 mmol, 1.7 eq), CuI (230 mg, 1.21 mmol, 0.3 eq), BINAP (502 mg, 806 μmol, 0.2 eq) and Pd(dppf)Cl$_2$ (294 mg, 403 μmol, 0.1 eq) in toluene (20 mL) was degassed and purged with N$_2$ for 3 times, and then the mixture was stirred at 100° C. for 12 hours under N$_2$ atmosphere. The reaction mixture was diluted with water (50 mL) and extracted with ethyl acetate (3×50 mL). The combined organic layers were washed with brine (50 mL), dried over Na$_2$SO$_4$, filtered and concentrated under reduced pressure to give a residue. The residue was purified by column chromatography (SiO$_2$, petroleum ether/ethyl acetate=20/1 to 3/1) and further purified by reversed phase flash chromatography [water (0.1% formic acid)/acetonitrile)] to give 4-amino-6-(8-bromonaphthalen-1-yl)-5-fluoronicotinonitrile (1 g, 23% yield). Yellow solid; $^1$H NMR (400 MHz, chloroform-d) δ=8.42 (s, 1H), 8.00 (dd, J=1.2, 8.0 Hz, 1H), 7.92 (d, J=8.0 Hz, 1H), 7.83 (dd, J=0.8, 7.6 Hz, 1H), 7.63-7.52 (m, 2H), 7.36 (t, J=8.0 Hz, 1H), 5.07 (br s, 2H). LCMS [ESI, M+1]: 344.

Step C. 4-amino-6-(8-bromonaphthalen-1-yl)-5-fluoronicotinamide. A solution of 4-amino-6-(8-bromonaphthalen-1-yl)-5-fluoronicotinonitrile (500 mg, 1.46 mmol, 1.0 eq) in H2SO$_4$ (4.60 g, 46.9 mmol, 2.50 mL, 32.1 eq) was stirred at 30° C. for 1 hour. After completion of the reaction, the reaction mixture was poured into ice-cold water (10 mL). The mixture was adjusted to pH~8 with saturated Na$_2$CO$_3$ aqueous solution and extracted with ethyl acetate (3×20 mL). The combined organic layers were washed with brine (20 mL), dried over Na$_2$SO$_4$, filtered and concentrated under reduced pressure to give 4-amino-6-(8-bromonaphthalen-1-yl)-5-fluoronicotinamide (400 mg, 76% yield) as a yellow solid and used to next step without purification. LCMS [ESI, M+1]: 362.

Step D. 7-(8-bromonaphthalen-1-yl)-8-fluoropyrido[4,3-d]pyrimidine-2,4-diol. To a solution of 4-amino-6-(8-bromonaphthalen-1-yl)-5-fluoronicotinamide (400 mg, 1.11 mmol, 1.0 eq) in DMF (8 mL) was added NaH (88.8 mg, 2.22 mmol, 60% purity, 2.0 eq) at 0° C. The reaction mixture was stirred at 0° C. for 1 hour. To the mixture was added CDI (270 mg, 1.67 mmol, 1.5 eq). The reaction mixture was stirred at 75° C. for 2 hours. The reaction mixture was poured into ice water (20 mL) and acidified by HCl (2 M) to pH~5. The mixture was filtered and the filter cake was washed with water (3×10 mL). 7-(8-bromonaphthalen-1-yl)-8-fluoropyrido[4,3-d]pyrimidine-2,4-diol (300 mg, 70% yield) was obtained as a yellow solid and used to next step without purification. LCMS [ESI, M+1]: 388.

Step E. 7-(8-bromonaphthalen-1-yl)-2,4-dichloro-8-fluoropyrido[4,3-d]pyrimidine. To a solution of 7-(8-bromonaphthalen-1-yl)-8-fluoropyrido[4,3-d]pyrimidine-2,4-diol (250 mg, 647 μmol, 1.0 eq) in POCl$_3$ (4.12 g, 26.9 mmol, 2.50 mL, 41.5 eq) was added DIEA (418 mg, 3.24 mmol, 563 μL, 5.0 eq) and the mixture was stirred at 110° C. for 1 hour. The mixture was concentrated under vacuum to give 7-(8-bromonaphthalen-1-yl)-2,4-dichloro-8-fluoropyrido[4,3-d]pyrimidine (270 mg, crude) as a brown oil and used to next step without purification. LCMS [ESI, M+1]: 424.

Step F. (1R,5S)-tert-butyl 3-(7-(8-bromonaphthalen-1-yl)-2-chloro-8-fluoropyrido[4,3-d]pyrimidin-4-yl)-3,8-diazabicyclo[3.2.1]octane-8-carboxylate. To a solution of 7-(8-bromonaphthalen-1-yl)-2,4-dichloro-8-fluoropyrido[4,3-d]pyrimidine (270 mg, 638 μmol, 1.0 eq) in dichloromethane (5 mL) was added DIEA (824 mg, 6.38 mmol, 1.11 mL, 10.0 eq) and tert-butyl 3,8-diazabicyclo[3.2.1]octane-8-carboxylate (203 mg, 957 μmol, 1.5 eq). The mixture was stirred at −40° C. for 0.5 hour. The reaction mixture was diluted with water (20 mL) and extracted with dichloromethane (3×30 mL). The combined organic layers were washed with brine (20 mL), dried over Na$_2$SO$_4$, filtered and concentrated under reduced pressure to give a residue. The residue was purified by column chromatography (SiO$_2$, petroleum ether/ethyl acetate=10/1 to 3/1) to give the title compound (290 mg, 73% yield) as a yellow solid. $^1$H NMR (400 MHz, chloroform-d) δ=9.13 (s, 1H), 8.06-7.98 (m, 1H), 7.96-7.91 (m, 1H), 7.81 (dd, J=1.2, 7.6 Hz, 1H), 7.65-7.56 (m, 2H), 7.36 (t, J=8.0 Hz, 1H), 4.77-4.30 (m, 4H), 3.76 (br s, 2H), 2.04-1.92 (m, 2H), 1.88-1.69 (m, 2H), 1.56-1.47 (m, 9H). LCMS [ESI, M+1]: 600.

Step G. tert-butyl (1R,5S)-3-(7-(8-bromonaphthalen-1-yl)-8-fluoro-2-((tetrahydro-1H-pyrrolizin-7a(5H)-yl)methoxy)pyrido[4,3-d]pyrimidin-4-yl)-3,8-diazabicyclo [3.2.1]octane-8-carboxylate. To a solution of (1R,5S)-tert-butyl 3-(7-(8-bromonaphthalen-1-yl)-2-chloro-8-fluoropyrido[4,3-d] pyrimidin-4-yl)-3,8-diazabicyclo[3.2.1] octane-8-carboxylate (200 mg, 333 μmol, 1.0 eq) in dioxane (5 mL) were added DIEA (129 mg, 1.0 mmol, 174 μL, 3.0 eq) and tert-butyl (1R,5S)-3-(7-chloro-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (94.3 mg, 667 μmol, 2.0 eq). The mixture was stirred at 90° C. for 12 hours. The reaction mixture was diluted with water (10 mL) and extracted with ethyl acetate (3×10 mL). The combined organic layers were washed with brine (10 mL), dried over Na$_2$SO$_4$, filtered and concentrated under reduced pressure to give a residue. The residue was purified by reversed phase flash chromatography [water (0.1% formic acid)/acetonitrile)] to give the title compound (130 mg, 54% yield) as a yellow solid. LCMS [ESI, M+1]: 705.

Step H. 4-((1R,5S)-3,8-diazabicyclo[3.2.1]octan-3-yl)-7-(8-bromonaphthalen-1-yl)-8-fluoro-2-((tetrahydro-1H-pyrrolizin-7a(5H)-yl)methoxy)pyrido[4,3-d]pyrimidine. To a solution of (tert-butyl (1R,5S)-3-(7-(8-bromonaphthalen-1-yl)-8-fluoro-2-((tetrahydro-1H-pyrrolizin-7a(5H)-yl)methoxy)pyrido[4,3-d]pyrimidin-4-yl)-3,8-diazabicyclo [3.2.1]octane-8-carboxylate (40 mg, 56.8 μmol, 1.0 eq) in ACN (0.5 mL) was added HCl·dioxane (4 M, 284 μL, 1.0 eq). The mixture was stirred at 30° C. for 1 hour. The reaction mixture was concentrated under vacuum and diluted with water (2 mL). The mixture was adjusted to pH~8 with saturated NaHCO$_3$ aqueous solution and extracted with ethyl acetate (3×10 mL). The combined organic layers were washed with brine (10 mL), dried over Na$_2$SO$_4$, filtered and concentrated under reduced pressure to give the residue. The residue was purified by prep-HPLC (column: Waters Xbridge 150*25 mm*5um; mobile phase: [water (10 mM NH$_4$HCO$_3$)-ACN]; B %: 20%-50%, 10 min). The desired fraction was collected and lyophilized to give the title compound (10 mg, 29% yield) as a white solid. $^1$H NMR (400 MHz, methanol-d4) δ=9.07 (s, 1H), 8.14 (dd, J=1.2, 8.0 Hz, 1H), 8.06 (dd, J=1.0, 8.0 Hz, 1H), 7.85 (dd, J=1.2, 7.6 Hz, 1H), 7.72-7.60 (m, 2H), 7.43 (t, J=7.6 Hz, 1H), 4.64 (dd, J=5.2, 12.0 Hz, 2H), 4.38 (s, 2H), 3.80-3.61 (m, 4H), 3.29-3.21 (m, 2H), 2.98-2.79 (m, 2H), 2.21-2.10 (m, 2H), 2.07-1.72 (m, 10H). LCMS [ESI, M+1]: 605.

Example 236

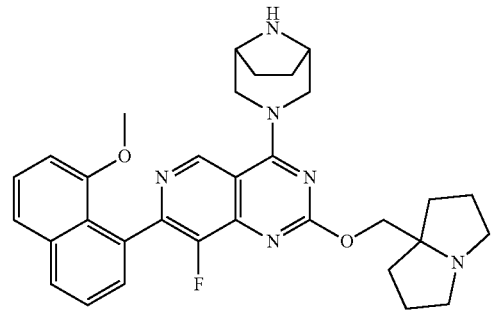 [SMILES: COc1cccc2cccc(-c3ncc4c(N5CC6CCC(C5)N6)nc(OCC56CCCN5CCC6)nc4c3F)c12]

4-((1R,5S)-3,8-diazabicyclo[3.2.1]octan-3-yl)-8-fluoro-2-((hexahydro-1H-pyrrolizin-7a-yl)methoxy)-7-(8-methoxynaphthalen-1-yl)pyrido[4,3-d]pyrimidine

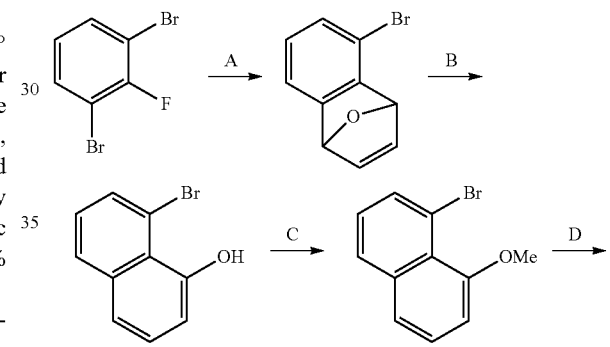

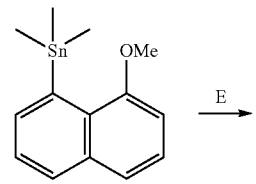

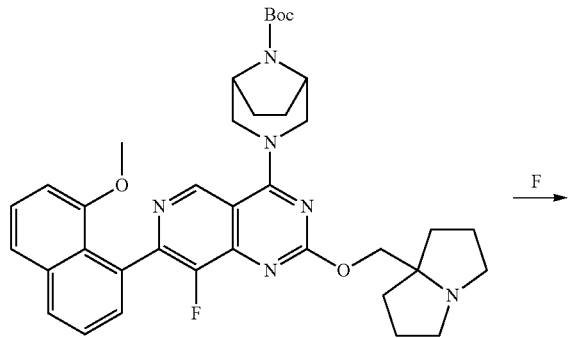

-continued

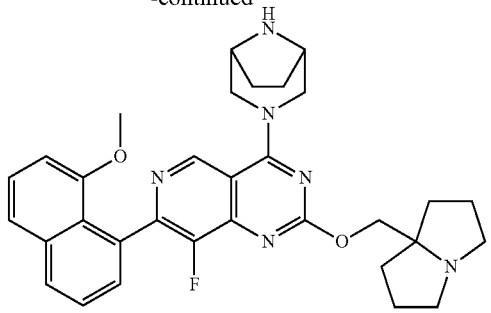

Step A. 5-bromo-1,4-dihydro-1,4-epoxynaphthalene. To a mixture of 1,3-dibromo-2-fluorobenzene (5.0 g, 19.7 mmol, 1.0 eq) and furan (2.68 g, 39.4 mmol, 2.86 mL, 2.0 eq) in toluene (70 mL) was added n-BuLi (2.5 M in hexane, 9.45 mL, 1.2 eq) in one portion at −20° C. under $N_2$. The mixture was stirred at −20° C. for 30 minutes, then warmed up to 25° C. and stirred for 15.5 hours. Upon completion, the reaction mixture was quenched by water (100 mL). The reaction mixture was filtered and the solution was separated. The aqueous layer was extracted with ethyl acetate (3×100 mL). The combined organic layers were dried over $Na_2SO_4$, filtered and concentrated under vacuum. The residue was purified by reversed phase flash chromatography [C18, 0.1% FA in water, 0-65% MeCN] to give 5-bromo-1,4-dihydro-1,4-epoxynaphthalene (2.1 g, 47% yield); Yellow oil; $^1$H NMR (400 MHz, $CDCl_3$-d) δ=7.17 (d, J=7.2 Hz, 1H), 7.12-7.06 (m, 3H), 6.86 (dd, J=7.2, 8.0 Hz, 1H), 5.65-5.55 (m, 2H).

Step B. 8-bromonaphthalen-1-ol. To a solution of 5-bromo-1,4-dihydro-1,4-epoxynaphthalene (2.10 g, 1.0 eq) in EtOH (50.0 mL) was added HCl (5.15 g, 141 mmol, 11.7 mL, 30% purity, 15.0 eq) in one portion at 25° C. under $N_2$. The mixture was stirred at 78° C. for 2 hours. Upon completion, the reaction mixture was concentrated under vacuum. The residue was purified by reversed phase flash chromatography [C18, 0.1% FA in water, 0-80% MeCN] to give 8-bromonaphthalen-1-ol (1.8 g, 88% yield). Red oil; $^1$H NMR (400 MHz, $CDCl_3$-d) δ=7.98 (s, 1H), 7.70 (dd, J=0.8, 8.4 Hz, 1H), 7.55 (dd, J=1.2, 7.6 Hz, 1H), 7.38-7.30 (m, 2H), 7.15 (dd, J=8.0, 15.6 Hz, 1H), 7.00 (dd, J=1.6, 7.2 Hz, 1H)

Step C. 1-bromo-8-methoxy-naphthalene. To a mixture of 8-bromonaphthalen-1-ol (2.90 g, 1.0 eq) in $CH_3CN$ (30 mL) were added $K_2CO_3$ (5.39 g, 3.0 eq) and MeI (18.5 g, 10.0 eq) in one portion at 25° C. under $N_2$. The mixture was stirred at 25° C. for 3 hours. The reaction mixture was diluted with $H_2O$ (30 mL) and extracted with ethyl acetate (3×30 mL). The combined organic layers were washed with brine (80 mL), dried over $Na_2SO_4$, filtered and concentrated under reduced pressure to give a residue. The residue was purified by reversed phase flash chromatography [C18, 0.1% FA in water, 0-78% MeCN] to give 1-bromo-8-methoxy-naphthalene (2.86 g, 93%). White solid; $^1$H NMR (400 MHz, $CDCl_3$-d) δ=7.80-7.72 (m, 2H), 7.48-7.38 (m, 2H), 7.26-7.21 (m, 1H), 6.94 (dd, J=1.6, 7.2 Hz, 1H), 3.98 (s, 3H).

Step D. (8-methoxy-1-naphthyl)-trimethyl-stannane. To a mixture of 1-bromo-8-methoxy-naphthalene (2.56 g, 1.0 eq) and trimethyl(trimethylstannyl)stannane (10.6 g, 32.4 mmol, 6.72 mL, 3.0 eq) in toluene (30 mL) was added $Pd(PPh_3)_4$ (1.25 g, 1.08 mmol, 0.1 eq) in one portion at 25° C. under $N_2$. The reaction mixture was stirred at 110° C. for 16 hours. The reaction mixture was diluted with $H_2O$ (30 mL) and extracted with ethyl acetate (3×30 mL). The combined organic layers were washed with brine (80 mL), dried over $Na_2SO_4$, filtered and concentrated under reduced pressure to give a residue. The residue was purified by column chromatography ($SiO_2$, petroleum ether/ethyl acetate=1/0 to 100/1) to give (8-methoxy-1-naphthyl)-trimethyl-stannane (12.6 g, 73% yield). White solid; $^1$H NMR (400 MHz, $CDCl_3$-d) δ 7.82 (dd, J=1.2, 8.0 Hz, 1H), 7.70 (dd, J=1.2, 6.8 Hz, 1H), 7.51-7.43 (m, 2H), 7.41-7.36 (m, 1H), 6.84 (d, J=7.6 Hz, 1H), 3.97 (s, 3H), 0.31 (s, 9H).

Step E. tert-butyl (1R,5S)-3-(8-fluoro-7-(8-methoxynaphthalen-1-yl)-2-((tetrahydro-1H-pyrrolizin-7a(5H)-yl)methoxy)pyrido[4,3-d]pyrimidin-4-yl)-3,8-diazabicyclo[3.2.1]octane-8-carboxylate. To a solution of tert-butyl (1R,5S)-3-(7-chloro-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (100 mg, 1.0 eq) and (8-methoxy-1-naphthyl)-trimethyl-stannane (150 mg, 2.5 eq) in dioxane (20.0 mL) and toluene (8 mL) were added $Pd(dppf)Cl_2$ (13.7 mg, 18.8 μmol, 0.1 eq) and BINAP (23.4 mg, 37.5 μmol, 0.2 eq) and CuI (10.7 mg, 56.3 μmol, 0.3 eq) in one portion at 25° C. under $N_2$. The mixture was stirred at 90° C. for 12 hours under $N_2$. Upon completion, the reaction mixture was diluted with $H_2O$ (20 mL) and extracted with ethyl acetate (3×30 mL). The combined organic layers were washed with brine (80 mL), dried over $Na_2SO_4$, filtered and concentrated under reduced pressure to give a residue. The residue was purified by reversed phase flash chromatography [C18, 0.1% FA in water, 0-60% MeCN] to give tert-butyl (1R,5S)-3-(8-fluoro-7-(8-methoxynaphthalen-1-yl)-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (40.0 mg, 29% yield). Yellow oil; $^1$H NMR (400 MHz, $CDCl_3$-d) δ=8.97 (s, 1H), 7.88 (d, J=8.0 Hz, 1H), 7.53-7.46 (m, 2H), 7.41-7.35 (m, 2H), 6.77 (d, J=7.6 Hz, 1H), 4.59 (br t, J=10.4 Hz, 2H), 4.36 (br s, 2H), 4.25 (s, 2H), 3.66 (br s, 2H), 3.46 (s, 3H), 3.20-3.10 (m, 2H), 2.70-2.55 (m, 2H), 2.15-2.04 (m, 2H), 1.90-1.83 (m, 5H), 1.76-1.65 (m, 5H), 1.48-1.46 (m, 9H). LCMS [ESI, M+1]: 655.

Step F. 4-((1R,5S)-3,8-diazabicyclo[3.2.1]octan-3-yl)-8-fluoro-7-(8-methoxynaphthalen-1-yl)-2-((tetrahydro-1H-pyrrolizin-7a(5H)-yl)methoxy)pyrido[4,3-d]pyrimidine. To a solution of tert-butyl (1R,5S)-3-(8-fluoro-7-(8-methoxynaphthalen-1-yl)-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (45 mg, 68.7 μmol, 1.0 eq) in ACN (0.5 mL) was added HCl·dioxane (4 M, 0.5 mL,) in one portion at 0° C. under $N_2$. The mixture was stirred at 0° C. for 1 hour. Upon completion, the reaction mixture was diluted with $H_2O$ (10 mL), basified and extracted with ethyl acetate (3×10 mL). The combined organic layers were washed with brine (20 mL), dried over $Na_2SO_4$, filtered and concentrated under reduced pressure to give a residue. The residue was purified by prep-HPLC (Waters Xbridge 150*25 mm*5um; mobile phase: [water (10 mM $NH_4HCO_3$)-ACN]; B %: 22%-52%, 10 min) and then lyophilized affording 4-((1R,5S)-3,8-diazabicyclo[3.2.1]octan-3-yl)-8-fluoro-7-(8-methoxynaphthalen-1-yl)-2-((tetrahydro-1H-pyrrolizin-7a(5H)-yl)methoxy)pyrido[4,3-d]pyrimidine (13.9 mg, 35% yield). White solid; $^1$H NMR (400 MHz, $CDCl_3$-d) δ=9.00 (s, 1H), 7.92 (d, J=8.0 Hz, 1H), 7.60-7.50 (m, 2H), 7.45-7.38 (m, 2H), 6.81 (d, J=7.6 Hz, 1H), 4.75 (s, 1H), 4.65-4.55 (m, 2H), 4.20 (s, 2H), 3.70-3.60 (m, 4H), 3.52 (s, 3H), 3.13-3.06 (m, 2H), 2.70-2.60 (m, 2H), 2.15-2.05 (m, 2H), 1.90-1.76 (m, 10H). LCMS [ESI, M+1]:555.

Example 237

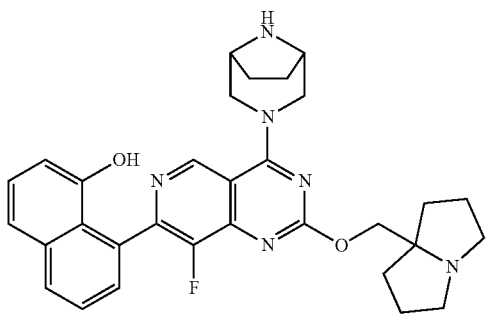

8-(4-((1R,5S)-3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)naphthalen-1-ol

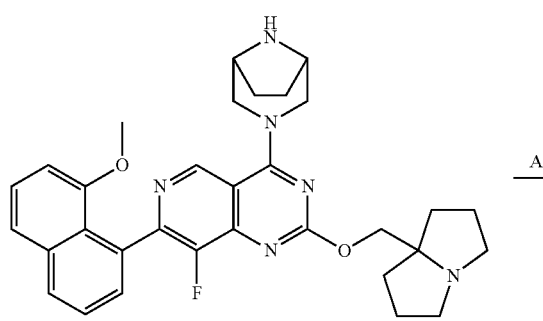


Step A. 8-(4-((1R,5S)-3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)naphthalen-1-ol. To a solution of 4-((1R,5S)-3,8-diazabicyclo[3.2.1]octan-3-yl)-8-fluoro-7-(8-methoxynaphthalen-1-yl)-2-((tetrahydro-1H-pyrrolizin-7a(5H)-yl)methoxy)pyrido[4,3-d]pyrimidine (40.0 mg, 61.1 μmol, 1.0 eq) in DCM (0.5 mL) was added BBr₃ (115 mg, 458 μmol, 7.5 eq) in one portion at 0° C. under N₂. The mixture was stirred at 0° C. for 0.5 hour. The reaction mixture was diluted with H₂O (5 mL) and ACN (1 mL). The solution was purified by prep-HPLC(column: Phenomenex Synergi C18 150*25*10 um; mobile phase: [water (0.225% FA)-ACN]; B %: 10%-40%, 10 min. The desired fraction was collected and lyophilized to affording 8-(4-((1R,5S)-3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)naphthalen-1-ol (4.89 mg, 14% yield). Yellow solid; ¹H NMR (400 MHz, CDCl₃-d) δ=9.06 (s, 1H), 8.44 (br s, 2H), 8.02-7.93 (m, 1H), 7.56 (dd, J=7.2, 8.0 Hz, 1H), 7.52-7.45 (m, 1H), 7.38-7.28 (m, 2H), 6.81 (dd, J=1.2, 7.6 Hz, 1H), 4.75-4.71 (m, 2H), 4.61-4.52 (m, 2H), 3.94 (br s, 2H), 3.84 (br d, J=13.2 Hz, 2H), 3.70-3.60 (m, 2H), 3.27-3.22 (m, 2H), 2.35-2.06 (m, 8H), 2.05-1.86 (m, 4H). LCMS [ESI, M+1]: 541.

Example 238

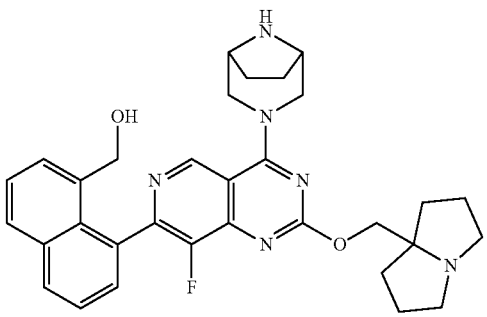 [SMILES: OCc1cccc2cccc(-c3ncc4c(N5CC6CCC(C5)N6)nc(OCC56CCCN5CCC6)nc4c3F)c12]

(8-(4-((1R,5S)-3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)naphthalen-1-yl)methanol

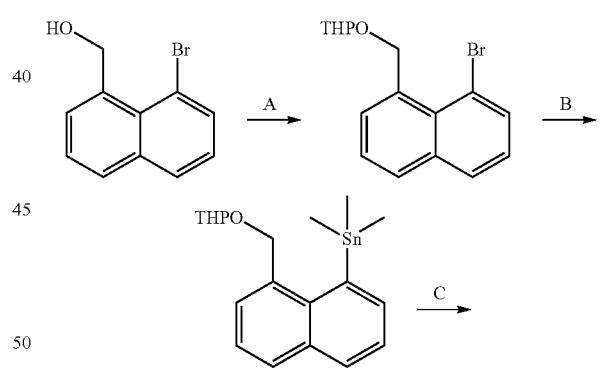

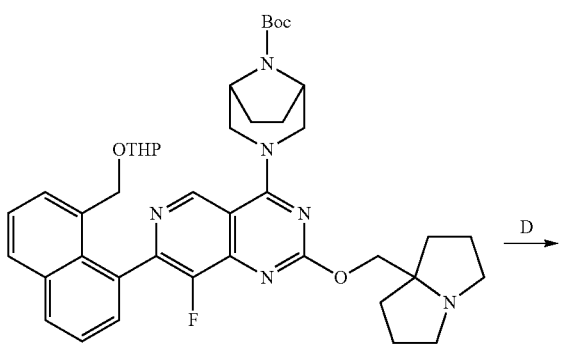

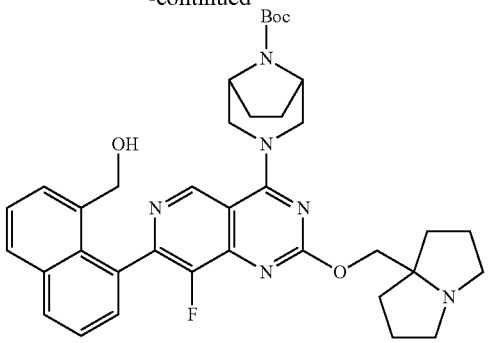

Step A. 2-[(8-bromo-1-naphthyl)methoxy]tetrahydropyran. To a solution of (8-bromo-1-naphthyl)methanol (2.1 g, 8.86 mmol, 1.0 eq) in dichloromethane (42 mL) was added TsOH·H$_2$O (168 mg, 886 µmol, 0.1 eq) and DHP (1.49 g, 17.7 mmol, 1.62 mL, 2.0 eq). The mixture was stirred at 25° C. for 2 hours, and the mixture was concentrated under vacuum. The residue was purified by silica gel chromatography (petroleum ether/ethyl acetate 10/1 to 3/1) to give 2-[(8-bromo-1-naphthyl)methoxy]tetrahydropyran (2.7 g, 95% yield). Colourless oil; Rf=0.80 (petroleum ether/ethyl acetate 10/1).

Step B. trimethyl-[8-(tetrahydropyran-2-yloxymethyl)-1-naphthyl]stannane. To a solution of 2-[(8-bromo-1-naphthyl)methoxy]tetrahydropyran (700 mg, 2.18 mmol, 1.0 eq) in toluene (14 mL) were added Pd(PPh$_3$)$_4$ (252 mg, 218 µmol, 0.1 eq) and trimethyl(trimethylstannyl)stannane (2.86 g, 8.72 mmol, 1.81 mL, 4.0 eq). The mixture was stirred at 110° C. for 12 hours under N$_2$. The reaction mixture was diluted with water (20 mL) and extracted with ethyl acetate (3×20 mL). The combined organic layers were washed with brine (20 mL), dried over Na$_2$SO$_4$, filtered and concentrated under reduced pressure. The residue was purified by reversed phase flash chromatography [water (0.1% formic acid)/acetonitrile] to give trimethyl-[8-(tetrahydropyran-2-yloxymethyl)-1-naphthyl]stannane (500 mg, 56% yield). Yellow oil; $^1$H NMR (400 MHz, chloroform-d) δ=7.90-7.72 (m, 4H), 7.53-7.38 (m, 2H), 5.47 (br d, J=13.2 Hz, 1H), 5.13 (d, J=9.2 Hz, 1H), 4.85-4.77 (m, 1H), 3.99-3.90 (m, 1H), 3.65-3.54 (m, 1H), 2.04-1.91 (m, 1H), 1.87-1.76 (m, 2H), 1.71-1.59 (m, 3H), 0.58-0.36 (m, 9H).

Step C. tert-butyl (1R,5S)-3-(8-fluoro-2-((tetrahydro-1H-pyrrolizin-7a(5H)-yl)methoxy)-7-(8-(((tetrahydro-2H-pyran-2-yl)oxy)methyl)naphthalen-1-yl)pyrido[4,3-d]pyrimidin-4-yl)-3,8-diazabicyclo[3.2.1]octane-8-carboxylate. A mixture of tert-butyl (1R,5S)-3-(7-chloro-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (270 mg, 506 µmol, 1.0 eq), trimethyl-[8-(tetrahydropyran-2-yloxymethyl)-1-naphthyl]stannane (410 mg, 1.01 mmol, 2.0 eq), BINAP (63.1 mg, 101 µmol, 0.2 eq), CuI (28.9 mg, 152 µmol, 0.3 eq) and Pd(dppf)Cl$_2$ (37.1 mg, 50.6 µmol, 0.1 eq) in toluene (6.0 mL) was degassed and purged with N$_2$ for 3 times, and then the mixture was stirred at 100° C. for 16 hrs under N$_2$ atmosphere. The reaction mixture was diluted with water (15 mL) and extracted with ethyl acetate (3×20 mL). The combined organic layers were washed with brine (15 mL), dried over Na$_2$SO$_4$, filtered and concentrated under reduced pressure. The residue was purified by reversed phase flash chromatography [water (0.1% formic acid)/acetonitrile] to tert-butyl (1R,5S)-3-(8-fluoro-2-((tetrahydro-1H-pyrrolizin-7a(5H)-yl)methoxy)-7-(8-(((tetrahydro-2H-pyran-2-yl)oxy)methyl)naphthalen-1-yl)pyrido[4,3-d]pyrimidin-4-yl)-3,8-diazabicyclo[3.2.1]octane-8-carboxylate (100 mg, 23% yield). Yellow solid; LCMS [ESI, M+1]:739.

Step D. (8-(4-((1R,5S)-3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)naphthalen-1-yl)methanol. To a solution of tert-butyl (1R,5S)-3-(8-fluoro-2-((tetrahydro-1H-pyrrolizin-7a(5H)-yl)methoxy)-7-(8-(((tetrahydro-2H-pyran-2-yl)oxy)methyl)naphthalen-1-yl)pyrido[4,3-d]pyrimidin-4-yl)-3,8-diazabicyclo[3.2.1]octane-8-carboxylate (50 mg, 67.7 µmol, 1.0 eq) in acetonitrile (0.5 mL) was added HCl·dioxane (4 M, 1.0 mL). The mixture was stirred at 0° C. for 30 minutes. The mixture was concentrated, and the reaction mixture was diluted with water (1.0 mL). Then the mixture was adjusted pH~8 with saturated NaHCO$_3$ aqueous solution and extracted with dichloromethane (3×5.0 mL), washed with brine (5.0 mL), dried over Na$_2$SO$_4$, filtered and concentrated. The residue was purified by prep-HPLC (column: Waters X bridge 150*25 mm*5 um; mobile phase: [water (10 mM NH$_4$HCO$_3$)-ACN]; B %: 15%-45%, 10 min). The desired fraction was collected and concentrated under vacuum to remove acetonitrile. The mixture was lyophilized to give the title compound (11.9 mg, 31% yield). Yellow solid; $^1$H NMR (400 MHz, chloroform-d) δ=8.96 (s, 1H), 8.01 (d, J=8.0 Hz, 1H), 7.91 (d, J=8.0 Hz, 1H), 7.64 (dd, J=0.9, 7.2 Hz, 1H), 7.58-7.49 (m, 2H), 7.44 (d, J=6.8 Hz, 1H), 4.70 (br d, J=12.0 Hz, 1H), 4.49-4.28 (m, 3H), 4.18 (s, 2H), 3.75-3.61 (m, 3H), 3.59-3.50 (m, 1H), 3.15-3.05 (m, 2H), 2.69-2.60 (m, 2H), 2.15-2.06 (m, 2H), 1.94-1.84 (m, 6H), 1.75-1.62 (m, 4H); LCMS [ESI, M+1]:555.

Example 239

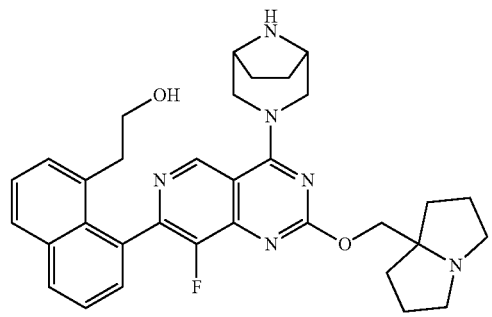 [SMILES: OCCc1cccc2cccc(-c3ncc4c(N5CC6CCC(C5)N6)nc(OCC56CCCN5CCC6)nc4c3F)c12]

2-(8-(4-((1R,5S)-3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)naphthalen-1-yl)ethan-1-ol

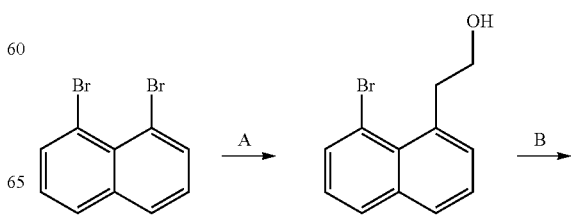

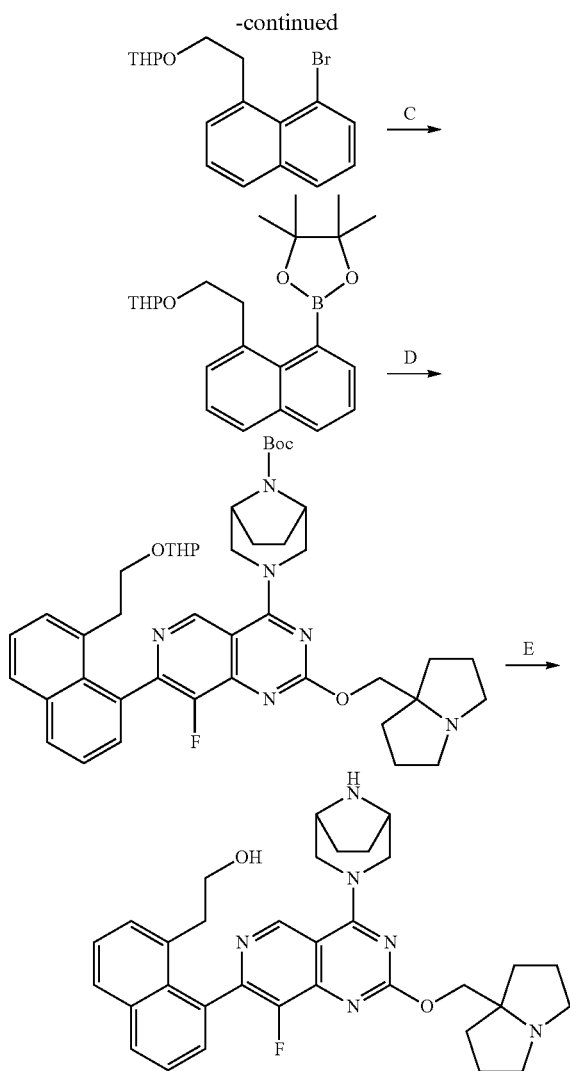

-continued

Step A. 2-(8-bromo-1-naphthyl)ethanol. To a solution of 1,8-dibromonaphthalene (10 g, 35.0 mmol, 1.0 eq) in THF (150 mL) at −65° C. was added n-Buli (2.5 M, 15.4 mL, 1.1 eq), and the resulted solution was stirred at −65° C. for 30 min. Then oxirane (30.8 g, 699 mmol, 34.9 mL, 20 eq) was added, and the resulted solution was stirred at 0° C. for 0.5 hour. After completion, the reaction mixture was diluted with $H_2O$ (100 mL) and extracted with ethyl acetate (2×300 mL). The combined organic layers were washed with saturated brine (3×200 mL), dried over $Na_2SO_4$, filtered and concentrated under vacuum. The residue was purified by column chromatography ($SiO_2$, Petroleum ether:Ethyl acetate=1:0 to Petroleum ether:Ethyl acetate=3:1) to give 2-(8-bromo-1-naphthyl)ethanol (4.7 g, 54% yield). Yellow solid. Rf=0.43. $^1$H NMR (400 MHz, CHLOROFORM-d) δ=7.75-7.64 (m, 3H), 7.35-7.26 (m, 2H), 7.16-7.09 (m, 1H), 3.94-3.85 (m, 2H), 3.77-3.70 (m, 2H).

Step B. 2-[2-(8-bromo-1-naphthyl)ethoxy]tetrahydropyran. A mixture of 2-(8-bromo-1-naphthyl)ethanol (3.0 g, 12.0 mmol, 1.0 eq), DHP (1.51 g, 17.9 mmol, 1.64 mL, 1.5 eq) and TsOH·$H_2O$ (227 mg, 1.19 mmol, 0.10 eq) in dichloromethane (40 mL) was degassed and purged with $N_2$ for 3 times, and then the mixture was stirred at 25° C. for 2 hours under $N_2$ atmosphere. After completion, the mixture was diluted with water (20 mL) and separated. Then the organic layer was washed with saturated brine (15 mL), dried over $Na_2SO_4$, filtered and concentrated under vacuum. The residue was purified by reversed phase flash chromatography [water (FA, 0.10%)/acetonitrile] to give 2-[2-(8-bromo-1-naphthyl)ethoxy]tetrahydropyran (2.8 g, 69% yield). Yellow oil. Rf=0.8 (3:1, petroleum ether/ethyl acetate). $^1$H NMR (400 MHz, $CDCl_3$-d) δ=7.81 (tdd, J=1.2, 7.6, 19.6 Hz, 3H), 7.49 (dd, J=1.2, 6.8 Hz, 1H), 7.41 (t, J=7.6 Hz, 1H), 7.23 (t, J=7.6 Hz, 1H), 4.63 (t, J=3.6 Hz, 1H), 4.15-4.05 (m, 1H), 3.94-3.87 (m, 2H), 3.84-3.75 (m, 2H), 3.49-3.40 (m, 1H), 1.89-1.78 (m, 1H), 1.76-1.62 (m, 2H), 1.59-1.48 (m, 3H).

Step C. 4,4,5,5-tetramethyl-2-[8-(2-tetrahydropyran-2-yloxyethyl)-1-naphthyl]-1,3,2-dioxaborolane. To a mixture of 2-[2-(8-bromo-1-naphthyl)ethoxy]tetrahydropyran (1.50 g, 4.47 mmol, 1.0 eq), 4,4,5,5-tetramethyl-2-(4,4,5,5-tetramethyl-1,3,2-dioxaborolan-2-yl)-1,3,2-dioxaborolane (2.27 g, 8.95 mmol, 2.0 eq) and KOAc (1.32 g, 13.4 mmol, 3.0 eq) in dioxane (20 mL) was added Pd(dppf)$Cl_2$ (327 mg, 447 μmol, 0.10 eq) under $N_2$. The mixture was degassed and then heated to 110° C. for 1 hour under $N_2$. After completion, the mixture was diluted with ethyl acetate (5 mL) and water (10 mL) and then separated. The aqueous phase was extracted with ethyl acetate (10 mL). The combined organic layer was washed with saturated brine (15 mL), dried over $Na_2SO_4$, filtered and concentrated under vacuum. The residue was purified by reversed phase flash chromatography [water (FA, 0.1%)/acetonitrile] and column chromatography ($SiO_2$, petroleum ether/ethyl acetate=30/1) to give 4,4,5,5-tetramethyl-2-[8-(2-tetrahydropyran-2-yloxyethyl)-1-naphthyl]-1,3,2-dioxaborolane (596 mg, 28% yield). Brown oil. Rf=0.4 (10:1, petroleum ether/ethyl acetate). $^1$H NMR (400 MHz, $CDCl_3$-d) δ=7.87 (dd, J=1.2, 8.0 Hz, 1H), 7.74-7.69 (m, 1H), 7.67 (dd, J=1.2, 6.8 Hz, 1H), 7.46-7.39 (m, 3H), 4.64 (t, J=3.6 Hz, 1H), 4.16-4.07 (m, 1H), 3.85-3.76 (m, 2H), 3.62-3.43 (m, 3H), 1.87-1.77 (m, 1H), 1.74-1.66 (m, 1H), 1.59-1.48 (m, 4H), 1.47 (d, J=4.4 Hz, 12H).

Step D. tert-butyl (1R,5S)-3-(8-fluoro-2-((tetrahydro-1H-pyrrolizin-7a(5H)-yl)methoxy)-7-(8-(2-((tetrahydro-2H-pyran-2-yl)oxy)ethyl)naphthalen-1-yl)pyrido[4,3-d]pyrimidin-4-yl)-3,8-diazabicyclo[3.2.1]octane-8-carboxylate. To a mixture of tert-butyl (1R,5S)-3-(7-chloro-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (420 mg, 788 μmol, 1.0 eq), 4,4,5,5-tetramethyl-2-[8-(2-tetrahydropyran-2-yloxyethyl)-1-naphthyl]-1,3,2-dioxaborolane (602 mg, 1.58 mmol, 2.0 eq) and $Cs_2CO_3$ (770 mg, 2.36 mmol, 3.0 eq) in dioxane (9 mL) and $H_2O$ (3 mL) was degassed. Then Pd(dppf)$Cl_2$ (57.7 mg, 78.8 μmol, 0.10 eq) was added into the above mixture and the mixture was stirred at 90° C. for 3 hours under $N_2$. After completion, the mixture was diluted with ethyl acetate (8 mL) and water (8 mL) and then separated. The aqueous phase was extracted with ethyl acetate (8 mL). The combined organic layers were washed with saturated brine (10 mL), dried over $Na_2SO_4$, filtered and concentrated under vacuum. The residue was purified by column chromatography ($SiO_2$, ethyl acetate/methanol=10/1) and reversed phase flash [water (FA, 0.1%)/acetonitrile] to give the title compound (170 mg, 27% yield). Brown solid. Rf=0.4 (10:1, Dichloromethane:Methanol). LCMS [ESI, M+1]: 753.

Step E. 2-(8-(4-((1R,5S)-3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)naphthalen-1-yl)ethan-1-ol. To a mixture of tert-butyl (1R,5S)-3-(8-fluoro-2-((tetrahydro-1H-pyrrolizin-7a(5H)-yl)methoxy)-7-(8-(2-((tetrahydro-2H-pyran-2-yl)oxy)ethyl)naphthalen-1-yl)

pyrido[4,3-d]pyrimidin-4-yl)-3,8-diazabicyclo[3.2.1]octane-8-carboxylate e (100 mg, 133 μmol, 1.0 eq) in acetonitrile (0.5 mL) was added HCl·dioxane (4 M, 1 mL, 30 eq) at 0° C. The mixture was stirred at 0° C. for 0.5 hour. After completion, the mixture was concentrated under vacuum. Then the residue was purified by prep-HPLC (column: Phenomenex luna C18 150*40 mm*15 um; mobile phase: [water (0.225% FA)-ACN]; B %: 1%-30%, 9 min) to give the title compound (15.1 mg, 20% yield, 2FA). Yellow solid. ¹H NMR (400 MHz, METHANOL-d4) δ=9.13 (s, 1H), 8.07 (dd, J=1.2, 8.0 Hz, 1H), 7.91 (dd, J=1.2, 8.0 Hz, 1H), 7.59 (dd, J=6.8, 8.0 Hz, 1H), 7.52-7.45 (m, 2H), 7.40 (dd, J=1.2, 6.8 Hz, 1H), 4.78 (br d, J=13.6 Hz, 2H), 4.68 (s, 2H), 4.05 (br s, 2H), 3.97 (br d, J=13.6 Hz, 1H), 3.85 (br d, J=13.6 Hz, 1H), 3.75-3.66 (m, 2H), 3.55-3.43 (m, 2H), 3.30-3.25 (m, 2H), 2.60-2.52 (m, 2H), 2.33 (ddd, J=2.0, 6.8, 12.4 Hz, 2H), 2.24-1.96 (m, 10H). LCMS [ESI, M+1]: 569.

Example 240

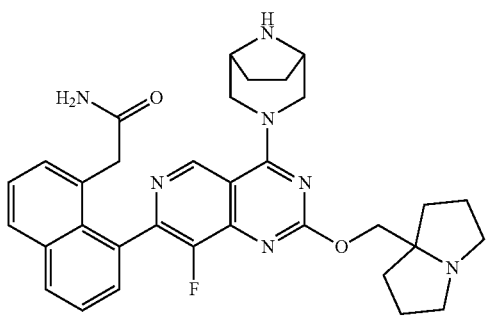 [SMILES: NC(=O)Cc1cccc2cccc(-c3ncc4c(N5CC6CCC(C5)N6)nc(OCC56CCCN5CCC6)nc4c3F)c12]

2-(8-(4-((1R,5S)-3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)naphthalen-1-yl)acetamide

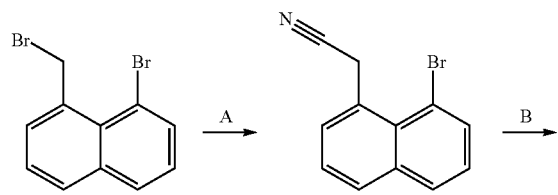

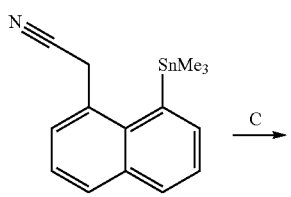

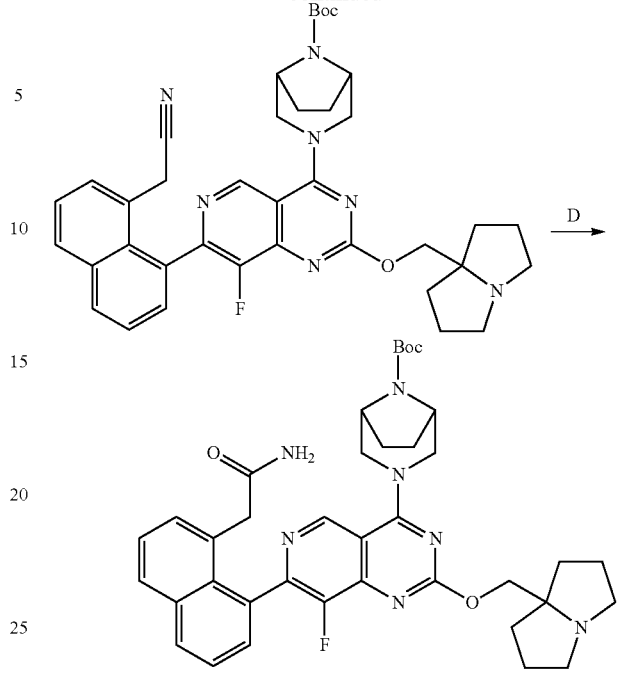

Step A. 2-(8-bromonaphthalen-1-yl)acetonitrile. To a solution of bromo-8-(bromomethyl)naphthalene (100 mg, 333 μmol, 1.0 eq) in DMF (2 mL) were added NaCN (24.5 mg, 500 μmol, 1.5 eq) and H₂O (300 ul). The reaction was stirred for 1 hour at 50° C. To the reaction was added water (2 mL), saturated NaHCO₃ (1 mL) and ethyl acetate (5 mL). The layers were separated, and the aqueous layer was extracted with ethyl acetate (3×5 mL). The combined organics were washed with brine (2 mL), dried over Na₂SO₄, filtered, and concentrated. The residue was purified by column chromatography (SiO₂, petroleum ether/ethyl acetate=300/1 to 10/1) to give 2-(8-bromonaphthalen-1-yl)acetonitrile (80 mg, 97% yield). White solid. ¹H NMR (400 MHz, chloroform-d) δ=7.95-7.82 (m, 3H), 7.73 (d, J=7.2 Hz, 1H), 7.49 (t, J=7.6 Hz, 1H), 7.32 (t, J=7.6 Hz, 1H), 4.79 (s, 2H).

Step B. 2-(8-(trimethylstannyl)naphthalen-1-yl)acetonitrile. A mixture of 2-(8-bromonaphthalen-1-yl)acetonitrile (100 mg, 406 μmol, 1.0 eq), trimethyl(trimethylstannyl)stannane (532 mg, 1.63 mmol, 337 μL, 4.0 eq), Pd(PPh₃)₄ (46.9 mg, 40.6 μmol, 0.1 eq) in toluene (2 mL) was degassed and purged with N₂ for 3 times. The mixture was stirred at 100° C. for 12 hours under N₂ atmosphere. The reaction mixture was diluted with ethyl acetate (10 mL) and washed with water (3×10 mL). The organic layer was washed with brine (10 mL), dried over Na₂SO₄, filtered and concentrated under reduced pressure to give a residue. The residue was purified by reversed phase flash chromatography [water (0.1% formic acid)/acetonitrile)] to give 2-(8-(trimethylstannyl)naphthalen-1-yl)acetonitrile (60 mg, 45% yield). Black solid. ¹H NMR (400 MHz, chloroform-d) δ=7.91-7.81 (m, 3H), 7.78 (dd, J=1.2, 6.8 Hz, 1H), 7.54-7.43 (m, 2H), 4.41 (s, 2H), 0.49 (S, 9H).

Step C. tert-butyl (1R,5S)-3-(7-(8-(cyanomethyl)naphthalen-1-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate. A mixture of 2-(8-(trimethylstannyl)naphthalen-1-yl)acetonitrile (330 mg, 999 μmol, 2.67 eq), tert-butyl (1R,5S)-3-(7-chloro-8-fluoro-2-

((tetrahydro-1H-pyrrolizin-7a(5H)-yl)methoxy)pyrido[4,3-d]pyrimidin-4-yl)-3,8-diazabicyclo[3.2.1]octane-8-carboxylate (200 mg, 375 µmol, 1.0 eq), CuI (21.4 mg, 112 µmol, 0.3 eq), BINAP (46.7 mg, 75.0 µmol, 0.2 eq) and Pd(dppf)Cl₂ (27.4 mg, 37.5 µmol, 0.1 eq) in toluene (10 mL) was degassed and purged with N₂ for 3 times. The mixture was stirred at 100° C. for 12 hours under N₂ atmosphere. The reaction mixture was diluted with water (20 mL) and extracted with ethyl acetate (3×30 mL). The combined organic layers were washed with brine (20 mL), dried over Na₂SO₄, filtered and concentrated under reduced pressure to give a residue. The residue was purified by reversed phase flash chromatography [water (0.1% formic acid)/acetonitrile)] to give the title compound (80 mg, 29% yield). Yellow solid. LCMS [ESI, M+1]: 664.

Step D. 2-(8-(4-((1R,5S)-3,8-diazabicyclo[3.2.1]octan-3-yl)-8-fluoro-2-((tetrahydro-1H-pyrrolizin-7a(5H)-yl) methoxy)pyrido[4,3-d]pyrimidin-7-yl)naphthalen-1-yl)acetamide. A solution of tert-butyl (1R,5S)-3-(7-(8-(cyanomethyl)naphthalen-1-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (40 mg, 60.2 µmol, 1 eq) in H2SO₄ (368 mg, 3.68 mmol, 200 µL, 98% purity, 61.0 eq) and TFA (1.54 g, 13.5 mmol, 1 mL, 224 eq) was stirred at 30° C. for 2 hours. After completion, the reaction mixture was poured into ice-cold water (1 mL). The mixture was adjusted to pH~9 with saturated Na₂CO₃ aqueous solution and extracted with dichloromethane (3×5 mL). The combined organic layers were washed with brine (3 mL), dried over Na₂SO₄, filtered and concentrated under reduced pressure. The residue was purified by prep-HPLC (column: Waters Xbridge 150*25 mm*5 um; mobile phase: [water (10 mM NH₄HCO₃)-ACN]; B %: 10%-40%, 10 min). The desired fraction was collected and lyophilized to give the title compound (5.84 mg, 16% yield). White solid. ¹H NMR (400 MHz, chloroform-d) δ=8.95 (s, 1H), 8.02 (d, J=1.2, 8.0 Hz, 1H), 7.95 (d, J=8.0 Hz, 1H), 7.63-7.56 (m, 1H), 7.55-7.47 (m, 2H), 7.44-7.38 (m, 1H), 5.35 (s, 1H), 5.22 (s, 1H), 4.76-4.53 (m, 2H), 4.18 (s, 2H), 3.74-3.37 (m, 6H), 3.21-3.02 (m, 2H), 2.73-2.58 (m, 2H), 2.19-2.03 (m, 2H), 1.96-1.77 (m, 10H). LCMS [ESI, M+1]: 582.

Example 241

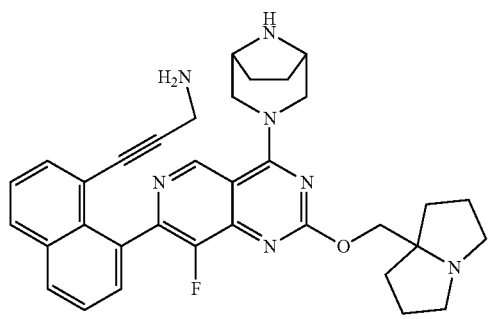 [SMILES: NCC#Cc1cccc2cccc(-c3ncc4c(N5CC6CCC(C5)N6)nc(OCC56CCCN5CCC6)nc4c3F)c12]

3-(8-(4-((1R,5S)-3,8-diazabicyclo[3.2.1]octan-3-yl)-8-fluoro-2-((tetrahydro-1H-pyrrolizin-7a(5H)-yl) methoxy)pyrido[4,3-d]pyrimidin-7-yl)naphthalen-1-yl)prop-2-yn-1

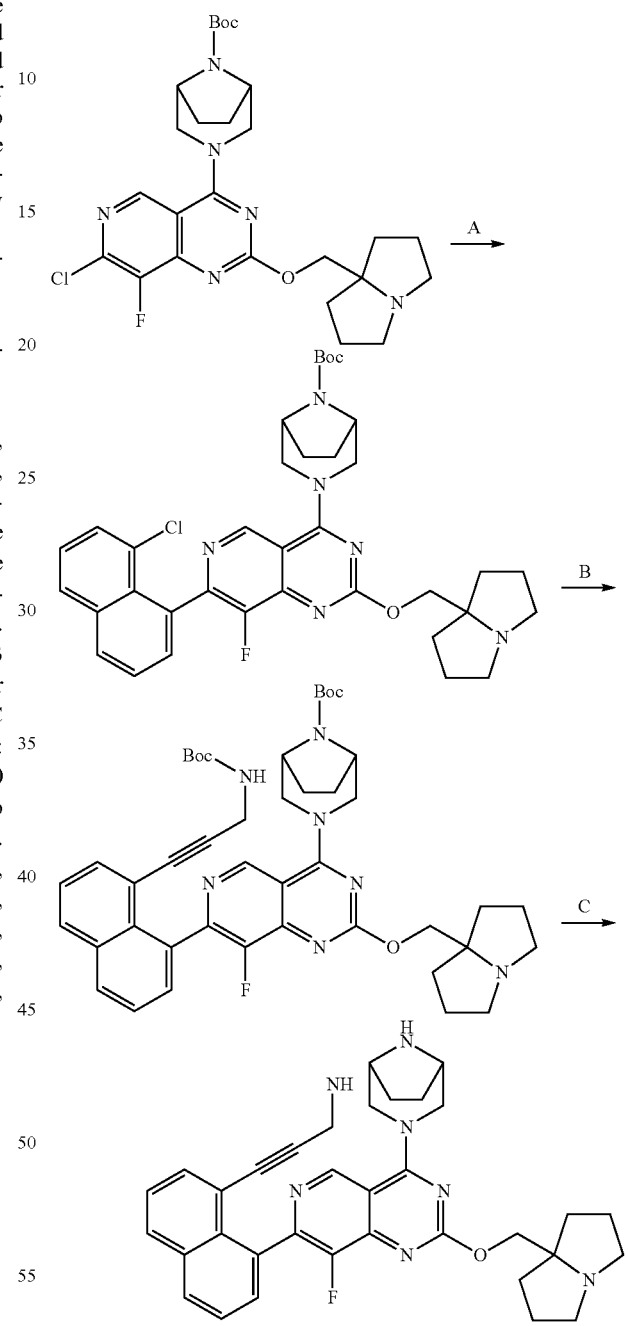

Step A. tert-butyl (1R,5S)-3-(7-(8-chloronaphthalen-1-yl)-8-fluoro-2-((tetrahydro-1H-pyrrolizin-7a(5H)-yl) methoxy)pyrido[4,3-d]pyrimidin-4-yl)-3,8-diazabicyclo [3.2.1]octane-8-carboxylate. A mixture of tert-butyl (1R,5S)-3-(7-chloro-8-fluoro-2-((tetrahydro-1H-pyrrolizin-7a (5H)-yl)methoxy)pyrido[4,3-d]pyrimidin-4-yl)-3,8-diazabicyclo[3.2.1]octane-8-carboxylate (1.55 g, 2.91 mmol, 1.0 eq), (8-chloro-1-naphthyl)-trimethyl-stannane (3.79 g, 11.6 mmol, 4.0 eq), CuI (166 mg, 872 µmol, 0.3 eq), BINAP (362 mg, 582 μmol, 0.2 eq) and Pd(dppf)Cl₂ (213 mg, 291 μmol, 0.1 eq) in toluene (20 mL) was stirred at 100° C. for 6 hours under N₂. After completion, the mixture was diluted with water (20 mL), extracted with ethyl acetate (3×20 mL), the combined organic layer was washed with brine (20 mL), dried over Na₂SO₄, filtered and concentrated under vacuum. The residue was purified by reversed phase flash chromatography [water (FA, 0.1%)/acetonitrile] to give tert-butyl (1R,5S)-3-(7-(8-chloronaphthalen-1-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (700 mg, 36% yield). Yellow solid; LCMS [ESI, M+1]: 659.

Step B. tert-butyl (1R,5S)-3-(7-(8-(3-((tert-butoxycarbonyl)amino)prop-1-yn-1-yl)naphthalen-1-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate. A mixture of tert-butyl (1R,5S)-3-(7-(8-chloronaphthalen-1-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (100 mg, 151 μmol, 1.0 eq), tert-butyl N-prop-2-ynylcarbamate (471 mg, 3.03 mmol, 20 eq), XPhos (43.4 mg, 91.0 μmol, 0.6 eq), acetonitrile; dichloropalladium (7.87 mg, 30.3 μmol, 0.2 eq) and Cs₂CO₃ (148 mg, 455 μmol, 3.0 eq) in acetonitrile (5.0 mL) was stirred at 90° C. for 5 hours under N₂. After completion, the mixture was diluted with water (10 mL), and extracted with ethyl acetate (2×10 mL). The combined organic layer was washed with brine (10 mL), dried over Na₂SO₄, filtered and concentrated under vacuum. The residue was purified by column chromatography (SiO₂, ethyl acetate/methanol=10/1, Rf=0.15) and reversed phase flash [water (FA, 0.1%)/acetonitrile] to give tert-butyl (1R,5S)-3-(7-(8-(3-((tert-butoxycarbonyl)amino)prop-1-yn-1-yl)naphthalen-1-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (24 mg, 16% yield). Yellow oil. LCMS [ESI, M+1]: 778.

Step C. 3-(8-(4-((1R,5S)-3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)naphthalen-1-yl)prop-2-yn-1-amine. A mixture of tert-butyl (1R,5S)-3-(7-(8-(3-((tert-butoxycarbonyl)amino)prop-1-yn-1-yl)naphthalen-1-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (55 mg, 70.7 μmol, 1.0 eq) in HCl·dioxane (4 M, 1.0 mL, 56.6 eq) and acetonitrile (0.5 mL) was stirred at 0° C. for 0.5 hour. After completion, the mixture was concentrated under vacuum. The residue was adjusted pH to 8 by saturated sodium carbonate (2.0 mL), extracted with ethyl acetate/methanol=10/1 (5 mL), dried over Na₂SO₄, filtered and concentrated under vacuum. The residue was purified by prep-HPLC (column: Waters Xbridge 150*25 mm*5um; mobile phase: [water (10 mM NH₄HCO₃)-ACN]; B %: 22%-52%, 10 min) to give 3-(8-(4-((1R,5S)-3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)naphthalen-1-yl)prop-2-yn-1-amine (18.9 mg, 46% yield). Yellow solid. ¹H NMR (400 MHz, chloroform-d) δ=9.06 (s, 1H), 7.97 (dd, J=1.2, 8.0 Hz, 1H), 7.91 (dd, J=0.8, 8.0 Hz, 1H), 7.66 (dd, J=1.2, 7.2 Hz, 1H), 7.61-7.56 (t, J=7.6 Hz, 1H), 7.55-7.52 (m, 1H), 7.45 (dd, J=7.2, 8.0 Hz, 1H), 4.67-4.53 (m, 2H), 4.42-4.31 (m, 2H), 3.72-3.61 (m, 4H), 3.44-3.31 (m, 2H), 2.95-2.85 (m, 1H), 2.81-2.72 (m, 3H), 2.26-2.20 (m, 2H), 1.98 (m, 4H), 1.83-1.73 (m, 6H). LCMS [ESI, M+1]: 578.

Example 242

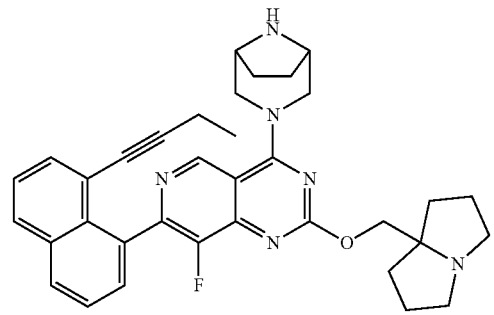 [SMILES: CCC#Cc1cccc2cccc(-c3ncc4c(N5CC6CCC(C5)N6)nc(OCC56CCCN5CCC6)nc4c3F)c12]

4-((1R,5S)-3,8-diazabicyclo[3.2.1]octan-3-yl)-7-(8-(but-1-yn-1-yl)naphthalen-1-yl)-8-fluoro-2-((tetrahydro-1H-pyrrolizin-7a(5H)-yl)methoxy)pyrido[4,3-d]pyrimidine

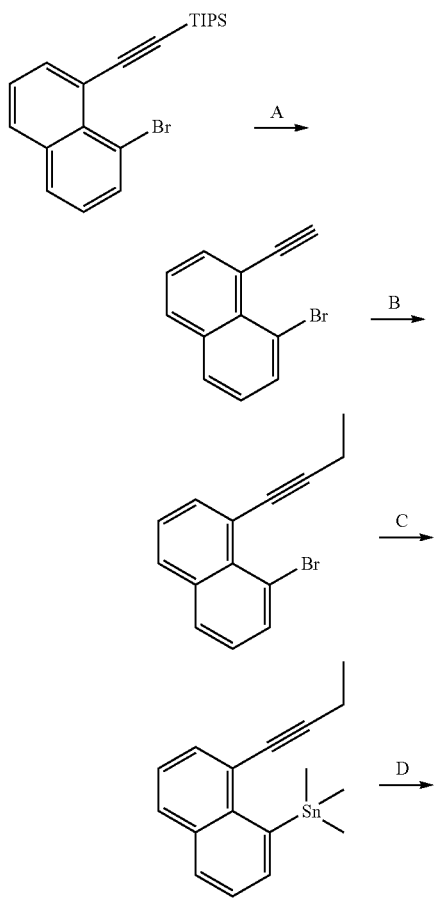

-continued

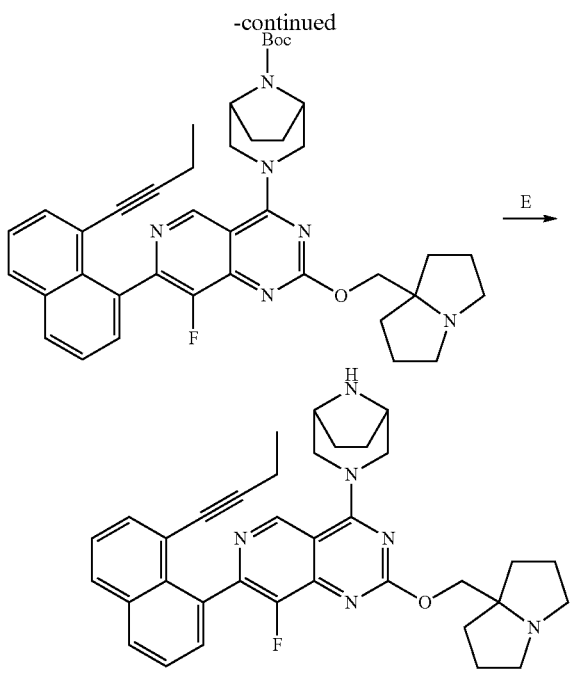

Step A. 1-bromo-8-ethynyl-naphthalene. To a solution of 2-(8-bromo-1-naphthyl) ethynyl-triisopropyl-silane (synthesized according to Example 179, 5.0 g, 12.9 mmol, 1.0 eq) in DMF (40 mL) was added CsF (9.80 g, 64.5 mmol, 5.0 eq). The mixture was stirred at 25° C. for 30 minutes. The mixture was diluted with ethyl acetate (40 mL) and water (50 mL) and separated. The organic layer was washed with water (3×50 mL) and brine (50 mL), dried over $Na_2SO_4$, filtered and concentrated under vacuum. The residue was purified by reversed phase flash chromatography [water (0.1% formic acid)/acetonitrile)] to give 1-bromo-8-ethynyl-naphthalene (2.0 g, 67% yield). Brown solid. $^1$H NMR (400 MHz, chloroform-d) δ=7.91-7.72 (m, 4H), 7.45-7.35 (m, 1H), 7.28-7.21 (m, 1H), 3.56 (s, 1H).

Step B. 1-bromo-8-but-1-ynyl-naphthalene. To a solution of 1-bromo-8-ethynyl-naphthalene (1.2 g, 5.19 mmol, 1.0 eq) and HMPA (1.21 g, 6.75 mmol, 1.19 mL, 1.3 eq) in THF (20 mL) was added dropwise LiHMDS (1 M, 6.75 mL, 1.3 eq) at −70° C. After addition, the mixture was stirred at −70° C. for 1 hour and $CH_3CH_2I$ (4.05 g, 25.9 mmol, 2.08 mL, 5.0 eq) was added dropwise at −70° C. The resulting mixture was stirred at 25° C. for 12 hours. The reaction mixture was diluted with saturated $NH_4Cl$ aqueous solution (20 mL) and extracted with ethyl acetate (3×30 mL). The combined organic layers were washed with brine (30 mL), dried over $Na_2SO_4$, filtered and concentrated under reduced pressure. The residue was purified by reversed phase flash chromatography [water (0.1% formic acid)/acetonitrile)] to give 1-bromo-8-but-1-ynyl-naphthalene (600 mg, 44% yield). Yellow oil. $^1$H NMR (400 MHz, chloroform-d) δ=7.86-7.73 (m, 4H), 7.39 (t, J=7.6 Hz, 1H), 7.27-7.23 (m, 1H), 2.54 (q, J=7.6 Hz, 2H), 1.31 (t, J=7.6 Hz, 3H).

Step C. (8-but-1-ynyl-1-naphthyl)-trimethyl-stannane. A mixture of 1-bromo-8-but-1-ynyl-naphthalene (100 mg, 386 μmol, 1.0 eq), trimethyl(trimethylstannyl)stannane (379 mg, 1.16 mmol, 240 μL, 3.0 eq), Pd(PPh$_3$)$_4$ (44.6 mg, 38.6 μmol, 0.1 eq) in toluene (2.0 mL) was degassed and purged with $N_2$ for 3 times, and then the mixture was stirred at 110° C. for 12 hours under $N_2$ atmosphere. The reaction mixture was diluted with water (5.0 mL) and extracted with ethyl acetate (3×5.0 mL). The combined organic layers were washed with brine (5.0 mL), dried over $Na_2SO_4$, filtered and concentrated under reduced pressure. The residue was purified by reversed phase flash chromatography [water (0.1% formic acid)/acetonitrile)] to give (8-but-1-ynyl-1-naphthyl)-trimethyl-stannane (80 mg, 60% yield). Yellow oil. $^1$H NMR (400 MHz, chloroform-d) δ=7.88-7.68 (m, 4H), 7.47-7.35 (m, 2H), 2.53 (q, J=7.6 Hz, 2H), 1.32 (t, J=7.6 Hz, 3H), 0.44 (s, 9H).

Step D. tert-butyl (1R,5S)-3-(7-(8-(but-1-yn-1-yl)naphthalen-1-yl)-8-fluoro-2-((tetrahydro-1H-pyrrolizin-7a(5H)-yl)methoxy)pyrido[4,3-d]pyrimidin-4-yl)-3,8-diazabicyclo [3.2.1]octane-8-carboxylate. A mixture of tert-butyl (1R,5S)-3-(7-chloro-8-fluoro-2-((tetrahydro-1H-pyrrolizin-7a (5H)-yl)methoxy)pyrido[4,3-d]pyrimidin-4-yl)-3,8-diazabicyclo[3.2.1]octane-8-carboxylate (300 mg, 563 μmol, 1.0 eq), (8-but-1-ynyl-1-naphthyl)-trimethyl-stannane (386 mg, 1.13 mmol, 2.0 eq), CuI (32.2 mg, 169 μmol, 0.3 eq), BINAP (70.1 mg, 112 μmol, 0.2 eq) and Pd(dppf)Cl$_2$ (41.2 mg, 56.3 μmol, 0.1 eq) in toluene (6.0 mL) was degassed and purged with $N_2$ for 3 times, and then the mixture was stirred at 90° C. for 12 hours under $N_2$ atmosphere. The reaction mixture was diluted with water (20 mL) and extracted with ethyl acetate (3×30 mL). The combined organic layers were washed with brine (30 mL), dried over $Na_2SO_4$, filtered and concentrated under reduced pressure. The residue was purification by column chromatography (SiO$_2$, petroleum ether/ethyl acetate=10/1 to ethyl acetate/methanol=10/1). The residue was further purified by reversed phase flash chromatography [water (0.1% formic acid)/acetonitrile)] to give tert-butyl (1R,5S)-3-(7-(8-(but-1-yn-1-yl)naphthalen-1-yl)-8-fluoro-2-((tetrahydro-1H-pyrrolizin-7a(5H)-yl)methoxy)pyrido[4,3-d]pyrimidin-4-yl)-3, 8-diazabicyclo[3.2.1]octane-8-carboxylate (85 mg, 20% yield). White solid. LCMS [ESI, M+1]: 677.

Step E. 4-((1R,5S)-3,8-diazabicyclo[3.2.1]octan-3-yl)-7-(8-(but-1-yn-1-yl)naphthalen-1-yl)-8-fluoro-2-((tetrahydro-1H-pyrrolizin-7a(5H)-yl)methoxy)pyrido[4,3-d]pyrimidine. To a solution of tert-butyl (1R,5S)-3-(7-(8-(but-1-yn-1-yl) naphthalen-1-yl)-8-fluoro-2-((tetrahydro-1H-pyrrolizin-7a (5H)-yl)methoxy)pyrido[4,3-d]pyrimidin-4-yl)-3,8-diazabicyclo[3.2.1]octane-8-carboxylate (80 mg, 118 μmol, 1.0 eq) in acetonitrile (1.5 mL) was added HCl·dioxane (4.0 M, 0.75 mL). The mixture was stirred at 0° C. for 30 minutes. The mixture was concentrated, and the residue was diluted with water (1.0 mL). Then the mixture was adjusted pH~8 with saturated NaHCO$_3$ aqueous solution and extracted with (dichloromethane/methanol=10/1) (3×5.0 mL). The combined organic layers were dried over Na$_2$SO$_4$, filtered and concentrated. The residue was purified by prep-HPLC (column: Waters X bridge C18 150*50 mm*10 um; mobile phase: [water (10 mM NH$_4$HCO$_3$)-ACN]; B %: 35%-65%, 10 min). The desired fraction was collected and concentrated under vacuum to remove acetonitrile. The mixture was lyophilized to give the title compound (29.2 mg, 42% yield). White solid, $^1$H NMR (400 MHz, chloroform-d) δ=9.05 (s, 1H), 7.95 (dd, J=1.6, 8.0 Hz, 1H), 7.87 (d, J=8.0 Hz, 1H), 7.64 (d, J=7.2 Hz, 1H), 7.59-7.50 (m, 2H), 7.42 (t, J=8.0 Hz, 1H), 4.63 (br d, J=12.4 Hz, 1H), 4.54 (br d, J=11.6 Hz, 1H), 4.21 (d, J=1.2 Hz, 2H), 3.71-3.55 (m, 4H), 3.07-3.14 (m, 2H), 2.56-2.69 (m, 2H), 2.04-2.14 (m, 2H), 1.87-1.74 (m, 8H), 1.71-1.62 (m, 4H), 0.75 (t, J=7.6 Hz, 3H); LCMS [ESI, M+1]: 577.

Example 243

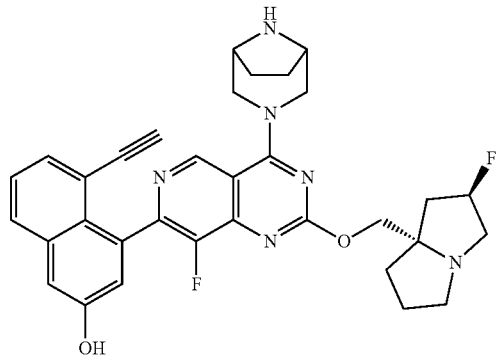 [SMILES: C#Cc1cccc2cc(O)cc(-c3ncc4c(N5CC6CCC(C5)N6)nc(OC[C@@]56CCCN5C[C@H](F)C6)nc4c3F)c12]

4-(4-((1R,5S)-3,8-diazabicyclo[3.2.1]octan-3-yl)-8-fluoro-2-(((2R,7aS)-2-fluorohexahydro-1H-pyrrolizin-7a-yl)methoxy)pyrido[4,3-d]pyrimidin-7-yl)-5-ethynylnaphthalen-2-ol

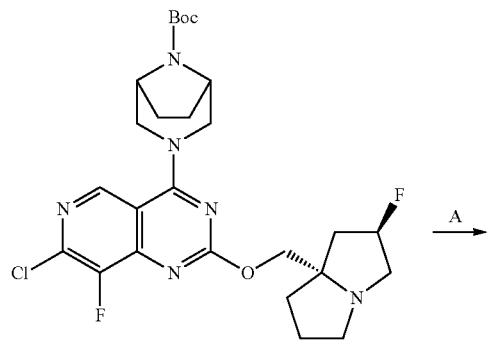

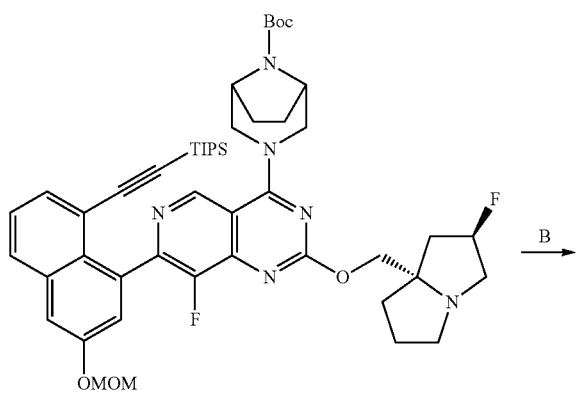

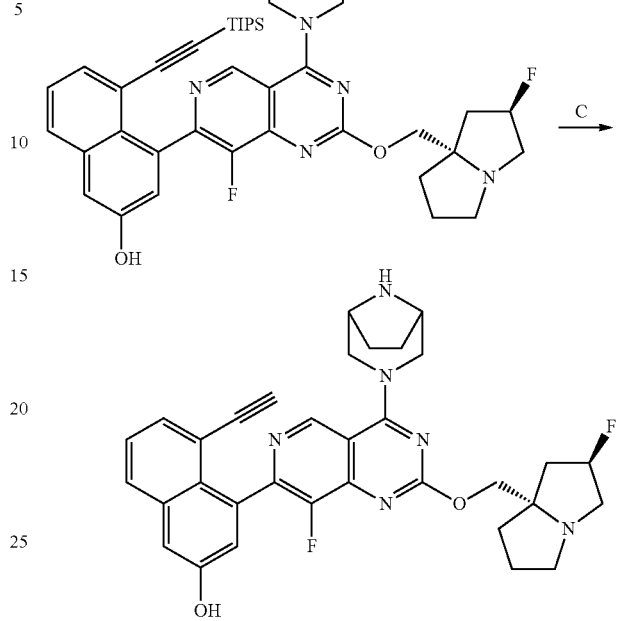

Step A. tert-butyl (1R,5 S)-3-(8-fluoro-2-(((2R,7aS)-2-fluorotetrahydro-1H-pyrrolizin-7a(5H)-yl)methoxy)-7-(3-(methoxymethoxy)-8-((triisopropylsilyl)ethynyl)naphthalen-1-yl) pyrido[4,3-d]pyrimidin-4-yl)-3,8-diazabicyclo[3.2.1]octane-8-carboxylate. To a mixture of tert-butyl (1R, 5S)-3-(7-chloro-8-fluoro-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (71.5 mg, 129.87 μmol, 1.0 eq) and $Cs_2CO_3$ (127 mg, 390 μmol, 3.0 eq) in dioxane (3 mL) and $H_2O$ (1 mL) were added Pd(dppf)$Cl_2$ (19.0 mg, 26.0 μmol, 0.2 eq), triisopropyl((6-(methoxymethoxy)-8-(4,4,5,5-tetramethyl-1,3,2-dioxaborolan-2-yl)naphthalen-1-yl)ethynyl)silane (86.5 mg, 169 μmol, 1.3 eq) in one portion under $N_2$. The mixture was stirred at 100° C. for 2 hours. After completion, the reaction mixture was diluted with $H_2O$ (10 mL) and extracted with EtOAc mL (20 mL). The combined organic layers were washed with saturated sodium chloride solution (20 mL), dried over anhydrous sodium sulfate, filtered and concentrated under reduced pressure. The residue was purified by reversed phase flash chromatography [water (0.1% FA)/acetonitrile] to give the title compound (60 mg, 40% yield). Yellow solid. LCMS (ESI, M+1). 883.

Step B. 4-(4-((1R,5S)-3,8-diazabicyclo[3.2.1]octan-3-yl)-8-fluoro-2-(((2R,7aS)-2-fluorohexahydro-1H-pyrrolizin-7a-yl)methoxy)pyrido[4,3-d]pyrimidin-7-yl)-5-((triisopropylsilyl)ethynyl)naphthalen-2-ol. To a mixture of tert-butyl (1R,5S)-3-(8-fluoro-2-(((2R,7aS)-2-fluorotetrahydro-1H-pyrrolizin-7a(5H)-yl)methoxy)-7-(3-(methoxymethoxy)-8-((triisopropylsilyl)ethynyl)naphthalen-1-yl)pyrido[4,3-d]pyrimidin-4-yl)-3,8-diazabicyclo[3.2.1]octane-8-carboxylate (55 mg, 62.28 μmol, 1 eq) in MeCN (2.5 mL) was added HCl·dioxane (4 M, 0.5 mL, 32.11 eq) in one portion under $N_2$. The mixture was stirred at 0° C. for 30 min. After completion, the residue was concentrated under reduced pressure to give the title compound (50 mg, 80% yield), which was used into the next step without further purification. Yellow solid; LCMS [ESI, M+1]: 739.

Step C. 4-(4-((1R,5S)-3,8-diazabicyclo[3.2.1]octan-3-yl)-8-fluoro-2-(((2R,7aS)-2-fluorohexahydro-1H-pyrrolizin-7a-yl)methoxy)pyrido[4,3-d]pyrimidin-7-yl)-5-ethynylnaphthalen-2-ol. To a mixture of 4-(4-((1R,5S)-3,8-diazabicyclo[3.2.1]octan-3-yl)-8-fluoro-2-(((2R,7aS)-2-fluorohexahydro-1H-pyrrolizin-7a-yl)methoxy)pyrido[4,3-d]pyrimidin-7-yl)-5-((triisopropylsilyl)ethynyl)naphthalen-2-ol (50 mg, 67.66 μmol, 1 eq) in DMF (2 mL) was added CsF (51.39 mg, 338.30 μmol, 12.47 μL, 5 eq) in one portion under N₂. The mixture was stirred at 20° C. for 1 hour. After completion, the mixture was purified by prep-HPLC (column: Waters Xbridge C18 150*50 mm*10 um; mobile phase: [water (10 mM NH₄HCO₃)-ACN]; B %: 25%-55%, 10 min) to give the title compound (7.28 mg, 18% yield). Yellow solid; ¹H NMR (400 MHz, METHANOL-d4) δ=9.01 (s, 1H), 7.83 (d, J=7.3 Hz, 1H), 7.52 (d, J=6.2 Hz, 1H), 7.44-7.38 (m, 1H), 7.34 (d, J=2.6 Hz, 1H), 7.18 (d, J=2.4 Hz, 1H), 5.42-5.22 (m, 1H), 4.70-4.54 (m, 4H), 4.36-4.20 (m, 2H), 3.78-3.70 (m, 2H), 3.29-3.14 (m, 3H), 3.09-2.99 (m, 2H), 2.40-2.21 (m, 2H), 2.19-2.11 (m, 1H), 2.07-1.96 (m, 2H), 1.96-1.77 (m, 5H); LCMS [ESI, M+1]: 583.

Example 244

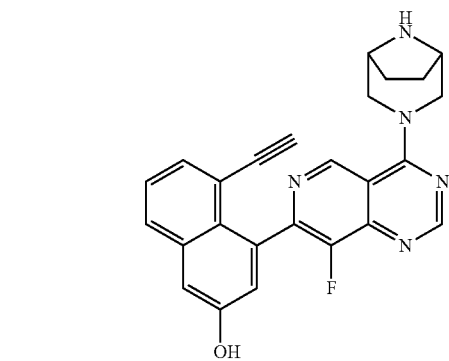 [SMILES: C#Cc1cccc2cc(O)cc(-c3ncc4c(N5CC6CCC(C5)N6)ncnc4c3F)c12]

4-(4-((1R,5S)-3,8-diazabicyclo[3.2.1]octan-3-yl)-8-fluoropyrido[4,3-d]pyrimidin-7-yl)-5-ethynylnaphthalen-2-ol

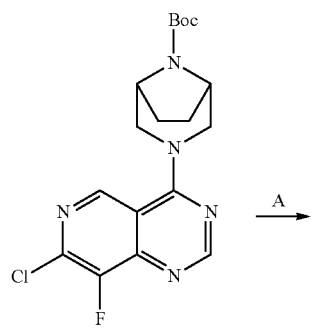

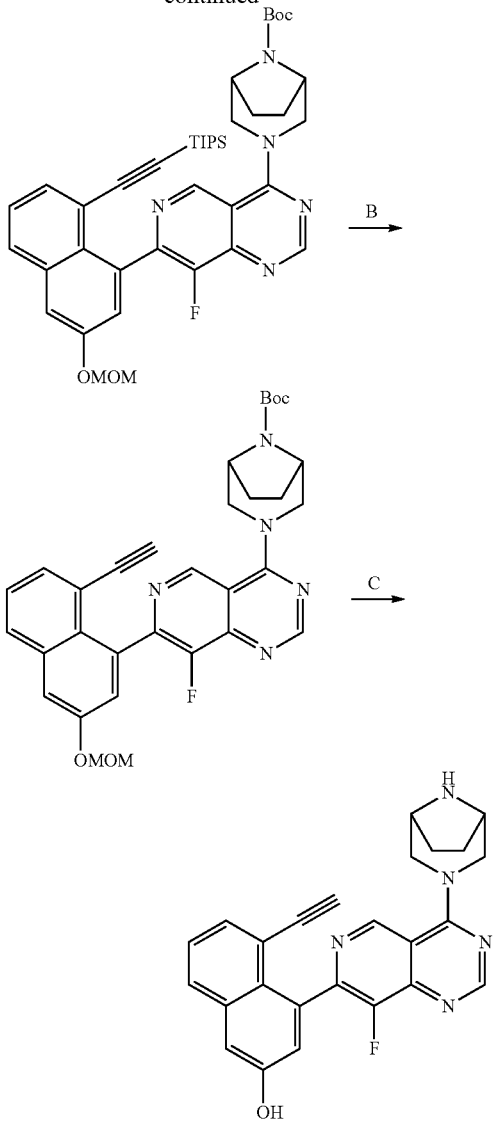

Step A. tert-butyl 3-[8-fluoro-7-[3-(methoxymethoxy)-8-(2-triisopropylsilylethynyl)-1-naphthyl]pyrido[4,3-d]pyrimidin-4-yl]-3,8-diazabicyclo[3.2.1]octane-8-carboxylate. A mixture of tert-butyl (1R,5S)-3-(7-chloro-8-fluoropyrido[4,3-d]pyrimidin-4-yl)-3,8-diazabicyclo[3.2.1]octane-8-carboxylate (150 mg, 381 μmol, 1.0 eq) and Cs₂CO₃ (372 mg, 1.14 mmol, 3.0 eq) in dioxane (9 mL) and H₂O (3 mL) was degassed. Then Pd(dppf)Cl₂ (27.9 mg, 38.1 μmol, 0.1 eq) and triisopropyl((6-(methoxymethoxy)-8-(4,4,5,5-tetramethyl-1,3,2-dioxaborolan-2-yl)naphthalen-1-yl)ethynyl)silane (282 mg, 571 μmol, 1.5 eq) were added and the mixture was stirred at 95° C. for 3.5 hours under N₂. After completion, the mixture was diluted with ethyl acetate (10 mL) and water (10 mL) and then separated. The aqueous phase was extracted with ethyl acetate (10 mL). The combined organic layer was washed with saturated brine (15 mL), dried over Na₂SO₄, filtered and concentrated under vacuum. The residue was purified by column chromatography (SiO₂, petroleum ether/ethyl acetate=1/1) and reversed phase flash [water (FA, 0.1%)/acetonitrile] to give the title compound (102 mg, 35% yield). Yellow oil. Rf=0.4 (3:1, petroleum ether/ethyl acetate). LCMS [ESI, M+1]: 726.

519

Step B. tert-butyl 3-[7-[8-ethynyl-3-(methoxymethoxy)-1-naphthyl]-8-fluoro-pyrido[4,3-d] pyrimidin-4-yl]-3,8-diazabicyclo[3.2.1]octane-8-carboxylate. To a mixture of 3-[8-fluoro-7-[3-(methoxymethoxy)-8-(2-triisopropylsilyl-ethynyl)-1-naphthyl] pyrido[4,3-d]pyrimidin-4-yl]-3,8-azabicyclo[3.2.1]octane-8-carboxylate (170 mg, 234 μmol, 1.0 eq) in DMF (3 mL) was added CsF (178 mg, 1.17 mmol, 43.2 μL, 5.0 eq). The mixture was stirred at 25° C. for 0.5 hour. After completion, the mixture was purified directly without work up. The residue was purified by reversed phase flash chromatography [water (FA, 0.1%)/acetonitrile] to give the title compound (130 mg, 97% yield). Yellow solid. LCMS [ESI, M+1]: 570.

Step C. 4-[4-(3,8-diazabicyclo[3.2.1]octan-3-yl)-8-fluoro-pyrido[4,3-d]pyrimidin-7-yl]-5-ethynyl-naphthalen-2-ol. To a mixture of tert-butyl 3-[7-[8-ethynyl-3-(methoxymethoxy)-1-naphthyl]-8-fluoro-pyrido[4,3-d]pyrimidin-4-yl]-3,8-diazabicyclo[3.2.1]octane-8-carboxylate (100 mg, 175 μmol, 1.0 eq) in acetonitrile (1 mL) was added HCl/dioxane (4 M, 2 mL, 45 eq) at 0° C. The mixture was stirred at 0° C. for 0.5 hours. After completion, the mixture was concentrated under vacuum and the pH was adjusted to 9 with concentrate NaHCO₃ (4 mL). Then the mixture was diluted with ethyl acetate (6 mL) and water (4 mL), and then separated. The aqueous phase was extracted with ethyl acetate (2×5 mL), and the combine organic layer was washed with brine (8 mL), dried over Na₂SO₄, filtered and concentrated under vacuum. The residue was purified by prep-HPLC (column: Waters Xbridge 150*25 mm*5um; mobile phase: [water (10 mM NH₄HCO₃)-ACN]; B %: 20%-50%, 10 min) to give the title compound (30.2 mg, 40% yield). orange solid. ¹H NMR (400 MHz, CDCl₃-d) δ=9.06 (s, 1H), 8.75 (s, 1H), 7.72 (d, J=8.0 Hz, 1H), 7.53 (d, J=6.8 Hz, 1H), 7.33 (t, J=7.6 Hz, 1H), 7.27 (s, 2H), 4.72 (br d, J=12.0 Hz, 1H), 4.51 (br d, J=12.0 Hz, 1H), 3.79-3.71 (br d, J=12.0 Hz, 1H), 3.67 (br s, 2H), 3.60 (br d, J=12.0 Hz, 1H), 2.44 (s, 1H), 1.82-1.76 (m, 3H), 1.64-1.57 (m, 1H). LCMS [ESI, M/2+1, M+1]: 214, 426.

Example 245

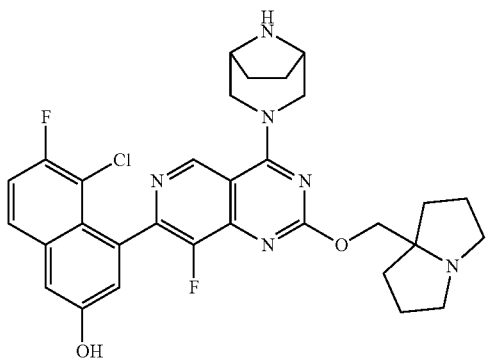 [SMILES: Oc1cc(-c2ncc3c(N4CC5CCC(C4)N5)nc(OCC45CCCN4CCC5)nc3c2F)c2c(Cl)c(F)ccc2c1]

520

4-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)-5-chloro-6-fluoronaphthalen-2-ol

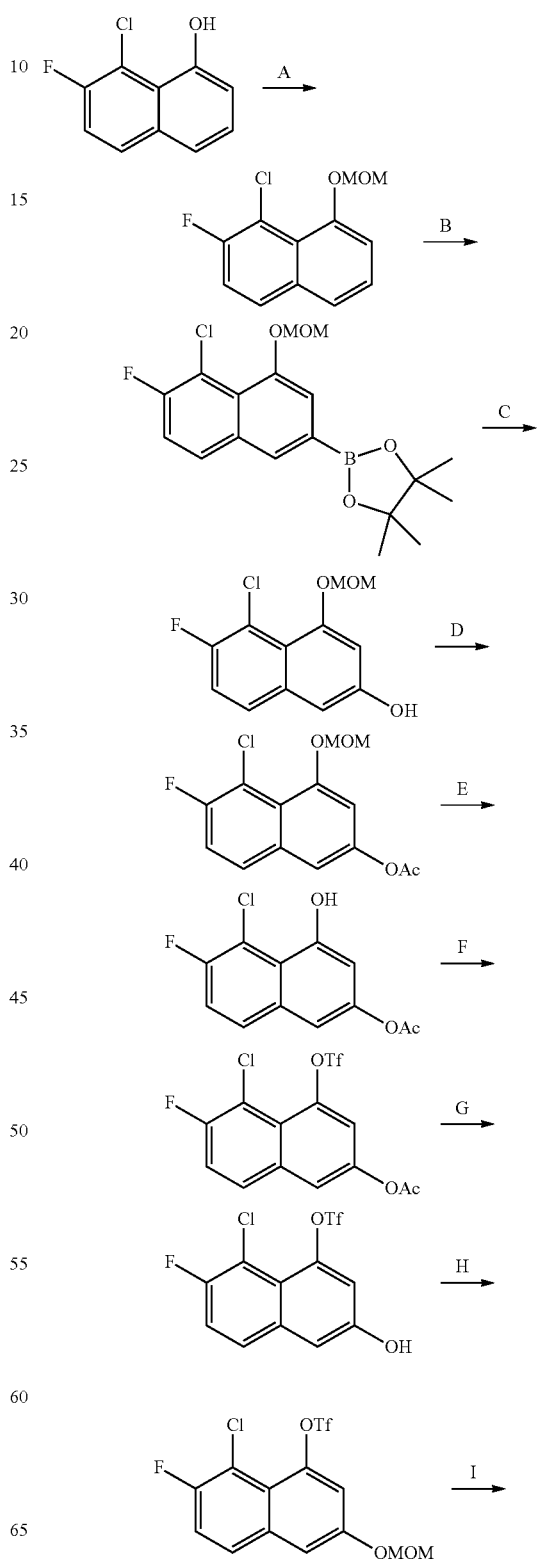

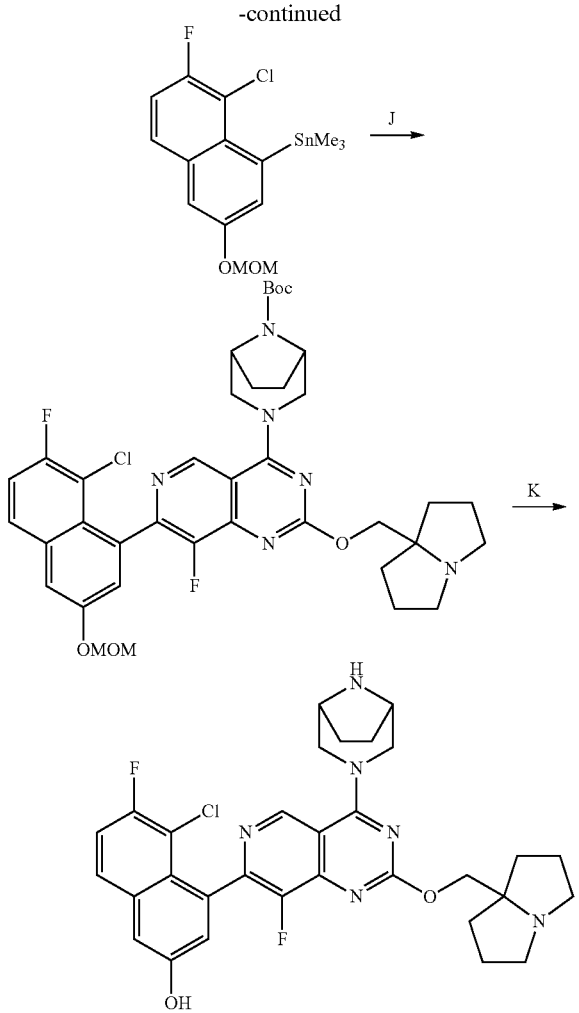

Step A. 1-chloro-2-fluoro-8-(methoxymethoxy)naphthalene. To a mixture of 8-chloro-7-fluoronaphthalen-1-ol (50.0 g, 254 mmol, 1.0 eq) and DCM (1000 mL) were added DIEA (98.7 g, 763 mmol, 3.0 eq) and chloro(methoxy)methane (41.0 g, 509 mmol, 2.0 eq) in one portion at 0° C. under N$_2$. The mixture was stirred at 25° C. for 1 hour. After completion, the mixture was quenched with water (800 mL). The organic phase was separated, and concentrated. To the residue was added saturated NH$_4$Cl solution (600 mL). The mixture was extracted with ethyl acetate (500 mL×2). The combined organic phase was dried over anhydrous sodium sulfate, filtered, concentrated, and purified by column chromatography (SiO$_2$, Petroleum ether/Ethyl acetate=30/1 to 10/1) to give the title compound (52.0 g, 82% yield). Colorless oil. $^1$H NMR (400 MHz, CHLOROFORM-d) δ=7.66 (dd, J=5.6, 9.2 Hz, 1H), 7.45 (dd, J=0.8, 8.4 Hz, 1H), 7.33 (t, J=8.0 Hz, 1H), 7.29-7.24 (m, 1H), 7.19 (d, J=7.6 Hz, 1H), 5.30 (s, 2H), 3.57 (s, 3H).

Step B. 2-[5-chloro-6-fluoro-4-(methoxymethoxy)-2-naphthyl]-4,4,5,5-tetramethyl-1,3,2-dioxaborolane. A mixture of 1-chloro-2-fluoro-8-(methoxymethoxy)naphthalene (25.0 g, 104 mmol, 1.0 eq), 4,4,4',4',5,5,5',5'-octamethyl-2,2'-bi(1,3,2-dioxaborolane) (26.4 g, 104 mmol, 1.0 eq), Ir(OMe)(cod))$_2$ (3.44 g, 5.19 mmol, 0.05 eq), dtbbpy (3.35 g, 12.5 mmol, 0.12 eq) in THF (500 mL) was degassed, and then the mixture was stirred at 60° C. for 1 hour. After completion, the mixture was concentrated to give a residue. The residue was purified by column chromatography (SiO$_2$, Petroleum ether/Ethyl acetate=20/1 to 8/1) to give the title compound (40.0 g, crude). Yellow oil.

Step C. 5-chloro-6-fluoro-4-(methoxymethoxy)naphthalen-2-ol. To a solution of 2-[5-chloro-6-fluoro-4-(methoxymethoxy)-2-naphthyl]-4,4,5,5-tetramethyl-1,3,2-dioxaborolane (40.0 g, crude) in THF (400 mL) and H$_2$O (200 mL) were added H$_2$O$_2$ (100 g, 882 mmol, 30% purity, 8.08 eq) and AcOH (328 g, 5.46 mol, 50.0 eq) at 10° C. The mixture was stirred at 25° C. for 1 hour. After completion, the mixture was quenched with saturated Na$_2$SO$_3$ solution (800 mL×2) and extracted with ethyl acetate (500 mL×2). The combined organic phases were washed with saturated brine (800 mL), dried over anhydrous sodium sulfate, filtered and concentrated to give a residue. The residue was purified by column chromatography (SiO$_2$, Petroleum ether/Ethyl acetate=20/1 to 8/1) to give the title compound (3.95 g, two steps 15% yield). Off-white solid. $^1$H NMR (400 MHz, CHLOROFORM-d) δ=7.49 (dd, J=5.2, 8.8 Hz, 1H), 7.24 (t, J=8.8 Hz, 1H), 6.89 (d, J=2.0 Hz, 1H), 6.82 (d, J=2.4 Hz, 1H), 5.32 (s, 2H), 5.27 (br s, 1H), 3.60 (s, 3H). LCMS [ESI, M+1]: 257

Step D. [5-chloro-6-fluoro-4-(methoxymethoxy)-2-naphthyl] acetate. To the solution of 5-chloro-6-fluoro-4-(methoxymethoxy)naphthalen-2-ol (0.500 g, 1.95 mmol, 1.0 eq), TEA (394 mg, 3.90 mmol, 2.0 eq), DMAP (23.8 mg, 195 μmol, 0.1 eq) in DCM (10 mL) was added dropwise acetyl chloride (229 mg, 2.92 mmol, 1.5 eq) at 0° C. The reaction mixture was then warmed to 25° C. and stirred for 0.5 hour. After completion, the mixture was diluted with water (20 mL). The organic layer was separated, and the aqueous phase was extracted with DCM (30 mL×2). The combined organic phase was washed with brine, dried over anhydrous sodium sulfate, filtered and concentrated. The residue was purified by column chromatography (SiO$_2$, Petroleum ether/Ethyl acetate=20/1 to 6/1) to give the title compound (540 mg, 93% yield). White solid; $^1$H NMR (400 MHz, CHLOROFORM-d) δ=7.64 (dd, J=5.2, 8.8 Hz, 1H), 7.32 (t, J=8.8 Hz, 1H), 7.25 (d, J=2.0 Hz, 1H), 7.01 (d, J=2.0 Hz, 1H), 5.34 (s, 2H), 3.59 (s, 3H), 2.35 (s, 3H).

Step E. (5-chloro-6-fluoro-4-hydroxy-2-naphthyl) acetate. To the solution of [5-chloro-6-fluoro-4-(methoxymethoxy)-2-naphthyl] acetat (540 mg, 1.81 mmol, 1.0 eq) in ACN (5 mL) was added HCl·dioxane (4 M, 5 mL, 11.1 eq) at 0° C., and then the mixture was stirred at 0° C. for 1 hr. After completion, the mixture was concentrated. The residue was quenched with saturated NaHCO$_3$ solution (15 mL) and extracted with ethyl acetate (30 mL×2). The combined organic phase was washed with brine 50 mL, dried over anhydrous sodium sulfate, filtered and concentrated to give the title compound (400 mg, 86% yield) which was used in the next step without further purification. White solid; $^1$H NMR (400 MHz, CHLOROFORM-d) δ=8.06 (s, 1H), 7.70 (dd, J=5.2, 9.2 Hz, 1H), 7.31 (t, J=8.8 Hz, 1H), 7.19 (d, J=2.4 Hz, 1H), 6.87 (d, J=2.0 Hz, 1H), 2.35 (s, 3H).

Step F. [5-chloro-6-fluoro-4-(trifluoromethylsulfonyloxy)-2-naphthyl] acetate. To the solution of (5-chloro-6-fluoro-4-hydroxy-2-naphthyl) acetate (400 mg, 1.57 mmol, 1 eq), DIPEA (609 mg, 4.71 mmol, 3.0 eq) in DCM (8 mL) was added dropwise trifluoromethylsulfonyl trifluoromethanesulfonate (665 mg, 2.36 mmol, 1.5 eq) at −40° C., and then the reaction was warmed to 25° C. and stirred for 0.5 hour. After completion, the mixture was quenched with water (15 mL) and extracted with DCM (20 mL×2). The combined organic phase was washed with brine 30 mL, dried over anhydrous sodium sulfate, filtered and concentrated to give a residue. The residue was purified by column chromatography (SiO₂, Petroleum ether/Ethyl acetate=15/1 to 3/1) to give the title compound (270 mg, 44% yield). Yellow solid. ¹H NMR (400 MHz, CHLOROFORM-d) δ=7.79 (dd, J=5.2, 9.0 Hz, 1H), 7.71 (d, J=2.0 Hz, 1H), 7.50-7.40 (m, 2H), 2.39 (s, 3H).

Step G. (8-chloro-7-fluoro-3-hydroxy-1-naphthyl) trifluoromethanesulfonate. To the mixture of [5-chloro-6-fluoro-4-(trifluoromethylsulfonyloxy)-2-naphthyl] acetate (1.70 g, 4.40 mmol, 1.0 eq), H₂O (8 mL) and THF (30 mL) was added LiOH (211 mg, 8.79 mmol, 2.0 eq) at 0° C. The mixture was stirred at 0° C. for 1 hr. After completion, the mixture was concentrated, and its pH was adjusted to 6 with AcOH. The resulting mixture was extracted with ethyl acetate (60 mL×2), and the combined organic phase was washed with brine 50 mL, dried over anhydrous sodium sulfate, filtered and concentrated to give the title compound (1.80 g, crude). Brown oil; ¹H NMR (400 MHz, CHLOROFORM-d) δ=7.62 (dd, J=5.2, 8.8 Hz, 1H), 7.35 (t, J=8.8 Hz, 1H), 7.28 (d, J=2.4 Hz, 1H), 7.23 (d, J=2.4 Hz, 1H)

Step H. 8-chloro-7-fluoro-3-(methoxymethoxy)naphthalen-1-yl trifluoromethanesulfonate. To the solution of (8-chloro-7-fluoro-3-hydroxy-1-naphthyl) trifluoromethanesulfonate (1.80 g, crude) and DIEA (2.02 g, 15.7 mmol, 3.0 eq) in DCM (40 mL) was added MOMCl (841 mg, 10.5 mmol, 2.0 eq) at 0° C., the mixture was stirred at 0° C. for 1 hr. After completion, the reaction was quenched by water 40 mL at 0° C., and then extracted with DCM 100 mL. The organic layer was washed with brine 60 mL, dried over Na₂SO₄, filtered and concentrated under reduced pressure to give a residue. The residue was purified by column chromatography (SiO₂, Petroleum ether/Ethyl acetate=10/1 to 6/1) to give the title compound (920 mg, two steps 54% yield) as a yellow oil. ¹H NMR (400 MHz, CHLOROFORM-d) δ=7.70 (dd, J=5.2, 8.8 Hz, 1H), 7.47 (d, J=2.4 Hz, 1H), 7.42-7.35 (m, 2H), 5.30 (s, 2H), 3.53 (s, 3H).

Step I. (8-chloro-7-fluoro-3-(methoxymethoxy)naphthalen-1-yl)trimethylstannane. To the mixture of 8-chloro-7-fluoro-3-(methoxymethoxy)naphthalen-1-yl trifluoromethanesulfonate (620 mg, 1.59 mmol, 1.0 eq), trimethyl(trimethylstannyl) stannane (1.57 g, 4.78 mmol, 3.0 eq), LiCl (203 mg, 4.78 mmol, 3.0 eq) in toluene (15 mL) was added Pd(PPh₃)₄ (184 mg, 160 µmol, 0.1 eq) under N₂. The mixture was degassed and stirred at 110° C. for 16 hours. After completion, the mixture was quenched with water (50 mL) and extracted with ethyl acetate (60 mL×2). The combined organic phase was washed with saturated brine 60 mL, dried over anhydrous sodium sulfate, filtered and concentrated to give a residue. The residue was purified by column chromatography (SiO₂, Petroleum ether/Ethyl acetate=1/0 to 10/1). Colorless oil. Then the oil was purified by reversed phase flash chromatography [water (FA 0.1%)/acetonitrile] to give the title compound (416 mg, 64% yield). Colorless oil. ¹H NMR (400 MHz, CHLOROFORM-d) δ=7.70-7.64 (m, 1H), 7.59 (d, J=2.4 Hz, 1H), 7.38 (d, J=2.4 Hz, 1H), 7.31 (t, J=8.8 Hz, 1H), 5.30 (s, 2H), 3.54 (s, 3H), 0.44 (s, 9H).

Step J. (1R,5S)-tert-butyl 3-(7-(8-chloro-7-fluoro-3-(methoxymethoxy)naphthalen-1-yl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate. To the mixture of tert-butyl (1R,5S)-3-(7-chloro-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (216 mg, 405 µmol, 1.0 eq), (8-chloro-7-fluoro-3-(methoxymethoxy)naphthalen-1-yl)trimethylstannane (245 mg, 607 µmol, 1.5 eq), CuI (23.2 mg, 122 µmol, 0.3 eq), BINAP (50.5 mg, 81.1 µmol, 0.2 eq) in toluene (2 mL) was added Pd(dppf)Cl₂ (29.7 mg, 40.5 µmol, 0.1 eq) under N₂, and the mixture was stirred at 90° C. for 5.5 hours. After completion, the reaction mixture was quenched with water 50 mL and extracted with ethyl acetate (50 mL). The aqueous layer was extracted with ethyl acetate (60 mL×2), and the combined organic phase was dried over anhydrous sodium sulfate, filtered and concentrated to give a residue. The residue was purified by column chromatography (Al₂O₃, Petroleum ether/Ethyl acetate=1/1 to 0/1, then MeOH/Ethyl acetate=1:10) to give a yellow oil. Then the oil was purified by reversed phase flash chromatography [water (FA 0.10%)/acetonitrile] to give title compound (76.7 mg, 25% yield). Colourless oil. LCMS [ESI, M+1]:737.

Step K. 4-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)-5-chloro-6-fluoronaphthalen-2-ol. To the solution of (1R,5S)-tert-butyl 3-(7-(8-chloro-7-fluoro-3-(methoxymethoxy)naphthalen-1-yl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (60.0 mg, 81.4 µmol, 1.0 eq) in ACN (1 mL) was added HCl/dioxane (4 M, 2 mL, 98.3 eq) at 0° C., and the mixture was stirred at 0° C. for 0.5 hour. After completion, the reaction mixture was concentrated at 25° C. The residue was purified by prep-HPLC (column: 3_Phenomenex Luna C18 75*30 mm*3 um; mobile phase: [water (0.225% FA)-ACN]; B %: 7%-27%, 8 min) to give title compound (25.7 mg, 45% yield). Yellow solid. ¹H NMR (400 MHz, METHANOL-d4) δ=9.13 (s, 1H), 7.83 (dd, J=5.2, 8.8 Hz, 1H), 7.45-7.37 (m, 2H), 7.22 (d, J=2.4 Hz, 1H), 4.78 (br s, 2H), 4.67 (s, 2H), 4.00 (br s, 2H), 3.87 (br t, J=12.0 Hz, 2H), 3.74-3.64 (m, 2H), 3.28 (br s, 2H), 2.39-2.28 (m, 2H), 2.27-1.94 (m, 10H). LCMS [ESI, M+1]: 593.

Example 246

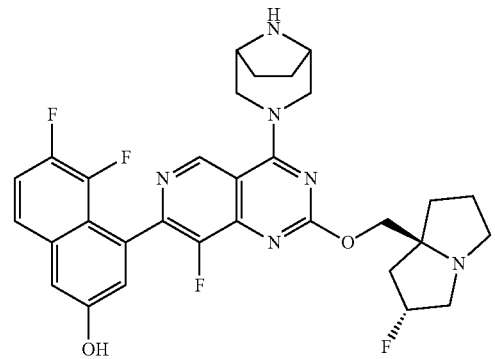 [SMILES: Oc1cc(-c2ncc3c(N4CC5CCC(C4)N5)nc(OC[C@@]45CCCN4C[C@H](F)C5)nc3c2F)c2c(F)c(F)ccc2c1]

4-(4-((1R,5S)-3,8-diazabicyclo[3.2.1]octan-3-yl)-8-fluoro-2-(((2R,7aS)-2-fluorohexahydro-1H-pyrrolizin-7a-yl)methoxy)pyrido[4,3-d]pyrimidin-7-yl)-5,6-difluoronaphthalen-2-ol

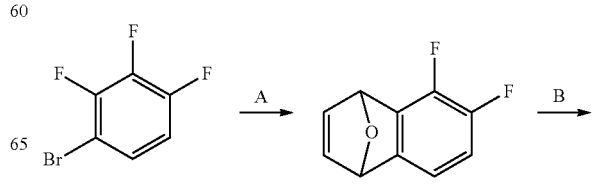

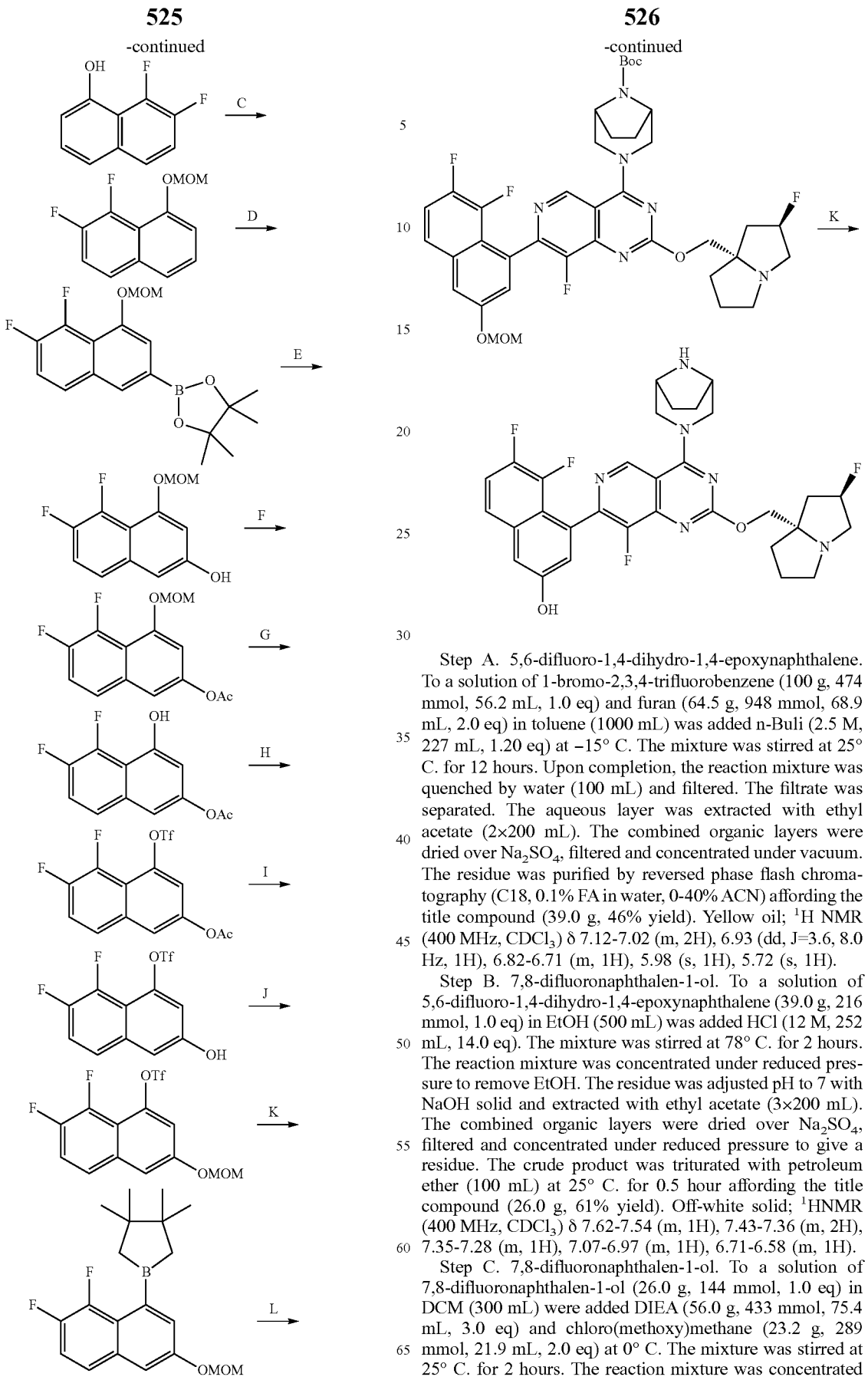

Step A. 5,6-difluoro-1,4-dihydro-1,4-epoxynaphthalene. To a solution of 1-bromo-2,3,4-trifluorobenzene (100 g, 474 mmol, 56.2 mL, 1.0 eq) and furan (64.5 g, 948 mmol, 68.9 mL, 2.0 eq) in toluene (1000 mL) was added n-Buli (2.5 M, 227 mL, 1.20 eq) at −15° C. The mixture was stirred at 25° C. for 12 hours. Upon completion, the reaction mixture was quenched by water (100 mL) and filtered. The filtrate was separated. The aqueous layer was extracted with ethyl acetate (2×200 mL). The combined organic layers were dried over $Na_2SO_4$, filtered and concentrated under vacuum. The residue was purified by reversed phase flash chromatography (C18, 0.1% FA in water, 0-40% ACN) affording the title compound (39.0 g, 46% yield). Yellow oil; $^1$H NMR (400 MHz, $CDCl_3$) δ 7.12-7.02 (m, 2H), 6.93 (dd, J=3.6, 8.0 Hz, 1H), 6.82-6.71 (m, 1H), 5.98 (s, 1H), 5.72 (s, 1H).

Step B. 7,8-difluoronaphthalen-1-ol. To a solution of 5,6-difluoro-1,4-dihydro-1,4-epoxynaphthalene (39.0 g, 216 mmol, 1.0 eq) in EtOH (500 mL) was added HCl (12 M, 252 mL, 14.0 eq). The mixture was stirred at 78° C. for 2 hours. The reaction mixture was concentrated under reduced pressure to remove EtOH. The residue was adjusted pH to 7 with NaOH solid and extracted with ethyl acetate (3×200 mL). The combined organic layers were dried over $Na_2SO_4$, filtered and concentrated under reduced pressure to give a residue. The crude product was triturated with petroleum ether (100 mL) at 25° C. for 0.5 hour affording the title compound (26.0 g, 61% yield). Off-white solid; $^1$HNMR (400 MHz, $CDCl_3$) δ 7.62-7.54 (m, 1H), 7.43-7.36 (m, 2H), 7.35-7.28 (m, 1H), 7.07-6.97 (m, 1H), 6.71-6.58 (m, 1H).

Step C. 7,8-difluoronaphthalen-1-ol. To a solution of 7,8-difluoronaphthalen-1-ol (26.0 g, 144 mmol, 1.0 eq) in DCM (300 mL) were added DIEA (56.0 g, 433 mmol, 75.4 mL, 3.0 eq) and chloro(methoxy)methane (23.2 g, 289 mmol, 21.9 mL, 2.0 eq) at 0° C. The mixture was stirred at 25° C. for 2 hours. The reaction mixture was concentrated under reduced pressure to remove DCM. The residue was diluted with H₂O (200 mL) and extracted with ethyl acetate (3×200 mL). The combined organic layers were washed with saturated brine (300 mL), dried over Na₂SO₄, filtered and concentrated under reduced pressure to give a residue. The residue was purified by column chromatography (SiO₂, Petroleum ether/Ethyl acetate=100/1 to 5/1) affording the title compound (28.8 g, 89% yield). White solid; ¹H NMR (400 MHz, CDCl₃) δ 7.57-7.51 (m, 1H), 7.48-7.43 (m 1H), 7.39-7.29 (m, 2H), 7.17 (d, J=8.0 Hz, 1H), 5.37 (s, 2H), 3.60 (s, 3H).

Step D. 2-(5,6-difluoro-4-(methoxymethoxy)naphthalen-2-yl)-4,4,5,5-tetramethyl-1,3,2-dioxaborolane. To a solution of 7,8-difluoronaphthalen-1-ol (1.75 g, 7.81 mmol, 1 eq) and 4,4,5,5-tetramethyl-1,3,2-dioxaborolane (2.50 g, 19.5 mmol, 2.83 mL, 2.5 eq) in THF (20.0 mL) was added (Ir(OMe)(cod))₂ (517 mg, 781 μmol, 0.1 eq) and dtbbpy (251 mg, 937 μmol, 0.12 eq). The mixture was stirred at 70° C. for 2 hours. Upon completion, the reaction mixture was concentrated under vacuum affording the title compound (22 g, crude). Black brown oil.

Step E. 5,6-difluoro-4-(methoxymethoxy)naphthalen-2-ol. To a solution of 2-(5,6-difluoro-4-(methoxymethoxy)naphthalen-2-yl)-4,4,5,5-tetramethyl-1,3,2-dioxaborolane (22.0 g, 62.8 mmol, 1 eq) in THF (200 mL) were added AcOH (264 g, 4.40 mol, 252 mL, 70 eq) and H₂O₂ (64.1 g, 565 mmol, 54.3 mL, 30% purity, 9 eq) at 0° C. The mixture was stirred at 25° C. for 1 hour. Upon completion, the reaction mixture was diluted with saturated NaHSO₃ aqueous (500 mL) and extracted with EA (3×200 mL). The combined organic layers were dried over Na₂SO₄, filtered and concentrated under vacuum. The residue was purified by column chromatography (SiO₂, PE/EA=100/1 to 5/1) and re-purified by prep-HPLC (column: Phenomenex luna c18 250 mm*100 mm*15 um; mobile phase: [water (0.05% HCl)-ACN]; B %: 35%-60%, 25 min) affording the title compound (700 mg, 2.89 mmol, two steps 4.6% yield, 99.2% purity). Yellow solid; ¹H NMR (400 MHz, CDCl₃) δ=7.33-7.28 (m, 1H), 7.26-7.20 (m, 1H), 6.82 (d, J=2.0 Hz, 1H), 6.76 (t, J=2.0 Hz, 1H), 5.33 (s, 2H), 5.25 (br s, 1H), 3.56 (s, 3H); LCMS [ESI, M−1]: 239.0.

Step F. 5,6-difluoro-4-(methoxymethoxy)naphthalen-2-yl acetate. To a solution of 5,6-difluoro-4-(methoxymethoxy)naphthalen-2-ol (740 mg, 3.08 mmol, 1 eq) in DCM (4 mL) were added Et₃N (623 mg, 6.16 mmol, 858 μL, 2 eq) and DMAP (37.6 mg, 308 μmol, 0.1 eq). Then acetyl chloride (484 mg, 6.16 mmol, 440 μL, 2 eq) in DCM (3.00 mL) was added drop-wise at 0° C. The mixture was stirred at 25° C. for 0.5 hour. Upon completion, the reaction mixture was diluted with water (15.0 mL) and extracted with DCM (3×5.00 mL). The combined organic layers were dried over Na₂SO₄, filtered and concentrated under vacuum. The residue was purified by column chromatography (SiO₂, PE/EA=100/1 to 20/1) affording the title compound (710 mg, 2.39 mmol, 78% yield, 95.0% purity). Yellow oil; ¹H NMR (400 MHz, CDCl₃) δ=7.51-7.44 (m, 1H), 7.37-7.29 (m, 1H), 7.23-7.19 (m, 1H), 6.95 (d, J=2.0 Hz, 1H), 5.36 (s, 2H), 3.58 (s, 3H), 2.35 (s, 3H).

Step G. 5,6-difluoro-4-hydroxynaphthalen-2-yl acetate. To a solution of 5,6-difluoro-4-(methoxymethoxy)naphthalen-2-yl acetate (710 mg, 2.52 mmol, 1 eq) in EA (1.00 mL) was added HCl/EA (4 M, 7.00 mL, 11.13 eq) at −40° C. The mixture was stirred at −40° C. for 0.5 hour and at 0° C. for another 0.5 hour. Upon completion, the reaction mixture was diluted with saturated NaHCO₃ (50.0 mL) and extracted with EA (3×20.0 mL). The combined organic layers were washed with brine (30.0 mL), dried over Na₂SO₄, filtered and concentrated under vacuum affording the title compound (600 mg, crude). Yellow solid; LCMS [ESI, M−1]: 237.0.

Step H. 5,6-difluoro-4-(((trifluoromethyl)sulfonyl)oxy) naphthalen-2-yl acetate. To a solution of 5,6-difluoro-4-hydroxynaphthalen-2-yl acetate (580 mg, 2.44 mmol, 1 eq) and DIPEA (944 mg, 7.31 mmol, 1.27 mL, 3 eq) in DCM (6.00 mL) was added Tf₂O (824 mg, 2.92 mmol, 482 μL, 1.2 eq) at −78° C. The mixture was stirred at −78° C. for 0.5 hour. Upon completion, the reaction mixture was diluted with water (20.0 mL) and extracted with DCM (3×15.0 mL). The combined organic layers were washed with brine (20.0 mL), dried over Na₂SO₄, filtered and concentrated under vacuum. The residue was purified by column chromatography (SiO₂, PE/EA=1/0 to 30/1) affording the title compound (450 mg, 1.15 mmol, two steps 47% yield, 95.0% purity). White solid; ¹H NMR (400 MHz, CDCl₃) δ=7.69-7.67 (m, 1H), 7.66-7.61 (m, 1H), 7.52-7.44 (m, 1H), 7.36 (d, J=2.0 Hz, 1H), 2.39 (s, 3H).

Step I. 7,8-difluoro-3-hydroxynaphthalen-1-yl trifluoromethanesulfonate. To a solution of 5,6-difluoro-4-(((trifluoromethyl)sulfonyl)oxy)naphthalen-2-yl acetate (430 mg, 1.16 mmol, 1 eq) in THF (3.00 mL) and H₂O (1.00 mL) was added LiOH (33.4 mg, 1.39 mmol, 1.2 eq) at 0° C. The mixture was stirred at 0° C. for 0.5 hour. Upon completion, the reaction mixture was adjusted pH~6 with AcOH. The mixture was diluted with water (20 mL) and extracted with EA (3×20.0 mL). The combined organic layers were washed with brine (30.0 mL), dried over Na₂SO₄, filtered and concentrated under vacuum affording the title compound (400 mg, crude). Yellow oil.

Step J. 7,8-difluoro-3-(methoxymethoxy)naphthalen-1-yl trifluoromethanesulfonate. To a solution of 7,8-difluoro-3-hydroxynaphthalen-1-yl trifluoromethanesulfonate (400 mg, 1.22 mmol, 1 eq) in DCM (5.00 mL) was added DIPEA (473 mg, 3.66 mmol, 637 μL, 3 eq) at 0° C., and then MOMCl (196 mg, 2.44 mmol, 185 μL, 2 eq) was added drop-wise. The mixture was stirred at 0° C. for 1 hour. Upon completion, the reaction mixture was diluted with water (30.0 mL) and extracted with DCM (3×20.0 mL). The combined organic layers were washed with brine (30.0 mL), dried over Na₂SO₄, filtered and concentrated under vacuum. The residue was purified by column chromatography (SiO₂, PE/EA=1/0 to 30/1) affording the title compound (350 mg, 846 μmol, 69% yield, 90.0% purity). White solid; ¹H NMR (400 MHz, CDCl₃) δ=7.58-7.52 (m, 1H), 7.46-7.44 (m, 1H), 7.43-7.36 (m, 1H), 7.29 (d, J=2.0 Hz, 1H), 5.30 (s, 2H), 3.54 (s, 3H).

Step K. 2-(7,8-difluoro-3-(methoxymethoxy)naphthalen-1-yl)-4,4,5,5-tetramethyl-1,3,2-dioxaborolane. To a solution of 7,8-difluoro-3-(methoxymethoxy)naphthalen-1-yl trifluoromethanesulfonate (330 mg, 886 μmol, 1 eq) and 4,4,5,5-tetramethyl-2-(4,4,5,5-tetramethyl-1,3,2-dioxaborolan-2-yl)-1,3,2-dioxaborolane (450 mg, 1.77 mmol, 2 eq) in DMF (4.00 mL) were added Pd(dppf)Cl₂ (64.9 mg, 88.7 μmol, 0.1 eq) and KOAc (435 mg, 4.43 mmol, 5 eq). The mixture was stirred at 80° C. for 12 hours under N₂ atmosphere. Upon completion, the reaction mixture was diluted with water (20.0 mL) and extracted with EA (3×10.0 mL). The combined organic layers were washed with brine (20.0 mL), dried over Na₂SO₄, filtered and concentrated under vacuum. The residue was purified by column chromatography (SiO₂, PE/EA=1/0 to 100/1) affording the title compound (230 mg, 624 μmol, 70% yield, 95.0% purity). White solid; ¹H NMR (400 MHz, CDCl₃) δ=7.49-7.44 (m, 1H), 7.44-7.41 (m, 1H), 7.41-7.38 (m, 1H), 7.33-7.27 (m, 1H), 5.29 (s, 2H), 3.51 (s, 3H), 1.45 (s, 12H).

Step L. (1R,5S)-tert-butyl 3-(7-(7,8-difluoro-3-(methoxymethoxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-3,8-diazabicyclo[3.2.1]octane-8-carboxylate. To a solution of tert-butyl (1R,5S)-3-(7-chloro-8-fluoro-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (157 mg, 286 μmol, 1 eq) and 2-(7,8-difluoro-3-(methoxymethoxy)naphthalen-1-yl)-4,4,5,5-tetramethyl-1,3,2-dioxaborolane (200 mg, 571 μmol, 2 eq) in H$_2$O (500 ul) and dioxane (3.00 mL) were added K$_3$PO$_4$ (182 mg, 857 μmol, 57.1 μL, 3 eq), 4-di-tert-butylphosphanyl-N,N-dimethyl-aniline (15.2 mg, 57.1 μmol, 0.2 eq) and Pd$_2$(dba)$_3$ (26.2 mg, 28.6 μmol, 0.1 eq) under N$_2$ atmosphere. The mixture was stirred at 70° C. for 12 hours under N$_2$ atmosphere. Upon completion, the reaction mixture was filtered. The filtrate was diluted with water (20.0 mL) and extracted with EA (3×10.0 mL). The combined organic layers were washed with brine (15.0 mL), dried over Na$_2$SO$_4$, filtered and concentrated under vacuum. The residue was purified by prep-TLC (SiO$_2$, DCM/MeOH=10/1) affording the title compound (100 mg, 126 μmol, 44% yield, 93.8% purity). Yellow oil; LCMS [ESI, M+1]: 739.4.

Step M. 4-(4-((1R,5S)-3,8-diazabicyclo[3.2.1]octan-3-yl)-8-fluoro-2-(((2R,7aS)-2-fluorohexahydro-1H-pyrrolizin-7a-yl)methoxy)pyrido[4,3-d]pyrimidin-7-yl)-5,6-difluoronaphthalen-2-ol. A solution of (1R,5S)-tert-butyl 3-(7-(7,8-difluoro-3-(methoxymethoxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-3,8-diazabicyclo[3.2.1]octane-8-carboxylate (90.0 mg, 122 μmol, 1 eq) in HCl·EtOAc (2.00 mL) was stirred at 0° C. for 1 hour. Upon completion, the reaction mixture was diluted with saturated NaHCO$_3$ (20.0 mL) and extracted with ethyl acetate (3×10.0 mL). The combined organic layers were washed with brine (15.0 mL), dried over Na$_2$SO$_4$, filtered and concentrated under vacuum. The residue was purified by prep-HPLC (column: Waters Xbridge BEH C18 100*25 mm*5 um; mobile phase: [water (10 mM NH$_4$HCO$_3$)-ACN]; B %: 30%-70%, 10 min) affording the title compound (18.8 mg, 31.0 μmol, 25% yield, 98.4% purity). White solid; $^1$H NMR (400 MHz, MeOD-d4) δ=9.06 (s, 1H), 7.66-7.56 (m, 1H), 7.46-7.35 (m, 1H), 7.34-7.31 (m, 1H), 7.23 (d, J=2.0 Hz, 1H), 5.44-5.20 (m, 1H), 4.69-4.54 (m, 2H), 4.38-4.18 (m, 2H), 3.82-3.58 (m, 4H), 3.27-3.12 (m, 3H), 3.08-2.94 (m, 1H), 2.41-2.09 (m, 3H), 2.07-1.69 (m, 7H); LCMS [ESI, M+1]: 595.1.

Example 247

4-((1R,5S)-3,8-diazabicyclo[3.2.1]octan-3-yl)-7-(8-(2,2-difluoroethyl)naphthalen-1-yl)-8-fluoro-2-((hexahydro-1H-pyrrolizin-7a-yl)methoxy)pyrido[4,3-d]pyrimidine

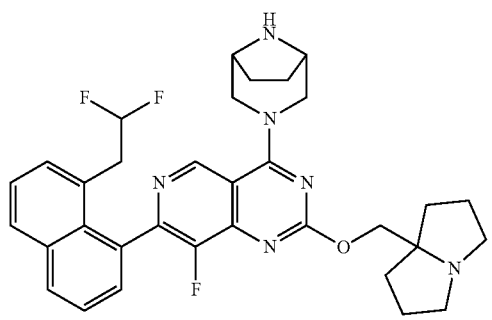 [SMILES: Fc1c(-c2cccc3cccc(CC(F)F)c23)ncc2c(N3CC4CCC(C3)N4)nc(OCC34CCCN3CCC4)nc12]

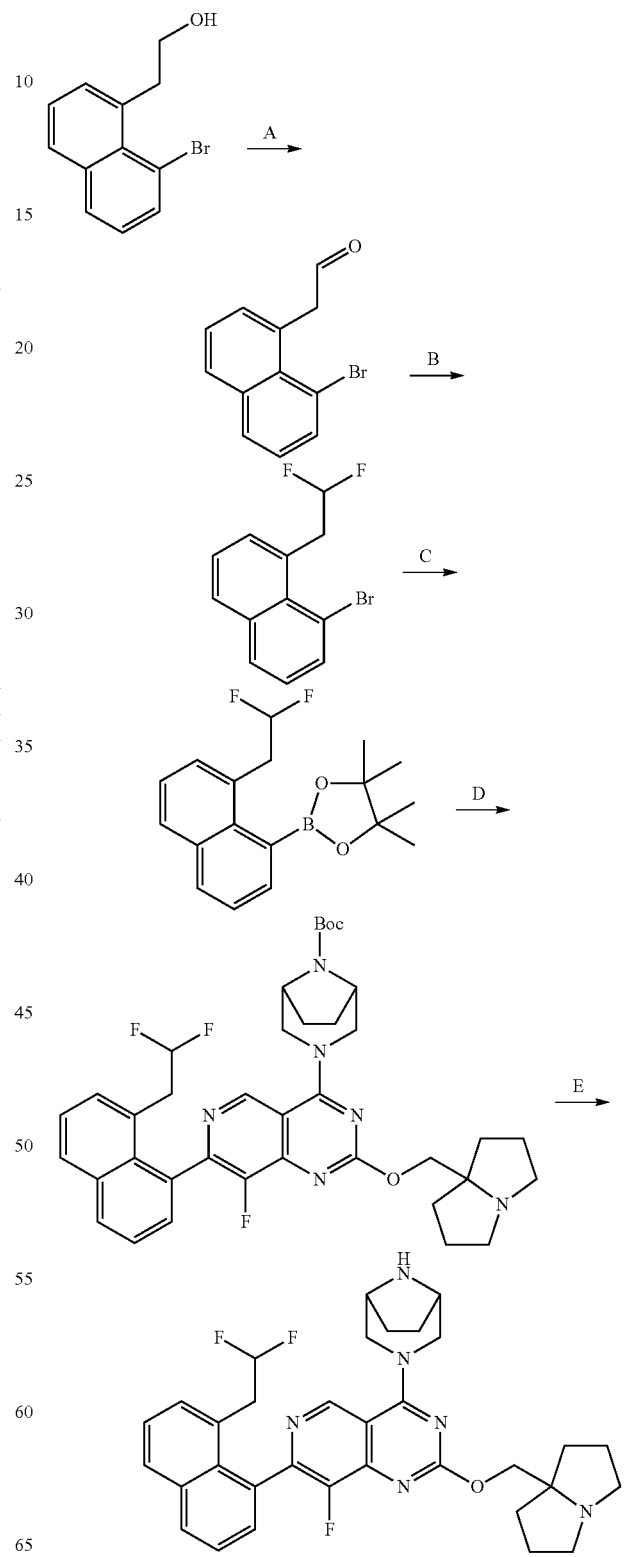

Step A. 2-(8-bromo-1-naphthyl)acetaldehyde. Dess-Martin reagent (1.18 g, 2.79 mmol, 863 μL, 1.4 eq) was added to a solution of 2-(8-bromonaphthalen-1-yl)ethan-1-ol (synthesized according to Example 239, 0.5 g, 1.99 mmol, 1.0 eq) in dry DCM (10 mL) at 0° C. The mixture was stirred at 25° C. for 1 hour, and quenched by of saturated aqueous $Na_2S_2O_3$ (10 mL). After stirred at room temperature (25° C.) for 15 minutes, the layers were separated. The aqueous phase was extracted with ethyl acetate (10 mL). Combined organic layers were dried over $Na_2SO_4$, filtered and concentrated under vacuum. The residue was purified by silica gel chromatography (petroleum ether/ethyl acetate 10/1 to 4/1) to give the title compound (0.2 g, 40%). Yellow oil; Rf=0.43 (3/1 petroleum ether/ethyl acetate); $^1$H NMR (400 MHz, $CDCl_3$): δ 10.05-10.00 (m, 1H), 7.88-7.82 (m, 3H), 7.49-7.43 (m, 1H), 7.36 (d, J=7.2 Hz, 1H), 7.32-7.27 (m, 1H), 4.73-4.67 (m, 2H).

Step B. 1-bromo-8-(2,2-difluoroethyl)naphthalene. To a solution of 2-(8-bromo-1-naphthyl)acetaldehyde (195 mg, 783 μmol, 1.0 eq) in DCM (4.0 mL) was added DAST (505 mg, 3.13 mmol, 414 μL, 4.0 eq) slowly at −40° C. The reaction mixture was stirred at 25° C. for 1 hour, and quenched with ice saturated aqueous $NaHCO_3$ (6 mL). The layers were separated. The aqueous phase was extracted with ethyl acetate (4 mL). Combined organic layers were dried over $Na_2SO_4$, filtered and concentrated under vacuum. The residue was purified by silica gel chromatography (petroleum ether/ethyl acetate 1/0 to 100/1) to give the title compound (160 mg, 75%). Yellow oil; Rf=0.90 (petroleum ether/ethyl acetate 100/1); $^1$H NMR (400 MHz, $CDCl_3$): δ 7.95-7.79 (m, 3H), 7.53-7.41 (m, 2H), 7.32-7.23 (m, 1H), 6.49-6.13 (m, 1H), 4.26-4.09 (m, 2H).

Step C. 2-[8-(2,2-difluoroethyl)-1-naphthyl]-4,4,5,5-tetramethyl-1,3,2-dioxaborolane. 1-bromo-8-(2,2-difluoroethyl)naphthalene (50 mg, 184 μmol, 1.0 eq), 4,4,5,5-tetramethyl-2-(4,4,5,5-tetramethyl-1,3,2-dioxaborolan-2-yl)-1,3,2-dioxaborolane (141 mg, 553 μmol, 3.0 eq), Pd(dppf)$Cl_2$ (13.5 mg, 18.4 μmol, 0.1 eq) and KOAc (54.3 mg, 553 μmol, 3.0 eq) in DMSO (0.5 mL) were degassed and then heated to 110° C. for 0.5 hours under $N_2$. After completion, the mixture was diluted with water (1 mL) and extracted with ethyl acetate (2×3 mL). The organic layers were dried over $Na_2SO_4$ and concentrated under vacuum. The residue was purified by silica gel chromatography (petroleum ether/ethyl acetate I/O to 100/1) to give the title compound (40 mg, 68%). Yellow oil; Rf=0.10 (petroleum ether); $^1$H NMR (400 MHz, $CDCl_3$): δ 7.92 (dd, J=1.2, 8.4 Hz, 1H), 7.85-7.76 (m, 2H), 7.51-7.43 (m, 3H), 6.33-5.99 (m, 1H), 3.82-3.68 (m, 2H), 1.45 (s, 12H).

Step D. tert-butyl (1R,5S)-3-(7-(8-(2,2-difluoroethyl)naphthalen-1-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate. A mixture of tert-butyl (1R,5S)-3-(7-chloro-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (20 mg, 37.5 μmol, 1.0 eq), 2-[8-(2,2-difluoroethyl)-1-naphthyl]-4,4,5,5-tetramethyl-1,3,2-dioxaborolane (19.1 mg, 60.0 μmol, 1.6 eq), Pd(PPh$_3$)$_4$ (4.34 mg, 3.75 μmol, 0.1 eq) and $Cs_2CO_3$ (24.5 mg, 75.0 μmol, 2.0 eq) in $H_2O$ (0.1 mL) and dioxane (0.5 mL) was degassed and then heated to 90° C. for 5 hours under $N_2$. After completion, the solvent was removed under reduced pressure. The residue was purified by reversed phase flash chromatography [water (0.1% FA)/acetonitrile]. The desired fractions were collected and neutralized with solid $NaHCO_3$, concentrated under vacuum to remove MeCN and extracted with ethyl acetate (2×5 mL). The organic layers were dried over $Na_2SO_4$ and concentrated under vacuum to give the title compound (12 mg, 40%). Yellow solid; LCMS [ESI, M+1]: 689.

Step E. 4-((1R,5S)-3,8-diazabicyclo[3.2.1]octan-3-yl)-7-(8-(2,2-difluoroethyl)naphthalen-1-yl)-8-fluoro-2-((hexahydro-1H-pyrrolizin-7a-yl)methoxy)pyrido[4,3-d]pyrimidine. To a mixture of tert-butyl (1R,5S)-3-(7-(8-(2,2-difluoroethyl)naphthalen-1-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (37 mg, 46.2 μmol, 1.0 eq) in MeCN (0.4 mL) was added HCl/dioxane (4 M, 0.37 mL, 32.0 eq). The mixture was stirred at 25° C. for 0.5 hour, the solvent was removed under reduced pressure. The residue was neutralized with saturated aqueous $Na_2CO_3$ (0.5 mL) and extracted with ethyl acetate (5×1 mL). The organic layers were dried over $Na_2SO_4$ and concentrated under vacuum. The residue was purified by prep-HPLC (column: Waters Xbridge 150*25 mm*5um; mobile phase: [water (10 mM $NH_4HCO_3$)-ACN]; B %: 24%-54%, 10 min). The desired fractions were collected and lyophilized to give the title compound (8.91 mg, 32%). White solid; $^1$H NMR (400 MHz, $CDCl_3$): δ 8.99 (s, 1H), 8.04-7.98 (m, 1H), 7.95-7.89 (m, 1H), 7.60-7.53 (m, 1H), 7.53-7.45 (m, 2H), 7.45-7.38 (m, 1H), 6.06-5.68 (m, 1H), 4.79-4.62 (m, 1H), 4.59-4.44 (m, 1H), 4.20 (s, 2H), 3.76-3.63 (m, 3H), 3.62-3.54 (m, 1H), 3.20-3.06 (m, 2H), 3.01-2.86 (m, 2H), 2.65 (td, J=7.2, 9.6 Hz, 2H), 2.19-2.05 (m, 2H), 1.96-1.72 (m, 10H); LCMS [ESI, M+1]: 589.

Example 248

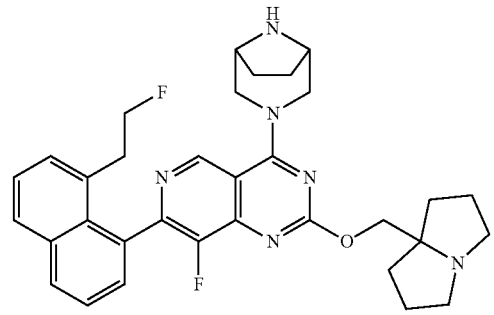 [SMILES: FCCc1cccc2cccc(-c3ncc4c(N5CC6CCC(C5)N6)nc(OCC56CCCN5CCC6)nc4c3F)c12]

4-((1R,5S)-3,8-diazabicyclo[3.2.1]octan-3-yl)-8-fluoro-7-(8-(2-fluoroethyl)naphthalen-1-yl)-2-((tetrahydro-1H-pyrrolizin-7a(5H)-yl)methoxy)pyrido[4,3-d]pyrimidine

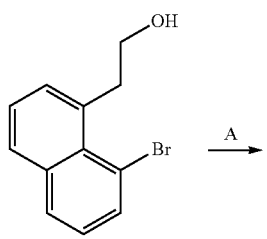

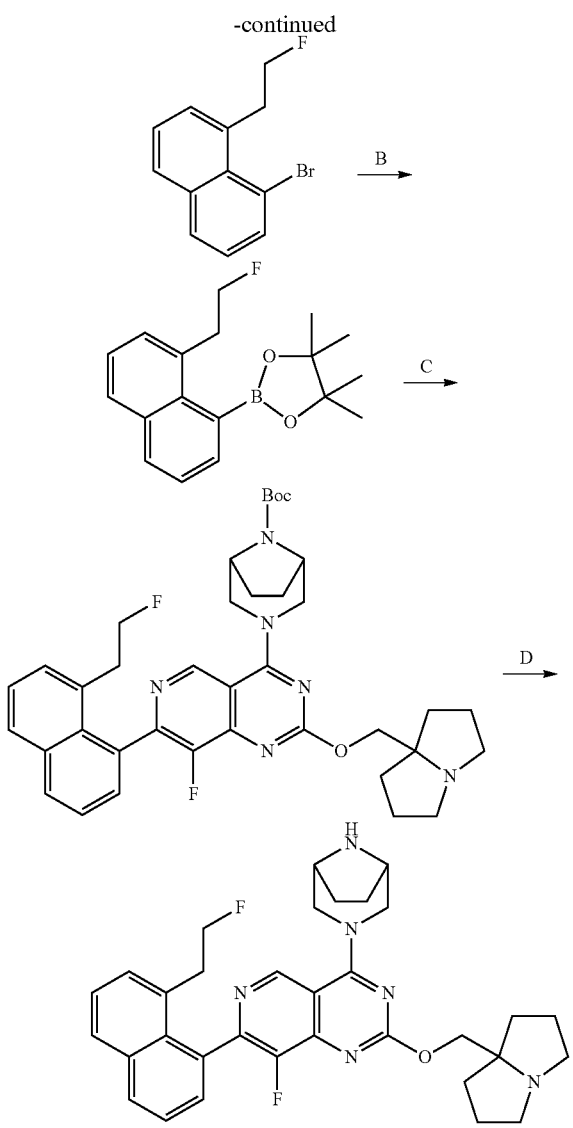

Step A. 1-bromo-8-(2-fluoroethyl)naphthalene. To a solution of 2-(8-bromonaphthalen-1-yl)ethan-1-ol (synthesized according to Example 239, 900 mg, 3.58 mmol, 1 eq) in DCM (12 mL) was added DAST (671.00 mg, 4.16 mmol, 1.16 eq) in DCM (0.5 mL) dropwise at 0 to 5° C. and the mixture was stirred at 5 to 30° C. for 45 minutes. The reaction mixture was quenched with H₂O (20 mL) below 10° C. and extracted with DCM (2×20 mL). The combined organic layers were washed with saturated brine (10 mL), dried over anhydrous Na₂SO₄, filtered and concentrated under reduced pressure to give a residue. The residue was purified by silica gel chromatography (petroleum ether/ethyl acetate=1/0) to give the title compound (606 mg, 66% yield). Light yellow liquid; Rf=0.90 (petroleum ether/ethyl acetate=3/1); $^1$H NMR (400 MHz, METHANOL-d4) δ=7.92-7.83 (m, 3H), 7.52-7.47 (m, 1H), 7.46-7.40 (m, 1H), 7.32-7.26 (m, 1H), 4.78-4.81 (m, 1H), 4.69-4.66 (m, 1H), 4.03-3.99 (m, 1H), 3.98-3.94 (m, 1H).

Step B. 2-[8-(2-fluoroethyl)-1-naphthyl]-4,4,5,5-tetramethyl-1,3,2-dioxaborolane. A mixture of 4,4,5,5-tetramethyl-2-(4,4,5,5-tetramethyl-1,3,2-dioxaborolan-2-yl)-1,3,2-dioxaborolane (870.00 mg, 3.43 mmol, 1.5 eq), 1-bromo-8-(2-fluoroethyl)naphthalene (580 mg, 2.29 mmol, 1.0 eq), AcOK (453 mg, 4.62 mmol, 2.0 eq) and Pd(dppf)Cl₂ (84 mg, 115 μmol, 0.05 eq) in dioxane (12 mL) was degassed and purged with N₂ for 4 times. The mixture was stirred at 100° C. for 3 hours under N₂ atmosphere. The reaction mixture was diluted with H₂O (50 mL) and extracted with EA (4×25 mL). The combined organic layers were washed with brine (10 mL), dried over anhydrous Na₂SO₄, filtered and concentrated under reduced pressure to give a residue. The residue was purified by silica gel chromatography (petroleum ether/ethyl acetate 1/0 to 50/1) to give the title compound (350 mg, 50% yield). Yellow foam; Rf=0.05 (petroleum ether/ethyl acetate=1/0); $^1$H NMR (400 MHz, CDCl₃) δ=7.91-7.90 (m, 1H), 7.89-7.88 (m, 1H), 7.47-7.45 (m, 1H), 7.43-7.41 (m, 3H), 4.86-4.71 (m, 2H), 3.66-3.58 (m, 2H), 1.48-1.36 (m, 12H); $^{19}$F NMR (376 MHz, METHANOL-d4) δ=−212.78.

Step C. tert-butyl (1R,5S)-3-(8-fluoro-7-(8-(2-fluoroethyl)naphthalen-1-yl)-2-((tetrahydro-1H-pyrrolizin-7a(5H)-yl)methoxy)pyrido[4,3-d]pyrimidin-4-yl)-3,8-diazabicyclo[3.2.1]octane-8-carboxylate. A mixture of tert-butyl (1R,5S)-3-(7-chloro-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (120 mg, 225 μmol, 1.0 eq), 2-[8-(2-fluoroethyl)-1-naphthyl]-4,4,5,5-tetramethyl-1,3,2-dioxaborolane (110 mg, 366 μmol, 1.63 eq), Cs₂CO₃ (220 mg, 675 μmol, 3 eq) and Pd(dppf)Cl₂ (20 mg, 27.3 μmol, 0.12 eq) in dioxane (3 mL) and H₂O (1 mL) was degassed and purged with N₂ for 4 times. The mixture was stirred at 100° C. for 6 hours under N₂ atmosphere. The reaction mixture was diluted with H₂O (15 mL) and brine (5 mL), extracted with EA (4×20 mL). The combined organic layers were dried over anhydrous Na₂SO₄, filtered and concentrated under reduced pressure. The residue was purified reversed phase flash [water (FA, 0.1%)/acetonitrile=11/9] to give the title compound (100 mg, 60% yield). Light yellow gum; LCMS [ESI, M+1]: 671.

Step D. 4-((1R,5S)-3,8-diazabicyclo[3.2.1]octan-3-yl)-8-fluoro-7-(8-(2-fluoroethyl)naphthalen-1-yl)-2-((tetrahydro-1H-pyrrolizin-7a(5H)-yl)methoxy)pyrido[4,3-d]pyrimidine. To a solution of tert-butyl (1R,5S)-3-(8-fluoro-7-(8-(2-fluoroethyl)naphthalen-1-yl)-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (45 mg, 61.57 μmol, 1.0 eq) in MeCN (0.6 mL) was added HCl·dioxane (4 M, 0.6 mL) below 10° C. The mixture was stirred at 25° C. for 1 hour. The reaction mixture was diluted with H₂O (10 mL) and EA (5 mL). The pH of the mixture was adjusted to 8-9 with solid NaHCO₃ below 10° C. The mixture was extracted with ethyl acetate (3×20 mL). The combined organic layers were dried over anhydrous Na₂SO₄, filtered and concentrated under reduced pressure to give a residue. The residue was purified by prep-HPLC (column: Phenomenex Synergi C18 150*25*10 um; mobile phase: [water (0.225% FA)-ACN]; B %: 6%-36%, 10 min). The desired fractions were collected and lyophilized to give the title compound (10.30 mg, 26% yield, 2FA). Yellow solid; $^1$H NMR (400 MHz, METHANOL-d4) δ=9.21-9.09 (m, 1H), 8.63-8.38 (m, 2H), 8.13-8.03 (m, 1H), 8.00-7.90 (m, 1H), 7.68-7.56 (m, 1H), 7.55-7.47 (m, 2H), 7.46-7.41 (m, 1H), 4.79-4.71 (m, 2H), 4.70-4.63 (m, 2H), 4.50-4.19 (m, 2H), 4.04-3.94 (m, 2H), 3.93-3.82 (m, 2H), 3.77-3.60 (m, 2H), 3.27 (q, J=6.0 Hz, 1H), 2.82-2.66 (m, 2H), 2.40-2.29 (m, 2H), 2.28-1.90 (m, 10H); $^{19}$F NMR (377 MHz, METHANOL-d4) δ=−139.76, −214.10; LCMS [ESI, M+1]: 571.

Example 249

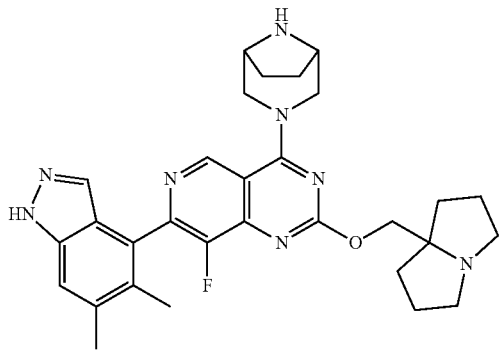 [SMILES: Cc1cc2[nH]ncc2c(-c2ncc3c(N4CC5CCC(C4)N5)nc(OCC45CCCN4CCC5)nc3c2F)c1C]

4-((1R,5S)-3,8-diazabicyclo[3.2.1]octan-3-yl)-7-(5,6-dimethyl-1H-indazol-4-yl)-8-fluoro-2-((hexahydro-1H-pyrrolizin-7a-yl)methoxy)pyrido[4,3-d]pyrimidine

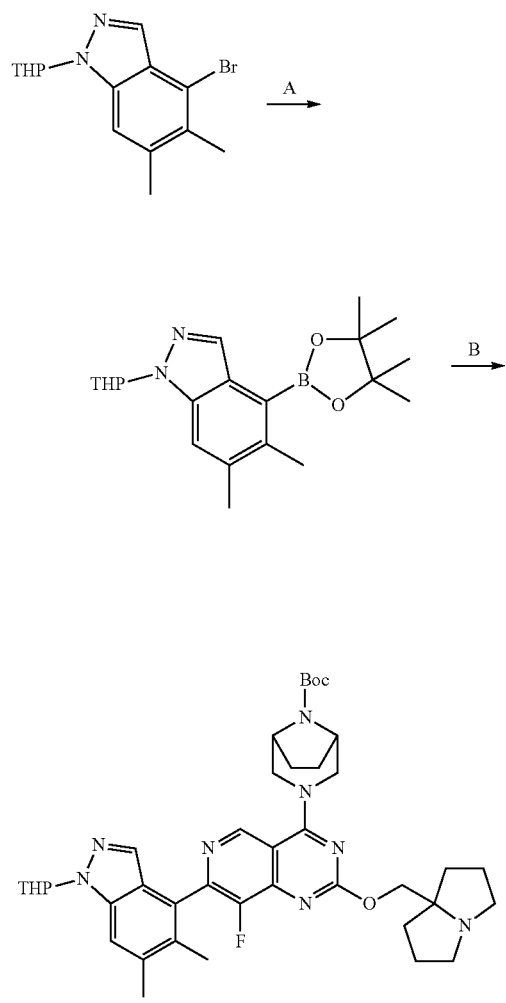

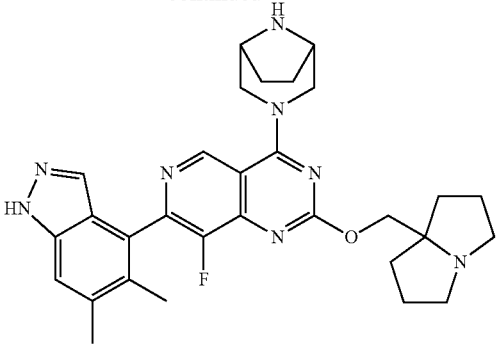

Step A. 5,6-dimethyl-1-(tetrahydro-2H-pyran-2-yl)-4-(4,4,5,5-tetramethyl-1,3,2-dioxaborolan-2-yl)-1H-indazole. To a solution of 4-bromo-5,6-dimethyl-1-(tetrahydro-2H-pyran-2-yl)-1H-indazole (500 mg, 1.62 mmol, 1.0 eq), 4,4,5,5-tetramethyl-2-(4,4,5,5-tetramethyl-1,3,2-dioxaborolan-2-yl)-1,3,2-dioxaborolane (1.23 g, 4.85 mmol, 3.0 eq) in DMSO (5.0 mL) were added KOAc (476 mg, 4.85 mmol, 3.0 eq) and Pd(dppf)Cl$_2$ (118 mg, 162 μmol, 0.1 eq). The mixture was stirred at 110° C. for 0.5 hour and filtered through a pad of Al$_2$O$_3$. The filtrate was diluted with water (10 mL) and extracted with ethyl acetate (5.0 mL×3). The combined organic phase was washed with brine (10 mL), dried with anhydrous Na$_2$SO$_4$, filtered and concentrated in vacuum. The residue was purified by silica gel chromatography (Petroleum ether/Ethyl acetate 300/1 to 10/1) to give the title compound (400 mg, 67%). Yellow oil; $^1$H NMR (400 MHz, chloroform-d) δ=8.30 (s, 1H), 7.45 (s, 1H), 5.68 (dd, J=2.8, 9.2 Hz, 1H), 4.04-3.97 (m, 1H), 3.77-3.69 (m, 1H), 2.54 (s, 4H), 2.41 (s, 3H), 2.22-2.10 (m, 1H), 2.05-1.98 (m, 1H), 1.83-1.64 (m, 3H), 1.42 (s, 12H); LCMS [ESI, M+1]: 357.

Step B. (1R,5S)-tert-butyl 3-(7-(5,6-dimethyl-1-(tetrahydro-2H-pyran-2-yl)-1H-indazol-4-yl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate. A mixture of 5,6-dimethyl-1-(tetrahydro-2H-pyran-2-yl)-4-(4,4,5,5-tetramethyl-1,3,2-dioxaborolan-2-yl)-1H-indazole (134 mg, 375 μmol, 2.0 eq), tert-butyl (1R,5S)-3-(7-chloro-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (100 mg, 188 μmol, 1.0 eq), Pd(PPh$_3$)$_4$ (22.0 mg, 18.8 μmol, 0.1 eq) and Cs$_2$CO$_3$ (122 mg, 375 μmol, 2.0 eq) in dioxane (2.0 mL) and H$_2$O (0.4 mL) was degassed and purged with N$_2$ for 3 times. Then the mixture was stirred at 90° C. for 1 hour. Water (3.0 mL) was added and the aqueous phase was extracted with ethyl acetate (3.0 mL×2). The combined organic phase was dried with anhydrous Na$_2$SO$_4$, filtered and concentrated in vacuum. The mixture was purified by reversed phase flash chromatography [water (0.1% FA)/acetonitrile]. The desired fractions were collected, neutralized with solid NaHCO$_3$, and concentrated under vacuum to remove MeCN. The aqueous phase was extracted with ethyl acetate (10 mL×2). The combined organic phase was dried with anhydrous Na$_2$SO$_4$, filtered and concentrated in vacuum to give the title compound (90 mg, 60%). White solid; $^1$H NMR (400 MHz, chloroform-d) δ=9.08 (d, J=4.4 Hz, 1H), 7.64 (d, J=3.2 Hz, 1H), 7.51 (d, J=9.6 Hz, 1H), 5.75-5.68 (m, 1H), 4.66 (br d, J=12.0 Hz, 1H), 4.54 (br d, J=12.8 Hz, 1H), 4.48-4.30 (m, 2H), 4.29-4.16 (m, 2H), 4.04 (br dd, J=13.6, 16.4 Hz, 1H), 3.84-3.56 (m, 3H), 3.19-3.08 (m, 2H), 2.65 (td, J=6.8, 10.0

Hz, 2H), 2.61-2.51 (m, 1H), 2.51-2.47 (m, 3H), 2.21 (s, 3H), 2.10 (td, J=6.0, 12.8 Hz, 3H), 2.02-1.81 (m, 10H), 1.69 (td, J=7.6, 12.8 Hz, 4H), 1.53 (s, 9H); LCMS [ESI, M+1]: 727.

Step C. 4-((1R,5S)-3,8-diazabicyclo[3.2.1]octan-3-yl)-7-(5,6-dimethyl-1H-indazol-4-yl)-8-fluoro-2-((hexahydro-1H-pyrrolizin-7a-yl)methoxy)pyrido[4,3-d]pyrimidine. To a solution of (1R,5S)-tert-butyl 3-(7-(5,6-dimethyl-1-(tetrahydro-2H-pyran-2-yl)-1H-indazol-4-yl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (50.0 mg, 68.8 µmol, 1.0 eq) in ACN (0.5 mL) was added HCl/dioxane (4 M, 0.5 mL, 29 eq) at 0° C. The mixture was stirred at 25° C. for 30 minutes. The solvent was concentrated under vacuum. The residue was diluted with methanol (1.0 mL) and neutralized with solid $Na_2CO_3$. The mixture was filtered and the filtrate was purified by prep-HPLC (column: Waters X bridge 150*25 mm*5 um; mobile phase: [water (10 mM $NH_4HCO_3$)-ACN]; B %: 28%-58%, 10 min). The desired fractions were collected and lyophilized to give the title compound (11.3 mg, 30%). White solid; $^1$H NMR (400 MHz, chloroform-d) δ 10.85-9.91 (m, 1H), 9.10 (s, 1H), 7.72 (s, 1H), 7.38 (s, 1H), 4.69-4.50 (m, 2H), 4.25-4.14 (m, 2H), 3.73-3.57 (m, 4H), 3.19-3.08 (m, 2H), 2.65 (td, J=6.9, 10.1 Hz, 2H), 2.47 (s, 3H), 2.23 (d, J=1.2 Hz, 3H), 2.11 (td, J=6.0, 12.4 Hz, 2H), 1.96-1.84 (m, 8H), 1.72-1.65 (m, 2H); LCMS [ESI, M+1]: 543.

Example 250

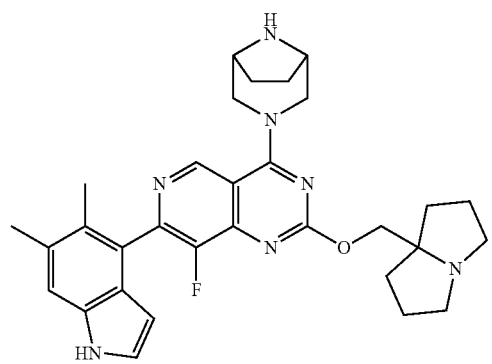 [SMILES: Cc1cc2[nH]ccc2c(-c2ncc3c(N4CC5CCC(C4)N5)nc(OCC45CCCN4CCC5)nc3c2F)c1C]

4-((1R,5S)-3,8-diazabicyclo[3.2.1]octan-3-yl)-7-(5,6-dimethyl-1H-indol-4-yl)-8-fluoro-2-((hexahydro-1H-pyrrolizin-7a-yl)methoxy)pyrido[4,3-d]pyrimidine

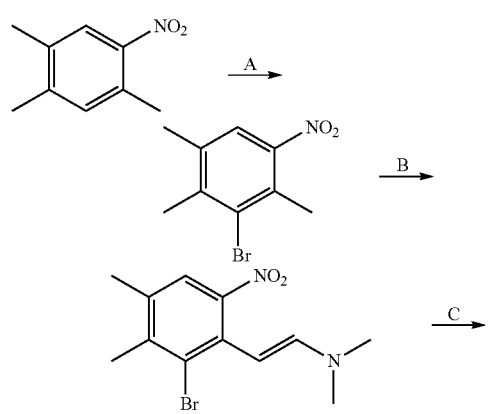

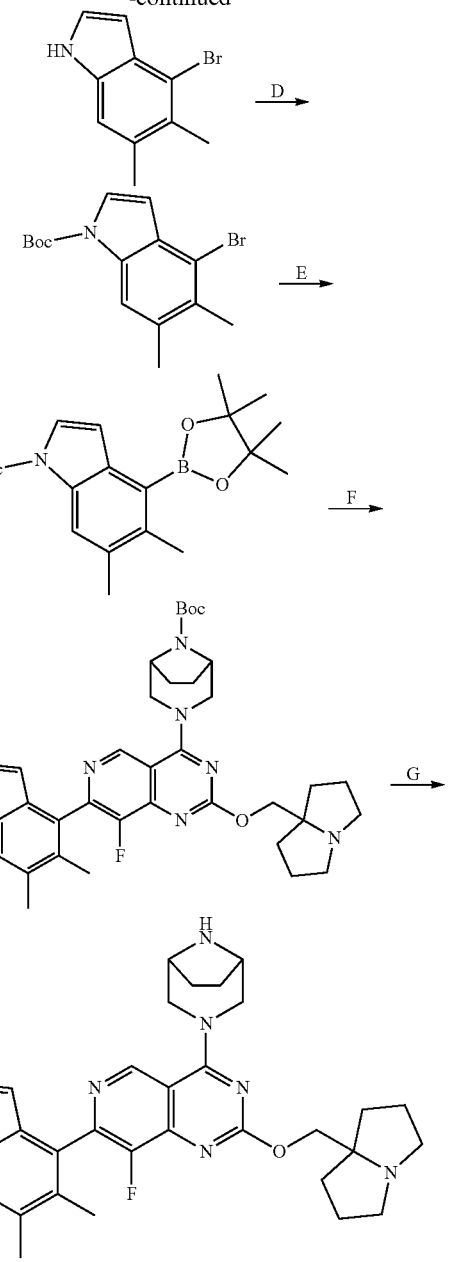

Step A. 3-bromo-1,2,4-trimethyl-5-nitrobenzene. To a mixture of 1,2,4-trimethyl-5-nitrobenzene (10 g, 60.5 mmol, 1 eq) and DCE (200 mL) were added $FeBr_3$ (358 mg, 1.21 mmol, 0.02 eq), Fe (879 mg, 15.7 mmol, 0.26 eq) and $Br_2$ (24.2 g, 151 mmol, 7.80 mL, 2.5 eq) in one portion at 25° C. The mixture was heated to 40° C. and stirred for 12 hours. The mixture was cooled to 25° C. and added saturated $Na_2SO_3$ (200 mL). The mixture was separated, and the aqueous phase was extracted with ethyl acetate (3×200 mL). The combined organic layers were washed with brine (200 mL). The combined organic layers were dried over anhydrous $Na_2SO_4$, filtered and concentrated under vacuum to give the title compound (17 g, crude). Yellow solid.

Step B. (E)-2-(2-bromo-3,4-dimethyl-6-nitrophenyl)-N,N-dimethylethenamine. To a mixture of 3-bromo-1,2,4-trimethyl-5-nitrobenzene (17 g, 69.7 mmol, 1 eq) in DMF (100 mL) was added DMF-DMA (49.8 g, 418 mmol, 55.5 mL, 6 eq) in one portion at 25° C. The mixture was heated to 130° C. and stirred for 10 hours. After completion, the mixture was cooled to 25° C. and concentrated in reduced pressure at 40° C. to afford the compound (25 g, crude).

Step C. 4-bromo-5,6-dimethyl-1H-indole. To a mixture of (E)-2-(2-bromo-3,4-dimethyl-6-nitrophenyl)-N,N-dimethylethenamine (25 g, 83.6 mmol, 1 eq) and AcOH (50.2 g, 836 mmol, 47.8 mL, 10 eq) in EtOH (200 mL) was added Fe (23.4 g, 418 mmol, 5 eq) in one portion at 25° C. under $N_2$. The mixture was heated to 60° C. and stirred for 3 hours. After completion, the mixture was filtered and concentrated in vacuum. The residue was purified by silica gel chromatography (column height: 250 mm, diameter: 100 mm, 100-200 mesh silica gel, Petroleum ether/Ethyl acetate=5/1, 3/1) to afford the title compound (1 g, three steps 5% yield). Yellow oil; LCMS [ESI, M+1]: 226.

Step D. tert-butyl 4-bromo-5,6-dimethyl-1H-indole-1-carboxylate. To the mixture of 4-bromo-5,6-dimethyl-1H-indole (1.00 g, 4.46 mmol, 1 eq) and $Boc_2O$ (4.87 g, 22.3 mmol, 5.13 mL, 5 eq) was added DMAP (54.5 mg, 446 μmol, 0.1 eq), and the mixture was stirred at 40° C. for 0.5 hour. The mixture was cooled to 25° C., and then N,N-Dimethylethylenediamine (5 mL) was added. The mixture was stirred at 25° C. for 10 minutes. The mixture was diluted with water (10 mL), and then the aqueous phase was extracted with ethyl acetate (3×10 mL). The combined organic phase was washed with brine (10 mL), dried with anhydrous $Na_2SO_4$, filtered and concentrated in vacuum. The residue was purified by silica gel chromatography (Petroleum ether) to give the title compound (1.5 g, 93% yield). White solid; $^1H$ NMR (400 MHz, $CDCl_3$-d) δ=7.94 (s, 1H), 7.50 (d, J=3.6 Hz, 1H), 6.58 (d, J=4.0 Hz, 1H), 2.45 (s, 6H), 1.67 (s, 9H).

Step E. tert-butyl 5,6-dimethyl-4-(4,4,5,5-tetramethyl-1,3,2-dioxaborolan-2-yl)-1H-indole-1-carboxylate. To a mixture of tert-butyl 4-bromo-5,6-dimethyl-1H-indole-1-carboxylate (1 g, 3.08 mmol, 1 eq) and 4,4,5,5-tetramethyl-2-(4,4,5,5-tetramethyl-1,3,2-dioxaborolan-2-yl)-1,3,2-dioxaborolane (1.17 g, 4.63 mmol, 1.5 eq) in dioxane (10 mL) were added KOAc (605 mg, 6.17 mmol, 2 eq) and $Pd(dppf)Cl_2$ (226 mg, 308 μmol, 0.1 eq) in one portion at 25° C. under $N_2$. The mixture was heated to 110° C. and stirred for 3 hours. The mixture was filtered and concentrated under reduced pressure to give a residue. The residue was purified by prep-HPLC (TFA condition) to afford the title compound (490 mg, 40% yield). White oil; $^1H$ NMR (400 MHz, $CDCl_3$-d) δ=8.04 (br s, 1H), 7.47 (br s, 1H), 6.91 (d, J=3.6 Hz, 1H), 2.52 (s, 3H), 2.38 (s, 3H), 1.67 (s, 9H), 1.42 (s, 12H).

Step F. tert-butyl 4-(4-((1R,5S)-8-(tert-butoxycarbonyl)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)-5,6-dimethyl-1H-indole-1-carboxylate. To a mixture of tert-butyl (1R,5S)-3-(7-chloro-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (300 mg, 563 μmol, 1 eq) and tert-butyl 5,6-dimethyl-4-(4,4,5,5-tetramethyl-1,3,2-dioxaborolan-2-yl)-1H-indole-1-carboxylate (230 mg, 619 μmol, 1.1 eq) in dioxane (5 mL) and $H_2O$ (1 mL) were added $Pd(dppf)Cl_2$ (41.2 mg, 56.3 μmol, 0.1 eq) and $Cs_2CO_3$ (367 mg, 1.13 mmol, 2 eq) in one portion at 25° C. under $N_2$. The mixture was heated to 90° C. and stirred for 2 hours. The mixture was filtered and concentrated in vacuum. The residue was purified by prep-HPLC (TFA condition) to afford the title compound (60 mg, 14% yield). Yellow solid; LCMS [ESI, M+1]: 742.

Step G. 4-((1R,5S)-3,8-diazabicyclo[3.2.1]octan-3-yl)-7-(5,6-dimethyl-1H-indol-4-yl)-8-fluoro-2-((hexahydro-1H-pyrrolizin-7a-yl)methoxy)pyrido[4,3-d]pyrimidine. To a solution of tert-butyl 4-(4-((1R,5S)-8-(tert-butoxycarbonyl)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)-5,6-dimethyl-1H-indole-1-carboxylate (60 mg, 80.8 μmol, 1 eq) was added HCl·MeOH (4 M, 20.2 μL, 1 eq) in one portion at 0° C. under $N_2$. The mixture was stirred at 0° C. for 30 minutes. The mixture was concentrated in vacuum. The residue was purified by prep-HPLC column: Phenomenex Gemini-NX C18 75*30 mm*3 um; mobile phase: [water (0.225% FA)-ACN]; (B %: 6%-36%, 7 min) to afford the title compound (7.69 mg, 15% yield, 2FA). Yellow solid; $^1H$ NMR (400 MHz, DMSO+D2O) δ=9.14 (s, 1H), 7.33 (s, 1H), 7.17 (d, J=2.8 Hz, 1H), 5.88 (br s, 1H), 4.62-4.50 (m, 2H), 4.46 (s, 2H), 3.78-3.72 (m, 4H), 3.47-3.36 (m, 2H), 3.13-3.03 (m, 2H), 2.35 (s, 3H), 2.16-1.91 (m, 11H), 1.86-1.69 (m, 4H); LCMS [ESI, M+1]: 542.

Example 251

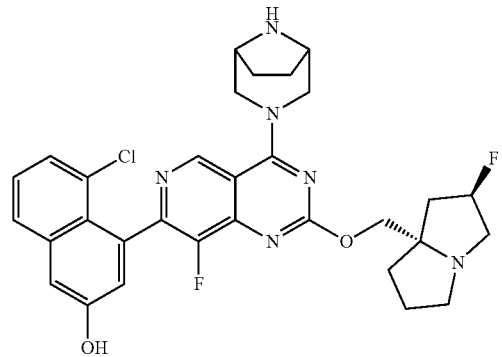 [SMILES: Oc1cc(-c2ncc3c(N4CC5CCC(C4)N5)nc(OC[C@@]45CCCN4C[C@H](F)C5)nc3c2F)c2c(Cl)cccc2c1]

4-(4-((1R,5S)-3,8-diazabicyclo[3.2.1]octan-3-yl)-8-fluoro-2-(((2R,7aS)-2-fluorohexahydro-1H-pyrrolizin-7a-yl)methoxy)pyrido[4,3-d]pyrimidin-7-yl)-5-chloronaphthalen-2-ol

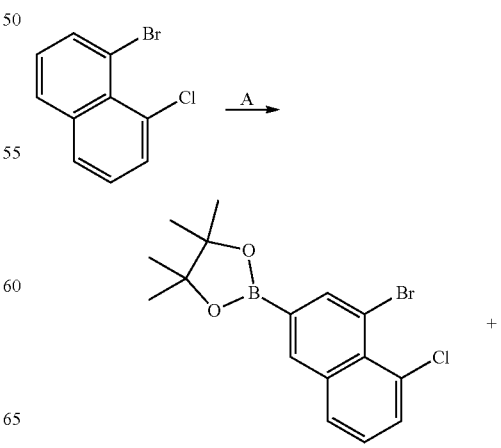

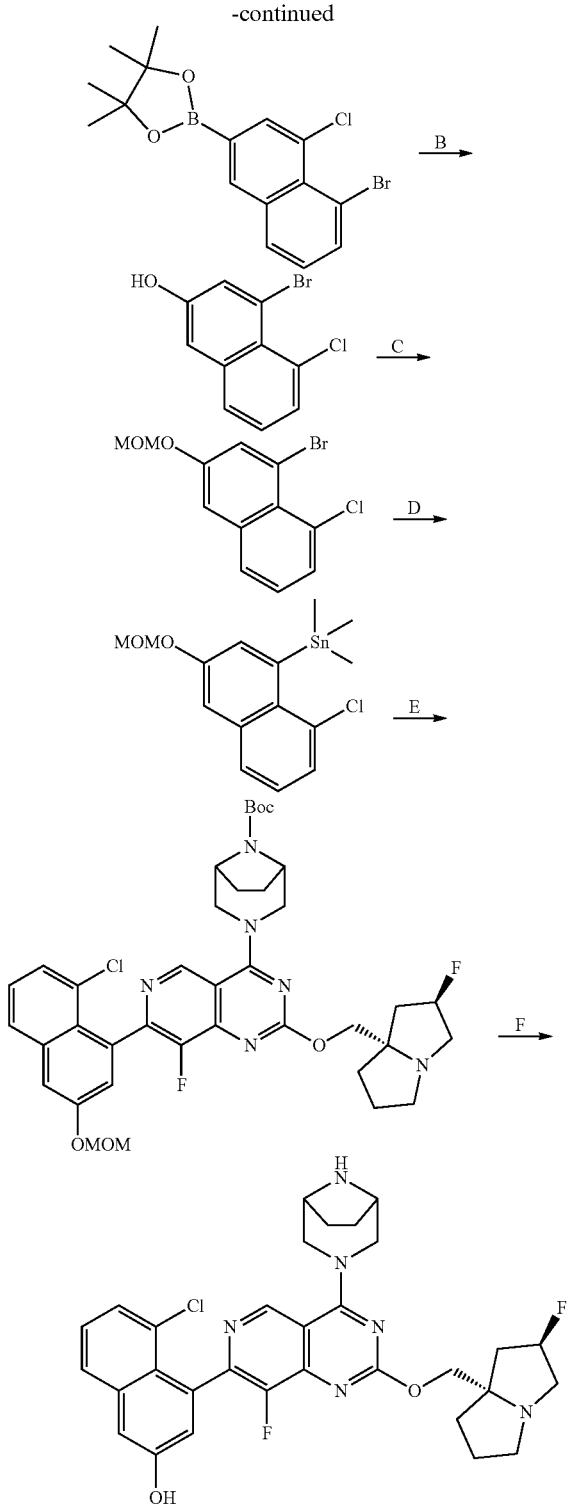

Step A. 2-(4-bromo-5-chloronaphthalen-2-yl)-4,4,5,5-tetramethyl-1,3,2-dioxaborolane and 2-(5-bromo-4-chloronaphthalen-2-yl)-4,4,5,5-tetramethyl-1,3,2-dioxaborolane. A mixture of 1-bromo-8-chloro-naphthalene (1.5 g, 6.21 mmol, 1.0 eq), 4,4,5,5-tetramethyl-1,3,2-dioxaborolane (2.38 g, 18.6 mmol, 2.70 mL, 3.0 eq), (Ir(OMe)(cod))$_2$ (205 mg, 310 μmol, 0.05 eq), 4-tert-butyl-2-(4-tert-butyl-2-pyridyl)pyridine (100 mg, 372 μmol, 0.06 eq) in THF (20 mL) was degassed and purged with N$_2$ for 3 times. The mixture was stirred at 60° C. for 10 hours under N$_2$ atmosphere. The reaction mixture was concentrated under vacuum. The residue was purified by reversed phase flash chromatography [water (0.1% formic acid)/acetonitrile)] to give the title compounds (total 4.5 g) as brown oil.

Step B. 4-bromo-5-chloronaphthalen-2-ol. To a solution of 2-(4-bromo-5-chloronaphthalen-2-yl)-4,4,5,5-tetramethyl-1,3,2-dioxaborolane and 2-(5-bromo-4-chloronaphthalen-2-yl)-4,4,5,5-tetramethyl-1,3,2-dioxaborolane (3.5 g, 9.52 mmol, 1.0 eq) in H$_2$O (35 mL) and THF (10 mL) was added AcOH (36.7 g, 611 mmol, 35.0 mL, 64.2 eq) and H$_2$O$_2$ (20.6 g, 182 mmol, 17.5 mL, 30% purity, 19.1 eq). The mixture was stirred at 10° C. for 1 hour. The reaction mixture was quenched with saturated NaHSO$_3$ solution (30 mL) and extracted with ethyl acetate (3×50 mL). The combined organic layers were washed with brine (30 mL), dried over Na$_2$SO$_4$, filtered and concentrated under reduced pressure to give the residue. The residue was purified by column chromatography (SiO$_2$, petroleum ether/ethyl acetate=10/1 to 3/1) and further purified twice by SFC (column: DAICEL CHIRALPAK AD-H (250 mm*30 mm, 5 um); mobile phase: [0.1% NH$_3$H$_2$O MEOH]; B %: 30%-30%, 3.4 min; 950 min) and (column: DAICEL CHIRALPAK AD-H (250 mm*30 mm, 5 um); mobile phase: [0.1% NH$_3$H$_2$O MEOH]; B %: 35%-35%, 2.4 min, 680 min) to give the title compound (1.5 g, 61% yield). Yellow solid. LCMS [ESI, M−1]: 257.

Step C. 1-bromo-8-chloro-3-(methoxymethoxy)naphthalene. To a solution of 4-bromo-5-chloronaphthalen-2-ol (700 mg, 2.72 mmol, 1.0 eq) in dichloromethane (15 mL) was added MOMCl (1.7 g, 21.1 mmol, 1.60 mL, 7.77 eq) and DIEA (702 mg, 5.44 mmol, 946 uL, 2.0 eq) at 0° C. The mixture was stirred at 10° C. for 1 hour. The reaction mixture was diluted with water (10 mL) and extracted with dichloromethane (3×20 mL). The combined organic layers were washed with brine (20 mL), dried over Na$_2$SO$_4$, filtered and concentrated under reduced pressure to give a residue. The residue was purified by column chromatography (SiO$_2$, petroleum ether/ethyl acetate=50/1 to 3/1) to give the title compound (700 mg, 85% yield). White solid. $^1$H NMR (400 MHz, chloroform-d) δ=7.71-7.63 (m, 2H), 7.51 (dd, J=1.2, 7.6 Hz, 1H), 7.38 (d, J=2.4 Hz, 1H), 7.31 (t, J=8.0 Hz, 1H), 5.28 (s, 2H), 3.52 (s, 3H).

Step D. (8-chloro-3-(methoxymethoxy)naphthalen-1-yl) trimethylstannane. A mixture of 1-bromo-8-chloro-3-(methoxymethoxy)naphthalene (2.3 g, 7.63 mmol, 1.0 eq), trimethyl(trimethylstannyl) stannane (7.50 g, 22.9 mmol, 4.74 mL, 3.0 eq), Pd(PPh$_3$)$_4$ (881 mg, 762 μmol, 0.1 eq) in toluene (50 mL) was degassed and purged with N$_2$ for 3 times. The mixture was stirred at 110° C. for 12 hours under N$_2$ atmosphere. The reaction mixture was diluted with water (30 mL) and extracted with ethyl acetate (3×50 mL). The combined organic layers were washed with brine (30 mL), dried over Na$_2$SO$_4$, filtered and concentrated under reduced pressure. The residue was purified by column chromatography (SiO$_2$, petroleum ether/ethyl acetate=20/1 to 5/1) to give the title compound (1.5 g, 51% yield). Colorless oil. $^1$H NMR (400 MHz, chloroform-d) δ=7.72-7.66 (m, 1H), 7.57 (d, J=2.8 Hz, 1H), 7.50-7.45 (m, 1H), 7.38 (d, J=2.8 Hz, 1H), 7.36-7.30 (m, 1H), 5.32 (s, 2H), 3.54 (s, 3H), 0.45 (s, 9H).

Step E. tert-butyl (1R,5S)-3-(7-(8-chloro-3-(methoxymethoxy)naphthalen-1-yl)-8-fluoro-2-(((2R,7aS)-2-fluorotetrahydro-1H-pyrrolizin-7a(5H)-yl)methoxy) pyrido[4,3-d]pyrimidin-4-yl)-3,8-diazabicyclo[3.2.1] octane-8-carboxylate. To a mixture of tert-butyl (1R,5S)-3-(7-chloro-8-fluoro-2-(((2R,7aS)-2-fluorotetrahydro-1H-pyrrolizin-7a(5H)-yl)methoxy)pyrido[4,3-d]pyrimidin-4- yl)-3,8-diazabicyclo[3.2.1]octane-8-carboxylate (0.5 g, 907 μmol, 1.0 eq) and (8-chloro-3-(methoxymethoxy)naphthalen-1-yl)trimethylstannane (770 mg, 2.00 mmol, 2.2 eq) in toluene (5 mL) were added Pd(dppf)Cl$_2$ (66.4 mg, 90.7 μmol, 0.1 eq), BINAP (113 mg, 181 μmol, 0.2 eq) and CuI (51.8 mg, 272 μmol, 0.3 eq) in one portion at 25° C. under N$_2$. Then it was degassed and purged with N$_2$ for 3 times. The mixture was stirred at 90° C. for 12 hours. Upon completion, the reaction mixture was quenched with water (20 mL). The aqueous layer was extracted with ethyl acetate (3×30 mL). The combined organic layers were washed with brine (30 mL), dried over Na$_2$SO$_4$, filtered and concentrated under vacuum. The residue was purified by column chromatography (SiO$_2$, petroleum ether/ethyl acetate=10/1 to ethyl acetate/methanol=10/1) and further purified by reversed phase flash chromatography [water (0.1% formic acid)/acetonitrile)] to give the title compound (100 mg, 15% yield). Yellow solid; LCMS [ESI, M+1]:737.3.

Step F. 4-(4-((1R,5S)-3,8-diazabicyclo[3.2.1]octan-3-yl)-8-fluoro-2-(((2R,7aS)-2-fluorohexahydro-1H-pyrrolizin-7a-yl)methoxy)pyrido[4,3-d]pyrimidin-7-yl)-5-chloronaphthalen-2-ol. To tert-butyl (1R,5S)-3-(7-(8-chloro-3-(methoxymethoxy)naphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (330 mg, 448 μmol, 1.0 eq) was added HCl/MeOH (4 M, 5.21 mL, 47.0 eq) in one portion at 0° C. under N$_2$. The mixture was stirred at 0° C. for 10 minutes. Upon completion, the mixture was concentrated under reduced pressure. The residue was purified by prep-HPLC (column: Phenomenex luna C18 150*40 mm*15 um; mobile phase: [water (0.225% FA)-ACN]; B %: 1%-30%, 10 min). The desired fraction was collected and lyophilized to afford the title compound (140 mg, 43% yield, 2 FA). Yellow solid; $^1$H NMR (400 MHz, CDCl$_3$) δ=9.11 (s, 1H), 7.82-7.76 (m, 1H), 7.43-7.34 (m, 3H), 7.17 (d, J=2.4 Hz, 1H), 5.59-5.40 (m, 1H), 4.84-4.74 (m, 2H), 4.63-4.51 (m, 2H), 4.06 (br s, 2H), 3.95-3.59 (m, 5H), 3.32-3.26 (m, 1H), 2.66-2.44 (m, 2H), 2.39-2.17 (m, 3H), 2.16-1.95 (m, 5H). LCMS [ESI, M+1]:593.2.

Example 252

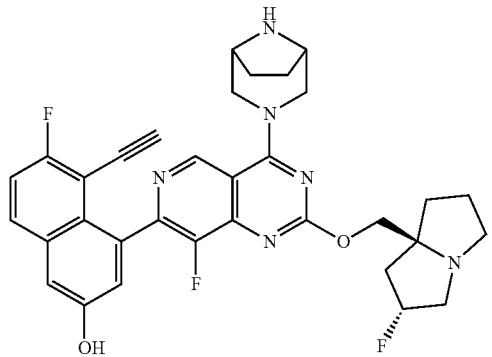 [SMILES: C#Cc1c(F)ccc2cc(O)cc(-c3ncc4c(N5CC6CCC(C5)N6)nc(OC[C@@]56CCCN5C[C@H](F)C6)nc4c3F)c12]

4-(4-((1R,5S)-3,8-diazabicyclo[3.2.1]octan-3-yl)-8-fluoro-2-(((2R,7aS)-2-fluorohexahydro-1H-pyrrolizin-7a-yl)methoxy)pyrido[4,3-d]pyrimidin-7-yl)-5-ethynyl-6-fluoronaphthalen-2-ol

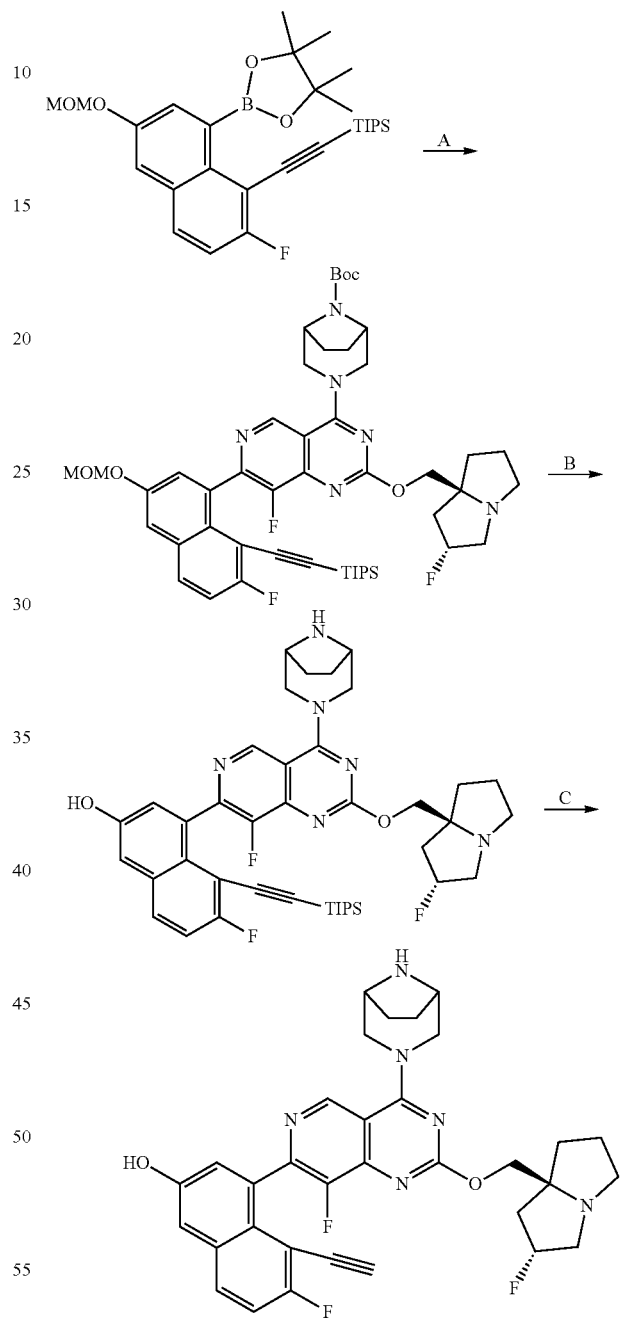

Step A. (1R,5S)-tert-butyl 3-(8-fluoro-7-(7-fluoro-3-(methoxymethoxy)-8-((triisopropylsilyl)ethynyl)naphthalen-1-yl)-2-(((2R,7aS)-2-fluorohexahydro-1H-pyrrolizin-7a-yl)methoxy)pyrido[4,3-d]pyrimidin-4-yl)-3,8-diazabicyclo[3.2.1] octane-8-carboxylate. A mixture of tert-butyl (1R,5S)-3-(7-chloro-8-fluoro-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (100 mg, 181 μmol, 1.0 eq) and Cs$_2$CO$_3$ (177 mg, 544 μmol, 3.0 eq) in dioxane (7.5 mL) and H₂O (2.5 mL) was degassed. Then Pd(dppf)Cl₂ (13.3 mg, 18.1 μmol, 0.1 eq) and ((2-fluoro-6-(methoxymethoxy)-8-(4,4,5,5-tetramethyl-1,3,2-dioxaborolan-2-yl)naphthalen-1-yl)ethynyl)triisopropylsilane (121 mg, 236 μmol, 1.3 eq) were added and the mixture was stirred at 100° C. for 2.5 hours under N₂. After completion, the reaction mixture was quenched with water (10 mL) and extracted with ethyl acetate (5 mL×3). The combined organic layers were washed with saturated brine (5 mL×2), dried over Na₂SO₄, filtered and concentrated under reduced pressure. The crude product was purified by reversed phase flash chromatography (0.1% FA condition) to give the title compound (76 mg, crude). Yellow oil. LCMS (ESI, M+1): 901.4.

Step B. 4-(4-((1R,5S)-3,8-diazabicyclo[3.2.1]octan-3-yl)-8-fluoro-2-(((2R,7aS)-2-fluorotetrahydro-1H-pyrrolizin-7a(5H)-yl)methoxy)pyrido[4,3-d]pyrimidin-7-yl)-6-fluoro-5-((triisopropylsilyl)ethynyl)naphthalen-2-ol. To a mixture of (1R,5S)-tert-butyl 3-(8-fluoro-7-(7-fluoro-3-(methoxymethoxy)-8-((triisopropylsilyl)ethynyl)naphthalen-1-yl)-2-(((2R,7aS)-2-fluorohexahydro-1H-pyrrolizin-7a-yl)methoxy)pyrido[4,3-d]pyrimidin-4-yl)-3,8-diazabicyclo[3.2.1]octane-8-carboxylate (55 mg, 61.0 μmol, 1.0 eq) and MeCN (2.5 mL) was added HCl/dioxane (4 M, 0.5 mL) in one portion under N₂. The mixture was stirred at 0° C. for 30 minutes. After completion, the residue was concentrated under reduced pressure to give the title compound (40 mg, crude), which was used into the next step without further purification. Yellow solid; LCMS (ESI, M+1): 757.7.

Step C. 4-(4-((1R,5S)-3,8-diazabicyclo[3.2.1]octan-3-yl)-8-fluoro-2-(((2R,7aS)-2-fluorohexahydro-1H-pyrrolizin-7a-yl)methoxy)pyrido[4,3-d]pyrimidin-7-yl)-5-ethynyl-6-fluoronaphthalen-2-ol. To a mixture of (4-(4-((1R,5S)-3,8-diazabicyclo[3.2.1]octan-3-yl)-8-fluoro-2-(((2R,7aS)-2-fluorotetrahydro-1H-pyrrolizin-7a(5H)-yl)methoxy)pyrido[4,3-d]pyrimidin-7-yl)-6-fluoro-5-((triisopropylsilyl)ethynyl)naphthalen-2-ol (40 mg, crude) in DMF (1 mL) was added CsF (40.13 mg, 264 μmol, 5.0 eq) in one portion under N₂. The mixture was stirred at 20° C. for 1 hour. After completion, the mixture was purified by prep-HPLC (column: Waters Xbridge C18 150*50 mm*10 um; mobile phase: [water (10 mM NH₄HCO₃)-ACN]; B %: 25%-55%, 10 min) to give the title compound (4.88 mg, 15% yield). Yellow solid; ¹H NMR (400 MHz, methanol-d₄) δ=9.03 (s, 1H), 7.88 (dd, J=5.7, 9.1 Hz, 1H), 7.38-7.31 (m, 2H), 7.23 (d, J=2.5 Hz, 1H), 5.42-5.23 (m, 1H), 4.70-4.55 (m, 5H), 4.36-4.21 (m, 2H), 3.73 (br dd, J=7.1, 12.4 Hz, 2H), 3.37 (s, 1H), 3.25 (br s, 1H), 3.23-3.19 (m, 1H), 3.03 (dt, J=5.8, 9.5 Hz, 1H), 2.41-2.21 (m, 2H), 2.20-2.11 (m, 1H), 2.06-1.97 (m, 2H), 1.92-1.78 (m, 5H); LCMS [ESI, M+1]: 601.3.

Example 253

4-(4-((1R,5S)-3,8-diazabicyclo[3.2.1]octan-3-yl)-8-fluoro-2-(((2R,7aS)-2-fluorohexahydro-1H-pyrrolizin-7a-yl)methoxy)pyrido[4,3-d]pyrimidin-7-yl)-5-ethyl-6-fluoronaphthalen-2-ol

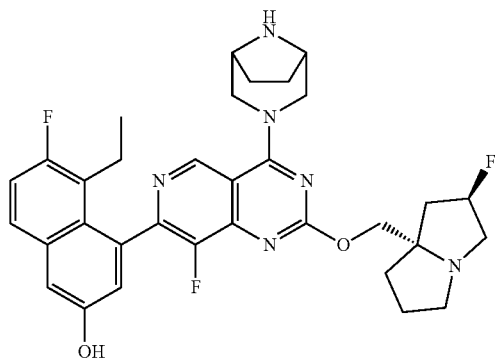 [SMILES: CCc1c(F)ccc2cc(O)cc(-c3ncc4c(N5CC6CCC(C5)N6)nc(OC[C@@]56CCCN5C[C@H](F)C6)nc4c3F)c12]

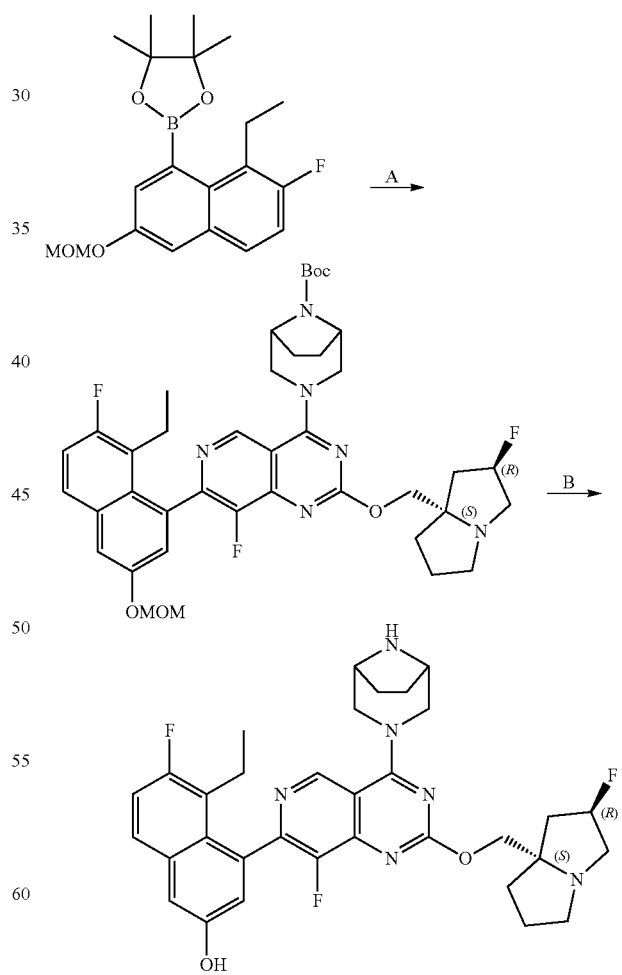

Step A. (1R,5S)-tert-butyl 3-(7-(8-ethyl-7-fluoro-3-(methoxymethoxy)naphthalen-1-yl)-8-fluoro-2-(((2R,7aS)-2-fluorohexahydro-1H-pyrrolizin-7a-yl)methoxy)pyrido[4, 3-d]pyrimidin-4-yl)-3,8-diazabicyclo[3.2.1]octane-8-carboxylate. To the mixture of tert-butyl (1R,5S)-3-(7-chloro-8-fluoro-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (40.0 mg, 72.6 μmol, 1.0 eq), 2-(8-ethyl-7-fluoro-3-(methoxymethoxy)naphthalen-1-yl)-4,4,5,5-tetramethyl-1,3,2-dioxaborolane (36.0 mg, 100 μmol, 1.4 eq), $K_3PO_4$ (1.5 M, 145 μL, 3.0 eq) in THF (1.5 mL) was added [2-(2-aminophenyl)phenyl]palladium(1+); bis(1-adamantyl)-butyl-phosphane; methanesulfonate (5.29 mg, 7.26 μmol, 0.1 eq) under $N_2$. The mixture was warmed to 60° C. for 1 hour. After completion, the reaction mixture was diluted with ethyl acetate (10 mL) and water (5 mL), and then extracted with ethyl acetate (5 mL). The combined organic phases were washed with saturated brine 10 mL, dried over $Na_2SO_4$ and concentrated. The residue was purified by reversed phase flash chromatography [water (FA 0.10%)/acetonitrile] to give the title compound (39.4 mg, 71% yield). Yellow solid. LCMS [ESI, M+1]:749.2.

Step B. 4-(4-((1R,5S)-3,8-diazabicyclo[3.2.1]octan-3-yl)-8-fluoro-2-(((2R,7aS)-2-fluorohexahydro-1H-pyrrolizin-7a-yl)methoxy)pyrido[4,3-d]pyrimidin-7-yl)-5-ethyl-6-fluoronaphthalen-2-ol. To the solution of (1R,5S)-tert-butyl 3-(7-(8-ethyl-7-fluoro-3-(methoxymethoxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)-3,8-diazabicyclo[3.2.1]octane-8-carboxylate (60.0 mg, 80.1 μmol, 1.0 eq) in ACN (1 mL) was added HCl·dioxane (4 M, 2 mL) at 0° C., and the mixture was stirred at 0° C. for 0.5 hr. After completion, the mixture was concentrated at 20° C. The residue was purified by prep-HPLC (column: Unisil 3-100 C18 ultra 150*50 mm*3 um; mobile phase: [water (0.225% FA)-ACN]; B %: 8%-28%, 10 min) to give the title compound (15.24 mg, 26% yield, 2FA). Off-white solid. $^1H$ NMR (400 MHz, METHANOL-d4) δ=9.13 (s, 1H), 8.40 (br s, 2H), 7.73-7.65 (m, 1H), 7.35-7.20 (m, 2H), 7.04 (d, J=2.4 Hz, 1H), 5.63-5.35 (m, 1H), 4.85-4.73 (m, 2H), 4.65-4.52 (m, 2H), 4.11 (br d, J=9.2 Hz, 2H), 4.00-3.86 (m, 2H), 3.85-3.62 (m, 3H), 3.39-3.32 (m, 1H), 2.71-2.41 (m, 3H), 2.40-2.31 (m, 1H), 2.30-2.15 (m, 3H), 2.14-1.96 (m, 5H), 0.85-0.73 (m, 3H). LCMS [ESI, M+1]:605.2.

Example 254

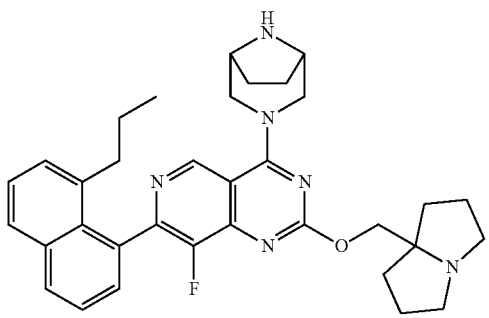 [SMILES: CCCc1cccc2cccc(-c3ncc4c(N5CC6CCC(C5)N6)nc(OCC56CCCN5CCC6)nc4c3F)c12]

4-((1R,5S)-3,8-diazabicyclo[3.2.1]octan-3-yl)-8-fluoro-2-((hexahydro-1H-pyrrolizin-7a-yl)methoxy)-7-(8-propylnaphthalen-1-yl)pyrido[4,3-d]pyrimidine

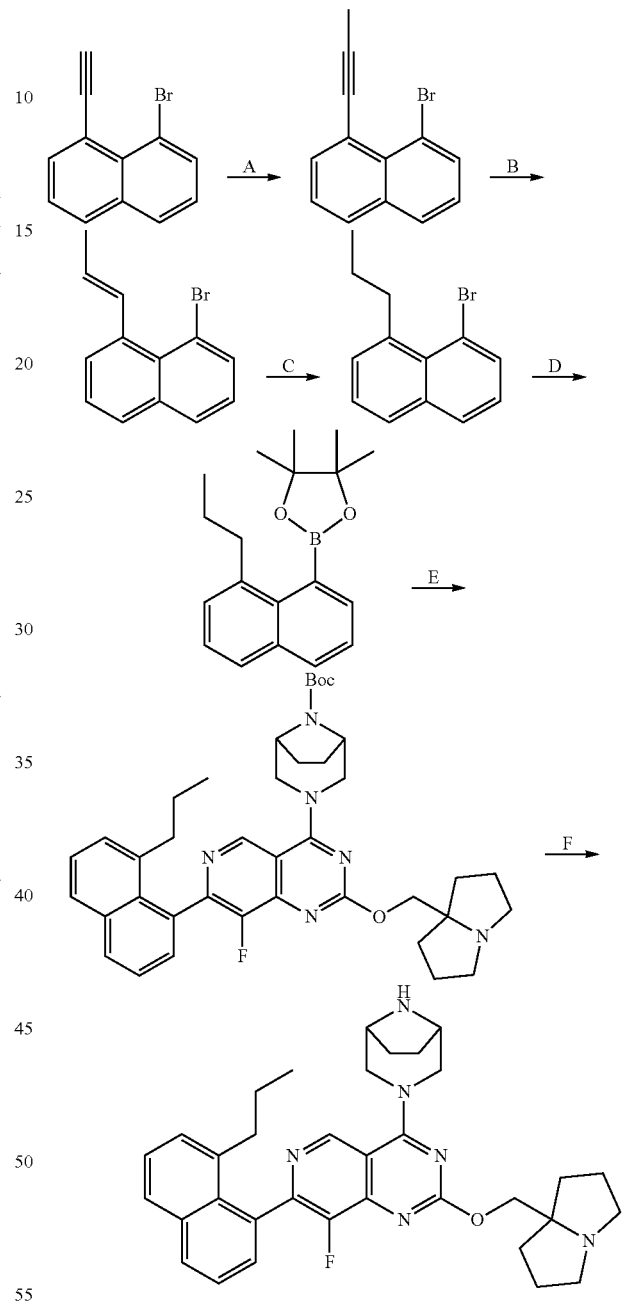

Step A. 1-bromo-8-prop-1-ynyl-naphthalene. To a solution of 1-bromo-8-ethynylnaphthalene (2.80 g, 12.1 mmol, 1.0 eq) and HMPA (3.91 g, 21.8 mmol, 3.8 mL, 1.8 eq) in THF (30 mL) was added dropwise LiHMDS (1 M, 21.8 mL, 1.8 eq) at −70° C. After addition, the mixture was stirred at −70° C. for 1 hour, and then $CH_3I$ (17.2 g, 121 mmol, 7.5 mL, 10 eq) was added dropwise at −70° C. The resulting mixture was stirred at 25° C. for 12 hours. The reaction mixture was diluted with saturated $NH_4Cl$ aqueous solution (30 mL) and extracted with ethyl acetate (3×30 mL). The combined organic layers were washed with brine (30 mL), dried over Na$_2$SO$_4$, filtered and concentrated under reduced pressure. The residue was purified by reversed phase flash chromatography [water (0.1% formic acid)/acetonitrile)] to give the title compound (2.3 g, 77% yield). Yellow oil; $^1$H NMR (400 MHz, chloroform-d) δ=7.87-7.72 (m, 4H), 7.39 (t, J=7.6 Hz, 1H), 7.26-7.22 (m, 1H), 2.16 (s, 3H).

Step B. 1-bromo-8-[(E)-prop-1-enyl]naphthalene. To a solution of 1-bromo-8-prop-1-ynyl-naphthalene (2.0 g, 8.16 mmol, 1.0 eq) in ethyl acetate (20 mL) was added PtO$_2$ (1.85 g, 8.16 mmol, 1.0 eq) under N$_2$. The suspension was degassed under vacuum and purged with H2 several times. The mixture was stirred under H$_2$ (15 psi) at 25° C. for 1 hour. The reaction mixture was filtered and the filter was concentrated. The residue was purified by reversed phase flash chromatography [water (0.1% formic acid/acetonitrile)] to give the title compound (1.3 g, 64% yield). Yellow oil.

Step C. 1-bromo-8-propyl-naphthalene. To a solution of 1-bromo-8-[(E)-prop-1-enyl]naphthalene (1.0 g, 4.05 mmol, 1.0 eq) in ethyl acetate (20 mL) was added PtO$_2$ (459 mg, 2.02 mmol, 0.5 eq) under N$_2$. The suspension was degassed under vacuum and purged with H2 several times. The mixture was stirred under H$_2$ (15 psi) at 25° C. for 3 hours. The reaction mixture was filtered and the solution was concentrated. The residue was purified by reversed phase flash chromatography [water (0.1% formic acid)/acetonitrile)] to give the title compound (340 mg, 34% yield). Yellow oil; $^1$H NMR (400 MHz, chloroform-d) δ=7.85 (dd, J=1.6, 7.2 Hz, 1H), 7.81 (dd, J=1.2, 8.0 Hz, 1H), 7.76-7.70 (m, 1H), 7.43-7.36 (m, 2H), 7.25-7.19 (m, 1H), 3.52-3.45 (m, 2H), 1.82-1.71 (m, 2H), 1.04 (t, J=7.2 Hz, 3H).

Step D. 4,4,5,5-tetramethyl-2-(8-propylnaphthalen-1-yl)-1,3,2-dioxaborolane. To the mixture of 1-bromo-8-propyl-naphthalene, 4,4,5,5-tetramethyl-2-(4,4,5,5-tetramethyl-1,3,2-ioxaborolan 2-yl)-1,3,2-dioxaborolane (583 mg, 2.30 mmol, 1.5 eq), KOAc (450 mg, 4.59 mmol, 3.0 eq) in dioxane (3.0 mL) was added Pd(dppf)Cl$_2$ (114 mg, 156 μmol, 0.1 eq) under N$_2$. The mixture was degassed and stirred at 100° C. for 2 hours. After completion, the mixture was diluted with ethyl acetate (20 mL), filtered and concentrated. The residue was purified by column chromatography (SiO$_2$, petroleum ether/ethyl acetate=1/0 to 20/1) to give the title compound (220 mg, 48% yield). Yellow oil; $^1$H NMR (400 MHz, chloroform-d) δ=7.92-7.83 (m, 1H), 7.74-7.62 (m, 2H), 7.49-7.35 (m, 3H), 3.27-3.13 (m, 2H), 1.91-1.75 (m, 2H), 1.46 (s, 12H), 1.02 (t, J=7.2 Hz, 3H)

Step E. (1R,5S)-tert-butyl 3-(8-fluoro-2-((hexahydro-1H-pyrrolizin-7a-yl)methoxy)-7-(8-propylnaphthalen-1-yl)pyrido[4,3-d]pyrimidin-4-yl)-3,8-diazabicyclo[3.2.1]octane-8-carboxylate. To the solution of tert-butyl (1R,5S)-3-(7-chloro-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (240 mg, 450 μmol, 1.0 eq), 4,4,5,5-tetramethyl-2-(8-propylnaphthalen-1-yl)-1,3,2-dioxaborolane (160 mg, 540 μmol, 1.2 eq) in THF (4.0 mL) was added K$_3$PO$_4$ (1.5 M, 905 μL, 3.0 eq) and [2-(2-aminophenyl)phenyl]palladium(1+); bis(1-adamantyl)-butyl-phosphane; methanesulfonate (65.6 mg, 90.1 μmol, 0.2 eq), and the mixture was degassed and stirred at 60° C. for 2 hours. After completion, the reaction mixture was diluted with ethyl acetate (20 mL), then washed with brine (10 mL), dried over anhydrous sodium sulfate, filtered and concentrated to give a residue. The residue was purified by reversed phase flash chromatography [water (FA 0.1%)/acetonitrile] to give the title compound (125 mg, 41% yield). Yellow solid; LCMS [ESI, M+1]: 667.4.

Step F. 4-((1R,5S)-3,8-diazabicyclo[3.2.1]octan-3-yl)-8-fluoro-2-((hexahydro-1H-pyrrolizin-7a-yl)methoxy)-7-(8-propylnaphthalen-1-yl)pyrido[4,3-d]pyrimidine. To the solution of (1R,5S)-tert-butyl 3-(8-fluoro-2-((hexahydro-1H-pyrrolizin-7a-yl)methoxy)-7-(8-propylnaphthalen-1-yl)pyrido[4,3-d]pyrimidin-4-yl)-3,8-diazabicyclo[3.2.1]octane-8-carboxylate (70.0 mg, 105 μmol, 1.0 eq) in acetonitrile (1.0 mL) was added HCl·dioxane (4 M, 2.0 mL) at 0° C., and the mixture was stirred at 0° C. for 30 minutes. After completion, the mixture was concentrated at 25° C. The residue was purified by prep-HPLC (column: Unisil 3-100 C18 ultra 150*50 mm*3 um; mobile phase: [water (0.225% FA)-ACN]; B %: 8%-38%, 10 min) to give the title compound (28.8 mg, 41% yield). Yellow solid; $^1$H NMR (400 MHz, methanol-d4) δ=9.14 (s, 1H), 8.12-8.01 (m, 1H), 7.88 (d, J=8.0 Hz, 1H), 7.60-7.54 (m, 1H), 7.51-7.45 (m, 1H), 7.45-7.42 (m, 1H), 7.38 (d, J=6.4 Hz, 1H), 4.81-4.74 (m, 2H), 4.68 (s, 2H), 4.02-3.98 (m, 2H), 3.89 (br d, J=13.6 Hz, 2H), 3.75-3.64 (m, 2H), 3.34-3.32 (m, 1H), 3.29-3.26 (m, 1H), 2.27 (br d, J=3.2 Hz, 4H), 2.26-2.15 (m, 4H), 2.14-2.07 (m, 2H), 2.06-1.97 (m, 2H), 1.96-1.83 (m, 2H), 1.40-1.25 (m, 2H), 0.42 (t, J=7.2 Hz, 3H); LCMS [ESI, M+1]: 567.3.

Example 255

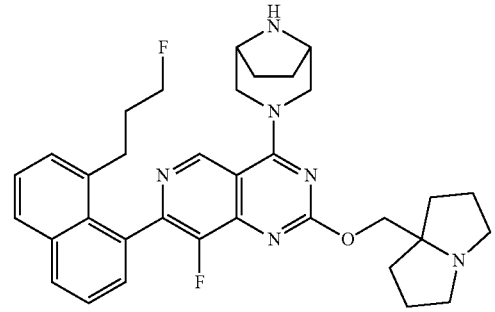 [SMILES: FCCCc1cccc2cccc(-c3ncc4c(N5CC6CCC(C5)N6)nc(OCC56CCCN5CCC6)nc4c3F)c12]

4-((1R,5S)-3,8-diazabicyclo[3.2.1]octan-3-yl)-8-fluoro-7-(8-(3-fluoropropyl)naphthalen-1-yl)-2-((hexahydro-1H-pyrrolizin-7a-yl)methoxy)pyrido[4,3-d]pyrimidine

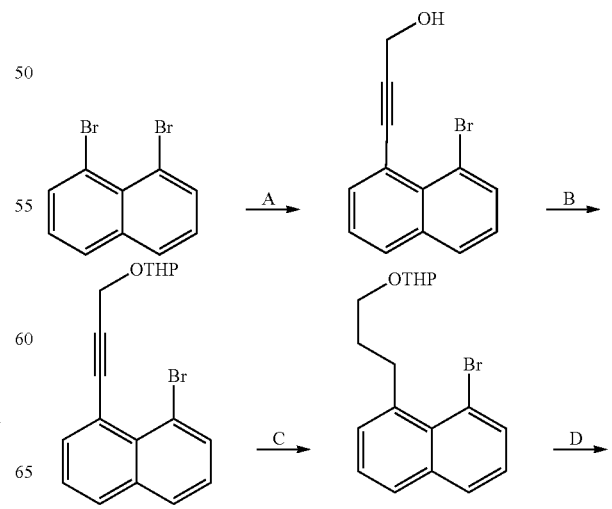

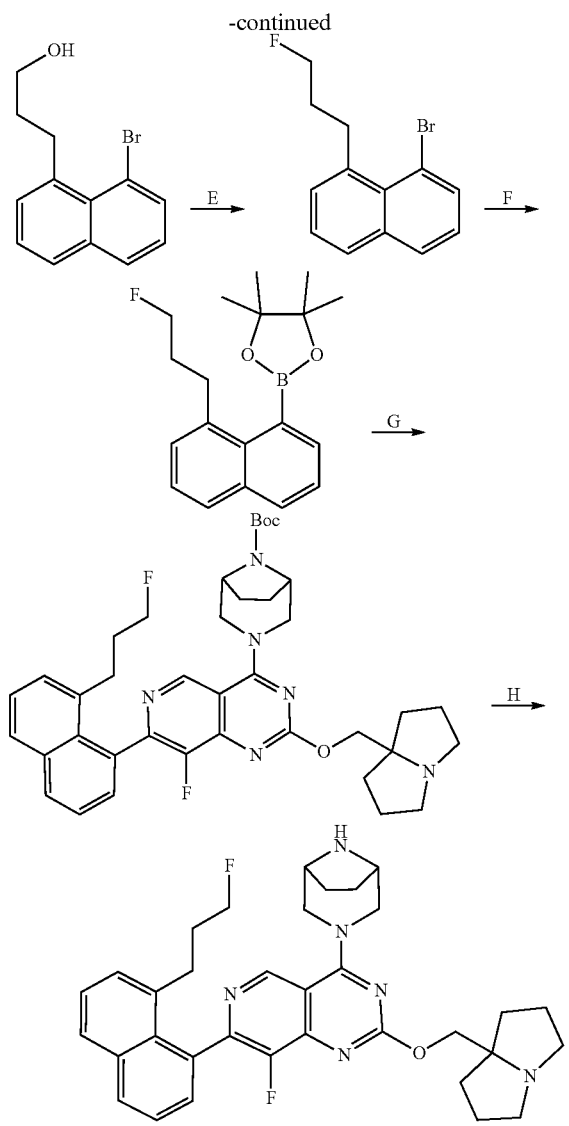

Step A. 3-(8-bromo-1-naphthyl)prop-2-yn-1-ol. A mixture of 1,8-dibromonaphthalene (10 g, 35.0 mmol, 1.0 eq), prop-2-yn-1-ol (1.96 g, 35.0 mmol, 2.07 mL, 1.0 eq), CuI (2.00 g, 10.5 mmol, 0.3 eq), PPh₃ (1.83 g, 6.99 mmol, 0.2 eq) and Pd(PPh₃)₂Cl₂ (2.45 g, 3.50 mmol, 0.1 eq) in TEA (100 mL) was stirred at 80° C. for 2 hours under N₂. After completion, the mixture was diluted with water (200 mL), ethyl acetate (200 mL) and filtered. The mixture was separated. The organic layer was washed with brine (100 mL), dried over Na₂SO₄, filtered and concentrated under vacuum. The residue was purified by column chromatography (SiO₂, petroleum ether/ethyl acetate=3/1, Rf=0.22) to give the title compound (4 g, 43% yield). Yellow solid. ¹H NMR (400 MHz, chloroform-d) δ=7.87-7.75 (m, 4H), 7.41 (t, J=7.6 Hz, 1H), 7.27 (t, J=7.6 Hz, 1H), 4.61 (s, 2H).

Step B. 2-[3-(8-bromo-1-naphthyl)prop-2-ynoxy]tetrahydropyran. A mixture of 3-(8-bromo-1-naphthyl)prop-2-yn-1-ol (2.5 g, 9.57 mmol, 1.0 eq), DHP (1.21 g, 14.4 mmol, 1.31 mL, 1.5 eq) and TsOH·H₂O (182 mg, 957 μmol, 0.1 eq) in dichloromethane (25 mL) was stirred at 20° C. for 1 hour. After completion, the mixture was concentrated under vacuum. The residue was purified by column chromatography (SiO₂, petroleum ether/ethyl acetate=3/1, Rf=0.53) to give the title compound (3 g, 89% yield). Yellow oil. ¹H NMR (400 MHz, chloroform-d) δ=7.87-7.75 (m, 4H), 7.41 (dd, J=7.2, 8.4 Hz, 1H), 7.30-7.25 (m, 1H), 5.01 (t, J=3.2 Hz, 1H), 4.60 (s, 2H), 3.99-3.90 (m, 1H), 3.63-3.55 (m, 1H), 1.91-1.61 (m, 6H).

Step C. 2-[3-(8-bromo-1-naphthyl)propoxy]tetrahydropyran. A mixture of 2-[3-(8-bromo-1-naphthyl)prop-2-ynoxy]tetrahydropyran (2.4 g, 6.95 mmol, 1 eq) and PtO₂ (30 mg) in ethyl acetate (6 mL) was stirred at 25° C. for 2 hours under H₂ at 15 psi. After completion, the mixture was filtered and concentrated under vacuum. The residue was purified by column chromatography (SiO₂, petroleum ether/ethyl acetate=5/1, Rf=0.64) to give the title compound (0.5 g, 21% yield). Yellow oil. ¹H NMR (400 MHz, chloroform-d) δ=7.89-7.70 (m, 3H), 7.46-7.36 (m, 2H), 7.25-7.19 (m, 1H), 4.71-4.58 (m, 1H), 3.96-3.82 (m, 2H), 3.66-3.58 (m, 2H), 3.57-3.47 (m, 2H), 2.12-2.02 (m, 2H), 1.91-1.81 (m, 1H), 1.79-1.72 (m, 1H), 1.67-1.55 (m, 4H).

Step D. 3-(8-bromo-1-naphthyl)propan-1-ol. A mixture of 2-[3-(8-bromo-1-naphthyl)propoxy]tetrahydropyran (450 mg, 1.29 mmol, 1.0 eq) in HCl/MeOH (4 M, 3 mL, 9.3 eq) was stirred at 25° C. for 0.5 hour. After completion, the mixture was concentrated under vacuum. The mixture was adjusted to pH>8 with saturated sodium bicarbonate, and extracted with ethyl acetate (2×3.0 mL). The combined organic layer was washed with saturated brine (3.0 mL), dried over Na₂SO₄, filtered and concentrated under vacuum to give the title compound (400 mg, crude), which was used into next step without further purification. Yellow oil. LCMS [ESI, M−15]: 249.1.

Step E. 1-bromo-8-(3-fluoropropyl)naphthalene. To a mixture of 3-(8-bromo-1-naphthyl)propan-1-ol (400 mg, 1.51 mmol, 1.0 eq) in dichloromethane (10 mL) was added DAST (365 mg, 2.26 mmol, 299 μL, 1.5 eq) at 0° C. The mixture was stirred at 0° C. for 0.5 hour. After completion, the mixture was concentrated under vacuum. The residue was purified by column chromatography (SiO₂, petroleum ether/ethyl acetate=10/1) to give the title compound (260 mg, two steps 76% yield). Yellow oil. ¹H NMR (400 MHz, chloroform-d) δ=7.78-7.64 (m, 3H), 7.36-7.29 (m, 2H), 7.18-7.12 (m, 1H), 4.50 (t, J=6.0 Hz, 1H), 4.38 (t, J=6.0 Hz, 1H), 3.65-3.51 (m, 2H), 2.14-2.00 (m, 2H).

Step F. 2-[8-(3-fluoropropyl)-1-naphthyl]-4,4,5,5-tetramethyl-1,3,2-dioxaborolane. A mixture of 1-bromo-8-(3-fluoropropyl)naphthalene (0.15 g, 562 μmol, 1.0 eq), 4,4,5,5-tetramethyl-2-(4,4,5,5-tetramethyl-1,3,2-dioxaborolan-2-yl)-1,3,2-dioxaborolane (285 mg, 1.12 mmol, 2.0 eq), Pd(dppf)Cl₂ (41.1 mg, 56.2 μmol, 0.1 eq) and KOAc (165 mg, 1.68 mmol, 3.0 eq) in dioxane (3 mL) was stirred at 110° C. for 1 hour. After completion, the mixture was diluted with water (5.0 mL), and extracted with ethyl acetate (2×5.0 mL). The combined organic layer was washed with brine (5.0 mL), dried over Na₂SO₄, filtered and concentrated under vacuum. The residue was purified by column chromatography (SiO₂, petroleum ether/ethyl acetate=10/1, Rf=0.66) to give the title compound (50 mg, 28% yield). Yellow oil. ¹H NMR (400 MHz, chloroform-d) δ=7.82-7.78 (m, 1H), 7.63 (ddd, J=1.6, 7.2, 11.6 Hz, 2H), 7.40-7.29 (m, 3H), 4.47 (t, J=6.0 Hz, 1H), 4.35 (t, J=6.0 Hz, 1H), 3.33-3.21 (m, 2H), 2.19-2.01 (m, 2H), 1.40-1.35 (m, 12H).

Step G. tert-butyl (1R,5S)-3-(8-fluoro-7-(8-(3-fluoropropyl)naphthalen-1-yl)-2-((tetrahydro-1H-pyrrolizin-7a(5H)-yl)methoxy)pyrido[4,3-d]pyrimidin-4-yl)-3,8-diazabicyclo[3.2.1]octane-8-carboxylate. A mixture of tert-butyl (1R,5S)-3-(7-chloro-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (30 mg, 56.3 μmol, 1.0 eq), 2-[8-(3-fluoropropyl)-1-naphthyl]-4,4,5,5-tetramethyl-1,3,2-dioxaborolane (21.2 mg, 67.5 μmol, 1.2 eq), Pd(dppf)Cl$_2$ (4.12 mg, 5.63 μmol, 0.1 eq) and Cs$_2$CO$_3$ (55.0 mg, 169 μmol, 3.0 eq) in dioxane (1 mL) and H$_2$O (0.3 mL) was stirred at 90° C. for 2 hours. After completion, the mixture was concentrated under vacuum. The residue was purified by reversed phase flash chromatography [water (FA, 0.1%)/acetonitrile] to give the title compound (20 mg, 44% yield). Yellow oil. LCMS [ESI, M+1]: 658.4.

Step H. 4-((1R,5S)-3,8-diazabicyclo[3.2.1]octan-3-yl)-8-fluoro-7-(8-(3-fluoropropyl)naphthalen-1-yl)-2-((tetrahydro-1H-pyrrolizin-7a(5H)-yl)methoxy)pyrido[4,3-d]pyrimidine. A mixture of tert-butyl (1R,5S)-3-(8-fluoro-7-(8-(3-fluoropropyl)naphthalen-1-yl)-2-((tetrahydro-1H-pyrrolizin-7a(5H)-yl)methoxy)pyrido[4,3-d]pyrimidin-4-yl)-3,8-diazabicyclo[3.2.1]octane-8-carboxylate in HCl/dioxane (4 M, 2 mL) and acetonitrile (0.1 mL) was stirred at 15° C. for 10 mins. After completion, the mixture was concentrated under vacuum. The residue was purified by prep-HPLC (column: Shim-pack C18 150*25*10 um; mobile phase: [water (0.225% FA)-ACN]; B %: 15%-35%, 9 min) to give the title compound (4.62 mg, 24% yield, 2FA) as a yellow oil. $^1$H NMR (400 MHz, METHANOL-d$_4$) δ=9.11 (s, 1H), 8.48 (br s, 2H), 8.08 (dd, J=1.2, 8.4 Hz, 1H), 7.91 (d, J=7.6 Hz, 1H), 7.59 (t, J=7.6 Hz, 1H), 7.53-7.40 (m, 3H), 4.72-4.56 (m, 4H), 4.19-4.07 (m, 1H), 4.04-3.91 (m, 4H), 3.79 (br d, J=12.8 Hz, 1H), 3.73-3.65 (m, 2H), 3.30-3.23 (m, 2H), 2.63-2.42 (m, 2H), 2.39-2.29 (m, 2H), 2.28-2.08 (m, 6H), 2.03-1.81 (m, 4H), 1.78-1.62 (m, 2H). FNMR: −139.603, −221.664. LCMS [ESI, M+1]: 585.3.

Example 256

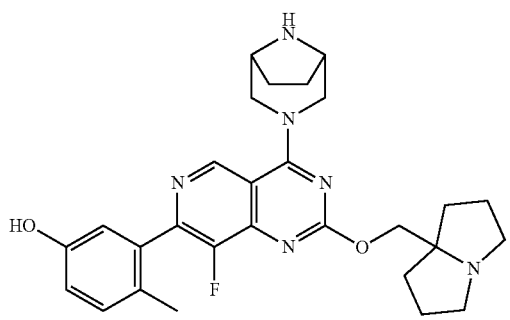 [SMILES: Cc1ccc(O)cc1-c1ncc2c(N3CC4CCC(C3)N4)nc(OCC34CCCN3CCC4)nc2c1F]

3-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)-4-methylphenol

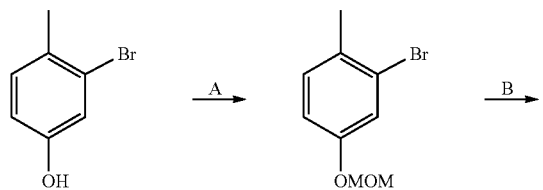

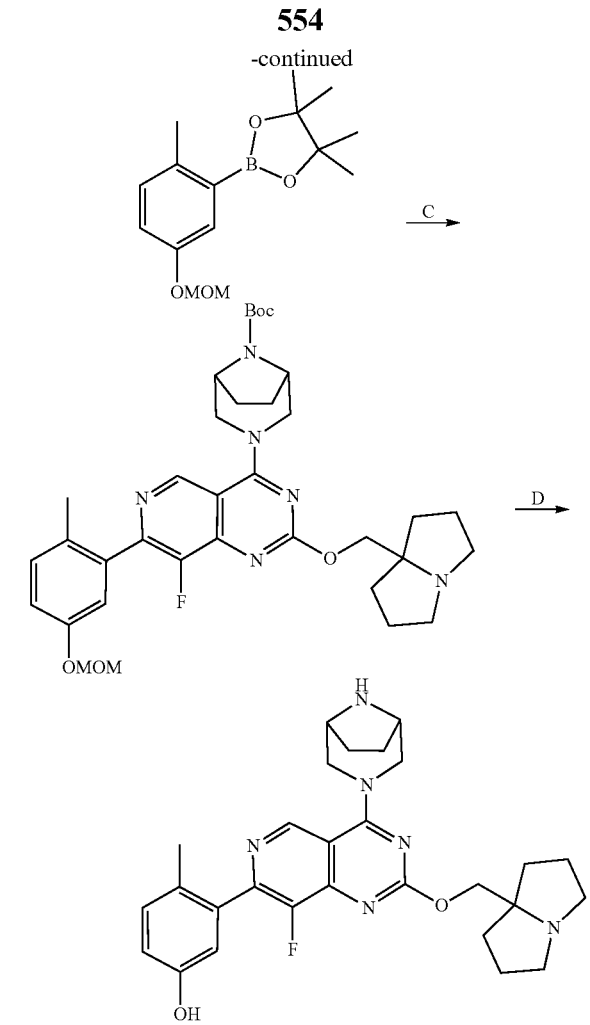

Step A. 2-bromo-4-(methoxymethoxy)-1-methyl-benzene. To a mixture of 3-bromo-4-methylphenol (2.0 g, 10.7 mmol, 1.0 eq) and DIEA (3.46 g, 26.7 mmol, 4.66 mL, 2.5 eq) in DCM (20 mL) was added MOMCl (1.12 g, 13.9 mmol, 1.3 eq) in one portion at 0° C. under N$_2$. The mixture was stirred at 0° C. for 0.5 hour. Upon completion, the mixture was concentrated. The reaction mixture was diluted with water (10 mL) and the aqueous layer was extracted with ethyl acetate (3×10 mL). The combined organic layers were dried over Na$_2$SO$_4$, filtered and concentrated under vacuum. The residue was purified by column chromatography (SiO$_2$, petroleum ether/ethyl acetate=1/0 to 100/1) to give the title compound (2.1 g, 85% yield); Colorless oil; $^1$H NMR (400 MHz, CDCl$_3$-d) δ=7.27 (s, 1H), 7.14 (d, J=8.4 Hz, 1H), 6.90 (dd, J=2.4, 8.4 Hz, 1H), 5.14 (s, 2H), 3.48 (s, 3H), 2.34 (s, 3H).

Step B. 2-[5-(methoxymethoxy)-2-methyl-phenyl]-4,4,5,5-tetramethyl-1,3,2-dioxaborolane. To a mixture of 2-bromo-4-(methoxymethoxy)-1-methyl-benzene (1.90 g, 8.22 mmol, 1.0 eq) and 4,4,5,5-tetramethyl-2-(4,4,5,5-tetramethyl-1,3,2-dioxaborolan-2-yl)-1,3,2-dioxaborolane (5.22 g, 20.6 mmol, 2.5 eq) in dioxane (20 mL) were added KOAc (2.42 g, 24.7 mmol, 3.0 eq) and Pd(dppf)Cl$_2$ (602 mg, 822 μmol, 0.1 eq) in one portion at 25° C. under N$_2$. The mixture was stirred at 100° C. for 16 hours. Upon completion, the reaction mixture was diluted with water (50 mL) and extracted with ethyl acetate (3×50 mL). The combined organic layers were dried over Na$_2$SO$_4$, filtered and concentrated under vacuum. The residue was purified by column chromatography (SiO₂, petroleum ether: ethyl acetate=500/1 to 10/1) and further purified by revered phase flash chromatography [water (0.1% formic acid)/acetonitrile)] to give the title compound (1.7 g, 73% yield). Yellow oil; ¹H NMR (400 MHz, CDCl₃-d) δ=7.41 (d, J=2.8 Hz, 1H), 7.11-7.07 (m, 1H), 7.04-6.98 (m, 1H), 5.17 (s, 2H), 3.48 (s, 3H), 2.47 (s, 3H), 1.34 (s, 12H).

Step C. tert-butyl (1R,5S)-3-(8-fluoro-7-(5-(methoxymethoxy)-2-methylphenyl)-2-((tetrahydro-1H-pyrrolizin-7a(5H)-yl)methoxy)pyrido[4,3-d]pyrimidin-4-yl)-3,8-diazabicyclo[3.2.1]octane-8-carboxylate. To a mixture of tert-butyl (1R,5S)-3-(7-chloro-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (300 mg, 563 μmol, 1.0 eq) and 2-[5-(methoxymethoxy)-2-methyl-phenyl]-4,4,5,5-tetramethyl-1,3,2-dioxaborolane (313 mg, 1.13 mmol, 2.0 eq) in dioxane (8 mL) and H₂O (2 mL) were added Pd(dppf)Cl₂ (41.2 mg, 56.3 μmol, 0.1 eq) and Cs₂CO₃ (550 mg, 1.69 mmol, 3.0 eq) in one portion at 25° C. under N₂. The mixture was stirred at 90° C. for 1 hour. The reaction mixture was diluted with H₂O (20 mL) and extracted with ethyl acetate (3×30 mL). The combined organic layers were washed with brine (30 mL), dried over Na₂SO₄, filtered and concentrated under reduced pressure. The residue was purified by reversed phase flash chromatography [water (0.1% formic acid)/acetonitrile)] to give the title compound (200 mg, 55% yield). Yellow solid; ¹H NMR (400 MHz, CDCl₃-d) δ=9.00 (s, 1H), 7.23 (d, J=8.4 Hz, 1H), 7.12 (d, J=2.4 Hz, 1H), 7.05 (dd, J=2.8, 8.4 Hz, 1H), 5.19 (s, 2H), 4.57 (br d, J=12.4 Hz, 2H), 4.38 (br s, 2H), 3.79-3.55 (m, 2H), 3.48 (s, 3H), 3.17-3.05 (m, 2H), 2.70-2.60 (m, 2H), 2.24 (s, 3H), 2.14-2.05 (m, 2H), 2.00-1.93 (m, 2H), 1.95-1.82 (m, 4H), 1.80-1.74 (m, 2H), 1.72-1.66 (m, 4H), 1.53 (s, 9H); LCMS [ESI, M+1]: 649.7.

Step D. 3-(4-((1R,5S)-3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)-4-methylphenol. To a mixture of tert-butyl (1R,5S)-3-(8-fluoro-7-(5-(methoxymethoxy)-2-methylphenyl)-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (100 mg, 154 μmol, 1.0 eq) in ACN (2 mL) was added HCl·dioxane (4 M, 2.00 mL, 52.0 eq) in one portion at 0° C. under N₂. The mixture was stirred at 0° C. for 0.5 hours. The reaction mixture was filtered and concentrated under reduced pressure. The residue was purified by prep-HPLC (column: 3_Phenomenex Luna C18 75*30 mm*3 um; mobile phase: [water (0.225% FA)-ACN]; B %: 0%-18%, 8 min). The desired fraction was collected and concentrated under vacuum to remove acetonitrile. The desired fraction was collected and lyophilized to affording the title compound (26.7 mg, 28% yield, 2FA). Yellow solid; ¹H NMR (400 MHz, CDCl₃-d) δ=9.14 (s, 1H), 7.20 (d, J=8.4 Hz, 1H), 6.91-6.81 (m, 2H), 4.85-4.80 (m, 2H), 4.69 (s, 2H), 4.05 (br s, 2H), 3.90 (br d, J=13.2 Hz, 2H), 3.78-3.66 (m, 2H), 3.32-3.26 (m, 2H), 2.40-2.29 (m, 2H), 2.23-2.17 (m, 4H), 2.16 (s, 3H), 2.15-2.09 (m, 2H), 2.08-2.02 (m, 2H), 2.01-1.92 (m, 2H); LCMS [ESI, M+1]: 505.5.

Example 257

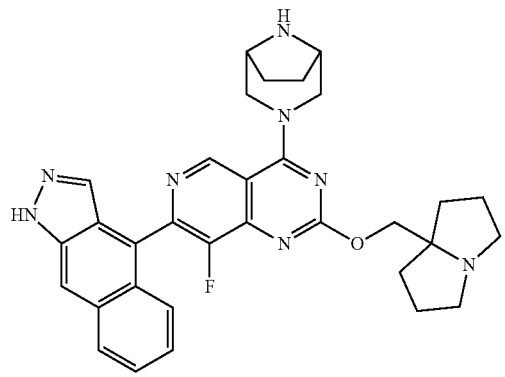 [SMILES: Fc1c(-c2c3ccccc3cc3[nH]ncc23)ncc2c(N3CC4CCC(C3)N4)nc(OCC34CCCN3CCC4)nc12]

4-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)-1H-benzo[f]indazole

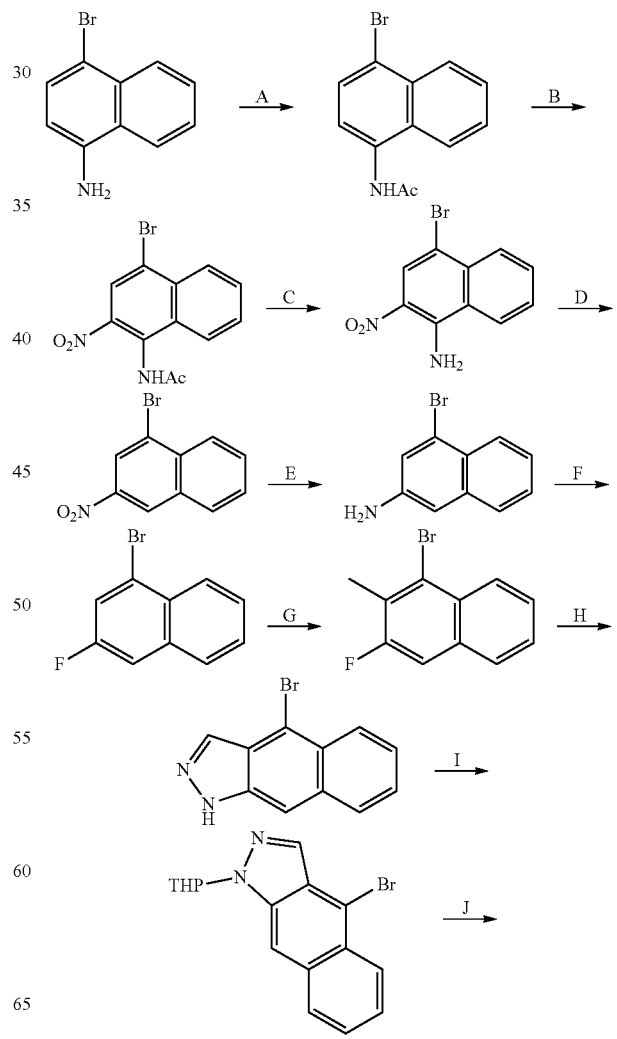

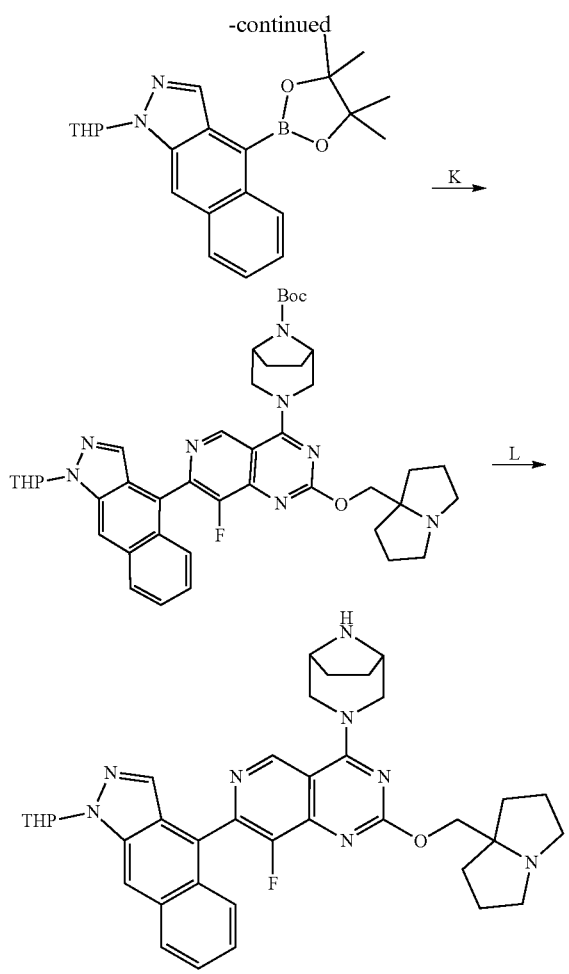

Step A. N-(4-bromonaphthalen-1-yl)acetamide. To a solution of 4-bromonaphthalen-1-amine (50.0 g, 225 mmol, 1.0 eq) in MeOH (400 mL) was added acetic anhydride (27.6 g, 270 mmol, 25.3 mL, 1.2 eq). The reaction mixture was stirred at 60° C. for 1 hour. After completion, the reaction mixture was concentrated under vacuum. The mixture was triturated with MTBE (200 mL). The mixture was filtered and the filter cake was washed with MTBE (100 mL), dried in vacuum to give the title compound (57.0 g, 94% yield). Yellow solid; $^1$H NMR (400 MHz, DMSO-d6) δ=10.02 (br s, 1H), 8.20-8.13 (m, 2H), 7.87 (d, J=8.2 Hz, 1H), 7.76-7.64 (m, 3H), 2.21 (s, 3H). [ESI, M+1]: 265.9.

Step B. N-(4-bromo-2-nitronaphthalen-1-yl)acetamide. To a solution of N-(4-bromonaphthalen-1-yl)acetamide (50.0 g, 189 mmol, 1.0 eq) in AcOH (400 mL) was added Fuming Nitric Acid (13.1 g, 208 mmol, 8.57 mL, 1.1 eq) dropwise at 45° C. The mixture was stirred at 75° C. for 0.5 hour. After completion, the suspension was filtered and washed with cold MeOH (120 mL) and MTBE (360 mL), dried in vacuum to give the title compound (45.0 g, 77% yield). Yellow solid; $^1$H NMR (400 MHz, DMSO-d6) δ=10.62 (s, 1H), 8.35 (t, J=4.0 Hz, 2H), 8.26 (d, J=8.3 Hz, 1H), 7.98-7.91 (m, 1H), 7.90-7.83 (m, 1H), 2.19 (s, 3H). [ESI, M+1]: 310.9. The product was used for next step without further purification.

Step C. 4-Bromo-2-nitronaphthalen-1-amine. A solution of N-(4-bromo-2-nitronaphthalen-1-yl)acetamide (45.0 g, 145 mmol, 1.0 eq) in HCl (4 M, 270 mL, 7.4 eq) and EtOH (250 mL) and THF (500 mL) were heated to 80° C. for 50 hours. After completion, the reaction mixture was concentrated under vacuum. The mixture was filtered and washed with EA (300 mL) and dried in vacuum to give the title compound (36.5 g, 88% yield). Red solid; $^1$H NMR (400 MHz, DMSO-d6) δ=8.99-8.71 (m, 1H), 8.67 (d, J=8.4 Hz, 1H), 8.25 (s, 1H), 8.05 (d, J=8.3 Hz, 1H), 7.87 (t, J=7.6 Hz, 1H), 7.74-7.67 (m, 1H). [ESI, M+1]: 268.9. The product was used for next step without further purification.

Step D. 1-Bromo-3-nitronaphthalene. To a solution of 4-Bromo-2-nitronaphthalen-1-amine (10.0 g, 37.4 mmol, 1.0 eq) in AcOH (100 mL) and H$_2$SO$_4$ (184 g, 1.84 mol, 100 mL, 98% purity, 49.1 eq) was added NaNO$_2$ (4.65 g, 67.4 mmol, 1.8 eq) at 5° C. The reaction was stirred at 5-20° C. for 2 hours. To the mixture was added EtOH (100 mL). The resulting solution was added to the mixture of CuSO4 (7.17 g, 44.9 mmol, 6.9 mL, 1.2 eq) and H$_3$PO$_2$ (30.0 g, 148 mmol, 100 mL, 32% purity, 3.9 eq) and the reaction was stirred at 65° C. for 1 hour. After completion, the reaction mixture was concentrated under vacuum. The residue was diluted with H$_2$O (150 mL) and extracted with EA (3×100 mL). The combined organic layers were washed with brine (100 mL), dried over Na$_2$SO$_4$, filtered and concentrated under vacuum. The residue was purified by silica gel chromatography (SiO$_2$, PE:EA=10:1) to give the title compound (7.8 g, 88% yield). Yellow solid; $^1$H NMR (400 MHz, CHLOROFORM-d) δ=8.81 (d, J=1.8 Hz, 1H), 8.60 (d, J=2.1 Hz, 1H), 8.36 (d, J=8.4 Hz, 1H), 8.08 (d, J=8.2 Hz, 1H), 7.85 (ddd, J=1.2, 7.1, 8.4 Hz, 1H), 7.78-7.70 (m, 1H).

Step E. 4-Bromonaphthalen-2-amine. To a solution of 1-Bromo-3-nitronaphthalene (7.80 g, 30.9 mmol, 1.0 eq), HCl (3.05 g, 30.9 mmol, 3.0 mL, 37% purity, 1.0 eq) in EtOH (80 mL) and H$_2$O (40 mL) was added Fe (8.64 g, 155 mmol, 5.0 eq) at 80° C. The reaction mixture was stirred at 80° C. for 0.5 hour. After completion, the mixture was filtered and the filtrate was concentrated under vacuum. The residue was purified by silica gel chromatography (SiO$_2$, PE:EA=5:1) to give the title compound (6.3 g, 83% yield). Yellow solid; $^1$H NMR (400 MHz, DMSO-d6) δ=7.84 (d, J=8.5 Hz, 1H), 7.55 (d, J=8.2 Hz, 1H), 7.39-7.31 (m, 2H), 7.22 (ddd, J=1.3, 6.9, 8.3 Hz, 1H), 6.87 (d, J=2.0 Hz, 1H). [ESI, M+1]: 221.9.

Step F. 1-Bromo-3-fluoronaphthalene. To a mixture of 4-Bromonaphthalen-2-amine (5.00 g, 22.5 mmol, 1.0 eq) and hydrofluoride pyridine (55.0 g, 555 mmol, 50 mL, 24.6 eq) was added NaNO$_2$ (2.02 g, 29.3 mmol, 1.3 eq) in one portion at 0° C. under N$_2$. The mixture was stirred at 80° C. for 8 hours. After completion, the reaction mixture was concentrated under vacuum. The residue was diluted with H$_2$O (100 mL), and extracted with EA (2×100 mL). The combined organic layers were washed with brine (100 mL), dried over Na$_2$SO$_4$, filtered and concentrated under vacuum. The residue was purified by silica gel chromatography (SiO$_2$, PE:EA=10:1) to give the title compound (2.5 g, 49% yield). Yellow solid; $^1$H NMR (400 MHz, DMSO-d6) δ=8.09-8.04 (m, 1H), 7.96-7.92 (m, 1H), 7.88 (dd, J=2.6, 8.4 Hz, 1H), 7.79 (dd, J=2.4, 9.7 Hz, 1H), 7.63-7.57 (m, 2H).

Step G. 1-Bromo-3-fluoro-2-naphthaldehyde. To a solution of diisopropylamine (1.08 g, 10.7 mmol, 1.51 mL, 1.2 eq) in anhydrous THF (20 mL) was added N-butyllithium (2.5 M, 3.55 mL, 1.0 eq) dropwise over 5 min under N$_2$ at 0° C. After 10 min, the reaction mixture was cooled to −78° C. and 1-Bromo-3-fluoronaphthalene (2.0 g, 8.89 mmol, 1.0 eq) was added dropwise over 5 min. After 1 hour at −78° C., DMF (779 mg, 10.7 mmol, 820 μL, 1.2 eq) was added dropwise over 10 min. After completion, the reaction mixture was quenched with water (50 mL) at 20° C., and then diluted with water (50 mL). The mixture was extracted with EtOAc (50 mL×2). The combined organic layers were washed with saturated sodium chloride solution (100 mL), dried over anhydrous sodium sulfate, filtered and concentrated under vacuum to give the title compound (2.0 g, 83% yield). Yellow solid; ¹H NMR (400 MHz, DMSO-d6) δ=10.49 (s, 1H), 8.44 (dd, J=1.0, 8.0 Hz, 1H), 8.12-8.07 (m, 1H), 8.02 (d, J=11.8 Hz, 1H), 7.89-7.78 (m, 2H). The product was used for next step without further purification.

Step H. 4-Bromo-1H-benzo[f]indazole. To a mixture of 1-Bromo-3-fluoro-2-naphthaldehyde (2.0 g, 7.90 mmol, 1.0 eq) in DMSO (20 mL) were added hydrazine hydrate (2.02 g, 39.5 mmol, 1.96 mL, 98% purity, 5.0 eq) and DIEA (8.17 g, 63.2 mmol, 11.0 mL, 8.0 eq) in one portion under N₂. The mixture was stirred at 130° C. for 8 hours. After completion, the reaction mixture was concentrated under reduced pressure to give a residue. The residue was purified by prep-HPLC (C18, 0.1% FA in water, 0-100% MeCN) to give the title compound (410 mg, 18% yield). Off-white solid; [ESI, M+1]: 246.9.

Step I. 4-Bromo-1-(tetrahydro-2H-pyran-2-yl)-1H-benzo[f]indazole. To a mixture of 4-Bromo-1H-benzo[f]indazole (150 mg, 607 μmol, 1.0 eq) and DHP (153 mg, 1.82 mmol, 166 μL, 3.0 eq) in DCM (2 mL) was added TsOH (5.23 mg, 30.3 μmol, 0.05 eq) in one portion at 20° C. under N₂. The mixture was stirred at 20° C. for 12 hours. After completion, the reaction mixture was concentrated under reduced pressure to give a residue. The residue was purified by column chromatography (SiO₂, PE:EA=20/1 to 10/1) to give the title compound (110 mg, 54% yield). Yellow solid; [ESI, M+1]: 331.0.

Step J. 1-(tetrahydro-2H-pyran-2-yl)-4-(4,4,5,5-tetramethyl-1,3,2-dioxaborolan-2-yl)-1H-benzo[f]indazole. To a mixture of 4-Bromo-1-(tetrahydro-2H-pyran-2-yl)-1H-benzo[f]indazole (110 mg, 332 μmol, 1.0 eq) and 4,4,5,5-tetramethyl-2-(4,4,5,5-tetramethyl-1,3,2-dioxaborolan-2-yl)-1,3,2-dioxaborolane (101 mg, 398 μmol, 1.2 eq) in dioxane (2 mL) were added KOAc (97.8 mg, 996 μmol, 3.0 eq) and Pd(dppf)Cl₂ (24.3 mg, 33.2 μmol, 0.1 eq) in one portion under N₂. The mixture was stirred at 90° C. for 1 hour. After completion, the reaction mixture was concentrated under reduced pressure to give a residue. The residue was purified by column chromatography (SiO₂, PE:EA=20/1 to 10/1) to give the title compound (90 mg, 55% yield). Yellow solid; [ESI, M+1]: 379.2.

Step K. (1R,5S)-tert-butyl 3-(8-fluoro-2-((hexahydro-1H-pyrrolizin-7a-yl)methoxy)-7-(1-(tetrahydro-2H-pyran-2-yl)-1H-benzo[f]indazol-4-yl)pyrido[4,3-d]pyrimidin-4-yl)-3,8-diazabicyclo[3.2.1]octane-8-carboxylate. To a mixture of 1-(tetrahydro-2H-pyran-2-yl)-4-(4,4,5,5-tetramethyl-1,3,2-dioxaborolan-2-yl)-1H-benzo[f]indazole (90 mg, 238 μmol, 1.0 eq) and tert-butyl (1R,5S)-3-(7-chloro-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (127 mg, 238 μmol, 1.0 eq) in toluene (2 mL) were added Ad₂nBup-Pd-G3 (26 mg, 35.7 μmol, 0.15 eq) and K₃PO₄ (1.5 M, 476 μL, 3.0 eq) in one portion under N₂. The mixture was stirred at 90° C. for 2 hours. After completion, the reaction mixture was concentrated under reduced pressure to give a residue. The residue was purified by prep-HPLC (C18, 0.1% FA in water, 0-100% MeCN) to give the title compound (45 mg, 23% yield). Yellow solid; [ESI, M+1]: 749.4

Step L. 4-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)-1H-benzo[f]indazole. To a mixture of (1R,5S)-tert-butyl 3-(8-fluoro-2-((hexahydro-1H-pyrrolizin-7a-yl)methoxy)-7-(1-(tetrahydro-2H-pyran-2-yl)-1H-benzo[f]indazol-4-yl)pyrido[4,3-d]pyrimidin-4-yl)-3,8-diazabicyclo[3.2.1]octane-8-carboxylate (40 mg, 53.4 μmol, 1.0 eq) in DCM (2.0 mL) was added TFA (3.08 g, 27.0 mmol, 2.0 mL, 506 eq) in one portion at 0° C. under N₂. The mixture was stirred at 20° C. for 10 min. After completion, the reaction mixture was concentrated under reduced pressure. The residue was purified by prep-HPLC (column: Phenomenex Synergi C18 150*25*10 um; mobile phase: [water (0.225% FA)-ACN]; B %: 5%-35%, 8.5 min) to give the title compound (5.39 mg, 16% yield, 1.1 FA). Yellow solid; ¹H NMR (400 MHz, METHANOL-d4) δ=9.31 (s, 1H), 8.25 (s, 1H), 8.11 (d, J=8.7 Hz, 1H), 8.07 (s, 1H), 7.85-7.79 (m, 1H), 7.55-7.48 (m, 1H), 7.38 (ddd, J=1.2, 6.6, 8.7 Hz, 1H), 4.94-4.91 (m, 1H), 4.84 (br s, 1H), 4.72 (s, 2H), 4.08 (br s, 2H), 3.95 (br t, J=13.5 Hz, 2H), 3.78-3.66 (m, 2H), 3.32-3.26 (m, 2H), 2.45-2.32 (m, 1H), 2.30-2.01 (m, 10H). [ESI, M+1]: 565.3.

Example 258

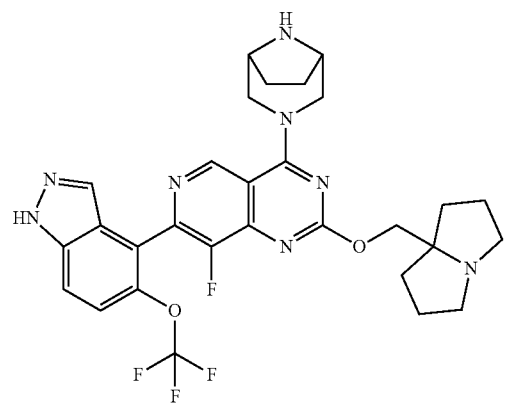 [SMILES: Fc1c(-c2c(OC(F)(F)F)ccc3[nH]ncc23)ncc2c(N3CC4CCC(C3)N4)nc(OCC34CCCN3CCC4)nc12]

4-((1R,5S)-3,8-diazabicyclo[3.2.1]octan-3-yl)-8-fluoro-2-((hexahydro-1H-pyrrolizin-7a-yl)methoxy)-7-(5-(trifluoromethoxy)-1H-indazol-4-yl)pyrido[4,3-d]pyrimidine

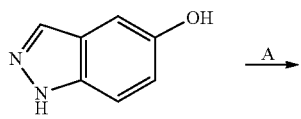

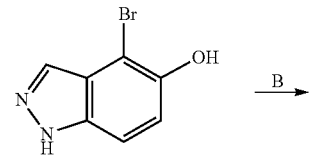

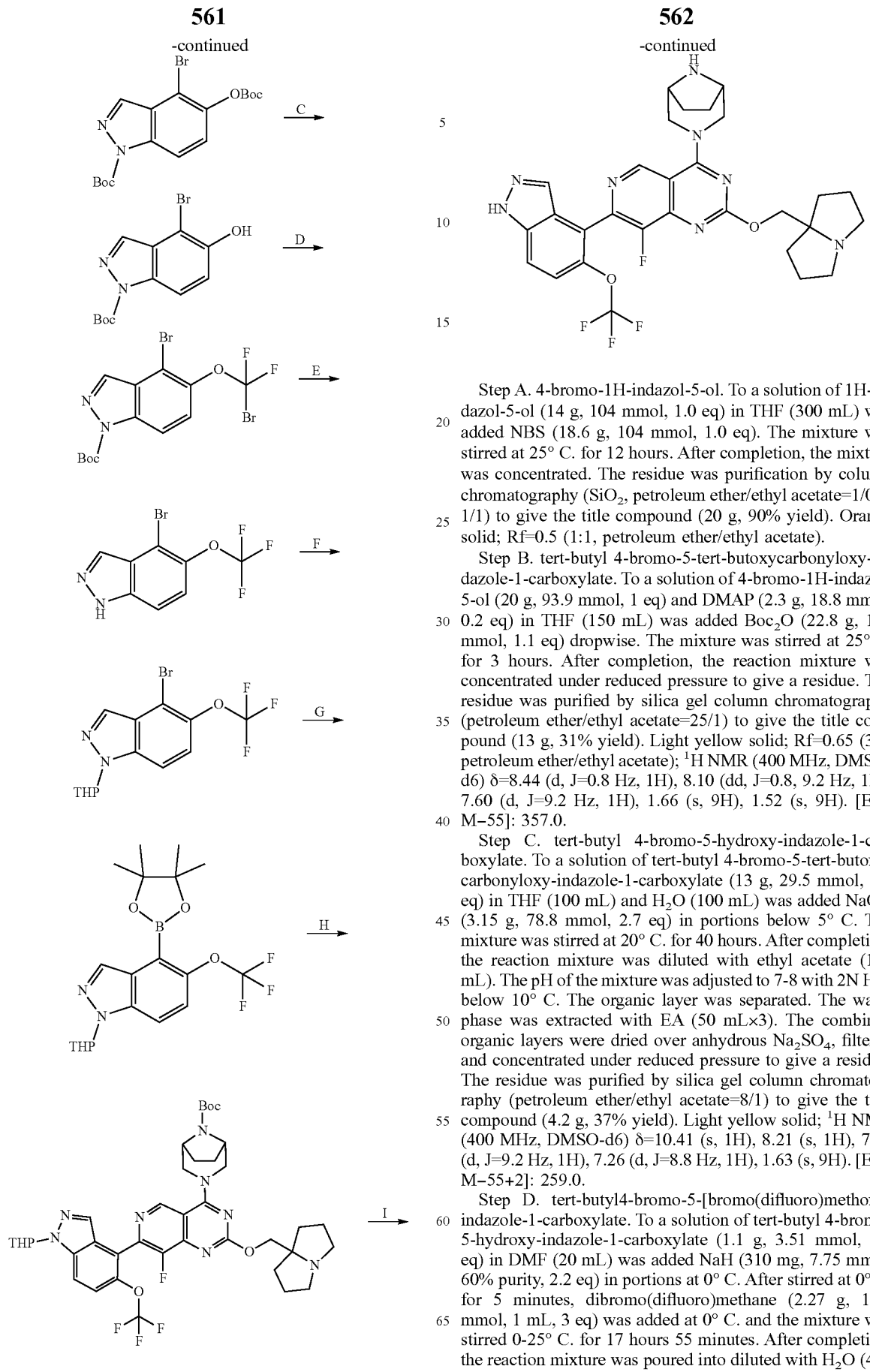

Step A. 4-bromo-1H-indazol-5-ol. To a solution of 1H-indazol-5-ol (14 g, 104 mmol, 1.0 eq) in THF (300 mL) was added NBS (18.6 g, 104 mmol, 1.0 eq). The mixture was stirred at 25° C. for 12 hours. After completion, the mixture was concentrated. The residue was purification by column chromatography (SiO$_2$, petroleum ether/ethyl acetate=1/0 to 1/1) to give the title compound (20 g, 90% yield). Orange solid; Rf=0.5 (1:1, petroleum ether/ethyl acetate).

Step B. tert-butyl 4-bromo-5-tert-butoxycarbonyloxy-indazole-1-carboxylate. To a solution of 4-bromo-1H-indazol-5-ol (20 g, 93.9 mmol, 1 eq) and DMAP (2.3 g, 18.8 mmol, 0.2 eq) in THF (150 mL) was added Boc$_2$O (22.8 g, 104 mmol, 1.1 eq) dropwise. The mixture was stirred at 25° C. for 3 hours. After completion, the reaction mixture was concentrated under reduced pressure to give a residue. The residue was purified by silica gel column chromatography (petroleum ether/ethyl acetate=25/1) to give the title compound (13 g, 31% yield). Light yellow solid; Rf=0.65 (3:1, petroleum ether/ethyl acetate); $^1$H NMR (400 MHz, DMSO-d6) δ=8.44 (d, J=0.8 Hz, 1H), 8.10 (dd, J=0.8, 9.2 Hz, 1H), 7.60 (d, J=9.2 Hz, 1H), 1.66 (s, 9H), 1.52 (s, 9H). [ESI, M−55]: 357.0.

Step C. tert-butyl 4-bromo-5-hydroxy-indazole-1-carboxylate. To a solution of tert-butyl 4-bromo-5-tert-butoxycarbonyloxy-indazole-1-carboxylate (13 g, 29.5 mmol, 1.0 eq) in THF (100 mL) and H$_2$O (100 mL) was added NaOH (3.15 g, 78.8 mmol, 2.7 eq) in portions below 5° C. The mixture was stirred at 20° C. for 40 hours. After completion, the reaction mixture was diluted with ethyl acetate (150 mL). The pH of the mixture was adjusted to 7-8 with 2N HCl below 10° C. The organic layer was separated. The water phase was extracted with EA (50 mL×3). The combined organic layers were dried over anhydrous Na$_2$SO$_4$, filtered and concentrated under reduced pressure to give a residue. The residue was purified by silica gel column chromatography (petroleum ether/ethyl acetate=8/1) to give the title compound (4.2 g, 37% yield). Light yellow solid; $^1$H NMR (400 MHz, DMSO-d6) δ=10.41 (s, 1H), 8.21 (s, 1H), 7.90 (d, J=9.2 Hz, 1H), 7.26 (d, J=8.8 Hz, 1H), 1.63 (s, 9H). [ESI, M−55+2]: 259.0.

Step D. tert-butyl 4-bromo-5-[bromo(difluoro)methoxy]indazole-1-carboxylate. To a solution of tert-butyl 4-bromo-5-hydroxy-indazole-1-carboxylate (1.1 g, 3.51 mmol, 1.0 eq) in DMF (20 mL) was added NaH (310 mg, 7.75 mmol, 60% purity, 2.2 eq) in portions at 0° C. After stirred at 0° C. for 5 minutes, dibromo(difluoro)methane (2.27 g, 10.8 mmol, 1 mL, 3 eq) was added at 0° C. and the mixture was stirred 0-25° C. for 17 hours 55 minutes. After completion, the reaction mixture was poured into diluted with H$_2$O (400 mL) and EA (60 mL). The mixture was extracted with EA (50 mL×5). The combined organic layers were dried over anhydrous Na₂SO₄, filtered and concentrated under reduced pressure to give a residue. The residue was purified by reversed phase flash chromatography [water (FA, 0.1%)/acetonitrile=3/17] to give the title compound (0.6 g, 38% yield). Brown solid; ¹H NMR (400 MHz, DMSO-d6) δ=8.52 (d, J=0.8 Hz, 1H), 8.19 (d, J=9.2 Hz, 1H), 7.74 (d, J=9.2 Hz, 1H), 1.66 (s, 9H). [ESI, M−55+2]: 386.8.

Step E. 4-bromo-5-(trifluoromethoxy)-1H-indazole. To a solution of tert-butyl-4-bromo-5-[bromo(difluoro)methoxy]indazole-1-carboxylate (2.4 g, 5.37 mmol, 1 eq) in DCE (50 mL) was added AgBF4 (7.40 g, 38.0 mmol, 7 eq) below 15° C. under N₂ atmosphere. The mixture was stirred at 65° C. for 3 hours. After completion, the reaction mixture was poured into ice water (300 mL), and diluted with EA (300 mL). The mixture was filtered through a pad of Celite. The organic layer was separated. The aqueous layer was extracted with EA (100 mL). The combined organic layers were dried over anhydrous Na₂SO₄, filtered and concentrated under reduced pressure to give a residue. The residue was purified by reversed phase flash chromatography [water (FA, 0.1%)/acetonitrile=1/9] to give the title compound (1.2 g, 77% yield). Brown solid; ¹H NMR (400 MHz, DMSO-d6) δ=13.69 (s, 1H), 8.16 (s, 1H), 7.69 (d, J=8.8 Hz, 1H), 7.47 (dd, J=0.8, 8.8 Hz, 1H); [ESI, M+H]: 281.0.

Step F. 4-bromo-1-tetrahydropyran-2-yl-5-(trifluoromethoxy)indazole. To a solution of 4-bromo-5-(trifluoromethoxy)-1H-indazole (0.6 g, 2.09 mmol, 1 eq) and TsOH·H₂O (41 mg, 216 μmol, 0.1 eq) in THF (10 mL) was added DHP (540 mg, 6.42 mmol, 3 eq) dropwise at 0° C. The mixture was stirred at 25° C. for 4 hours. After completion, the reaction mixture was quenched with H₂O (30 mL) and EA (10 mL). The pH of the mixture was adjusted to 8-9 with NaHCO₃ solid below 10° C. The mixture was extracted with EA (15 mL×4). The combined organic layers were dried over anhydrous Na₂SO₄, filtered and concentrated under reduced pressure to give a residue. The residue was purified by reversed phase flash chromatography [water (FA, 0.1%)/acetonitrile=3/17] to give the title compound (0.64 g, 80% yield). Brown solid; ¹H NMR (400 MHz, methanol-d4) δ=8.51 (s, 1H), 7.71 (dd, J=0.8, 9.2 Hz, 1H), 7.33 (dd, J=1.2, 9.2 Hz, 1H), 5.78-5.75 (m, 1H), 4.15-4.10 (m, 1H), 3.86-3.80 (m, 1H), 2.24-2.15 (m, 2H), 2.08-2.03 (m, 1H), 1.87-1.64 (m, 3H);

Step G. 1-tetrahydropyran-2-yl-4-(4,4,5,5-tetramethyl-1,3,2-dioxaborolan-2-yl) 5-(trifluoromethoxy)indazole. A mixture of 4-bromo-1-tetrahydropyran-2-yl-5-(trifluoromethoxy)indazole (640 mg, 1.69 mmol, 1 eq) 4,4,5,5-tetramethyl-2-(4,4,5,5-tetramethyl-1,3,2-dioxaborolan-2-yl)-1,3,2-dioxaborolane (890 mg, 3.50 mmol, 2 eq), KOAc (517 mg, 5.27 mmol, 3 eq) and Pd(dppf)Cl₂ (130 mg, 178 μmol, 0.1 eq) in dioxane (15 mL) was degassed and purged with N₂ for 3 times. The mixture was stirred at 100° C. for 1.5 hours under N₂ atmosphere. After completion, the reaction mixture was diluted with H₂O (30 mL) and extracted with EA (15 mL×4). The combined organic layers were washed with brine (10 mL), dried over anhydrous Na₂SO₄, filtered and concentrated under reduced pressure to give a residue. The residue was purified by reversed phase flash chromatography [water (FA, 0.1%)/acetonitrile=1/9] to give the title compound (0.19 g, 21% yield). Gray solid; [ESI, M+1]: 413.1.

Step: H. tert-butyl (1R,5S)-3-(8-fluoro-2-((tetrahydro-1H-pyrrolizin-7a(5H)-yl)methoxy)-7-(1-(tetrahydro-2H-pyran-2-yl)-5-(trifluoromethoxy)-1H-indazol-4-yl)pyrido[4,3-d]pyrimidin-4-yl)-3,8-diazabicyclo[3.2.1]octane-8-carboxylate. To a mixture of (1R,5S)-tert-butyl 3-(7-chloro-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (100 mg, 188 μmol, 1 eq) in THF (2.5 mL) and K₃PO₄ (1.5 M in H₂O, 0.5 mL, 4.00 eq) was degassed and purged with N₂ for 3 times. [2-(2-aminophenyl)phenyl]palladium(1+); bis(1-adamantyl)-butyl-phosphane; methanesulfonate (21 mg, 28.8 μmol, 0.15 eq) was added, followed by 1-tetrahydropyran-2-yl-4-(4,4,5,5-tetramethyl-1,3,2-dioxaborolan-2-yl) 5-(trifluoromethoxy)indazole (170 mg, 326 μmol, 1.7 eq). The mixture was stirred at 60° C. for 3 hours. After completion, the reaction mixture was diluted with H₂O (5 mL) and extracted with EA (10 mL×4). The combined organic layers were dried over anhydrous Na₂SO₄, filtered and concentrated under reduced pressure to give a residue. The residue was purified by reversed phase flash chromatography [water (FA, 0.1%)/acetonitrile=3/2] to give the title compound (62.5 mg, 37% yield). Light yellow gum; [ESI, M+1]: 783.3.

Step I. 4-((1R,5S)-3,8-diazabicyclo[3.2.1]octan-3-yl)-8-fluoro-2-((hexahydro-1H-pyrrolizin-7a-yl)methoxy)-7-(5-(trifluoromethoxy)-1H-indazol-4-yl)pyrido[4,3-d]pyrimidine. To a solution of tert-butyl (1R,5S)-3-(8-fluoro-2-((tetrahydro-1H-pyrrolizin-7a(5H)-yl)methoxy)-7-(1-(tetrahydro-2H-pyran-2-yl)-5-(trifluoromethoxy)-1H-indazol-4-yl)pyrido[4,3-d]pyrimidin-4-yl)-3,8-diazabicyclo[3.2.1]octane-8-carboxylate (70 mg, 79.6 μmol, 1 eq) in ACN (2 mL) was added HCl·dioxane (4 M, 6 mL) dropwise below 15° C. The mixture was stirred at 15° C. for 0.5 hour. After completion, the reaction mixture was concentrated under reduced pressure to give a residue at 15° C. (without heating). The residue was dissolved in DCM (5 mL) and H₂O (5 mL). The pH of the mixture was adjusted to 8-9 with NaHCO₃ solid below 5° C. The mixture was extracted with DCM (5 mL×5). The combined organic layers were dried over anhydrous Na₂SO₄, filtered and concentrated under reduced pressure to give a residue. The residue was purified by prep-HPLC (column: Shim-pack C18 150*25*10 um; mobile phase: [water (0.225% FA)-ACN]; B %: 9%-29%, 9 min) to give the title compound (5.37 mg, 10% yield, 1.8FA). Off-white solid; ¹H NMR (400 MHz, methanol-d4) δ=9.26 (s, 1H), 7.99 (s, 1H), 7.82 (d, J=9.2 Hz, 1H), 7.54 (dd, J=1.2, 9.2 Hz, 1H), 4.77 (d, J=12.4 Hz, 2H), 4.67 (s, 2H), 3.93 (s, 2H), 3.84 (br d, J=12.8 Hz, 2H), 3.73-3.67 (m, 2H), 3.29-3.26 (m, 2H), 2.38-2.32 (m, 2H), 2.26-2.08 (m, 6H), 2.00-1.91 (m, 4H). ¹⁹F NMR (377 MHz, methanol-d4) δ=−59.1, −138. [ESI, M+1]: 599.2.

Example 259

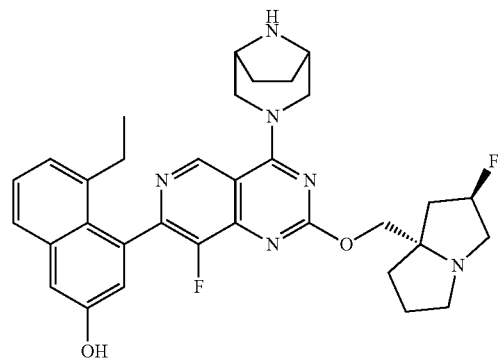 [SMILES: CCc1cccc2cc(O)cc(-c3ncc4c(N5CC6CCC(C5)N6)nc(OC[C@@]56CCCN5C[C@H](F)C6)nc4c3F)c12]

4-(4-((1R,5S)-3,8-diazabicyclo[3.2.1]octan-3-yl)-8-fluoro-2-(((2R,7aS)-2-fluorotetrahydro-1H-pyrrolizin-7a(5H)-yl)methoxy)pyrido[4,3-d]pyrimidin-7-yl)-5-ethylnaphthalen-2-ol

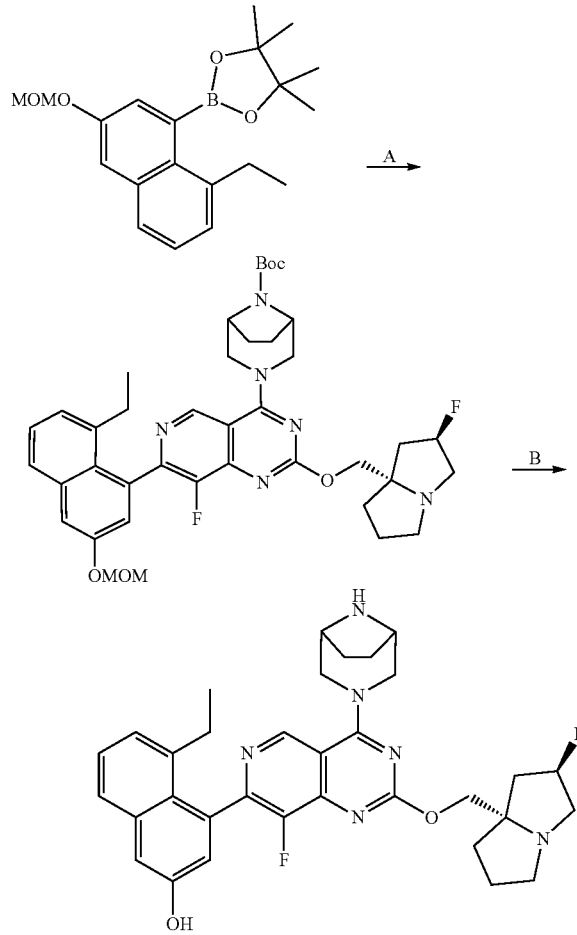

Step A. tert-butyl (1R,5S)-3-(7-(8-ethyl-3-(methoxymethoxy)naphthalen-1-yl)-8-fluoro-2-(((2R,7a5)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate. A mixture 2-(8-ethyl-3-(methoxymethoxy)naphthalen-1-yl)-4,4,5,5-tetramethyl-1,3,2-dioxaborolane (547 mg, 1.60 mmol, 1.1 eq), tert-butyl (1R,5S)-3-(7-chloro-8-fluoro-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (800 mg, 1.45 mmol, 1 eq), $K_3PO_4$ (1.5 M in $H_2O$, 2.90 mL, 3 eq) and [2-(2-aminophenyl)phenyl]palladium(1+); bis(1-adamantyl)-butyl-phosphane; methanesulfonate (106 mg, 145 μmol, 0.1 eq) in THF (18 mL) was stirred at 60° C. for 2 hours under $N_2$. After completion, the mixture was diluted with water (10 mL) and extracted with ethyl acetate (2×20 mL). The combined organic layer was washed with brine (20 mL), dried over $Na_2SO_4$, filtered and concentrated under vacuum. The residue was purified by reversed phase flash chromatography [water (FA, 0.1%)/acetonitrile] to give the title compound (650 mg, 60% yield). Yellow solid. LCMS [ESI, M+1]: 731.4.

Step B. 4-(4-((1R,5S)-3,8-diazabicyclo[3.2.1]octan-3-yl)-8-fluoro-2-(((2R,7aS)-2-fluorotetrahydro-1H-pyrrolizin-7a(5H)-yl)methoxy)pyrido[4,3-d]pyrimidin-7-yl)-5-ethylnaphthalen-2-ol. A mixture of tert-butyl (1R,5S)-3-(7-(8-ethyl-3-(methoxymethoxy)naphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (900 mg, 1.23 mmol, 1 eq) in HCl/dioxane (4 M, 3.79 mL, 12.3 eq) and acetonitrile (10 mL) was stirred at 20° C. for 0.5 hour. After completion, the mixture was concentrated under vacuum. The residue was purified by prep-HPLC (column: Phenomenex luna C18 150*40 mm*15 um; mobile phase: [water (0.225% FA)-ACN]; B %: 3%-33%, 10 min) to give the title compound (450 mg formic acid salt, 57% yield). Off-white solid. SFC: "Column: Chiralpak IC-3 50×4.6 mm I.D., 3 um Mobile phase: Phase A for $CO_2$, and Phase B for MeOH+ACN (0.05% DEA); Gradient elution: 60% MeOH+ACN (0.05% DEA) in $CO_2$. Flow rate: 3 mL/min; Detector: PDA; Column Temp: 35 C; Back Pressure: 100 Bar". $^1H$ NMR (400 MHz, METHANOL-d4) δ=9.11 (s, 1H), 7.64 (d, J=8.0 Hz, 1H), 7.37 (t, J=7.6 Hz, 1H), 7.30 (d, J=2.4 Hz, 1H), 7.17 (d, J=7.2 Hz, 1H), 7.00 (d, J=2.4 Hz, 1H), 5.54 (d, J=8.4 Hz, 1H), 4.80-4.68 (m, 2H), 4.61-4.49 (m, 2H), 4.13-4.01 (m, 2H), 3.98-3.61 (m, 5H), 3.37-3.33 (m, 1H), 2.68-2.17 (m, 7H), 2.04 (br d, J=13.2 Hz, 5H), 0.89 (dt, J=1.6, 7.6 Hz, 3H). [ESI, M+1]: 587.2.

Example 260

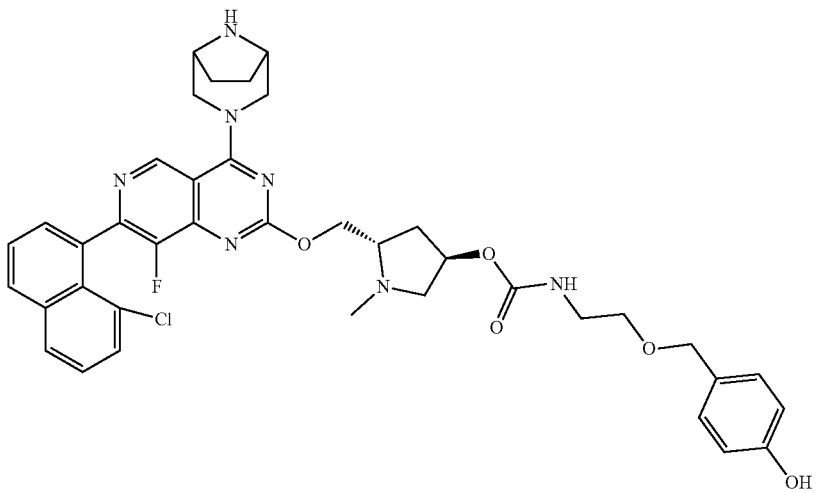 [SMILES: CN1C[C@H](OC(=O)NCCOCc2ccc(O)cc2)C[C@H]1COc1nc(N2CC3CCC(C2)N3)c2cnc(-c3cccc4cccc(Cl)c34)c(F)c2n1]

(3R,5S)-5-(((4-((1R,5S)-3,8-diazabicyclo[3.2.1]oc-tan-3-yl)-7-(8-chloronaphthalen-1-yl)-8-fluoropyrido[4,3-d]pyrimidin-2-yl)oxy)methyl)-1-methylpyrrolidin-3-yl (2-((4-hydroxybenzyl)oxy)ethyl)carbamate
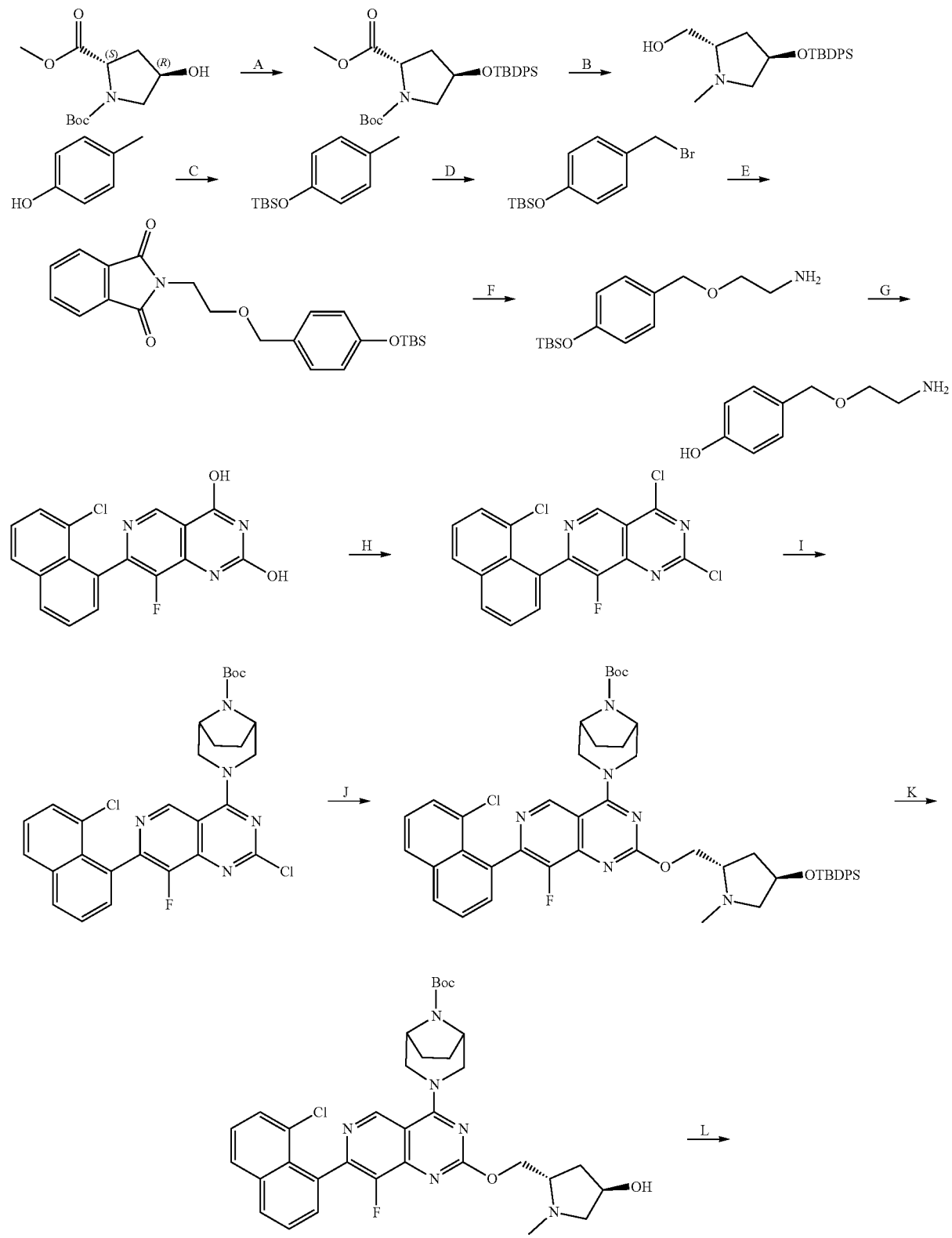

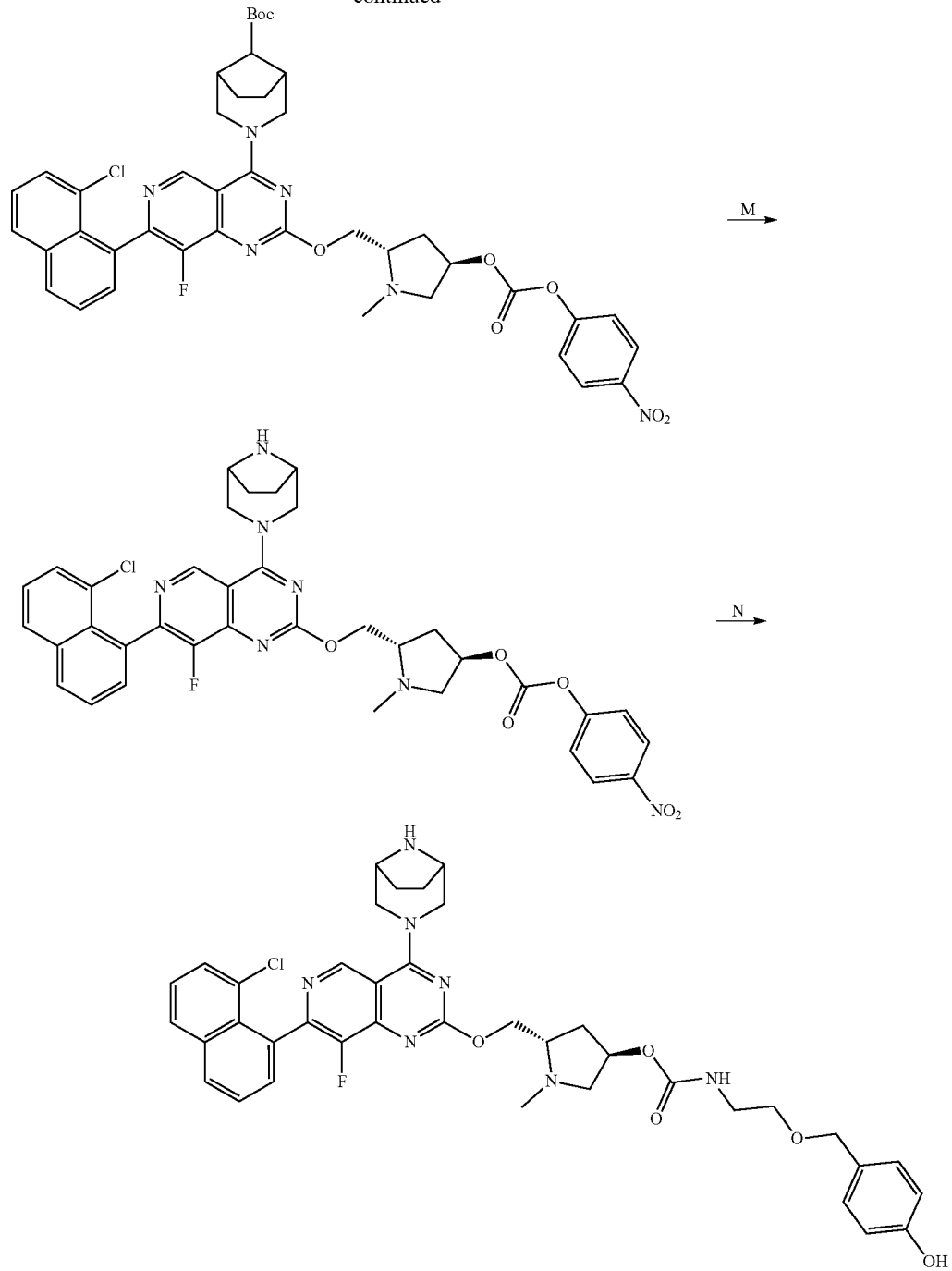

Step A. (2S,4R)-1-tert-butyl2-methyl4-((tert-butyldiphenylsilyl)oxy)pyrrolidine-1,2-dicarboxylate. To a mixture of (2S,4R)-1-tert-butyl 2-methyl 4-hydroxypyrrolidine-1,2-dicarboxylate (10.0 g, 40.8 mmol, 1 eq) and imidazole (8.33 g, 122.3 mmol, 3.0 eq) in DCM (100 mL) was added TBDPS-Cl (16.8 g, 61.2 mmol, 15.7 mL, 1.5 eq) in one portion at 0° C. under N₂. The mixture was stirred at 25° C. for 2 hours. After completion, the reaction mixture was concentrated under reduced pressure to give a residue. The residue was purified by reversed phase flash chromatography (C18, 0.1% FA in water, 0-100% MeCN) to give the title compound (13.5 g, 62% yield). White solid; ¹H NMR (400 MHz, DMSO-d6) δ=7.58 (br s, 4H), 7.52-7.41 (m, 6H), 4.45-4.36 (m, 1H), 4.35-4.26 (m, 1H), 4.03 (q, J=7.1 Hz, 1H), 3.60 (s, 1H), 3.33 (s, 4H), 1.99 (s, 2H), 1.41-1.29 (m, 9H), 1.00 (s, 9H). [ESI, M−99]: 384.1.

Step B. ((2S,4R)-4-((tert-butyldiphenylsilyl)oxy)-1-methylpyrrolidin-2-yl)methanol. To a mixture of (2S,4R)-1-tert-butyl2-methyl4-((tert-butyldiphenylsilyl)oxy)pyrrolidine-1,2-dicarboxylate (3.00 g, 6.20 mmol, 1.0 eq) in THF (30 mL) was added LiAlH₄ (1.41 g, 37.2 mmol, 6.0 eq) in one portion at −40° C. under N₂. The mixture was stirred at −40° C. for 1 hour, then heated to 40° C. and stirred for 1 hour. After completion, the reaction mixture was diluted with water (1.4 mL), 15% sodium hydroxide solution (1.4 ml), water (5.2 mL) and extracted with EtOAc (3×30 mL). The combined organic layers were washed with saturated brine (60 mL), dried over anhydrous sodium sulfate, filtered and concentrated under vacuum to give the residue. The residue was purified by reversed phase flash chromatography (C18, 0.1% FA in water, 0-100% MeCN) to give the title compound (650 mg, 28% yield). White solid; $^1$H NMR (400 MHz, DMSO-d6) δ=7.61 (ddd, J=1.6, 5.0, 7.7 Hz, 4H), 7.54-7.42 (m, 6H), 4.49-4.41 (m, 1H), 3.71 (br d, J=8.4 Hz, 1H), 3.56-3.48 (m, 1H), 3.07 (br s, 1H), 2.86 (s, 3H), 2.30 (s, 2H), 2.04-1.83 (m, 2H), 1.04 (s, 9H). [ESI, M+1]: 370.1.

Step C. tert-butyldimethyl(p-tolyloxy)silane. To a mixture of p-cresol (10.0 g, 92.5 mmol, 9.71 mL, 1.0 eq) and imidazole (18.9 g, 277.4 mmol, 3.0 eq) in DCM (100 mL) was added TBDMSCl (20.9 g, 138.7 mmol, 17.0 mL, 1.5 eq) in one portion at 0° C. under $N_2$. The mixture was stirred at 20° C. for 2 hours. After completion, the reaction mixture was concentrated under reduced pressure to give a residue. The residue was purified by column chromatography (SiO$_2$, Petroleum ether) to give the title compound (17.6 g, 86% yield). Colorless oil; $^1$H NMR (400 MHz, DMSO-d6) δ=6.88 (d, J=8.2 Hz, 2H), 6.57 (d, J=8.3 Hz, 2H), 2.07 (s, 3H), 0.82-0.74 (m, 9H), 0.00 (s, 6H).

Step D. (4-(Bromomethyl)phenoxy)(tert-butyl)dimethylsilane. To a mixture of tert-butyldimethyl(p-tolyloxy)silane (5.00 g, 22.5 mmol, 1.0 eq) in CCl$_4$ (50.0 mL) were added NBS (4.40 g, 24.7 mmol, 1.1 eq), and benzoyl peroxide (54.46 mg, 224.82 μmol, 0.01 eq) in one portion under $N_2$. The mixture was stirred at 80° C. for 2 hours. After completion, the reaction mixture was filtered and the solution was concentrated under vacuum to give the title compound (8.5 g, crude), Which was used in the next step without further purification. Red oil.

Step E. 2-(2-((4-((tert-butyldimethylsilyl)oxy)benzyl)oxy)ethyl)isoindoline-1,3-dione. To a solution of 2-(2-hydroxyethyl)isoindoline-1,3-dione (2.64 g, 13.8 mmol, 1.0 eq) in THF (30 mL) was added NaH (1.11 g, 27.7 mmol, 60% purity, 2.0 eq) at 0° C. over a period of 30 minutes under $N_2$. Then (4-(Bromomethyl)phenoxy)(tert-butyl)dimethylsilane (5.00 g, 16.6 mmol, 1.2 eq) was added to the mixture at 0° C. over another 30 mins under $N_2$. The reaction mixture was warmed to 20° C. for 1 hour. After completion, the reaction mixture was quenched by water (120 mL) and extracted with EtOAc (120 mL). The combined organic layers were washed with saturated brine (120 mL), dried over anhydrous sodium sulfate, filtered and concentrated under reduced pressure. The residue was purified by column chromatography (SiO$_2$, Petroleum ether/Ethyl acetate=20/1 to 5/1) to give the title compound (650 mg, two steps 11% yield). Yellow solid; $^1$H NMR (400 MHz, DMSO-d6) δ=7.75-7.66 (m, 4H), 6.96 (d, J=8.6 Hz, 2H), 6.56 (d, J=8.4 Hz, 2H), 4.23 (s, 2H), 3.68-3.59 (m, 2H), 3.52-3.41 (m, 2H), 0.78 (s, 9H), 0.00 (s, 6H).

Step F: 2-((4-((tert-butyldimethylsilyl)oxy)benzyl)oxy)ethanamine. To a mixture of 2-(2-((4-((Tert-butyldimethylsilyl)oxy)benzyl)oxy)ethyl)isoindoline-1,3-dione (100 mg, 243.0 μmol, 1.0 eq) in EtOH (2 mL) was added hydrazine hydrate (57.2 mg, 971.9 μmol, 55.8 μL, 85% purity, 4.0 eq) in one portion under $N_2$. The mixture was stirred at 80° C. for 2 hours. After completion, the reaction mixture was filtered and the filtrate was concentrated under vacuum to give the title compound (70 mg, crude), Which was used in the next step without further purification. Yellow solid; $^1$H NMR (400 MHz, DMSO-d6) δ=7.03 (d, J=8.5 Hz, 2H), 6.66-6.61 (m, 2H), 4.20 (s, 2H), 3.21-3.18 (m, 2H), 2.52-2.48 (m, 2H), 0.77 (s, 9H), 0.00 (s, 6H); [ESI, M+1]: 282.2.

Step G. 4-((2-Aminoethoxy)methyl)phenol. To a mixture of 2-((4-((Tert-butyldimethylsilyl)oxy)benzyl)oxy)ethanamine (60 mg, 213.2 μmol, 1.0 eq) in THF (1.0 mL) was added TBAF (1 M in THF, 213.17 μL, 1.0 eq) in one portion under $N_2$. The mixture was stirred at 20° C. for 1 hour. After completion, the reaction mixture was concentrated under reduced pressure to give a residue. The residue was purified by reversed phase flash chromatography [C18, 0.1% FA in water, 0-100% MeCN] to give the title compound (30 mg, crude). White oil; $^1$H NMR (400 MHz, DMSO-d6) δ=8.44 (br s, 1H), 7.14 (br d, J=7.2 Hz, 2H), 6.73 (br d, J=7.6 Hz, 2H), 4.35 (br s, 2H), 3.45 (br s, 2H), 3.15 (br s, 2H). [ESI, M+1]: 168.1.

Step H. 2,4-Dichloro-7-(8-chloronaphthalen-1-yl)-8-fluoropyrido[4,3-d]pyrimidine. To a mixture of 7-(8-chloronaphthalen-1-yl)-8-fluoropyrido[4,3-d]pyrimidine-2,4-diol (1.50 g, 4.39 mmol, 1.0 eq) in POCl$_3$ (23.6 g, 154 mmol, 14.3 mL, 35 eq) was added DIEA (2.84 g, 21.9 mmol, 3.82 mL, 5.0 eq) in one portion at 20° C. under $N_2$. The mixture was stirred at 110° C. for 1 hour. After completion, the reaction mixture was concentrated under reduced pressure to give the title compound (2.00 g, crude). Brown oil. The crude product was used into the next step without further purification.

Step I. (1R,5S)-tert-butyl 3-(2-chloro-7-(8-chloronaphthalen-1-yl)-8-fluoropyrido[4,3-d]pyrimidin-4-yl)-3,8-diazabicyclo[3.2.1]octane-8-carboxylate. To a solution of 2,4-Dichloro-7-(8-chloronaphthalen-1-yl)-8-fluoropyrido[4,3-d]pyrimidine (1.6 g, 4.23 mmol, 1 eq) and DIEA (819.26 mg, 6.34 mmol, 1.10 mL, 1.5 eq) in DCM (15 mL) was added a solution of tert-butyl 3,8-diazabicyclo[3.2.1]octane-8-carboxylate (807.4 mg, 3.80 mmol, 0.9 eq) in DCM (15 mL) drop-wise at −40° C. over a period of 5 min under $N_2$ and the mixtures was stirred at −40° C. for 25 minutes. After completion, the reaction mixture was concentrated under reduced pressure to give a residue. The residue was purified by reversed phase flash chromatography [C18, 0.1% FA in water, 0-100% MeCN] to give the title compound (750 mg, two steps 30% yield). Yellow solid; $^1$H NMR (400 MHz, DMSO-d6) δ=9.30 (s, 1H), 8.25 (dd, J=1.0, 8.3 Hz, 1H), 8.14 (dd, J=1.0, 8.2 Hz, 1H), 7.80-7.73 (m, 1H), 7.71-7.58 (m, 3H), 4.56 (br d, J=9.7 Hz, 2H), 4.39-4.27 (m, 2H), 3.85-3.67 (m, 2H), 1.85 (br d, J=3.4 Hz, 2H), 1.77-1.67 (m, 2H), 1.49 (s, 9H). [ESI, M+1]: 554.1.

Step J. (1R,5S)-tert-butyl 3-(2-(((2S,4R)-4-((tert-butyldiphenylsilyl)oxy)-1-methylpyrrolidin-2-yl)methoxy)-7-(8-chloronaphthalen-1-yl)-8-fluoropyrido[4,3-d]pyrimidin-4-yl)-3,8-diazabicyclo[3.2.1]octane-8-carboxylate. To a mixture of (1R,5S)-tert-butyl 3-(2-chloro-7-(8-chloronaphthalen-1-yl)-8-fluoropyrido[4,3-d] pyrimidin-4-yl)-3,8-diazabicyclo[3.2.1]octane-8-carboxylate (500 mg, 902 μmol, 1.0 eq) and ((2S,4R)-4-((tert-butyldiphenylsilyl)oxy)-1-methylpyrrolidin-2-yl)methanol (500 mg, 1.35 mmol, 1.5 eq) in toluene (8.0 mL) was added tBuONa (260 mg, 2.71 mmol, 3.0 eq) in one portion under $N_2$. The mixture was stirred at 0° C. for 1 hour. After completion, the reaction mixture was concentrated under reduced pressure to give a residue. The residue was purified by reversed phase flash chromatography [C18, 0.1% FA in water, 0-100% MeCN] to give the title compound (600 mg, 60% yield). Yellow solid; $^1$H NMR (400 MHz, DMSO-d6) δ=9.14 (s, 1H), 8.21 (dd, J=1.0, 8.3 Hz, 1H), 8.10 (d, J=8.1 Hz, 1H), 7.73 (t, J=7.6 Hz, 1H), 7.68-7.63 (m, 1H), 7.63-7.54 (m, 6H), 7.49-7.38 (m, 6H), 4.55-4.45 (m, 2H), 4.44-4.23 (m, 5H), 3.64 (br t, J=14.2 Hz, 2H), 1.99 (s, 4H), 1.90-1.78 (m, 3H), 1.67 (br d, J=7.7 Hz, 2H), 1.47 (s, 9H), 1.18 (t, J=7.2 Hz, 3H), 1.01 (s, 9H). [ESI, M+1]: 887.3.

Step K. (1R,5S)-tert-butyl 3-(7-(8-chloronaphthalen-1-yl)-8-fluoro-2-(((2S,4R)-4-hydroxy-1-methylpyrrolidin-2-yl)methoxy)pyrido[4,3-d]pyrimidin-4-yl)-3,8-diazabicyclo[3.2.1]octane-8-carboxylate. To a mixture of (1R,5S)-tert-butyl 3-(2-(((2S,4R)-4-((tert-butyldiphenylsilyl)oxy)-1-methylpyrrolidin-2-yl)methoxy)-7-(8-chloronaphthalen-1-yl)-8-fluoropyrido[4,3-d]pyrimidin-4-yl)-3,8-diazabicyclo[3.2.1]octane-8-carboxylate (450 mg, 507 µmol, 1 eq) in THF (2.0 mL) was added TBAF (1 M in THF, 507 µL, 1.0 eq) in one portion under N₂. The mixture was stirred at 20° C. for 1 hour. After completion, the reaction mixture was concentrated under reduced pressure to give a residue. The residue was purified by column chromatography (Al₂O₃, dichloromethane/methanol=10/1) to give the title compound (580 mg, crude). Yellow oil; [ESI, M+1]: 649.2.

Step L. (1R,5S)-tert-butyl 3-(7-(8-chloronaphthalen-1-yl)-8-fluoro-2-(((2S,4R)-1-methyl-4-(((4-nitrophenoxy)carbonyl)oxy)pyrrolidin-2-yl)methoxy)pyrido[4,3-d]pyrimidin-4-yl)-3,8-diazabicyclo[3.2.1]octane-8-carboxylate. To a mixture of (1R,5S)-tert-butyl 3-(7-(8-chloronaphthalen-1-yl)-8-fluoro-2-(((2S,4R)-4-hydroxy-1-methylpyrrolidin-2-yl)methoxy)pyrido[4,3-d]pyrimidin-4-yl)-3,8-diazabicyclo[3.2.1]octane-8-carboxylate (50 mg, 77.0 µmol, 1.0 eq) and (4-nitrophenyl) carbonochloridate (46.6 mg, 231. µmol, 3.0 eq) in THF (1 mL) was added tBuOK (1 M, 154 µL, 2.0 eq) in one portion at 20° C. under N₂. The mixture was stirred at 20° C. for 1 hour. After completion, the reaction mixture was quenched by water (5.0 mL) at 20° C., diluted with water (5.0 mL), and extracted with EtOA (10 mL×2). The combined organic layers were washed with saturated sodium chloride solution (20 mL), dried over anhydrous sodium sulfate, filtered and concentrated under vacuum. The residue was purified by reversed phase flash chromatography [C18, 0.1% FA in water, 0-100% MeCN] to give the title compound (50 mg, 78% yield). Yellow solid; [ESI, M+1]: 814.2.

Step M. (3R,5S)-5-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)-1-methylpyrrolidin-3-yl (4-nitrophenyl) carbonate. To a solution of (1R,5S)-tert-butyl 3-(7-(8-chloronaphthalen-1-yl)-8-fluoro-2-(((2S,4R)-1-methyl-4-(((4-nitrophenoxy)carbonyl)oxy)pyrrolidin-2-yl)methoxy)pyrido[4,3-d]pyrimidin-4-yl)-3,8-diazabicyclo[3.2.1]octane-8-carboxylate (50 mg, 61.4 µmol, 1.0 eq) in MeCN (0.5 mL) was added HCl/dioxane (4 M, 0.25 mL, 16.3 eq) under N₂. The mixture was stirred at 0° C. for 0.5 hour. After completion, the reaction mixture was concentrated under reduced pressure to give the title compound (30 mg, crude). Brown oil. [ESI, M+1]: 714.2. The crude product was used into the next step without further purification.

Step N. (3R,5S)-5-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)-1-methylpyrrolidin-3-yl (2-((4-hydroxybenzyl)oxy)ethyl)carbamate. To a mixture of (3R,5S)-5-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)-1-methylpyrrolidin-3-yl (4-nitrophenyl) carbonate (30 mg, 42.0 µmol, 1.0 eq) and 4-((2-aminoethoxy)methyl)phenol (17.6 mg, 105 µmol, 2.5 eq) in DMF (1 mL) was added DIEA (27.1 mg, 210 µmol, 36.6 µL, 5.0 eq) in one portion under N₂. The mixture was stirred at 20° C. for 12 hours. After completion, the reaction mixture was concentrated under reduced pressure to give a residue. The residue was purified by prep-HPLC (column: Phenomenex Synergi C18 150*25*10 um; mobile phase: [water (0.225% FA)-ACN]; B %: 13%-43%, 8.5 min) to give the title compound (2.27 mg, two steps 6.5% yield). White solid; ¹H NMR (400 MHz, DMSO+D2O) δ=9.07 (s, 1H), 8.27 (s, 1H), 8.20-8.15 (m, 1H), 8.09-8.04 (m, 1H), 7.71 (t, J=7.7 Hz, 1H), 7.66-7.62 (m, 1H), 7.60-7.52 (m, 2H), 7.10 (br d, J=8.5 Hz, 2H), 6.73-6.67 (m, 2H), 4.94-4.85 (m, 1H), 4.57 (br d, J=13.1 Hz, 2H), 4.47-4.39 (m, 1H), 4.38-4.26 (m, 3H), 3.99 (br s, 2H), 3.78 (br t, J=11.8 Hz, 2H), 3.41-3.31 (m, 3H), 3.16-3.06 (m, 2H), 2.88 (br d, J=2.0 Hz, 1H), 2.36 (s, 3H), 2.28 (br dd, J=5.0, 10.4 Hz, 1H), 2.04-1.76 (m, 6H). [ESI, M+1]: 742.3.

Example 261

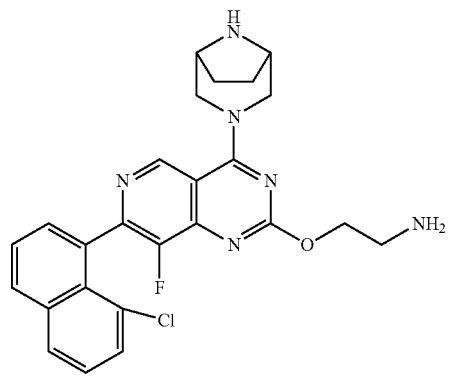 [SMILES: NCCOc1nc(N2CC3CCC(C2)N3)c2cnc(-c3cccc4cccc(Cl)c34)c(F)c2n1]

2-((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)ethanamine

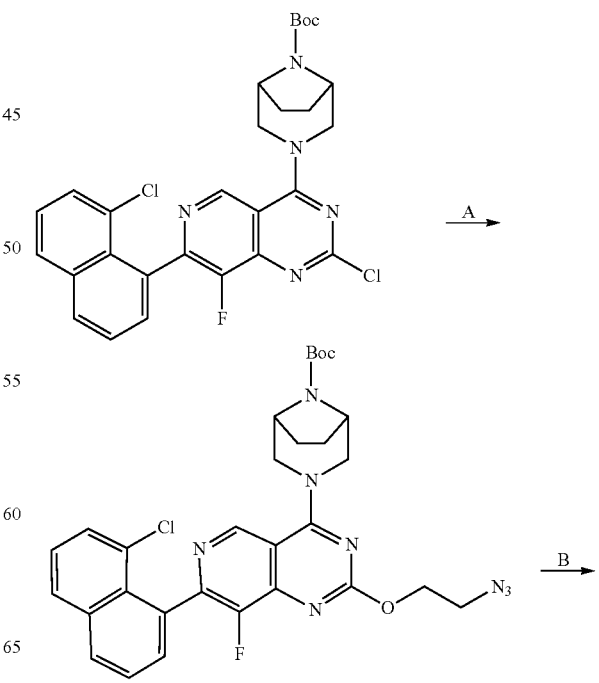

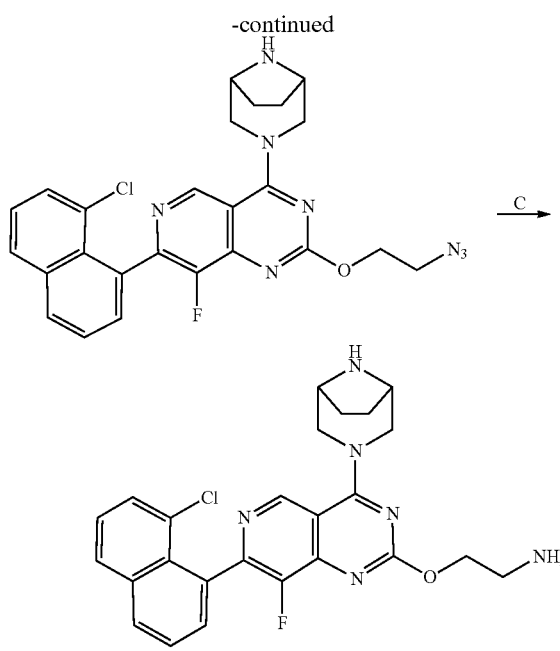

Step A. tert-butyl 3-[2-(2-azidoethoxy)-7-(8-chloro-1-naphthyl)-8-fluoro-pyrido[4,3-d]pyrimidin-4-yl]-3,8-diazabicyclo[3.2.1]octane-8-carboxylate. A mixture of (1R,5S)-tert-butyl 3-(2-chloro-7-(8-chloronaphthalen-1-yl)-8-fluoropyrido[4,3-d] pyrimidin-4-yl)-3,8-diazabicyclo[3.2.1] octane-8-carboxylate (120 mg, 216 μmol, 1.0 eq), 2-azidoethanol (37.7 mg, 433 μmol, 2.0 eq), Cs$_2$CO$_3$ (211 mg, 649 μmol, 3.0 eq) in acetonitrile (2.0 mL) was degassed, and purged with N$_2$ for 3 times. The mixture was stirred at 60° C. for 3 hours under N$_2$ atmosphere. The reaction mixture was diluted with water (3.0 mL) and extracted with ethyl acetate (3×2.0 mL). The combined organic layers were dried over Na$_2$SO$_4$, filtered and concentrated under reduced pressure. The residue was purified by reversed phase flash chromatography [water (0.1% formic acid)/acetonitrile)] to give the title compound (120 mg, 91% yield). Yellow oil; $^1$H NMR (400 MHz, chloroform-d) δ=9.04 (s, 1H), 8.01 (dd, J=1.6, 7.6 Hz, 1H), 7.89 (d, J=8.4 Hz, 1H), 7.66-7.52 (m, 3H), 7.47-7.39 (m, 1H), 4.67 (t, J=5.2 Hz, 2H), 4.62 (br d, J=12.4 Hz, 1H), 4.57-4.48 (m, 1H), 4.47-4.32 (m, 2H), 3.78-3.63 (m, 4H), 2.02-1.95 (m, 2H), 1.89-1.76 (m, 2H), 1.51 (s, 9H). [ESI, M+1]: 605.2.

Step B. 2-(2-azidoethoxy)-7-(8-chloro-1-naphthyl)-4-(3,8-diazabicyclo[3.2.1]octan-3-yl)-8-fluoro-pyrido[4,3-d]pyrimidine. To a solution of tert-butyl 3-[2-(2-azidoethoxy)-7-(8-chloro-1-naphthyl)-8-fluoro-pyrido[4,3-d]pyrimidin-4-yl]-3,8-diazabicyclo[3.2.1]octane-8-carboxylate (90 mg, 149 μmol, 1.0 eq) in acetonitrile (1.0 mL) was added HCl·dioxane (4 M, 0.5 mL). The mixture was stirred at 0° C. for 30 minutes. The mixture was concentrated, and then the reaction mixture was diluted with water (1.0 mL). Then the mixture was adjusted pH~8 with saturated NaHCO$_3$ aqueous solution, extracted with dichloromethane (3×2.0 mL), dried over Na$_2$SO$_4$, filtered and concentrated to give the title compound (60 mg, crude). Yellow solid.

Step C. 2-[7-(8-chloro-1-naphthyl)-4-(3,8-diazabicyclo [3.2.1]octan-3-yl)-8-fluoro-pyrido[4,3-d]pyrimidin-2-yl] oxyethanamine. To a solution of 2-(2-azidoethoxy)-7-(8-chloro-1-naphthyl)-4-(3,8-diazabicyclo[3.2.1]octan-3-yl)-8-fluoro-pyrido[4,3-d]pyrimidine (60 mg, 119 μmol, 1.0 eq) in H$_2$O (1.0 mL) and THF (3.0 mL) was added PPh$_3$ (156 mg, 594 μmol, 5.0 eq). The mixture was stirred at 25° C. for 12 hours. The mixture was concentrated under vacuum. The residue was purified by prep-HPLC (column: Waters X bridge C18 150*50 mm*10 um; mobile phase: [water (10 mM NH$_4$HCO$_3$)-ACN]; B %: 18%-48%, 10 min) to give the title compound (6.83 mg, 11% yield). White solid; $^1$H NMR (400 MHz, DMSO+D2O) δ=8.93-8.78 (m, 1H), 8.22-8.13 (m, 1H), 8.06 (br d, J=8.4 Hz, 1H), 7.72-7.66 (m, 1H), 7.64-7.60 (m, 1H), 7.59-7.51 (m, 2H), 4.69-4.55 (m, 1H), 4.42 (br d, J=14.0 Hz, 1H), 4.15-4.09 (m, 2H), 3.81-3.62 (m, 2H), 3.59-3.52 (m, 2H), 3.51-3.40 (m, 2H), 2.09-1.82 (m, 4H). [ESI, M+1]: 479.2.

Example 262

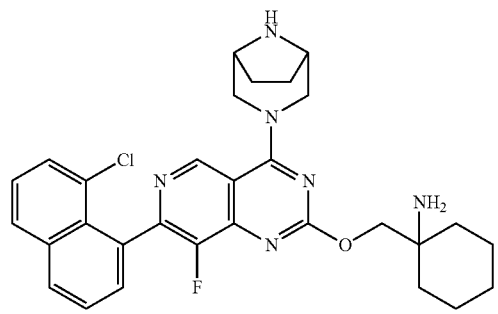 [SMILES: NC1(COc2nc(N3CC4CCC(C3)N4)c3cnc(-c4cccc5cccc(Cl)c45)c(F)c3n2)CCCCC1]

1-(((4-((1R,5S)-3,8-diazabicyclo[3.2.1]octan-3-yl)-7-(8-chloronaphthalen-1-yl)-8-fluoropyrido[4,3-d] pyrimidin-2-yl)oxy)methyl)cyclohexanamine

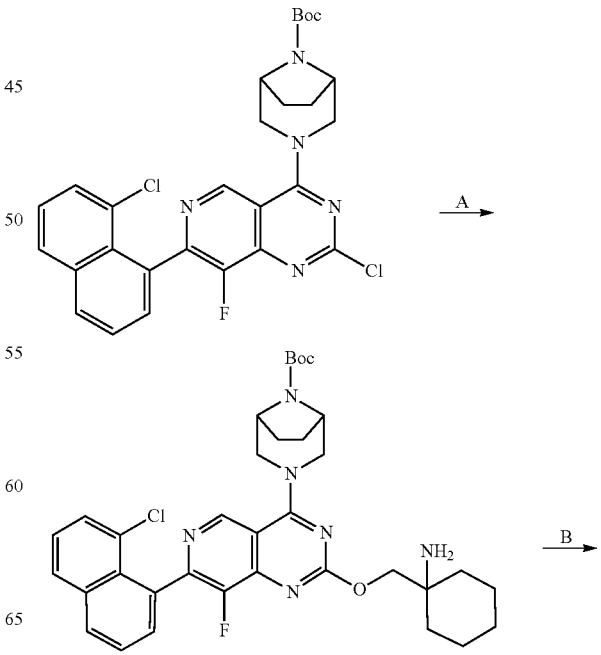

577
-continued

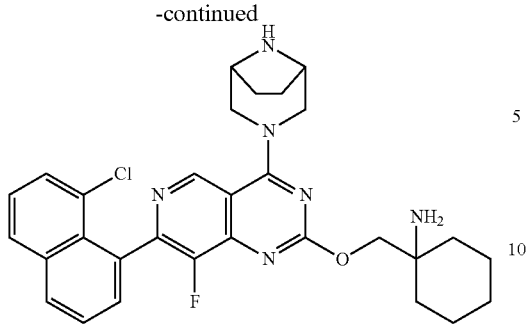

Step A. (1R,5S)-tert-butyl 3-(2-((1-aminocyclohexyl) methoxy)-7-(8-chloronaphthalen-1-yl)-8-fluoropyrido[4,3-d]pyrimidin-4-yl)-3,8-diazabicyclo[3.2.1]octane-8-carboxylate. To a solution of (1-aminocyclohexyl)methanol (51.3 mg, 397 μmol, 1.1 eq) in THF (4 mL) was added NaH (43.3 mg, 1.08 mmol, 60% purity, 3.0 eq) at −10° C. over a period of 5 min under $N_2$. Then (1R,5S)-tert-butyl 3-(2-chloro-7-(8-chloronaphthalen-1-yl)-8-fluoropyrido[4,3-d]pyrimidin-4-yl)-3,8-diazabicyclo[3.2.1]octane-8-carboxylate (200 mg, 361 μmol, 1.0 eq) was added to the mixture at −10° C. under $N_2$. The reaction mixture was stirred at 0° C. for 1 hour 55 minutes. After completion, the reaction mixture was quenched by water (10 mL), diluted with water (10 mL), and extracted with EtOA (20 mL). The combined organic layers were washed with saturated sodium chloride solution (20 mL), dried over anhydrous sodium sulfate, filtered and concentrated under reduced pressure to give a residue. The residue was purified by reversed phase flash chromatography [C18, 0.1% FA in water, 0-80% MeCN] give the title compound (70 mg, 29% yield). Yellow solid; $^1$H NMR (400 MHz, DMSO-d6) δ=8.87 (s, 1H), 8.24-8.15 (m, 1H), 8.13-8.06 (m, 1H), 7.75-7.63 (m, 2H), 7.63-7.53 (m, 2H), 4.52-4.20 (m, 4H), 3.71-3.49 (m, 4H), 1.90-1.69 (m, 5H), 1.46 (s, 14H), 1.32-1.22 (m, 4H); LCMS [ESI, M+1]: 647.3.

Step B. 1-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)cyclohexanamine. To a mixture of (1R,5S)-tert-butyl 3-(2-((1-aminocyclohexyl)methoxy)-7-(8-chloronaphthalen-1-yl)-8-fluoropyrido[4,3-d]pyrimidin-4-yl)-3,8-diazabicyclo[3.2.1]octane-8-carboxylate (52.0 mg, 80.3 μmol, 1.0 eq) in DCM (1 mL) was added 2,6-dimethylpyridine (103 mg, 963 μmol, 112.2 μL, 12 eq), trimethylsilyl trifluoromethanesulfonate (107 mg, 482 μmol, 87.1 μL, 6.0 eq) in one portion at −40° C. under $N_2$. The mixture was stirred at 20° C. for 1 hour. After completion, the residue was concentrated under reduced pressure and the residue was purified by reversed phase flash chromatography [C18, 0.1% FA in water, 0-100% MeCN] give the title compound (6.08 mg, 13% yield). Yellow solid; $^1$H NMR (400 MHz, DMSO-d6) δ=8.84 (br s, 1H), 8.20-8.15 (m, 1H), 8.11-8.05 (m, 1H), 7.74-7.68 (m, 1H), 7.65 (dd, J=0.9, 7.3 Hz, 1H), 7.61-7.52 (m, 2H), 6.77-6.57 (m, 1H), 5.54-5.39 (m, 1H), 4.70-4.40 (m, 1H), 4.29 (br d, J=13.0 Hz, 1H), 3.77 (br s, 2H), 3.65 (br s, 2H), 3.58 (br d, J=12.4 Hz, 2H), 2.25 (br s, 2H), 1.78 (br s, 4H), 1.46 (br s, 7H), 1.35-1.19 (m, 1H); LCMS [ESI, M+1]: 547.2.

Example 263

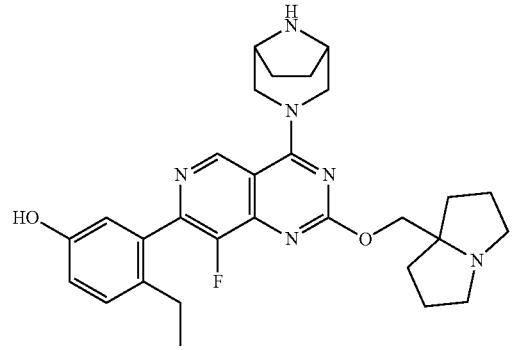 [SMILES: CCc1ccc(O)cc1-c1ncc2c(N3CC4CCC(C3)N4)nc(OCC34CCCN3CCC4)nc2c1F]

3-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)-4-ethylphenol

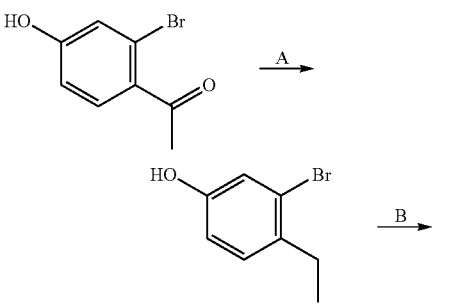

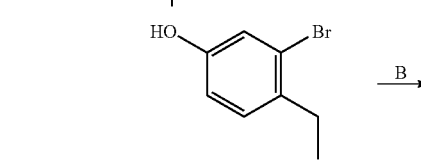

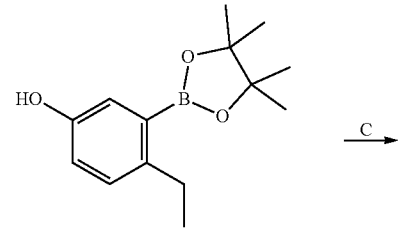

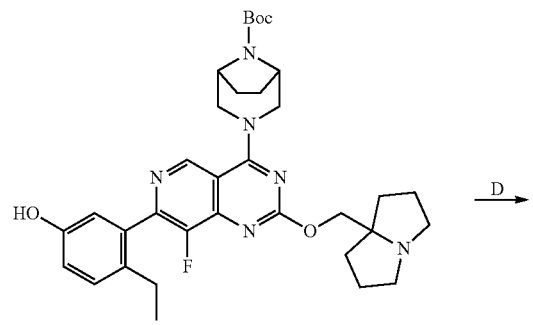

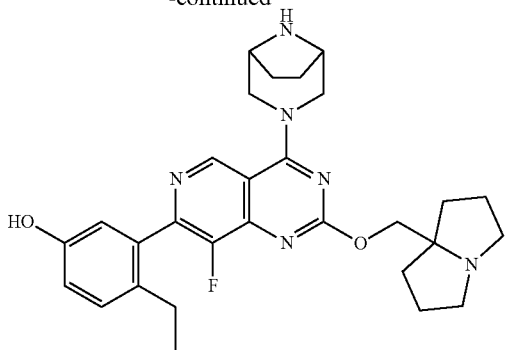

Step A. 3-bromo-4-ethylphenol. To a solution of 1-(2-bromo-4-hydroxy-phenyl)ethanone (2 g, 9.30 mmol, 1.0 eq) in DCM (40 mL) were added BF₃·Et₂O (2.64 g, 18.6 mmol, 2.30 mL, 2.0 eq) and triethylsilane (3.24 g, 27.9 mmol, 4.46 mL, 3.0 eq) at 0° C. The reaction mixture was stirred at 30° C. for 12 hours. The reaction mixture was diluted with water (20 mL) and extracted with DCM (3×30 mL). The combined organic layers were washed with brine (30 mL), dried over Na₂SO₄, filtered and concentrated under reduced pressure to give a residue. The residue was purified by column chromatography (SiO₂, petroleum ether/ethyl acetate=100/1 to 5/1) to give the title compound (1.8 g, 96% yield). Yellow oil; ¹H NMR (400 MHz, chloroform-d) δ=7.13-7.04 (m, 2H), 6.75 (dd, J=2.8, 8.4 Hz, 1H), 2.69 (q, J=7.6 Hz, 2H), 1.20 (t, J=7.6 Hz, 3H).

Step B. 4-ethyl-3-(4,4,5,5-tetramethyl-1,3,2-dioxaborolan-2-yl)phenol. A mixture of 3-bromo-4-ethylphenol (100 mg, 497 µmol, 1.0 eq), 4,4,4',4',5,5,5',5'-octamethyl-2,2'-bi(1,3,2-dioxaborolane) (315 mg, 1.24 mmol, 2.5 eq), Pd(dppf)Cl₂ (36.4 mg, 49.7 µmol, 0.1 eq), KOAc (146 mg, 1.49 mmol, 3.0 eq) in DMF (2 mL) was degassed and purged with N₂ for 3 times. The mixture was stirred at 90° C. for 8 hours under N₂ atmosphere. The reaction mixture was diluted with ethyl acetate (20 mL) and washed with water (3×30 mL). The combined organic layers were washed with brine (20 mL), dried over Na₂SO₄, filtered and concentrated under reduced pressure to give a residue. The residue was purified by column chromatography (SiO₂, petroleum ether/ethyl acetate=100/1 to 5/1) to give the title compound (60 mg, 49% yield). White solid; ¹H NMR (400 MHz, chloroform-d) δ=7.22 (d, J=2.8 Hz, 1H), 7.08 (d, J=8.0 Hz, 1H), 6.85 (dd, J=2.8, 8.4 Hz, 1H), 4.74 (s, 1H), 2.84 (q, J=7.6 Hz, 2H), 1.35 (s, 12H), 1.17 (t, J=7.6 Hz, 3H).

Step C. (1R,5S)-tert-butyl 3-(7-(2-ethyl-5-(methoxymethoxy)phenyl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate. A mixture of tert-butyl (1R,5S)-tert-butyl 3-(7-chloro-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (200 mg, 375 µmol, 1.0 eq), 4-ethyl-3-(4,4,5,5-tetramethyl-1,3,2-dioxaborolan-2-yl)phenol (186 mg, 750 µmol, 2.0 eq), Pd(dppf)Cl₂ (27.4 mg, 37.5 µmol, 0.1 eq), Cs₂CO₃ (366 mg, 1.13 mmol, 3.0 eq) in H₂O (1 mL) and dioxane (4 mL) was degassed and purged with N₂ for 3 times, and then the mixture was stirred at 90° C. for 2 hours under N₂ atmosphere. The reaction mixture was diluted with water (20 mL) and extracted with ethyl acetate (3×30 mL). The combined organic layers were washed with brine (20 mL), dried over Na₂SO₄, filtered and concentrated under reduced pressure to give a residue. The residue was purified by reversed phase flash chromatography [water (0.1% formic acid)/acetonitrile)] to give the title compound (130 mg, 53% yield). Yellow solid; LCMS [ESI, M+1]: 619.4.

Step D. 3-(4-(((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)-4-ethylphenol. To a solution of (1R,5S)-tert-butyl 3-(7-(2-ethyl-5-(methoxymethoxy)phenyl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (70 mg, 113 µmol, 1.0 eq) in ACN (1 mL) was added HCl·dioxane (4 M, 1 mL). The mixture was stirred at 20° C. for 0.5 hour. The mixture was concentrated under vacuum. The residue was purified by prep-HPLC (column: Waters Xbridge C18 150*50 mm*10 um; mobile phase: [water (10 mM NH₄HCO₃)-ACN]; B %: 22%-52%, 10 min) to give the title compound (11.5 mg, 19% yield). White solid; ¹H NMR (400 MHz, methanol-d4) δ=9.03 (s, 1H), 7.21 (d, J=8.4 Hz, 1H), 6.87 (dd, J=2.4, 8.4 Hz, 1H), 6.75 (d, J=2.4 Hz, 1H), 4.61 (br d, J=12.4 Hz, 2H), 4.28 (s, 2H), 3.74-3.60 (m, 4H), 3.17-3.06 (m, 2H), 2.79-2.68 (m, 2H), 2.47 (q, J=7.6 Hz, 2H), 2.14-2.02 (m, 2H), 2.01-1.72 (m, 10H), 1.02 (t, J=7.6 Hz, 3H). LCMS [ESI, M+1]: 519.3.

Example 264

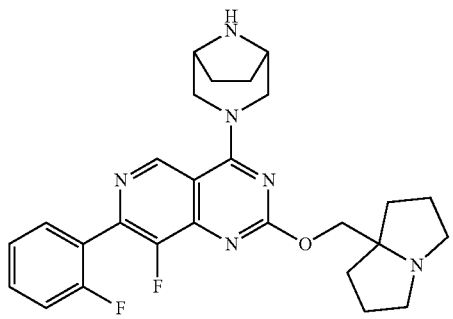 [SMILES: Fc1ccccc1-c1ncc2c(N3CC4CCC(C3)N4)nc(OCC34CCCN3CCC4)nc2c1F]

4-((1R,5S)-3,8-diazabicyclo[3.2.1]octan-3-yl)-8-fluoro-7-(2-fluorophenyl)-2-((hexahydro-1H-pyrrolizin-7a-yl)methoxy)pyrido[4,3-d]pyrimidine

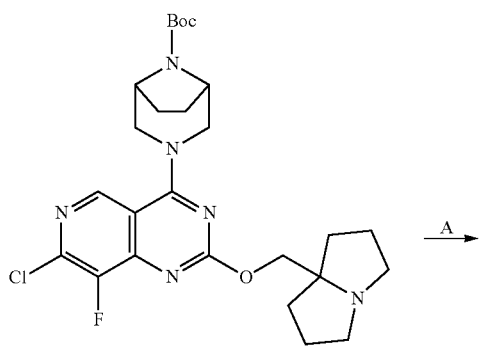

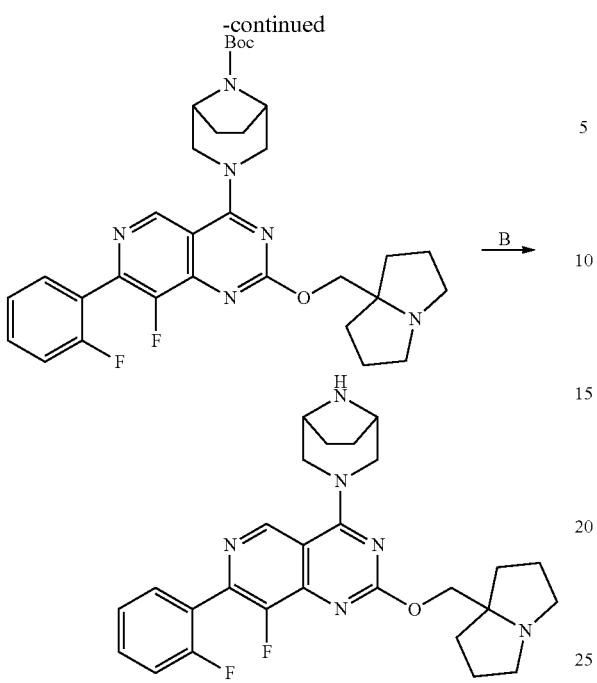

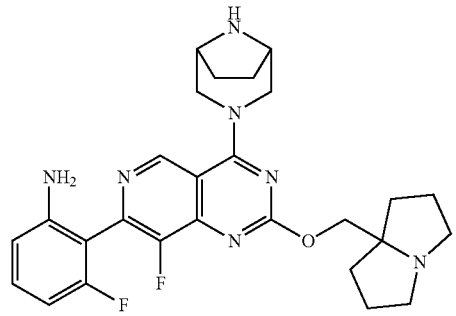 [SMILES: Nc1cccc(F)c1-c1ncc2c(N3CC4CCC(C3)N4)nc(OCC34CCCN3CCC4)nc2c1F]

Step A. (1R,5S)-tert-butyl 3-(8-fluoro-7-(2-fluorophenyl)-2-((hexahydro-1H-pyrrolizin-7a-yl)methoxy)pyrido[4,3-d]pyrimidin-4-yl)-3,8-diazabicyclo[3.2.1] octane-8-carboxylate. A mixture of (1R,5S)-tert-butyl 3-(7-chloro-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (100 mg, 188 μmol, 1.0 eq), (2-fluorophenyl)boronic acid (78.7 mg, 563 μmol, 3.0 eq), Pd(dppf)Cl₂ (27.4 mg, 37.5 μmol, 0.2 eq) and Cs₂CO₃ (183 mg, 563 μmol, 3.0 eq) in dioxane (3 mL) and H₂O (1 mL) was degassed and purged with N₂ for 3 times. The mixture was stirred at 90° C. for 2 hours under N₂ atmosphere. Upon completion, the reaction mixture was diluted with H₂O (10 mL) and extracted with ethyl acetate (3×10 mL). The combined organic layers were washed with saturated brine (30 mL), dried over Na₂SO₄, filtered and concentrated under reduced pressure to give a residue. The residue was purified by reversed phase flash chromatography [C18, 0.1% FA in water, 0-60% MeCN] affording the title compound (50 mg, 40% yield). Yellow oil; LCMS [ESI, M+1]: 593.4.

Step B. 4-((1R,5S)-3,8-diazabicyclo[3.2.1]octan-3-yl)-8-fluoro-7-(2-fluorophenyl)-2-((hexahydro-1H-pyrrolizin-7a-yl)methoxy)pyrido[4,3-d]pyrimidine. To a solution of (1R, 5S)-tert-butyl 3-(8-fluoro-7-(2-fluorophenyl)-2-((hexahydro-1H-pyrrolizin-7a-yl)methoxy)pyrido[4,3-d]pyrimidin-4-yl)-3,8-diazabicyclo[3.2.1]octane-8-carboxylate (45 mg, 75.9 μmol, 1.0 eq) in MeCN (0.5 mL) was added HCl·dioxane (4 M, 1 mL) at 0° C. The mixture was stirred at 0° C. for 0.5 hour. Upon completion, the reaction mixture was diluted with saturated Na₂CO₃ aqueous (5 mL) and extracted with ethyl acetate (3×10 mL). The combined organic layers were washed with saturated brine (20 mL), dried over Na₂SO₄, filtered and concentrated under reduced pressure to give a residue. The residue was purified by prep-HPLC (column: Waters Xbridge 150*25 mm*5um; mobile phase: [water (10 mM NH₄HCO₃)-ACN]; B %: 12%-42%, 10 min) and lyophilized to afford the title compound (7.36 mg, 19% yield). Off-white solid; ¹H NMR (400 MHz, CDCl₃-d) δ 9.02 (s, 1H), 7.67 (td, J=1.6, 7.6 Hz, 1H), 7.49-7.43 (m, 1H), 7.32-7.27 (m, 1H), 7.21 (t, J=9.2 Hz, 1H), 4.56 (br d, J=11.6 Hz, 2H), 4.19 (s, 2H), 3.68-3.58 (m, 4H), 3.15-3.08 (m, 2H), 2.68-2.61 (m, 2H), 2.14-2.05 (m, 2H), 1.91-1.84 (m, 4H), 1.81-1.75 (m, 4H), 1.71-1.63 (m, 2H); LCMS [ESI, M+1]: 493.3.

Example 265

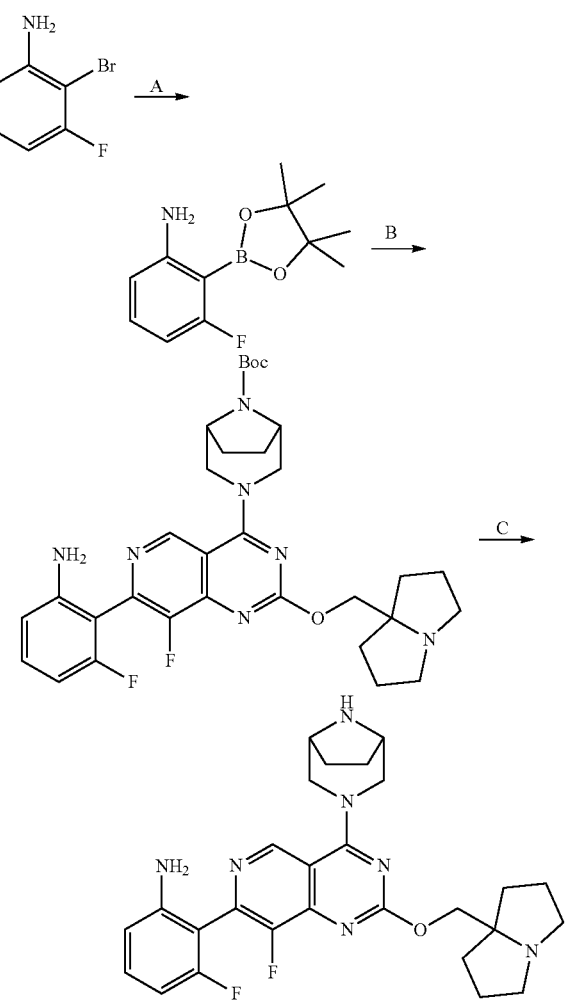

2-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)-3-fluoroaniline Step A. 3-fluoro-2-(4,4,5,5-tetramethyl-1,3,2-dioxaborolan-2-yl)aniline. A mixture of 2-bromo-3-fluoroaniline (1.20 g, 6.32 mmol, 1.0 eq), 4,4,5,5-tetramethyl-2-(4,4,5,5-tetramethyl-1,3,2-dioxaborolan-2-yl)-1,3,2-dioxaborolane (3.21 g, 12.6 mmol, 2.0 eq), Pd(dppf)Cl₂ (924 mg, 1.26 mmol, 0.2 eq) and KOAc (3.10 g, 31.6 mmol, 5.0 eq) in DMF (15 mL) was degassed and purged with N₂ for 3 times. The mixture was stirred at 80° C. for 12 hours under N₂ atmosphere. Upon completion, the reaction mixture was diluted with H₂O (20 mL) and extracted with ethyl acetate (3×30 mL). The combined organic layers were washed with saturated brine (80 mL), dried over Na₂SO₄, filtered and concentrated under reduced pressure to give a residue. The residue was purified by column chromatography (SiO₂, petroleum ether: ethyl acetate=1:0 to 10:1) affording the title compound (1.2 g, 80% yield). White solid; ¹H NMR (400 MHz, CDCl₃-d) δ=7.15-7.08 (m, 1H), 6.37-6.27 (m, 2H), 4.96 (br s, 2H), 1.36 (s, 12H).

Step B. (1R,5S)-tert-butyl 3-(7-(2-amino-6-fluorophenyl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate. A mixture of (1R,5S)-tert-butyl 3-(7-chloro-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (300 mg, 563 μmol, 1.0 eq), 3-fluoro-2-(4,4,5,5-tetramethyl-1,3,2-dioxaborolan-2-yl)aniline (400 mg, 1.69 mmol, 3.0 eq), K₃PO₄ (1.5 M, 1.13 mL, 3.0 eq), [2-(2-aminophenyl)phenyl]palladium(1+); bis(1-adamantyl)-butyl-phosphane; methanesulfonate (61.5 mg, 84.4 μmol, 0.15 eq) in THF (4 mL) was degassed and purged with N₂ for 3 times. The mixture was stirred at 60° C. for 3 hours under N₂ atmosphere. Upon completion, the reaction mixture was diluted with H₂O (10 mL) and extracted with ethyl acetate (3×10 mL). The combined organic layers were washed with saturated brine (20 mL), dried over Na₂SO₄, filtered and concentrated under reduced pressure to give a residue. The residue was purified by reversed phase flash chromatography [C18, 0.10% FA in water, 0-70% MeCN] affording the title compound (320 mg, 84% yield). Yellow solid; LCMS [ESI, M+1]: 608.4.

Step C. 2-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)-3-fluoroaniline. To a solution of (1R,5S)-tert-butyl 3-(7-(2-amino-6-fluorophenyl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (100 mg, 165 μmol, 1.00 eq) in MeCN (1 mL) was added HCl·dioxane (4 M, 2 mL) at 0° C. The mixture was stirred at 0° C. for 0.5 hour. Upon completion, the reaction mixture was diluted with saturated Na₂CO₃ aqueous (5 mL) and extracted with ethyl acetate (3×10 mL). The combined organic layers were washed with saturated brine (20 mL), dried over Na₂SO₄, filtered and concentrated under reduced pressure to give a residue. The residue was purified by prep-HPLC (column: Phenomenex luna C18 150*40 mm*15 um; mobile phase: [water (0.225% FA)-ACN]; B %: 1%-30%, 10 min) and lyophilized affording the title compound (29.2 mg, 33% yield, 2FA). Yellow solid; ¹H NMR (400 MHz, methanol-d4) δ=9.17 (s, 1H), 7.24-7.16 (m, 1H), 6.69 (d, J=8.4 Hz, 1H), 6.53-6.46 (m, 1H), 4.83-4.76 (m, 2H), 4.68 (s, 2H), 4.09 (br s, 2H), 3.92 (br d, J=13.6 Hz, 2H), 3.76-3.67 (m, 2H), 3.31-3.26 (m, 2H), 2.41-2.29 (m, 2H), 2.28-2.16 (m, 4H), 2.15-2.04 (m, 4H), 2.01-1.93 (m, 2H); LCMS [ESI, M+1]: 508.3.

Example 266

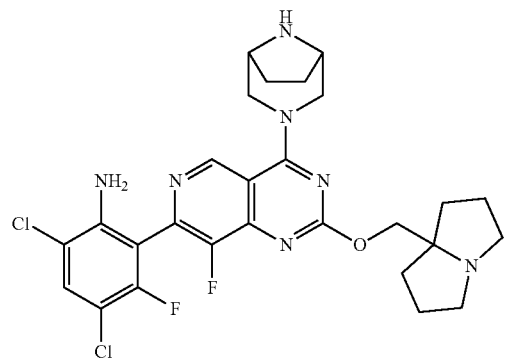 [SMILES: Nc1c(Cl)cc(Cl)c(F)c1-c1ncc2c(N3CC4CCC(C3)N4)nc(OCC34CCCN3CCC4)nc2c1F]

2-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)-4,6-dichloro-3-fluoroaniline

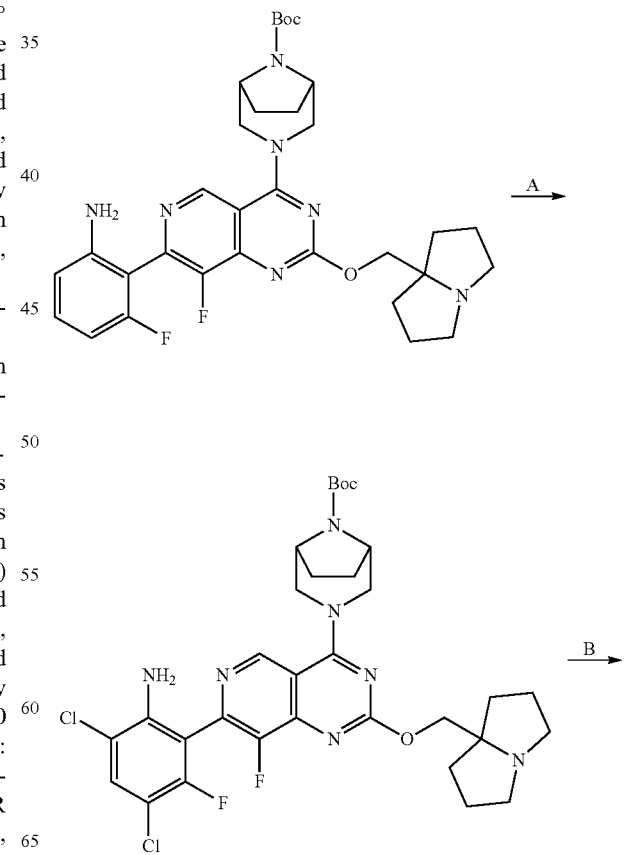

585

-continued

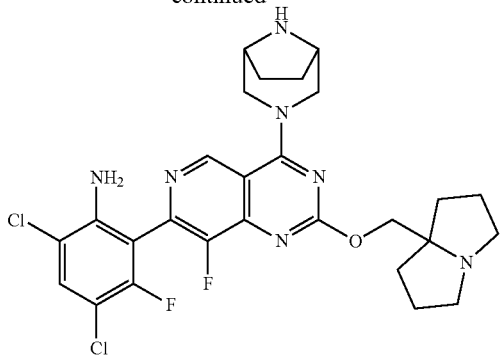

Step A. (1R,5S)-tert-butyl 3-(7-(2-amino-3,5-dichloro-6-fluorophenyl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate. To a solution of (1R,5S)-tert-butyl 3-(7-(2-amino-6-fluorophenyl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (90 mg, 148 μmol, 1.0 eq) in ACN (2 mL) was added NCS (59.3 mg, 444 μmol, 3.0 eq). The mixture was stirred at 80° C. for 2 hours. Upon completion, the reaction mixture was concentrated under reduced pressure to give a residue. The residue was purified by reversed phase flash chromatography (C18, 0.1% FA in water, 0-40% ACN) affording the title compound (10 mg, 9.0% yield). Brown solid; LCMS [ESI, M+1]: 676.2.

Step B. 2-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)-4,6-dichloro-3-fluoroaniline. To a solution of 1R,5S)-tert-butyl 3-(7-(2-amino-3,5-dichloro-6-fluorophenyl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (20 mg, 29.6 μmol, 1.00 eq) in MeCN (1 mL) was added HCl·dioxane (4 M, 0.5 mL) at 0° C. The mixture was stirred at 0° C. for 0.5 hour. Upon completion, the reaction mixture was concentrated under reduced pressure to give a residue. The residue was purified by prep-HPLC (column: Phenomenex Synergi C18 150*25*10 um; mobile phase: [water (0.225% F A)-ACN]; B %: 10%-50%, 8 min) and lyophilized affording the title compound (11.2 mg, 56% yield, 2FA). Yellow solid; ¹H NMR (400 MHz, methanol-d4) δ 9.18 (s, 1H), 7.51 (d, J=7.2 Hz, 1H), 4.76 (br d, J=13.2 Hz, 2H), 4.66 (s, 2H), 4.04-3.93 (m, 2H), 3.88 (br d, J=13.2 Hz, 2H), 3.75-3.64 (m, 2H), 3.30-3.23 (m, 2H), 2.39-2.29 (m, 2H), 2.26-2.07 (m, 2H), 2.04-1.86 (m, 4H); LCMS [ESI, M+1]: 576.2.

Example 267

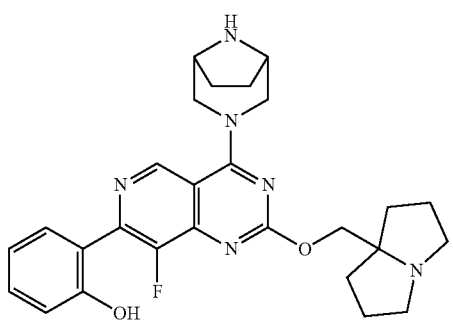 [SMILES: Oc1ccccc1-c1ncc2c(N3CC4CCC(C3)N4)nc(OCC34CCCN3CCC4)nc2c1F]

586

2-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)phenol

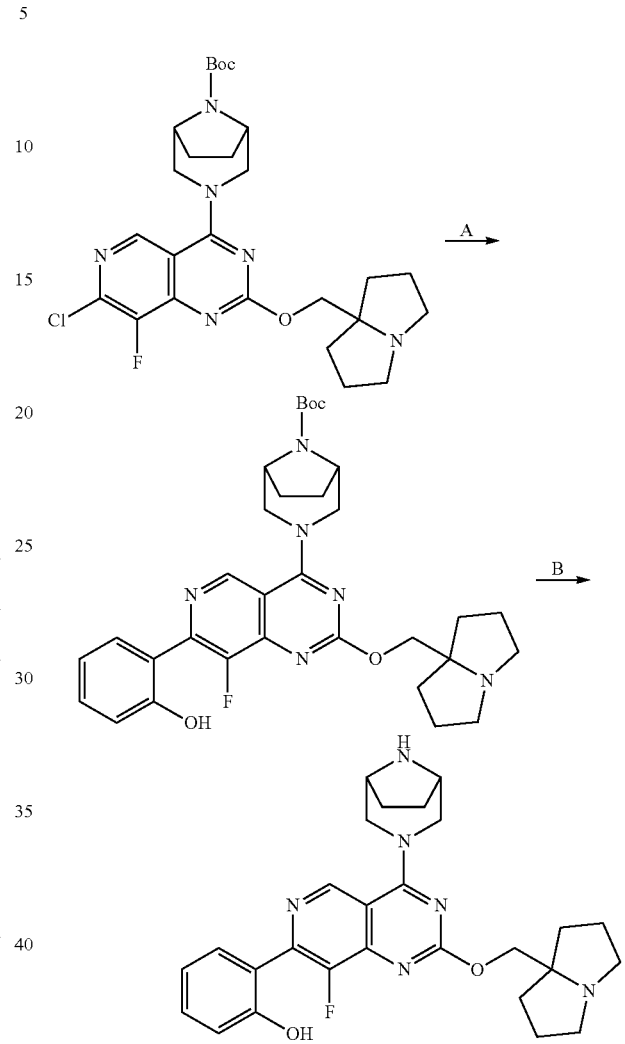

Step A. (1R,5S)-tert-butyl 3-(8-fluoro-2-((hexahydro-1H-pyrrolizin-7a-yl)methoxy)-7-(2-hydroxyphenyl)pyrido[4,3-d]pyrimidin-4-yl)-3,8-diazabicyclo[3.2.1]octane-8-carboxylate. To a solution of (1R,5S)-tert-butyl 3-(7-chloro-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (150 mg, 281 μmol, 1.0 eq) and 2-(4,4,5,5-tetramethyl-1,3,2-dioxaborolan-2-yl)phenol (186 mg, 844 μmol, 3.0 eq) in dioxane (2 mL) and H₂O (0.5 mL) was added Pd(dppf)Cl₂ (30.9 mg, 42.2 μmol, 0.15 eq) and Cs₂CO₃ (275 mg, 844 μmol, 3.0 eq). The mixture was stirred at 90° C. for 2 hours. After completion, the reaction mixture was diluted with H₂O (10 mL) and extracted with ethyl acetate (3×10 mL). The combined organic layers were dried over Na₂SO₄, filtered and concentrated under reduced pressure to give a residue. The residue was purified by reversed phase flash chromatography (C18, 0.1% FA in water, 0-40% ACN) affording the title compound (60 mg, 27% yield). Off-white solid; LCMS [ESI, M+1]: 591.2.

Step B. 2-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)phenol. To a mixture of (1R, 5S)-tert-butyl 3-(8-fluoro-2-((hexahydro-1H-pyrrolizin-7a-yl)methoxy)-7-(2-hydroxyphenyl)pyrido[4,3-d]pyrimidin-4-yl)-3,8-diazabicyclo[3.2.1]octane-8-carboxylate (50 mg, 64.3 µmol, 1.0 eq) in acetonitrile (0.5 mL) was added HCl·dioxane (4 M, 1.5 mL) at 0° C. The mixture was stirred at 0° C. for 0.5 hour. After completion, the reaction mixture was concentrated under reduced pressure to give a residue. The residue was diluted with MeOH (10 mL) and adjusted pH to 7 with NaHCO₃ solid, filtered and concentrated under reduced pressure to give a residue. The residue was purified by prep-HPLC (column: Waters Xbridge C18 150*50 mm*10 um; mobile phase: [water (10 mM NH₄HCO₃)-ACN]; B %: 25%-55%, 10 min) to give the title compound (17.6 mg, 55% yield). Off-white solid; ¹H NMR (400 MHz, CDCl₃) δ 13.34 (br s, 1H), 8.89 (s, 1H), 8.18 (dd, J=1.2, 8.0 Hz, 1H), 7.43-7.32 (m, 1H), 7.06 (dd, J=1.2, 8.4 Hz, 1H), 7.03-6.93 (m, 1H), 4.56 (br d, J=11.6 Hz, 2H), 4.21 (s, 2H), 3.74-3.58 (m, 4H), 3.22-3.08 (m, 2H), 2.73-2.61 (m, 2H), 2.16-2.08 (m, 2H), 1.98-1.82 (m, 6H), 1.76-1.64 (m, 4H); LCMS [ESI, M+1]: 491.2.

Example 268

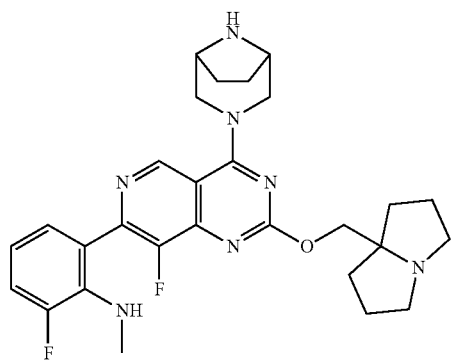 [SMILES: CNc1c(F)cccc1-c1ncc2c(N3CC4CCC(C3)N4)nc(OCC34CCCN3CCC4)nc2c1F]

2-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)-6-fluoro-N-methylaniline

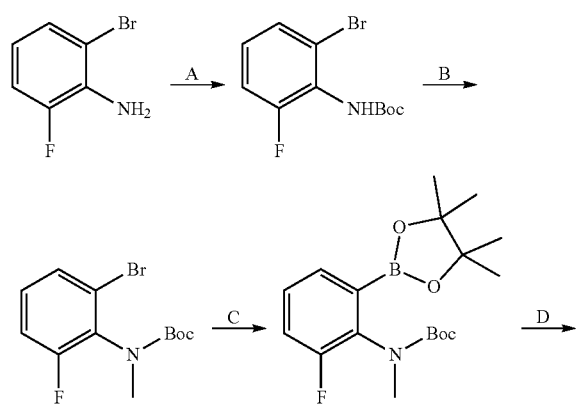

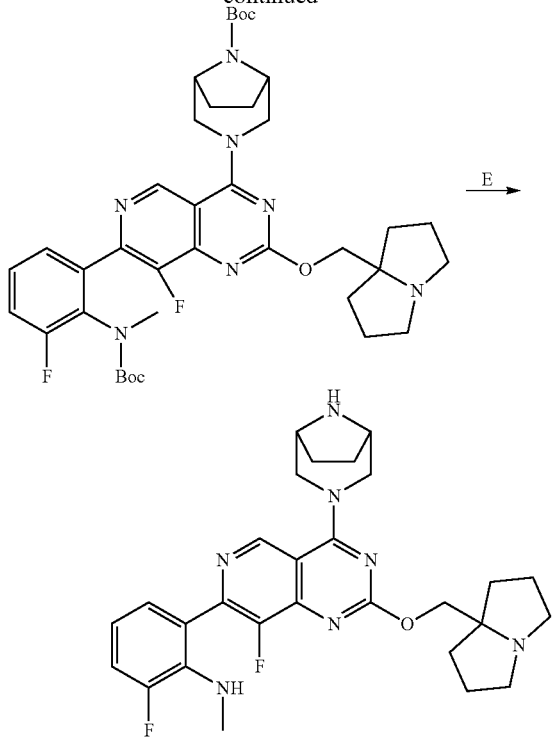

Step A. tert-butyl (2-bromo-6-fluorophenyl)carbamate. To a solution of 2-bromo-6-fluoroaniline (5 g, 26.3 mmol, 2.99 mL, 1.0 eq) in THF (30 mL) was added dropwise LiHMDS (1 M, 27.1 mL, 1.03 eq) at −40° C. After addition, the mixture was stirred at this temperature for 20 minutes, and then (Boc)₂O (5.17 g, 23.7 mmol, 5.44 mL, 0.9 eq) was added dropwise at −40° C. The resulting mixture was stirred at −40° C. for 30 minutes. Upon completion, the reaction mixture was diluted with H₂O (20 mL) and extracted with ethyl acetate (3×30 mL). The combined organic layers were dried over Na₂SO₄, filtered and concentrated under reduced pressure to give a residue. The residue was purified by reversed phase flash chromatography [C18, 0.1% FA in water, 0-100% MeCN] and further purified by column chromatography (SiO₂, petroleum ether: ethyl acetate=1:0 to 10:1) to give the title compound (1.6 g, 21% yield). White solid; ¹H NMR (400 MHz, CDCl₃-d) δ=7.40-7.37 (m, 1H), 7.12-7.06 (m, 2H), 6.06 (br s, 1H), 1.51 (s, 9H).

Step B. tert-butyl (2-bromo-6-fluorophenyl)(methyl)carbamate. To a solution of tert-butyl (2-bromo-6-fluorophenyl)carbamate (1.60 g, 5.51 mmol, 1.0 eq) in THF (15 mL) was added LiHMDS (1 M, 8.27 mL, 1.5 eq) dropwise at 0° C. After addition, the mixture was stirred at this temperature for 0.5 hour, and then CH₃I (3.91 g, 27.6 mmol, 1.72 mL, 5.0 eq) was added dropwise at 0° C. The resulting mixture was stirred at 0° C. for 1.5 hours. Upon completion, the reaction mixture was diluted with saturated NH₄Cl aqueous (20 mL) and extracted with ethyl acetate (3×20 mL). The combined organic layers were washed with saturated brine (80 mL), dried over Na₂SO₄, filtered and concentrated under reduced pressure to give a residue. The residue was purified by column chromatography (SiO₂, petroleum ether: ethyl acetate=1:0 to 10:1) to give the title compound (1.6 g, 94% yield). Colorless oil; [ESI, M−55]: 250.1.

Step C. tert-butyl (2-fluoro-6-(4,4,5,5-tetramethyl-1,3,2-dioxaborolan-2-yl)phenyl) (methyl)carbamate. A mixture of tert-butyl (2-bromo-6-fluorophenyl)(methyl)carbamate (800 mg, 2.63 mmol, 1.0 eq), 4,4,5,5-tetramethyl-2-(4,4,5,5-tetramethyl-1,3,2-dioxaborolan-2-yl)-1,3,2-dioxaborolane (1.00 g, 3.95 mmol, 1.5 eq), KOAc (1.29 g, 13.1 mmol, 5.0 eq) and Pd(dppf)Cl$_2$ (289 mg, 394 μmol, 0.15 eq) in DMF (10 mL) was degassed and purged with N$_2$ for 3 times. The mixture was stirred at 80° C. for 12 hours under N$_2$ atmosphere. Upon completion, the reaction mixture was diluted with H$_2$O (15 mL) and extracted with ethyl acetate (3×15 mL). The combined organic layers were washed with saturated brine (40 mL), dried over Na$_2$SO$_4$, filtered and concentrated under reduced pressure to give a residue. The residue was purified by column chromatography (SiO$_2$, petroleum ether: ethyl acetate=1:0 to 20:1) to give the title compound (750 mg, 81% yield). White solid; $^1$H NMR (400 MHz, CDCl$_3$-d) δ=7.53-7.50 (m, 1H), 7.24-7.21 (m, 1H), 7.19-7.15 (m, 1H), 3.12 (s, 3H), 1.32 (s, 12H), 1.29 (s, 9H).

Step D. (1R,5S)-tert-butyl 3-(7-(2-((tert-butoxycarbonyl)(methyl)amino)-3-fluorophenyl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate. A mixture of (1R,5S)-tert-butyl 3-(7-chloro-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (350 mg, 657 μmol, 1.0 eq), tert-butyl (2-fluoro-6-(4,4,5,5-tetramethyl-1,3,2-dioxaborolan-2-yl)phenyl) (methyl)carbamate (692 mg, 1.97 mmol, 3.0 eq), [2-(2-aminophenyl)phenyl]palladium (1+); bis(1-adamantyl)-butyl-phosphane; methanesulfonate (71.7 mg, 98.5 μmol, 0.15 eq) and K$_3$PO$_4$ (1.5 M, 1.5 mL, 3.43 eq) and in THF (6 mL) was degassed and purged with N$_2$ for 3 times, and then the mixture was stirred at 60° C. for 3 hours under N$_2$ atmosphere. Upon completion, the reaction mixture was diluted with H$_2$O (10 mL) and extracted with ethyl acetate (3×10 mL). The combined organic layers were washed with saturated brine (20 mL), dried over Na$_2$SO$_4$, filtered and concentrated under reduced pressure to give a residue. The residue was purified by reversed phase flash chromatography [C18, 0.1% FA in water, 0-50% MeCN] to give the title compound (260 mg, 54% yield). Yellow solid; [ESI, M+1]: 722.4.

Step E. 2-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)-6-fluoro-N-methylaniline. To a solution of (1R,5S)-tert-butyl 3-(7-(2-((tert-butoxycarbonyl)(methyl)amino)-3-fluorophenyl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (240 mg, 332 μmol, 1.0 eq) in acetonitrile (2 mL) was added HCl·dioxane (4 M, 2 mL). The mixture was stirred at 0° C. for 20 minutes. Upon completion, the reaction mixture was diluted with H$_2$O (10 mL) and extracted with ethyl acetate (3×10 mL). The combined organic layers were washed with saturated brine (20 mL), dried over Na$_2$SO$_4$, filtered and concentrated under reduced pressure to give a residue. The residue was purified by prep-HPLC (column: Unisil 3-100 C18 ultra 150*50 mm*3 um; mobile phase: [water (0.225% FA)-ACN]; B %: 1%-30%, 10 min) and lyophilized to give the title compound (99.9 mg, 48% yield, 2FA). Yellow solid; $^1$H NMR (400 MHz, methanol-d4) δ=9.13 (s, 1H), 7.17-7.10 (m, 2H), 6.87-6.80 (m, 1H), 4.79 (d, J=13.2 Hz, 2H), 4.67 (s, 2H), 4.13-4.06 (m, 2H), 3.92 (d, J=13.2 Hz, 2H), 3.76-3.65 (m, 2H), 3.31-3.25 (m, 2H), 2.74 (d, J=3.2 Hz, 3H), 2.39-2.29 (m, 2H), 2.27-2.17 (m, 4H), 2.15-2.04 (m, 4H), 2.01-1.94 (m, 2H). [ESI, M+1]: 522.4.

Example 269

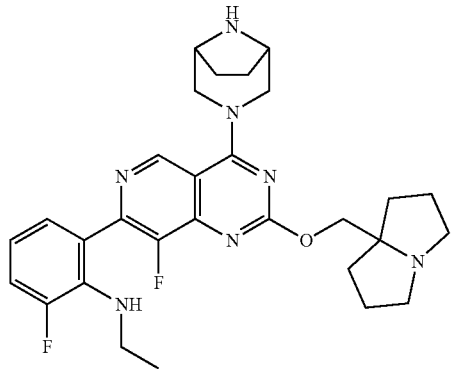 [SMILES: CCNc1c(F)cccc1-c1ncc2c(N3CC4CCC(C3)N4)nc(OCC34CCCN3CCC4)nc2c1F]

2-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)-N-ethyl-6-fluoroaniline Synthesized according to Example 268, substituting iodoethane in place of iodomethane and increasing reaction temperature to 20° C. in step B. Yellow solid (12.5 mg 1.7 eq HCOOH); $^1$H NMR (400 MHz, CDCl$_3$) δ 9.03 (s, 1H), 7.19 (br d, J=7.6 Hz, 1H), 7.12-7.03 (m, 1H), 6.84-6.76 (m, 1H), 4.72-4.54 (m, 4H), 4.10-3.69 (m, 6H), 3.24-3.09 (m, 2H), 3.04-2.84 (m, 2H), 2.44-2.30 (m, 2H), 2.27-2.15 (m, 2H), 2.12-1.85 (m, 8H), 1.09 (t, J=7.2 Hz, 3H). [ESI, M+1]: 536.3.

Example 270

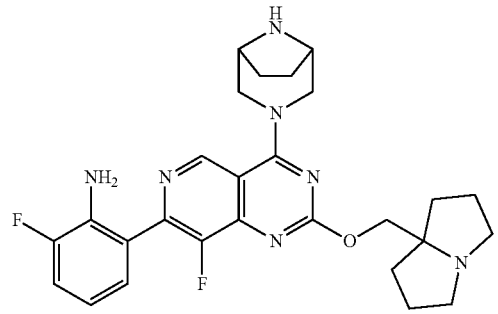 [SMILES: Nc1c(F)cccc1-c1ncc2c(N3CC4CCC(C3)N4)nc(OCC34CCCN3CCC4)nc2c1F]

2-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)-6-fluoroaniline

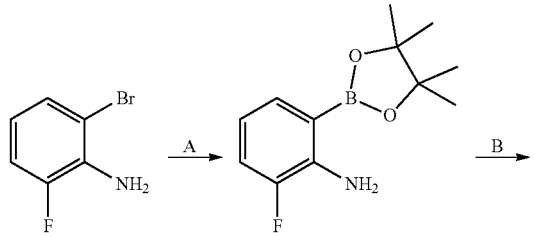

-continued

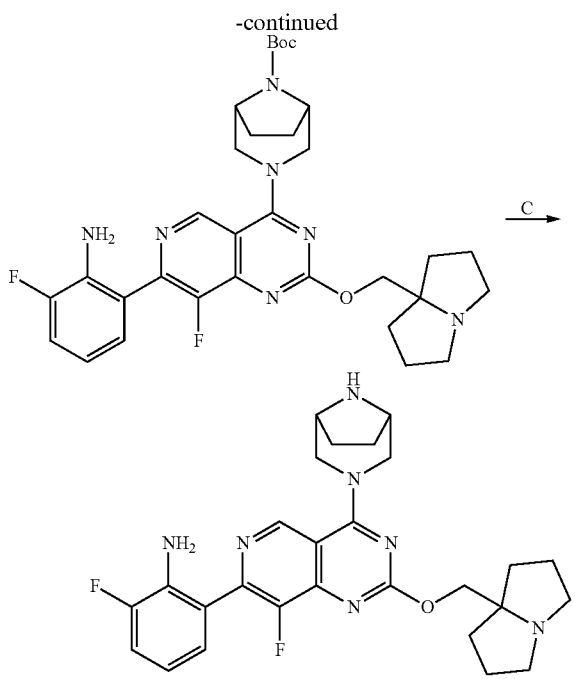

Step A. 2-fluoro-6-(4,4,5,5-tetramethyl-1,3,2-dioxaborolan-2-yl)aniline. To a solution of 2-bromo-6-fluoroaniline (1.0 g, 5.26 mmol, 599 μL, 1.0 eq), 4,4,5,5-tetramethyl-2-(4,4,5,5-tetramethyl-1,3,2-dioxaborolan-2-yl)-1,3,2-dioxaborolane (2.67 g, 10.5 mmol, 2.0 eq) and KOAc (2.58 g, 26.3 mmol, 5.0 eq) in DMF (10 mL) was added Pd(dppf)Cl$_2$ (385 mg, 526 μmol, 0.10 eq). The mixture was stirred at 80° C. for 12 hours. After completion, the reaction mixture was added water (10 mL) and extracted with ethyl acetate (3×10 mL). The organic layer was dried over Na$_2$SO$_4$, filtered and concentrated. The residue was purified by column chromatography (SiO$_2$, petroleum ether: ethyl acetate=100:1-20:1) to give the title compound (610 mg, 49% yield). White solid; $^1$H NMR (400 MHz, CDCl$_3$) δ=7.39 (dd, J=0.8, 7.6 Hz, 1H), 7.08-7.00 (m, 1H), 6.65-6.55 (m, 1H), 4.83 (br s, 2H), 1.36 (s, 12H).

Step B. (1R,5S)-tert-butyl 3-(7-(2-amino-3-fluorophenyl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate. To a solution of (1R,5S)-tert-butyl 3-(7-chloro-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (200 mg, 375 μmol, 1.0 eq) and Cs$_2$CO$_3$ (367 mg, 1.13 mmol, 3.0 eq) in dioxane (3 mL) and H$_2$O (1 mL) was added Pd(dppf)Cl$_2$ (54.9 mg, 75.0 μmol, 0.2 eq). Then 2-fluoro-6-(4,4,5,5-tetramethyl-1,3,2-dioxaborolan-2-yl)aniline (178 mg, 750 μmol, 2.0 eq) was added to the mixture. The suspension was degassed under vacuum and purged with N$_2$ for several times. The mixture was stirred at 90° C. for 3 hours. After completion, the mixture was diluted with water (5 mL) and extracted with ethyl acetate (3×5 mL) The combined organic layers were dried over Na$_2$SO$_4$, filtered and concentrated. The residue was purified by reversed phase flash chromatography (C18, 0.1% formic acid condition) to give the title compound (120 mg, 49% yield). Yellow solid; $^1$H NMR (400 MHz, CDCl$_3$) δ=8.96 (s, 1H), 7.38 (dd, J=2.8, 7.6 Hz, 1H), 7.12-7.03 (m, 1H), 6.81-6.72 (m, 1H), 5.13 (s, 2H), 4.55 (br d, J=12.4 Hz, 2H), 4.46-4.26 (m, 2H), 4.19 (s, 2H), 3.81-3.54 (m, 2H), 3.17-3.06 (m, 2H), 2.71-2.59 (m, 2H), 2.14-2.06 (m, 2H), 2.00-1.93 (m, 2H), 1.92-1.82 (m, 4H), 1.79-1.60 (m, 8H), 1.53 (s, 9H). [ESI, M+1]: 608.3.

Step C. 2-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)-6-fluoroaniline. To a solution of (1R,5S)-tert-butyl 3-(7-(2-amino-3-fluorophenyl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (90 mg, 148 μmol, 1.0 eq) in MeCN (0.5 mL) was added HCl·dioxane (4 M, 13.5 mL, 365 eq). The mixture was stirred at 0° C. for 0.5 hour. After completion, the mixture was concentrated. The residue was purified by prep-HPLC (column: Unisil 3-100 C18 ultra 150*50 mm*3 um; mobile phase: [water (0.225% FA)-ACN]; B %: 1%-30%, 10 min) to give the title compound (14.8 mg, 19% yield). Yellow solid; $^1$H NMR (400 MHz, methanol-d4) δ=9.18 (br s, 1H), 7.27 (br d, J=7.2 Hz, 1H), 7.20-7.06 (m, 1H), 6.71 (br s, 1H), 4.76 (br d, J=12.4 Hz, 2H), 4.66 (s, 2H), 4.00 (br s, 2H), 3.87 (br d, J=13.2 Hz, 2H), 3.75-3.66 (m, 2H), 3.30-3.24 (m, 2H), 2.40-2.28 (m, 2H), 2.27-2.14 (m, 4H), 2.13-2.06 (m, 2H), 2.05-1.96 (m, 2H), 1.95-1.87 (m, 2H). [ESI, M+1]: 508.3.

Example 271

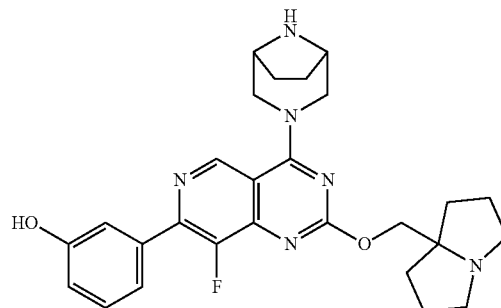

3-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)phenol

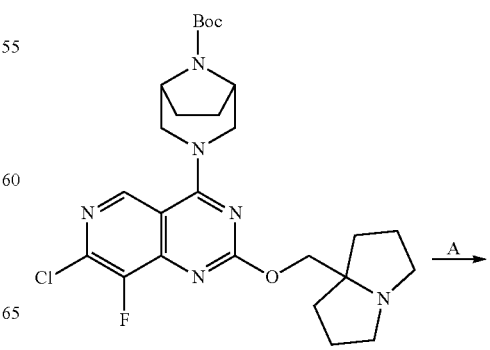

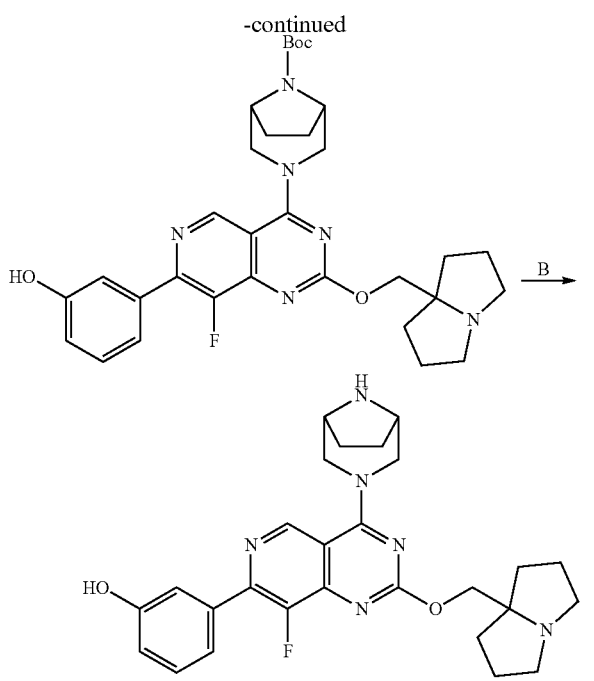

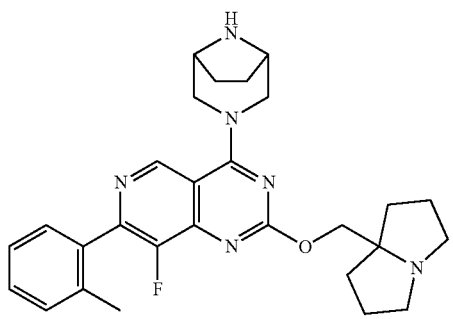 [SMILES: Cc1ccccc1-c1ncc2c(N3CC4CCC(C3)N4)nc(OCC34CCCN3CCC4)nc2c1F]

Step A. (1R,5S)-tert-butyl 3-(8-fluoro-2-((hexahydro-1H-pyrrolizin-7a-yl)methoxy)-7-(3-hydroxyphenyl)pyrido[4,3-d]pyrimidin-4-yl)-3,8-diazabicyclo[3.2.1]octane-8-carboxylate. To a mixture of (1R,5S)-tert-butyl 3-(7-chloro-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (150 mg, 282 μmol, 1.0 eq) and (3-hydroxyphenyl)boronic acid (77.7 mg, 563 μmol, 2.0 eq) in dioxane (3 mL), H$_2$O (1 mL) were added Pd(dppf)Cl$_2$ (20.6 mg, 28.2 μmol, 0.1 eq), Cs$_2$CO$_3$ (275 mg, 845 μmol, 3.0 eq) in one portion under N$_2$. The mixture was stirred at 90° C. for 2 hours. After completion, the reaction mixture was extracted with EtOAc (20 mL×3). The combined organic layers were washed with saturated brine (20 mL), dried over anhydrous sodium sulfate, filtered and concentrated under reduced pressure. The residue was purified by reversed phase flash chromatography [water (0.1% FA)/acetonitrile] to give the title compound (90.0 mg, 53% yield). Off-white solid; $^1$H NMR (400 MHz, DMSO-d6) δ=9.68 (br s, 1H), 9.13 (s, 1H), 7.51-7.42 (m, 2H), 7.35 (t, J=8.1 Hz, 1H), 6.96-6.84 (m, 1H), 4.51 (br d, J=12.3 Hz, 2H), 4.27 (br s, 2H), 4.08 (s, 3H), 3.62 (br d, J=12.2 Hz, 2H), 3.02-2.90 (m, 2H), 2.61-2.57 (m, 1H), 1.94-1.87 (m, 2H), 1.86-1.72 (m, 6H), 1.70-1.55 (m, 4H), 1.47 (s, 9H). (ESI, M+1): 591.2.

Step B. 3-(4-((1R,5S)-3,8-diazabicyclo[3.2.1]octan-3-yl)-8-fluoro-2-((hexahydro-1H-Pyrrolizin-7a-yl)methoxy)pyrido[4,3-d]pyrimidin-7-yl)phenol. To a mixture of (1R,5S)-tert-butyl 3-(8-fluoro-2-((hexahydro-1H-pyrrolizin-7a-yl)methoxy)-7-(3-hydroxyphenyl)pyrido[4,3-d]pyrimidin-4-yl)-3,8-diazabicyclo[3.2.1]octane-8-carboxylate (40 mg, 67.7 μmol, 1.0 eq) in MeCN (2 mL) was added HCl·dioxane (4 M, 320 μL, 18.9 eq) in one portion under N$_2$. The mixture was stirred at 0° C. for 30 minutes. After completion, the residue was concentrated under reduced pressure. The residue was purified by prep-HPLC (column: Waters Xbridge C18 150*50 mm*10 um; mobile phase: [water (10 mM NH$_4$HCO$_3$)-ACN]; B %: 30%-60%, 10 min) to give the title compound (13.35 mg, 39% yield). White solid; $^1$H NMR (400 MHz, DMSO-d6) δ=9.66 (br s, 1H), 9.09 (s, 1H), 7.49-7.42 (m, 2H), 7.34 (t, J=8.1 Hz, 1H), 6.93-6.86 (m, 1H), 4.40 (br d, J=12.0 Hz, 2H), 4.05 (s, 2H), 3.62-3.48 (m, 4H), 2.99-2.90 (m, 2H), 2.59-2.53 (m, 3H), 1.93-1.85 (m, 2H), 1.85-1.71 (m, 4H), 1.66-1.53 (m, 6H). [ESI, M+1]: 491.2.

Example 272

4-((1R,5S)-3,8-diazabicyclo[3.2.1]octan-3-yl)-8-fluoro-2-((hexahydro-1H-pyrrolizin-7a-yl)methoxy)-7-(o-tolyl)pyrido[4,3-d]pyrimidine

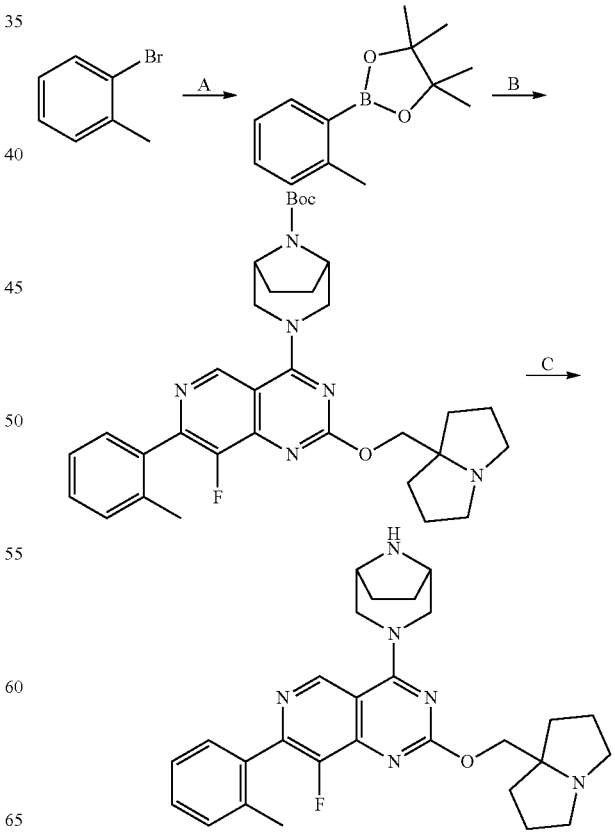

Step A. 4,4,5,5-tetramethyl-2-(o-tolyl)-1,3,2-dioxaborolane. To a mixture of 1-bromo-2-methylbenzene (2.0 g, 11.7 mmol, 1.41 mL, 1.0 eq) and 4,4,5,5-tetramethyl-2-(4,4,5,5-tetramethyl-1,3,2-dioxaborolan-2-yl)-1,3,2-dioxaborolane (5.94 g, 23.4 mmol, 2.0 eq) in dioxane (25 mL) was added KOAc (3.44 g, 35.1 mmol, 3.0 eq). The mixture was degassed then Pd(dppf)Cl$_2$ (855 mg, 1.17 mmol, 0.10 eq) was added into the above mixture under N$_2$. The mixture was stirred at 100° C. for 1 hour under N$_2$. After completion, the mixture was diluted with ethyl acetate (15 mL) and water (15 mL). The organic layer was separated. The aqueous phase was extracted with ethyl acetate (15 mL). The combined organic layer was washed with saturated brine (20 mL), dried over Na$_2$SO$_4$, filtered and concentrated under vacuum. The residue was purified by column chromatography (SiO$_2$, petroleum ether: ethyl acetate=50/1-30/1) twice to give the title compound (1.7 g, 67% yield). Colorless oil; Rf=0.25 (petroleum ether: ethyl acetate=10:1); $^1$H NMR (400 MHz, CDCl$_3$-d) δ=7.80-7.76 (m, 1H), 7.31 (td, J=1.2, 12.6 Hz, 1H), 7.21-7.15 (m, 2H), 2.56 (s, 3H), 1.36 (s, 12H).

Step B. tert-butyl (1R,5S)-3-(8-fluoro-2-((tetrahydro-1H-pyrrolizin-7a(5H)-yl)methoxy)-7-(o-tolyl)pyrido[4,3-d]pyrimidin-4-yl)-3,8-diazabicyclo[3.2.1]octane-8-carboxylate. To a mixture of (1R,5S)-tert-butyl 3-(7-chloro-8-fluoro-2-((hexahydro-1H-pyrrolizin-7a-yl)methoxy)pyrido [4,3-d]pyrimidin-4-yl)-3,8-diazabicyclo[3.2.1]octane-8-carboxylate (120 mg, 225 μmol, 1.0 eq), 4,4,5,5-tetramethyl-2-(o-tolyl)-1,3,2-dioxaborolane (147 mg, 675 μmol, 3.0 eq) and Cs$_2$CO$_3$ (220 mg, 675 μmol, 3.0 eq) in dioxane (3 mL) and H$_2$O (1 mL) was added Pd(dppf)Cl$_2$ (16.5 mg, 22.5 μmol, 0.10 eq) under N$_2$. The mixture was stirred at 90° C. for 1 hour. After completion, the mixture was diluted with ethyl acetate (8 mL) and water (8 mL). The organic layer was separated. The aqueous phase was extracted with ethyl acetate (8 mL). The combined organic layer was washed with saturated brine (8 mL), dried over Na$_2$SO$_4$, filtered and concentrated under vacuum. The residue was purified by reversed phase flash chromatography [water (FA, 0.1%)/acetonitrile] to give the title compound (91 mg, 67% yield). Yellow oil; LCMS [ESI, M+1]: 589.3.

Step C. 4-((1R,5S)-3,8-diazabicyclo[3.2.1]octan-3-yl)-8-fluoro-2-((hexahydro-1H-pyrrolizin-7a-yl)methoxy)-7-(o-tolyl)pyrido[4,3-d]pyrimidine. To a mixture of (1R,5S)-tert-butyl 3-(8-fluoro-2-((hexahydro-1H-pyrrolizin-7a-yl)methoxy)-7-(o-tolyl)pyrido[4,3-d]pyrimidin-4-yl)-3,8-diazabicyclo[3.2.1]octane-8-carboxylate (109 mg, 185 μmol, 1.0 eq) in acetonitrile (1 mL) was added HCl·dioxane (4 M, 2 mL, 43 eq) at 0° C. The mixture was stirred at 0° C. for 1 hour. After completion, the mixture was concentrated under vacuum. The residue was purified by prep-HPLC (column: 3_Phenomenex Luna C18 75*30 mm*3 um; mobile phase: [water (0.225% FA)-ACN]; B %: 3%-23%, 7 min) to give the title compound (6.95 mg, 7.6% yield, 2FA). Off-white solid; $^1$H NMR (400 MHz, methanol-d4) δ=9.14 (s, 1H), 7.44-7.31 (m, 4H), 4.78 (br d, J=13.2 Hz, 2H), 4.67 (s, 2H), 4.03 (br s, 2H), 3.89 (br d, J=13.2 Hz, 2H), 3.75-3.66 (m, 2H), 3.30-3.26 (m, 2H), 2.38-2.30 (m, 2H), 2.26 (s, 3H), 2.20 (m, 4H), 2.14-2.08 (m, 2H), 2.07-2.00 (m, 2H), 1.99-1.92 (m, 2H); LCMS [ESI, M+1]: 489.3.

Example 273

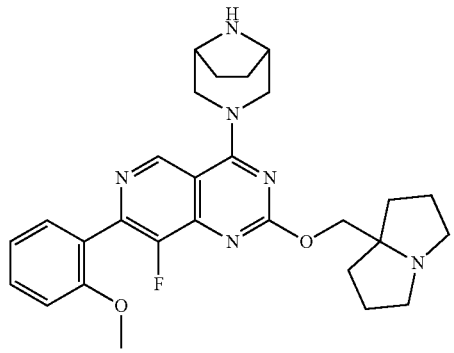 [SMILES: COc1ccccc1-c1ncc2c(N3CC4CCC(C3)N4)nc(OCC34CCCN3CCC4)nc2c1F]

4-((1R,5S)-3,8-diazabicyclo[3.2.1]octan-3-yl)-8-fluoro-2-((hexahydro-1H-pyrrolizin-7a-yl)methoxy)-7-(2-methoxyphenyl)pyrido[4,3-d]pyrimidine

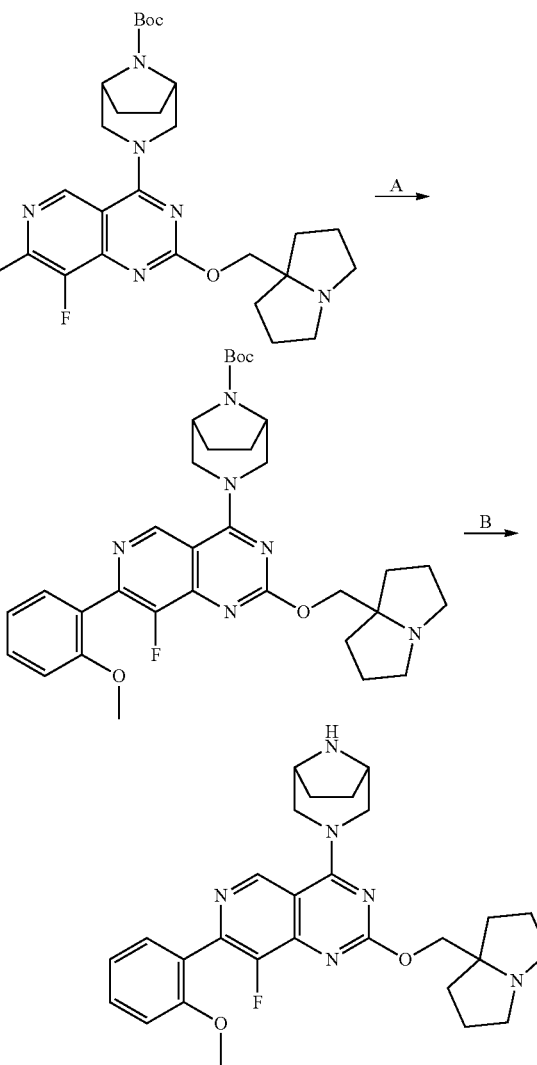

Step A. (1R,5S)-tert-butyl 3-(8-fluoro-2-((hexahydro-1H-pyrrolizin-7a-yl)methoxy)-7-(2-methoxyphenyl)pyrido[4,3-d]pyrimidin-4-yl)-3,8-diazabicyclo[3.2.1]octane-8-carboxylate. To the mixture of (1R,5S)-tert-butyl 3-(7-chloro-8-fluoro-2-((hexahydro-1H-pyrrolizin-7a-yl) methoxy) pyrido[4,3-d]pyrimidin-4-yl)-3,8-diazabicyclo[3.2.1] octane-8-carboxylate (120 mg, 225 μmol, 1 eq), (2-methoxyphenyl)boronic acid (103 mg, 675 μmol, 3 eq), Cs$_2$CO$_3$ (293 mg, 900 μmol, 4 eq) in dioxane (3 mL) and H$_2$O (1 mL) was added Pd(dppf)Cl$_2$ (16.5 mg, 22.5 μmol, 0.1 eq) under N$_2$, the mixture was degassed and stirred at 90° C. for 3 hours. After completion, the reaction mixture was diluted with water (30 mL) and extracted with ethyl acetate (2×40 mL). The combined organic phase was washed with brine (50 mL), dried over anhydrous sodium sulfate, filtered and concentrated to give a residue. The residue was purified by reversed phase flash chromatography [water (FA 0.1%)/acetonitrile] to give the title compound (44.6 mg, 33% yield). Colorless oil; LCMS [ESI, M+1]: 605.4.

Step B. 4-((1R,5S)-3,8-diazabicyclo[3.2.1]octan-3-yl)-8-fluoro-2-((hexahydro-1H-pyrrolizin-7a-yl)methoxy)-7-(2-methoxyphenyl)pyrido[4,3-d]pyrimidine. To the solution of (1R,5S)-tert-butyl 3-(8-fluoro-2-((hexahydro-1H-pyrrolizin-7a-yl)methoxy)-7-(2-methoxyphenyl)pyrido[4,3-d]pyrimidin-4-yl)-3,8-diazabicyclo[3.2.1]octane-8-carboxylate (50 mg, 82.7 μmol, 1 eq) in ACN (0.5 mL) was added HCl·dioxane (4 M, 1 mL, 48.4 eq) at 0° C., the mixture was stirred at 0° C. for 0.5 hour. After completion, the mixture was concentrated. Then the residue was adjusted with saturated NaHCO$_3$ to pH~8, and extracted with the solvent (DCM:MeOH=10:1) (2×20 mL). The combined organic phase was dried over anhydrous sodium sulfate, filtered and concentrated to give a residue. The residue was purified by prep-HPLC (column: Waters Xbridge C18 150*50 mm*10 um; mobile phase: [water (10 mM NH$_4$HCO$_3$)-ACN]; B %: 18%-48%, 10 min) to give the title compound (16.3 mg, 38% yield). Off-white solid; $^1$H NMR (400 MHz, chloroform-d) δ=9.02 (s, 1H), 7.51 (dd, J=1.6, 7.6 Hz, 1H), 7.48-7.42 (m, 1H), 7.10 (td, J=0.8, 7.6 Hz, 1H), 7.04 (d, J=8.0 Hz, 1H), 4.57 (br d, J=11.6 Hz, 2H), 4.18 (s, 2H), 3.85 (s, 3H), 3.69-3.55 (m, 4H), 3.17-3.02 (m, 2H), 2.68-2.61 (m, 2H), 2.16-2.04 (m, 2H), 1.91-1.83 (m, 4H), 1.70-1.64 (m, 6H); LCMS [ESI, M+1]: 505.4.

Example 274

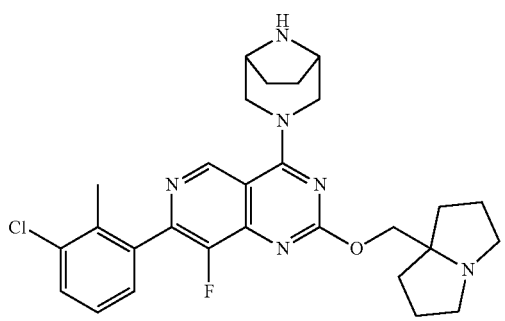 [SMILES: Cc1c(Cl)cccc1-c1ncc2c(N3CC4CCC(C3)N4)nc(OCC34CCCN3CCC4)nc2c1F]

4-((1R,5S)-3,8-diazabicyclo[3.2.1]octan-3-yl)-7-(3-chloro-2-methylphenyl)-8-fluoro-2-((hexahydro-1H-pyrrolizin-7a-yl)methoxy)pyrido[4,3-d]pyrimidine

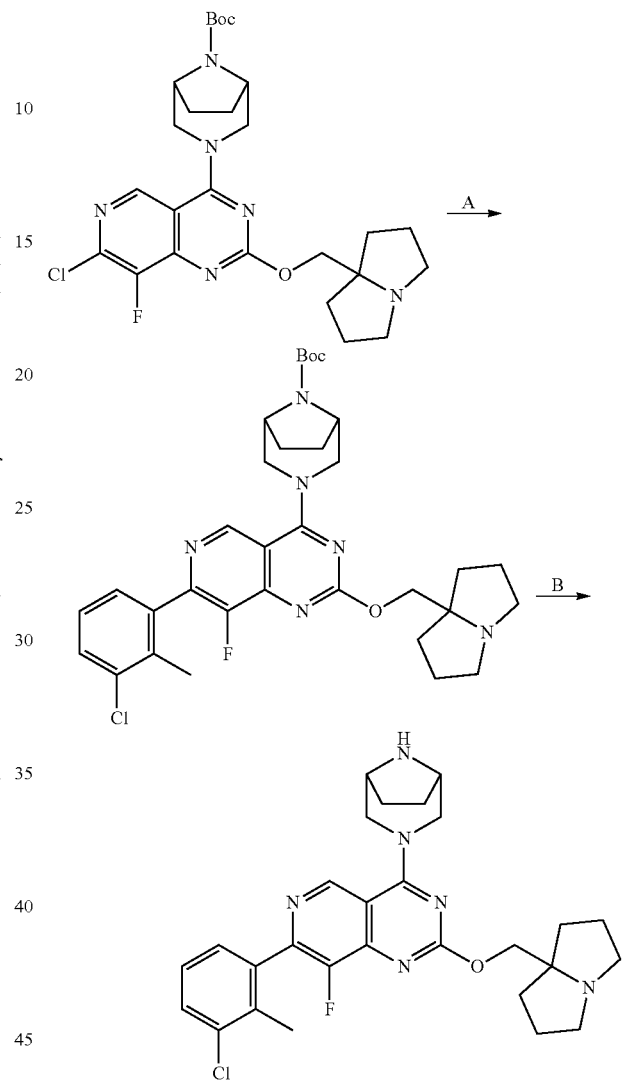

Step A. (1R,5S)-tert-butyl 3-(7-(3-chloro-2-methylphenyl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate. To the mixture of (1R,5S)-tert-butyl 3-(7-chloro-8-fluoro-2-((hexahydro-1H-pyrrolizin-7a-yl) methoxy)pyrido[4,3-d]pyrimidin-4-yl)-3,8-diazabicyclo [3.2.1]octane-8-carboxylate (100 mg, 188 μmol, 1.0 eq), (3-chloro-2-methylphenyl)boronic acid (160 mg, 938 μmol, 5.0 eq), Cs$_2$CO$_3$ (306 mg, 938 μmol, 5.0 eq) in dioxane (2 mL) and H$_2$O (0.6 mL) was added ditert-butyl(cyclopentyl) phosphane; dichloropalladium; iron (12.2 mg, 18.8 μmol, 0.1 eq) under N$_2$, the mixture was stirred at 65° C. for 2 hours. After completion, the mixture was quenched with water (10 mL), filtered and extracted with ethyl acetate (30 mL×2). The combined organic phase was washed with brine 30 mL, dried over anhydrous sodium sulfate, filtered and concentrated to give a residue. The residue was purified by reversed phase flash chromatography [water (FA 0.1%)/acetonitrile] to give the title compound (70.0 mg, 60% yield). Yellow Oil. LCMS [ESI, M+1]: 623.3.

Step B. 4-((1R,5S)-3,8-diazabicyclo[3.2.1]octan-3-yl)-7-(3-chloro-2-methylphenyl)-8-fluoro-2-((hexahydro-1H-pyrrolizin-7a-yl)methoxy)pyrido[4,3-d]pyrimidine. To the solution of (1R,5S)-tert-butyl 3-(7-(3-chloro-2-methylphenyl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (70.0 mg, 112 μmol, 1.0 eq) in ACN (0.5 mL) was added HCl·dioxane (4 M, 1 mL, 36 eq) at 0° C., and then the mixture was stirred at 0° C. for 0.5 hour. After completion, the mixture was concentrated at 25° C. The residue was purified by prep-HPLC (column: 3_Phenomenex Luna C18 75*30 mm*3 um; mobile phase: [water (0.225% FA)-ACN]; B %: 6%-26%, 8 min) to give the title compound (10.0 mg, 14% yield). Yellow Solid. $^1$H NMR (400 MHz, METHANOL-d4) δ=9.15 (s, 1H), 7.56 (t, J=4.8 Hz, 1H), 7.35 (d, J=4.4 Hz, 2H), 4.78 (br d, J=13.2 Hz, 2H), 4.67 (s, 2H), 4.02 (br s, 2H), 3.88 (br d, J=13.2 Hz, 2H), 3.75-3.65 (m, 2H), 3.30-3.26 (m, 2H), 2.33 (dd, J=6.8, 12.4 Hz, 2H), 2.29-2.25 (m, 3H), 2.25-1.87 (m, 10H). LCMS [ESI, M+1]: 523.3.

Example 275

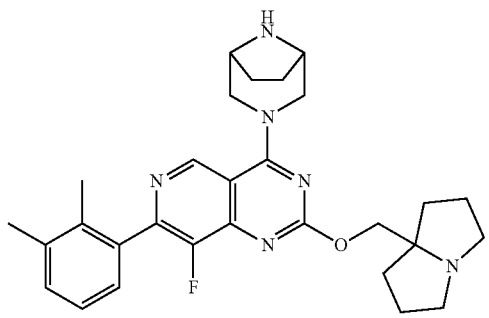 [SMILES: Cc1cccc(-c2ncc3c(N4CC5CCC(C4)N5)nc(OCC45CCCN4CCC5)nc3c2F)c1C]

4-((1R,5S)-3,8-diazabicyclo[3.2.1]octan-3-yl)-7-(2,3-dimethylphenyl)-8-fluoro-2-((hexahydro-1H-pyrrolizin-7a-yl)methoxy)pyrido[4,3-d]pyrimidine

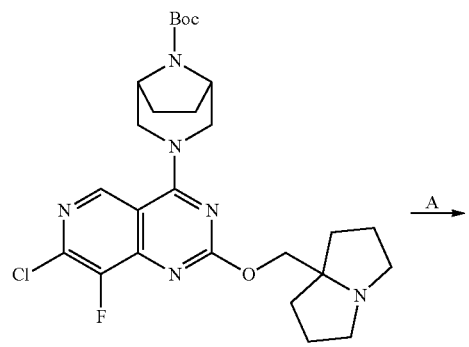

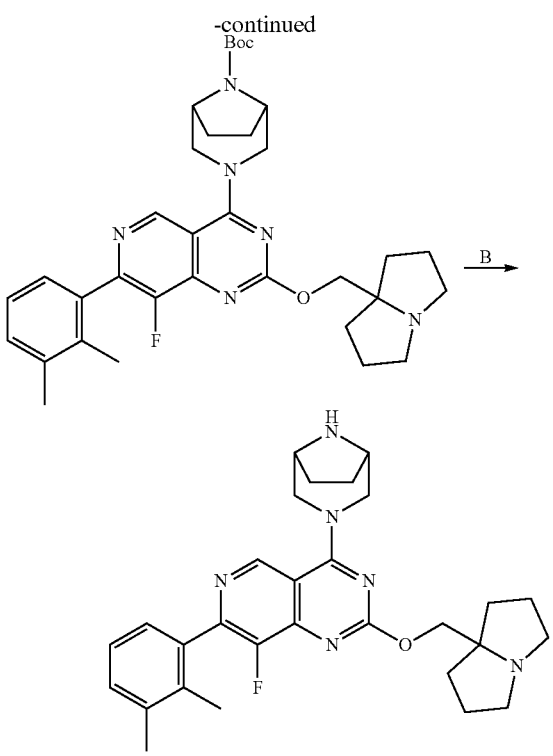

Step A. tert-butyl (1R,5S)-3-(7-(2,3-dimethylphenyl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate. To a mixture of (1R,5S)-tert-butyl 3-(7-chloro-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (120 mg, 225 μmol, 1.0 eq), (2,3-dimethylphenyl)boronic acid (101 mg, 675 μmol, 3.0 eq) and Cs$_2$CO$_3$ (220 mg, 675 μmol, 3.0 eq) in dioxane (3 mL) and H$_2$O (1 mL) was added Pd(dppf)Cl$_2$ (16.5 mg, 22.5 μmol, 0.10 eq) under N$_2$. The mixture was stirred at 90° C. for 1 hour. After completion, the mixture was diluted with ethyl acetate (6 mL) and water (6 mL). The organic layer was separated. The aqueous phase was extracted with ethyl acetate (8 mL). The combined organic layers were washed with saturated brine (10 mL), dried over Na$_2$SO$_4$, filtered and concentrated under vacuum. The residue was purified by reversed phase flash chromatography [water (FA, 0.1%)/acetonitrile] to give the title compound (120 mg, 60% yield). Yellow solid. LCMS [ESI, M+1, M/2+1]:603.4, 302.4.

Step B. 4-((1R,5S)-3,8-diazabicyclo[3.2.1]octan-3-yl)-7-(2,3-dimethylphenyl)-8-fluoro-2-((hexahydro-1H-pyrrolizin-7a-yl)methoxy)pyrido[4,3-d]pyrimidine. To a mixture of (1R,5S)-tert-butyl 3-(7-(2,3-dimethylphenyl)-8-fluoro-2-((hexahydro-1H-pyrrolizin-7a-yl) methoxy)pyrido[4,3-d]pyrimidin-4-yl)-3,8-diazabicyclo[3.2.1]octane-8-carboxylate (140 mg, 158 μmol, 1.0 eq) in acetonitrile (1 mL) was added HCl·dioxane (4 M, 2 mL, 51 eq) at 0° C. The mixture was stirred at 0° C. for 0.5 hour. After completion, the mixture was concentrated under vacuum. The residue was purified by prep-HPLC (column: 3_Phenomenex Luna C18 75*30 mm*3 um; mobile phase: [water (0.225% FA)-ACN]; B %: 6%-26%, 8 min) to give the title compound (21.3 mg, 22% yield, 2FA). White solid. $^1$H NMR (400 MHz, METHANOL-d4) δ=9.13 (s, 1H), 7.32 (d, J=7.2 Hz, 1H), 7.27-7.18 (m, 2H), 4.80 (br d, J=13.2 Hz, 2H), 4.67 (s, 2H), 4.08 (br s, 2H), 3.91 (br d, J=13.2 Hz, 2H), 3.74-3.67

(m, 2H), 3.30-3.26 (m, 2H), 2.38 (s, 3H), 2.37-2.30 (m, 2H), 2.27-2.18 (m, 4H), 2.14 (s, 3H), 2.12-1.97 (m, 6H). LCMS [ESI, M+1, M12+1]: 252.4, 503.3.

Example 276

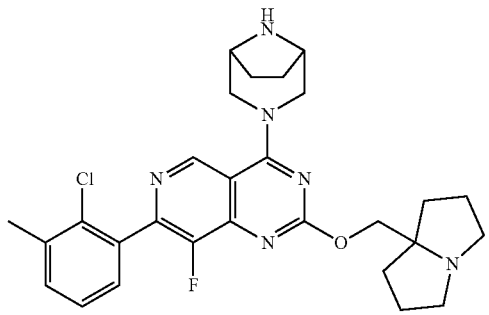 [SMILES: Cc1cccc(-c2ncc3c(N4CC5CCC(C4)N5)nc(OCC45CCCN4CCC5)nc3c2F)c1Cl]

4-((1R,5S)-3,8-diazabicyclo[3.2.1]octan-3-yl)-7-(2-chloro-3-methylphenyl)-8-fluoro-2-((hexahydro-1H-pyrrolizin-7a-yl)methoxy)pyrido[4,3-d]pyrimidine

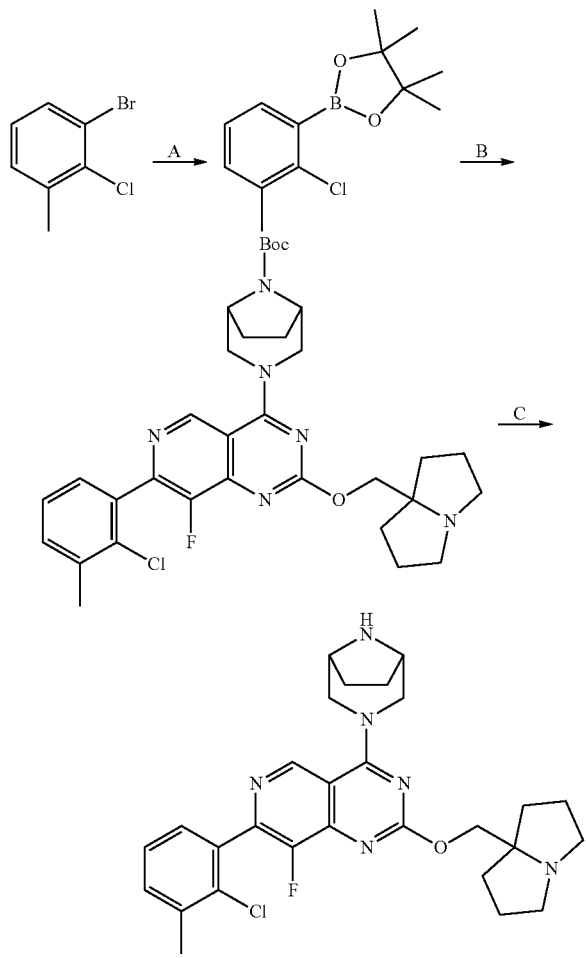

Step A. 2-(2-chloro-3-methyl-phenyl)-4,4,5,5-tetramethyl-1,3,2-dioxaborolane. A mixture of 1-bromo-2-chloro-3-methylbenzene (1 g, 4.87 mmol, 1.0 eq), 4,4,5,5-tetramethyl-2-(4,4,5,5-tetramethyl-1,3,2-dioxaborolan-2-yl)-1,3,2-dioxaborolane (1.85 g, 7.30 mmol, 1.5 eq), AcOK (1 g, 10.2 mmol, 2.1 eq) and Pd(dppf)Cl$_2$ (356 mg, 486 µmol, 0.1 eq) in dioxane (20 mL) was degassed and purged with N$_2$ for 3 times. The mixture was stirred at 100° C. for 2 hours under N$_2$ atmosphere. The reaction mixture was diluted with H$_2$O (100 mL) and extracted with ethyl acetate (25 mL×4). The combined organic layers were washed with saturated brine (10 mL), dried over anhydrous Na$_2$SO$_4$, filtered and concentrated under reduced pressure. The residue was purified by reversed phase flash chromatography [water (FA, 0.1%)/acetonitrile=0/1] to give the title compound (0.9 g, 73% yield). Red brown Oil; $^1$H NMR (400 MHz, METHANOL-d4) δ=7.44-7.43 (m, 1H), 7.35-7.34 (m, 1H), 7.18-7.14 (m, 1H), 2.36 (s, 3H), 1.36 (s, 12H).

Step B. tert-butyl (1R,5S)-3-(7-(2-chloro-3-methylphenyl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate. A mixture of (1R,5S)-tert-butyl 3-(7-chloro-8-fluoro-2-((hexahydro-1H-pyrrolizin-7a-yl)methoxy)pyrido [4,3-d]pyrimidin-4-yl)-3,8-diazabicyclo [3.2.1]octane-8-carboxylate (150 mg, 281 µmol, 1.0 eq), 2-(2-chloro-3-methylphenyl)-4,4,5,5-tetramethyl-1,3,2-dioxaborolane (360 mg, 1.43 mmol, 5.1 eq) and Cs$_2$CO$_3$ (459 mg, 1.41 mmol, 5.0 eq) and Pd(dtbpf)Cl$_2$ (19 mg, 29.15 µmol, 0.1 eq) in dioxane (4 mL) and H$_2$O (0.8 mL) was degassed and purged with N$_2$ for 3 times. The mixture was stirred at 65° C. for 2 hours under N$_2$ atmosphere. The reaction mixture was diluted with H$_2$O (5 mL) and extracted with ethyl acetate (10 mL×3). The combined organic layers were dried over anhydrous Na$_2$SO$_4$, filtered and concentrated under reduced pressure to give a residue. The residue was purified by reversed phase flash chromatography [water (FA, 0.1%)/acetonitrile=7/13] to give the title compound (140 mg, 78% yield). Light yellow Foam; LCMS [ESI, M+1]: 623.

Step C. 4-((1R,5S)-3,8-diazabicyclo[3.2.1]octan-3-yl)-7-(2-chloro-3-methylphenyl)-8-fluoro-2-((hexahydro-1H-pyrrolizin-7a-yl)methoxy)pyrido[4,3-d]pyrimidine. To a solution of (1R,5S)-tert-butyl 3-(7-(2-chloro-3-methylphenyl)-8-fluoro-2-((hexahydro-1H-pyrrolizin-7a-yl)methoxy) pyrido[4,3-d]pyrimidin-4-yl)-3,8-diazabicyclo[3.2.1] octane-8-carboxylate (75 mg, 118 µmol, 1.0 eq) in MeCN (3 mL) was added HCl·dioxane (4 M, 0.7 mL, 24 eq) dropwise below 5° C. The mixture was stirred at 5 to 15° C. for 0.5 hour. The reaction mixture was concentrated without heating under reduced pressure. The residue was purified by prep-HPLC (column: 3_Phenomenex Luna C18 75*30 mm*3 um; mobile phase: [water (0.225% FA)-ACN]; B %: 9%-29%, 8 min). The desired fractions were collected and lyophilized to give the title compound (29.4 mg, 39% yield, 2FA). Off-white Solid; $^1$H NMR (400 MHz, METHANOL-d4) δ=9.04 (s, 1H), 8.36 (s, 2H), 7.39 (dd, J=7.6, 1.22 Hz, 1H), 7.31-7.24 (m, 2H), 4.68 (d, J=13.2 Hz, 2H), 4.57 (s, 2H), 3.92 (s, 2H), 3.78 (d, J=13.2 Hz, 2H), 3.64-3.57 (m, 2H), 3.20-3.17 (m, 2H), 2.39 (s, 3H), 2.26-1.98 (m, 8H), 1.94-1.84 (m, 4H); LCMS [ESI, M+1]: 523.

Example 277

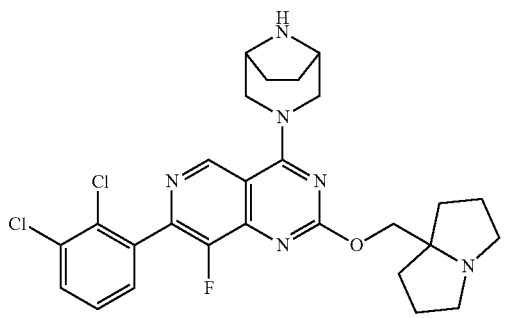 [SMILES: Fc1c(-c2cccc(Cl)c2Cl)ncc2c(N3CC4CCC(C3)N4)nc(OCC34CCCN3CCC4)nc12]

4-((1R,5S)-3,8-diazabicyclo[3.2.1]octan-3-yl)-7-(2,3-dichlorophenyl)-8-fluoro-2-((hexahydro-1H-pyrrolizin-7a-yl)methoxy)pyrido[4,3-d]pyrimidine

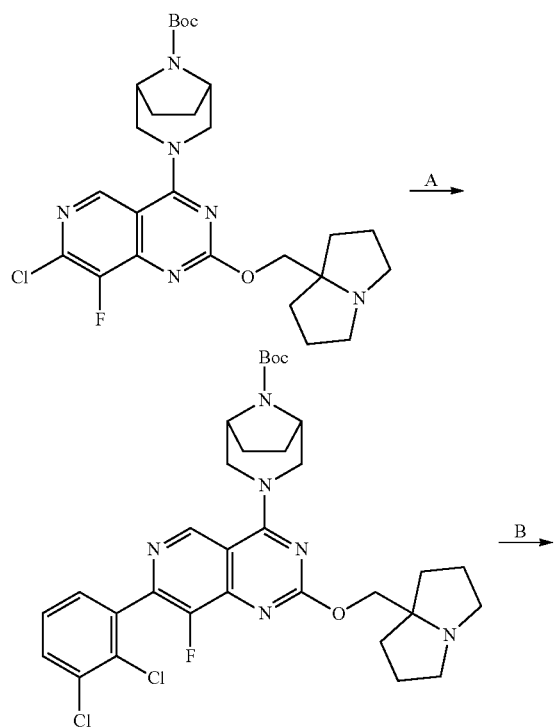

Step A. tert-butyl (1R,5S)-3-(7-(2,3-dichlorophenyl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate. A mixture of (1R,5S)-tert-butyl 3-(7-chloro-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (200 mg, 375 μmol, 1.0 eq), (2,3-dichlorophenyl)boronic acid (358 mg, 1.88 mmol, 5.0 eq) and Cs$_2$CO$_3$ (612 mg, 1.88 mmol, 5.0 eq) in dioxane (5 mL) and H$_2$O (1 mL) was degassed and purged with N$_2$ for 4 times. Pd(dtbpf)Cl$_2$ (26.0 mg, 39.9 μmol, 0.11 eq) was added. The mixture was degassed and purged with N$_2$ for 4 times. The reaction was stirred at 65° C. for 2 hours under N$_2$ atmosphere. Then the reaction mixture was diluted with H$_2$O (10 mL) and extracted with ethyl acetate (20 mL×3). The combined organic layers were washed with saturated brine (10 mL), dried over anhydrous Na$_2$SO$_4$, filtered and concentrated under reduced pressure to give a residue. The residue was purified by reversed phase flash chromatography [water (FA, 0.1%)/acetonitrile=7/13] to give the title compound (80 mg, 32% yield). Light yellow foam; LCMS [ESI, M+1]: 643.

Step B. 4-((1R,5S)-3,8-diazabicyclo[3.2.1]octan-3-yl)-7-(2,3-dichlorophenyl)-8-fluoro-2-((hexahydro-1H-pyrrolizin-7a-yl)methoxy)pyrido[4,3-d]pyrimidine. To a solution of (1R,5S)-tert-butyl 3-(7-(2,3-dichlorophenyl)-8-fluoro-2-((hexahydro-1H-pyrrolizin-7a-yl) methoxy)pyrido[4,3-d]pyrimidin-4-yl)-3,8-diazabicyclo[3.2.1]octane-8-carboxylate (72 mg, 110 μmol, 1.0 eq) in MeCN (3.6 mL) was added HCl·dioxane (4 M, 0.9 mL) below 10° C. The mixture was stirred at 5 to 15° C. for 0.5 hour. The reaction mixture was concentrated without heating under reduced pressure. The residue was purified by prep-HPLC (column: 3_Phenomenex Luna C18 75*30 mm*3 um; mobile phase: [water (0.225% FA)-ACN]; B %: 8%-28%, 8 min). The desired fractions were collected and lyophilized to give the title compound (12.91 mg, 18% yield, 2FA). Off-white solid; $^1$H NMR (400 MHz, METHANOL-d4) δ=9.15 (s, 1H), 8.46 (s, 2H), 7.79-7.67 (m, 1H), 7.49 (d, J=4.8 Hz, 2H), 4.73 (br d, J=12.96 Hz, 2H), 4.66 (s, 2H), 3.91 (br s, 2H), 3.83 (br d, J=13.20 Hz, 2H), 3.75-3.64 (m, 2H), 3.30-3.24 (m, 2H), 2.35-2.07 (m, 8H), 1.98-1.89 (m, 4H); LCMS [ESI, M+1]: 543.

Example 278

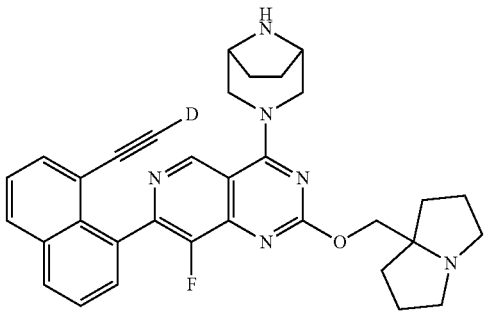 [SMILES: [2H]C#Cc1cccc2cccc(-c3ncc4c(N5CC6CCC(C5)N6)nc(OCC56CCCN5CCC6)nc4c3F)c12]

4-((1R,5S)-3,8-diazabicyclo[3.2.1]octan-3-yl)-7-(8-(ethynyl-d)naphthalen-1-yl)-8-fluoro-2-((tetrahydro-1H-pyrrolizin-7a(5H)-yl)methoxy)pyrido[4,3-d]pyrimidine

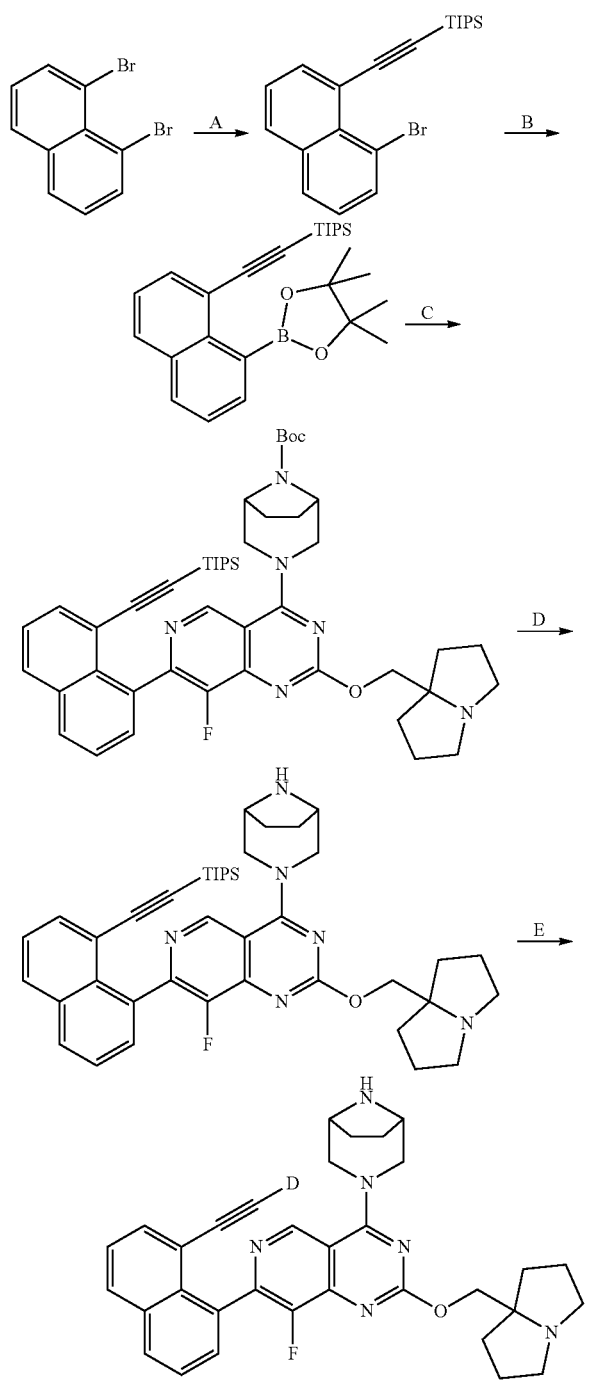

Step A. ((8-bromonaphthalen-1-yl)ethynyl)triisopropylsilane. To a mixture of 1,8-dibromonaphthalene (5.00 g, 17.5 mmol, 1.00 eq) and ethynyl(triisopropyl)silane (3.19 g, 17.5 mmol, 3.92 mL, 1.00 eq) in TEA (60.0 mL) were added CuI (333 mg, 1.75 mmol, 0.10 eq), Pd(PPh$_3$)$_2$Cl$_2$ (614 mg, 874 μmol, 0.05 eq) and PPh$_3$ (459 mg, 1.75 mmol, 0.10 eq) at N$_2$ atmosphere, and then the mixture was stirred at 80° C. for 3 hours. Upon completion, the reaction mixture was diluted with ethyl acetate (200 mL) and washed with water (3×100 mL). The organic layer was washed with brine (50 mL), dried over Na$_2$SO$_4$, filtered and concentrated under reduced pressure. The residue was purified by column chromatography (SiO$_2$, PE/EA=1/0) to give the title compound (5.50 g, 14.2 mmol, 81% yield). Light yellow oil.

Step B. triisopropyl((8-(4,4,5,5-tetramethyl-1,3,2-dioxaborolan-2-yl)naphthalen-1-yl) ethynyl)silane. To a mixture of ((8-bromonaphthalen-1-yl)ethynyl)triisopropylsilane (2.00 g, 5.16 mmol, 1.00 eq), 4,4,5,5-tetramethyl-2-(4,4,5,5-tetramethyl-1,3,2-dioxaborolan-2-yl)-1,3,2-dioxaborolane (2.62 g, 10.3 mmol, 2.00 eq) and KOAc (2.53 g, 25.8 mmol, 5.00 eq) in toluene (20 mL) was added Pd(dppf)Cl$_2$ (378 mg, 516 μmol, 0.10 eq) at N$_2$ atmosphere, and then the mixture was stirred at 80° C. for 12 hours. Upon completion, the reaction mixture was filtered and the filtrate was concentrated in vacuo. The residue was purified by column chromatography (SiO$_2$, PE/EA=1/0 to 5/1) to give the title compound (1.60 g, 3.31 mmol, 64% yield). Light yellow solid; $^1$H NMR (400 MHz, CDCl$_3$) δ 7.85-7.77 (m, 4H), 7.47-7.38 (m, 2H), 1.44 (s, 12H), 1.23-1.12 (m, 21H).

Step C. tert-butyl (1R,5S)-3-(8-fluoro-2-((tetrahydro-1H-pyrrolizin-7a(5H)-yl)methoxy)-7-(8-((triisopropylsilyl) ethynyl)naphthalen-1-yl)pyrido[4,3-d]pyrimidin-4-yl)-3,8-diazabicyclo[3.2.1]octane-8-carboxylate. To a solution of triisopropyl((8-(4,4,5,5-tetramethyl-1,3,2-dioxaborolan-2-yl)naphthalen-1-yl)ethynyl)silane (543 mg, 1.13 mmol, 2.00 eq) and (1R,5S)-tert-butyl 3-(7-chloro-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (300 mg, 563 μmol, 1.00 eq) in THF (5 mL) was added [2-(2-aminophenyl)phenyl]palladium(1+); bis(1-adamantyl)-butyl-phosphane; methanesulfonate (61.5 mg, 84.4 μmol, 0.15 eq), K$_3$PO$_4$ (1.50 M, 1.13 mL, 3.00 eq), and then the mixture was stirred at 60° C. for 12 hours at N$_2$ atmosphere. Upon completion, the mixture was quenched by H$_2$O (40 mL), and then extracted with EA (60 mL). The organic layer was washed with brine (20 mL), dried over Na$_2$SO$_4$, filtered and concentrated under reduced pressure to give the residue. The residue was purified by prep-TLC (SiO$_2$, DCM: MeOH=10:1) to give the title compound (300 mg, 354 μmol, 63% yield). Light yellow solid; $^1$H NMR (400 MHz, CDCl$_3$) δ 9.06 (s, 1H), 7.98-7.90 (m, 2H), 7.80 (d, J=7.2 Hz, 1H), 7.59-7.53 (m, 2H), 7.45 (t, J=7.6 Hz, 1H), 4.87-4.82 (m, 1H), 4.43-4.18 (m, 5H), 3.84-3.80 (m, 1H), 3.45-3.41 (m, 1H), 3.22-3.17 (m, 1H), 2.74-2.68 (m, 1H), 2.16-1.68 (m, 14H), 1.53 (s, 9H), 0.91-0.83 (m, 18H), 0.58-0.49 (m, 3H); LCMS [ESI, M+1]: 805.8.

Step D. 4-((1R,5S)-3,8-diazabicyclo[3.2.1]octan-3-yl)-8-fluoro-2-((tetrahydro-1H-pyrrolizin-7a(5H)-yl)methoxy)-7-(8-((triisopropylsilyl)ethynyl)naphthalen-1-yl)pyrido[4,3-d]pyrimidine. To a solution of tert-butyl (1R,5S)-3-(8-fluoro-2-((tetrahydro-1H-pyrrolizin-7a(5H)-yl)methoxy)-7-(8-((triisopropylsilyl)ethynyl)naphthalen-1-yl)pyrido[4,3-d]pyrimidin-4-yl)-3,8-diazabicyclo[3.2.1]octane-8-carboxylate (50.0 mg, 59.0 μmol, 1.00 eq) in EtOAc (0.2 mL) was added HCl·EtOAc (1 mL), the mixture was stirred at 20° C. for 1 hour. The mixture was quenched with saturated NaHCO$_3$ (20 mL), then extracted with EA (60 mL), the organic layer was washed with brine (20 mL), dried over Na$_2$SO$_4$, filtered and concentrated under reduced pressure to give the title compound (40.0 mg, 56.2 μmol, 95% yield). Light yellow solid; LCMS [ESI, M+1]: 705.6.

Step E. 74-((1R,5S)-3,8-diazabicyclo[3.2.1]octan-3-yl)-7-(8-(ethynyl-d)naphthalen-1-yl)-8-fluoro-2-((tetrahydro-1H-pyrrolizin-7a(5H)-yl)methoxy)pyrido[4,3-d]pyrimidine.

To a solution of 4-((1R,5S)-3,8-diazabicyclo[3.2.1]octan-3-yl)-8-fluoro-2-((tetrahydro-1H-pyrrolizin-7a(5H)-yl)methoxy)-7-(8-((triisopropylsilyl)ethynyl)naphthalen-1-yl)pyrido[4,3-d]pyrimidine (40.0 mg, 56.2 μmol, 1.00 eq) in DMAc (1 mL) were added CH₃OD (1 mL) and CsF (76.8 mg, 505 μmol, 18.6 μL, 9 eq), and the mixture was stirred at 40° C. for 12 hours. Upon completion, the mixture was concentrated under reduced pressure. The residue was purified by prep-HPLC (column: Waters Xbridge BEH C18 100*25 mm*5 um; mobile phase: [water (10 mM NH₄HCO₃)-ACN]; B %: 25%-70%, 10 min) to give the title compound (5.14 mg, 8.90 μmol, 16% yield, 95.2% purity). Light yellow solid; ¹H NMR (400 MHz, MeOD) δ 9.02 (s, 1H), 8.11-8.05 (m, 2H), 7.76-7.74 (m, 1H), 7.66 (t, J=8.0 Hz, 1H), 7.59 (dd, J=0.8, 6.8 Hz, 1H), 7.52 (t, J=8.0 Hz, 1H), 4.65-4.58 (m, 2H), 4.29 (s, 2H), 3.72 (br dd, J=4.4, 12.4 Hz, 2H), 3.68-3.63 (m, 2H), 3.17-3.11 (m, 2H), 2.79-2.73 (m, 2H), 2.12-2.06 (m, 2H), 1.99-1.75 (m, 10H); LCMS [ESI, M+1]: 550.3.

Example 279

3-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)-4-(prop-2-yn-1-yl)phenol

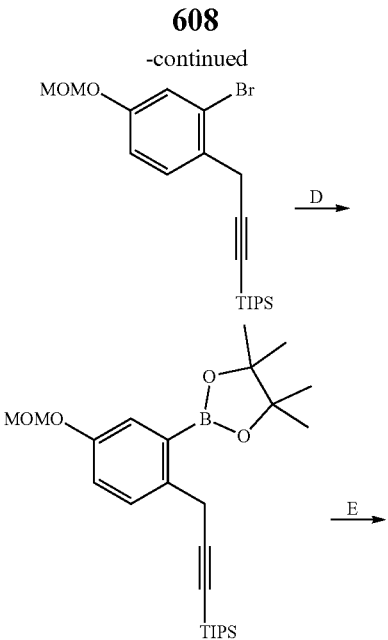

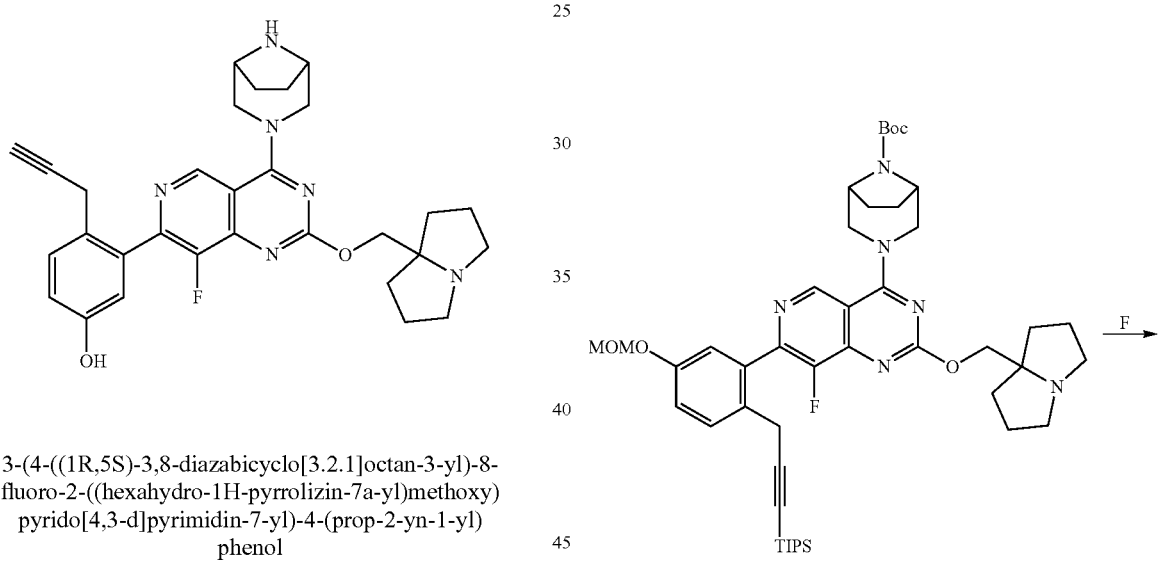

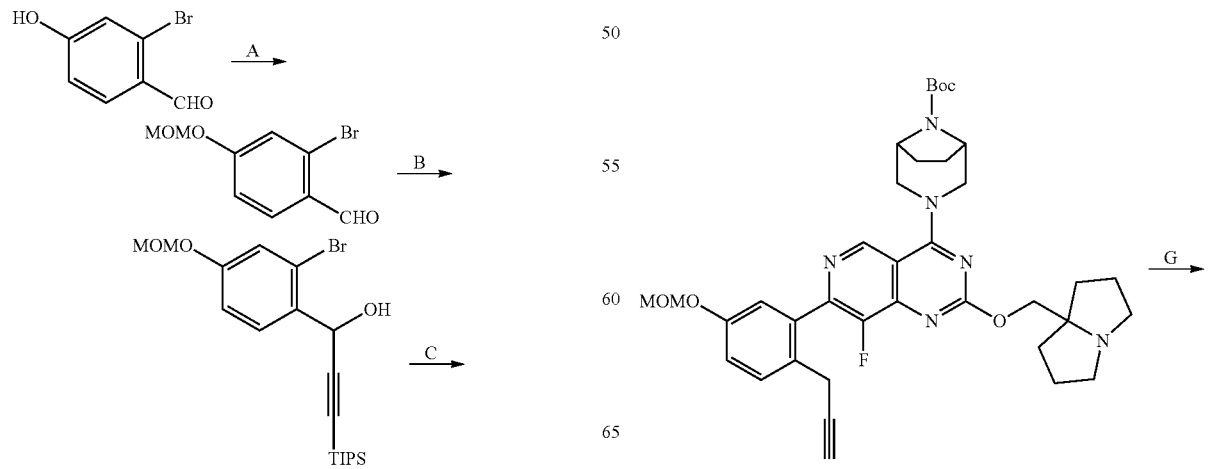

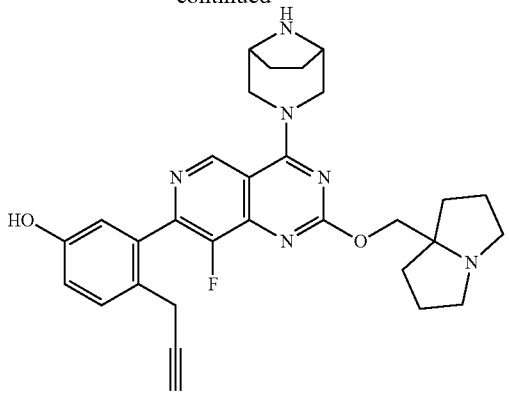

Step A. 2-bromo-4-(methoxymethoxy)benzaldehyde. A solution of 2-bromo-4-hydroxybenzaldehyde (5 g, 24.9 mmol, 1 eq) in THF (60 mL) was cooled to 0° C. and NaH (2.49 g, 62.2 mmol, 60% purity, 2.5 eq) was added. The mixture was stirred at 0° C. for 0.5 hour, and then chloro(methoxy)methane (5.01 g, 62.2 mmol, 4.72 mL, 2.5 eq) was added at 0° C. The mixture was stirred at 20° C. for 1.5 hours. Upon completion, the reaction mixture was quenched by saturated NH$_4$Cl aqueous (100 mL) at 0° C. The mixture was extracted with EA (3×50 mL). The organic layers were washed with brine (60 mL), dried over Na$_2$SO$_4$, filtered and concentrated under vacuum. The residue was purified by column chromatography (SiO$_2$, PE/EA=1/0 to 100/1) to give the title compound (3.80 g, 62% yield). Yellow oil; $^1$H NMR (400 MHz, DMSO-d6) δ 7.83 (d, J=8.4 Hz, 1H), 7.39-7.43 (m, 1H), 7.17-7.21 (m, 1H), 5.34 (s, 2H), 3.40 (s, 3H).

Step B. 1-(2-bromo-4-(methoxymethoxy)phenyl)-3-(triisopropylsilyl)prop-2-yn-1-ol. A solution of ethynyl(triisopropyl)silane (2.95 g, 16.2 mmol, 3.63 mL, 1.1 eq) in THF (35 mL) was cooled to 0° C., and n-BuLi (2.5 M, 6.46 mL, 1.1 eq) was added dropwise under N$_2$. The mixture was stirred at 0° C. for 1 hour, and then 2-bromo-4-(methoxymethoxy)benzaldehyde (3.60 g, 14.7 mmol, 1 eq) was added dropwise at 0° C. The mixture was stirred at 20° C. for 4 hours under N$_2$. Upon completion, the reaction mixture was quenched by aq. NH$_4$Cl (100 mL) at 0° C. The mixture was extracted with EtOAc (3×50 mL). The organic layers were washed with brine (50 mL), dried over Na$_2$SO$_4$, filtered and concentrated under vacuum. The residue was purified by column chromatography (SiO$_2$, PE/EA=1/0 to 5/1) to give the title compound (4.50 g, 72% yield). Yellow oil; $^1$H NMR (400 MHz, DMSO-d6) δ 7.62 (d, J=8.4 Hz, 1H), 7.25 (d, J=2.8 Hz, 1H), 7.07-7.10 (m, 1H), 6.12 (d, J=5.6 Hz, 1H), 5.49 (d, J=5.6 Hz, 1H), 5.21 (s, 2H), 3.37 (s, 3H), 1.00-1.02 (m, 21H).

Step C. (3-(2-bromo-4-(methoxymethoxy)phenyl)prop-1-yn-1-yl)triisopropylsilane. To a solution of 1-(2-bromo-4-(methoxymethoxy)phenyl)-3-(triisopropylsilyl)prop-2-yn-1-ol in DCM (50 mL) was added triethylsilane (2.47 g, 21.3 mmol, 3.39 mL, 2.02 eq), and then TFA (4.82 g, 42.3 mmol, 3.13 mL, 4.02 eq) was added dropwise. The mixture was stirred at 20° C. for 20 minutes. Upon completion, the reaction mixture was quenched by aq. NH$_4$Cl (120 mL) at 0° C. The mixture was extracted with DCM (3×60 mL). The organic layers were washed with brine (70 mL), dried over Na$_2$SO$_4$, filtered and concentrated under vacuum. The residue was purified by column chromatography (SiO$_2$, PE/EA=1/0 to 0/1) to give the title compound (3.50 g, 81% yield). Yellow oil; $^1$H NMR (400 MHz, DMSO-d6) δ 7.49 (d, J=8.8 Hz, 1H), 7.28 (d, J=2.4 Hz, 1H), 7.03-7.08 (m, 1H), 5.20 (s, 2H), 3.69 (s, 2H), 3.36 (s, 3H), 1.01-1.07 (m, 21H).

Step D. triisopropyl(3-(4-(methoxymethoxy)-2-(4,4,5,5-tetramethyl-1,3,2-dioxaborolan-2-yl)phenyl)prop-1-yn-1-yl)silane. To a solution of (3-(2-bromo-4-(methoxymethoxy)phenyl)prop-1-yn-1-yl)triisopropylsilane (1.5 g, 3.65 mmol, 1 eq), 4,4,5,5-tetramethyl-2-(4,4,5,5-tetramethyl-1,3,2-dioxaborolan-2-yl)-1,3,2-dioxaborolane (1.85 g, 7.29 mmol, 2 eq) in DMF (15 mL), KOAc (1.79 g, 18.2 mmol, 5 eq) and Pd(dppf)Cl$_2$ (267 mg, 365 μmol, 0.1 eq) was degassed and purged with N$_2$ for 3 times. The mixture was stirred at 80° C. for 12 hours under N$_2$. Upon completion, the reaction mixture was diluted with H$_2$O (100 mL). The mixture was extracted with EA (4×50 mL). The combined organic layers were washed with saturated brine (50 mL), dried over Na$_2$SO$_4$, filtered and concentrated under vacuum. The residue was purified by column chromatography (SiO$_2$, PE/EA=1/0 to 5/1) to give the title compound (1.32 g, 79% yield). Yellow oil; $^1$H NMR (400 MHz, CDCl$_3$) δ 7.64 (d, J=8.4 Hz, 1H), 7.43 (d, J=2.8 Hz, 1H), 7.09-7.14 (m, 1H), 5.19 (s, 2H), 3.98 (s, 2H), 3.48 (s, 3H), 1.33 (s, 12H), 1.07-1.12 (m, 21H).

Step E. (1R,5S)-tert-butyl 3-(8-fluoro-2-((hexahydro-1H-pyrrolizin-7a-yl)methoxy)-7-(5-(methoxymethoxy)-2-(3-(triisopropylsilyl)prop-2-yn-1-yl)phenyl)pyrido[4,3-d]pyrimidin-4-yl)-3,8-diazabicyclo[3.2.1]octane-8-carboxylate. To a solution of (1R,5S)-tert-butyl 3-(7-chloro-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (80 mg, 150 μmol, 1 eq) and triisopropyl(3-(4-(methoxymethoxy)-2-(4,4,5,5-tetramethyl-1,3,2-dioxaborolan-2-yl)phenyl)prop-1-yn-1-yl)silane (138 mg, 300 μmol, 2 eq) in THF (2 mL) were added [2-(2-aminophenyl)phenyl]palladium(1+); bis(1-adamantyl)-butyl-phosphane; methanesulfonate (21.8 mg, 30.0 μmol, 0.2 eq), and K$_3$PO$_4$ (1.5 M, 400 μL, 4 eq). The mixture was degassed and purged with N$_2$ for 3 times. The mixture was stirred at 60° C. for 12 hours under N$_2$. Upon completion, the reaction mixture was diluted with H$_2$O (30 mL), and extracted with EA (3×20 mL). The organic layers were washed with brine (30 mL), dried over Na$_2$SO$_4$, filtered and concentrated under vacuum. The residue was purified by prep-TLC (EA:NH$_4$OH=10:1) to give the title compound (55.0 mg, 44% yield). Yellow oil; LCMS [ESI, M+1]: 829.5.

Step F. (1R,5S)-tert-butyl 3-(8-fluoro-2-((hexahydro-1H-pyrrolizin-7a-yl)methoxy)-7-(5-(methoxymethoxy)-2-(prop-2-yn-1-yl)phenyl)pyrido[4,3-d]pyrimidin-4-yl)-3,8-diazabicyclo[3.2.1]octane-8-carboxylate. To a solution of (1R,5S)-tert-butyl 3-(8-fluoro-2-((hexahydro-1H-pyrrolizin-7a-yl)methoxy)-7-(5-(methoxymethoxy)-2-(3-(triisopropylsilyl)prop-2-yn-1-yl)phenyl)pyrido[4,3-d]pyrimidin-4-yl)-3,8-diazabicyclo[3.2.1]octane-8-carboxylate (50 mg, 60.3 μmol, 1 eq) in DMF (1 mL) was added CsF (82.4 mg, 543 μmol, 20.0 μL, 9 eq). The mixture was stirred at 30° C. for 5 hours. Upon completion, the reaction mixture was diluted with H$_2$O (20 mL). The mixture was extracted with EtOAc (3×10 mL). The combined organic layers were washed with brine (20 mL), dried over Na$_2$SO$_4$, filtered and concentrated under vacuum. The residue was purified by prep-TLC (EA:NH$_4$OH=20:1) to give the title compound (20.0 mg, 49% yield). Yellow oil; LCMS [ESI, M+1]: 673.3.

Step G. 3-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)-4-(prop-2-yn-1-yl)phenol. To a solution of (1R,5S)-tert-butyl 3-(8-fluoro-2-((hexahydro-1H-pyrrolizin-7a-yl)methoxy)-7-(5-(methoxymethoxy)-2-(prop-2-yn-1-yl)phenyl)pyrido[4,3-d]pyrimidin-4-yl)-3,8- diazabicyclo[3.2.1]octane-8-carboxylate (20 mg, 29.7 μmol, 1 eq) in EtOAc (1 mL) was added drop-wise HCl·EtOAc (4 M, 1 mL, 134 eq). The mixture was stirred at 25° C. for 10 minutes. Upon completion, the reaction mixture was concentrated under reduced pressure to give a residue. Then the residue was dissolved in MeCN (1 mL) and NH$_3$·H$_2$O (7 M) was added dropwise to pH~9. The residue was purified by prep-HPLC (column: Waters Xbridge BEH C18 100*25 mm*5 um; mobile phase: [water (10 mM NH$_4$HCO$_3$)-ACN]; B %: 15%-55%, 10 min) to give the title compound (6.34 mg, 37% yield). White solid; $^1$H NMR (400 MHz, MeOD-d4) δ 9.04 (s, 1H), 7.46 (d, J=8.8 Hz, 1H), 6.90 (dd, J=2.8, 8.4 Hz, 1H), 6.84 (d, J=2.4 Hz, 1H), 4.63-4.59 (m, 2H), 4.28 (s, 2H), 3.73-3.66 (m, 2H), 3.65-3.59 (m, 2H), 3.46 (d, J=2.4 Hz, 2H), 3.17-3.09 (m, 2H), 2.80-2.70 (m, 2H), 2.26 (t, J=2.4 Hz, 1H), 2.13-2.04 (m, 2H), 1.99-1.75 (m, 10H); LCMS [ESI, M+1]: 529.3.

Example 280

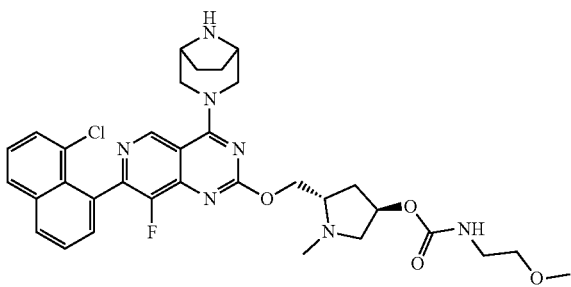 [SMILES: COCCNC(=O)O[C@@H]1C[C@@H](COc2nc(N3CC4CCC(C3)N4)c3cnc(-c4cccc5cccc(Cl)c45)c(F)c3n2)N(C)C1]

(3R,5S)-5-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)-1-methylpyrrolidin-3-yl (2-methoxyethyl)carbamate

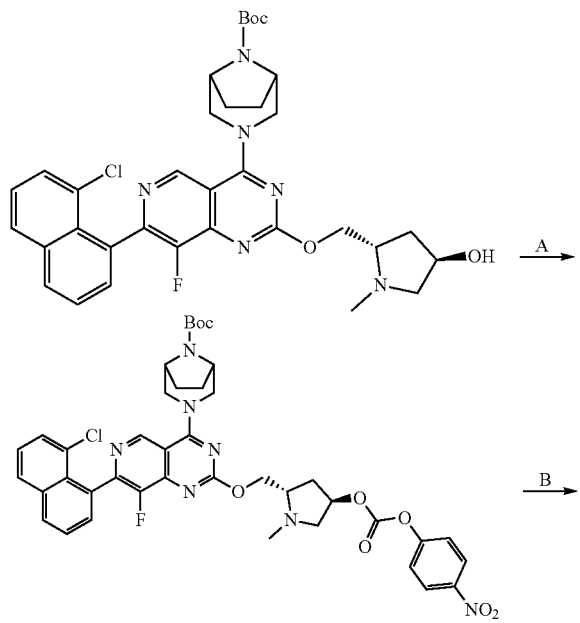

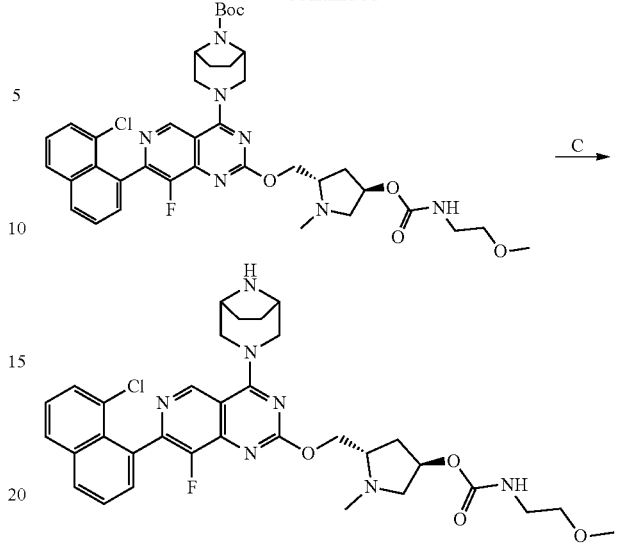

Step A. (1R,5S)-tert-butyl 3-(7-(8-chloronaphthalen-1-yl)-8-fluoro-2-(((2S,4R)-1-methyl-4-(((4-nitrophenoxy)carbonyl)oxy)pyrrolidin-2-yl)methoxy)pyrido[4,3-d]pyrimidin-4-yl)-3,8-diazabicyclo[3.2.1]octane-8-carboxylate. To a mixture of (1R,5S)-tert-butyl 3-(7-(8-chloronaphthalen-1-yl)-8-fluoro-2-(((2S,4R)-4-hydroxy-1-methylpyrrolidin-2-yl)methoxy)pyrido[4,3-d]pyrimidin-4-yl)-3,8-diazabicyclo[3.2.1]octane-8-carboxylate (synthesized according to Example 260, step H-K, 100 mg, 154 μmol, 1.0 eq) and (4-nitrophenyl) carbonochloridate (93.1 mg, 462 μmol, 3.0 eq) in THF (2.0 mL) was added t-BuOK (1 M, 308 μL, 2.0 eq) in one portion at 20° C. under N$_2$. The mixture was stirred at 20° C. for 1 hour. After completion, the reaction mixture was quenched by water (10 mL) at 20° C., then diluted with water (10 mL), and extracted with EtOA (20 mL×2). The combined organic layers were washed with brine (20 mL), dried over anhydrous sodium sulfate, filtered and concentrated under vacuum to give the residue. The residue was purified by reversed phase flash chromatography (C18, 0.1% FA in water, 0-100% MeCN) to give the title compound (70.0 mg, 54% yield). Yellow solid; LCMS [ESI, M+1]: 814.2.

Step B. tert-butyl (1R,5S)-3-(7-(8-chloronaphthalen-1-yl)-8-fluoro-2-(((2S,4R)-4-(((2-methoxyethyl)carbamoyl)oxy)-1-methylpyrrolidin-2-yl)methoxy)pyrido[4,3-d]pyrimidin-4-yl)-3,8-diazabicyclo[3.2.1]octane-8-carboxylate. To a mixture of (1R,5S)-tert-butyl 3-(7-(8-chloronaphthalen-1-yl)-8-fluoro-2-(((2S,4R)-1-methyl-4-(((4-nitrophenoxy)carbonyl)oxy)pyrrolidin-2-yl)methoxy)pyrido[4,3-d]pyrimidin-4-yl)-3,8-diazabicyclo[3.2.1]octane-8-carboxylate (70.0 mg, 86.0 μmol, 1.0 eq) and 2-methoxyethanamine (16.1 mg, 215 μmol, 18.7 μL, 2.5 eq) in DMF (1.0 mL) was added DIEA (55.5 mg, 430 μmol, 74.9 μL, 5.0 eq) in one portion under N$_2$. The mixture was stirred at 20° C. for 8 hours. After completion, the mixture was concentrated under reduced pressure to give the residue and the residue was purified by reversed phase flash chromatography (C18, 0.1% FA in water, 0-100% MeCN) to give the title compound (45.0 mg, 57% yield). Yellow solid; LCMS [ESI, M+1]: 750.2.

Step C. (3R,5S)-5-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)-1-methylpyrrolidin-3-yl (2-methoxyethyl)carbamate. To a mixture of tert-butyl (1R, 5S)-3-(7-(8-chloronaphthalen-1-yl)-8-fluoro-2-(((2S,4R)-4-(((2-methoxyethyl)carbamoyl)oxy)-1-methylpyrrolidin-2-yl)methoxy)pyrido[4,3-d]pyrimidin-4-yl)-3,8-diazabicyclo[3.2.1]octane-8-carboxylate (40.0 mg, 53.3 μmol, 1.0 eq) in MeCN (1.0 mL) was added HCl·dioxane (4.0 M, 0.2 mL, 15.0 eq) in one portion under $N_2$. The mixture was stirred at 0° C. for 0.5 hour. After completion, the mixture was concentrated under reduced pressure to give the residue and the residue was purified by prep-HPLC (column: Waters Xbridge C18 150*50 mm*10 um; mobile phase: [water (10 mM $NH_4HCO_3$)-ACN]; B %: 30%-60%, 10 min) to give the title compound (2.21 mg, 6.2% yield). White solid; $^1$H NMR (400 MHz, methanol-d4) δ=9.06 (s, 1H), 8.15 (dd, J=1.2, 8.4 Hz, 1H), 8.03 (dd, J=1.0, 8.2 Hz, 1H), 7.73-7.68 (m, 1H), 7.65-7.60 (m, 2H), 7.56-7.49 (m, 1H), 5.14-5.04 (m, 1H), 4.66-4.57 (m, 2H), 4.53-4.47 (m, 2H), 3.79-3.65 (m, 4H), 3.56-3.49 (m, 1H), 3.47-3.42 (m, 2H), 3.35 (s, 3H), 3.30-3.26 (m, 2H), 3.12-3.02 (m, 1H), 2.55 (s, 3H), 2.48 (dd, J=4.8, 10.8 Hz, 1H), 2.20-2.09 (m, 2H), 1.93-1.77 (m, 4H); LCMS [ESI, M+1]: 650.4.

Example 281

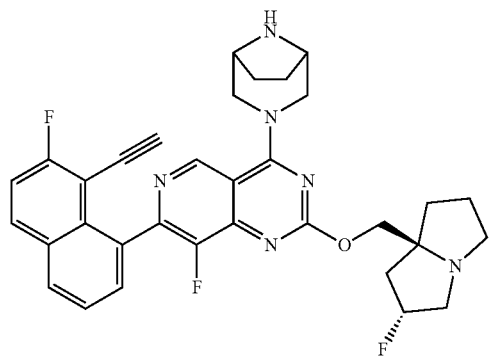 [SMILES: C#Cc1c(F)ccc2cccc(-c3ncc4c(N5CC6CCC(C5)N6)nc(OC[C@@]56CCCN5C[C@H](F)C6)nc4c3F)c12]

4-((1R,5S)-3,8-diazabicyclo[3.2.1]octan-3-yl)-7-(8-ethynyl-7-fluoronaphthalen-1-yl)-8-fluoro-2-(((2R,7aS)-2-fluorohexahydro-1H-pyrrolizin-7a-yl)methoxy)pyrido[4,3-d]pyrimidine

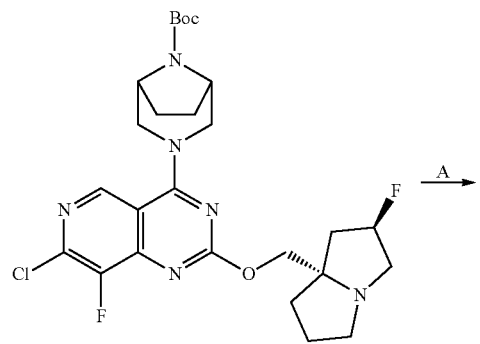

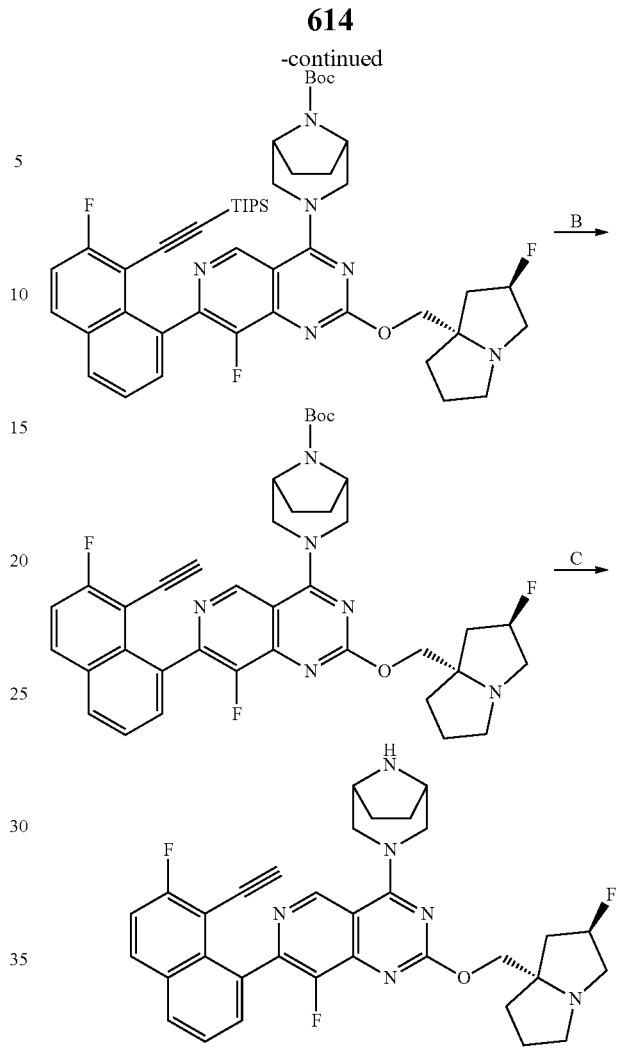

Step A. tert-butyl (1R,5S)-3-(8-fluoro-7-(7-fluoro-8-((triisopropylsilyl)ethynyl)naphthalen-1-yl)-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate. A mixture of (1R,5S)-tert-butyl 3-(7-chloro-8-fluoro-2-(((2R,7aS)-2-fluorohexahydro-1H-pyrrolizin-7a-yl)methoxy)pyrido[4,3-d]pyrimidin-4-yl)-3,8-diazabicyclo[3.2.1]octane-8-carboxylate (1 g, 1.81 mmol, 1 eq) and $K_3PO_4$ (1.5 M, 4.00 mL, 3.31 eq, in $H_2O$) in THF (20 mL) was degassed and purged with $N_2$ for 3 times. Then [2-(2-aminophenyl)phenyl]palladium(1+); bis(1-adamantyl)-butyl-phosphane; methanesulfonate (140 mg, 192 μmol, 1.06 e-1 eq) was added, followed by ((2-fluoro-8-(4,4,5,5-tetramethyl-1,3,2-dioxaborolan-2-yl)naphthalen-1-yl)ethynyl)triisopropylsilane (1.00 g, 2.21 mmol, 1.22 eq). The mixture was stirred at 60° C. for 2.5 hours under $N_2$ atmosphere. The reaction mixture was diluted with $H_2O$ (15 mL) and extracted with EtOAc (30 mL×3). The combined organic layers were dried over anhydrous $Na_2SO_4$, filtered and concentrated under reduced pressure to give a residue. The residue was purified by reversed phase flash chromatography [water (FA, 0.1%)/acetonitrile=11/9] to give the title compound (1.45 g, 93% yield). Light red foam; LCMS [ESI, M+1]: 841.4.

Step B. tert-butyl (1R,5S)-3-(7-(8-ethynyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4- yl)-3,8-diazabicyclo[3.2.1]octane-8-carboxylate. To a solution of tert-butyl (1R,5S)-3-(8-fluoro-7-(7-fluoro-8-((triisopropylsilyl)ethynyl)naphthalen-1-yl)-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (1.60 g, 1.86 mmol, 1.0 eq, 98% purity) in DMF (10 mL) was added CsF (2.90 g, 19.1 mmol, 704 µL, 10.2 eq). The mixture was stirred at 25° C. for 1.25 hours. The reaction mixture was diluted with acetonitrile (2 mL) and purified by reversed phase flash chromatography [water (FA, 0.1%)/acetonitrile=2/3] to give the title compound (1.20 g, 93% yield). Light yellow foam; LCMS [ESI, M+1]: 685.3.

Step C. 4-((1R,5S)-3,8-diazabicyclo[3.2.1]octan-3-yl)-7-(8-ethynyl-7-fluoronaphthalen-1-yl)-8-fluoro-2-(((2R,7aS)-2-fluorohexahydro-1H-pyrrolizin-7a-yl)methoxy)pyrido[4,3-d]pyrimidine. To a solution tert-butyl (1R,5S)-3-(7-(8-ethynyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (1.20 g, 1.73 mmol, 1.0 eq) in MeCN (15 mL) was added HCl·dioxane (4.0 M, 15 mL, 34.6 eq) dropwise below 5° C. The mixture was stirred at 15° C. for 0.5 hour. The reaction mixture was concentrated under reduced pressure at room temperature (without heating) to give a residue. The residue was dissolved in DCM (30 mL) and H$_2$O (10 mL). The pH of the mixture was adjusted to 8-9 with NaHCO$_3$ solid in portions below 5° C. The mixture was extracted with DCM (20 mL×4). The combined organic layers were dried over anhydrous Na$_2$SO$_4$, filtered and concentrated under reduced pressure to give a residue. The residue was purified by prep-HPLC (Phenomenex luna C18 150*40 mm*15 um; mobile phase: [water (0.225% FA)-ACN]; B %: 3%-33%, 10 min). The desired fractions were collected and lyophilized to give the title compound (986 mg, 68% yield, 2FA). Yellow solid; $^1$H NMR (400 MHz, methanol-d4) δ=9.10 (s, 1H), 8.15-8.11 (m, 2H), 7.69-7.63 (m, 2H), 7.48-7.43 (m, 1H), 5.57-5.43 (m, 1H), 4.83-4.76 (m, 2H), 4.62-4.54 (m, 2H), 4.10 (s, 2H), 3.96-3.88 (m, 2H), 3.84-3.61 (m, 3H), 3.44 (s, 1H), 3.36-3.32 (m, 1H), 2.65-2.00 (m, 10H); $^{19}$F NMR (376 MHz, methanol-d4) δ=-106.77, -139.32, -173.93; LCMS [ESI, M+1]: 585.3.

Example 282

4-(4-((1R,5S)-3,8-diazabicyclo[3.2.1]octan-3-yl)-8-fluoro-2-(((2R,7aS)-2-fluorohexahydro-1H-pyrrolizin-7a-yl)methoxy)pyrido[4,3-d]pyrimidin-7-yl)-5-fluoronaphthalen-2-ol

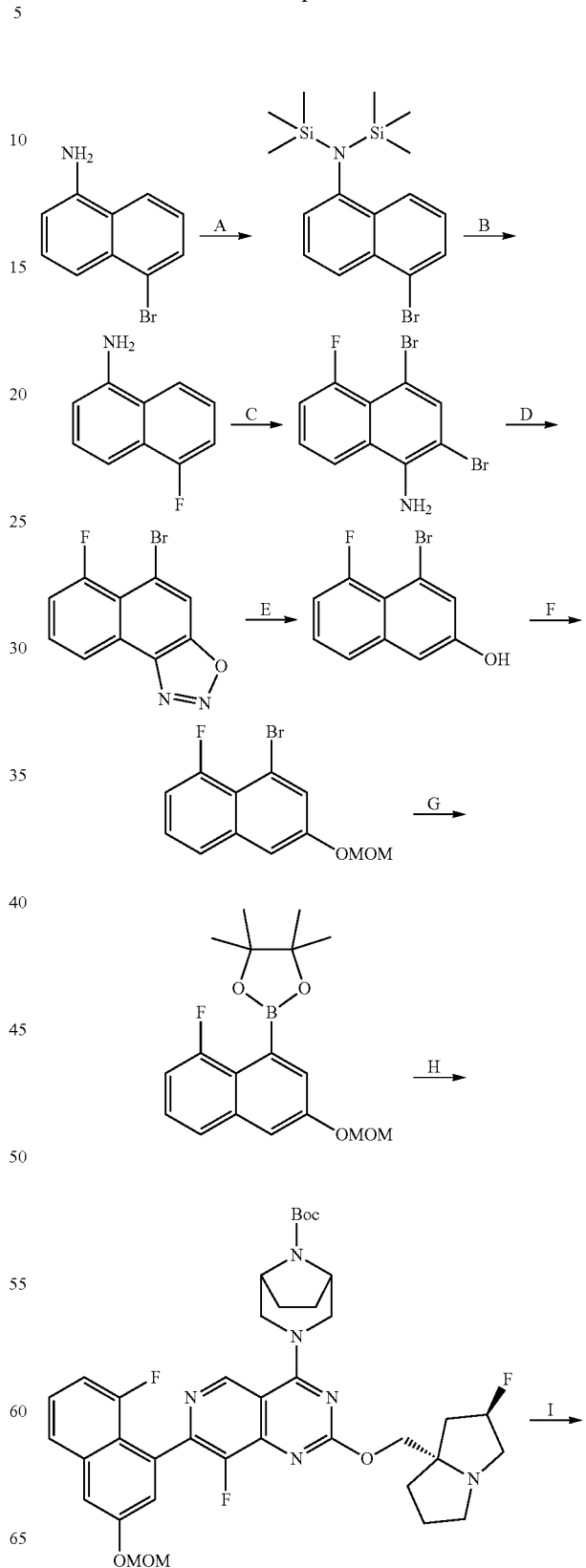

-continued

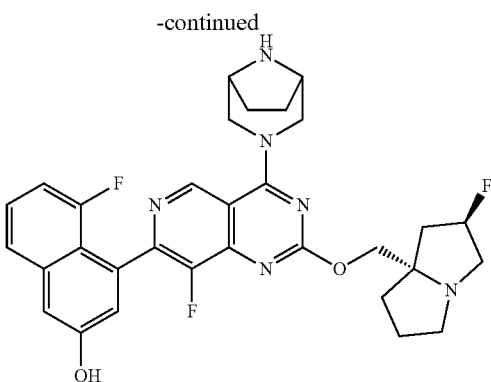

Step A. N-(5-bromonaphthalen-1-yl)-1,1,1-trimethyl-N-(trimethylsilyl)silanamine. To a solution of 5-bromonaphthalen-1-amine (10.0 g, 45.0 mmol, 1.0 eq) in THF (150 mL) under $N_2$ at −78° C. was added LiHMDS (1 M in THF, 99.1 mL, 2.2 eq). The mixture immediately turned into a dark red solution. After addition, the mixture was warmed to 20° C. The mixture initially became brown cloudy and then turned into a dark red solution as it was warmed to 20° C. Stirring was continued at 20° C. for 5 minutes. Then, the solution was cooled to −78° C. again and TMSCl (10.3 g, 94.6 mmol, 12.0 mL, 2.1 eq) was added dropwise. After addition, the resulting mixture was slowly warmed to 20° C. and stirred at 20° C. for 1 hour. The mixture was concentrated to dryness and the residue was extracted with hexanes. Solid was filtered and further extracted with hexanes. The combined extract was concentrated to give the title compound (16.5 g, crude) as red oil.

Step B. 5-fluoronaphthalen-1-amine. N-(5-bromonaphthalen-1-yl)-1,1,1-trimethyl-N-(trimethylsilyl)silanamine (57.8 g, 157 mmol, 1.0 eq) was dissolved in THF (700 mL) under $N_2$ and cooled to −78° C., followed by dropwise addition of n-Buli (2.5 M, 94.7 mL, 1.5 eq). After addition, the mixture was stirred for 15 minutes and N-fluoro-N-(phenylsulfonyl)benzenesulfonamide (79.5 g, 252 mmol, 1.6 eq) was added. The resulting mixture was slowly warmed to 20° C. for 1 hour. The reaction mixture was diluted with water (200 mL) and extracted with ethyl acetate (3×300 mL). The extract was washed with brine, dried over $Na_2SO_4$ and concentrated. The residue was then purified by column chromatography ($SiO_2$, petroleum). All the fractions containing the desired product were combined and concentrated under vacuum. The residue was treated with MeOH (200 mL) and HCl (30 mL, 1.0 M) for 3 minutes. Then the mixture was concentrated and basified with $NaHCO_3$. The mixture was extracted with ethyl acetate and concentrated under reduced pressure to give a residue. The residue was subject to reverse phase purification using MeCN in water (0-95% with 0.1 TFA) to give the title compound (10 g, 39% yield) as a brown solid. $^1$H NMR (400 MHz, chloroform-d) δ=7.59 (t, J=8.4 Hz, 2H), 7.43-7.31 (m, 2H), 7.21-7.08 (m, 1H), 6.84 (dd, J=0.8, 7.6 Hz, 1H), 4.17 (s, 2H).

Step C. 2,4-dibromo-5-fluoronaphthalen-1-amine. To a solution of 5-fluoronaphthalen-1-amine (8.55 g, 53.0 mmol, 1.0 eq) in AcOH (80 mL) was added a solution of $Br_2$ (18.5 g, 115 mmol, 5.96 mL, 2.18 eq) in AcOH (80 mL) at 0° C. The mixture was stirred at 70° C. for 1 hour. The reaction mixture was filtered, and the filter cake was washed with AcOH (200 mL). Then the residue was added to 15% aqueous of NaOH (100 mL). The mixture was stirred for 20 minutes and filtered. The solid was washed with water (200 mL) and dried under vacuum to give the title compound (15.5 g, 81% yield) as a black solid which was used to the next step without purification. $^1$H NMR (400 MHz, chloroform-d) δ=7.84 (s, 1H), 7.65-7.58 (m, 1H), 7.49-4.41 (m, 1H), 7.26-7.21 (m, 1H), 4.66 (br s, 2H).

Step D. 5-bromo-6-fluoronaphtho[1,2-d][1,2,3]oxadiazole. The 2,4-dibromo-5-fluoronaphthalen-1-amine (15.5 g, 48.6 mmol, 1.0 eq) was dissolved in AcOH (325 g, 5.42 mol, 310 mL, 111 eq) and propionic acid (38.5 g, 519 mmol, 38.7 mL, 10.7 eq) and cooled to 0° C. Then $NaNO_2$ (5.03 g, 72.9 mmol, 1.5 eq) was added. The mixture was stirred at 0° C. for 30 minutes and warmed up to 20° C. for 1 hour. The reaction mixture was filtered and the filter cake was washed with water (200 mL). The title compound (9 g, 69% yield) was obtained as a yellow solid and used in next step without purification. $^1$H NMR (400 MHz, chloroform-d) δ=7.53 (td, J=4.8, 8.0 Hz, 1H), 7.19 (s, 1H), 7.09 (d, J=8.0 Hz, 1H), 7.03 (ddd, J=0.8, 8.0, 12.4 Hz, 1H).

Step E. 4-bromo-5-fluoronaphthalen-2-ol. To a suspension of 5-bromo-6-fluoronaphtho[1,2-d][1,2,3]oxadiazole (9.0 g, 33.70 mmol, 1.0 eq) in EtOH (120 mL) and THF (60 mL) at 0° C. was added $NaBH_4$ (2.6 g, 68.7 mmol, 2.0 eq). Bubbles evolved immediately. The mixture was stirred at 0° C. for 0.5 hour. The mixture was quenched with $NaHSO_4$ (10%, 100 ml) and concentrated under vacuum to remove EtOH. Then the mixture was extracted with ethyl acetate (3×100 mL). The combined organic layers were washed with brine (50 mL), dried over $Na_2SO_4$, filtered and concentrated under reduced pressure to give a residue. The residue was purified by column chromatography ($SiO_2$, petroleum ether/ethyl acetate=20/1 to 3/1) to give the title compound (5.2 g, 52% yield) as a black solid. LCMS [ESI, M−1]: 238.9.

Step F. bromo-8-fluoro-3-(methoxymethoxy)naphthalene. To a solution of 4-bromo-5-fluoronaphthalen-2-ol (5.2 g, 21.6 mmol, 1.0 eq) in DCM (100 mL) were added DIEA (6.97 g, 53.9 mmol, 9.39 mL, 2.5 eq) and MOMCl (3.1 g, 38.5 mmol, 2.92 mL, 1.78 eq). The mixture was stirred at 0° C. for 0.5 hour. The reaction mixture was diluted with water (100 mL) and extracted with DCM (3×100 mL). The combined organic layers were washed with brine (100 mL), dried over $Na_2SO_4$, filtered and concentrated under reduced pressure to give a residue. The residue was purified by column chromatography ($SiO_2$, petroleum ether/ethyl acetate=50/1 to 5/1) to give the title compound (4.2 g, 65% yield) as a yellow solid. $^1$H NMR (400 MHz, chloroform-d) δ=7.58 (d, J=2.4 Hz, 1H), 7.53 (d, J=8.4 Hz, 1H), 7.42-7.34 (m, 2H), 7.09 (ddd, J=1.2, 7.6, 13.2 Hz, 1H), 5.28 (s, 2H), 3.52 (s, 3H).

Step G. 2-(8-fluoro-3-(methoxymethoxy)naphthalen-1-yl)-4,4,5,5-tetramethyl-1,3,2-dioxaborolane. A mixture of bromo-8-fluoro-3-(methoxymethoxy)naphthalene (1.0 g, 3.51 mmol, 1.0 eq), Pin2B2 (2.23 g, 8.77 mmol, 2.5 eq), KOAc (1.03 g, 10.5 mmol, 3 eq), Pd(dppf)Cl$_2$ (256 mg, 350 μmol, 0.1 eq) in dioxane (20 mL) was degassed and purged with $N_2$ for 3 times. Then the mixture was stirred at 110° C. for 1 hour under $N_2$ atmosphere. The reaction mixture was diluted with water (50 mL) and extracted with ethyl acetate (3×50 mL). The combined organic layers were washed with brine (50 mL), dried over $Na_2SO_4$, filtered and concentrated under reduced pressure to give a residue. The residue was purified by column chromatography ($SiO_2$, petroleum ether/ethyl acetate=50/1 to 5/1) to give the title compound (1.4 g, 103% yield) as a white solid. $^1$H NMR (400 MHz, chloroform-d) δ=7.51 (d, J=8.0 Hz, 1H), 7.42 (t, J=2.0 Hz, 1H), 7.39-7.30 (m, 2H), 7.02 (ddd, J=1.2, 7.6, 11.6 Hz, 1H), 5.30 (s, 2H), 3.51 (s, 3H), 1.45 (s, 12H).

Step H. (1R,5S)-tert-butyl 3-(8-fluoro-7-(8-fluoro-3-(methoxymethoxy)naphthalen-1-yl)-2-(((2R,7aS)-2-fluorohexahydro-1H-pyrrolizin-7a-yl)methoxy)pyrido[4,3-d]pyrimidin-4-yl)-3,8-diazabicyclo[3.2.1]octane-8-carboxylate. A mixture of (1R,5S)-tert-butyl 3-(7-chloro-8-fluoro-2-(((2R,7aS)-2-fluorohexahydro-1H-pyrrolizin-7a-yl)methoxy)pyrido[4,3-d]pyrimidin-4-yl)-3,8-diazabicyclo[3.2.1]octane-8-carboxylate (500 mg, 907 μmol, 1.0 eq), 2-(8-fluoro-3-(methoxymethoxy)naphthalen-1-yl)-4,4,5,5-tetramethyl-1,3,2-dioxaborolane (421 mg, 1.27 mmol, 1.4 eq), K₃PO₄ (1.5 M, 1.81 mL, 3.0 eq), [2-(2-aminophenyl)phenyl] palladium(1+); bis(1-adamantyl)-butyl-phosphane; methanesulfonate (66.1 mg, 90.7 μmol, 0.1 eq) in THF (10 mL) was degassed and purged with N₂ for 3 times. The mixture was stirred at 60° C. for 2 hours under N₂ atmosphere. The reaction mixture was diluted with water (20 mL) and extracted with ethyl acetate (3×30 mL). The combined organic layers were washed with brine (20 mL), dried over Na₂SO₄, filtered and concentrated under reduced pressure to give a residue. The residue was purified by reversed phase flash chromatography [water (0.1% formic acid)/acetonitrile)] to give the title compound (650 mg, 98% yield) as a yellow solid. LCMS [ESI, M+1]: 721.3.

Step I. 4-(4-((1R,5S)-3,8-diazabicyclo[3.2.1]octan-3-yl)-8-fluoro-2-(((2R,7aS)-2-fluorohexahydro-1H-pyrrolizin-7a-yl)methoxy)pyrido[4,3-d]pyrimidin-7-yl)-5-fluoronaphthalen-2-ol. To a solution of (1R,5S)-tert-butyl 3-(8-fluoro-7-(8-fluoro-3-(methoxymethoxy)naphthalen-1-yl)-2-(((2R,7aS)-2-fluorohexahydro-1H-pyrrolizin-7a-yl)methoxy)pyrido[4,3-d]pyrimidin-4-yl)-3,8-diazabicyclo[3.2.1]octane-8-carboxylate (630 mg, 874 μmol, 1.0 eq) in ACN (7 mL) was added HCl·dioxane (4 M, 7 mL). The mixture was stirred at 0° C. for 0.5 hour. The mixture was concentrated under vacuum. The residue was purified by prep-HPLC (column: Phenomenex luna C18 150*40 mm*15 um; mobile phase: [water (0.225% FA)-ACN]; B %: 1%-30%, 11 min). The desired fraction was collected and lyophilized to give the title compound (400.1 mg, 68% yield, 1.7FA) as a off-white solid. ¹H NMR (400 MHz, methanol-d4) δ=9.11 (s, 1H), 8.43 (s, 2H), 7.60 (d, J=8.4 Hz, 1H), 7.40 (td, J=5.2, 8.0 Hz, 1H), 7.34 (t, J=2.0 Hz, 1H), 7.19-7.14 (m, 1H), 6.92 (dd, J=7.6, 13.2 Hz, 1H), 5.53 (dt, J=3.2, 52.4 Hz, 1H), 4.84-4.76 (m, 2H), 4.67-4.52 (m, 2H), 4.13 (br s, 2H), 4.01-3.89 (m, 2H), 3.86-3.64 (m, 3H), 3.41-3.32 (m, 1H), 2.71-2.43 (m, 2H), 2.42-2.19 (m, 3H), 2.17-1.95 (m, 5H). LCMS [ESI, M+1]: 577.3.

Example 283

3-(4-((1R,5S)-3,8-diazabicyclo[3.2.1]octan-3-yl)-8-fluoro-2-(((2R,7aS)-2-fluorohexahydro-1H-pyrrolizin-7a-yl)methoxy)pyrido[4,3-d]pyrimidin-7-yl)-5-chloro-4-cyclopropylphenol

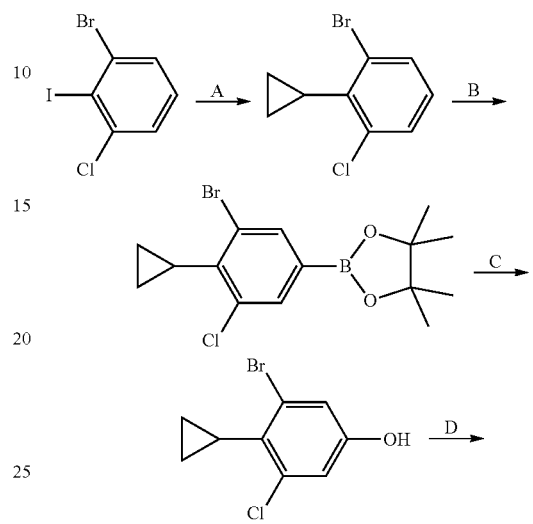
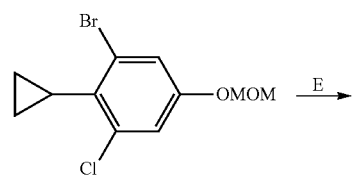
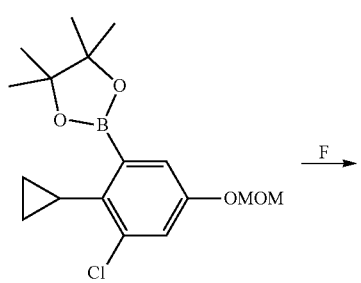
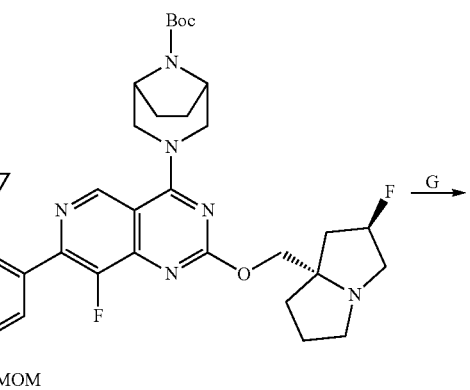
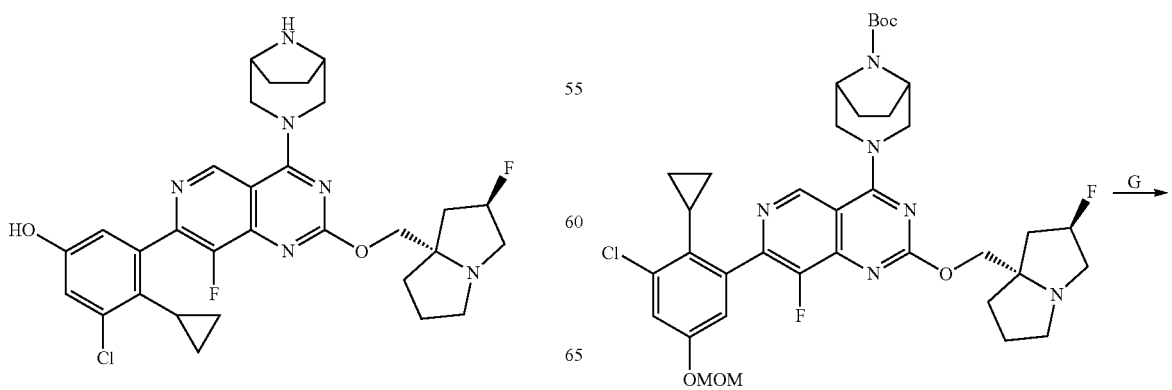

-continued

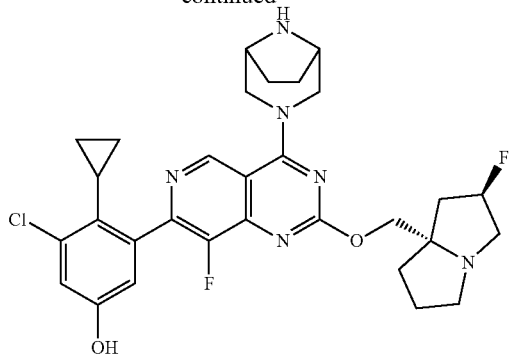

Step A. 1-bromo-3-chloro-2-cyclopropylbenzene. To a solution of 1-bromo-3-chloro-2-iodobenzene (5.0 g, 15.8 mmol, 1.0 eq) and $K_3PO_4$ (12.0 g, 56.7 mmol, 3.60 eq) in dioxane (9 mL) and $H_2O$ (3 mL) was added $Pd(dppf)Cl_2$ (576 mg, 788 μmol, 0.05 eq). Then cyclopropylboronic acid (1.76 g, 20.5 mmol, 1.30 eq) was added to the mixture. The mixture was stirred at 100° C. for 18 hours. Upon completion, the reaction mixture was diluted with water (5 mL) and extracted with ethyl acetate (3×5 mL). The combined organic layers were dried over $Na_2SO_4$, filtered and concentrated under reduced pressure to give a residue. The residue was purified by column chromatography ($SiO_2$, Petroleum ether:Ethyl acetate=100:1-20:1) affording the title compound (3.30 g, 72% yield). White solid; $^1$H NMR (400 MHz, $CDCl_3$) δ=7.47 (dd, J=1.2, 8.0 Hz, 1H), 7.31 (dd, J=1.2, 8.0 Hz, 1H), 7.00 (td, J=0.8, 8.0 Hz, 1H), 1.83-1.73 (m, 1H), 1.24-1.16 (m, 2H), 0.81-0.76 (m, 2H).

Step B. 2-(3-bromo-5-chloro-4-cyclopropylphenyl)-4,4,5,5-tetramethyl-1,3,2-dioxaborolane. A mixture of 1-bromo-3-chloro-2-cyclopropylbenzene (2.30 g, 9.93 mmol, 1.0 eq), 4,4,5,5-tetramethyl-1,3,2-dioxaborolane (3.81 g, 29.8 mmol, 4.32 mL, 3.0 eq), $(Ir(OMe)(cod))_2$ (329 mg, 497 μmol, 0.05 eq) and 4-tert-butyl-2-(4-tert-butyl-2-pyridyl)pyridine (160 mg, 596 μmol, 0.06 eq) in hexane (40 mL) was degassed and purged with $N_2$ for 3 times. The mixture was stirred at 60° C. for 2 hours under $N_2$ atmosphere. After completion, the reaction mixture was concentrated affording the title compound (4.0 g, crude). Brown oil.

Step C. 3-bromo-5-chloro-4-cyclopropylphenol. To a solution of 2-(3-bromo-5-chloro-4-cyclopropylphenyl)-4,4,5,5-tetramethyl-1,3,2-dioxaborolane (3.6 g, 10.1 mmol, 1.0 eq) in THF (30 mL) and $H_2O$ (15 mL) were added AcOH (38.8 g, 647 mmol, 37.0 mL, 64.2 eq) and $H_2O_2$ (21.8 g, 192 mmol, 18.5 mL, 19.1 eq). The mixture was stirred at 0° C. for 1 hour. Upon completion, the reaction mixture was diluted with $H_2O$ (5 mL) and extracted with ethyl acetate (3×5 mL). The combined organic layers were dried over $Na_2SO_4$, filtered and concentrated under reduced pressure. The residue was purified by reversed phase flash chromatography (C18, 0.1% formic acid condition) affording the title compound (1.7 g, two steps 68% yield). Yellow solid; $^1$H NMR (400 MHz, $CDCl_3$) δ=7.00 (d, J=2.0 Hz, 1H), 6.84 (d, J=2.4 Hz, 1H), 5.31 (br s, 1H), 1.72-1.62 (m, 1H), 1.18-1.07 (m, 2H), 0.77-0.68 (m, 2H).

Step D. 1-bromo-3-chloro-2-cyclopropyl-5-(methoxymethoxy)benzene. To a solution of 3-bromo-5-chloro-4-cyclopropylphenol (1.70 g, 6.87 mmol, 1.0 eq) and DIEA (2.66 g, 20.6 mmol, 3.59 mL, 3.0 eq) in dichloromethane (20 mL) was added chloro(methoxy)methane (1.11 g, 13.7 mmol, 1.04 mL, 2.0 eq) at 0° C. The mixture was stirred at 20° C. for 1 hour. Upon completion, the reaction mixture was concentrated under reduced pressure. The residue was purified by column chromatography ($SiO_2$, petroleum ether: ethyl acetate=100:1-30:1) affording the title compound (1.3 g, 65% yield). Colorless oil; $^1$H NMR (400 MHz, $CDCl_3$) δ 7.20 (d, J=2.8 Hz, 1H), 7.04 (d, J=2.8 Hz, 1H), 5.12 (s, 2H), 3.47 (s, 3H), 1.76-1.65 (m, 1H), 1.19-1.11 (m, 2H), 0.76-0.67 (m, 2H).

Step E. 2-(3-chloro-2-cyclopropyl-5-(methoxymethoxy)phenyl)-4,4,5,5-tetramethyl-1,3,2-dioxaborolane. To a solution of 1-bromo-3-chloro-2-cyclopropyl-5-(methoxymethoxy)benzene (200 mg, 686 μmol, 1.0 eq), KOAc (202 mg, 2.06 mmol, 3.0 eq) and 4,4,5,5-tetramethyl-2-(4,4,5,5-tetramethyl-1,3,2-dioxaborolan-2-yl)-1,3,2-dioxaborolane (348 mg, 1.37 mmol, 2.0 eq) in dioxane (3 mL) was added $Pd(dppf)Cl_2$ (50.2 mg, 68.6 μmol, 0.1 eq). The mixture was stirred at 100° C. for 4 hours. Upon completion, the reaction mixture was added water (5 mL) and extracted with ethyl acetate (3×5 mL). The organic layer was dried over $Na_2SO_4$, filtered and concentrated. The residue was purified by column chromatography ($SiO_2$, petroleum ether: ethyl acetate=100:1-50:1) affording the title compound (160 mg, 69% yield); Colorless oil; $^1$H NMR (400 MHz, $CDCl_3$) δ 7.12-7.09 (m, 2H), 5.14 (s, 2H), 3.46 (s, 3H), 2.03-1.93 (m, 1H), 1.38 (s, 12H), 1.02-0.95 (m, 2H), 0.56-0.50 (m, 2H).

Step F. (1R,5S)-tert-butyl-3-(7-(3-chloro-2-cyclopropyl-5-(methoxymethoxy)phenyl)-8-fluoro-2-(((2R,7aS)-2-fluorohexahydro-1H-pyrrolizin-7a-yl)methoxy)pyrido[4,3-d]pyrimidin-4-yl)-3,8-diazabicyclo[3.2.1]octane-8-carboxylate. To a mixture of (1R,5S)-tert-butyl 3-(7-chloro-8-fluoro-2-(((2R,7aS)-2-fluorohexahydro-1H-pyrrolizin-7a-yl)methoxy)pyrido[4,3-d]pyrimidin-4-yl)-3,8-diazabicyclo[3.2.1]octane-8-carboxylate (100 mg, 181 μmol, 1.0 eq), 2-(3-chloro-2-cyclopropyl-5-(methoxymethoxy)phenyl)-4,4,5,5-tetramethyl-1,3,2-dioxaborolane (120 mg, 354 μmol, 1.95 eq) and $K_3PO_4$ (1.5 M, 363 μL, 3.0 eq) in THF (2 mL) was added [2-(2-aminophenyl)phenyl]palladium (1+); bis(1-adamantyl)-butyl-phosphane; methanesulfonate (13.2 mg, 18.2 μmol, 0.10 eq). The mixture was stirred at 60° C. for 2 hours. Upon completion, the reaction mixture was added water (5 mL) and extracted with ethyl acetate (3×5 mL). The organic layer was dried over $Na_2SO_4$, filtered and concentrated. The residue was purified by reversed phase flash chromatography (C18, 0.1% formic acid condition) affording the title compound (60 mg, 45% yield); Yellow solid.

Step G. 3-(4-((1R,5S)-3,8-diazabicyclo[3.2.1]octan-3-yl)-8-fluoro-2-(((2R,7aS)-2-fluorohexahydro-1H-pyrrolizin-7a-yl)methoxy)pyrido[4,3-d]pyrimidin-7-yl)-5-chloro-4-cyclopropylphenol. To a solution of (1R,5S)-tert-butyl-3-(7-(3-chloro-2-cyclopropyl-5-(methoxymethoxy)phenyl)-8-fluoro-2-(((2R,7aS)-2-fluorohexahydro-1H-pyrrolizin-7a-yl)methoxy)pyrido[4,3-d]pyrimidin-4-yl)-3,8-diazabicyclo[3.2.1]octane-8-carboxylate (55 mg, 75.6 μmol, 1.0 eq) in MeCN (1 mL) was added HCl·dioxane (4 M, 2 mL, 106 eq). The mixture was stirred at 20° C. for 0.5 hour. After completion, the mixture was concentrated. The residue was purified by prep-HPLC (column: Shim-pack C18 150*25*10 um; mobile phase: [water (0.225% FA)-ACN]; B %: 12%-32%, 9 min) affording the title compound (9.71 mg, 22% yield, 1.7 HCOOH). Yellow solid; SFC analysis: Column: Chiralpak IC-3 50×4.6 mm I.D., 3 um Mobile phase: Phase A for $CO_2$, and Phase B for MeOH+CAN (0.05% DEA); Gradient elution: 50% MeOH+CAN (0.05% DEA) in CO2 Flow rate: 3 mL/min; Detector: PDAColumn Temp: 35° C.; Back Pressure: 100 Bar; $^1$H NMR (400 MHz, methanol-d4) δ 9.12 (s, 1H), 6.98 (d, J=2.4 Hz, 1H), 6.80 (d, J=2.8 Hz, 1H), 5.62-5.40 (m, 1H), 4.85-4.75 (m, 2H), 4.63-4.52 (m, 2H), 4.09 (br s, 2H), 3.89 (br dd, J=5.2, 13.6 Hz, 2H), 3.85-3.74 (m, 1H), 3.73-3.62 (m, 2H), 3.39-3.32 (m, 1H), 2.68-2.42 (m, 2H), 2.40-2.31 (m, 1H), 2.30-2.19 (m, 2H), 2.16-1.96 (m, 5H), 1.89-1.79 (m, 1H), 0.62 (br d, J=7.6 Hz, 2H), 0.07 (br d, J=3.6 Hz, 2H); LCMS [ESI, M+1]: 583.3.

Example 284

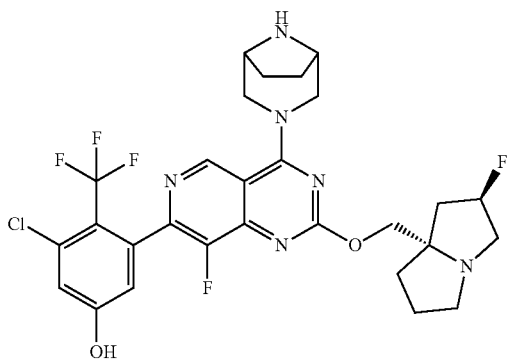 [SMILES: Oc1cc(Cl)c(C(F)(F)F)c(-c2ncc3c(N4CC5CCC(C4)N5)nc(OC[C@@]45CCCN4C[C@H](F)C5)nc3c2F)c1]

3-(4-((1R,5S)-3,8-diazabicyclo[3.2.1]octan-3-yl)-8-fluoro-2-(((2R,7aS)-2-fluorohexahydro-1H-pyrrolizin-7a-yl)methoxy)pyrido[4,3-d]pyrimidin-7-yl)-5-chloro-4-(trifluoromethyl)phenol

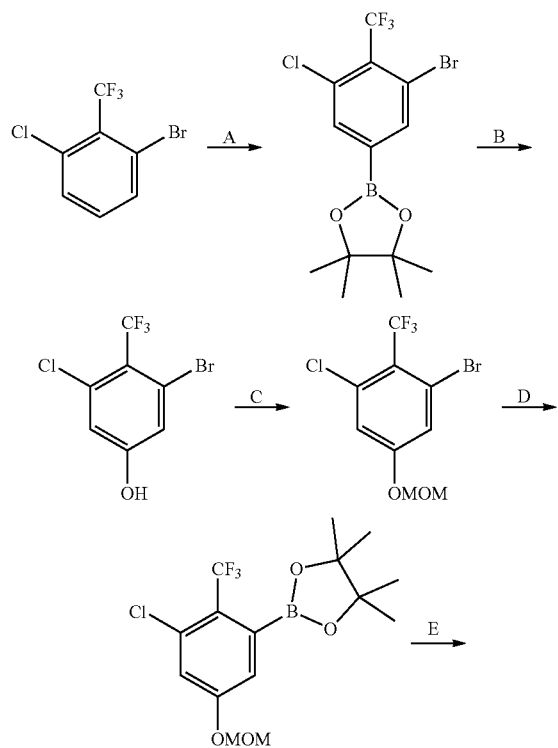

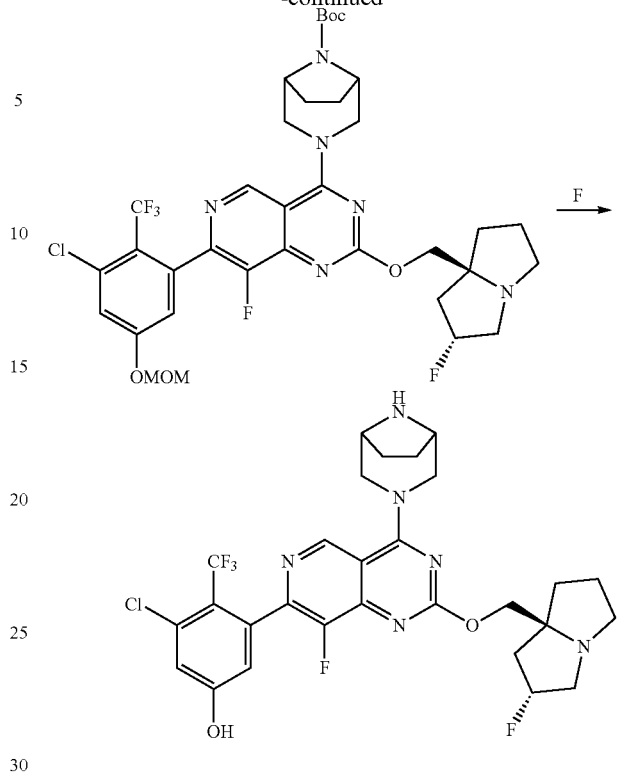

Step A. 2-(3-bromo-5-chloro-4-(trifluoromethyl)phenyl)-4,4,5,5-tetramethyl-1,3,2-dioxaborolane. To a solution of 1-bromo-3-chloro-2-(trifluoromethyl)benzene (5.00 g, 19.3 mmol, 1.0 eq), 4,4,5,5-tetramethyl-1,3,2-dioxaborolane (4.93 g, 38.5 mmol, 2.0 eq) in THF (60 mL) were added dtbbpy (621 mg, 2.31 mmol, 0.12 eq) and (Ir(OMe)(cod))$_2$ (1.28 g, 1.93 mmol, 0.1 eq) under N$_2$, the mixture was stirred at 60° C. for 2 hours. After completion, The mixture was concentrated to give the title compound (12.0 g, crude) which was used into the next step without further purification. Black Oil.

Step B. 3-bromo-5-chloro-4-(trifluoromethyl)phenol. To a solution of 2-(3-bromo-5-chloro-4-(trifluoromethyl)phenyl)-4,4,5,5-tetramethyl-1,3,2-dioxaborolane (12.0 g, 31.1 mmol, 1.0 eq) in THF (100 mL) and H$_2$O (50 mL) were added AcOH (74.8 g, 1.25 mol, 40.0 eq) and H$_2$O$_2$ (70.6 g, 623 mmol, 30% purity, 20.0 eq) at 10° C. The mixture was stirred at 10° C. for 1 hour. After completion, the mixture was added water (200 mL) and EtOAc (200 mL). The organic phase was separated, washed with saturated Na$_2$SO$_3$ (200 mL×2) and then brine (100 mL), dried over anhydrous sodium sulfate, filtered and concentrated to give a residue. The residue was purified by reversed phase flash chromatography [water (FA 0.1%)/acetonitrile] to give the title compound (5.20 g, two steps 83% yield). Black Oil. $^1$H NMR (400 MHz, chloroform-d) δ=7.02 (d, J=2.0 Hz, 1H), 6.82 (d, J=2.0 Hz, 1H).

Step C. 1-bromo-3-chloro-5-(methoxymethoxy)-2-(trifluoromethyl)benzene. To the mixture of 3-bromo-5-chloro-4-(trifluoromethyl)phenol (5.20 g, 18.9 mmol, 1.0 eq), DIEA (7.33 g, 56.7 mmol, 3.0 eq) in DCM (70 mL) was added MOMCl (3.05 g, 37.9 mmol, 2.0 eq) at 0° C., and the mixture was stirred at 20° C. for 1 hour. After completion, the mixture was quenched with water (50 mL) and extracted with DCM (50 mL). The combined organic phases were washed with brine (50 mL), dried over anhydrous sodium sulfate, filtered and concentrated to give a residue. The residue was purified by column chromatography (SiO$_2$, Petroleum ether/Ethyl acetate=20/1 to 5/1) to give the title compound (4.05 g, 84% yield). White Solid. $^1$H NMR (400 MHz, chloroform-d) δ=7.33 (d, J=2.0 Hz, 1H), 7.15 (d, J=2.0 Hz, 1H), 5.19 (s, 2H), 3.48 (s, 3H).

Step D. 2-(3-chloro-5-(methoxymethoxy)-2-(trifluoromethyl)phenyl)-4,4,5,5-tetramethyl-1,3,2-dioxaborolane. To the mixture of 1-bromo-3-chloro-5-(methoxymethoxy)-2-(trifluoromethyl)benzene (1.00 g, 3.13 mmol, 1.0 eq), 4,4,5,5-tetramethyl-2-(4,4,5,5-tetramethyl-1,3,2-dioxaborolan-2-yl)-1,3,2-dioxaborolane (1.59 g, 6.26 mmol, 2.0 eq), AcOK (923 mg, 9.40 mmol, 3.0 eq) in dioxane (10 mL) was added Pd(dppf)Cl$_2$ (233 mg, 318 μmol, 0.1 eq) under N$_2$, the mixture was stirred at 100° C. for 2 hours. The mixture was diluted with ethyl acetate (20 mL), washed with saturated brine (20 mL), dried over anhydrous sodium sulfate, filtered and concentrated to give a residue. The residue was purified by reversed phase flash chromatography [water (FA 0.1%)/acetonitrile] to give the title compound (600 mg, 52% yield). Black Solid. $^1$H NMR (400 MHz, chloroform-d) δ=7.19 (d, J=2.4 Hz, 1H), 6.98 (d, J=2.4 Hz, 1H), 5.20 (s, 2H), 3.47 (s, 3H), 1.37 (s, 12H).

Step E. (1R,5S)-tert-butyl 3-(7-(3-chloro-5-(methoxymethoxy)-2-(trifluoromethyl)phenyl)-8-fluoro-2-(((2R,7aS)-2-fluorohexahydro-1H-pyrrolizin-7a-yl)methoxy)pyrido[4,3-d]pyrimidin-4-yl)-3,8-diazabicyclo[3.2.1]octane-8-carboxylate. To the mixture of (1R,5S)-tert-butyl 3-(7-chloro-8-fluoro-2-(((2R,7aS)-2-fluorohexahydro-1H-pyrrolizin-7a-yl)methoxy)pyrido[4,3-d]pyrimidin-4-yl)-3,8-diazabicyclo[3.2.1]octane-8-carboxylate (25.0 mg, 45.4 μmol, 1.0 eq), 2-(3-chloro-5-(methoxymethoxy)-2-(trifluoromethyl)phenyl)-4,4,5,5-tetramethyl-1,3,2-dioxaborolane (20.0 mg, 54.6 μmol, 1.2 eq), and K$_3$PO$_4$ (1.5 M, 90.8 μL, 3.0 eq) in toluene (2 mL) was added [2-(2-aminophenyl)phenyl]palladium(1+); bis(1-adamantyl)-butyl-phosphane; methanesulfonate (3.31 mg, 4.55 μmol, 0.1 eq) under N$_2$, and then the mixture was stirred at 60° C. for 2 hours. The reaction mixture was diluted with water (10 mL), then extracted with ethyl acetate (2×15 mL). The combined organic phase was washed with brine (10 mL), dried over Na$_2$SO$_4$ and concentrated. The residue was purified by reversed phase flash chromatography [water (FA 0.10%)/acetonitrile] to give the title compound (14.0 mg, 37% yield). Yellow oil. LCMS [ESI, M+1]: 755.2.

Step F. 3-(4-((1R,5S)-3,8-diazabicyclo[3.2.1]octan-3-yl)-8-fluoro-2-(((2R,7aS)-2-fluorohexahydro-1H-pyrrolizin-7a-yl)methoxy)pyrido[4,3-d]pyrimidin-7-yl)-5-chloro-4-(trifluoromethyl)phenol. To the solution of (1R,5S)-tert-butyl 3-(7-(3-chloro-5-(methoxymethoxy)-2-(trifluoromethyl)phenyl)-8-fluoro-2-(((2R,7aS)-2-fluorohexahydro-1H-pyrrolizin-7a-yl)methoxy)pyrido[4,3-d]pyrimidin-4-yl)-3,8-diazabicyclo[3.2.1]octane-8-carboxylate (40.0 mg, 53.0 μmol, 1.0 eq) in ACN (0.8 mL) was added HCl·dioxane (4 M, 1.6 mL, 121 eq) at 0° C., the mixture was stirred at 0° C. for 0.5 hour. The mixture was concentrated at 20° C. to give a residue, and then saturated NaHCO$_3$ was added to adjust the pH to 8. The mixture was diluted with MeOH (2 mL), filtered and concentrated to give a residue. The residue was purified by prep-HPLC (column: Waters Xbridge C18 150*50 mm*10 um; mobile phase: [water (10 mM NH$_4$HCO$_3$)-ACN]; B %: 25%-55%, 10 min) to give the title compound (9.72 mg, 29% yield). White Solid. $^1$H NMR (400 MHz, methanol-d4) δ=9.01 (s, 1H), 7.09 (d, J=2.0 Hz, 1H), 6.70 (d, J=2.4 Hz, 1H), 5.43-5.18 (m, 1H), 4.67-4.51 (m, 2H), 4.37-4.14 (m, 2H), 3.75-3.60 (m, 4H), 3.30-3.16 (m, 3H), 3.10-2.96 (m, 1H), 2.42-2.19 (m, 2H), 2.18-2.07 (m, 1H), 2.06-1.94 (m, 2H), 1.93-1.73 (m, 5H). LCMS [ESI, M+1]: 611.1.

Example 285

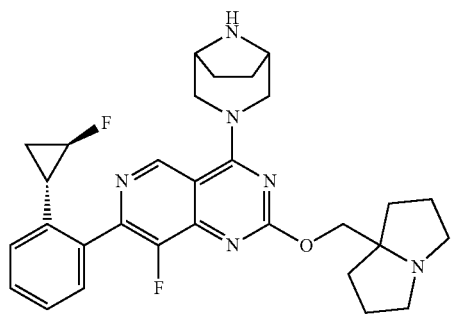 [SMILES: Fc1c(-c2ccccc2[C@@H]2C[C@H]2F)ncc2c(N3CC4CCC(C3)N4)nc(OCC34CCCN3CCC4)nc12]

4-((1R,5S)-3,8-diazabicyclo[3.2.1]octan-3-yl)-8-fluoro-7-(2-(trans-2-fluorocyclopropyl)phenyl)-2-((hexahydro-1H-pyrrolizin-7a-yl)methoxy)pyrido[4,3-d]pyrimidine

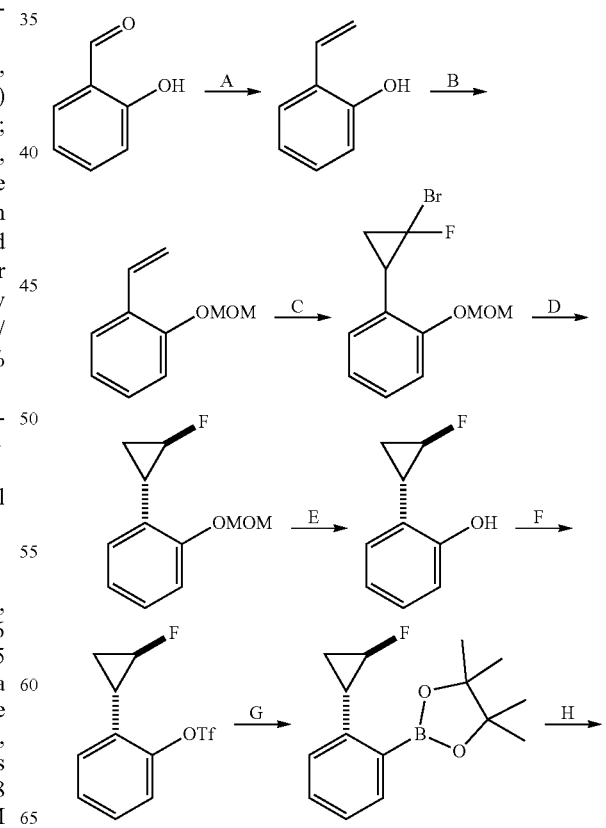

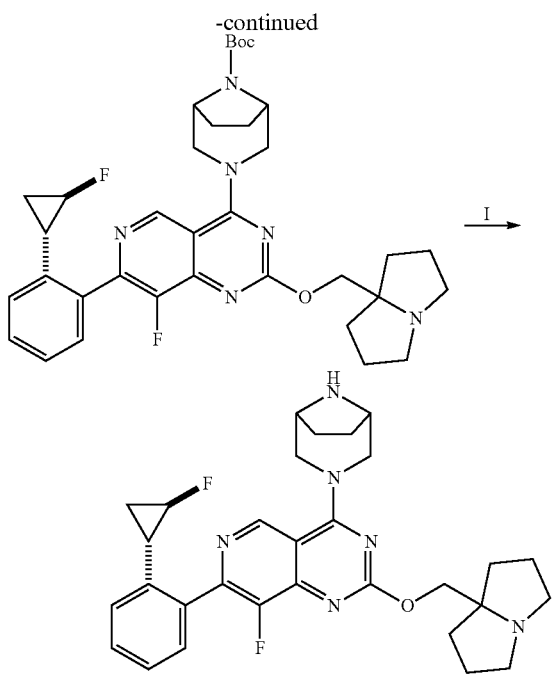

Step A. 2-vinylphenol. To a solution of methyltriphenylphosphonium bromide (121 g, 338 mmol, 1.38 eq) in THF (300 mL) was added t-BuOK (38.0 g, 339 mmol, 1.38 eq) in portions. The mixture was stirred at 20° C. for 1 hour. The mixture was cooled to −70° C. and 2-hydroxybenzaldehyde (30 g, 246 mmol, 26.1 mL, 1.0 eq) was added to the mixture in portions. The mixture was stirred at 20° C. for 12 hours. Upon completion, the reaction mixture was quenched with water (300 mL) and extracted with dichloromethane (3×300 mL). The organic layer was dried over Na$_2$SO$_4$, filtered and concentrated. The residue was purified by column chromatography (SiO$_2$, petroleum ether: ethyl acetate=300:1-50:1) affording the title compound (71 g, crude). Yellow solid; $^1$H NMR (400 MHz, CDCl$_3$) δ=7.41 (dd, J=1.2, 7.6 Hz, 1H), 7.13-6.99 (m, 2H), 6.97-6.92 (m, 1H), 6.82 (td, J=8.0, 1.2 Hz, 1H), 5.74 (dd, J=1.6, 18.0 Hz, 1H), 5.24 (dd, J=1.6, 11.2 Hz, 1H).

Step B. 1-(methoxymethoxy)-2-vinylbenzene. To a solution of 2-vinylphenol (60 g, 499 mmol, 1.0 eq) and DIEA (193 g, 1.50 mol, 261 mL, 3.0 eq) in dichloromethane (500 mL) was added MOMCl (40.2 g, 499 mmol, 37.9 mL, 1.0 eq) at 0° C. The mixture was stirred at 0-20° C. for 1 hour. Upon completion, the reaction mixture was quenched with water (400 mL) and separated. The aqueous layer was extracted with ethyl acetate (3×400 mL). The combined organic layers were dried over Na$_2$SO$_4$, filtered and concentrated. The residue was purified by column chromatography (SiO$_2$, petroleum ether: ethyl acetate=100:1-20:1) affording the title compound (15 g, 18% yield). Colorless oil; $^1$H NMR (400 MHz, CDCl$_3$) δ=7.52 (dd, J=1.6, 7.6 Hz, 1H), 7.26-7.20 (m, 1H), 7.15-7.05 (m, 2H), 7.04-6.97 (m, 1H), 5.76 (dd, J=1.6, 18.0 Hz, 1H), 5.30 (dd, J=1.2, 11.2 Hz, 1H), 5.23 (s, 2H), 3.51 (s, 3H).

Step C. 1-(2-bromo-2-fluorocyclopropyl)-2-(methoxymethoxy)benzene. To a solution of 1-(methoxymethoxy)-2-vinylbenzene (14.0 g, 85.3 mmol, 1.0 eq), dibromo(fluoro)methane (40.9 g, 213 mmol, 2.50 eq) and TEBAC (971 mg, 4.26 mmol, 0.05 eq) in dichloromethane (140 mL) was added a solution of NaOH (20.5 g, 512 mmol, 6.0 eq) in H$_2$O (10.5 mL) in portions at 0° C. The mixture was stirred at 20° C. for 72 hours. After completion, water (200 mL) was added and the organic phase was separated. The aqueous layer was extracted with ethyl acetate (3×150 mL). The combined organic layer was dried over Na$_2$SO$_4$, filtered and concentrated. The residue was purified by prep-HPLC (column: Phenomenex luna c18 250 mm*100 mm*10 um; mobile phase: [water (0.225% FA)-ACN]; B %: 55ACN %-85ACN %, 16 min) affording the title compound (13 g, 55% yield). Brown solid; $^1$H NMR (400 MHz, CDCl$_3$) δ=7.30-7.22 (m, 1H), 7.17-7.07 (m, 2H), 7.01-6.93 (m, 1H), 5.33-5.23 (m, 2H), 3.56-3.53 (m, 3H), 2.97-2.82 (m, 1H), 2.07-1.62 (m, 2H); LCMS [ESI, M−31]: 243.1.

Step D. 1-(trans-2-fluorocyclopropyl)-2-(methoxymethoxy)benzene. To a solution of 1-(2-bromo-2-fluorocyclopropyl)-2-(methoxymethoxy)benzene (13 g, 47.3 mmol, 1.0 eq) in THF (130 mL) was added LiAlH$_4$ (5.38 g, 142 mmol, 3.0 eq) at 0° C. The mixture was stirred at 0-20° C. for 2 hours. Upon completion, the reaction mixture was quenched with saturated Na$_2$SO$_4$ aqueous solution (16.2 mL) and filtered. The filter cake was washed with THF (3×30 mL). The filtrate was combined and concentrated. The residue was purified by prep-HPLC (column: Phenomenex Synergi Max-RP 250*50 mm*10 um; mobile phase: [water (0.225% FA)-ACN]; B %: 38%-66%, 20 min) affording the cis isomer (4 g, 41% yield). Colorless oil; $^1$H NMR (400 MHz, CDCl$_3$) δ=7.25-7.18 (m, 2H), 7.12 (d, J=7.6 Hz, 1H), 7.02-6.96 (m, 1H), 5.26 (s, 2H), 4.97-4.73 (m, 1H), 3.53 (s, 3H), 2.33-2.19 (m, 1H), 1.36-1.12 (m, 2H); LCMS [ESI, M−31]: 165.2. And the title compound 2 (2.6 g, 27% yield). Colorless oil; $^1$H NMR (400 MHz, CDCl$_3$) δ=7.22-7.14 (m, 1H), 7.12-7.06 (m, 1H), 6.93 (td, J=1.2, 7.6 Hz, 1H), 6.78 (dd, J=1.6, 7.6 Hz, 1H), 5.26 (s, 2H), 4.77-4.51 (m, 1H), 3.53 (s, 3H), 2.73-2.58 (m, 1H), 1.55-1.42 (m, 1H), 1.16-1.05 (m, 1H); LCMS [ESI, M−31]: 165.2.

Step E. 2-(trans-2-fluorocyclopropyl)phenol. To a solution of 1-(trans-2-fluorocyclopropyl)-2-(methoxymethoxy)benzene (500 mg, 2.55 mmol, 1.0 eq) in MeCN (2.5 mL) was added HCl·dioxane (4 M, 5 mL, 7.85 eq). The mixture was stirred at 0° C. for 0.5 hour. Upon completion, the reaction mixture was concentrated. The pH of the residue was adjusted with saturated NaHCO$_3$ aqueous solution to ~7. The mixture was extracted with ethyl acetate (3×5 mL). The combined organic layers were dried over Na$_2$SO$_4$, filtered and concentrated affording the title compound (360 mg, crude). Yellow oil.

Step F. 2-(trans-2-fluorocyclopropyl)phenyl trifluoromethanesulfonate. To a solution of 2-(trans-2-fluorocyclopropyl)phenol (350.00 mg, 2.30 mmol, 1.0 eq), 4 Å molecular sieve (100 mg) and DIEA (1.19 g, 9.20 mmol, 1.60 mL, 4.0 eq) in dichloromethane (4 mL) was added Tf$_2$O (1.30 g, 4.60 mmol, 759 μL, 2.0 eq) at −40° C. The mixture was stirred at −40° C. for 0.5 hour. Upon completion, the reaction mixture was added water (5 mL) and separated. The aqueous layer was extracted with ethyl acetate (3×5 mL). The combined organic layer was dried over Na$_2$SO$_4$, filtered and concentrated. The residue was purified by column chromatography (SiO$_2$, petroleum ether: ethyl acetate=20:1-3:1) affording the title compound (450 mg, 68% yield). Yellow oil; $^1$H NMR (400 MHz, CDCl$_3$) δ=7.34-7.27 (m, 3H), 7.01-6.93 (m, 1H), 4.81-4.52 (m, 1H), 2.67-2.51 (m, 1H), 1.74-1.58 (m, 1H), 1.19-1.09 (m, 1H).

Step G. 2-(2-(trans-2-fluorocyclopropyl)phenyl)-4,4,5,5-tetramethyl-1,3,2-dioxaborolane. To a solution of 2-(trans-2-fluorocyclopropyl)phenyl trifluoromethanesulfonate (200 mg, 704 μmol, 1.0 eq), 4,4,5,5-tetramethyl-2-(4,4,5,5-tetramethyl-1,3,2-dioxaborolan-2-yl)-1,3,2-dioxaborolane (357 mg, 1.41 mmol, 2.0 eq) and KOAc (276 mg, 2.81 mmol, 4.0 eq) in dioxane (3 mL) was added Pd(dppf)Cl$_2$ (51.5 mg, 70.4 μmol, 0.1 eq). The mixture was stirred at 110° C. for 1 hour. Upon completion, the reaction mixture was added water (5 mL) and extracted with ethyl acetate (3×5 mL). The combined organic layer was dried over Na$_2$SO$_4$, filtered and concentrated. The residue was purified by reversed phase flash chromatography (C18, 0.1% formic acid condition) affording the title compound (160 mg, 87% yield). Yellow solid; $^1$H NMR (400 MHz, CDCl$_3$) δ=7.78 (dd, J=1.2, 7.6 Hz, 1H), 7.34 (dt, J=1.6, 7.6 Hz, 1H), 7.20 (dt, J=1.2, 7.2 Hz, 1H), 6.75 (d, J=8.0 Hz, 1H), 4.73-4.44 (m, 1H), 3.27-3.09 (m, 1H), 1.55-1.43 (m, 1H), 1.13-1.02 (m, 1H).

Step H. tert-butyl3-(8-fluoro-7-(2-(trans-2-fluorocyclopropyl)phenyl)-2-((hexahydro-1H-pyrrolizin-7a-yl)methoxy)pyrido[4,3-d]pyrimidin-4-yl)-3,8-diazabicyclo[3.2.1]octane-8-carboxylate. To a solution of (1R,5S)-tert-butyl 3-(7-chloro-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (220 mg, 413 μmol, 1.0 eq) and K$_3$PO$_4$ (1.5 M, 825 μL, 3.0 eq) in toluene (3 mL) were added Ad2nBuP-Pd-G3 (cataCXium® A Pd G3) (60.1 mg, 82.6 μmol, 0.2 eq) and 2-(2-((1S,2R)-2-fluorocyclopropyl)phenyl)-4,4,5,5-tetramethyl-1,3,2-dioxaborolane (200 mg, 763 μmol, 1.85 eq). The mixture was stirred at 90° C. for 1 hour. Upon completion, the reaction mixture was diluted with water (8 mL) and extracted with ethyl acetate (3×8 mL). The organic layer was combined, dried over Na$_2$SO$_4$, filtered and concentrated. The residue was purified by reversed phase flash chromatography (C18, 0.1% formic acid condition) affording the title compound (160 mg, 60% yield). Yellow solid; $^1$H NMR (400 MHz, CDCl$_3$) δ=9.03 (s, 1H), 7.46 (d, J=7.6 Hz, 1H), 7.42-7.31 (m, 2H), 7.02 (d, J=7.6 Hz, 1H), 4.65-4.26 (m, 5H), 4.24-4.15 (m, 2H), 3.80-3.55 (m, 2H), 3.19-3.05 (m, 2H), 2.73-2.59 (m, 2H), 2.58-2.45 (m, 1H), 2.17-2.06 (m, 2H), 2.00-1.93 (m, 2H), 1.93-1.83 (m, 4H), 1.81-1.75 (m, 2H), 1.72-1.64 (m, 2H), 1.53 (s, 9H), 1.42-1.30 (m, 1H), 1.06-0.96 (m, 1H); LCMS [ESI, M+1]: 633.5.

Step I. 4-((1R,5S)-3,8-diazabicyclo[3.2.1]octan-3-yl)-8-fluoro-7-(2-(trans-2-fluorocyclopropyl)phenyl)-2-((hexahydro-1H-pyrrolizin-7a-yl)methoxy)pyrido[4,3-d]pyrimidine. To a solution of tert-butyl3-(8-fluoro-7-(2-(trans-2-fluorocyclopropyl)phenyl)-2-((hexahydro-1H-pyrrolizin-7a-yl)methoxy)pyrido[4,3-d]pyrimidin-4-yl)-3,8-diazabicyclo[3.2.1]octane-8-carboxylate (150 mg, 237 μmol, 1.0 eq) in MeCN (1 mL) was added HCl·dioxane (4 M, 3 mL, 50.6 eq). The mixture was stirred at 10° C. for 0.5 hour. Upon completion, the reaction mixture was concentrated. The residue was purified by prep-HPLC (column: Unisil 3-100 C18 ultra 150*50 mm*3 um; mobile phase: [water (0.225% FA)-ACN]; B %: 1%-30%, 10 min) affording the title compound (5.44 mg, 4.2% yield). Yellow solid; $^1$H NMR (400 MHz, methanol-d4) δ=9.18 (s, 1H), 7.48-7.34 (m, 3H), 7.09 (d, J=7.6 Hz, 1H), 4.83-4.76 (m, 2H), 4.68 (s, 2H), 4.66-4.45 (m, 1H), 4.07 (br s, 2H), 3.96-3.87 (m, 2H), 3.76-3.65 (m, 2H), 3.31-3.25 (m, 2H), 2.40-2.28 (m, 3H), 2.28-2.16 (m, 4H), 2.15-2.03 (m, 4H), 2.01-1.94 (m, 2H), 1.38-1.25 (m, 1H), 1.15-1.06 (m, 1H); LCMS [ESI, M+1]: 533.3.

Example 286

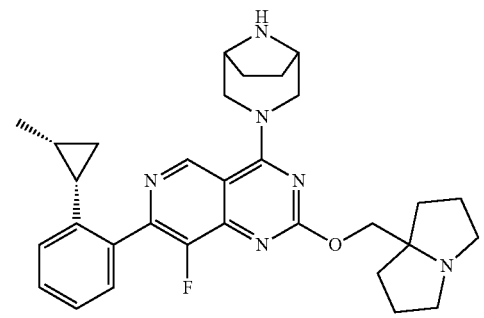 [SMILES: C[C@@H]1C[C@@H]1c1ccccc1-c1ncc2c(N3CC4CCC(C3)N4)nc(OCC34CCCN3CCC4)nc2c1F]

4-((1R,5S)-3,8-diazabicyclo[3.2.1]octan-3-yl)-8-fluoro-2-((hexahydro-1H-pyrrolizin-7a-yl)methoxy)-7-(2-((1S,2R)-2-methylcyclopropyl)phenyl)pyrido[4,3-d]pyrimidine

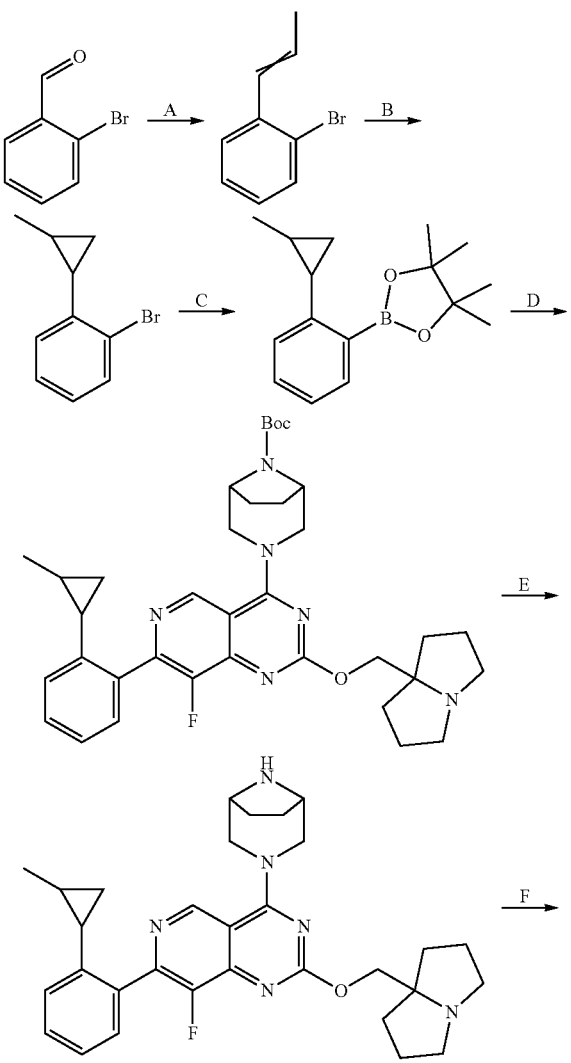

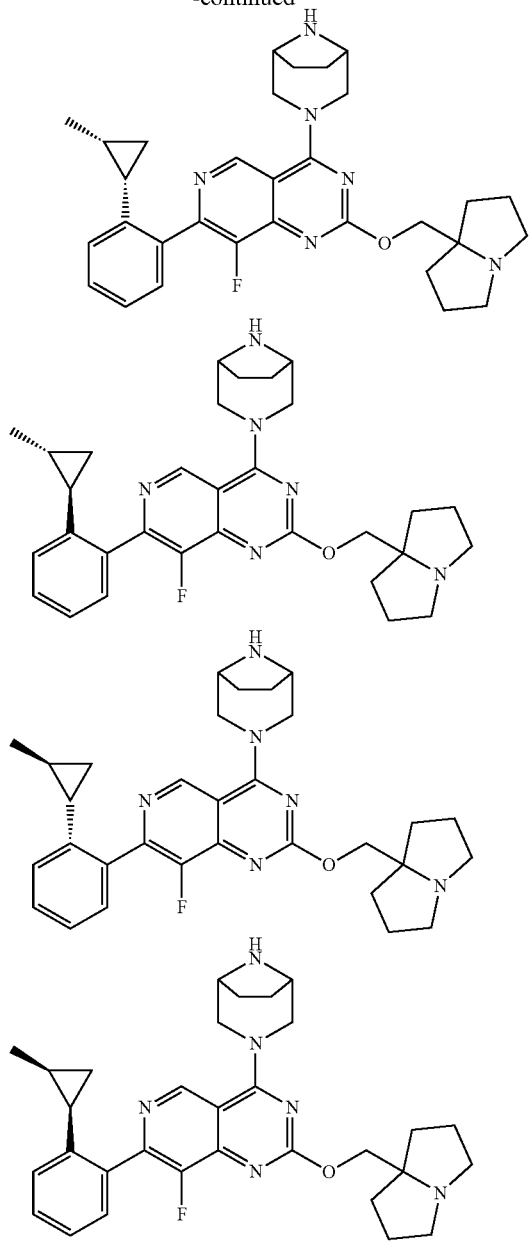

Step A. 1-bromo-2-(prop-1-en-1-yl) benzene. To a solution of ethyltriphenyl phosphonium bromide (55.4 g, 149 mmol, 1.38 eq) in THF (200 mL) was added t-BuOK (16.7 g, 149 mmol, 1.38 eq). The reaction mixture was stirred at 25° C. for 30 minutes. Then 2-bromobenzaldehyde (20 g, 108 mmol, 12.5 mL, 1 eq) was added to the reaction mixture. The solution was stirred at 25° C. for 3 hours. The reaction was concentrated under reduced pressure to remove THF. The residue was purified by silica gel chromatography (column height: 250 mm, diameter: 100 mm, 200-300 mesh silica gel, Petroleum ether/Ethyl acetate=1/0) to afford the title compound (12 g, crude). White oil. $^1$H NMR (400 MHz, CDCl$_3$-d) δ=7.62-7.52 (m, 1H), 7.52-7.25 (m, 2H), 7.14-7.04 (m, 1H), 6.78-6.47 (m, 1H), 6.25-5.86 (m, 1H), 1.94 (dd, J=1.6, 6.8 Hz, 1H), 1.80 (dd, J=1.6, 7.2 Hz, 2H).

Step B. 1-bromo-2-(2-methylcyclopropyl)benzene. To freshly distilled DCM (100 mL) was added ZnEt$_2$ (1 M, 96.4 mL, 2 eq) under N$_2$, and the solution was cooled to 0° C. Then TFA (11.0 g, 96.4 mmol, 7.14 mL, 2 eq) was added very slowly into the reaction via syringe. After the mixture was stirred for 20 minutes, CH$_2$I$_2$ (25.8 g, 96.4 mmol, 7.78 mL, 2 eq) was added. After an additional 20 minutes of stirring, 1-bromo-2-(prop-1-en-1-yl)benzene (9.50 g, 48.2 mmol, 1 eq) was added and stirred for 16 hours at 25° C. The mixture was poured into water (20 mL) and stirred for 10 minutes. The aqueous phase was extracted with ethyl acetate (3×20 mL). The combined organic phase was washed with brine (3×20 mL), dried with anhydrous Na$_2$SO$_4$, filtered and concentrated in vacuum. The residue was purified by silica gel chromatography (column height: 250 mm, diameter: 100 mm, 200-300 mesh silica gel, Petroleum ether/Ethyl acetate=1/0) to afford a residue. Then the residue was purified by prep-HPLC (TFA condition) to afford the title compound (1 g, 4.60 mmol, 10% yield). Yellow oil.

Step C. 4,4,5,5-tetramethyl-2-(2-(2-methylcyclopropyl)phenyl)-1,3,2-dioxaborolane. To a mixture of 1-bromo-2-(2-methylcyclopropyl)benzene (950 mg, 4.50 mmol, 1 eq) and 4,4,5-trimethyl-2-(4,4,5-trimethyl-1,3,2-dioxaborolan-2-yl)-1,3,2-dioxaborolane (1.52 g, 6.75 mmol, 1.5 eq) in dioxane (10 mL) were added AcOK (884 mg, 9.00 mmol, 2 eq) and Pd(dppf)Cl$_2$ (330 mg, 450 μmol, 0.1 eq) in one portion under N$_2$. The mixture was heated to 100° C. and stirred for 3 hours. After completion, the mixture was cooled to 25° C. and concentrated under reduced pressure at 40° C. The residue was poured into water (20 mL). The aqueous phase was extracted with ethyl acetate (3×20 mL). The combined organic phase was washed with brine (20 mL), dried with anhydrous Na$_2$SO$_4$, filtered and concentrated in vacuum. The residue was purified by prep-HPLC (FA condition) to afford the title compound (580 mg, crude). Brown oil; LCMS [ESI, M+3]: 259.2.

Step D. (1R,5S)-tert-butyl 3-(8-fluoro-2-((hexahydro-1H-pyrrolizin-7a-yl)methoxy)-7-(2-(2-methylcyclopropyl)phenyl)pyrido[4,3-d]pyrimidin-4-yl)-3,8-diazabicyclo[3.2.1]octane-8-carboxylate. To a mixture of (1R,5S)-tert-butyl 3-(7-chloro-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (454 mg, 852 μmol, 1 eq), dioxane (10 mL) and H$_2$O (2 mL) were added Pd(dppf)Cl$_2$ (62.4 mg, 85.2 μmol, 0.1 eq) and Cs$_2$CO$_3$ (555 mg, 1.70 mmol, 2 eq) in one portion at 25° C. under N$_2$. Then 4,4,5,5-tetramethyl-2-[2-(2-methylcyclopropyl)phenyl]-1,3,2-dioxaborolane (330 mg, 1.28 mmol, 1.5 eq) was added. The reaction was heated to 90° C. and stirred for 2 hours. The mixture was cooled to 25° C. and concentrated under reduced pressure at 40° C. The residue was poured into water (20 mL). The aqueous phase was extracted with ethyl acetate (3×20 mL). The combined organic phase was washed with brine (20 mL), dried with anhydrous Na$_2$SO$_4$, filtered and concentrated in vacuum. The residue was purified by prep-HPLC (FA condition) to give the title compound (270 mg, 46% yield). Brown Solid; LCMS [ESI, M−100]: 629.3

Step E. 4-((1R,5S)-3,8-diazabicyclo[3.2.1]octan-3-yl)-8-fluoro-2-((hexahydro-1H-pyrrolizin-7a-yl)methoxy)-7-(2-(2-methylcyclopropyl)phenyl)pyrido[4,3-d]pyrimidine. To a mixture of (1R,5S)-tert-butyl 3-(8-fluoro-2-((hexahydro-1H-pyrrolizin-7a-yl)methoxy)-7-(2-(2-methylcyclopropyl)phenyl)pyrido[4,3-d]pyrimidin-4-yl)-3,8-diazabicyclo[3.2.1]octane-8-carboxylate (270 mg, 429 μmol, 1 eq) in MeCN (5 mL) was added HCl·dioxane (4 M, 5 mL, 46.6 eq) at 0° C. and stirred at 20° C. for 1 hour. The mixture was concentrated in reduced pressure at 20° C. to give crude the title compound.

Step F. 4-((1R,5S)-3,8-diazabicyclo[3.2.1]octan-3-yl)-8-fluoro-2-((hexahydro-1H-pyrrolizin-7a-yl)methoxy)-7-(2-((1S,2R)-2-methylcyclopropyl)phenyl)pyrido[4,3-d]pyrimidine (Example 286). 4-((1R,5S)-3,8-diazabicyclo[3.2.1]octan-3-yl)-8-fluoro-2-((hexahydro-1H-pyrrolizin-7a-yl)methoxy)-7-(2-((1R,2R)-2-methylcyclopropyl)phenyl)pyrido[4,3-d]pyrimidine (Example 288). 4-((1R,5S)-3,8-diazabicyclo[3.2.1]octan-3-yl)-8-fluoro-2-((hexahydro-1H-pyrrolizin-7a-yl)methoxy)-7-(2-((1S,2S)-2-methylcyclopropyl)phenyl)pyrido[4,3-d]pyrimidine (Example 289). 4-((1R,5S)-3,8-diazabicyclo[3.2.1]octan-3-yl)-8-fluoro-2-((hexahydro-1H-pyrrolizin-7a-yl)methoxy)-7-(2-((1R,2S)-2-methylcyclopropyl)phenyl)pyrido[4,3-d]pyrimidine (Example 287). The mixture of stereoisomers was purified by SFC (column: DAICEL CHIRALCEL OD (250 mm*30 mm, 10 um); mobile phase: [0.1% $NH_3 \cdot H_2O$ IPA]; B %: 55%-55%, 50 min; 180 min) to afford Peak 3 (Rt=6.440) and Peak 4 (Rt=7.435), peak 3 was purified by prep-HPLC (column: Phenomenex Synergi C18 150*25*10 um; mobile phase: [water (0.225% FA)-ACN]; B %: 8%-38%, 8.5 min) to afford Example 289 (14.8 mg, 23.2 μmol, 5% yield). Off-white Gum; LCMS [ESI, M+1]: 529.2. $^1$H NMR (400 MHz, $CDCl_3$-d) δ=9.08 (s, 1H), 8.43 (s, 2H), 7.40-7.33 (m, 2H), 7.30-7.25 (m, 1H), 7.07 (d, J=7.2 Hz, 1H), 4.71-4.57 (m, 5H), 3.96-3.74 (m, 7H), 2.98-2.87 (m, 2H), 2.43-2.32 (m, 2H), 2.26-2.15 (m, 2H), 2.14-2.04 (m, 2H), 2.04-1.93 (m, 4H), 1.92-1.85 (m, 2H), 1.64-1.57 (m, 1H), 0.93 (m, 4H), 0.88-0.80 (m, 1H), 0.61-0.53 (m, 1H). Peak 4 was purified by prep-HPLC (column: Phenomenex Synergi C18 150*25*10 um; mobile phase: [water (0.225% FA)-ACN]; B %: 8%-38%, 8.5 min) to Example 287 (5.39 mg, 8.61 μmol, 2% yield). Off-white Gum; $^1$H NMR (400 MHz, $CDCl_3$-d) δ=9.05 (s, 1H), 8.47 (s, 1H), 7.45-7.40 (m, 1H), 7.38 (dd, J=1.6, 7.6 Hz, 1H), 7.36-7.30 (m, 1H), 7.28-7.25 (m, 1H), 4.64-4.56 (m, 4H), 3.91-3.66 (m, 6H), 2.89 (td, J=6.4, 11.2 Hz, 2H), 2.41-2.29 (m, 2H), 2.24-2.12 (m, 3H), 2.12-2.00 (m, 2H), 1.99-1.83 (m, 6H), 0.94-0.79 (m, 2H), 0.65 (d, J=6.0 Hz, 3H), 0.39 (q, J=5.2 Hz, 1H). LCMS [ESI, M+1]: 529.2. The other two peaks was purified by SFC (column: DAICEL CHIRALPAK IC (250 mm*30 mm, 10 um); mobile phase: [0.1% $NH_3 \cdot H_2O$ IPA]; B %: 25%-25%, 14.2 min; 241 min) to afford Peak 1 (Rt=3.964) and Peak 2 (Rt=5.402). Then Peak 1 was purified by prep-HPLC (column: Phenomenex Synergi C18 150*25*10 um; mobile phase: [water (0.225% FA)-ACN]; B %: 10%-40%, 8.5 min) to afford Example 286 (4.22 mg, 6.65 μmol, 2% yield). Yellow Gum; LCMS [ESI, M+1]: 529.2. $^1$H NMR (400 MHz, $CDCl_3$-d) δ=9.07 (s, 1H), 8.38 (br s, 2H), 7.46-7.31 (m, 3H), 7.29 (br s, 1H), 4.69-4.57 (m, 4H), 3.88-3.78 (m, 6H), 2.98-2.87 (m, 2H), 2.39 (m, 2H), 2.25-2.16 (m, 3H), 2.10 (m, 2H), 2.02-1.87 (m, 6H), 0.93-0.82 (m, 2H), 0.65 (d, J=6.0 Hz, 3H), 0.44-0.36 (m, 1H). Peak 2 was purified by prep-HPLC (column: Phenomenex Synergi C18 150*25*10 um; mobile phase: [water (0.225% FA)-ACN]; B %: 10%-40%, 8.5 min) to afford Example 288 (11.4 mg, 19.8 μmol, 5% yield), White Solid; LCMS [ESI, M+1]: 529.2; $^1$H NMR (400 MHz, $CDCl_3$-d) δ=9.05 (s, 1H), 7.40-7.33 (m, 2H), 7.29-7.25 (m, 1H), 7.06 (d, J=8.0 Hz, 1H), 4.65-4.36 (m, 4H), 3.74-3.36 (m, 6H), 2.85-2.70 (m, 2H), 2.32-2.19 (m, 2H), 2.05-1.94 (m, 4H), 1.81 (br s, 6H), 0.92 (d, J=1.6 Hz, 3H), 0.92-0.81 (m, 2H), 0.60-0.54 (m, 1H).

Example 287

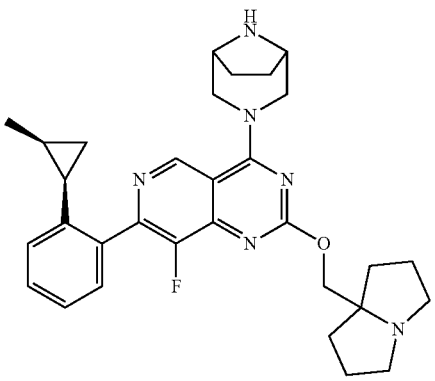 [SMILES: C[C@H]1C[C@H]1c1ccccc1-c1ncc2c(N3CC4CCC(C3)N4)nc(OCC34CCCN3CCC4)nc2c1F]

4-((1R,5S)-3,8-diazabicyclo[3.2.1]octan-3-yl)-8-fluoro-2-((hexahydro-1H-pyrrolizin-7a-yl)methoxy)-7-(2-((1R,2S)-2-methylcyclopropyl)phenyl)pyrido[4,3-d]pyrimidine See the synthesis of Example 286.

Example 288

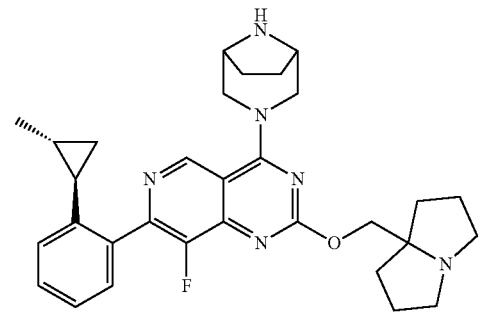 [SMILES: C[C@@H]1C[C@H]1c1ccccc1-c1ncc2c(N3CC4CCC(C3)N4)nc(OCC34CCCN3CCC4)nc2c1F]

4-((1R,5S)-3,8-diazabicyclo[3.2.1]octan-3-yl)-8-fluoro-2-((hexahydro-1H-pyrrolizin-7a-yl)methoxy)-7-(2-((1R,2R)-2-methylcyclopropyl)phenyl)pyrido[4,3-d]pyrimidine See the synthesis of Example 286.

Example 289

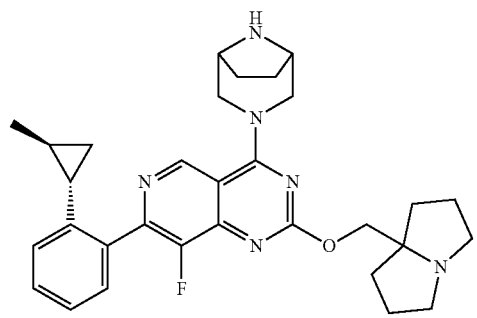 [SMILES: C[C@H]1C[C@@H]1c1ccccc1-c1ncc2c(N3CC4CCC(C3)N4)nc(OCC34CCCN3CCC4)nc2c1F]

4-((1R,5S)-3,8-diazabicyclo[3.2.1]octan-3-yl)-8-fluoro-2-((hexahydro-1H-pyrrolizin-7a-yl)methoxy)-7-(2-((1S,2S)-2-methylcyclopropyl)phenyl)pyrido[4,3-d]pyrimidine See the synthesis of Example 286.

Example 290

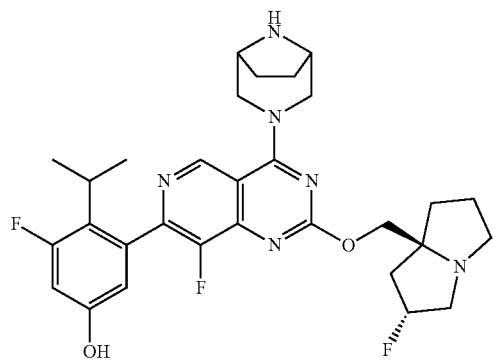 [SMILES: CC(C)c1c(F)cc(O)cc1-c1ncc2c(N3CC4CCC(C3)N4)nc(OC[C@@]34CCCN3C[C@H](F)C4)nc2c1F]

3-(4-((1R,5S)-3,8-diazabicyclo[3.2.1]octan-3-yl)-8-fluoro-2-(((2R,7aS)-2-fluorotetrahydro-1H-pyrrolizin-7a(5H)-yl)methoxy)pyrido[4,3-d]pyrimidin-7-yl)-5-fluoro-4-isopropylphenol

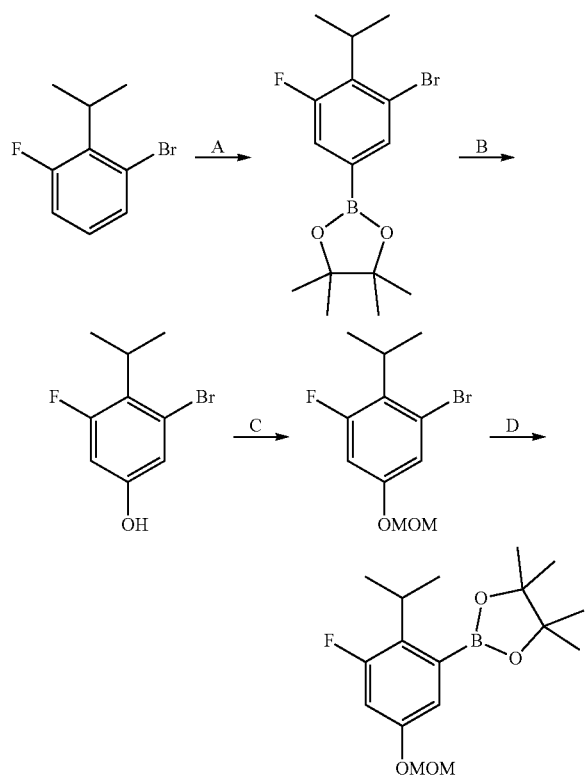

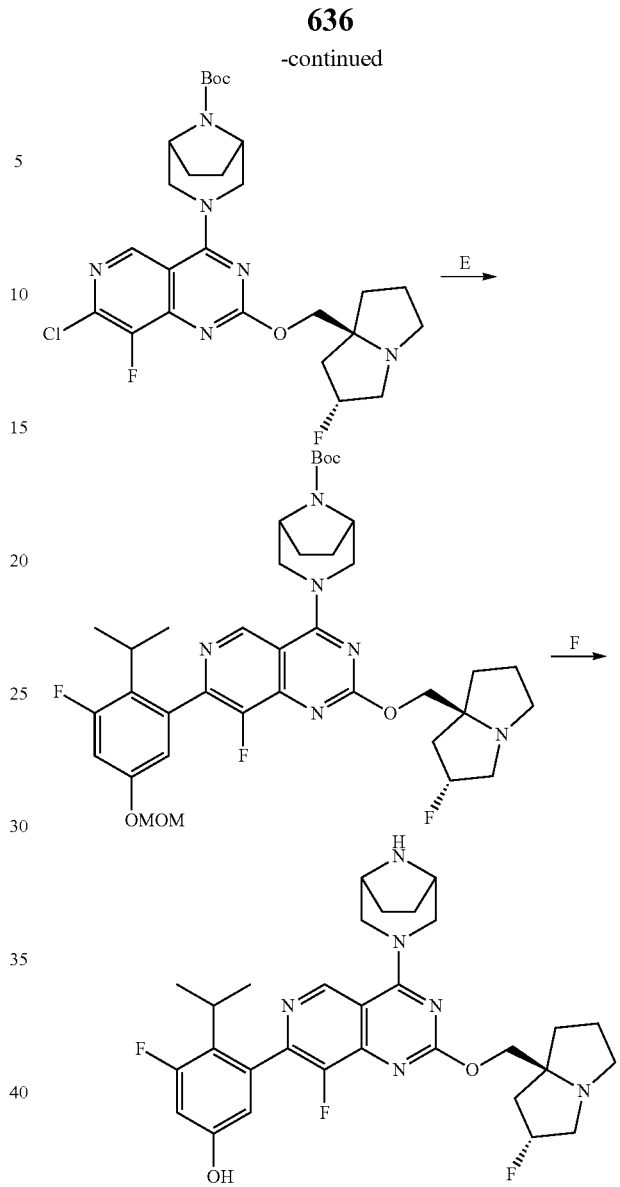

Step A. 2-(3-bromo-5-fluoro-4-isopropylphenyl)-4,4,5,5-tetramethyl-1,3,2-dioxaborolane. A mixture of 1-bromo-3-fluoro-2-isopropylbenzene (1.83 g, 8.43 mmol, 1.0 eq), 4,4,5,5-tetramethyl-1,3,2-dioxaborolane (3.24 g, 25.3 mmol, 3.67 mL, 3.0 eq), (Ir(OMe)(cod))$_2$ (559 mg, 843 μmol, 0.10 eq) and 4-tert-butyl-2-(4-tert-butyl-2-pyridyl)pyridine (271 mg, 1.01 mmol, 0.12 eq) in hexane (20 mL) was stirred at 60° C. for 2 hours under N$_2$. After completion, the mixture was concentrated under vacuum to give the title compound (14.77 g, crude). Brown oil.

Step B. 3-bromo-5-fluoro-4-isopropylphenol. To a mixture of 2-(3-bromo-5-fluoro-4-isopropylphenyl)-4,4,5,5-tetramethyl-1,3,2-dioxaborolane (14.8 g, crude) in H$_2$O (74 mL) and THF (148 mL) were added AcOH (77.7 g, 1.29 mol, 74 mL) and H$_2$O$_2$ (46.4 g, 409 mmol, 39.3 mL, 30% purity) at 0° C. The mixture was stirred at 15° C. for 0.5 hour. After completion, the mixture was quenched by saturated Na$_2$SO$_3$ solution (200 mL) and diluted with ethyl acetate (150 mL). The organic layer was separated. The aqueous phase was extracted with ethyl acetate (100 mL). The combined organic layer was washed with saturated brine (150 mL), dried over Na$_2$SO$_4$, filtered and concentrated under vacuum. The residue was purified by column chromatography (SiO₂, petroleum ether: ethyl acetate=20:1-10:1) to give the title compound (2.67 g, crude). Yellow oil; LCMS [ESI, M+1]: 233.1.

Step C. 1-bromo-3-fluoro-2-isopropyl-5-(methoxymethoxy)benzene. To a mixture of 3-bromo-5-fluoro-4-isopropylphenol (2.67 g, crude) in dichloromethane (30 mL) were added DIEA (4.44 g, 34.4 mmol, 5.99 mL) and MOMCl (1.63 g, 20.2 mmol, 1.54 mL) at 0° C. The mixture was stirred at 0° C. for 0.5 hour. After completion, the mixture was quenched with water (10 mL) then separated. The aqueous phase was extracted with dichloromethane (20 mL). The combined organic layer was washed with saturated brine (25 mL), dried over Na₂SO₄, filtered and concentrated under vacuum. The residue was purified by reversed phase flash chromatography [water (FA, 0.10%)/acetonitrile] to give the title compound (1.15 g, three steps 16% yield). Yellow oil; ¹H NMR (400 MHz, CDCl₃-d) δ=7.06 (br t, J=2.0, 1H), 6.71 (dd, J=2.4, 12.8 Hz, 1H), 5.12 (s, 2H), 3.47 (s, 3H), 3.46-3.40 (m, 1H), 1.32 (d, J=1.6 Hz, 3H), 1.30 (d, J=1.2 Hz, 3H).

Step D. 2-[3-fluoro-2-isopropyl-5-(methoxymethoxy)phenyl]-4,4,5,5-tetramethyl-1,3,2-dioxaborolane. To a mixture of 1-bromo-3-fluoro-2-isopropyl-5-(methoxymethoxy)benzene (600 mg, 2.17 mmol, 1.0 eq) and 4,4,5,5-tetramethyl-2-(4,4,5,5-tetramethyl-1,3,2-dioxaborolan-2-yl)-1,3,2-dioxaborolane (1.10 g, 4.33 mmol, 2.0 eq) in dioxane (12 mL) was added KOAc (637 mg, 6.50 mmol, 3.0 eq). The mixture was degassed, then Pd(dppf)Cl₂ (158 mg, 216 µmol, 0.10 eq) was added under N₂. The mixture was stirred at 110° C. for 1 hour under N₂. After completion, the mixture was diluted with ethyl acetate (10 mL) and water (15 mL) and the organic layer was separated. The aqueous phase was extracted with ethyl acetate (10 mL). The combined organic layer was washed with saturated brine (15 mL), dried over Na₂SO₄, filtered and concentrated under vacuum. The residue was purified by reversed phase flash chromatography [water (FA, 0.1%)/acetonitrile] to give the title compound (413 mg, 34%). Brown solid; ¹H NMR (400 MHz, CDCl₃-d) δ=7.10 (d, J=2.4 Hz, 1H), 6.79 (dd, J=2.8, 13.6 Hz, 1H), 5.14 (s, 2H), 3.62-3.52 (m, 1H), 3.47 (s, 3H), 1.35 (s, 12H), 1.32-1.31 (m, 3H), 1.31-1.29 (m, 3H).

Step E. tert-butyl (1R,5S)-3-(8-fluoro-7-(3-fluoro-2-isopropyl-5-(methoxymethoxy)phenyl)-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate. To a mixture of (1R,5S)-tert-butyl 3-(7-chloro-8-fluoro-2-(((2R,7aS)-2-fluorohexahydro-1H-pyrrolizin-7a-yl)methoxy)pyrido[4,3-d]pyrimidin-4-yl)-3,8-diazabicyclo[3.2.1]octane-8-carboxylate (150 mg, 272 µmol, 1.0 eq), 2-[3-fluoro-2-isopropyl-5-(methoxymethoxy)phenyl]-4,4,5,5-tetramethyl-1,3,2-dioxaborolane (176 mg, 544 µmol, 2 eq) and K₃PO₄ (1.5 M in H₂O, 544 µL, 3.0 eq) in toluene (3 mL) was added Ad₂nBuP-Pd-G3 (19.7 mg, 27.2 µmol, 0.10 eq) under N₂. The mixture was stirred at 90° C. for 1 hour under N₂. The mixture was diluted with ethyl acetate (6 mL) and water (8 mL), and then separated. The aqueous phase was extracted with ethyl acetate (8 mL). The combined organic layer was washed with saturated brine (8 mL), dried over Na₂SO₄, filtered and concentrated under vacuum. The residue was purified by reversed phase flash chromatography [water (FA, 0.1%)/acetonitrile] to give the title compound (59 mg, 30% yield). Yellow solid; LCMS [ESI, M/2+1, M+1]: 357.4, 713.3.

Step F. 3-(4-((1R,5S)-3,8-diazabicyclo[3.2.1]octan-3-yl)-8-fluoro-2-(((2R,7aS)-2-fluorotetrahydro-1H-pyrrolizin-7a(5H)-yl)methoxy)pyrido[4,3-d]pyrimidin-7-yl)-5-fluoro-4-isopropylphenol. To a mixture of tert-butyl (1R,5S)-3-(8-fluoro-7-(3-fluoro-2-isopropyl-5-(methoxymethoxy)phenyl)-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (45.0 mg, 63.1 µmol, 1.0 eq) in MeCN (0.5 mL) was added HCl·dioxane (4 M, 1 mL, 63 eq) at 10° C. The mixture was stirred at 10° C. for 0.5 hour. After completion, the mixture was concentrated under vacuum. Then the pH value was adjusted to 9 with saturated Na₂CO₃ solution and the mixture was filtered (solid was washed with methanol) and concentrated under vacuum. The residue was purified by prep-HPLC (column: Waters Xbridge C18 150*50 mm*10 um; mobile phase: [water (10 mM NH₄HCO₃)-ACN]; B %: 40%-70%, 10 min) to give the title compound (19.5 mg, 54% yield). White solid; ¹H NMR (400 MHz, methanol-d4) δ=9.03 (d, J=3.2 Hz, 1H), 6.61 (dt, J=2.8, 13.6 Hz, 1H), 6.55-6.50 (m, 1H), 5.30 (d, J=54.8 Hz, 1H), 4.64-4.57 (m, 2H), 4.31-4.20 (m, 2H), 3.72-3.61 (m, 4H), 3.29-3.18 (m, 3H), 3.06-2.97 (m, 1H), 2.68-2.60 (m, 1H), 2.33-2.13 (m, 3H), 1.99 (br s, 2H), 1.91-1.74 (m, 5H), 1.31-1.20 (m, 6H). ¹⁹F NMR (400 MHz, methanol-d4) δ=−113.963, −140.053, −173.647. SFC condition: "Column: Chiralcel OD-3 50×4.6 mm I.D., 3 um; Mobile phase: Phase A for CO₂, and Phase B for MeOH+ACN (0.05% DEA); Gradient elution: 50% MeOH+ACN (0.05% DEA) in CO₂; Flow rate: 3 mL/min; Detector: PDA; Column Temp: 35 C; Back Pressure: 100 Bar". LCMS [ESI, M/2+1, M+1]: 285.4, 569.2.

Example 291

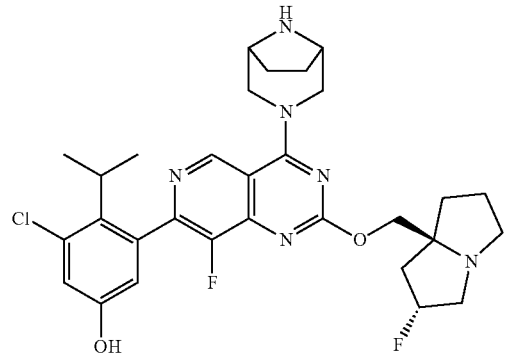 [SMILES: CC(C)c1c(Cl)cc(O)cc1-c1ncc2c(N3CC4CCC(C3)N4)nc(OC[C@@]34CCCN3C[C@H](F)C4)nc2c1F]

3-(4-((1R,5S)-3,8-diazabicyclo[3.2.1]octan-3-yl)-8-fluoro-2-(((2R,7aS)-2-fluorohexahydro-1H-pyrrolizin-7a-yl)methoxy)pyrido[4,3-d]pyrimidin-7-yl)-5-chloro-4-isopropylphenol

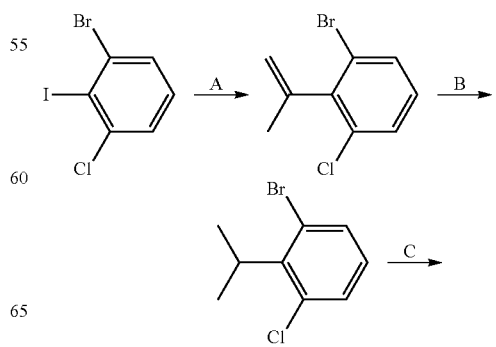

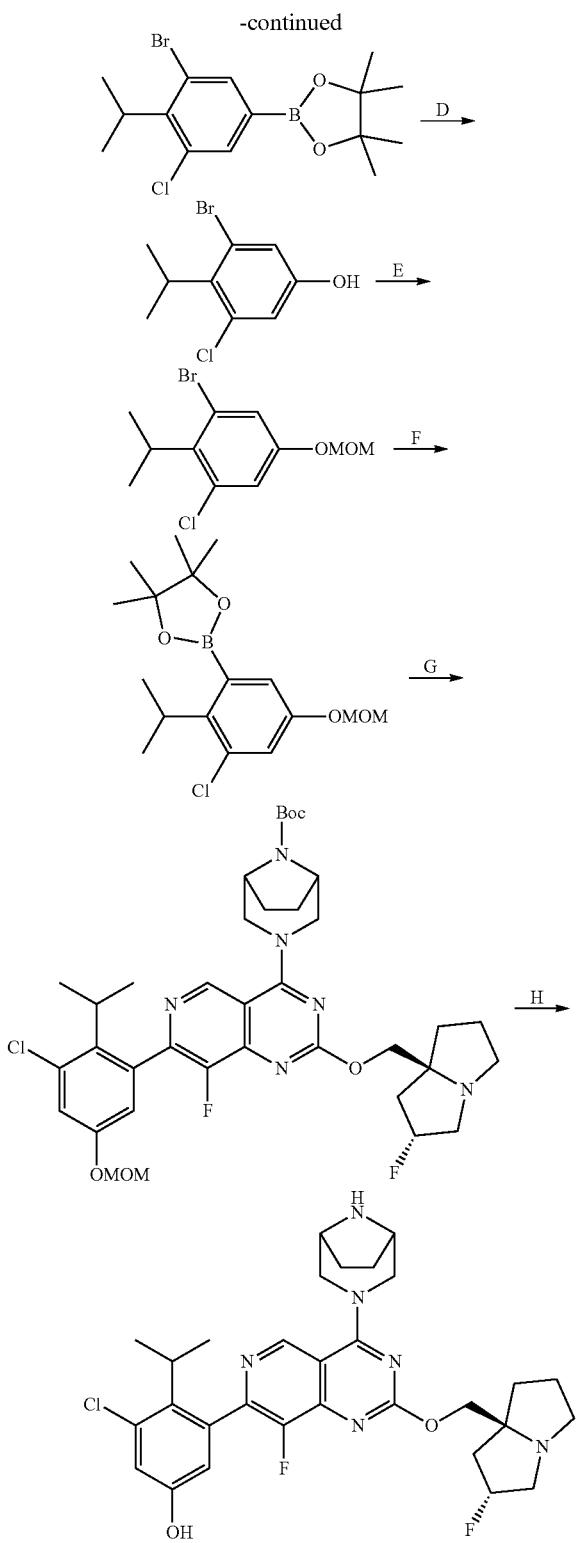

was diluted with water (50 mL) and extracted with ethyl acetate (3×50 mL). The combined organic layers were washed with brine (50 mL), dried over $Na_2SO_4$, filtered and concentrated under reduced pressure to give a residue. The residue was purified by column chromatography ($SiO_2$, petroleum ether) to give the title compound (2.7 g, 74% yield). Colourless oil, $^1$H NMR (400 MHz, chloroform-d) δ=7.50 (dd, J=0.8, 8.0 Hz, 1H), 7.35 (dd, J=0.8, 8.0 Hz, 1H), 7.05 (t, J=8.0 Hz, 1H), 5.40-5.34 (m, 1H), 4.92 (s, 1H), 2.07-2.02 (m, 3H).

Step B. 1-bromo-3-chloro-2-isopropylbenzene. To a solution of 1-bromo-3-chloro-2-(prop-1-en-2-yl)benzene (1 g, 4.32 mmol, 1.0 eq) in ethyl acetate (20 mL) was added $PtO_2$ (200 mg) under $N_2$. The suspension was degassed under vacuum and purged with $H_2$ several times. The mixture was stirred under $H_2$ (15 psi) at 20° C. for 0.5 hour. The mixture was concentrated under vacuum. The residue was purified by column chromatography ($SiO_2$, petroleum ether) to give the title compound (760 mg, 75% yield). Colourless oil; $^1$H NMR (400 MHz, methanol-d4) δ=7.57-7.49 (m, 1H), 7.39-7.29 (m, 1H), 7.03 (t, J=8.0 Hz, 1H), 3.92 (br s, 1H), 1.42 (d, J=7.2 Hz, 6H).

Step C. 2-(3-bromo-5-chloro-4-isopropylphenyl)-4,4,5,5-tetramethyl-1,3,2-dioxaborolane. A mixture of 1-bromo-3-chloro-2-isopropylbenzene (1 g, 4.28 mmol, 1.0 eq), 4,4,5,5-tetramethyl-1,3,2-dioxaborolane (1.64 g, 12.8 mmol, 1.86 mL, 3.0 eq), $(Ir(OMe)(cod))_2$ (170 mg, 256 μmol, 0.06 eq), 4-tert-butyl-2-(4-tert-butyl-2-pyridyl)pyridine (80.4 mg, 299 μmol, 0.07 eq) in hexane (20 mL) was degassed and purged with $N_2$ for 3 times. The mixture was stirred at 70° C. for 10 hours under $N_2$ atmosphere. The mixture was concentrated under vacuum to give the title compound (1.54 g, crude). Brown solid.

Step D. 3-bromo-5-chloro-4-isopropylphenol. To a solution of 2-(3-bromo-5-chloro-4-isopropylphenyl)-4,4,5,5-tetramethyl-1,3,2-dioxaborolane (2.4 g, 6.68 mmol, 1.0 eq) in THF (24 mL) and $H_2O$ (12 mL) were added AcOH (25.2 g, 419 mmol, 24 mL, 62.8 eq) and $H_2O_2$ (5.90 g, 52.0 mmol, 5 mL, 7.79 eq). The mixture was stirred at 0° C. for 0.5 hour. The reaction mixture was quenched with saturated $NaHSO_3$ solution (30 mL) and extracted with ethyl acetate (3×50 mL). The combined organic layers were washed with brine (30 mL), dried over $Na_2SO_4$, filtered and concentrated under reduced pressure to give the residue. The residue was purified by column chromatography ($SiO_2$, petroleum ether/ethyl acetate=50/1 to 5/1) to give the title compound (1 g, 60% yield). Colourless oil; $^1$H NMR (400 MHz, chloroform-d) δ=7.02 (d, J=2.4 Hz, 1H), 6.85 (s, 1H), 3.78 (br s, 1H), 1.39 (d, J=7.2 Hz, 6H).

Step E. 1-bromo-3-chloro-2-isopropyl-5-(methoxymethoxy)benzene. To a solution of 3-bromo-5-chloro-4-isopropylphenol (1 g, 4.01 mmol, 1.0 eq) in DCM (20 mL) were added DIEA (1.29 g, 10.0 mmol, 1.75 mL, 2.5 eq) and MOMCl (0.87 g, 10.8 mmol, 820 μL, 2.70 eq). The mixture was stirred at 0° C. for 0.5 hour. The reaction mixture was diluted with water (20 mL) and extracted with DCM (3×30 mL). The combined organic layers were washed with brine (20 mL), dried over $Na_2SO_4$, filtered and concentrated under reduced pressure to give a residue. The residue was purified by column chromatography ($SiO_2$, petroleum ether/ethyl acetate=100/1 to 5/1) to give the title compound (800 mg, 68% yield). Colourless oil; $^1$H NMR (400 MHz, DMSO-d6) δ=7.28 (d, J=2.0 Hz, 1H), 7.13 (br s, 1H), 5.22 (s, 2H), 3.74 (br s, 1H), 3.37 (s, 3H), 1.35 (d, J=7.2 Hz, 6H).

Step F. 2-(3-chloro-2-isopropyl-5-(methoxymethoxy)phenyl)-4,4,5,5-tetramethyl-1,3,2-dioxaborolane. A mixture Step A. 1-bromo-3-chloro-2-(prop-1-en-2-yl)benzene. A mixture of 1-bromo-3-chloro-2-iodo-benzene (5 g, 15.7 mmol, 1.0 eq), 2-isopropenyl-4,4,5,5-tetramethyl-1,3,2-dioxaborolane (2.91 g, 17.3 mmol, 1.1 eq), $Pd(dppf)Cl_2$ (576 mg, 787 μmol, 0.05 eq), $K_3PO_4$ (10.0 g, 47.2 mmol, 3.0 eq) in dioxane (90 mL) and $H_2O$ (30 mL) was degassed and purged with $N_2$ for 3 times. The mixture was stirred at 90° C. for 5 hours under $N_2$ atmosphere. The reaction mixture of 1-bromo-3-chloro-2-isopropyl-5-(methoxymethoxy) benzene (200 mg, 681 μmol, 1.0 eq), Pin2B2 (432 mg, 1.70 mmol, 2.5 eq), Pd(dppf)Cl$_2$ (49.8 mg, 68.1 μmol, 0.1 eq), KOAc (200 mg, 2.04 mmol, 3.0 eq) in dioxane (2 mL) was degassed and purged with N$_2$ for 3 times. Then the mixture was stirred at 110° C. for 1 hour under N$_2$ atmosphere. The reaction mixture was diluted with water (10 mL) and extracted with ethyl acetate (3×20 mL). The combined organic layers were washed with brine (20 mL), dried over Na$_2$SO$_4$, filtered and concentrated under reduced pressure to give a residue. The residue was purified by prep-TLC (SiO$_2$, petroleum ether/ethyl acetate=10/1) to give the title compound (130 mg, 56% yield). Colourless oil; $^1$H NMR (400 MHz, chloroform-d) δ=7.13 (d, J=2.8 Hz, 1H), 7.09 (d, J=2.8 Hz, 1H), 5.14 (s, 2H), 3.69-3.58 (m, 1H), 3.46 (s, 3H), 1.38 (s, 3H), 1.37 (s, 12H), 1.36 (s, 3H).

Step G. (1R,5S)-tert-butyl 3-(7-(3-chloro-2-isopropyl-5-(methoxymethoxy)phenyl)-8-fluoro-2-(((2R,7aS)-2-fluorohexahydro-1H-pyrrolizin-7a-yl)methoxy)pyrido[4,3-d]pyrimidin-4-yl)-3,8-diazabicyclo[3.2.1]octane-8-carboxylate. A mixture of tert-butyl (1R,5S)-3-(7-chloro-8-fluoro-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (40 mg, 72.5 μmol, 1.0 eq), 2-(3-chloro-2-isopropyl-5-(methoxymethoxy)phenyl)-4,4,5,5-tetramethyl-1,3,2-dioxaborolane (37.1 mg, 108 μmol, 1.5 eq), K$_3$PO$_4$ (1.5 M in H$_2$O, 145 μL, 3.0 eq), APhos Pd G3 (4.61 mg, 7.26 μmol, 0.1 eq) in toluene (2 mL) was degassed and purged with N$_2$ for 3 times. Then the mixture was stirred at 60° C. for 1 hour under N$_2$ atmosphere. The reaction mixture was diluted with water (10 mL) and extracted with ethyl acetate (3×10 mL). The combined organic layers were washed with brine (10 mL), dried over Na$_2$SO$_4$, filtered and concentrated under reduced pressure to give a residue. The residue was purified by reversed phase flash chromatography [water (0.1% formic acid)/acetonitrile)] to give the title compound (40 mg, 74% yield). Yellow solid; LCMS [ESI, M+1]: 729.5.

Step H. 3-(4-((1R,5S)-3,8-diazabicyclo[3.2.1]octan-3-yl)-8-fluoro-2-(((2R,7aS)-2-fluorohexahydro-1H-pyrrolizin-7a-yl)methoxy)pyrido[4,3-d]pyrimidin-7-yl)-5-chloro-4-isopropylphenol. To a solution of (1R,5S)-tert-butyl 3-(7-(3-chloro-2-isopropyl-5-(methoxymethoxy)phenyl)-8-fluoro-2-(((2R,7aS)-2-fluorohexahydro-1H-pyrrolizin-7a-yl)methoxy)pyrido[4,3-d]pyrimidin-4-yl)-3,8-diazabicyclo[3.2.1]octane-8-carboxylate (35 mg, 47.9 μmol, 1.0 eq) in ACN (0.5 mL) was added HCl·dioxane (4 M, 700 ul). The mixture was stirred at 20° C. for 0.5 hour. The mixture was concentrated under vacuum. The residue was diluted with saturated NaHCO$_3$ aqueous solution (0.5 mL) and purified by prep-HPLC (column: Waters Xbridge C18 150*50 mm*10 um; mobile phase: [water (10 mM NH$_4$HCO$_3$)-ACN]; B %: 30%-60%, 10 min). The desired fraction was collected and lyophilized to give the title compound (11.8 mg, 40% yield). White solid; $^1$H NMR (400 MHz, chloroform-d) δ=8.93 (s, 1H), 6.87 (d, J=2.4 Hz, 1H), 6.54 (d, J=2.4 Hz, 1H), 5.40-5.13 (m, 1H), 4.52 (br d, J=12.0 Hz, 2H), 4.20 (d, J=10.4 Hz, 1H), 4.14 (d, J=10.0 Hz, 1H), 3.72-3.52 (m, 4H), 3.31-3.10 (m, 3H), 3.04-2.86 (m, 2H), 2.27-2.09 (m, 3H), 2.00-1.74 (m, 7H), 1.24 (br d, J=6.8 Hz, 6H). LCMS [ESI, M+1]: 585.2.

Example 292

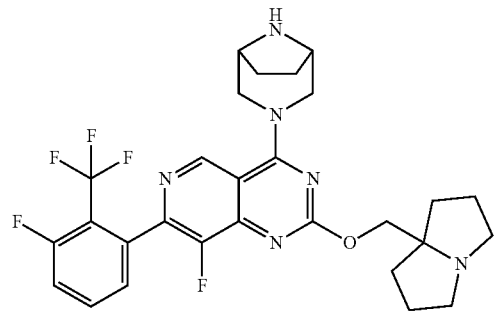 [SMILES: Fc1cccc(-c2ncc3c(N4CC5CCC(C4)N5)nc(OCC45CCCN4CCC5)nc3c2F)c1C(F)(F)F]

4-((1R,5S)-3,8-diazabicyclo[3.2.1]octan-3-yl)-8-fluoro-7-(3-fluoro-2-(trifluoromethyl)phenyl)-2-((tetrahydro-1H-pyrrolizin-7a(5H)-yl)methoxy)pyrido[4,3-d]pyrimidine

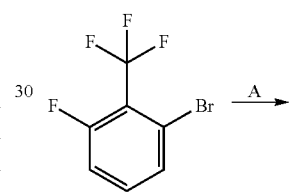

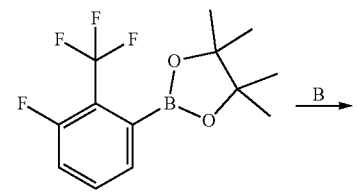

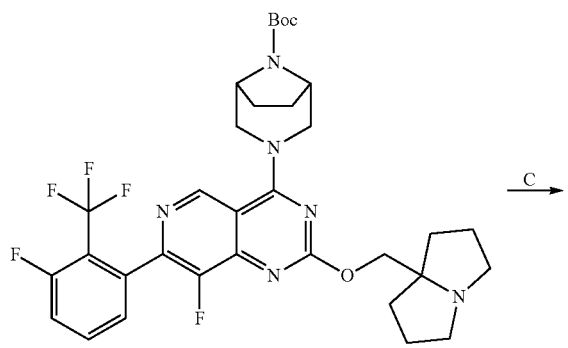

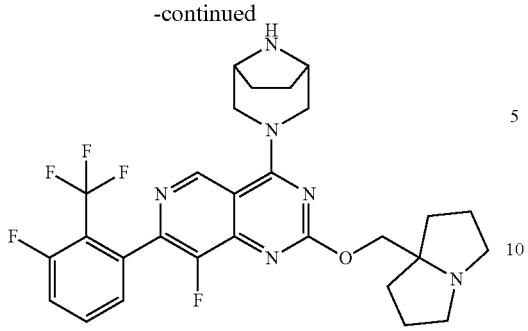

Step A. 2-[3-fluoro-2-(trifluoromethyl)phenyl]-4,4,5,5-tetramethyl-1,3,2-dioxaborolane. A mixture of 1-bromo-3-fluoro-2-(trifluoromethyl)benzene (1 g, 4.12 mmol, 1 eq), 4,4,5,5-tetramethyl-2-(4,4,5,5-tetramethyl-1,3,2-dioxaborolan-2-yl)-1,3,2-dioxaborolane (2.62 g, 10.3 mmol, 2.5 eq), KOAc (1.21 g, 12.4 mmol, 3 eq) and Pd(dppf)Cl$_2$ (301 mg, 412 μmol, 0.1 eq) in dioxane (10 mL) was stirred at 110° C. for 1 hour. After completion, the mixture was diluted with water (10 mL), extracted with ethyl acetate (2×10 mL), the combined organic layer was washed with brine (10 mL), dried over Na$_2$SO$_4$, filtered and concentrated under vacuum. The residue was purified by column chromatography (SiO$_2$, petroleum ether/ethyl acetate=10/1, Rf=0.42) to give the title compound (0.7 g, 59% yield). Yellow oil; $^1$H NMR (400 MHz, chloroform-d) δ=7.43 (dt, J=5.2, 7.6 Hz, 1H), 7.24 (d, J=7.2 Hz, 1H), 7.16-7.07 (m, 1H), 1.30 (s, 12H).

Step B. tert-butyl (1R,5S)-3-(8-fluoro-7-(3-fluoro-2-(trifluoromethyl)phenyl)-2-((tetrahydro-1H-pyrrolizin-7a(5H)-yl)methoxy)pyrido[4,3-d]pyrimidin-4-yl)-3,8-diazabicyclo[3.2.1]octane-8-carboxylate. A mixture of (1R,5S)-tert-butyl 3-(7-chloro-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (100 mg, 188 μmol, 1 eq), 2-[3-fluoro-2-(trifluoromethyl)phenyl]-4,4,5,5-tetramethyl-1,3,2-dioxaborolane (109 mg, 375 μmol, 2 eq), K$_3$PO$_4$ (1.5 M in H$_2$O, 375 μL, 3 eq) and [2-(2-aminophenyl)phenyl]palladium(1+); bis(1-adamantyl)-butyl-phosphane; methanesulfonate (13.7 mg, 18.8 μmol, 0.1 eq) in THF (2 mL) was stirred at 60° C. for 2 hours. After completion, the mixture was diluted with water (5.0 mL), extracted with ethyl acetate (2×5.0 mL). The combined organic layer was washed with brine (10 mL), dried over Na$_2$SO$_4$, filtered and concentrated under vacuum. The residue was purified by reversed phase flash chromatography [water (FA, 0.1%)/acetonitrile] to give the title compound (110 mg, 88% yield). Yellow oil; LCMS [ESI, M+1]: 661.3.

Step C. 4-((1R,5S)-3,8-diazabicyclo[3.2.1]octan-3-yl)-8-fluoro-7-(3-fluoro-2-(trifluoromethyl)phenyl)-2-((tetrahydro-1H-pyrrolizin-7a(5H)-yl)methoxy)pyrido[4,3-d]pyrimidine. A mixture of tert-butyl (1R,5S)-3-(8-fluoro-7-(3-fluoro-2-(trifluoromethyl)phenyl)-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (95 mg, 144 μmol, 1 eq) in HCl·dioxane (4 M, 2 mL, 55.6 eq) and acetonitrile (1 mL) was stirred at 25° C. for 0.5 hour. After completion, the mixture was concentrated under vacuum. The residue was purified by prep-HPLC (column: 3_Phenomenex Luna C18 75*30 mm*3 um; mobile phase: [water (0.225% FA)-ACN]; B %: 9%-29%, 8 min) to give the title compound (25.6 mg, 27% yield, 2FA). White solid; $^1$H NMR (400 MHz, methanol-d4) δ=9.14 (s, 1H), 7.82 (dt, J=5.2, 8.0 Hz, 1H), 7.59-7.48 (m, 1H), 7.36 (d, J=7.6 Hz, 1H), 4.77 (br d, J=13.2 Hz, 2H), 4.66 (s, 2H), 4.05 (br d, J=13.6 Hz, 2H), 3.95-3.84 (m, 2H), 3.75-3.66 (m, 2H), 3.30-3.24 (m, 2H), 2.39-2.30 (m, 2H), 2.27-1.94 (m, 10H); LCMS [ESI, M+1]: 561.3.

Example 293

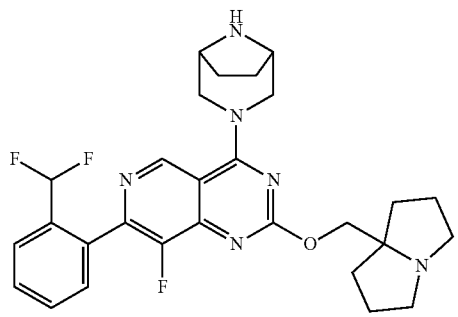 [SMILES: Fc1c(-c2ccccc2C(F)F)ncc2c(N3CC4CCC(C3)N4)nc(OCC34CCCN3CCC4)nc12]

4-((1R,5S)-3,8-diazabicyclo[3.2.1]octan-3-yl)-7-(2-(difluoromethyl)phenyl)-8-fluoro-2-((hexahydro-1H-pyrrolizin-7a-yl)methoxy)pyrido[4,3-d]pyrimidine

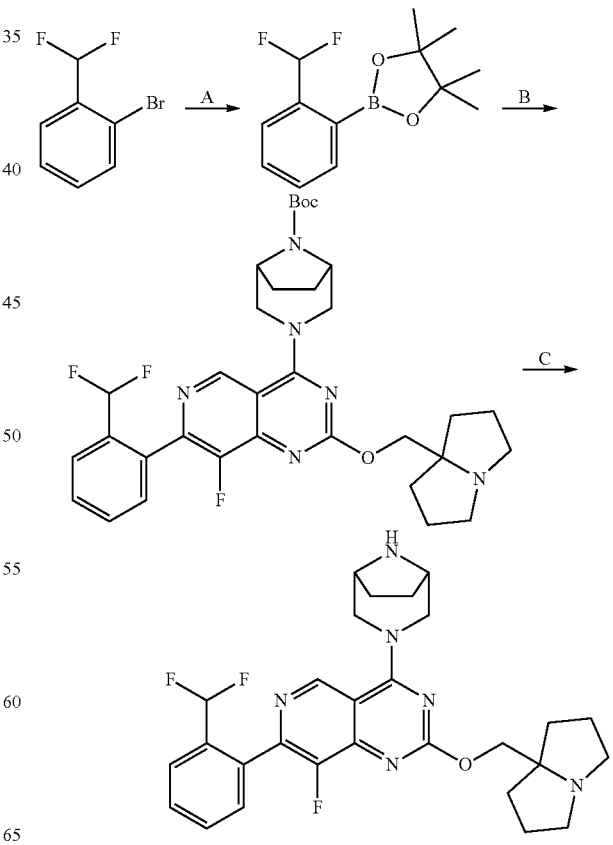

Step A. 2-(2-(difluoromethyl)phenyl)-4,4,5,5-tetramethyl-1,3,2-dioxaborolane. To the mixture of 1-bromo-2-(difluoromethyl)benzene (500 mg, 2.42 mmol, 1.0 eq), 4,4,5,5-tetramethyl-2-(4,4,5,5-tetramethyl-1,3,2-dioxaborolan-2-yl)-1,3,2-dioxaborolane (920 mg, 3.62 mmol, 1.5 eq), AcOK (711 mg, 7.24 mmol, 3.0 eq) in dioxane (4 mL) was added Pd(dppf)Cl₂ (177 mg, 242 μmol, 0.1 eq) under N₂, and the mixture was stirred at 100° C. for 3 hours. After completion, the reaction solution was diluted with ethyl acetate 8 mL, filtered, washed with brine 8 mL, and extracted with ethyl acetate 5 mL. The combined organic phase was dried over anhydrous sodium sulfate, filtered and concentrated. The residue was purified by reversed phase flash chromatography [water (FA 0.1%)/acetonitrile] to give the title compound (450 mg, 69% yield). Yellow Oil; ¹H NMR (400 MHz, chloroform-d) δ=7.78 (br d, J=7.2 Hz, 1H), 7.61 (d, J=7.6 Hz, 1H), 7.49-7.40 (m, 1H), 7.38-7.32 (m, 1H), 7.29-7.10 (m, 1H), 1.25 (s, 12H).

Step B. (1R,5S)-tert-butyl 3-(7-(2-(difluoromethyl)phenyl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate. To the solution of (1R,5S)-tert-butyl 3-(7-chloro-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (100 mg, 188 μmol, 1.0 eq), 2-(2-(difluoromethyl)phenyl)-4,4,5,5-tetramethyl-1,3,2-dioxaborolane (95.3 mg, 375 μmol, 2.0 eq), K₃PO₄ (1.5 M, 374 μL, 3.0 eq) in THF (1.5 mL) was added [2-(2-aminophenyl)phenyl]palladium(1+); bis(1-adamantyl)-butylphosphane; methanesulfonate (13.7 mg, 18.8 μmol, 0.1 eq) under N₂, the mixture was stirred at 60° C. for 2 hours. After completion, the mixture was diluted with Ethyl acetate 5 mL, and washed with saturated brine 5 mL. The aqueous layer was extracted with ethyl acetate 5 mL The combined organic phase was dried over anhydrous sodium sulfate, filtered and concentrated to give a residue. The residue was purified by reversed phase flash chromatography [water (FA 0.1%)/acetonitrile] to give the title compound (75.0 mg, 64% yield). Yellow Solid; LCMS [ESI, M+1]: 625.

Step C. 4-((1R,5S)-3,8-diazabicyclo[3.2.1]octan-3-yl)-7-(2-(difluoromethyl)phenyl)-8-fluoro-2-((hexahydro-1H-pyrrolizin-7a-yl)methoxy)pyrido[4,3-d]pyrimidine. To the solution of (1R,5S)-tert-butyl 3-(7-(2-(difluoromethyl)phenyl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (65.0 mg, 104 μmol, 1.0 eq) in ACN (1 mL) was added HCl/dioxane (4 M, 2 mL, 76.9 eq) at 0° C., the mixture was stirred at 0° C. for 1 hour. After completion, the mixture was concentrated at 25° C. The residue was purified by prep-HPLC (column: Unisil 3-100 C18 ultra 150*50 mm*3 um; mobile phase: [water (0.225% FA)-ACN]; B %: 1%-30%, 10 min) to give the title compound (31.45 mg, 49% yield, 2FA). Yellow Solid; ¹H NMR (400 MHz, chloroform-d) δ=9.05 (s, 1H), 7.87-7.82 (m, 1H), 7.60 (d, J=3.2 Hz, 3H), 7.15-6.86 (m, 1H), 4.67 (s, 2H), 4.61 (br d, J=12.4 Hz, 2H), 3.98-3.87 (m, 4H), 3.84-3.76 (m, 2H), 3.00-2.88 (m, 2H), 2.42-2.31 (m, 2H), 2.26-2.16 (m, 2H), 2.14-1.84 (m, 8H). LCMS [ESI, M+1]: 525.

Example 294

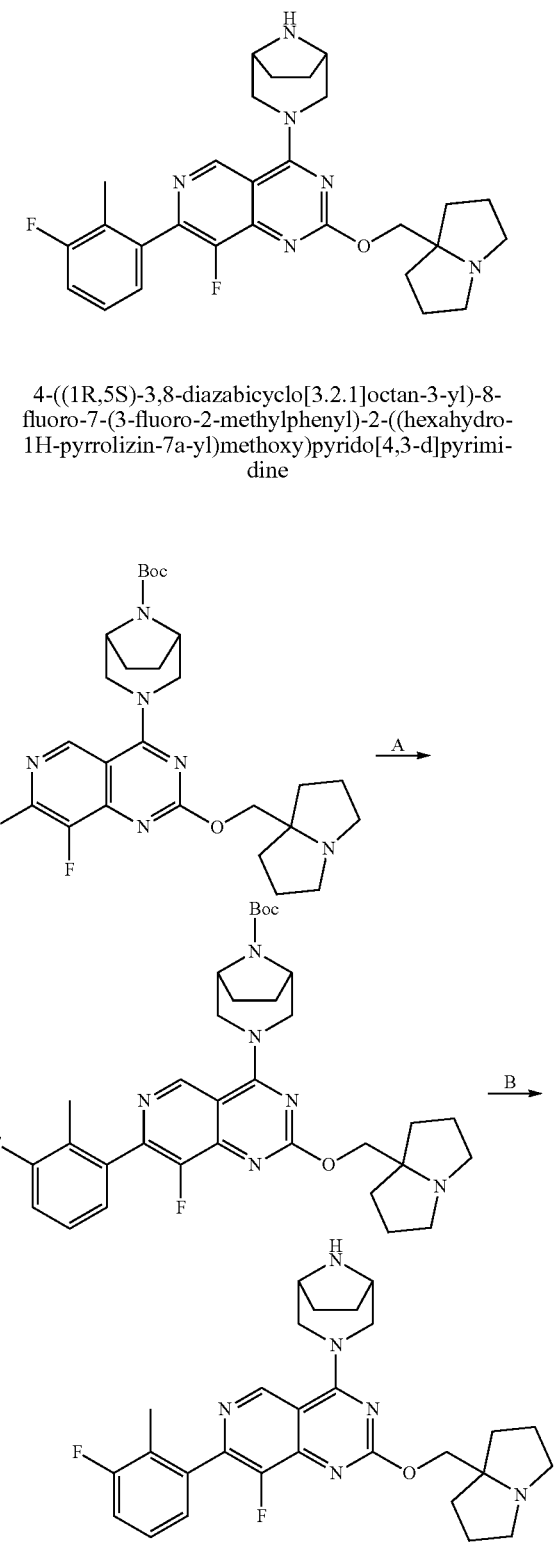

4-((1R,5S)-3,8-diazabicyclo[3.2.1]octan-3-yl)-8-fluoro-7-(3-fluoro-2-methylphenyl)-2-((hexahydro-1H-pyrrolizin-7a-yl)methoxy)pyrido[4,3-d]pyrimidine Step A. tert-butyl (1R,5S)-tert-butyl 3-(8-fluoro-7-(3-fluoro-2-methylphenyl)-2-((hexahydro-1H-pyrrolizin-7a-yl)methoxy)pyrido[4,3-d]pyrimidin-4-yl)-3,8-diazabicyclo[3.2.1]octane-8-carboxylate. A mixture of (1R,5S)-tert-butyl 3-(7-chloro-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (100 mg, 187 μmol, 1.0 eq), (3-fluoro-2-methyl-phenyl)boronic acid (43.3 mg, 281 μmol, 1.5 eq), K₃PO₄ (1.5 M in H₂O, 375 μL, 3.0 eq) and [2-(2-aminophenyl)phenyl]palladium(1+); bis(1-adamantyl)-butyl-phosphane; methanesulfonate (13.7 mg, 18.8 μmol, 0.1 eq) in THF (2 mL) was stirred at 60° C. for 2 hours. After completion, the mixture was diluted with water (5.0 mL), extracted with ethyl acetate (2×5 mL). The combined organic layer was washed with brine (10 mL), dried over Na₂SO₄, filtered and concentrated under vacuum. The residue was purified by reversed phase flash chromatography [water (FA, 0.1%)/acetonitrile] to give the title compound (105 mg, 91% yield). Yellow oil; LCMS [ESI, M+1]: 607.4.

Step B. 4-((1R,5S)-3,8-diazabicyclo[3.2.1]octan-3-yl)-8-fluoro-7-(3-fluoro-2-methylphenyl)-2-((hexahydro-1H-pyrrolizin-7a-yl)methoxy)pyrido[4,3-d]pyrimidine. A mixture of (1R,5S)-tert-butyl 3-(8-fluoro-7-(3-fluoro-2-methylphenyl)-2-((hexahydro-1H-pyrrolizin-7a-yl)methoxy)pyrido[4,3-d]pyrimidin-4-yl)-3,8-diazabicyclo[3.2.1]octane-8-carboxylate (95 mg, 157 μmol, 1.0 eq), HCl·dioxane (4 M, 2 mL, 51.1 eq) and acetonitrile (1 mL) was stirred at 25° C. for 0.5 hour. After completion, the mixture was concentrated under vacuum. The residue was purified by prep-HPLC (column: 3_Phenomenex Luna C18 75*30 mm*3 um; mobile phase: [water (0.225% FA)-ACN]; B %: 6%-26%, 8 min) to give the title compound (15.1 mg, 16% yield, 2FA). White solid; ¹H NMR (400 MHz, methanol-d4) δ=9.15 (s, 1H), 7.41-7.33 (m, 1H), 7.26-7.20 (m, 2H), 4.80 (br d, J=13.2 Hz, 2H), 4.67 (s, 2H), 4.09 (br s, 2H), 3.92 (br d, J=13.6 Hz, 2H), 3.75-3.66 (m, 2H), 3.30-3.26 (m, 2H), 2.39-2.30 (m, 2H), 2.26-2.05 (m, 11H), 2.02-1.95 (m, 2H); LCMS [ESI, M+1]: 507.3.

Example 295

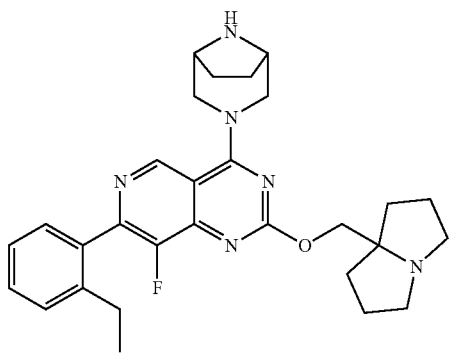 [SMILES: CCc1ccccc1-c1ncc2c(N3CC4CCC(C3)N4)nc(OCC34CCCN3CCC4)nc2c1F]

4-((1R,5S)-3,8-diazabicyclo[3.2.1]octan-3-yl)-7-(2-ethylphenyl)-8-fluoro-2-((hexahydro-1H-pyrrolizin-7a-yl)methoxy)pyrido[4,3-d]pyrimidine

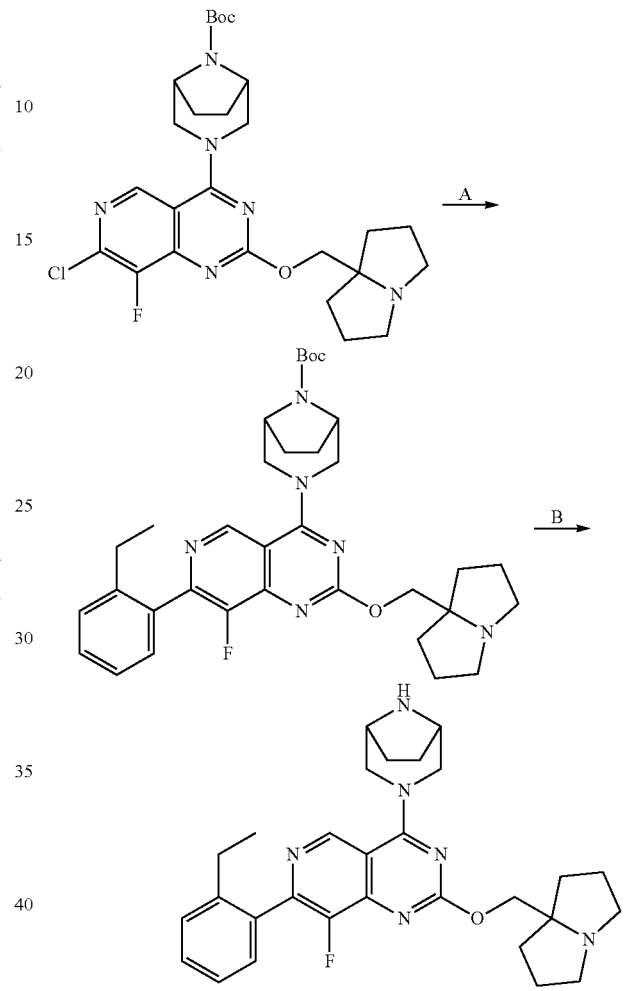

Step A. (tert-butyl (1R,5S)-3-(7-(2-ethylphenyl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate. To a mixture of (1R,5S)-tert-butyl 3-(7-chloro-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (100 mg, 188 μmol, 1.0 eq), (2-ethylphenyl)boronic acid (56.3 mg, 375 μmol, 2.0 eq) and K₃PO₄ (1.5 M, 375 μL, 3.0 eq) in THF (2.28 mL) was added [2-(2-aminophenyl)phenyl]palladium(1+); bis(1-adamantyl)-butyl-phosphane; methanesulfonate (13.7 mg, 18.8 μmol, 0.10 eq) under N₂. The mixture was stirred at 60° C. for 1 hour. After completion, the mixture was diluted with ethyl acetate (2 mL) and water (3 mL), and then separated. The aqueous phase was extracted with ethyl acetate (3 mL). The combined organic layer was washed with saturated brine (4 mL), dried over Na₂SO₄, filtered and concentrated under vacuum. The residue was purified by reversed phase flash chromatography [water (FA, 0.1%)/acetonitrile] to give the title compound (70 mg, 61% yield). Brown solid. LCMS [ESI, M/2+1, M+1]: 302.4, 603.4.

Step B. 4-((1R,5S)-3,8-diazabicyclo[3.2.1]octan-3-yl)-7-(2-ethylphenyl)-8-fluoro-2-((hexahydro-1H-pyrrolizin-7a- yl)methoxy)pyrido[4,3-d]pyrimidine. To a mixture of tert-butyl (1R,5S)-3-(7-(2-ethylphenyl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (65 mg, 108 μmol, 1.0 eq) in MeCN (1 mL) was added HCl·dioxane (4 M, 2 mL, 74 eq) at 0° C. The mixture was stirred at 0° C. for 0.5 hour. After completion, the mixture was concentrated under vacuum. The residue was purified by prep-HPLC (column: 3_Phenomenex Luna C18 75*30 mm*3 um; mobile phase: [water (0.225% FA)-ACN]; B %: 7%-27%, 8 min) to give the title compound (23.0 mg, 37% yield, 1.5 FA). Off-white solid. $^1$H NMR (400 MHz, methanol-d4) δ=9.14 (s, 1H), 7.49-7.41 (m, 2H), 7.37-7.31 (m, 2H), 4.84-4.78 (m, 2H), 4.68 (s, 2H), 4.13 (br s, 2H), 3.95 (br d, J=13.6 Hz, 2H), 3.76-3.68 (m, 2H), 3.31-3.25 (m, 2H), 2.60 (q, J=7.6 Hz, 2H), 2.39-2.31 (m, 2H), 2.28-2.16 (m, 4H), 2.15-2.07 (m, 4H), 2.05-1.98 (m, 2H), 1.08 (t, J=7.6 Hz, 3H). LCMS [ESI, M/2+1, M+1]: 252.3, 503.3.

Example 296

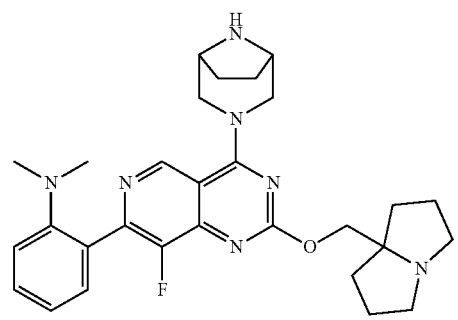 [SMILES: CN(C)c1ccccc1-c1ncc2c(N3CC4CCC(C3)N4)nc(OCC34CCCN3CCC4)nc2c1F]

2-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)-N,N-dimethylaniline

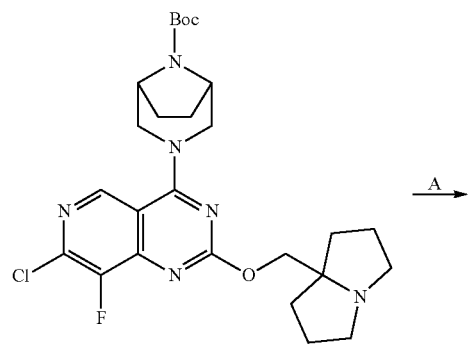

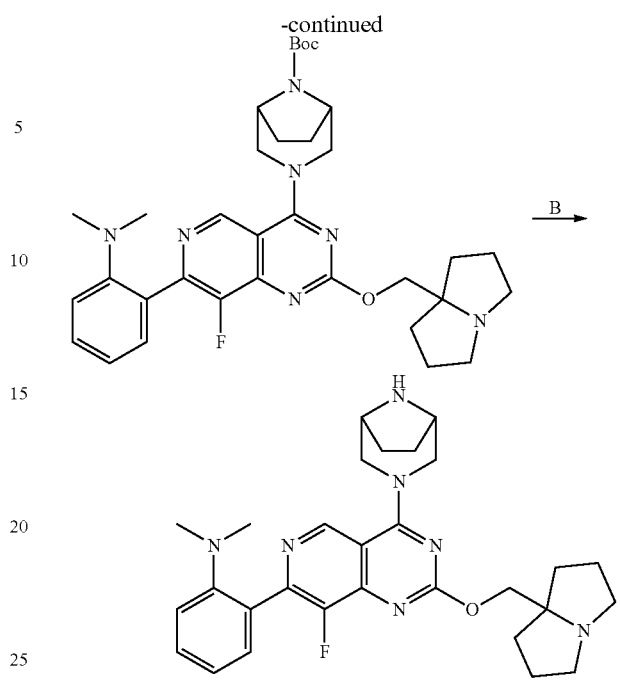

Step A. (1R,5S)-tert-butyl 3-(7-(2-(dimethylamino)phenyl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate. To a mixture of (1R,5S)-tert-butyl 3-(7-chloro-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (100 mg, 188 μmol, 1.0 eq), N,N-dimethyl-2-(4,4,5,5-tetramethyl-1,3,2-dioxaborolan-2-yl)aniline (92.7 mg, 375 μmol, 2.0 eq) and K$_3$PO$_4$ (1.5 M, 375 μL, 3.0 eq) in THF (2.28 mL) was added [2-(2-aminophenyl)phenyl]palladium(1+); bis(1-adamantyl)-butyl-phosphane; methanesulfonate (13.7 mg, 18.8 μmol, 0.10 eq) under N$_2$. The mixture was stirred at 60° C. for 1 hour. After completion, the mixture was diluted with ethyl acetate (2 mL) and water (3 mL), and the organic layer was separated. The aqueous phase was extracted with ethyl acetate (3 mL). The combined organic layer was washed with saturated brine (4 mL), dried over Na$_2$SO$_4$, filtered and concentrated under vacuum. The residue was purified by reversed phase flash chromatography [water (FA, 0.1%)/acetonitrile] to give the title compound (96 mg, 82% yield). Yellow solid. LCMS [ESI, M/2+1, M+1]: 309.9, 618.4.

Step B. 2-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)-N,N-dimethylaniline. To a mixture of (1R,5S)-tert-butyl 3-(7-(2-(dimethylamino)phenyl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (91.0 mg, 147 μmol, 1.0 eq) in MeCN (1 mL) was added HCl·dioxane (4 M, 2 mL, 54.0 eq) at 0° C. The mixture was stirred at 0° C. for 0.5 hour. After completion, the mixture was concentrated under vacuum. The residue was purified by prep-HPLC (column: 3_Phenomenex Luna C18 75*30 mm*3 um; mobile phase: [water (0.225% FA)-ACN]; B %: 0%-20%, 8 min) to give the title compound (19.4 mg, 21% yield, 2FA). Yellow solid. $^1$H NMR (400 MHz, methanol-d4) δ=9.14 (s, 1H), 7.48-7.41 (m, 1H), 7.33 (dd, J=1.2, 7.6 Hz, 1H), 7.23 (d, J=7.6 Hz, 1H), 7.10 (td, J=0.8, 7.6 Hz, 1H), 4.80 (br d, J=13.2 Hz, 2H), 4.67 (s, 2H), 4.13 (br s, 2H), 3.94 (br d, J=13.6 Hz, 2H), 3.76-3.66 (m, 2H), 3.30-3.25 (m, 2H), 2.56 (s, 6H), 2.38-2.31 (m, 2H), 2.28-2.16 (m, 4H), 2.15-2.06 (m, 4H), 2.04-1.97 (m, 2H). LCMS [ESI, M/2+1, M+1]: 259.9, 518.3.

Example 297

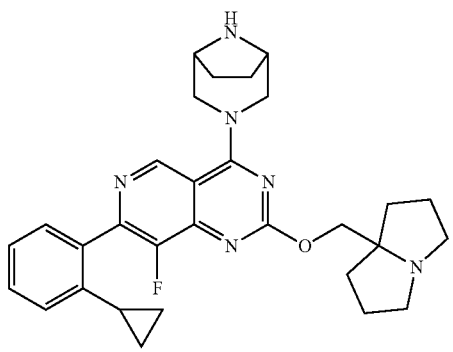 [SMILES: Fc1c(-c2ccccc2C2CC2)ncc2c(N3CC4CCC(C3)N4)nc(OCC34CCCN3CCC4)nc12]

4-((1R,5S)-3,8-diazabicyclo[3.2.1]octan-3-yl)-7-(2-cyclopropylphenyl)-8-fluoro-2-((hexahydro-1H-pyrrolizin-7a-yl)methoxy)pyrido[4,3-d]pyrimidine

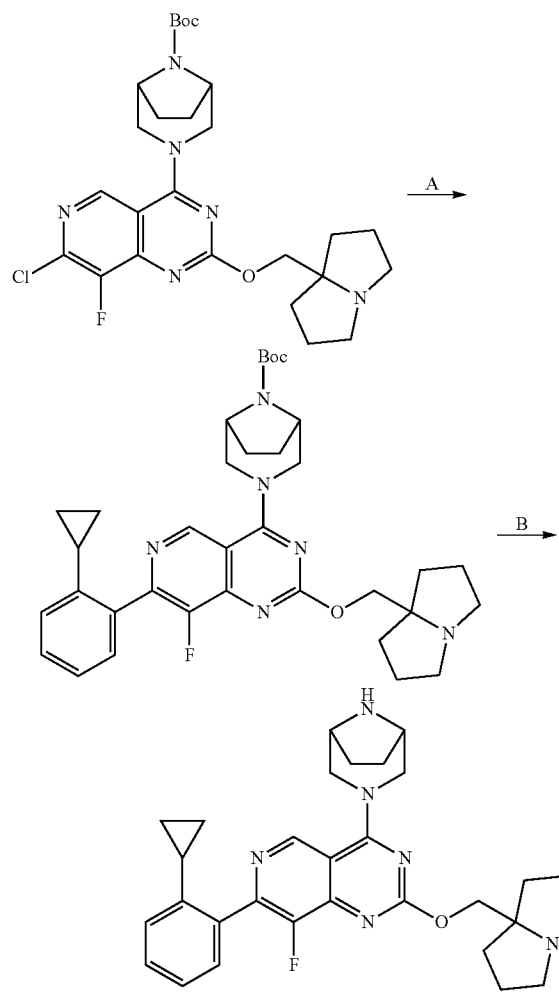

Step A. (1R,5S)-tert-butyl 3-(7-(2-cyclopropylphenyl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate. To the mixture of (1R,5S)-tert-butyl 3-(7-chloro-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (100 mg, 188 µmol, 1.0 eq), (2-cyclopropylphenyl)boronic acid (61.0 mg, 377 µmol, 2.01 eq) in THF (1.5 mL) were added K$_3$PO$_4$ (1.5 M, 374 µL, 2.99 eq) and [2-(2-aminophenyl)phenyl]palladium(1+); bis(1-adamantyl)-butyl-phosphane; methanesulfonate (13.7 mg, 18.8 µmol, 0.1 eq) under N$_2$, and the mixture was stirred at 60° C. for 2 hours. After completion, the reaction solution was diluted with water (5 mL), and extracted with ethyl acetate (5 mL×2). The combined organic phase was washed with brine, dried over anhydrous sodium sulfate, filtered and concentrated to give a residue. The residue was purified by reversed phase flash chromatography [water (FA 0.1%)/acetonitrile] to give the title compound (70.0 mg, 61% yield). Yellow Solid. LCMS [ESI, M+1]: 615.4.

Step B. 4-((1R,5S)-3,8-diazabicyclo[3.2.1]octan-3-yl)-7-(2-cyclopropylphenyl)-8-fluoro-2-((hexahydro-1H-pyrrolizin-7a-yl)methoxy)pyrido[4,3-d]pyrimidine. To the solution of (1R,5S)-tert-butyl 3-(7-(2-cyclopropylphenyl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (60.0 mg, 97.6 µmol, 1.0 eq) in ACN (1 mL) was added HCl·dioxane (4 M, 2.0 mL, 82.0 eq) at 0° C., and the mixture was stirred at 0° C. for 0.5 hour. After completion, the mixture was concentrated at 20° C. to give a residue. The residue was purified by prep-HPLC (column: Unisil 3-100 C18 ultra 150*50 mm*3 um; mobile phase: [water (0.225% FA)-ACN]; B %: 3%-33%, 10 min) to give the title compound (29.45 mg, 51% yield). White Solid. $^1$H NMR (400 MHz, CHLOROFORM-d) δ=9.08 (s, 1H), 8.43 (br s, 2H), 7.42-7.34 (m, 2H), 7.29 (d, J=7.6 Hz, 1H), 7.06 (d, J=8.0 Hz, 1H), 4.65 (s, 2H), 4.61 (br d, J=12.4 Hz, 2H), 3.94-3.70 (m, 6H), 2.98-2.83 (m, 2H), 2.43-2.28 (m, 2H), 2.26-2.14 (m, 2H), 2.14-2.04 (m, 2H), 1.92-1.84 (m, 2H), 2.02-1.84 (m, 5H), 0.87-0.73 (m, 2H), 0.69-0.57 (m, 2H). LCMS [ESI, M+1]: 515.3.

Example 298

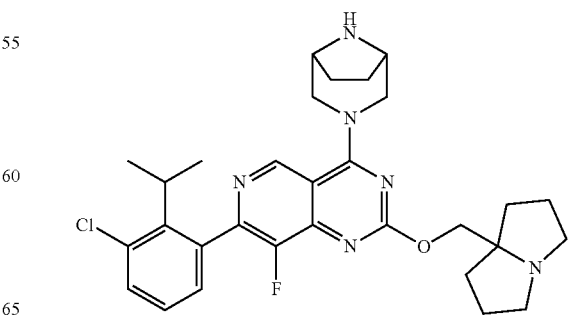

4-((1R,5S)-3,8-diazabicyclo[3.2.1]octan-3-yl)-7-(3-chloro-2-isopropylphenyl)-8-fluoro-2-((hexahydro-1H-pyrrolizin-7a-yl)methoxy)pyrido[4,3-d]pyrimidine

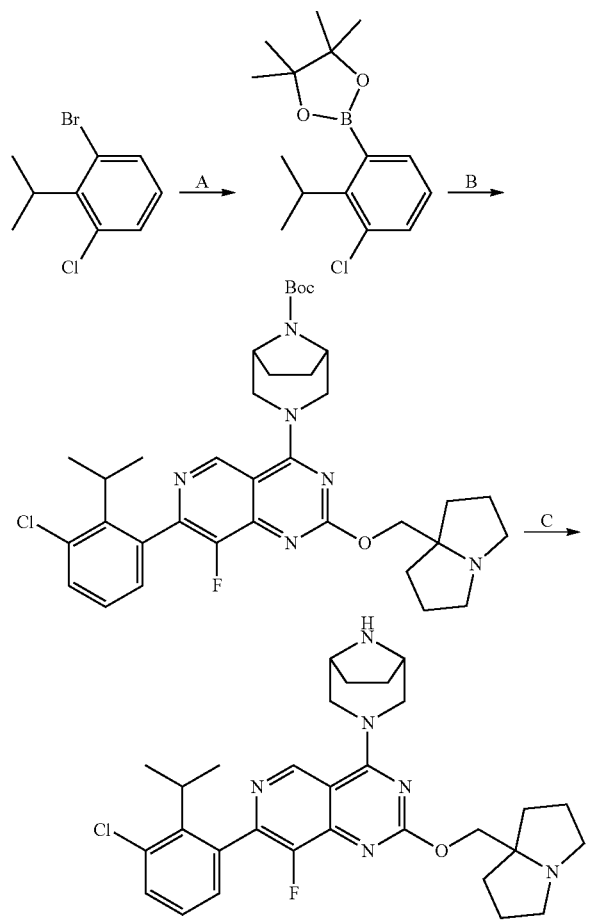

Step A. 2-(3-chloro-2-isopropyl-phenyl)-4,4,5,5-tetramethyl-1,3,2-dioxaborolane. To a mixture of 1-bromo-3-chloro-2-isopropylbenzene (500 mg, 2.14 mmol, 1.0 eq), 4,4,4',4',5,5,5',5'-octamethyl-2,2'-bi(1,3,2-dioxaborolane) (1.36 g, 5.35 mmol, 2.5 eq) and KOAc (630 mg, 6.42 mmol, 3.0 eq) in dioxane (10 mL) was added Pd(dppf)Cl$_2$ (156 mg, 214 μmol, 0.1 eq) in one portion at 20° C. under N$_2$. The mixture was stirred at 100° C. for 2 hours. Upon completion, the reaction mixture was diluted with water (20 mL) and extracted with ethyl acetate (3×30 mL). The combined organic layers were washed with brine (60 mL), dried over Na$_2$SO$_4$, filtered and concentrated under reduced pressure. The residue was purified by column chromatography (SiO$_2$, PE/EA=1/0 to 50/1) to give the title compound (300 mg, 50% yield); Yellow oil. $^1$H NMR (400 MHz, CDCl$_3$-d) δ=7.50-7.45 (m, 1H), 7.38-7.34 (m, 1H), 7.09 (t, J=7.6 Hz, 1H), 3.78-3.66 (m, 1H), 1.40 (d, J=7.2 Hz, 6H), 1.37 (s, 12H).

Step B. tert-butyl (1R,5S)-3-(7-(3-chloro-2-isopropylphenyl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate. To a mixture of (1R,5S)-tert-butyl 3-(7-chloro-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (200 mg, 375 μmol, 1.0 eq) and 2-(3-chloro-2-isopropyl-phenyl)-4,4,5,5-tetramethyl-1,3,2-dioxaborolane (158 mg, 563 μmol, 1.5 eq) in THF (4 mL) were added [2-(2-aminophenyl)phenyl]palladium (1+); bis(1-adamantyl)-butyl-phosphane; methanesulfonate (54.7 mg, 75 μmol, 0.2 eq) and tripotassium; phosphate (1.5 M, 750 μL, 3.0 eq) in one portion at 25° C. under N$_2$. The mixture was stirred at 60° C. for 2 hours. Upon completion, the reaction mixture was diluted with H$_2$O (20 mL) and extracted with ethyl acetate (3×20 mL). The combined organic layers were washed with brine (40 mL), dried over Na$_2$SO$_4$, filtered and concentrated under reduced pressure to give a residue. The residue was purified by reversed phase flash chromatography [water (0.1% formic acid)/acetonitrile] to give the title compound (180 mg, 74% yield); Yellow solid; LCMS [ESI, M+1]:651.3.

Step C. 4-((1R,5S)-3,8-diazabicyclo[3.2.1]octan-3-yl)-7-(3-chloro-2-isopropylphenyl)-8-fluoro-2-((hexahydro-1H-pyrrolizin-7a-yl)methoxy)pyrido[4,3-d]pyrimidine. To a mixture of tert-butyl (1R,5S)-3-(7-(3-chloro-2-isopropylphenyl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (80 mg, 123 μmol, 1.0 eq) in ACN (0.5 mL) was added HCl·dioxane (4 M, 0.5 mL, 16 eq) in one portion at 0° C. under N$_2$. The mixture was stirred at 20° C. for 0.5 hour. Upon completion, the mixture was concentrated. Then the residue was basified to pH~8 with saturated NaHCO$_3$ aqueous solution and extracted with DCM (3×15 mL). The combined organic layers were washed with brine (15 mL), dried over Na$_2$SO$_4$, filtered and concentrated. The residue was purified by prep-HPLC (column: Phenomenex Gemini NX—C18 (75*30 mm*3 um); mobile phase: [water (10 mM NH$_4$HCO$_3$)-ACN]; B %: 24%-54%, 8 min). The desired fraction was collected and concentrated under vacuum to remove acetonitrile. The mixture was lyophilized to give the title compound (17.3 mg, 25% yield); White solid; $^1$H NMR (400 MHz, CDCl$_3$-d) δ=8.99 (s, 1H), 7.47-7.41 (m, 1H), 7.25-7.18 (m, 1H), 7.18-7.13 (m, 1H), 4.58 (br d, J=12.0 Hz, 2H), 4.19 (s, 2H), 3.72-3.58 (m, 4H), 3.19-3.07 (m, 3H), 2.71-2.60 (m, 2H), 2.16-2.06 (m, 2H), 1.99-1.81 (m, 7H), 1.75-1.60 (m, 3H), 1.33 (br d, J=6.8 Hz, 6H). LCMS [ESI, M+1]:551.3.

Example 299

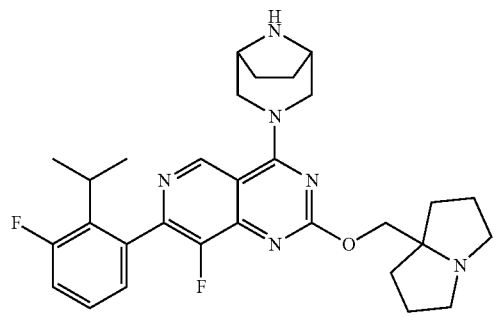 [SMILES: CC(C)c1c(F)cccc1-c1ncc2c(N3CC4CCC(C3)N4)nc(OCC34CCCN3CCC4)nc2c1F]

4-((1R,5S)-3,8-diazabicyclo[3.2.1]octan-3-yl)-8-fluoro-7-(3-fluoro-2-isopropylphenyl)-2-((hexahydro-1H-pyrrolizin-7a-yl)methoxy)pyrido[4,3-d]pyrimidine

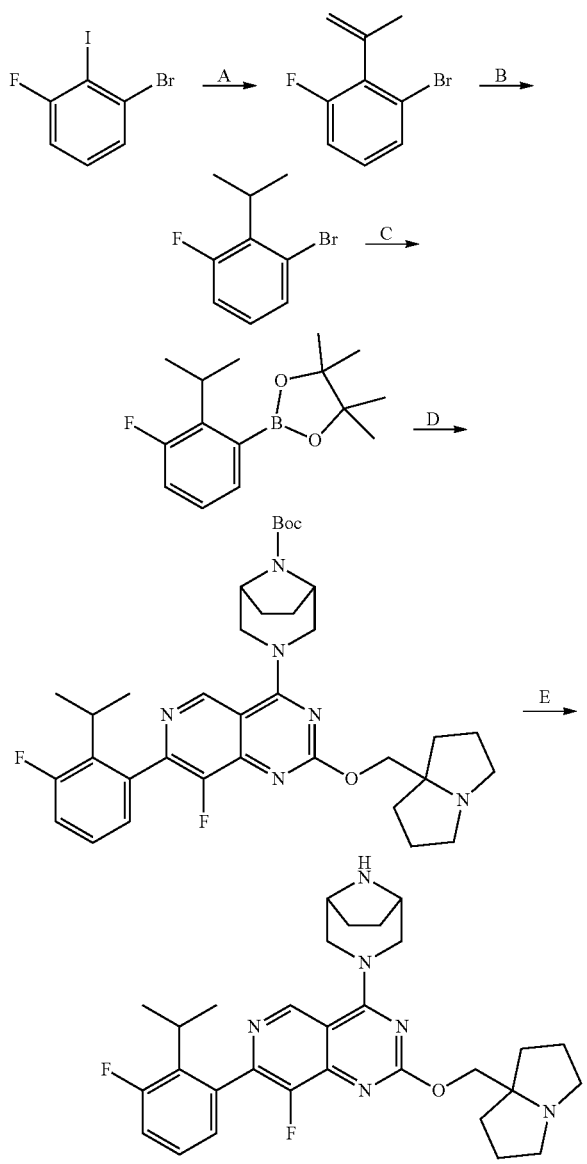

Step A. 1-bromo-3-fluoro-2-isopropenyl-benzene. A mixture of 1-bromo-3-fluoro-2-iodo-benzene (4.5 g, 14.96 mmol, 1 eq), 2-isopropenyl-4,4,5,5-tetramethyl-1,3,2-dioxaborolane (2.77 g, 16.5 mmol, 1.1 eq), $K_3PO_4$ (9.53 g, 44.9 mmol, 3 eq) and Pd(dppf)Cl$_2$ (1.09 g, 1.50 mmol, 0.1 eq) in dioxane (60 mL) and H$_2$O (15 mL) was stirred at 100° C. for 2 hours under N$_2$. After completion, the mixture was diluted with water (50 mL), and extracted with ethyl acetate (2×50 mL). The combined organic layer was washed with brine (50 mL), dried over Na$_2$SO$_4$, filtered and concentrated under vacuum. The residue was purified by column chromatography (SiO$_2$, ethyl acetate/petroleum ether=0/1) to give the title compound (2.6 g, 81% yield). Yellow oil. Rf=0.77 (0:1, ethyl acetate/petroleum ether). $^1$H NMR (400 MHz, CDCl$_3$-d) δ=7.41-7.35 (m, 1H), 7.11 (dt, J=6.0, 8.0 Hz, 1H), 7.06-7.00 (m, 1H), 5.43-5.37 (m, 1H), 4.98 (s, 1H), 2.05 (s, 3H).

Step B. 1-bromo-3-fluoro-2-isopropyl-benzene. To a mixture of 1-bromo-3-fluoro-2-isopropenyl-benzene (2.60 g, 12.1 mmol, 1.0 eq) in ethyl acetate (60 mL) was added PtO$_2$ (260 mg) under N$_2$. The mixture was stirred at 25° C. under 15 psi of H$_2$ for 3.5 hours. After completion, the reaction mixture was filtered and concentrated in vacuum to give the title compound (2.43 g, 92% yield) which was used in the next step without further purification. Yellow oil. Rf=0.9 (0:1, ethyl acetate/petroleum ether). $^1$H NMR (400 MHz, CDCl$_3$-d) δ=7.35-7.32 (m, 1H), 7.04-6.93 (m, 2H), 3.60-3.48 (m, 1H), 1.36 (d, J=1.6 Hz, 3H), 1.34 (d, J=1.6 Hz, 3H).

Step C. 2-(3-fluoro-2-isopropyl-phenyl)-4,4,5,5-tetramethyl-1,3,2-dioxaborolane. To a mixture of 1-bromo-3-fluoro-2-isopropyl-benzene (500 mg, 2.30 mmol, 1.0 eq), 4,4,5,5-tetramethyl-2-(4,4,5,5-tetramethyl-1,3,2-dioxaborolan-2-yl)-1,3,2-dioxaborolane (1.17 g, 4.61 mmol, 2.0 eq) and KOAc (678 mg, 6.91 mmol, 3.0 eq) in dioxane (10 mL) was added Pd(dppf)Cl$_2$ (168 mg, 230 μmol, 0.10 eq) under N$_2$. The mixture was stirred at 110° C. for 1.5 hours under N$_2$. After completion, the mixture was diluted with ethyl acetate (8 mL) and water (10 mL). and then the organic layer was separated. The aqueous phase was extracted with ethyl acetate (2×8 mL). The combined organic layer was washed with saturated brine (15 mL), dried over Na$_2$SO$_4$, filtered and concentrated under vacuum. The residue was purified by column chromatography (SiO$_2$, petroleum ether: ethyl acetate=30:1-20:1) to give the title compound (240 mg, 37% yield). Yellow oil. Rf=0.7 (10:1, petroleum ether/ethyl acetate). $^1$H NMR (400 MHz, CDCl$_3$-d) δ=7.46-7.43 (m, 1H), 7.14 (dt, J=5.2, 7.6 Hz, 1H), 7.04 (ddd, J=1.2, 8.0, 12.0 Hz, 1H), 3.69-3.59 (m, 1H), 1.36-1.35 (m, 15H), 1.33 (d, J=1.6 Hz, 3H).

Step D. tert-butyl (1R,5S)-3-(8-fluoro-7-(3-fluoro-2-isopropylphenyl)-2-((tetrahydro-1H-pyrrolizin-7a(5H)-yl)methoxy)pyrido[4,3-d]pyrimidin-4-yl)-3,8-diazabicyclo[3.2.1]octane-8-carboxylate. A mixture of (1R,5S)-tert-butyl 3-(7-chloro-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (260 mg, 488 μmol, 1.0 eq), 2-(3-fluoro-2-isopropyl-phenyl)-4,4,5,5-tetramethyl-1,3,2-dioxaborolane (193 mg, 732 μmol, 1.5 eq), K$_3$PO$_4$ (1.5 M, 975 μL, 3.0 eq) and [2-(2-aminophenyl)phenyl]palladium(1+); bis(1-adamantyl)-butyl-phosphane; methanesulfonate (35.5 mg, 48.8 μmol, 0.10 eq) in THF (4 mL) was stirred at 60° C. for 1 hour under N$_2$. After completion, the mixture was concentrated under vacuum. The residue was purified by reversed phase flash chromatography [water (FA, 0.1%)/acetonitrile] to give the title compound (256 mg, 83% yield). Yellow solid. LCMS [ESI, M+1]: 635.3.

Step E. 4-((1R,5S)-3,8-diazabicyclo[3.2.1]octan-3-yl)-8-fluoro-7-(3-fluoro-2-isopropylphenyl)-2-((tetrahydro-1H-pyrrolizin-7a(5H)-yl)methoxy)pyrido[4,3-d]pyrimidine. To a mixture of tert-butyl (1R,5S)-3-(8-fluoro-7-(3-fluoro-2-isopropylphenyl)-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (100 mg, 157 μmol, 1.0 eq) in MeCN (1 mL) was added HCl·dioxane (4 M, 2 mL, 51 eq) at 0° C. The mixture was stirred at 0° C. for 0.5 hour. After completion, the mixture was concentrated under vacuum. The residue was purified by prep-HPLC (column: Shimpack C18 150*25*10 um; mobile phase: [water (0.225% FA)-ACN]; B %: 12%-32%, 9 min) to give the title compound (53.0 mg, 55% yield, FA). Yellow solid. $^1$H NMR (400 MHz, METHANOL-d4) δ=9.14 (s, 1H), 7.36 (td, J=5.2, 8.0 Hz, 1H), 7.24-7.18 (m, 1H), 7.13 (d, J=7.6 Hz, 1H), 4.82 (br d, J=13.2 Hz, 2H), 4.68 (s, 2H), 4.12 (br s, 2H), 3.95 (br d, J=13.6 Hz, 2H), 3.72 (m, 2H), 3.34-3.26 (m, 2H), 2.79 (m, 1H), 2.39-2.30 (m, 2H), 2.28-2.17 (m, 4H), 2.16-2.05 (m, 4H), 2.04-1.97 (m, 2H), 1.31 (s, 3H), 1.29 (s, 3H). LCMS [ESI, M/2+1, M+1]: 268.4, 535.3.

Example 300

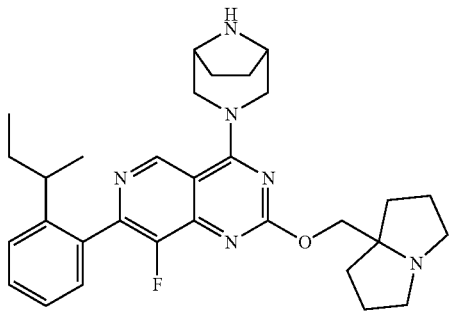 [SMILES: CCC(C)c1ccccc1-c1ncc2c(N3CC4CCC(C3)N4)nc(OCC34CCCN3CCC4)nc2c1F]

4-((1R,5S)-3,8-diazabicyclo[3.2.1]octan-3-yl)-7-(2-(sec-butyl)phenyl)-8-fluoro-2-((hexahydro-1H-pyrrolizin-7a-yl)methoxy)pyrido[4,3-d]pyrimidine

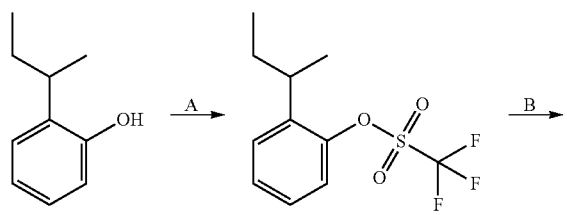

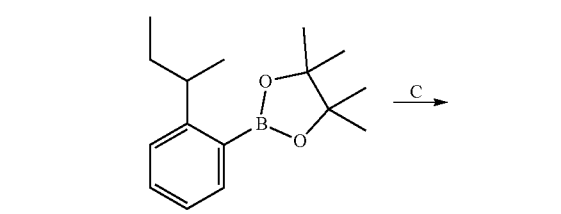

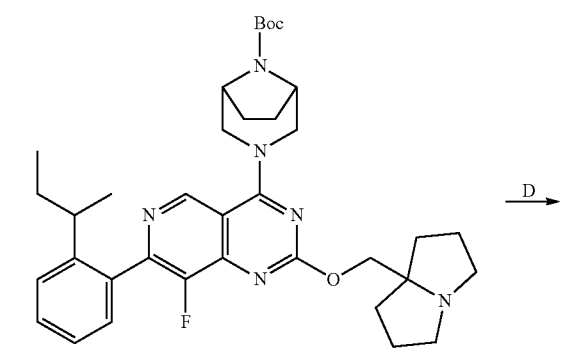

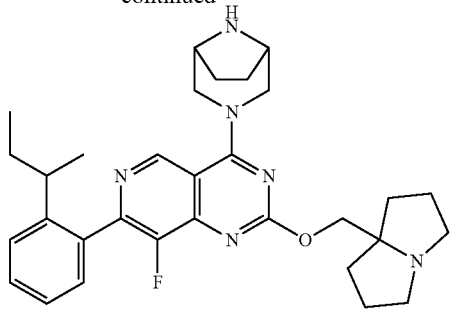

Step A. 2-(sec-butyl)phenyl trifluoromethanesulfonate. To a mixture of 2-(sec-butyl)phenol (1.0 g, 6.66 mmol, 1.0 eq) in dichloromethane (30 mL) was added DIEA (3.44 g, 26.6 mmol, 4.64 mL, 4.0 eq) and Tf$_2$O (2.82 g, 9.99 mmol, 1.65 mL, 1.5 eq) at −40° C. The mixture was stirred at −40° C. for 0.5 hour. After completion, the mixture was quenched by H$_2$O (10 mL) and separated. The aqueous phase was extracted with dichloromethane (10 mL). The combined organic layer was washed with saturated brine (20 mL), dried over Na$_2$SO$_4$, filtered and concentrated under vacuum. The residue was purified by column chromatography (SiO$_2$, petroleum ether/ethyl acetate=5/1) to give the title compound (1.78 g, 95% yield). Colorless oil. Rf=0.7 (5:1, petroleum ether/ethyl acetate). $^1$H NMR (400 MHz, CHLOROFORM-d) δ=7.39-7.31 (m, 2H), 7.29-7.22 (m, 2H), 3.05 (m, 1H), 1.63 (m, 2H), 1.25 (d, J=6.8 Hz, 3H), 0.85 (t, J=7.2 Hz, 3H).

Step B. 2-(2-(sec-butyl)phenyl)-4,4,5,5-tetramethyl-1,3,2-dioxaborolane. To a mixture of 2-(sec-butyl)phenyl trifluoromethanesulfonate (1.78 g, 6.31 mmol, 1.0 eq) and 4,4,5,5-tetramethyl-2-(4,4,5,5-tetramethyl-1,3,2-dioxaborolan-2-yl)-1,3,2-dioxaborolane (3.20 g, 12.6 mmol, 2.0 eq) in dioxane (16 mL) was added KOAc (1.86 g, 18.9 mmol, 3.0 eq). The mixture was degassed then Pd(dppf)Cl$_2$ (461 mg, 631 μmol, 0.10 eq) was added under N$_2$. The mixture was stirred at 110° C. for 1 hour under N$_2$. After completion, the mixture was diluted with ethyl acetate (10 mL) and water (15 mL) and then the organic layer was separated. The aqueous phase was extracted with ethyl acetate (10 mL). The combined organic layer was washed with saturated brine (20 mL), dried over Na$_2$SO$_4$, filtered and concentrated under vacuum. The residue was purified by reversed phase flash chromatography [water (FA, 0.1%)/acetonitrile] to give to give the title compound (1.23 g, 75% yield). Brown oil. $^1$H NMR (400 MHz, CDCl$_3$-d) δ=7.74 (dd, J=1.2, 7.6 Hz, 1H), 7.42-7.36 (td, J=1.2, 7.2 Hz, 1H), 7.29-7.25 (m, 1H), 7.17 (td, J=1.2, 7.2 Hz, 1H), 3.44 (m, 1H), 1.67-1.59 (m, 1H), 1.56-1.48 (m, 1H), 1.36 (s, 12H), 1.23 (d, J=6.8 Hz, 3H), 0.84 (t, J=7.2 Hz, 3H).

Step C. (1R,5S)-tert-butyl 3-(7-(2-(sec-butyl)phenyl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate. To a mixture of (1R,5S)-tert-butyl 3-(7-chloro-8-fluoro-2-((hexahydro-1H-pyrrolizin-7a-yl) methoxy)pyrido[4,3-d]pyrimidin-4-yl)-3,8-diazabicyclo[3.2.1]octane-8-carboxylate (100 mg, 188 μmol, 1.0 eq), 2-(2-(sec-butyl)phenyl)-4,4,5,5-tetramethyl-1,3,2-dioxaborolane (97.6 mg, 375 μmol, 2.0 eq) and K$_3$PO$_4$ aqueous solution (1.5 M, 375 μL, 3.0 eq) in THF (2.28 mL) was added [2-(2-aminophenyl) phenyl]palladium(1+); bis(1-adamantyl)-butyl-phosphane; methanesulfonate (13.66 mg, 18.76 μmol, 0.1 eq) under N$_2$. The mixture was stirred at 60° C. for 1 hour. After completion, the mixture was diluted with ethyl acetate (2 mL) and water (4 mL) and then the organic layer was separated. The aqueous phase was extracted with ethyl acetate (5 mL). The combined organic layer was washed with saturated brine (5 mL), dried over Na$_2$SO$_4$, filtered and concentrated under vacuum. The residue was purified by reversed phase flash chromatography [water (FA, 0.1%)/acetonitrile] to give to give the title compound (110 mg, 90% yield). Yellow solid. LCMS [ESI, M+1]: 631.4.

Step D. 4-((1R,5S)-3,8-diazabicyclo[3.2.1]octan-3-yl)-7-(2-(sec-butyl)phenyl)-8-fluoro-2-((hexahydro-1H-pyrrolizin-7a-yl)methoxy)pyrido[4,3-d]pyrimidine. To a mixture of (1R,5S)-tert-butyl 3-(7-(2-(sec-butyl)phenyl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (105 mg, 166 μmol, 1.0 eq) in MeCN (1 mL) was added HCl·dioxane (4 M, 2 mL, 48 eq) at 0° C. The mixture was stirred at 0° C. for 0.5 hour. After completion, the mixture was concentrated under vacuum. The residue was purified by prep-HPLC (column: Shim-pack C18 150*25*10 um; mobile phase: [water (0.225% FA)-ACN]; B %: 15%-35%, 8 min) to give to give the title compound (51.4 mg, 58% yield). Yellow solid. $^1$H NMR (400 MHz, METHANOL-d4) δ=9.14 (s, 1H), 7.53-7.45 (m, 2H), 7.36-7.28 (m, 2H), 4.84-4.79 (m, 2H), 4.68 (s, 2H), 4.13 (br s, 2H), 3.94 (br d, J=14.4 Hz, 2H), 3.76-3.67 (m, 2H), 3.34-3.32 (m, 1H), 3.30-3.26 (m, 1H), 2.61-2.51 (m, 1H), 2.39-2.31 (m, 2H), 2.28-2.16 (m, 4H), 2.14-1.99 (m, 6H), 1.68-1.47 (m, 2H), 1.21 (d, J=6.8 Hz, 3H), 0.68 (t, J=7.2 Hz, 3H). LCMS [ESI, M/2+1, M+1]: 266.4, 531.4.

Example 301

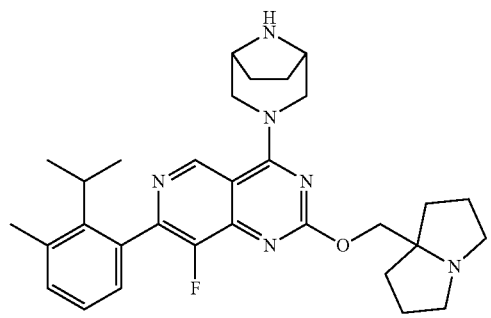 [SMILES: Cc1cccc(-c2ncc3c(N4CC5CCC(C4)N5)nc(OCC45CCCN4CCC5)nc3c2F)c1C(C)C]

4-((1R,5S)-3,8-diazabicyclo[3.2.1]octan-3-yl)-8-fluoro-2-((hexahydro-1H-pyrrolizin-7a-yl)methoxy)-7-(2-isopropyl-3-methylphenyl)pyrido[4,3-d]pyrimidine

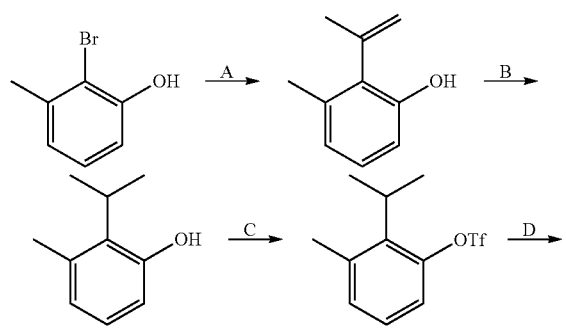

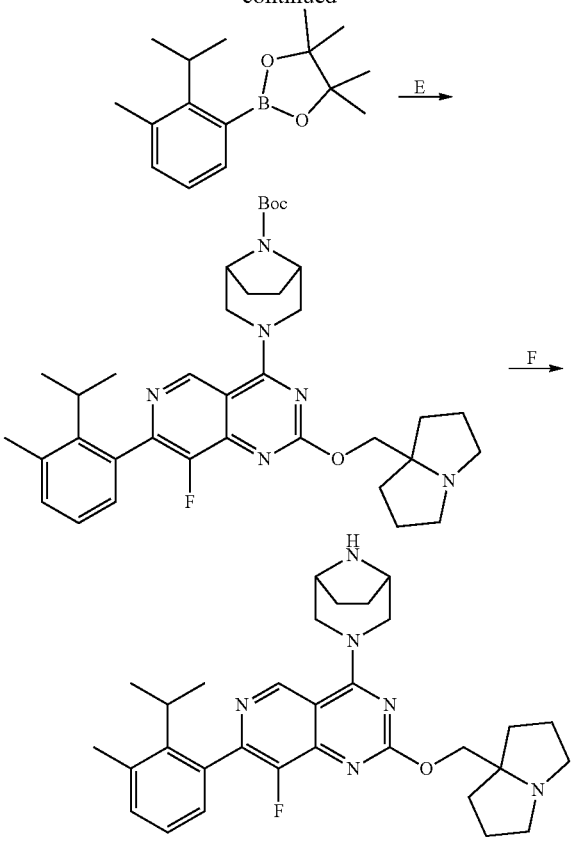

Step A. 3-methyl-2-(prop-1-en-2-yl)phenol. A mixture of 2-bromo-3-methyl-phenol (5 g, 26.7 mmol, 1.0 eq), 4,4,5,5-tetramethyl-2-(prop-1-en-2-yl)-1,3,2-dioxaborolane (8.98 g, 53.4 mmol, 2.0 eq), K$_3$PO$_4$ (17.0 g, 80.2 mmol, 3.0 eq), Pd(dppf)Cl$_2$ (1.96 g, 2.67 mmol, 0.1 eq) in dioxane (42 mL) and H$_2$O (14 mL) was degassed and purged with N$_2$ for 3 times, and then the mixture was stirred at 90° C. for 12 hours under N$_2$ atmosphere. The reaction mixture was diluted with water (60 mL) and extracted with ethyl acetate (3×100 mL). The combined organic layers were washed with brine (100 mL), dried over Na$_2$SO$_4$, filtered and concentrated under reduced pressure. The residue was purification by column chromatography (SiO$_2$, petroleum ether/ethyl acetate=1/0 to 30/1) to give this title compound (3 g, 76% yield). Yellow oil. $^1$H NMR (400 MHz, chloroform-d) δ=7.08 (t, J=8.0 Hz, 1H), 6.78 (t, J=8.0 Hz, 2H), 5.54-5.51 (m, 1H), 5.39-5.31 (m, 1H), 5.10-5.03 (m, 1H), 2.26 (s, 3H), 2.04 (d, J=0.8 Hz, 3H).

Step B. 2-isopropyl-3-methylphenol. To a solution of 3-methyl-2-(prop-1-en-2-yl)phenol (3 g, 20.2 mmol, 1.0 eq) in ethyl acetate (30 mL) was added PtO$_2$ (460 mg, 2.02 mmol, 0.1 eq) under N$_2$. The suspension was degassed under vacuum and purged with H$_2$ several times. The mixture was stirred under H$_2$ (15 psi) at 10° C. for 6 hours. The reaction mixture was filtered and the filtrate was concentrated to give the title compound (3 g, 98% yield). White solid. $^1$H NMR (400 MHz, chloroform-d) δ=6.95 (t, J=8.0 Hz, 1H), 6.74 (d, J=7.6 Hz, 1H), 6.56 (d, J=8.0 Hz, 1H), 4.64 (s, 1H), 3.37-3.25 (m, 1H), 2.35 (s, 3H), 1.40 (s, 3H), 1.38 (s, 3H).

Step C. 2-isopropyl-3-methylphenyl trifluoromethanesulfonate. To a solution of 2-isopropyl-3-methylphenol (2.9 g, 19.3 mmol, 1.0 eq) in DCM (60 mL) was added DIEA (7.49 g, 57.9 mmol, 10.1 mL, 3.0 eq) and Tf$_2$O (8.17 g, 28.9 mmol, 4.78 mL, 1.5 eq) at −40° C. The mixture was stirred at −40° C. for 3 hours. The reaction mixture was diluted with water (60 mL) and the organic layer was separated. The aqueous phase was extracted with ethyl acetate (3×30 mL). The combined organic layers were washed with brine (50 mL), dried over Na$_2$SO$_4$, filtered and concentrated under reduced pressure. The residue was purification by column chromatography (SiO$_2$, petroleum ether/ethyl acetate=1/0 to 50/1) to give the title compound (3 g, 55% yield). Colorless oil.

Step D. 2-(2-isopropyl-3-methylphenyl)-4,4,5,5-tetramethyl-1,3,2-dioxaborolane. A mixture of 2-isopropyl-3-methylphenyl trifluoromethanesulfonate (3 g, 10.6 mmol, 1.0 eq), Pin2B2 (5.40 g, 21.3 mmol, 2.0 eq), KOAc (3.13 g, 31.9 mmol, 3.0 eq), and Pd(dppf)Cl$_2$ (778 mg, 1.06 mmol, 0.1 eq) in dioxane (25 mL) was degassed and purged with N$_2$ for 3 times, and then the mixture was stirred at 110° C. for 1 hour under N$_2$ atmosphere. The reaction mixture was diluted with water (30 mL) and extracted with ethyl acetate (3×30 mL). The combined organic layers were washed with brine (30 mL), dried over Na$_2$SO$_4$, filtered and concentrated under reduced pressure. The residue was purification by column chromatography (SiO$_2$, PE/EA=1/0 to 50/1) to give the title compound (2.1 g, 76% yield). Yellow oil. $^1$H NMR (400 MHz, chloroform-d) δ=7.43 (d, J=7.2 Hz, 1H), 7.18-7.13 (m, 1H), 7.10-7.03 (m, 1H), 3.52-3.42 (m, 1H), 2.39 (s, 3H), 1.38 (s, 12H), 1.37 (s, 3H), 1.35 (s, 3H).

Step E. tert-butyl (1R,5S)-3-(8-fluoro-7-(2-isopropyl-3-methylphenyl)-2-((tetrahydro-1H-pyrrolizin-7a(5H)-yl)methoxy)pyrido[4,3-d]pyrimidin-4-yl)-3,8-diazabicyclo[3.2.1]octane-8-carboxylate. A mixture of (1R,5S)-tert-butyl 3-(7-chloro-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (200 mg, 375 μmol, 1.0 eq), 2-(2-isopropyl-3-methylphenyl)-4,4,5,5-tetramethyl-1,3,2-dioxaborolane (195 mg, 750 μmol, 2.0 eq), K$_3$PO$_4$ (1.5 M in water, 750 μL, 3.0 eq), and [2-(2-aminophenyl)phenyl]palladium(1+); bis(1-adamantyl)-butyl-phosphane; methanesulfonate (27.3 mg, 37.5 μmol, 0.1 eq) in toluene (4.0 mL) was degassed and purged with N$_2$ for 3 times. The mixture was stirred at 90° C. for 1 hour under N$_2$ atmosphere. The reaction mixture was diluted with water (10 mL) and extracted with ethyl acetate (3×5 mL). The combined organic layers were washed with brine (5 mL), dried over Na$_2$SO$_4$, filtered and concentrated under reduced pressure. The residue was purified by reversed phase flash chromatography [water (0.1% formic acid)/acetonitrile)] to give the title compound (130 mg, 54% yield). Yellow solid. LCMS [ESI, M+1]:631.5.

Step F. 4-((1R,5S)-3,8-diazabicyclo[3.2.1]octan-3-yl)-8-fluoro-2-((hexahydro-1H-pyrrolizin-7a-yl)methoxy)-7-(2-isopropyl-3-methylphenyl)pyrido[4,3-d]pyrimidine. To a solution of (1R,5S)-tert-butyl 3-(8-fluoro-2-((hexahydro-1H-pyrrolizin-7a-yl) methoxy)-7-(2-isopropyl-3-methylphenyl)pyrido[4,3-d]pyrimidin-4-yl)-3,8-diazabicyclo[3.2.1]octane-8-carboxylate (60 mg, 95.1 μmol, 1.0 eq) in MeCN (0.5 mL) was added HCl·dioxane (4 M, 1.0 mL). The mixture was stirred at 0° C. for 30 minutes. The mixture was concentrated, and then the reaction mixture was diluted with water (0.5 mL). The mixture was basified to pH~8 with saturated NaHCO$_3$ aqueous solution. The residue was purified by prep-HPLC (column: Waters X bridge C18 150*50 mm*10 um; mobile phase: [water (10 mM NH$_4$HCO$_3$)-ACN]; B %: 30%-60%, 10 min). The desired fraction was collected and concentrated under vacuum to remove acetonitrile. The mixture was lyophilized to give the title compound (25.66 mg 51% yield). White solid. $^1$H NMR (400 MHz, chloroform-d) δ=8.99 (s, 1H), 7.24-7.20 (m, 1H), 7.20-7.14 (m, 1H), 7.08-7.03 (m, 1H), 4.58 (br d, J=11.6 Hz, 2H), 4.16 (s, 2H), 3.69-3.56 (m, 4H), 3.15-3.04 (m, 3H), 2.68-2.58 (m, 2H), 2.51 (s, 3H), 2.15-2.04 (m, 2H), 1.93-1.79 (m, 7H), 1.76-1.56 (m, 3H), 1.23 (br d, J=6.0 Hz, 6H); LCMS [ESI, M+1]:531.4.

Example 302

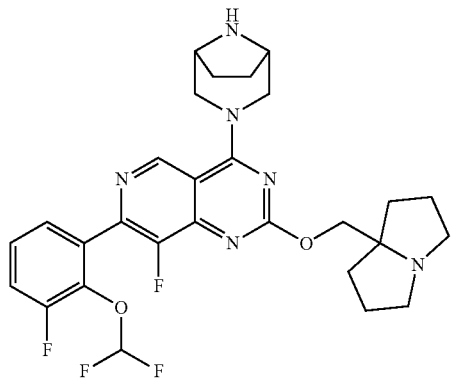 [SMILES: Fc1cccc(-c2ncc3c(N4CC5CCC(C4)N5)nc(OCC45CCCN4CCC5)nc3c2F)c1OC(F)F]

4-((1R,5S)-3,8-diazabicyclo[3.2.1]octan-3-yl)-7-(2-(difluoromethoxy)-3-fluorophenyl)-8-fluoro-2-((hexahydro-1H-pyrrolizin-7a-yl)methoxy)pyrido[4,3-d]pyrimidine

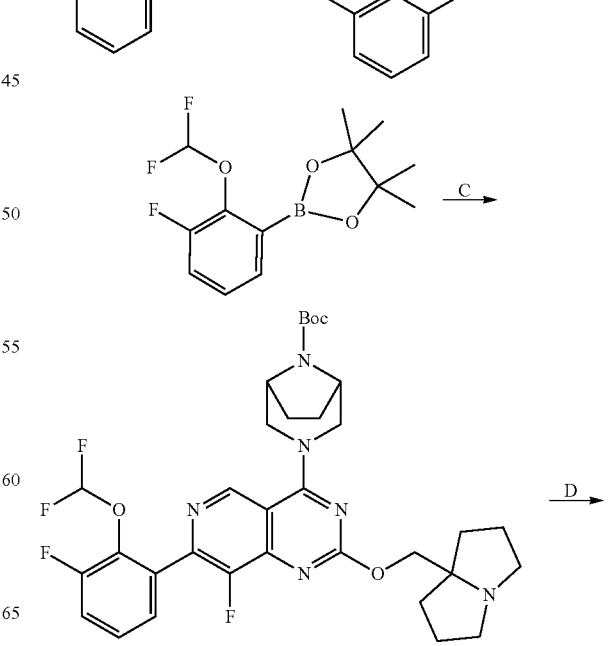

-continued

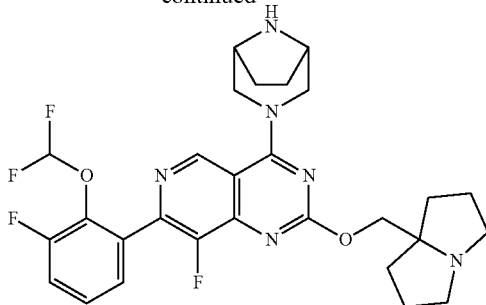

Step A. 1-bromo-2-(difluoromethoxy)-3-fluorobenzene. To a mixture of 2-bromo-6-fluorophenol (2 g, 10.5 mmol, 1 eq) in DMF (50 mL) and H₂O (7 mL) was added Cs₂CO₃ (6.82 g, 20.9 mmol, 2 eq) and sodium 2-chloro-2,2-difluoro-acetate (3.99 g, 26.2 mmol, 2.5 eq). The mixture was stirred at 100° C. for 6 hours under N₂. After completion, the mixture was diluted with ethyl acetate (100 mL), washed with brine (3×100 mL), dried over Na₂SO₄, filtered and concentrated under vacuum to give the title compound (2.4 g, 95% yield) and used into next step without further purification. Colourless oil. ¹H NMR (400 MHz, chloroform-d) δ=7.33 (td, J=1.6, 7.6 Hz, 1H), 7.11-7.01 (m, 2H), 6.73-6.30 (m, 1H).

Step B. 2-(2-(difluoromethoxy)-3-fluorophenyl)-4,4,5,5-tetramethyl-1,3,2-dioxaborolane. A mixture of 1-bromo-2-(difluoromethoxy)-3-fluorobenzene (700 mg, 2.90 mmol, 1 eq), 4,4,5,5-tetramethyl-2-(4,4,5,5-tetramethyl-1,3,2-dioxaborolan-2-yl)-1,3,2-dioxaborolane (1.48 g, 5.81 mmol, 2 eq), Pd(dppf)Cl₂ (213 mg, 290 μmol, 0.1 eq) and KOAc (855 mg, 8.71 mmol, 3 eq) in dioxane (10 mL) was stirred at 110° C. for 1 hour. After completion, the mixture was diluted with water (20 mL) and extracted with ethyl acetate (2×20 mL). The combined organic layer was washed with brine (20 mL), dried over Na₂SO₄, filtered and concentrated under vacuum. The residue was purified by reversed phase flash chromatography [water (FA, 0.1%)/acetonitrile]. to give the title compound (400 mg, 48% yield). Yellow oil. ¹H NMR (400 MHz, chloroform-d) δ=7.54-7.47 (m, 1H), 7.29-7.19 (m, 2H), 6.79-6.37 (m, 1H), 1.36 (s, 12H).

Step C. (1R,5S)-tert-butyl 3-(7-(2-(difluoromethoxy)-3-fluorophenyl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate. A mixture of (1R,5S)-tert-butyl 3-(7-chloro-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (100 mg, 188 μmol, 1 eq), 2-(2-(difluoromethoxy)-3-fluorophenyl)-4,4,5,5-tetramethyl-1,3,2-dioxaborolane (108 mg, 375 μmol, 2 eq), [2-(2-aminophenyl)phenyl]palladium(1+); bis(1-adamantyl)-butyl-phosphane; methanesulfonate (13.7 mg, 18.7 μmol, 0.1 eq) and K₃PO₄ (1.5 M in THF, 375 μL, 3 eq) in THF (2 mL) was stirred at 60° C. for 2 hours. After completion, the mixture was diluted with water (5.0 mL), and extracted with ethyl acetate (2×5.0 mL). The combined organic layer was washed with brine (5.0 mL), dried over Na₂SO₄, filtered concentrated under vacuum. The residue was purified by reversed phase flash chromatography [water (FA, 0.1%)/acetonitrile] to give the title compound (110 mg, 89% yield). Yellow oil. LCMS [ESI, M+1]: 659.3.

Step D. 4-((1R,5S)-3,8-diazabicyclo[3.2.1]octan-3-yl)-7-(2-(difluoromethoxy)-3-fluorophenyl)-8-fluoro-2-((hexahydro-1H-pyrrolizin-7a-yl)methoxy)pyrido[4,3-d]pyrimidine. A mixture of (1R,5S)-tert-butyl 3-(7-(2-(difluoromethoxy)-3-fluorophenyl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (100 mg, 152 μmol, 1 eq) and HCl/dioxane (4 M, 1 mL, 26.4 eq) and acetonitrile (0.5 mL) was stirred at 15° C. for 0.5 hour. After completion, the mixture was concentrated under vacuum. The residue was purified by prep-HPLC (column: Shim-pack C18 150*25*10 um; mobile phase: [water (0.225% FA)-ACN]; B %: 9%-29%, 8 min) to give the title compound (57.39 mg, 60% yield, 1.4 FA). Off-white solid. ¹H NMR (400 MHz, METHANOL-d4) δ=9.17 (s, 1H), 8.45 (br s, 1H), 7.54-7.39 (m, 3H), 6.95-6.55 (m, 1H), 4.82 (br d, J=13.2 Hz, 2H), 4.69 (s, 2H), 4.16 (br s, 2H), 3.97 (br d, J=13.6 Hz, 2H), 3.72 (td, J=6.8, 11.6 Hz, 2H), 3.33-3.26 (m, 2H), 2.40-2.30 (m, 2H), 2.30-1.99 (m, 10H). FNMR: −83.170, −130.150, −139.040. LCMS [ESI, M+1]: 559.3.

Example 303

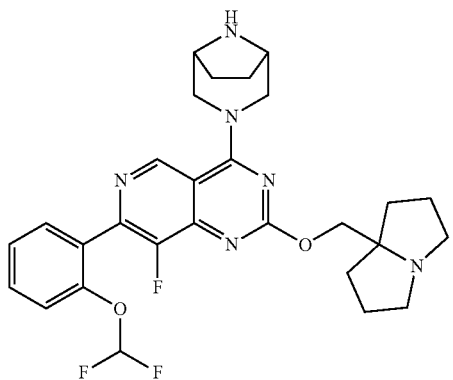 [SMILES: Fc1c(-c2ccccc2OC(F)F)ncc2c(N3CC4CCC(C3)N4)nc(OCC34CCCN3CCC4)nc12]

4-((1R,5S)-3,8-diazabicyclo[3.2.1]octan-3-yl)-7-(2-(difluoromethoxy)phenyl)-8-fluoro-2-((hexahydro-1H-pyrrolizin-7a-yl)methoxy)pyrido[4,3-d]pyrimidine

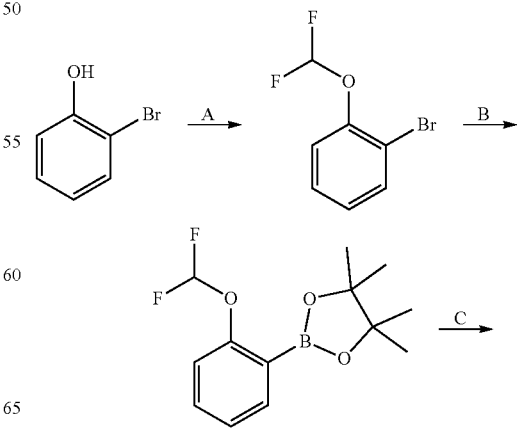

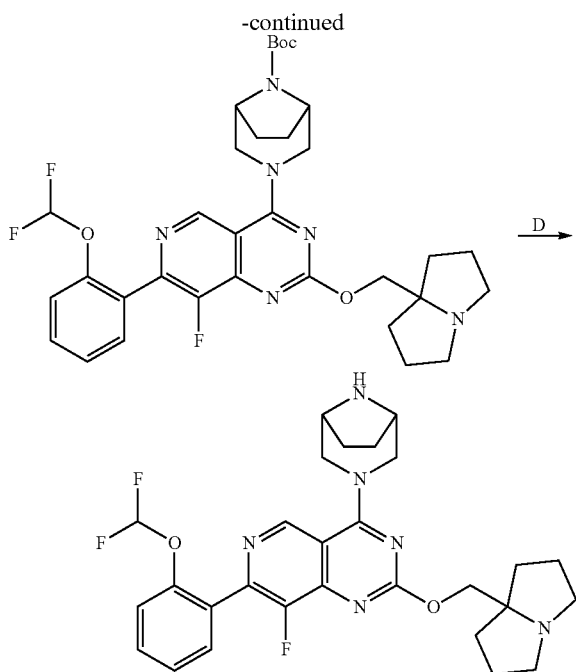

Step A. 1-bromo-2-(difluoromethoxy)benzene. A mixture of 2-bromophenol (2 g, 11.6 mmol, 1 eq), sodium 2-chloro-2, 2-difluoro-acetate (3.08 g, 20.2 mmol, 1.75 eq), $Cs_2CO_3$ (7.53 g, 23.1 mmol, 2 eq) in DMF (25 mL) was stirred at 105° C. for 3 hours under $N_2$ atmosphere. The reaction mixture was poured into ice water (1 L) and extracted with EA (30 mL×4). The combined organic layers were washed with $H_2O$ (25 mL×4), brine (25 mL×5), dried over anhydrous $Na_2SO_4$, filtered and concentrated under reduced pressure to give the title compound (6 g, crude), which was used in the next step without further purification. White gum; Rf=0.47 (10/1 petroleum ether/ethyl acetate); $^1H$ NMR (400 MHz, chloroform-d) δ=7.62 (dd, J=1.6, 8.0 Hz, 1H), 7.33-7.29 (m, 1H), 7.22 (dd, J=1.2, 8.0 Hz, 1H), 7.11 (dt, J=1.6, 7.6 Hz, 1H), 6.71-6.71 (m, 1H); $^{19}F$ NMR (376 MHz, chloroform-d) δ=−81.3.

Step B. 2-(2-(difluoromethoxy)phenyl)-4,4,5,5-tetramethyl-1,3,2-dioxaborolane. A mixture of 1-bromo-2-(difluoromethoxy)benzene (1.2 g, crude, real amount was 3 g), 4,4,5,5-tetramethyl-2-(4,4,5,5-tetramethyl-1,3,2-dioxaborolan-2-yl)-1,3,2-dioxaborolane (2.05 g, 8.07 mmol, 1.5 eq), AcOK (1.06 g, 10.8 mmol, 2 eq) and $Pd(dppf)Cl_2$ (400 mg, 546 μmol, 1.02e-1 eq) in dioxane (25 mL) was degassed and purged with $N_2$ for 3 times. The mixture was stirred at 100° C. for 1.5 hours under $N_2$ atmosphere. The reaction mixture was diluted with $H_2O$ (100 mL) and extracted with EA (25 mL×4). The combined organic layers were washed with brine (15 mL), dried over anhydrous $Na_2SO_4$, filtered and concentrated under reduced pressure to give a residue. The residue was purified by reversed phase flash chromatography [water (FA, 0.10%)/acetonitrile=3/17] to give the title compound (0.55 g, 27% yield two steps). Red brown oil; $^1H$ NMR (400 MHz, DMSO-d6) δ=7.66 (dd, J=2.0, 7.6 Hz, 1H), 7.55 (dt, J=2.0, 8.0 Hz, 1H), 7.28 (dt, J=0.8, 7.2 Hz, 1H), 7.04 (t, 1H), 7.27-6.80 (m, 1H), 1.29 (s, 12H); $^{19}F$ NMR (376 MHz, DMSO-d6) δ=−81.5; RT=1.05 min.

Step C. (1R,5S)-tert-butyl 3-(7-(2-(difluoromethoxy)phenyl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate. A mixture of (1R,5S)-tert-butyl 3-(7-chloro-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (120 mg, 225 μmol, 1 eq) and $K_3PO_4$ (1.5M, 0.5 mL, 3.33 eq, in $H_2O$) in THF (2.5 mL) was degassed and purged with $N_2$ for 3 times. [2-(2-aminophenyl)phenyl]palladium (1+); bis(1-adamantyl)-butylphosphane; methanesulfonate (17 mg, 23.3 μmol, 1.04e-1 eq) was added, followed by 2-(2-(difluoromethoxy)phenyl)-4,4,5,5-tetramethyl-1,3,2-dioxaborolane (100 mg, 270 μmol, 1.20 eq, 73% purity). The mixture was stirred at 60° C. for 2.5 hours. The reaction mixture was diluted with $H_2O$ (10 mL), and extracted with EA (15 mL×4). The combined organic layers were washed with brine (10 mL), dried over anhydrous $Na_2SO_4$, filtered and concentrated under reduced pressure to give a residue. The residue was purified reversed phase flash [water (FA, 0.1%)/acetonitrile=1/1] to give the title compound (130 mg, 89% yield). Light yellow gum; LCMS [ESI, M+1]: 641.3.

Step D. 4-((1R,5S)-3,8-diazabicyclo[3.2.1]octan-3-yl)-7-(2-(difluoromethoxy) phenyl)-8-fluoro-2-((hexahydro-1H-pyrrolizin-7a-yl)methoxy)pyrido[4,3-d]pyrimidine. To a solution of (1R,5S)-tert-butyl 3-(7-(2-(difluoromethoxy) phenyl)-8-fluoro-2-((hexahydro-1H-pyrrolizin-7a-yl) methoxy)pyrido[4,3-d]pyrimidin-4-yl)-3,8-diazabicyclo[3.2.1]octane-8-carboxylate (90 mg, 139 μmol, 1 eq) in MeCN (2 mL) was added HCl·dioxane (4 M, 0.5 mL) below 15° C. The mixture was stirred at 15° C. for 0.5 hour. The reaction mixture was concentrated under reduced pressure to give a residue at room temperature (without heating). The residue was dissolved in DCM (20 mL) and $H_2O$ (5 mL). The pH of the mixture was adjusted to 8 with $NaHCO_3$ solid below 10° C. The mixture was extracted with DCM (10 mL×4). The combined organic layers were dried over anhydrous $Na_2SO_4$, filtered and concentrated under reduced pressure to give a residue. The residue was purified by prep-HPLC (column: 3_Phenomenex Luna C18 75*30 mm*3 um; mobile phase: [water (0.225% FA)-ACN]; B %: 5%-25%, 8 min). The desired fractions were collected and lyophilized to give the title compound (30.5 mg, 34% yield, 1.8FA). Off-white solid; $^1H$ NMR (400 MHz, methanol-d4) δ=9.16 (s, 1H), 8.47 (s, 1.8H), 7.63-7.58 (m, 2H), 7.44-7.34 (m, 2H), 6.86 (t, 1H), 4.79 (d, J=13.2 Hz, 2H), 4.67 (s, 2H), 4.07 (s, 2H), 3.91 (d, J=13.2 Hz, 2H), 3.74-3.68 (m, 2H), 3.30-3.26 (m, 2H), 2.38-2.32 (m, 2H), 2.26-2.16 (m, 4H), 2.14-1.94 (m, 6H); $^{19}F$ NMR (376 MHz, methanol-d4) δ=−82.7, -139; LCMS [ESI, M+1]: 541.2.

Example 304

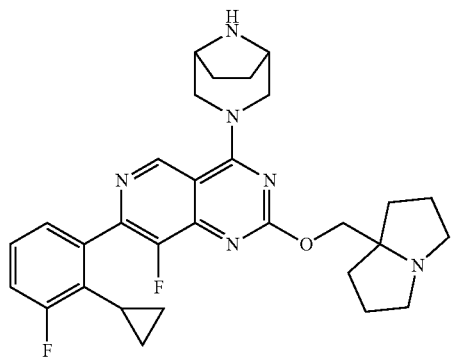 [SMILES: Fc1cccc(-c2ncc3c(N4CC5CCC(C4)N5)nc(OCC45CCCN4CCC5)nc3c2F)c1C1CC1]

4-((1R,5S)-3,8-diazabicyclo[3.2.1]octan-3-yl)-7-(2-cyclopropyl-3-fluorophenyl)-8-fluoro-2-((hexahydro-1H-pyrrolizin-7a-yl)methoxy)pyrido[4,3-d]pyrimidine

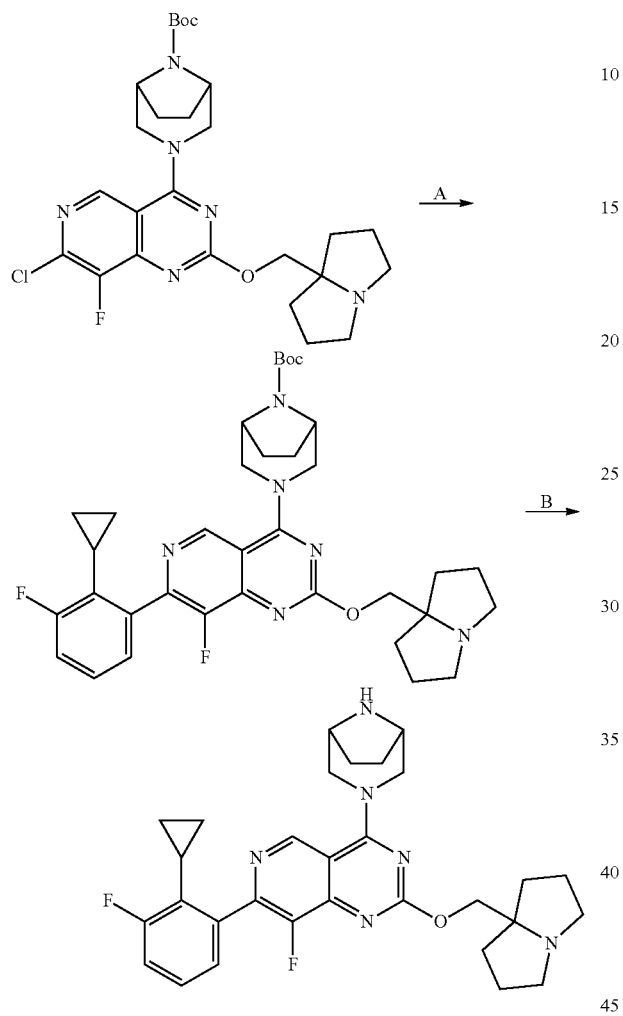

Step A. tert-butyl 3-(7-(2-cyclopropyl-3-fluorophenyl)-8-fluoro-2-((hexahyro-1H-pyrrolizin-7a-yl)methoxy)pyrido[4,3-d]pyrimidin-4-yl)-3,8-diazabicyclo[3.2.1]octane-8-carboxylate. A mixture of tert-butyl 3-(7-chloro-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (100 mg, 187 µmol, 1.0 eq), (2-cyclopropyl-3-fluoro-phenyl)boronic acid (67.5 mg, 375 µmol, 2.0 eq), [2-(2-aminophenyl)phenyl]palladium(1+); bis(1-adamantyl)-butyl-phosphane; methanesulfonate (13.6 mg, 18.7 µmol, 0.1 eq), and K₃PO₄ (1.5 M, 375 µL, 3.0 eq) in THF (3 mL) was degassed and purged with N₂ for 3 times, and then the mixture was stirred at 60° C. for 3 hours under N₂ atmosphere. The reaction mixture was diluted with water (10 mL) and extracted with ethyl acetate (3×10 mL). The combined organic layers were washed with brine (10 mL), dried over Na₂SO₄, filtered and concentrated under reduced pressure to give a residue. The residue was purified by reversed phase flash chromatography [water (0.1% formic acid)/acetonitrile)] to give the title compound (40 mg, 28% yield) as a yellow oil. LCMS [ESI, M+1]: 633.4.

Step B. 4-(3,8-diazabicyclo[3.2.1]octan-3-yl)-7-(2-cyclopropyl-3-fluorophenyl)-8-fluoro-2-((hexahydro-1H-pyrrolizin-7a-yl)methoxy)pyrido[4,3-d]pyrimidine. To a solution of tert-butyl 3-(7-(2-cyclopropyl-3-fluorophenyl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (35 mg, 55.3 µmol, 1.0 eq) in ACN (0.1 mL) was added HCl·dioxane (4 M, 1.75 mL). The mixture was stirred at 20° C. for 0.5 hour. The mixture was concentrated under vacuum. The residue was purified by prep-HPLC (column: Phenomenex luna C18 150*25 mm*10 um; mobile phase: [water (0.225% FA)-ACN]; B %: 3%-33%, 10 min). The desired fraction was collected and lyophilized to give the title compound (13.7 mg, 39% yield, 1.9 FA) as off-white solid. ¹H NMR (400 MHz, methanol-d4) δ=9.15 (s, 1H), 7.42-7.32 (m, 1H), 7.27-7.16 (m, 2H), 4.79 (br d, J=13.2 Hz, 2H), 4.67 (s, 2H), 4.06 (br s, 2H), 3.90 (br d, J=13.2 Hz, 2H), 3.75-3.65 (m, 2H), 3.30-3.23 (m, 2H), 2.39-2.30 (m, 2H), 2.27-1.94 (m, 10H), 1.89-1.80 (m, 1H), 0.73-0.60 (m, 2H), 0.43-0.31 (m, 2H); LCMS [ESI, M+1]: 533.3.

Example 305

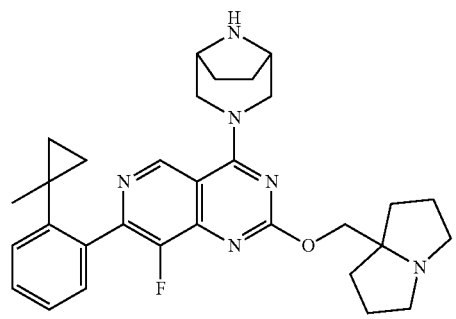 [SMILES: CC1(c2ccccc2-c2ncc3c(N4CC5CCC(C4)N5)nc(OCC45CCCN4CCC5)nc3c2F)CC1]

4-((1R,5S)-3,8-diazabicyclo[3.2.1]octan-3-yl)-8-fluoro-2-((hexahydro-1H-pyrrolizin-7a-yl)methoxy)-7-(2-(1-methylcyclopropyl)phenyl)pyrido[4,3-d]pyrimidine

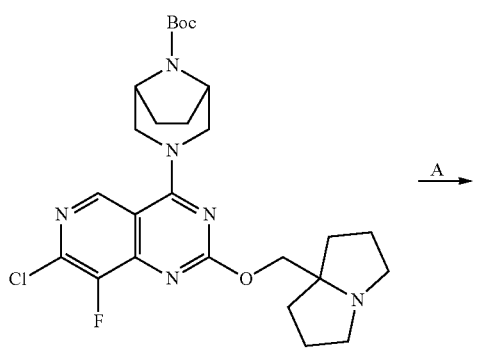

669

-continued

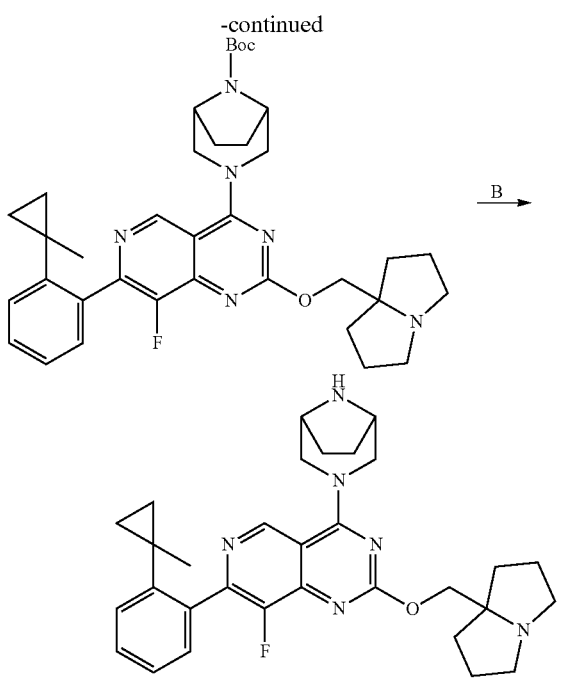

Step A. tert-butyl 3-(8-fluoro-2-((hexahydro-1H-pyr-rolizin-7a-yl)methoxy)-7-(2-(1-methylcyclopropyl)phenyl)pyrido[4,3-d]pyrimidin-4-yl)-3,8-diazabicyclo[3.2.1]octane-8-carboxylate. To a mixture of tert-butyl 3-(7-chloro-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (150 mg, 281 µmol, 1.0 eq), 4,4,5,5-tetramethyl-2-[2-(1-methylcyclopropyl)phenyl]-1,3,2-dioxaborolane (145 mg, 563 µmol, 2.0 eq) and K$_3$PO$_4$ (1.5 M, 563 µL, 3.0 eq) in THF (4 mL) was added [2-(2-aminophenyl)phenyl]palladium(1+); bis(1-adamantyl)-butyl-phosphane; methanesulfonate (20.5 mg, 28.1 µmol, 0.10 eq) under N$_2$. The mixture was stirred at 60° C. for 1 hour under N$_2$. After completion, the mixture was concentrated under vacuum. The residue was purified by reversed phase flash chromatography [water (FA, 0.1%)/acetonitrile] to give the title compound (165 mg, 93% yield). Yellow solid. LCMS [ESI, M+1]: 629.4.

Step B. 4-(3,8-diazabicyclo[3.2.1]octan-3-yl)-8-fluoro-2-((hexahydro-1H-pyrrolizin-7a-yl)methoxy)-7-(2-(1-methylcyclopropyl)phenyl)pyrido[4,3-d]pyrimidine. To a mixture of tert-butyl 3-(8-fluoro-2-((hexahydro-1H-pyrrolizin-7a-yl)methoxy)-7-(2-(1-methylcyclopropyl)phenyl)pyrido[4,3-d]pyrimidin-4-yl)-3,8-diazabicyclo[3.2.1]octane-8-carboxylate (100 mg, 159 µmol, 1.0 eq) and acetonitrile (1 mL) was added HCl·dioxane (4 M, 2 mL, 50 eq) at 0° C. The mixture was stirred at 0° C. for 0.5 hour. After completion, the mixture was concentrated under vacuum. The residue was purified by prep-HPLC (column: Shim-pack C18 150*25*10 um; mobile phase: [water (0.225% FA)-ACN]; B %: 10%-30%, 9 min) to give the title compound (67.1 mg, 73% yield, FA). Off-white. $^1$H NMR (400 MHz, METHANOL-d4) δ=9.15 (s, 1H), 7.59 (dd, J=0.8, 8.0 Hz, 1H), 7.46 (td, J=1.2, 7.6 Hz, 1H), 7.34 (dt, J=1.2, 7.6 Hz, 1H), 7.25 (dd, J=1.2, 7.6 Hz, 1H), 4.80 (br d, J=13.6 Hz, 2H), 4.68 (s, 2H), 4.11 (br s, 2H), 3.92 (br d, J=13.2 Hz, 2H), 3.75-3.67 (m, 2H), 3.34-3.26 (m, 2H), 2.39-2.32 (m, 2H), 2.21 (m, 4H), 2.15-2.06 (m, 4H), 2.04-1.98 (m, 2H), 1.32 (s, 3H), 0.61-0.56 (m, 2H), 0.40-0.34 (m, 2H). LCMS [ESI, M/2+1, M+1]: 265.4, 529.3.

670

Example 306

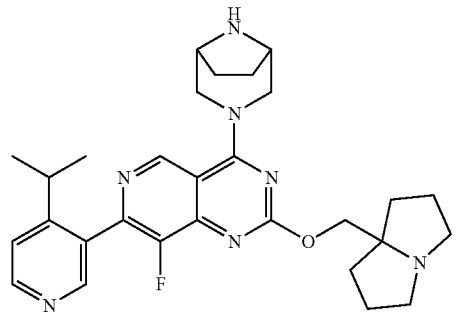 [SMILES: CC(C)c1ccncc1-c1ncc2c(N3CC4CCC(C3)N4)nc(OCC34CCCN3CCC4)nc2c1F]

4-((1R,5S)-3,8-diazabicyclo[3.2.1]octan-3-yl)-8-fluoro-2-((hexahydro-1H-pyrrolizin-7a-yl)methoxy)-7-(4-isopropylpyridin-3-yl)pyrido[4,3-d]pyrimidine

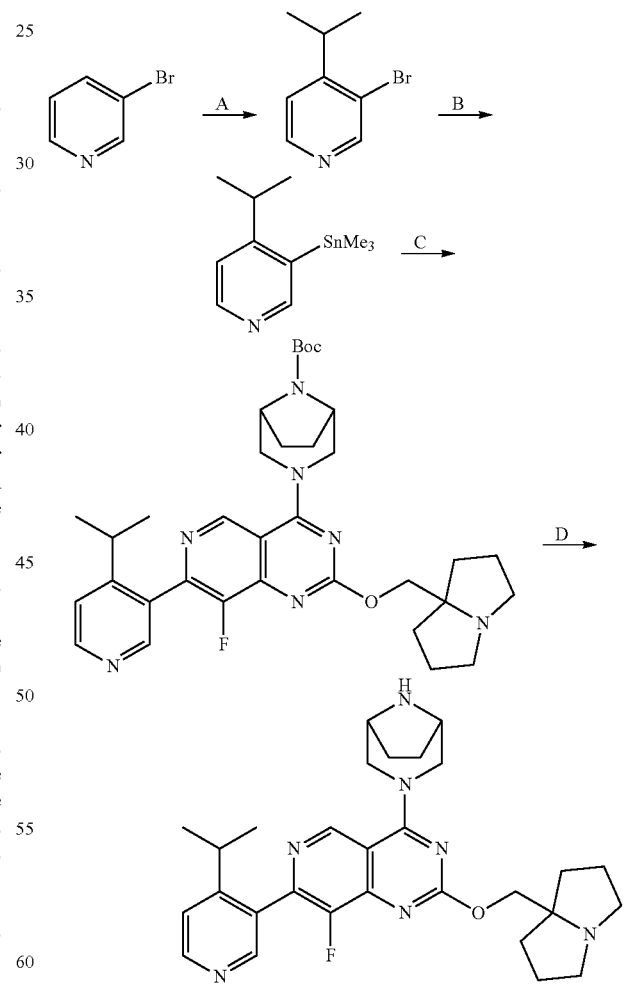

Step A. 3-bromo-4-isopropylpyridine. To a solution of 3-bromopyridine (10 g, 63.3 mmol, 6.10 mL, 1.0 eq) in THF (200 mL) and cooled to 0° C. Then BF$_3$·Et$_2$O (9.88 g, 69.6 mmol, 8.59 mL, 1.1 eq) was added drop wise and stirred for 15 minutes at 0° C. The reaction mixture was cooled to −50°

C. followed by dropwise addition of lithium; chloro(isopropyl)magnesium; chloride (58.4 mL, 1.3 M, 1.2 eq), and stirring the reaction mixture at −50° C. for 30 minutes. Then 2,3,5,6-tetrachloro-1,4-benzoquinone (31.1 g, 126 mmol, 2.0 eq) was added dropwise and the mixture was warmed up to 20° C. and stirred for 2 hours. Upon completion, the mixture was concentrated, then reaction mixture was diluted with water (200 mL). The aqueous layer was extracted with ethyl acetate (3×200 mL). The combined organic layers were washed with brine (300 mL), dried over $Na_2SO_4$, filtered and concentrated under reduced pressure. The residue was purification by column chromatography ($SiO_2$, Petroleum ether:Ethyl acetate=1/0 to 20:1) to give the title compound (5.1 g, 37% yield); Red oil; LCMS [ESI, M+1]: 200.1.

Step B. 4-isopropyl-3-(trimethylstannyl)pyridine. To a mixture of 3-bromo-4-isopropylpyridine (1 g, 5.00 mmol, 1.0 eq) and trimethyl(trimethylstannyl)stannane (4.09 g, 12.5 mmol, 2.59 mL, 2.5 eq) in toluene (20 mL) was added $Pd(PPh_3)_4$ (578 mg, 500 μmol, 0.1 eq). The reaction was degassed and purged with $N_2$ for 3 times, then heated to 110° C. and stirred for 10 hours. Upon completion, the reaction mixture was diluted with water (50 mL) and extracted with ethyl acetate (3×30 mL). The combined organic layers were washed with brine (30 mL), dried over $Na_2SO_4$, filtered and concentrated under reduced pressure The residue was purified by column chromatography ($SiO_2$, Petroleum ether: Ethyl acetate=1/0 to 15:1) to give the title compound (0.66 g, 47% yield). Yellow oil; $^1$H NMR (400 MHz, CHLOROFORM-d) δ=8.52-8.47 (m, 2H), 7.20 (d, J=5.6 Hz, 1H), 2.81-2.68 (m, 1H), 1.26 (d, J=6.6 Hz, 6H), 0.48-0.26 (m, 9H).

Step C. tert-butyl 3-(8-fluoro-2-((hexahydro-1H-pyrrolizin-7a-yl)methoxy)-7-(4-isopropylpyridin-3-yl)pyrido[4,3-d]pyrimidin-4-yl)-3,8-diazabicyclo[3.2.1]octane-8-carboxylate. To a mixture of tert-butyl 3-(7-chloro-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (375 mg, 704 μmol, 1.0 eq) and 4-isopropyl-3-(trimethylstannyl)pyridine (400 mg, 1.41 mmol, 2.0 eq) in toluene (8 mL) were added $Pd(dppf)Cl_2$ (51.5 mg, 70.4 μmol, 0.1 eq) and BINAP (87.7 mg, 141 μmol, 0.2 eq) and CuI (40.2 mg, 211 μmol, 0.3 eq). Then it was degassed and purged with $N_2$ for 3 times. The reaction was stirred at 105° C. for 10 hours. Upon completion, the reaction mixture was diluted with $H_2O$ (20 mL) and extracted with ethyl acetate (3×20 mL). The combined organic layers were washed with brine (30 mL), dried over $Na_2SO_4$, filtered and concentrated under reduced pressure to give a residue. The residue was purified by reversed phase flash chromatography [water (0.1% formic acid)/acetonitrile)] to give the title compound (100 mg, 23% yield), Red oil; $^1$H NMR (400 MHz, CHLOROFORM-d) δ=9.03 (s, 1H), 8.67-8.53 (m, 2H), 7.37 (d, J=5.2 Hz, 1H), 4.58 (br d, J=12.4 Hz, 2H), 4.48-4.30 (m, 2H), 4.21 (br s, 2H), 3.79-3.61 (m, 2H), 3.21-3.06 (m, 2H), 3.04-2.94 (m, 1H), 2.70-2.60 (m, 2H), 2.16-2.06 (m, 2H), 2.01-1.68 (m, 10H), 1.53 (s, 9H), 1.21 (d, J=6.8 Hz, 6H) LCMS [ESI, M+1]:618.3.

Step D. 4-(3,8-diazabicyclo[3.2.1]octan-3-yl)-8-fluoro-2-((hexahydro-1H-pyrrolizin-7a-yl)methoxy)-7-(4-isopropylpyridin-3-yl)pyrido[4,3-d]pyrimidine. To a mixture of tert-butyl3-(8-fluoro-2-((hexahydro-1H-pyrrolizin-7a-yl) methoxy)-7-(4-isopropylpyridin-3-yl)pyrido[4,3-d] pyrimidin-4-yl)-3,8-diazabicyclo[3.2.1]octane-8-carboxylate (90 mg, 146 μmol, 1.0 eq) and ACN (2 mL) was added HCl·dioxane (4 M, 2 mL, 54.9 eq) at 0° C. Then it was degassed and purged with $N_2$ for 3 times. The reaction was stirred at 15° C. for 20 minutes. Upon completion, the mixture was concentrated. The residue was adjusted to pH=8 with saturated $NaHCO_3$ aqueous solution. The mixture was diluted by MeOH and purified by prep-HPLC (column: Waters Xbridge C18 150*50 mm*10 um; mobile phase: [water (10 mM $NH_4HCO_3$)-ACN]; B %: 16%-46%, 10 min). The desired fraction was collected and concentrated under vacuum to remove ACN. The desired fraction was collected and lyophilized to affording the title compound (25.3 mg, 33% yield), Off-white solid; $^1$H NMR (400 MHz, CHLOROFORM-d) δ=9.03 (s, 1H), 8.62 (d, J=5.6 Hz, 1H), 8.55 (s, 1H), 7.36 (d, J=5.6 Hz, 1H), 4.64-4.55 (m, 2H), 4.17 (s, 2H), 3.72-3.59 (m, 4H), 3.15-3.06 (m, 2H), 3.05-2.96 (m, 1H), 2.69-2.59 (m, 2H), 2.16-2.05 (m, 2H), 1.95-1.79 (m, 8H), 1.71-1.62 (m, 2H), 1.20 (d, J=6.8 Hz, 6H). LCMS [ESI, M+1]:518.3.

Example 307

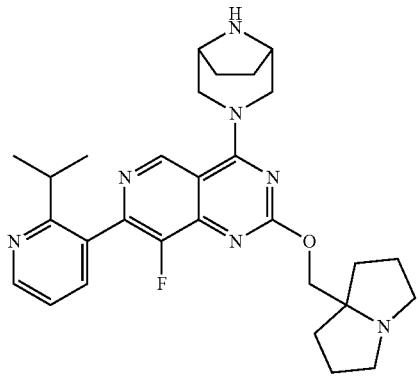 [SMILES: CC(C)c1ncccc1-c1ncc2c(N3CC4CCC(C3)N4)nc(OCC34CCCN3CCC4)nc2c1F]

4-((1R,5S)-3,8-diazabicyclo[3.2.1]octan-3-yl)-8-fluoro-2-((hexahydro-1H-pyrrolizin-7a-yl)methoxy)-7-(2-isopropylpyridin-3-yl)pyrido[4,3-d]pyrimidine

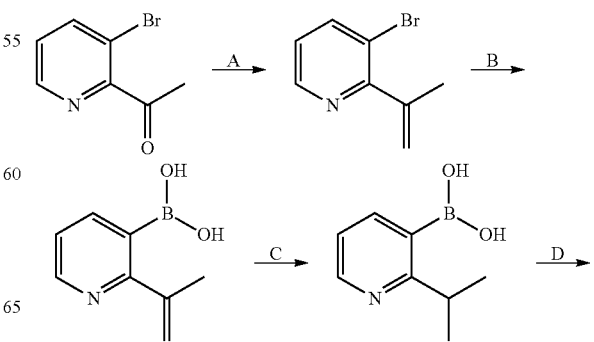

-continued

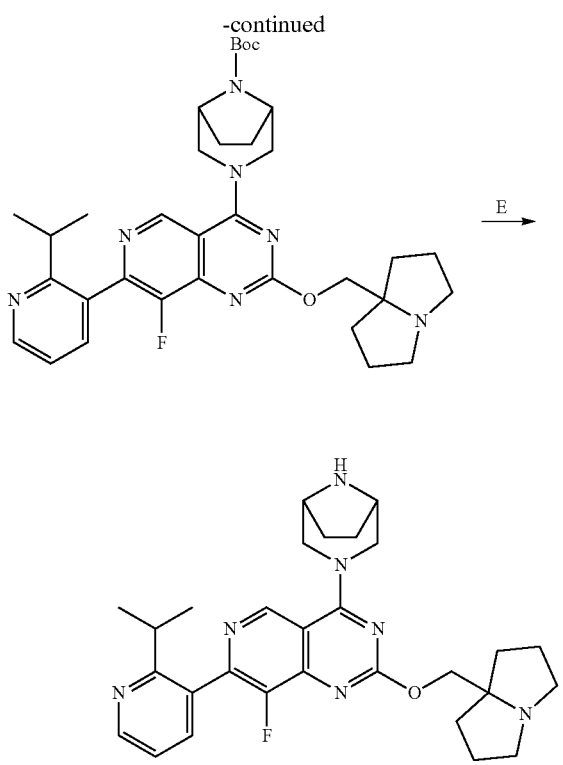

Step A. 3-bromo-2-(prop-1-en-2-yl)pyridine. To a mixture of methyl(triphenyl)phosphonium; bromide (2.68 g, 7.50 mmol, 1.5 eq), THF (15 mL) and DMF (15 mL) was added t-BuOK (842 mg, 7.50 mmol, 1.5 eq) at 0° C. The mixture was stirred at 20° C. for 0.5 hour. 1-(3-bromopyridin-2-yl)ethanone (1 g, 5.0 mmol, 1.0 eq) in THF (3 mL) was added at 0° C. The mixture was stirred at 20° C. for 2 hours. After completion, the reaction was poured into ice water (500 mL) and extracted with ethyl acetate (150 mL×6). The combined organic layers were dried over anhydrous $Na_2SO_4$, filtered and concentrated under reduced pressure to give a residue. The residue was purified by column chromatography ($SiO_2$, petroleum ether/ethyl acetate=15/1) to give the title compound (0.6 g, 60% yield). Colorless oil; Rf=0.57 (10:1, petroleum ether/ethyl acetate); $^1$H NMR (400 MHz, chloroform-d) δ=8.52 (dd, J=1.6, 4.8 Hz, 1H), 7.90 (dd, J=1.2, 8.0 Hz, 1H), 7.07 (dd, J=4.4, 8.4 Hz, 1H), 5.47-5.38 (m, 1H), 5.30-5.23 (m, 1H), 2.22-2.17 (m, 3H).

Step B. (2-(prop-1-en-2-yl)pyridin-3-yl)boronic acid. A solution of 3-bromo-2-(prop-1-en-2-yl)pyridine (200 mg, 1.01 mmol, 1.0 eq) in THF (5 mL) was degassed and purged with $N_2$ for 3 times. n-Buli (2.5 M, 0.5 mL, 1.24 eq) was added dropwise at −70° C. and the mixture was stirred at −70° C. for 0.5 hour under $N_2$ atmosphere. 2-isopropoxy-4,6-dimethyl-1,3,2-dioxaborinane (208 mg, 1.21 mmol, 1.2 eq) was added at −70° C. and the mixture was stirred at −70° C. for 0.5 hour. Then the mixture was stirred at −70~ 15° C. for 1 hour. HCl (2 M in $H_2O$) was added dropwise at 0° C. (the pH of the mixture was adjusted to 2) and the mixture was stirred at 0~15° C. for 0.5 hour. After completion, the pH of the reaction mixture was adjusted to 8~ 9 with 25% $NH_3·H_2O$ below 5° C. and concentrated under reduced pressure to give a residue. The residue was purified with reversed phase flash chromatography [water (FA, 0.1%)/acetonitrile=1/0] to give the title compound (250 mg, crude). Yellow solid; LCMS [ESI, M+1]: 164.1.

Step C. (2-isopropylpyridin-3-yl)boronic acid. To a solution of (2-(prop-1-en-2-yl)pyridin-3-yl)boronic acid (250 mg, crude) in MeOH (10 mL) was added $PtO_2$ (50 mg). The mixture was stirred at 15° C. for 2 hours under $H_2$ atmosphere (15 psi). After completion, the reaction mixture was filtered and the filtrate was concentrated under reduced pressure to give the title compound (210 mg, crude). Light yellow solid; LCMS [ESI, M+1]: 166.1.

Step D. tert-butyl (1R,5S)-3-(8-fluoro-7-(2-isopropylpyridin-3-yl)-2-((tetrahydro-1H-pyrrolizin-7a(5H)-yl)methoxy)pyrido[4,3-d]pyrimidin-4-yl)-3,8-diazabicyclo[3.2.1]octane-8-carboxylate. A mixture of tert-butyl 3-(7-chloro-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (110 mg, 206 μmol, 1.0 eq), (2-isopropylpyridin-3-yl)boronic acid (70 mg, crude), $K_2CO_3$ (86 mg, 622 μmol, 3.02 eq), dicyclohexyl-[2-(2,6-diisopropoxyphenyl)phenyl] phosphane (10 mg, 21.4 μmol, 0.1 eq) in dioxane (1.2 mL) and $H_2O$ (0.3 mL) was degassed and purged with $N_2$ for 3 times. [2-(2-aminophenyl)phenyl]-methylsulfonyloxy-palladium; dicyclohexyl-[2-(2,6-diisopropoxyphenyl)phenyl]phosphane (18 mg, 21.5 μmol, 0.1 eq) was added and the mixture was stirred at 110° C. for 4 hours under $N_2$. After completion, the reaction mixture was diluted with ethyl acetate (1 mL) and $H_2O$ (3 mL). The mixture was extracted with ethyl acetate (2 mL×4). The combined organic layers were dried over anhydrous $Na_2SO_4$, filtered and concentrated under reduced pressure to give a residue. The residue was purified by reversed phase flash chromatography [water (FA, 0.1%)/acetonitrile=13/7] to give the title compound (23 mg, 17% yield). Light yellow gum; LCMS [ESI, M+1]: 618.3.

Step E. 4-((1R,5S)-3,8-diazabicyclo[3.2.1]octan-3-yl)-8-fluoro-2-((hexahydro-1H-pyrrolizin-7a-yl)methoxy)-7-(2-isopropylpyridin-3-yl)pyrido[4,3-d]pyrimidine. To a solution tert-butyl (1R,5S)-3-(8-fluoro-7-(2-isopropylpyridin-3-yl)-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (23 mg, 37.2 μmol, 1.0 eq) in ACN (1 mL) was added HCl·dioxane (4 M, 1 mL) dropwise below 10° C. The mixture was stirred at 10° C. for 1 hour. The reaction mixture was concentrated under reduced pressure to give a residue at 10° C. (without heating). The residue was dissolved in MeOH (0.5 mL) and MeCN (1 mL). The pH of the mixture was adjusted to 7-8 with 25% $NH_3·H_2O$ (0.1 mL) dissolved in MeCN (3 mL)]. The residue was purified by prep-HPLC (column: Shim-pack C18 150*25*10 um; mobile phase: [water (0.225% FA)-ACN]; B %: 0%-20%, 10 min) to give the title compound (7.36 mg, 31% yield, 1.8 FA). Yellow solid; $^1$H NMR (400 MHz, methanol-d4) δ=9.19 (s, 1H), 8.68 (dd, J=1.6, 4.8 Hz, 1H), 7.82 (dd, J=1.6, 8.0 Hz, 1H), 7.43 (dd, J=4.8, 8.0 Hz, 1H), 4.79 (d, J=13.2 Hz, 2H), 4.69 (s, 2H), 4.02 (s, 2H), 3.90 (d, J=12.8 Hz, 2H), 3.75-3.69 (m, 2H), 3.32-3.28 (m, 2H), 3.10-3.00 (m, 1H), 2.40-2.33 (m, 2H), 2.28-2.20 (m, 4H), 2.16-2.09 (m, 2H), 2.06-1.95 (m, 4H), 1.25 (d, J=6.8 Hz, 6H); LCMS [ESI, M+1]: 518.3.

Example 308
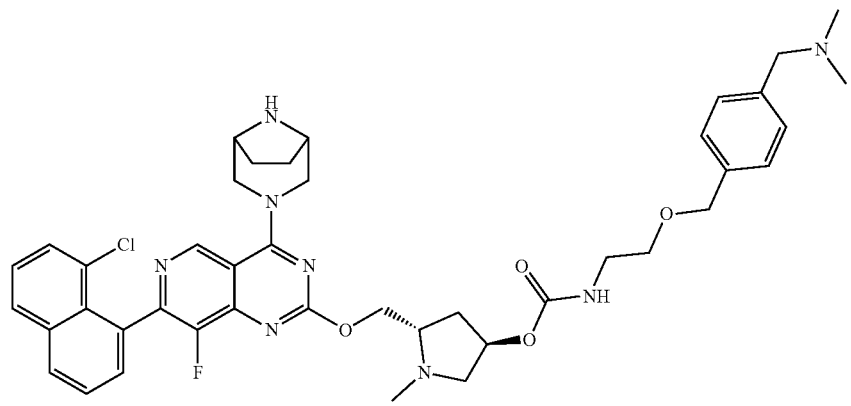 [SMILES: CN(C)Cc1ccc(COCCNC(=O)O[C@@H]2C[C@@H](COc3nc(N4CC5CCC(C4)N5)c4cnc(-c5cccc6cccc(Cl)c56)c(F)c4n3)N(C)C2)cc1]
(3R,5S)-5-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)-1-methylpyrrolidin-3-yl (2-((4-((dimethylamino)methyl)benzyl)oxy)ethyl)carbamate
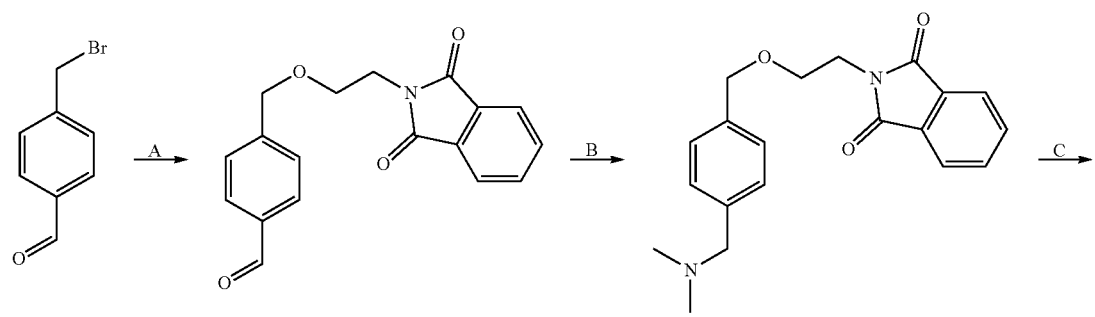
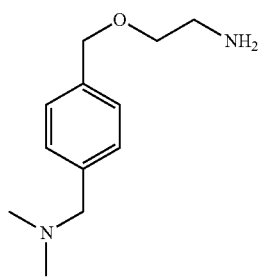

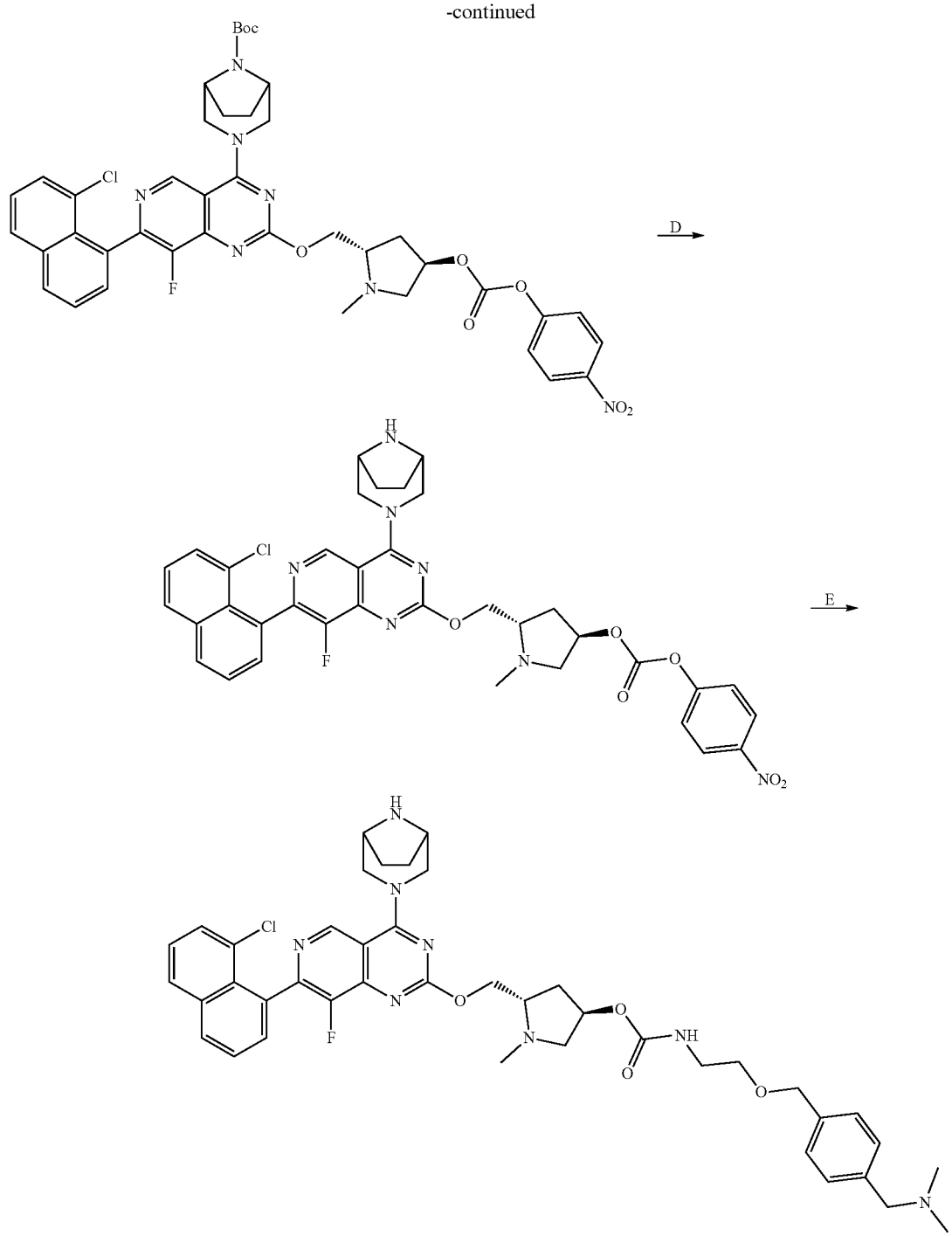

Step A. 4-((2-(1,3-Dioxoisoindolin-2-yl)ethoxy)methyl)benzaldehyde. To a solution of 2-(2-hydroxyethyl)isoindoline-1,3-dione (2.0 g, 10.5 mmol, 1.0 eq) in THF (40 mL) was added NaH (836 mg, 20.9 mmol, 60% purity, 2.0 eq) at 0° C., and the mixture was stirred at 20° C. for 0.5 hour. Then 4-(bromomethyl)benzaldehyde (2.5 g, 12.5 mmol, 1.2 eq) was added at 0° C. and the reaction was warmed up to 20° C. for 12 hours. After completion, the reaction mixture was filtered and the filtrate was concentrated under reduced pressure to give a residue. The residue was purified by column chromatography (SiO$_2$, petroleum ether:ethyl acetate=6:1) to give the title compound (1.31 g, 40% yield). White solid; $^1$H NMR (400 MHz, chloroform-d) δ=9.96 (s, 1H), 7.89-7.82 (m, 2H), 7.78 (d, J=8.0 Hz, 2H), 7.76-7.68 (m, 2H), 7.43 (d, J=7.6 Hz, 2H), 4.62 (s, 2H), 4.01-3.93 (m, 2H), 3.82-3.75 (m, 2H).

Step B. 2-(2-((4-((Dimethylamino)methyl)benzyl)oxy)ethyl)isoindoline-1,3-dione. To a solution of 4-((2-(1,3-dioxoisoindolin-2-yl)ethoxy)methyl)benzaldehyde (1.31 g, 4.24 mmol, 1.0 eq) in THF (20 mL) was added N-methylmethanamine (2 M in THF, 3.18 mL, 1.5 eq) at 0° C. and the mixture was stirred at 20° C. for 3 hours. Then sodium triacetoxyborohydride (1.80 g, 8.47 mmol, 2.0 eq) was added at 0° C. The mixture was warmed up to 20° C. and stirred for 3 hours. After completion, the reaction mixture was filtered and the filtrate was concentrated under reduced pressure to give a residue. The residue was purified by reversed phase flash chromatography (water (0.1% formic acid)/acetonitrile)) to give the title compound (0.63 g, 43% yield). Colorless oil. $^1$H NMR (400 MHz, chloroform-d) δ=7.85 (dd, J=2.8, 5.2 Hz, 2H), 7.72 (dd, J=3.2, 5.2 Hz, 2H), 7.26-7.17 (m, 4H), 4.53 (s, 2H), 3.94 (t, J=6.0 Hz, 2H), 3.73 (t, J=5.6 Hz, 2H), 3.37 (s, 2H), 2.22 (s, 6H). LCMS [ESI, M+1]: 339.1.

Step C. 2-((4-((Dimethylamino)methyl)benzyl)oxy)ethanamine. To a solution of 2-(2-((4-((dimethylamino)methyl)benzyl)oxy)ethyl)isoindoline-1,3-dione (0.63 g, 1.86 mmol, 1.0 eq) in ethyl alcohol (15 mL) was added hydrazine; hydrate (1.10 g, 18.6 mmol, 1.07 mL, 85% purity, 10.0 eq). The mixture was stirred at 80° C. for 1 hour. After completion, the reaction mixture was filtered and the filtrate was concentrated under reduced pressure to give the title compound (575 mg, crude). White solid. $^1$H NMR (400 MHz, methanol-d4) δ=7.36-7.27 (m, 4H), 4.55 (s, 2H), 3.57 (t, J=5.2 Hz, 2H), 3.47 (s, 2H), 2.89 (t, J=5.2 Hz, 2H), 2.23 (s, 6H).

Step D. (3R,5S)-5-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)-1-methylpyrrolidin-3-yl (4-nitrophenyl) carbonate. To a solution of (1R,5S)-tert-butyl-3-(7-(8-chloronaphthalen-1-yl)-8-fluoro-2-(((2S,4R)-1-methyl-4-(((4-nitrophenoxy)carbonyl)oxy)pyrrolidin-2-yl)methoxy)pyrido[4,3-d]pyrimidin-4-yl)-3,8-diazabicyclo[3.2.1]octane-8-carboxylate (synthesized according to Example 280, step A, 50.0 mg, 61.4 μmol, 1.0 eq) in CH₃CN (1 mL) was added HCl·dioxane (4 M, 500 μL, 32.5 eq). The mixture was stirred at 0° C. for 1 hour. After completion, the mixture was directly concentrated under reduced pressure to give the title compound (57 mg, crude). Yellow solid. LCMS [ESI, M+1]: 714.3.

Step E. (3R,5S)-5-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)-1-methylpyrrolidin-3-yl (2-((4-((dimethylamino)methyl)benzyl)oxy)ethyl)carbamate. To a solution of (3R,5S)-5-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)-1-methylpyrrolidin-3-yl (4-nitrophenyl) carbonate (57 mg, 79.8 mol, 1.0 eq) and 2-((4-((dimethylamino)methyl)benzyl)oxy)ethanamine (49.9 mg, 239 mol, 3.0 eq) in DMF (1 mL) was added DIEA (51.6 mg, 399 mol, 69.5 μL, 5.0 eq). The mixture was stirred at 20° C. for 12 hours. After completion, The mixture was filtrated and the filtrate was purified by prep-HPLC (column: Phenomenex Gemini-NX C18 75*30 mm*3 um; mobile phase: [water (0.1% TFA)-ACN]; B %: 20%-30%, 7 min). The desired fraction was collected and lyophilized to give the title compound (10.5 mg, 10% yield, 3TFA). Yellow solid; $^1$H NMR (400 MHz, methanol-d4) δ=9.14 (s, 1H), 8.16 (dd, J=1.2, 8.4 Hz, 1H), 8.03 (dd, J=1.2, 8.4 Hz, 1H), 7.74-7.66 (m, 1H), 7.64-7.57 (m, 2H), 7.56-7.44 (m, 5H), 5.35 (br s, 1H), 5.03-4.89 (m, 3H), 4.80-4.72 (m, 1H), 4.59 (s, 2H), 4.33-4.24 (m, 4H), 4.23-4.02 (m, 2H), 4.02-3.93 (m, 2H), 3.58 (t, J=5.2 Hz, 2H), 3.51-3.34 (m, 3H), 3.18 (br s, 3H), 2.84 (s, 6H), 2.56-2.35 (m, 2H), 2.24-2.06 (m, 4H); LCMS [ESI, M+1]: 783.0.

Example 309

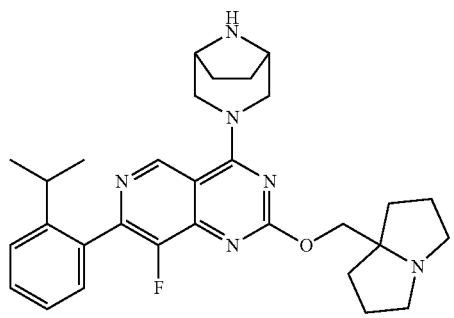 [SMILES: CC(C)c1ccccc1-c1ncc2c(N3CC4CCC(C3)N4)nc(OCC34CCCN3CCC4)nc2c1F]

4-((1R,5S)-3,8-diazabicyclo[3.2.1]octan-3-yl)-8-fluoro-7-(2-isopropylphenyl)-2-((tetrahydro-1H-pyrrolizin-7a(5H)-yl)methoxy)pyrido[4,3-d]pyrimidine

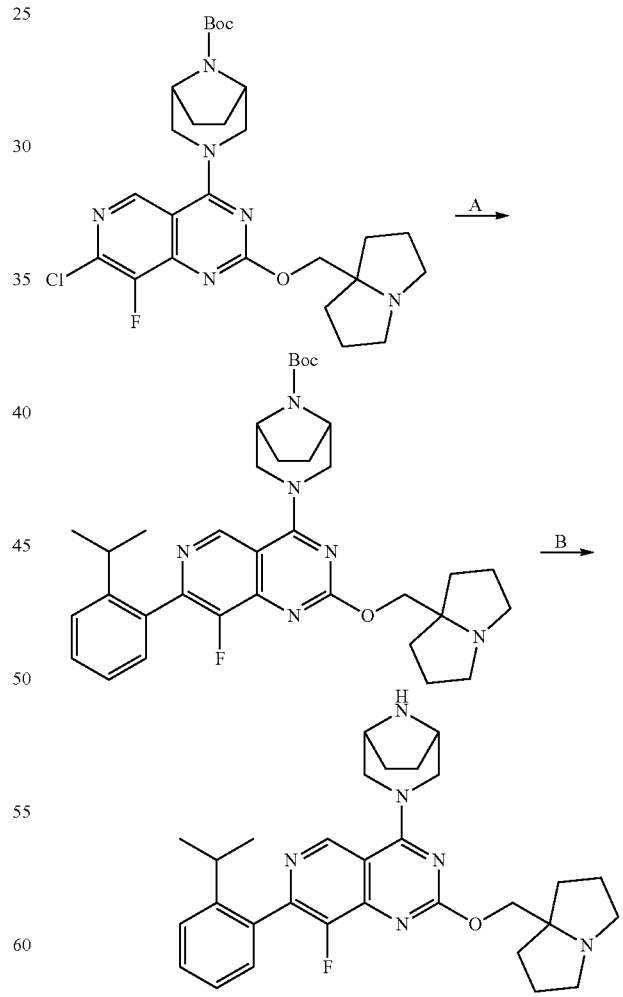

Step A. tert-butyl (1R,5S)-3-(8-fluoro-7-(2-isopropylphenyl)-2-((tetrahydro-1H-pyrrolizin-7a(5H)-yl)methoxy)pyrido[4,3-d]pyrimidin-4-yl)-3,8-diazabicyclo[3.2.1]octane-8-carboxylate. To a solution of (1R,5S)-tert-butyl 3-(7- chloro-8-fluoro-2-((hexahydro-1H-pyrrolizin-7a-yl) methoxy)pyrido[4,3-d]pyrimidin-4-yl)-3,8-diazabicyclo [3.2.1]octane-8-carboxylate (110 mg, 206 μmol, 1 eq) and K₃PO₄ (1.5 M in H₂O, 0.5 mL, 3.6 eq) in THF (1.5 mL) was degassed and purged with N₂ for 3 times, 2-(2-isopropylphenyl)-4,4,5,5-tetramethyl-1,3,2-dioxaborolane (51 mg, 310 μmol, 1.5 eq) and [2-(2-aminophenyl)phenyl]palladium (1+); bis(1-adamantyl)-butyl-phosphane; methanesulfonate (15 mg, 20.6 μmol, 0.1 eq) was added. The mixture was stirred at 60° C. for 2 hours under N₂ atmosphere. After completion, the reaction mixture was diluted with H₂O (2 mL) and brine (1 mL), and extracted with EtOAc (2 mL×4). The combined organic layers were concentrated under reduced pressure to give a residue. The residue was purified by reversed phase flash chromatography [water (FA, 0.1%)/acetonitrile=2/3] to give the title compound (120 mg, 93% yield). Light yellow gum; LCMS [ESI, M+1]: 617.3.

Step B. 4-((1R,5S)-3,8-diazabicyclo[3.2.1]octan-3-yl)-8-fluoro-7-(2-isopropylphenyl)-2-((tetrahydro-1H-pyrrolizin-7a(5H)-yl)methoxy)pyrido[4,3-d]pyrimidine. To a solution of tert-butyl (1R,5S)-3-(8-fluoro-7-(2-isopropylphenyl)-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (120 mg, 194 μmol, 1 eq) in MeCN (4 mL) was added HCl·dioxane (4 M, 1 mL) at 0° C. The mixture was stirred at 0-15° C. for 0.5 hour. After completion, the reaction mixture was concentrated under reduced pressure at room temperature (without heating) to give a residue. The residue was dissolved in EtOAc (5 mL) and H₂O (2 mL). The pH of the mixture was adjusted to 7-8 with NaHCO₃ solid below 10° C. The mixture was extracted with EtOAc (5 mL×4). The combined organic layers were dried over anhydrous Na₂SO₄, filtered and concentrated under reduced pressure to give a residue. The residue was purified by prep-HPLC (column: Shim-pack C18 150*25*10 um; mobile phase: [water (0.225% FA)-ACN]; B %: 11%-31%, 9 min). The desired fractions were collected and lyophilized to give the title compound (74.2 mg, 62% yield, 2FA). Off-white solid; ¹H NMR (400 MHz, methanol-d4) δ=9.14 (s, 1H), 7.54-7.48 (m, 2H), 7.35-7.28 (m, 2H), 4.80 (d, J=13.2 Hz, 2H), 4.67 (s, 2H), 4.06 (br s, 2H), 3.91 (d, J=13.2 Hz, 2H), 3.74-3.68 (m, 2H), 3.30-3.26 (m, 2H), 2.87-2.82 (m, 1H), 2.38-2.31 (m, 2H), 2.26-1.95 (m, 10H), 1.18 (d, J=6.8 Hz, 6H); LCMS [ESI, M+1]: 517.3.

Example 310

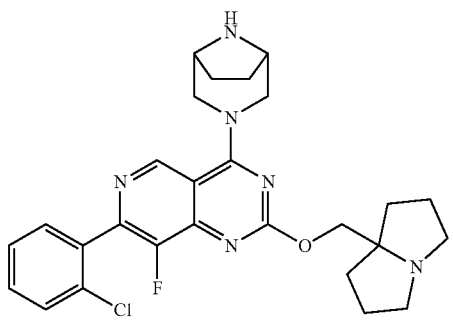 [SMILES: Fc1c(-c2ccccc2Cl)ncc2c(N3CC4CCC(C3)N4)nc(OCC34CCCN3CCC4)nc12]

4-((1R,5S)-3,8-diazabicyclo[3.2.1]octan-3-yl)-7-(2-chlorophenyl)-8-fluoro-2-((hexahydro-1H-pyrrolizin-7a-yl)methoxy)pyrido[4,3-d]pyrimidine

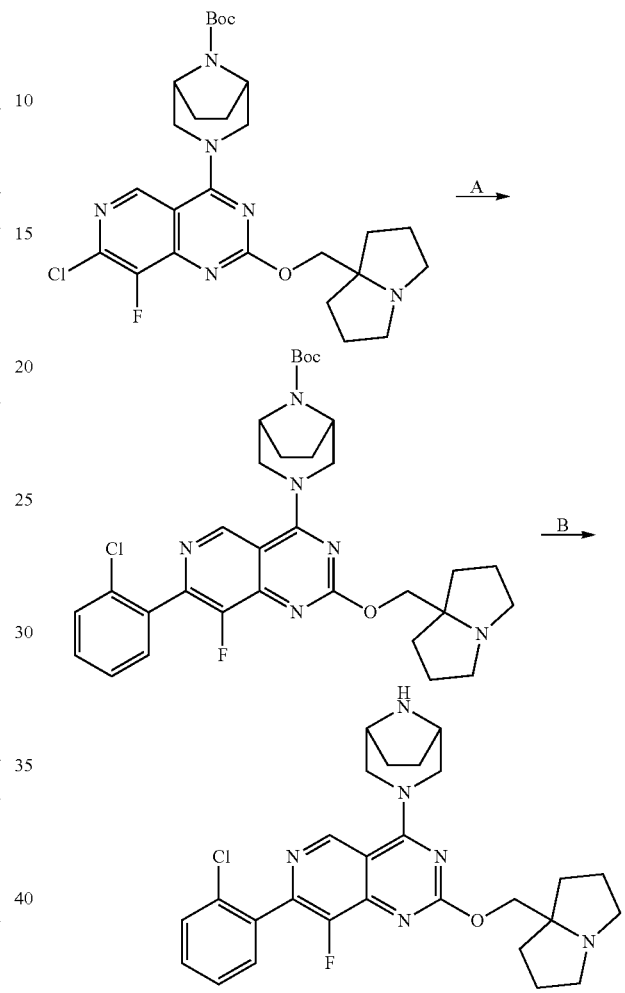

Step A. (1R,5S)-tert-butyl 3-(7-(2-chlorophenyl)-8-fluoro-2-((hexahydro-1H-pyrrolizin-7a-yl)methoxy)pyrido [4,3-d]pyrimidin-4-yl)-3,8-diazabicyclo[3.2.1]octane-8-carboxylate. To a mixture of (1R,5S)-tert-butyl 3-(7-chloro-8-fluoro-2-((hexahydro-1H-pyrrolizin-7a-yl)methoxy)pyrido [4,3-d]pyrimidin-4-yl)-3,8-diazabicyclo[3.2.1]octane-8-carboxylate (300 mg, 562 μmol, 1.0 eq) and toluene (5 mL) was added K₃PO₄ (1.5 M, 1.13 mL, 3 eq) in one portion at 25° C. under N₂. Then [2-(2-aminophenyl)phenyl] palladium(1+); bis(1-adamantyl)-butyl-phosphane; methanesulfonate (61.4 mg, 84.4 μmol, 0.15 eq) and (2-chlorophenyl)boronic acid (440 mg. 2.81 μmol, 5.0 eq) were added. The suspension was degassed under vacuum and purged with N₂ several times. The mixture was heated to 80° C. and stirred for 1 hour. Upon completion, the mixture was filtered and concentrated in vacuum to give a residue. The crude product was purified by reversed phase flash chromatography (0.1% FA condition) affording the title compound (180 mg, 49% yield, 93% purity). Yellow solid; LCMS [ESI, M+1]: 609.1.

Step B. 4-((1R,5S)-3,8-diazabicyclo[3.2.1]octan-3-yl)-7-(2-chlorophenyl)-8-fluoro-2-((hexahydro-1H-pyrrolizin-7a- yl)methoxy)pyrido[4,3-d]pyrimidine. To a mixture of (1R,5S)-tert-butyl 3-(7-(2-chlorophenyl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (180 mg, 295 μmol, 1 eq) and ACN (0.5 mL) was added HCl·dioxane (0.5 mL), and the reaction mixture was stirred at 25° C. for 10 minutes. Upon completion, the mixture was concentrated in vacuum to give a residue. The residue was purified by prep-HPLC (column: Phenomenex Luna C18 150*25 mm*10 um; mobile phase: [water (0.225% FA)-ACN]; B %: 1%-30%, 10 min) affording the title compound (70.1 mg, 43% yield, 1.9FA). Off-white solid; $^1$H NMR (400 MHz, methanol-d4) δ=9.15 (s, 1H), 7.62-7.47 (m, 4H), 4.80 (br d, J=13.2 Hz, 2H), 4.67 (s, 2H), 4.11-4.06 (m, 2H), 3.92 (br d, J=13.2 Hz, 2H), 3.76-3.65 (m, 2H), 3.30-3.26 (m, 2H), 2.40-2.30 (m, 2H), 2.25-1.96 (m, 10H); LCMS [ESI, M+1]: 509.

Example 311

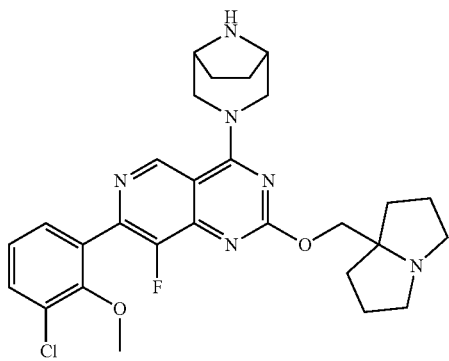

4-((1R,5S)-3,8-diazabicyclo[3.2.1]octan-3-yl)-7-(3-chloro-2-methoxyphenyl)-8-fluoro-2-((hexahydro-1H-pyrrolizin-7a-yl)methoxy)pyrido[4,3-d]pyrimidine

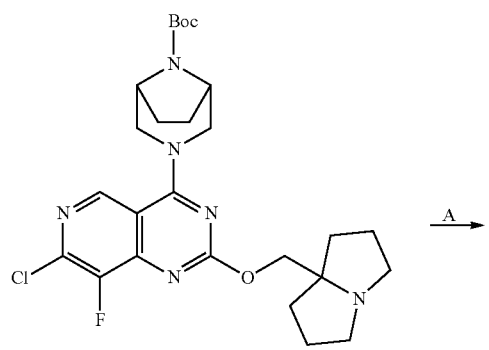

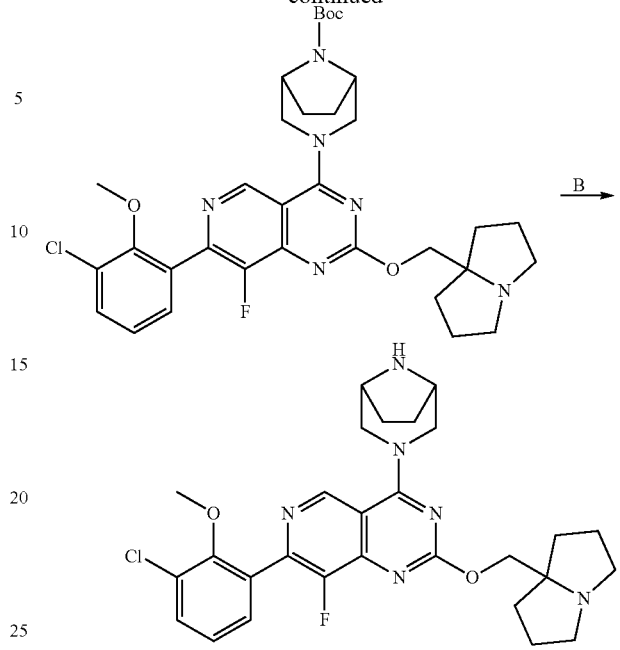

Step A. Tert-butyl-3-(7-(3-chloro-2-methoxyphenyl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate. To a solution of (1R,5S)-tert-butyl 3-(7-chloro-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (100 mg, 188 mol, 1.0 eq) and K$_3$PO$_4$ (1.5 M in H$_2$O, 375 μL, 3.6 eq) in THF (2 mL) was degassed and purged with N$_2$ for 3 times, and (3-chloro-2-methoxyphenyl) boronic acid (52.4 mg, 281.4 mol, 1.5 eq) and [2-(2-aminophenyl)phenyl]palladium(1+); bis(1-adamantyl)-butyl-phosphane; methanesulfonate (13.6 mg, 18.7 mol, 0.1 eq) were added. The mixture was stirred at 60° C. for 2 hours under N$_2$ atmosphere. After completion, the reaction mixture was diluted with H$_2$O (5 mL), and extracted with EA (5 mL×3). The combined organic layers were concentrated under reduced pressure to give a residue. The residue was purified reversed phase flash [water (FA, 0.10%)/acetonitrile=2/3] to give the title compound (60 mg, 49% yield). Light yellow gum; LCMS [ESI, M+1]: 639.2.

Step B. 4-(3,8-Diazabicyclo[3.2.1]octan-3-yl)-7-(3-chloro-2-methoxyphenyl)-8-fluoro-2-((hexahydro-1H-pyrrolizin-7a-yl)methoxy)pyrido[4,3-d]pyrimidine. To a solution of Tert-butyl-3-(7-(3-chloro-2-methoxyphenyl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (50 mg, 78.2 mol, 1.0 eq) in MeCN (1 mL) was added HCl·dioxane (4 M, 1 mL) at 20° C. The mixture was stirred at 20° C. for 1 hour. After completion, the reaction mixture was concentrated under reduced pressure at room temperature to give a residue. The residue was dissolved in MeOH (1 mL). The pH of the mixture was adjusted to 7-8 with saturated Na$_2$CO$_3$ solution. The mixture was purified by prep-HPLC (column: Shim-pack C18 150*25*10 um; mobile phase: [water (0.225% FA)-ACN]; B %: 7%-27%, 9 min). The desired fractions were collected and lyophilized to give the title compound (23.8 mg, 49% yield, 1.7FA). Off-white solid; $^1$H NMR (400 MHz, methanol-d4) δ=9.16 (s, 1H), 7.61 (dd, J=1.6, 8.0 Hz, 1H), 7.42 (dd, J=1.6, 8.0 Hz, 1H), 7.33-7.23 (m, 1H), 4.79 (br d, J=13.2 Hz, 2H), 4.67 (s, 2H), 4.05 (br s, 2H), 3.90 (br d, J=13.6 Hz, 2H), 3.76-3.64 (m, 5H), 3.31-3.26 (m, 2H), 2.38-1.94 (m, 12H); LCMS [ESI, M+1]: 539.2.

Example 312

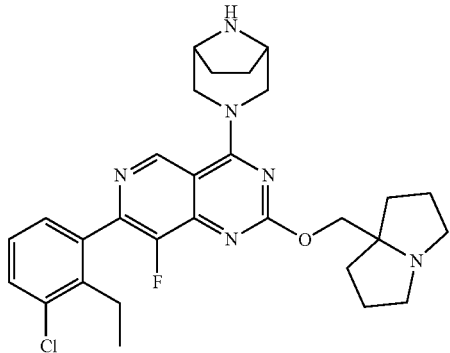 [SMILES: COc1c(Cl)cccc1-c1ncc2c(N3CC4CCC(C3)N4)nc(OCC34CCCN3CCC4)nc2c1F]

4-((1R,5S)-3,8-diazabicyclo[3.2.1]octan-3-yl)-7-(3-chloro-2-ethylphenyl)-8-fluoro-2-((hexahydro-1H-pyrrolizin-7a-yl)methoxy)pyrido[4,3-d]pyrimidine

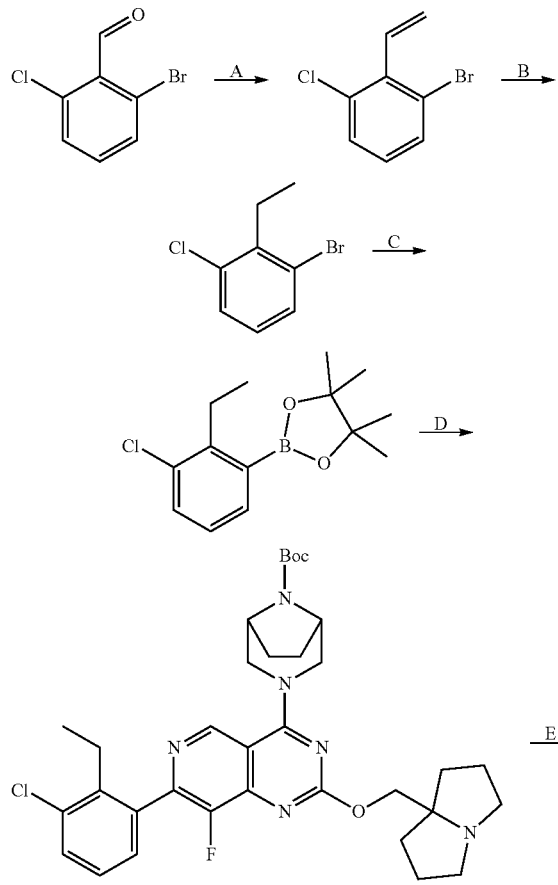

-continued

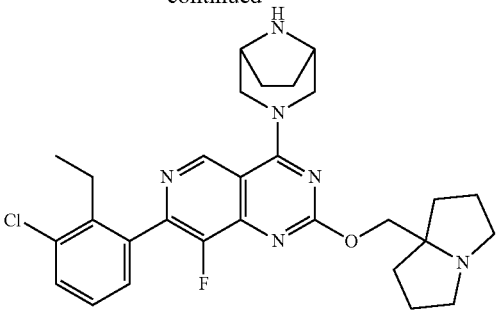

Step A. 1-bromo-3-chloro-2-vinyl-benzene. To a mixture of methyl(triphenyl)phosphonium; bromide (895 mg, 2.51 mmol, 1.1 eq) in THF (5 mL) was added t-BuOK (1 M in THF, 2.73 mL, 1.2 eq) dropwise at 0° C. After the mixture was stirred at 0° C. for 0.5 hour and at 10° C. for 10 minutes, 2-bromo-6-chloro-benzaldehyde (500 mg, 2.28 mmol, 1.0 eq) in THF (5 mL) was added and the mixture was stirred at 10° C. for 21 hours. After completion, the mixture was diluted with ethyl acetate (10 mL) and water (10 mL) and the organic layer was separated. The aqueous phase was extracted with ethyl acetate (10 mL). The combined organic layer was washed with saturated brine (15 mL), dried over $Na_2SO_4$, filtered and concentrated under vacuum. The residue was purified by column chromatography ($SiO_2$, petroleum ether/ethyl acetate=100/1) to give the title compound (308 mg, 59% yield). Colorless oil. Rf=0.8 (5:1, petroleum ether/ethyl acetate). $^1$H NMR (400 MHz, $CDCl_3$-d) δ=7.52 (dd, J=0.8, 8.0 Hz, 1H), 7.37 (dd, J=0.8, 8.0 Hz, 1H), 7.03 (t, J=8.0 Hz, 1H), 6.67 (dd, J=11.6, 18.0 Hz, 1H), 5.73 (dd, J=1.2, 9.2 Hz, 1H), 5.71-5.68 (m, 1H).

Step B. 1-bromo-3-chloro-2-ethyl-benzene. To a solution of 1-bromo-3-chloro-2-vinylbenzene (308 mg, 1.42 mmol, 1.0 eq) in ethyl acetate (10 mL) was added $PtO_2$ (40 mg) under $N_2$. The suspension was degassed under vacuum and purged with $H_2$ several times. The mixture was stirred under $H_2$ (15 psi) at 10° C. for 1 hour. After completion, the reaction mixture was filtered through a pad of Celite and concentrated in vacuum to give the title compound (240 mg, 65% yield) which was used in next step without further purification. Green oil. Rf=0.95 (0:1, ethyl acetate/petroleum ether). $^1$H NMR (400 MHz, $CDCl_3$-d) δ=7.46 (dd, J=0.8, 8.0 Hz, 1H), 7.33-7.29 (m, 1H), 6.98 (t, J=8.0 Hz, 1H), 3.00 (q, J=7.6 Hz, 2H), 1.19 (t, J=7.2 Hz, 3H).

Step C. 2-(3-chloro-2-ethyl-phenyl)-4,4,5,5-tetramethyl-1,3,2-dioxaborolane. To a mixture of 1-bromo-3-chloro-2-ethylbenzene (240 mg, 1.09 mmol, 1.0 eq) and 4,4,5,5-tetramethyl-2-(4,4,5,5-tetramethyl-1,3,2-dioxaborolan-2-yl)-1,3,2-dioxaborolane (553 mg, 2.18 mmol, 2.0 eq) in dioxane (5 mL) was added KOAc (321 mg, 3.27 mmol, 3.0 eq). The mixture was degassed, and then Pd(dppf)Cl$_2$ (79.8 mg, 109 μmol, 0.10 eq) was added under $N_2$. The mixture was stirred at 110° C. for 1 hour under $N_2$. After completion, the mixture was diluted with ethyl acetate (8 mL) and water (8 mL), and then separated. The aqueous phase was extracted with ethyl acetate (8 mL). The combined organic layer was washed with saturated brine (10 mL), dried over $Na_2SO_4$, filtered and concentrated under vacuum. The residue was purified by reversed phase flash chromatography [water (FA, 0.10%)/acetonitrile] to give the title compound (175 mg, 58% yield). Brown oil. Rf=0.6 (10:1, petroleum ether/ethyl acetate). $^1$H NMR (400 MHz, $CDCl_3$-d) δ=7.68-

7.64 (m, 1H), 7.41 (dd, J=1.2, 8.0 Hz, 1H), 7.11 (t, J=7.6 Hz, 1H), 3.08 (q, J=7.6 Hz, 2H), 1.36 (s, 12H), 1.17 (t, J=7.6 Hz, 3H).

Step D. tert-butyl (1R,5S)-3-(7-(3-chloro-2-ethylphenyl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate. To a mixture of (1R,5S)-tert-butyl 3-(7-chloro-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (120 mg, 225 μmol, 1.0 eq) and 2-(3-chloro-2-ethylphenyl)-4,4,5,5-tetramethyl-1,3,2-dioxaborolane (120 mg, 450 μmol, 2.0 eq) in THF (3 mL) was added K$_3$PO$_4$ (1.5 M in water, 450 μL, 3.0 eq). The mixture was degassed and then [2-(2-aminophenyl)phenyl]palladium(1+); bis(1-adamantyl)-butyl-phosphane; methanesulfonate (16.40 mg, 22.51 μmol, 0.1 eq) was added. The mixture was stirred at 60° C. for 1 hour under N$_2$. After completion, the mixture was concentrated under vacuum. The residue was purified by reversed phase flash chromatography [water (FA, 0.1%)/acetonitrile] to give the title compound (96 mg, 66% yield). yellow solid. LCMS [ESI, M+1]: 637.2.

Step E. 4-((1R,5S)-3,8-diazabicyclo[3.2.1]octan-3-yl)-7-(3-chloro-2-ethylphenyl)-8-fluoro-2-((hexahydro-1H-pyrrolizin-7a-yl)methoxy)pyrido[4,3-d]pyrimidine. To a mixture of tert-butyl (1R,5S)-3-(7-(3-chloro-2-ethylphenyl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (60.0 mg, 94.2 μmol, 1.0 eq) and MeCN (0.5 mL) was added HCl·dioxane (4 M, 1 mL, 42 eq) at 10° C. The mixture was stirred at 10° C. for 0.5 hour. After completion, the mixture was concentrated under vacuum. The residue was purified by prep-HPLC (column: Shimpack C18 150*25*10 um; mobile phase: [water (0.225% FA)-ACN]; B %: 13%-33%, 9 min) to give the title compound (12.5 mg, 22% yield, 1.5 FA). $^1$H NMR (400 MHz, METHANOL-d4) δ=9.15 (s, 1H), 7.55 (dd, J=0.8, 7.6 Hz, 1H), 7.36-7.31 (m, 1H), 7.29-7.24 (m, 1H), 4.81 (br d, J=13.6 Hz, 2H), 4.68 (s, 2H), 4.12 (br s, 2H), 3.94 (br d, J=13.6 Hz, 2H), 3.76-3.67 (m, 2H), 3.34-3.25 (m, 2H), 2.74-2.66 (m, 2H), 2.39-2.31 (m, 2H), 2.28-2.16 (m, 4H), 2.14-1.97 (m, 6H), 1.05 (t, J=7.2 Hz, 3H). LCMS [ESI, M/2+1, M+1]: 269.4, 537.1.

Example 313

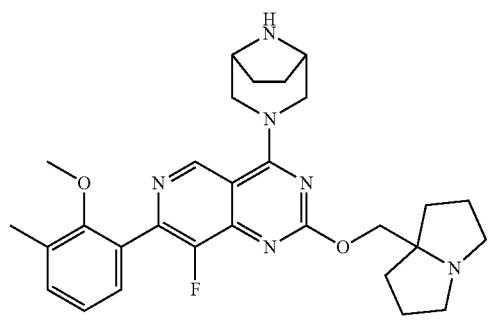 [SMILES: COc1c(C)cccc1-c1ncc2c(N3CC4CCC(C3)N4)nc(OCC34CCCN3CCC4)nc2c1F]

4-((1R,5S)-3,8-diazabicyclo[3.2.1]octan-3-yl)-8-fluoro-2-((hexahydro-1H-pyrrolizin-7a-yl)methoxy)-7-(2-methoxy-3-methylphenyl)pyrido[4,3-d]pyrimidine

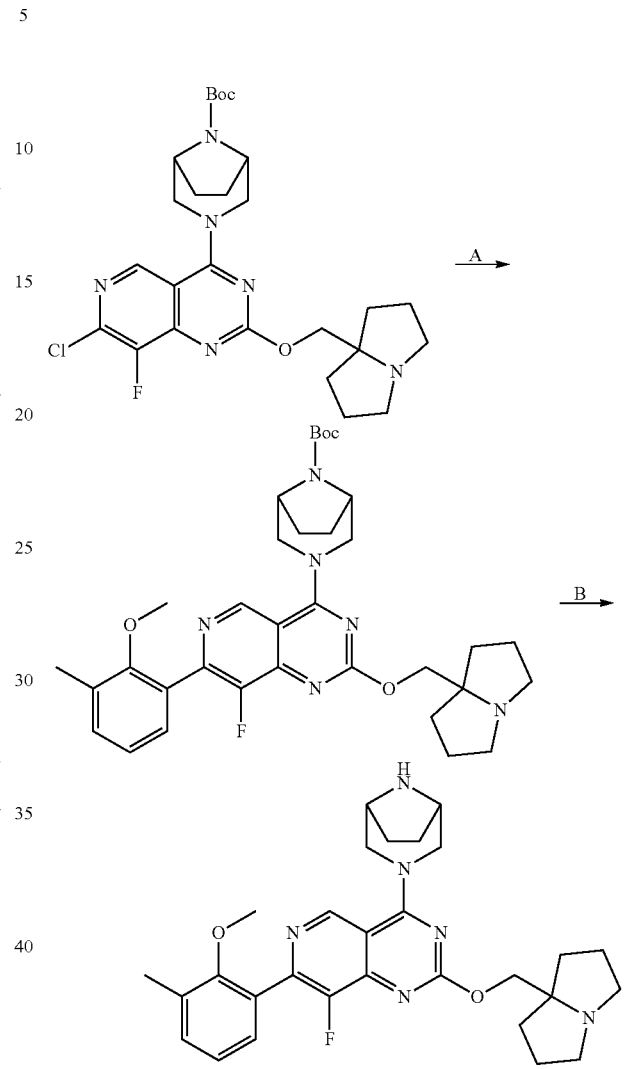

Step A. (1R,5S)-tert-butyl 3-(8-fluoro-2-((hexahydro-1H-pyrrolizin-7a-yl)methoxy)-7-(2-methoxy-3-methylphenyl)pyrido[4,3-d]pyrimidin-4-yl)-3,8-diazabicyclo[3.2.1]octane-8-carboxylate. A mixture of (1R,5S)-tert-butyl 3-(7-chloro-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (150 mg, 281 μmol, 1.00 eq), (2-methoxy-3-methyl-phenyl) boronic acid (142 mg, 855 μmol, 3.04 eq), [2-(2-aminophenyl)phenyl]palladium(1+); bis(1-adamantyl)-butyl-phosphane; methanesulfonate (41.0 mg, 56.3 μmol, 0.20 eq), and K$_3$PO$_4$ (1.50 M, 500 μL, 2.67 eq) in THF (2.0 mL) was degassed and purged with N$_2$ for 3 times, and then the mixture was stirred at 60° C. for 2 hours under N$_2$ atmosphere. After completion, the reaction mixture was diluted with H$_2$O (5.0 mL) and extracted with ethyl acetate (3×10 mL). The combined organic layers were washed with saturated brine (30 mL), dried over Na$_2$SO$_4$, filtered and concentrated under reduced pressure to give a residue. The residue was purified by reversed phase flash chromatography [C18, 0.1% FA in water, 0-50% MeCN] affording the title compound (120 mg, 69% yield). White solid; ¹H NMR (400 MHz, CDCl₃-d) δ=9.02 (s, 1H), 7.32-7.27 (m, 2H), 7.16-7.11 (m, 1H), 4.56 (br d, J=12.4 Hz, 2H), 4.39-4.36 (m, 2H), 4.19 (s, 2H), 3.77-3.58 (m, 2H), 3.55 (s, 3H), 3.15-3.07 (m, 2H), 2.68-2.60 (m, 2H), 2.38 (s, 3H), 2.13-2.04 (m, 2H), 1.99-1.93 (m, 2H), 1.90-1.83 (m, 4H), 1.81-1.73 (m, 2H), 1.71-1.62 (m, 2H), 1.53 (s, 9H); LCMS [ESI, M+1]: 619.3.

Step B. 4-((1R,5S)-3,8-diazabicyclo[3.2.1]octan-3-yl)-8-fluoro-2-((hexahydro-1H-pyrrolizin-7a-yl)methoxy)-7-(2-methoxy-3-methylphenyl)pyrido[4,3-d]pyrimidine. To a solution of (1R,5S)-tert-butyl 3-(8-fluoro-2-((hexahydro-1H-pyrrolizin-7a-yl)methoxy)-7-(2-methoxy-3-methylphenyl)pyrido[4,3-d]pyrimidin-4-yl)-3,8-diazabicyclo[3.2.1]octane-8-carboxylate (100 mg, 162 μmol, 1.00 eq) in MeCN (2.0 mL) was added HCl·dioxane (4 M, 1.0 mL). The mixture was stirred at 0° C. for 15 minutes. After completion, the reaction mixture was diluted with H₂O (5 mL) and extracted with ethyl acetate (3×5 mL). The combined organic layers were washed with saturated brine (10 mL), dried over Na₂SO₄, filtered and concentrated under reduced pressure to give a residue. The residue was purified by prep-HPLC (column: Shim-pack C18 150*25*10 um; mobile phase: [water (0.225% FA)-ACN]; B %: 7%-27%, 9 min) and lyophilized affording the title compound (53.4 mg, 54% yield, 1.9FA). Off-white solid; ¹H NMR (400 MHz, CDCl₃-d) δ=9.14 (s, 1H), 7.38 (d, J=7.2 Hz, 1H), 7.32-7.25 (m, 1H), 7.19 (t, J=7.6 Hz, 1H), 4.83-4.75 (m, 2H), 4.67 (s, 2H), 4.11-4.05 (m, 2H), 3.91 (d, J=13.2 Hz, 2H), 3.76-3.66 (m, 2H), 3.50 (s, 3H), 3.30-3.25 (m, 2H), 2.41-2.37 (m, 3H), 2.36-2.31 (m, 2H), 2.30-2.15 (m, 4H), 2.14-1.96 (m, 6H); LCMS [ESI, M+1]: 519.2.

Example 314

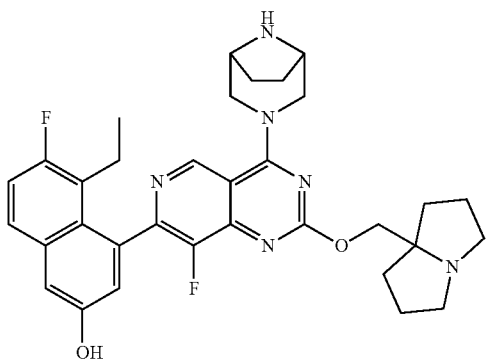 [SMILES: CCc1c(F)ccc2cc(O)cc(-c3ncc4c(N5CC6CCC(C5)N6)nc(OCC56CCCN5CCC6)nc4c3F)c12]

4-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)-5-ethyl-6-fluoronaphthalen-2-ol

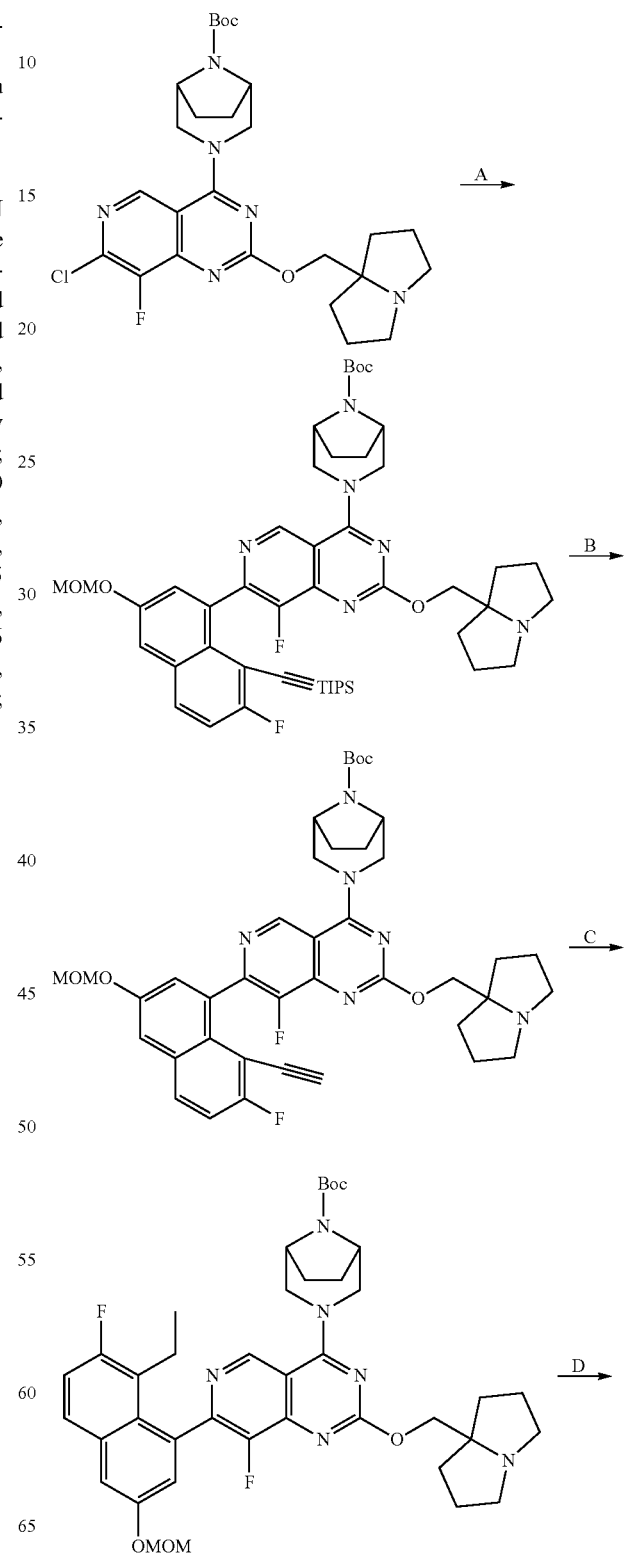

-continued

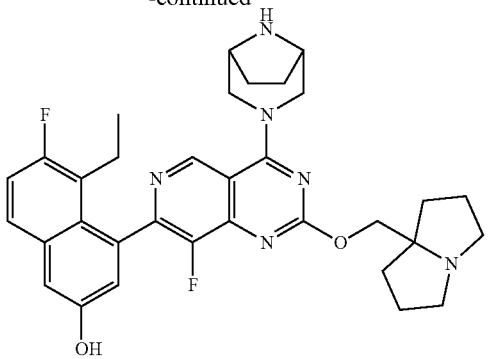

Step A. (1R,5S)-tert-butyl 3-(8-fluoro-7-(7-fluoro-3-(methoxymethoxy)-8-((triisopropylsilyl)ethynyl)naphthalen-1-yl)-2-((hexahydro-1H-pyrrolizin-7a-yl)methoxy)pyrido[4,3-d]pyrimidin-4-yl)-3,8-diazabicyclo[3.2.1]octane-8-carboxylate. To a mixture of (1R,5S)-tert-butyl 3-(7-chloro-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (150 mg, 281 µmol, 1.0 eq), ((2-fluoro-6-(methoxymethoxy)-8-(4,4,5,5-tetramethyl-1,3,2-dioxaborolan-2-yl)naphthalen-1-yl)ethynyl)triisopropylsilane (188 mg, 367 µmol, 1.3 eq), and $K_3PO_4$ (1.5 M in water, 563 µL, 3.0 eq) in THF (2 mL) was added [2-(2-aminophenyl)phenyl]palladium(1+); bis(1-adamantyl)-butyl-phosphane; methanesulfonate (20.5 mg, 28.1 µmol, 0.1 eq), and the mixture was degassed and stirred at 60° C. for 2 hours. After completion, the mixture was diluted with EA (10 mL) and water (5 mL), and extracted with EA (10 mL). The combined organic phase was washed with brine (10 mL), dried over anhydrous sodium sulfate, filtered and concentrated to give a residue. The residue was purified by reversed phase flash chromatography [water (FA, 0.1%)/acetonitrile] to give the title compound (185 mg, 74% yield). Yellow solid; LCMS [ESI, M+1]: 883.5.

Step B. (1R,5S)-tert-butyl 3-(7-(8-ethynyl-7-fluoro-3-(methoxymethoxy)naphthalen-1-yl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate. To the solution of (1R,5S)-tert-butyl 3-(8-fluoro-7-(7-fluoro-3-(methoxymethoxy)-8-((triisopropylsilyl)ethynyl)naphthalen-1-yl)-2-((hexahydro-1H-pyrrolizin-7a-yl)methoxy)pyrido[4,3-d]pyrimidin-4-yl)-3,8-diazabicyclo[3.2.1]octane-8-carboxylate (185 mg, 209 µmol, 1.0 eq) in DMF (3 mL) was added CsF (318 mg, 2.09 mmol, 10 eq), and the mixture was stirred at 20° C. for 2 hours. After completion, the reaction mixture was filtered and the filtrate was purified by reversed phase flash chromatography [water (FA 0.1%)/acetonitrile] to give the title compound (135 mg, 88% yield). Yellow Solid. LCMS [ESI, M+1]: 727.4.

Step C. (1R,5S)-tert-butyl 3-(7-(8-ethyl-7-fluoro-3-(methoxymethoxy)naphthalen-1-yl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate. To the solution of (1R,5S)-tert-butyl 3-(7-(8-ethynyl-7-fluoro-3-(methoxymethoxy)naphthalen-1-yl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (130 mg, 179 µmol, 1.0 eq) in MeOH (3 mL) was added Pd/C (26.0 mg, 10% purity). The suspension was degassed under vacuum and purged with $H_2$ several times. The mixture was stirred under $H_2$ (15 psi) at 15° C. for 0.5 hour. After completion, the mixture was filtered and concentrated to give the title compound (110 mg, 82% yield). Yellow Solid. LCMS [ESI, M+1]: 731.4.

Step D. 4-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)-5-ethyl-6-fluoronaphthalen-2-ol. To a solution of (1R,5S)-tert-butyl 3-(7-(8-ethyl-7-fluoro-3-(methoxymethoxy)naphthalen-1-yl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (105 mg, 144 µmol, 1.0 eq) in ACN (1 mL) was added HCl·dioxane (4 M, 2 mL) at 0° C., and the mixture was stirred at 0° C. for 0.5 hour. After completion, the mixture was concentrated at 20° C. to give a residue. The pH of the residue was adjusted to ~8 with saturated $NaHCO_3$ solution. The mixture was purified by prep-HPLC (column: Shim-pack C18 150*25*10 um; mobile phase: [water (0.225% FA)-ACN]; B %: 13%-33%, 10 min) to give the title compound (47.65 mg, 51% yield). Off-white Solid. $^1$H NMR (400 MHz, methanol-d4) δ=9.14 (s, 1H), 7.74-7.63 (m, 1H), 7.32 (d, J=2.4 Hz, 1H), 7.26 (t, J=9.6 Hz, 1H), 7.05 (d, J=2.8 Hz, 1H), 4.86-4.74 (m, 2H), 4.67 (s, 2H), 4.06 (br d, J=7.6 Hz, 2H), 4.00-3.84 (m, 2H), 3.78-3.64 (m, 2H), 3.30-3.25 (m, 2H), 2.56-2.42 (m, 1H), 2.41-2.29 (m, 2H), 2.29-1.95 (m, 11H), 0.79 (t, J=7.6 Hz, 3H). LCMS [ESI, M+1]: 587.4.

Example 315

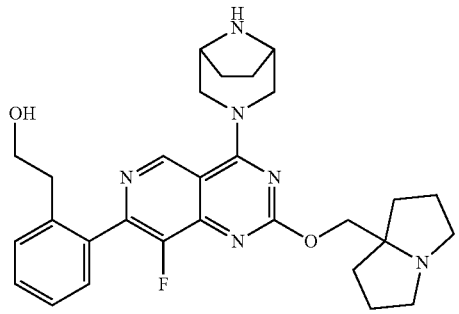 [SMILES: OCCc1ccccc1-c1ncc2c(N3CC4CCC(C3)N4)nc(OCC34CCCN3CCC4)nc2c1F]

2-(2-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)phenyl)ethanol

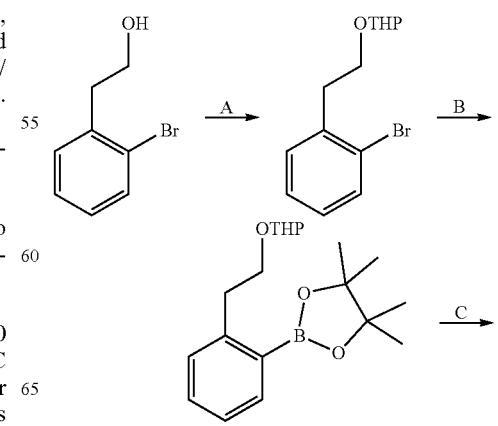

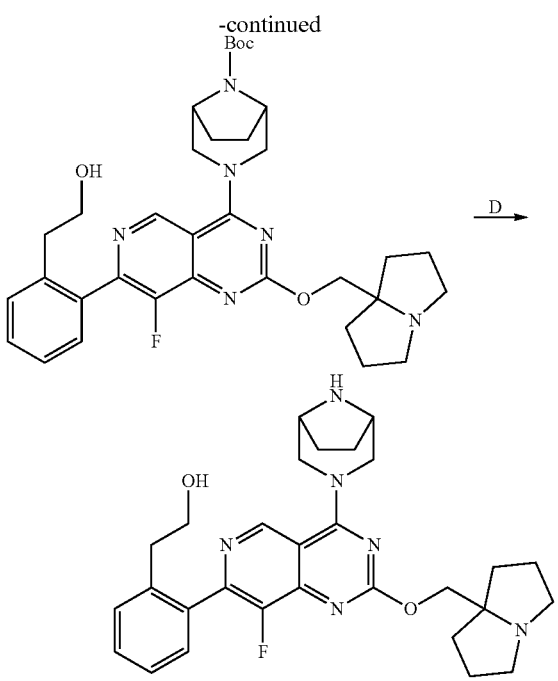

Step A. 2-(2-bromophenethoxy)tetrahydro-2H-pyran. To a solution of 2-(2-bromophenyl)ethanol (2 g, 9.95 mmol, 1 eq), TsOH·H₂O (94.6 mg, 497 μmol, 0.05 eq) in dichloromethane (40 mL) was added DHP (1.26 g, 14.9 mmol, 1.5 eq) dropwise at 0° C. The mixture was stirred at 15° C. for 2 hours. After completion, the reaction mixture was diluted with H₂O (30 mL) and saturated NaHCO₃ aqueous (5 mL). The dichloromethane layer was separated, dried over anhydrous Na₂SO₄, filtered and concentrated under reduced pressure to give a residue. The residue was purified by column chromatography (SiO₂, petroleum ether/ethyl acetate=10/1) to give the title compound (2.4 g, 84% yield). Colorless oil; Rf=0.71 (3:1, petroleum ether/ethyl acetate); ¹H NMR (400 MHz, chloroform-d) δ=7.54 (dd, J=1.2, 8.0 Hz, 1H), 7.32-7.29 (m, 1H), 7.24 (dt, J=1.2, 7.6 Hz, 1H), 7.08 (td, J=1.6, 7.6 Hz, 1H), 4.62 (t, J=3.2 Hz, 1H), 3.96 (dt, J=7.2, 9.8 Hz, 1H), 3.85-3.70 (m, 1H), 3.66 (dt, J=7.2, 9.8 Hz, 1H), 3.52-3.45 (m, 1H), 3.07 (t, J=7.2 Hz, 2H), 1.86-1.62 (m, 3H), 1.57-1.49 (m, 3H).

Step B. 4,4,5,5-tetramethyl-2-(2-(2-((tetrahydro-2H-pyran-2-yl)oxy)ethyl)phenyl)-1,3,2-dioxaborolane. A mixture of 2-(2-bromophenethoxy)tetrahydro-2H-pyran (1 g, 3.51 mmol, 1.0 eq), 4,4,5,5-tetramethyl-2-(4,4,5,5-tetramethyl-1,3,2-dioxaborolan-2-yl)-1,3,2-dioxaborolane (1.34 g, 5.26 mmol, 1.5 eq), and AcOK (860 mg, 8.76 mmol, 2.5 eq) in dioxane (25 mL) was degassed and purged with N₂ for 3 times. Pd(dppf)Cl₂ (154 mg, 210 μmol, 0.06 eq) was added. The mixture was stirred at 105° C. for 3 hours under N₂. After completion, the reaction mixture was diluted with H₂O (100 mL) and extracted with ethyl acetate (15 mL×3). The combined organic layers were concentrated under reduced pressure to give a residue. The residue was purified by reversed phase flash chromatography [water (FA, 0.1%)/acetonitrile=1/9] to give the title compound (1 g, 85% yield). Black brown liquid; ¹H NMR (400 MHz, chloroform-d) δ=7.82-7.75 (m, 1H), 7.38-7.34 (m, 1H), 7.27-7.23 (m, 1H), 7.22-7.19 (m, 1H), 4.63-4.59 (m, 1H), 4.00-3.87 (m, 1H), 3.78-3.72 (m, 1H), 3.67-3.57 (m, 1H), 3.48-3.41 (m, 1H), 3.25-3.17 (m, 2H), 1.84-1.60 (m, 3H), 1.55-1.44 (m, 3H), 1.35 (s, 12H).

Step C. (1R,5R)-tert-butyl 3-(8-fluoro-2-((hexahydro-1H-pyrrolizin-7a-yl)methoxy)-7-(2-(2-((tetrahydro-2H-pyran-2-yl)oxy)ethyl)phenyl)pyrido[4,3-d]pyrimidin-4-yl)-3,8-diazabicyclo[3.2.1]octane-8-carboxylate. A mixture of (1R, 5S)-tert-butyl 3-(7-chloro-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (150 mg, 281 μmol, 1.0 eq), and K₃PO₄ (1.5 M in H₂O, 0.6 mL, 3.20 eq) in THF (2.4 mL) was degassed and purged with N₂ for 3 times. [2-(2-aminophenyl)phenyl]palladium(1+); bis(1-adamantyl)-butyl-phosphane; methanesulfonate (21 mg, 28.8 μmol, 0.1 eq) and 4,4,5,5-tetramethyl-2-(2-(2-((tetrahydro-2H-pyran-2-yl)oxy)ethyl)phenyl)-1,3,2-dioxaborolane (150 mg, 451 μmol, 1.60 eq) were added. The mixture was stirred at 65° C. for 2.5 hours under N₂. After completion, the reaction mixture was diluted with H₂O (2 mL) and extracted with ethyl acetate (2 mL×4). The combined organic layers were concentrated under reduced pressure to give a residue. The residue was purified by reversed phase flash chromatography [water (FA, 0.1%)/acetonitrile=1/1] to give the title compound (140 mg, 65% yield). Light yellow foam; LCMS [ESI, M+1]: 703.4.

Step D. 2-(2-(4-((1R,5R)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)phenyl)ethanol. To a solution of (1R,5S)-tert-butyl 3-(8-fluoro-2-((hexahydro-1H-pyrrolizin-7a-yl)methoxy)-7-(2-(2-((tetrahydro-2H-pyran-2-yl)oxy)ethyl)phenyl)pyrido[4,3-d]pyrimidin-4-yl)-3,8-diazabicyclo[3.2.1]octane-8-carboxylate (80 mg, 114 μmol, 1.0 eq) in MeCN (2 mL) was added HCl·dioxane (4 M, 4 mL, 140 eq) dropwise at 10° C. The mixture was stirred at 10° C. for 0.5 hour. After completion, the reaction mixture was concentrated under reduced pressure to give a residue at 10° C. (without heating). The residue was dissolved in MeOH (0.5 mL) and MeCN (1 mL). The pH of the mixture was adjusted to 7-8 with 25% NH₃·H₂O (0.1 mL dissolved in MeCN (3 mL)). The mixture was purified by prep-HPLC (column: Shim-pack C18 150*25*10 um; mobile phase: [water (0.225% FA)-ACN]; B %: 2%-22%, 10 min) to give the title compound (13.3 mg, 19% yield, 1.8FA). Yellow solid; ¹H NMR (400 MHz, methanol-d4) δ=9.14 (s, 1H), 7.49-7.39 (m, 4H), 4.79 (d, J=13.2 Hz, 2H), 4.67 (s, 2H), 4.05 (s, 2H), 3.90 (d, J=13.6 Hz, 2H), 3.73-3.60 (m, 4H), 2.82 (t, J=6.4 Hz, 2H), 2.36-1.89 (m, 14H); LCMS [ESI, M+1]: 519.3.

Example 316

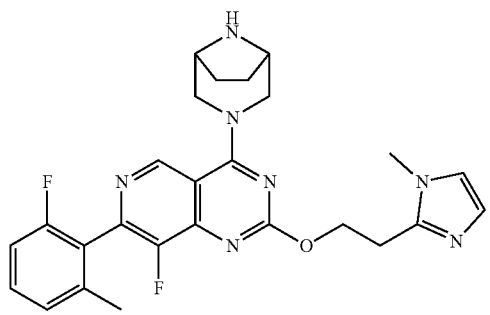 [SMILES: Cc1cccc(F)c1-c1ncc2c(N3CC4CCC(C3)N4)nc(OCCc3nccn3C)nc2c1F]

4-((1R,5S)-3,8-diazabicyclo[3.2.1]octan-3-yl)-8-fluoro-7-(2-fluoro-6-methylphenyl)-2-(2-(1-methyl-1H-imidazol-2-yl)ethoxy)pyrido[4,3-d]pyrimidine Synthesized according to Example 3, Steps H-I substituting (2-fluoro-6-methylphenyl)boronic acid in place of 4-(4, 4,5,5-tetramethyl-1,3,2-dioxaborolan-2-yl)naphthalen-2-ol in Step H to afford 4-((1R,5S)-3,8-diazabicyclo[3.2.1]octan-3-yl)-8-fluoro-7-(2-fluoro-6-methylphenyl)-2-(2-(1-methyl-1H-imidazol-2-yl)ethoxy)pyrido[4,3-d]pyrimidine (12 mg, 71%). LCMS (MM-ES+APCI, Pos): m/z 492.2 (M+H).

Example 317

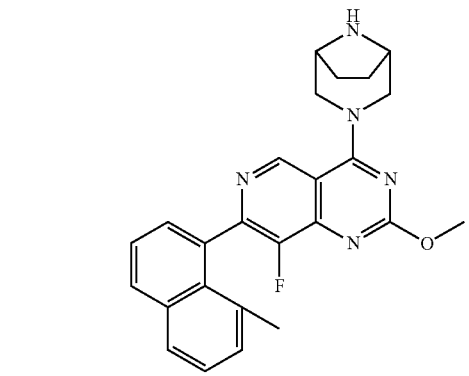 [SMILES: COc1nc(N2CC3CCC(C2)N3)c2cnc(-c3cccc4cccc(C)c34)c(F)c2n1]

4-((1R,5S)-3,8-diazabicyclo[3.2.1]octan-3-yl)-8-fluoro-2-methoxy-7-(8-methylnaphthalen-1-yl)pyrido[4,3-d]pyrimidine

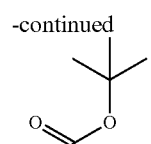

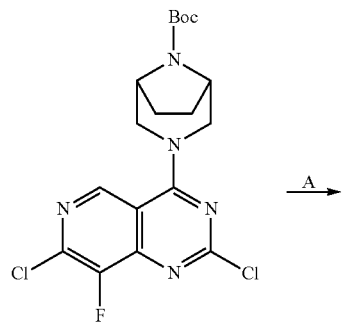

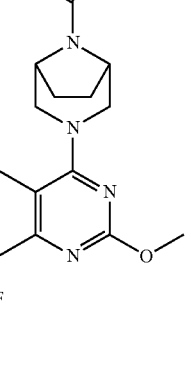

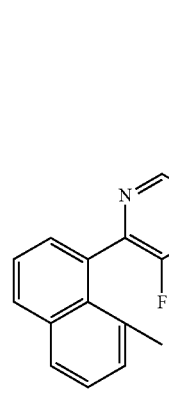

Step A. tert-butyl (1R,5S)-3-(7-chloro-8-fluoro-2-methoxypyrido[4,3-d]pyrimidin-4-yl)-3,8-diazabicyclo[3.2.1]octane-8-carboxylate. To a solution of tert-butyl (1R,5S)-3-(2,7-dichloro-8-fluoropyrido[4,3-d]pyrimidin-4-yl)-3,8-diazabicyclo[3.2.1]octane-8-carboxylate (0.20 g, 0.47 mmol) in anhydrous THF (20 mL) at room temperature was added NaOMe (0.20 mL, 0.47 mmol). After stirred for 30 minutes, the mixture was partitioned between sat. NH₄Cl (75 mL) and EtOAc (30 mL) and the aqueous layer extracted with EtOAc (2×30 mL). The combined organic phases were washed with brine (40 mL), dried over sodium sulfate, filtered, and concentrated in vacuo. The residue was purified by column chromatography eluting with 10-60% EtOAc/hexanes to afford tert-butyl (1R,5S)-3-(7-chloro-8-fluoro-2-methoxypyrido[4,3-d]pyrimidin-4-yl)-3,8-diazabicyclo[3.2.1]octane-8-carboxylate (0.18 g, 90%) as a white powder. LCMS (MM-ES+APCI, Pos): m/z 424.1 (M+H).

Step B. tert-butyl (1R,5S)-3-(8-fluoro-2-methoxy-7-(8-methylnaphthalen-1-yl)pyrido[4,3-d]pyrimidin-4-yl)-3,8-diazabicyclo[3.2.1]octane-8-carboxylate. A solution of 4,4,5,5-tetramethyl-2-(8-methylnaphthalen-1-yl)-1,3,2-dioxaborolane (0.17 g, 0.62 mmol), tert-butyl (1R,5S)-3-(7-chloro-8-fluoro-2-methoxypyrido[4,3-d]pyrimidin-4-yl)-3,8-diazabicyclo[3.2.1]octane-8-carboxylate (0.18 g, 0.42 mmol), and 2 M K₂CO₃ in water (0.65 mL, 1.3 mmol), and Pd(PPh₃)₄ (48 mg, 0.042 mmol) in dioxane (4 mL) was sparged with argon and heated at 85° C. overnight. More 4,4,5,5-tetramethyl-2-(8-methylnaphthalen-1-yl)-1,3,2-dioxaborolane (50 mg) and Pd(PPh₃)₄ (15 mg) were added and the reaction was heated to 85° C. for 3 hours. The mixture was diluted with water (60 mL) and extracted with EtOAc

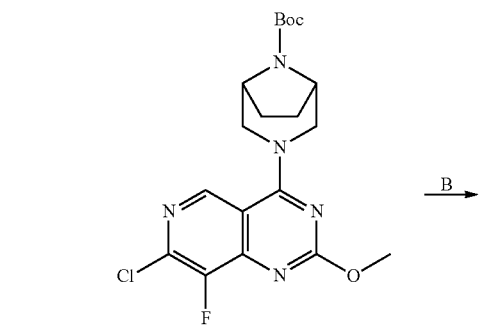

(3×30 mL). The combined organic layers were washed with brine (50 mL), dried over sodium sulfate, filtered, and concentrated in vacuo. The residue was purified by column chromatography eluting with 0-35% EtOAc/hexanes to afford tert-butyl (1R,5S)-3-(8-fluoro-2-methoxy-7-(8-methylnaphthalen-1-yl)pyrido[4,3-d]pyrimidin-4-yl)-3,8-diazabicyclo[3.2.1]octane-8-carboxylate (44 mg, 20%) as a yellow foam. LCMS (MM-ES+APCI, Pos): m/z 530.2 (M+H).

Step C. 4-((1R,5S)-3,8-diazabicyclo[3.2.1]octan-3-yl)-8-fluoro-2-methoxy-7-(8-methylnaphthalen-1-yl)pyrido[4,3-d]pyrimidine. To a 0° C. solution of tert-butyl (1R,5S)-3-(8-fluoro-2-methoxy-7-(8-methylnaphthalen-1-yl)pyrido[4,3-d]pyrimidin-4-yl)-3,8-diazabicyclo[3.2.1]octane-8-carboxylate (44 mg, 0.084 mmol) in DCM (2 mL) was added TFA (0.15 mL, 1.7 mmol). The mixture was stirred at room temperature for 4.5 hours. The solution was poured into a mixture of saturated bicarbonate (20 mL) and EtOAc (15 mL). The aqueous layer was extracted with EtOAc (2×15 mL). The combined organic layers were washed with saturated bicarbonate (15 mL), brine (15 mL), dried over sodium sulfate, and concentrated in vacuo. The residue was purified by column chromatography eluting with 0-20% MeOH/DCM to afford 4-((1R,5S)-3,8-diazabicyclo[3.2.1]octan-3-yl)-8-fluoro-2-methoxy-7-(8-methylnaphthalen-1-yl)pyrido[4,3-d]pyrimidine (33 mg, 90%) as a yellow foam. LCMS (MM-ES+APCI, Pos): m/z 430.2 (M+H).

Example 318

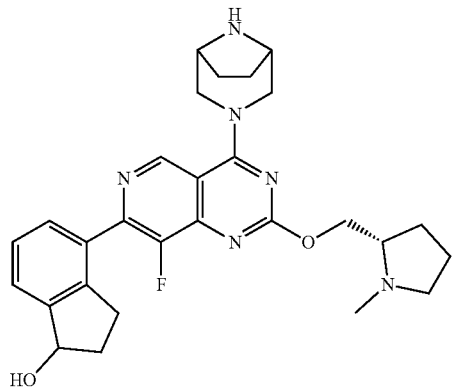 [SMILES: CN1CCC[C@H]1COc1nc(N2CC3CCC(C2)N3)c2cnc(-c3cccc4c3CCC4O)c(F)c2n1]

4-(4-((1R,5S)-3,8-diazabicyclo[3.2.1]octan-3-yl)-8-fluoro-2-(((S)-1-methylpyrrolidin-2-yl)methoxy)pyrido[4,3-d]pyrimidin-7-yl)-2,3-dihydro-1H-inden-1-ol

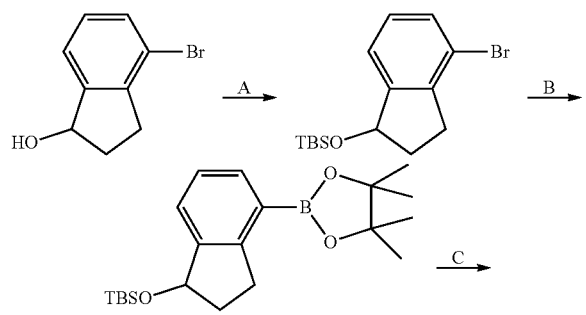

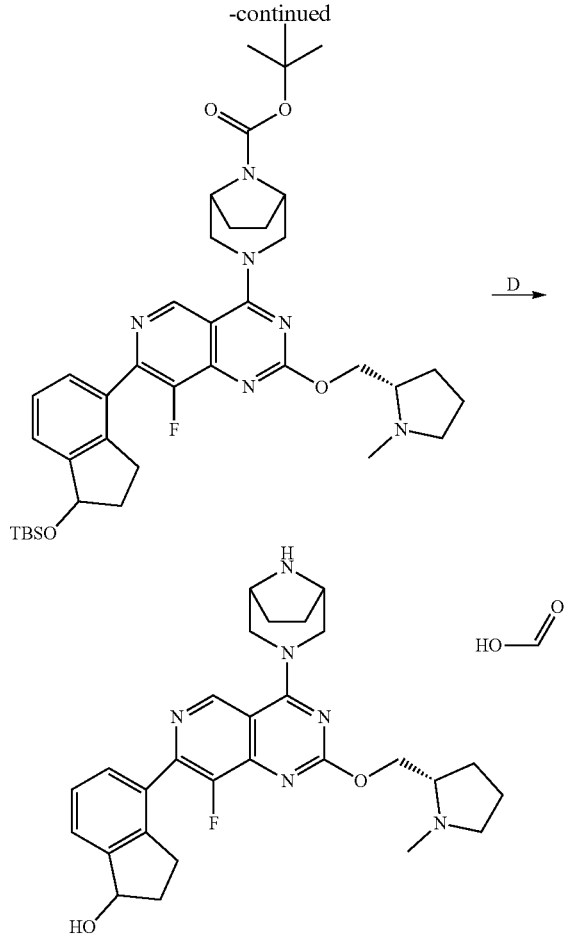

Step A. ((4-bromo-2,3-dihydro-1H-inden-1-yl)oxy)(tert-butyl)dimethylsilane. To a solution of 4-bromo-2,3-dihydro-1H-inden-1-ol (1.0 g, 4.7 mmol) and imidazole (0.42 g, 6.1 mmol) in DMF (12 mL) under $N_2$ was added TBS-Cl (0.85 g, 5.6 mmol). The solution was stirred at rt for 2 h. The mixture was quenched with ethyl acetate (30 mL), washed with water (20 mL×2), dried ($Na_2SO_4$), and concentrated to dryness. The residue was purified by flash chromatography eluting with ethyl acetate/hexanes (0-20%) to give the title compound (1.5 g, 95%) as a colorless oil. $^1$H NMR (400 MHz, (CDCl$_3$): δ 7.38 (d, J=8.0 Hz, 1H), 7.23 (d, J=7.6 Hz, 1H), 7.09 (t, J=7.8 Hz, 1H), 5.30 (m, 1H), 3.13 (m, 1H), 2.74 (m, 1H), 2.44 (m, 1H), 1.93 (m, 1H), 0.93 (s, 9H), 0.17 (s, 3H), 0.15 (s, 3H).

Step B. tert-butyldimethyl((4-(4,4,5,5-tetramethyl-1,3,2-dioxaborolan-2-yl)-2,3-dihydro-1H-inden-1-yl)oxy)silane. To a solution of ((4-bromo-2,3-dihydro-1H-inden-1-yl)oxy)(tert-butyl)dimethylsilane (0.28 g, 0.86 mmol) in THF (20 mL) at −70° C. was added n-butyllithium (0.51 mL, 1.3 mmol). The reaction was stirred at −70° C. for 0.5 h, followed by addition of 2-isopropoxy-4,4,5,5-tetramethyl-1,3,2-dioxaborolane (0.26 mL, 1.3 mmol). The reaction mixture was warmed to rt, quenched with NH$_4$Cl (sat.), and extracted with ethyl acetate. The organic solution was dried (Na$_2$SO$_4$), concentrated and purified by flash chromatography eluting with ethyl acetate/hexanes (0-30%) to give the title compound (0.23 g, 72%) as a colorless oil. $^1$H NMR (400 MHz, (CDCl$_3$): δ 7.67 (d, J=7.2 Hz, 1H), 7.39 (d, J=7.6 Hz, 1H), 7.24-7.16 (m, 1H), 5.30-5.16 (m, 1H), 3.32-3.20

(m, 1H), 2=3.00-2.72 (m, 1H), 2.48-2.32 (m, 1H), 1.96-1.80 (m, 1H), 1.32 (s, 12H), 0.94 (s, 9H), 0.16 (s, 3H), 0.14 (s, 3H).

Step C. tert-butyl (1R,5S)-3-(7-(1-(((tert-butyldimethylsilyl)oxy)-2,3-dihydro-1H-inden-4-yl)-8-fluoro-2-(((S)-1-methylpyrrolidin-2-yl)methoxy)pyrido[4,3-d]pyrimidin-4-yl)-3,8-diazabicyclo[3.2.1]octane-8-carboxylate. To a vial with a stir bar were added tert-butyl (1R,5S)-3-(7-chloro-8-fluoro-2-(((S)-1-methylpyrrolidin-2-yl)methoxy)pyrido[4,3-d]pyrimidin-4-yl)-3,8-diazabicyclo[3.2.1]octane-8-carboxylate (synthesized according to Example 3, Step A-G substituting (S)-(1-methylpyrrolidin-2-yl)methanol in place of 2-(1-methyl-1H-imidazol-2-yl)ethan-1-ol) (50 mg, 0.10 mmol), tert-butyldimethyl((4-(4,4,5,5-tetramethyl-1,3,2-dioxaborolan-2-yl)-2,3-dihydro-1H-inden-1-yl)oxy)silane (55 mg, 0.15 mmol), and Pd(PPh$_3$)$_4$ (11 mg, 0.010 mmol). The vial was flushed with N$_2$ and closed with a septum. To the vial were added Na$_2$CO$_3$ (2.0 M, 0.15 mL, 0.30 mmol) and dioxane (1 mL) under N$_2$. The mixture was heated at 100° C. for 15 h, cooled to rt, and purified by preparative C18 HPLC (Gilson, 0-95% CH$_3$CN/H$_2$O with 0.1% TFA). The desired fractions were combined, basified with NaHCO$_3$ (sat.) and extracted with ethyl acetate. The ethyl acetate extract was washed with water, washed with brine, and dried (Na$_2$SO$_4$). The solution was concentrated to yield the title compound (17 mg, 24%) as a white solid. LCMS (MM-ES+APCI, Pos): m/z 719.3 (M+H).

Step D. 4-(4-((1R,5S)-3,8-diazabicyclo[3.2.1]octan-3-yl)-8-fluoro-2-(((S)-1-methylpyrrolidin-2-yl)methoxy)pyrido[4,3-d]pyrimidin-7-yl)-2,3-dihydro-1H-inden-1-ol formate. To a solution of tert-butyl (1R,5S)-3-(7-(1-(((tert-butyldimethylsilyl)oxy)-2,3-dihydro-1H-inden-4-yl)-8-fluoro-2-(((S)-1-methylpyrrolidin-2-yl)methoxy)pyrido[4,3-d]pyrimidin-4-yl)-3,8-diazabicyclo[3.2.1]octane-8-carboxylate (17 mg, 0.024 mmol) in DCM (1.2 mL) was added TFA (0.3 mL). The mixture was stirred at rt for 1 h and concentrated to dryness. The residue was dissolved in dioxane (1 mL) and treated with ammonium hydroxide (0.5 mL) at rt for 15 min. The mixture was concentrated to dryness and purified by preparative C18 HPLC (Gilson, 0-95% CH$_3$CN/H$_2$O with 0.1% formic acid). The desired fractions were combined and concentrated to dryness to give the title product (10 mg, 84%) as the bis formic acid salt. LCMS (MM-ES+APCI, Pos): m/z 505.3 (M+H).

Example 319

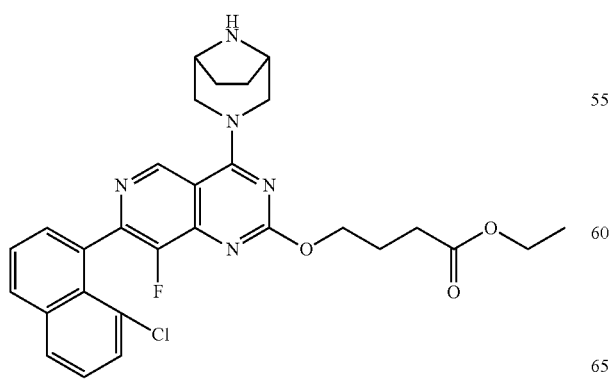

Ethyl 4-((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)butanoate Synthesized according to Example 29, Step H and I, substituting ethyl 4-hydroxybutanoate in place of (S)-(1-isopropylpyrrolidin-2-yl)methanol in step H to give the title product (2.2 mg, 14%). LCMS (MM-ES+APCI, Pos): m/z 550.2 (M+H).

Example 320

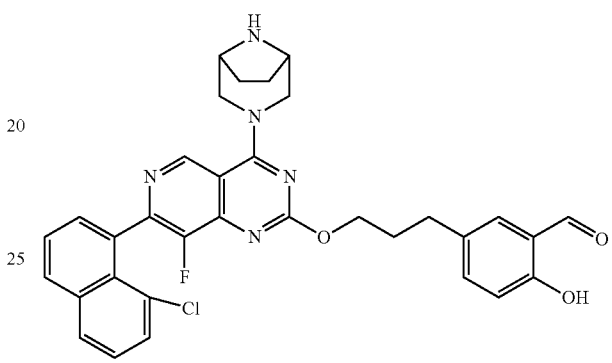

5-(3-((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)propyl)-2-hydroxybenzaldehyde Synthesized according to Example 62, substituting 2-hydroxy-5-(3-hydroxypropyl)benzaldehyde in place of 2-hydroxy-5-(2-hydroxyethyl)-benzaldehyde to give the title product (4.6 mg, 15%). LCMS (MM-ES+APCI, Pos): m/z 598.2 (M+H).

Example 321

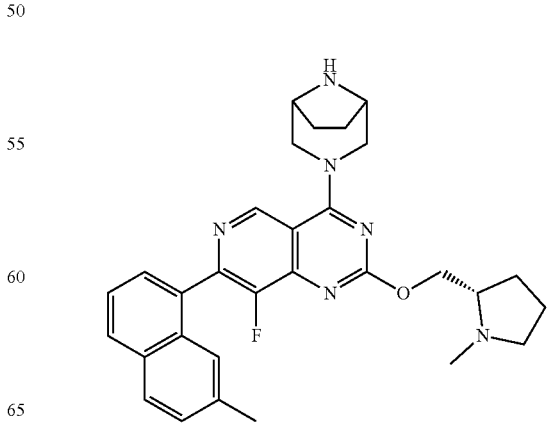

701

4-((1R,5S)-3,8-diazabicyclo[3.2.1]octan-3-yl)-8-fluoro-7-(7-methylnaphthalen-1-yl)-2-(((S)-1-methylpyrrolidin-2-yl)methoxy)pyrido[4,3-d]pyrimidine

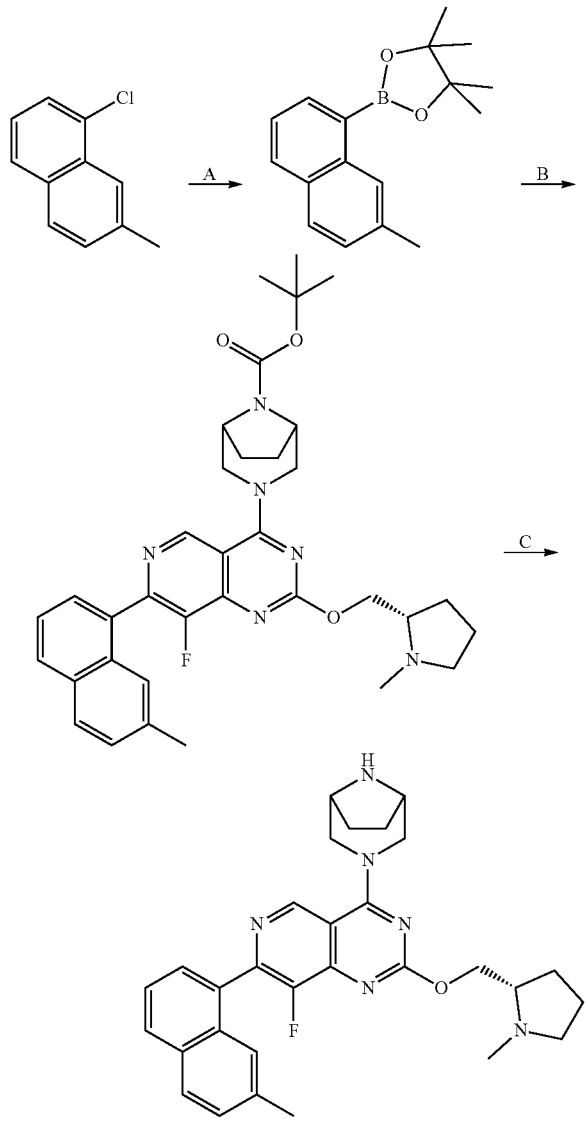

Step A. 4,4,5,5-tetramethyl-2-(7-methylnaphthalen-1-yl)-1,3,2-dioxaborolane. To a vial containing Pd$_2$(dba)$_3$ (23 mg, 0.025 mmol) and 2-dicyclohexylphosphino-2',6'-dimethoxy-1,1'-biphenyl (31 mg, 0.076 mmol) under N$_2$ was added toluene (0.50 mL). The mixture was stirred under N$_2$ for 3 min and a solution of 1-chloro-7-methylnaphthalene (89 mg, 0.50 mmol) and 4,4,4',4',5,5,5',5'-octamethyl-2,2'-bi(1,3,2-dioxaborolane) (0.21 g, 0.81 mmol) in toluene (1 mL) was added. The vial was closed with a cap and heated at 110° C. for 20 h. The mixture was cooled, quenched with ethyl acetate/hexanes, and filtered. The filtrate was concentrated and purified by flash chromatography eluting with ethyl acetate/hexanes (0-20%) to give the title compound (94 mg, 70%) as a light yellow solid. $^1$H NMR (400 MHz, (CDCl$_3$) δ 8.50 (s, 1H), 8.03 (d, J=6.8 Hz, 1H), 7.88 (d, J=8.1 Hz, 1H), 7.73 (d, J=8.3 Hz, 1H), 7.39 (m, 1H), 7.30 (d, J=8.3 Hz, 1H), 2.55 (s, 3H), 1.43 (s, 12H).

702

Step B. tert-butyl (1R,5S)-3-(8-fluoro-7-(7-methylnaphthalen-1-yl)-2-(((S)-1-methylpyrrolidin-2-yl)methoxy)pyrido[4,3-d]pyrimidin-4-yl)-3,8-diazabicyclo[3.2.1]octane-8-carboxylate. To a mixture of tert-butyl (1R,5S)-3-(7-chloro-8-fluoro-2-(((S)-1-methylpyrrolidin-2-yl)methoxy)pyrido[4,3-d]pyrimidin-4-yl)-3,8-diazabicyclo[3.2.1]octane-8-carboxylate (synthesized according to Example 3, Step A-G substituting (S)-(1-methylpyrrolidin-2-yl)methanol in place of 2-(1-methyl-1H-imidazol-2-yl)ethan-1-ol) (30 mg, 0.059 mmol), 4,4,5,5-tetramethyl-2-(7-methylnaphthalen-1-yl)-1,3,2-dioxaborolane (24 mg, 0.089 mmol), Na$_2$CO$_3$ (2.0 M, 0.90 mL, 0.18 mmol), and dioxane (2 mL) in a vial under N$_2$ was added Pd(PPh$_3$)$_4$ (14 mg, 0.012 mmol). The mixture was sparged with N$_2$ and heated at 95° C. for 20 h. The mixture was cooled to rt and purified by preparative C18 HPLC (Gilson, 0-95% CH$_3$CN/H$_2$O with 0.1% TFA). The desired fractions were combined, basified, and extracted with DCM. The combined extracts were dried (Na$_2$SO$_4$) and concentrated to give the title compound (19 mg, 52%) as a white solid. LCMS (MM-ES+APCI, Pos): m/z 613.4 (M+H).

Step C. 4-((1R,5S)-3,8-diazabicyclo[3.2.1]octan-3-yl)-8-fluoro-7-(7-methylnaphthalen-1-yl)-2-(((S)-1-methylpyrrolidin-2-yl)methoxy)pyrido[4,3-d]pyrimidine. To a solution of tert-butyl (1R,5S)-3-(8-fluoro-7-(7-methylnaphthalen-1-yl)-2-(((S)-1-methylpyrrolidin-2-yl)methoxy)pyrido[4,3-d]pyrimidin-4-yl)-3,8-diazabicyclo[3.2.1]octane-8-carboxylate (19 mg, 0.031 mmol) in DCM (1 mL) was added TFA (0.5 mL). The mixture was stirred at rt for 1 h and concentrated to dryness. The residue was neutralized with NH$_3$·H$_2$O and purified by preparative C18 HPLC (Gilson, 0-90% CH$_3$CN/H$_2$O with 0.2% NH$_4$·HCO$_3$). The desired fractions were combined and concentrated to give the title compound (15 mg, 94%) as a white solid. LCMS (MM-ES+APCI, Pos): m/z 513.3 (M+H).

Example 322

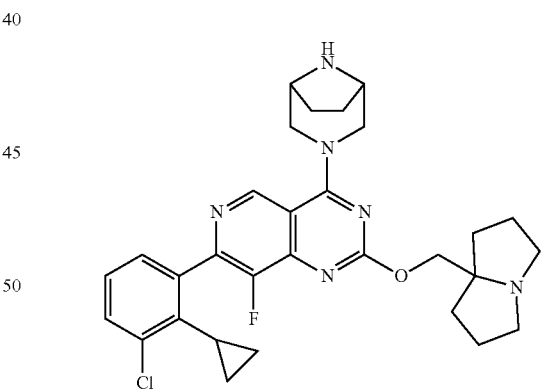

4-((1R,5S)-3,8-diazabicyclo[3.2.1]octan-3-yl)-7-(3-chloro-2-cyclopropylphenyl)-8-fluoro-2-((tetrahydro-1H-pyrrolizin-7a(5H)-yl)methoxy)pyrido[4,3-d]pyrimidine Synthesized according to Example 196 substituting 2-(3-chloro-2-cyclopropylphenyl)-4,4,5,5-tetramethyl-1,3,2-dioxaborolane in place of 2,2-difluorobenzo[1,3]dioxole-4-boronic acid in step B to afford 4-((1R,5S)-3,8-diazabicyclo[3.2.1]octan-3-yl)-7-(3-chloro-2-cyclopropylphenyl)-8-fluoro-2-((tetrahydro-1H-pyrrolizin-7a(5H)-yl)methoxy)

Example 323

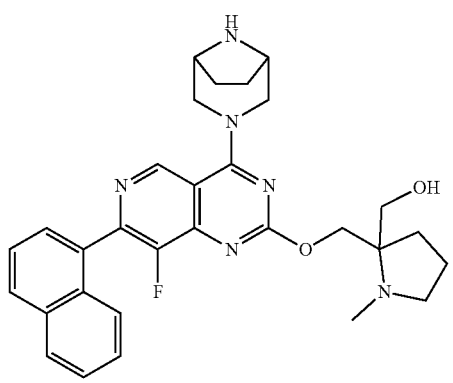 [SMILES: CN1CCCC1(CO)COc1nc(N2CC3CCC(C2)N3)c2cnc(-c3cccc4ccccc34)c(F)c2n1]

(2-(((4-((1R,5S)-3,8-diazabicyclo[3.2.1]octan-3-yl)-8-fluoro-7-(naphthalen-1-yl)pyrido[4,3-d]pyrimidin-2-yl)oxy)methyl)-1-methylpyrrolidin-2-yl)methanol

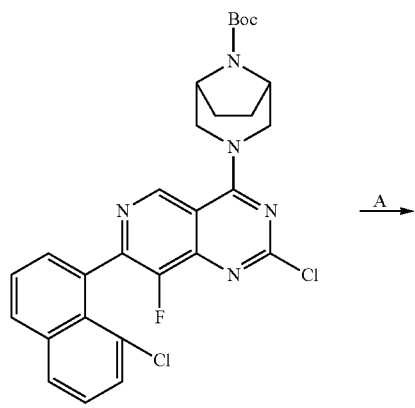

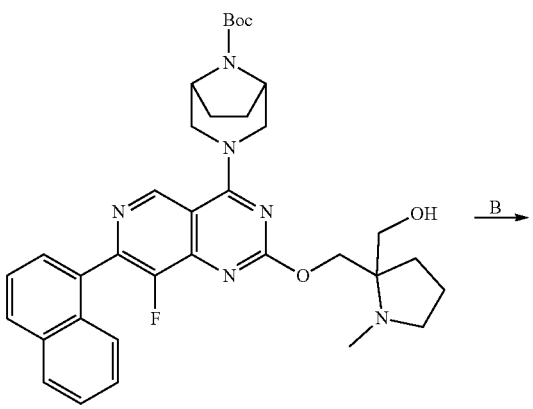

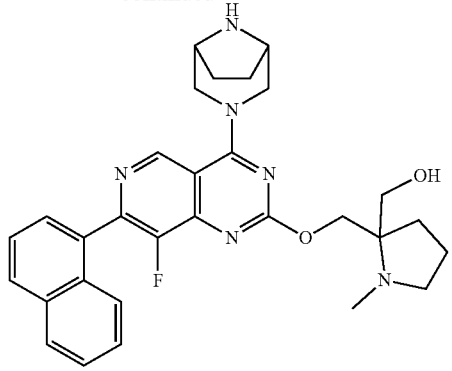

Step A. tert-butyl (1R,5S)-3-(8-fluoro-2-((2-(hydroxymethyl)-1-methylpyrrolidin-2-yl)methoxy)-7-(naphthalen-1-yl)pyrido[4,3-d]pyrimidin-4-yl)-3,8-diazabicyclo[3.2.1]octane-8-carboxylate: To a stirred solution of (1-methylpyrrolidine-2,2-diyl)dimethanol hydrochloride (0.25 g, 1.4 mmol), tert-butyl (1R,5S)-3-(2-chloro-7-(8-chloronaphthalen-1-yl)-8-fluoropyrido[4,3-d]pyrimidin-4-yl)-3,8-diazabicyclo[3.2.1]octane-8-carboxylate (0.17 g, 0.308 mmol), and BINAP (38 mg, 0.061 mmol) in toluene (1.5 mL) was added Cs₂CO₃ (300 mg, 0.93 mmol) at room temperature under nitrogen. The reaction mixture was sparged with argon for five minutes. Palladium (II) acetate (7 mg, 0.03 mmol) was added, and the reaction was heated at 110° C. overnight. The reaction was cooled to RT, water was added, and the aqueous layer was extracted two times with ethyl acetate. The pooled organic layers were dried over magnesium sulfate, filtered, and concentrated. The residue was purified by a silica gel column (0 to 100% MeOH/DCM) to give a crude product (37 mg, 19%).

Step B. (2-(((4-((1R,5S)-3,8-diazabicyclo[3.2.1]octan-3-yl)-8-fluoro-7-(naphthalen-1-yl)pyrido[4,3-d]pyrimidin-2-yl)oxy)methyl)-1-methylpyrrolidin-2-yl)methanol bis(2,2,2-trifluoroacetate): Synthesized according to Example 2, Step I, substituting tert-butyl (1R,5S)-3-(8-fluoro-2-((2-(hydroxymethyl)-1-methylpyrrolidin-2-yl)methoxy)-7-(naphthalen-1-yl)pyrido[4,3-d]pyrimidin-4-yl)-3,8-diazabicyclo[3.2.1]octane-8-carboxylate in place of tert-butyl (1R,5S)-3-(8-fluoro-7-(3-hydroxynaphthalen-1-yl)-2-(((S)-1-methylpyrrolidin-2-yl)methoxy)pyrido[4,3-d]pyrimidin-4-yl)-3,8-diazabicyclo[3.2.1]octane-8-carboxylate to give the title product (1.1 mg, 3%) as the bis TFA salt. LCMS (MM-ES+APCI, Pos): m/z 529.3 (M+H).

Example 324

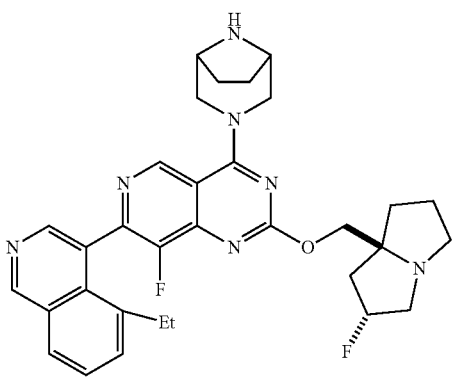

705

4-((1R,5S)-3,8-diazabicyclo[3.2.1]octan-3-yl)-7-(5-ethylisoquinolin-4-yl)-8-fluoro-2-((2-fluorotetrahydro-1H-pyrrolizin-7a(5H)-yl)methoxy)pyrido[4,3-d]pyrimidine (racemic, trans)

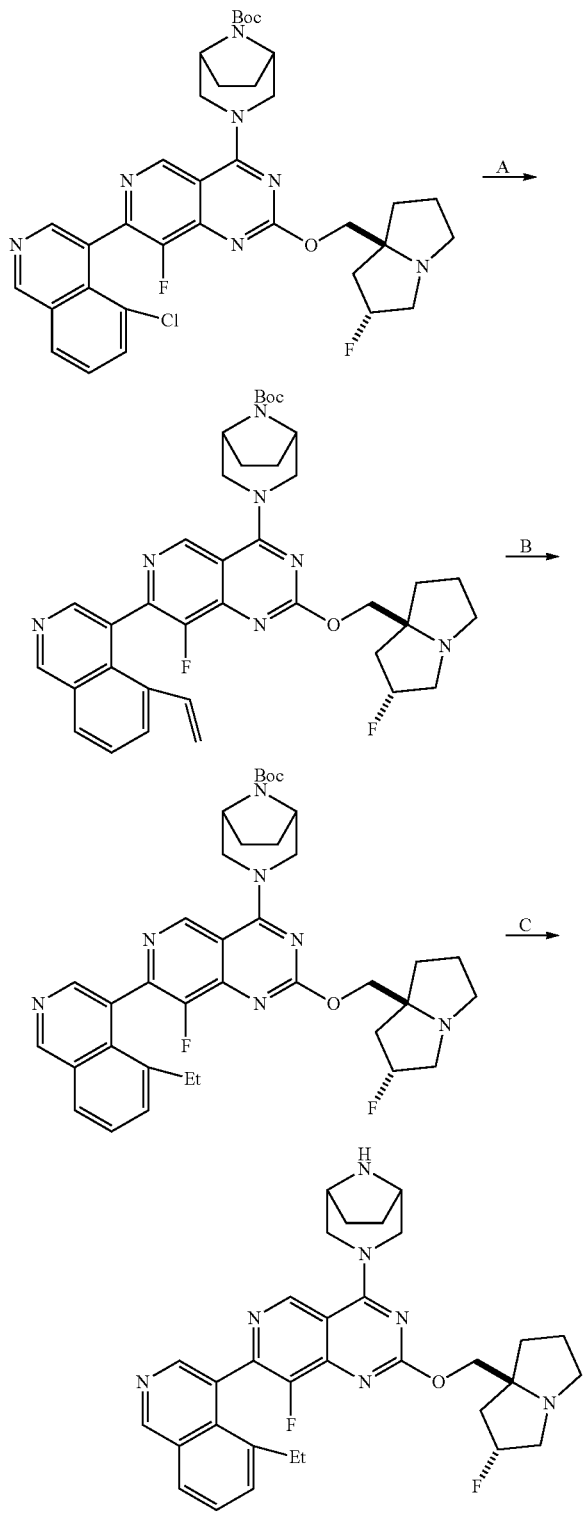

706

Step A. Tert-butyl (1R,5S)-3-(8-fluoro-2-((2-fluorotetrahydro-1H-pyrrolizin-7a(5H)-yl)methoxy)-7-(5-vinylisoquinolin-4-yl)pyrido[4,3-d]pyrimidin-4-yl)-3,8-diazabicyclo[3.2.1]octane-8-carboxylate (racemic, trans): Tert-butyl 3-(7-(5-chloroisoquinolin-4-yl)-8-fluoro-2-((2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (racemic, trans) (Synthesized according to Example 203, step A, 65 mg, 0.096 mmol), potassium vinyltrifluoroborate (39 mg, 0.290 mmol), CsF (66 mg, 0.430 mmol), and tetrakis(triphenylphosphine)palladium (0) (11 mg, 0.010 mmol) were suspended in a mixture of 1,4-dioxane (4 mL) and water (0.7 mL). After degassed with argon, the sealed vial was heated to 95° C. for 18 hours. The reaction mixture was filtered through Celite, the filtrate was condensed, and the residue was purified by prep HPLC (5-95% MeCN/$H_2O$+0.1% TFA in 15 minutes). The desired fractions were partitioned between DCM and saturated aqueous $NaHCO_3$. The organics were separated, dried over $MgSO_4$, and condensed to give tert-butyl (1R,5S)-3-(8-fluoro-2-((2-fluorotetrahydro-1H-pyrrolizin-7a(5H)-yl)methoxy)-7-(5-vinylisoquinolin-4-yl)pyrido[4,3-d]pyrimidin-4-yl)-3,8-diazabicyclo[3.2.1]octane-8-carboxylate (racemic, trans) (26 mg, 41%). LCMS (MM-ES+APCI, Pos): m/z 670.3 (M+H).

Step B. Tert-butyl (1R,5S)-3-(7-(5-ethylisoquinolin-4-yl)-8-fluoro-2-((2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (racemic, trans): Tert-butyl (1R,5S)-3-(8-fluoro-2-((2-fluorotetrahydro-1H-pyrrolizin-7a(5H)-yl)methoxy)-7-(5-vinylisoquinolin-4-yl)pyrido[4,3-d]pyrimidin-4-yl)-3,8-diazabicyclo[3.2.1]octane-8-carboxylate (racemic, trans) (26 mg, 0.039 mmol) was dissolved in ethanol (1 mL). The solution was degassed with argon, and 10% Pd(OH)2/C (10 mg, 0.007 mmol) was added, and the vial was flushed with hydrogen. The reaction was stirred under a hydrogen atmosphere for 1 hour, the mixture was filtered through Celite, and the filtrate was condensed to afford tert-butyl (1R,5S)-3-(7-(5-ethylisoquinolin-4-yl)-8-fluoro-2-((2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (racemic, trans) (26 mg, 100%). LCMS (MM-ES+APCI, Pos): m/z 672.3 (M+H).

Step C. 4-(3,8-diazabicyclo[3.2.1]octan-3-yl)-7-(5-ethylisoquinolin-4-yl)-8-fluoro-2-((2-fluorotetrahydro-1H-pyrrolizin-7a(5H)-yl)methoxy)pyrido[4,3-d]pyrimidine dihydrochloride (racemic, trans): Synthesized according to Example 229, Step B substituting tert-butyl (1R,5S)-3-(7-(5-ethylisoquinolin-4-yl)-8-fluoro-2-((2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (racemic, trans) in place of tert-butyl (1R,5S)-3-(8-fluoro-2-((tetrahydro-1H-pyrrolizin-7a(5H)-yl)methoxy)-7-(2-(trifluoromethoxy)phenyl)pyrido[4,3-d]pyrimidin-4-yl)-3,8-diazabicyclo[3.2.1]octane-8-carboxylate to afford 4-(3,8-diazabicyclo[3.2.1]octan-3-yl)-7-(5-ethylisoquinolin-4-yl)-8-fluoro-2-((2-fluorotetrahydro-1H-pyrrolizin-7a(5H)-yl)methoxy)pyrido[4,3-d]pyrimidine dihydrochloride (racemic, trans) (5 mg, 24%). LCMS (MM-ES+APCI, Pos): m/z 572.3 (M+H).

707
Example 325

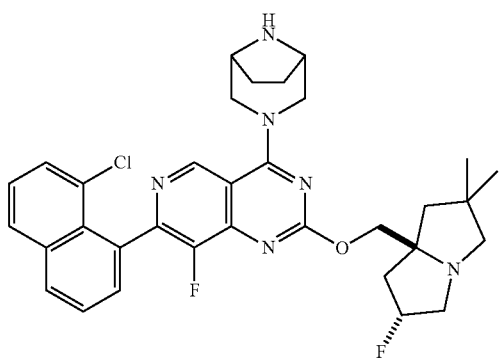

4-((1R,5S)-3,8-diazabicyclo[3.2.1]octan-3-yl)-7-(8-chloronaphthalen-1-yl)-8-fluoro-2-((6-fluoro-2,2-dimethyltetrahydro-1H-pyrrolizin-7a(5H)-yl)methoxy)pyrido[4,3-d]pyrimidine (racemic, trans)

Synthesized according to Example 219, steps E and F substituting ((6S,7aR)-6-fluoro-2,2 dimethyltetrahydro-1H-pyrrolizin-7a(5H)-yl)methanol hydrochloride (trans racemate) for (2-methoxytetrahydro-1H-pyrrolizin-7a(5H)-yl) methanol (trans racemate) to yield 4-((1R,5S)-3,8-diazabicyclo[3.2.1]octan-3-yl)-7-(8-chloronaphthalen-1-yl)-8-fluoro-2-((6-fluoro-2,2-dimethyltetrahydro-1H-pyrrolizin-7a(5H)-yl)methoxy)pyrido[4,3-d]pyrimidine bis-hydrochloride salt (racemic, trans) (25 mg, 0.037 mmol, 100%). LCMS (MM-ES+APCI, Pos): m/z 605.2 (M+H).

Example 326

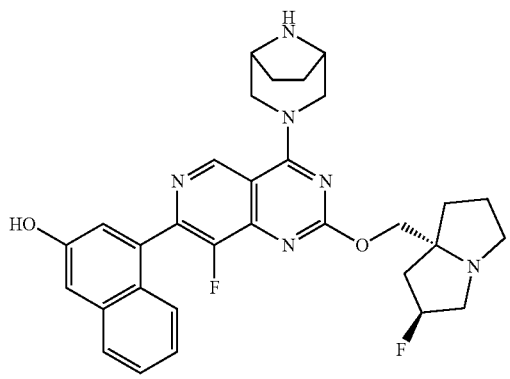

708
4-(4-((1R,5S)-3,8-diazabicyclo[3.2.1]octan-3-yl)-8-fluoro-2-(((2S,7aR)-2-fluorotetrahydro-1H-pyrrolizin-7a(5H)-yl)methoxy)pyrido[4,3-d]pyrimidin-7-yl)naphthalen-2-ol

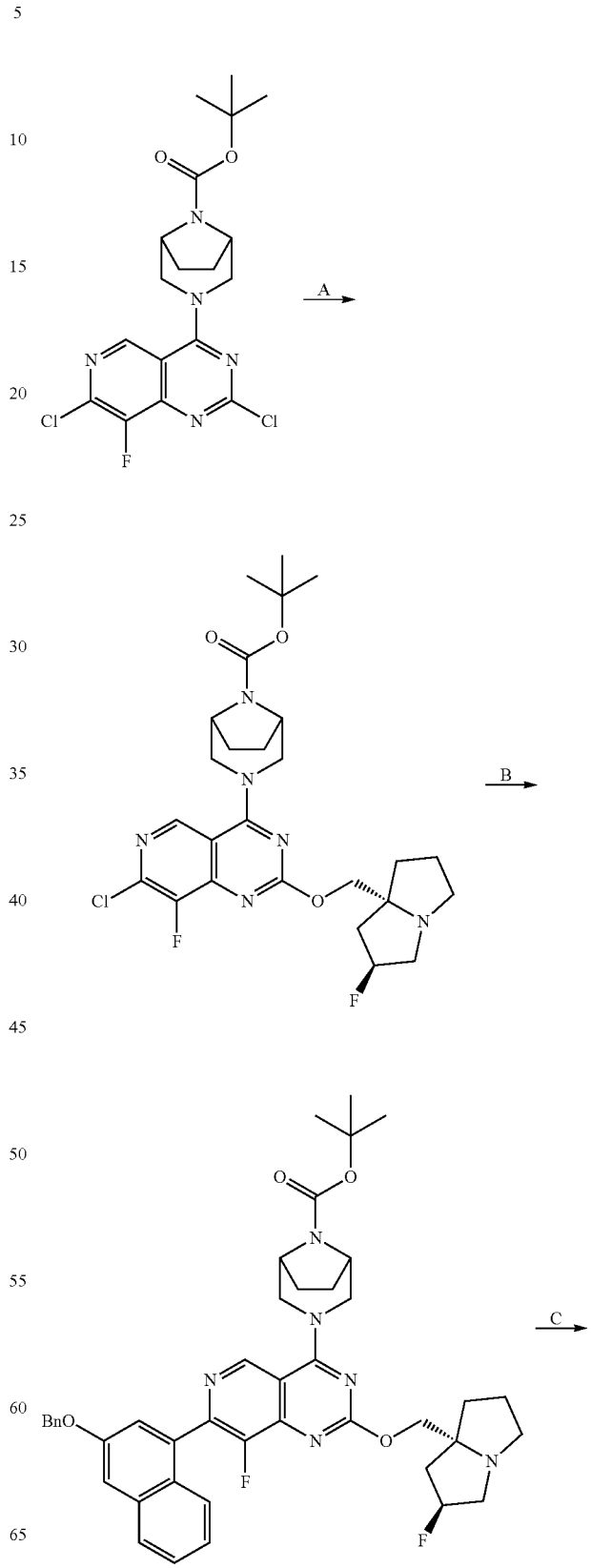

-continued

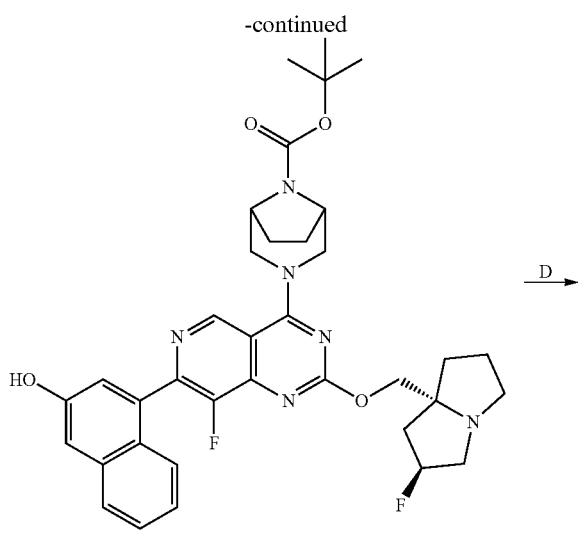

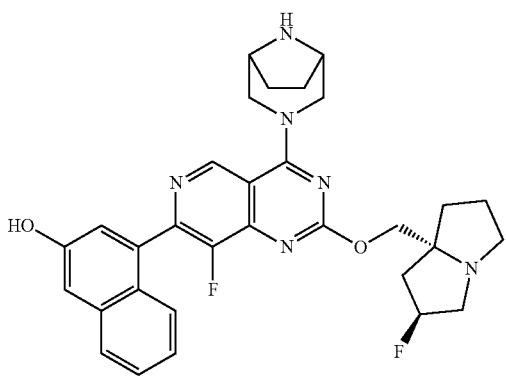 [SMILES: Oc1cc(-c2ncc3c(N4CC5CCC(C4)N5)nc(OC[C@]45CCCN4C[C@@H](F)C5)nc3c2F)c2ccccc2c1]

Step A. tert-butyl (1R,5S)-3-(7-chloro-8-fluoro-2-(((2S,7aR)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate. A mixture of tert-butyl (1R,5S)-3-(2,7-dichloro-8-fluoropyrido[4,3-d]pyrimidin-4-yl)-3,8-diazabicyclo[3.2.1]octane-8-carboxylate (0.10 g, 0.23 mmol) in 1,4-dioxane (3 mL) was treated with ((2S,7aR)-2-fluorotetrahydro-1H-pyrrolizin-7a(5H)-yl)methanol (74 mg, 0.47 mmol) and cesium carbonate (0.23 g, 0.70 mmol) at room temperature. The mixture was stirred at 95° C. overnight. The mixture was diluted with water (60 mL) and extracted with EtOAc (3×20 mL). The combined organic layers were washed with brine (30 mL), dried over sodium sulfate, filtered, and conc. in vacuo. The residue was purified by column chromatography eluting with 10-100% EtOAc/hexanes to afford tert-butyl (1R,5S)-3-(7-chloro-8-fluoro-2-(((2S,7aR)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (67 mg, 52%) as a white solid. LCMS (MM-ES+APCI, Pos). m/z 551.2 (M+H).

Step B. tert-butyl (1R,5S)-3-(7-(3-(benzyloxy)naphthalen-1-yl)-8-fluoro-2-(((2S,7aR)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate. tert-butyl (1R,5S)-3-(7-chloro-8-fluoro-2-(((2S,7aR)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (67 mg, 0.122 mmol), 2-(3-(benzyloxy)naphthalen-1-yl)-4,4,5,5-tetramethyl-1,3,2-dioxaborolane (0.13 g, 0.37 mmol), Pd(PPh$_3$)$_4$ (3.2 mg, 0.012 mmol), and K$_2$CO$_3$ (0.19 mL, 0.36 mmol) were combined in dioxane (1.5 mL) and purged with argon. The mixture was heated to 100° C. in a sealed tube overnight. The cooled mixture was partitioned between water (30 mL) and EtOAc (20 mL) and the aqueous layer was extracted with EtOAc (2×15 mL). The combined organic phases were washed with brine (20 mL), dried over sodium sulfate, filtered, and concentrated in vacuo. The residue was purified by column chromatography eluting with 50-100% EtOAc/hexanes to afford tert-butyl (1R,5S)-3-(7-(3-(benzyloxy)naphthalen-1-yl)-8-fluoro-2-(((2S,7aR)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (72 mg, 79%) as an orange foam. LCMS (MM-ES+APCI, Pos): m/z 749.3 (M+H).

Step C. tert-butyl (1R,5S)-3-(8-fluoro-2-(((2S,7aR)-2-fluorotetrahydro-1H-pyrrolizin-7a(5H)-yl)methoxy)-7-(3-hydroxynaphthalen-1-yl)pyrido[4,3-d]pyrimidin-4-yl)-3,8-diazabicyclo[3.2.1]octane-8-carboxylate. A stirred mixture of tert-butyl (1R,5S)-3-(7-(3-(benzyloxy)naphthalen-1-yl)-8-fluoro-2-(((2S,7aR)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (72 mg, 0.097 mmol), and palladium on carbon, 5%, Degussa type (40 mg, 0.38 mmol) in methanol (0.5 mL) was degassed and stirred under H$_2$ atmosphere for 5 hours. More palladium on carbon, 5%, Degussa type (40 mg, 0.38 mmol) and THF (0.5 mL) were added and the reaction was stirred under a H$_2$ atmosphere for 2 hours. The reaction was filtered through Celite, and the Celite was washed with MeOH. The combined filtrate was concentrated in vacuo. The residue was purified by reverse phase chromatography eluting with 5-95% MeCN/water to afford tert-butyl (1R,5S)-3-(8-fluoro-2-(((2S,7aR)-2-fluorotetrahydro-1H-pyrrolizin-7a(5H)-yl)methoxy)-7-(3-hydroxynaphthalen-1-yl)pyrido[4,3-d]pyrimidin-4-yl)-3,8-diazabicyclo[3.2.1]octane-8-carboxylate (19 mg, 30%) as yellow flakes. LCMS (MM-ES+APCI, Pos): m/z 659.3 (M+H).

Step D. 4-(4-((1R,5S)-3,8-diazabicyclo[3.2.1]octan-3-yl)-8-fluoro-2-(((2S,7aR)-2-fluorotetrahydro-1H-pyrrolizin-7a(5H)-yl)methoxy)pyrido[4,3-d]pyrimidin-7-yl)naphthalen-2-ol dihydrochloride. To a solution of tert-butyl (1R,5S)-3-(8-fluoro-2-(((2S,7aR)-2-fluorotetrahydro-1H-pyrrolizin-7a(5H)-yl)methoxy)-7-(3-hydroxynaphthalen-1-yl)pyrido[4,3-d]pyrimidin-4-yl)-3,8-diazabicyclo[3.2.1]octane-8-carboxylate (0.19 g, 0.029 mmol) in DCM (0.5 mL) was added 4 M HCl in dioxanes (0.5 mL, 2.00 mmol). More HCl (100 ul) was added to the reaction after 1 hour. After stirred for 90 minutes at room temperature, the reaction was concentrated in vacuo. The solid was triturated with ether and filtered to afford 4-(4-((1R,5S)-3,8-diazabicyclo[3.2.1]octan-3-yl)-8-fluoro-2-(((2S,7aR)-2-fluorotetrahydro-1H-pyrrolizin-7a(5H)-yl)methoxy)pyrido[4,3-d]pyrimidin-7-yl)naphthalen-2-ol dihydrochloride (10 mg, 58%) as a yellow powder. LCMS (MM-ES+APCI, Pos): m/z 559.2 (M+H).

Example 327

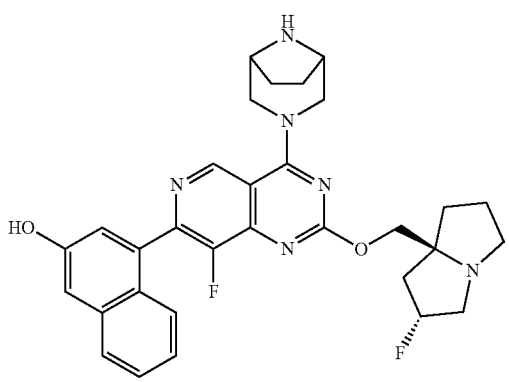 [SMILES: Oc1cc(-c2ncc3c(N4CC5CCC(C4)N5)nc(OC[C@@]45CCCN4C[C@H](F)C5)nc3c2F)c2ccccc2c1]

4-(4-((1R,5S)-3,8-diazabicyclo[3.2.1]octan-3-yl)-8-fluoro-2-(((2R,7aS)-2-fluorotetrahydro-1H-pyrrolizin-7a(5H)-yl)methoxy)pyrido[4,3-d]pyrimidin-7-yl)naphthalen-2-ol Synthesized according to Example 326, Steps A-D substituting ((2R,7aS)-2-fluorotetrahydro-1H-pyrrolizin-7a(5H)-yl)methanol in place of((2S,7aR)-2-fluorotetrahydro-1H-pyrrolizin-7a(5H)-yl)methanol (racemic, trans) in Step A to afford 4-(4-((1R,5S)-3,8-diazabicyclo[3.2.1]octan-3-yl)-8-fluoro-2-(((2R,7aS)-2-fluorotetrahydro-1H-pyrrolizin-7a(5H)-yl)methoxy)pyrido[4,3-d]pyrimidin-7-yl)naphthalen-2-ol dihydrochloride (18 mg, 69%). LCMS (MM-ES+APCI, Pos): m/z 559.3 (M+H).

Example 328

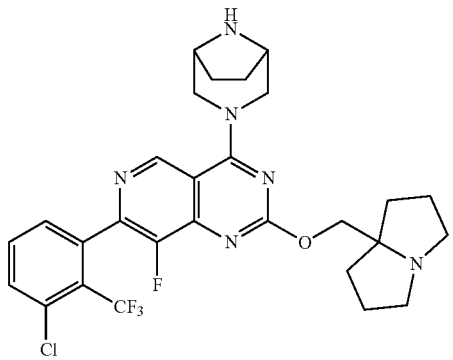 [SMILES: Fc1c(-c2cccc(Cl)c2C(F)(F)F)ncc2c(N3CC4CCC(C3)N4)nc(OCC34CCCN3CCC4)nc12]

4-((1R,5S)-3,8-diazabicyclo[3.2.1]octan-3-yl)-7-(3-chloro-2-(trifluoromethyl)phenyl)-8-fluoro-2-((tetrahydro-1H-pyrrolizin-7a(5H)-yl)methoxy)pyrido[4,3-d]pyrimidine Synthesized according to Example 196 substituting 2-(3-chloro-2-(trifluoromethyl)phenyl)-4,4,5,5-tetramethyl-1,3,2-dioxaborolane in place of 2,2-difluorobenzo[1,3]dioxole-4-boronic acid in step B to afford 4-((1R,5S)-3,8-diazabicyclo[3.2.1]octan-3-yl)-7-(3-chloro-2-(trifluoromethyl)phenyl)-8-fluoro-2-((tetrahydro-1H-pyrrolizin-7a(5H)-yl)methoxy)pyrido[4,3-d]pyrimidine (12 mg, 68%). LCMS (MM-ES+APCI, Pos): m/z 577.2 (M+H).

Example 329

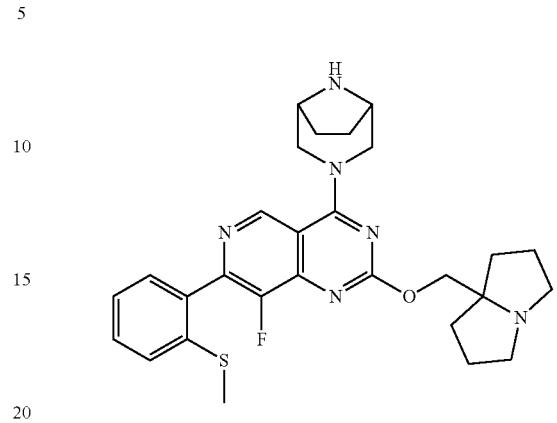

4-((1R,5S)-3,8-diazabicyclo[3.2.1]octan-3-yl)-8-fluoro-7-(2-(methylthio)phenyl)-2-((tetrahydro-1H-pyrrolizin-7a(5H)-yl)methoxy)pyrido[4,3-d]pyrimidine Synthesized according to Example 196 substituting 2-(methylthio)phenylboronic acid in place of 2,2-difluorobenzo[1,3]dioxole-4-boronic acid in step B to afford 4-((1R,5S)-3,8-diazabicyclo[3.2.1]octan-3-yl)-8-fluoro-7-(2-(methylthio)phenyl)-2-((tetrahydro-1H-pyrrolizin-7a(5H)-yl)methoxy)pyrido[4,3-d]pyrimidine (22 mg, 24%). LCMS (MM-ES+APCI, Pos): m/z 521.3 (M+H).

Example 330

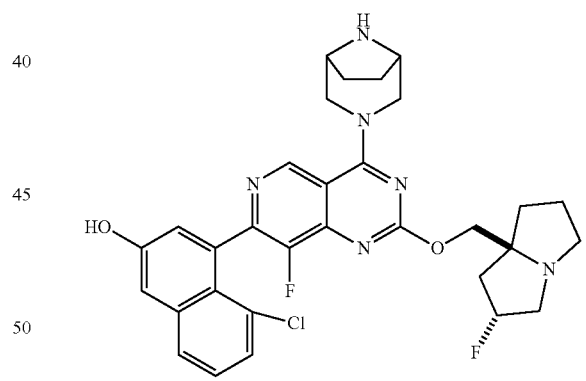

4-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-5-chloronaphthalen-2-ol (racemic, trans)

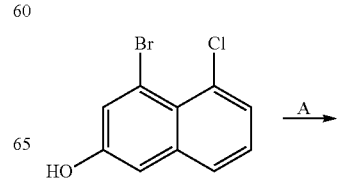

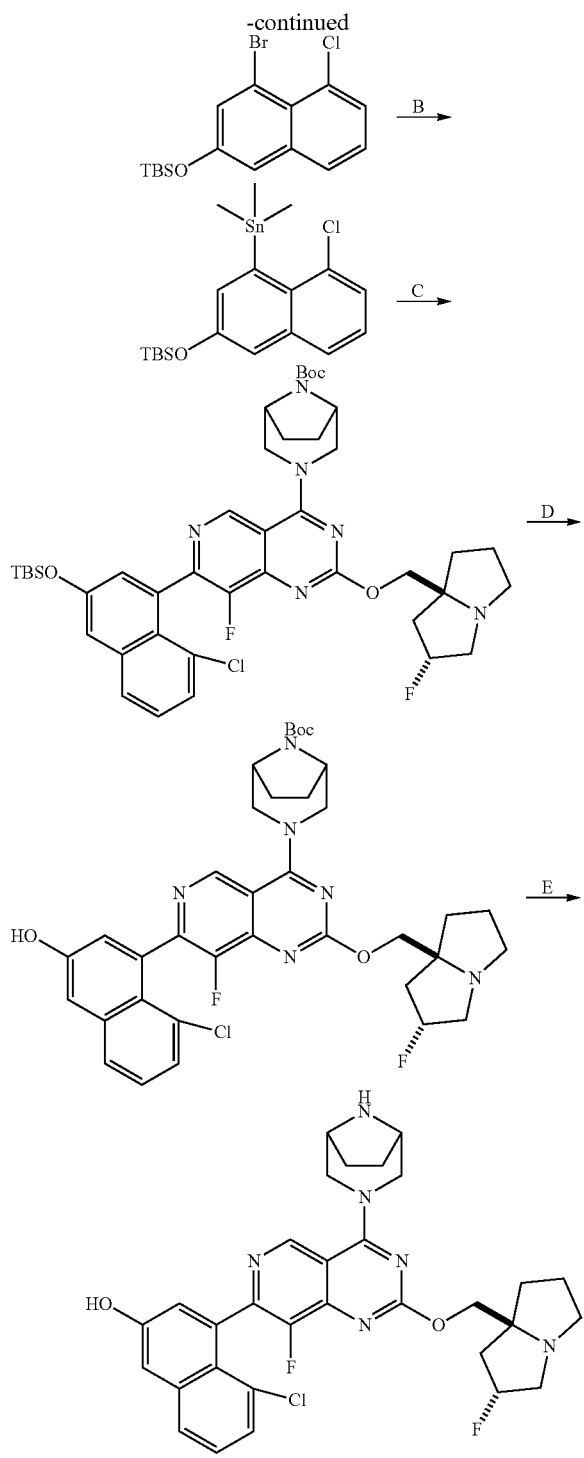

Step A. ((4-bromo-5-chloronaphthalen-2-yl)oxy)(tert-butyl)dimethylsilane.

Imidazole (271 mg, 3.98 mmol) and tert-butyldimethylchlorosilane (0.24 g, 1.6 mmol) were added to a solution of 4-bromo-5-chloronaphthalen-2-ol (synthesized according to Example 36, step A-C, 0.41 g, 1.6 mmol) in DCM (10 mL). The reaction was stirred for 30 minutes and quenched with water. The organics were separated and washed with aqueous 1 N HCl and saturated aqueous NaHCO₃. The organics were dried over MgSO₄ and condensed. The residue was purified by flash chromatography (RediSep Gold 24 g column, 0-5% EtOAc/hexanes) to afford ((4-bromo-5-chloronaphthalen-2-yl)oxy)(tert-butyl)dimethylsilane (0.48 g, 82%). $^1$H NMR (400 MHz, CDCl₃): δ 7.60 (d, J=7.9 Hz, 1H), 7.54 (d, J=2.6 Hz, 1H), 7.48 (dd, J=1.2, 7.5 Hz, 1H), 7.28 (t, J=7.8 Hz, 1H), 7.15 (d, J=2.4 Hz, 1H), 1.01 (s, 9H), 0.26 (s, 6H).

Step B. Tert-butyl((5-chloro-4-(trimethylstannyl)naphthalen-2-yl)oxy)dimethylsilane. ((4-Bromo-5-chloronaphthalen-2-yl)oxy)(tert-butyl)dimethylsilane (0.48 g, 1.3 mmol) and hexamethylditin (1.4 mL, 6.5 mmol) were taken up in toluene (8 mL). The mixture was degassed and purged with argon, tetrakis(triphenylphosphine) Pd(0) (0.15 g, 0.13 mmol) was added, and the mixture was degassed and purged with argon. The reaction was sealed and heated to 110° C. for 16 hours. The cooled mixture was filtered through Celite and condensed. The residue was purified by flash chromatography (RediSep Gold 40 g column, 0-5% EtOAc/hexanes) to afford tert-butyl((5-chloro-4-(trimethylstannyl)naphthalen-2-yl)oxy)dimethylsilane (0.50 mg, 84%). $^1$H NMR (400 MHz, CDCl₃): δ 7.62 (d, J=8.5 Hz, 1H), 7.45-7.43 (m, 2H), 7.29 (t, J=7.8 Hz, 1H), 7.17 (d, J=2.7 Hz, 1H), 1.03 (s, 9H), 0.48-0.34 (m, 9H), 0.26 (s, 6H).

Step C. Tert-butyl (1R,5S)-3-(7-(3-((tert-butyldimethylsilyl)oxy)-8-chloronaphthalen-1-yl)-8-fluoro-2-((2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (racemic, trans). Synthesized according to Example 33, Step B substituting tert-butyl((5-chloro-4-(trimethylstannyl)naphthalen-2-yl)oxy)dimethylsilane in place of 5-chloro-4-(trimethylstannyl)isoquinoline to afford tert-butyl (1R,5S)-3-(7-(3-((tert-butyldimethylsilyl)oxy)-8-chloronaphthalen-1-yl)-8-fluoro-2-((2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (racemic, trans) (26 mg, 35%). LCMS (MM-ES+APCI, Pos): m/z 808.3 (M+H).

Step D. Tert-butyl 3-(7-(8-chloro-3-hydroxynaphthalen-1-yl)-8-fluoro-2-((2-fluorotetrahydro-1H-pyrrolizin-7a (5H)-yl)methoxy)pyrido[4,3-d]pyrimidin-4-yl)-3,8-diazabicyclo[3.2.1]octane-8-carboxylate (racemic, trans). Tert-butyl (1R,5S)-3-(7-(3-((tert-butyldimethylsilyl)oxy)-8-chloronaphthalen-1-yl)-8-fluoro-2-((2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (racemic, trans) (20 mg, 0.025 mmol) was dissolved in THF (1.5 mL). 1 N THF solution of tetra-n-butylammonium fluoride (0.12 mL, 0.12 mmol) was added and the reaction was stirred for 30 minutes. The reaction was quenched with water and extracted with EtOAc 3 times. The combined organics were dried over MgSO₄ and condensed. Purification by flash chromatography (RediSep Gold 4 g column, 0-10% MeOH/DCM) afforded tert-butyl 3-(7-(8-chloro-3-hydroxynaphthalen-1-yl)-8-fluoro-2-((2-fluorotetrahydro-1H-pyrrolizin-7a (5H)-yl)methoxy)pyrido[4,3-d]pyrimidin-4-yl)-3,8-diazabicyclo[3.2.1]octane-8-carboxylate (racemic, trans) (9.0 mg, 52%). LCMS (MM-ES+APCI, Pos): m/z 693.3 (M+H).

Step E. 4-(4-((1R,5S)-3,8-diazabicyclo[3.2.1]octan-3-yl)-8-fluoro-2-((2-fluorotetrahydro-1H-pyrrolizin-7a(5H)-yl) methoxy)pyrido[4,3-d]pyrimidin-7-yl)-5-chloronaphthalen-2-ol (racemic, trans). Synthesized according to Example 229, Step B substituting tert-butyl 3-(7-(8-chloro-3-hydroxynaphthalen-1-yl)-8-fluoro-2-((2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (racemic, trans) in place of tert-butyl (1R,5S)-3-(8-fluoro-2-((tetrahydro-1H-pyrrolizin-7a(5H)-yl)methoxy)-7-(2-(trifluoromethoxy)phenyl)pyrido[4,3-d]pyrimidin-4-yl)-3,8-diazabicyclo[3.2.1]octane-8-carboxylate to afford the title compound (4.0 mg, 46%). LCMS (MM-ES+APCI, Pos): m/z 593.2 (M+H).

Example 331

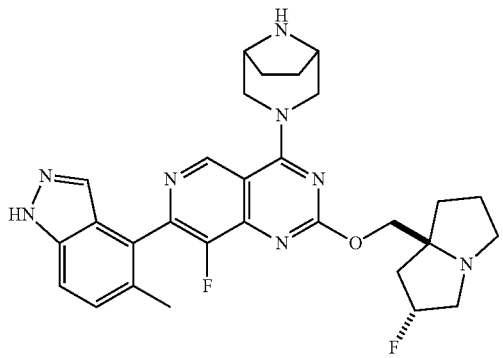

4-((1R,5S)-3,8-diazabicyclo[3.2.1]octan-3-yl)-8-fluoro-2-((2-fluorotetrahydro-1H-pyrrolizin-7a(5H)-yl)methoxy)-7-(5-methyl-1H-indazol-4-yl)pyrido[4,3-d]pyrimidine (racemic, trans)

Synthesized according to Example 3, Steps G-I substituting (2-fluorotetrahydro-1H-pyrrolizin-7a(5H)-yl)methanol (racemic, trans) in place of 2-(1-methyl-1H-imidazol-2-yl)ethan-1-ol in Step G and (5-methyl-1H-indazol-4-yl)boronic acid in place of 4-(4,4,5,5-tetramethyl-1,3,2-dioxaborolan-2-yl)naphthalen-2-ol in Step H to afford 4-((1R,5S)-3,8-diazabicyclo[3.2.1]octan-3-yl)-8-fluoro-2-((2-fluorotetrahydro-1H-pyrrolizin-7a(5H)-yl)methoxy)-7-(5-methyl-1H-indazol-4-yl)pyrido[4,3-d]pyrimidine bis(2,2,2-trifluoroacetate) (racemic, trans) (27 mg, 68%). LCMS (MM-ES+APCI, Pos): m/z 547.3 (M+H).

Example 332

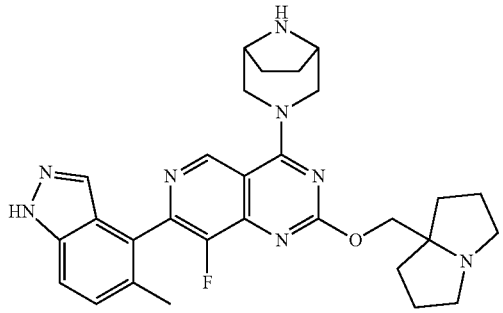 [SMILES: Cc1ccc2[nH]ncc2c1-c1ncc2c(N3CC4CCC(C3)N4)nc(OCC34CCCN3CCC4)nc2c1F]

4-((1R,5S)-3,8-diazabicyclo[3.2.1]octan-3-yl)-8-fluoro-7-(5-methyl-1H-indazol-4-yl)-2-((tetrahydro-1H-pyrrolizin-7a(5H)-yl)methoxy)pyrido[4,3-d]pyrimidine Synthesized according to Example 3, Steps G-I substituting (tetrahydro-1H-pyrrolizin-7a(5H)-yl)methanol in place of 2-(1-methyl-1H-imidazol-2-yl)ethan-1-ol in Step G and (5-methyl-1H-indazol-4-yl)boronic acid in place of 4-(4,4,5,5-tetramethyl-1,3,2-dioxaborolan-2-yl)naphthalen-2-ol in Step H to afford 4-((1R,5S)-3,8-diazabicyclo[3.2.1]octan-3-yl)-8-fluoro-7-(5-methyl-1H-indazol-4-yl)-2-((tetrahydro-1H-pyrrolizin-7a(5H)-yl)methoxy)pyrido[4,3-d]pyrimidine bis(2,2,2-trifluoroacetate) (14 mg, 45%). LCMS (MM-ES+APCI, Pos): m/z 529.3 (M+H).

Example 333

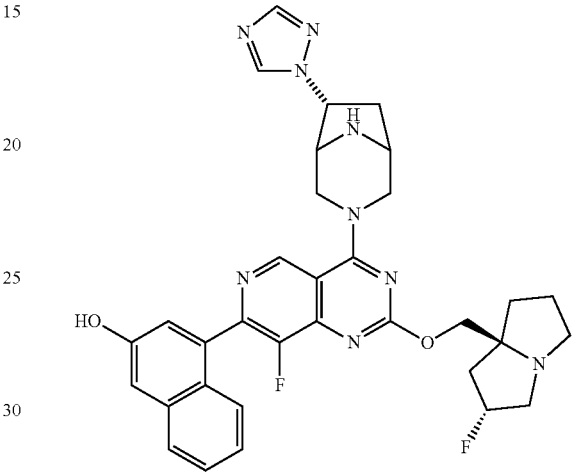

4-(4-((6R)-6-(1H-1,2,4-triazol-1-yl)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)naphthalen-2-ol (racemic, trans)

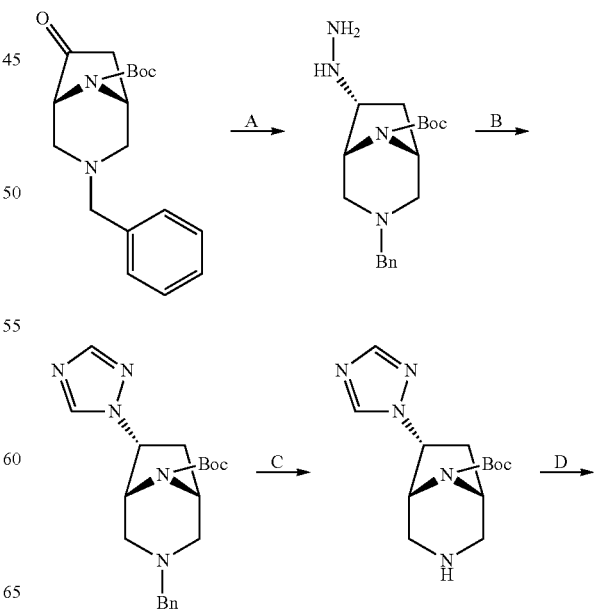

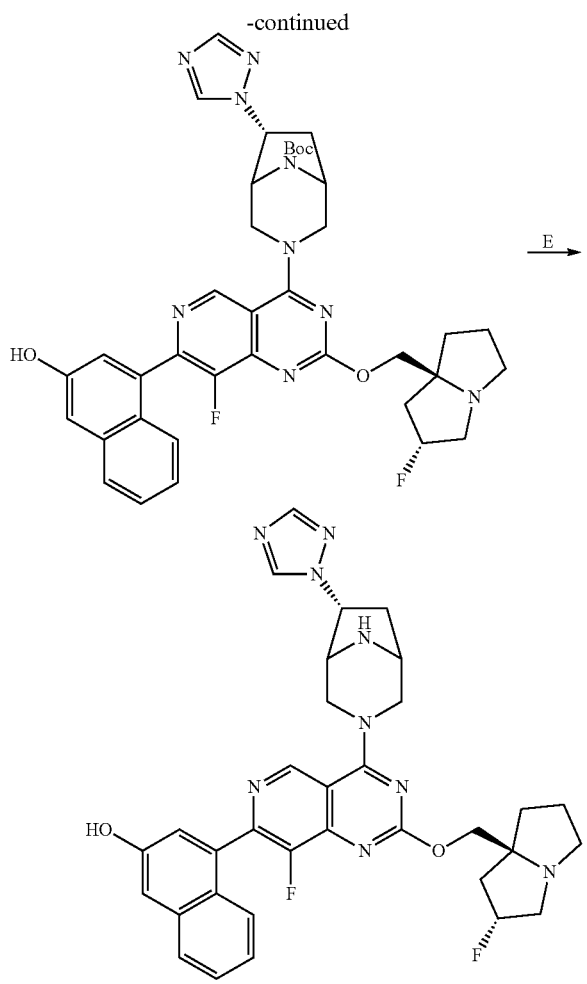

Step A. Tert-butyl (1R,5R,6R)-3-benzyl-6-hydrazinyl-3,8-diazabicyclo[3.2.1]octane-8-carboxylate. A stirred mixture of tert-butyl (1R,5R)-3-benzyl-6-oxo-3,8-diazabicyclo[3.2.1]octane-8-carboxylate (0.10 g, 0.32 mmol) and 1M hydrazine in THF (3 mL) under $N_2$ was brought to reflux for 6 h. The reaction mixture was evaporated under $N_2$ flow and dried under high vacuum overnight. The residue was dissolved in THF (2 mL) and cooled on ice-salt bath. 1M borane in THF (y0.32 mL, 0.32 mmol) was added dropwise. The solution was heated to reflux for 1 h, THF was evaporated under $N_2$, and toluene (2 mL) was added. The reaction mixture was heated to 90° C. for 1 h under $N_2$, cooled to r.t., evaporated, and chromatographed on silica gel in 2 to 20% MeOH/DCM to yield the desired product as a colorless solid (47 mg, 28%). LCMS (MM-ES+APCI, Pos): m/z 333.3 (M+H).

Step B. Tert-butyl (1R,5R)-3-benzyl-6-(1H-1,2,4-triazol-1-yl)-3,8-diazabicyclo[3.2.1]octane-8-carboxylate. A stirred solution of crude tert-butyl (1R,5R)-3-benzyl-6-hydrazinyl-3,8-diazabicyclo[3.2.1]octane-8-carboxylate (47 mg, 0.085 mmol) in absolute ethanol (0.2 mL) under $N_2$ was cooled to −78° C. and 4M hydrogen chloride in dioxane (21 μL, 0.085 mmol) was added dropwise. The solution was warmed to r.t., and 1,3,5-triazine (14 mg, 0.17 mmol) was added at once. The reaction mixture was heated to reflux for 3 h, cooled to r.t., concentrated under $N_2$ flow, and partitioned between EtOAc (20 mL) and 0.5M $NaHCO_3$ (10 mL). The organic layer was washed with brine, dried over $Na_2CO_3$, evaporated in vacuo and chromatographed on silica gel in 20 to 100% EtOAc/hexane to yield the desired product as colorless viscous oil (15 mg, 43%). LCMS (MM-ES+APCI, Pos): m/z 370.3 (M+H).

Step C. Tert-butyl (1R,5R,6R)-6-(1H-1,2,4-triazol-1-yl)-3,8-diazabicyclo[3.2.1]octane-8-carboxylate. Synthesized according to Example 168, Step D, substituting tert-butyl (1R,5R,6R)-3-benzyl-6-(1H-1,2,4-triazol-1-yl)-3,8-diazabicyclo[3.2.1]octane-8-carboxylate in place of 1-(2-(benzyloxy)ethyl)-2-(fluoromethyl)-1H-imidazole. The crude product was dissolved in MTBE (2 mL), filtered through a cotton plug, and evaporated. The material was used crude in the next reaction. LCMS (MM-ES+APCI, Pos): m/z 280.2 (M+H).

Step D. Tert-butyl (6R)-3-(8-fluoro-2-((2-fluorotetrahydro-1H-pyrrolizin-7a(5H)-yl)methoxy)-7-(3-hydroxynaphthalen-1-yl)pyrido[4,3-d]pyrimidin-4-yl)-6-(1H-1,2,4-triazol-1-yl)-3,8-diazabicyclo[3.2.1]octane-8-carboxylate (racemic, trans). Synthesized according to Example 31, Step F, substituting tert-butyl (1R,5R,6R)-6-(1H-1,2,4-triazol-1-yl)-3,8-diazabicyclo[3.2.1]octane-8-carboxylate in place of tert-butyl 6-((triethylsilyl)oxy)-3,8-diazabicyclo[3.2.1]octane-8-carboxylate and 8-fluoro-2-(((2R,7aS)-2-fluorotetrahydro-1H-pyrrolizin-7a(5H)-yl)methoxy)-7-(3-hydroxynaphthalen-1-yl)pyrido[4,3-d]pyrimidin-4-ol in place of (S)-8-fluoro-7-(3-hydroxynaphthalen-1-yl)-2-((1-methylpyrrolidin-2-yl)methoxy)pyrido[4,3-d]pyrimidin-4-ol. Chromatographed on the reverse phase, C18, 5-95% MeCN—$H_2O$+0.1% TFA to yield the desired compound as the TFA salt (15 mg, 45%). LCMS (MM-ES+APCI, Pos): m/z 726.3 (M+H).

Step E. 4-(4-((6R)-6-(1H-1,2,4-triazol-1-yl)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)naphthalen-2-ol (racemic, trans). Synthesized according to Example 3, Step I, substituting tert-butyl (6R)-3-(8-fluoro-2-((2-fluorotetrahydro-1H-pyrrolizin-7a(5H)-yl)methoxy)-7-(3-hydroxynaphthalen-1-yl)pyrido[4,3-d]pyrimidin-4-yl)-6-(1H-1,2,4-triazol-1-yl)-3,8-diazabicyclo[3.2.1]octane-8-carboxylate (racemic, trans) in place of tert-butyl (1R,5S)-3-(8-fluoro-7-(3-hydroxynaphthalen-1-yl)-2-(2-(1-methyl-1H-imidazol-2-yl)ethoxy)pyrido[4,3-d]pyrimidin-4-yl)-3,8-diazabicyclo[3.2.1]octane-8-carboxylate (4.5 mg, 41%). LCMS (MM-ES+APCI, Pos): m/z 626.4 (M+H).

Example 334

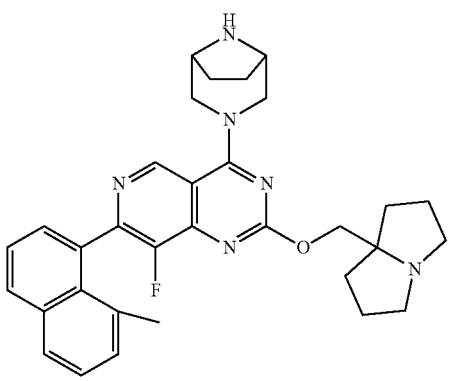 [SMILES: Cc1cccc2cccc(-c3ncc4c(N5CC6CCC(C5)N6)nc(OCC56CCCN5CCC6)nc4c3F)c12]

719

4-((1R,5S)-3,8-diazabicyclo[3.2.1]octan-3-yl)-8-fluoro-7-(8-methylnaphthalen-1-yl)-2-((tetrahydro-1H-pyrrolizin-7a(5H)-yl)methoxy)pyrido[4,3-d]pyrimidine Synthesized according to Example 196 substituting 4,4,5,5-tetramethyl-2-(8-methylnaphthalen-1-yl)-1,3,2-dioxaborolane in place of 2,2-difluorobenzo[1,3]dioxole-4-boronic acid in step B to afford 4-((1R,5S)-3,8-diazabicyclo[3.2.1]octan-3-yl)-8-fluoro-7-(8-methylnaphthalen-1-yl)-2-((tetrahydro-1H-pyrrolizin-7a(5H)-yl)methoxy)pyrido[4,3-d]pyrimidine (13 mg, 29%). LCMS (MM-ES+APCI, Pos): m/z 539.3 (M+H).

Example 335

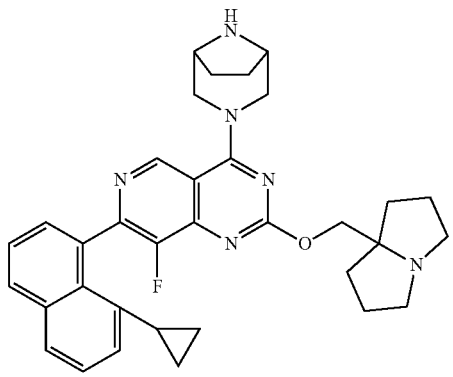 [SMILES: Fc1c(-c2cccc3cccc(C4CC4)c23)ncc2c(N3CC4CCC(C3)N4)nc(OCC34CCCN3CCC4)nc12]

4-((1R,5S)-3,8-diazabicyclo[3.2.1]octan-3-yl)-7-(8-cyclopropylnaphthalen-1-yl)-8-fluoro-2-((tetrahydro-1H-pyrrolizin-7a(5H)-yl)methoxy)pyrido[4,3-d]pyrimidine

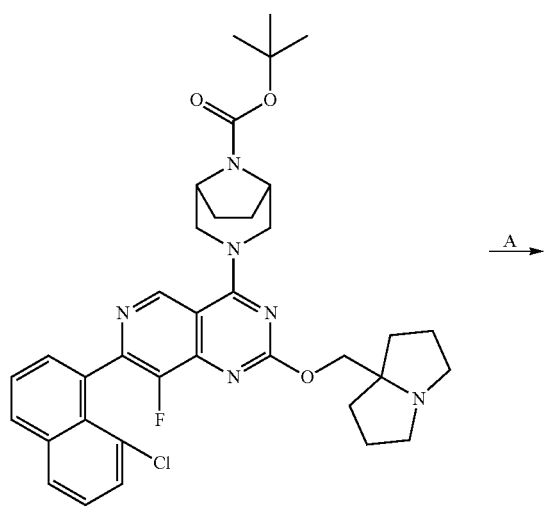

720

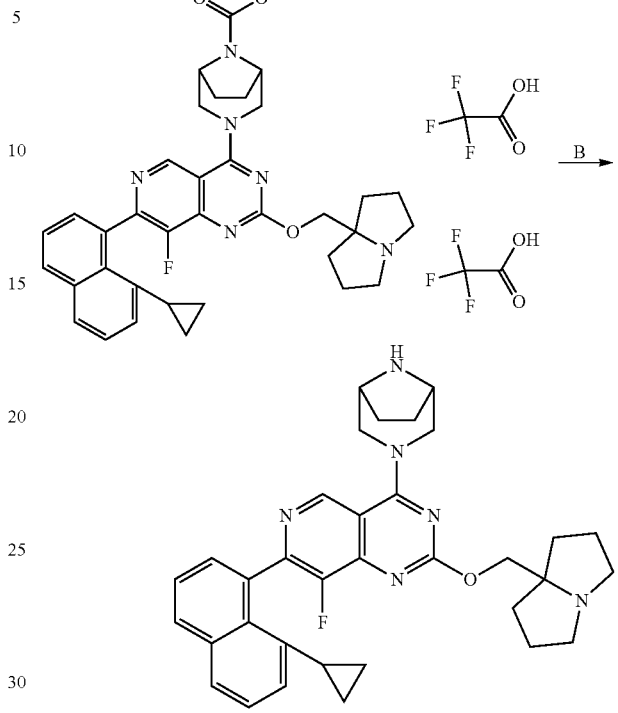

Step A. tert-butyl (1R,5S)-3-(7-(8-cyclopropylnaphthalen-1-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate bis(2,2,2-trifluoroacetate). To a mixture of tert-butyl (1R,5S)-3-(7-(8-chloronaphthalen-1-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (synthesized according to Example 241, step A, 33 mg, 0.050 mmol), cyclopropylboronic acid pinacol ester (42 mg, 0.25 mmol), and cesium carbonate (49 mg, 0.15 mmol) in a vial were added DMF (0.50 mL) and water (0.10 mL), followed by addition of butyl di-1-adamantylphosphine (7.2 mg, 0.020 mmol) and Pd(OAc)$_2$ (2.2 mg, 0.010 mmol) under N$_2$. The vial was closed and heated at 100° C. for 15 h. The mixture was cooled to rt and was purified by preparative C18 HPLC (Gilson, 0-95% CH$_3$CN/H$_2$O with 0.1% TFA). The desired fractions were combined and concentrated to give the crude title compound (4 mg, 5%) as a yellow solid. LCMS (MM-ES+APCI, Pos): m/z 665.3 (M+H).

Step B. 4-((1R,5S)-3,8-diazabicyclo[3.2.1]octan-3-yl)-7-(8-cyclopropylnaphthalen-1-yl)-8-fluoro-2-((tetrahydro-1H-pyrrolizin-7a(5H)-yl)methoxy)pyrido[4,3-d]pyrimidine tris(2,2,2-trifluoroacetate). To a solution of tert-butyl (1R,5S)-3-(7-(8-cyclopropylnaphthalen-1-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate bis(2,2,2-trifluoroacetate) (4 mg, 0.002 mmol) in DCM (0.4 mL) was added TFA (0.2 mL). The mixture was stirred at rt for 0.5 h and concentrated. The residue was purified by preparative C18 HPLC (Gilson, 0-95% CH$_3$CN/H$_2$O with 0.1% TFA). The desired fractions were combined and concentrated to give the title compound (0.5 mg, 28%) as the bis TFA salt. LCMS (MM-ES+APCI, Pos): m/z 565.2 (M+H).

Example 336

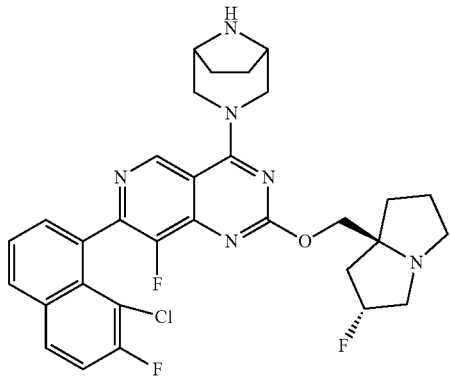 [SMILES: Fc1ccc2cccc(-c3ncc4c(N5CC6CCC(C5)N6)nc(OC[C@@]56CCCN5C[C@H](F)C6)nc4c3F)c2c1Cl]

4-((1R,5S)-3,8-diazabicyclo[3.2.1]octan-3-yl)-7-(8-chloro-7-fluoronaphthalen-1-yl)-8-fluoro-2-((2-fluorotetrahydro-1H-pyrrolizin-7a(5H)-yl)methoxy)pyrido[4,3-d]pyrimidine (racemic, trans)

Synthesized according to Example 29, Steps C-H substituting 2-(8-chloro-7-fluoronaphthalen-1-yl)-4,4,5,5-tetramethyl-1,3,2-dioxaborolane (synthesized according to Example 44, step A-C) in place of 2-(8-chloronaphthalen-1-yl)-4,4,5,5-tetramethyl-1,3,2-dioxaborolane in Step C and (2-fluorotetrahydro-1H-pyrrolizin-7a(5H)-yl)methanol (racemic, trans) in place of (S)-(1-isopropylpyrrolidin-2-yl)methanol in Step H followed by deprotection using Example 391, Step A to afford 4-((1R,5S)-3,8-diazabicyclo[3.2.1]octan-3-yl)-7-(8-chloro-7-fluoronaphthalen-1-yl)-8-fluoro-2-((2-fluorotetrahydro-1H-pyrrolizin-7a(5H)-yl)methoxy)pyrido[4,3-d]pyrimidine dihydrochloride (racemic, trans) (11 mg, 56%). LCMS (MM-ES+APCI, Pos): m/z 595.2 (M+H).

Example 337

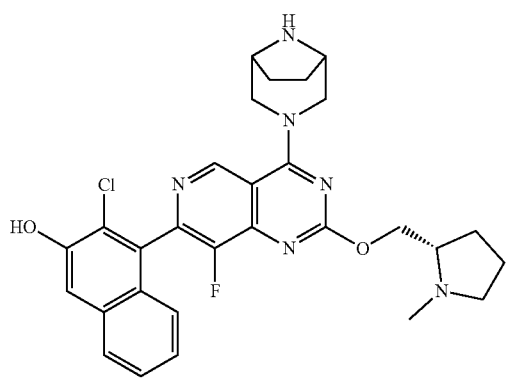 [SMILES: CN1CCC[C@H]1COc1nc(N2CC3CCC(C2)N3)c2cnc(-c3c(Cl)c(O)cc4ccccc34)c(F)c2n1]

4-(4-(3,8-diazabicyclo[3.2.1]octan-3-yl)-8-fluoro-2-(((S)-1-methylpyrrolidin-2-yl)methoxy)pyrido[4,3-d]pyrimidin-7-yl)-3-chloronaphthalen-2-ol

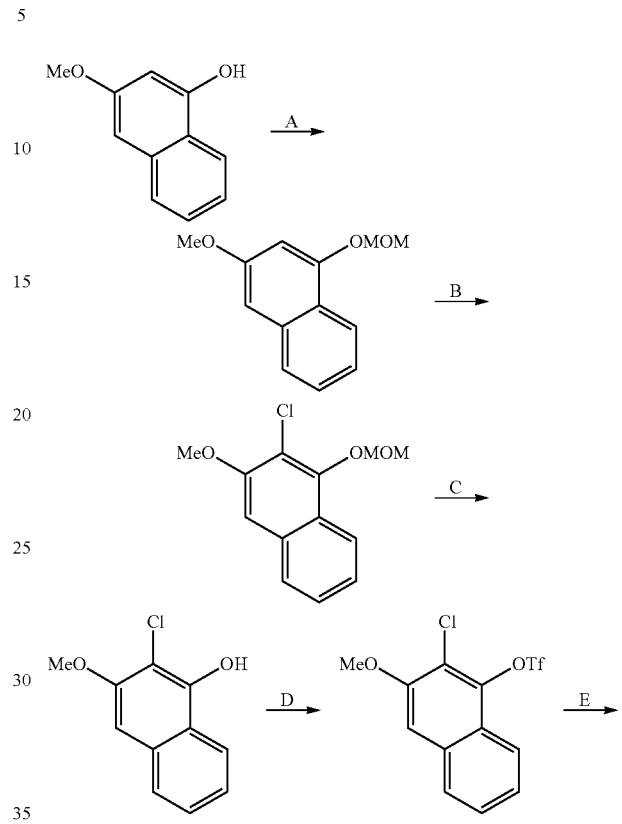

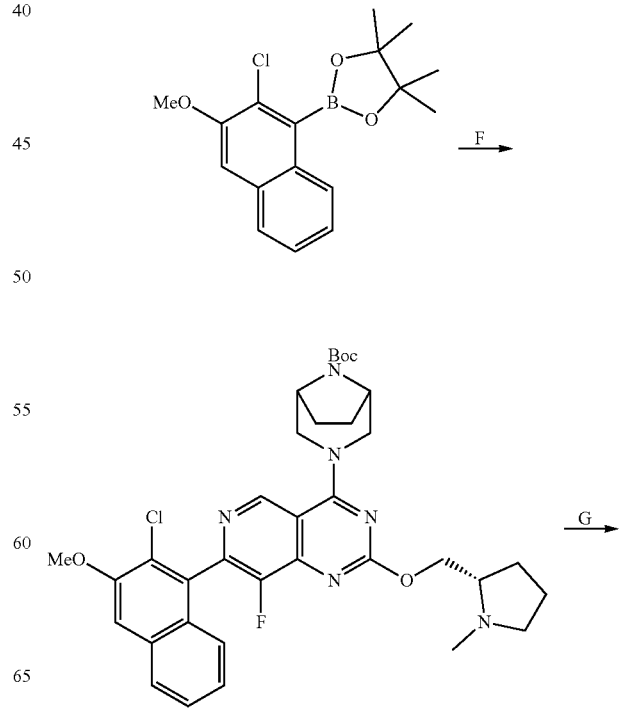

-continued

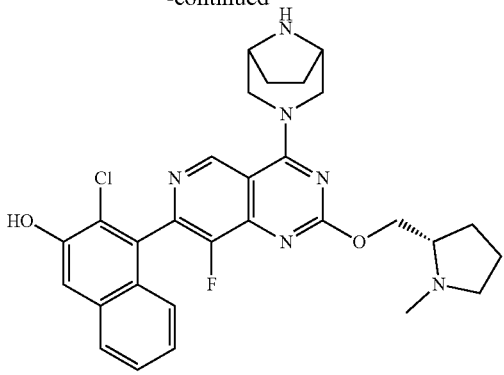

Step A. 3-methoxy-1-(methoxymethoxy)naphthalene. To a solution of 3-methoxynaphthalen-1-ol (0.52 g, 3.0 mmol) in tetrahydrofuran (15 mL) at 0° C. was added NaH (60%, 0.14 g, 3.6 mmol). The mixture was stirred at 0° C. for 10 min followed by dropwise addition of MOM-Cl (0.25 mL, 3.3 mmol). The mixture was stirred at 0° C. for 0.5 h and warmed to rt. The mixture was quenched with water and extracted with ethyl acetate. The extract was dried ($Na_2SO_4$) and concentrated. The residue was purified by flash chromatography eluting with ethyl acetate/hexanes (0-10%) to give the title compound (0.42 g, 64%) as a pale-yellow oil. LCMS (MM-ES+APCI, Pos): m/z 219.2 (M+H).

Step B. 2-chloro-3-methoxy-1-(methoxymethoxy)naphthalene. To a solution of 3-methoxy-1-(methoxymethoxy) naphthalene (0.10 mg, 0.48 mmol) in THF (3 mL) at 0° C. was added n-Buli (2.5 M in hexanes, 0.38 mL, 0.95 mmol). The solution was stirred at 0° C. for 1 h, followed by addition of hexachloroethane (0.22 g, 0.95 mmol). The resulting mixture was stirred at 0° C. for 30 min. and warmed to rt. The reaction was diluted with water and extracted with ethyl acetate. The extract was dried ($Na_2SO_4$), concentrated and purified by flash chromatography eluting with ethyl acetate/hexanes (0-10%) to give the title compound (98 mg, 81%) as a colorless oil. LCMS (MM-ES+APCI, Pos): m/z 253.1 (M+H).

Step C. 2-chloro-3-methoxynaphthalen-1-ol. To a solution of 2-chloro-3-methoxy-1-(methoxymethoxy)naphthalene (90 mg, 0.36 mmol) in methanol (1.2 mL) was added HCl (6.0 M, 0.24 mL, 1.44 mmol). The solution was stirred at rt for 2 h and heated at 50° C. for 2 h. The mixture was cooled to r.t, diluted with ethyl acetate, and washed with water and brine. The resulting solution was dried ($Na_2SO_4$) and concentrated to give the crude title compound (70 mg, 94%) as a pinkish solid. $^1$H NMR (400 MHz, ($CDCl_3$) δ 8.13 (d, J=8.4 Hz, 1H), 7.68 (d, J=8.2 Hz, 1H), 7.48 (m, 1H), 7.37 (m, 1H), 6.82 (s, 1H), 6.11 (s, 1H), 4.00 (s, 3H).

Step D. 2-chloro-3-methoxynaphthalen-1-yl trifluoromethanesulfonate. To a solution of 2-chloro-3-methoxynaphthalen-1-ol (70 mg, 0.34 mmol) in DCM (4 mL) at 0° C. was added $Et_3N$ (61 μL, 0.44 mmol), followed by $Tf_2O$ (74 μL, 0.44 mmol). The mixture was stirred at 0° C. for 15 min and concentrated. The residue was purified by flash chromatography eluting with ethyl acetate/hexanes (0-10%) to give the title compound (0.11 g, 97%) as a white solid. $^1$H NMR (400 MHz, ($CDCl_3$) δ 7.99 (d, J=8.0 Hz, 1H), 7.78 (d, J=7.5 Hz, 1H), 7.53 (m, 2H), 7.23 (s, 1H), 4.10 (s, 3H).

Step E. 2-(2-chloro-3-methoxynaphthalen-1-yl)-4,4,5,5-tetramethyl-1,3,2-dioxaborolane. To a vial containing a mixture of 2-chloro-3-methoxynaphthalen-1-yl trifluoromethanesulfonate (0.10 mg, 0.29 mmol), 4,4,4',4',5,5,5',5'-octamethyl-2,2'-bi(1,3,2-dioxaborolane) (0.15 mg, 0.59 mmol), $PdCl_2$(dppf) (21 mg, 0.029 mmol), and KOAc (58 mg, 0.59 mmol) under $N_2$ was added 1,4-dioxane (2 mL). The vial was closed, and the mixture was heated at 90° C. for 18 h. The mixture was cooled to rt and $PdCl_2$(dppf) (21 mg, 0.029 mmol), KOAc (58 mg, 0.59 mmol), and 4,4,4',4',5,5,5',5'-octamethyl-2,2'-bi(1,3,2-dioxaborolane) (0.15 mg, 0.59 mmol) were added under $N_2$. The mixture was heated at 90° C. for 15 h, cooled to rt, filtered, and extracted with ethyl acetate. The filtrate was concentrated and purified by flash chromatography eluting with ethyl acetate/hexanes (0-10%) to give the title compound (80 mg, 86%) as a light green solid. $^1$H NMR (400 MHz, ($CDCl_3$) δ 7.78 (d, J=8.2 Hz, 1H), 7.70 (d, J=8.1 Hz, 1H), 7.42 (m, 1H), 7.35 (m, 1H), 7.18 (s, 1H), 3.99 (s, 3H), 1.26 (s, 12H).

Step F. tert-butyl 3-(7-(2-chloro-3-methoxynaphthalen-1-yl)-8-fluoro-2-(((S)-1-methylpyrrolidin-2-yl)methoxy) pyrido[4,3-d]pyrimidin-4-yl)-3,8-diazabicyclo[3.2.1]octane-8-carboxylate. To a vial containing 2-(2-chloro-3-methoxynaphthalen-1-yl)-4,4,5,5-tetramethyl-1,3,2-dioxaborolane (32 mg, 0.10 mmol), tert-butyl (1R,5S)-3-(7-chloro-8-fluoro-2-(((S)-1-methylpyrrolidin-2-yl)methoxy) pyrido[4,3-d]pyrimidin-4-yl)-3,8-diazabicyclo[3.2.1] octane-8-carboxylate (synthesized according to Example 3, Step A-G substituting (S)-(1-methylpyrrolidin-2-yl)methanol in place of 2-(1-methyl-1H-imidazol-2-yl)ethan-1-ol, 17 mg, 0.034 mmol), Pd(OAc)$_2$ (1.5 mg, 0.0067 mmol), and 2-dicyclohexylphosphino-2',6'-dimethoxy-1,1'-biphenyl (5.5 mg, 0.013 mmol) under $N_2$ was added $CH_3CN$ (0.5 mL), followed by $K_2CO_3$ (2.0 M, 40 μL, 0.080 mmol). The vial was closed and heated at 80° C. for 2.5 h. The mixture was cooled to rt and was purified by preparative C18 HPLC (Gilson, 0-95% $CH_3CN/H_2O$ with 0.1% TFA). The desired fractions were combined, basified with $NaHCO_3$ (sat.) and extracted with ethyl acetate. The extract was washed with water, washed with brine, and dried ($Na_2SO_4$). The solution was concentrated to give the title compound (10 mg, 44%) as a white solid. LCMS (MM-ES+APCI, Pos): m/z 663.3 (M+H).

Step G. 4-(4-(3,8-diazabicyclo[3.2.1]octan-3-yl)-8-fluoro-2-(((S)-1-methylpyrrolidin-2-yl)methoxy)pyrido[4,3-d]pyrimidin-7-yl)-3-chloronaphthalen-2-ol tris(2,2,2-trifluoroacetate). To a solution of tert-butyl (1R,5S)-3-(7-(2-chloro-3-methoxynaphthalen-1-yl)-8-fluoro-2-(((S)-1-methylpyrrolidin-2-yl)methoxy)pyrido[4,3-d]pyrimidin-4-yl)-3,8-diazabicyclo[3.2.1]octane-8-carboxylate (10 mg, 0.0151 mmol) in DCM (0.50 mL) at 0° C. was added dropwise a solution of BCl3 (1.0 M in DCM, 75 μL, 0.075 mmol). The mixture was stirred at 0° C. for 15 min and at rt for 1 h. The mixture was cooled to 0° C. and BBr$_3$ (1.0 M in DCM, 0.1 mL, 0.10 mmol) was added. The mixture was stirred at r.t. for 0.5 h. Additional BBr$_3$ (1.0 M in DCM, 0.1 mL, 0.10 mmol) was added and the mixture was stirred at r.t. for 2 h. The reaction was quenched with $Na_2CO_3$ (2.0 M, 0.5 mL, 1.0 mmol). The mixture was concentrated to dryness and the residue was purified by preparative C18 HPLC (Gilson, 0-95% $CH_3CN/H_2O$ with 0.1% TFA). The desired fractions were combined and lyophilized to give the title compound (6 mg, 39%) as a TFA salt. LCMS (MM-ES+APCI, Pos): m/z 549.2 (M+H).

Example 338

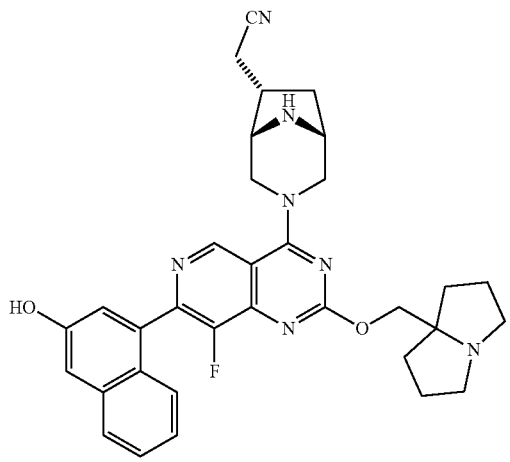 [SMILES: N#CC[C@@H]1C[C@@H]2CN(c3nc(OCC45CCCN4CCC5)nc4c(F)c(-c5cc(O)cc6ccccc56)ncc34)C[C@H]1N2]

2-((1R,5S,6S)-3-(8-fluoro-7-(3-hydroxynaphthalen-1-yl)-2-((tetrahydro-1H-pyrrolizin-7a(5H)-yl)methoxy)pyrido[4,3-d]pyrimidin-4-yl)-3,8-diazabicyclo[3.2.1]octan-6-yl)acetonitrile

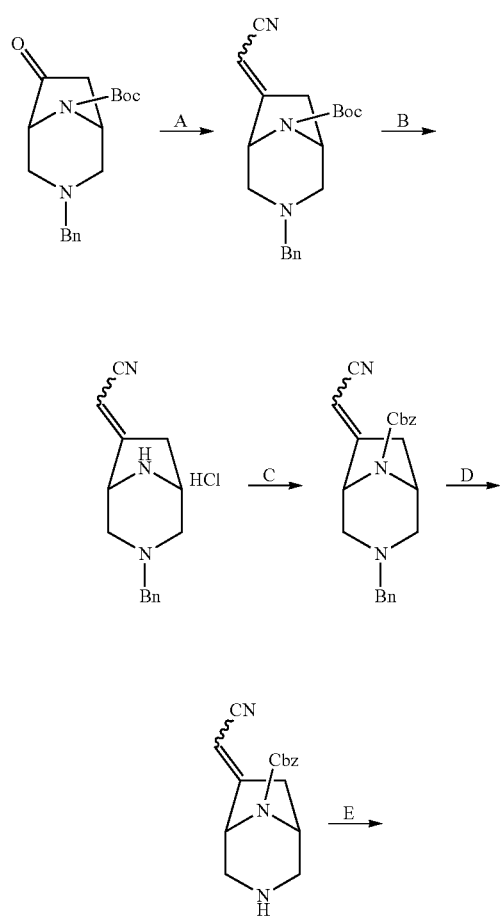

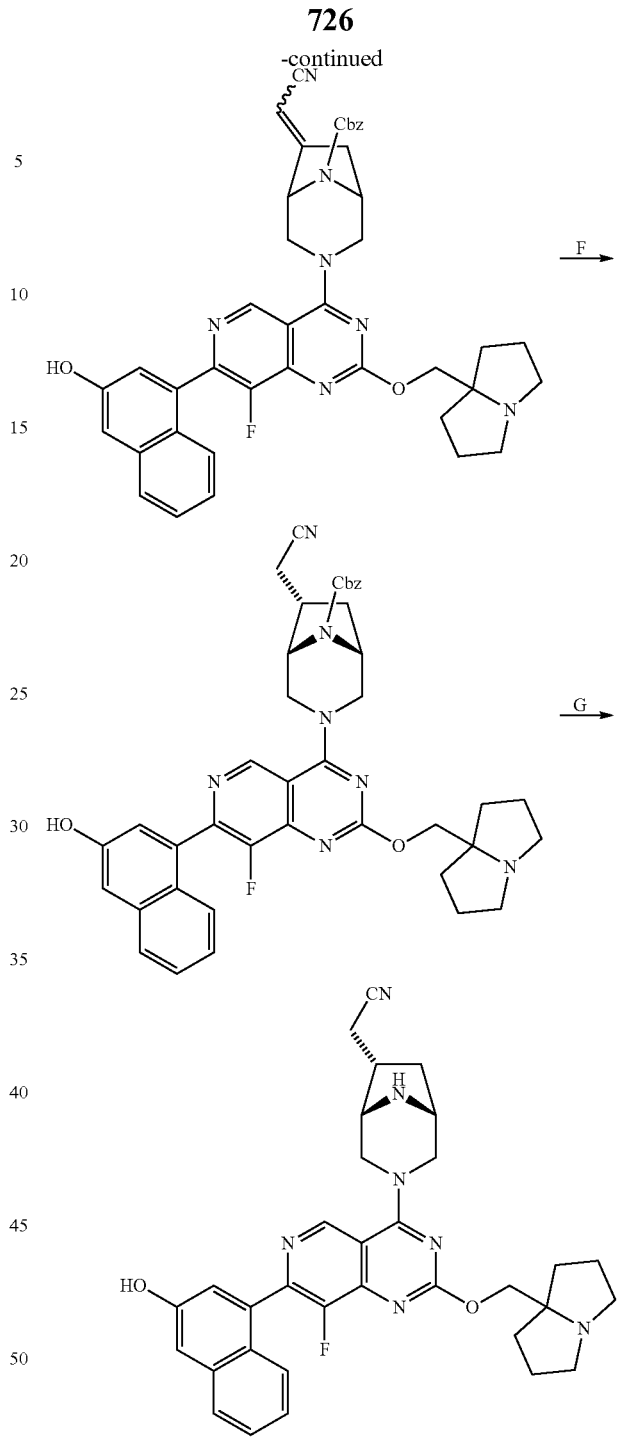

Step A. tert-butyl 3-benzyl-6-(cyanomethylene)-3,8-diazabicyclo[3.2.1]octane-8-carboxylate. To a stirred suspension of (cyanomethyl)trimethylphosphonium iodide (0.41 mg, 1.7 mmol) in tetrahydrofuran (11 mL) under $N_2$ was added NaH (60%, 70 mg, 1.8 mmol) in one portion and the mixture was stirred at rt for 1 h. To the mixture was added tert-butyl (1R,5R)-3-benzyl-6-oxo-3,8-diazabicyclo[3.2.1]octane-8-carboxylate (0.36 g, 1.1 mmol). The mixture was stirred at rt for 1 h. The reaction mixture was quenched with $NH_4Cl$ (sat.) and extracted with ethyl acetate. The extract was dried ($Na_2SO_4$), concentrated, and purified by flash chromatography eluting with ethyl acetate/hexanes (0-30%) to give the title compound (0.38 g, 98%) as a colorless oil. LCMS (MM-ES+APCI, Pos): m/z 340.3 (M+H).

Step B. 2-(3-benzyl-3,8-diazabicyclo[3.2.1]octan-6-ylidene)acetonitrile hydrochloride. To a solution of tert-butyl (1R,5S)-3-benzyl-6-(cyanomethylene)-3,8-diazabicyclo[3.2.1]octane-8-carboxylate (0.24 g, 0.71 mmol) in 1,2-dichloroethane (7 mL) in a vial was added 1-chloroethyl chloroformate (0.31 mL, 2.8 mmol). The vial was closed, and the solution was heated at 80° C. for 18 h. The solution was cooled and concentrated to dryness. The residue was treated with MeOH (10 mL) at 50° C. for 2 h and was concentrated to dryness to give the crude title compound as a black solid. LCMS (MM-ES+APCI, Pos): m/z 240.2 (M+H).

Step C. benzyl 3-benzyl-6-(cyanomethylene)-3,8-diazabicyclo[3.2.1]octane-8-carboxylate. To a suspension of 2-((1R,5S)-3-benzyl-3,8-diazabicyclo[3.2.1]octan-6-ylidene)acetonitrile hydrochloride in DCM (7.0 mL) at 0° C. was added Et₃N (0.29 mL, 2.1 mmol) followed by benzyl chloroformate (0.12 mL, 0.84 mmol). The mixture was stirred at rt for 0.5 h. The mixture was concentrated and purified by flash chromatography eluting with ethyl acetate/hexanes (0-30%) to give the title compound (0.17 g, 66% over 2 steps) as a yellow oil. LCMS (MM-ES+APCI, Pos): m/z 374.2 (M+H).

Step D. benzyl 6-(cyanomethylene)-3,8-diazabicyclo[3.2.1]octane-8-carboxylate hydrochloride. To a solution of benzyl (1R,5S,E)-3-benzyl-6-(cyanomethylene)-3,8-diazabicyclo[3.2.1]octane-8-carboxylate (98 mg, 0.26 mmol) in 1,2-dichloroethane (3 mL) in a vial was added 1-chloroethyl chloroformate (0.11 mL, 1.0 mmol). The vial was closed, and the mixture was heated at 80° C. for 2 days and 90° C. for 18 h. The mixture was cooled, concentrated to dryness, and quenched with methanol (2 mL). The solution was heated at 50° C. for 2 h and concentrated to dryness. The residue was triturated with hexanes and dried to give the crude title compound as a white solid. LCMS (MM-ES+APCI, Pos): m/z 284.2 (M+H).

Step E. benzyl 6-(cyanomethylene)-3-(8-fluoro-7-(3-hydroxynaphthalen-1-yl)-2-((tetrahydro-1H-pyrrolizin-7a (5H)-yl)methoxy)pyrido[4,3-d]pyrimidin-4-yl)-3,8-diazabicyclo[3.2.1]octane-8-carboxylate. To a mixture of 8-fluoro-7-(3-hydroxynaphthalen-1-yl)-2-((tetrahydro-1H-pyrrolizin-7a(5H)-yl)methoxy)pyrido[4,3-d]pyrimidin-4-ol (25 mg, 0.056 mmol), benzyl 6-(cyanomethylene)-3,8-diazabicyclo[3.2.1]octane-8-carboxylate hydrochloride (38 mg, 0.12 mmol), 2-(3H-[1,2,3]triazolo[4,5-b]pyridin-3-yl)-1,1,3,3-tetramethylisouronium hexafluorophosphate(V) (64 mg, 0.17 mmol) in a flask was added DMA (1 mL), followed by DIPEA (68 µL, 0.39 mmol). The mixture was stirred at rt for 1.5 h and was heated at 60° C. for 10 min. The solution was cooled to r.t. and quenched with two drops of NH₃·H₂O (28%). The mixture was purified by preparative C18 HPLC (Gilson, 0-95% CH₃CN/H₂O with 0.1% TFA). The desired fractions were combined and concentrated to remove CH₃CN. The remaining solution was basified with NaHCO₃ (sat.) and extracted with ethyl acetate. The combined extract was dried (Na₂SO₄) and concentrated to give the title compound (17 mg, 43%) as a white solid. LCMS (MM-ES+APCI, Pos): m/z 712.3 (M+H).

Step F. benzyl (1R,5S,6S)-6-(cyanomethyl)-3-(8-fluoro-7-(3-hydroxynaphthalen-1-yl)-2-((tetrahydro-1H-pyrrolizin-7a(5H)-yl)methoxy)pyrido[4,3-d]pyrimidin-4-yl)-3,8-diazabicyclo[3.2.1]octane-8-carboxylate. To a solution of benzyl (1R,5S,E)-6-(cyanomethylene)-3-(8-fluoro-7-(3-hydroxynaphthalen-1-yl)-2-((tetrahydro-1H-pyrrolizin-7a (5H)-yl)methoxy)pyrido[4,3-d]pyrimidin-4-yl)-3,8-diazabicyclo[3.2.1]octane-8-carboxylate (17 mg, 0.024 mmol) in THF (0.80 mL) at −20° C. was added dropwise L-Selectride (1.0 M in THF, 72 µL, 0.072 mmol). The solution was stirred at −20° C. for 0.5 h, quenched with NH₄Cl (sat., 0.2 mL), and warmed to rt. The mixture was purified by preparative C18 HPLC (Gilson, 0-95% CH₃CN/H₂O with 0.1% TFA). The desired fractions were combined and concentrated to remove CH₃CN. The remaining solution was basified with NaHCO₃ (sat.) and extracted with DCM. The combined DCM extract was dried (Na₂SO₄) and was concentrated to give the title compound (12 mg, 70%) as a white solid. LCMS (MM-ES+APCI, Pos): m/z 714.3 (M+H).

Step G. 2-((1R,5S,6S)-3-(8-fluoro-7-(3-hydroxynaphthalen-1-yl)-2-((tetrahydro-1H-pyrrolizin-7a(5H)-yl)methoxy)pyrido[4,3-d]pyrimidin-4-yl)-3,8-diazabicyclo[3.2.1]octan-6-yl)acetonitrile trihydrochloride. To a solution of benzyl (1R,5S,6S)-6-(cyanomethyl)-3-(8-fluoro-7-(3-hydroxynaphthalen-1-yl)-2-((tetrahydro-1H-pyrrolizin-7a (5H)-yl)methoxy)pyrido[4,3-d]pyrimidin-4-yl)-3,8-diazabicyclo[3.2.1]octane-8-carboxylate (12 mg, 0.017 mmol) in DCM (0.80 mL) at rt was added BCl₃ (1.0 M in hexanes, 84 µL, 0.084 mmol). The mixture was stirred at rt for 10 min. To the mixture was added additional BCl₃ (1.0 M in hexanes, 0.10 mL, 0.10 mmol) and the reaction stirred at rt for 0.5 h. The mixture was concentrated to dryness and the residue was purified by preparative C18 HPLC (Gilson, 0-95% CH₃CN/H₂O with 0.1% TFA). The desired fractions were combined and lyophilized to give the title compound (8 mg, 67%) as the bis TFA salt. LCMS (MM-ES+APCI, Pos): m/z 580.3 (M+H).

Example 339

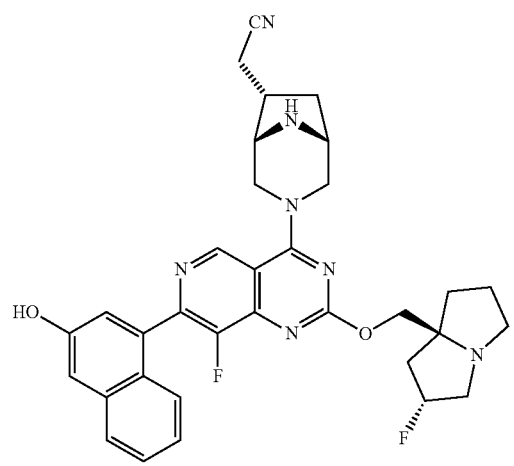

729

2-((1R,5S,6S)-3-(8-fluoro-2-((2-fluorotetrahydro-1H-pyrrolizin-7a(5H)-yl)methoxy)-7-(3-hydroxynaphthalen-1-yl)pyrido[4,3-d]pyrimidin-4-yl)-3,8-diazabicyclo[3.2.1]octan-6-yl)acetonitrile (racemic, trans)

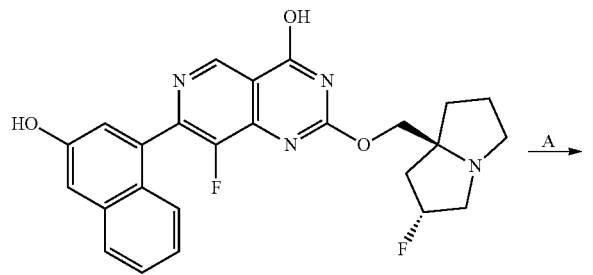

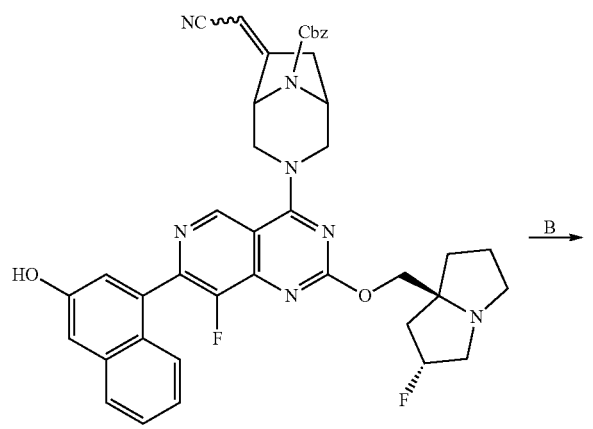

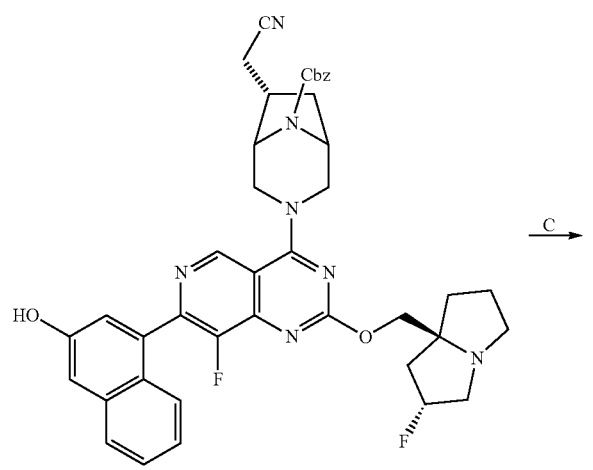

730

-continued

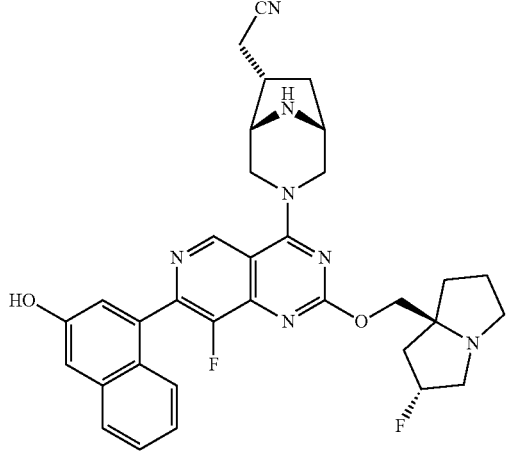 [SMILES: N#CC[C@@H]1C[C@@H]2CN(c3nc(OCC45CCCN4CCC5)nc4c(F)c(-c5cc(O)cc6ccccc56)ncc34)C[C@H]1N2]

Step A. benzyl 6-(cyanomethylene)-3-(8-fluoro-2-((2-fluorotetrahydro-1H-pyrrolizin-7a(5H)-yl)methoxy)-7-(3-hydroxynaphthalen-1-yl)pyrido[4,3-d]pyrimidin-4-yl)-3,8-diazabicyclo[3.2.1]octane-8-carboxylate (racemic, trans). To a solution of 8-fluoro-2-((2-fluorotetrahydro-1H-pyrrolizin-7a(5H)-yl)methoxy)-7-(3-hydroxynaphthalen-1-yl)pyrido[4,3-d]pyrimidin-4-ol (racemic, trans) (25 mg, 0.054 mmol) and 2-(3H-[1,2,3]triazolo[4,5-b]pyridin-3-yl)-1,1,3,3-tetramethylisouronium hexafluorophosphate(V) (45 mg, 0.12 mmol) in DMA (1 mL) was added DIPEA (47 µL, 0.27 mmol). The solution was stirred at r.t. for 3 min, followed by addition of benzyl (1R,5S,Z)-6-(cyanomethylene)-3,8-diazabicyclo[3.2.1]octane-8-carboxylate hydrochloride (34 mg, 0.11 mmol) over 2 min. The solution was stirred at r.t. for 5 min. and quenched with two drops of NH$_3$·H$_2$O (28%). The mixture was purified by preparative C18 HPLC (Gilson, 0-95% CH$_3$CN/H$_2$O with 0.1% TFA). The desired fractions were combined and concentrated. The aqueous layer was neutralized with NaHCO$_3$ (sat.) and extracted with ethyl acetate. The combined extract was dried (Na$_2$SO$_4$) and concentrated to give the title compound (25 mg, 64%) as a highly impure yellow solid. LCMS (MM-ES+APCI, Pos): m/z 730.2 (M+H).

Step B. benzyl (6S)-6-(cyanomethyl)-3-(8-fluoro-2-((2-fluorotetrahydro-1H-pyrrolizin-7a(5H)-yl)methoxy)-7-(3-hydroxynaphthalen-1-yl)pyrido[4,3-d]pyrimidin-4-yl)-3,8-diazabicyclo[3.2.1]octane-8-carboxylate (racemic, trans). To a solution of benzyl (1R,5S,Z)-6-(cyanomethylene)-3-(8-fluoro-2-((2-fluorotetrahydro-1H-pyrrolizin-7a(5H)-yl)methoxy)-7-(3-hydroxynaphthalen-1-yl)pyrido[4,3-d]pyrimidin-4-yl)-3,8-diazabicyclo[3.2.1]octane-8-carboxylate (racemic, trans) (25 mg, 0.034 mmol) in THF (1.1 mL) at −20° C. was added dropwise L-Selectride (1.0 M in THF, 0.10 mL, 0.10 mmol). The solution was stirred at −20° C. for 0.5 h and was quenched with MeOH. The solution was concentrated to dryness and the residue was purified by flash chromatography eluting with MeOH/DCM (0-40%) to give the title compound (4 mg, 16%) as a white solid. LCMS (MM-ES+APCI, Pos): m/z 732.2 (M+H).

Step C. 2-((1R,5S,6S)-3-(8-fluoro-2-((2-fluorotetrahydro-1H-pyrrolizin-7a(5H)-yl)methoxy)-7-(3-hydroxynaphthalen-1-yl)pyrido[4,3-d]pyrimidin-4-yl)-3,8-diazabicyclo[3.2.1]octan-6-yl)acetonitrile trihydrochloride (racemic, trans). To a solution of benzyl (1R,5S,6S)-6-(cyanomethyl)-3-(8-fluoro-2-((2-fluorotetrahydro-1H-pyrrolizin-7a(5H)-yl)methoxy)-7-(3-hydroxynaphthalen-1-yl)pyrido[4,3-d]pyrimidin-4-yl)-3,8-diazabicyclo[3.2.1]

octane-8-carboxylate (racemic, trans) (4 mg, 0.00547 mmol) in DCM (1.1 mL) at r.t. was added BCl$_3$ (1.0 M in hexanes, 0.11 mL, 0.11 mmol). The mixture was stirred at r.t. for 30 min., concentrated to dryness, and the residue was purified by preparative C18 HPLC (Gilson, 0-95% CH$_3$CN/H$_2$O with 0.1% TFA). The desired fractions were combined and lyophilized to give the title compound (2.5 mg, 65%) as the bis TFA salt. LCMS (MM-ES+APCI, Pos): m/z 598.2 (M+H).

Example 340

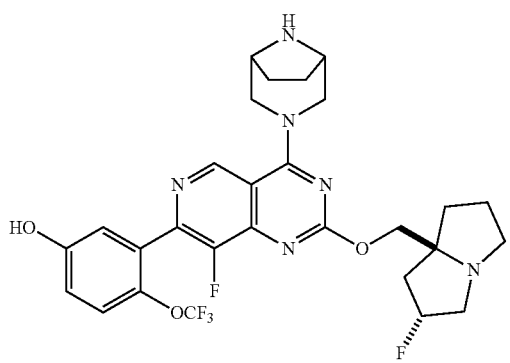

3-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-4-(trifluoromethoxy)phenol (racemic, trans)

Synthesized according to Example 3, Steps G-I substituting (2-fluorotetrahydro-1H-pyrrolizin-7a(5H)-yl)methanol (racemic, trans) in place of 2-(1-methyl-1H-imidazol-2-yl)ethan-1-ol in Step G and (5-hydroxy-2-(trifluoromethoxy)phenyl)boronic acid in place of 4-(4,4,5,5-tetramethyl-1,3,2-dioxaborolan-2-yl)naphthalen-2-ol in Step H to afford 3-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-4-(trifluoromethoxy)phenol bis(2,2,2-trifluoroacetate) (racemic, trans) (20 mg, 32%). LCMS (MM-ES+APCI, Pos): m/z 593.2 (M+H).

Example 341

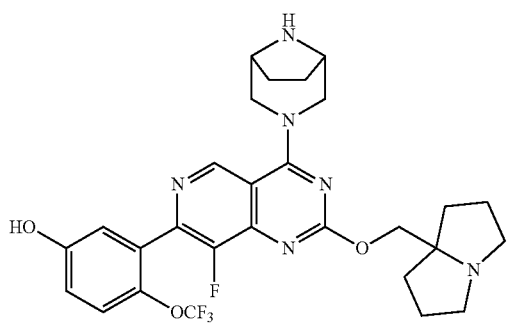 [SMILES: Oc1ccc(OC(F)(F)F)c(-c2ncc3c(N4CC5CCC(C4)N5)nc(OCC45CCCN4CCC5)nc3c2F)c1]

3-(4-((1R,5S)-3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)-4-(trifluoromethoxy)phenol Synthesized according to Example 3, Steps G-I substituting (tetrahydro-1H-pyrrolizin-7a(5H)-yl)methanol in place of 2-(1-methyl-1H-imidazol-2-yl)ethan-1-ol in Step G and (5-hydroxy-2-(trifluoromethoxy)phenyl)boronic acid in place of 4-(4,4,5,5-tetramethyl-1,3,2-dioxaborolan-2-yl)naphthalen-2-ol in Step H to afford 3-(4-((1R,5S)-3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)-4-(trifluoromethoxy)phenol bis(2,2,2-trifluoroacetate) (17 mg, 32%). LCMS (MM-ES+APCI, Pos): m/z 575.2 (M+H).

Example 342

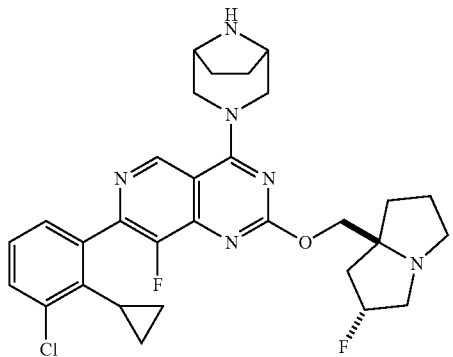

4-((1R,5S)-3,8-diazabicyclo[3.2.1]octan-3-yl)-7-(3-chloro-2-cyclopropylphenyl)-8-fluoro-2-((2-fluorotetrahydro-1H-pyrrolizin-7a(5H)-yl)methoxy)pyrido[4,3-d]pyrimidine (racemic, trans)

Synthesized according to Example 196 substituting (2-fluorotetrahydro-1H-pyrrolizin-7a(5H)-yl)methanol (racemic, trans) in place of (tetrahydro-1H-pyrrolizin-7a(5H)-yl)methanol in step A and also substituting (3-chloro-2-cyclopropylphenyl)boronic acid in place of 2,2-difluorobenzo[1,3]dioxole-4-boronic acid in step B to afford 4-((1R,5S)-3,8-diazabicyclo[3.2.1]octan-3-yl)-7-(3-chloro-2-cyclopropylphenyl)-8-fluoro-2-((2-fluorotetrahydro-1H-pyrrolizin-7a(5H)-yl)methoxy)pyrido[4,3-d]pyrimidine (racemic, trans) (19 mg, 48%). LCMS (MM-ES+APCI, Pos): m/z 567.2 (M+H).

Example 343

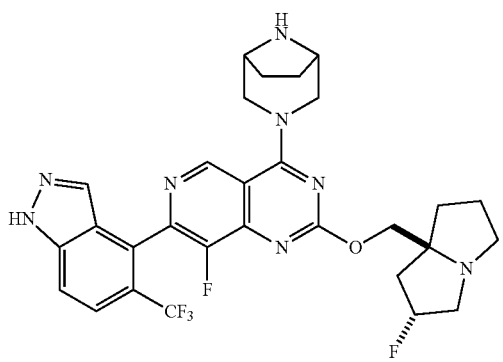

4-((1R,5S)-3,8-diazabicyclo[3.2.1]octan-3-yl)-8-fluoro-2-((2-fluorotetrahydro-1H-pyrrolizin-7a(5H)-yl)methoxy)-7-(5-(trifluoromethyl)-1H-indazol-4-yl)pyrido[4,3-d]pyrimidine (racemic, trans)

Synthesized according to Example 3, Steps G-H substituting (2-fluorotetrahydro-1H-pyrrolizin-7a(5H)-yl)methanol (racemic, trans) in place of 2-(1-methyl-1H-imidazol-2-yl)ethan-1-ol in Step G and 1-(tetrahydro-2H-pyran-2-yl)-4-(4,4,5,5-tetramethyl-1,3,2-dioxaborolan-2-yl)-5-(trifluoromethyl)-1H-indazole in place of 4-(4,4,5,5-tetramethyl-1,3,2-dioxaborolan-2-yl)naphthalen-2-ol in Step H followed by deprotection using Example 391, Step A to afford 4-((1R,5S)-3,8-diazabicyclo[3.2.1]octan-3-yl)-8-fluoro-2-((2-fluorotetrahydro-1H-pyrrolizin-7a(5H)-yl)methoxy)-7-(5-(trifluoromethyl)-1H-indazol-4-yl)pyrido[4,3-d]pyrimidine (racemic, trans) (28 mg, 84%). LCMS (MM-ES+APCI, Pos): m/z 601.2 (M+H).

Example 344

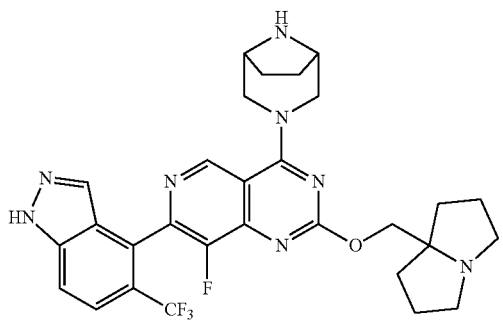 [SMILES: Fc1c(-c2c(C(F)(F)F)ccc3[nH]ncc23)ncc2c(N3CC4CCC(C3)N4)nc(OCC34CCCN3CCC4)nc12]

4-((1R,5S)-3,8-diazabicyclo[3.2.1]octan-3-yl)-8-fluoro-2-((tetrahydro-1H-pyrrolizin-7a(5H)-yl)methoxy)-7-(5-(trifluoromethyl)-1H-indazol-4-yl)pyrido[4,3-d]pyrimidine Synthesized according to Example 3, Steps G-H substituting (tetrahydro-1H-pyrrolizin-7a(5H)-yl)methanol in place of 2-(1-methyl-1H-imidazol-2-yl)ethan-1-ol in Step G and 1-(tetrahydro-2H-pyran-2-yl)-4-(4,4,5,5-tetramethyl-1,3,2-dioxaborolan-2-yl)-5-(trifluoromethyl)-1H-indazole in place of 4-(4,4,5,5-tetramethyl-1,3,2-dioxaborolan-2-yl)naphthalen-2-ol in Step H followed by deprotection using Example 391, Step A to afford 4-((1R,5S)-3,8-diazabicyclo[3.2.1]octan-3-yl)-8-fluoro-2-((tetrahydro-1H-pyrrolizin-7a(5H)-yl)methoxy)-7-(5-(trifluoromethyl)-1H-indazol-4-yl)pyrido[4,3-d]pyrimidine (9.8 mg, 63%). LCMS (MM-ES+APCI, Pos): m/z 583.3 (M+H).

Example 345

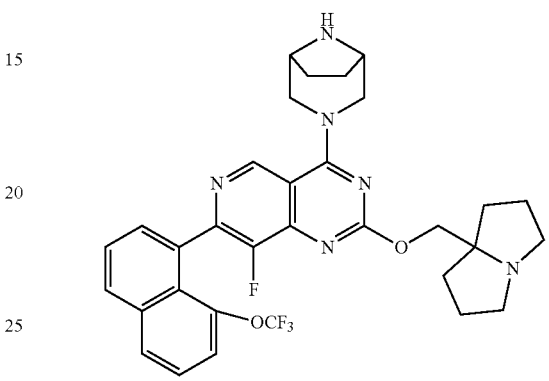

4-((1R,5S)-3,8-diazabicyclo[3.2.1]octan-3-yl)-8-fluoro-2-((tetrahydro-1H-pyrrolizin-7a(5H)-yl)methoxy)-7-(8-(trifluoromethoxy)naphthalen-1-yl)pyrido[4,3-d]pyrimidine

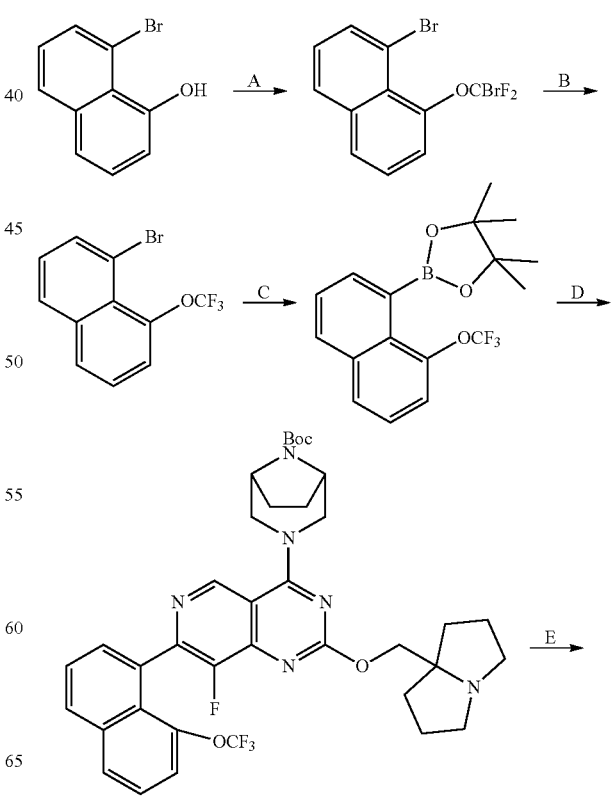

-continued

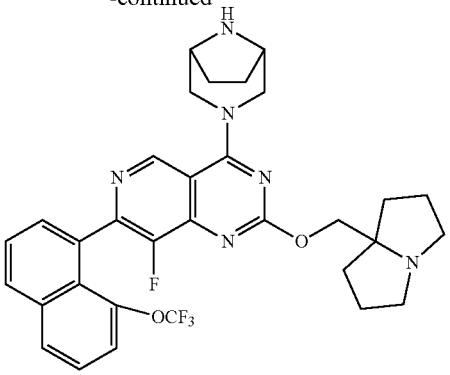

Step A. 1-bromo-8-(bromodifluoromethoxy)naphthalene and 1-bromo-8-(difluoromethoxy)naphthalene. To a solution of 8-bromonaphthalen-1-ol (0.23 g, 1.0 mmol) in DMF (2.6 mL) under N₂ at 0° C. was added NaH (60%, 0.12 g, 3.1 mmol). The mixture was stirred at 0° C. for 10 min KOtBu (0.13 g, 1.1 mmol) was added, followed by slow addition of difluorodibromomethane (0.38 mL, 4.1 mmol). The vial was closed and heated at 70° C. for 16 h. The mixture was cooled to r.t., diluted with ethyl acetate, and washed with water. The organic layer was dried (Na₂SO₄), concentrated, and purified by flash chromatography eluting with ethyl acetate/hexanes (0-20%) to give 1-bromo-8-(bromodifluoromethoxy)naphthalene (0.20 g, 0.58 mmol, 570%) and bromo-8-(difluoromethoxy)naphthalene (23 mg, 80%). 1-bromo-8-(bromodifluoromethoxy)naphthalene HNMR (400 MHz, (CDCl₃) δ 7.90 (d, J=7.4 Hz, 1H), 7.84 (d, J=8.2 Hz, 2H), 7.52 (m, 2H), 7.33 (in, 1H). ¹H NMR (400 MHz, (CDCl₃). δ 7.86 (d, J=7.5 Hz, 1H), 7.82 (d, J=8.2 Hz, 1H), 7.75 (d, J=8.2 Hz, 1H), 7.45 (t, J=7.9 Hz, 1H), 7.37 (d, J=7.6 Hz, 1H), 7.30 (t, J=7.8 Hz, 1H), 6.62 (t, J=7.4 Hz, 1H).

Step B. 1-bromo-8-(trifluoromethoxy)naphthalene. To a solution of 1-bromo-8-(bromodifluoromethoxy)naphthalene (0.20 mg, 0.56 mmol) in DCM (4 mL) at −78° C. was added silver tetrafluoroborate (0.21 g, 1.1 mmol) under N₂. The mixture was slowly warmed to r.t. and stirred over the weekend. The mixture was quenched with NaHCO₃ (sat.) and DCM. The suspension was filtered, and the two layers were separated. The organic layer was dried (Na₂SO₄), concentrated, and purified by flash chromatography eluting with hexanes to give the title compound (0.14 g, 85%) as a yellow oil. ¹H NMR (400 MHz, (CDCl₃): δ 7.89 (d, J=7.6 Hz, 1H), 7.83 (m, 2H), 7.49 (m, 2H), 7.32 (t, J=7.8 Hz, 1H).

Step C. 4,4,5,5-tetramethyl-2-(8-(trifluoromethoxy)naphthalen-1-yl)-1,3,2-dioxaborolane. To a mixture of 1-bromo-8-(trifluoromethoxy)naphthalene (0.13 g, 0.45 mmol), 4,4,4',4',5,5,5',5'-octamethyl-2,2'-bi(1,3,2-dioxaborolane) (0.28 g, 1.1 mmol), PdCl₂(dppf) (33 mg, 0.045 mmol), and KOAc (0.11 g, 1.1 mmol) under N₂ was added 1,4-dioxane (3 mL). The mixture was heated at 90° C. for 18 h. The mixture was cooled to rt, diluted with ethyl acetate, and filtered. The filtrate was concentrated and purified by flash chromatography eluting with ethyl acetate/hexanes (0-20%) to give the title compound (87 mg, 58%) as a white solid. ¹H NMR (400 MHz, (CDCl₃): δ 7.89 (d, J=8.2 Hz, 1H), 7.75 (m, 2H), 7.52 (t, J=7.5 Hz, 1H), 7.44 (m, 2H), 1.43 (s, 12H).

Step D. tert-butyl (1R,5S)-3-(8-fluoro-2-((tetrahydro-1H-pyrrolizin-7a(5H)-yl)methoxy)-7-(8-(trifluoromethoxy)naphthalen-1-yl)pyrido[4,3-d]pyrimidin-4-yl)-3,8-diazabicyclo[3.2.1]octane-8-carboxylate. To a vial containing 4,4,5,5-tetramethyl-2-(8-(trifluoromethoxy)naphthalen-1-yl)-1, 3,2-dioxaborolane (23 mg, 0.068 mmol), tert-butyl (1R,5S)-3-(7-chloro-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (20 mg, 0.038 mmol), Pd(OAc)₂ (1.7 mg, 0.008 mmol), and 2-dicyclohexylphosphino-2',6'-dimethoxy-1,1'-biphenyl (6.2 mg, 0.015 mmol) under N₂ was added 1,4-dioxane (1 mL), followed by K₂CO₃ (2.0 M, 50 µL, 0.10 mmol). The vial was closed, and the mixture was heated at 80° C. for 3 h. The mixture was cooled to rt and purified by preparative C18 HPLC (Gilson, 0-95% CH₃CN/H₂O with 0.1% TFA). The desired fractions were combined, basified with NaHCO₃ (sat.) and extracted with ethyl acetate. The extract was washed with water, washed with brine, and dried (Na₂SO₄). The solution was concentrated to give the title compound (14 mg, 53%) as a white solid. LCMS (MM-ES+APCI, Pos): m/z 709.3 (M+H).

Step E. 4-((1R,5S)-3,8-diazabicyclo[3.2.1]octan-3-yl)-8-fluoro-2-((tetrahydro-1H-pyrrolizin-7a(5H)-yl)methoxy)-7-(8-(trifluoromethoxy)naphthalen-1-yl)pyrido[4,3-d]pyrimidine tris(2,2,2-trifluoroacetate). To a solution of tert-butyl (1R,5S)-3-(8-fluoro-2-((tetrahydro-1H-pyrrolizin-7a(5H)-yl)methoxy)-7-(8-(trifluoromethoxy)naphthalen-1-yl) pyrido[4,3-d]pyrimidin-4-yl)-3,8-diazabicyclo[3.2.1]octane-8-carboxylate (14 mg, 0.020 mmol) in DCM (1 mL) at rt was added TFA (0.50 mL). The solution was stirred at rt for 2 h and concentrated to dryness. The residue was purified by preparative C18 HPLC (Gilson, 0-95% CH₃CN/H₂O with 0.1% TFA). The desired fractions were combined and lyophilized to give the title compound (13 mg, 69%) as a bis TFA salt. LCMS (MM-ES+APCI, Pos): m/z 609.3 (M+H).

Example 346

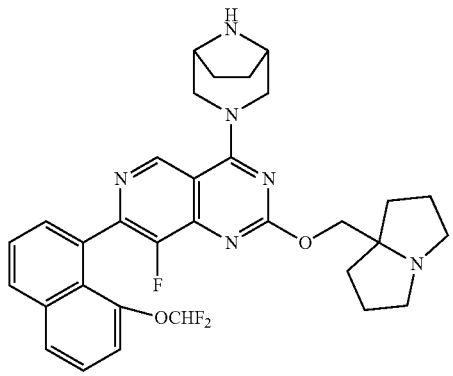 [SMILES: Fc1c(-c2cccc3cccc(OC(F)F)c23)ncc2c(N3CC4CCC(C3)N4)nc(OCC34CCCN3CCC4)nc12]

4-((1R,5S)-3,8-diazabicyclo[3.2.1]octan-3-yl)-7-(8-(difluoromethoxy)naphthalen-1-yl)-8-fluoro-2-((tetrahydro-1H-pyrrolizin-7a(5H)-yl)methoxy)pyrido[4,3-d]pyrimidine

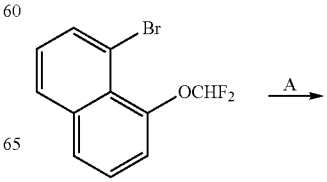

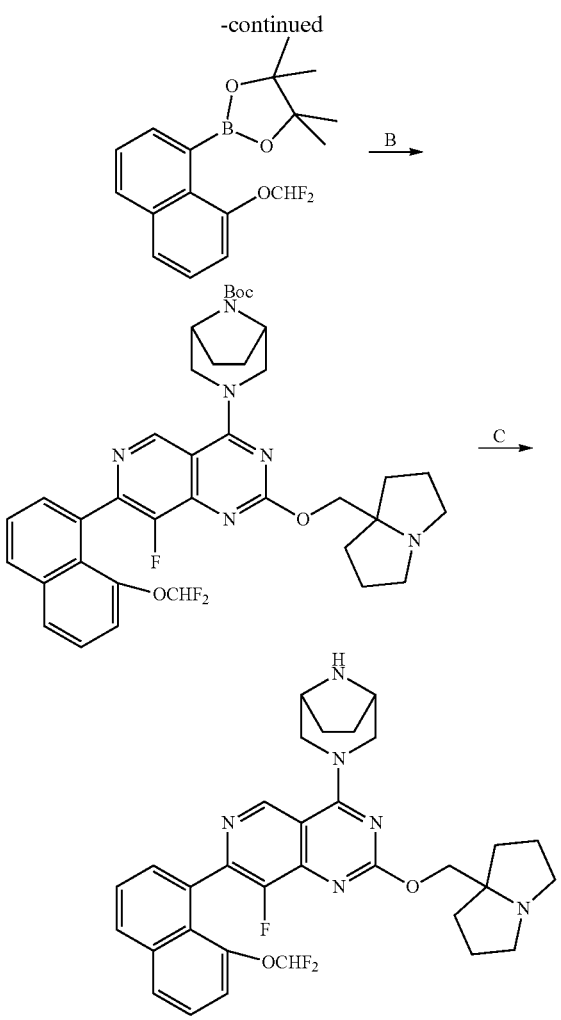

Step A. 2-(8-(difluoromethoxy)naphthalen-1-yl)-4,4,5,5-tetramethyl-1,3,2-dioxaborolane. To a mixture of 1-bromo-8-(difluoromethoxy)naphthalene (synthesized according to Example 345, Step A, 23 mg, 0.084 mmol), 4,4,4',4',5,5,5',5'-octamethyl-2,2'-bi(1,3,2-dioxaborolane) (64 mg, 0.25 mmol), PdCl$_2$(dppf) (6.2 mg, 0.0084 mmol), and KOAc (25 mg, 0.25 mmol) under N$_2$ was added 1,4-dioxane (1 mL). The mixture was heated at 90° C. for 18 h, cooled to rt, and charged with PdCl$_2$(dppf) (6.2 mg, 0.0084 mmol), KOAc (25 mg, 0.25 mmol), and 4,4,4',4',5,5,5',5'-octamethyl-2,2'-bi(1,3,2-dioxaborolane) (64 mg, 0.25 mmol) under N$_2$. The mixture was heated at 90° C. for 15 h. The mixture was cooled r.t. and filtered. The filter cake was washed with ethyl acetate. The filtrate was concentrated, and the residue was purified by flash chromatography eluting with ethyl acetate/hexanes (0-20%) to give the title compound (17 mg, 63%) as a colorless oil. $^1$H NMR 400 MHz, (CDCl$_3$): δ 7.85 (d, J=8.2 Hz, 1H), 7.67 (m, 2H), 7.51 (t, J=7.5 Hz, 1H), 7.39 (t, J=7.9 Hz, 1H), 7.18 (d, J=7.6 Hz, 1H), 6.66 (t, J=74 Hz, 1H), 1.44 (s, 12H).

Step B. tert-butyl (1R,5S)-3-(7-(8-(difluoromethoxy)naphthalen-1-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate. To a vial containing 2-(8-(difluoromethoxy)naphthalen-1-yl)-4,4,5,5-tetramethyl-1,3,2-dioxaborolane (16 mg, 0.051 mmol), tert-butyl (1R,5S)-3-(7-chloro-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (27 mg, 0.051 mmol), Pd(OAc)$_2$ (2.3 mg, 0.010 mmol), and 2-dicyclohexylphosphino-2',6'-dimethoxy-1,1'-biphenyl (8.3 mg, 0.020 mmol) under N$_2$ was added acetonitrile (0.50 mL), followed by K$_2$CO$_3$ (2.0 M, 60 μL, 0.12 mmol). The vial was closed, and the mixture was heated at 80° C. for 4 h and at 90° C. for 2 h. The mixture was cooled to rt and purified by preparative C18 HPLC (Gilson, 0-95% CH$_3$CN/H$_2$O with 0.1% TFA). The desired fractions were combined, concentrated to remove CH$_3$CN, and basified with NaHCO$_3$ (sat.) and extracted with ethyl acetate. The extract was dried (Na$_2$SO$_4$) and concentrated to give the title compound (5 mg, 14%) as a yellow solid. LCMS (MM-ES+APCI, Pos): m/z 691.3 (M+H).

Step C. 4-((1R,5S)-3,8-diazabicyclo[3.2.1]octan-3-yl)-7-(8-(difluoromethoxy)naphthalen-1-yl)-8-fluoro-2-((tetrahydro-1H-pyrrolizin-7a(5H)-yl)methoxy)pyrido[4,3-d]pyrimidine tris(2,2,2-trifluoroacetate). To a solution of tert-butyl (1R,5S)-3-(7-(8-(difluoromethoxy)naphthalen-1-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (5 mg, 0.007 mmol) in DCM (1 mL) at rt was added TFA (0.50 mL). The solution was stirred at rt for 0.5 h and concentrated to dryness. The residue was purified by preparative C18 HPLC (Gilson, 0-95% CH$_3$CN/H$_2$O with 0.1% TFA). The desired fractions were combined and lyophilized to give the title compound (3 mg, 44%) as the bis TFA salt. LCMS (MM-ES+APCI, Pos): m/z 591.3 (M+H).

Example 347

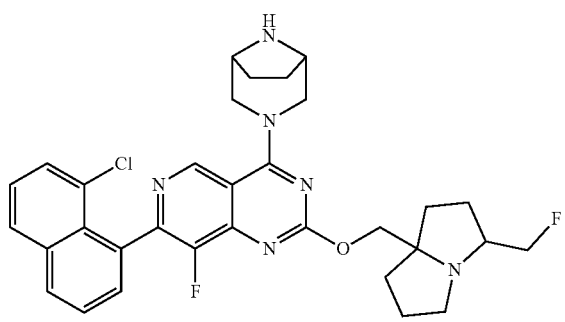 [SMILES: FCC1CCC2(COc3nc(N4CC5CCC(C4)N5)c4cnc(-c5cccc6cccc(Cl)c56)c(F)c4n3)CCCN12]

4-((1R,5S)-3,8-diazabicyclo[3.2.1]octan-3-yl)-7-(8-chloronaphthalen-1-yl)-8-fluoro-2-((3-(fluoromethyl)tetrahydro-1H-pyrrolizin-7a(5H)-yl)methoxy)pyrido[4,3-d]pyrimidine (mixture of isomers)

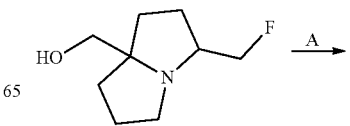

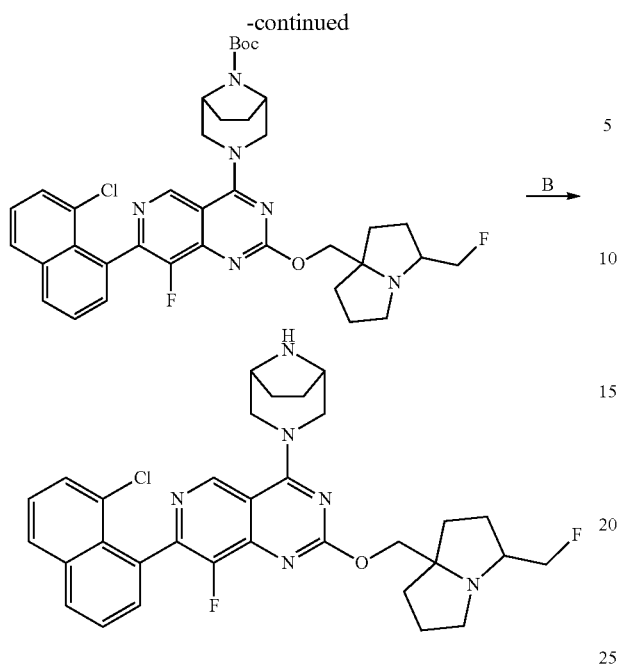

Step A. Tert-butyl (1R,5S)-3-(7-(8-chloronaphthalen-1-yl)-8-fluoro-2-((3-(fluoromethyl)tetrahydro-1H-pyrrolizin-7a(5H)-yl)methoxy)pyrido[4,3-d]pyrimidin-4-yl)-3,8-diazabicyclo[3.2.1]octane-8-carboxylate (mixture of isomers). A solution of (3-(fluoromethyl)tetrahydro-1H-pyrrolizin-7a (5H)-yl)methanol (mixture of isomers, synthesized according to Example 400, Step A-I, 10 mg, 0.06 mmol), tert-butyl (1R,5S)-3-(2-chloro-7-(8-chloronaphthalen-1-yl)-8-fluoro-pyrido[4,3-d]pyrimidin-4-yl)-3,8-diazabicyclo[3.2.1]octane-8-carboxylate (48 mg, 0.087 mmol), RuPhos Pd Gen3 precatalyst (5 mg, 0.006 mmol), and Cs₂CO₃ (75 mg, 0.23 mmol) in 1,4-dioxane (0.6 mL) was sparged with argon for 5 minutes and heated to 90° C. overnight in a sealed vial. The solution was purified by silica gel chromatography (1-20% MeOH/DCM with 1% NH₄OH as modifier). The fractions containing product were concentrated and purified by reverse-phase chromatography (5-95% MeCN/water with 0.1% TFA as modifier). The fractions containing the product were combined and partitioned between dichloromethane and saturated NaHCO₃. The organics were washed with brine, dried with Na₂SO₄, filtered, and concentrated to give tert-butyl (1R,5S)-3-(7-(8-chloronaphthalen-1-yl)-8-fluoro-2-((3-(fluoromethyl)tetrahydro-1H-pyrrolizin-7a(5H)-yl)methoxy)pyrido[4,3-d]pyrimidin-4-yl)-3,8-diazabicyclo[3.2.1]octane-8-carboxylate (16 mg, 40%). LCMS (MM-ES+APCI, Pos): m/z 691.3 (M+H).

Step B. 4-((1R,5S)-3,8-diazabicyclo[3.2.1]octan-3-yl)-7-(8-chloronaphthalen-1-yl)-8-fluoro-2-(((3R,7aR)-3-(fluoromethyl)tetrahydro-1H-pyrrolizin-7a(5H)-yl)methoxy)pyrido[4,3-d]pyrimidine. A solution of tert-butyl (1R,5S)-3-(7-(8-chloronaphthalen-1-yl)-8-fluoro-2-(((3S,7aR)-3-(fluoromethyl)tetrahydro-1H-pyrrolizin-7a(5H)-yl)methoxy)pyrido[4,3-d]pyrimidin-4-yl)-3,8-diazabicyclo[3.2.1]octane-8-carboxylate (16 mg, 0.023 mmol) in 4M HCl/dioxane (0.1 mL) and DCM (0.1 mL) was stirred for 45 minutes. Diethyl ether (0.3 mL) was added and the slurry was filtered. The solid was dried in vacuo to give the crude product which was purified by reverse-phase chromatography (5-95% MeCN/water with 0.1% TFA as modifier). The pooled product fractions were lyophilized to give 4-((1R,5S)-3,8-diazabicyclo[3.2.1]octan-3-yl)-7-(8-chloronaphthalen-1-yl)-8-fluoro-2-(((3R,7aR)-3-(fluoromethyl)tetrahydro-1H-pyrrolizin-7a(5H)-yl)methoxy)pyrido[4,3-d]pyrimidine (1.5 mg, 11%). LCMS (MM-ES+APCI, Pos): m/z 591.2 (M+H).

Example 348

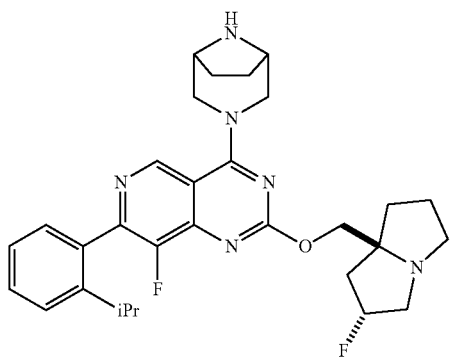

4-((1R,5S)-3,8-diazabicyclo[3.2.1]octan-3-yl)-8-fluoro-2-((2-fluorotetrahydro-1H-pyrrolizin-7a(5H)-yl)methoxy)-7-(2-isopropylphenyl)pyrido[4,3-d]pyrimidine (racemic, trans)

Step A. Tert-butyl (1R,5S)-3-(8-fluoro-2-((2-fluorotetrahydro-1H-pyrrolizin-7a(5H)-yl)methoxy)-7-(2-isopropylphenyl)pyrido[4,3-d]pyrimidin-4-yl)-3,8-diazabicyclo[3.2.1]octane-8-carboxylate (racemic, trans). Synthesized according to Example 424, Step A substituting (2-isopropylphenyl)boronic acid in place of 2-(5-(benzyloxy)-2-(2,2,2-trifluoroethyl)phenyl)-4,4,5,5-tetramethyl-1,3,2-dioxaborolane to afford tert-butyl (1R,5S)-3-(8-fluoro-2-((2-fluorotetrahydro-1H-pyrrolizin-7a(5H)-yl)methoxy)-7-(2-isopropylphenyl)pyrido[4,3-d]pyrimidin-4-yl)-3,8-diazabicyclo[3.2.1]octane-8-carboxylate (racemic, trans) (57 mg, 89%). LCMS (MM-ES+APCI, Pos): m/z 635.3 (M+H).

Step B. 4-((1R,5S)-3,8-diazabicyclo[3.2.1]octan-3-yl)-8-fluoro-2-((2-fluorotetrahydro-1H-pyrrolizin-7a(5H)-yl)methoxy)-7-(2-isopropylphenyl)pyrido[4,3-d]pyrimidine dihydrochloride (racemic, trans). Synthesized according to Example 229, Step B substituting tert-butyl (1R,5S)-3-(8-fluoro-2-((2-fluorotetrahydro-1H-pyrrolizin-7a(5H)-yl)methoxy)-7-(2-isopropylphenyl)pyrido[4,3-d]pyrimidin-4-yl)-3,8-diazabicyclo[3.2.1]octane-8-carboxylate (racemic, trans) in place of tert-butyl (1R,5S)-3-(8-fluoro-2-((tetrahydro-1H-pyrrolizin-7a(5H)-yl)methoxy)-7-(2-(trifluoromethoxy)phenyl)pyrido[4,3-d]pyrimidin-4-yl)-3,8-diazabicyclo[3.2.1]octane-8-carboxylate to afford 4-((1R,5S)-3,8-diazabicyclo[3.2.1]octan-3-yl)-8-fluoro-2-((2-fluorotetrahydro-1H-pyrrolizin-7a(5H)-yl)methoxy)-7-(2-isopropylphenyl)pyrido[4,3-d]pyrimidine dihydrochloride (racemic, trans) (1 mg, 2%). LCMS (MM-ES+APCI, Pos): m/z 535.3 (M+H).

Example 349

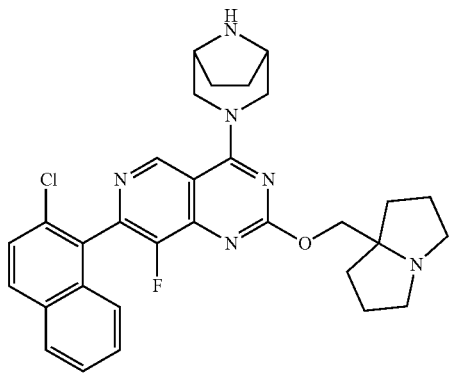 [SMILES: Fc1c(-c2c(Cl)ccc3ccccc23)ncc2c(N3CC4CCC(C3)N4)nc(OCC34CCCN3CCC4)nc12]

4-((1R,5S)-3,8-diazabicyclo[3.2.1]octan-3-yl)-7-(2-chloronaphthalen-1-yl)-8-fluoro-2-((tetrahydro-1H-pyrrolizin-7a(5H)-yl)methoxy)pyrido[4,3-d]pyrimidine

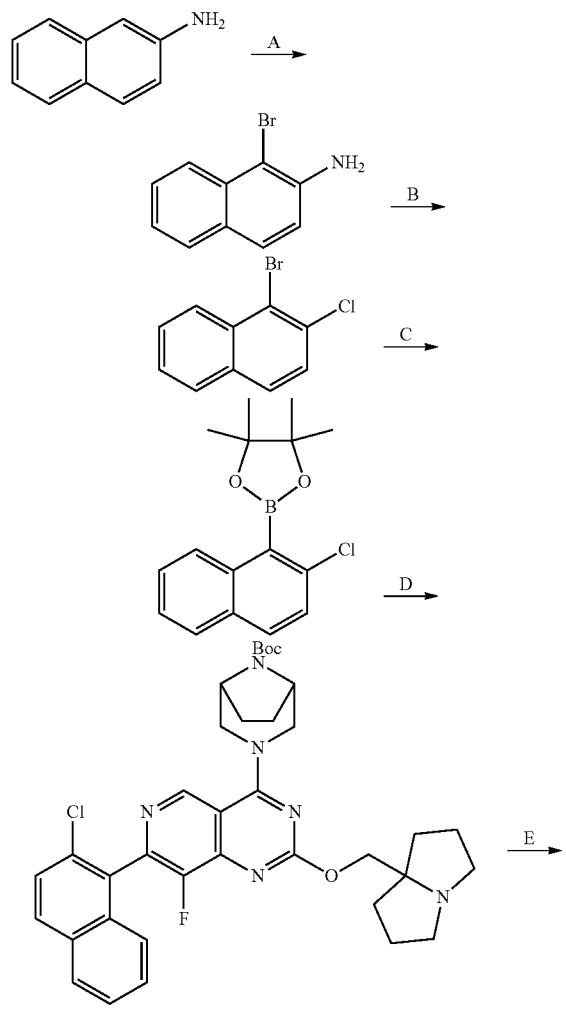

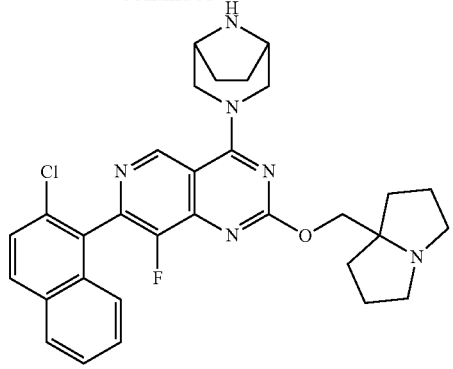

Step A. 1-bromonaphthalen-2-amine. N-Bromosuccinimide (934 mg, 5.25 mmol) was added to a solution of naphthalen-2-amine (0.72 g, 5.0 mmol) in DMF (14 mL) at 0° C. The reaction was warmed to room temperature and stirred for 1 hour. The reaction was diluted with saturated Na$_2$CO$_3$ and extracted with EtOAc. The EtOAc layer was dried with Na$_2$SO$_4$, filtered, and concentrated. The residue was purified via flash chromatography (silica, hexanes) to yield 1-bromonaphthalen-2-amine as a purple solid (0.87 g, 79%). $^1$H NMR (CDCl$_3$, 400 MHz): δ 8.04 (d, J=8.5 Hz, 1H), 7.69 (d, J=8.1 Hz, 1H), 7.62 (d, J=8.7 Hz, 1H), 7.51 (dd, J=8.3, 7.1 Hz, 1H), 7.29 (dd, J=8.6, 7.1 Hz, 1H), 7.01 (d, J=8.7 Hz, 1H).

Step B. 1-bromo-2-chloronaphthalene. A solution of NaNO$_2$ (0.72 g, 10 mmol) in water (5 mL) was added to a solution of 1-bromonaphthalen-2-amine (0.92 g, 4.2 mmol) in 12.5 M HCl (4.2 mL, 52 mmol) and water (5.2 mL) at 0° C. A solution of CuCl (2.9 g, 29 mmol) in 12.5 M HCl (4.2 mL, 52 mmol) was added to the reaction mixture at 0° C. The reaction was warmed to room temperature, heated at 65° C. for 1 hour, and stirred at room temperature overnight. The reaction was diluted with EtOAc and washed with water three times. The EtOAc layer was dried with Na$_2$SO$_4$, filtered, and concentrated. The residue was purified via flash chromatography (silica, hexanes) to yield 1-bromo-2-chloronaphthalene as a white solid (0.51 g, 51%). $^1$H NMR (CDCl$_3$, 400 MHz): δ 8.28 (d, J=8.5 Hz, 1H), 7.82 (d, J=8.0 Hz, 1H), 7.74 (d, J=8.8 Hz, 1H), 7.62 (dd, J=8.8, 6.9 Hz, 1H), 7.56-7.49 (m, 2H).

Step C. 2-(2-chloronaphthalen-1-yl)-4,4,5,5-tetramethyl-1,3,2-dioxaborolane. 1-Bromo-2-chloronaphthalene (0.24 g, 1.0 mmol), potassium acetate (0.29 g, 3.0 mmol), 4,4,4',4',5,5,5',5'-octamethyl-2,2'-bi(1,3,2-dioxaborolane) (0.76 g, 3.0 mmol), and dioxane (5.0 mL) were added to a vial with a stir bar. The vial was sparged with N$_2$ for 15 minutes before Pd(dppf)Cl$_2$ (73 mg, 0.10 mmol) was added. The reaction was heated to 95° C. for 14 hours. The reaction was diluted with water and extracted with EtOAc 2 times. The EtOAc layers were combined, dried with Na$_2$SO$_4$, filtered, and concentrated. The residue was purified by flash chromatography (silica, 0-10% EtOAc in hexanes) to yield 2-(2-chloronaphthalen-1-yl)-4,4,5,5-tetramethyl-1,3,2-dioxaborolane as a white solid (0.11 g, 38%). $^1$H NMR (CDCl$_3$, 400 MHz): δ 7.90 (d, J=8.2 Hz, 1H), 7.81-7.74 (m, 2H), 7.53-7.42 (m, 2H), 7.40 (d, J=8.8 Hz, 1H) 1.51 (s, 12H).

Step D. tert-butyl (1R,5S)-3-(7-(2-chloronaphthalen-1-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate. Tert-butyl (1R,5S)-3-(7-chloro-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (27 mg, 0.05 mmol), 2-(2-chloronaphthalen-1-yl)-4,4,5,5-tetramethyl-1,3,2-dioxaborolane (22 mg, 0.075 mmol), and XPhos Pd G2 (8 mg, 0.01 mmol) were added to a vial with a stir bar. The vial was degassed and purged with N₂ 3 times before degassed THF (0.1 mL) and degassed 0.5 M aqueous K₃PO₄ (0.2 mL, 0.1 mmol) were added. The reaction was heated to 40° C. for 1 hour. The reaction was diluted with water and extracted with DCM 3 times. The DCM layers were combined, dried with Na₂SO₄, filtered, and concentrated. The residue was purified by flash chromatography (silica, 0-20% MeOH in DCM) to yield tert-butyl (1R,5S)-3-(7-(2-chloronaphthalen-1-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate as a colorless oil (10 mg, 30%). LCMS (MM-ES+APCI, Pos): m/z 659.3 (M+H).

Step E. 4-((1R,5S)-3,8-diazabicyclo[3.2.1]octan-3-yl)-7-(2-chloronaphthalen-1-yl)-8-fluoro-2-((tetrahydro-1H-pyrrolizin-7a(5H)-yl)methoxy)pyrido[4,3-d]pyrimidine. Tert-butyl (1R,5S)-3-(7-(2-chloronaphthalen-1-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (10 mg, 0.015 mmol) was added to a vial with a stir bar. DCM (0.5 mL) and TFA (0.15 mL) were added. The reaction was stirred at room temperature for 30 minutes before being diluted with saturated NaHCO₃ and extracted with DCM 3 times. The DCM layers were combined, dried with Na₂SO₄, filtered, and concentrated to yield 4-((1R,5S)-3,8-diazabicyclo[3.2.1]octan-3-yl)-7-(2-chloronaphthalen-1-yl)-8-fluoro-2-((tetrahydro-1H-pyrrolizin-7a(5H)-yl)methoxy)pyrido[4,3-d]pyrimidine (9.3 mg, 100%). LCMS (MM-ES+APCI, Pos): m/z 559.2 (M+H).

Example 350

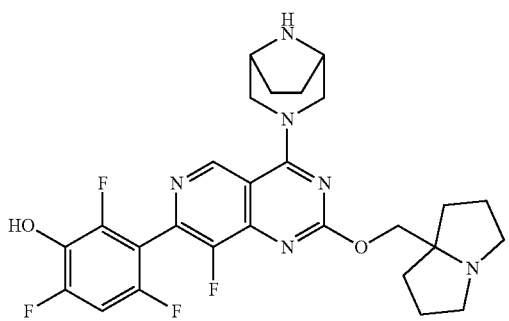 [SMILES: Oc1c(F)cc(F)c(-c2ncc3c(N4CC5CCC(C4)N5)nc(OCC45CCCN4CCC5)nc3c2F)c1F]

3-(4-((1R,5S)-3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)-2,4,6-trifluorophenol

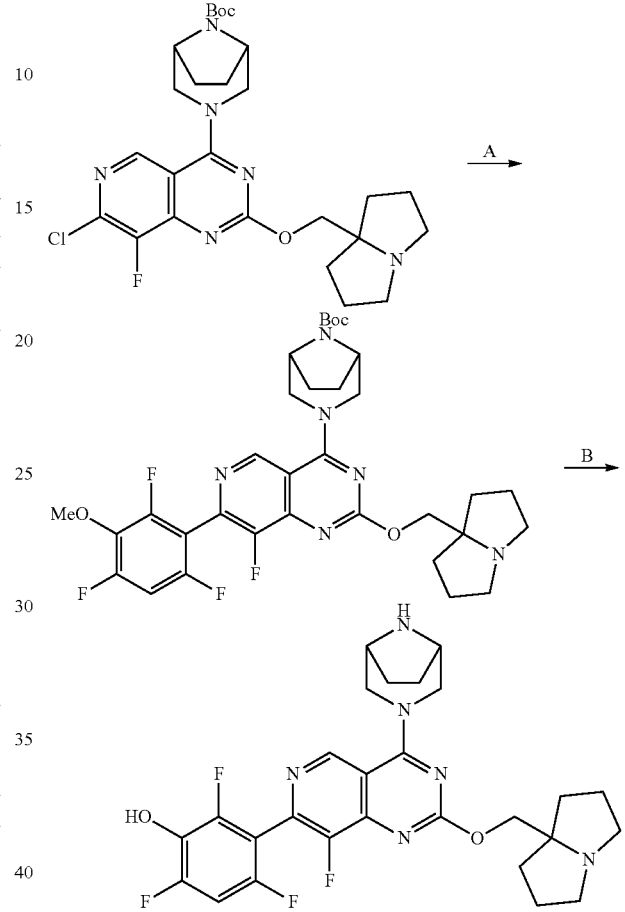

Step A. tert-butyl (1R,5S)-3-(8-fluoro-2-((tetrahydro-1H-pyrrolizin-7a(5H)-yl)methoxy)-7-(2,4,6-trifluoro-3-methoxyphenyl)pyrido[4,3-d]pyrimidin-4-yl)-3,8-diazabicyclo[3.2.1]octane-8-carboxylate. Tert-butyl (1R,5S)-3-(7-chloro-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (53 mg, 0.1 mmol), 3-methoxy-2,4,6-trifluorophenylboronic acid (31 mg, 0.15 mmol), and XPhos Pd G2 (8 mg, 0.01 mmol) were added to a vial with a stir bar. The vial was degassed and purged with N₂ 3 times before degassed THF (0.2 mL) and degassed 0.5 M aqueous K₃PO₄ (0.4 mL, 0.2 mmol) were added. The reaction was heated to 40° C. for 2 hours. The reaction was diluted with water and extracted with DCM 3 times. The DCM layers were combined, dried with Na₂SO₄, filtered, and concentrated. The residue was purified by flash chromatography (silica, 0-20% MeOH in DCM) to yield 29 mg of tert-butyl (1R,5S)-3-(8-fluoro-2-((tetrahydro-1H-pyrrolizin-7a(5H)-yl)methoxy)-7-(2,4,6-trifluoro-3-methoxyphenyl)pyrido[4,3-d]pyrimidin-4-yl)-3,8-diazabicyclo[3.2.1]octane-8-carboxylate and tert-butyl (1R,5S)-3-(7-chloro-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate as a 2:1 mixture. LCMS (MM-ES+APCI, Pos): m/z 659.3 (M+H).

Step B. 3-(4-((1R,5S)-3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)-2,4,6-trifluorophenol tris(2,2,2-trifluoroacetate). The 2:1 mixture of tert-butyl (1R,5S)-3-(8-fluoro-2-((tetrahydro-1H-pyrrolizin-7a(5H)-yl)methoxy)-7-(2,4,6-trifluoro-3-methoxyphenyl)pyrido[4,3-d]pyrimidin-4-yl)-3,8-diazabicyclo[3.2.1]octane-8-carboxylate and tert-butyl (1R,5S)-3-(7-chloro-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (29 mg) was added to a round bottom flask with a stir bar and septa. The round bottom flask was degassed and purged with $N_2$ 3 times before dry DCM was added. The round bottom flask was cooled to 0° C. and 1M trichloroborane (0.10 mL, 0.10 mmol) was added dropwise. The reaction was stirred at 0° C. for 30 minutes. 1M $BBr_3$ (0.10 mL, 0.10 mmol) was added at room temperature and the reaction was stirred for 1 hour. Additional $BBr_3$ (0.10 mL, 0.10 mmol) was added and the reaction was stirred for 30 minutes. 1M NaOH (1.5 mL) was added to quench the reaction. The aqueous layer was washed with DCM 6 times before being purified via a Biotage (0-100% MeCN in water with 0.1% TFA). The fractions containing the product were combined, frozen, and lyophilized to yield 3-(4-((1R,5S)-3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)-2,4,6-trifluorophenol tris(2,2,2-trifluoroacetate) (7.7 mg, 39%). LCMS (MM-ES+APCI, Pos): m/z 545.3 (M+H).

Example 351

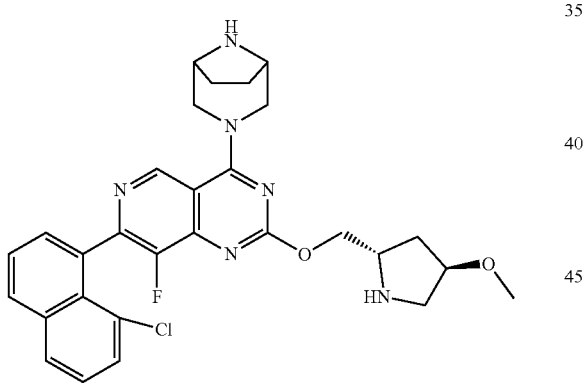

4-((1R,5S)-3,8-diazabicyclo[3.2.1]octan-3-yl)-7-(8-chloronaphthalen-1-yl)-8-fluoro-2-(((2S,4R)-4-methoxypyrrolidin-2-yl)methoxy)pyrido[4,3-d]pyrimidine Synthesized according to Example 29, Step H substituting tert-butyl (2S,4R)-2-(hydroxymethyl)-4-methoxypyrrolidine-1-carboxylate in place of (S)-(1-isopropylpyrrolidin-2-yl) methanol followed by deprotection using Example 2, Step I, (21 mg, 10%). LCMS (MM-ES+APCI, Pos): m/z 549.3 (M+H).

Example 352

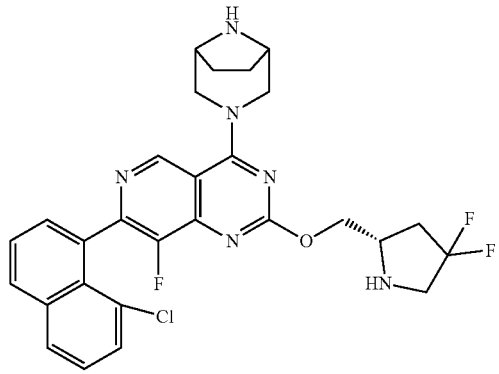 [SMILES: Fc1c(-c2cccc3cccc(Cl)c23)ncc2c(N3CC4CCC(C3)N4)nc(OC[C@@H]3CC(F)(F)CN3)nc12]

4-((1R,5S)-3,8-diazabicyclo[3.2.1]octan-3-yl)-7-(8-chloronaphthalen-1-yl)-2-(((S)-4,4-difluoropyrrolidin-2-yl)methoxy)-8-fluoropyrido[4,3-d]pyrimidine bis(2,2,2-trifluoroacetate)

Synthesized according to Example 29, Step H substituting (S)-tert-butyl 4,4-difluoro-2-(hydroxymethyl) pyrrolidine-1-carboxylate in place of (S)-(1-isopropylpyrrolidin-2-yl) methanol followed by deprotection using Example 2, Step I, (29 mg, 15%). LCMS (MM-ES+APCI, Pos): m/z 555.2 (M+H).

Example 353

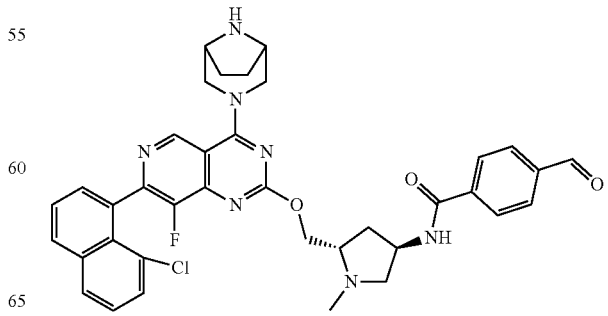

N-((3R,5S)-5-(((4-((1R,5S)-3,8-diazabicyclo[3.2.1]
octan-3-yl)-7-(8-chloronaphthalen-1-yl)-8-fluoro-
pyrido[4,3-d]pyrimidin-2-yl)oxy)methyl)-1-meth-
ylpyrrolidin-3-yl)-4-formylbenzamide

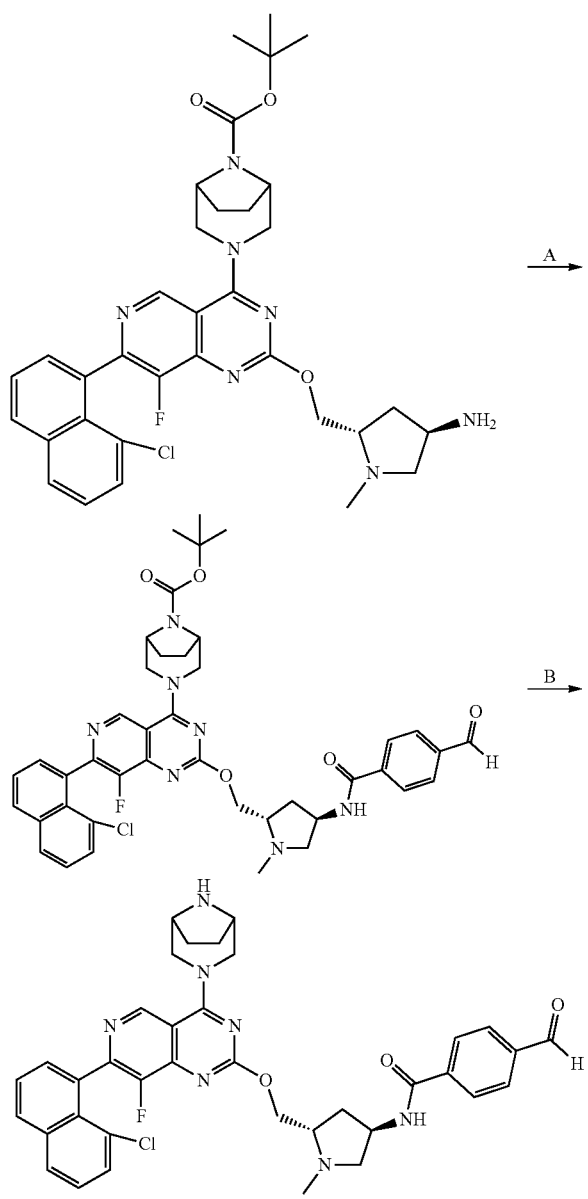

Step A. tert-butyl (1R,5S)-3-(7-(8-chloronaphthalen-1-yl)-8-fluoro-2-(((2S,4R)-4-(4-formylbenzamido)-1-methylpyrrolidin-2-yl)methoxy)pyrido[4,3-d]pyrimidin-4-yl)-3,8-diazabicyclo[3.2.1]octane-8-carboxylate. To a vial containing a mixture of tert-butyl (1R,5S)-3-(2-(((2S,4R)-4-amino-1-methylpyrrolidin-2-yl)methoxy)-7-(8-chloronaphthalen-1-yl)-8-fluoropyrido[4,3-d]pyrimidin-4-yl)-3,8-diazabicyclo[3.2.1]octane-8-carboxylate (Synthesized according to Example 165, Step A, 20 mg, 0.031 mmol, synthesis in Example 165), 4-formylbenzoic acid (9.3 mg, 0.062 mmol), HOBT (8.3 mg, 0.062 mmol), and EDC (12 mg, 0.062 mmol) was added DMF (0.6 mL), followed by DIPEA (22 □L, 0.12 mmol). The solution was stirred at rt for 3 hrs. The mixture was purified by preparative C18 HPLC (Gilson, 0-95% CH₃CN/H₂O with 0.1% TFA). The desired fractions were combined, basified with NaHCO₃ (sat.), and extracted with ethyl acetate. The combined extract was washed with water, brine, dried (Na₂SO₄), and concentrated to give the title compound (14 mg, 58%) as a yellow solid. LCMS (MM-ES+APCI, Pos): m/z 780.3 (M+H).

Step B. N-((3R,5S)-5-(((4-((1R,5S)-3,8-diazabicyclo[3.2.1]octan-3-yl)-7-(8-chloronaphthalen-1-yl)-8-fluoro-pyrido[4,3-d]pyrimidin-2-yl)oxy)methyl)-1-methylpyrrolidin-3-yl)-4-formylbenzamide tris(2,2,2-trifluoroacetate). To a solution of tert-butyl (1R,5S)-3-(7-(8-chloronaphthalen-1-yl)-8-fluoro-2-(((2S,4R)-4-(4-formylbenzamido)-1-methylpyrrolidin-2-yl)methoxy)pyrido[4,3-d]pyrimidin-4-yl)-3,8-diazabicyclo[3.2.1]octane-8-carboxylate (14 mg, 0.018 mmol) in DCM (0.60 mL) was added TFA (0.30 mL). The solution was stirred at rt for 45 min and concentrated to dryness. The residue was purified by preparative C18 HPLC (Gilson, 0-95% CH₃CN/H₂O with 0.1% TFA). The desired fractions were combined and lyophilized to give the title product (7.0 mg, 38%) as a bis TFA salt. LCMS (MM-ES+APCI, Pos): m/z 680.3 (M+H).

Example 354

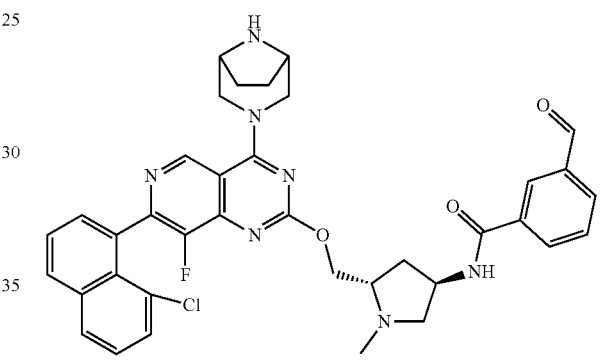

N-((3R,5S)-5-(((4-((1R,5S)-3,8-diazabicyclo[3.2.1]
octan-3-yl)-7-(8-chloronaphthalen-1-yl)-8-fluoro-
pyrido[4,3-d]pyrimidin-2-yl)oxy)methyl)-1-meth-
ylpyrrolidin-3-yl)-3-formylbenzamide Synthesized according to Example 353 substituting 3-formyl benzoic acid for 4-formyl benzoic acid in Step A to give product as the bis TFA salt (11 mg, 66%). LCMS (MM-ES+APCI, Pos): m/z 680.3 (M+H).

Example 355

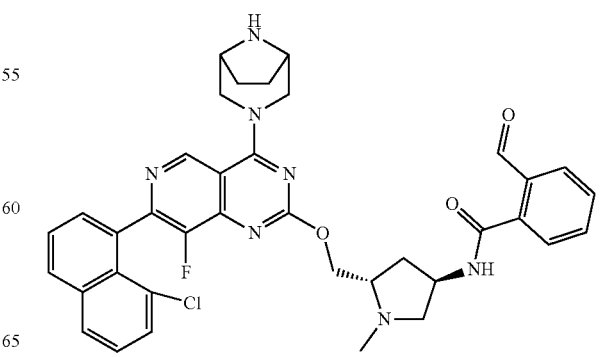

749

N-((3R,5S)-5-(((4-((1R,5S)-3,8-diazabicyclo[3.2.1]
octan-3-yl)-7-(8-chloronaphthalen-1-yl)-8-fluoro-
pyrido[4,3-d]pyrimidin-2-yl)oxy)methyl)-1-meth-
ylpyrrolidin-3-yl)-2-formylbenzamide Synthesized according to Example 353 substituting 2-formyl benzoic acid for 4-formyl benzoic acid in Step A to give product as the bis TFA salt (4.5 mg, 37%). LCMS (MM-ES+APCI, Pos): m/z 680.3 (M+H).

Example 356

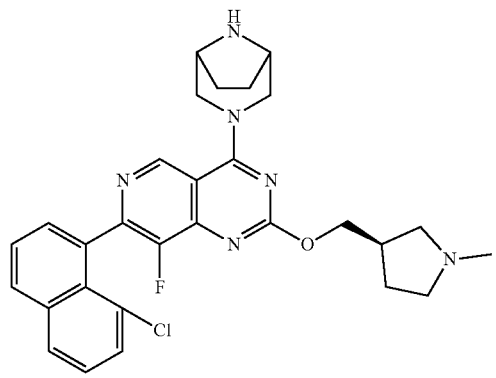 [SMILES: CN1CC[C@@H](COc2nc(N3CC4CCC(C3)N4)c3cnc(-c4cccc5cccc(Cl)c45)c(F)c3n2)C1]

4-((1R,5S)-3,8-diazabicyclo[3.2.1]octan-3-yl)-7-(8-chloronaphthalen-1-yl)-8-fluoro-2-(((R)-1-methylpyrrolidin-3-yl)methoxy)pyrido[4,3-d]pyrimidine

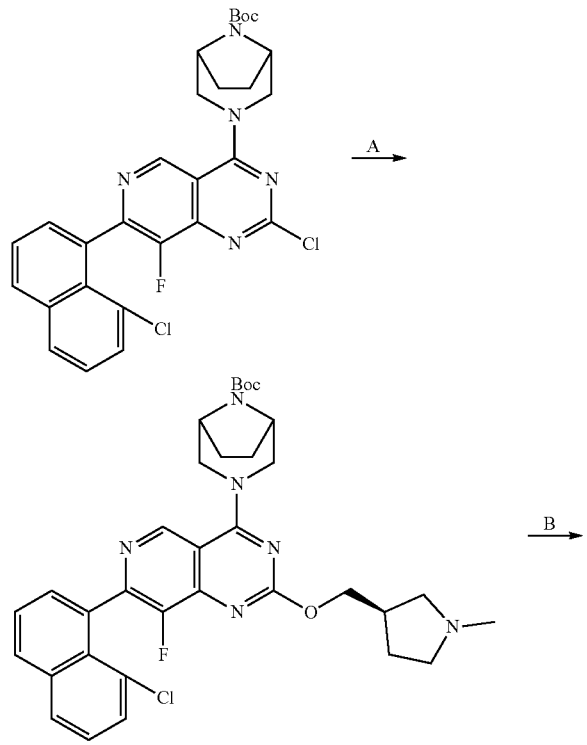

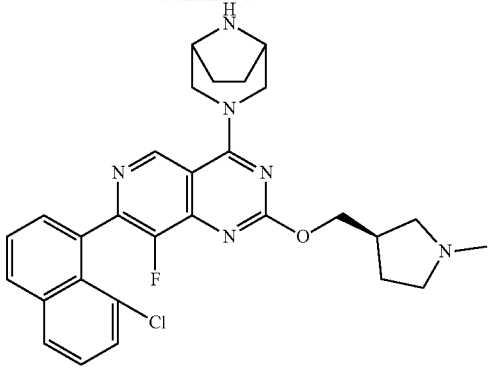

Step A. tert-butyl (1R,5S)-3-(7-(8-chloronaphthalen-1-yl)-8-fluoro-2-(((R)-1-methylpyrrolidin-3-yl)methoxy)pyrido[4,3-d]pyrimidin-4-yl)-3,8-diazabicyclo[3.2.1]octane-8-carboxylate. (R)-(1-methylpyrrolidin-3-yl)methanol (16 mg, 0.14 mmol) was added to solution of 60% NaH (6 mg, 0.15 mmol) in THF (0.2 mL) at 0° C. The reaction was stirred for 30 minutes at 0° C. before a solution of tert-butyl (1R,5S)-3-(2-chloro-7-(8-chloronaphthalen-1-yl)-8-fluoro-pyrido[4,3-d]pyrimidin-4-yl)-3,8-diazabicyclo[3.2.1]octane-8-carboxylate (55 mg, 0.1 mmol) in THF (0.3 mL) was added. The reaction was stirred at 0° C. for 30 minutes before being warmed to room temperature. The reaction was diluted with saturated aqueous NH₄Cl and extracted with DCM 3 times. The DCM layers were combined, dried with Na₂SO₄, and concentrated. The residue was purified by flash chromatography (silica, 0-20% MeOH in DCM) to yield tert-butyl (1R,5S)-3-(7-(8-chloronaphthalen-1-yl)-8-fluoro-2-(((R)-1-methylpyrrolidin-3-yl)methoxy)pyrido[4,3-d]pyrimidin-4-yl)-3,8-diazabicyclo[3.2.1]octane-8-carboxylate (36 mg, 56%). LCMS (MM-ES+APCI, Pos): m/z 633.3 (M+H).

Step B. 4-((1R,5S)-3,8-diazabicyclo[3.2.1]octan-3-yl)-7-(8-chloronaphthalen-1-yl)-8-fluoro-2-(((R)-1-methylpyrrolidin-3-yl)methoxy)pyrido[4,3-d]pyrimidine bis(2,2,2-trifluoroacetate). Tert-butyl (1R,5S)-3-(7-(8-chloronaphthalen-1-yl)-8-fluoro-2-(((S)-1-methylpyrrolidin-3-yl)methoxy)pyrido[4,3-d]pyrimidin-4-yl)-3,8-diazabicyclo[3.2.1]octane-8-carboxylate (36 mg, 0.056 mmol) was added to a round bottom flask with a stir bar. DCM (1 mL) and TFA (0.5 mL) were added at room temperature and the reaction was stirred for 2 hours. The reaction was concentrated to dryness, and the residue was purified via reverse phase chromatography (C18, 0-60% MeCN in water with 0.1% TFA). The fractions containing the product were combined, frozen, and lyophilized to yield 4-((1R,5S)-3,8-diazabicyclo[3.2.1]octan-3-yl)-7-(8-chloronaphthalen-1-yl)-8-fluoro-2-(((R)-1-methylpyrrolidin-3-yl)methoxy)pyrido[4,3-d]pyrimidine bis(2,2,2-trifluoroacetate) as a white solid (42 mg, 98%). LCMS (MM-ES+APCI, Pos): m/z 533.3 (M+H).

Example 357

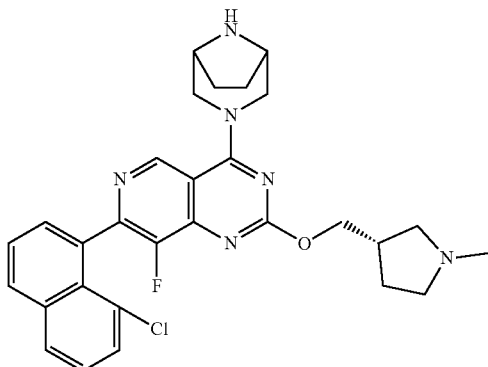

4-((1R,5S)-3,8-diazabicyclo[3.2.1]octan-3-yl)-7-(8-chloronaphthalen-1-yl)-8-fluoro-2-(((S)-1-methylpyrrolidin-3-yl)methoxy)pyrido[4,3-d]pyrimidine Synthesized according to Example 356 substituting (S)-(1-methylpyrrolidin-3-yl)methanol for (R)-(1-methylpyrrolidin-3-yl)methanol in step A to give 4-((1R,5S)-3,8-diazabicyclo[3.2.1]octan-3-yl)-7-(8-chloronaphthalen-1-yl)-8-fluoro-2-(((S)-1-methylpyrrolidin-3-yl)methoxy)pyrido[4,3-d]pyrimidine as the bis TFA salt (54 mg, 85% as). LCMS (MM-ES+APCI, Pos): m/z 533.2 (M+H).

Example 358

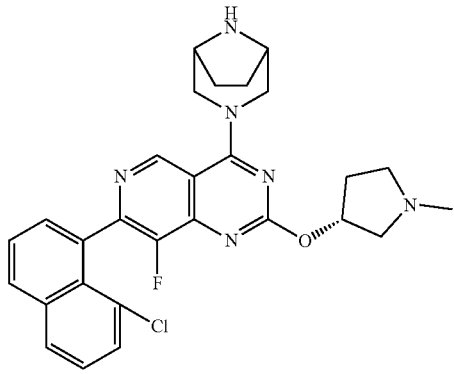 [SMILES: CN1CC[C@@H](Oc2nc(N3CC4CCC(C3)N4)c3cnc(-c4cccc5cccc(Cl)c45)c(F)c3n2)C1]

4-((1R,5S)-3,8-diazabicyclo[3.2.1]octan-3-yl)-7-(8-chloronaphthalen-1-yl)-8-fluoro-2-(((R)-1-methylpyrrolidin-3-yl)oxy)pyrido[4,3-d]pyrimidine Synthesized according to Example 356 substituting (R)-1-methylpyrrolidin-3-ol for (R)-(1-methylpyrrolidin-3-yl)methanol in step A to give 4-((1R,5S)-3,8-diazabicyclo[3.2.1]octan-3-yl)-7-(8-chloronaphthalen-1-yl)-8-fluoro-2-(((R)-1-methylpyrrolidin-3-yl)oxy)pyrido[4,3-d]pyrimidine as the bis TFA salt (30 mg, 56%). LCMS (MM-ES+APCI, Pos): m/z 519.2 (M+H).

Example 359

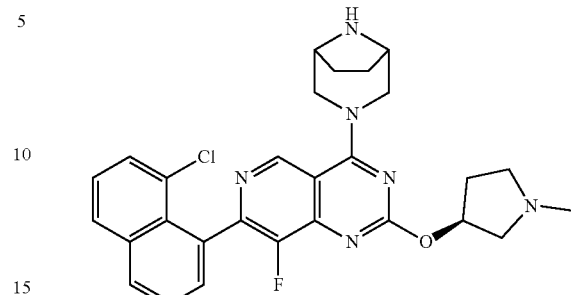

4-((1R,5S)-3,8-diazabicyclo[3.2.1]octan-3-yl)-7-(8-chloronaphthalen-1-yl)-8-fluoro-2-(((S)-1-methylpyrrolidin-3-yl)oxy)pyrido[4,3-d]pyrimidine Synthesized according to Example 356 substituting (S)-1-methylpyrrolidin-3-ol in for (R)-(1-methylpyrrolidin-3-yl)methanol in step A to give 4-((1R,5S)-3,8-diazabicyclo[3.2.1]octan-3-yl)-7-(8-chloronaphthalen-1-yl)-8-fluoro-2-(((S)-1-methylpyrrolidin-3-yl)oxy)pyrido[4,3-d]pyrimidine bis(2,2,2-trifluoroacetate) as the bis TFA salt (27 mg, 62%). LCMS (MM-ES+APCI, Pos): m/z 519.2 (M+H).

Example 360

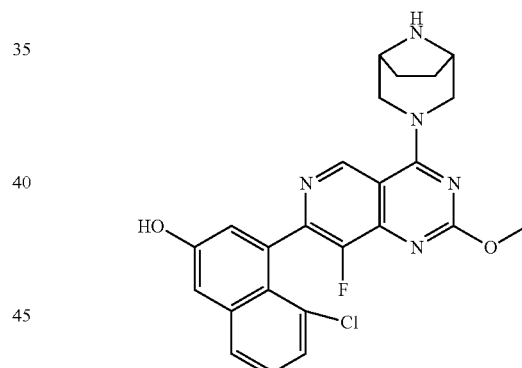

4-(4-((1R,5S)-3,8-diazabicyclo[3.2.1]octan-3-yl)-8-fluoro-2-methoxypyrido[4,3-d]pyrimidin-7-yl)-5-chloronaphthalen-2-ol

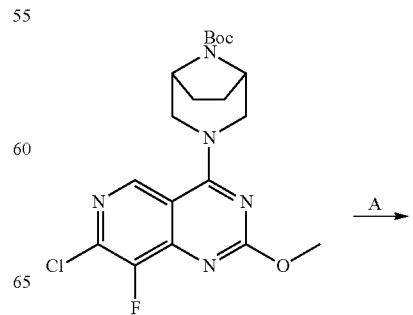

fluoro-2-methoxypyrido[4,3-d]pyrimidin-4-yl)-3,8-diazabi-cyclo[3.2.1]octane-8-carboxylate (21 mg, 26%). LCMS (MM-ES+APCI, Pos): m/z 680.3 [M+H].

Step B. tert-butyl (1R,5S)-3-(7-(8-chloro-3-hydroxynaphthalen-1-yl)-8-fluoro-2-methoxypyrido[4,3-d]pyrimidin-4-yl)-3,8-diazabicyclo[3.2.1]octane-8-carboxylate: To a solution of tert-butyl (1R,5S)-3-(7-(3-((tert-butyldimethylsilyl)oxy)-8-chloronaphthalen-1-yl)-8-fluoro-2-methoxypyrido[4,3-d]pyrimidin-4-yl)-3,8-diazabicyclo[3.2.1]octane-8-carboxylate (21 mg, 0.031 mmol) in THF (1 mL) was added TBAF (150 µL, 1.0 M, 0.15 mmol). The mixture was stirred at ambient temperature for 2 hours and then partitioned between sat. NaHCO₃ (10 mL) and EtOAc (10 mL). The aqueous layer was extracted with EtOAc (2×10 mL) and the combined organic phases were washed with brine (10 mL), dried over Na₂SO₄, filtered, and concentrated. The residue was purified by flash column chromatography eluting with 0-60% EtOAc/hexanes to afford tert-butyl (1R,5S)-3-(7-(8-chloro-3-hydroxynaphthalen-1-yl)-8-fluoro-2-methoxy-pyrido[4,3-d]pyrimidin-4-yl)-3,8-diazabicyclo[3.2.1]oc-tane-8-carboxylate (6.1 mg, 35%). LCMS (MM-ES+APCI, Pos): m/z 566.2 [M+H].

Step C. 4-(4-((1R,5S)-3,8-diazabicyclo[3.2.1]octan-3-yl)-8-fluoro-2-methoxypyrido[4,3-d]pyrimidin-7-yl)-5-chloronaphthalen-2-ol: To a solution of tert-butyl (1R,5S)-3-(7-(8-chloro-3-hydroxynaphthalen-1-yl)-8-fluoro-2-methoxypyrido[4,3-d]pyrimidin-4-yl)-3,8-diazabicyclo[3.2.1]octane-8-carboxylate (6.1 mg, 0.011 mmol) in DCM (0.5 mL) was added 4N HCl/dioxane (0.5 mL). The mixture was stirred at ambient temperature for 1 hour, concentrated, and dried in vacuo. The residue was triturated with Et₂O, filtered, and dried in vacuo to afford 4-(4-((1R,5S)-3,8-diazabicyclo[3.2.1]octan-3-yl)-8-fluoro-2-methoxypyrido[4,3-d]pyrimidin-7-yl)-5-chloronaphthalen-2-ol HCl salt. LCMS (MM-ES+APCI, Pos): m/z 466.1 [M+H].

Example 361

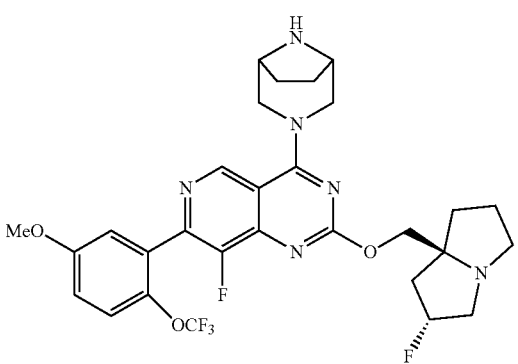 [SMILES: COc1ccc(OC(F)(F)F)c(-c2ncc3c(N4CC5CCC(C4)N5)nc(OC[C@@]45CCCN4C[C@H](F)C5)nc3c2F)c1]

4-((1R,5S)-3,8-diazabicyclo[3.2.1]octan-3-yl)-8-fluoro-2-((2-fluorotetrahydro-1H-pyrrolizin-7a(5H)-yl)methoxy)-7-(5-methoxy-2-(trifluoromethoxy)phenyl)pyrido[4,3-d]pyrimidine (racemic, trans)

Step A. Tert-butyl (1R,5S)-3-(8-fluoro-2-((2-fluorotetrahydro-1H-pyrrolizin-7a(5H)-yl)methoxy)-7-(5-methoxy-2-(trifluoromethoxy)phenyl)pyrido[4,3-d]pyrimidin-4-yl)-3,8-diazabicyclo[3.2.1]octane-8-carboxylate (racemic, trans). Synthesized according to Example 424, Step A substituting (5-methoxy-2-(trifluoromethoxy)phenyl)boronic acid in place of 2-(5-(benzyloxy)-2-(2,2,2-trifluoroethyl)phenyl)-4,4,5,5-tetramethyl-1,3,2-dioxaborolane to afford tert-butyl (1R,5S)-3-(8-fluoro-2-((2-fluorotetrahydro-1H-pyrrolizin-7a(5H)-yl)methoxy)-7-(5-methoxy-2-(trifluoromethoxy)phenyl)pyrido[4,3-d]pyrimidin-4-yl)-3,8-diazabicyclo[3.2.1]octane-8-carboxylate (racemic, trans) (39 mg, 61%). LCMS (MM-ES+APCI, Pos): m/z 707.3 (M+H).

Step B. 4-((1R,5S)-3,8-diazabicyclo[3.2.1]octan-3-yl)-8-fluoro-2-((2-fluorotetrahydro-1H-pyrrolizin-7a(5H)-yl)methoxy)-7-(5-methoxy-2-(trifluoromethoxy)phenyl)pyrido[4,3-d]pyrimidine dihydrochloride (racemic, trans). Synthesized according to Example 229, Step B substituting tert-butyl (1R,5S)-3-(8-fluoro-2-((2-fluorotetrahydro-1H-pyrrolizin-7a(5H)-yl)methoxy)-7-(5-methoxy-2-(trifluoromethoxy)phenyl)pyrido[4,3-d]pyrimidin-4-yl)-3,8-diazabicyclo[3.2.1]octane-8-carboxylate (racemic, trans) in place of tert-butyl (1R,5S)-3-(8-fluoro-2-((tetrahydro-1H-pyrrolizin-7a(5H)-yl)methoxy)-7-(2-(trifluoromethoxy)phenyl)pyrido[4,3-d]pyrimidin-4-yl)-3,8-diazabicyclo[3.2.1]octane-8-carboxylate to afford 4-((1R,5S)-3,8-diazabicyclo[3.2.1]octan-3-yl)-8-fluoro-2-((2-fluorotetrahydro-1H-pyrrolizin-7a(5H)-yl)methoxy)-7-(5-methoxy-2-(trifluoromethoxy)phenyl)pyrido[4,3-d]pyrimidine dihydrochloride (racemic, trans) (15 mg, 40%). LCMS (MM-ES+APCI, Pos): m/z 607.2 (M+H).

Example 362

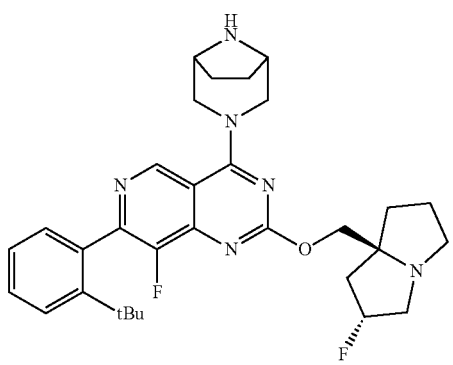 [SMILES: CC(C)(C)c1ccccc1-c1ncc2c(N3CC4CCC(C3)N4)nc(OC[C@@]34CCCN3C[C@H](F)C4)nc2c1F]

4-((1R,5S)-3,8-diazabicyclo[3.2.1]octan-3-yl)-7-(2-(tert-butyl)phenyl)-8-fluoro-2-((2-fluorotetrahydro-1H-pyrrolizin-7a(5H)-yl)methoxy)pyrido[4,3-d]pyrimidine (racemic, trans)

Step A. Tert-butyl (1R,5S)-3-(7-(2-(tert-butyl)phenyl)-8-fluoro-2-((2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (racemic, trans). Synthesized according to Example 424, Step A substituting (2-(tert-butyl)phenyl)boronic acid in place of 2-(5-(benzyloxy)-2-(2,2,2-trifluoroethyl)phenyl)-4,4,5,5-tetramethyl-1,3,2-dioxaborolane to afford tert-butyl (1R,5S)-3-(7-(2-(tert-butyl)phenyl)-8-fluoro-2-((2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (racemic, trans) (24 mg, 41%). LCMS (MM-ES+APCI, Pos): m/z 649.4 (M+H).

Step B. 4-((1R,5S)-3,8-diazabicyclo[3.2.1]octan-3-yl)-7-(2-(tert-butyl)phenyl)-8-fluoro-2-((2-fluorotetrahydro-1H-pyrrolizin-7a(5H)-yl)methoxy)pyrido[4,3-d]pyrimidine dihydrochloride (racemic, trans). Synthesized according to Example 229, Step B substituting tert-butyl (1R,5S)-3-(7-(2-(tert-butyl)phenyl)-8-fluoro-2-((2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (racemic, trans) in place of tert-butyl (1R,5S)-3-(8-fluoro-2-((tetrahydro-1H-pyrrolizin-7a(5H)-yl)methoxy)-7-(2-(trifluoromethoxy)phenyl)pyrido[4,3-d]pyrimidin-4-yl)-3,8-diazabicyclo[3.2.1]octane-8-carboxylate to afford 4-((1R,5S)-3,8-diazabicyclo[3.2.1]octan-3-yl)-7-(2-(tert-butyl)phenyl)-8-fluoro-2-((2-fluorotetrahydro-1H-pyrrolizin-7a(5H)-yl)methoxy)pyrido[4,3-d]pyrimidine dihydrochloride (racemic, trans) (15 mg, 65%). LCMS (MM-ES+APCI, Pos): m/z 549.3 (M+H).

Example 363

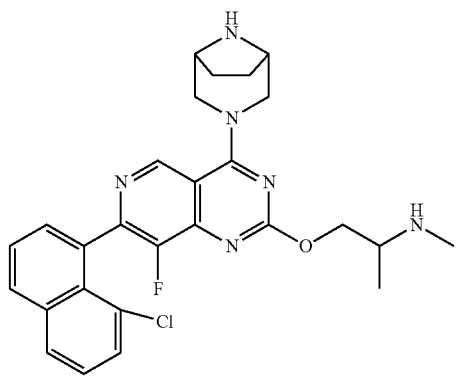 [SMILES: CNC(C)COc1nc(N2CC3CCC(C2)N3)c2cnc(-c3cccc4cccc(Cl)c34)c(F)c2n1]

4-((1R,5S)-3,8-diazabicyclo[3.2.1]octan-3-yl)-7-(8-chloronaphthalen-1-yl)-2-(((S)-4,4-difluoropyrrolidin-2-yl)methoxy)-8-fluoropyrido[4,3-d]pyrimidine bis(2,2,2-trifluoroacetate)

Synthesized according to Example 29, Step H substituting 2-(methylamino)-1-propanol in place of (S)-(1-isopropylpyrrolidin-2-yl) methanol followed by deprotection using Example 2, Step I (19 mg, 21%). LCMS (MM-ES+APCI, Pos): m/z 507.2 (M+H).

Example 364

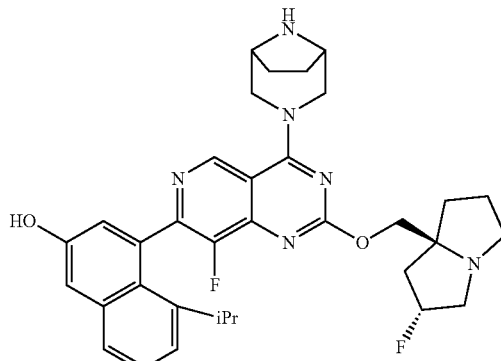

757

4-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-5-isopropylnaphthalen-2-ol (racemic, trans)

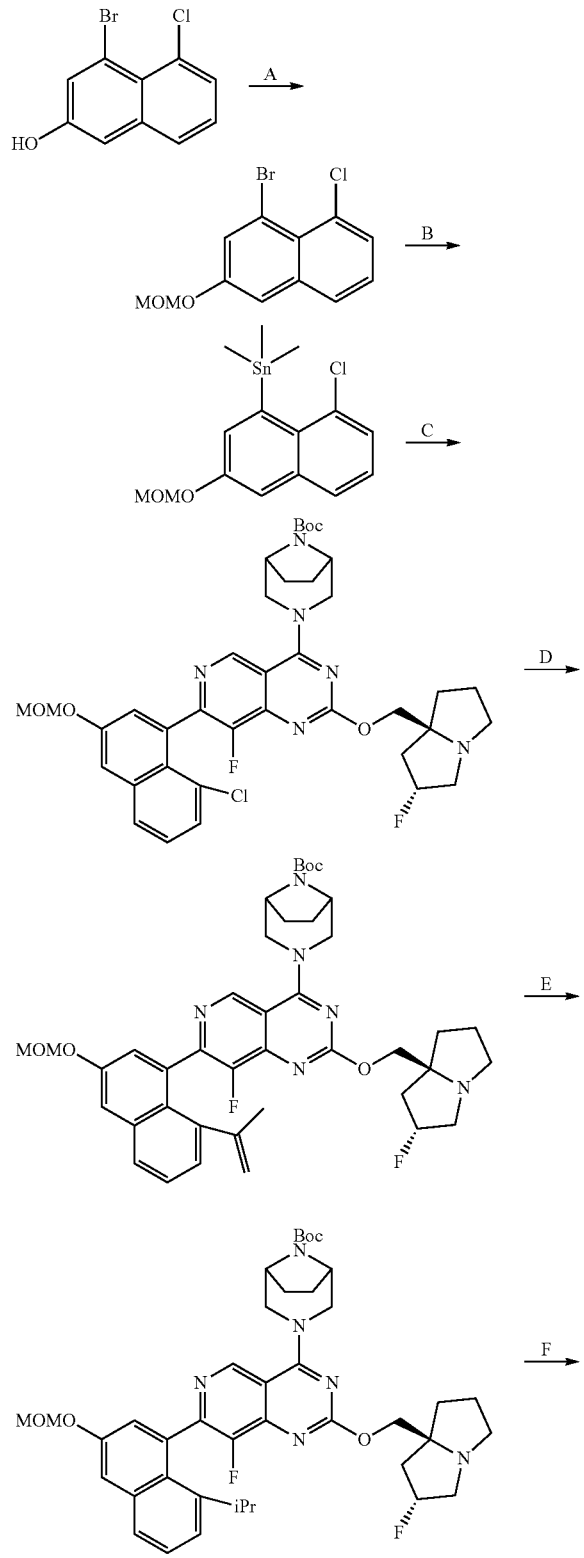

758

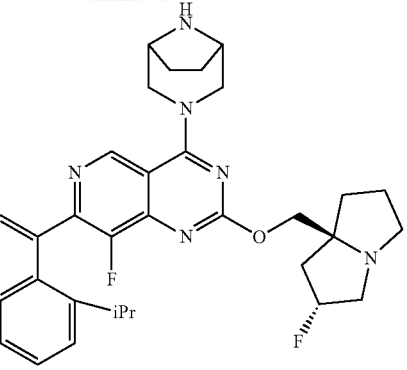

Step A. 1-bromo-8-chloro-3-(methoxymethoxy)naphthalene. A solution of 4-bromo-5-chloronaphthalen-2-ol (0.40 g, 1.6 mmol) in THF (8 mL) was cooled to 0° C. NaH (60% in mineral oil, 93 mg, 2.3 mmol) was added in one portion, and the mixture was stirred for 30 minutes at 0° C. Chloromethyl methyl ether (0.15 mL, 2 mmol) was added, and the mixture was stirred at room temperature for 16 hours. The mixture was diluted with water and extracted with EtOAc 3 times. The combined organics were dried over MgSO$_4$ and condensed. Purification by flash chromatography (RediSep Gold 24 g column, 0-10% EtOAc/hexanes) afforded 1-bromo-8-chloro-3-(methoxymethoxy)naphthalene (0.34 g, 73%). $^1$H NMR (400 MHz, CDCl$_3$): δ 7.69 (s, 1H), 7.66 (d, J=8.3 Hz, 1H), 7.50 (d, J=7.3 Hz, 1H), 7.37 (s, 1H), 7.30 (t, J=7.7 Hz, 1H), 5.27 (s, 2H), 3.51 (s, 3H).

Step B. (8-chloro-3-(methoxymethoxy)naphthalen-1-yl)trimethylstannane. Synthesized according to Example 330, Step B substituting 1-bromo-8-chloro-3-(methoxymethoxy)naphthalene in place of ((4-bromo-5-chloronaphthalen-2-yl)oxy)(tert-butyl)dimethylsilane to afford (8-chloro-3-(methoxymethoxy)naphthalen-1-yl)trimethylstannane (0.35 g, 80%). $^1$H NMR (400 MHz, CDCl$_3$): δ 7.67 (d, J=8.3 Hz, 1H), 7.56 (d, J=2.6 Hz, 1H), 7.46 (d, J=7.4 Hz, 1H), 7.38 (d, J=2.4 Hz, 1H), 7.31 (t, J=7.6 Hz, 1H), 5.31 (s, 2H), 3.53 (s, 3H), 0.49-0.36 (m, 9H).

Step C. Tert-butyl (1R,5S)-3-(7-(8-chloro-3-(methoxymethoxy)naphthalen-1-yl)-8-fluoro-2-((2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (racemic, trans). Synthesized according to Example 330, Step C substituting (8-chloro-3-(methoxymethoxy)naphthalen-1-yl)trimethylstannane in place of tert-butyl((5-chloro-4-(trimethylstannyl)naphthalen-2-yl)oxy)dimethylsilane to afford tert-butyl (1R,5S)-3-(7-(8-chloro-3-(methoxymethoxy)naphthalen-1-yl)-8-fluoro-2-((2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (racemic, trans) (30 mg, 45%). LCMS (MM-ES+APCI, Pos): m/z 737.3 (M+H).

Step D. Tert-butyl (1R,5S)-3-(8-fluoro-2-((2-fluorotetrahydro-1H-pyrrolizin-7a(5H)-yl)methoxy)-7-(3-(methoxymethoxy)-8-(prop-1-en-2-yl)naphthalen-1-yl)pyrido[4,3-d]pyrimidin-4-yl)-3,8-diazabicyclo[3.2.1]octane-8-carboxylate (racemic, trans). Tert-butyl (1R,5S)-3-(7-(8-chloro-3-(methoxymethoxy)naphthalen-1-yl)-8-fluoro-2-((2-fluorotetrahydro-1H-pyrrolizin-7a(5H)-yl)

methoxy)pyrido[4,3-d]pyrimidin-4-yl)-3,8-diazabicyclo[3.2.1]octane-8-carboxylate (racemic, trans) (50 mg, 0.068 mmol) and 4,4,5,5-tetramethyl-2-(prop-1-en-2-yl)-1,3,2-dioxaborolane (0.051 mL, 0.271 mmol) were dissolved in 1,4-dioxane (1 mL). Aqueous K$_2$CO$_3$ (2 N, 0.10 mL, 0.20 mmol) was added. After degassing with argon, tetrakis(triphenylphosphine)palladium(0) (7.8 mg, 0.007 mmol) was added. The vial was degassed with argon, sealed, and heated to 100° C. for 16 hours. The mixture was filtered through MgSO$_4$ and condensed. The residue was purified by prep HPLC (5-95% MeCN/H$_2$O/0.1% TFA in 15 minutes) to afford tert-butyl (1R,5S)-3-(8-fluoro-2-(((2-fluorotetrahydro-1H-pyrrolizin-7a(5H)-yl)methoxy)-7-(3-(methoxymethoxy)-8-(prop-1-en-2-yl)naphthalen-1-yl)pyrido[4,3-d]pyrimidin-4-yl)-3,8-diazabicyclo[3.2.1]octane-8-carboxylate (racemic, trans) (26 mg, 52%). LCMS (MM-ES+APCI, Pos): m/z 743.4 (M+H).

Step E. Tert-butyl (1R,5S)-3-(8-fluoro-2-((2-fluorotetrahydro-1H-pyrrolizin-7a(5H)-yl)methoxy)-7-(8-isopropyl-3-(methoxymethoxy)naphthalen-1-yl)pyrido[4,3-d]pyrimidin-4-yl)-3,8-diazabicyclo[3.2.1]octane-8-carboxylate (racemic, trans). Tert-butyl (1R,5S)-3-(8-fluoro-2-((2-fluorotetrahydro-1H-pyrrolizin-7a(5H)-yl)methoxy)-7-(3-(methoxymethoxy)-8-(prop-1-en-2-yl)naphthalen-1-yl)pyrido[4,3-d]pyrimidin-4-yl)-3,8-diazabicyclo[3.2.1]octane-8-carboxylate (racemic, trans) was dissolved in a mixture of MeOH (0.5 mL) and EtOAc (0.5 mL). The solution was degassed and purged with argon, and 10% palladium on carbon (4 mg, 0.004 mmol) was added. The reaction mixture was flushed with hydrogen and stirred under a hydrogen atmosphere for 2 hours. The reaction mixture was filtered through Celite, condensed, and purified by prep HPLC (50-95% MeCN/H$_2$O/0.1% TFA in 15 minutes) to afford tert-butyl (1R,5S)-3-(8-fluoro-2-((2-fluorotetrahydro-1H-pyrrolizin-7a(5H)-yl)methoxy)-7-(8-isopropyl-3-(methoxymethoxy)naphthalen-1-yl)pyrido[4,3-d]pyrimidin-4-yl)-3,8-diazabicyclo[3.2.1]octane-8-carboxylate (racemic, trans) (8 mg, 53%). LCMS (MM-ES+APCI, Pos): m/z 745.4 (M+H).

Step F. 4-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-5-isopropylnaphthalen-2-ol dihydrochloride (racemic, trans). Synthesized according to Example 229, Step B substituting tert-butyl (1R,5S)-3-(8-fluoro-2-((2-fluorotetrahydro-1H-pyrrolizin-7a(5H)-yl)methoxy)-7-(8-isopropyl-3-(methoxymethoxy)naphthalen-1-yl)pyrido[4,3-d]pyrimidin-4-yl)-3,8-diazabicyclo[3.2.1]octane-8-carboxylate to afford 4-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-5-isopropylnaphthalen-2-ol dihydrochloride (racemic, trans) (4.0 mg, 55%). LCMS (MM-ES+APCI, Pos): m/z 601.3 (M+H).

Example 365

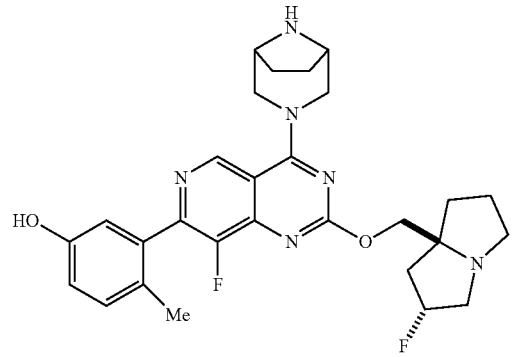

3-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-4-methylphenol (racemic, trans)

Step A. Tert-butyl (1R,5S)-3-(8-fluoro-2-((2-fluorotetrahydro-1H-pyrrolizin-7a(5H)-yl)methoxy)-7-(5-hydroxy-2-methylphenyl)pyrido[4,3-d]pyrimidin-4-yl)-3,8-diazabicyclo[3.2.1]octane-8-carboxylate (racemic, trans). Synthesized according to Example 424, Step A substituting (5-hydroxy-2-methylphenyl)boronic acid in place of 2-(5-(benzyloxy)-2-(2,2,2-trifluoroethyl)phenyl)-4,4,5,5-tetramethyl-1,3,2-dioxaborolane to afford tert-butyl (1R,5S)-3-(8-fluoro-2-((2-fluorotetrahydro-1H-pyrrolizin-7a(5H)-yl)methoxy)-7-(5-hydroxy-2-methylphenyl)pyrido[4,3-d]pyrimidin-4-yl)-3,8-diazabicyclo[3.2.1]octane-8-carboxylate (racemic, trans) (31 mg, 55%). LCMS (MM-ES+APCI, Pos): m/z 623.3 (M+H).

Step B. 3-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-4-methylphenol dihydrochloride (racemic, trans). Synthesized according to Example 229, Step B substituting tert-butyl (1R,5S)-3-(8-fluoro-2-((2-fluorotetrahydro-1H-pyrrolizin-7a(5H)-yl)methoxy)-7-(5-hydroxy-2-methylphenyl)pyrido[4,3-d]pyrimidin-4-yl)-3,8-diazabicyclo[3.2.1]octane-8-carboxylate (racemic, trans) in place of tert-butyl (1R,5S)-3-(8-fluoro-2-((tetrahydro-1H-pyrrolizin-7a(5H)-yl)methoxy)-7-(2-(trifluoromethoxy)phenyl)pyrido[4,3-d]pyrimidin-4-yl)-3,8-diazabicyclo[3.2.1]octane-8-carboxylate to afford 3-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-4-methylphenol dihydrochloride (racemic, trans) (34 mg, 100%). LCMS (MM-ES+APCI, Pos): m/z 523.2 (M+H).

Example 366

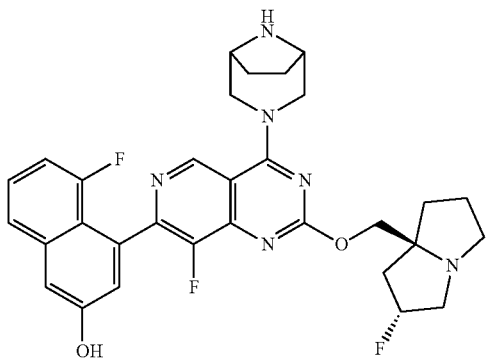 [SMILES: Oc1cc(-c2ncc3c(N4CC5CCC(C4)N5)nc(OC[C@@]45CCCN4C[C@H](F)C5)nc3c2F)c2c(F)cccc2c1]

4-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-5-fluoronaphthalen-2-ol (racemic, trans)

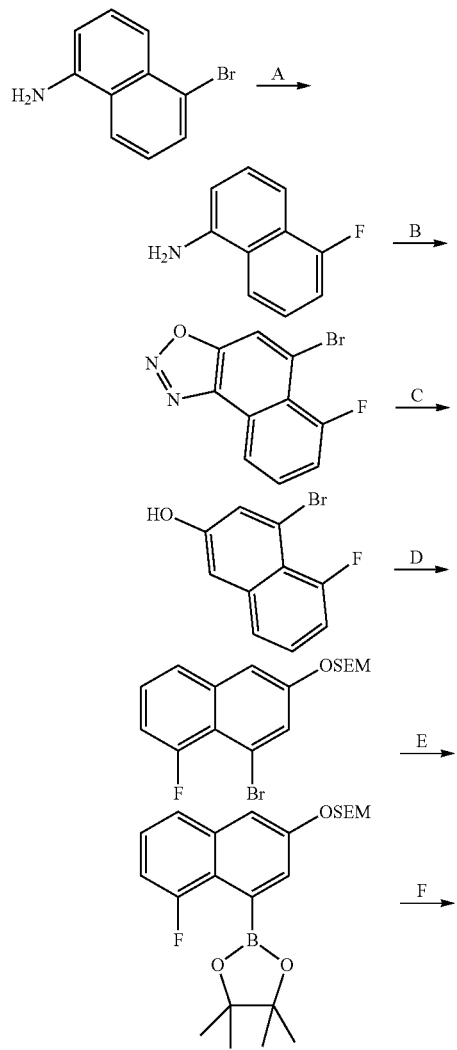

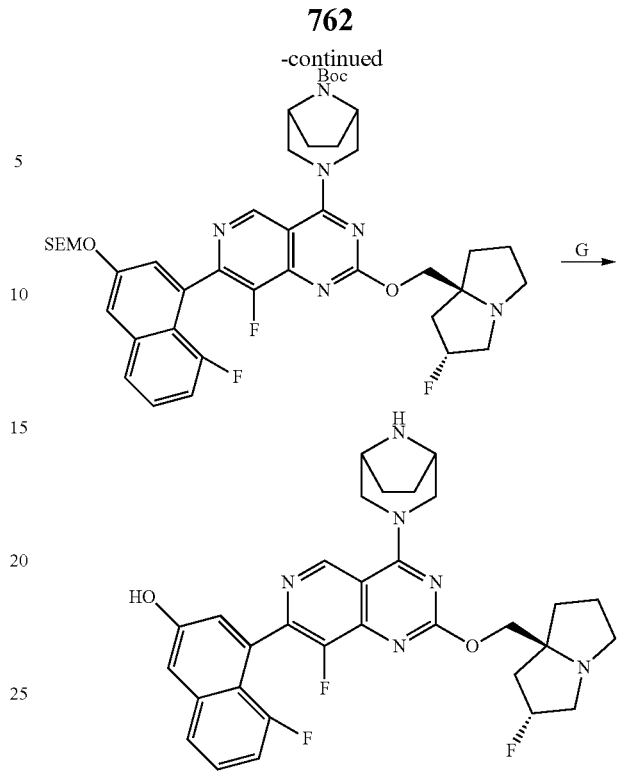

Step A. 5-fluoronaphthalen-1-amine. To a solution of 5-bromonaphthalen-1-amine (2.2 g, 10 mmol) in THF (33 mL) under $N_2$ at −78° C. was added LHMDS (1.0 M, 22.0 mL, 22.0 mmol). The mixture was warmed to rt and stirred for 5 min. The solution was cooled to −78° C. TMS-Cl (2.7 mL, 21 mmol) was added dropwise, and the mixture was slowly warmed to rt and stirred for 2 days. The solution was concentrated to dryness and the residue was extracted with hexanes and solids filtered. The filtrate was concentrated to a red oil. The oil was dissolved in THF (40.0 mL) under $N_2$ and the solution was cooled to −78° C. n-BuLi (2.5 M in hexanes, 5.6 mL, 14 mmol) was added slowly. The mixture was stirred for 15 min and N-fluoro-N-(phenylsulfonyl)benzenesulfonamide (4.7 g, 15 mmol) was added in one portion. The mixture was slowly warmed to rt. The mixture was quenched with water and extracted with ethyl acetate. The extract was washed with brine, dried ($Na_2SO_4$), and concentrated. The residue was dissolved in MeOH (10 mL), HCl (1.0 M, 2.0 mL) was added, and the reaction was stirred at rt for 3 min. The mixture was concentrated, basified with $NaHCO_3$, and extracted with ethyl acetate. The extract was concentrated and purified by preparative C18 HPLC (Gilson, 0-95% $CH_3CN/H_2O$ with 0.1% TFA). The desired fractions were combined, basified with $NaHCO_3$ (sat.), and concentrated to remove $CH_3CN$. The remaining mixture was extracted with ethyl acetate. The extract was dried ($Na_2SO_4$) and concentrated to give the title compound (0.50 g, 31%) as a black solid. LCMS (MM-ES+APCI, Pos): m/z 162.2 (M+H).

Step B. 5-bromo-6-fluoronaphtho[1,2-d][1,2,3]oxadiazole. To a solution of 5-fluoronaphthalen-1-amine (0.42 g, 2.6 mmol) in $CH_3CN$ (13 mL) at 0° C. was added NBS (0.92 g, 5.2 mmol). The mixture was stirred at 0° C. for 0.5 h and quenched with water (20 mL). The suspension was sonicated and filtered, the filter cake was rinsed with water and air dried to give a brown solid. The solid was dissolved in acetic acid (13 mL) and propionic acid (2.6 mL) and the mixture was cooled to 0° C. Sodium nitrite (0.22 g, 3.1 mmol) was added. The mixture was stirred at 0° C. for 30 min and at rt for 1 h. The mixture was diluted with ethyl acetate and washed with water. The organic layer was dried (Na₂SO₄), concentrated, and purified by flash chromatography eluting with ethyl acetate/hexanes (0-100%) to give the title compound (0.63 g, 91%) as a dark brown solid. LCMS (MM-ES+APCI, Pos): m/z 267.0 (M+H).

Step C. 4-bromo-5-fluoronaphthalen-2-ol. To a suspension of 5-bromo-6-fluoronaphtho[1,2-d][1,2,3]oxadiazole (0.60 g, 2.3 mmol) in EtOH (23 mL) and THF (11 mL) at 0° C. was added NaBH₄ (0.17 g, 4.5 mmol). The mixture was stirred at 0° C. for 1.5 h and quenched with NaHSO₄ (2.5%, 40 mL). The aqueous layer was extracted with ethyl acetate. The combined extract was washed with brine, dried (Na₂SO₄), concentrated, and purified by flash chromatography eluting with ethyl acetate/hexanes (0-50%) to give the title compound (0.30 g, 55%) as a light brown solid. ¹H NMR (400 MHz, (CDCl₃) δ 7.46 (m, 2H), 7.35 (m, 1H), 7.13 (s, 1H), 7.05 (m, 1H), 5.18 (s, 1H).

Step D. (2-(((4-bromo-5-fluoronaphthalen-2-yl)oxy)methoxy)ethyl)trimethylsilane. To a solution of 4-bromo-5-fluoronaphthalen-2-ol (0.30 g, 1.2 mmol) in THF (12 mL) at 0° C. was added NaH (60%, 60 mg, 1.5 mmol). The mixture was stirred at 0° C. for 5 min followed by addition of SEM-Cl (0.27 mL, 1.5 mmol). The mixture was warmed to r.t. and stirred for 1 h. The mixture was concentrated and purified by flash chromatography eluting with ethyl acetate/hexanes (0-10%) to give the title compound (0.29 g, 62%) as a red oil. ¹H NMR (400 MHz, (CDCl₃): δ 7.56 (s, 1H), 7.51 (d, J=8.3 Hz, 1H), 7.35 (m, 2H), 7.06 (m, 1H), 5.31 (s, 2H), 3.78 (t, J=8.3 Hz, 2H), 0.97 (t, J=8.3 Hz, 2H), 0.00 (s, 9H).

Step E. (2-(((5-fluoro-4-(4,4,5,5-tetramethyl-1,3,2-dioxaborolan-2-yl)naphthalen-2-yl)oxy)methoxy)ethyl)trimethylsilane. 1,4-Dioxane (4.7 mL) was added to a flask containing a mixture of (2-(((4-bromo-5-fluoronaphthalen-2-yl)oxy)methoxy)ethyl)trimethylsilane (0.18 g, 0.47 mmol), 4,4,4',4',5,5,5',5'-octamethyl-2,2'-bi(1,3,2-dioxaborolane) (0.30 g, 1.2 mmol), PdCl₂(dppf) (38 mg, 0.047 mmol), and KOAc (0.14 g, 1.4 mmol) under N₂. The mixture was heated at 90° C. for 2 h, cooled to rt, and quenched with ethyl acetate. The mixture was filtered, the filtrate was concentrated, and the residue was purified by flash chromatography eluting with ethyl acetate/hexanes (0-30%) to give the title compound (0.11 g, 55%) as a yellow oil. LCMS (MM-ES+APCI, Pos): m/z 301.2 (M-TMSCH2CH₂O).

Step F. tert-butyl (1R,5S)-3-(8-fluoro-7-(8-fluoro-3-((2-(trimethylsilyl)ethoxy)methoxy)naphthalen-1-yl)-2-((2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (racemic, trans). To a vial containing (2-(((5-fluoro-4-(4,4,5,5-tetramethyl-1,3,2-dioxaborolan-2-yl)naphthalen-2-yl)oxy)methoxy)ethyl)trimethylsilane (49 mg, 0.12 mmol), tert-butyl (1R,5S)-3-(7-chloro-8-fluoro-2-((2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (racemic, trans) (40 mg, 0.073 mmol), Pd(OAc)₂ (3.3 mg, 0.015 mmol), and 2-dicyclohexylphosphino-2',6'-dimethoxy-1,1'-biphenyl (12 mg, 0.029 mmol) under N₂ was added CH₃CN (0.73 mL) followed by K₂CO₃ (2.0 M, 0.11 mL, 0.22 mmol). The vial was closed, and the mixture was heated at 80° C. for 3 h. The mixture was cooled to rt and purified by preparative C18 HPLC (Gilson, 0-95% CH₃CN/H₂O with 0.1% TFA). The desired fractions were combined, basified with NaHCO₃ (sat.) and extracted with ethyl acetate. The extract was washed with water and brine, dried (Na₂SO₄), and concentrated to yield the title compound (26 mg, 44%) as a white solid. LCMS (MM-ES+APCI, Pos): m/z 807.3 (M+H).

Step G. 4-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-5-fluoronaphthalen-2-ol tris(2,2,2-trifluoroacetate) (racemic, trans). To a vial containing tert-butyl (1R,5S)-3-(8-fluoro-7-(8-fluoro-3-((2-(trimethylsilyl)ethoxy)methoxy)naphthalen-1-yl)-2-((2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (racemic, trans) (20 mg, 0.025 mmol) was added DCM (0.5 mL) and TFA (1 mL). The mixture was stirred at rt for 0.5 h and concentrated to dryness. The residue was purified by preparative C18 HPLC (Gilson, 0-95% CH₃CN/H₂O with 0.1% TFA). The desired fractions were combined and lyophilized to give the title compound (23 mg, 101%) as the bis TFA salt. LCMS (MM-ES+APCI, Pos): m/z 577.3 (M+H).

Example 367

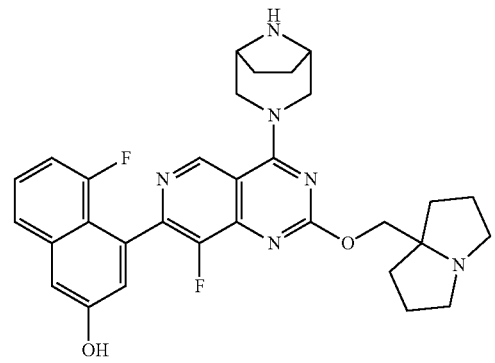 [SMILES: Oc1cc(-c2ncc3c(N4CC5CCC(C4)N5)nc(OCC45CCCN4CCC5)nc3c2F)c2c(F)cccc2c1]

4-(4-((1R,5S)-3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)-5-fluoronaphthalen-2-ol tris(2,2,2-trifluoroacetate)

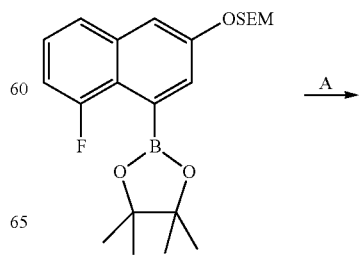

-continued

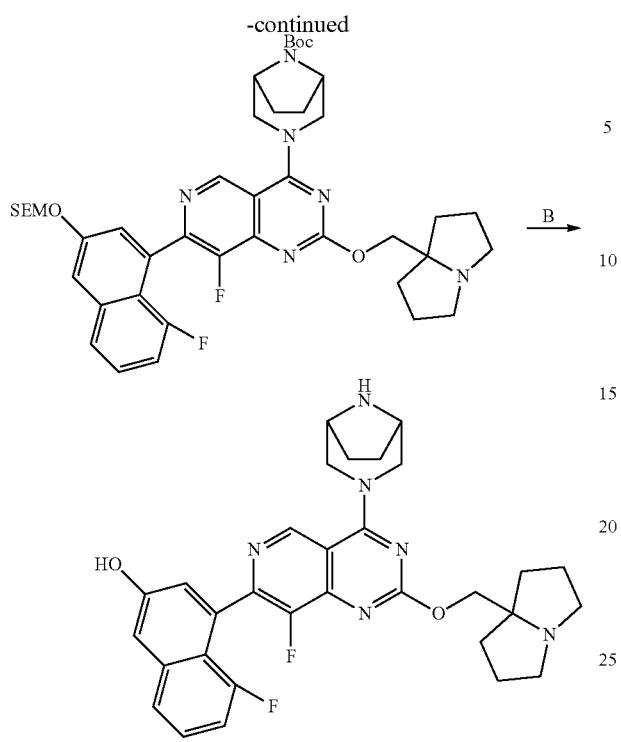

Step A. tert-butyl (1R,5S)-3-(8-fluoro-7-(8-fluoro-3-((2-(trimethylsilyl)ethoxy)methoxy)naphthalen-1-yl)-2-((tetrahydro-1H-pyrrolizin-7a(5H)-yl)methoxy)pyrido[4,3-d]pyrimidin-4-yl)-3,8-diazabicyclo[3.2.1]octane-8-carboxylate. To a vial containing (2-(((5-fluoro-4-(4,4,5,5-tetramethyl-1,3,2-dioxaborolan-2-yl)naphthalen-2-yl)oxy)methoxy)ethyl)trimethylsilane (38 mg, 0.090 mmol), tert-butyl (1R,5S)-3-(7-chloro-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (30 mg, 0.056 mmol), Pd(OAc)$_2$ (2.5 mg, 0.011 mmol) and 2-dicyclohexylphosphino-2',6'-dimethoxy-1,1'-biphenyl (9.2 mg, 0.023 mmol) under N$_2$ was added CH$_3$CN (0.6 mL), followed by K$_2$CO$_3$ (2.0 M, 85 µL, 0.17 mmol). The vial was closed, and the mixture was heated at 90° C. for 2 h. The mixture was cooled to rt and purified by preparative C18 HPLC (Gilson, 0-95% CH$_3$CN/H$_2$O with 0.1% TFA). The desired fractions were combined, basified with NaHCO$_3$ (sat.), and extracted with ethyl acetate. The extract was washed with water, washed with brine, dried (Na$_2$SO$_4$), and concentrated to yield the title compound (20 mg, 45%) as a yellow solid. LCMS (MM-ES+APCI, Pos): m/z 789.3 (M+H).

Step B. 4-(4-((1R,5S)-3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)-5-fluoronaphthalen-2-ol tris (2,2,2-trifluoroacetate). To a vial containing tert-butyl (1R,5S)-3-(8-fluoro-7-(8-fluoro-3-((2-(trimethylsilyl)ethoxy)methoxy)naphthalen-1-yl)-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (20 mg, 0.025 mmol) was added TFA (1 mL). The mixture was stirred at rt for 0.5 h and concentrated to dryness. The residue was purified by preparative C18 HPLC (Gilson, 0-95% CH$_3$CN/H$_2$O with 0.1% TFA). The desired fractions were combined and lyophilized to give the title compound (23 mg, 101%) as the bis TFA salt. LCMS (MM-ES+APCI, Pos): m/z 559.3 (M+H).

Example 368

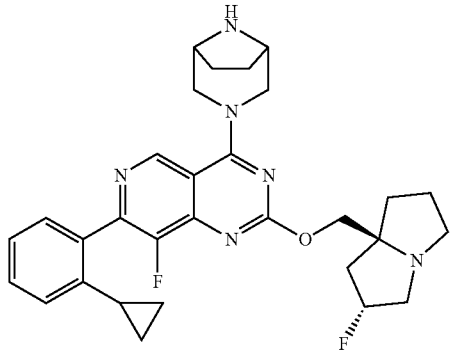 [SMILES: Fc1c(-c2ccccc2C2CC2)ncc2c(N3CC4CCC(C3)N4)nc(OC[C@@]34CCCN3C[C@H](F)C4)nc12]

4-((1R,5S)-3,8-diazabicyclo[3.2.1]octan-3-yl)-7-(2-cyclopropylphenyl)-8-fluoro-2-((2-fluorotetrahydro-1H-pyrrolizin-7a(5H)-yl)methoxy)pyrido[4,3-d]pyrimidine (racemic, trans)

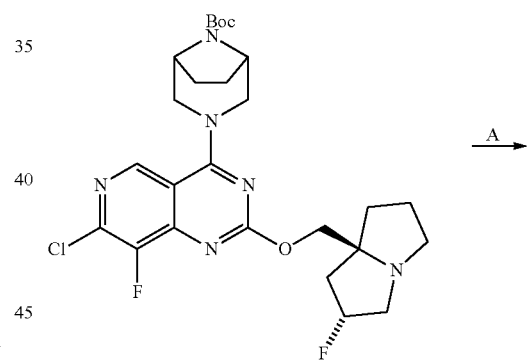

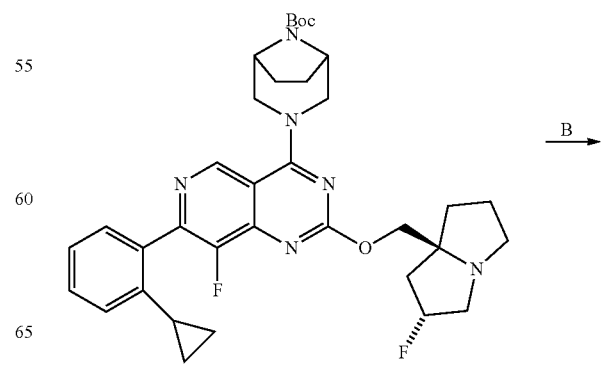

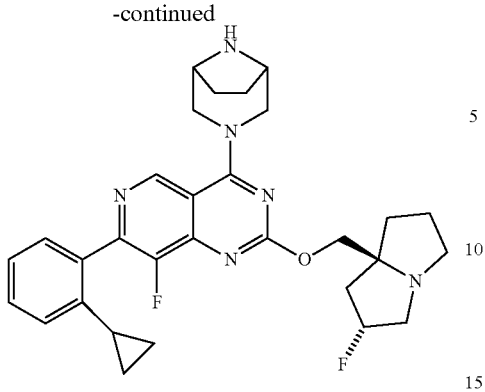

Step A. Tert-butyl (1R,5S)-3-(7-(2-cyclopropylphenyl)-8-fluoro-2-((2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (racemic, trans). Tert-butyl (1R,5S)-3-(7-chloro-8-fluoro-2-((2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (racemic, trans) (50 mg, 0.091 mmol), (2-cyclopropylphenyl)boronic acid (30 mg, 0.18 mmol), (2-dicyclohexylphosphino-2',6'-diisopropoxy-1,1'-biphenyl)[2-(2'-amino-1,1'-biphenyl)]palladium(II) methanesulfonate (30 mg, 0.036 mmol), and a 2 M aqueous solution of K₂CO₃ (0.13 mL, 0.27 mmol) were suspended in 1,4-dioxane (1 mL). The vial was degassed with argon, sealed, and heated to 100° C. for 20 hours. The mixture was cooled and condensed to a black oil. The residue was purified by prep HPLC (5-95% MeCN/H₂O/0.1% TFA in 15 minutes). The reaction was partitioned between DCM and saturated aqueous NaHCO₃. The organic layer was separated, dried over MgSO₄, and concentrated in vacuo to afford tert-butyl (1R,5S)-3-(7-(2-cyclopropylphenyl)-8-fluoro-2-((2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (racemic, trans) (48 mg, 83%). LCMS (MM-ES+APCI, Pos): m/z 633.3 (M+H).

Step B. 4-((1R,5S)-3,8-diazabicyclo[3.2.1]octan-3-yl)-7-(2-cyclopropylphenyl)-8-fluoro-2-((2-fluorotetrahydro-1H-pyrrolizin-7a(5H)-yl)methoxy)pyrido[4,3-d]pyrimidine dihydrochloride (racemic, trans). Synthesized according to Example 229, Step B substituting tert-butyl (1R,5S)-3-(7-(2-cyclopropylphenyl)-8-fluoro-2-((2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (racemic, trans) in place of tert-butyl (1R,5S)-3-(8-fluoro-2-((tetrahydro-1H-pyrrolizin-7a(5H)-yl)methoxy)-7-(2-(trifluoromethoxy)phenyl)pyrido[4,3-d]pyrimidin-4-yl)-3,8-diazabicyclo[3.2.1]octane-8-carboxylate to afford 4-((1R,5S)-3,8-diazabicyclo[3.2.1]octan-3-yl)-7-(2-cyclopropylphenyl)-8-fluoro-2-((2-fluorotetrahydro-1H-pyrrolizin-7a(5H)-yl)methoxy)pyrido[4,3-d]pyrimidine dihydrochloride (racemic, trans) (25 mg, 55%). LCMS (MM-ES+APCI, Pos): m/z 533.3 (M+H).

Example 369

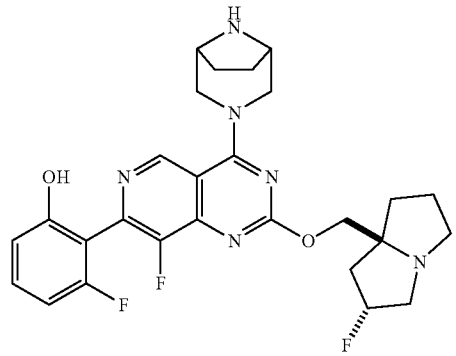

2-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-3-fluorophenol (racemic, trans)

Synthesized according to Example 3, Steps G-I substituting (2-fluorotetrahydro-1H-pyrrolizin-7a(5H)-yl)methanol (racemic, trans) in place of 2-(1-methyl-1H-imidazol-2-yl)ethan-1-ol in Step G and (2-fluoro-6-hydroxyphenyl)boronic acid in place of 4-(4,4,5,5-tetramethyl-1,3,2-dioxaborolan-2-yl)naphthalen-2-ol in Step H to afford 2-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-3-fluorophenol bis(2,2,2-trifluoroacetate) (racemic, trans) (31 mg, 83%). LCMS (MM-ES+APCI, Pos): m/z 527.2 (M+H).

Example 370

4-((1R,5S)-3,8-diazabicyclo[3.2.1]octan-3-yl)-8-fluoro-2-((tetrahydro-1H-pyrrolizin-7a(5H)-yl)methoxy)-7-(2-(trifluoromethyl)phenyl)pyrido[4,3-d]pyrimidine

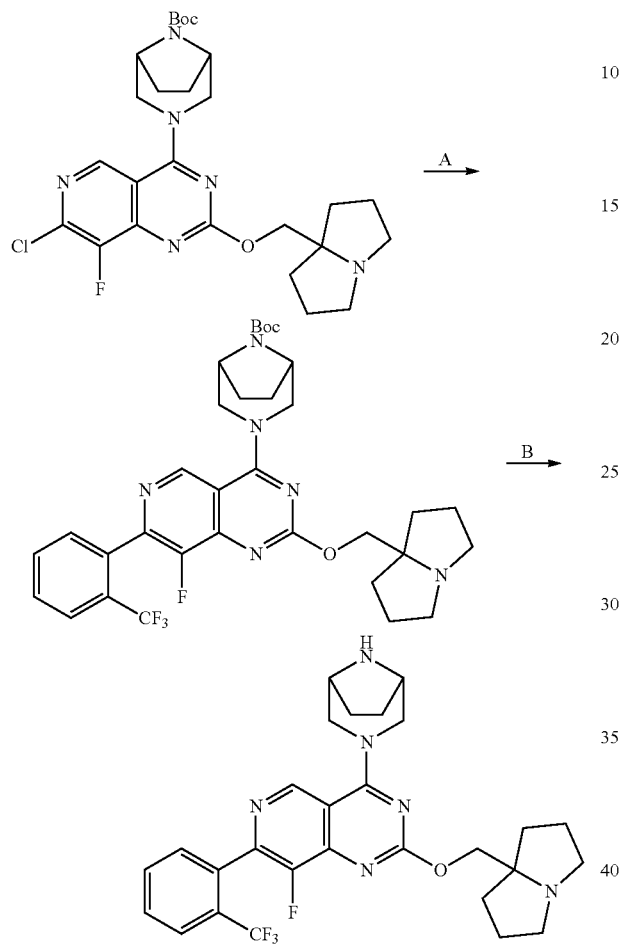

Step A. tert-butyl (1R,5S)-3-(8-fluoro-2-((tetrahydro-1H-pyrrolizin-7a(5H)-yl)methoxy)-7-(2-(trifluoromethyl)phenyl)pyrido[4,3-d]pyrimidin-4-yl)-3,8-diazabicyclo[3.2.1]octane-8-carboxylate. Tert-butyl (1R,5S)-3-(7-chloro-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (53 mg, 0.1 mmol), (2-(trifluoromethyl)phenyl)boronic acid (38 mg, 0.2 mmol) and XPhos Pd G2 (8 mg, 0.01 mmol) were added to a vial with a stir bar. The vial was degassed and purged with N₂ 3 times before degassed THF (0.2 mL) and degassed 0.5 M aqueous K₃PO₄ (0.4 mL, 0.2 mmol) were added. The reaction was heated to 40° C. for 2 hours. The reaction was diluted with water and extracted with DCM 3 times. The DCM layers were combined, dried with Na₂SO₄, filtered, and concentrated. The residue was purified by flash chromatography (silica, 0-20% MeOH in DCM) to yield tert-butyl (1R,5S)-3-(8-fluoro-2-((tetrahydro-1H-pyrrolizin-7a(5H)-yl)methoxy)-7-(2-(trifluoromethyl)phenyl)pyrido[4,3-d]pyrimidin-4-yl)-3,8-diazabicyclo[3.2.1]octane-8-carboxylate (36 mg, 56%). LCMS (MM-ES+APCI, Pos): m/z 643.3 (M+H).

Step B. 4-((1R,5S)-3,8-diazabicyclo[3.2.1]octan-3-yl)-8-fluoro-2-((tetrahydro-1H-pyrrolizin-7a(5H)-yl)methoxy)-7-(2-(trifluoromethyl)phenyl)pyrido[4,3-d]pyrimidine bis(2,2,2-trifluoroacetate). Tert-butyl (1R,5S)-3-(8-fluoro-2-((tetrahydro-1H-pyrrolizin-7a(5H)-yl)methoxy)-7-(2-(trifluoromethyl)phenyl)pyrido[4,3-d]pyrimidin-4-yl)-3,8-diazabicyclo[3.2.1]octane-8-carboxylate (36 mg, 0.056 mmol) was added to a round bottom flask with a stir bar. DCM (1 mL) and TFA (0.5 mL) were added at room temperature, and the reaction was stirred for 1 hour. The reaction was concentrated to dryness and the residue was purified via reverse phase chromatography (C18, 0-80% MeCN in water with 0.1% TFA). The fractions containing the product were combined, frozen, and lyophilized to yield 4-((1R,5S)-3,8-diazabicyclo[3.2.1]octan-3-yl)-8-fluoro-2-((tetrahydro-1H-pyrrolizin-7a(5H)-yl)methoxy)-7-(2-(trifluoromethyl)phenyl)pyrido[4,3-d]pyrimidine bis(2,2,2-trifluoroacetate) (35 mg, 82%). LCMS (MM-ES+APCI, Pos): m/z 543.3 (M+H).

Example 371

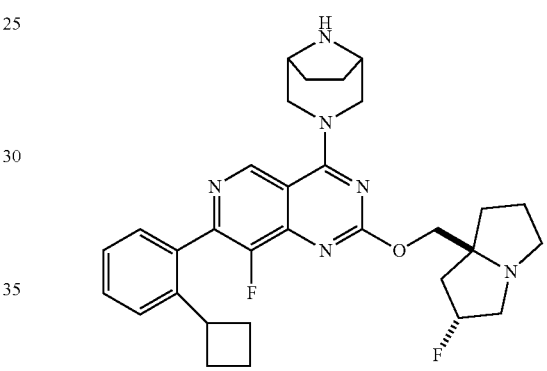

4-((1R,5S)-3,8-diazabicyclo[3.2.1]octan-3-yl)-7-(2-cyclobutylphenyl)-8-fluoro-2-((2-fluorotetrahydro-1H-pyrrolizin-7a(5H)-yl)methoxy)pyrido[4,3-d]pyrimidine (racemic, trans)

Step A. Tert-butyl (1R,5S)-3-(7-(2-cyclobutylphenyl)-8-fluoro-2-((2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (racemic, trans). Synthesized according to Example 368, Step A substituting (2-cyclobutylphenyl)boronic acid in place of (2-cyclopropylphenyl)boronic acid to afford tert-butyl (1R,5S)-3-(7-(2-cyclobutylphenyl)-8-fluoro-2-((2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (racemic, trans) (30 mg, 51%). LCMS (MM-ES+APCI, Pos): m/z 647.3 (M+H).

Step B. 4-((1R,5S)-3,8-diazabicyclo[3.2.1]octan-3-yl)-7-(2-cyclobutylphenyl)-8-fluoro-2-((2-fluorotetrahydro-1H-pyrrolizin-7a(5H)-yl)methoxy)pyrido[4,3-d]pyrimidine dihydrochloride (racemic, trans). Synthesized according to Example 229, Step B substituting tert-butyl (1R,5S)-3-(7-(2-cyclobutylphenyl)-8-fluoro-2-((2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (racemic, trans) in place of tert-butyl (1R,5S)-3-(8-fluoro-2-((tetrahydro-1H-pyrrolizin-7a(5H)-yl)methoxy)-7-(2-(trifluoromethoxy)phenyl)pyrido[4,3-d]pyrimidin-4-yl)-3,8-diaz-abicyclo[3.2.1]octane-8-carboxylate to afford 4-((1R,5S)-3,8-diazabicyclo[3.2.1]octan-3-yl)-7-(2-cyclobutylphenyl)-8-fluoro-2-((2-fluorotetrahydro-1H-pyrrolizin-7a(5H)-yl)methoxy)pyrido[4,3-d]pyrimidine dihydrochloride (racemic, trans) (9.0 mg, 31%). LCMS (MM-ES+APCI, Pos): m/z 547.3 (M+H).

Example 372

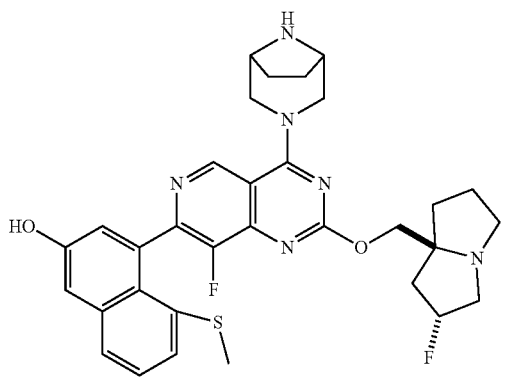

4-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-5-(methylthio)naphthalen-2-ol (racemic, trans)

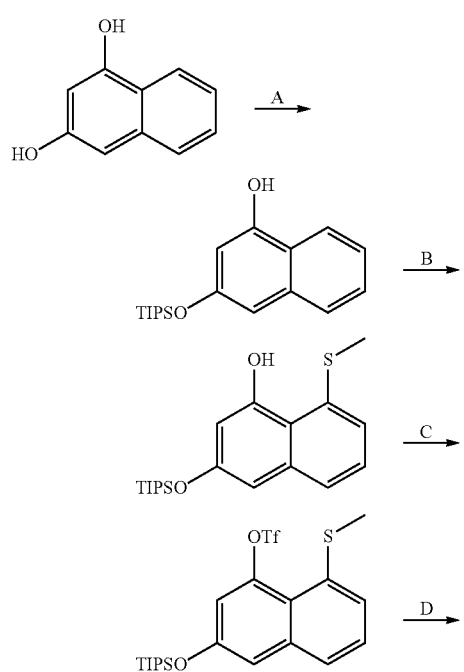

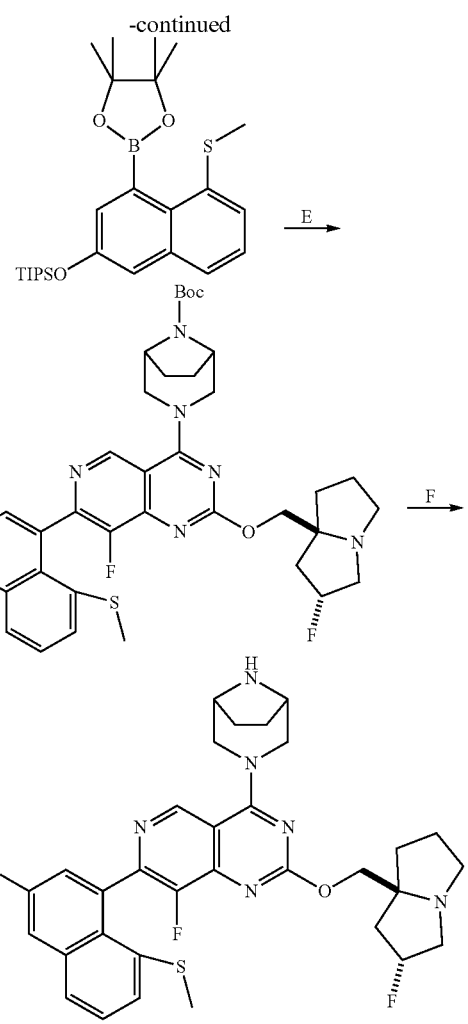

Step A. 3-((triisopropylsilyl)oxy)naphthalen-1-ol. A mixture of 1,3-dihydroxynaphthalene (2.0 g, 13 mmol), N,N-dimethylformamide (13 mL), 1H-imidazole (1.3 g, 19 mmol) and chlorotriisopropylsilane (2.9 mL, 14 mmol) was stirred at r.t. overnight. The reaction mixture was partitioned between water (50 mL) and MTBE (50 mL). The organic layer was washed with water (15 mL), washed with brine (15 mL), dried over $Na_2SO_4$, concentrated in vacuo, and chromatographed on silica gel in 5 to 20% EtOAc/hexane to yield the product as a colorless oil (1.0 g, 26%). The first-eluted isomer is the desired product. $^1$H NMR (CDCl$_3$, 400 MHz): 8.03 (d, J=8.3 Hz, 1H), 7.63 (d, J=8.2 Hz, 1H), 7.41 (ddd, J=8.0, 6.0, 1.0 Hz, 1H), 7.31 (ddd, J=8.0, 6.0, 1.0 Hz, 1H), 6.84 (d, J=2.0 Hz, 1H), 6.52 (d, J=2.1 Hz, 1H), 5.26 (s, 1H), 1.31 (sept, J=7.7 Hz, 3H), 1.13 (d, J=7.4 Hz, 18H).

Step B. 8-(methylthio)-3-((triisopropylsilyl)oxy)naphthalen-1-ol. To a stirred solution of 2.5M n-butyllithium (2.7 mL, 6.7 mmol) in hexanes, N1,N1,N2,N2-tetramethylethane-1,2-diamine (0.29 mL, 1.9 mmol) was added dropwise and the mixture was stirred at r.t. for 30 min. The reaction mixture was cooled to −20° C. and a solution of 3-((triisopropylsilyl)oxy)naphthalen-1-ol (0.61 g, 1.9 mmol) in tetrahydrofuran (1 mL) was added dropwise over 10 min. The reaction mixture was warmed to r.t and stirred for 24 h. The mixture was cooled to −10° C. and 1,2-dimethyldisulfane (0.51 mL, 5.8 mmol) was added dropwise. The mixture was warmed to r.t. over 10 min, diluted with MTBE (3 mL), and quenched with 1M HCl. The mixture was partitioned between water (10 mL) and MTBE (10 mL) and the layers were separated. The organic layer was washed with water (5 mL), washed with brine (5 mL), and dried over $Na_2SO_4$. The organic layer was evaporated under a stream of $N_2$ and chromatographed on silica gel in 2% EtOAc/hexane to yield the desired product as yellow oil (0.32 g, 45%). $^1$H NMR (CDCl$_3$, 400 MHz): 10.75 (s, 1H), 7.65 (d, J=8.3 Hz, 1H), 7.48 (d, J=7.1 Hz, 1H), 7.27 (t, J=7.5 Hz, 1H), 6.82 (d, J=2.4 Hz, 1H), 6.70 (d, J=2.4 Hz, 1H), 2.51 (s, 3H), 1.32 (sept, J=7.6 Hz, 3H), 1.13 (d, J=7.4 Hz, 18H).

Step C. 8-(methylthio)-3-((triisopropylsilyl)oxy)naphthalen-1-yl trifluoromethanesulfonate. A stirred solution of 8-(methylthio)-3-((triisopropylsilyl)oxy)naphthalen-1-ol (0.32 g, 0.87 mmol) and N-ethyl-N-isopropylpropan-2-amine (0.23 mL, 1.3 mmol) in dichloromethane (9 mL) was cooled to −78° C. and trifluoromethanesulfonic anhydride (0.18 mL, 1.0 mmol) was added dropwise. The reaction mixture was stirred while warming to r.t. overnight. and partitioned between 0.5M NaHCO$_3$ (10 mL) and hexane (10 mL). The organic phase was washed with water (5 mL) and brine (5 mL), dried over $Na_2SO_4$, evaporated under $N_2$ stream and chromatographed on silica gel in 2% EtOAc/hexane to yield the desired product as yellow oil (0.31 g, 72%).

Step D. Triisopropyl((5-(methylthio)-4-(4,4,5,5-tetramethyl-1,3,2-dioxaborolan-2-yl)naphthalen-2-yl)oxy)silane. A mixture of 8-(methylthio)-3-((triisopropylsilyl)oxy)naphthalen-1-yl trifluoromethanesulfonate (0.10 g, 0.20 mmol), bis(pinacolato)diboron (0.15 g, 0.61 mmol), potassium acetate (60 mg, 0.61 mmol), Pd(dppf)Cl$_2$*CH$_2$Cl$_2$ (16 mg, 0.020 mmol), and 1,4-dioxane (0.5 mL) was degassed and heated to 80° C. with stirring under $N_2$ for 3 h. The reaction mixture was cooled to r.t. and partitioned between 0.5M NaHCO$_3$ (10 mL) and MTBE (15 mL). The organic phase was washed with water (5 mL) and brine (5 mL), dried over $Na_2SO_4$, evaporated in vacuo and chromatographed on silica gel in 2% EtOAc/hexane to yield the desired products as colorless crystalline solid (64 mg, 67%). $^1$H NMR (CDCl$_3$, 400 MHz): 7.65-7.57 (m, 2H), 7.33 (t, J=7.7 Hz, 1H), 7.23 (d, J=2.4 Hz, 1H), 7.18 (t, J=2.4 Hz, 1H), 2.41 (s, 3H), 1.44 (s, 12H), 1.32 (sept, J=7.6 Hz, 3H), 1.13 (d, J=7.4 Hz, 18H).

Step E. tert-butyl (1R,5S)-3-(8-fluoro-2-((2-fluorotetrahydro-1H-pyrrolizin-7a(5H)-yl)methoxy)-7-(8-(methylthio)-3-((triisopropylsilyl)oxy)naphthalen-1-yl)pyrido[4,3-d]pyrimidin-4-yl)-3,8-diazabicyclo[3.2.1]octane-8-carboxylate (racemic, trans). A stirred mixture of tert-butyl (1R,5S)-3-(7-chloro-8-fluoro-2-((2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (racemic, trans) (35 mg, 0.064 mmol), triisopropyl((5-(methylthio)-4-(4,4,5,5-tetramethyl-1,3,2-dioxaborolan-2-yl)naphthalen-2-yl)oxy)silane (64 mg, 0.14 mmol), Pd(PPh$_3$)$_4$ (7.3 mg, 0.0064 mmol), 1,4-dioxane (0.6 mL), and 2M Na$_2$CO$_3$ (95 μL, 0.19 mmol) was degassed and heated to 80° C. under $N_2$ for 16 h. The reaction mixture was cooled to r.t. and partitioned between water (10 mL) and EtOAc (10 mL). The organic phase was washed with brine (5 mL), dried over Na$_2$SO$_4$, and evaporated in vacuo. The material was chromatographed on the reverse phase eluting with 5 to 99% MeCN-H$_2$O+0.1% TFA to yield the desired product as yellow solid (12 mg, 22%).

Step F. 4-(4-((1R,5S)-3,8-diazabicyclo[3.2.1]octan-3-yl)-8-fluoro-2-((2-fluorotetrahydro-1H-pyrrolizin-7a(5H)-yl) methoxy)pyrido[4,3-d]pyrimidin-7-yl)-5-(methylthio)naphthalen-2-ol (racemic, trans). A stirred solution of tert-butyl (1R,5S)-3-(8-fluoro-2-((2-fluorotetrahydro-1H-pyrrolizin-7a(5H)-yl)methoxy)-7-(8-(methylthio)-3-((triisopropylsilyl)oxy)naphthalen-1-yl)pyrido[4,3-d]pyrimidin-4-yl)-3,8-diazabicyclo[3.2.1]octane-8-carboxylate (racemic, trans) (12 mg, 0.014 mmol) in DCM was cooled to −20° C. and 4M hydrogen chloride in dioxane (0.35 mL, 1.4 mmol) was added. The reaction mixture was stirred at r.t. for 1.5 h, diluted with chloroform, cooled to −70° C., and evaporated under high vacuum. The residue was dissolved in 1M tetrabutylammonium fluoride in THF (0.14 mL, 0.14 mmol) and stirred at r.t. for 15 min. The solution was diluted with aq. buffer pH~8 (3 mL) and saturated with NaCl. The solution was extracted with DCM (5×7 mL) and 10% MeOH/DCM (3×5 mL). The combined organic phases were chromatographed on a reverse phase column, C18, using 5-95% MeCN/H$_2$O+0.1% TFA and freebased (Agilent PL-HCO3 MP SPE tube) to yield the target product as yellow solid (6.0 mg, 65%). LCMS (MM-ES+APCI, Pos): m/z 605.3 (M+H).

Example 373

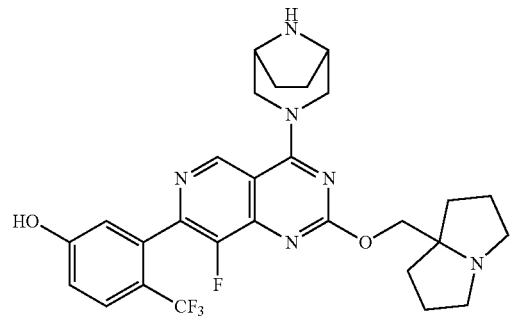 [SMILES: Oc1ccc(C(F)(F)F)c(-c2ncc3c(N4CC5CCC(C4)N5)nc(OCC45CCCN4CCC5)nc3c2F)c1]

3-(4-((1R,5S)-3,8-diazabicyclo[3.2.1]octan-3-yl)-8-fluoro-2-((tetrahydro-1H-pyrrolizin-7a(5H)-yl) methoxy)pyrido[4,3-d]pyrimidin-7-yl)-4-(trifluoromethyl)phenol

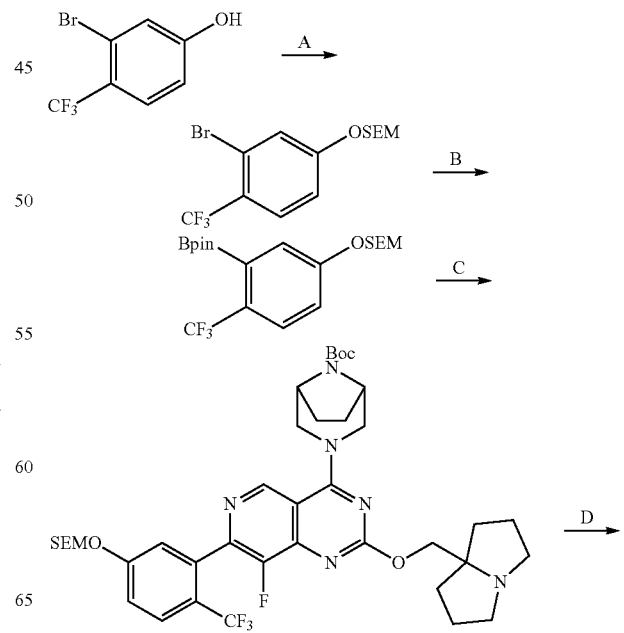

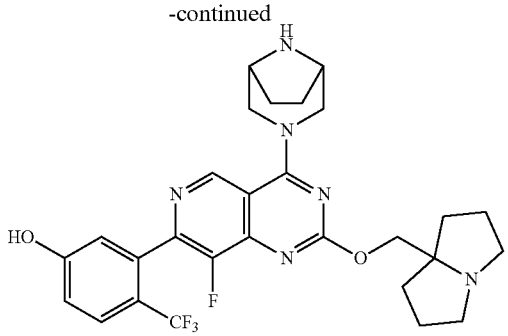

Step A. (2-((3-bromo-4-(trifluoromethyl)phenoxy)methoxy)ethyl)trimethylsilane. 3-Bromo-4-(trifluoromethyl)phenol (0.50 g, 2.1 mmol) and THF (21 mL) were added to a round bottom flask with a stir bar. The round bottom flask was cooled to 0° C. before 60% sodium hydride (60 mg, 2.49 mmol) was added in one portion. The reaction was stirred at 0° C. for 15 minutes before SEM-Cl (0.44 mL, 2.5 mmol) was added dropwise. The reaction was warmed to room temperature and stirred for 45 minutes. The reaction was diluted with H₂O and extracted with DCM 2 times. The DCM layers were combined, dried with Na₂SO₄, filtered, and concentrated. The residue was purified by flash chromatography (silica, hexanes) to yield (2-((3-bromo-4-(trifluoromethyl)phenoxy)methoxy)ethyl)trimethylsilane (0.45 g, 58%). ¹H NMR (CDCl₃, 400 MHz): δ 7.58 (d, J=8.8 Hz, 1H), 7.39 (s, 1H), 7.04 (d, J=8.8 Hz, 1H), 5.25 (s, 2H), 3.76 (t, J=8.2 Hz, 2H), 0.96 (t, J=8.2 Hz, 2H), 0.01 (s, 9H).

Step B. trimethyl(2-((3-(4,4,5,5-tetramethyl-1,3,2-dioxaborolan-2-yl)-4-(trifluoromethyl)phenoxy)methoxy)ethyl)silane. (2-((3-Bromo-4-(trifluoromethyl)phenoxy)methoxy)ethyl)trimethylsilane (0.45 g, 1.2 mmol), 4,4,4',4',5,5,5',5'-octamethyl-2,2'-bi(1,3,2-dioxaborolane) (0.92 g, 3.6 mmol), potassium acetate (0.36 mg, 3.6 mmol), dichloro[1,1'-bis(diphenylphosphino)ferrocene]palladium dichloromethane adduct (0.20 g, 0.24 mmol), and dioxane (6.0 mL) were added to a vial with a stir bar. The vial was sparged with N₂ for 15 minutes and the reaction was heated to 95° C. for 5 hours. The reaction was diluted with H₂O and extracted with hexanes 2 times. The hexanes layers were combined, dried with Na₂SO₄, filtered, and concentrated. The residue was purified by flash chromatography (silica, hexanes) to yield trimethyl(2-((3-(4,4,5,5-tetramethyl-1,3,2-dioxaborolan-2-yl)-4-(trifluoromethyl)phenoxy)methoxy)ethyl)silane (0.29 g, 58%). ¹H NMR (CDCl₃, 400 MHz): δ 7.58 (d, J=8.7 Hz, 1H), 7.32 (s, 1H), 7.12 (d, J=8.7 Hz, 1H), 5.25 (s, 2H), 3.75 (t, J=7.9 Hz, 2H), 1.36 (s, 12H), 0.94 (t, J=7.8 Hz, 2H), 0.00 (s, 9H).

Step C. tert-butyl (1R,5S)-3-(8-fluoro-2-((tetrahydro-1H-pyrrolizin-7a(5H)-yl)methoxy)-7-(2-(trifluoromethyl)-5-((2-(trimethylsilyl)ethoxy)methoxy)phenyl)pyrido[4,3-d]pyrimidin-4-yl)-3,8-diazabicyclo[3.2.1]octane-8-carboxylate. Tert-butyl (1R,5S)-3-(7-chloro-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (53 mg, 0.1 mmol), trimethyl(2-((3-(4,4,5,5-tetramethyl-1,3,2-dioxaborolan-2-yl)-4-(trifluoromethyl)phenoxy)methoxy)ethyl)silane (63 mg, 0.15 mmol) and XPhos Pd G2 (16 mg, 0.02 mmol) were added to a vial with a stir bar. The vial was degassed and purged with N₂ 3 times before degassed THF (0.2 mL) and degassed 0.5 M aqueous K₃PO₄ (0.4 mL, 0.2 mmol) were added. The reaction was heated to 40° C. for 2 hours. The reaction was diluted with water and extracted with DCM 3 times. The DCM layers were combined, dried with Na₂SO₄, filtered, and concentrated. The residue was purified by flash chromatography (silica, 0-20% OMeOH in DCM) to yield tert-butyl (1R,5S)-3-(8-fluoro-2-((tetrahydro-1H-pyrrolizin-7a(5H)-yl)methoxy)-7-(2-(trifluoromethyl)-5-((2-(trimethylsilyl)ethoxy)methoxy)phenyl)pyrido[4,3-d]pyrimidin-4-yl)-3,8-diazabicyclo[3.2.1]octane-8-carboxylate (41 mg, 53%). LCMS (MM-ES+APCI, Pos): m/z 789.4 (M+H).

Step D. 3-(4-((1R,5S)-3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)-4-(trifluoromethyl)phenol bis(2,2,2-trifluoroacetate). Tert-butyl (1R,5S)-3-(8-fluoro-2-((tetrahydro-1H-pyrrolizin-7a(5H)-yl)methoxy)-7-(2-(trifluoromethyl)-5-((2-(trimethylsilyl)ethoxy)methoxy)phenyl)pyrido[4,3-d]pyrimidin-4-yl)-3,8-diazabicyclo[3.2.1]octane-8-carboxylate (41 mg, 0.053 mmol) was added to a round bottom flask with a stir bar. DCM (1 mL) and TFA (0.5 mL) were added at room temperature and the reaction was stirred for 1 hour. The reaction was concentrated, and the residue was purified via reverse phase chromatography (C18, 0-80% MeCN in water with 0.1% TFA). The fractions containing the product were combined, frozen, and lyophilized to yield 3-(4-((1R,5S)-3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)-4-(trifluoromethyl)phenol bis(2,2,2-trifluoroacetate) (30 mg, 72%). LCMS (MM-ES+APCI, Pos): m/z 559.3 (M+H).

Example 374

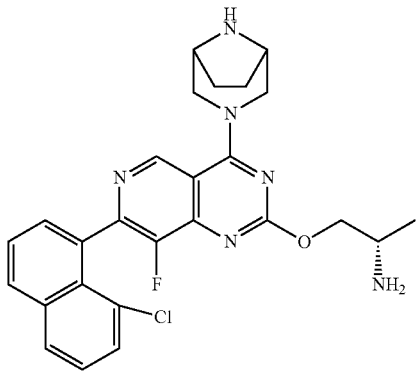 [SMILES: C[C@H](N)COc1nc(N2CC3CCC(C2)N3)c2cnc(-c3cccc4cccc(Cl)c34)c(F)c2n1]

(S)-1-((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)propan-2-amine bis(2,2,2-trifluoroacetate)

Synthesized according to Example 29, Step H substituting BOC-L-alaninol in place of (S)-(1-isopropylpyrrolidin-2-yl)methanol followed by deprotection using Example 2, Step I, (9 mg, 23%). LCMS (MM-ES+APCI, Pos): m/z 493.2 (M+H).

Example 375

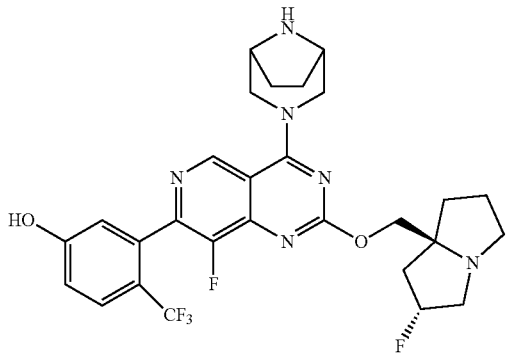 [SMILES: Oc1ccc(C(F)(F)F)c(-c2ncc3c(N4CC5CCC(C4)N5)nc(OC[C@@]45CCCN4C[C@H](F)C5)nc3c2F)c1]

3-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-4-(trifluoromethyl)phenol (racemic, trans)

Step A. Tert-butyl (1R,5S)-3-(8-fluoro-2-((2-fluorotetrahydro-1H-pyrrolizin-7a(5H)-yl)methoxy)-7-(2-(trifluoromethyl)-5-((2-(trimethylsilyl)ethoxy)methoxy)phenyl)pyrido[4,3-d]pyrimidin-4-yl)-3,8-diazabicyclo[3.2.1]octane-8-carboxylate (racemic, trans). Synthesized according to Example 424, Step A substituting trimethyl(2-((3-(4,4,5,5-tetramethyl-1,3,2-dioxaborolan-2-yl)-4-(trifluoromethyl)phenoxy)methoxy)ethyl)silane in place of 2-(5-(benzyloxy)-2-(2,2,2-trifluoroethyl)phenyl)-4,4,5,5-tetramethyl-1,3,2-dioxaborolane to afford tert-butyl (1R,5S)-3-(8-fluoro-2-((2-fluorotetrahydro-1H-pyrrolizin-7a(5H)-yl)methoxy)-7-(2-(trifluoromethyl)-5-((2-(trimethylsilyl)ethoxy)methoxy)phenyl)pyrido[4,3-d]pyrimidin-4-yl)-3,8-diazabicyclo[3.2.1]octane-8-carboxylate (racemic, trans) (43 mg, 59%). LCMS (MM-ES+APCI, Pos): m/z 807.3 (M+H).

Step B. 3-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-4-(trifluoromethyl)phenol bis(2,2,2-trifluoroacetate) (racemic, trans). Synthesized according to Example 417, Step B substituting tert-butyl (1R,5S)-3-(8-fluoro-2-((2-fluorotetrahydro-1H-pyrrolizin-7a(5H)-yl)methoxy)-7-(2-(trifluoromethyl)-5-((2-(trimethylsilyl)ethoxy)methoxy)phenyl)pyrido[4,3-d]pyrimidin-4-yl)-3,8-diazabicyclo[3.2.1]octane-8-carboxylate (racemic, trans) in place of tert-butyl (1R,5S)-3-(8-fluoro-2-((2-fluorotetrahydro-1H-pyrrolizin-7a(5H)-yl)methoxy)-7-(2-isobutylphenyl)pyrido[4,3-d]pyrimidin-4-yl)-3,8-diazabicyclo[3.2.1]octane-8-carboxylate (racemic, trans) to afford 3-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-4-(trifluoromethyl)phenol bis(2,2,2-trifluoroacetate) (racemic, trans) (30 mg, 59%). LCMS (MM-ES+APCI, Pos): m/z 577.3 (M+H).

Example 376

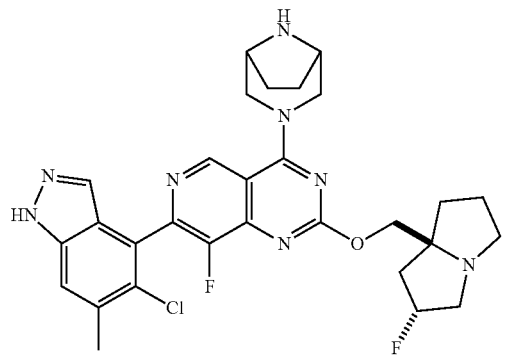

4-((1R,5S)-3,8-diazabicyclo[3.2.1]octan-3-yl)-7-(5-chloro-6-methyl-1H-indazol-4-yl)-8-fluoro-2-((2-fluorotetrahydro-1H-pyrrolizin-7a(5H)-yl)methoxy)pyrido[4,3-d]pyrimidine (racemic, trans)

Synthesized according to Example 3, Steps G-I substituting (2-fluorotetrahydro-1H-pyrrolizin-7a(5H)-yl)methanol (racemic, trans) in place of 2-(1-methyl-1H-imidazol-2-yl)ethan-1-ol in Step G and 5-chloro-6-methyl-1-(tetrahydro-2H-pyran-2-yl)-4-(4,4,5,5-tetramethyl-1,3,2-dioxaborolan-2-yl)-1H-indazole in place of 4-(4,4,5,5-tetramethyl-1,3,2-dioxaborolan-2-yl)naphthalen-2-ol in Step H to afford 4-((1R,5S)-3,8-diazabicyclo[3.2.1]octan-3-yl)-7-(5-chloro-6-methyl-1H-indazol-4-yl)-8-fluoro-2-((2-fluorotetrahydro-1H-pyrrolizin-7a(5H)-yl)methoxy)pyrido[4,3-d]pyrimidine (racemic, trans) (18 mg, 59%). LCMS (MM-ES+APCI, Pos): m/z 581.3 (M+H).

Example 377

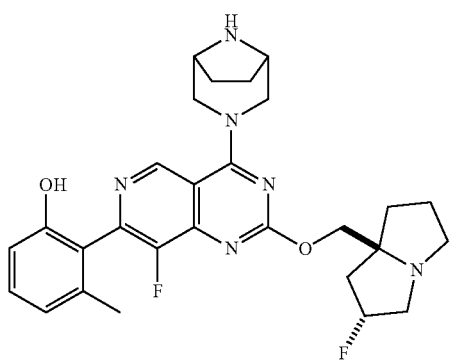

2-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-3-methylphenol (racemic, trans)

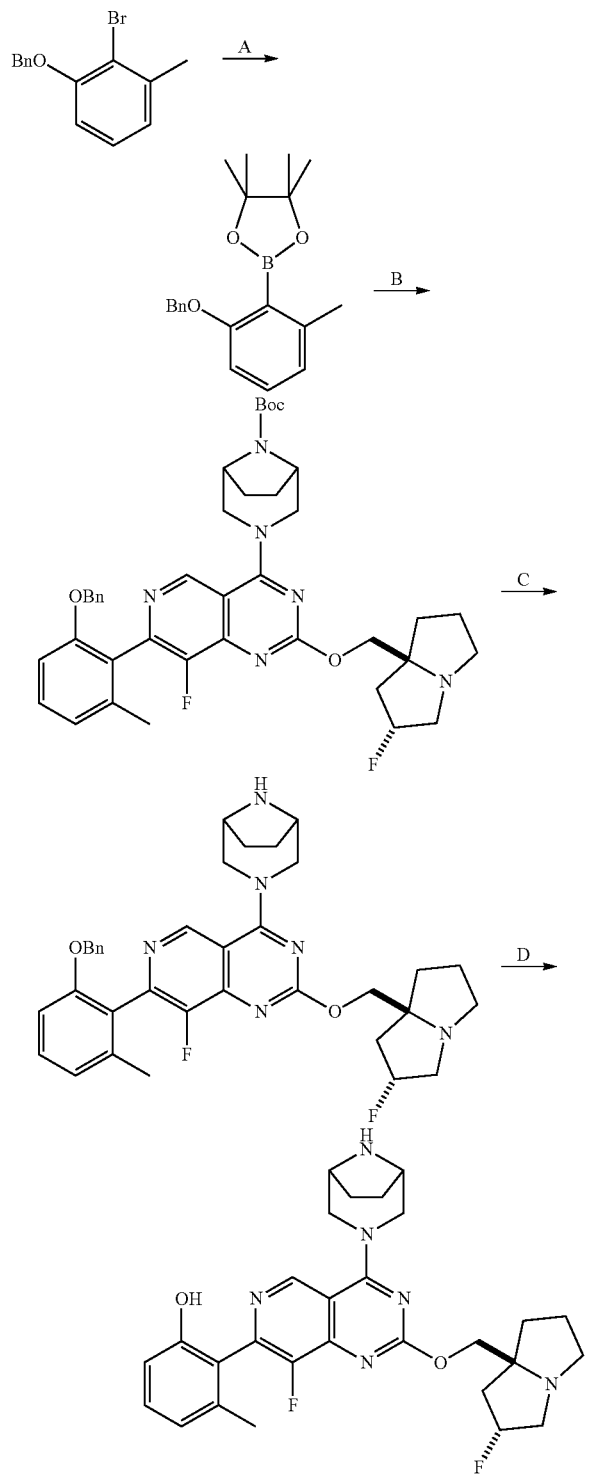

Step A. 2-(2-(benzyloxy)-6-methylphenyl)-4,4,5,5-tetramethyl-1,3,2-dioxaborolane. In a round bottom flask under $N_2$, tetrahydrofuran (7 mL) was cooled to −78° C. n-Butyllithium (0.35 mL, 0.87 mmol) was added dropwise over 2 min followed by a solution of 1-(benzyloxy)-2-bromo-3-methylbenzene (0.20 g, 0.72 mmol) in THF (0.5 mL). The solution was stirred for 1 h and 2-isopropoxy-4,4,5,5-tetramethyl-1,3,2-dioxaborolane (0.16 g, 0.87 mmol) was added dropwise. The reaction mixture was stirred while warming to r.t. overnight. The reaction was quenched with 0.5M NaHCO$_3$ (10 mL) and extracted with MTBE (15 mL). The organic phase was washed with brine, dried over Na$_2$SO$_4$, evaporated in vacuo, and chromatographed on silica gel eluting with 2% EtOAc/hexane to yield the desired product as colorless crystalline solid (0.14 g, 59%). $^1$H NMR (CDCl$_3$, 400 MHz): 7.50-7.43 (m, 2H), 7.38-7.31 (m, 2H), 7.29 (d, J=7.2 Hz, 1H), 7.17 (t, J=7.9 Hz, 1H), 6.75 (d, J=7.6 Hz, 1H), 6.69 (d, J=8.3 Hz, 1H), 5.02 (s, 2H), 2.36 (s, 3H), 1.30 (s, 12H).

Step B. Tert-butyl (1R,5S)-3-(7-(2-(benzyloxy)-6-methylphenyl)-8-fluoro-2-((2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (racemic, trans). A mixture of tert-butyl (1R,5S)-3-(7-chloro-8-fluoro-2-((2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (racemic, trans) (50 mg, 0.091 mmol), 2-(2-(benzyloxy)-6-methylphenyl)-4,4,5,5-tetramethyl-1,3,2-dioxaborolane (64 mg, 0.20 mmol), Pd(PPh$_3$)$_4$ (10 mg, 0.0091 mmol), 1,4-dioxane (1 mL), and 2M Na$_2$CO$_3$ (0.14 mL, 0.27 mmol) was degassed and stirred under N$_2$ at 80° C. for 3 days. The reaction mixture was cooled to r.t., partitioned between water (10 mL) and EtOAc (10 mL), and the layers were separated. The organic phase was washed with brine, dried over Na$_2$SO$_4$, evaporated in vacuo, and chromatographed on silica gel eluting with 2 to 4% MeOH/DCM to yield the desired product as colorless solid (30 mg, 46%). LCMS (MM-ES+APCI, Pos): m/z 713.4 (M+H).

Step C. 7-(2-(benzyloxy)-6-methylphenyl)-4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidine (racemic, trans). A stirred solution of tert-butyl (1R,5S)-3-(7-(2-(benzyloxy)-6-methylphenyl)-8-fluoro-2-((2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (racemic, trans) (30 mg, 0.042 mmol) in DCM was cooled on an ice-salt bath and 4M hydrogen chloride in dioxane (0.53 mL, 2.1 mmol) was added. The reaction mixture was stirred while warming to r.t. for 2 h. The mixture was evaporated under vacuum, basified with 2M Na$_2$CO$_3$, and extracted with DCM (3×5 mL). The combined extract was dried over Na$_2$SO$_4$, filtered, and evaporated under N$_2$ overnight. The material was used crude in the next reaction. LCMS (MM-ES+APCI, Pos): m/z 613.3 (M+H).

Step D. 2-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-3-methylphenol (racemic, trans). A mixture of 7-(2-(benzyloxy)-6-methylphenyl)-4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidine (racemic, trans) (26 mg, 0.042 mmol), methanol (4 mL) and 10% palladium on carbon (20 mg) was degassed and stirred under hydrogen atmosphere for 5 h. The reaction mixture was filtered through Celite, the filtrate was evaporated in vacuo and chromatographed on a reverse phase column, C18, Gilson, eluting with 5-95% MeCN/H$_2$O+0.1% TFA. Fractions containing product were concentrated in vacuo, basified with phosphate buffer to pH 10 and extracted with DCM twice to give the product (4.0 mg, 18%) as a colorless solid. LCMS (MM-ES+APCI, Pos): m/z 523.3 (M+H).

Example 378

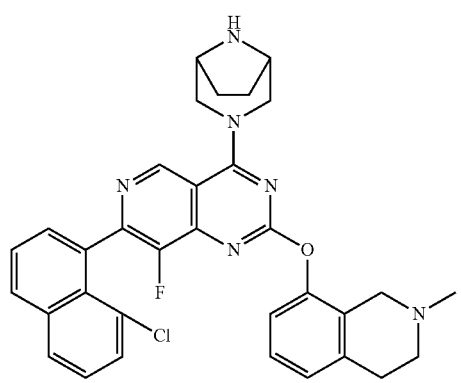 [SMILES: CN1CCc2cccc(Oc3nc(N4CC5CCC(C4)N5)c4cnc(-c5cccc6cccc(Cl)c56)c(F)c4n3)c2C1]

4-((1R,5S)-3,8-diazabicyclo[3.2.1]octan-3-yl)-7-(8-chloronaphthalen-1-yl)-8-fluoro-2-((2-methyl-1,2,3,4-tetrahydroisoquinolin-8-yl)oxy)pyrido[4,3-d]pyrimidine Synthesized according to Example 356 substituting 2-methyl-1,2,3,4-tetrahydroisoquinolin-8-ol for (R)-(1-methylpyrrolidin-3-yl)methanol in step A to give 4-((1R,5S)-3,8-diazabicyclo[3.2.1]octan-3-yl)-7-(8-chloronaphthalen-1-yl)-8-fluoro-2-((2-methyl-1,2,3,4-tetrahydroisoquinolin-8-yl)oxy)pyrido[4,3-d]pyrimidine as the bis TFA salt (45 mg, 60%). LCMS (MM-ES+APCI, Pos): m/z 581.2 (M+H).

Example 379

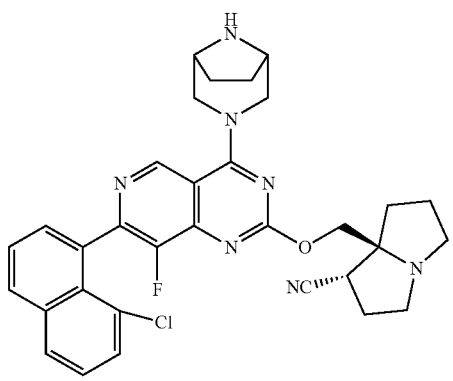 [SMILES: N#C[C@H]1CCN2CCC[C@@]12COc1nc(N2CC3CCC(C2)N3)c2cnc(-c3cccc4cccc(Cl)c34)c(F)c2n1]

7a-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)hexahydro-1H-pyrrolizine-1-carbonitrile (mixture of trans diastereomers)

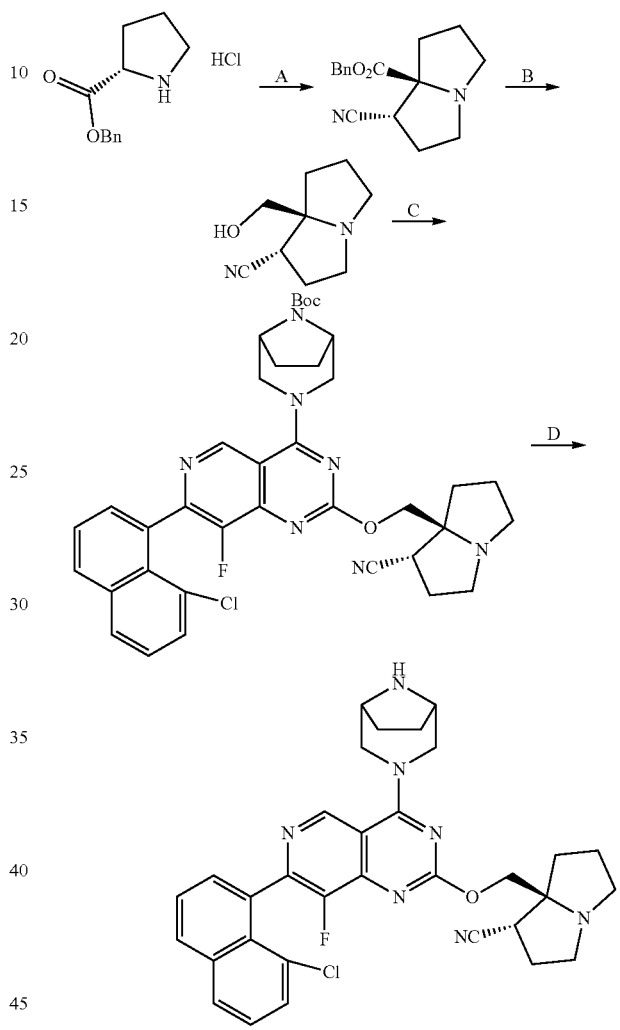

Step A. benzyl 1-cyanotetrahydro-1H-pyrrolizine-7a(5H)-carboxylate (mixture of trans diastereomers). To a mixture of benzyl L-prolinate hydrochloride (0.24 g, 1.0 mmol), paraformaldehyde (30 mg, 1.0 mmol), and acrylonitrile (0.10 mL, 1.5 mmol) in Et$_3$N (0.14 mL, 1.02 mmol) and toluene (4 mL) was added AgOAc (0.17 g, 1.0 mmol). The mixture was stirred in the dark at 50° C. for 15 h, cooled to rt, filtered, and the filter cake was washed with MTBE. The filtrate was concentrated and the residue was purified by flash chromatography eluting with ethyl acetate/hexanes (0-35%) to give the title compound (0.22 g, 80%) as a colorless oil. LCMS (MM-ES+APCI, Pos): m/z 271.2 (M+H).

Step B. 7a-(hydroxymethyl)hexahydro-1H-pyrrolizine-1-carbonitrile (mixture of trans diastereomers). To a solution of benzyl 1-cyanotetrahydro-1H-pyrrolizine-7a(5H)-carboxylate (mixture of trans diastereomers) (0.13 g, 0.49 mmol) in THF (3 mL) at 0° C. was added LiBH$_4$ (1.0 M, 0.49 mL, 0.49 mmol). The solution was stirred at rt for 5 h. The mixture was quenched with Rochelle's salt (1.0 M, 1.0 mL) and stirred at rt for 10 min. The mixture was extracted with ethyl acetate (2 mL×5). The combined extracts were concentrated and the residue was purified by flash chromatography eluting with ethyl acetate/hexanes (0-50%) to give the title compound (41 mg, 51%) as a colorless oil. LCMS (MM-ES+APCI, Pos): m/z 167.2 (M+H).

Step C. tert-butyl (1R,5S)-3-(7-(8-chloronaphthalen-1-yl)-2-((1-cyanotetrahydro-1H-pyrrolizin-7a(5H)-yl)methoxy)-8-fluoropyrido[4,3-d]pyrimidin-4-yl)-3,8-diazabicyclo[3.2.1]octane-8-carboxylate (mixture of trans diastereomers). A mixture of tert-butyl (1R,5S)-3-(2-chloro-7-(8-chloronaphthalen-1-yl)-8-fluoropyrido[4,3-d]pyrimidin-4-yl)-3,8-diazabicyclo[3.2.1]octane-8-carboxylate (27 mg, 0.049 mmol), Cs$_2$CO$_3$ (64 mg, 0.19 mmol), 7a-(hydroxymethyl)hexahydro-1H-pyrrolizine-1-carbonitrile (mixture of trans diastereomers) (16 mg, 0.10 mmol), and DMA (0.4 mL) was heated to 110° C. for 5 h. The reaction mixture was cooled to room temperature and purified by preparative C18 HPLC (Gilson, 0-95% CH$_3$CN/H$_2$O with 0.1% TFA). The desired fractions were combined, basified with NaHCO$_3$ (sat.) and extracted with ethyl acetate. The extract was washed with water, washed with brine, and dried (Na$_2$SO$_4$). The solution was concentrated to give the title compound (4.0 mg, 12%) as a white solid. LCMS (MM-ES+APCI, Pos): m/z 684.3 (M+H).

Step D. 7a-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)hexahydro-1H-pyrrolizine-1-carbonitrile (mixture of trans diastereomers). To a solution of tert-butyl (1R,5S)-3-(7-(8-chloronaphthalen-1-yl)-2-((1-cyanotetrahydro-1H-pyrrolizin-7a(5H)-yl)methoxy)-8-fluoropyrido[4,3-d]pyrimidin-4-yl)-3,8-diazabicyclo[3.2.1]octane-8-carboxylate (mixture of trans diastereomers) (4.0 mg, 0.0058 mmol) in DCM (0.5 mL) at rt was added TFA (0.25 mL). The solution was stirred at r.t. for 0.5 h and concentrated to dryness. The residue was purified by preparative C18 HPLC (Gilson, 0-95% CH$_3$CN/H$_2$O with 0.1% TFA). The desired fractions were combined, basified with NaHCO$_3$ (sat.), and extracted with DCM. The combined extract was dried (Na$_2$SO$_4$) and concentrated to give the title compound (3.0 mg, 88%) as a white solid. LCMS (MM-ES+APCI, Pos): m/z 584.2 (M+H).

Example 380

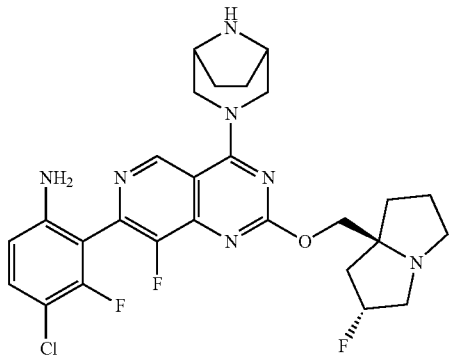 [SMILES: Nc1ccc(Cl)c(F)c1-c1ncc2c(N3CC4CCC(C3)N4)nc(OC[C@@]34CCCN3C[C@H](F)C4)nc2c1F]

2-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-4-chloro-3-fluoroaniline bis(2,2,2-trifluoroacetate) (racemic, trans)

Synthesized according to Example 196 substituting (2-fluorotetrahydro-1H-pyrrolizin-7a(5H)-yl)methanol (racemic, trans) in place of (tetrahydro-1H-pyrrolizin-7a(5H)-yl)methanol in step A and substituting (6-amino-3-chloro-2-fluorophenyl)boronic acid in place of 2,2-difluorobenzo[1,3]dioxole-4-boronic acid in step B to afford 2-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-4-chloro-3-fluoroaniline bis(2,2,2-trifluoroacetate) (racemic, trans) (5.6 mg, 39%). LCMS (MM-ES+APCI, Pos): m/z 560.2 (M+H).

Example 381

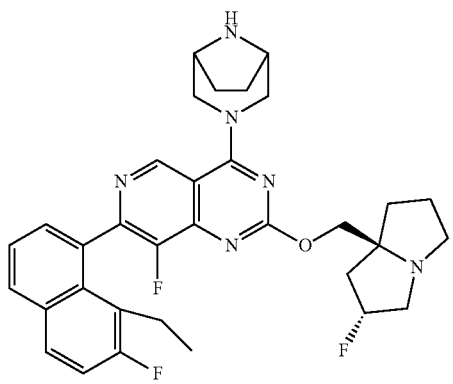 [SMILES: CCc1c(F)ccc2cccc(-c3ncc4c(N5CC6CCC(C5)N6)nc(OC[C@@]56CCCN5C[C@H](F)C6)nc4c3F)c12]

4-((1R,5S)-3,8-diazabicyclo[3.2.1]octan-3-yl)-7-(8-ethyl-7-fluoronaphthalen-1-yl)-8-fluoro-2-((2-fluorotetrahydro-1H-pyrrolizin-7a(5H)-yl)methoxy)pyrido[4,3-d]pyrimidine

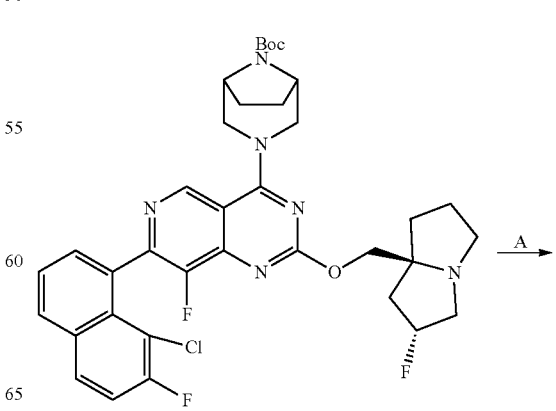

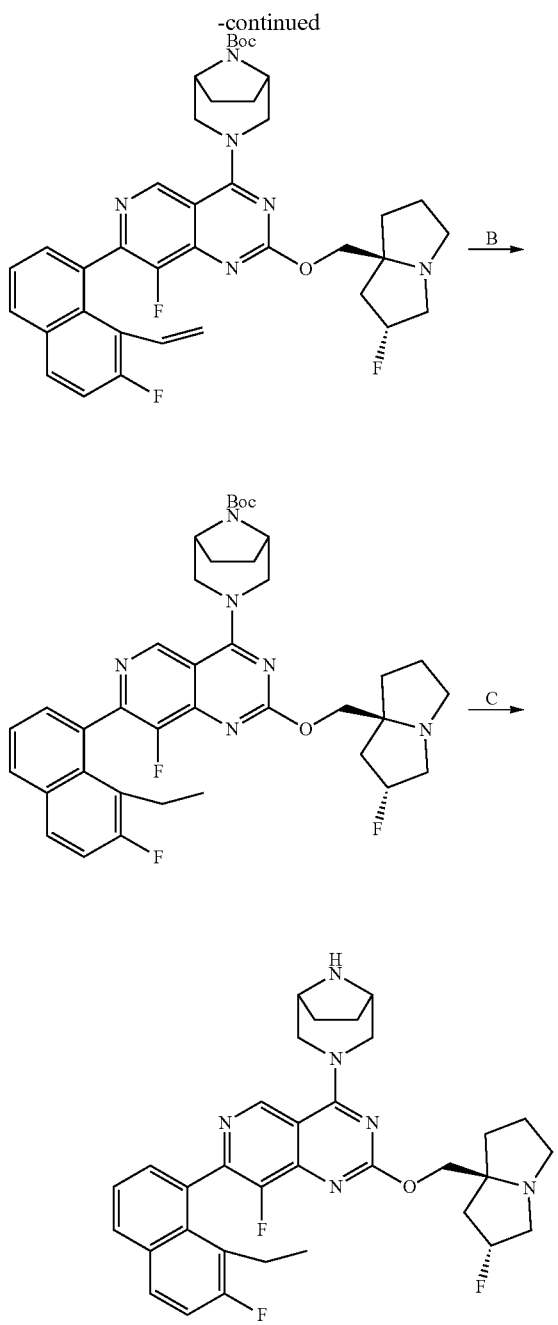

tert-butyl (1R,5S)-3-(7-(8-chloro-7-fluoronaphthalen-1-yl)-8-fluoro-2-((2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate. Synthesized according to Example 29 Step A-H, substituting 2-(8-chloro-7-fluoronaphthalen-1-yl)-4,4,5,5-tetramethyl-1,3,2-dioxaborolane (Synthesized according to Example 44, Step A-C) in place of 2-(8-chloronaphthalen-1-yl)-4,4,5,5-tetramethyl-1,3,2-dioxaborolane in Step C and (2-fluorotetrahydro-1H-pyrrolizin-7a(5H)-yl)methanol (racemic, trans) in place of (S)-(1-isopropylpyrrolidin-2-yl)methanol in Step H (49 mg, 40%). LCMS (MM-ES+APCI, Pos): m/z 695.2 [M+H].

Step A. tert-butyl (1R,5S)-3-(8-fluoro-7-(7-fluoro-8-vinylnaphthalen-1-yl)-2-((2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate: A mixture of tert-butyl (1R,5S)-3-(7-(8-chloro-7-fluoronaphthalen-1-yl)-8-fluoro-2-((2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (racemic, trans) (49 mg, 0.07 mmol), potassium vinyltrifluoroborate (0.028 g, 0.21 mmol), cesium fluoride (0.048 g, 0.32 mmol), and tetrakis(triphenylphosphine)palladium (0) (0.008 g, 0.007 mmol) in dioxane (2.8 mL) and water (0.54 mL) was purged with Ar and heated at 95° C. for 18 hours in a sealed vial. The mixture was partitioned between water (10 mL) and EtOAc (10 mL). The aqueous layer was extracted with EtOAc (2×10 mL). The combined organic phases were washed with brine (10 mL), dried over $Na_2SO_4$, filtered, and concentrated to afford tert-butyl (1R,5S)-3-(8-fluoro-7-(7-fluoro-8-vinylnaphthalen-1-yl)-2-((2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (racemic, trans) which was used crude in the next reaction. LCMS (MM-ES+APCI, Pos): m/z 687.3 [M+H].

Step B. tert-butyl (1R,5S)-3-(7-(8-ethyl-7-fluoronaphthalen-1-yl)-8-fluoro-2-((2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate: A solution of tert-butyl (1R,5S)-3-(8-fluoro-7-(7-fluoro-8-vinylnaphthalen-1-yl)-2-((2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (racemic, trans) (48 mg, 0.07 mmol) in EtOH (2 mL) was treated with 20% Pd(OH)2/C (5 mg) and stirred under a $H_2$ atmosphere for 16 hours. The mixture was treated with methanol (2 mL), additional Pd(OH)2/C (10 mg), and stirred under a $H_2$ atmosphere for 16 hours. Additional Pd(OH)2/C (10 mg) was added and the slurry stirred under a $H_2$ atmosphere for an additional 16 hours. The mixture was filtered through GF paper and the filtrate was concentrated. The residue was purified by flash column chromatography eluting with 0-7.5% MeOH/DCM to afford tert-butyl (1R,5S)-3-(7-(8-ethyl-7-fluoronaphthalen-1-yl)-8-fluoro-2-((2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (racemic, trans) (19 mg, 39%). LCMS (MM-ES+APCI, Pos): m/z 689.3 [M+H].

Step C. 4-((1R,5S)-3,8-diazabicyclo[3.2.1]octan-3-yl)-7-(8-ethyl-7-fluoronaphthalen-1-yl)-8-fluoro-2-((2-fluorotetrahydro-1H-pyrrolizin-7a(5H)-yl)methoxy)pyrido[4,3-d]pyrimidine (racemic, trans): A solution of tert-butyl (1R,5S)-3-(7-(8-ethyl-7-fluoronaphthalen-1-yl)-8-fluoro-2-((2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (racemic, trans) (18.5 mg, 0.03 mmol) in DCM (0.5 mL) was treated with 4N HCl in dioxane (0.5 mL). The reaction was stirred at ambient temperature for 1 hour and concentrated. The residue was purified by Gilson prep HPLC (5-95% ACN/water+0.1% TFA as modifier). Lyophilization afforded 4-((1R,5S)-3,8-diazabicyclo[3.2.1]octan-3-yl)-7-(8-ethyl-7-fluoronaphthalen-1-yl)-8-fluoro-2-((2-fluorotetrahydro-1H-pyrrolizin-7a(5H)-yl)methoxy)pyrido[4,3-d]pyrimidine di-TFA salt (racemic, trans) (11 mg, 51%). LCMS (MM-ES+APCI, Pos): m/z 589.3 [M+H].

Example 382

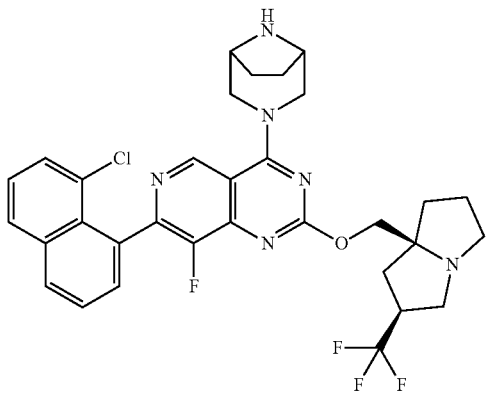 [SMILES: Fc1c(-c2cccc3cccc(Cl)c23)ncc2c(N3CC4CCC(C3)N4)nc(OC[C@@]34CCCN3C[C@@H](C(F)(F)F)C4)nc12]

4-((1R,5S)-3,8-diazabicyclo[3.2.1]octan-3-yl)-7-(8-chloronaphthalen-1-yl)-8-fluoro-2-(((2S,7aS)-2-(trifluoromethyl)tetrahydro-1H-pyrrolizin-7a(5H)-yl)methoxy)pyrido[4,3-d]pyrimidine) (mixture of cis diastereomers)

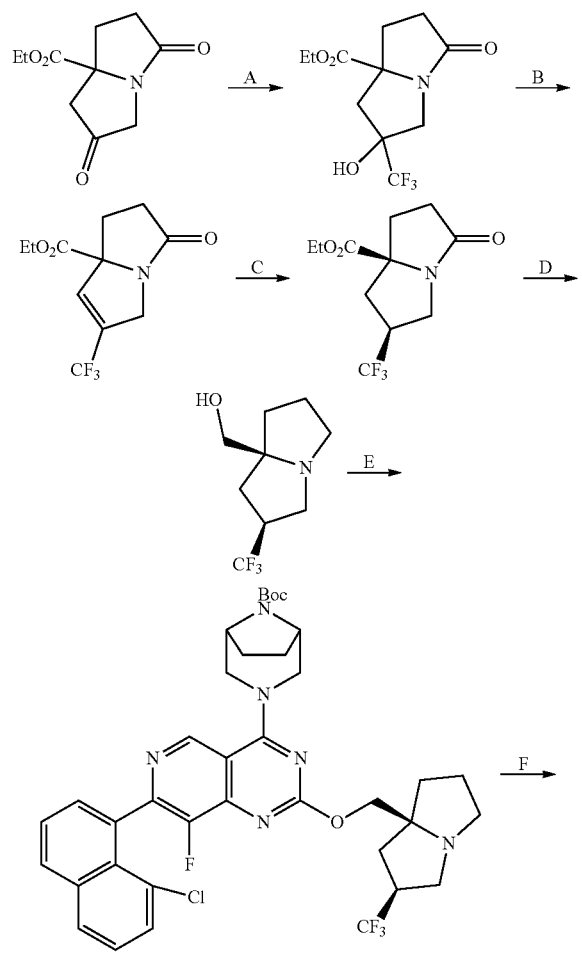

-continued

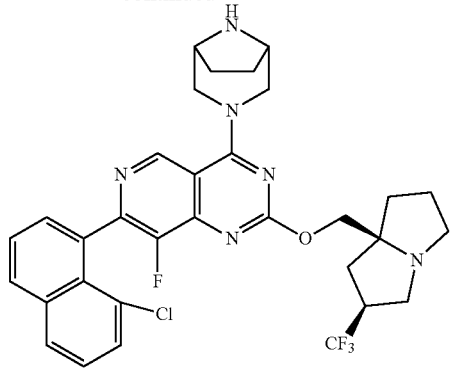

Step A. ethyl 2-hydroxy-5-oxo-2-(trifluoromethyl)tetrahydro-1H-pyrrolizine-7a(5H)-carboxylate. To a solution of ethyl 2,5-dioxotetrahydro-1H-pyrrolizine-7a(5H)-carboxylate (0.42 g, 2.0 mmol) in THF (5 mL) at 0° C. was added (trifluoromethyl)trimethylsilane (0.31 mL, 2.1 mmol), followed by TBAF (1.0 M in THF, 3.0 mL, 3.0 mmol). The mixture was warmed to rt and stirred for 20 h. (Trifluoromethyl)trimethylsilane (0.059 mL, 0.40 mmol) was added and the mixture was stirred for 20 h. To the mixture was added sat. NH$_4$Cl (2 mL). The reaction stirred at rt for 10 min and TBAF (1.0 mL, 0.020 mL, 0.020 mmol) was added. The mixture was stirred at rt for 1 h and was quenched with water. The mixture was extracted with ethyl acetate/hexanes (1:1). The organic extract was dried (Na$_2$SO$_4$) and concentrated to give the crude title compound (0.49 g, 87%) as a brown oil. LCMS (MM-ES+APCI, Pos): m/z 282.2 (M+H).

Step B. ethyl 3-oxo-6-(trifluoromethyl)-2,3-dihydro-1H-pyrrolizine-7a(5H)-carboxylate. To a solution of ethyl 2-hydroxy-5-oxo-2-(trifluoromethyl)tetrahydro-1H-pyrrolizine-7a(5H)-carboxylate (0.50 g, 1.8 mmol) in pyridine (12 mL) at r.t. under N$_2$ was added thionyl chloride (1.3 mL, 18 mmol). The mixture was heated at 80° C. for 1 h, cooled to rt, and concentrated to dryness. The residue was diluted with HCl (1 M, 80 mL) and extracted with EtOAc 2 times. The combined extracts were washed with HCl (1 M, 30 mL) and NaHCO$_3$ (sat.). The EtOAc layer was dried (Na$_2$SO$_4$), concentrated, and the residue purified by flash chromatography eluting with ethyl acetate/hexanes (0-50%) to give the title compound (0.17 g, 37%) as a yellow solid. LCMS (MM-ES+APCI, Pos): m/z 264.2 (M+H).

Step C. ethyl 5-oxo-2-(trifluoromethyl)tetrahydro-1H-pyrrolizine-7a(5H)-carboxylate (mixture of cis diastereomers). A mixture of ethyl 3-oxo-6-(trifluoromethyl)-2,3-dihydro-1H-pyrrolizine-7a(5H)-carboxylate (0.16 g, 0.59 mmol), Pd—C (10%, 31 mg, 0.029 mmol), and ethanol (6 mL) was stirred under a balloon of H$_2$ at rt for 2 h. The mixture was filtered through Celite and the filtrate was concentrated to yield the crude title compound (0.16 g, 101%) as a colorless oil. LCMS (MM-ES+APCI, Pos): m/z 266.1 (M+H).

Step D. (2-(trifluoromethyl)tetrahydro-1H-pyrrolizin-7a(5H)-yl)methanol (mixture of cis diastereomers). To a solution of ethyl 5-oxo-2-(trifluoromethyl)tetrahydro-1H-pyrrolizine-7a(5H)-carboxylate (mixture of cis diastereomers) (0.15 g, 0.57 mmol) in THF (3 mL) at 0° C. was added LAH (2.4 M, in THF, 0.47 mL, 1.13 mmol) dropwise. The solution was heated at 60° C. for 3 h. The mixture was cooled to 0° C. and Rochelle's Salt (1 M, 0.5 mL) was added. The mixture was stirred at 0° C. for 10 min. The suspension was filtered and the solid was washed with THF.

The combined filtrate was concentrated to give the crude title compound (80 mg, 68%) as a white solid. LCMS (MM-ES+APCI, Pos): m/z 210.3 (M+H).

Step E. tert-butyl (1R,5S)-3-(7-(8-chloronaphthalen-1-yl)-8-fluoro-2-((2-(trifluoromethyl)tetrahydro-1H-pyrrolizin-7a(5H)-yl)methoxy)pyrido[4,3-d]pyrimidin-4-yl)-3,8-diazabicyclo[3.2.1]octane-8-carboxylate (mixture of cis diastereomers). To a solution of tert-butyl (1R,5S)-3-(2-chloro-7-(8-chloronaphthalen-1-yl)-8-fluoropyrido[4,3-d]pyrimidin-4-yl)-3,8-diazabicyclo[3.2.1]octane-8-carboxylate (27 mg, 0.049 mmol) and (2-(trifluoromethyl)tetrahydro-1H-pyrrolizin-7a(5H)-yl)methanol (mixture of cis diastereomers) (15 mg, 0.073 mmol) in THF (0.50 mL) at 0° C. was added NaH (60%, 3.9 mg, 0.097 mmol). The solution was stirred at 0° C. for 30 min and at rt for 6 h. The solution was purified by preparative C18 HPLC (Gilson, 0-95% CH₃CN/H₂O with 0.1% TFA). The desired fractions were combined and concentrated to remove CH₃CN. The solution was basified with NaHCO₃ (sat.) and extracted with ethyl acetate. The extract was dried (Na₂SO₄) and concentrated to yield the title compound (22 mg, 62%) as a white solid. LCMS (MM-ES+APCI, Pos): m/z 727.2 (M+H).

Step F. 4-((1R,5S)-3,8-diazabicyclo[3.2.1]octan-3-yl)-7-(8-chloronaphthalen-1-yl)-8-fluoro-2-((2-(trifluoromethyl)tetrahydro-1H-pyrrolizin-7a(5H)-yl)methoxy)pyrido[4,3-d]pyrimidine bis(2,2,2-trifluoroacetate) (mixture of cis diastereomers). To a solution of tert-butyl (1R,5S)-3-(7-(8-chloronaphthalen-1-yl)-8-fluoro-2-((2-(trifluoromethyl)tetrahydro-1H-pyrrolizin-7a(5H)-yl)methoxy)pyrido[4,3-d]pyrimidin-4-yl)-3,8-diazabicyclo[3.2.1]octane-8-carboxylate (mixture of cis diastereomers) (22 mg, 0.030 mmol) in DCM (1 mL) was added TFA (0.50 mL). The solution was stirred at r.t. for 0.5 h and was concentrated. The residue was purified by preparative C18 HPLC (Gilson, 0-95% CH₃CN/H₂O with 0.1% TFA). The desired fractions were combined and lyophilized to give the title compound (22 mg, 73%) as the bis TFA salt. LCMS (MM-ES+APCI, Pos): m/z 627.2 (M+H).

Example 383

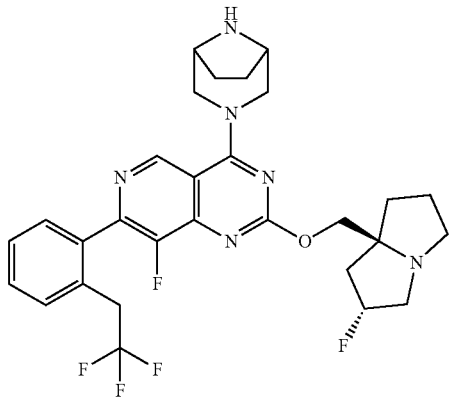 [SMILES: Fc1c(-c2ccccc2CC(F)(F)F)ncc2c(N3CC4CCC(C3)N4)nc(OC[C@@]34CCCN3C[C@H](F)C4)nc12]

4-((1R,5S)-3,8-diazabicyclo[3.2.1]octan-3-yl)-8-fluoro-2-((2-fluorotetrahydro-1H-pyrrolizin-7a(5H)-yl)methoxy)-7-(2-(2,2,2-trifluoroethyl)phenyl)pyrido[4,3-d]pyrimidine (racemic, trans)

Step A. Tert-butyl (1R,5S)-3-(8-fluoro-2-((2-fluorotetrahydro-1H-pyrrolizin-7a(5H)-yl)methoxy)-7-(2-(2,2,2-trifluoroethyl)phenyl)pyrido[4,3-d]pyrimidin-4-yl)-3,8-diazabicyclo[3.2.1]octane-8-carboxylate (racemic, trans). Synthesized according to Example 424, Step A substituting 4,4,5,5-tetramethyl-2-(2-(2,2,2-trifluoroethyl)phenyl)-1,3,2-dioxaborolane in place of 2-(5-(benzyloxy)-2-(2,2,2-trifluoroethyl)phenyl)-4,4,5,5-tetramethyl-1,3,2-dioxaborolane to afford tert-butyl (1R,5S)-3-(8-fluoro-2-((2-fluorotetrahydro-1H-pyrrolizin-7a(5H)-yl)methoxy)-7-(2-(2,2,2-trifluoroethyl)phenyl)pyrido[4,3-d]pyrimidin-4-yl)-3,8-diazabicyclo[3.2.1]octane-8-carboxylate (racemic, trans) (40 mg, 65%). LCMS (MM-ES+APCI, Pos): m/z 675.3 (M+H).

Step B. 4-((1R,5S)-3,8-diazabicyclo[3.2.1]octan-3-yl)-8-fluoro-2-((2-fluorotetrahydro-1H-pyrrolizin-7a(5H)-yl)methoxy)-7-(2-(2,2,2-trifluoroethyl)phenyl)pyrido[4,3-d]pyrimidine dihydrochloride (racemic, trans). Synthesized according to Example 229, Step B substituting tert-butyl (1R,5S)-3-(8-fluoro-2-((2-fluorotetrahydro-1H-pyrrolizin-7a(5H)-yl)methoxy)-7-(2-(2,2,2-trifluoroethyl)phenyl)pyrido[4,3-d]pyrimidin-4-yl)-3,8-diazabicyclo[3.2.1]octane-8-carboxylate (racemic, trans) in place of tert-butyl (1R,5S)-3-(8-fluoro-2-((tetrahydro-1H-pyrrolizin-7a(5H)-yl)methoxy)-7-(2-(trifluoromethoxy)phenyl)pyrido[4,3-d]pyrimidin-4-yl)-3,8-diazabicyclo[3.2.1]octane-8-carboxylate to afford 4-((1R,5S)-3,8-diazabicyclo[3.2.1]octan-3-yl)-8-fluoro-2-((2-fluorotetrahydro-1H-pyrrolizin-7a(5H)-yl)methoxy)-7-(2-(2,2,2-trifluoroethyl)phenyl)pyrido[4,3-d]pyrimidine dihydrochloride (racemic, trans) (26 mg, 67%). LCMS (MM-ES+APCI, Pos): m/z 575.3 (M+H).

Example 384

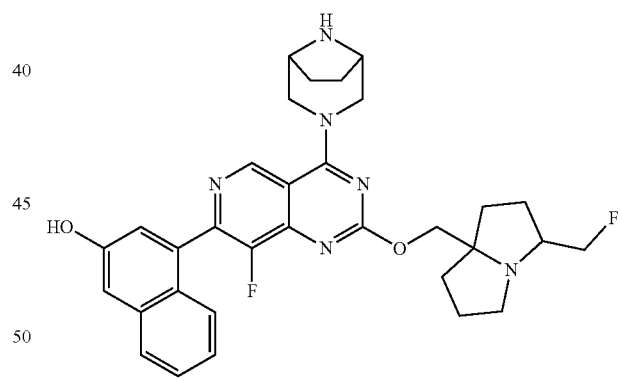

4-(4-((1R,5S)-3,8-diazabicyclo[3.2.1]octan-3-yl)-8-fluoro-2-((3-(fluoromethyl)tetrahydro-1H-pyrrolizin-7a(5H)-yl)methoxy)pyrido[4,3-d]pyrimidin-7-yl)naphthalen-2-ol (mixture of isomers)

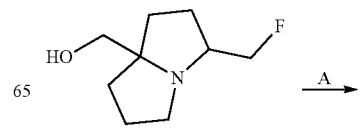

-continued

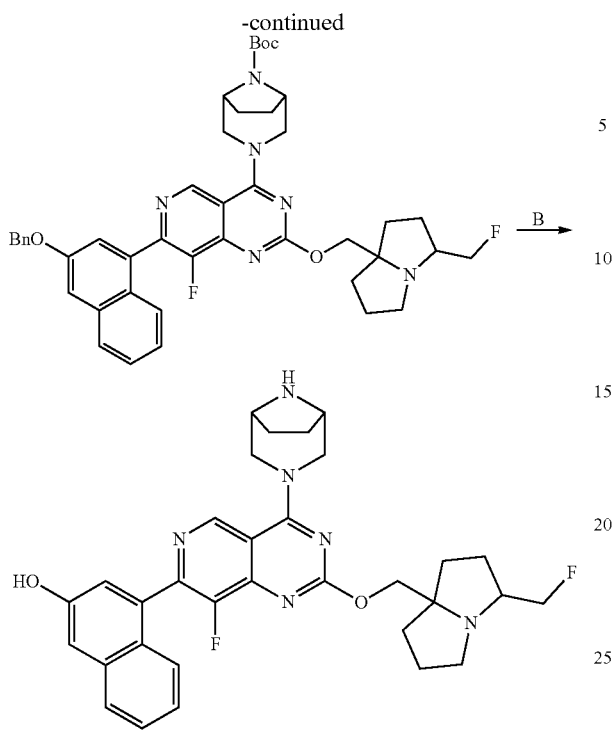

B→ modifier). The fractions containing product were pooled and partitioned between dichloromethane and saturated NaHCO₃. The organics were washed with brine, dried with Na₂SO₄, filtered, and concentrated to give 4-(4-((1R,5S)-3,8-diazabicyclo[3.2.1]octan-3-yl)-8-fluoro-2-((3-(fluoromethyl)tetrahydro-1H-pyrrolizin-7a(5H)-yl)methoxy)pyrido[4,3-d]pyrimidin-7-yl)naphthalen-2-ol (mixture of isomers) (3.5 mg, 25%). LCMS (MM-ES+APCI, Pos): m/z 573.3 (M+H).

Example 385

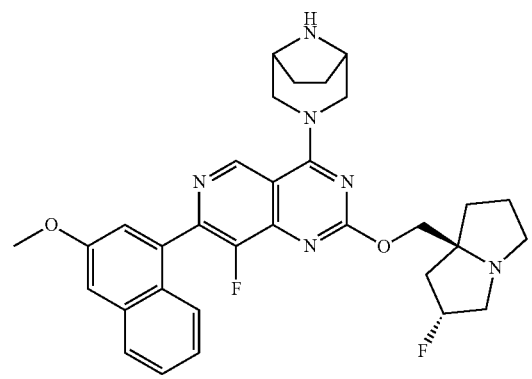 [SMILES: COc1cc(-c2ncc3c(N4CC5CCC(C4)N5)nc(OC[C@@]45CCCN4C[C@H](F)C5)nc3c2F)c2ccccc2c1]

4-((1R,5S)-3,8-diazabicyclo[3.2.1]octan-3-yl)-8-fluoro-2-((2-fluorotetrahydro-1H-pyrrolizin-7a(5H)-yl)methoxy)-7-(3-methoxynaphthalen-1-yl)pyrido[4,3-d]pyrimidine (racemic, trans)

Synthesized according to Example 3, Steps G-H substituting (2-fluorotetrahydro-1H-pyrrolizin-7a(5H)-yl)methanol (racemic, trans) in place of 2-(1-methyl-1H-imidazol-2-yl)ethan-1-ol in Step G and (3-methoxynaphthalen-1-yl)boronic acid in place of 4-(4,4,5,5-tetramethyl-1,3,2-dioxaborolan-2-yl)naphthalen-2-ol in Step H followed by deprotection using Example 391, Step A to afford 4-((1R,5S)-3,8-diazabicyclo[3.2.1]octan-3-yl)-8-fluoro-2-((2-fluorotetrahydro-1H-pyrrolizin-7a(5H)-yl)methoxy)-7-(3-methoxynaphthalen-1-yl)pyrido[4,3-d]pyrimidine (racemic, trans) (38 mg, 85%). LCMS (MM-ES+APCI, Pos): m/z 573.3 (M+H).

Example 386

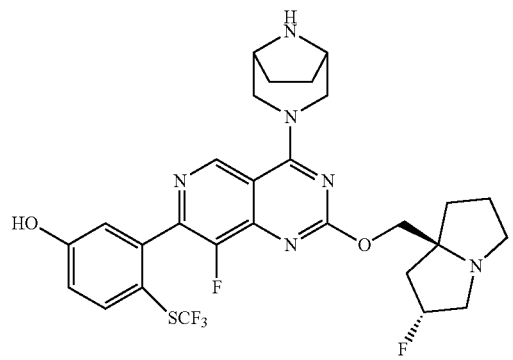

Step A. Tert-butyl (1R,5S)-3-(7-(3-(benzyloxy)naphthalen-1-yl)-8-fluoro-2-669'C3 (fluoromethyl)tetrahydro-1H-pyrrolizin-7a(5H)-yl)methoxy)pyrido[4,3-d]pyrimidin-4-yl)-3,8-diazabicyclo[3.2.1]octane-8-carboxylate (mixture of isomers). A solution of (3-(fluoromethyl)tetrahydro-1H-pyrrolizin-7a(5H)-yl)methanol (mixture of isomers, synthesized according to Example 400, Step A-I, 10 mg, 0.06 mmol), tert-butyl (1R,5S)-3-(7-(3-(benzyloxy)naphthalen-1-yl)-2-chloro-8-fluoropyrido[4,3-d]pyrimidin-4-yl)-3,8-diazabicyclo[3.2.1]octane-8-carboxylate (54 mg, 0.087 mmol), RuPhos Pd Gen3 precatalyst (5 mg, 0.006 mmol), and Cs₂CO₃ (75 mg, 0.23 mmol) in 1,4-dioxane (0.5 mL) was sparged with argon for 5 minutes and heated to 90° C. overnight in a sealed vial. The solution was purified by silica gel chromatography (1-20% MeOH/DCM with 1% NH₄OH as a modifier). The fractions containing the product were pooled and concentrated to give tert-butyl (1R,5S)-3-(7-(3-(benzyloxy)naphthalen-1-yl)-8-fluoro-2-((3-(fluoromethyl)tetrahydro-1H-pyrrolizin-7a(5H)-yl)methoxy)pyrido[4,3-d]pyrimidin-4-yl)-3,8-diazabicyclo[3.2.1]octane-8-carboxylate (mixture of isomers) (19 mg, 43%). LCMS (MM-ES+APCI, Pos): m/z 763.4 (M+H).

Step B. 4-(4-((1R,5S)-3,8-diazabicyclo[3.2.1]octan-3-yl)-8-fluoro-2-((3-(fluoromethyl)tetrahydro-1H-pyrrolizin-7a(5H)-yl)methoxy)pyrido[4,3-d]pyrimidin-7-yl)naphthalen-2-ol (mixture of isomers). To a solution of tert-butyl (1R,5S)-3-(7-(3-(benzyloxy)naphthalen-1-yl)-8-fluoro-2-((3-(fluoromethyl)tetrahydro-1H-pyrrolizin-7a(5H)-yl)methoxy)pyrido[4,3-d]pyrimidin-4-yl)-3,8-diazabicyclo[3.2.1]octane-8-carboxylate (mixture of isomers) (19 mg, 0.025 mmol) in dichloromethane (0.5 mL) at −78° C. was added 1,2,3,4,5-pentamethylbenzene (18 mg, 0.12 mmol) and trichloroborane (130 µL, 0.12 mmol). The solution was stirred for 30 minutes at −78° C. and 1 hour at 0° C. The solution was quenched with NaHCO₃ and partitioned with 4:1 DCM:IPA. The organics were washed with brine, dried with Na₂SO₄, filtered, concentrated, and purified by reverse-phase column (5-95% MeCN/water with 0.1% TFA as a

793

3-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-4-((trifluoromethyl)thio)phenol (racemic, trans)

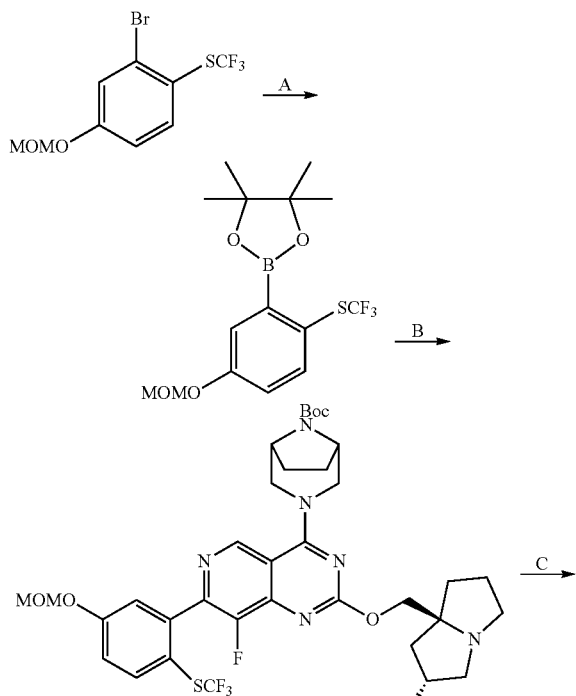

Step A. 2-(5-(methoxymethoxy)-2-((trifluoromethyl)thio)phenyl)-4,4,5,5-tetramethyl-1,3,2-dioxaborolane. Synthesized according to Example 399, Step E substituting (2-bromo-4-(methoxymethoxy)phenyl)(trifluoromethyl)sulfane in place of 2-isopropyl-5-(methoxymethoxy)phenyl trifluoromethanesulfonate to afford 2-(5-(methoxymethoxy)-2-((trifluoromethyl)thio)phenyl)-4,4,5,5-tetramethyl-1,3,2-dioxaborolane (50 mg, 55%). $^1$H NMR (400 MHz, CDCl$_3$): δ 7.60 (d, J=8.9 Hz, 1H), 7.35 (s, 1H), 7.10 (d, J=8.8 Hz, 1H), 5.21 (s, 2H), 3.47 (s, 3H), 1.37 (s, 12H).

Step B. Tert-butyl (1R,5S)-3-(8-fluoro-2-((2-fluorotetrahydro-1H-pyrrolizin-7a(5H)-yl)methoxy)-7-(5-(methoxymethoxy)-2-((trifluoromethyl)thio)phenyl)pyrido[4,3-d]pyrimidin-4-yl)-3,8-diazabicyclo[3.2.1]octane-8-carboxylate (racemic, trans). Synthesized according to Example 424, Step A substituting 2-(5-(methoxymethoxy)-2-((trifluoromethyl)thio)phenyl)-4,4,5,5-tetramethyl-1,3,2-dioxaborolane in place of 2-(5-(benzyloxy)-2-(2,2,2-trifluoroethyl)phenyl)-4,4,5,5-tetramethyl-1,3,2-dioxaborolane to afford tert-butyl (1R,5S)-3-(8-fluoro-2-((2-fluorotetrahydro-1H-pyrrolizin-7a(5H)-yl)methoxy)-7-(5-(methoxymethoxy)-2-((trifluoromethyl)thio)phenyl)pyrido[4,3-d]pyrimidin-4-yl)-3,8-diazabicyclo[3.2.1]octane-8-carboxylate (racemic, trans) (49 mg, 72%). LCMS (MM-ES+APCI, Pos): m/z 753.3 (M+H).

Step C. 3-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-4-((trifluoromethyl)thio)phenol (racemic, trans). Synthesized according to Example 422, Step B substituting tert-butyl (1R,5S)-3-(8-fluoro-2-((2-fluorotetrahydro-1H-pyrrolizin-7a(5H)-yl)methoxy)-7-(5-(methoxymethoxy)-2-((trifluoromethyl)thio)phenyl)pyrido[4,3-d]pyrimidin-4-yl)-3,8-diazabicyclo[3.2.1]octane-8-carboxylate (racemic, trans) in place of tert-butyl (1R,5S)-3-(8-fluoro-2-((tetrahydro-1H-pyrrolizin-7a(5H)-yl)methoxy)-7-(8-(trifluoromethyl)naphthalen-1-yl)pyrido[4,3-d]pyrimidin-4-yl)-3,8-diazabicyclo[3.2.1]octane-8-carboxylate to afford 3-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-4-((trifluoromethyl)thio)phenol (racemic, trans) (29 mg, 73%). LCMS (MM-ES+APCI, Pos): m/z 609.2 (M+H).

Example 387

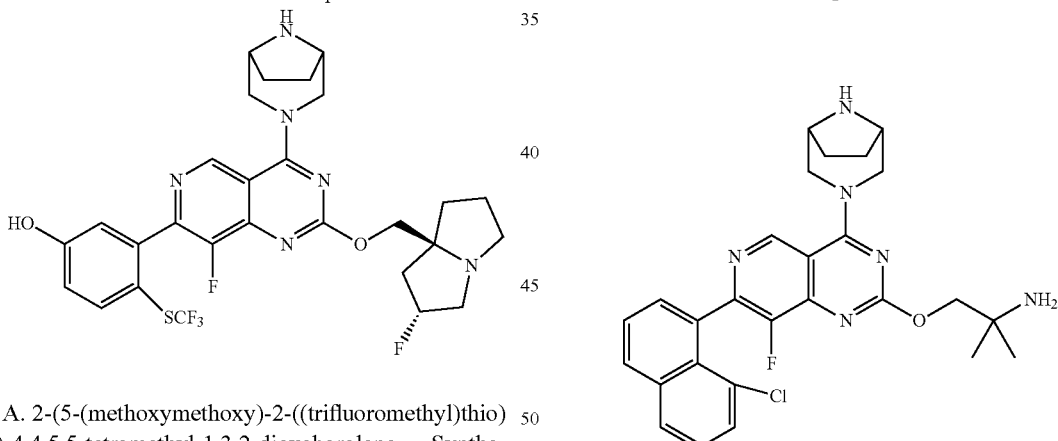

(S)-1-((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)propan-2-amine bis(2,2,2-trifluoroacetate)

Synthesized according to Example 29, Step H substituting N-Boc-2-amino-2-methyl-1-propanol in place of (S)-(1-isopropylpyrrolidin-2-yl) methanol followed by deprotection using Example 2, Step I, (28 mg, 30%). LCMS (MM-ES+APCI, Pos): m/z 507.2 (M+H).

Example 388

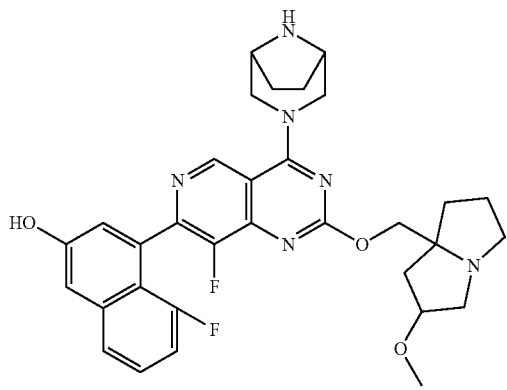 [SMILES: COC1CN2CCCC2(COc2nc(N3CC4CCC(C3)N4)c3cnc(-c4cc(O)cc5cccc(F)c45)c(F)c3n2)C1]

4-(4-((1R,5S)-3,8-diazabicyclo[3.2.1]octan-3-yl)-8-fluoro-2-((2-methoxytetrahydro-1H-pyrrolizin-7a(5H)-yl)methoxy)pyrido[4,3-d]pyrimidin-7-yl)-5-fluoronaphthalen-2-ol (mixture of trans diastereomers)

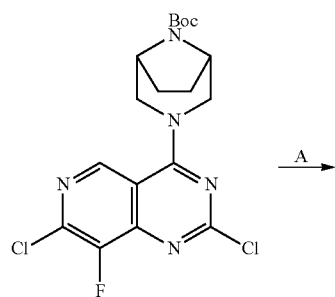

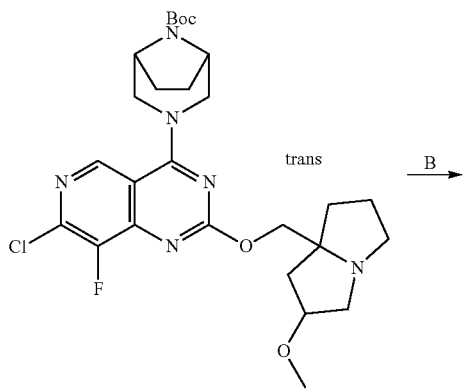

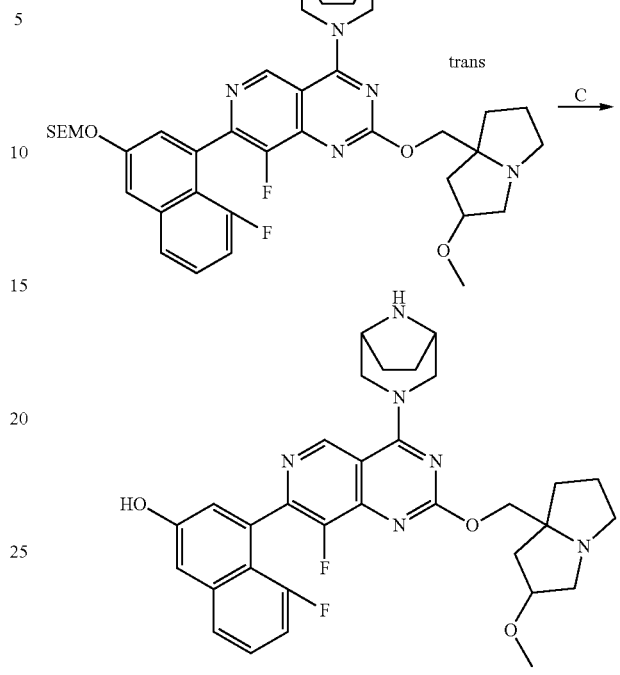

Step A. tert-butyl (1R,5S)-3-(7-chloro-8-fluoro-2-((2-methoxytetrahydro-1H-pyrrolizin-7a(5H)-yl)methoxy)pyrido[4,3-d]pyrimidin-4-yl)-3,8-diazabicyclo[3.2.1]octane-8-carboxylate (mixture of trans diastereomers). Tert-butyl (1R,5S)-3-(2,7-dichloro-8-fluoropyrido[4,3-d]pyrimidin-4-yl)-3,8-diazabicyclo[3.2.1]octane-8-carboxylate (0.18 g, 0.41 mmol), (2-methoxytetrahydro-1H-pyrrolizin-7a(5H)-yl)methanol (mixture of trans diastereomers, synthesized according to Example 219, Step A-C, 70 mg, 0.41 mmol), and cesium carbonate (0.40 g, 1.2 mmol) were added to a vial with a stir bar and septa cap. The vial was degassed and purged with $N_2$ 3 times before dioxane (4.1 mL) was added. The reaction was heated to 95° C. for 18 hours. The reaction was diluted with water and extracted with DCM 3 times. The DCM layers were combined, dried with $Na_2SO_4$, filtered, and concentrated. The residue was purified by flash chromatography (silica, 0-20% MeOH in DCM) to yield tert-butyl (1R,5S)-3-(7-chloro-8-fluoro-2-((2-methoxytetrahydro-1H-pyrrolizin-7a(5H)-yl)methoxy)pyrido[4,3-d]pyrimidin-4-yl)-3,8-diazabicyclo[3.2.1]octane-8-carboxylate (mixture of trans diastereomers) (99 mg, 43%). LCMS (MM-ES+APCI, Pos): m/z 563.3 (M+H).

Step B. tert-butyl (1R,5S)-3-(8-fluoro-7-(8-fluoro-3-((2-(trimethylsilyl)ethoxy)methoxy)naphthalen-1-yl)-2-((2-methoxytetrahydro-1H-pyrrolizin-7a(5H)-yl)methoxy)pyrido[4,3-d]pyrimidin-4-yl)-3,8-diazabicyclo[3.2.1]octane-8-carboxylate (mixture of trans diastereomers). Tert-butyl (1R,5S)-3-(7-chloro-8-fluoro-2-((2-methoxytetrahydro-1H-pyrrolizin-7a(5H)-yl)methoxy)pyrido[4,3-d]pyrimidin-4-yl)-3,8-diazabicyclo[3.2.1]octane-8-carboxylate (mixture of trans diastereomers) (42 mg, 0.075 mmol), (2-(((5-fluoro-4-(4,4,5,5-tetramethyl-1,3,2-dioxaborolan-2-yl)naphthalen-2-yl)oxy)methoxy)ethyl)trimethylsilane (46 mg, 0.11 mmol, synthesized according to Example 366, Step A-F), and XPhos Pd G2 (12 mg, 0.015 mmol) were added to a vial with a stir bar. The vial was degassed and purged with N₂ 3 times before degassed THF (0.15 mL) and degassed 0.5 M aqueous K₃PO₄ (0.3 mL, 0.15 mmol) were added. The reaction was heated to 40° C. for 1.5 hours. The reaction was diluted with water and extracted with DCM 3 times. The DCM layers were combined, dried with Na₂SO₄, filtered, and concentrated. The residue was purified by flash chromatography (silica, 0-20% MeOH in DCM) to yield tert-butyl (1R,5S)-3-(8-fluoro-7-(8-fluoro-3-((2-(trimethylsilyl)ethoxy)methoxy)naphthalen-1-yl)-2-((2-methoxytetrahydro-1H-pyrrolizin-7a(5H)-yl)methoxy) pyrido[4,3-d]pyrimidin-4-yl)-3,8-diazabicyclo[3.2.1] octane-8-carboxylate (mixture of trans diastereomers) (29 mg, 47%). LCMS (MM-ES+APCI, Pos): m/z 819.4 (M+H).

Step C. 4-(4-((1R,5S)-3,8-diazabicyclo[3.2.1]octan-3-yl)-8-fluoro-2-((2-methoxytetrahydro-1H-pyrrolizin-7a(5H)-yl) methoxy)pyrido[4,3-d]pyrimidin-7-yl)-5-fluoronaphthalen-2-ol bis(2,2,2-trifluoroacetate) (mixture of trans diastereomers). Tert-butyl (1R,5S)-3-(8-fluoro-7-(8-fluoro-3-((2-(trimethylsilyl)ethoxy)methoxy)naphthalen-1-yl)-2-((2-methoxytetrahydro-1H-pyrrolizin-7a(5H)-yl)methoxy) pyrido[4,3-d]pyrimidin-4-yl)-3,8-diazabicyclo[3.2.1] octane-8-carboxylate (mixture of trans diastereomers) (29 mg, 0.035 mmol) was added to a round bottom flask with a stir bar. DCM (1 mL) and TFA (0.5 mL) were added at room temperature and the reaction was stirred for 1 hour. The reaction was concentrated to dryness and the residue was purified via reverse phase chromatography (C18, 0-80% MeCN in water with 0.1% TFA). The fractions containing the product were combined, frozen, and lyophilized to yield 4-(4-((1R,5S)-3,8-diazabicyclo[3.2.1]octan-3-yl)-8-fluoro-2-((2-methoxytetrahydro-1H-pyrrolizin-7a(5H)-yl) methoxy)pyrido[4,3-d]pyrimidin-7-yl)-5-fluoronaphthalen-2-ol bis(2,2,2-trifluoroacetate) (mixture of trans diastereomers) (21 mg, 71%). LCMS (MM-ES+APCI, Pos): m/z 589.3 (M+H).

Example 389

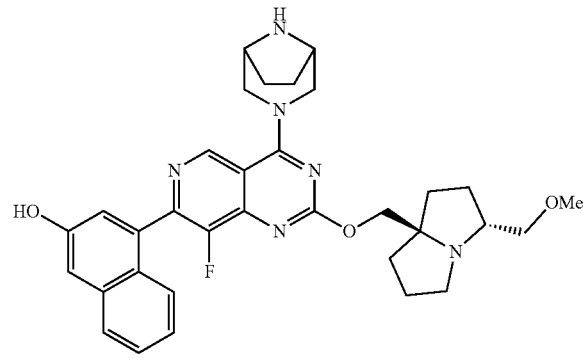 [SMILES: COC[C@H]1CC[C@@]2(COc3nc(N4CC5CCC(C4)N5)c4cnc(-c5cc(O)cc6ccccc56)c(F)c4n3)CCCN12]

4-(4-((1R,5S)-3,8-diazabicyclo[3.2.1]octan-3-yl)-8-fluoro-2-((3-(methoxymethyl)tetrahydro-1H-pyrrolizin-7a(5H)-yl)methoxy)pyrido[4,3-d]pyrimidin-7-yl)naphthalen-2-ol (mixture of trans diastereomers)

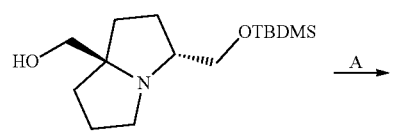

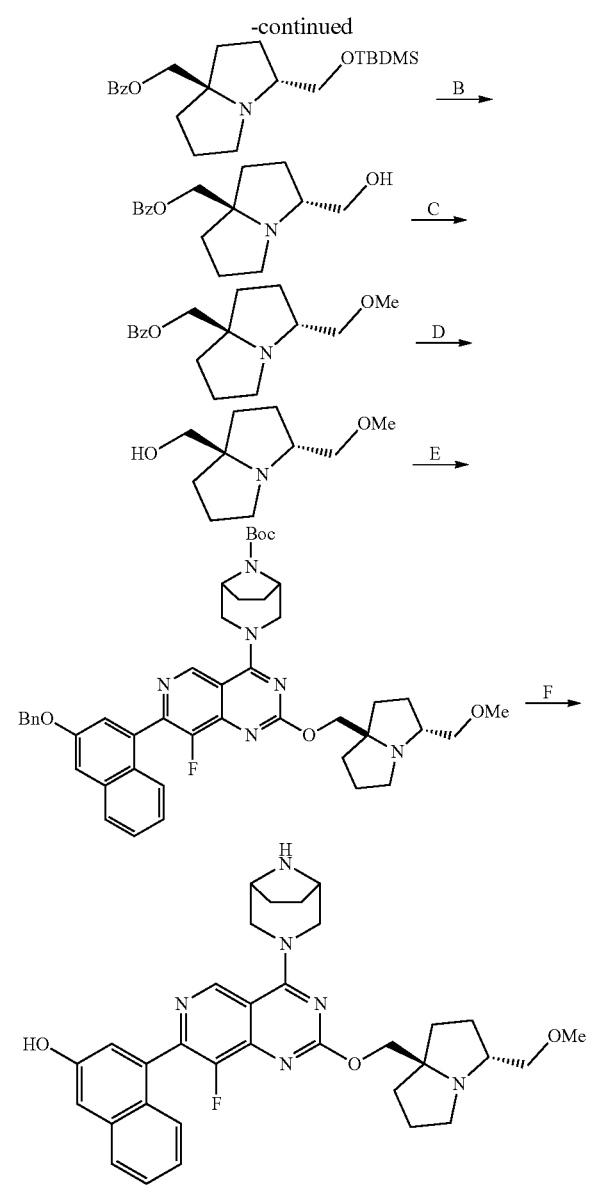

Step A. (3-(((tert-butyldimethylsilyl)oxy)methyl)tetrahydro-1H-pyrrolizin-7a(5H)-yl)methyl benzoate (mixture of trans diastereomers). To a solution of (3-(((tert-butyldimethylsilyl)oxy)methyl)tetrahydro-1H-pyrrolizin-7a(5H)-yl) methanol (mixture of trans diastereomers) (0.30 g, 1.1 mmol) and triethylamine (0.59 mL, 4.2 mmol) in dichloromethane (5 mL) at 0° C. was added benzoyl chloride (0.24 mL, 2.1 mmol) and the reaction was stirred at room temperature for 1 hour. The solution was partitioned between dichloromethane and saturated NaHCO₃. The organics were washed with brine, dried with Na₂SO₄, filtered, concentrated, and purified by silica gel chromatography (1-10% MeOH/DCM with 1% NH₄OH as a modifier) to give (3-(((tert-butyldimethylsilyl)oxy)methyl)tetrahydro-1H-pyrrolizin-7a(5H)-yl)methyl benzoate (mixture of trans diastereomers) (0.23 g, 56%). LCMS (MM-ES+APCI, Pos): m/z 390.2 (M+H).

Step B. (3-(hydroxymethyl)tetrahydro-1H-pyrrolizin-7a (5H)-yl)methyl benzoate (mixture of trans diastereomers). To a solution of (3-(((tert-butyldimethylsilyl)oxy)methyl) tetrahydro-1H-pyrrolizin-7a(5H)-yl)methyl benzoate (racemic, trans) (0.23 g, 0.59 mmol) in THF (3 mL) was added 1M tetrabutylammonium fluoride (1.2 mL, 1.2 mmol) and the reaction stirred for 1 hour. The solution was concentrated and purified by silica gel chromatography (1-20% MeOH/DCM with 1% NH₄OH as modifier) to give (3-(hydroxymethyl)tetrahydro-1H-pyrrolizin-7a(5H)-yl)methyl benzoate (mixture of trans diastereomers) (147 mg, 90%). LCMS (MM-ES+APCI, Pos): m/z 276.2 (M+H).

Step C. (3-(methoxymethyl)tetrahydro-1H-pyrrolizin-7a (5H)-yl)methyl benzoate (mixture of trans diastereomers). To a solution of (3-(hydroxymethyl)tetrahydro-1H-pyrrolizin-7a(5H)-yl)methyl benzoate (mixture of trans diastereomers) (44 mg, 0.16 mmol) in tetrahydrofuran (1 mL) at 0° C. was added 60% sodium hydride in mineral oil (13 mg, 0.32 mmol). The reaction was stirred at 0° C. for 10 minutes. Iodomethane (10 µL, 0.16 mmol) was added and the solution was stirred at room temperature for 30 minutes. The solution was partitioned between dichloromethane and saturated NaHCO₃. The organics were concentrated and purified by silica gel chromatography (1-20% MeOH/DCM with 1% NH₄OH as modifier) to give (3-(methoxymethyl)tetrahydro-1H-pyrrolizin-7a(5H)-yl)methyl benzoate (mixture of trans diastereomers) (3.2 mg, 7%). LCMS (MM-ES+APCI, Pos): m/z 290.2 (M+H).

Step D. (3-(methoxymethyl)tetrahydro-1H-pyrrolizin-7a (5H)-yl)methanol (mixture of trans diastereomers). To a solution of (3-(methoxymethyl)tetrahydro-1H-pyrrolizin-7a (5H)-yl)methyl benzoate (mixture of trans diastereomers) (3.2 mg, 0.011 mmol) in tetrahydrofuran (0.1 mL) at 0° C. was added 1M LiAlH₄ (44 µL, 0.044 mmol) and the reaction was stirred at 0° C. for 30 minutes. The reaction was diluted with diethyl ether (0.1 mL), and cooled to 0° C. Water (10 µL), 15% NaOH (15 µL), and water (30 µL) were added and the slurry was stirred at room temperature for 15 minutes. MgSO₄ was added and the slurry was stirred for 15 minutes. The slurry was filtered and the filtrate was evaporated under a stream of nitrogen to give (3-(methoxymethyl)tetrahydro-1H-pyrrolizin-7a(5H)-yl)methanol (mixture of trans diastereomers) (2.0 mg, 98%). LCMS (MM-ES+APCI, Pos): m/z 186.2 (M+H).

Step E. Tert-butyl (1R,5S)-3-(7-(3-(benzyloxy)naphthalen-1-yl)-8-fluoro-2-((3-(methoxymethyl)tetrahydro-1H-pyrrolizin-7a(5H)-yl)methoxy)pyrido[4,3-d]pyrimidin-4-yl)-3,8-diazabicyclo[3.2.1]octane-8-carboxylate (mixture of trans diastereomers). A solution of (3-(methoxymethyl)tetrahydro-1H-pyrrolizin-7a(5H)-yl)methanol (mixture of trans diastereomers) (5.8 mg, 0.031 mmol), tert-butyl (1R, 5S)-3-(7-(3-(benzyloxy)naphthalen-1-yl)-2-chloro-8-fluoropyrido[4,3-d]pyrimidin-4-yl)-3,8-diazabicyclo[3.2.1]octane-8-carboxylate (59 mg, 0.094 mmol), RuPhos Pd Gen3 precatalyst (2.6 mg, 0.0031 mmol), and Cs₂CO₃ (41 mg, 0.13 mmol) in 1,4-dioxane (0.5 mL) was sparged with argon for 5 minutes and heated to 90° C. overnight in a sealed vial. The solution was purified by silica gel chromatography (1-10% MeOH/DCM with 1% NH₄OH as a modifier) to give tert-butyl (1R,5S)-3-(7-(3-(benzyloxy)naphthalen-1-yl)-8-fluoro-2-((3-(methoxymethyl)tetrahydro-1H-pyrrolizin-7a(5H)-yl)methoxy)pyrido[4,3-d]pyrimidin-4-yl)-3,8-diazabicyclo[3.2.1]octane-8-carboxylate (mixture of trans diastereomers) (13 mg, 54%). LCMS (MM-ES+APCI, Pos): m/z 775.4 (M+H).

Step F. 4-(4-((1R,5S)-3,8-diazabicyclo[3.2.1]octan-3-yl)-8-fluoro-2-((3-(methoxymethyl)tetrahydro-1H-pyrrolizin-7a(5H)-yl)methoxy)pyrido[4,3-d]pyrimidin-7-yl)naphthalen-2-ol (mixture of trans diastereomers). To a solution of tert-butyl (1R,5S)-3-(7-(3-(benzyloxy)naphthalen-1-yl)-8-fluoro-2-((3-(methoxymethyl)tetrahydro-1H-pyrrolizin-7a (5H)-yl)methoxy)pyrido[4,3-d]pyrimidin-4-yl)-3,8-diazabicyclo[3.2.1]octane-8-carboxylate (mixture of trans diastereomers) (13 mg, 0.017 mmol) in dichloromethane (0.5 mL) at −78° C. was added 1,2,3,4,5-pentamethylbenzene (12 mg, 0.084 mmol) and trichloroborane (84 µL, 0.084 mmol). The solution was stirred for 30 minutes at −78° C. and for 1 hour at 0° C. The solution was quenched with NaHCO₃ and partitioned with 4:1 DCM/IPA. The organics were washed with brine, dried with Na₂SO₄, filtered, concentrated, and purified by reverse-phase column (5-95% MeCN/water with 0.1% TFA as modifier). Fractions containing product were pooled and lyophilized to give 4-(4-((1R,5S)-3,8-diazabicyclo[3.2.1]octan-3-yl)-8-fluoro-2-((3-(methoxymethyl)tetrahydro-1H-pyrrolizin-7a(5H)-yl) methoxy)pyrido[4,3-d]pyrimidin-7-yl)naphthalen-2-ol (mixture of trans diastereomers) (7.7 mg, 79%). LCMS (MM-ES+APCI, Pos): m/z 585.3 (M+H).

Example 390

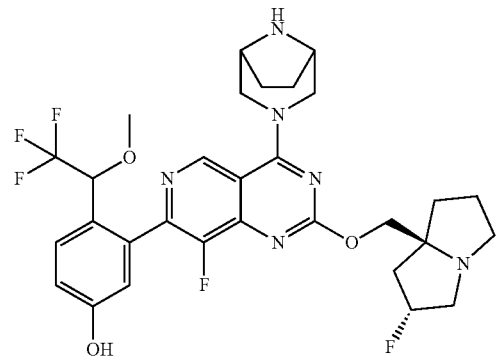 [SMILES: COC(c1ccc(O)cc1-c1ncc2c(N3CC4CCC(C3)N4)nc(OC[C@@]34CCCN3C[C@H](F)C4)nc2c1F)C(F)(F)F]

3-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-4-(2,2,2-trifluoro-1-methoxyethyl)phenol (racemic, trans)

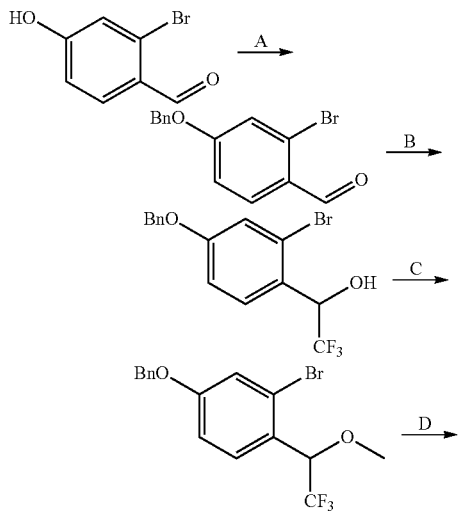

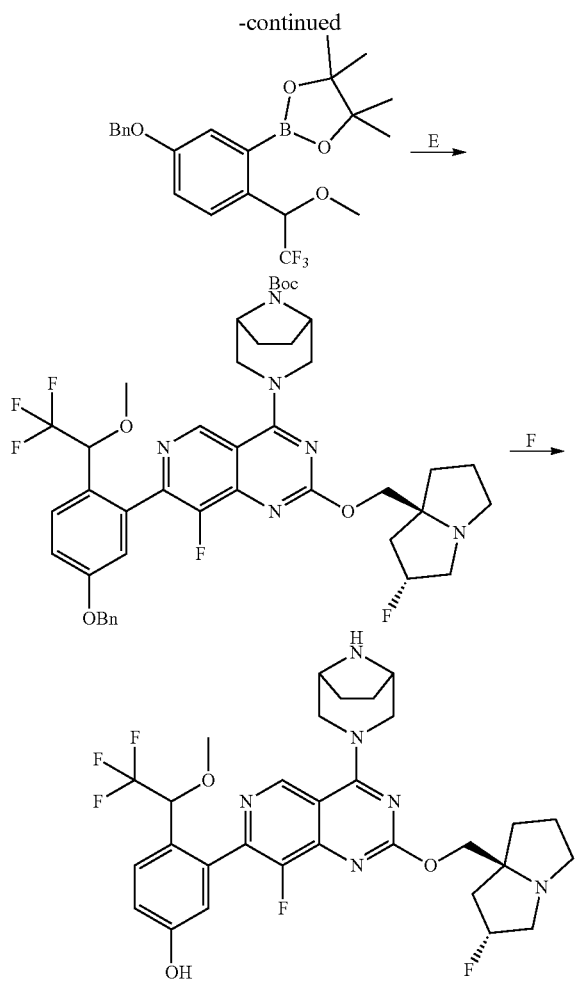

Step A. 4-benzyloxy-2-bromo-benzaldehyde. To a solution of 2-bromo-4-hydroxy-benzaldehyde (25 g, 124 mmol) in DMF (250 mL) was added K₂CO₃ (51.6 g, 373 mmol). The mixture was stirred at 25° C. for 0.5 h and BnBr (25.5 g, 149 mmol) was added. The mixture was stirred at 25° C. for 2 h. The suspension was filtered and the filter cake was washed with EtOAc (200 mL). The filtrate was diluted with water (750 mL). The mixture was transferred to a separatory funnel, and the aqueous layer mixture was extracted with ethyl acetate (200 mL×2). The combined organic layers were washed with brine (100 mL), dried over anhydrous sodium sulfate, filtered, and concentrated under reduced pressure. The crude product was purified by silica gel column chromatography eluting with 3+10% ethyl acetate/pet. ether to give the desired product (30 g, 83% yield) as yellow solid. ¹H NMR (400 MHz, CDCl₃) δ 10.23 (d, J=0.8 Hz, 1H), 7.90 (d, J=8.8 Hz, 1H), 7.48-7.33 (m, 5H), 7.24 (d, J=2.4 Hz, 1H), 7.01 (dd, J=2.0, 8.8 Hz, 1H), 5.14 (s, 2H)

Step B. 1-(4-benzyloxy-2-bromo-phenyl)-2,2,2-trifluoro-ethanol. To a solution of 4-benzyloxy-2-bromo-benzaldehyde (30 g, 103 mmol) in THF (300 mL) was added TBAF (1 M, 155 mL) at 25° C. The mixture was cooled to 0° C. and TMSCF₃ (43.0 g, 309 mmol) was added dropwise at 0° C. The mixture was warmed to 25° C. and stirred for 1 h. The suspension was filtered and the filter cake was washed with EtOAc (200 mL). The filtrate was diluted with water (500 mL). The mixture was transferred to a separatory funnel, and the aqueous layer was extracted with ethyl acetate (100 mL×2). The combined organic layers were washed with brine (40 mL), dried over anhydrous sodium sulfate, filtered, and concentrated under reduced pressure. The crude product was purified by silica gel column chromatography eluting with 3+10% ethyl acetate/pet. ether to give the desired product (25 g, 67% yield) as a yellow solid.

Step C. 4-benzyloxy-2-bromo-1-(2,2,2-trifluoro-1-methoxy-ethyl)benzene. To a solution of 1-(4-benzyloxy-2-bromo-phenyl)-2,2,2-trifluoro-ethanol (3.3 g, 9.14 mmol) in THF (30 mL) was added NaH (548 mg, 60% dispersion in mineral oil, 13.7 mmol) at 0° C. The mixture was warmed to 25° C. and stirred for 0.5 h. CH₃I (2.59 g, 18.3 mmol) was added. The mixture was stirred at 25° C. for 12 h. The reaction was quenched by addition of saturated aqueous ammonium chloride (20 mL). The mixture was transferred to a separatory funnel, and the aqueous layer was extracted with ethyl acetate (50 mL×2). The combined organic layers were washed with brine (10 mL), dried over anhydrous sodium sulfate, filtered, and concentrated under reduced pressure. The crude product was purified by silica gel column chromatography with 0+3% ethyl acetate/pet. ether to give 4-benzyloxy-2-bromo-1-(2,2,2-trifluoro-1-methoxy-ethyl)benzene (2.1 g, 61% yield) as a white solid. ¹H NMR (400 MHz, CDCl₃) δ 7.50 (d, J=8.8 Hz, 1H), 7.46-7.34 (m, 5H), 7.24 (d, J=2.4 Hz, 1H), 7.02 (dd, J=2.4, 8.8 Hz, 1H), 5.13-5.04 (m, 3H), 3.40 (s, 3H).

Step D. 2-[5-benzyloxy-2-(2,2,2-trifluoro-1-methoxy-ethyl)phenyl]-4,4,5,5-tetramethyl-1,3,2-dioxaborolane. To a 100 mL round-bottom flask equipped with a magnetic stir bar were added 4-benzyloxy-2-bromo-1-(2,2,2-trifluoro-1-methoxy-ethyl)benzene (4.7 g, 12.53 mmol) and 4,4,5,5-tetramethyl-2-(4,4,5,5-tetramethyl-1,3,2-dioxaborolan-2-yl)-1,3,2-dioxaborolane (3.82 g, 15.0 mmol) followed by the addition of 1,4-dioxane (50 mL). KOAc (3.69 g, 37.6 mmol) and cyclopentyl(diphenyl)phosphane; dichloropalladium; iron (917 mg, 1.25 mmol) were added. The flask was evacuated and backfilled with nitrogen three times. The mixture was stirred at 95° C. under an atmosphere of nitrogen for 12 h. The suspension was filtrated and the filter cake was washed with ethyl acetate (20 mL). The filtrate was concentrated under reduced pressure to give the crude product. The crude product was purified by silica gel column chromatography eluting with 0→2% ethyl acetate/pet. ether to give 2-[5-benzyloxy-2-(2,2,2-trifluoro-1-methoxy-ethyl)phenyl]-4,4,5,5-tetramethyl-1,3,2-dioxaborolane (1.15 g, 21% yield) as a white solid. ¹H NMR (400 MHz, CDCl₃) δ 7.58 (d, J=8.8 Hz, 1H), 7.50 (d, J=2.8 Hz, 1H), 7.48-7.44 (m, 2H), 7.43-7.32 (m, 3H), 7.12 (dd, J=2.8, 8.8 Hz, 1H), 5.64 (q, J=6.8 Hz, 1H), 5.10 (s, 2H), 3.42 (s, 3H), 1.36 (s, 12H).

Step E. Tert-butyl (1R,5S)-3-(7-(5-(benzyloxy)-2-(2,2,2-trifluoro-1-methoxyethyl)phenyl)-8-fluoro-2-((2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (racemic, trans). Synthesized according to Example 424, Step A substituting 2-(5-(benzyloxy)-2-(2,2,2-trifluoro-1-methoxyethyl)phenyl)-4,4,5,5-tetramethyl-1,3,2-dioxaborolane in place of 2-(5-(benzyloxy)-2-(2,2,2-trifluoroethyl)phenyl)-4,4,5,5-tetramethyl-1,3,2-dioxaborolane to afford tert-butyl (1R,5S)-3-(7-(5-(benzyloxy)-2-(2,2,2-trifluoro-1-methoxyethyl)phenyl)-8-fluoro-2-((2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (racemic, trans) (40 mg, 54%). LCMS (MM-ES+APCI, Pos): m/z 811.3 (M+H).

Step F. 3-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-4-(2,2,2-trifluoro-1- methoxyethyl)phenol (racemic, trans). Synthesized according to Example 424, Step B substituting tert-butyl (1R,5S)-3-(7-(5-(benzyloxy)-2-(2,2,2-trifluoro-1-methoxyethyl)phenyl)-8-fluoro-2-((2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (racemic, trans) in place of tert-butyl (1R,5S)-3-(7-(5-(benzyloxy)-2-(2,2,2-trifluoroethyl)phenyl)-8-fluoro-2-((2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (racemic, trans) to afford 3-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-4-(2,2,2-trifluoro-1-methoxyethyl)phenol (racemic, trans) (10 mg, 26%). LCMS (MM-ES+APCI, Pos): m/z 621.3 (M+H).

Example 391

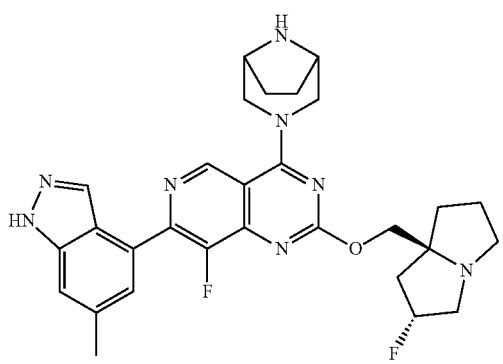 [SMILES: Cc1cc(-c2ncc3c(N4CC5CCC(C4)N5)nc(OC[C@@]45CCCN4C[C@H](F)C5)nc3c2F)c2cn[nH]c2c1]

4-((1R,5S)-3,8-diazabicyclo[3.2.1]octan-3-yl)-8-fluoro-2-((2-fluorotetrahydro-1H-pyrrolizin-7a(5H)-yl)methoxy)-7-(6-methyl-1H-indazol-4-yl)pyrido[4,3-d]pyrimidine (racemic, trans)

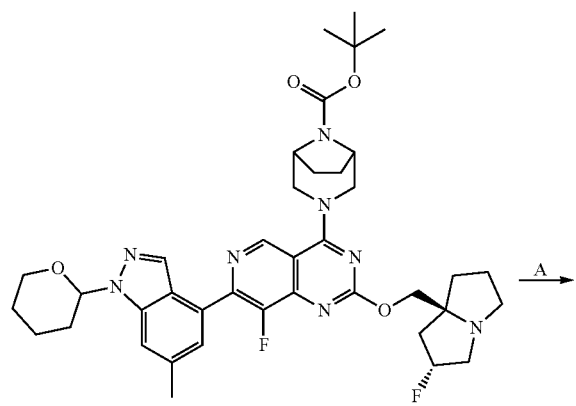

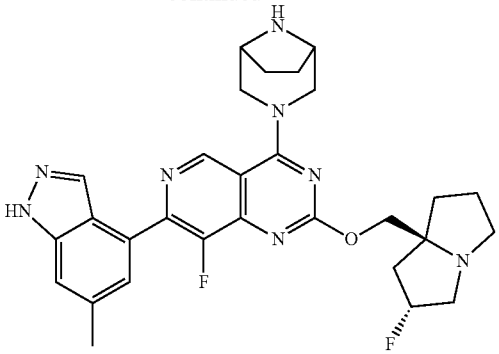

Synthesized according to Example 3, Steps G-H substituting (2-fluorotetrahydro-1H-pyrrolizin-7a(5H)-yl)methanol (racemic, trans) in place of 2-(1-methyl-1H-imidazol-2-yl)ethan-1-ol in Step G and 6-methyl-1-(tetrahydro-2H-pyran-2-yl)-4-(4,4,5,5-tetramethyl-1,3,2-dioxaborolan-2-yl)-1H-indazole in place of 4-(4,4,5,5-tetramethyl-1,3,2-dioxaborolan-2-yl)naphthalen-2-ol in Step H to afford tert-butyl (1R,5S)-3-(8-fluoro-2-((2-fluorotetrahydro-1H-pyrrolizin-7a(5H)-yl)methoxy)-7-(6-methyl-1-(tetrahydro-2H-pyran-2-yl)-1H-indazol-4-yl)pyrido[4,3-d]pyrimidin-4-yl)-3,8-diazabicyclo[3.2.1]octane-8-carboxylate (racemic, trans) (34 mg, 52%). LCMS (MM-ES+APCI, Pos): m/z 731.4 (M+H).

Step A. 4-((1R,5S)-3,8-diazabicyclo[3.2.1]octan-3-yl)-8-fluoro-2-((2-fluorotetrahydro-1H-pyrrolizin-7a(5H)-yl)methoxy)-7-(6-methyl-1H-indazol-4-yl)pyrido[4,3-d]pyrimidine (racemic, trans). To a solution of tert-butyl (1R,5S)-3-(8-fluoro-2-((2-fluorotetrahydro-1H-pyrrolizin-7a(5H)-yl)methoxy)-7-(6-methyl-1-(tetrahydro-2H-pyran-2-yl)-1H-indazol-4-yl)pyrido[4,3-d]pyrimidin-4-yl)-3,8-diazabicyclo[3.2.1]octane-8-carboxylate (racemic, trans) (34 mg, 0.048 mmol) in DCM (1 mL) was added 4 M HCl in dioxane (1 ml, 4 mmol). After stirring for 2.5 hours at room temperature, more 4 M HCl in dioxane (1 ml, 4 mmol) was added. After 7 hours the reaction was concentrated in vacuo. The residue was purified by reverse phase chromatography eluting with 5-95% MeCN/water to afford 4-((1R,5S)-3,8-diazabicyclo[3.2.1]octan-3-yl)-8-fluoro-2-((2-fluorotetrahydro-1H-pyrrolizin-7a(5H)-yl)methoxy)-7-(6-methyl-1H-indazol-4-yl)pyrido[4,3-d]pyrimidine (racemic, trans) (13 mg, 51%) as a yellow foam. LCMS (MM-ES+APCI, Pos): m/z 547.3 (M+H).

Example 392

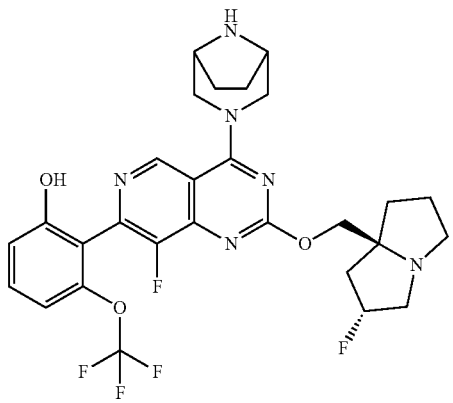 [SMILES: Oc1cccc(OC(F)(F)F)c1-c1ncc2c(N3CC4CCC(C3)N4)nc(OC[C@@]34CCCN3C[C@H](F)C4)nc2c1F]

2-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-3-(trifluoromethoxy)phenol (racemic, trans)

Step A. Tert-butyl (1R,5S)-3-(8-fluoro-2-((2-fluorotetrahydro-1H-pyrrolizin-7a(5H)-yl)methoxy)-7-(2-hydroxy-6-(trifluoromethoxy)phenyl)pyrido[4,3-d]pyrimidin-4-yl)-3,8-diazabicyclo[3.2.1]octane-8-carboxylate (racemic, trans). Synthesized according to Example 424, Step A substituting 2-(4,4,5,5-tetramethyl-1,3,2-dioxaborolan-2-yl)-3-(trifluoromethoxy)phenol in place of 2-(5-(benzyloxy)-2-(2,2,2-trifluoroethyl)phenyl)-4,4,5,5-tetramethyl-1,3,2-dioxaborolane to afford tert-butyl (1R,5S)-3-(8-fluoro-2-((2-fluorotetrahydro-1H-pyrrolizin-7a(5H)-yl)methoxy)-7-(2-hydroxy-6-(trifluoromethoxy)phenyl)pyrido[4,3-d]pyrimidin-4-yl)-3,8-diazabicyclo[3.2.1]octane-8-carboxylate (racemic, trans) (40 mg, 64%). LCMS (MM-ES+APCI, Pos): m/z 693.3 (M+H).

Step B. 2-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-3-(trifluoromethoxy)phenol (racemic, trans). Synthesized according to Example 422, Step B substituting tert-butyl (1R,5S)-3-(8-fluoro-2-((2-fluorotetrahydro-1H-pyrrolizin-7a(5H)-yl)methoxy)-7-(2-hydroxy-6-(trifluoromethoxy)phenyl)pyrido[4,3-d]pyrimidin-4-yl)-3,8-diazabicyclo[3.2.1]octane-8-carboxylate (racemic, trans) in place of tert-butyl (1R,5S)-3-(8-fluoro-2-((tetrahydro-1H-pyrrolizin-7a(5H)-yl)methoxy)-7-(8-(trifluoromethyl)naphthalen-1-yl)pyrido[4,3-d]pyrimidin-4-yl)-3,8-diazabicyclo[3.2.1]octane-8-carboxylate to afford 2-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-3-(trifluoromethoxy)phenol (racemic, trans) (14 mg, 86%). LCMS (MM-ES+APCI, Pos): m/z 593.3 (M+H).

Example 393

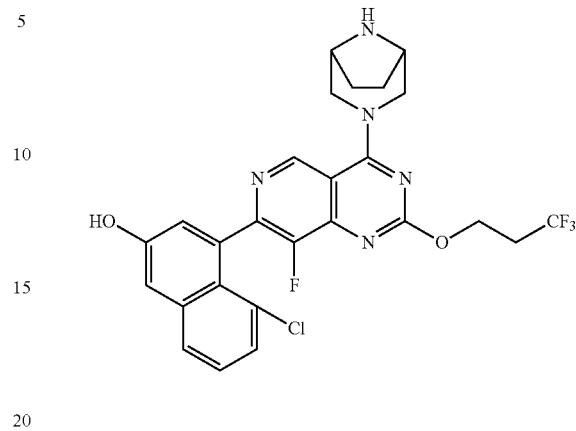

4-(4-((1R,5S)-3,8-diazabicyclo[3.2.1]octan-3-yl)-8-fluoro-2-(3,3,3-trifluoropropoxy)pyrido[4,3-d]pyrimidin-7-yl)-5-chloronaphthalen-2-ol Synthesized according to Example 36, substituting 4-((1R,5S)-3,8-diazabicyclo[3.2.1]octan-3-yl)-7-chloro-8-fluoro-2-(3,3,3-trifluoropropoxy)pyrido[4,3-d]pyrimidine in place of tert-butyl (1R,5S)-3-(7-chloro-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate in Step F to afford 4-(4-((1R,5S)-3,8-diazabicyclo[3.2.1]octan-3-yl)-8-fluoro-2-(3,3,3-trifluoropropoxy)pyrido[4,3-d]pyrimidin-7-yl)-5-chloronaphthalen-2-ol (10 mg, 74%). LCMS (MM-ES+APCI, Pos): m/z 548.2 [M+H].

Example 394

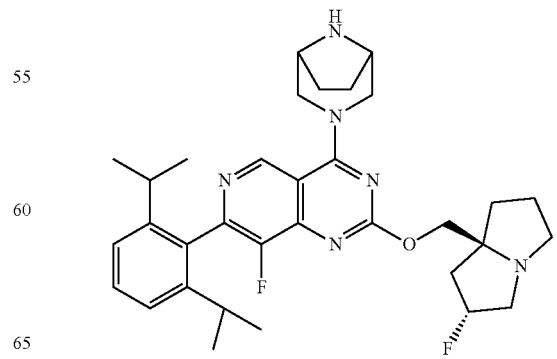

807

4-((1R,5S)-3,8-diazabicyclo[3.2.1]octan-3-yl)-7-(2,6-diisopropylphenyl)-8-fluoro-2-((2-fluorotetrahydro-1H-pyrrolizin-7a(5H)-yl)methoxy)pyrido[4,3-d]pyrimidine (racemic, trans)

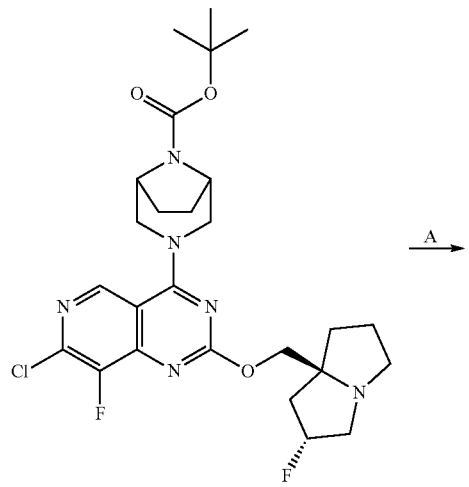

A →

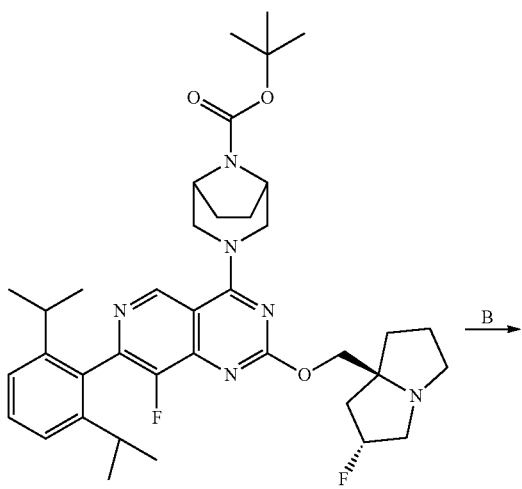

B →

808

Step A. tert-butyl (1R,5S)-3-(7-(2,6-diisopropylphenyl)-8-fluoro-2-((2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (racemic, trans): A mixture of tert-butyl (1R,5S)-3-(7-chloro-8-fluoro-2-((2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (racemic, trans) (50 mg, 0.09 mmol), (2,6-diisopropylphenyl)boronic acid (37 mg, 0.18 mmol), PdCl$_2$(PPh$_3$)$_2$ (6.4 mg, 0.009 mmol), and Cs$_2$CO$_3$ (89 mg, 0.27 mmol) in dioxane (1 mL) was degassed with Ar for 5 minutes. The reaction was sealed and stirred at 80° C. for 16 hours. The mixture was partitioned between water (10 mL) and EtOAc (10 mL) and the aqueous layer was extracted with EtOAc (2×10 mL). The combined organic phases were washed with brine (10 mL), dried over Na$_2$SO$_4$, filtered, and concentrated. The residue was purified by flash column chromatography eluting with 0-10% MeOH/DCM to afford tert-butyl (1R,5S)-3-(7-(2,6-diisopropylphenyl)-8-fluoro-2-((2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (racemic, trans) (38 mg 62%). LCMS (MM-ES+APCI, Pos): m/z 677.4 [M+H].

Step B. 4-((1R,5S)-3,8-diazabicyclo[3.2.1]octan-3-yl)-7-(2,6-diisopropylphenyl)-8-fluoro-2-((2-fluorotetrahydro-1H-pyrrolizin-7a(5H)-yl)methoxy)pyrido[4,3-d]pyrimidine (racemic, trans): To a solution of tert-butyl (1R,5S)-3-(7-(2,6-diisopropylphenyl)-8-fluoro-2-((2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (racemic, trans) (38 mg, 0.056 mmol) in DCM (1 mL) was added 4N HCl (1 mL). The mixture was stirred at ambient temperature for 2 hours and concentrated. The residue was dissolved in methanol (0.5 mL) and freebased by filtering through an Agilent MP carbonate frit, rinsing 3× with methanol. The filtrate was concentrated to afford 4-((1R,5S)-3,8-diazabicyclo[3.2.1]octan-3-yl)-7-(2,6-diisopropylphenyl)-8-fluoro-2-((2-fluorotetrahydro-1H-pyrrolizin-7a(5H)-yl)methoxy)pyrido[4,3-d]pyrimidine (racemic, trans) (31 mg, 96%). LCMS (MM-ES+APCI, Pos): m/z 577.3 [M+H].

Example 395

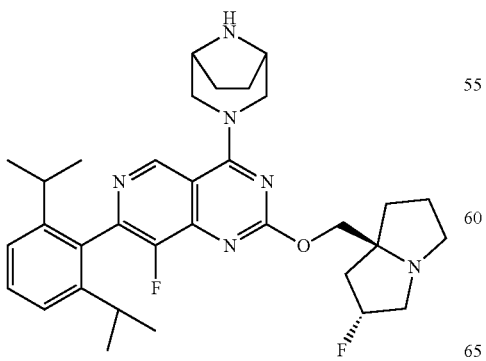

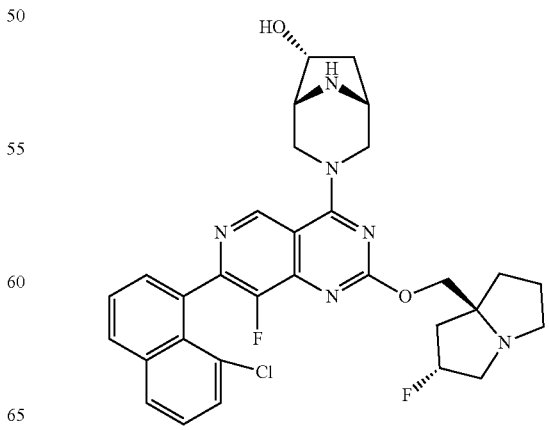

809

(1R,5R,6R)-3-(7-(8-chloronaphthalen-1-yl)-8-fluoro-2-((2-fluorotetrahydro-1H-pyrrolizin-7a(5H)-yl)methoxy)pyrido[4,3-d]pyrimidin-4-yl)-3,8-diazabicyclo[3.2.1]octan-6-ol (racemic, trans)

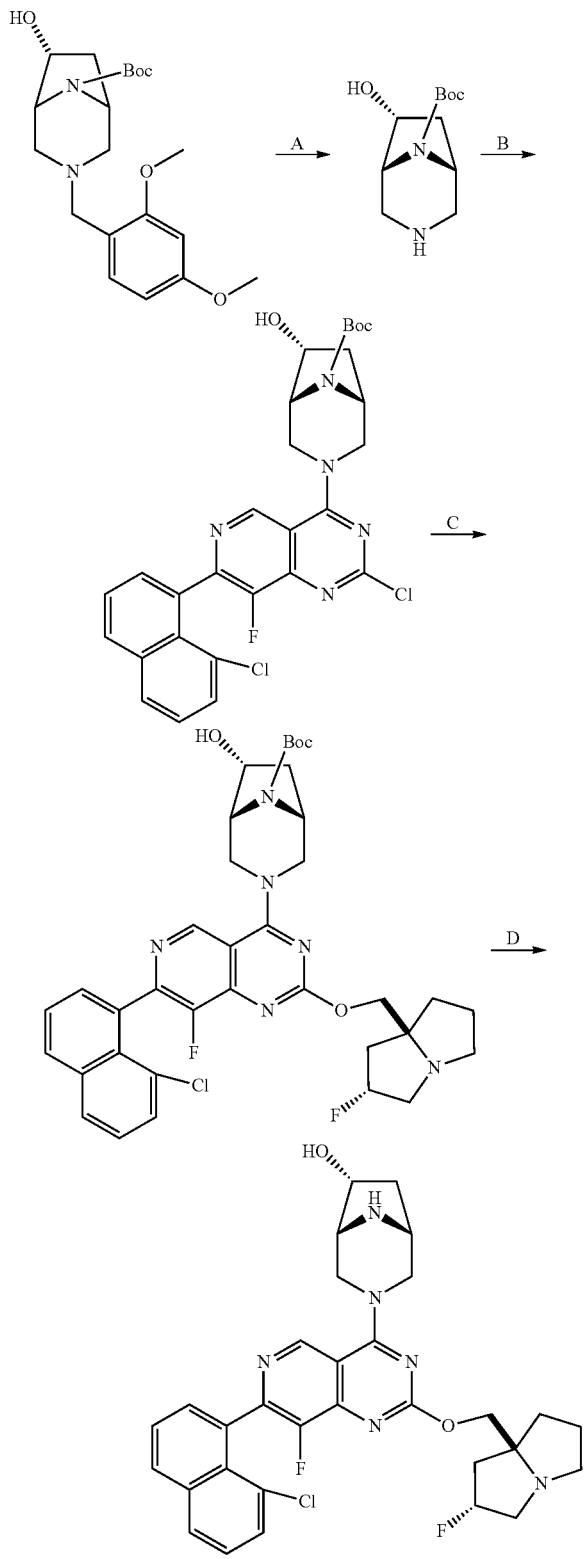

810

Step A. tert-butyl (1R,5R,6R)-6-hydroxy-3,8-diazabicyclo[3.2.1]octane-8-carboxylate: To a stirred solution of tert-butyl (1R,5R,6R)-3-(2,4-dimethoxybenzyl)-6-hydroxy-3,8-diazabicyclo[3.2.1]octane-8-carboxylate (0.30 g, 0.79 mmol, synthesized according to Example 31, Step A-D) in methanol (8 mL) was added 20% palladium hydroxide on carbon (0.10 g, 0.14 mmol). The reaction mixture was degassed with $N_2$ and a hydrogen atmosphere (from a balloon) was introduced. The reaction was stirred under $H_2$ for 3 hours. The reaction mixture was filtered through Celite and the Celite was washed with MeOH (3*2 mL). The filtrate was evaporated in vacuo. The residue was dissolved in MTBE and filtered through a cotton plug. The filtrate was evaporated under a stream of nitrogen to give tert-butyl (1R,5R,6R)-6-hydroxy-3,8-diazabicyclo[3.2.1]octane-8-carboxylate which was used as crude in the next reaction. LCMS (MM-ES+APCI, Pos): m/z 229.3 (M+H).

Step B. tert-butyl (1R,5R,6R)-3-(2-chloro-7-(8-chloronaphthalen-1-yl)-8-fluoropyrido[4,3-d]pyrimidin-4-yl)-6-hydroxy-3,8-diazabicyclo[3.2.1]octane-8-carboxylate. To a solution of 2,4-dichloro-7-(8-chloronaphthalen-1-yl)-8-fluoropyrido[4,3-d]pyrimidine (0.16 g, 0.42 mmol) in DCM (4 mL) at rt was added tert-butyl (1R,5R,6R)-6-hydroxy-3,8-diazabicyclo[3.2.1]octane-8-carboxylate (80 mg, 0.35 mmol) followed by $Et_3N$ (59 μL, 0.42 mmol). The solution was stirred at r.t. for 0.5 h. The mixture was concentrated, and the residue was purified by flash chromatography eluting with ethyl acetate/hexanes (0-100%) to give the title compound (0.17 g, 86%) as a light yellow solid. LCMS (MM-ES+APCI, Pos): m/z 570.2 (M+H).

Step C. tert-butyl (1R,5R,6R)-3-(7-(8-chloronaphthalen-1-yl)-8-fluoro-2-((2-fluorotetrahydro-1H-pyrrolizin-7a(5H)-yl)methoxy)pyrido[4,3-d]pyrimidin-4-yl)-6-hydroxy-3,8-diazabicyclo[3.2.1]octane-8-carboxylate (racemic, trans). To a solution of tert-butyl (1R,5R,6R)-3-(2-chloro-7-(8-chloronaphthalen-1-yl)-8-fluoropyrido[4,3-d]pyrimidin-4-yl)-6-hydroxy-3,8-diazabicyclo[3.2.1]octane-8-carboxylate (0.17 g, 0.29 mmol) and (2-fluorotetrahydro-1H-pyrrolizin-7a(5H)-yl)methanol (racemic, trans) (0.14 g, 0.87 mmol) in THF (6 mL) at 0° C. was added NaH (60%, 29 mg, 0.72 mmol). The mixture was stirred at r.t. for 4 h and concentrated to about 1 mL. The mixture was purified by preparative C18 HPLC (Gilson, 0-95% $CH_3CN/H_2O$ with 0.1% TFA). The desired fractions were combined and concentrated to remove $CH_3CN$. The solution was basified with $NaHCO_3$ (sat.), extracted with ethyl acetate, dried ($Na_2SO_4$), and concentrated to give the title compound (0.10 g, 52%) as a white solid. LCMS (MM-ES+APCI, Pos): m/z 693.2 (M+H).

Step D. (1R,5R,6R)-3-(7-(8-chloronaphthalen-1-yl)-8-fluoro-2-((2-fluorotetrahydro-1H-pyrrolizin-7a(5H)-yl)methoxy)pyrido[4,3-d]pyrimidin-4-yl)-3,8-diazabicyclo[3.2.1]octan-6-ol bis(2,2,2-trifluoroacetate) (racemic, trans). To a solution of tert-butyl (1R,5R,6R)-3-(7-(8-chloronaphthalen-1-yl)-8-fluoro-2-((2-fluorotetrahydro-1H-pyrrolizin-7a(5H)-yl)methoxy)pyrido[4,3-d]pyrimidin-4-yl)-6-hydroxy-3,8-diazabicyclo[3.2.1]octane-8-carboxylate (racemic, trans) (7.0 mg, 0.010 mmol) in DCM (0.50 mL) was added TFA (0.25 mL). The mixture was stirred at r.t. for 20 min, concentrated, and was purified by preparative C18 HPLC (Gilson, 0-95% $CH_3CN/H_2O$ with 0.1% TFA). The desired fractions were combined and lyophilized to give the title compound (7.0 mg, 84%) as the bis TFA salt. LCMS (MM-ES+APCI, Pos): m/z 593.2 (M+H).

811

Example 396

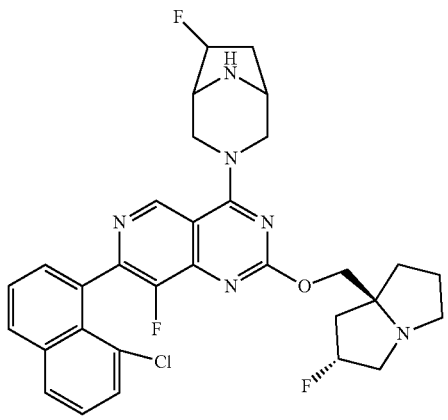 [SMILES: Fc1c(-c2cccc3cccc(Cl)c23)ncc2c(N3CC4CC(F)C(C3)N4)nc(OC[C@@]34CCCN3C[C@H](F)C4)nc12]

7-(8-chloronaphthalen-1-yl)-8-fluoro-4-(6-fluoro-3,8-diazabicyclo[3.2.1]octan-3-yl)-2-((2-fluorotetrahydro-1H-pyrrolizin-7a(5H)-yl)methoxy)pyrido[4,3-d]pyrimidine (racemic, trans)

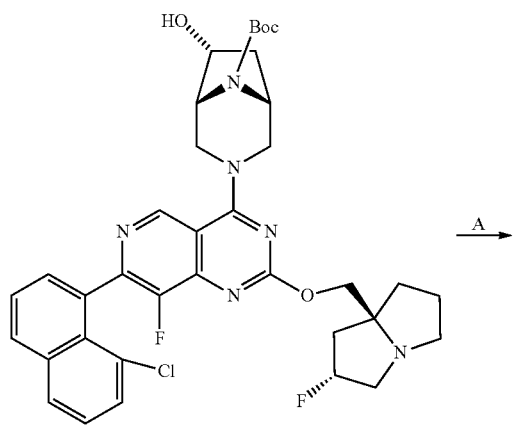

A→

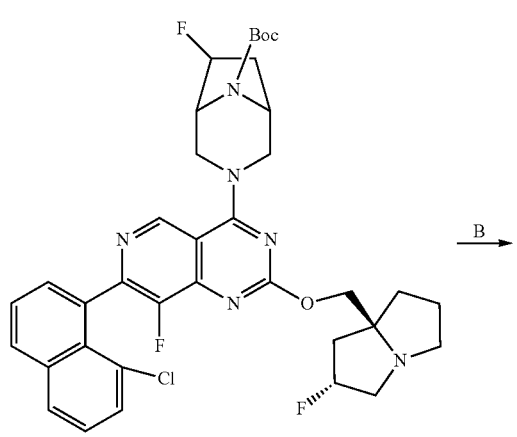

B→

812

-continued

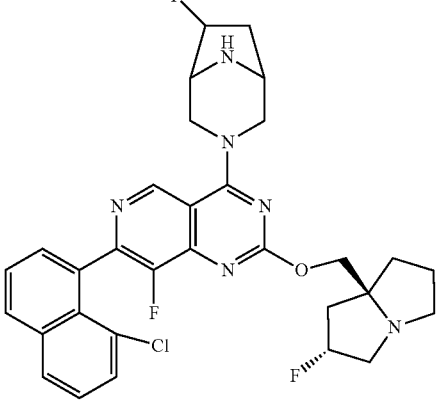

Step A. tert-butyl 3-(7-(8-chloronaphthalen-1-yl)-8-fluoro-2-((2-fluorotetrahydro-1H-pyrrolizin-7a(5H)-yl)methoxy)pyrido[4,3-d]pyrimidin-4-yl)-6-fluoro-3,8-diazabicyclo[3.2.1]octane-8-carboxylate (racemic, trans). To a solution of tert-butyl (1R,5R,6R)-3-(7-(8-chloronaphthalen-1-yl)-8-fluoro-2-((2-fluorotetrahydro-1H-pyrrolizin-7a (5H)-yl)methoxy)pyrido[4,3-d]pyrimidin-4-yl)-6-hydroxy-3,8-diazabicyclo[3.2.1]octane-8-carboxylate (racemic, trans) (36 mg, 0.052 mmol) in DCM (1 mL) at rt was added DAST (27 µL, 0.21 mmol). The mixture was stirred at rt for 3 h, concentrated, and the residue was purified by preparative C18 HPLC (Gilson, 0-95% CH$_3$CN/H$_2$O with 0.1% TFA). The desired fractions were combined, basified with NaHCO$_3$ (sat.), and extracted with ethyl acetate. The combined extract was washed with brine, dried (Na$_2$SO$_4$), and concentrated to give the impure title compound (14 mg, 39%) as a white solid. LCMS (MM-ES+APCI, Pos): m/z 695.3 (M+H).

Step B. 7-(8-chloronaphthalen-1-yl)-8-fluoro-4-(6-fluoro-3,8-diazabicyclo[3.2.1]octan-3-yl)-2-((2-fluorotetrahydro-1H-pyrrolizin-7a(5H)-yl)methoxy)pyrido[4,3-d]pyrimidine bis(2,2,2-trifluoroacetate) (racemic, trans). To a solution of tert-butyl 3-(7-(8-chloronaphthalen-1-yl)-8-fluoro-2-((2-fluorotetrahydro-1H-pyrrolizin-7a(5H)-yl)methoxy)pyrido[4,3-d]pyrimidin-4-yl)-6-fluoro-3,8-diazabicyclo[3.2.1]octane-8-carboxylate (racemic, trans) (5 mg, 0.007 mmol) in DCM (1 mL) was added TFA (0.5 mL). The solution was stirred at rt for 15 min, and concentrated to dryness. The residue was purified by preparative C18 HPLC (Gilson, 0-95% CH$_3$CN/H$_2$O with 0.1% TFA). The desired fractions were combined and lyophilized to give the title compound (2.0 mg, 34%) as the bis TFA salt. LCMS (MM-ES+APCI, Pos): m/z 595.2 (M+H).

Example 397

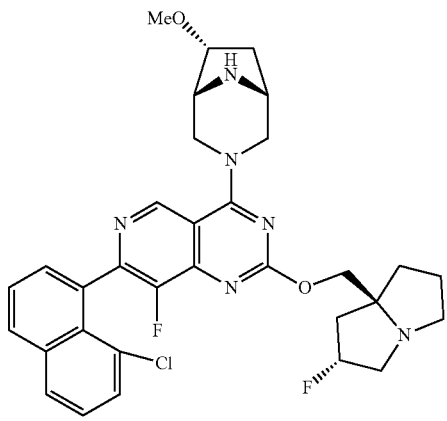 [SMILES: CO[C@@H]1C[C@@H]2CN(c3nc(OC[C@@]45CCCN4C[C@H](F)C5)nc4c(F)c(-c5cccc6cccc(Cl)c56)ncc34)C[C@H]1N2]

7-(8-chloronaphthalen-1-yl)-8-fluoro-2-((2-fluorotetrahydro-1H-pyrrolizin-7a(5H)-yl)methoxy)-4-((1R,5R,6R)-6-methoxy-3,8-diazabicyclo[3.2.1]octan-3-yl)pyrido[4,3-d]pyrimidine (racemic, trans)

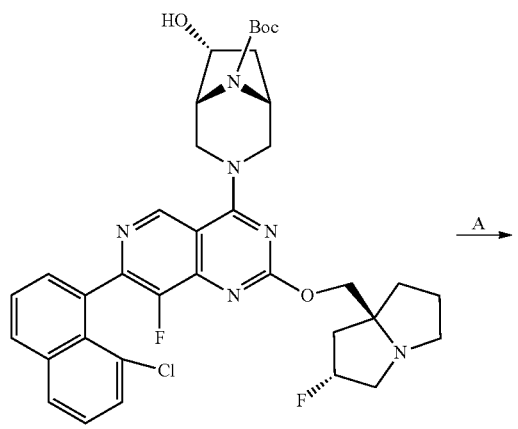

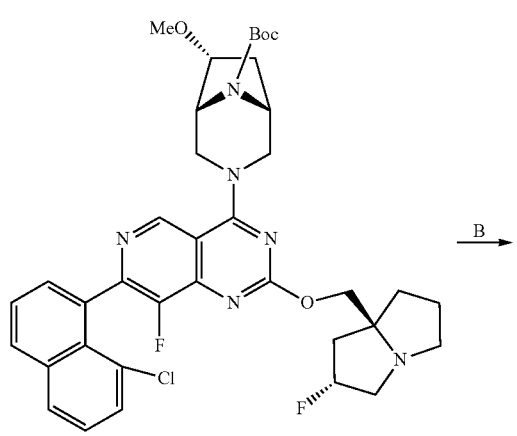

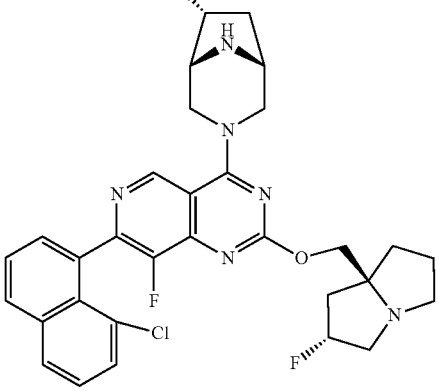

Step A. tert-butyl (1R,5R,6R)-3-(7-(8-chloronaphthalen-1-yl)-8-fluoro-2-((2-fluorotetrahydro-1H-pyrrolizin-7a(5H)-yl)methoxy)pyrido[4,3-d]pyrimidin-4-yl)-6-methoxy-3,8-diazabicyclo[3.2.1]octane-8-carboxylate (racemic, trans). To a solution of tert-butyl (1R,5R,6R)-3-(7-(8-chloronaphthalen-1-yl)-8-fluoro-2-((2-fluorotetrahydro-1H-pyrrolizin-7a(5H)-yl)methoxy)pyrido[4,3-d]pyrimidin-4-yl)-6-hydroxy-3,8-diazabicyclo[3.2.1]octane-8-carboxylate (racemic, trans) (24 mg, 0.035 mmol) in THF (0.7 mL) at rt was added MeI (13 µL, 0.20 mmol) followed by NaH (60%, 4.2 mg, 0.10 mmol). The mixture was stirred at r.t. for 1 h, concentrated, and was purified by preparative C18 HPLC (Gilson, 0-95% CH₃CN/H₂O with 0.1% TFA). The desired fractions were combined, basified with NaHCO₃ (sat.) and extracted with DCM. The combined extract was washed with brine, dried (Na₂SO₄), and concentrated to give the title compound (5.0 mg, 20%) as a white solid. LCMS (MM-ES+APCI, Pos): m/z 707.2 (M+H).

Step B. 7-(8-chloronaphthalen-1-yl)-8-fluoro-2-((2-fluorotetrahydro-1H-pyrrolizin-7a(5H)-yl)methoxy)-4-((1R,5R,6R)-6-methoxy-3,8-diazabicyclo[3.2.1]octan-3-yl)pyrido[4,3-d]pyrimidine bis(2,2,2-trifluoroacetate) (racemic, trans). To a solution of tert-butyl (1R,5R,6R)-3-(7-(8-chloronaphthalen-1-yl)-8-fluoro-2-((2-fluorotetrahydro-1H-pyrrolizin-7a(5H)-yl)methoxy)pyrido[4,3-d]pyrimidin-4-yl)-6-methoxy-3,8-diazabicyclo[3.2.1]octane-8-carboxylate (racemic, trans) (5.0 mg, 0.0071 mmol) in DCM (1 mL) was added TFA (0.50 mL). The solution was stirred at rt for 30 min, concentrated to dryness, and the residue was purified by preparative C18 HPLC (Gilson, 0-95% CH₃CN/H₂O with 0.1% TFA). The desired fractions were combined and lyophilized to give the title compound (3 mg, 51%) as the bis TFA salt. LCMS (MM-ES+APCI, Pos): m/z 607.2 (M+H).

Example 398

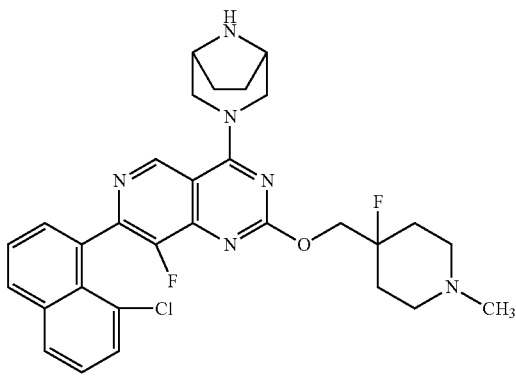 [SMILES: CN1CCC(F)(COc2nc(N3CC4CCC(C3)N4)c3cnc(-c4cccc5cccc(Cl)c45)c(F)c3n2)CC1]

4-((1R,5S)-3,8-diazabicyclo[3.2.1]octan-3-yl)-7-(8-chloronaphthalen-1-yl)-8-fluoro-2-((4-fluoro-1-methylpiperidin-4-yl)methoxy)pyrido[4,3-d]pyrimidine

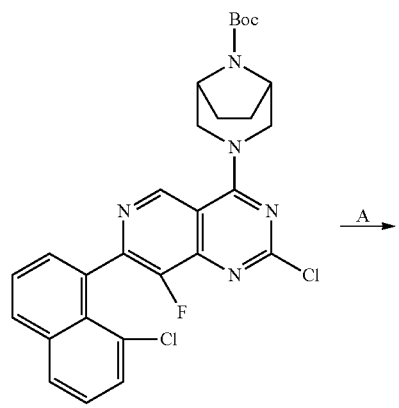

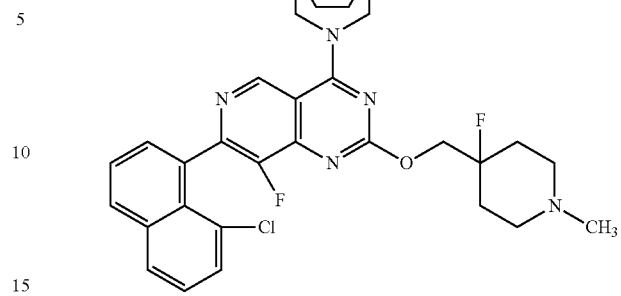

Step A. Tert-butyl (1R,5S)-3-(7-(8-chloronaphthalen-1-yl)-8-fluoro-2-((4-fluoro-1-methylpiperidin-4-yl)methoxy)pyrido[4,3-d]pyrimidin-4-yl)-3,8-diazabicyclo[3.2.1]octane-8-carboxylate. A mixture of tert-butyl (1R,5S)-3-(2-chloro-7-(8-chloronaphthalen-1-yl)-8-fluoropyrido[4,3-d]pyrimidin-4-yl)-3,8-diazabicyclo[3.2.1]octane-8-carboxylate (50 mg, 0.090 mmol), (4-fluoro-1-methylpiperidin-4-yl)methanol (13 mg, 0.090 mmol), Cs$_2$CO$_3$ (88 mg, 0.27 mmol) and 1,4-dioxane (1 mL) under N$_2$ was stirred at 60° C. for 24 h. The reaction mixture was cooled to r.t. and partitioned between water (5 mL) and EtOAc (15 mL). The organic phase was washed with water (5 mL), washed with brine (5 mL), dried over Na$_2$SO$_4$, evaporated in vacuo, and chromatographed on silica gel in 4% MeOH+10% NH$_4$OH in DCM to yield the target product as colorless solid (37 mg, 62%). LCMS (MM-ES+APCI, Pos): m/z 665.3 (M+H).

Step B. 4-((1R,5S)-3,8-diazabicyclo[3.2.1]octan-3-yl)-7-(8-chloronaphthalen-1-yl)-8-fluoro-2-((4-fluoro-1-methylpiperidin-4-yl)methoxy)pyrido[4,3-d]pyrimidine. A stirred solution of tert-butyl (1R,5S)-3-(7-(8-chloronaphthalen-1-yl)-8-fluoro-2-((4-fluoro-1-methylpiperidin-4-yl)methoxy)pyrido[4,3-d]pyrimidin-4-yl)-3,8-diazabicyclo[3.2.1]octane-8-carboxylate (37 mg, 0.056 mmol) in dichloromethane (0.5 mL) was cooled to −20° C. and 4M hydrogen chloride in dioxane (1 mL, 4.0 mmol) was added. The reaction mixture was stirred for 1 h at r.t. and concentrated in vacuo. The residue was freebased by partitioning between sat. NaHCO$_3$ and DCM to yield the target compound (28 mg, 89%) as yellow solid. LCMS (MM-ES+APCI, Pos): m/z 565.2 (M+H).

Example 399

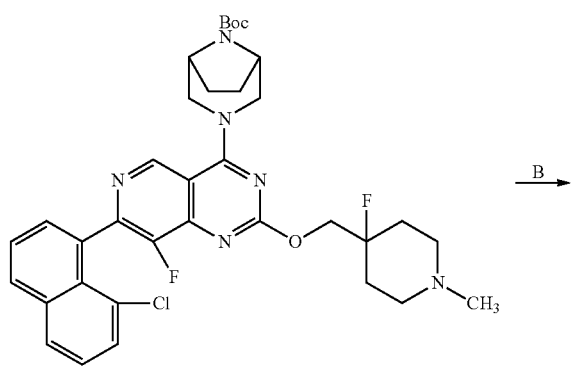

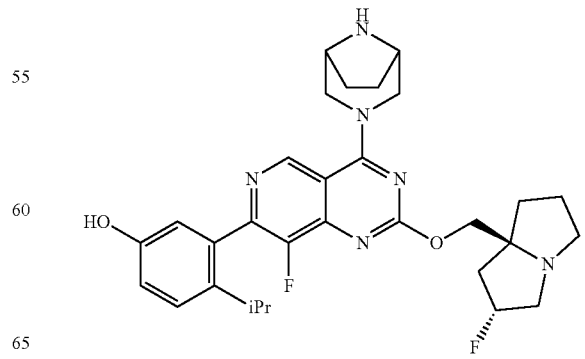

3-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-4-isopropylphenol (racemic, trans)

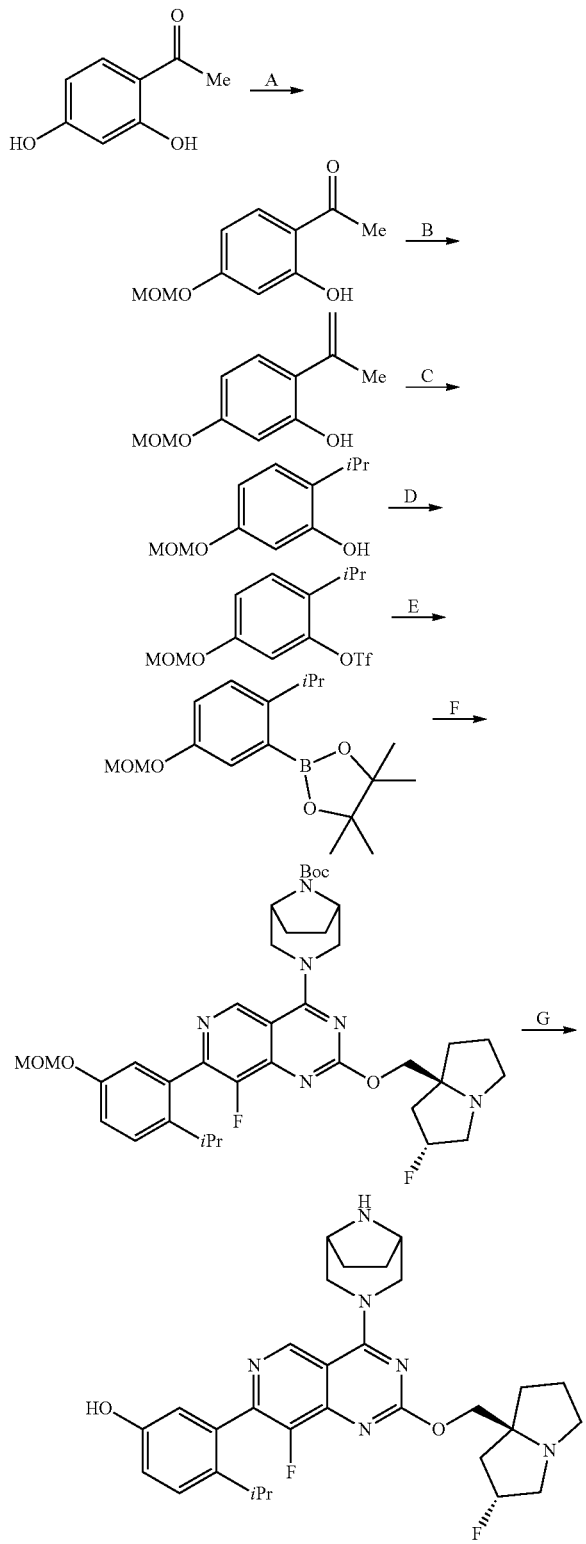

Step A. 1-(2-hydroxy-4-(methoxymethoxy)phenyl)ethan-1-one. 1-(2,4-Dihydroxyphenyl)ethan-1-one (1.0 g, 6.6 mmol) and N,N-diisopropylethylamine (2.9 mL, 16 mmol) were dissolved in DCM (20 mL). The mixture was cooled to 0° C. and chloromethyl methyl ether (0.75 mL, 9.9 mmol) was added. After stirred at room temperature for 1 hour, the reaction mixture was diluted with H₂O and EtOAc. The organics were separated and the aqueous was extracted with EtOAc. The combined organics were dried over MgSO₄ and condensed. The residue was purified by flash chromatography (24 g RediSep Gold column, 0-10% EtOAc/hexane) to afford 1-(2-hydroxy-4-(methoxymethoxy)phenyl)ethan-1-one (1.2 g, 89%). ¹H NMR (400 MHz, CDCl₃) δ: 12.62 (s, 1H), 7.66 (d, J=9.0 Hz, 1H), 6.60 (s, 1H), 6.55 (d, J=8.9 Hz, 1H), 5.21 (s, 2H), 3.48 (s, 3H), 2.58 (s, 3H).

Step B. 5-(methoxymethoxy)-2-(prop-1-en-2-yl)phenol. Methyltriphenylphosphonium bromide (2.2 g, 6.2 mmol) was suspended in diethyl ether (40.0 mL) and cooled to 0° C. Potassium tert-butoxide (1.4 g, 12 mmol) was added in one portion. After the mixture was stirred for 15 minutes, 1-(2-hydroxy-4-(methoxymethoxy)phenyl)ethan-1-one (1.2 g, 5.9 mmol) was added as a solution in diethyl ether (20 mL). The reaction was stirred at room temperature for 16 hours, quenched with saturated aqueous NH₄Cl, and extracted with DCM. The organics were separated, dried over MgSO₄, and condensed. The material was purified by flash chromatography (24 g RediSep Gold column, 0-15% EtOAc/hexanes) to afford 5-(methoxymethoxy)-2-(prop-1-en-2-yl)phenol (0.26 g, 23%). ¹H NMR (400 MHz, CDCl₃): δ 7.05 (d, J=8.6 Hz, 1H), 6.65 (d, J=2.6 Hz, 1H), 6.59 (dd, J=2.6, 8.4 Hz, 1H), 5.77 (s, 1H), 5.36 (m, 1H), 5.15 (s, 2H), 5.10 (br s, 1H), 3.48 (s, 3H), 2.09 (s, 3H).

Step C. 2-isopropyl-5-(methoxymethoxy)phenol. 5-(Methoxymethoxy)-2-(prop-1-en-2-yl)phenol (270 mg, 1.4 mmol) was dissolved in MeOH (20 mL) and the solution was purged with argon. 10% Palladium on carbon (0.15 g, 0.14 mmol) was added, the mixture was purged with hydrogen, and the reaction was stirred under a hydrogen atmosphere for 16 hours. The mixture was filtered through Celite and condensed to afford 2-isopropyl-5-(methoxymethoxy)phenol (0.20 g, 74%). ¹H NMR (400 MHz, CDCl₃): δ 7.08 (d, J=8.6 Hz, 1H), 6.60 (dd, J=2.4, 8.4 Hz, 1H), 6.50 (d, J=2.4 Hz, 1H), 5.13 (s, 2H), 4.77 (s, 1H), 3.47 (s, 3H), 3.16-3.09 (m, 1H), 1.23 (d, J=6.9 Hz, 6H).

Step D. 2-isopropyl-5-(methoxymethoxy)phenyl trifluoromethanesulfonate. A solution of 2-isopropyl-5-(methoxymethoxy)phenol (0.20 g, 1 mmol) and 2,6-lutidine (0.15 mL, 1.3 mmol) in DCM (5 mL) was cooled to −78° C. Trifluoromethanesulfonic anhydride (0.20 mL, 1.2 mmol) was added dropwise. The mixture was stirred for 1 hour at room temperature and quenched with saturated aqueous NaHCO₃. The organics were separated, condensed, and purified by flash chromatography (RediSep Gold 12 g column, 0-15% EtOAc/hexanes) to afford 2-isopropyl-5-(methoxymethoxy)phenyl trifluoromethanesulfonate (0.18 g, 54%). ¹H NMR (400 MHz, CDCl₃): δ 7.29 (d, J=8.5 Hz, 1H), 7.05 (dd, J=2.5, 8.8 Hz, 1H), 6.94 (d, J=2.5 Hz, 1H), 5.15 (s, 2H), 3.48 (s, 3H), 3.25-3.18 (m, 1H), 1.24 (d, J=6.9 Hz, 6H).

Step E. 2-(2-isopropyl-5-(methoxymethoxy)phenyl)-4,4,5,5-tetramethyl-1,3,2-dioxaborolane. 2-Isopropyl-5-(methoxymethoxy)phenyl trifluoromethanesulfonate (50 mg, 0.15 mmol), bis(pinacolato)diboron (58 mg, 0.23 mmol), and K₂CO₃ (45 mg, 0.46 mmol) were suspended in 1,4-dioxane (1 mL). After degassing with argon, [1,1′-bis(diphenylphosphino)ferrocene]dichloropalladium(II) dichloromethane adduct (12 mg, 0.015 mmol) was added.

The vial was sealed and heated to 90° C. for 2 hours. The mixture was cooled, filtered through Celite, condensed, and purified (RediSep Gold 12 g column, 0-10% EtOAc/hexanes) to afford 2-(2-isopropyl-5-(methoxymethoxy)phenyl)-4,4,5,5-tetramethyl-1,3,2-dioxaborolane (32 mg, 69%). $^1$H NMR (400 MHz, CDCl$_3$): δ 7.30 (d, J=2.9 Hz, 1H), 7.16 (d, J=8.6 Hz, 1H), 7.00 (dd, J=3.0, 8.6 Hz, 1H), 5.09 (s, 2H), 3.58-3.49 (m, 1H), 3.40 (s, 3H), 1.27 (s, 12H), 1.13 (d, J=6.9 Hz, 6H).

Step F. Tert-butyl (1R,5S)-3-(8-fluoro-2-((2-fluorotetrahydro-1H-pyrrolizin-7a(5H)-yl)methoxy)-7-(2-isopropyl-5-(methoxymethoxy)phenyl)pyrido[4,3-d]pyrimidin-4-yl)-3,8-diazabicyclo[3.2.1]octane-8-carboxylate (racemic, trans). Synthesized according to Example 424, Step A substituting 2-(2-isopropyl-5-(methoxymethoxy)phenyl)-4,4,5,5-tetramethyl-1,3,2-dioxaborolane in place of 2-(5-(benzyloxy)-2-(2,2,2-trifluoroethyl)phenyl)-4,4,5,5-tetramethyl-1,3,2-dioxaborolane to afford tert-butyl (1R,5S)-3-(8-fluoro-2-((2-fluorotetrahydro-1H-pyrrolizin-7a(5H)-yl)methoxy)-7-(2-isopropyl-5-(methoxymethoxy)phenyl)pyrido[4,3-d]pyrimidin-4-yl)-3,8-diazabicyclo[3.2.1]octane-8-carboxylate (racemic, trans) (30 mg, 53%). LCMS (MM-ES+APCI, Pos): m/z 695.4 (M+H).

Step G. 3-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-4-isopropylphenol dihydrochloride (racemic, trans). Synthesized according to Example 229, Step B substituting tert-butyl (1R,5S)-3-(8-fluoro-2-((2-fluorotetrahydro-1H-pyrrolizin-7a(5H)-yl)methoxy)-7-(2-isopropyl-5-(methoxymethoxy)phenyl)pyrido[4,3-d]pyrimidin-4-yl)-3,8-diazabicyclo[3.2.1]octane-8-carboxylate (racemic, trans) in place of tert-butyl (1R,5S)-3-(8-fluoro-2-((tetrahydro-1H-pyrrolizin-7a(5H)-yl)methoxy)-7-(2-(trifluoromethoxy)phenyl)pyrido[4,3-d]pyrimidin-4-yl)-3,8-diazabicyclo[3.2.1]octane-8-carboxylate to afford 3-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-4-isopropylphenol dihydrochloride (racemic, trans) (10 mg, 37%). LCMS (MM-ES+APCI, Pos): m/z 551.3 (M+H).

Example 400

4-(4-((1R,5S)-3,8-diazabicyclo[3.2.1]octan-3-yl)-8-fluoro-2-((3-(fluoromethyl)tetrahydro-1H-pyrrolizin-7a(5H)-yl)methoxy)pyrido[4,3-d]pyrimidin-7-yl)-5-chloronaphthalen-2-ol (mixture of isomers)

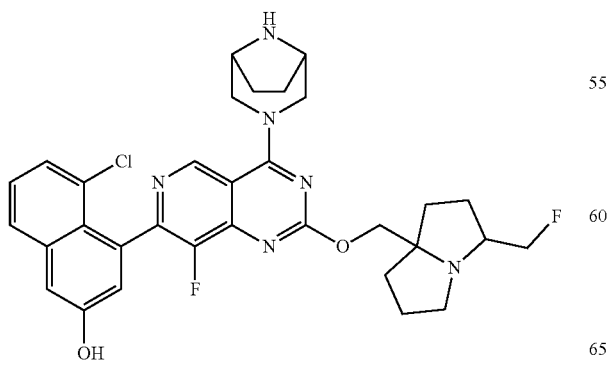

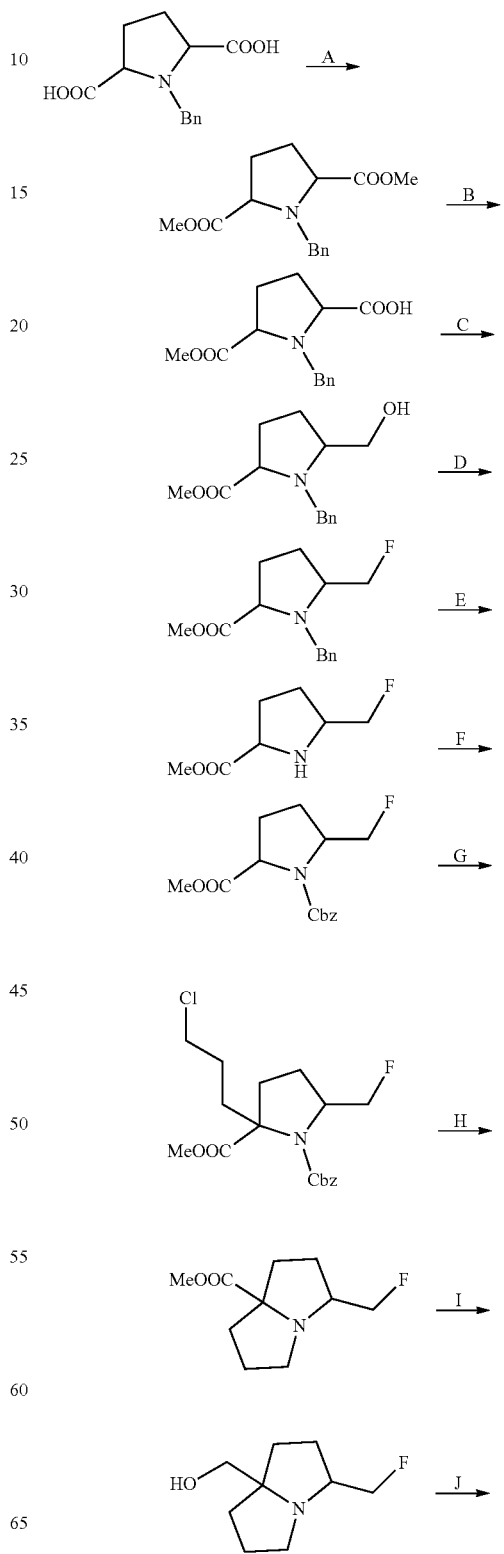

-continued

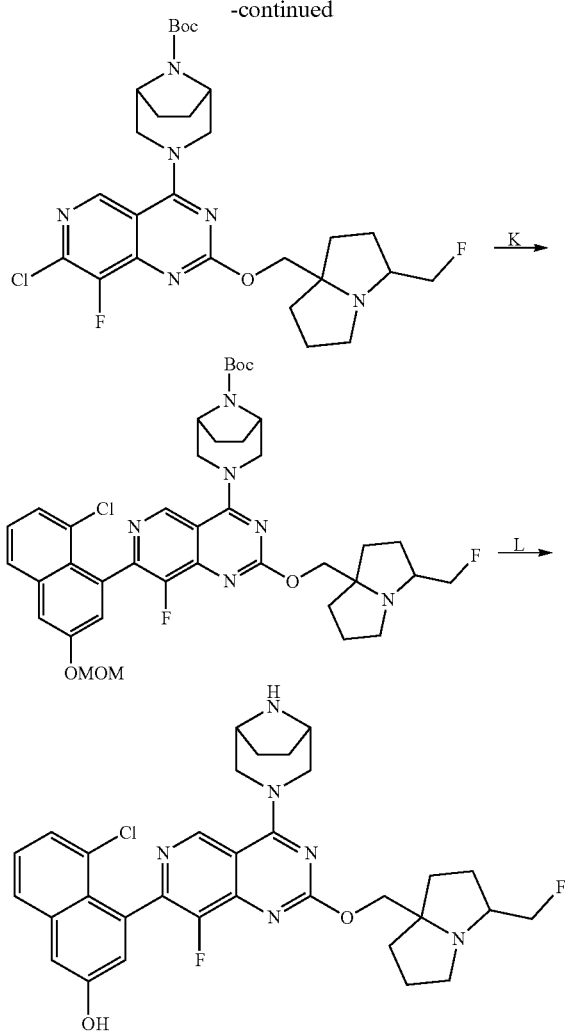

Step A. Dimethyl 1-benzylpyrrolidine-2,5-dicarboxylate (mixture of isomers). To a solution of 1-benzylpyrrolidine-2,5-dicarboxylic acid hydrochloride (1.5 g, 5.2 mmol) in tetrahydrofuran (21 mL) and methanol (5 mL) at 0° C. was added (diazomethyl)trimethylsilane (13 mL, 26 mmol) and the reaction was stirred at room temperature for 45 minutes. The solution was partitioned between dichloromethane and saturated NaHCO₃. The organics were washed with brine, dried with Na₂SO₄, filtered, concentrated, and purified by silica gel chromatography (5-95% EtOAc/hex) to give dimethyl 1-benzylpyrrolidine-2,5-dicarboxylate (mixture of isomers) (0.9 g, 62%). LCMS (MM-ES+APCI, Pos): m/z 278.1 (M+H).

Step B. 1-benzyl-5-(methoxycarbonyl)pyrrolidine-2-carboxylic acid (mixture of isomers). To a solution of dimethyl 1-benzylpyrrolidine-2,5-dicarboxylate (mixture of isomers) (0.73 g, 2.6 mmol) in methanol (4 mL) and water (4 mL) was added 2M NaOH (1.3 mL, 2.6 mmol) and the reaction was stirred overnight. The reaction mixture was concentrated to remove the MeOH and the aqueous solution was washed with EtOAc. The aqueous layer's pH was adjusted to 5 with 4.0 M HCl and was extracted with EtOAc. The EtOAc layer was dried with Na₂SO₄, filtered, and concentrated to give 1-benzyl-5-(methoxycarbonyl)pyrrolidine-2-carboxylic acid (mixture of isomers) (0.19 g, 28%). LCMS (MM-ES+APCI, Pos): m/z 264.1 (M+H).

Step C. Methyl 1-benzyl-5-(hydroxymethyl)pyrrolidine-2-carboxylate (mixture of isomers). To a solution of 1-benzyl-5-(methoxycarbonyl)pyrrolidine-2-carboxylic acid (mixture of isomers) (190 mg, 0.73 mmol) in tetrahydrofuran (7 mL) at 0° C. was added triethylamine (0.11 mL, 0.80 mmol) and ethyl chloroformate (76 μL, 0.80 mmol) and stirred for 90 minutes. The reaction mixture was filtered and the filtrate was added to a suspension of sodium borohydride (110 mg, 2.9 mmol) in water (0.4 mL). The reaction was stirred for 1 hour at 0° C. The solution was partitioned with EtOAc. The organics were dried with Na₂SO₄, filtered, and concentrated to give methyl 1-benzyl-5-(hydroxymethyl)pyrrolidine-2-carboxylate (mixture of isomers) (0.17 g, 92%). LCMS (MM-ES+APCI, Pos): m/z 250.1 (M+H).

Step D. Methyl 1-benzyl-5-(fluoromethyl)pyrrolidine-2-carboxylate (mixture of isomers). To a solution of 4-(trifluoro-k4-sulfanyl)morpholine (37 μL, 0.31 mmol) in dichloromethane (1.5 mL) at 0° C. was added methyl 1-benzyl-5-(hydroxymethyl)pyrrolidine-2-carboxylate (0.97 g, 3.9 mmol). The reaction was slowly warmed to room temperature over 2 hours. The solution was partitioned between dichloromethane and saturated NaHCO₃. The organics were concentrated and purified by silica gel chromatography (5-15% EtOAc/Hex) to give methyl 1-benzyl-5-fluoropiperidine-2-carboxylate (23 mg, 0.092 mmol, 44%) and methyl 1-benzyl-5-(fluoromethyl)pyrrolidine-2-carboxylate (mixture of isomers) (24 mg, 46%). LCMS (MM-ES+APCI, Pos): m/z 251.3 (M+H).

Step E. Methyl 5-(fluoromethyl)pyrrolidine-2-carboxylate (mixture of isomers). A solution of methyl 1-benzyl-5-(fluoromethyl)pyrrolidine-2-carboxylate (mixture of isomers) (15 mg, 0.060 mmol) and Pd/C Degussa type (6.4 mg, 0.006 mmol) in methanol (0.4 mL) was stirred under a balloon of hydrogen for 4 hours. The solution was filtered and concentrated to give methyl 5-(fluoromethyl)pyrrolidine-2-carboxylate (mixture of isomers) (9 mg, 94%). LCMS (MM-ES+APCI, Pos): m/z 161.2 (M+H).

Step F. 1-benzyl 2-methyl 5-(fluoromethyl)pyrrolidine-1,2-dicarboxylate (mixture of isomers). To a solution of methyl 5-(fluoromethyl)pyrrolidine-2-carboxylate (mixture of isomers) (35 mg, 0.217 mmol) and triethylamine (0.12 mL, 0.869 mmol) in dichloromethane (1 mL) was added benzyl carbonochloridate (61 μL, 0.43 mmol). The reaction was stirred for 1 hour. The solution was partitioned between dichloromethane and saturated NaHCO₃. The organics were washed with brine, dried with Na₂SO₄, filtered, concentrated, and purified by silica gel chromatography (5-95% EtOAc/Hex) to give 1-benzyl 2-methyl 5-(fluoromethyl)pyrrolidine-1,2-dicarboxylate (mixture of isomers) (61 mg, 95%). LCMS (MM-ES+APCI, Pos): m/z 296.2 (M+H).

Step G. 1-benzyl 2-methyl 2-(3-chloropropyl)-5-(fluoromethyl)pyrrolidine-1,2-dicarboxylate (mixture of isomers). To a solution of 1-benzyl 2-methyl 5-(fluoromethyl)pyrrolidine-1,2-dicarboxylate (mixture of isomers) (0.11 g, 0.38 mmol) in tetrahydrofuran (2 mL) at −70° C. was added LDA (1 mL, 1.9 mmol) and the reaction was stirred for 1 hour at −75° C. 1-Chloro-3-iodopropane (0.29 mL, 2.7 mmol) was added and the solution was stirred for 1 hour at room temperature. The solution was partitioned between dichloromethane and saturated NaHCO₃. The organics were concentrated and purified by silica gel chromatography (5-95% EtOAc/hex) to give 1-benzyl 2-methyl 2-(3-chloropropyl)-5-(fluoromethyl)pyrrolidine-1,2-dicarboxylate (mixture of isomers) (55 mg, 39%). LCMS (MM-ES+APCI, Pos): m/z 372.2 (M+H).

Step H. Methyl 3-(fluoromethyl)tetrahydro-1H-pyrrolizine-7a(5H)-carboxylate (mixture of isomers). A mixture of 1-benzyl 2-methyl 2-(3-chloropropyl)-5-(fluoromethyl)pyrrolidine-1,2-dicarboxylate (mixture of isomers) (3.6 mg, 0.0097 mmol) and Pd/C Degussa (1 mg, 0.001 mmol) in methanol (0.1 mL) was stirred under a balloon of hydrogen for 3 hours. The reaction was filtered and concentrated to give methyl 3-(fluoromethyl)tetrahydro-1H-pyrrolizine-7a (5H)-carboxylate (mixture of isomers) (1.8 mg, 92%). LCMS (MM-ES+APCI, Pos): m/z 202.1 (M+H)

Step I. (3-(fluoromethyl)tetrahydro-1H-pyrrolizin-7a (5H)-yl)methanol (mixture of isomers). To a solution of methyl 3-(fluoromethyl)tetrahydro-1H-pyrrolizine-7a(5H)-carboxylate (mixture of isomers) (29 mg, 0.14 mmol) in tetrahydrofuran (0.4 mL) at 0° C. was added 1M LiAlH4 (0.58 mL, 0.58 mmol). The reaction was stirred at 0° C. for 30 minutes and diluted with ether (0.3 mL). The mixture was cooled to 0° C. and water (30 μL) was added followed by 15% NaOH (30 μL) and additional water (90 μL). The slurry was stirred at room temperature for 15 minutes. MgSO$_4$ was added and the solution stirred for 15 minutes. The mixture was filtered and the filtrate was evaporated under a stream of N$_2$ to give (3-(fluoromethyl)tetrahydro-1H-pyrrolizin-7a (5H)-yl)methanol (mixture of isomers) (23 mg, 92%). LCMS (MM-ES+APCI, Pos): m/z 174.1 (M+H)

Step J. Tert-butyl (1R,5S)-3-(7-chloro-8-fluoro-2-((3-(fluoromethyl)tetrahydro-1H-pyrrolizin-7a(5H)-yl)methoxy)pyrido[4,3-d]pyrimidin-4-yl)-3,8-diazabicyclo[3.2.1]octane-8-carboxylate (mixture of isomers). A solution of tert-butyl (1R,5S)-3-(2,7-dichloro-8-fluoropyrido[4,3-d]pyrimidin-4-yl)-3,8-diazabicyclo[3.2.1]octane-8-carboxylate (59 mg, 0.14 mmol), (3-(fluoromethyl)tetrahydro-1H-pyrrolizin-7a(5H)-yl)methanol (mixture of isomers) (12 mg, 0.069 mmol), and cesium carbonate (68 mg, 0.21 mmol) in 1,4-dioxane (1 mL) was heated to 95° C. in a sealed vial for 3 days. The solution was partitioned between dichloromethane and saturated NaHCO$_3$. The organics were dried with Na$_2$SO$_4$, filtered, concentrated, and purified by reverse-phase chromatography (5-95% MeCN/water, 0.1% TFA). The product was partitioned between dichloromethane and saturated NaHCO$_3$. The organics were washed with brine, dried with Na$_2$SO$_4$, filtered, and concentrated to give tert-butyl (1R,5S)-3-(7-chloro-8-fluoro-2-((3-(fluoromethyl)tetrahydro-1H-pyrrolizin-7a(5H)-yl)methoxy)pyrido[4,3-d]pyrimidin-4-yl)-3,8-diazabicyclo[3.2.1]octane-8-carboxylate (mixture of isomers) (2.2 mg, 6%). LCMS (MM-ES+APCI, Pos): m/z 565.3 (M+H).

Step K. Tert-butyl (1R,5S)-3-(7-(8-chloro-3-(methoxymethoxy)naphthalen-1-yl)-8-fluoro-2-((3-(fluoromethyl)tetrahydro-1H-pyrrolizin-7a(5H)-yl)methoxy)pyrido[4,3-d]pyrimidin-4-yl)-3,8-diazabicyclo[3.2.1]octane-8-carboxylate (mixture of isomers). A solution of tert-butyl (1R,5S)-3-(7-chloro-8-fluoro-2-((3-(fluoromethyl)tetrahydro-1H-pyrrolizin-7a(5H)-yl)methoxy)pyrido[4,3-d]pyrimidin-4-yl)-3,8-diazabicyclo[3.2.1]octane-8-carboxylate (mixture of isomers) (2.2 mg, 0.0039 mmol), (8-chloro-3-(methoxymethoxy)naphthalen-1-yl)trimethylstannane (3.0 mg, 0.0078 mmol), BINAP (0.48 mg, 0.00078 mmol), PdCl$_2$(dppf)-DCM (0.32 mg, 0.00039 mmol), and copper (I) iodide (0.22 mg, 0.0012 mmol) in toluene (0.1 mL) was sparged with argon for 5 minutes, sealed, and heated to 95° C. overnight. The solution was filtered, concentrated, and purified by reverse-phase chromatography (5-95% MeCN/water with 0.1% TFA as modifier). The fractions containing product were pooled and partitioned between dichloromethane and saturated NaHCO$_3$. The organics were washed with brine, dried with Na$_2$SO$_4$, filtered, and concentrated to give tert-butyl (1R,5S)-3-(7-(8-chloro-3-(methoxymethoxy)naphthalen-1-yl)-8-fluoro-2-((3-(fluoromethyl)tetrahydro-1H-pyrrolizin-7a(5H)-yl)methoxy)pyrido[4,3-d]pyrimidin-4-yl)-3,8-diazabicyclo[3.2.1]octane-8-carboxylate (mixture of isomers) (1.2 mg, 41%). LCMS (MM-ES+APCI, Pos): m/z 751.1 (M+H).

Step L. 4-(4-((1R,5S)-3,8-diazabicyclo[3.2.1]octan-3-yl)-8-fluoro-2-((3-(fluoromethyl)tetrahydro-1H-pyrrolizin-7a (5H)-yl)methoxy)pyrido[4,3-d]pyrimidin-7-yl)-5-chloronaphthalen-2-ol (mixture of isomers). A solution of tert-butyl (1R,5S)-3-(7-(8-chloro-3-(methoxymethoxy)naphthalen-1-yl)-8-fluoro-2-((3-(fluoromethyl)tetrahydro-1H-pyrrolizin-7a(5H)-yl)methoxy)pyrido[4,3-d]pyrimidin-4-yl)-3,8-diazabicyclo[3.2.1]octane-8-carboxylate (1.2 mg, 0.0016 mmol) in TFA (0.1 mL) and DCM (0.1 mL) was stirred for 1 hour. The solution was concentrated to give 4-(4-((1R,5S)-3,8-diazabicyclo[3.2.1]octan-3-yl)-8-fluoro-2-((3-(fluoromethyl)tetrahydro-1H-pyrrolizin-7a(5H)-yl)methoxy)pyrido[4,3-d]pyrimidin-7-yl)-5-chloronaphthalen-2-ol bis(2,2,2-trifluoroacetate) (mixture of isomers) (0.7 mg, 52%). LCMS (MM-ES+APCI, Pos): m/z 607.2 (M+H).

Example 401

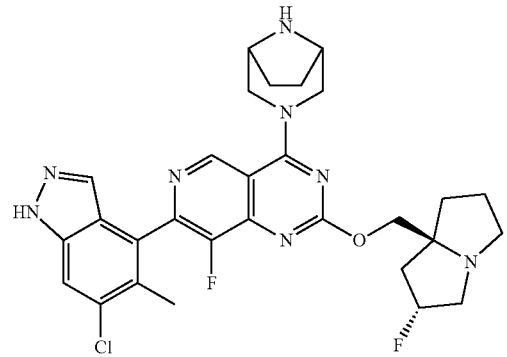 [SMILES: Cc1c(Cl)cc2[nH]ncc2c1-c1ncc2c(N3CC4CCC(C3)N4)nc(OC[C@@]34CCCN3C[C@H](F)C4)nc2c1F]

4-((1R,5S)-3,8-diazabicyclo[3.2.1]octan-3-yl)-7-(6-chloro-5-methyl-1H-indazol-4-yl)-8-fluoro-2-((2-fluorotetrahydro-1H-pyrrolizin-7a(5H)-yl)methoxy)pyrido[4,3-d]pyrimidine (racemic, trans)

Synthesized according to Example 3, Steps G-H substituting (2-fluorotetrahydro-1H-pyrrolizin-7a(5H)-yl)methanol (racemic, trans) in place of 2-(1-methyl-1H-imidazol-2-yl)ethan-1-ol in Step G and 6-chloro-5-methyl-1-(tetrahydro-2H-pyran-2-yl)-4-(4,4,5,5-tetramethyl-1,3,2-dioxaborolan-2-yl)-1H-indazole in place of 4-(4,4,5,5-tetramethyl-1,3,2-dioxaborolan-2-yl)naphthalen-2-ol in Step H followed by deprotection using Example 391, Step A to afford 4-((1R,5S)-3,8-diazabicyclo[3.2.1]octan-3-yl)-7-(6-chloro-5-methyl-1H-indazol-4-yl)-8-fluoro-2-((2-fluorotetrahydro-1H-pyrrolizin-7a(5H)-yl)methoxy)pyrido[4,3-d]pyrimidine (racemic, trans) (6.9 mg, 28%). LCMS (MM-ES+APCI, Pos): m/z 581.3 (M+H).

Example 402

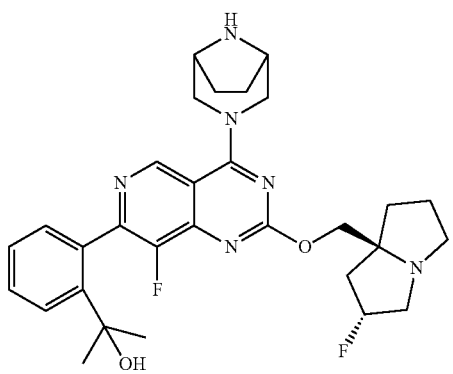 [SMILES: CC(C)(O)c1ccccc1-c1ncc2c(N3CC4CCC(C3)N4)nc(OC[C@@]34CCCN3C[C@H](F)C4)nc2c1F]

2-(2-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)phenyl)propan-2-ol (racemic, trans)

Step A. Tert-butyl (1R,5S)-3-(8-fluoro-2-((2-fluorotetrahydro-1H-pyrrolizin-7a(5H)-yl)methoxy)-7-(2-(2-hydroxypropan-2-yl)phenyl)pyrido[4,3-d]pyrimidin-4-yl)-3,8-diazabicyclo[3.2.1]octane-8-carboxylate (racemic, trans). Synthesized according to Example 424, Step A substituting 3,3-dimethylbenzo[c][1,2]oxaborol-1 (3H)-ol in place of 2-(5-(benzyloxy)-2-(2,2,2-trifluoroethyl)phenyl)-4,4,5,5-tetramethyl-1,3,2-dioxaborolane to afford tert-butyl (1R,5S)-3-(8-fluoro-2-((2-fluorotetrahydro-1H-pyrrolizin-7a(5H)-yl)methoxy)-7-(2-(2-hydroxypropan-2-yl)phenyl)pyrido[4,3-d]pyrimidin-4-yl)-3,8-diazabicyclo[3.2.1]octane-8-carboxylate (racemic, trans) (59 mg, 99%). LCMS (MM-ES+APCI, Pos): m/z 651.3 (M+H).

Step B. 2-(2-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)phenyl)propan-2-ol (racemic, trans). Synthesized according to Example 417, Step B substituting tert-butyl (1R,5S)-3-(8-fluoro-2-((2-fluorotetrahydro-1H-pyrrolizin-7a(5H)-yl)methoxy)-7-(2-(2-hydroxypropan-2-yl)phenyl)pyrido[4,3-d]pyrimidin-4-yl)-3,8-diazabicyclo[3.2.1]octane-8-carboxylate (racemic, trans) in place of tert-butyl (1R,5S)-3-(8-fluoro-2-((2-fluorotetrahydro-1H-pyrrolizin-7a(5H)-yl)methoxy)-7-(2-isobutylphenyl)pyrido[4,3-d]pyrimidin-4-yl)-3,8-diazabicyclo[3.2.1]octane-8-carboxylate (racemic, trans) to afford 2-(2-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)phenyl)propan-2-ol (racemic, trans) (5.0 mg, 10%). LCMS (MM-ES+APCI, Pos): m/z 551.3 (M+H).

Example 403

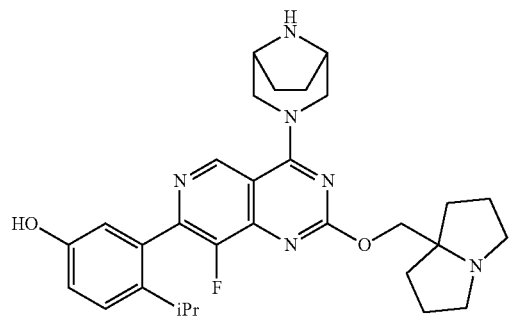 [SMILES: CC(C)c1ccc(O)cc1-c1ncc2c(N3CC4CCC(C3)N4)nc(OCC34CCCN3CCC4)nc2c1F]

3-(4-((1R,5S)-3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)-4-isopropylphenol

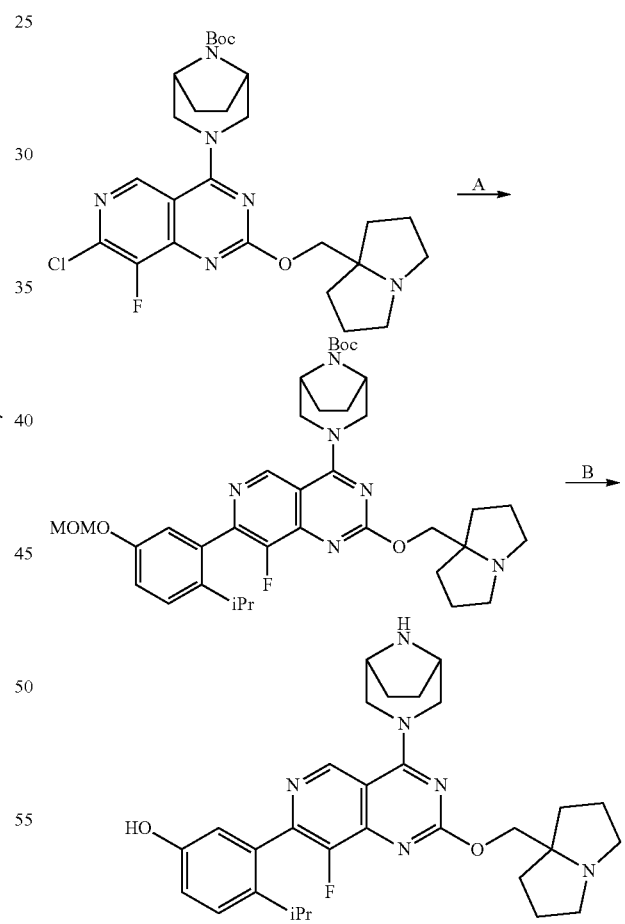

Step A. tert-butyl (1R,5S)-3-(8-fluoro-7-(2-isopropyl-5-(methoxymethoxy)phenyl)-2-((tetrahydro-1H-pyrrolizin-7a(5H)-yl)methoxy)pyrido[4,3-d]pyrimidin-4-yl)-3,8-diazabicyclo[3.2.1]octane-8-carboxylate. Tert-butyl (1R,5S)-3-(7-chloro-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (53 mg, 0.10 mmol), 2-(2- isopropyl-5-(methoxymethoxy)phenyl)-4,4,5,5-tetramethyl-1,3,2-dioxaborolane (43 mg, 0.14 mmol), and XPhos Pd G2 (16 mg, 0.02 mmol) were added to a vial with a stir bar and septa cap. The vial was degassed and purged with $N_2$ 3 times before degassed THF (0.2 mL) and degassed 0.5 M aqueous $K_3PO_4$ (0.4 mL, 0.2 mmol) were added. The reaction was heated to 40° C. for 1 hour. The reaction was diluted with water and extracted with DCM 3 times. The DCM layers were combined, dried with $Na_2SO_4$, filtered, and concentrated. The residue was purified by flash chromatography (silica, 0-20% MeOH in DCM) to yield tert-butyl (1R,5S)-3-(8-fluoro-7-(2-isopropyl-5-(methoxymethoxy)phenyl)-2-((tetrahydro-1H-pyrrolizin-7a(5H)-yl)methoxy)pyrido[4,3-d]pyrimidin-4-yl)-3,8-diazabicyclo[3.2.1]octane-8-carboxylate as a colorless oil (33 mg, 49%). LCMS (MM-ES+APCI, Pos): m/z 677.3 (M+H).

Step B. 3-(4-((1R,5S)-3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)-4-isopropylphenol. Tert-butyl (1R,5S)-3-(8-fluoro-7-(2-isopropyl-5-(methoxymethoxy)phenyl)-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (33 mg, 0.049 mmol) was added to a round bottom flask with a stir bar. DCM (1.5 mL) and 4M HCl in dioxanes (1.5 mL) were added at room temperature and the reaction was stirred for 40 minutes. The reaction was concentrated to dryness, and the residue was purified via reverse phase chromatography (C18, 0-80% MeCN in water with 0.1% TFA). The fractions containing the product were combined, frozen, and lyophilized. The acid salt was passed through two PL-HCO3 ME Resin plugs with methanol and concentrated to yield a solid. The solid was triturated with ether and dried to give 3-(4-((1R,5S)-3,8-diazabicyclo[3.2.1]octan-3-yl)-8-fluoro-2-((tetrahydro-1H-pyrrolizin-7a(5H)-yl)methoxy)pyrido[4,3-d]pyrimidin-7-yl)-4-isopropylphenol (9.2 mg, 34%). LCMS (MM-ES+APCI, Pos): m/z 533.3 (M+H).

Example 404

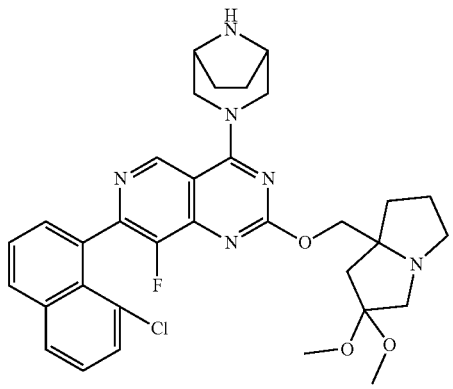 [SMILES: COC1(OC)CN2CCCC2(COc2nc(N3CC4CCC(C3)N4)c3cnc(-c4cccc5cccc(Cl)c45)c(F)c3n2)C1]

4-((1R,5S)-3,8-diazabicyclo[3.2.1]octan-3-yl)-7-(8-chloronaphthalen-1-yl)-2-((2,2-dimethoxytetrahydro-1H-pyrrolizin-7a(5H)-yl)methoxy)-8-fluoropyrido[4,3-d]pyrimidine (Mixture of Isomers)

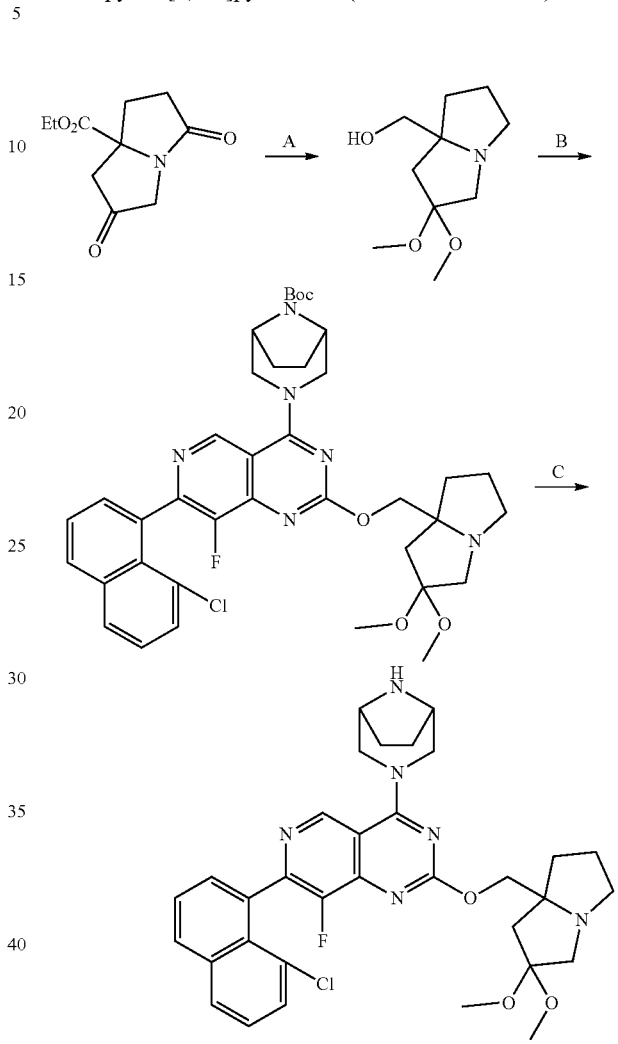

Step A. (2,2-dimethoxytetrahydro-1H-pyrrolizin-7a(5H)-yl)methanol (mixture of isomers). Thionyl chloride (0.50 mL, 6.91 mmol) was added to a solution of ethyl 2,5-dioxotetrahydro-1H-pyrrolizine-7a(5H)-carboxylate (mixture of isomers) (0.29 g, 1.4 mmol) in methanol (7 mL) at 0° C. The reaction was warmed to room temperature and stirred for 1 hour. The reaction mixture was concentrated to dryness and partitioned between saturated $NaHCO_3$ and DCM. The DCM layer was dried with $Na_2SO_4$ and concentrated to give a yellow oil. The oil was dissolved in THF (3.5 mL) and 2.4 M LAH (1.2 mL, 2.8 mmol) was added dropwise at 0° C. The reaction was warmed to room temperature and stirred for 1 hour. The reaction was heated to 45° C. for 1 hour and 50° C. for 10 hours. The reaction was quenched with ice and 2M NaOH (10 ml). The mixture was extracted with DCM 4 times. The DCM layers were combined and concentrated to give (2,2-dimethoxytetrahydro-1H-pyrrolizin-7a(5H)-yl)methanol (mixture of isomers) as a yellow oil (0.17 g, 60%). LCMS (MM-ES+APCI, Pos): m/z 202.3 (M+H).

Step B. tert-butyl (1R,5S)-3-(7-(8-chloronaphthalen-1-yl)-2-((2,2-dimethoxytetrahydro-1H-pyrrolizin-7a(5H)-yl)

829 methoxy)-8-fluoropyrido[4,3-d]pyrimidin-4-yl)-3,8-diazabicyclo[3.2.1]octane-8-carboxylate (mixture of isomers). (2,2-Dimethoxytetrahydro-1H-pyrrolizin-7a(5H)-yl)methanol (mixture of isomers) (0.13 g, 0.65 mmol) was added to a vial with a stir bar and septa cap. The vial was degassed and purged with $N_2$ 3 times before dry THF (4 mL) was added. The vial was cooled to 0° C. and 60% NaH (26 mg, 0.66 mmol) was added in one portion. The reaction was stirred at 0° C. for 30 minutes before tert-butyl (1R,5S)-3-(2-chloro-7-(8-chloronaphthalen-1-yl)-8-fluoropyrido[4,3-d]pyrimidin-4-yl)-3,8-diazabicyclo[3.2.1]octane-8-carboxylate (0.28 g, 0.50 mmol) was added portion wise as a solid. The reaction was stirred at 0° C. for 15 minutes and at room temperature for 4.5 hours. The reaction was diluted with water and extracted with DCM 3 times. The DCM layers were combined, dried with $Na_2SO_4$, filtered, and concentrated. The residue was purified by flash chromatography (silica, 0-20% MeOH in DCM) to yield tert-butyl (1R,5S)-3-(7-(8-chloronaphthalen-1-yl)-2-((2,2-dimethoxytetrahydro-1H-pyrrolizin-7a(5H)-yl)methoxy)-8-fluoropyrido[4,3-d]pyrimidin-4-yl)-3,8-diazabicyclo[3.2.1]octane-8-carboxylate (mixture of isomers) as an off-white solid (0.26 g, 73%). LCMS (MM-ES+APCI, Pos): m/z 719.3 (M+H).

Step C. 4-((1R,5S)-3,8-diazabicyclo[3.2.1]octan-3-yl)-7-(8-chloronaphthalen-1-yl)-2-((2,2-dimethoxytetrahydro-1H-pyrrolizin-7a(5H)-yl)methoxy)-8-fluoropyrido[4,3-d]pyrimidine (mixture of isomers). Tert-butyl (1R,5S)-3-(7-(8-chloronaphthalen-1-yl)-2-((2,2-dimethoxytetrahydro-1H-pyrrolizin-7a(5H)-yl)methoxy)-8-fluoropyrido[4,3-d]pyrimidin-4-yl)-3,8-diazabicyclo[3.2.1]octane-8-carboxylate (mixture of isomers) (10 mg, 0.014 mmol) was added to a round bottom flask with a stir bar. DCM (1 mL) was added followed by TFA (0.5 mL). The reaction stirred at room temperature for 1 hour before being concentrated to dryness. The TFA salt was passed through three PL-HCO3 ME Resin plugs with methanol and concentrated to give a solid. The solid was triturated with ether and dried to yield 4-((1R,5S)-3,8-diazabicyclo[3.2.1]octan-3-yl)-7-(8-chloronaphthalen-1-yl)-2-((2,2-dimethoxytetrahydro-1H-pyrrolizin-7a(5H)-yl)methoxy)-8-fluoropyrido[4,3-d]pyrimidine (mixture of isomers) as a waxy white solid (1.8 mg, 21%). LCMS (MM-ES+APCI, Pos): m/z 619.3 (M+H).

Example 405

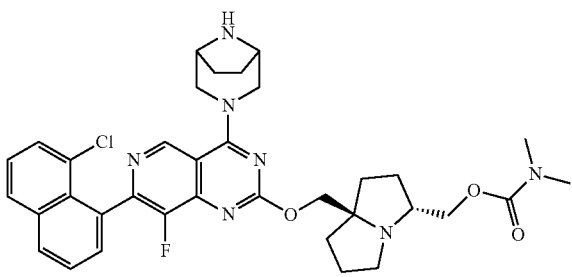 [SMILES: CN(C)C(=O)OC[C@H]1CC[C@@]2(COc3nc(N4CC5CCC(C4)N5)c4cnc(-c5cccc6cccc(Cl)c56)c(F)c4n3)CCCN12]

830

(7a-(((4-(3,8-diazabicyclo[3.2.1]octan-3-yl)-7-(8-chloronaphthalen-1-yl)-8-fluoropyrido[4,3-d]pyrimidin-2-yl)oxy)methyl)hexahydro-1H-pyrrolizin-3-yl) methyl dimethylcarbamate (Mixture of Trans Diastereomers)

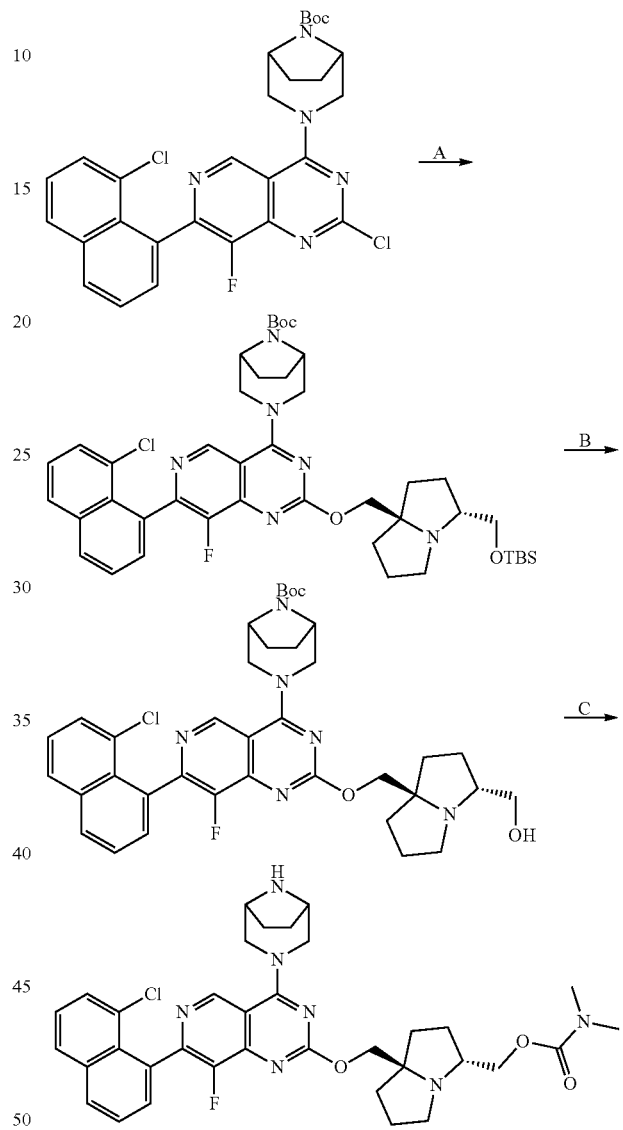

Step A. tert-butyl 3-(2-((3-(((tert-butyldimethylsilyl)oxy) methyl)tetrahydro-1H-pyrrolizin-7a(5H)-yl)methoxy)-7-(8-chloronaphthalen-1-yl)-8-fluoropyrido[4,3-d]pyrimidin-4-yl)-3,8-diazabicyclo[3.2.1]octane-8-carboxylate (mixture of trans diastereomers). To a solution of tert-butyl (1R,5S)-3-(2-chloro-7-(8-chloronaphthalen-1-yl)-8-fluoropyrido[4,3-d]pyrimidin-4-yl)-3,8-diazabicyclo[3.2.1]octane-8-carboxylate (554 mg, 1.00 mmol) and (3-(((tert-butyldimethylsilyl)oxy)methyl)tetrahydro-1H-pyrrolizin-7a (5H)-yl)methanol (mixture of trans diastereomers) (0.34 g, 1.2 mmol) in THF (10 mL) at 0° C. was added NaH (60%, 48 mg, 1.2 mmol). The mixture was warmed to rt and stirred for 4 h. The mixture was purified by flash chromatography eluting with 0-20% MeOH (with 5% $NH_3 \cdot H_2O$)/DCM to give the title compound (0.65 g, 80%) as an off-white solid. LCMS (MM-ES+APCI, Pos): m/z 803.2 (M+H).

Step B. tert-butyl 3-(7-(8-chloronaphthalen-1-yl)-8-fluoro-2-((3-(hydroxymethyl)tetrahydro-1H-pyrrolizin-7a(5H)-yl)methoxy)pyrido[4,3-d]pyrimidin-4-yl)-3,8-diazabicyclo[3.2.1]octane-8-carboxylate (mixture of trans diastereomers). To a solution of tert-butyl (1R,5S)-3-(2-((3-(((tert-butyldimethylsilyl)oxy)methyl)tetrahydro-1H-pyrrolizin-7a(5H)-yl)methoxy)-7-(8-chloronaphthalen-1-yl)-8-fluoropyrido[4,3-d]pyrimidin-4-yl)-3,8-diazabicyclo[3.2.1]octane-8-carboxylate (mixture of trans diastereomers) (0.64 g, 0.79 mmol) in THF (4 mL) at rt was added TBAF (1.0 M in THF, 1.5 mL, 1.20 mmol). The mixture was stirred at r.t. for 0.5 h, quenched with NaHCO₃ (sat.), and extracted with ethyl acetate. The combined extract was washed with water (50 mL×2), washed with brine, and dried (Na₂SO₄). The solution was concentrated to dryness to give a solid, which was triturated with hexanes and dried to give the crude title compound (0.61 g, 112%) as a light yellow solid. LCMS (MM-ES+APCI, Pos): m/z 689.3 (M+H).

Step C. (7a-(((4-(3,8-diazabicyclo[3.2.1]octan-3-yl)-7-(8-chloronaphthalen-1-yl)-8-fluoropyrido[4,3-d]pyrimidin-2-yl)oxy)methyl)hexahydro-1H-pyrrolizin-3-yl)methyl dimethylcarbamate (mixture of trans diastereomers). To a solution of crude tert-butyl 3-(7-(8-chloronaphthalen-1-yl)-8-fluoro-2-((3-(hydroxymethyl)tetrahydro-1H-pyrrolizin-7a(5H)-yl)methoxy)pyrido[4,3-d]pyrimidin-4-yl)-3,8-diazabicyclo[3.2.1]octane-8-carboxylate (mixture of trans diastereomers) (25 mg, 0.036 mmol) and Et₃N (0.010 mL, 0.073 mmol) in THF (0.7 mL) was added 4-nitrophenyl chloroformate (8.8 mg, 0.044 mmol). The mixture was stirred at r.t. for 0.5 h and dimethylamine (2.0 M, 0.073 mL, 0.15 mmol) was added. The mixture was stirred at r.t. for 0.5 h and concentrated to dryness. The residue was dissolved in DCM (1 mL), TFA (0.50 mL) was added at r.t., and the reaction was stirred for 30 min. The solution was concentrated to dryness and the residue purified by preparative C18 HPLC (Gilson, 0-95% CH₃CN/H₂O with 0.1% TFA). The desired fractions were combined, basified with NaHCO₃ (sat.), and extracted with DCM/IPA (5:1). The combined extract was dried (Na₂SO₄) and concentrated to give the title compound (11 mg, 46%) as a yellow solid. LCMS (MM-ES+APCI, Pos): m/z 660.3 (M+H).

Example 406

4-(4-((1R,5S)-3,8-diazabicyclo[3.2.1]octan-3-yl)-8-fluoro-2-((2-methoxytetrahydro-1H-pyrrolizin-7a(5H)-yl)methoxy)pyrido[4,3-d]pyrimidin-7-yl)-5-fluoronaphthalen-2-ol (mixture of cis diastereomers)

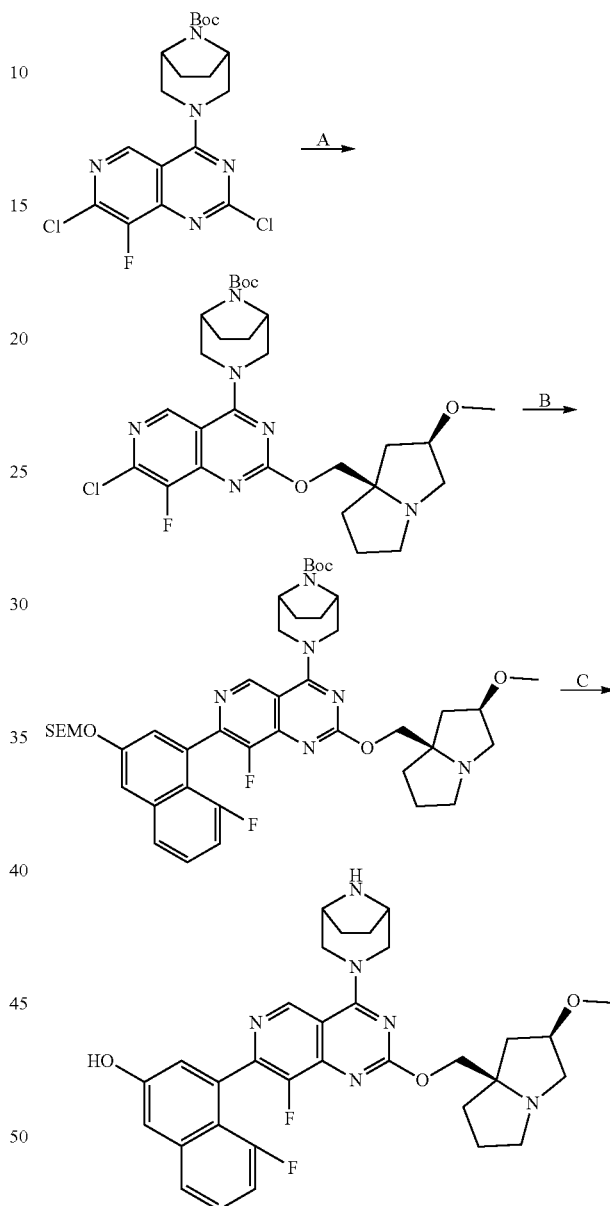

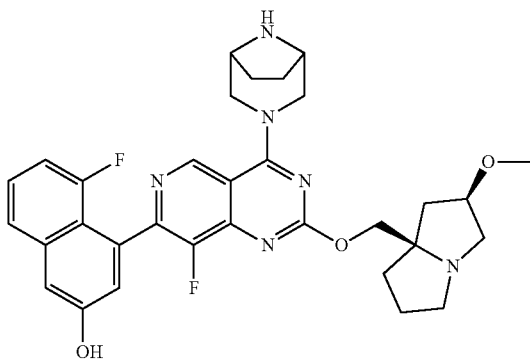 [SMILES: CO[C@H]1CN2CCC[C@]2(COc2nc(N3CC4CCC(C3)N4)c3cnc(-c4cc(O)cc5cccc(F)c45)c(F)c3n2)C1]

Step A. tert-butyl (1R,5S)-3-(7-chloro-8-fluoro-2-((2-methoxytetrahydro-1H-pyrrolizin-7a(5H)-yl)methoxy)pyrido[4,3-d]pyrimidin-4-yl)-3,8-diazabicyclo[3.2.1]octane-8-carboxylate (mixture of cis diastereomers). Tert-butyl (1R,5S)-3-(2,7-dichloro-8-fluoropyrido[4,3-d]pyrimidin-4-yl)-3,8-diazabicyclo[3.2.1]octane-8-carboxylate (0.32 g, 0.76 mmol), (2-methoxytetrahydro-1H-pyrrolizin-7a(5H)-yl)methanol (mixture of cis diastereomers, synthesized according to Example 225, Step A-C) (0.13 g, 0.76 mmol), and Cs₂CO₃ (0.74 g, 2.3 mmol) were added to a vial with a stir bar and septa cap. The vial was degassed and purged with N₂ 3 times before dioxane (8 mL) was added. The reaction was heated to 95° C. for 19 hours. The reaction was diluted with water and extracted with DCM 3 times. The DCM layers were combined, dried with Na₂SO₄, filtered, and concentrated. The residue was purified by flash chromatography (silica, 0-20% MeOH in DCM) to yield tert-butyl (1R,5S)-3-(7-chloro-8-fluoro-2-((2-methoxytetrahydro-1H-pyrrolizin-7a(5H)-yl)methoxy)pyrido[4,3-d]pyrimidin-4-yl)-3,8-diazabicyclo[3.2.1]octane-8-carboxylate (mixture of cis diastereomers) (0.24 g, 57%). LCMS (MM-ES+APCI, Pos): m/z 563.3 (M+H).

Step B. tert-butyl (1R,5S)-3-(8-fluoro-7-(8-fluoro-3-((2-(trimethylsilyl)ethoxy)methoxy)naphthalen-1-yl)-2-((2-methoxytetrahydro-1H-pyrrolizin-7a(5H)-yl)methoxy)pyrido[4,3-d]pyrimidin-4-yl)-3,8-diazabicyclo[3.2.1]octane-8-carboxylate (mixture of cis diastereomers). tert-butyl (1R,5S)-3-(7-chloro-8-fluoro-2-((2-methoxytetrahydro-1H-pyrrolizin-7a(5H)-yl)methoxy)pyrido[4,3-d]pyrimidin-4-yl)-3,8-diazabicyclo[3.2.1]octane-8-carboxylate (mixture of cis diastereomers) (25 mg, 0.044 mmol), (2-(((5-fluoro-4-(4,4,5,5-tetramethyl-1,3,2-dioxaborolan-2-yl)naphthalen-2-yl)oxy)methoxy)ethyl)trimethylsilane (18 mg, 0.044 mmol, synthesized according to Example 366, Step A-F), and XPhos Pd G2 (7 mg, 0.009 mmol) were added to a vial with a stir bar and septa cap. The vial was degassed and purged with N₂ 3 times before degassed THF (88 µL) and degassed 0.5 M aqueous K₃PO₄ (0.18 mL, 0.088 mmol) were added. The reaction was heated to 40° C. for 1 hour. The reaction was diluted with water and extracted with DCM 3 times. The DCM layers were combined, dried with Na₂SO₄, filtered, and concentrated. The residue was purified by flash chromatography (silica, 0-16% MeOH in DCM) to yield 7.8 mg of an 8:1 mixture of tert-butyl (1R,5S)-3-(8-fluoro-7-(8-fluoro-3-((2-(trimethylsilyl)ethoxy)methoxy)naphthalen-1-yl)-2-((2-methoxytetrahydro-1H-pyrrolizin-7a(5H)-yl)methoxy)pyrido[4,3-d]pyrimidin-4-yl)-3,8-diazabicyclo[3.2.1]octane-8-carboxylate (mixture of cis diastereomers) and tert-butyl (1R,5S)-3-(7-chloro-8-fluoro-2-((2-methoxytetrahydro-1H-pyrrolizin-7a(5H)-yl)methoxy)pyrido[4,3-d]pyrimidin-4-yl)-3,8-diazabicyclo[3.2.1]octane-8-carboxylate (mixture of cis diastereomers). LCMS (MM-ES+APCI, Pos): m/z 819.4 (M+H).

Step C. 4-(4-((1R,5S)-3,8-diazabicyclo[3.2.1]octan-3-yl)-8-fluoro-2-((2-methoxytetrahydro-1H-pyrrolizin-7a(5H)-yl)methoxy)pyrido[4,3-d]pyrimidin-7-yl)-5-fluoronaphthalen-2-ol (mixture of cis diastereomers). The mixture of tert-butyl (1R,5S)-3-(8-fluoro-7-(8-fluoro-3-((2-(trimethylsilyl)ethoxy)methoxy)naphthalen-1-yl)-2-((2-methoxytetrahydro-1H-pyrrolizin-7a(5H)-yl)methoxy)pyrido[4,3-d]pyrimidin-4-yl)-3,8-diazabicyclo[3.2.1]octane-8-carboxylate (mixture of cis diastereomers) and tert-butyl (1R,5S)-3-(7-chloro-8-fluoro-2-((2-methoxytetrahydro-1H-pyrrolizin-7a(5H)-yl)methoxy)pyrido[4,3-d]pyrimidin-4-yl)-3,8-diazabicyclo[3.2.1]octane-8-carboxylate (mixture of cis diastereomers) from step B were added to a round bottom flask with a stir bar. DCM (1 mL) and TFA (0.5 mL) were added at room temperature and the reaction was stirred for 1 hour. The reaction was concentrated to dryness, and the residue was purified via reverse phase chromatography (C18, 0-80% MeCN in water with 0.1% TFA). The fractions containing the product were combined, frozen, and lyophilized. The TFA salt was passed through two PL-HCO3 ME Resin plugs with methanol and concentrated to give 4-(4-((1R,5S)-3,8-diazabicyclo[3.2.1]octan-3-yl)-8-fluoro-2-((2-methoxytetrahydro-1H-pyrrolizin-7a(5H)-yl)methoxy)pyrido[4,3-d]pyrimidin-7-yl)-5-fluoronaphthalen-2-ol (mixture of cis diastereomers) as a pale yellow solid (2.8 mg, 51%). LCMS (MM-ES+APCI, Pos): m/z 589.2 (M+H).

Example 407

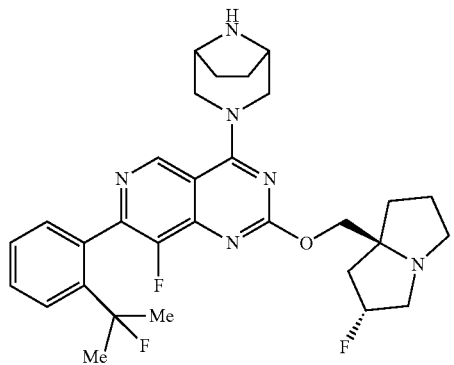 [SMILES: CC(C)(F)c1ccccc1-c1ncc2c(N3CC4CCC(C3)N4)nc(OC[C@@]34CCCN3C[C@H](F)C4)nc2c1F]

4-((1R,5S)-3,8-diazabicyclo[3.2.1]octan-3-yl)-8-fluoro-7-(2-(2-fluoropropan-2-yl)phenyl)-2-((2-fluorotetrahydro-1H-pyrrolizin-7a(5H)-yl)methoxy)pyrido[4,3-d]pyrimidine (racemic, trans)

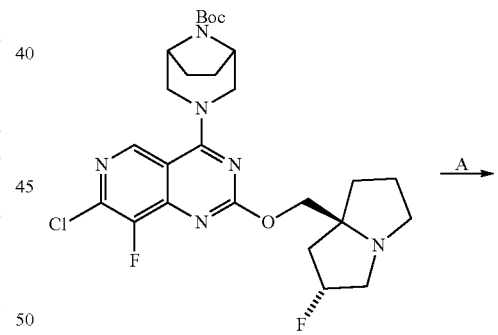

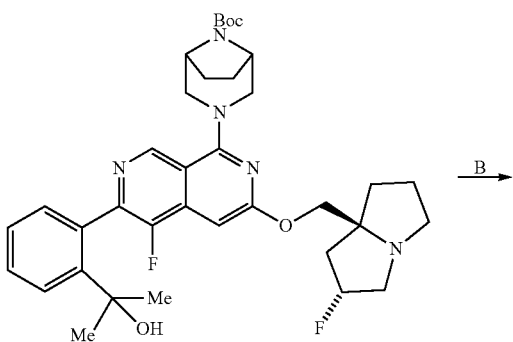

-continued

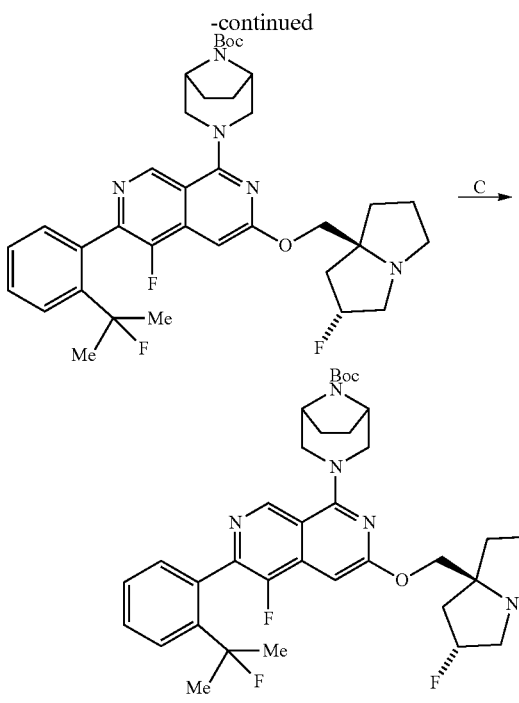

Step A. Tert-butyl (1R,5S)-3-(8-fluoro-2-((2-fluorotetrahydro-1H-pyrrolizin-7a(5H)-yl)methoxy)-7-(2-(2-hydroxypropan-2-yl)phenyl)pyrido[4,3-d]pyrimidin-4-yl)-3,8-diazabicyclo[3.2.1]octane-8-carboxylate (racemic, trans). Synthesized according to Example 424, Step A substituting 3,3-dimethylbenzo[c][1,2]oxaborol-1 (3H)-ol in place of 2-(5-(benzyloxy)-2-(2,2,2-trifluoroethyl)phenyl)-4,4,5,5-tetramethyl-1,3,2-dioxaborolane to afford tert-butyl (1R,5S)-3-(8-fluoro-2-((2-fluorotetrahydro-1H-pyrrolizin-7a(5H)-yl)methoxy)-7-(2-(2-hydroxypropan-2-yl)phenyl)pyrido[4,3-d]pyrimidin-4-yl)-3,8-diazabicyclo[3.2.1]octane-8-carboxylate (racemic, trans) (39 mg, 66%). LCMS (MM-ES+APCI, Pos): m/z 651.3 (M+H).

Step B. Tert-butyl (1R,5S)-3-(8-fluoro-7-(2-(2-fluoropropan-2-yl)phenyl)-2-((2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (racemic, trans). Tert-butyl (1R,5S)-3-(8-fluoro-2-((2-fluorotetrahydro-1H-pyrrolizin-7a(5H)-yl)methoxy)-7-(2-(2-hydroxypropan-2-yl)phenyl)pyrido[4,3-d]pyrimidin-4-yl)-3,8-diazabicyclo[3.2.1]octane-8-carboxylate (racemic, trans) (39 mg, 0.060 mmol) was dissolved in DCM (2 mL). After cooling to −78° C., bis(2-methoxyethyl)aminosulfur trifluoride (0.033 mL, 0.180 mmol) was added. After 90 minutes, the reaction was diluted with ethyl acetate and quenched with saturated aqueous NaHCO$_3$. The organics were separated, dried over MgSO$_4$, and condensed. The residue was purified by flash chromatography (4 g RediSep Gold column, 0-10% MeOH/DCM) to give tert-butyl (1R,5S)-3-(8-fluoro-7-(2-(2-fluoropropan-2-yl)phenyl)-2-((2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (racemic, trans) (22 mg, 56%). LCMS (MM-ES+APCI, Pos): m/z 653.3 (M+H).

Step C. 4-((1R,5S)-3,8-diazabicyclo[3.2.1]octan-3-yl)-8-fluoro-7-(2-(2-fluoropropan-2-yl)phenyl)-2-((2-fluorotetrahydro-1H-pyrrolizin-7a(5H)-yl)methoxy)pyrido[4,3-d]pyrimidine bis(2,2,2-trifluoroacetate) (racemic, trans). Synthesized according to Example 417, Step B substituting tert-butyl (1R,5S)-3-(8-fluoro-7-(2-(2-fluoropropan-2-yl)phenyl)-2-((2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (racemic, trans) in place of tert-butyl (1R,5S)-3-(8-fluoro-2-((2-fluorotetrahydro-1H-pyrrolizin-7a(5H)-yl)methoxy)-7-(2-isobutylphenyl)pyrido[4,3-d]pyrimidin-4-yl)-3,8-diazabicyclo[3.2.1]octane-8-carboxylate (racemic, trans) to afford 4-((1R,5S)-3,8-diazabicyclo[3.2.1]octan-3-yl)-8-fluoro-7-(2-(2-fluoropropan-2-yl)phenyl)-2-((2-fluorotetrahydro-1H-pyrrolizin-7a(5H)-yl)methoxy)pyrido[4,3-d]pyrimidine bis(2,2,2-trifluoroacetate) (racemic, trans) (1.2 mg, 5%). LCMS (MM-ES+APCI, Pos): m/z 553.3 (M+H).

Example 408

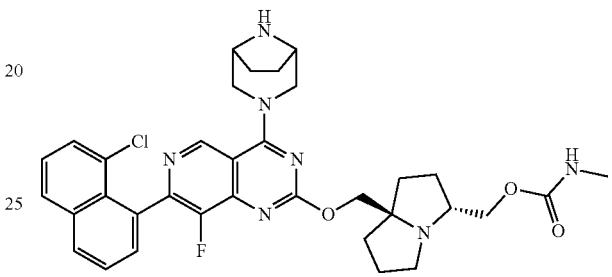

(7a-(((4-(3,8-diazabicyclo[3.2.1]octan-3-yl)-7-(8-chloronaphthalen-1-yl)-8-fluoropyrido[4,3-d]pyrimidin-2-yl)oxy)methyl)hexahydro-1H-pyrrolizin-3-yl)methyl methylcarbamate (mixture of trans diastereomers)

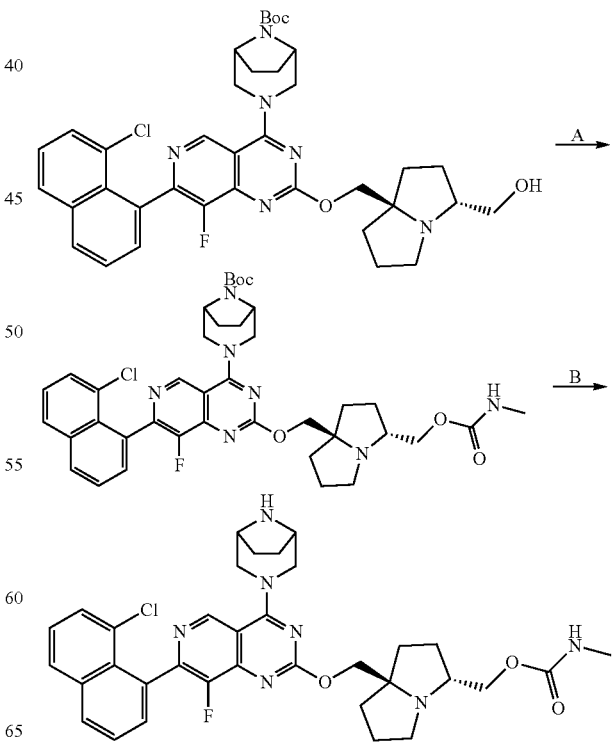

Step A. tert-butyl 3-(7-(8-chloronaphthalen-1-yl)-8-fluoro-2-((3-(((methylcarbamoyl)oxy)methyl)tetrahydro-1H-pyrrolizin-7a(5H)-yl)methoxy)pyrido[4,3-d]pyrimidin-4-yl)-3,8-diazabicyclo[3.2.1]octane-8-carboxylate (mixture of trans diastereomers).

To a solution of tert-butyl 3-(7-(8-chloronaphthalen-1-yl)-8-fluoro-2-((3-(hydroxymethyl)tetrahydro-1H-pyrrolizin-7a(5H)-yl)methoxy)pyrido[4,3-d]pyrimidin-4-yl)-3,8-diazabicyclo[3.2.1]octane-8-carboxylate (mixture of trans diastereomers) (28 mg, 0.041 mmol, synthesized according to Example 405, Step A-B) in tetrahydrofuran (0.83 mL) was added 4-nitrophenyl chloroformate (12 mg, 0.061 mmol), followed by Et$_3$N (11 μL, 0.081 mmol). The mixture was stirred at rt for 15 min and methylamine (2.0 M, 0.16 mL, 0.32 mmol) was added. The mixture was stirred at r.t. for 1 h and was purified by preparative C18 HPLC (Gilson, 0-95% CH$_3$CN/H$_2$O with 0.1% TFA). The desired fractions were combined, basified with NaHCO$_3$ (sat.), and extracted with ethyl acetate. The combined extract was dried (Na$_2$SO$_4$) and concentrated to give the title compound (16 mg, 53%) as a white solid. LCMS (MM-ES+APCI, Pos): m/z 746.3 (M+H).

Step B. (7a-(((4-(3,8-diazabicyclo[3.2.1]octan-3-yl)-7-(8-chloronaphthalen-1-yl)-8-fluoropyrido[4,3-d]pyrimidin-2-yl)oxy)methyl)hexahydro-1H-pyrrolizin-3-yl)methyl methylcarbamate (mixture of trans diastereomers). To a solution of tert-butyl 3-(7-(8-chloronaphthalen-1-yl)-8-fluoro-2-((3-(((methylcarbamoyl)oxy)methyl)tetrahydro-1H-pyrrolizin-7a(5H)-yl)methoxy)pyrido[4,3-d]pyrimidin-4-yl)-3,8-diazabicyclo[3.2.1]octane-8-carboxylate (mixture of trans diastereomers) (15 mg, 0.020 mmol) in DCM (1 mL) was added TFA (0.5 mL). The solution was stirred at r.t. for 0.5 h. The solution was concentrated to dryness, basified with NaHCO$_3$ (sat.), and extracted with DCM/IPA (5:1). The extract was dried (Na$_2$SO$_4$) and concentrated to give the title compound (12 mg, 92%) as a white solid. LCMS (MM-ES+APCI, Pos): m/z 646.3 (M+H).

Example 409

2-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)benzonitrile (racemic, trans)

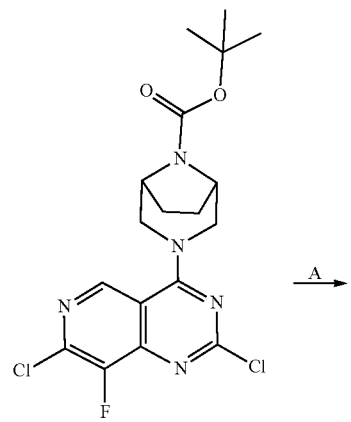

A →

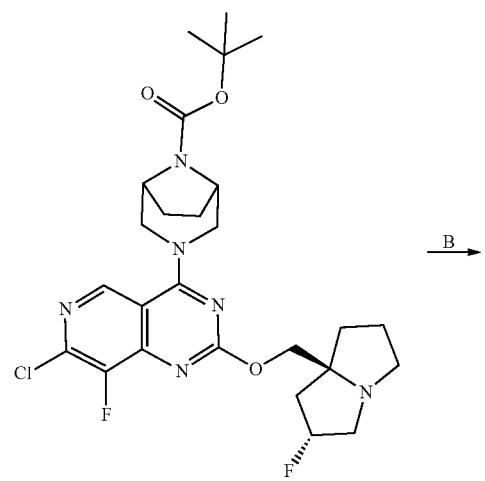

B →

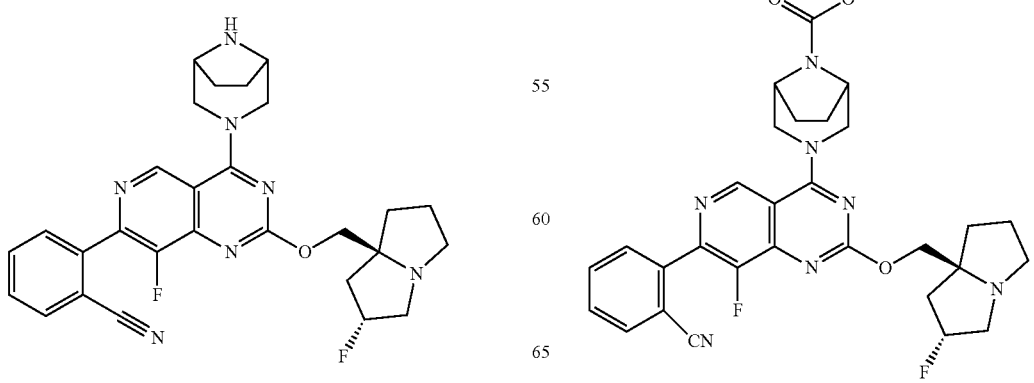

C →

-continued

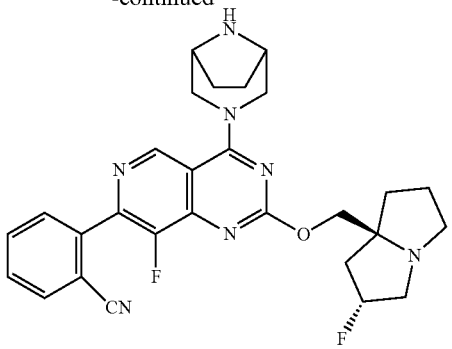

Step A: tert-butyl(1R,5S)-3-(7-chloro-8-fluoro-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate. A mixture of tert-butyl (1R,5S)-3-(2,7-dichloro-8-fluoropyrido[4,3-d]pyrimidin-4-yl)-3,8-diazabicyclo[3.2.1]octane-8-carboxylate (2.0 g, 4.7 mmol) and 1,4-dioxane (45 ml) was treated with ((2R,7as)-2-fluorotetrahydro-1H-pyrrolizin-7a(5H)-yl)methanol (1.5 g, 9.3 mmol) and Cesium Carbonate (4.5 g, 14 mmol) at room temperature. 3 A powdered mol sieves (1.5 g) were added and the mixture was stirred at 95° C. for 3 days. The cooled mixture was diluted with EtOAc and filtered. The filtrate was washed with water and the aqueous layer extracted with EtOAc. The combined organic layers were washed with brine, dried over sodium sulfate, filtered, and concentrated in vacuo. The concentrate was purified by normal phase chromatography eluting with 0% to 10% DCM/MeOH+2% NH₄OH to afford tert-butyl (1R,5S)-3-(7-chloro-8-fluoro-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (0.98 g, 38% yield). LCMS (MM-ES+APCI, Pos): m/z 551.3 (M+H).

Step B: tert-butyl(1R,5S)-3-(7-(2-cyanophenyl)-8-fluoro-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate. A mixture of tert-butyl(1R,5S)-3-(7-chloro-8-fluoro-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (0.10 g, 0.18 mmol), 2-Cyanophenylboronic acid (40 mg, 0.27 mmol), and potassium carbonate (0.18 mL, 0.36 mmol) (2M aq.) in dioxane (2 ml) was sparged with Argon for 15 minutes. To this was added Tetrakis (triphenylphosphine) palladium (0) (21 mg, 0.02 mmol) and the reaction stirred at 90° C. for 1.5 hours. The reaction was cooled to room temp and partitioned between water and EtOAc. The combined organics were washed with brine, dried over sodium sulfate and concentrated in vacuo. The concentrate was purified by normal phase chromatography eluting with 0% to 10% DCM/MeOH+2% NH₄OH modifier to give tert-butyl (1R,5S)-3-(7-(2-cyanophenyl)-8-fluoro-2-(((2R,7aS)-2-fluoro-tetrahydro-1H-pyrrolizin-7a(5H)-yl)methoxy)pyrido[4,3-d]pyrimidin-4-yl)-3,8-diazabicyclo[3.2.1]octane-8-carboxylate (30 mg, 27% yield). LCMS (MM-ES+APCI, Pos): m/z 618.3 (M+H).

Step C 2-(4-((1R,5S)-3,8-diazabicyclo[3.2.1]octan-3-yl)-8-fluoro-2-(((2R,7aS)-2-fluorotetrahydro-1H-pyrrolizin-7a(5H)-yl)methoxy)pyrido[4,3-d]pyrimidin-7-yl)benzonitrile. tert-butyl(1R,5S)-3-(7-(2-cyanophenyl)-8-fluoro-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (30 mg, 0.05 mmol) was dissolved in DCM (0.5 mL) and treated with TFA (15 µL, 0.19 mmol). The reaction stirred at room temperature for 1 hour and was concentrated in vacuo. The concentrate was purified by prep HPLC (Gilson, 5 to 95% ACN/water+0.1% TFA as modifier) and lyophilized overnight. The solid was resuspended in 1 mL of methanol and free based with a PL-HCO3 MP SPE cartridge. The organics were concentrated in vacuo to give 2-(4-((1R,5S)-3,8-diazabicyclo[3.2.1]octan-3-yl)-8-fluoro-2-(((2R,7aS)-2-fluorotetrahydro-1H-pyrrolizin-7a(5H)-yl)methoxy)pyrido[4,3-d]pyrimidin-7-yl)benzonitrile (9.4 mg, 37% yield). LCMS (MM-ES+APCI, Pos): m/z 518.2 (M+H).

Example 410

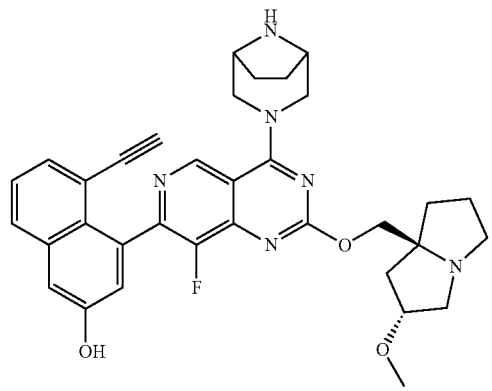 [SMILES: C#Cc1cccc2cc(O)cc(-c3ncc4c(N5CC6CCC(C5)N6)nc(OC[C@@]56CCCN5C[C@H](OC)C6)nc4c3F)c12]

4-(4-((1R,5S)-3,8-diazabicyclo[3.2.1]octan-3-yl)-8-fluoro-2-((2-methoxytetrahydro-1H-pyrrolizin-7a (5H)-yl)methoxy)pyrido[4,3-d]pyrimidin-7-yl)-5-ethynylnaphthalen-2-ol (mixture of trans diastereomers)

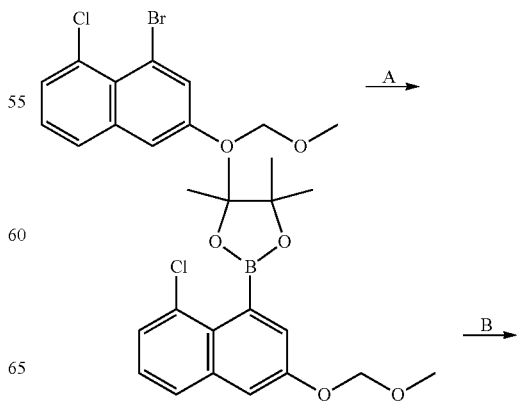

-continued

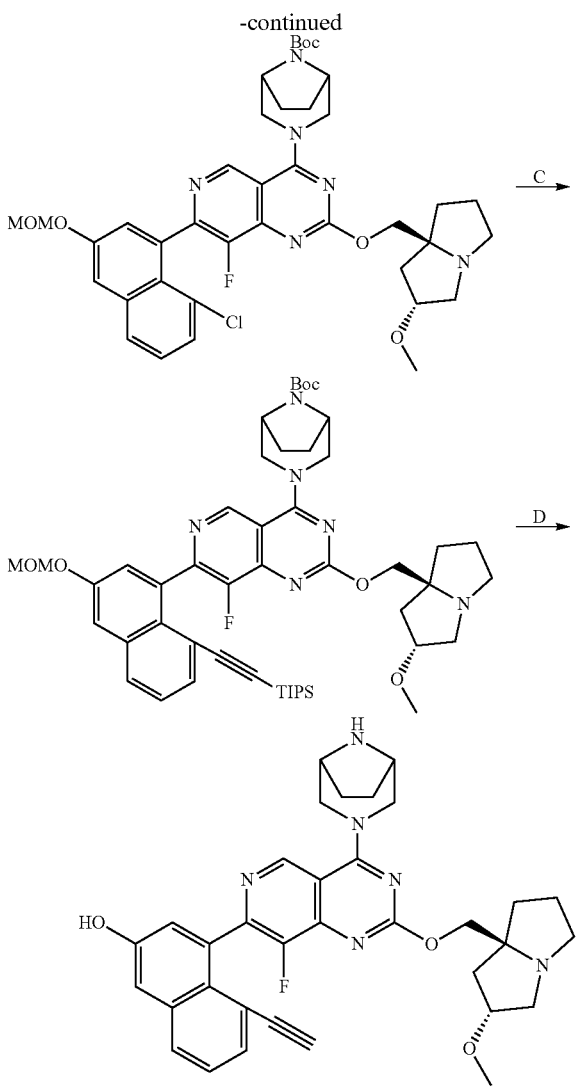

Step A. 2-(8-chloro-3-(methoxymethoxy)naphthalen-1-yl)-4,4,5,5-tetramethyl-1,3,2-dioxaborolane. 1-Bromo-8-chloro-3-(methoxymethoxy)naphthalene (0.25 g, 0.82 mmol), 4,4,4',4',5,5,5',5'-octamethyl-2,2'-bi(1,3,2-dioxaborolane) (0.62 g, 2.4 mmol), PdCl$_2$(dppf) (60 mg, 0.082 mmol), and KOAc (0.24 g, 2.4 mmol) were added to a vial with stir bar and septa cap. The vial was degassed and purged with N$_2$ 3 times before dioxane (4 mL) was added. The vial was sparged with N$_2$ for 15 minutes and the reaction was heated to 95° C. for 18 hours. The reaction was diluted with water and extracted with DCM 2 times. The DCM layers were combined, dried with Na$_2$SO$_4$, filtered, and concentrated. The residue was purified by flash chromatography (silica, 0-20% EtOAc in hexanes) four times. 2-(8-Chloro-3-(methoxymethoxy)naphthalen-1-yl)-4,4,5,5-tetramethyl-1,3,2-dioxaborolane was isolated as a colorless oil (0.17 g, 59%). $^1$H NMR (400 MHz, CDCl$_3$): δ 7.64 (dd, J=8.2, 0.7 Hz, 1H), 7.45-7.38 (m, 2H), 7.35 (d, J=2.5 Hz, 1H), 7.30 (t, J=7.8 Hz, 1H), 5.28 (s, 2H), 3.50 (s, 3H), 1.43 (s, 12H).

Step B. tert-butyl (1R,5S)-3-(7-(8-chloro-3-(methoxymethoxy)naphthalen-1-yl)-8-fluoro-2-((2-methoxytetrahydro-1H-pyrrolizin-7a(5H)-yl)methoxy)pyrido[4,3-d]pyrimidin-4-yl)-3,8-diazabicyclo[3.2.1]octane-8-carboxylate (mixture of trans diastereomers). Tert-butyl (1R,5S)-3-(7-chloro-8-fluoro-2-((2-methoxytetrahydro-1H-pyrrolizin-7a(5H)-yl)methoxy)pyrido[4,3-d]pyrimidin-4-yl)-3,8-diazabicyclo[3.2.1] octane-8-carboxylate (trans diastereomers, synthesized according to Example 388, Step A, 39 mg, 0.068 mmol), 2-(8-chloro-3-(methoxymethoxy)naphthalen-1-yl)-4,4,5,5-tetramethyl-1,3,2-dioxaborolane (36 mg, 0.10 mmol), and XPhos Pd Gen 2 (5.4 mg, 0.007 mmol) were added to a vial with a stir bar and septa cap. The vial was degassed and purged with N$_2$ 3 times before degassed THF (0.2 mL) and degassed 0.5 M aqueous K$_3$PO$_4$ (0.3 mL, 0.14 mmol) were added. The reaction was heated to 40° C. for 2 hours. The reaction was diluted with water and extracted with DCM 3 times. The DCM layers were combined, dried with Na$_2$SO$_4$, filtered, and concentrated. The residue was purified via reverse phase chromatography (C18, 0-80% MeCN in water with 0.1% TFA). The fractions containing the product were combined, diluted with DCM, and washed with saturated Na$_2$CO$_3$. The DCM layer was dried with Na$_2$SO$_4$, filtered, and concentrated to yield tert-butyl (1R,5S)-3-(7-(8-chloro-3-(methoxymethoxy)naphthalen-1-yl)-8-fluoro-2-((2-methoxytetrahydro-1H-pyrrolizin-7a(5H)-yl)methoxy)pyrido[4,3-d]pyrimidin-4-yl)-3,8-diazabicyclo[3.2.1] octane-8-carboxylate (mixture of trans diastereomers) (10 mg 20%). LCMS (MM-ES+APCI, Pos): m/z 749.4 (M+H).

Step C. tert-butyl (1R,5S)-3-(8-fluoro-7-(3-(methoxymethoxy)-8-((triisopropylsilyl)ethynyl)naphthalen-1-yl)-2-((2-methoxytetrahydro-1H-pyrrolizin-7a(5H)-yl)methoxy)pyrido[4,3-d]pyrimidin-4-yl)-3,8-diazabicyclo [3.2.1]octane-8-carboxylate (mixture of trans diastereomers). Tert-butyl (1R,5S)-3-(7-(8-chloro-3-(methoxymethoxy)naphthalen-1-yl)-8-fluoro-2-((2-methoxytetrahydro-1H-pyrrolizin-7a(5H)-yl)methoxy) pyrido[4,3-d]pyrimidin-4-yl)-3,8-diazabicyclo[3.2.1] octane-8-carboxylate (mixture of trans diastereomers) (10 mg, 0.014 mmol), dichlorobis(acetonitrile)palladium(II) (3.6 mg, 0.014 mmol), 2-(dicyclohexylphosphino)-2,4,6-triisopropylbiphenyl (6.7 mg, 0.014 mmol), and Cs$_2$CO$_3$ (14 mg, 0.042 mmol) were added to a vial with a stir bar and septa cap. The vial was degassed and purged with N$_2$ 3 times before ethynyltriisopropylsilane (31 μL, 0.14 mmol) and MeCN (0.5 mL) were added. The vial was sparged with N$_2$ for 10 minutes before the reaction was heated to 80° C. for 2 hours. The reaction was diluted with water and extracted with DCM 3 times. The DCM layers were combined, dried with Na$_2$SO$_4$, filtered, and concentrated. The residue was purified by flash chromatography (silica, 0-15% MeOH in DCM) to yield tert-butyl (1R,5S)-3-(8-fluoro-7-(3-(methoxymethoxy)-8-((triisopropylsilyl)ethynyl)naphthalen-1-yl)-2-((2-methoxytetrahydro-1H-pyrrolizin-7a(5H)-yl)methoxy)pyrido[4,3-d]pyrimidin-4-yl)-3,8-diazabicyclo [3.2.1]octane-8-carboxylate (mixture of trans diastereomers) (9 mg, 72%). LCMS (MM-ES+APCI, Pos): m/z 895.4 (M+H).

Step D. 4-(4-((1R,5S)-3,8-diazabicyclo[3.2.1]octan-3-yl)-8-fluoro-2-((2-methoxytetrahydro-1H-pyrrolizin-7a (5H)-yl)methoxy)pyrido[4,3-d]pyrimidin-7-yl)-5-ethynylnaphthalen-2-ol (mixture of trans diastereomers). Tert-butyl (1R,5S)-3-(8-fluoro-7-(3-(methoxymethoxy)-8-((triisopropylsilyl)ethynyl)naphthalen-1-yl)-2-((2-methoxytetrahydro-1H-pyrrolizin-7a(5H)-yl)methoxy) pyrido[4,3-d]pyrimidin-4-yl)-3,8-diazabicyclo[3.2.1] octane-8-carboxylate (mixture of trans diastereomers) (9 mg, 0.01 mmol) was added to a vial with a stir bar and septa. THF (0.2 mL) was added followed by 1.0 M TBAF in THF (60 μL, 0.06 mmol). The reaction was stirred at room temperature for 1 hour. The reaction was diluted with water and extracted with DCM 3 times. The DCM layers were combined, dried with Na₂SO₄, filtered, and concentrated. To the residue DCM (1 mL) and 4M HCl in dioxanes (1 mL) were added. The reaction was stirred at room temperature for 1 hour before being concentrated down. The residue was purified using a reverse phase column (C18, 0-80% MeCN in water with 0.1% TFA). The fractions containing the product were combined, frozen, and lyophilized. The acid salt was passed through a PL-HCO3 ME Resin plug with methanol and concentrated to yield 4-(4-((1R,5S)-3,8-diazabicyclo[3.2.1]octan-3-yl)-8-fluoro-2-((2-methoxytetrahydro-1H-pyrrolizin-7a(5H)-yl)methoxy)pyrido[4,3-d]pyrimidin-7-yl)-5-ethynylnaphthalen-2-ol (mixture of trans diastereomers) as a brown solid (1.1 mg, 18%). LCMS (MM-ES+APCI, Pos): m/z 595.2 (M+H).

Example 411

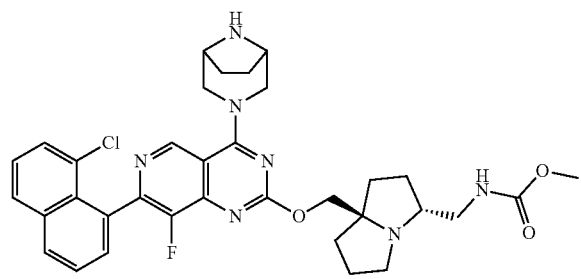 [SMILES: COC(=O)NC[C@H]1CC[C@@]2(COc3nc(N4CC5CCC(C4)N5)c4cnc(-c5cccc6cccc(Cl)c56)c(F)c4n3)CCCN12]

methyl ((7a-(((4-(3,8-diazabicyclo[3.2.1]octan-3-yl)-7-(8-chloronaphthalen-1-yl)-8-fluoropyrido[4,3-d]pyrimidin-2-yl)oxy)methyl)hexahydro-1H-pyrrolizin-3-yl)methyl)carbamate (Mixture of Trans Diastereomers)

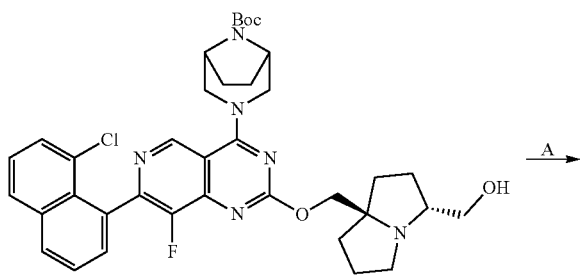

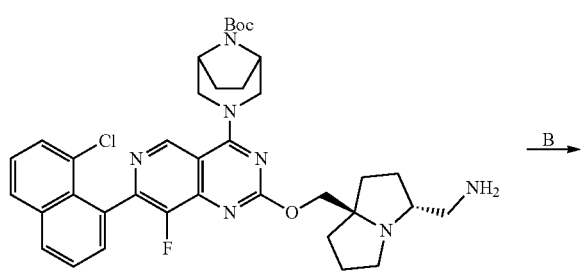

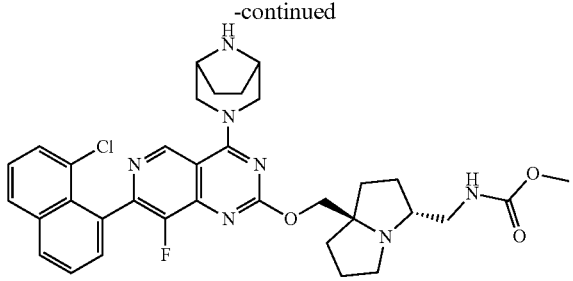

Step A. tert-butyl 3-(2-((3-(aminomethyl)tetrahydro-1H-pyrrolizin-7a(5H)-yl)methoxy)-7-(8-chloronaphthalen-1-yl)-8-fluoropyrido[4,3-d]pyrimidin-4-yl)-3,8-diazabicyclo[3.2.1]octane-8-carboxylate bis(2,2,2-trifluoroacetate) (mixture of trans diastereomers). To a solution of tert-butyl (1R,5S)-3-(7-(8-chloronaphthalen-1-yl)-8-fluoro-2-((3-(hydroxymethyl)tetrahydro-1H-pyrrolizin-7a(5H)-yl)methoxy)pyrido[4,3-d]pyrimidin-4-yl)-3,8-diazabicyclo[3.2.1]octane-8-carboxylate (mixture of trans diastereomers, synthesized according to Example 405, step A-B, 69 mg, 0.10 mmol) in THF (1 mL) at 0° C. was added Et₃N (0.021 mL, 0.15 mmol), followed by Ms-Cl (0.012 mL, 0.15 mmol). The solution was warmed to rt, concentrated, dissolved in MeOH (1 mL), and treated with NH₃·H₂O (28%, 1 mL). The vial was closed, and the solution was heated at 50° C. for 36 h. The mixture was cooled to rt and was purified by preparative C18 HPLC (Gilson, 0-95% CH₃CN/H₂O with 0.1% TFA). The desired fractions were combined and lyophilized to give the title compound (25 mg, 27%) as a white solid. LCMS (MM-ES+APCI, Pos): m/z 688.3 (M+H).

Step B. methyl ((7a-(((4-(3,8-diazabicyclo[3.2.1]octan-3-yl)-7-(8-chloronaphthalen-1-yl)-8-fluoropyrido[4,3-d]pyrimidin-2-yl)oxy)methyl)hexahydro-1H-pyrrolizin-3-yl)methyl)carbamate bis(2,2,2-trifluoroacetate) (mixture of trans diastereomers). To a solution of tert-butyl (1R,5S)-3-(2-((3-(aminomethyl)tetrahydro-1H-pyrrolizin-7a(5H)-yl)methoxy)-7-(8-chloronaphthalen-1-yl)-8-fluoropyrido[4,3-d]pyrimidin-4-yl)-3,8-diazabicyclo[3.2.1]octane-8-carboxylate bis(2,2,2-trifluoroacetate) (mixture of trans diastereomers) (8 mg, 0.009 mmol) in DCM (0.5 mL) at rt was added Et₃N (5 µL, 0.035 mmol) followed by addition of methyl chloroformate (3 µL, 0.03 mmol). The solution was stirred at rt for 0.5 h followed by addition of TFA (0.44 mL). The mixture was stirred at r.t. for 0.5 h, concentrated, and was purified by preparative C18 HPLC (Gilson, 0-95% CH₃CN/H₂O with 0.1% TFA). The desired fractions were combined and lyophilized to give the title compound (5.0 mg, 66%) as the bis TFA salt. LCMS (MM-ES+APCI, Pos): m/z 646.3 (M+H).

Example 412

845

3-((7a-(((4-(3,8-diazabicyclo[3.2.1]octan-3-yl)-7-(8-chloronaphthalen-1-yl)-8-fluoropyrido[4,3-d]pyrimidin-2-yl)oxy)methyl)hexahydro-1H-pyrrolizin-3-yl)methyl)-1,1-dimethylurea (Mixture of Trans Diastereomers)

846

N-((7a-(((4-(3,8-diazabicyclo[3.2.1]octan-3-yl)-7-(8-chloronaphthalen-1-yl)-8-fluoropyrido[4,3-d]pyrimidin-2-yl)oxy)methyl)hexahydro-1H-pyrrolizin-3-yl)methyl)acetamide (mixture of trans diastereomers)

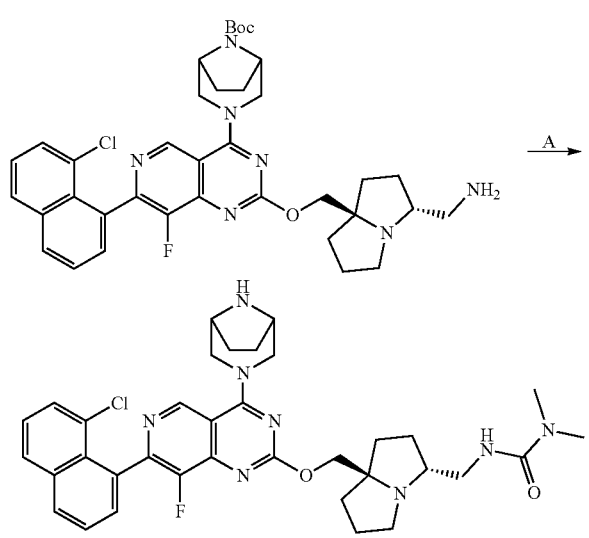

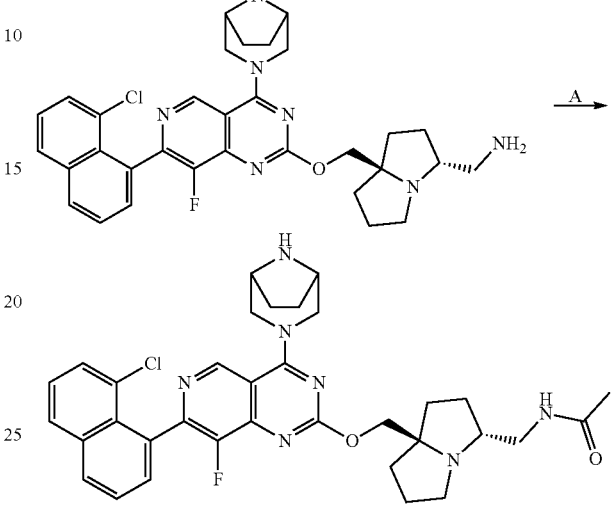

Step A. 3-((7a-(((4-(3,8-diazabicyclo[3.2.1]octan-3-yl)-7-(8-chloronaphthalen-1-yl)-8-fluoropyrido[4,3-d]pyrimidin-2-yl)oxy)methyl)hexahydro-1H-pyrrolizin-3-yl)methyl)-1,1-dimethylurea bis(2,2,2-trifluoroacetate) (mixture of trans diastereomers). To a solution of tert-butyl (1R,5S)-3-(2-((3-(aminomethyl)tetrahydro-1H-pyrrolizin-7a(5H)-yl)methoxy)-7-(8-chloronaphthalen-1-yl)-8-fluoropyrido[4,3-d]pyrimidin-4-yl)-3,8-diazabicyclo[3.2.1]octane-8-carboxylate bis(2,2,2-trifluoroacetate) (mixture of trans diastereomers) (8.0 mg, 0.0087 mmol) in DCM (0.5 mL) at rt was added Et₃N (5 μL, 0.04 mmol) followed by addition of dimethylcarbamyl chloride (3 μL, 0.04 mmol). The solution was stirred at r.t. for 15 h followed by addition of TFA (0.44 mL). The mixture was stirred at r.t. for 0.5 h, concentrated, and was purified by preparative C18 HPLC (Gilson, 0-95% CH₃CN/H₂O with 0.1% TFA). The desired fractions were combined and lyophilized to give the title compound (6 mg, 77%) as the bis TFA salt. LCMS (MM-ES+APCI, Pos): m/z 659.3 (M+H).

Example 413

Step A. N-((7a-(((4-(3,8-diazabicyclo[3.2.1]octan-3-yl)-7-(8-chloronaphthalen-1-yl)-8-fluoropyrido[4,3-d]pyrimidin-2-yl)oxy)methyl)hexahydro-1H-pyrrolizin-3-yl)methyl)acetamide bis(2,2,2-trifluoroacetate) (mixture of trans diastereomers). To a solution of tert-butyl (1R,5S)-3-(2-((3-(aminomethyl)tetrahydro-1H-pyrrolizin-7a(5H)-yl)methoxy)-7-(8-chloronaphthalen-1-yl)-8-fluoropyrido[4,3-d]pyrimidin-4-yl)-3,8-diazabicyclo[3.2.1]octane-8-carboxylate bis(2,2,2-trifluoroacetate) (mixture of trans diastereomers) (8 mg, 0.009 mmol) in DCM (0.5 mL) was added Et₃N (5 μL, 0.04 mmol) at r.t. followed by addition of acetic anhydride (3 μL, 0.03 mmol). The solution was stirred at r.t. for 0.5 h and TFA (0.5 mL) was added. The mixture was stirred at r.t. for 1 h, concentrated, and was purified by preparative C18 HHPLC (Gilson, 0-95% CH₃CN/H₂O with 0.1% TFA). The desired fractions were combined and lyophilized to give the title compound (4 mg, 53%) as the bis TFA salt. LCMS (MM-ES+APCI, Pos): m/z 630.4 (M+H).

Example 414

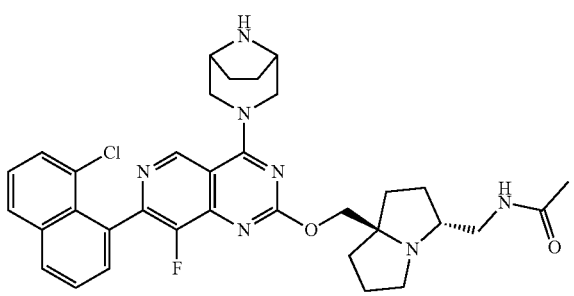 [SMILES: CC(=O)NC[C@H]1CC[C@@]2(COc3nc(N4CC5CCC(C4)N5)c4cnc(-c5cccc6cccc(Cl)c56)c(F)c4n3)CCCN12]

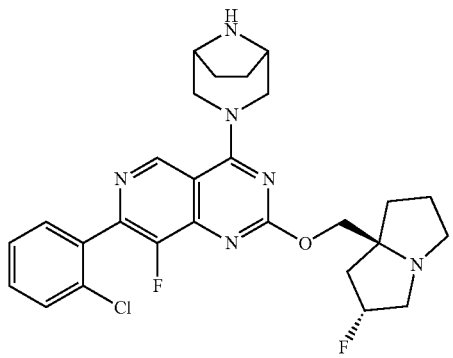 [SMILES: Fc1c(-c2ccccc2Cl)ncc2c(N3CC4CCC(C3)N4)nc(OC[C@@]34CCCN3C[C@H](F)C4)nc12]

4-((1R,5S)-3,8-diazabicyclo[3.2.1]octan-3-yl)-7-(2-chlorophenyl)-8-fluoro-2-((2-fluorotetrahydro-1H-pyrrolizin-7a(5H)-yl)methoxy)pyrido[4,3-d]pyrimidine (racemic, trans)

Synthesized according to Example 409 substituting (2-chlorophenyl)boronic acid in place of 2-cyanophenylboronic acid in step B to afford 4-((1R,5S)-3,8-diazabicyclo[3.2.1]octan-3-yl)-7-(2-chlorophenyl)-8-fluoro-2-((2-fluorotetrahydro-1H-pyrrolizin-7a(5H)-yl)methoxy)pyrido[4,3-d]pyrimidine (racemic, trans) (29 mg, 39%). LCMS (MM-ES+APCI, Pos): m/z 527.2 (M+H).

Example 415

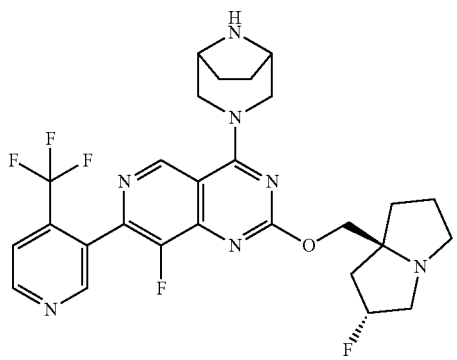 [SMILES: Fc1c(-c2cnccc2C(F)(F)F)ncc2c(N3CC4CCC(C3)N4)nc(OC[C@@]34CCCN3C[C@H](F)C4)nc12]

4-((1R,5S)-3,8-diazabicyclo[3.2.1]octan-3-yl)-8-fluoro-2-((2-fluorotetrahydro-1H-pyrrolizin-7a(5H)-yl)methoxy)-7-(4-(trifluoromethyl)pyridin-3-yl)pyrido[4,3-d]pyrimidine (racemic, trans)

Synthesized according to Example 409 substituting (2-(trifluoromethyl)pyridin-3-yl)boronic acid in place of 2-cyanophenylboronic acid in step B to afford 4-((1R,5S)-3,8-diazabicyclo[3.2.1]octan-3-yl)-8-fluoro-2-((2-fluorotetrahydro-1H-pyrrolizin-7a(5H)-yl)methoxy)-7-(4-(trifluoromethyl)pyridin-3-yl)pyrido[4,3-d]pyrimidine (racemic, trans) (20 mg, 67%). LCMS (MM-ES+APCI, Pos): m/z 562.2 (M+H).

Example 416

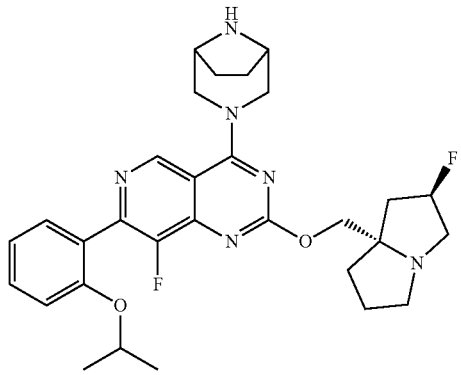 [SMILES: CC(C)Oc1ccccc1-c1ncc2c(N3CC4CCC(C3)N4)nc(OC[C@@]34CCCN3C[C@H](F)C4)nc2c1F]

4-((1R,5S)-3,8-diazabicyclo[3.2.1]octan-3-yl)-8-fluoro-2-((2-fluorotetrahydro-1H-pyrrolizin-7a(5H)-yl)methoxy)-7-(2-isopropoxyphenyl)pyrido[4,3-d]pyrimidine (racemic, trans)

Step A. Tert-butyl (1R,5S)-3-(8-fluoro-2-((2-fluorotetrahydro-1H-pyrrolizin-7a(5H)-yl)methoxy)-7-(2-isopropoxyphenyl)pyrido[4,3-d]pyrimidin-4-yl)-3,8-diazabicyclo[3.2.1]octane-8-carboxylate (racemic, trans). Synthesized according to Example 424, Step A substituting (2-isopropoxyphenyl)boronic acid in place of 2-(5-(benzyloxy)-2-(2,2,2-trifluoroethyl)phenyl)-4,4,5,5-tetramethyl-1,3,2-dioxaborolane to afford tert-butyl (1R,5S)-3-(8-fluoro-2-((2-fluorotetrahydro-1H-pyrrolizin-7a(5H)-yl)methoxy)-7-(2-isopropoxyphenyl)pyrido[4,3-d]pyrimidin-4-yl)-3,8-diazabicyclo[3.2.1]octane-8-carboxylate (racemic, trans) (45 mg, 76%). LCMS (MM-ES+APCI, Pos): m/z 651.3 (M+H).

Step B. 4-((1R,5S)-3,8-diazabicyclo[3.2.1]octan-3-yl)-8-fluoro-2-((2-fluorotetrahydro-1H-pyrrolizin-7a(5H)-yl)methoxy)-7-(2-isopropoxyphenyl)pyrido[4,3-d]pyrimidine (racemic, trans). Synthesized according to Example 417, Step B substituting tert-butyl (1R,5S)-3-(8-fluoro-2-((2-fluorotetrahydro-1H-pyrrolizin-7a(5H)-yl)methoxy)-7-(2-isopropoxyphenyl)pyrido[4,3-d]pyrimidin-4-yl)-3,8-diazabicyclo[3.2.1]octane-8-carboxylate (racemic, trans) in place of tert-butyl (1R,5S)-3-(8-fluoro-2-((2-fluorotetrahydro-1H-pyrrolizin-7a(5H)-yl)methoxy)-7-(2-isobutylphenyl)pyrido[4,3-d]pyrimidin-4-yl)-3,8-diazabicyclo[3.2.1]octane-8-carboxylate (racemic, trans) to afford 4-((1R,5S)-3,8-diazabicyclo[3.2.1]octan-3-yl)-8-fluoro-2-((2-fluorotetrahydro-1H-pyrrolizin-7a(5H)-yl)methoxy)-7-(2-isopropoxyphenyl)pyrido[4,3-d]pyrimidine (racemic, trans) (22 mg, 58%). LCMS (MM-ES+APCI, Pos): m/z 551.3 (M+H).

Example 417

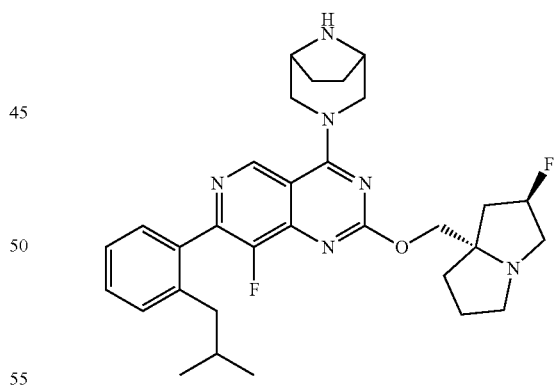

4-((1R,5S)-3,8-diazabicyclo[3.2.1]octan-3-yl)-8-fluoro-2-((2-fluorotetrahydro-1H-pyrrolizin-7a(5H)-yl)methoxy)-7-(2-isobutylphenyl)pyrido[4,3-d]pyrimidine (racemic, trans)

Step A. Tert-butyl (1R,5S)-3-(8-fluoro-2-((2-fluorotetrahydro-1H-pyrrolizin-7a(5H)-yl)methoxy)-7-(2-isobutylphenyl)pyrido[4,3-d]pyrimidin-4-yl)-3,8-diazabicyclo[3.2.1]octane-8-carboxylate (racemic, trans). Synthesized according to Example 424, Step A substituting 2-(2- isobutylphenyl)-4,4,5,5-tetramethyl-1,3,2-dioxaborolane in place of 2-(5-(benzyloxy)-2-(2,2,2-trifluoroethyl)phenyl)-4,4,5,5-tetramethyl-1,3,2-dioxaborolane to afford tert-butyl (1R,5S)-3-(8-fluoro-2-((2-fluorotetrahydro-1H-pyrrolizin-7a(5H)-yl)methoxy)-7-(2-isobutylphenyl)pyrido[4,3-d]pyrimidin-4-yl)-3,8-diazabicyclo[3.2.1]octane-8-carboxylate (racemic, trans) (41 mg, 70%). LCMS (MM-ES+APCI, Pos): m/z 649.3 (M+H).

Step B. 4-((1R,5S)-3,8-diazabicyclo[3.2.1]octan-3-yl)-8-fluoro-2-((2-fluorotetrahydro-1H-pyrrolizin-7a(5H)-yl)methoxy)-7-(2-isobutylphenyl)pyrido[4,3-d]pyrimidine bis(2,2,2-trifluoroacetate) (racemic, trans). Synthesized according to Example 426, Step D substituting tert-butyl (1R,5S)-3-(8-fluoro-2-((fluorotetrahydro-1H-pyrrolizin-7a(5H)-yl)methoxy)-7-(2-isobutylphenyl)pyrido[4,3-d]pyrimidin-4-yl)-3,8-diazabicyclo[3.2.1]octane-8-carboxylate (racemic, trans) in place of tert-butyl (1R,5S)-3-(7-(8-ethyl-7-fluoronaphthalen-1-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate. The dihydrochloride salt was purified by prep HPLC (0-95% MeCN/H₂O+0.1% TFA) and lyophilized to afford 4-((1R,5S)-3,8-diazabicyclo[3.2.1]octan-3-yl)-8-fluoro-2-((2-fluorotetrahydro-1H-pyrrolizin-7a(5H)-yl)methoxy)-7-(2-isobutylphenyl)pyrido[4,3-d]pyrimidine bis(2,2,2-trifluoroacetate) (racemic, trans) (29 mg, 68%). LCMS (MM-ES+APCI, Pos): m/z 549.3 (M+H).

Example 418

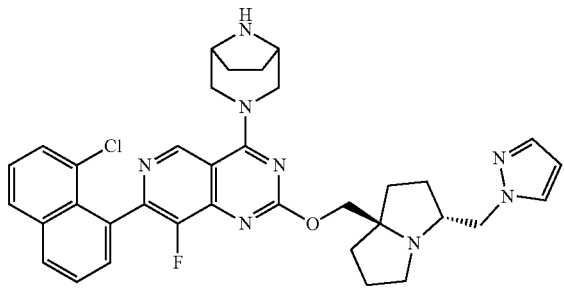 [SMILES: Fc1c(-c2cccc3cccc(Cl)c23)ncc2c(N3CC4CCC(C3)N4)nc(OC[C@]34CCCN3[C@@H](Cn3cccn3)CC4)nc12]

2-(((3R,7aR)-3-((1H-pyrazol-1-yl)methyl)hexahydro-1H-pyrrolizin-7a-yl)methoxy)-4-((1R,5S)-3,8-diazabicyclo[3.2.1]octan-3-yl)-7-(8-chloronaphthalen-1-yl)-8-fluoropyrido[4,3-d]pyrimidine (mixture of trans diastereomers)

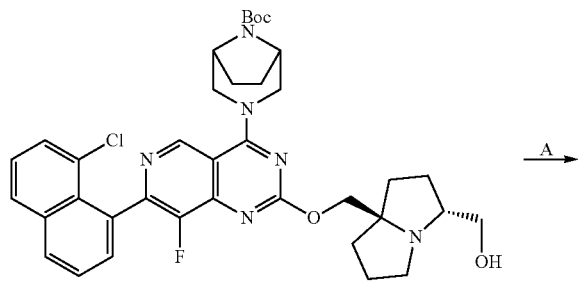

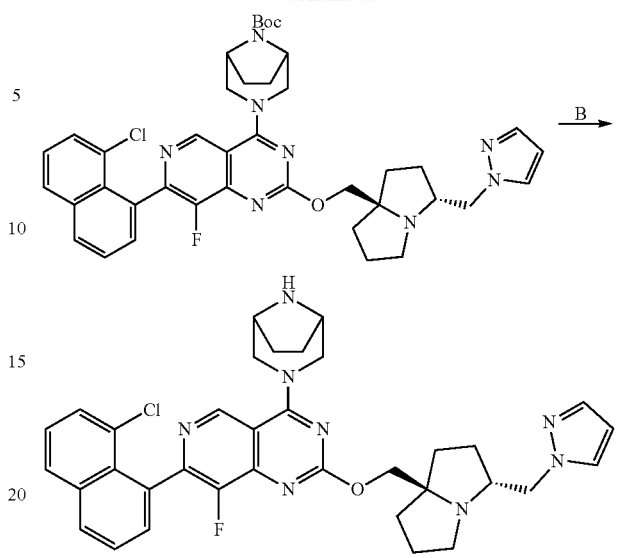

Step A. tert-butyl 3-(2-((3-((1H-pyrazol-1-yl)methyl)tetrahydro-1H-pyrrolizin-7a(5H)-yl)methoxy)-7-(8-chloronaphthalen-1-yl)-8-fluoropyrido[4,3-d]pyrimidin-4-yl)-3,8-diazabicyclo[3.2.1]octane-8-carboxylate (mixture of trans diastereomers). To a solution of tert-butyl (1R,5S)-3-(7-(8-chloronaphthalen-1-yl)-8-fluoro-2-((3-(hydroxymethyl)tetrahydro-1H-pyrrolizin-7a(5H)-yl)methoxy)pyrido[4,3-d]pyrimidin-4-yl)-3,8-diazabicyclo[3.2.1]octane-8-carboxylate (mixture of trans diastereomers, synthesized according to Example 405, Step A-B, 20 mg, 0.029 mmol) in DCM (0.3 mL) at 0° C. was added Et₃N (12 µL, 0.087 mmol), followed by Ms-Cl (7 µL, 0.09 mmol). The mixture was stirred at r.t. for 30 min., diluted with DCM and washed with NaHCO₃ (sat.). The solution was dried (Na₂SO₄) and concentrated to give an oil. The oil was dissolved in DMF (0.6 mL) and treated with 1H-pyrazole (9.9 mg, 0.15 mmol) and NaH (60%, 5.8 mg, 0.15 mmol). The mixture was stirred at r.t. for 15 h and at 50° C. for 5 h. The mixture was cooled to r.t. and was purified by preparative C18 HPLC (Gilson, 0-95% CH₃CN/H₂O with 0.1% TFA). The desired fractions were combined, basified with NaHCO₃ (sat.), and extracted with DCM/IPA (5:1). The extract was dried (Na₂SO₄) and concentrated to give crude title compound (7.0 mg, 33%) as a white solid. LCMS (MM-ES+APCI, Pos): m/z 739.3 (M+H).

Step B. 2-((3-((1H-pyrazol-1-yl)methyl)tetrahydro-1H-pyrrolizin-7a(5H)-yl)methoxy)-4-(3,8-diazabicyclo[3.2.1]octan-3-yl)-7-(8-chloronaphthalen-1-yl)-8-fluoropyrido[4,3-d]pyrimidine bis(2,2,2-trifluoroacetate) (mixture of trans diastereomers). To a solution of tert-butyl 3-(2-((3-((1H-pyrazol-1-yl)methyl)tetrahydro-1H-pyrrolizin-7a(5H)-yl)methoxy)-7-(8-chloronaphthalen-1-yl)-8-fluoropyrido[4,3-d]pyrimidin-4-yl)-3,8-diazabicyclo[3.2.1]octane-8-carboxylate (mixture of trans diastereomers) (7 mg, 0.009 mmol) in DCM (0.50 mL) was added TFA (0.25 mL). The solution was stirred at r.t. for 0.5 h, concentrated, and was purified by preparative C18 HPLC (Gilson, 0-95% CH₃CN/H₂O with 0.1% TFA). The desired fractions were combined and lyophilized to give the title compound (4.0 mg, 49%) as the bis TFA salt. LCMS (MM-ES+APCI, Pos): m/z 639.3 (M+H).

Example 419

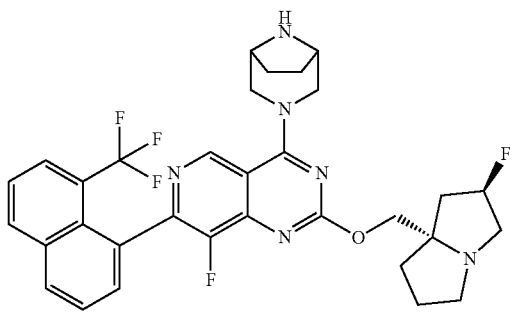 [SMILES: Fc1c(-c2cccc3cccc(C(F)(F)F)c23)ncc2c(N3CC4CCC(C3)N4)nc(OC[C@@]34CCCN3C[C@H](F)C4)nc12]

4-((1R,5S)-3,8-diazabicyclo[3.2.1]octan-3-yl)-8-fluoro-2-(((2R,7aS)-2-fluorotetrahydro-1H-pyrrolizin-7a(5H)-yl)methoxy)-7-(8-(trifluoromethyl)naphthalen-1-yl)pyrido[4,3-d]pyrimidine (racemic, trans)

Step A. Tert-butyl (1R,5S)-3-(8-fluoro-2-((2-fluorotetrahydro-1H-pyrrolizin-7a(5H)-yl)methoxy)-7-(8-(trifluoromethyl)naphthalen-1-yl)pyrido[4,3-d]pyrimidin-4-yl)-3,8-diazabicyclo[3.2.1]octane-8-carboxylate (racemic, trans). Synthesized according to Example 426, Step A substituting tert-butyl (1R,5S)-3-(7-chloro-8-fluoro-2-((2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate in place of tert-butyl (1R,5S)-3-(7-chloro-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate and 4,4,5,5-tetramethyl-2-(8-(trifluoromethyl)naphthalen-1-yl)-1,3,2-dioxaborolane in place of ((2-fluoro-8-(4,4,5,5-tetramethyl-1,3,2-dioxaborolan-2-yl)naphthalen-1-yl)ethynyl)triisopropylsilane to afford tert-butyl (1R,5S)-3-(8-fluoro-2-((2-fluorotetrahydro-1H-pyrrolizin-7a(5H)-yl)methoxy)-7-(8-(trifluoromethyl)naphthalen-1-yl)pyrido[4,3-d]pyrimidin-4-yl)-3,8-diazabicyclo[3.2.1]octane-8-carboxylate (racemic, trans) (42 mg, 65%). LCMS (MM-ES+APCI, Pos): m/z 711.3 (M+H).

Step B. 4-((1R,5S)-3,8-diazabicyclo[3.2.1]octan-3-yl)-7-chloro-8-fluoro-2-((2-fluorotetrahydro-1H-pyrrolizin-7a(5H)-yl)methoxy)pyrido[4,3-d]pyrimidine (racemic, trans). Synthesized according to Example 422, Step B substituting tert-butyl (1R,5S)-3-(8-fluoro-2-((2-fluorotetrahydro-1H-pyrrolizin-7a(5H)-yl)methoxy)-7-(8-(trifluoromethyl)naphthalen-1-yl)pyrido[4,3-d]pyrimidin-4-yl)-3,8-diazabicyclo[3.2.1]octane-8-carboxylate (racemic, trans) in place of tert-butyl (1R,5S)-3-(8-fluoro-2-((tetrahydro-1H-pyrrolizin-7a(5H)-yl)methoxy)-7-(8-(trifluoromethyl)naphthalen-1-yl)pyrido[4,3-d]pyrimidin-4-yl)-3,8-diazabicyclo[3.2.1]octane-8-carboxylate to afford 4-((1R,5S)-3,8-diazabicyclo[3.2.1]octan-3-yl)-7-chloro-8-fluoro-2-((2-fluorotetrahydro-1H-pyrrolizin-7a(5H)-yl)methoxy)pyrido[4,3-d]pyrimidine (racemic, trans) (20 mg, 55%). LCMS (MM-ES+APCI, Pos): m/z 611.2 (M+H).

Example 420

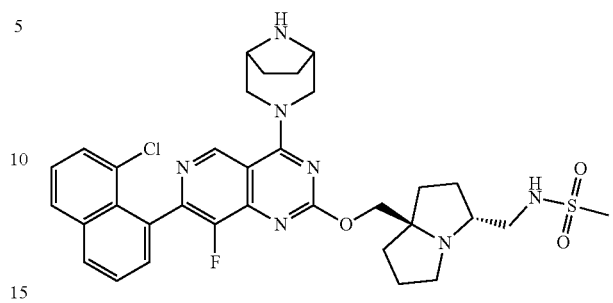

N-(((3R,7aR)-7a-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)hexahydro-1H-pyrrolizin-3-yl)methyl)methanesulfonamide (mixture of trans diastereomers)

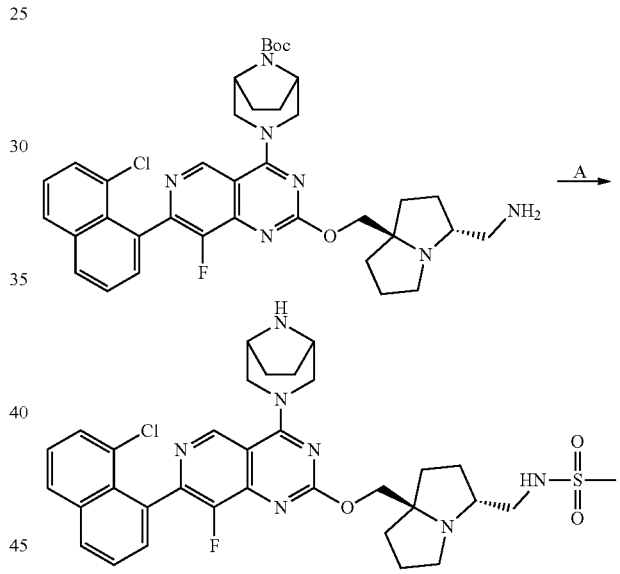

Step A. N-((7a-(((4-(3,8-diazabicyclo[3.2.1]octan-3-yl)-7-(8-chloronaphthalen-1-yl)-8-fluoropyrido[4,3-d]pyrimidin-2-yl)oxy)methyl)hexahydro-1H-pyrrolizin-3-yl)methyl)methanesulfonamide bis(2,2,2-trifluoroacetate) (mixture of trans diastereomers). To a solution of tert-butyl (1R,5S)-3-(2-((3-(aminomethyl)tetrahydro-1H-pyrrolizin-7a(5H)-yl)methoxy)-7-(8-chloronaphthalen-1-yl)-8-fluoropyrido[4,3-d]pyrimidin-4-yl)-3,8-diazabicyclo[3.2.1]octane-8-carboxylate (mixture of trans diastereomers) (9 mg, 0.01 mmol) in DCM (1 mL) was added Et₃N (0.013 mL, 0.092 mmol), followed by Ms-Cl (0.0051 mL 0.065 mmol). The mixture was stirred at r.t. for 15 min. MeOH (1 drop) was added and the mixture was concentrated to dryness. The residue was dissolved in DCM (1 mL) and TFA (0.50 mL) and the reaction was stirred for 30 min. The solution was concentrated and the residue was purified by preparative C18 HPLC (Gilson, 0-95% CH₃CN/H₂O with 0.1% TFA). The desired fractions were combined and lyophilized to give the title compound (6 mg, 51%) the bis TFA salt. LCMS (MM-ES+APCI, Pos): m/z 666.2 (M+H).

Example 421

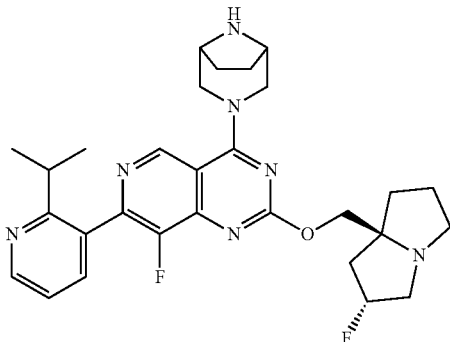

4-((1R,5S)-3,8-diazabicyclo[3.2.1]octan-3-yl)-8-fluoro-2-(((2R,7aS)-2-fluorohexahydro-1H-pyrrolizin-7a-yl)methoxy)-7-(2-isopropylpyridin-3-yl)pyrido[4,3-d]pyrimidine Synthesized according to Example 394, substituting (2-isopropylpyridin-3-yl)boronic acid in place of (2,6-diisopropylphenyl)boronic acid in Step A (7.3 mg, 16%). LCMS (MM-ES+APCI, Pos): m/z 536.3 [M+H].

Example 422

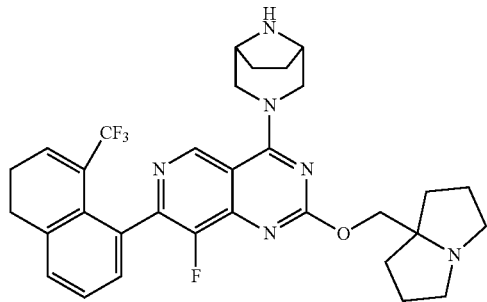 [SMILES: Fc1c(-c2cccc3c2C(C(F)(F)F)=CCC3)ncc2c(N3CC4CCC(C3)N4)nc(OCC34CCCN3CCC4)nc12]

4-((1R,5S)-3,8-diazabicyclo[3.2.1]octan-3-yl)-8-fluoro-2-((hexahydro-1H-pyrrolizin-7a-yl)methoxy)-7-(8-(trifluoromethyl)naphthalen-1-yl)pyrido[4,3-d]pyrimidine

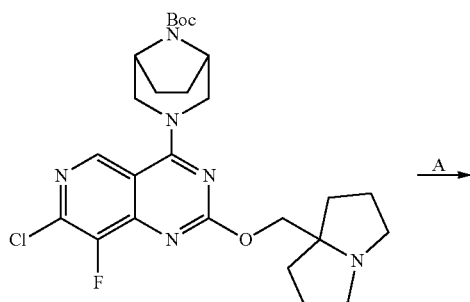

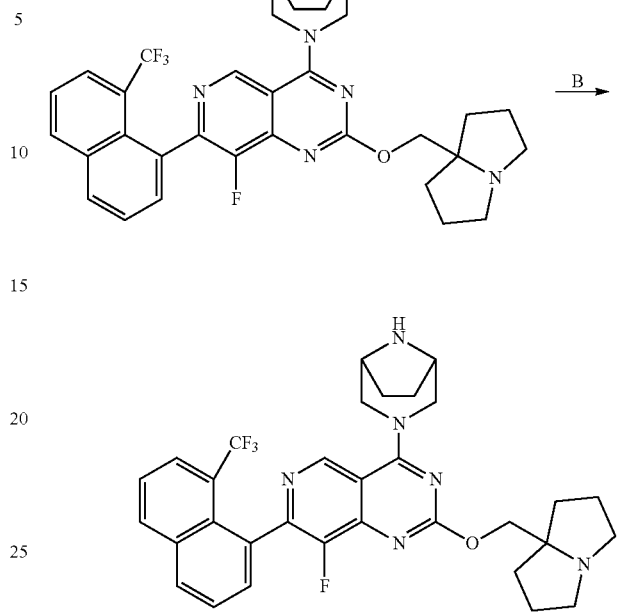

Step A. Tert-butyl (1R,5S)-3-(8-fluoro-2-((tetrahydro-1H-pyrrolizin-7a(5H)-yl)methoxy)-7-(8-(trifluoromethyl)naphthalen-1-yl)pyrido[4,3-d]pyrimidin-4-yl)-3,8-diazabicyclo[3.2.1]octane-8-carboxylate. Synthesized according to Example 426, Step A substituting 4,4,5,5-tetramethyl-2-(8-(trifluoromethyl)naphthalen-1-yl)-1,3,2-dioxaborolane in place of ((2-fluoro-8-(4,4,5,5-tetramethyl-1,3,2-dioxaborolan-2-yl)naphthalen-1-yl)ethynyl)triisopropylsilane to afford tert-butyl (1R,5S)-3-(8-fluoro-2-((tetrahydro-1H-pyrrolizin-7a(5H)-yl)methoxy)-7-(8-(trifluoromethyl)naphthalen-1-yl)pyrido[4,3-d]pyrimidin-4-yl)-3,8-diazabicyclo[3.2.1]octane-8-carboxylate (47 mg, 72%). LCMS (MM-ES+APCI, Pos): m/z 693.3 (M+H).

Step B. 4-((1R,5S)-3,8-diazabicyclo[3.2.1]octan-3-yl)-8-fluoro-2-((tetrahydro-1H-pyrrolizin-7a(5H)-yl)methoxy)-7-(8-(trifluoromethyl)naphthalen-1-yl)pyrido[4,3-d]pyrimidine. Tert-butyl (1R,5S)-3-(8-fluoro-2-((tetrahydro-1H-pyrrolizin-7a(5H)-yl)methoxy)-7-(8-(trifluoromethyl)naphthalen-1-yl)pyrido[4,3-d]pyrimidin-4-yl)-3,8-diazabicyclo[3.2.1]octane-8-carboxylate (47 mg, 0.068 mmol) was dissolved in DCM (1.5 mL). To this solution was added HCl (4N in 1,4-dioxane). The suspension was stirred for 30 minutes at room temperature and condensed to afford 4-((1R,5S)-3,8-diazabicyclo[3.2.1]octan-3-yl)-8-fluoro-2-((tetrahydro-1H-pyrrolizin-7a(5H)-yl)methoxy)-7-(8-(trifluoromethyl)naphthalen-1-yl)pyrido[4,3-d]pyrimidine dihydrochloride. The freebase was obtained by dissolving the material in a minimal amount of MeOH and eluting through a column of carbonate resin. Condensation afforded 4-((1R,5S)-3,8-diazabicyclo[3.2.1]octan-3-yl)-8-fluoro-2-((tetrahydro-1H-pyrrolizin-7a(5H)-yl)methoxy)-7-(8-(trifluoromethyl)naphthalen-1-yl)pyrido[4,3-d]pyrimidine (20 mg, 50%). LCMS (MM-ES+APCI, Pos): m/z 593.3 (M+H).

Example 423

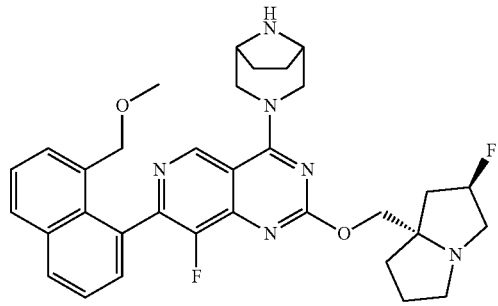 [SMILES: COCc1cccc2cccc(-c3ncc4c(N5CC6CCC(C5)N6)nc(OC[C@@]56CCCN5C[C@H](F)C6)nc4c3F)c12]

4-((1R,5S)-3,8-diazabicyclo[3.2.1]octan-3-yl)-8-fluoro-2-(((2R,7aS)-2-fluorohexahydro-1H-pyrrolizin-7a-yl)methoxy)-7-(8-(methoxymethyl)naphthalen-1-yl)pyrido[4,3-d]pyrimidine (racemic, trans)

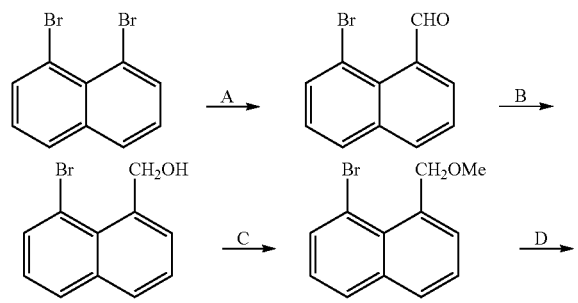

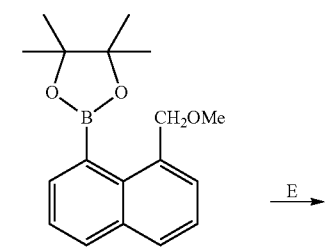

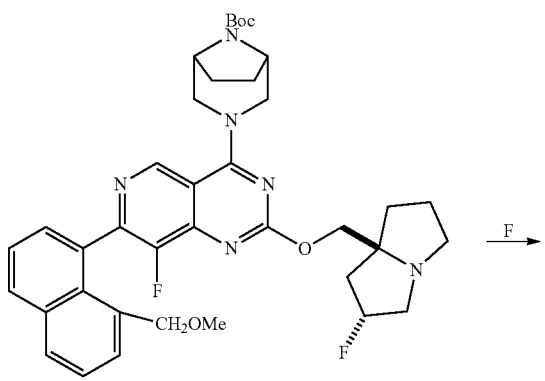

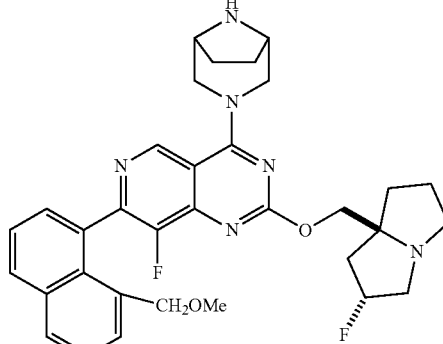

Step A. 8-bromo-1-naphthaldehyde. A solution of 1,8-dibromonaphthalene (1.0 g, 3.5 mmol) in THF (18 mL) was cooled to −70° C. To this solution was added n-butyllithium (2.1 N in hexanes, 2.0 mL, 4.2 mmol) dropwise. After the mixture was stirred at −70° C. for 30 minutes, N,N-dimethylformamide (0.6 mL) was added dropwise. The solution warmed to room temperature over one hour. The reaction was quenched with saturated aqueous NH$_4$Cl, the organics were separated, and the aqueous phase was extracted twice with DCM. The organics were dried over MgSO$_4$ and condensed. The material was purified by flash chromatography (RediSep Gold 24 g column, 0-10% EtOAc/hexane) to afford 8-bromo-1-naphthaldehyde (0.44 g, 53%). $^1$H NMR (400 MHz, CDCl$_3$): δ 11.44 (s, 1H), 8.01 (d, J=8.2 Hz, 1H), 7.91 (q, J=7.6 Hz, 3H), 7.57 (t, J=7.7 Hz, 1H), 7.40 (t, J=7.7 Hz, 1H).

Step B. (8-bromonaphthalen-1-yl)methanol. 8-Bromo-1-naphthaldehyde (0.24 g, 1.0 mmol) was suspended in ethanol (5 mL). After the mixture was cooled to 0° C., NaBH$_4$ (57 mg, 1.5 mmol) was added. The mixture was warmed to room temperature, diluted with EtOAc, and quenched with saturated aqueous NH$_4$Cl. The organics were separated and the aqueous phase was extracted with ethyl acetate. The combined organics were dried over MgSO$_4$ and condensed to afford (8-bromonaphthalen-1-yl)methanol (0.24 g, 99%). $^1$H NMR (400 MHz, CDCl$_3$): δ 7.89-7.83 (m, 3H), 7.71 (d, J=7.0 Hz, 1H), 7.48 (t, J=7.6 Hz, 1H), 7.28 (t, J=7.7 Hz, 1H), 5.47 (d, J=7.0 Hz, 2H).

Step C. 1-bromo-8-(methoxymethyl)naphthalene. (8-Bromonaphthalen-1-yl)methanol (0.24 g, 0.99 mmol) was dissolved in THF (5 mL) and cooled to 0° C. NaH (60% in mineral oil, 79 mg, 2.0 mmol) was added and the reaction was stirred for 30 minutes. Methyl iodide (0.093 mL, 1.5 mmol) was added, the solution was slowly warmed to room temperature, and the reaction was stirred for 16 hours. The reaction was diluted with EtOAc and quenched with saturated aqueous NH$_4$Cl. The organics were separated and the aqueous phase was extracted with EtOAc. The organics were dried over MgSO$_4$, condensed, and purified by flash chromatography (RediSep Gold 12 g column, 0-10% EtOAc/hexane) to afford 1-bromo-8-(methoxymethyl)naphthalene (0.18 g, 71%). $^1$H NMR (CDCl$_3$, 400 MHz): δ 7.87-7.79 (m, 3H), 7.74 (d, J=7.1 Hz, 1H), 7.46 (t, J=7.7 Hz, 1H), 7.25 (t, J=7.8 Hz, 1H), 5.33 (s, 2H), 3.52 (s, 3H).

Step D. 2-(8-(methoxymethyl)naphthalen-1-yl)-4,4,5,5-tetramethyl-1,3,2-dioxaborolane. Synthesized according to Example 187, Step B substituting 1-bromo-8-(methoxymethyl)naphthalene in place of 1-bromo-8-ethyl-naphthalene to afford 2-(8-(methoxymethyl)naphthalen-1-yl)-4,4,5,5-tetramethyl-1,3,2-dioxaborolane (46 mg, 39%). $^1$H NMR (400

MHz, CDCl₃): δ 7.86 (d, J=8.2 Hz, 1H), 7.77 (dd, J=7.5, 14.5 Hz, 2H), 7.47 (t, J=6.9 Hz, 1H), 7.40-7.33 (m, 2H), 5.21 (s, 2H), 3.11 (s, 3H), 1.42 (s, 12H).

Step E. Tert-butyl (1R,5S)-3-(8-fluoro-2-((2-fluorotetrahydro-1H-pyrrolizin-7a(5H)-yl)methoxy)-7-(8-(methoxymethyl)naphthalen-1-yl)pyrido[4,3-d]pyrimidin-4-yl)-3,8-diazabicyclo[3.2.1]octane-8-carboxylate (racemic, trans). Synthesized according to Example 426, Step A substituting tert-butyl (1R,5S)-3-(7-chloro-8-fluoro-2-((2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (racemic, trans) in place of tert-butyl (1R,5S)-3-(7-chloro-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate and 2-(8-(methoxymethyl)naphthalen-1-yl)-4,4,5,5-tetramethyl-1,3,2-dioxaborolane in place of ((2-fluoro-8-(4,4,5,5-tetramethyl-1,3,2-dioxaborolan-2-yl)naphthalen-1-yl)ethynyl)triisopropylsilane to afford tert-butyl (1R,5S)-3-(8-fluoro-2-((2-fluorotetrahydro-1H-pyrrolizin-7a(5H)-yl)methoxy)-7-(8-(methoxymethyl)naphthalen-1-yl)pyrido[4,3-d]pyrimidin-4-yl)-3,8-diazabicyclo[3.2.1]octane-8-carboxylate (racemic, trans) (9 mg, 14%). LCMS (MM-ES+APCI, Pos): m/z 687.4 (M+H).

Step F. 4-((1R,5S)-3,8-diazabicyclo[3.2.1]octan-3-yl)-8-fluoro-2-((2-fluorotetrahydro-1H-pyrrolizin-7a(5H)-yl)methoxy)-7-(8-(methoxymethyl)naphthalen-1-yl)pyrido[4,3-d]pyrimidine dihydrochloride (racemic, trans). Synthesized according to Example 229, Step B substituting tert-butyl (1R,5S)-3-(8-fluoro-2-((2-fluorotetrahydro-1H-pyrrolizin-7a(5H)-yl)methoxy)-7-(8-(methoxymethyl)naphthalen-1-yl)pyrido[4,3-d]pyrimidin-4-yl)-3,8-diazabicyclo[3.2.1]octane-8-carboxylate (racemic, trans) in place of tert-butyl (1R,5S)-3-(8-fluoro-2-((tetrahydro-1H-pyrrolizin-7a(5H)-yl)methoxy)-7-(2-(trifluoromethoxy)phenyl)pyrido[4,3-d]pyrimidin-4-yl)-3,8-diazabicyclo[3.2.1]octane-8-carboxylate to afford 4-((1R,5S)-3,8-diazabicyclo[3.2.1]octan-3-yl)-8-fluoro-2-((2-fluorotetrahydro-1H-pyrrolizin-7a(5H)-yl)methoxy)-7-(8-(methoxymethyl)naphthalen-1-yl)pyrido[4,3-d]pyrimidine dihydrochloride (racemic, trans) (5 mg, 58%). LCMS (MM-ES+APCI, Pos): m/z 587.3 (M+H).

Example 424

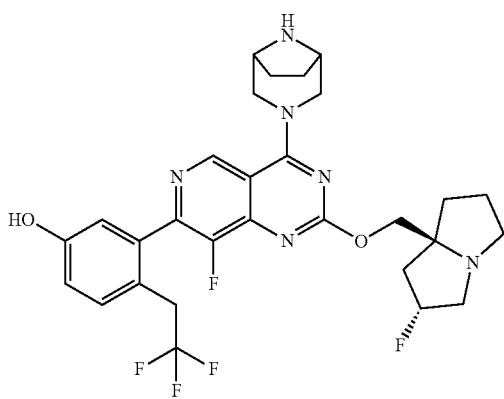 [SMILES: Oc1ccc(CC(F)(F)F)c(-c2ncc3c(N4CC5CCC(C4)N5)nc(OC[C@@]45CCCN4C[C@H](F)C5)nc3c2F)c1]

3-(4-((1R,5S)-3,8-diazabicyclo[3.2.1]octan-3-yl)-8-fluoro-2-(((2R,7aS)-2-fluorohexahydro-1H-pyrrolizin-7a-yl)methoxy)pyrido[4,3-d]pyrimidin-7-yl)-4-(2,2,2-trifluoroethyl)phenol (racemic, trans)

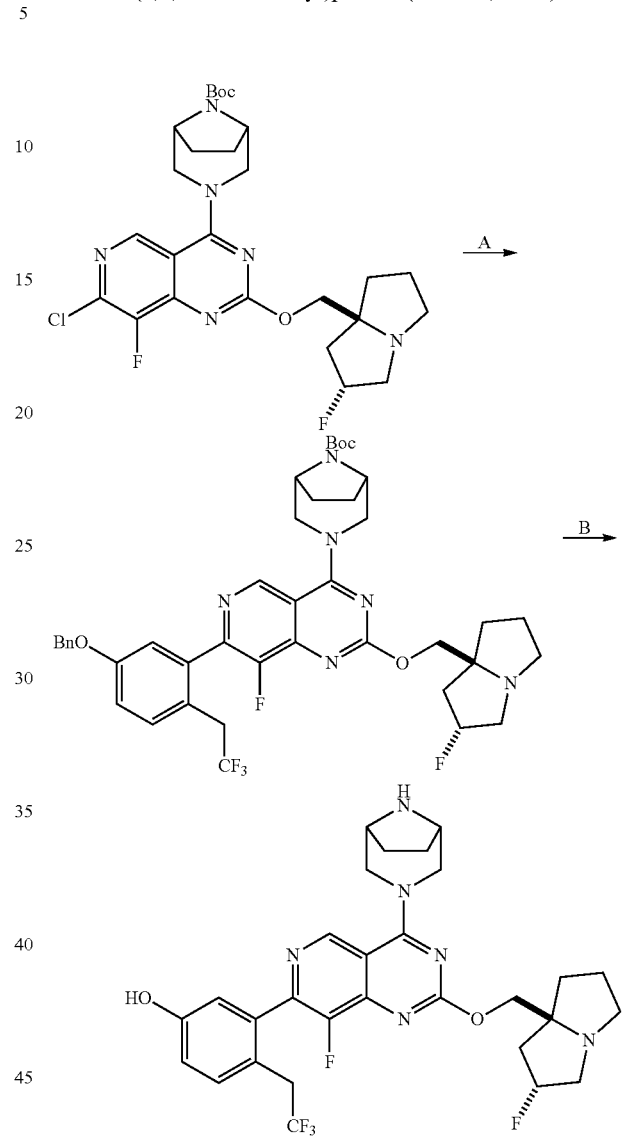

Step A. Tert-butyl (1R,5S)-3-(7-(5-(benzyloxy)-2-(2,2,2-trifluoroethyl)phenyl)-8-fluoro-2-((2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (racemic, trans). Tert-butyl (1R,5S)-3-(7-chloro-8-fluoro-2-((2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (racemic, trans) (50 mg, 0.091 mmol), 2-(5-(benzyloxy)-2-(2,2,2-trifluoroethyl)phenyl)-4,4,5,5-tetramethyl-1,3,2-dioxaborolane (53 mg, 0.14 mmol), and tetrakis(triphenylphosphine)palladium(0) (10 mg, 0.0090 mmol) were suspended in 1,4,-dioxane (1 mL). A 2 M aqueous solution of K₂CO₃ (0.14 mL, 0.28 mmol) was added. The vial was degassed with argon, sealed, and heated to 95° C. for 16 hours. The reaction mixture was cooled and diluted with EtOAc. The organics were separated and condensed to a red oil. The oil was purified by prep HPLC (5-95% MeCN/H₂O+0.1% TFA). The desired fractions were combined and partitioned between DCM and saturated aqueous NaHCO₃. The organic layer was separated and dried over MgSO₄ to afford tert-butyl (1R,5S)-3-(7-(5-(benzyloxy)-2-(2,2,2-trifluoroethyl)phenyl)-8-fluoro-2-((2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (racemic, trans) (42 mg, 59%). LCMS (MM-ES+APCI, Pos): m/z 780.9 (M+H).

Step B. 3-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-4-(2,2,2-trifluoroethyl)phenol bis(2,2,2-trifluoroacetate) (racemic, trans). Tert-butyl (1R,5S)-3-(7-(5-(benzyloxy)-2-(2,2,2-trifluoroethyl)phenyl)-8-fluoro-2-((2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (racemic, trans) (42 mg, 0.054 mmol) and pentamethylbenzene (24 mg, 0.16 mmol) were dissolved in DCM (2 mL). The solution was cooled to −78° C. and 1 M boron trichloride in DCM (0.3 mL) was added dropwise. The mixture was warmed to 0° C. over 30 minutes. The reaction was quenched with 1:1 MeCN:MeOH (5 mL) and condensed. The residue was purified (prep HPLC, 5-95% MeCN/H₂O/0.1% TFA) and lyophilization gave 3-(4-((1R,5S)-3,8-diazabicyclo[3.2.1]octan-3-yl)-8-fluoro-2-((2-fluorotetrahydro-1H-pyrrolizin-7a(5H)-yl)methoxy)pyrido[4,3-d]pyrimidin-7-yl)-4-(2,2,2-trifluoroethyl)phenol bis(2,2,2-trifluoroacetate) (racemic, trans) (10 mg, 27%). LCMS (MM-ES+APCI, Pos): m/z 591 (M+H).

Example 425

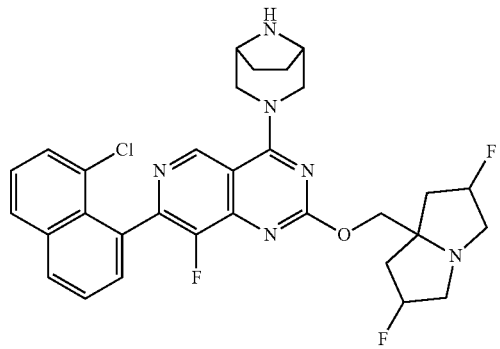 [SMILES: Fc1c(-c2cccc3cccc(Cl)c23)ncc2c(N3CC4CCC(C3)N4)nc(OCC34CC(F)CN3CC(F)C4)nc12]

4-((1R,5S)-3,8-diazabicyclo[3.2.1]octan-3-yl)-7-(8-chloronaphthalen-1-yl)-2-((2,6-difluorohexahydro-1H-pyrrolizin-7a-yl)methoxy)-8-fluoropyrido[4,3-d]pyrimidine (mixture of isomers)

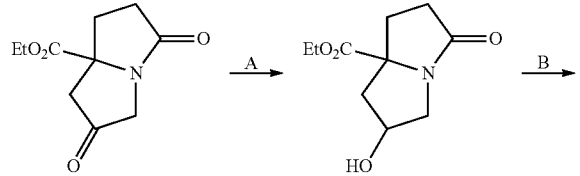

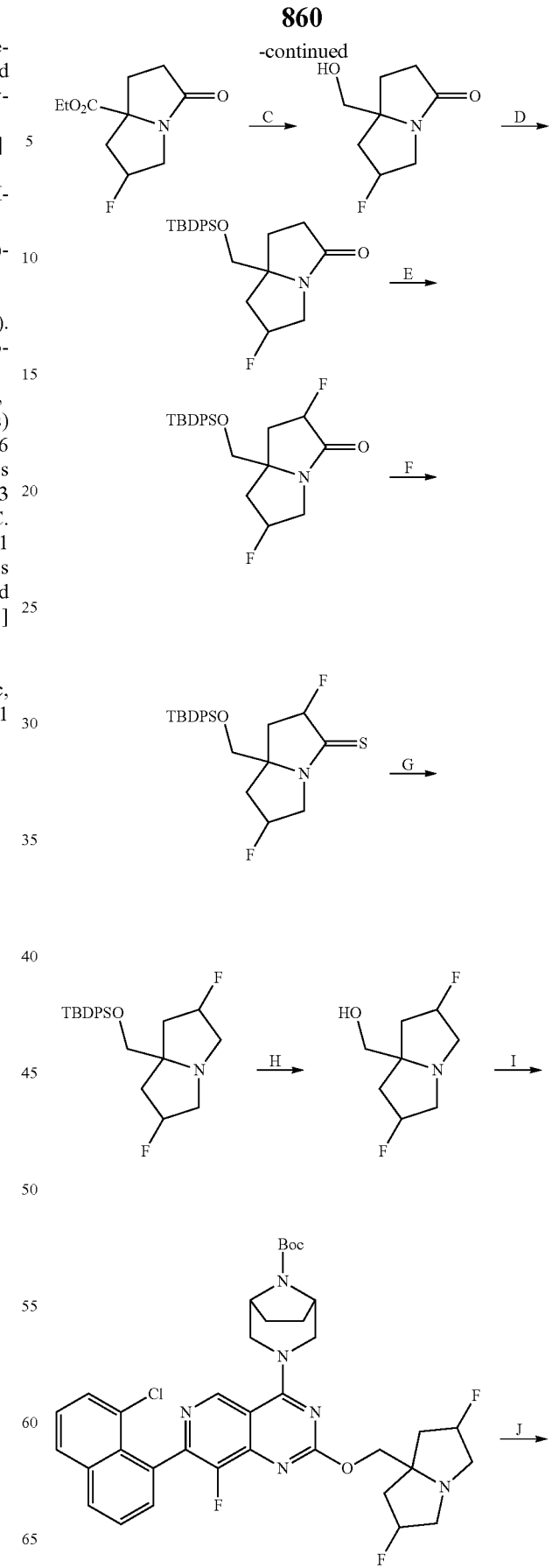

-continued

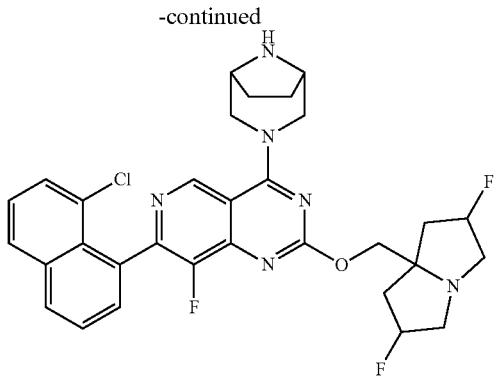

Step A. ethyl 2-hydroxy-5-oxotetrahydro-1H-pyrrolizine-7a(5H)-carboxylate (mixture of isomers). To a solution of ethyl 2,5-dioxotetrahydro-1H-pyrrolizine-7a(5H)-carboxylate (2.9 g, 14 mmol) in methanol (46 mL) was added sodium borohydride (0.13 g, 3.4 mmol) and stirred for 30 minutes. The solution was concentrated and purified by silica gel chromatography (1 to 20% MeOH/DCM, 1% NH$_4$OH) to give ethyl 2-hydroxy-5-oxotetrahydro-1H-pyrrolizine-7a(5H)-carboxylate (mixture of isomers) (2.4 g, 81%). LCMS (MM-ES+APCI, Pos): m/z 214.1 (M+H).

Step B. ethyl 2-fluoro-5-oxotetrahydro-1H-pyrrolizine-7a (5H)-carboxylate (mixture of isomers). To a solution of ethyl 2-hydroxy-5-oxotetrahydro-1H-pyrrolizine-7a(5H)-carboxylate (mixture of isomers) (2.4 g, 11.2 mmol) in dichloromethane (37 mL) at −78° C. was added DeoxoFluor (2.5 mL, 13 mmol). The solution was slowly warmed to room temperature and stirred for 5 hours. The solution was quenched with methanol, diluted with DCM, and washed with NaHCO$_3$. The organics were concentrated and purified by reverse-phase chromatography (5 to 95% MeCN/water with 0.1% TFA). The product was diluted with DCM and washed with NaHCO$_3$ and brine. The organic layer was dried with Na$_2$SO$_4$, filtered, and concentrated to give ethyl 2-fluoro-5-oxotetrahydro-1H-pyrrolizine-7a(5H)-carboxylate (mixture of isomers) (1.1 g, 46%). LCMS (MM-ES+APCI, Pos): m/z 216.1 (M+H)

Step C. 6-fluoro-7a-(hydroxymethyl)hexahydro-3H-pyrrolizin-3-one (mixture of isomers). To a solution of ethyl 2-fluoro-5-oxotetrahydro-1H-pyrrolizine-7a(5H)-carboxylate (mixture of isomers) (1.1 g, 5.2 mmol) in THF (26 mL) at 0° C. was added lithium borohydride (2.0 M in THF) (5.2 mL, 10 mmol). The reaction was warmed to room temperature and stirred for 1 hour. Lithium borohydride (2.5 mL, 5.0 mmol) was added and the reaction was stirred for 45 minutes. The reaction mixture was quenched with methanol, concentrated, and partitioned between dichloromethane and saturated NaHCO$_3$. The organics were washed with brine, dried with Na$_2$SO$_4$, filtered, and concentrated. The aqueous layer was filtered, frozen and lyophilized. The two materials were combined to give 6-fluoro-7a-(hydroxymethyl)hexahydro-3H-pyrrolizin-3-one (mixture of isomers) (0.89 g, 100%). LCMS (MM-ES+APCI, Pos): m/z 174.1 (M+H)

Step D. 7a-(((tert-butyldiphenylsilyl)oxy)methyl)-6-fluorohexahydro-3H-pyrrolizin-3-one (mixture of isomers). To a solution of 6-fluoro-7a-(hydroxymethyl)hexahydro-3H-pyrrolizin-3-one (mixture of isomers) (0.71 g, 4.1 mmol) and 1H-imidazole (0.42 g, 6.2 mmol) in DCM (8 mL) at 0° C. was added tert-butylchlorodiphenylsilane (1.4 mL, 5.3 mmol). The reaction was stirred at room temperature for 90 minutes. The reaction mixture was diluted with DCM and washed with NaHCO$_3$ and brine. The organic layer was dried with Na$_2$SO$_4$, filtered, concentrated, and purified by silica gel chromatography (5 to 95% EtOAc/hexanes) to give 7a-(((tert-butyldiphenylsilyl)oxy)methyl)-6-fluorohexahydro-3H-pyrrolizin-3-one (mixture of isomers) (1.1 g, 66%). LCMS (MM-ES+APCI, Pos): m/z 412.2 (M+H).

Step E. 7a-(((tert-butyldiphenylsilyl)oxy)methyl)-2,6-difluorohexahydro-3H-pyrrolizin-3-one (mixture of isomers). To a solution of 7a-(((tert-butyldiphenylsilyl)oxy)methyl)-6-fluorohexahydro-3H-pyrrolizin-3-one (mixture of isomers) (1.1 g, 2.7 mmol) in tetrahydrofuran (11 mL) at −78° C. was added 2M LDA (4.1 mL, 8.2 mmol). The reaction was stirred for 10 minutes at −40° C. The reaction was cooled to −78° C. and a solution of NFSI (1.7 g, 5.4 mmol) in THF (3 mL) was added. The reaction was warmed to room temperature and stirred for 1 hour. The solution was quenched with NH$_4$Cl. The solution was diluted with DCM and washed with NaHCO$_3$. The organics were concentrated and purified by silica gel chromatography (5 to 95% EtOAc/hex) to give 7a-(((tert-butyldiphenylsilyl)oxy)methyl)-2,6-difluorohexahydro-3H-pyrrolizin-3-one (mixture of isomers) (520 mg, 44%). LCMS (MM-ES+APCI, Pos): m/z 430.2 (M+H).

Step F. 7a-(((tert-butyldiphenvlsilyl)oxy)methyl)-2,6-difluorohexahydro-3H-pyrrolizine-3-thione (mixture of isomers). A solution of 7a-(((tert-butyldiphenylsilyl)oxy)methyl)-2,6-difluorohexahydro-3H-pyrrolizin-3-one (mixture of isomers) (0.52 g, 1.2 mmol) and Lawesson's Reagent (0.64 g, 1.6 mmol) in benzene (8 mL) was heated to 70° C. under nitrogen for 45 minutes. The solution was cooled to room temperature, diluted with DCM, and washed with NaHCO$_3$. The organics were concentrated and purified by silica gel chromatography (5 to 95% EtOAc/hex) to give 7a-(((tert-butyldiphenylsilyl)oxy)methyl)-2,6-difluorohexahydro-3H-pyrrolizine-3-thione (mixture of isomers) (0.43 g, 80%). LCMS (MM-ES+APCI, Pos): m/z 446.2 (M+H).

Step G. 7a-(((tert-butyldiphenvlsilyl)oxy)methyl)-2,6-difluorohexahydro-1H-pyrrolizine (mixture of isomers). To a solution of 7a-(((tert-butyldiphenylsilyl)oxy)methyl)-2,6-difluorohexahydro-3H-pyrrolizine-3-thione (mixture of isomers) (0.43 g, 0.96 mmol) in ethanol (10 mL) was added Raney Ni (0.10 mL, 0.96 mmol). The reaction was heated to 70° C. overnight. The reaction was filtered, diluted with DCM, and washed with NaHCO$_3$. The organics were concentrated and purified by reverse-phase chromatography (5 to 95% MeCN/water with 0.1% TFA as modifier). The product was lyophilized to give 7a-(((tert-butyldiphenylsilyl)oxy)methyl)-2,6-difluorohexahydro-1H-pyrrolizine (mixture of isomers) (25 mg, 6%). LCMS (MM-ES+APCI, Pos): m/z 416.2 (M+H).

Step H. (2,6-difluorotetrahydro-1H-pyrrolizin-7a(5H)-yl) methanol (mixture of isomers). To a solution of 7a-(((tert-butyldiphenylsilyl)oxy)methyl)-2,6-difluorohexahydro-1H-pyrrolizine (mixture of isomers) (25 mg, 0.060 mmol) in tetrahydrofuran (0.3 mL) at 0° C. was added 1M TBAF (0.3 mL, 0.30 mmol) and the reaction was stirred at room temperature for 1 hour. The solution was warmed to 45° C.

and stirred for 1 hour. The solution was cooled to rt, concentrated, and diluted with DCM and washed with water. The aqueous layer was lyophilized to give crude (2,6-difluorotetrahydro-1H-pyrrolizin-7a(5H)-yl)methanol (mixture of isomers) (11 mg, 103%). LCMS (MM-ES+APCI, Pos): m/z 178.1 (M+H).

Step I. tert-butyl (1R,5S)-3-(7-(8-chloronaphthalen-1-yl)-2-((2,6-difluorotetrahydro-1H-pyrrolizin-7a(5H)-yl)methoxy)-8-fluoropyrido[4,3-d]pyrimidin-4-yl)-3,8-diazabicyclo[3.2.1]octane-8-carboxylate (mixture of isomers). A mixture of 4 A mol sieves (30 mg), tert-butyl (1R,5S)-3-(2-chloro-7-(8-chloronaphthalen-1-yl)-8-fluoropyrido[4,3-d]pyrimidin-4-yl)-3,8-diazabicyclo[3.2.1]octane-8-carboxylate (14 mg, 0.025 mmol), (2,6-difluorotetrahydro-1H-pyrrolizin-7a(5H)-yl)methanol (mixture of isomers) (3 mg, 0.017 mmol), RuPhos Pd Gen3 precatalyst (1.4 mg, 0.0017 mmol), and $Cs_2CO_3$ (22 mg, 0.068 mmol) in 1,4-dioxane (0.2 mL) was sparged with argon for 5 minutes and stirred at 90° C. in a sealed vial overnight. The solution was filtered and purified by reverse-phase chromatography (5→95% MeCN/water with 0.1% TFA as modifier). The fractions containing the product were pooled and lyophilized to give tert-butyl (1R,5S)-3-(7-(8-chloronaphthalen-1-yl)-2-((2,6-difluorotetrahydro-1H-pyrrolizin-7a(5H)-yl)methoxy)-8-fluoropyrido[4,3-d]pyrimidin-4-yl)-3,8-diazabicyclo[3.2.1]octane-8-carboxylate (mixture of isomers) (3 mg, 25%). LCMS (MM-ES+APCI, Pos): m/z 695.2 (M+H).

Step J. 4-((1R,5S)-3,8-diazabicyclo[3.2.1]octan-3-yl)-7-(8-chloronaphthalen-1-yl)-2-((2,6-difluorotetrahydro-1H-pyrrolizin-7a(5H)-yl)methoxy)-8-fluoropyrido[4,3-d]pyrimidine bis(2,2,2-trifluoroacetate) (mixture of isomers). A solution of tert-butyl (1R,5S)-3-(7-(8-chloronaphthalen-1-yl)-2-((2,6-difluorotetrahydro-1H-pyrrolizin-7a(5H)-yl)methoxy)-8-fluoropyrido[4,3-d]pyrimidin-4-yl)-3,8-diazabicyclo[3.2.1]octane-8-carboxylate 2,2,2-trifluoroacetate (mixture of isomers) (3 mg, 0.004 mmol) in TFA (0.1 mL) and DCM (0.1 mL) was stirred for 30 minutes. The solution was concentrated and purified by reverse-phase chromatography (5→95% MeCN/water with 0.1% TFA as a modifier). Fractions containing product were pooled and lyophilized to give 4-((1R,5S)-3,8-diazabicyclo[3.2.1]octan-3-yl)-7-(8-chloronaphthalen-1-yl)-2-((2,6-difluorotetrahydro-1H-pyrrolizin-7a(5H)-yl)methoxy)-8-fluoropyrido[4,3-d]pyrimidine bis(2,2,2-trifluoroacetate) (mixture of isomers) (1.3 mg, 43%). LCMS (MM-ES+APCI, Pos): m/z 595.2 (M+H).

Example 426

4-((1R,5S)-3,8-diazabicyclo[3.2.1]octan-3-yl)-7-(8-ethyl-7-fluoronaphthalen-1-yl)-8-fluoro-2-((hexahydro-1H-pyrrolizin-7a-yl)methoxy)pyrido[4,3-d]pyrimidine

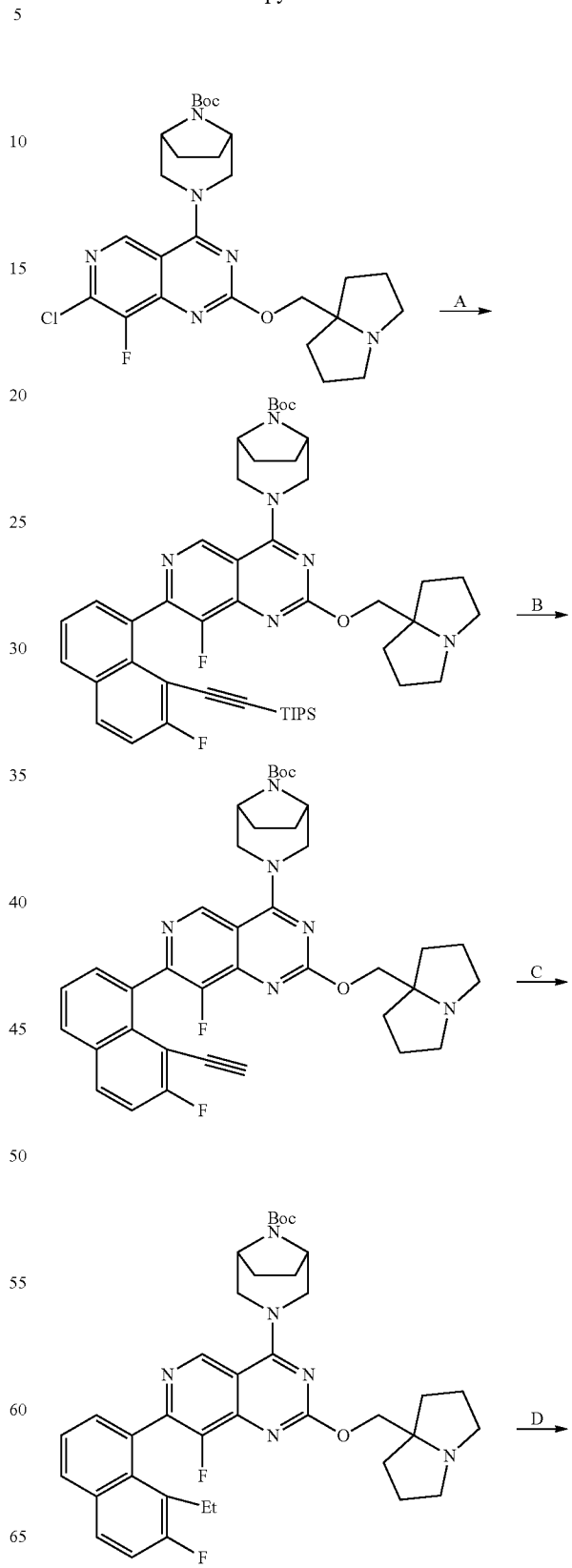

-continued

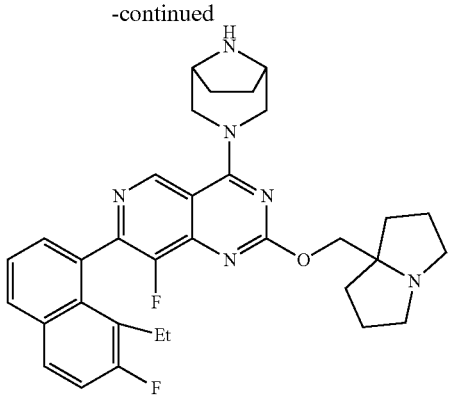

Step A. Tert-butyl (1R,5S)-3-(8-fluoro-7-(7-fluoro-8-((triisopropylsilyl)ethynyl)naphthalen-1-yl)-2-((tetrahydro-1H-pyrrolizin-7a(5H)-yl)methoxy)pyrido[4,3-d]pyrimidin-4-yl)-3,8-diazabicyclo[3.2.1]octane-8-carboxylate: ((2-Fluoro-8-(4,4,5,5-tetramethyl-1,3,2-dioxaborolan-2-yl)naphthalen-1-yl)ethynyl)triisopropylsilane (51 mg, 0.11 mmol), tert-butyl (1R,5S)-3-(7-chloro-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (50 mg, 0.094 mmol), and mesylate[(di(1-adamantyl)-n-butylphosphine)-2-(2'-amino-1,1'-biphenyl)]palladium(II) (14 mg, 0.019 mmol) were suspended in THF (1 mL) and K$_3$PO$_4$ (0.28 mL, 1M in water) was added. The vial was degassed with argon, sealed, and heated to 60° C. for 16 hours. The mixture was cooled and diluted with EtOAc. The organics were washed with water, dried over MgSO$_4$, and condensed to a brown oil. The residue was purified (prep HPLC, 5-95% MeCN/H$_2$O/0.1% TFA in 15 min) and isolated as the freebase by partitioning between saturated aqueous NaHCO$_3$ and DCM. The organics were dried over MgSO$_4$ and condensed to afford tert-butyl (1R,5S)-3-(8-fluoro-7-(7-fluoro-8-((triisopropylsilyl)ethynyl)naphthalen-1-yl)-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (51 mg, 66%). LCMS (MM-ES+APCI, Pos): m/z 823.9 (M+H).

Step B. Tert-butyl (1R,5S)-3-(7-(8-ethynyl-7-fluoronaphthalen-1-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate. Synthesized according to Example 204, Step B substituting tert-butyl (1R,5S)-3-(8-fluoro-7-(7-fluoro-8-((triisopropylsilyl)ethynyl)naphthalen-1-yl)-2-((tetrahydro-1H-pyrrolizin-7a(5H)-yl)methoxy)pyrido[4,3-d]pyrimidin-4-yl)-3,8-diazabicyclo[3.2.1]octane-8-carboxylate in place of tert-butyl (1R,5S)-3-(8-fluoro-2-(((2S,7aR)-2-fluorotetrahydro-1H-pyrrolizin-7a(5H)-yl)methoxy)-7-(5-((triisopropylsilyl)ethynyl)isoquinolin-4-yl)pyrido[4,3-d]pyrimidin-4-yl)-3,8-diazabicyclo[3.2.1]octane-8-carboxylate to afford tert-butyl (1R,5S)-3-(7-(8-ethynyl-7-fluoronaphthalen-1-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (28 mg, 68%). LCMS (MM-ES+APCI, Pos): m/z 666.9 (M+H).

Step C. Tert-butyl (1R,5S)-3-(7-(8-ethyl-7-fluoronaphthalen-1-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate. A solution of tert-butyl (1R,5S)-3-(7-(8-ethynyl-7-fluoronaphthalen-1-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (28 mg, 0.042 mmol) in MeOH (2 mL) was degassed with argon. To this solution palladium hydroxide (20% on carbon) was added. The solution was purged with hydrogen and the suspension was stirred under a H$_2$ atmosphere for 2 hours. The suspension was filtered and condensed to give tert-butyl (1R,5S)-3-(7-(8-ethyl-7-fluoronaphthalen-1-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (28 mg, 99%). LCMS (MM-ES+APCI, Pos): m/z 670.9 (M+H).

Step D. 4-((1R,5S)-3,8-diazabicyclo[3.2.1]octan-3-yl)-7-(8-ethyl-7-fluoronaphthalen-1-yl)-8-fluoro-2-((tetrahydro-1H-pyrrolizin-7a(5H)-yl)methoxy)pyrido[4,3-d]pyrimidine dihydrochloride. Synthesized according to Example 229, Step B substituting tert-butyl (1R,5S)-3-(7-(8-ethyl-7-fluoronaphthalen-1-yl)-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate in place of tert-butyl (1R,5S)-3-(8-fluoro-2-((tetrahydro-1H-pyrrolizin-7a(5H)-yl)methoxy)-7-(2-(trifluoromethoxy)phenyl)pyrido[4,3-d]pyrimidin-4-yl)-3,8-diazabicyclo[3.2.1]octane-8-carboxylate to afford 4-((1R,5S)-3,8-diazabicyclo[3.2.1]octan-3-yl)-7-(8-ethyl-7-fluoronaphthalen-1-yl)-8-fluoro-2-((tetrahydro-1H-pyrrolizin-7a(5H)-yl)methoxy)pyrido[4,3-d]pyrimidine dihydrochloride (15 mg, 56%). LCMS (MM-ES+APCI, Pos): m/z 571.0 (M+H).

Example 427

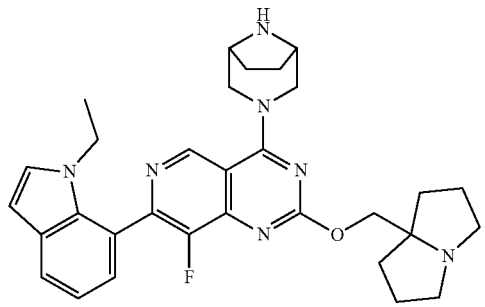 [SMILES: CCn1ccc2cccc(-c3ncc4c(N5CC6CCC(C5)N6)nc(OCC56CCCN5CCC6)nc4c3F)c21]

4-((1R,5S)-3,8-diazabicyclo[3.2.1]octan-3-yl)-7-(1-ethyl-1H-indol-7-yl)-8-fluoro-2-((hexahydro-1H-pyrrolizin-7a-yl)methoxy)pyrido[4,3-d]pyrimidine

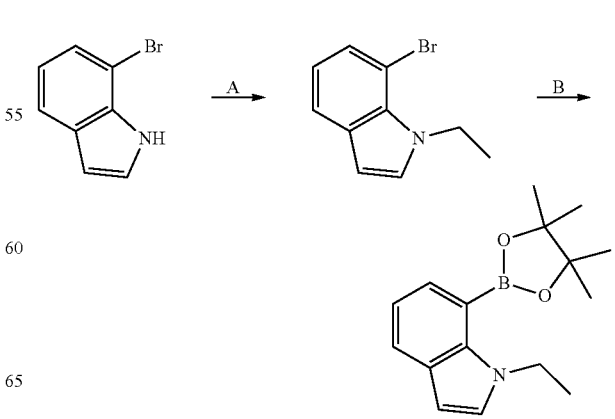

-continued

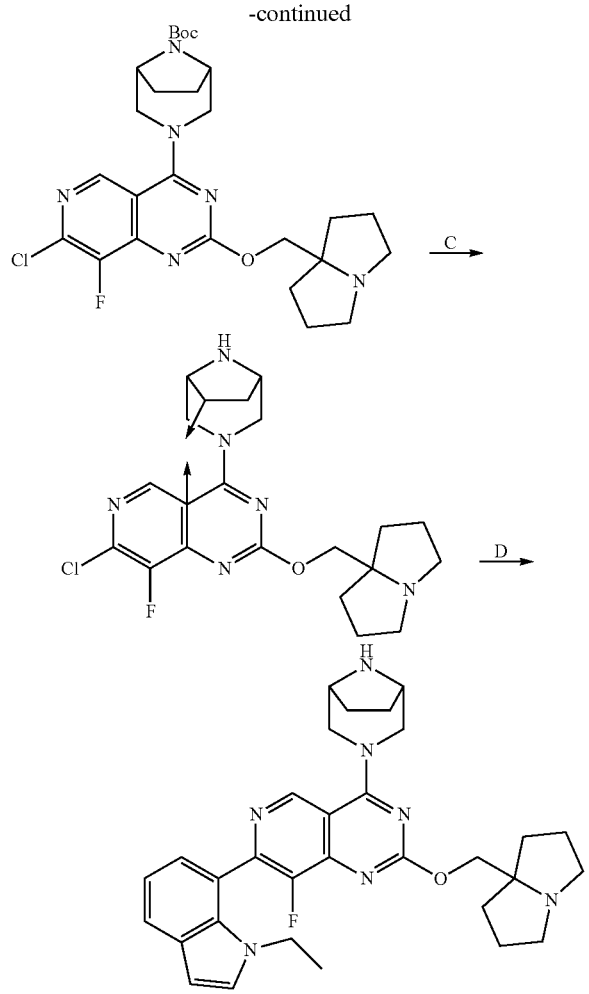

Step A. 7-bromo-1-ethyl-1H-indole. 7-Bromo-1H-indole (500 mg, 2.55 mmol) was added to a round bottom flask with a stir bar and septa. The round bottom flask was degassed and purged with $N_2$ 3 times before dry THF (9 mL) was added. The round bottom flask was cooled to 0° C. and 60% NaH (0.15 g, 3.8 mmol) was added portion wise. The reaction was warmed to room temperature and stirred for 30 minutes. The round bottom flask was cooled to 0° C. and iodoethane (0.27 mL, 3.32 mmol) was added dropwise. The reaction warmed to room temperature. Additional iodoethane (0.27 mL, 3.3 mmol) was added and the reaction was heated to 65° C. for 1 hour. The round bottom flask was cooled to 0° C. and water was slowly added. The reaction was extracted with DCM. The DCM layer was dried with $Na_2SO_4$, filtered, and concentrated. The residue was purified via reverse phase chromatography (C18, 0-100% MeCN in water with 0.1% TFA). The fractions containing the product were combined, diluted with EtOAc, and washed with saturated $NaHCO_3$ followed by water. The EtOAc layer was dried with $Na_2SO_4$, filtered, and concentrated to yield 7-bromo-1-ethyl-1H-indole as a pale-yellow oil (0.41 g, 72%). LCMS (MM-ES+APCI, Pos): m/z 272.2 (M+H).

Step B. 1-ethyl-7-(4,4,5,5-tetramethyl-1,3,2-dioxaborolan-2-yl)-1H-indole. 7-Bromo-1-ethyl-1H-indole (0.20 g, 0.89 mmol), 4,4,4',4',5,5,5',5'-octamethyl-2,2'-bi(1,3,2-di- oxaborolane) (0.68 g, 2.7 mmol), $PdCl_2(dppf)$ (65 mg, 0.089 mmol), and KOAc (0.26 g, 2.7 mmol) were added to a vial with stir bar and septa cap. The vial was degassed and purged with $N_2$ 3 times before dioxane (5 mL) was added. The vial was sparged with $N_2$ for 15 minutes and the reaction was heated to 95° C. for 2 hours. The reaction was diluted with DCM and filtered through a Celite plug and the filtrate concentrated. The residue was purified via reverse phase chromatography (C18, 0-100% MeCN in water with 0.1% TFA). The fractions containing the product were combined, diluted with $Et_2O$, and washed with saturated $NaHCO_3$ followed by water. The $Et_2O$ layer was dried with $Na_2SO_4$, filtered, and concentrated to yield 1-ethyl-7-(4,4,5,5-tetramethyl-1,3,2-dioxaborolan-2-yl)-1H-indole as a brown oil (0.14 g, 59%). LCMS (MM-ES+APCI, Pos): m/z 272.3 (M+H).

Step C. 4-((1R,5S)-3,8-diazabicyclo[3.2.1]octan-3-yl)-7-chloro-8-fluoro-2-((tetrahydro-1H-pyrrolizin-7a(5H)-yl)methoxy)pyrido[4,3-d]pyrimidine. Tert-butyl (1R,5S)-3-(7-chloro-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (0.10 g, 0.19 mmol) was added to a vial with a stir bar. DCM (1 mL) was added followed by TFA (0.5 mL). The reaction was stirred at room temperature for 30 minutes before being concentrated. The residue was purified via reverse phase chromatography eluting with 0-80% MeCN/water with 0.1% TFA as modifier. The fractions containing the product were combined, frozen, and lyophilized. The TFA salt was passed through a PL-HCO3 ME Resin plug with methanol and concentrated to yield 4-((1R,5S)-3,8-diazabicyclo[3.2.1]octan-3-yl)-7-chloro-8-fluoro-2-((tetrahydro-1H-pyrrolizin-7a(5H)-yl)methoxy)pyrido[4,3-d]pyrimidine as a white solid (76 mg, 91%). LCMS (MM-ES+APCI, Pos): m/z 433.3 (M+H).

Step D. 4-((1R,5S)-3,8-diazabicyclo[3.2.1]octan-3-yl)-7-(1-ethyl-1H-indol-7-yl)-8-fluoro-2-((tetrahydro-1H-pyrrolizin-7a(5H)-yl)methoxy)pyrido[4,3-d]pyrimidine. 4-((1R,5S)-3,8-diazabicyclo[3.2.1]octan-3-yl)-7-chloro-8-fluoro-2-((tetrahydro-1H-pyrrolizin-7a(5H)-yl)methoxy)pyrido[4,3-d]pyrimidine (21 mg, 0.05 mmol), 1-ethyl-7-(4,4,5,5-tetramethyl-1,3,2-dioxaborolan-2-yl)-1H-indole (20 mg, 0.075 mmol) and XPhos Pd G2 (8 mg, 0.01 mmol) were added to a vial with a stir bar and septa cap. The vial was degassed and purged with $N_2$ 3 times before degassed THF (0.25 mL) and degassed 0.5 M aqueous $K_3PO_4$ (0.2 mL, 0.10 mmol) were added. The reaction was heated to 40° C. for 1 hour. The reaction was diluted with water and extracted with DCM 3 times. The DCM layers were combined, dried with $Na_2SO_4$, filtered, and concentrated. The residue was purified via reverse phase chromatography eluting with 0-80% MeCN/water with 0.1% TFA as modifier. The fractions containing the product were combined, frozen, and lyophilized. The TFA salt was passed through a PL-HCO3 ME Resin plug with methanol and concentrated to yield 4-((1R,5S)-3,8-diazabicyclo[3.2.1]octan-3-yl)-7-(1-ethyl-1H-indol-7-yl)-8-fluoro-2-((tetrahydro-1H-pyrrolizin-7a(5H)-yl)methoxy)pyrido[4,3-d]pyrimidine as a white solid (10 mg, 35%). LCMS (MM-ES+APCI, Pos): m/z 542.4 (M+H).

Example 428

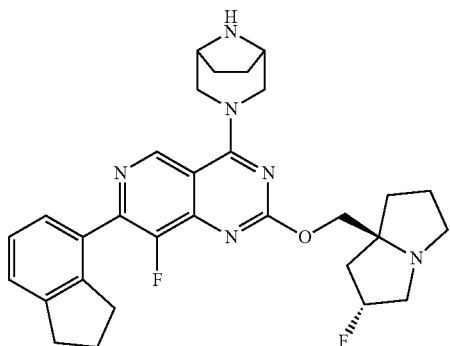 [SMILES: Fc1c(-c2cccc3c2CCC3)ncc2c(N3CC4CCC(C3)N4)nc(OC[C@@]34CCCN3C[C@H](F)C4)nc12]

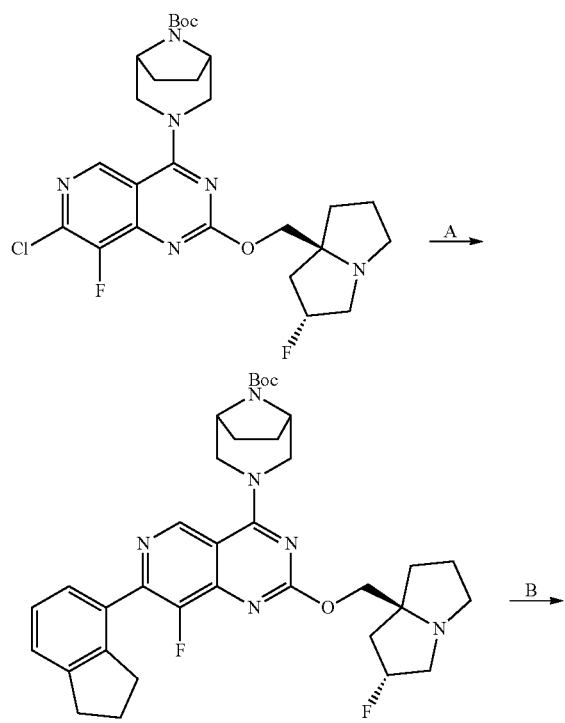

4-(3,8-diazabicyclo[3.2.1]octan-3-yl)-7-(2,3-di-hydro-1H-inden-4-yl)-8-fluoro-2-(((2R,7aS)-2-fluorotetrahydro-1H-pyrrolizin-7a(5H)-yl)methoxy)pyrido[4,3-d]pyrimidine (racemic, trans)

Step A. tert-butyl 3-(7-(2,3-dihydro-1H-inden-4-yl)-8-fluoro-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate. To a vial containing tert-butyl 3-(7-chloro-8-fluoro-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (40 mg, 0.073 mmol), 2-(2,3-dihydro-1H-inden-4-yl)-4,4,5,5-tetramethyl-1,3,2-dioxaborolane (35 mg, 0.15 mmol), Pd(PPh$_3$)$_4$ (8.4 mg, 0.0073 mmol) under N$_2$ was added K$_2$CO$_3$ (1.0 M, 0.11 ml, 0.22 mmol), followed by 1,4-dioxane (0.7 ml). The vial was closed, and the mixture was heated at 80° C. for 4 h. The solution was cooled to rt, diluted with water and extracted with EtOAc. The extract was dried over Na$_2$SO$_4$ and concentrated to give the crude title compound as a brown oil. LCMS (MM-ES+APCI, Pos): m/z 633.4 (M+H).

Step B. 4-(3,8-diazabicyclo[3.2.1]octan-3-yl)-7-(2,3-dihydro-1H-inden-4-yl)-8-fluoro-2-(((2R,7aS)-2-fluorotetrahydro-1H-pyrrolizin-7a(5H)-yl)methoxy)pyrido[4,3-d]pyrimidine. To the above crude tert-butyl 3-(7-(2,3-dihydro-1H-inden-4-yl)-8-fluoro-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate in DCM (1.0 ml) was added TFA (0.50 ml). The solution was stirred at rt for 0.5 h, concentrated and the residue was purified by preparative C18 HPLC eluting with 0-95% CH$_3$CN/H$_2$O with 0.1% TFA as modifier. The desired fractions were combined, basified with NaHCO$_3$(Sat.) and extracted with DCM. The combined extract was dried over Na$_2$SO$_4$ and concentrated to give the title compound as a white solid (6.0 mg, 15% over 2 steps). LCMS (MM-ES+APCI, Pos): m/z 533.4 (M+H).

Example 429

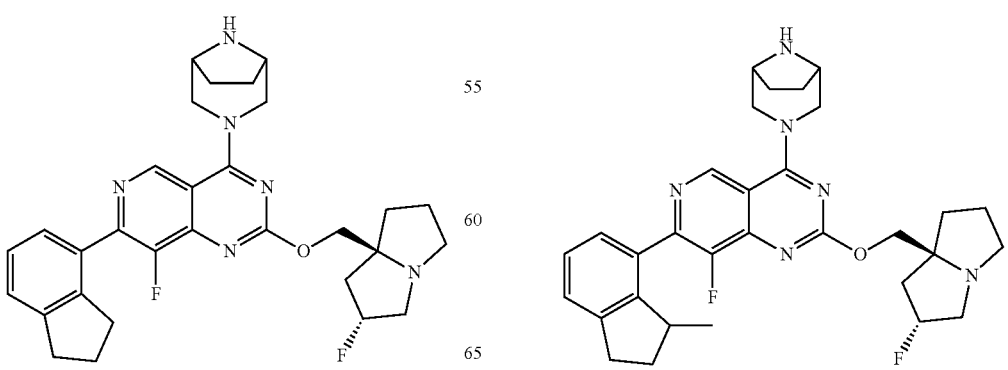

871

4-(3,8-diazabicyclo[3.2.1]octan-3-yl)-8-fluoro-2-(((2R,7aS)-2-fluorotetrahydro-1H-pyrrolizin-7a(5H)-yl)methoxy)-7-(3-methyl-2,3-dihydro-1H-inden-4-yl)pyrido[4,3-d]pyrimidine (Racemic, Trans)

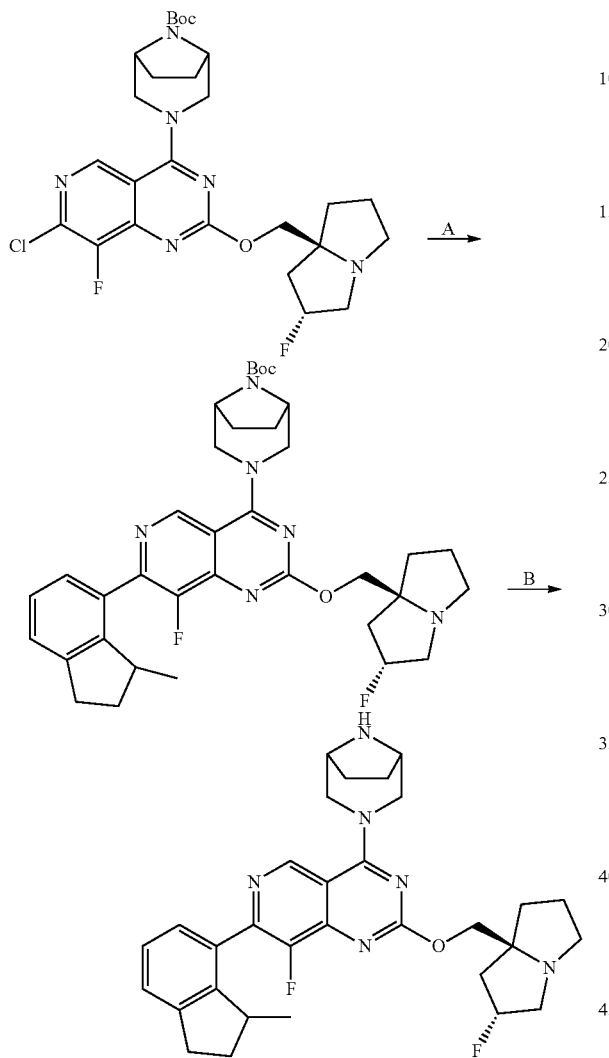

Step A. tert-butyl 3-(8-fluoro-2-(((2R,7aS)-2-fluorotetrahydro-1H-pyrrolizin-7a(5H)-yl)methoxy)-7-(3-methyl-2,3-dihydro-1H-inden-4-yl)pyrido[4,3-d]pyrimidin-4-yl)-3,8-diazabicyclo[3.2.1]octane-8-carboxylate. To a vial containing tert-butyl 3-(7-chloro-8-fluoro-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (55 mg, 0.10 mmol), 4,4,5,5-tetramethyl-2-(3-methyl-2,3-dihydro-1H-inden-4-yl)-1,3,2-dioxaborolane (52 mg, 0.20 mmol), Pd(PPh$_3$)$_4$ (12 mg, 0.010 mmol) under N$_2$ was added K$_2$CO$_3$ (2.0 M, 0.30 mmol), followed by 1,4-dioxane (1.0 ml). The vial was closed, and the mixture was heated at 80° C. for 15 h. The solution was cooled to rt, diluted with water and extracted with EtOAc. The extract was dried over Na$_2$SO$_4$ and concentrated to give the crude title compound as a brown oil. LCMS (MM-ES+APCI, Pos): m/z 647.3 (M+H).

Step B. 4-(3,8-diazabicyclo[3.2.1]octan-3-yl)-8-fluoro-2-(((2R,7aS)-2-fluorotetrahydro-1H-pyrrolizin-7a(5H)-yl)

872 methoxy)-7-(3-methyl-2,3-dihydro-1H-inden-4-yl)pyrido[4,3-d]pyrimidine. To a solution of tert-butyl 3-(8-fluoro-2-(((2R,7aS)-2-fluorotetrahydro-1H-pyrrolizin-7a(5H)-yl)methoxy)-7-(3-methyl-2,3-dihydro-1H-inden-4-yl)pyrido[4,3-d]pyrimidin-4-yl)-3,8-diazabicyclo[3.2.1]octane-8-carboxylate in DCM (1.0 ml) was added TFA (0.50 ml). The solution was stirred at rt for 0.5 h, and concentrated. The residue was purified by preparative C18 HPLC eluting with 0-95% CH$_3$CN/H$_2$O with 0.1% TFA as modifier. The desired fractions were combined, basified with NaHCO$_3$(Sat.) and extracted with DCM. The combined extract was dried over Na$_2$SO$_4$ and concentrated to give the title compound as a white solid (40 mg, 73% over 2 steps). LCMS (MM-ES+APCI, Pos): m/z 547.3 (M+H).

Example 430

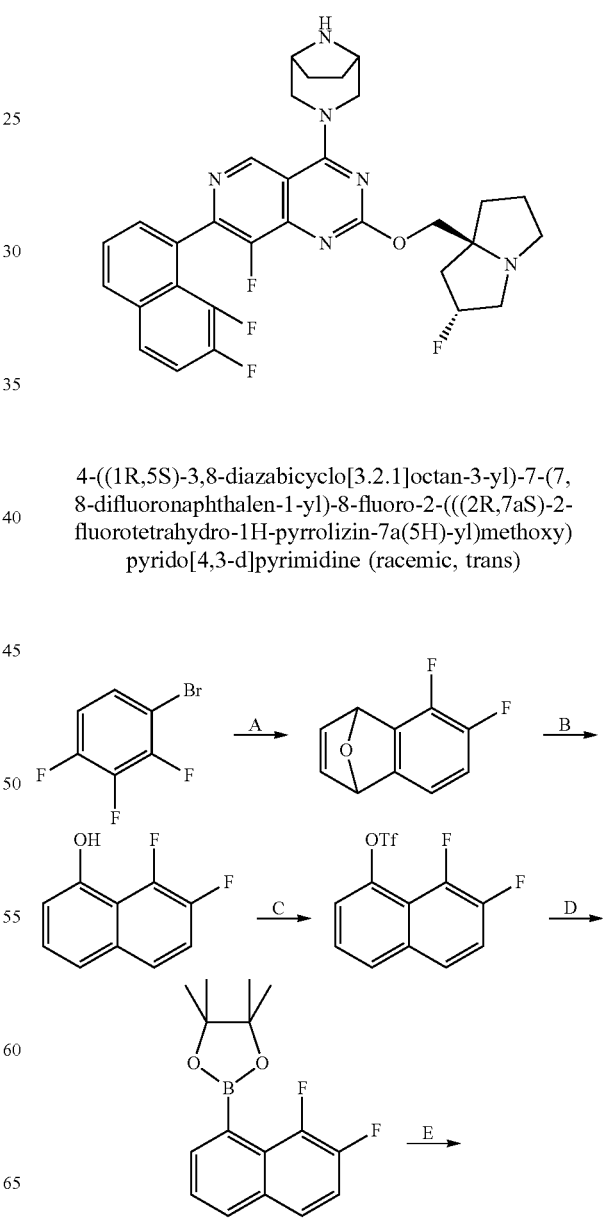

4-((1R,5S)-3,8-diazabicyclo[3.2.1]octan-3-yl)-7-(7,8-difluoronaphthalen-1-yl)-8-fluoro-2-(((2R,7aS)-2-fluorotetrahydro-1H-pyrrolizin-7a(5H)-yl)methoxy)pyrido[4,3-d]pyrimidine (racemic, trans)

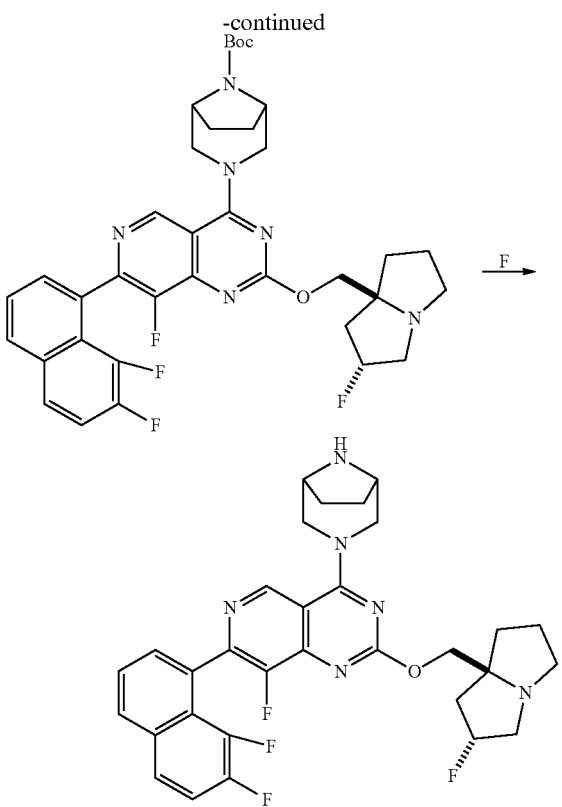

Step A. 5,6-difluoro-1,4-dihydro-1,4-epoxynaphthalene. A stirred mixture of tetrahydrofuran (20 ml, 10 mmol), furan (3.6 ml, 50. mmol) and magnesium (0.31 g, 13 mmol) under $N_2$ atmosphere was brought to reflux and a solution of 1-bromo-2,3,4-trifluorobenzene (2.1 g, 10 mmol) in THF (3 mL) was added dropwise over 1 h. The reaction mixture was stirred and heated for 24 h. The mixture was cooled to r.t. and quenched with water. The suspension was partitioned between MTBE (50 mL) and water (20 mL). The organic phase was washed with water and brine (15 mL each), dried over $Na_2SO_4$, evaporated in vacuo and chromatographed on silica gel eluting with 2 to 10% EtOAc/hexane to yield the desired product (0.90 g, 50%). $^1$H NMR (CDCl$_3$, 400 MHz): 7.07 (1H, dd, J=5.6, 2.4 Hz), 7.04 (1H, dd, J=5.6, 2.4 Hz), 6.92 (1H, dd, J=7.5, 3.7 Hz), 6.75 (1H, ddd, J=10.7, 7.6, 6.9 Hz), 5.97 (1H, s), 5.71 (1H, m).

Step B. 7,8-difluoronaphthalen-1-ol. A stirred mixture of 5,6-difluoro-1,4-dihydro-1,4-epoxynaphthalene (0.90 g, 5.0 mmol), hexane (3 mL), methanol (5 ml) and 12M hydrochloric acid (1.2 ml, 15 mmol) was brought to reflux under $N_2$ for 1 h. Additional HCl was added (1.2 ml, 15 mmol) and the reaction mixture was refluxed for 2 h. The mixture was cooled and partitioned between water and DCM (20 mL each). The layers were separated. The aqueous layer was extracted with DCM (10 mL). The combined organic phases were washed with phosphate buffer (pH 6-7), dried over $Na_2SO_4$ and evaporated in vacuo. The residue was chromatographed on silica gel eluting with 10 to 20% EtOAc/hexane to yield the desired product (0.59 g, 66%). $^1$H NMR (CD$_2$Cl$_2$, 400 MHz): 7.53 (1H, ddd, J=8.1, 5.0, 2.2 Hz), 7.36-7.19 (3H, m), 6.91 (1H, d, J=7.3 Hz), 6.46 (1H, d, J=20.1 Hz).

Step C. 7,8-difluoronaphthalen-1-yl trifluoromethanesulfonate. A stirred solution of 7,8-difluoronaphthalen-1-ol (0.58 g, 3.22 mmol) and N-ethyl-N-isopropylpropan-2-amine (0.84 ml, 4.8 mmol) in dichloromethane (16 mL) was cooled to −78° C. and triflic anhydride (0.60 mL, 3.5 mmol) was added dropwise. The reaction mixture was warmed to r.t., washed with sat. NaHCO$_3$, dried over Na$_2$SO$_4$, and evaporated in vacuo. The solid was chromatographed on silica gel eluting with 2 to 20% EtOAc/hexane to yield product (0.80 g, 80%).

Step D. 2-(7,8-difluoronaphthalen-1-yl)-4,4,5,5-tetramethyl-1,3,2-dioxaborolane. A stirred mixture of 7,8-difluoronaphthalen-1-yl trifluoromethanesulfonate (0.80 g, 2.5 mmol), bis(pinacolato)diboron (1.9 g, 7.7 mmol), potassium acetate (0.75 g, 7.7 mmol), Pd(dppf)Cl$_2$*CH$_2$Cl$_2$ (0.21 g, 0.26 mmol) and 1,4-dioxane (5 mL) was degassed and stirred at 80° C. overnight. The reaction mixture was cooled to r.t. and partitioned between MTBE and water (20 mL each). The layers were separated. The combined organic phases were washed with brine, dried over Na$_2$SO$_4$, evaporated in vacuo and chromatographed eluting with 5% EtOAc/hexane to yield the product (0.62 g, 83%). $^1$H NMR (CD$_2$Cl$_2$, 400 MHz): 7.80 (1H, d, J=8.3 Hz), 7.61 (1H, d, J=6.8 Hz), 7.56 (1H, ddd, J=9.0, 4.9, 2.2 Hz), 7.40 (1H, t, J~7.6 Hz), 7.32-7.23 (1H, m), 1.33 (12H, s).

Step E. Tert-butyl (1R,5S)-3-(7-(7,8-difluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate. A mixture of tert-butyl (1R,5S)-3-(7-chloro-8-fluoro-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (50 mg, 0.091 mmol), 2-(7,8-difluoronaphthalen-1-yl)-4,4,5,5-tetramethyl-1,3,2-dioxaborolane (53 mg, 0.18 mmol), Pd(PPh$_3$)$_4$ (10 mg, 0.0091 mmol), 1,4-dioxane (0.9 mL) and 2M Na$_2$CO$_3$ (0.14 mL, 0.27 mmol) was degassed, the vial was capped, and the reaction stirred at 80° C. overnight. The reaction mixture was cooled to r.t. and partitioned between water and EtOAc (15 mL each). The layers were separated. The organic phase was washed with brine, dried over Na$_2$SO$_4$, evaporated in vacuo and chromatographed on silica gel eluting with 4% MeOH/DCM with 1% NH$_4$OH as modifier. The residue was purified on reverse phase eluting with 5-95% MeCN/water with 0.1% TFA as modifier. The target fractions were combined, concentrated in vacuo, basified with Na$_2$CO$_3$ and extracted with DCM (2*15 mL). The combined extracts were dried over Na$_2$SO$_4$, filtered and evaporated in vacuo to yield the product (23 mg, 37%). LCMS (MM-ES+APCI, Pos): m/z 679.3 (M+H)$^+$.

Step F. 4-((1R,5S)-3,8-diazabicyclo[3.2.1]octan-3-yl)-7-(7,8-difluoronaphthalen-1-yl)-8-fluoro-2-(((2R,7aS)-2-fluorotetrahydro-1H-pyrrolizin-7a(5H)-yl)methoxy)pyrido[4,3-d]pyrimidine. A mixture of tert-butyl (1R,5S)-3-(7-(7,8-difluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (23 mg, 0.034 mmol) and DCM (0.8 mL) was cooled to 0° C. with stirring and 4 M hydrogen chloride in dioxane (0.84 mL, 3.4 mmol) was added at once. The reaction mixture was kept at r.t. for 2 h. The dioxane-HCl phase was decanted and discarded. The precipitate was dried under a stream of nitrogen, wetted with 2 drops of water, mixed with DCM (10 mL) and 2M Na$_2$CO$_3$ (0.5 mL), and sonicated. The organic phase was dried over Na$_2$CO$_3$, filtered and evaporated in vacuo to yield the target compound (20 mg, 97%). LCMS (MM-ES+APCI, Pos): m/z 579.3 (M+H)$^+$.

Example 431
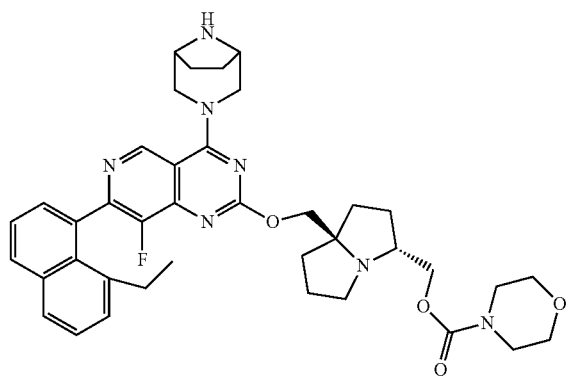 [SMILES: CCc1cccc2cccc(-c3ncc4c(N5CC6CCC(C5)N6)nc(OC[C@]56CCCN5[C@@H](COC(=O)N5CCOCC5)CC6)nc4c3F)c12]
((3R,7aR)-7a-(((4-(3,8-diazabicyclo[3.2.1]octan-3-yl)-7-(8-ethylnaphthalen-1-yl)-8-fluoropyrido[4,3-d]pyrimidin-2-yl)oxy)methyl)hexahydro-1H-pyrrolizin-3-yl)methyl morpholine-4-carboxylate (trans enantiomer)
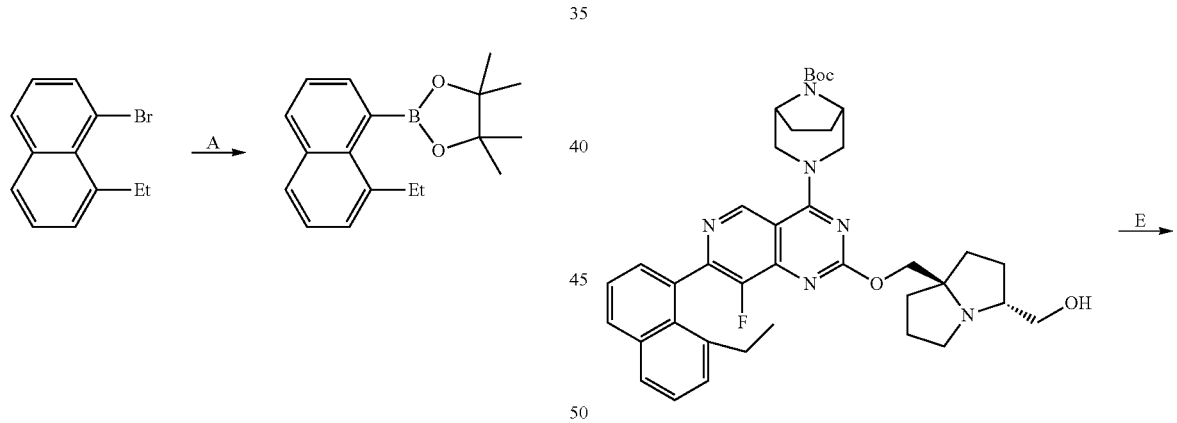
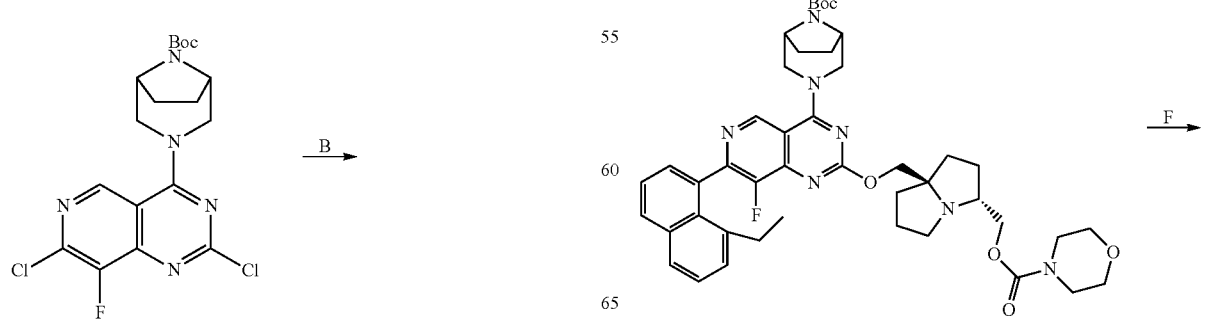
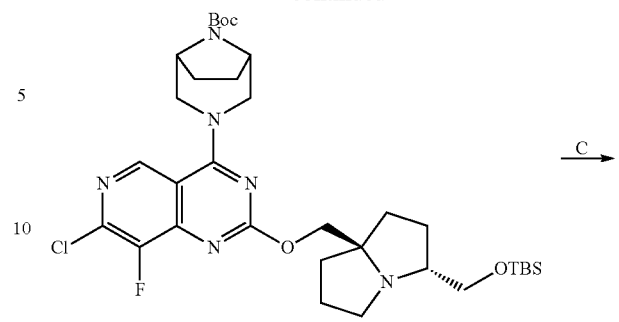
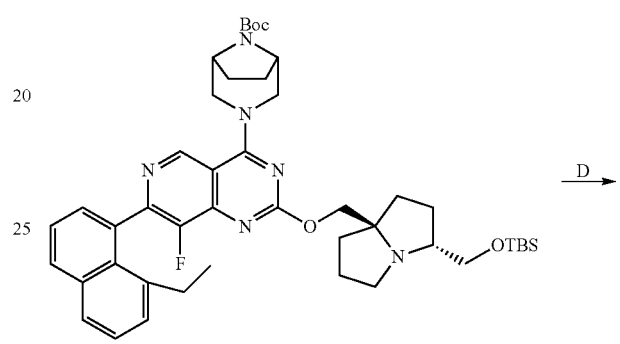

-continued

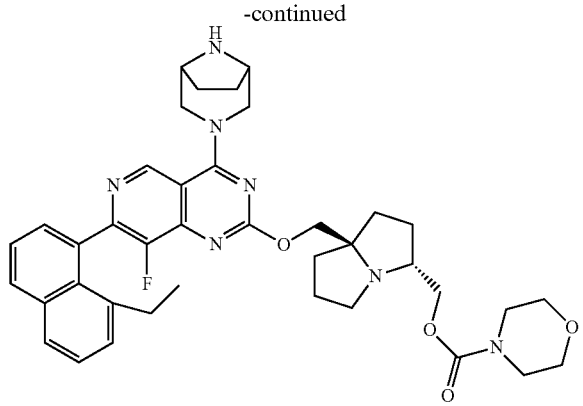

Step A. 2-(8-ethylnaphthalen-1-yl)-4,4,5,5-tetramethyl-1,3,2-dioxaborolane. To a solution of 1-bromo-8-ethylnaphthalene (4.7 g, 20 mmol) in 1,4-dioxane (67 ml) were added KOAc (3.9 g, 40 mmol), 4,4,4',4',5,5,5',5'-octamethyl-2,2'-bi(1,3,2-dioxaborolane) (10 g, 40 mmol) and PdCl$_2$(dppf).DCM (0.73 g, 1.00 mmol). The mixture was heated under N$_2$ at 90° C. for 15 h. The mixture was cooled to rt and quenched with hexanes. The mixture was filtered, the filtrate was concentrated, and purified by flash chromatography eluting with 0 to 5% EtOAc/hexanes to give the title compound (2.5 g 45%) as a white solid. $^1$H NMR (400 MHz, (CDCl$_3$) δ 7.86 (d, J=8.0 Hz, 1H), 7.70 (d, J=7.8 Hz, 1H), 7.68 (d, J=7.8 Hz, 1H), 7.45-7.35 (m, 3H), 3.23 (q, J=7.3 Hz, 2H), 1.44 (s, 12H), 1.37 (t, J=7.3 Hz, 3H).

Step B. tert-butyl 3-(2-(((3R,7aR)-3-(((tert-butyldimethylsilyl)oxy)methyl)tetrahydro-1H-pyrrolizin-7a(5H)-yl)methoxy)-7-chloro-8-fluoropyrido[4,3-d]pyrimidin-4-yl)-3,8-diazabicyclo[3.2.1]octane-8-carboxylate. To a solution of tert-butyl 3-(2,7-dichloro-8-fluoropyrido[4,3-d]pyrimidin-4-yl)-3,8-diazabicyclo[3.2.1]octane-8-carboxylate (0.92 g, 2.2 mmol) and ((3R,7aR)-3-(((tert-butyldimethylsilyl)oxy)methyl)tetrahydro-1H-pyrrolizin-7a(5H)-yl)methanol (0.54 g, 1.9 mmol) in THF (9 ml) at 0° C. was added NaH (90 mg, 2.3 mmol). The mixture was warmed to rt and stirred at rt for 18 h. The mixture purified by flash chromatography eluting with 0 to 10% MeOH/EtOAc with 5% NH$_3$·H$_2$O as eluent to give the title compound (0.82 g, 64%) as a yellow solid. LCMS (MM-ES+APCI, Pos): m/z 677.4 (100%), 679.4 (40%) (M+H, M+3).

Step C. tert-butyl 3-(2-(((3R,7aR)-3-(((tert-butyldimethylsilyl)oxy)methyl)tetrahydro-1H-pyrrolizin-7a(5H)-yl)methoxy)-7-chloro-8-fluoropyrido[4,3-d]pyrimidin-4-yl)-3,8-diazabicyclo[3.2.1]octane-8-carboxylate. To a vial containing tert-butyl 3-(2-(((3R,7aR)-3-(((tert-butyldimethylsilyl)oxy)methyl)tetrahydro-1H-pyrrolizin-7a(5H)-yl)methoxy)-7-chloro-8-fluoropyrido[4,3-d]pyrimidin-4-yl)-3,8-diazabicyclo[3.2.1]octane-8-carboxylate (68 mg, 0.10 mmol), 2-(8-ethylnaphthalen-1-yl)-4,4,5,5-tetramethyl-1,3,2-dioxaborolane (57 mg, 0.20 mmol), CataCXium® A Pd G3 (22 mg, 0.030 mmol) were added THF (1.0 ml) and K$_3$PO$_4$ (0.20 ml, 0.20 mmol). The vial was purged with Ar and closed with a septum. The mixture was heated at 70° C. for 6 h, cooled to rt, and purified by flash chromatography eluting with 0 to 10% MeOH/EtOAc with 5% NH$_3$·H$_2$O to give the title compound (64 mg, 80%) as an off-white solid. LCMS (MM-ES+APCI, Pos): m/z 797.5 (M+H).

Step D. tert-butyl 3-(7-(8-ethylnaphthalen-1-yl)-8-fluoro-2-(((3R,7aR)-3-(hydroxymethyl)tetrahydro-1H-pyrrolizin-7a(5H)-yl)methoxy)pyrido[4,3-d]pyrimidin-4-yl)-3,8-diazabicyclo[3.2.1]octane-8-carboxylate. To a solution of tert-butyl 3-(2-(((3R,7aR)-3-(((tert-butyldimethylsilyl)oxy)methyl)tetrahydro-1H-pyrrolizin-7a(5H)-yl)methoxy)-7-(8-ethylnaphthalen-1-yl)-8-fluoropyrido[4,3-d]pyrimidin-4-yl)-3,8-diazabicyclo[3.2.1]octane-8-carboxylate (64 mg, 0.080 mmol) in THF (0.40 ml) was added TBAF (0.16 ml, 0.16 mmol). The solution was stirred at rt for 2 h and purified by preparative C18 HPLC eluting with 0-95% CH$_3$CN/H$_2$O with 0.1% TFA as modifier. The desired fractions were combined, basified with NaHCO$_3$(Sat.), and extracted with EtOAc. The combined extract was dried over Na$_2$SO$_4$ and concentrated to give the title compound (58 mg, 106%) as a yellow oil. LCMS (MM-ES+APCI, Pos): m/z 683.4 (M+H).

Step E. tert-butyl 3-(7-(8-ethylnaphthalen-1-yl)-8-fluoro-2-(((3R,7aR)-3-(((((4-nitrophenoxy)carbonyl)oxy)methyl)tetrahydro-1H-pyrrolizin-7a(5H)-yl)methoxy)pyrido[4,3-d]pyrimidin-4-yl)-3,8-diazabicyclo[3.2.1]octane-8-carboxylate. To a solution of tert-butyl 3-(7-(8-ethylnaphthalen-1-yl)-8-fluoro-2-(((3R,7aR)-3-(hydroxymethyl)tetrahydro-1H-pyrrolizin-7a(5H)-yl)methoxy)pyrido[4,3-d]pyrimidin-4-yl)-3,8-diazabicyclo[3.2.1]octane-8-carboxylate (58 mg, 0.085 mmol) and Et$_3$N (24 µl, 0.17 mmol) in THF (1.7 ml) at 0° C. was added 4-nitrophenyl carbonochloridate (26 mg, 0.13 mmol). The solution was stirred at 0° C. for 1 h. To the suspension at 0° C. was added morpholine (17 µl, 0.20 mmol) dropwise. The mixture was stirred at 0° C. for 1 h and purified by preparative C18 HPLC eluting with 0-95% CH$_3$CN/H$_2$O with 0.1% TFA as modifier. The desired fractions were combined, basified with NaHCO$_3$(Sat.) and extracted with EtOAc. The combined extract was washed with brine, dried over Na$_2$SO$_4$ and concentrated to give the title compound (10 mg, 31% over 2 steps) as a white solid. LCMS (MM-ES+APCI, Pos): m/z 796.3 (M+H).

Step F. ((3R,7aR)-7a-(((4-(3,8-diazabicyclo[3.2.1]octan-3-yl)-7-(8-ethylnaphthalen-1-yl)-8-fluoropyrido[4,3-d]pyrimidin-2-yl)oxy)methyl)hexahydro-1H-pyrrolizin-3-yl)methyl morpholine-4-carboxylate. To a solution of ((3R,7aR)-7a-(((4-(8-(tert-butoxycarbonyl)-3,8-diazabicyclo[3.2.1]octan-3-yl)-7-(8-ethylnaphthalen-1-yl)-8-fluoropyrido[4,3-d]pyrimidin-2-yl)oxy)methyl)hexahydro-1H-pyrrolizin-3-yl)methyl morpholine-4-carboxylate (10 mg, 0.013 mmol) in DCM (1.0 ml) was added TFA (0.50 ml). The solution was stirred at rt for 45 min and concentrated. The residue was purified by preparative C18 HPLC eluting with 0-95% CH$_3$CN/H$_2$O with 0.1% TFA as modifier. The desired fractions were combined, basified with NaHCO$_3$ and extracted with DCM/IPA (10:1). The combined extract was dried over Na$_2$SO$_4$ and concentrated to give the title compound (5 mg, 57%) as a white solid. LCMS (MM-ES+APCI, Pos): m/z 696.4 (M+H).

879
Example 432

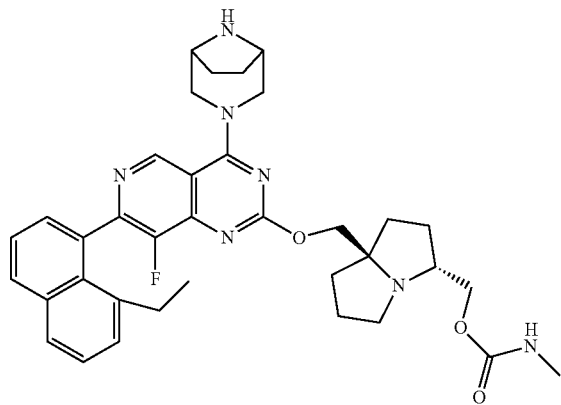

((3R,7aR)-7a-(((4-(3,8-diazabicyclo[3.2.1]octan-3-yl)-7-(8-ethylnaphthalen-1-yl)-8-fluoropyrido[4,3-d]pyrimidin-2-yl)oxy)methyl)hexahydro-1H-pyrrolizin-3-yl)methyl methylcarbamate. (trans enantiomer)

Synthesized according to Example 431 substituting methyl amine for morpholine in step E. LCMS (MM-ES+ APCI, Pos): m/z 640.4 (M+H).

880
Example 433

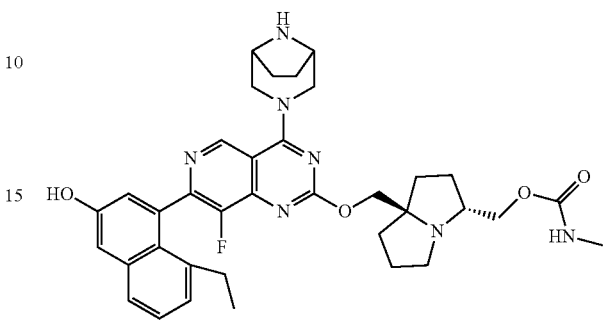

((3R,7aR)-7a-(((4-((1R,5S)-3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)hexahydro-1H-pyrrolizin-3-yl)methyl methylcarbamate (trans racemic)

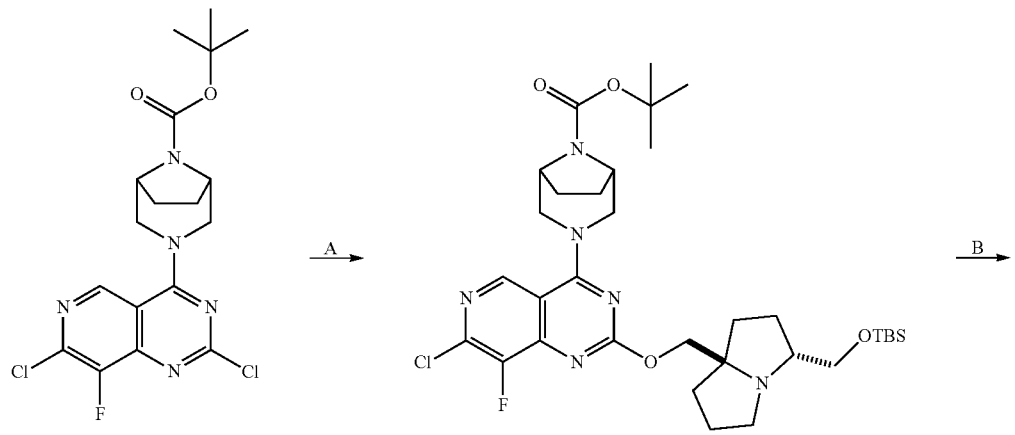

-continued
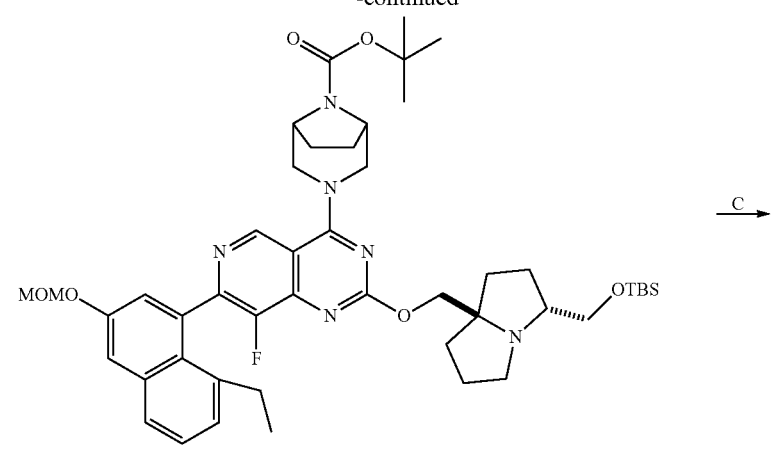
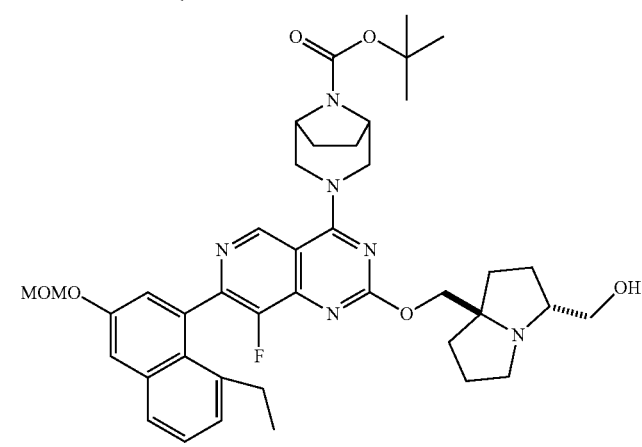
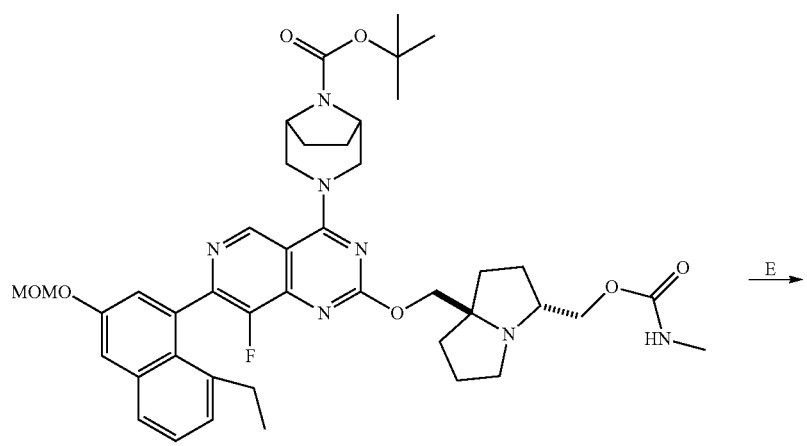
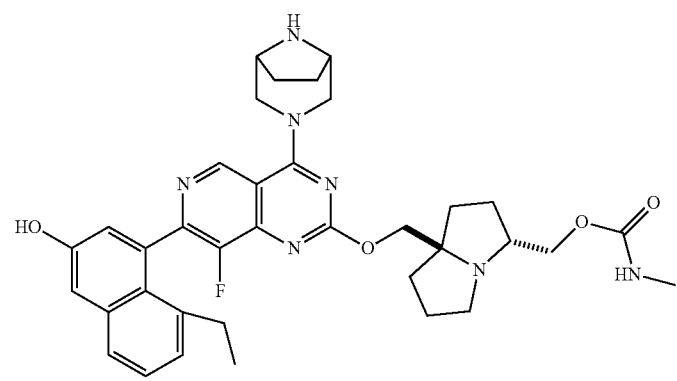

Step A. tert-butyl 3-(2-(((3R,7aR)-3-(((tert-butyldimethylsilyl)oxy)methyl)tetrahydro-1H-pyrrolizin-7a(5H)-yl)methoxy)-7-chloro-8-fluoropyrido[4,3-d]pyrimidin-4-yl)-3,8-diazabicyclo[3.2.1]octane-8-carboxylate. To a solution of tert-butyl (1R,5S)-3-(2,7-dichloro-8-fluoropyrido[4,3-d]pyrimidin-4-yl)-3,8-diazabicyclo[3.2.1]octane-8-carboxylate (1.04 g, 2.42 mmol) and 3-(((tert-butyldimethylsilyl)oxy)methyl)tetrahydro-1H-pyrrolizin-7a(5H)-yl)methanol (0.60 g, 2.1 mmol) in THF (50 mL) at 0° C. was added sodium hydride (93 mg, 2.3 mmol). The mixture was warmed to ambient temperature, stirred for 16 hours, quenched with sat. NH$_4$Cl (50 mL) and extracted with EtOAc (3×30 mL). The combined organic phases were washed with brine (30 mL), dried over Na$_2$SO$_4$, filtered and concentrated in vacuo. The residue was purified by flash chromatography eluting with 0 to 20% MeOH/DCM to give the title compound (0.71 g, 50%) as a pale yellow solid. LCMS (MM-ES+APCI, Pos): m/z 678.3 (M+H).

Step B. tert-butyl 3-(2-(((3R,7aR)-3-(((tert-butyldimethylsilyl)oxy)methyl)tetrahydro-1H-pyrrolizin-7a(5H)-yl)methoxy)-7-(8-ethyl-3-(methoxymethoxy)naphthalen-1-yl)-8-fluoropyrido[4,3-d]pyrimidin-4-yl)-3,8-diazabicyclo[3.2.1]octane-8-carboxylate. tert-butyl 3-(2-((-3-(((tert-butyldimethylsilyl)oxy)methyl)tetrahydro-1H-pyrrolizin-7a(5H)-yl)methoxy)-7-chloro-8-fluoropyrido[4,3-d]pyrimidin-4-yl)-3,8-diazabicyclo[3.2.1]octane-8-carboxylate (0.10 g, 0.15 mmol), 2-(8-ethyl-3-(methoxymethoxy)naphthalen-1-yl)-4,4,5,5-tetramethyl-1,3,2-dioxaborolane (61 mg, 0.18 mmol) and Mesylate[(di(1-adamantyl)-n-butylphosphine)-2-(2'-amino-1,1'-biphenyl)]palladium(II) (22 mg, 0.03 mmol) were combined in THF (2 mL) and treated with potassium phosphate (0.44 mL, 1.0 M, 0.44 mmol). The mixture was purged with Ar and then heated in a sealed vial at 60° C. for 16 hours. The cooled mixture was partitioned between water (10 mL) and EtOAc (10 mL), and the aqueous layer was extracted with EtOAc (2×10 mL). The combined organic phases were washed with brine (10 mL), dried over Na$_2$SO$_4$, filtered and concentrated in vacuo. The residue was purified by flash chromatography eluting with 0-16% MeOH/DCM to give the title compound (89 mg, 70%) as a pale yellow foam. LCMS (MM-ES+APCI, Pos): m/z 858.4 (M+H).

Step C. tert-butyl 3-(7-(8-ethyl-3-(methoxymethoxy)naphthalen-1-yl)-8-fluoro-2-(((3R,7aR)-3-(hydroxymethyl)tetrahydro-1H-pyrrolizin-7a(5H)-yl)methoxy)pyrido[4,3-d]pyrimidin-4-yl)-3,8-diazabicyclo[3.2.1]octane-8-carboxylate. To a solution of tert-butyl (1R,5S)-3-(2-((-3-(((tert-butyldimethylsilyl)oxy)methyl)tetrahydro-1H-pyrrolizin-7a(5H)-yl)methoxy)-7-(8-ethyl-3-(methoxymethoxy)naphthalen-1-yl)-8-fluoropyrido[4,3-d]pyrimidin-4-yl)-3,8-diazabicyclo[3.2.1]octane-8-carboxylate (89 mg, 0.10 mmol) in THF (5 mL) was added TBAF (0.30 mL, 0.30 mmol). The solution was stirred at ambient temperature for 30 min., partitioned between water (10 mL) and EtOAc (10 mL) and the layers separated. The aqueous layer was extracted with EtOAc (2×10 mL) and the combined organic phases were washed with brine (10 mL), dried over Na$_2$SO$_4$, filtered and concentrated to afford the title compound which was used directly in the next reaction. LCMS (MM-ES+APCI, Pos): m/z 743.4 (M+H).

Step D. tert-butyl 3-(7-(8-ethyl-3-(methoxymethoxy)naphthalen-1-yl)-8-fluoro-2-(((3R,7aR)-3-(((methylcarbamoyl)oxy)methyl)tetrahydro-1H-pyrrolizin-7a(5H)-yl)methoxy)pyrido[4,3-d]pyrimidin-4-yl)-3,8-diazabicyclo[3.2.1]octane-8-carboxylate. To a solution of tert-butyl (1R,5S)-3-(7-(8-ethyl-3-(methoxymethoxy)naphthalen-1-yl)-8-fluoro-2-((-3-(hydroxymethyl)tetrahydro-1H-pyrrolizin-7a(5H)-yl)methoxy)pyrido[4,3-d]pyrimidin-4-yl)-3,8-diazabicyclo[3.2.1]octane-8-carboxylate (38 mg, 0.050 mmol) in THF (1 mL) was added triethylamine (21 μL, 0.15 mmol) followed by p-nitrophenylchloroformate (15 mg, 0.08 mmol). The mixture was stirred for 10 minutes and methylamine (0.25 mL, 0.50 mmol) was added. After stirred for 10 minutes, the mixture was partitioned between sat. NaHCO$_3$ (10 mL) and EtOAc (10 mL), the layers were separated. The aqueous layer was extracted with EtOAc (2×5 mL). The combined organic phases were washed with brine (5 mL), dried over Na$_2$SO$_4$, filtered and concentrated in vacuo. The residue was purified by flash chromatography eluting with 0-20% MeOH/DCM to give the title compound (15 mg, 36%) as a colorless glass. LCMS (MM-ES+APCI, Pos): m/z 800.4 (M+H).

Step E. ((3R,7aR)-7a-(((4-((1R,5S)-3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)hexahydro-1H-pyrrolizin-3-yl)methyl methylcarbamate. To a solution of tert-butyl (1R,5S)-3-(7-(8-ethyl-3-(methoxymethoxy)naphthalen-1-yl)-8-fluoro-2-((-3-(((methylcarbamoyl)oxy)methyl)tetrahydro-1H-pyrrolizin-7a(5H)-yl)methoxy)pyrido[4,3-d]pyrimidin-4-yl)-3,8-diazabicyclo[3.2.1]octane-8-carboxylate (15 mg, 0.018 mmol) in DCM (0.5 mL) was added 4N HCl/dioxane (0.5 mL). The mixture was stirred for 1 hour and then concentrated in vacuo. The residue was triturated with Et$_2$O, filtered and dried in vacuo to give the title compound as the HCl salt (10 mg, 72%) as a yellow solid. LCMS (MM-ES+APCI, Pos): m/z 656.4 (M+H).

Example 434

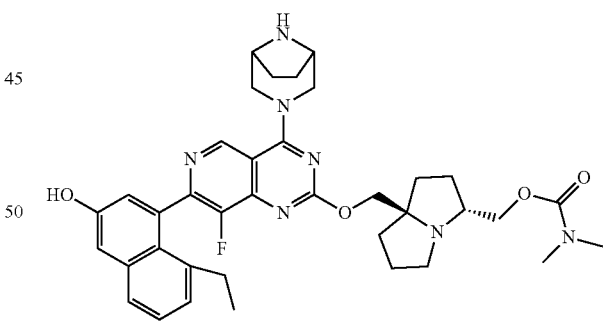

7a-(((4-((1R,5S)-3,8-diazabicyclo[3.2.1]octan-3-yl)-7-(8-ethyl-3-hydroxynaphthalen-1-yl)-8-fluoropyrido[4,3-d]pyrimidin-2-yl)oxy)methyl)hexahydro-1H-pyrrolizin-3-yl)methyl dimethyl carbamate
(trans racemic)

Synthesized according to Example 433 substituting dimethylamine in place of methylamine in Step D to give title product as the HCl salt (18 mg, 77%). LCMS (MM-ES+APCI, Pos): m/z 670.4 (M+H).

Example 435

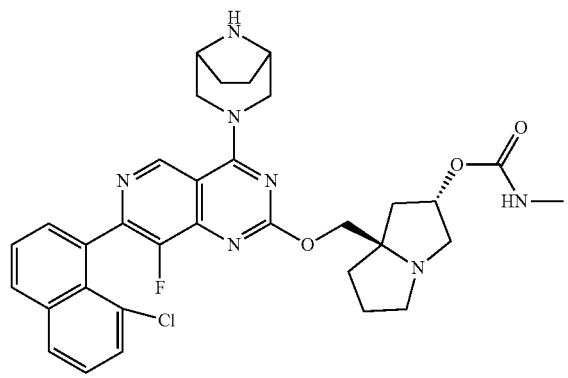 [SMILES: CNC(=O)O[C@@H]1CN2CCC[C@]2(COc2nc(N3CC4CCC(C3)N4)c3cnc(-c4cccc5cccc(Cl)c45)c(F)c3n2)C1]

(2S,7aR)-7a-(((4-(((1R,5S)-3,8-diazabicyclo[3.2.1]
octan-3-yl)-7-(8-chloronaphthalen-1-yl)-8-fluoro-
pyrido[4,3-d]pyrimidin-2-yl)oxy)methyl)hexahydro-
1H-pyrrolizin-2-yl methylcarbamate (racemic,
trans)

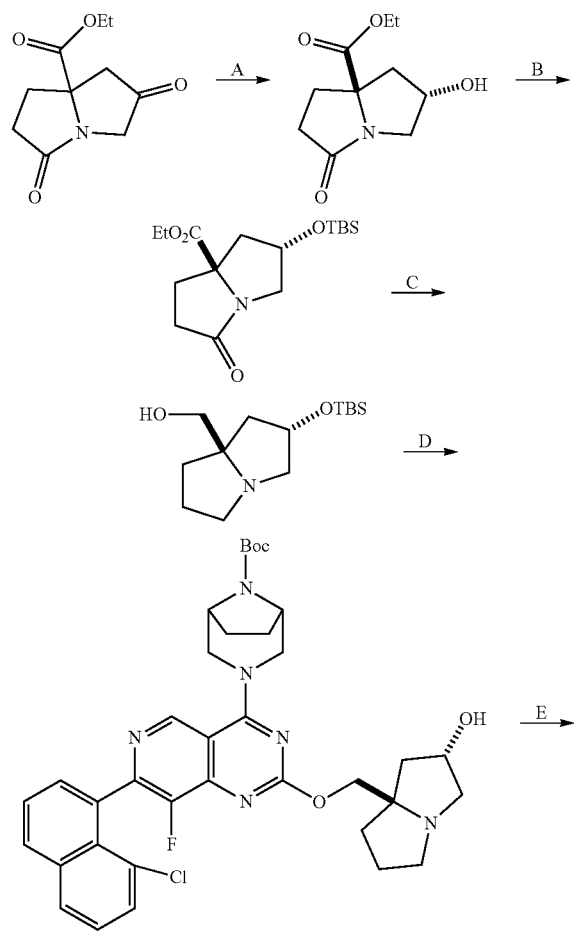

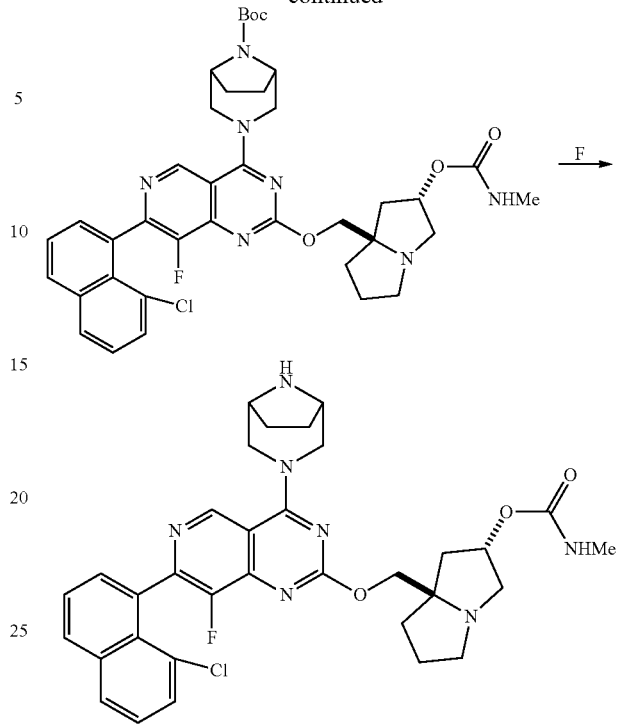

Step A. ethyl (2S,7aR)-2-hydroxy-5-oxotetrahydro-1H-pyrrolizine-7a(5H)-carboxylate. To a solution of ethyl 2,5-dioxotetrahydro-1H-pyrrolizine-7a(5H)-carboxylate (2.4 g, 11 mmol) in EtOH (29 ml) at 0° C. was added NaBH₄ (0.12 g, 3.1 mmol). The mixture was stirred at 0° C. for 0.5 h and quenched with NH₄Cl (Sat., 30 ml) and water (5 ml). The mixture was extracted with chloroform/IPA (4:1). The combined extract was dried over Na₂SO₄, and concentrated. The residue was purified by flash chromatography eluting with 0 to 100% EtOAc/hexanes to give the title compound (0.44 g, 2.1 mmol, 18%) as a white solid, and the cis isomer (1.22 g, 50%) as a white solid. LCMS (MM-ES+APCI, Pos): m/z 214.3 (M+H) for both isomers.

Step B. ethyl (2S,7aR)-2-((tert-butyldimethylsilyl)oxy)-5-oxotetrahydro-1H-pyrrolizine-7a(5H)-carboxylate. To a solution of ethyl (2S,7aR)-2-hydroxy-5-oxotetrahydro-1H-pyrrolizine-7a(5H)-carboxylate (0.43 g, 2.0 mmol) in DMF (10 ml) were added imidazole (0.34 g, 5.0 mmol) and TBS-Cl (0.61 g, 4.0 mmol). The mixture was stirred at rt for 15 h and quenched with EtOAc. The solution was washed with water and brine. The solution was dried over Na₂SO₄, concentrated and purified by flash chromatography eluting with 0 to 80% EtOAc/hexanes to give the title compound (0.52 g, 79%) as a colorless oil. LCMS (MM-ES+APCI, Pos): m/z 328.2 (M+H).

Step C. ((2S,7aR)-2-((tert-butyldimethylsilyl)oxy)tetrahydro-1H-pyrrolizin-7a(5H)-yl)methanol. To a flask containing LAH (2.4 M THF, 0.84 ml, 2.00 mmol) at 0° C. was added THF (2.5 ml) followed by slow addition of a solution of ethyl (2S,7aR)-2-((tert-butyldimethylsilyl)oxy)-5-oxotetrahydro-1H-pyrrolizine-7a(5H)-carboxylate (0.16 g, 0.50 mmol) in THF (2.5 ml). The mixture was warmed to rt and then heated at 50° C. for 3 h and 70° C. for 3 h. The solution was cooled to 0° C. and quenched with brine (0.50 ml). The mixture was filtered, and the filter cake was further washed with DCM/MeOH (9:1). The combined organic solution was washed with brine, dried over Na₂SO₄ and concentrated to give the crude title compound (33 mg, 24%) as a colorless oil. LCMS (MM-ES+APCI, Pos): m/z 372.3 (M+H).

Step D. tert-butyl (1R,5S)-3-(2-(((2S,7aR)-2-((tert-butyldimethylsilyl)oxy)tetrahydro-1H-pyrrolizin-7a(5H)-yl)methoxy)-7-(8-chloronaphthalen-1-yl)-8-fluoropyrido[4,3-d]pyrimidin-4-yl)-3,8-diazabicyclo[3.2.1]octane-8-carboxylate. To a solution of tert-butyl (1R,5S)-3-(2-chloro-7-(8-chloronaphthalen-1-yl)-8-fluoropyrido[4,3-d]pyrimidin-4-yl)-3,8-diazabicyclo[3.2.1]octane-8-carboxylate (55 mg, 0.10 mmol) and ((2S,7aR)-2-((tert-butyldimethylsilyl)oxy)tetrahydro-1H-pyrrolizin-7a(5H)-yl)methanol (30 mg, 0.11 mmol) in THF (1.0 ml) at rt was added NaH (4.8 mg, 0.20 mmol). The mixture was stirred at rt for 4 h and quenched with water. The mixture was extracted with EtOAc. The combined extract was dried over Na₂SO₄ and concentrated. The material was taken up in THF (1.0 ml) and TBAF (0.10 ml, 0.20 mmol) was added. The solution was stirred at rt for 3.5 h and purified by preparative C18 HPLC eluting with 0-95% CH₃CN/H₂O with 0.1% TFA as modifier. The desired fractions were combined, neutralized with NaHCO₃(Sat.) and extracted with EtOAc. The combined extract was dried over Na₂SO₄ and concentrated to give the title compound (29 mg, 43%) as of a white solid. LCMS (MM-ES+APCI, Pos): m/z 675.3 (M+H).

Step E. tert-butyl (1R,5S)-3-(2-(((2S,7aR)-2-((1H-imidazole-1-carbonyl)oxy)tetrahydro-1H-pyrrolizin-7a(5H)-yl)methoxy)-7-(8-chloronaphthalen-1-yl)-8-fluoropyrido[4,3-d]pyrimidin-4-yl)-3,8-diazabicyclo[3.2.1]octane-8-carboxylate. To a flask containing tert-butyl (1R,5S)-3-(7-(8-chloronaphthalen-1-yl)-8-fluoro-2-(((2S,7aR)-2-hydroxytetrahydro-1H-pyrrolizin-7a(5H)-yl)methoxy)pyrido[4,3-d]pyrimidin-4-yl)-3,8-diazabicyclo[3.2.1]octane-8-carboxylate (29 mg, 0.043 mmol) and CDI (14 mg, 0.086 mmol) under N₂ was added THF (0.9 ml). The solution was stirred at rt for 15 h. To the solution at 0° C. was added MeNH2 (2.0 M in THF, 0.050 ml, 0.10 mmol). The solution was stirred at 0° C. for 1 h, warmed to rt and purified by preparative C18 HPLC eluting with 0-95% CH₃CN/H₂O with 0.1% TFA as modifier. The desired fractions were combined, neutralized with NaHCO₃(Sat.) and extracted with EtOAc. The combined extract was dried over Na₂SO₄ and concentrated to give the title compound (8.0 mg, 55%) as a white solid. LCMS (MM-ES+APCI, Pos): m/z 732.3 (M+H).

Step F. (2S,7aR)-7a-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)hexahydro-1H-pyrrolizin-2-yl methylcarbamate. To a solution of tert-butyl (1R,5S)-3-(7-(8-chloronaphthalen-1-yl)-8-fluoro-2-(((2S,7aR)-2-((methylcarbamoyl)oxy)tetrahydro-1H-pyrrolizin-7a(5H)-yl)methoxy)pyrido[4,3-d]pyrimidin-4-yl)-3,8-diazabicyclo[3.2.1]octane-8-carboxylate (8.0 mg, 0.011 mmol) in DCM (0.60 ml) was added TFA (0.30 ml). The solution was stirred at rt for 0.5 h, and concentrated. The residue was purified by preparative C18 HPLC eluting with 0-95% CH₃CN/H₂O with 0.1% TFA as modifier. The desired fractions were combined, basified with NaHCO₃ (sat.) and extracted with CHCl3/IPA (5:1). The combined extract was dried over Na₂SO₄ and concentrated to give the title compound (5.0 mg, 72%) as a light yellow solid. LCMS (MM-ES+APCI, Pos): m/z 632.4 (100%) (M+H).

Example 436

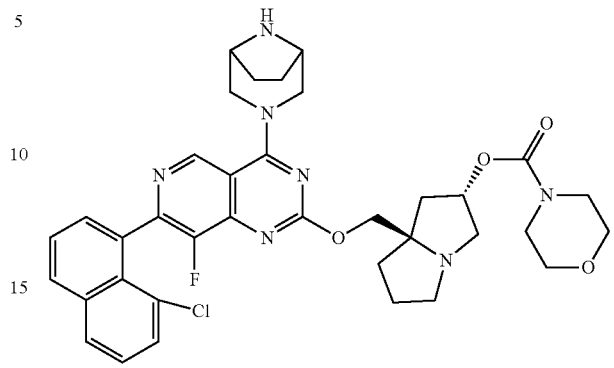

(2S,7aR)-7a-(((4-((1R,5S)-3,8-diazabicyclo[3.2.1]octan-3-yl)-7-(8-chloronaphthalen-1-yl)-8-fluoropyrido[4,3-d]pyrimidin-2-yl)oxy)methyl)hexahydro-1H-pyrrolizin-2-yl morpholine-4-carboxylate (racemic, trans)

Synthesized according to Example 435 substituting morpholine for methyl amine in step E to give product (7.0 mg, 80%) as a light yellow solid. LCMS (MM-ES+APCI, Pos): m/z 688.5 (M+H).

Example 437

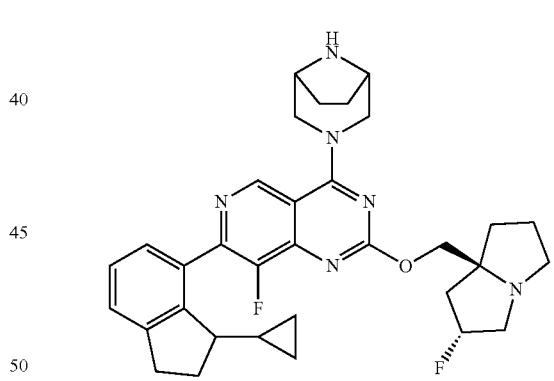

4-(3,8-diazabicyclo[3.2.1]octan-3-yl)-7-(3-cyclopropyl-2,3-dihydro-1H-inden-4-yl)-8-fluoro-2-(((2R,7aS)-2-fluorotetrahydro-1H-pyrrolizin-7a(5H)-yl)methoxy)pyrido[4,3-d]pyrimidine (racemic, trans)

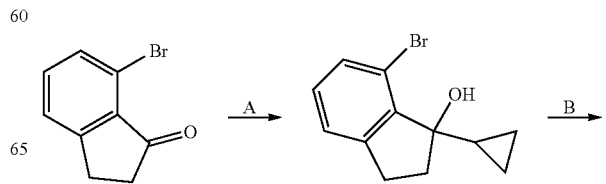

-continued

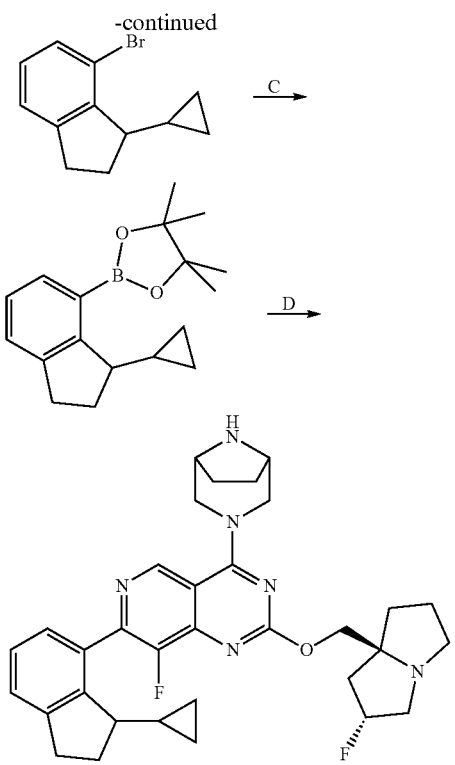

Step A. 7-bromo-1-cyclopropyl-2,3-dihydro-1H-inden-1-ol. To a suspension of 7-bromo-2,3-dihydro-1H-inden-1-one (0.21 g, 1.0 mmol) in THF (5.0 ml) at rt was added cyclopropylmagnesium bromide (4.0 ml, 2.0 mmol) under $N_2$. The solution was heated at 60° C. for 3 h and cooled to rt. The mixture was purified by flash chromatography eluting with 0 to 25% EtOAc/hexanes to give the title compound (116 mg, 46%) as a colorless oil. 1H NMR (400 MHz, (CDCl$_3$) δ 7.34 (d, J=7.8 Hz, 1H), 7.16 (d, J=7.4 Hz, 1H), 7.10-7.05 (m, 1H), 2.90-2.70 (m, 1H), 2.30-2.05 (m, 2H), 1.50-1.35 (m, 1H), 0.60-0.50 (m, 1H), 0.50-0.35 (m, 4H).

Step B. 7-bromo-1-cyclopropyl-2,3-dihydro-1H-indene. To a solution of 7-bromo-1-cyclopropyl-2,3-dihydro-1H-inden-1-ol (0.11 g, 0.43 mmol) and triethylsilane (0.21 ml, 1.3 mmol) in DCM (2 ml) at 0° C. was added BF$_3$·Et$_2$O (0.16 ml, 1.3 mmol). The solution was stirred at 0° C. for 1 h and quenched with NaHCO$_3$(Sat.). The two layers were separated. The organic layer was dried over Na$_2$SO$_4$, and concentrated. The residue was purified by flash chromatography eluting with hexanes to give the title compound (91 mg, 89%) as a colorless oil. 1H NMR (400 MHz, (CDCl$_3$) δ 7.31 (d, J=7.9 Hz, 1H), 7.14 (d, J=7.4 Hz, 1H), 7.05-6.95 (m, 1H), 3.20-3.05 (m, 1H), 2.95-2.75 (m, 2H), 2.25-2.10 (m, 1H), 2.05-1.90 (m, 1H), 1.05-0.90 (m, 1H), 0.65-0.50 (m, 2H), 0.45-0.35 (m, 1H), 0.25-0.15 (m, 1H).

Step C. 2-(3-cyclopropyl-2,3-dihydro-1H-inden-4-yl)-4,4,5,5-tetramethyl-1,3,2-dioxaborolane. To a mixture of 7-bromo-1-cyclopropyl-2,3-dihydro-1H-indene (53 mg, 0.22 mmol), 4,4,4',4',5,5,5',5'—Octamethyl-2,2'-bi-1,3,2-dioxaborolane (0.11 g, 0.45 mmol), KOAc (66 mg, 0.67 mmol) in 1,4-dioxane (2.2 ml) was added PdCl$_2$(dppf). DCM (18 mg, 0.022 mmol) under $N_2$. The mixture was sparged with Ar for 5 minutes and heated at 100° C. for 15 h. The mixture was cooled to rt, quenched with EtOAc and filtered. The filtrate was concentrated, and the residue was purified by flash chromatography eluting with 0 to 30% EtOAc/hexanes to give the title compound (48 mg, 76%) as a yellow oil. LCMS (MM-ES+APCI, Pos): m/z 285.3 (M+H).

Step D. tert-butyl 3-(7-(3-cyclopropyl-2,3-dihydro-1H-inden-4-yl)-8-fluoro-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate. To a vial containing tert-butyl 3-(7-chloro-8-fluoro-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (43 mg, 0.15 mmol), 2-(3-cyclopropyl-2,3-dihydro-1H-inden-4-yl)-4,4,5,5-tetramethyl-1,3,2-dioxaborolane (55 mg, 0.10 mmol), Pd(Ph3)4 (12 mg, 0.010 mmol) under $N_2$ was added K2CO3 (2.0 M, 0.15 ml, 0.30 mmol) followed by 1,4-dioxane (1.0 ml). The vial was closed and the mixture was heated at 80° C. for 15 h. The mixture was cooled to rt, diluted with water and extracted with EtOAc. The extract was dried over Na2SO4 and concentrated to give the crude title compound as a yellow oil. The material was taken up in DCM (1.0 ml) and TFA (0.50 ml) was added. The solution was stirred at rt for 2 h, concentrated, and the residue was purified by preparative C18 HPLC eluting with 0-95% CH3CN/H2O with 0.1% TFA as modifier. The desired fractions were combined, basified with NaHCO$_3$ (sat.) and extracted with DCM. The combined extract was dried over Na$_2$SO$_4$ and concentrated to give the title compound (32 mg, 52%). LCMS (MM-ES+APCI, Pos): m/z 573.3 (M+H).

Example 438

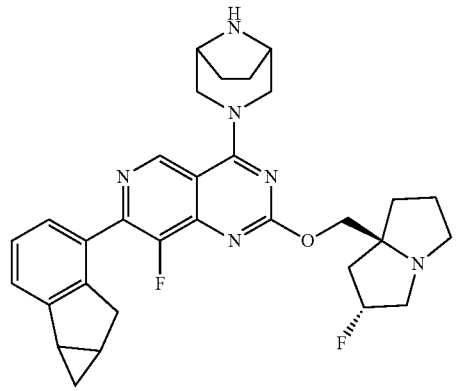 [SMILES: Fc1c(-c2cccc3c2CC2CC32)ncc2c(N3CC4CCC(C3)N4)nc(OC[C@@]34CCCN3C[C@H](F)C4)nc12]

4-(3,8-diazabicyclo[3.2.1]octan-3-yl)-8-fluoro-2-(((2R,7aS)-2-fluorotetrahydro-1H-pyrrolizin-7a(5H)-yl)methoxy)-7-(1,1a,6,6a-tetrahydrocyclopropa[a]inden-5-yl)pyrido[4,3-d]pyrimidine (racemic, trans)

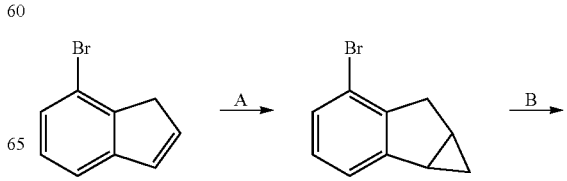

-continued

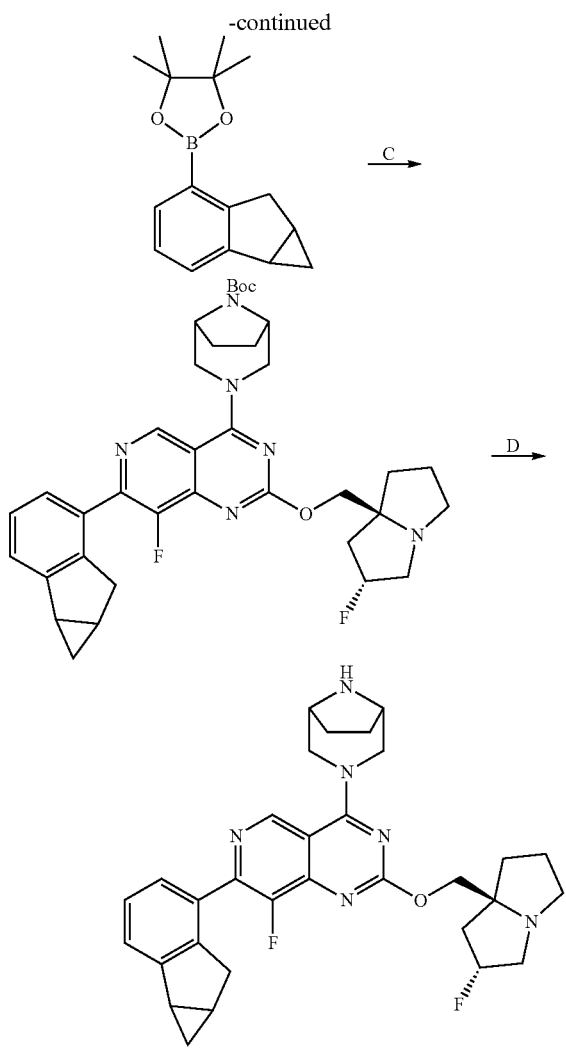

Step A. 5-bromo-1,1a,6,6a-tetrahydrocyclopropa[a]indene. To a solution of Et₂Zn (4.0 ml, 4.0 mmol) was added DCM (4.0 ml) under N₂. The solution was cooled to 0° C., followed by dropwise addition of a solution of TFA (0.31 ml, 4.0 mmol) in DCM (2.0 ml). After stirred for 20 min, a solution of CH2I2 (0.32 ml, 4.0 mmol) in DCM (2.0 ml, 2.0 mmol) was added. After an additional 20 min of stirring, a solution of 5-bromo-1,1a,6,6a-tetrahydrocyclopropa[a]indene (0.42 g, 2.0 mmol) in DCM (2.0 ml) was added. The mixture was warmed to rt and continued to be stirred at rt for 2 h. The reaction mixture was quenched with NaHCO₃ (5 ml). After stirring at rt for 5 min NH₄Cl (Sat.) was added. The two layers were separated. The organic layer was dried over Na₂SO₄, and concentrated. The residue was purified by flash chromatography eluting with hexanes to give the title compound (0.42 g, 100%) as a colorless oil. 1H NMR (400 MHz, (CDCl₃) δ 7.23-7.17 (m, 2H), 7.00-6.93 (m, 1H), 3.12 (dd, J=6.7 Hz, 17.6 Hz, 1H), 2.96 (d, J=17.6 Hz, 1H), 2.47-2.37 (m, 1H), 1.92-1.82 (m, 1H), 1.13-0.92 (m, 2H).

Step B. 4,4,5,5-tetramethyl-2-(1,1a,6,6a-tetrahydrocyclopropa[a]inden-5-yl)-1,3,2-dioxaborolane. To a vial containing a mixture of 5-bromo-1,1a,6,6a-tetrahydrocyclopropa[a]indene (84 mg, 0.40 mmol), 4,4,4',4',5,5,5',5'—Octamethyl-2,2'-bi-1,3,2-dioxaborolane (0.20 g, 0.80 mmol), KOAc (0.12 g, 1.2 mmol) and 1,4-dioxane (4.0 ml) was added PdCl2(dppf)*DCM (33 mg, 0.040 mmol). The vial was closed and heated at 105° C. for 6 h. The mixture was cooled to rt, quenched with EtOAc and filtered. The filtrate was concentrated and the residue was purified by flash chromatography eluting with EtOAc/hexanes to give the impure title compound (48 mg, 46%) as a yellow oil. 1H NMR (400 MHz, (CDCl3) δ 7.52 (d, J=7.9 Hz, 1H), 7.37 (d, J=7.3 Hz, 1H), 7.13-7.07 (m, 1H), 3.28 (dd, J=6.7 Hz, 17.6 Hz, 1H), 3.18 (d, J=17.6 Hz, 1H), 2.40-2.25 (m, 1H), 1.90-1.78 (m, 1H), 1.26 (s, 12H), 1.10-0.95 (m, 1H), 0.06-0.01 (m, 1H).

Step C. tert-butyl 3-(8-fluoro-2-(((2R,7aS)-2-fluorotetrahydro-1H-pyrrolizin-7a(5H)-yl)methoxy)-7-(1,1a,6,6a-tetrahydrocyclopropa[a]inden-5-yl)pyrido[4,3-d]pyrimidin-4-yl)-3,8-diazabicyclo[3.2.1]octane-8-carboxylate. To a vial containing 4,4,5,5-tetramethyl-2-(1,1a,6,6a-tetrahydrocyclopropa[a]inden-5-yl)-1,3,2-dioxaborolane (10 mg, 0.041 mmol), tert-butyl 3-(7-chloro-8-fluoro-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (15 mg, 0.027 mmol), Pd(Ph3)4 (6.3 mg, 0.0054 mmol) under N₂ was added K2CO3 (54 µl, 0.11 mmol), followed by 1,4-dioxane (0.50 ml). The vial was closed, and the mixture was heated at 90° C. for 7 h. The mixture was cooled to rt and purified by preparative C18 HPLC eluting with 0-95% CH3CN/H₂O with 0.1% TFA as modifier. The desired fractions were combined, basified with NaHCO3 (sat.) and extracted with DCM. The combined extract was dried over Na2SO4 and concentrated to give the impure title compound (15 mg, 85%) as a yellow oil. LCMS (MM-ES+APCI, Pos): m/z 645.3 (M+H).

Step D. 4-(3,8-diazabicyclo[3.2.1]octan-3-yl)-8-fluoro-2-(((2R,7aS)-2-fluorotetrahydro-1H-pyrrolizin-7a(5H)-yl)methoxy)-7-(1,1a,6,6a-tetrahydrocyclopropa[a]inden-5-yl)pyrido[4,3-d]pyrimidine. To a solution of tert-butyl 3-(8-fluoro-2-(((2R,7aS)-2-fluorotetrahydro-1H-pyrrolizin-7a(5H)-yl)methoxy)-7-(1,1a,6,6a-tetrahydrocyclopropa[a]inden-5-yl)pyrido[4,3-d]pyrimidin-4-yl)-3,8-diazabicyclo[3.2.1]octane-8-carboxylate (15 mg, 0.023 mmol) in DCM (1.0 ml) was added TFA (0.50 ml). The solution was stirred at rt for 30 min, and concentrated. The residue was purified by preparative C18 HPLC eluting with 0-95% CH3CN/H2O with 0.1% TFA as modifier. The desired fractions were combined, basified with NaHCO3 (sat.) and extracted with DCM/IPA (5:1). The combined extract was dried over Na2SO4 and concentrated to give the title compound (7.0 mg, 55%) as a white solid. LCMS (MM-ES+APCI, Pos): m/z 545.2 (M+H).

Example 439

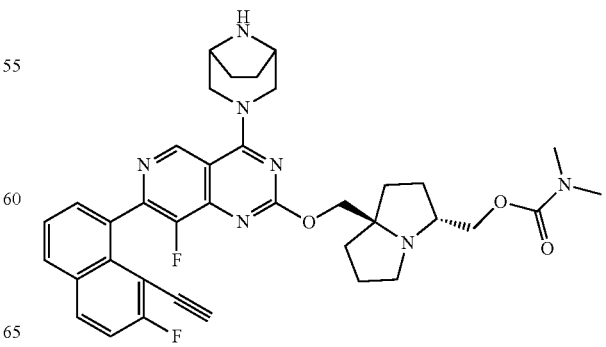

893

((3R,7aR)-7a-(((4-((1R,5S)-3,8-diazabicyclo[3.2.1]octan-3-yl)-7-(8-ethynyl-7-fluoronaphthalen-1-yl)-8-fluoropyrido[4,3-d]pyrimidin-2-yl)oxy)methyl)hexahydro-1H-pyrrolizin-3-yl)methyl dimethylcarbamate (trans racemic)

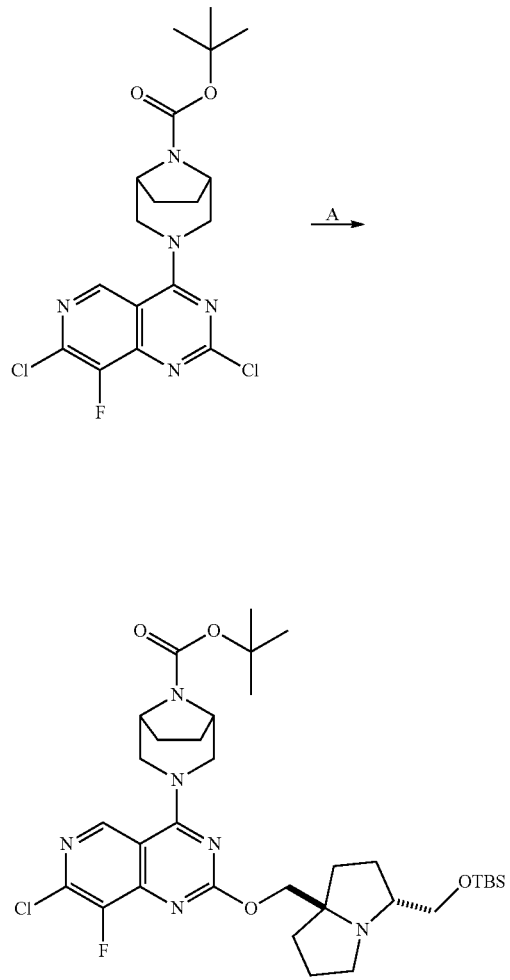

894

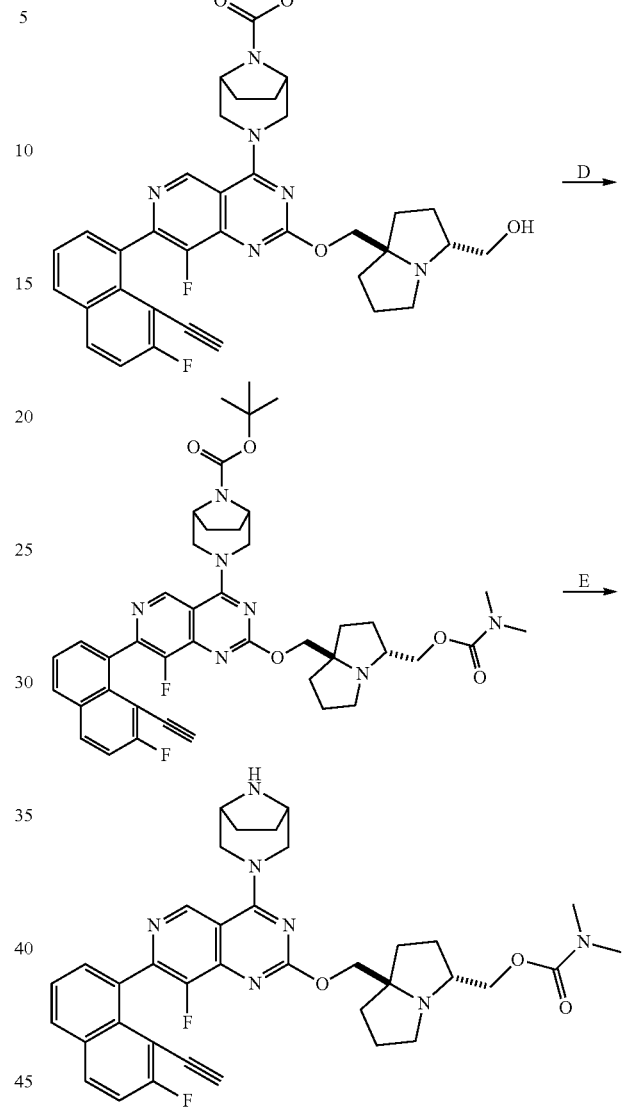

-continued

Step A. tert-butyl (1R,5S)-3-(2-(((3R,7aR)-3-(((tert-butyldimethylsilyl)oxy)methyl)tetrahydro-1H-pyrrolizin-7a(5H)-yl)methoxy)-7-chloro-8-fluoropyrido[4,3-d]pyrimidin-4-yl)-3,8-diazabicyclo[3.2.1]octane-8-carboxylate. To a solution of tert-butyl (1R,5S)-3-(2,7-dichloro-8-fluoropyrido[4,3-d]pyrimidin-4-yl)-3,8-diazabicyclo[3.2.1]octane-8-carboxylate (1.0 g, 2.4 mmol) and ((3R,7aR)-3-(((tert-butyldimethylsilyl)oxy)methyl)tetrahydro-1H-pyrrolizin-7a(5H)-yl)methanol (0.60 g, 2.1 mmol) in THF (50 mL) at 0° C. was added 60% sodium hydride (0.93 g, 2.3 mmol). The mixture was warmed to room temperature and stirred overnight. The mixture was quenched with saturated NH₄Cl (50 mL) and extracted with EtOAc (3×30 mL). The combined organic phases were washed with brine (30 mL), dried over Na₂SO₄, filtered, and concentrated in vacuo. The residue was purified by flash chromatography eluting with 0-20% MeOH/DCM to afford tert-butyl (1R,5S)-3-(2-(((3R,7aR)-3-(((tert-butyldimethylsilyl)oxy)methyl)tetrahydro-1H-pyrrolizin-7a(5H)-yl)methoxy)-7-chloro-8-fluoropyrido

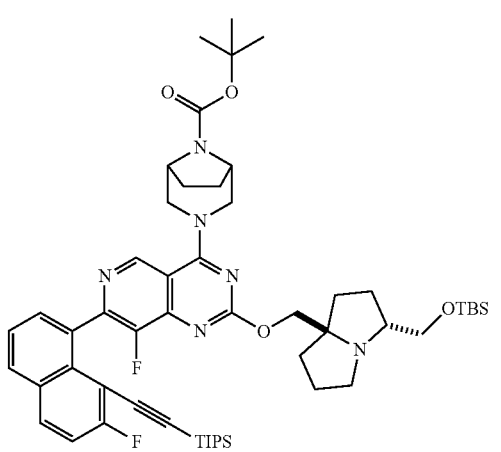

[4,3-d]pyrimidin-4-yl)-3,8-diazabicyclo[3.2.1]octane-8-carboxylate (0.71 g, 50% yield). LCMS (MM-ES+APCI, Pos): m/z 677.3 (M+H).

Step B. tert-butyl (1R,5S)-3-(2-(((3R,7aR)-3-(((tert-butyldimethylsilyl)oxy)methyl)tetrahydro-1H-pyrrolizin-7a (5H)-yl)methoxy)-8-fluoro-7-(7-fluoro-8-((triisopropylsilyl)ethynyl)naphthalen-1-yl)pyrido[4,3-d]pyrimidin-4-yl)-3,8-diazabicyclo[3.2.1]octane-8-carboxylate. A solution of tert-butyl (1R,5S)-3-(2-(((3R,7aR)-3-(((tert-butyldimethylsilyl)oxy)methyl)tetrahydro-1H-pyrrolizin-7a(5H)-yl)methoxy)-7-chloro-8-fluoropyrido[4,3-d]pyrimidin-4-yl)-3,8-diazabicyclo[3.2.1]octane-8-carboxylate (0.20 g, 0.29 mmol), ((2-fluoro-8-(4,4,5,5-tetramethyl-1,3,2-dioxaborolan-2-yl)naphthalen-1-yl)ethynyl)triisopropylsilane (0.16 g, 0.35 mmol), mesylate[(di(1-adamantyl)-n-butylphosphine)-2-(2'-amino-1,1'-biphenyl)]palladium(II) (43 mg, 0.059 mmol), and 1 M K3PO4 (0.9 mL, 0.9 mmol) in THF (4 mL) were added to a capped vial. The reaction was purged with argon and heated to 60° C. overnight. The reaction was quenched with water (35 mL) and washed with EtOAc (3×15 mL). The combined organic layers were washed with brine (30 mL), dried over Na2SO4, filtered, and concentrated in vacuo. The residue was purified by flash chromatography eluting with 0-100% EtOAc/hexanes to afford tert-butyl (1R,5S)-3-(2-(((3R,7aR)-3-(((tert-butyldimethylsilyl)oxy)methyl)tetrahydro-1H-pyrrolizin-7a(5H)-yl) methoxy)-8-fluoro-7-(7-fluoro-8-((triisopropylsilyl)ethynyl)naphthalen-1-yl)pyrido[4,3-d]pyrimidin-4-yl)-3,8-diazabicyclo[3.2.1]octane-8-carboxylate (0.21 g, 0.21 mmol, 74% yield). LCMS (MM-ES+APCI, Pos): m/z 968.5 (M+H).

Step C. tert-butyl (1R,5S)-3-(7-(8-ethynyl-7-fluoronaphthalen-1-yl)-8-fluoro-2-(((3R,7aR)-3-(hydroxymethyl)tetrahydro-1H-pyrrolizin-7a(5H)-yl)methoxy)pyrido[4,3-d]pyrimidin-4-yl)-3,8-diazabicyclo[3.2.1]octane-8-carboxylate. tert-butyl (1R,5S)-3-(2-(((3R,7aR)-3-(((tert-butyldimethylsilyl)oxy)methyl)tetrahydro-1H-pyrrolizin-7a(5H)-yl) methoxy)-8-fluoro-7-(7-fluoro-8-((triisopropylsilyl)ethynyl)naphthalen-1-yl)pyrido[4,3-d]pyrimidin-4-yl)-3,8-diazabicyclo[3.2.1]octane-8-carboxylate (0.21 g, 0.21 mmol) in THF (1 mL) was cooled to 0° C. 1 M TBAF in THF (0.32 mL, 0.32 mmol) was added. The reaction was warmed to room temperature and stirred for 3.5 hours. The solution was diluted with water (40 mL) and extracted with DCM (3×15 mL). The combined organic layers were washed with brine (20 mL), dried with Na2SO4, filtered, and concentrated in vacuo. The residue was purified by flash chromatography eluting with 0-75% (20% MeOH/DCM)/DCM to afford tert-butyl (1R,5S)-3-(7-(8-ethynyl-7-fluoronaphthalen-1-yl)-8-fluoro-2-(((3R,7aR)-3-(hydroxymethyl)tetrahydro-1H-pyrrolizin-7a(5H)-yl)methoxy)pyrido[4,3-d]pyrimidin-4-yl)-3,8-diazabicyclo[3.2.1]octane-8-carboxylate (0.15 g, 97% yield). LCMS (MM-ES+APCI, Pos): m/z 697.3 (M+H).

Step D. tert-butyl (1R,5S)-3-(2-(((3R,7aR)-3-(((dimethylcarbamoyl)oxy)methyl)tetrahydro-1H-pyrrolizin-7a(5H)-yl)methoxy)-7-(8-ethynyl-7-fluoronaphthalen-1-yl)-8-fluoropyrido[4,3-d]pyrimidin-4-yl)-3,8-diazabicyclo[3.2.1] octane-8-carboxylate. To a solution of tert-butyl (1R,5S)-3-(7-(8-ethynyl-7-fluoronaphthalen-1-yl)-8-fluoro-2-(((3R,7aR)-3-(hydroxymethyl)tetrahydro-1H-pyrrolizin-7a(5H)-yl)methoxy)pyrido[4,3-d]pyrimidin-4-yl)-3,8-diazabicyclo[3.2.1]octane-8-carboxylate (50 mg, 0.072 mmol) in THF (1.5 mL) was added triethylamine (30 µl, 0.22 mmol) followed by addition of 4-nitrophenyl carbonochloridate (22 mg, 0.11 mmol). The reaction was stirred at room temperature for 75 minutes and 2 M dimethylamine in THF (0.22 mL, 0.43 mmol) was added. The reaction was stirred at room temperature for 75 minutes. The solution was diluted with water (35 mL) and washed with EtOAc (3×15 mL). The combined organic layers were washed with brine (30 mL), dried over Na2SO4, and concentrated in vacuo. The residue was purified by flash chromatography eluting with 0-50% (20% MeOH/DCM)/DCM to afford tert-butyl (1R,5S)-3-(2-(((3R,7aR)-3-(((dimethylcarbamoyl)oxy)methyl)tetrahydro-1H-pyrrolizin-7a(5H)-yl)methoxy)-7-(8-ethynyl-7-fluoronaphthalen-1-yl)-8-fluoropyrido[4,3-d]pyrimidin-4-yl)-3,8-diazabicyclo[3.2.1]octane-8-carboxylate (7.1 mg, 13% yield). LCMS (MM-ES+APCI, Pos): m/z 768.3 (M+H).

Step E. ((3R,7aR)-7a-(((4-((1R,5S)-3,8-diazabicyclo[3.2.1]octan-3-yl)-7-(8-ethynyl-7-fluoronaphthalen-1-yl)-8-fluoropyrido[4,3-d]pyrimidin-2-yl)oxy)methyl)hexahydro-1H-pyrrolizin-3-yl)methyl dimethylcarbamate dihydrochloride. To a solution of tert-butyl (1R,5S)-3-(2-(((3R,7aR)-3-(((dimethylcarbamoyl)oxy)methyl)tetrahydro-1H-pyrrolizin-7a(5H)-yl)methoxy)-7-(8-ethynyl-7-fluoronaphthalen-1-yl)-8-fluoropyrido[4,3-d]pyrimidin-4-yl)-3,8-diazabicyclo[3.2.1]octane-8-carboxylate (7.1 mg, 0.009 mmol) in DCM (1 mL) was added 4 M HCl in dioxanes (1 mL). After stirred for 30 minutes at room temp, the solution was concentrated in vacuo. The solid was triturated with ether and dried to afford ((3R,7aR)-7a-(((4-((1R,5S)-3,8-diazabicyclo[3.2.1]octan-3-yl)-7-(8-ethynyl-7-fluoronaphthalen-1-yl)-8-fluoropyrido[4,3-d]pyrimidin-2-yl)oxy)methyl)hexahydro-1H-pyrrolizin-3-yl)methyl dimethylcarbamate as the HCl salt (6.8 mg, 79% yield). LCMS (MM-ES+APCI, Pos): m/z 668.3 (M+H).

Example 440

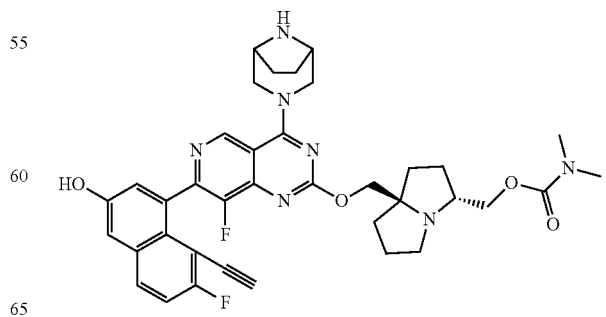

((3R,7aR)-7a-(((4-((1R,5S)-3,8-diazabicyclo[3.2.1]octan-3-yl)-7-(8-ethynyl-7-fluoro-3-hydroxynaphthalen-1-yl)-8-fluoropyrido[4,3-d]pyrimidin-2-yl)oxy)methyl)hexahydro-1H-pyrrolizin-3-yl)methyl dimethyl carbamate (trans racemic)
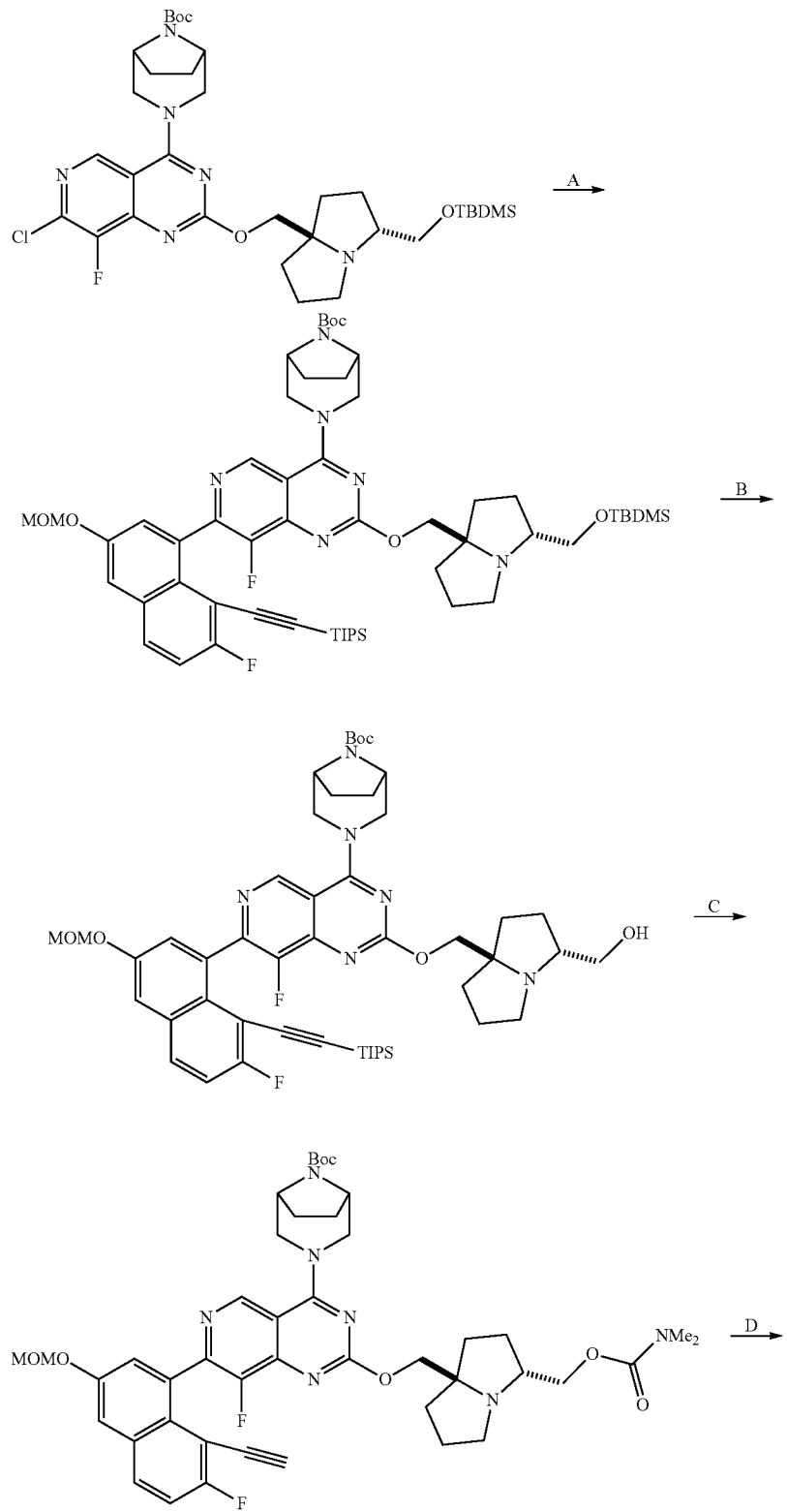

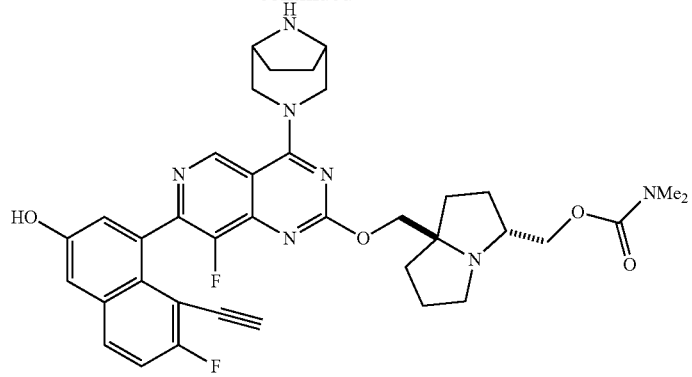

Step A. Tert-butyl (1R,5S)-3-(2-(((3R,7aR)-3-(((tert-butyldimethylsilyl)oxy)methyl)tetrahydro-1H-pyrrolizin-7a(5H)-yl)methoxy)-8-fluoro-7-(7-fluoro-3-(methoxymethoxy)-8-((triisopropylsilyl)ethynyl)naphthalen-1-yl)pyrido[4,3-d]pyri mi din-4-yl)-3,8-diazabicyclo[3.2.1] octane-8-carboxylate (trans racemic). Synthesized according to Example 433, step B substituting and ((2-fluoro-6-(methoxymethoxy)-8-(4,4,5,5-tetramethyl-1,3,2-dioxaborolan-2-yl)naphthalen-1-yl)ethynyl)triisopropylsilane in place of 2-(8-ethyl-3-(methoxymethoxy)naphthalen-1-yl)-4,4,5,5-tetramethyl-1,3,2-dioxaborolane to afford tert-butyl (1R,5S)-3-(2-(((3R,7aR)-3-(((tert-butyldimethylsilyl)oxy)methyl)tetrahydro-1H-pyrrolizin-7a(5H)-yl)methoxy)-8-fluoro-7-(7-fluoro-3-(methoxymethoxy)-8-((triisopropylsilyl)ethynyl)naphthalen-1-yl)pyrido[4,3-d]pyrimidin-4-yl)-3,8-diazabicyclo[3.2.1]octane-8-carboxylate (0.18 g, 77%). LCMS (MM-ES+APCI, Pos). m/z 1028.6 (M+H).

Step B. Tert-butyl (1R,5S)-3-(7-(8-ethynyl-7-fluoro-3-(methoxymethoxy)naphthalen-1-yl)-8-fluoro-2-(((3R,7aR)-3-(hydroxymethyl)tetrahydro-1H-pyrrolizin-7a(5H)-yl)methoxy)pyrido[4,3-d]pyrimidin-4-yl)-3,8-diazabicyclo[3.2.1]octane-8-carboxylate. To a solution of tert-butyl (1R,5S)-3-(2-(((3R,7aR)-3-(((tert-butyldimethylsilyl)oxy)methyl)tetrahydro-1H-pyrrolizin-7a(5H)-yl)methoxy)-8-fluoro-7-(7-fluoro-3-(methoxymethoxy)-8-((triisopropylsilyl)ethynyl)naphthalen-1-yl)pyrido[4,3-d]pyrimidin-4-yl)-3,8-diazabicyclo[3.2.1]octane-8-carboxylate (0.18 g, 0.17 mmol) in THF (3.0 mL) was added 1 N tetra-n-butylammonium fluoride in THF (0.51 mL, 0.51 mmol). After stirred at room temperature for 2 hours, the mixture was condensed in vacuo, and the residue was taken up in EtOAc. After washed with water, the organics were dried over sodium sulfate and condensed in vacuo. The residue was purified by flash chromatography eluting with 0-20% MeOH/DCM to afford tert-butyl (1R,5S)-3-(7-(8-ethynyl-7-fluoro-3-(methoxymethoxy)naphthalen-1-yl)-8-fluoro-2-(((3R,7aR)-3-(hydroxymethyl)tetrahydro-1H-pyrrolizin-7a(5H)-yl)methoxy)pyrido[4,3-d]pyrimidin-4-yl)-3,8-diazabicyclo[3.2.1]octane-8-carboxylate (96 mg, 74%). LCMS (MM-ES+APCI, Pos): m/z 757.3 (M+H).

Step C. Tert-butyl (1R,5S)-3-(2-(((3R,7aR)-3-(((dimethylcarbamoyl)oxy)methyl)tetrahydro-1H-pyrrolizin-7a(5H)-yl)methoxy)-7-(8-ethynyl-7-fluoro-3-(methoxymethoxy)naphthalen-1-yl)-8-fluoropyrido[4,3-d]pyrimidin-4-yl)-3,8-diazabicyclo[3.2.1]octane-8-carboxylate. Synthesized according to Example 433, Step D substituting tert-butyl (1R,5S)-3-(7-(8-ethynyl-7-fluoro-3-(methoxymethoxy)naphthalen-1-yl)-8-fluoro-2-(((3R,7aR)-3-(hydroxymethyl)tetrahydro-1H-pyrrolizin-7a(5H)-yl)methoxy)pyrido[4,3-d]pyrimidin-4-yl)-3,8-diazabicyclo[3.2.1]octane-8-carboxylate and dimethylamine in place of tert-butyl (1R,5S)-3-(7-(8-ethyl-3-(methoxymethoxy)naphthalen-1-yl)-8-fluoro-2-((-3-(hydroxymethyl)tetrahydro-1H-pyrrolizin-7a(5H)-yl)methoxy)pyrido[4,3-d]pyrimidin-4-yl)-3,8-diazabicyclo[3.2.1]octane-8-carboxylate and methylamine to afford tert-butyl (1R,5S)-3-(2-(((3R,7aR)-3-(((dimethylcarbamoyl)oxy)methyl)tetrahydro-1H-pyrrolizin-7a(5H)-yl)methoxy)-7-(8-ethynyl-7-fluoro-3-(methoxymethoxy)naphthalen-1-yl)-8-fluoropyrido[4,3-d]pyrimidin-4-yl)-3,8-diazabicyclo[3.2.1]octane-8-carboxylate (28 mg, 56%). LCMS (MM-ES+APCI, Pos): m/z 828.4 (M+H).

Step D. ((3R,7aR)-7a-(((4-((1R,5S)-3,8-diazabicyclo[3.2.1]octan-3-yl)-7-(8-ethynyl-7-fluoro-3-hydroxynaphthalen-1-yl)-8-fluoropyrido[4,3-d]pyrimidin-2-yl)oxy)methyl)hexahydro-1H-pyrrolizin-3-yl)methyl dimethylcarbamate. Tert-butyl (1R,5S)-3-(2-(((3R,7aR)-3-(((dimethylcarbamoyl)oxy)methyl)tetrahydro-1H-pyrrolizin-7a(5H)-yl)methoxy)-7-(8-ethynyl-7-fluoro-3-(methoxymethoxy)naphthalen-1-yl)-8-fluoropyrido[4,3-d]pyrimidin-4-yl)-3,8-diazabicyclo[3.2.1]octane-8-carboxylate (28 mg, 0.034 mmol) was dissolved in DCM (1.0 mL). HCl (1.0 mL, 4 N in dioxane) was added and the suspension was stirred 30 minutes at room temperature. After condensed in vacuo, the residue was purified by prep HPLC eluting with 5-50% MeCN/H$_2$O with 0.1% TFA as modifier. Fractions containing product were lyophilized to afford ((3R,7aR)-7a-(((4-((1R,5S)-3,8-diazabicyclo[3.2.1]octan-3-yl)-7-(8-ethynyl-7-fluoro-3-hydroxynaphthalen-1-yl)-8-fluoropyrido[4,3-d]pyrimidin-2-yl)oxy)methyl)hexahydro-1H-pyrrolizin-3-yl)methyl dimethylcarbamate as the TFA salt (17 mg, 55%). LCMS (MM-ES+APCI, Pos): m/z 684.3 (M+H).

Example 441

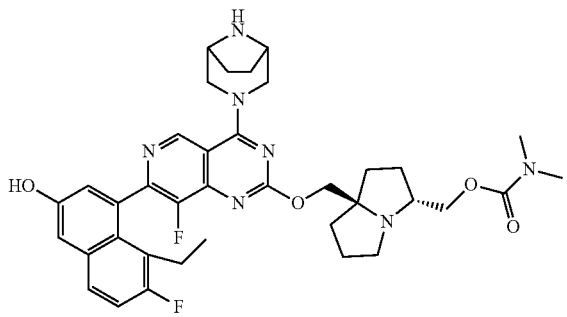 [SMILES: CCc1c(F)ccc2cc(O)cc(-c3ncc4c(N5CC6CCC(C5)N6)nc(OC[C@]56CCCN5[C@@H](COC(=O)N(C)C)CC6)nc4c3F)c12]

((3R,7aR)-7a-(((4-((1R,5S)-3,8-diazabicyclo[3.2.1]
octan-3-yl)-7-(8-ethyl-7-fluoro-3-hydroxynaphtha-
len-1-yl)-8-fluoropyrido[4,3-d]pyrimidin-2-yl)oxy)
methyl)hexahydro-1H-pyrrolizin-3-yl)methyl
dimethylcarbamate (trans racemic)

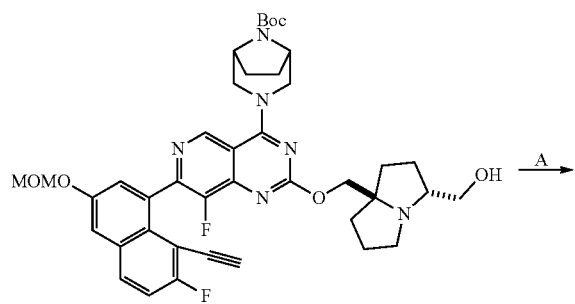 A →

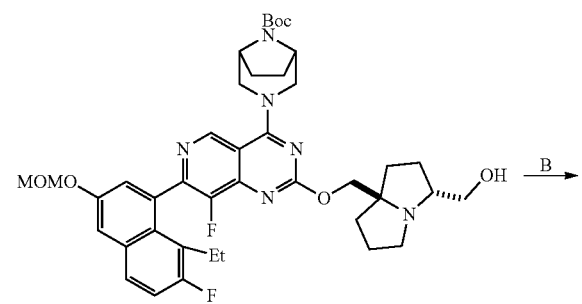 B →

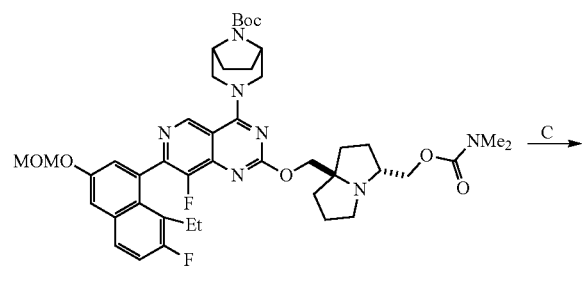 C →

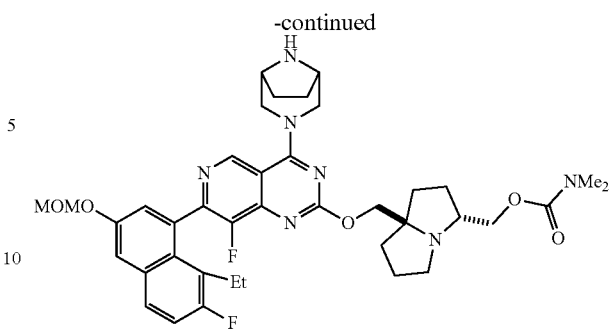

Step A. Tert-butyl (1R,5S)-3-(7-(8-ethyl-7-fluoro-3-(methoxymethoxy)naphthalen-1-yl)-8-fluoro-2-(((3R,7aR)-3-(hydroxymethyl)tetrahydro-1H-pyrrolizin-7a(5H)-yl)methoxy)pyrido[4,3-d]pyrimidin-4-yl)-3,8-diazabicyclo[3.2.1]octane-8-carboxylate. Tert-butyl (1R,5S)-3-(7-(8-ethynyl-7-fluoro-3-(methoxymethoxy)naphthalen-1-yl)-8-fluoro-2-(((3R,7aR)-3-(hydroxymethyl)tetrahydro-11H-pyrrolizin-7a(5H)-yl)methoxy)pyrido[4,3-d]pyrimidin-4-yl)-3,8-diazabicyclo[3.2.1]octane-8-carboxylate (synthesized according to Example 440, step A-B, 67 mg, 0.089 mmol) was dissolved in MeOH (3.0 mL). The mixture was degassed with argon. 10% Pd(OH)2/carbon was added. The suspension was purged with hydrogen and the mixture stirred for 2 hours. The mixture was filtered through Celite and condensed in vacuo to afford tert-butyl (1R,5S)-3-(7-(8-ethyl-7-fluoro-3-(methoxymethoxy)naphthalen-1-yl)-8-fluoro-2-(((3R,7aR)-3-(hydroxymethyl)tetrahydro-1H-pyrrolizin-7a(5H)-yl)methoxy)pyrido[4,3-d]pyrimidin-4-yl)-3,8-diazabicyclo[3.2.1]octane-8-carboxylate (67 mg, 100%). LCMS (MM-ES+APCI, Pos). m/z 761.4 (M+H).

Step B. Tert-butyl (1R,5S)-3-(2-(((3R,7aR)-3-(((dimethylcarbamoyl)oxy)methyl)tetrahydro-1H-pyrrolizin-7a(5H)-yl)methoxy)-7-(8-ethyl-7-fluoro-3-(methoxymethoxy)naphthalen-1-yl)-8-fluoropyrido[4,3-d]pyrimidin-4-yl)-3,8-diazabicyclo[3.2.1]octane-8-carboxylate. Synthesized according to Example 433, Step D substituting tert-butyl (1R,5S)-3-(7-(8-ethyl-7-fluoro-3-(methoxymethoxy)naphthalen-1-yl)-8-fluoro-2-(((3R,7aR)-3-(hydroxymethyl)tetrahydro-11H-pyrrolizin-7a(5H)-yl)methoxy)pyrido[4,3-d]pyrimidin-4-yl)-3,8-diazabicyclo[3.2.1]octane-8-carboxylate in place of tert-butyl (1R,5S)-3-(7-(8-ethyl-3-(methoxymethoxy)naphthalen-1-yl)-8-fluoro-2-((-3-(hydroxymethyl)tetrahydro-1H-pyrrolizin-7a(5H)-yl)methoxy)pyrido[4,3-d]pyrimidin-4-yl)-3,8-diazabicyclo[3.2.1]octane-8-carboxylate and dimethylamine in place of methylamine to afford tert-butyl (1R,5S)-3-(2-(((3R,7aR)-3-(((dimethylcarbamoyl)oxy)methyl)tetrahydro-1H-pyrrolizin-7a(5H)-yl)methoxy)-7-(8-ethyl-7-fluoro-3-(methoxymethoxy)naphthalen-1-yl)-8-fluoropyrido[4,3-d]pyrimidin-4-yl)-3,8-diazabicyclo[3.2.1]octane-8-carboxylate (34 mg, 46%). LCMS (MM-ES+APCI, Pos): m/z 832.4 (M+H).

Step C. ((3R,7aR)-7a-(((4-((1R,5S)-3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)hexahydro-1H-pyrrolizin-3-yl)methyl dimethylcarbamate bis(2,2,2-trifluoroacetate). Synthesized according to Example 440, Step D substituting tert-butyl (1R,5S)-3-(2-(((3R,7aR)-3-(((dimethylcarbamoyl)oxy)methyl)tetrahydro-1H-pyrrolizin-7a(5H)-yl)methoxy)-7-(8-ethyl-7-fluoro-3-(methoxymethoxy)naphthalen-1-yl)-8-fluoropyrido[4,3-d]pyrimidin-4-yl)-3,8-diazabicyclo[3.2.1]octane-8-carboxylate in place of tert-butyl (1R,5S)-3-(2-

(((3R,7aR)-3-(((dimethylcarbamoyl)oxy)methyl)tetrahydro-1H-pyrrolizin-7a(5H)-yl)methoxy)-7-(8-ethynyl-7-fluoro-3-(methoxymethoxy)naphthalen-1-yl)-8-fluoropyrido[4,3-d]pyrimidin-4-yl)-3,8-diazabicyclo[3.2.1]octane-8-carboxylate to afford ((3R,7aR)-7a-(((4-((1R,5S)-3,8-diazabicyclo[3.2.1]octan-3-yl)-7-(8-ethyl-7-fluoro-3-hydroxynaphthalen-1-yl)-8-fluoropyrido[4,3-d]pyrimidin-2-yl)oxy)methyl)hexahydro-1H-pyrrolizin-3-yl)methyl dimethylcarbamate as the TFA salt (18 mg, 48%). LCMS (MM-ES+APCI, Pos): m/z 688.3 (M+H).

Example 442

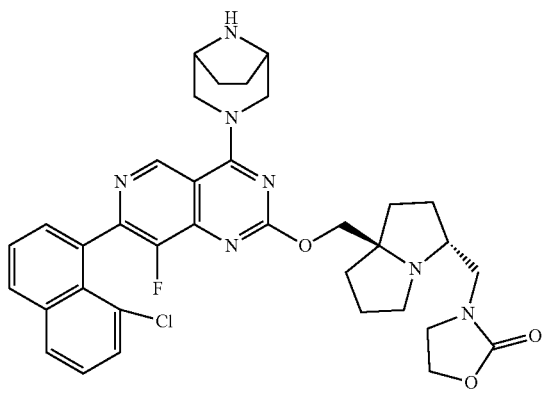 [SMILES: O=C1OCCN1C[C@H]1CC[C@@]2(COc3nc(N4CC5CCC(C4)N5)c4cnc(-c5cccc6cccc(Cl)c56)c(F)c4n3)CCCN12]

3-(((3R,7aR)-7a-(((4-(3,8-diazabicyclo[3.2.1]octan-3-yl)-7-(8-chloronaphthalen-1-yl)-8-fluoropyrido[4,3-d]pyrimidin-2-yl)oxy)methyl)hexahydro-1H-pyrrolizin-3-yl)methyl)oxazolidin-2-one (trans racemic)

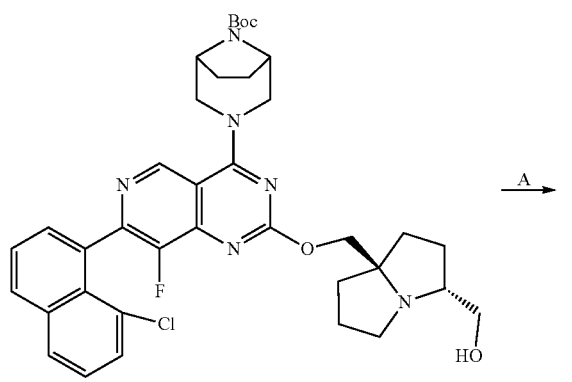

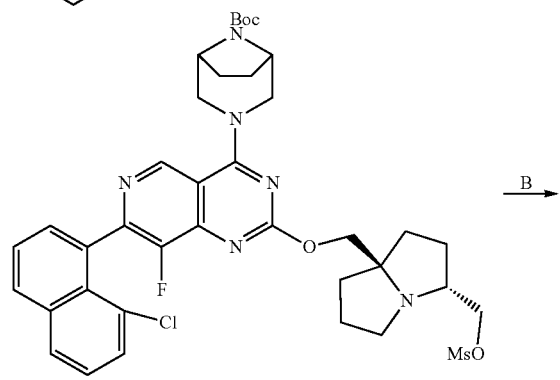

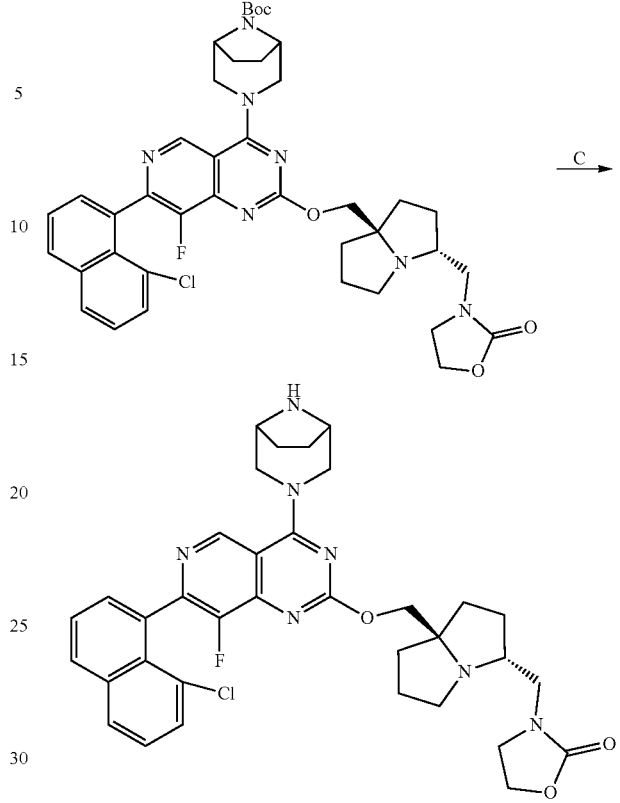

Step A. tert-butyl 3-(7-(8-chloronaphthalen-1-yl)-8-fluoro-2-(((3R,7aR)-3-(((methylsulfonyl)oxy)methyl)tetrahydro-1H-pyrrolizin-7a(5H)-yl)methoxy)pyrido[4,3-d]pyrimidin-4-yl)-3,8-diazabicyclo[3.2.1]octane-8-carboxylate. To a solution of tert-butyl (1R,5S)-3-(7-(8-chloronaphthalen-1-yl)-8-fluoro-2-(((3R,7aR)-3-(hydroxymethyl)tetrahydro-1H-pyrrolizin-7a(5H)-yl)methoxy)pyrido[4,3-d]pyrimidin-4-yl)-3,8-diazabicyclo[3.2.1]octane-8-carboxylate (0.11 g, 0.16 mmol, synthesized according to Example 405, Step A-B) in DCM (1.6 ml) at 0° C. was added Et₃N (33 µl, 0.24 mmol), followed by mesyl chloride (19 µl, 0.24 mmol). The solution was warmed to rt and stirred at rt for 15 min. The mixture was diluted with DCM and washed with NaHCO₃(Sat.). The solution was dried over Na₂SO₄ and concentrated to give the crude title compound (116 mg, 95%) as a white solid. LCMS (MM-ES+APCI, Pos): m/z 767.3 (M+H).

Step B. tert-butyl 3-(7-(8-chloronaphthalen-1-yl)-8-fluoro-2-(((3R,7aR)-3-((2-oxooxazolidin-3-yl)methyl)tetrahydro-1H-pyrrolizin-7a(5H)-yl)methoxy)pyrido[4,3-d]pyrimidin-4-yl)-3,8-diazabicyclo[3.2.1]octane-8-carboxylate. To a solution of tert-butyl (1R,5S)-3-(7-(8-chloronaphthalen-1-yl)-8-fluoro-2-(((3R,7aR)-3-(((methylsulfonyl)oxy)methyl)tetrahydro-1H-pyrrolizin-7a(5H)-yl)methoxy)pyrido[4,3-d]pyrimidin-4-yl)-3,8-diazabicyclo[3.2.1]octane-8-carboxylate (30 mg, 0.039 mmol) and oxazolidin-2-one (17 mg, 0.20 mmol) in DMA (0.40 ml) was added NaH (7.8 mg, 0.20 mmol). The mixture was stirred at 80° C. for 15 h, cooled to rt and purified by preparative C18 HPLC eluting with 0-95% CH3CN/H2O with 0.1% TFA as modifier. The desired fractions were combined, neutralized with NaHCO₃(Sat.) and extracted with DCM. The extract was dried over Na2SO4 and concentrated to give title compound (6.0 mg, 20%) as an off-white solid LCMS (MM-ES+APCI, Pos): m/z 758.3 (M+H).

Step C. 3-(((3R,7aR)-7a-(((4-(3,8-diazabicyclo[3.2.1]octan-3-yl)-7-(8-chloronaphthalen-1-yl)-8-fluoropyrido[4,3-d]pyrimidin-2-yl)oxy)methyl)hexahydro-1H-pyrrolizin-3-yl)methyl)oxazolidin-2-one bis(2,2,2-trifluoroacetate). To a solution of tert-butyl 3-(7-(8-chloronaphthalen-1-yl)-8-fluoro-2-(((3R,7aR)-3-((2-oxooxazolidin-3-yl)methyl)tetrahydro-1H-pyrrolizin-7a(5H)-yl)methoxy)pyrido[4,3-d]pyrimidin-4-yl)-3,8-diazabicyclo[3.2.1]octane-8-carboxylate (6 mg, 0.0079 mmol) in DCM (1.0 ml) was added TFA (0.50 ml). The solution was stirred at rt for 35 min, concentrated and the residue was purified by preparative C18 HPLC eluting with 0-95% CH3CN/H2O with 0.1% TFA as modifier. The desired fractions were combined and lyophilized to give about the title compound (2.0 mg, 29%) as the TFA salt. LCMS (MM-ES+APCI, Pos): m/z 658.3 (M+H).

Example 443

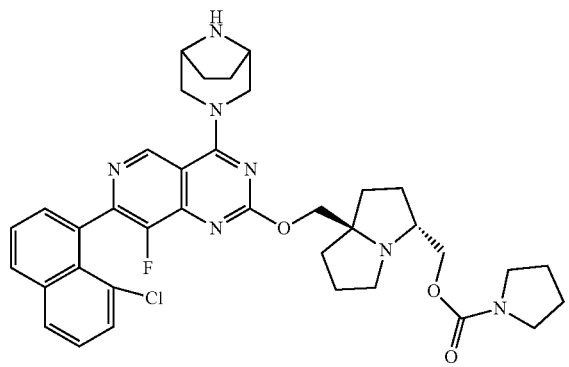 [SMILES: O=C(OC[C@H]1CC[C@@]2(COc3nc(N4CC5CCC(C4)N5)c4cnc(-c5cccc6cccc(Cl)c56)c(F)c4n3)CCCN12)N1CCCC1]

((3R,7aR)-7a-(((4-(3,8-diazabicyclo[3.2.1]octan-3-yl)-7-(8-chloronaphthalen-1-yl)-8-fluoropyrido[4,3-d]pyrimidin-2-yl)oxy)methyl)hexahydro-1H-pyrrolizin-3-yl)methyl pyrrolidine-1-carboxylate (trans racemic)

Synthesized according to Example 445 substituting pyrrolidine for morpholine in step A to give the title compound (6.0 mg, 53%) as a white solid. LCMS (MM-ES+APCI, Pos): m/z 686.3 (M+H).

Example 444

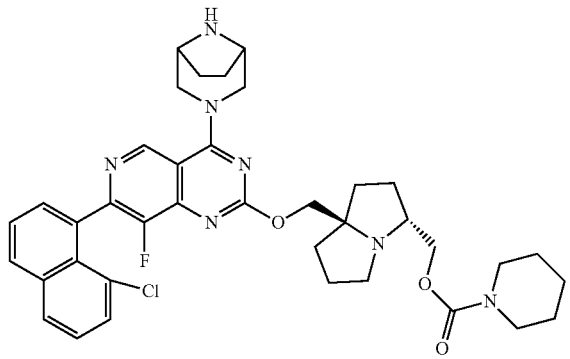 [SMILES: O=C(OC[C@H]1CC[C@@]2(COc3nc(N4CC5CCC(C4)N5)c4cnc(-c5cccc6cccc(Cl)c56)c(F)c4n3)CCCN12)N1CCCCC1]

((3R,7aR)-7a-(((4-(3,8-diazabicyclo[3.2.1]octan-3-yl)-7-(8-chloronaphthalen-1-yl)-8-fluoropyrido[4,3-d]pyrimidin-2-yl)oxy)methyl)hexahydro-1H-pyrrolizin-3-yl)methyl piperidine-1-carboxylate (trans racemic)

Synthesized according to Example 445 substituting piperidine for morpholine in step A to give the title compound (8.0 mg, 44%) as a white solid. LCMS (MM-ES+APCI, Pos): m/z 700.3 (M+H).

Example 445

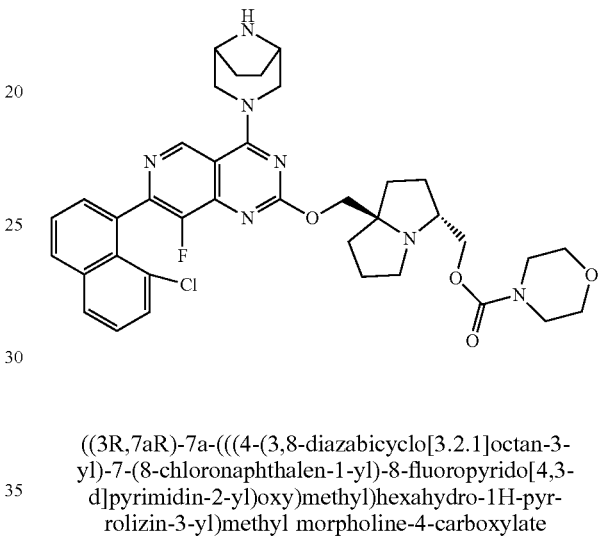

((3R,7aR)-7a-(((4-(3,8-diazabicyclo[3.2.1]octan-3-yl)-7-(8-chloronaphthalen-1-yl)-8-fluoropyrido[4,3-d]pyrimidin-2-yl)oxy)methyl)hexahydro-1H-pyrrolizin-3-yl)methyl morpholine-4-carboxylate

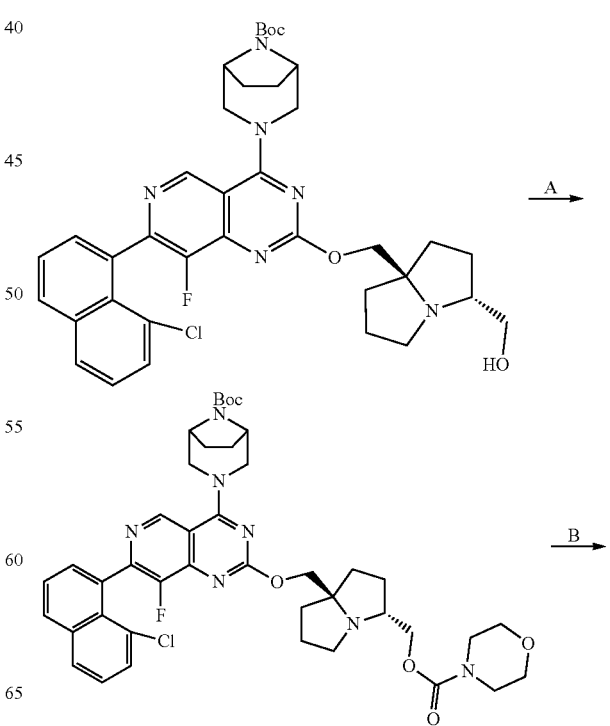

907

-continued

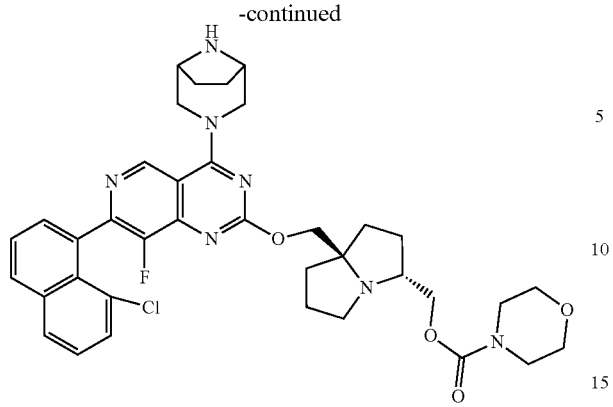

908

Example 446

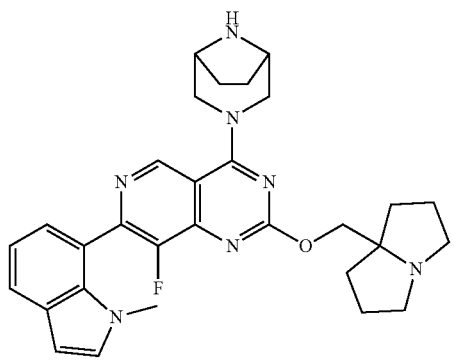 [SMILES: Cn1ccc2cccc(-c3ncc4c(N5CC6CCC(C5)N6)nc(OCC56CCCN5CCC6)nc4c3F)c21]

4-((1R,5S)-3,8-diazabicyclo[3.2.1]octan-3-yl)-8-fluoro-7-(1-methyl-1H-indol-7-yl)-2-((tetrahydro-1H-pyrrolizin-7a(5H)-yl)methoxy)pyrido[4,3-d]pyrimidine

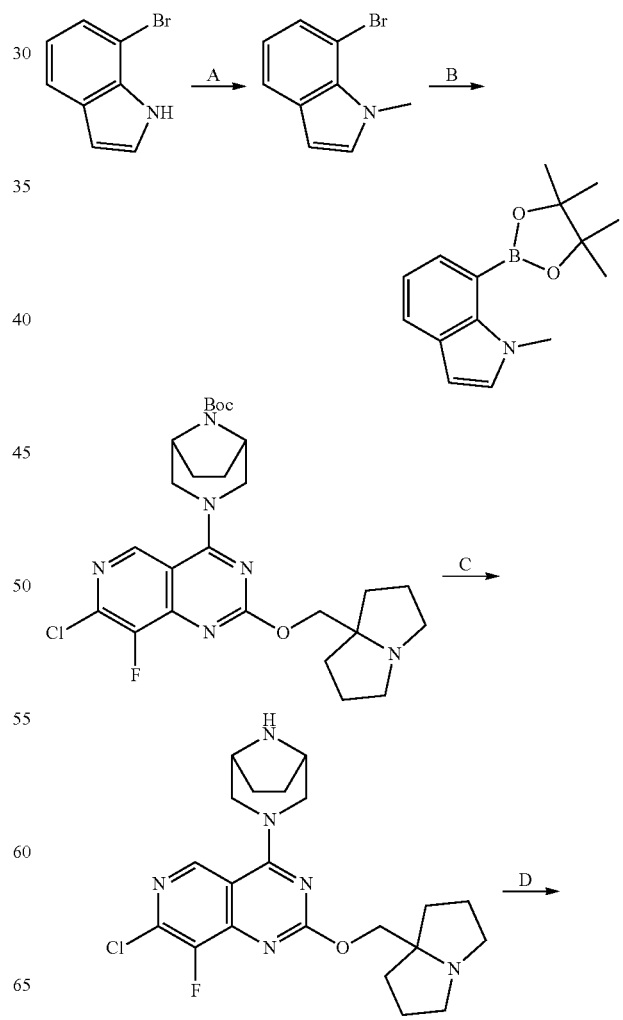

Step A. ((3R,7aR)-7a-(((4-(8-(tert-butoxycarbonyl)-3,8-diazabicyclo[3.2.1]octan-3-yl)-7-(8-chloronaphthalen-1-yl)-8-fluoropyrido[4,3-d]pyrimidin-2-yl)oxy)methyl)hexahydro-1H-pyrrolizin-3-yl)methyl morpholine-4-carboxylate. To a solution of tert-butyl (1R,5S)-3-(7-(8-chloronaphthalen-1-yl)-8-fluoro-2-(((3R,7aR)-3-(hydroxymethyl)tetrahydro-1H-pyrrolizin-7a(5H)-yl)methoxy)pyrido[4,3-d]pyrimidin-4-yl)-3,8-diazabicyclo[3.2.1]octane-8-carboxylate (69 mg, 0.10 mmol, synthesized according to Example 405, Step A-B) and Et₃N (56 μl, 0.40 mmol) in THF (2.0 ml) at rt was added 4-nitrophenyl carbonochloridate (40 mg, 0.20 mmol). The solution was stirred at rt for 1 h. The mixture was divided into three equal portions. One portion was treated with morpholine (0.026 ml, 0.030 mmol) at rt for 1 h. The mixture was purified by preparative C18 HPLC eluting with 0-95% CH3CN/H2O with 0.1% TFA as modifier. The desired fractions were combined, basified with NaHCO3 (Sat.) and extracted with EtOAc. The combined extract was washed with water, brine, dried over Na2SO4 and concentrated to give the title compound (10 mg, 42%) as a white solid. LCMS (MM-ES+APCI, Pos): m/z 802.3 (M+H).

Step B. ((3R,7aR)-7a-(((4-(3,8-diazabicyclo[3.2.1]octan-3-yl)-7-(8-chloronaphthalen-1-yl)-8-fluoropyrido[4,3-d]pyrimidin-2-yl)oxy)methyl)hexahydro-1H-pyrrolizin-3-yl)methyl morpholine-4-carboxylate. To a solution of ((3R,7aR)-7a-(((4-(8-(tert-butoxycarbonyl)-3,8-diazabicyclo[3.2.1]octan-3-yl)-7-(8-chloronaphthalen-1-yl)-8-fluoropyrido[4,3-d]pyrimidin-2-yl)oxy)methyl)hexahydro-1H-pyrrolizin-3-yl)methyl morpholine-4-carboxylate (10 mg, 0.012 mmol) in DCM (1.0 ml) was added TFA (0.50 ml). The solution was stirred at rt for 30 min and concentrated. The residue was purified by preparative C18 HPLC eluting with 0-95% CH3CN/H2O with 0.1% TFA as modifier. The desired fractions were combined, basified with NaHCO₃(Sat.) and extracted with DCM. The combined extract was dried over Na2SO4 and concentrated to give the title compound (8.0 mg, 91%) as a white solid. LCMS (MM-ES+APCI, Pos): m/z 702.3 (M+H).

909
-continued

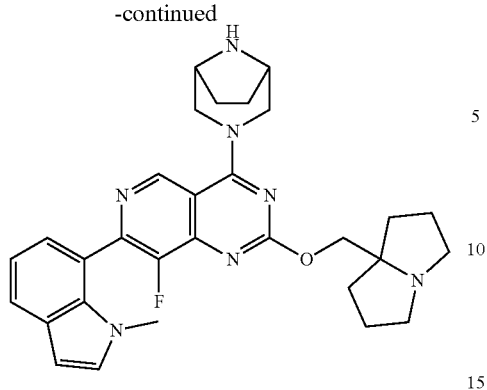

Step A. 7-bromo-1-methyl-1H-indole. 7-Bromo-1H-indole (0.50 g, 2.6 mmol) was added to a round bottom flask with a stir bar and septa. The round bottom flask was degassed and purged with $N_2$ 3 times before dry THF (9 mL) was added. The round bottom flask was cooled to 0° C. and 60% NaH (0.15 g, 3.8 mmol) was added portion wise. The reaction was warmed to room temperature and stirred for 30 minutes. The round bottom flask was cooled to 0° C. and iodomethane (0.21 mL, 3.3 mmol) was added dropwise. The reaction warmed to room temperature. Water was added at 0° C. and the reaction mixture was extracted with DCM. The DCM layer was dried with Na2SO4, filtered, and concentrated. The residue was purified via flash chromatography (silica, 0-10% EtOAc in hexanes) to yield 7-bromo-1-methyl-1H-indole as a white solid (0.41 g, 72%). 1H NMR (CDCl$_3$, 400 MHz): 7.54 (dd, J=7.8, 0.9 Hz, 1H), 7.35 (dd, J=7.6, 0.7 Hz, 1H), 7.00 (d, J=3.2 Hz, 1H), 6.91 (t, J=7.7 Hz, 1H), 6.46 (d, J=3.2 Hz, 1H), 4.17 (s, 3H).

Step B. 1-methyl-7-(4,4,5,5-tetramethyl-1,3,2-dioxaborolan-2-yl)-1H-indole. 7-Bromo-1-methyl-1H-indole (0.11 g, 0.50 mmol), 4,4,4',4',5,5,5',5'-octamethyl-2,2'-bi(1,3,2-dioxaborolane) (0.38 g, 1.5 mmol), PdCl2(dppf) (37 mg, 0.05 mmol), and KOAc (0.15 g, 1.5 mmol) were added to a vial with stir bar and septa cap. The vial was degassed and purged with N2 3 times before dioxane (3 mL) was added. The vial was sparged with N2 for 15 minutes and the reaction was heated to 95° C. for 2 hours. The reaction was diluted with DCM, filtered through a Celite plug, and the filtrate was concentrated. The residue was purified via reverse phase chromatography eluting with 0-100% MeCN/water with 0.1% TFA as modifier. The fractions containing the product were combined, diluted with Et2O, and washed with saturated NaHCO3 followed by water. The Et2O layer was dried with Na2SO4, filtered, and concentrated to yield 1-methyl-7-(4,4,5,5-tetramethyl-1,3,2-dioxaborolan-2-yl)-1H-indole as a light brown solid (75 mg, 59%). LCMS (MM-ES+APCI, Pos): m/z 258.3 (M+H).

Step C and D. Synthesized according to Example 427, Step C-D, substituting 1-methyl-7-(4,4,5,5-tetramethyl-1,3,2-dioxaborolan-2-yl)-1H-indole for 1-ethyl-7-(4,4,5,5-tetramethyl-1,3,2-dioxaborolan-2-yl)-1H-indole. (9.5 mg, 32%). LCMS (MM-ES+APCI, Pos): m/z 528.3 (M+H).

910
Example 447

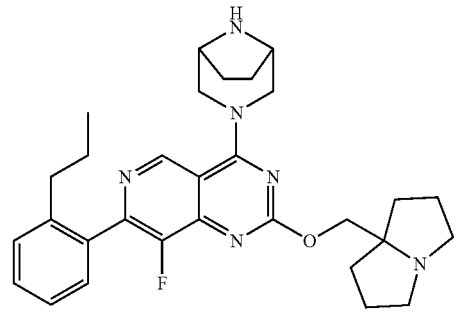 [SMILES: CCCc1ccccc1-c1ncc2c(N3CC4CCC(C3)N4)nc(OCC34CCCN3CCC4)nc2c1F]

4-((1R,5S)-3,8-diazabicyclo[3.2.1]octan-3-yl)-8-fluoro-7-(2-propylphenyl)-2-((tetrahydro-1H-pyrrolizin-7a(5H)-yl)methoxy)pyrido[4,3-d]pyrimidine

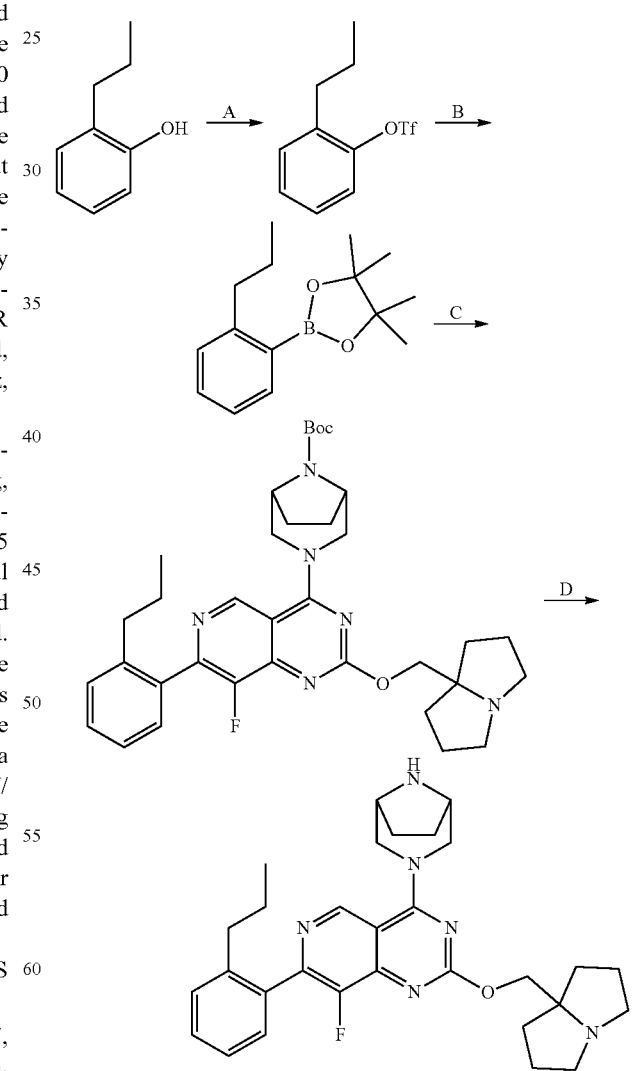

Step A. 2-propylphenyl trifluoromethanesulfonate. To a solution of 2-propylphenol (2 g, 14.7 mmol, 1.0 eq) in DCM (40 mL) were added DIEA (5.69 g, 44.1 mmol, 7.67 mL, 3.0 eq) and Tf₂O (6.21 g, 22.0 mmol, 3.63 mL, 1.5 eq). The mixture was stirred at −40° C. for 2 hours. After completion, the mixture was quenched with H₂O (50 mL), and extracted with dichloromethane (3×30 mL). The combined organic layers were washed with brine (2×20 mL), dried over anhydrous Na₂SO₄, filtered and concentrated under reduced pressure to give a residue. The residue was purified by column chromatography (SiO₂, petroleum ether/ethyl acetate=1 to 40/1) to give the title compound (2.8 g, 71% yield). Colorless oil; ¹H NMR (400 MHz, DMSO-d6) δ=7.53-7.26 (m, 4H), 2.68-2.57 (m, 2H), 1.65-1.50 (m, 2H), 0.89 (t, J=7.2 Hz, 3H).

Step B. 4,4,5,5-tetramethyl-2-(2-propylphenyl)-1,3,2-dioxaborolane. A mixture of 2-propylphenyl trifluoromethanesulfonate (300 mg, 1.12 mmol, 1.0 eq), Pin2B2 (567 mg, 2.24 mmol, 2.0 eq), KOAc (329 mg, 3.36 mmol, 3.0 eq), Pd(dppf)Cl₂ (81.8 mg, 111 μmol, 0.1 eq) in dioxane (5 mL) was degassed and purged with N₂ for 3 times, and then the mixture was stirred at 110° C. for 1 hour under N₂ atmosphere. After completion, the reaction was diluted with H₂O (20 mL) and extracted with ethyl acetate (3×30 mL). The combined organic layers were washed with brine (2×20 mL), dried over anhydrous Na₂SO₄, filtered and concentrated under reduced pressure to give a residue. The residue was purified by reversed phase flash chromatography (water (0.1% formic acid)/acetonitrile) to give the title compound (198 mg, 72% yield). Brown oil. ¹H NMR (400 MHz, chloroform-d) δ=7.77 (dd, J=1.6, 8.0 Hz, 1H), 7.38-7.31 (m, 1H), 7.21-7.14 (m, 2H), 2.90-2.83 (m, 2H), 1.62-1.55 (m, 2H), 1.35 (s, 12H), 0.95 (t, J=7.2 Hz, 3H).

Step C. tert-butyl 3-(8-fluoro-2-((hexahydro-1H-pyrrolizin-7a-yl)methoxy)-7-(2-propylphenyl)pyrido[4,3-d]pyrimidin-4-yl)-3,8-diazabicyclo[3.2.1]octane-8-carboxylate. A mixture of tert-butyl (1R,5S)-3-(7-chloro-8-fluoro-2-((tetrahydro-1H-pyrrolizin-7a(5H)-yl)methoxy)pyrido[4,3-d]pyrimidin-4-yl)-3,8-diazabicyclo[3.2.1]octane-8-carboxylate (60 mg, 113 μmol, 1.0 eq), 4,4,5,5-tetramethyl-2-(2-propylphenyl)-1,3,2-dioxaborolane (55.4 mg, 225 μmol, 2.0 eq), K₃PO₄ (1.5 M in H₂O, 225 μL, 3.0 eq), APhos Pd G3 (7.15 mg, 11.3 μmol, 0.1 eq) in toluene (1 mL) was degassed and purged with N₂ for 3 times, and then the mixture was stirred at 90° C. for 1 hour under N₂ atmosphere. After completion, the mixture was added H₂O (5 mL), then extracted with ethyl acetate (3×10 mL). The combined organic layers were washed with brine (2×10 mL), dried over anhydrous Na₂SO₄, filtered and concentrated under reduced pressure to give a residue. The residue was purified by reversed phase flash chromatography (water (0.1% formic acid)/acetonitrile)) to give the title compound (54 mg, 67% yield). Yellow solid. LCMS [ESI, M+1]: 617.4.

Step D. 4-((1R,5S)-3,8-diazabicyclo[3.2.1]octan-3-yl)-8-fluoro-7-(2-propylphenyl)-2-((tetrahydro-1H-pyrrolizin-7a(5H)-yl)methoxy)pyrido[4,3-d]pyrimidine. To a solution of 3-(8-fluoro-2-((hexahydro-1H-pyrrolizin-7a-yl)methoxy)-7-(2-propylphenyl)pyrido[4,3-d]pyrimidin-4-yl)-3,8-diazabicyclo[3.2.1]octane-8-carboxylate (54 mg, 87.5 μmol, 1.0 eq) in CH₃CN (1 mL) was added HCl·dioxane (4 M, 1 mL, 45.7 eq). The mixture was stirred at 20° C. for 0.5 hour. After completion, the mixture was directly concentrated under reduced pressure. Then the residue was diluted with MeOH (1 mL) and the pH was adjusted to 8 with saturated Na₂CO₃ solution. The mixture was purified by prep-HPLC (column: Shim-pack C18 150*25*10 um; mobile phase: [water (0.225% FA)-ACN]; B %: 12%-32%, 10 min). The desired fraction was collected and lyophilized to give the title compound (23.4 mg, 44% yield, 1.8FA). Yellow solid; ¹H NMR (400 MHz, methanol-d4) δ=9.14 (s, 1H), 7.53-7.25 (m, 4H), 4.78 (br d, J=13.2 Hz, 2H), 4.67 (s, 2H), 4.03 (br s, 2H), 3.88 (br d, J=13.2 Hz, 2H), 3.78-3.62 (m, 2H), 3.30-3.24 (m, 2H), 2.57 (br t, J=7.6 Hz, 2H), 2.41-1.89 (m, 12H), 1.56-1.40 (m, 2H), 0.77 (t, J=7.2 Hz, 3H); LCMS [ESI, M+1]: 517.3.

Example 448

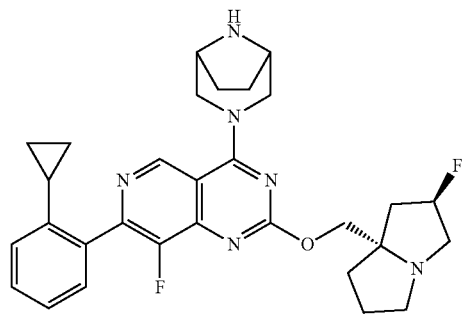 [SMILES: Fc1c(-c2ccccc2C2CC2)ncc2c(N3CC4CCC(C3)N4)nc(OC[C@@]34CCCN3C[C@H](F)C4)nc12]

4-((1R,5S)-3,8-diazabicyclo[3.2.1]octan-3-yl)-7-(2-cyclopropylphenyl)-8-fluoro-2-(((2R,7aS)-2-fluorohexahydro-1H-pyrrolizin-7a-yl)methoxy)pyrido[4,3-d]pyrimidine

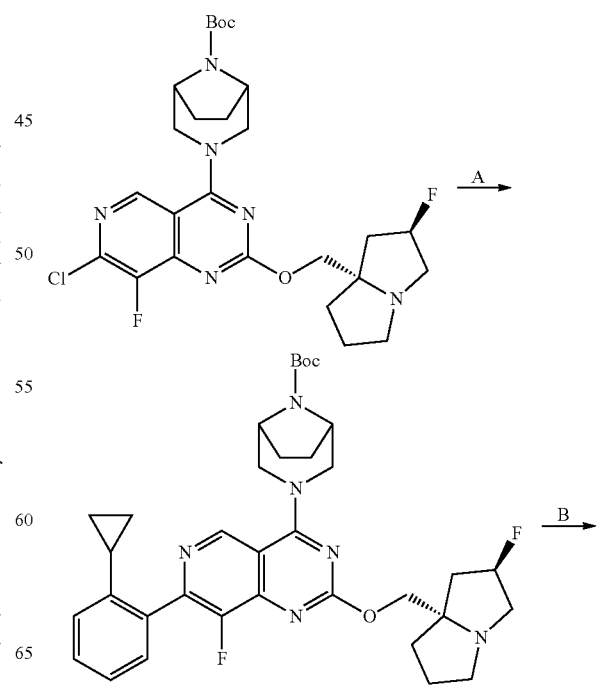

913

-continued

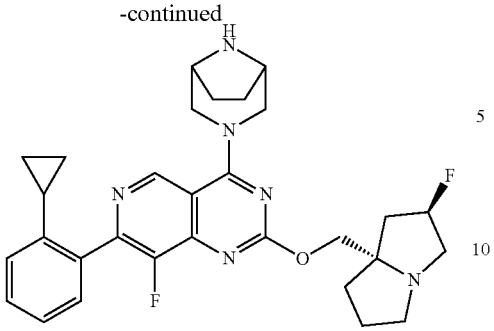

Step A. (1R,5S)-tert-butyl 3-(7-(2-cyclopropylphenyl)-8-fluoro-2-(((2R,7aS)-2-fluorohexahydro-1H-pyrrolizin-7a-yl)methoxy)pyrido[4,3-d]pyrimidin-4-yl)-3,8-diazabicyclo[3.2.1]octane-8-carboxylate. To a solution of tert-butyl (1R,5S)-3-(7-chloro-8-fluoro-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (170 mg, 309 μmol, 1.0 eq), K$_3$PO$_4$ (1.5 M, 617 μL, 3.0 eq) and (2-cyclopropylphenyl)boronic acid (90.0 mg, 556 μmol, 1.80 eq) in THF (2 mL) was added Ad2nBuP Pd G3 (cataCXium® A Pd G3) (22.5 mg, 30.9 μmol, 0.10 eq). The mixture was stirred at 60° C. for 2 hours. Upon completion, the reaction mixture was added water (5 mL) and extracted with ethyl acetate (3×5 mL). The organic layer was dried over Na$_2$SO$_4$, filtered and concentrated. The residue was purified by reversed phase flash chromatography (C18, 0.1% formic acid condition) affording the title compound (150 mg, 76% yield). Yellow solid; $^1$H NMR (400 MHz, CDCl$_3$) δ=9.04 (s, 1H), 7.42-7.35 (m, 2H), 7.32-7.27 (m, 1H), 7.06 (d, J=7.6 Hz, 1H), 5.40-5.18 (m, 1H), 4.62-4.50 (m, 2H), 4.47-4.32 (m, 2H), 4.27 (d, J=10.0 Hz, 1H), 4.16 (d, J=3.6 Hz, 1H), 3.80-3.53 (m, 2H), 3.32-3.11 (m, 3H), 3.03-2.94 (m, 1H), 2.37-2.15 (m, 3H), 1.91-1.82 (m, 2H), 1.81-1.67 (m, 6H), 1.53 (s, 9H), 0.82-0.75 (m, 2H), 0.67-0.59 (m, 2H); LCMS [ESI, M+1, M+23]: 633.2, 655.2.

Step B. 4-((1R,5S)-3,8-diazabicyclo[3.2.1]octan-3-yl)-7-(2-cyclopropylphenyl)-8-fluoro-2-(((2R,7aS)-2-fluorohexahydro-1H-pyrrolizin-7a-yl)methoxy)pyrido[4,3-d]pyrimidine. To a solution of (1R,5S)-tert-butyl 3-(7-(2-cyclopropylphenyl)-8-fluoro-2-(((2R,7aS)-2-fluorohexahydro-1H-pyrrolizin-7a-yl)methoxy)pyrido[4,3-d]pyrimidin-4-yl)-3,8-diazabicyclo[3.2.1]octane-8-carboxylate (130 mg, 205 μmol, 1.0 eq) in MeCN (1 mL) was added HCl·dioxane (4 M, 3.0 mL, 58.4 eq). The mixture was stirred at 15° C. for 0.5 hour. After completion, the mixture was added water (5 mL) and extracted with ethyl acetate (3×5 mL). The organic layer was dried over Na$_2$SO$_4$, filtered and concentrated. The residue was purified by prep-HPLC (column: Waters Xbridge 150*25 mm*5 um; mobile phase: [water (10 mM NH$_4$HCO$_3$)-ACN]; B %: 28%-58%, 8 min) affording the title compound (48.9 mg, 45% yield). White solid; SFC analysis: Column: Chiralcel OD-3 50×4.6 mm I.D., 3 um Mobile phase: Phase A for CO2, and Phase B for MeOH+CAN (0.05% DEA); Gradient elution: 60% MeOH+ACN (0.05% DEA) in CO2 Flow rate: 3 mL/min; Detector: PDA Column Temp: 35° C.; Back Pressure: 100 Bar; $^1$H NMR (400 MHz, CDCl$_3$) δ=9.04 (s, 1H), 7.42-7.34 (m, 2H), 7.31-7.25 (m, 1H), 7.05 (d, J=8.0 Hz, 1H), 5.44-

914

5.16 (m, 1H), 4.56 (br t, J=10.4 Hz, 2H), 4.27 (d, J=10.4 Hz, 1H), 4.14 (d, J=10.0 Hz, 1H), 3.73-3.58 (m, 4H), 3.35-3.23 (m, 2H), 3.22-3.12 (m, 1H), 3.04-2.94 (m, 1H), 2.37-2.13 (m, 3H), 2.03-1.81 (m, 8H), 0.84-0.76 (m, 2H), 0.68-0.60 (m, 2H); LCMS [ESI, M+1]: 533.2.

Example 449

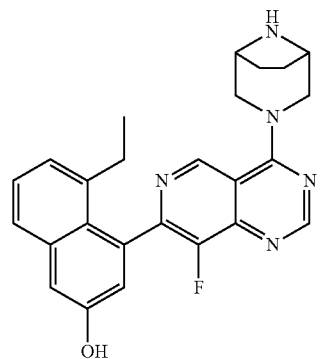 [SMILES: CCc1cccc2cc(O)cc(-c3ncc4c(N5CC6CCC(C5)N6)ncnc4c3F)c12]

4-(4-((1R,5S)-3,8-diazabicyclo[3.2.1]octan-3-yl)-8-fluoropyrido[4,3-d]pyrimidin-7-yl)-5-ethylnaphthalen-2-ol

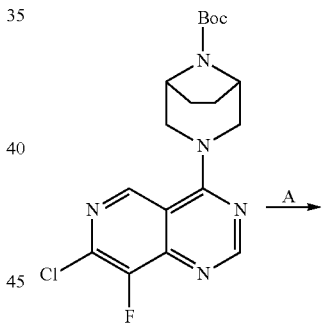

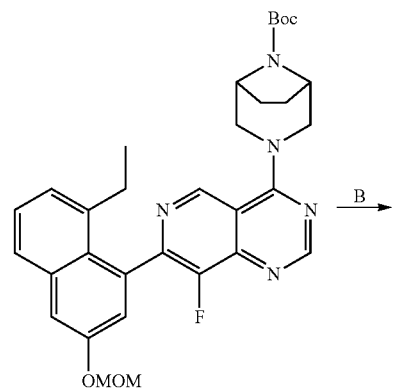

915
-continued

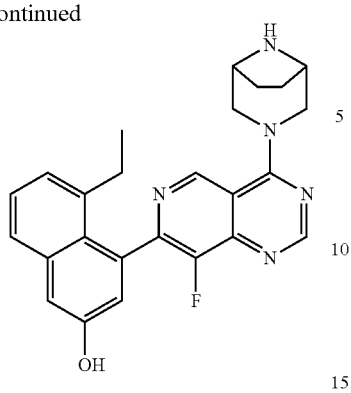

Step A. (1R,5S)-tert-butyl 3-(7-(8-ethyl-3-(methoxymethoxy)naphthalen-1-yl-8-fluoropyrido[4,3-d]pyrimidin-4-yl)-3,8-diazabicyclo[3.2.1]octane-8-carboxylate. A mixture of tert-butyl (1R,5S)-3-(7-chloro-8-fluoropyrido[4,3-d]pyrimidin-4-yl)-3,8-diazabicyclo[3.2.1]octane-8-carboxylate (100 mg, 254 μmol, 1 eq), 2-(8-ethyl-3-(methoxymethoxy)naphthalen-1-yl)-4,4,5,5-tetramethyl-1,3,2-dioxaborolane (113 mg, 330 μmol, 1.3 eq), [2-(2-aminophenyl)phenyl]palladium(1+); bis(1-adamantyl)-butyl-phosphane; methanesulfonate (18.5 mg, 25.4 μmol, 0.1 eq) and $K_3PO_4$ (1.5 M, 508 μL, 3 eq) in dioxane (3.00 mL) was degassed and purged with $N_2$ for 3 times, and then the mixture was stirred at 100° C. for 1.5 hours under $N_2$ atmosphere. The mixture was diluted with water (20.0 mL) and extracted with ethyl acetate (3×5.00 mL). The organic layers were dried over $Na_2SO_4$, concentrated under vacuum, purified by prep-TLC (Ethyl acetate/Petroleum ether=2:1) to give the title compound (110 mg, 60% yield). Yellow solid. LCMS [ESI, M+1]: 574.3.

Step B. 4-((1R,5S)-3,8-diazabicyclo[3.2.1]octan-3-yl)-7-(8-ethylnaphthalen-1-yl)-8-fluoropyrido[4,3-d]pyrimidine. A solution of (1R,5S)-tert-butyl 3-(7-(8-ethyl-3-(methoxymethoxy)naphthalen-1-yl)-8-fluoropyrido[4,3-d]pyrimidin-4-yl)-3,8-diazabicyclo[3.2.1]octane-8-carboxylate (100 mg, 174 μmol, 1 eq) in HCl/EtOAc (4 M, 1.00 mL) was stirring at 20° C. for 1 hour. Upon completion, the reaction mixture was adjust pH~8 with sat. $NaHCO_3$ (20.0 mL) and extracted with ethyl acetate (3×10.0 mL). The combined organic layer was washed with brine (20 mL), dried over $Na_2SO_4$, filtered and concentrated under reduced pressure to give a residue. the mixture was concentrated under vacuum and was purified by prep-HPLC(column: Waters Xbridge BEH C18 100*25 mm*5 um; mobile phase: [water (10 mM $NH_4HCO_3$)-ACN]; B %: 25%-55%, 10 min) to give the title compound (20.7 mg, 27% yield); White solid; $^1H$ NMR (400 MHz, DMSO-d6) δ=9.90 (s, 1H), 9.21 (s, 1H), 8.67 (s, 1H), 7.67 (d, J=8.0 Hz, 1H), 7.37 (t, J=7.6 Hz, 1H), 7.29 (d, J=2.4 Hz, 1H), 7.12 (d, J=7.2 Hz, 1H), 7.00 (d, J=2.4 Hz, 1H), 4.56-4.40 (m, 2H), 3.73-3.57 (m, 2H), 3.53 (d, J=10.4 Hz, 2H), 2.71 (s, 1H), 2.28-2.10 (m, 2H), 1.67-1.53 (m, 4H), 0.79 (t, J=7.2 Hz, 3H); $^1H$ NMR (400 MHz, DMSO-d6+D2O) δ 9.16 (s, 1H), 8.63 (s, 1H), 7.65 (d, J=801 Hz, 1H), 7.37 (t, J=7.6 Hz, 1H), 7.29 (d, J=2.4 Hz, 1H), 7.12 (d, J=7.2 Hz, 1H), 6.98 (d, J=2.4 Hz, 1H), 4.54-4.37 (m, 2H), 3.71-3.57 (m, 2H), 3.52 (s, 2H), 2.26-2.04 (m, 2H), 1.73-1.58 (m, 2H), 1.58-1.44 (m, 2H), 0.76 (t, J=7.2 Hz, 3H). LCMS [ESI, M+1]: 430.3.

916
Example 450

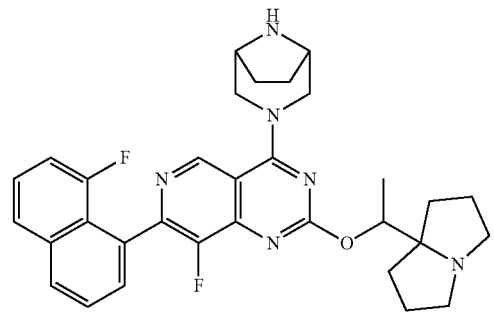 [SMILES: CC(Oc1nc(N2CC3CCC(C2)N3)c2cnc(-c3cccc4cccc(F)c34)c(F)c2n1)C12CCCN1CCC2]

4-((1R,5S)-3,8-diazabicyclo[3.2.1]octan-3-yl)-8-fluoro-7-(8-fluoronaphthalen-1-yl)-2-(1-(hexahydro-1H-pyrrolizin-7a-yl)ethoxy)pyrido[4,3-d]pyrimidine

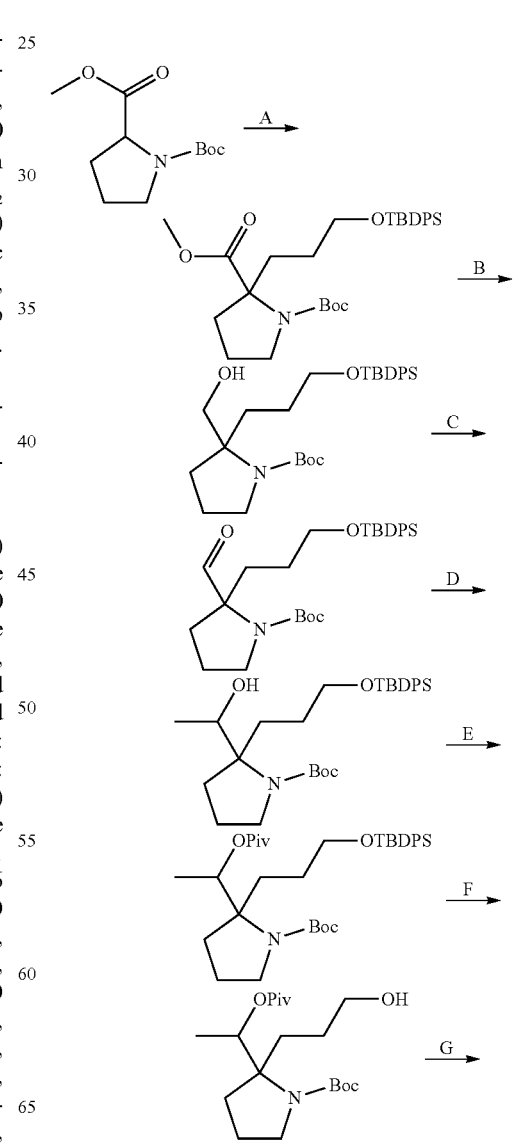

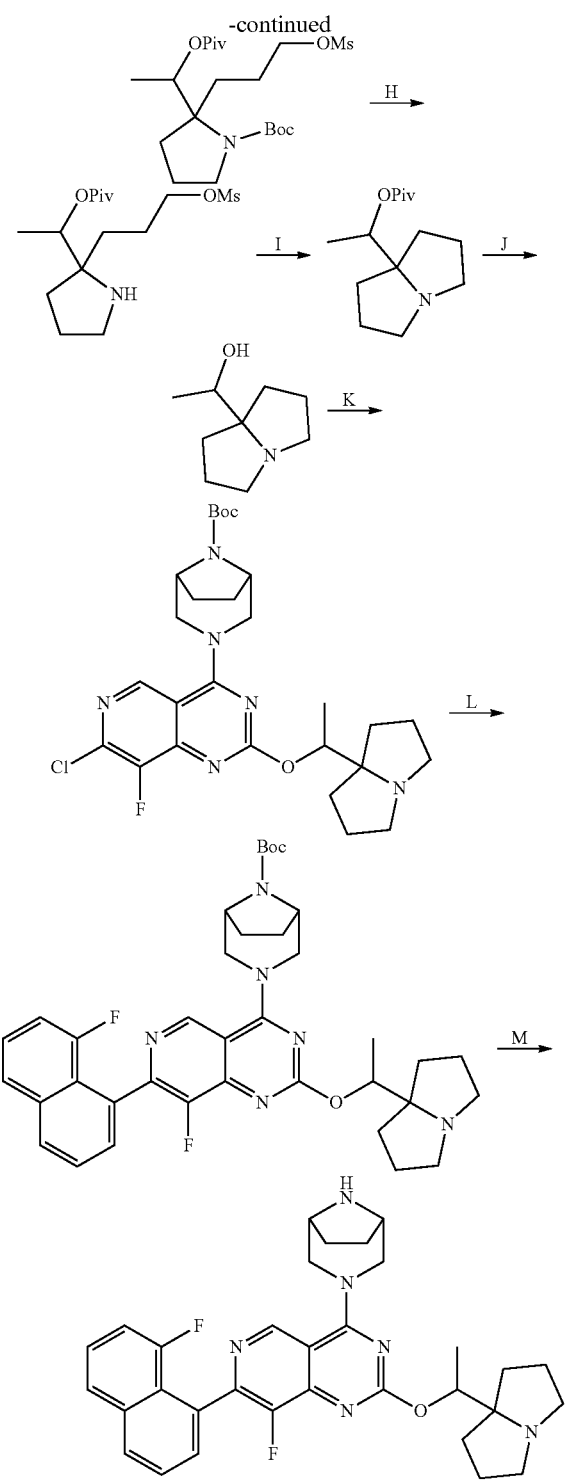

combined organic layers were dried over Na₂SO₄, filtered and concentrated under reduced pressure to give a residue. The residue was purified by column chromatography (SiO₂, Petroleum ether/Ethyl acetate 1/0 to 1/1) affording the title compound (9.50 g, 41% yield). Yellow oil; ¹H NMR (400 MHz, chloroform-d) δ 7.71-7.62 (m, 4H), 7.48-7.33 (m, 6H), 3.78-3.57 (m, 6H), 3.44-3.31 (m, 1H), 2.34-2.05 (m, 2H), 2.03-1.69 (m, 4H), 1.64-1.48 (m, 2H), 1.47-1.33 (m, 9H), 1.11-1.02 (m, 9H). LCMS [ESI, M−99]: 426.1.

Step B. tert-butyl 2-(3-((tert-butyldiphenylsilyl)oxy)propyl)-2-(hydroxymethyl)pyrrolidine-1-carboxylate. To a solution of 1-tert-butyl 2-methyl 2-(3-((tert-butyldiphenylsilyl)oxy)propyl)pyrrolidine-1,2-dicarboxylate (5.0 g, 9.51 mmol, 1.0 eq) in THF (100 mL) was added LiAlH4 (1.08 g, 28.5 mmol, 3.0 eq) in portions during a period of 30 minutes at −40° C. under N₂ atmosphere and the mixture was stirred at −40° C. for 1 hour. After completion, the reaction mixture was quenched by saturated Na₂SO₄ aqueous (10 mL) at 0° C. The mixture was dried over Na₂SO₄, filtered and concentrated under reduced pressure to give the title compound (4.2 g, 88% yield). White solid. ¹H NMR (400 MHz, DMSO-d6) δ=7.65-7.55 (m, 4H), 7.49-7.38 (m, 6H), 4.78-4.63 (m, 1H), 3.71-3.47 (m, 4H), 3.41-3.34 (m, 1H), 3.25-3.12 (m, 1H), 2.08-1.99 (m, 1H), 1.94-1.42 (m, 7H), 1.34 (d, J=7.6 Hz, 9H), 0.98 (d, J=3.2 Hz, 9H). LCMS [ESI, M−99, M+1]: 398.4, 498.3.

Step C. tert-butyl 2-(3-((tert-butyldiphenylsilyl)oxy)propyl)-2-formylpyrrolidine-1-carboxylate. To a solution of tert-butyl 2-(3-((tert-butyldiphenylsilyl)oxy)propyl)-2-(hydroxymethyl)pyrrolidine-1-carboxylate (1.0 g, 2.01 mmol, 1.0 eq) in DCM (20 mL) was added (1,1-diacetoxy-3-oxo-1,2-benziodoxol-1-yl) acetate (1.28 g, 3.01 mmol, 1.5 eq) at 0° C. The mixture was stirred at 0° C. for 1 hour. After completion, the reaction mixture was concentrated under reduced pressure and purified by column chromatography (SiO₂, petroleum ether: ethyl acetate=20/1 to 8/1) to give the title compound (0.85 g, 85% yield). Colorless oil; ¹H NMR (400 MHz, DMSO-d6) δ=9.34 (d, J=6.0 Hz, 1H), 7.61 (br d, J=7.2 Hz, 4H), 7.48-7.39 (m, 6H), 3.69-3.60 (m, 2H), 3.55-3.43 (m, 1H), 1.88-1.78 (m, 2H), 1.86-1.41 (m, 7H), 1.39-1.27 (m, 9H), 0.99 (d, J=4.8 Hz, 9H). LCMS [ESI, M−99]: 396.1.

Step D. tert-butyl 2-(3-((tert-butyldiphenylsilyl)oxy)propyl)-2-(1-hydroxyethyl)pyrrolidine-1-carboxylate. To a mixture of tert-butyl 2-(3-((tert-butyldiphenylsilyl)oxy)propyl)-2-formylpyrrolidine-1-carboxylate (0.8 g, 1.61 mmol, 1.0 eq) in THF (10 mL) was added bromo(methyl)magnesium (3 M, 5.38 mL, 10 eq) at −60° C. and the mixture was stirred for 1 hour. After completion, the reaction mixture was diluted with water (20 mL) and extracted with ethyl acetate (3×30 mL). The combined organic layers were washed with brine (30 mL), dried over Na₂SO₄, filtered and concentrated under reduced pressure and purification by column chromatography (SiO₂, petroleum ether:ethyl acetate=50/1 to 3/1) to give the title compound (0.8 g, 97% yield). Colorless oil. ¹H NMR (400 MHz, DMSO-d6) δ=7.63-7.57 (m, 4H), 7.49-7.39 (m, 6H), 4.71-4.59 (m, 1H), 3.68-3.57 (m, 2H), 3.29-3.18 (m, 2H), 2.16-2.01 (m, 1H), 1.96-1.39 (m, 7H), 1.36-1.30 (m, 9H), 0.99 (d, J=4.4 Hz, 9H), 0.94-0.86 (m, 3H).

Step E. tert-butyl 2-(3-((tert-butyldiphenylsilyl)oxy)propyl)-2-(1-(pivaloyloxy)ethyl)pyrrolidine-1-carboxylate. To a mixture of tert-butyl 2-(3-((tert-butyldiphenylsilyl)oxy)propyl)-2-(1-hydroxyethyl)pyrrolidine-1-carboxylate (0.7 g, 1.37 mmol, 1.0 eq), TEA (277 mg, 2.74 mmol, 380 μL, 2.0 eq) in DCM (7 mL) were added DMAP (334 mg, 2.74 mmol, 2.0 eq) and 2,2-dimethyl propanoyl chloride (247 mg, 2.05

Step A. 1-tert-butyl 2-methyl 2-(3-((tert-butyldiphenylsilyl) oxy)propyl)pyrrolidine-1,2-dicarboxylate. To a solution of 1-(tert-butyl) 2-methyl pyrrolidine-1,2-dicarboxylate (10.0 g, 43.6 mmol, 1.0 eq) in THF (200 mL) was added LDA (2.0 M, 26.2 mL, 1.20 eq). The mixture was stirred at −70° C. for 1 hour. To the reaction mixture was added (3-bromopropoxy)(tert-butyl)diphenylsilane (16.5 g, 43.6 mmol, 1.0 eq). The mixture was stirred at 20° C. for 12 hours. The reaction mixture was diluted with H₂O (200 mL) and extracted with ethyl acetate (3×200 mL). The mmol, 1.5 eq) at 0° C. under N₂ atmosphere. Then the mixture was warmed to 15° C. and stirred for 12 hours. After completion, the reaction mixture was diluted with water (10 mL) and extracted with ethyl acetate (3×30 mL). The combined organic layers were washed with brine (50 mL), dried over Na₂SO₄, filtered and concentrated under reduced pressure and purified by reversed phase flash chromatography [water (0.1% formic acid)/acetonitrile)] to give the title compound (530 mg, 65% yield). Yellow oil; LCMS [ESI, M−99]: 496.5.

Step F. tert-butyl 2-(3-hydroxypropyl)-2-(1-(pivaloyloxy) ethyl)pyrrolidine-1-carboxylate. To a solution of tert-butyl 2-(3-((tert-butyldiphenylsilyl)oxy)propyl)-2-(1-(pivaloyloxy)ethyl)pyrrolidine-1-carboxylate (1.9 g, 3.19 mmol, 1.0 eq) in THF (20 mL) was added TBAF (1 M in THF, 9.57 mL, 3.0 eq). The mixture was stirred at 20° C. for 1 hour. The reaction mixture was diluted with water (20 mL) and extracted with ethyl acetate (3×20 mL). The combined organic layers were washed with brine (20 mL), dried over Na₂SO₄, filtered and concentrated under reduced pressure to give a residue. The residue was purified by column chromatography (SiO₂, petroleum ether/ethyl acetate=10/1 to 1/1) and further purified by reversed phase flash chromatography [water (0.1% formic acid)/acetonitrile)] to give the title compound (800 mg, 70% yield). Yellow oil. ¹H NMR (400 MHz, chloroform-d) δ=5.62-5.45 (m, 1H), 3.72-3.32 (m, 4H), 2.41-2.13 (m, 1H), 2.03-1.91 (m, 1H), 1.88-1.71 (m, 3H), 1.61-1.41 (m, 12H), 1.22-1.15 (m, 9H), 1.10 (d, J=6.4 Hz, 3H).

Step G. tert-butyl 2-(3-((methylsulfonyl)oxy)propyl)-2-(1-(pivaloyloxy)ethyl)pyrrolidine-1-carboxylate. To a solution of tert-butyl 2-(3-hydroxypropyl)-2-(1-(pivaloyloxy) ethyl)pyrrolidine-1-carboxylate (800 mg, 2.24 mmol, 1.0 eq) in DCM (10 mL) were added TEA (452 mg, 4.48 mmol, 622 μL, 2.0 eq) and MsCl (307 mg, 2.69 mmol, 207 μL, 1.2 eq). The mixture was stirred at 0° C. for 1 hour. The reaction mixture was diluted with water (20 mL) and extracted with DCM (3×30 mL). The combined organic layers were washed with brine (20 mL), dried over Na₂SO₄, filtered and concentrated under reduced pressure to give a residue. The residue was purified by column chromatography (SiO₂, petroleum ether/ethyl acetate=20/1 to 3/1) to give the title compound (900 mg, 92% yield). Yellow oil. ¹H NMR (400 MHz, chloroform-d) δ=5.64-5.47 (m, 1H), 4.30-4.15 (m, 2H), 3.62-3.34 (m, 2H), 2.99 (s, 3H), 2.41-2.06 (m, 2H), 1.90-1.64 (m, 6H), 1.55-1.41 (m, 9H), 1.22-1.16 (m, 9H), 1.11 (dd, J=2.0, 6.4 Hz, 3H).

Step H. 1-(2-(3-((methylsulfonyl)oxy)propyl)pyrrolidin-2-yl)ethyl pivalate. To a solution of tert-butyl 2-(3-((methylsulfonyl)oxy)propyl)-2-(1-(pivaloyloxy)ethyl)pyrrolidine-1-carboxylate (900 mg, 2.07 mmol, 1.0 eq) in MeCN (5 mL) was added HCl·dioxane (4 M, 5.17 mL, 10 eq). The mixture was stirred at 10° C. for 0.5 hour. The mixture was concentrated under vacuum to give the title compound (760 mg, HCl), which was used in the next step without purification. White solid.

Step I. 1-(hexahydro-1H-pyrrolizin-7a-yl)ethyl pivalate. To a solution of 1-(2-(3-((methylsulfonyl)oxy)propyl)pyrrolidin-2-yl)ethyl pivalate (760 mg, 2.27 mmol, 1.0 eq) in MeCN (10 mL) was added K₂CO₃ (1.57 g, 11.3 mmol, 5.0 eq). The mixture was stirred at 20° C. for 0.5 hour. The reaction mixture was filtered and the filtrate was concentrated to give the title compound (400 mg, 74% yield), which was used in the next step without purification. Yellow oil. ¹H NMR (400 MHz, chloroform-d) δ=4.73 (q, J=6.4 Hz, 1H), 3.06-2.88 (m, 2H), 2.72-2.52 (m, 2H), 1.97-1.88 (m, 1H), 1.86-1.64 (m, 5H), 1.57-1.43 (m, 2H), 1.24-1.14 (m, 12H).

Step J. 1-(hexahydro-1H-pyrrolizin-7a-yl)ethanol. To a solution of 1-(hexahydro-1H-pyrrolizin-7a-yl)ethyl pivalate (350 mg, 1.46 mmol, 1.0 eq) in MeOH (4.2 mL) and H₂O (1.4 mL) was added NaOH (58.5 mg, 1.46 mmol, 1.0 eq). The mixture was stirred at 60° C. for 12 hours. After completion, the reaction mixture was concentrated under vacuum and the residue was diluted with DCM (1 mL). The reaction mixture was filtered and the filtrate was concentrated to give the title compound (163 mg, 72% yield). Light yellow oil.

Step K. (1R,5S)-tert-butyl 3-(7-chloro-8-fluoro-2-(1-(hexahydro-1H-pyrrolizin-7a-yl)ethoxy) pyrido[4,3-d]pyrimidin-4-yl)-3,8-diazabicyclo[3.2.1]octane-8-carboxylate. To a solution of tert-butyl (1R,5S)-3-(2,7-dichloro-8-fluoropyrido[4,3-d]pyrimidin-4-yl)-3,8-diazabicyclo[3.2.1]octane-8-carboxylate (844 mg, 1.97 mmol, 2.0 eq) and 1-(hexahydro-1H-pyrrolizin-7a-yl)ethanol ((153 mg, 985 μmol, 1.0 eq) in dioxane (15 mL) were added 4 Å Molecular Sieve (844 mg) and DIPEA (637 mg, 4.93 mmol, 858 μL, 5.0 eq) at 20° C., and the suspension was stirred at 95° C. for 16 hours. After completion, the suspension was filtered. The filtrate was purified by reversed phase flash chromatography (0.1% FA condition) to give the title compound (285 mg, 52% yield). Yellow solid. ¹H NMR (400 MHz, methanoL-d4) δ=8.84 (s, 1H), 5.17 (q, J=6.4 Hz, 1H), 4.66-4.48 (m, 2H), 4.37 (br d, J=1.6 Hz, 2H), 3.70 (br t, J=11.6 Hz, 2H), 3.16-2.94 (m, 2H), 2.79-2.65 (m, 2H), 2.28-2.14 (m, 1H), 2.09-2.02 (m, 1H), 1.98-1.83 (m, 5H), 1.81-1.59 (m, 5H), 1.58-1.43 (m, 9H), 1.39 (d, J=6.4 Hz, 3H). LCMS [ESI, M+1]: 547.2.

Step L. (1R,5S)-tert-butyl 3-(8-fluoro-7-(8-fluoronaphthalen-1-yl)-2-(1-(hexahydro-1H-pyrrolizin-7a-yl)ethoxy) pyrido[4,3-d]pyrimidin-4-yl)-3,8-diazabicyclo[3.2.1]octane-8-carboxylate. A mixture of (1R,5S)-tert-butyl 3-(7-chloro-8-fluoro-2-(1-(hexahydro-1H-pyrrolizin-7a-yl) ethoxy)pyrido[4,3-d]pyrimidin-4-yl)-3,8-diazabicyclo [3.2.1]octane-8-carboxylate (80 mg, 146 μmol, 1.0 eq), 2-(8-fluoro-1-naphthyl)-4,4,5,5-tetramethyl-1,3,2-dioxaborolane (59.7 mg, 219 μmol, 1.5 eq), K₃PO₄ (1.5 M, 292 μL, 3.0 eq), [2-(2-aminophenyl)phenyl]palladium(1+); bis (1-adamantyl)-butyl-phosphane; methanesulfonate (10.6 mg, 14.6 μmol, 0.1 eq) in THF (1 mL) was degassed and purged with N₂ for 3 times, and then the mixture was stirred at 60° C. for 3 hours under N₂ atmosphere. After completion, the reaction mixture was quenched by water (2 mL) at 20° C., and then extracted with ethyl acetate (3×2 mL). The combined organic layers were dried over Na₂SO₄, filtered and concentrated under reduced pressure to give a residue. The crude product was purified by reversed phase flash chromatography (0.1% FA condition) to give the title compound (63 mg, 63% yield). Yellow solid. ¹H NMR (400 MHz, chloroform-d) δ=9.01 (s, 1H), 7.99 (br d, J=7.6 Hz, 1H), 7.74 (d, J=8.4 Hz, 1H), 7.66-7.54 (m, 2H), 7.44 (dt, J=4.8, 7.6 Hz, 1H), 7.14-7.09 (m, 1H), 5.26 (q, J=6.0 Hz, 1H), 4.69-4.27 (m, 4H), 3.81-3.49 (m, 2H), 3.16-2.96 (m, 2H), 2.73-2.59 (m, 2H), 2.19-2.06 (m, 2H), 2.00-1.93 (m, 2H), 1.90-1.73 (m, 6H), 1.70-1.56 (m, 2H), 1.53 (s, 9H), 1.44-1.36 (m, 3H).

Step M. 4-((1R,5S)-3,8-diazabicyclo[3.2.1]octan-3-yl)-8-fluoro-7-(8-fluoronaphthalen-1-yl)-2-(1-(hexahydro-1H-pyrrolizin-7a-yl)ethoxy)pyrido[4,3-d]pyrimidine. To a solution of (1R,5S)-tert-butyl 3-(8-fluoro-7-(8-fluoronaphthalen-1-yl)-2-(1-(hexahydro-1H-pyrrolizin-7a-yl)ethoxy)pyrido[4,3-d]pyrimidin-4-yl)-3,8-diazabicyclo [3.2.1]octane-8-carboxylate (63 mg, 95.9 μmol, 1.0 eq) in CH₃CN (2 mL) was added HCl·dioxane (4 M, 1 mL, 41.70 eq) at 0° C., and the mixture was stirred under N₂ at 0° C.

for 30 minutes. After completion, the reaction mixture was concentrated under reduced pressure below 30° C., and then basified with saturated NaHCO₃ solution to pH~8. The mixture was extracted with ethyl acetate (3×10 mL), and the combined organic phases were dried over Na₂SO₄, filtered and concentrated. The residue was purified by prep-HPLC (column: Phenomenex Gemini-NX C18 75*30 mm*3 um; mobile phase: [water (0.225% FA)-ACN]; B %: 15%-25%, 9 min). The fractions were collected, basified with saturated NaHCO₃ solution to pH~8, and then extracted with DCM (3×5 mL). The organic phase was dried over Na₂SO₄, filtered, concentrated and lyophilized to give the title compound (12.0 mg, 22% yield). White solid. $^1$H NMR (400 MHz, methanol-d4) δ=9.05 (s, 1H), 8.12 (d, J=8.8 Hz, 1H), 7.85 (d, J=8.4 Hz, 1H), 7.70 (dd, J=7.2, 8.4 Hz, 1H), 7.60 (d, J=7.2 Hz, 1H), 7.57-7.48 (m, 1H), 7.20 (dd, J=7.2, 13.2 Hz, 1H), 5.21 (dd, J=4.8, 6.0 Hz, 1H), 4.70-4.53 (m, 2H), 3.75-3.64 (m, 4H), 3.19-2.98 (m, 2H), 2.79-2.68 (m, 2H), 2.30-2.19 (m, 1H), 2.12-2.00 (m, 1H), 1.97-1.62 (m, 10H), 1.43 (d, J=6.4 Hz, 3H). $^{19}$F NMR (400 MHz, methanol-d4) δ−115.18, −141.14. LCMS [ESI, M+1]: 557.2.

Example 451

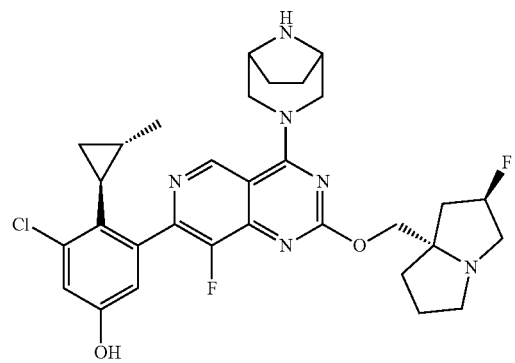 [SMILES: C[C@H]1C[C@@H]1c1c(Cl)cc(O)cc1-c1ncc2c(N3CC4CCC(C3)N4)nc(OC[C@@]34CCCN3C[C@H](F)C4)nc2c1F]

3-(4-((1R,5S)-3,8-diazabicyclo[3.2.1]octan-3-yl)-8-fluoro-2-(((2R,7aS)-2-fluorotetrahydro-1H-pyrrolizin-7a(5H)-yl)methoxy)pyrido[4,3-d]pyrimidin-7-yl)-5-chloro-4-((1S,2S)-2-methylcyclopropyl)phenol

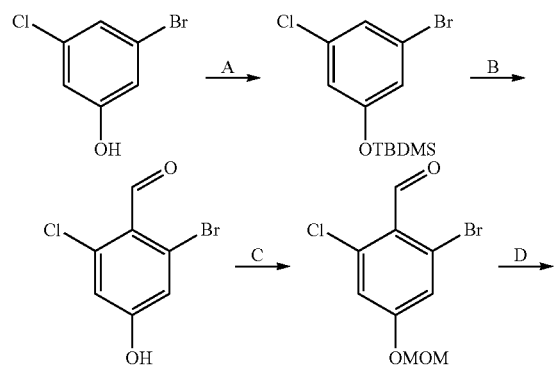

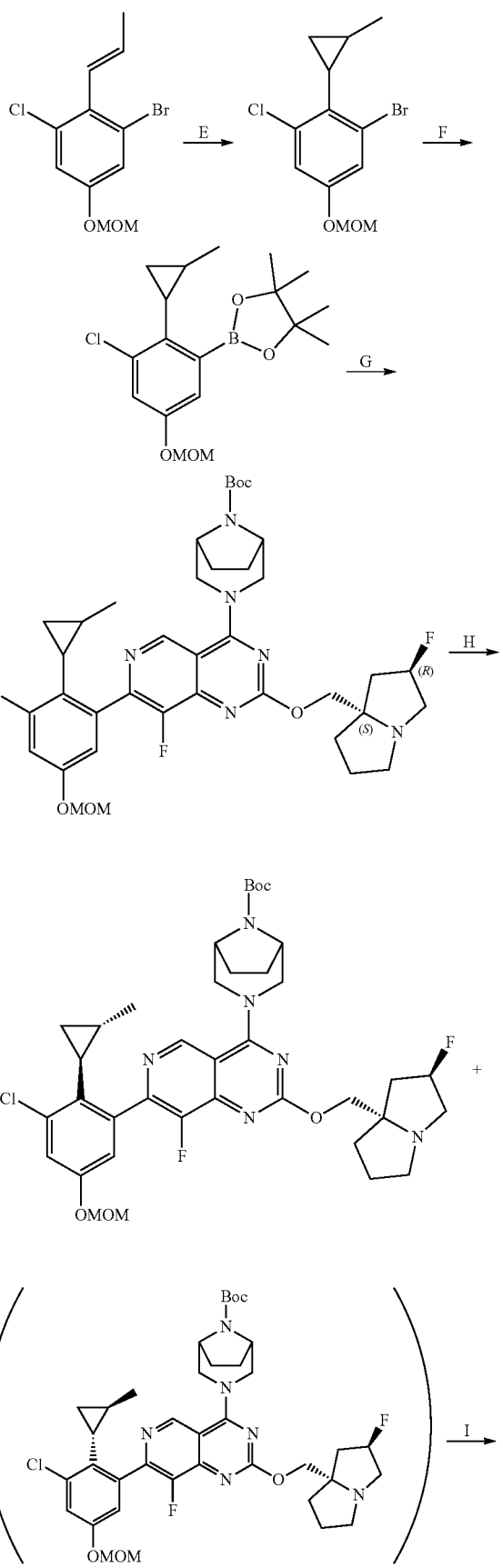

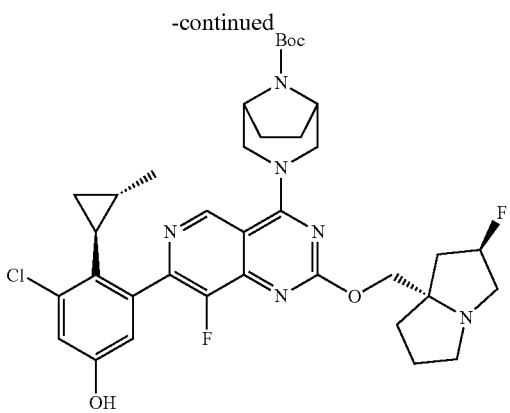

Step A. (3-bromo-5-chloro-phenoxy)-tert-butyl-dimethyl-silane. To a mixture of 3-bromo-5-chlorophenol (10.0 g, 48.2 mmol, 1.0 eq) and imidazole (7.22 g, 106 mmol, 2.2 eq) in DMF (100 mL) was added TBDMSCl (7.99 g, 53.0 mmol, 6.50 mL, 1.1 eq) at 0° C. The mixture was stirred at 25° C. for 15 hours. After completion, the mixture was diluted with ethyl acetate (110 mL) and washed with water (110 mL) then separated. The aqueous phase was extracted with ethyl acetate (80 mL) and the organic layer was washed with saturated brine (3×50 mL), dried over Na2SO4, filtered and concentrated under vacuum. The residue was purified by column chromatography (SiO$_2$, ethyl acetate/petroleum ether=0/1) to give the title compound (14.24 g, 92% yield). Colorless oil. Rf=0.9 (5:1, petroleum ether/ethyl acetate). $^1$H NMR (400 MHz, CDCl$_3$-d) δ=7.13 (t, J=1.6 Hz, 1H), 6.90 (t, J=1.6 Hz, 1H), 6.78 (t, J=2.0 Hz, 1H), 0.98 (s, 8H), 0.23-0.21 (m, 6H).

Step B. 2-bromo-6-chloro-4-hydroxy-benzaldehyde. LDA (2 M in hexane, 8.57 mL, 1.3 eq) in THF (15 mL) was cooled to −65° C. Then (3-bromo-5-chloro-phenoxy)-tert-butyl-dimethyl-silane (4.24 g, 13.2 mmol, 1.0 eq) in THF (43 mL) was added into the above mixture and the mixture was stirred at −65° C. for 1 hour. DMF (1.93 g, 26.4 mmol, 2.03 mL, 2.0 eq) in THF (8 mL) was added into the above mixture at −65° C. and the mixture was stirred at −65° C. for 1 hour. After completion, the pH value was adjusted to 2 with 1M HCl. Then the mixture was diluted with ethyl acetate (40 mL) and separated. The aqueous phase was extracted with ethyl acetate (40 mL). The combined organic layer was washed with saturated brine (50 mL), dried over Na2SO4, filtered and concentrated under vacuum. The residue was purified by column chromatography (SiO2, petroleum ether/ethyl acetate=3/1-1/1) to give the title compound (2.40 g, 74% yield). Yellow solid. Rf=0.2 (5:1, petroleum ether/ethyl acetate). 1H NMR (400 MHz, METHANOL-d4) δ=10.24 (s, 1H), 7.10 (d, J=2.4 Hz, 1H), 6.92 (d, J=2.4 Hz, 1H). LCMS [ESI, M+1]:237.0.

Step C. 2-bromo-6-chloro-4-(methoxymethoxy)benzaldehyde. To a mixture of 2-bromo-6-chloro-4-hydroxy-benzaldehyde (2.40 g, 10.2 mmol, 1.0 eq) in dichloromethane (30 mL) was added DIEA (3.95 g, 30.6 mmol, 5.33 mL, 3.0 eq) and MOMCl (1.23 g, 15.3 mmol, 1.16 mL, 1.5 eq) at 0° C. The mixture was stirred at 0° C. for 0.5 hour. After completion, the mixture was quenched by water (5 mL) and diluted with water (10 mL) then separated. The aqueous phase was extracted with dichloromethane (10 mL). The organic layer was washed with saturated brine (15 mL), dried over Na$_2$SO$_4$, filtered and concentrated under vacuum. The residue was purified by column chromatography (SiO$_2$, petroleum ether/ethyl acetate=10/1-5/1) to give the title compound (2.09 g, 72% yield). White solid. Rf=0.5 (5:1, petroleum ether/ethyl acetate). $^1$H NMR (400 MHz, CDCl$_3$-d) δ=10.33 (s, 1H), 7.29 (d, J=2.4 Hz, 1H), 7.12 (d, J=2.4 Hz, 1H), 5.23 (s, 2H), 3.50 (s, 3H). LCMS [ESI, M+1]: 280.9.

Step D. 1-bromo-3-chloro-5-(methoxymethoxy)-2-[(E)-prop-1-enyl]benzene. To a mixture of ethyl(triphenyl)phosphonium; bromide (35.9 g, 96.6 mmol, 1.5 eq) in THF (180 mL) was added t-BuOK (1 M in THF, 83.72 mL, 1.3 eq) dropwise at 0° C. The mixture was stirred at 10° C. for 1 hour. 2-bromo-6-chloro-4-hydroxy-benzaldehyde (18 g, 64.4 mmol, 1.0 eq) was dissolved in THF (90 mL) was added to the above mixture and the mixture was stirred at 10° C. for 40 mins. After completion, the mixture was quenched by H$_2$O (220 mL) and concentrated under vacuum. Then the mixture was diluted with ethyl acetate (200 mL) then separated. The aqueous phase was extracted with ethyl acetate (100 mL). The combined organic layer was washed with saturated brine (150 mL), dried over Na$_2$SO$_4$, filtered and concentrated under vacuum. The residue was purified by column chromatography (SiO$_2$, petroleum ether/ethyl acetate=50/1) to give the title compound (18.0 g, 95% yield). Yellow oil. Rf=0.6 (10:1, petroleum ether/ethyl acetate). Yellow oil. $^1$H NMR (400 MHz, CDCl$_3$-d) δ=7.25-7.22 (m, 1H), 7.11-7.07 (m, 1H), 6.30-6.17 (m, 1H), 6.13-5.90 (m, 1H), 5.16-5.13 (m, 2H), 3.50-3.47 (m, 3H), 1.95-1.56 (m, 3H).

Step E. 1-bromo-3-chloro-5-(methoxymethoxy)-2-(2-methylcyclopropyl)benzene. To a mixture of ZnEt2 (1 M, 103 mL, 6.0 eq) in dichloromethane (100 mL) was added TFA (11.7 g, 103 mmol, 7.62 mL, 6.0 eq) in dichloromethane (10 mL) dropwise slowly at −40° C. under N2. After stirring for 0.5 hour, diiodomethane (27.6 g, 103 mmol, 8.30 mL, 6.0 eq) was added into the above mixture at −40° C. The mixture was stirred at −40° C. for 0.5 hour then 1-bromo-3-chloro-5-(methoxymethoxy)-2-[(E)-prop-1-enyl]benzene (5.0 g, 17.1 mmol, 1.0 eq) in dichloromethane (20 mL) was added to the above mixture at −40° C. The mixture was stirred at 20° C. for 18 hours. After completion, the mixture was quenched by water (150 mL) and diluted with dichloromethane (20 mL) and then filtered. The mixture was separated and the aqueous phase was extracted with dichloromethane (30 mL). The combined organic layer was washed with saturated brine (50 mL), dried over Na$_2$SO$_4$, filtered and concentrated under vacuum. The residue was purified by reversed phase flash [water (FA, 0.1%)/acetonitrile] to give the title compound (1.58 g, 29% yield). Yellow oil. Rf=0.55 (10:1, petroleum ether/ethyl acetate). 1H NMR (400 MHz, CDCl$_3$-d) δ=7.23-7.18 (m, 1H), 7.06-7.02 (m, 1H), 5.12 (s, 2H), 3.48-3.46 (m, 3H), 1.38-1.32 (m, 1H), 1.28 (d, J=6.0 Hz, 3H), 1.08-0.98 (m, 1H), 0.94-0.85 (m, 2H).

Step F. 2-[3-chloro-5-(methoxymethoxy)-2-(2-methylcyclopropyl)phenyl]-4,4,5,5-tetramethyl-1,3,2-dioxaborolane. To a mixture of 1-bromo-3-chloro-5-(methoxymethoxy)-2-(2-methylcyclopropyl)benzene (1.7 g, 5.56 mmol, 1.0 eq), 4,4,5,5-tetramethyl-2-(4,4,5,5-tetramethyl-1,3,2-dioxaborolan-2-yl)-1,3,2-dioxaborolane (2.83 g, 11.1 mmol, 2.0 eq) and KOAc (1.91 g, 19.5 mmol, 3.5 eq) in dioxane (20 mL) was added Pd(dppf)Cl2 (407 mg, 556 μmol, 0.10 eq) under N$_2$. The mixture was degassed and then heated to 80° C. for 5 hours under N$_2$. After completion, the mixture was diluted with ethyl acetate (20 mL) and water (20 mL) then separated. The aqueous phase was extracted with ethyl acetate (15 mL). The combined organic layer was washed with saturated brine (20 mL), dried over Na$_2$SO$_4$, filtered and concentrated under vacuum. The residue was purified by reversed phase flash [water (FA, 0.1%)/acetonitrile] to give the title compound (1.15 g, 56% yield). Yellow oil. Rf=0.5 (10:1, petroleum ether/ethyl acetate). 1H NMR (400 MHz, CDCl3-d) δ=7.12-7.10 (m, 1H), 7.10-7.09 (m, 1H), 5.14-5.11 (m, 2H), 3.46 (s, 3H), 1.65 (dt, J=5.2, 8.4 Hz, 1H), 1.38 (d, J=2.4 Hz, 12H), 1.27 (d, J=6.0 Hz, 3H), 0.86-0.80 (m, 1H), 0.75-0.67 (m, 2H).

Step G. tert-butyl (1R,5S)-3-(7-(3-chloro-5-(methoxymethoxy)-2-(2-methylcyclopropyl)phenyl)-8-fluoro-2-(((2R,7aS)-2-fluorotetrahydro-1H-pyrrolizin-7a (5H)-yl)methoxy)pyrido[4,3-d]pyrimidin-4-yl)-3,8-diazabicyclo[3.2.1]octane-8-carboxylate. A mixture of tert-butyl (1R,5S)-3-(7-chloro-8-fluoro-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (1.30 g, 2.36 mmol, 1.0 eq), 2-[3-chloro-5-(methoxymethoxy)-2-(2-methylcyclopropyl)phenyl]-4,4,5,5-tetramethyl-1,3,2-dioxaborolane (1.08 g, 3.07 mmol, 1.3 eq), K3PO4 (1.5 M, 4.72 mL, 3.0 eq) and [2-(2-aminophenyl)phenyl]palladium(1+); bis(1-adamantyl)-butyl-phosphane; methanesulfonate (172 mg, 236 µmol, 0.1 eq) in THF (15 mL) was stirred at 60° C. for 4.5 hours under N2. After completion, the mixture was diluted with ethyl acetate (10 mL) and water (15 mL) then separated. The aqueous phase was extracted with ethyl acetate (10 mL). The combined organic layer was washed with saturated brine (15 mL), dried over Na2SO4, filtered and concentrated under vacuum. The residue was purified by reversed phase flash [water (FA, 0.1%)/acetonitrile] to give the title compound (1.03 g, 58% yield). Yellow solid. 1H NMR (400 MHz, CDCl3-d) δ=9.01 (s, 1H), 7.19 (d, J=2.4 Hz, 1H), 7.03 (d, J=2.4 Hz, 1H), 5.37-5.33 (m, 1H), 5.23-5.20 (m, 1H), 5.20-5.15 (m, 2H), 4.60-4.51 (m, 2H), 4.46-4.33 (m, 2H), 4.30-4.15 (m, 2H), 3.79-3.61 (m, 2H), 3.49-3.47 (m, 3H), 3.29-3.11 (m, 3H), 3.02-2.95 (m, 1H), 2.34-2.15 (m, 3H), 2.03-1.61 (m, 11H), 1.53 (s, 9H), 0.57-0.20 (m, 3H). LCMS [ESI, M+1]:741.2.

Step H. tert-butyl (1R,5S)-3-(7-(3-chloro-5-(methoxymethoxy)-2-((1S,2S)-2-methylcyclopropyl)phenyl)-8-fluoro-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate and tert-butyl (1R,5S)-3-(7-(3-chloro-5-(methoxymethoxy)-2-((1R,2R)-2-methylcyclopropyl)phenyl)-8-fluoro-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate. tert-butyl (1R,5S)-3-(7-(3-chloro-5-(methoxymethoxy)-2-(2-methylcyclopropyl)phenyl)-8-fluoro-2-(((2R,7aS)-2-fluorotetrahydro-1H-pyrrolizin-7a (5H)-yl)methoxy)pyrido[4,3-d]pyrimidin-4-yl)-3,8-diazabicyclo[3.2.1]octane-8-carboxylate (1.23 g) was separated by SFC (column: DAICEL CHIRALCEL OD (250 mm*30 mm, 10 um); mobile phase: [0.1% NH3H2O MEOH]; B %: 50%-50%, 9 min; 120 min) to give tert-butyl (1R,5S)-3-(7-(3-chloro-5-(methoxymethoxy)-2-((1S,2S)-2-methylcyclopropyl)phenyl)-8-fluoro-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (540 mg, 44%) and tert-butyl (1R,5S)-3-(7-(3-chloro-5-(methoxymethoxy)-2-((1R,2R)-2-methylcyclopropyl)phenyl)-8-fluoro-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (527 mg, 43%) (the absolute stereochemistry of methylarylcyclopropyl group is arbitrarily assigned).

Step I. 3-(4-((1R,5S)-3,8-diazabicyclo[3.2.1]octan-3-yl)-8-fluoro-2-(((2R,7aS)-2-fluorotetrahydro-1H-pyrrolizin-7a (5H)-yl)methoxy)pyrido[4,3-d]pyrimidin-7-yl)-5-chloro-4-((1S,2S)-2-methylcyclopropyl)phenol. To a mixture of tert-butyl (1R,5S)-3-(7-(3-chloro-5-(methoxymethoxy)-2-((1S,2S)-2-methylcyclopropyl)phenyl)-8-fluoro-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (200 mg, 2701 µmol, 1.0 eq) in MeCN (1.5 mL) was added HCl·dioxane (4 M, 3 mL, 44 eq) at 0° C. and the mixture was stirred at 0° C. for 0.5 hour. After completion, the mixture was concentrated under vacuum. Then the pH value was adjusted to 8 with saturated Na2CO3 solution and the mixture was washed with methanol (2×20 mL), filtered and concentrated under vacuum. The residue was purified by prep-HPLC (column: Shim-pack C18 150*25*10 um; mobile phase: [water (0.225% FA)-ACN]; B %: 12%-32%, 10 min) to give the title compound (100 mg, 57% yield, FA). White solid. 1H NMR (400 MHz, METHANOL-d4) δ=9.13 (s, 1H), 6.97 (d, J=2.4 Hz, 1H), 6.77 (d, J=2.4 Hz, 1H), 5.58-5.42 (m, 1H), 4.79 (br dd, J=5.6, 13.2 Hz, 2H), 4.61-4.55 (m, 2H), 4.10 (br s, 2H), 3.92 (br dd, J=5.6, 13.2 Hz, 2H), 3.86-3.62 (m, 3H), 3.37-3.32 (m, 1H), 2.67-2.33 (m, 3H), 2.28-2.20 (m, 2H), 2.16-1.97 (m, 5H), 1.55-1.48 (m, 1H), 0.83 (br s, 3H), 0.49-0.19 (m, 3H). LCMS [ESI, M/2+1, M+1]: 299.5, 597.2.

Example 452

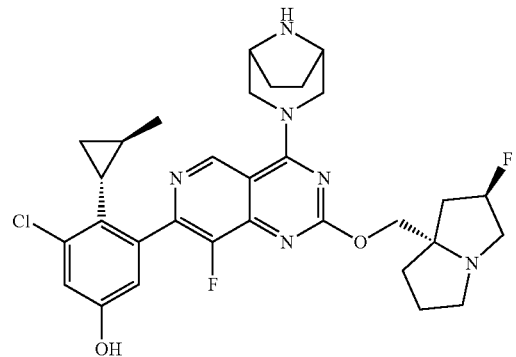 [SMILES: C[C@@H]1C[C@H]1c1c(Cl)cc(O)cc1-c1ncc2c(N3CC4CCC(C3)N4)nc(OC[C@@]34CCCN3C[C@H](F)C4)nc2c1F]

3-(4-((1R,5S)-3,8-diazabicyclo[3.2.1]octan-3-yl)-8-fluoro-2-(((2R,7aS)-2-fluorotetrahydro-1H-pyrrolizin-7a(5H)-yl)methoxy)pyrido[4,3-d]pyrimidin-7-yl)-5-chloro-4-((1R,2R)-2-methylcyclopropyl)phenol Synthesized according to Example 451, Step I substituting tert-butyl (1R,5S)-3-(7-(3-chloro-5-(methoxymethoxy)-2-((1R,2R)-2-methylcyclopropyl)phenyl)-8-fluoro-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate in place of (1R,5S)-3-(7-(3-chloro-5-(methoxymethoxy)-2-((1S,2S)-2-methylcyclopropyl)phenyl)-8-fluoro-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate to afford the title compound (100 mg, 57% yield, FA). White solid. 1H NMR (400 MHz, METHANOL-d4) δ=9.13 (s, 1H), 6.97 (d, J=2.8 Hz, 1H), 6.78 (d, J=2.4 Hz, 1H), 5.59-5.43 (m, 1H), 4.83-4.77 (m, 2H), 4.63-4.55 (m, 2H), 4.11 (br s, 2H), 3.92 (br dd, J=6.4, 13.6 Hz, 2H), 3.88-3.64 (m, 3H), 3.38-3.32 (m, 1H), 2.68-2.34 (m, 3H), 2.29-2.21 (m, 2H), 2.16-1.97

(m, 5H), 1.55-1.49 (m, 1H), 0.83 (br s, 3H), 0.48-0.20 (m, 3H). LCMS [ESI, M/2+1, M+1]: 299.4, 597.1.

Example 453

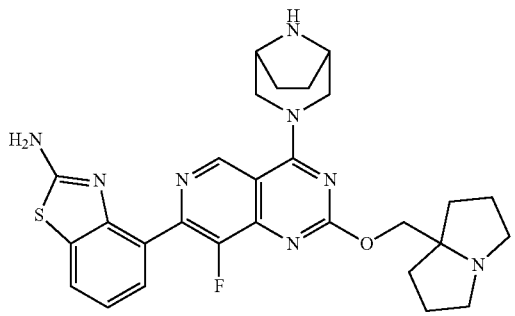 [SMILES: Nc1nc2c(-c3ncc4c(N5CC6CCC(C5)N6)nc(OCC56CCCN5CCC6)nc4c3F)cccc2s1]

4-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)benzo[d]thiazol-2-amine

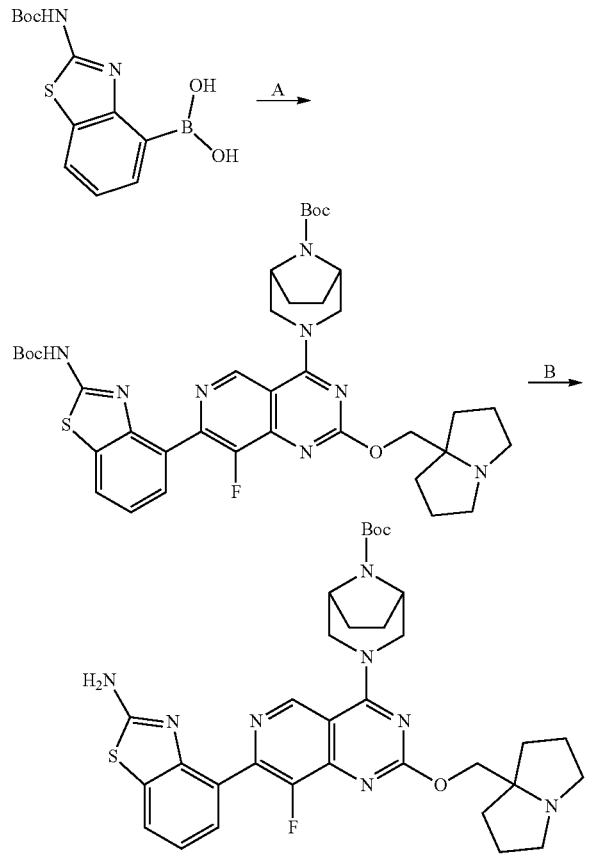

Step A: (1R,5S)-tert-butyl 3-(7-(2-((tert-butoxycarbonyl)amino)benzo[d]thiazol-4-yl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate. To a solution of (1R,5S)-tert-butyl 3-(7-chloro-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (500 mg, 938 μmol, 1.0 eq) in THF (5.0 mL) was added K$_3$PO$_4$ (1.5 M, 1.88 mL, 3.0 eq) and (2-((tert-butoxycarbonyl)amino)benzo[d]thiazol-4-yl)boronic acid (386 mg, 1.31 mmol, 1.40 eq). The reaction was degassed with Ar for 15 minutes followed by the addition of BrettPhos Pd G3 (85.0 mg, 93.8 μmol, 0.10 eq). The mixture was stirred at 60° C. for 12 hours. Water (10.0 mL) was added and the reaction mixture was extracted with EtOAc (2×10.0 mL). The combined organic layers were dried over Na$_2$SO$_4$, filtered and concentrated to give a residue. The residue was purified by reversed phase flash chromatography (C18, 0.1% formic acid condition) to afford product as yellow solid (440 mg, 59% yield); LCMS [ESI, M+1]: 747.3.

Step B: 4-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)benzo[d]thiazol-2-amine. To a solution of (1R,5S)-tert-butyl 3-(7-(2-((tert-butoxycarbonyl)amino)benzo[d]thiazol-4-yl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (400 mg, 536 μmol, 1.0 eq) in DCM (4.0 mL) was added TFA (6.16 g, 54.0 mmol, 4.0 mL, 101 eq). The reaction mixture was stirred at 20° C. for 1 hour. The reaction mixture was concentrated at 20° C. to give a residue. The pH of the residue was adjusted with saturated Na$_2$CO$_3$ aqueous solution to ~7 and the mixture was extracted with EtOAc (2×5 mL). The combined organic layers were dried over Na$_2$SO$_4$, filtered and concentrated to give a residue. The residue was purified by prep-HPLC (column: Phenomenex luna C18 150*25 mm*10 um; mobile phase: [water (0.225% FA)-ACN]; B %: 6%-36%, 10 min), followed by prep-HPLC(column: Phenomenex luna C18 150*25 mm*10 um; mobile phase: [water (0.225% FA)-ACN]; B %: 6%-36%, 10 min) to afford product as yellow solid (107 mg, 36% yield). $^1$H NMR (400 MHz, METHANOL-d$_4$) δ=9.12 (s, 1H), 7.78 (dd, J=1.2, 8.0 Hz, 1H), 7.46 (dd, J=1.2, 7.6 Hz, 1H), 7.25 (t, J=8.0 Hz, 1H), 4.80 (br d, J=13.2 Hz, 4H), 4.07 (br s, 2H), 3.90 (br d, J=13.2 Hz, 2H), 3.75-3.64 (m, 2H), 3.35-3.32 (m, 1H), 3.30-3.26 (m, 1H), 2.40-2.29 (m, 2H), 2.28-2.02 (m, 8H), 2.01-1.93 (m, 2H); LCMS [ESI, M+1]:547.1.

Example 454

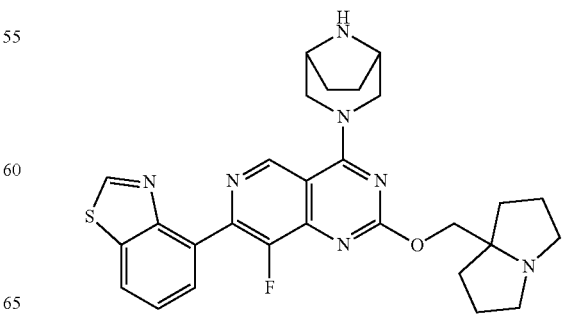

929

4-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)benzo[d]thiazole

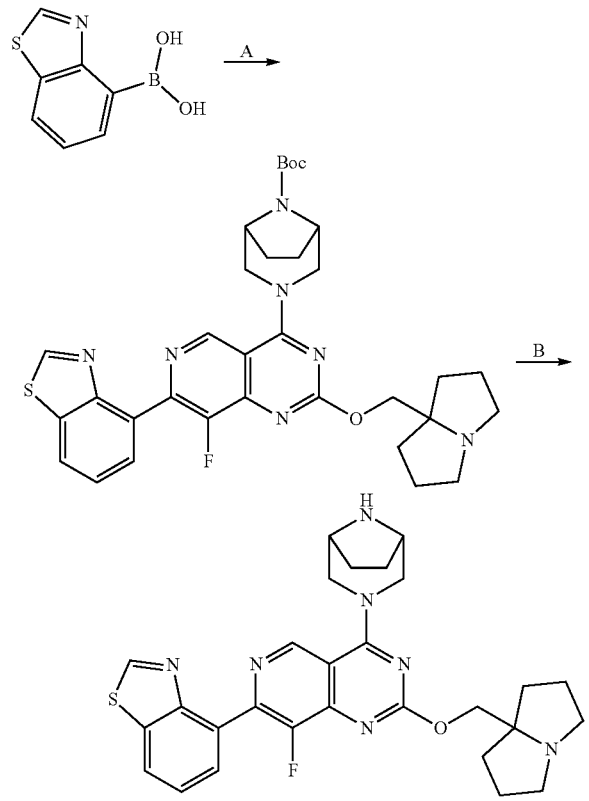

Step A: (1R,5S)-tert-butyl 3-(7-(benzo[d]thiazol-4-yl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate. To a mixture of (1R,5S)-tert-butyl 3-(7-chloro-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (107 mg, 201 μmol, 0.8 eq) and benzo[d]thiazol-4-ylboronic acid (45 mg, 251p mol, 1.0 eq) in THF (4.0 mL) was added K₃PO₄ (1.5 M, 675 uL, 4.0 eq). The reaction mixture was degassed with Ar for 15 minutes followed by the addition of Ad₂nBuP Pd G3 (cataCXium® A Pd G3) (27.5 mg, 37.7 μmol, 0.15 eq). The reaction mixture was heated to 60° C. and stirred for 2 hours. The reaction mixture was filtered and concentrated in vacuum to give a residue. The residue was purified by reversed-phase flash chromatography (0.1% FA condition) to afford product as white solid (80 mg, 50% yield). LCMS [ESI, M+1]: 632.1.

Step B: 4-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)benzo[d]thiazole. To a solution of (1R,5S)-tert-butyl 3-(7-(benzo[d]thiazol-4-yl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (70 mg, 111 μmol, 1.0 eq) in ACN (0.2 mL) was added HCl·dioxane (4 M, 27.7 uL, 1.0 eq). The reaction mixture was stirred at 25° C. for 30 minutes. The reaction mixture was concentrated in vacuum to give a residue. The residue was purified by prep-HPLC (column: Phenomenex Luna C18 150*25 mm*10 um; mobile phase: [water (0.225% FA)-ACN]; B %: 1%-30%, 10 min) to afford product as yellow solid (4.34 mg, 7% yield). ¹H NMR (400 MHz, methanol-d₄) δ 9.30 (s, 1H) 9.18 (s, 1H), 8.44 (s, 2H), 8.29 (dd, J=1.2 Hz, 8.0 Hz, 1H), 7.79 (dd, J=1.2 Hz, 7.6 Hz, 1H), 7.70 (t, J=7.6 Hz, 1H), 4.80 (d, J=12.8 Hz, 2H), 4.68 (s, 2H), 4.00 (s, 2H), 3.88 (d, J=12.8 Hz, 2H), 3.74-3.66 (m, 2H), 3.30-3.26 (m, 2H), 2.40-2.30 (m, 2H), 2.29-2.09 (m, 6H), 2.06-1.91 (m, 4H); LCMS [ESI, M+1]: 532.3

Example 455

4-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)-7-fluorobenzo[d]thiazol-2-amine

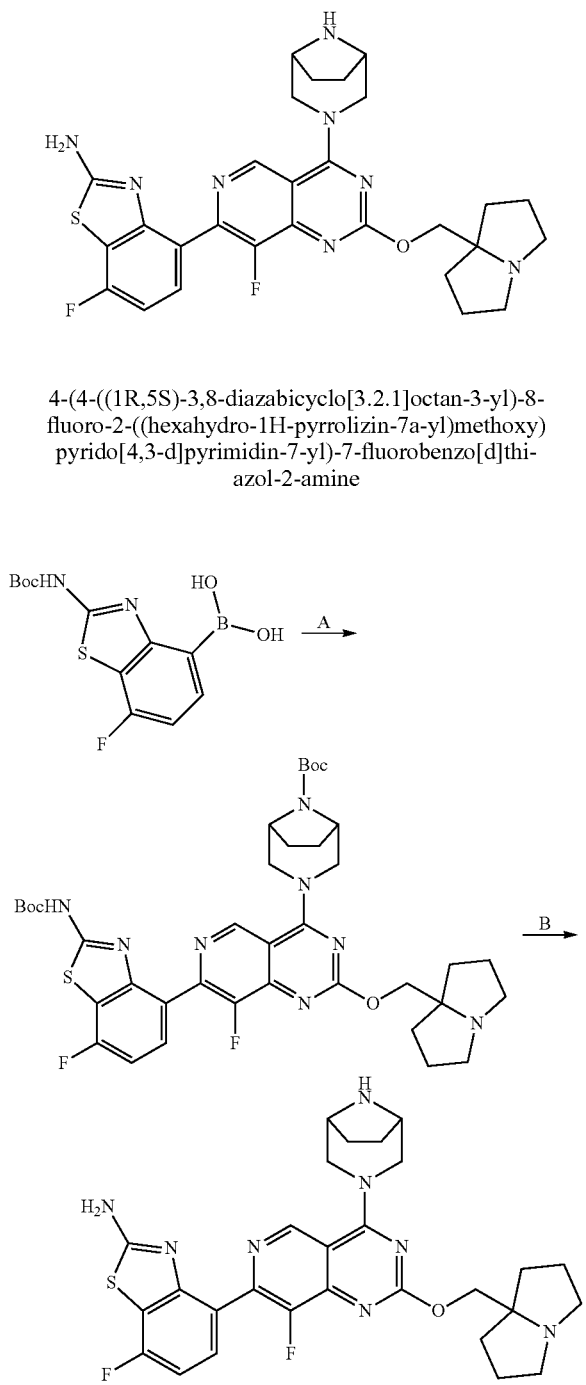

931

Step A: (1R,5S)-tert-butyl 3-(7-(2-((tert-butoxycarbonyl)amino)-7-fluorobenzo[d]thiazol-4-yl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate. To a mixture of (1R,5S)-tert-butyl 3-(7-chloro-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (91.1 mg, 171 μmol, 1.0 eq) and (2-((tert-butoxycarbonyl)amino)-7-fluorobenzo[d]thiazol-4-yl)boronic acid (80 mg, 256.31 μmol, 1.5 eq) in THF (1.0 mL) was added K₃PO₄ (1.5 M, 342 uL, 3.0 eq). The reaction mixture was degassed with N₂ for 15 minutes followed by the addition of BrettPhos Pd G3 (31.0 mg, 34.2 μmol, 0.2 eq). The reaction mixture was heated to 60° C. and stirred for 2 hours. Water (5.0 mL) was added and the reaction mixture was extracted with ethyl acetate (5.0 mL×5). The combined organic phase was washed with brine (5.0 mL) and dried with anhydrous Na₂SO₄. Then the mixture was filtered and concentrated to give a residue. The residue was purified by reversed-phase flash chromatography (0.1% FA condition) to afford product as yellow solid (65 mg, 47% yield). LCMS [ESI, M+1]: 765.3

Step B: 4-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)-7-fluorobenzo[d]thiazol-2-amine. To a mixture of (1R,5S)-tert-butyl 3-(7-(2-((tert-butoxycarbonyl)amino)-7-fluorobenzo[d]thiazol-4-yl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (50 mg, 65.4 μmol, 1.0 eq) in DCM (0.1 mL) was added TFA (1.54 g, 13.5 mmol, 1000.0 uL, 207 eq) at 0° C. under N₂. The reaction mixture was stirred at 25° C. for 1 hour. Then sat. Na₂CO₃ aqueous (5 mL) was added and the reaction mixture was extracted with ethyl acetate (5.0 mL×3). The combined organic phase was washed with brine (5.0 mL) and dried with anhydrous Na₂SO₄. The mixture was filtered and concentrated to give a residue. The residue was purified by prep-HPLC (column: Phenomenex luna C18 150*25 mm*10 um; mobile phase: [water (0.225% FA)-ACN]; B %: 8%-38%, 10 min) to afford product as yellow gum (9.59 mg, 26% yield). ¹H NMR (400 MHz, MeOH-d₄) δ 9.12 (s, 1H) 7.49 (dd, J=5.6 Hz, 8.8 Hz, 1H), 7.04 (t, J=8.8 Hz, 1H), 4.83-4.80 (m, 2H), 4.70-4.68 (m, 2H), 4.13 (s, 2H), 3.95 (d, J=14.0 Hz, 2H), 3.76-3.65 (m, 2H), 3.35-3.32 (m, 2H), 2.40-2.30 (m, 2H), 2.30-1.95 (m, 10H); LCMS [ESI, M+1]: 565.3

Example 456

932

4-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)-5,6-dimethylbenzo[d]thiazol-2-amine

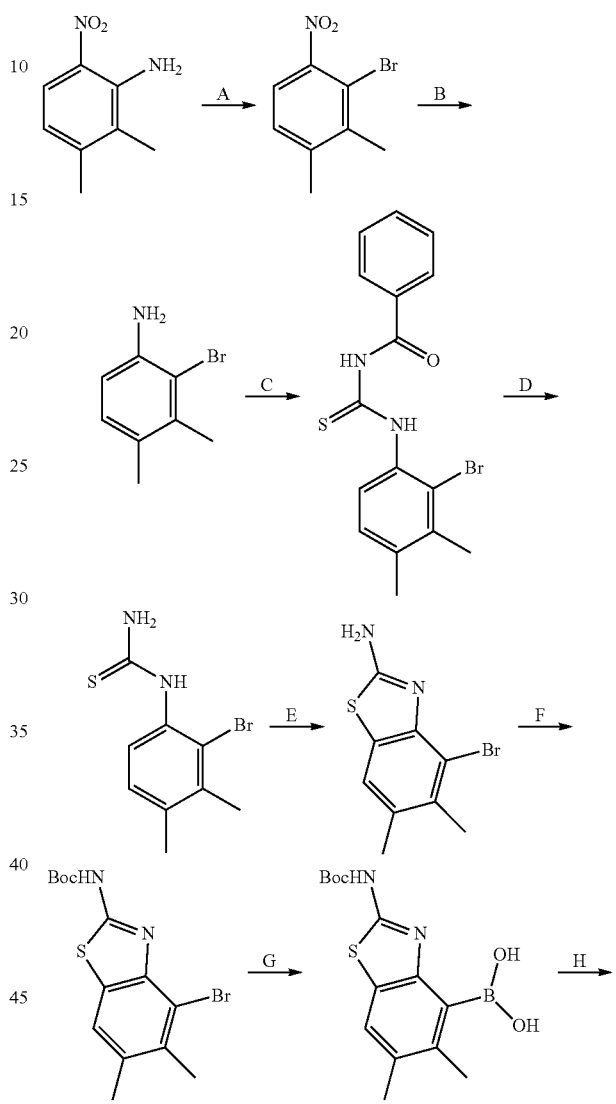

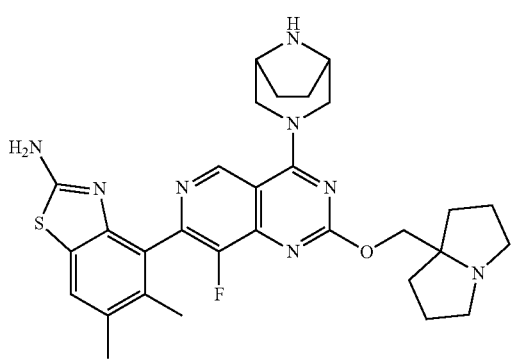 [SMILES: Cc1cc2sc(N)nc2c(-c2ncc3c(N4CC5CCC(C4)N5)nc(OCC45CCCN4CCC5)nc3c2F)c1C]

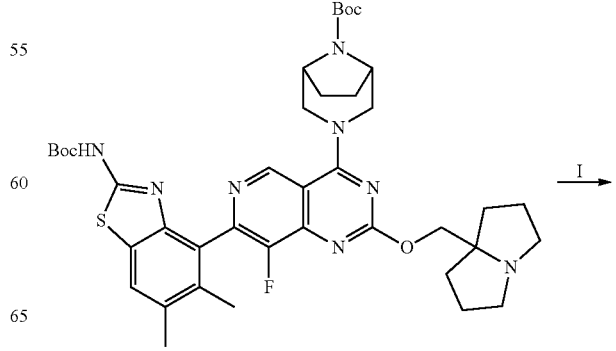

-continued

[Chemical structure shown]

Step A: 2-bromo-3,4-dimethyl-1-nitrobenzene. To a solution of 2,3-dimethyl-6-nitroaniline (10 g, 60.2 mmol, 1.0 eq) in MeCN (200 mL) was added tert-butyl nitrite (13.0 g, 126 mmol, 2.1 eq) drop-wise at 0° C. and the reaction was stirred at 0° C. for 1 hour. Then $CuBr_2$ (20 g, 89.5 mmol, 1.5 eq) was added at 0° C. and the mixture was stirred at 25° C. for 15 hours. The reaction mixture was diluted with ethyl acetate (100 mL) and then poured into saturated $NaHCO_3$ aqueous solution (500 mL). The reaction mixture was filtered through a pad of Celite. The mixture was extracted with ethyl acetate (100 mL×3). The combined organic layers were dried over anhydrous $Na_2SO_4$ and filtered. The mixture was concentrated to give a residue. The residue was purified by column chromatography ($SiO_2$, Petroleum ether) and reversed phase flash [water (FA, 0.1%)/acetonitrile=1/9] to give 2-bromo-3,4-dimethyl-1-nitrobenzene (8.5 g, 61% yield) as a light yellow solid. 1H NMR (400 MHz, DMSO-d6) δ=7.68 (d, J=8.0 Hz, 1H), 7.41 (d, J=8.4 Hz, 1H), 2.41 (s, 3H), 2.40 (s, 3H).

Step B: 2-bromo-3,4-dimethylaniline. A mixture of 2-bromo-3,4-dimethyl-1-nitrobenzene (3.0 g, 13.0 mmol, 1.0 eq), Fe (2.2 g, 39.4 mmol, 3.0 eq) and $NH_4Cl$ (4.2 g, 78.5 mmol, 6.0 eq) in EtOH (30 mL) and $H_2O$ (10 mL) was stirred at 80° C. for 3.5 hours under $N_2$ atmosphere. The reaction mixture was filtered through a pad of Celite. The filter cake was washed with EtOH (20.0 mL) and ethyl acetate (90.0 mL). The filtrate was concentrated to give a residue. The residue was dissolved in saturated $NaHCO_3$ aqueous (40.0 mL) and ethyl acetate (30.0 mL). The mixture was extracted with ethyl acetate (20.0 mL×3). The combined organic layers were dried over anhydrous $Na_2SO_4$, filtered and concentrated to give a residue. The residue was purified by reversed phase flash chromatography [water (FA, 0.1%)/acetonitrile=1/4] to give 2-bromo-3,4-dimethylaniline (2.17 g, 81% yield) as a red oil; LCMS [ESI, M+H]: 200.0.

Step C: N-((2-bromo-3,4-dimethylphenyl)carbamothioyl)benzamide. To a solution of 2-bromo-3,4-dimethylaniline (2.17 g, 10.9 mmol, 1.0 eq) in acetone (30.0 mL) was added benzoyl isothiocyanate (1.9 g, 11.6 mmol, 1.05 eq) in acetone (10 mL) at 25° C. The mixture was stirred at 25° C. for 5 minutes. The reaction mixture was concentrated to give a residue. The residue was dispersed in petroleum ether/ethyl acetate=20/1 (40.0 mL) and stirred for 0.5 hour. The mixture was filtered and the solid was dried under reduced pressure to give N-((2-bromo-3,4-dimethylphenyl)carbamothioyl)benzamide (3.56 g, 90% yield) as a light yellow solid; $^1$H NMR (400 MHz, chloroform-d) δ=12.45 (br s, 1H), 9.21 (br s, 1H), 7.95-7.92 (m, 2H), 7.79 (d, J=8.0 Hz, 1H), 7.67-7.59 (m, 1H), 7.58-7.56 (m, 2H), 7.19 (d, J=8.0 Hz, 1H), 2.44 (s, 3H), 2.37 (s, 3H).

Step D: 1-(2-bromo-3,4-dimethylphenyl)thiourea. A mixture of N-((2-bromo-3,4-dimethylphenyl)carbamothioyl)benzamide (3.3 g, 9.08 mmol, 1.0 eq) in NaOH (50 mL, 10% aqueous, 1.38 eq) was stirred at 80° C. for 3 hours. The reaction mixture was cooled to 10° C. and filtered. The filter cake was washed with $H_2O$ and petroleum ether (10.0 mL) and dried under reduced pressure to give 1-(2-bromo-3,4-dimethylphenyl)thiourea (2.2 g, 90% yield) as a white solid; LCMS [ESI, M+H+2]: 261.0.

Step E: 4-bromo-5,6-dimethylbenzo[d]thiazol-2-amine. To a solution of 1-(2-bromo-3,4-dimethylphenyl)thiourea (2.2 g, 8.49 mmol, 1.0 eq) in $CHCl_3$ (30.0 mL) was added drop-wise $Br_2$ (1.36 g, 8.49 mmol, 1.0 eq) in $CHCl_3$ (2 mL) at 0° C. The mixture was stirred at 70° C. for 1 hour. The reaction mixture was concentrated under reduced pressure to give a residue. The residue was diluted with ethyl acetate (200 mL), saturated $Na_2S_2O_3$ aqueous (50 mL) and saturated $NaHCO_3$ aqueous solution (50.0 mL). The mixture was extracted with ethyl acetate (50.0 mL×3). The combined organic layers were dried over anhydrous $Na_2SO_4$, filtered and concentrated under reduced pressure to give 4-bromo-5,6-dimethylbenzo[d]thiazol-2-amine (2 g, 88% yield) as a white solid; $^1$H NMR (400 MHz, DMSO-d6) δ=7.66 (s, 2H), 7.43 (s, 1H), 2.34 (s, 3H), 2.29 (s, 3H). LCMS [ESI, M+H+2]: 259.0.

Step F: tert-butyl (4-bromo-5,6-dimethylbenzo[d]thiazol-2-yl)carbamate. A mixture of 4-bromo-5,6-dimethylbenzo[d]thiazol-2-amine (2.0 g, 7.78 mmol, 1.0 eq), (Boc)20 (2.1 g, 9.62 mmol, 1.25 equiv), DIPEA (3.04 g, 23.5 mmol, 3.0 eq) and DMAP (96 mg, 786 μmol, 0.1 eq) in THF (40.0 mL) was stirred at 25° C. for 16 hours. The reaction mixture was diluted with $H_2O$ (50.0 mL) and ethyl acetate (200 mL). The mixture was extracted with ethyl acetate (50.0 mL×3). The combined organic layers were washed with brine (20.0 mL) and dried over anhydrous $Na_2SO_4$. The mixture was filtered and concentrated under reduced pressure to give a residue. The residue was purified by reversed phase flash chromatography [water (FA, 0.1%)/acetonitrile=1/19] to give tert-butyl (4-bromo-5,6-dimethylbenzo[d]thiazol-2-yl)carbamate (2.6 g, 91% yield) as a light yellow solid; LCMS [ESI, M+H+2]: 359.0.

Step G: (2-((tert-butoxycarbonyl)amino)-5,6-dimethylbenzo[d]thiazol-4-yl)boronic acid. A mixture of tert-butyl (4-bromo-5,6-dimethylbenzo[d]thiazol-2-yl)carbamate (1.0 g, 2.80 mmol, 1.0 eq), 2-(5,5-dimethyl-1,3,2-dioxaborinan-2-yl)-5,5-dimethyl-1,3,2-dioxaborinane (1.58 g, 7.00 mmol, 2.5 eq) and KOAc (1.00 g, 10.2 mmol, 3.6 eq) in dioxane (15.0 mL) was degassed and purged with N2 for 3 times. [2-(2-aminophenyl)phenyl]-chloro-palladium; tricyclohexylphosphane (100 mg, 169 μmol, 0.06 eq) was added and the mixture was stirred at 80° C. for 40 hours under N2 atmosphere. The reaction mixture was diluted with H2O (1.0 mL) and saturated brine (1 mL). The mixture was extracted with ethyl acetate (2.0 mL×4). The combined organic layers were dried over anhydrous Na2SO4, filtered and concentrated under reduced pressure to give a residue. The residue was purified by reversed phase flash chromatography [water (FA, 0.1%)/acetonitrile=1/9] to give (2-((tert-butoxycarbonyl)amino)-5,6-dimethylbenzo[d]thiazol-4-yl)boronic acid (0.73 g, 65% yield) as a light yellow solid; LCMS [ESI, M+H]: 323.1.

Step H: (1R,5S)-tert-butyl 3-(7-(2-((tert-butoxycarbonyl)amino)-5,6-dimethylbenzo[d]thiazol-4-yl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate. A mixture of (2-((tert-butoxycarbonyl)amino)-5,6-dimethylbenzo[d]thiazol-4-yl)boronic acid (150 mg, 465 μmol, 1.65 eq), (1R,5S)-tert-butyl 3-(7-chloro-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (150 mg, 281 μmol, 1.0 eq) and K₃PO₄ (1.5 M, 0.6 mL, 3.2 eq, aqueous) in THF (3.0 mL) was degassed and purged with N₂ for 3 times. [2-(2-aminophenyl)phenyl]-methylsulfonyloxy-palladium; dicyclohexyl-[3,6-dimethoxy-2-(2,4,6-triisopropylphenyl)phenyl]phosphane (26 mg, 28.7 μmol, 0.1 eq) was added and the mixture was stirred at 60° C. for 13 hours under N₂ atmosphere. The reaction mixture was diluted with H₂O (1.0 mL) and brine (1.0 mL). The mixture was extracted with ethyl acetate (1.0 mL×6). The combined organic layers were dried over anhydrous Na₂SO₄, filtered and concentrated under reduced pressure to give a residue. The residue was purified by reversed phase flash chromatography [water (FA, 0.1%)/acetonitrile=1/1] to give product as light yellow foam (170 mg, 76% yield). LCMS [ESI, M+H]: 775.4.

Step I: 4-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)-5,6-dimethylbenzo[d]thiazol-2-amine. To a solution of (1R,5S)-tert-butyl 3-(7-(2-((tert-butoxycarbonyl)amino)-5,6-dimethylbenzo[d]thiazol-4-yl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (80 mg, 103 μmol, 1.0 eq) in DCM (1.2 mL) was added TFA (1.85 g, 16.2 mmol) at 0° C. The mixture was stirred at 0~15° C. for 1 hour. The reaction mixture was concentrated under reduced pressure to give a residue. The residue was dissolved in ethyl acetate (20.0 mL) and H₂O (5.0 mL). The pH of the mixture was adjusted to 8~9 with NaHCO₃ solid. The mixture was extracted with ethyl acetate (15.0 mL×4) and the combined organic layers were dried over anhydrous Na₂SO₄. The mixture was filtered and concentrated under reduced pressure to give a residue. The residue was purified by prep-HPLC (column: Phenomenex luna C18 150*25 mm*10 um; mobile phase: [water (0.225% FA)-ACN]; B %: 7%-37%, 10 min) and lyophilized to give product as an off-white solid (41.50 mg, 65% yield, 0.7FA). ¹H NMR (400 MHz, methanol-d4) δ=9.14 (s, 1H), 7.56 (s, 1H), 4.80-4.75 (m, 2H), 4.68 (s, 2H), 4.13 (br s, 2H), 3.99 (d, J=13.6 Hz, 1H), 3.89 (d, J=14.0 Hz, 1H), 3.74-3.69 (m, 2H), 3.31-3.24 (m, 2H), 2.39 (s, 3H), 2.24-2.19 (m, 2H), 2.14-2.08 (m, 13H). LCMS [ESI, M+1]: 575.3.

Example 457

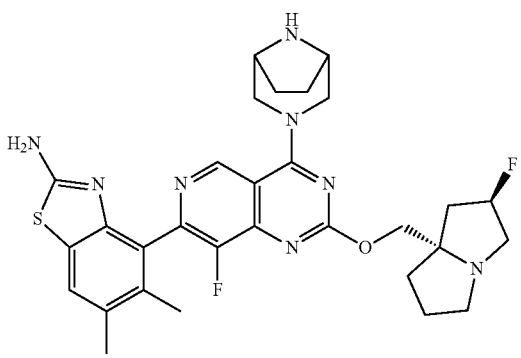 [SMILES: Cc1cc2sc(N)nc2c(-c2ncc3c(N4CC5CCC(C4)N5)nc(OC[C@@]45CCCN4C[C@H](F)C5)nc3c2F)c1C]

4-(4-((1R,5S)-3,8-diazabicyclo[3.2.1]octan-3-yl)-8-fluoro-2-(((2R,7aS)-2-fluorohexahydro-1H-pyrrolizin-7a-yl)methoxy)pyrido[4,3-d]pyrimidin-7-yl)-5,6-dimethylbenzo[d]thiazol-2-amine

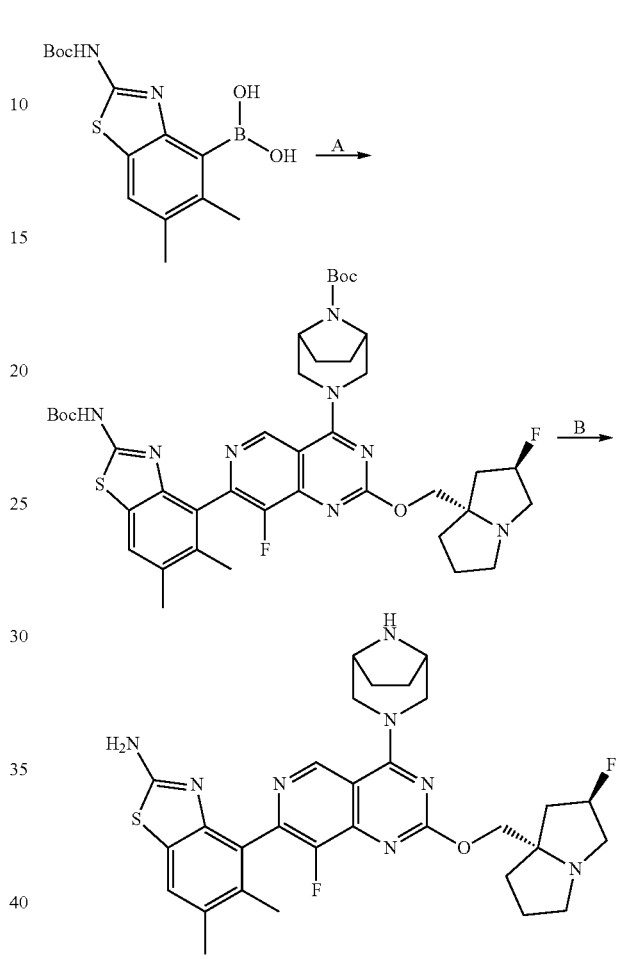

Step A: (1R,5S)-tert-butyl 3-(7-(2-((tert-butoxycarbonyl)amino)-5,6-dimethylbenzo[d]thiazol-4-yl)-8-fluoro-2-(((2R,7aS)-2-fluorohexahydro-1H-pyrrolizin-7a-yl)methoxy)pyrido[4,3-d]pyrimidin-4-yl)-3,8-diazabicyclo[3.2.1]octane-8-carboxylate. To a mixture of (1R,5S)-tert-butyl 3-(7-chloro-8-fluoro-2-(((2R,7aS)-2-fluorohexahydro-1H-pyrrolizin-7a-yl)methoxy)pyrido[4,3-d]pyrimidin-4-yl)-3,8-diazabicyclo[3.2.1]octane-8-carboxylate (150 mg, 272 μmol, 1.0 eq) and (2-((tert-butoxycarbonyl)amino)-5,6-dimethylbenzo[d]thiazol-4-yl)boronic acid (150 mg, 466 μmol, 1.71 eq) in THF (3.0 mL) was added K3PO4 (1.5 M, 544 uL, 3.0 eq). The reaction mixture was degassed with N2 for 15 minutes followed by the addition of BrettPhos Pd G3 (24.7 mg, 27.2 μmol, 0.1 eq) under N₂. The mixture was heated to 60° C. and stirred for 12 hours. Water (5.0 mL) was added and the reaction mixture was extracted with ethyl acetate (5.0 mL×4). The combined organic phase was washed with brine (5.0 mL) and dried with anhydrous Na2SO4. The reaction mixture was filtered and concentrated in vacuum to give a residue. The residue was purified by reversed-phase flash chromatography (0.1% FA condition) to afford the product as yellow solid (120 mg, 54% yield). LCMS [ESI, M+1]: 793.4.

Step B: 4-(4-((1R,5S)-3,8-diazabicyclo[3.2.1]octan-3-yl)-8-fluoro-2-(((2R,7aS)-2-fluorohexahydro-1H-pyrrolizin-7a-yl)methoxy)pyrido[4,3-d]pyrimidin-7-yl)-5,6-dimethylbenzo[d]thiazol-2-amine. To a mixture of (1R,5S)-tert-butyl 3-(7-(2-((tert-butoxycarbonyl)amino)-5,6-dimethylbenzo[d]thiazol-4-yl)-8-fluoro-2-(((2R,7aS)-2-fluorohexahydro-1H-pyrrolizin-7a-yl)methoxy)pyrido[4,3-d]pyrimidin-4-yl)-3,8-diazabicyclo[3.2.1]octane-8-carboxylate (110 mg, 139 μmol, 1.0 eq) in DCM (0.1 mL) was added TFA (1.69 g, 14.9 mmol, 1.10 mL, 107 eq) at 0° C. under $N_2$. The mixture was stirred at 20° C. for 1 hour. Then the pH of the mixture was adjusted to 8 with the saturated $Na_2CO_3$ aqueous and the mixture was extracted with ethyl acetate (3.0 mL×5). The combined organic phase was washed with brine (5.0 mL) and dried over anhydrous $Na_2SO_4$. The mixture was filtered and concentrated to give a residue. The residue was purified by prep-HPLC (column: Phenomenex luna C18 150*25 mm*10 um; mobile phase: [water (0.225% FA)-ACN]; B %: 8%-38%, 10 min) to afford the product as a white solid (28.5 mg, 34% yield). $^1$H NMR (400 MHz, methanol-d4) δ 9.12 (s, 1H), 7.56 (s, 1H), 5.50 (d, J=52.4 Hz, 1H), 4.78-4.72 (m, 1H), 4.65-4.55 (m, 1H), 4.10 (s, 2H), 4.01-3.92 (m, 1H), 3.90-3.68 (m, 4H), 3.40-3.32 (m, 2H), 2.68-2.47 (m, 2H), 2.41-2.32 (m, 4H), 2.30-2.20 (m, 2H), 2.17-1.92 (m, 8H); LCMS [ESI, M+1]: 593.3.

Example 458

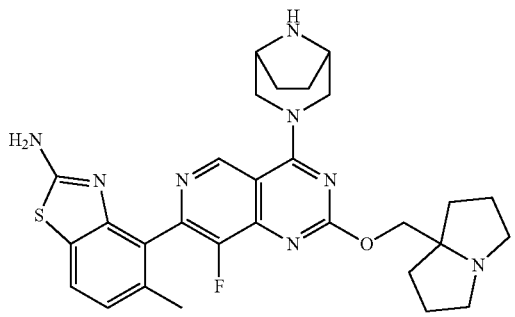 [SMILES: Cc1ccc2sc(N)nc2c1-c1ncc2c(N3CC4CCC(C3)N4)nc(OCC34CCCN3CCC4)nc2c1F]

4-(4-((1R,5S)-3,8-diazabicyclo[3.2.1]octan-3-yl)-8-fluoro-2-((hexahydro-1H-pyrrolizin-7a-yl)methoxy)pyrido[4,3-d]pyrimidin-7-yl)-5-methylbenzo[d]thiazol-2-amine

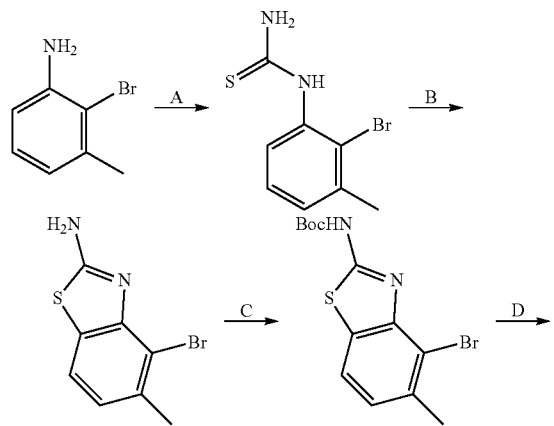

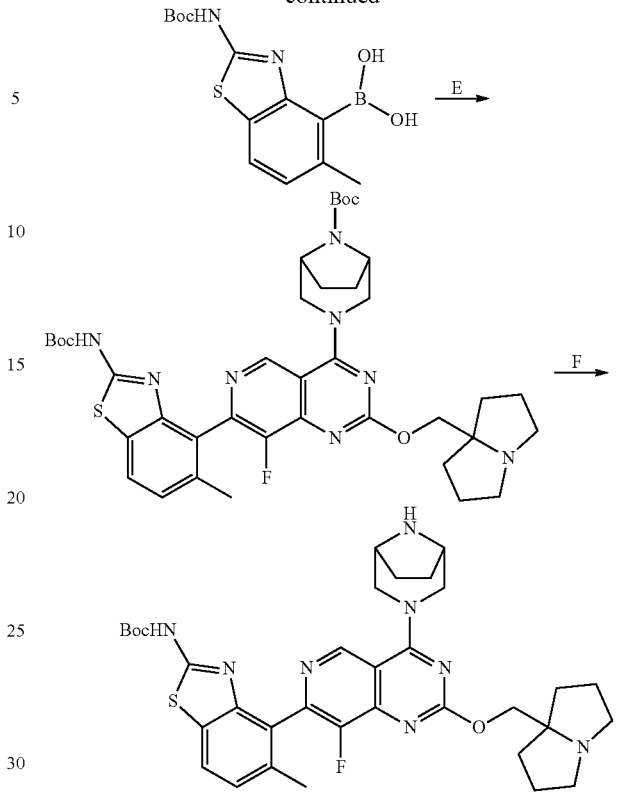

Step A. 1-(2-bromo-3-methylphenyl)thiourea. To a solution of $NH_4SCN$ (532 mg, 6.99 mmol, 532 uL, 1.30 eq) in acetone (5.0 mL) was added benzoyl chloride (907 mg, 6.45 mmol, 749 uL, 1.20 eq) dropwise. The mixture was stirred at 60° C. for 0.5 hour. The mixture was cooled to 25° C. and a solution of 2-bromo-3-methylaniline (1.0 g, 5.37 mmol, 1.0 eq) in acetone (5.0 mL) was dropwise added. The reaction mixture was stirred at 60° C. for 1 hour. The mixture was added to water (20.0 mL) and then filtered. The precipitate was washed with water (3×10.0 mL), then 50% MeOH (10.0 mL) and dried to give a residue. The residue was added in to 10% NaOH aqueous solution (20.0 mL) and the reaction was stirred at 80° C. for 1 hour. The mixture was cooled to 25° C. and the pH was adjusted to ~8 with HCl (12 M). The mixture was filtered. The precipitate was washed with water (3×10.0 mL) and dried to afford the title compound as yellow solid (930 mg, 68% yield). LCMS [ESI, M+1]:247.0.

Step B. 4-bromo-5-methylbenzo[d]thiazol-2-amine. To a solution of 1-(2-bromo-3-methylphenyl)thiourea (500 mg, 2.04 mmol, 1.0 eq) in CHCl3 (5.0 mL) was dropwise added a solution of bromine (326 mg, 2.04 mmol, 105 uL, 1.0 eq) in CHCl3 (2.0 mL) at 0° C. The reaction mixture was stirred at 65° C. for 2 hours. The reaction mixture was concentrated under vacuum to give a residue. The residue was dissolved in ethyl acetate (15 mL) and washed with saturated NaHCO3 aqueous solution (2×15.0 mL), saturated Na2S2O3 aqueous solution (2×15.0 mL) and brine (2×15.0 mL). The organic layer was concentrated to afford title compound as yellow solid (440 mg, 86% yield). 1H NMR (400 MHz, CDCl3) δ=7.40 (d, J=7.6 Hz, 1H), 7.01 (d, J=8.0 Hz, 1H), 5.97 (br s, 2H), 2.49 (s, 3H); LCMS [ESI, M+1]:244.9.

Step C. tert-butyl (4-bromo-5-methylbenzo[d]thiazol-2-yl)carbamate. To a solution of 4-bromo-5-methylbenzo[d]

thiazol-2-amine (3.70 g, 15.2 mmol, 1.0 eq), DIEA (3.93 g, 30.4 mmol, 5.30 mL, 2.0 eq) and DMAP (37.2 mg, 304 μmol, 0.02 eq) in THF (40.0 mL) was added (Boc)₂O (3.99 g, 18.3 mmol, 4.20 mL, 1.20 eq). The reaction mixture was stirred at 20° C. for 1 hour. The reaction mixture was diluted with water (50.0 mL) and extracted with EtOAc (2×50.0 mL). The combined organic layer was dried over Na₂SO₄, then filtered and concentrated to give a residue. The residue was purified by reversed phase flash chromatography (C18, 0.1% formic acid condition) to afford title compound as yellow solid (2.70 g, 51% yield). LCMS [ESI, M+1]:288.9.

Step D. (2-((tert-butoxycarbonyl)amino)-5-methylbenzo [d]thiazol-4-yl)boronic acid. To a solution of tert-butyl (4-bromo-5-methylbenzo[d]thiazol-2-yl)carbamate (1.0 g, 2.91 mmol, 1.0 eq), 4,4,5,5-tetramethyl-2-(4,4,5,5-tetramethyl-1,3,2-dioxaborolan-2-yl)-1,3,2-dioxaborolane (1.48 g, 5.83 mmol, 2.0 eq) and KOAc (858 mg, 8.74 mmol, 3.0 eq) in dioxane (10 mL) was added [2-(2-aminophenyl)phenyl]-chloro-palladium; tricyclohexylphosphane (172 mg, 291 μmol, 0.10 eq). The mixture was degassed and stirred at 80° C. for 24 hours. The reaction mixture was diluted with water (10.0 mL) and extracted with EtOAc (2×10.0 mL). The combined organic layer was dried over Na₂SO₄, then filtered and concentrated to give a residue. The residue was purified by reversed phase flash chromatography (C18, 0.1% formic acid condition) to afford title compound as yellow solid (440 mg, 49% yield). LCMS [ESI, M−55, M−100]: 253.0, 209.1.

Step E. (1R,5S)-tert-butyl 3-(7-(2-((tert-butoxycarbonyl) amino)-5-methylbenzo[d]thiazol-4-yl)-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate. To a solution of (1R,5S)-tert-butyl 3-(7-chloro-8-fluoro-2-((hexahydro-1H-pyrrolizin-7a-yl)methoxy)pyrido[4,3-d]pyrimidin-4-yl)-3,8-diazabicyclo[3.2.1]octane-8-carboxylate (320 mg, 600 μmol, 1.0 eq) and K₃PO₄ (1.5 M, 1.20 mL, 3.0 eq) in THF (4.0 mL) were added BrettPhos Pd G3 (54.4 mg, 60.0 μmol, 0.10 eq) and (2-((tert-butoxycarbonyl)amino)-5-methylbenzo[d]thiazol-4-yl)boronic acid (370 mg, 1.20 mmol, 2.0 eq). The mixture was degassed and stirred at 60° C. for 12 hours. The reaction mixture was diluted with water (10.0 mL) and extracted with EtOAc (2×10.0 mL). The combined organic layer was dried over Na₂SO₄, then filtered and concentrated to give a residue. The residue was purified by reversed phase flash chromatography (C18, 0.1% formic acid condition) to afford title compound as yellow solid (110 mg, 24% yield). LCMS [ESI, M+1]:761.4

Step F. 4-(4-((1R,5S)-3,8-diazabicyclo[3.2.1]octan-3-yl)-8-fluoro-2-((hexahydro-1H-pyrrolizin-7a-yl)methoxy) pyrido[4,3-d]pyrimidin-7-yl)-5-methylbenzo[d]thiazol-2-amine: To a solution of (1R,5S)-tert-butyl 3-(7-(2-((tert-butoxycarbonyl)amino)-5-methylbenzo[d]thiazol-4-yl)-8-fluoro-2-((hexahydro-1H-pyrrolizin-7a-yl)methoxy)pyrido [4,3-d]pyrimidin-4-yl)-3,8-diazabicyclo[3.2.1]octane-8-carboxylate (81.5 mg, 107 μmol, 1.0 eq) in DCM (1.50 mL) was added TFA (2.31 g, 20.3 mmol, 1.50 mL, 189 eq). The reaction mixture was stirred at 20° C. for 0.5 hour. Then the mixture was diluted with water (10.0 mL) and extracted with EtOAc (2×10.0 mL). The combined organic layer was dried over Na₂SO₄, then filtered and concentrated to give a residue. The residue was purified by prep-HPLC (column: Phenomenex luna C18 150*25 mm*10 um; mobile phase: [water (0.225% FA)-ACN]; B %: 7%-37%, 10 min) to afford title compound as yellow solid (26.3 mg, 42% yield). ¹H NMR (400 MHz, METHANOL-d4) δ=9.14 (s, 1H), 7.64 (d, J=8.0 Hz, 1H), 7.12 (d, J=8.0 Hz, 1H), 4.77 (br d, J=13.6 Hz, 2H), 4.68 (s, 2H), 4.13 (br s, 2H), 3.99 (br d, J=13.6 Hz, 1H), 3.89 (br d, J=13.6 Hz, 1H), 3.76-3.66 (m, 2H), 3.34-3.32 (m, 1H), 3.30-3.25 (m, 1H), 2.39-2.29 (m, 2H), 2.28-2.16 (m, 7H), 2.15-2.04 (m, 5H), 2.04-1.95 (m, 1H); LCMS [ESI, M+1]:561.2.

Example A

KRas G12D Surface Plasmon Resonance (SPR) Binding Assay

This Example illustrates that exemplary compounds of the present invention bind to KRas G12D as measured by surface plasmon resonance (SPR).

Briefly, 1 L of 1.05×HBS-Mg buffer (262.5 mM Bioultra Hepes, pH 7.5, 157.5 mM NaCl, 105 mM MgCl₂, 0.525 mM TCEP, 0.0305% Brij-35) was prepared and filter sterilized using a 0.22 μm bottle top filter. Approximately 50 mL of 1.05×HBS-Mg buffer was removed and saved for future dilutions. A 50 mL aliquot of DMSO (Sigma Aldrich DMSO Lot. #SHBK2079) was added and continued to stir for 10 minutes, creating the final 1.0×HBS-Mg buffer (250 mM Bioultra Hepes pH 7.5, 150 mM NaCl, 100 mM MgCl₂, 0.5 mM TCEP, 0.03% Brij-35).

Biacore T200 instrument was primed using 1.0×HBS-Mg buffer before docking a GE Streptavidin (SA) chip and then primed two additional times prior to beginning the immobilization step. All immobilized protein mixtures were created using 3-5 mg/mL Biotinylated Avidin-tagged KRAS protein using the following immobilization settings: SA chip type, 1 flow cells per cycle, 720 second contact time, and 5 ul/min flow rate. Normalization of the detector was also performed during the immobilization step using the GE BiaNormalize solution.

All compounds were diluted to 10 mM in 100% DMSO prior to being diluted 20× in 1.05× buffer. Another 10× dilution was created using 1.0× buffer prior to performing a series of 3× dilutions to create a compound concentration curve using the following assay settings: 20 C analysis temperature, General Settings=10 Hz data collection rate and multi-detection; Assay Steps=all set to LMW kinetics; Cycle Types=LMW kinetics (60 s contact time, 120 s dissociation time, 100 ul/min flow rate, extra wash after injection with 50% DMSO, flow path 1,2,3,4); Flow path detection=2-1, 4-3). Data evaluation was performed using the Biacore T200 Evaluation software and data fit to 1:1 binding model.

The results for exemplary compounds of Formula (I) are shown in Table 1. ND=not determined.

TABLE 1

Determination of KRas G12D $K_D$ for Exemplary Compounds of Formula (I)

| Example No. | $K_D$ (nM) | Example No. | $K_D$ (nM) |
|---|---|---|---|
| 1 | 97.7 | 86 | 527559.5 |
| 2 | 2.4 | 87 | 195.8 |
| 3 | 8.3 | 88 | 15593.2 |
| 4 | 155.7 | 89 | 4308.7 |
| 5 | 294.8 | 90 | 7805.4 |
| 6 | 442.2 | 91 | 25.9 |
| 7 | 463.5 | 92 | 2303.5 |
| 8 | 2143.7 | 94 | 7462.4 |
| 9 | 258.9 | 95 | 1129.0 |
| 10 | 33.8 | 96 | 709.6 |
| 11 | 4.9 | 97 | 5916.9 |
| 12 | 11.0 | 99 | 896.6 |
| 13 | 510.7 | 100 | 1089.4 |
| 14 | 5.1 | 101 | 11958.2 |
| 15 | 208.5 | 102 | 259.1 |

TABLE 1-continued

Determination of KRas G12D $K_D$ for Exemplary Compounds of Formula (I)

| Example No. | $K_D$ (nM) | Example No. | $K_D$ (nM) |
|---|---|---|---|
| 16 | 31.3 | 103 | 271.2 |
| 17 | 2209.6 | 104 | 362.0 |
| 18 | 3.1 | 105 | 2264.8 |
| 19 | 664.8 | 106 | 53.5 |
| 20 | 967.0 | 107 | 1437.0 |
| 21 | 447.5 | 108 | 63516.8 |
| 22 | 19.6 | 109 | >500000 |
| 23 | 807.2 | 110 | 42.3 |
| 24 | 5.0 | 111 | 275.8 |
| 25 | 269.7 | 112 | 983.3 |
| 26 | 27.9 | 113 | 2503.9 |
| 27 | 25.9 | 114 | 383.7 |
| 28 | 58.7 | 115 | 333377.0 |
| 29 | 169.6 | 116 | 3628.8 |
| 30 | 179.5 | 117 | 1004.8 |
| 33 | 71.7 | 118 | 1061.5 |
| 34 | 119.3 | 119 | 511.4 |
| 35 | 1381.8 | 120 | 42.1 |
| 37 | 494.5 | 121 | 197.0 |
| 38 | 750.3 | 122 | 3417.4 |
| 39 | 67770.0 | 123 | 785.7 |
| 40 | 1.7 | 124 | 22.7 |
| 41 | 180.8 | 126 | 16.1 |
| 42 | 5.6 | 127 | 864.1 |
| 43 | 188.0 | 131 | 1553.0 |
| 44 | 31.7 | 132 | 64.7 |
| 45 | 5.1 | 133 | 112.6 |
| 46 | 797.8 | 134 | 6.9 |
| 47 | 509.9 | 139 | 25.4 |
| 48 | 930.8 | 140 | 5591.7 |
| 49 | 0.4 | 142 | 13834.0 |
| 50 | 2.1 | 143 | 14933.6 |
| 51 | 611.1 | 147 | 18778.9 |
| 52 | 507.4 | 151 | 448.0 |
| 53 | 4369.4 | 153 | 70.5 |
| 54 | 117.5 | 156 | 500006.0 |
| 55 | 22441.7 | 157 | 22.9 |
| 56 | 5168.9 | 158 | 329.9 |
| 57 | >1000000 | 160 | 0.3 |
| 58 | 4733.6 | 161 | 403.2 |
| 59 | 1118.3 | 162 | 554.6 |
| 60 | >1000000 | 173 | 116.7 |
| 61 | 115.5 | 174 | 186.1 |
| 67 | 1151.1 | 179 | 0.1 |
| 68 | 292.8 | 185 | 0.0 |
| 69 | 521.6 | 190 | 76.1 |
| 70 | 416.7 | 214 | 283.6 |
| 71 | 137.6 | 215 | 70.4 |
| 72 | 507.2 | 216 | 1.7 |
| 73 | 666744.3 | 217 | 2977.0 |
| 74 | 140.6 | 219 | 8.1 |
| 75 | 303.7 | 316 | 157480.3 |
| 76 | 196.9 | 317 | 91269.8 |
| 77 | 3065.8 | 318 | 367549.7 |
| 78 | 367.5 | 319 | 255881.2 |
| 79 | >1000000 | 320 | 71584.2 |
| 80 | >500000 | 339 | 21.6 |
| 81 | 320.6 | 395 | 2.6 |
| 82 | 214.8 | 396 | 34.8 |
| 84 | 14.4 | 397 | 183.2 |
| 85 | 147.8 | | |

Example B

Kras G12D Binding Assay

This Example illustrates that exemplary compounds of the present invention bind to KRas G12D and are capable of displacing a labeled tracer ligand occupying the KRas G12D binding site.

The ability of a compound to bind to KRAS G12D was measured using a TR-FRET displacement assay. Biotinylated GDP-loaded recombinant human KRAS G12D (corresponding to amino acids 1:169, produced at Array BioPharma) was incubated with a custom-made Cy5 labelled tracer, europium labelled streptavidin and compound (2% DMSO final) in buffer (50 mM HEPES [pH 7.5], 5 mM $MgCl_2$, 0.005% Tween-20 & 1 mM DTT). After a 60 minute incubation at 22° C., the reaction was measured using a PerkinElmer EnVision multimode plate reader via TR-FRET dual wavelength detection, and the percent of control (POC) calculated using a ratiometric emission factor. 100 POC is determined using no test compound and 0 POC is determined using a concentration of control compound that completely inhibits binding of the tracer to KRAS. The POC values were fit to a 4-parameter logistic curve and the $IC_{50}$ value was determined as the concentration where the curve crosses 50 POC.

The results for exemplary compounds of Formula (I) are shown in Table 2. ND stands for "not determined."

TABLE 2

Binding to KRas G12D by Exemplary Compounds of Formula (I)

| Example No. | $IC_{50}$ (nM) | Example No. | $IC_{50}$ (nM) |
|---|---|---|---|
| 1 | 124.7 | 235 | 1.2 |
| 2 | 2.7 | 236 | 25.0 |
| 3 | 9.5 | 237 | 500.3 |
| 4 | 496.2 | 238 | 16.1 |
| 5 | 722.9 | 239 | 2.0 |
| 6 | 434.1 | 240 | 314.8 |
| 7 | 1867.3 | 241 | 79.2 |
| 8 | 1522.0 | 242 | 82.2 |
| 9 | 820.7 | 243 | 0.4 |
| 14 | 73.9 | 244 | 4.2 |
| 15 | 260.3 | 245 | 0.5 |
| 16 | 54.1 | 246 | 0.6 |
| 17 | 666.2 | 247 | 12.6 |
| 18 | 76.8 | 248 | 3.2 |
| 19 | 122.0 | 249 | 3.5 |
| 20 | 691.8 | 250 | 28.2 |
| 21 | 262.9 | 251 | 0.2 |
| 22 | 50.3 | 252 | 0.4 |
| 24 | 7.9 | 253 | 0.8 |
| 25 | 338.4 | 254 | 6.1 |
| 26 | 42.1 | 255 | 8.7 |
| 29 | 160.4 | 256 | 13.2 |
| 30 | 417.6 | 257 | 5.1 |
| 31 | 1.6 | 258 | 6.5 |
| 32 | 2145.0 | 259 | 0.8 |
| 33 | 21.1 | 260 | 107.1 |
| 34 | 135.4 | 261 | 8304.2 |
| 35 | 475.0 | 262 | 2255.6 |
| 36 | 0.4 | 263 | 1.5 |
| 37 | 404.8 | 264 | 4698.9 |
| 38 | 174.2 | 265 | 794.0 |
| 39 | >10000 | 266 | 278.0 |
| 40 | 4.0 | 267 | 3261.6 |
| 41 | 76.7 | 268 | 1546.3 |
| 42 | 3.1 | 269 | 4037.9 |
| 43 | 72.2 | 270 | 4492.4 |
| 44 | 33.7 | 271 | 1621.9 |
| 45 | 5.5 | 272 | 1178.7 |
| 46 | 720.8 | 273 | 1340.8 |
| 47 | 264.6 | 274 | 35.9 |
| 48 | 433.9 | 275 | 53.8 |
| 49 | 5.9 | 276 | 16.2 |
| 50 | 2.5 | 277 | 35.2 |
| 51 | 291.7 | 278 | 0.7 |
| 52 | 318.3 | 279 | 1.6 |
| 53 | 1881.4 | 280 | 99.8 |
| 54 | 68.7 | 281 | 0.9 |
| 55 | 6131.3 | 282 | 0.7 |
| 56 | 5916.7 | 283 | 0.7 |
| 57 | 7285.9 | 284 | 0.1 |
| 58 | 2326.7 | 285 | 279.0 |

TABLE 2-continued

Binding to KRas G12D by Exemplary Compounds of Formula (I)

| Example No. | IC$_{50}$ (nM) | Example No. | IC$_{50}$ (nM) |
| --- | --- | --- | --- |
| 59 | 946.3 | 286 | 17.2 |
| 60 | 1660.7 | 287 | 90.7 |
| 61 | 4081.0 | 288 | 589.5 |
| 62 | 8407.4 | 289 | 218.4 |
| 63 | 0.4 | 290 | 2.1 |
| 64 | 3.3 | 291 | 1.6 |
| 65 | 3.2 | 292 | 13.1 |
| 66 | 544.4 | 293 | 692.3 |
| 67 | 1245.6 | 294 | 620.4 |
| 68 | 256.6 | 295 | 191.5 |
| 69 | 529.9 | 296 | 111.5 |
| 70 | 356.2 | 297 | 88.9 |
| 71 | 125.7 | 298 | 8.3 |
| 72 | 512.9 | 299 | 131.7 |
| 73 | 572.7 | 300 | 767.8 |
| 74 | 188.2 | 301 | 35.1 |
| 75 | 240.4 | 302 | 43.6 |
| 76 | 131.2 | 303 | 357.3 |
| 77 | 3137.6 | 304 | 29.2 |
| 78 | 358.3 | 305 | 366.8 |
| 79 | 336.5 | 306 | 260.4 |
| 80 | 646.9 | 307 | 3164.3 |
| 81 | 152.9 | 308 | 117.4 |
| 82 | 226.8 | 309 | 204.7 |
| 83 | 8694.9 | 310 | 558.7 |
| 84 | 31.7 | 311 | 135.3 |
| 85 | 453.7 | 312 | 9.0 |
| 86 | 7919.9 | 313 | 231.3 |
| 87 | 535.6 | 314 | 0.6 |
| 88 | 7021.4 | 315 | 2537.4 |
| 89 | 679.3 | 316 | >10000 |
| 90 | 4494.9 | 317 | >10000 |
| 91 | 32.7 | 318 | >10000 |
| 92 | 1348.4 | 319 | >10000 |
| 93 | 104.6 | 320 | >10000 |
| 94 | 3652.5 | 321 | 612.8 |
| 95 | 561.0 | 322 | 4.9 |
| 96 | 2221.0 | 323 | 1689.3 |
| 97 | 934.1 | 324 | 10.2 |
| 98 | 1.0 | 325 | 140.9 |
| 99 | 623.8 | 326 | 1.9 |
| 100 | 1949.7 | 327 | 1.9 |
| 101 | 8081.6 | 328 | 9.4 |
| 102 | 95.8 | 329 | 202.5 |
| 103 | 371.0 | 330 | 2.5 |
| 104 | 1675.8 | 331 | 114.4 |
| 105 | 867.1 | 332 | 163.9 |
| 106 | 155.9 | 333 | 450.5 |
| 107 | 2118.9 | 334 | 10.0 |
| 108 | 4841.5 | 335 | 25.8 |
| 109 | 0.5 | 336 | 3.1 |
| 110 | 57.5 | 337 | 2.2 |
| 111 | 281.0 | 338 | 33.1 |
| 112 | 718.4 | 339 | 21.0 |
| 113 | 2866.1 | 340 | 0.4 |
| 114 | 482.1 | 341 | 0.7 |
| 115 | 174.3 | 342 | 3.4 |
| 116 | 1437.7 | 343 | 10.4 |
| 117 | 731.5 | 344 | 10.9 |
| 118 | 476.6 | 345 | 10.6 |
| 119 | 684.3 | 346 | 10.5 |
| 120 | 28.8 | 347 | 2.1 |
| 121 | 204.2 | 348 | 15.5 |
| 122 | 3265.3 | 349 | 560.7 |
| 123 | 754.4 | 350 | 3822.1 |
| 124 | 8.6 | 351 | 94.8 |
| 125 | 667.5 | 352 | 844.8 |
| 126 | 9.9 | 353 | 333.4 |
| 127 | 250.9 | 354 | 368.1 |
| 128 | 500.6 | 355 | 869.9 |
| 129 | 4092.5 | 356 | 87.2 |
| 130 | 1647.0 | 357 | 438.0 |
| 131 | 423.9 | 358 | 1980.6 |
| 132 | 60.5 | 359 | 1637.1 |
| 133 | 48.8 | 360 | 50.8 |
| 134 | 3.7 | 361 | 2700.3 |
| 135 | 2.1 | 362 | 105.8 |
| 136 | 5150.6 | 363 | 3932.5 |
| 137 | 2633.4 | 364 | 2.3 |
| 138 | 8067.8 | 365 | 34.9 |
| 139 | 113.3 | 366 | 0.5 |
| 140 | 5161.4 | 367 | 0.7 |
| 141 | 891.1 | 368 | 207.6 |
| 142 | 8846.4 | 369 | 221.4 |
| 143 | 4563.2 | 370 | 86.1 |
| 144 | 1702.3 | 371 | 394.2 |
| 145 | 5002.5 | 372 | 0.7 |
| 146 | 2285.7 | 373 | 1.6 |
| 147 | 5876.2 | 374 | 347.9 |
| 148 | 5180.0 | 375 | 1.7 |
| 149 | 869.5 | 376 | 2.6 |
| 150 | 1981.1 | 377 | 416.9 |
| 151 | 387.5 | 378 | 6250.0 |
| 152 | 2647.1 | 379 | 248.7 |
| 153 | 50.8 | 380 | 65.7 |
| 154 | 6533.8 | 381 | 0.7 |
| 155 | 3417.0 | 382 | 21.1 |
| 156 | 9.1 | 383 | 585.9 |
| 157 | 26.6 | 384 | 2.4 |
| 158 | 73.7 | 385 | 3083.3 |
| 159 | 331.0 | 386 | 2.0 |
| 160 | 120.3 | 387 | 532.8 |
| 161 | 273.2 | 388 | 0.6 |
| 162 | 677.3 | 389 | 1.4 |
| 163 | 5552.5 | 390 | 36.8 |
| 164 | 4046.0 | 391 | 661.7 |
| 165 | 97.8 | 392 | 208.2 |
| 166 | 1286.1 | 393 | 76.3 |
| 167 | 226.2 | 394 | 2500.0 |
| 168 | 583.0 | 395 | 6.9 |
| 169 | 656.9 | 396 | 206.8 |
| 170 | 841.7 | 397 | 886.9 |
| 171 | 757.4 | 398 | 593.2 |
| 172 | 689.1 | 399 | 2.7 |
| 173 | 99.2 | 400 | 4.2 |
| 174 | 63.9 | 401 | 2.8 |
| 175 | 63.8 | 402 | 8017.6 |
| 176 | 235.1 | 403 | 1.9 |
| 177 | 187.1 | 404 | 60.8 |
| 178 | 105.0 | 405 | 2.2 |
| 179 | 1.1 | 406 | 0.9 |
| 180 | 76.1 | 407 | 560.0 |
| 181 | 572.5 | 408 | 3.1 |
| 182 | 269.1 | 409 | 2231.4 |
| 183 | 393.3 | 410 | 1.0 |
| 184 | 1990.6 | 411 | 17.0 |
| 185 | 0.3 | 412 | 17.7 |
| 186 | 29.2 | 413 | 9.2 |
| 187 | 1.7 | 414 | 873.2 |
| 188 | 1919.7 | 415 | 2578.3 |
| 189 | 0.5 | 416 | 1946.5 |
| 190 | 64.1 | 417 | 594.7 |
| 191 | 69.1 | 418 | 7.5 |
| 192 | 224.9 | 419 | 50.9 |
| 193 | 12.5 | 420 | 20.0 |
| 194 | 150.8 | 421 | 7746.7 |
| 195 | 20.7 | 422 | 11.4 |
| 196 | 467.0 | 423 | 238.0 |
| 197 | 99.9 | 424 | 5.0 |
| 198 | 20.3 | 425 | 90.2 |
| 199 | 2.0 | 426 | 0.9 |
| 200 | 229.7 | 427 | 35.3 |
| 201 | 70.2 | 428 | 92.1 |
| 202 | 94.0 | 429 | 18.5 |
| 203 | 28.1 | 430 | 1.0 |
| 204 | 4.4 | 431 | 1.4 |
| 205 | 1.2 | 432 | 1.9 |
| 206 | 5.1 | 433 | 0.9 |
| 207 | 4906.8 | 434 | 0.7 |
| 208 | 1836.7 | 435 | 28.2 |

TABLE 2-continued

Binding to KRas G12D by Exemplary Compounds of Formula (I)

| Example No. | IC$_{50}$ (nM) | Example No. | IC$_{50}$ (nM) |
|---|---|---|---|
| 209 | 2746.7 | 436 | 48.3 |
| 210 | 5464.7 | 437 | 233.7 |
| 211 | 211.5 | 438 | 20.1 |
| 212 | 1218.4 | 439 | 0.4 |
| 213 | 7529.0 | 440 | 0.8 |
| 216 | 0.9 | 441 | 0.5 |
| 218 | 1600 | 442 | 25.0 |
| 219 | 8.1 | 443 | 3.2 |
| 220 | 8.7 | 444 | 5.5 |
| 221 | 15.7 | 445 | 2.7 |
| 222 | 1126.7 | 446 | 357.0 |
| 223 | 7.1 | 447 | 297.0 |
| 224 | 27.0 | 448 | 130.0 |
| 225 | 9.2 | 449 | 71.0 |
| 226 | 25.9 | 450 | 37.0 |
| 227 | 6.4 | 451 | 1.0 |
| 228 | 87.7 | 452 | 1.0 |
| 229 | 121.0 | 453 | 27 |
| 230 | 1433.1 | 454 | 295 |
| 231 | 19.8 | 455 | 17 |
| 232 | 0.6 | 456 | 966 |
| 233 | 387.2 | 457 | 475 |
| 234 | 5.9 | 458 | 143 |

Example C

Inhibition of KRas G12D-Mediated Phosphorylation of ERK by Exemplary Compounds of Formula (I)

This Example illustrates that exemplary compounds of the present invention inhibit the phosphorylation of ERK downstream of KRAS G12D.

AGS cells (ATCC CRL-1739) expressing G12D were grown in DMEM medium supplemented with 10% fetal bovine serum, 10 mM HEPES, and Penicillin/Streptomycin. Cells were plated in tissue culture treated 96 well plates at a density of 40,000 cells/well and allowed to attach for 12-14 hours. Diluted compounds were then added in a final concentration of 0.5% DMSO. After 3 hours, the medium was removed, 150 μL of 4.0% formaldehyde was added and the plates incubated at room temperature for 20 minutes. The plates were washed with PBS, and permeabilized with 150 μL of ice cold 100% methanol for 10 minutes. Non-specific antibody binding to the plates was blocked using 100 μL Licor blocking buffer (Li-Cor Biotechnology, Lincoln NE) for 1 hour at room temperature.

The amount of phospho-ERK was determined using an antibody specific for the phosphorylated form of ERK and compared to the amount of GAPDH. Primary antibodies used for the detection were added as follows: Phospho-ERK (Cell Signaling cs-9101) diluted 1:500 and GAPDH (Millipore MAB374) diluted 1:5000 in Licor block+0.05% Tween 20. The plates were incubated for 2 hours at room temperature. The plates were washed with PBS+0.05% Tween 20.

Secondary antibodies used to visualize primary antibodies were added as follows: Anti-rabbit-680 diluted 1:1000 and Anti-mouse-800 diluted 1:1000 both in Licor block+0.05% TweeN$_2$O, and were incubated for 1 hour at room temperature. The plates were washed with PBS+0.05% Tween 20. A 100 μL aliquot of PBS was added to each well and the plates were read on a Li-Cor Odyssey CLX plate reader.

The phospho-ERK(Thr202/Tyr204) signal was normalized to the GAPDH signal for each well and percent of DMSO control values were calculated. IC50 values were generated using a 4-parameter fit of the dose response curve The results for exemplary compounds of Formula (I) are shown in Table 3. ND is not determined.

TABLE 3

Inhibition of KRas G12D-mediated Phosphorylation of ERK by Exemplary Compounds of Formula (I)

| Example No. | IC$_{50}$ (nM) | Example No. | IC$_{50}$ (nM) |
|---|---|---|---|
| 1 | 3159.1 | 234 | 409.0 |
| 2 | 721.4 | 235 | 338.6 |
| 3 | 10283.1 | 236 | 2626.3 |
| 4 | 8530.0 | 238 | 4656.9 |
| 5 | 8193.8 | 239 | 2951.1 |
| 6 | 11518.2 | 240 | >16666.7 |
| 10 | 8115.5 | 241 | >16666.7 |
| 11 | 1078.2 | 242 | >16666.7 |
| 12 | 4905.2 | 243 | 0.8 |
| 14 | 4843.5 | 244 | 763.0 |
| 15 | >16666.7 | 245 | 23.4 |
| 16 | 3834.5 | 246 | 1.0 |
| 18 | 3742.5 | 247 | 4310.5 |
| 19 | >16666.7 | 248 | 1082.8 |
| 22 | 1888.7 | 249 | 7705.6 |
| 24 | 2890.0 | 250 | 7477.7 |
| 26 | 4282.7 | 251 | 10.3 |
| 27 | 1275.8 | 252 | 0.8 |
| 28 | 11736.0 | 253 | 2.0 |
| 29 | 13630.9 | 254 | 2428.8 |
| 30 | 9600.4 | 255 | 673.4 |
| 31 | 2425.6 | 256 | >16666.7 |
| 32 | >50000 | 257 | 530.7 |
| 33 | 2052.1 | 258 | 1460.4 |
| 34 | 4207.8 | 259 | 3.9 |
| 35 | 11332.1 | 260 | >16666.7 |
| 36 | 107.8 | 263 | 7641.0 |
| 40 | 4241.8 | 274 | 4706.4 |
| 41 | 6647.2 | 275 | 7058.7 |
| 42 | 637.6 | 276 | 3789.2 |
| 43 | 6204.1 | 277 | 3675.0 |
| 44 | 2290.1 | 278 | 104.4 |
| 45 | 840.0 | 279 | 7401.8 |
| 47 | 4445.6 | 280 | 6115.7 |
| 48 | 4875.6 | 281 | 97.8 |
| 49 | 2123.1 | 282 | 4.9 |
| 50 | 15404.5 | 283 | 7.0 |
| 51 | 12066.6 | 284 | 17.4 |
| 52 | 8380.0 | 286 | 1733.1 |
| 54 | >16666.7 | 287 | 8067.4 |
| 60 | >16666.7 | 290 | 110.5 |
| 63 | 186.7 | 291 | 46.5 |
| 64 | 3971.0 | 292 | 1696.0 |
| 65 | 1332.6 | 296 | 8472.0 |
| 68 | 7530.9 | 297 | 6562.0 |
| 69 | >16666.7 | 298 | 1228.7 |
| 71 | >16666.7 | 299 | >5555.6 |
| 72 | 7260.8 | 301 | 3173.2 |
| 73 | >5555.6 | 302 | 1993.3 |
| 74 | 5465.1 | 304 | 1415.1 |
| 75 | >16666.7 | 308 | >5555.6 |
| 76 | 7412.9 | 312 | 1877.6 |
| 78 | >16666.7 | 314 | 3.7 |
| 81 | 8288.3 | 321 | >16666.7 |
| 82 | >16666.7 | 322 | 664.8 |
| 84 | 5722.3 | 324 | 863.9 |
| 85 | >16666.7 | 325 | >16666.7 |
| 87 | 10553.8 | 326 | 121.6 |
| 91 | 5514.1 | 327 | 31.4 |
| 93 | >16666.7 | 328 | 896.9 |
| 98 | 388.6 | 330 | 11.8 |
| 102 | 7955.9 | 331 | 10826.0 |
| 103 | >16666.7 | 332 | >16666.7 |
| 104 | >16666.7 | 334 | 2909.3 |
| 106 | 3096.3 | 335 | 10440.5 |
| 109 | 330.5 | 336 | 1057.2 |

TABLE 3-continued

Inhibition of KRas G12D-mediated Phosphorylation
of ERK by Exemplary Compounds of Formula (I)

| Example No. | IC$_{50}$ (nM) | Example No. | IC$_{50}$ (nM) |
|---|---|---|---|
| 110 | >16666.7 | 337 | 1620.7 |
| 114 | 10259.6 | 338 | >16666.7 |
| 115 | 9514.0 | 339 | 8659.5 |
| 118 | >16666.7 | 340 | 51.5 |
| 119 | 3700.2 | 341 | 837.3 |
| 120 | 2092.9 | 342 | 1001.2 |
| 121 | 4077.1 | 343 | 1616.5 |
| 122 | >16666.7 | 344 | 8069.6 |
| 124 | 11087.4 | 345 | 1468.2 |
| 126 | 3470.6 | 346 | 1351.5 |
| 127 | >16666.7 | 347 | 458.9 |
| 131 | >16666.7 | 348 | 778.6 |
| 132 | 2558.7 | 351 | >16666.7 |
| 133 | 2048.8 | 356 | 11920.1 |
| 134 | 895.4 | 360 | 8353.4 |
| 135 | 4820.9 | 362 | 10457.0 |
| 139 | 5245.1 | 364 | 322.0 |
| 141 | >16666.7 | 365 | 3949.0 |
| 152 | >50000 | 366 | 7.0 |
| 153 | 2369.2 | 367 | 111.8 |
| 156 | 1786.9 | 370 | 10730.6 |
| 157 | 7998.7 | 372 | 10.5 |
| 158 | 4222.3 | 373 | >16666.7 |
| 159 | >16666.7 | 375 | 1310.3 |
| 160 | 6930.7 | 376 | 582.3 |
| 161 | >16666.7 | 380 | >16666.7 |
| 162 | >16666.7 | 381 | 708.4 |
| 163 | >16666.7 | 382 | >16666.7 |
| 164 | >16666.7 | 384 | 398.2 |
| 165 | 11068.5 | 385 | >16666.7 |
| 167 | 16142.4 | 386 | 320.3 |
| 168 | >16666.7 | 388 | 40.2 |
| 173 | 10504.3 | 389 | 780.7 |
| 174 | 12816.8 | 390 | 6108.7 |
| 175 | >5555.6 | 393 | 7579.3 |
| 178 | >16666.7 | 395 | 1089.1 |
| 179 | 71.2 | 396 | 8173.3 |
| 180 | >16666.7 | 397 | >16666.7 |
| 181 | 12839.1 | 399 | 509.9 |
| 182 | 13549.2 | 400 | 260.6 |
| 183 | 5252.5 | 401 | 603.5 |
| 185 | 7.1 | 403 | 2881.0 |
| 186 | 3383.1 | 404 | 8331.6 |
| 187 | 450.1 | 405 | 297.0 |
| 189 | 24.1 | 406 | 440.3 |
| 190 | 16314.3 | 408 | 238.0 |
| 191 | 5047.0 | 410 | 8.0 |
| 193 | 8517.9 | 411 | 745.3 |
| 195 | 2461.5 | 412 | 4779.3 |
| 197 | >16666.7 | 413 | 2156.3 |
| 198 | 2425.5 | 418 | 2741.5 |
| 199 | 464.8 | 419 | 2776.1 |
| 201 | 13915.2 | 420 | 7816.4 |
| 202 | 10186.8 | 422 | 2357.8 |
| 203 | 2183.2 | 424 | 680.9 |
| 204 | 306.7 | 425 | 5414.1 |
| 205 | 242.1 | 426 | 228.0 |
| 206 | 899.6 | 427 | 1981.7 |
| 208 | >16666.7 | 428 | 6964.4 |
| 209 | >16666.7 | 429 | 1696.0 |
| 210 | >16666.7 | 430 | 141.0 |
| 211 | 13506.7 | 431 | 74.3 |
| 214 | >16666.7 | 432 | 106.3 |
| 215 | >16666.7 | 433 | 43.2 |
| 216 | 51.0 | 434 | 6.7 |
| 219 | 2032.0 | 435 | 1822.4 |
| 220 | 1344.9 | 436 | 3989.5 |
| 221 | 15840.8 | 438 | 1630.8 |
| 223 | 4272.7 | 439 | 12.8 |
| 224 | 6375.8 | 440 | 8.4 |
| 225 | 3058.3 | 441 | 4.1 |
| 226 | 6745.4 | 442 | 1162.0 |
| 227 | 2976.0 | 443 | 160.0 |
| 228 | 13718.5 | 444 | 365.0 |
| 229 | 11330.3 | 445 | 130.0 |

TABLE 3-continued

Inhibition of KRas G12D-mediated Phosphorylation
of ERK by Exemplary Compounds of Formula (I)

| Example No. | IC$_{50}$ (nM) | Example No. | IC$_{50}$ (nM) |
|---|---|---|---|
| 231 | 2806.1 | 451 | 78.3 |
| 232 | 15.2 | 452 | 13.7 |
| 233 | 15568.1 | | |

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A compound selected from:

[Chemical structure 1]

[Chemical structure 2]

[Chemical structure 3]

949
-continued
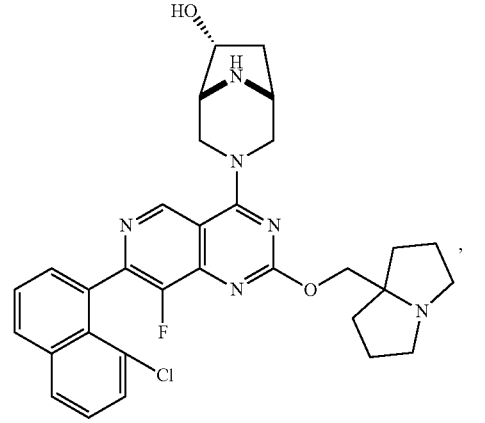
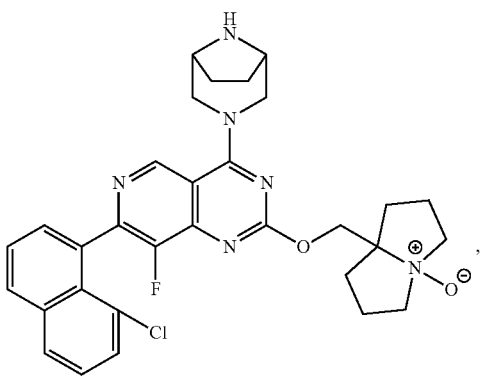
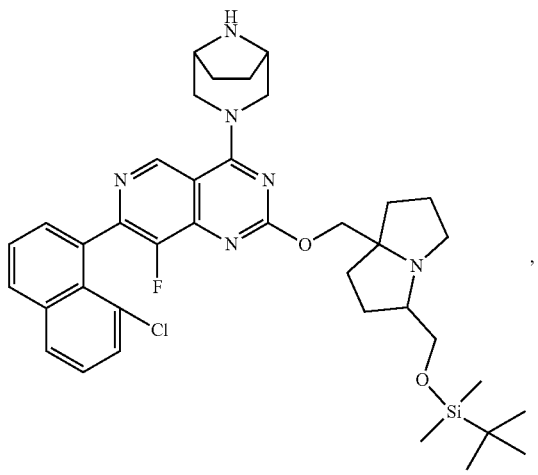
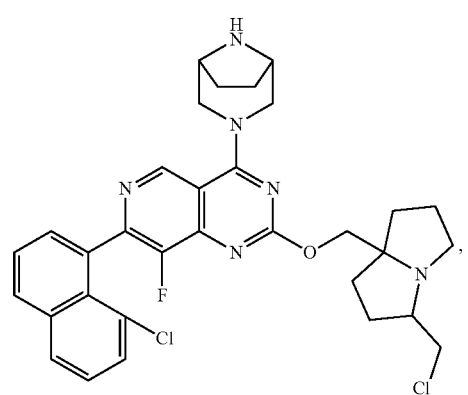
950
-continued
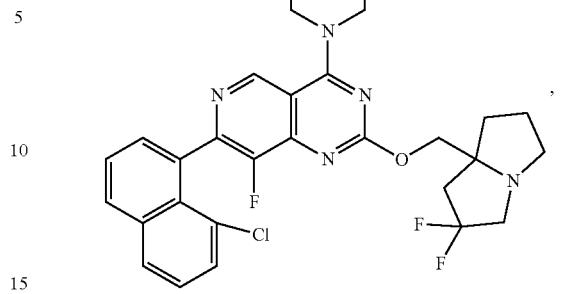
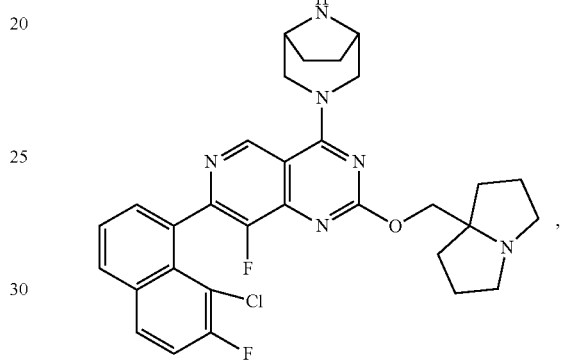
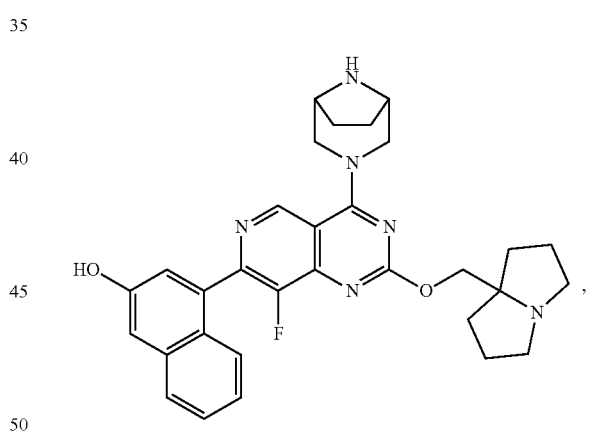
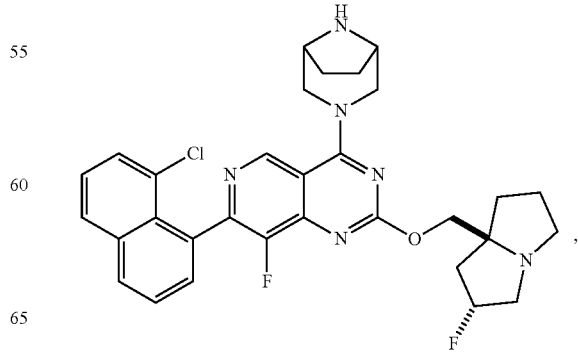

951 -continued
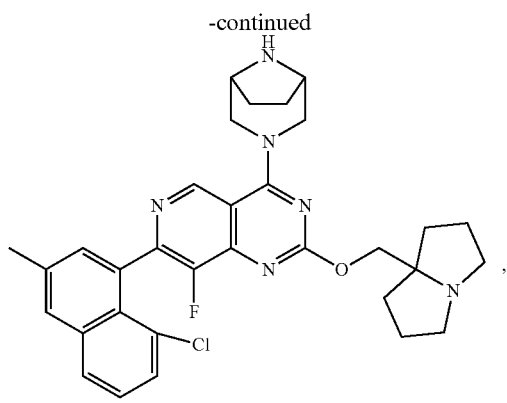
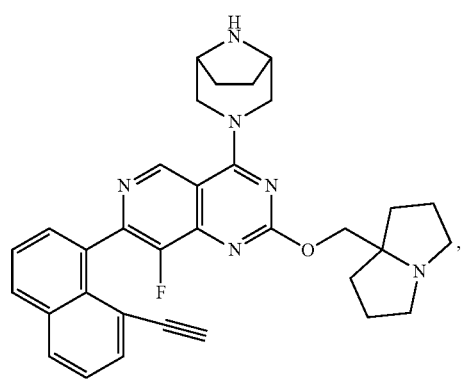
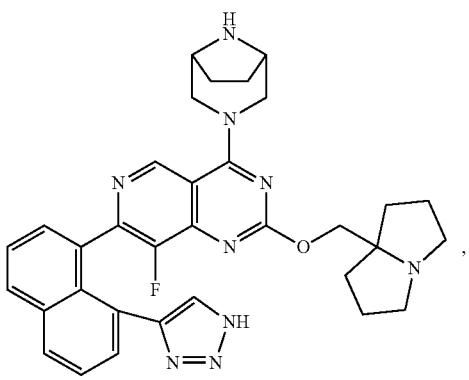
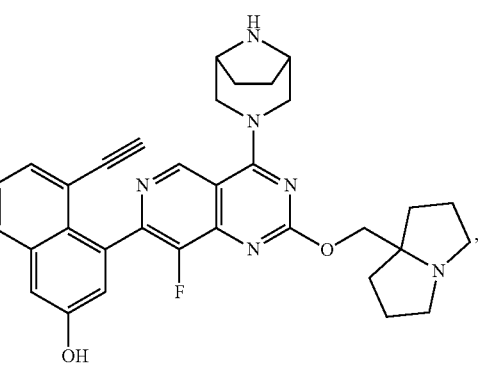
952 -continued
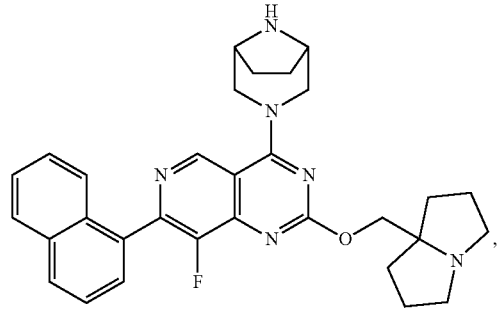
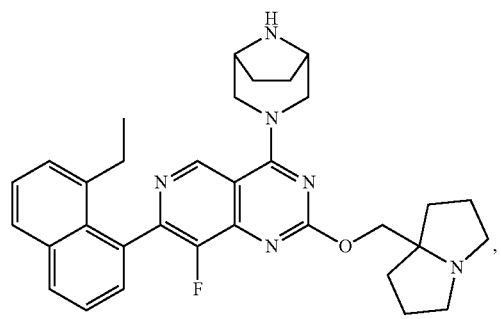
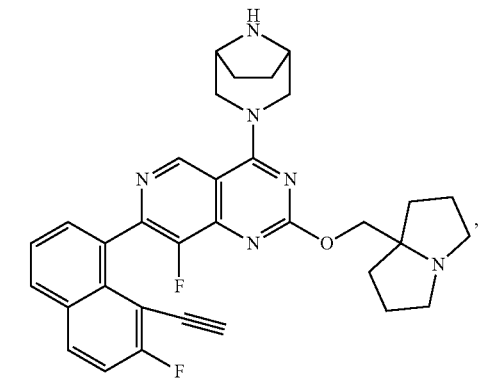
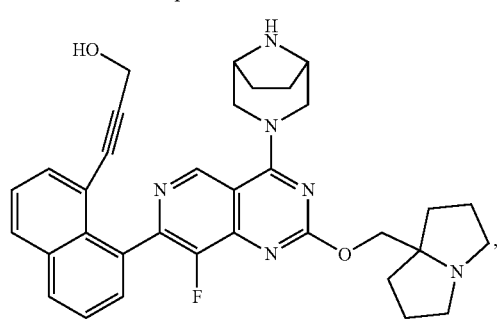
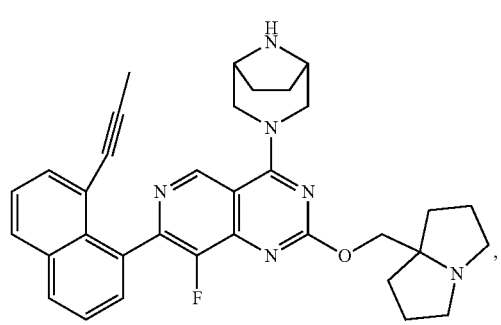

953
-continued
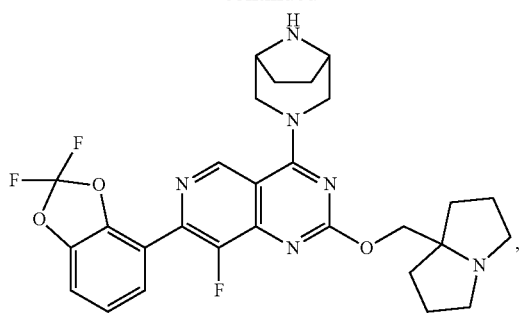
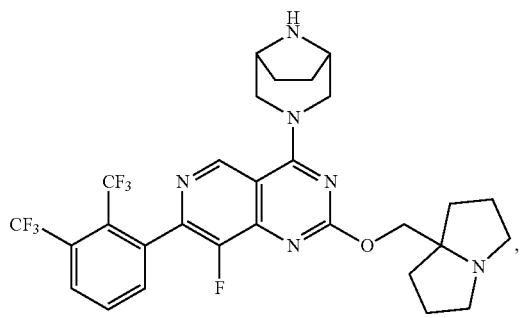
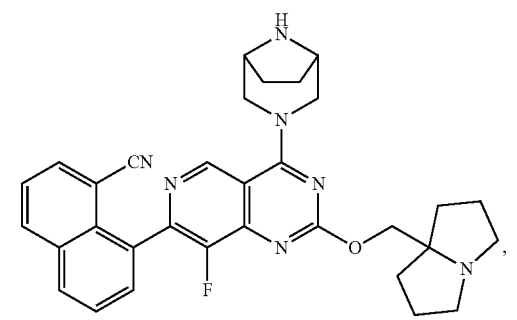
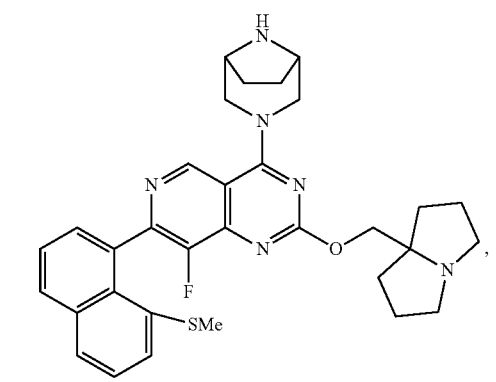
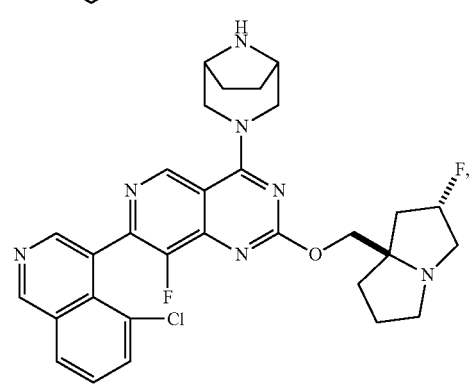
954
-continued
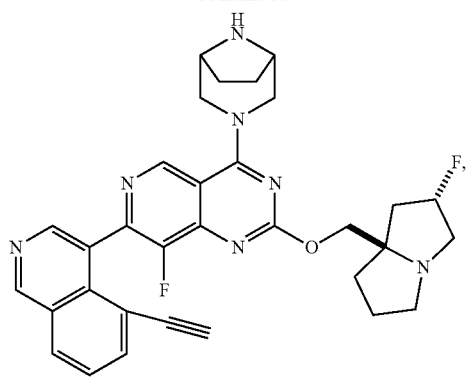
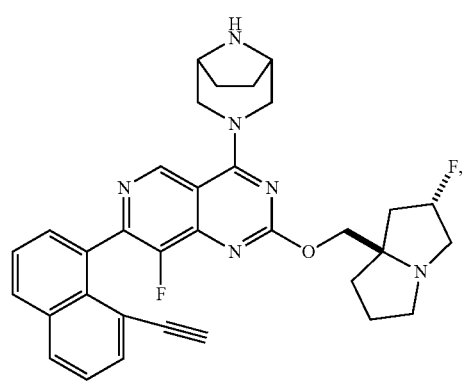
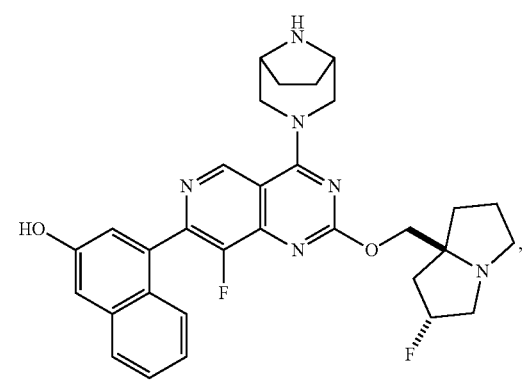
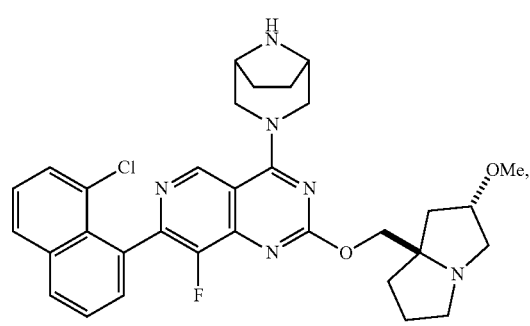

955
-continued
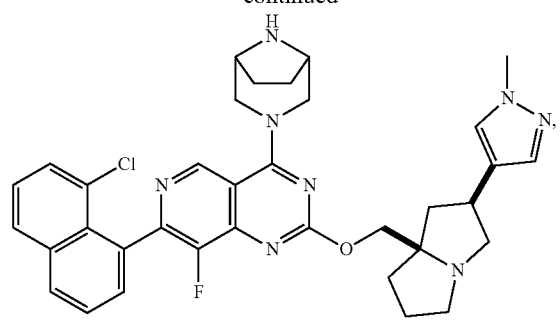
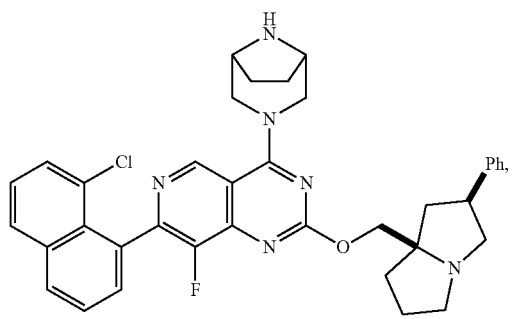
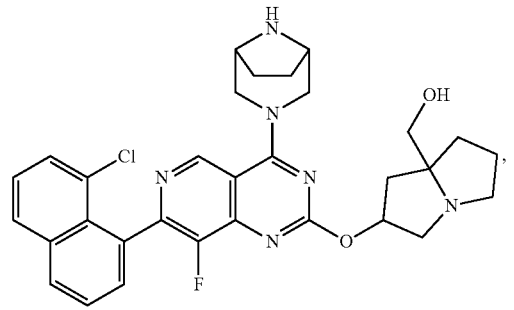
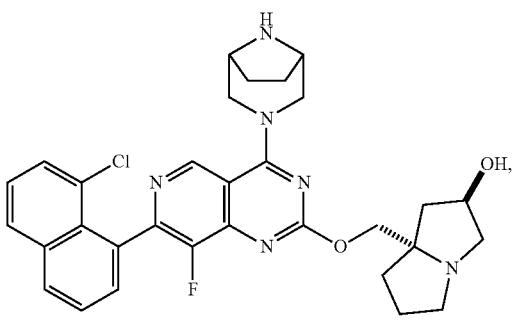
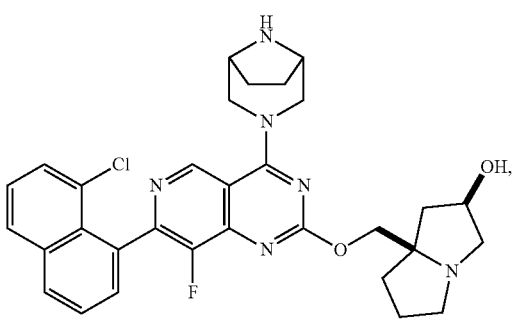
956
-continued
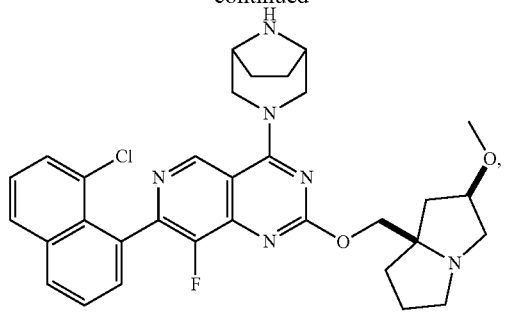
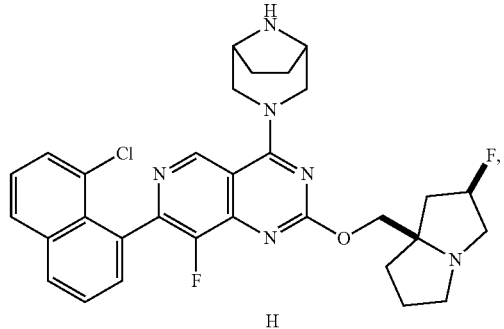
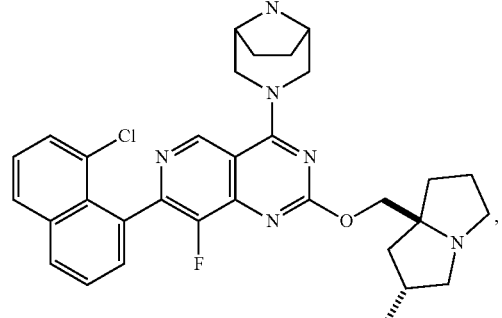
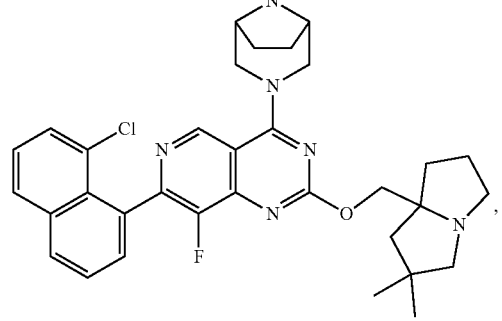
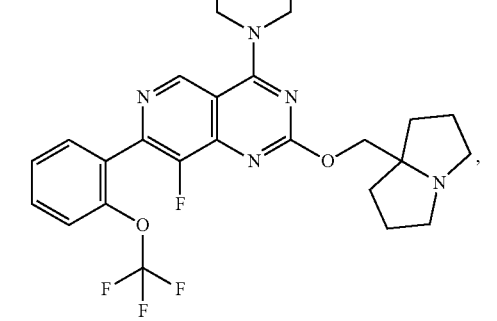

957
-continued
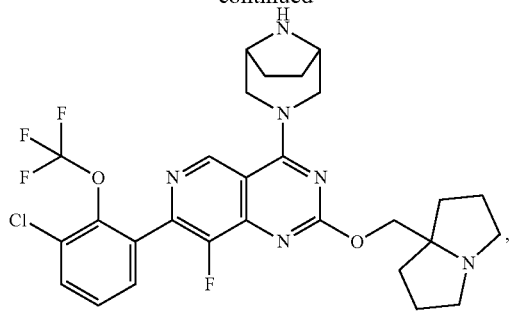
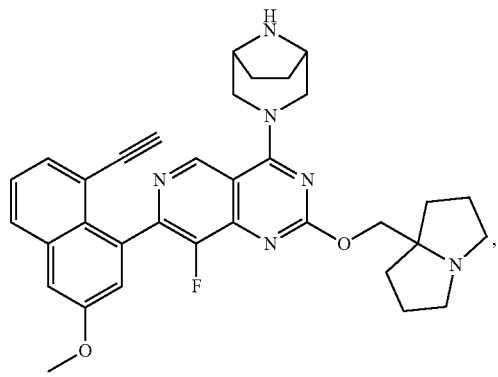
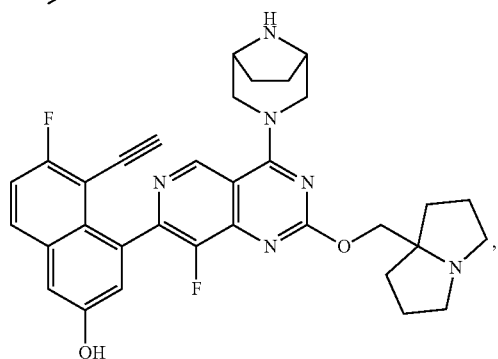
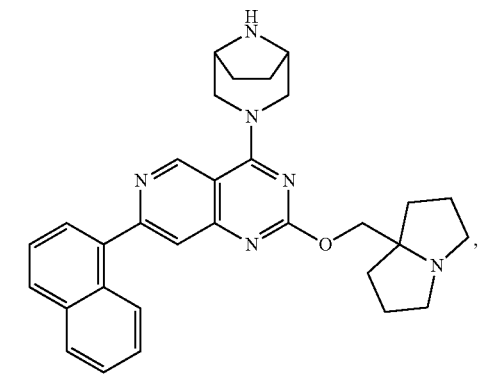
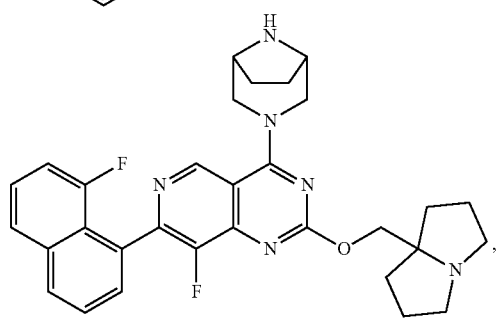
958
-continued
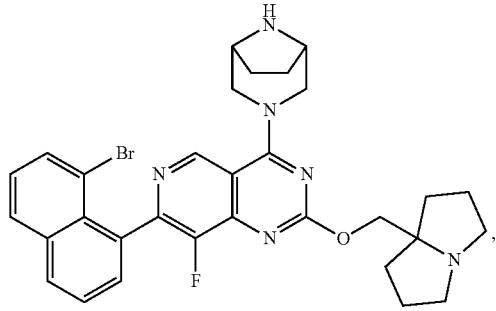
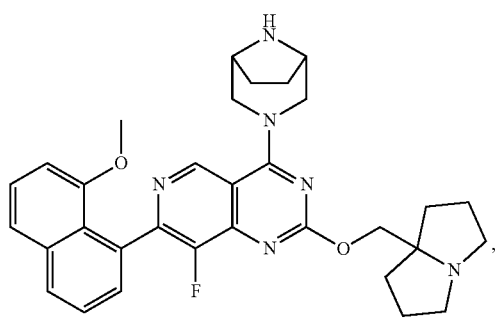
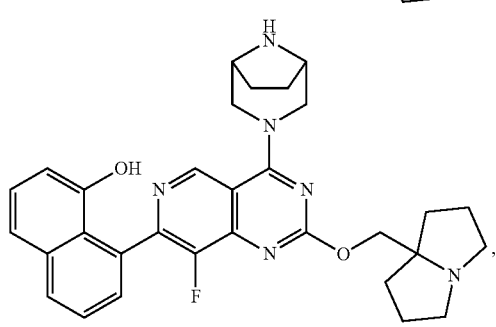
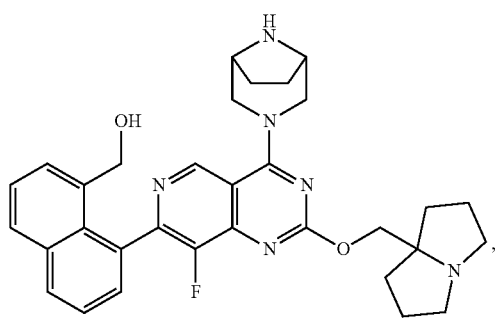
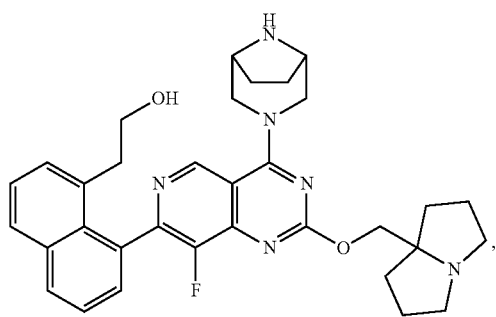

959
-continued
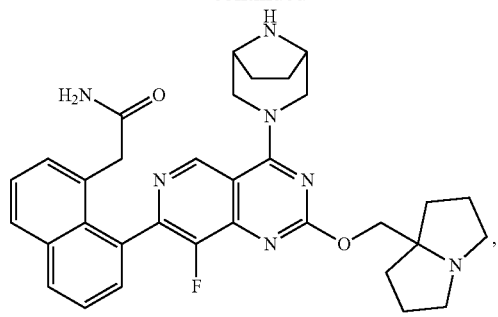
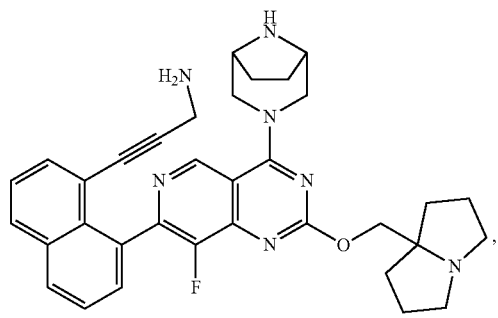
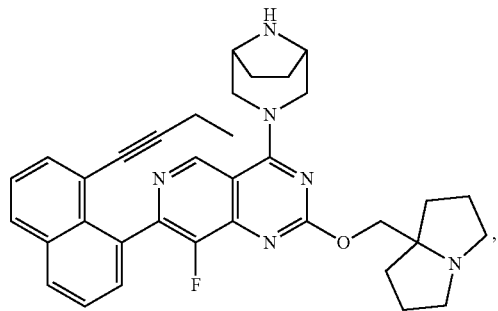
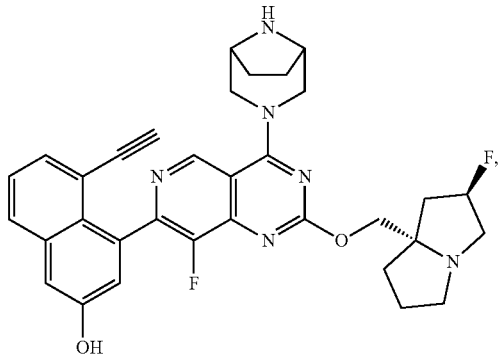
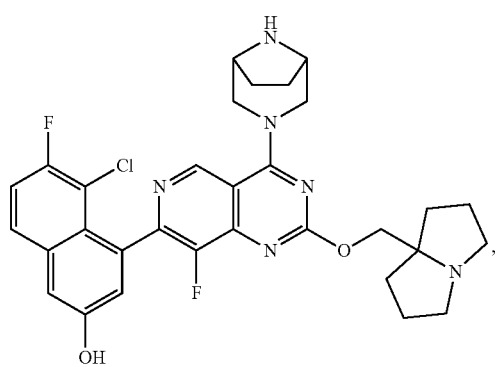
960
-continued
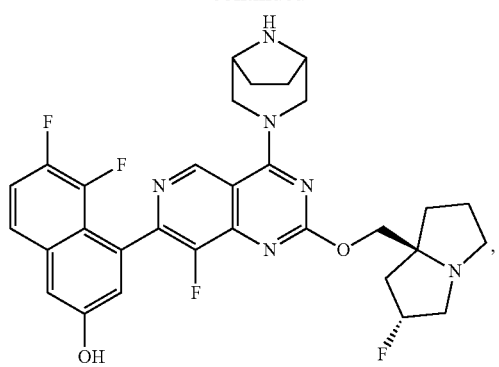
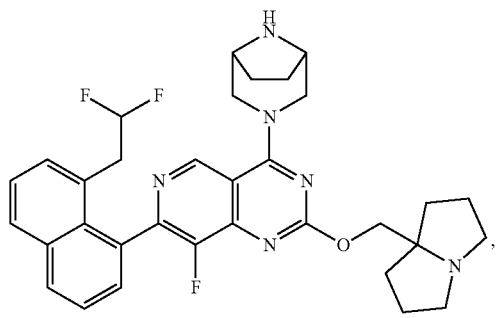
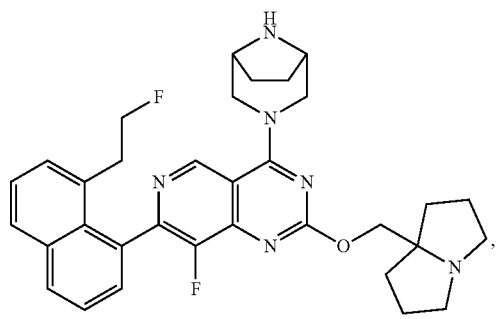
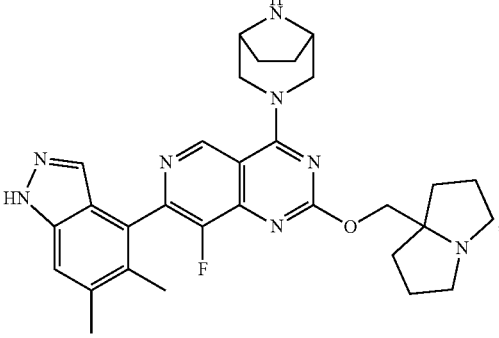
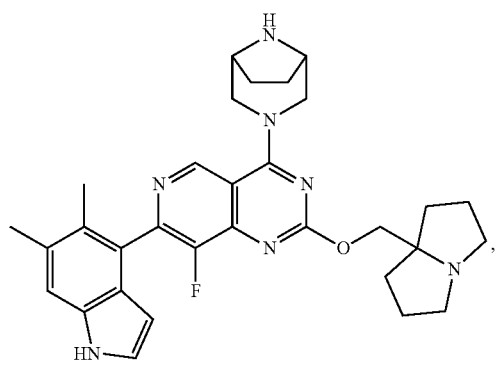

-continued
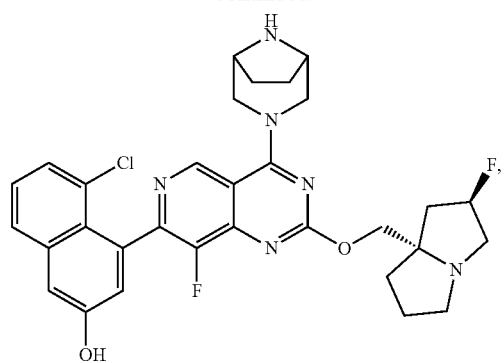
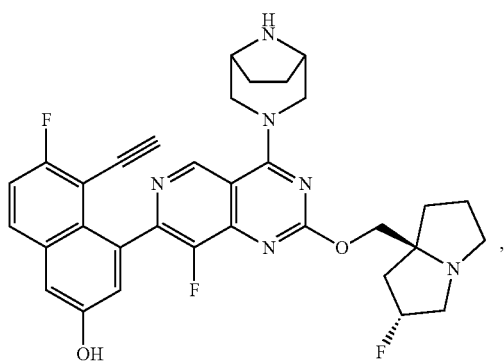
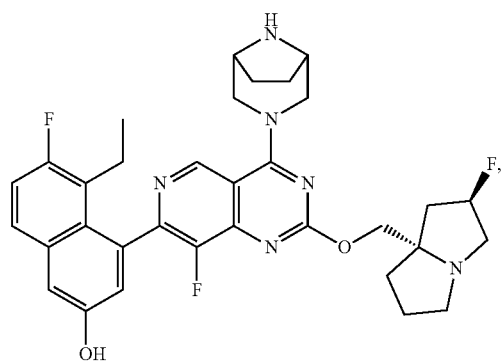
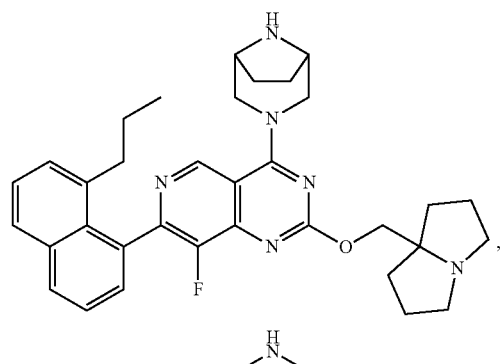
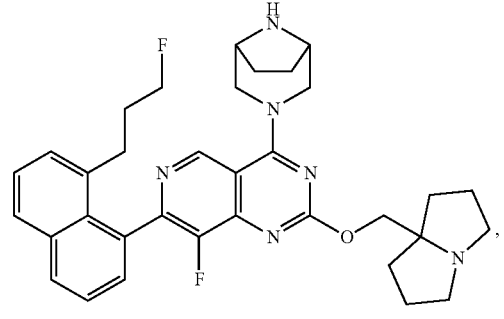
-continued
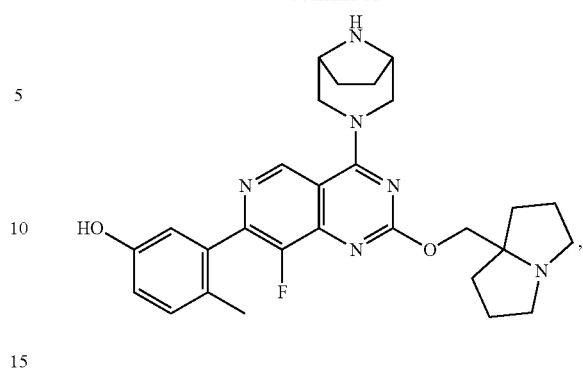
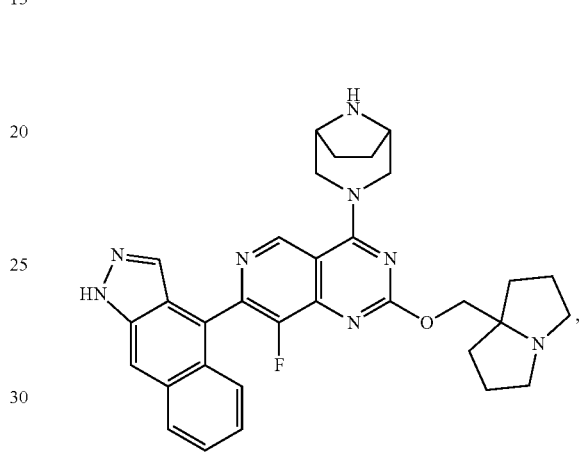
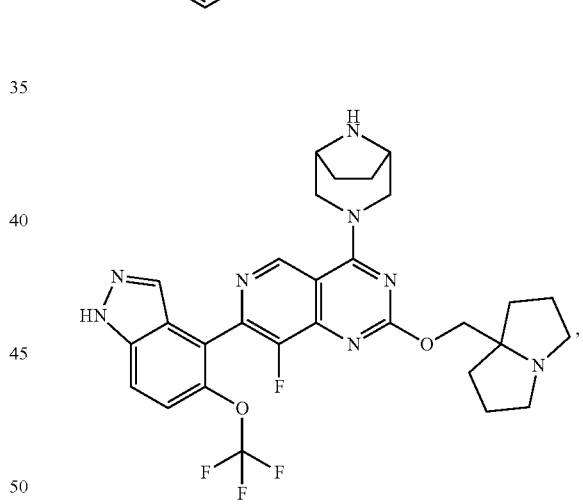
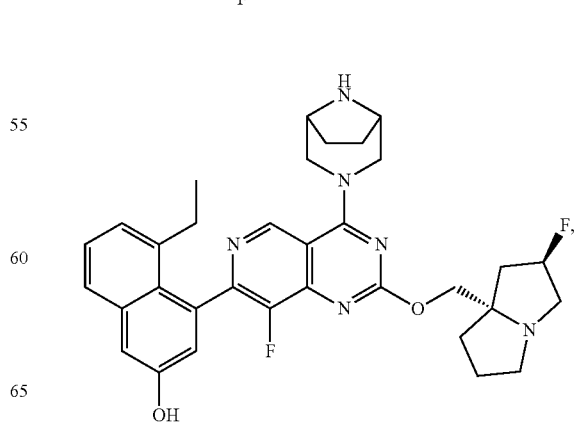

963
-continued
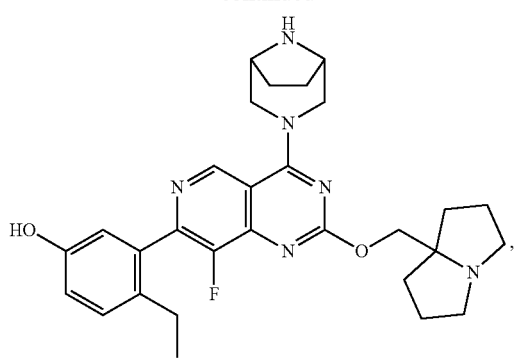
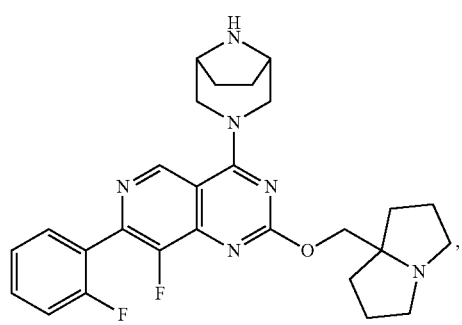
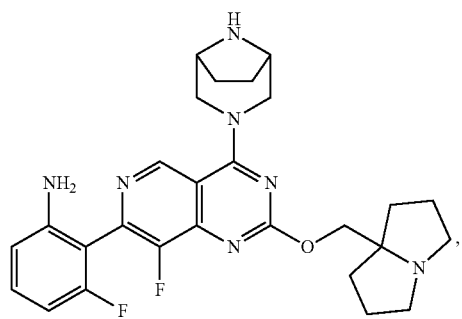
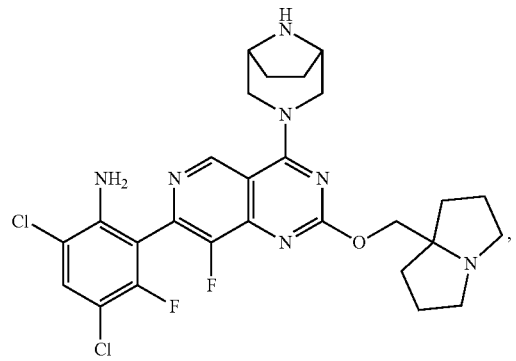
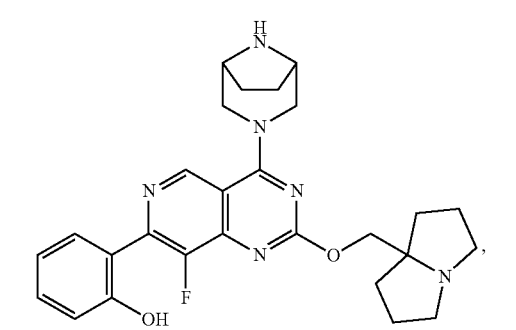
964
-continued
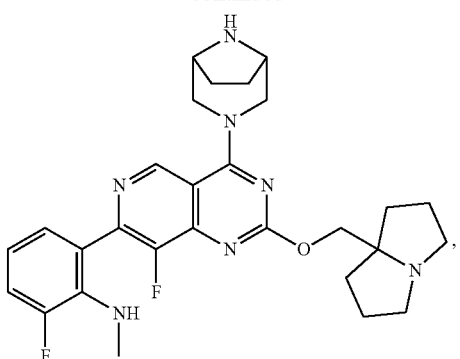
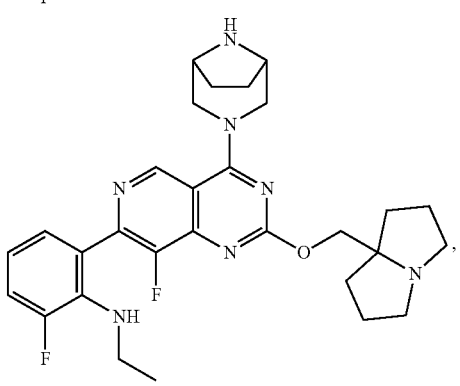
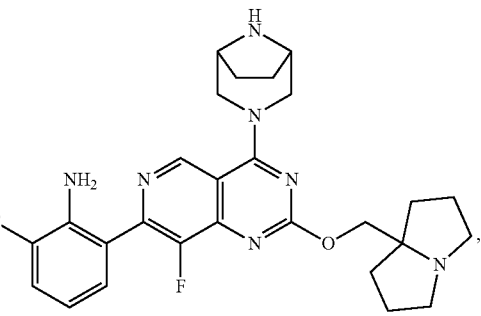
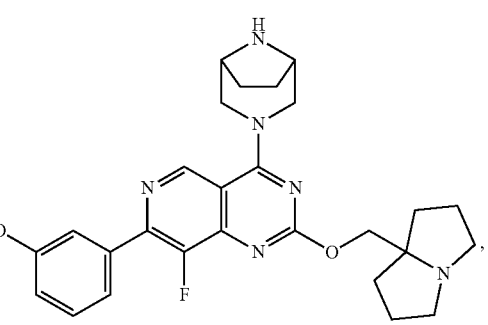
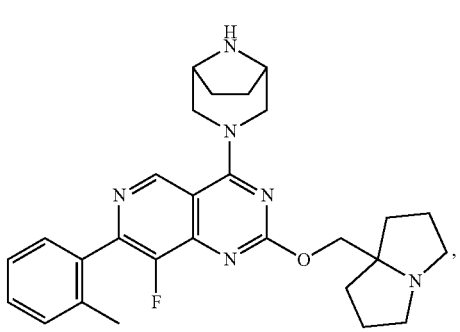

965
-continued
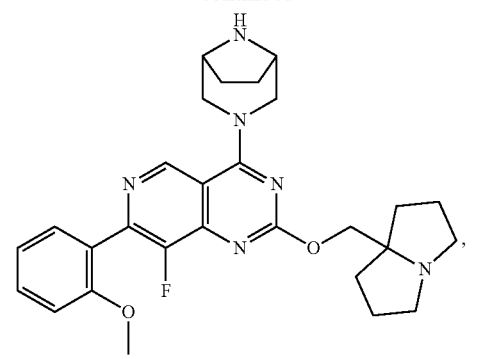
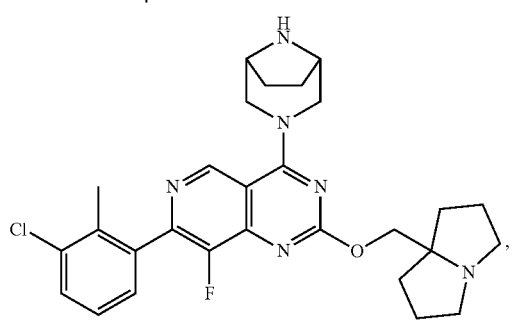
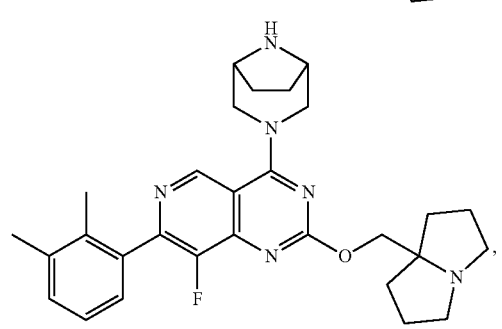
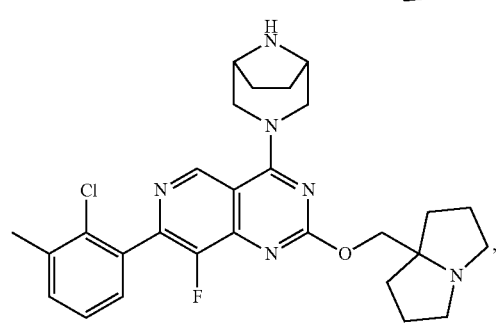
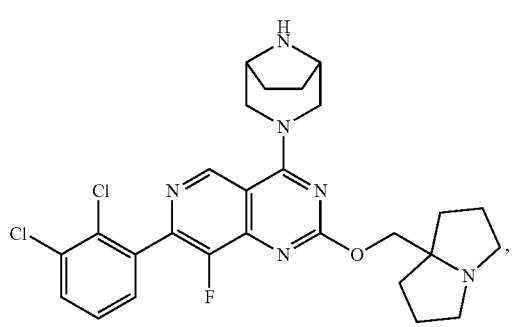
966
-continued
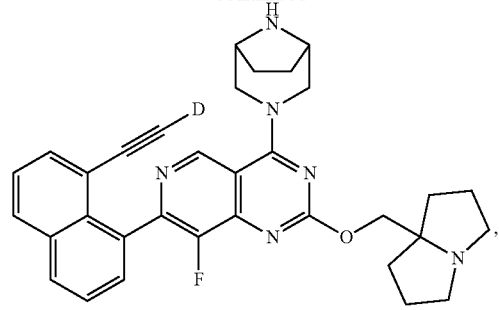
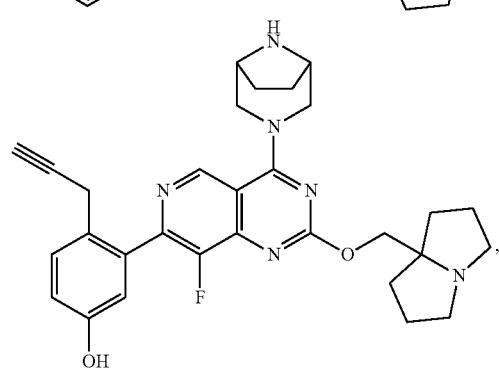
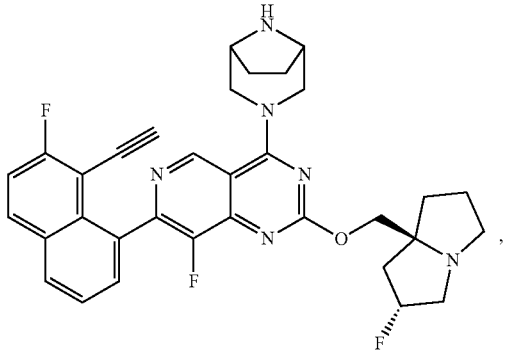
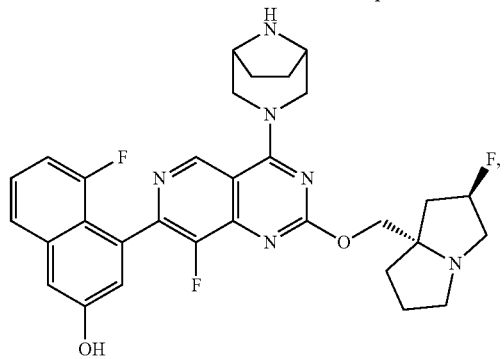
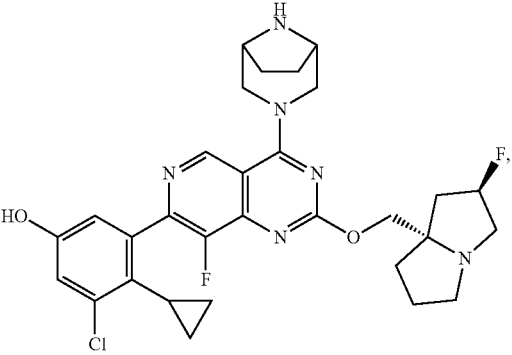

967
-continued
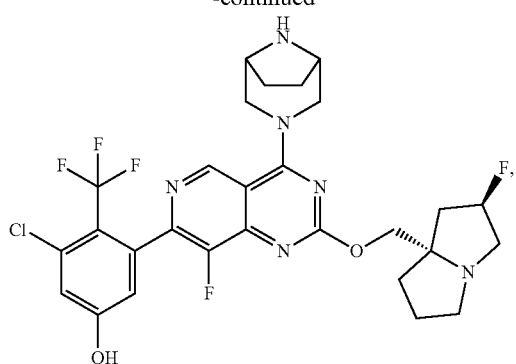
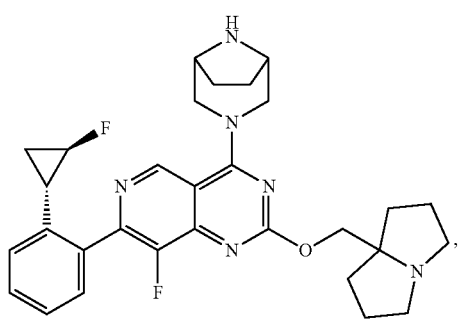
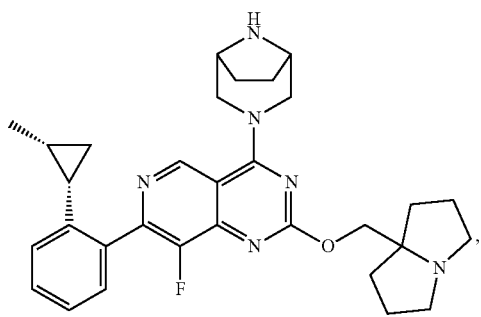
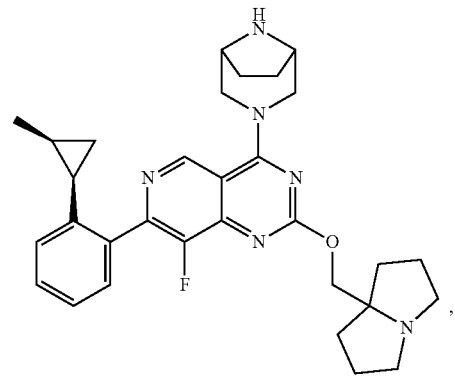
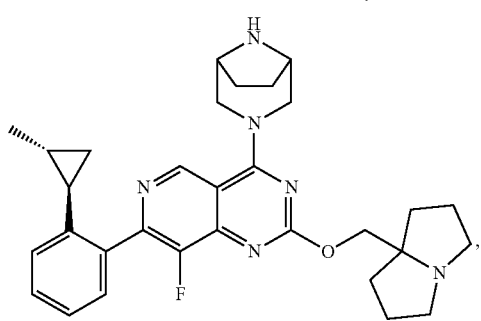
968
-continued
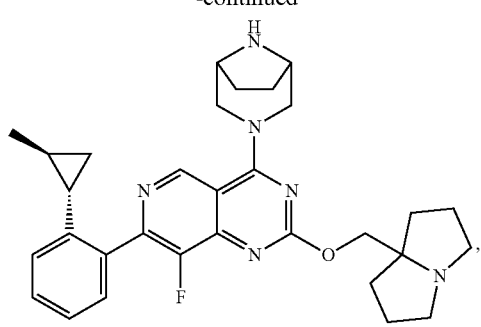
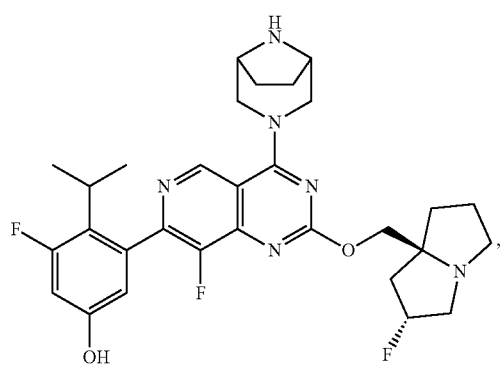
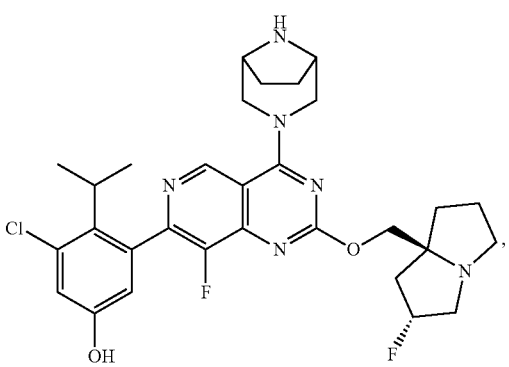
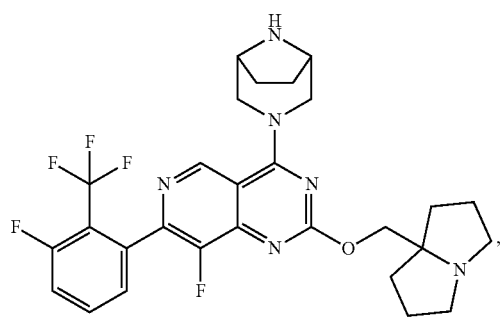
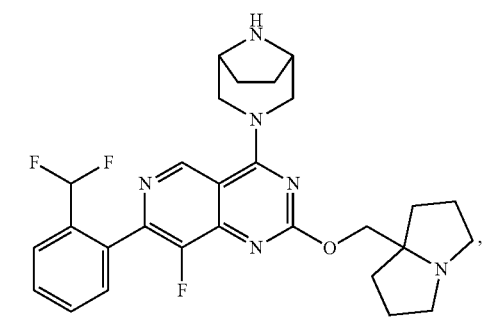

969
-continued
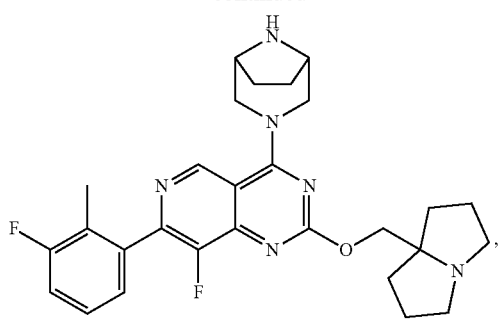
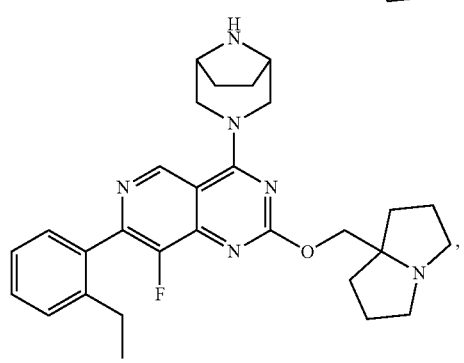
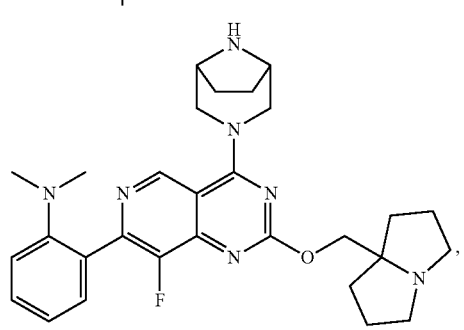
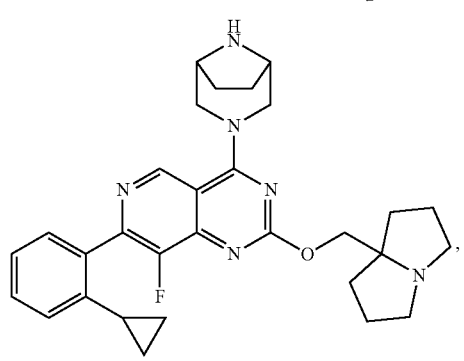
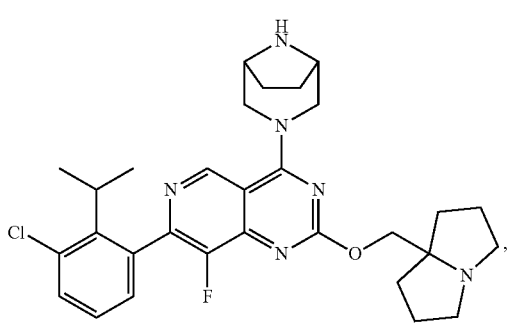
970
-continued
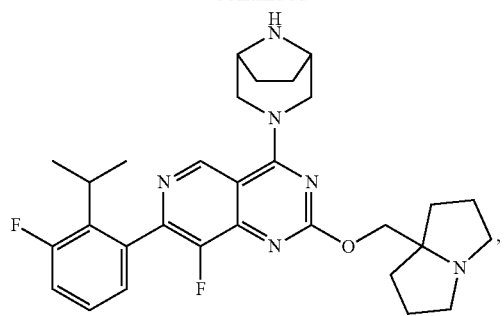
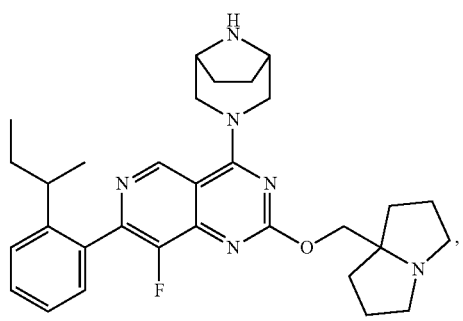
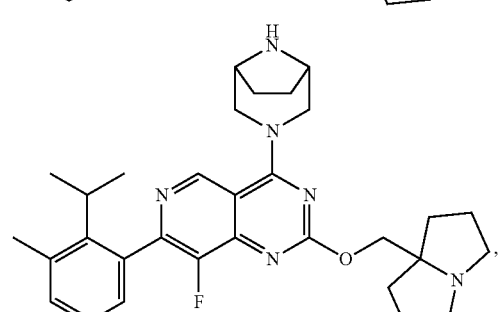
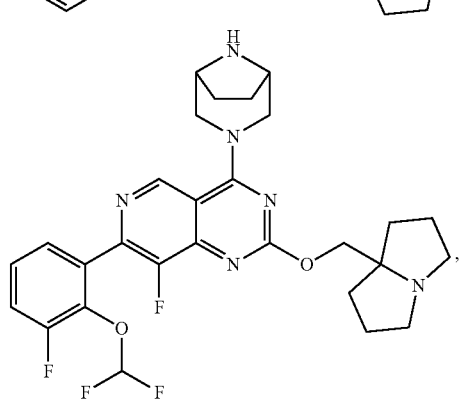

971
-continued
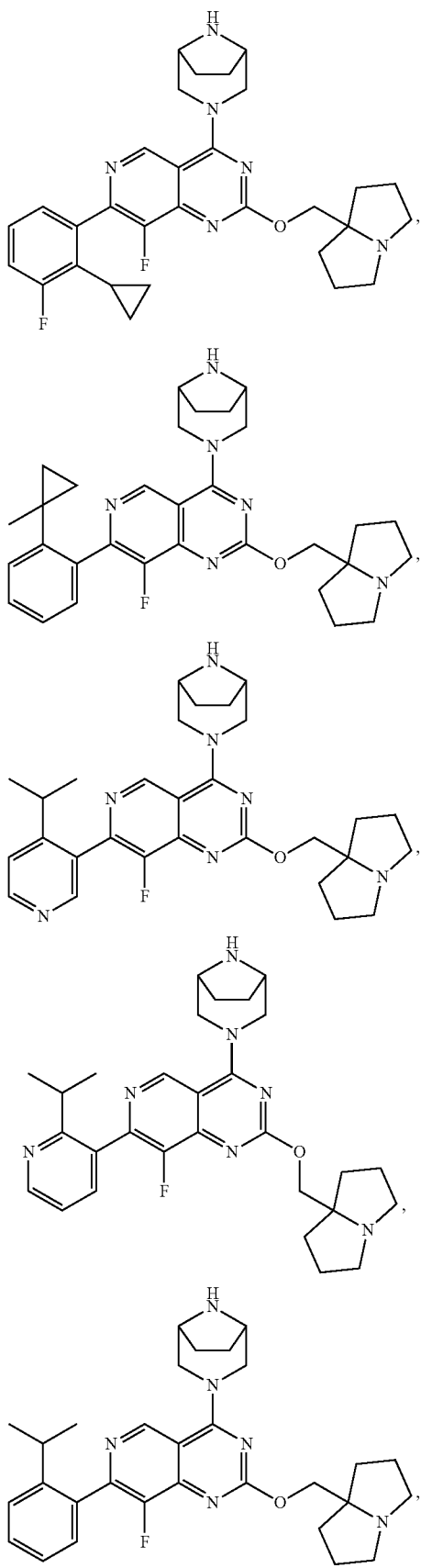
972
-continued
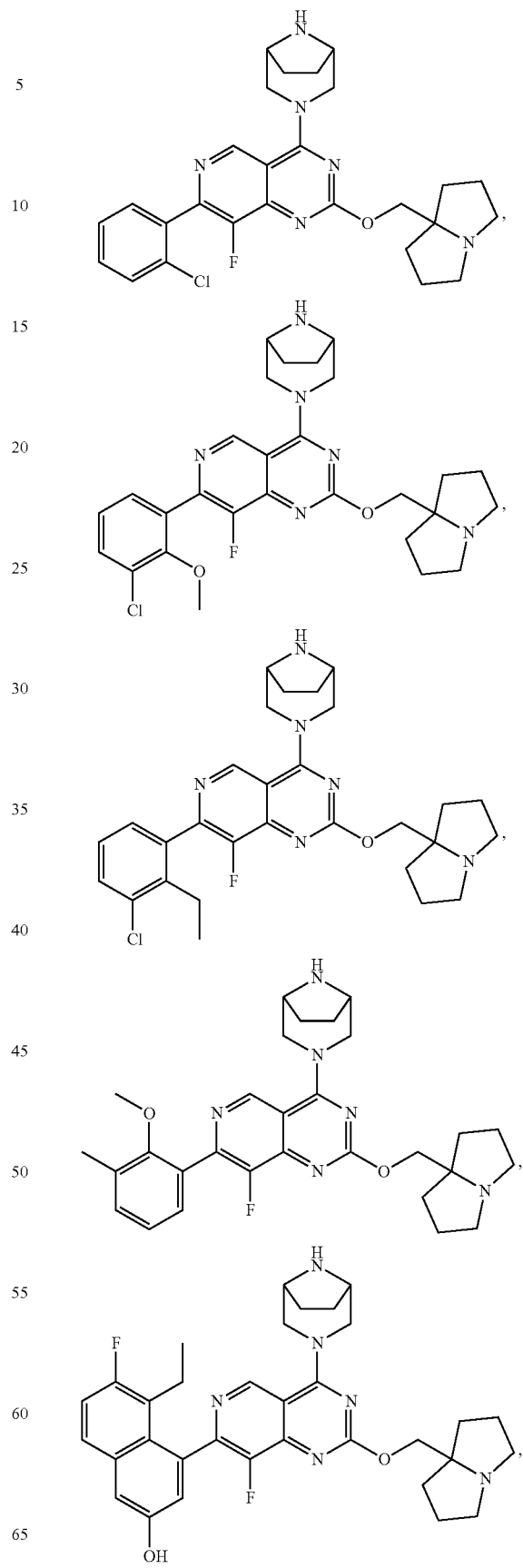

973
-continued
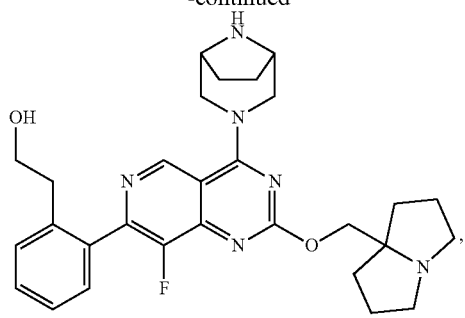
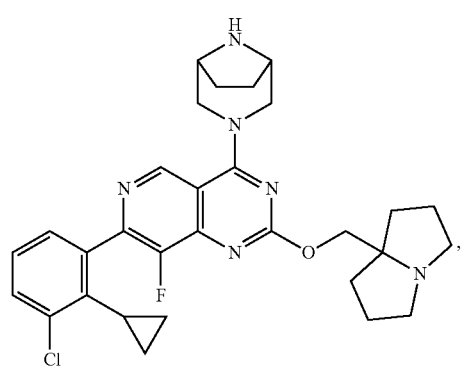
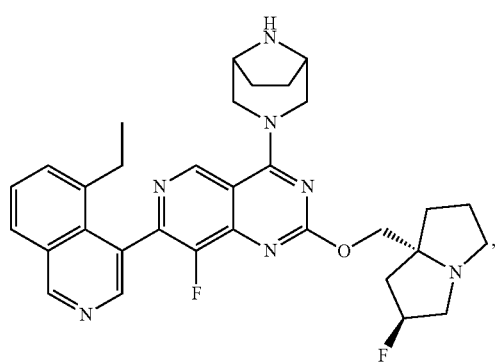
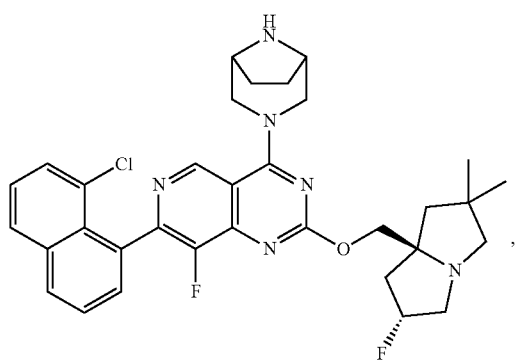
974
-continued
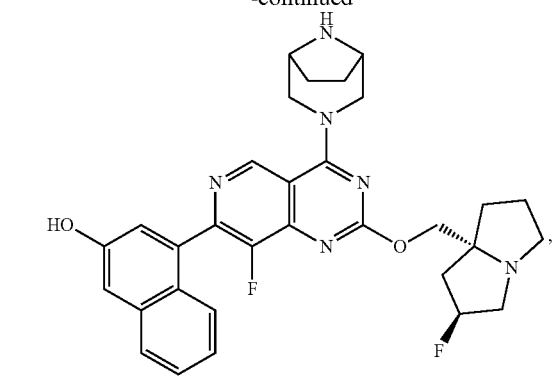
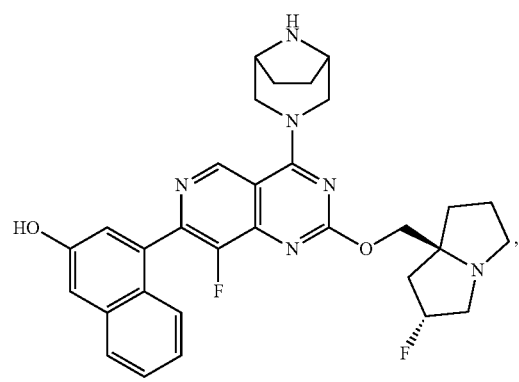
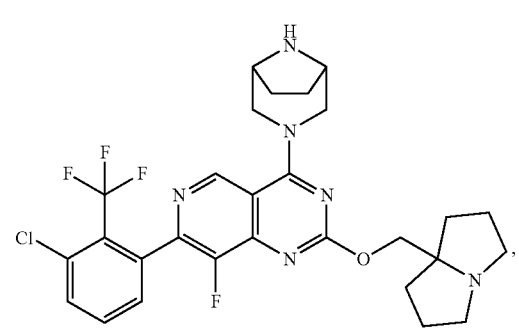
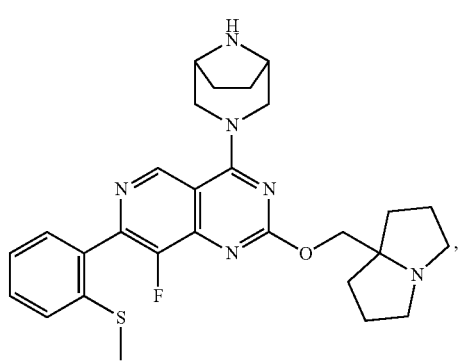

975
-continued
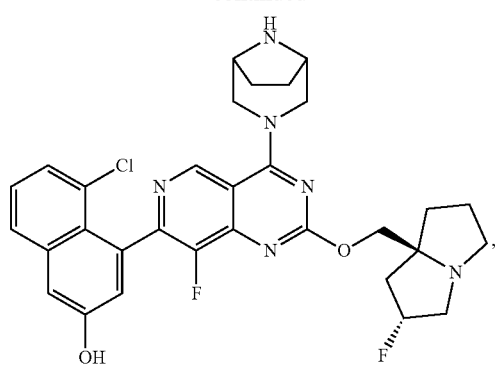
976
-continued
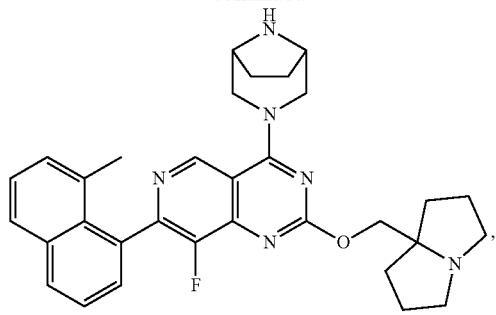
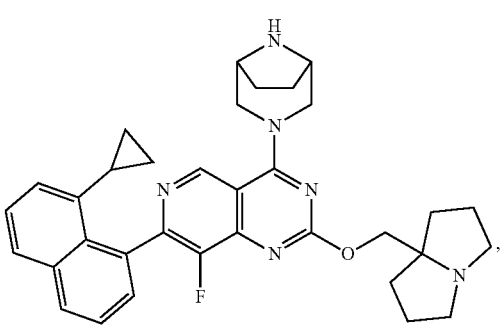
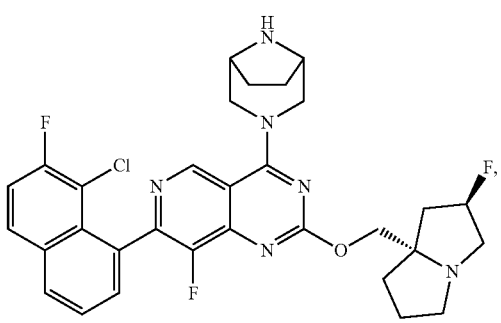
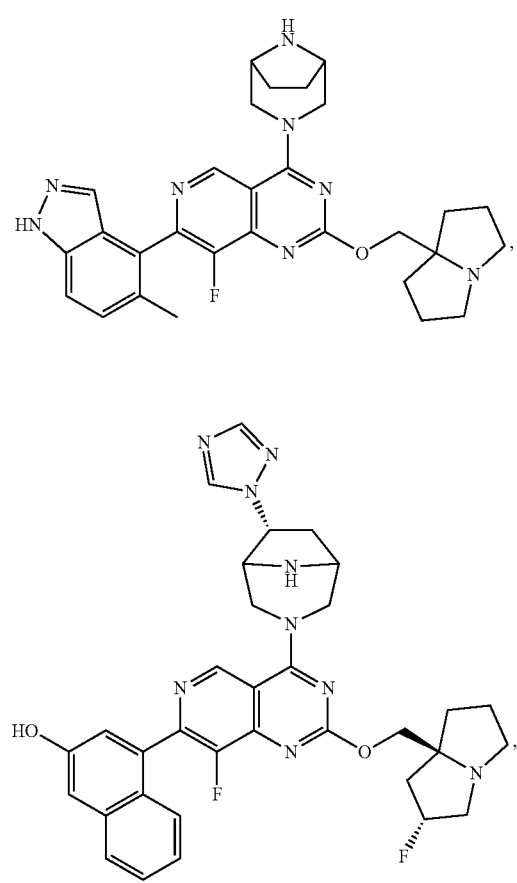

977
-continued
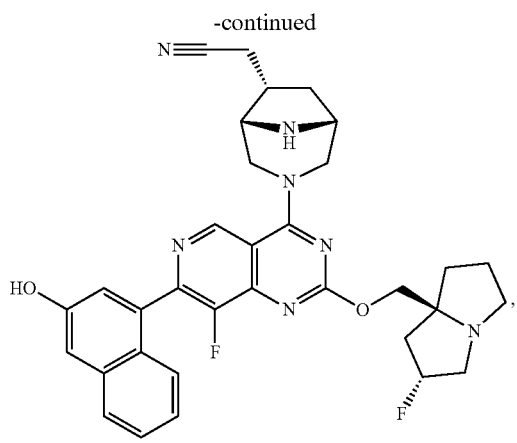
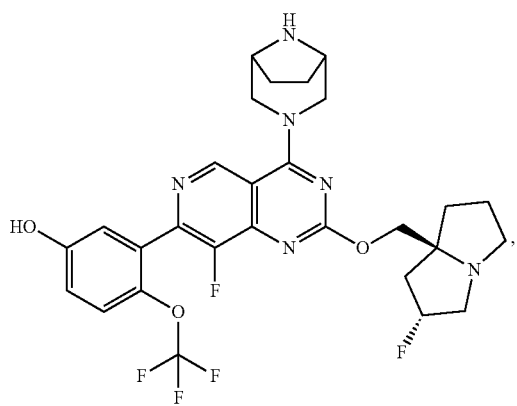
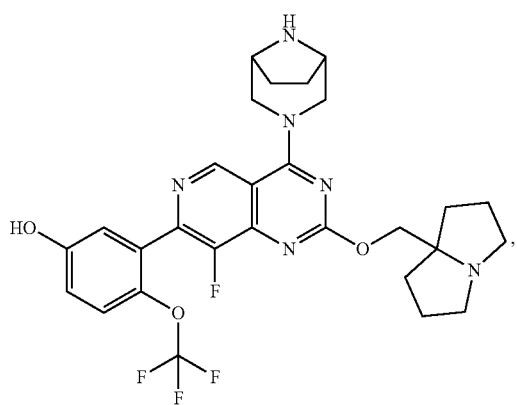
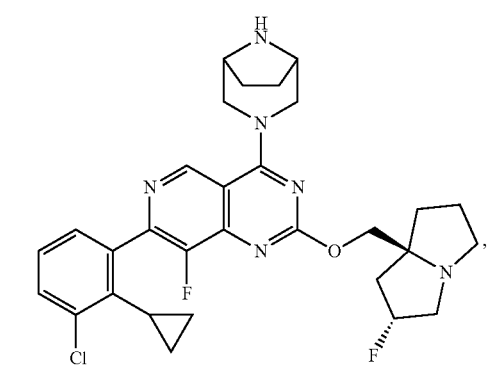
978
-continued
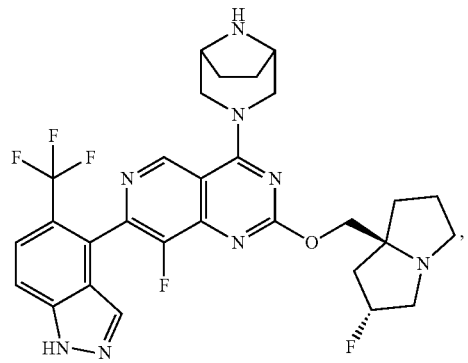
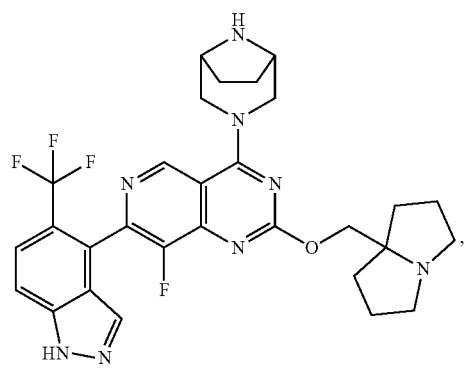
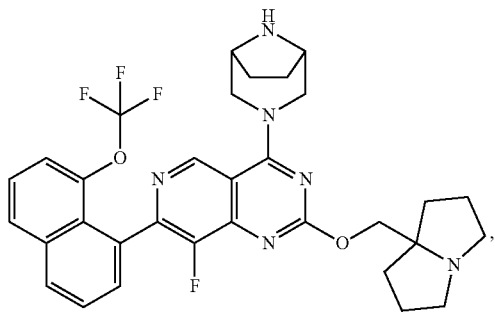
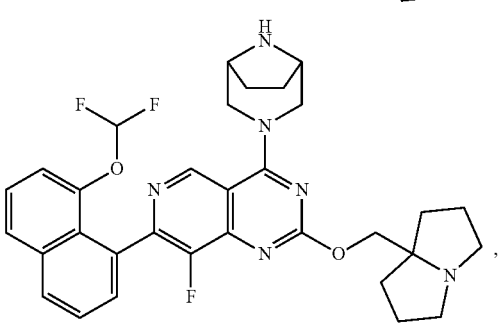
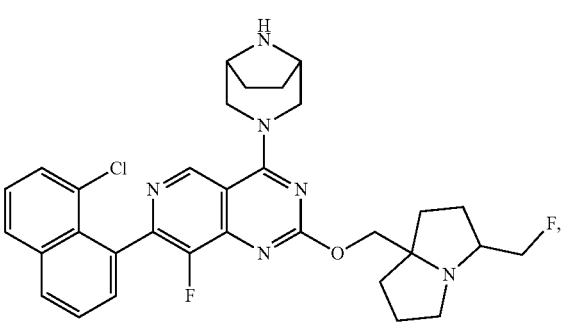

979
-continued
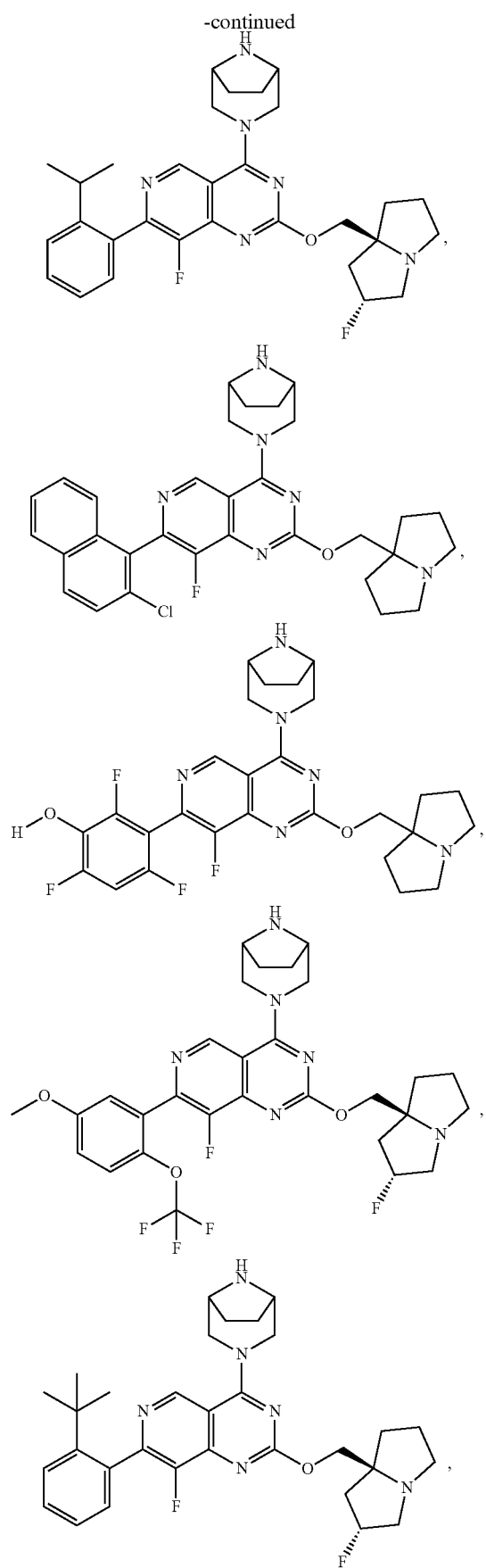
980
-continued
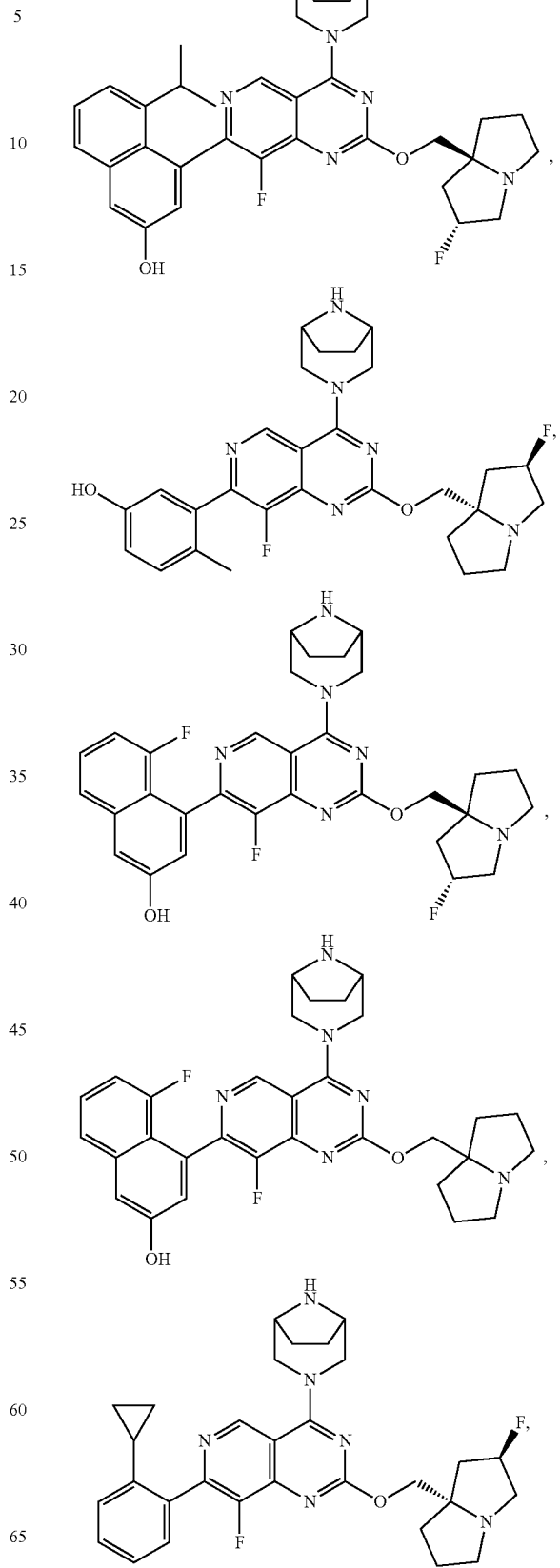

981
-continued
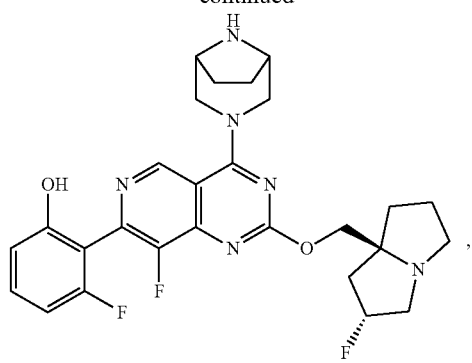,
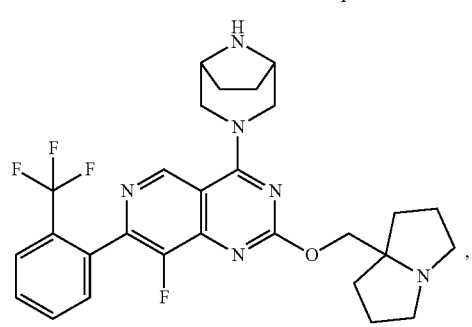,
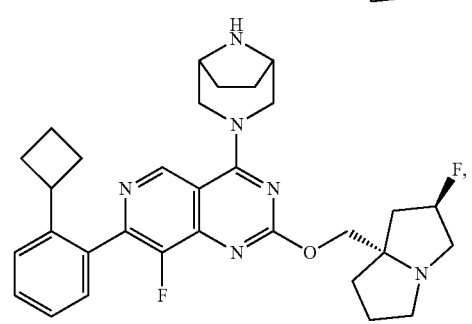,
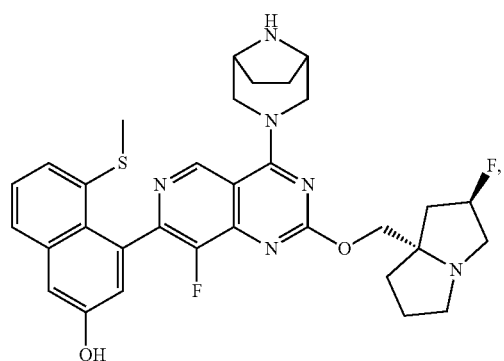,
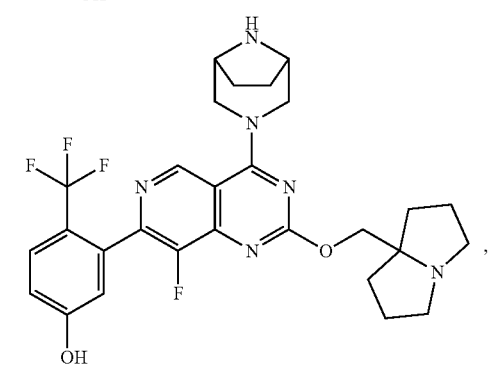,
982
-continued
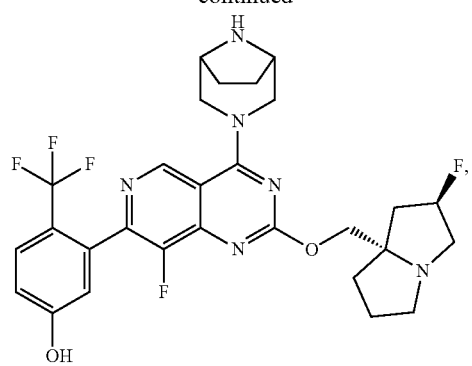,
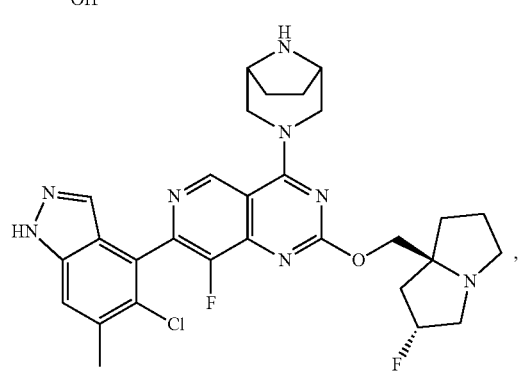,
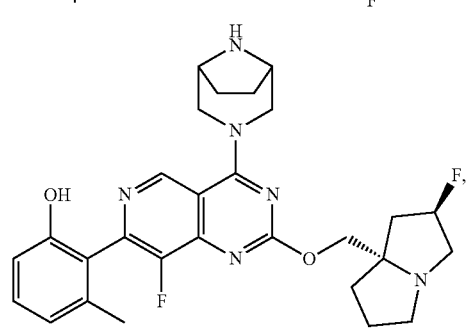,
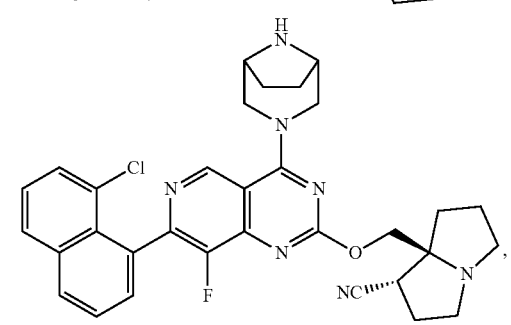,
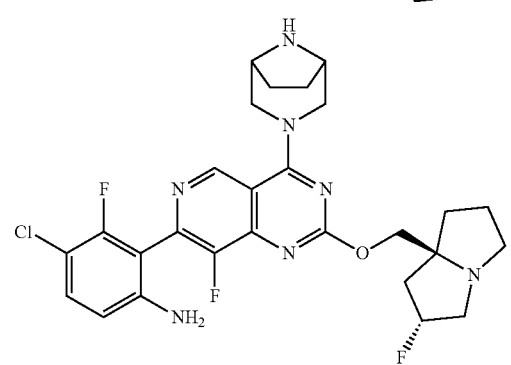, 983
-continued
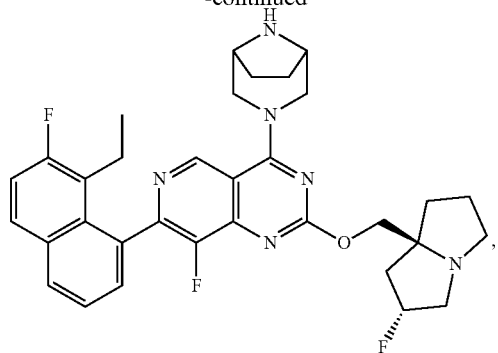
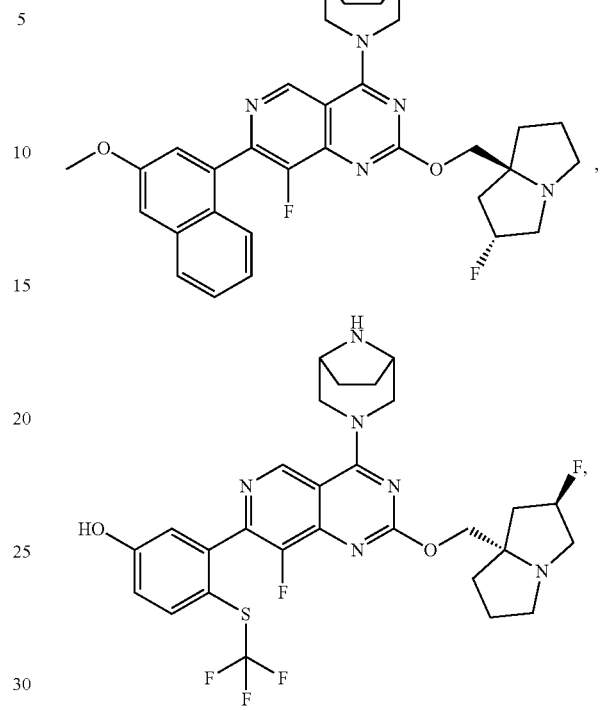
984
-continued
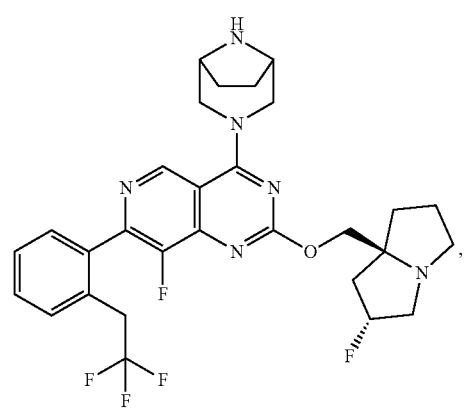
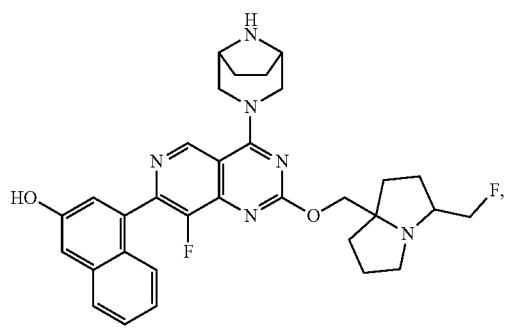
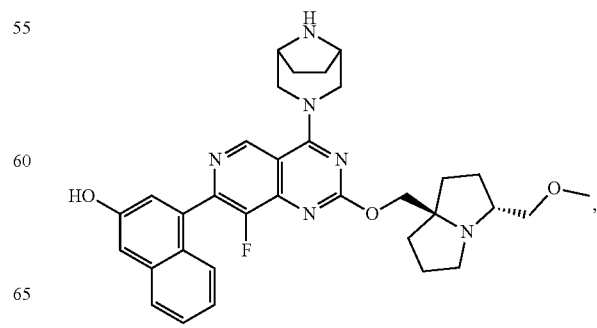

985
-continued
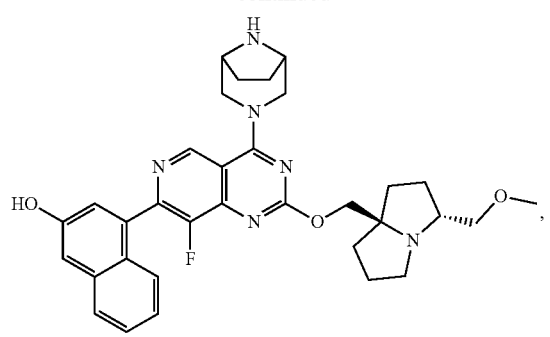
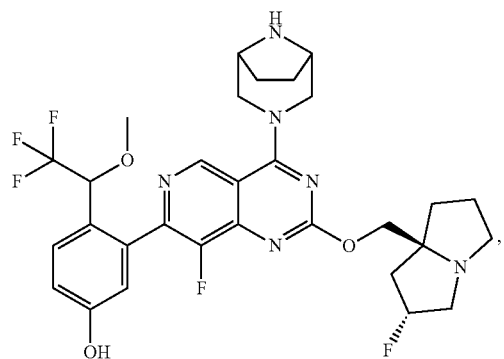
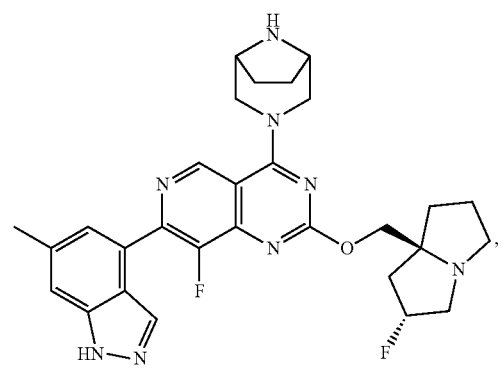
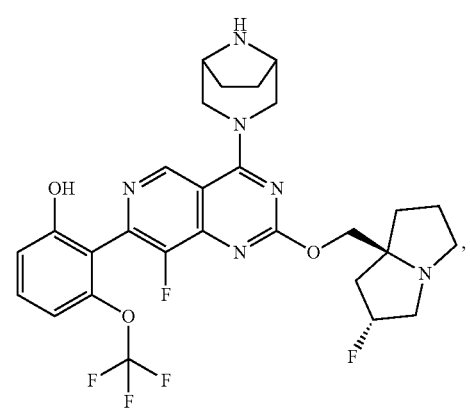
986
-continued
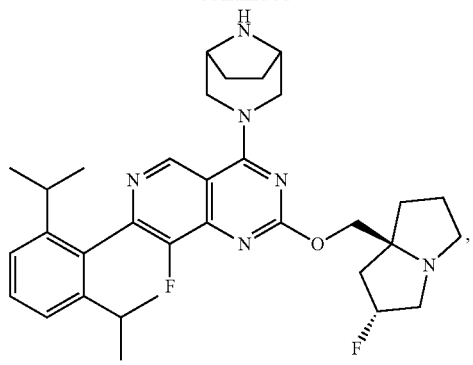
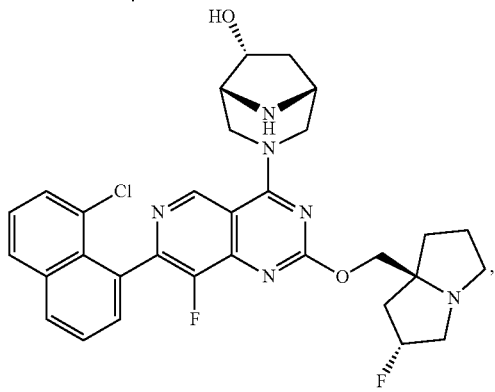
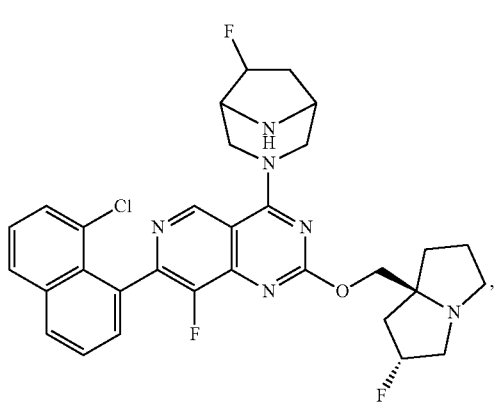
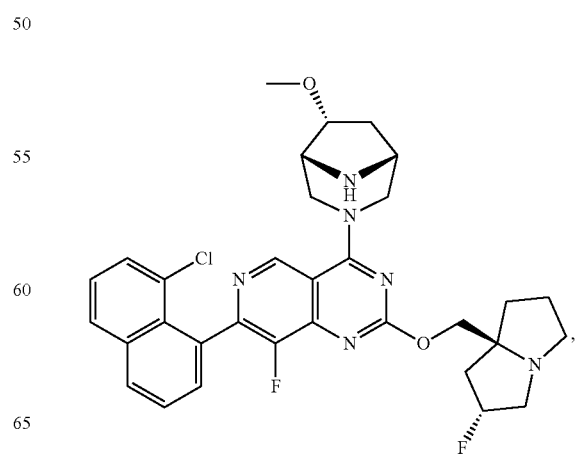

987
-continued
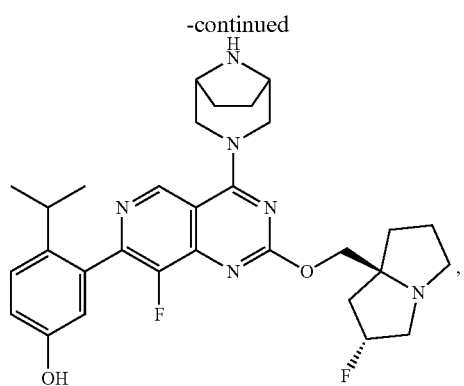
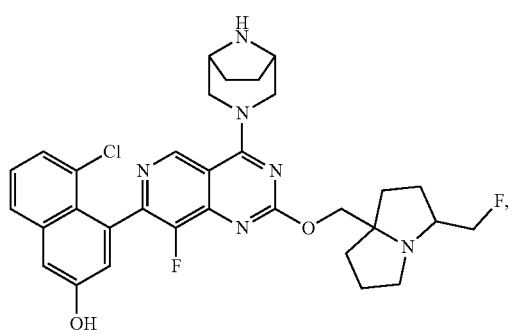
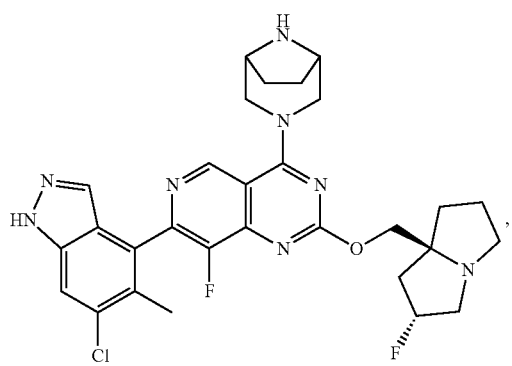
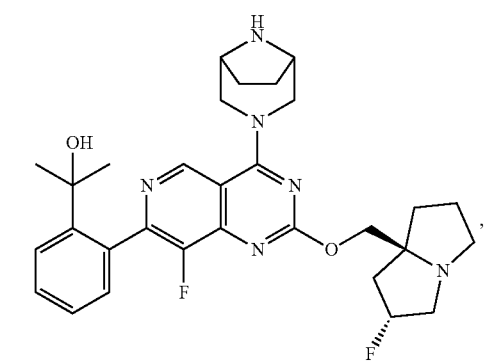
988
-continued
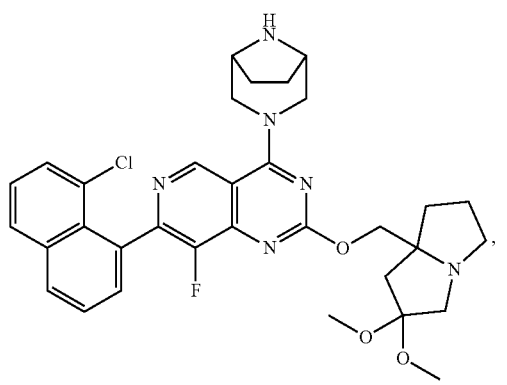
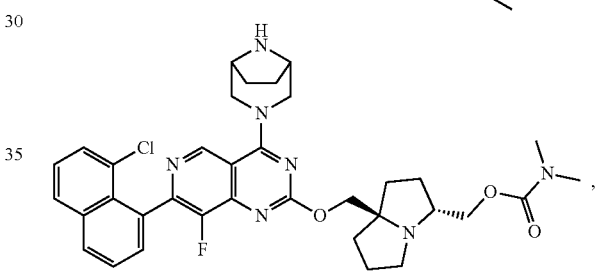
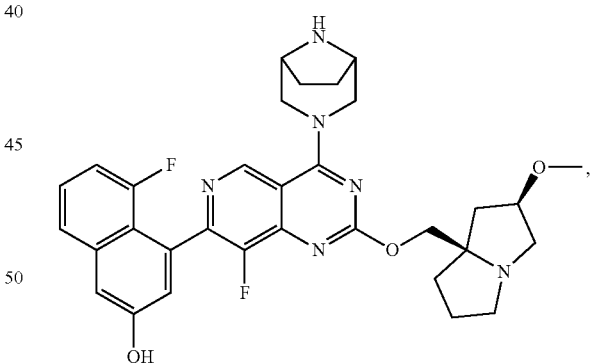
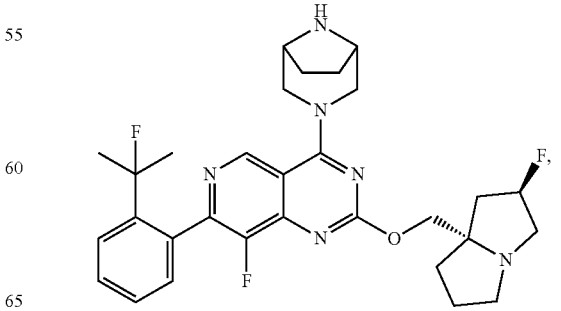

-continued
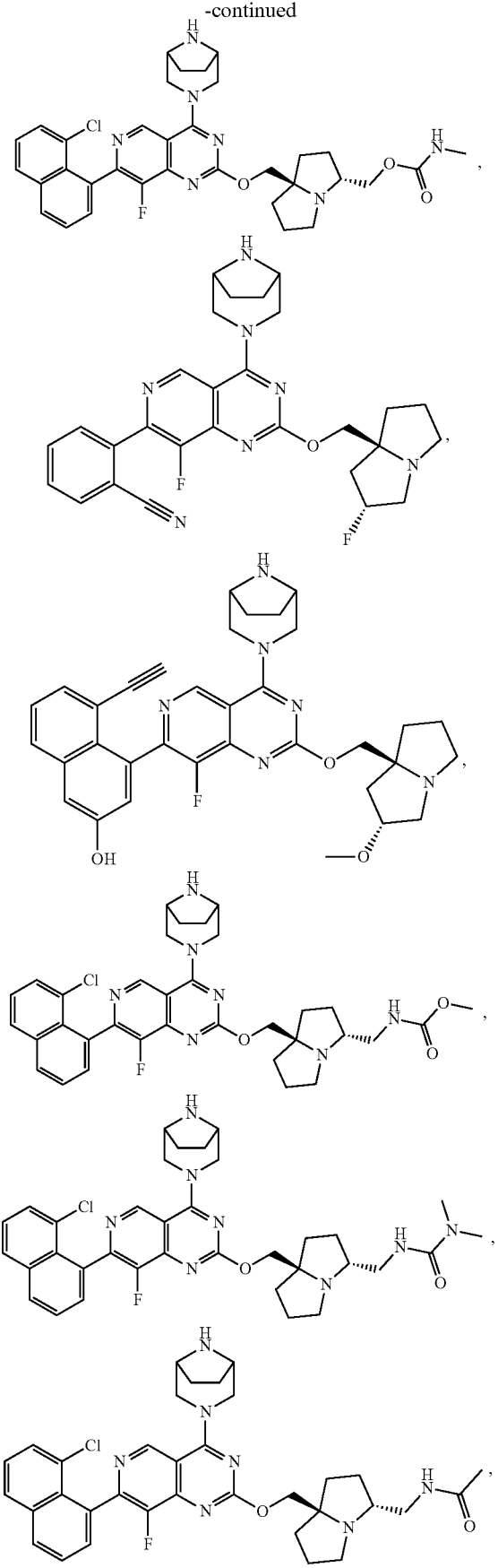
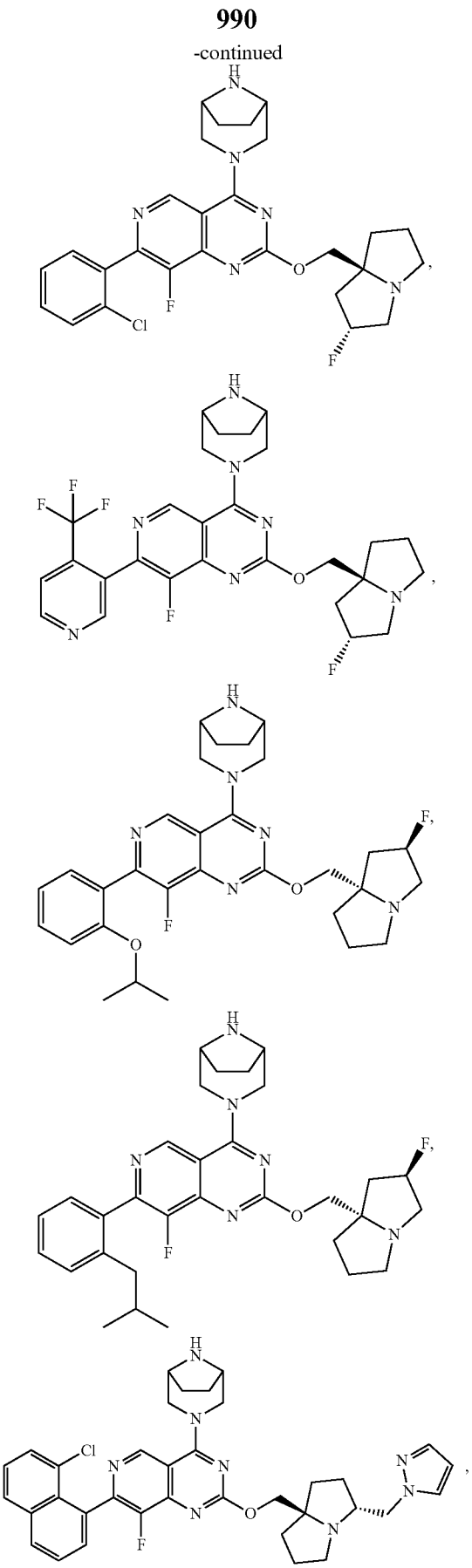

991
-continued
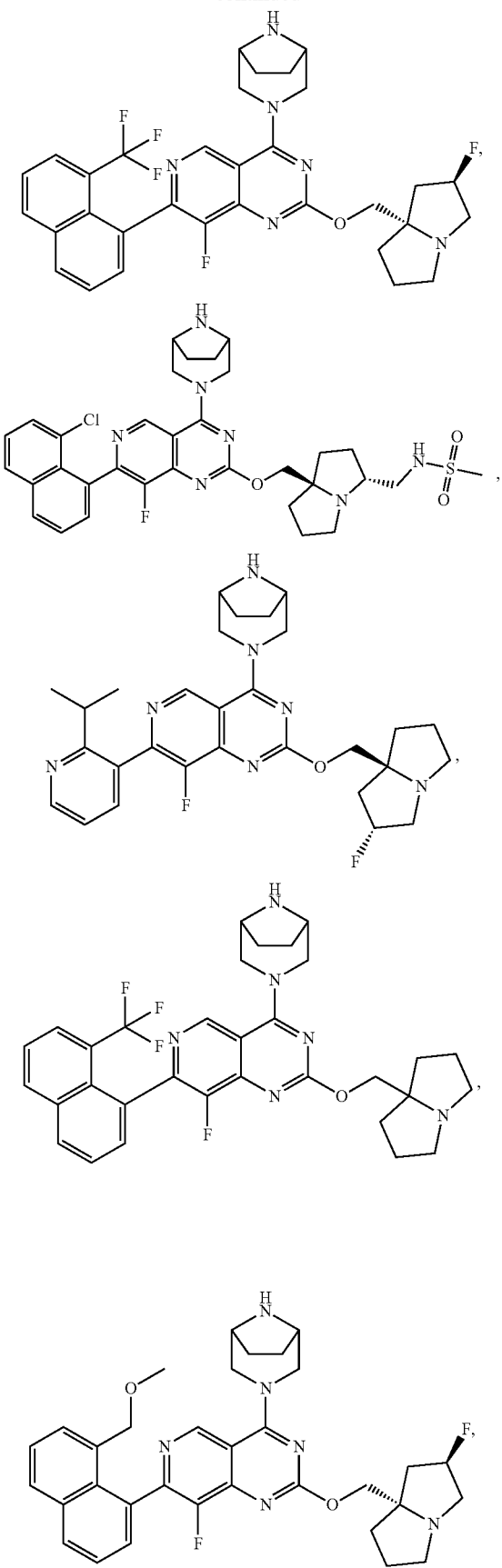
992
-continued
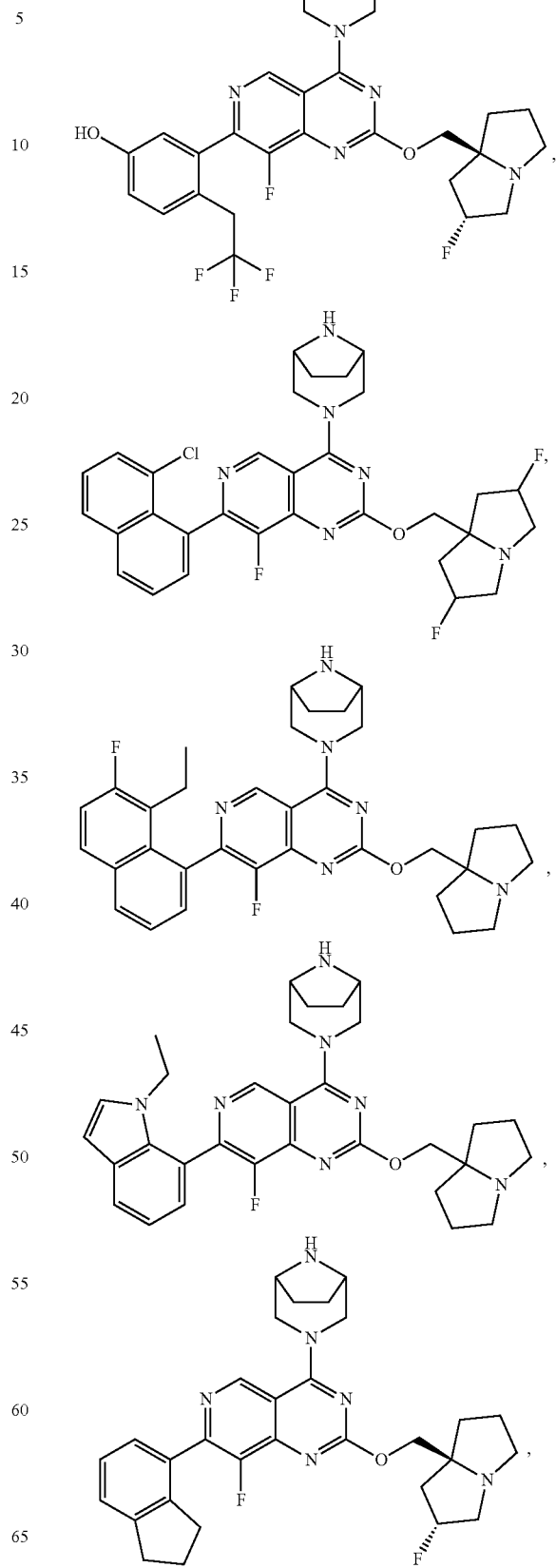

993
-continued
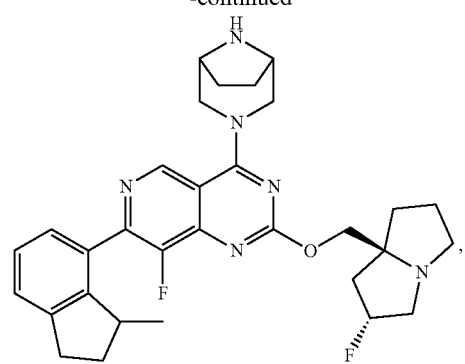
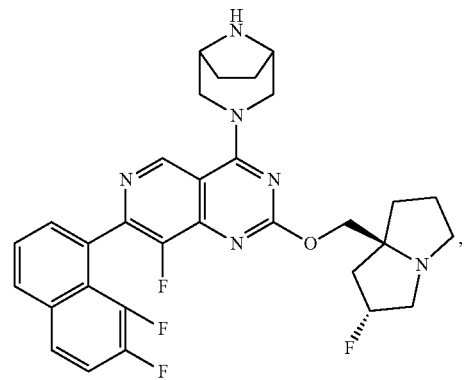
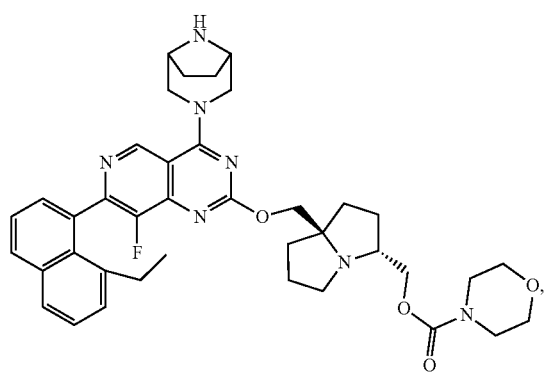
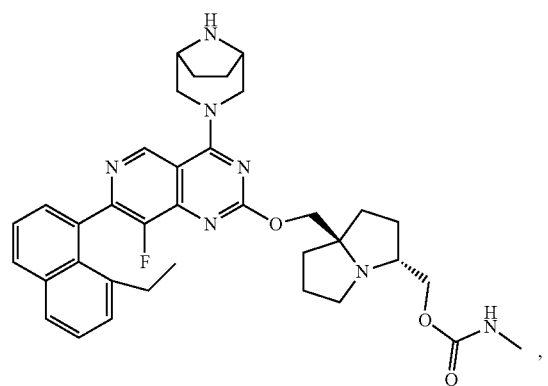
994
-continued
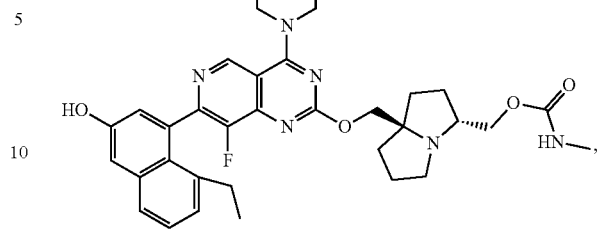
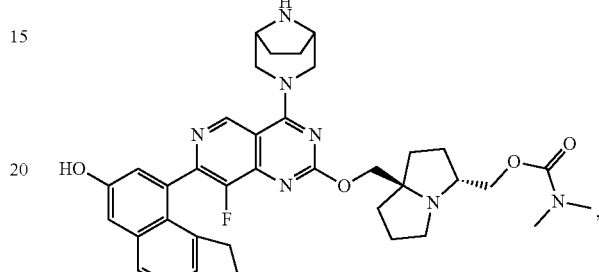
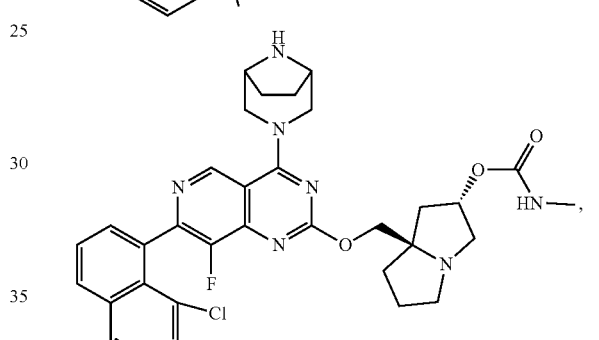
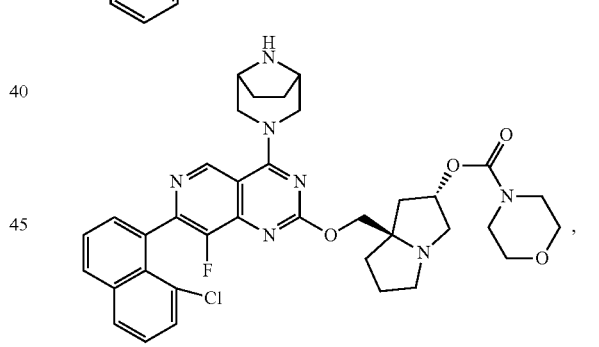
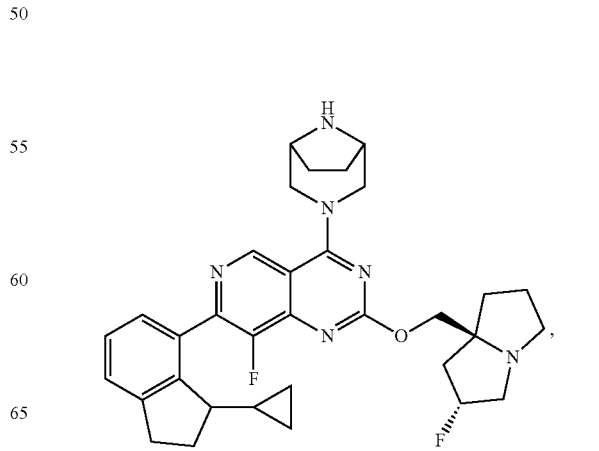

995
-continued
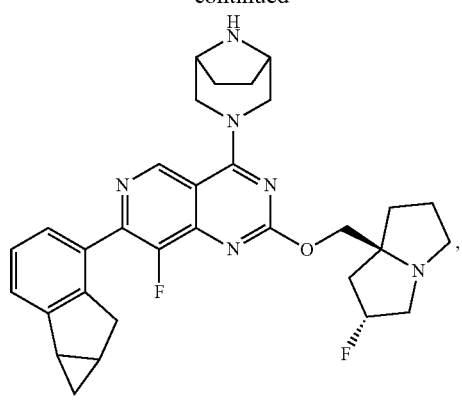
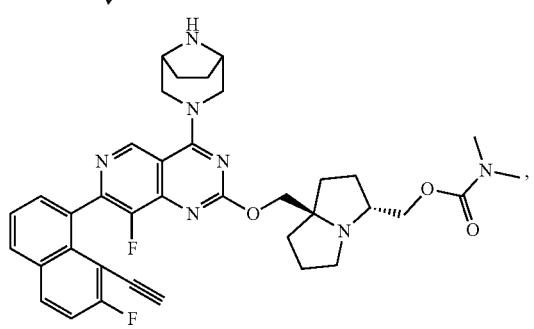
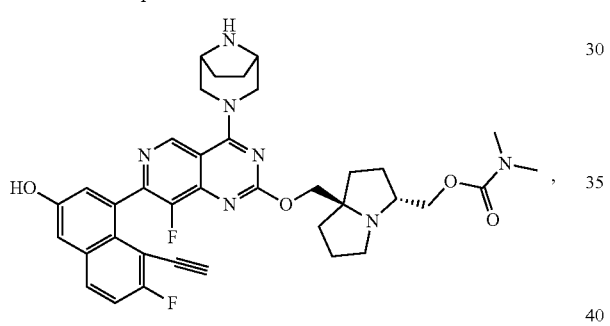
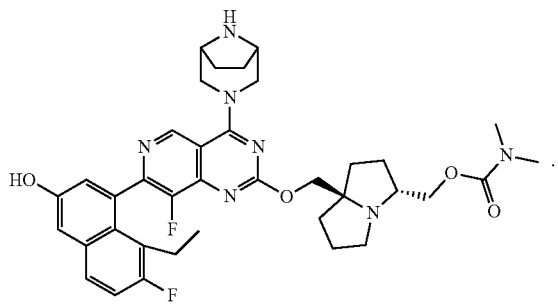
996
-continued
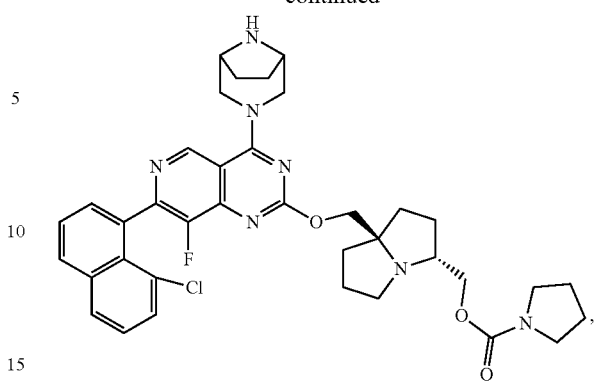
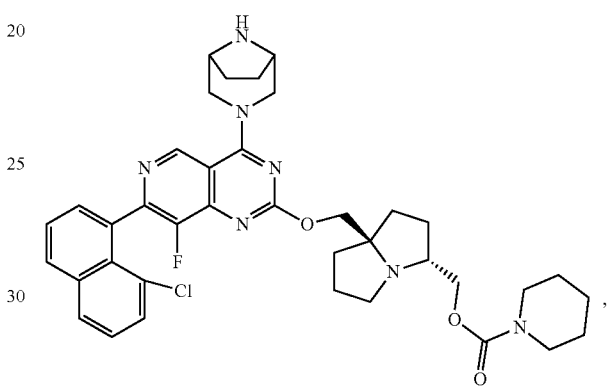
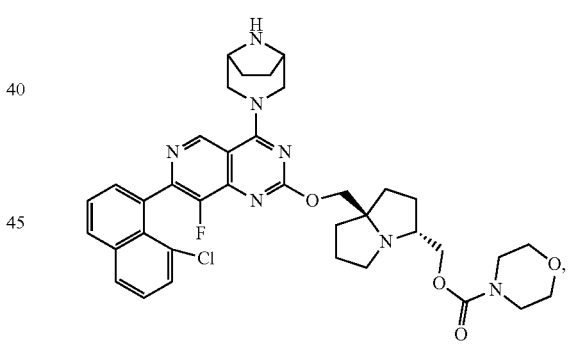
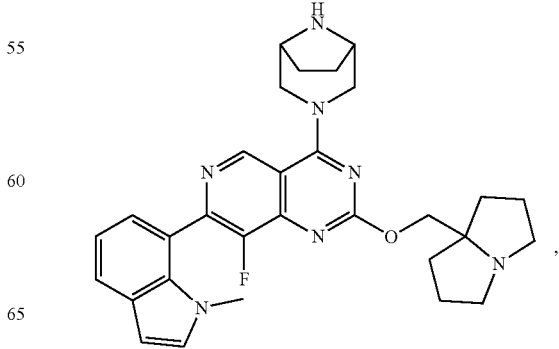

997
-continued
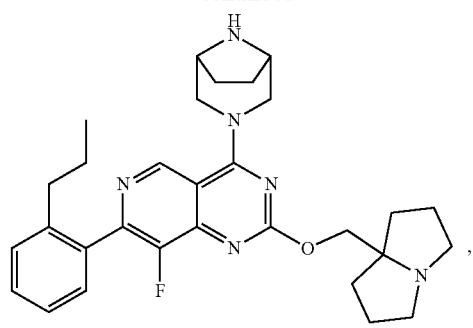
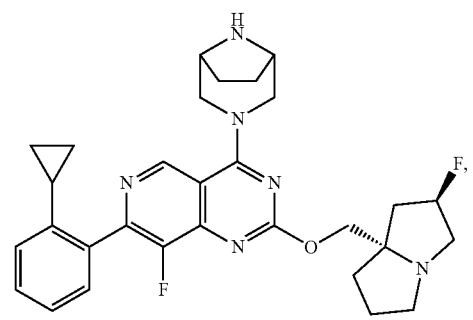
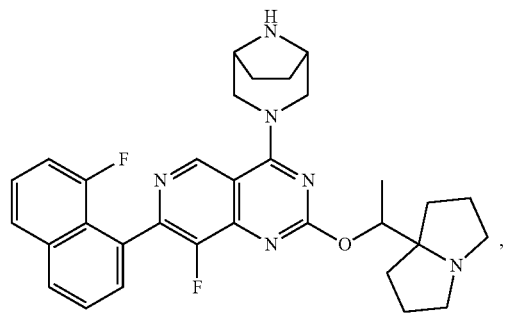
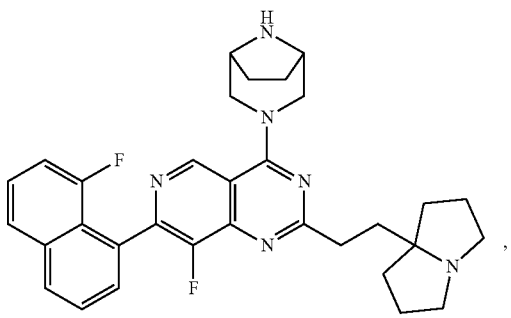
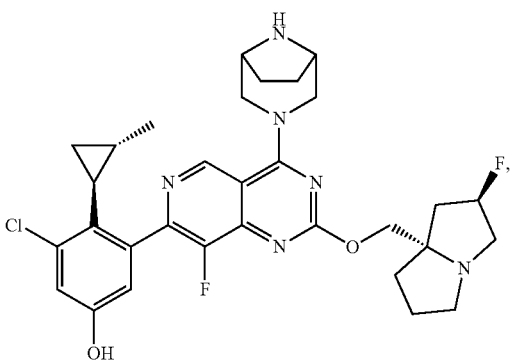
998
-continued
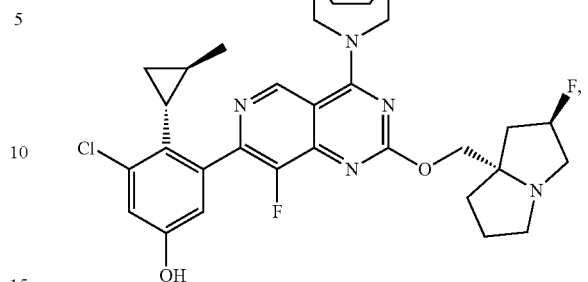
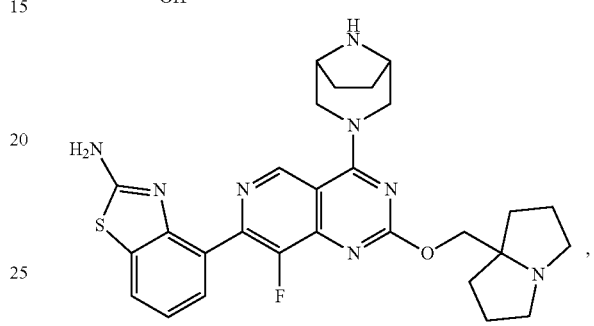
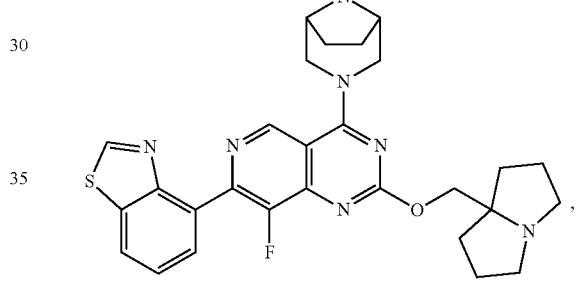
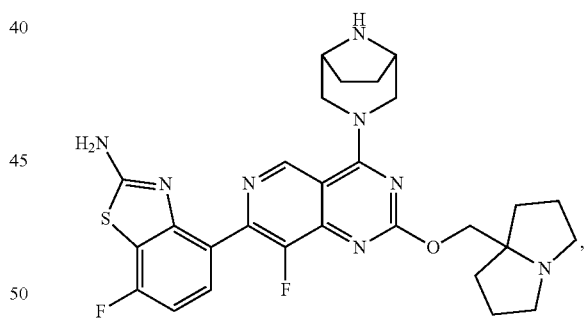
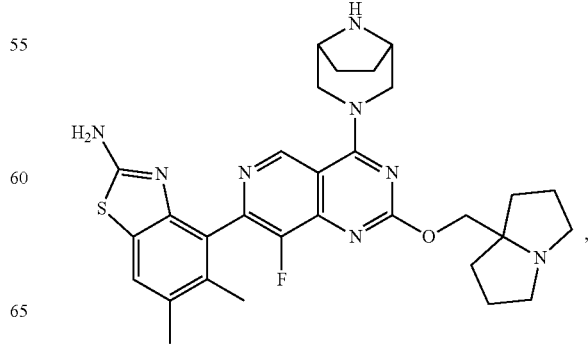

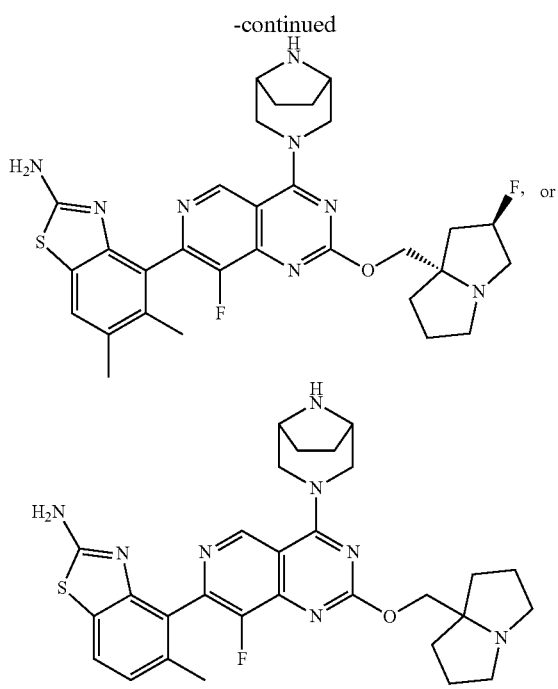

and pharmaceutically acceptable salts thereof.

2. A pharmaceutical composition, comprising a therapeutically effective amount of a compound of claim 1 or a pharmaceutically acceptable salt thereof, and a pharmaceutically acceptable excipient.

3. A method for inhibiting KRas G12D activity in a cell, comprising contacting the cell in which inhibition of KRas G12D activity is desired with an effective amount of a compound of according to claim 1 or a pharmaceutically acceptable salt thereof.

4. A method for inhibiting KRas G12D activity in a cell, comprising contacting the cell in which inhibition of KRas G12D activity is desired with the pharmaceutical composition of claim 2.

5. A method for treating a KRas G12D-associated cancer comprising administering to a patient in need thereof a therapeutically effective amount of a compound according to claim 1 or a pharmaceutically acceptable salt thereof.

6. A method for treating a KRas G12D-associated cancer comprising administering to a patient in need thereof the pharmaceutical composition of claim 2.

7. The method of claim 5, wherein the therapeutically effective amount of the compound is between about 0.01 to 100 mg/kg per day.

8. The method of claim 5, wherein the KRas G12D-associated cancer is selected from the group consisting of Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Biliary tract: gall bladder carcinoma, ampullary carcinoma, cholangiocarcinoma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma); Skin: malignant melanoma, basal cell carcinoma, squamous cell carcinoma, Kaposi's sarcoma, moles dysplastic nevi, lipoma, angioma, dermatofibroma, keloids, psoriasis; and Adrenal glands: neuroblastoma.

9. The method of claim 5, wherein the cancer is non-small cell lung cancer, small cell lung cancer, colorectal cancer, rectal cancer or pancreatic cancer.

10. A method for treating cancer in a patient in need thereof, the method comprising (a) determining that the cancer is associated with a KRas G12D mutation; and (b) administering to the patient a therapeutically effective amount of a compound according to claim 1.

11. A method for treating cancer in a patient in need thereof, the method comprising (a) determining that the cancer is associated with a KRas G12D mutation; and (b) administering to the patient the pharmaceutical composition of claim 2.

12. The method of claim 5 wherein the administering is done via a route selected from the group consisting of parenteral, intraperitoneal, intradermal, intracardiac, intraventricular, intracranial, intracerebrospinal, intrasynovial, intrathecal administration, intramuscular injection, intravitreous injection, intravenous injection, intra-arterial injection, oral, buccal, sublingual, transdermal, topical, intratracheal, intrarectal, subcutaneous, and topical administration.

13. The method of claim 12, wherein the administering is done via an intravenous injection.

14. The method of claim 12, wherein the administering is done via an intramuscular injection.

15. The method of claim 12, wherein the administering is done via an intra-arterial injection.

16. The method of claim 12, wherein the administering comprises utilizing a delivery device.

17. The method of claim 12, wherein the administering is done in a hospital setting.

18. The method of claim 10, wherein the cancer is a KRas G12D-associated cancer.

19. The method of claim 11, wherein the cancer is a KRas G12D-associated cancer.

\* \* \* \* \*